US012590062B2

(12) United States Patent
Aktoudianakis et al.

(10) Patent No.: US 12,590,062 B2
(45) Date of Patent: Mar. 31, 2026

(54) PD-1/PD-L1 INHIBITORS

(71) Applicant: Gilead Sciences, Inc., Foster City, CA (US)

(72) Inventors: Evangelos Aktoudianakis, Redwood City, CA (US); Todd Appleby, San Francisco, CA (US); Aesop Cho, Mountain View, CA (US); Zhimin Du, Belmont, CA (US); Michael Graupe, Pacifica, CA (US); Juan A. Guerrero, Concord, CA (US); Salman Y. Jabri, San Francisco, CA (US); Lateshkumar Thakorlal Lad, Belmont, CA (US); Paulo A. Machicao Tello, Oakland, CA (US); Jonathan William Medley, San Mateo, CA (US); Samuel E. Metobo, Newark, CA (US); Prasenjit Kumar Mukherjee, South San Francisco, CA (US); Devan Naduthambi, San Bruno, CA (US); Gregory Notte, Redwood City, CA (US); Eric Q. Parkhill, Union City, CA (US); Barton W. Phillips, San Mateo, CA (US); Scott Preston Simonovich, San Francisco, CA (US); Neil H. Squires, San Francisco, CA (US); Chandrasekar Venkataramani, San Carlos, CA (US); Peiyuan Wang, San Mateo, CA (US); William J. Watkins, Saratoga, CA (US); Jie Xu, Foster City, CA (US); Kin Shing Yang, San Mateo, CA (US); Christopher Allen Ziebenhaus, San Francisco, CA (US)

(73) Assignee: Gilead Sciences, Inc., Foster City, CA (US)

( * ) Notice: Subject to any disclaimer, the term of this patent is extended or adjusted under 35 U.S.C. 154(b) by 1075 days.

(21) Appl. No.: 17/098,171

(22) Filed: Nov. 13, 2020

(65) Prior Publication Data

US 2021/0323922 A1 Oct. 21, 2021

Related U.S. Application Data

(63) Continuation of application No. 16/840,217, filed on Apr. 3, 2020, now abandoned, which is a continuation (Continued)

(51) Int. Cl.

| | |
|---|---|
| ***C07D 213/69*** | (2006.01) |
| ***A61K 31/44*** | (2006.01) |
| ***A61K 31/444*** | (2006.01) |
| ***A61K 31/4545*** | (2006.01) |
| ***A61K 31/497*** | (2006.01) |
| ***A61K 31/5377*** | (2006.01) |
| ***A61K 45/06*** | (2006.01) |

(Continued)

(52) U.S. Cl.

CPC ............ *C07D 213/69* (2013.01); *A61K 31/44* (2013.01); *A61K 31/444* (2013.01); *A61K 31/4545* (2013.01); *A61K 31/497* (2013.01); *A61K 31/5377* (2013.01); *A61K 45/06* (2013.01); *C07D 213/30* (2013.01); *C07D 213/61* (2013.01); *C07D 213/64* (2013.01); *C07D 213/85* (2013.01); *C07D 295/088* (2013.01); *C07D 401/04* (2013.01); *C07D 401/14* (2013.01); *C07D 405/14* (2013.01); *C07D 487/08* (2013.01); *C07D 487/10* (2013.01); *C07D 491/107* (2013.01); *C07D 498/04* (2013.01); *C07D 519/00* (2013.01)

(58) Field of Classification Search

CPC .. A61K 31/5377; A61K 31/44; A61K 31/444; A61K 31/4545; A61K 31/497; A61K 45/06; C07D 213/85; C07D 295/088; C07D 491/107; C07D 401/12; C07D 405/12; C07D 413/12; C07D 213/69; C07D 213/30; C07D 213/61; C07D 213/64; C07D 401/04; C07D 401/14; C07D 405/14; C07D 487/08; C07D 487/10; C07D 498/04; C07D 519/00; C07D 417/14; C07D 487/04; C07D 471/04; A61P 35/02; A61P 35/00

See application file for complete search history.

(56) References Cited

U.S. PATENT DOCUMENTS

| | | | |
|---|---|---|---|
| 6,319,494 | B1 | 11/2001 | Capon et al. |
| 7,405,295 | B2 | 7/2008 | Currie et al. |

(Continued)

FOREIGN PATENT DOCUMENTS

| | | | |
|---|---|---|---|
| AU | 2018256423 | A1 | 10/2019 |
| AU | 2021200639 | A1 | 3/2021 |

(Continued)

OTHER PUBLICATIONS

International Search Report and Written Opinion for International Application No. PCT/US2018/028386 dated Jun. 22, 2018. (14 pages).

(Continued)

*Primary Examiner* — Jeffrey H Murray
*Assistant Examiner* — Luisalberto Gonzalez
(74) *Attorney, Agent, or Firm* — Schwegman Lundberg & Woessner, P.A.

(57) ABSTRACT

Compounds according to formula (I), methods of using said compounds singly or in combination with additional agents and compositions of said compounds for the treatment of cancer are disclosed.

18 Claims, No Drawings

Related U.S. Application Data of application No. 16/551,550, filed on Aug. 26, 2019, now abandoned, which is a continuation of application No. 15/957,739, filed on Apr. 19, 2018, now abandoned.

(60) Provisional application No. 62/507,678, filed on May 17, 2017, provisional application No. 62/488,017, filed on Apr. 20, 2017.

(51) Int. Cl.

| | |
|---|---|
| ***C07D 213/30*** | (2006.01) |
| ***C07D 213/61*** | (2006.01) |
| ***C07D 213/64*** | (2006.01) |
| ***C07D 213/85*** | (2006.01) |
| ***C07D 295/088*** | (2006.01) |
| ***C07D 401/04*** | (2006.01) |
| ***C07D 401/14*** | (2006.01) |
| ***C07D 405/14*** | (2006.01) |
| ***C07D 487/08*** | (2006.01) |
| ***C07D 487/10*** | (2006.01) |
| ***C07D 491/107*** | (2006.01) |
| ***C07D 498/04*** | (2006.01) |
| ***C07D 519/00*** | (2006.01) |

(56) References Cited

U.S. PATENT DOCUMENTS

| | | | |
|---|---|---|---|
| 7,446,190 | B2 | 11/2008 | Sadelain et al. |
| 7,687,522 | B2 | 3/2010 | Bellon et al. |
| 7,741,465 | B1 | 6/2010 | Eshhar et al. |
| 7,750,048 | B2 | 7/2010 | Kuo et al. |
| 7,943,743 | B2 | 5/2011 | Korman et al. |
| 8,008,449 | B2 | 8/2011 | Korman et al. |
| 8,273,341 | B2 | 9/2012 | Guo et al. |
| 8,450,321 | B2 | 5/2013 | Mitchell et al. |
| 8,450,460 | B2 | 5/2013 | Hill et al. |
| 8,513,184 | B2 | 8/2013 | Appleby et al. |
| 8,541,424 | B2 | 9/2013 | Degoey et al. |
| 8,575,353 | B2 | 11/2013 | Cannizzaro et al. |
| 8,722,054 | B2 | 5/2014 | Apelian et al. |
| 8,835,451 | B2 | 9/2014 | Serrano-Wu et al. |
| 9,089,520 | B2 | 7/2015 | Brenner |
| 9,181,288 | B2 | 11/2015 | Hartman et al. |
| 9,186,337 | B2 | 11/2015 | Baker et al. |
| 10,710,986 | B2 | 7/2020 | Aktoudianakis et al. |
| 10,774,071 | B2 | 9/2020 | Aktoudianakis et al. |
| 11,155,520 | B2 | 10/2021 | Loy et al. |
| 2002/0091116 | A1 | 7/2002 | Zhu et al. |
| 2003/0013028 | A1 | 1/2003 | Kaoru et al. |
| 2003/0119844 | A1 | 6/2003 | Huang et al. |
| 2004/0209936 | A1 | 10/2004 | Bratton et al. |
| 2004/0235877 | A1 | 11/2004 | Natsuki et al. |
| 2005/0224524 | A1 | 10/2005 | Khan et al. |
| 2006/0019967 | A1 | 1/2006 | Wu et al. |
| 2007/0155726 | A1 | 7/2007 | Arnaiz et al. |
| 2008/0234251 | A1 | 9/2008 | Doherty et al. |
| 2008/0306050 | A1 | 12/2008 | Doherty et al. |
| 2009/0047249 | A1 | 2/2009 | Graupe et al. |
| 2009/0142345 | A1 | 6/2009 | Satou et al. |
| 2010/0015178 | A1 | 1/2010 | Combs et al. |
| 2010/0029585 | A1 | 2/2010 | Howbert et al. |
| 2010/0143301 | A1 | 6/2010 | Desai et al. |
| 2010/0249175 | A1 | 9/2010 | Wilson et al. |
| 2011/0092485 | A1 | 4/2011 | Howbert et al. |
| 2011/0098248 | A1 | 4/2011 | Halcomb et al. |
| 2011/0118235 | A1 | 5/2011 | Howbert et al. |
| 2011/0287011 | A1 | 11/2011 | Gurney et al. |
| 2012/0082658 | A1 | 4/2012 | Hershberg |
| 2012/0189539 | A1 | 7/2012 | Wang et al. |
| 2012/0219615 | A1 | 8/2012 | Hershberg et al. |
| 2012/0225851 | A1 | 9/2012 | Cardone et al. |
| 2012/0289558 | A1 | 11/2012 | Kounnas et al. |
| 2012/0309701 | A1 | 12/2012 | Janetka et al. |
| 2013/0022629 | A1 | 1/2013 | Sharpe et al. |
| 2013/0023495 | A1 | 1/2013 | Meyers et al. |
| 2013/0079327 | A1 | 3/2013 | Yamamoto et al. |
| 2013/0217880 | A1 | 8/2013 | Yamamoto et al. |
| 2013/0225552 | A1 | 8/2013 | Allen et al. |
| 2013/0251673 | A1 | 9/2013 | Hartman et al. |
| 2013/0267517 | A1 | 10/2013 | Guo et al. |
| 2013/0310379 | A1 | 11/2013 | Albrecht et al. |
| 2013/0324514 | A1 | 12/2013 | Hamprecht et al. |
| 2013/0344029 | A1 | 12/2013 | Aciro et al. |
| 2013/0344030 | A1 | 12/2013 | Steadman et al. |
| 2014/0030221 | A1 | 1/2014 | Aciro et al. |
| 2014/0045849 | A1 | 2/2014 | McGowan et al. |
| 2014/0064053 | A1 | 3/2014 | Tsuyama et al. |
| 2014/0066432 | A1 | 3/2014 | Howbert et al. |
| 2014/0073631 | A1 | 3/2014 | Shetty |
| 2014/0073642 | A1 | 3/2014 | Mcgowan et al. |
| 2014/0088085 | A1 | 3/2014 | Burgess et al. |
| 2014/0171432 | A1 | 6/2014 | Kanouni et al. |
| 2014/0178337 | A1 | 6/2014 | Hartman et al. |
| 2014/0194469 | A1 | 7/2014 | Nie et al. |
| 2014/0213591 | A1 | 7/2014 | Chen et al. |
| 2014/0275084 | A1 | 9/2014 | Kanouni et al. |
| 2014/0275092 | A1 | 9/2014 | Albrecht et al. |
| 2014/0275167 | A1 | 9/2014 | Hartman |
| 2014/0330015 | A1 | 11/2014 | Yamamoto et al. |
| 2014/0343032 | A1 | 11/2014 | Guo et al. |
| 2014/0350031 | A1 | 11/2014 | Mc et al. |
| 2014/0371195 | A1 | 12/2014 | Labelle et al. |
| 2014/0371214 | A1 | 12/2014 | Labelle et al. |
| 2015/0031687 | A1 | 1/2015 | Guo et al. |
| 2015/0132258 | A1 | 5/2015 | Hartman |
| 2015/0175616 | A1 | 6/2015 | Blomgren et al. |
| 2015/0197533 | A1 | 7/2015 | Hartman et al. |
| 2015/0197538 | A1 | 7/2015 | Janetka et al. |
| 2015/0210682 | A1 | 7/2015 | Han et al. |
| 2015/0225355 | A1 | 8/2015 | Hartman |
| 2015/0252057 | A1 | 9/2015 | Guo et al. |
| 2015/0259324 | A1 | 9/2015 | Hartman et al. |
| 2015/0274652 | A1 | 10/2015 | Hartman |
| 2015/0315159 | A1 | 11/2015 | Hartman |
| 2015/0352206 | A1 | 12/2015 | Gajewsi et al. |
| 2016/0039808 | A1 | 2/2016 | Kanouni et al. |
| 2016/0102096 | A1 | 4/2016 | Boesen et al. |
| 2016/0122344 | A1 | 5/2016 | Han et al. |
| 2016/0137652 | A1 | 5/2016 | Beck et al. |
| 2016/0145304 | A1 | 5/2016 | Baumann et al. |
| 2016/0166592 | A1 | 6/2016 | Bae et al. |
| 2016/0176899 | A1 | 6/2016 | Schwitter et al. |
| 2016/0194307 | A1 | 7/2016 | Chupak et al. |
| 2016/0207923 | A1 | 7/2016 | Youngman et al. |
| 2016/0220586 | A1 | 8/2016 | Andre et al. |
| 2016/0237090 | A1 | 8/2016 | Hu et al. |
| 2016/0333009 | A1 | 11/2016 | Bartlett et al. |
| 2016/0333013 | A1 | 11/2016 | Norris et al. |
| 2017/0037040 | A1 | 2/2017 | Eckhardt et al. |
| 2017/0088532 | A1 | 3/2017 | Cohen et al. |
| 2017/0100414 | A1 | 4/2017 | Dunman et al. |
| 2017/0107202 | A1 | 4/2017 | Yeung et al. |
| 2017/0107216 | A1 | 4/2017 | Wu et al. |
| 2017/0145025 | A1 | 5/2017 | Li et al. |
| 2017/0174671 | A1 | 6/2017 | Wu et al. |
| 2017/0174679 | A1 | 6/2017 | Lajkiewicz et al. |
| 2017/0210715 | A1 | 7/2017 | Shao et al. |
| 2017/0239351 | A1 | 8/2017 | Hamdy et al. |
| 2017/0252432 | A1 | 9/2017 | Allen et al. |
| 2017/0262253 | A1 | 9/2017 | Silva et al. |
| 2017/0266211 | A1 | 9/2017 | David et al. |
| 2017/0283462 | A1 | 10/2017 | Miller et al. |
| 2017/0283463 | A1 | 10/2017 | Miller et al. |
| 2017/0320875 | A1 | 11/2017 | Li et al. |
| 2017/0331067 | A1 | 11/2017 | Park et al. |
| 2017/0362253 | A1 | 12/2017 | Xiao et al. |
| 2018/0008554 | A1 | 1/2018 | Lange et al. |
| 2018/0044303 | A1 | 2/2018 | Sasikumar et al. |
| 2018/0044304 | A1 | 2/2018 | Sasikumar et al. |
| 2018/0044305 | A1 | 2/2018 | Sasikumar et al. |
| 2018/0044329 | A1 | 2/2018 | Sasikumar et al. |

(56) References Cited

U.S. PATENT DOCUMENTS

| | | | |
|---|---|---|---|
| 2018/0044350 | A1 | 2/2018 | Sasikumar et al. |
| 2018/0045142 | A1 | 2/2018 | Dierksmeier et al. |
| 2018/0057455 | A1 | 3/2018 | Yeung et al. |
| 2018/0057486 | A1 | 3/2018 | Wu et al. |
| 2018/0065917 | A1 | 3/2018 | Webber et al. |
| 2018/0086793 | A1 | 3/2018 | Gillman et al. |
| 2018/0273519 | A1 | 9/2018 | Wu et al. |
| 2018/0305315 | A1 | 10/2018 | Aktoudianakis et al. |
| 2019/0040082 | A1 | 2/2019 | Xiao et al. |
| 2019/0062345 | A1 | 2/2019 | Xiao et al. |
| 2019/0071439 | A1 | 3/2019 | Li et al. |
| 2019/0135745 | A1 | 5/2019 | Lange et al. |
| 2019/0144402 | A1 | 5/2019 | Sasikumar et al. |
| 2019/0144439 | A1 | 5/2019 | Wu et al. |
| 2019/0202824 | A1 | 7/2019 | Wu et al. |
| 2019/0276435 | A1 | 9/2019 | Shepard et al. |
| 2019/0282555 | A1 | 9/2019 | Lange et al. |
| 2019/0345131 | A1 | 11/2019 | Aktoudianakis et al. |
| 2020/0157094 | A1 | 5/2020 | Du et al. |
| 2021/0024494 | A1 | 1/2021 | Aktoudianakis et al. |
| 2021/0053946 | A1 | 2/2021 | Aktoudianakis et al. |
| 2023/0212155 | A1 | 7/2023 | Aktoudianakis et al. |

FOREIGN PATENT DOCUMENTS

| | | | |
|---|---|---|---|
| AU | 2018256423 | B2 | 6/2021 |
| AU | 2021200639 | B2 | 12/2022 |
| AU | 2022279537 | A1 | 2/2023 |
| CA | 2984638 | | 12/2016 |
| CA | 3175847 | A1 | 10/2018 |
| CN | 103848820 | | 6/2014 |
| CN | 104341407 | | 2/2015 |
| CN | 104876912 | | 9/2015 |
| CN | 110799509 | B | 7/2024 |
| CN | 118878461 | A | 11/2024 |
| DE | 10104279 | | 8/2002 |
| EP | 2002838 | | 12/2008 |
| EP | 3363790 | | 8/2018 |
| EP | 3612525 | B1 | 10/2021 |
| EP | 4026835 | A2 | 7/2022 |
| IN | 202418035368 | A | 11/2024 |
| JP | 2001002661 | | 1/2001 |
| JP | 2001335476 | | 12/2001 |
| JP | 2012036168 | | 2/2012 |
| JP | 2013147443 | | 8/2013 |
| JP | 2016053633 | | 4/2016 |
| JP | 2016536333 | A | 11/2016 |
| JP | 2019530732 | A | 10/2019 |
| JP | 2019531274 | A | 10/2019 |
| JP | 2020518561 | A | 6/2020 |
| JP | 2022116244 | A | 8/2022 |
| JP | 7161491 | B2 | 10/2022 |
| JP | 2024009851 | A | 1/2024 |
| JP | 7512323 | B2 | 6/2024 |
| SG | 11201908619 | | 10/2019 |
| TW | 202432535 | A | 8/2024 |
| TW | I893530 | B | 8/2025 |
| UY | 35733 | A | 4/2016 |
| WO | WO 97/31910 | | 9/1997 |
| WO | WO-9917777 | | 4/1999 |
| WO | WO 2001/019798 | | 3/2001 |
| WO | WO 2001/056989 | | 8/2001 |
| WO | WO 2002/000647 | | 1/2002 |
| WO | WO 2002/020436 | | 3/2002 |
| WO | WO 2002/051775 | | 7/2002 |
| WO | WO 2004/052848 | | 6/2004 |
| WO | WO 2004/054582 | | 7/2004 |
| WO | WO 2004/084824 | | 10/2004 |
| WO | WO 2005/044797 | | 5/2005 |
| WO | WO 2005/051890 | | 6/2005 |
| WO | WO 2005/086808 | | 9/2005 |
| WO | WO 2005/095338 | | 10/2005 |
| WO | WO-2005097136 | | 10/2005 |
| WO | WO-2005113556 | A1 | 12/2005 |
| WO | WO 2006/011615 | | 2/2006 |
| WO | WO 2006/038738 | | 4/2006 |
| WO | WO-2006040646 | | 4/2006 |
| WO | WO 2006/052566 | | 5/2006 |
| WO | WO 2006/083612 | | 8/2006 |
| WO | WO 2006/083781 | | 8/2006 |
| WO | WO 2006/091394 | | 8/2006 |
| WO | WO 2006/123257 | | 11/2006 |
| WO | WO 2006/127503 | | 11/2006 |
| WO | WO 2007/013689 | | 2/2007 |
| WO | WO 2007/033002 | | 3/2007 |
| WO | WO 2007/047591 | | 4/2007 |
| WO | WO 2007/049050 | | 5/2007 |
| WO | WO 2007/052466 | | 5/2007 |
| WO | WO 2007/096142 | | 8/2007 |
| WO | WO 2007/104560 | | 9/2007 |
| WO | WO 2007/106469 | | 9/2007 |
| WO | WO 2007/109376 | | 9/2007 |
| WO | WO 2007/123225 | | 11/2007 |
| WO | WO 2007/128460 | | 11/2007 |
| WO | WO 2007/131619 | | 11/2007 |
| WO | WO 2007/131620 | | 11/2007 |
| WO | WO 2007/131621 | | 11/2007 |
| WO | WO 2007/131622 | | 11/2007 |
| WO | WO 2007/132307 | | 11/2007 |
| WO | WO 2007/136572 | | 11/2007 |
| WO | WO 2008/001931 | | 1/2008 |
| WO | WO 2008/014236 | | 1/2008 |
| WO | WO 2008/021936 | | 2/2008 |
| WO | WO 2008/030520 | | 3/2008 |
| WO | WO 2008/037266 | | 4/2008 |
| WO | WO 2008/054674 | | 5/2008 |
| WO | WO 2008/054675 | | 5/2008 |
| WO | WO 2008/063768 | | 5/2008 |
| WO | WO 2008/065409 | | 6/2008 |
| WO | WO 2008/066097 | | 6/2008 |
| WO | WO 2008/067644 | | 6/2008 |
| WO | WO 2008/073865 | | 6/2008 |
| WO | WO 2008/079965 | | 7/2008 |
| WO | WO 2008/083027 | | 7/2008 |
| WO | WO 2008/090327 | | 7/2008 |
| WO | WO 2008/090356 | | 7/2008 |
| WO | WO 2008/106202 | | 9/2008 |
| WO | WO-2008109943 | A1 | 9/2008 |
| WO | WO 2008/130514 | | 10/2008 |
| WO | WO 2008/139987 | | 11/2008 |
| WO | WO 2008/144925 | | 12/2008 |
| WO | WO 2008/147852 | | 12/2008 |
| WO | WO 2008/156656 | | 12/2008 |
| WO | WO 2009/017822 | | 2/2009 |
| WO | WO 2009/025983 | | 2/2009 |
| WO | WO-2009017833 | A2 | 2/2009 |
| WO | WO 2009/038204 | | 3/2009 |
| WO | WO-2009035791 | A1 | 3/2009 |
| WO | WO 2009/039942 | | 4/2009 |
| WO | WO 2009/039943 | | 4/2009 |
| WO | WO 2009/047798 | | 4/2009 |
| WO | WO 2009/048527 | | 4/2009 |
| WO | WO 2009/054390 | | 4/2009 |
| WO | WO 2009/054468 | | 4/2009 |
| WO | WO 2009/054479 | | 4/2009 |
| WO | WO 2009/058237 | | 5/2009 |
| WO | WO 2009/102568 | | 8/2009 |
| WO | WO 2009/102633 | | 8/2009 |
| WO | WO 2009/111056 | | 9/2009 |
| WO | WO 2009/112445 | | 9/2009 |
| WO | WO 2010/012650 | | 2/2010 |
| WO | WO 2010/017870 | | 2/2010 |
| WO | WO 2010/039238 | | 4/2010 |
| WO | WO 2010/045258 | | 4/2010 |
| WO | WO 2010/066682 | | 6/2010 |
| WO | WO 2010/082563 | | 7/2010 |
| WO | WO 2010/085522 | | 7/2010 |
| WO | WO 2010/085525 | | 7/2010 |
| WO | WO 2010/085528 | | 7/2010 |
| WO | WO 2010/091176 | | 8/2010 |
| WO | WO 2010/091413 | | 8/2010 |
| WO | WO 2010/096462 | | 8/2010 |
| WO | WO 2010/099527 | | 9/2010 |
| WO | WO 2010/111534 | | 9/2010 |

(56) References Cited

FOREIGN PATENT DOCUMENTS

| | | | |
|---|---|---|---|
| WO | WO 2010/123016 | | 10/2010 |
| WO | WO 2010/123017 | | 10/2010 |
| WO | WO 2010/132601 | | 11/2010 |
| WO | WO 2010/143733 | | 12/2010 |
| WO | WO 2010/144646 | | 12/2010 |
| WO | WO 2011/008709 | | 1/2011 |
| WO | WO 2011/024001 | | 3/2011 |
| WO | WO 2011/031934 | | 3/2011 |
| WO | WO 2011/031965 | | 3/2011 |
| WO | WO 2011/044073 | | 4/2011 |
| WO | WO 2011/046851 | | 4/2011 |
| WO | WO 2011/049825 | | 4/2011 |
| WO | WO 2011/052756 | | 5/2011 |
| WO | WO 2011/066183 | | 6/2011 |
| WO | WO 2011/066241 | | 6/2011 |
| WO | WO 2011/073376 | | 6/2011 |
| WO | WO 2011/076732 | | 6/2011 |
| WO | WO 2011/076734 | | 6/2011 |
| WO | WO 2011/078371 | | 6/2011 |
| WO | WO 2011/080755 | | 7/2011 |
| WO | WO 2011/082400 | | 7/2011 |
| WO | WO 2011/092284 | | 8/2011 |
| WO | WO-2011097513 | A1 | 8/2011 |
| WO | WO 2011/119858 | | 9/2011 |
| WO | WO 2011/119870 | | 9/2011 |
| WO | WO 2011/138665 | | 11/2011 |
| WO | WO 2011/143208 | | 11/2011 |
| WO | WO 2011/143466 | | 11/2011 |
| WO | WO 2011/151436 | | 12/2011 |
| WO | WO 2011/161030 | | 12/2011 |
| WO | WO 2012/004269 | | 1/2012 |
| WO | WO 2012/004270 | | 1/2012 |
| WO | WO 2012/010413 | | 1/2012 |
| WO | WO 2012/011124 | | 1/2012 |
| WO | WO 2012/012627 | | 1/2012 |
| WO | WO 2012/036168 | | 3/2012 |
| WO | WO-2012027721 | A2 | 3/2012 |
| WO | WO 2012/046869 | | 4/2012 |
| WO | WO 2012/050918 | | 4/2012 |
| WO | WO 2012/065904 | | 5/2012 |
| WO | WO 2012/068234 | | 5/2012 |
| WO | WO 2012/072691 | | 6/2012 |
| WO | WO 2012/078802 | | 6/2012 |
| WO | WO 2012/083043 | | 6/2012 |
| WO | WO 2012/083048 | | 6/2012 |
| WO | WO 2012/083053 | | 6/2012 |
| WO | WO 2012/083059 | | 6/2012 |
| WO | WO 2012/083061 | | 6/2012 |
| WO | WO-2012079000 | A1 | 6/2012 |
| WO | WO 2012/098033 | | 7/2012 |
| WO | WO 2012/111849 | | 8/2012 |
| WO | WO 2012/129562 | | 9/2012 |
| WO | WO 2012/136221 | | 10/2012 |
| WO | WO 2012/147518 | | 11/2012 |
| WO | WO 2012/154608 | | 11/2012 |
| WO | WO 2013/009259 | | 1/2013 |
| WO | WO 2013/025424 | | 2/2013 |
| WO | WO-2013027802 | A1 | 2/2013 |
| WO | WO-2013034933 | A1 | 3/2013 |
| WO | WO 2013/057743 | | 4/2013 |
| WO | WO-2013052699 | A2 | 4/2013 |
| WO | WO-2013096744 | A1 | 6/2013 |
| WO | WO 2013/102626 | | 7/2013 |
| WO | WO 2013/104257 | | 7/2013 |
| WO | WO 2013/106520 | | 7/2013 |
| WO | WO 2013/109521 | | 7/2013 |
| WO | WO 2013/122028 | | 8/2013 |
| WO | WO 2013/122029 | | 8/2013 |
| WO | WO-2013112741 | A1 | 8/2013 |
| WO | WO-2013116562 | A1 | 8/2013 |
| WO | WO 2013/128378 | | 9/2013 |
| WO | WO 2013/144097 | | 10/2013 |
| WO | WO 2013/154163 | | 10/2013 |
| WO | WO-2013144129 | A1 | 10/2013 |
| WO | WO 2013/164292 | | 11/2013 |
| WO | WO 2013/170113 | | 11/2013 |
| WO | WO 2013/170115 | | 11/2013 |
| WO | WO 2013/178575 | | 12/2013 |
| WO | WO 2014/014129 | | 1/2014 |
| WO | WO 2014/014530 | | 1/2014 |
| WO | WO 2014/019186 | | 2/2014 |
| WO | WO-2014023813 | A1 | 2/2014 |
| WO | WO 2014/035827 | | 3/2014 |
| WO | WO-2014033167 | A1 | 3/2014 |
| WO | WO-2014033170 | A1 | 3/2014 |
| WO | WO-2014033176 | A1 | 3/2014 |
| WO | WO-2014037480 | A1 | 3/2014 |
| WO | WO-2014047624 | A1 | 3/2014 |
| WO | WO-2014056953 | A1 | 4/2014 |
| WO | WO 2014/073904 | | 5/2014 |
| WO | WO 2014/078608 | | 5/2014 |
| WO | WO 2014/078609 | | 5/2014 |
| WO | WO 2014/078610 | | 5/2014 |
| WO | WO 2014/081689 | | 5/2014 |
| WO | WO-2014073738 | A1 | 5/2014 |
| WO | WO-2014076221 | A1 | 5/2014 |
| WO | WO 2014/082918 | | 6/2014 |
| WO | WO 2014/086712 | | 6/2014 |
| WO | WO-2014100765 | A1 | 6/2014 |
| WO | WO-2014100767 | A1 | 6/2014 |
| WO | WO 2014/122067 | | 8/2014 |
| WO | WO 2014/130608 | | 8/2014 |
| WO | WO-2014128189 | A1 | 8/2014 |
| WO | WO 2014/133361 | | 9/2014 |
| WO | WO 2014/134243 | | 9/2014 |
| WO | WO 2014/145817 | | 9/2014 |
| WO | WO 2014/146604 | | 9/2014 |
| WO | WO-2014131847 | A1 | 9/2014 |
| WO | WO 2014/169817 | | 10/2014 |
| WO | WO 2014/170842 | | 10/2014 |
| WO | WO 2014/171762 | | 10/2014 |
| WO | WO-2014161888 | A1 | 10/2014 |
| WO | WO-2014164708 | A1 | 10/2014 |
| WO | WO 2014/187343 | | 11/2014 |
| WO | WO-2014182929 | A1 | 11/2014 |
| WO | WO-2014184350 | A1 | 11/2014 |
| WO | WO-2014184365 | A1 | 11/2014 |
| WO | WO-2014201409 | A1 | 12/2014 |
| WO | WO 2015/000412 | | 1/2015 |
| WO | WO 2015/010655 | | 1/2015 |
| WO | WO-2015011281 | A1 | 1/2015 |
| WO | WO 2015/020184 | | 2/2015 |
| WO | WO 2015/024448 | | 2/2015 |
| WO | WO 2015/024526 | | 2/2015 |
| WO | WO-2015017460 | A1 | 2/2015 |
| WO | WO 2015/028960 | | 3/2015 |
| WO | WO 2015/032328 | | 3/2015 |
| WO | WO 2015/034820 | | 3/2015 |
| WO | WO 2015/044073 | | 4/2015 |
| WO | WO 2015/051496 | | 4/2015 |
| WO | WO-2015059212 | A1 | 4/2015 |
| WO | WO 2015/062486 | | 5/2015 |
| WO | WO 2015/065621 | | 5/2015 |
| WO | WO 2015/073342 | | 5/2015 |
| WO | WO 2015/076800 | | 5/2015 |
| WO | WO 2015/078802 | | 6/2015 |
| WO | WO 2015/078949 | | 6/2015 |
| WO | WO 2015/084692 | | 6/2015 |
| WO | WO 2015/088868 | | 6/2015 |
| WO | WO 2015/089809 | | 6/2015 |
| WO | WO 2015/097713 | | 7/2015 |
| WO | WO 2015/105779 | | 7/2015 |
| WO | WO 2015/105786 | | 7/2015 |
| WO | WO 2018/121560 | | 7/2015 |
| WO | WO-2015100217 | A1 | 7/2015 |
| WO | WO-2015108861 | | 7/2015 |
| WO | WO 2015/119899 | | 8/2015 |
| WO | WO-2015118057 | A1 | 8/2015 |
| WO | WO 2015/140717 | | 9/2015 |
| WO | WO 2015/150097 | | 10/2015 |
| WO | WO 2015/160641 | | 10/2015 |
| WO | WO-2015157386 | A1 | 10/2015 |
| WO | WO 2015/171722 | | 11/2015 |
| WO | WO 2015/171733 | | 11/2015 |

(56) References Cited

FOREIGN PATENT DOCUMENTS

| | | | |
|---|---|---|---|
| WO | WO 2015/171757 | | 11/2015 |
| WO | WO 2015/176267 | | 11/2015 |
| WO | WO-2015173164 | A1 | 11/2015 |
| WO | WO 2015/198045 | | 12/2015 |
| WO | WO 2015/198046 | | 12/2015 |
| WO | WO-201588085 | A1 | 12/2015 |
| WO | WO-2015191745 | | 12/2015 |
| WO | WO 2016/007714 | | 1/2016 |
| WO | WO-2016012470 | A1 | 1/2016 |
| WO | WO 2016/019587 | | 2/2016 |
| WO | WO 2016/022446 | | 2/2016 |
| WO | WO 2016/022448 | | 2/2016 |
| WO | WO 2016/022742 | | 2/2016 |
| WO | WO 2016/026772 | | 2/2016 |
| WO | WO-2016023877 | A1 | 2/2016 |
| WO | WO 2016/032120 | | 3/2016 |
| WO | WO 2016/039749 | | 3/2016 |
| WO | WO 2016/041511 | | 3/2016 |
| WO | WO-2016033570 | A1 | 3/2016 |
| WO | WO-2016049211 | A1 | 3/2016 |
| WO | WO 2016/060517 | | 4/2016 |
| WO | WO 2016/060963 | | 4/2016 |
| WO | WO-2016057924 | A1 | 4/2016 |
| WO | WO-2016065226 | | 4/2016 |
| WO | WO 2016/071283 | | 5/2016 |
| WO | WO 2016/071293 | | 5/2016 |
| WO | WO 2016/073774 | | 5/2016 |
| WO | WO-2016068451 | | 5/2016 |
| WO | WO-2016090190 | A1 | 6/2016 |
| WO | WO-2016100236 | A2 | 6/2016 |
| WO | WO-2016102438 | A1 | 6/2016 |
| WO | WO 2016/110821 | | 7/2016 |
| WO | WO-2016107832 | A1 | 7/2016 |
| WO | WO-2016107833 | A1 | 7/2016 |
| WO | WO 2016/128908 | | 8/2016 |
| WO | WO-2016120186 | A1 | 8/2016 |
| WO | WO-2016128335 | A1 | 8/2016 |
| WO | WO 2016/142833 | | 9/2016 |
| WO | WO 2016/142835 | | 9/2016 |
| WO | WO 2016/142852 | | 9/2016 |
| WO | WO 2016/142886 | | 9/2016 |
| WO | WO 2016/142894 | | 9/2016 |
| WO | WO-2016141092 | | 9/2016 |
| WO | WO-2016165613 | | 10/2016 |
| WO | WO-2016186967 | A1 | 11/2016 |
| WO | WO 2016/195776 | | 12/2016 |
| WO | WO 2016/197987 | | 12/2016 |
| WO | WO-2016196381 | | 12/2016 |
| WO | WO-2016196388 | A1 | 12/2016 |
| WO | WO 2017/011279 | | 1/2017 |
| WO | WO 2017/025368 | | 2/2017 |
| WO | WO 2017/027309 | | 2/2017 |
| WO | WO 2017/027310 | | 2/2017 |
| WO | WO 2017/027312 | | 2/2017 |
| WO | WO 2017/031392 | | 2/2017 |
| WO | WO-2017031392 | A1 | 2/2017 |
| WO | WO 2017/042121 | | 3/2017 |
| WO | WO-2017049166 | A1 | 3/2017 |
| WO | WO 2017/066227 | | 4/2017 |
| WO | WO 2017/070089 | | 4/2017 |
| WO | WO 2017/079669 | | 5/2017 |
| WO | WO 2017/087777 | | 5/2017 |
| WO | WO 2017/099034 | | 6/2017 |
| WO | WO 2017/106634 | | 6/2017 |
| WO | WO 2017/107979 | | 6/2017 |
| WO | WO 2017/112730 | | 6/2017 |
| WO | WO 2017/118762 | | 7/2017 |
| WO | WO 2017/143220 | | 8/2017 |
| WO | WO 2017/151830 | | 9/2017 |
| WO | WO 2017/162284 | | 9/2017 |
| WO | WO 2017/172505 | | 10/2017 |
| WO | WO 2017/176608 | | 10/2017 |
| WO | WO 2017/180457 | | 10/2017 |
| WO | WO 2017/180571 | | 10/2017 |
| WO | WO 2017/180769 | | 10/2017 |
| WO | WO 2017/192961 | | 11/2017 |
| WO | WO 2017/201683 | | 11/2017 |
| WO | WO 2017/202273 | | 11/2017 |
| WO | WO 2017/202274 | | 11/2017 |
| WO | WO 2017/202275 | | 11/2017 |
| WO | WO 2017/202276 | | 11/2017 |
| WO | WO 2017/202744 | | 11/2017 |
| WO | WO 2017/205464 | | 11/2017 |
| WO | WO 2017/222976 | | 12/2017 |
| WO | WO 2018/005374 | | 1/2018 |
| WO | WO 2018/009505 | | 1/2018 |
| WO | WO-2018013597 | | 1/2018 |
| WO | WO 2018/026971 | | 2/2018 |
| WO | WO 2018/029150 | | 2/2018 |
| WO | WO-2018026871 | | 2/2018 |
| WO | WO 2018/044783 | | 3/2018 |
| WO | WO 2018/044963 | | 3/2018 |
| WO | WO 2018/045142 | | 3/2018 |
| WO | WO 2018/051254 | | 3/2018 |
| WO | WO 2018/051255 | | 3/2018 |
| WO | WO 2018/053302 | | 3/2018 |
| WO | WO-2018044329 | A1 | 3/2018 |
| WO | WO 2018/077699 | | 5/2018 |
| WO | WO 2018/081047 | | 5/2018 |
| WO | WO 2018/095877 | | 5/2018 |
| WO | WO 2018/106518 | | 6/2018 |
| WO | WO 2018/111012 | | 6/2018 |
| WO | WO 2018/118664 | | 6/2018 |
| WO | WO 2018/118670 | | 6/2018 |
| WO | WO 2018/118848 | | 6/2018 |
| WO | WO 2018/119221 | | 6/2018 |
| WO | WO 2018/119224 | | 6/2018 |
| WO | WO 2018/119236 | | 6/2018 |
| WO | WO 2018/119263 | | 6/2018 |
| WO | WO 2018/119266 | | 6/2018 |
| WO | WO 2018/119286 | | 6/2018 |
| WO | WO 2018/138026 | | 8/2018 |
| WO | WO 2018/138027 | | 8/2018 |
| WO | WO 2018/138028 | | 8/2018 |
| WO | WO 2018/138029 | | 8/2018 |
| WO | WO 2018/138030 | | 8/2018 |
| WO | WO 2018/146008 | | 8/2018 |
| WO | WO 2018/172727 | | 9/2018 |
| WO | WO 2018/181847 | | 10/2018 |
| WO | WO 2018/182050 | | 10/2018 |
| WO | WO 2018/183171 | | 10/2018 |
| WO | WO 2018/195321 | | 10/2018 |
| WO | WO 2018/196768 | | 11/2018 |
| WO | WO 2019/008156 | | 1/2019 |
| WO | WO 2019/023575 | | 1/2019 |
| WO | WO 2019/032547 | | 2/2019 |
| WO | WO 2019/034172 | | 2/2019 |
| WO | WO 2019/059411 | | 3/2019 |
| WO | WO 2019/070643 | | 4/2019 |
| WO | WO 2019/074241 | | 4/2019 |
| WO | WO 2019/076343 | | 4/2019 |
| WO | WO 2019/128918 | | 7/2019 |
| WO | WO 2019/160882 | | 8/2019 |
| WO | WO 2019/165043 | | 8/2019 |
| WO | WO 2019/174533 | | 9/2019 |
| WO | WO 2019/175897 | | 9/2019 |
| WO | WO-2019170745 | | 9/2019 |
| WO | WO-2019173665 | | 9/2019 |
| WO | WO 2019/191624 | | 10/2019 |
| WO | WO 2019/191707 | | 10/2019 |
| WO | WO 2019/192506 | | 10/2019 |
| WO | WO 2019/204609 | | 10/2019 |
| WO | WO 2019/217821 | | 11/2019 |
| WO | WO-2019226213 | | 11/2019 |
| WO | WO 2020/011246 | | 1/2020 |
| WO | WO 2020/014643 | | 1/2020 |
| WO | WO-2020086556 | | 4/2020 |

OTHER PUBLICATIONS

International Search Report and Written Opinion for International Application No. PCT/US2018/028388 dated Jun. 28, 2018. (14 pages).

(56) References Cited

OTHER PUBLICATIONS

International Search Report and Written Opinion for International Application No. PCT/US2019/017721 dated Apr. 8, 2019. (15 pages).
International Search Report and Written Opinion for International Application No. PCT/US2019/028129 dated Jul. 22, 2019. (14 pages).
Cancer Progression 2017, Current status of clinical study on treatment of non-small cell lung cancer with PD-1 and PD-L1 such as Shilixia. 3 pages.
Examination Report for Australian Application No. 2021200639 dated Nov. 24, 2021. 3 pages.
Examination Report for Australian Application No. 2022279537 dated Sep. 14, 2023. 5 pages.
Examination Report for Canada Application No. 3,057,864 dated Dec. 10, 2021. 4 pages.
Examination Report for Canada Application No. 3,057,864 dated Feb. 16, 2023. 4 pages.
Examination Report for Canada Application No. 3,057,864 dated May 28, 2021. 5 pages.
Extended European Search Report for European Application No. 21204444.0 dated Aug. 24, 2022. 10 pages.
Garcia et al. (2016). Allosteric Inhibition of SHP2: Identification of a Potent, Selective, and Orally Efficacious Phosphatase Inhibitor. Journal of Medicinal Chemistry, 59(17), pp. 7773-7782. Recovering in: osti.gov/pages/servlets/purl/1404987.
J. G. Cannon, Chapter Nineteen in Burger's Medicinal Chemistry and Drug Discovery, Fifth Edition, vol. I: Principles and Practice, Wiley-Interscience 1995, pp. 783-802. (Year: 1995).
Jiani, etc. Research progress of PD-1/PD-L1 inhibitors in tumor therapy, Chin J of Clinical Rational Drug Use, Feb. 2017, vol. 10, No. 2A.
Notice of Final Rejection for Korean Application No. 10-2022-7006264 dated Oct. 18, 2022. 7 pages.
Notice of Preliminary Rejection for Korean Application No. 10-2019-7033795 dated May 30, 2021. 11 pages.
Notice of Preliminary Rejection for Korean Application No. 10-2022-7006264 dated May 18, 2022. 11 pages.
Office Action and Search Report for Chinese Application No. 201880040834.1 dated Sep. 1, 2022. 21 pages.
Office Action and Search Report for Taiwan Application No. 107113386 dated Mar. 10, 2022. 7 pages.
Office Action for Chinese Application No. 201880040834.1 dated May 19, 2023. 12 pages.
Office Action for Chinese Application No. 201880040834.1 dated Nov. 14, 2023. 12 pages.
Office Action for Taiwan Application No. 111141601 dated May 17, 2023. 7 pages.
Official Action for Japanese Application No. 2022-088597 dated Jun. 30, 2023. 3 pages.
Partial European Search Report for European Application No. 21204444.0 dated May 24, 2022. 13 pages.
Penultimate Official Action for Japanese Application No. 2019-556921 dated Dec. 1, 2021. 5 pages.
Penultimate Official Action for Japanese Application No. 2022-088597 dated Jan. 4, 2024. 6 pages.
Skalniak et al. (2017). Small-molecule inhibitors of PD-1/PD-L1 immune checkpoint alleviate the PD-L1-induced exhaustion of T-cells. Oncotarget, 8(42), p. 72167-72181, pubmed.ncbi.nlm.nih.gov/29069777/.
Sunshine et al., PD-1/PD-L1 inhibitors, Current Opinion in Pharmacology 2015, 23:32-38.
Zak et al. (2017). Structural basis for small molecule targeting of the programmed death ligand 1 (PD-L1). Oncotarget, 7(21), p. 30323-30335, pubmed.ncbi.nlm.nih.gov/27083005/.
U.S. Appl. No. 16/551,550, filed Aug. 26, 2019, Aktoudianakis et al.
U.S. Appl. No. 16/840,217, filed Apr. 3, 2020, Aktoudianakis et al.
Examination Report dated Feb. 10, 2021 for Australia Application No. 2018256423. 3 pages.
Examination Report dated Jun. 29, 2020 for India Application No. 201917044547. 6 pages.
Gura, et al. Systems for Identifying New Drugs Are Often Faulty. Science. 1997; 278:1041-1042.
International Search Report and Written Opinion for International Application No. PCT/US2018/028382 dated Sep. 11, 2018. (17 pages).
International Search Report and Written Opinion for International Application No. PCT/US2019/041657 dated Sep. 12, 2019. (12 pages).
International Search Report and Written Opinion for International Application No. PCT/US2019/057407 dated Feb. 18, 2020. (11 pages).
Johnson, et al. Relationships between drug activity in NCI preclinical in vitro and in vivo models and early clinical trials. British Journal of Cancer. 2001; 84:1424-1431.
Office Action dated Mar. 15, 2021 for Chile Application No. 201902895. 10 pages. (in Spanish).
Office Action dated Aug. 17, 2020 for Eurasian Application No. 18723183.2. 5 pages.
Office Action dated Sep. 15, 2020 for Chile Application No. 201902895. 13 pages.
Office Action dated Nov. 6, 2020 for Eurasian Application No. 201992045. 2 pages.
Office Action dated Dec. 7, 2020 for JP Application No. 2019-556921. 5 pages.
Office Action dated Dec. 14, 2020 for CA Application No. 3057864. 3 pages.
Sham, K-C. et al.: Acid-induced formation of hydrogen-bonded double helix based on chiral polyphenyl-bridged bis(2,2'-bipyridine) ligands. RSC Advances, vol. 4, pp. 14513-14526, 2014.
Written Opinion and Search Report dated Jan. 4, 2021 for Singapore Application No. 11201908619T. 9 pages.
Zarganes-Tzitzikes et al., "Inhibitors of programmed cell death 1 (PD-1): a patent review (2010-2015)", Expert Opinion on Therapeutic Patents, 2016, vol. 26, No. 9, pp. 973-977.
Examination Report for Canada Patent Application No. 3,175,847 dated Mar. 8, 2024. 7 pages.
"U.S. Appl. No. 15/957,739, Non Final Office Action mailed Feb. 26, 2019", 5 pgs.
"U.S. Appl. No. 15/957,739, Preliminary Amendment filed Sep. 17, 2018", 16 pgs.
"U.S. Appl. No. 15/957,739, Response filed Jan. 8, 2019 to Restriction Requirement mailed Oct. 9, 2018", 17 pgs.
"U.S. Appl. No. 15/957,739, Restriction Requirement mailed Oct. 9, 2018", 9 pgs.
"Australian Application Serial No. 2018256423, Response filed Feb. 1, 2021 to First Examination Report mailed Feb. 10, 2020", 50 pgs.
"Australian Application Serial No. 2021200639, Response filed Nov. 7, 2022 to First Examination Report mailed Nov. 2024, 21", 61 pgs.
"Canadian Application Serial No. 3,175,847, Examiners Rule 86(2) Requisition mailed Mar. 8, 2024", 7 pgs.
"European Application Serial No. 18723183.2, Communication Pursuant to Article 94(3) EPC mailed Aug. 17, 2020", 5 pgs.
"European Application Serial No. 18723183.2, Response filed Dec. 18, 2020 to Communication Pursuant to Article 94(3) EPC mailed Aug. 17, 2020", 242 pgs.
"European Application Serial No. 18723183.2, Response to Communication pursuant to Rules 161(1) and 162 EPC filed Jun. 16, 2020", 48 pgs.
"European Application Serial No. 21204444.0, Partial European search report mailed May 24, 2022", 10 pgs.
"European Application Serial No. 21204444.0, Response filed Mar. 14, 2023 to Extended European Search Report mailed Aug. 24, 2022", 51 pgs.
"International Application Serial No. PCT/US2018/028382, International Preliminary Report on Patentability mailed Oct. 31, 2019", 12 pgs.

(56) References Cited

OTHER PUBLICATIONS

"International Application Serial No. PCT/US2018/028382, Invitation to Pay Additional Fees mailed Jul. 18, 2018", 8 pgs.
"International Application Serial No. PCT/US2019/028129, International Search Report mailed Jul. 22, 2019", 4 pgs.
"International Application Serial No. PCT/US2019/028129, Written Opinion mailed Jul. 22, 2019", 5 pgs.
"Japanese Application Serial No. 2019-556921, Response filed May 31, 2022 to Notification of Reasons for Refusal mailed Dec. 1, 2021", w/ English Translation, 203 pgs.
"Japanese Application Serial No. 2019-556921, Response filed Jun. 7, 2021 to Notification of Reasons for Refusal mailed Dec. 7, 2020", w/ English Translation, 112 pgs.
"Japanese Application Serial No. 2022-088597, Response filed Apr. 3, 2024 to Notification of Reasons for Refusal mailed Jan. 3, 2024", With English Machine Translation, 156 pgs.
"Japanese Application Serial No. 2022-088597, Response filed Oct. 2, 2023 to Notification of Reasons for Refusal mailed Jun. 30, 2023", With English Machine Translation, 155 pgs.
"Japanese Application Serial No. 2023-171563, Notification of Reasons for Refusal mailed Aug. 30, 2024", w/ English translation, 3 pgs.
Greene, Theodora W, et al., "Protecting Groups in Organic Synthesis", John Wiley & Sons Inc, (1999), 52 pgs.
Morton, Lindsay M., et al., "Lymphoma Incidence Patterns by WHO Subtype in the United States 1992 2001", Blood vol. 107 1, (Jan. 2006), 12 pgs.
Wierda, W. G, "Current and Investigational Therapies for Patients with CLL", Hematology, (2006), 10 pgs.
U.S. Appl. No. 15/957,739, filed Apr. 19, 2018.
U.S. Appl. No. 16/551,550, filed Aug. 26, 2019.
U.S. Appl. No. 16/840,217, filed Apr. 3, 2020.
Canadian Application Serial No. 3175847, Response filed Jul. 8, 2024 to Examiners Rule 86(2) Report mailed Mar. 8, 2024, 519 pgs.
Korean Application Serial No. 10-2024-7019039, Notice of Preliminary Rejection mailed Nov. 25, 2024, W/English Translation, 8 pgs.
Taiwanese Application Serial No. 112144378, First Examination Report mailed Oct. 4, 2024, With English Machine Translation, 11 pgs.
Canadian Application Serial No. 3175847, Voluntary Amendment Filed Jun. 17, 2025, 363 pgs.

PD-1/PD-L1 INHIBITORS

CROSS-REFERENCE TO RELATED APPLICATIONS

This application is a continuation of U.S. application Ser. No. 16/840,217, filed Apr. 3, 2020, now abandoned, which is a continuation of U.S. application Ser. No. 16/551,550, filed Aug. 26, 2019, now abandoned, which is a continuation of U.S. application Ser. No. 15/957,739, filed Apr. 19, 2018, now abandoned, which claims the benefit under 35 U.S.C. § 119 (e) of U.S. Provisional Application No. 62/488,017, filed Apr. 20, 2017, and U.S. Provisional Application No. 62/507,678, filed May 17, 2017, each of which are hereby incorporated by reference in their entireties.

FIELD

The present disclosure generally relates to compounds useful as inhibitors of PD-1, PD-L1 or the PD-1/PD-L1 interaction. Provided herein are compounds, compositions comprising such compounds, and methods for their use.

BACKGROUND

Programmed death-1 (CD279) is a receptor on T cells that has been shown to suppress activating signals from the T cell receptor when bound by either of its ligands, Programmed death-ligand 1 (PD-L1, CD274, B7-H1) or PD-L2 (CD273, B7-DC). When PD-1 expressing T cells contact cells expressing its ligands, functional activities in response to antigenic stimuli, including proliferation, cytokine secretion, and cytotoxicity are reduced. PD-1/PD-Ligand interactions down regulate immune responses during resolution of an infection or tumor, or during the development of self-tolerance. Chronic antigen stimulation, such as that which occurs during tumor disease or chronic infections, results in T cells that express elevated levels of PD-1 and are dysfunctional with respect to activity towards the chronic antigen. This is termed "T cell exhaustion." B cells also display PD-1/PD-ligand suppression and "exhaustion."

Blockade of the PD-1/PD-L1 ligation using antibodies to PD-L1 has been shown to restore and augment T cell activation in many systems. Patients with advanced cancer benefit from therapy with a monoclonal antibody to PD-L1. Preclinical animal models of tumors and chronic infections have shown that blockade of the PD-1/PD-L1 pathway by monoclonal antibodies can enhance the immune response and result in tumor rejection or control of infection. Antitumor immunotherapy via PD-1/PD-L1 blockade may augment therapeutic immune response to a number of histologically distinct tumors.

Interference with the PD-1/PD-L1 interaction has also shown enhanced T cell activity in chronic infection systems. Chronic lymphocytic chorio meningitis virus infection of mice also exhibits improved virus clearance and restored immunity with blockade of PD-L1. Humanized mice infected with HIV-1 show enhanced protection against viremia and viral depletion of CD4+ T cells. Blockade of PD-1/PD-L1 through monoclonal antibodies to PD-L1 can restore in vitro antigen-specific functionality to T cells from HIV patients, HCV patients or HBV.

Accordingly, agents that block PD-1, PD-L1 and/or the PD-1/PD-L1 interaction are desired. Small molecule agents that block or inhibit PD-1, PD-L1 and/or the PD-1/PD-L1 interaction are particularly desired. Applicants have discovered small molecule compounds that have activity as inhibitors of PD-1, PD-L1 or inhibitors of the interaction of PD-1 with PD-L1, and thus may be useful for treating patients having cancer.

SUMMARY

The present disclosure provides a compound of formula (I):

$$R^W\text{-}Q^W\text{-}L^W\text{-}Ar^W\text{—}Ar^E\text{-}L^E\text{-}Q^E\text{-}R^E \qquad (I)$$

wherein:

$Ar^E$ and $Ar^W$ are each independently cycloalkyl, aryl, heteroaryl, or heterocyclyl;

wherein each cycloalkyl, aryl, heteroaryl, or heterocyclyl is optionally substituted with 1 to 4 groups independently selected from halo, —$OR^a$, —$NO_2$, —CN, —$NR^aR^b$, —$N_3$, —$SO_2R^a$, —$C_{1-6}$ alkyl, —$C_{1-6}$ haloalkyl, —$C_{2-6}$alkenyl, —$C_{2-6}$ alkynyl, —$OC_{1-6}$ alkyl, —$OC_{1-6}$ haloalkyl, —$C_{3-8}$ cycloalkyl, and —$C_{1-6}$ alkyl$C_{3-8}$cycloalkyl;

wherein each alkyl, alkenyl, alkynyl, and cycloalkyl group is optionally substituted with 1 to 4 groups independently selected from oxo, —$NO_2$, —$N_3$, —$OR^a$, halo, and cyano;

$L^E$ and $L^W$ are each independently a bond, —O—, —S—, —SO—, —$SO_2$, —$(CR^3R^4)_m$—, —$(CR^3R^4)_m O(CR^3R^4)_m$—, —$(CR^3R^4)_m S(CR^3R^4)_m$—, —$(CR^3R^4)_m NR^3 (CR^3R^4)_m$—, —C(O)—, —$(CR^3R^4)_m C(O)(CR^3R^4)_m$—, —$(CR^3R^4)_m C(O)NR^3(CR^3R^4)_m$—, —$(CR^3R^4)_m NR^3C(O) (CR^3R^4)_m$—, $C_{2-6}$ alkenylene, $C_{2-6}$ alkynylene,

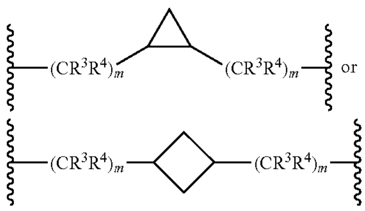
or ;

wherein each m is independently 0, 1, 2, 3 or 4;

$Q^E$ and $Q^W$ are each independently aryl, heteroaryl, or heterocyclyl, wherein each aryl, heteroaryl, or heterocyclyl is optionally substituted with 1 to 4 groups independently selected from halo, oxo, —$OR^a$, —$N_3$, —$NO_2$, —CN, —$NR^1R^2$, —$SO_2R^a$, —$SO_2NR^aR^b$, —$NR^aSO_2R^a$, —$NR^aC(O)R^a$, —$C(O)R^a$, —$C(O)OR^a$, —C(O) $NR^aR^b$, —$NR^aC(O)OR^a$, —$NR^aC(O)NR^1R^2$, —OC (O)$NR^aR^b$, —$NR^aSO_2NR^aR^b$, —$C(O)NR^aSO_2NR^aR^b$, —$C_{1-6}$ alkyl, —$C_{2-6}$ alkenyl, —$C_{2-6}$ alkynyl, —$OC_{1-6}$ alkyl, —$C_{3-8}$cycloalkyl, —$C_{1-6}$ alkyl$C_{3-8}$cycloalkyl, aryl, heteroaryl, heterocyclyl, and $R^N$;

wherein each alkyl, alkenyl, alkynyl, $C_{3-8}$ cycloalkyl, aryl, heteroaryl, or heterocyclyl is optionally substituted with 1 to 4 groups independently selected from oxo, —$NO_2$, —$N_3$, —$OR^a$, halo, cyano, —$NR^aR^b$, —$C(O)R^a$, —$C(O)OR^a$, —$OC_{1-6}$ alkyCN, —C(O) $NR^aR^b$, $NR^aC(O)R^a$, —$NR^aC(O)OR^a$, —$SO_2R^a$, —$NR^aSO_2R^b$, —$SO_2NR^aR^b$, —$NR^aSO_2NR^aR^b$, —$C(O)NR^aSO_2NR^aR^b$ and —$C_{3-8}$ cycloalkyl; and wherein the heteroaryl or heterocyclic group may be oxidized on a nitrogen atom to form an N-oxide or oxidized on a sulfur atom to form a sulfoxide or sulfone;

wherein $R^N$ is independently $—C_{1-6}$ $alkyNR^1R^2$, $—OC_{1-6}$ $alkyNR^1R^2$, $—C_{1-6}$ $alkylOC_{1-6}$ $alkylNR^1R^2$, $—NR^aC_{1-6}$ $alkylNR^1R^2$, $—C_{1-6}$ $alkylC(O)NR^1R^2$, $—OC_{1-6}$ $alkylC(O)NR^1R^2$, $—OC_{1-6}$ $alkylC(O)OR^1$, $—SC_{1-6}$ $alkylNR^1R^2$, $—C_{1-6}$ $alkylOR^a$, or

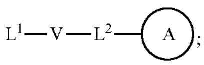;

wherein $L^1$ is independently a bond, O, $NR^a$, S, SO, or $SO_2$;

V is independently selected from a bond, $C_{1-6}alkyl$, $C_{2-6}alkenyl$, and $C_{2-6}alkynyl$;

wherein each alkyl, alkenyl, or alkynyl is optionally independently substituted with $OR^a$, halo, cyano, $—NR^aR^b$ or $—C_{3-8}$ cycloalkyl;

$L^2$ is independently a bond, O, $NR^a$, S, SO, or $SO_2$;

ring A is independently cycloalkyl, aryl, heteroaryl, or heterocyclyl;

wherein each cycloalkyl, aryl, heteroaryl, or heterocyclyl is optionally substituted with 1 to 4 groups independently selected from oxo, $—NO_2$, $—N_3$, $—OR^a$, halo, cyano, $—C_{1-6}$ alkyl, $—C_{1-6}$ haloalkyl, $—C_{2-6}alkenyl$, $—C_{2-6}$ alkynyl, $—OC_{1-6}$ haloalkyl, $NR^aR^b$, $—C(O)R^a$, $—C(O)OR^a$, $—OC_{1-6}$ alkylCN, $—C(O)NR^aR^b$, $—NR^aC(O)R^a$, $—NR^aC(O)OR^a$, $—NR^aC(O)OR^a$, $—C(O)N(R^a)OR^b$, $—SO_2R^a$, $—SO_2NR^aR^b$, $—NR^aSO_2R$, $—NR^aSO_2NR^aR^b$, $—C(O)NR^aSO_2NR^aR^b$, $C_{3-8}cycloalkyl$, and $C_{1-6}alkylC_{3-8}$ cycloalkyl;

wherein each alkyl, alkenyl, or alkynyl is optionally independently substituted with $OR^a$, halo, cyano, $—NR^aR^b$ and $—C_{3-8}$ cycloalkyl;

$R^E$ and $R^W$ are each independently $—NR^1R^2$, $—C_{1-6}$ $alkyNR^1R^2$, $—OC_{1-6}$ $alkylNR^1R^2$, $—C_{1-6}$ $alkylOC_{1-6}alkyNR^1R^2$, $—NR^aC_{1-6}$ $alkylNR^1R^2$, $—C_{1-6}$ $alkylN^+R^1R^2R^3$, $—SC_{1-6}$ $alkylNR^1R^2$, $—C(O)NR^1R^2$, $—SO_2R^a$, $—(CH_2)_uSO_2NR^1R^2$, $—(CH_2)_uNR^aSO_2NR^aR^b$, $—SO_2NR^aC_{1-6}alkyNR^1R^2$, $—NR^aSO_2C_{1-6}$ $alkylNR^1R^2$, $—(CH_2)_uC(O)NR^aSO_2NR^aR^b$, $—(CH_2)_uN^+R^1R^2O^-$, $—(CH_2)_uP^+R^bR^cR^d$, $—(CH_2)_uP^+R^cR^dO^-$, $—(CH_2)_uP^+O[NR^aR^b][NR^cR^d]$, $—(CH_2)_uNR^cP(O)(OR^c)_2$, $—(CH_2)_uNR^c(CH_2)_uP(O)(OR^c)_2$, $—(CH_2)_uCH_2OP(O)(OR^c)(OR^d)$; $—(CH_2)_uOP(O)(OR^c)(OR^d)$, $—(CH_2)_uOP(O)NR^aR^b)(OR^a)$, or

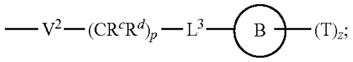;

wherein:

$V^2$ is independently a bond, O, $NR^a$, S, SO, $SO_2$, $C(O)NR^a$, $NR^aC(O)$, $SO_2NR^1R^2$, or $NR^aSO_2$;

$L^3$ is independently a bond, O, $NR^a$, S, SO, $SO_2$, $C(O)NR^a$, $NR^aC(O)$, $SO_2NR^1R^2$, or $NR^aSO_2$;

ring B is independently cycloalkyl, aryl, heteroaryl, or heterocyclyl;

T is independently H, $OR^a$, $(CH_2)NR^1R^2$, $(CH_2)_qNR^aC(O)R^e$, $(CH_2)OR^a$, or $(CH_2)_qC(O)R^e$;

p is independently 0, 1, 2, 3, 4, or 5;

q is independently 0, 1, 2, 3, 4, or 5;

u is 0, 1, 2, 3, or 4; and z is 0, 1, 2, or 3;

wherein each cycloalkyl, aryl, heteroaryl, or heterocyclyl of $R^E$ or $R^W$ is optionally substituted with 1 to 3 substituents independently selected from $NR^aR^b$, halo, cyano, oxo, $OR^a$, $—C_{1-6}alkyl$, $—C_{1-6}haloalkyl$, $—C_{1-6}cyanoalkyl$, $—C_{1-6}alkylNR^aR^b$, $—C_{1-6}alkylOH$, $—C_{3-8}cycloalkyl$, and $—C_{1-3}$ $alkylC_{3-8}cycloalkyl$;

provided that at least one of $V^2$, $L^3$, ring B and T contains a nitrogen atom;

$R^1$ is independently selected from H, $—C_{1-8}$ alkyl, $—C_{2-6}$ alkenyl, $—C_{2-6}$ alkynyl, $—C_{3-6}$ cycloalkyl, aryl, heteroaryl, heterocyclyl, $—C_{1-6}alkylaryl$, $—C_{1-6}alkylheteroaryl$, $—C_{1-6}alkylheterocyclyl$, $—C_{1-6}$ $alkylC(O)OR^a$, $—C_{2-6}$ $alkenylC(O)OR^a$, $—SO_2R^a$, $—SO_2NR^aR^b$, $—C(O)NR^aSO_2R^a$, and $C_{1-6}$ $alkylC_{3-8}cycloalkyl$;

wherein each alkyl, alkenyl, cycloalkyl, aryl, heteroaryl, or heterocyclyl is optionally substituted with 1 to 4 groups independently selected from $—OR^a$, —CN, halo, $C_{1-6}alkyl$, $—C_{1-6}alkylOR^a$, $—C_{1-6}$ cyanoalkyl, $—C_{1-6}haloalkyl$, $C_{3-8}$ cycloalkyl, $—C_{1-3}$ $alkylC_{3-8}cycloalkyl$, $—C(O)R^a$, $—C_{1-6}$ alkyl $C(O)R^a$, $—C(O)OR^a$, $—C_{1-6}alkylC(O)OR^a$, $—NR^aR^b$, $—OC(O)NR^aR^b$, $NR^aC(O)OR^b$, $—C_{1-6}$ $alkylNR^aR^b$, $—C(O)NR^aR^b$, $—C_{1-6}alkylC(O)NR^aR^b$, $—SO_2R^a$, $—C_{1-6}alkylSO_2R^a$, $—SO_2N^aR^b$, $—C_{1-6}$ $alkylSO_2NR^aR^b$, $—C(O)NR^aSO_2R^b$, $—C_{1-6}$ $alkylC(O)NR^aSO_2R^b$, $—NR^aC(O)R^b$, and $—C_{1-6}alkylNR^aC(O)R^b$;

$R^2$ is independently selected from H, $—C_{1-6}alkyl$, $—C_{2-6}$ alkenyl, $—C_{2-6}$ alkynyl, $—C_{3-6}$ cycloalkyl, aryl, heteroaryl, heterocyclyl, $—C_{1-6}alkylaryl$, $—C_{1-6}alkylheteroaryl$, $—C_{1-6}$ alkylheterocyclyl, $—C_{2-6}alkyl-OR^a$, $—C_{1-6}$ $alkylC(O)OR^a$, and $—C_{2-6}$ $alkenylC(O)OR^a$;

wherein each alkyl, alkenyl, alkynyl, cycloalkyl, aryl, heteroaryl, or heterocyclyl is optionally substituted with 1 to 4 groups independently selected from $—OR^a$, —CN, halo, $C_{1-6}alkyl$, $—C_{1-6}alkylOR^a$, $—C_{1-6}cyanoalkyl$, $—C_{1-6}haloalkyl$, $—C_{3-8}cycloalkyl$, $—C_{1-3}alkylC_{3-8}cycloalkyl$, $—C(O)R^a$, $—C_{1-6}$ $alkylC(O)R^a$, $—C(O)OR^a$, $—C_{1-6}$ $alkylC(O)OR^a$, $—NR^aR^b$, $—C_{1-6}$ $alkylNR^aR^b$, $—C(O)NR^aR^b$, $—C_{1-6}alkylC(O)NR^aR^b$, $—SO_2R^a$, $—C_{1-6}alkylSO_2R^a$, $—SO_2NR^aR^b$, $—C_{1-6}$ $alkylSO_2NR^aR^b$, $—C(O)NR^aSO_2R^b$ and $—NR^aC(O)R^b$;

or $R^1$ and $R^2$ combine to form a heterocyclyl group optionally containing 1, 2, or 3 additional heteroatoms independently selected from oxygen, sulfur and nitrogen, and optionally substituted with 1 to 3 groups independently selected from oxo, $—C_{1-6}alkyl$, $—C_{3-8}cycloalkyl$, $—C_{2-6}$ alkenyl, $—C_{2-6}$ alkynyl, $—OR^a$, $—C(O)OR^a$, $—C_{1-6}$ cyanoalkyl, $—C_{1-6}$ $alkylOR^a$, $—C_{1-6}haloalkyl$, $—C_{1-3}$ alkyl $C_{3-8}cycloalkyl$, $—C(O)R^a$, $C_{1-6}alkylC(O)R^a$, $—C_{1-6}alkylC(O)OR^a$, $—NR^aR^b$, $—C_{1-6}alkyNR^aR^b$, $—C(O)NR^aR^b$, $—C_{1-6}alkylC(O)NR^aR^b$, $—SO_2R^a$, $—C_{1-6}$ $alkylSO_2R^a$, $—SO_2NR^aR^b$, and $C_{1-6}$ $alkylSO_2NR^aR^b$;

$R^3$ is independently H, $—C_{1-6}alkyl$, $—C_{2-6}$ alkenyl, $—C_{3-6}$ cycloalkyl, aryl, heteroaryl, heterocyclyl, $—C_{1-6}alkylaryl$, $—C_{1-6}alkylheteroaryl$, $—C_{1-6}$ alkylheterocyclyl, $—C_{2-6}alkyl-OR^a$, $—C_{1-6}alkylC(O)OR^a$, or $—C_{2-6}$ $alkenylC(O)OR^a$;

$R^4$ is independently H, $—C_{1-6}alkyl$, $—C_{2-6}$ alkenyl, $—C_{3-6}$ cycloalkyl, aryl, heteroaryl, heterocyclyl, $—C_{1-6}alkylaryl$, $—C_{1-6}alkylheteroaryl$, $—C_{1-6}$ alkylheterocyclyl, $—C_{2-6}alkyl-OR^a$, $—C_{1-6}alkylC(O)OR^a$, or $—C_{2-6}$ $alkenylC(O)OR^a$;

$R^a$ is independently selected from H, $—C_{1-6}alkyl$, $—C_{3-8}$ cycloalkyl, aryl, heteroaryl, heterocyclyl, $—C_{1-3}$ alkyl $C_{3-8}cycloalkyl$, $—C_{1-6}$ alkylaryl, $—C_{1-6}$ alkylheteroaryl, and $—C_{1-6}alkylheterocyclyl$;

$R^b$ is independently selected from H, —$C_{1-6}$alkyl, —$C_{3-8}$ cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$ alkylheterocyclyl;

or $R^a$ and $R^b$ may combine together to form a ring consisting of 3-8 ring atoms that are C, N, O, or S; wherein the ring is optionally substituted with 1 to 4 groups independently selected from —$OR^f$, —CN, halo, —$C_{1-6}$ alkyl$OR^f$, —$C_{1-6}$ cyanoalkyl, —$C_{1-6}$haloalkyl, —$C_{3-8}$ cycloalkyl, —$C_{1-3}$ alkyl$C_{3-8}$cycloalkyl, —C(O)$R^f$, —$C_{1-6}$ alkylC(O)$R^f$, —C(O)$OR^f$, —$C_{1-6}$ alkylC(O)$OR^f$, —$NR^fR^g$, —$C_{1-6}$ alkyl$NR^fR^g$, —C(O)$NR^fR^g$, —$C_{1-6}$ alkylC(O)$NR^fR^g$, —$SO_2R^f$, —$C_{1-6}$ alkyl$SO_2R^f$, —$SO_2NR^fR^g$, —$C_{1-6}$ alkyl$SO_2NR^fR^g$, —C(O)$NR^fSO_2R^g$ and —$NR^f$C(O)$R^g$;

$R^c$ is independently selected from H, OH, —$C_{1-6}$alkyl, —$C_{3-8}$ cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl;

$R^d$ is independently selected from H, —$C_{1-6}$alkyl, —$C_3$-$C_8$cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl;

$R^e$ is independently selected from H, —$C_{1-6}$alkyl, —$OC_{1-6}$alkyl, —$C_{3-8}$ cycloalkyl, aryl, heteroaryl, heterocyclyl, —$OC_{3-8}$cycloalkyl, —Oaryl, —Oheteroaryl, —Oheterocyclyl, —$C_{1-3}$ alkyl$C_{3-8}$cycloalkyl, —$C_{1-6}$alkylaryl, —$C_{1-6}$alkylheteroaryl, —$NR^fR^g$, —$C_{1-6}$alkyl$NR^fR^g$, —C(O)$NR^fR^g$, —$C_{1-6}$alkylC(O)$NR^fR^g$, —$NHSO_2R^f$, —$C_{1-6}$alkyl$SO_2R^f$, and —$C_{1-6}$alkyl$SO_2NR^fR^g$;

$R^f$ is independently selected from H, —$C_{1-6}$alkyl, —$C_{3-8}$ cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl; and $R^g$ is independently selected from H, —$C_{1-6}$ alkyl, —$C_{3-8}$ cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl;

or a pharmaceutically acceptable salt, stereoisomer, mixture of stereoisomers, or tautomer thereof.

The present disclosure further provides a compound of formula (I):

$$R^W\text{-}Q^W\text{-}L^W\text{-}Ar^W\text{—}Ar^E\text{-}L^E\text{-}Q^E\text{-}R^E \quad \text{(I)}$$

wherein:

$Ar^E$ and $Ar^W$ are each independently cycloalkyl, aryl, heteroaryl, or heterocyclyl;

wherein each cycloalkyl, aryl, heteroaryl, or heterocyclyl is optionally substituted with 1 to 4 groups independently selected from halo, —$OR^a$, —$NO_2$, —CN, —$NR^aR^b$, —$N_3$, —$SO_2R^a$, —$C_{1-6}$ alkyl, —$C_{1-6}$ haloalkyl, —$C_{2-6}$alkenyl, —$C_{2-6}$ alkynyl, —$OC_{1-6}$ alkyl, —$OC_{1-6}$ haloalkyl, —$C_{3-8}$cycloalkyl, and —$C_{1-6}$ alkyl$C_{3-8}$ cycloalkyl;

wherein each alkyl, alkenyl, alkynyl, and cycloalkyl group is optionally substituted with 1 to 4 groups independently selected from oxo, —$NO_2$, —$N_3$, —$OR^a$, halo, and cyano;

$L^E$ and $L^W$ are each independently a bond, —O—, —S—, —SO—, —$SO_2$—, —$(CR^3R^4)_m$—, —$(CR^3R^4)_m$O$(CR^3R^4)_m$—, —$(CR^3R^4)_m$S$(CR^3R^4)_m$—, —$(CR^3R^4)_m$$NR^3$$(CR^3R^4)_m$—, —C(O)—, —$(CR^3R^4)_m$C(O)$(CR^3R^4)_m$—, —$(CR^3R^4)_m$C(O)$NR^3$$(CR^3R^4)_m$—, —$(CR^3R^4)_m$$NR^3$C(O)$(CR^3R^4)_m$—, $C_{2-6}$ alkenylene, $C_{2-6}$ alkynylene,

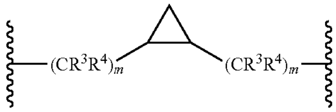 or

-continued

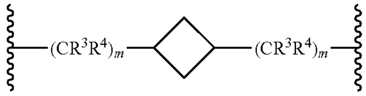 ;

wherein each m is independently 1, 2, 3 or 4;

provided that when one of $Ar^E$ and $Ar^W$ is optionally substituted phenyl and the other is optionally substituted phenyl or optionally substituted 2,3-dihydrobenzo[b][1,4]dioxine, and one of $L^E$ and $L^W$ is —$CH_2O$—, —$CH_2CH_2$—, —CHCH—, and —C(O)N—; then the other of $L^E$ and $L^W$ is a bond, —O— or —$CH_2O$— of the formula Ar—$CH_2$O-Q;

$Q^E$ and $Q^W$ are each independently aryl, heteroaryl, or heterocyclyl, wherein each aryl, heteroaryl, or heterocyclyl is optionally substituted with 1 to 4 groups independently selected from halo, oxo, —$OR^a$, —$N_3$, —$NO_2$, —CN, —$NR^1R^2$, —$SO_2R^a$, —$SO_2NR^aR^b$, —$NR^aSO_2R^a$, —$NR^a$C(O)$R^a$, —C(O)$R^a$, —C(O)$OR^a$, —C(O)$NR^aR^b$, —$NR^a$C(O)$OR^a$, —$NR^a$C(O)$NR^1R^2$, —OC(O)$NR^aR^b$, —$NR^aSO_2NR^aR^b$, —C(O)$NR^aSO_2NR^aR^b$, —$C_{1-6}$ alkyl, —$C_{2-6}$ alkenyl, —$C_{2-6}$ alkynyl, —$OC_{1-6}$ alkyl, —$C_{1-6}$ alkyl$C_{3-8}$ cycloalkyl, and $R^N$;

wherein each alkyl, alkenyl, alkynyl, is optionally substituted with 1 to 4 groups independently selected from oxo, —$NO_2$, —$N_3$, —$OR^a$, halo, cyano, —$NR^aR^b$, —C(O)$R^a$, —C(O)$OR^a$, —$OC_{1-6}$alkylCN, —C(O)$NR^aR^b$, $NR^a$C(O)$R^a$, —$NR^a$C(O)$OR^a$, —$SO_2R^a$, —$NR^aSO_2R^b$, —$SO_2NR^aR^b$, —$NR^aSO_2NR^aR^b$, —C(O)$NR^aSO_2NR^aR^b$ and —$C_{3-8}$ cycloalkyl;

wherein $R^N$ is independently —$C_{1-6}$ alkyl$NR^1R^2$, —$OC_{1-6}$ alky$NR^1R^2$, —$C_{1-6}$ alkyl$OC_{1-6}$ alkyl$NR^1R^2$, —$NR^aC_{1-6}$ alkyl$NR^1R^2$, —$C_{1-6}$ alkylC(O)$NR^1R^2$, —$OC_{1-6}$ alkylC(O)$NR^1R^2$, —$OC_{1-6}$ alkylC(O)$OR^1$, —$SC_{1-6}$ alkyl$NR^1R^2$, —$C_{1-6}$ alkyl$OR^a$, or

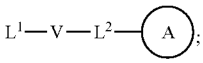 ;

wherein $L^1$ is independently a bond, O, $NR^a$, S, SO, or $SO_2$;

V is independently selected from a bond, $C_{1-6}$alkyl, $C_{2-6}$alkenyl, and $C_{2-6}$alkynyl;

wherein each alkyl, alkenyl, or alkynyl is optionally independently substituted with $OR^a$, halo, cyano, —$NR^aR^b$ or —$C_{3-8}$ cycloalkyl;

$L^2$ is independently a bond, O, $NR^a$, S, SO, or $SO_2$;

provided at least one of $L^1$, V an $L^2$ is other than a bond;

ring A is independently cycloalkyl, aryl, heteroaryl, or heterocyclyl;

wherein each cycloalkyl, aryl, heteroaryl, or heterocyclyl is optionally substituted with 1 to 4 groups independently selected from oxo, —$NO_2$, —$N_3$, —$OR^a$, halo, cyano, —$C_{1-6}$ alkyl, —$C_{1-6}$ haloalkyl, —$C_{2-6}$alkenyl, —$C_{2-6}$ alkynyl, —$OC_{1-6}$ haloalkyl, $NR^aR^b$, —C(O)$R^a$, —C(O)$OR^a$, —$OC_{1-6}$ alkylCN, —C(O)$NR^aR^b$, —$NR^a$C(O)$R^a$, —$NR^a$C(O)$OR^a$, —$NR^a$C(O)$OR^a$, —C(O)N($R^a$)$OR^b$, —$SO_2R^a$, —$SO_2NR^aR^b$, —$NR^aSO_2R^b$, —$NR^aSO_2NR^aR^b$, —$C(O)NR^aSO_2NR^aR^b$, $C_{3-8}$cycloalkyl, and $C_{1-6}$alkyl$C_{3-8}$ cycloalkyl;

wherein each alkyl, alkenyl, or alkynyl is optionally independently substituted with $OR^a$, halo, cyano, —$NR^aR^b$ and —$C_{3-8}$ cycloalkyl;

$R^E$ and $R^W$ are each independently —$NR^1R^2$, —$C_{1-6}$ alkyNR$^1$R$^2$, —$OC_{1-6}$ alkylNR$^1$R$^2$, —$C_{1-6}$ alkylOC$_{1-6}$alkylNR$^1$R$^2$, —$NR^aC_{1-6}$ alkylNR$^1$R$^2$, —$C_{1-6}$ alkylN$^+$R$^1$R$^2$R$^3$, —$SC_{1-6}$ alkylNR$^1$R$^2$, —C(O)NR$^1$R$^2$, —$SO_2R^a$, —$(CH_2)_uSO_2NR^1R^2$, —$(CH_2)_uNR^aSO_2NR^aR^b$, —$SO_2NR^aC_{1-6}$alkyNR$^1$R$^2$, —$NR^aSO_2C_{1-6}$alkylNR$^1$R$^2$, —$(CH_2)_uC(O)NR^aSO_2NR^aR^b$, —$(CH_2)_uN^+R^1R^2O^-$, —$(CH_2)_uP^+R^bR^cR^d$, —$(CH_2)_uP^+R^cR^dO^-$, —$(CH_2)_uP^+O[NR^aR^b][NR^cR^d]$, —$(CH_2)_uNR^cP(O)(OR^c)_2$, —$(CH_2)_uNR^c(CH_2)_uP(O)(OR^c)_2$, —$(CH_2)_uCH_2OP(O)(OR^c)(OR^d)$; —$(CH_2)_uOP(O)(OR^c)(OR^d)$, —$(CH_2)_uOP(O)NR^aR^b)(OR^a)$, or

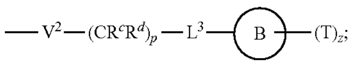

wherein:

$V^2$ is independently a bond, O, $NR^a$, S, SO, $SO_2$, C(O)NR$^a$, NR$^a$C(O), SO$_2$NR$^1$R$^2$, or NR$^a$SO$_2$;

$L^3$ is independently a bond, O, $NR^a$, S, SO, $SO_2$, C(O)NR$^a$, NR$^a$C(O), SO$_2$NR$^1$R$^2$, or NR$^a$SO$_2$;

ring B is independently cycloalkyl, aryl, heteroaryl, or heterocyclyl;

T is independently H, $OR^a$, $(CH_2)_qNR^1R^2$, $(CH_2)_qNR^aC(O)R^e$, $(CH_2)_qOR^a$, or $(CH_2)_qC(O)R^e$;

p is independently 0, 1, 2, 3, 4, or 5;

q is independently 0, 1, 2, 3, 4, or 5;

u is 0, 1, 2, 3, or 4; and z is 0, 1, 2, or 3;

wherein each cycloalkyl, aryl, heteroaryl, or heterocyclyl is optionally substituted with 1 to 3 substituents independently selected from $NR^aR^b$, halo, cyano, oxo, $OR^a$, —$C_{1-6}$alkyl, —$C_{1-6}$haloalkyl, —$C_{1-6}$cyanoalkyl, —$C_{1-6}$alkylNR$^a$R$^b$, —$C_{1-6}$alkylOH, —$C_{3-8}$cycloalkyl, and —$C_{1-3}$ alkyl$C_{3-8}$cycloalkyl;

provided that at least one of $V^2$, $L^3$, ring B and T contains a nitrogen atom, and when each of $V^2$ and $L^3$ is a bond and p is 0, then either (i) neither of $L^E$ or $L^W$ is a bond or (ii) ring B is not a 5,6-membered fused heteroaryl where the 5-membered ring of the fused heteroaryl is bound to the corresponding $Q^E$ or $Q^W$;

$R^1$ is independently selected from H, —$C_{1-8}$ alkyl, —$C_{2-6}$ alkenyl, —$C_{2-6}$ alkynyl, —$C_{3-6}$ cycloalkyl, aryl, heteroaryl, heterocyclyl, —$C_{1-6}$alkylaryl, —$C_{1-6}$alkylheteroaryl, —$C_{1-6}$alkylheterocyclyl, —$C_{1-6}$ alkylC(O)OR$^a$, —$C_{2-6}$ alkenylC(O)OR$^a$, —$SO_2R^a$, —$SO_2NR^aR^b$, —$C(O)NR^aSO_2R^a$, and $C_{1-6}$ alkyl$C_{3-8}$cycloalkyl;

wherein each alkyl, alkenyl, cycloalkyl, aryl, heteroaryl, or heterocyclyl is optionally substituted with 1 to 4 groups independently selected from —$OR^a$, —CN, halo, $C_{1-6}$alkyl, —$C_{1-6}$alkylOR$^a$, —$C_{1-6}$ cyanoalkyl, —$C_{1-6}$haloalkyl, $C_{3-8}$ cycloalkyl, —$C_{1-3}$ alkyl$C_{3-8}$cycloalkyl, —C(O)R$^a$, —$C_{1-6}$ alkyl C(O)R$^a$, —C(O)OR$^a$, —$C_{1-6}$alkylC(O)OR$^a$, —$NR^aR^b$, —OC(O)NR$^a$R$^b$, NR$^a$C(O)OR$^b$, —$C_{1-6}$ alkylNR$^a$R$^b$, —C(O)NR$^a$R$^b$, —$C_{1-6}$alkylC(O)NR$^a$R$^b$, —$SO_2R^a$, —$C_{1-6}$alkylSO$_2$R$^a$, —$SO_2NR^aR^b$, —$C_{1-6}$ alkylSO$_2$NR$^a$R$^b$, —C(O)NR$^a$SO$_2$R$^b$, —$C_{1-6}$ alkylC(O)NR$^a$SO$_2$R$^b$, —NR$^a$C(O)R$^b$, and —$C_{1-6}$alkylNR$^a$C(O)R$^b$;

$R^2$ is independently selected from H, —$C_{1-6}$alkyl, —$C_{2-6}$ alkenyl, —$C_{2-6}$ alkynyl, —$C_{3-6}$ cycloalkyl, aryl, heteroaryl, heterocyclyl, —$C_{1-6}$alkylaryl, —$C_{1-6}$alkylheteroaryl, —$C_{1-6}$ alkylheterocyclyl, —$C_{2-6}$alkyl-OR$^a$, —$C_{1-6}$ alkylC(O)OR$^a$, and —$C_{2-6}$ alkenylC(O)OR$^a$;

wherein each alkyl, alkenyl, alkynyl, cycloalkyl, aryl, heteroaryl, or heterocyclyl is optionally substituted with 1 to 4 groups independently selected from —$OR^a$, —CN, halo, $C_{1-6}$alkyl, —$C_{1-6}$alkylOR$^a$, —$C_{1-6}$cyanoalkyl, —$C_{1-6}$haloalkyl, —$C_{3-8}$cycloalkyl, —$C_{1-3}$alkyl$C_{3-8}$cycloalkyl, —C(O)R$^a$, —$C_{1-6}$ alkylC(O)R$^a$, —C(O)OR$^a$, —$C_{1-6}$ alkylC(O)OR$^a$, —$NR^aR^b$, —$C_{1-6}$ alkylNR$^a$R$^b$, —C(O)NR$^a$R$^b$, —$C_{1-6}$alkylC(O)NR$^a$R$^b$, —$SO_2R^a$, —$C_{1-6}$alkylSO$_2$R$^a$, —$SO_2NR^aR^b$, —$C_{1-6}$ alkylSO$_2$NR$^a$R$^b$, —C(O)NR$^a$SO$_2$R$^b$ and —NR$^a$C(O)R$^b$;

or $R^1$ and $R^2$ combine to form a heterocyclyl group optionally containing 1, 2, or 3 additional heteroatoms independently selected from oxygen, sulfur and nitrogen, and optionally substituted with 1 to 3 groups independently selected from oxo, —$C_{1-6}$alkyl, —$C_{3-8}$cycloalkyl, —$C_{2-6}$ alkenyl, —$C_{2-6}$ alkynyl, —$OR^a$, —C(O)OR$^a$, —$C_{1-6}$ cyanoalkyl, —$C_{1-6}$ alkylOR$^a$, —$C_{1-6}$haloalkyl, —$C_{1-3}$ alkyl $C_{3-8}$cycloalkyl, —C(O)R$^a$, $C_{1-6}$alkylC(O)R$^a$, —$C_{1-6}$alkylC(O)OR$^a$, —$NR^aR^b$, —$C_{1-6}$alkylNR$^a$R$^b$, —C(O)NR$^a$R$^b$, —$C_{1-6}$alkylC(O)NR$^a$R$^b$, —$SO_2R^a$, —$C_{1-6}$ alkylSO$_2$R$^a$, —$SO_2NR^aR^b$, and $C_{1-6}$ alkylSO$_2$NR$^a$R$^b$;

$R^3$ is independently H, —$C_{1-6}$alkyl, —$C_{2-6}$ alkenyl, —$C_{1-6}$ alkylaryl, —$C_{1-6}$ alkylheteroaryl, —$C_{1-6}$ alkylheterocyclyl, —$C_{2-6}$alkyl-OR$^a$, —$C_{1-6}$ alkylC(O)OR$^a$, or —$C_{2-6}$ alkenylC(O)OR$^a$;

$R^4$ is independently H, —$C_{1-6}$alkyl, —$C_{2-6}$ alkenyl, —$C_{1-6}$ alkylaryl, —$C_{1-6}$ alkylheteroaryl, —$C_{1-6}$ alkylheterocyclyl, —$C_{2-6}$alkyl-OR$^a$, —$C_{1-6}$ alkylC(O)OR$^a$, or —$C_{2-6}$ alkenylC(O)OR$^a$;

$R^a$ is independently selected from H, —$C_{1-6}$alkyl, —$C_{3-8}$cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl;

$R^b$ is independently selected from H, —$C_{1-6}$alkyl, —$C_{3-8}$cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$ alkylheterocyclyl;

or $R^a$ and $R^b$ may combine together to form a ring consisting of 3-8 ring atoms that are C, N, O, or S; wherein the ring is optionally substituted with 1 to 4 groups independently selected from —$OR^f$, —CN, halo, —$C_{1-6}$ alkylOR$^f$, —$C_{1-6}$ cyanoalkyl, —$C_{1-6}$haloalkyl, —$C_{3-8}$cycloalkyl, —$C_{1-3}$ alkyl$C_{3-8}$cycloalkyl, —C(O)R$^f$, —$C_{1-6}$ alkylC(O)R$^f$, —C(O)OR$^f$, —$C_{1-6}$ alkylC(O)OR$^f$, —$NR^fR^g$, —$C_{1-6}$ alkylNR$^f$R$^g$, —C(O)NR$^f$R$^g$, —$C_{1-6}$ alkylC(O)NR$^f$R$^g$, —$SO_2R^f$, —$C_{1-6}$ alkylSO$_2$R$^f$, —$SO_2NR^fR^g$, —$C_{1-6}$ alkylSO$_2$NR$^f$R$^g$, —C(O)NR$^f$SO$_2$R$^g$ and —NR$^f$C(O)R$^g$;

$R^c$ is independently selected from H, OH, —$C_{1-6}$alkyl, —$C_{3-8}$cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl;

$R^d$ is independently selected from H, —$C_{1-6}$alkyl, —$C_3$-$C_8$cycloalkyl, aryl, heteroaryl, heterocyclyl, —$C_{1-3}$ alkyl $C_{3-8}$cycloalkyl, —$C_{1-6}$ alkylaryl, —$C_{1-6}$ alkylheteroaryl, and —$C_{1-6}$alkylheterocyclyl;

$R^e$ is independently selected from H, —$C_{1-6}$alkyl, —$OC_{1-6}$alkyl, —$C_{3-8}$cycloalkyl, aryl, heteroaryl, heterocyclyl, —$OC_{3-8}$cycloalkyl, —Oaryl, —Oheteroaryl, —Oheterocyclyl, —$C_{1-3}$ alkyl$C_{3-8}$cycloalkyl, —$C_{1-6}$alkylaryl, —$C_{1-6}$alkylheteroaryl, —$NR^fR^g$, —$C_{1-6}$alkylNR$^f$R$^g$, —$C(O)NR^fR^g$, —$C_{1-6}$alkylC(O)$NR^fR^g$, —$NHSO_2R^f$, —$C_{1-6}$alkyl$SO_2R^f$, and —$C_{1-6}$alkyl$SO_2NR^fR^g$;

$R^f$ is independently selected from H, —$C_{1-6}$alkyl, —$C_{3-8}$cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl; and $R^g$ is independently selected from H, —$C_{1-6}$ alkyl, —$C_{3-8}$ cycloalkyl, aryl, heteroaryl, heterocyclyl, —$C_{1-3}$ alkyl $C_{3-8}$cycloalkyl, —$C_{1-6}$ alkylaryl, —$C_{1-6}$ alkylheteroaryl, and —$C_{1-6}$alkylheterocyclyl;

or a pharmaceutically acceptable salt, stereoisomer, mixture of stereoisomers, or tautomer thereof.

The present disclosure further provides a compound of formula (I):

$$R^W\text{-}Q^W\text{-}L^W\text{-}Ar^W\text{—}Ar^E\text{-}L^E\text{-}Q^E\text{-}R^E \quad (I)$$

wherein:

$Ar^E$ and $Ar^W$ are each independently a cycloalkyl, aryl, heteroaryl, or heterocyclyl;

wherein each cycloalkyl, aryl, heteroaryl, or heterocyclyl is optionally substituted with 1 to 4 groups independently selected from halo, —$OR^a$, —$NO_2$, —CN, —$NR^aR^b$, —$N_3$, —$SO_2R^a$, —$C_{1-6}$ alkyl, —$C_{1-6}$ haloalkyl, —$C_{2-6}$alkenyl, —$C_{2-6}$alkynyl, —$OC_{1-6}$alkyl, —$OC_{1-6}$haloalkyl, —$C_{3-8}$cycloalkyl, and —$C_{1-6}$ alkyl$C_{3-8}$ cycloalkyl; and wherein each alkyl, alkenyl, alkynyl, and cycloalkyl is optionally substituted with 1 to 4 groups independently selected from oxo, —$NO_2$, —$N_3$, —$OR^a$, halo, and cyano;

$L^E$ and $L^W$ are each independently a bond, —O—, —S—, —SO—, —$SO_2$—, —$(CR^3R^4)_m$—, —$(CR^3R^4)_mO(CR^3R^4)_m$—, —$(CR^3R^4)_mS(CR^3R^4)_m$—, —$(CR^3R^4)_mNR^3(CR^3R^4)_m$—, —C(O)—, —$(CR^3R^4)_mC(O)(CR^3R^4)_m$—, —$(CR^3R^4)_mC(O)NR^3(CR^3R^4)_m$—, —$(CR^3R^4)_mNR^3C(O)(CR^3R^4)_m$—, $C_{2-6}$ alkenylene, $C_{2-6}$ alkynylene,

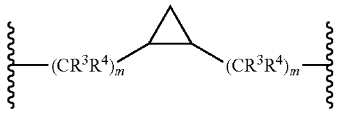
or
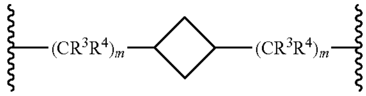
;

wherein each m is independently 0, 1, 2, 3 or 4;

$Q^E$ and $Q^W$ are each independently aryl, heteroaryl, or heterocyclyl;

wherein each aryl, heteroaryl, or heterocyclyl is optionally substituted with 1 to 4 groups independently selected from halo, oxo, —$OR^a$, —$N_3$, —$NO_2$, —CN, —$NR^1R^2$, —$SO_2R^a$, —$SO_2NR^aR^b$, —$NR^aSO_2R^a$, —$NR^aC(O)R^a$, —$C(O)R^a$, —$C(O)OR^a$, —$C(O)NR^aR^b$, —$NR^aC(O)OR^a$, —$NR^aC(O)NR^1R^2$, —$OC(O)NR^aR^b$, —$NR^aSO_2NR^aR^b$, —$C(O)NR^aSO_2NR^aR^b$, —$C_{1-6}$ alkyl, —$C_{2-6}$ alkenyl, —$C_{2-6}$ alkynyl, —$OC_{1-6}$ alkyl, —$C_{3-8}$ cycloalkyl, —$C_{1-6}$ alkyl$C_{3-8}$ cycloalkyl, aryl, heteroaryl, heterocyclyl, and $R^N$; and wherein the alkyl, alkenyl, alkynyl, $C_{3-8}$ cycloalkyl, aryl, heteroaryl, or heterocyclyl group is optionally substituted with 1 to 4 groups independently selected from oxo, —$NO_2$, —$N_3$, —$OR^a$, halo, cyano, —$NR^aR^b$, —$C(O)R^a$, —$C(O)OR^a$, —$OC_{1-6}$cyanoalkyl, —$C(O)NR^aR^b$, $NR^aC(O)R^a$, —$NR^aC(O)OR^a$, —$SO_2R^a$, —$NR^aSO_2R^b$, —$SO_2NR^aR^b$, —$NR^aSO_2NR^aR^b$, —$C(O)NR^aSO_2NR^aR^b$ and —$C_{3-8}$ cycloalkyl; and further wherein the heteroaryl or heterocyclic group may be oxidized on a nitrogen atom to form an N-oxide or oxidized on a sulfur atom to form a sulfoxide or sulfone;

$R^N$ is independently —$C_{1-6}$alkyl$NR^1R^2$, —$OC_{1-6}$ alky$NR^1R^2$, —$C_{1-6}$ alkyl$OC_{1-6}$ alkyl$NR^1R^2$, —$NR^aC_{1-6}$ alkyl$NR^1R^2$, —$C_{1-6}$ alkylC(O)$NR^1R^2$, —$OC_{1-6}$ alkylC(O)$NR^1R^2$, —$OC_{1-6}$ alkylC(O)$OR^1$, —$SC_{1-6}$alkyl$NR^1R^2$, —$C_{1-6}$alkyl$OR^a$, or

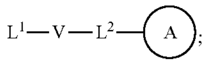
;

wherein: $L^1$ is independently a bond, O, $NR^a$, S, SO, or $SO_2$;

V is independently selected from a bond, $C_{1-6}$alkyl, $C_{2-6}$alkenyl, and $C_{2-6}$alkynyl;

wherein each alkyl, alkenyl, or alkynyl is optionally independently substituted with $OR^a$, halo, cyano, —$NR^aR^b$ or —$C_{3-8}$ cycloalkyl;

$L^2$ is independently a bond, O, $NR^a$, S, SO, or $SO_2$;

ring A is independently cycloalkyl, aryl, heteroaryl, or heterocyclyl;

wherein each cycloalkyl, aryl, heteroaryl, or heterocyclyl is optionally substituted with 1 to 4 groups independently selected from oxo, —$NO_2$, —$N_3$, —$OR^a$, halo, cyano, —$C_{1-6}$ alkyl, —$C_{1-6}$ haloalkyl, —$C_{2-6}$alkenyl, —$C_{2-6}$ alkynyl, —$OC_{1-6}$ haloalkyl, $NR^aR^b$, —$C(O)R^a$, —$C(O)OR^a$, —$OC_{1-6}$ alkylCN, —$C(O)NR^aR^b$, —$NR^aC(O)R^a$, —$NR^aC(O)OR^a$, —$NR^aC(O)OR^a$, —$C(O)N(R^a)OR^b$, —$SO_2R^a$, —$SO_2NR^aR^b$, —$NR^aSO_2R^b$, —$NR^aSO_2NR^aR^b$, —$C(O)NR^aSO_2NR^aR^b$, $C_{3-8}$cycloalkyl, and $C_{1-6}$alkyl$C_{3-8}$ cycloalkyl; and wherein the alkyl, alkenyl, or alkynyl group is optionally independently substituted with —$OR^a$, halo, cyano, —$NR^aR^b$ or —$C_{3-8}$ cycloalkyl;

$R^E$ and $R^W$ are each independently —$NR^1R^2$, —$C_{1-6}$ alky$NR^1R^2$, —$OC_{1-6}$ alkyl$NR^1R^2$, —$C_{1-6}$ alkyl$OC_{1-6}$alkyl$NR^1R^2$, —$NR^aC_{1-6}$ alkyl$NR^1R^2$, —$C_{1-6}$ alkyl$N^+R^1R^2R^3$, —$SC_{1-6}$ alkyl$NR^1R^2$, —$C(O)NR^1R^2$, —$SO_2R^a$, —$(CH_2)_uSO_2NR^1R^2$, —$(CH_2)_uNR^aSO_2NR^aR^b$, —$SO_2NR^aC_{1-6}$alky$NR^1R^2$, —$NR^aSO_2C_{1-6}$ alkyl$NR^1R^2$, —$(CH_2)_uC(O)NR^aSO_2NR^aR^b$, —$(CH_2)_uN^+R^1R^2O^-$, —$(CH_2)_uP^+R^bR^cR^d$, —$(CH_2)_uP^+R^cR^dO^-$, —$(CH_2)_uP^+O[NR^aR^b][NR^cR^d]$, —$(CH_2)_uNR^cP(O)(OR^c)_2$, —$(CH_2)_uCH_2OP(O)(OR^c)(OR^d)$, —$(CH_2)_uOP(O)(OR^c)(OR^d)$, —$(CH_2)_uOP(O)NR^aR^b)(OR^a)$, or

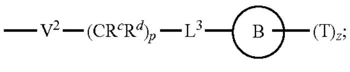
;

wherein:

$V^2$ is independently a bond, O, $NR^a$, S, SO, $SO_2$, C(O)$NR^a$, $NR^aC(O)$, $SO_2NR^1R^2$, or $NR^aSO_2$;

$L^3$ is independently a bond, O, $NR^a$, S, SO, $SO_2$, C(O)$NR^a$, $NR^aC(O)$, $SO_2NR^1R^2$, or $NR^aSO_2$;

ring B is independently cycloalkyl, aryl, heteroaryl, or heterocyclyl;

T is independently H, $OR^a$, $(CH_2)_qNR^1R^2$, $(CH_2)_qNR^aC(O)R^e$, or $(CH_2)_qC(O)R^e$;

p is independently 0, 1, 2, 3, 4, or 5;

q is independently 0, 1, 2, 3, 4, or 5;

u is 0, 1, 2, 3, or 4;

z is 0, 1, 2, or 3; and wherein the alkyl, cycloalkyl, aryl, heteroaryl, or heterocyclyl of $R^E$ or $R^W$ is optionally substituted with 1 to 3 substituents independently selected from the group consisting of $NR^aR^b$, halo, cyano, oxo, $OR^a$, —$C_{1-6}$alkyl, —$C_{1-6}$ haloalkyl, —$C_{1-6}$ cyanoalkyl, —$C_{1-6}$alkyN$R^aR^b$, —$C_{1-6}$ alkylOH, $C_{3-8}$ cycloalkyl, and —$C_{1-3}$ alkyl$C_{3-8}$cycloalkyl;

provided that at least one of $V^2$, $L^3$, ring B and T contains a nitrogen atom;

$R^1$ is independently selected from H, —$C_{1-8}$ alkyl, —$C_{2-6}$ alkenyl, —$C_{2-6}$ alkynyl, —$C_{3-6}$ cycloalkyl, aryl, heteroaryl, heterocyclyl, —$C_{1-6}$ alkylaryl, —$C_{1-6}$ alkylheteroaryl, —$C_{1-6}$ alkylheterocyclyl, —$C_{1-6}$ alkylC(O)O$R^a$, —$C_{2-6}$ alkenylC(O)O$R^a$, —$SO_2R^a$, —$SO_2NR^aR^b$, —C(O)N$R^a$$SO_2R^a$, and $C_{1-6}$alkyl$C_{3-8}$cycloalkyl;

wherein each alkyl, alkenyl, cycloalkyl, aryl, heteroaryl, or heterocyclyl is optionally substituted with 1 to 4 groups independently selected from —O$R^a$, —CN, halo, $C_{1-6}$alkyl, —$C_{1-6}$ alkylO$R^a$, —$C_{1-6}$ cyanoalkyl, —$C_{1-6}$haloalkyl, $C_{3-8}$ cycloalkyl, —$C_{1-3}$alkyl$C_{3-8}$cycloalkyl, —C(O)$R^a$, —$C_{1-6}$ alkylC(O)$R^a$, —C(O)O$R^a$, —$C_{1-6}$ alkylC(O)O$R^a$, —N$R^aR^b$, —OC(O)N$R^aR^b$, N$R^a$C(O)O$R^b$, —$C_{1-6}$alkylN$R^aR^b$, —C(O)N$R^aR^b$, —$C_{1-6}$ alkylC(O)N$R^aR^b$, —$SO_2R^a$, —$C_{1-6}$alkyl$SO_2R^a$, —$SO_2NR^aR^b$, —$C_{1-6}$ alkyl$SO_2NR^aR^b$, —C(O)N$R^a$$SO_2R^b$, —$C_{1-6}$ alkylC(O)N$R^a$$SO_2R^b$, —N$R^a$C(O)$R^b$, and —$C_{1-6}$alkylN$R^a$C(O)$R^b$;

$R^2$ is independently selected from H, —$C_{1-6}$ alkyl, —$C_{2-6}$ alkenyl, —$C_{2-6}$ alkynyl, —$C_{3-6}$ cycloalkyl, aryl, heteroaryl, heterocyclyl, —$C_{1-6}$ alkylaryl, —$C_{1-6}$ alkylheteroaryl, —$C_{1-6}$ alkylheterocyclyl, —$C_{2-6}$alkyl-O$R^a$, —$C_{1-6}$ alkylC(O)O$R^a$, and —$C_{2-6}$ alkenylC(O)O$R^a$;

wherein each alkyl, alkenyl, alkynyl, cycloalkyl, aryl, heteroaryl, or heterocyclyl is optionally substituted with 1 to 4 groups independently selected from —O$R^a$, —CN, halo, $C_{1-6}$alkyl, —$C_{1-6}$ alkylO$R^a$, —$C_{1-6}$ cyanoalkyl, —$C_{1-6}$ haloalkyl, —$C_{3-8}$ cycloalkyl, —$C_{1-3}$alkyl$C_{3-8}$cycloalkyl, —C(O)$R^a$, —$C_{1-6}$ alkylC(O)$R^a$, —C(O)O$R^a$, —$C_{1-6}$ alkylC(O)O$R^a$, —N$R^aR^b$, —$C_{1-6}$ alkylN$R^aR^b$, —C(O)N$R^aR^b$, $C_{1-6}$alkylC(O)N$R^aR^b$, —$SO_2R^a$, —$C_{1-6}$alkyl$SO_2R^a$, —$SO_2NR^aR^b$, —$C_{1-6}$alkyl$SO_2NR^aR^b$, —C(O)N$R^a$$SO_2R^b$ and —N$R^a$C(O)$R^b$;

or $R^1$ and $R^2$ combine to form a heterocyclyl group optionally containing 1, 2, or 3 additional heteroatoms independently selected from oxygen, sulfur and nitrogen, and optionally substituted with 1 to 3 groups independently selected from oxo, —$C_{1-6}$ alkyl, —$C_{3-8}$ cycloalkyl, —$C_{2-6}$ alkenyl, —$C_{2-6}$ alkynyl, —O$R^a$, —C(O)O$R^a$, —$C_{1-6}$ cyanoalkyl, —$C_{1-6}$ alkylO$R^a$, —$C_{1-6}$haloalkyl, —$C_{1-3}$ alkyl $C_{3-8}$cycloalkyl, —C(O)$R^a$, $C_{1-6}$alkylC(O)$R^a$, —$C_{1-6}$alkylC(O)O$R^a$, —N$R^aR^b$, —$C_{1-6}$alkylN$R^aR^b$, —C(O)N$R^aR^b$, —$C_{1-6}$alkylC(O)N$R^aR^b$, —$SO_2R^a$, —$C_{1-6}$ alkyl$SO_2R^a$, —$SO_2NR^aR^b$, and $C_{1-6}$ alkyl$SO_2NR^aR^b$;

$R^3$ is independently H, —$C_{1-6}$ alkyl, —$C_{2-6}$ alkenyl, —$C_{3-6}$ cycloalkyl, aryl, heteroaryl, heterocyclyl, —$C_{1-6}$alkylaryl, —$C_{1-6}$alkylheteroaryl, —$C_{1-6}$ alkylheterocyclyl, —$C_{2-6}$alkyl-O$R^a$, —$C_{1-6}$alkylC(O)O$R^a$, or —$C_{2-6}$ alkenylC(O)O$R^a$;

$R^4$ is independently H, —$C_{1-6}$ alkyl, —$C_{2-6}$ alkenyl, —$C_{3-6}$ cycloalkyl, aryl, heteroaryl, heterocyclyl, —$C_{1-6}$ alkylaryl, —$C_{1-6}$ alkylheteroaryl, —$C_{1-6}$ alkylheterocyclyl, —$C_{2-6}$alkyl-O$R^a$, —$C_{1-6}$alkylC(O)O$R^a$, or —$C_{2-6}$ alkenylC(O)O$R^a$;

$R^a$ is independently selected from H, —$C_{1-6}$ alkyl, —$C_{3-8}$ cycloalkyl, aryl, heteroaryl, heterocyclyl, —$C_{1-3}$ alkyl $C_{3-8}$cycloalkyl, —$C_{1-6}$ alkylaryl, —$C_{1-6}$ alkylheteroaryl, and —$C_{1-6}$alkylheterocyclyl;

$R^b$ is independently selected from H, —$C_{1-6}$ alkyl, —$C_{3-8}$ cycloalkyl, aryl, heteroaryl, heterocyclyl, —$C_{1-3}$ alkyl $C_{3-8}$cycloalkyl, —$C_{1-6}$ alkylaryl, —$C_{1-6}$ alkylheteroaryl, and —$C_{1-6}$ alkylheterocyclyl;

or $R^a$ and $R^b$ may combine together to form a ring consisting of 3-8 ring atoms that are C, N, O, or S; wherein the ring is optionally substituted with 1 to 4 groups independently selected from —O$R^f$, —CN, halo, —$C_{1-6}$ alkylO$R^f$, —$C_{1-6}$ cyanoalkyl, —$C_{1-6}$haloalkyl, —$C_{3-8}$ cycloalkyl, —$C_{1-3}$ alkyl$C_{3-8}$cycloalkyl, —C(O)$R^f$, —$C_{1-6}$ alkylC(O)$R^f$, —C(O)O$R^f$, —$C_{1-6}$ alkylC(O)O$R^f$, —N$R^fR^g$, —$C_{1-6}$ alkylN$R^fR^g$, —C(O)N$R^fR^g$, —$C_{1-6}$alkyl(O)N$R^fR^g$, —$SO_2NR^fR^g$, —$C_{1-6}$ alkyl$SO_2NR^fR^g$, —C(O)N$R^f$$SO_2R^g$ and —N$R^f$C(O)$R^g$;

$R^c$ is independently selected from H, OH, —$C_{1-6}$ alkyl, —$C_{3-8}$ cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$ alkylheterocyclyl;

$R^d$ is independently selected from H, —$C_{1-6}$ alkyl, —$C_3$-$C_8$cycloalkyl, aryl, heteroaryl, heterocyclyl, —$C_{1-3}$ alkyl $C_{3-8}$cycloalkyl, —$C_{1-6}$ alkylaryl, —$C_{1-6}$ alkylheteroaryl, and —$C_{1-6}$ alkylheterocyclyl;

$R^e$ is independently selected from H, —$C_{1-6}$ alkyl, —O$C_{1-6}$alkyl, —$C_{3-8}$ cycloalkyl, aryl, heteroaryl, heterocyclyl, —O$C_{3-8}$ cycloalkyl, —Oaryl, —Oheteroaryl, —Oheterocyclyl, —$C_{1-3}$ alkyl$C_{3-8}$cycloalkyl, —$C_{1-6}$ alkylaryl, —$C_{1-6}$alkylheteroaryl, —N$R^fR^g$, —$C_{1-6}$ alkylN$R^fR^g$, —C(O)N$R^fR^g$, —$C_{1-6}$alkylC(O)N$R^fR^g$, —NH$SO_2R^f$, —$C_{1-6}$alkyl$SO_2R^f$, and —$C_{1-6}$alkyl$SO_2NR^fR^g$;

$R^f$ is independently selected from H, —$C_{1-6}$ alkyl, —$C_{3-8}$ cycloalkyl, aryl, heteroaryl, heterocyclyl, —$C_{1-3}$ alkyl $C_{3-8}$cycloalkyl, —$C_{1-6}$ alkylaryl, —$C_{1-6}$ alkylheteroaryl, and —$C_{1-6}$ alkylheterocyclyl; and $R^g$ is independently selected from H, —$C_{1-6}$ alkyl, —$C_{3-8}$ cycloalkyl, aryl, heteroaryl, heterocyclyl, —$C_{1-3}$ alkyl $C_{3-8}$cycloalkyl, —$C_{1-6}$ alkylaryl, —$C_{1-6}$ alkylheteroaryl, and —$C_{1-6}$ alkylheterocyclyl;

or a pharmaceutically acceptable salt, stereoisomer, mixture of stereoisomers, solvate, or tautomer thereof.

In one embodiment of formula (I), both $Ar^E$ and $Ar^W$ are optionally substituted bicyclic rings, wherein neither is an optionally substituted fused 5,6-aromatic or 5,6-heteromatic ring. In one embodiment of formula (I), both $L^E$ and $L^W$ are —O—. In one embodiment of formula (I), both $L^E$ and $L^W$ are -Q-O—$CH_2$—Ar—. In one embodiment of formula (I), each of $Ar^E$, $Ar^W$, $Q^E$, and are monocyclic, provided at least two are heteroaryl, and neither of $R^E$, and $R^W$ is an optionally substituted fused 5,6-aromatic or 5,6-heteromatic ring. In one embodiment of formula (I), at least one L is a bond, and none of $Ar^E$, $Ar^W$, $Q^E$, $Q^W$, $R^E$, and $R^W$ is an optionally substituted fused 5,6-aromatic or 5,6-heteromatic ring. In one embodiment of formula (I), at least one of the following occurs: a) both $Ar^E$ and $Ar^W$ are optionally substituted bicyclic rings, wherein neither is an optionally substituted fused 5,6-aromatic or 5,6-heteromatic ring; or both $L^E$ and $L^W$ are —O—; b) both $L^E$ and $L^W$ are -Q-O—$CH_2$—Ar—; c) each of $Ar^E$, $Ar^w$, $Q^E$, and $Q^W$ are monocyclic, provided at least two are heteroaryl, and neither of $R^E$, and $R^W$ is an optionally substituted fused 5,6-aromatic or 5,6-heteromatic ring; or d) at least one L is a bond, and none of $Ar^E$, $Ar^W$, $Q^E$, $Q^W$, $R^E$, and $R^W$ is an optionally substituted fused 5,6-aromatic or 5,6-heteromatic ring.

The present disclosure provides a method of inhibiting PD-1, PD-L1 and/or the PD-1/PD-L1 interaction comprising administering a compound of formula (I) or a pharmaceutically acceptable salt, stereoisomer, mixture of stereoisomers or tautomer thereof, to a patient in need thereof.

The present disclosure provides a method of treating cancer comprising administering a therapeutically effective amount of a compound formula (I) or a pharmaceutically acceptable salt, stereoisomer, mixture of stereoisomers, or tautomer thereof, to a patient in need thereof.

One embodiment provides the use of a compound of formula (I) or a pharmaceutically acceptable salt, stereoisomer, mixture of stereoisomers or tautomer thereof, for the treatment of cancer or a condition in a patient that is amenable to treatment by inhibiting PD-1, PD-L1 or the PD-1/PD-L1 interaction comprising administering said compound of formula (I) to said patient in need thereof.

In one embodiment, provided is a method for treating a cancer wherein the cancer is pancreatic cancer, bladder cancer, colorectal cancer, breast cancer, prostate cancer, renal cancer, hepatocellular cancer, lung cancer, ovarian cancer, cervical cancer, gastric cancer, esophageal cancer, head and neck cancer, melanoma, neuroendocrine cancer, CNS cancer, brain cancer, bone cancer, soft tissue sarcoma, non-small cell lung cancer, small-cell lung cancer or colon cancer, comprising administering a therapeutically effective amount of formula (I) or a pharmaceutically acceptable salt, stereoisomer, mixture of stereoisomers, or tautomer thereof to a patient in need thereof.

In one embodiment, provided is a method for treating a cancer or a condition in a patient that is amenable to treatment by inhibiting PD-1, PD-L1 or the PD-1/PD-L1 interaction selected from pancreatic cancer, bladder cancer, colorectal cancer, breast cancer, prostate cancer, renal cancer, hepatocellular cancer, lung cancer, ovarian cancer, cervical cancer, gastric cancer, esophageal cancer, head and neck cancer, melanoma, neuroendocrine cancer, CNS cancer, brain cancer, bone cancer, soft tissue sarcoma, non-small cell lung cancer, small-cell lung cancer and colon cancer comprising administering a therapeutically effective amount of a compound of formula (I) or a pharmaceutically acceptable salt, stereoisomer, mixture of stereoisomers, or tautomer thereof to a patient in need thereof, further comprising at least one additional anticancer agent or therapy selected from nivolumab, pembrolizumab, atezolizumab, ipilimumab, chemotherapy, radiation therapy, and resection therapy, to a patient in need thereof.

In one embodiment, provided is a method for treating HBV, comprising administering a therapeutically effective amount of formula (I) or a pharmaceutically acceptable salt, stereoisomer, mixture of stereoisomers, or tautomer thereof to a patient in need thereof.

In one embodiment, provided is a compound of formula (I) or a pharmaceutically acceptable salt, stereoisomer, mixture of stereoisomers or tautomer thereof, for the treatment of cancer or a condition in a patient selected from lymphoma, multiple myeloma, and leukemia. Additional diseases or conditions that may be treated include, but are not limited to acute lymphocytic leukemia (ALL), acute myeloid leukemia (AML), chronic lymphocytic leukemia (CLL), small lymphocytic lymphoma (SLL), myelodysplastic syndrome (MDS), myeloproliferative disease (MPD), chronic myeloid leukemia (CML), multiple myeloma (MM), non-Hodgkin's lymphoma (NHL), mantle cell lymphoma (MCL), follicular lymphoma, Waldestrom's macroglobulinemia (WM), T-cell lymphoma, B-cell lymphoma and diffuse large B-cell lymphoma (DLBCL).

In one embodiment, the present disclosure provides a compound of formula (I) or a pharmaceutically acceptable salt, stereoisomer, mixture of stereoisomers or tautomer thereof, in combination with at least one additional anticancer agent selected from rituxan, doxorubicin, gemcitabine, nivolumab, pembrolizumab, and ipilimumab.

In one embodiment, the present disclosure provides a compound of formula (I) or a pharmaceutically acceptable salt, stereoisomer, mixture of stereoisomers or tautomer thereof, in combination with at least one additional checkpoint inhibitor selected from nivolumab, pembrolizumab, atezolizumab, and ipilimumab.

In one embodiment, the present disclosure provides a pharmaceutical composition comprising a compound of formula (I) or a pharmaceutically acceptable salt, stereoisomer, mixture of stereoisomers or tautomer thereof, and a pharmaceutically acceptable carrier or excipient.

In one embodiment, the present disclosure provides a pharmaceutical composition comprising a compound of formula (I) or a pharmaceutically acceptable salt, stereoisomer, mixture of stereoisomers or tautomer thereof, and at least one additional anticancer agent and at least one pharmaceutically acceptable carrier or excipient.

In one embodiment, the present disclosure provides a pharmaceutical composition comprising a compound of formula (I) or a pharmaceutically acceptable salt, stereoisomer, mixture of stereoisomers or tautomer thereof, at least one additional therapeutic agent suitable for treating an HBV infection, and at least one pharmaceutically acceptable carrier or excipient.

In one embodiment, the present disclosure provides a kit that includes a compound of formula (I) or a pharmaceutically acceptable salt, stereoisomer, mixture of stereoisomers or tautomer thereof, a label and/or instructions for use of the compound in the treatment of cancer or a disease or condition mediated by PD-1, PD-L1 activity or the PD-1/PD-L interaction.

In one embodiment, the present disclosure provides a kit that includes a compound of formula (I) or a pharmaceutically acceptable salt, stereoisomer, mixture of stereoisomers or tautomer thereof, at least one additional anticancer agent, a label(s) and/or instructions for use of the compound(s) in the treatment of a disease or condition mediated by PD-1, PD-L1 activity or PD-1/PD-L interaction.

In one embodiment, the present disclosure provides articles of manufacture that include a compound of formula (I) or a pharmaceutically acceptable salt, or solvate thereof; and a container. In one embodiment, the container may be a vial, jar, ampoule, preloaded syringe, or an intravenous bag.

In one embodiment, the present disclosure provides a compound of formula (I) for use in therapy.

In another embodiment, the present disclosure provides a compound of formula (I) for use in the manufacture of a medicament for treating cancer.

DETAILED DESCRIPTION

Definitions

As used in the present disclosure, the following words and phrases are generally intended to have the meanings as set forth below unless expressly indicated otherwise or the context in which they are used indicates otherwise.

The following description sets forth exemplary methods, parameters and the like. It should be recognized, however, that such description is not intended as a limitation on the scope of the present disclosure but is instead provided as a description of exemplary embodiments.

As used in the present specification, the following words, phrases and symbols are generally intended to have the meanings as set forth below, except to the extent that the context in which they are used indicates otherwise.

A dash ("—") that is not between two letters or symbols is used to indicate a point of attachment for a substituent. For example, —$C(O)NH_2$ is attached through the carbon atom. A dash at the front or end of a chemical group is a matter of convenience; chemical groups may be depicted with or without one or more dashes without losing their ordinary meaning. Unless chemically or structurally required, no directionality is indicated or implied by the order in which a chemical group is written or named.

A squiggly line on a chemical group as shown below, for example,

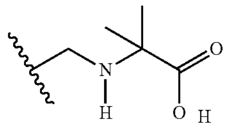

indicates a point of attachment, i.e., it shows the broken bond by which the group is connected to another described group.

The prefix "$C_{u-v}$" indicates that the following group has from u to v carbon atoms. For example, "$C_{1-6}$ alkyl" indicates that the alkyl group has from 1 to 6 carbon atoms.

Reference to "about" a value or parameter herein includes (and describes) embodiments that are directed to that value or parameter per se. In certain embodiments, the term "about" includes the indicated amount ±10%. In other embodiments, the term "about" includes the indicated amount ±5%. In certain other embodiments, the term "about" includes the indicated amount ±1%. Also, to the term "about X" includes description of "X". Also, the singular forms "a" and "the "include plural references unless the context clearly dictates otherwise. Thus, e.g., reference to" the compound" includes a plurality of such compounds and reference to "the assay" includes reference to one or more assays and equivalents thereof known to those skilled in the art.

The term "substituted" means that any one or more hydrogen atoms on the designated atom or group is replaced with one or more substituents other than hydrogen, provided that the designated atom's normal valence is not exceeded. The one or more substituents include, but are not limited to, alkyl, alkenyl, alkynyl, alkoxy, acyl, amino, amido, amidino, aryl, azido, carbamoyl, carboxyl, carboxyl ester, cyano, guanidino, halo, haloalkyl, heteroalkyl, heteroaryl, heterocycloalkyl, hydroxy, hydrazino, imino, oxo, nitro, alkylsulfinyl, sulfonic acid, alkylsulfonyl, thiocyanate, thiol, thione, or combinations thereof. Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl)substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein. For example, the term "substituted aryl" includes, but is not limited to, "alkylaryl." Unless specified otherwise, where a group is described as optionally substituted, any substituents of the group are themselves unsubstituted.

A "substituted" group also includes embodiments in which a monoradical substituent is bound to a single atom of the substituted group (e.g., forming a branch), and also includes embodiments in which the substituent may be a diradical bridging group bound to two adjacent atoms of the substituted group, thereby forming a fused ring on the substituted group.

"Alkyl" refers to an unbranched or branched saturated hydrocarbon chain. As used herein, alkyl has 1 to 20 carbon atoms (i.e., $C_{1-20}$ alkyl), 1 to 8 carbon atoms (i.e., $C_{1-8}$ alkyl), 1 to 6 carbon atoms (i.e., $C_{1-6}$ alkyl), or 1 to 4 carbon atoms (i.e., $C_{1-4}$alkyl). Examples of alkyl groups include methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl, and 3-methylpentyl. When an alkyl residue having a specific number of carbons is named by chemical name or identified by molecular formula, all positional isomers having that number of carbons may be encompassed; thus, for example, "butyl" includes n-butyl (i.e., —$(CH_2)_3CH_3$), sec-butyl (i.e., —$CH(CH_3)CH_2CH_3$), isobutyl (i.e., —$CH_2CH(CH_3)_2$) and tert-butyl (i.e., —$C(CH_3)_3$); and "propyl" includes n-propyl (i.e., —$(CH_2)_2CH_3$) and isopropyl (i.e., —$CH(CH_3)_2$).

"Alkenyl" refers to an aliphatic group containing at least one carbon-carbon double bond and having from 2 to 20 carbon atoms (i.e., $C_{2-20}$ alkenyl), 2 to 8 carbon atoms (i.e., $C_{2-8}$ alkenyl), 2 to 6 carbon atoms (i.e., $C_{2-6}$ alkenyl), or 2 to 4 carbon atoms (i.e., $C_{2-4}$alkenyl). Examples of alkenyl groups include ethenyl, propenyl, butadienyl (including 1,2-butadienyl, and 1,3-butadienyl).

"Alkynyl" refers to an aliphatic group containing at least one carbon-carbon triple bond and having from 2 to 20 carbon atoms (i.e., $C_{2-20}$ alkynyl), 2 to 8 carbon atoms (i.e., $C_{2-8}$ alkynyl), 2 to 6 carbon atoms (i.e., $C_{2-6}$ alkynyl), or 2 to 4 carbon atoms (i.e., $C_{2-4}$alkynyl). The term "alkynyl" also includes those groups having one triple bond and one double bond.

"Alkoxy" refers to the group "alkyl-O—" or "—O-alkyl". Examples of alkoxy groups include methoxy, ethoxy, n-propoxy, iso-propoxy, n-butoxy, tert-butoxy, sec-butoxy, n-pentoxy, n-hexoxy, and 1,2-dimethylbutoxy.

"Haloalkoxy" refers to an alkoxy group as defined above, wherein one or more hydrogen atoms are replaced by a halogen.

"Amino" refers to the group —$NR^yR^z$ wherein R and $R^z$ are independently selected from hydrogen, alkyl, haloalkyl, cycloalkyl, aryl, heterocyclyl, or heteroaryl; each of which may be optionally substituted.

"Aryl" refers to a monoradical or diradical aromatic carbocyclic group having a single ring (e.g., monocyclic) or multiple rings (e.g., bicyclic or tricyclic) including fused ring systems wherein one or more fused rings is/are fully or partially unsaturated. As used herein, aryl has 6 to 20 ring carbon atoms (i.e., $C_{6-20}$ aryl), 6 to 12 carbon ring atoms (i.e., $C_{6-12}$ aryl), or 6 to 10 carbon ring atoms (i.e., $C_{6-10}$ aryl). Non-limiting examples of aryl groups as used herein include phenyl, naphthyl, fluorenyl, indanyl, tetrahydroindanuyl, and anthryl. Aryl, however, does not encompass or overlap in any way with heteroaryl defined below. If one or more aryl groups are fused with a heteroaryl ring, the resulting ring system is heteroaryl. The classification of mono or diradical indicates whether the aryl group terminates the chain (monoradical) or is within a chain (diradical). The above definition does not preclude additional substituents on the aryl group. For example, as used herein, the aryl group in "A-aryl-B" is a diradical whereas the aryl group in "A-B-aryl" is monoradical, though additional substituents may be present on each aryl group.

The term "alkylsulfinyl" refers to the group —SO-alkyl, where alkyl is as defined above, and includes optionally substituted alkyl groups as also defined above.

The term "alkylsulfonyl" refers to the group-$SO_2$-alkyl, where alkyl is as defined above, and includes optionally substituted alkyl groups as also defined above.

"Cycloalkyl" refers to a saturated or partially saturated cyclic alkyl group having a single ring or multiple rings including fused, bridged, and spiro ring systems. As used herein, cycloalkyl has from 3 to 20 ring carbon atoms (i.e., $C_{3-20}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). Examples of cycloalkyl groups include cyclopropyl, cyclobutyl, cyclopentyl, and cyclohexyl.

As used herein the term "cycloalkenyl" groups means the non-aromatic carbocyclic group having at least one double bond.

"Cyanoalkyl" refers to an alkyl group substituted with cyano (CN).

"Halogen" or "halo" includes fluoro, chloro, bromo, and iodo.

The term "haloalkyl" refers to a monoradical or diradical having the indicated carbon atoms of the alkyl group wherein one or more hydrogen atoms have been substituted by a halogen. Examples of haloalkyl groups include $—CH_2F$, $—CHF_2$, $—CF_3$, $—CH_2CF_3$, $—CHFCH_2F$, $—CF_2—$, —CHF—, and the like. Similarly, the term "haloalkoxy", e.g., —O—$C_{1-3}$haloalkyl, refers to an alkoxy group wherein one or more hydrogen atoms of the alkyl group have been substituted by a halogen. Examples of haloalkoxy groups include $—OCH_2F$, $—OCHF_2$, $—OCF_3$, $—OCH_2CF_3$, $—OCHFCH_2F$, and the like. One of skill in the art is aware that similar definitions apply for the alkenyl and alkynyl analogs (e.g., $C_{2-4}$haloalkenyl, —O—$C_{2-4}$haloalkynyl) of the above.

"Heteroalkyl" refers to an alkyl group in which one or more of the carbon atoms (and any associated hydrogen atoms) are each independently replaced with the same or different heteroatomic group. The term "heteroalkyl" includes unbranched or branched saturated chain having carbon and heteroatoms. By way of example, 1, 2 or 3 carbon atoms may be independently replaced with the same or different heteroatomic group. Heteroatomic groups include, but are not limited to, —NR—, —O—, —S—, —SO—, $—SO_2—$, and the like, where R is H, alkyl, aryl, cycloalkyl, heteroalkyl, heteroaryl, or heterocycloalkyl, each of which may be optionally substituted. Examples of heteroalkyl groups include $—OCH_3$, $—CH_2OCH_3$, $—SCH_3$, $—CH_2SCH_3$, $—NRCH_3$, and $—CH_2NRCH_3$, where R is hydrogen, alkyl, aryl, arylalkyl, heteroalkyl, or heteroaryl, each of which may be optionally substituted. As used herein, heteroalkyl includes 1 to 10 carbon atoms, 1 to 8 carbon atoms, or 1 to 4 carbon atoms; and 1 to 3 heteroatoms, 1 to 2 heteroatoms, or 1 heteroatom.

"Heteroaryl" refers to a monoradical or diradical aromatic group having a single ring, multiple rings, or multiple fused rings, with one or more ring heteroatoms independently selected from nitrogen, oxygen, and sulfur. The term includes fused ring systems wherein one or more fused rings is/are fully or partially unsaturated. As used herein, heteroaryl include 1 to 20 ring carbon atoms (i.e., $C_{1-20}$ heteroaryl), 3 to 12 ring carbon atoms (i.e., $C_{3-12}$ heteroaryl), or 3 to 8 carbon ring atoms (i.e., $C_{3-8}$ heteroaryl); and 1 to 5 heteroatoms, 1 to 4 heteroatoms, 1 to 3 ring heteroatoms, 1 to 2 ring heteroatoms, or 1 ring heteroatom independently selected from nitrogen, oxygen, and sulfur. Non-limiting examples of heteroaryl groups include pyrimidinyl, purinyl, pyridyl, pyridazinyl, benzothiazolyl, benzodioxanyl, indolinyl, and pyrazolyl. The classification of mono or diradical indicates whether the heteroaryl group terminates the chain (monoradical) or is within a chain (diradical). The above definition does not preclude additional substituents on the heteroaryl group. For example, the heteroaryl group in "A-heteroaryl-B" is a diradical whereas the heteroaryl group in "A-B-heteroaryl" is monoradical, though additional substituents may be present on each heteroaryl group. Heteroaryl does not encompass or overlap with aryl as defined above.

"Heterocycloalkyl" refers to a saturated or unsaturated cyclic alkyl group, with one or more ring heteroatoms independently selected from nitrogen, oxygen and sulfur. A heterocycloalkyl may be a single ring or multiple rings wherein the multiple rings may be fused, bridged, or spiro. As used herein, heterocycloalkyl has 2 to 20 ring carbon atoms (i.e., $C_{2-20}$ heterocycloalkyl), 2 to 12 ring carbon atoms (i.e., $C_{2-12}$ heterocycloalkyl), 2 to 10 ring carbon atoms (i.e., $C_{2-10}$ heterocycloalkyl), 2 to 8 ring carbon atoms (i.e., $C_{2-8}$ heterocycloalkyl), 3 to 12 ring carbon atoms (i.e., $C_{3-12}$ heterocycloalkyl), 3 to 8 ring carbon atoms (i.e., $C_{3-8}$ heterocycloalkyl), or 3 to 6 ring carbon atoms (i.e., $C_{3-6}$ heterocycloalkyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. Examples of heterocycloalkyl groups include pyrrolidinyl, piperidinyl, piperazinyl, oxetanyl, dioxolanyl, azetidinyl, and morpholinyl. As used herein, the term "bridged-heterocycloalkyl" refers to a four- to ten-membered cyclic moiety connected at two non-adjacent atoms of the heterocycloalkyl with one or more (e.g., 1 or 2) four- to ten-membered cyclic moiety having at least one heteroatom where each heteroatom is independently selected from nitrogen, oxygen, and sulfur. As used herein, bridged-heterocycloalkyl includes bicyclic and tricyclic ring systems. Also used herein, the term "spiro-heterocycloalkyl" refers to a ring system in which a three- to ten-membered heterocycloalkyl has one or more additional ring, wherein the one or more additional ring is three- to ten-membered cycloalkyl or three- to ten-membered heterocycloalkyl, where a single atom of the one or more additional ring is also an atom of the three- to ten-membered heterocycloalkyl. Examples of spiro-heterocycloalkyl include bicyclic and tricyclic ring systems, such as 2-oxa-7-azaspiro[3.5]nonanyl, 2-oxa-6-azaspiro[3.4]octanyl, and 6-oxa-1-azaspiro[3.3]heptanyl.

The term "heterocyclyl," "heterocycle," or "heterocyclic" refers to a monoradical or diradical saturated or unsaturated group having a single ring or multiple condensed rings, having from 3 to 12 carbon atoms, from 1 to 6 hetero atoms, or from 1 to 4 heteroatoms, selected from nitrogen, sulfur, phosphorus, and/or oxygen within the ring. Where the group does not terminate the molecule, it is a diradical and is construed as such i.e., also referred to as heterocyclylene or heterocyclene.

Exemplary "heterocyclyl" groups include, but are not limited to, pyrrolidin-2-one, azetidine, piperidine, pyrrolidine, 4,5,6,7-tetrahydro-1H-imidazo[4,5-c]pyridine, morpholine, piperazin-2-one, 2,6-diazaspiro[3.3]heptane, 2,6-diazaspiro[3.4]octan-7-one, 2,5-diazaspiro[3.4]octan-6-one, 2,7-diazaspiro[4.4]nonan-3-one, 2,9-diazaspiro[5.5]undecan-1-one, 1,7-diazaspiro[3.5]nonan-2-one, 2,8-diazaspiro[4.5]decan-3-one, piperazine, 2-azaspiro[3.3]heptane, and 2-azabicyclo[2.2.2]octane.

The term "heterocyclyl" includes heterocycloalkenyl groups (i.e., the heterocyclyl group having at least one double bond), bridged-heterocyclyl groups, fused-heterocyclyl groups, and spiro-heterocyclyl groups. A heterocyclyl may be a single ring or multiple rings wherein the multiple rings may be fused, bridged, or spiro. Any non-aromatic ring containing at least one heteroatom is considered a heterocyclyl, regardless of the attachment (i.e., can be bound through a carbon atom or a heteroatom). Further, the term heterocyclyl is intended to encompass any non-aromatic ring containing at least one heteroatom, which ring may be fused to an aryl or heteroaryl ring, regardless of the attachment to the remainder of the molecule. A heterocyclyl may contain one or more oxo and/or thioxo groups.

"Acyl" refers to a group —C(═O)R, wherein R is hydrogen, alkyl, cycloalkyl, heterocycloalkyl, aryl, heteroalkyl, or heteroaryl; each of which may be optionally substituted, as defined herein. Examples of acyl include formyl, acetyl, cyclohexylcarbonyl, cyclohexylmethyl-carbonyl, and benzoyl.

The term "N-alkylated" means an alkyl group is substituted for one of the hydrogen atoms of a mono substituted amine, or a di-substituted amine group or a tri substituted amine group. When the alkylation is on a tri-substituted amine group an alkonium salt is generated i.e., a positive charge is generated on the nitrogen atom. N-alkylation is commonly associated with alkyl substitution on a ring nitrogen atom.

The term "oxo" refers to a group ═O.

The term "carboxy" refers to a group —C(O)—OH.

The term "ester" or "carboxyl ester" refers to the group —C(O)OR, where R is alkyl, cycloalkyl, aryl, heteroaryl, or heterocyclyl, which may be optionally further substituted, for example, by alkyl, alkoxy, halogen, $CF_3$, amino, substituted amino, cyano or —$SO_nR^f$, in which $R^f$ is alkyl, aryl, or heteroaryl, and n is 0, 1 or 2.

The term "substituted amino" refers to the group —NRR, where each R is independently hydrogen, alkyl, cycloalkyl, aryl, heteroaryl, or heterocyclyl, each of which may be optionally substituted, or a group as described or exemplified herein, or where both R groups are joined to form a heterocyclic group (e.g., morpholino) as described or exemplified herein, which also may be optionally substituted.

The term "amido" refers to the group —C(O)NRR where each R is independently hydrogen, alkyl, cycloalkyl, aryl, heteroaryl, or heterocyclyl, each of which may be optionally substituted, or a group as described or exemplified herein, or where both R groups are joined to form a heterocyclic group (e.g., morpholino) as described or exemplified herein, which also may be optionally substituted.

The term "sulfoxide" refers to a group —SOR, in which R is alkyl, cycloalkyl, heterocyclyl, aryl, or heteroaryl, each of which may be optionally substituted.

The term "sulfone" refers to a group —$SO_2R$, in which R is alkyl, cycloalkyl, heterocyclyl, aryl, or heteroaryl, each of which may be optionally substituted.

As used herein, the terms "alkylcycloalkyl," "alkylaryl," "alkylheteroaryl" and "alkylheterocyclyl" are intended to refer to a cycloalkyl, aryl, heteroaryl or heterocyclyl group which is bound to the remainder of the molecule via an alkyl moiety, where the terms "alkyl," "cycloalkyl," "aryl," "heteroaryl" and "heterocyclyl" are as defined herein. Exemplary alkylaryl groups include benzyl, phenethyl, and the like.

"Optional" or "optionally" means that the subsequently described event or circumstance may or may not occur, and that the description includes instances where said event or circumstance occurs and instances in which it does not.

Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively. Also, unless indicated explicitly otherwise, where combinations of groups are referred to herein as one moiety, e.g., arylalkyl, the last mentioned group contains the atom by which the moiety is attached to the rest of the molecule.

Where a group is represented by a bond, multiple adjacent groups whether the same or different, when represented by bonds, constitute a single bond. For example the group "-$L^1$-$V^1$-$L^2$-" constitutes a single bond if each of $L^1$, $V^1$ and $L^2$ is a bond.

Where a given group (moiety) is described herein as being attached to a second group and the site of attachment is not explicit, the given group may be attached at any available site of the given group or to any available site of the second group. For example, an "alkyl-substituted phenyl", where the attachment sites are not explicit, may have any available site of the alkyl group attached to any available site of the phenyl group. In this regard, an "available site" is a site of the group at which hydrogen of the group may be replaced with a substituent.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. Also not included are infinite numbers of substituents, whether the substituents are the same or different. In such cases, the maximum number of such substituents is three. Each of the above definitions is thus constrained by a limitation that, for example, substituted aryl groups are limited to -substituted aryl-(substituted aryl)-substituted aryl.

"Isomers" are different compounds that have the same molecular formula. Isomers include stereoisomers, enantiomers and diastereomers.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. The term "(±)" is used to designate a racemic mixture where appropriate.

"Diastereoisomers" are stereoisomers that have at least two asymmetric atoms, but which are not mirror-images of each other.

The compounds of the disclosure may possess one or more asymmetric centers and may be produced as a racemic mixture or as individual enantiomers or diastereoisomers.

The number of stereoisomers present in any given compound of a given formula depends upon the number of asymmetric centers present (there are $2^n$ stereoisomers possible where n is the number of asymmetric centers). The individual stereoisomers may be obtained by resolving a racemic or non-racemic mixture of an intermediate at some appropriate stage of the synthesis or by resolution of the compound by conventional means. The individual stereoisomers (including individual enantiomers and diastereoisomers) as well as racemic and non-racemic mixture of stereoisomers are encompassed within the scope of the present disclosure, all of which are intended to be depicted by the structures of this specification unless otherwise specifically indicated.

The absolute stereochemistry is specified according to the Cahn Ingold Prelog R S system. When the compound is a pure enantiomer the stereochemistry at each chiral carbon may be specified by either R or S. A resolved compound whose absolute configuration is unknown may be designated (+) or (−) depending on the direction (dextro- or laevorotary) that it rotates the plane of polarized light at the wavelength of the sodium D line.

Some of the compounds exist as tautomeric isomers. Tautomeric isomers are in equilibrium with one another. For example, amide containing compounds may exist in equilibrium with imidic acid tautomers. Regardless of which tautomer is shown, and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

The term "polymorph" refers to different crystal structures of a crystalline compound. The different polymorphs may result from differences in crystal packing (packing polymorphism) or differences in packing between different conformers of the same molecule (conformational polymorphism).

The term "solvate" refers to a complex formed by combining a compound of formula (I), or any other formula as disclosed herein and a solvent.

The term "hydrate" refers to the complex formed by the combining of a compound of formula (I), or any formula disclosed herein, and water.

The term "prodrug" refers to compounds of formula (I), or derivatives of formula (I) disclosed herein, that include chemical groups which, in vivo, can be converted and/or can be split off from the remainder of the molecule to provide for the active drug. Pharmaceutically acceptable salts or biologically active metabolites thereof of the prodrug of a compound of formula (I) are also within the ambit of the present disclosure.

Any formula or structure given herein, including formula (I), or any formula disclosed herein, is intended to represent unlabeled forms as well as isotopically labeled forms of the compounds. Isotopically labeled compounds have structures depicted by the formulas given herein except that one or more atoms are replaced by an isotope having a selected atomic mass or mass number. Examples of isotopes that can be incorporated into compounds of the disclosure include isotopes of hydrogen, carbon, nitrogen, oxygen, phosphorus, fluorine and chlorine, such as, but not limited to $^2H$ (deuterium, D), $^3H$ (tritium), $^{11}C$, $^{13}C$, $^{14}C$, $^{15}N$, $^{18}F$, $^{31}P$, $^{32}P$, $^{35}S$, $^{36}Cl$, and $^{125}I$. Various isotopically labeled compounds of the present disclosure, for example those into which radioactive isotopes such as $^3H$, $^{13}C$ and $^{14}C$ are incorporated, are within the ambit of the present disclosure. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in treatment of patients. Such isotopically labeled analogs of compounds of the present disclosure may also be useful for treatment of diseases disclosed herein because they may provide improved pharmacokinetic and/or pharmacodynamic properties over the unlabeled forms of the same compounds. Such isotopically leveled forms of or analogs of compounds herein are within the ambit of the present disclosure. One of skill in the art is able to prepare and use such isotopically labeled forms following procedures for isotopically labeling compounds or aspects of compounds to arrive at isotopic or radiolabeled analogs of compounds disclosed herein.

The term "pharmaceutically acceptable salt" of a given compound refers to salts that retain the biological effectiveness and properties of the given compound, and which are not biologically or otherwise undesirable. Pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, di-substituted cycloalkyl amine, tri-substituted cycloalkyl amines, cycloalkenyl amines, di(cycloalkenyl) amines, tri(cycloalkenyl) amines, substituted cycloalkenyl amines, di-substituted cycloalkenyl amine, tri-substituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group. Amines are of general structure $N(R^{30})(R^{31})(R^{32})$, wherein mono-substituted amines have two of the three substituents on nitrogen ($R^{30}$, $R^{31}$, and $R^{32}$) as hydrogen, di-substituted amines have one of the three substituents on nitrogen ($R^{30}$, $R^{31}$, and $R^{32}$) as hydrogen, whereas tri-substituted amines have none of the three substituents on nitrogen ($R^{30}$, $R^{31}$, and $R^{32}$) as hydrogen. $R^{30}$, $R^{31}$, and $R^{32}$ are selected from a variety of substituents such as hydrogen, optionally substituted alkyl, aryl, heteroaryl, cycloalkyl, cycloalkenyl, heterocyclyl, and the like.

Specific examples of suitable amines include, by way of example only, isopropyl amine, trimethyl amine, diethyl amine, tri(iso-propyl) amine, tri(n-propyl) amine, ethanolamine, diethanolamine, 2-dimethylamino ethanol, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, “pharmaceutically acceptable carrier” or “pharmaceutically acceptable excipient” includes any and all solvents, dispersion media, coatings, antibacterial, and antifungal agents, isotonic and absorption delaying agents and the like. The use of such media and agents for pharmaceutically active substances is well known in the art. Except insofar as any conventional media or agent is incompatible with the active ingredient, or unless otherwise indicated herein, its use in the therapeutic compositions is contemplated. Supplementary active ingredients can also be incorporated into the compositions.

The term “anticancer agent” is any drug that is effective in the treatment of a malignant, or cancerous disease. Effectiveness may mean inhibition, partial, or full remission, prolongation of life, improvement in quality of life, or cure. There are several major classes of anticancer drugs including chemical compositions as disclosed herein or known to one of skill in the art e.g., PD-1, PD-L1, PD-1/PD-L1 interaction inhibitors, alkylating agents, antimetabolites, natural products, and hormones.

The term “additional anticancer agent” as used herein means the use or combination of a second, third, fourth, fifth, etc., anticancer agent(s) in addition to a compound according to formula (I) disclosed herein.

The term “anticancer therapy” means any currently known therapeutic methods for the treatment of cancer.

The term “blockade agent” or “check point inhibitors” are classes of immune oncology agents that inhibit PD-1, PD-L1, or the PD-1/PD-L1 interaction.

The term “treatment” or “treating” means any administration of a compound or compounds according to the present disclosure to a subject (e.g., a human) having or susceptible to a condition or disease disclosed herein for the purpose of: 1) preventing or protecting against the disease or condition, that is, causing the clinical symptoms not to develop; 2) inhibiting the disease or condition, that is, arresting or suppressing the development of clinical symptoms; or 3) relieving the disease or condition that is causing the regression of clinical symptoms. In some embodiments, the term “treatment” or “treating” refers to relieving the disease or condition or causing the regression of clinical symptoms.

As used herein, the term “preventing” refers to the prophylactic treatment of a patient in need thereof. The prophylactic treatment can be accomplished by providing an appropriate dose of a therapeutic agent to a subject at risk of suffering from an ailment, thereby substantially averting onset of the ailment. The presence of a genetic mutation or the predisposition to having a mutation may not be alterable. However, prophylactic treatment (prevention) as used herein has the potential to avoid/ameliorate the symptoms or clinical consequences of having the disease engendered by such genetic mutation or predisposition.

It will be understood by those of ordinary skill in the art that in human medicine, it is not always possible to distinguish between “preventing” and “suppressing” since the ultimate inductive event or events may be unknown, latent, or the patient is not ascertained until well after the occurrence of the event or events. Therefore, as used herein, the term “prophylaxis” is intended as an element of “treatment” to encompass both “preventing” and “suppressing” as defined herein. The term “protection,” as used herein, is meant to include “prophylaxis.”

The term “patient” typically refers to a “mammal” which includes, without limitation, human, monkeys, rabbits, mice, domestic animals, such as dogs and cats, farm animals, such as cows, horses, or pigs, and laboratory animals. In some embodiments, the term patient refers to a human in need of treatment as defined herein.

Compounds

Provided herein are compounds that function as PD-1 inhibitors, PD-L1 inhibitors, and/or PD-1/PD-L1 interaction inhibitors, methods of using such compounds and compositions comprising such compounds optionally in combination with one or more additional anticancer agents or therapies. In all embodiments discussed herein where there is more than one occurrence of a group or variable, it is intended that the group or variable is independently selected the list that follows. It is further contemplated that all embodiments directed to compounds include any pharmaceutically acceptable salt, stereoisomer, mixture of stereoisomers, solvate, prodrug or tautomer thereof.

The present disclosure provides a compound of formula (I):

$$R^W\text{-}Q^W\text{-}L^W\text{-}Ar^W\text{—}Ar^E\text{-}L^E\text{-}Q^E\text{-}R^E \quad (I)$$

wherein:

$Ar^E$ and $Ar^W$ are each independently cycloalkyl, aryl, heteroaryl, or heterocyclyl;

wherein each cycloalkyl, aryl, heteroaryl, or heterocyclyl is optionally substituted with 1 to 4 groups independently selected from halo, —$OR^a$, —$NO_2$, —CN, —$NR^aR^b$, —$N_3$, —$SO_2R^a$, —$C_{1-6}$ alkyl, —$C_{1-6}$ haloalkyl, —$C_{2-6}$alkenyl, —$C_{2-6}$alkynyl, —$OC_{1-6}$alkyl, —$OC_{1-6}$haloalkyl, —$C_{3-8}$cycloalkyl, and —$C_{1-6}$ alkyl$C_{3-8}$cycloalkyl;

wherein each alkyl, alkenyl, alkynyl, and cycloalkyl group is optionally substituted with 1 to 4 groups independently selected from oxo, —$NO_2$, —$N_3$, —$OR^a$, halo, and cyano;

$L^E$ and $L^W$ are each independently a bond, —O—, —S—, —SO—, —$SO_2$—, —$(CR^3R^4)_m$—, —$(CR^3R^4)_mO(CR^3R^4)_m$—, —$(CR^3R^4)_mS(CR^3R^4)_m$—, —$(CR^3R^4)_mNR^3(CR^3R^4)_m$—, —C(O)—, —$(CR^3R^4)_mC(O)(CR^3R^4)_m$—, —$(CR^3R^4)_mC(O)NR^3(CR^3R^4)_m$—, —$(CR^3R^4)_mNR^3C(O)(CR^3R^4)_m$—, $C_{2-6}$ alkenylene, $C_{2-6}$ alkynylene,

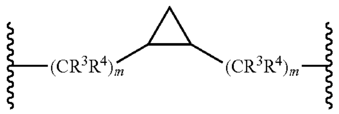 or

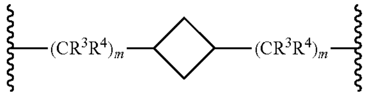 ;

wherein each m is independently 0, 1, 2, 3 or 4;

$Q^E$ and $Q^W$ are each independently aryl, heteroaryl, or heterocyclyl, wherein each aryl, heteroaryl, or heterocyclyl is optionally substituted with 1 to 4 groups independently selected from halo, oxo, —$OR^a$, —$N_3$, —$NO_2$, —CN, —$NR^1R^2$, —$SO_2R^a$, —$SO_2NR^aR^b$, —$NR^aSO_2R^a$, —$NR^aC(O)R^a$, —$C(O)R^a$, —$C(O)OR^a$, —$C(O)NR^aR^b$, —$NR^aC(O)OR^a$, —$NR^aC(O)NR^1R^2$, —$OC(O)NR^aR^b$, —$NR^aSO_2NR^aR^b$, —$C(O)NR^aSO_2NR^aR^b$, —$C_{1-6}$ alkyl, —$C_{2-6}$ alkenyl, —$C_{2-6}$ alkynyl, —$OC_{1-6}$ alkyl, —$C_{3-8}$cycloalkyl, —$C_{1-6}$ alkyl$C_{3-8}$ cycloalkyl, aryl, heteroaryl, heterocyclyl, and $R^N$;

wherein each alkyl, alkenyl, alkynyl, $C_{3-8}$ cycloalkyl, aryl, heteroaryl, or heterocyclyl is optionally substituted with 1 to 4 groups independently selected from oxo, —$NO_2$, —$N_3$, —$OR^a$, halo, cyano, —$NR^aR^b$, —$C(O)R^a$, —$C(O)OR^a$, —$OC_{1-6}$ alkyCN, —$C(O)NR^aR^b$, $NR^aC(O)R^a$, —$NR^aC(O)OR^a$, —$SO_2R^a$, —$NR^aSO_2R^b$, —$SO_2NR^aR^b$, —$NR^aSO_2NR^aR^b$, —$C(O)NR^aSO_2NR^aR^b$ and —$C_{3-8}$ cycloalkyl; and wherein the heteroaryl or heterocyclic group may be oxidized on a nitrogen atom to form an N-oxide or oxidized on a sulfur atom to form a sulfoxide or sulfone;

wherein $R^N$ is independently —$C_{1-6}$ alkyl$NR^1R^2$, —$OC_{1-6}$ alky$NR^1R^2$, —$C_{1-6}$ alkyl$OC_{1-6}$ alkyl$NR^1R^2$, —$NR^aC_{1-6}$ alkyl$NR^1R^2$, —$C_{1-6}$ alkyl$C(O)NR^1R^2$, —$OC_{1-6}$ alkyl$C(O)NR^1R^2$, —$OC_{1-6}$ alkyl$C(O)OR^1$, —$SC_{1-6}$ alkyl$NR^1R^2$, —$C_{1-6}$ alkyl$OR^a$, or

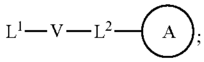;

wherein $L^1$ is independently a bond, O, $NR^a$, S, SO, or $SO_2$;

V is independently selected from a bond, $C_{1-6}$alkyl, $C_{2-6}$alkenyl, and $C_{2-6}$alkynyl;

wherein each alkyl, alkenyl, or alkynyl is optionally independently substituted with $OR^a$, halo, cyano, —$NR^aR^b$ or —$C_{3-8}$ cycloalkyl;

$L^2$ is independently a bond, O, $NR^a$, S, SO, or $SO_2$;

ring A is independently cycloalkyl, aryl, heteroaryl, or heterocyclyl;

wherein each cycloalkyl, aryl, heteroaryl, or heterocyclyl is optionally substituted with 1 to 4 groups independently selected from oxo, —$NO_2$, —$N_3$, —$OR^a$, halo, cyano, —$C_{1-6}$ alkyl, —$C_{1-6}$ haloalkyl, —$C_{2-6}$alkenyl, —$C_{2-6}$ alkynyl, —$OC_{1-6}$ haloalkyl, $NR^aR^b$, —$C(O)R^a$, —$C(O)OR^a$, —$OC_{1-6}$ alkylCN, —$C(O)NR^aR^b$, —$NR^aC(O)R^a$, —$NR^aC(O)OR^a$, —$NR^aC(O)OR^a$, —$C(O)N(R^a)OR^b$, —$SO_2R^a$, —$SO_2NR^aR^b$, —$NR^aSO_2R^b$, —$NR^aSO_2NR^aR^b$, —$C(O)NR^aSO_2NR^aR^b$, $C_{3-8}$cycloalkyl, and $C_{1-6}$alkyl$C_{3-8}$ cycloalkyl;

wherein each alkyl, alkenyl, or alkynyl is optionally independently substituted with $OR^a$, halo, cyano, —$NR^aR^b$ and —$C_{3-8}$ cycloalkyl;

$R^E$ and $R^W$ are each independently —$NR^1R^2$, —$C_{1-6}$ alky$NR^1R^2$, —$OC_{1-6}$ alkyl$NR^1R^2$, —$C_{1-6}$ alkyl$OC_{1-6}$alkyl$NR^1R^2$, —$NR^aC_{1-6}$ alkyl$NR^1R^2$, —$C_{1-6}$ alkyl$N^+R^1R^2R^3$, —$SC_{1-6}$ alkyl$NR^1R^2$, —$C(O)NR^1R^2$, —$SO_2R^a$, —$(CH_2)_uSO_2NR^1R^2$, —$(CH_2)_uNR^aSO_2NR^aR^b$, —$SO_2NR^aC_{1-6}$alky$NR^1R^2$, —$NR^aSO_2C_{1-6}$ alkyl$NR^1R^2$, —$(CH_2)_uC(O)NR^aSO_2NR^aR^b$, —$(CH_2)_uN^+R^1R^2O^-$, —$(CH_2)_uP^+R^bR^cR^d$, —$(CH_2)_uP^+R^cR^dO^-$, —$(CH_2)_uP^+O[NR^aR^b][NR^cR^d]$, —$(CH_2)_uNR^cP(O)(OR^c)_2$, —$(CH_2)_uNR^c(CH_2)_uP(O)(OR^c)_2$, —$(CH_2)_uCH_2OP(O)(OR^c)(OR^d)$; —$(CH_2)_uOP(O)(OR^c)(OR^d)$, —$(CH_2)_uOP(O)NR^aR^b)(OR^a)$, or

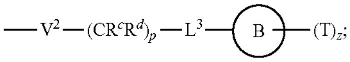;

wherein:

$V^2$ is independently a bond, O, $NR^a$, S, SO, $SO_2$, $C(O)NR^a$, $NR^aC(O)$, $SO_2NR^1R^2$, or $NR^aSO_2$;

$L^3$ is independently a bond, O, $NR^a$, S, SO, $SO_2$, $C(O)NR^a$, $NR^aC(O)$, $SO_2NR^1R^2$, or $NR^aSO_2$;

ring B is independently cycloalkyl, aryl, heteroaryl, or heterocyclyl;

T is independently H, $OR^a$, $(CH_2)_qNR^1R^2$, $(CH_2)_qNR^aC(O)R^e$, $(CH_2)_qOR^a$, or$(CH_2)_qC(O)R^e$;

p is independently 0, 1, 2, 3, 4, or 5;

q is independently 0, 1, 2, 3, 4, or 5;

u is 0, 1, 2, 3, or 4; and z is 0, 1, 2, or 3;

wherein each cycloalkyl, aryl, heteroaryl, or heterocyclyl of $R^E$ or $R^W$ is optionally substituted with 1 to 3 substituents independently selected from $NR^aR^b$, halo, cyano, oxo, $OR^a$, —$C_{1-6}$alkyl, —$C_{1-6}$haloalkyl, —$C_{1-6}$cyanoalkyl, —$C_{1-6}$alkyl$NR^aR^b$, —$C_{1-6}$alkylOH, —$C_{3-8}$cycloalkyl, and —$C_{1-3}$ alkyl$C_{3-8}$cycloalkyl;

provided that at least one of $V^2$, $L^3$, ring B and T contains a nitrogen atom;

$R^1$ is independently selected from H, —$C_{1-8}$ alkyl, —$C_{2-6}$ alkenyl, —$C_{2-6}$ alkynyl, —$C_{3-6}$ cycloalkyl, aryl, heteroaryl, heterocyclyl, —$C_{1-6}$ alkylaryl, —$C_{1-6}$ alkylheteroaryl, —$C_{1-6}$ alkylheterocyclyl, —$C_{1-6}$ alkyl$C(O)OR^a$, —$C_{2-6}$ alkenyl$C(O)OR^a$, —$SO_2R^a$, —$SO_2NR^aR^b$, —$C(O)NR^aSO_2R^a$, and $C_{1-6}$ alkyl$C_{3-8}$cycloalkyl;

wherein each alkyl, alkenyl, cycloalkyl, aryl, heteroaryl, or heterocyclyl is optionally substituted with 1 to 4 groups independently selected from —$OR^a$, —CN, halo, $C_{1-6}$alkyl, —$C_{1-6}$ alkyl$OR^a$, —$C_{1-6}$ cyanoalkyl, —$C_{1-6}$haloalkyl, $C_{3-8}$ cycloalkyl, —$C_{1-3}$ alkyl$C_{3-8}$cycloalkyl, —$C(O)R^a$, —$C_{1-6}$ alkyl $C(O)R^a$, —$C(O)OR^a$, —$C_{1-6}$alkyl$C(O)OR^a$, —$NR^aR^b$, —$OC(O)NR^aR^b$, $NR^aC(O)OR^b$, —$C_{1-6}$ alkyl$NR^aR^b$, —$C(O)NR^aR^b$, —$C_{1-6}$alkyl$C(O)NR^aR^b$, —$SO_2R^a$, —$C_{1-6}$alkyl$SO_2R^a$, —$SO_2N^aR^b$, —$C_{1-6}$ alkyl$SO_2NR^aR^b$, —$C(O)NR^aSO_2R^b$, —$C_{1-6}$ alkyl$C(O)NR^aSO_2R^b$, —$NR^aC(O)R^b$, and —$C_{1-6}$alkyl$NR^aC(O)R^b$;

$R^2$ is independently selected from H, —$C_{1-6}$ alkyl, —$C_{2-6}$ alkenyl, —$C_{2-6}$ alkynyl, —$C_{3-6}$ cycloalkyl, aryl, heteroaryl, heterocyclyl, —$C_{1-6}$ alkylaryl, —$C_{1-6}$ alkylheteroaryl, —$C_{1-6}$ alkylheterocyclyl, —$C_{2-6}$ alkyl-$OR^a$, —$C_{1-6}$ alkyl$C(O)OR^a$, and —$C_{2-6}$ alkenyl$C(O)OR^a$;

wherein each alkyl, alkenyl, alkynyl, cycloalkyl, aryl, heteroaryl, or heterocyclyl is optionally substituted with 1 to 4 groups independently selected from —$OR^a$, —CN, halo, $C_{1-6}$alkyl, —$C_{1-6}$alkyl$OR^a$, —$C_{1-6}$cyanoalkyl, —$C_{1-6}$haloalkyl, —$C_{3-8}$cycloalkyl, —$C_{1-3}$alkyl$C_{3-8}$cycloalkyl, —$C(O)R^a$, —$C_{1-6}$ alkyl$C(O)R^a$, —$C(O)OR^a$, —$C_{1-6}$ alkyl$C(O)OR^a$, —$NR^aR^b$, —$C_{1-6}$ alkyl$NR^aR^b$, —$C(O)NR^aR^b$, —$C_{1-6}$alkyl$C(O)NR^aR^b$, —$SO_2R^a$, —$C_{1-6}$alkyl$SO_2R^a$, —$SO_2NR^aR^b$, —$C_{1-6}$ alkyl$SO_2NR^aR^b$, —$C(O)NR^aSO_2R^b$ and —$NR^aC(O)R^b$;

or $R^1$ and $R^2$ combine to form a heterocyclyl group optionally containing 1, 2, or 3 additional heteroatoms independently selected from oxygen, sulfur and nitrogen, and optionally substituted with 1 to 3 groups independently selected from oxo, —$C_{1-6}$ alkyl, —$C_{3-8}$ cycloalkyl, —$C_{2-6}$ alkenyl, —$C_{2-6}$ alkynyl, —$OR^a$, —$C(O)OR^a$, —$C_{1-6}$ cyanoalkyl, —$C_{1-6}$ alkyl$OR^a$, —$C_{1-6}$haloalkyl, —$C_{1-3}$ alkyl$C_{3-8}$cycloalkyl, —C(O)$R^a$, $C_{1-6}$alkylC(O)$R^a$, —$C_{1-6}$alkylC(O)O$R^a$, —N$R^a$$R^b$, —$C_{1-6}$alkylN$R^a$$R^b$, —C(O)N$R^a$$R^b$, —$C_{1-6}$alkylC(O)N$R^a$$R^b$, —$SO_2R^a$, —$C_{1-6}$ alkyl$SO_2R^a$, —$SO_2NR^aR^b$, and $C_{1-6}$ alkyl$SO_2NR^aR^b$;

$R^3$ is independently H, —$C_{1-6}$ alkyl, —$C_{2-6}$ alkenyl, —$C_{3-6}$ cycloalkyl, aryl, heteroaryl, heterocyclyl, —$C_{1-6}$alkylaryl, —$C_{1-6}$alkylheteroaryl, —$C_{1-6}$ alkylheterocyclyl, —$C_{2-6}$alkyl-O$R^a$, —$C_{1-6}$alkylC(O)O$R^a$, or —$C_{2-6}$ alkenylC(O)O$R^a$;

$R^4$ is independently H, —$C_{1-6}$ alkyl, —$C_{2-6}$ alkenyl, —$C_{3-6}$ cycloalkyl, aryl, heteroaryl, heterocyclyl, —$C_{1-6}$alkylaryl, —$C_{1-6}$alkylheteroaryl, —$C_{1-6}$ alkylheterocyclyl, —$C_{2-6}$alkyl-O$R^a$, —$C_{1-6}$alkylC(O)O$R^a$, or —$C_{2-6}$ alkenylC(O)O$R^a$;

$R^a$ is independently selected from H, —$C_{1-6}$ alkyl, —$C_{3-8}$ cycloalkyl, aryl, heteroaryl, heterocyclyl, —$C_{1-3}$ alkyl $C_{3-8}$cycloalkyl, —$C_{1-6}$ alkylaryl, —$C_{1-6}$ alkylheteroaryl, and —$C_{1-6}$alkylheterocyclyl;

$R^b$ is independently selected from H, —$C_{1-6}$ alkyl, —$C_{3-8}$ cycloalkyl, aryl, heteroaryl, heterocyclyl, —$C_{1-3}$ alkyl $C_{3-8}$cycloalkyl, —$C_{1-6}$ alkylaryl, —$C_{1-6}$ alkylheteroaryl, and —$C_{1-6}$ alkylheterocyclyl;

or $R^a$ and $R^b$ may combine together to form a ring consisting of 3-8 ring atoms that are C, N, O, or S; wherein the ring is optionally substituted with 1 to 4 groups independently selected from —O$R^f$, —CN, halo, —$C_{1-6}$ alkylO$R^f$, —$C_{1-6}$ cyanoalkyl, —$C_{1-6}$haloalkyl, —$C_{3-8}$ cycloalkyl, —$C_{1-3}$ alkyl$C_{3-8}$cycloalkyl, —C(O)$R^f$, —$C_{1-6}$ alkylC(O)$R^f$, —C(O)O$R^f$, —$C_{1-6}$ alkylC(O)O$R^f$, —N$R^f$$R^g$, —$C_{1-6}$ alkylN$R^f$$R^g$, —C(O)N$R^f$$R^g$, —$C_{1-6}$ alkylC(O)N$R^f$$R^g$, —$SO_2R^f$, —$C_{1-6}$ alkyl$SO_2R^f$, —$SO_2NR^fR^g$, —$C_{1-6}$ alkyl$SO_2NR^fR^g$, —C(O)N$R^f$$SO_2R^g$ and —N$R^f$C(O)$R^g$;

$R^c$ is independently selected from H, OH, —$C_{1-6}$ alkyl, —$C_{3-8}$ cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl;

$R^d$ is independently selected from H, —$C_{1-6}$ alkyl, —$C_3$-$C_8$cycloalkyl, aryl, heteroaryl, heterocyclyl, —$C_{1-3}$ alkyl $C_{3-8}$cycloalkyl, —$C_{1-6}$ alkylaryl, —$C_{1-6}$ alkylheteroaryl, and —$C_{1-6}$alkylheterocyclyl;

$R^e$ is independently selected from H, —$C_{1-6}$ alkyl, —O$C_{1-6}$alkyl, —$C_{3-8}$ cycloalkyl, aryl, heteroaryl, heterocyclyl, —O$C_{3-8}$cycloalkyl, —Oaryl, —Oheteroaryl, —Oheterocyclyl, —$C_{1-3}$ alkyl$C_{3-8}$cycloalkyl, —$C_{1-6}$alkylaryl, —$C_{1-6}$alkylheteroaryl, —N$R^f$$R^g$, —$C_{1-6}$alkylN$R^f$$R^g$, —C(O)N$R^f$$R^g$, —$C_{1-6}$alkylC(O)N$R^f$$R^g$, —NH$SO_2R^f$, —$C_{1-6}$alkyl$SO_2R^f$, and —$C_{1-6}$alkyl$SO_2NR^fR^g$;

$R^f$ is independently selected from H, —$C_{1-6}$ alkyl, —$C_{3-8}$cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$ alkylheterocyclyl; and $R^g$ is independently selected from H, —$C_{1-6}$ alkyl, —$C_{3-8}$ cycloalkyl, aryl, heteroaryl, heterocyclyl, —$C_{1-3}$ alkyl$C_{3-8}$ cycloalkyl, —$C_{1-6}$ alkylaryl, —$C_{1-6}$ alkylheteroaryl, and —$C_{1-6}$ alkylheterocyclyl;

or a pharmaceutically acceptable salt, stereoisomer, mixture of stereoisomers, or tautomer thereof.

The present disclosure further provides a compound of formula (I):

$$R^W\text{-}Q^W\text{-}L^W\text{-}Ar^W\text{—}Ar^E\text{-}L^E\text{-}Q^E\text{-}R^E \quad (I)$$

wherein:

$Ar^E$ and $Ar^W$ are each independently cycloalkyl, aryl, heteroaryl, or heterocyclyl;

wherein each cycloalkyl, aryl, heteroaryl, or heterocyclyl is optionally substituted with 1 to 4 groups independently selected from halo, —O$R^a$, —$NO_2$, —CN, —N$R^a$$R^b$, —$N_3$, —$SO_2R^a$, —$C_{1-6}$ alkyl, —$C_{1-6}$ haloalkyl, —$C_{2-6}$alkenyl, —$C_{2-6}$alkynyl, —O$C_{1-6}$ alkyl, —O$C_{1-6}$haloalkyl, —$C_{3-8}$cycloalkyl, and —$C_{1-6}$ alkyl$C_{3-8}$ cycloalkyl;

wherein each alkyl, alkenyl, alkynyl, and cycloalkyl group is optionally substituted with 1 to 4 groups independently selected from oxo, —$NO_2$, —$N_3$, —O$R^a$, halo, and cyano;

$L^E$ and $L^W$ are each independently a bond, —O—, —S—, —SO—, —$SO_2$—, —$(CR^3R^4)_m$—, —$(CR^3R^4)_m$O$(CR^3R^4)_m$, —$(CR^3R^4)_m$S$(CR^3R^4)_m$—, —$(CR^3R^4)_m$N$R^3$$(CR^3R^4)_m$—, —C(O)—, —$(CR^3R^4)_m$C(O)$(CR^3R^4)_m$—, —$(CR^3R^4)_m$C(O)N$R^3$$(CR^3R^4)_m$—, —$(CR^3R^4)_m$N$R^3$C(O)$(CR^3R^4)_m$—, $C_{2-6}$ alkenylene, $C_{2-6}$ alkynylene,

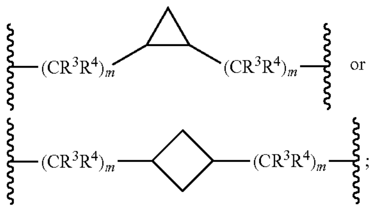

wherein each m is independently 1, 2, 3 or 4;

provided that when one of $Ar^E$ and $Ar^W$ is optionally substituted phenyl and the other is optionally substituted phenyl or optionally substituted 2,3-dihydrobenzo[b][1,4]dioxine, and one of $L^E$ and $L^W$ is —$CH_2$O—, —$CH_2CH_2$—, —CHCH—, and —C(O)N—; then the other of $L^E$ and $L^W$ is a bond, —O— or —$CH_2$— of the formula Ar—$CH_2$O-Q;

$Q^E$ and $Q^W$ are each independently aryl, heteroaryl, or heterocyclyl, wherein each aryl, heteroaryl, or heterocyclyl is optionally substituted with 1 to 4 groups independently selected from halo, oxo, —O$R^a$, —$N_3$, —$NO_2$, —CN, —N$R^1$$R^2$, —$SO_2R^a$, —$SO_2NR^aR^b$, —N$R^a$$SO_2R^a$, —N$R^a$C(O)$R^a$, —C(O)$R^a$, —C(O)O$R^a$, —C(O)N$R^a$$R^b$, —N$R^a$C(O)O$R^a$, —N$R^a$C(O)N$R^1$$R^2$, —OC(O)N$R^a$$R^b$, —N$R^a$$SO_2NR^aR^b$, —C(O)N$R^a$$SO_2NR^aR^b$, —$C_{1-6}$ alkyl, —$C_{2-6}$ alkenyl, —$C_{2-6}$ alkynyl, —O$C_{1-6}$ alkyl, —$C_{1-6}$ alkyl$C_{3-8}$ cycloalkyl, and $R^N$;

wherein each alkyl, alkenyl, alkynyl, is optionally substituted with 1 to 4 groups independently selected from oxo, —$NO_2$, —$N_3$, —O$R^a$, halo, cyano, —N$R^a$$R^b$, —C(O)$R^a$, —C(O)O$R^a$, —O$C_{1-6}$alkylCN, —C(O)N$R^a$$R^b$, N$R^a$C(O)$R^a$, —N$R^a$C(O)O$R^a$, —$SO_2R^a$, —N$R^a$$SO_2R^b$, —$SO_2NR^aR^b$, —N$R^a$$SO_2NR^aR^b$, —C(O)N$R^a$$SO_2NR^aR^b$ and —$C_{3-8}$ cycloalkyl;

wherein $R^N$ is independently —$C_{1-6}$ alkylN$R^1$$R^2$, —O$C_{1-6}$ alkyN$R^1$$R^2$, —$C_{1-6}$ alkylO$C_{1-6}$ alkylN$R^1$$R^2$, —N$R^a$$C_{1-6}$ alkylN$R^1$$R^2$, —$C_{1-6}$ alkylC(O)N$R^1$$R^2$, —O$C_{1-6}$ alkylC(O)N$R^1$$R^2$, —O$C_{1-6}$ alkylC(O)O$R^1$, —S$C_{1-6}$alkylN$R^1$$R^2$, —$C_{1-6}$alkylO$R^a$, or

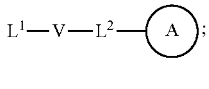

;

wherein $L^1$ is independently a bond, O, $NR^a$, S, SO, or $SO_2$;

V is independently selected from a bond, $C_{1-6}$alkyl, $C_{2-6}$alkenyl, and $C_{2-6}$alkynyl;

wherein each alkyl, alkenyl, or alkynyl is optionally independently substituted with $OR^a$, halo, cyano, $—NR^aR^b$ or $—C_{3-8}$ cycloalkyl;

$L^2$ is independently a bond, O, $NR^a$, S, SO, or $SO_2$;

provided at least one of $L^1$, V an $L^2$ is other than a bond;

ring A is independently cycloalkyl, aryl, heteroaryl, or heterocyclyl;

wherein each cycloalkyl, aryl, heteroaryl, or heterocyclyl is optionally substituted with 1 to 4 groups independently selected from oxo, $—NO_2$, $—N_3$, $—OR^a$, halo, cyano, $—C_{1-6}$ alkyl, $—C_{1-6}$ haloalkyl, $—C_{2-6}$alkenyl, $—C_{2-6}$ alkynyl, $—OC_{1-6}$haloalkyl, $NR^aR^b$, $—C(O)R^a$, $—C(O)OR^a$, $—OC_{1-6}$alkylCN, $—C(O)NR^aR^b$, $—NR^aC(O)R^a$, $—NR^aC(O)OR^a$, $—NR^aC(O)OR^a$, $—C(O)N(R^a)OR^b$, $—SO_2R^a$, $—SO_2NR^aR^b$, $—NR^aSO_2R^b$, $—NR^aSO_2NR^aR^b$, $—C(O)NR^aSO_2NR^aR^b$, $C_{3-8}$cycloalkyl, and $C_{1-6}$alkyl$C_{3-8}$ cycloalkyl;

wherein each alkyl, alkenyl, or alkynyl is optionally independently substituted with $OR^a$, halo, cyano, $—NR^aR^b$ and $—C_{3-8}$ cycloalkyl;

$R^E$ and $R^W$ are each independently $—NR^1R^2$, $—C_{1-6}$ alkyNR$^1R^2$, $—OC_{1-6}$ alkylNR$^1R^2$, $—C_{1-6}$ alkylO$C_{1-6}$alkyNR$^1R^2$, $—NR^aC_{1-6}$ alkylNR$^1R^2$, $—C_{1-6}$ alkylN$^+R^1R^2R^3$, $—SC_{1-6}$ alkylNR$^1R^2$, $—C(O)NR^1R^2$, $—SO_2R^a$, $—(CH_2)_uSO_2NR^1R^2$, $—(CH_2)_uNR^aSO_2NR^aR^b$, $—SO_2NR^aC_{1-6}$alkyNR$^1R^2$, $—NR^aSO_2C_{1-6}$ alkylNR$^1R^2$, $—(CH_2)_uC(O)NR^aSO_2NR^aR^b$, $—(CH_2)_uN^+R^1R^2O^-$, $—(CH_2)_uP^+R^bR^cR^d$, $—(CH_2)_uP^+R^cR^dO^-$, $—(CH_2)_uP^+O[NR^aR^b][NR^cR^d]$, $—(CH_2)_uNR^cP(O)(OR^c)_2$, $—(CH_2)_uNR^c(CH_2)_uP(O)(OR^c)_2$, $—(CH_2)_uCH_2OP(O)(OR^c)(OR^d)$; $—(CH_2)_uOP(O)(OR^c)(OR^d)$, $—(CH_2)_uOP(O)NR^aR^b)(OR^a)$, or

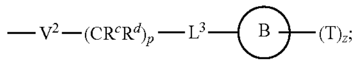

wherein:

$V^2$ is independently a bond, O, $NR^a$, S, SO, $SO_2$, $C(O)NR^a$, $NR^aC(O)$, $SO_2NR^1R^2$, or $NR^aSO_2$;

$L^3$ is independently a bond, O, $NR^a$, S, SO, $SO_2$, $C(O)NR^a$, $NR^aC(O)$, $SO_2NR^1R^2$, or $NR^aSO_2$;

ring B is independently cycloalkyl, aryl, heteroaryl, or heterocyclyl;

T is independently H, $OR^a$, $(CH_2)NR^1R^2$, $(CH_2)_qNR^aC(O)R^e$, $(CH_2)_qOR^a$, or $(CH_2)_qC(O)R^e$;

p is independently 0, 1, 2, 3, 4, or 5;

q is independently 0, 1, 2, 3, 4, or 5;

u is 0, 1, 2, 3, or 4; and z is 0, 1, 2, or 3;

wherein each cycloalkyl, aryl, heteroaryl, or heterocyclyl is optionally substituted with 1 to 3 substituents independently selected from $NR^aR^b$, halo, cyano, oxo, $OR^a$, $—C_{1-6}$ alkyl, $—C_{1-6}$haloalkyl, $—C_{1-6}$cyanoalkyl, $—C_{1-6}$alkylNR$^aR^b$, $—C_{1-6}$alkylOH, $—C_{3-8}$cycloalkyl, and $—C_{1-3}$ alkyl$C_{3-8}$cycloalkyl;

provided that at least one of $V^2$, $L^3$, ring B and T contains a nitrogen atom, and when each of $V^2$ and $L^3$ is a bond and p is 0, then either (i) neither of $L^E$ or $L^W$ is a bond or (ii) ring B is not a 5,6-membered fused heteroaryl where the 5-membered ring of the fused heteroaryl is bound to the corresponding $Q^E$ or $Q^W$;

$R^1$ is independently selected from H, $—C_{1-8}$ alkyl, $—C_{2-6}$ alkenyl, $—C_{2-6}$ alkynyl, $—C_{3-6}$ cycloalkyl, aryl, heteroaryl, heterocyclyl, $—C_{1-6}$ alkylaryl, $—C_{1-6}$ alkylheteroaryl, $—C_{1-6}$ alkylheterocyclyl, $—C_{1-6}$ alkylC(O)OR$^a$, $—C_{2-6}$ alkenylC(O)OR$^a$, $—SO_2R^a$, $—SO_2NR^aR^b$, $—C(O)NR^aSO_2R^a$, and $C_{1-6}$ alkyl$C_{3-8}$cycloalkyl;

wherein each alkyl, alkenyl, cycloalkyl, aryl, heteroaryl, or heterocyclyl is optionally substituted with 1 to 4 groups independently selected from $—OR^a$, —CN, halo, $C_{1-6}$alkyl, $—C_{1-6}$ alkylOR$^a$, $—C_{1-6}$ cyanoalkyl, $—C_{1-6}$haloalkyl, $C_{3-8}$ cycloalkyl, $—C_{1-3}$ alkyl$C_{3-8}$cycloalkyl, $—C(O)R^a$, $—C_{1-6}$ alkyl $C(O)R^a$, $—C(O)OR^a$, $—C_{1-6}$alkylC(O)OR$^a$, $—NR^aR^b$, $—OC(O)NR^aR^b$, $NR^aC(O)OR^b$, $—C_{1-6}$ alkylNR$^aR^b$, $—C(O)NR^aR^b$, $—C_{1-6}$alkylC(O)NR$^aR^b$, $—SO_2R^a$, $—C_{1-6}$alkylSO$_2R^a$, $—SO_2N^aR^b$, $—C_{1-6}$ alkylSO$_2NR^aR^b$, $—C(O)NR^aSO_2R^b$, $—C_{1-6}$ alkylC(O)NR$^aSO_2R^b$, $—NR^aC(O)R^b$, and $—C_{1-6}$alkylNR$^aC(O)R^b$;

$R^2$ is independently selected from H, $—C_{1-6}$alkyl, $—C_{2-6}$ alkenyl, $—C_{2-6}$ alkynyl, $—C_{3-6}$ cycloalkyl, aryl, heteroaryl, heterocyclyl, $—C_{1-6}$alkylaryl, $—C_{1-6}$alkylheteroaryl, $—C_{1-6}$ alkylheterocyclyl, $—C_{2-6}$alkyl-OR$^a$, $—C_{1-6}$ alkylC(O)OR$^a$, and $—C_{2-6}$ alkenylC(O)OR$^a$;

wherein each alkyl, alkenyl, alkynyl, cycloalkyl, aryl, heteroaryl, or heterocyclyl is optionally substituted with 1 to 4 groups independently selected from $—OR^a$, —CN, halo, $C_{1-6}$alkyl, $—C_{1-6}$alkylOR$^a$, $—C_{1-6}$cyanoalkyl, $—C_{1-6}$haloalkyl, $—C_{3-8}$cycloalkyl, $—C_{1-3}$alkyl$C_{3-8}$cycloalkyl, $—C(O)R^a$, $—C_{1-6}$ alkylC(O)R$^a$, $—C(O)OR^a$, $—C_{1-6}$ alkylC(O)OR$^a$, $—NR^aR^b$, $—C_{1-6}$ alkylNR$^aR^b$, $—C(O)NR^aR^b$, $—C_{1-6}$alkylC(O)NR$^aR^b$, $—SO_2R^a$, $—C_{1-6}$alkylSO$_2R^a$, $—SO_2NR^aR^b$, $—C_{1-6}$ alkylSO$_2NR^aR^b$, $—C(O)NR^aSO_2R^b$ and $—NR^aC(O)R^b$;

or $R^1$ and $R^2$ combine to form a heterocyclyl group optionally containing 1, 2, or 3 additional heteroatoms independently selected from oxygen, sulfur and nitrogen, and optionally substituted with 1 to 3 groups independently selected from oxo, $—C_{1-6}$alkyl, $—C_{3-8}$cycloalkyl, $—C_{2-6}$ alkenyl, $—C_{2-6}$ alkynyl, $—OR^a$, $—C(O)OR^a$, $—C_{1-6}$ cyanoalkyl, $—C_{1-6}$ alkylOR$^a$, $—C_{1-6}$haloalkyl, $—C_{1-3}$ alkyl $C_{3-8}$cycloalkyl, $—C(O)R^a$, $C_{1-6}$alkylC(O)R$^a$, $—C_{1-6}$alkylC(O)OR$^a$, $—NR^aR^b$, $—C_{1-6}$alkyNR$^aR^b$, $—C(O)NR^aR^b$, $—C_{1-6}$alkylC(O)NR$^aR^b$, $—SO_2R^a$, $—C_{1-6}$ alkylSO$_2R^a$, $—SO_2NR^aR^b$, and $C_{1-6}$ alkylSO$_2NR^aR^b$;

$R^3$ is independently H, $—C_{1-6}$alkyl, $—C_{2-6}$ alkenyl, $—C_{1-6}$ alkylaryl, $—C_{1-6}$ alkylheteroaryl, $—C_{1-6}$ alkylheterocyclyl, $—C_{2-6}$alkyl-OR$^a$, $—C_{1-6}$ alkylC(O)OR$^a$, or $—C_{2-6}$ alkenylC(O)OR$^a$;

$R^4$ is independently H, $—C_{1-6}$alkyl, $—C_{2-6}$ alkenyl, $—C_{1-6}$ alkylaryl, $—C_{1-6}$ alkylheteroaryl, $—C_{1-6}$ alkylheterocyclyl, $—C_{2-6}$alkyl-OR$^a$, $—C_{1-6}$ alkylC(O)OR$^a$, or $—C_{2-6}$ alkenylC(O)OR$^a$;

$R^a$ is independently selected from H, $—C_{1-6}$alkyl, $—C_{3-8}$cycloalkyl, aryl, heteroaryl, heterocyclyl, $—C_{1-3}$ alkyl$C_{3-8}$cycloalkyl, $—C_{1-6}$ alkylaryl, $—C_{1-6}$ alkylheteroaryl, and $—C_{1-6}$alkylheterocyclyl;

$R^b$ is independently selected from H, $—C_{1-6}$alkyl, $—C_{3-8}$cycloalkyl, aryl, heteroaryl, heterocyclyl, $—C_{1-3}$ alkyl$C_{3-8}$cycloalkyl, $—C_{1-6}$ alkylaryl, $—C_{1-6}$ alkylheteroaryl, and $—C_{1-6}$ alkylheterocyclyl;

or $R^a$ and $R^b$ may combine together to form a ring consisting of 3-8 ring atoms that are C, N, O, or S; wherein the ring is optionally substituted with 1 to 4 groups independently selected from $—OR^f$, —CN, halo, $—C_{1-6}$ alkylOR$^f$, $—C_{1-6}$ cyanoalkyl, —$C_{1-6}$haloalkyl, —$C_{3-8}$cycloalkyl, —$C_{1-3}$ alkyl$C_{3-8}$cycloalkyl, —C(O)$R^f$, —$C_{1-6}$ alkylC(O)$R^f$, —C(O)O$R^f$, —$C_{1-6}$ alkylC(O)O$R^f$, —N$R^fR^g$, —$C_{1-6}$ alkylN$R^fR^g$, —C(O)N$R^fR^g$, —$C_{1-6}$ alkylC(O)N$R^fR^g$, —$SO_2R^f$, —$C_{1-6}$ alkyl$SO_2R^f$, —$SO_2NR^fR^g$, —$C_{1-6}$ alkyl$SO_2NR^fR^g$, —C(O)N$R^fSO_2R^g$ and —N$R^f$C(O)$R^g$;

$R^c$ is independently selected from H, OH, —$C_{1-6}$ alkyl, —$C_{3-8}$cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl;

$R^d$ is independently selected from H, —$C_{1-6}$alkyl, —$C_3$-$C_8$cycloalkyl, aryl, heteroaryl, heterocyclyl, —$C_{1-3}$ alkyl $C_{3-8}$cycloalkyl, —$C_{1-6}$ alkylaryl, —$C_{1-6}$ alkylheteroaryl, and —$C_{1-6}$alkylheterocyclyl;

$R^e$ is independently selected from H, —$C_{1-6}$alkyl, —O$C_{1-6}$alkyl, —$C_{3-8}$cycloalkyl, aryl, heteroaryl, heterocyclyl, —O$C_{3-8}$cycloalkyl, —Oaryl, —Oheteroaryl, —Oheterocyclyl, —$C_{1-3}$ alkyl$C_{3-8}$cycloalkyl, —$C_{1-6}$alkylaryl, —$C_{1-6}$alkylheteroaryl, —N$R^fR^g$, —$C_{1-6}$alkylN$R^fR^g$, —C(O)N$R^fR^g$, —$C_{1-6}$alkylC(O)N$R^fR^g$, —NH$SO_2R^f$, —$C_{1-6}$alkyl$SO_2R^f$, and —$C_{1-6}$alkyl$SO_2NR^fR^g$;

$R^f$ is independently selected from H, —$C_{1-6}$ alkyl, —$C_{3-8}$cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl; and $R^g$ is independently selected from H, —$C_{1-6}$ alkyl, —$C_{3-8}$ cycloalkyl, aryl, heteroaryl, heterocyclyl, —$C_{1-3}$ alkyl $C_{3-8}$cycloalkyl, —$C_{1-6}$ alkylaryl, —$C_{1-6}$ alkylheteroaryl, and —$C_{1-6}$alkylheterocyclyl;

or a pharmaceutically acceptable salt, stereoisomer, mixture of stereoisomers, or tautomer thereof.

The present disclosure further provides a compound of formula (I):

$$R^W\text{-}Q^W\text{-}L^W\text{-}Ar^W\text{—}Ar^EL^E\text{-}Q^E\text{-}R^E \quad (I)$$

wherein:

$Ar^E$ and $Ar^W$ are each independently a cycloalkyl, aryl, heteroaryl, or heterocyclyl;

wherein each cycloalkyl, aryl, heteroaryl, or heterocyclyl is optionally substituted with 1 to 4 groups independently selected from halo, —O$R^a$, —$NO_2$, —CN, —N$R^aR^b$, —$N_3$, —$SO_2R^a$, —$C_{1-6}$ alkyl, —$C_{1-6}$ haloalkyl, —$C_{2-6}$alkenyl, —$C_{2-6}$alkynyl, —O$C_{1-6}$alkyl, —O$C_{1-6}$haloalkyl, —$C_{3-8}$cycloalkyl, and —$C_{1-6}$ alkyl$C_{3-8}$ cycloalkyl; and wherein each alkyl, alkenyl, alkynyl, and cycloalkyl is optionally substituted with 1 to 4 groups independently selected from oxo, —$NO_2$, —$N_3$, —O$R^a$, halo, and cyano;

$L^E$ and $L^W$ are each independently a bond, —O—, —S—, —SO—, —$SO_2$—, —$(CR^3R^4)_m$—, —$(CR^3R^4)_m$O$(CR^3R^4)_m$—, —$(CR^3R^4)_m$S$(CR^3R^4)_m$—, —$(CR^3R^4)_m$N$R^3$$(CR^3R^4)_m$—, —C(O)—, —$(CR^3R^4)_m$C(O)$(CR^3R^4)_m$—, —$(CR^3R^4)_m$C(O)N$R^3$$(CR^3R^4)_m$—, —$(CR^3R^4)_m$N$R^3$C(O)$(CR^3R^4)_m$—, $C_{2-6}$ alkenylene, $C_{2-6}$ alkynylene,

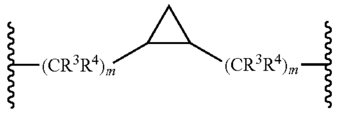

or

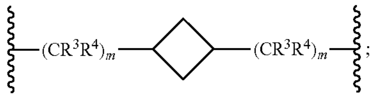

wherein each m is independently 0, 1, 2, 3 or 4;

$Q^E$ and $Q^W$ are each independently aryl, heteroaryl, or heterocyclyl;

wherein each aryl, heteroaryl, or heterocyclyl is optionally substituted with 1 to 4 groups independently selected from halo, oxo, —O$R^a$, —$N_3$, —$NO_2$, —CN, —N$R^1R^2$, —$SO_2R^a$, —$SO_2NR^aR^b$, —N$R^aSO_2R^a$, —N$R^a$C(O)$R^a$, —C(O)$R^a$, —C(O)O$R^a$, —C(O)N$R^aR^b$, —N$R^a$C(O)O$R^a$, —N$R^a$C(O)N$R^1R^2$, —OC(O)N$R^aR^b$, —N$R^aSO_2NR^aR^b$, —C(O)N$R^aSO_2NR^aR^b$, —$C_{1-6}$ alkyl, —$C_{2-6}$ alkenyl, —$C_{2-6}$ alkynyl, —O$C_{1-6}$ alkyl, —$C_{3-8}$ cycloalkyl, —$C_{1-6}$ alkyl$C_{3-8}$ cycloalkyl, aryl, heteroaryl, heterocyclyl, and $R^N$; and wherein the alkyl, alkenyl, alkynyl, $C_{3-8}$ cycloalkyl, aryl, heteroaryl, or heterocyclyl group is optionally substituted with 1 to 4 groups independently selected from oxo, —$NO_2$, —$N_3$, —O$R^a$, halo, cyano, —N$R^aR^b$, —C(O)$R^a$, —C(O)O$R^a$, —O$C_6$cyanoalkyl, —C(O)N$R^aR^b$, N$R^a$C(O)$R^a$, —N$R^a$C(O)O$R^a$, —$SO_2R^a$, —N$R^aSO_2R^b$, —$SO_2NR^aR^b$, —N$R^aSO_2NR^aR^b$, —C(O)N$R^aSO_2NR^aR^b$ and —$C_{3-8}$ cycloalkyl; and further wherein the heteroaryl or heterocyclic group may be oxidized on a nitrogen atom to form an N-oxide or oxidized on a sulfur atom to form a sulfoxide or sulfone;

$R^N$ is independently —$C_{1-6}$ alkylN$R^1R^2$, —O$C_{1-6}$ alkyN$R^1R^2$, —$C_{1-6}$ alkylO$C_{1-6}$ alkylN$R^1R^2$, —N$R^a$$C_{1-6}$ alkylN$R^1R^2$, —$C_{1-6}$ alkylC(O)N$R^1R^2$, —O$C_{1-6}$ alkylC(O)N$R^1R^2$, —O$C_{1-6}$ alkylC(O)O$R^1$, —S$C_{1-6}$alkylN$R^1R^2$, —$C_{1-6}$alkylO$R^a$, or

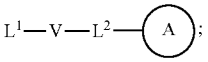

wherein: $L^1$ is independently a bond, O, N$R^a$, S, SO, or $SO_2$;

V is independently selected from a bond, $C_{1-6}$alkyl, $C_{2-6}$alkenyl, and $C_{2-6}$alkynyl;

wherein each alkyl, alkenyl, or alkynyl is optionally independently substituted with O$R^a$, halo, cyano, —N$R^aR^b$ or —$C_{3-8}$ cycloalkyl;

$L^2$ is independently a bond, O, N$R^a$, S, SO, or $SO_2$;

ring A is independently cycloalkyl, aryl, heteroaryl, or heterocyclyl;

wherein each cycloalkyl, aryl, heteroaryl, or heterocyclyl is optionally substituted with 1 to 4 groups independently selected from oxo, —$NO_2$, —$N_3$, —O$R^a$, halo, cyano, —$C_{1-6}$ alkyl, —$C_{1-6}$ haloalkyl, —$C_{2-6}$alkenyl, —$C_{2-6}$ alkynyl, —O$C_{1-6}$ haloalkyl, N$R^aR^b$, —C(O)$R^a$, —C(O)O$R^a$, —O$C_{1-6}$ alkylCN, —C(O)N$R^aR^b$, —N$R^a$C(O)$R^a$, —N$R^a$C(O)O$R^a$, —N$R^a$C(O)O$R^a$, —C(O)N($R^a$)O$R^b$, —$SO_2R^a$, —$SO_2NR^aR^b$, —N$R^aSO_2R^b$, —N$R^aSO_2NR^aR^b$, —C(O)N$R^aSO_2NR^aR^b$, $C_{3-8}$cycloalkyl, and $C_{1-6}$alkyl$C_{3-8}$ cycloalkyl; and wherein the alkyl, alkenyl, or alkynyl group is optionally independently substituted with —O$R^a$, halo, cyano, —N$R^aR^b$ or —$C_{3-8}$cycloalkyl;

$R^E$ and $R^W$ are each independently —N$R^1R^2$, —$C_{1-6}$ alkyN$R^1R^2$, —O$C_{1-6}$ alkylN$R^1R^2$, —$C_{1-6}$ alkylO$C_{1-6}$alkylN$R^1R^2$, —N$R^a$$C_{1-6}$ alkylN$R^1R^2$, —$C_{1-6}$ alkyl$N^+R^1R^2R^3$, —S$C_{1-6}$ alkylN$R^1R^2$, —C(O)N$R^1R^2$, —$SO_2R^a$, —$(CH_2)_u SO_2NR^1R^2$, —$(CH_2)_u NR^aSO_2NR^aR^b$, —$SO_2NR^a$$C_{1-6}$alkyN$R^1R^2$, $—NR^aSO_2C_{1-6}$ alkyl$NR^1R^2$, $—(CH_2)_uC(O)NR^aSO_2NR^aR^b$, $—(CH_2)_uN^+R^1R^2O^-$, $—(CH_2)_uP^+R^bR^cR^d$, $—(CH_2)_uP^+R^cR^dO^-$, $—(CH_2)_uP^+O[NR^aR^b][NR^cR^d]$, $—(CH_2)_uNR^cP(O)(OR^c)_2$, $—(CH_2)_uCH_2OP(O)(OR^c)(OR^d)$, $—(CH_2)_uOP(O)(OR^c)(OR^d)$, $—(CH_2)_uOP(O)NR^aR^b)(OR^a)$, or

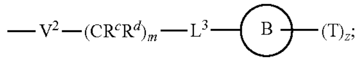

wherein:

$V^2$ is independently a bond, O, $NR^a$, S, SO, $SO_2$, C(O)$NR^a$, $NR^a$C(O), $SO_2NR^1R^2$, or $NR^aSO_2$;

$L^3$ is independently a bond, O, $NR^a$, S, SO, $SO_2$, C(O)$NR^a$, $NR^a$C(O), $SO_2NR^1R^2$, or $NR^aSO_2$;

ring B is independently cycloalkyl, aryl, heteroaryl, or heterocyclyl;

T is independently H, $OR^a$, $(CH_2)NR^1R^2$, $(CH_2)_qNR^aC(O)R^e$, or $(CH_2)_qC(O)R^e$;

p is independently 0, 1, 2, 3, 4, or 5;

q is independently 0, 1, 2, 3, 4, or 5;

u is 0, 1, 2, 3, or 4;

z is 0, 1, 2, or 3; and wherein the alkyl, cycloalkyl, aryl, heteroaryl, or heterocyclyl of $R^E$ or $R^W$ is optionally substituted with 1 to 3 substituents independently selected from the group consisting of $NR^aR^b$, halo, cyano, oxo, $OR^a$, $—C_{1-6}$alkyl, $—C_{1-6}$haloalkyl, $—C_{1-6}$cyanoalkyl, $—C_{1-6}$alkyl$NR^aR^b$, $—C_{1-6}$ alkylOH, $—C_{3-8}$ cycloalkyl, and $—C_{1-3}$ alkyl$C_{3-8}$cycloalkyl;

provided that at least one of $V^2$, $L^3$, ring B and T contains a nitrogen atom;

$R^1$ is independently selected from H, $—C_{1-8}$ alkyl, $—C_{2-6}$ alkenyl, $—C_{2-6}$ alkynyl, $—C_{3-6}$ cycloalkyl, aryl, heteroaryl, heterocyclyl, $—C_{1-6}$alkylaryl, $—C_{1-6}$alkylheteroaryl, $—C_{1-6}$alkylheterocyclyl, $—C_{1-6}$ alkylC(O)$OR^a$, $—C_{2-6}$ alkenylC(O)$OR^a$, $—SO_2R^a$, $—SO_2N^aR^b$, $—C(O)NR^aSO_2R^a$, and $C_{1-6}$ alkyl$C_{3-8}$cycloalkyl;

wherein each alkyl, alkenyl, cycloalkyl, aryl, heteroaryl, or heterocyclyl is optionally substituted with 1 to 4 groups independently selected from $—OR^a$, —CN, halo, $C_{1-6}$alkyl, $—C_{1-6}$alkyl$OR^a$, $—C_{1-6}$cyanoalkyl, $—C_{1-6}$haloalkyl, $C_{3-8}$cycloalkyl, $—C_{1-3}$alkyl$C_{3-8}$cycloalkyl, $—C(O)R^a$, $—C_{1-6}$ alkylC(O)$R^a$, $—C(O)OR^a$, $—C_{1-6}$ alkylC(O)$OR^a$, $—NR^aR^b$, $—OC(O)NR^aR^b$, $NR^aC(O)OR^b$, $—C_{1-6}$alkyl$NR^aR^b$, $—C(O)NR^aR^b$, $—C_{1-6}$alkylC(O)$NR^aR^b$, $—SO_2R^a$, $—C_{1-6}$alkyl$SO_2R^a$, $—SO_2NR^aR^b$, $—C_{1-6}$ alkyl$SO_2NR^aR^b$, $—C(O)NR^aSO_2R^b$, $—C_{1-6}$ alkylC(O)$NR^aSO_2R^b$, $—NR^aC(O)R^b$, and $—C_{1-6}$alkyl$NR^aC(O)R^b$;

$R^2$ is independently selected from H, $—C_{1-6}$ alkyl, $—C_{2-6}$ alkenyl, $—C_{2-6}$ alkynyl, $—C_{3-6}$ cycloalkyl, aryl, heteroaryl, heterocyclyl, $—C_{1-6}$alkylaryl, $—C_{1-6}$alkylheteroaryl, $—C_{1-6}$ alkylheterocyclyl, $—C_{2-6}$alkyl-$OR^a$, $—C_{1-6}$ alkylC(O)$OR^a$, and $—C_{2-6}$ alkenylC(O)$OR^a$;

wherein each alkyl, alkenyl, alkynyl, cycloalkyl, aryl, heteroaryl, or heterocyclyl is optionally substituted with 1 to 4 groups independently selected from $—OR^a$, —CN, halo, $C_{1-6}$alkyl, $—C_{1-6}$alkyl$OR^a$, $—C_{1-6}$cyanoalkyl, $—C_{1-6}$haloalkyl, $—C_{3-8}$cycloalkyl, $—C_{1-3}$alkyl$C_{3-8}$cycloalkyl, $—C(O)R^a$, $—C_{1-6}$ alkylC(O)$R^a$, $—C(O)OR^a$, $—C_{1-6}$ alkylC(O)$OR^a$, $—NR^aR^b$, $—C_{1-6}$ alkyl$NR^aR^b$, $—C(O)NR^aR^b$, $C_{1-6}$alkylC(O)$NR^aR^b$, $—SO_2R^a$, $—C_{1-6}$alkyl$SO_2R^a$, $—SO_2NR^aR^b$, $—C_{1-6}$alkyl$SO_2NR^aR^b$, $—C(O)NR^aSO_2R^b$ and $—NR^aC(O)R^b$;

or $R^1$ and $R^2$ combine to form a heterocyclyl group optionally containing 1, 2, or 3 additional heteroatoms independently selected from oxygen, sulfur and nitrogen, and optionally substituted with 1 to 3 groups independently selected from oxo, $—C_{1-6}$alkyl, $—C_{3-8}$cycloalkyl, $—C_{2-6}$ alkenyl, $—C_{2-6}$ alkynyl, $—OR^a$, $—C(O)OR^a$, $—C_{1-6}$ cyanoalkyl, $—C_{1-6}$ alkyl$OR^a$, $—C_{1-6}$haloalkyl, $—C_{1-3}$ alkyl $C_{3-8}$cycloalkyl, $—C(O)R^a$, $C_{1-6}$alkylC(O)$R^a$, $—C_{1-6}$alkylC(O)$OR^a$, $—NR^aR^b$, $—C_{1-6}$alky$NR^aR^b$, $—C(O)NR^aR^b$, $—C_{1-6}$alkylC(O)$NR^aR^b$, $—SO_2R^a$, $—C_{1-6}$ alkyl$SO_2R^a$, $—SO_2NR^aR^b$, and $C_{1-6}$ alkyl$SO_2NR^aR^b$;

$R^3$ is independently H, $—C_{1-6}$alkyl, $—C_{2-6}$ alkenyl, $—C_{3-6}$ cycloalkyl, aryl, heteroaryl, heterocyclyl, $—C_{1-6}$alkylaryl, $—C_{1-6}$alkylheteroaryl, $—C_{1-6}$ alkylheterocyclyl, $—C_{2-6}$alkyl-$OR^a$, $—C_{1-6}$alkylC(O)$OR^a$, or $—C_{2-6}$ alkenylC(O)$OR^a$;

$R^4$ is independently H, $—C_{1-6}$alkyl, $—C_{2-6}$ alkenyl, $—C_{3-6}$ cycloalkyl, aryl, heteroaryl, heterocyclyl, $—C_{1-6}$alkylaryl, $—C_{1-6}$alkylheteroaryl, $—C_{1-6}$ alkylheterocyclyl, $—C_{2-6}$alkyl-$OR^a$, $—C_{1-6}$alkylC(O)$OR^a$, or $—C_{2-6}$ alkenylC(O)$OR^a$;

$R^a$ is independently selected from H, $—C_{1-6}$alkyl, $—C_{3-8}$ cycloalkyl, aryl, heteroaryl, heterocyclyl, $—C_{1-3}$ alkyl $C_{3-8}$cycloalkyl, $—C_{1-6}$ alkylaryl, $—C_{1-6}$ alkylheteroaryl, and $—C_{1-6}$alkylheterocyclyl;

$R^b$ is independently selected from H, $—C_{1-6}$alkyl, $—C_{3-8}$ cycloalkyl, aryl, heteroaryl, heterocyclyl, $—C_{1-3}$ alkyl $C_{3-8}$cycloalkyl, $—C_{1-6}$ alkylaryl, $—C_{1-6}$ alkylheteroaryl, and $—C_{1-6}$ alkylheterocyclyl;

or $R^a$ and $R^b$ may combine together to form a ring consisting of 3-8 ring atoms that are C, N, O, or S; wherein the ring is optionally substituted with 1 to 4 groups independently selected from $—OR^f$, —CN, halo, $—C_{1-6}$ alkyl$OR^f$, $—C_{1-6}$ cyanoalkyl, $—C_{1-6}$haloalkyl, $—C_{3-8}$ cycloalkyl, $—C_{1-3}$ alkyl$C_{3-8}$cycloalkyl, $—C(O)R^f$, $—C_{1-6}$ alkylC(O)$R^f$, $—C(O)OR^f$, $—C_{1-6}$ alkylC(O)$OR^f$, $—NR^fR^g$, $—C_{1-6}$ alkyl$NR^fR^g$, $—C(O)NR^fR^g$, $—C_{1-6}$ alkylC(O)$NR^fR^g$, $—SO_2R^f$, $—C_{1-6}$ alkyl$SO_2R^f$, $—SO_2NR^fR^g$, $—C_{1-6}$ alkyl$SO_2NR^fR^g$, $—C(O)NR^fSO_2R^g$ and $—NR^fC(O)R^g$;

$R^c$ is independently selected from H, OH, $—C_{1-6}$alkyl, $—C_{3-8}$ cycloalkyl, aryl, heteroaryl, heterocyclyl, $—C_{1-3}$ alkyl$C_{3-8}$cycloalkyl, $—C_{1-6}$ alkylaryl, $—C_{1-6}$ alkylheteroaryl, and $—C_{1-6}$alkylheterocyclyl;

$R^d$ is independently selected from H, $—C_{1-6}$alkyl, $—C_3$-$C_8$cycloalkyl, aryl, heteroaryl, heterocyclyl, $—C_{1-3}$ alkyl $C_{3-8}$cycloalkyl, $—C_{1-6}$ alkylaryl, $—C_{1-6}$ alkylheteroaryl, and $—C_{1-6}$alkylheterocyclyl;

$R^e$ is independently selected from H, $—C_{1-6}$alkyl, $—OC_{1-6}$alkyl, $—C_{3-8}$ cycloalkyl, aryl, heteroaryl, heterocyclyl, $—OC_{3-8}$cycloalkyl, —Oaryl, —Oheteroaryl, —Oheterocyclyl, $—C_{1-3}$ alkyl$C_{3-8}$cycloalkyl, $—C_{1-6}$alkylaryl, $—C_{1-6}$alkylheteroaryl, $—NR^fR^g$, $—C_{1-6}$alkyl$NR^fR^g$, $—C(O)NR^fR^g$, $—C_{1-6}$alkylC(O)$NR^fR^g$, $—NHSO_2R^f$, $—C_{1-6}$alkyl$SO_2R^f$, and $—C_{1-6}$alkyl$SO_2NR^fR^g$;

$R^f$ is independently selected from H, $—C_{1-6}$alkyl, $—C_{3-8}$ cycloalkyl, aryl, heteroaryl, heterocyclyl, $—C_{1-3}$ alkyl $C_{3-8}$cycloalkyl, $—C_{1-6}$ alkylaryl, $—C_{1-6}$ alkylheteroaryl, and $—C_{1-6}$alkylheterocyclyl; and $R^g$ is independently selected from H, $—C_{1-6}$ alkyl, $—C_{3-8}$ cycloalkyl, aryl, heteroaryl, heterocyclyl, $—C_{1-3}$ alkyl $C_{3-8}$cycloalkyl, $—C_{1-6}$ alkylaryl, $—C_{1-6}$ alkylheteroaryl, and $—C_{1-6}$alkylheterocyclyl;

or a pharmaceutically acceptable salt, stereoisomer, mixture of stereoisomers, solvate, or tautomer thereof.

In one embodiment, provided is a compound of formula (I):

$$R^W\text{-}Q^W\text{-}L^W\text{-}Ar^W\text{—}Ar^E\text{-}L^E\text{-}Q^E\text{-}R^E \quad (I)$$

wherein:

$Ar^E$ and $Ar^W$ are each independently a cycloalkyl, aryl, heteroaryl, or heterocyclyl;

wherein each cycloalkyl, aryl, heteroaryl, or heterocyclyl is optionally substituted with 1 to 2 groups independently selected from halo, —$OR^a$, —$NO_2$, —CN, —$NR^aR^b$, —$N_3$, —$SO_2R^a$, —$C_{1-6}$ alkyl, —$C_{1-6}$haloalkyl, $OC_{1-6}$ alkyl, —$OC_{1-6}$haloalkyl, and —$C_{3-8}$ cycloalkyl;

wherein each alkyl, and cycloalkyl group is optionally substituted with 1 to 4 groups independently selected from $NO_2$, —$N_3$, —$OR^a$, halo, and cyano.

In one embodiment, $Ar^E$ and $Ar^W$ are each independently an aryl, heteroaryl, or heterocyclyl;

wherein each cycloalkyl, aryl, heteroaryl, or heterocyclyl is optionally substituted with 1 to 2 groups independently selected from halo, —$OR^a$, CN, —$C_{1-6}$ alkyl, —$C_{1-6}$haloalkyl, and —$OC_{1-6}$ alkyl; and wherein each alkyl group is optionally substituted with 1 to 4 groups independently selected from $OR^a$, halo, or cyano.

In one embodiment, $Ar^W$ and $Ar^E$ are each independently selected from phenyl, pyridinyl, indanyl, and indolinyl;

wherein each phenyl, pyridinyl, indanyl, and indolinyl is optionally substituted with 1 to 2 groups independently selected from halo, cyano, —$OR^a$, —$C_{1-6}$alkyl, —$C_{1-6}$alkyl-$OR^a$, —$C_{1-6}$haloalkyl, —$OC_{1-6}$haloalkyl, and —$C_{1-6}$cyanoalkyl.

In one embodiment, $Ar^W$ is the same as $Ar^E$ and is selected from phenyl, pyridinyl, indanyl, and indolinyl;

wherein each phenyl, pyridinyl, indanyl, and indolinyl is optionally substituted with 1 to 3 groups independently selected from halo, cyano, —$OR^a$, —$C_{1-6}$ alkyl, —$C_{1-6}$alkyl-$OR^a$, —$C_{1-6}$haloalkyl, and —$C_{1-6}$cyanoalkyl.

In one embodiment, the group $Ar^W$ is selected from phenyl, pyridinyl, indanyl, naphthyl, indazolyl, indolinyl, quinolinyl, quinazolinyl, benzimidazolinyl, benzthiazolyl, thiazolyl, and thienyl. In another embodiment, the group $Ar^W$ is selected from phenyl, pyridinyl, indanyl, indolinyl, quinolinyl, and benzimidazolinyl.

In one embodiment, the group $Ar^E$ is selected from phenyl, pyridinyl, indanyl, naphthyl, indazolyl, indolinyl, quinolinyl, quinazolinyl, benzimidazolinyl, benzthiazolyl, thiazolyl, and thienyl. In another embodiment, the group $Ar^E$ is selected from phenyl, pyridinyl, indanyl, indolinyl, quinolinyl, and benzimidazolinyl.

In one embodiment, the groups $Ar^W$ and $Ar^E$ are the same. In one embodiment, the groups $Ar^W$ and $Ar^E$ are the same and have the same substituents. In one embodiment, the groups $Ar^W$ and $Ar^E$ both phenyl each optionally substituted with methyl. In one embodiment, the groups $Ar^W$ and $Ar^E$ both phenyl each optionally substituted with chloro. In one embodiment, the groups $Ar^W$ and $Ar^E$ both indanyl each optionally substituted with methyl. In one embodiment, the groups $Ar^W$ and $Ar^E$ both indolinyl each optionally substituted with methyl. In one embodiment, the groups $Ar^W$ and $Ar^E$ both benzimidazole each optionally substituted with methyl. In one embodiment, the groups $Ar^W$ and $Ar^E$ are both indolyl. In one embodiment, the groups $Ar^W$ and $Ar^E$ are both indolyl each optionally substituted with methyl. In another embodiment of the disclosure, the groups $Ar^W$ and $Ar^E$ different and are independently selected from phenyl, indanyl, thienyl, benzimidazolyl, indolyl, and indolinyl.

In one embodiment, the optional substituents on $Ar^W$ and $Ar^E$ are independently selected from halo, cyano, $C_{1-6}$alkyl, $C_{1-3}$haloalkyl, $C_{2-5}$alkynyl, and —O—$C_{1-6}$alkyl.

In one embodiment, $Ar^E$ is the same as $Ar^W$ and each is optionally substituted with 1 to 2 groups independently selected from methyl, chloro, bromo, CN, —$OCF_3$, $CF_3$, $CH_2CF_3$, and ethyl.

In one embodiment, $Ar^E$ is different from Mw and each is optionally substituted with 1 to 2 groups independently selected from methyl, chloro, bromo, CN, —$OCF_3$, $CF_3$, $CH_2CF_3$, and ethyl.

In one embodiment, $Ar^W$ is indolinyl and $Ar^E$ is indolinyl each optionally substituted with 1 to 2 groups independently selected from methyl, ethyl, methoxy, chloro, and $CF_3$.

In one embodiment, $Ar^W$ is phenyl and $Ar^E$ is phenyl each optionally substituted with 1 to 2 groups independently selected from methyl, ethyl, methoxy, chloro, and $CF_3$.

In another embodiment of the disclosure, the optional substituents on $Ar^W$ and $Ar^E$ independently selected from CN, Cl, F, —$OCF_3$, —O—$CH_3$, $CH_3$, and —$C_2H_5$.

In another embodiment of the disclosure, the optional substituents on $Ar^W$ and $Ar^E$ independently selected from CN, Cl, F, —$OCF_3$, —$OCH_3$, —$CH_3$, and —$C_2H_5$.

In another embodiment of the disclosure, the optional substituents on $Ar^W$ and $Ar^E$ is $CH_3$.

In one embodiment, the present disclosure provides a compound of formula (I) wherein the group —$Ar^W$—$Ar^E$— is selected from:

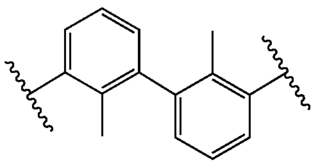
,

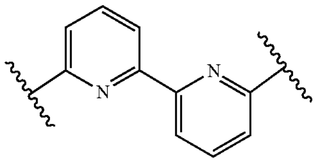
,

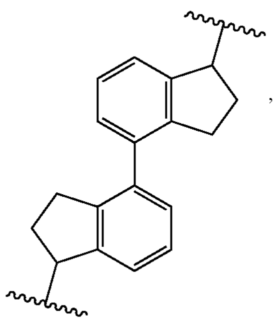
,

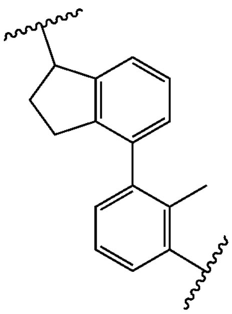
,

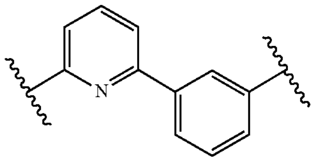
,

-continued

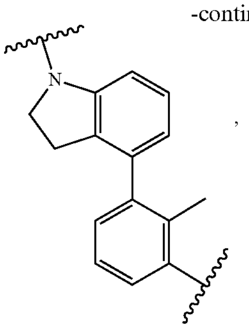
,

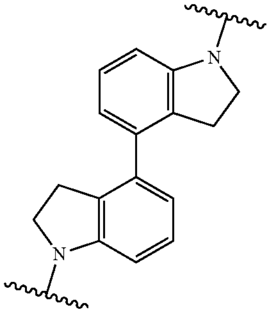
,

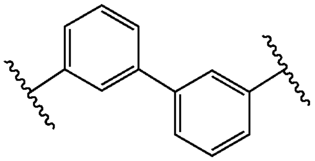
, and

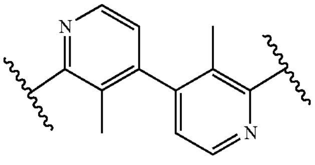
.

wherein each ring is optionally substituted with 1 or 2 groups independently selected from halo, cyano, $C_{1-6}$alkyl, $C_{1-3}$haloalkyl, —O$C_{1-6}$alkyl, and —O$C_{1-3}$haloalkyl.

In one embodiment, $L^E$ and $L^W$ are each independently a bond, —O—, —$(CR^3R^4)_m$—, —$(CR^3R^4)_m$O$(CR^3R^4)_m$—, —$(CR^3R^4)_m$NR$^3(CR^3R^4)_m$—, —C(O)—, $C_{2-6}$ alkenylene, $C_{2-6}$ alkynylene,

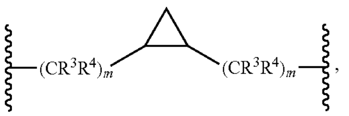
or

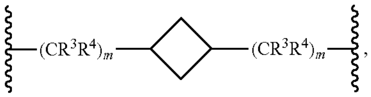
, wherein each m is independently 0, 1, 2, 3 or 4.

In one embodiment, $L^E$ and $L^W$ are each independently a bond, —$(CR^3R^4)_m$—, —$(CR^3R^4)_m$O$(CR^3R^4)_m$—, —C(O)—,

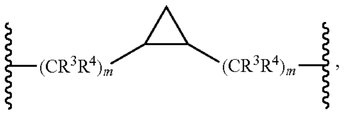
or

-continued

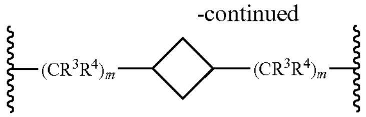
, wherein each m is independently 0, 1, 2, or 3;

$R^3$ is independently H, —$C_{1-6}$alkyl, —OH, —$OCH_3$, or —$OCH_2CH_3$; and $R^4$ is independently H, halo, —$C_{1-6}$alkyl, —OH, —$OCH_3$, or —$OCH_2CH_3$.

In one embodiment, $L^E$ and $L^W$ are each independently a bond, —$(CR^3R^4)_m$—, —$(CR^3R^4)_m$O$(CR^3R^4)_m$—, —C(O)—,

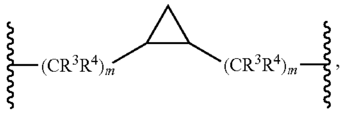
or

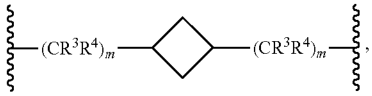
, wherein each m is independently 0, 1 or 2;

$R^3$ is independently H, —$C_{1-6}$alkyl, —OH, —$OCH_3$, or —$OCH_2CH_3$; and $R^4$ is independently H, halo, —$C_{1-6}$alkyl, —OH, —$OCH_3$, or —$OCH_2CH_3$.

In one embodiment, $L^E$ and $L^W$ are each independently O—, —S—, —SO—, —$SO_2$—, —$(CR^3R^4)_m$NR$^3(CR^3R^4)_m$—, —C(O)—, —$(CR^3R^4)_m$C(O)NR$^3(CR^3R^4)_m$—, or —$(CR^3R^4)_m$NR$^3$C(O)$(CR^3R^4)_m$—, wherein each m is independently 0, 1, or 2; and $R^3$ and $R^4$ are each independently H, or —$C_{1-6}$alkyl.

In one embodiment, $L^E$ and $L^W$ are each independently a bond, —$(CR^3R^4)_m$—, —O$(CR^3R^4)_m$, —$(CR^3R^4)_m$O, or —C(O)—, wherein m is independently 0, 1, 2, or 3; and $R^3$ and $R^4$ are each independently H, —$C_{1-6}$alkyl, —OH, —$OCH_3$, or —$OCH_2CH_3$.

In one embodiment, $L^E$ and $L^W$ are each independently a bond, —$(CR^3R^4)_m$—, —O$(CR^3R^4)_m$, —$(CR^3R^4)_m$O, or —C(O)—;

wherein m is independently 0, 1 or 2; and $R^3$ and $R^4$ are each independently H, or —$C_{1-6}$alkyl.

In one embodiment, $L^E$ and $L^W$ are each independently a bond, —$CH_2$—, —$OCH_2$, —$CH_2O$— or —C(O)—.

In one embodiment, $L^W$ is —O$(CR^3R^4)_m$— or —$(CR^3R^4)_m$O—.

In another embodiment, $L^W$ is —$(CR^3R^4)_m$—. In another embodiment, $L^W$ is —NR$^3(CHR^4)_n$ or —$(CHR^4)_n$ NR$^3$—. In another embodiment, $L^W$ is —NR$^3(CHR^4)_m$. In another embodiment, the group $L^W$ is —C(O)—. In yet another embodiment, $L^W$ is a bond.

In one embodiment, $L^E$ is —$(CR^3R^4)_m$O— or —$(CR^3R^4)_m$O—.

In another embodiment, $L^E$ is —$(CR^3R^4)_m$—. In another embodiment, $L^E$ is —NR$^3(CHR^4)_n$ or —$(CHR^4)_n$ NR$^3$—. In another embodiment, $L^E$ is —$NR^3(CHR^4)_m$. In another embodiment, the group $L^E$ is —C(O)—. In yet another embodiment, $L^E$ is a bond.

In one embodiment, one of $L^W$ and $L^E$ is a bond and the other is —$OCH_2$— or —$CH_2O$—.

In one embodiment, $Q^E$ and $Q^W$ are each independently an aryl, heteroaryl, or heterocyclyl;

wherein each aryl, heteroaryl, or heterocyclyl is optionally substituted with 1 to 2 groups independently selected from halo, oxo, —$OR^a$, —$N_3$, —$NO_2$, —CN, —$NR^1R^2$, —$SO_2R^a$, —$SO_2NR^aR^b$, —$NR^aSO_2R^a$, —$NR^aC(O)R^a$, —$C(O)R^a$, —$C(O)OR^a$, —$C(O)NR^aR^b$, —$NR^aSO_2NR^aR^b$, —$C(O)NR^aSO_2NR^aR^b$, —$C_{1-6}$ alkyl, —$C_{2-6}$ alkenyl, —$C_{2-6}$ alkynyl, —$OC_{1-6}$ alkyl, —$C_{3-8}$cycloalkyl, —$C_{1-6}$ alkyl$C_{3-8}$ cycloalkyl, aryl, heteroaryl, heterocyclyl, and $R^N$;

wherein the alkyl, alkenyl, alkynyl, $C_{3-8}$ cycloalkyl, aryl, heteroaryl, or heterocyclyl group is optionally substituted with 1 to 4 groups independently selected from oxo, —$NO_2$, —$N_3$, —$OR^a$, halo, cyano, —$NR^aR^b$, —$C(O)R^a$, —$C(O)OR^a$, —$C(O)NR^aR^b$, $NR^aC(O)R^a$, —$NR^aC(O)OR^a$, —$SO_2R^a$, —$NR^aSO_2R^b$, —$SO_2NR^aR^b$, —$NR^aSO_2NR^aR^b$, —$C(O)NR^aSO_2NR^aR^b$ and —$C_{3-8}$ cycloalkyl;

wherein the heteroaryl or heterocyclic group may be oxidized on a nitrogen atom to form an N-oxide, or may be $C_{1-6}$ alkylated to form a N—$C_{1-6}$ alkylated ion, or oxidized on a sulfur atom to form a sulfoxide or sulfone;

wherein $R^N$ is independently —$C_{1-6}$ alkyl$NR^1R^2$, —$OC_{1-6}$ alky$NR^1R^2$, —$C_{1-6}$ alkyl$OC_{1-6}$ alkyl$NR^1R^2$, —$NR^aC_{1-6}$ alkyl$NR^1R^2$, —$C_{1-6}$ alkyl$C(O)NR^1R^2$, —$OC_{1-6}$ alkyl$C(O)NR^1R^2$, —$OC_{1-6}$ alkyl$C(O)OR^1$, —$SC_{1-6}$alkyl$NR^1R^2$, —$C_{1-6}$alkyl$OR^a$, or

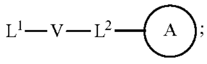;

wherein $L^1$ is independently a bond, O, $NR^a$ or;

wherein $L^2$ is independently a bond, O, $NR^a$ or;

V is independently selected from a bond, $C_{1-6}$alkyl, and $C_{2-6}$alkenyl; and ring A is independently cycloalkyl, aryl, heteroaryl, or heterocyclyl;

wherein the cycloalkyl, aryl, heteroaryl, or heterocyclyl is optionally independently substituted with 1 to 3 groups independently selected from oxo, —$NO_2$, —$N_3$, —$OR^a$, halo, cyano, —$NR^aR^b$, —$C(O)R^a$, —$C(O)OR^a$, —$OC_{1-6}$alkyCN, —$C(O)NR^aR^b$, —$NR^aC(O)R^a$, —$NR^aC(O)OR^a$, —$NR^aC(O)OR^a$, —$C(O)N(R^a)OR^b$, —$SO_2R^a$, —$SO_2NR^aR^b$, —$NR^aSO_2R^b$, —$NR^aSO_2NR^aR^b$, —$C(O)NR^aSO_2NR^aR^b$ and $C_{3-8}$ cycloalkyl.

In one embodiment, $Q^E$ and $Q^W$ are each independently an aryl, heteroaryl, or heterocyclyl optionally substituted with $R^N$;

wherein $R^N$ is independently —$C_{1-6}$ alky$NR^1R^2$, —$OC_{1-6}$ alkyl$NR^1R^2$, —$C_{1-6}$ alkyl$OC_{1-6}$ alkyl$NR^1R^2$, —$NR^aC_{1-6}$alkyl$NR^1R^2$, —$C_{1-6}$alkyl$OR^a$, or

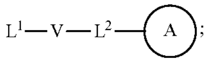;

wherein $L^1$ is independently a bond, O, $NR^a$ or;

$L^2$ is independently a bond, O, $NR^a$ or S

V is independently selected from a bond, $C_{1-6}$alkyl, and $C_{2-6}$alkenyl;

ring A is independently cycloalkyl, aryl, heteroaryl, or heterocyclyl;

wherein the cycloalkyl, aryl, heteroaryl, or heterocyclyl is optionally independently substituted with 1 to 3 groups independently selected from oxo, —$NO_2$, —$N_3$, —$OR^a$, halo, cyano, —$NR^aR^b$, —$C(O)R^a$, —$C(O)OR^a$, —$OC_{1-6}$alkylCN, —$C(O)NR^aR^b$, —$NR^aC(O)R^a$, —$NR^aC(O)OR^a$, —$NR^aC(O)OR^a$, —$C(O)N(R^a)OR^b$, —$SO_2R^a$, —$SO_2N^aR^b$, —$NR^aSO_2R^b$, —$NR^aSO_2NR^aR^b$, —$C(O)NR^aSO_2NR^aR^b$ and $C_{3-8}$ cycloalkyl.

In one embodiment, $Q^E$ and $Q^W$ are each independently an aryl, or heteroaryl group optionally substituted with $R^N$; wherein $R^N$ is independently —$C_{1-6}$ alky$NR^1R^2$, —$OC_{1-6}$ alky$NR^1R^2$, —$C_{1-6}$ alkyl$OC_{1-6}$ alkyl$NR^1R^2$, —$NR^a$ $C_{1-6}$alkyl$NR^1R^2$, —$C_{1-6}$alkyl$OR^a$, or

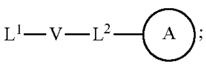;

wherein $L^1$ is independently a bond, O, $NR^a$ or S $L^2$ is independently a bond, O, $NR^a$ or S V is independently selected from a bond, $C_{1-6}$alkyl, and $C_{2-6}$alkenyl; and ring A is independently cycloalkyl, aryl, heteroaryl, or heterocyclyl;

wherein the cycloalkyl, aryl, heteroaryl, or heterocyclyl is optionally independently substituted with 1 to 3 groups independently selected from oxo, —$NO_2$, —$N_3$, —$OR^a$, halo, cyano, —$NR^aR^b$, —$C(O)R^a$, —$C(O)OR^a$, —$OC_{1-6}$alkylCN, —$C(O)NR^aR^b$, —$NR^aC(O)R^a$, —$NR^aC(O)OR^a$, —$NR^aC(O)OR^a$, —$C(O)N(R^a)OR^b$, —$SO_2R^a$, —$SO_2N^aR^b$, —$NR^aSO_2R^b$, —$NR^aSO_2NR^aR^b$, —$C(O)NR^aSO_2NR^aR^b$ and $C_{3-8}$ cycloalkyl.

In one embodiment, $Q^E$ and $Q^W$ are each independently phenyl, pyridine, indanyl, naphthyl, indolyl, indolinyl, benzthiazolyl, indazolyl, benzimidazolyl, imidazolyl, thiazolyl, or thienyl;

wherein each phenyl, pyridine, indanyl, naphthyl, indolyl, indolinyl, benzthiazolyl, indazolyl, benzimidazolyl, imidazolyl, thiazolyl, or thienyl is optionally substituted with 1 to 3 groups independently selected from halo, —$OR^a$, —$N_3$, —$NO_2$, —CN, —$NR^aR^b$, —$C_{1-6}$ alkyl, $C_{3-8}$ cycloalkyl, and —$C_{1-6}$alkyl$C_{3-8}$ cycloalkyl.

In one embodiment, $Q^E$ and $Q^W$ are each independently phenyl, pyridine, indanyl, naphthyl, indolyl, indolinyl, benzthiazolyl, indazolyl, benzimidazolyl, imidazolyl, thiazolyl, or thienyl;

wherein each phenyl, pyridine, indanyl, naphthyl, indolyl, indolinyl, benzthiazolyl, indazolyl, benzimidazolyl, imidazolyl, thiazolyl, or thienyl is optionally substituted with 1 to 3 groups independently selected from halo, —$OR^a$, —$N_3$, —$NO_2$, —CN, —$NR^aR^b$, —$C_{1-6}$ alkyl, $C_{3-8}$ cycloalkyl, —$C_{1-6}$alkyl$C_{3-8}$cycloalkyl, and $R^N$;

wherein $R^N$ is independently —$C_{1-6}$ alkyNR$^1$R$^2$, —OC$_{1-6}$ alkyNR$^1$R$^2$, —$C_{1-6}$ alkylOC$_{1-6}$ alkylNR$^1$R$^2$, —NR$^a$C$_{1-6}$ alkylNR$^1$R$^2$, —$C_{1-6}$ alkylC(O)NR$^1$R$^2$, —OC$_{1-6}$ alkylC(O)NR$^1$R$^2$, —OC$_{1-6}$ alkylC(O)OR$^1$, —SC$_{1-6}$ alkylNR$^1$R$^2$, —$C_{1-6}$ alkylOR$^a$, or

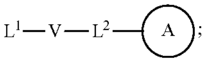;

$L^1$ is independently a bond, O, NR$^a$, S, SO, or $SO_2$;

$L^2$ is independently a bond, O, NR$^a$, S, SO, or $SO_2$;

V is independently selected from a bond, $C_{1-6}$alkyl, $C_{2-6}$alkenyl, and $C_{2-6}$alkynyl;

wherein each alkyl, alkenyl, or alkynyl is optionally independently substituted with OR$^a$, halo, cyano, —NR$^a$R$^b$ or —$C_{3-8}$ cycloalkyl; and ring A is independently cycloalkyl, aryl, heteroaryl, or heterocyclyl;

wherein the cycloalkyl, aryl, heteroaryl, or heterocyclyl is optionally substituted with 1 to 2 groups independently selected from oxo, —$NO_2$, —$N_3$, —OR$^a$, halo, —CN, NR$^a$R$^b$, —C(O)R$^a$, —C(O)OR$^a$, —OC$_{1-6}$ alkylCN, —C(O)NR$^a$R$^b$, —NR$^a$C(O)R$^a$, —NR$^a$C(O)OR$^a$, —NR$^a$C(O)OR$^a$, —C(O)N(R$^a$)OR$^b$, —SO$_2$R$^a$, —SO$_2$NR$^a$R$^b$, —NR$^a$SO$_2$R$^b$, —NR$^a$SO$_2$NR$^a$R$^b$, —C(O)NR$^a$SO$_2$NR$^a$R$^b$ and $C_{3-8}$ cycloalkyl.

In one embodiment, $Q^E$ and $Q^W$ are each independently phenyl, pyridine, indanyl, naphthyl, indolyl, indolinyl, benzthiazolyl, indazolyl, benzimidazolyl, or benzthiazolyl;

wherein each group is optionally substituted with 1 to 3 groups independently selected from halo, —OR$^a$, —$N_3$, —$NO_2$, —CN, —NR$^a$R$^b$, —$C_{1-6}$ alkyl, $C_{3-8}$ cycloalkyl, —$C_{1-6}$alkyl$C_{3-8}$ cycloalkyl, and $R^N$;

wherein $R^N$ is independently —$C_{1-6}$ alkyNR$^1$R$^2$, —OC$_{1-6}$ alkyNR$^1$R$^2$, —$C_{1-6}$ alkylOC$_{1-6}$ alkylNR$^1$R$^2$, —NR$^a$C$_{1-6}$ alkylNR$^1$R$^2$, —$C_{1-6}$ alkylC(O)NR$^1$R$^2$, —OC$_{1-6}$ alkylC(O)NR$^1$R$^2$, —OC$_{1-6}$ alkylC(O)OR$^1$, —SC$_{1-6}$ alkylNR$^1$R$^2$, —$C_{1-6}$ alkylOR$^a$, or

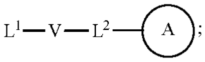;

wherein $L^1$ is independently a bond, O, NR$^a$, S, SO, or $SO_2$;

$L^2$ is independently a bond, O, NR$^a$, S, SO, or $SO_2$;

V is independently selected from a bond, $C_{1-6}$alkyl, $C_{2-6}$alkenyl, and $C_{2-6}$alkynyl;

wherein the alkyl, alkenyl, or alkynyl is optionally independently substituted with —OR$^a$, halo, cyano, —NR$^a$R$^b$ or —$C_{3-8}$ cycloalkyl;

ring A is independently cycloalkyl, aryl, heteroaryl, or heterocyclyl;

wherein the cycloalkyl, aryl, heteroaryl, or heterocyclyl is optionally substituted with 1 to 2 groups independently selected from oxo, —$NO_2$, —$N_3$, —OR$^a$, halo, CN, —NR$^a$R$^b$, —C(O)R$^a$, —C(O)OR$^a$, —OC$_{1-6}$ alkyCN, —C(O)NR$^a$R$^b$, —NR$^a$C(O)R$^a$, —NR$^a$C(O)OR$^a$, —NR$^a$C(O)OR$^a$, —C(O)N(R$^a$)OR$^b$, —SO$_2$R$^a$, —SO$_2$NR$^a$R$^b$, —NR$^a$SO$_2$R, —NR$^a$SO$_2$NR$^a$R$^b$, —C(O)NR$^a$SO$_2$NR$^a$R$^b$ and $C_{3-8}$ cycloalkyl.

In one embodiment, $Q^E$ and $Q^W$ are each independently phenyl, indanyl, naphthyl, indolyl, indolinyl, benzthiazolyl, indazolyl, benzimidazolyl, or benzthiazolyl;

wherein each phenyl, indanyl, naphthyl, indolyl, indolinyl, benzthiazolyl, indazolyl, benzimidazolyl, or benzthiazolyl is optionally substituted with 1 to 3 groups independently selected from halo, —OR$^a$, —$N_3$, —$NO_2$, —CN, —NR$^a$R$^b$, —$C_{1-6}$ alkyl, $C_{3-8}$ cycloalkyl, —$C_{1-6}$alkyl$C_{3-8}$cycloalkyl, and $R^N$;

wherein $R^N$ is independently —$C_{1-6}$ alkyNR$^1$R$^2$, —OC$_{1-6}$ alkyNR$^1$R$^2$, —$C_{1-6}$ alkylOC$_{1-6}$ alkylNR$^1$R$^2$, —NR$^a$C$_{1-6}$ alkylNR$^1$R$^2$, —$C_{1-6}$ alkylC(O)NR$^1$R$^2$, —OC$_{1-6}$ alkylC(O)NR$^1$R$^2$, —OC$_{1-6}$ alkylC(O)OR$^1$, —SC$_{1-6}$ alkylNR$^1$R$^2$, —$C_{1-6}$ alkylOR$^a$, or

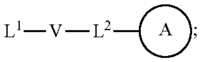;

wherein $L^1$ is independently a bond, O, NR$^a$, S, SO, or $SO_2$;

$L^2$ is independently a bond, O, NR$^a$, S, SO, or $SO_2$;

V is independently selected from a bond, $C_{1-6}$alkyl, $C_{2-6}$alkenyl, and $C_{2-6}$alkynyl;

wherein each alkyl, alkenyl, or alkynyl is optionally independently substituted with OR$^a$, halo, cyano, —NR$^a$R$^b$, or —$C_{3-8}$ cycloalkyl; and ring A is independently cycloalkyl, aryl, heteroaryl, or heterocyclyl;

wherein the cycloalkyl, aryl, heteroaryl, or heterocyclyl is optionally substituted with 1 to 2 groups independently selected from oxo, —$NO_2$, —$N_3$, —OR$^a$, halo, —CN, NR$^a$R$^b$, —C(O)R$^a$, —C(O)OR$^a$, —OC$_{1-6}$ alkylCN, —C(O)NR$^a$R$^b$, —NR$^a$C(O)R$^a$, —NR$^a$C(O)OR$^a$, —NR$^a$C(O)OR$^a$, —C(O)N(R$^a$)OR$^b$, —SO$_2$R$^a$, —SO$_2$NR$^a$R$^b$, —NR$^a$SO$_2$R$^b$, —NR$^a$SO$_2$NR$^a$R$^b$, —C(O)NR$^a$SO$_2$NR$^a$R$^b$, and $C_{3-8}$ cycloalkyl.

In one embodiment, $Q^E$ and $Q^W$ are each independently phenyl, pyridine, indazolyl, thiazolyl, or indolinyl;

wherein each phenyl, pyridine, indazolyl, thiazolyl, or indolinyl is optionally substituted with 1 to 3 groups independently selected from halo, —OR$^a$, —CN, —NR$^a$R$^b$, —SO$_2$R$^a$, —SO$_2$NR$^a$R$^b$, —NR$^a$SO$_2$R$^a$, —NR$^a$C(O)R$^a$, —C(O)NR$^a$R$^b$, —$C_{1-6}$ alkyl, —$C_{2-6}$ alkenyl, —$C_{2-6}$ alkynyl, —$C_{3-8}$ cycloalkyl, and $R^N$;

wherein $R^N$ is independently —$C_{1-6}$ alkylNR$^1$R$^2$, —OC$_{1-6}$ alkyNR$^1$R$^2$, —$C_{1-6}$ alkylOC$_{1-6}$ alkylNR$^1$R$^2$, —NR$^a$C$_{1-6}$alkylNR$^1$R$^2$, —$C_{1-6}$alkylOR$^a$, or

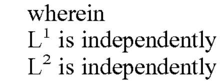;

wherein $L^1$ is independently a bond, O, NR$^a$, S, SO, or $SO_2$;

$L^2$ is independently a bond, O, NR$^a$, S, SO, or $SO_2$;

V is independently selected from a bond, $C_{1-6}$alkyl, $C_{2-6}$alkenyl, and $C_{2-6}$ alkynyl;

wherein each alkyl, alkenyl, or alkynyl is optionally independently substituted with OR$^a$, halo, cyano, —NR$^a$R$^b$, or —$C_{3-8}$ cycloalkyl;

ring A is independently cycloalkyl, aryl, heteroaryl, or heterocyclyl;

wherein the cycloalkyl, aryl, heteroaryl, or heterocyclyl is optionally independently substituted with 1 to 2 groups independently selected from oxo, —$NO_2$, —$N_3$, —$OR^a$, halo, —CN, $NR^aR^b$, —$C(O)R^a$, —$C(O)OR^a$, —$OC_{1-6}$ alkylCN, —$C(O)NR^aR^b$, —$NR^aC(O)R^a$, —$NR^aC(O)OR^a$, —$NR^aC(O)OR^a$, —$C(O)N(R^a)OR^b$, —$SO_2R^a$, —$SO_2NR^aR^b$, —$NR^aSO_2R^b$, —$NR^aSO_2NR^aR^b$, —$C(O)NR^aSO_2NR^aR^b$ and $C_{3-8}$ cycloalkyl.

In another embodiment, $Q^W$ is selected from phenyl, pyridinyl, indazolyl, and thienyl, wherein each phenyl, pyridinyl, indazolyl, and thienyl is optionally substituted with 1 to 2 groups independently selected from halo, —$OR^a$, —$N_3$, —$NO_2$, —CN, —$NR^aR^b$, —$SO_2R^a$, —$SO_2NR^aR^b$, —$NR^aSO_2R^a$, —$NR^aC(O)R^a$, —$C(O)NR^aR^b$, —$C_{1-6}$ alkyl, —$OC_{1-6}$alkyl, $C_{3-8}$ cycloalkyl, and —$C_{1-6}$alkyl$C_{3-8}$ cycloalkyl.

In another embodiment, $Q^W$ is selected from phenyl, pyridine and indanyl, wherein each phenyl, pyridine and indanyl is optionally substituted with 1 to 3 groups independently selected from halo, —$OR^a$, —$N_3$, —$NO_2$, —CN, —$NR^aR^b$, —$SO_2R^a$, —$SO_2NR^aR^b$, —$NR^aSO_2R^a$, —$NR^aC(O)R^a$, —$C(O)NR^aR^b$, —$C_{1-6}$ alkyl, —$OC_{1-6}$alkyl, $C_{3-8}$ cycloalkyl, and —$C_{1-6}$alkyl$C_{3-8}$ cycloalkyl.

In one embodiment, $Q^E$ is selected from phenyl, pyridinyl, indazolyl, and thienyl, wherein each phenyl, pyridinyl, indazolyl, and thienyl is optionally substituted with 1 to 2 groups independently selected from halo, —$OR^a$, —$N_3$, —$NO_2$, —CN, —$NR^aR^b$, —$SO_2R^a$, —$SO_2NR^aR^b$, —$NR^aSO_2R^a$, —$NR^aC(O)R^a$, —$C(O)NR^aR^b$, —$C_{1-6}$ alkyl, —$OC_{1-6}$ alkyl, $C_{3-8}$ cycloalkyl, and —$C_{1-6}$alkyl$C_{3-8}$ cycloalkyl.

In another embodiment, $Q^E$ is selected from phenyl, pyridine and indanyl, wherein each phenyl, pyridine and indanyl is optionally substituted with 1 to 3 groups independently selected from halo, —$OR^a$, —$N_3$, —$NO_2$, —CN, —$NR^aR^b$, —$SO_2R^a$, —$SO_2NR^aR^b$, —$NR^aSO_2R^a$, —$NR^aC(O)R^a$, —$C(O)NR^aR^b$, —$C_{1-6}$ alkyl, —$OC_{1-6}$ alkyl, $C_{3-8}$ cycloalkyl, and —$C_{1-6}$alkyl$C_{3-8}$ cycloalkyl.

In one embodiment, $Q^W$ and $Q^E$ are each independently

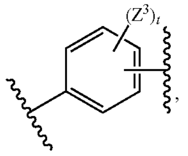,
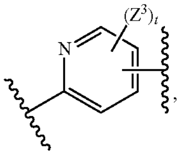,
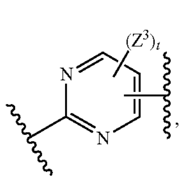,
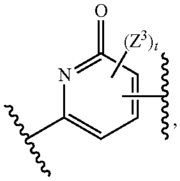,
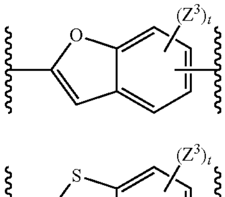,
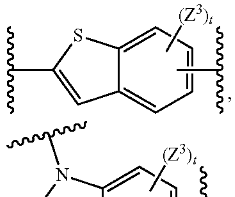,
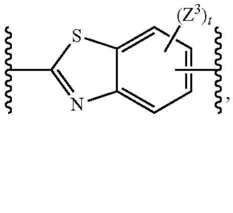,
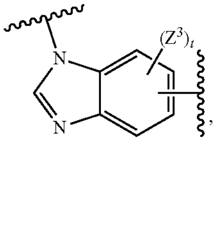, or -continued

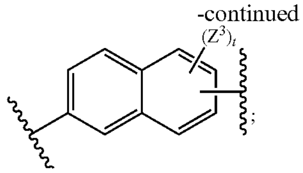;

wherein each $Z^3$ is independently halo, —$OR^a$, —$N_3$, —$NO_2$, —CN, —$NR^1R^2$, —$SO_2R^a$, —$SO_2N^aR^b$, —$NR^aSO_2R^a$, —$NR^aC(O)R^a$, —$C(O)R^a$, —$C(O)OR^a$, —$C(O)NR^aR^b$, —$NR^aC(O)OR^a$, —$NR^aC(O)NR^1R^2$, —$OC(O)NR^aR^b$, —$NR^aSO_2NR^aR^b$, —$C(O)NR^aSO_2NR^aR^b$, —$C_{1-6}$ alkyl, —$C_{2-6}$ alkenyl, —$C_{2-6}$ alkynyl, —$OC_{1-6}$ alkyl, —$C_{3-8}$ cycloalkyl, —$C_{1-6}$ alkyl$C_{3-8}$ cycloalkyl, aryl, heteroaryl, heterocyclyl, and $R^N$; and wherein the alkyl, alkenyl, alkynyl, $C_{3-8}$ cycloalkyl, aryl, heteroaryl, or heterocyclyl group is optionally substituted with 1 to 4 groups independently selected from oxo, —$NO_2$, —$N_3$, —$OR^a$, halo, cyano, —$NR^aR^b$, —$C(O)R^a$, —$C(O)OR^a$, —$OC_{1-6}$alkylCN, —$C(O)NR^aR^b$, $NR^aC(O)R^a$, —$NR^aC(O)OR^a$, —$SO_2R^a$, —$NR^aSO_2R^b$, —$SO_2NR^aR^b$, —$NR^aSO_2NR^aR^b$, —$C(O)NR^aSO_2NR^aR^b$ and —$C_{3-8}$ cycloalkyl; and further wherein the heteroaryl or heterocyclic group may be oxidized on a nitrogen atom to form an N-oxide or oxidized on a sulfur atom to form a sulfoxide or sulfone;

$R^N$ is independently —$C_{1-6}$alkyl$NR^1R^2$, —$OC_{1-6}$ alky$NR^1R^2$, —$C_{1-6}$ alkyl$OC_{1-6}$ alkyl$NR^1R^2$, —$NR^aC_{1-6}$ alkyl$NR^1R^2$, —$C_{1-6}$ alkyl$C(O)NR^1R^2$, —$OC_{1-6}$ alkyl$C(O)NR^1R^2$, —$OC_{1-6}$ alkyl$C(O)OR^1$, —$SC_{1-6}$alkyl$NR^1R^2$, —$C_{1-6}$alkyl$OR^a$, or

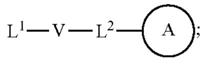;

wherein $L^1$ is independently a bond, O, $NR^a$, S, SO, or $SO_2$;

V is independently selected from a bond, $C_{1-6}$alkyl, $C_{2-6}$alkenyl, and $C_{2-6}$alkynyl;

wherein each alkyl, alkenyl, or alkynyl is optionally independently substituted with $OR^a$, halo, cyano, —$NR^aR^b$, or —$C_{3-8}$ cycloalkyl;

$L^2$ is independently a bond, O, $NR^a$, S, SO, or $SO_2$;

ring A is independently cycloalkyl, aryl, heteroaryl, or heterocyclyl;

wherein each cycloalkyl, aryl, heteroaryl, or heterocyclyl is optionally substituted with 1 to 4 groups independently selected from oxo, —$NO_2$, —$N_3$, —$OR^a$, halo, cyano, —$C_{1-6}$ alkyl, —$C_{1-6}$ haloalkyl, —$C_{2-6}$alkenyl, —$C_{2-6}$ alkynyl, —$OC_{1-6}$ haloalkyl, $NR^aR^b$, —$C(O)R^a$, —$C(O)OR^a$, —$OC_{1-6}$ alkylCN, —$C(O)NR^aR^b$, —$NR^aC(O)R^a$, —$NR^aC(O)OR^a$, —$NR^aC(O)OR^a$, —$C(O)N(R^a)OR^b$, —$SO_2R^a$, —$SO_2NR^aR^b$, —$NR^aSO_2R$, —$NR^aSO_2NR^aR^b$, —$C(O)NR^aSO_2NR^aR^b$, $C_{3-8}$cycloalkyl, and $C_{1-6}$alkyl$C_{3-8}$cycloalkyl; and wherein the alkyl, alkenyl, or alkynyl group is optionally independently substituted with —$OR^a$, halo, cyano, —$NR^aR^b$, or —$C_{3-8}$cycloalkyl.

In one embodiment, t is 0, 1, 2 or 3. In one embodiment, t is 1, 2 or 3. In one embodiment, t is 0, 1 or 2. In one embodiment, t is 0. In one embodiment, t is 1. In one embodiment, t is 2. In one embodiment, t is 3.

In one embodiment, substituents on $Q^W$ or E are independently selected from

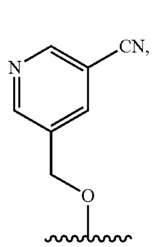
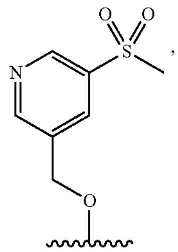,
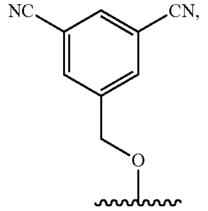
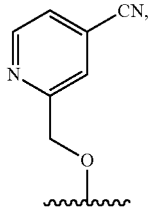
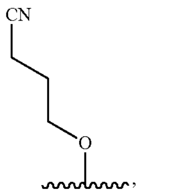,
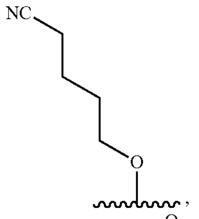,
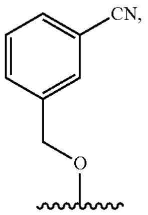
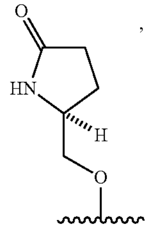,
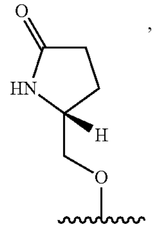,
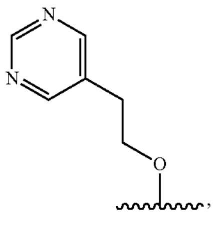 and
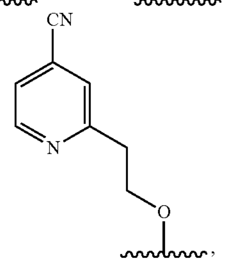, or a pharmaceutically acceptable salt thereof.

In one embodiment, $Q^E$ and $Q^W$ are each optionally substituted with halo. In one embodiment, $Q^E$ and $Q^W$ are each optionally substituted with —$C_{1-6}$alkyl. In one embodiment, $Q^E$ and $Q^W$ are each optionally substituted with —$OC_{1-6}$alkyl. In one embodiment, $Q^E$ and $Q^W$ are each optionally substituted with methoxy.

In one embodiment, $Q^E$ and $Q^W$ are different and each is optionally substituted with 1 to 3 groups independently selected from OH, halo, CN, —$SO_2R^a$, —$C_{1-6}$alkyl, and —$OC_{1-6}$alkyl.

In one embodiment, $Q^E$ and $Q^W$ are the same and each is optionally substituted with 1 to 3 groups independently selected from OH, halo, CN, —$SO_2R^a$, —$C_{1-6}$alkyl, and —$OC_{1-6}$alkyl.

In one embodiment, $R^E$ an $R^W$ are independently selected from —$NR^1R^2$, —$C_{1-6}$ alkyl$NR^1R^2$, —$OC_{1-6}$ alkyl$NR^1R^2$, —$C_{1-6}$ alkyl$OC_{1-6}$alky$NR^1R^2$, —$NR^aC_{1-6}$ alkyl$NR^1R^2$, —$C_{1-6}$ alkyl$N^+R^1R^2R^3$, —$SC_{1-6}$ alky$NR^1R^2$, —C(O)$NR^1R^2$, —$SO_2R^a$, —$(CH_2)_uSO_2NR^1R^2$, —$(CH_2)NR^aSO_2NR^aR^b$, —$SO_2NR^aC_{1-6}$ alkyl$NR^1R^2$, —$NR^aSO_2C_{1-6}$ alkyl$NR^1R^2$, —$(CH_2)_uC(O)NR^aSO_2NR^aR^b$, —$(CH_2)_uN^+R^1R^2O^-$, —$(CH_2)_uP^+R^bR^cR^d$, —$(CH_2)_uP^+R^cR^dO^-$, —$(CH_2)_uP^+O[NR^aR^b][NR^cR^d]$, —$(CH_2)_uNR^cP(O)(OR^c)_2$, —$(CH_2)_uCH_2OP(O)(OR^c)(OR)$; —$(CH_2)_uOP(O)(OR^c)(OR)$, and —$(CH_2)_uOP(O)NR^aR^b)(OR^a)$; wherein $R^1$ is selected from H, —$C_{1-6}$alkyl, —$C_{3-6}$cycloalkyl, heterocyclyl, —$C_{2-6}$alkyl-$OR^a$, or —$C_{1-6}$alkylC(O)$OR^a$;

wherein each alkyl, cycloalkyl, or heterocyclyl is optionally substituted with 1 to 2 groups independently selected from —$OR^a$, —CN, halo, —$C_{1-6}$alkyl$OR^a$, —$C_{1-6}$cyanoalkyl, —$C_{1-3}$haloalkyl, —C(O)$R^a$, —$C_{1-6}$alkyl C(O)$R^a$, —C(O)$OR^a$, —$C_{1-6}$ alkylC(O)$OR^a$, —C(O)$NR^aR^b$, and —$C_{1-6}$ alkylC(O)$NR^aR^b$;

$R^2$ is selected from —$C_{1-6}$alkyl, —$C_{3-6}$cycloalkyl, heterocyclyl, —$C_{2-6}$alkyl-$OR^a$, and —$C_{1-6}$ alkylC(O)$OR^a$;

wherein each alkyl, cycloalkyl, or heterocyclyl is optionally substituted with 1 to 2 groups independently selected from —$OR^a$, —CN, —$C_{1-6}$alkyl$OR^a$, —$C_{1-6}$cyanoalkyl, —$C_{1-3}$haloalkyl, —$C_{3-8}$cycloalkyl, —$C_{1-3}$alkyl$C_{3-8}$cycloalkyl, —C(O)$R^a$, —$C_{1-6}$alkylC(O)$R^a$, —C(O)$OR^a$, —$C_{1-6}$ alkylC(O)$OR^a$, —C(O)$NR^aR^b$, and $C_{1-6}$ alkylC(O)$NR^aR^b$;

or $R^1$ and $R^2$ combine to form a heterocyclyl group optionally containing an additional heteroatom selected from oxygen, sulfur or nitrogen, and optionally substituted with 1 to 3 groups independently selected from oxo, —$C_{1-6}$alkyl, —$OR^a$, —C(O)$OR^a$, —C(O)$R^a$, $C_{1-6}$ alkylC(O)$R^a$, —$C_{1-6}$alkylC(O)$OR^a$, —$NR^aR^b$, —$C_{1-6}$alkyl$NR^aR^b$, and —C(O)$NR^aR^b$;

$R^3$ is independently H, —$C_{1-6}$alkyl, —$C_{2-6}$ alkenyl, —$C_{3-6}$cycloalkyl, aryl, heteroaryl, heterocyclyl, —$C_{1-6}$ alkylaryl;

$R^a$ is independently H or —$C_{1-6}$alkyl;

$R^b$ is independently H or —$C_{1-6}$alkyl;

$R^c$ is independently selected from H, —$C_{1-6}$alkyl, —$C_{3-8}$ cycloalkyl, and —$C_{1-3}$ alkyl$C_{3-8}$ cycloalkyl;

$R^d$ is independently selected from H, —$C_{1-6}$alkyl, —$C_3$-$C_8$cycloalkyl, and —$C_{1-3}$ alkyl$C_{3-8}$cycloalkyl; and u is 0, 1, 2, or 3.

In one embodiment, $R^E$ an $R^W$ are independently selected from —C(O)$NR^1R^2$, —$SO_2R^a$, —$(CH_2)_uSO_2NR^1R^2$, —$(CH_2)_uNR^aSO_2NR^aR^b$, —$SO_2NR^aC_{1-6}$alkyl$NR^1R^2$, —$NR^aSO_2C_{1-6}$alkyl$NR^1R^2$, and —$(CH_2)_uC(O)NR^aSO_2NR^aR^b$; wherein $R^1$ is selected from H, —$C_{1-6}$alkyl, —$C_{3-6}$cycloalkyl, heterocyclyl, —$C_{2-6}$alkyl-$OR^a$, or —$C_{1-6}$alkylC(O)$OR^a$;

wherein each alkyl, cycloalkyl, or heterocyclyl is optionally substituted with 1 to 2 groups independently selected from —$OR^a$, —CN, halo, —$C_{1-6}$alkyl$OR^a$, —$C_{1-6}$cyanoalkyl, —$C_{1-3}$haloalkyl, —C(O)$R^a$, —$C_{1-6}$alkyl C(O)$R^a$, —C(O)$OR^a$, —$C_{1-6}$ alkylC(O)$OR^a$, —C(O)$NR^aR^b$, and —$C_{1-6}$ alkylC(O)$NR^aR^b$;

$R^2$ is selected from —$C_{1-6}$alkyl, —$C_{3-6}$cycloalkyl, heterocyclyl, —$C_{2-6}$alkyl-$OR^a$, and —$C_{1-6}$ alkylC(O)$OR^a$;

wherein each alkyl, cycloalkyl, or heterocyclyl is optionally substituted with 1 to 2 groups independently selected from $—OR^a$, —CN, $—C_{1-6}alkylOR^a$, $—C_{1-6}cyanoalkyl$, $—C_{1-3}haloalkyl$, $—C_{3-8}cycloalkyl$, $—C_{1-3}alkylC_{3-8}cycloalkyl$, $—C(O)R^a$, $—C_{1-6}alkylC(O)R^a$, $—C(O)OR^a$, $—C_{1-6}$ alkylC(O)$OR^a$, $—C(O)NR^aR^b$, and $C_{1-6}$ alkylC(O)$NR^aR^b$;

or $R^1$ and $R^2$ combine to form a heterocyclyl optionally containing an additional heteroatom selected from oxygen, sulfur or nitrogen, and optionally substituted with 1 to 3 groups independently selected from oxo, $—C_{1-6}alkyl$, $—OR^a$, $—C(O)OR^a$, $—C(O)R^a$, $C_{1-6}$ alkylC(O)$R^a$, $—C_{1-6}alkylC(O)OR^a$, $—NR^aR^b$, $—C_{1-6}alkyNR^aR^b$, and $—C(O)NR^aR^b$;

$R^a$ is independently H or $—C_{1-6}alkyl$;

$R^b$ is independently H or $—C_{1-6}alkyl$; and u is 0, 1, 2, or 3.

In one embodiment, $R^E$ an $R^W$ are independently selected from $—(CH_2)_uN^+R^1R^2O^-$, $—(CH_2)_uP^+R^bR^cR^d$, $—(CH_2)_uP^+R^cR^dO^-$, $—(CH_2)_uP^+O[NR^aR^b][NR^cR^d]$, $—(CH_2)_uNR^cP(O)(OR^c)_2$, $—(CH_2)_uCH_2OP(O)(OR)(OR)$, $—(CH_2)_uOP(O)(OR^c)(OR)$, and $—(CH_2)_uOP(O)NR^aR^b)(OR^a)$; wherein $R^1$ is selected from H, $—C_{1-6}alkyl$, $—C_{3-6}cycloalkyl$, heterocyclyl, $—C_{2-6}alkyl\text{-}OR^a$, and $—C_{1-6}alkylC(O)OR^a$;

wherein each alkyl, cycloalkyl, or heterocyclyl is optionally substituted with 1 to 2 groups independently selected from $—OR^a$, —CN, halo, $—C_{1-6}alkylOR^a$, $—C_{1-6}cyanoalkyl$, $—C_{1-3}haloalkyl$, $—C(O)R^a$, $—C_{1-6}alkyl$ C(O)$R^a$, $—C(O)OR^a$, $—C_{1-6}$ alkylC(O)$OR^a$, $—C(O)NR^aR^b$, and $—C_{1-6}$ alkylC(O)$NR^aR^b$;

$R^2$ is selected from $—C_{1-6}$ alkyl, $—C_{3-6}$ cycloalkyl, heterocyclyl, $—C_{2-6}$ alkyl-$OR^a$, and $—C_{1-6}$ alkylC(O)$OR^a$;

wherein each alkyl, cycloalkyl, or heterocyclyl is optionally substituted with 1 to 2 groups independently selected from $—OR^a$, —CN, $—C_{1-6}alkylOR^a$, $—C_{1-6}cyanoalkyl$, $—C_{1-3}haloalkyl$, $—C_{3-8}cycloalkyl$, $—C_{1-3}alkylC_{3-8}cycloalkyl$, $—C(O)R^a$, $—C_{1-6}alkylC(O)R^a$, $—C(O)OR^a$, $—C_{1-6}$ alkylC(O)$OR^a$, $—C(O)NR^aR^b$, and $C_{1-6}$ alkylC(O)$NR^aR^b$;

or $R^1$ and $R^2$ combine to form a heterocyclyl optionally containing an additional heteroatom selected from oxygen, sulfur or nitrogen, and optionally substituted with 1 to 3 groups independently selected from oxo, $—C_{1-6}alkyl$, $—OR^a$, $—C(O)OR^a$, $—C(O)R^a$, $C_{1-6}$ alkylC(O)$R^a$, $—C_{1-6}alkylC(O)OR^a$, $—NR^aR^b$, $—C_{1-6}alkyNR^aR^b$, and $—C(O)NR^aR^b$;

$R^a$ is independently H or $—C_{1-6}$ alkyl;

$R^b$ is independently H or $—C_{1-6}$ alkyl;

$R^c$ is independently selected from H, $—C_{1-6}$ alkyl, $—C_{3-8}$ cycloalkyl, and $—C_{1-3}$ alkyl$C_{3-8}$ cycloalkyl;

$R^d$ is independently selected from H, $—C_{1-6}$ alkyl, $—C_3\text{-}C_8$cycloalkyl, and $—C_{1-3}$ alkyl$C_{3-8}$cycloalkyl; and u is 0, 1, 2 or 3.

In one embodiment, $R^E$ and $R^W$ are each independently $—NR^1R^2$, $—C_{1-6}$ alkyNR^1R^2$, $—OC_{1-6}$ alkylNR^1R^2$, $—C_{1-6}alkylOC_{1-6}alkylNR^1R^2$, $—NR^aC_{1-6}alkylNR^1R^2$, or

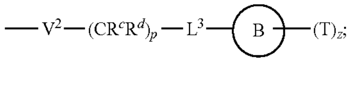

wherein $V^2$ is independently a bond, O, $NR^a$, S, SO or $SO_2$;

$R^c$ is independently selected from H, OH, $—C_{1-6}$ alkyl, and $—C_{3-8}$ cycloalkyl;

$R^d$ is independently selected from H, $—C_{1-6}$ alkyl, and $—C_3\text{-}C_8$cycloalkyl;

$L^3$ is independently a bond, O, $NR^a$, S, SO, or $SO_2$;

ring B is independently cycloalkyl, aryl, heteroaryl, or heterocyclyl;

T is independently H, $OR^a$, $(CH_2)_qNR^1R^2$, $(CH_2)_qNR^aC(O)R$ or $(CH_2)C(O)R^e$;

$R^c$ is independently selected from H, $—C_{1-6}$ alkyl, $—OC_{1-6}alkyl$, $—C_{3-8}cycloalkyl$, aryl, heteroaryl, heterocyclyl, $—OC_{3-8}cycloalkyl$, —Oaryl, —Oheteroaryl, —Oheterocyclyl, $—C_{1-3}$ alkyl$C_{3-8}$cycloalkyl, $—C_{1-6}$ alkylaryl, $—C_{1-6}alkylheteroaryl$, $—NR^fR^g$, $—C_{1-6}$ alkylNR^fR^g$, $—C(O)NR^fR^g$, $—C_{1-6}$ alkylC(O)$NR^fR^g$, $—NHSO_2R^f$, $—C_{1-6}$ alkyl$SO_2R^f$, and $—C_{1-6}$ alkyl$SO_2NR^fR^g$;

p is independently 0, 1, 2, 3, 4, or 5;

q is independently 0, 1, 2, 3, 4, or 5; and z is 0, 1, or 2;

and wherein the alkyl, cycloalkyl, aryl, heteroaryl, or heterocyclyl of $R^E$ or $R^W$ is optionally substituted with 1 to 3 substituents independently selected from the group consisting of $NR^aR^b$, halo, cyano, $OR^a$, $—C_{1-6}alkyl$, $—C_{1-6}haloalkyl$, $—C_{1-6}cyanoalkyl$, $—C_{1-6}alkyNR^aR^b$, $—C_{1-6}alkylOH$, $—C_{3-8}cycloalkyl$, and $—C_{1-3}$ alkyl$C_{3-8}$cycloalkyl;

provided that at least one of $V^2$, $L^3$, ring B and T contains a nitrogen atom;

$R^1$ is selected from H, $—C_{1-6}alkyl$, $—C_{3-6}cycloalkyl$, heterocyclyl, $—C_{2-6}alkyl\text{-}OR^a$, or $—C_{1-6}alkylC(O)OR^a$;

wherein each alkyl, cycloalkyl, or heterocyclyl is optionally substituted with 1 to 2 groups independently selected from $—OR^a$, —CN, halo, $—C_{1-6}alkylOR^a$, $—C_{1-6}cyanoalkyl$, $—C_{1-3}haloalkyl$, $—C(O)R^a$, $—C_{1-6}alkyl$ C(O)$R^a$, $—C(O)OR^a$, $—C_{1-6}$ alkylC(O)$OR^a$, $—C(O)NR^aR^b$, and $—C_{1-6}$ alkylC(O)$NR^aR^b$;

$R^2$ is selected from $—C_{1-6}alkyl$, $—C_{3-6}$ cycloalkyl, heterocyclyl, $—C_{2-6}alkyl\text{-}OR^a$, and $—C_{1-6}$ alkylC(O)$OR^a$;

wherein each alkyl, cycloalkyl, or heterocyclyl is optionally substituted with 1 to 2 groups independently selected from $—OR^a$, —CN, $—C_{1-6}alkylOR^a$, $—C_{1-6}cyanoalkyl$, $—C_{1-3}haloalkyl$, $—C_{3-8}cycloalkyl$, $—C_{1-3}alkylC_{3-8}cycloalkyl$, $—C(O)R^a$, $—C_{1-6}alkylC(O)R^a$, $—C(O)OR^a$, $—C_{1-6}alkylC(O)OR^a$, $—C(O)NR^aR^b$, and $C_{1-6}alkylC(O)NR^aR^b$;

or $R^1$ and $R^2$ combine to form a heterocyclyl group optionally containing an additional heteroatom selected from oxygen, sulfur or nitrogen, and optionally substituted with 1 to 3 groups independently selected from oxo, $—C_{1-6}alkyl$, $—OR^a$, $—C(O)OR^a$, $—C(O)R^a$, $C_{1-6}$ alkylC(O)$R^a$, $—C_{1-6}alkylC(O)OR^a$, $—NR^aR^b$, $—C_{1-6}$ alkylNR^aR^b$, and $—C(O)NR^aR^b$;

$R^a$ is independently H or $—C_{1-6}alkyl$; and $R^b$ is independently H or $—C_{1-6}alkyl$.

In one embodiment, $R^E$ and $R^W$ are each independently $—NR^1R^2$, $—C_{1-6}$ alkyNR^1R^2$, $—OC_{1-6}$ alkyNR^1R^2$, $—C_{1-6}alkylOC_{1-6}alkylNR^1R^2$, $—NR^aC_{1-6}alkylNR^1R^2$, or

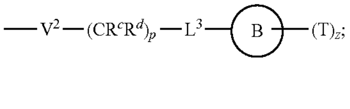

wherein $V^2$ is independently a bond, O, $NR^a$, S, SO or $SO_2$;

$L^3$ is independently a bond, O, $NR^a$, S, SO, or $SO_2$;

ring B is cycloalkyl, aryl, heteroaryl, or heterocyclyl;

T is independently H, $OR^a$, $(CH_2)_qNR^1R^2$, $(CH_2)_qNR^aC(O)R^e$ or $(CH_2)C(O)R^e$;

p is independently 0, 1, 2, or 3;

q is independently 0, 1, 2, or 3;

z is 0, 1, 2, or 3;

and wherein the alkyl, cycloalkyl, aryl, heteroaryl, or heterocyclyl of $R^E$ or $R^W$ is optionally substituted with 1 to 3 substituents independently selected from the group consisting of $NR^aR^b$, halo, cyano, $OR^a$, —$C_{1-6}$alkyl, —$C_{1-6}$haloalkyl, —$C_{1-6}$cyanoalkyl, —$C_{1-6}$alkyNR$^a$R$^b$, —$C_{1-6}$alkylOH, —$C_{3-8}$ cycloalkyl, and —$C_{1-3}$ alkyl$C_{3-8}$cycloalkyl;

provided that at least one of $V^2$, $L^3$, ring B and T contains a nitrogen atom;

$R^1$ is selected from H, —$C_{1-6}$alkyl, —$C_{3-6}$cycloalkyl, heterocyclyl, —$C_{2-6}$alkyl-OR$^a$, or —$C_{1-6}$alkylC(O)OR$^a$;

wherein each alkyl, cycloalkyl, or heterocyclyl group is optionally substituted with 1 to 2 groups independently selected from —OR$^a$, —CN, halo, —$C_{1-6}$alkylOR$^a$, —$C_{1-6}$cyanoalkyl, —$C_{1-3}$haloalkyl, —C(O)R$^a$, —$C_{1-6}$alkyl C(O)R$^a$, —C(O)OR$^a$, —$C_{1-6}$ alkylC(O)OR$^a$, —C(O)NR$^a$R$^b$, and —$C_{1-6}$ alkylC(O)NR$^a$R$^b$;

$R^2$ is selected from —$C_{1-6}$alkyl, —$C_{3-6}$ cycloalkyl, heterocyclyl, —$C_{2-6}$alkyl-OR$^a$, and —$C_{1-6}$ alkylC(O)OR$^a$;

wherein each alkyl, cycloalkyl, or heterocyclyl is optionally substituted with 1 to 2 groups independently selected from —OR$^a$, —CN, —$C_{1-6}$alkylOR$^a$, —$C_{1-6}$cyanoalkyl, —$C_{1-3}$haloalkyl, —$C_{3-8}$cycloalkyl, —$C_{1-3}$alkyl$C_{3-8}$cycloalkyl, —C(O)R$^a$, —$C_{1-6}$alkylC(O)R$^a$, —C(O)OR$^a$, —$C_{1-6}$ alkylC(O)OR$^a$, —C(O)NR$^a$R$^b$, and $C_{1-6}$ alkylC(O)NR$^a$R$^b$;

or $R^1$ and $R^2$ combine to form a heterocyclyl optionally containing an additional heteroatom selected from oxygen, sulfur or nitrogen, and optionally substituted with 1 to 3 groups independently selected from oxo, —$C_{1-6}$alkyl, —OR$^a$, —C(O)OR$^a$, —C(O)R$^a$, $C_{1-6}$alkylC(O)R$^a$, —$C_{1-6}$alkylC(O)OR$^a$, —NR$^a$R$^b$, —$C_{1-6}$ alkylNR$^a$R$^b$, and —C(O)NR$^a$R$^b$;

$R^a$ is independently H or —$C_{1-6}$alkyl;

$R^b$ is independently H or —$C_{1-6}$alkyl;

$R^c$ is independently selected from H, OH, —$C_{1-6}$alkyl, and —$C_{3-8}$ cycloalkyl;

$R^d$ is independently selected from H, —$C_{1-6}$alkyl, and —$C_3$-$C_8$cycloalkyl;

$R^c$ is selected from H, —$C_{1-6}$alkyl, —O$C_{1-6}$alkyl, —$C_{3-8}$ cycloalkyl, aryl, heteroaryl, heterocyclyl, —O$C_{3-8}$cycloalkyl, —Oaryl, —Oheteroaryl, —Oheterocyclyl, —$C_{1-3}$ alkyl$C_{3-8}$cycloalkyl, —$C_{1-6}$alkylaryl, —$C_{1-6}$alkylheteroaryl, —NR$^f$R$^g$, —$C_{1-6}$ alkylNR$^f$R$^g$, —C(O)NR$^h$R$^g$, —$C_{1-6}$ alkylC(O)NR$^f$R$^g$, —NHSO$_2$R$^f$, —$C_{1-6}$ alkylSO$_2$R$^f$, and —$C_{1-6}$ alkylSO$_2$NR$^f$R$^g$;

$R^f$ is independently selected from H, —$C_{1-6}$alkyl, and —$C_{3-8}$ cycloalkyl;

$R^g$ is independently selected from H, —$C_{1-6}$alkyl, and —$C_{3-8}$ cycloalkyl.

In one embodiment, $R^E$ and $R^W$ are each

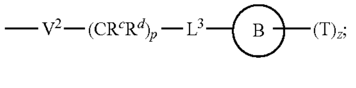

wherein $V^2$ is independently a bond, O, $NR^a$, S, SO or $SO_2$;

$R^c$ is independently selected from H, OH, —$C_{1-6}$alkyl, and —$C_{3-8}$ cycloalkyl;

$R^d$ is independently selected from H, —$C_{1-6}$alkyl, and —$C_3$-$C_8$cycloalkyl;

$L^3$ is independently a bond, O, $NR^a$, S, SO, or $SO_2$;

ring B is cycloalkyl, aryl, heteroaryl, or heterocyclyl;

T is independently H, $OR^a$, $(CH_2)_qNR^1R^2$, $(CH_2)NR^aC(O)R^e$ or $(CH_2)_qC(O)R^e$;

$R^e$ is selected from H, —$C_{1-6}$ alkyl, —O$C_{1-6}$alkyl, —$C_{3-8}$ cycloalkyl, aryl, heteroaryl, heterocyclyl, —O$C_{3-8}$ cycloalkyl, —Oaryl, —Oheteroaryl, —Oheterocyclyl, —$C_{1-3}$ alkyl$C_{3-8}$cycloalkyl, —$C_{1-6}$ alkylaryl, —$C_{1-6}$alkylheteroaryl, —NR$^f$R$^g$, —$C_{1-6}$ alkylNR$^f$R$^g$, —C(O)NR$^f$R$^g$, —$C_{1-6}$ alkylC(O)NR$^f$R$^g$, —NHSO$_2$R$^f$, —$C_{1-6}$ alkylSO$_2$R$^f$, and —$C_{1-6}$ alkylSO$_2$NR$^f$R$^g$;

$R^f$ is independently selected from H, —$C_{1-6}$ alkyl, and —$C_{3-8}$ cycloalkyl;

$R^g$ is independently selected from H, —$C_{1-6}$ alkyl, and —$C_{3-8}$ cycloalkyl;

p is independently 0, 1, 2, or 3;

q is independently 0, 1, 2, or 3;

z is 0, 1, 2, or 3;

and wherein the alkyl, cycloalkyl, aryl, heteroaryl, or heterocyclyl of $R^E$ or $R^W$ is optionally substituted with 1 to 3 substituents independently selected from the group consisting of $NR^aR^b$, halo, cyano, $OR^a$, —$C_{1-6}$ alkyl, —$C_{1-6}$haloalkyl, —$C_{1-6}$ cyanoalkyl, —$C_{1-6}$ alkylNR$^a$R$^b$, —$C_{1-6}$ alkylOH, —$C_{3-8}$ cycloalkyl, and —$C_{1-3}$ alkyl$C_{3-8}$cycloalkyl;

provided that at least one of $V^2$, $L^3$, ring B and T contains a nitrogen atom.

In one embodiment, $R^E$ and $R^W$ are each independently —NR$^1$R$^2$, —$C_{1-6}$ alkyNR$^1$R$^2$, or —O$C_{1-6}$alkylNR$^1$R$^2$;

$R^1$ is independently selected from H, —$C_{1-6}$alkyl, —$C_{3-6}$cycloalkyl, heterocyclyl, —$C_{2-6}$alkyl-OR$^a$, or —$C_{1-6}$alkylC(O)OR$^a$;

wherein each alkyl, cycloalkyl, or heterocyclyl is optionally substituted with 1 to 2 groups independently selected from —OR$^a$, —CN, halo, —$C_{1-6}$alkylOR$^a$, —$C_{1-6}$cyanoalkyl, —$C_{1-3}$haloalkyl, —C(O)R$^a$, —$C_{1-6}$alkyl C(O)R$^a$, —C(O)OR$^a$, —$C_{1-6}$ alkylC(O)OR$^a$, —C(O)NR$^a$R$^b$, and —$C_{1-6}$ alkylC(O)NR$^a$R$^b$;

$R^2$ is independently selected from —$C_{1-6}$alkyl, —$C_{3-6}$cycloalkyl, heterocyclyl, —$C_{2-6}$alkyl-OR$^a$, and —$C_{1-6}$ alkylC(O)OR$^a$;

wherein each alkyl, cycloalkyl, or heterocyclyl is optionally substituted with 1 to 2 groups independently selected from —OR$^a$, —CN, —$C_{1-6}$alkylOR$^a$, —$C_{1-6}$cyanoalkyl, —$C_{1-3}$haloalkyl, —$C_{3-8}$cycloalkyl, —$C_{1-3}$alkyl$C_{3-8}$cycloalkyl, —C(O)R$^a$, —$C_{1-6}$alkylC(O)R$^a$, —C(O)OR$^a$, —$C_{1-6}$alkylC(O)OR$^a$, —C(O)NR$^a$R$^b$, and $C_{1-6}$alkylC(O)NR$^a$R$^b$;

or $R^1$ and $R^2$ combine to form a heterocyclyl optionally containing 1 or 2 additional heteroatoms independently selected from oxygen, sulfur or nitrogen, and optionally substituted with 1 to 3 groups independently selected from oxo, —$C_{1-6}$alkyl, —OR$^a$, —C(O)OR$^a$, —C(O)R$^a$, $C_{1-6}$ alkylC(O)R$^a$, —$C_{1-6}$alkylC(O)OR$^a$, —NR$^a$R$^b$, —$C_{1-6}$alkylNR$^a$R$^b$, and —C(O)NR$^a$R$^b$;

$R^a$ is independently H or —$C_{1-6}$alkyl;

$R^b$ is independently H or —$C_{1-6}$alkyl.

In one embodiment, $R^E$ and $R^W$ are each —$C_{1-6}$alkylO$C_{1-6}$ alkyNR$^1$R$^2$;

$R^1$ is selected from H, —$C_{1-6}$alkyl, —$C_{3-6}$cycloalkyl, heterocyclyl, —$C_{2-6}$alkyl-$OR^a$, and —$C_{1-6}$alkylC(O)$OR^a$;

wherein each alkyl, cycloalkyl, or heterocyclyl is optionally substituted with 1 to 2 groups independently selected from —$OR^a$, —CN, halo, —$C_{1-6}$alkyl$OR^a$, —$C_{1-6}$cyanoalkyl, —$C_{1-3}$haloalkyl, —C(O)$R^a$, —$C_{1-6}$alkyl C(O)$R^a$, —C(O)$OR^a$, —$C_{1-6}$alkylC(O)$OR^a$, —C(O)$NR^aR^b$, and —$C_{1-6}$alkylC(O)$NR^aR^b$;

$R^2$ is selected from —$C_{1-6}$alkyl, —$C_{3-6}$cycloalkyl, heterocyclyl, —$C_{2-6}$alkyl-$OR^a$, and —$C_{1-6}$alkylC(O)$OR^a$;

wherein each alkyl, cycloalkyl, or heterocyclyl is optionally substituted with 1 to 2 groups independently selected from —$OR^a$, —CN, —$C_{1-6}$alkyl$OR^a$, —$C_{1-6}$cyanoalkyl, —$C_{1-3}$haloalkyl, —$C_{3-8}$cycloalkyl, —$C_{1-3}$alkyl$C_{3-8}$cycloalkyl, —C(O)$R^a$, —$C_{1-6}$alkylC(O)$R^a$, —C(O)$OR^a$, —$C_{1-6}$alkylC(O)$OR^a$, —C(O)$NR^aR^b$, and $C_{1-6}$alkylC(O)$NR^aR^b$; or $R^1$ and $R^2$ combine to form a heterocyclyl optionally containing 1 or 2 additional heteroatoms independently selected from oxygen, sulfur or nitrogen, and optionally substituted with 1 to 3 groups independently selected from oxo, —$C_{1-6}$alkyl, —$OR^a$, —C(O)$OR^a$, —C(O)$R^a$, $C_{1-6}$alkylC(O)$R^a$, —$C_{1-6}$alkylC(O)$OR^a$, —$NR^aR^b$, —$C_{1-6}$alkyl$NR^aR^b$, and —C(O)$NR^aR^b$;

$R^a$ is independently H or —$C_{1-6}$alkyl; and $R^b$ is independently H or —$C_{1-6}$alkyl.

In one embodiment, provided is a compound of formula (I), wherein $R^E$ and $R^W$ are each —$OC_{1-6}$ alky$NR^1R^2$;

$R^1$ is selected from H, —$C_{1-6}$alkyl, —$C_{3-6}$cycloalkyl, heterocyclyl, —$C_{2-6}$alkyl-$OR^a$, and —$C_{1-6}$alkylC(O)$OR^a$;

wherein each alkyl, cycloalkyl, or heterocyclyl is optionally substituted with 1 to 2 groups independently selected from —$OR^a$, —CN, halo, —$C_{1-6}$alkyl$OR^a$, —$C_{1-6}$cyanoalkyl, —$C_{1-3}$haloalkyl, —C(O)$R^a$, —$C_{1-6}$alkyl C(O)$R^a$, —C(O)$OR^a$, —$C_{1-6}$alkylC(O)$OR^a$, —C(O)$NR^aR^b$, and —$C_{1-6}$alkylC(O)$NR^aR^b$;

$R^2$ is selected from —$C_{1-6}$alkyl, —$C_{3-6}$cycloalkyl, heterocyclyl, —$C_{2-6}$alkyl-$OR^a$, and —$C_{1-6}$alkylC(O)$OR^a$;

wherein each alkyl, cycloalkyl, or heterocyclyl is optionally substituted with 1 to 2 groups independently selected from —$OR^a$, —CN, —$C_{1-6}$alkyl$OR^a$, —$C_{1-6}$cyanoalkyl, —$C_{1-3}$haloalkyl, —$C_{3-8}$cycloalkyl, —$C_{1-3}$alkyl$C_{3-8}$cycloalkyl, —C(O)$R^a$, —$C_{1-6}$alkylC(O)$R^a$, —C(O)$OR^a$, —$C_{1-6}$alkylC(O)$OR^a$, —C(O)$NR^aR^b$, and $C_{1-6}$alkylC(O)$NR^aR^b$; or $R^1$ and $R^2$ combine to form a heterocyclyl group optionally containing 1 or 2 additional heteroatoms independently selected from oxygen, sulfur or nitrogen, and optionally substituted with 1 to 3 groups independently selected from oxo, —$C_{1-6}$alkyl, —$OR^a$, —C(O)$OR^a$, —C(O)$R^a$, $C_{1-6}$alkylC(O)$R^a$, —$C_{1-6}$alkylC(O)$OR^a$, —$NR^aR^b$, —$C_{1-6}$alkyl$NR^aR^b$, and —C(O)$NR^aR^b$;

$R^a$ is independently H or —$C_{1-6}$alkyl; and $R^b$ is independently H or —$C_{1-6}$alkyl.

In one embodiment, $R^E$ and $R^W$ are each —$NR^1R^2$;

$R^1$ is selected from H, —$C_{1-6}$alkyl, —$C_{3-6}$cycloalkyl, heterocyclyl, —$C_{2-6}$alkyl-$OR^a$, and —$C_{1-6}$alkylC(O)$OR^a$;

wherein each alkyl, cycloalkyl, or heterocyclyl is optionally substituted with 1 to 2 groups independently selected from —$OR^a$, —CN, halo, —$C_{1-6}$alkyl$OR^a$, —$C_{1-6}$cyanoalkyl, —$C_{1-3}$haloalkyl, —C(O)$R^a$, —$C_{1-6}$alkyl C(O)$R^a$, —C(O)$OR^a$, —$C_{1-6}$alkylC(O)$OR^a$, —C(O)$NR^aR^b$, and —$C_{1-6}$alkylC(O)$NR^aR^b$;

$R^2$ is selected from —$C_{1-6}$alkyl, —$C_{3-6}$cycloalkyl, heterocyclyl, —$C_{2-6}$alkyl-$OR^a$, and —$C_{1-6}$alkylC(O)$OR^a$;

wherein each alkyl, cycloalkyl, or heterocyclyl group is optionally substituted with 1 to 2 groups independently selected from —$OR^a$, —CN, —$C_{1-6}$alkyl$OR^a$, —$C_{1-6}$cyanoalkyl, —$C_{1-3}$haloalkyl, —$C_{3-8}$cycloalkyl, —$C_{1-3}$alkyl$C_{3-8}$cycloalkyl, —C(O)$R^a$, —$C_{1-6}$alkylC(O)$R^a$, —C(O)$OR^a$, —$C_{1-6}$alkylC(O)$OR^a$, —C(O)$NR^aR^b$, and $C_{1-6}$alkylC(O)$NR^aR^b$;

or $R^1$ and $R^2$ combine to form a heterocyclyl group optionally containing an additional heteroatom selected from oxygen, sulfur or nitrogen, and optionally substituted with 1 to 3 groups independently selected from oxo, —$C_{1-6}$alkyl, —$OR^a$, —C(O)$OR^a$, —C(O)$R^a$, $C_{1-6}$alkylC(O)$R^a$, —$C_{1-6}$alkylC(O)$OR^a$, —$NR^aR^b$, —$C_{1-6}$alkyl$NR^aR^b$, and —C(O)$NR^aR^b$;

$R^a$ is independently H or —$C_{1-6}$alkyl; and $R^b$ is independently H or —$C_{1-6}$alkyl.

In one embodiment, $R^E$ and $R^W$ are each independently —$NR^1R^2$, —$C_{1-6}$ alky$NR^1R^2$, or —$OC_{1-6}$ alkyl$NR^1R^2$; wherein $R^1$ and $R^2$ combine to form a heterocyclyl selected from

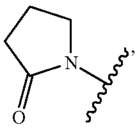,
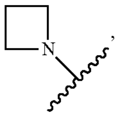,
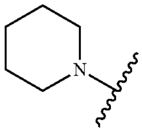,
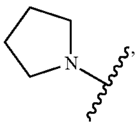,
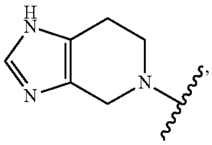,
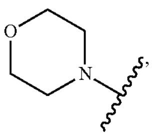,
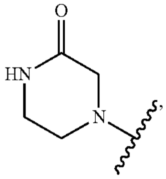,
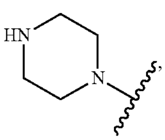,
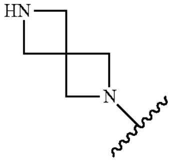,
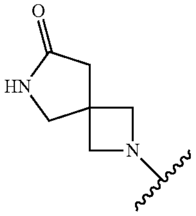,
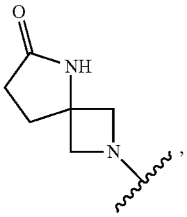,
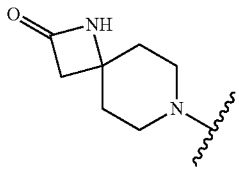, -continued

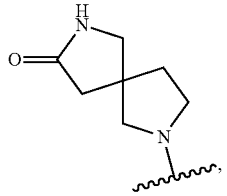
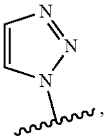
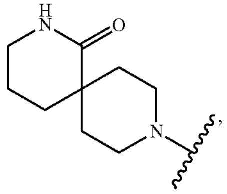
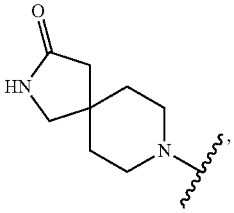
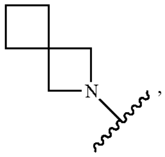
and
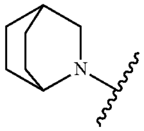

wherein each is optionally substituted with 1 to 3 groups independently selected from —$C_{1-6}$alkyl, —$OR^a$, —C(O)$OR^a$, —C(O)$R^a$, $C_{1-6}$alkylC(O)$R^a$, —$C_{1-6}$alkylC(O)$OR^a$, —$NR^aR^b$, —$C_{1-6}$alkyNR$^aR^b$, and —C(O)NR$^aR^b$;

$R^a$ is independently H or —$C_{1-6}$ alkyl; and $R^b$ is independently H or —$C_{1-6}$ alkyl.

In one embodiment, $R^W$ and $R^E$ are each independently selected from:

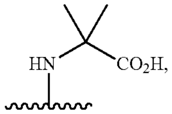
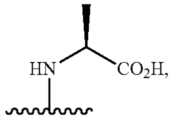
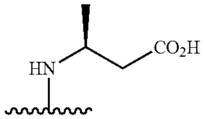
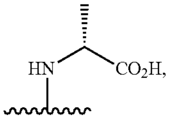
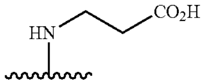
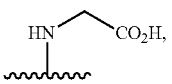
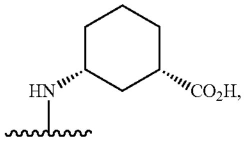
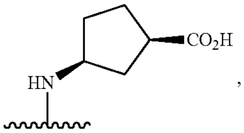
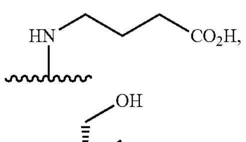
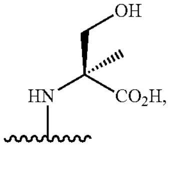
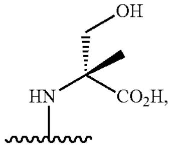
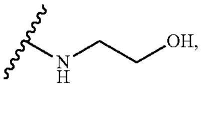

-continued

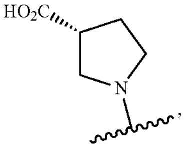
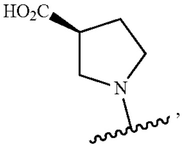
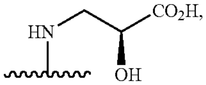
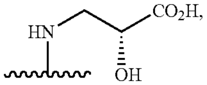
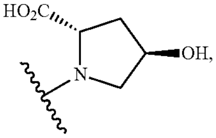
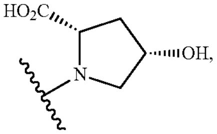
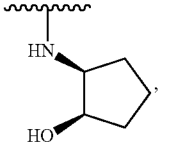
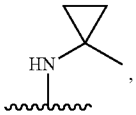
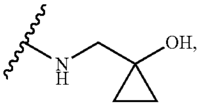
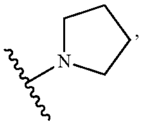
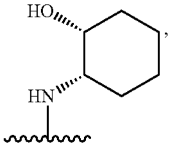
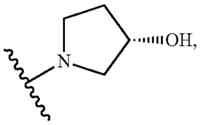
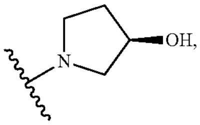
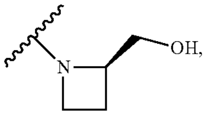
and
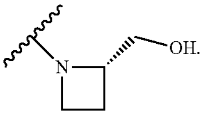

In one embodiment, each $R^W$ and $R^E$ is independently selected from:

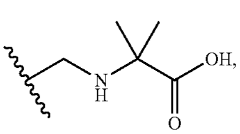
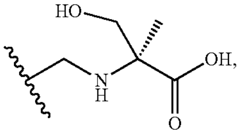
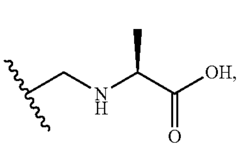
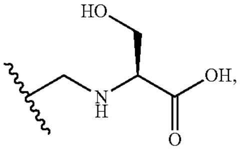
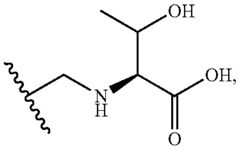
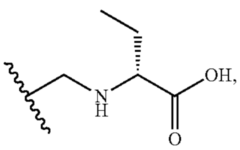

-continued
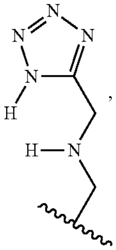,
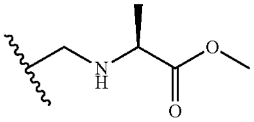,
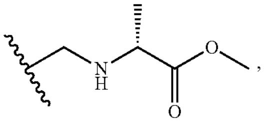,
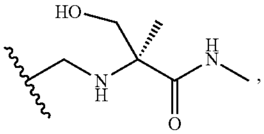,
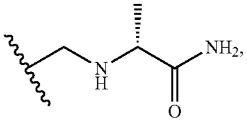 and
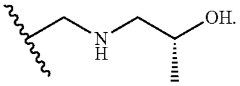
In one embodiment, each $R^W$ and $R^E$ is independently selected from:
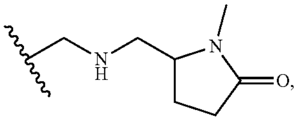
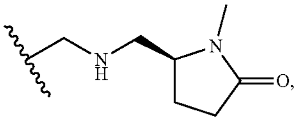
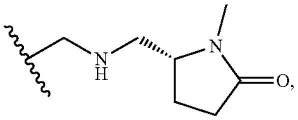
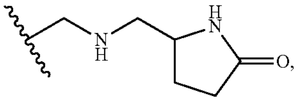
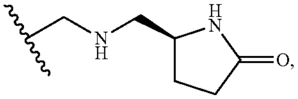
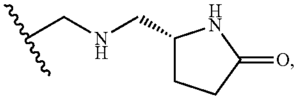
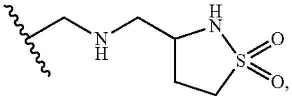
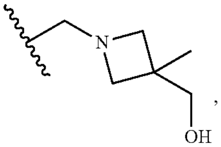,
-continued
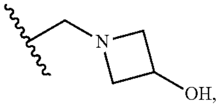
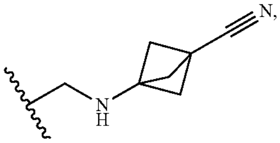,
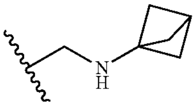
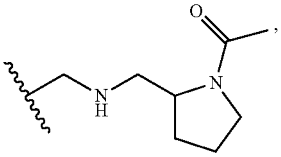
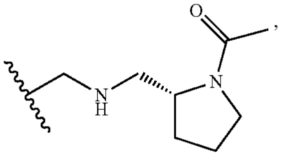
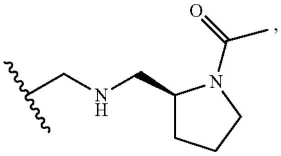
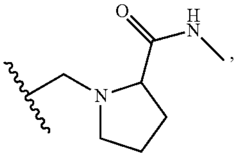
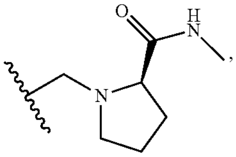
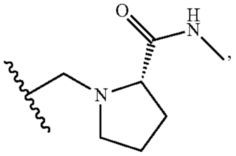
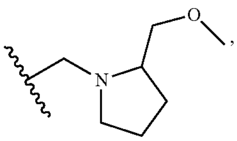
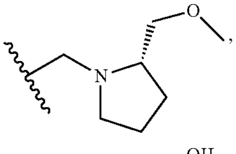
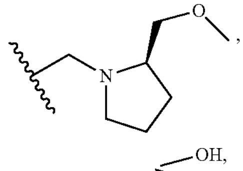
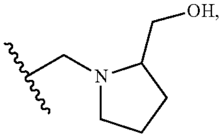
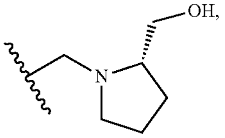
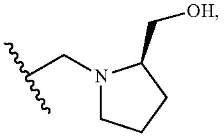
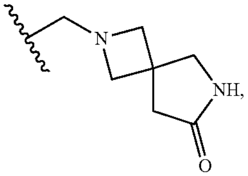 and -continued

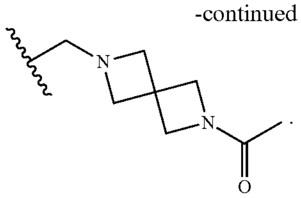

In one embodiment, each $R^W$ and $R^E$ is independently selected from:

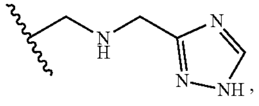

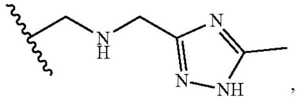

,

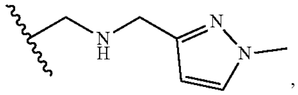

,

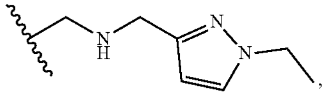

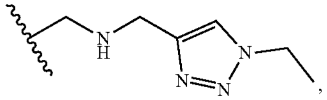

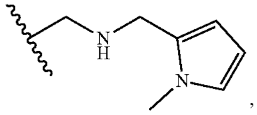

,

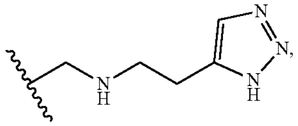

and

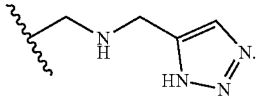

In another embodiment of the disclosure, provided is a compound of formula (I):

$$R^W\text{-}Q^W\text{-}L^W\text{-}Ar^W\text{—}Ar^E\text{-}L^E\text{-}Q^E\text{-}R^E \quad (I)$$

wherein:

$Ar^E$ and $Ar^W$ are each independently aryl, heteroaryl, or heterocyclyl, wherein each aryl, heteroaryl, or heterocyclyl is optionally substituted with 1 to 2 groups independently selected from halo, —$OR^a$, —$C_{1-6}$ alkyl, —$OC_{1-6}$ alkyl, —$C_{1-6}$ haloalkyl, and —$C_{3-8}$cycloalkyl;

$L^E$ and $L^W$ are each independently a bond, —O—, —$(CR^3R^4)_m$—, —$O(CR^3R^4)_m$, —$(CR^3R^4)_mO$, —$(CR^3R^4)_mNR^3$—, —$NR^3(CR^3R^4)_m$—, or —C(O)—, m is independently 0, 1, 2, 3 or 4;

$Q^E$ and $Q^W$ are each independently aryl, heteroaryl, or heterocyclyl, wherein each aryl, heteroaryl, or heterocyclyl is optionally substituted with 1 to 4 groups independently selected from halo, —$OR^a$, —$N_3$, —$NO_2$, —CN, —$NR^aR^b$, —$SO_2R^a$, —$SO_2N^aR^b$, —$NR^aSO_2R^a$, —$NR^aC(O)R^a$, —$C(O)NR^aR^b$, —$C_{1-6}$ alkyl, —$OC_{1-6}$ alkyl, —$C_{3-8}$ cycloalkyl, and $R^N$;

wherein $R^N$ is

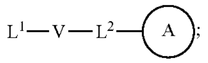

wherein $L^1$ is independently a bond, O, $NR^a$, S, SO, or $SO_2$;

V is independently selected from a bond, $C_{1-6}$alkyl, $C_{2-6}$alkenyl, and $C_{2-6}$alkynyl;

wherein each alkyl, alkenyl, or alkynyl is optionally independently substituted with —$OR^a$, halo, cyano, —$NR^aR^b$ or —$C_{3-8}$ cycloalkyl;

$L^2$ is independently a bond, O, $NR^a$, S, SO, or $SO_2$;

ring A is independently cycloalkyl, aryl, heteroaryl, or heterocyclyl;

wherein the cycloalkyl, aryl, heteroaryl, or heterocyclyl is optionally independently substituted with 1 to 2 groups independently selected from oxo, —$NO_2$, —$N_3$, —$OR^a$, halo, cyano, —$NR^aR^b$, —$C(O)R^a$, —$C(O)OR^a$, —$OC_{1-6}$alkyCN, —$C(O)NR^aR^b$, —$NR^aC(O)R^a$, —$NR^aC(O)OR^a$, —$NR^aC(O)OR^a$, —$C(O)N(R^a)OR^b$, —$SO_2R^a$, —$SO_2NR^aR^b$, —$NR^aSO_2R^b$, —$NR^aSO_2NR^aR^b$, —$C(O)NR^aSO_2NR^aR^b$, $C_{3-8}$cycloalkyl, and $C_{1-6}$alkyl $C_{3-8}$cycloalkyl;

$R^E$ and $R^W$ are each independently —$NR^1R^2$, —$C_{1-6}$ alkyNR$^1$R$^2$, —$OC_{1-6}$ alkylNR$^1$R$^2$, —$C_{1-6}$ alkylOC$_{1-6}$alkylNR$^1$R$^2$, —$NR^aC_{1-6}$ alkylNR$^1$R$^2$, —$C(O)NR^1R^2$, —$(CH_2)_uSO_2NR^1R^2$, —$SO_2NR^a$ $C_{1-6}$alkylNR$^1$R$^2$, —$NR^aSO_2C_{1-6}$alkylNR$^1$R$^2$ or

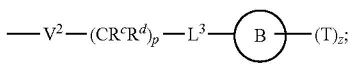

wherein $V^2$ is independently a bond, O, $NR^a$, S, SO or $SO_2$ $L^3$ is independently a bond, O, $NR^a$, S, SO, or $SO_2$;

ring B is cycloalkyl, aryl, heteroaryl, or heterocyclyl;

T is $(CH_2)_qNR^1R^2$ or $(CH_2)_qC(O)R^e$;

p is 0, 1, 2, or 3;

q is 0, 1, 2, or 3;

u is 0, 1, 2, or 3;

and wherein the alkyl, cycloalkyl, aryl, heteroaryl, or heterocyclyl group is optionally substituted with 1 to 3 substituents independently selected from the group consisting of $NR^aR^b$, halo, cyano, oxo, $OR^a$, —$C_{1-6}$ alkyl, —$C_{1-6}$haloalkyl, —$C_{1-6}$ cyanoalkyl, —$C_{1-6}$ alkylNR$^a$R$^b$, —$C_{1-6}$ alkylOH, —$C_{3-8}$cycloalkyl, and —$C_{1-3}$ alkylC$_{3-8}$cycloalkyl;

provided that at least one of $V^2$, $L^3$, ring B and T contains a nitrogen atom;

$R^1$ is independently selected from H, —$C_{1-6}$ alkylaryl, heterocyclyl, —$C_{1-6}$ alkylheteroaryl, —$C_{1-6}$ alkylheterocyclyl, —$C_{1-6}$ alkylC(O)OR$^a$, —$C_{2-6}$ alkenylC(O)OR$^a$, and $C_{1-6}$ alkylC$_{3-8}$cycloalkyl;

wherein each alkyl, cycloalkyl, aryl, heteroaryl, or heterocyclyl is optionally substituted with 1 to 2 groups independently selected from —$OR^a$, oxo, —CN, halo, $C_{1-6}$ alkyl, —$C_{1-6}$ alkylOR$^a$, —$C_{1-6}$cyanoalkyl, —$C_{1-6}$haloalkyl, $C_{3-8}$cycloalkyl, —$C_{1-3}$alkylC$_{3-8}$cycloalkyl, —$C(O)R^a$, —$C_{1-6}$ alkylC(O)R$^a$, —$C(O)OR^a$, —$C_{1-6}$ alkylC(O)OR$^a$, —$NR^aR^b$, —$C_{1-6}$ alkylNR$^a$R$^b$, —$C(O)NR^aR^b$, —$C_{1-6}$ alkylC(O)NR$^a$R$^b$, —$SO_2R^a$, $—C_{1-6}$ alkyl$SO_2R^a$, $—SO_2N^aR^b$, $—C_{1-6}$ alkyl$SO_2NR^aR^b$, $—C(O)NR^aSO_2R$, $—C_{1-6}$ alkylC(O)$NR^aSO_2R^b$, $—NR^aC(O)R^b$, and $—C_{1-6}$alky$NR^aC(O)R^b$;

$R^2$ is selected from $—C_{1-6}$ alkyl, $—C_{2-6}$ alkenyl, $—C_{3-6}$ cycloalkyl, aryl, heteroaryl, heterocyclyl, $—C_{1-6}$ alkylaryl, $—C_{1-6}$ alkylheteroaryl, $—C_{1-6}$ alkylheterocyclyl, $—C_{2-6}$ alkyl-$OR^a$, $—C_{1-6}$ alkylC(O)$OR^a$, and $—C_{2-6}$ alkenylC(O)$OR^a$;

wherein each alkyl, alkenyl, cycloalkyl, aryl, heteroaryl, or heterocycle is optionally substituted with 1 to 3 groups independently selected from $—OR^a$, —CN, halo, $—C_{1-6}$ alkyl$OR^a$, $—C_{1-6}$ cyanoalkyl, $—C_{1-6}$haloalkyl, $—C_{3-8}$ cycloalkyl, $—C_{1-3}$ alkyl$C_{3-8}$cycloalkyl, $—C(O)R^a$, $—C_{1-6}$ alkylC(O)$R^a$, $—C(O)OR^a$, $—C_{1-6}$alkylC(O)$OR^a$, $—NR^aR^b$, $—C_{1-6}$alkyl$NR^aR^b$, $—C(O)NR^aR^b$, $—C_{1-6}$alkylC(O)$NR^aR^b$, $—SO_2R^a$, $—C_{1-6}$ alkyl$SO_2R^a$, $—SO_2N_aR^b$, $—C_{1-6}$ alkyl$SO_2NR^aR^b$, $—C(O)NR^aSO_2R^b$ and $—NR^aC(O)R^b$;

or $R^1$ and $R^2$ combine to form a heterocyclyl group optionally containing 1, 2, or 3 additional heteroatoms independently selected from oxygen, sulfur or nitrogen, and optionally substituted with 1 to 3 groups independently selected from oxo, $—C_{1-6}$ alkyl, $—C_{3-8}$ cycloalkyl, $—C_{2-6}$ alkenyl, $—C_{2-6}$ alkynyl, $—OR^a$, $—C(O)OR^a$, $—C_{1-6}$ cyanoalkyl, $—C_{1-6}$alkyl$OR^a$, $—C_{1-6}$haloalkyl, $—C_{1-3}$alkyl$C_{3-8}$cycloalkyl, $—C(O)R^a$, $C_{1-6}$alkylC(O)$R^a$, $—C_{1-6}$alkylC(O)$OR^a$, $—NR^aR^b$, $—C_{1-6}$alkyl$NR^aR^b$, $—C(O)NR^aR^b$, $—C_{1-6}$alkylC(O)$NR^aR^b$, $—SO_2R^a$, $—C_{1-6}$ alkyl$SO_2R^a$, $—SO_2NR^aR^b$, and $C_{1-6}$ alkyl$SO_2NR^aR^b$;

$R^3$ is independently H, halo, $—C_{1-6}$alkyl, —OH, $—OCH_3$, or $—OCH_2CH_3$;

$R^4$ is independently H, halo, $—C_{1-6}$alkyl, —OH, $—OCH_3$, or $—OCH_2CH_3$;

$R^a$ is independently selected from H, $—C_{1-6}$ alkyl, $—C_{3-8}$ cycloalkyl, and $—C_{1-3}$ alkyl$C_{3-8}$cycloalkyl;

$R^b$ is independently selected from H, $—C_{1-6}$ alkyl, $—C_{3-8}$ cycloalkyl, and $—C_{1-3}$ alkyl$C_{3-8}$cycloalkyl;

$R^c$ is independently selected from H, $—C_{1-6}$ alkyl, $—C_{3-8}$ cycloalkyl, and $—C_{1-3}$ alkyl$C_{3-8}$ cycloalkyl;

$R^d$ is independently selected from H, $—C_{1-6}$ alkyl, $—C_3$-$C_8$cycloalkyl, and $—C_{1-3}$ alkyl$C_{3-8}$cycloalkyl;

or wherein any two $R^c$, any two $R^d$ or any $R^c$ and $R^d$ optionally combine to form a 3-6 membered cycloalkyl ring;

$R^e$ is independently selected from H, $—C_{1-6}$ alkyl, $—OC_{1-6}$alkyl, $—C_{3-8}$ cycloalkyl, aryl, heteroaryl, heterocyclyl, $—OC_{3-8}$cycloalkyl, —Oaryl, —Oheteroaryl, —Oheterocyclyl, $—C_{1-3}$ alkyl$C_{3-8}$cycloalkyl, $—C_{1-6}$ alkylaryl, $—C_{1-6}$alkylheteroaryl, $—NR^fR^g$, $—C_{1-6}$ alkyl$NR^fR^g$, $C_{1-6}$ alkylC(O)$NR^fR^g$, $—NHSO_2R^f$, $—C_{1-6}$ alkyl$SO_2R^f$, and $—C_{1-6}$ alkyl$SO_2NR^fR^g$;

$R^f$ is independently selected from H, $—C_{1-6}$ alkyl, $—C_{3-8}$ cycloalkyl, aryl, heteroaryl, heterocyclyl, $—C_{1-3}$ alkyl$C_{3-8}$ cycloalkyl, $—C_{1-6}$ alkylaryl, $—C_{1-6}$ alkylheteroaryl, and $—C_{1-6}$ alkylheterocyclyl;

$R^g$ is independently selected from H, $—C_{1-6}$ alkyl, $—C_{3-8}$ cycloalkyl, aryl, heteroaryl, heterocyclyl, $—C_{1-3}$ alkyl$C_{3-8}$ cycloalkyl, $—C_{1-6}$ alkylaryl, $—C_{1-6}$ alkylheteroaryl, and $—C_{1-6}$ alkylheterocyclyl, or a pharmaceutically acceptable salt thereof.

In another embodiment of the disclosure, provided is a compound of formula (I)

$$R^W\text{-}Q^W\text{-}L^W\text{-}Ar^W—Ar^E\text{-}L^E\text{-}Q^E\text{-}R^E \quad (I)$$

wherein:

$Ar^E$ and $Ar^W$ are each independently aryl, heteroaryl, or heterocyclyl;

wherein each aryl, heteroaryl, or heterocyclyl is optionally substituted with 1 to 2 groups independently selected from halo, $—OR^a$, $—C_{1-6}$ alkyl, $—OC_{1-6}$ alkyl, $—C_{1-6}$ haloalkyl, and $—C_{3-8}$cycloalkyl;

$L^E$ and $L^W$ are each independently a bond, —O—, $—(CR^3R^4)_m—$, $—O(CR^3R^4)_m$, $—(CR^3R^4)_mO$, $—(CR^3R^4)_mNR^3$, $—NR^3(CR^3R^4)_m—$, or —C(O)—;

m is independently 0, 1, 2, 3, or 4;

$Q^E$ and $Q^W$ are each independently an aryl or heteroaryl, wherein each aryl or heteroaryl is optionally substituted with 1 to 4 groups independently selected from halo, $—OR^a$, $—N_3$, $—NO_2$, —CN, $—NR^aR^b$, $—SO_2R^a$, $—SO_2NR^aR^b$, $—NR^aSO_2R^a$, $—NR^aC(O)R^a$, $—C(O)NR^aR^b$, $—C_{1-6}$ alkyl, $—OC_{1-6}$alkyl, $—C_{3-8}$cycloalkyl, and $R^N$;

wherein $R^N$ is

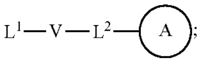;

and $L^1$ is independently a bond, O, $NR^a$, S, SO, or $SO_2$;

V is independently selected from a bond, $C_{1-6}$alkyl, $C_{2-6}$alkenyl, and $C_{2-6}$alkynyl;

wherein the alkyl, alkenyl, or alkynyl group is optionally independently substituted with $OR^a$, halo, cyano, $—NR^aR^b$ or $—C_{3-8}$cycloalkyl;

$L^2$ is independently a bond, O, $NR^a$, S, SO, or $SO_2$;

wherein ring A is independently cycloalkyl, aryl, heteroaryl, or heterocyclyl;

wherein each cycloalkyl, aryl, heteroaryl, or heterocyclyl is optionally independently substituted with 1 to 2 groups independently selected from oxo, $—NO_2$, $—N_3$, $—OR^a$, halo, cyano, $—NR^aR^b$, $—C(O)R^a$, $—C(O)OR^a$, $—OC_{1-6}$alkyCN, $—C(O)NR^aR^b$, $—NR^aC(O)R^a$, $—NR^aC(O)OR^a$, $—NR^aC(O)OR^a$, $—C(O)N(R^a)OR^b$, $—SO_2R^a$, $—SO_2NR^aR^b$, $—NR^aSO_2R^b$, $—NR^aSO_2NR^aR^b$, $—C(O)NR^aSO_2NR^aR^b$, $C_{3-8}$cycloalkyl, and $C_{1-6}$alkyl$C_{3-8}$cycloalkyl;

$R^E$ and $R^W$ are each independently $—NR^1R^2$, $—C_{1-6}$ alky$NR^1R^2$, $—OC_{1-6}$ alkyl$NR^1R^2$, $—C_{1-6}$ alkyl$OC_{1-6}$alkyl$NR^1R^2$, $—NR^aC_{1-6}$ alkyl$NR^1R^2$, $—C(O)NR^1R^2$, $—(CH_2)_uSO_2NR^1R^2$, $—SO_2NR^aC_{1-6}$alkyl$NR^1R^2$, $—NR^aSO_2C_{1-6}$alkyl$NR^1R^2$, or

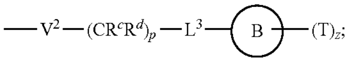;

wherein $V^2$ is independently a bond, O, $NR^a$, S, SO, or $SO_2$ $L^3$ is independently a bond, O, $NR^a$, S, SO, or $SO_2$;

ring B is cycloalkyl, aryl, heteroaryl, or heterocyclyl;

T is $(CH_2)_qNR^1R^2$, or $(CH_2)_qC(O)R^e$;

p is 0, 1, 2, or 3;

q is 0, 1, 2, or 3;

u is 0, 1, 2, or 3;

and wherein the alkyl, cycloalkyl, aryl, heteroaryl, or heterocyclyl group is optionally substituted with 1 to 3 substituents independently selected from the group consisting of —$NR^aR^b$, halo, cyano, oxo, $OR^a$, —$C_{1-6}$alkyl, —$C_{1-6}$haloalkyl, —$C_{1-6}$cyanoalkyl, —$C_{1-6}$alkyNR$^a$R$^b$, —$C_{1-6}$alkylOH, —$C_{3-8}$cycloalkyl, and —$C_{1-3}$ alkyl$C_{3-8}$cycloalkyl;

provided that at least one of $V^2$, $L^3$, ring B and T contains a nitrogen atom;

$R^1$ is selected from H, —$C_{1-6}$ alkylaryl, heterocyclyl, —$C_{1-6}$ alkylheteroaryl, —$C_{1-6}$ alkylheterocyclyl, —$C_{1-6}$ alkylC(O)OR$^a$, —$C_{2-6}$ alkenylC(O)OR$^a$, and $C_{1-6}$ alkyl$C_{3-8}$cycloalkyl;

wherein each alkyl, cycloalkyl, aryl, heteroaryl, or heterocyclyl is optionally substituted with 1 to 2 groups independently selected from —$OR^a$, oxo, —CN, halo, $C_{1-6}$alkyl, —$C_{1-6}$ alkylOR$^a$, —$C_{1-6}$cyanoalkyl, —$C_{1-6}$haloalkyl, $C_{3-8}$cycloalkyl, —$C_{1-3}$alkyl$C_{3-8}$cycloalkyl, —C(O)R$^a$, —$C_{1-6}$ alkylC(O)R$^a$, —C(O)OR$^a$, —$C_{1-6}$ alkylC(O)OR$^a$, —$NR^aR^b$, —$C_{1-6}$ alkylNR$^a$R$^b$, —C(O)NR$^a$R$^b$, —$C_{1-6}$ alkylC(O)NR$^a$R$^b$, —$SO_2R^a$, —$C_{1-6}$ alkylSO$_2$R$^a$, —$SO_2N^aR^b$, —$C_{1-6}$ alkylSO$_2$NR$^a$R$^b$, —C(O)NR$^a$SO$_2$R, —$C_{1-6}$ alkylC(O)NR$^a$SO$_2$R$^b$, —NR$^a$C(O)R$^b$, and —$C_{1-6}$alkyNR$^a$C(O)R$^b$;

$R^2$ is selected from —$C_{1-6}$alkyl, —$C_{2-6}$ alkenyl, —$C_{3-6}$ cycloalkyl, aryl, heteroaryl, heterocyclyl, —$C_{1-6}$ alkylaryl, —$C_{1-6}$ alkylheteroaryl, —$C_{1-6}$ alkylheterocyclyl, —$C_{2-6}$alkyl-OR$^a$, —$C_{1-6}$ alkylC(O)OR$^a$, and —$C_{2-6}$ alkenylC(O)OR$^a$;

wherein each alkyl, alkenyl, cycloalkyl, aryl, heteroaryl, or heterocycle is optionally substituted with 1 to 3 groups independently selected from —$OR^a$, —CN, halo, —$C_{1-6}$ alkylOR$^a$, —$C_{1-6}$ cyanoalkyl, —$C_{1-6}$haloalkyl, —$C_{3-8}$ cycloalkyl, —$C_{1-3}$ alkyl $C_{3-8}$cycloalkyl, —C(O)R$^a$, —$C_{1-6}$ alkylC(O)R$^a$, —C(O)OR$^a$, —$C_{1-6}$alkylC(O)OR$^a$, —$NR^aR^b$, —$C_{1-6}$alkyNR$^a$R$^b$, —C(O)NR$^a$R$^b$, $C_{1-6}$alkylC(O)NR$^a$R$^b$, —$SO_2R^a$, —$C_{1-6}$ alkylSO$_2$R$^a$, —$SO_2NR^aR^b$, —$C_{1-6}$ alkylSO$_2$NR$^a$R$^b$, —C(O)NR$^a$SO$_2$R$^b$, and —NR$^a$C(O)R$^b$;

or $R^1$ and $R^2$ combine to form a heterocyclyl group optionally containing 1, 2, or 3 additional heteroatoms independently selected from oxygen, sulfur or nitrogen, and optionally substituted with 1 to 3 groups independently selected from oxo, —$C_{1-6}$alkyl, —$C_{3-8}$cycloalkyl, —$C_{2-6}$ alkenyl, —$C_{2-6}$ alkynyl, —$OR^a$, —C(O)OR$^a$, —$C_{1-6}$cyanoalkyl, —$C_{1-6}$alkylOR$^a$, —$C_{1-6}$haloalkyl, —$C_{1-3}$alkyl$C_{3-8}$cycloalkyl, —C(O)R$^a$, $C_{1-6}$alkylC(O)R$^a$, —$C_{1-6}$alkylC(O)OR$^a$, —$NR^aR^b$, —$C_{1-6}$alkyNR$^a$R$^b$, —C(O)NR$^a$R$^b$, —$C_{1-6}$alkylC(O)NR$^a$R$^b$, —$SO_2R^a$, —$C_{1-6}$ alkylSO$_2$R$^a$, —$SO_2NR^aR^b$, and $C_{1-6}$ alkylSO$_2$NR$^a$R$^b$;

$R^3$ is independently H, halo, —$C_{1-6}$alkyl, —OH, —$OCH_3$, or —$OCH_2CH_3$;

$R^4$ is independently H, halo, —$C_{1-6}$alkyl, —OH, —$OCH_3$, or —$OCH_2CH_3$;

$R^a$ is independently selected from H, —$C_{1-6}$alkyl, —$C_{3-8}$ cycloalkyl, and —$C_{1-3}$ alkyl$C_{3-8}$cycloalkyl;

$R^b$ is independently selected from H, —$C_{1-6}$alkyl, —$C_{3-8}$ cycloalkyl, and —$C_{1-3}$ alkyl$C_{3-8}$cycloalkyl;

$R^c$ is independently selected from H, —$C_{1-6}$alkyl, —$C_3$-8cycloalkyl, and —$C_{1-3}$ alkyl$C_{3-8}$cycloalkyl;

$R^d$ is independently selected from H, —$C_{1-6}$alkyl, —$C_3$-$C_8$cycloalkyl, and —$C_{1-3}$alkyl$C_{3-8}$cycloalkyl;

and wherein any two $R^c$, any two $R^d$ or any $R^c$ and $R^d$ optionally combine to form a 3-6 membered cycloalkyl ring;

$R^e$ is independently selected from H, —$C_{1-6}$alkyl, —O$C_{1-6}$alkyl, —$C_{3-8}$cycloalkyl, aryl, heteroaryl, heterocyclyl, —O$C_{3-8}$cycloalkyl, —Oaryl, —Oheteroaryl, —Oheterocyclyl, —$C_{1-3}$ alkyl$C_{3-8}$cycloalkyl, —$C_{1-6}$ alkylaryl, —$C_{1-6}$alkylheteroaryl, —$NR^fR^g$, —$C_{1-6}$ alkylNR$^f$R$^g$, $C_{1-6}$ alkylC(O)NR$^f$R$^g$, —NHSO$_2$R$^f$, —$C_{1-6}$ alkylSO$_2$R$^f$, and —$C_{1-6}$ alkylSO$_2$NR$^f$R$^g$;

$R^f$ is independently selected from H, —$C_{1-6}$alkyl, —$C_{3-8}$ cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl;

$R^g$ is independently selected from H, —$C_{1-6}$alkyl, —$C_{3-8}$ cycloalkyl, aryl, heteroaryl, heterocyclyl, —$C_{1-3}$ alkyl$C_{3-8}$ cycloalkyl, —$C_{1-6}$ alkylaryl, —$C_{1-6}$ alkylheteroaryl, and —$C_{1-6}$alkylheterocyclyl, or a pharmaceutically acceptable salt thereof.

In another embodiment of the disclosure is provided a compound of formula (I)

$$R^W\text{-}Q^W\text{-}L^W\text{-}Ar^W\text{—}Ar^E\text{-}L^E\text{-}Q^E\text{-}R^E \quad (I)$$

wherein:

$Ar^E$ and $Ar^W$ are each independently aryl, heteroaryl, or heterocyclyl;

wherein each aryl, heteroaryl, or heterocyclyl is optionally substituted with 1 to 2 groups independently selected from halo, —$OR^a$, —$C_{1-6}$ alkyl, —O$C_{1-6}$alkyl, —$C_{1-6}$ haloalkyl, and —$C_{3-8}$cycloalkyl;

$L^E$ and $L^W$ are each independently a bond, —O—, —$(CR^3R^4)_m$—, —O$(CR^3R^4)_m$, —$(CR^3R^4)_m$O, —$(CR^3R^4)_m$NR$^3$, —NR$^3$$(CR^3R^4)_m$—, or —C(O)— m is independently 0, 1, 2, 3 or 4; and $Q^E$ and $Q^W$ are each an aryl group optionally substituted with 1 to 4 groups independently selected from halo, —$OR^a$, —$N_3$, —$NO_2$, —CN, —$NR^aR^b$, —$SO_2R^a$, —$SO_2NR^aR^b$, —$NR^aSO_2R^a$, —NR$^a$C(O)R$^a$, —C(O)NR$^a$R$^b$, —$C_{1-6}$ alkyl, —O$C_{1-6}$alkyl, —$C_{3-8}$cycloalkyl, and $R^N$;

wherein $R^N$ is

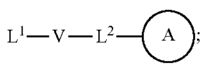

wherein $L^1$ is independently a bond, O, NR$^a$, S, SO, or SO$_2$;

V is independently selected from a bond, $C_{1-6}$alkyl, $C_{2-6}$alkenyl, and $C_{2-6}$alkynyl;

wherein each alkyl, alkenyl, or alkynyl is optionally independently substituted with OR$^a$, halo, cyano, —$NR^aR^b$ and —$C_{3-8}$cycloalkyl;

$L^2$ is independently a bond, O, NR$^a$, S, SO, or SO$_2$;

ring A is independently cycloalkyl, aryl, heteroaryl, or heterocyclyl;

wherein each cycloalkyl, aryl, heteroaryl, or heterocyclyl is optionally independently substituted with 1 to 2 groups independently selected from oxo, —$NO_2$, —$N_3$, —$OR^a$, halo, cyano, —$NR^aR^b$, —C(O)R$^a$, —C(O)OR$^a$, —O$C_{1-6}$alkyCN, —C(O)NR$^a$R$^b$, —NR$^a$C(O)R$^a$, —NR$^a$C(O)OR$^a$, —NR$^a$C(O)OR$^a$, —C(O)N(R$^a$)OR$^b$, —$SO_2R^a$, —$SO_2NR^aR^b$, —$NR^aSO_2R^b$, —$NR^aSO_2NR^aR^b$, —$C(O)NR^aSO_2NR^aR^b$, $C_{3-8}$cycloalkyl, and $C_{1-6}$alkyl$C_{3-8}$cycloalkyl;

$R^E$ and $R^W$ are each independently —$NR^1R^2$, —$C_{1-6}$ alkyNR$^1$R$^2$, —$OC_{1-6}$ alkylNR$^1$R$^2$, —$C_{1-6}$ alkyl $OC_{1-6}$alkylNR$^1$R$^2$, —$NR^aC_{1-6}$ alkylNR$^1$R$^2$, —C(O) $NR^1R^2$, —$(CH_2)_uSO_2NR^1R^2$, —$SO_2NR^a$ $C_{1-6}$alkylNR$^1$R$^2$, —$NR^aSO_2C_{1-6}$alkylNR$^1$R$^2$ or

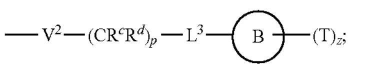

wherein $V^2$ is independently a bond, O, $NR^a$, S, SO, or $SO_2$ $L^3$ is independently a bond, O, $NR^a$, S, SO, or $SO_2$;

ring B is cycloalkyl, aryl, heteroaryl, or heterocyclyl;

T is $(CH_2)_qNR^1R^2$ or $(CH_2)_qC(O)R^e$;

p is 0, 1, 2, or 3;

q is 0, 1, 2, or 3;

u is 0, 1, 2, or 3;

and wherein the alkyl, cycloalkyl, aryl, heteroaryl, or heterocyclyl group is optionally substituted with 1 to 3 substituents independently selected from the group consisting of $NR^aR^b$, halo, cyano, oxo, $OR^a$, —$C_{1-6}$alkyl, —$C_{1-6}$haloalkyl, —$C_{1-6}$cyanoalkyl, —$C_{1-6}$alkyNR$^a$R$^b$, —$C_{1-6}$alkylOH, —$C_{3-8}$ cycloalkyl, and —$C_{1-3}$ alkyl$C_{3-8}$cycloalkyl;

provided that at least one of $V^2$, $L^3$, ring B and T contains a nitrogen atom;

$R^1$ is selected from H, —$C_{1-6}$ alkylaryl, heterocyclyl, —$C_{1-6}$ alkylheteroaryl, —$C_{1-6}$ alkylheterocyclyl, —$C_{1-6}$ alkylC(O)OR$^a$, —$C_{2-6}$ alkenylC(O)OR$^a$, and $C_{1-6}$ alkyl$C_{3-8}$cycloalkyl;

wherein each alkyl, cycloalkyl, aryl, heteroaryl, or heterocyclyl is optionally substituted with 1 to 2 groups independently selected from —$OR^a$, oxo, —CN, halo, $C_{1-6}$ alkyl, —$C_{1-6}$ alkylOR$^a$, —$C_{1-6}$cyanoalkyl, —$C_{1-6}$haloalkyl, $C_{3-8}$cycloalkyl, —$C_{1-3}$alkyl$C_{3-8}$cycloalkyl, —$C(O)R^a$, —$C_{1-6}$ alkylC(O)R$^a$, —$C(O)OR^a$, —$C_{1-6}$ alkylC(O)OR$^a$, —$NR^aR^b$, —$C_{1-6}$ alkylNR$^a$R$^b$, —$C(O)NR^aR^b$, —$C_{1-6}$ alkylC (O)NR$^a$R$^b$, —$SO_2R^a$, —$C_{1-6}$ alkylSO$_2$R$^a$, —$SO_2N^aR^b$, —$C_{1-6}$ alkylSO$_2$NR$^a$R$^b$, —C(O) $NR^aSO_2R$, —$C_{1-6}$alkylC(O)NR$^a$SO$_2$R$^b$, —$NR^aC$ (O)R$^b$, and —$C_{1-6}$alkyNR$^a$C(O)R$^b$;

$R^2$ is selected from —$C_{1-6}$alkyl, —$C_{2-6}$ alkenyl, —$C_{3-6}$ cycloalkyl, aryl, heteroaryl, heterocyclyl, —$C_{1-6}$ alkylaryl, —$C_{1-6}$ alkylheteroaryl, —$C_{1-6}$ alkylheterocyclyl, —$C_{2-6}$alkyl-OR$^a$, —$C_{1-6}$ alkylC(O)OR$^a$, and —$C_{2-6}$ alkenylC(O)OR$^a$;

wherein each alkyl, alkenyl, cycloalkyl, aryl, heteroaryl, or heterocyclyl is optionally substituted with 1 to 3 groups independently selected from —$OR^a$, —CN, halo, —$C_{1-6}$ alkylOR$^a$, —$C_{1-6}$ cyanoalkyl, —$C_{1-6}$haloalkyl, —$C_{3-8}$cycloalkyl, —$C_{1-3}$ alkyl $C_{3-8}$cycloalkyl, —$C(O)R^a$, —$C_{1-6}$ alkylC(O)R$^a$, —$C(O)OR^a$, —$C_{1-6}$alkylC(O)OR$^a$, —$NR^aR^b$, —$C_{1-6}$alkylNR$^a$R$^b$, —$C(O)NR^aR^b$, —$C_{1-6}$alkylC (O)NR$^a$R$^b$, —$SO_2R^a$, —$C_{1-6}$ alkylSO$_2$R$^a$, —$SO_2NR^aR^b$, —$C_{1-6}$ alkylSO$_2$NR$^a$R$^b$, —C(O) $NR^aSO_2R^b$, and —$NR^aC(O)R^b$;

or $R^1$ and $R^2$ combine to form a heterocyclyl optionally containing 1, 2, or 3 additional heteroatoms independently selected from oxygen, sulfur or nitrogen, and optionally substituted with 1 to 3 groups independently selected from oxo, —$C_{1-6}$alkyl, —$C_{3-8}$ cycloalkyl, —$C_{2-6}$ alkenyl, —$C_{2-6}$ alkynyl, —$OR^a$, —$C(O)OR^a$, —$C_{1-6}$cyanoalkyl, —$C_{1-6}$alkylOR$^a$, —$C_{1-6}$haloalkyl, —$C_{1-3}$alkyl$C_{3-8}$cycloalkyl, —$C(O)R^a$, —$C_{1-6}$ alkylC (O)R$^a$, —$C_{1-6}$ alkylC(O)OR$^a$, —$NR^aR^b$, —$C_{1-6}$alkylNR$^a$R$^b$, —$C(O)NR^aR^b$, —$C_{1-6}$ alkylC(O)NR$^a$R$^b$, —$SO_2R^a$, —$C_{1-6}$ alkylSO$_2$R$^a$, —$SO_2NR^aR^b$, and $C_{1-6}$ alkylSO$_2$NR$^a$R$^b$;

$R^3$ is independently H, halo, —$C_{1-6}$alkyl, —OH, —$OCH_3$, or —$OCH_2CH_3$;

$R^4$ is independently H, halo, —$C_{1-6}$alkyl, —OH, —$OCH_3$, or —$OCH_2CH_3$;

$R^a$ is independently selected from H, —$C_{1-6}$alkyl, —$C_{3-8}$ cycloalkyl, and —$C_{1-3}$ alkyl$C_{3-8}$cycloalkyl;

$R^b$ is independently selected from H, —$C_{1-6}$alkyl, —$C_{3-8}$ cycloalkyl, and —$C_{1-3}$ alkyl$C_{3-8}$cycloalkyl;

$R^c$ is independently selected from H, —$C_{1-6}$alkyl, —$C_{3-8}$ cycloalkyl, and —$C_{1-3}$ alkyl$C_{3-8}$ cycloalkyl;

$R^d$ is independently selected from H, —$C_{1-6}$alkyl, —$C_3$-$C_8$cycloalkyl, and —$C_{1-3}$alkyl$C_{3-8}$cycloalkyl;

and wherein any two $R^c$, any two $R^d$ or any $R^c$ and $R^d$ optionally combine to form a 3-6 membered cycloalkyl ring;

$R^e$ is independently selected from H, —$C_{1-6}$alkyl, —$OC_{1-6}$alkyl, —$C_{3-8}$cycloalkyl, aryl, heteroaryl, heterocyclyl, —$OC_{3-8}$cycloalkyl, —Oaryl, —Oheteroaryl, —Oheterocyclyl, —$C_{1-3}$ alkyl$C_{3-8}$cycloalkyl, —$C_{1-6}$ alkylaryl, —$C_{1-6}$alkylheteroaryl, —$NR^fR^g$, —$C_{1-6}$ alkylNR$^f$R$^g$, $C_{1-6}$ alkylC(O)NR$^f$R$^g$, —$NHSO_2R^f$, —$C_{1-6}$ alkylSO$_2$R$^f$, and —$C_{1-6}$ alkylSO$_2$NR$^f$R$^g$;

$R^f$ is independently selected from H, —$C_{1-6}$alkyl, —$C_{3-8}$ cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl;

$R^g$ is independently selected from H, —$C_{1-6}$ alkyl, —$C_{3-8}$ cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl, or a pharmaceutically acceptable salt thereof.

In one embodiment, at least one of $Ar^E$ and $Ar^W$ is other than optionally substituted aryl. In one embodiment, at least one of $Ar^E$ and $Ar^W$ is other than optionally substituted phenyl.

In one embodiment, when both of $Ar^E$ and $Ar^W$ are optionally substituted aryl, then the moiety -$L^E$-$Ar^E$$Ar^W$-$L^W$- is —O—$(CR^3R^4)_m$—$Ar^E$—$Ar^W$-$L^W$-$(CR^3R^4)_m$—O—. In one embodiment, the moiety -$L^E$-$Ar^E$—$Ar^W$-$L^W$- is —O—$(CR^3R^4)_m$—$Ar_E$—$Ar^W$-$L^W$-$(CR^3R^4)_m$—O—.

In one embodiment, both of $Q^E$ and $Q^W$ are independently optionally substituted aryl. In one embodiment, both of $Q^E$ and $Q^W$ are independently optionally substituted phenyl. In one embodiment, both of $Q^E$ and $Q^W$ are independently optionally substituted pyridyl.

In one embodiment of any compound described herein, both $Ar^E$ and $Ar^W$ are optionally substituted bicyclic rings, wherein neither is an optionally substituted fused 5,6-aromatic or 5,6-heteromatic ring. In one embodiment of any compound described herein, both $L^E$ and $L^W$ are —O—. In one embodiment of any compound described herein, both $L^E$ and $L^W$ are -Q-O—$CH_2$—Ar—. In one embodiment of any compound described herein, each of $Ar^E$ W $Q^E$, and $Q^W$ are monocyclic, provided at least two are heteroaryl, and neither of $R^E$, and $R^W$ is an optionally substituted fused 5,6-aromatic or 5,6-heteromatic ring. In one embodiment of any compound described herein, at least one L is a bond, and none of $Ar^E$, $Ar^W$, $Q^E$, $Q^W$, $R^E$, and $R^W$ is an optionally substituted fused 5,6-aromatic or 5,6-heteromatic ring. In one embodiment of any compound described herein, at least one of the following occurs: a) both $Ar^E$ and $Ar^W$ are optionally substituted bicyclic rings, wherein neither is an optionally substituted fused 5,6-aromatic or 5,6-heteromatic ring; b) both $L^E$ and $L^W$ are —O—; c) both $L^E$ and $L^W$ are -Q-O—$CH_2$—Ar—; d) each of $Ar^E$, $Ar^W$, $Q^E$, and $Q^W$ are monocyclic, provided at least two are heteroaryl, and neither of $R^E$, and $R^W$ is an optionally substituted fused 5,6-aromatic or 5,6-heteromatic ring; or e) at least one L is a bond, and none of $Ar^E$, $Ar^W$, $Q^E$, $Q^W$, $R^E$, and $R^W$ is an optionally substituted fused 5,6-aromatic or 5,6-heteromatic ring.

In one embodiment provided is a compound selected from Example 92, 209, 124, 121, 402, 123, 43, 122, 16, 240, 167, 90, 210, 178, 42, 148, 93, 32, 111, 74, 172, 166, 160, 183, 225, 125, 162, 214, 40, 220, 213, 114, 41, 127, 113, 185, 34, 144, 94, 143, 286, 128, 142, 140, 279, 29, 49, 221, 241, 112, 133, 242, 35, 253, 168, 66, 161, 126, 153, 232, 252, 163, 57, 165, 110, 145, 79, 75, 244, 132, 138, 243, 78, 48, 215, 258, 182, 234, 282, 260, 157, 281, 164, 47, 259, 216, 91, 136, 159, 248, 68, 219, 217, 280, 152, 227, 95, 12, 179, 257, 134, 109, 28, 149, 218, 31, 254, 203, 116, 53, 256, 226, 247, 117, 175, 135, 230, 58, 118, 404, 222, 200, 37, 70, 96, 204, 231, 131, 268, 54, 71, 76, 36, 201, 246, 147, 405, 59, 264, 120, 67, 21, 266, 184, 137, 284, 55, 207, 17, 83, 82, 69, 202, 276, 22, 199, 146, 73, 38, 261, 245, 88, 236, 19, 15, 155, 61, 265, 85, 64, 84, 233, 14, 62, 1394, 158, 272, 30, 77, 150, 80, 151, 81, 154, 255, 235, 56, 141, 23, 86, 104, 39, 60, 269, 87, 115, 173, 174, 270, 271, 223, 273, 406, 237, 277, 249, 170, 18, 63, 105, ((5-bromo-6-((3'-(((3-bromo-5-(((carboxymethyl)amino)methyl)-6-(((R)-5-oxopyrrolidin-2-yl)methoxy)pyridin-2-yl)oxy)methyl)-2,2'-dimethyl-[1,1'-biphenyl]-3-yl)methoxy)-2-(((S)-5-oxopyrrolidin-2-yl)methoxy)pyridin-3-yl)methyl)glycine, (S)-4-(((5-(3'-((4-((((S)-3-carboxy-2-hydroxypropyl)amino)methyl)-2-chloro-5-((5-cyanopyridin-3-yl)methoxy)phenoxy)methyl)-2,2'-dimethyl-[1,1'-biphenyl]-3-yl)benzo[b]thiophen-2-yl)methyl)amino)-3-hydroxybutanoic acid, and (S)-4-((5-bromo-4-((3'-((2-bromo-4-((((S)-3-carboxy-2-hydroxypropyl)amino)methyl)-5-((5-cyanopyridin-3-yl)methoxy)phenoxy)methyl)-2,2'-dimethyl-[1,1'-biphenyl]-3-yl)methoxy)-2-((5-isocyanopyridin-3-yl)methoxy)benzyl)amino)-3-hydroxybutanoic acid, or a pharmaceutically acceptable salt thereof.

In one embodiment provided is a compound selected from Example 191, 198, 197, 193, 189, 196, 192, 195, 190, 20, 194, 186, 188, 72, 187, 25, and 285, or a pharmaceutically acceptable salt thereof.

In one embodiment provided is a compound selected from Example 4, 5, 3, 7, 6, 8, 9, 2, 10, 1, 407, and 13, or a pharmaceutically acceptable salt thereof.

In one embodiment provided is a compound selected from Example 267, 180, 181, 408, 409, 410, 411, 412, 413, 414, 415, 416, 417, 418, 419, and 420, or a pharmaceutically acceptable salt thereof.

In one embodiment provided is a compound selected from Example 191, 198, 197, 193, 189, 196, 192, 195, 190, 20, 194, 186, 188, 72, 187, 25, and 285, or a pharmaceutically acceptable salt thereof.

In one embodiment provided is a compound selected from Example 287, 102, 103, 27, 251, and 107, or a pharmaceutically acceptable salt thereof.

In one embodiment provided is a compound selected from Example 239 and 238, or a pharmaceutically acceptable salt thereof.

In one embodiment provided is a compound selected from Example 97, 44, 98, 50, 51, 45, 99, 169, 100, 89, 274, 422, 24, 176, 65, 171, 26, 52, 156, and 263, or a pharmaceutically acceptable salt thereof.

In one embodiment provided is a compound selected from Example 423, 29, 113, 34, 240, 6, 7, 66, 16, and 19, or a pharmaceutically acceptable salt thereof.

In one embodiment, the compound is represented by formula (Ia):

(Ia)

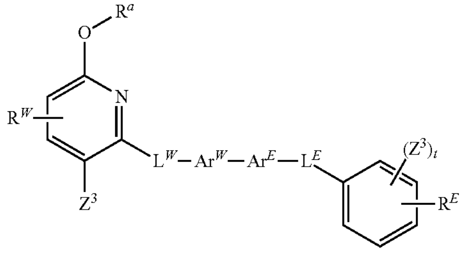

where, each $Z^3$ is independently halo, —$OR^a$, —$N_3$, —$NO_2$, —CN, —$NR^1R^2$, —$SO_2R^a$, —$SO_2N^aR^b$, —$NR^aSO_2R^a$, —$NR^aC(O)R^a$, —$C(O)R^a$, —$C(O)OR^a$, —$C(O)NR^aR^b$, —$NR^aC(O)OR^a$, —$NR^aC(O)NR^1R^2$, —$OC(O)NR^aR^b$, —$NR^aSO_2NR^aR^b$, —$C(O)NR^aSO_2NR^aR^b$, —$C_{1-6}$ alkyl, —$C_{2-6}$ alkenyl, —$C_{2-6}$ alkynyl, —$OC_{1-6}$ alkyl, —$C_{3-8}$ cycloalkyl, —$C_{1-6}$ alkyl$C_{3-8}$ cycloalkyl, aryl, heteroaryl, heterocyclyl, and $R^N$;

wherein the alkyl, alkenyl, alkynyl, $C_{3-8}$ cycloalkyl, aryl, heteroaryl, or heterocyclyl group is optionally substituted with 1 to 4 groups independently selected from oxo, —$NO_2$, —$N_3$, —$OR^a$, halo, cyano, —$NR^aR^b$, —$C(O)R^a$, —$C(O)OR^a$, —$OC_{1-6}$ alkyCN, —$C(O)NR^aR^b$, $NR^aC(O)R^a$, —$NR^aC(O)OR^a$, —$SO_2R^a$, —$NR^aSO_2R$, —$SO_2NR^aR^b$, —$NR^aSO_2NR^aR^b$, —$C(O)NR^aSO_2NR^aR^b$ and —$C_{3-8}$ cycloalkyl; and wherein the heteroaryl or heterocyclic group may be oxidized on a nitrogen atom to form an N-oxide or oxidized on a sulfur atom to form a sulfoxide or sulfone; and t is 0, 1 or 2; and each of $Ar^E$, $Ar^W$, $R^E$, $R^W$, $L^E$, $L^W$, $R^N$, $R^a$, and $R^b$ are as defined herein.

In one embodiment of formula (Ia), $L^E$ is other than —$CH_2O$—, —$(CH_2)_2$—, —CH═CH—, and —C(O)NH—. In one embodiment of formula (Ia), none of $Ar^E$, $Ar^W$, $Q^E$, $Q^W$, $R^E$, and $R^W$ is an optionally substituted fused 5,6-aromatic or 5,6-heteromatic ring.

In one embodiment, the compound is represented by any one of formula (Ib):

(Ib)

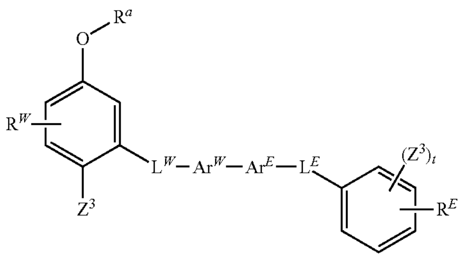

where each $Z^3$ is independently halo, $—OR^a$, $—N_3$, $—NO_2$, —CN, $—NR^1R^2$, $—SO_2R^a$, $—SO_2NR^aR^b$, $—NR^aSO_2R^a$, $—NR^aC(O)R^a$, $—C(O)R^a$, $—C(O)OR^a$, $—C(O)NR^aR^b$, $—NR^aC(O)OR^a$, $—NR^aC(O)NR^1R^2$, $—OC(O)NR^aR^b$, $—NR^aSO_2NR^aR^b$, $—C(O)NR^aSO_2NR^aR^b$, $—C_{1-6}$ alkyl, $—C_{2-6}$ alkenyl, $—C_{2-6}$ alkynyl, $—OC_{1-6}$ alkyl, $—C_{3-8}$ cycloalkyl, $—C_{1-6}$ alkyl$C_{3-8}$ cycloalkyl, aryl, heteroaryl, heterocyclyl, and $R^N$;

wherein the alkyl, alkenyl, alkynyl, $C_{3-8}$ cycloalkyl, aryl, heteroaryl, or heterocyclyl group is optionally substituted with 1 to 4 groups independently selected from oxo, $—NO_2$, $—N_3$, $—OR^a$, halo, cyano, $—NR^aR^b$, $—C(O)R^a$, $—C(O)OR^a$, $—OC_{1-6}$ alkyCN, $—C(O)NR^aR^b$, $NR^aC(O)R^a$, $—NR^aC(O)OR^a$, $—SO_2R^a$, $—NR^aSO_2R$, $—SO_2NR^aR^b$, $—NR^aSO_2NR^aR^b$, $—C(O)NR^aSO_2NR^aR^b$ and $—C_{3-8}$ cycloalkyl; and wherein the heteroaryl or heterocyclic group may be oxidized on a nitrogen atom to form an N-oxide or oxidized on a sulfur atom to form a sulfoxide or sulfone; and t is 0, 1 or 2; and each of $Ar^E$, $Ar^W$, $R^E$, $R^W$, $L^E$, $L^W$, $R^N$, $R^a$, and $R^b$ are as defined herein.

In one embodiment of formula (Ib), $L^W$ and $L^E$ are other than $—CH_2O—$, $—(CH_2)_2—$, —CH═CH—, and —C(O)NH—. In one embodiment of formula (Ib), $L^E$ is other than $—CH_2—$, $—(CH_2)_2—$, —CH═CH—, and —C(O)NH—. In one embodiment of formula (Ib), $L^W$ is other than $—CH_2—$, $—(CH_2)_2—$, —CH═CH—, and —C(O)NH—. In one embodiment of formula (Ib), none of $Ar^E$, $Ar^W$, $Q^E$, $Q^W$, $R^E$, and $R^W$ is an optionally substituted fused 5,6-aromatic or 5,6-heteromatic ring.

In one embodiment, the compound is represented by formula (Ic):

(Ic)

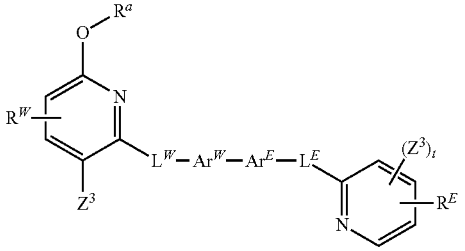

where each $Z^3$ is independently halo, $—OR^a$, $—N_3$, $—NO_2$, —CN, $—NR^1R^2$, $—SO_2R^a$, $—SO_2N^aR^b$, $—NR^aSO_2R^a$, $—NR^aC(O)R^a$, $—C(O)R^a$, $—C(O)OR^a$, $—C(O)NR^aR^b$, $—NR^aC(O)OR^a$, $—NR^aC(O)NR^1R^2$, $—OC(O)NR^aR^b$, $—NR^aSO_2NR^aR^b$, $—C(O)NR^aSO_2NR^aR^b$, $—C_{1-6}$ alkyl, $—C_{2-6}$ alkenyl, $—C_{2-6}$ alkynyl, $—OC_{1-6}$ alkyl, $—C_{3-8}$ cycloalkyl, $—C_{1-6}$ alkyl$C_{3-8}$ cycloalkyl, aryl, heteroaryl, heterocyclyl, and $R^N$;

wherein the alkyl, alkenyl, alkynyl, $C_{3-8}$ cycloalkyl, aryl, heteroaryl, or heterocyclyl group is optionally substituted with 1 to 4 groups independently selected from oxo, $—NO_2$, $—N_3$, $—OR^a$, halo, cyano, $—NR^aR^b$, $—C(O)R^a$, $—C(O)OR^a$, $—OC_{1-6}$ alkyCN, $—C(O)NR^aR^b$, $NR^aC(O)R^a$, $—NR^aC(O)OR^a$, $—SO_2R^a$, $—NR^aSO_2R^b$, $—SO_2NR^aR^b$, $—NR^aSO_2NR^aR^b$, $—C(O)NR^aSO_2NR^aR^b$ and $—C_{3-8}$ cycloalkyl; and wherein the heteroaryl or heterocyclic group may be oxidized on a nitrogen atom to form an N-oxide or oxidized on a sulfur atom to form a sulfoxide or sulfone; and t is 0, 1 or 2; and each of $Ar^E$, $Ar^W$, $R^E$, $R^W$, $L^E$, $L^W$, $R^N$, $R^a$, and $R^b$ are as defined herein.

In one embodiment of formula (Ic), none of $Ar^E$, $Ar^W$, $Q^E$, $Q^W$, $R^E$, and $R^W$ is an optionally substituted fused 5,6-aromatic or 5,6-heteromatic ring.

In one embodiment, the compound is represented by formula (Id):

(Id)

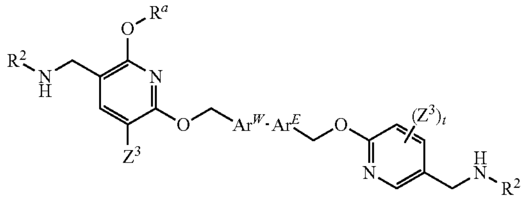

where each $Z^3$ is independently halo, $—OR^a$, $—N_3$, $—NO_2$, —CN, $—NR^1R^2$, $—SO_2R^a$, $—SO_2N^aR^b$, $—NR^aSO_2R^a$, $—NR^aC(O)R^a$, $—C(O)R^a$, $—C(O)OR^a$, $—C(O)NR^aR^b$, $—NR^aC(O)OR^a$, $—NR^aC(O)NR^1R^2$, $—OC(O)NR^aR^b$, $—NR^aSO_2NR^aR^b$, $—C(O)NR^aSO_2NR^aR^b$, $—C_{1-6}$ alkyl, $—C_{2-6}$ alkenyl, $—C_{2-6}$ alkynyl, $—OC_{1-6}$ alkyl, $—C_{3-8}$ cycloalkyl, $—C_{1-6}$ alkyl$C_{3-8}$ cycloalkyl, aryl, heteroaryl, heterocyclyl, and $R^N$;

wherein the alkyl, alkenyl, alkynyl, $C_{3-8}$ cycloalkyl, aryl, heteroaryl, or heterocyclyl group is optionally substituted with 1 to 4 groups independently selected from oxo, $—NO_2$, $—N_3$, $—OR^a$, halo, cyano, $—NR^aR^b$, $—C(O)R^a$, $—C(O)OR^a$, $—OC_{1-6}$ alkyCN, $—C(O)NR^aR^b$, $NR^aC(O)R^a$, $—NR^aC(O)OR^a$, $—SO_2R^a$, $—NR^aSO_2R$, $—SO_2NR^aR^b$, $—NR^aSO_2NR^aR^b$, $—C(O)NR^aSO_2NR^aR^b$ and $—C_{3-8}$ cycloalkyl; and wherein the heteroaryl or heterocyclic group may be oxidized on a nitrogen atom to form an N-oxide or oxidized on a sulfur atom to form a sulfoxide or sulfone;

t is 0, 1 or 2; and each $Ar^E$, $Ar^W$, $R^2$, $R^N$, $R^a$, and $R^b$ are as defined herein.

In one embodiment, the compound is represented by formulas (Ie):

(Ie)

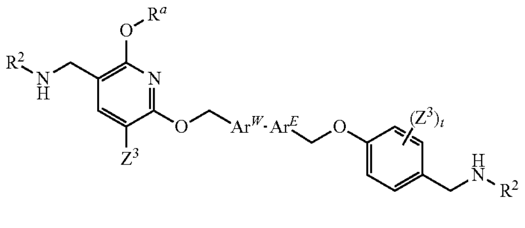

where each $Z^3$ is independently halo, —$OR^a$, —$N_3$, —$NO_2$, —CN, —$NR^1R^2$, —$SO_2R^a$, —$SO_2N^aR^b$, —$NR^aSO_2R^a$, —$NR^aC(O)R^a$, —$C(O)R^a$, —$C(O)OR^a$, —$C(O)NR^aR^b$, —$NR^aC(O)OR^a$, —$NR^aC(O)NR^1R^2$, —$OC(O)NR^aR^b$, —$NR^aSO_2NR^aR^b$, —$C(O)NR^aSO_2NR^aR^b$, —$C_{1-6}$ alkyl, —$C_{2-6}$ alkenyl, —$C_{2-6}$ alkynyl, —$OC_{1-6}$ alkyl, —$C_{3-8}$cycloalkyl, —$C_{1-6}$ alkyl$C_{3-8}$ cycloalkyl, aryl, heteroaryl, heterocyclyl, and $R^N$;

wherein the alkyl, alkenyl, alkynyl, $C_{3-8}$ cycloalkyl, aryl, heteroaryl, or heterocyclyl group is optionally substituted with 1 to 4 groups independently selected from oxo, —$NO_2$, —$N_3$, —$OR^a$, halo, cyano, —$NR^aR^b$, —$C(O)R^a$, —$C(O)OR^a$, —$OC_{1-6}$ alkyCN, —$C(O)NR^aR^b$, $NR^aC(O)R^a$, —$NR^aC(O)OR^a$, —$SO_2R^a$, —$NR^aSO_2R$, —$SO_2NR^aR^b$, —$NR^aSO_2NR^aR^b$, —$C(O)NR^aSO_2NR^aR^b$ and —$C_{3-8}$ cycloalkyl; and wherein the heteroaryl or heterocyclic group may be oxidized on a nitrogen atom to form an N-oxide or oxidized on a sulfur atom to form a sulfoxide or sulfone;

t is 0, 1 or 2; and each $Ar^E$, $Ar^W$, $R^2$, $R^N$, $R^a$, and $R^b$ are as defined herein.

In one embodiment, the compound is represented by formula (If):

(If)

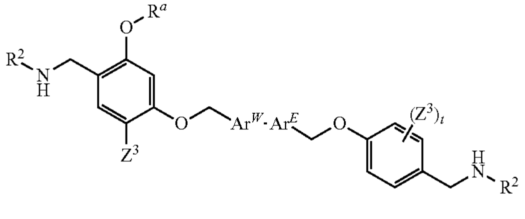

where each $Z^3$ is independently halo, —$OR^a$, —$N_3$, —$NO_2$, —CN, —$NR^1R^2$, —$SO_2R^a$, —$SO_2N^aR^b$, —$NR^aSO_2R^a$, —$NR^aC(O)R^a$, —$C(O)R^a$, —$C(O)OR^a$, —$C(O)NR^aR^b$, —$NR^aC(O)OR^a$, —$NR^aC(O)NR^1R^2$, —$OC(O)NR^aR^b$, —$NR^aSO_2NR^aR^b$, —$C(O)NR^aSO_2NR^aR^b$, —$C_{1-6}$ alkyl, —$C_{2-6}$ alkenyl, —$C_{2-6}$ alkynyl, —$OC_{1-6}$ alkyl, —$C_{3-8}$ cycloalkyl, —$C_{1-6}$ alkyl$C_{3-8}$ cycloalkyl, aryl, heteroaryl, heterocyclyl, and $R^N$;

wherein the alkyl, alkenyl, alkynyl, $C_{3-8}$ cycloalkyl, aryl, heteroaryl, or heterocyclyl group is optionally substituted with 1 to 4 groups independently selected from oxo, —$NO_2$, —$N_3$, —$OR^a$, halo, cyano, —$NR^aR^b$, —$C(O)R^a$, —$C(O)OR^a$, —$OC_{1-6}$ alkyCN, —$C(O)NR^aR^b$, $NR^aC(O)R^a$, —$NR^aC(O)OR^a$, —$SO_2R^a$, —$NR^aSO_2R$, —$SO_2NR^aR^b$, —$NR^aSO_2NR^aR^b$, —$C(O)NR^aSO_2NR^aR^b$ and —$C_{3-8}$ cycloalkyl; and wherein the heteroaryl or heterocyclic group may be oxidized on a nitrogen atom to form an N-oxide or oxidized on a sulfur atom to form a sulfoxide or sulfone;

t is 0, 1 or 2; and each $Ar^E$, $Ar^W$, $R^2$, $R^N$, $R^a$, and $R^b$ are as defined herein.

In one embodiment, the compound is represented by formula (Ig):

(Ig)

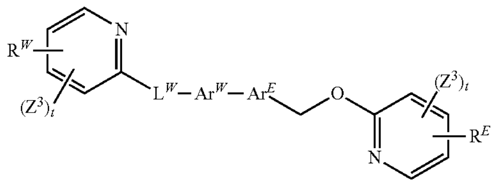

where each $Z^3$ is independently halo, $OR^a$, —$N_3$, —$NO_2$, —CN, —$NR^1R^2$, —$SO_2R^a$, —$SO_2NR^aR^b$, —$NR^aSO_2R^a$, —$NR^aC(O)R^a$, —$C(O)R^a$, —$C(O)OR^a$, —$C(O)NR^aR^b$, —$NR^aC(O)OR^a$, —$NR^aC(O)NR^1R^2$, —$OC(O)NR^aR^b$, —$NR^aSO_2NR^aR^b$, —$C(O)NR^aSO_2NR^aR^b$, —$C_{1-6}$ alkyl, —$C_{2-6}$ alkenyl, —$C_{2-6}$ alkynyl, —$OC_{1-6}$ alkyl, —$C_{3-8}$ cycloalkyl, —$C_{1-6}$ alkyl$C_{3-8}$ cycloalkyl, aryl, heteroaryl, heterocyclyl, and $R^N$;

wherein the alkyl, alkenyl, alkynyl, $C_{3-8}$ cycloalkyl, aryl, heteroaryl, or heterocyclyl group is optionally substituted with 1 to 4 groups independently selected from oxo, —$NO_2$, —$N_3$, —$OR^a$, halo, cyano, —$NR^aR^b$, —$C(O)R^a$, —$C(O)OR^a$, —$OC_{1-6}$ alkylCN, —$C(O)NR^aR^b$, $NR^aC(O)R^a$, —$NR^aC(O)OR^a$, —$SO_2R^a$, —$NR^aSO_2R$, —$SO_2NR^aR^b$, —$NR^aSO_2NR^aR^b$, —$C(O)NR^aSO_2NR^aR^b$ and —$C_{3-8}$ cycloalkyl; and wherein the heteroaryl or heterocyclic group may be oxidized on a nitrogen atom to form an N-oxide or oxidized on a sulfur atom to form a sulfoxide or sulfone;

each t is independently 0, 1 or 2; and each $L^W$, $Ar^E$, $Ar^W$, $R^E$, $R^W$, $R^N$, $R^a$, and $R^b$ are as defined herein.

In one embodiment of formula (Ig), none of $Ar^E$, $Ar^W$, $R^E$, and $R^W$ is an optionally substituted fused 5,6-aromatic or 5,6-heteromatic ring.

In one embodiment, the compound is represented by formula (Ih):

(Ih)

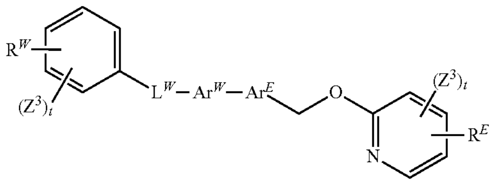

where each $Z^3$ is independently halo, —$OR^a$, —$N_3$, —$NO_2$, —CN, —$NR^1R^2$, —$SO_2R^a$, —$SO_2N^aR^b$, —$NR^aSO_2R^a$, —$NR^aC(O)R^a$, —$C(O)R^a$, —$C(O)OR^a$, —$C(O)NR^aR^b$, —$NR^aC(O)OR^a$, —$NR^aC(O)NR^1R^2$, —$OC(O)NR^aR^b$, —$NR^aSO_2NR^aR^b$, —$C(O)NR^aSO_2NR^aR^b$, —$C_{1-6}$ alkyl, —$C_{2-6}$ alkenyl, —$C_{2-6}$ alkynyl, —$OC_{1-6}$ alkyl, —$C_{3-8}$cycloalkyl, —$C_{1-6}$ alkyl$C_{3-8}$ cycloalkyl, aryl, heteroaryl, heterocyclyl, and $R^N$;

wherein the alkyl, alkenyl, alkynyl, $C_{3-8}$ cycloalkyl, aryl, heteroaryl, or heterocyclyl group is optionally substituted with 1 to 4 groups independently selected from oxo, —$NO_2$, —$N_3$, —$OR^a$, halo, cyano, —$NR^aR^b$, —$C(O)R^a$, —$C(O)OR^a$, —$OC_{1-6}$ alkyCN, —$C(O)NR^aR^b$, $NR^aC(O)R^a$, —$NR^aC(O)OR^a$, —$SO_2R^a$, —$NR^aSO_2R$, —$SO_2NR^aR^b$, —$NR^aSO_2NR^aR^b$, —$C(O)NR^aSO_2NR^aR^b$ and —$C_{3-8}$ cycloalkyl; and wherein the heteroaryl or heterocyclic group may be oxidized on a nitrogen atom to form an N-oxide or oxidized on a sulfur atom to form a sulfoxide or sulfone;

each t is independently 0, 1 or 2; and each $L^W$, $Ar^E$, $Ar^W$, $R^E$, $R^W$, $R^N$, $R^a$, and $R^b$ are as defined herein.

In one embodiment of formula (Ig), none of $Ar^E$, $Ar^W$, $R^E$, and $R^W$ is an optionally substituted fused 5,6-aromatic or 5,6-heteromatic ring.

In one embodiment, the compound is represented by formula (Ii):

(Ii)

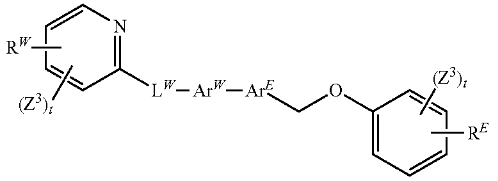

where each $Z^3$ is independently halo, $OR^a$, —$N_3$, —$NO_2$, —CN, —$NR^1R^2$, —$SO_2R^a$, —$SO_2NR^aR^b$, —$NR^aSO_2R^a$, —$NR^aC(O)R^a$, —$C(O)R^a$, —$C(O)OR^a$, —$C(O)NR^aR^b$, —$NR^aC(O)OR^a$, —$NR^aC(O)NR^1R^2$, —$OC(O)NR^aR^b$, —$NR^aSO_2NR^aR^b$, —$C(O)NR^aSO_2NR^aR^b$, —$C_{1-6}$ alkyl, —$C_{2-6}$ alkenyl, —$C_{2-6}$ alkynyl, —$OC_{1-6}$ alkyl, —$C_{3-8}$ cycloalkyl, —$C_{1-6}$ alkyl$C_{3-8}$ cycloalkyl, aryl, heteroaryl, heterocyclyl, and $R^N$;

wherein the alkyl, alkenyl, alkynyl, $C_{3-8}$ cycloalkyl, aryl, heteroaryl, or heterocyclyl group is optionally substituted with 1 to 4 groups independently selected from oxo, —$NO_2$, —$N_3$, —$OR^a$, halo, cyano, —$NR^aR^b$, —$C(O)R^a$, —$C(O)OR^a$, —$OC_{1-6}$ alkyCN, —$C(O)NR^aR^b$, $NR^aC(O)R^a$, —$NR^aC(O)OR^a$, —$SO_2R^a$, —$NR^aSO_2R$, —$SO_2NR^aR^b$, —$NR^aSO_2NR^aR^b$, —$C(O)NR^aSO_2NR^aR^b$ and —$C_{3-8}$ cycloalkyl; and wherein the heteroaryl or heterocyclic group may be oxidized on a nitrogen atom to form an N-oxide or oxidized on a sulfur atom to form a sulfoxide or sulfone;

each t is independently 0, 1 or 2; and each $L^W$, $Ar^E$, $Ar^W$, $R^E$, $R^W$, $R^N$, $R^a$, and $R^b$ are as defined herein.

In one embodiment of formula (Ii), $L^W$ is a bond, —O—, or —$CH_2O$—, where the 0 is bonded to the pyridine ring and the —$CH_2$— is bonded to $Ar^W$. In one embodiment of formula (Ii), none of $Ar^E$, $Ar^W$, $R^E$ and $R^W$ is an optionally substituted fused 5,6-aromatic or 5,6-heteromatic ring.

In one embodiment, the compound is represented by formula (Ij):

(Ij)

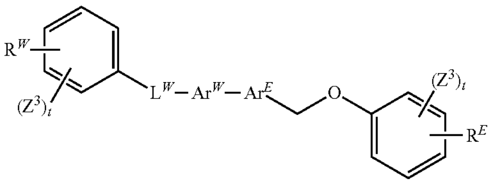

where each $Z^3$ is independently halo, $OR^a$, —$N_3$, —$NO_2$, —CN, —$NR^1R^2$, —$SO_2R^a$, —$SO_2NR^aR^b$, —$NR^aSO_2R^a$, —$NR^aC(O)R^a$, —$C(O)R^a$, —$C(O)OR^a$, —$C(O)NR^aR^b$, —$NR^aC(O)OR^a$, —$NR^aC(O)NR^1R^2$, —$OC(O)NR^aR^b$, —$NR^aSO_2NR^aR^b$, —$C(O)NR^aSO_2NR^aR^b$, —$C_{1-6}$ alkyl, —$C_{2-6}$ alkenyl, —$C_{2-6}$ alkynyl, —$OC_{1-6}$ alkyl, —$C_{3-8}$ cycloalkyl, —$C_{1-6}$ alkyl$C_{3-8}$ cycloalkyl, aryl, heteroaryl, heterocyclyl, and $R^N$;

wherein the alkyl, alkenyl, alkynyl, $C_{3-8}$ cycloalkyl, aryl, heteroaryl, or heterocyclyl group is optionally substituted with 1 to 4 groups independently selected from oxo, —$NO_2$, —$N_3$, —$OR^a$, halo, cyano, —$NR^aR^b$, —$C(O)R^a$, —$C(O)OR^a$, —$OC_{1-6}$ alkylCN, —$C(O)NR^aR^b$, $NR^aC(O)R^a$, —$NR^aC(O)OR^a$, —$SO_2R^a$, —$NR^aSO_2R$, —$SO_2NR^aR^b$, —$NR^aSO_2NR^aR^b$, —$C(O)NR^aSO_2NR^aR^b$ and —$C_{3-8}$ cycloalkyl; and wherein the heteroaryl or heterocyclic group may be oxidized on a nitrogen atom to form an N-oxide or oxidized on a sulfur atom to form a sulfoxide or sulfone;

each t is independently 0, 1 or 2; and each $L^W$, $Ar^E$, $Ar^W$, $R^E$, $R^W$, $R^N$, $R^a$, and $R^b$ are as defined herein.

In one embodiment of formula (Ij), $L^W$ is a bond, —O—, or —$CH_2O$—, where the O is bonded to the pyridine ring and the —$CH_2$— is bonded to $Ar^W$. In one embodiment of formula (Ij), none of $Ar^E$, $Ar^W$, $R^E$ and $R^W$ is an optionally substituted fused 5,6-aromatic or 5,6-heteromatic ring.

In one embodiment, $Ar^W$ and $Ar^E$ are each independently

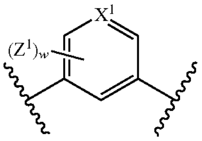
or
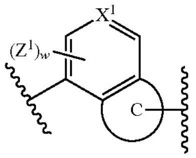
, wherein ring C is independently a 5- or 6-membered ring, optionally comprising 1 or 2 heteroatoms; $Z^1$ is independently halo, —$OR^a$, —$C_{1-6}$ alkyl, —$OC_{1-6}$ alkyl, —$C_{1-6}$ haloalkyl, or —$C_{3-8}$ cycloalkyl; and w is 0, 1, or 2.

In one embodiment, $Ar^W$ and $Ar^E$ are each independently

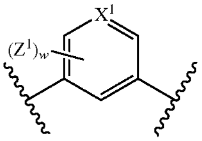
or
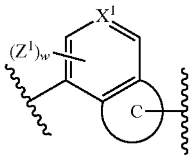
, wherein ring C is independently a non-aromatic 5- or 6-membered ring, optionally comprising 1 or 2 heteroatoms; $Z^1$ is independently halo, —$OR^a$, —$C_{1-6}$ alkyl, —$OC_{1-6}$ alkyl, —$C_{1-6}$ haloalkyl, or —$C_{3-8}$ cycloalkyl; and w is 0, 1, or 2.

In one embodiment, $Ar^W$ and $Ar^E$ are each independently

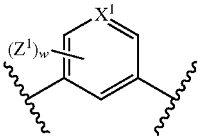
or
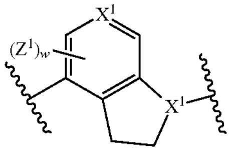
, wherein each $X^1$ is independently N or CH; $Z^1$ is independently halo, —$OR^a$, —$C_{1-6}$ alkyl, —$OC_{1-6}$ alkyl, —$C_{1-6}$ haloalkyl, or —$C_{3-8}$ cycloalkyl; and w is 0, 1, or 2.

In one embodiment, $Ar^W$ and $Ar^E$ are each independently

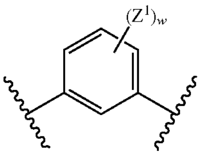
,
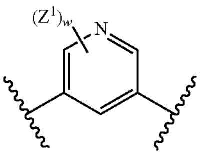
,
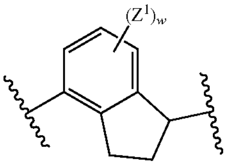
,
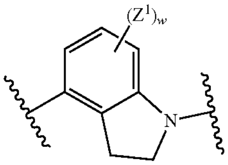
or
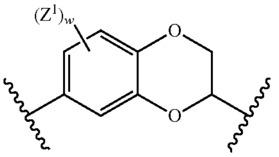
.

wherein each $Z^1$ is independently halo, —$OR^a$, —$C_{1-6}$ alkyl, —$OC_{1-6}$ alkyl, —$C_{1-6}$ haloalkyl, or —$C_{3-8}$ cycloalkyl, and u is 0, 1, or 2. In one embodiment, $Ar^W$ and $Ar^E$ are each

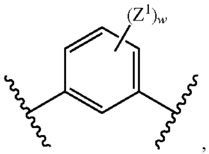
, wherein each $Z^1$ is independently halo, —$OR^a$, —$C_{1-6}$ alkyl, —$OC_{1-6}$ alkyl, —$C_{1-6}$ haloalkyl, or —$C_{3-8}$ cycloalkyl, and w is 0, 1, or 2. In one embodiment, $Ar^W$ and $Ar^E$ are each

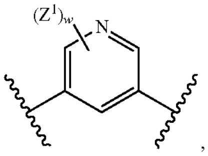
, wherein each $Z^1$ is independently halo, —$OR^a$, —$C_{1-6}$ alkyl, —$OC_{1-6}$ alkyl, —$C_{1-6}$ haloalkyl, or —$C_{3-8}$ cycloalkyl, and w is 0, 1, or 2. In one embodiment, $Ar^W$ and $Ar^E$ are each

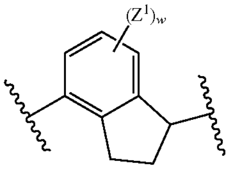
, wherein each $Z^1$ is independently halo, —$OR^a$, —$C_{1-6}$ alkyl, —$OC_{1-6}$ alkyl, —$C_{1-6}$ haloalkyl, or —$C_{3-8}$ cycloalkyl, and w is 0, 1, or 2. In one embodiment, $Ar^W$ and $Ar^E$ are each

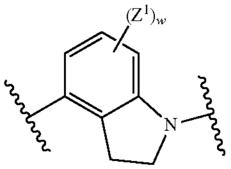
, wherein each $Z^1$ is independently halo, —$OR^a$, —$C_{1-6}$ alkyl, —$OC_{1-6}$ alkyl, —$C_{1-6}$ haloalkyl, or —$C_{3-8}$ cycloalkyl, and w is 0, 1, or 2. In one embodiment, $Ar^W$ and $Ar^E$ are each

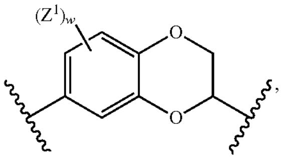
, wherein each $Z^1$ is independently halo, —$OR^a$, —$C_{1-6}$ alkyl, —$OC_{1-6}$ alkyl, —$C_{1-6}$ haloalkyl, or —$C_3$-8 cycloalkyl, and w is 0, 1, or 2.

In one embodiment, the compound is represented by formula (IIa):

(IIa)

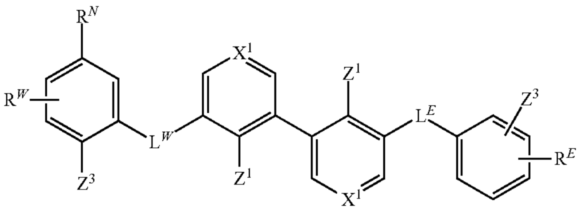

wherein each $X^1$ is independently N or CH;

each $Z^1$ is independently halo, $—OR^a$, $—C_{1-6}$ alkyl, $—OC_{1-6}$ alkyl, $—C_{1-6}$ haloalkyl, or $—C_{3-8}$ cycloalkyl;

each $Z^3$ is independently halo, $—OR^a$, $—N_3$, $—NO_2$, —CN, $—NR^1R^2$, $—SO_2R^a$, $—SO_2N^aR^b$, $—NR^aSO_2R^a$, $—NR^aC(O)R^a$, $—C(O)R^a$, $—C(O)OR^a$, $—C(O)NR^aR^b$, $—NR^aC(O)OR^a$, $—NR^aC(O)NR^1R^2$, $—OC(O)NR^aR^b$, $—NR^aSO_2NR^aR^b$, $—C(O)NR^aSO_2NR^aR^b$, $—C_{1-6}$ alkyl, $—C_{2-6}$ alkenyl, $—C_{2-6}$ alkynyl, $—OC_{1-6}$ alkyl, $—C_{3-8}$ cycloalkyl, $—C_{1-6}$ alkyl$C_{3-8}$ cycloalkyl, aryl, heteroaryl, heterocyclyl, and $R^N$;

wherein the alkyl, alkenyl, alkynyl, $C_{3-8}$ cycloalkyl, aryl, heteroaryl, or heterocyclyl group is optionally substituted with 1 to 4 groups independently selected from oxo, $—NO_2$, $—N_3$, $—OR^a$, halo, cyano, $—NR^aR^b$, $—C(O)R^a$, $—C(O)OR^a$, $—OC_{1-6}$alkyCN, $—C(O)NR^aR^b$, $NR^aC(O)R^a$, $—NR^aC(O)OR^a$, $—SO_2R^a$, $—NR^aSO_2R$, $—SO_2NR^aR^b$, $—NR^aSO_2NR^aR^b$, $—C(O)NR^aSO_2NR^aR^b$ and $—C_{3-8}$ cycloalkyl; and wherein the heteroaryl or heterocyclic group may be oxidized on a nitrogen atom to form an N-oxide or oxidized on a sulfur atom to form a sulfoxide or sulfone;

$R^N$ is independently $—C_{1-6}$alkyl$NR^1R^2$, $—OC_{1-6}$ alky$NR^1R^2$, $—C_{1-6}$ alkyl$OC_{1-6}$ alkyl$NR^1R^2$, $—NR^aC_{1-6}$ alkyl$NR^1R^2$, $—C_{1-6}$ alkyl$C(O)NR^1R^2$, $—OC_{1-6}$ alkyl$C(O)NR^1R^2$, $—OC_{1-6}$ alkyl$C(O)OR^1$, $—SC_{1-6}$alkyl$NR^1R^2$, $—C_{1-6}$alkyl$OR^a$, or

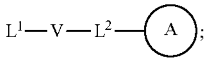

wherein: $L^1$ is independently a bond, O, $NR^a$, S, SO, or $SO_2$;

V is independently selected from a bond, $C_{1-6}$alkyl, $C_{2-6}$alkenyl, and $C_{2-6}$alkynyl;

wherein each alkyl, alkenyl, or alkynyl is optionally independently substituted with $OR^a$, halo, cyano, $—NR^aR^b$ and $—C_{3-8}$ cycloalkyl;

$L^2$ is independently a bond, O, $NR^a$, S, SO, or $SO_2$;

ring A is independently cycloalkyl, aryl, heteroaryl, or heterocyclyl;

wherein each cycloalkyl, aryl, heteroaryl, or heterocyclyl is optionally substituted with 1 to 4 groups independently selected from oxo, $—NO_2$, $—N_3$, $—OR^a$, halo, cyano, $—C_{1-6}$ alkyl, $—C_{1-6}$ haloalkyl, $—C_{2-6}$alkenyl, $—C_{2-6}$ alkynyl, $—OC_{1-6}$ haloalkyl, $NR^aR^b$, $—C(O)R^a$, $—C(O)OR^a$, $—OC_{1-6}$ alkylCN, $—C(O)NR^aR^b$, $—NR^aC(O)R^a$, $—NR^aC(O)OR^a$, $—NR^aC(O)OR^a$, $—C(O)N(R^a)OR^b$, $—SO_2R^a$, $—SO_2NR^aR^b$, $—NR^aSO_2R$, $—NR^aSO_2NR^aR^b$, $—C(O)NR^aSO_2NR^aR^b$, $C_{3-8}$cycloalkyl, and $C_{1-6}$alkyl$C_{3-8}$ cycloalkyl; and wherein the alkyl, alkenyl, or alkynyl group is optionally independently substituted with $—OR^a$, halo, cyano, $—NR^aR^b$ or $—C_{3-8}$cycloalkyl $L^E$ and $L^W$ are each independently a bond, —O—, —S—, —SO—, $—SO_2—$, $—(CR^3R^4)_m—$, $—(CR^3R^4)_mO(CR^3R^4)_m—$, $—(CR^3R^4)_mS(CR^3R^4)_m—$, $—(CR^3R^4)_mNR^3(CR^3R^4)_m—$, —C(O)—, $—(CR^3R^4)_mC(O)(CR^3R^4)_m—$, $—(CR^3R^4)_mC(O)NR^3(CR^3R^4)_m—$, $—(CR^3R^4)_mNR^3C(O)(CR^3R^4)_m—$, $C_{2-6}$ alkenylene, $C_{2-6}$ alkynylene,

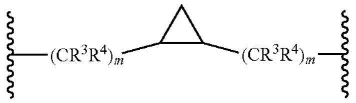

or

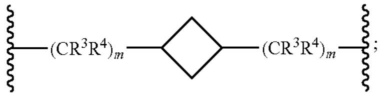

each m is independently 0, 1, 2, 3 or 4;

$R^E$ and $R^W$ are each independently $—NR^1R^2$, $—C_{1-6}$ alky$NR^1R^2$, $—OC_{1-6}$ alkyl$NR^1R^2$, $—C_{1-6}$ alkyl $OC_{1-6}$alkyl$NR^1R^2$, $—NR^aC_{1-6}$ alkyl$NR^1R^2$, $—C_{1-6}$ alkyl$N^+R^1R^2R^3$, $—SC_{1-6}$ alkyl$NR^1R^2$, $—C(O)NR^1R^2$, $—SO_2R^a$, $—(CH_2)_uSO_2NR^1R^2$, $—(CH_2)_uNR^aSO_2NR^aR^b$, $—SO_2NR^aC_{1-6}$ alky$NR^1R^2$, $—NR^aSO_2C_{1-6}$ alkyl$NR^1R^2$, $—(CH_2)_uC(O)NR^aSO_2NR^aR^b$, $—(CH_2)_uN^+R^1R^2O^-$, $—(CH_2)_uP^+R^bR^cR^d$, $—(CH_2)_uP^+R^cR^dO^-$, $—(CH_2)_uP^+O[NR^aR^b][NR^cR^d]$, $—(CH_2)_uNR^cP(O)(OR^c)_2$, $—(CH_2)_uCH_2OP(O)(OR^c)(OR^d)$, $—(CH_2)_uOP(O)(OR^c)(OR^d)$, $—(CH_2)_uOP(O)NR^aR^b)(OR^a)$, or

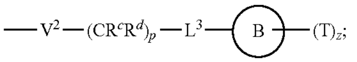

wherein:

$V^2$ is independently a bond, O, $NR^a$, S, SO, $SO_2$, $C(O)NR^a$, $NR^aC(O)$, $SO_2NR^1R^2$, or $NR^aSO_2$;

$L^3$ is independently a bond, O, $NR^a$, S, SO, $SO_2$, $C(O)NR^a$, $NR^aC(O)$, $SO_2NR^1R^2$, or $NR^aSO_2$;

ring B is cycloalkyl, aryl, heteroaryl, or heterocyclyl; T is independently H, $OR^a$, $(CH_2)_qNR^1R^2$, $(CH_2)_qNR^aC(O)R^e$ or $(CH_2)_qC(O)R$;

p is independently 0, 1, 2, 3, 4, or 5;

q is independently 0, 1, 2, 3, 4, or 5;

u is 0, 1, 2, 3, or 4;

z is 0, 1, 2, or 3; and wherein the alkyl, cycloalkyl, aryl, heteroaryl, or heterocyclyl of $R^E$ or $R^W$ is optionally substituted with 1 to 3 substituents independently selected from the group consisting of $NR^aR^b$, halo, cyano, oxo, $OR^a$, $—C_{1-6}$alkyl, $—C_{1-6}$haloalkyl, $—C_{1-6}$cyanoalkyl, —$C_{1-6}$alkyNR$^a$R$^b$, —$C_{1-6}$ alkylOH, —$C_{3-8}$ cycloalkyl, and —$C_{1-3}$ alkyl$C_{3-8}$cycloalkyl;

provided that at least one of $V^2$, $L^3$, ring B and T contains a nitrogen atom;

$R^1$ is independently selected from H, —$C_{1-8}$ alkyl, —$C_{2-6}$ alkenyl, —$C_{2-6}$ alkynyl, —$C_{3-6}$ cycloalkyl, aryl, heteroaryl, heterocyclyl, —$C_{1-6}$ alkylaryl, —$C_{1-6}$ alkylheteroaryl, —$C_{1-6}$ alkylheterocyclyl, —$C_{1-6}$ alkylC(O)OR$^a$, —$C_{2-6}$ alkenylC(O)OR$^a$, —$SO_2R^a$, —$SO_2NR^aR^b$, —C(O)NR$^a$SO$_2$R$^a$, and $C_{1-6}$ alkyl $C_{3-8}$cycloalkyl;

wherein each alkyl, alkenyl, cycloalkyl, aryl, heteroaryl, or heterocyclyl is optionally substituted with 1 to 4 groups independently selected from —OR$^a$, —CN, halo, $C_{1-6}$alkyl, —$C_{1-6}$ alkylOR$^a$, —$C_{1-6}$ cyanoalkyl, —$C_{1-6}$haloalkyl, $C_{3-8}$ cycloalkyl, —$C_{1-3}$alkyl$C_{3-8}$cycloalkyl, —C(O)R$^a$, —$C_{1-6}$ alkylC(O)R$^a$, —C(O)OR$^a$, —$C_{1-6}$ alkylC(O)OR$^a$, —NR$^a$R$^b$, —OC(O)NR$^a$R$^b$, NR$^a$C(O)OR$^b$, —$C_{1-6}$alkylNR$^a$R$^b$, —C(O)NR$^a$R$^b$, —$C_{1-6}$ alkylC(O)NR$^a$R$^b$, —$SO_2R^a$, —$C_{1-6}$alkylSO$_2$R$^a$, —$SO_2NR^aR^b$, —$C_{1-6}$ alkylSO$_2$NR$^a$R$^b$, —C(O)NR$^a$SO$_2$R$^b$, —$C_{1-6}$ alkylC(O)NR$^a$SO$_2$R$^b$, —NR$^a$C(O)R$^b$, and —$C_{1-6}$alkylNR$^a$C(O)R$^b$;

$R^2$ is independently selected from H, —$C_{1-6}$ alkyl, —$C_{2-6}$ alkenyl, —$C_{2-6}$ alkynyl, —$C_{3-6}$ cycloalkyl, aryl, heteroaryl, heterocyclyl, —$C_{1-6}$ alkylaryl, —$C_{1-6}$ alkylheteroaryl, —$C_{1-6}$ alkylheterocyclyl, —$C_{2-6}$ alkyl-OR$^a$, —$C_{1-6}$ alkylC(O)OR$^a$, and —$C_{2-6}$ alkenylC(O)OR$^a$;

wherein each alkyl, alkenyl, alkynyl, cycloalkyl, aryl, heteroaryl, or heterocyclyl is optionally substituted with 1 to 4 groups independently selected from —OR$^a$, —CN, halo, $C_{1-6}$alkyl, —$C_{1-6}$ alkylOR$^a$, —$C_{1-6}$ cyanoalkyl, —$C_{1-6}$ haloalkyl, —$C_{3-8}$ cycloalkyl, —$C_{1-3}$alkyl$C_{3-8}$cycloalkyl, —C(O)R$^a$, —$C_{1-6}$ alkylC(O)R$^a$, —C(O)OR$^a$, —$C_{1-6}$ alkylC(O)OR$^a$, —NR$^a$R$^b$, —$C_{1-6}$ alkylNR$^a$R$^b$, —C(O)NR$^a$R$^b$, $C_{1-6}$alkylC(O)NR$^a$R$^b$, —$SO_2R^a$, —$C_{1-6}$alkylSO$_2$R$^a$, —$SO_2NR^aR^b$, —$C_{1-6}$alkylSO$_2$NR$^a$R$^b$, —C(O)NR$^a$SO$_2$R, and —NR$^a$C(O)R$^b$;

or $R^1$ and $R^2$ combine to form a heterocyclyl group optionally containing 1, 2, or 3 additional heteroatoms independently selected from oxygen, sulfur and nitrogen, and optionally substituted with 1 to 3 groups independently selected from oxo, —$C_{1-6}$alkyl, —$C_{3-8}$cycloalkyl, —$C_{2-6}$ alkenyl, —$C_{2-6}$ alkynyl, —OR$^a$, —C(O)OR$^a$, —$C_{1-6}$ cyanoalkyl, —$C_{1-6}$ alkylOR$^a$, —$C_{1-6}$haloalkyl, —$C_{1-3}$ alkyl$C_{3-8}$cycloalkyl, —C(O)R$^a$, —$C_{1-6}$ alkylC(O)R$^a$, —$C_{1-6}$ alkylC(O)OR$^a$, —NR$^a$R$^b$, —$C_{1-6}$alkyNR$^a$R$^b$, —C(O)NR$^a$R$^b$, —$C_{1-6}$ alkylC(O)NR$^a$R$^b$, —$SO_2R^a$, —$C_{1-6}$ alkylSO$_2$R$^a$, —$SO_2NR^aR^b$, and $C_{1-6}$ alkylSO$_2$NR$^a$R$^b$;

$R^3$ is independently H, —$C_{1-6}$alkyl, —$C_{2-6}$ alkenyl, —$C_{3-6}$ cycloalkyl, aryl, heteroaryl, heterocyclyl, —$C_{1-6}$alkylaryl, —$C_{1-6}$alkylheteroaryl, —$C_{1-6}$ alkylheterocyclyl, —$C_{2-6}$alkyl-OR$^a$, —$C_{1-6}$alkylC(O)OR$^a$, or —$C_{2-6}$ alkenylC(O)OR$^a$;

$R^4$ is independently H, —$C_{1-6}$alkyl, —$C_{2-6}$ alkenyl, —$C_{3-6}$ cycloalkyl, aryl, heteroaryl, heterocyclyl, —$C_{1-6}$alkylaryl, —$C_{1-6}$alkylheteroaryl, —$C_{1-6}$ alkylheterocyclyl, —$C_{2-6}$alkyl-OR$^a$, —$C_{1-6}$alkylC(O)OR$^a$, or —$C_{2-6}$ alkenylC(O)OR$^a$;

$R^a$ is independently selected from H, —$C_{1-6}$alkyl, —$C_{3-8}$cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl;

$R^b$ is independently selected from H, —$C_{1-6}$alkyl, —$C_{3-8}$cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$ alkylheterocyclyl;

or $R^a$ and $R^b$ may combine together to form a ring consisting of 3-8 ring atoms that are C, N, O, or S; wherein the ring is optionally substituted with 1 to 4 groups independently selected from —OR$^f$, —CN, halo, —$C_{1-6}$ alkylOR$^f$, —$C_{1-6}$ cyanoalkyl, —$C_{1-6}$haloalkyl, —$C_{3-8}$ cycloalkyl, —$C_{1-3}$ alkyl$C_{3-8}$cycloalkyl, —C(O)R$^f$, —$C_{1-6}$ alkylC(O)R$^f$, —C(O)OR$^f$, —$C_{1-6}$ alkylC(O)OR$^f$, —NR$^f$R$^g$, —$C_{1-6}$ alkylNR$^f$R$^g$, —C(O)NR$^f$R$^g$, —$C_{1-6}$ alkylC(O)NR$^f$R$^g$, —$SO_2R^f$, —$C_{1-6}$ alkylSO$_2$R$^f$, —$SO_2NR^fR^g$, —$C_{1-6}$ alkylSO$_2$NR$^f$R$^g$, —C(O)NR$^f$SO$_2$R$^g$ and —NR$^f$C(O)R$^g$;

$R^c$ is independently selected from H, OH, —$C_{1-6}$alkyl, —$C_{3-8}$ cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl;

$R^d$ is independently selected from H, —$C_{1-6}$alkyl, —$C_3$-$C_8$cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl;

$R^e$ is independently selected from H, —$C_{1-6}$alkyl, —O$C_{1-6}$alkyl, —$C_{3-8}$ cycloalkyl, aryl, heteroaryl, heterocyclyl, —O$C_{3-8}$cycloalkyl, —Oaryl, —Oheteroaryl, —Oheterocyclyl, —$C_{1-3}$ alkyl$C_{3-8}$cycloalkyl, —$C_{1-6}$alkylaryl, —$C_{1-6}$alkylheteroaryl, —NR$^f$R$^g$, —$C_{1-6}$alkylNR$^f$R$^g$, —C(O)NR$^f$R$^g$, —$C_{1-6}$alkylC(O)NR$^f$R$^g$, —NHSO$_2$R$^f$, —$C_{1-6}$alkylSO$_2$R$^f$, and —$C_{1-6}$alkylSO$_2$NR$^f$R$^g$;

$R^f$ is independently selected from H, —$C_{1-6}$alkyl, —$C_{3-8}$ cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl; and $R^g$ is independently selected from H, —$C_{1-6}$ alkyl, —$C_{3-8}$ cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl;

or a pharmaceutically acceptable salt, stereoisomer, mixture of stereoisomers, or tautomer thereof.

In one embodiment of formula (IIa), when one of $L^E$ or $L^W$ is —$CH_2$O—, —$(CH_2)_2$—, —CH═CH—, or —C(O)NH—; then the other of $L^E$ and $L^W$ is a bond, —O—, or —O—$CH_2$—, where the oxygen is bonded to the Q ring and the —$CH_2$— is bonded to the Ar ring. In one embodiment of formula (IIa), both $L^E$ and $L^W$ are —O—$CH_2$—, where the oxygen is bonded to the Q ring and the $CH_2$ is bonded to the Ar ring. In one embodiment of formula (IIa), one or both of $L^E$ or $L^W$ is a bond or —O—. In one embodiment of formula (IIa), one or both of $X^1$ is N. In one embodiment of formula (IIa), neither of $R^E$ or $R^W$ is an optionally substituted fused 5,6-aromatic or 5,6-heteromatic ring.

In one embodiment, the compound is represented by formula (IIb):

(IIb)

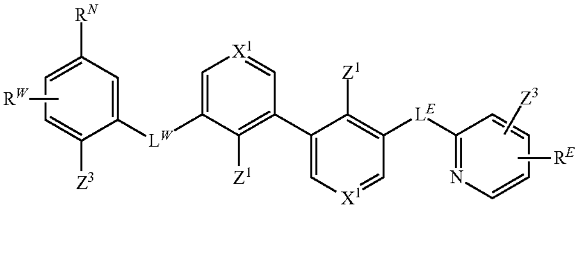

wherein each $X^1$ is independently N or CH;

each $Z^1$ is independently halo, $—OR^a$, $—C_{1-6}$ alkyl, $—OC_{1-6}$ alkyl, $—C_{1-6}$ haloalkyl, or $—C_{3-8}$ cycloalkyl;

each $Z^3$ is independently halo, $—OR^a$, $—N_3$, $—NO_2$, —CN, $—NR^1R^2$, $—SO_2R^a$, $—SO_2N^aR^b$, $—NR^aSO_2R^a$, $—NR^aC(O)R^a$, $—C(O)R^a$, $—C(O)OR^a$, $—C(O)NR^aR^b$, $—NR^aC(O)OR^a$, $—NR^aC(O)NR^1R^2$, $—OC(O)NR^aR^b$, $—NR^aSO_2NR^aR^b$, $—C(O)NR^aSO_2NR^aR^b$, $—C_{1-6}$ alkyl, $—C_{2-6}$ alkenyl, $—C_{2-6}$ alkynyl, $—OC_{1-6}$ alkyl, $—C_{3-8}$ cycloalkyl, $—C_{1-6}$ alkyl$C_{3-8}$ cycloalkyl, aryl, heteroaryl, heterocyclyl, and $R^N$;

wherein the alkyl, alkenyl, alkynyl, $C_{3-8}$ cycloalkyl, aryl, heteroaryl, or heterocyclyl group is optionally substituted with 1 to 4 groups independently selected from oxo, $—NO_2$, $—N_3$, $—OR^a$, halo, cyano, $—NR^aR^b$, $—C(O)R^a$, $—C(O)OR^a$, $—OC_{1-6}$alkylCN, $—C(O)NR^aR^b$, $NR^aC(O)R^a$, $—NR^aC(O)OR^a$, $—SO_2R^a$, $—NR^aSO_2R$, $—SO_2NR^aR^b$, $—NR^aSO_2NR^aR^b$, $—C(O)NR^aSO_2NR^aR^b$ and $—C_{3-8}$ cycloalkyl; and wherein the heteroaryl or heterocyclic group may be oxidized on a nitrogen atom to form an N-oxide or oxidized on a sulfur atom to form a sulfoxide or sulfone;

$R^N$ is independently $—C_{1-6}$ alkyl$NR^1R^2$, $—OC_{1-6}$ alky$NR^1R^2$, $—C_{1-6}$ alkyl$OC_{1-6}$ alkyl$NR^1R^2$, $—NR^aC_{1-6}$alkyl$NR^1R^2$, $—C_{1-6}$alkyl$C(O)NR^1R^2$, $—OC_{1-6}$alkyl$C(O)NR^1R^2$, $—OC_{1-6}$ alkyl$C(O)OR^1$, $—SC_{1-6}$alkyl$NR^1R^2$, $—C_{1-6}$alkyl$OR^a$, or

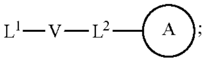;

wherein: $L^1$ is independently a bond, O, $NR^a$, S, SO, or $SO_2$;

V is independently selected from a bond, $C_{1-6}$alkyl, $C_{2-6}$alkenyl, and $C_{2-6}$alkynyl;

wherein each alkyl, alkenyl, or alkynyl is optionally independently substituted with $OR^a$, halo, cyano, $—NR^aR^b$ and $—C_{3-8}$ cycloalkyl;

$L^2$ is independently a bond, O, $NR^a$, S, SO, or $SO_2$;

ring A is independently cycloalkyl, aryl, heteroaryl, or heterocyclyl;

wherein each cycloalkyl, aryl, heteroaryl, or heterocyclyl is optionally substituted with 1 to 4 groups independently selected from oxo, $—NO_2$, $—N_3$, $—OR^a$, halo, cyano, $—C_{1-6}$ alkyl, $—C_{1-6}$ haloalkyl, $—C_{2-6}$alkenyl, $—C_{2-6}$ alkynyl, $—OC_{1-6}$ haloalkyl, $NR^aR^b$, $—C(O)R^a$, $—C(O)OR^a$, $—OC_{1-6}$ alkylCN, $—C(O)NR^aR^b$, $—NR^aC(O)R^a$, $—NR^aC(O)OR^a$, $—NR^aC(O)OR^a$, $—C(O)N(R^a)OR^b$, $—SO_2R^a$, $—SO_2NR^aR^b$, $—NR^aSO_2R$, $—NR^aSO_2NR^aR^b$, $—C(O)NR^aSO_2NR^aR^b$, $C_{3-8}$cycloalkyl, and $C_{1-6}$alkyl$C_{3-8}$ cycloalkyl; and wherein the alkyl, alkenyl, or alkynyl group is optionally independently substituted with $—OR^a$, halo, cyano, $—NR^aR^b$ or $—C_{3-8}$cycloalkyl $L^E$ and $L^W$ are each independently a bond, —O—, —S—, —SO—, $—SO_2—$, $—(CR^3R^4)_m—$, $—(CR^3R^4)_mO(CR^3R^4)_m—$, $—(CR^3R^4)_mS(CR^3R^4)_m—$, $—(CR^3R^4)_mNR^3(CR^3R^4)_m—$, —C(O)—, $—(CR^3R^4)_mC(O)(CR^3R^4)_m—$, $—(CR^3R^4)_mC(O)NR^3(CR^3R^4)_m—$, $—(CR^3R^4)_mNR^3C(O)(CR^3R^4)_m—$, $C_{2-6}$ alkenylene, $C_{2-6}$ alkynylene,

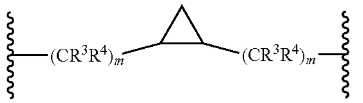

or

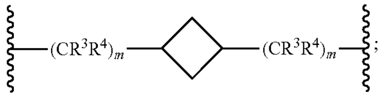;

each m is independently 0, 1, 2, 3 or 4;

$R^E$ and $R^W$ are each independently $—NR^1R^2$, $—C_{1-6}$ alky$NR^1R^2$, $—OC_{1-6}$ alky$lNR^1R^2$, $—C_{1-6}$ alkyl$OC_{1-6}$alkyl$NR^1R^2$, $—NR^aC_{1-6}$ alkyl$NR^1R^2$, $—C_{1-6}$ alkyl$N^+R^1R^2R^3$, $—SC_{1-6}$ alkyl$NR^1R^2$, $—C(O)NR^1R^2$, $—SO_2R^a$, $—(CH_2)_uSO_2NR^1R^2$, $—(CH_2)_uNR^aSO_2NR^aR^b$, $—SO_2NR^aC_{1-6}$ alky$NR^1R^2$, $—NR^aSO_2C_{1-6}$ alkyl$NR^1R^2$, $—(CH_2)_uC(O)NR^aSO_2NR^aR^b$, $—(CH_2)_uN^+R^1R^2O^-$, $—(CH_2)_uP^+R^bR^cR^d$, $—(CH_2)_uP^+R^cR^dO^-$, $—(CH_2)_uP^+O[NR^aR^b][NR^cR^d]$, $—(CH_2)_uNR^cP(O)(OR^c)_2$, $—(CH_2)_uCH_2OP(O)(OR^c)(OR^d)$, $—(CH_2)_uOP(O)(OR^c)(OR^d)$, $—(CH_2)_uOP(O)NR^aR^b)(OR^a)$, or

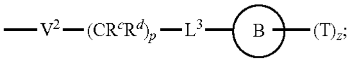;

wherein:

$V^2$ is independently a bond, O, $NR^a$, S, SO, $SO_2$, $C(O)NR^a$, $NR^aC(O)$, $SO_2NR^1R^2$, or $NR^aSO_2$;

$L^3$ is independently a bond, O, $NR^a$, S, SO, $SO_2$, $C(O)NR^a$, $NR^aC(O)$, $SO_2NR^1R^2$, or $NR^aSO_2$;

ring B is cycloalkyl, aryl, heteroaryl, or heterocyclyl;

T is independently H, $OR^a$, $(CH_2)_qNR^1R^2$, $(CH_2)_qNR^aC(O)R^e$ or $(CH_2)C(O)R^e$;

p is independently 0, 1, 2, 3, 4, or 5;

q is independently 0, 1, 2, 3, 4, or 5;

u is 0, 1, 2, 3, or 4;

z is 0, 1, 2, or 3; and wherein the alkyl, cycloalkyl, aryl, heteroaryl, or heterocyclyl of $R^E$ or $R^W$ is optionally substituted with 1 to 3 substituents independently selected from the group consisting of $NR^aR^b$, halo, cyano, oxo, $OR^a$, $—C_{1-6}$alkyl, $—C_{1-6}$haloalkyl, $—C_{1-6}$cyanoalkyl, $—C_{1-6}$alky$NR^aR^b$, $—C_{1-6}$ alkylOH, $—C_{3-8}$ cycloalkyl, and $—C_{1-3}$ alkyl$C_{3-8}$cycloalkyl;

provided that at least one of $V^2$, $L^3$, ring B and T contains a nitrogen atom;

$R^1$ is independently selected from H, $—C_{1-8}$ alkyl, $—C_{2-6}$ alkenyl, $—C_{2-6}$ alkynyl, $—C_{3-6}$ cycloalkyl, aryl, heteroaryl, heterocyclyl, $—C_{1-6}$alkylaryl, $—C_{1-6}$alkylheteroaryl, $—C_{1-6}$alkylheterocyclyl, $—C_{1-6}$ alkyl$C(O)OR^a$, $—C_{2-6}$ alkenyl$C(O)OR^a$, $—SO_2R^a$, $—SO_2NR^aR^b$, $—C(O)NR^aSO_2R^a$, and $C_{1-6}$ alkyl $C_{3-8}$cycloalkyl;

wherein each alkyl, alkenyl, cycloalkyl, aryl, heteroaryl, or heterocyclyl is optionally substituted with 1 to 4 groups independently selected from $—OR^a$, —CN, halo, $C_{1-6}$alkyl, $—C_{1-6}$alkyl$OR^a$, $—C_{1-6}$cyanoalkyl, $—C_{1-6}$haloalkyl, $C_{3-8}$cycloalkyl, $—C_{1-3}$alkyl$C_{3-8}$cycloalkyl, —C(O)$R^a$, —$C_{1-6}$ alkylC(O)$R^a$, —C(O)O$R^a$, —$C_{1-6}$ alkylC(O)O$R^a$, —N$R^aR^b$, —OC(O)N$R^aR^b$, N$R^a$C(O)O$R^b$, —$C_{1-6}$alkylN$R^aR^b$, —C(O)N$R^aR^b$, —$C_{1-6}$alkylC(O)N$R^aR^b$, —$SO_2R^a$, —$C_{1-6}$alkyl$SO_2R^a$, —$SO_2NR^aR^b$, —$C_{1-6}$ alkyl$SO_2NR^aR^b$, —C(O)N$R^aSO_2R^b$, —$C_{1-6}$ alkylC(O)N$R^aSO_2R^b$, —N$R^a$C(O)$R^b$, and —$C_{1-6}$alkylN$R^a$C(O)$R^b$;

$R^2$ is independently selected from H, —$C_{1-6}$alkyl, —$C_{2-6}$ alkenyl, —$C_{2-6}$ alkynyl, —$C_{3-6}$ cycloalkyl, aryl, heteroaryl, heterocyclyl, —$C_{1-6}$alkylaryl, —$C_{1-6}$alkylheteroaryl, —$C_{1-6}$ alkylheterocyclyl, —$C_{2-6}$alkyl-O$R^a$, —$C_{1-6}$ alkylC(O)O$R^a$, and —$C_{2-6}$ alkenylC(O)O$R^a$;

wherein each alkyl, alkenyl, alkynyl, cycloalkyl, aryl, heteroaryl, or heterocyclyl is optionally substituted with 1 to 4 groups independently selected from —O$R^a$, —CN, halo, $C_{1-6}$alkyl, —$C_{1-6}$alkylO$R^a$, —$C_{1-6}$cyanoalkyl, —$C_{1-6}$haloalkyl, —$C_{3-8}$cycloalkyl, —$C_{1-3}$alkyl$C_{3-8}$cycloalkyl, —C(O)$R^a$, —$C_{1-6}$ alkylC(O)$R^a$, —C(O)O$R^a$, —$C_{1-6}$ alkylC(O)O$R^a$, —N$R^aR^b$, —$C_{1-6}$ alkylN$R^aR^b$, —C(O)N$R^aR^b$, $C_{1-6}$alkylC(O)N$R^aR^b$, —$SO_2R^a$, —$C_{1-6}$alkyl$SO_2R^a$, —$SO_2NR^aR^b$, —$C_{1-6}$alkyl$SO_2NR^aR^b$, —C(O)N$R^aSO_2$R, and —N$R^a$C(O)$R^b$;

or $R^1$ and $R^2$ combine to form a heterocyclyl group optionally containing 1, 2, or 3 additional heteroatoms independently selected from oxygen, sulfur and nitrogen, and optionally substituted with 1 to 3 groups independently selected from oxo, —$C_{1-6}$alkyl, —$C_{3-8}$ cycloalkyl, —$C_{2-6}$ alkenyl, —$C_{2-6}$ alkynyl, —O$R^a$, —C(O)O$R^a$, —$C_{1-6}$cyanoalkyl, —$C_{1-6}$ alkylO$R^a$, —$C_{1-6}$haloalkyl, —$C_{1-3}$ alkyl$C_{3-8}$cycloalkyl, —C(O)$R^a$, —$C_{1-6}$ alkylC(O)$R^a$, —$C_{1-6}$ alkylC(O)O$R^a$, —N$R^aR^b$, —$C_{1-6}$alkyN$R^aR^b$, —C(O)N$R^aR^b$, —$C_{1-6}$ alkylC(O)N$R^aR^b$, —$SO_2R^a$, —$C_{1-6}$ alkyl$SO_2R^a$, —$SO_2NR^aR^b$, and $C_{1-6}$ alkyl$SO_2NR^aR^b$;

$R^3$ is independently H, —$C_{1-6}$alkyl, —$C_{2-6}$ alkenyl, —$C_{3-6}$ cycloalkyl, aryl, heteroaryl, heterocyclyl, —$C_{1-6}$alkylaryl, —$C_{1-6}$alkylheteroaryl, —$C_{1-6}$ alkylheterocyclyl, —$C_{2-6}$alkyl-O$R^a$, —$C_{1-6}$alkylC(O)O$R^a$, or —$C_{2-6}$ alkenylC(O)O$R^a$;

$R^4$ is independently H, —$C_{1-6}$alkyl, —$C_{2-6}$ alkenyl, —$C_{3-6}$ cycloalkyl, aryl, heteroaryl, heterocyclyl, —$C_{1-6}$alkylaryl, —$C_{1-6}$alkylheteroaryl, —$C_{1-6}$ alkylheterocyclyl, —$C_{2-6}$alkyl-O$R^a$, —$C_{1-6}$alkylC(O)O$R^a$, or —$C_{2-6}$ alkenylC(O)O$R^a$;

$R^a$ is independently selected from H, —$C_{1-6}$alkyl, —$C_{3-8}$ cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl;

$R^b$ is independently selected from H, —$C_{1-6}$alkyl, —$C_{3-8}$ cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$ alkylheterocyclyl;

or $R^a$ and $R^b$ may combine together to form a ring consisting of 3-8 ring atoms that are C, N, O, or S; wherein the ring is optionally substituted with 1 to 4 groups independently selected from —O$R^f$, —CN, halo, —$C_{1-6}$ alkylO$R^f$, —$C_{1-6}$ cyanoalkyl, —$C_{1-6}$haloalkyl, —$C_{3-8}$ cycloalkyl, —$C_{1-3}$ alkyl$C_{3-8}$cycloalkyl, —C(O)$R^f$, —$C_{1-6}$ alkylC(O)$R^f$, —C(O)O$R^f$, —$C_{1-6}$ alkylC(O)O$R^f$, —N$R^fR^g$, —$C_{1-6}$ alkylN$R^fR^g$, —C(O)N$R^fR^g$, —$C_{1-6}$ alkylC(O)N$R^fR^g$, —$SO_2R^f$, —$C_{1-6}$ alkyl$SO_2R^f$, —$SO_2NR^fR^g$, —$C_{1-6}$ alkyl$SO_2NR^fR^g$, —C(O)N$R^fSO_2R^g$ and —N$R^f$C(O)$R^g$;

$R^c$ is independently selected from H, OH, —$C_{1-6}$alkyl, —$C_{3-8}$ cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl;

$R^d$ is independently selected from H, —$C_{1-6}$alkyl, —$C_3$-$C_8$cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl;

$R^e$ is independently selected from H, —$C_{1-6}$alkyl, —O$C_{1-6}$alkyl, —$C_{3-8}$ cycloalkyl, aryl, heteroaryl, heterocyclyl, —O$C_{3-8}$cycloalkyl, —Oaryl, —Oheteroaryl, —Oheterocyclyl, —$C_{1-3}$ alkyl$C_{3-8}$cycloalkyl, —$C_{1-6}$alkylaryl, —$C_{1-6}$alkylheteroaryl, —N$R^fR^g$, —$C_{1-6}$alkylN$R^fR^g$, —C(O)N$R^fR^g$, —$C_{1-6}$alkylC(O)N$R^fR^g$, —NH$SO_2R^f$, —$C_{1-6}$alkyl$SO_2R^f$, and —$C_{1-6}$alkyl$SO_2NR^fR^g$;

$R^f$ is independently selected from H, —$C_{1-6}$alkyl, —$C_{3-8}$ cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl; and $R^g$ is independently selected from H, —$C_{1-6}$alkyl, —$C_{3-8}$ cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl;

or a pharmaceutically acceptable salt, stereoisomer, mixture of stereoisomers, or tautomer thereof.

In one embodiment of formula (IIb), $L^W$ is other than —$CH_2$O—, —$(CH_2)_2$—, —CH═CH—, and —C(O)NH—. In one embodiment of formula (IIb), $L^E$ is —O—$CH_2$—, where the oxygen is bonded to the Q group and the $CH_2$ is bonded to the Ar group. In one embodiment of formula (IIb), $L^E$ is a bond. In one embodiment of formula (IIb), one or both of $L^E$ or $L^W$ is a bond or —O—. In one embodiment of formula (IIb), one or both of $X^1$ is N. In one embodiment of formula (IIb), neither of $R^E$ or $R^W$ is an optionally substituted fused 5,6-aromatic or 5,6-heteromatic ring.

In one embodiment, the compound is represented by formula (IIc):

(IIc)

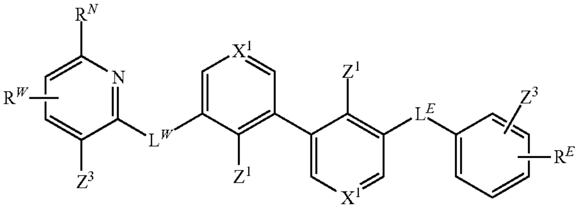

wherein each $X^1$ is independently N or CH;

each $Z^1$ is independently halo, —O$R^a$, —$C_{1-6}$ alkyl, —O$C_{1-6}$ alkyl, —$C_{1-6}$ haloalkyl, or —$C_{3-8}$ cycloalkyl;

each $Z^3$ is independently halo, —O$R^a$, —$N_3$, —$NO_2$, —CN, —N$R^1R^2$, —$SO_2R^a$, —$SO_2N^aR^b$, —N$R^aSO_2R^a$, —N$R^a$C(O)$R^a$, —C(O)$R^a$, —C(O)O$R^a$, —C(O)N$R^aR^b$, —N$R^a$C(O)O$R^a$, —N$R^a$C(O)N$R^1R^2$, —OC(O)N$R^aR^b$, —N$R^aSO_2NR^aR^b$, —C(O)N$R^aSO_2NR^aR^b$, —$C_{1-6}$ alkyl, —$C_{2-6}$ alkenyl, —$C_{2-6}$ alkynyl, —O$C_{1-6}$ alkyl, —$C_{3-8}$ cycloalkyl, —$C_{1-6}$ alkyl$C_{3-8}$ cycloalkyl, aryl, heteroaryl, heterocyclyl, and $R^N$;

wherein the alkyl, alkenyl, alkynyl, $C_{3-8}$ cycloalkyl, aryl, heteroaryl, or heterocyclyl group is optionally substituted with 1 to 4 groups independently selected from oxo, —$NO_2$, —$N_3$, —O$R^a$, halo, cyano, —N$R^aR^b$, —C(O)$R^a$, —C(O)O$R^a$, —O$C_{1-6}$alkyCN, —C(O)NR$^a$R$^b$, NR$^a$C(O)R$^a$, —NR$^a$C(O)OR$^a$, —SO$_2$R$^a$, —NR$^a$SO$_2$R, —SO$_2$NR$^a$R$^b$, —NR$^a$SO$_2$NR$^a$R$^b$, —C(O)NR$^a$SO$_2$NR$^a$R$^b$ and —C$_{3-8}$ cycloalkyl; and wherein the heteroaryl or heterocyclic group may be oxidized on a nitrogen atom to form an N-oxide or oxidized on a sulfur atom to form a sulfoxide or sulfone;

R$^N$ is independently —C$_{1-6}$ alkylNR$^1$R$^2$, —OC$_{1-6}$ alkyNR$^1$R$^2$, —C$_{1-6}$ alkylOC$_{1-6}$ alkylNR$^1$R$^2$, —NR$^a$C$_{1-6}$ alkylNR$^1$R$^2$, —C$_{1-6}$ alkylC(O)NR$^1$R$^2$, —OC$_{1-6}$ alkylC(O)NR$^1$R$^2$, —OC$_{1-6}$ alkylC(O)OR$^1$, —SC$_{1-6}$alkylNR$^1$R$^2$, —C$_{1-6}$ alkylOR$^a$, or

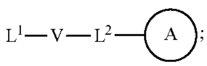;

wherein: L$^1$ is independently a bond, O, NR$^a$, S, SO, or SO$_2$;

V is independently selected from a bond, C$_{1-6}$alkyl, C$_{2-6}$alkenyl, and C$_{2-6}$alkynyl;

wherein each alkyl, alkenyl, or alkynyl is optionally independently substituted with OR$^a$, halo, cyano, —NR$^a$R$^b$ and —C$_{3-8}$ cycloalkyl;

L$^2$ is independently a bond, O, NR$^a$, S, SO, or SO$_2$;

ring A is independently cycloalkyl, aryl, heteroaryl, or heterocyclyl;

wherein each cycloalkyl, aryl, heteroaryl, or heterocyclyl is optionally substituted with 1 to 4 groups independently selected from oxo, —NO$_2$, —N$_3$, —OR$^a$, halo, cyano, —C$_{1-6}$ alkyl, —C$_{1-6}$ haloalkyl, —C$_{2-6}$alkenyl, —C$_{2-6}$ alkynyl, —OC$_{1-6}$ haloalkyl, NR$^a$R$^b$, —C(O)R$^a$, —C(O)OR$^a$, —OC$_{1-6}$ alkylCN, —C(O)NR$^a$R$^b$, —NR$^a$C(O)R$^a$, —NR$^a$C(O)OR$^a$, —NR$^a$C(O)OR$^a$, —C(O)N(R$^a$)OR$^b$, —SO$_2$R$^a$, —SO$_2$NR$^a$R$^b$, —NR$^a$SO$_2$R, —NR$^a$SO$_2$NR$^a$R$^b$, —C(O)NR$^a$SO$_2$NR$^a$R$^b$, C$_{3-8}$cycloalkyl, and C$_{1-6}$alkylC$_{3-8}$cycloalkyl; and wherein the alkyl, alkenyl, or alkynyl group is optionally independently substituted with —OR$^a$, halo, cyano, —NR$^a$R$^b$ or —C$_{3-8}$cycloalkyl L$^E$ and L$^W$ are each independently a bond, —O—, —S—, —SO—, —SO$_2$—, —(CR$^3$R$^4$)$_m$—, —(CR$^3$R$^4$)$_m$O(CR$^3$R$^4$)$_m$—, —(CR$^3$R$^4$)$_m$S(CR$^3$R$^4$)$_m$—, —(CR$^3$R$^4$)$_m$NR$^3$(CR$^3$R$^4$)$_m$—, —C(O)—, —(CR$^3$R$^4$)$_m$C(O)(CR$^3$R$^4$)$_m$—, —(CR$^3$R$^4$)$_m$C(O)NR$^3$(CR$^3$R$^4$)$_m$—, —(CR$^3$R$^4$)$_m$NR$^3$C(O)(CR$^3$R$^4$)$_m$—, C$_{2-6}$ alkenylene, C$_{2-6}$ alkynylene,

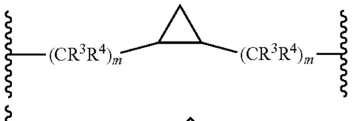
or
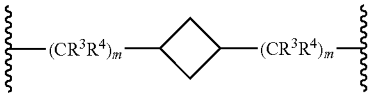;

each m is independently 0, 1, 2, 3 or 4;

R$^E$ and R$^W$ are each independently —NR$^1$R$^2$, —C$_{1-6}$ alkyNR$^1$R$^2$, —OC$_{1-6}$ alkylNR$^1$R$^2$, —C$_{1-6}$ alkyl OC$_{1-6}$alkylNR$^1$R$^2$, —NR$^a$C$_{1-6}$ alkylNR$^1$R$^2$, —C$_{1-6}$ alkylN$^+$R$^1$R$^2$R$^3$, —SC$_{1-6}$ alkylNR$^1$R$^2$, —C(O)NR$^1$R$^2$, —SO$_2$R$^a$, —(CH$_2$)$_u$SO$_2$NR$^1$R$^2$, —(CH$_2$)$_u$NR$^a$SO$_2$NR$^a$R$^b$, —SO$_2$NR$^a$C$_{1-6}$alkyNR$^1$R$^2$, —NR$^a$SO$_2$C$_{1-6}$ alkylNR$^1$R$^2$, —(CH$_2$)$_u$C(O)NR$^a$SO$_2$NR$^a$R$^b$, —(CH$_2$)$_u$N$^+$R$^1$R$^2$O$^-$, —(CH$_2$)$_u$P$^+$R$^b$R$^c$R$^d$, —(CH$_2$)$_u$P$^+$R$^c$R$^d$O$^-$, —(CH$_2$)$_u$P$^+$O[NR$^a$R$^b$][NR$^c$R$^d$], —(CH$_2$)$_u$NR$^c$P(O)(OR$^c$)$_2$, —(CH$_2$)$_u$CH$_2$OP(O)(OR$^c$)(OR$^d$), —(CH$_2$)$_u$OP(O)(OR$^c$)(OR$^d$), —(CH$_2$)$_u$OP(O)NR$^a$R$^b$)(OR$^a$), or

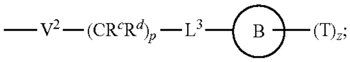;

wherein:

V$^2$ is independently a bond, O, NR$^a$, S, SO, SO$_2$, C(O)NR$^a$, NR$^a$C(O), SO$_2$NR$^1$R$^2$, or NR$^a$SO$_2$;

L$^3$ is independently a bond, O, NR$^a$, S, SO, SO$_2$, C(O)NR$^a$, NR$^a$C(O), SO$_2$NR$^1$R$^2$, or NR$^a$SO$_2$;

ring B is cycloalkyl, aryl, heteroaryl, or heterocyclyl; T is independently H, OR$^a$, (CH$_2$)$_q$NR$^1$R$^2$, (CH$_2$)$_q$NR$^a$C(O)R$^e$ or (CH$_2$)$_q$C(O)R$^e$;

p is independently 0, 1, 2, 3, 4, or 5;

q is independently 0, 1, 2, 3, 4, or 5;

u is 0, 1, 2, 3, or 4;

z is 0, 1, 2, or 3; and wherein the alkyl, cycloalkyl, aryl, heteroaryl, or heterocyclyl of R$^E$ or R$^W$ is optionally substituted with 1 to 3 substituents independently selected from the group consisting of NR$^a$R$^b$, halo, cyano, oxo, OR$^a$, —C$_{1-6}$alkyl, —C$_{1-6}$haloalkyl, —C$_{1-6}$cyanoalkyl, —C$_{1-6}$alkyNR$^a$R$^b$, —C$_{1-6}$alkylOH, —C$_{3-8}$ cycloalkyl, and —C$_{1-3}$ alkylC$_{3-8}$cycloalkyl;

provided that at least one of V$^2$, L$^3$, ring B and T contains a nitrogen atom;

R$^1$ is independently selected from H, —C$_{1-8}$ alkyl, —C$_{2-6}$ alkenyl, —C$_{2-6}$ alkynyl, —C$_{3-6}$ cycloalkyl, aryl, heteroaryl, heterocyclyl, —C$_{1-6}$alkylaryl, —C$_{1-6}$alkylheteroaryl, —C$_{1-6}$alkylheterocyclyl, —C$_{1-6}$ alkylC(O)OR$^a$, —C$_{2-6}$ alkenylC(O)OR$^a$, —SO$_2$R$^a$, —SO$_2$NR$^a$R$^b$, —C(O)NR$^a$SO$_2$R$^a$, and C$_{1-6}$ alkyl C$_{3-8}$cycloalkyl;

wherein each alkyl, alkenyl, cycloalkyl, aryl, heteroaryl, or heterocyclyl is optionally substituted with 1 to 4 groups independently selected from —OR$^a$, —CN, halo, C$_{1-6}$alkyl, —C$_{1-6}$alkylOR$^a$, —C$_{1-6}$cyanoalkyl, —C$_{1-6}$haloalkyl, C$_{3-8}$ cycloalkyl, —C$_{1-3}$ alkylC$_{3-8}$cycloalkyl, —C(O)R$^a$, —C$_{1-6}$ alkyl C(O)R$^a$, —C(O)OR$^a$, —C$_{1-6}$alkylC(O)OR$^a$, —NR$^a$R$^b$, —OC(O)NR$^a$R$^b$, NR$^a$C(O)OR$^b$, —C$_{1-6}$ alkylNR$^a$R$^b$, —C(O)NR$^a$R$^b$, —C$_{1-6}$alkylC(O)NR$^a$R$^b$, —SO$_2$R$^a$, —C$_{1-6}$alkylSO$_2$R$^a$, —SO$_2$N$^a$R$^b$, —C$_{1-6}$ alkylSO$_2$NR$^a$R$^b$, —C(O)NR$^a$SO$_2$R$^b$, —C$_{1-6}$ alkylC(O)NR$^a$SO$_2$R$^b$, —NR$^a$C(O)R$^b$, and —C$_{1-6}$alkylNR$^a$C(O)R$^b$;

R$^2$ is independently selected from H, —C$_{1-6}$alkyl, —C$_{2-6}$ alkenyl, —C$_{2-6}$ alkynyl, —C$_{3-6}$ cycloalkyl, aryl, heteroaryl, heterocyclyl, —C$_{1-6}$alkylaryl, —C$_{1-6}$alkylheteroaryl, —C$_{1-6}$ alkylheterocyclyl, —C$_{2-6}$alkyl-OR$^a$, —C$_{1-6}$ alkylC(O)OR$^a$, and —C$_{2-6}$ alkenylC(O)OR$^a$;

wherein each alkyl, alkenyl, alkynyl, cycloalkyl, aryl, heteroaryl, or heterocyclyl is optionally substituted with 1 to 4 groups independently selected from —OR$^a$, —CN, halo, C$_{1-6}$alkyl, —C$_{1-6}$alkylOR$^a$, —C$_{1-6}$cyanoalkyl, —C$_{1-6}$haloalkyl, —C$_{3-8}$cycloalkyl, —$C_{1-3}$alkyl$C_{3-8}$cycloalkyl, —C(O)$R^a$, —$C_{1-6}$ alkylC(O)$R^a$, —C(O)$OR^a$, —$C_{1-6}$ alkylC(O)$OR^a$, —$NR^aR^b$, —$C_{1-6}$ alkyl$NR^aR^b$, —C(O)$NR^aR^b$, $C_{1-6}$alkylC(O)$NR^aR^b$, —$SO_2R^a$, —$C_{1-6}$alkyl$SO_2R^a$, —$SO_2NR^aR^b$, —$C_{1-6}$alkyl$SO_2NR^aR^b$, —C(O) $NR^aSO_2R$, and —$NR^a$C(O)$R^b$;

or $R^1$ and $R^2$ combine to form a heterocyclyl group optionally containing 1, 2, or 3 additional heteroatoms independently selected from oxygen, sulfur and nitrogen, and optionally substituted with 1 to 3 groups independently selected from oxo, —$C_{1-6}$alkyl, —$C_{3-8}$cycloalkyl, —$C_{2-6}$ alkenyl, —$C_{2-6}$ alkynyl, —$OR^a$, —C(O)$OR^a$, —$C_{1-6}$cyanoalkyl, —$C_{1-6}$ alkyl$OR^a$, —$C_{1-6}$haloalkyl, —$C_{1-3}$ alkyl$C_{3-8}$cycloalkyl, —C(O)$R^a$, —$C_{1-6}$ alkylC(O)$R^a$, —$C_{1-6}$ alkylC(O)$OR^a$, —$NR^aR^b$, —$C_{1-6}$alkyl$NR^aR^b$, —C(O)$NR^aR^b$, —$C_{1-6}$ alkylC(O)$NR^aR^b$, —$SO_2R^a$, —$C_{1-6}$ alkyl$SO_2R^a$, —$SO_2NR^aR^b$, and $C_{1-6}$ alkyl$SO_2NR^aR^b$;

$R^3$ is independently H, —$C_{1-6}$alkyl, —$C_{2-6}$ alkenyl, —$C_{3-6}$ cycloalkyl, aryl, heteroaryl, heterocyclyl, —$C_{1-6}$alkylaryl, —$C_{1-6}$alkylheteroaryl, —$C_{1-6}$ alkylheterocyclyl, —$C_{2-6}$alkyl-$OR^a$, —$C_{1-6}$alkylC(O)$OR^a$, or —$C_{2-6}$ alkenylC(O)$OR^a$;

$R^4$ is independently H, —$C_{1-6}$alkyl, —$C_{2-6}$ alkenyl, —$C_{3-6}$ cycloalkyl, aryl, heteroaryl, heterocyclyl, —$C_{1-6}$alkylaryl, —$C_{1-6}$alkylheteroaryl, —$C_{1-6}$ alkylheterocyclyl, —$C_{2-6}$alkyl-$OR^a$, —$C_{1-6}$alkylC(O)$OR^a$, or —$C_{2-6}$ alkenylC(O)$OR^a$;

$R^a$ is independently selected from H, —$C_{1-6}$alkyl, —$C_{3-8}$cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl;

$R^b$ is independently selected from H, —$C_{1-6}$alkyl, —$C_{3-8}$ cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$ alkylheterocyclyl;

or $R^a$ and $R^b$ may combine together to form a ring consisting of 3-8 ring atoms that are C, N, O, or S; wherein the ring is optionally substituted with 1 to 4 groups independently selected from —$OR^f$, —CN, halo, —$C_{1-6}$ alkyl$OR^f$, —$C_{1-6}$ cyanoalkyl, —$C_{1-6}$haloalkyl, —$C_{3-8}$ cycloalkyl, —$C_{1-3}$ alkyl$C_{3-8}$cycloalkyl, —C(O)$R^f$, —$C_{1-6}$ alkylC(O)$R^f$, —C(O)$OR^f$, —$C_{1-6}$ alkylC(O)$OR^f$, —$NR^fR^g$, —$C_{1-6}$ alkyl$NR^fR^g$, —C(O) $NR^fR^g$, —$C_{1-6}$ alkylC(O)$NR^fR^g$, —$SO_2R^f$, —$C_{1-6}$ alkyl$SO_2R^f$, —$SO_2NR^fR^g$, —$C_{1-6}$ alkyl$SO_2NR^fR^g$, —C(O)$NR^fSO_2R^g$ and —$NR^f$C(O)$R^g$;

$R^c$ is independently selected from H, OH, —$C_{1-6}$alkyl, —$C_{3-8}$ cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl;

$R^d$ is independently selected from H, —$C_{1-6}$alkyl, —$C_3$-$C_8$cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl;

$R^e$ is independently selected from H, —$C_{1-6}$alkyl, —$OC_{1-6}$alkyl, —$C_{3-8}$ cycloalkyl, aryl, heteroaryl, heterocyclyl, —$OC_{3-8}$cycloalkyl, —Oaryl, —Oheteroaryl, —Oheterocyclyl, —$C_{1-3}$ alkyl$C_{3-8}$cycloalkyl, —$C_{1-6}$alkylaryl, —$C_{1-6}$alkylheteroaryl, —$NR^fR^g$, —$C_{1-6}$alkyl$NR^fR^g$, —C(O)$NR^fR^g$, —$C_{1-6}$alkylC(O) $NR^fR^g$, —$NHSO_2R^f$, —$C_{1-6}$alkyl$SO_2R^f$, and —$C_{1-6}$alkyl$SO_2NR^fR^g$;

$R^f$ is independently selected from H, —$C_{1-6}$alkyl, —$C_{3-8}$ cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl; and $R^g$ is independently selected from H, —$C_{1-6}$alkyl, —$C_{3-8}$ cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl;

or a pharmaceutically acceptable salt, stereoisomer, mixture of stereoisomers, or tautomer thereof.

In one embodiment of formula (IIc), $L^E$ is other than —$CH_2O$—, —$(CH_2)_2$—, —CH═CH—, and —C(O)NH—. In one embodiment of formula (IIc), $L^W$ is —O—$CH_2$—, where the oxygen is bonded to the Q ring and the $CH_2$ is bonded to the Ar ring. In certain embodiments of formula (IIc), one or both of $L^E$ or $L^W$ is a bond or —O—. In certain embodiments of formula (IIc), one or both of $X^1$ is N. In certain embodiments of formula (IIc), neither of $R^E$ or $R^W$ is an optionally substituted fused 5,6-aromatic or 5,6-heteromatic ring.

In one embodiment, the compound is represented by formula (IId):

(IId)

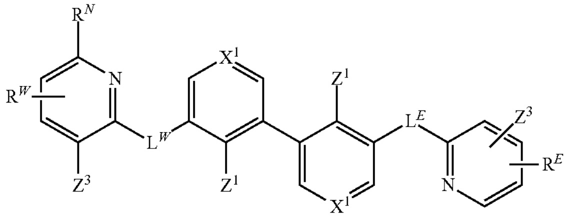

wherein each X is independently N or CH;

each $Z^1$ is independently halo, —$OR^a$, —$C_{1-6}$ alkyl, —$OC_{1-6}$ alkyl, —$C_{1-6}$ haloalkyl, or —$C_{3-8}$ cycloalkyl;

each $Z^3$ is independently halo, —$OR^a$, —$N_3$, —$NO_2$, —CN, —$NR^1R^2$, —$SO_2R^a$, —$SO_2N^aR^b$, —$NR^aSO_2R^a$, —$NR^a$C(O)$R^a$, —C(O)$R^a$, —C(O)$OR^a$, —C(O)$NR^aR^b$, —$NR^a$C(O)$OR^a$, —$NR^a$C(O)$NR^1R^2$, —OC(O)$NR^aR^b$, —$NR^aSO_2NR^aR^b$, —C(O) $NR^aSO_2NR^aR^b$, —$C_{1-6}$ alkyl, —$C_{2-6}$alkenyl, —$C_{2-6}$ alkynyl, —$OC_{1-6}$ alkyl, —$C_{3-8}$ cycloalkyl, —$C_{1-6}$ alkyl$C_{3-8}$ cycloalkyl, aryl, heteroaryl, heterocyclyl, and $R^N$;

wherein the alkyl, alkenyl, alkynyl, $C_{3-8}$ cycloalkyl, aryl, heteroaryl, or heterocyclyl group is optionally substituted with 1 to 4 groups independently selected from oxo, —$NO_2$, —$N_3$, —$OR^a$, halo, cyano, —$NR^aR^b$, —C(O)$R^a$, —C(O)$OR^a$, —$OC_{1-6}$alkyCN, —C(O)$NR^aR^b$, $NR^a$C(O)$R^a$, —$NR^a$C(O)$OR^a$, —$SO_2R^a$, —$NR^aSO_2R$, —$SO_2NR^aR^b$, —$NR^aSO_2NR^aR^b$, —C(O)$NR^aSO_2NR^aR^b$ and —$C_{3-8}$ cycloalkyl; and wherein the heteroaryl or heterocyclic group may be oxidized on a nitrogen atom to form an N-oxide or oxidized on a sulfur atom to form a sulfoxide or sulfone;

$R^N$ is independently —$C_{1-6}$ alkyl$NR^1R^2$, —$OC_{1-6}$ alky$NR^1R^2$, —$C_{1-6}$ alkyl$OC_{1-6}$ alkyl$NR^1R^2$, —$NR^aC_{1-6}$ alkyl$NR^1R^2$, —$C_{1-6}$ alkylC(O)$NR^1R^2$, —$OC_{1-6}$ alkylC(O)$NR^1R^2$, —$OC_{1-6}$ alkylC(O)$OR^1$, —$SC_{1-6}$alkyl$NR^1R^2$, —$C_{1-6}$alkyl$OR^a$, or

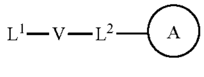;

wherein: $L^1$ is independently a bond, O, $NR^a$, S, SO, or $SO_2$;

V is independently selected from a bond, $C_{1-6}$alkyl, $C_{2-6}$alkenyl, and $C_{2-6}$alkynyl;

wherein each alkyl, alkenyl, or alkynyl is optionally independently substituted with $OR^a$, halo, cyano, —$NR^aR^b$ and —$C_{3-8}$ cycloalkyl;

$L^2$ is independently a bond, O, $NR^a$, S, SO, or $SO_2$;

ring A is independently cycloalkyl, aryl, heteroaryl, or heterocyclyl;

wherein each cycloalkyl, aryl, heteroaryl, or heterocyclyl is optionally substituted with 1 to 4 groups independently selected from oxo, —$NO_2$, —$N_3$, —$OR^a$, halo, cyano, —$C_{1-6}$ alkyl, —$C_{1-6}$ haloalkyl, —$C_{2-6}$alkenyl, —$C_{2-6}$ alkynyl, —$OC_{1-6}$ haloalkyl, $NR^aR^b$, —$C(O)R^a$, —$C(O)OR^a$, —$OC_{1-6}$ alkylCN, —$C(O)NR^aR^b$, —$NR^aC(O)R^a$, —$NR^aC(O)OR^a$, —$NR^aC(O)OR^a$, —$C(O)N(R^a)OR^b$, —$SO_2R^a$, —$SO_2NR^aR^b$, —$NR^aSO_2R^b$, —$NR^aSO_2NR^aR^b$, —$C(O)NR^aSO_2NR^aR^b$, $C_{3-8}$cycloalkyl, and $C_{1-6}$alkyl$C_{3-8}$ cycloalkyl; and wherein the alkyl, alkenyl, or alkynyl group is optionally independently substituted with —$OR^a$, halo, cyano, —$NR^aR^b$ or —$C_{3-8}$cycloalkyl $L^E$ and $L^W$ are each independently a bond, —O—, —S—, —SO—, —$SO_2$—, —$(CR^3R^4)_m$—, —$(CR^3R^4)_mO(CR^3R^4)_m$—, —$(CR^3R^4)_mS(CR^3R^4)_m$—, —$(CR^3R^4)_mNR^3(CR^3R^4)_m$—, —C(O)—, —$(CR^3R^4)_mC(O)(CR^3R^4)_m$—, —$(CR^3R^4)_mC(O)NR^3(CR^3R^4)_m$—, —$(CR^3R^4)_mNR^3C(O)(CR^3R^4)_m$—, $C_{2-6}$ alkenylene, $C_{2-6}$ alkynylene,

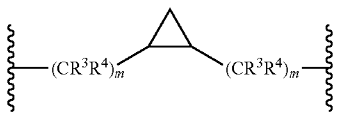

or

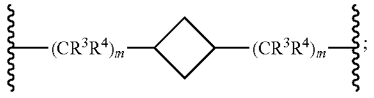

each m is independently 0, 1, 2, 3 or 4;

$R^E$ and $R^W$ are each independently —$NR^1R^2$, —$C_{1-6}$ alkyNR$^1$R$^2$, —$OC_{1-6}$ alkylNR$^1$R$^2$, —$C_{1-6}$ alkylO$C_{1-6}$alkylNR$^1$R$^2$, —$NR^aC_{1-6}$ alkylNR$^1$R$^2$, —$C_{1-6}$ alkylN$^+$R$^1$R$^2$R$^3$, —$SC_{1-6}$ alkylNR$^1$R$^2$, —$C(O)NR^1R^2$, —$SO_2R^a$, —$(CH_2)_uSO_2NR^1R^2$, —$(CH_2)_uNR^aSO_2NR^aR^b$, —$SO_2NR^aC_{1-6}$alkyNR$^1$R$^2$, —$NR^aSO_2C_{1-6}$ alkylNR$^1$R$^2$, —$(CH_2)_uC(O)NR^aSO_2NR^aR^b$, —$(CH_2)_uN^+R^1R^2O^-$, —$(CH_2)_uP^+R^bR^cR^d$, —$(CH_2)_uP^+R^cR^dO^-$, —$(CH_2)_uP^+O[NR^aR^b][NR^cR^d]$, —$(CH_2)_uNR^cP(O)(OR^c)_2$, —$(CH_2)_uCH_2OP(O)(OR^c)(OR^d)$, —$(CH_2)_uOP(O)(OR^c)(OR^d)$, —$(CH_2)_uOP(O)NR^aR^b)(OR^a)$, or

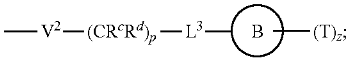

wherein:

$V^2$ is independently a bond, O, $NR^a$, S, SO, $SO_2$, $C(O)NR^a$, $NR^aC(O)$, $SO_2NR^1R^2$, or $NR^aSO_2$;

$L^3$ is independently a bond, O, $NR^a$, S, SO, $SO_2$, $C(O)NR^a$, $NR^aC(O)$, $SO_2NR^1R^2$, or $NR^aSO_2$;

ring B is cycloalkyl, aryl, heteroaryl, or heterocyclyl; T is independently H, $OR^a$, $(CH_2)_qNR^1R^2$, $(CH_2)_qNR^aC(O)R^e$ or $(CH_2)_qC(O)R$;

p is independently 0, 1, 2, 3, 4, or 5;

q is independently 0, 1, 2, 3, 4, or 5;

u is 0, 1, 2, 3, or 4;

z is 0, 1, 2, or 3; and wherein the alkyl, cycloalkyl, aryl, heteroaryl, or heterocyclyl of $R^E$ or $R^W$ is optionally substituted with 1 to 3 substituents independently selected from the group consisting of $NR^aR^b$, halo, cyano, oxo, $OR^a$, —$C_{1-6}$alkyl, —$C_{1-6}$haloalkyl, —$C_{1-6}$cyanoalkyl, —$C_{1-6}$alkyNR$^a$R$^b$, —$C_{1-6}$alkylOH, —$C_{3-8}$ cycloalkyl, and —$C_{1-3}$ alkyl$C_{3-8}$cycloalkyl;

provided that at least one of $V^2$, $L^3$, ring B and T contains a nitrogen atom;

$R^1$ is independently selected from H, —$C_{1-8}$ alkyl, —$C_{2-6}$ alkenyl, —$C_{2-6}$ alkynyl, —$C_{3-6}$ cycloalkyl, aryl, heteroaryl, heterocyclyl, —$C_{1-6}$alkylaryl, —$C_{1-6}$alkylheteroaryl, —$C_{1-6}$alkylheterocyclyl, —$C_{1-6}$ alkylC(O)OR$^a$, —$C_{2-6}$ alkenylC(O)OR$^a$, —$SO_2R^a$, —$SO_2N^aR^b$, —$C(O)NR^aSO_2R^a$, and $C_{1-6}$ alkyl$C_{3-8}$cycloalkyl;

wherein each alkyl, alkenyl, cycloalkyl, aryl, heteroaryl, or heterocyclyl is optionally substituted with 1 to 4 groups independently selected from —$OR^a$, —CN, halo, $C_{1-6}$alkyl, —$C_{1-6}$alkylOR$^a$, —$C_{1-6}$cyanoalkyl, —$C_{1-6}$haloalkyl, $C_{3-8}$cycloalkyl, —$C_{1-3}$alkyl$C_{3-8}$cycloalkyl, —$C(O)R^a$, —$C_{1-6}$ alkylC(O)R$^a$, —$C(O)OR^a$, —$C_{1-6}$ alkylC(O)OR$^a$, —$NR^aR^b$, —$OC(O)NR^aR^b$, $NR^aC(O)OR^b$, —$C_{1-6}$alkylNR$^a$R$^b$, —$C(O)NR^aR^b$, —$C_{1-6}$alkylC(O)NR$^a$R$^b$, —$SO_2R^a$, —$C_{1-6}$alkylSO$_2$R$^a$, —$SO_2NR^aR^b$, —$C_{1-6}$ alkylSO$_2$NR$^a$R$^b$, —$C(O)NR^aSO_2R^b$, —$C_{1-6}$ alkylC(O)NR$^a$SO$_2$R$^b$, —$NR^aC(O)R^b$, and —$C_{1-6}$alkylNR$^a$C(O)R$^b$;

$R^2$ is independently selected from H, —$C_{1-6}$alkyl, —$C_{2-6}$ alkenyl, —$C_{2-6}$ alkynyl, —$C_{3-6}$ cycloalkyl, aryl, heteroaryl, heterocyclyl, —$C_{1-6}$alkylaryl, —$C_{1-6}$alkylheteroaryl, —$C_{1-6}$ alkylheterocyclyl, —$C_{2-6}$alkyl-OR$^a$, —$C_{1-6}$ alkylC(O)OR$^a$, and —$C_{2-6}$ alkenylC(O)OR$^a$;

wherein each alkyl, alkenyl, alkynyl, cycloalkyl, aryl, heteroaryl, or heterocyclyl is optionally substituted with 1 to 4 groups independently selected from —$OR^a$, —CN, halo, $C_{1-6}$alkyl, —$C_{1-6}$alkylOR$^a$, —$C_{1-6}$cyanoalkyl, —$C_{1-6}$haloalkyl, —$C_{3-8}$cycloalkyl, —$C_{1-3}$alkyl$C_{3-8}$cycloalkyl, —$C(O)R^a$, —$C_{1-6}$ alkylC(O)R$^a$, —$C(O)OR^a$, —$C_{1-6}$ alkylC(O)OR$^a$, —$NR^aR^b$, —$C_{1-6}$ alkylNR$^a$R$^b$, —$C(O)NR^aR^b$, $C_{1-6}$alkylC(O)NR$^a$R$^b$, —$SO_2R^a$, —$C_{1-6}$alkylSO$_2$R$^a$, —$SO_2NR^aR^b$, —$C_{1-6}$alkylSO$_2$NR$^a$R$^b$, —$C(O)NR^aSO_2R$, and —$NR^aC(O)R^b$;

or $R^1$ and $R^2$ combine to form a heterocyclyl group optionally containing 1, 2, or 3 additional heteroatoms independently selected from oxygen, sulfur and nitrogen, and optionally substituted with 1 to 3 groups independently selected from oxo, —$C_{1-6}$alkyl, —$C_{3-8}$ cycloalkyl, —$C_{2-6}$ alkenyl, —$C_{2-6}$ alkynyl, —$OR^a$, —$C(O)OR^a$, —$C_{1-6}$cyanoalkyl, —$C_{1-6}$ alkylOR$^a$, —$C_{1-6}$haloalkyl, —$C_{1-3}$ alkyl$C_{3-8}$cycloalkyl, —$C(O)R^a$, —$C_{1-6}$ alkylC(O)R$^a$, —$C_{1-6}$ alkylC(O)OR$^a$, —$NR^aR^b$, —$C_{1-6}$alkyNR$^a$R$^b$, —$C(O)NR^aR^b$, —$C_{1-6}$ alkylC(O)NR$^a$R$^b$, —$SO_2R^a$, —$C_{1-6}$ alkylSO$_2$R$^a$, —$SO_2NR^aR^b$, and $C_{1-6}$ alkylSO$_2$NR$^a$R$^b$;

$R^3$ is independently H, —$C_{1-6}$alkyl, —$C_{2-6}$ alkenyl, —$C_{3-6}$ cycloalkyl, aryl, heteroaryl, heterocyclyl, —$C_{1-6}$alkylaryl, —$C_{1-6}$alkylheteroaryl, —$C_{1-6}$ alkylheterocyclyl, —$C_{2-6}$alkyl-$OR^a$, —$C_{1-6}$alkylC(O)$OR^a$, or —$C_{2-6}$ alkenylC(O)$OR^a$;

$R^4$ is independently H, —$C_{1-6}$alkyl, —$C_{2-6}$ alkenyl, —$C_{3-6}$ cycloalkyl, aryl, heteroaryl, heterocyclyl, —$C_{1-6}$ alkylaryl, —$C_{1-6}$ alkylheteroaryl, —$C_{1-6}$ alkylheterocyclyl, —$C_{2-6}$alkyl-$OR^a$, —$C_{1-6}$ alkylC(O)$OR^a$, or —$C_{2-6}$ alkenylC(O)$OR^a$;

$R^a$ is independently selected from H, —$C_{1-6}$alkyl, —$C_{3-8}$ cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl;

$R^b$ is independently selected from H, —$C_{1-6}$alkyl, —$C_{3-8}$ cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$ alkylheterocyclyl;

or $R^a$ and $R^b$ may combine together to form a ring consisting of 3-8 ring atoms that are C, N, O, or S; wherein the ring is optionally substituted with 1 to 4 groups independently selected from —$OR^f$, —CN, halo, —$C_{1-6}$ alkyl$OR^f$, —$C_{1-6}$cyanoalkyl, —$C_{1-6}$haloalkyl, —$C_{3-8}$ cycloalkyl, —$C_{1-3}$ alkyl$C_{3-8}$cycloalkyl, —C(O)$R^f$, —$C_{1-6}$alkylC(O)$R^f$, —C(O)$OR^f$, —$C_{1-6}$alkylC(O)$OR^f$, —$NR^fR^g$, —$C_{1-6}$alkyl$NR^fR^g$, —C(O)$NR^fR^g$, —$C_{1-6}$alkylC(O)$NR^fR^g$, —$SO_2R^f$, —$C_{1-6}$ alkyl$SO_2R^f$, —$SO_2NR^fR^g$, —$C_{1-6}$alkyl$SO_2NR^fR^g$, —C(O)$NR^fSO_2R^g$ and —$NR^f$C(O)$R^g$;

$R^c$ is independently selected from H, OH, —$C_{1-6}$alkyl, —$C_{3-8}$cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl;

$R^d$ is independently selected from H, —$C_{1-6}$alkyl, —$C_3$-$C_8$cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl;

$R^e$ is independently selected from H, —$C_{1-6}$alkyl, —$OC_{1-6}$alkyl, —$C_{3-8}$ cycloalkyl, aryl, heteroaryl, heterocyclyl, —$OC_{3-8}$cycloalkyl, —Oaryl, —Oheteroaryl, —Oheterocyclyl, —$C_{1-3}$ alkyl$C_{3-8}$cycloalkyl, —$C_{1-6}$alkylaryl, —$C_{1-6}$alkylheteroaryl, —$NR^fR^g$, —$C_{1-6}$alkyl$NR^f$RR, —C(O)$NR^fR^g$, —$C_{1-6}$alkylC(O)$NR^fR^g$, —$NHSO_2R^f$, —$C_{1-6}$alkyl$SO_2R^f$, and —$C_{1-6}$alkyl$SO_2NR^fR^g$;

$R^f$ is independently selected from H, —$C_{1-6}$alkyl, —$C_{3-8}$ cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl; and $R^g$ is independently selected from H, —$C_{1-6}$alkyl, —$C_{3-8}$ cycloalkyl, aryl, heteroaryl, heterocyclyl, —$C_{1-3}$ alkyl$C_{3-8}$ cycloalkyl, —$C_{1-6}$ alkylaryl, —$C_{1-6}$ alkylheteroaryl, and —$C_{1-6}$alkylheterocyclyl;

or a pharmaceutically acceptable salt, stereoisomer, mixture of stereoisomers, or tautomer thereof.

In one embodiment of formula (IId), neither of $R^E$ or $R^W$ is an optionally substituted fused 5,6-aromatic or 5,6-heteromatic ring.

In one embodiment, the compound is represented by any one of formula (IIe):

(IIe)

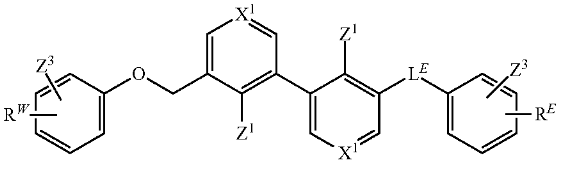

wherein each $X^1$ is independently N or CH;

each $Z^1$ is independently halo, —$OR^a$, —$C_{1-6}$ alkyl, —$OC_{1-6}$alkyl, —$C_{1-6}$ haloalkyl, or —$C_{3-8}$ cycloalkyl;

each $Z^3$ is independently halo, —$OR^a$, —$N_3$, —$NO_2$, —CN, —$NR^1R^2$, —$SO_2R^a$, —$SO_2N^aR^b$, —$NR^aSO_2R^a$, —$NR^a$C(O)$R^a$, —C(O)$R^a$, —C(O)$OR^a$, —C(O)$NR^aR^b$, —$NR^a$C(O)$OR^a$, —$NR^a$C(O)$NR^1R^2$, —OC(O)$NR^aR^b$, —$NR^aSO_2NR^aR^b$, —C(O)$NR^aSO_2NR^aR^b$, —$C_{1-6}$ alkyl, —$C_{2-6}$ alkenyl, —$C_{2-6}$ alkynyl, —$OC_{1-6}$alkyl, —$C_{3-8}$ cycloalkyl, —$C_{1-6}$ alkyl$C_{3-8}$ cycloalkyl, aryl, heteroaryl, heterocyclyl, and $R^N$;

wherein the alkyl, alkenyl, alkynyl, $C_{3-8}$ cycloalkyl, aryl, heteroaryl, or heterocyclyl group is optionally substituted with 1 to 4 groups independently selected from oxo, —$NO_2$, —$N_3$, —$OR^a$, halo, cyano, —$NR^aR^b$, —C(O)$R^a$, —C(O)$OR^a$, —$OC_{1-6}$alkyCN, —C(O)$NR^aR^b$, $NR^a$C(O)$R^a$, —$NR^a$C(O)$OR^a$, —$SO_2R^a$, —$NR^aSO_2$R, —$SO_2NR^aR^b$, —$NR^aSO_2NR^aR^b$, —C(O)$NR^aSO_2NR^aR^b$ and —$C_{3-8}$ cycloalkyl; and wherein the heteroaryl or heterocyclic group may be oxidized on a nitrogen atom to form an N-oxide or oxidized on a sulfur atom to form a sulfoxide or sulfone;

$R^N$ is independently —$C_{1-6}$alkyl$NR^1R^2$, —$OC_{1-6}$ alky$NR^1R^2$, —$C_{1-6}$ alkyl$OC_{1-6}$ alkyl$NR^1R^2$, —$NR^aC_{1-6}$ alkyl$NR^1R^2$, —$C_{1-6}$ alkylC(O)$NR^1R^2$, —$OC_{1-6}$ alkylC(O)$NR^1R^2$, —$OC_{1-6}$ alkylC(O)$OR^1$, —$SC_{1-6}$alkyl$NR^1R^2$, —$C_{1-6}$alkyl$OR^a$, or

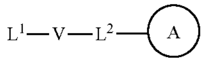;

wherein: $L^1$ is independently a bond, O, $NR^a$, S, SO, or $SO_2$;

V is independently selected from a bond, $C_{1-6}$alkyl, $C_{2-6}$alkenyl, and $C_{2-6}$alkynyl;

wherein each alkyl, alkenyl, or alkynyl is optionally independently substituted with $OR^a$, halo, cyano, —$NR^aR^b$ and —$C_{3-8}$ cycloalkyl;

$L^2$ is independently a bond, O, $NR^a$, S, SO, or $SO_2$;

ring A is independently cycloalkyl, aryl, heteroaryl, or heterocyclyl;

wherein each cycloalkyl, aryl, heteroaryl, or heterocyclyl is optionally substituted with 1 to 4 groups independently selected from oxo, —$NO_2$, —$N_3$, —$OR^a$, halo, cyano, —$C_{1-6}$ alkyl, —$C_{1-6}$ haloalkyl, —$C_{2-6}$alkenyl, —$C_{2-6}$ alkynyl, —$OC_{1-6}$ haloalkyl, $NR^aR^b$, —C(O)$R^a$, —C(O)$OR^a$, —$OC_{1-6}$ alkylCN, —C(O)$NR^aR^b$, —$NR^a$C(O)$R^a$, —$NR^a$C(O)$OR^a$, —$NR^a$C(O)$OR^a$, —C(O)N($R^a$)$OR^b$, —$SO_2R^a$, —$SO_2NR^aR^b$, —$NR^aSO_2R^b$, —$NR^aSO_2NR^aR^b$, —C(O)$NR^aSO_2NR^aR^b$, $C_{3-8}$cycloalkyl, and $C_{1-6}$alkyl$C_{3-8}$ cycloalkyl; and wherein the alkyl, alkenyl, or alkynyl group is optionally independently substituted with —$OR^a$, halo, cyano, —$NR^aR^b$ or —$C_{3-8}$ cycloalkyl $L^E$ is a bond, —O—, —S—, —SO—, —$SO_2$—, —$(CR^3R^4)_m$—, —$(CR^3R^4)_m$O$(CR^3R^4)_m$—, —$(CR^3R^4)_m$S$(CR^3R^4)_m$—, —$(CR^3R^4)_m$$NR^3$ $(CR^3R^4)_m$—, C(O)—, —$(CR^3R^4)_m$C(O)$(CR^3R^4)_m$—, —$(CR^3R^4)_m$C(O)$NR^3(CR^3R^4)_m$—, —$(CR^3R^4)_mNR^3$C(O)$(CR^3R^4)_m$—, $C_{2-6}$ alkenylene,

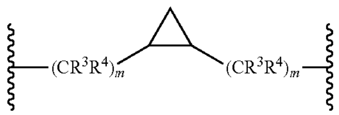

or

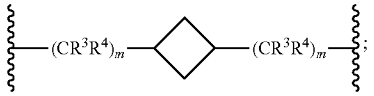

each m is independently 0, 1, 2, 3 or 4;

$R^E$ and $R^W$ are each independently —$NR^1R^2$, —$C_{1-6}$ alkyNR$^1R^2$, —OC$_{1-6}$ alkylNR$^1R^2$, —$C_{1-6}$ alkylOC$_{1-6}$alkylNR$^1R^2$, —NR$^a$C$_{1-6}$ alkylNR$^1R^2$, —$C_{1-6}$ alkylN$^+$R$^1$R$^2$R$^3$, —SC$_{1-6}$ alkylNR$^1R^2$, —C(O)NR$^1R^2$, —SO$_2$R$^a$, —(CH$_2$)$_u$SO$_2$NR$^1$R$^2$, —(CH$_2$)$_u$NR$^a$SO$_2$NR$^a$R$^b$, —SO$_2$NR$^a$C$_{1-6}$ alkyNR$^1$R$^2$, —NR$^a$SO$_2$C$_{1-6}$ alkylNR$^1$R$^2$, —(CH$_2$)$_u$C(O)NR$^a$SO$_2$NR$^a$R$^b$, —(CH$_2$)$_u$N$^+$R$^1$R$^2$O$^-$, —(CH$_2$)$_u$P$^+$R$^b$R$^c$R$^d$, —(CH$_2$)$_u$P$^+$R$^c$R$^d$O$^-$, —(CH$_2$)$_u$P$^+$O[NR$^a$R$^b$][NR$^c$R$^d$], —(CH$_2$)$_u$NR$^c$P(O)(OR$^c$)$_2$, —(CH$_2$)$_u$CH$_2$OP(O)(OR$^c$)(OR$^d$), —(CH$_2$)$_u$OP(O)(OR$^c$)(OR$^d$), —(CH$_2$)$_u$OP(O)NR$^a$R$^b$)(OR$^a$), or

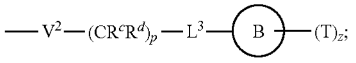

wherein:

$V^2$ is independently a bond, O, NR$^a$, S, SO, SO$_2$, C(O)NR$^a$, NR$^a$C(O), SO$_2$NR$^1$R$^2$, or NR$^a$SO$_2$;

$L^3$ is independently a bond, O, NR$^a$, S, SO, SO$_2$, C(O)NR$^a$, NR$^a$C(O), SO$_2$NR$^1$R$^2$, or NR$^a$SO$_2$;

ring B is cycloalkyl, aryl, heteroaryl, or heterocyclyl; T is independently H, OR$^a$, (CH$_2$)$_q$NR$^1$R$^2$, (CH$_2$)$_q$NR$^a$C(O)R$^e$ or (CH$_2$)$_q$C(O)R$^e$;

p is independently 0, 1, 2, 3, 4, or 5;

q is independently 0, 1, 2, 3, 4, or 5;

u is 0, 1, 2, 3, or 4;

z is 0, 1, 2, or 3; and wherein the alkyl, cycloalkyl, aryl, heteroaryl, or heterocyclyl of $R^E$ or $R^W$ is optionally substituted with 1 to 3 substituents independently selected from the group consisting of NR$^a$R$^b$, halo, cyano, oxo, OR$^a$, —C$_{1-6}$alkyl, —C$_{1-6}$haloalkyl, —C$_{1-6}$ cyanoalkyl, —C$_{1-6}$alkyNR$^a$R$^b$, —C$_{1-6}$alkylOH, —C$_{3-8}$ cycloalkyl, and —C$_{1-3}$ alkylC$_{3-8}$cycloalkyl;

provided that at least one of V$^2$, L$^3$, ring B and T contains a nitrogen atom;

$R^1$ is independently selected from H, —C$_{1-8}$ alkyl, —C$_{2-6}$ alkenyl, —C$_{2-6}$ alkynyl, —C$_{3-6}$ cycloalkyl, aryl, heteroaryl, heterocyclyl, —C$_{1-6}$ alkylaryl, —C$_{1-6}$ alkylheteroaryl, —C$_{1-6}$ alkylheterocyclyl, —C$_{1-6}$ alkylC(O)OR$^a$, —C$_{2-6}$ alkenylC(O)OR$^a$, —SO$_2$R$^a$, —SO$_2$NR$^a$R$^b$, —C(O)NR$^a$SO$_2$R$^a$, and C$_{1-6}$ alkylC$_{3-8}$cycloalkyl;

wherein each alkyl, alkenyl, cycloalkyl, aryl, heteroaryl, or heterocyclyl is optionally substituted with 1 to 4 groups independently selected from —OR$^a$, —CN, halo, C$_{1-6}$alkyl, —C$_{1-6}$ alkylOR$^a$, —C$_{1-6}$ cyanoalkyl, —C$_{1-6}$haloalkyl, C$_{3-8}$ cycloalkyl, —C$_{1-3}$alkylC$_{3-8}$cycloalkyl, —C(O)R$^a$, —C$_{1-6}$ alkylC(O)R$^a$, —C(O)OR$^a$, —C$_{1-6}$ alkylC(O)OR$^a$, —NR$^a$R$^b$, —OC(O)NR$^a$R$^b$, NR$^a$C(O)OR$^b$, —C$_{1-6}$alkylNR$^a$R$^b$, —C(O)NR$^a$R$^b$, —C$_{1-6}$ alkylC(O)NR$^a$R$^b$, —SO$_2$R$^a$, —C$_{1-6}$alkylSO$_2$R$^a$, —SO$_2$NR$^a$R$^b$, —C$_{1-6}$ alkylSO$_2$NR$^a$R$^b$, —C(O)NR$^a$SO$_2$R$^b$, —C$_{1-6}$ alkylC(O)NR$^a$SO$_2$R$^b$, —NR$^a$C(O)R$^b$, and —C$_{1-6}$alkylNR$^a$C(O)R$^b$;

$R^2$ is independently selected from H, —C$_{1-6}$ alkyl, —C$_{2-6}$ alkenyl, —C$_{2-6}$ alkynyl, —C$_{3-6}$ cycloalkyl, aryl, heteroaryl, heterocyclyl, —C$_{1-6}$ alkylaryl, —C$_{1-6}$ alkylheteroaryl, —C$_{1-6}$ alkylheterocyclyl, —C$_{2-6}$alkyl-OR$^a$, —C$_{1-6}$ alkylC(O)OR$^a$, and —C$_{2-6}$ alkenylC(O)OR$^a$;

wherein each alkyl, alkenyl, alkynyl, cycloalkyl, aryl, heteroaryl, or heterocyclyl is optionally substituted with 1 to 4 groups independently selected from —OR$^a$, —CN, halo, C$_{1-6}$alkyl, —C$_{1-6}$alkylOR$^a$, —C$_{1-6}$cyanoalkyl, —C$_{1-6}$haloalkyl, —C$_{3-8}$cycloalkyl, —C$_{1-3}$alkylC$_{3-8}$cycloalkyl, —C(O)R$^a$, —C$_{1-6}$ alkylC(O)R$^a$, —C(O)OR$^a$, —C$_{1-6}$ alkylC(O)OR$^a$, —NR$^a$R$^b$, —C$_{1-6}$ alkylNR$^a$R$^b$, —C(O)NR$^a$R$^b$, C$_{1-6}$alkylC(O)NR$^a$R$^b$, —SO$_2$R$^a$, —C$_{1-6}$alkylSO$_2$R$^a$, —SO$_2$NR$^a$R$^b$, —C$_{1-6}$alkylSO$_2$NR$^a$R$^b$, —C(O)NR$^a$SO$_2$R, and —NR$^a$C(O)R$^b$;

or $R^1$ and $R^2$ combine to form a heterocyclyl group optionally containing 1, 2, or 3 additional heteroatoms independently selected from oxygen, sulfur and nitrogen, and optionally substituted with 1 to 3 groups independently selected from oxo, —C$_{1-6}$ alkyl, —C$_{3-8}$ cycloalkyl, —C$_{2-6}$ alkenyl, —C$_{2-6}$ alkynyl, —OR$^a$, —C(O)OR$^a$, —C$_{1-6}$ cyanoalkyl, —C$_{1-6}$ alkylOR$^a$, —C$_{1-6}$haloalkyl, —C$_{1-3}$ alkylC$_{3-8}$cycloalkyl, —C(O)R$^a$, —C$_{1-6}$ alkylC(O)R$^a$, —C$_{1-6}$ alkylC(O)OR$^a$, —NR$^a$R$^b$, —C$_{1-6}$alkylNR$^a$R$^b$, —C(O)NR$^a$R$^b$, —C$_{1-6}$ alkylC(O)NR$^a$R$^b$, —SO$_2$R$^a$, —C$_{1-6}$ alkylSO$_2$R$^a$, —SO$_2$NR$^a$R$^b$, and C$_{1-6}$ alkylSO$_2$NR$^a$R$^b$;

$R^3$ is independently H, —C$_{1-6}$ alkyl, —C$_{2-6}$ alkenyl, —C$_{3-6}$ cycloalkyl, aryl, heteroaryl, heterocyclyl, —C$_{1-6}$alkylaryl, —C$_{1-6}$alkylheteroaryl, —C$_{1-6}$ alkylheterocyclyl, —C$_{2-6}$alkyl-OR$^a$, —C$_{1-6}$alkylC(O)OR$^a$, or —C$_{2-6}$ alkenylC(O)OR$^a$;

$R^4$ is independently H, —C$_{1-6}$ alkyl, —C$_{2-6}$ alkenyl, —C$_{3-6}$ cycloalkyl, aryl, heteroaryl, heterocyclyl, —C$_{1-6}$alkylaryl, —C$_{1-6}$alkylheteroaryl, —C$_{1-6}$ alkylheterocyclyl, —C$_{2-6}$alkyl-OR$^a$, —C$_{1-6}$alkylC(O)OR$^a$, or —C$_{2-6}$ alkenylC(O)OR$^a$;

$R^a$ is independently selected from H, —C$_{1-6}$ alkyl, —C$_{3-8}$ cycloalkyl, aryl, heteroaryl, heterocyclyl, —C$_{1-3}$ alkylC$_{3-8}$cycloalkyl, —C$_{1-6}$ alkylaryl, —C$_{1-6}$ alkylheteroaryl, and —C$_{1-6}$alkylheterocyclyl;

$R^b$ is independently selected from H, —C$_{1-6}$ alkyl, —C$_{3-8}$ cycloalkyl, aryl, heteroaryl, heterocyclyl, —C$_{1-3}$ alkylC$_{3-8}$cycloalkyl, —C$_{1-6}$ alkylaryl, —C$_{1-6}$ alkylheteroaryl, and —C$_{1-6}$ alkylheterocyclyl;

or $R^a$ and $R^b$ may combine together to form a ring consisting of 3-8 ring atoms that are C, N, O, or S; wherein the ring is optionally substituted with 1 to 4 groups independently selected from —OR$^f$, —CN, halo, —C$_{1-6}$ alkylOR$^f$, —C$_{1-6}$ cyanoalkyl, —C$_{1-6}$haloalkyl, —C$_{3-8}$ cycloalkyl, —C$_{1-3}$ alkylC$_{3-8}$cycloalkyl, —C(O)R$^f$, —C$_{1-6}$ alkylC(O)R$^f$, —C(O)OR$^f$, —C$_{1-6}$ alkylC(O)OR$^f$, —NR$^f$R$^g$, —C$_{1-6}$ alkylNR$^f$R$^g$, —C(O)NR$^f$R$^g$, —C$_{1-6}$ alkylC(O)NR$^f$R$^g$, —SO$_2$R$^f$, —C$_{1-6}$ alkylSO$_2$, —SO$_2$NR$^f$R$^g$, —C$_{1-6}$ alkylSO$_2$NR$^f$R$^g$, —C(O)NR$^f$SO$_2$R$^g$ and —NR$^f$C(O)R$^g$;

$R^c$ is independently selected from H, OH, —C$_{1-6}$ alkyl, —C$_{3-8}$ cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl;

$R^d$ is independently selected from H, —$C_{1-6}$ alkyl, —$C_3$-$C_8$cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl;

$R^e$ is independently selected from H, —$C_{1-6}$ alkyl, —$OC_{1-6}$alkyl, —$C_{3-8}$ cycloalkyl, aryl, heteroaryl, heterocyclyl, —$OC_{3-8}$cycloalkyl, —Oaryl, —Oheteroaryl, —Oheterocyclyl, —$C_{1-3}$ alkyl$C_{3-8}$cycloalkyl, —$C_{1-6}$alkylaryl, —$C_{1-6}$alkylheteroaryl, —$NR^fR^g$, —$C_{1-6}$alkyl$NR^fR^g$, —C(O)$NR^fR^g$, —$C_{1-6}$alkylC(O)$NR^fR^g$, —$NHSO_2R^f$, —$C_{1-6}$alkyl$SO_2R^f$, and —$C_{1-6}$alkyl$SO_2NR^fR^g$;

$R^f$ is independently selected from H, —$C_{1-6}$ alkyl, —$C_{3-8}$cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$ alkylheterocyclyl; and $R^g$ is independently selected from H, —$C_{1-6}$ alkyl, —$C_{3-8}$ cycloalkyl, aryl, heteroaryl, heterocyclyl, —$C_{1-3}$ alkyl$C_{3-8}$ cycloalkyl, —$C_{1-6}$ alkylaryl, —$C_{1-6}$ alkylheteroaryl, and —$C_{1-6}$ alkylheterocyclyl;

or a pharmaceutically acceptable salt, stereoisomer, mixture of stereoisomers, or tautomer thereof.

In one embodiment of formula (IIe), $L^E$ is a bond, —O—, or —O—$CH_2$—, where the oxygen is bonded to the Q ring and the $CH_2$ is bonded to the Ar ring. In one embodiment of formula (IIe), one or both $X^1$ is N. In one embodiment of formula (IIe), neither of $R^E$ or $R^W$ is an optionally substituted fused 5,6-aromatic or 5,6-heteromatic ring.

In one embodiment, the compound is represented by formula (IIf):

(IIf)

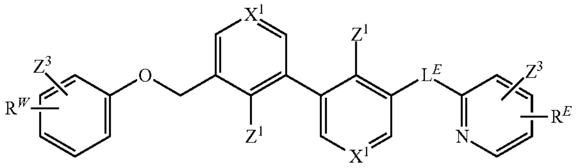

wherein each $X^1$ is independently N or CH;

each $Z^1$ is independently halo, —$OR^a$, —$C_{1-6}$ alkyl, —$OC_{1-6}$ alkyl, —$C_{1-6}$ haloalkyl, or —$C_{3-8}$ cycloalkyl;

each $Z^3$ is independently halo, —$OR^a$, —$N_3$, —$NO_2$, —CN, —$NR^1R^2$, —$SO_2R^a$, —$SO_2N^aR^b$, —$NR^aSO_2R^a$, —$NR^a$C(O)$R^a$, —C(O)$R^a$, —C(O)$OR^a$, —C(O)$NR^aR^b$, —$NR^a$C(O)$OR^a$, —$NR^a$C(O)$NR^1R^2$, —OC(O)$NR^aR^b$, —$NR^aSO_2NR^aR^b$, —C(O)$NR^aSO_2NR^aR^b$, —$C_{1-6}$ alkyl, —$C_{2-6}$ alkenyl, —$C_{2-6}$ alkynyl, —$OC_{1-6}$ alkyl, —$C_{3-8}$ cycloalkyl, —$C_{1-6}$ alkyl$C_{3-8}$ cycloalkyl, aryl, heteroaryl, heterocyclyl, and $R^N$;

wherein the alkyl, alkenyl, alkynyl, $C_{3-8}$ cycloalkyl, aryl, heteroaryl, or heterocyclyl group is optionally substituted with 1 to 4 groups independently selected from oxo, —$NO_2$, —$N_3$, —$OR^a$, halo, cyano, —$NR^aR^b$, —C(O)$R^a$, —C(O)$OR^a$, —$OC_{1-6}$alkylCN, —C(O)$NR^aR^b$, $NR^a$C(O)$R^a$, —$NR^a$C(O)$OR^a$, —$SO_2R^a$, —$NR^aSO_2R$, —$SO_2NR^aR^b$, —$NR^aSO_2NR^aR^b$, —C(O)$NR^aSO_2NR^aR^b$ and —$C_{3-8}$ cycloalkyl; and wherein the heteroaryl or heterocyclic group may be oxidized on a nitrogen atom to form an N-oxide or oxidized on a sulfur atom to form a sulfoxide or sulfone;

$R^N$ is independently —$C_{1-6}$ alkyl$NR^1R^2$, —$OC_{1-6}$ alky$NR^1R^2$, —$C_{1-6}$ alkyl$OC_{1-6}$ alkyl$NR^1R^2$, —$NR^aC_{1-6}$ alkyl$NR^1R^2$, —$C_{1-6}$ alkylC(O)$NR^1R^2$, —$OC_{1-6}$ alkylC(O)$NR^1R^2$, —$OC_{1-6}$ alkylC(O)$OR^1$, —$SC_{1-6}$ alkyl$NR^1R^2$, —$C_{1-6}$ alkyl$OR^a$, or

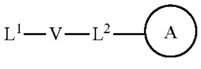;

wherein: $L^1$ is independently a bond, O, $NR^a$, S, SO, or $SO_2$;

V is independently selected from a bond, $C_{1-6}$alkyl, $C_{2-6}$alkenyl, and $C_{2-6}$alkynyl;

wherein each alkyl, alkenyl, or alkynyl is optionally independently substituted with $OR^a$, halo, cyano, —$NR^aR^b$ and —$C_{3-8}$ cycloalkyl;

$L^2$ is independently a bond, O, $NR^a$, S, SO, or $SO_2$;

ring A is independently cycloalkyl, aryl, heteroaryl, or heterocyclyl;

wherein each cycloalkyl, aryl, heteroaryl, or heterocyclyl is optionally substituted with 1 to 4 groups independently selected from oxo, —$NO_2$, —$N_3$, —$OR^a$, halo, cyano, —$C_{1-6}$ alkyl, —$C_{1-6}$ haloalkyl, —$C_{2-6}$alkenyl, —$C_{2-6}$ alkynyl, —$OC_{1-6}$ haloalkyl, $NR^aR^b$, —C(O)$R^a$, —C(O)$OR^a$, —$OC_{1-6}$ alkylCN, —C(O)$NR^aR^b$, —$NR^a$C(O)$R^a$, —$NR^a$C(O)$OR^a$, —$NR^a$C(O)$OR^a$, —C(O)N($R^a$)$OR^b$, —$SO_2R^a$, —$SO_2NR^aR^b$, —$NR^aSO_2R^b$, —$NR^aSO_2NR^aR^b$, —C(O)$NR^aSO_2NR^aR^b$, $C_{3-8}$cycloalkyl, and $C_{1-6}$alkyl$C_{3-8}$ cycloalkyl; and wherein the alkyl, alkenyl, or alkynyl group is optionally independently substituted with —$OR^a$, halo, cyano, —$NR^aR^b$ or —$C_{3-8}$ cycloalkyl;

$L^E$ is a bond, —O—, —S—, —SO—, —$SO_2$—, —$(CR^3R^4)_m$—, —$(CR^3R^4)_mO(CR^3R^4)_m$—, —$(CR^3R^4)_mS(CR^3R^4)_m$—, —$(CR^3R^4)_mNR^3(CR^3R^4)_m$—, —C(O)—, —$(CR^3R^4)_m$C(O)$(CR^3R^4)_m$—, —$(CR^3R^4)_m$C(O)$NR^3(CR^3R^4)_m$—, —$(CR^3R^4)_mNR^3$C(O)$(CR^3R^4)_m$—, $C_{2-6}$ alkenylene, $C_{2-6}$ alkynylene,

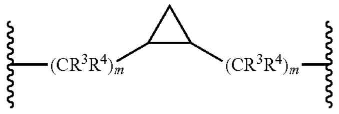 or

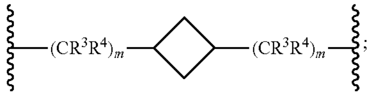;

each m is independently 0, 1, 2, 3 or 4;

$R^E$ and $R^W$ are each independently —$NR^1R^2$, —$C_{1-6}$ alky$NR^1R^2$, —$OC_{1-6}$ alkyl$NR^1R^2$, —$C_{1-6}$ alkyl $OC_{1-6}$alkyl$NR^1R^2$, —$NR^aC_{1-6}$ alkyl$NR^1R^2$, —$C_{1-6}$ alkyl$N^+R^1R^2R^3$, —$SC_{1-6}$ alkyl$NR^1R^2$, —C(O)$NR^1R^2$, —$SO_2R^a$, —$(CH_2)_uSO_2NR^1R^2$, —$(CH_2)_uNR^aSO_2NR^aR^b$, —$SO_2NR^aC_{1-6}$ alky$NR^1R^2$, $—NR^aSO_2C_{1-6}$ alkyl$NR^1R^2$, $—(CH_2)_uC(O)NR^aSO_2NR^aR^b$, $—(CH_2)_uN^+R^1R^2O^-$, $—(CH_2)_uP^+R^bR^cR^d$, $—(CH_2)_uP^+R^cR^dO^-$, $—(CH_2)_uP^+O[NR^aR^b][NR^cR^d]$, $—(CH_2)_uNR^cP(O)(OR^c)_2$, $—(CH_2)_uCH_2OP(O)(OR^c)(OR^d)$, $—(CH_2)_uOP(O)(OR^c)(OR^d)$, $—(CH_2)_uOP(O)NR^aR^b)(OR^a)$, or

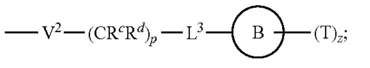

wherein:

$V^2$ is independently a bond, O, $NR^a$, S, SO, $SO_2$, $C(O)NR^a$, $NR^aC(O)$, $SO_2NR^1R^2$, or $NR^aSO_2$;

$L^3$ is independently a bond, O, $NR^a$, S, SO, $SO_2$, $C(O)NR^a$, $NR^aC(O)$, $SO_2NR^1R^2$, or $NR^aSO_2$; ring B is cycloalkyl, aryl, heteroaryl, or heterocyclyl; T is independently H, $OR^a$, $(CH_2)_qNR^1R^2$, $(CH_2)_qNR^aC(O)R^e$ or $(CH_2)_qC(O)R^e$;

p is independently 0, 1, 2, 3, 4, or 5;

q is independently 0, 1, 2, 3, 4, or 5;

u is 0, 1, 2, 3, or 4;

z is 0, 1, 2, or 3; and wherein the alkyl, cycloalkyl, aryl, heteroaryl, or heterocyclyl of $R^E$ or $R^W$ is optionally substituted with 1 to 3 substituents independently selected from the group consisting of $NR^aR^b$, halo, cyano, oxo, $OR^a$, $—C_{1-6}$alkyl, $—C_{1-6}$haloalkyl, $—C_{1-6}$cyanoalkyl, $—C_{1-6}$alky$NR^aR^b$, $—C_{1-6}$ alkylOH, $—C_{3-8}$ cycloalkyl, and $—C_{1-3}$ alkyl$C_{3-8}$cycloalkyl;

provided that at least one of $V^2$, $L^3$, ring B and T contains a nitrogen atom;

$R^1$ is independently selected from H, $—C_{1-8}$ alkyl, $—C_{2-6}$ alkenyl, $—C_{2-6}$ alkynyl, $—C_{3-6}$ cycloalkyl, aryl, heteroaryl, heterocyclyl, $—C_{1-6}$alkylaryl, $—C_{1-6}$alkylheteroaryl, $—C_{1-6}$alkylheterocyclyl, $—C_{1-6}$ alkylC(O)$OR^a$, $—C_{2-6}$ alkenylC(O)$OR^a$, $—SO_2R^a$, $—SO_2NR^aR^b$, $—C(O)NR^aSO_2R^a$, and $C_{1-6}$ alkyl $C_{3-8}$cycloalkyl;

wherein each alkyl, alkenyl, cycloalkyl, aryl, heteroaryl, or heterocyclyl is optionally substituted with 1 to 4 groups independently selected from $—OR^a$, —CN, halo, $C_{1-6}$alkyl, $—C_{1-6}$alkyl$OR^a$, $—C_{1-6}$cyanoalkyl, $—C_{1-6}$haloalkyl, $C_{3-8}$cycloalkyl, $—C_{1-3}$alkyl$C_{3-8}$cycloalkyl, $—C(O)R^a$, $—C_{1-6}$ alkylC(O)$R^a$, $—C(O)OR^a$, $—C_{1-6}$ alkylC(O)$OR^a$, $—NR^aR^b$, $—OC(O)NR^aR^b$, $NR^aC(O)OR^b$, $—C_{1-6}$alkyl$NR^aR^b$, $—C(O)NR^aR^b$, $—C_{1-6}$alkylC(O)$NR^aR^b$, $—SO_2R^a$, $—C_{1-6}$alkyl$SO_2R^a$, $—SO_2NR^aR^b$, $—C_{1-6}$ alkyl$SO_2NR^aR^b$, $—C(O)NR^aSO_2R^b$, $—C_{1-6}$ alkylC(O)$NR^aSO_2R^b$, $—NR^aC(O)R^b$, and $—C_{1-6}$alkyl$NR^aC(O)R^b$;

$R^2$ is independently selected from H, $—C_{1-6}$alkyl, $—C_{2-6}$ alkenyl, $—C_{2-6}$ alkynyl, $—C_{3-6}$ cycloalkyl, aryl, heteroaryl, heterocyclyl, $—C_{1-6}$alkylaryl, $—C_{1-6}$alkylheteroaryl, $—C_{1-6}$ alkylheterocyclyl, $—C_{2-6}$alkyl-$OR^a$, $—C_{1-6}$ alkylC(O)$OR^a$, and $—C_{2-6}$ alkenylC(O)$OR^a$;

wherein each alkyl, alkenyl, alkynyl, cycloalkyl, aryl, heteroaryl, or heterocyclyl is optionally substituted with 1 to 4 groups independently selected from $—OR^a$, —CN, halo, $C_{1-6}$alkyl, $—C_{1-6}$alkyl$OR^a$, $—C_{1-6}$cyanoalkyl, $—C_{1-6}$haloalkyl, $—C_{3-8}$cycloalkyl, $—C_{1-3}$alkyl$C_{3-8}$cycloalkyl, $—C(O)R^a$, $—C_{1-6}$ alkylC(O)$R^a$, $—C(O)OR^a$, $—C_{1-6}$ alkylC(O)$OR^a$, $—NR^aR^b$, $—C_{1-6}$ alkyl$NR^aR^b$, $—C(O)NR^aR^b$, $C_{1-6}$alkylC(O)$NR^aR^b$, $—SO_2R^a$, $—C_{1-6}$alkyl$SO_2R^a$, $—SO_2NR^aR^b$, $—C_{1-6}$alkyl$SO_2NR^aR^b$, $—C(O)NR^aSO_2R$, and $—NR^aC(O)R^b$;

or $R^1$ and $R^2$ combine to form a heterocyclyl group optionally containing 1, 2, or 3 additional heteroatoms independently selected from oxygen, sulfur and nitrogen, and optionally substituted with 1 to 3 groups independently selected from oxo, $—C_{1-6}$alkyl, $—C_{3-8}$ cycloalkyl, $—C_{2-6}$ alkenyl, $—C_{2-6}$ alkynyl, $—OR^a$, $—C(O)OR^a$, $—C_{1-6}$cyanoalkyl, $—C_{1-6}$ alkyl$OR^a$, $—C_{1-6}$haloalkyl, $—C_{1-3}$ alkyl$C_{3-8}$cycloalkyl, $—C(O)R^a$, $C_{1-6}$alkylC(O)$R^a$, $—C_{1-6}$alkylC(O)$OR^a$, $—NR^aR^b$, $—C_{1-6}$alkyl$NR^aR^b$, $—C(O)NR^aR^b$, $—C_{1-6}$alkylC(O)$NR^aR^b$, $—SO_2R^a$, $—C_{1-6}$ alkyl$SO_2R^a$, $—SO_2NR^aR^b$, and $C_{1-6}$ alkyl$SO_2NR^aR^b$;

$R^3$ is independently H, $—C_{1-6}$alkyl, $—C_{2-6}$ alkenyl, $—C_{3-6}$ cycloalkyl, aryl, heteroaryl, heterocyclyl, $—C_{1-6}$alkylaryl, $—C_{1-6}$alkylheteroaryl, $—C_{1-6}$ alkylheterocyclyl, $—C_{2-6}$alkyl-$OR^a$, $—C_{1-6}$alkylC(O)$OR^a$, or $—C_{2-6}$ alkenylC(O)$OR^a$;

$R^4$ is independently H, $—C_{1-6}$alkyl, $—C_{2-6}$ alkenyl, $—C_{3-6}$ cycloalkyl, aryl, heteroaryl, heterocyclyl, $—C_{1-6}$alkylaryl, $—C_{1-6}$alkylheteroaryl, $—C_{1-6}$ alkylheterocyclyl, $—C_{2-6}$alkyl-$OR^a$, $—C_{1-6}$alkylC(O)$OR^a$, or $—C_{2-6}$ alkenylC(O)$OR^a$;

$R^a$ is independently selected from H, $—C_{1-6}$alkyl, $—C_{3-8}$ cycloalkyl, aryl, heteroaryl, heterocyclyl, $—C_{1-3}$ alkyl$C_{3-8}$cycloalkyl, $—C_{1-6}$ alkylaryl, $—C_{1-6}$ alkylheteroaryl, and $—C_{1-6}$alkylheterocyclyl;

$R^b$ is independently selected from H, $—C_{1-6}$alkyl, $—C_{3-8}$ cycloalkyl, aryl, heteroaryl, heterocyclyl, $—C_{1-3}$ alkyl$C_{3-8}$cycloalkyl, $—C_{1-6}$ alkylaryl, $—C_{1-6}$ alkylheteroaryl, and $—C_{1-6}$ alkylheterocyclyl;

or $R^a$ and $R^b$ may combine together to form a ring consisting of 3-8 ring atoms that are C, N, O, or S; wherein the ring is optionally substituted with 1 to 4 groups independently selected from $—OR^f$, —CN, halo, $—C_{1-6}$ alkyl$OR^f$, $—C_{1-6}$ cyanoalkyl, $—C_{1-6}$haloalkyl, $—C_{3-8}$ cycloalkyl, $—C_{1-3}$ alkyl$C_{3-8}$cycloalkyl, $—C(O)R^f$, $—C_{1-6}$ alkylC(O)$R^f$, $—C(O)OR^f$, $—C_{1-6}$ alkylC(O)$OR^f$, $—NR^fR^g$, $—C_{1-6}$ alkyl$NR^fR^g$, $—C(O)NR^fR^g$, $—C_{1-6}$ alkylC(O)$NR^fR^g$, $—SO_2R^f$, $—C_{1-6}$ alkyl$SO_2R^f$, $—SO_2NR^fR^g$, $—C_{1-6}$ alkyl$SO_2NR^fR^g$, $—C(O)NR^fSO_2R^g$ and $—NR^fC(O)R^g$;

$R^c$ is independently selected from H, OH, $—C_{1-6}$alkyl, $—C_{3-8}$ cycloalkyl, aryl, heteroaryl, heterocyclyl, $—C_{1-3}$ alkyl$C_{3-8}$cycloalkyl, $—C_{1-6}$ alkylaryl, $—C_{1-6}$ alkylheteroaryl, and $—C_{1-6}$alkylheterocyclyl;

$R^d$ is independently selected from H, $—C_{1-6}$alkyl, $—C_3$-$C_8$cycloalkyl, aryl, heteroaryl, heterocyclyl, $—C_{1-3}$ alkyl$C_{3-8}$cycloalkyl, $—C_{1-6}$ alkylaryl, $—C_{1-6}$ alkylheteroaryl, and $—C_{1-6}$alkylheterocyclyl;

$R^e$ is independently selected from H, $—C_{1-6}$alkyl, $—OC_{1-6}$alkyl, $—C_{3-8}$ cycloalkyl, aryl, heteroaryl, heterocyclyl, $—OC_{3-8}$cycloalkyl, —Oaryl, —Oheteroaryl, —Oheterocyclyl, $—C_{1-3}$ alkyl$C_{3-8}$cycloalkyl, $—C_{1-6}$alkylaryl, $—C_{1-6}$alkylheteroaryl, $—NR^fR^g$, $—C_{1-6}$alkyl$NR^fR^g$, $—C(O)NR^fR^g$, $—C_{1-6}$alkylC(O)$NR^fR^g$, $—NHSO_2R^f$, $—C_{1-6}$alkyl$SO_2R^f$, and $—C_{1-6}$alkyl$SO_2NR^fR^g$;

$R^f$ is independently selected from H, $—C_{1-6}$alkyl, $—C_{3-8}$ cycloalkyl, aryl, heteroaryl, heterocyclyl, $—C_{1-3}$ alkyl$C_{3-8}$cycloalkyl, $—C_{1-6}$ alkylaryl, $—C_{1-6}$ alkylheteroaryl, and $—C_{1-6}$alkylheterocyclyl; and $R^g$ is independently selected from H, $—C_{1-6}$alkyl, $—C_{3-8}$ cycloalkyl, aryl, heteroaryl, heterocyclyl, $—C_{1-3}$ alkyl$C_{3-8}$cycloalkyl, $—C_{1-6}$ alkylaryl, $—C_{1-6}$ alkylheteroaryl, and $—C_{1-6}$alkylheterocyclyl;

or a pharmaceutically acceptable salt, stereoisomer, mixture of stereoisomers, or tautomer thereof.

In one embodiment of formula (IIf), $L^E$ is a bond, —O—, or —O—$CH_2$—, where the oxygen is bonded to the Q ring and the $CH_2$ is bonded to the Ar ring. In one embodiment of formula (IIf), one or both of $X^1$ is N. In one embodiment of formula (IIf), neither of $R^E$ or $R^W$ is an optionally substituted fused 5,6-aromatic or 5,6-heteromatic ring.

In one embodiment, the compound is represented by formula (IIg):

(IIg)

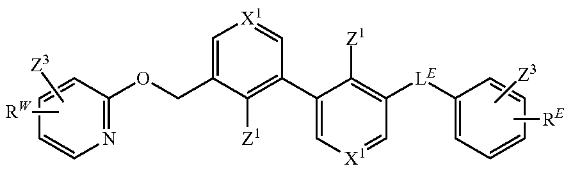

wherein each $X^1$ is independently N or CH;

each $Z^1$ is independently halo, —$OR^a$, —$C_{1-6}$ alkyl, —$OC_{1-6}$ alkyl, —$C_{1-6}$ haloalkyl, or —$C_{3-8}$ cycloalkyl;

each $Z^3$ is independently halo, —$OR^a$, —$N_3$, —$NO_2$, —CN, —$NR^1R^2$, —$SO_2R^a$, —$SO_2NR^aR^b$, —$NR^aSO_2R^a$, —$NR^aC(O)R^a$, —$C(O)R^a$, —$C(O)OR^a$, —$C(O)NR^aR^b$, —$NR^aC(O)OR^a$, —$NR^aC(O)NR^1R^2$, —$OC(O)NR^aR^b$, —$NR^aSO_2NR^aR^b$, —C(O)$NR^aSO_2NR^aR^b$, —$C_{1-6}$ alkyl, —$C_{2-6}$ alkenyl, —$C_{2-6}$ alkynyl, —$OC_{1-6}$ alkyl, —$C_{3-8}$ cycloalkyl, —$C_{1-6}$ alkyl$C_{3-8}$ cycloalkyl, aryl, heteroaryl, heterocyclyl, and $R^N$;

wherein the alkyl, alkenyl, alkynyl, $C_{3-8}$ cycloalkyl, aryl, heteroaryl, or heterocyclyl group is optionally substituted with 1 to 4 groups independently selected from oxo, —$NO_2$, —$N_3$, —$OR^a$, halo, cyano, —$NR^aR^b$, —$C(O)R^a$, —$C(O)OR^a$, —$OC_{1-6}$alkyCN, —$C(O)NR^aR^b$, $NR^aC(O)R^a$, —$NR^aC(O)OR^a$, —$SO_2R^a$, —$NR^aSO_2$R, —$SO_2NR^aR^b$, —$NR^aSO_2NR^aR^b$, —$C(O)NR^aSO_2NR^aR^b$ and —$C_{3-8}$ cycloalkyl; and wherein the heteroaryl or heterocyclic group may be oxidized on a nitrogen atom to form an N-oxide or oxidized on a sulfur atom to form a sulfoxide or sulfone;

$R^N$ is independently —$C_{1-6}$ alkyl$NR^1R^2$, —$OC_{1-6}$ alky$NR^1R^2$, —$C_{1-6}$ alkyl$OC_{1-6}$ alkyl$NR^1R^2$, —$NR^aC_{1-6}$ alkyl$NR^1R^2$, —$C_{1-6}$ alkylC(O)$NR^1R^2$, —$OC_{1-6}$ alkylC(O)$NR^1R^2$, —$OC_{1-6}$ alkylC(O)$OR^1$, —$SC_{1-6}$alkyl$NR^1R^2$, —$C_{1-6}$ alkyl$OR^a$, or

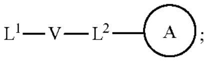

wherein: $L^1$ is independently a bond, O, $NR^a$, S, SO, or $SO_2$;

V is independently selected from a bond, $C_{1-6}$alkyl, $C_{2-6}$alkenyl, and $C_{2-6}$alkynyl;

wherein each alkyl, alkenyl, or alkynyl is optionally independently substituted with $OR^a$, halo, cyano, —$NR^aR^b$ and —$C_{3-8}$ cycloalkyl;

$L^2$ is independently a bond, O, $NR^a$, S, SO, or $SO_2$;

ring A is independently cycloalkyl, aryl, heteroaryl, or heterocyclyl;

wherein each cycloalkyl, aryl, heteroaryl, or heterocyclyl is optionally substituted with 1 to 4 groups independently selected from oxo, —$NO_2$, —$N_3$, —$OR^a$, halo, cyano, —$C_{1-6}$ alkyl, —$C_{1-6}$ haloalkyl, —$C_{2-6}$alkenyl, —$C_{2-6}$ alkynyl, —$OC_{1-6}$ haloalkyl, $NR^aR^b$, —$C(O)R^a$, —$C(O)OR^a$, —$OC_{1-6}$ alkylCN, —$C(O)NR^aR^b$, —$NR^aC(O)R^a$, —$NR^aC(O)OR^a$, —$NR^aC(O)OR^a$, —$C(O)N(R^a)OR^b$, —$SO_2R^a$, —$SO_2NR^aR^b$, —$NR^aSO_2R^b$, —$NR^aSO_2NR^aR^b$, —$C(O)NR^aSO_2NR^aR^b$, $C_{3-8}$cycloalkyl, and $C_{1-6}$alkyl$C_{3-8}$ cycloalkyl; and wherein the alkyl, alkenyl, or alkynyl group is optionally independently substituted with —$OR^a$, halo, cyano, —$NR^aR^b$ or —$C_{3-8}$ cycloalkyl $L^E$ is a bond, —O—, —S—, —SO—, —$SO_2$—, —$(CR^3R^4)_m$—, —$(CR^3R^4)_mO(CR^3R^4)_m$—, —$(CR^3R^4)_mS(CR^3R^4)_m$—, —$(CR^3R^4)_mNR^3(CR^3R^4)_m$—, —C(O)—, —$(CR^3R^4)_mC(O)(CR^3R^4)_m$—, —$(CR^3R^4)_mC(O)NR^3(CR^3R^4)_m$—, —$(CR^3R^4)_mNR^3C(O)(CR^3R^4)_m$—, $C_{2-6}$ alkenylene, $C_{2-6}$ alkynylene,

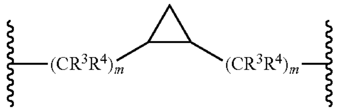

or

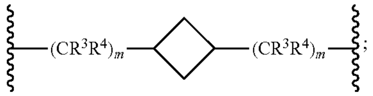

each m is independently 0, 1, 2, 3 or 4;

$R^E$ and $R^W$ are each independently —$NR^1R^2$, —$C_{1-6}$ alky$NR^1R^2$, —$OC_{1-6}$ alkyl$NR^1R^2$, —$C_{1-6}$ alkylO $C_{1-6}$alky$NR^1R^2$, —$NR^aC_{1-6}$ alky$NR^1R^2$, —$C_{1-6}$ alkyl$N^+R^1R^2R^3$, —$SC_{1-6}$ alkyl$NR^1R^2$, —C(O)$NR^1R^2$, —$SO_2R^a$, —$(CH_2)_uSO_2NR^1R^2$, —$(CH_2)_uNR^aSO_2NR^aR^b$, —$SO_2NR^aC_{1-6}$ alky$NR^1R^2$, —$NR^aSO_2C_{1-6}$ alkyl$NR^1R^2$, —$(CH_2)_u$C(O)$NR^aSO_2NR^aR^b$, —$(CH_2)_uN^+R^1R^2O^-$, —$(CH_2)_uP^+R^bR^cR^d$, —$(CH_2)_uP^+R^cR^dO^-$, —$(CH_2)_uP^+O[NR^aR^b][NR^cR^d]$, —$(CH_2)_uNR^cP(O)(OR^c)_2$, —$(CH_2)_uCH_2OP(O)(OR^c)(OR^d)$, —$(CH_2)_uOP(O)(OR^c)(OR^d)$, —$(CH_2)_uOP(O)NR^aR^b)(OR^a)$, or

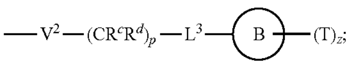

wherein:

$V^2$ is independently a bond, O, $NR^a$, S, SO, $SO_2$, C(O)$NR^a$, $NR^a$C(O), $SO_2NR^1R^2$, or $NR^aSO_2$;

$L^3$ is independently a bond, O, $NR^a$, S, SO, $SO_2$, C(O)$NR^a$, $NR^a$C(O), $SO_2NR^1R^2$, or $NR^aSO_2$;

ring B is cycloalkyl, aryl, heteroaryl, or heterocyclyl; T is independently H, $OR^a$, $(CH_2)_qNR^1R^2$, $(CH_2)_qN$-$R^aC(O)R^e$ or $(CH_2)_qC(O)R^e$;

p is independently 0, 1, 2, 3, 4, or 5;

q is independently 0, 1, 2, 3, 4, or 5;

u is 0, 1, 2, 3, or 4;

z is 0, 1, 2, or 3; and wherein the alkyl, cycloalkyl, aryl, heteroaryl, or heterocyclyl of $R^E$ or $R^W$ is optionally substituted with 1 to 3 substituents independently selected from the group consisting of $NR^aR^b$, halo, cyano, oxo, $OR^a$, —$C_{1-6}$alkyl, —$C_{1-6}$haloalkyl, —$C_{1-6}$cyanoalkyl, —$C_{1-6}$alkyNR$^a$R$^b$, —$C_{1-6}$ alkylOH, —$C_{3-8}$ cycloalkyl, and —$C_{1-3}$ alkyl$C_{3-8}$cycloalkyl;

provided that at least one of $V^2$, $L^3$, ring B and T contains a nitrogen atom;

$R^1$ is independently selected from H, —$C_{1-8}$ alkyl, —$C_{2-6}$ alkenyl, —$C_{2-6}$ alkynyl, —$C_{3-6}$ cycloalkyl, aryl, heteroaryl, heterocyclyl, —$C_{1-6}$alkylaryl, —$C_{1-6}$alkylheteroaryl, —$C_{1-6}$alkylheterocyclyl, —$C_{1-6}$ alkylC(O)OR$^a$, —$C_{2-6}$ alkenylC(O)OR$^a$, —$SO_2R^a$, —$SO_2NR^aR^b$, —C(O)NR$^a$SO$_2$R$^a$, and $C_{1-6}$ alkyl $C_{3-8}$cycloalkyl;

wherein each alkyl, alkenyl, cycloalkyl, aryl, heteroaryl, or heterocyclyl is optionally substituted with 1 to 4 groups independently selected from —OR$^a$, —CN, halo, $C_{1-6}$alkyl, —$C_{1-6}$alkylOR$^a$, —$C_{1-6}$cyanoalkyl, —$C_{1-6}$haloalkyl, $C_{3-8}$cycloalkyl, —$C_{1-3}$alkyl$C_{3-8}$cycloalkyl, —C(O)R$^a$, —$C_{1-6}$ alkylC(O)R$^a$, —C(O)OR$^a$, —$C_{1-6}$ alkylC(O)OR$^a$, —NR$^a$R$^b$, —OC(O)NR$^a$R$^b$, NR$^a$C(O)OR$^b$, —$C_{1-6}$alkylNR$^a$R$^b$, —C(O)NR$^a$R$^b$, —$C_{1-6}$alkylC(O)NR$^a$R$^b$, —SO$_2$R$^a$, —$C_{1-6}$alkylSO$_2$R$^a$, —SO$_2$NR$^a$R$^b$, —$C_{1-6}$ alkylSO$_2$NR$^a$R$^b$, —C(O)NR$^a$SO$_2$R$^b$, —$C_{1-6}$ alkylC(O)NR$^a$SO$_2$R$^b$, —NR$^a$C(O)R$^b$, and —$C_{1-6}$alkylNR$^a$C(O)R$^b$;

$R^2$ is independently selected from H, —$C_{1-6}$alkyl, —$C_{2-6}$ alkenyl, —$C_{2-6}$ alkynyl, —$C_{3-6}$ cycloalkyl, aryl, heteroaryl, heterocyclyl, —$C_{1-6}$alkylaryl, —$C_{1-6}$alkylheteroaryl, —$C_{1-6}$ alkylheterocyclyl, —$C_{2-6}$alkyl-OR$^a$, —$C_{1-6}$ alkylC(O)OR$^a$, and —$C_{2-6}$ alkenylC(O)OR$^a$;

wherein each alkyl, alkenyl, alkynyl, cycloalkyl, aryl, heteroaryl, or heterocyclyl is optionally substituted with 1 to 4 groups independently selected from —OR$^a$, —CN, halo, $C_{1-6}$alkyl, —$C_{1-6}$alkylOR$^a$, —$C_{1-6}$cyanoalkyl, —$C_{1-6}$haloalkyl, —$C_{3-8}$cycloalkyl, —$C_{1-3}$alkyl$C_{3-8}$cycloalkyl, —C(O)R$^a$, —$C_{1-6}$ alkylC(O)R$^a$, —C(O)OR$^a$, —$C_{1-6}$ alkylC(O)OR$^a$, —NR$^a$R$^b$, —$C_{1-6}$ alkylNR$^a$R$^b$, —C(O)NR$^a$R$^b$, $C_{1-6}$alkylC(O)NR$^a$R$^b$, —SO$_2$R$^a$, —$C_{1-6}$alkylSO$_2$R$^a$, —SO$_2$NR$^a$R$^b$, —$C_{1-6}$alkylSO$_2$NR$^a$R$^b$, —C(O)NR$^a$SO$_2$R, and —NR$^a$C(O)R$^b$;

or $R^1$ and $R^2$ combine to form a heterocyclyl group optionally containing 1, 2, or 3 additional heteroatoms independently selected from oxygen, sulfur and nitrogen, and optionally substituted with 1 to 3 groups independently selected from oxo, —$C_{1-6}$alkyl, —$C_{3-8}$ cycloalkyl, —$C_{2-6}$ alkenyl, —$C_{2-6}$ alkynyl, —OR$^a$, —C(O)OR$^a$, —$C_{1-6}$cyanoalkyl, —$C_{1-6}$ alkylOR$^a$, —$C_{1-6}$haloalkyl, —$C_{1-3}$ alkyl$C_{3-8}$cycloalkyl, —C(O)R$^a$, —$C_{1-6}$ alkylC(O)R$^a$, —$C_{1-6}$ alkylC(O)OR$^a$, —NR$^a$R$^b$, —$C_{1-6}$alkyNR$^a$R$^b$, —C(O)NR$^a$R$^b$, —$C_{1-6}$ alkylC(O)NR$^a$R$^b$, —SO$_2$R$^a$, —$C_{1-6}$ alkylSO$_2$R$^a$, —SO$_2$NR$^a$R$^b$, and $C_{1-6}$ alkylSO$_2$NR$^a$R$^b$;

$R^3$ is independently H, —$C_{1-6}$alkyl, —$C_{2-6}$ alkenyl, —$C_{3-6}$ cycloalkyl, aryl, heteroaryl, heterocyclyl, —$C_{1-6}$alkylaryl, —$C_{1-6}$alkylheteroaryl, —$C_{1-6}$ alkylheterocyclyl, —$C_{2-6}$alkyl-OR$^a$, —$C_{1-6}$alkylC(O)OR$^a$, or —$C_{2-6}$ alkenylC(O)OR$^a$;

$R^4$ is independently H, —$C_{1-6}$alkyl, —$C_{2-6}$ alkenyl, —$C_{3-6}$ cycloalkyl, aryl, heteroaryl, heterocyclyl, —$C_{1-6}$alkylaryl, —$C_{1-6}$alkylheteroaryl, —$C_{1-6}$ alkylheterocyclyl, —$C_{2-6}$alkyl-OR$^a$, —$C_{1-6}$alkylC(O)OR$^a$, or —$C_{2-6}$ alkenylC(O)OR$^a$;

$R^a$ is independently selected from H, —$C_{1-6}$alkyl, —$C_{3-8}$ cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl;

$R^b$ is independently selected from H, —$C_{1-6}$alkyl, —$C_{3-8}$ cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$ alkylheterocyclyl;

or $R^a$ and $R^b$ may combine together to form a ring consisting of 3-8 ring atoms that are C, N, O, or S; wherein the ring is optionally substituted with 1 to 4 groups independently selected from —OR$^f$, —CN, halo, —$C_{1-6}$ alkylOR$^f$, —$C_{1-6}$ cyanoalkyl, —$C_{1-6}$haloalkyl, —$C_{3-8}$ cycloalkyl, —$C_{1-3}$ alkyl$C_{3-8}$cycloalkyl, —C(O)R$^f$, —$C_{1-6}$ alkylC(O)R$^f$, —C(O)OR$^f$, —$C_{1-6}$ alkylC(O)OR$^f$, —NR$^f$R$^g$, —$C_{1-6}$ alkylNR$^f$R$^g$, —C(O)NR$^f$R$^g$, —$C_{1-6}$ alkylC(O)NR$^f$R$^g$, —SO$_2$R$^f$, —$C_{1-6}$ alkylSO$_2$R, —SO$_2$NR$^f$R$^g$, —$C_{1-6}$ alkylSO$_2$NR$^f$R$^g$, —C(O)NR$^f$SO$_2$R$^g$ and —NR$^f$C(O)R$^g$;

$R^c$ is independently selected from H, OH, —$C_{1-6}$alkyl, —$C_{3-8}$ cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl;

$R^d$ is independently selected from H, —$C_{1-6}$alkyl, —$C_3$-$C_8$cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl;

$R^e$ is independently selected from H, —$C_{1-6}$alkyl, —O$C_{1-6}$alkyl, —$C_{3-8}$ cycloalkyl, aryl, heteroaryl, heterocyclyl, —O$C_{3-8}$cycloalkyl, —Oaryl, —Oheteroaryl, —Oheterocyclyl, —$C_{1-3}$ alkyl$C_{3-8}$cycloalkyl, —$C_{1-6}$alkylaryl, —$C_{1-6}$alkylheteroaryl, —NR$^f$R$^g$, —$C_{1-6}$alkylNR$^f$R$^g$, —C(O)NR$^f$R$^g$, —$C_{1-6}$alkylC(O)NR$^f$R$^g$, —NHSO$_2$R$^f$, —$C_{1-6}$alkylSO$_2$R$^f$, and —$C_{1-6}$alkylSO$_2$NR$^f$R$^g$;

$R^f$ is independently selected from H, —$C_{1-6}$alkyl, —$C_{3-8}$ cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl; and $R^g$ is independently selected from H, —$C_{1-6}$alkyl, —$C_{3-8}$ cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl;

or a pharmaceutically acceptable salt, stereoisomer, mixture of stereoisomers, or tautomer thereof.

In one embodiment of formula (IIg), neither of $R^E$ or $R^W$ is an optionally substituted fused 5,6-aromatic or 5,6-heteromatic ring.

In one embodiment, the compound is represented by formula (IIh):

(IIh)

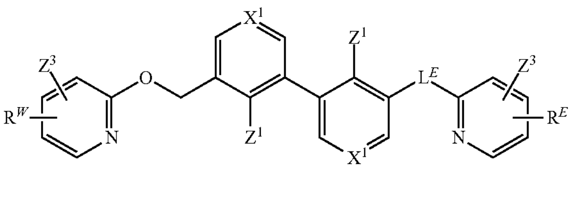

wherein each $X^1$ is independently N or CH;

each $Z^1$ is independently halo, —$OR^a$, —$C_{1-6}$ alkyl, —$OC_{1-6}$alkyl, —$C_{1-6}$ haloalkyl, or —$C_{3-8}$ cycloalkyl;

each $Z^3$ is independently halo, —$OR^a$, —$N_3$, —$NO_2$, —CN, —$NR^1R^2$, —$SO_2R^a$, —$SO_2NR^aR^b$, —$NR^aSO_2R^a$, —$NR^aC(O)R^a$, —$C(O)R^a$, —$C(O)OR^a$, —$C(O)NR^aR^b$, —$NR^aC(O)OR^a$, —$NR^aC(O)NR^1R^2$, —$OC(O)NR^aR^b$, —$NR^aSO_2NR^aR^b$, —$C(O)NR^aSO_2NR^aR^b$, —$C_{1-6}$ alkyl, —$C_{2-6}$ alkenyl, —$C_{2-6}$ alkynyl, —$OC_{1-6}$alkyl, —$C_{3-8}$ cycloalkyl, —$C_{1-6}$ alkyl$C_{3-8}$ cycloalkyl, aryl, heteroaryl, heterocyclyl, and $R^N$;

wherein the alkyl, alkenyl, alkynyl, $C_{3-8}$ cycloalkyl, aryl, heteroaryl, or heterocyclyl group is optionally substituted with 1 to 4 groups independently selected from oxo, —$NO_2$, —$N_3$, —$OR^a$, halo, cyano, —$NR^aR^b$, —$C(O)R^a$, —$C(O)OR^a$, —$OC_{1-6}$alkyCN, —$C(O)NR^aR^b$, $NR^aC(O)R^a$, —$NR^aC(O)OR^a$, —$SO_2R^a$, —$NR^aSO_2R$, —$SO_2NR^aR^b$, —$NR^aSO_2NR^aR^b$, —$C(O)NR^aSO_2NR^aR^b$ and —$C_{3-8}$ cycloalkyl; and wherein the heteroaryl or heterocyclic group may be oxidized on a nitrogen atom to form an N-oxide or oxidized on a sulfur atom to form a sulfoxide or sulfone;

$R^N$ is independently —$C_{1-6}$ alkyl$NR^1R^2$, —$OC_{1-6}$ alky$NR^1R^2$, —$C_{1-6}$ alkyl$OC_{1-6}$ alkyl$NR^1R^2$, —$NR^aC_{1-6}$ alkyl$NR^1R^2$, —$C_{1-6}$ alkyl$C(O)NR^1R^2$, —$OC_{1-6}$ alkyl$C(O)NR^1R^2$, —$OC_{1-6}$ alkyl$C(O)OR^1$, —$SC_{1-6}$ alkyl$NR^1R^2$, —$C_{1-6}$ alkyl$OR^a$, or

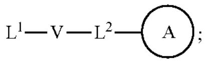;

wherein: $L^1$ is independently a bond, O, $NR^a$, S, SO, or $SO_2$;

V is independently selected from a bond, $C_{1-6}$alkyl, $C_{2-6}$alkenyl, and $C_{2-6}$alkynyl;

wherein each alkyl, alkenyl, or alkynyl is optionally independently substituted with $OR^a$, halo, cyano, —$NR^aR^b$ and —$C_{3-8}$ cycloalkyl;

$L^2$ is independently a bond, O, $NR^a$, S, SO, or $SO_2$;

ring A is independently cycloalkyl, aryl, heteroaryl, or heterocyclyl;

wherein each cycloalkyl, aryl, heteroaryl, or heterocyclyl is optionally substituted with 1 to 4 groups independently selected from oxo, —$NO_2$, —$N_3$, —$OR^a$, halo, cyano, —$C_{1-6}$ alkyl, —$C_{1-6}$ haloalkyl, —$C_{2-6}$alkenyl, —$C_{2-6}$ alkynyl, —$OC_{1-6}$ haloalkyl, $NR^aR^b$, —$C(O)R^a$, —$C(O)OR^a$, —$OC_{1-6}$ alkylCN, —$C(O)NR^aR^b$, —$NR^aC(O)R^a$, —$NR^aC(O)OR^a$, —$NR^aC(O)OR^a$, —$C(O)N(R^a)OR^b$, —$SO_2R^a$, —$SO_2NR^aR^b$, —$NR^aSO_2R^b$, —$NR^aSO_2NR^aR^b$, —$C(O)NR^aSO_2NR^aR^b$, $C_{3-8}$cycloalkyl, and $C_{1-6}$alkyl$C_{3-8}$ cycloalkyl; and wherein the alkyl, alkenyl, or alkynyl group is optionally independently substituted with —$OR^a$, halo, cyano, —$NR^aR^b$ or —$C_{3-8}$ cycloalkyl $L^E$ is a bond, —O—, —S—, —SO—, —$SO_2$—, —$(CR^3R^4)_m$—, —$(CR^3R^4)_mO(CR^3R^4)_m$—, —$(CR^3R^4)_mS(CR^3R^4)_m$—, —$(CR^3R^4)_mNR^3(CR^3R^4)_m$—, C(O)—, —$(CR^3R^4)_mC(O)(CR^3R^4)_m$—, —$(CR^3R^4)_mC(O)NR^3(CR^3R^4)_m$—, —$(CR^3R^4)_mNR^3C(O)(CR^3R^4)_m$—, $C_{2-6}$ alkenylene, $C_{2-6}$ alkynylene,

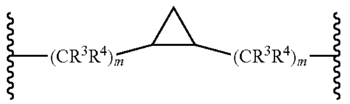

or

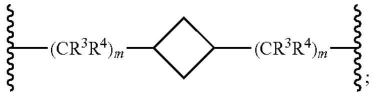;

each m is independently 0, 1, 2, 3 or 4;

$R^E$ and $R^W$ are each independently —$NR^1R^2$, —$C_{1-6}$ alky$NR^1R^2$, —$OC_{1-6}$ alkyl$NR^1R^2$, —$C_{1-6}$ alkyl$OC_{1-6}$alkyl$NR^1R^2$, —$NR^aC_{1-6}$ alkyl$NR^1R^2$, —$C_{1-6}$ alkyl$N^+R^1R^2R^3$, —$SC_{1-6}$ alkyl$NR^1R^2$, —$C(O)NR^1R^2$, —$SO_2R^a$, —$(CH_2)_uSO_2NR^1R^2$, —$(CH_2)_uNR^aSO_2NR^aR^b$, —$SO_2NR^aC_{1-6}$alkyl$NR^1R^2$, —$NR^aSO_2C_{1-6}$ alkyl$NR^1R^2$, —$(CH_2)_uC(O)NR^aSO_2NR^aR^b$, —$(CH_2)_uN^+R^1R^2O^-$, —$(CH_2)_uP^+R^bR^cR^d$, —$(CH_2)_uP^+R^cR^dO^-$, —$(CH_2)_uP^+O[NR^aR^b][NR^cR^d]$, —$(CH_2)_uNR^cP(O)(OR^c)_2$, —$(CH_2)_uCH_2OP(O)(OR^c)(OR^d)$, —$(CH_2)_uOP(O)(OR^c)(OR^d)$, —$(CH_2)_uOP(O)NR^aR^b)(OR^a)$, or

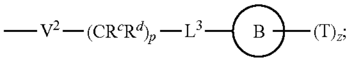;

wherein:

$V^2$ is independently a bond, O, $NR^a$, S, SO, $SO_2$, $C(O)NR^a$, $NR^aC(O)$, $SO_2NR^1R^2$, or $NR^aSO_2$;

$L^3$ is independently a bond, O, $NR^a$, S, SO, $SO_2$, $C(O)NR^a$, $NR^aC(O)$, $SO_2NR^1R^2$, or $NR^aSO_2$;

ring B is cycloalkyl, aryl, heteroaryl, or heterocyclyl;

T is independently H, $OR^a$, $(CH_2)NR^1R^2$, $(CH_2)_qNR^aC(O)R$ or $(CH_2)C(O)R^e$;

p is independently 0, 1, 2, 3, 4, or 5;

q is independently 0, 1, 2, 3, 4, or 5;

u is 0, 1, 2, 3, or 4;

z is 0, 1, 2, or 3; and wherein the alkyl, cycloalkyl, aryl, heteroaryl, or heterocyclyl of $R^E$ or $R^W$ is optionally substituted with 1 to 3 substituents independently selected from the group consisting of $NR^aR^b$, halo, cyano, oxo, $OR^a$, —$C_{1-6}$alkyl, —$C_{1-6}$haloalkyl, —$C_{1-6}$cyanoalkyl, —$C_{1-6}$alkyl$NR^aR^b$, —$C_{1-6}$ alkylOH, —$C_{3-8}$cycloalkyl, and —$C_{1-3}$ alkyl$C_{3-8}$cycloalkyl;

provided that at least one of $V^2$, $L^3$, ring B and T contains a nitrogen atom;

$R^1$ is independently selected from H, —$C_{1-8}$ alkyl, —$C_{2-6}$ alkenyl, —$C_{2-6}$ alkynyl, —$C_{3-6}$ cycloalkyl, aryl, heteroaryl, heterocyclyl, —$C_{1-6}$alkylaryl, —$C_{1-6}$alkylheteroaryl, —$C_{1-6}$alkylheterocyclyl, —$C_{1-6}$ alkyl$C(O)OR^a$, —$C_{2-6}$ alkenyl$C(O)OR^a$, —$SO_2R^a$, —$SO_2NR^aR^b$, —$C(O)NR^aSO_2R^a$, and $C_{1-6}$ alkyl$C_{3-8}$cycloalkyl;

wherein each alkyl, alkenyl, cycloalkyl, aryl, heteroaryl, or heterocyclyl is optionally substituted with 1 to 4 groups independently selected from —$OR^a$, —CN, halo, $C_{1-6}$alkyl, —$C_{1-6}$alkyl$OR^a$, —$C_{1-6}$cyanoalkyl, —$C_{1-6}$haloalkyl, $C_{3-8}$cycloalkyl, —$C_{1-3}$alkyl$C_{3-8}$cycloalkyl, —$C(O)R^a$, —$C_{1-6}$ alkyl $C(O)R^a$, —C(O)OR$^a$, —$C_{1-6}$ alkylC(O)OR$^a$, —NR$^a$R$^b$, —OC(O)NR$^a$R$^b$, NR$^a$C(O)OR$^b$, —$C_{1-6}$alkylNR$^a$R$^b$, —C(O)NR$^a$R$^b$, —$C_{1-6}$alkylC(O)NR$^a$R$^b$, —SO$_2$R$^a$, —$C_{1-6}$alkylSO$_2$R$^a$, —SO$_2$NR$^a$R$^b$, —$C_{1-6}$ alkylSO$_2$NR$^a$R$^b$, —C(O)NR$^a$SO$_2$R$^b$, —$C_{1-6}$ alkylC(O)NR$^a$SO$_2$R$^b$, —NR$^a$C(O)R$^b$, and —$C_{1-6}$alkylNR$^a$C(O)R$^b$;

$R^2$ is independently selected from H, —$C_{1-6}$ alkyl, —$C_{2-6}$ alkenyl, —$C_{2-6}$ alkynyl, —$C_{3-6}$ cycloalkyl, aryl, heteroaryl, heterocyclyl, —$C_{1-6}$alkylaryl, —$C_{1-6}$alkylheteroaryl, —$C_{1-6}$ alkylheterocyclyl, —$C_{2-6}$alkyl-OR$^a$, —$C_{1-6}$ alkylC(O)OR$^a$, and —$C_{2-6}$ alkenylC(O)OR$^a$;

wherein each alkyl, alkenyl, alkynyl, cycloalkyl, aryl, heteroaryl, or heterocyclyl is optionally substituted with 1 to 4 groups independently selected from —OR$^a$, —CN, halo, $C_{1-6}$alkyl, —$C_{1-6}$alkylOR$^a$, —$C_{1-6}$cyanoalkyl, —$C_{1-6}$haloalkyl, —$C_{3-8}$cycloalkyl, —$C_{1-3}$alkyl$C_{3-8}$cycloalkyl, —C(O)R$^a$, —$C_{1-6}$ alkylC(O)R$^a$, —C(O)OR$^a$, —$C_{1-6}$ alkylC(O)OR$^a$, —NR$^a$R$^b$, —$C_{1-6}$ alkylNR$^a$R$^b$, —C(O)NR$^a$R$^b$, $C_{1-6}$alkylC(O)NR$^a$R$^b$, —SO$_2$R$^a$, —$C_{1-6}$alkylSO$_2$R$^a$, —SO$_2$NR$^a$R$^b$, —$C_{1-6}$alkylSO$_2$NR$^a$R$^b$, —C(O)NR$^a$SO$_2$R, and —NR$^a$C(O)R$^b$;

or $R^1$ and $R^2$ combine to form a heterocyclyl group optionally containing 1, 2, or 3 additional heteroatoms independently selected from oxygen, sulfur and nitrogen, and optionally substituted with 1 to 3 groups independently selected from oxo, —$C_{1-6}$ alkyl, —$C_{3-8}$ cycloalkyl, —$C_{2-6}$ alkenyl, —$C_{2-6}$ alkynyl, —OR$^a$, —C(O)OR$^a$, —$C_{1-6}$ cyanoalkyl, —$C_{1-6}$ alkylOR$^a$, —$C_{1-6}$haloalkyl, —$C_{1-3}$ alkyl$C_{3-8}$cycloalkyl, —C(O)R$^a$, —$C_{1-6}$ alkylC(O)R$^a$, —$C_{1-6}$ alkylC(O)OR$^a$, —NR$^a$R$^b$, —$C_{1-6}$alkyNR$^a$R$^b$, —C(O)NR$^a$R$^b$, —$C_{1-6}$ alkylC(O)NR$^a$R$^b$, —SO$_2$R$^a$, —$C_{1-6}$ alkylSO$_2$R$^a$, —SO$_2$NR$^a$R$^b$, and $C_{1-6}$ alkylSO$_2$NR$^a$R$^b$;

$R^3$ is independently H, —$C_{1-6}$ alkyl, —$C_{2-6}$ alkenyl, —$C_{3-6}$ cycloalkyl, aryl, heteroaryl, heterocyclyl, —$C_{1-6}$alkylaryl, —$C_{1-6}$alkylheteroaryl, —$C_{1-6}$ alkylheterocyclyl, —$C_{2-6}$alkyl-OR$^a$, —$C_{1-6}$alkylC(O)OR$^a$, or —$C_{2-6}$ alkenylC(O)OR$^a$;

$R^4$ is independently H, —$C_{1-6}$ alkyl, —$C_{2-6}$ alkenyl, —$C_{3-6}$ cycloalkyl, aryl, heteroaryl, heterocyclyl, —$C_{1-6}$alkylaryl, —$C_{1-6}$alkylheteroaryl, —$C_{1-6}$ alkylheterocyclyl, —$C_{2-6}$alkyl-OR$^a$, —$C_{1-6}$alkylC(O)OR$^a$, or —$C_{2-6}$ alkenylC(O)OR$^a$;

$R^a$ is independently selected from H, —$C_{1-6}$ alkyl, —$C_{3-8}$ cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl;

$R^b$ is independently selected from H, —$C_{1-6}$ alkyl, —$C_{3-8}$ cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$ alkylheterocyclyl;

or $R^a$ and $R^b$ may combine together to form a ring consisting of 3-8 ring atoms that are C, N, O, or S; wherein the ring is optionally substituted with 1 to 4 groups independently selected from —OR$^f$, —CN, halo, —$C_{1-6}$ alkylOR$^f$, —$C_{1-6}$ cyanoalkyl, —$C_{1-6}$haloalkyl, —$C_{3-8}$ cycloalkyl, —$C_{1-3}$ alkyl$C_{3-8}$cycloalkyl, —C(O)R$^f$, —$C_{1-6}$ alkylC(O)R$^f$, —C(O)OR$^f$, —$C_{1-6}$ alkylC(O)OR$^f$, —NR$^f$R$^g$, —$C_{1-6}$ alkylNR$^f$R$^g$, —C(O)NR$^f$R$^g$, —$C_{1-6}$ alkylC(O)NR$^f$R$^g$, —SO$_2$R$^f$, —$C_{1-6}$ alkylSO$_2$R$^f$, —SO$_2$NR$^f$R$^g$, —$C_{1-6}$ alkylSO$_2$NR$^f$R$^g$, —$C_{1-6}$ alkylSO$_2$NR$^f$R$^g$, —C(O)NR$^f$SO$_2$R$^g$ and —NR$^f$C(O)R$^g$;

$R^c$ is independently selected from H, OH, —$C_{1-6}$ alkyl, —$C_{3-8}$ cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl;

$R^d$ is independently selected from H, —$C_{1-6}$ alkyl, —$C_3$-$C_8$cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl;

$R^e$ is independently selected from H, —$C_{1-6}$ alkyl, —O$C_{1-6}$alkyl, —$C_{3-8}$ cycloalkyl, aryl, heteroaryl, heterocyclyl, —O$C_{3-8}$cycloalkyl, —Oaryl, —Oheteroaryl, —Oheterocyclyl, —$C_{1-3}$ alkyl$C_{3-8}$cycloalkyl, —$C_{1-6}$alkylaryl, —$C_{1-6}$alkylheteroaryl, —NR$^f$R$^g$, —$C_{1-6}$alkylNR$^f$R$^g$, —C(O)NR$^f$R$^g$, —$C_{1-6}$alkylC(O)NR$^f$R$^g$, —NHSO$_2$R$^f$, —$C_{1-6}$alkylSO$_2$R$^f$, and —$C_{1-6}$alkylSO$_2$NR$^f$R$^g$;

$R^f$ is independently selected from H, —$C_{1-6}$ alkyl, —$C_{3-8}$cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl; and $R^g$ is independently selected from H, —$C_{1-6}$ alkyl, —$C_{3-8}$ cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl;

or a pharmaceutically acceptable salt, stereoisomer, mixture of stereoisomers, or tautomer thereof.

In one embodiment of formula (IIg), neither of $R^E$ or $R^W$ is an optionally substituted fused 5,6-aromatic or 5,6-heteromatic ring.

In one embodiment of formulas (IIe), (IIf), (IIg), or (IIh), $L^E$ is —O—CH$_2$—, where the oxygen is bonded to the Q ring and the —CH$_2$— is bonded to the Ar ring. In one embodiment of formulas (IIe), (IIf), (IIg), or (IIh), $L^E$ is a bond. In one embodiment of formulas (IIe), (IIf), (IIg), or (IIh), $L^E$ is —O—CH$_2$—, neither of $R^E$ or $R^W$ is an optionally substituted fused 5,6-aromatic or 5,6-heteromatic ring.

In one embodiment, the compound is represented by formula (IIIa):

(IIIa)

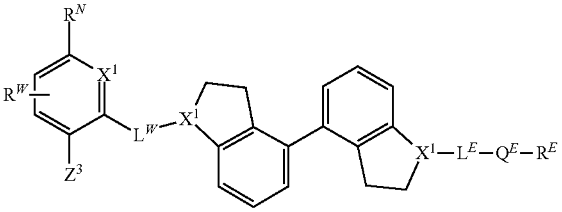

wherein each $X^1$ is independently N or CH;

$Z^3$ is halo, —OR$^a$, —N$_3$, —NO$_2$, —CN, —NR$^1$R$^2$, —SO$_2$R$^a$, —SO$_2$N$^a$R$^b$, —NR$^a$SO$_2$R$^a$, —NR$^a$C(O)R$^a$, —C(O)R$^a$, —C(O)OR$^a$, —C(O)NR$^a$R$^b$, —NR$^a$C(O)OR$^a$, —NR$^a$C(O)NR$^1$R$^2$, —OC(O)NR$^a$R$^b$, —NR$^a$SO$_2$NR$^a$R$^b$, —C(O)NR$^a$SO$_2$NR$^a$R$^b$, —$C_{1-6}$ alkyl, —$C_{2-6}$ alkenyl, —$C_{2-6}$ alkynyl, —O$C_{1-6}$ alkyl, —$C_{3-8}$cycloalkyl, —$C_{1-6}$ alkyl$C_{3-8}$ cycloalkyl, aryl, heteroaryl, heterocyclyl, and $R^N$;

wherein the alkyl, alkenyl, alkynyl, $C_{3-8}$ cycloalkyl, aryl, heteroaryl, or heterocyclyl group is optionally substituted with 1 to 4 groups independently selected from oxo, —NO$_2$, —N$_3$, —OR$^a$, halo, cyano, —NR$^a$R$^b$, —C(O)R$^a$, —C(O)OR$^a$, —O$C_{1-6}$alkyCN, —C(O)NR$^a$R$^b$, NR$^a$C(O)R$^a$, —NR$^a$C(O)OR$^a$, $—SO_2R^a$, $—NR^aSO_2R$, $—SO_2NR^aR^b$, $—NR^aSO_2NR^aR^b$, $—C(O)NR^aSO_2NR^aR^b$ and $—C_{3-8}$ cycloalkyl; and wherein the heteroaryl or heterocyclic group may be oxidized on a nitrogen atom to form an N-oxide or oxidized on a sulfur atom to form a sulfoxide or sulfone;

$R^N$ is independently $—C_{1-6}$ $alkyNR^1R^2$, $—OC_{1-6}$ $alkyNR^1R^2$, $—C_{1-6}$ $alkylOC_{1-6}$ $alkylNR^1R^2$, $—NR^aC_{1-6}$ $alkylNR^1R^2$, $—C_{1-6}$ $alkylC(O)NR^1R^2$, $—OC_{1-6}$ $alkylC(O)NR^1R^2$, $—OC_{1-6}$ $alkylC(O)OR^1$, $—SC_{1-6}alkylNR^1R^2$, $—C_{1-6}alkylOR^a$, or

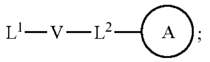

wherein: $L^1$ is independently a bond, O, $NR^a$, S, SO, or $SO_2$;

V is independently selected from a bond, $C_{1-6}$alkyl, $C_{2-6}$alkenyl, and $C_{2-6}$alkynyl;

wherein each alkyl, alkenyl, or alkynyl is optionally independently substituted with $OR^a$, halo, cyano, $—NR^aR^b$ and $—C_{3-8}$ cycloalkyl;

$L^2$ is independently a bond, O, $NR^a$, S, SO, or $SO_2$;

ring A is independently cycloalkyl, aryl, heteroaryl, or heterocyclyl;

wherein each cycloalkyl, aryl, heteroaryl, or heterocyclyl is optionally substituted with 1 to 4 groups independently selected from oxo, $—NO_2$, $—N_3$, $—OR^a$, halo, cyano, $—C_{1-6}$ alkyl, $—C_{1-6}$ haloalkyl, $—C_{2-6}$alkenyl, $—C_{2-6}$ alkynyl, $—OC_{1-6}$ haloalkyl, $NR^aR^b$, $—C(O)R^a$, $—C(O)OR^a$, $—OC_{1-6}$ alkylCN, $—C(O)NR^aR^b$, $—NR^aC(O)R^a$, $—NR^aC(O)OR^a$, $—NR^aC(O)OR^a$, $—C(O)N(R^a)OR^b$, $—SO_2R^a$, $—SO_2NR^aR^b$, $—NR^aSO_2R^b$, $—NR^aSO_2NR^aR^b$, $—C(O)NR^aSO_2NR^aR^b$, $C_{3-8}$cycloalkyl, and $C_{1-6}alkylC_{3-8}$ cycloalkyl; and wherein the alkyl, alkenyl, or alkynyl group is optionally independently substituted with $—OR^a$, halo, cyano, $—NR^aR^b$ or $—C_{3-8}$ cycloalkyl;

$L^E$ and $L^W$ are each independently a bond, —O—, —S—, —SO—, $—SO_2—$, $—(CR^3R^4)_m—$, $—(CR^3R^4)_mO(CR^3R^4)_m—$, $—(CR^3R^4)_mS(CR^3R^4)_m—$, $—(CR^3R^4)_mNR^3(CR^3R^4)_m—$, —C(O)—, $—(CR^3R^4)_mC(O)(CR^3R^4)_m—$, $—(CR^3R^4)_mC(O)NR^3(CR^3R^4)_m—$, $—(CR^3R^4)_mNR^3C(O)(CR^3R^4)_m—$, $C_{2-6}$ alkenylene, $C_{2-6}$ alkynylene,

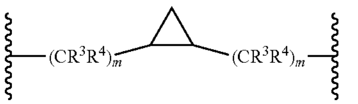

or

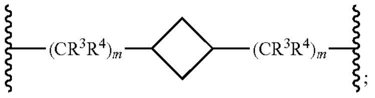

wherein each m is independently 0, 1, 2, 3 or 4;

$Q^E$ is aryl, heteroaryl, or heterocyclyl;

wherein each aryl, heteroaryl, or heterocyclyl is optionally substituted with 1 to 4 groups independently selected from halo, oxo, $—OR^a$, $—N_3$, $—NO_2$, —CN, $—NR^1R^2$, $—SO_2R^a$, $—SO_2NR^aR^b$, $—NR^aSO_2R^a$, $—NR^aC(O)R^a$, $—C(O)R^a$, $—C(O)OR^a$, $—C(O)NR^aR^b$, $—NR^aC(O)OR^a$, $—NR^aC(O)NR^1R^2$, $—OC(O)NR^aR^b$, $—NR^aSO_2NR^aR^b$, $—C(O)NR^aSO_2NR^aR^b$, $—C_{1-6}$ alkyl, $—C_{2-6}$ alkenyl, $—C_{2-6}$ alkynyl, $—OC_{1-6}$ alkyl, $—C_{3-8}$ cycloalkyl, $—C_{1-6}$ $alkylC_{3-8}$ cycloalkyl, aryl, heteroaryl, heterocyclyl, and $R^N$; and wherein the alkyl, alkenyl, alkynyl, $C_{3-8}$ cycloalkyl, aryl, heteroaryl, or heterocyclyl group is optionally substituted with 1 to 4 groups independently selected from oxo, $—NO_2$, $—N_3$, $—OR^a$, halo, cyano, $—NR^aR^b$, $—C(O)R^a$, $—C(O)OR^a$, $—OC_{1-6}$ alkyCN, $—C(O)NR^aR^b$, $NR^aC(O)R^a$, $—NR^aC(O)OR^a$, $—SO_2R^a$, $—NR^aSO_2R^b$, $—SO_2NR^aR^b$, $—NR^aSO_2NR^aR^b$, $—C(O)NR^aSO_2NR^aR^b$ and $—C_{3-8}$ cycloalkyl; and further wherein the heteroaryl or heterocyclic group may be oxidized on a nitrogen atom to form an N-oxide or oxidized on a sulfur atom to form a sulfoxide or sulfone;

$R^N$ is independently $—C_{1-6}alkylNR^1R^2$, $—OC_{1-6}$ $alkyNR^1R^2$, $—C_{1-6}$ $alkylOC_{1-6}$ $alkylNR^1R^2$, $—NR^aC_{1-6}$ $alkylNR^1R^2$, $—C_{1-6}$ $alkylC(O)NR^1R^2$, $—OC_{1-6}$ $alkylC(O)NR^1R^2$, $—OC_{1-6}$ $alkylC(O)OR^1$, $—SC_{1-6}alkylNR^1R^2$, $—C_{1-6}alkylOR^a$, or

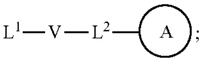

wherein: $L^1$ is independently a bond, O, $NR^a$, S, SO, or $SO_2$;

V is independently selected from a bond, $C_{1-6}$alkyl, $C_{2-6}$alkenyl, and $C_{2-6}$alkynyl;

wherein each alkyl, alkenyl, or alkynyl is optionally independently substituted with $OR^a$, halo, cyano, $—NR^aR^b$ or $—C_{3-8}$ cycloalkyl;

$L^2$ is independently a bond, O, $NR^a$, S, SO, or $SO_2$;

ring A is independently cycloalkyl, aryl, heteroaryl, or heterocyclyl;

wherein each cycloalkyl, aryl, heteroaryl, or heterocyclyl is optionally substituted with 1 to 4 groups independently selected from oxo, $—NO_2$, $—N_3$, $—OR^a$, halo, cyano, $—C_{1-6}$ alkyl, $—C_{1-6}$ haloalkyl, $—C_{2-6}$alkenyl, $—C_{2-6}$ alkynyl, $—OC_{1-6}$ haloalkyl, $NR^aR^b$, $—C(O)R^a$, $—C(O)OR^a$, $—OC_{1-6}$ alkylCN, $—C(O)NR^aR^b$, $—NR^aC(O)R^a$, $—NR^aC(O)OR^a$, $—NR^aC(O)OR^a$, $—C(O)N(R^a)OR^b$, $—SO_2R^a$, $—SO_2NR^aR^b$, $—NR^aSO_2R^b$, $—NR^aSO_2NR^aR^b$, $—C(O)NR^aSO_2NR^aR^b$, $C_{3-8}$cycloalkyl, and $C_{1-6}alkylC_{3-8}$ cycloalkyl; and wherein the alkyl, alkenyl, or alkynyl group is optionally independently substituted with $—OR^a$, halo, cyano, $—NR^aR^b$ or $—C_{3-8}$ cycloalkyl;

$R^E$ and $R^W$ are each independently $—NR^1R^2$, $—C_{1-6}$ $alkyNR^1R^2$, $—OC_{1-6}$ $alkylNR^1R^2$, $—C_{1-6}$ $alkylOC_{1-6}alkylNR^1R^2$, $—NR^aC_{1-6}$ $alkylNR^1R^2$, $—C_{1-6}$ $alkylN^+R^1R^2R^3$, $—SC_{1-6}$ $alkylNR^1R^2$, $—C(O)NR^1R^2$, $—SO_2R^a$, $—(CH_2)_uSO_2NR^1R^2$, $—(CH_2)_uNR^aSO_2NR^aR^b$, $—SO_2NR^aC_{1-6}alkyNR^1R^2$, $—NR^aSO_2C_{1-6}$ $alkylNR^1R^2$, $—(CH_2)_uC(O)$ $NR^aSO_2NR^aR^b$, $-(CH_2)_uN^+R^1R^2O^-$, $-(CH_2)_uP^+R^bR^cR^d$, $-(CH_2)_uP^+R^cR^dO^-$, $-(CH_2)_uP^+O[NR^aR^b][NR^cR^d]$, $-(CH_2)_uNR^cP(O)(OR^c)_2$, $-(CH_2)_uCH_2OP(O)(OR^c)(OR^d)$, $-(CH_2)_uOP(O)(OR^c)(OR^d)$, $-(CH_2)_uOP(O)NR^aR^b)(OR^a)$, or

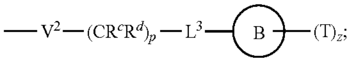

wherein:

$V^2$ is independently a bond, O, $NR^a$, S, SO, $SO_2$, $C(O)NR^a$, $NR^aC(O)$, $SO_2NR^1R^2$, or $NR^aSO_2$;

$L^3$ is independently a bond, O, $NR^a$, S, SO, $SO_2$, $C(O)NR^a$, $NR^aC(O)$, $SO_2NR^1R^2$, or $NR^aSO_2$;

ring B is cycloalkyl, aryl, heteroaryl, or heterocyclyl; T is independently H, $OR^a$, $(CH_2)_qNR^1R^2$, $(CH_2)_qNR^aC(O)R^e$ or $(CH_2)_qC(O)R^e$;

p is independently 0, 1, 2, 3, 4, or 5;

q is independently 0, 1, 2, 3, 4, or 5;

u is 0, 1, 2, 3, or 4;

z is 0, 1, 2, or 3; and wherein the alkyl, cycloalkyl, aryl, heteroaryl, or heterocyclyl of $R^E$ or $R^W$ is optionally substituted with 1 to 3 substituents independently selected from the group consisting of $NR^aR^b$, halo, cyano, oxo, $OR^a$, $-C_{1-6}$alkyl, $-C_{1-6}$haloalkyl, $-C_{1-6}$cyanoalkyl, $-C_{1-6}alkyNR^aR^b$, $-C_{1-6}$ alkylOH, $-C_{3-8}$ cycloalkyl, and $-C_{1-3}$ alkyl$C_{3-8}$cycloalkyl;

provided that at least one of $V^2$, $L^3$, ring B and T contains a nitrogen atom;

$R^1$ is independently selected from H, $-C_{1-8}$ alkyl, $-C_{2-6}$ alkenyl, $-C_{2-6}$ alkynyl, $-C_{3-6}$ cycloalkyl, aryl, heteroaryl, heterocyclyl, $-C_{1-6}$alkylaryl, $-C_{1-6}$alkylheteroaryl, $-C_{1-6}$alkylheterocyclyl, $-C_{1-6}$ alkyl$C(O)OR^a$, $-C_{2-6}$ alkenyl$C(O)OR^a$, $-SO_2R^a$, $-SO_2NR^aR^b$, $-C(O)NR^aSO_2R^a$, and $C_{1-6}$ alkyl $C_{3-8}$cycloalkyl;

wherein each alkyl, alkenyl, cycloalkyl, aryl, heteroaryl, or heterocyclyl is optionally substituted with 1 to 4 groups independently selected from $-OR^a$, $-CN$, halo, $C_{1-6}$alkyl, $-C_{1-6}$alkyl$OR^a$, $-C_{1-6}$cyanoalkyl, $-C_{1-6}$haloalkyl, $C_{3-8}$cycloalkyl, $-C_{1-3}$alkyl$C_{3-8}$cycloalkyl, $-C(O)R^a$, $-C_{1-6}$ alkyl$C(O)R^a$, $-C(O)OR^a$, $-C_{1-6}$ alkyl$C(O)OR^a$, $-NR^aR^b$, $-OC(O)NR^aR^b$, $NR^aC(O)OR^b$, $-C_{1-6}$alkyl$NR^aR^b$, $-C(O)NR^aR^b$, $-C_{1-6}$alkyl$C(O)NR^aR^b$, $-SO_2R^a$, $-C_{1-6}$alkyl$SO_2R^a$, $-SO_2NR^aR^b$, $-C_{1-6}$ alkyl$SO_2NR^aR^b$, $-C(O)NR^aSO_2R^b$, $-C_{1-6}$ alkyl$C(O)NR^aSO_2R^b$, $-NR^aC(O)R^b$, and $-C_{1-6}$alkyl$NR^aC(O)R^b$;

$R^2$ is independently selected from H, $-C_{1-6}$alkyl, $-C_{2-6}$ alkenyl, $-C_{2-6}$ alkynyl, $-C_{3-6}$ cycloalkyl, aryl, heteroaryl, heterocyclyl, $-C_{1-6}$alkylaryl, $-C_{1-6}$alkylheteroaryl, $-C_{1-6}$ alkylheterocyclyl, $-C_{2-6}$alkyl-$OR^a$, $-C_{1-6}$ alkyl$C(O)OR^a$, and $-C_{2-6}$ alkenyl$C(O)OR^a$;

wherein each alkyl, alkenyl, alkynyl, cycloalkyl, aryl, heteroaryl, or heterocyclyl is optionally substituted with 1 to 4 groups independently selected from $-OR^a$, $-CN$, halo, $C_{1-6}$alkyl, $-C_{1-6}$ alkyl$OR^a$, $-C_{1-6}$cyanoalkyl, $-C_{1-6}$haloalkyl, $-C_{3-8}$cycloalkyl, $-C_{1-3}$alkyl$C_{3-8}$cycloalkyl, $-C(O)R^a$, $-C_{1-6}$ alkyl$C(O)R^a$, $-C(O)OR^a$, $-C_{1-6}$ alkyl$C(O)OR^a$, $-NR^aR^b$, $-C_{1-6}$ alkyl$NR^aR^b$, $-C(O)NR^aR^b$, $C_{1-6}$ alkyl$C(O)NR^aR^b$, $-SO_2R^a$, $-C_{1-6}$ alkyl$SO_2R^a$, $-SO_2N^aR^b$, $-C_{1-6}$ alkyl$SO_2NR^aR^b$, $-C(O)NR^aSO_2R^b$, and $-NR^aC(O)R^b$;

or $R^1$ and $R^2$ combine to form a heterocyclyl group optionally containing 1, 2, or 3 additional heteroatoms independently selected from oxygen, sulfur and nitrogen, and optionally substituted with 1 to 3 groups independently selected from oxo, $-C_{1-6}$alkyl, $-C_{3-8}$ cycloalkyl, $-C_{2-6}$ alkenyl, $-C_{2-6}$ alkynyl, $-OR^a$, $-C(O)OR^a$, $-C_{1-6}$ cyanoalkyl, $-C_{1-6}$ alkyl$OR^a$, $-C_{1-6}$haloalkyl, $-C_{1-3}$ alkyl$C_{3-8}$cycloalkyl, $-C(O)R^a$, $-C_{1-6}$ alkyl$C(O)R^a$, $-C_{1-6}$ alkyl$C(O)OR^a$, $-NR^aR^b$, $-C_{1-6}$alkyl$NR^aR^b$, $-C(O)NR^aR^b$, $-C_{1-6}$ alkyl$C(O)NR^aR^b$, $-SO_2R^a$, $-C_{1-6}$ alkyl$SO_2R^a$, $-SO_2NR^aR^b$, and $C_{1-6}$ alkyl$SO_2NR^aR^b$;

$R^3$ is independently H, $-C_{1-6}$ alkyl, $-C_{2-6}$ alkenyl, $-C_{3-6}$ cycloalkyl, aryl, heteroaryl, heterocyclyl, $-C_{1-6}$alkylaryl, $-C_{1-6}$alkylheteroaryl, $-C_{1-6}$ alkylheterocyclyl, $-C_{2-6}$alkyl-$OR^a$, $-C_{1-6}$alkyl$C(O)OR^a$, or $-C_{2-6}$ alkenyl$C(O)OR^a$;

$R^4$ is independently H, $-C_{1-6}$ alkyl, $-C_{2-6}$ alkenyl, $-C_{3-6}$ cycloalkyl, aryl, heteroaryl, heterocyclyl, $-C_{1-6}$ alkylaryl, $-C_{1-6}$ alkylheteroaryl, $-C_{1-6}$ alkylheterocyclyl, $-C_{2-6}$alkyl-$OR^a$, $-C_{1-6}$alkyl$C(O)OR^a$, or $-C_{2-6}$ alkenyl$C(O)OR^a$;

$R^a$ is independently selected from H, $-C_{1-6}$ alkyl, $-C_{3-8}$ cycloalkyl, aryl, heteroaryl, heterocyclyl, $-C_{1-3}$ alkyl$C_{3-8}$cycloalkyl, $-C_{1-6}$ alkylaryl, $-C_{1-6}$ alkylheteroaryl, and $-C_{1-6}$alkylheterocyclyl;

$R^b$ is independently selected from H, $-C_{1-6}$ alkyl, $-C_{3-8}$ cycloalkyl, aryl, heteroaryl, heterocyclyl, $-C_{1-3}$ alkyl$C_{3-8}$cycloalkyl, $-C_{1-6}$ alkylaryl, $-C_{1-6}$ alkylheteroaryl, and $-C_{1-6}$ alkylheterocyclyl;

or $R^a$ and $R^b$ may combine together to form a ring consisting of 3-8 ring atoms that are C, N, O, or S; wherein the ring is optionally substituted with 1 to 4 groups independently selected from $-OR^f$, $-CN$, halo, $-C_{1-6}$ alkyl$OR^f$, $-C_{1-6}$ cyanoalkyl, $-C_{1-6}$haloalkyl, $-C_{3-8}$ cycloalkyl, $-C_{1-3}$ alkyl$C_{3-8}$cycloalkyl, $-C(O)R^f$, $-C_{1-6}$ alkyl$C(O)R^f$, $-C(O)OR^f$, $-C_{1-6}$ alkyl$C(O)OR^f$, $-NR^fR^g$, $-C_{1-6}$ alkyl$NR^fR^g$, $-C(O)NR^fR^g$, $-C_{1-6}$ alkyl$C(O)NR^fR^g$, $-SO_2R^f$, $-C_{1-6}$ alkyl$SO_2R$, $-SO_2NR^fR^g$, $-C_{1-6}$ alkyl$SO_2NR^fR^g$, $-C(O)NR^fSO_2R^g$ and $-NR^fC(O)R^g$;

$R^c$ is independently selected from H, OH, $-C_{1-6}$ alkyl, $-C_{3-8}$ cycloalkyl, aryl, heteroaryl, heterocyclyl, $-C_{1-3}$ alkyl$C_{3-8}$cycloalkyl, $-C_{1-6}$ alkylaryl, $-C_{1-6}$ alkylheteroaryl, and $-C_{1-6}$ alkylheterocyclyl;

$R^d$ is independently selected from H, $-C_{1-6}$ alkyl, $-C_3$-$C_8$cycloalkyl, aryl, heteroaryl, heterocyclyl, $-C_{1-3}$ alkyl$C_{3-8}$cycloalkyl, $-C_{1-6}$ alkylaryl, $-C_{1-6}$ alkylheteroaryl, and $-C_{1-6}$ alkylheterocyclyl;

$R^e$ is independently selected from H, $-C_{1-6}$ alkyl, $-OC_{1-6}$alkyl, $-C_{3-8}$ cycloalkyl, aryl, heteroaryl, heterocyclyl, $-OC_{3-8}$ cycloalkyl, —Oaryl, —Oheteroaryl, —Oheterocyclyl, $-C_{1-3}$ alkyl$C_{3-8}$cycloalkyl, $-C_{1-6}$ alkylaryl, $-C_{1-6}$alkylheteroaryl, $-NR^fR^g$, $-C_{1-6}$ alkyl$NR^fR^g$, $-C(O)NR^fR^g$, $-C_{1-6}$alkyl$C(O)NR^fR^g$, $-NHSO_2R^f$, $-C_{1-6}$alkyl$SO_2R^f$, and $-C_{1-6}$alkyl$SO_2NR^fR^g$;

$R^f$ is independently selected from H, $-C_{1-6}$ alkyl, $-C_{3-8}$ cycloalkyl, aryl, heteroaryl, heterocyclyl, $-C_{1-3}$ alkyl$C_{3-8}$cycloalkyl, $-C_{1-6}$ alkylaryl, $-C_{1-6}$ alkylheteroaryl, and $-C_{1-6}$ alkylheterocyclyl; and $R^g$ is independently selected from H, $-C_{1-6}$ alkyl, $-C_{3-8}$ cycloalkyl, aryl, heteroaryl, heterocyclyl, $-C_{1-3}$ alkyl$C_{3-8}$cycloalkyl, $-C_{1-6}$ alkylaryl, $-C_{1-6}$ alkylheteroaryl, and $-C_{1-6}$ alkylheterocyclyl;

or a pharmaceutically acceptable salt, stereoisomer, mixture of stereoisomers, or tautomer thereof.

In one embodiment of formula (IIIa), neither of $R^E$ or $R^W$ is an optionally substituted fused 5,6-aromatic or 5,6-heteromatic ring.

In one embodiment, the compound is represented by formula (IIIb):

(IIIb)

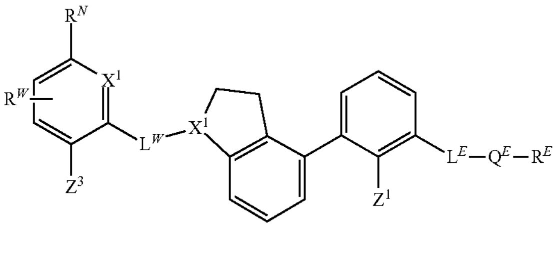

wherein each $X^1$ is independently N or CH;

$Z^1$ is halo, —$OR^a$, —$NO_2$, —CN, —$NR^aR^b$, —$N_3$, —$SO_2R^a$, —$C_{1-6}$ alkyl, —$C_{1-6}$ haloalkyl, —$C_{2-6}$alkenyl, —$C_{2-6}$ alkynyl, —$OC_{1-6}$ alkyl, —$OC_{1-6}$haloalkyl, —$C_{3-8}$ cycloalkyl, and —$C_{1-6}$ alkyl$C_{3-8}$ cycloalkyl;

wherein each alkyl, alkenyl, alkynyl, and cycloalkyl is optionally substituted with 1 to 4 groups independently selected from oxo, —$NO_2$, —$N_3$, —$OR^a$, halo, and cyano;

$Z^3$ is halo, —$OR^a$, —$N_3$, —$NO_2$, —CN, —$NR^1R^2$, —$SO_2R^a$, —$SO_2NR^aR^b$, —$NR^aSO_2R^a$, —$NR^aC(O)R^a$, —$C(O)R^a$, —$C(O)OR^a$, —$C(O)NR^aR^b$, —$NR^aC(O)OR^a$, —$NR^aC(O)NR^1R^2$, —$OC(O)NR^aR^b$, —$NR^aSO_2NR^aR^b$, —$C(O)NR^aSO_2NR^aR^b$, —$C_{1-6}$ alkyl, —$C_{2-6}$ alkenyl, —$C_{2-6}$ alkynyl, —$OC_{1-6}$ alkyl, —$C_{3-8}$ cycloalkyl, —$C_{1-6}$ alkyl$C_{3-8}$ cycloalkyl, aryl, heteroaryl, heterocyclyl, and $R^N$;

wherein the alkyl, alkenyl, alkynyl, $C_{3-8}$ cycloalkyl, aryl, heteroaryl, or heterocyclyl group is optionally substituted with 1 to 4 groups independently selected from oxo, —$NO_2$, —$N_3$, —$OR^a$, halo, cyano, —$NR^aR^b$, —$C(O)R^a$, —$C(O)OR^a$, —$OC_{1-6}$alkyCN, —$C(O)NR^aR^b$, $NR^aC(O)R^a$, —$NR^aC(O)OR^a$, —$SO_2R^a$, —$NR^aSO_2R$, —$SO_2NR^aR^b$, —$NR^aSO_2NR^aR^b$, —$C(O)NR^aSO_2NR^aR^b$ and —$C_{3-8}$ cycloalkyl; and wherein the heteroaryl or heterocyclic group may be oxidized on a nitrogen atom to form an N-oxide or oxidized on a sulfur atom to form a sulfoxide or sulfone;

$R^N$ is independently —$C_{1-6}$ alkyl$NR^1R^2$, —$OC_{1-6}$ alky$NR^1R^2$, —$C_{1-6}$ alkyl$OC_{1-6}$ alkyl$NR^1R^2$, —$NR^aC_{1-6}$ alkyl$NR^1R^2$, —$C_{1-6}$ alkyl$C(O)NR^1R^2$, —$OC_{1-6}$ alkyl$C(O)NR^1R^2$, —$OC_{1-6}$ alkyl$C(O)OR^1$, —$SC_{1-6}$alkyl$NR^1R^2$, —$C_{1-6}$alkyl$OR^a$, or

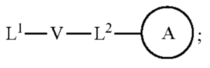;

wherein: $L^1$ is independently a bond, O, $NR^a$, S, SO, or $SO_2$;

V is independently selected from a bond, $C_{1-6}$alkyl, $C_{2-6}$alkenyl, and $C_{2-6}$alkynyl;

wherein each alkyl, alkenyl, or alkynyl is optionally independently substituted with $OR^a$, halo, cyano, —$NR^aR^b$ and —$C_{3-8}$ cycloalkyl;

$L^2$ is independently a bond, O, $NR^a$, S, SO, or $SO_2$;

ring A is independently cycloalkyl, aryl, heteroaryl, or heterocyclyl;

wherein each cycloalkyl, aryl, heteroaryl, or heterocyclyl is optionally substituted with 1 to 4 groups independently selected from oxo, —$NO_2$, —$N_3$, —$OR^a$, halo, cyano, —$C_{1-6}$ alkyl, —$C_{1-6}$ haloalkyl, —$C_{2-6}$alkenyl, —$C_{2-6}$ alkynyl, —$OC_{1-6}$ haloalkyl, $NR^aR^b$, —$C(O)R^a$, —$C(O)OR^a$, —$OC_{1-6}$ alkylCN, —$C(O)NR^aR^b$, —$NR^aC(O)R^a$, —$NR^aC(O)OR^a$, —$NR^aC(O)OR^a$, —$C(O)N(R^a)OR^b$, —$SO_2R^a$, —$SO_2NR^aR^b$, —$NR^aSO_2R^b$, —$NR^aSO_2NR^aR^b$, —$C(O)NR^aSO_2NR^aR^b$, $C_{3-8}$cycloalkyl, and $C_{1-6}$alkyl$C_{3-8}$ cycloalkyl; and wherein the alkyl, alkenyl, or alkynyl group is optionally independently substituted with —$OR^a$, halo, cyano, —$NR^aR^b$ or —$C_{3-8}$ cycloalkyl;

$L^E$ and $L^W$ are each independently a bond, —O—, —S—, —SO—, —$SO_2$—, —$(CR^3R^4)_m$—, —$(CR^3R^4)_mO(CR^3R^4)_m$—, —$(CR^3R^4)_mS(CR^3R^4)_m$—, —$(CR^3R^4)_mNR^3(CR^3R^4)_m$—, —C(O)—, —$(CR^3R^4)_mC(O)(CR^3R^4)_m$—, —$(CR^3R^4)_mC(O)NR^3(CR^3R^4)_m$—, —$(CR^3R^4)_mNR^3C(O)(CR^3R^4)_m$—, $C_{2-6}$ alkenylene, $C_{2-6}$ alkynylene,

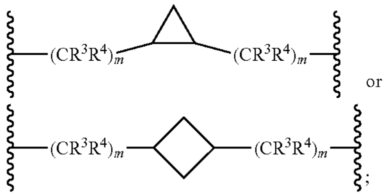

wherein each m is independently 0, 1, 2, 3 or 4;

$Q^E$ is aryl, heteroaryl, or heterocyclyl;

wherein each aryl, heteroaryl, or heterocyclyl is optionally substituted with 1 to 4 groups independently selected from halo, oxo, —$OR^a$, —$N_3$, —$NO_2$, —CN, —$NR^1R^2$, —$SO_2R^a$, —$SO_2NR^aR^b$, —$NR^aSO_2R^a$, —$NR^aC(O)R^a$, —$C(O)R^a$, —$C(O)OR^a$, —$C(O)NR^aR^b$, —$NR^aC(O)OR^a$, —$NR^aC(O)NR^1R^2$, —$OC(O)NR^aR^b$, —$NR^aSO_2NR^aR^b$, —$C(O)NR^aSO_2NR^aR^b$, —$C_{1-6}$ alkyl, —$C_{2-6}$ alkenyl, —$C_{2-6}$ alkynyl, —$OC_{1-6}$ alkyl, —$C_{3-8}$ cycloalkyl, —$C_{1-6}$ alkyl$C_{3-8}$ cycloalkyl, aryl, heteroaryl, heterocyclyl, and $R^N$; and wherein the alkyl, alkenyl, alkynyl, $C_{3-8}$ cycloalkyl, aryl, heteroaryl, or heterocyclyl group is optionally substituted with 1 to 4 groups independently selected from oxo, —$NO_2$, —$N_3$, —$OR^a$, halo, cyano, —$NR^aR^b$, —$C(O)R^a$, —$C(O)OR^a$, —$OC_{1-6}$alkylCN, —$C(O)NR^aR^b$, $NR^aC(O)R^a$, —$NR^aC(O)OR^a$, —$SO_2R^a$, —$NR^aSO_2R^b$, —$SO_2NR^aR^b$, —$NR^aSO_2NR^aR^b$, —$C(O)NR^aSO_2NR^aR^b$ and —$C_{3-8}$ cycloalkyl; and further wherein the heteroaryl or heterocyclic group may be oxidized on a nitrogen atom to form an N-oxide or oxidized on a sulfur atom to form a sulfoxide or sulfone;

$R^N$ is independently —$C_{1-6}$ alkyl$NR^1R^2$, —$OC_{1-6}$ alky$NR^1R^2$, —$C_{1-6}$ alkyl$OC_{1-6}$ alky$NR^1R^2$, —$NR^aC_{1-6}$ alkyl$NR^1R^2$, —$C_{1-6}$ alkylC(O)$NR^1R^2$, —$OC_{1-6}$ alkylC(O)$NR^1R^2$, —$OC_{1-6}$ alkylC(O)$OR^1$, —$SC_{1-6}$alkyl$NR^1R^2$, —$C_{1-6}$alkyl$OR^a$, or

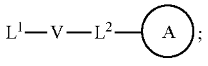

wherein: $L^1$ is independently a bond, O, $NR^a$, S, SO, or $SO_2$;

V is independently selected from a bond, $C_{1-6}$alkyl, $C_{2-6}$alkenyl, and $C_{2-6}$alkynyl;

wherein each alkyl, alkenyl, or alkynyl is optionally independently substituted with $OR^a$, halo, cyano, —$NR^aR^b$ or —$C_{3-8}$ cycloalkyl;

$L^2$ is independently a bond, O, $NR^a$, S, SO, or $SO_2$;

ring A is independently cycloalkyl, aryl, heteroaryl, or heterocyclyl;

wherein each cycloalkyl, aryl, heteroaryl, or heterocyclyl is optionally substituted with 1 to 4 groups independently selected from oxo, —$NO_2$, —$N_3$, —$OR^a$, halo, cyano, —$C_{1-6}$ alkyl, —$C_{1-6}$ haloalkyl, —$C_{2-6}$alkenyl, —$C_{2-6}$ alkynyl, —$OC_{1-6}$ haloalkyl, $NR^aR^b$, —C(O)$R^a$, —C(O)$OR^a$, —$OC_{1-6}$ alkylCN, —C(O)$NR^aR^b$, —$NR^a$C(O)$R^a$, —$NR^a$C(O)$OR^a$, —$NR^a$C(O)$OR^a$, —C(O)N($R^a$)$OR^b$, —$SO_2R^a$, —$SO_2NR^aR^b$, —$NR^aSO_2R^b$, —$NR^aSO_2NR^aR^b$, —C(O)$NR^aSO_2NR^aR^b$, $C_{3-8}$cycloalkyl, and $C_{1-6}$alkyl$C_{3-8}$cycloalkyl; and wherein the alkyl, alkenyl, or alkynyl group is optionally independently substituted with —$OR^a$, halo, cyano, —$NR^aR^b$ or —$C_{3-8}$cycloalkyl;

$R^E$ and $R^W$ are each independently —$NR^1R^2$, —$C_{1-6}$ alky$NR^1R^2$, —$OC_{1-6}$ alkyl$NR^1R^2$, —$C_{1-6}$ alkylO $C_{1-6}$alkyl$NR^1R^2$, —$NR^aC_{1-6}$ alkyl$NR^1R^2$, —$C_{1-6}$ alkyl$N^+R^1R^2R^3$, —$SC_{1-6}$ alkyl$NR^1R^2$, —C(O)$NR^1R^2$, —$SO_2R^a$, —$(CH_2)_uSO_2NR^1R^2$, —$(CH_2)_uNR^aSO_2NR^aR^b$, —$SO_2NR^aC_{1-6}$alky$NR^1R^2$, —$NR^aSO_2C_{1-6}$ alkyl$NR^1R^2$, —$(CH_2)_u$C(O)$NR^aSO_2NR^aR^b$, —$(CH_2)_uN^+R^1R^2O^-$, —$(CH_2)_uP^+R^bR^cR^d$, —$(CH_2)_uP^+R^cR^dO^-$, —$(CH_2)_uP^+O[NR^aR^b][NR^cR^d]$, —$(CH_2)_uNR^cP(O)(OR^c)_2$, —$(CH_2)_uCH_2OP(O)(OR^c)(OR^d)$, —$(CH_2)_uOP(O)(OR^c)(OR^d)$, —$(CH_2)_uOP(O)NR^aR^b)(OR^a)$, or

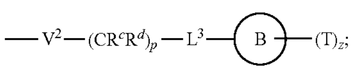

wherein:

$V^2$ is independently a bond, O, $NR^a$, S, SO, $SO_2$, C(O)$NR^a$, $NR^a$C(O), $SO_2NR^1R^2$, or $NR^aSO_2$;

$L^3$ is independently a bond, O, $NR^a$, S, SO, $SO_2$, C(O)$NR^a$, $NR^a$C(O), $SO_2NR^1R^2$, or $NR^aSO_2$;

ring B is cycloalkyl, aryl, heteroaryl, or heterocyclyl; T is independently H, $OR^a$, $(CH_2)_qNR^1R^2$, $(CH_2)_qNR^aC(O)R^e$ or $(CH_2)_qC(O)R$;

p is independently 0, 1, 2, 3, 4, or 5;

q is independently 0, 1, 2, 3, 4, or 5;

u is 0, 1, 2, 3, or 4;

z is 0, 1, 2, or 3; and wherein the alkyl, cycloalkyl, aryl, heteroaryl, or heterocyclyl of $R^E$ or $R^W$ is optionally substituted with 1 to 3 substituents independently selected from the group consisting of $NR^aR^b$, halo, cyano, oxo, $OR^a$, —$C_{1-6}$alkyl, —$C_{1-6}$haloalkyl, —$C_{1-6}$cyanoalkyl, —$C_{1-6}$alkyl$NR^aR^b$, —$C_{1-6}$ alkylOH, —$C_{3-8}$cycloalkyl, and —$C_{1-3}$ alkyl$C_{3-8}$cycloalkyl;

provided that at least one of $V^2$, $L^3$, ring B and T contains a nitrogen atom;

$R^1$ is independently selected from H, —$C_{1-8}$ alkyl, —$C_{2-6}$ alkenyl, —$C_{2-6}$ alkynyl, —$C_{3-6}$ cycloalkyl, aryl, heteroaryl, heterocyclyl, —$C_{1-6}$alkylaryl, —$C_{1-6}$alkylheteroaryl, —$C_{1-6}$alkylheterocyclyl, —$C_{1-6}$ alkylC(O)$OR^a$, —$C_{2-6}$ alkenylC(O)$OR^a$, —$SO_2R^a$, —$SO_2NR^aR^b$, —C(O)$NR^aSO_2R^a$, and $C_{1-6}$ alkyl $C_{3-8}$cycloalkyl;

wherein each alkyl, alkenyl, cycloalkyl, aryl, heteroaryl, or heterocyclyl is optionally substituted with 1 to 4 groups independently selected from —$OR^a$, —CN, halo, $C_{1-6}$alkyl, —$C_{1-6}$alkyl$OR^a$, —$C_{1-6}$cyanoalkyl, —$C_{1-6}$haloalkyl, $C_{3-8}$cycloalkyl, —$C_{1-3}$alkyl$C_{3-8}$cycloalkyl, —C(O)$R^a$, —$C_{1-6}$ alkylC(O)$R^a$, —C(O)$OR^a$, —$C_{1-6}$ alkylC(O)$OR^a$, —$NR^aR^b$, —OC(O)$NR^aR^b$, $NR^a$C(O)$OR^b$, —$C_{1-6}$alkyl$NR^aR^b$, —C(O)$NR^aR^b$, —$C_{1-6}$alkylC(O)$NR^aR^b$, —$SO_2R^a$, —$C_{1-6}$alkyl$SO_2R^a$, —$SO_2NR^aR^b$, —$C_{1-6}$ alkyl$SO_2NR^aR^b$, —C(O)$NR^aSO_2R^b$, —$C_{1-6}$ alkylC(O)$NR^aSO_2R^b$, —$NR^a$C(O)$R^b$, and —$C_{1-6}$alkyl$NR^a$C(O)$R^b$;

$R^2$ is independently selected from H, —$C_{1-6}$alkyl, —$C_{2-6}$ alkenyl, —$C_{2-6}$ alkynyl, —$C_{3-6}$ cycloalkyl, aryl, heteroaryl, heterocyclyl, —$C_{1-6}$alkylaryl, —$C_{1-6}$alkylheteroaryl, —$C_{1-6}$ alkylheterocyclyl, —$C_{2-6}$alkyl-$OR^a$, —$C_{1-6}$ alkylC(O)$OR^a$, and —$C_{2-6}$ alkenylC(O)$OR^a$;

wherein each alkyl, alkenyl, alkynyl, cycloalkyl, aryl, heteroaryl, or heterocyclyl is optionally substituted with 1 to 4 groups independently selected from —$OR^a$, —CN, halo, $C_{1-6}$alkyl, —$C_{1-6}$alkyl$OR^a$, —$C_{1-6}$cyanoalkyl, —$C_{1-6}$haloalkyl, —$C_{3-8}$cycloalkyl, —$C_{1-3}$alkyl$C_{3-8}$cycloalkyl, —C(O)$R^a$, —$C_{1-6}$ alkylC(O)$R^a$, —C(O)$OR^a$, —$C_{1-6}$ alkylC(O)$OR^a$, —$NR^aR^b$, —$C_{1-6}$ alkyl$NR^aR^b$, —C(O)$NR^aR^b$, $C_{1-6}$alkylC(O)$NR^aR^b$, —$SO_2R^a$, —$C_{1-6}$alkyl$SO_2R^a$, —$SO_2NR^aR^b$, —$C_{1-6}$alkyl$SO_2NR^aR^b$, —C(O)$NR^aSO_2$R, and —$NR^a$C(O)$R^b$;

or $R^1$ and $R^2$ combine to form a heterocyclyl group optionally containing 1, 2, or 3 additional heteroatoms independently selected from oxygen, sulfur and nitrogen, and optionally substituted with 1 to 3 groups independently selected from oxo, —$C_{1-6}$alkyl, —$C_{3-8}$ cycloalkyl, —$C_{2-6}$ alkenyl, —$C_{2-6}$ alkynyl, —$OR^a$, —C(O)$OR^a$, —$C_{1-6}$cyanoalkyl, —$C_{1-6}$ alkyl$OR^a$, —$C_{1-6}$haloalkyl, —$C_{1-3}$ alkyl$C_{3-8}$cycloalkyl, —C(O)$R^a$, —$C_{1-6}$ alkylC(O)$R^a$, —$C_{1-6}$ alkylC(O)$OR^a$, —$NR^aR^b$, —$C_{1-6}$alky$NR^aR^b$, —C(O)$NR^aR^b$, —$C_{1-6}$ alkylC(O)$NR^aR^b$, —$SO_2R^a$, —$C_{1-6}$ alkyl$SO_2R^a$, —$SO_2NR^aR^b$, and $C_{1-6}$ alkyl$SO_2NR^aR^b$;

$R^3$ is independently H, —$C_{1-6}$alkyl, —$C_{2-6}$ alkenyl, —$C_{3-6}$ cycloalkyl, aryl, heteroaryl, heterocyclyl, —$C_{1-6}$alkylaryl, —$C_{1-6}$alkylheteroaryl, —$C_{1-6}$ alkylheterocyclyl, —$C_{2-6}$alkyl-$OR^a$, —$C_{1-6}$alkylC(O)$OR^a$, or —$C_{2-6}$ alkenylC(O)$OR^a$;

$R^4$ is independently H, —$C_{1-6}$alkyl, —$C_{2-6}$ alkenyl, —$C_{3-6}$ cycloalkyl, aryl, heteroaryl, heterocyclyl, —$C_{1-6}$alkylaryl, —$C_{1-6}$alkylheteroaryl, —$C_{1-6}$ alkylheterocyclyl, —$C_{2-6}$alkyl-$OR^a$, —$C_{1-6}$alkylC(O)$OR^a$, or —$C_{2-6}$ alkenylC(O)$OR^a$;

$R^a$ is independently selected from H, —$C_{1-6}$alkyl, —$C_{3-8}$ cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl;

$R^b$ is independently selected from H, —$C_{1-6}$alkyl, —$C_{3-8}$cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$ alkylheterocyclyl;

or $R^a$ and $R^b$ may combine together to form a ring consisting of 3-8 ring atoms that are C, N, O, or S; wherein the ring is optionally substituted with 1 to 4 groups independently selected from —$OR^f$, —CN, halo, —$C_{1-6}$ alkyl$OR^f$, —$C_{1-6}$ cyanoalkyl, —$C_{1-6}$haloalkyl, —$C_{3-8}$ cycloalkyl, —$C_{1-3}$ alkyl$C_{3-8}$cycloalkyl, —C(O)$R^f$, —$C_{1-6}$ alkylC(O)$R^f$, —C(O)$OR^f$, —$C_{1-6}$ alkylC(O)$OR^f$, —$NR^fR^g$, —$C_{1-6}$ alkyl$NR^fR^g$, —C(O)$NR^fR^g$, —$C_{1-6}$ alkylC(O)$NR^fR^g$, —$SO_2R^f$, —$C_{1-6}$ alkyl$SO_2R^f$, —$SO_2NR^fR^g$, —$C_{1-6}$ alkyl$SO_2NR^fR^g$, —C(O)$NR^fSO_2R^g$ and —$NR^f$C(O)$R^g$;

$R^c$ is independently selected from H, OH, —$C_{1-6}$alkyl, —$C_{3-8}$ cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl;

$R^d$ is independently selected from H, —$C_{1-6}$alkyl, —$C_3$-$C_8$cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl;

$R^e$ is independently selected from H, —$C_{1-6}$alkyl, —$OC_{1-6}$alkyl, —$C_{3-8}$ cycloalkyl, aryl, heteroaryl, heterocyclyl, —$OC_{3-8}$cycloalkyl, —Oaryl, —Oheteroaryl, —Oheterocyclyl, —$C_{1-3}$ alkyl$C_{3-8}$cycloalkyl, —$C_{1-6}$alkylaryl, —$C_{1-6}$alkylheteroaryl, —$NR^fR^g$, —$C_{1-6}$alkyl$NR^fR^g$, —C(O)$NR^fR^g$, —$C_{1-6}$alkylC(O)$NR^fR^g$, —$NHSO_2R^f$, —$C_{1-6}$alkyl$SO_2R^f$, and —$C_{1-6}$alkyl$SO_2NR^fR^g$;

$R^f$ is independently selected from H, —$C_{1-6}$alkyl, —$C_{3-8}$ cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl; and $R^g$ is independently selected from H, —$C_{1-6}$alkyl, —$C_{3-8}$ cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl;

or a pharmaceutically acceptable salt, stereoisomer, mixture of stereoisomers, or tautomer thereof.

In one embodiment of formula (IIIb), none of $Q^E$, $R^E$ or $R^W$ is an optionally substituted fused 5,6-aromatic or 5,6-heteromatic ring.

In one embodiment, the compound is represented by formula (IVa):

(IVa)

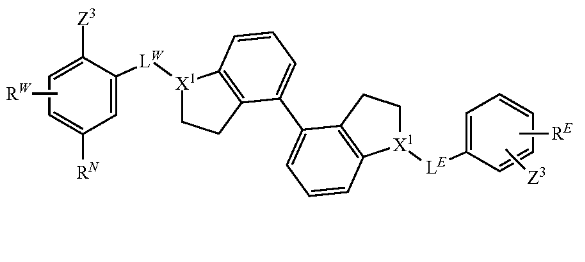

wherein each $X^1$ is independently N or CH;

each $Z^1$ is independently halo, —$OR^a$, —$C_{1-6}$ alkyl, —$OC_{1-6}$alkyl, —$C_{1-6}$ haloalkyl, or —$C_{3-8}$ cycloalkyl;

each $Z^3$ is independently halo, —$OR^a$, —$N_3$, —$NO_2$, —CN, —$NR^1R^2$, —$SO_2R^a$, —$SO_2NR^aR^b$, —$NR^aSO_2R^a$, —$NR^a$C(O)$R^a$, —C(O)$R^a$, —C(O)$OR^a$, —C(O)$NR^aR^b$, —$NR^a$C(O)$OR^a$, —$NR^a$C(O)$NR^1R^2$, —OC(O)$NR^aR^b$, —$NR^aSO_2NR^aR^b$, —C(O)$NR^aSO_2NR^aR^b$, —$C_{1-6}$ alkyl, —$C_{2-6}$alkenyl, —$C_{2-6}$ alkynyl, —$OC_{1-6}$ alkyl, —$C_{3-8}$ cycloalkyl, —$C_{1-6}$ alkyl$C_{3-8}$ cycloalkyl, aryl, heteroaryl, heterocyclyl, and $R^N$;

wherein the alkyl, alkenyl, alkynyl, $C_{3-8}$ cycloalkyl, aryl, heteroaryl, or heterocyclyl group is optionally substituted with 1 to 4 groups independently selected from oxo, —$NO_2$, —$N_3$, —$OR^a$, halo, cyano, —$NR^aR^b$, —C(O)$R^a$, —C(O)$OR^a$, —$OC_{1-6}$alkyCN, —C(O)$NR^aR^b$, $NR^a$C(O)$R^a$, —$NR^a$C(O)$OR^a$, —$SO_2R^a$, —$NR^aSO_2$R, —$SO_2NR^aR^b$, —$NR^aSO_2NR^aR^b$, —C(O)$NR^aSO_2NR^aR^b$ and —$C_{3-8}$ cycloalkyl; and wherein the heteroaryl or heterocyclic group may be oxidized on a nitrogen atom to form an N-oxide or oxidized on a sulfur atom to form a sulfoxide or sulfone;

$R^N$ is independently —$C_{1-6}$ alkyl$NR^1R^2$, —$OC_{1-6}$ alky$NR^1R^2$, —$C_{1-6}$ alkyl$OC_{1-6}$ alkyl$NR^1R^2$, —$NR^aC_{1-6}$ alkyl$NR^1R^2$, —$C_{1-6}$ alkylC(O)$NR^1R^2$, —$OC_{1-6}$ alkylC(O)$NR^1R^2$, —$OC_{1-6}$ alkylC(O)$OR^1$, —$SC_{1-6}$alkyl$NR^1R^2$, —$C_{1-6}$alkyl$OR^a$, or

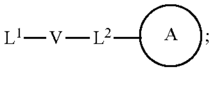;

wherein: $L^1$ is independently a bond, O, $NR^a$, S, SO, or $SO_2$;

V is independently selected from a bond, $C_{1-6}$alkyl, $C_{2-6}$alkenyl, and $C_{2-6}$alkynyl;

wherein each alkyl, alkenyl, or alkynyl is optionally independently substituted with $OR^a$, halo, cyano, —$NR^aR^b$, or —$C_{3-8}$ cycloalkyl;

$L^2$ is independently a bond, O, $NR^a$, S, SO, or $SO_2$;

ring A is independently cycloalkyl, aryl, heteroaryl, or heterocyclyl;

wherein each cycloalkyl, aryl, heteroaryl, or heterocyclyl is optionally substituted with 1 to 4 groups independently selected from oxo, —$NO_2$, —$N_3$, —$OR^a$, halo, cyano, —$C_{1-6}$ alkyl, —$C_{1-6}$ haloalkyl, —$C_{2-6}$alkenyl, —$C_{2-6}$ alkynyl, —$OC_{1-6}$ haloalkyl, $NR^aR^b$, —C(O)$R^a$, —C(O)$OR^a$, —$OC_{1-6}$ alkylCN, —C(O)$NR^aR^b$, —$NR^a$C(O)$R^a$, —$NR^a$C(O)$OR^a$, —$NR^a$C(O)$OR^a$, —C(O)N($R^a$)$OR^b$, —$SO_2R^a$, —$SO_2NR^aR^b$, —$NR^aSO_2R^b$, —$NR^aSO_2NR^aR^b$, —C(O)$NR^aSO_2NR^aR^b$, $C_{3-8}$cycloalkyl, and $C_{1-6}$alkyl$C_{3-8}$ cycloalkyl; and wherein the alkyl, alkenyl, or alkynyl group is optionally independently substituted with —$OR^a$, halo, cyano, —$NR^aR^b$, or —$C_{3-8}$ cycloalkyl;

$L^E$ and $L^W$ are each independently a bond, —O—, —S—, —SO—, —$SO_2$—, —$(CR^3R^4)_m$—, —$(CR^3R^4)_m$O$(CR^3R^4)_m$—, —$(CR^3R^4)_m$S$(CR^3R^4)_m$—, —$(CR^3R^4)_m NR^3(CR^3R^4)_m$—, —C(O)—, —$(CR^3R^4)_m C(O)(CR^3R^4)_m$—, —$(CR^3R^4)_m C(O)NR^3(CR^3R^4)_m$—, —$(CR^3R^4)_m NR^3C(O)(CR^3R^4)_m$—, $C_{2-6}$ alkenylene, $C_{2-6}$ alkynylene,

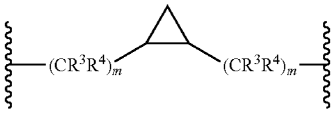

or

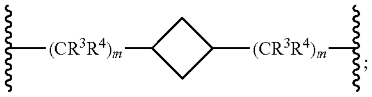

each m is independently 0, 1, 2, 3 or 4;

$R^E$ and $R^W$ are each independently —$NR^1R^2$, —$C_{1-6}$ alkyNR$^1$R$^2$, —$OC_{1-6}$ alkylNR$^1$R$^2$, —$C_{1-6}$ alkylO $C_{1-6}$alkylNR$^1$R$^2$, —$NR^aC_{1-6}$ alkylNR$^1$R$^2$, —$C_{1-6}$ alkylN$^+$R$^1$R$^2$R$^3$, —$SC_{1-6}$ alkylNR$^1$R$^2$, —C(O)NR$^1$R$^2$, —$SO_2R^a$, —$(CH_2)_uSO_2NR^1R^2$, —$(CH_2)_uNR^aSO_2NR^aR^b$, —$SO_2NR^aC_{1-6}$ alkyNR$^1$R$^2$, —$NR^aSO_2C_{1-6}$ alkylNR$^1$R$^2$, —$(CH_2)_uC(O)NR^aSO_2NR^aR^b$, —$(CH_2)_uN^+R^1R^2O^-$, —$(CH_2)_uP^+R^bR^cR^d$, —$(CH_2)_uP^+R^cR^dO$—, —$(CH_2)_uP^+O[NR^aR^b][NR^cR^d]$, —$(CH_2)_uNR^cP(O)(OR^c)_2$, —$(CH_2)_uCH_2OP(O)(OR^c)(OR^d)$, —$(CH_2)_uOP(O)(OR^c)(OR^d)$, —$(CH_2)_uOP(O)NR^aR^b)(OR^a)$, or

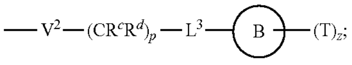

wherein:

$V^2$ is independently a bond, O, $NR^a$, S, SO, $SO_2$, C(O)NR$^a$, NR$^a$C(O), $SO_2NR^1R^2$, or $NR^aSO_2$;

$L^3$ is independently a bond, O, $NR^a$, S, SO, $SO_2$, C(O)NR$^a$, NR$^a$C(O), $SO_2NR^1R^2$, or $NR^aSO_2$;

ring B is cycloalkyl, aryl, heteroaryl, or heterocyclyl; T is independently H, $OR^a$, $(CH_2)_qNR^1R^2$, $(CH_2)_qNR^aC(O)R^e$, or $(CH_2)_qC(O)R^e$;

p is independently 0, 1, 2, 3, 4, or 5;

q is independently 0, 1, 2, 3, 4, or 5;

u is 0, 1, 2, 3, or 4;

z is 0, 1, 2, or 3; and wherein the alkyl, cycloalkyl, aryl, heteroaryl, or heterocyclyl of $R^E$ or $R^W$ is optionally substituted with 1 to 3 substituents independently selected from the group consisting of $NR^aR^b$, halo, cyano, oxo, $OR^a$, —$C_{1-6}$alkyl, —$C_{1-6}$haloalkyl, —$C_{1-6}$cyanoalkyl, —$C_{1-6}$alkyNR$^a$R$^b$, —$C_{1-6}$alkylOH, —$C_{3-8}$cycloalkyl, and —$C_{1-3}$ alkylC$_{3-8}$cycloalkyl;

provided that at least one of $V^2$, $L^3$, ring B and T contains a nitrogen atom;

$R^1$ is independently selected from H, —$C_{1-8}$ alkyl, —$C_{2-6}$ alkenyl, —$C_{2-6}$ alkynyl, —$C_{3-6}$ cycloalkyl, aryl, heteroaryl, heterocyclyl, —$C_{1-6}$alkylaryl, —$C_{1-6}$alkylheteroaryl, —$C_{1-6}$alkylheterocyclyl, —$C_{1-6}$ alkylC(O)OR$^a$, —$C_{2-6}$ alkenylC(O)OR$^a$, —$SO_2R^a$, —$SO_2NR^aR^b$, —C(O)NR$^a$SO$_2$R$^a$, and $C_{1-6}$ alkyl $C_{3-8}$cycloalkyl;

wherein each alkyl, alkenyl, cycloalkyl, aryl, heteroaryl, or heterocyclyl is optionally substituted with 1 to 4 groups independently selected from —$OR^a$, —CN, halo, $C_{1-6}$alkyl, —$C_{1-6}$alkylOR$^a$, —$C_{1-6}$ cyanoalkyl, —$C_{1-6}$haloalkyl, $C_{3-8}$ cycloalkyl, —$C_{1-3}$ alkylC$_{3-8}$cycloalkyl, —C(O)R$^a$, —$C_{1-6}$ alkyl C(O) R$^a$, —C(O)OR$^a$, —$C_{1-6}$alkylC(O)OR$^a$, —$NR^aR^b$, —OC(O)NR$^a$R$^b$, NR$^a$C(O)OR$^b$, —$C_{1-6}$ alkylNR$^a$R$^b$, —C(O)NR$^a$R$^b$, —$C_{1-6}$alkylC(O)NR$^a$R$^b$, —$SO_2R^a$, —$C_{1-6}$alkylSO$_2$R$^a$, —$SO_2N^aR^b$, —$C_{1-6}$ alkylSO$_2$NR$^a$R$^b$, —C(O)NR$^a$SO$_2$R$^b$, —$C_{1-6}$ alkylC(O)NR$^a$SO$_2$R$^b$, —NR$^a$C(O)R$^b$, and —$C_{1-6}$alkylNR$^a$C(O)R$^b$;

$R^2$ is independently selected from H, —$C_{1-6}$alkyl, —$C_{2-6}$ alkenyl, —$C_{2-6}$ alkynyl, —$C_{3-6}$ cycloalkyl, aryl, heteroaryl, heterocyclyl, —$C_{1-6}$alkylaryl, —$C_{1-6}$alkylheteroaryl, —$C_{1-6}$ alkylheterocyclyl, —$C_{2-6}$alkyl-OR$^a$, —$C_{1-6}$ alkylC(O)OR$^a$, and —$C_{2-6}$ alkenylC(O)OR$^a$;

wherein each alkyl, alkenyl, alkynyl, cycloalkyl, aryl, heteroaryl, or heterocyclyl is optionally substituted with 1 to 4 groups independently selected from —$OR^a$, —CN, halo, $C_{1-6}$alkyl, —$C_{1-6}$alkylOR$^a$, —$C_{1-6}$cyanoalkyl, —$C_{1-6}$haloalkyl, —$C_{3-8}$cycloalkyl, —$C_{1-3}$alkylC$_{3-8}$cycloalkyl, —C(O)R$^a$, —$C_{1-6}$ alkylC(O)R$^a$, —C(O)OR$^a$, —$C_{1-6}$ alkylC(O)OR$^a$, —$NR^aR^b$, —$C_{1-6}$ alkylNR$^a$R$^b$, —C(O)NR$^a$R$^b$, $C_{1-6}$alkylC(O)NR$^a$R$^b$, —$SO_2R^a$, —$C_{1-6}$alkylSO$_2$R$^a$, —$SO_2NR^aR^b$, —$C_{1-6}$alkylSO$_2$NR$^a$R$^b$, —C(O)NR$^a$SO$_2$R$^b$ and —NR$^a$C(O)R$^b$;

or $R^1$ and $R^2$ combine to form a heterocyclyl group optionally containing 1, 2, or 3 additional heteroatoms independently selected from oxygen, sulfur and nitrogen, and optionally substituted with 1 to 3 groups independently selected from oxo, —$C_{1-6}$alkyl, —$C_{3-8}$ cycloalkyl, —$C_{2-6}$ alkenyl, —$C_{2-6}$ alkynyl, —$OR^a$, —C(O)OR$^a$, —$C_{1-6}$ cyanoalkyl, —$C_{1-6}$ alkylOR$^a$, —$C_{1-6}$haloalkyl, —$C_{1-3}$ alkylC$_{3-8}$cycloalkyl, —C(O)R$^a$, —$C_{1-6}$ alkylC(O)R$^a$, —$C_{1-6}$ alkylC(O)OR$^a$, —$NR^aR^b$, —$C_{1-6}$alkyNR$^a$R$^b$, —C(O)NR$^a$R$^b$, —$C_{1-6}$ alkylC(O)NR$^a$R$^b$, —$SO_2R^a$, —$C_{1-6}$ alkylSO$_2$R$^a$, —$SO_2NR^aR^b$, and $C_{1-6}$ alkylSO$_2$NR$^a$R$^b$;

$R^3$ is independently H, —$C_{1-6}$alkyl, —$C_{2-6}$ alkenyl, —$C_{3-6}$ cycloalkyl, aryl, heteroaryl, heterocyclyl, —$C_{1-6}$alkylaryl, —$C_{1-6}$alkylheteroaryl, —$C_{1-6}$ alkylheterocyclyl, —$C_{2-6}$alkyl-OR$^a$, —$C_{1-6}$alkylC(O)OR$^a$, or —$C_{2-6}$ alkenylC(O)OR$^a$;

$R^4$ is independently H, —$C_{1-6}$alkyl, —$C_{2-6}$ alkenyl, —$C_{3-6}$ cycloalkyl, aryl, heteroaryl, heterocyclyl, —$C_{1-6}$alkylaryl, —$C_{1-6}$alkylheteroaryl, —$C_{1-6}$ alkylheterocyclyl, —$C_{2-6}$alkyl-OR$^a$, —$C_{1-6}$alkylC(O)OR$^a$, or —$C_{2-6}$ alkenylC(O)OR$^a$;

$R^a$ is independently selected from H, —$C_{1-6}$alkyl, —$C_{3-8}$cycloalkyl, aryl, heteroaryl, heterocyclyl, —$C_{1-3}$ alkylC$_{3-8}$cycloalkyl, —$C_{1-6}$ alkylaryl, —$C_{1-6}$ alkylheteroaryl, and —$C_{1-6}$alkylheterocyclyl;

$R^b$ is independently selected from H, —$C_{1-6}$alkyl, —$C_{3-8}$ cycloalkyl, aryl, heteroaryl, heterocyclyl, —$C_{1-3}$ alkylC$_{3-8}$cycloalkyl, —$C_{1-6}$ alkylaryl, —$C_{1-6}$ alkylheteroaryl, and —$C_{1-6}$ alkylheterocyclyl;

or $R^a$ and $R^b$ may combine together to form a ring consisting of 3-8 ring atoms that are C, N, O, or S; wherein the ring is optionally substituted with 1 to 4 groups independently selected from —$OR^f$, —CN, halo, —$C_{1-6}$ alkylOR$^f$, —$C_{1-6}$ cyanoalkyl, —$C_{1-6}$haloalkyl, —$C_{3-8}$cycloalkyl, —$C_{1-3}$ alkylC$_{3-8}$cycloalkyl, —C(O)R$^f$, —$C_{1-6}$ alkylC(O)R$^f$, —C(O)OR$^f$, —$C_{1-6}$ alkylC(O)OR$^f$, —NR$^f$R$^g$, —$C_{1-6}$ alkylNR$^f$R$^g$, —C(O)NR$^f$R$^g$, —$C_{1-6}$ alkylC(O)NR$^f$R$^g$, —$SO_2R^f$, —$C_{1-6}$ alkylSO$_2$R$^f$, —$SO_2NR^fR^g$, —$C_{1-6}$ alkylSO$_2$NR$^f$R$^g$, —C(O)NR$^f$SO$_2$R$^g$ and —NR$^f$C(O)R$^g$;

$R^c$ is independently selected from H, OH, —$C_{1-6}$alkyl, —$C_{3-8}$ cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl;

$R^d$ is independently selected from H, —$C_{1-6}$alkyl, —$C_3$-$C_8$cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl;

$R^e$ is independently selected from H, —$C_{1-6}$alkyl, —$OC_{1-6}$alkyl, —$C_{3-8}$cycloalkyl, aryl, heteroaryl, heterocyclyl, —$OC_{3-8}$cycloalkyl, —Oaryl, —Oheteroaryl, —Oheterocyclyl, —$C_{1-3}$ alkyl$C_{3-8}$cycloalkyl, —$C_{1-6}$alkylaryl, —$C_{1-6}$alkylheteroaryl, —$NR^fR^g$, —$C_{1-6}$alkyl$NR^fR^g$, —$C(O)NR^fR^g$, —$C_{1-6}$alkylC(O)$NR^fR^g$, —$NHSO_2R^f$, —$C_{1-6}$alkyl$SO_2R^f$, and —$C_{1-6}$alkyl$SO_2NR^fR^g$;

$R^f$ is independently selected from H, —$C_{1-6}$alkyl, —$C_{3-8}$ cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl; and $R^g$ is independently selected from H, —$C_{1-6}$alkyl, —$C_{3-8}$ cycloalkyl, aryl, heteroaryl, heterocyclyl, —$C_{1-3}$ alkyl$C_{3-8}$ cycloalkyl, —$C_{1-6}$ alkylaryl, —$C_{1-6}$ alkylheteroaryl, and —$C_{1-6}$alkylheterocyclyl;

or a pharmaceutically acceptable salt, stereoisomer, mixture of stereoisomers, or tautomer thereof.

In one embodiment of formula (IVa), neither of $R^E$ or $R^W$ is an optionally substituted fused 5,6-aromatic or 5,6-heteromatic ring.

In one embodiment, the compound is represented by formulas (IVb):

(IVb)

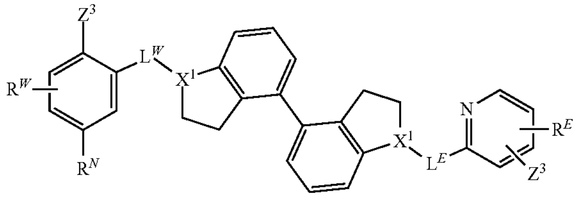

wherein each $X^1$ is independently N or CH;

each $Z^1$ is independently halo, —$OR^a$, —$C_{1-6}$ alkyl, —$OC_{1-6}$alkyl, —$C_{1-6}$ haloalkyl, or —$C_{3-8}$ cycloalkyl;

each $Z^3$ is independently halo, —$OR^a$, —$N_3$, —$NO_2$, —CN, —$NR^1R^2$, —$SO_2R^a$, —$SO_2N^aR^b$, —$NR^aSO_2R^a$, —$NR^aC(O)R^a$, —$C(O)R^a$, —$C(O)OR^a$, —$C(O)NR^aR^b$, —$NR^aC(O)OR^a$, —$NR^aC(O)NR^1R^2$, —$OC(O)NR^aR^b$, —$NR^aSO_2NR^aR^b$, —C(O) $NR^aSO_2NR^aR^b$, —$C_{1-6}$ alkyl, —$C_{2-6}$ alkenyl, —$C_{2-6}$ alkynyl, —$OC_{1-6}$alkyl, —$C_{3-8}$ cycloalkyl, —$C_{1-6}$ alkyl$C_{3-8}$ cycloalkyl, aryl, heteroaryl, heterocyclyl, and $R^N$;

wherein the alkyl, alkenyl, alkynyl, $C_{3-8}$ cycloalkyl, aryl, heteroaryl, or heterocyclyl group is optionally substituted with 1 to 4 groups independently selected from oxo, —$NO_2$, —$N_3$, —$OR^a$, halo, cyano, —$NR^aR^b$, —$C(O)R^a$, —$C(O)OR^a$, —$OC_{1-6}$alkyCN, —$C(O)NR^aR^b$, $NR^aC(O)R^a$, —$NR^aC(O)OR^a$, —$SO_2R^a$, —$NR^aSO_2R$, —$SO_2NR^aR^b$, —$NR^aSO_2NR^aR^b$, —$C(O)NR^aSO_2NR^aR^b$ and —$C_{3-8}$ cycloalkyl; and wherein the heteroaryl or heterocyclic group may be oxidized on a nitrogen atom to form an N-oxide or oxidized on a sulfur atom to form a sulfoxide or sulfone;

$R^N$ is independently —$C_{1-6}$ alkyl$NR^1R^2$, —$OC_{1-6}$ alky$NR^1R^2$, —$C_{1-6}$ alkyl$OC_{1-6}$ alkyl$NR^1R^2$, —$NR^aC_{1-6}$ alkyl$NR^1R^2$, —$C_{1-6}$ alkylC(O)$NR^1R^2$, —$OC_{1-6}$ alkylC(O)$NR^1R^2$, —$OC_{1-6}$ alkylC(O)$OR^1$, —$SC_{1-6}$alkyl$NR^1R^2$, —$C_{1-6}$alkyl$OR^a$, or

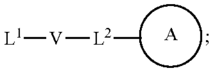;

wherein: $L^1$ is independently a bond, O, $NR^a$, S, SO, or $SO_2$;

V is independently selected from a bond, $C_{1-6}$alkyl, $C_{2-6}$alkenyl, and $C_{2-6}$alkynyl;

wherein each alkyl, alkenyl, or alkynyl is optionally independently substituted with $OR^a$, halo, cyano, —$NR^aR^b$, or —$C_{3-8}$cycloalkyl;

$L^2$ is independently a bond, O, $NR^a$, S, SO, or $SO_2$;

ring A is independently cycloalkyl, aryl, heteroaryl, or heterocyclyl;

wherein each cycloalkyl, aryl, heteroaryl, or heterocyclyl is optionally substituted with 1 to 4 groups independently selected from oxo, —$NO_2$, —$N_3$, —$OR^a$, halo, cyano, —$C_{1-6}$ alkyl, —$C_{1-6}$ haloalkyl, —$C_{2-6}$alkenyl, —$C_{2-6}$ alkynyl, —$OC_{1-6}$ haloalkyl, $NR^aR^b$, —$C(O)R^a$, —$C(O)OR^a$, —$OC_{1-6}$ alkylCN, —$C(O)NR^aR^b$, —$NR^aC(O)R^a$, —$NR^aC(O)OR^a$, —$NR^aC(O)$ $OR^a$, —$C(O)N(R^a)OR^b$, —$SO_2R^a$, —$SO_2NR^aR^b$, —$NR^aSO_2R^b$, —$NR^aSO_2NR^aR^b$, —$C(O)NR^aSO_2NR^aR^b$, $C_{3-8}$cycloalkyl, and $C_{1-6}$alkyl$C_{3-8}$ cycloalkyl; and wherein the alkyl, alkenyl, or alkynyl group is optionally independently substituted with —$OR^a$, halo, cyano, —$NR^aR^b$, or —$C_{3-8}$ cycloalkyl $L^E$ and $L^W$ are each independently a bond, —O—, —S—, —SO—, —$SO_2$—, —$(CR^3R^4)_m$—, —$(CR^3R^4)_mO(CR^3R^4)_m$—, —$(CR^3R^4)_mS(CR^3R^4)_m$—, —$(CR^3R^4)_mNR^3(CR^3R^4)_m$—, —C(O)—, —$(CR^3R^4)_mC(O)(CR^3R^4)_m$—, —$(CR^3R^4)_mC(O)NR^3(CR^3R^4)_m$—, —$(CR^3R^4)_mNR^3C(O)(CR^3R^4)_m$—, $C_{2-6}$ alkenylene, $C_{2-6}$ alkynylene,

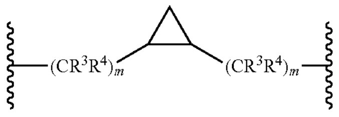

or

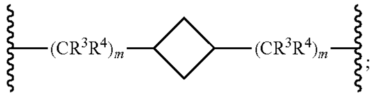;

each m is independently 0, 1, 2, 3 or 4;

$R^E$ and $R^W$ are each independently —$NR^1R^2$, —$C_{1-6}$ alky$NR^1R^2$, —$OC_{1-6}$ alkyl$NR^1R^2$, —$C_{1-6}$ alkylO $C_{1-6}$alkyl$NR^1R^2$, —$NR^aC_{1-6}$ alkyl$NR^1R^2$, —$C_{1-6}$ alkyl$N^+R^1R^2R^3$, —$SC_{1-6}$ alkyl$NR^1R^2$, —$C(O)NR^1R^2$, —$SO_2R^a$, —$(CH_2)_uSO_2NR^1R^2$, —$(CH_2)_uNR^aSO_2NR^aR^b$, —$SO_2NR^aC_{1-6}$alky$NR^1R^2$, —$NR^aSO_2C_{1-6}$ alkyl$NR^1R^2$, —$(CH_2)_uC(O)NR^aSO_2NR^aR^b$, —$(CH_2)_uN^+R^1R^2O^-$, —$(CH_2)_uP^+R^bR^cR^d$, —$(CH_2)_uP^+R^cR^dO^-$, —$(CH_2)_uP^+O[NR^aR^b]$ $[NR^cR^d]$, $—(CH_2)_uNR^cP(O)(OR^c)_2$, $—(CH_2)_uCH_2OP(O)(OR^c)(OR^d)$, $—(CH_2)_uOP(O)(OR^c)(OR^d)$, $—(CH_2)_uOP(O)NR^aR^b)(OR^a)$, or

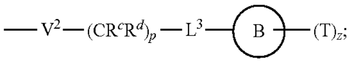

wherein:

$V^2$ is independently a bond, O, $NR^a$, S, SO, $SO_2$, $C(O)NR^a$, $NR^aC(O)$, $SO_2NR^1R^2$, or $NR^aSO_2$;

$L^3$ is independently a bond, O, $NR^a$, S, SO, $SO_2$, $C(O)NR^a$, $NR^aC(O)$, $SO_2NR^1R^2$, or $NR^aSO_2$;

ring B is cycloalkyl, aryl, heteroaryl, or heterocyclyl; T is independently H, $OR^a$, $(CH_2)_qNR^1R^2$, $(CH_2)_qNR^aC(O)R^e$, or $(CH_2)_qC(O)R^e$;

p is independently 0, 1, 2, 3, 4, or 5;

q is independently 0, 1, 2, 3, 4, or 5;

u is 0, 1, 2, 3, or 4;

z is 0, 1, 2, or 3; and wherein the alkyl, cycloalkyl, aryl, heteroaryl, or heterocyclyl of $R^E$ or $R^W$ is optionally substituted with 1 to 3 substituents independently selected from the group consisting of $NR^aR^b$, halo, cyano, oxo, $OR^a$, $—C_{1-6}$alkyl, $—C_{1-6}$haloalkyl, $—C_{1-6}$cyanoalkyl, $—C_{1-6}alkyNR^aR^b$, $—C_{1-6}$ alkylOH, $—C_{3-8}$ cycloalkyl, and $—C_{1-3}$ alkyl$C_{3-8}$cycloalkyl;

provided that at least one of $V^2$, $L^3$, ring B and T contains a nitrogen atom;

$R^1$ is independently selected from H, $—C_{1-8}$ alkyl, $—C_{2-6}$ alkenyl, $—C_{2-6}$ alkynyl, $—C_{3-6}$ cycloalkyl, aryl, heteroaryl, heterocyclyl, $—C_{1-6}$alkylaryl, $—C_{1-6}$alkylheteroaryl, $—C_{1-6}$alkylheterocyclyl, $—C_{1-6}$ alkylC(O)$OR^a$, $—C_{2-6}$ alkenylC(O)$OR^a$, $—SO_2R^a$, $—SO_2NR^aR^b$, $—C(O)NR^aSO_2R^a$, and $C_{1-6}$alkyl $C_{3-8}$cycloalkyl;

wherein each alkyl, alkenyl, cycloalkyl, aryl, heteroaryl, or heterocyclyl is optionally substituted with 1 to 4 groups independently selected from $—OR^a$, —CN, halo, $C_{1-6}$alkyl, $—C_{1-6}$alkyl$OR^a$, $—C_{1-6}$cyanoalkyl, $—C_{1-6}$haloalkyl, $C_{3-8}$cycloalkyl, $—C_{1-3}$alkyl$C_{3-8}$cycloalkyl, $—C(O)R^a$, $—C_{1-6}$ alkylC(O)$R^a$, $—C(O)OR^a$, $—C_{1-6}$ alkylC(O)$OR^a$, $—NR^aR^b$, $—OC(O)NR^aR^b$, $NR^aC(O)OR^b$, $—C_{1-6}$alkyl$NR^aR^b$, $—C(O)NR^aR^b$, $—C_{1-6}$alkylC(O)$NR^aR^b$, $—SO_2R^a$, $—C_{1-6}$alkyl$SO_2R^a$, $—SO_2NR^aR^b$, $—C_{1-6}$ alkyl$SO_2NR^aR^b$, $—C(O)NR^aSO_2R^b$, $—C_{1-6}$ alkylC(O)$NR^aSO_2R^b$, $—NR^aC(O)R^b$, and $—C_{1-6}$alkyl$NR^aC(O)R^b$;

$R^2$ is independently selected from H, $—C_{1-6}$alkyl, $—C_{2-6}$ alkenyl, $—C_{2-6}$ alkynyl, $—C_{3-6}$ cycloalkyl, aryl, heteroaryl, heterocyclyl, $—C_{1-6}$alkylaryl, $—C_{1-6}$alkylheteroaryl, $—C_{1-6}$ alkylheterocyclyl, $—C_{2-6}$alkyl-$OR^a$, $—C_{1-6}$ alkylC(O)$OR^a$, and $—C_{2-6}$ alkenylC(O)$OR^a$;

wherein each alkyl, alkenyl, alkynyl, cycloalkyl, aryl, heteroaryl, or heterocyclyl is optionally substituted with 1 to 4 groups independently selected from $—OR^a$, —CN, halo, $C_{1-6}$alkyl, $—C_{1-6}$alkyl$OR^a$, $—C_{1-6}$cyanoalkyl, $—C_{1-6}$haloalkyl, $—C_{3-8}$cycloalkyl, $—C_{1-3}$alkyl$C_{3-8}$cycloalkyl, $—C(O)R^a$, $—C_{1-6}$ alkylC(O)$R^a$, $—C(O)OR^a$, $—C_{1-6}$ alkylC(O)$OR^a$, $—NR^aR^b$, $—C_{1-6}$ alkyl$NR^aR^b$, $—C(O)NR^aR^b$, $C_{1-6}$alkylC(O)$NR^aR^b$, $—SO_2R^a$, $—C_{1-6}$alkyl$SO_2R^a$, $—SO_2NR^aR^b$, $—C_{1-6}$alkyl$SO_2NR^aR^b$, $—C(O)NR^aSO_2R^b$ and $—NR^aC(O)R^b$;

or $R^1$ and $R^2$ combine to form a heterocyclyl group optionally containing 1, 2, or 3 additional heteroatoms independently selected from oxygen, sulfur and nitrogen, and optionally substituted with 1 to 3 groups independently selected from oxo, $—C_{1-6}$alkyl, $—C_{3-8}$ cycloalkyl, $—C_{2-6}$ alkenyl, $—C_{2-6}$ alkynyl, $—OR^a$, $—C(O)OR^a$, $—C_{1-6}$ cyanoalkyl, $—C_{1-6}$ alkyl$OR^a$, $—C_{1-6}$haloalkyl, $—C_{1-3}$ alkyl$C_{3-8}$cycloalkyl, $—C(O)R^a$, $—C_{1-6}$ alkylC(O)$R^a$, $—C_{1-6}$ alkylC(O)$OR^a$, $—NR^aR^b$, $—C_{1-6}$alkyl$NR^aR^b$, $—C(O)NR^aR^b$, $—C_{1-6}$ alkylC(O)$NR^aR^b$, $—SO_2R^a$, $—C_{1-6}$ alkyl$SO_2R^a$, $—SO_2NR^aR^b$, and $C_{1-6}$ alkyl$SO_2NR^aR^b$;

$R^3$ is independently H, $—C_{1-6}$ alkyl, $—C_{2-6}$ alkenyl, $—C_{3-6}$ cycloalkyl, aryl, heteroaryl, heterocyclyl, $—C_{1-6}$alkylaryl, $—C_{1-6}$alkylheteroaryl, $—C_{1-6}$ alkylheterocyclyl, $—C_{2-6}$alkyl-$OR^a$, $—C_{1-6}$alkylC(O)$OR^a$, or $—C_{2-6}$ alkenylC(O)$OR^a$;

$R^4$ is independently H, $—C_{1-6}$ alkyl, $—C_{2-6}$ alkenyl, $—C_{3-6}$ cycloalkyl, aryl, heteroaryl, heterocyclyl, $—C_{1-6}$ alkylaryl, $—C_{1-6}$ alkylheteroaryl, $—C_{1-6}$ alkylheterocyclyl, $—C_{2-6}$alkyl-$OR^a$, $—C_{1-6}$alkylC(O)$OR^a$, or $—C_{2-6}$ alkenylC(O)$OR^a$;

$R^a$ is independently selected from H, $—C_{1-6}$ alkyl, $—C_{3-8}$ cycloalkyl, aryl, heteroaryl, heterocyclyl, $—C_{1-3}$ alkyl$C_{3-8}$cycloalkyl, $—C_{1-6}$ alkylaryl, $—C_{1-6}$ alkylheteroaryl, and $—C_{1-6}$alkylheterocyclyl;

$R^b$ is independently selected from H, $—C_{1-6}$ alkyl, $—C_{3-8}$ cycloalkyl, aryl, heteroaryl, heterocyclyl, $—C_{1-3}$ alkyl$C_{3-8}$cycloalkyl, $—C_{1-6}$ alkylaryl, $—C_{1-6}$ alkylheteroaryl, and $—C_{1-6}$ alkylheterocyclyl;

or $R^a$ and $R^b$ may combine together to form a ring consisting of 3-8 ring atoms that are C, N, O, or S; wherein the ring is optionally substituted with 1 to 4 groups independently selected from $—OR^f$, —CN, halo, $—C_{1-6}$ alkyl$OR^f$, $—C_{1-6}$ cyanoalkyl, $—C_{1-6}$haloalkyl, $—C_{3-8}$ cycloalkyl, $—C_{1-3}$ alkyl$C_{3-8}$cycloalkyl, $—C(O)R^f$, $—C_{1-6}$ alkylC(O)$R^f$, $—C(O)OR^f$, $—C_{1-6}$ alkylC(O)$OR^f$, $—NR^fR^g$, $—C_{1-6}$ alkyl$NR^fR^g$, $—C(O)NR^fR^g$, $—C_{1-6}$ alkylC(O)$NR^fR^g$, $—SO_2R^f$, $—C_{1-6}$ alkyl$SO_2R$, $—SO_2NR^fR^g$, $—C_{1-6}$ alkyl$SO_2NR^f$Ry, $—C(O)NR^fSO_2R^g$ and $—NR^fC(O)R^g$;

$R^c$ is independently selected from H, OH, $—C_{1-6}$ alkyl, $—C_{3-8}$ cycloalkyl, aryl, heteroaryl, heterocyclyl, $—C_{1-3}$ alkyl$C_{3-8}$cycloalkyl, $—C_{1-6}$ alkylaryl, $—C_{1-6}$ alkylheteroaryl, and $—C_{1-6}$ alkylheterocyclyl;

$R^d$ is independently selected from H, $—C_{1-6}$ alkyl, $—C_3$-$C_8$cycloalkyl, aryl, heteroaryl, heterocyclyl, $—C_{1-3}$ alkyl$C_{3-8}$cycloalkyl, $—C_{1-6}$ alkylaryl, $—C_{1-6}$ alkylheteroaryl, and $—C_{1-6}$ alkylheterocyclyl;

$R^e$ is independently selected from H, $—C_{1-6}$ alkyl, $—OC_{1-6}$alkyl, $—C_{3-8}$ cycloalkyl, aryl, heteroaryl, heterocyclyl, $—OC_{3-8}$ cycloalkyl, —Oaryl, —Oheteroaryl, —Oheterocyclyl, $—C_{1-3}$ alkyl$C_{3-8}$cycloalkyl, $—C_{1-6}$ alkylaryl, $—C_{1-6}$alkylheteroaryl, $—NR^fR^g$, $—C_{1-6}$ alkyl$NR^fR^g$, $—C(O)NR^fR^g$, $—C_{1-6}$alkylC(O)$NR^fR^g$, $—NHSO_2R^f$, $—C_{1-6}$alkyl$SO_2R^f$, and $—C_{1-6}$alkyl$SO_2NR^fR^g$;

$R^f$ is independently selected from H, $—C_{1-6}$ alkyl, $—C_{3-8}$ cycloalkyl, aryl, heteroaryl, heterocyclyl, $—C_{1-3}$ alkyl$C_{3-8}$cycloalkyl, $—C_{1-6}$ alkylaryl, $—C_{1-6}$ alkylheteroaryl, and $—C_{1-6}$ alkylheterocyclyl; and $R^g$ is independently selected from H, $—C_{1-6}$ alkyl, $—C_{3-8}$ cycloalkyl, aryl, heteroaryl, heterocyclyl, $—C_{1-3}$ alkyl$C_{3-8}$cycloalkyl, $—C_{1-6}$ alkylaryl, $—C_{1-6}$ alkylheteroaryl, and $—C_{1-6}$ alkylheterocyclyl;

or a pharmaceutically acceptable salt, stereoisomer, mixture of stereoisomers, or tautomer thereof.

In one embodiment of formula (IVb), neither of $R^E$ or $R^W$ is an optionally substituted fused 5,6-aromatic or 5,6-heteromatic ring.

In one embodiment, the compound is represented by formula (IVc):

(IVc)

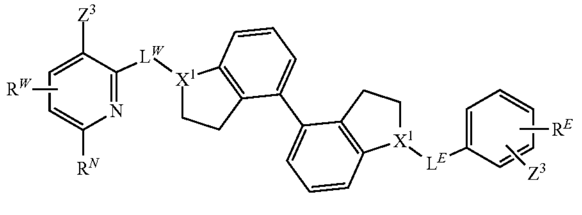

wherein each $X^1$ is independently N or CH;

each $Z^1$ is independently halo, —$OR^a$, —$C_{1-6}$ alkyl, —$OC_{1-6}$ alkyl, —$C_{1-6}$ haloalkyl, or —$C_{3-8}$ cycloalkyl;

each $Z^3$ is independently halo, —$OR^a$, —$N_3$, —$NO_2$, —CN, —$NR^1R^2$, —$SO_2R^a$, —$SO_2NR^aR^b$, —$NR^aSO_2R^a$, —$NR^aC(O)R^a$, —$C(O)R^a$, —$C(O)OR^a$, —$C(O)NR^aR^b$, —$NR^aC(O)OR^a$, —$NR^aC(O)NR^1R^2$, —$OC(O)NR^aR^b$, —$NR^aSO_2NR^aR^b$, —$C(O)NR^aSO_2NR^aR^b$, —$C_{1-6}$ alkyl, —$C_{2-6}$ alkenyl, —$C_{2-6}$ alkynyl, —$OC_{1-6}$ alkyl, —$C_{3-8}$ cycloalkyl, —$C_{1-6}$ alkyl$C_{3-8}$ cycloalkyl, aryl, heteroaryl, heterocyclyl, and $R^N$;

wherein the alkyl, alkenyl, alkynyl, $C_{3-8}$ cycloalkyl, aryl, heteroaryl, or heterocyclyl group is optionally substituted with 1 to 4 groups independently selected from oxo, —$NO_2$, —$N_3$, —$OR^a$, halo, cyano, —$NR^aR^b$, —$C(O)R^a$, —$C(O)OR^a$, —$OC_{1-6}$alkyCN, —$C(O)NR^aR^b$, $NR^aC(O)R^a$, —$NR^aC(O)OR^a$, —$SO_2R^a$, —$NR^aSO_2R$, —$SO_2NR^aR^b$, —$NR^aSO_2NR^aR^b$, —$C(O)NR^aSO_2NR^aR^b$ and —$C_{3-8}$ cycloalkyl; and wherein the heteroaryl or heterocyclic group may be oxidized on a nitrogen atom to form an N-oxide or oxidized on a sulfur atom to form a sulfoxide or sulfone;

$R^N$ is independently —$C_{1-6}$ alkyl$NR^1R^2$, —$OC_{1-6}$ alky$NR^1R^2$, —$C_{1-6}$ alkyl$OC_{1-6}$ alkyl$NR^1R^2$, —$NR^aC_{1-6}$ alkyl$NR^1R^2$, —$C_{1-6}$ alkyl$C(O)NR^1R^2$, —$OC_{1-6}$ alkyl$C(O)NR^1R^2$, —$OC_{1-6}$ alkyl$C(O)OR^1$, —$SC_{1-6}$alkyl$NR^1R^2$, $C_{1-6}$alkyl$OR^a$, or

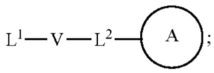;

wherein: $L^1$ is independently a bond, O, $NR^a$, S, SO, or $SO_2$;

V is independently selected from a bond, $C_{1-6}$alkyl, $C_{2-6}$alkenyl, and $C_{2-6}$alkynyl;

wherein each alkyl, alkenyl, or alkynyl is optionally independently substituted with $OR^a$, halo, cyano, —$NR^aR^b$, or —$C_{3-8}$ cycloalkyl;

$L^2$ is independently a bond, O, $NR^a$, S, SO, or $SO_2$;

ring A is independently cycloalkyl, aryl, heteroaryl, or heterocyclyl;

wherein each cycloalkyl, aryl, heteroaryl, or heterocyclyl is optionally substituted with 1 to 4 groups independently selected from oxo, —$NO_2$, —$N_3$, —$OR^a$, halo, cyano, —$C_{1-6}$ alkyl, —$C_{1-6}$ haloalkyl, —$C_{2-6}$alkenyl, —$C_{2-6}$ alkynyl, —$OC_{1-6}$ haloalkyl, $NR^aR^b$, —$C(O)R^a$, —$C(O)OR^a$, —$OC_{1-6}$ alkylCN, —$C(O)NR^aR^b$, —$NR^aC(O)R^a$, —$NR^aC(O)OR^a$, —$NR^aC(O)OR^a$, —$C(O)N(R^a)OR^b$, —$SO_2R^a$, —$SO_2NR^aR^b$, —$NR^aSO_2R^b$, —$NR^aSO_2NR^aR^b$, —$C(O)NR^aSO_2NR^aR^b$, $C_{3-8}$cycloalkyl, and $C_{1-6}$alkyl$C_{3-8}$ cycloalkyl; and wherein the alkyl, alkenyl, or alkynyl group is optionally independently substituted with —$OR^a$, halo, cyano, —$NR^aR^b$, or —$C_{3-8}$ cycloalkyl;

$L^E$ and $L^W$ are each independently a bond, —O—, —S—, —SO—, —$SO_2$—, —$(CR^3R^4)_m$—, —$(CR^3R^4)_mO(CR^3R^4)_m$—, —$(CR^3R^4)_mS(CR^3R^4)_m$—, —$(CR^3R^4)_mNR^3(CR^3R^4)_m$—, —C(O)—, —$(CR^3R^4)_mC(O)(CR^3R^4)_m$—, —$(CR^3R^4)_mC(O)NR^3(CR^3R^4)_m$—, —$(CR^3R^4)_mNR^3C(O)(CR^3R^4)_m$—, $C_{2-6}$ alkenylene, $C_{2-6}$ alkynylene,

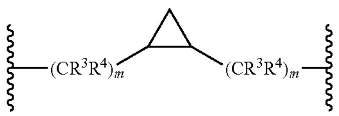

or

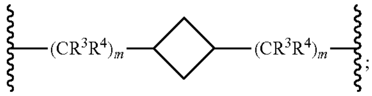;

each m is independently 0, 1, 2, 3 or 4;

$R^E$ and $R^W$ are each independently —$NR^1R^2$, —$C_{1-6}$ alky$NR^1R^2$, —$OC_{1-6}$ alkyl$NR^1R^2$, —$C_{1-6}$ alkyl$OC_{1-6}$alkyl$NR^1R^2$, —$NR^aC_{1-6}$ alkyl$NR^1R^2$, —$C_{1-6}$ alkyl$N^+R^1R^2R^3$, —$SC_{1-6}$ alkyl$NR^1R^2$, —$C(O)NR^1R^2$, —$SO_2R^a$, —$(CH_2)_uSO_2NR^1R^2$, —$(CH_2)_uNR^aSO_2NR^aR^b$, —$SO_2NR^aC_{1-6}$alky$NR^1R^2$, —$NR^aSO_2C_{1-6}$ alkyl$NR^1R^2$, —$(CH_2)_uC(O)NR^aSO_2NR^aR^b$, —$(CH_2)_uN^+R^1R^2O^-$, —$(CH_2)_uP^+R^bR^cR^d$, —$(CH_2)_uP^+R^cR^dO^-$, —$(CH_2)_uP^+O[NR^aR^b][NR^cR^d]$, —$(CH_2)_uNR^cP(O)(OR^c)_2$, —$(CH_2)_uCH_2OP(O)(OR^c)(OR^d)$, —$(CH_2)_uOP(O)(OR^c)(OR^d)$, —$(CH_2)_uOP(O)NR^aR^b)(OR^a)$, or

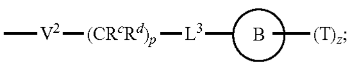;

wherein:

$V^2$ is independently a bond, O, $NR^a$, S, SO, $SO_2$, $C(O)NR^a$, $NR^aC(O)$, $SO_2NR^1R^2$, or $NR^aSO_2$;

$L^3$ is independently a bond, O, $NR^a$, S, SO, $SO_2$, $C(O)NR^a$, $NR^aC(O)$, $SO_2NR^1R^2$, or $NR^aSO_2$;

ring B is cycloalkyl, aryl, heteroaryl, or heterocyclyl; T is independently H, $OR^a$, $(CH_2)NR^1R^2$ $(CH_2)_qNR^aC(O)R$, or $(CH_2)_qC(O)R$;

p is independently 0, 1, 2, 3, 4, or 5;

q is independently 0, 1, 2, 3, 4, or 5;

u is 0, 1, 2, 3, or 4;

z is 0, 1, 2, or 3; and wherein the alkyl, cycloalkyl, aryl, heteroaryl, or heterocyclyl of $R^E$ or $R^W$ is optionally substituted with 1 to 3 substituents independently selected from the group consisting of $NR^aR^b$, halo, cyano, oxo, $OR^a$, —$C_{1-6}$alkyl, —$C_{1-6}$ haloalkyl, —$C_{1-6}$ cyanoalkyl, —$C_{1-6}$alkyN$R^aR^b$, —$C_{1-6}$ alkylOH, —$C_{3-8}$ cycloalkyl, and —$C_{1-3}$ alkyl$C_{3-8}$cycloalkyl;

provided that at least one of $V^2$, $L^3$, ring B and T contains a nitrogen atom;

$R^1$ is independently selected from H, —$C_{1-8}$ alkyl, —$C_{2-6}$ alkenyl, —$C_{2-6}$ alkynyl, —$C_{3-6}$ cycloalkyl, aryl, heteroaryl, heterocyclyl, —$C_{1-6}$alkylaryl, —$C_{1-6}$alkylheteroaryl, —$C_{1-6}$alkylheterocyclyl, —$C_{1-6}$ alkylC(O)O$R^a$, —$C_{2-6}$ alkenylC(O)O$R^a$, —$SO_2R^a$, —$SO_2NR^aR^b$, —C(O)N$R^a$$SO_2R^a$, and $C_{1-6}$ alkyl $C_{3-8}$cycloalkyl;

wherein each alkyl, alkenyl, cycloalkyl, aryl, heteroaryl, or heterocyclyl is optionally substituted with 1 to 4 groups independently selected from —O$R^a$, —CN, halo, $C_{1-6}$alkyl, —$C_{1-6}$alkylO$R^a$, —$C_{1-6}$cyanoalkyl, —$C_{1-6}$haloalkyl, $C_{3-8}$cycloalkyl, —$C_{1-3}$alkyl$C_{3-8}$cycloalkyl, —C(O)$R^a$, —$C_{1-6}$ alkylC(O)$R^a$, —C(O)O$R^a$, —$C_{1-6}$ alkylC(O)O$R^a$, —N$R^aR^b$, —OC(O)N$R^aR^b$, N$R^a$C(O)O$R^b$, —$C_{1-6}$alkylN$R^aR^b$, —C(O)N$R^aR^b$, —$C_{1-6}$alkylC(O)N$R^aR^b$, —$SO_2R^a$, —$C_{1-6}$alkyl$SO_2R^a$, —$SO_2NR^aR^b$, —$C_{1-6}$ alkyl$SO_2NR^aR^b$, —C(O)N$R^a$$SO_2R^b$, —$C_{1-6}$ alkylC(O)N$R^a$$SO_2R^b$, —N$R^a$C(O)$R^b$, and —$C_{1-6}$alkylN$R^a$C(O)$R^b$;

$R^2$ is independently selected from H, —$C_{1-6}$alkyl, —$C_{2-6}$ alkenyl, —$C_{2-6}$ alkynyl, —$C_{3-6}$ cycloalkyl, aryl, heteroaryl, heterocyclyl, —$C_{1-6}$alkylaryl, —$C_{1-6}$alkylheteroaryl, —$C_{1-6}$ alkylheterocyclyl, —$C_{2-6}$alkyl-O$R^a$, —$C_{1-6}$ alkylC(O)O$R^a$, and —$C_{2-6}$ alkenylC(O)O$R^a$;

wherein each alkyl, alkenyl, alkynyl, cycloalkyl, aryl, heteroaryl, or heterocyclyl is optionally substituted with 1 to 4 groups independently selected from —O$R^a$, —CN, halo, $C_{1-6}$alkyl, —$C_{1-6}$alkylO$R^a$, —$C_{1-6}$cyanoalkyl, —$C_{1-6}$haloalkyl, —$C_{3-8}$cycloalkyl, —$C_{1-3}$alkyl$C_{3-8}$cycloalkyl, —C(O)$R^a$, —$C_{1-6}$ alkylC(O)$R^a$, —C(O)O$R^a$, —$C_{1-6}$ alkylC(O)O$R^a$, —N$R^aR^b$, —$C_{1-6}$ alkylN$R^aR^b$, —C(O)N$R^aR^b$, $C_{1-6}$alkylC(O)N$R^aR^b$, —$SO_2R^a$, —$C_{1-6}$alkyl$SO_2R^a$, —$SO_2NR^aR^b$, —$C_{1-6}$alkyl$SO_2NR^aR^b$, —C(O)N$R^a$$SO_2R^b$ and —N$R^a$C(O)$R^b$;

or $R^1$ and $R^2$ combine to form a heterocyclyl group optionally containing 1, 2, or 3 additional heteroatoms independently selected from oxygen, sulfur and nitrogen, and optionally substituted with 1 to 3 groups independently selected from oxo, —$C_{1-6}$alkyl, —$C_{3-8}$ cycloalkyl, —$C_{2-6}$ alkenyl, —$C_{2-6}$ alkynyl, —O$R^a$, —C(O)O$R^a$, —$C_{1-6}$cyanoalkyl, —$C_{1-6}$ alkylO$R^a$, —$C_{1-6}$haloalkyl, —$C_{1-3}$ alkyl$C_{3-8}$cycloalkyl, —C(O)$R^a$, $C_{1-6}$alkylC(O)$R^a$, —$C_{1-6}$alkylC(O)O$R^a$, —N$R^aR^b$, —$C_{1-6}$alkyN$R^aR^b$, —C(O)N$R^aR^b$, —$C_{1-6}$alkylC(O)N$R^aR^b$, —$SO_2R^a$, —$C_{1-6}$ alkyl$SO_2R^a$, —$SO_2NR^aR^b$, and $C_{1-6}$ alkyl$SO_2NR^aR^b$;

$R^3$ is independently H, —$C_{1-6}$alkyl, —$C_{2-6}$ alkenyl, —$C_{3-6}$ cycloalkyl, aryl, heteroaryl, heterocyclyl, —$C_{1-6}$alkylaryl, —$C_{1-6}$alkylheteroaryl, —$C_{1-6}$ alkylheterocyclyl, —$C_{2-6}$alkyl-O$R^a$, —$C_{1-6}$alkylC(O)O$R^a$, or —$C_{2-6}$ alkenylC(O)O$R^a$;

$R^4$ is independently H, —$C_{1-6}$alkyl, —$C_{2-6}$ alkenyl, —$C_{3-6}$ cycloalkyl, aryl, heteroaryl, heterocyclyl, —$C_{1-6}$alkylaryl, —$C_{1-6}$alkylheteroaryl, —$C_{1-6}$ alkylheterocyclyl, —$C_{2-6}$alkyl-O$R^a$, —$C_{1-6}$alkylC(O)O$R^a$, or —$C_{2-6}$ alkenylC(O)O$R^a$;

$R^a$ is independently selected from H, —$C_{1-6}$alkyl, —$C_{3-8}$ cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl;

$R^b$ is independently selected from H, —$C_{1-6}$alkyl, —$C_{3-8}$cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$ alkylheterocyclyl;

or $R^a$ and $R^b$ may combine together to form a ring consisting of 3-8 ring atoms that are C, N, O, or S; wherein the ring is optionally substituted with 1 to 4 groups independently selected from —O$R^f$, —CN, halo, —$C_{1-6}$ alkylO$R^f$, —$C_{1-6}$ cyanoalkyl, —$C_{1-6}$haloalkyl, —$C_{3-8}$ cycloalkyl, —$C_{1-3}$ alkyl$C_{3-8}$cycloalkyl, —C(O)$R^f$, —$C_{1-6}$ alkylC(O)$R^f$, —C(O)O$R^f$, —$C_{1-6}$ alkylC(O)O$R^f$, —N$R^fR^g$, —$C_{1-6}$ alkylN$R^fR^g$, —C(O)N$R^fR^g$, —$C_{1-6}$ alkylC(O)N$R^fR^g$, —$SO_2R^f$, —$C_{1-6}$ alkyl$SO_2$ N$R^fR^g$, —$C_{1-6}$ alkyl$SO_2NR^fR^g$, —C(O)N$R^f$$SO_2R^g$ and —N$R^f$C(O)$R^g$;

$R^c$ is independently selected from H, OH, —$C_{1-6}$alkyl, —$C_{3-8}$ cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl;

$R^d$ is independently selected from H, —$C_{1-6}$alkyl, —$C_3$-$C_8$cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl;

$R^e$ is independently selected from H, —$C_{1-6}$alkyl, —O$C_{1-6}$alkyl, —$C_{3-8}$ cycloalkyl, aryl, heteroaryl, heterocyclyl, —O$C_{3-8}$cycloalkyl, —Oaryl, —Oheteroaryl, —Oheterocyclyl, —$C_{1-3}$ alkyl$C_{3-8}$cycloalkyl, —$C_{1-6}$alkylaryl, —$C_{1-6}$alkylheteroaryl, —N$R^fR^g$, —$C_{1-6}$alkylN$R^fR^g$, —C(O)N$R^fR^g$, —$C_{1-6}$alkylC(O)N$R^fR^g$, —NH$SO_2R^f$, —$C_{1-6}$alkyl$SO_2R^f$, and —$C_{1-6}$alkyl$SO_2NR^fR^g$;

$R^f$ is independently selected from H, —$C_{1-6}$alkyl, —$C_{3-8}$ cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl; and $R^g$ is independently selected from H, —$C_{1-6}$alkyl, —$C_{3-8}$ cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl;

or a pharmaceutically acceptable salt, stereoisomer, mixture of stereoisomers, or tautomer thereof.

In one embodiment of formula (IVc), neither of $R^E$ or $R^W$ is an optionally substituted fused 5,6-aromatic or 5,6-heteromatic ring.

In one embodiment, the compound is represented by formula or (IVd):

(IVd)

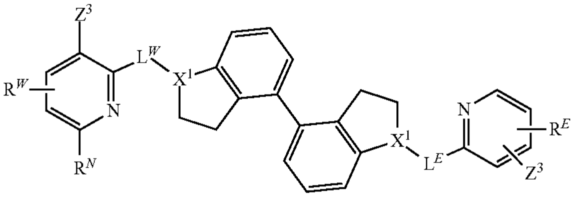

wherein each $X^1$ is independently N or CH;

each $Z^1$ is independently halo, —O$R^a$, —$C_{1-6}$ alkyl, —O$C_{1-6}$alkyl, —$C_{1-6}$ haloalkyl, or —$C_{3-8}$ cycloalkyl;

each $Z^3$ is independently halo, —O$R^a$, —$N_3$, —$NO_2$, —CN, —N$R^1R^2$, —$SO_2R^a$, —$SO_2NR^aR^b$, $—NR^aSO_2R^a$, $—NR^aC(O)R^a$, $—C(O)R^a$, $—C(O)OR^a$, $—C(O)NR^aR^b$, $—NR^aC(O)OR^a$, $—NR^aC(O)NR^1R^2$, $—OC(O)NR^aR^b$, $—NR^aSO_2NR^aR^b$, $—C(O)NR^aSO_2NR^aR^b$, $—C_{1-6}$ alkyl, $—C_{2-6}$alkenyl, $—C_{2-6}$ alkynyl, $—OC_{1-6}$ alkyl, $—C_{3-8}$ cycloalkyl, $—C_{1-6}$ alkyl$C_{3-8}$ cycloalkyl, aryl, heteroaryl, heterocyclyl, and $R^N$;

wherein the alkyl, alkenyl, alkynyl, $C_{3-8}$ cycloalkyl, aryl, heteroaryl, or heterocyclyl group is optionally substituted with 1 to 4 groups independently selected from oxo, $—NO_2$, $—N_3$, $—OR^a$, halo, cyano, $—NR^aR^b$, $—C(O)R^a$, $—C(O)OR^a$, $—OC_{1-6}$alkyCN, $—C(O)NR^aR^b$, $NR^aC(O)R^a$, $—NR^aC(O)OR^a$, $—SO_2R^a$, $—NR^aSO_2R$, $—SO_2NR^aR^b$, $—NR^aSO_2NR^aR^b$, $—C(O)NR^aSO_2NR^aR^b$ and $—C_{3-8}$ cycloalkyl; and wherein the heteroaryl or heterocyclic group may be oxidized on a nitrogen atom to form an N-oxide or oxidized on a sulfur atom to form a sulfoxide or sulfone;

$R^N$ is independently $—C_{1-6}$ alkyl$NR^1R^2$, $—OC_{1-6}$ alky$NR^1R^2$, $—C_{1-6}$ alkyl$OC_{1-6}$ alkyl$NR^1R^2$, $—NR^aC_{1-6}$ alkyl$NR^1R^2$, $—C_{1-6}$ alkyl$C(O)NR^1R^2$, $—OC_{1-6}$ alkyl$C(O)NR^1R^2$, $—OC_{1-6}$ alkyl$C(O)OR^1$, $—SC_{1-6}$alkyl$NR^1R^2$, $—C_{1-6}$alkyl$OR^a$, or

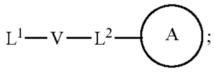;

wherein: $L^1$ is independently a bond, O, $NR^a$, S, SO, or $SO_2$;

V is independently selected from a bond, $C_{1-6}$alkyl, $C_{2-6}$alkenyl, and $C_{2-6}$alkynyl;

wherein each alkyl, alkenyl, or alkynyl is optionally independently substituted with $OR^a$, halo, cyano, $—NR^aR^b$, or $—C_{3-8}$ cycloalkyl;

$L^2$ is independently a bond, O, $NR^a$, S, SO, or $SO_2$;

ring A is independently cycloalkyl, aryl, heteroaryl, or heterocyclyl;

wherein each cycloalkyl, aryl, heteroaryl, or heterocyclyl is optionally substituted with 1 to 4 groups independently selected from oxo, $—NO_2$, $—N_3$, $—OR^a$, halo, cyano, $—C_{1-6}$ alkyl, $—C_{1-6}$ haloalkyl, $—C_{2-6}$alkenyl, $—C_{2-6}$ alkynyl, $—OC_{1-6}$ haloalkyl, $NR^aR^b$, $—C(O)R^a$, $—C(O)OR^a$, $—OC_{1-6}$ alkylCN, $—C(O)NR^aR^b$, $—NR^aC(O)R^a$, $—NR^aC(O)OR^a$, $—NR^aC(O)OR^a$, $—C(O)N(R^a)OR^b$, $—SO_2R^a$, $—SO_2NR^aR^b$, $—NR^aSO_2R^b$, $—NR^aSO_2NR^aR^b$, $—C(O)NR^aSO_2NR^aR^b$, $C_{3-8}$cycloalkyl, and $C_{1-6}$alkyl$C_{3-8}$ cycloalkyl; and wherein the alkyl, alkenyl, or alkynyl group is optionally independently substituted with $—OR^a$, halo, cyano, $—NR^aR^b$, or $—C_{3-8}$ cycloalkyl $L^E$ and $L^W$ are each independently a bond, —O—, —S—, —SO—, $—SO_2—$, $—(CR^3R^4)_m—$, $—(CR^3R^4)_mO(CR^3R^4)_m—$, $—(CR^3R^4)_mS(CR^3R^4)_m—$, $—(CR^3R^4)_mNR^3(CR^3R^4)_m—$, —C(O)—, $—(CR^3R^4)_mC(O)(CR^3R^4)_m—$, $—(CR^3R^4)_mC(O)NR^3(CR^3R^4)_m—$, $—(CR^3R^4)_mNR^3C(O)(CR^3R^4)_m—$, $C_{2-6}$ alkenylene, $C_{2-6}$ alkynylene,

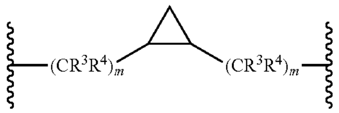

or

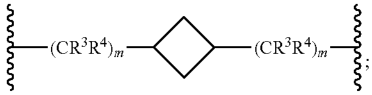;

each m is independently 0, 1, 2, 3 or 4;

$R^E$ and $R^W$ are each independently $—NR^1R^2$, $—C_{1-6}$ alky$NR^1R^2$, $—OC_{1-6}$ alkyl$NR^1R^2$, $—C_{1-6}$ alkyl$OC_{1-6}$alkyl$NR^1R^2$, $—NR^aC_{1-6}$ alkyl$NR^1R^2$, $—C_{1-6}$ alkyl$N^+R^1R^2R^3$, $—SC_{1-6}$ alkyl$NR^1R^2$, $—C(O)NR^1R^2$, $—SO_2R^a$, $—(CH_2)_uSO_2NR^1R^2$, $—(CH_2)_uNR^aSO_2NR^aR^b$, $—SO_2NR^aC_{1-6}$alky$NR^1R^2$, $—NR^aSO_2C_{1-6}$ alkyl$NR^1R^2$, $—(CH_2)_uC(O)NR^aSO_2NR^aR^b$, $—(CH_2)_uN^+R^1R^2O^-$, $—(CH_2)_uP^+R^bR^cR^d$, $—(CH_2)_uP^+R^cR^dO—$, $—(CH_2)_uP^+O[NR^aR^b][NR^cR^d]$, $—(CH_2)_uNR^cP(O)(OR^c)_2$, $—(CH_2)_uCH_2OP(O)(OR^c)(OR^d)$, $—(CH_2)_uOP(O)(OR^c)(OR^d)$, $—(CH_2)_uOP(O)NR^aR^b)(OR^a)$, or

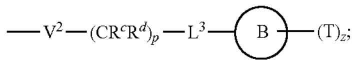

wherein:

$V^2$ is independently a bond, O, $NR^a$, S, SO, $SO_2$, $C(O)NR^a$, $NR^aC(O)$, $SO_2NR^1R^2$, or $NR^aSO_2$;

$L^3$ is independently a bond, O, $NR^a$, S, SO, $SO_2$, $C(O)NR^a$, $NR^aC(O)$, $SO_2NR^1R^2$, or $NR^aSO_2$;

ring B is cycloalkyl, aryl, heteroaryl, or heterocyclyl; T is independently H, $OR^a$, $(CH_2)_qNR^1R^2$, $(CH_2)_qNR^aC(O)R^e$, or $(CH_2)_qC(O)R^e$;

p is independently 0, 1, 2, 3, 4, or 5;

q is independently 0, 1, 2, 3, 4, or 5;

u is 0, 1, 2, 3, or 4;

z is 0, 1, 2, or 3; and wherein the alkyl, cycloalkyl, aryl, heteroaryl, or heterocyclyl of $R^E$ or $R^W$ is optionally substituted with 1 to 3 substituents independently selected from the group consisting of $NR^aR^b$, halo, cyano, oxo, $OR^a$, $—C_{1-6}$alkyl, $—C_{1-6}$haloalkyl, $—C_{1-6}$cyanoalkyl, $—C_{1-6}$alkyl$NR^aR^b$, $—C_{1-6}$ alkylOH, $—C_{3-8}$ cycloalkyl, and $—C_{1-3}$ alkyl$C_{3-8}$cycloalkyl;

provided that at least one of $V^2$, $L^3$, ring B and T contains a nitrogen atom;

$R^1$ is independently selected from H, $—C_{1-8}$ alkyl, $—C_{2-6}$ alkenyl, $—C_{2-6}$ alkynyl, $—C_{3-6}$ cycloalkyl, aryl, heteroaryl, heterocyclyl, $—C_{1-6}$alkylaryl, $—C_{1-6}$alkylheteroaryl, $—C_{1-6}$alkylheterocyclyl, $—C_{1-6}$ alkyl$C(O)OR^a$, $—C_{2-6}$ alkenyl$C(O)OR^a$, $—SO_2R^a$, $—SO_2NR^aR^b$, $—C(O)NR^aSO_2R^a$, and $C_{1-6}$alkyl $C_{3-8}$cycloalkyl;

wherein each alkyl, alkenyl, cycloalkyl, aryl, heteroaryl, or heterocyclyl is optionally substituted with 1 to 4 groups independently selected from $—OR^a$, —CN, halo, $C_{1-6}$alkyl, $—C_{1-6}$alkyl$OR^a$, $—C_{1-6}$cyanoalkyl, $—C_{1-6}$haloalkyl, $C_{3-8}$cycloalkyl, $—C_{1-3}$alkyl$C_{3-8}$cycloalkyl, $—C(O)R^a$, $—C_{1-6}$ alkyl$C(O)R^a$, $—C(O)OR^a$, $—C_{1-6}$ alkyl$C(O)OR^a$, $—NR^aR^b$, $—OC(O)NR^aR^b$, $NR^aC(O)OR^b$, $—C_{1-6}$alkyl$NR^aR^b$, $—C(O)NR^aR^b$, $—C_{1-6}$alkyl$C(O)NR^aR^b$, $—SO_2R^a$, $—C_{1-6}$alkyl$SO_2R^a$, $—SO_2NR^aR^b$, $—C_{1-6}$ alkyl$SO_2NR^aR^b$, —$C(O)NR^aSO_2R^b$, —$C_{1-6}$ alkylC(O)$NR^aSO_2R^b$, —$NR^aC(O)R^b$, and —$C_{1-6}$alkyl$NR^aC(O)R^b$;

$R^2$ is independently selected from H, —$C_{1-6}$alkyl, —$C_{2-6}$ alkenyl, —$C_{2-6}$ alkynyl, —$C_{3-6}$ cycloalkyl, aryl, heteroaryl, heterocyclyl, —$C_{1-6}$alkylaryl, —$C_{1-6}$alkylheteroaryl, —$C_{1-6}$ alkylheterocyclyl, —$C_{2-6}$alkyl-$OR^a$, —$C_{1-6}$ alkylC(O)$OR^a$, and —$C_{2-6}$ alkenylC(O)$OR^a$;

wherein each alkyl, alkenyl, alkynyl, cycloalkyl, aryl, heteroaryl, or heterocyclyl is optionally substituted with 1 to 4 groups independently selected from —$OR^a$, —CN, halo, $C_{1-6}$alkyl, —$C_{1-6}$alkyl$OR^a$, —$C_{1-6}$cyanoalkyl, —$C_{1-6}$haloalkyl, —$C_{3-8}$cycloalkyl, —$C_{1-3}$alkyl$C_{3-8}$cycloalkyl, —$C(O)R^a$, —$C_{1-6}$ alkylC(O)$R^a$, —$C(O)OR^a$, —$C_{1-6}$ alkylC(O)$OR^a$, —$NR^aR^b$, —$C_{1-6}$ alkyl$NR^aR^b$, —$C(O)NR^aR^b$, $C_{1-6}$alkylC(O)$NR^aR^b$, —$SO_2R^a$, —$C_{1-6}$alkyl$SO_2R^a$, —$SO_2NR^aR^b$, —$C_{1-6}$alkyl$SO_2NR^aR^b$, —C(O)$NR^aSO_2R^b$ and —$NR^aC(O)R^b$;

or $R^1$ and $R^2$ combine to form a heterocyclyl group optionally containing 1, 2, or 3 additional heteroatoms independently selected from oxygen, sulfur and nitrogen, and optionally substituted with 1 to 3 groups independently selected from oxo, —$C_{1-6}$alkyl, —$C_{3-8}$ cycloalkyl, —$C_{2-6}$ alkenyl, —$C_{2-6}$ alkynyl, —$OR^a$, —$C(O)OR^a$, —$C_{1-6}$ cyanoalkyl, —$C_{1-6}$ alkyl$OR^a$, —$C_{1-6}$haloalkyl, —$C_{1-3}$ alkyl$C_{3-8}$cycloalkyl, —C(O)$R^a$, —$C_{1-6}$ alkylC(O)$R^a$, —$C_{1-6}$ alkylC(O)$OR^a$, —$NR^aR^b$, —$C_{1-6}$alky$NR^aR^b$, —$C(O)NR^aR^b$, —$C_{1-6}$ alkylC(O)$NR^aR^b$, —$SO_2R^a$, —$C_{1-6}$ alkyl$SO_2R^a$, —$SO_2NR^aR^b$, and $C_{1-6}$ alkyl$SO_2NR^aR^b$;

$R^3$ is independently H, —$C_{1-6}$alkyl, —$C_{2-6}$ alkenyl, —$C_{3-6}$ cycloalkyl, aryl, heteroaryl, heterocyclyl, —$C_{1-6}$alkylaryl, —$C_{1-6}$alkylheteroaryl, —$C_{1-6}$ alkylheterocyclyl, —$C_{2-6}$alkyl-$OR^a$, —$C_{1-6}$alkylC(O)$OR^a$, or —$C_{2-6}$ alkenylC(O)$OR^a$;

$R^4$ is independently H, —$C_{1-6}$alkyl, —$C_{2-6}$ alkenyl, —$C_{3-6}$ cycloalkyl, aryl, heteroaryl, heterocyclyl, —$C_{1-6}$alkylaryl, —$C_{1-6}$alkylheteroaryl, —$C_{1-6}$ alkylheterocyclyl, —$C_{2-6}$alkyl-$OR^a$, —$C_{1-6}$alkylC(O)$OR^a$, or —$C_{2-6}$ alkenylC(O)$OR^a$;

$R^a$ is independently selected from H, —$C_{1-6}$alkyl, —$C_{3-8}$cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl;

$R^b$ is independently selected from H, —$C_{1-6}$alkyl, —$C_{3-8}$ cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$ alkylheterocyclyl;

or $R^a$ and $R^b$ may combine together to form a ring consisting of 3-8 ring atoms that are C, N, O, or S; wherein the ring is optionally substituted with 1 to 4 groups independently selected from —$OR^f$, —CN, halo, —$C_{1-6}$ alkyl$OR^f$, —$C_{1-6}$ cyanoalkyl, —$C_{1-6}$haloalkyl, —$C_{3-8}$cycloalkyl, —$C_{1-3}$ alkyl$C_{3-8}$cycloalkyl, —C(O)$R^f$, —$C_{1-6}$ alkylC(O)$R^f$, —C(O)$OR^f$, —$C_{1-6}$ alkylC(O)$OR^f$, —$NR^fR^g$, —$C_{1-6}$ alkyl$NR^fR^g$, —C(O)$NR^fR^g$, —$C_{1-6}$ alkylC(O)$NR^fR^g$, —$SO_2R^f$, —$C_{1-6}$ alkyl$SO_2R^f$, —$SO_2NR^fR^g$, —$C_{1-6}$ alkyl$SO_2NR^fR^g$, —C(O)$NR^fSO_2R^g$ and —$NR^fC(O)R^g$;

$R^c$ is independently selected from H, OH, —$C_{1-6}$alkyl, —$C_{3-8}$ cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl;

$R^d$ is independently selected from H, —$C_{1-6}$alkyl, —$C_3$-$C_8$cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl;

$R^e$ is independently selected from H, —$C_{1-6}$alkyl, —$OC_{1-6}$alkyl, —$C_{3-8}$cycloalkyl, aryl, heteroaryl, heterocyclyl, —$OC_{3-8}$cycloalkyl, —Oaryl, —Oheteroaryl, —Oheterocyclyl, —$C_{1-3}$ alkyl$C_{3-8}$cycloalkyl, —$C_{1-6}$ alkylaryl, —$C_{1-6}$alkylheteroaryl, —$NR^fR^g$, —$C_{1-6}$ alkyl$NR^fR^g$, —C(O)$NR^fR^g$, —$C_{1-6}$ alkylC(O)$NR^fR^g$, —$NHSO_2R^f$, —$C_{1-6}$alkyl$SO_2R^f$, and —$C_{1-6}$alkyl$SO_2NR^fR^g$;

$R^f$ is independently selected from H, —$C_{1-6}$alkyl, —$C_{3-8}$ cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl; and $R^g$ is independently selected from H, —$C_{1-6}$alkyl, —$C_{3-8}$ cycloalkyl, aryl, heteroaryl, heterocyclyl, —$C_{1-3}$ alkyl$C_{3-8}$ cycloalkyl, —$C_{1-6}$ alkylaryl, —$C_{1-6}$ alkylheteroaryl, and —$C_{1-6}$alkylheterocyclyl;

or a pharmaceutically acceptable salt, stereoisomer, mixture of stereoisomers, or tautomer thereof.

In one embodiment of formula (IVd), neither of $R^E$ or $R^W$ is an optionally substituted fused 5,6-aromatic or 5,6-heteromatic ring.

In one embodiment, the compound is represented by formula or (Va):

(Va)

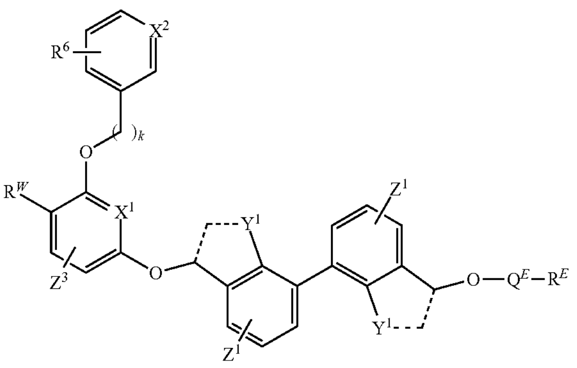

wherein the dotted lines are optionally a single bond or absent, such that when the dotted lines are absent, each $Y^1$ is independently halo, —$OR^a$, —$NO_2$, —CN, —$NR^aR^b$, —$N_3$, —$SO_2R^a$, —$C_{1-6}$ alkyl, —$C_{1-6}$ haloalkyl, —$C_{2-6}$alkenyl, —$C_{2-6}$ alkynyl, —$OC_{1-6}$alkyl, —$OC_{1-6}$haloalkyl, —$C_{3-8}$ cycloalkyl, and —$C_{1-6}$ alkyl$C_{3-8}$ cycloalkyl;

wherein each alkyl, alkenyl, alkynyl, and cycloalkyl is optionally substituted with 1 to 4 groups independently selected from oxo, —$NO_2$, —$N_3$, —$OR^a$, halo, and cyano;

or the dotted lines are single bonds and $Y^1$ is $CH_2$, such that they form a fused 5-membered ring;

k is 0, 1, 2, 3, 4, 5, or 6;

each $X^1$ is independently N or CH;

$X^2$ is N or CH;

each $Z^1$ is independently halo, —$OR^a$, —$NO_2$, —CN, —$NR^aR^b$, —$N_3$, —$SO_2R^a$, —$C_{1-6}$ alkyl, —$C_{1-6}$ haloalkyl, —$C_{2-6}$alkenyl, —$C_{2-6}$ alkynyl, —$OC_{1-6}$alkyl, —$OC_{1-6}$haloalkyl, —$C_{3-8}$ cycloalkyl, and —$C_{1-6}$ alkyl$C_{3-8}$ cycloalkyl;

wherein each alkyl, alkenyl, alkynyl, and cycloalkyl is optionally substituted with 1 to 4 groups independently selected from oxo, —$NO_2$, —$N_3$, —$OR^a$, halo, and cyano;

each $Z^3$ is independently halo, —$OR^a$, —$N_3$, —$NO_2$, —CN, —$NR^1R^2$, —$SO_2R^a$, —$SO_2N^aR^b$, —$NR^aSO_2R^a$, —$NR^aC(O)R^a$, —$C(O)R^a$, —$C(O)OR^a$, —$C(O)NR^aR^b$, —$NR^aC(O)OR^a$, —$NR^aC(O)NR^1R^2$, —$OC(O)NR^aR^b$, —$NR^aSO_2NR^aR^b$, —C(O)$NR^aSO_2NR^aR^b$, —$C_{1-6}$ alkyl, —$C_{2-6}$alkenyl, —$C_{2-6}$ alkynyl, —$OC_{1-6}$ alkyl, —$C_{3-8}$ cycloalkyl, —$C_{1-6}$ alkyl$C_{3-8}$ cycloalkyl, aryl, heteroaryl, heterocyclyl, and $R^N$;

wherein the alkyl, alkenyl, alkynyl, $C_{3-8}$ cycloalkyl, aryl, heteroaryl, or heterocyclyl group is optionally substituted with 1 to 4 groups independently selected from oxo, —$NO_2$, —$N_3$, —$OR^a$, halo, cyano, —$NR^aR^b$, —$C(O)R^a$, —$C(O)OR^a$, —$OC_{1-6}$alkyCN, —$C(O)NR^aR^b$, $NR^aC(O)R^a$, —$NR^aC(O)OR^a$, —$SO_2R^a$, —$NR^aSO_2R$, —$SO_2NR^aR^b$, —$NR^aSO_2NR^aR^b$, —$C(O)NR^aSO_2NR^aR^b$ and —$C_{3-8}$ cycloalkyl; and wherein the heteroaryl or heterocyclic group may be oxidized on a nitrogen atom to form an N-oxide or oxidized on a sulfur atom to form a sulfoxide or sulfone;

$R^N$ is independently —$C_{1-6}$alkyl$NR^1R^2$, —$OC_{1-6}$ alky$NR^1R^2$, —$C_{1-6}$ alkyl$OC_{1-6}$ alkyl$NR^1R^2$, —$NR^aC_{1-6}$ alkyl$NR^1R^2$, —$C_{1-6}$ alkylC(O)$NR^1R^2$, —$OC_{1-6}$ alkylC(O)$NR^1R^2$, —$OC_{1-6}$ alkylC(O)$OR^1$, —$SC_{1-6}$alkyl$NR^1R^2$, —$C_{1-6}$alkyl$OR^a$, or

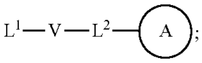;

wherein: $L^1$ is independently a bond, O, $NR^a$, S, SO, or $SO_2$,

V is independently selected from a bond, $C_{1-6}$alkyl, $C_{2-6}$alkenyl, and $C_{2-6}$alkynyl;

wherein each alkyl, alkenyl, or alkynyl is optionally independently substituted with $OR^a$, halo, cyano, —$NR^aR^b$, or —$C_{3-8}$ cycloalkyl;

$L^2$ is independently a bond, O, $NR^a$, S, SO, or $SO_2$;

ring A is independently cycloalkyl, aryl, heteroaryl, or heterocyclyl;

wherein each cycloalkyl, aryl, heteroaryl, or heterocyclyl is optionally substituted with 1 to 4 groups independently selected from oxo, —$NO_2$, —$N_3$, —$OR^a$, halo, cyano, —$C_{1-6}$ alkyl, —$C_{1-6}$ haloalkyl, —$C_{2-6}$alkenyl, —$C_{2-6}$ alkynyl, —$OC_{1-6}$ haloalkyl, $NR^aR^b$, —$C(O)R^a$, —$C(O)OR^a$, —$OC_{1-6}$ alkylCN, —$C(O)NR^aR^b$, —$NR^aC(O)R^a$, —$NR^aC(O)OR^a$, —$NR^aC(O)OR^a$, —$C(O)N(R^a)OR^b$, —$SO_2R^a$, —$SO_2NR^aR^b$, —$NR^aSO_2R^b$, —$NR^aSO_2NR^aR^b$, —$C(O)NR^aSO_2NR^aR^b$, $C_{3-8}$cycloalkyl, and $C_{1-6}$alkyl$C_{3-8}$ cycloalkyl; and wherein the alkyl, alkenyl, or alkynyl group is optionally independently substituted with —$OR^a$, halo, cyano, —$NR^aR^b$, or —$C_{3-8}$ cycloalkyl $R^6$ is —$NO_2$, —$N_3$, —$OR^a$, halo, cyano, —$C_{1-6}$ alkyl, —$C_{1-6}$ haloalkyl, —$C_{2-6}$alkenyl, —$C_{2-6}$ alkynyl, —$OC_{1-6}$haloalkyl, $NR^aR^b$, —$C(O)R^a$, —$C(O)OR^a$, —$OC_{1-6}$alkylCN, —$C(O)NR^aR^b$, —$NR^aC(O)R^a$, —$NR^aC(O)OR^a$, —$NR^aC(O)OR^a$, —$C(O)N(R^a)OR^b$, —$SO_2R^a$, —$SO_2NR^aR^b$, —$NR^aSO_2R^b$, —$NR^aSO_2NR^aR^b$, —$C(O)NR^aSO_2NR^aR^b$, $C_{3-8}$cycloalkyl, and $C_{1-6}$alkyl$C_{3-8}$ cycloalkyl;

wherein the alkyl, alkenyl, or alkynyl group is optionally independently substituted with —$OR^a$, halo, cyano, —$NR^aR^b$ or —$C_{3-8}$ cycloalkyl;

$Q^E$ is aryl, heteroaryl, or heterocyclyl;

wherein each aryl, heteroaryl, or heterocyclyl is optionally substituted with 1 to 4 groups independently selected from halo, oxo, —$OR^a$, —$N_3$, —$NO_2$, —CN, —$NR^1R^2$, —$SO_2R^a$, —$SO_2NR^aR^b$, —$NR^aSO_2R^a$, —$NR^aC(O)R^a$, —$C(O)R^a$, —C(O)$OR^a$, —$C(O)NR^aR^b$, —$NR^aC(O)OR^a$, —$NR^aC(O)$ $NR^1R^2$, —$OC(O)NR^aR^b$, —$NR^aSO_2NR^aR^b$, —$C(O)NR^aSO_2NR^aR^b$, —$C_{1-6}$ alkyl, —$C_{2-6}$ alkenyl, —$C_{2-6}$ alkynyl, —$OC_{1-6}$ alkyl, —$C_{3-8}$ cycloalkyl, —$C_{1-6}$ alkyl$C_{3-8}$ cycloalkyl, aryl, heteroaryl, heterocyclyl, and $R^N$; and wherein the alkyl, alkenyl, alkynyl, $C_{3-8}$ cycloalkyl, aryl, heteroaryl, or heterocyclyl group is optionally substituted with 1 to 4 groups independently selected from oxo, —$NO_2$, —$N_3$, —$OR^a$, halo, cyano, —$NR^aR^b$, —$C(O)R^a$, —$C(O)OR^a$, —$OC_{1-6}$ alkylCN, —$C(O)NR^aR^b$, $NR^aC(O)R^a$, —$NR^aC(O)OR^a$, —$SO_2R^a$, —$NR^aSO_2R^b$, —$SO_2NR^aR^b$, —$NR^aSO_2NR^aR^b$, —C(O)$NR^aSO_2NR^aR^b$ and —$C_{3-8}$ cycloalkyl; and further wherein the heteroaryl or heterocyclic group may be oxidized on a nitrogen atom to form an N-oxide or oxidized on a sulfur atom to form a sulfoxide or sulfone;

$R^N$ is independently —$C_{1-6}$alky$NR^1R^2$, —$OC_{1-6}$ alky$NR^1R^2$, —$C_{1-6}$ alkyl$OC_{1-6}$ alkyl$NR^1R^2$, —$NR^aC_{1-6}$ alkyl$NR^1R^2$, —$C_{1-6}$ alkylC(O)$NR^1R^2$, —$OC_{1-6}$ alkylC(O)$NR^1R^2$, —$OC_{1-6}$ alkylC(O)$OR^1$, —$SC_{1-6}$alkyl$NR^1R^2$, —$C_{1-6}$alkyl$OR^a$, or

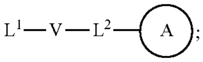;

wherein: $L^1$ is independently a bond, O, $NR^a$, S, SO, or $SO_2$;

V is independently selected from a bond, $C_{1-6}$alkyl, $C_{2-6}$alkenyl, and $C_{2-6}$alkynyl;

wherein each alkyl, alkenyl, or alkynyl is optionally independently substituted with $OR^a$, halo, cyano, —$NR^aR^b$ or —$C_{3-8}$ cycloalkyl;

$L^2$ is independently a bond, O, $NR^a$, S, SO, or $SO_2$;

ring A is independently cycloalkyl, aryl, heteroaryl, or heterocyclyl;

wherein each cycloalkyl, aryl, heteroaryl, or heterocyclyl is optionally substituted with 1 to 4 groups independently selected from oxo, —$NO_2$, —$N_3$, —$OR^a$, halo, cyano, —$C_{1-6}$ alkyl, —$C_{1-6}$ haloalkyl, —$C_{2-6}$alkenyl, —$C_{2-6}$ alkynyl, —$OC_{1-6}$ haloalkyl, $NR^aR^b$, —$C(O)R^a$, —$C(O)OR^a$, —$OC_{1-6}$ alkylCN, —$C(O)NR^aR^b$, —$NR^aC(O)R^a$, —$NR^aC(O)OR^a$, —$NR^aC(O)OR^a$, —$C(O)N(R^a)OR^b$, —$SO_2R^a$, —$SO_2NR^aR^b$, —$NR^aSO_2R^b$, —$NR^aSO_2NR^aR^b$, —$C(O)NR^aSO_2NR^aR^b$, $C_{3-8}$cycloalkyl, and $C_{1-6}$alkyl$C_{3-8}$ cycloalkyl; and wherein the alkyl, alkenyl, or alkynyl group is optionally independently substituted with —$OR^a$, halo, cyano, —$NR^aR^b$ or —$C_{3-8}$ cycloalkyl;

$R^E$ and $R^W$ are each independently —$NR^1R^2$, —$C_{1-6}$ alkyNR$^1$R$^2$, —$OC_{1-6}$ alkylNR$^1$R$^2$, —$C_{1-6}$ alkylO $C_{1-6}$alkylNR$^1$R$^2$, —$NR^aC_{1-6}$ alkylNR$^1$R$^2$, —$C_{1-6}$ alkylN$^+$R$^1$R$^2$R$^3$, —$SC_{1-6}$ alkylNR$^1$R$^2$, —C(O)NR$^1$R$^2$, —$SO_2R^a$, —$(CH_2)_uSO_2NR^1R^2$, —$(CH_2)_uNR^aSO_2NR^aR^b$, —$SO_2NR^aC_{1-6}$alkyNR$^1$R$^2$, —$NR^aSO_2C_{1-6}$ alkylNR$^1$R$^2$, —$(CH_2)_u$C(O)NR$^a$SO$_2$NR$^a$R$^b$, —$(CH_2)_uN^+R^1R^2O^-$, —$(CH_2)_uP^+R^bR^cR^d$, —$(CH_2)_uP^+R^cR^dO^-$, —$(CH_2)_uP^+O[NR^aR^b][NR^cR^d]$, —$(CH_2)_uNR^cP(O)(OR^c)_2$, —$(CH_2)_uCH_2OP(O)(OR^c)(OR^d)$, —$(CH_2)_uOP(O)(OR^c)(OR^d)$, —$(CH_2)_uOP(O)NR^aR^b)(OR^a)$, or

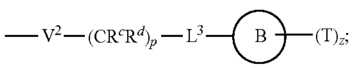

wherein:

$V^2$ is independently a bond, O, $NR^a$, S, SO, $SO_2$, C(O)NR$^a$, NR$^a$C(O), $SO_2NR^1R^2$, or $NR^aSO_2$;

$L^3$ is independently a bond, O, $NR^a$, S, SO, $SO_2$, C(O)NR$^a$, NR$^a$C(O), $SO_2NR^1R^2$, or $NR^aSO_2$;

ring B is cycloalkyl, aryl, heteroaryl, or heterocyclyl; T is independently H, OR$^a$, $(CH_2)_qNR^1R^2$, $(CH_2)_qNR^aC(O)R^e$, or $(CH_2)_qC(O)R^e$;

p is independently 0, 1, 2, 3, 4, or 5;

q is independently 0, 1, 2, 3, 4, or 5;

u is 0, 1, 2, 3, or 4;

z is 0, 1, 2, or 3; and wherein the alkyl, cycloalkyl, aryl, heteroaryl, or heterocyclyl of $R^E$ or $R^W$ is optionally substituted with 1 to 3 substituents independently selected from the group consisting of $NR^aR^b$, halo, cyano, oxo, OR$^a$, —$C_{1-6}$alkyl, —$C_{1-6}$ haloalkyl, —$C_{1-6}$ cyanoalkyl, —$C_{1-6}$alkylNR$^a$R$^b$, —$C_{1-6}$ alkylOH, —$C_{3-8}$ cycloalkyl, and —$C_{1-3}$ alkyl$C_{3-8}$cycloalkyl;

provided that at least one of $V^2$, $L^3$, ring B and T contains a nitrogen atom;

$R^1$ is independently selected from H, —$C_{1-8}$ alkyl, —$C_{2-6}$ alkenyl, —$C_{2-6}$ alkynyl, —$C_{3-6}$ cycloalkyl, aryl, heteroaryl, heterocyclyl, —$C_{1-6}$ alkylaryl, —$C_{1-6}$ alkylheteroaryl, —$C_{1-6}$ alkylheterocyclyl, —$C_{1-6}$ alkylC(O)OR$^a$, —$C_{2-6}$ alkenylC(O)OR$^a$, —$SO_2R^a$, —$SO_2NR^aR^b$, —C(O)NR$^a$SO$_2$R$^a$, and $C_{1-6}$ alkyl $C_{3-8}$cycloalkyl;

wherein each alkyl, alkenyl, cycloalkyl, aryl, heteroaryl, or heterocyclyl is optionally substituted with 1 to 4 groups independently selected from —OR$^a$, —CN, halo, $C_{1-6}$alkyl, —$C_{1-6}$ alkylOR$^a$, —$C_{1-6}$ cyanoalkyl, —$C_{1-6}$haloalkyl, $C_{3-8}$ cycloalkyl, —$C_{1-3}$alkyl$C_{3-8}$cycloalkyl, —C(O)R$^a$, —$C_{1-6}$ alkylC(O)R$^a$, —C(O)OR$^a$, —$C_{1-6}$ alkylC(O)OR$^a$, —NR$^a$R$^b$, —OC(O)NR$^a$R$^b$, NR$^a$C(O)OR$^b$, —$C_{1-6}$alkylNR$^a$R$^b$, —C(O)NR$^a$R$^b$, —$C_{1-6}$alkylC(O)NR$^a$R$^b$, —SO$_2$R$^a$, —$C_{1-6}$alkylSO$_2$R$^a$, —SO$_2$NR$^a$R$^b$, —$C_{1-6}$ alkylSO$_2$NR$^a$R$^b$, —C(O)NR$^a$SO$_2$R$^b$, —$C_{1-6}$ alkylC(O)NR$^a$SO$_2$R$^b$, —NR$^a$C(O)R$^b$, and —$C_{1-6}$alkylNR$^a$C(O)R$^b$;

$R^2$ is independently selected from H, —$C_{1-6}$alkyl, —$C_{2-6}$ alkenyl, —$C_{2-6}$ alkynyl, —$C_{3-6}$ cycloalkyl, aryl, heteroaryl, heterocyclyl, —$C_{1-6}$alkylaryl, —$C_{1-6}$alkylheteroaryl, —$C_{1-6}$ alkylheterocyclyl, —$C_{2-6}$alkyl-OR$^a$, —$C_{1-6}$ alkylC(O)OR$^a$, and —$C_{2-6}$ alkenylC(O)OR$^a$;

wherein each alkyl, alkenyl, alkynyl, cycloalkyl, aryl, heteroaryl, or heterocyclyl is optionally substituted with 1 to 4 groups independently selected from —OR$^a$, —CN, halo, $C_{1-6}$alkyl, —$C_{1-6}$alkylOR$^a$, —$C_{1-6}$cyanoalkyl, —$C_{1-6}$haloalkyl, —$C_{3-8}$cycloalkyl, —$C_{1-3}$alkyl$C_{3-8}$cycloalkyl, —C(O)R$^a$, —$C_{1-6}$ alkylC(O)R$^a$, —C(O)OR$^a$, —$C_{1-6}$ alkylC(O)OR$^a$, —NR$^a$R$^b$, —$C_{1-6}$ alkylNR$^a$R$^b$, —C(O)NR$^a$R$^b$, $C_{1-6}$alkylC(O)NR$^a$R$^b$, —SO$_2$R$^a$, —$C_{1-6}$alkylSO$_2$R$^a$, —SO$_2$NR$^a$R$^b$, —$C_{1-6}$alkylSO$_2$NR$^a$R$^b$, —C(O)NR$^a$SO$_2$R$^b$ and —NR$^a$C(O)R$^b$;

or $R^1$ and $R^2$ combine to form a heterocyclyl group optionally containing 1, 2, or 3 additional heteroatoms independently selected from oxygen, sulfur and nitrogen, and optionally substituted with 1 to 3 groups independently selected from oxo, —$C_{1-6}$alkyl, —$C_{3-8}$ cycloalkyl, —$C_{2-6}$ alkenyl, —$C_{2-6}$ alkynyl, —OR$^a$, —C(O)OR$^a$, —$C_{1-6}$ cyanoalkyl, —$C_{1-6}$ alkylOR$^a$, —$C_{1-6}$haloalkyl, —$C_{1-3}$ alkyl$C_{3-8}$cycloalkyl, —C(O)R$^a$, —$C_{1-6}$ alkylC(O)R$^a$, —$C_{1-6}$ alkylC(O)OR$^a$, —NR$^a$R$^b$, —$C_{1-6}$alkyNR$^a$R$^b$, —C(O)NR$^a$R$^b$, —$C_{1-6}$ alkylC(O)NR$^a$R$^b$, —SO$_2$R$^a$, —$C_{1-6}$ alkylSO$_2$R$^a$, —SO$_2$NR$^a$R$^b$, and $C_{1-6}$ alkylSO$_2$NR$^a$R$^b$;

$R^3$ is independently H, —$C_{1-6}$alkyl, —$C_{2-6}$ alkenyl, —$C_{3-6}$ cycloalkyl, aryl, heteroaryl, heterocyclyl, —$C_{1-6}$alkylaryl, —$C_{1-6}$alkylheteroaryl, —$C_{1-6}$ alkylheterocyclyl, —$C_{2-6}$alkyl-OR$^a$, —$C_{1-6}$alkylC(O)OR$^a$, or —$C_{2-6}$ alkenylC(O)OR$^a$;

$R^4$ is independently H, —$C_{1-6}$alkyl, —$C_{2-6}$ alkenyl, —$C_{3-6}$ cycloalkyl, aryl, heteroaryl, heterocyclyl, —$C_{1-6}$alkylaryl, —$C_{1-6}$alkylheteroaryl, —$C_{1-6}$ alkylheterocyclyl, —$C_{2-6}$alkyl-OR$^a$, —$C_{1-6}$alkylC(O)OR$^a$, or —$C_{2-6}$ alkenylC(O)OR$^a$;

$R^a$ is independently selected from H, —$C_{1-6}$alkyl, —$C_{3-8}$cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl;

$R^b$ is independently selected from H, —$C_{1-6}$alkyl, —$C_{3-8}$cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$ alkylheterocyclyl;

or $R^a$ and $R^b$ may combine together to form a ring consisting of 3-8 ring atoms that are C, N, O, or S; wherein the ring is optionally substituted with 1 to 4 groups independently selected from —OR$^f$, —CN, halo, —$C_{1-6}$ alkylOR$^f$, —$C_{1-6}$ cyanoalkyl, —$C_{1-6}$haloalkyl, —$C_{3-8}$ cycloalkyl, —$C_{1-3}$ alkyl$C_{3-8}$cycloalkyl, —C(O)R$^f$, —$C_{1-6}$ alkylC(O)R$^f$, —C(O)OR$^f$, —$C_{1-6}$ alkylC(O)OR$^f$, —NR$^f$R$^g$, —$C_{1-6}$ alkylNR$^f$R$^g$, —C(O)NR$^f$R$^g$, —$C_{1-6}$ alkylC(O)NR$^f$R$^g$, —SO$_2$R$^f$, —$C_{1-6}$ alkylSO$_2$R$^f$, —SO$_2$NR$^f$R$^g$, —$C_{1-6}$ alkylSO$_2$NR$^f$R$^g$, —C(O)NR$^f$SO$_2$R$^g$ and —NR$^f$C(O)R$^g$;

$R^c$ is independently selected from H, OH, —$C_{1-6}$alkyl, —$C_{3-8}$cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl;

$R^d$ is independently selected from H, —$C_{1-6}$alkyl, —$C_3$-$C_8$cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl;

$R^e$ is independently selected from H, —$C_{1-6}$alkyl, —O$C_{1-6}$alkyl, —$C_{3-8}$ cycloalkyl, aryl, heteroaryl, heterocyclyl, —O$C_{3-8}$cycloalkyl, —Oaryl, —Oheteroaryl, —Oheterocyclyl, —$C_{1-3}$ alkyl$C_{3-8}$cycloalkyl, —$C_{1-6}$alkylaryl, —$C_{1-6}$alkylheteroaryl, —NR$^f$R$^g$, —$C_{1-6}$alkyl$NR^fR^g$, —$C(O)NR^fR^g$, —$C_{1-6}$alkylC(O)$NR^fR^g$, —$NHSO_2R^f$, —$C_{1-6}$alkyl$SO_2R^f$, and —$C_{1-6}$alkyl$SO_2NR^fR^g$;

$R^f$ is independently selected from H, —$C_{1-6}$alkyl, —$C_{3-8}$ cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl; and $R^g$ is independently selected from H, —$C_{1-6}$alkyl, —$C_{3-8}$ cycloalkyl, aryl, heteroaryl, heterocyclyl, —$C_{1-3}$ alkyl$C_{3-8}$ cycloalkyl, —$C_{1-6}$ alkylaryl, —$C_{1-6}$ alkylheteroaryl, and —$C_{1-6}$alkylheterocyclyl;

or a pharmaceutically acceptable salt, stereoisomer, mixture of stereoisomers, or tautomer thereof.

In one embodiment of formula (Va), neither of $R^E$ or $R^W$ is an optionally substituted fused 5,6-aromatic or 5,6-heteromatic ring.

In one embodiment, the compound is represented by formula or (Vb):

(Vb)

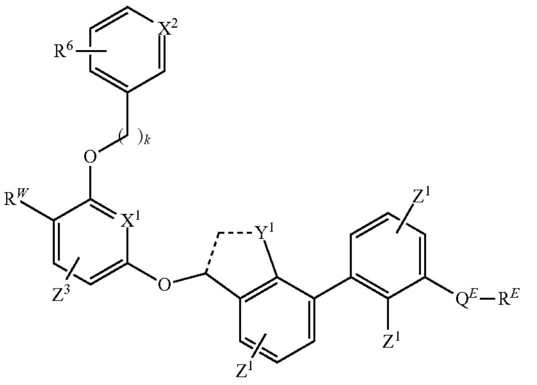

wherein the dotted lines are optionally a single bond or absent, such that when the dotted lines are absent, $Y^1$ is halo, —$OR^a$, —$NO_2$, —CN, —$NR^aR^b$, —$N_3$, —$SO_2R^a$, —$C_{1-6}$ alkyl, —$C_{1-6}$ haloalkyl, —$C_{2-6}$alkenyl, —$C_{2-6}$ alkynyl, —$OC_{1-6}$alkyl, —$OC_{1-6}$haloalkyl, —$C_{3-8}$ cycloalkyl, and —$C_{1-6}$ alkyl$C_{3-8}$ cycloalkyl;

wherein each alkyl, alkenyl, alkynyl, and cycloalkyl is optionally substituted with 1 to 4 groups independently selected from oxo, —$NO_2$, —$N_3$, —$OR^a$, halo, and cyano;

or the dotted lines are single bonds and $Y^1$ is $CH_2$, such that they form a fused 5-membered ring;

k is 0, 1, 2, 3, 4, 5, or 6;

each $X^1$ is independently N or CH;

$X^2$ is N or CH;

each $Z^1$ is independently halo, —$OR^a$, —$NO_2$, —CN, —$NR^aR^b$, —$N_3$, —$SO_2R^a$, —$C_{1-6}$ alkyl, —$C_{1-6}$ haloalkyl, —$C_{2-6}$alkenyl, —$C_{2-6}$ alkynyl, —$OC_{1-6}$ alkyl, —$OC_{1-6}$haloalkyl, —$C_{3-8}$ cycloalkyl, and —$C_{1-6}$ alkyl$C_{3-8}$ cycloalkyl;

wherein each alkyl, alkenyl, alkynyl, and cycloalkyl is optionally substituted with 1 to 4 groups independently selected from oxo, —$NO_2$, —$N_3$, —$OR^a$, halo, and cyano;

each $Z^3$ is independently halo, —$OR^a$, —$N_3$, —$NO_2$, —CN, —$NR^1R^2$, —$SO_2R^a$, —$SO_2NR^aR^b$, —$NR^aSO_2R^a$, —$NR^aC(O)R^a$, —$C(O)R^a$, —$C(O)OR^a$, —$C(O)NR^aR^b$, —$NR^aC(O)OR^a$, —$NR^aC(O)NR^1R^2$, —$OC(O)NR^aR^b$, —$NR^aSO_2NR^aR^b$, —$C(O)NR^aSO_2NR^aR^b$, —$C_{1-6}$ alkyl, —$C_{2-6}$ alkenyl, —$C_{2-6}$ alkynyl, —$OC_{1-6}$ alkyl, —$C_{3-8}$ cycloalkyl, —$C_{1-6}$ alkyl$C_{3-8}$ cycloalkyl, aryl, heteroaryl, heterocyclyl, and $R^N$;

wherein the alkyl, alkenyl, alkynyl, $C_{3-8}$ cycloalkyl, aryl, heteroaryl, or heterocyclyl group is optionally substituted with 1 to 4 groups independently selected from oxo, —$NO_2$, —$N_3$, —$OR^a$, halo, cyano, —$NR^aR^b$, —$C(O)R^a$, —$C(O)OR^a$, —$OC_{1-6}$alkyCN, —$C(O)NR^aR^b$, $NR^aC(O)R^a$, —$NR^aC(O)OR^a$, —$SO_2R^a$, —$NR^aSO_2R$, —$SO_2NR^aR^b$, —$NR^aSO_2NR^aR^b$, —$C(O)NR^aSO_2NR^aR^b$ and —$C_{3-8}$ cycloalkyl; and wherein the heteroaryl or heterocyclic group may be oxidized on a nitrogen atom to form an N-oxide or oxidized on a sulfur atom to form a sulfoxide or sulfone;

$R^N$ is independently —$C_{1-6}$ alkyl$NR^1R^2$, —$OC_{1-6}$ alky$NR^1R^2$, —$C_{1-6}$ alkyl$OC_{1-6}$ alkyl$NR^1R^2$, —$NR^aC_{1-6}$ alkyl$NR^1R^2$, —$C_{1-6}$ alkylC(O)$NR^1R^2$, —$OC_{1-6}$ alkylC(O)$NR^1R^2$, —$OC_{1-6}$ alkylC(O)$OR^1$, —$SC_{1-6}$alkyl$NR^1R^2$, —$C_{1-6}$alkyl$OR^a$, or

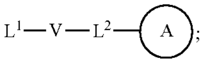;

wherein: $L^1$ is independently a bond, O, $NR^a$, S, SO, or $SO_2$;

V is independently selected from a bond, $C_{1-6}$alkyl, $C_{2-6}$alkenyl, and $C_{2-6}$alkynyl;

wherein each alkyl, alkenyl, or alkynyl is optionally independently substituted with $OR^a$, halo, cyano, —$NR^aR^b$, or —$C_{3-8}$ cycloalkyl;

$L^2$ is independently a bond, O, $NR^a$, S, SO, or $SO_2$;

ring A is independently cycloalkyl, aryl, heteroaryl, or heterocyclyl;

wherein each cycloalkyl, aryl, heteroaryl, or heterocyclyl is optionally substituted with 1 to 4 groups independently selected from oxo, —$NO_2$, —$N_3$, —$OR^a$, halo, cyano, —$C_{1-6}$ alkyl, —$C_{1-6}$ haloalkyl, —$C_{2-6}$alkenyl, —$C_{2-6}$ alkynyl, —$OC_{1-6}$ haloalkyl, $NR^aR^b$, —$C(O)R^a$, —$C(O)OR^a$, —$OC_{1-6}$ alkylCN, —$C(O)NR^aR^b$, —$NR^aC(O)R^a$, —$NR^aC(O)OR^a$, —$NR^aC(O)OR^a$, —$C(O)N(R^a)OR^b$, —$SO_2R^a$, —$SO_2NR^aR^b$, —$NR^aSO_2R^b$, —$NR^aSO_2NR^aR^b$, —$C(O)NR^aSO_2NR^aR^b$, $C_{3-8}$cycloalkyl, and $C_{1-6}$alkyl$C_{3-8}$ cycloalkyl; and wherein the alkyl, alkenyl, or alkynyl group is optionally independently substituted with —$OR^a$, halo, cyano, —$NR^aR^b$, or —$C_{3-8}$ cycloalkyl $R^6$ is —$NO_2$, —$N_3$, —$OR^a$, halo, cyano, —$C_{1-6}$ alkyl, —$C_{1-6}$ haloalkyl, —$C_{2-6}$alkenyl, —$C_{2-6}$ alkynyl, —$OC_{1-6}$haloalkyl, $NR^aR^b$, —$C(O)R^a$, —$C(O)OR^a$, —$OC_{1-6}$alkylCN, —$C(O)NR^aR^b$, —$NR^aC(O)R^a$, —$NR^aC(O)OR^a$, —$NR^aC(O)OR^a$, —$C(O)N(R^a)OR^b$, —$SO_2R^a$, —$SO_2NR^aR^b$, —$NR^aSO_2R^b$, —$NR^aSO_2NR^aR^b$, —$C(O)NR^aSO_2NR^aR^b$, $C_{3-8}$cycloalkyl, and $C_{1-6}$alkyl$C_{3-8}$cycloalkyl;

wherein the alkyl, alkenyl, or alkynyl group is optionally independently substituted with —$OR^a$, halo, cyano, —$NR^aR^b$ or —$C_{3-8}$cycloalkyl;

$Q^E$ is aryl, heteroaryl, or heterocyclyl;

wherein each aryl, heteroaryl, or heterocyclyl is optionally substituted with 1 to 4 groups independently selected from halo, oxo, —$OR^a$, —$N_3$, —$NO_2$, —CN, —$NR^1R^2$, —$SO_2R^a$, —$SO_2NR^aR^b$, —$NR^aSO_2R^a$, —$NR^aC(O)R^a$, —$C(O)R^a$, —$C(O)OR^a$, —$C(O)NR^aR^b$, —$NR^aC(O)OR^a$, —$NR^aC(O)NR^1R^2$, —$OC(O)NR^aR^b$, —$NR^aSO_2NR^aR^b$, —$C(O)NR^aSO_2NR^aR^b$, —$C_{1-6}$ alkyl, —$C_{2-6}$alkenyl, —$C_{2-6}$ alkynyl, —$OC_{1-6}$ alkyl, —$C_{3-8}$cycloalkyl, —$C_{1-6}$ alkyl$C_{3-8}$cycloalkyl, aryl, heteroaryl, heterocyclyl, and $R^N$; and wherein the alkyl, alkenyl, alkynyl, $C_{3-8}$cycloalkyl, aryl, heteroaryl, or heterocyclyl group is optionally substituted with 1 to 4 groups independently selected from oxo, —$NO_2$, —$N_3$, —$OR^a$, halo, cyano, —$NR^aR^b$, —$C(O)R^a$, —$C(O)OR^a$, —$OC_{1-6}$ alkyCN, —$C(O)NR^aR^b$, $NR^aC(O)R^a$, —$NR^aC(O)OR^a$, —$SO_2R^a$, —$NR^aSO_2R^b$, —$SO_2NR^aR^b$, —$NR^aSO_2NR^aR^b$, —$C(O)NR^aSO_2NR^aR^b$ and —$C_{3-8}$cycloalkyl; and further wherein the heteroaryl or heterocyclic group may be oxidized on a nitrogen atom to form an N-oxide or oxidized on a sulfur atom to form a sulfoxide or sulfone;

$R^N$ is independently —$C_{1-6}$ alkyl$NR^1R^2$, —$OC_{1-6}$ alky$NR^1R^2$, —$C_{1-6}$ alkyl$OC_{1-6}$ alkyl$NR^1R^2$, —$NR^aC_{1-6}$ alkyl$NR^1R^2$, —$C_{1-6}$ alkyl$C(O)NR^1R^2$, —$OC_{1-6}$ alkyl$C(O)NR^1R^2$, —$OC_{1-6}$ alkyl$C(O)OR^1$, —$SC_{1-6}$alkyl$NR^1R^2$, —$C_{1-6}$alkyl$OR^a$, or

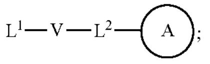

wherein: $L^1$ is independently a bond, O, $NR^a$, S, SO, or $SO_2$;

V is independently selected from a bond, $C_{1-6}$alkyl, $C_{2-6}$alkenyl, and $C_{2-6}$alkynyl;

wherein each alkyl, alkenyl, or alkynyl is optionally independently substituted with $OR^a$, halo, cyano, —$NR^aR^b$ or —$C_{3-8}$cycloalkyl;

$L^2$ is independently a bond, O, $NR^a$, S, SO, or $SO_2$;

ring A is independently cycloalkyl, aryl, heteroaryl, or heterocyclyl;

wherein each cycloalkyl, aryl, heteroaryl, or heterocyclyl is optionally substituted with 1 to 4 groups independently selected from oxo, —$NO_2$, —$N_3$, —$OR^a$, halo, cyano, —$C_{1-6}$ alkyl, —$C_{1-6}$ haloalkyl, —$C_{2-6}$alkenyl, —$C_{2-6}$ alkynyl, —$OC_{1-6}$ haloalkyl, $NR^aR^b$, —$C(O)R^a$, —$C(O)OR^a$, —$OC_{1-6}$ alkylCN, —$C(O)NR^aR^b$, —$NR^aC(O)R^a$, —$NR^aC(O)OR^a$, —$NR^aC(O)OR^a$, —$C(O)N(R^a)OR^b$, —$SO_2R^a$, —$SO_2NR^aR^b$, —$NR^aSO_2R^b$, —$NR^aSO_2NR^aR^b$, —$C(O)NR^aSO_2NR^aR^b$, $C_{3-8}$cycloalkyl, and $C_{1-6}$alkyl$C_{3-8}$ cycloalkyl; and wherein the alkyl, alkenyl, or alkynyl group is optionally independently substituted with —$OR^a$, halo, cyano, —$NR^aR^b$ or —$C_{3-8}$ cycloalkyl;

$R^E$ and $R^W$ are each independently —$NR^1R^2$, —$C_{1-6}$ alky$NR^1R^2$, —$OC_{1-6}$ alkyl$NR^1R^2$, —$C_{1-6}$ alkyl$OC_{1-6}$alkyl$NR^1R^2$, —$NR^aC_{1-6}$ alkyl$NR^1R^2$, —$C_{1-6}$ alkyl$N^+R^1R^2R^3$, —$SC_{1-6}$ alkyl$NR^1R^2$, —$C(O)NR^1R^2$, —$SO_2R^a$, —$(CH_2)_uSO_2NR^1R^2$, —$(CH_2)_uNR^aSO_2NR^aR^b$, —$SO_2NR^aC_{1-6}$ alky$NR^1R^2$, —$NR^aSO_2C_{1-6}$ alkyl$NR^1R^2$, —$(CH_2)_uC(O)NR^aSO_2NR^aR^b$, —$(CH_2)_uN^+R^1R^2O^-$, —$(CH_2)_uP^+R^bR^cR^d$, —$(CH_2)_uP^+R^cR^dO^-$, —$(CH_2)_uP^+O[NR^aR^b][NR^cR^d]$, —$(CH_2)_uNR^cP(O)(OR^c)_2$, —$(CH_2)_uCH_2OP(O)(OR^c)(OR^d)$, —$(CH_2)_uOP(O)(OR^c)(OR^d)$, —$(CH_2)_uOP(O)NR^aR^b)(OR^a)$, or

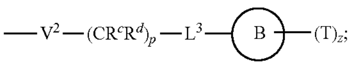

wherein:

$V^2$ is independently a bond, O, $NR^a$, S, SO, $SO_2$, $C(O)NR^a$, $NR^aC(O)$, $SO_2NR^1R^2$, or $NR^aSO_2$;

$L^3$ is independently a bond, O, $NR^a$, S, SO, $SO_2$, $C(O)NR^a$, $NR^aC(O)$, $SO_2NR^1R^2$, or $NR^aSO_2$;

ring B is cycloalkyl, aryl, heteroaryl, or heterocyclyl; T is independently H, $OR^a$, $(CH_2)_qNR^1R^2$, $(CH_2)_qNR^aC(O)R^e$, or $(CH_2)_qC(O)R^e$;

p is independently 0, 1, 2, 3, 4, or 5;

q is independently 0, 1, 2, 3, 4, or 5;

u is 0, 1, 2, 3, or 4;

z is 0, 1, 2, or 3; and wherein the alkyl, cycloalkyl, aryl, heteroaryl, or heterocyclyl of $R^E$ or $R^W$ is optionally substituted with 1 to 3 substituents independently selected from the group consisting of $NR^aR^b$, halo, cyano, oxo, $OR^a$, —$C_{1-6}$alkyl, —$C_{1-6}$ haloalkyl, —$C_{1-6}$ cyanoalkyl, —$C_{1-6}$alky$NR^aR^b$, —$C_{1-6}$ alkylOH, —$C_{3-8}$ cycloalkyl, and —$C_{1-3}$ alkyl$C_{3-8}$cycloalkyl;

provided that at least one of $V^2$, $L^3$, ring B and T contains a nitrogen atom;

$R^1$ is independently selected from H, —$C_{1-8}$ alkyl, —$C_{2-6}$ alkenyl, —$C_{2-6}$ alkynyl, —$C_{3-6}$ cycloalkyl, aryl, heteroaryl, heterocyclyl, —$C_{1-6}$ alkylaryl, —$C_{1-6}$ alkylheteroaryl, —$C_{1-6}$ alkylheterocyclyl, —$C_{1-6}$ alkyl$C(O)OR^a$, —$C_{2-6}$ alkenyl$C(O)OR^a$, —$SO_2R^a$, —$SO_2NR^aR^b$, —$C(O)NR^aSO_2R^a$, and $C_{1-6}$alkyl $C_{3-8}$cycloalkyl;

wherein each alkyl, alkenyl, cycloalkyl, aryl, heteroaryl, or heterocyclyl is optionally substituted with 1 to 4 groups independently selected from —$OR^a$, —CN, halo, $C_{1-6}$alkyl, —$C_{1-6}$alkyl$OR^a$, —$C_{1-6}$cyanoalkyl, —$C_{1-6}$haloalkyl, $C_{3-8}$cycloalkyl, —$C_{1-3}$alkyl$C_{3-8}$cycloalkyl, —$C(O)R^a$, —$C_{1-6}$ alkyl$C(O)R^a$, —$C(O)OR^a$, —$C_{1-6}$ alkyl$C(O)OR^a$, —$NR^aR^b$, —$OC(O)NR^aR^b$, $NR^aC(O)OR^b$, —$C_{1-6}$alkyl$NR^aR^b$, —$C(O)NR^aR^b$, —$C_{1-6}$alkyl$C(O)NR^aR^b$, —$SO_2R^a$, —$C_{1-6}$alkyl$SO_2R^a$, —$SO_2NR^aR^b$, —$C_{1-6}$ alkyl$SO_2NR^aR^b$, —$C(O)NR^aSO_2R^b$, —$C_{1-6}$ alkyl$C(O)NR^aSO_2R^b$, —$NR^aC(O)R^b$, and —$C_{1-6}$alkyl $NR^aC(O)R^b$;

$R^2$ is independently selected from H, —$C_{1-6}$alkyl, —$C_{2-6}$ alkenyl, —$C_{2-6}$ alkynyl, —$C_{3-6}$ cycloalkyl, aryl, heteroaryl, heterocyclyl, —$C_{1-6}$alkylaryl, —$C_{1-6}$alkylheteroaryl, —$C_{1-6}$ alkylheterocyclyl, —$C_{2-6}$alkyl-$OR^a$, —$C_{1-6}$ alkyl$C(O)OR^a$, and —$C_{2-6}$ alkenyl$C(O)OR^a$;

wherein each alkyl, alkenyl, alkynyl, cycloalkyl, aryl, heteroaryl, or heterocyclyl is optionally substituted with 1 to 4 groups independently selected from —$OR^a$, —CN, halo, $C_{1-6}$alkyl, —$C_{1-6}$alkyl$OR^a$, —$C_{1-6}$cyanoalkyl, —$C_{1-6}$haloalkyl, —$C_{3-8}$cycloalkyl, —$C_{1-3}$alkyl$C_{3-8}$cycloalkyl, —$C(O)R^a$, —$C_{1-6}$ alkyl$C(O)R^a$, —$C(O)OR^a$, —$C_{1-6}$ alkyl$C(O)OR^a$, —$NR^aR^b$, —$C_{1-6}$ alkyl$NR^aR^b$, —C(O)$NR^aR^b$, $C_{1-6}$alkylC(O)$NR^aR^b$, —$SO_2R^a$, —$C_{1-6}$alkyl$SO_2R^a$, —$SO_2NR^aR^b$, —$C_{1-6}$alkyl$SO_2NR^aR^b$, —C(O)$NR^aSO_2R^b$ and —$NR^a$C(O)$R^b$;

or $R^1$ and $R^2$ combine to form a heterocyclyl group optionally containing 1, 2, or 3 additional heteroatoms independently selected from oxygen, sulfur and nitrogen, and optionally substituted with 1 to 3 groups independently selected from oxo, —$C_{1-6}$alkyl, —$C_{3-8}$ cycloalkyl, —$C_{2-6}$ alkenyl, —$C_{2-6}$ alkynyl, —$OR^a$, —C(O)$OR^a$, —$C_{1-6}$cyanoalkyl, —$C_{1-6}$ alkyl$OR^a$, —$C_{1-6}$haloalkyl, —$C_{1-3}$ alkyl$C_{3-8}$cycloalkyl, —C(O)$R^a$, —$C_{1-6}$ alkylC(O)$R^a$, —$C_{1-6}$ alkylC(O)$OR^a$, —$NR^aR^b$, —$C_{1-6}$alky$NR^aR^b$, —C(O)$NR^aR^b$, —$C_{1-6}$ alkylC(O)$NR^aR^b$, —$SO_2R^a$, —$C_{1-6}$ alkyl$SO_2R^a$, —$SO_2NR^aR^b$, and $C_{1-6}$ alkyl$SO_2NR^aR^b$;

$R^3$ is independently H, —$C_{1-6}$alkyl, —$C_{2-6}$ alkenyl, —$C_{3-6}$ cycloalkyl, aryl, heteroaryl, heterocyclyl, —$C_{1-6}$alkylaryl, —$C_{1-6}$alkylheteroaryl, —$C_{1-6}$ alkylheterocyclyl, —$C_{2-6}$alkyl-$OR^a$, —$C_{1-6}$alkylC(O)$OR^a$, or —$C_{2-6}$ alkenylC(O)$OR^a$;

$R^4$ is independently H, —$C_{1-6}$alkyl, —$C_{2-6}$ alkenyl, —$C_{3-6}$ cycloalkyl, aryl, heteroaryl, heterocyclyl, —$C_{1-6}$alkylaryl, —$C_{1-6}$alkylheteroaryl, —$C_{1-6}$ alkylheterocyclyl, —$C_{2-6}$alkyl-$OR^a$, —$C_{1-6}$alkylC(O)$OR^a$, or —$C_{2-6}$ alkenylC(O)$OR^a$;

$R^a$ is independently selected from H, —$C_{1-6}$alkyl, —$C_{3-8}$ cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl;

$R^b$ is independently selected from H, —$C_{1-6}$alkyl, —$C_{3-8}$ cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$ alkylheterocyclyl;

or $R^a$ and $R^b$ may combine together to form a ring consisting of 3-8 ring atoms that are C, N, O, or S; wherein the ring is optionally substituted with 1 to 4 groups independently selected from —$OR^f$, —CN, halo, —$C_{1-6}$ alkyl$OR^f$, —$C_{1-6}$cyanoalkyl, —$C_{1-6}$haloalkyl, —$C_{3-8}$ cycloalkyl, —$C_{1-3}$ alkyl$C_{3-8}$cycloalkyl, —C(O)$R^f$, —$C_{1-6}$alkylC(O)$R^f$, —C(O)$OR^f$, —$C_{1-6}$alkylC(O)$OR^f$, —$NR^fR^g$, —$C_{1-6}$alkyl$NR^fR^g$, —C(O)$NR^fR^g$, —$C_{1-6}$ alkylC(O)$NR^fR^g$, —$SO_2R^f$, —$C_{1-6}$ alkyl$SO_2R^f$, —$SO_2NR^fR^g$, —$C_{1-6}$ alkyl$SO_2NR^fR^g$, —C(O)$NR^fSO_2R^g$ and —$NR^f$C(O)$R^g$;

$R^c$ is independently selected from H, OH, —$C_{1-6}$alkyl, —$C_{3-8}$cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl;

$R^d$ is independently selected from H, —$C_{1-6}$alkyl, —$C_3$-$C_8$cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl;

$R^e$ is independently selected from H, —$C_{1-6}$alkyl, —$OC_{1-6}$alkyl, —$C_{3-8}$ cycloalkyl, aryl, heteroaryl, heterocyclyl, —$OC_{3-8}$cycloalkyl, —Oaryl, —Oheteroaryl, —Oheterocyclyl, —$C_{1-3}$ alkyl$C_{3-8}$cycloalkyl, —$C_{1-6}$alkylaryl, —$C_{1-6}$alkylheteroaryl, —$NR^fR^g$, —$C_{1-6}$alkyl$NR^fR^g$, —C(O)$NR^fR^g$, —$C_{1-6}$alkylC(O)$NR^fR^g$, —$NHSO_2R^f$, —$C_{1-6}$alkyl$SO_2R^f$, and —$C_{1-6}$alkyl$SO_2NR^fR^g$;

$R^f$ is independently selected from H, —$C_{1-6}$alkyl, —$C_{3-8}$ cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl; and $R^g$ is independently selected from H, —$C_{1-6}$alkyl, —$C_{3-8}$ cycloalkyl, aryl, heteroaryl, heterocyclyl, —$C_{1-3}$ alkyl$C_{3-8}$ cycloalkyl, —$C_{1-6}$ alkylaryl, —$C_{1-6}$ alkylheteroaryl, and —$C_{1-6}$alkylheterocyclyl;

or a pharmaceutically acceptable salt, stereoisomer, mixture of stereoisomers, or tautomer thereof.

In one embodiment of formula (Vb), neither of $R^E$ or $R^W$ is an optionally substituted fused 5,6-aromatic or 5,6-heteromatic ring.

In one embodiment, provided is a compound of formula (VIa):

(VIa)

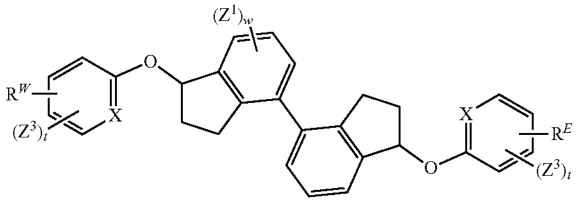

wherein $R^E$, $R^W$, $Z^1$ and $Z^3$ are as defined herein, each w is independently 0, 1 or 2, each t is independently 0, 1 or 2, and each X is independently $CZ^3$, CH or N. In one embodiment, provided is a compound of formula (VIb):

(VIb)

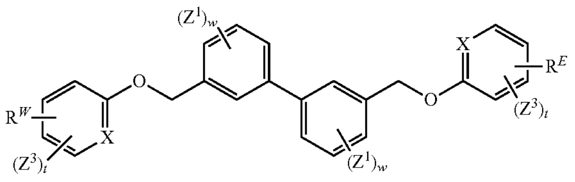

wherein $R^E$, $R^W$, $Z^1$ and $Z^3$ are as defined herein, each w is independently 0, 1 or 2, each t is independently 0, 1 or 2, and each X is independently $CZ^3$, CH or N. In one embodiment, provided is a compound of formula (VIc):

(VIc)

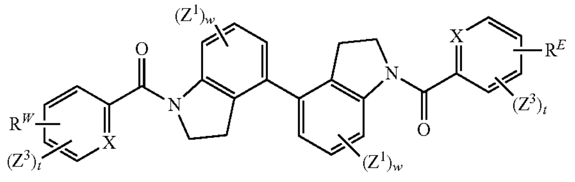

wherein $R^E$, $R^W$, $Z^1$ and $Z^3$ are as defined herein, each w is independently 0, 1 or 2, each t is independently 0, 1 or 2, and each X is independently $CZ^3$, CH or N. In one embodiment, provided is a compound of formula (VId):

(VId)

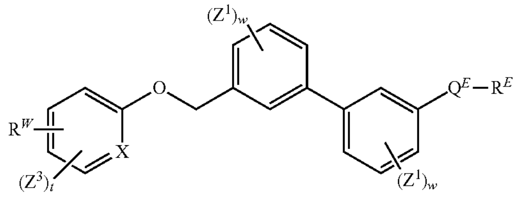

wherein $R^E$, $R^W$, $Z^1$ and $Z^3$ are as defined herein, each w is independently 0, 1 or 2, each t is independently 0, 1 or 2, and $Q^E$ is heteroaryl. In one embodiment, provided is a compound of formula (VIe):

(VIe)

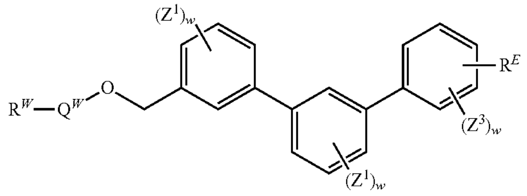

wherein $R^E$, $R^W$, $Z^1$, $Z^3$ and $Q^W$ are as defined herein, each w is independently 0, 1 or 2, each t is independently 0, 1 or 2. In one embodiment, provided is a compound of formula (VIf):

(VIf)

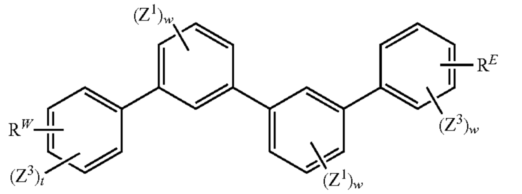

wherein $R^E$, $R^W$, $Z^1$ and $Z^3$ are as defined herein, each w is independently 0, 1 or 2, each t is independently 0, 1 or 2. In one embodiment, provided is a compound of formula (VIIa):

(VIIa)

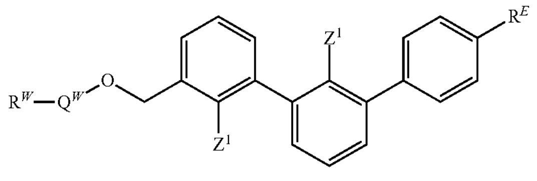

wherein $R^W$, Q, $Z^1$ and $R^E$ are as defined herein. In one embodiment, provided is a compound of formula (VIIb):

(VIIb)

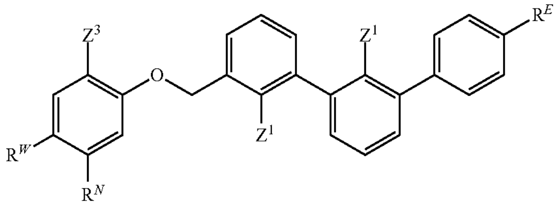

wherein $R^W$, $R^N$, $Z^3$, $Z^1$ and $R^E$ are as defined herein.

In certain embodiments of any one of formulas (VIa)-(VIf) or formulas (VIIa)-(VIIb), each $Z^1$ is independently halo. In certain embodiments of any one of formulas (VIa)-(VIf) or formulas (VIIa)-(VIIb), each $Z^3$ is independently $C_{1-6}$ alkoxy.

In certain embodiments of any one of formulas (VIa)-(VIf) or formulas (VIIa)-(VIIb), each $Z^1$ is chloro. In certain embodiments of any one of formulas (VIa)-(VIf) or formulas (VIIa)-(VIIb), each $Z^3$ is methoxy.

In certain embodiments of formula (VIa)-(VIf) or formulas (VIIa)-(VIIb), neither of $R^E$ or $R^W$ is an optionally substituted fused 5,6-aromatic or 5,6-heteromatic ring directly bound to the Q ring via a covalent bond.

In one embodiment, provided is a compound of formula (VIII):

(VIII)

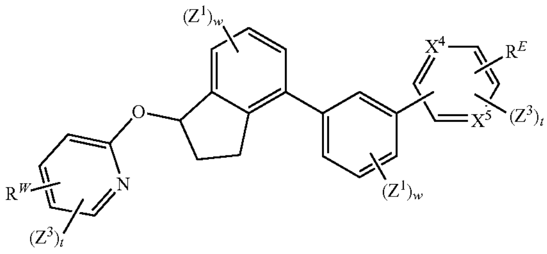

wherein:

each of $X^4$ and $X^5$ are independently N, CH or $CZ^3$;

each $Z^1$ is independently is halo, —$OR^a$, —$NO_2$, —CN, —$NR^aR^b$, —$N_3$, —$SO_2R^a$, —$C_{1-6}$ alkyl, —$C_{1-6}$ haloalkyl, —$C_{2-6}$alkenyl, —$C_{2-6}$ alkynyl, —O—$C_{1-6}$ alkyl, —O—$C_{1-6}$ haloalkyl, —$C_{3-8}$ cycloalkyl, or —$C_{1-6}$ alkyl$C_{3-8}$ cycloalkyl; and wherein each alkyl, alkenyl, alkynyl, and cycloalkyl is optionally substituted with 1 to 4 groups independently selected from oxo, —$NO_2$, —$N_3$, —$OR^a$, halo, and cyano;

each w is independently 0, 1 or 2;

each $Z^3$ is independently halo, —$OR^a$, —$N_3$, —$NO_2$, —CN, —$NR^1R^2$, —$SO_2R^a$, —$SO_2N^aR^b$, —$NR^aSO_2R^a$, —$NR^aC(O)R^a$, —$C(O)R^a$, —$C(O)OR^a$, —$C(O)NR^aR^b$, —$NR^aC(O)OR^a$, —$NR^aC(O)NR^1R^2$, —$OC(O)NR^aR^b$, —$NR^aSO_2NR^aR^b$, —C(O)$NR^aSO_2NR^aR^b$, —$C_{1-6}$ alkyl, —$C_{2-6}$ alkenyl, —$C_{2-6}$ alkynyl, —O—$C_{1-6}$ alkyl, —$C_{3-8}$ cycloalkyl, —$C_{1-6}$ alkyl$C_{3-8}$ cycloalkyl, aryl, heteroaryl, heterocyclyl, and $R^N$; and wherein the alkyl, alkenyl, alkynyl, $C_{3-8}$ cycloalkyl, aryl, heteroaryl, or heterocyclyl group is optionally substituted with 1 to 4 groups independently selected from oxo, —$NO_2$, —$N_3$, —$OR^a$, halo, cyano, —$NR^aR^b$, —$C(O)R^a$, —$C(O)OR^a$, —O—$C_{1-6}$cyanoalkyl, —$C(O)NR^aR^b$, $NR^aC(O)R^a$, —$NR^aC(O)OR^a$, —$SO_2R^a$, —$NR^aSO_2R^b$, —$SO_2NR^aR^b$, —$NR^aSO_2NR^aR^b$, —$C(O)NR^aSO_2NR^aR^b$ and —$C_{3-8}$ cycloalkyl; and further wherein the heteroaryl or heterocyclic group may be oxidized on a nitrogen atom to form an N-oxide or oxidized on a sulfur atom to form a sulfoxide or sulfone;

$R^N$ is independently —$C_{1-6}$ alkyl$NR^1R^2$, —$OC_{1-6}$ alky$NR^1R^2$, —$C_{1-6}$ alkyl$OC_{1-6}$ alkyl$NR^1R^2$, —$NR^aC_{1-6}$ alkyl$NR^1R^2$, —$C_{1-6}$ alkyl$C(O)NR^1R^2$, —$OC_{1-6}$ alkyl$C(O)NR^1R^2$, —$OC_{1-6}$ alkyl$C(O)OR^1$, —$SC_{1-6}$alkyl$NR^1R^2$, —$C_{1-6}$alkyl$OR^a$, or

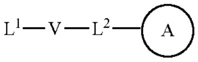;

wherein: $L^1$ is independently a bond, O, $NR^a$, S, SO, or $SO_2$;

V is independently selected from a bond, $C_{1-6}$alkyl, $C_{2-6}$alkenyl, and $C_{2-6}$alkynyl;

wherein each alkyl, alkenyl, or alkynyl is optionally independently substituted with $OR^a$, halo, cyano, —$NR^aR^b$ or —$C_{3-8}$ cycloalkyl;

$L^2$ is independently a bond, O, $NR^a$, S, SO, or $SO_2$;

ring A is independently cycloalkyl, aryl, heteroaryl, or heterocyclyl;

wherein each cycloalkyl, aryl, heteroaryl, or heterocyclyl is optionally substituted with 1 to 4 groups independently selected from oxo, —$NO_2$, —$N_3$, —$OR^a$, halo, cyano, —$C_{1-6}$ alkyl, —$C_{1-6}$ haloalkyl, —$C_{2-6}$alkenyl, —$C_{2-6}$ alkynyl, —O—$C_{1-6}$ haloalkyl, $NR^aR^b$, —$C(O)R^a$, —$C(O)OR^a$, —$OC_{1-6}$ alkylCN, —$C(O)NR^aR^b$, —$NR^aC(O)R^a$, —$NR^aC(O)OR^a$, —$NR^aC(O)OR^a$, —$C(O)N(R^a)OR^b$, —$SO_2R^a$, —$SO_2NR^aR^b$, —$NR^aSO_2R^b$, —$NR^aSO_2NR^aR^b$, —$C(O)NR^aSO_2NR^aR^b$, $C_{3-8}$cycloalkyl, and $C_{1-6}$alkyl$C_{3-8}$ cycloalkyl; and wherein the alkyl, alkenyl, or alkynyl group is optionally independently substituted with —$OR^a$, halo, cyano, —$NR^aR^b$ or —$C_{3-8}$ cycloalkyl;

each t is independently 0, 1 or 2;

$R^E$ and $R^W$ are each independently —$NR^1R^2$, —$C_{1-6}$ alky$NR^1R^2$, —O—$C_{1-6}$ alky$NR^1R^2$, —$C_{1-6}$alkyl$OC_{1-6}$alky$NR^1R^2$, —$NR^a$—$C_{1-6}$alkyl$NR^1R^2$, —$C_{1-6}$alkyl$N^+R^1R^2R^3$, —S—$C_{1-6}$alkyl$NR^1R^2$, —$C(O)NR^1R^2$, —$SO_2R^a$, —$(CH_2)_uSO_2NR^1R^2$, —$(CH_2)_uNR^aSO_2NR^aR^b$, —$SO_2NR^aC_{1-6}$ alky$NR^1R^2$, —$NR^aSO_2C_{1-6}$ alkyl$NR^1R^2$, —$(CH_2)_uC(O)NR^aSO_2NR^aR^b$, —$(CH_2)_uN^+R^1R^2O^-$, —$(CH_2)_uP^+R^bR^cR^d$, —$(CH_2)_uP^+R^cR^dO^-$, —$(CH_2)_uP^+O[NR^aR^b][NR^cR^d]$, —$(CH_2)_uNR^cP(O)(OR^c)_2$, —$(CH_2)_uCH_2OP(O)(OR^c)(OR^d)$, —$(CH_2)_uOP(O)(OR^c)(OR^d)$, —$(CH_2)_uOP(O)NR^aR^b)(OR^a)$, or

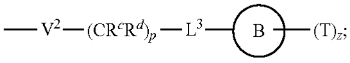;

wherein:

$V^2$ is independently a bond, O, $NR^a$, S, SO, $SO_2$, $C(O)NR^a$, $NR^aC(O)$, $SO_2NR$, or $NR^aSO_2$;

$L^3$ is independently a bond, O, $NR^a$, S, SO, $SO_2$, $C(O)NR^a$, $NR^aC(O)$, $SO_2NR$, or $NR^aSO_2$;

ring B is independently cycloalkyl, aryl, heteroaryl, or heterocyclyl;

T is independently H, $OR^a$, $(CH_2)NR^1R^2$, $(CH_2)_qNR^aC(O)R$, or $(CH_2)C(O)R^e$;

p is independently 0, 1, 2, 3, 4, or 5;

q is independently 0, 1, 2, 3, 4, or 5;

u is 0, 1, 2, 3, or 4;

z is 0, 1, 2, or 3; and wherein the alkyl, cycloalkyl, aryl, heteroaryl, or heterocyclyl of $R^E$ or $R^W$ is optionally substituted with 1 to 3 substituents independently selected from the group consisting of $NR^aR^b$, halo, cyano, oxo, $OR^a$, —$C_{1-6}$alkyl, —$C_{1-6}$haloalkyl, —$C_{1-6}$cyanoalkyl, —$C_{1-6}$alky$NR^aR^b$, —$C_{1-6}$alkylOH, —$C_{3-8}$cycloalkyl, and —$C_{1-3}$ alkyl$C_{3-8}$cycloalkyl;

provided that at least one of $V^2$, $L^3$, ring B and T contains a nitrogen atom;

each $R^1$ is independently selected from H, —$C_{1-8}$ alkyl, —$C_{2-6}$ alkenyl, —$C_{2-6}$ alkynyl, —$C_{3-6}$ cycloalkyl, aryl, heteroaryl, heterocyclyl, —$C_{1-6}$alkylaryl, —$C_{1-6}$alkylheteroaryl, —$C_{1-6}$alkylheterocyclyl, —$C_{1-6}$ alkyl$C(O)OR^a$, —$C_{2-6}$ alkenyl$C(O)OR^a$, —$SO_2R^a$, —$SO_2NR^aR^b$, —$C(O)NR^aSO_2R^a$, and $C_{1-6}$ alkyl $C_{3-8}$cycloalkyl;

wherein each alkyl, alkenyl, cycloalkyl, aryl, heteroaryl, or heterocyclyl is optionally substituted with 1 to 4 groups independently selected from —$OR^a$, —CN, halo, $C_{1-6}$alkyl, —$C_{1-6}$alkyl$OR^a$, —$C_{1-6}$cyanoalkyl, —$C_{1-6}$haloalkyl, $C_{3-8}$cycloalkyl, —$C_{1-3}$alkyl$C_{3-8}$cycloalkyl, —$C(O)R^a$, —$C_{1-6}$ alkyl$C(O)R^a$, —$C(O)OR^a$, —$C_{1-6}$ alkyl$C(O)OR^a$, —$NR^aR^b$, —$OC(O)NR^aR^b$, $NR^aC(O)OR^b$, —$C_{1-6}$alkyl$NR^aR^b$, —$C(O)NR^aR^b$, —$C_{1-6}$alkyl$C(O)NR^aR^b$, —$SO_2R^a$, —$C_{1-6}$alkyl$SO_2R^a$, —$SO_2NR^aR^b$, —$C_{1-6}$ alkyl$SO_2NR^aR^b$, —$C(O)NR^aSO_2R^b$, —$C_{1-6}$ alkyl$C(O)NR^aSO_2R^b$, —$NR^aC(O)R^b$, and —$C_{1-6}$alkyl$NR^aC(O)R^b$;

each $R^2$ is independently selected from H, —$C_{1-6}$ alkyl, —$C_{2-6}$ alkenyl, —$C_{2-6}$ alkynyl, —$C_{3-6}$ cycloalkyl, aryl, heteroaryl, heterocyclyl, —$C_{1-6}$alkylaryl, —$C_{1-6}$alkylheteroaryl, —$C_{1-6}$ alkylheterocyclyl, —$C_{2-6}$alkyl-$OR^a$, —$C_{1-6}$ alkyl$C(O)OR^a$, and —$C_{2-6}$ alkenyl$C(O)OR^a$;

wherein each alkyl, alkenyl, alkynyl, cycloalkyl, aryl, heteroaryl, or heterocyclyl is optionally substituted with 1 to 4 groups independently selected from —$OR^a$, —CN, halo, $C_{1-6}$alkyl, —$C_{1-6}$alkyl$OR^a$, —$C_{1-6}$cyanoalkyl, —$C_{1-6}$haloalkyl, —$C_{3-8}$cycloalkyl, —$C_{1-3}$alkyl$C_{3-8}$cycloalkyl, —$C(O)R^a$, —$C_{1-6}$ alkyl$C(O)R^a$, —$C(O)OR^a$, —$C_{1-6}$ alkyl$C(O)OR^a$, —$NR^aR^b$, —$C_{1-6}$ alkyl$NR^aR^b$, —$C(O)NR^aR^b$, $C_{1-6}$alkyl$C(O)NR^aR^b$, —$SO_2R^a$, —$C_{1-6}$alkyl$SO_2R^a$, —$SO_2NR^aR^b$, —$C_{1-6}$alkyl$SO_2NR^aR^b$, —$C(O)NR^aSO_2R^b$ and —$NR^aC(O)R^b$;

or $R^1$ and $R^2$ combine to form a heterocyclyl group optionally containing 1, 2, or 3 additional heteroatoms independently selected from oxygen, sulfur and nitrogen, and optionally substituted with 1 to 3 groups independently selected from oxo, —$C_{1-6}$ alkyl, —$C_{3-8}$cycloalkyl, —$C_{2-6}$ alkenyl, —$C_{2-6}$ alkynyl, —$OR^a$, —$C(O)OR^a$, —$C_{1-6}$ cyanoalkyl, —$C_{1-6}$ alkyl$OR^a$, —$C_{1-6}$haloalkyl, —$C_{1-3}$ alkyl$C_{3-8}$cycloalkyl, —$C(O)R^a$, $C_{1-6}$alkyl$C(O)R^a$, —$C_{1-6}$alkyl$C(O)OR^a$, —$NR^aR^b$, —$C_{1-6}alkyNR^aR^b$, —$C(O)NR^aR^b$, —$C_{1-6}alkylC(O)NR^aR^b$, —$SO_2R^a$, —$C_{1-6}$ $alkylSO_2R^a$, —$SO_2NR^aR^b$, and $C_{1-6}$ $alkylSO_2NR^aR^b$;

each $R^3$ is independently H, —$C_{1-6}$ alkyl, —$C_{2-6}$ alkenyl, —$C_{3-6}$ cycloalkyl, aryl, heteroaryl, heterocyclyl, —$C_{1-6}$alkylaryl, —$C_{1-6}$alkylheteroaryl, —$C_{1-6}$ alkyl-heterocyclyl, —$C_{2-6}$alkyl-$OR^a$, —$C_{1-6}alkylC(O)OR^a$, or —$C_{2-6}$ $alkenylC(O)OR^a$;

each $R^a$ is independently selected from H, —$C_{1-6}$ alkyl, —$C_{3-8}$cycloalkyl, aryl, heteroaryl, heterocyclyl, —$C_{1-3}$ $alkylC_{3-8}$cycloalkyl, —$C_{1-6}$ alkylaryl, —$C_{1-6}$ alkylheteroaryl, and —$C_{1-6}$alkylheterocyclyl;

$R^b$ is independently selected from H, —$C_{1-6}$ alkyl, —$C_{3-8}$cycloalkyl, aryl, heteroaryl, heterocyclyl, —$C_{1-3}$ $alkylC_{3-8}$cycloalkyl, —$C_{1-6}$ alkylaryl, —$C_{1-6}$ alkylheteroaryl, and —$C_{1-6}$ alkylheterocyclyl;

or $R^a$ and $R^b$ may combine together to form a ring consisting of 3-8 ring atoms that are C, N, O, or S; wherein the ring is optionally substituted with 1 to 4 groups independently selected from —$OR^f$, —CN, halo, —$C_{1-6}$ $alkylOR^f$, —$C_{1-6}$ cyanoalkyl, —$C_{1-6}$haloalkyl, —$C_{3-8}$cycloalkyl, —$C_{1-3}$ $alkylC_{3-8}$cycloalkyl, —$C(O)R^f$, —$C_{1-6}$ $alkylC(O)R^f$, —$C(O)OR^1$, —$C_{1-6}$ $alkylC(O)OR^f$, —$NR^fR^g$, —$C_{1-6}$ $alkylNR^fR^g$, —$C(O)NR^fR^g$, —$C_{1-6}$ $alkylC(O)NR^fR^g$, —$SO_2R^f$, —$C_{1-6}$ $alkylSO_2R$, —$SO_2NR^fR^g$, —$C_{1-6}$ $alkylSO_2NR^fR^g$, —$C(O)NR^fSO_2R^g$ and —$NR^fC(O)R^g$;

each $R^c$ is independently selected from H, OH, —$C_{1-6}$ alkyl, —$C_{3-8}$cycloalkyl, aryl, heteroaryl, heterocyclyl, —$C_{1-3}$ $alkylC_{3-8}$cycloalkyl, —$C_{1-6}$ alkylaryl, —$C_{1-6}$ alkylheteroaryl, and —$C_{1-6}$alkylheterocyclyl;

each $R^d$ is independently selected from H, —$C_{1-6}$ alkyl, —$C_3$-$C_8$cycloalkyl, aryl, heteroaryl, heterocyclyl, —$C_{1-3}$ $alkylC_{3-8}$cycloalkyl, —$C_{1-6}$ alkylaryl, —$C_{1-6}$ alkylheteroaryl, and —$C_{1-6}$alkylheterocyclyl;

each $R^c$ is independently selected from H, —$C_{1-6}$ alkyl, —O—$C_{1-6}$alkyl, —$C_{3-8}$cycloalkyl, aryl, heteroaryl, heterocyclyl, —O—$C_{3-8}$cycloalkyl, —O-aryl, —O-heteroaryl, —O-heterocyclyl, —$C_{1-3}$ $alkylC_{3-8}$cycloalkyl, —$C_{1-6}$alkylaryl, —$C_{1-6}$alkylheteroaryl, —$NR^fR^g$, —$C_{1-6}alkylNR^fR^g$, —$C(O)NR^fR^g$, —$C_{1-6}alkylC(O)NR^fR^g$, —$NHSO_2R^f$, —$C_{1-6}alkylSO_2R^f$, and —$C_{1-6}alkylSO_2NR^fR^g$;

each $R^f$ is independently selected from H, —$C_{1-6}$ alkyl, —$C_{3-8}$cycloalkyl, aryl, heteroaryl, heterocyclyl, —$C_{1-3}$ $alkylC_{3-8}$cycloalkyl, —$C_{1-6}$ alkylaryl, —$C_{1-6}$ alkylheteroaryl, and —$C_{1-6}$alkylheterocyclyl; and each $R^g$ is independently selected from H, —$C_{1-6}$ alkyl, —$C_{3-8}$cycloalkyl, aryl, heteroaryl, heterocyclyl, —$C_{1-3}$ $alkylC_{3-8}$ cycloalkyl, —$C_{1-6}$ alkylaryl, —$C_{1-6}$ alkylheteroaryl, and —$C_{1-6}$alkylheterocyclyl;

or a pharmaceutically acceptable salt, stereoisomer, mixture of stereoisomers, solvate, or tautomer thereof.

In one embodiment, provided is a compound of formula (VIIIa):

(VIIIa)

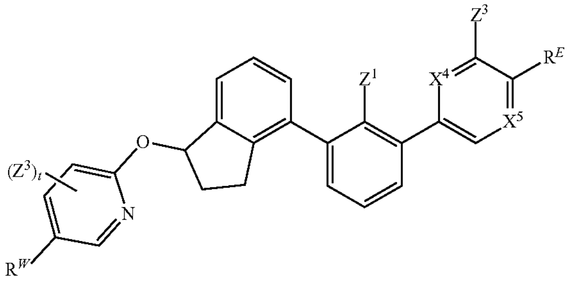

wherein $X^4$, $X^5$, $Z^1$, $Z^3$, t, $R^W$ and $R^E$ are as defined herein. In one embodiment, provided is a compound of formula (VIIIb):

(VIIIb)

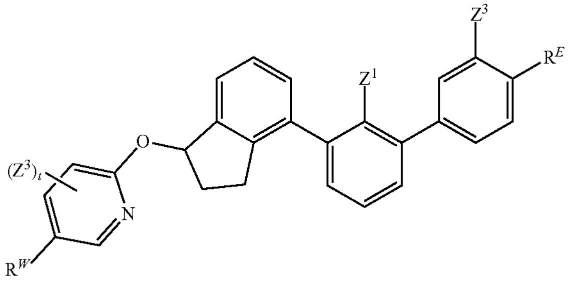

wherein $Z^1$, $Z^3$, t, $R^W$ and $R^E$ are as defined herein. In one embodiment, provided is a compound of formula (VIIIc):

(VIIIc)

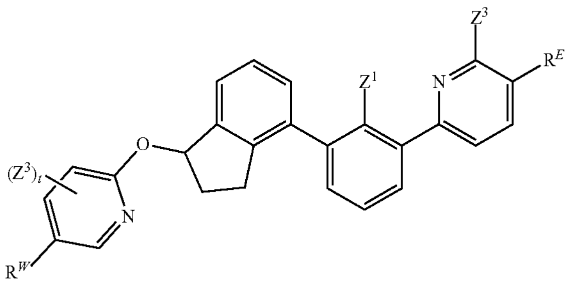

wherein $Z^1$, $Z^3$, t, $R^W$ and $R^E$ are as defined herein. In one embodiment, provided is a compound of formula (VIIId):

(VIIId)

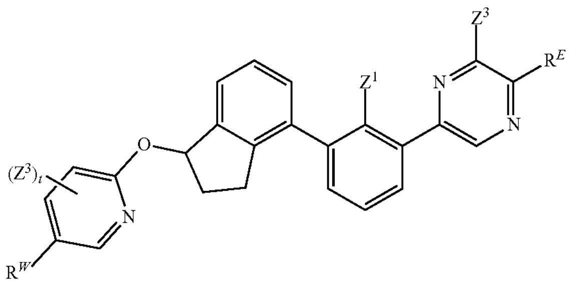

wherein $Z^1$, $Z^3$, t, $R^W$ and $R^E$ are as defined herein.

In one embodiment, provided is a compound of formula (VIIIe):

(VIIIe)

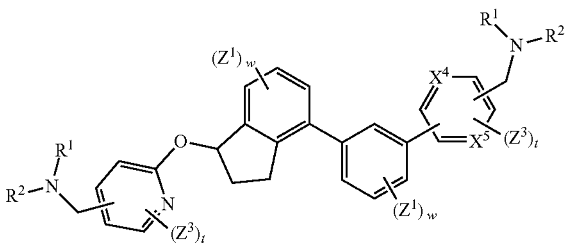

wherein:

each of $X^4$ and $X^5$ are independently N, CH or $CZ^3$;

each $Z^1$ is independently halo, —$OR^a$, —CN, or —$C_{1-6}$ alkyl;

each w is independently 0, 1 or 2;

each $Z^3$ is independently halo, —$OR^a$, —$N_3$, —$NO_2$, —CN, —$NR^1R^2$, —$SO_2R^a$, —$SO_2NR^aR^b$, —$NR^aSO_2R^a$, —$NR^aC(O)R^a$, —$C(O)R^a$, —$C(O)OR^a$, —$C(O)NR^aR^b$, —$NR^aC(O)OR^a$, —$NR^aC(O)NR^1R^2$, —$OC(O)NR^aR^b$, —$NR^aSO_2NR^aR^b$, —$C(O)NR^aSO_2NR^aR^b$, —$C_{1-6}$ alkyl, —$C_{2-6}$ alkenyl, —$C_{2-6}$ alkynyl, —O—$C_{1-6}$ alkyl, —$C_{3-8}$ cycloalkyl, —$C_{1-6}$ alkyl$C_{3-8}$ cycloalkyl, aryl, heteroaryl, heterocyclyl, and $R^N$; and wherein the alkyl, alkenyl, alkynyl, $C_{3-8}$ cycloalkyl, aryl, heteroaryl, or heterocyclyl group is optionally substituted with 1 to 4 groups independently selected from oxo, —$NO_2$, —$N_3$, —$OR^a$, halo, cyano, —$NR^aR^b$, —$C(O)R^a$, —$C(O)OR^a$, —O—$C_{1-6}$cyanoalkyl, —$C(O)NR^aR^b$, $NR^aC(O)R^a$, —$NR^aC(O)OR^a$, —$SO_2R^a$, —$NR^aSO_2R^b$, —$SO_2NR^aR^b$, —$NR^aSO_2NR^aR^b$, —$C(O)NR^aSO_2NR^aR^b$ and —$C_{3-8}$ cycloalkyl; and further wherein the heteroaryl or heterocyclic group may be oxidized on a nitrogen atom to form an N-oxide or oxidized on a sulfur atom to form a sulfoxide or sulfone;

$R^N$ is independently —$C_{1-6}$ alky$NR^1R^2$, —$OC_{1-6}$ alky$NR^1R^2$, —$C_{1-6}$ alkyl$OC_{1-6}$ alkyl$NR^1R^2$, —$NR^a$—$C_{1-6}$ alkyl$NR^1R^2$, —$C_{1-6}$ alkyl$C(O)NR^1R^2$, —O—$C_{1-6}$ alkyl$C(O)NR^1R^2$, —O—$C_{1-6}$ alkyl$C(O)OR^1$, —S—$C_{1-6}$alkyl$NR^1R^2$, —$C_{1-6}$ alkyl$OR^a$, or

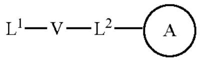;

wherein: $L^1$ is independently a bond, O, $NR^a$, S, SO, or $SO_2$;

V is independently selected from a bond, $C_{1-6}$alkyl, $C_{2-6}$alkenyl, and $C_{2-6}$alkynyl;

wherein each alkyl, alkenyl, or alkynyl is optionally independently substituted with $OR^a$, halo, cyano, —$NR^aR^b$ or —$C_{3-8}$cycloalkyl;

$L^2$ is independently a bond, O, $NR^a$, S, SO, or $SO_2$;

ring A is independently cycloalkyl, aryl, heteroaryl, or heterocyclyl;

wherein each cycloalkyl, aryl, heteroaryl, or heterocyclyl is optionally substituted with 1 to 4 groups independently selected from oxo, —$NO_2$, —$N_3$, —$OR^a$, halo, cyano, —$C_{1-6}$ alkyl, —$C_{1-6}$ haloalkyl, —$C_{2-6}$alkenyl, —$C_{2-6}$ alkynyl, —O—$C_{1-6}$ haloalkyl, $NR^aR^b$, —$C(O)R^a$, —$C(O)OR^a$, —$OC_{1-6}$ alkylCN, —$C(O)NR^aR^b$, —$NR^aC(O)R^a$, —$NR^aC(O)OR^a$, —$NR^aC(O)OR^a$, —$C(O)N(R^a)OR^b$, —$SO_2R^a$, —$SO_2NR^aR^b$, —$NR^aSO_2R^b$, —$NR^aSO_2NR^aR^b$, —$C(O)NR^aSO_2NR^aR^b$, $C_{3-8}$cycloalkyl, and $C_{1-6}$alkyl$C_{3-8}$ cycloalkyl; and wherein the alkyl, alkenyl, or alkynyl group is optionally independently substituted with —$OR^a$, halo, cyano, —$NR^aR^b$ or —$C_{3-8}$ cycloalkyl;

each t is independently 0, 1 or 2;

each $R^1$ is independently selected from H, —$C_{1-8}$ alkyl, —$C_{2-6}$ alkenyl, —$C_{2-6}$ alkynyl, —$C_{3-6}$ cycloalkyl, aryl, heteroaryl, heterocyclyl, —$C_{1-6}$alkylaryl, —$C_{1-6}$alkylheteroaryl, —$C_{1-6}$alkylheterocyclyl, —$C_{1-6}$ alkyl$C(O)OR^a$, —$C_{2-6}$ alkenyl$C(O)OR^a$, —$SO_2R^a$, —$SO_2NR^aR^b$, —$C(O)NR^aSO_2R^a$, and $C_{1-6}$ alkyl $C_{3-8}$cycloalkyl;

wherein each alkyl, alkenyl, cycloalkyl, aryl, heteroaryl, or heterocyclyl is optionally substituted with 1 to 4 groups independently selected from —$OR^a$, —CN, halo, $C_{1-6}$alkyl, —$C_{1-6}$alkyl$OR^a$, —$C_{1-6}$cyanoalkyl, —$C_{1-6}$haloalkyl, $C_{3-8}$cycloalkyl, —$C_{1-3}$alkyl$C_{3-8}$cycloalkyl, —$C(O)R^a$, —$C_{1-6}$ alkyl$C(O)R^a$, —$C(O)OR^a$, —$C_{1-6}$ alkyl$C(O)OR^a$, —$NR^aR^b$, —$OC(O)NR^aR^b$, $NR^aC(O)OR^b$, —$C_{1-6}$alkyl$NR^aR^b$, —$C(O)NR^aR^b$, —$C_{1-6}$alkyl$C(O)NR^aR^b$, —$SO_2R^a$, —$C_{1-6}$alkyl$SO_2R^a$, —$SO_2NR^aR^b$, —$C_{1-6}$ alkyl$SO_2NR^aR^b$, —$C(O)NR^aSO_2R^b$, —$C_{1-6}$ alkyl$C(O)NR^aSO_2R^b$, —$NR^aC(O)R^b$, and —$C_{1-6}$alkyl$NR^aC(O)R^b$;

each $R^2$ is independently selected from H, —$C_{1-6}$alkyl, —$C_{2-6}$ alkenyl, —$C_{2-6}$ alkynyl, —$C_{3-6}$ cycloalkyl, aryl, heteroaryl, heterocyclyl, —$C_{1-6}$alkylaryl, —$C_{1-6}$alkylheteroaryl, —$C_{1-6}$ alkylheterocyclyl, —$C_{2-6}$alkyl-$OR^a$, —$C_{1-6}$ alkyl$C(O)OR^a$, and —$C_{2-6}$ alkenyl$C(O)OR^a$;

wherein each alkyl, alkenyl, alkynyl, cycloalkyl, aryl, heteroaryl, or heterocyclyl is optionally substituted with 1 to 4 groups independently selected from —$OR^a$, —CN, halo, $C_{1-6}$alkyl, —$C_{1-6}$alkyl$OR^a$, —$C_{1-6}$cyanoalkyl, —$C_{1-6}$haloalkyl, —$C_{3-8}$cycloalkyl, —$C_{1-3}$alkyl$C_{3-8}$cycloalkyl, —$C(O)R^a$, —$C_{1-6}$ alkyl$C(O)R^a$, —$C(O)OR^a$, —$C_{1-6}$ alkyl$C(O)OR^a$, —$NR^aR^b$, —$C_{1-6}$ alkyl$NR^aR^b$, —$C(O)NR^aR^b$, $C_{1-6}$alkyl$C(O)NR^aR^b$, —$SO_2R^a$, —$C_{1-6}$alkyl$SO_2R^a$, —$SO_2NR^aR^b$, —$C_{1-6}$alkyl$SO_2NR^aR^b$, —$C(O)NR^aSO_2R^b$ and —$NR^aC(O)R^b$;

or $R^1$ and $R^2$ combine to form a heterocyclyl group optionally containing 1, 2, or 3 additional heteroatoms independently selected from oxygen, sulfur and nitrogen, and optionally substituted with 1 to 3 groups independently selected from oxo, $-C_{1-6}$ alkyl, $-C_{3-8}$cycloalkyl, $-C_{2-6}$ alkenyl, $-C_{2-6}$ alkynyl, $-OR^a$, $-C(O)OR^a$, $-C_{1-6}$ cyanoalkyl, $-C_{1-6}$ alkylOR$^a$, $-C_{1-6}$haloalkyl, $-C_{1-3}$ alkylC$_{3-8}$cycloalkyl, $-C(O)R^a$, $C_{1-6}$alkylC(O)R$^a$, $-C_{1-6}$alkylC(O)OR$^a$, $-NR^aR^b$, $-C_{1-6}$alkyNR$^a$R$^b$, $-C(O)NR^aR^b$, $-C_{1-6}$alkylC(O)NR$^a$R$^b$, $-SO_2R^a$, $-C_{1-6}$ alkylSO$_2$R$^a$, $-SO_2NR^aR^b$, and $C_{1-6}$ alkylSO$_2$NR$^a$R$^b$;

each $R^3$ is independently H, $-C_{1-6}$ alkyl, $-C_{2-6}$ alkenyl, $-C_{3-6}$ cycloalkyl, aryl, heteroaryl, heterocyclyl, $-C_{1-6}$alkylaryl, $-C_{1-6}$alkylheteroaryl, $-C_{1-6}$ alkylheterocyclyl, $-C_{2-6}$alkyl-OR$^a$, $-C_{1-6}$alkylC(O)OR$^a$, or $-C_{2-6}$ alkenylC(O)OR$^a$;

each $R^a$ is independently selected from H, $-C_{1-6}$ alkyl, $-C_{3-8}$cycloalkyl, aryl, heteroaryl, heterocyclyl, $-C_{1-3}$ alkylC$_{3-8}$cycloalkyl, $-C_{1-6}$ alkylaryl, $-C_{1-6}$ alkylheteroaryl, and $-C_{1-6}$alkylheterocyclyl;

each $R^b$ is independently selected from H, $-C_{1-6}$ alkyl, $-C_{3-8}$cycloalkyl, aryl, heteroaryl, heterocyclyl, $-C_{1-3}$ alkylC$_{3-8}$cycloalkyl, $-C_{1-6}$ alkylaryl, $-C_{1-6}$ alkylheteroaryl, and $-C_{1-6}$ alkylheterocyclyl;

or $R^a$ and $R^b$ may combine together to form a ring consisting of 3-8 ring atoms that are C, N, O, or S; wherein the ring is optionally substituted with 1 to 4 groups independently selected from $-OR^f$, $-CN$, halo, $-C_{1-6}$ alkylOR$^f$, $-C_{1-6}$ cyanoalkyl, $-C_{1-6}$haloalkyl, $-C_{3-8}$cycloalkyl, $-C_{1-3}$ alkylC$_{3-8}$cycloalkyl, $-C(O)R^f$, $-C_{1-6}$ alkylC(O)R$^f$, $-C(O)OR^f$, $-C_{1-6}$ alkylC(O)OR$^f$, $-NR^fR^g$, $-C_{1-6}$ alkylNR$^f$R$^g$, $-C(O)NR^fR^g$, $-C_{1-6}$ alkylC(O)NR$^f$R$^g$, $-SO_2R^f$, $-C_{1-6}$ alkylSO$_2$NR$^f$R$^g$, $-C_{1-6}$ alkylSO$_2$NR$^f$R$^g$, $-C(O)NR^fSO_2R^g$ and $-NR^fC(O)R^g$;

each $R^c$ is independently selected from H, OH, $-C_{1-6}$ alkyl, $-C_{3-8}$ cycloalkyl, aryl, heteroaryl, heterocyclyl, $-C_{1-3}$ alkylC$_{3-8}$cycloalkyl, $-C_{1-6}$ alkylaryl, $-C_{1-6}$ alkylheteroaryl, and $-C_{1-6}$alkylheterocyclyl;

$R^d$ is independently selected from H, $-C_{1-6}$ alkyl, $-C_3$-C$_8$cycloalkyl, aryl, heteroaryl, heterocyclyl, $-C_{1-3}$ alkylC$_{3-8}$cycloalkyl, $-C_{1-6}$ alkylaryl, $-C_{1-6}$ alkylheteroaryl, and $-C_{1-6}$alkylheterocyclyl;

each $R^f$ is independently selected from H, $-C_{1-6}$ alkyl, $-C_{3-8}$ cycloalkyl, aryl, heteroaryl, heterocyclyl, $-C_{1-3}$ alkylC$_{3-8}$cycloalkyl, $-C_{1-6}$ alkylaryl, $-C_{1-6}$ alkylheteroaryl, and $-C_{1-6}$alkylheterocyclyl; and each $R^g$ is independently selected from H, $-C_{1-6}$ alkyl, $-C_{3-8}$ cycloalkyl, aryl, heteroaryl, heterocyclyl, $-C_{1-3}$ alkylC$_{3-8}$cycloalkyl, $-C_{1-6}$ alkylaryl, $-C_{1-6}$ alkylheteroaryl, and $-C_{1-6}$alkylheterocyclyl;

or a pharmaceutically acceptable salt, stereoisomer, mixture of stereoisomers, solvate, or tautomer thereof.

In one embodiment, provided is a compound of formula (VIIIf):

(VIIIf)

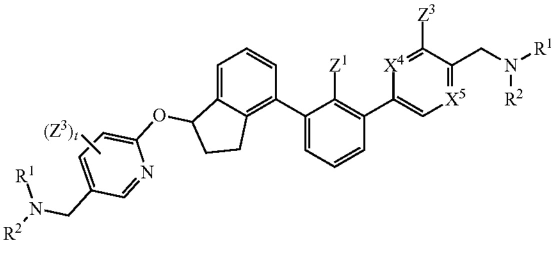

wherein $X^4$, $X^5$, $Z^1$, $Z^3$, t, $R^1$ and $R^2$ are as defined herein.

In one embodiment, provided is a compound of formula (VIIIg):

(VIIIg)

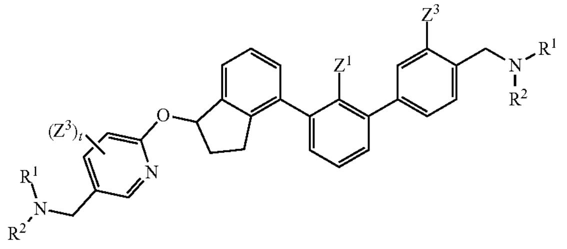

wherein $Z^1$, $Z^3$, t, $R^1$ and $R^2$ are as defined herein. In one embodiment, provided is a compound of formula (VIIIh):

(VIIIh)

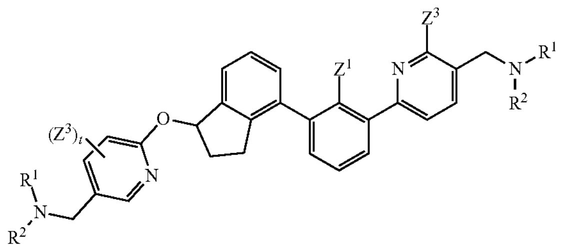

wherein $Z^1$, $Z^3$, t, $R^1$ and $R^2$ are as defined herein. In one embodiment, provided is a compound of formula (VIIIi):

(VIIIi)

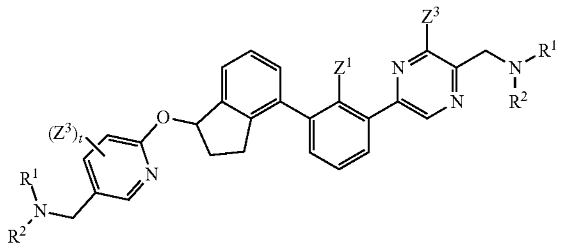

wherein $Z^1$, $Z^3$, t, $R^1$ and $R^2$ are as defined herein.

In certain embodiments of any one of formulas (VIII)-(VIIIi), each $Z^1$ is independently halo. In certain embodiments of any one of formulas (VIII)-(VIIIi), each $Z^3$ is independently halo or $C_{1-6}$ alkoxy.

In certain embodiments of any one of formulas (VIII)-(VIIIi), each $Z^1$ is independently chloro. In certain embodiments of any one of formulas (VIII)-(VIIIi), each $Z^3$ is independently chloro or methoxy.

In one embodiment provided is a compound selected from Examples 637-803.

In certain embodiments, the compound as provided herein has a molecular weight of less than about 1200 g/mol, or less than about 1100 g/mol, or less than about 1000 g/mol, or less than about 900 g/mol, or less than about 800 g/mol, or between about 1200 to about 600 g/mol, or between about 1000 to about 700 g/mol, or between about 1000 to about 800 g/mol.

One of skill in the art is aware that each and every embodiment of a group (e.g., $Ar^E$) disclosed herein may be combined with any other embodiment of each of the remaining groups (e.g., $Q^E$, $Ar^W$ $Q^W$, etc.) to generate a complete compound of formula (I) as disclosed herein; each of which is deemed within the ambit of the present disclosure.

Formulations and Methods

Methods

In one embodiment, the present disclosure provides a compound of formula (I) useful as an inhibitor of PD-1, PD-L1 and/or the PD-1/PD-L1 interaction. In some embodiments, compounds disclosed herein inhibit the PD-1/PD-L1 interaction by dimerizing PD-L1, or by inducing or stabilizing PD-L1 dimer formation.

In one embodiment, the present disclosure provides a method of treating cancer comprising administering a compound of formula (I) in combination with one or more check-point inhibitors selected from nivolumab, pembrolizumab, and artezolizumab.

In one embodiment, the present disclosure provides a pharmaceutical composition comprising a compound of formula (I) and a pharmaceutically acceptable carrier.

In one embodiment, the present disclosure provides a pharmaceutical composition comprising a compound of formula (I) or a pharmaceutically acceptable salt, stereoisomer, mixture of stereoisomers or tautomer thereof, and at least one additional anticancer agent and at least one pharmaceutically acceptable excipient.

The present disclosure provides a compound of formula (I) for use in therapy.

In another embodiment, the present disclosure provides a compound of formula (I) for use in the manufacture of a medicament for treating cancer.

In one embodiment, provided is a compound of formula (I) or a pharmaceutically acceptable salt, stereoisomer, mixture of stereoisomers or tautomer thereof, useful for the treatment of cancer or a condition in a patient that is amenable to treatment by inhibiting PD-1, PD-L1 or the PD-1/PD-L interaction. Cancers that may be treated with the compounds of formula (I) disclosed herein include pancreatic cancer, bladder cancer, colorectal cancer, breast cancer, prostate cancer, renal cancer, hepatocellular cancer, lung cancer, ovarian cancer, cervical cancer, gastric cancer, esophageal cancer, head and neck cancer, melanoma, neuroendocrine cancer, CNS cancer, brain cancer, bone cancer, soft tissue sarcoma, non-small cell lung cancer, small-cell lung cancer and colon cancer.

In one embodiment, provided is a compound of formula (I) or a pharmaceutically acceptable salt, stereoisomer, mixture of stereoisomers or tautomer thereof, useful for the treatment of cancer or a condition in a patient that is amenable to treatment by inhibiting PD-1, PD-L1 or the PD-1/PD-L1 interaction including, but not limited to, lymphoma, multiple myeloma, and leukemia. Additional diseases or conditions that may be treated include, but are not limited to acute lymphocytic leukemia (ALL), acute myeloid leukemia (AML), chronic lymphocytic leukemia (CLL), small lymphocytic lymphoma (SLL), myelodysplastic syndrome (MDS), myeloproliferative disease (MPD), chronic myeloid leukemia (CML), multiple myeloma (MM), non-Hodgkin's lymphoma (NHL), mantle cell lymphoma (MCL), follicular lymphoma, Waldestrom's macroglobulinemia (WM), T-cell lymphoma, B-cell lymphoma and diffuse large B-cell lymphoma (DLBCL).

In one embodiment, provided is a method of treating HBV, comprising administering to a patient in need thereof a compound of formula (I), or a pharmaceutically acceptable salt, stereoisomer, mixture of stereoisomers or tautomer thereof.

"Administering" or "administration" refers to the delivery of one or more therapeutic agents to a patient. In one embodiment, the administration is a monotherapy wherein a compound of formula (I) is the only active ingredient administered to the patient in need of therapy. In another embodiment, the administration is co-administration such that two or more therapeutic agents are delivered together during the course of the treatment. In one embodiment, two or more therapeutic agents may be co-formulated into a single dosage form or "combined dosage unit", or formulated separately and subsequently combined into a combined dosage unit, as is typically for intravenous administration or oral administration as a mono or bilayer tablet or capsule.

In one embodiment, the compound of formula (I) or a pharmaceutically acceptable salt thereof is administered to a human patient in need thereof in an effective amount, such as, from about 0.1 mg to about 1000 mg per day of said compound. In one embodiment, the effective amount is from about 0.1 mg to about 200 mg per day. In one embodiment, the effective amount is from about 1 mg to about 100 mg per day. In other embodiments, the effective amount is about 1 mg, about 3 mg, about 5 mg, about 10 mg, about 15 mg, about 18 mg, about 20 mg, about 30 mg, about 40 mg, about 60 mg, about 80 mg, or about 100 mg per day.

In one embodiment, the compound of formula (I) or a pharmaceutically acceptable salt thereof and at least one additional anticancer agent is administered to a human patient in need thereof in an effective amount of each agent, independently from about 0.1 mg to about 1000 mg per compound or formulation per day per compounds. In one embodiment, the effective amount of the combination treatment of a compound of formula (I) and an additional compound is independently from about 0.1 mg to about 200 mg per compound per day. In one embodiment, the effective amount of the combination treatment of a compound of formula (I) and an additional compound is independently from about 1 mg to about 100 mg per compound per day. In other embodiments, the effective amount of the combination treatment of a compound of formula (I) and an additional compound is for each component, about 1 mg, about 3 mg, about 5 mg, about 10 mg, about 15 mg, about 18 mg, about 20 mg, about 30 mg, about 40 mg, about 60 mg, about 80 mg, about 100 mg, about 200 mg, or about 500 mg each per day.

In one embodiment, the compound of formula (I) and/or a combination of the compound of formula (I) and an additional anticancer agent or a pharmaceutically acceptable salt thereof is administered once a day. In yet another embodiment, the compound of formula (I) and/or an additional anticancer agent or a pharmaceutically acceptable salt thereof is administered as a loading dose of from about 10 mg to about 500 mg per compound on the first day and each day or on alternate days or weekly for up to a month followed by a regular regimen of a compound of formula (I) and/or one or more additional anticancer agents or therapies. The maintenance dose may be 1-500 mg daily or weekly for each component of a multi component drug regimen. A qualified care giver or treating physician is aware of what dose regimen is best for a particular patient or particular presenting conditions and will make appropriate treating regimen decisions for that patient. Thus, in another embodiment, the qualified caregiver is able to tailor a dose regimen of the compound of formula (I) and/or an additional agent(s) as disclosed herein to fit with the particular needs of the patient. Thus, it will be understood that the amount of the compound of formula (I), or a pharmaceutically acceptable salt thereof and the amount of an additional agent actually administered will usually be determined by a physician, in light of the relevant circumstances, including the condition(s) to be treated, the chosen route of administration, the actual compound (e.g., salt or free base) administered and its relative activity, the age, weight, and response of the individual patient, the severity of the patient's symptoms, and the like.

Co-administration may also include administering component drugs e.g., one on more compounds of formula (I) and one or more additional (e.g., a second, third, fourth or fifth) anticancer or other therapeutic agent(s). Such combination of one on more compounds of formula (I) and one or more additional anticancer or other therapeutic agent(s) may be administered simultaneously or in sequence (one after the other) within a reasonable period of time of each administration (e.g., about 1 minute to 24 hours) depending on the pharmacokinetic and/or pharmacodynamics properties of each agent or the combination. Co-administration may also involve treatment with a fixed combination wherein agents of the treatment regimen are combinable in a fixed dosage or combined dosage medium e.g., solid, liquid or aerosol. In one embodiment, a kit may be used to administer the drug or drug components.

Thus, one embodiment of the present disclosure is a method of treating a disease amenable to treatment with a PD-1, PD-L1 inhibitor or a PD-1/PD-L1 interaction inhibitor e.g., cancer comprising administering therapeutically effective amounts of formulations of one on more compounds of formula (I) and one or more additional anticancer agents, including for example, via a kit to a patient in need thereof. It will be understood that a qualified care giver will administer or direct the administration of a therapeutically effective amount of any of the compound(s) or combinations of compounds of the present disclosure.

"Intravenous administration" is the administration of substances directly into a vein, or "intravenously." Compared with other routes of administration, the intravenous (IV) route is a faster way to deliver fluids and medications throughout the body. An infusion pump can allow precise control over the flow rate and total amount of medication delivered. However, in cases where a change in the flow rate would not have serious consequences, or if pumps are not available, the drip is often left to flow simply by placing the bag above the level of the patient and using the clamp to regulate the rate. Alternatively, a rapid infuser can be used if the patient requires a high flow rate and the IV access device is of a large enough diameter to accommodate it. This is either an inflatable cuff placed around the fluid bag to force the fluid into the patient or a similar electrical device that may also heat the fluid being infused. When a patient requires medications only at certain times, intermittent infusion is used which does not require additional fluid. It can use the same techniques as an intravenous drip (pump or gravity drip), but after the complete dose of medication has been given, the tubing is disconnected from the IV access device. Some medications are also given by IV push or bolus, meaning that a syringe is connected to the IV access device and the medication is injected directly (slowly, if it might irritate the vein or cause a too-rapid effect). Once a medicine has been injected into the fluid stream of the IV tubing there must be some means of ensuring that it gets from the tubing to the patient. Usually this is accomplished by allowing the fluid stream to flow normally and thereby carry the medicine into the bloodstream; however, a second fluid injection is sometimes used, as a "flush", following the injection to push the medicine into the bloodstream more quickly. Thus in one embodiment, compound(s) or combination of compounds described herein may be administered by IV administration alone or in combination with administration of certain components of the treatment regimen by oral or parenteral routes.

"Oral administration" is a route of administration where a substance is taken through the mouth, and includes buccal, sub labial, and sublingual administration, as well as enteral administration and that through the respiratory tract, unless made through e.g., tubing so the medication is not in direct contact with any of the oral mucosa. Typical form for the oral administration of therapeutic agents includes the use of tablets or capsules. Thus in one embodiment, compound(s) or combination of compounds described herein may be administered by oral route alone or in combination with administration of certain components of the treatment regimen by IV or parenteral routes.

Pharmaceutical Formulations

The compound(s) of formula (I) or a pharmaceutically acceptable salt thereof may be administered in a pharmaceutical formulation. Pharmaceutical formulations/compositions contemplated by the present disclosure comprise, in addition to a carrier, the compound of formula (I), or a pharmaceutically acceptable salt thereof, or a combination of compound of formula (I), or a pharmaceutically acceptable salt thereof, optionally in combination with an additional agent such as for example, ipilimumab, or a pharmaceutically acceptable salt thereof.

Pharmaceutical formulations/compositions contemplated by the present disclosure may also be intended for administration by injection and include aqueous solutions, oil suspensions, emulsions (with sesame oil, corn oil, cottonseed oil, or peanut oil) as well as elixirs, mannitol, dextrose, or a sterile aqueous solution, and similar pharmaceutical vehicles. Aqueous solutions in saline are also conventionally used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and/or by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the component compound(s) in the required amount in the appropriate solvent with various other ingredients as enumerated above or as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient(s) plus any additional desired ingredient from a previously sterile-filtered solution thereof.

In making pharmaceutical compositions that comprise compound of formula (I), or a pharmaceutically acceptable salt thereof, optionally in combination with an additional agent/therapy useful for the purpose or pharmaceutically acceptable salt thereof, the active ingredient is usually diluted by an excipient or carrier and/or enclosed or mixed with such a carrier that may be in the form of a capsule, sachet, paper or other container. When the excipient serves as a diluent, it can be a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 20% by weight of the active compounds, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents.

The compositions of the disclosure may be formulated so as to provide quick, sustained or delayed release of the active ingredient after administration to the patient by employing procedures known in the art. In one embodiment, sustained release formulations are used. Controlled release drug delivery systems for oral administration include osmotic pump systems and dissolutional systems containing polymer-coated reservoirs or drug-polymer matrix formulations.

Certain compositions are preferably formulated in a unit dosage form. The term "unit dosage forms" or "combined dosage unit" refers to physically discrete units suitable as unitary dosages for human subjects and other mammals, each unit containing a predetermined quantity of one or more of the active materials (e.g., compound (I), optionally in combination with an additional agent calculated to produce the desired effect, in association with a suitable pharmaceutical excipient in for example, a tablet, capsule, ampoule or vial for injection. It will be understood, however, that the amount of each active agent actually administered will be determined by a physician, in the light of the relevant circumstances, including the condition to be treated, the chosen route of administration, the actual compounds administered and their relative activity, the age, weight, and response of the individual patient, the severity of the patient's symptoms, and the like.

For preparing solid compositions such as tablets, the principal active ingredient(s) is/are mixed with a pharmaceutical excipient to form a solid pre-formulation composition containing a homogeneous mixture of a compound of the present disclosure. When referring to these pre-formulation compositions as homogeneous, it is meant that the active ingredient(s) are dispersed evenly throughout the composition so that the composition may be readily subdivided into equally effective unit dosage forms such as tablets, pills and capsules.

The tablets or pills comprising compound of formula (I) or a pharmaceutically acceptable salt thereof of the present disclosure optionally in combination with the second agent may be coated or otherwise compounded to provide a dosage form affording the advantage of prolonged action, or to protect from the acidic conditions of the stomach. For example, the tablet or pill can comprise an inner dosage and an outer dosage element, the latter being in the form of an envelope over the former. In one embodiment, the inner dosage element may comprise the compound (I) and the outer dosage element may comprise the second or additional agent or vice versa. Alternatively, the combined dosage unit may be side by side configuration as in a capsule or tablet where one portion or half of the tablet or capsule is filled with a formulation of the compound of formula (I) while the other portion or half of the table or capsule comprises the additional agent A variety of materials may be used for such enteric layers or coatings, such materials including a number of polymeric acids and mixtures of polymeric acids with such materials as shellac, cetyl alcohol, and cellulose acetate. One of ordinary skill in the art is aware of techniques and materials used in the manufacture of dosages of formulations disclosed herein.

A "sustained release formulation" or "extended release formulation" is a formulation which is designed to slowly release a therapeutic agent into the body over an extended period of time, whereas an "immediate release formulation" is a formulation which is designed to quickly release a therapeutic agent into the body over a shortened period of time. In some cases the immediate release formulation may be coated such that the therapeutic agent is only released once it reaches the desired target in the body (e.g., the stomach). One of ordinary skill in the art is able to develop sustained release formulations of the presently disclosed compounds without undue experimentation. Thus in one embodiment, compound(s) or combination of compounds described herein may be delivered via sustained released formulations alone or in combination with administration of certain components of the treatment regimen by oral, IV or parenteral routes.

A lyophilized formulation may also be used to administer a compound of formula (I) singly or in combination with an additional anticancer agent. One of skill in the art is aware of how to make and use lyophilized formulations of drug substances amenable to lyophilization.

Spray-dried formulation may also be used to administer a compound of formula (I) singly or in combination with an additional anti-cancer agent. One of skill in the art is aware of how to make and use spray-dried formulations of drug substances amenable to spray-drying. Other known formulation techniques may also be employed to formulate a compound or combination of compounds disclosed herein.

Combination Therapy

Also provided are methods of treatment in which a compound of formula (I) or a pharmaceutically acceptable salt thereof, is given to a patient in combination with one or more additional active agents or therapy.

Thus in one embodiment, a method of treating cancer and/or diseases or symptoms that co-present or are exacerbated or triggered by the cancer e.g., an allergic disorder and/or an autoimmune and/or inflammatory disease, and/or an acute inflammatory reaction, comprises administering to a patient in need thereof an effective amount of a compound of formula (I) or a pharmaceutically acceptable salt thereof, optionally in combination with an additional agent (e.g., a second, third, fourth or fifth active agent) which can be useful for treating a cancer, an allergic disorder and/or an autoimmune and/or inflammatory disease, and/or an acute inflammatory reaction incident to or co-presenting with a cancer. Treatment with the second, third, fourth or fifth active agent may be prior to, concomitant with, or following treatment with a compound of formula (I) or a pharmaceutically acceptable salt thereof. In one embodiment, a compound of formula (I) or a pharmaceutically acceptable salt thereof is combined with another active agent in a single dosage form. Suitable antitumor or anticancer therapeutics that may be used in combination with a compound of formula (I) or a pharmaceutically acceptable salt thereof include, but are not limited to, chemotherapeutic agents, for example mitomycin C, carboplatin, taxol, cisplatin, paclitaxel, etoposide, doxorubicin, or a combination comprising at least one of the foregoing chemotherapeutic agents. Radiotherapeutic antitumor agents may also be used, alone or in combination with chemotherapeutic agents.

A compound of formula (I) or a pharmaceutically acceptable salt thereof can be useful as chemo-sensitizing agents, and thus, can be useful in combination with other chemotherapeutic drugs, in particular, drugs that induce apoptosis. Thus, in one embodiment, the present disclosure provides a method for increasing sensitivity of cancer cells to chemotherapy, comprising administering to a patient in need of or undergoing chemotherapy, a chemotherapeutic agent together with a compound of formula (I), or a pharmaceutically acceptable salt thereof in an amount sufficient to increase the sensitivity of cancer cells to the chemotherapeutic agent.

Examples of other chemotherapeutic drugs that can be used in combination with compounds of formula (I), or a pharmaceutically acceptable salt thereof include topoisomerase I inhibitors (camptothesin or topotecan), topoisomerase II inhibitors (e.g., daunomycin and etoposide), alkylating agents (e.g., cyclophosphamide, melphalan and BCNU), tubulin directed agents (e.g., taxol and vinblastine), and biological agents (e.g., antibodies such as anti CD20 antibody, IDEC 8, immunotoxins, and cytokines).

In some embodiments, the compound(s) of formula (I), or a pharmaceutically acceptable salt thereof is used in combination with Rituxan® (Rituximab) and/or other agents that work by selectively depleting CD20+ B-cells.

Included herein are methods of treatment in which a compound of formula (I), or a pharmaceutically acceptable salt thereof is administered in combination with an anti-inflammatory agent. Anti-inflammatory agents include but are not limited to NSAIDs, non-specific and COX-2 specific cyclooxgenase enzyme inhibitors, gold compounds, corticosteroids, methotrexate, tumor necrosis factor receptor (TNF) receptors antagonists, immunosuppressants and methotrexate.

Examples of NSAIDs include, but are not limited to ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. Examples of NSAIDs also include COX-2 specific inhibitors (i.e., a compound that inhibits COX-2 with an $IC_{50}$ that is at least 50-fold lower than the $IC_{50}$ for COX-1) such as celecoxib, valdecoxib, lumiracoxib, etoricoxib and/or rofecoxib.

In a further embodiment, the anti-inflammatory agent is a salicylate. Salicylates include but are not limited to acetylsalicylic acid or aspirin, sodium salicylate, and choline and magnesium salicylates.

The anti-inflammatory agent may also be a corticosteroid. For example, the corticosteroid may be chosen from cortisone, dexamethasone, methylprednisolone, prednisolone, prednisolone sodium phosphate, and prednisone.

In some embodiments, the anti-inflammatory therapeutic agent is a gold compound such as gold sodium thiomalate or auranofin.

In some embodiments, the anti-inflammatory agent is a metabolic inhibitor such as a dihydrofolate reductase inhibitor, such as methotrexate or a dihydroorotate dehydrogenase inhibitor, such as leflunomide.

In one embodiment, the compound(s) of formula (I), or a pharmaceutically acceptable salt thereof is used in combination with at least one anti-inflammatory compound that is an anti-C5 monoclonal antibody (such as eculizumab or pexelizumab), a TNF antagonist, such as entanercept, or infliximab, which is an anti-TNF alpha monoclonal antibody.

In one embodiment, the compound(s) of formula (I), or a pharmaceutically acceptable salt thereof is used in combination with at least one active agent that is an immunosuppressant compound such as methotrexate, leflunomide, cyclosporine, tacrolimus, azathioprine, or mycophenolate mofetil.

In other embodiments, the compound(s) of formula (I), or a pharmaceutically acceptable salt thereof is used in combination with one or more phosphatidylinositol 3-kinase (PI3K) inhibitors, including for example, Compounds A, B and C (whose structures are provided below), or a pharmaceutically acceptable salt thereof.

Compound A

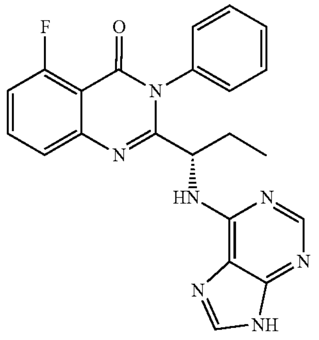

Compound B

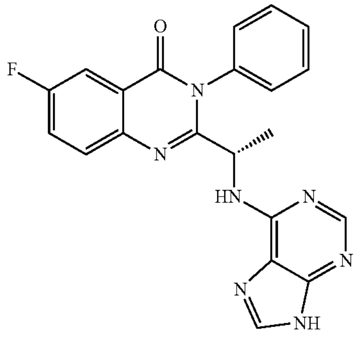

-continued

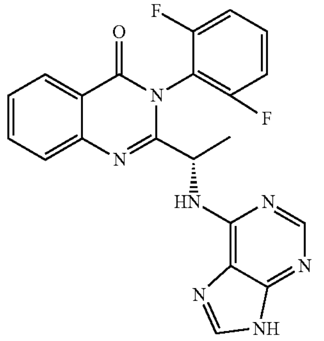

Compound C

Compounds A, B and C are disclosed in WO2015/017460 and WO2015/100217. Additional examples of PI3K inhibitors include, but are not limited to, ACP-319, AEZA-129, AMG-319, AS252424, AZD8186, BAY 10824391, BEZ235, buparlisib (BKM120), BYL719 (alpelisib), CH5132799, copanlisib (BAY 80-6946), duvelisib, GDC-0941, GDC-0980, GSK2636771, GSK2269557, idelalisib (Zydelig®), IPI-145, IPI-443, IPI-549, KAR4141, LY294002, LY3023414, MLN1117, OXY111A, PA799, PX-866, RG7604, rigosertib, RP5090, taselisib, TG100115, TGR-1202, TGX221, WX-037, X-339, X-414, XL147 (SAR245408), XL499, XL756, wortmannin, ZSTK474, and the compounds described in WO 2005/113556 (ICOS), WO 2013/052699 (Gilead Calistoga), WO 2013/116562 (Gilead Calistoga), WO 2014/100765 (Gilead Calistoga), WO 2014/100767 (Gilead Calistoga), and WO 2014/201409 (Gilead Sciences).

In yet another embodiment, the compound(s) of formula (I) may be used in combination with Spleen Tyrosine Kinase (SYK) Inhibitors. Examples of SYK inhibitors include, but are not limited to, 6-(1H-indazol-6-yl)-N-(4-morpholinophenyl)imidazo[1,2-a]pyrazin-8-amine, BAY-61-3606, cerdulatinib (PRT-062607), entospletinib, fostamatinib (R788), HMPL-523, NVP-QAB 205 AA, R112, R343, tamatinib (R406), and those described in U.S. Pat. No. 8,450,321 (Gilead Connecticut) and those described in U.S. 2015/0175616.

In yet another embodiment, the compounds of formula (I) may be used in combination with Tyrosine-kinase Inhibitors (TKIs). TKIs may target epidermal growth factor receptors (EGFRs) and receptors for fibroblast growth factor (FGF), platelet-derived growth factor (PDGF), and vascular endothelial growth factor (VEGF). Examples of TKIs include, but are not limited to, afatinib, ARQ-087, asp5878, AZD3759, AZD4547, bosutinib, brigatinib, cabozantinib, cediranib, crenolanib, dacomitinib, dasatinib, dovitinib, E-6201, erdafitinib, erlotinib, gefitinib, gilteritinib (ASP-2215), FP-1039, HM61713, icotinib, imatinib, KX2-391 (Src), lapatinib, lestaurtinib, midostaurin, nintedanib, ODM-203, osimertinib (AZD-9291), ponatinib, poziotinib, quizartinib, radotinib, rociletinib, sulfatinib (HMPL-012), sunitinib, and TH-4000.

In yet other embodiments, the compound(s) of formula (I), or a pharmaceutically acceptable salt thereof is used in combination with one or more inhibitors of lysyl oxidase-like 2 (LOXL) or a substance that binds to LOXL, including for example, a humanized monoclonal antibody (mAb) with an immunoglobulin IgG4 isotype directed against human LOXL2. Examples of LOXL inhibitors include, but are not limited to, the antibodies described in WO 2009/017833 (Arresto Biosciences). Examples of LOXL2 inhibitors include, but are not limited to, the antibodies described in WO 2009/017833 (Arresto Biosciences), WO 2009/035791 (Arresto Biosciences), and WO 2011/097513 (Gilead Biologics).

In yet another embodiment, the compounds of formula (I) may be used in combination with Toll-like receptor 8 (TLR8) inhibitors. Examples of TLR8 inhibitors include, but are not limited to, E-6887, IMO-4200, IMO-8400, IMO-9200, MCT-465, MEDI-9197, motolimod, resiquimod, VTX-1463, and VTX-763.

In yet another embodiment, the compounds of formula (I) may be used in combination with Toll-like receptor (TLR9) inhibitors. Examples of TLR9 inhibitors include, but are not limited to, IMO-2055, IMO-2125, lefitolimod, litenimod, MGN-1601, and PUL-042.

In one embodiment, the compound of formula (I) is useful for the treatment of cancer in combination with a BTK (Bruting's Tyrosine kinase) inhibitor. An example of such BTK inhibitor is a compound disclosed in U.S. Pat. No. 7,405,295. Additional examples of BTK inhibitors include, but are not limited to, (S)-6-amino-9-(1-(but-2-ynoyl)pyrrolidin-3-yl)-7-(4-phenoxyphenyl)-7H-purin-8(9H)-one, acalabrutinib (ACP-196), BGB-3111, HM71224, ibrutinib, M-2951, tirabrutinib (ONO-4059), PRN-1008, spebrutinib (CC-292), and TAK-020.

In one embodiment, the compound of formula (I) is useful for the treatment of cancer in combination with a BET inhibitor. An example of such BET inhibitor is a compound disclosed in WO2014/182929, the entire contents of which are incorporated herein by reference.

In one embodiment, the compound of formula (I) is useful for the treatment of cancer in combination with a TBK (Tank Binding kinase) inhibitor. An example of such TBK inhibitor is a compound disclosed in WO2016/049211.

In one embodiment, the compound of formula (I) is useful for the treatment of cancer in combination with a OX40 inhibitor. An example of such OX40 inhibitor is a compound disclosed in U.S. Pat. No. 8,450,460, the entire contents of which are incorporated herein by reference.

In one embodiment, the compound of formula (I) is useful for the treatment of cancer in combination with a JAK-1 inhibitor. An example of such JAK-1 inhibitor is a compound disclosed in WO2008/109943. Examples of other JAK inhibitors include, but are not limited to, AT9283, AZD1480, baricitinib, BMS-911543, fedratinib, filgotinib (GLPG0634), gandotinib (LY2784544), INCB039110, lestaurtinib, momelotinib (CYT0387), NS-018, pacritinib (SB1518), peficitinib (ASP015K), ruxolitinib, tofacitinib (formerly tasocitinib), and XL019.

In one embodiment, the compound of formula (I) is useful for the treatment of cancer in combination with an Indoleamine-pyrrole-2,3-dioxygenase (IDO) inhibitors. An example of such IDO inhibitor is a compound disclosed in WO2016/186967. In one embodiment, the compounds of formula (I) are useful for the treatment of cancer in combination with IDO1 inhibitors including but not limited to BLV-0801, epacadostat, F-001287, GBV-1012, GBV-1028, GDC-0919, indoximod, NKTR-218, NLG-919-based vaccine, PF-06840003, pyranonaphthoquinone derivatives (SN-35837), resminostat, SBLK-200802, and shIDO-ST.

In one embodiment, the compound of formula (I) is useful for the treatment of cancer in combination with a Mitogen-activated Protein Kinase (MEK) Inhibitors. MEK inhibitors useful for combination treatment with a compound(s) of formula (I) includes antroquinonol, binimetinib, cobimetinib (GDC-0973, XL-518), MT-144, selumetinib (AZD6244), sorafenib, trametinib (GSK1120212), uprosertib and trametinib.

In one embodiment, the compound of formula (I) is useful for the treatment of cancer in combination with an Apoptosis Signal-Regulating Kinase (ASK) Inhibitors: ASK inhibitors include but are not limited to those described in WO 2011/008709 (Gilead Sciences) and WO 2013/112741 (Gilead Sciences) including for example selonsertib.

In one embodiment, the compounds of formula (I) may be combined with Cluster of Differentiation 47 (CD47) inhibitors. Examples of CD47 inhibitors include, but are not limited to anti-CD47 mAbs (Vx-1004), anti-human CD47 mAbs (CNTO-7108), CC-90002, CC-90002-ST-001, humanized anti-CD47 antibody (Hu5F9-G4), NI-1701, NI-1801, RCT-1938, and TTI-621.

In one embodiment, the compounds of formula (I) may be combined with Cyclin-dependent Kinase (CDK) Inhibitors. CDK inhibitors include inhibitors of CDK 1, 2, 3, 4, 6 and 9, such as abemaciclib, alvocidib (HMR-1275, flavopiridol), AT-7519, FLX-925, LEE001, palbociclib, ribociclib, rigosertib, selinexor, UCN-01, and TG-02.

In one embodiment, the compounds of formula (I) may be combined with Discoidin Domain Receptor (DDR) Inhibitors for the treatment of cancer. DDR inhibitors include inhibitors of DDR1 and/or DDR2. Examples of DDR inhibitors include, but are not limited to, those disclosed in WO 2014/047624 (Gilead Sciences), US 2009-0142345 (Takeda Pharmaceutical), US 2011-0287011 (Oncomed Pharmaceuticals), WO 2013/027802 (Chugai Pharmaceutical), and WO 2013/034933 (Imperial Innovations).

In one embodiment, the compounds of formula (I) may be combined with Histone Deacetylase (HDAC) Inhibitors such as those disclosed in U.S. Pat. No. 8,575,353 and equivalents thereof. Additional examples of HDAC inhibitors include, but are not limited to, abexinostat, ACY-241, AR-42, BEBT-908, belinostat, CKD-581, CS-055 (HBI-8000), CUDC-907, entinostat, givinostat, mocetinostat, panobinostat, pracinostat, quisinostat (JNJ-26481585), resminostat, ricolinostat, SHP-141, valproic acid (VAL-001), vorinostat.

In one embodiment, the compound of formula (I) is useful for the treatment of cancer in combination with a standard of care in the treatment of the respective cancer. One of skill in the art is aware of the standard of care as of a given date in the particular field of cancer therapy or with respect to a given cancer.

Certain embodiments of the present application include or use one or more additional therapeutic agent. The one or more additional therapeutic agent may be an agent useful for the treatment of cancer, inflammation, autoimmune disease and/or related conditions. The one or more additional therapeutic agent may be a chemotherapeutic agent, an anti-angiogenic agent, an antifibrotic agent, an anti-inflammatory agent, an immune modulating agent, an immunotherapeutic agent, a therapeutic antibody, a radiotherapeutic agent, an anti-neoplastic agent, an anti-cancer agent, an anti-proliferation agent, or any combination thereof. In some embodiments, the compound(s) described herein may be used or combined with a chemotherapeutic agent, an anti-angiogenic agent, an anti-fibrotic agent, an anti-inflammatory agent, an immune modulating agent, an immunotherapeutic agent, a therapeutic antibody, a radiotherapeutic agent, an antineoplastic agent or an anti-cancer agent, an anti-proliferation agent, or any combination thereof.

In one embodiment, a compound(s) of formula (I) optionally in combination with an additional anticancer agent described herein, may be used or combined with an anti-neoplastic agent or an anti-cancer agent, anti-fibrotic agent, an anti-anti-inflammatory agent, or an immune modulating agent.

In one embodiment, provided are kits comprising a pharmaceutical composition comprising a compound of formula (I) or a pharmaceutically acceptable salt, or a compound of formula (I) and at least one additional anticancer agent, or a pharmaceutically acceptable salt thereof, and at least one pharmaceutically acceptable carrier. In one embodiment, the kit comprises instructions for use in the treatment of cancer or inflammatory conditions. In one embodiment, the instructions in the kit are directed to use of the pharmaceutical composition for the treatment of cancer selected from pancreatic cancer, bladder cancer, colorectal cancer, breast cancer, prostate cancer, renal cancer, hepatocellular cancer, lung cancer, ovarian cancer, cervical cancer, gastric cancer, esophageal cancer, head and neck cancer, melanoma, neuroendocrine cancer, CNS cancer, brain cancer, bone cancer, soft tissue sarcoma, non-small cell lung cancer, small-cell lung cancer and colon cancer.

The application also provides method for treating a subject who is undergoing one or more standard therapies, such as chemotherapy, radiotherapy, immunotherapy, surgery, or combination thereof comprising administering or co-administering a compound of formula (I) to said subject. Accordingly, one or more compound(S) of formula (I), or pharmaceutically acceptable salt thereof, may be administered before, during, or after administration of a chemotherapy, radiotherapy, immunotherapy, surgery or combination thereof.

In one embodiment, the subject may be a human who is (i) substantially refractory to at least one chemotherapy treatment, or (ii) in relapse after treatment with chemotherapy, or both (i) and (ii). In some of embodiments, the subject is refractory to at least two, at least three, or at least four chemotherapy treatments (including standard or experimental chemotherapies).

In one embodiment, the subject is refractory to at least one, at least two, at least three, or at least four chemotherapy treatment (including standard or experimental chemotherapy) selected from fludarabine, rituximab, obinutuzumab, alkylating agents, alemtuzumab and other chemotherapy treatments such as CHOP (cyclophosphamide, doxorubicin, vincristine, prednisone); R-CHOP (rituximab-CHOP); hyperCVAD (hyperfractionated cyclophosphamide, vincristine, doxorubicin, dexamethasone, methotrexate, cytarabine); R-hyperCVAD (rituximab-hyperCVAD); FCM (fludarabine, cyclophosphamide, mitoxantrone); R-FCM (rituximab, fludarabine, cyclophosphamide, mitoxantrone); bortezomib and rituximab; temsirolimus and rituximab; temsirolimus and Velcade®; Iodine-131 tositumomab (Bexxar) and CHOP; CVP (cyclophosphamide, vincristine, prednisone); R-CVP (rituximab-CVP); ICE (iphosphamide, carboplatin, etoposide); R-ICE (rituximab-ICE); FCR (fludarabine, cyclophosphamide, rituximab); FR (fludarabine, rituximab); and D.T. PACE (dexamethasone, thalidomide, cisplatin, Adriamycin, cyclophosphamide, etoposide).

Other examples of chemotherapy treatments (including standard or experimental chemotherapies) are described below. In addition, treatment of certain lymphomas is reviewed in Cheson, B. D., Leonard, J. P., "Monoclonal Antibody Therapy for B-Cell Non-Hodgkin's Lymphoma" *The New England Journal of Medicine* 2008, 359(6), p. 613-626; and Wierda, W. G., "Current and Investigational Therapies for Patients with CLL" *Hematology* 2006, p. 285-294. Lymphoma incidence patterns in the United States is profiled in Morton, L. M., et al. "Lymphoma Incidence Patterns by WHO Subtype in the United States, 1992-2001" *Blood* 2006, 107(1), p. 265-276.

Examples of immunotherapeutic agents treating lymphoma or leukemia include, but are not limited to, rituximab (such as Rituxan), alemtuzumab (such as Campath, MabCampath), anti-CD19 antibodies, anti-CD20 antibodies, anti-MN-14 antibodies, anti-TRAIL, Anti-TRAIL DR4 and DR5 antibodies, anti-CD74 antibodies, apolizumab, bevacizumab, CHIR-12.12, epratuzumab (hLL2-anti-CD22 humanized antibody), galiximab, ha20, ibritumomab tiuxetan, lumiliximab, milatuzumab, ofatumumab, PRO131921, SGN-40, WT-1 analog peptide vaccine, WT1 126-134 peptide vaccine, tositumomab, autologous human tumor-derived HSPPC-96, and veltuzumab. Additional immunotherapy agents includes using cancer vaccines based upon the genetic makeup of an individual patient's tumor, such as lymphoma vaccine example is GTOP-99 (MyVax®).

Examples of chemotherapy agents for treating lymphoma or leukemia include aldesleukin, alvocidib, antineoplaston AS2-1, antineoplaston A10, anti-thymocyte globulin, amifostine trihydrate, aminocamptothecin, arsenic trioxide, beta alethine, Bcl-2 family protein inhibitor ABT-263, BMS-345541, bortezomib (Velcade®), bryostatin 1, busulfan, carboplatin, campath-1H, CC-5103, carmustine, caspofungin acetate, clofarabine, cisplatin, Cladribine (Leustarin), Chlorambucil (Leukeran), Curcumin, cyclosporine, Cyclophosphamide (Cyloxan, Endoxan, Endoxana, Cyclostin), cytarabine, denileukin diftitox, dexamethasone, DT PACE, docetaxel, dolastatin 10, Doxorubicin (Adriamycin, Adriblastine), doxorubicin hydrochloride, enzastaurin, epoetin alfa, etoposide, Everolimus (RAD001), fenretinide, filgrastim, melphalan, mesna, Flavopiridol, Fludarabine (Fludara), Geldanamycin (17-AAG), ifosfamide, irinotecan hydrochloride, ixabepilone, Lenalidomide (Revlimid®, CC-5013), lymphokine-activated killer cells, melphalan, methotrexate, mitoxantrone hydrochloride, motexafin gadolinium, mycophenolate mofetil, nelarabine, oblimersen (Genasense) Obatoclax (GX15-070), oblimersen, octreotide acetate, omega-3 fatty acids, oxaliplatin, paclitaxel, PD0332991, PEGylated liposomal doxorubicin hydrochloride, pegfilgrastim, Pentstatin (Nipent), perifosine, Prednisolone, Prednisone, R-roscovitine (Selicilib, CYC202), recombinant interferon alfa, recombinant interleukin-12, recombinant interleukin-11, recombinant flt3 ligand, recombinant human thrombopoietin, rituximab, sargramostim, sildenafil citrate, simvastatin, sirolimus, Styryl sulphones, tacrolimus, tanespimycin, Temsirolimus (CCl-779), Thalidomide, therapeutic allogeneic lymphocytes, thiotepa, tipifarnib, Velcade® (bortezomib or PS-341), Vincristine (Oncovin), vincristine sulfate, vinorelbine ditartrate, Vorinostat (SAHA), vorinostat, and FR (fludarabine, rituximab), CHOP (cyclophosphamide, doxorubicin, vincristine, prednisone), CVP (cyclophosphamide, vincristine and prednisone), FCM (fludarabine, cyclophosphamide, mitoxantrone), FCR (fludarabine, cyclophosphamide, rituximab), hyperCVAD (hyperfractionated cyclophosphamide, vincristine, doxorubicin, dexamethasone, methotrexate, cytarabine), ICE (iphosphamide, carboplatin and etoposide), MCP (mitoxantrone, chlorambucil, and prednisolone), R-CHOP (rituximab plus CHOP), R-CVP (rituximab plus CVP), R-FCM (rituximab plus FCM), R-ICE (rituximab-ICE), and R-MCP (Rituximab-MCP).

In some embodiments, the cancer is melanoma. Suitable agents for use in combination with the compounds described herein include, without limitation, dacarbazine (DTIC), optionally, along with other chemotherapy drugs such as carmustine (BCNU) and cisplatin; the "Dartmouth regimen," which consists of DTIC, BCNU, cisplatin and tamoxifen; a combination of cisplatin, vinblastine, and DTIC, temozolomide or YERVOY™. Compounds disclosed herein may also be combined with immunotherapy drugs, including cytokines such as interferon alpha, interleukin 2, and tumor necrosis factor (TNF) in the treatment of melanoma.

Compounds described here may also be used in combination with vaccine therapy in the treatment of melanoma. Anti-melanoma vaccines are, in some ways, similar to the anti-virus vaccines which are used to prevent diseases caused by viruses such as polio, measles, and mumps. Weakened melanoma cells or parts of melanoma cells called antigens may be injected into a patient to stimulate the body's immune system to destroy melanoma cells.

Melanomas that are confined to the arms or legs may also be treated with a combination of agents including one or more compounds described herein, using for example, a hyperthermic isolated limb perfusion technique. This treatment protocol temporarily separates the circulation of the involved limb from the rest of the body and injects high doses of chemotherapy into the artery feeding the limb, thus providing high doses to the area of the tumor without exposing internal organs to these doses that might otherwise cause severe side effects. Usually the fluid is warmed to 102° to 104° F. Melphalan is the drug most often used in this chemotherapy procedure. This can be given with another agent called tumor necrosis factor (TNF) and optionally in combination with a compound of formula (I).

The therapeutic treatments can be supplemented or combined with any of the aforementioned therapies with stem cell transplantation or treatment. One example of modified approach is radioimmunotherapy, wherein a monoclonal antibody is combined with a radioisotope particle, such as indium In 111, yttrium Y 90, iodine I-131. Examples of combination therapies include, but are not limited to, Iodine-131 tositumomab (Bexxar), Yttrium-90 ibritumomab tiuxetan (Zevalin), Bexxar with CHOP.

Other therapeutic procedures useful in combination with treatment with a compound of formula (I) include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme technique, pharmacological study, low-LET cobalt-60 gamma ray therapy, bleomycin, conventional surgery, radiation therapy, and nonmyeloablative allogeneic hematopoietic stem cell transplantation.

In some embodiments, the application provides pharmaceutical compositions comprising a compound of formula (I) in combination with an MMP9 binding protein and/or one or more additional therapeutic agent, and a pharmaceutically acceptable diluent, carrier or excipient. In one embodiment, the pharmaceutical compositions comprise an MMP9 binding protein, one or more additional therapeutic agent, and a pharmaceutically acceptable excipient, carrier or diluent. In some embodiments, the pharmaceutical compositions comprise the compound of formula (I) and anti-MMP9 antibody AB0045.

In one embodiment, the pharmaceutical compositions comprise the compound of formula (I), anti-MMP9 antibody AB0045, at least one additional therapeutic agent that is an immunomodulating agent, and a pharmaceutically acceptable diluent, carrier or excipient. In certain other embodiments, the pharmaceutical compositions comprise the anti-MMP9 antibody AB0045, at least one additional therapeutic agent that is an anti-inflammatory agent, and a pharmaceutically acceptable diluent, carrier or excipient. In certain other embodiments, the pharmaceutical compositions comprise compound of formula (I), the anti-MMP9 antibody AB0045, at least one additional therapeutic agent that is an antineoplastic agent or anti-cancer agent, and a pharmaceutically acceptable diluent, carrier or excipient. In one embodiment, MMP9 compounds useful for combination treatment with a compound of formula (I) include but are not limited to marimastat (BB-2516), cipemastat (Ro 32-3555) and those described in WO 2012/027721 (Gilead Biologics).

In one embodiment, the one or more additional therapeutic agent is an immune modulating agent, e.g., an immunostimulant or an immunosuppressant. In certain other embodiments, an immune modulating agent is an agent capable of altering the function of immune checkpoints, including the CTLA-4, LAG-3, B7-H3, B7-H4, Tim3, BTLA, KIR, A2aR, CD200 and/or PD-1 pathways. In other embodiments, the immune modulating agent is immune checkpoint modulating agents. Exemplary immune checkpoint modulating agents include anti-CTLA-4 antibody (e.g., ipilimumab), anti-LAG-3 antibody, anti-B7-H3 antibody, anti-B7-H4 antibody, anti-Tim3 antibody, anti-BTLA antibody, anti-KIR antibody, anti-A2aR antibody, anti CD200 antibody, anti-PD-1 antibody, anti-PD-L1 antibody, anti-CD28 antibody, anti-CD80 or -CD86 antibody, anti-B7RP1 antibody, anti-B7-H3 antibody, anti-HVEM antibody, anti-CD137 or -CD137L antibody, anti-OX40 or -OX40L antibody, anti-CD40 or -CD40L antibody, anti-GAL9 antibody, anti-IL-10 antibody and A2aR drug. For certain such immune pathway gene products, the use of either antagonists or agonists of such gene products is contemplated, as are small molecule modulators of such gene products. In one embodiment, the immune modulatory agent is an anti-PD-1 or anti-PD-L1 antibody. In some embodiments, immune modulating agents include those agents capable of altering the function of mediators in cytokine mediated signaling pathways.

In some embodiments, the one or more additional therapy or anti-cancer agent is cancer gene therapy or cell therapy. Cancer gene therapy and cell therapy include the insertion of a normal gene into cancer cells to replace a mutated or altered gene; genetic modification to silence a mutated gene; genetic approaches to directly kill the cancer cells; including the infusion of immune cells designed to replace most of the patient's own immune system to enhance the immune response to cancer cells, or activate the patient's own immune system (T cells or Natural Killer cells) to kill cancer cells, or find and kill the cancer cells; genetic approaches to modify cellular activity to further alter endogenous immune responsiveness against cancer. Non limiting examples are Algenpantucel-L (2 pancreatic cell lines), Sipuleucel-T, SGT-53 liposomal nanodelivery (scL) of gene p53; T-cell therapy, such as CD19 CAR-T tisagenlecleucel-T (CTL019) WO2012079000, WO2017049166, axicabtagene ciloleucel (KTE-C19) U.S. Pat. Nos. 7,741,465, 6,319,494, JCAR-015 U.S. Pat. No. 7,446,190, JCAR-014, JCAR-020, JCAR-024, JCAR-023, JTCR-016, JCAR-018 WO2016090190, JCAR-017, (WO2016196388, WO2016033570, WO2015157386), BPX-501 U.S. Pat. No. 9,089,520, WO2016100236, AU-105, UCART-22, ACTR-087, P-BCMA-101; activated allogeneic natural killer cells CNDO-109-AANK, FATE-NK100, LFU-835 hematopoietic stem cells.

In one embodiment, the one or more additional therapeutic agent is an immune checkpoint inhibitor. Tumors subvert the immune system by taking advantage of a mechanism known as T-cell exhaustion, which results from chronic exposure to antigens and is characterized by the up-regulation of inhibitory receptors. These inhibitory receptors serve as immune checkpoints in order to prevent uncontrolled immune reactions.

PD-1 and co-inhibitory receptors such as cytotoxic T-lymphocyte antigen 4 (CTLA-4, B and T Lymphocyte Attenuator (BTLA; CD272), T cell Immunoglobulin and Mucin domain-3 (Tim-3), Lymphocyte Activation Gene-3 (Lag-3; CD223), and others are often referred to as a checkpoint regulators. They act as molecular determinants to influence whether cell cycle progression and other intracellular signaling processes should proceed based upon extracellular information.

In addition to specific antigen recognition through the T-cell receptor (TCR), T-cell activation is regulated through a balance of positive and negative signals provided by costimulatory receptors. These surface proteins are typically members of either the TNF receptor or B7 superfamilies. Agonistic antibodies directed against activating co-stimulatory molecules and blocking antibodies against negative co-stimulatory molecules may enhance T-cell stimulation to promote tumor destruction.

Programmed Cell Death Protein 1, (PD-1 or CD279), a 55-kD type 1 transmembrane protein, is a member of the CD28 family of T cell co-stimulatory receptors that include immunoglobulin superfamily member CD28, CTLA-4, inducible co-stimulator (ICOS), and BTLA. PD-1 is highly expressed on activated T cells and B cells. PD-1 expression can also be detected on memory T-cell subsets with variable levels of expression. Two ligands specific for PD-1 have been identified: programmed death-ligand 1 (PD-L1, also known as B7-H1 or CD274) and PD-L2 (also known as B7-DC or CD273). PD-L1 and PD-L2 have been shown to down-regulate T cell activation upon binding to PD-1 in both mouse and human systems (Okazaki et al., *Int. Immunol.,* 2007; 19: 813-824). The interaction of PD-1 with its ligands, PD-L1 and PD-L2, which are expressed on antigen-presenting, cells (APCs) and dendritic cells (DCs), transmits negative regulatory stimuli to down-modulate the activated T cell immune response. Blockade of PD-1 suppresses this negative signal and amplifies T cell responses. Numerous studies indicate that the cancer microenvironment manipulates the PD-L1/PD-1 signaling pathway and that induction of PD-L1 expression is associated with inhibition of immune responses against cancer, thus permitting cancer progression and metastasis. The PD-L1/PD-1 signaling pathway is a primary mechanism of cancer immune evasion for several reasons. This pathway is involved in negative regulation of immune responses of activated T effector cells found in the periphery. PD-L1 is up-regulated in cancer microenvironments, while PD-1 is also up-regulated on activated tumor infiltrating T cells, thus possibly potentiating a vicious cycle of inhibition. This pathway is also intricately involved in both innate and adaptive immune regulation through bi-directional signaling. These factors make the PD-1/PD-L1 complex a central point through which cancer can manipulate immune responses and promote its own progression.

The first immune-checkpoint inhibitor to be tested in a clinical trial was ipilimumab (Yervoy, Bristol-Myers Squibb), a CTLA-4 mAb. CTLA-4 belongs to the immunoglobulin superfamily of receptors, which also includes PD-1, BTLA, TIM-3, and V-domain immunoglobulin suppressor of T cell activation (VISTA). Anti-CTLA-4 mAb is a powerful checkpoint inhibitor which removes "the break" from both naive and antigen-experienced cells.

Therapy enhances the antitumor function of CD8+ T cells, increases the ratio of CD8+ T cells to Foxp3+ T regulatory cells, and inhibits the suppressive function of T regulatory cells. TIM-3 has been identified as another important inhibitory receptor expressed by exhausted CD8+ T cells. In mouse models of cancer, it has been shown that the most dysfunctional tumor-infiltrating CD8+ T cells actually co-express PD-1 and LAG-3. LAG-3 is another recently identified inhibitory receptor that acts to limit effector T-cell function and augment the suppressive activity of T regulatory cells. It has recently been revealed that PD-1 and LAG-3 are extensively co-expressed by tumor-infiltrating T cells in mice, and that combined blockade of PD-1 and LAG-3 provokes potent synergistic antitumor immune responses in mouse models of cancer.

Thus in one embodiment, the present disclosure provides the use of immune checkpoint inhibitors of formula (I) disclosed herein in combination with one or more additional immune checkpoint inhibitors. In one embodiment, the present disclosure provides the use of immune checkpoint inhibitors of formula (I) disclosed herein in combination with one or more additional immune checkpoint inhibitors and an anti-MMP9 antibody or antigen binding fragment thereof to treat or prevent cancer. In some embodiments, the immune checkpoint inhibitors may be an anti-PD-1 and/or an anti-PD-L1 antibody or an anti PD-1/PD-L1 interaction inhibitor. In some embodiments, the anti-PD-L1 antibody may be B7-H1 antibody, BMS 936559 antibody, MPDL3280A (atezolizumab) antibody, MEDI-4736 antibody, MSB0010718C antibody or combinations thereof. According to another embodiment, the anti-PD-1 antibody may be nivolumab antibody, pembrolizumab antibody, pidilizumab antibody or combinations thereof.

In addition, PD-1 may also be targeted with AMP-224, which is a PD-L2-IgG recombinant fusion protein. Additional antagonists of inhibitory pathways in the immune response include IMP321, a soluble LAG-3 Ig fusion protein and MHC class II agonist, which is used to increase an immune response to tumors. Lirilumab is an antagonist to the KIR receptor and BMS 986016 is an antagonist of LAG3. The TIM-3-Galectin-9 pathway is another inhibitory checkpoint pathway that is also a promising target for checkpoint inhibition. RX518 targets and activates the glucocorticoid-induced tumor necrosis factor receptor (GITR), a member of the TNF receptor superfamily that is expressed on the surface of multiple types of immune cells, including regulatory T cells, effector T cells, B cells, natural killer (NK) cells, and activated dendritic cells. Thus, in one embodiment, the compound(s) of formula (I) may be used in combination with IMP321, Lirilumab and/or BMS 986016.

Anti-PD-1 antibodies that may be used in the compositions and methods described herein include but are not limited to: Nivolumab/MDX-1106/BMS-936558/ONO1152, a fully human IgG4 anti-PD-1 monoclonal antibody; pidilizumab (MDV9300/CT-011), a humanized IgG1 monoclonal antibody; pembrolizumab (MK-3475/pembrolizumab/lambrolizumab), a humanized monoclonal IgG4 antibody; durvalumab (MEDI-4736) and atezolizumab. Anti-PD-L1 antibodies that may be used in compositions and methods described herein include but are not limited to: avelumab; BMS-936559, a fully human IgG4 antibody; atezolizumab (MPDL3280A/RG-7446), a human monoclonal antibody; MEDI4736; MSB0010718C, and MDX1105-01.

In one embodiment, the compound of formula (I) is administered in combination with the anti-PD-1 antibody nivolumab, pembrolizumab, and/or pidilizumab to a patient in need thereof. In one embodiment, the anti-PD-L1 antibody useful for combination treatment with a compound of formula (I) is BMS-936559, atezolizumab, or avelumab. In one embodiment, the immune modulating agent inhibits an immune checkpoint pathway. In another embodiment, the immune checkpoint pathway is selected from CTLA-4, LAG-3, B7-H3, B7-H4, Tim3, BTLA, KIR, A2aR, CD200 and PD-1. Additional antibodies that may be used in combination with a compound of formula (I) in compositions and methods described herein include the anti-PD-1 and anti-PD-L1 antibodies disclosed in U.S. Pat. Nos. 8,008,449 and 7,943,743, respectively.

In one embodiment, the one or more additional therapeutic agent is an anti-inflammatory agent. In certain other embodiments, the anti-inflammatory agent is a tumor necrosis factor alpha (TNF-$\alpha$) inhibitor. As used herein, the terms "TNF alpha," "TNF-$\alpha$," and "TNF$\alpha$," are interchangeable. TNF-$\alpha$ is a pro-inflammatory cytokine secreted primarily by macrophages but also by a variety of other cell types including lymphoid cells, mast cells, endothelial cells, cardiac myocytes, adipose tissue, fibroblasts, and neuronal tissue. TNF-$\alpha$ is also known as endotoxin-induced factor in serum, cachectin, and differentiation inducing factor. The tumor necrosis factor (TNF) family includes TNF alpha, TNF beta, CD40 ligand (CD40L), Fas ligand (FasL), TNF-related apoptosis inducing ligand (TRAIL), and LIGHT (homologous to lymphotoxins, exhibits inducible expression, and competes with HSV glycoprotein D for HVEM, a receptor expressed by T lymphocytes), some of the most important cytokines involved in, among other physiological processes, systematic inflammation, tumor lysis, apoptosis and initiation of the acute phase reaction.

The above therapeutic agents when employed in combination with a compound(s) disclosed herein, may be used, for example, in those amounts indicated in the referenced manuals e.g., Physicians Desk Reference or in amounts generally known to a qualified care giver, i.e., one of ordinary skill in the art. In the methods of the present disclosure, such other therapeutic agent(s) may be administered prior to, simultaneously with, or following the administration of the compound(s) of formula (I). Certain other therapeutic agents may be combined into a single formulation or kit when amenable to such. For example, tablet, capsule or liquid formulations may be combined with other tablet, capsule or liquid formulations into one fixed or combined dose formulation or regimen. Other combinations may be given separately, contemporaneously or otherwise.

In one embodiment, the instructions are directed to use of the pharmaceutical composition for the treatment of cancer, including for example, leukemia or lymphoma. In specific embodiments, the cancer is acute lymphocytic leukemia (ALL), acute myeloid leukemia (AML), chronic lymphocytic leukemia (CLL), small lymphocytic lymphoma (SLL), myelodysplastic syndrome (MDS), myeloproliferative disease (MPD), chronic myeloid leukemia (CML), multiple myeloma (MM), indolent non-Hodgkin's lymphoma (iNHL), refractory iNHL, non-Hodgkin's lymphoma (NHL), mantle cell lymphoma (MCL), follicular lymphoma, Waldestrom's macroglobulinemia (WM), T-cell lymphoma, B-cell lymphoma, and diffuse large B-cell lymphoma (DLBCL). In one embodiment, the cancer is T-cell acute lymphoblastic leukemia (T-ALL), or B-cell acute lymphoblastic leukemia (B-ALL). The non-Hodgkin lymphoma encompasses the indolent B-cell diseases that include, for example, follicular lymphoma, lymphoplasmacytic lymphoma, Waldenstrom macroglobulinemia, and marginal zone lymphoma, as well as the aggressive lymphomas that include, for example, Burkitt lymphoma, diffuse large B-cell lymphoma (DLBCL) and mantle cell lymphoma (MCL). In one embodiment, the cancer is indolent non-Hodgkin's lymphoma (iNHL)

In a particular variation, the instructions are directed to use of the pharmaceutical composition for the treatment of an autoimmune disease. Specific embodiments of an autoimmune disease include asthma, rheumatoid arthritis, multiple sclerosis, and lupus.

Combination Therapy for HBV

In certain embodiments, a method for treating or preventing an HBV infection in a human having or at risk of having the infection is provided, comprising administering to the human a therapeutically effective amount of a compound disclosed herein, or a pharmaceutically acceptable salt thereof, in combination with a therapeutically effective amount of one or more (e.g., one, two, three, four, one or two, one to three, or one to four) additional therapeutic agents. In one embodiment, a method for treating an HBV infection in a human having or at risk of having the infection is provided, comprising administering to the human a therapeutically effective amount of a compound disclosed herein, or a pharmaceutically acceptable salt thereof, in combination with a therapeutically effective amount of one or more (e.g., one, two, three, four, one or two, one to three, or one to four) additional therapeutic agents.

In certain embodiments, the present disclosure provides a method for treating an HBV infection, comprising administering to a patient in need thereof a therapeutically effective amount of a compound disclosed herein or a pharmaceutically acceptable salt thereof, in combination with a therapeutically effective amount of one or more (e.g., one, two, three, four, one or two, one to three, or one to four) additional therapeutic agents which are suitable for treating an HBV infection.

In certain embodiments, a compound disclosed herein, or a pharmaceutically acceptable salt thereof, is combined with one, two, three, four, or more additional therapeutic agents. In certain embodiments, a compound disclosed herein, or a pharmaceutically acceptable salt thereof, is combined with two additional therapeutic agents. In other embodiments, a compound disclosed herein, or a pharmaceutically acceptable salt thereof, is combined with three additional therapeutic agents. In further embodiments, a compound disclosed herein, or a pharmaceutically acceptable salt thereof, is combined with four additional therapeutic agents. The one, two, three, four, or more additional therapeutic agents can be different therapeutic agents selected from the same class of therapeutic agents, and/or they can be selected from different classes of therapeutic agents.

Administration of HBV Combination Therapy

In certain embodiments, when a compound disclosed herein is combined with one or more additional therapeutic agents as described above, the components of the composition are administered as a simultaneous or sequential regimen. When administered sequentially, the combination may be administered in two or more administrations.

Co-administration of a compound disclosed herein with one or more additional therapeutic agents generally refers to simultaneous or sequential administration of a compound disclosed herein and one or more additional therapeutic agents, such that therapeutically effective amounts of each agent are present in the body of the patient.

Co-administration includes administration of unit dosages of the compounds disclosed herein before or after administration of unit dosages of one or more additional therapeutic agents. The compound disclosed herein may be administered within seconds, minutes, or hours of the administration of one or more additional therapeutic agents. For example, in some embodiments, a unit dose of a compound disclosed herein is administered first, followed within seconds or minutes by administration of a unit dose of one or more additional therapeutic agents. Alternatively, in other embodiments, a unit dose of one or more additional therapeutic agents is administered first, followed by administration of a unit dose of a compound disclosed herein within seconds or minutes. In some embodiments, a unit dose of a compound disclosed herein is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of a compound disclosed herein.

In certain embodiments, a compound disclosed herein is combined with one or more additional therapeutic agents in a unitary dosage form for simultaneous administration to a patient, for example as a solid dosage form for oral administration.

In certain embodiments a compound of Formula (I) is formulated as a tablet, which may optionally contain one or more other compounds useful for treating HBV. In certain embodiments, the tablet can contain another active ingredient for treating HBV.

In certain embodiments, such tablets are suitable for once daily dosing.

The compounds described herein may be used or combined with one or more of a chemotherapeutic agent, an immunomodulator, an immunotherapeutic agent, a therapeutic antibody, a therapeutic vaccine, a bispecific antibody and "antibody-like" therapeutic protein (such as DARTs®, Duobodies®, Bites®, XmAbs®, TandAbs®, Fab derivatives), an antibody-drug conjugate (ADC), gene modifiers or gene editors (such as CRISPR Cas9, zinc finger nucleases, homing endonucleases, synthetic nucleases, TALENs), cell therapies such as CAR-T (chimeric antigen receptor T-cell), and TCR-T (an engineered T cell receptor) agent or any combination thereof.

In the above embodiments, the additional therapeutic agent may be an anti-HBV agent. For example, the additional therapeutic agent may be selected from the group consisting of HBV combination drugs, other drugs for treating HBV, 3-dioxygenase (IDO) inhibitors, antisense oligonucleotide targeting viral mRNA, Apolipoprotein A1 modulator, arginase inhibitors, B- and T-lymphocyte attenuator inhibitors, Bruton's tyrosine kinase (BTK) inhibitors, CCR2 chemokine antagonist, CD137 inhibitors, CD160 inhibitors, CD305 inhibitors, CD4 agonist and modulator, compounds targeting HBcAg, compounds targeting hepatitis B core antigen (HBcAg), covalently closed circular DNA (cccDNA) inhibitors, cyclophilin inhibitors, cytokines, cytotoxic T-lymphocyte-associated protein 4 (ipi4) inhibitors, DNA polymerase inhibitor, Endonuclease modulator, epigenetic modifiers, Farnesoid X receptor agonist, gene modifiers or editors, HBsAg inhibitors, HBsAg secretion or assembly inhibitors, HBV antibodies, HBV DNA polymerase inhibitors, HBV replication inhibitors, HBV RNAse inhibitors, HBV vaccines, HBV viral entry inhibitors, HBx inhibitors, Hepatitis B large envelope protein modulator, Hepatitis B large envelope protein stimulator, Hepatitis B structural protein modulator, hepatitis B surface antigen (HBsAg) inhibitors, hepatitis B surface antigen (HBsAg) secretion or assembly inhibitors, hepatitis B virus E antigen inhibitors, hepatitis B virus replication inhibitors, Hepatitis virus structural protein inhibitor, HIV-1 reverse transcriptase inhibitor, Hyaluronidase inhibitor, IAPs inhibitors, IL-2 agonist, IL-7 agonist, Immunoglobulin agonist, Immunoglobulin G modulator, immunomodulators, indoleamine-2, inhibitors of ribonucleotide reductase, Interferon agonist, Interferon alpha 1 ligand, Interferon alpha 2 ligand, Interferon alpha 5 ligand modulator, Interferon alpha ligand, Interferon alpha ligand modulator, interferon alpha receptor ligands, Interferon beta ligand, Interferon ligand, Interferon receptor modulator, Interleukin-2 ligand, ipi4 inhibitors, lysine demethylase inhibitors, histone demethylase inhibitors, KDM5 inhibitors, KDM1 inhibitors, killer cell lectin-like receptor subfamily G member 1 inhibitors, lymphocyte-activation gene 3 inhibitors, lymphotoxin beta receptor activators, microRNA (miRNA) gene therapy agents, modulators of Axl, modulators of B7-H3, modulators of B7-H4, modulators of CD160, modulators of CD161, modulators of CD27, modulators of CD47, modulators of CD70, modulators of GITR, modulators of HEVEM, modulators of ICOS, modulators of Mer, modulators of NKG2A, modulators of NKG2D, modulators of OX40, modulators of SIRPalpha, modulators of TIGIT, modulators of Tim-4, modulators of Tyro, Na+-taurocholate cotransporting polypeptide (NTCP) inhibitors, natural killer cell receptor 2B4 inhibitors, NOD2 gene stimulator, Nucleoprotein inhibitor, nucleoprotein modulators, PD-1 inhibitors, PD-L1 inhibitors, PEG-Interferon Lambda, Peptidylprolyl isomerase inhibitor, phosphatidylinositol-3 kinase (PI3K) inhibitors, recombinant scavenger receptor A (SRA) proteins, recombinant thymosin alpha-1, Retinoic acid-inducible gene 1 stimulator, Reverse transcriptase inhibitor, Ribonuclease inhibitor, RNA DNA polymerase inhibitor, short interfering RNAs (siRNA), short synthetic hairpin RNAs (sshRNAs), SLC10A1 gene inhibitor, SMAC mimetics, Src tyrosine kinase inhibitor, stimulator of interferon gene (STING) agonists, stimulators of NOD1, T cell surface glycoprotein CD28 inhibitor, T-cell surface glycoprotein CD8 modulator, Thymosin agonist, Thymosin alpha 1 ligand, Tim-3 inhibitors, TLR-3 agonist, TLR-7 agonist, TLR-9 agonist, TLR9 gene stimulator, toll-like receptor (TLR) modulators, Viral ribonucleotide reductase inhibitor, zinc finger nucleases or synthetic nucleases (TALENs), and combinations thereof.

In certain embodiments, a compound of Formula (I) is formulated as a tablet, which may optionally contain one or more other compounds useful for treating HBV. In certain embodiments, the tablet can contain another active ingredient for treating HBV, such as 3-dioxygenase (IDO) inhibitors, Apolipoprotein A1 modulator, arginase inhibitors, B- and T-lymphocyte attenuator inhibitors, Bruton's tyrosine kinase (BTK) inhibitors, CCR2 chemokine antagonist, CD137 inhibitors, CD160 inhibitors, CD305 inhibitors, CD4 agonist and modulator, compounds targeting HBcAg, compounds targeting hepatitis B core antigen (HBcAg), core protein allosteric modulators, covalently closed circular DNA (cccDNA) inhibitors, cyclophilin inhibitors, cytotoxic T-lymphocyte-associated protein 4 (ipi4) inhibitors, DNA polymerase inhibitor, Endonuclease modulator, epigenetic modifiers, Farnesoid X receptor agonist, HBsAg inhibitors, HBsAg secretion or assembly inhibitors, HBV DNA polymerase inhibitors, HBV replication inhibitors, HBV RNAse inhibitors, HBV viral entry inhibitors, HBx inhibitors, Hepatitis B large envelope protein modulator, Hepatitis B large envelope protein stimulator, Hepatitis B structural protein modulator, hepatitis B surface antigen (HBsAg) inhibitors, hepatitis B surface antigen (HBsAg) secretion or assembly inhibitors, hepatitis B virus E antigen inhibitors, hepatitis B virus replication inhibitors, Hepatitis virus structural protein inhibitor, HIV-1 reverse transcriptase inhibitor, Hyaluronidase inhibitor, IAPs inhibitors, IL-2 agonist, IL-7 agonist, immunomodulators, indoleamine-2 inhibitors, inhibitors of ribonucleotide reductase, Interleukin-2 ligand, ipi4 inhibitors, lysine demethylase inhibitors, histone demethylase inhibitors, KDM1 inhibitors, KDM5 inhibitors, killer cell lectin-like receptor subfamily G member 1 inhibitors, lymphocyte-activation gene 3 inhibitors, lymphotoxin beta receptor activators, modulators of Axl, modulators of B7-H3, modulators of B7-H4, modulators of CD160, modulators of CD161, modulators of CD27, modulators of CD47, modulators of CD70, modulators of GITR, modulators of HEVEM, modulators of ICOS, modulators of Mer, modulators of NKG2A, modulators of NKG2D, modulators of OX40, modulators of SIRPalpha, modulators of TIGIT, modulators of Tim-4, modulators of Tyro, Na+-taurocholate cotransporting polypeptide (NTCP) inhibitors, natural killer cell receptor 2B4 inhibitors, NOD2 gene stimulator, Nucleoprotein inhibitor, nucleoprotein modulators, PD-1 inhibitors, PD-L1 inhibitors, Peptidylprolyl isomerase inhibitor, phosphatidylinositol-3 kinase (PI3K) inhibitors, Retinoic acid-inducible gene 1 stimulator, Reverse transcriptase inhibitor, Ribonuclease inhibitor, RNA DNA polymerase inhibitor, SLC10A1 gene inhibitor, SMAC mimetics, Src tyrosine kinase inhibitor, stimulator of interferon gene (STING) agonists, stimulators of NOD1, T cell surface glycoprotein CD28 inhibitor, T-cell surface glycoprotein CD8 modulator, Thymosin agonist, Thymosin alpha 1 ligand, Tim-3 inhibitors, TLR-3 agonist, TLR-7 agonist, TLR-9 agonist, TLR9 gene stimulator, toll-like receptor (TLR) modulators, Viral ribonucleotide reductase inhibitor, and combinations thereof.

In certain embodiments, a compound of the present disclosure, or a pharmaceutically acceptable salt thereof, is combined with one, two, three, four or more additional therapeutic agents selected from HBV combination drugs, HBV vaccines, HBV DNA polymerase inhibitors, immunomodulators toll-like receptor (TLR) modulators, interferon alpha receptor ligands, hyaluronidase inhibitors, hepatitis b surface antigen (HBsAg) inhibitors, cytotoxic T-lymphocyte-associated protein 4 (ipi4) inhibitors, cyclophilin inhibitors, HBV viral entry inhibitors, antisense oligonucleotide targeting viral mRNA, short interfering RNAs (siRNA) and ddRNAi endonuclease modulators, ribonucelotide reductase inhibitors, HBV E antigen inhibitors, covalently closed circular DNA (cccDNA) inhibitors, farnesoid X receptor agonists, HBV antibodies, CCR2 chemokine antagonists, thymosin agonists, cytokines, nucleoprotein modulators, retinoic acid-inducible gene 1 stimulators, NOD2 stimulators, phosphatidylinositol 3-kinase (PI3K) inhibitors, indoleamine-2, 3-dioxygenase (IDO) pathway inhibitors, PD-1 inhibitors, PD-L1 inhibitors, recombinant thymosin alpha-1, bruton's tyrosine kinase (BTK) inhibitors, KDM inhibitors, HBV replication inhibitors, arginase inhibitors, and other HBV drugs.

HBV Combination Drugs

Examples of combination drugs for the treatment of HBV include TRUVADA® (tenofovir disoproxil fumarate and emtricitabine); ABX-203, lamivudine, and PEG-IFN-alpha; ABX-203 adefovir, and PEG-IFNalpha; and INO-1800 (INO-9112 and RG7944).

Other HBV Drugs

Examples of other drugs for the treatment of HBV include alpha-hydroxytropolones, amdoxovir, beta-hydroxycytosine nucleosides, AL-034, CCC-0975, elvucitabine, ezetimibe, cyclosporin A, gentiopicrin (gentiopicroside), JNJ-56136379, nitazoxanide, birinapant, NJK14047, NOV-205

(molixan, BAM-205), oligotide, mivotilate, feron, GST-HG-131, levamisole, Ka Shu Ning, alloferon, WS-007, Y-101 (Ti Fen Tai), rSIFN-co, PEG-IIFNm, KW-3, BP-Inter-014, oleanolic acid, HepB-nRNA, cTP-5 (rTP-5), HSK-II-2, HEISCO-106-1, HEISCO-106, Hepbarna, IBPB-006A, Hepuyinfen, DasKloster 0014-01, ISA-204, Jiangantai (Ganxikang), MIV-210, OB-AI-004, PF-06, picroside, DasKloster-0039, hepulantai, IMB-2613, TCM-800B, reduced glutathione, RO-6864018, RG-7834, UB-551, and ZH-2N, and the compounds disclosed in US20150210682, (Roche), US 2016/0122344 (Roche), WO2015173164, WO2016023877, US2015252057A (Roche), WO1628335A1 (Roche), WO16120186A1 (Roche), US2016237090A (Roche), WO16107833A1 (Roche), WO16107832A1 (Roche), US2016176899A (Roche), WO16102438A1 (Roche), WO2016012470A1 (Roche), US2016220586A (Roche), and US2015031687A (Roche).

HBV Vaccines

HBV vaccines include both prophylactic and therapeutic vaccines. Examples of HBV prophylactic vaccines include Vaxelis, Hexaxim, Heplisav, Mosquirix, DTwP-HBV vaccine, Bio-Hep-B, D/T/P/HBV/M (LBVP-0101; LBVW-0101), DTwP-Hepb-Hib-IPV vaccine, Heberpenta L, DTwP-HepB-Hib, V-419, CVI-HBV-001, Tetrabhay, hepatitis B prophylactic vaccine (Advax Super D), Hepatrol-07, GSK-223192A, ENGERIX B®, recombinant hepatitis B vaccine (intramuscular, Kangtai Biological Products), recombinant hepatitis B vaccine (Hansenual polymorpha yeast, intramuscular, Hualan Biological Engineering), recombinant hepatitis B surface antigen vaccine, Bimmugen, Euforavac, Eutravac, anrix-DTaP-IPV-Hep B, HBAI-20, Infanrix-DTaP-IPV-Hep B-Hib, Pentabio Vaksin DTP—HB-Hib, Comvac 4, Twinrix, Euvax-B, Tritanrix HB, Infanrix Hep B, Comvax, DTP-Hib-HBV vaccine, DTP-HBV vaccine, Yi Tai, Heberbiovac HB, Trivac HB, GerVax, DTwP-Hep B-Hib vaccine, Bilive, Hepavax-Gene, SUPER-VAX, Comvac5, Shanvac-B, Hebsulin, Recombivax HB, Revac B mcf, Revac B+, Fendrix, DTwP-HepB-Hib, DNA-001, Shan5, Shan6, rhHBsAG vaccine, HBI pentavalent vaccine, LBVD, Infanrix HeXa, and DTaP-rHB-Hib vaccine.

Examples of HBV therapeutic vaccines include HBsAG-HBIG complex, ARB-1598, Bio-Hep-B, NASVAC, abi-HB (intravenous), ABX-203, Tetrabhay, GX-110E, GS-4774, peptide vaccine (epsilonPA-44), Hepatrol-07, NASVAC (NASTERAP), IMP-321, BEVAC, Revac B mcf, Revac B+, MGN-1333, KW-2, CVI-HBV-002, AltraHepB, VGX-6200, FP-02, FP-02.2, TG-1050, NU-500, HBVax, im/TriGrid/antigen vaccine, Mega-CD40L-adjuvanted vaccine, HepB-v, RG7944 (INO-1800), recombinant VLP-based therapeutic vaccine (HBV infection, VLP Biotech), AdTG-17909, AdTG-17910 AdTG-18202, ChronVac-B, TG-1050, and Lm HBV.

HBV DNA Polymerase Inhibitors

Examples of HBV DNA polymerase inhibitors include adefovir (HEPSERA®), emtricitabine (EMTRIVA®), tenofovir disoproxil fumarate (VIREAD®), tenofovir alafenamide, tenofovir, tenofovir disoproxil, tenofovir alafenamide fumarate, tenofovir alafenamide hemifumarate, tenofovir dipivoxil, tenofovir dipivoxil fumarate, tenofovir octadecyloxyethyl ester, CMX-157, besifovir, entecavir (BARACLUDE®), entecavir maleate, telbivudine (TYZEKA®), pradefovir, clevudine, ribavirin, lamivudine (EPIVIR-HBV®), phosphazide, famciclovir, fusolin, metacavir, SNC-019754, FMCA, AGX-1009, AR-II-04-26, HIP-1302, tenofovir disoproxil aspartate, tenofovir disoproxil orotate, and HS-10234.

Immunomodulators

Examples of immunomodulators include rintatolimod, imidol hydrochloride, ingaron, dermaVir, plaquenil (hydroxychloroquine), proleukin, hydroxyurea, mycophenolate mofetil (MPA) and its ester derivative mycophenolate mofetil (MMF), WF-10, ribavirin, IL-12, INO-9112, polymer polyethyleneimine (PEI), Gepon, VGV-1, MOR-22, BMS-936559, RO-7011785, RO-6871765, AIC-649, and IR-103.

Toll-Like Receptor (TLR) Modulators

TLR modulators include modulators of TLR1, TLR2, TLR3, TLR4, TLR5, TLR6, TLR7, TLR8, TLR9, TLR10, TLR11, TLR12, and TLR13. Examples of TLR3 modulators include rintatolimod, poly-ICLC, RIBOXXON®, Apoxxim, RIBOXXIM®, IPH-33, MCT-465, MCT-475, GS-9688 and ND-1.1.

Examples of TLR7 modulators include GS-9620, GSK-2245035, imiquimod, resiquimod, DSR-6434, DSP-3025, IMO-4200, MCT-465, MEDI-9197, 3M-051, SB-9922, 3M-052, Limtop, TMX-30X, TMX-202, RG-7863, RG-7795, RG-7854, and the compounds disclosed in US20100143301 (Gilead Sciences), US20110098248 (Gilead Sciences), and US20090047249 (Gilead Sciences).

Examples of TLR8 modulators include motolimod, resiquimod, 3M-051, 3M-052, MCT-465, IMO-4200, VTX-763, VTX-1463, and the compounds disclosed in US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics).

Examples of TLR9 modulators include BB-001, BB-006, CYT-003, IMO-2055, IMO-2125, IMO-3100, IMO-8400, IR-103, IMO-9200, agatolimod, DIMS-9054, DV-1079, DV-1179, AZD-1419, leftolimod (MGN-1703), litenimod, and CYT-003-QbG10.

Interferon Alpha Receptor Ligands

Examples of interferon alpha receptor ligands include interferon alpha-2b (INTRON A®), pegylated interferon alpha-2a (PEGASYS®), PEGylated interferon alpha-1b, interferon alpha 1b (HAPGEN®), Veldona, Infradure, Roferon-A, YPEG-interferon alfa-2a (YPEG-rhIFNalpha-2a), P-1101, Algeron, Alfarona, Ingaron (interferon gamma), rSIFN-co (recombinant super compound interferon), Ypeginterferon alfa-2b (YPEG-rhIFNalpha-2b), MOR-22, peginterferon alfa-2b (PEG-INTRON®), Bioferon, Novaferon, Inmutag (Inferon), MULTIFERON®, interferon alfa-n1 (HUMOFERON®), interferon beta-1a (AVONEX®), Shaferon, interferon alfa-2b (Axxo), Alfaferone, interferon alfa-2b (BioGeneric Pharma), interferon-alpha 2 (CJ), Laferonum, VIPEG, BLAUFERON-A, BLAUFERON-B, Intermax Alpha, Realdiron, Lanstion, Pegaferon, PDferon-B PDferon-B, interferon alfa-2b (IFN, Laboratorios Bioprofarma), alfainterferona 2b, Kalferon, Pegnano, Feronsure, PegiHep, interferon alfa 2b (Zydus-Cadila), interferon alfa 2a, Optipeg A, Realfa 2B, Reliferon, interferon alfa-2b (Amega), interferon alfa-2b (Virchow), ropeginterferon alfa-2b, rHSA-IFN alpha-2a (recombinant human serum albumin intereferon alpha 2a fusion protein), rHSA-IFN alpha 2b, recombinant human interferon alpha-(1b, 2a, 2b), peginterferon alfa-2b (Amega), peginterferon alfa-2a, Reaferon-EC, Proquiferon, Uniferon, Urifron, interferon alfa-2b (Changchun Institute of Biological Products), Anterferon, Shanferon, Layfferon, Shang Sheng Lei Tai, INTEFEN, SINOGEN, Fukangtai, Pegstat, rHSA-IFN alpha-2b, SFR-9216, and Interapo (Interapa).

Hyaluronidase Inhibitors

Examples of hyaluronidase inhibitors include astodrimer.

Hepatitis B Surface Antigen (HBsAg) Inhibitors

Examples of HBsAg inhibitors include HBF-0259, PBHBV-001, PBHBV-2-15, PBHBV-2-1, REP-9AC, REP-9C, REP-9, REP-2139, REP-2139-Ca, REP-2165, REP-2055, REP-2163, REP-2165, REP-2053, REP-2031 and REP-006, and REP-9AC'.

Examples of HBsAg secretion inhibitors include BM601.

Cytotoxic T-Lymphocyte-Associated Protein 4 (Ipi4) Inhibitors

Examples of Cytotoxic T-lymphocyte-associated protein 4 (ipi4) inhibitors include AGEN-2041, AGEN-1884, ipilumimab, belatacept, PSI-001, PRS-010, Probody mAbs, tremelimumab, and JHL-1155.

Cyclophilin Inhibitors

Examples of cyclophilin inhibitors include CPI-431-32, EDP-494, OCB-030, SCY-635, NVP-015, NVP-018, NVP-019, STG-175, and the compounds disclosed in U.S. Pat. No. 8,513,184 (Gilead Sciences), US20140030221 (Gilead Sciences), US20130344030 (Gilead Sciences), and US20130344029 (Gilead Sciences).

HBV Viral Entry Inhibitors

Examples of HBV viral entry inhibitors include Myrcludex B.

Antisense Oligonucleotide Targeting Viral mRNA

Examples of antisense oligonucleotide targeting viral mRNA include ISIS-HBVRx, IONIS-HBVRx, IONIS-GSK6-LRx, GSK-3389404, RG-6004.

Short Interfering RNAs (siRNA) and ddRNAi.

Examples of siRNA include TKM-HBV (TKM-HepB), ALN-HBV, SR-008, HepB-nRNA, and ARC-520, ARC-521, ARB-1740, ARB-1467.

Examples of DNA-directed RNA interference (ddRNAi) include BB-HB-331.

Endonuclease Modulators

Examples of endonuclease modulators include PGN-514.

Ribonucelotide Reductase Inhibitors

Examples of inhibitors of ribonucleotide reductase include Trimidox.

HBV E Antigen Inhibitors

Examples of HBV E antigen inhibitors include wogonin.

Covalently Closed Circular DNA (cccDNA) Inhibitors

Examples of cccDNA inhibitors include BSBI-25, and CHR-101.

Farnesoid X Receptor Agonist

Example of farnesoid x receptor agonist such as EYP-001.

HBV Antibodies

Examples of HBV antibodies targeting the surface antigens of the hepatitis B virus include GC-1102, XTL-17, XTL-19, KN-003, IV Hepabulin SN, and fully human monoclonal antibody therapy (hepatitis B virus infection, Humabs BioMed). Examples of HBV antibodies, including monoclonal antibodies and polyclonal antibodies, include Zutectra, Shang Sheng Gan Di, Uman Big (Hepatitis B Hyperimmune), Omri-Hep-B, Nabi-HB, Hepatect CP, HepaGam B, igantibe, Niuliva, CT-P24, hepatitis B immunoglobulin (intravenous, pH4, HBV infection, Shanghai RAAS Blood Products), and Fovepta (BT-088). Fully human monoclonal antibodies such as HBC-34.

CCR2 Chemokine Antagonists

Examples of CCR2 chemokine antagonists include propagermanium.

Thymosin Agonists

Examples of thymosin agonists include Thymalfasin, recombinant thymosin alpha 1 (GeneScience).

Cytokines

Examples of cytokines include recombinant IL-7, CYT-107, interleukin-2 (IL-2, Immunex), recombinant human interleukin-2 (Shenzhen Neptunus), IL-15, IL-21, IL-24, and celmoleukin.

Nucleoprotein Modulators

Nucleoprotein modulators may be either HBV core or capsid protein inhibitors. Examples of nucleoprotein modulators include AB-423, AT-130, GLS4, NVR-1221, NVR-3778, BAY 41-4109, morphothiadine mesilate, JNJ-379, RG-7907, ABI-H0731, ABI-H2158 and DVR-23.

Examples of capsid inhibitors include the compounds disclosed in US20140275167 (Novira Therapeutics), US20130251673 (Novira Therapeutics), US20140343032 (Roche), WO2014037480 (Roche), US20130267517 (Roche), WO2014131847 (Janssen), WO2014033176 (Janssen), WO2014033170 (Janssen), WO2014033167 (Janssen), WO2015/059212 (Janssen), WO2015118057 (Janssen), WO2015011281 (Janssen), WO2014184365 (Janssen), WO2014184350 (Janssen), WO2014161888 (Janssen), WO2013096744 (Novira), US20150225355 (Novira), US20140178337 (Novira), US20150315159 (Novira), US20150197533 (Novira), US20150274652 (Novira), US20150259324, (Novira), US20150132258 (Novira), U.S. Pat. No. 9,181,288 (Novira), WO2014184350 (Janssen), WO2013144129 (Roche).

Retinoic Acid-Inducible Gene 1 Stimulators

Examples of stimulators of retinoic acid-inducible gene 1 include SB-9200, SB-40, SB-44, ORI-7246, ORI-9350, ORI-7537, ORI-9020, ORI-9198, and ORI-7170, RGT-100.

NOD2 Stimulators

Examples of stimulators of NOD2 include SB-9200.

Phosphatidylinositol 3-kinase (PI3K) Inhibitors

Examples of PI3K inhibitors include idelalisib, ACP-319, AZD-8186, AZD-8835, buparlisib, CDZ-173, CLR-457, pictilisib, neratinib, rigosertib, rigosertib sodium, EN-3342, TGR-1202, alpelisib, duvelisib, IPI-549, UCB-5857, taselisib, XL-765, gedatolisib, ME-401, VS-5584, copanlisib, CAI orotate, perifosine, RG-7666, GSK-2636771, DS-7423, panulisib, GSK-2269557, GSK-2126458, CUDC-907, PQR-309, INCB-40093, pilaralisib, BAY-1082439, puquitinib mesylate, SAR-245409, AMG-319, RP-6530, ZSTK-474, MLN-1117, SF-1126, RV-1729, sonolisib, LY-3023414, SAR-260301, TAK-117, HMPL-689, tenalisib, voxtalisib, and CLR-1401.

Indoleamine-2, 3-Dioxygenase (IDO) Pathway Inhibitors

Examples of IDO inhibitors include epacadostat (INCB24360), resminostat (4SC-201), indoximod, F-001287, SN-35837, NLG-919, GDC-0919, GBV-1028, GBV-1012, NKTR-218, and the compounds disclosed in US20100015178 (Incyte), US2016137652 (Flexus Biosciences, Inc.), WO2014073738 (Flexus Biosciences, Inc.), and WO2015188085 (Flexus Biosciences, Inc.).

PD-1 Inhibitors

Examples of PD-1 inhibitors include nivolumab, pembrolizumab, pidilizumab, BGB-108, SHR-1210, PDR-001, PF-06801591, IBI-308, GB-226, STI-1110, and mDX-400.

PD-L1 Inhibitors

Examples of PD-L1 inhibitors include atezolizumab, avelumab, AMP-224, MEDI-0680, RG-7446, GX-P2, durvalumab, KY-1003, KD-033, MSB-0010718C, TSR-042, ALN-PDL, STI-A1014, CX-072, and BMS-936559.

In a particular embodiment, a compound disclosed herein, or a pharmaceutically acceptable salt thereof, is combined with compounds such as those disclosed in WO2018026971, US20180044329, US20180044305, US20180044304, US20180044303, US20180044350, US20180057455, US20180057486, US20180045142, WO20180044963, WO2018044783, WO2018009505, WO20180044329, WO2017066227, WO2017087777, US20170145025, WO2017079669, WO2017070089, US2017107216, WO2017222976, US20170262253, WO2017205464, US20170320875, WO2017192961, WO2017112730, US20170174679, WO2017106634, WO2017202744, WO2017202275, WO2017202273, WO2017202274, WO2017202276, WO2017180769, WO2017118762, WO2016041511, WO2016039749, WO2016142835, WO2016142852, WO2016142886, WO2016142894, and WO2016142833.

Recombinant Thymosin Alpha-1

Examples of recombinant thymosin alpha-1 include NL-004 and PEGylated thymosin alpha-1.

Bruton's Tyrosine Kinase (BTK) Inhibitors

Examples of BTK inhibitors include ABBV-105, acalabrutinib (ACP-196), ARQ-531, BMS-986142, dasatinib, ibrutinib, GDC-0853, PRN-1008, SNS-062, ONO-4059, BGB-3111, ML-319, MSC-2364447, RDX-022, X-022, AC-058, RG-7845, spebrutinib, TAS-5315, TP-0158, TP-4207, HM-71224, KBP-7536, M-2951, TAK-020, AC-0025, and the compounds disclosed in US20140330015 (Ono Pharmaceutical), US20130079327 (Ono Pharmaceutical), and US20130217880 (Ono Pharmaceutical).

KDM Inhibitors

Examples of KDM5 inhibitors include the compounds disclosed in WO2016057924 (Genentech/Constellation Pharmaceuticals), US20140275092 (Genentech/Constellation Pharmaceuticals), US20140371195 (Epitherapeutics) and US20140371214 (Epitherapeutics), US20160102096 (Epitherapeutics), US20140194469 (Quanticel), US20140171432, US20140213591 (Quanticel), US20160039808 (Quanticel), US20140275084 (Quanticel), WO2014164708 (Quanticel).

Examples of KDM1 inhibitors include the compounds disclosed in U.S. Pat. No. 9,186,337B2 (Oryzon Genomics), and GSK-2879552, RG-6016, ORY-2001.

HBV Replication Inhibitors

Examples of hepatitis B virus replication inhibitors include isothiafludine, IQP-HBV, RM-5038, and Xingantie.

Arginase Inhibitors

Examples of Arginase inhibitors include CB-1158, C-201, and resminostat.

Gene Therapy and Cell Therapy

Gene Therapy and Cell Therapy including the genetic modification to silence a gene; genetic approaches to directly kill the infected cells; the infusion of immune cells designed to replace most of the patient's own immune system to enhance the immune response to infected cells, or activate the patient's own immune system to kill infected cells, or find and kill the infected cells; genetic approaches to modify cellular activity to further alter endogenous immune responsiveness against the infection.

Gene Editors

The genome editing system is selected from the group consisting of: a CRISPR/Cas9 system, a zinc finger nuclease system, a TALEN system, a homing endonucleases system, and a meganuclease system; e.g., cccDNA elimination via targeted cleavage, and altering one or more of the hepatitis B virus (HBV) viral genes. Altering (e.g., knocking out and/or knocking down) the PreC, C, X, PreSI, PreS2, S, P or SP gene refers to (1) reducing or eliminating PreC, C, X, PreSI, PreS2, S, P or SP gene expression, (2) interfering with Precore, Core, X protein, Long surface protein, middle surface protein, S protein (also known as HBs antigen and HBsAg), polymerase protein, and/or Hepatitis B spliced protein function (HBe, HBc, HBx, PreS1, PreS2, S, Pol, and/or HBSP or (3) reducing or eliminating the intracellular, serum and/or intraparenchymal levels of HBe, HBc, HBx, LHBs, MHBs, SHBs, Pol, and/or HBSP proteins. Knockdown of one or more of the PreC, C, X, PreSI, PreS2, S, P and/or SP gene(s) is performed by targeting the gene(s) within HBV cccDNA and/or integrated HBV DNA.

CAR-T Cell Therapy

A population of immune effector cells engineered to express a chimeric antigen receptor (CAR), wherein the CAR comprises an HBV antigen-binding domain. The immune effector cell is a T cell or an NK cell. In some embodiments, the T cell is a CD4+ T cell, a CD8+ T cell, or a combination thereof. Cells can be autologous or allogeneic.

TCR-T Cell Therapy

T cells expressing HBV-specific T cell receptors. TCR-T cells are engineered to target HBV derived peptides presented on the surface of virus-infected cells.

T-Cells expressing HBV surface antigen (HBsAg)-specific TCR.

TCR-T therapy directed to treatment of HBV, such as LTCR-H2-1

HBV Combination Therapy

In a particular embodiment, a compound disclosed herein, or a pharmaceutically acceptable salt thereof, is combined with one, two, three, or four additional therapeutic agent selected from the group consisting of adefovir (HEPSERA®), tenofovir disoproxil fumarate (VIREAD), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPIVIR-HBV®). In a particular embodiment, a compound disclosed herein, or a pharmaceutically acceptable salt thereof, is combined with a first additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPIVIR-HBV®). In one embodiment, pharmaceutical compositions comprising a compound disclosed herein, or a pharmaceutically acceptable salt thereof, in combination with one or more (e.g., one, two, three, four, one or two, or one to three, or one to four) additional therapeutic agents and a pharmaceutically acceptable carrier, diluent, or excipient are provided.

HBV DNA Polymerase Inhibitor Combination Therapy

In a specific embodiment, a compound disclosed herein, or a pharmaceutically acceptable salt thereof, is combined with an HBV DNA polymerase inhibitor. In another specific embodiment, a compound disclosed herein, or a pharmaceutically acceptable salt thereof, is combined with an HBV DNA polymerase inhibitor and at least one additional therapeutic agent selected from the group consisting of: immunomodulators, TLR modulators, interferon alpha receptor ligands, hyaluronidase inhibitors, recombinant IL-7, HBsAg inhibitors, HBsAg secretion or assembly inhibitors, compounds targeting HBcAg, cyclophilin inhibitors, HBV vaccines, HBV viral entry inhibitors, NTCP inhibitors, antisense oligonucleotide targeting viral mRNA, siRNA, miRNA gene therapy agents, endonuclease modulators, inhibitors of ribonucleotide reductase, hepatitis B virus E antigen inhibitors, recombinant SRA proteins, src kinase inhibitors, HBx inhibitors, cccDNA inhibitors, sshRNAs, HBV antibodies including HBV antibodies targeting the surface antigens of the hepatitis B virus and bispecific antibodies and “antibody-like” therapeutic proteins (such as DARTs®, DUOBODIES®, BITES®, XmAbs®, TandAbs, Fab derivatives, or TCR-like antibodies), CCR2 chemokine antagonists, thymosin agonists, cytokines, nucleoprotein modulators (HBV core or capsid protein modulators), stimulators of retinoic acid-inducible gene 1, stimulators of RIG-I like receptors, stimulators of NOD2, stimulators of NOD1, Arginase inhibitors, STING agonists, PI3K inhibitors, lymphotoxin beta receptor activators, natural killer cell receptor 2B4 inhibitors, Lymphocyte-activation gene 3 inhibitors, CD160 inhibitors, cytotoxic T-lymphocyte-associated protein 4 (ipi4) inhibitors, CD137 inhibitors, Killer cell lectin-like receptor subfamily G member 1 inhibitors, TIM-3 inhibitors, B- and T-lymphocyte attenuator inhibitors, CD305 inhibitors, PD-1 inhibitors, PD-L1 inhibitors, PEG-Interferon Lambda, recombinant thymosin alpha-1, BTK inhibitors, modulators of TIGIT, modulators of CD47, modulators of SIRPalpha, modulators of ICOS, modulators of CD27, modulators of CD70, modulators of OX40, epigenetic modifiers, modulators of NKG2D, modulators of Tim-4, modulators of B7-H4, modulators of B7-H3, modulators of NKG2A, modulators of GITR, modulators of CD160, modulators of HEVEM, modulators of CD161, modulators of Axl, modulators of Mer, modulators of Tyro, gene modifiers or editors such as CRISPR (including CRISPR Cas9), zinc finger nucleases or synthetic nucleases (TALENs), IAPs inhibitors, SMAC mimetics, KDM5 inhibitors, IDO inhibitors, and hepatitis B virus replication inhibitors.

In another specific embodiment, a compound disclosed herein, or a pharmaceutically acceptable salt thereof, is combined with an HBV DNA polymerase inhibitor, one or two additional therapeutic agents selected from the group consisting of immunomodulators, TLR modulators, HBsAg inhibitors, HBsAg secretion or assembly inhibitors, HBV therapeutic vaccines, HBV antibodies including HBV antibodies targeting the surface antigens of the hepatitis B virus and bispecific antibodies and “antibody-like” therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, and stimulators of NOD2, and one or two additional therapeutic agents selected from the group consisting of HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein modulators).

In another specific embodiment, a compound disclosed herein, or a pharmaceutically acceptable salt thereof, is combined with an HBV DNA polymerase inhibitor and at least a second additional therapeutic agent selected from the group consisting of: immunomodulators, TLR modulators, HBsAg inhibitors, HBV therapeutic vaccines, HBV antibodies including HBV antibodies targeting the surface antigens of the hepatitis B virus and bispecific antibodies and “antibody-like” therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, and stimulators of NOD2.

In another specific embodiment, a compound disclosed herein, or a pharmaceutically acceptable salt thereof, is combined with an HBV DNA polymerase inhibitor and at least a second additional therapeutic agent selected from the group consisting of: HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein inhibitors).

HBV Drug Combination Therapy

In a particular embodiment, a compound disclosed herein, or a pharmaceutically acceptable salt thereof, is combined with a first additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPIVIR-HBV®), and at least a second additional therapeutic agent selected from the group consisting of immunomodulators, TLR modulators, interferon alpha receptor ligands, hyaluronidase inhibitors, recombinant IL-7, HBsAg inhibitors, HBsAg secretion or assembly inhibitors, compounds targeting HBcAg, cyclophilin inhibitors, HBV vaccines, HBV viral entry inhibitors, NTCP inhibitors, antisense oligonucleotide targeting viral mRNA, siRNA, miRNA gene therapy agents, endonuclease modulators, inhibitors of ribonucleotide reductase, hepatitis B virus E antigen inhibitors, recombinant SRA proteins, src kinase inhibitors, HBx inhibitors, cccDNA inhibitors, sshRNAs, HBV antibodies including HBV antibodies targeting the surface antigens of the hepatitis B virus and bispecific antibodies and “antibody-like” therapeutic proteins (such as DARTs®, DUOBODIES®, BITES®, XmAbs®, TandAbs®, Fab derivatives, and TCR-like antibodies), CCR2 chemokine antagonists, thymosin agonists, cytokines, nucleoprotein modulators (HBV core or capsid protein modulators), stimulators of retinoic acid-inducible gene 1, stimulators of RIG-I like receptors, stimulators of NOD2, stimulators of NOD1, IDO inhibitors, recombinant thymosin alpha-1, Arginase inhibitors, STING agonists, PI3K inhibitors, lymphotoxin beta receptor activators, natural killer cell receptor 2B4 inhibitors, Lymphocyte-activation gene 3 inhibitors, CD160 inhibitors, ipi4 inhibitors, CD137 inhibitors, killer cell lectin-like receptor subfamily G member 1 inhibitors, TIM-3 inhibitors, B- and T-lymphocyte attenuator inhibitors, epigenetic modifiers, CD305 inhibitors, PD-1 inhibitors, PD-L1 inhibitors, PEG-Interferon Lambd, BTK inhibitors, modulators of TIGIT, modulators of CD47, modulators of SIRPalpha, modulators of ICOS, modulators of CD27, modulators of CD70, modulators of OX40, modulators of NKG2D, modulators of Tim-4, modulators of B7-H4, modulators of B7-H3, modulators of NKG2A, modulators of GITR, modulators of CD160, modulators of HEVEM, modulators of CD161, modulators of Axl, modulators of Mer, modulators of Tyro, gene modifiers or editors such as CRISPR (including CRISPR Cas9), zinc finger nucleases or synthetic nucleases (TALENs), IAPs inhibitors, SMAC mimetics, KDM5 inhibitors, and hepatitis B virus replication inhibitors.

In a particular embodiment, a compound disclosed herein, or a pharmaceutically acceptable salt thereof, is combined with a first additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®) or lamivudine (EPIVIR-HBV®) and at least a second additional therapeutic agent selected from the group consisting of peginterferon alfa-2b (PEG-INTRON), MULTIFERON®, interferon alpha 1b (HAPGEN®), interferon alpha-2b (INTRON A®), pegylated interferon alpha-2a (PEGASYS®), interferon alfa-n1 (HUMOFERON®), ribavirin, interferon beta-1a (AVONEX®), Bioferon, Ingaron, Inmutag (Inferon), Algeron, Roferon-A, Oligotide, Zutectra, Shaferon, interferon alfa-2b (AXXO), Alfaferone, interferon alfa-2b (BioGeneric Pharma), Feron, interferon-alpha 2 (CJ), BEVAC, Laferonum, VIPEG, BLAUFERON-B, BLAUFERON-A, Intermax Alpha, Realdiron, Lanstion, Pegaferon, PDferon-B, interferon alfa-2b (IFN, Laboratorios Bioprofarma), alfainterferona 2b, Kalferon, Pegnano, Feronsure, PegiHep, interferon alfa 2b (Zydus-Cadila), Optipeg A, Realfa 2B, Reliferon, interferon alfa-2b (Amega), interferon alfa-2b (Virchow), peginterferon alfa-2b (Amega), Reaferon-EC, Proquiferon, Uniferon, Urifron, interferon alfa-2b (Changchun Institute of Biological Products), Anterferon, Shanferon, MOR-22, interleukin-2 (IL-2, Immunex), recombinant human interleukin-2 (Shenzhen Neptunus), Layfferon, Ka Shu Ning, Shang Sheng Lei Tai, INTEFEN, SINOGEN, Fukangtai, Alloferon, and celmoleukin.

In a particular embodiment, a compound disclosed herein, or a pharmaceutically acceptable salt thereof, is combined with a first additional therapeutic agent selected from the group consisting of adefovir (HEPSERA), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPIVIR-HBV®), and at least a second additional therapeutic agent selected from the group consisting of immunomodulators, TLR modulators, HBsAg inhibitors, HBsAg secretion or assembly inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, Arginase inhibitors, PI3K inhibitors, PD-1 inhibitors, PD-L1 inhibitors, IDO inhibitors, and stimulators of NOD2.

In a particular embodiment, a compound disclosed herein, or a pharmaceutically acceptable salt thereof, is combined with a first additional therapeutic agent selected from the group consisting of: adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPIVIR-HBV®), and at least a second additional therapeutic agent selected from the group consisting of HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein modulators).

In a particular embodiment, a compound disclosed herein, or a pharmaceutically acceptable salt thereof, is combined with a first additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPIVIR-HBV®); one, two, or three additional therapeutic agents selected from the group consisting of immunomodulators, TLR modulators, HBsAg inhibitors, HBsAg secretion or assembly inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, and stimulators of NOD2; and one or two additional therapeutic agents selected from the group consisting of HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein modulators).

In a particular embodiment, a compound disclosed herein, or a pharmaceutically acceptable salt thereof, is combined with a first additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPIVIR-HBV®); one or two additional therapeutic agents selected from the group consisting of immunomodulators, TLR modulators, HBsAg inhibitors, HBsAg secretion or assembly inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, and stimulators of NOD2; and one or two additional therapeutic agents selected from the group consisting of HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein modulators).

In a particular embodiment, a compound disclosed herein, or a pharmaceutically acceptable salt thereof, is combined with a first additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPIVIR-HBV®); and one, two, three, or four additional therapeutic agents selected from the group consisting of immunomodulators, TLR7 modulators, TLR8 modulators, HBsAg inhibitors, HBsAg secretion or assembly inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, stimulators of NOD2 HBV viral entry inhibitors, NTCP inhibitors, HBx inhibitors, cccDNA inhibitors, siRNA, miRNA gene therapy agents, sshRNAs, KDM5 inhibitors, and nucleoprotein modulators (HBV core or capsid protein modulators).

In a particular embodiment, a compound disclosed herein, or a pharmaceutically acceptable salt thereof, is combined with compounds such as those disclosed in U.S. Publication No. 2010/0143301 (Gilead Sciences), U.S. Publication No. 2011/0098248 (Gilead Sciences), U.S. Publication No. 2009/0047249 (Gilead Sciences), U.S. Pat. No. 8,722,054 (Gilead Sciences), U.S. Publication No. 2014/0045849 (Janssen), U.S. Publication No. 2014/0073642 (Janssen), WO2014/056953 (Janssen), WO2014/076221 (Janssen), WO2014/128189 (Janssen), U.S. Publication No. 2014/0350031 (Janssen), WO2014/023813 (Janssen), U.S. Publication No. 2008/0234251 (Array Biopharma), U.S. Publication No. 2008/0306050 (Array Biopharma), U.S. Publication No. 2010/0029585 (Ventirx Pharma), U.S. Publication No. 2011/0092485 (Ventirx Pharma), US2011/0118235 (Ventirx Pharma), U.S. Publication No. 2012/0082658 (Ventirx Pharma), U.S. Publication No. 2012/0219615 (Ventirx Pharma), U.S. Publication No. 2014/0066432 (Ventirx Pharma), U.S. Publication No. 2014/0088085 (Ventirx Pharma), U.S. Publication No. 2014/0275167 (Novira Therapeutics), U.S. Publication No. 2013/0251673 (Novira Therapeutics), U.S. Pat. No. 8,513,184 (Gilead Sciences), U.S. Publication No. 2014/0030221 (Gilead Sciences), U.S. Publication No. 2013/0344030 (Gilead Sciences), U.S. Publication No. 2013/0344029 (Gilead Sciences), US20140275167 (Novira Therapeutics), US20130251673 (Novira Therapeutics), U.S. Publication No. 2014/0343032 (Roche), WO2014037480 (Roche), U.S. Publication No. 2013/0267517 (Roche), WO2014131847 (Janssen), WO2014033176 (Janssen), WO2014033170 (Janssen), WO2014033167 (Janssen), WO2015/059212 (Janssen), WO2015118057 (Janssen), WO2015011281 (Janssen), WO2014184365 (Janssen), WO2014184350 (Janssen), WO2014161888 (Janssen), WO2013096744 (Novira), US20150225355 (Novira), US20140178337 (Novira), US20150315159 (Novira), US20150197533 (Novira), US20150274652 (Novira), US20150259324, (Novira), US20150132258 (Novira), U.S. Pat. No. 9,181,288 (Novira), WO2014184350 (Janssen), WO2013144129 (Roche), US20100015178 (Incyte), US2016137652 (Flexus Biosciences, Inc.), WO2014073738 (Flexus Biosciences, Inc.), WO2015188085 (Flexus Biosciences, Inc.), U.S. Publication No. 2014/0330015 (Ono Pharmaceutical), U.S. Publication No. 2013/0079327 (Ono Pharmaceutical), U.S. Publication No. 2013/0217880 (Ono pharmaceutical), WO2016057924 (Genentech/Constellation Pharmaceuticals), US20140275092 (Genentech/Constellation Pharmaceuticals), US20140371195 (Epitherapeutics) and US20140371214 (Epitherapeutics), US20160102096 (Epitherapeutics), US20140194469 (Quanticel), US20140171432, US20140213591 (Quanticel), US20160039808 (Quanticel), US20140275084 (Quanticel), WO2014164708 (Quanticel), U.S. Pat. No. 9,186,337B2 (Oryzon Genomics), and other drugs for treating HBV, and combinations thereof.

In certain embodiments, a compound as disclosed herein (e.g., any compound of Formula I) may be combined with one or more (e.g., one, two, three, four, one or two, one to three, or one to four) additional therapeutic agents in any dosage amount of the compound of Formula (I) (e.g., from 10 mg to 1000 mg of compound).

In certain embodiments, a compound disclosed herein, or a pharmaceutically acceptable salt thereof, is combined with 5-30 mg tenofovir alafenamide fumarate, tenofovir alafenamide hemifumarate, or tenofovir alafenamide. In certain embodiments, a compound disclosed herein, or a pharmaceutically acceptable salt thereof, is combined with 5-10; 5-15; 5-20; 5-25; 25-30; 20-30; 15-30; or 10-30 mg tenofovir alafenamide fumarate, tenofovir alafenamide hemifumarate, or tenofovir alafenamide. In certain embodiments, a compound disclosed herein, or a pharmaceutically acceptable salt thereof, is combined with 10 mg tenofovir alafenamide fumarate, tenofovir alafenamide hemifumarate, or tenofovir alafenamide. In certain embodiments, a compound disclosed herein, or a pharmaceutically acceptable salt thereof, is combined with 25 mg tenofovir alafenamide fumarate, tenofovir alafenamide hemifumarate, or tenofovir alafenamide. A compound as disclosed herein (e.g., a compound of Formula I) may be combined with the agents provided herein in any dosage amount of the compound (e.g., from 50 mg to 500 mg of compound) the same as if each combination of dosages were specifically and individually listed.

In certain embodiments, a compound disclosed herein, or a pharmaceutically acceptable salt thereof, is combined with 100-400 mg tenofovir disoproxil fumarate, tenofovir disoproxil hemifumarate, or tenofovir disoproxil. In certain embodiments, a compound disclosed herein, or a pharmaceutically acceptable salt thereof, is combined with 100 mg to 150 mg; 100 mg to 200 mg; 100 mg to 250 mg; 100 mg to 300 mg; 100 mg to 350 mg; 150 mg to 200 mg; 150 mg to 250 mg; 150 mg to 300 mg; 150 mg to 350 mg; 150 mg to 400 mg; 200 mg to 250 mg; 200 mg to 300 mg; 200 mg to 350 mg; 200 mg to 400 mg; 250 mg to 350 mg; 250 mg to 400 mg; 350 mg to 400 or 300 mg to 400 mg tenofovir disoproxil fumarate, tenofovir disoproxil hemifumarate, or tenofovir disoproxil. In certain embodiments, a compound disclosed herein, or a pharmaceutically acceptable salt thereof, is combined with 300 mg tenofovir disoproxil fumarate, tenofovir disoproxil hemifumarate, or tenofovir disoproxil. In certain embodiments, a compound disclosed herein, or a pharmaceutically acceptable salt thereof, is combined with 250 mg tenofovir disoproxil fumarate, tenofovir disoproxil hemifumarate, or tenofovir disoproxil. In certain embodiments, a compound disclosed herein, or a pharmaceutically acceptable salt thereof, is combined with 150 mg tenofovir disoproxil fumarate, tenofovir disoproxil hemifumarate, or tenofovir disoproxil. A compound as disclosed herein (e.g., a compound of Formula I) may be combined with the agents provided herein in any dosage amount of the compound (e.g., from 50 mg to 500 mg of compound) the same as if each combination of dosages were specifically and individually listed.

In one embodiment, kits comprising a compound disclosed herein, or a pharmaceutically acceptable salt thereof, in combination with one or more (e.g., one, two, three, four, one or two, or one to three, or one to four) additional therapeutic agents are provided.

All of the U.S. patents, U.S. patent application publications, U.S. patent applications, foreign patents, foreign patent applications and non-patent publications referred to in this specification are incorporated herein by reference, in their entirety to the extent not inconsistent with the present description.

Any pharmaceutical composition provided in the present disclosure may be used in the kits, the same as if each and every composition were specifically and individually listed for use in a kit.

Articles of Manufacture

Articles of manufacture comprising a container in which a compound of formula (I) or a pharmaceutically acceptable salt thereof, and at least one pharmaceutically acceptable carrier are contained are provided. The article of manufacture may be a bottle, vial, ampoule, single-use disposable applicator, or the like, containing the pharmaceutical composition provided in the present disclosure. The container may be formed from a variety of materials, such as glass or plastic and in one aspect also contains a label on, or associated with, the container which indicates directions for use in the treatment of cancer or inflammatory conditions.

It should be understood that the active ingredient may be packaged in any material capable of providing reasonable chemical and physical stability, such as an aluminum foil bag.

Unit dosage forms of the pharmaceutical composition comprising a compound of formula (I), or a pharmaceutically acceptable salt thereof, and at least one pharmaceutically acceptable carrier are also provided.

Any pharmaceutical composition provided in the present disclosure may be used in the articles of manufacture, the same as if each and every composition were specifically and individually listed for use an article of manufacture.

Also provided is a kit that includes a compound of formula (I) or a pharmaceutically acceptable salt, stereoisomer, mixture of stereoisomers or tautomer thereof; a label, and/or instructions for use of the compound in the treatment of a disease or condition mediated by PD-1, PD-L1 activity or PD-1/PD-L1 interaction.

Also provided is an article of manufacture which includes a compound of formula (I) or a pharmaceutically acceptable salt, prodrug, or solvate thereof; and a container. In one embodiment, the container may be a vial, jar, ampoule, preloaded syringe, or an intravenous bag.

Formulations of compound(s) of the present disclosure i.e., a compound of formula (I) or the combination of a compound of formula (I) and an additional agent may be accomplished by admixing said compounds or salt thereof with one or more non-toxic, pharmaceutically acceptable vehicles, carriers and/or diluents and/or adjuvants collectively referred to herein as excipients or carrier materials. The compounds of the disclosure may be administered by any suitable route, preferably in the form of a pharmaceutical composition adapted to such route, and in a therapeutically effective dose. The compounds or the combination of compounds for the disclosure may be delivered orally, mucosally, parenterally, including intravascularly, intravenously, intraperitoneally, subcutaneously, intramuscularly, and intranasally in dosage formulations containing conventional pharmaceutical excipients.

In one embodiment, the combination of a compound formula (I), or a pharmaceutically acceptable salt thereof, and an additional agent useful for the treatment of cancer may be formulated in a fixed dose or combined dose formulation in a tablet, capsule or premixed IV solution. In another embodiment, the fixed dose combination preferably comprises of compound formula (I), and an additional anticancer agent. Other fixed dose formulations may include premixed liquids, suspensions, elixirs, aerosolized sprays or patch presentations. As used herein fixed dose or combined dose formulations are synonymous with simultaneous co-administration of the active ingredients of the compound (I) and at least one additional agent.

Synthesis

The compounds of the disclosure may be prepared using methods disclosed herein and routine modifications thereof which will be apparent given the disclosure herein and methods well known in the art. Conventional and well-known synthetic methods may be used in addition to the teachings herein. The synthesis of typical compounds of formula (I), or a pharmaceutically acceptable salt thereof, e.g., compounds having structures described by one or more of formula (I), or other formulas or compounds disclosed herein, may be accomplished as described in the following examples. If available, reagents may be purchased commercially, e.g., from Sigma Aldrich or other chemical suppliers.

General Syntheses

Typical embodiments of compounds in accordance with the present disclosure may be synthesized using the general reaction schemes and/or examples described below. It will be apparent given the description herein that the general schemes may be altered by substitution of the starting materials with other materials having similar structures to result in products that are correspondingly different. Descriptions of syntheses follow to provide numerous examples of how the starting materials may vary to provide corresponding products. Starting materials are typically obtained from commercial sources or synthesized using published methods for synthesizing compounds which are embodiments of the present disclosure, inspection of the structure of the compound to be synthesized will provide the identity of each substituent group. The identity of the final product will generally render apparent the identity of the necessary starting materials by a simple process of inspection, given the examples herein. Group labels (e.g., $R^1$, $R^a$, $R^b$) used in the reaction schemes herein are for illustrative purposes only and unless otherwise specified do not necessarily match by name or function the labels used elsewhere to describe compounds of formula (I) or aspects or fragments thereof.

Synthetic Reaction Parameters

The compounds of this disclosure can be prepared from readily available starting materials using, for example, the following general methods and procedures. It will be appreciated that where typical or preferred process conditions (i.e., reaction temperatures, times, mole ratios of reactants, solvents, pressures, etc.) are given; other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts (1999) Protecting Groups in Organic Synthesis, 3rd Edition, Wiley, New York, and references cited therein.

Furthermore, the compounds of this disclosure may contain one or more chiral centers. Accordingly, if desired, such compounds can be prepared or isolated as pure stereoisomers, i.e., as individual enantiomers or diastereomers or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA). Others may be prepared by procedures or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989) organic Reactions, Volumes 1-40 (John Wiley, and Sons, 1991), March's Advanced Organic Chemistry, (John Wiley, and Sons, $5^{th}$ Edition, 2001), and Larock's Comprehensive Organic Transformations (VCH Publishers Inc., 1989).

The terms "solvent," "inert organic solvent" or "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, pyridine and the like). Unless specified to the contrary, the solvents used in the reactions of the present disclosure are inert organic solvents, and the reactions are carried out under an inert gas, preferably nitrogen.

The term "q.s." means adding a quantity sufficient to achieve a stated function, e.g., to bring a solution to the desired volume (i.e., 100%).

The compounds as disclosed herein may be prepared according to the general schemes provided below. Scheme 1 shows the general synthesis of building block 7.

Scheme 1

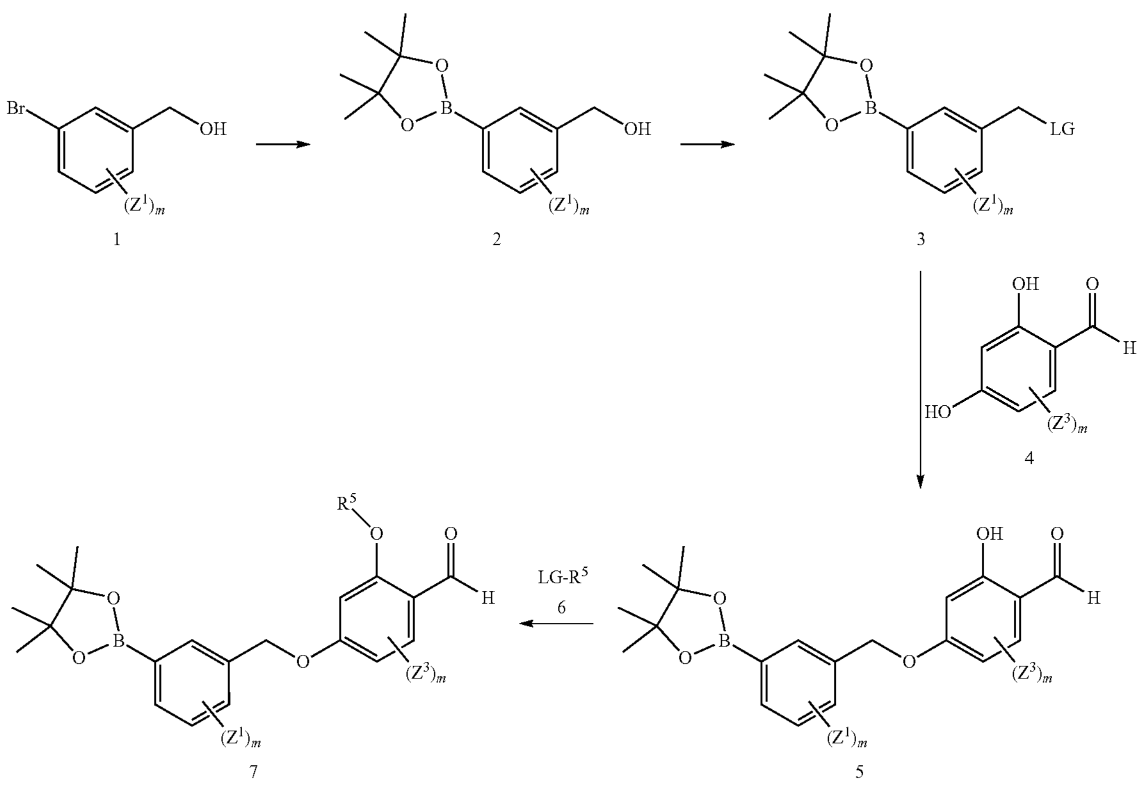

1 2 3 4 5 7

Suitably substituted 3-bromobenzyl alcohol (1) is converted to boronate ester (2) using standard conditions (4,4,4',4',5,5,5',5'-octamethyl-2,2'-bi(1,3,2-dioxaborolane), a suitable palladium catalyst such as [1,1'-Bis(diphenylphosphino)ferrocene]dichloropalladium(II) and base such as potassium acetate, in a suitable solvent such as 1,4-dioxane under heating. The alcohol is converted to a leaving group such as mesylate, chloride, bromide or iodide (3) which is used to selectively alkylate dihydroxybenzaldehyde (4) using a mild base such as sodium bicarbonate. The second hydroxyl group is alkylated with an appropriate alkylating agent (6) to provide building block (7).

As used in the following schemes, $Z^1$ is halo, —$OR^a$, —$NO_2$, —CN, —$NR^aR^b$, —$N_3$, —$SO_2R^a$, —$C_{1-6}$ alkyl, —$C_{1-6}$ haloalkyl, —$C_{2-6}$alkenyl, —$C_{2-6}$alkynyl, —$OC_{1-6}$alkyl, —$OC_{1-6}$haloalkyl, —$C_{3-8}$cycloalkyl, and —$C_{1-6}$ alkyl$C_{3-8}$ cycloalkyl, wherein each alkyl, alkenyl, alkynyl, and cycloalkyl group is optionally substituted with 1 to 4 groups independently selected from oxo, —$NO_2$, —$N_3$, $OR^a$, halo, and cyano; $Z^3$ is halo, —$OR^a$, —$N_3$, —$NO_2$, —CN, —$NR^1R^2$, —$SO_2R^a$, —$SO_2NR^aR^b$, —$NR^aSO_2R^a$, —$NR^aC(O)R^a$, —$C(O)R^a$, —$C(O)OR^a$, —$C(O)NR^aR^b$, —$NR^aC(O)OR^a$, —$NR^aC(O)NR^1R^2$, —$OC(O)NR^aR^b$, —$NR^aSO_2NR^aR^b$, —$C(O)NR^aSO_2NR^aR^b$, —$C_{1-6}$ alkyl, —$C_{2-6}$ alkenyl, —$C_{2-6}$ alkynyl, —$OC_{1-6}$ alkyl, —$C_{3-8}$ cycloalkyl, —$C_{1-6}$ alkyl$C_{3-8}$ cycloalkyl, aryl, heteroaryl, heterocyclyl, and $R^N$, wherein the alkyl, alkenyl, alkynyl, $C_{3-8}$ cycloalkyl, aryl, heteroaryl, or heterocyclyl group is optionally substituted with 1 to 4 groups independently selected from oxo, —$NO_2$, —$N_3$, —$OR^a$, halo, cyano, —$NR^aR^b$, —$C(O)R^a$, —$C(O)OR^a$, —$OC_{1-6}$ alkylCN, —$C(O)NR^aR^b$, $NR^aC(O)R^a$, —$NR^aC(O)OR^a$, —$SO_2R^a$, —$NR^aSO_2R^b$, —$SO_2NR^aR^b$, —$NR^aSO_2NR^aR^b$, —C(O) $NR^aSO_2NR^aR^b$ and —$C_{3-8}$ cycloalkyl; and wherein the heteroaryl or heterocyclic group may be oxidized on a nitrogen atom to form an N-oxide or oxidized on a sulfur atom to form a sulfoxide or sulfone; m is 0, 1, 2, 3, or 4; $R^5$ may be any appropriate substituent on Q as defined herein, such as

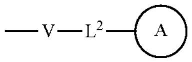

or $R^a$; and the remaining variables are as defined herein.

Scheme 2 shows the general synthesis of building block (11) using similar chemistry as in Scheme 1.

Scheme 2

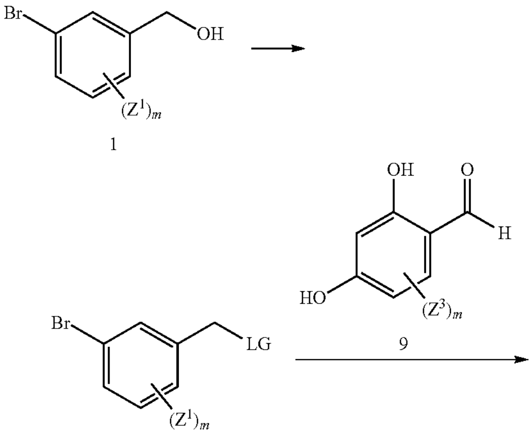

1

9

8

-continued

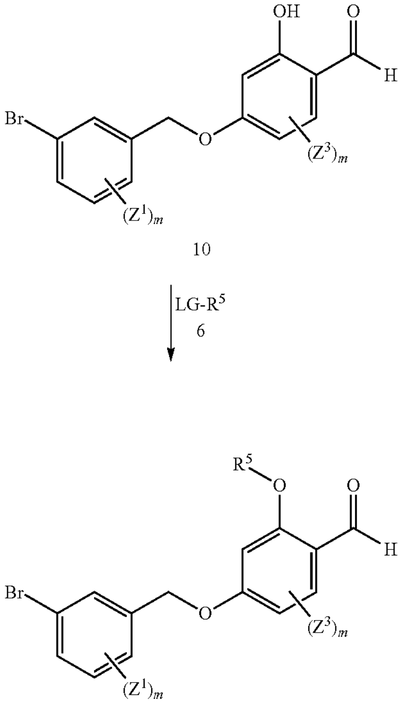

10

6

11

Building blocks (7) and (11) can be coupled in a palladium catalyzed reaction to form dialdehyde (12) (Scheme 3). For example, boronic ester (7) is coupled with coupling partner (11) using a palladium catalyst, such as $Pd(PPh_3)_4$, to afford (14). Palladium mediated cross-coupling reactions that enable the biaryl formation but employ alternative coupling partners and reagents include, for example, the Negishi, Kumada, and Stille reactions. Dialdehyde (12) is subjected to reductive amination conditions in the presence of an appropriate amine to give target compound (14). Reducing agents which can be used for this reaction include but are not limited to sodium cyanoborohydride, sodium triacetoxyborohydride, borane-picoline complex in the presence or absence of an acid such as acetic acid in a variety of solvents and solvent mixtures including but not limited to N,N-dimethylformamide, methanol, ethanol, and dimethyl sulfoxide.

Scheme 3

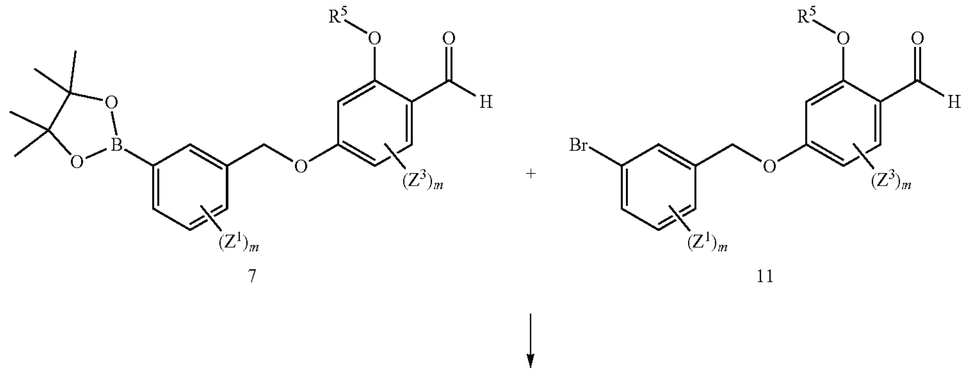

7

+

11

-continued
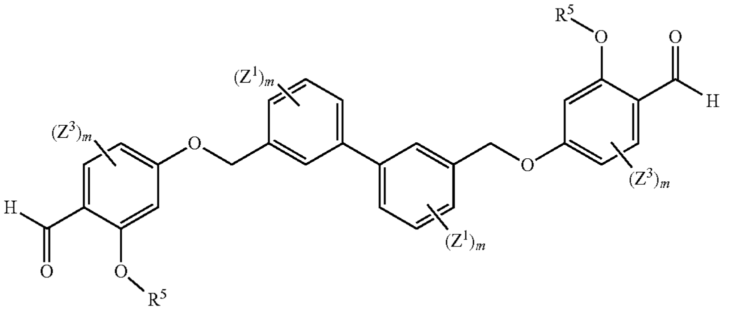
12
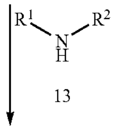
13
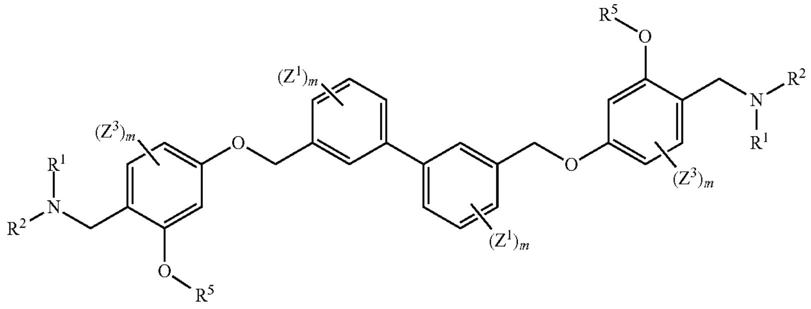
14
Alternatively, compounds disclosed herein can be built as shown in scheme 4 using similar chemistry as described above.
Scheme 4
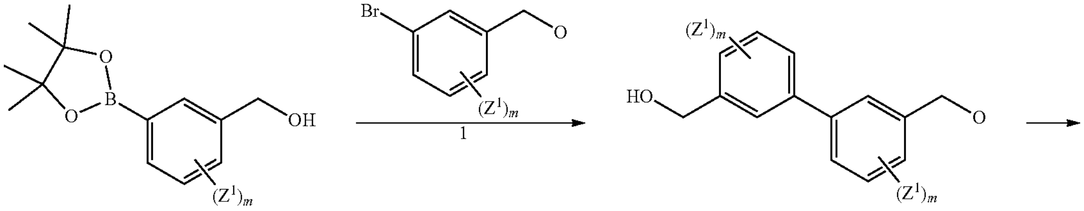
2 1 15

-continued
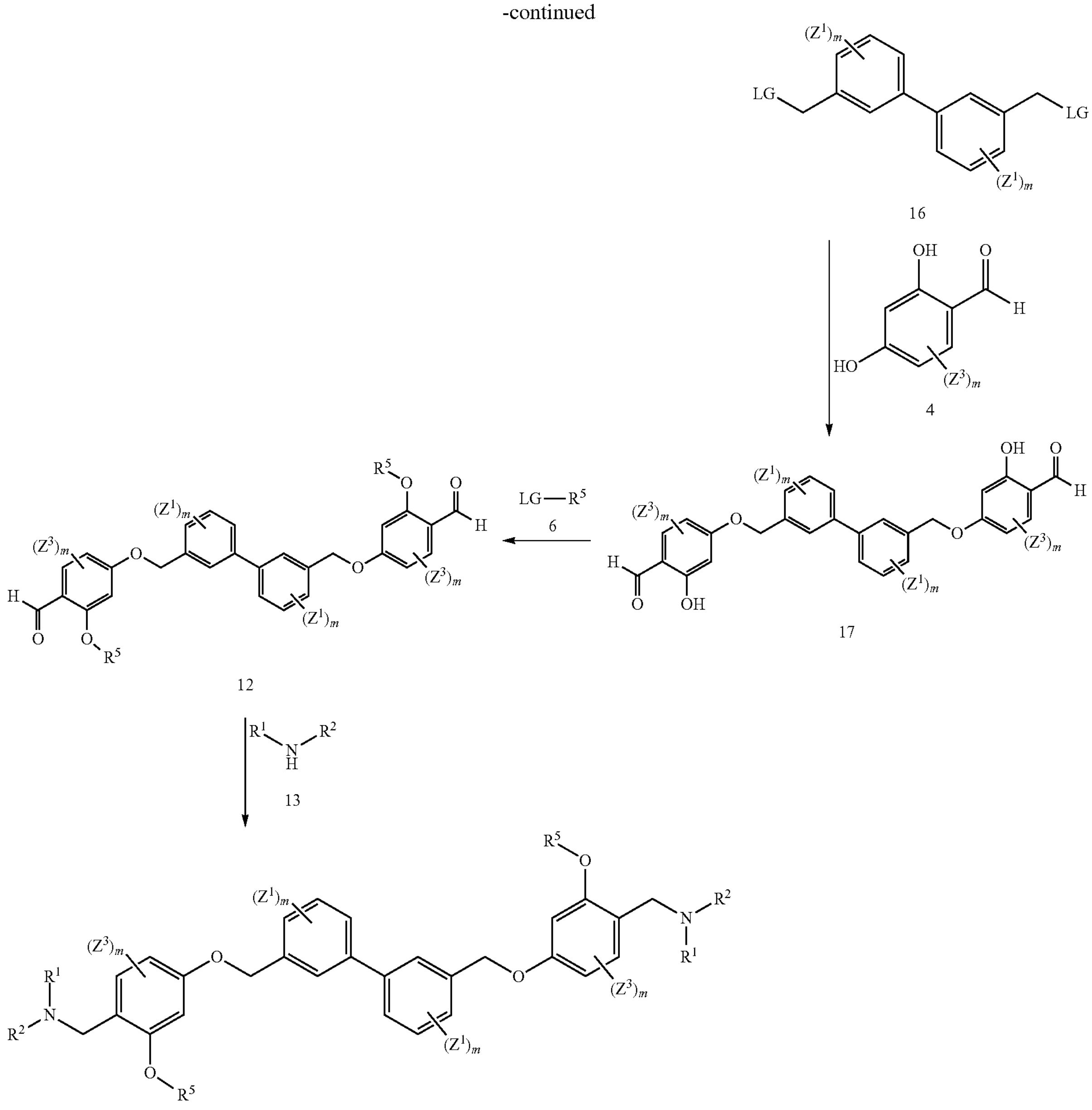
14
Alternatively, an already suitably substituted phenol (27) can be used in the dialkylation reaction. (Scheme 5).
Scheme 5
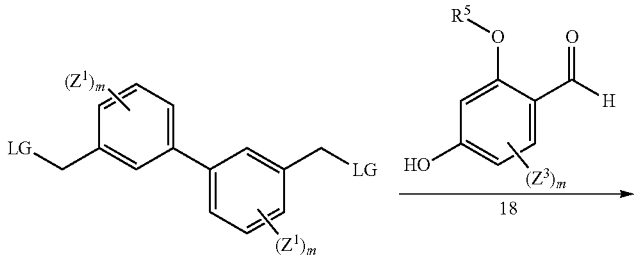
16

-continued

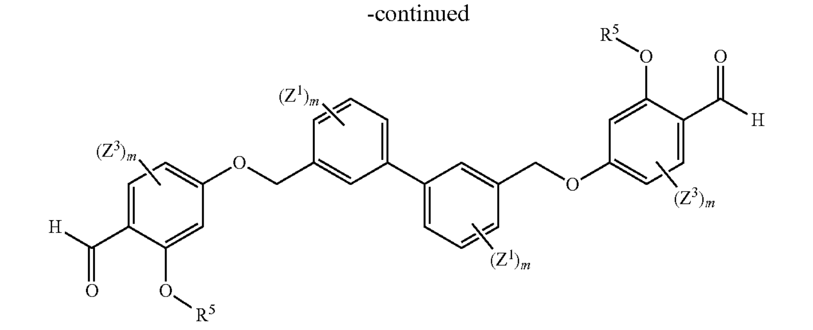

19

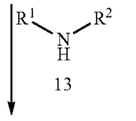

13

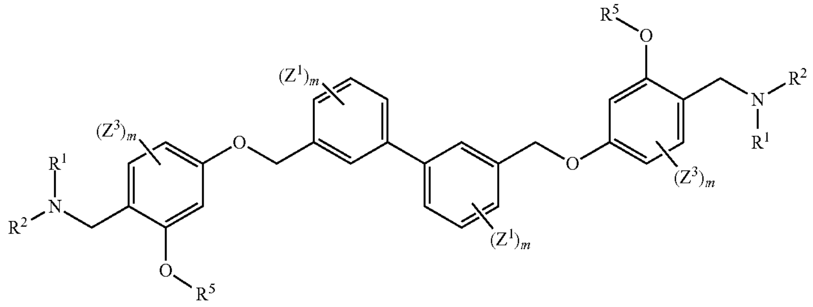

14

Scheme 6 shows the general synthesis of pyridine containing compounds. A bis-benzylic alcohol can be coupled to a suitably substituted 2-chloropyridine (20) using either a strong base such as sodium hydride under heating, or alternatively using transition metal catalyzed coupling conditions (as described in the literature, such as Ullmann ether synthesis, which uses copper based catalysts, and Buchwald -Hartwig reaction, which uses a palladium catalyst, such as $Pd(dba)_2$, a suitable ligand, such as XPhos, in the presence of a base, such as cesium carbonate) to give (21). If desired, a halogen (X=Cl, Br, I) can be introduced via electrophilic aromatic substitution, using a N-halosuccinimide, Palau'Chlor, bromine, or similar, to give (22). After removal of the protecting group, the hydroxypyridine (23) is alkylated with a suitable alkylating agent (6) to provide dialdehyde (24). The dialdehyde (24) is then converted to the target compound (25) using an appropriate amine (13)under reductive amination conditions.

Scheme 6

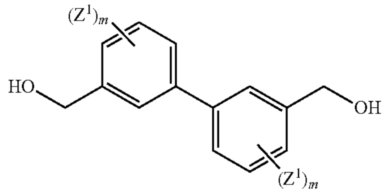

15

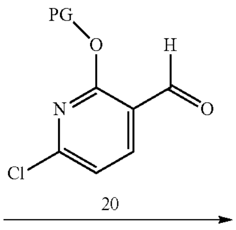

20

-continued
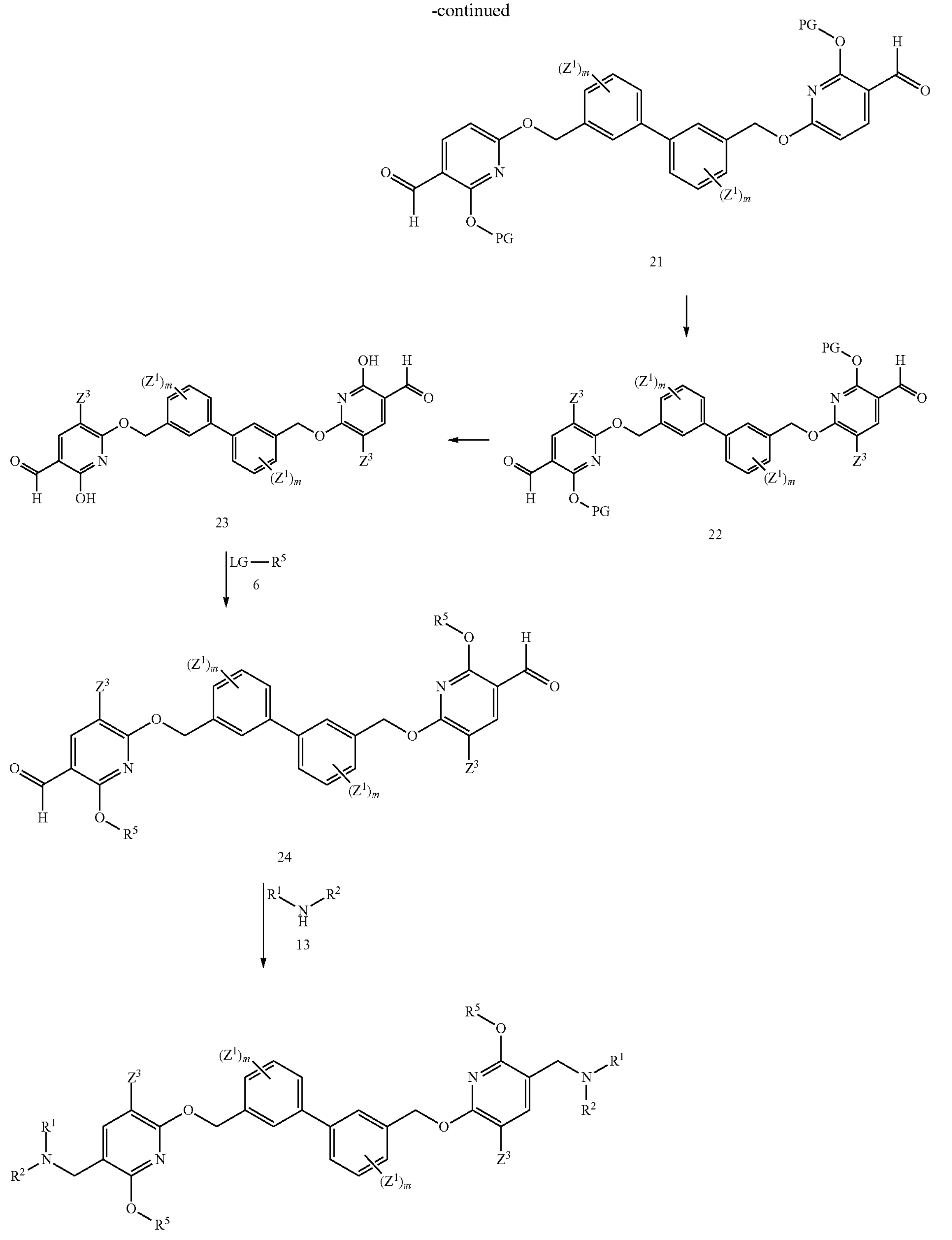
21
22
23
24
25
Alternatively (Scheme 7), a substituted 2-chloropyridine (26) can be coupled with a substituted 3-bromobenzyl alcohol (1) using a strong base (such as sodium hydride) under heating followed by borylation and biaryl formation to give dialdehyde (24). Target compound (25) can be achieved as described in Scheme 6.

Scheme 7

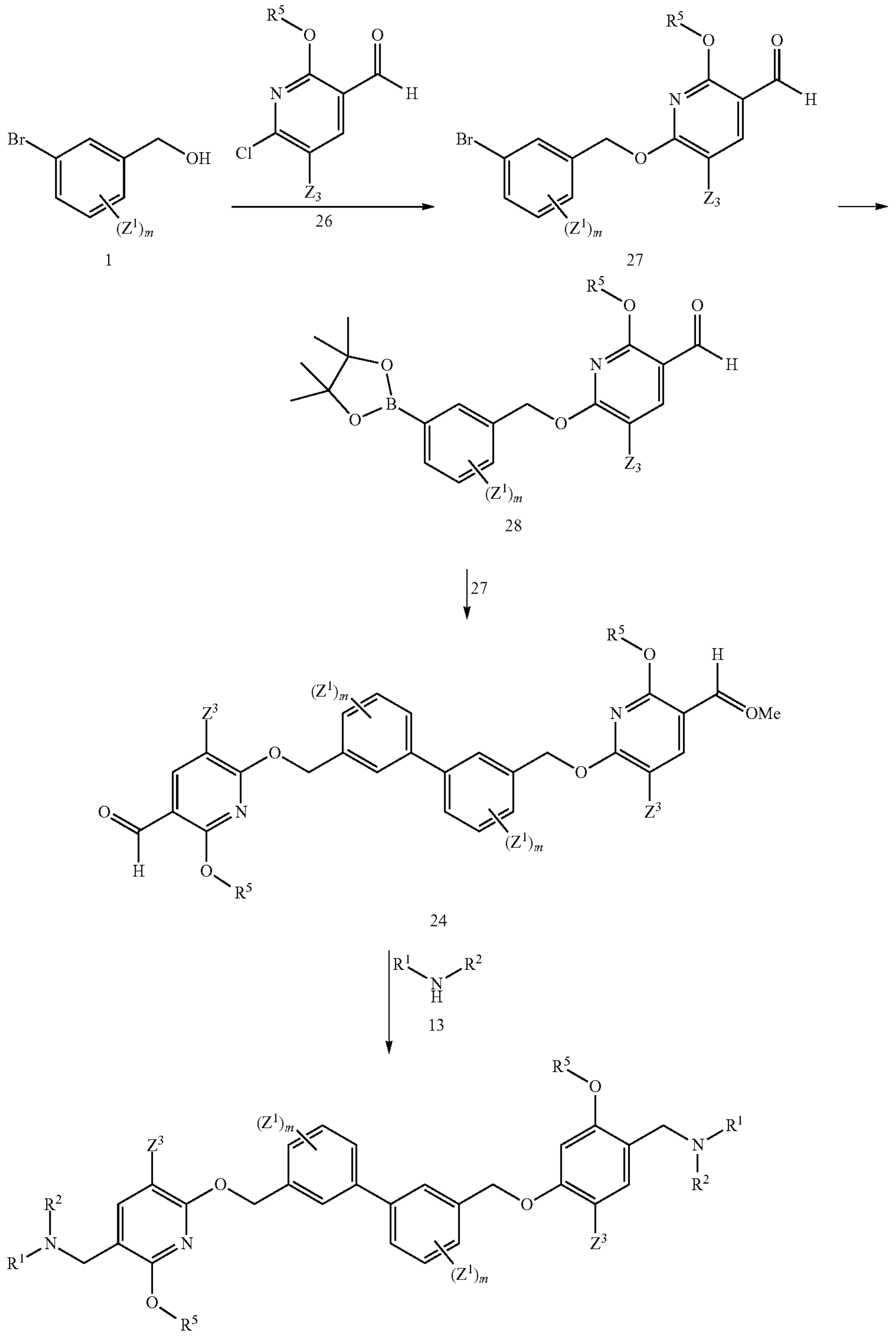

1 26 27 28 27 24 13 25

General synthesis of bis-indanols is shown in Scheme 8. A suitably substituted bromoindanone (29) is reduced to the indanol (30) using one of the many available reduction conditions (sodium borohydride, lithium aluminum hydride, and others). If enantiomerically enriched (30) is desired, asymmetric reduction conditions are also available, for example Corey's CBS reduction. Borylation followed by transition metal catalyzed biaryl coupling gives bis-indanol (32), which can be further elaborated to target compounds as shown in Schemes 4, 5, and 6.

Scheme 8

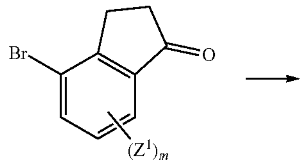

29

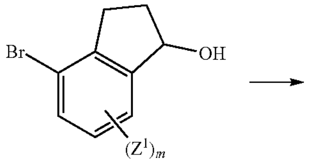

30

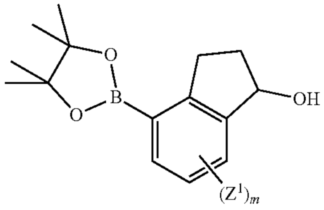

31

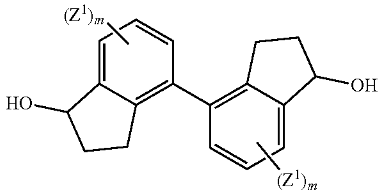

32

Bromoindanol (30) can be coupled to a substituted 2-chloropyridine (26), using either a strong base such as sodium hydride under heating, or alternatively using transition metal catalyzed coupling conditions (as described in the literature, such as Ullmann ether synthesis, which uses copper based catalysts, and Buchwald-Hartwig reaction, which uses a palladium catalyst, such as $Pd(dba)_2$, a ligand, such as XPhos, in the presence of a base, such as cesium carbonate), optionally followed by borylation to give building blocks (33) and (34) (Scheme 9).

Scheme 9

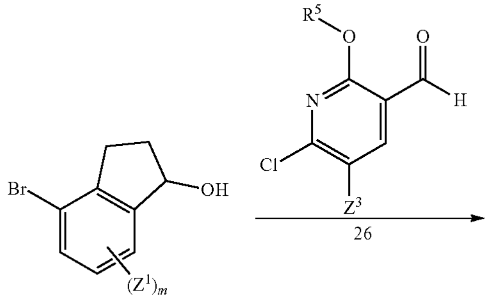

30

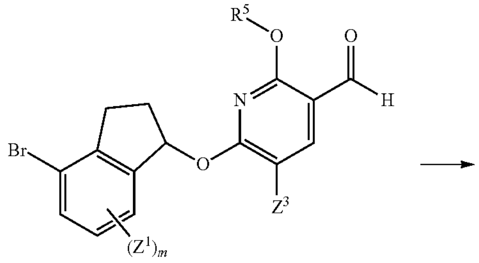

33

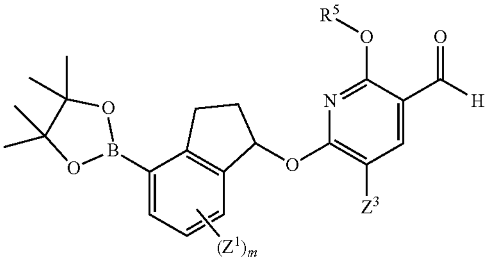

34

Generic synthesis of non-symmetric compounds is shown in Scheme 10 ($R^{10}$ is alkyl). Building blocks (35) and (36) as well as (37) and (38) can be coupled in a palladium catalyzed reaction to give (39). Boronic ester (35 or 38) is coupled with the respective coupling partner (36 or 37) using a palladium catalyst, such as $Pd(PPh_3)_4$, to afford (39). Palladium mediated cross-coupling reactions that enable the formation of the $Ar^E$—$Ar^W$ bond, but employ alternative coupling partners and reagents, include for example the Negishi, Kumada, and Stille reactions. (36) can be obtained from (43) via standard acetal formation from an aldehyde and can be converted to boronate (38) using standard borylation conditions. Treatment of (39) with a suitable amine (13)under reductive amination conditions gives (40). Acetal deprotection under acidic conditions followed by a second reductive amination using a different amine gives non-symmetric compound (42).

Scheme 10

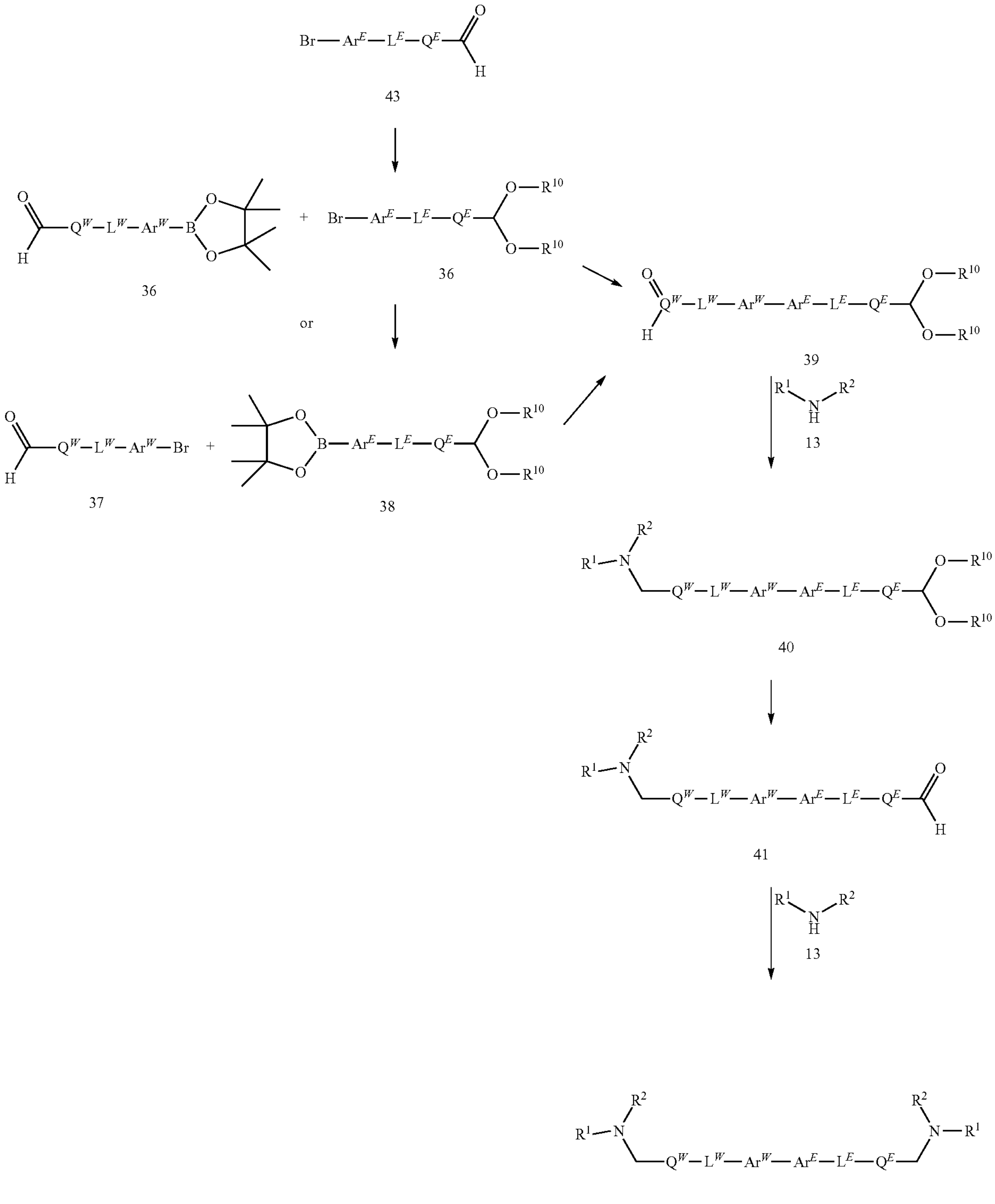

43

36

36 or

37

38

39

13

40

41

13

42

Generic synthesis of compounds where $L^E$ is a bond and $Q^E$ is phenyl is shown in Scheme 11. A boronate ester (35) and a substituted 1,3-dibromobenzene (43) can be coupled in a palladium catalyzed reaction to give arylbromide (44). A second palladium catalyzed coupling reaction with boronate (45) gives (46), which can undergo reductive amination with an amine (13) to give (47). Acetal hydrolysis of (47)under acidic conditions gives aldehyde (48), which can undergo another reductive amination with a different amine (13) to give (50). Acidic hydrolysis of the acetal (46) gives dialdehyde (49), which is subjected to reductive amination with an appropriate amine to give (51).

Scheme 11
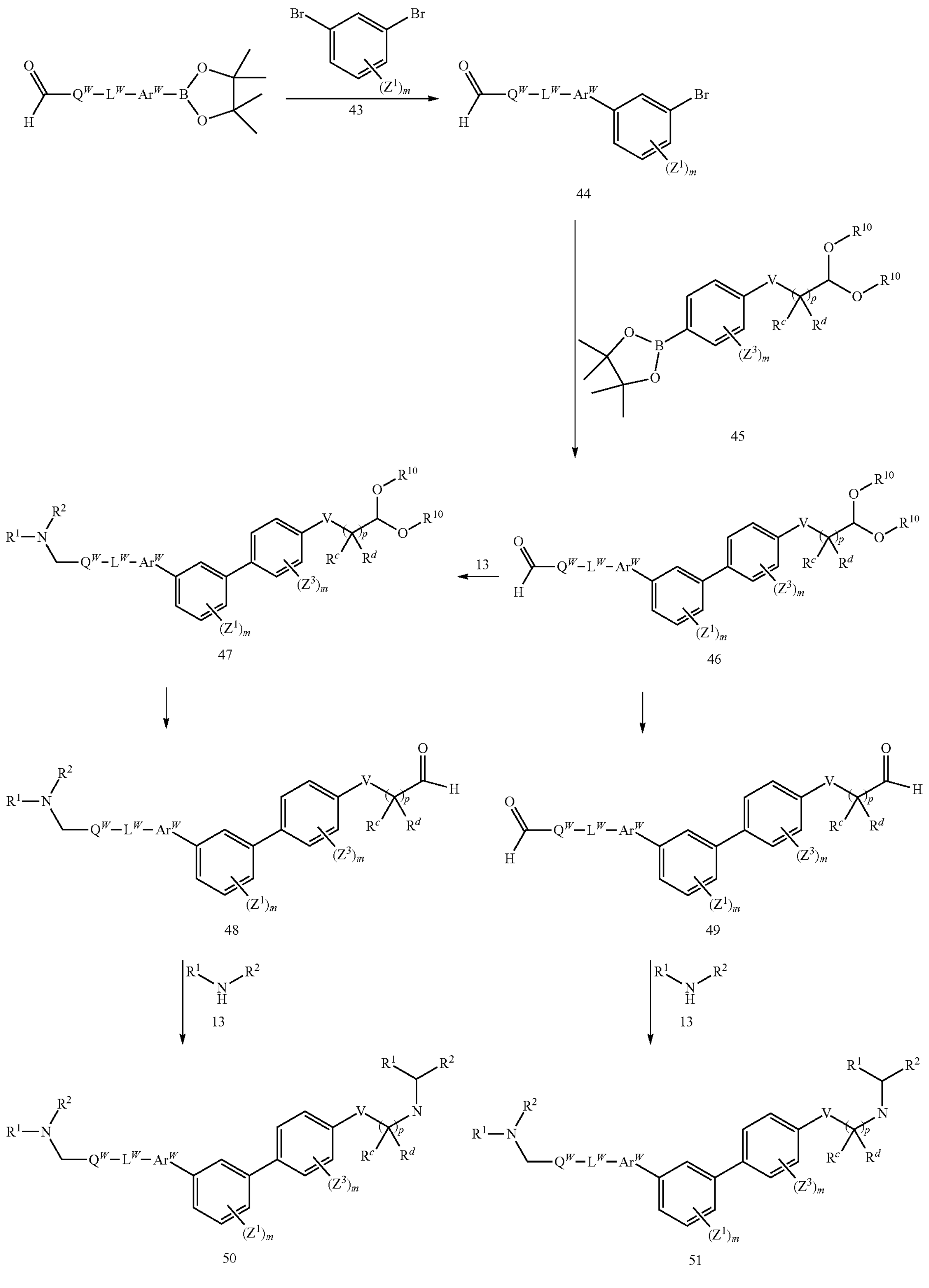

Building block (44) can be converted to boronate (52) (Scheme 12) and coupled to a substituted heteroaryl bromide (53) in a palladium catalyzed reaction to give (55). Conversion to target compounds (58) and (59) can be performed similar to Scheme 11.
Scheme 12
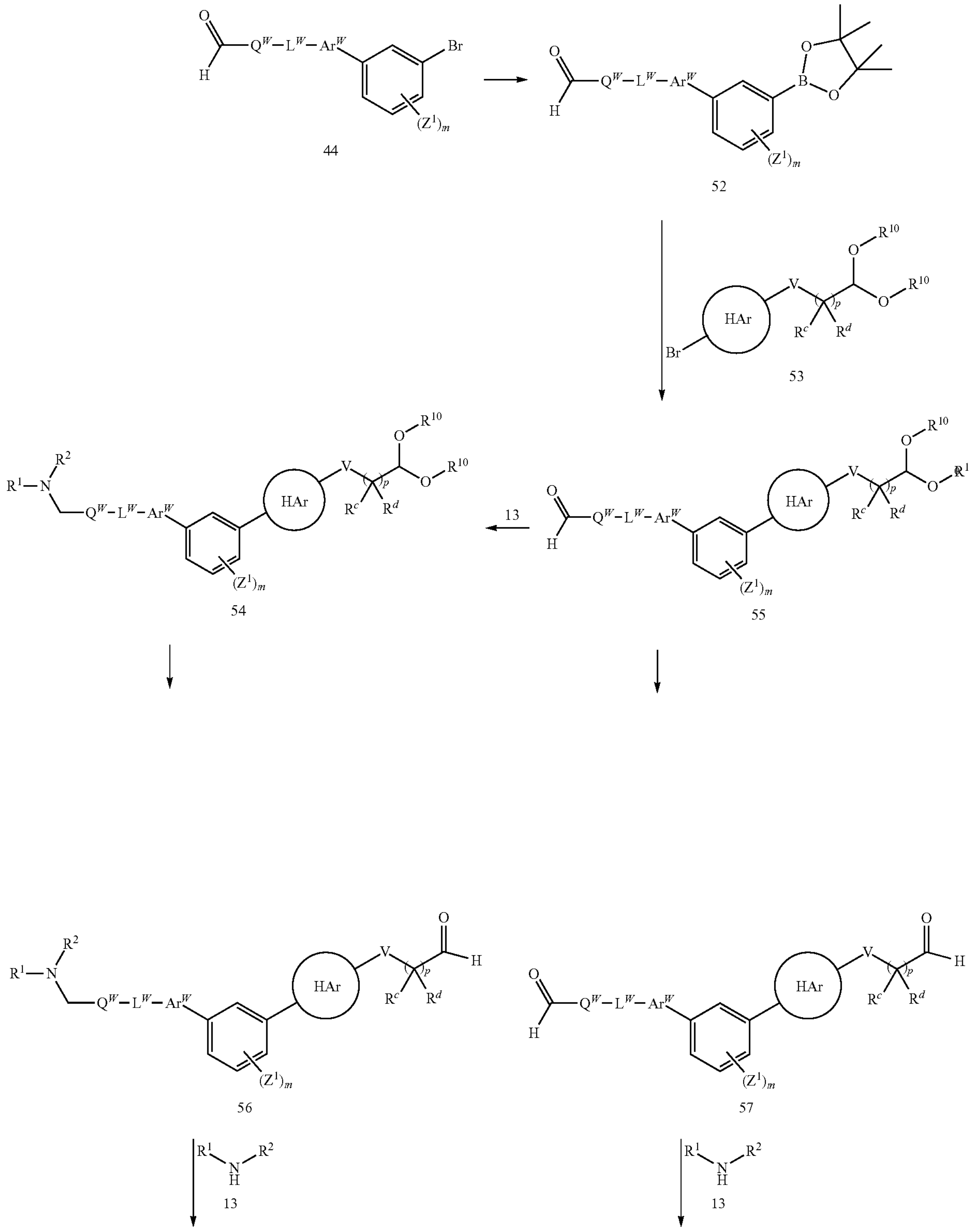
44, 52, 53, 55, 54, 56, 57

-continued

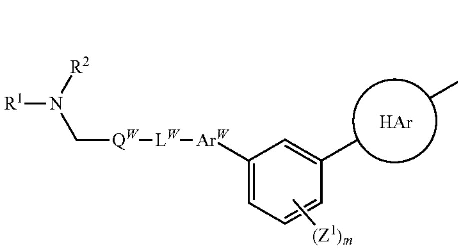

58

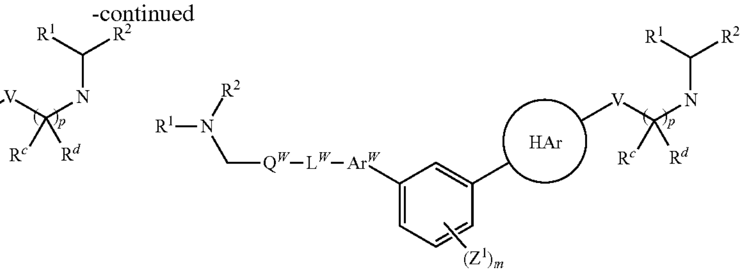

59

Generic synthesis of indoline containing compounds is shown in Scheme 13. Substituted 4-bromoindole (60) can be converted to boronate (61) and coupled with another substituted 4-bromoindole in a palladium catalyzed reaction to give bis-indole (63). Reduction using a suitable reducing agent such as sodium cyanoborohydride in acetic acid gives bis-indoline (64), which can be acylated with a suitable carboxylic acid (65) in the presence of a coupling agent such as HATU or EDCI to give dialdehyde (66). Treatment with an amine under reductive amination conditions gives compound (67).

Scheme 13

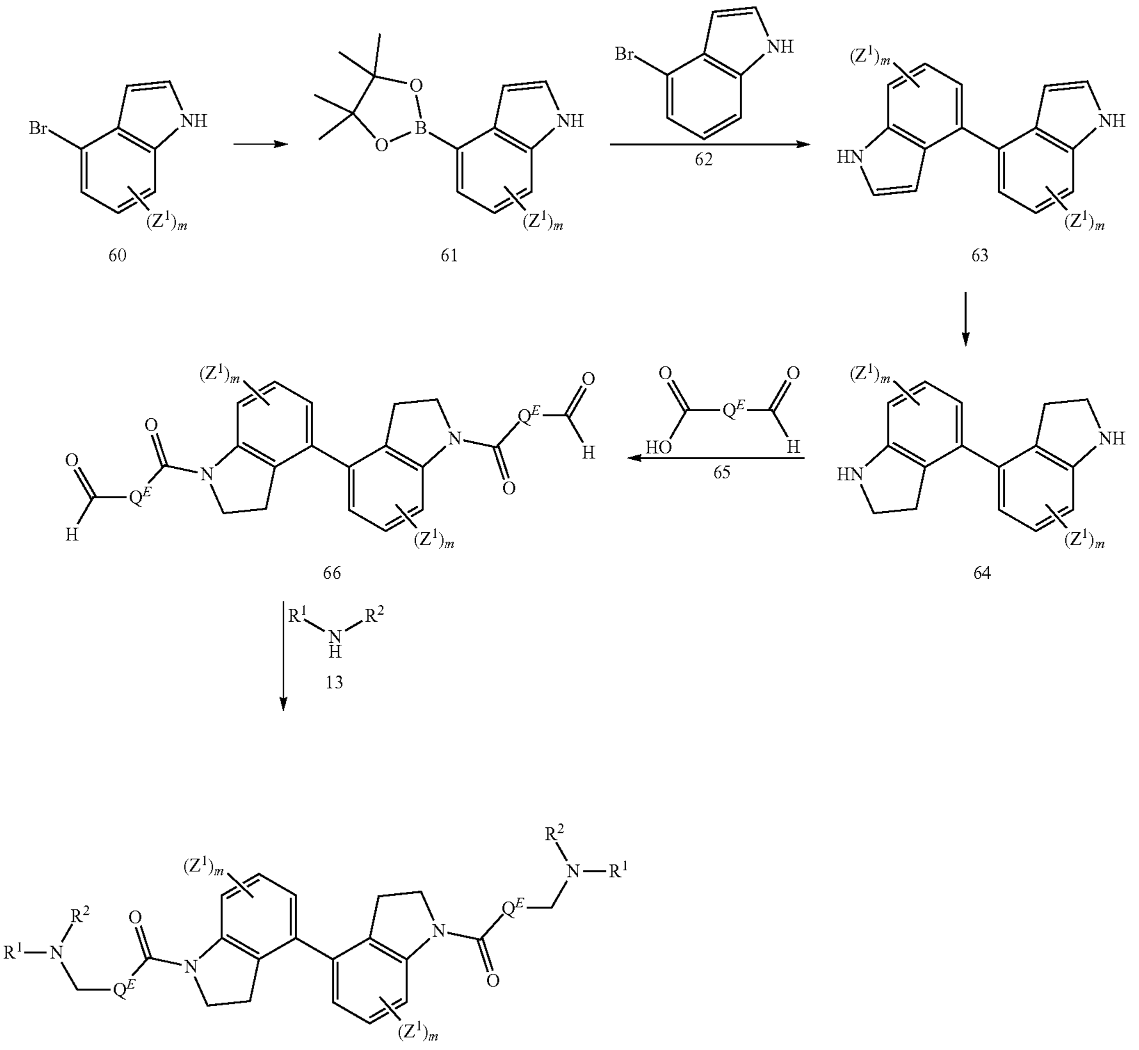

60 61 62 63 64 65 66 13 67

Boronate (52) can be coupled to a substituted, N-protected 4-bromoindoline (68) in a palladium catalyzed reaction to give (69). Removal of the protecting group followed by acylation with carboxylic acid (71) in the presence of a coupling agent such as HATU or EDCI gives dialdehyde (72). Treatment with an amine under reductive amination conditions gives compound (73).

Alternatively, compound (73) can be made by acylating a substituted 4-bromoindoline (74) with a suitable carboxylic acid (71) in the presence of a coupling agent such as HATU or EDCI to (75) followed by coupling with boronate (52) in a palladium catalyzed reaction to give dialdehyde (72). Treatment with an amine under reductive amination conditions gives compound (73).

Scheme 14

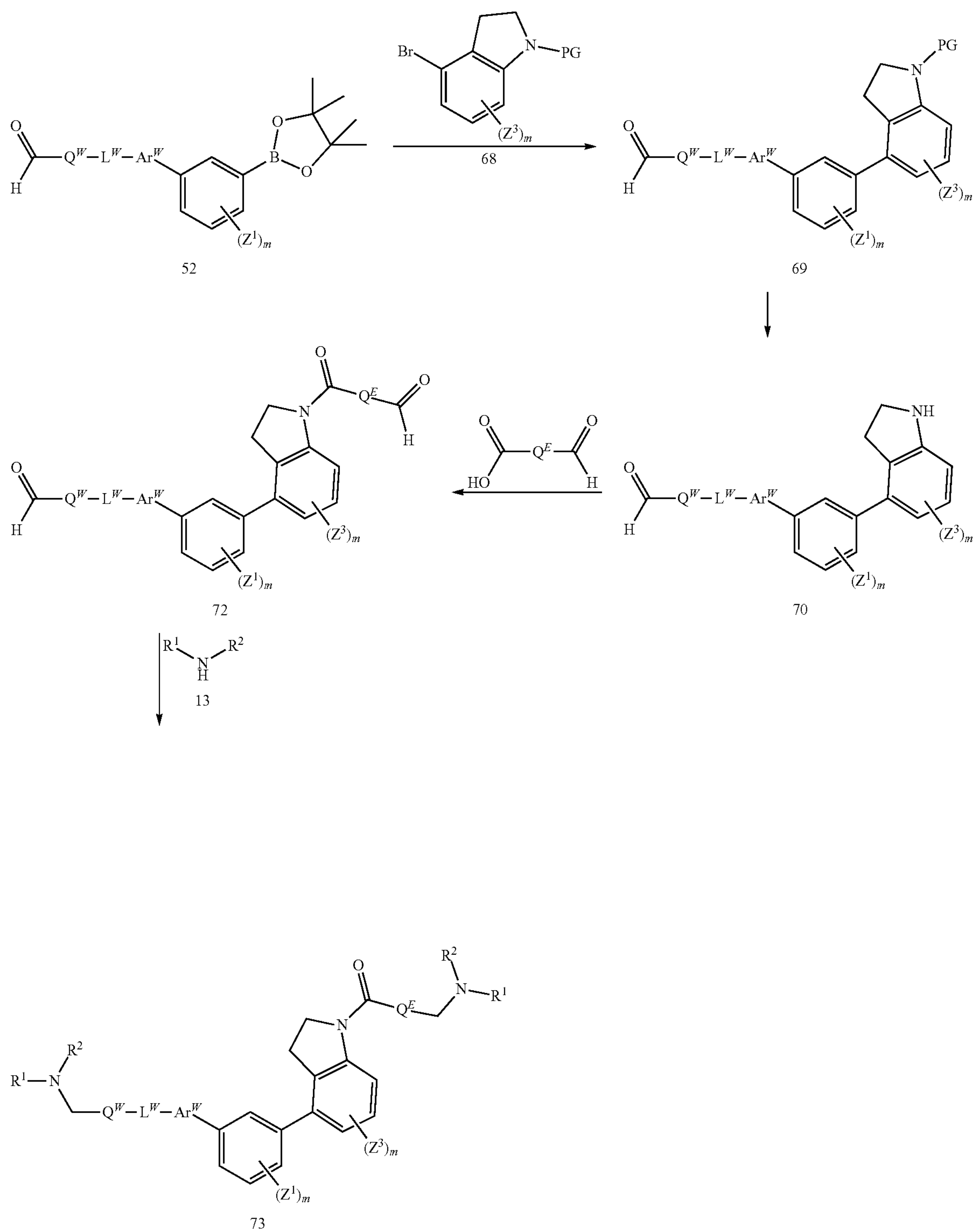

52

68

69

70

72

13

73

Scheme 15

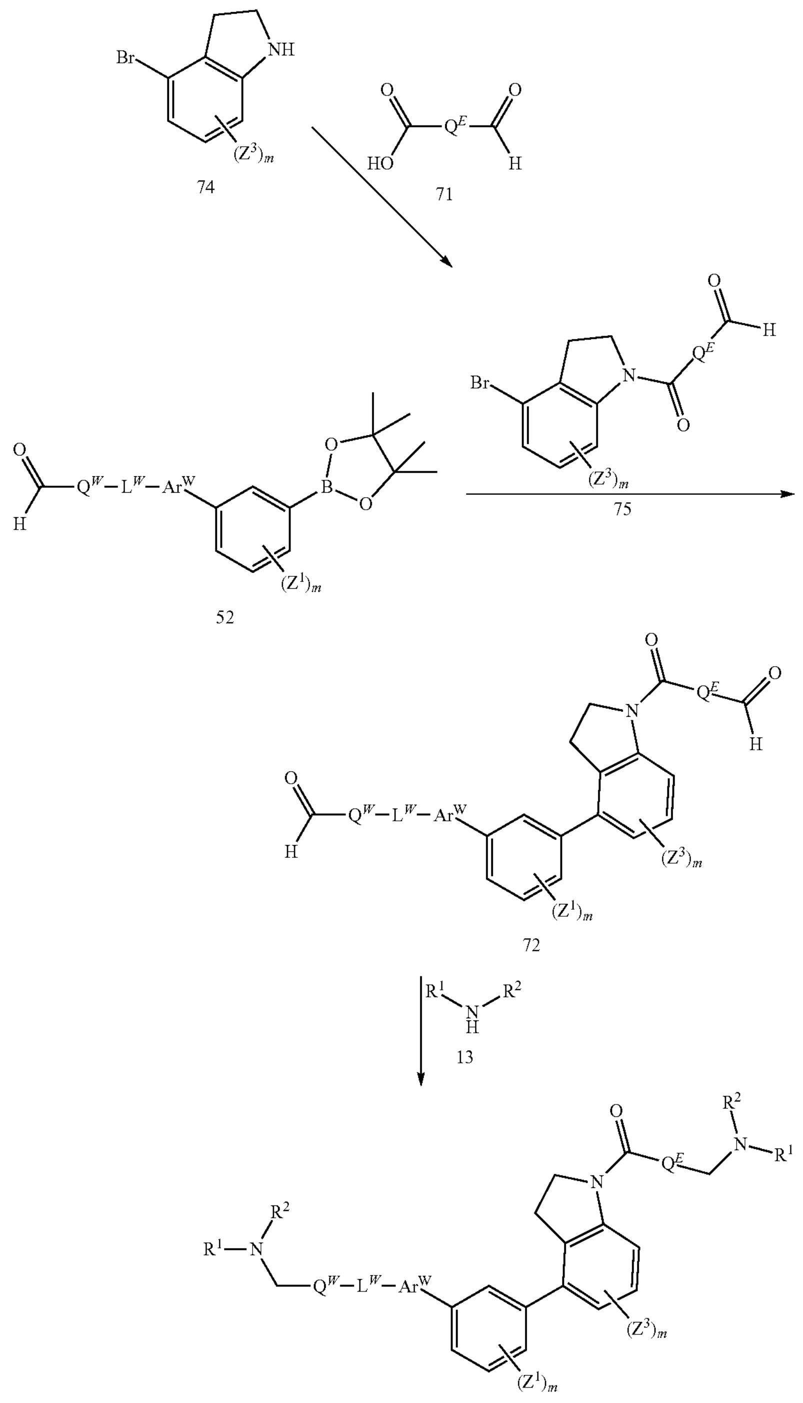

74

71

75

52

72

13

73

EXAMPLES

The compounds were named using the IUPAC naming convention or using ChemBioDraw Ultra Version 14.0. Structures are drawn ChemBioDraw Ultra Version 14.0.

When production of starting materials is not particularly described, the compounds are known or may be prepared analogously to methods known in the art or as disclosed in the Examples. One of skill in the art will appreciate that synthetic methodologies described herein are only representative of methods for preparation of the compounds described herein, and that other known methods and variants of methods described herein may be used. The methods or features described in various Examples may be combined or adapted in various ways to provide additional ways of making the compounds described herein.

Intermediate 1: (1S,1'S)-2,2',3,3'-tetrahydro-1H,1'H-[4,4'-biindene]-1,1'-diol

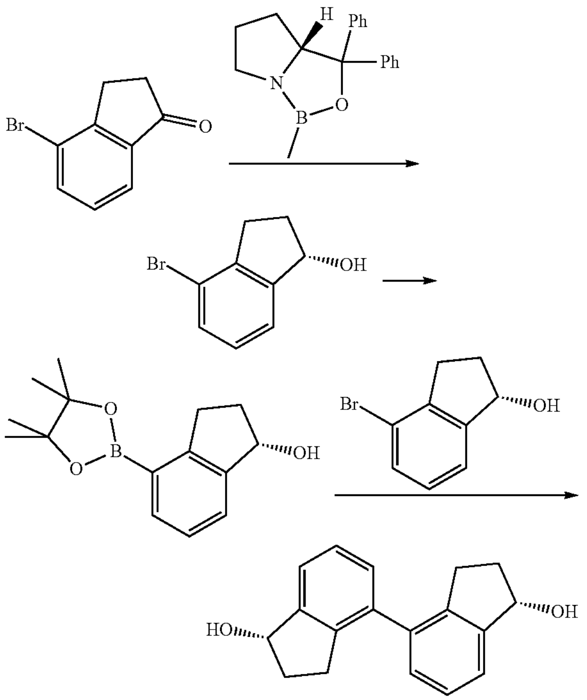

Step 1: To a 500 mL round bottom flask was added (R)-(+)-2-methyl-CBS-oxazaborolidine (985 mg, 3.55 mmol), toluene (5 mL) and borane-dimethylsulfide (12.36 mL, 130 mmol)under $N_2$. The reaction was stirred at room temperature for 10 min then diluted with DCM (20 mL) and cooled to −20° C. A solution of 4-Bromo-2,3-dihydro-1H-inden-1-one (5 g, 23.69 mmol) in DCM (20 mL) was added dropwise over 30 min while maintaining the reaction temperature at -20±5° C. The reaction was stirred for 2 h after the addition was complete, then quenched by the dropwise addition of MeOH (50 mL). The reaction mixture was diluted with an additional MeOH (60 mL) and the solvent distilled at atmospheric pressure. MeOH (60 mL) was added in two portions and the distillation was repeated twice. Finally all the solvent was evaporated under reduced pressure to give a solid which was purified by silica gel column chromatography (EA/hexanes) provided (S)-4-bromo-2,3-dihydro-1H-inden-1-ol as a solid. Product can be recrystallized from 5:1 hexanes-EtOAc.

$^1$H NMR (400 MHz, DMSO-$d_6$) δ 7.47-7.37 (m, 1H), 7.31 (d, J=7.4 Hz, 1H), 7.23-7.05 (m, 1H), 5.36 (dd, J=6.1, 2.0 Hz, 1H), 5.10 (q, J=6.2 Hz, 1H), 2.97-2.79 (m, 1H), 2.68 (dt, J=15.6, 7.6 Hz, 1H), 2.41-2.22 (m, 1H), 1.77 (dt, J=19.0, 7.0 Hz, 1H).

Step 2: To a solution of (S)-4-bromo-2,3-dihydro-1H-inden-1-ol (1.10 g, 5.16 mmol) in dioxane (15 mL) was added bis(pinacolato)diboron (1.57 g, 6.195 mmol), KOAc (1.52 g, 15 mmol) and [1,1'-bis(diphenylphosphino)ferrocene]palladium(II) dichloride (377 mg, 0.516 mmol). $N_2$ was bubbled thru the mixture for 2 min, and the flask heated to 90° C. for 2 h. The reaction was cooled to room temperature (rt) and diluted with 100 mL EtOAc, washed with water (3 times), dried with $Na_2SO_4$ and concentrated to yield an oil. This was purified by silica gel chromatography, eluting with EtOAc and hexanes to provide (S)-4-(4,4,5,5-tetramethyl-1,3,2-dioxaborolan-2-yl)-2,3-dihydro-1H-inden-1-ol as an oil that slowly crystallized on standing. $^1$H NMR (400 MHz, DMSO-$d_6$) δ 7.49 (d, J=7.2 Hz, 1H), 7.41 (d, J=7.4 Hz, 1H), 7.16 (t, J=7.1 Hz, 1H), 5.20-5.08 (m, 1H), 4.98 (q, J=6.1, 5.6 Hz, 1H), 3.18-3.01 (m, 1H), 2.78 (dt, J=16.3, 7.9 Hz, 1H), 2.36-2.19 (m, 1H), 1.82-1.61 (m, 1H), 1.27 (d, J=1.9 Hz, 14H). LCMS-ESI$^+$ (m/z): [M−OH]$^+$ calc'd for $C_{15}H_{20}BO_2$: 243.1; found: 243.2.

Step 3: A mixture of (S)-4-(4,4,5,5-tetramethyl-1,3,2-dioxaborolan-2-yl)-2,3-dihydro-1H-inden-1-ol (1.53 g, 5.90 mmol), (S)-4-bromo-2,3-dihydro-1H-inden-1-ol (1.32 g, 6.19 mmol), $Pd(dppf)Cl_2CH_2Cl_2$ (0.431 g, 0.59 mmol) and $Na_2CO_3$ (5.89 mL, 12 mmol, 2M)under $N_2$ in 30 mL dioxane was heated to 85° C. in a heating block for 2 h, at which time all SM was consumed by LCMS. After cooling to room temperature, the reaction was diluted with EtOAc and water. The organic layer was separated, dried with $Na_2SO_4$ and concentrated. Purified by silica gel chromatography (eluting with EtOAc-Hex) to provide (1S,1'S)-2,2',3,3'-tetrahydro-1H,1'H-[4,4'-biindene]-1,1'-diol as a light oil that crystallized on standing. [M−OH]+=249.2. $^1$H NMR (400 MHz, DMSO-$d_6$) δ 7.49 (d, J=7.2 Hz, 1H), 7.41 (d, J=7.4 Hz, 1H), 7.16 (t, J=7.1 Hz, 1H), 5.20-5.08 (m, 1H), 4.98 (q, J=6.1, 5.6 Hz, 1H), 3.18-3.01 (m, 1H), 2.78 (dt, J=16.3, 7.9 Hz, 1H), 2.36-2.19 (m, 1H), 1.82-1.61 (m, 1H), 1.27 (d, J=1.9 Hz, 14H). LCMS-ESI (m/z): [M−OH]$^+$ calc'd for $C_{18}H_{17}O$: 249.1; found: 249.2.

Intermediate 2: 5,5'-((((((1S,1'S)-2,2',3,3'-tetrahydro-1H,1'H-[4,4'-biindene]-1,1'-diyl)bis(oxy))bis(5-bromo-3-formylpyridine-6,2-diyl))bis(oxy))bis(methylene))dinicotinonitrile

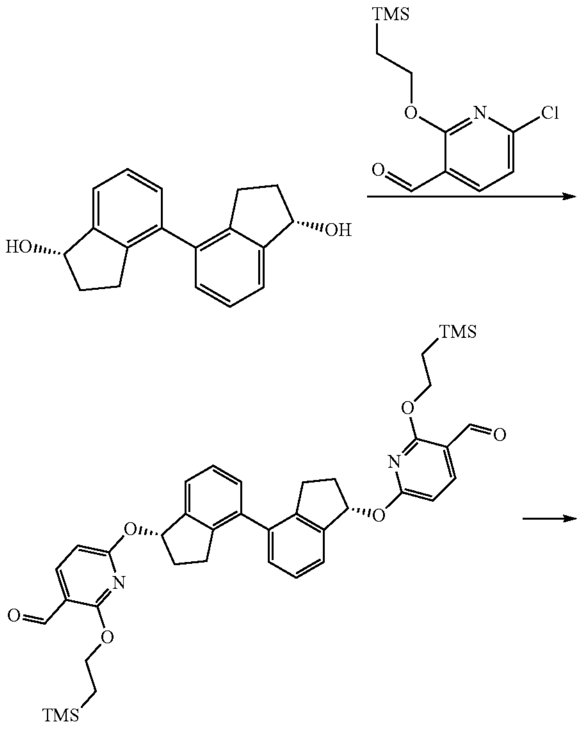

-continued

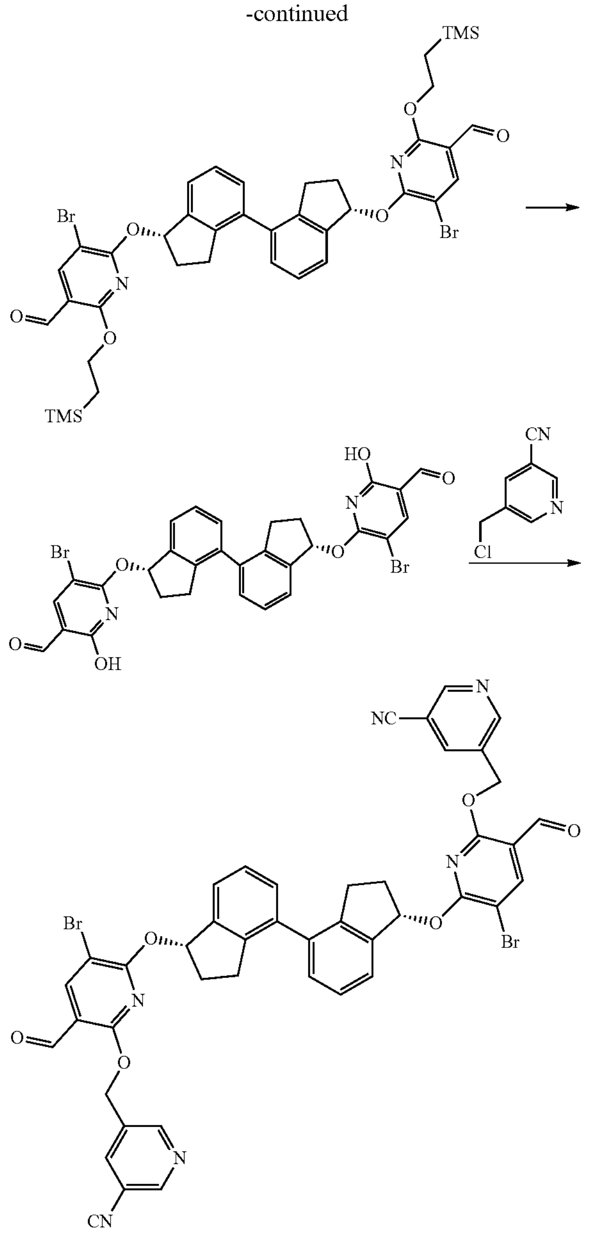

Step 1: 6,6'-(((1S,1'S)-2,2',3,3'-tetrahydro-1H,1'H-[4,4'-biindene]-1,1'-diyl)bis(oxy))bis(2-(2-(trimethylsilyl) ethoxy)nicotinaldehyde) was prepared using the same method as Intermediate 3, by substituting 6-chloro-2-(2-(trimethylsilyl)ethoxy)nicotinaldehyde for 6-chloro-2-methoxynicotinaldehyde. $^{1}$H NMR (400 MHz, Chloroform-d) δ 10.25 (s, 2H), 8.06 (d, J=8.4 Hz, 2H), 7.46 (d, J=7.3 Hz, 2H), 7.32 (t, J=7.4 Hz, 2H), 7.00 (s, 2H), 6.59 (dd, J=6.8, 4.7 Hz, 2H), 6.38 (d, J=8.3 Hz, 2H), 4.67-4.51 (m, 5H), 4.12 (q, J=7.1 Hz, 2H), 3.08-2.85 (m, 4H), 2.78 (dt, J=15.8, 7.0 Hz, 2H), 2.62 (dq, J=13.6, 7.1 Hz, 2H), 2.50 (s, 2H), 2.29-2.14 (m, 2H), 0.08 (s, 18H).

Step 2 A solution of 6,6'-(((1S,1'S)-2,2',3,3'-tetrahydro-1H,1'H-[4,4'-biindene]-1,1'-diyl)bis(oxy))bis(2-(2-(trimethylsilyl)ethoxy)nicotinaldehyde) (200 mg, 0.231 mmol) and cesium fluoride (140 mg, 0.923 mmol) in DMF (2 mL) heated to 60° C. for 2 h. The reaction was cooled to rt and diluted with 100 mL DCM, washed with pH 3.0 citrate buffer (3 times), dried with $Na_2SO_4$ and concentrated to yield 6,6'-(((1S,1'S)-2,2',3,3'-tetrahydro-1H,1'H-[4,4'-biindene]-1,1'-diyl)bis(oxy))bis(5-bromo-2-hydroxynicotinaldehyde) as an oil.

$^{1}$H NMR (400 MHz, Chloroform-d) δ 10.18 (s, 2H), 8.25 (s, 2H), 7.48 (d, J=7.4 Hz, 2H), 7.38-7.23 (m, 4H), 6.57 (t, J=6.2 Hz, 2H), 4.67-4.58 (m, 4H), 3.03 (ddd, J=15.9, 8.7, 4.3 Hz, 2H), 2.88-2.63 (m, 4H), 2.31-2.15 (m, 2H), 1.32-1.17 (m, 4H), 0.08 (s, 18H).

Step 3: 6,6'-(((1S,1'S)-2,2',3,3'-tetrahydro-1H,1'H-[4,4'-biindene]-1,1'-diyl)bis(oxy))bis(5-bromo-2-hydroxynicotinaldehyde (100 mg, 0.15 mmol) was taken up in 2 mL DMF in a 20 mL vial and treated with K2CO3 (155 mg, 1.12 mmol), 5-(chloromethyl)nicotinonitrile hydrochloride (71 mg, 0.325 mmol) and sodium iodide (45 mg, 0.3 mmol). Stirred under $N_2$ at 65° C. for 2 h. The reaction was partitioned between pH 3 citrate buffer and DCM. The organic was washed with water 3 times, dried with MgSO4, filtered and concentrated to provide 6,6'-(((1S,1'S)-2,2',3,3'-tetrahydro-1H,1'H-[4,4'-biindene]-1,1'-diyl)bis(oxy))bis(5-bromo-2-hydroxynicotinaldehyde) as a semi-solid. This material was used in the reaction below without purification.

Step 4: A mixture of 6,6'-(((1S,1'S)-2,2',3,3'-tetrahydro-1H,1'H-[4,4'-biindene]-1,1'-diyl)bis(oxy))bis(5-bromo-2-hydroxynicotinaldehyde) (100 mg, 0.15 mmol), 5-(chloromethyl)nicotinonitrile hydrochloride (74 mg, 0.357 mmol), $K_2CO_3$ (155 mg, 1.13 mmol) and NaI (45 mg, 0.30 mmol) in 2 mL DMF was heated to 85° C. in a heating block for 1h, by which time all SM appeared consumed by LCMS. After cooling to room temperature, the reaction was diluted with DCM and water. The organic layer was separated, dried with $Na_2SO_4$ and concentrated. Purified by silica gel chromatography (eluting with EtOAc-DCM) to provide 5,5'-((((((1S, 1'S)-2,2',3,3'-tetrahydro-1H,1'H-[4,4'-biindene]-1,1'-diyl) bis(oxy))bis(5-bromo-3-formylpyridine-6,2-diyl))bis(oxy)) bis(methylene))dinicotinonitrile as a powder.

LCMS-ESI$^{+}$ (m/z): $[M+H]^{+}$ calculated for C44H30Br2N6O6: 898.07; found: 898.06.

Intermediate 3: 6,6'-(((1S,1'S)-2,2',3,3'-tetrahydro-1H,1'H-[4,4'-biindene]-1,1'-diyl)bis(oxy))bis(2-methoxynicotinaldehyde)

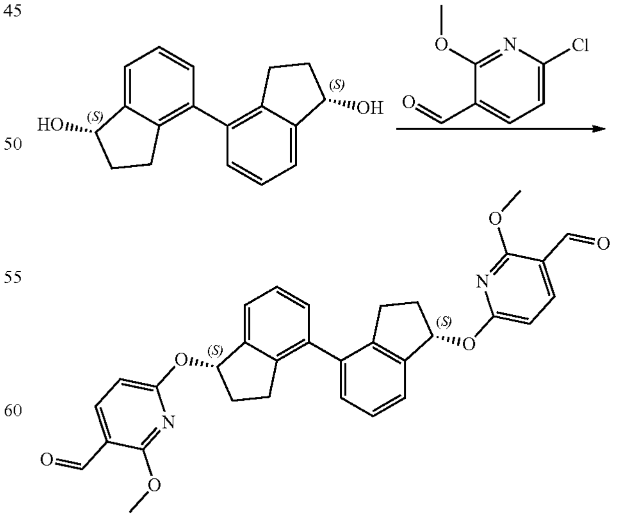

A solution of Intermediate 1 (250 mg, 0.939 mmol) and 6-chloro-2-methoxynicotinaldehyde(403 mg, 2.43 mmol)

was taken up in 4 mL toluene and $N_2$ was bubbled thru the solution for 5 min. Palladium (II) acetate (32 mg, 0.141 mmol), 2-di-tert-butylphosphino-2',4',6'-triisopropylbiphenyl (60 mg, 0.141 mmol) and $Cs_2CO_3$ (1.22 g, 3.76 mmol) were added and $N_2$ was bubbled for an additional 2 min. The reaction was then heated to 85° C. with vigorous stirring for 16 h. After cooling to rt the reaction was diluted with 50 mL DCM and filtered thru Celite®. The filtrate was purified by silica gel chromatography (eluting with EtOAc-hexanes) to provide 6,6'-(((1S,1'S)-2,2',3,3'-tetrahydro-1H,1'H-[4,4'-biindene]-1,1'-diyl)bis(oxy))bis(2-methoxynicotinaldehyde) as a solid. $^1H$ NMR (400 MHz, Chloroform-d) δ 10.24 (d, J=0.8 Hz, 2H), 8.07 (d, J=8.3 Hz, 2H), 7.47 (d, J=7.3 Hz, 2H), 7.37-7.22 (m, 6H), 6.66 (dd, J=7.0, 4.6 Hz, 2H), 6.41 (dd, J=8.3, 0.7 Hz, 2H), 4.11 (s, 6H), 3.02 (ddd, J=15.7, 8.6, 5.3 Hz, 2H), 2.79 (ddd, J=16.1, 8.4, 5.8 Hz, 2H), 2.64 (dddd, J=13.6, 8.4, 7.0, 5.2 Hz, 2H), 2.22 (ddt, J=13.7, 8.7, 5.4 Hz, 2H).

Intermediate 4: 6,6'-(((1S,1'S)-2,2',3,3'-tetrahydro-1H,1'H-[4,4'-biindene]-1,1'-diyl)bis(oxy))bis(5-bromo-2-methoxynicotinaldehyde)

A solution of Intermediate 3 (468 mg, 0.87 mmol) in 20 mL $CHCl_3$ was diluted with 10 mL DMF and treated with NBS (310 mg, 1.74 mmol) and TFA (0.01 mL, 0.131 mmol). The reaction was stirred at 50° C. for 2 h, then cooled to rt and stirred overnight. Reaction was diluted with 50 mL DCM and stirred with sat. sodium thiosulfate solution for 15 min. The organic layer was dried with sodium sulfate and concentrated. Purification by silica gel chromatography, eluting with EtOAc-hexanes provided 6,6'-(((1S,1'S)-2,2',3,3'-tetrahydro-1H,1'H-[4,4'-biindene]-1,1'-diyl)bis(oxy))bis(5-bromo-2-methoxynicotinaldehyde) as a solid. $^1H$ NMR (400 MHz, Chloroform-d) δ 10.17 (s, 2H), 8.26 (s, 2H), 7.49 (d, J=7.4 Hz, 2H), 7.39-7.26 (m, 6H), 6.64 (t, J=6.2 Hz, 2H), 4.11 (s, 6H), 3.03 (ddd, J=16.0, 8.7, 4.4 Hz, 2H), 2.83 (dt, J=15.7, 7.2 Hz, 2H), 2.72 (ddd, J=13.8, 7.3, 4.6 Hz, 2H), 2.25 (ddt, J=14.2, 8.8, 6.0 Hz, 2H).

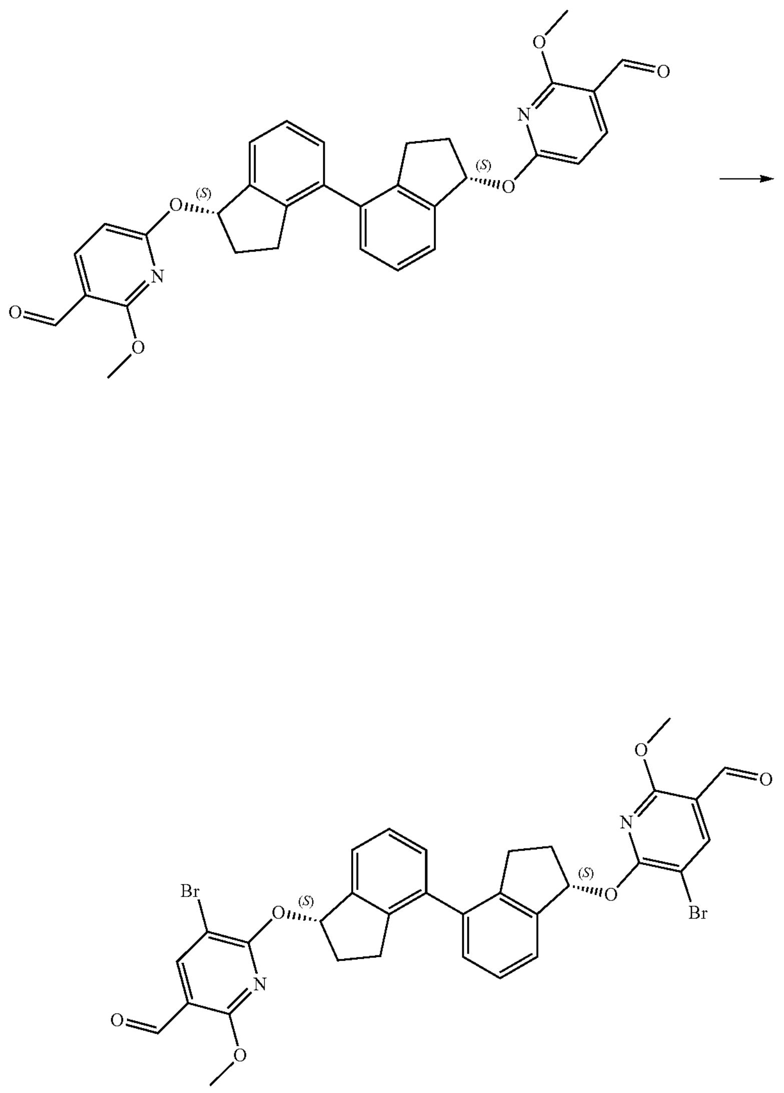

Intermediate 5: 6,6'-(((1S,1'S)-2,2',3,3'-tetrahydro-1H,1'H-[4,4'-biindene]-1,1'-diyl)bis(oxy))bis(5-chloro-2-methoxynicotinaldehyde) and Intermediate 6: 5-chloro-6-(((1S,1'S)-1'-((5-formyl-6-methoxypyridin-2-yl)oxy)-2,2',3,3'-tetrahydro-1H,1'H-[4,4'-biinden]-1-yl)oxy)-2-methoxynicotinaldehyde

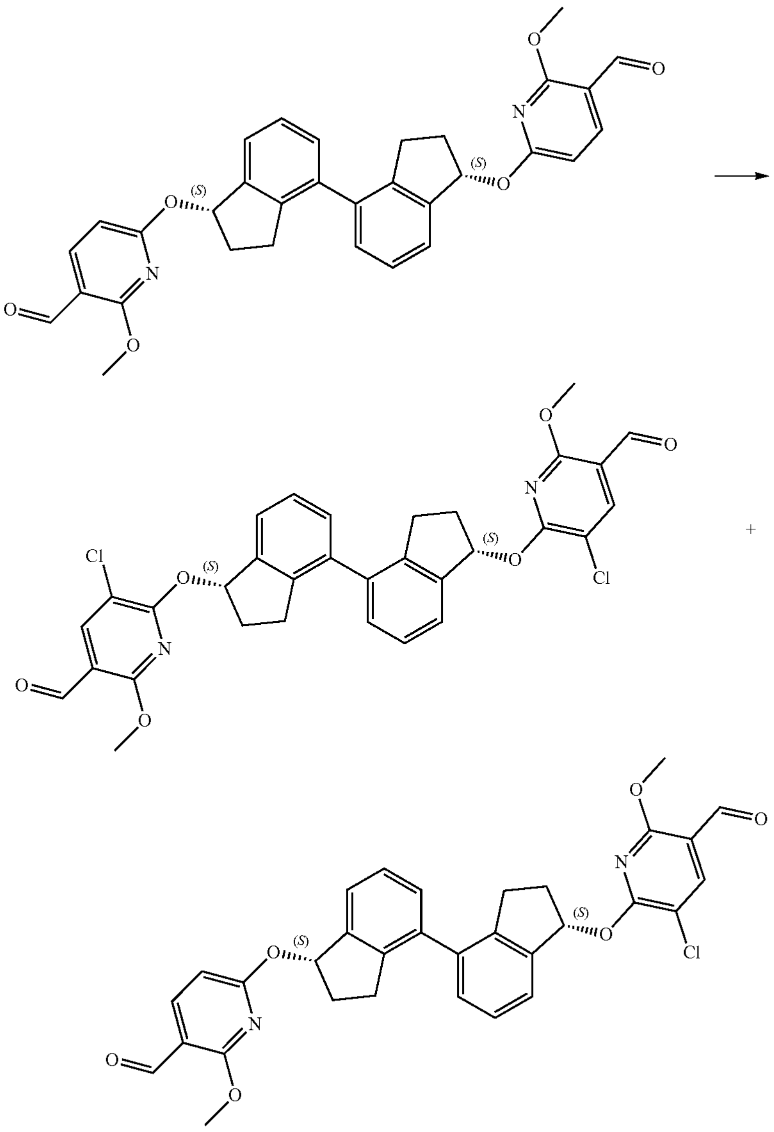

A solution of Intermediate 3 (94 mg, 0.175 mmol) in 720 mL CHCl3 was diluted with 3 mL DMF and treated with Palau-Cl (81 mg, 0.38 mmol) and TFA (0.0033 mL, 0.044 mmol). The reaction was stirred at 40° C. for 2 days. Reaction was diluted with 50 mL DCM and stirred with sat. sodium thiosulfate for 15 min. The organic layer was washed with pH 3 citrate buffer (2×) dried with sodium sulfate and concentrated. Purification by silica gel chromatography, eluting with EtOAc-hexanes provided Intermediate 5 and Intermediate 6.

Intermediate 5: $^{1}$H NMR (400 MHz, Chloroform-d) δ 10.19 (s, 2H), 8.11 (s, 2H), 7.52-7.45 (m, 2H), 7.37-7.24 (m, 4H), 6.71-6.63 (m, 2H), 4.12 (s, 6H), 3.04 (ddd, J=16.0, 8.7, 4.6 Hz, 2H), 2.88-2.76 (m, 2H), 2.77-2.64 (m, 2H), 2.33-2.20 (m, 2H).

Intermediate 6: $^{1}$H NMR (400 MHz, Chloroform-d) δ 10.29 (s, 1H), 10.19 (s, 1H), 8.23 (d, J=8.1 Hz, 1H), 8.11 (s, 1H), 7.48 (m, 2H), 7.32 (m, 4H), 6.75 (d, J=8.2 Hz, 1H), 6.67 (t, J=6.1 Hz, 1H), 4.11 (s, 3H), 3.93 (s, 3H), 3.03 (td, J=10.4, 8.7, 4.9 Hz, 2H), 2.82 (dt, J=15.8, 7.4 Hz, 2H), 2.71 (dt, J=13.7, 6.5 Hz, 2H), 2.27 (dd, J=16.4, 8.2 Hz, 2H).

Intermediate 7: (2-methyl-3-(4,4,5,5-tetramethyl-1,3,2-dioxaborolan-2-yl)phenyl)methanol

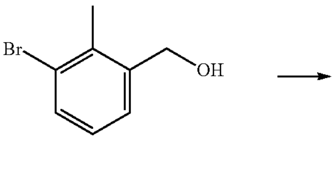

-continued

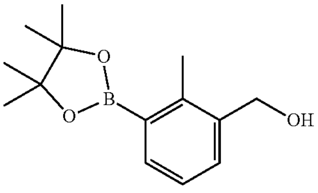

To a solution of (3-bromo-2-methylphenyl)methanol (7.00 g, 34.8 mmol) in DMF (15 mL) was added bis (pinacolato)diboron (10.61 g, 41.8 mmol), KOAc (10.24 g, 104 mmol) and [1,1'-bis(diphenylphosphino)ferrocene]palladium(II) dichloride (2.545 g, 3.48 mmol). $N_2$ was bubbled thru the mixture for 2 min, and the flask heated to 90 C for 2 h. The reaction was cooled to rt and diluted with 100 mL EtOAc, washed with water (3 times), dried with $Na_2SO_4$ and concentrated to yield an oil. This was purified by silica gel chromatography, eluting with EtOAc and hexanes to provide (2-methyl-3-(4,4,5,5-tetramethyl-1,3,2-dioxaborolan-2-yl) phenyl)methanol as an oil that slowly crystallized on standing. $[M-OH]^+=231$. H NMR (400 MHz, DMSO-d6) δ 7.52-7.40 (m, 2H), 7.17-7.09 (m, 1H), 5.04 (t, J=5.4 Hz, 1H), 4.47 (d, J=5.4 Hz, 2H), 2.38 (s, 3H), 1.28 (s, 12H).

Intermediate 8: (2,2'-dimethyl-[1,1'-biphenyl]-3,3'-diyl)dimethanol

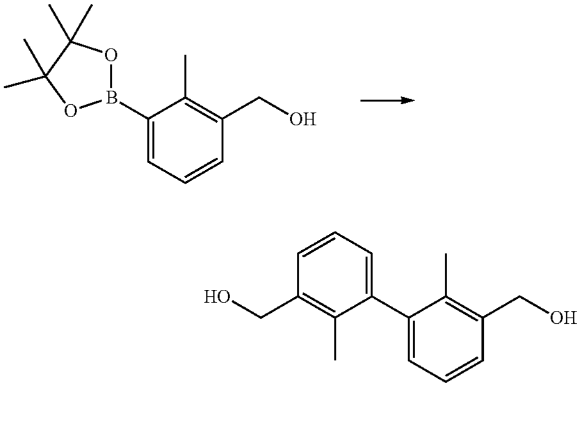

To a mixture of (2-methyl-3-(4,4,5,5-tetramethyl-1,3,2-dioxaborolan-2-yl)phenyl)methanol (1.728 g, 6.96 mmol), (3-bromo-2-methylphenyl)methanol (1.40 g, 6.96 mmol), $Pd(dppf)Cl_2CH_2Cl_2$ (0.509 g, 0.696 mmol) and potassium carbonate (1.922 g, 13.93 mmol)under $N_2$ was added a mixture of solvents (20 mL dioxane and 5 mL water) and heated to 85° C. in a heating block for 2 h, at which time all SM was consumed by LCMS. After cooling to room temperature, the reaction was diluted with EtOAc and water. The organic layer was separated, dried with $Na_2SO_4$ and concentrated. Purified by silica gel chromatography (eluting with EtOAc-Hex) to provide (2,2'-dimethyl-[1,1'-biphenyl]-3,3'-diyl)dimethanol as a light oil that crystallized on standing. $[M-OH]^+=225$. $^1$H NMR (400 MHz, DMSO-d6) δ 7.37 (dd, J=7.6, 1.3 Hz, 2H), 7.19 (t, J=7.5 Hz, 2H), 6.92 (dd, J=7.6, 1.4 Hz, 2H), 5.10 (t, J=5.4 Hz, 2H), 4.52 (d, J=5.4 Hz, 4H), 1.88 (s, 6H).

Intermediate 9: 3,3'-bis(chloromethyl)-2,2'-dimethyl-1,1'-biphenyl

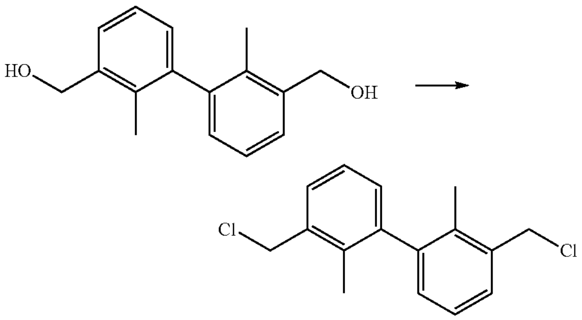

(2,2'-Dimethyl-[1,1'-biphenyl]-3,3'-diyl)dimethanol (3.0 g, 12.8 mmol) was taken up in 10 mL DCM and cooled to 0 C. TEA (17.25 mL, 123.8 mmol) and MsCl (9.58 mL, 123.8 mmol) added and the reaction allowed to warm to rt and stir for 24h. The reaction was diluted with water and DCM with vigorous stirring. The layers were separated and the organic layer washed with 1N HCl, dried with MgSO4 and concentrated. The residue was taken up in toluene and concentrated again (2×) to provide the product as an oil.

Intermediate 10: 6,6'-(((2,2'-dimethyl-[1,1'-biphenyl]-3,3'-diyl)bis(methylene))bis(oxy))bis(2-methoxynicotinaldehyde)

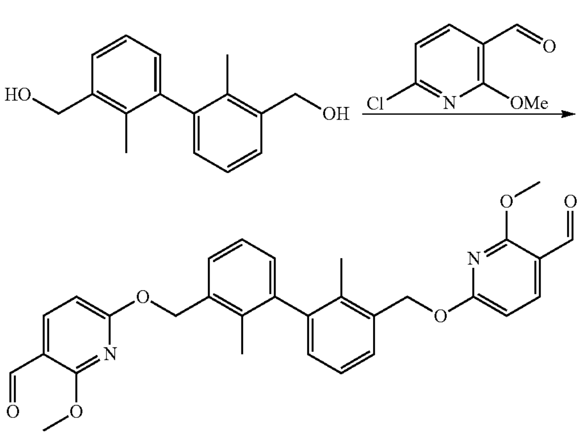

A mixture of Cesium carbonate (1.3 g, 4.04 mmol), palladium (II) acetate (43 mg, 0.40 mmol), 2-di-tert-butylphosphino-2',4',6'-triisopropylbiphenyl(t-butyl Xphos) (171 mg, 0.40 mmol), +6-chloro-2-methoxynicotinaldehyde (434 mg, 2.53 mmol) and (2,2'-dimethyl-[1,1'-biphenyl]-3,3'-diyl)dimethanol (245 mg, 1.01 mmol) in toluene (3 mL) was heated at 85° C. in 20 mL sealed microwave vial (20 mL). After 4h, reaction mixture was cooled down and purified by column Chromatography (ISCO (40 g column, 1% ethyl acetate/hexanes-50% ethyl acetate/hexanes over 15 min-load with dry amount) to give the product as a solid. ES/MS m/z: 513.0 (M+1). $^1$H NMR (400 MHz, DMSO-$d_6$) δ 10.08 (s, 2H), 8.02 (d, J=8.3 Hz, 2H), 7.46 (dd, J=7.7, 1.4 Hz, 2H), 7.27 (t, J=7.6 Hz, 2H), 7.08 (dd, J=7.6, 1.4 Hz, 2H), 6.59 (dd, J=8.3, 0.8 Hz, 2H), 5.54 (s, 4H), 4.01 (s, 6H), 1.98 (d, J=12.3 Hz, 6H).

Intermediate 11: 4,4'-(((2,2'-dimethyl-[1,1'-biphenyl]-3,3'-diyl)bis(methylene))bis(oxy))bis(5-chloro-2-hydroxybenzaldehyde)

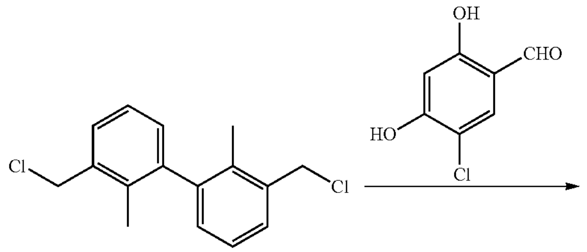

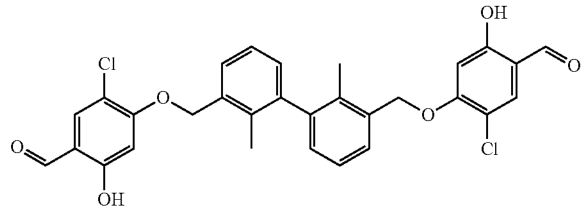

A suspension of 5-chloro-2,4-dihydroxybenzaldehyde (1.36 g, 8 mmol) in 10 mL DMF was treated with $NaHCO_3$ (1.50 g, 8 mmol) and stirred for 30 min under $N_2$. 3,3'-bis(chloromethyl)-2,2'-dimethyl-1,1'-biphenyl (1.00 g, 8 mmol) in 2 mL DMF was added, followed by NaI (1.07 g, 7 mmol). The reaction mixture was heated at 55 C for 4h, at which time the reaction was cooled to rt and diluted with EtOAc and pH 4 citrate buffer. After stirring for 5 min the mixture was filtered providing a light colored precipitate. The filtrate was separated and the aqueous layer washed with additional EtOAc. The organic layers were combined, dried with $Na_2SO_4$ and concentrated to provide a semi-solid. The precipitate and semisolid were combined to provide the desire product 4,4'-(((2,2'-dimethyl-[1,1'-biphenyl]-3,3'-diyl)bis(methylene))bis(oxy))bis(5-chloro-2-hydroxybenzaldehyde). [M+H]=550.72. $^1$H NMR (400 MHz, DMSO-$d_6$) δ 11.14 (s, 2H), 10.01 (s, 2H), 7.69 (s, 2H), 7.50 (d, J=7.7 Hz, 2H), 7.31 (t, J=7.6 Hz, 2H), 7.11 (d, J=7.4 Hz, 2H), 6.85 (s, 2H), 5.31 (s, 4H), 2.00 (s, 6H).

Intermediate 12: 5,5'-((((((2,2'-dimethyl-[1,1'-biphenyl]-3,3'-diyl)bis(methylene))bis(oxy))bis(4-chloro-6-formyl-3,1-phenylene))bis(oxy))bis(methylene))dinicotinonitrile

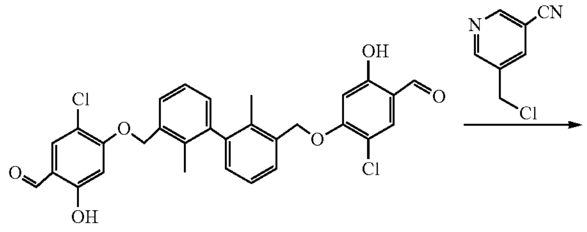

-continued

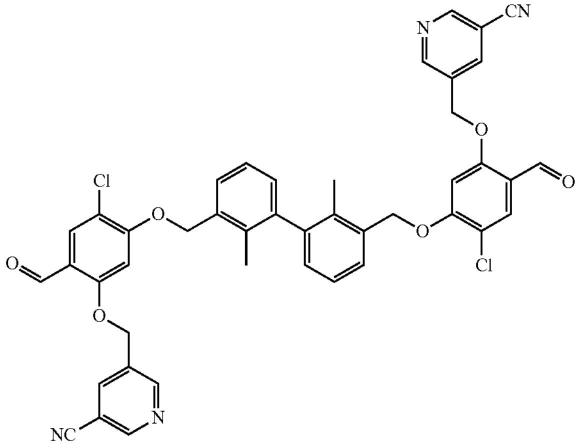

A solution of 4,4'-(((2,2'-dimethyl-[1,1'-biphenyl]-3,3'-diyl)bis(methylene)) bis(oxy))bis(3-chloro-2-hydroxybenzaldehyde) (277 mg, 0.502 mmol) in 1 mL DMF under $N_2$ was treated with $Cs_2CO_3$ (816 mg, 2.5 mmol) and the mixture stirred under $N_2$ at rt for 15 min. 5-(Chloromethyl) nicotinonitrile (230 mg, 1.5 mmol) and NaI (151 mg, 1.00 mmol) and the reaction stirred under $N_2$ at 60 C for 6 h. The mixture was diluted with EtOAc and water and stirred vigorously for 15 min. The precipitate was filtered to provide the desired product as a solid. The filtrate was washed with 5% LiCl (2×), dried with $Na_2SO_4$ and concentrated. Purification of the filtrate derived material by ISCO (DCM-MeOH) provided additional product as a solid. An analytical sample was prepared by RP-HPLC purification to provide a solid. [M+H]=783.01. $^1$H NMR (400 MHz, DMSO-$d_6$) δ 10.21 (s, 2H), 9.02 (m, 4H), 8.54 (t, J=2.1 Hz, 2H), 7.71 (s, 2H), 7.53 (dd, J=7.7, 1.4 Hz, 2H), 7.36-7.25 (m, 4H), 7.14 (dd, J=7.7, 1.4 Hz, 2H), 5.47 (s, 4H), 5.42 (s, 4H), 2.02 (s, 3H).

Intermediate 13: 5-((4-chloro-2-formyl-5-((2-methyl-3-(4,4,5,5-tetramethyl-1,3,2-dioxaborolan-2-yl)benzyl)oxy)phenoxy)methyl)nicotinonitrile

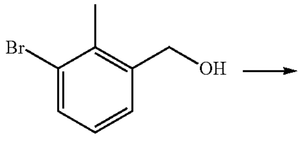

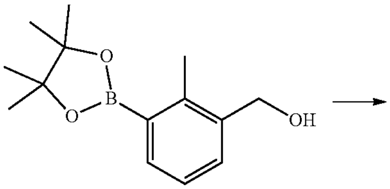

-continued

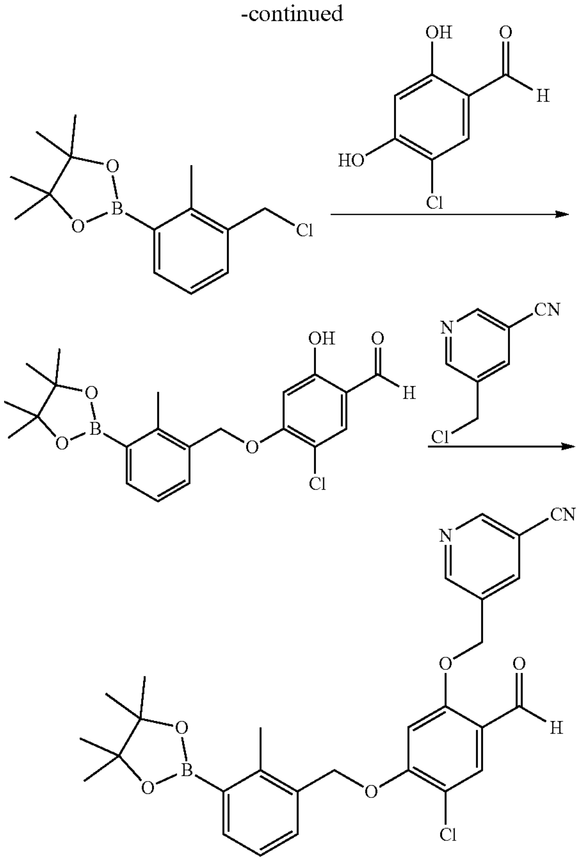

Step-1:

To a stirred solution of (3-bromo-2-methylphenyl)methanol (1.0 g, 5.0 mmol), $B_2(pin)_2$ (2.0 g, 8.0 mmol), Pd(dppf) $Cl_2 \cdot CH_2Cl_2$ (600 mg, 0.75 mmol) in dioxane (200 mL)under argon atmosphere was added KOAc (1.5 g, 15 mmol) at once. The reaction mixture was stirred at 85° C. for 16h, filtered through pad of Celite and washed with EtOAc. The crude product was purified by flash column chromatography (0-50% EtOAc in hexanes). The fractions containing product were combined, solvent was removed under reduced pressure to yield an oil which was stirred in hexanes (or triturated) and filtered to yield product (2-methyl-3-(4,4,5,5-tetramethyl-1,3,2-dioxaborolan-2-yl)phenyl)methanol. $^1H$ NMR: ($CDCl_3$, 400 MHz): δ 7.72-7.70 (m, 1H), 7.44-7.42 (m, 1H), 7.21-7.17 (m, 1H), 4.69 (s, 2H), 2.54 (s, 3H), 1.36 (s, 12H).

Step-2:

To a stirred solution of (2-methyl-3-(4,4,5,5-tetramethyl-1,3,2-dioxaborolan-2-yl)phenyl)methanol-2 (250 mg, 1.0 mmol), DIPEA (260 mg, 2.0 mmol)under argon atmosphere was added methanesulfonyl chloride (140 mg, 1.2 mmol) drop wise at 0° C., and the reaction mixture was allowed to warm to rt and stir overnight. After 16 hours, partitioned between water and $CH_2Cl_2$, separated organic layer dried over anhydrous $Na_2SO_4$. The solvent was concentrated under reduced pressure and the crude product-2-(3-(chloromethyl)-2-methylphenyl)-4,4,5,5-tetramethyl-1,3,2-dioxaborolane was used for next step without further purification. $^1H$ NMR: ($CDCl_3$, 400 MHz): δ 7.76-7.75 (m, 1H), 7.40-7.38 (m, 1H), 7.20-7.16 (m, 1H), 4.64 (s, 2H), 2.64 (s, 3H), 1.36 (s, 12H).

Step-3:

To a stirred solution of 5-chloro-2,4-dihydroxybenzaldehyde-4 (170 mg, 0.81 mmol) in DMF (6 mL) was added sodium bicarbonate (120 mg, 1.4 mmol)under argon atmosphere. The mixture was stirred for 15 minutes at room temperature, and a solution of 2-(3-(chloromethyl)-2-methylphenyl)-4,4,5,5-tetramethyl-1,3,2-dioxaborolane (180 mg, 0.68 mmol) in THF (6 mL) followed by sodium iodide (100 mg, 0.68 mmol) were added at once. The reaction was stirred at 60° C. for 16 h. The reaction mixture was diluted with $CH_2Cl_2$, quenched with saturated aqueous $NH_4Cl$, and extracted with $CH_2Cl_2$(3×10 mL). The organic layer was dried over $Na_2SO_4$, solvent was removed under reduced pressure, and purified by flash column chromatography (0→50% EtOAc in hexanes) to yield 5-chloro-2-hydroxy-4-((2-methyl-3-(4,4,5,5-tetramethyl-1,3,2-dioxaborolan-2-yl)benzyl)oxy)benzaldehyde. $^1H$ NMR: ($CDCl_3$, 400 MHz): δ 11.43 (s, 1H), 9.68 (s, 1H), 7.80-7.78 (m, 1H), 7.62-7.45 (m, 2H), 7.26-7.22 (m, 1H), 6.59 (s, 1H), 5.17 (s, 2H), 2.58 (s, 3H), 1.37 (s, 12H).

Step-4:

To a stirred solution of 5-chloro-2-hydroxy-4-((2-methyl-3-(4,4,5,5-tetramethyl-1,3,2-dioxaborolan-2-yl)benzyl)oxy)benzaldehyde (100 mg, 0.25 mmol) and cesium carbonate (160 mg 0.50 mmol) in DMF (3 mL)under argon atmosphere was added 5-(chloromethyl)nicotinonitrile (75 mg, 0.5 mmol) and sodium iodide (37 mg, 0.25 mmol) at rt, then heated to 75° C. After two hours, quenched with sat. aq. $NH_4Cl$, extracted with $CH_2Cl_2$, dried over anhydrous $Na_2SO_4$. The solvent was removed under reduced pressure, and purified by flash column chromatography to yield product 5-((4-chloro-2-formyl-5-((2-methyl-3-(4,4,5,5-tetramethyl-1,3,2-dioxaborolan-2-yl)benzyl)oxy)phenoxy)methyl)nicotinonitrile. $^1H$ NMR: ($CDCl_3$, 400 MHz): δ 10.25 (s, 1H), 8.89-8.88 (m, 2H), 8.10-8.05 (m, 1H), 7.88 (s, 1H), 7.79-7.77 (m, 1H), 7.46-7.44 (m, 1H), 7.23-7.19 (m, 1H), 6.56 (s, 1H), 5.21 (s, 2H), 5.17 (s, 2H), 2.57 (s, 3H), 1.37 (s, 12H).

Intermediate 14: 4-((3-bromo-2-methylbenzyl)oxy)-5-chloro-2-hydroxybenzaldehyde

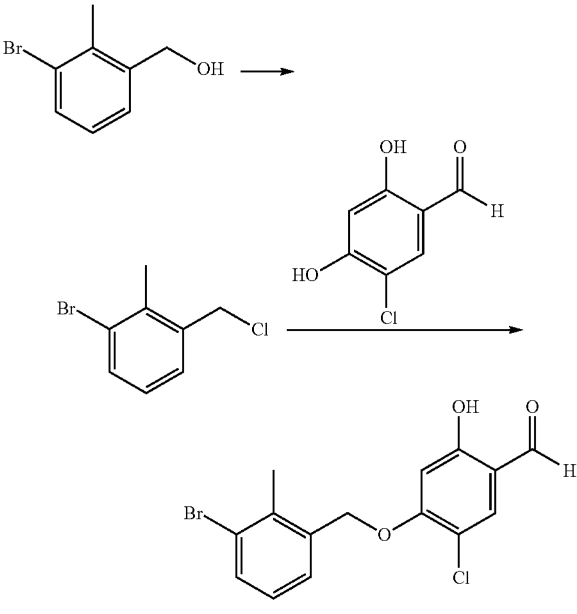

Step-1

To a solution of (3-bromo-2-methylphenyl)methanol (5 g, 24.9 mmol), TEA (5.2 mL) in dichloromethane under argon atmosphere at 0° C. was added MsCl (2.3 mL, 29.8 mmol) drop wise. The solution was allowed to warm to ambient temperature and stirred for 16h. The reaction mix was partitioned btw DCM/water, extracted, dried over $Na_2SO_4$, filtered, and concentrated to afford 1-bromo-3-(chloromethyl)-2-methylbenzene as a liquid 5.1 g (>95% pure, stable at RT over 2 weeks).

Step-2

To a solution of 5-chloro-2,4-dihydroxybenzaldehyde (1.6 g, 9.27 mmol) in DMF (15 mL) was added $NaHCO_3$ (1.04 g, 16.86 mmol)under argon and stirred for 10 min. A solution of 1-bromo-3-(chloromethyl)-2-methylbenzene (1.85 g, 8.43 mmol) in THF (15 mL) was added followed by NaI (1.26 g, 8.43 mmol) at once. The mixture was heated at 60° C. overnight. To the reaction was added water (~50 mL) precipitation occur and stirred at RT for 10 min (product crashes out with small impurity), the solid was filtered, washed with water, dried under vacuum to afford crude product. To the crude product (~85% pure) was added 2% MeOH/DCM (~60-80 mL) warmed at 50° C. for 5 min to maximum dissolution (or sonicate 2 min), the insoluble mat (solid impurity) was filtered, rinsed with ice-cold 2% MeOH/DCM (10 mL×2) and pure product crystallized out in the cold solution while filtering. The filtrate was left at 0° C. for 30 min. The solid product (pure product) was filtered, rinsed with cold 2% MeOH/DCM (10 mL×2) to afford 4-((3-bromo-2-methylbenzyl)oxy)-5-chloro-2-hydroxybenzaldehyde as a solid and the mother liquor was left at 0° C. for 30 min to isolate second crop.

Intermediate 15: 5-((5-((3-bromo-2-methylbenzyl)oxy)-4-chloro-2-formylphenoxy)methyl)nicotinonitrile

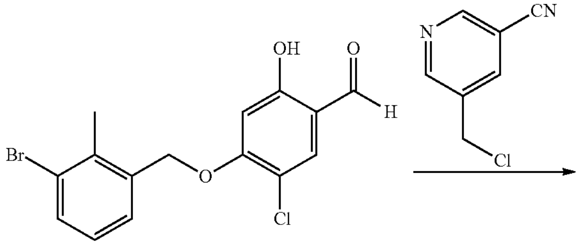

-continued

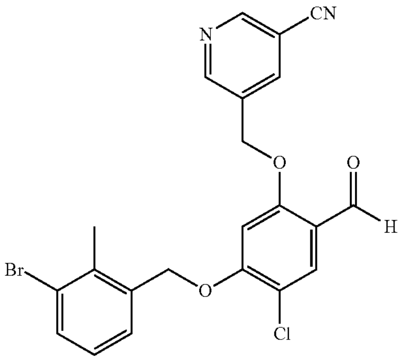

A mixture of 4-((3-bromo-2-methylbenzyl)oxy)-5-chloro-2-hydroxybenzaldehyde (1.7 g, 4.78 mmol) and $Cs_2CO_3$ (3.11 g, 9.56 mmol), DMF (25 mL) were taken in a 100 mL RB-flask, and stirred for 5 min under argon. To the well stirred mixture was added 5-(chloromethyl)nicotinonitrile (1.45 g, 9.56 mmol) followed by NaI (716 mg, 4.78 mmol) at once and heated at 75° C. for 3 h. Diluted with water (~50-60 mL) precipitation occur and stirred at RT for 10 min (product crashes out with small impurity) the solid product was filtered, washed with water, dried under vacuum to afford >80% pure product. To further purify, the (>80% pure) material was added to 2% MeOH/DCM (~70 mL), sonicated for 2 min (or warm at 50° C. for 5 min) to dissolve. Left it to cool at 0° C. for 30 min. Filtered, rinsed with cold solution of 2% MeOH/DCM (10 mL×2) to afford pure 5-((5-((3-bromo-2-methylbenzyl)oxy)-4-chloro-2-formylphenoxy)methyl)nicotinonitrile. The mother liquor was left to cool at 0° C. for 1 h for second crop of product.

Intermediate 16: 5-((4-chloro-5-((2,2'-dimethyl-4"-(2-oxoethoxy)-[1,1':3',1"-terphenyl]-3-yl)methoxy)-2-formylphenoxy)methyl)nicotinonitrile

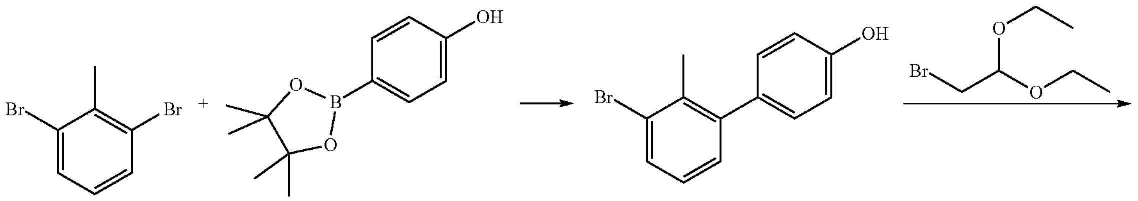

-continued

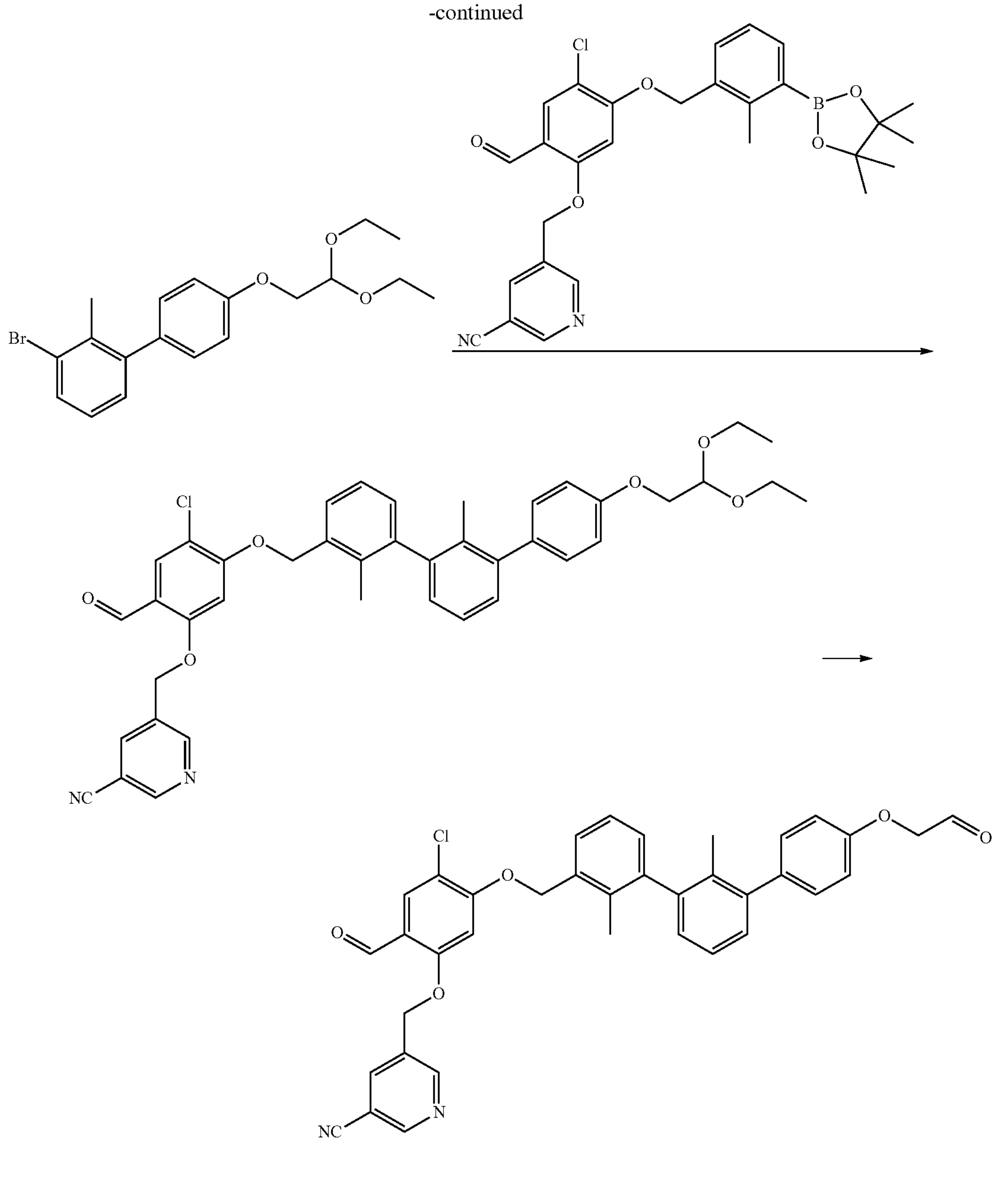

A mixture of 1,3-dibromo-2-methylbenzene (7.5 g, 30 mmol), 4-(4,4,5,5-tetramethyl-1,3,2-dioxaborolan-2-yl)phenol (2.2 g, 10 mmol), DMF (15 mL) and 2N potassium carbonate (5 mL) was purged with argon for 10 min. [1,1'-Bis(diphenylphosphino)ferrocene]dichloropalladium (I) complex with dichloromethane (410 mg, 0.5 mmol) was then added. The resulting mixture was stirred at 50° C. for 16 h and then at 80° C. for 2 h. After cooling, the mixture was partitioned between ethyl acetate and 3% LiCl in water. The ethyl acetate layer was taken and concentrated. The residue was purified by Combiflash, affording 3'-bromo-2'-methyl-[1,1'-biphenyl]-4-ol as a solid. $^1$H NMR ($CDCl_3$) 7.53 (d, 1H), 7.13-7.16 (m, 3H), 7.05 (t, 1H), 6.87 (d, 2H), 4.74 (brs, 1H), 2.31 (s, 3H).

To a solution of 3'-bromo-2'-methyl-[1,1'-biphenyl]-4-ol (1.0 g, 3.8 mmol) in NMP (5 mL) was added 60% sodium hydride in mineral oil (460 mg, 11 mmol). After the gas evolution had ceased, 2-bromo-1,1-diethoxyethane (2.25 g, 11.4 mmol) was added. The resulting mixture was stirred at 80° C. for 4 h. After cooling, the mixture was partitioned between ethyl acetate and 3% LiCl in water. The ethyl acetate layer was taken and concentrated. The residue was purified by Combiflash, affording 3-bromo-4'-(2,2-diethoxyethoxy)-2-methyl-1,1'-biphenyl as an oil. $^1$H NMR (CDCl3) 7.52 (d, 1H), 7.13-7.20 (m, 3H), 7.05 (t, 1H), 6.96 (d, 2H), 4.86 (t, 1H), 4.05 (d, 2H), 3.78 (dq, 2H), 3.66 (dq, 2H), 2.30 (s, 3H), 1.26 (m, 6H).

A mixture of 3-bromo-4'-(2,2-diethoxyethoxy)-2-methyl-1,1'-biphenyl (380 mg, 1 mmol), 5-((4-chloro-2-formyl-5-((2-methyl-3-(4,4,5,5-tetramethyl-1,3,2-dioxaborolan-2-yl)benzyl)oxy)phenoxy)methyl)nicotinonitrile (519 mg, 1 mmol), DMF (4 mL) and 2N potassium carbonate (0.5 mL) was purged with argon for 10 min. [1,1'-Bis(diphenylphosphino)ferrocene]dichloropalladium(II) complex with dichloromethane (41 mg, 0.05 mmol) was then added. The resulting mixture was stirred at 90° C. for 1 h. After cooling, the mixture was partitioned between ethyl acetate and 3% LiCl in water. The ethyl acetate layer was taken and concentrated. The residue was purified by Combiflash, affording 5-((4-chloro-5-((4"-(2,2-diethoxyethoxy)-2,2'-dimethyl-[1,1':3',1"-terphenyl]-3-yl)methoxy)-2-formylphenoxy)methyl)nicotinonitrile as a solid. $[M+H]^+$ 690.1.

To an ice-cold solution of 5-((4-chloro-5-((4"-(2,2-diethoxyethoxy)-2,2'-dimethyl-[1,1':3',1"-terphenyl]-3-yl)methoxy)-2-formylphenoxy)methyl)nicotinonitrile (390 mg, 0.56 mmol) in dioxane (5 mL) was added concentrated HCl (0.5 mL). The mixture was then stirred at room temperature for 1 h. After neutralizing with saturated aqueous sodium bicarbonate, the mixture was extracted with ethyl acetate. The ethyl acetate layer was dried over sodium sulfate and concentrated, affording 5-((4-chloro-5-((2,2'-dimethyl-4"-(2-oxoethoxy)-[1,1':3',1"-terphenyl]-3-yl)methoxy)-2-formylphenoxy)methyl)nicotinonitrile, which was used without further purification. $[M+H]^+$ 617.0.

Intermediate 17: 2-methoxy-6-((2-methyl-3-(4,4,5,5-tetramethyl-1,3,2-dioxaborolan-2-yl)benzyl)oxy)nicotinaldehyde

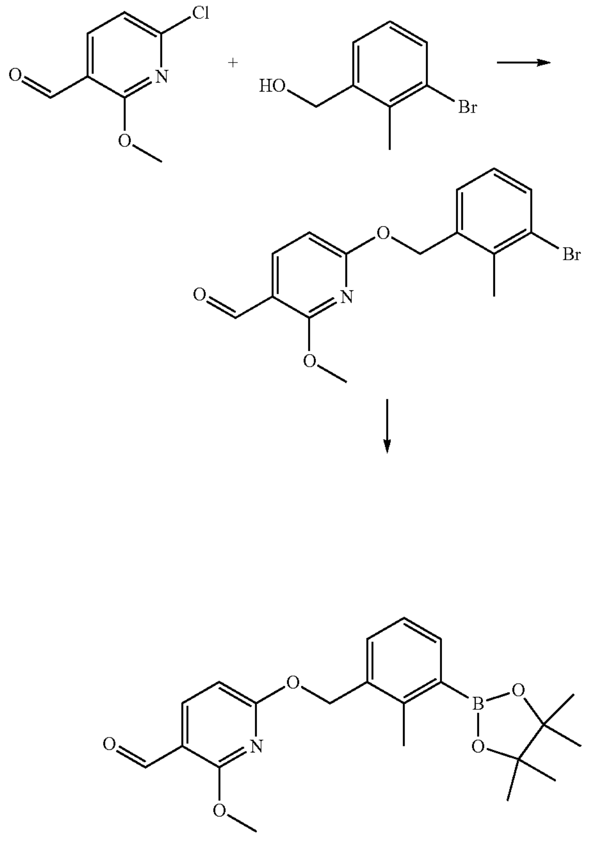

(3-Bromo-2-methylphenyl) methanol (300 mg, 1.49 mmol) was dissolved in DMF (6 ml). Sodium hydride (60% dispersion in mineral oil, 72 mg, and 1.79 mmol) was added. The suspension was stirred at room temperature for 5 min before 6-chloro-2-methoxynicotinaldehyde (256 mg, 1.49 mmol) was added in one portion. Complete conversion was detected after stirring at room temperature for 30 min. EtOAc and water were added to the mixture. The organic layer was evaporated under reduced pressure. The residue was purified by silica gel chromatography using Hexanes/EtOAc as the eluent to afford 6-((3-bromo-2-methylbenzyl)oxy)-2-methoxynicotinaldehyde.

6-((3-bromo-2-methylbenzyl) oxy)-2-methoxynicotinaldehyde (348 mg, 1.035 mmol) was dissolved in DMF (5 mL), treated with bis(pinacolato)diboron (551 mg, 2.17 mmol), Pd(dppf)$Cl_2$-DCM (114 mg, 0.156 mmol) and potassium acetate (406 mg, 4.14 mmol). The mixture was purged with argon and then heated at 85° C. for 1.5 h. After cooling to room temperature, the mixture was diluted with EtOAc and water. The organic layer was concentrated and the residue was purified by silica gel chromatography using Hexanes/EtOAc as the eluent to afford 2-methoxy-6-((2-methyl-3-(4,4,5,5-tetramethyl-1,3,2-dioxaborolan-2-yl)benzyl)oxy)nicotinaldehyde.

Intermediate 18: 6,6'-(((2,2'-dimethyl-[1,1'-biphenyl]-3,3'-diyl)bis(methylene))bis(oxy))bis(5-chloro-2-methoxynicotinaldehyde)

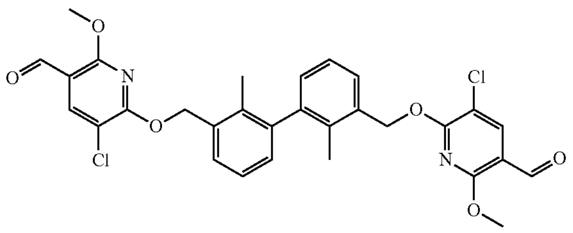 [SMILES: COc1nc(OCc2cccc(-c3cccc(COc4nc(OC)c(C=O)cc4Cl)c3C)c2C)c(Cl)cc1C=O]

To a solution of 6,6'-(((2,2'-dimethyl-[1,1'-biphenyl]-3,3'-diyl)bis(methylene))bis(oxy))bis(2-methoxynicotinaldehyde) (10.1 g, 19.7 mmol) and Palau'Chlor (9.08 g, 43.4 mmol) in DMF/$CHCl_3$ (1:1 v/v, 600 mL) was added HCl (4 M in dioxane, 10.8 mL, 43.3 mmol) dropwise. The mixture was stirred at ambient temperature for 30 min, then diluted with $CH_2Cl_2$ (500 mL), and washed with $NaHCO_3$ (saturated aq., 3×300 mL), then $H_2O$ (3×300 mL), then brine (100 mL). The organic layer was dried ($Na_2SO_4$) and concentrated, and the residue was purified by column chromatography ($SiO_2$, 0-100% EtOAc in hexanes) to yield the product as a solid.

Intermediate 19: 5-((5-((3'-bromo-2,2'-dimethyl-[1,1'-biphenyl]-3-yl)methoxy)-4-chloro-2-formylphenoxy)methyl)nicotinonitrile

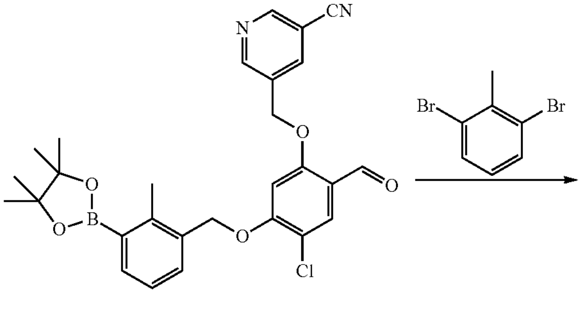

-continued

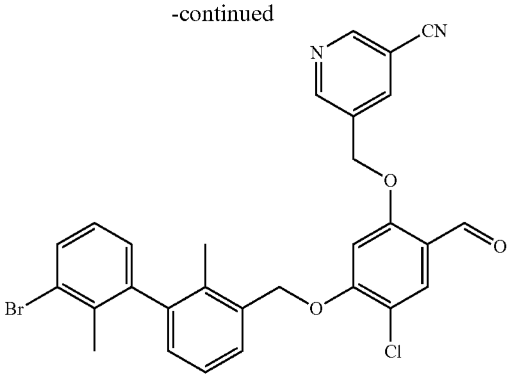

A suspension of 5-((4-chloro-2-formyl-5-((2-methyl-3-(4,4,5,5-tetramethyl-1,3,2-dioxaborolan-2-yl)benzyl)oxy)phenoxy)methyl)nicotinonitrile (600 mg, 1.16 mmol) and 1,3-dibromo-2-methylbenzene (578.1 mg, 2.31 mmol, 2 equiv) in 6 mL 9:1 dioxane:water was degassed by bubbling $N_2$ for 30 minutes. To the reaction was added dichloro 1,1-bis (diphenylphosphino)ferrocene palladium(II) (8.46 mg, 0.0116 mmol, 1% mol), and potassium carbonate (0.16 g, 1.16 mmol) was added to the reaction. The vessel was sealed and heated at 100° C. for 16 h. The reaction was diluted with water and extracted with DCM, the organic layer was dried with $Na_2SO_4$, filtered, and concentrated. The residue was purified by silica flash chromatography eluting with 70% EA:Hex to afford product as a solid. LCMS 93% m/z=563.0.

Intermediate 20: 5,5'-((((((2,2'-dimethyl-[1,1'-biphenyl]-3,3'-diyl)bis(methylene))bis(oxy))bis(5-chloro-3-formylpyridine-6,2-diyl))bis(oxy))bis(methylene)) dinicotinonitrile

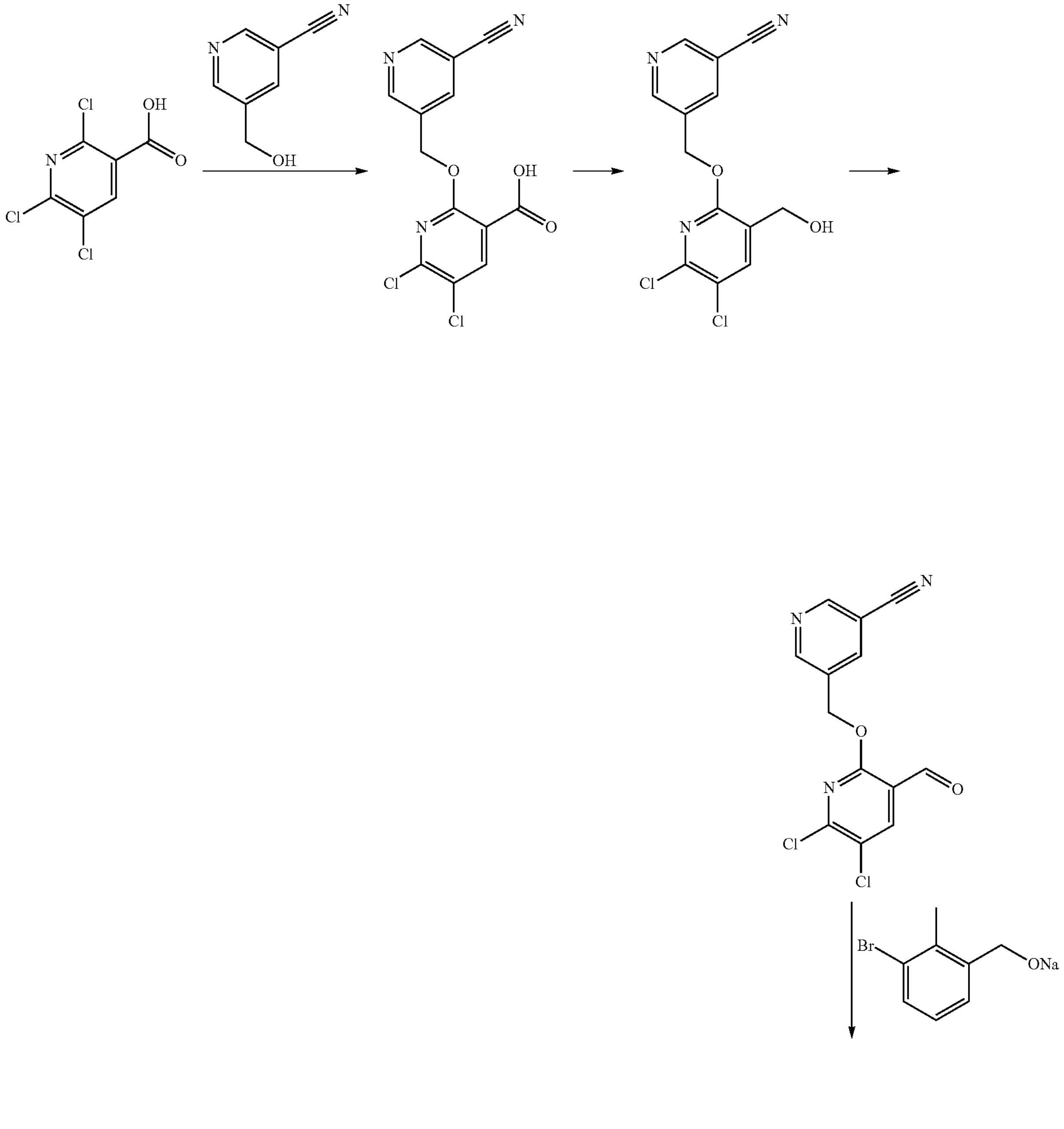

-continued

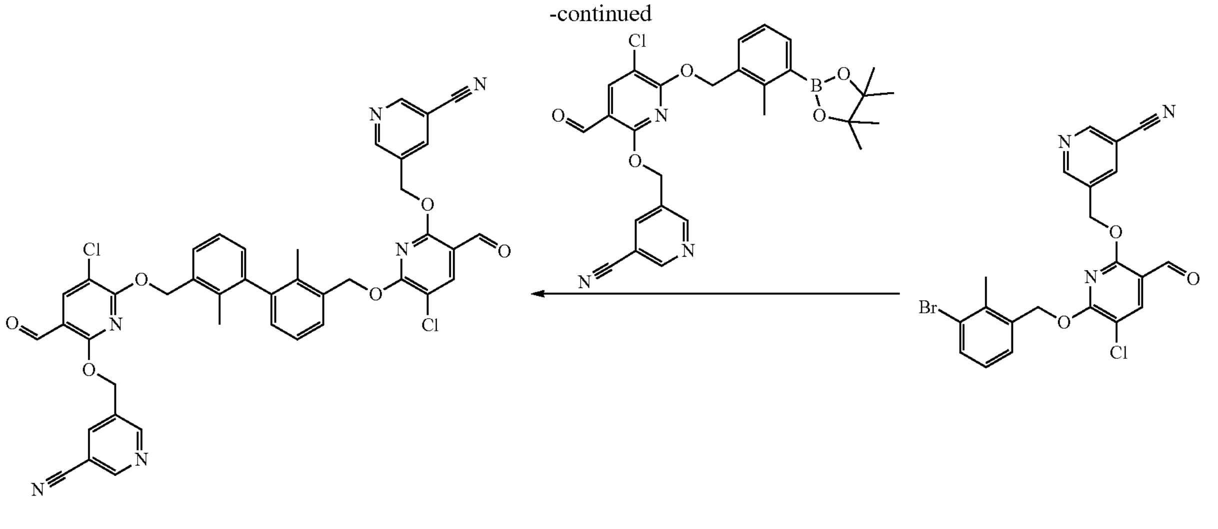

To a solution of 5-(hydroxymethyl)nicotinonitrile (1.51 g, 9.7 mmol, 1 equiv) in THF (10 mL) at 0° C. was added NaH (292 mg, 12.2 mmol, 1.25 equiv). After an additional 20 minutes of stirring the slurry was added to a stirred solution of 2,5,6-trichloronicotinic acid (2.2 g, 9.7 mmol, 1 equiv) in THF at 0° C. To a solution was slowly allowed to war, to room temperature and stirred for 1 hour. The reaction mixture was then acidified with 1 M HCl and the precipitated 5,6-dichloro-2-((5-cyanopyridin-3-yl)methoxy)nicotinic acid was collected by vacuum filtration.

To a stirred solution of 5,6-dichloro-2-((5-cyanopyridin-3-yl)methoxy)nicotinic acid (3.0 g, 9.4 mmol, 1 equiv) in THF was added catalytic DMF (1 drop), followed by oxalyl chloride (1 equiv). After 10 minutes gas evolution had ceased and the reaction was cooled to −78° C. Then $Li((OtBu)_3AlH)$ (1 M, 11.3 mL, 1.2 equiv) was added dropwise. After full consumption of starting material by LCMS the reaction was quenched with excess 4M NaOH and water then warmed to room temperature. The organic and aqueous layers were separated and the aqueous layer was extracted with ethyl acetate. The combined organic layers were dried over sodium sulfate, filtered and concentrated in vacuo. The crude material was used without any further purification. LCMS found 310.1 (M+1).

To a slurry of 5-(((5,6-dichloro-3-(hydroxymethyl)pyridin-2-yl)oxy)methyl)nicotinonitrile (2.5 g, 8.06 mmol, 1 equiv) in methylene chloride at room temperature was added Dess-Martin periodane (3.76 g, 8.87 mmol, 1.1 equiv). The solution was allowed to stir until LCMS showed full consumption of alcohol. The reaction mixture was purified directly by silica gel chromatography (Hex/EtOAc, 0 to 50%) to afford 5-(((5,6-dichloro-3-formylpyridin-2-yl)oxy)methyl)nicotinonitrile as a solid.

To a solution of (3-bromo-2-methylphenyl)methanol (750 mg, 2.4 mmol, 1 equiv) in DMF (4 mL) at room temperature was added NaH (97 mg, 2.4 mmol, 1.0 equiv). After an additional 20 minutes of stirring the slurry was added to a stirred DMF (4 mL) solution of 5-(((5,6-dichloro-3-formylpyridin-2-yl)oxy)methyl)nicotinonitrile (490 mg, 2.4 mmol, 1 equiv). Upon complete consumption of starting material by LCMS the reaction was diluted with water (5 mL) and extracted three times with 5 mL ethyl acetate. The combined organic layers were washed with brine, dried over sodium sulfate, filtered, and concentrated in vacuo. Purification by silica gel chromatography (Hex/EtOAc, 0 to 100%) afforded 5-(((6-((3-bromo-2-methylbenzyl)oxy)-5-chloro-3-formylpyridin-2-yl)oxy)methyl)nicotinonitrile as a solid.

A vial with a stir bar was charged with 5-(((6-((3-bromo-2-methylbenzyl)oxy)-5-chloro-3-formylpyridin-2-yl)oxy)methyl)nicotinonitrile (80 mg, 0.17 mmol, 1 equiv), bis(pinacolato)diboron (43 mg, 0.17 mmol, 1 equiv), Pd(dppf)$Cl_2$ (14 mg, 0.017 mmol, 0.1 equiv), and potassium acetate (33 mg, 0.34 mmol, 2 equiv). The vial sealed and dioxane (2 mL) was added via syringe. The reaction mixture was sparged with argon for 10 minutes then heated to 100 C until full consumption of starting material was observed by LCMS. To the reaction mixture was then added 5-(((6-((3-bromo-2-methylbenzyl)oxy)-5-chloro-3-formylpyridin-2-yl)oxy)methyl)nicotinonitrile (80 mg, 0.17 mmol, 1 equiv), Pd(dppf)$Cl_2$ (14 mg, 0.017 mmol, 0.1 equiv), and potassium carbonate (47 mg, 0.34 mmol, 2 equiv). The vial was sealed and water (0.4 mL) was added via syringe. The reaction mixture was sparged with argon for 10 minutes then heated to 100 C until complete consumption of starting materials was observed by LCMS. The reaction mixture was then diluted with EtOAc, filtered through celites, and concentrated in vacuo to dryness. Purification of crude material by silica gel chromatography afforded 5,5'-((((((2,2'-dimethyl-[1,1'-biphenyl]-3,3'-diyl)bis(methylene))bis(oxy))bis(5-chloro-3-formylpyridine-6,2-diyl))bis(oxy))bis(methylene))dinicotinonitrile as a solid.

Intermediate 21: 5,5'-((((((2,2'-dimethyl-[1,1'-biphenyl]-3,3'-diyl)bis(methylene))bis(oxy))bis(5-bromo-3-formylpyridine-6,2-diyl))bis(oxy))bis(methylene))dinicotinonitrile

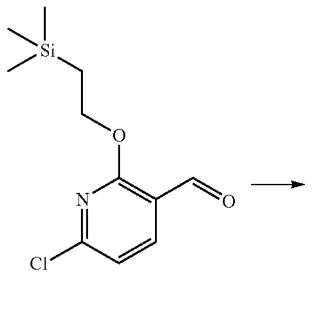

-continued

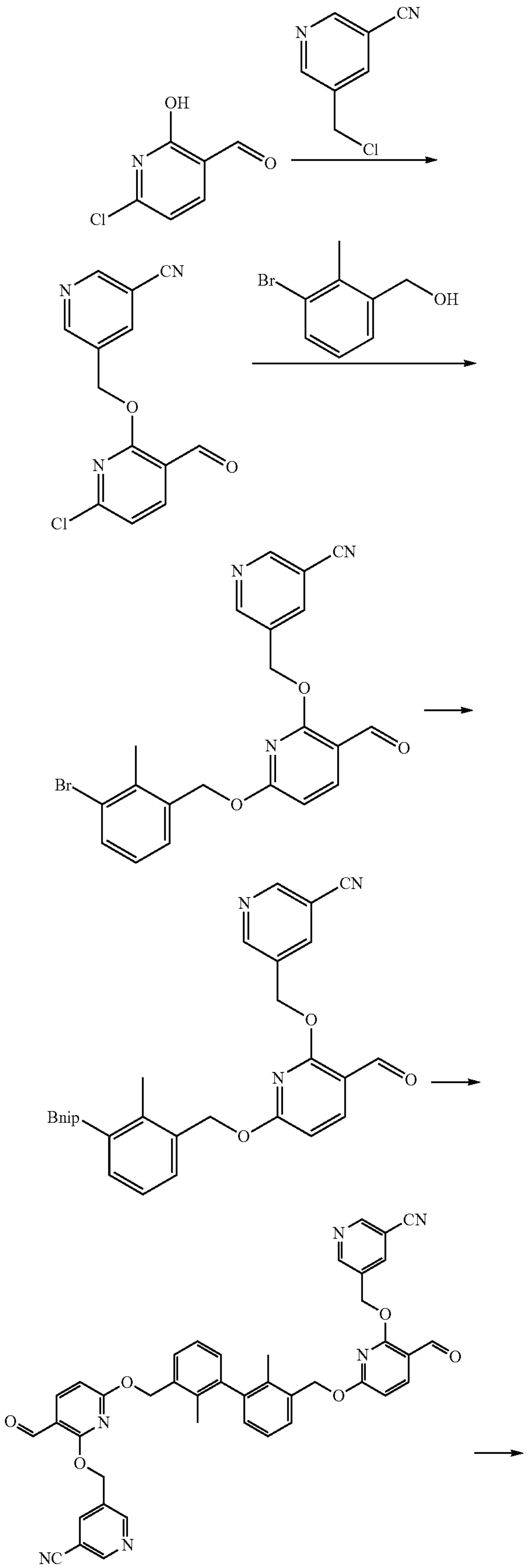

-continued

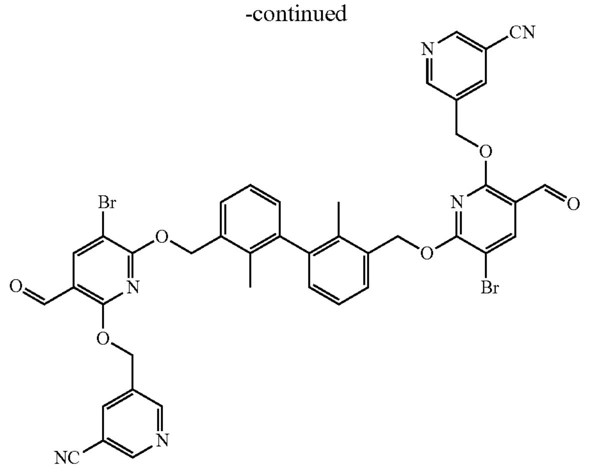

To a 20 mL vial was added 6-chloro-2-(2-(trimethylsilyl)ethoxy)nicotinaldehyde (500 mg, 1.9 mmol), cesium fluoride (591 mg, 3.9 mmol, 2.0 equiv), and N,N-dimethylformamide (7.0 mL, 0.27 M) at room temperature. The vessel was heated at 60° C. for 1 hour before being cooled back to room temperature. To the vessel was then added 5-(chloromethyl)nicotinonitrile (350 mg, 2.3 mmol, 1.2 equiv), potassium carbonate (390 mg, 2.9 mmol, 1.5 equiv), and sodium iodide (72 mg, 0.47 mmol, 25 mol %). The reaction mixture was stirred at 60° C. for 1 hour before being cooled to room temperature and diluted with ethyl acetate (40 mL). Finally, water (30 mL) was added, and the organic layer was washed ×1 (once) with brine, dried over magnesium sulfate, filtered, and concentrated under vacuum. The crude material was purified by silica gel column chromatography using a 0-10% methanol in methylene chloride eluent gradient to provide 5-(((6-chloro-3-formylpyridin-2-yl)oxy)methyl)nicotinonitrile.

To a 20 mL vial was added (3-bromo-2-methylphenyl)methanol (220 mg, 1.1 mmol) and N,N-dimethylformamide (5.5 mL, 0.2 M) at room temperature. To the vessel was added sodium hydride (53 mg, 60 wt % dispersion in mineral oil, 1.3 mmol, 1.2 equiv), and the mixture was stirred for 30 minutes. In a separate 20 mL vial was added 5-(((6-chloro-3-formylpyridin-2-yl)oxy)methyl)nicotinonitrile (300 mg, 1.1 mmol, 1.0 equiv) and N,N-dimethylformamide (5.5 mL, 0.2 M) at room temperature. To the mixture was added the suspension of (3-bromo-2-methylphenyl)methanol sodium salt in and N,N-dimethylformamide dropwise at room temperature. The mixture was stirred for 1 hour before being diluted with ethyl acetate (40 mL). Finally, water (30 mL) was added, and the organic layer was washed ×1 with brine, dried over magnesium sulfate, filtered, and concentrated under vacuum. The crude material was purified by silica gel column chromatography using a 0-10% methanol in methylene chloride eluent gradient to provide 5-(((6-((3-bromo-2-methylbenzyl)oxy)-3-formylpyridin-2-yl)oxy)methyl)nicotinonitrile.

To a 20 mL vial was added 5-(((6-((3-bromo-2-methylbenzyl)oxy)-3-formylpyridin-2-yl)oxy)methyl)nicotinonitrile (473 mg, 0.47 mmol), 4,4,4',4',5,5,5',5'-octamethyl-2,2'-bi(1,3,2-dioxaborolane) (161 mg, 0.63 mmol, 1.35 equiv), [1,1'-Bis(diphenylphosphino)ferrocene]dichloropalladium (II) (34 mg, 0.05 mmol, 10 mol %), potassium acetate (94 mg, 0.94 mmol, 2.0 equiv), and 1,4-dioxane (4.7 mL, 0.1M) at room temperature. The vessel was sealed, and the mixture was sparged with nitrogen for 5 minutes before being heated to 90° C. for 3 hours. The reaction mixture was then cooled to room temperature, ethyl acetate (10 mL) was added, and the contents of the vial were filtered through celite. The filtrate was concentrated under vacuum, and the crude 5-(((3-formyl-6-((2-methyl-3-(4,4,5,5-tetramethyl-1,3,2-dioxaborolan-2-yl)benzyl)oxy)pyridin-2-yl)oxy)methyl)nicotinonitrile was used without further purification.

To a 20 mL vial was added the crude 5-(((3-formyl-6-((2-methyl-3-(4,4,5,5-tetramethyl-1,3,2-dioxaborolan-2-yl)benzyl)oxy)pyridin-2-yl)oxy)methyl)nicotinonitrile, added 5-(((6-((3-bromo-2-methylbenzyl)oxy)-3-formylpyridin-2-yl)oxy)methyl)nicotinonitrile (473 mg, 0.47 mmol), [1,1'-Bis(diphenylphosphino)ferrocene]dichloropalladium(II) (34 mg, 0.05 mmol, 10 mol %), potassium carbonate (130 mg, 0.94 mmol, 2.0 equiv), N,N-dimethylformamide (4.7 mL, 0.1M), and water (0.5 mL) at room temperature. The vessel was sealed, and the mixture was sparged with nitrogen for 5 minutes before being heated to 90° C. for 1 hours. The reaction mixture was then cooled to room temperature, ethyl acetate (10 mL) was added, and the contents of the vial were filtered through celite. The filtrate was diluted with ethyl acetate (50 mL) and washed ×1 with water then brine. The organic layer was then dried over magnesium sulfate, filtered, and concentrated under vacuum. The crude material was purified by silica gel column chromatography using a 0-10% methanol in methylene chloride eluent gradient to provide 5,5'-((((((2,2'-dimethyl-[1,1'-biphenyl]-3,3'-diyl)bis(methylene))bis(oxy))bis(3-formylpyridine-6,2-diyl))bis(oxy))bis(methylene))dinicotinonitrile.

To a 20 mL vial was added 5,5'-((((((2,2'-dimethyl-[1,1'-biphenyl]-3,3'-diyl)bis(methylene))bis(oxy))bis(3-formylpyridine-6,2-diyl))bis(oxy))bis(methylene))dinicotinonitrile (716 mg, 1.0 mmol), potassium acetate (294 mg, 3.0 mmol, 3.0 equiv), and acetic acid (6.7 mL, 0.15 M) at room temperature. To the mixture was added bromine (2.2 mL, 1M in acetic acid, 2.2 mmol, 2.2 equiv) dropwise. After 1 hour, 1M aqueous sodium sulfite was added until the red color disappeared. To this mixture was added 5N aqueous sodium hydroxide until pH=7. Finally, ethyl acetate (10 mL) and water (10 mL) were added, and the organic layer was washed ×1 with brine, dried over magnesium sulfate, filtered, and concentrated under vacuum. The crude residue of 5,5'-((((((2,2'-dimethyl-[1,1'-biphenyl]-3,3'-diyl)bis(methylene))bis(oxy))bis(5-bromo-3-formylpyridine-6,2-diyl))bis(oxy))bis(methylene))dinicotinonitrile was used without further purification.

Intermediate 22: 6-chloro-2-(2-(trimethylsilyl)ethoxy)nicotinaldehyde

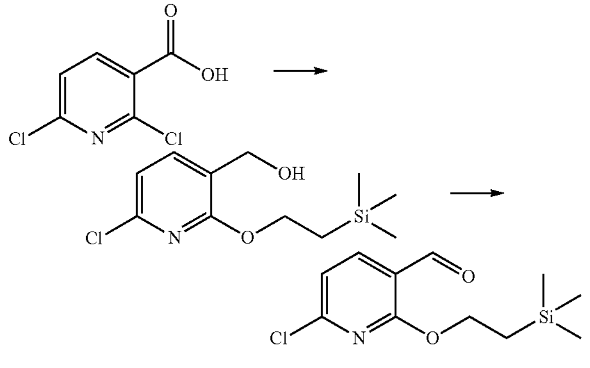

120 mL of THF was charged to a 500 mL RB containing 2.5 g (62.5 mmol) of NaH. 2-Trimethylsilylethanol (6.7 mL, 46.9 mmol) was added dropwise and the resulting suspension was stirred for 1 h at rt. Dichloronicotinic acid (3 g, 15.6 mmol) in 100 mL of THF was added drop-wise via addition funnel. After 2 h, borane-dimethyl sulfide (2M, 75 mL) was added over 15 min. The reaction was stirred for 15h at rt. The reaction was quenched with slow addition of MeOH (50 mL), 50 mL $H_2O$ and 10 mL sat aq. $NH_4Cl$, followed by heating to 90 C for 30 min. The solution was concentrated, diluted with DCM 100 mL, and washed with sat aq. $NH_4Cl$ and Brine. The organic layer was separated, and the aqueous extracted once with 100 mL DCM. The combined organics were dried over $Na_2SO_4$, and concentrated. The residual clear oil was added a stirring bar, and stirred in vacuo (0.3 mmHg) for 4h at 45° C. to remove most of TMS-ethanol. Column 10% Ethyl Acetate in Hexanes afforded the alcohol as a solid.

The alcohol (2.73 g, 10.51 mmol) was dissolved in 40 mL DCM in a 250 mL round bottom flask. Dess-Martin Periodinane (4.97 g, 11.77 mmol)) added in one portion. The solution was stirred for 2 min before 0.21 mL (11.77 mmol) of $H_2O$ was added dropwise. The clear solution becomes a milky suspension. The suspension was stirred for 45 min before 50 mL of a 1M NaOH solution was added, and the reaction was stirred vigorously for 15 min. The organic layer was separated, and the aqueous extracted twice with DCM (25 mL). The combined organics were dried, concentrated, and flashed through a column (10-20% EA) to afford the aldehyde as clusters. $^1H$ NMR (400 MHz, Chloroform-d) δ 10.31 (d, J=0.8 Hz, 1H), 8.04 (d, J=7.9 Hz, 1H), 6.98 (dd, J=7.9, 0.9 Hz, 1H), 4.87-4.21 (m, 2H), 1.27-1.06 (m, 2H), 0.09 (s, 9H).

Intermediate 23: 5,5'-((((((2,2'-dimethyl-[1,1'-biphenyl]-3,3'-diyl)bis(methylene))bis(oxy))bis(4-bromo-6-formyl-3,1-phenylene))bis(oxy))bis(methylene))dinicotinonitrile

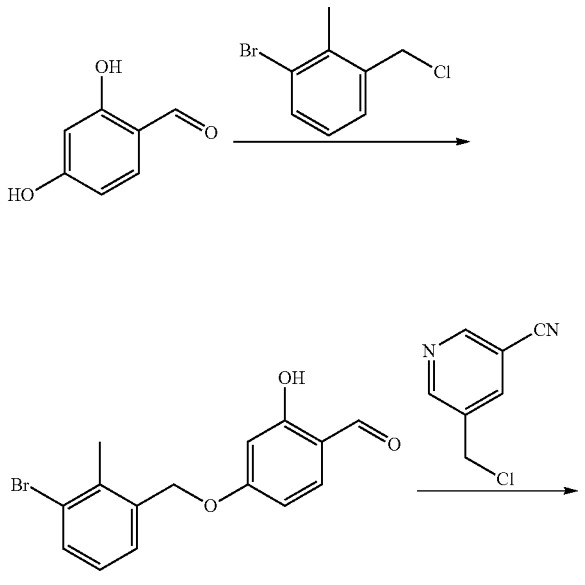

-continued

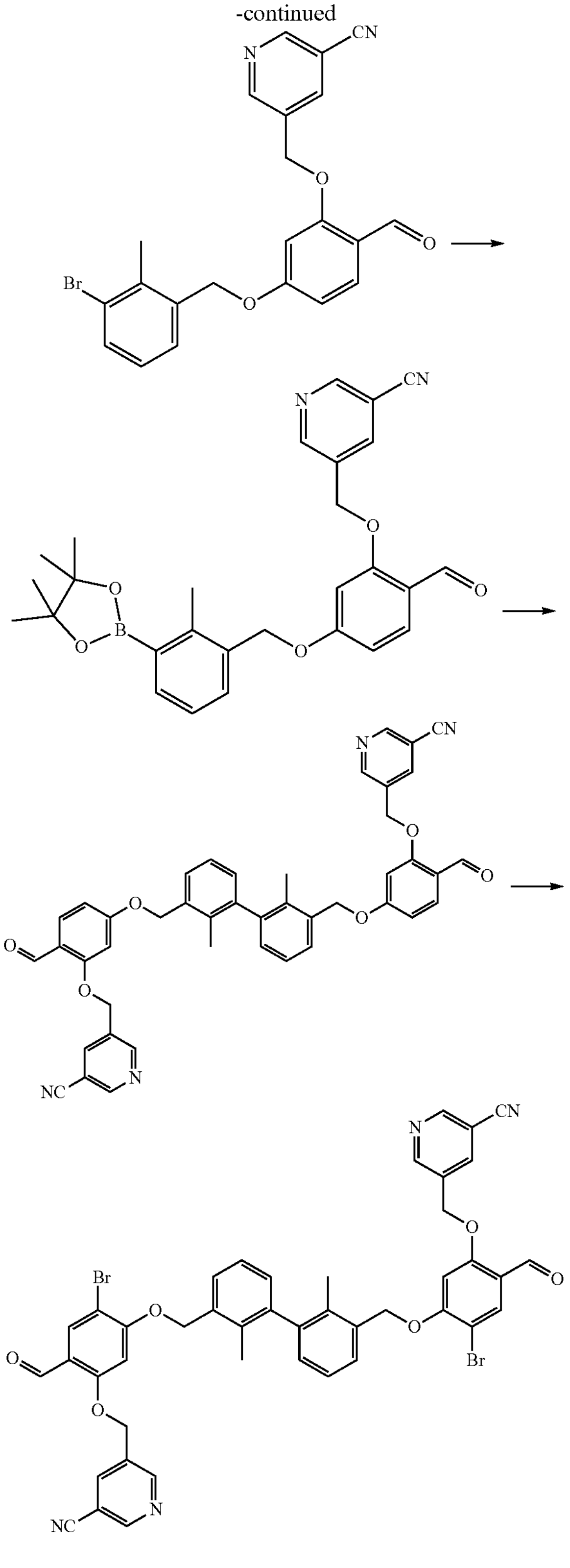

To a 100 mL round bottom flask was added 2,4-dihydroxybenzaldehyde (1.0 g, 7.25 mmol, 3.0 equiv), 1-bromo-3-(chloromethyl)-2-methylbenzene (527 mg, 2.4 mmol), potassium carbonate (828 mg, 6.0 mmol, 2.5 equiv), sodium iodide (36 mg, 0.24 mmol, 10 mol %) and N,N-dimethylformamide (20 mL, 0.12M) at room temperature. The reaction mixture was stirred at 60° C. for 2 hours before being cooled to room temperature and diluted with ethyl acetate (50 mL). The mixture was then acidified to pH=3 with 1N aqueous hydrochloric acid then washed once with water and once with brine. The organic layer was then dried over magnesium sulfate, filtered, and concentrated under vacuum. The crude material was purified by silica gel column chromatography using a 0-10% methanol in methylene chloride eluent gradient to provide 4-((3-bromo-2-methylbenzyl)oxy)-2-hydroxybenzaldehyde.

To a 100 mL round bottom flask was added 4-((3-bromo-2-methylbenzyl)oxy)-2-hydroxybenzaldehyde (422 mg, 1.32 mmol), 5-(chloromethyl)nicotinonitrile (241 mg, 1.6 mmol, 1.2 equiv), potassium carbonate (273 mg, 2.0 mmol, 1.5 equiv), sodium iodide (50 mg, 0.33 mmol, 25 mol %) and N,N-dimethylformamide (13.2 mL, 0.1M)) at room temperature. The reaction mixture was stirred at 60° C. for 1hourbeforebeingcooledtoroomtemperatureanddilutedwith-ethylacetate(40 mL). The mixture was washed once with water and once with brine. The organic layer was then dried over magnesium sulfate, filtered, and concentrated under vacuum. The crude material was purified by silica gel column chromatography using a 0-10% methanol in methylene chloride eluent gradient to provide 5-((5-((3-bromo-2-methylbenzyl)oxy)-2-formylphenoxy)methyl)nicotinonitrile.

To a 20 mL vial was added 5-((5-((3-bromo-2-methylbenzyl)oxy)-2-formylphenoxy)methyl)nicotinonitrile (460 mg, 1.1 mmol), 4,4,4',4',5,5,5',5'-octamethyl-2,2'-bi(1,3,2-dioxaborolane) (377 mg, 1.49 mmol, 1.35 equiv), [1,1'-Bis(diphenylphosphino)ferrocene]dichloropalladium(II) (81 mg, 0.11 mmol, 10 mol %), potassium acetate (215 mg, 2.20 mmol, 2.0 equiv), and 1,4-dioxane (11.0 mL, 0.1M) at room temperature. The vessel was sealed, and the mixture was sparged with nitrogen for 5 minutes before being heated to 90° C. for 3 hours. The reaction mixture was then cooled to room temperature, ethyl acetate (10 mL) was added, and the contents of the vial were filtered through celite. The filtrate was concentrated under vacuum, and the crude 5-((2-formyl-5-((2-methyl-3-(4,4,5,5-tetramethyl-1,3,2-dioxaborolan-2-yl)benzyl)oxy)phenoxy)methyl)nicotinonitrile was used without further purification.

To a 20 mL vial was added the crude 5-((2-formyl-5-((2-methyl-3-(4,4,5,5-tetramethyl-1,3,2-dioxaborolan-2-yl)benzyl)oxy)phenoxy)methyl)nicotinonitrile, 5-((5-((3-bromo-2-methylbenzyl)oxy)-2-formylphenoxy)methyl) nicotinonitrile (460 mg, 1.1 mmol), [1,1'-Bis(diphenylphosphino)ferrocene]dichloropalladium(II) ((81 mg, 0.11 mmol, 10 mol %), potassium carbonate (304 mg, 2.2 mmol, 2.0 equiv), N,N-dimethylformamide (11.0 mL, 0.1M), and water (1.1 mL) at room temperature. The vessel was sealed, and the mixture was sparged with nitrogen for 5 minutes before being heated to 90° C. for 1 hours. The reaction mixture was then cooled to room temperature, ethyl acetate (10 mL) was added, and the contents of the vial were filtered through celite. The filtrate was diluted with ethyl acetate (50 mL) and washed once with water then brine. The organic layer was then dried over magnesium sulfate, filtered, and concentrated under vacuum. The crude material was purified by silica gel column chromatography using a 0-10% methanol in methylene chloride eluent gradient to provide 5,5'-((((((2,2'-dimethyl-[1,1'-biphenyl]-3,3'-diyl)bis(methylene))bis(oxy))bis(6-formyl-3,1-phenylene))bis(oxy))bis(methylene))dinicotinonitrile.

To a 20 mL vial was added 5,5'-((((((2,2'-dimethyl-[1,1'-biphenyl]-3,3'-diyl)bis(methylene))bis(oxy))bis(6-formyl-3,1-phenylene))bis(oxy))bis(methylene))dinicotinonitrile (432 mg, 0.61 mmol), potassium acetate (180 mg, 1.8 mmol, 3.0 equiv), and acetic acid (4.0 mL, 0.15 M) at room temperature. To the mixture was added bromine (1.3 mL, 1M in acetic acid, 1.3 mmol, 2.2 equiv) dropwise. After 1 hour, 1M aqueous sodium sulfite was added until the red color disappeared. To this mixture was added 5N aqueous sodium hydroxide until pH=7. Finally, ethyl acetate (10 mL) and water (10 mL) were added, and the organic layer was washed once with brine, dried over magnesium sulfate, filtered, and concentrated under vacuum. The crude residue of 5,5'-((((((2,2'-dimethyl-[1,1'-biphenyl]-3,3'-diyl)bis(methylene))bis(oxy))bis(4-bromo-6-formyl-3,1-phenylene))bis(oxy))bis(methylene))dinicotinonitrile was used without further purification.

Intermediate 24: 6,6'-(((2,2'-dimethyl-[1,1'-biphenyl]-3,3'-diyl)bis(methylene))bis(oxy))bis(5-bromo-2-hydroxynicotinaldehyde)

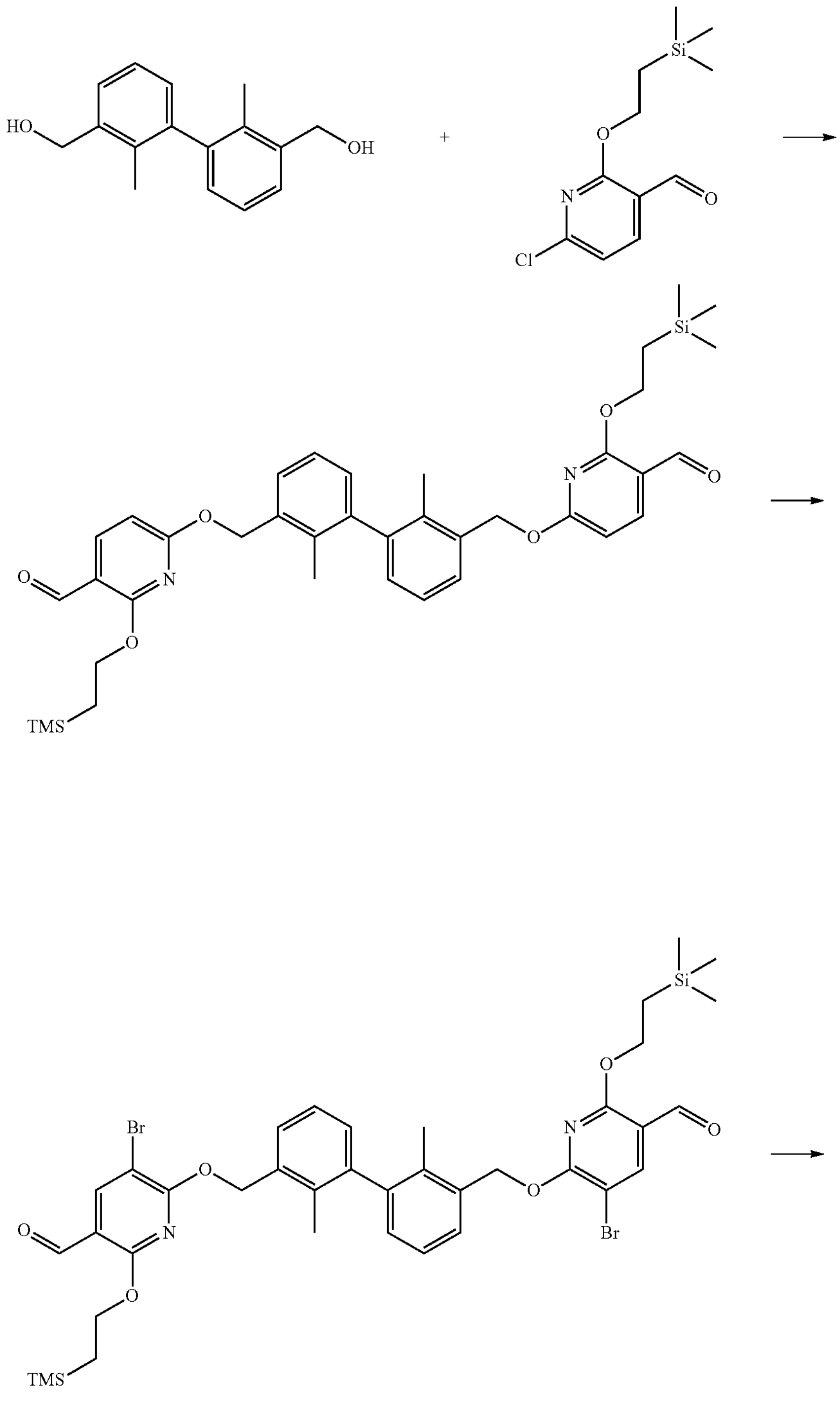

-continued

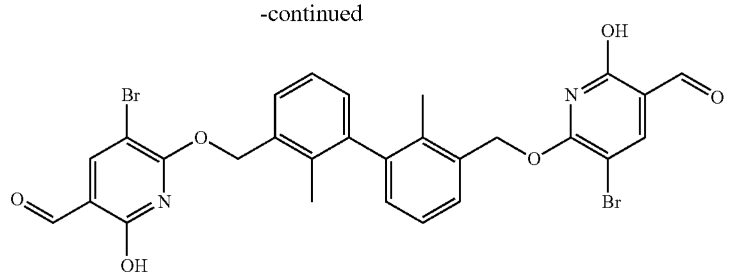

(2,2'-dimethyl-[1,1'-biphenyl]-3,3'-diyl)dimethanol (969 mg, 4 mmol), 6-chloro-2-(2-(trimethylsilyl)ethoxy)nicotinaldehyde (2.37 g, 9.2 mmol), 2-Di-tert-butylphosphino-2',4',6'-triisopropylbiphenyl (424.65 mg, 1 mmol), palladium (II) acetate (179.2 mg, 0.8 mmol), and cesium carbonate (5.2 g, 16 mmol) were charged into a 150 mL sealed tube. The contents were suspended in toluene (28 mL) and sparged with argon for 15 minutes. The tube was sealed, and heated to 90° C. After 3 h, the solution was cooled to room temperature, and filtered through a pad of celite. The celite pad was rinsed thoroughly with methylene chloride, and the filtrate was concentrated and purified via column chromatography to provide 6,6'-(((2,2'-dimethyl-[1,1'-biphenyl]-3,3'-diyl)bis(methylene))bis(oxy))bis(2-(2-(trimethylsilyl)ethoxy)nicotinaldehyde) as a solid (2.3 g 85%). $^1$H NMR (400 MHz, DMSO-$d_6$) δ 10.08 (d, J=0.9 Hz, 2H), 8.01 (d, J=8.4 Hz, 2H), 7.47-7.33 (m, 2H), 7.25 (t, J=7.6 Hz, 2H), 7.06 (dd, J=7.6, 1.4 Hz, 2H), 6.57 (dd, J=8.3, 0.8 Hz, 2H), 5.53 (s, 4H), 4.71-4.40 (m, 4H), 1.98 (s, 6H), 1.28-0.97 (m, 4H), 0.02 (s, 18H).

6,6'-(((2,2'-Dimethyl-[1,1'-biphenyl]-3,3'-diyl)bis(methylene))bis(oxy))bis(2-(2-(trimethylsilyl)ethoxy)nicotinaldehyde) (2.3 g, 3.39 mmol), and sodium acetate (694 mg, 8.47 mmol) was suspended in 15 mL acetic acid, and the resulting suspension was sonicated for 5 min. Bromine (0.44 mL, 8.47 mmol) was diluted in acetic acid (2 mL) and the resulting solution was added dropwise to the stirring dialdehyde. After 40 min, the reaction was diluted with methylene chloride (100 mL) and aqueous 2M NaOH (150 mL). After stirring for 10 min, the organic layer was separated, and the aqueous extracted with methylene chloride (75 mL). The combined organic layers were dried, concentrated, and purified via column chromatography to provide 6,6'-(((2,2'-dimethyl-[1,1'-biphenyl]-3,3'-diyl)bis(methylene))bis(oxy))bis(5-bromo-2-(2-(trimethylsilyl)ethoxy)nicotinaldehyde) (2.5 g, 88%) as a solid. $^1$H NMR (400 MHz, Chloroform-d) δ 10.15 (s, 2H), 8.24 (s, 2H), 7.54-7.35 (m, 2H), 7.29-7.24 (m, 2H), 7.14 (dd, J=7.7, 1.4 Hz, 2H), 5.55 (s, 4H), 4.65-4.39 (m, 4H), 2.10 (s, 6H), 1.24-1.14 (m, 4H), 0.09 (s, 18H).

6,6'-(((2,2'-Dimethyl-[1,1'-biphenyl]-3,3'-diyl)bis(methylene))bis(oxy))bis(5-bromo-2-(2-(trimethylsilyl)ethoxy)nicotinaldehyde) (1.25 g, 1.48 mmol) and cesium fluoride (0.9 g, 5.93 mmol) were suspended in N,N-dimethylformamide (10 mL). The suspension was heated to 60° C. for 1.5 h. The reaction was diluted with sat. aqueous ammonium chloride, brine, and extracted with ethyl acetate (2×). The combined organics were dried over anhydrous sodium sulfate, and concentrated to provide 0.9 g (94.5%) of 6,6'-(((2,2'-dimethyl-[1,1'-biphenyl]-3,3'-diyl)bis(methylene))bis(oxy))bis(5-bromo-2-hydroxynicotinaldehyde) as a powder. $^1$H NMR (400 MHz, DMSO-$d_6$) δ 12.50 (s, 2H), 9.98 (s, 2H), 8.12 (s, 2H), 7.53 (dd, J=7.8, 1.4 Hz, 2H), 7.29 (t, J=7.6 Hz, 2H), 7.10 (dd, J=7.8, 1.4 Hz, 2H), 5.53 (s, 4H), 2.01 (s, 6H).

Intermediate 25: 6,6'-(((2,2'-dimethyl-[1,1'-biphenyl]-3,3'-diyl)bis(methylene))bis(oxy))bis(5-bromo-2-methoxynicotinaldehyde)

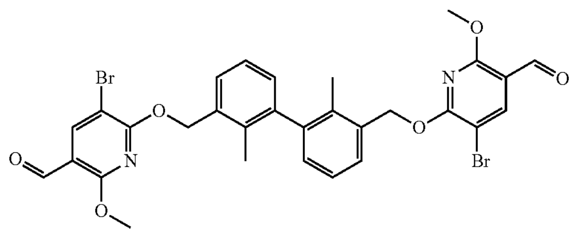 [SMILES: COc1nc(OCc2cccc(-c3cccc(COc4nc(OC)c(C=O)cc4Br)c3C)c2C)c(Br)cc1C=O]

6,6'-(((2,2'-dimethyl-[1,1'-biphenyl]-3,3'-diyl)bis(methylene))bis(oxy))bis(5-bromo-2-methoxynicotinaldehyde) was obtained from 6,6'-(((2,2'-dimethyl-[1,1'-biphenyl]-3,3'-diyl)bis(methylene))bis(oxy))bis(2-methoxynicotinaldehyde) using the same bromination procedure as described for Intermediate 24.

Intermediate 26: 5-((4-chloro-2-formyl-5-((3'-((4-formylphenoxy)methyl)-2,2'-dimethyl-[1,1'-biphenyl]-3-yl)methoxy)phenoxy)methyl)nicotinonitrile

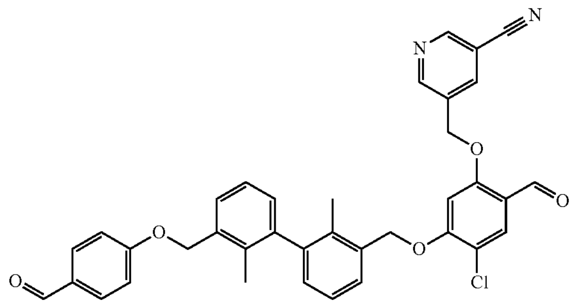 [SMILES: Cc1c(COc2ccc(C=O)cc2)cccc1-c1cccc(COc2cc(OCc3cncc(C#N)c3)c(C=O)cc2Cl)c1C]

The title compound was prepared following a similar procedure used to synthesize intermediate 11 and 12 using 1 equivalent of 5-chloro-2,4-dihydroxybenzaldehyde followed by 4-hydroxybenzaldehyde.

Intermediate 27: 3,3'-bis(((5-formyl-6-methoxypyridin-2-yl)oxy)methyl)-2'-methyl-[1,1'-biphenyl]-2-carbonitrile

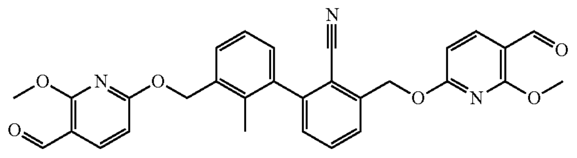

A mixture of (2-methyl-3-(4,4,5,5-tetramethyl-1,3,2-dioxaborolan-2-yl)phenyl)methanol (399 mg, 1.6 mmol), 2-bromo-6-(hydroxymethyl)benzonitrile (310 mg, 1.46 mmol), and Pd(dppf)$Cl_2$ (88 mg) in a mixture of DMF and water 2:15 mL was treated with $K_2CO_3$ (172 mg, 0.002 mol). The mixture was heated at 85° C. for 2 hrs. Mixture was diluted with EtOAc and water. Organic phase was dried over $Mg_2SO_4$ and evaporated under reduced pressure to afford 3,3'-bis(hydroxymethyl)-2'-methyl-[1,1'-biphenyl]-2-carbonitrile.

A mixture of 3,3'-bis(hydroxymethyl)-2'-methyl-[1,1'-biphenyl]-2-carbonitrile (150 mg, 0.59 mmol), 6-chloro-2-methoxynicotinaldehyde (223 mg, 1.3 mmol), $Pd(OAc)_2$ (25 mg, 0.237 mmol), t-Butyl-X-Phos (100 mg, 0.237 mmol) and $Cs_2CO_3$ (771 mg, 2.37 mmol) in toluene 9 mL was heated under stirring conditions at 85 C for 18 hrs. The residue was purified by column chromatography (Hexanes: Ethyl acetate=2:1) to give the title intermediate 3,3'-bis(((5-formyl-6-methoxypyridin-2-yl)oxy)methyl)-2'-methyl-[1,1'-biphenyl]-2-carbonitrile.

Intermediate 28: Tert-Butyl(S)-((2-methoxy-6-((4-(2-methyl-4'-(2-oxoethoxy)-[1,1'-biphenyl]-3-yl)-2,3-dihydro-1H-inden-1-yl)oxy)pyridin-3-yl)methyl) glycinate

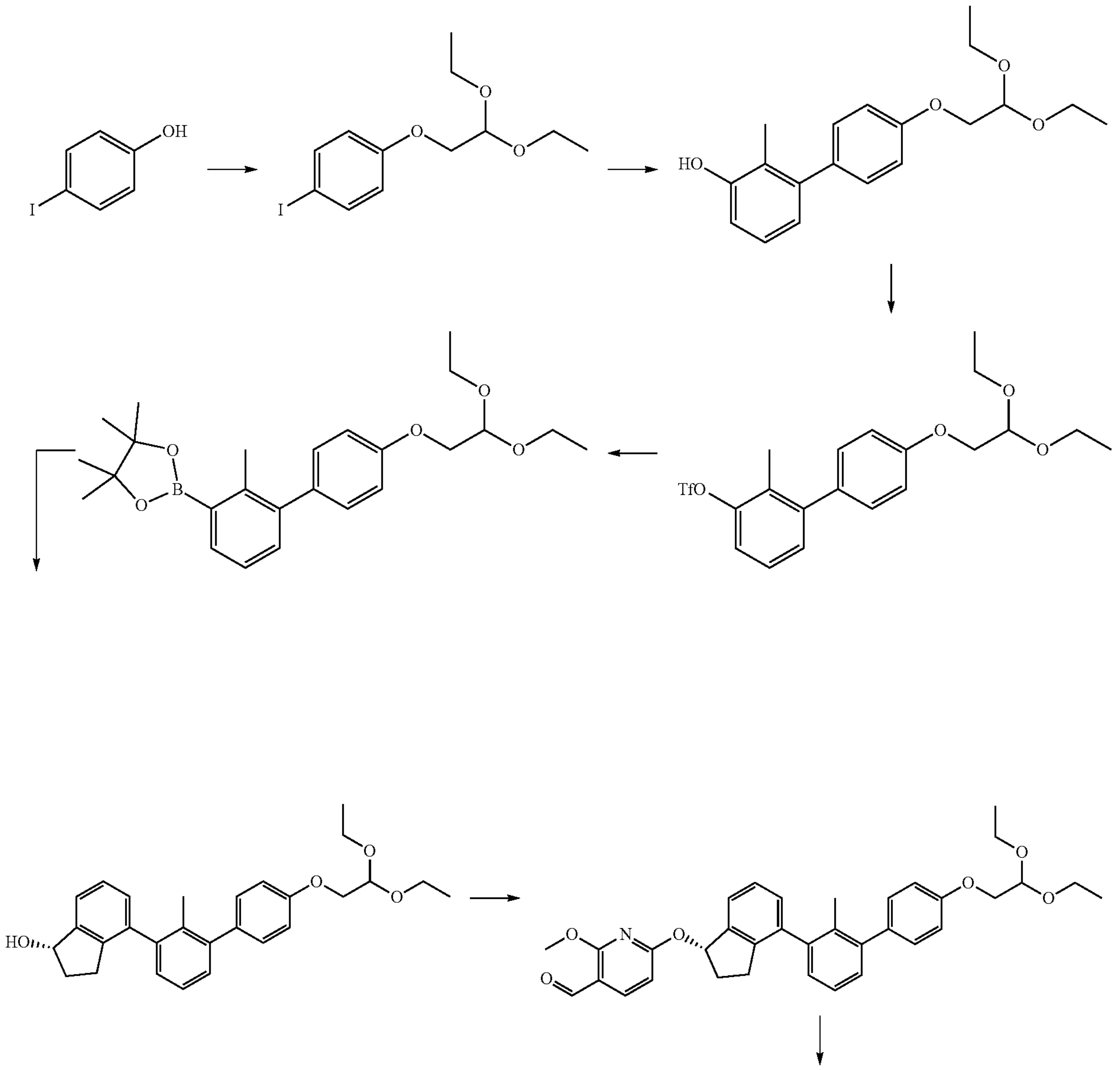

-continued

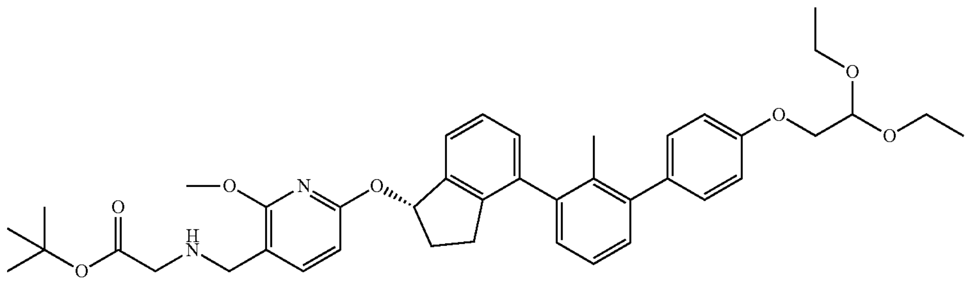

Step 1. A stirred mixture of 4-iodophenol (5.0 g, 23 mmol), 2-bromo-1,1-diethoxyethane (4.45 mL, 29.5 mmol), potassium carbonate (4.71 g, 34.1 mmol), and potassium iodide (1.89 g, 11.4 mmol) in N,N-dimethylformamide (30 mL) was heated to 109° C. After 15 h, the resulting mixture was allowed to cool to room temperature. Diethyl ether (500 mL) was added, and the organic layer was washed with water (3×500 mL), was dried over anhydrous magnesium sulfate, was filtered, and was concentrated under reduced pressure. The residue was purified by flash column chromatography (0 to 10% ethyl acetate in hexanes) to give 1-(2,2-diethoxyethoxy)-4-iodobenzene.

Step 2. A stirred mixture of 3-bromo-2-methylphenol (8.17 g, 43.7 mmol), 4,4,4',4',5,5,5',5'-octamethyl-2,2'-bi(1,3,2-dioxaborolane) (11.1 g, 43.7 mmol), potassium acetate (12.9 g, 131 mmol), and [1,1'-bis(diphenylphosphino)ferrocene]dichloropalladium(II) (640 mg, 0.87 mmol) in dioxane (80 mL) was heated to 110° C. After 3 h, 1-(2,2-diethoxyethoxy)-4-iodobenzene, aqueous sodium carbonate solution (2 M, 68 mL, 140 mmol), and [1,1'-bis(diphenylphosphino)ferrocene]dichloropalladium(II) (640 mg, 0.87 mmol) were added. After 18 h, the reaction mixture was allowed to cool to room temperature and ethyl acetate (500 mL) was added. The organic layer was washed with a mixture of water and brine (1:1 v:v, 300 mL), was dried over anhydrous sodium sulfate, was filtered, and was concentrated under reduced pressure. The residue was purified by flash column chromatography (0 to 30% ethyl acetate in hexanes) to give 4'-(2,2-diethoxyethoxy)-2-methyl-[1,1'-biphenyl]-3-ol.

Step 3. Trifluoromethanesulfonic anhydride (0.798 mL, 4.74 mmol) was added via syringe to a stirred mixture of 4'-(2,2-diethoxyethoxy)-2-methyl-[1,1'-biphenyl]-3-ol (1.00 g, 3.16 mmol) and N,N-diisopropylethylamine (1.38 mL, 7.90 mmol) in dichloromethane (10 mL) at 0° C. After 30 min, ethanol (0.5 mL) was added. After 5 min, the reaction mixture was concentrated under reduced pressure. The residue was purified by flash column chromatography (0 to 10% ethyl acetate in hexanes) to give 4'-(2,2-diethoxyethoxy)-2-methyl-[1,1'-biphenyl]-3-yl trifluoromethanesulfonate.

Step 4. A stirred mixture of 4'-(2,2-diethoxyethoxy)-2-methyl-[1,1'-biphenyl]-3-y trifluoromethanesulfonate (1.06 g, 2.370 mmol), 4,4,4',4',5,5,5',5'-octamethyl-2,2'-bi(1,3,2-dioxaborolane) (722 mg, 2.84 mmol), potassium acetate (744 mg, 7.59 mmol), and [1,1'-bis(diphenylphosphino)ferrocene]dichloropalladium(II) (173 mg, 0.237 mmol) in dioxane (8.0 mL) was heated to 95° C. After 17 h, the resulting mixture was allowed to cool to room temperature, was filtered through celite, and was concentrated under reduced pressure. The residue was purified by flash column chromatography (0 to 10% ethyl acetate in hexanes) to give 2-(4'-(2,2-diethoxyethoxy)-2-methyl-[1,1'-biphenyl]-3-yl)-4,4,5,5-tetramethyl-1,3,2-dioxaborolane.

Step 5. A stirred mixture of 2-(4'-(2,2-diethoxyethoxy)-2-methyl-[1,1'-biphenyl]-3-yl)-4,4,5,5-tetramethyl-1,3,2-dioxaborolane (785 mg, 1.84 mmol), (S)-4-bromo-2,3-dihydro-1H-inden-1-ol (432 mg, 2.03 mmol), aqueous sodium carbonate solution (2 M, 3.7 mL, 7 mmol), and chloro(2-dicyclohexylphosphino-2',4',6'-triisopropyl-1,1'-biphenyl)[2-(2'-amino-1,1'-biphenyl)]palladium(II) (73 mg, 0.092 mmol) in dioxane (8.0 mL) and water (0.5 mL) was heated to 200° C. After 15 h, the resulting mixture was allowed to cool to room temperature, was filtered through celite, and the filter cake was extracted with ethyl acetate (60 mL). The organic layer was washed with a mixture of water and brine (1:1 v:v, 50 mL), was dried over anhydrous sodium sulfate, and was concentrated under reduced pressure. The residue was purified by flash column chromatography (0 to 50% ethyl acetate in hexanes) to give (S)-4-(4'-(2,2-diethoxyethoxy)-2-methyl-[1,1'-biphenyl]-3-yl)-2,3-dihydro-1H-inden-1-ol.

Step 6. A stirred mixture of (S)-4-(4'-(2,2-diethoxyethoxy)-2-methyl-[1,1'-biphenyl]-3-yl)-2,3-dihydro-1H-inden-1-ol (797 mg, 1.84 mmol), 6-chloro-2-methoxynicotinaldehyde (442 mg, 2.58 mmol), cesium carbonate (1.08 g, 3.32 mmol), and [(2-di-tert-butylphosphino-2',4',6'-triisopropyl-1,1'-biphenyl)-2-(2'-amino-1,1'-biphenyl)] palladium(II) methanesulfonate (73 mg, 0.092 mmol) in toluene (8.0 mL) was heated to 200° C. After 15 h, the resulting mixture was allowed to cool to room temperature, was filtered through celite, and was concentrated under reduced pressure. The residue was purified by flash column chromatography (0 to 40% ethyl acetate in hexanes) to give (S)-6-((4-(4'-(2,2-diethoxyethoxy)-2-methyl-[1,1'-biphenyl]-3-yl)-2,3-dihydro-1H-inden-1-yl)oxy)-2-methoxynicotinaldehyde.

Step 7. N,N-Diisopropylethylamine (0.77 mL, 4.4 mmol) was added via syringe to a stirred mixture of (S)-6-((4-(4'-(2,2-diethoxyethoxy)-2-methyl-[1,1'-biphenyl]-3-yl)-2,3-dihydro-1H-inden-1-yl)oxy)-2-methoxynicotinaldehyde (250 mg, 0.44 mmol) and tert-butyl glycinate hydrochloride (591 mg, 3.52 mmol) in N,N-dimethylformamide (3.0 mL) at room temperature. After 23 min, acetic acid (0.3 mL), sodium cyanoborohydride (221 mg, 3.52 mmol), and sodium triacetoxyborohydride (747 mg, 3.52 mmol) were added sequentially. After 10 min, the reaction mixture was purified by reverse phase preparative HPLC (0.1% trifluoroacetic acid in acetonitrile/water) to give tert-butyl (S)-((6-((4-(4'-(2,2-diethoxyethoxy)-2-methyl-[1,1'-biphenyl]-3-yl)-2,3-dihydro-1H-inden-1-yl)oxy)-2-methoxypyridin-3-yl)methyl)glycinate.

Intermediate 29: 5-((4-chloro-5-((2,2'-dimethyl-3"-nitro-4"-(2-oxoethoxy)-[1,1':3',1"-terphenyl]-3-yl)methoxy)-2-formylphenoxy)methyl)nicotinonitrile

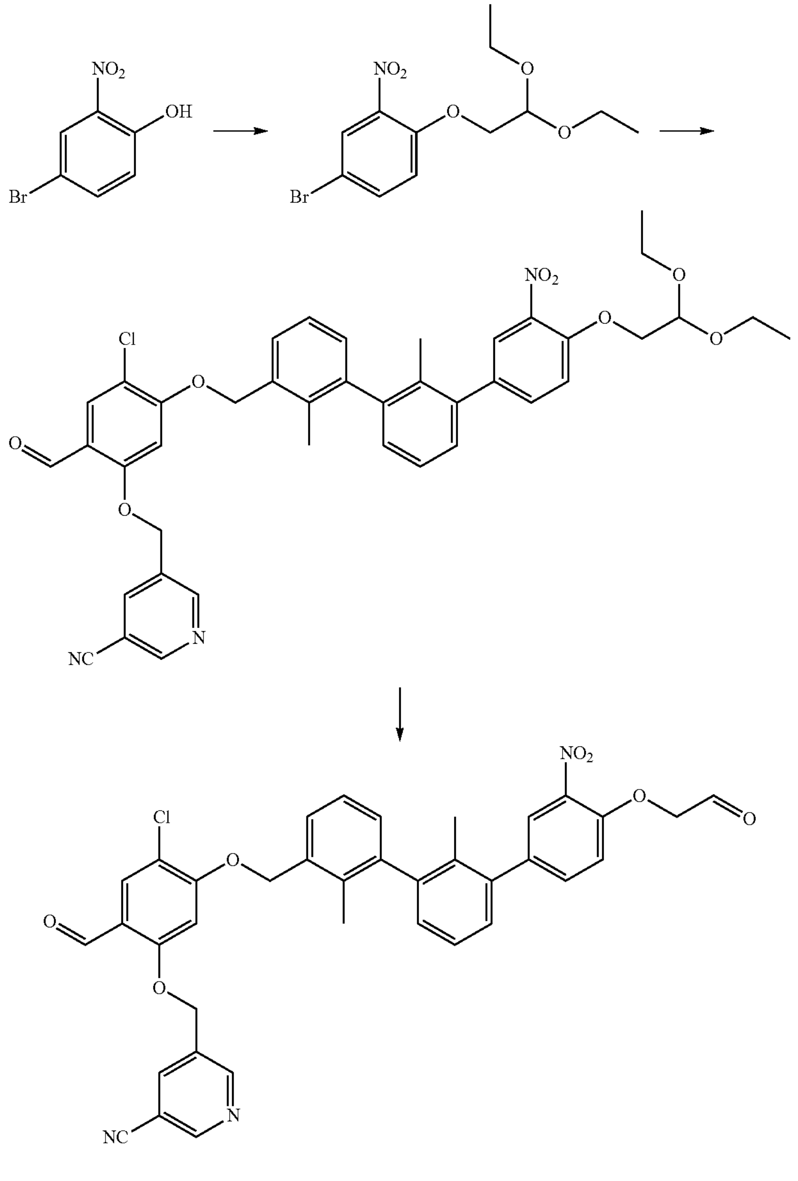

Step 1. A stirred mixture of 4-bromo-2-nitrophenol (1.00 g, 4.59 mmol), 2-bromo-1,1-diethoxyethane (1.04 mL, 6.88 mmol), potassium carbonate (1.27 g, 9.17 mmol), and potassium iodide (152 mg, 0.917 mmol) in 1-methylpyrrolidin-2-one (7.0 mL) was heated to 100° C. After 18 h, the resulting mixture was allowed to cool to room temperature. Diethyl ether (150 mL) was added, and the organic layer was washed with water (2×100 mL), was dried over anhydrous magnesium sulfate, was filtered, and was concentrated under reduced pressure. The residue was purified by flash column chromatography (0 to 15% ethyl acetate in hexanes) to give 4-bromo-1-(2,2-diethoxyethoxy)-2-nitrobenzene.

Step 2. A stirred mixture of 4-bromo-1-(2,2-diethoxyethoxy)-2-nitrobenzene (123 mg, 0.370 mmol), 5-((4-chloro-5-((2,2'-dimethyl-3'-(4,4,5,5-tetramethyl-1,3,2-dioxaborolan-2-yl)-[1,1'-biphenyl]-3-yl)methoxy)-2-formylphenoxy)methyl)nicotinonitrile (150 mg, 0.246 mmol), aqueous sodium carbonate solution (2 M, 0.49 mL, 1 mmol), and chloro(2-dicyclohexylphosphino-2',4',6'-triisopropyl-1,1'-biphenyl)[2-(2'-amino-1,1'-biphenyl)]palladium(II) (9.7 mg, 0.012 mmol) in dioxane (2.0 mL) and water (0.5 mL) was heated to 91° C. After 14 h, the reaction mixture was allowed to cool to room temperature and ethyl acetate (60 mL) was added. The organic layer was washed with a mixture of water and brine (1:1 v:v, 30 mL), was dried over anhydrous sodium sulfate, was filtered, and was concentrated under reduced pressure. The residue was purified by flash column chromatography (0 to 70% ethyl acetate in hexanes) to give 5-((4-chloro-5-((4"-(2,2-diethoxyethoxy)-2,2'-dimethyl-3"-nitro-[1,1':3',1"-terphenyl]-3-yl)methoxy)-2-formylphenoxy)methyl)nicotinonitrile.

Step 3. Concentrated hydrochloric acid (0.25 mL) was added to a stirred solution of 5-((4-chloro-5-((4"-(2,2-diethoxyethoxy)-2,2'-dimethyl-3"-nitro-[1,1':3',1"-terphenyl]-3-yl)methoxy)-2-formylphenoxy)methyl)nicotinonitrile (181 mg, 0.246 mmol) in dioxane (3.0 mL) at room temperature. After 60 min, ethyl acetate (60 mL) and saturated aqueous sodium bicarbonate solution (5.0 mL) were added sequentially. The organic layer was washed with brine (30 mL), was dried over anhydrous sodium sulfate, was filtered, and was concentrated under reduced pressure to give 5-((4-chloro-5-((2,2'-dimethyl-3"-nitro-4"-(2-oxoethoxy)-[1,1':3',1"-terphenyl]-3-yl)methoxy)-2-formylphenoxy)methyl)nicotinonitrile, which was used without further purification.

Intermediate 30: 5-((4-chloro-5-((2,2'-dimethyl-4"-(2-oxoethoxy)-3"-(trifluoromethyl)-[1,1':3',1"-terphenyl]-3-yl)methoxy)-2-formylphenoxy)methyl)nicotinonitrile

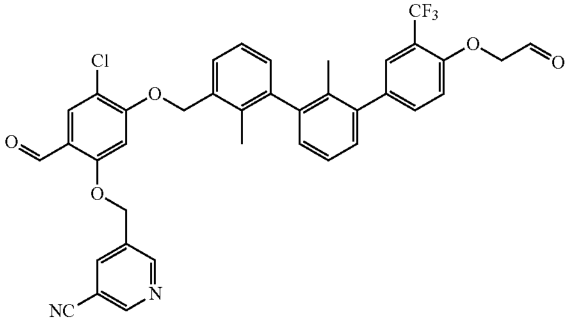 [SMILES: Cc1c(COc2cc(OCc3cncc(C#N)c3)c(C=O)cc2Cl)cccc1-c1cccc(-c2ccc(OCC=O)c(C(F)(F)F)c2)c1C]

5-((4-chloro-5-((2,2'-dimethyl-4"-(2-oxoethoxy)-3"-(trifluoromethyl)-[1,1':3',1"-terphenyl]-3-yl)methoxy)-2-formylphenoxy)methyl)nicotinonitrile was synthesized in a manner similar to 5-((4-chloro-5-((2,2'-dimethyl-3"-nitro-4"-(2-oxoethoxy)-[1,1':3',1"-terphenyl]-3-yl)methoxy)-2-formylphenoxy)methyl)nicotinonitrile using 4-bromo-2-(trifluoromethyl)phenol in place of 4-bromo-2-nitrophenol.

Intermediate 31: 3-carboxy-3,3-difluoro-2-hydroxypropan-1-aminium 2,2,2-trifluoroacetate

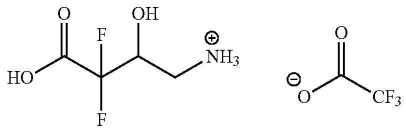 [SMILES: [NH3+]CC(O)C(F)(F)C(=O)O ; O=C([O-])C(F)(F)F]

Aqueous sodium hydroxide solution (1 M, 10 mL, 10 mmol) was added via syringe to a stirred solution of ethyl 4-((tert-butoxycarbonyl)amino)-2,2-difluoro-3-hydroxybutanoate (1.44 g, 5.08 mmol) in tetrahydrofuran (10 mL) and methanol (20 mL) at room temperature. After 20 min, diethyl ether (140 mL) was added, and the organic layer was washed with a mixture of 0.5 M aqueous hydrogen chloride solution and brine (1:2 v:v, 60 mL), was dried over magnesium sulfate, was filtered, and was concentrated under reduced pressure. The residue was dissolved in dichloromethane (10 mL), and the resulting mixture was stirred at room temperature. Trifluoroacetic acid (5 mL) was added. After 2.5 h, the reaction mixture was concentrated under reduced pressure and dried azeotropically by concentration of a toluene solution under reduced pressure (3×20 mL) to give 3-carboxy-3,3-difluoro-2-hydroxypropan-1-aminium 2,2,2-trifluoroacetate.

Intermediate 32: 6,6'-(((2,2'-dimethyl-[1,1'-biphenyl]-3,3'-diyl)bis(methylene))bis(oxy))bis(5-chloro-2-hydroxynicotinaldehyde)

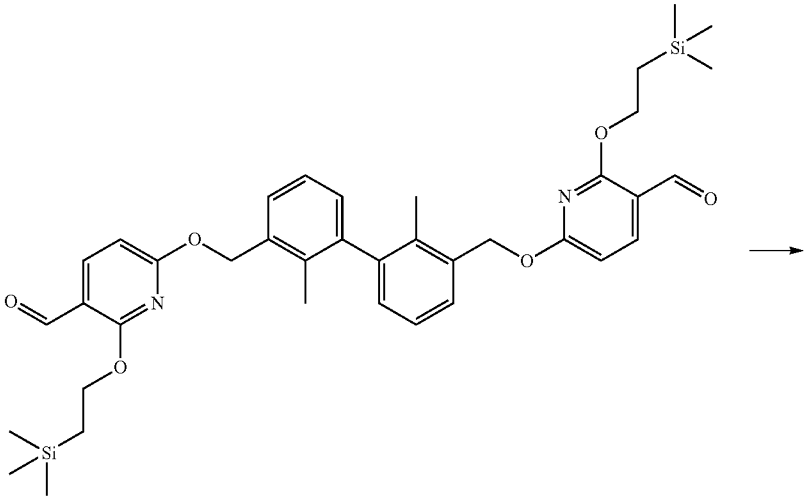

-continued

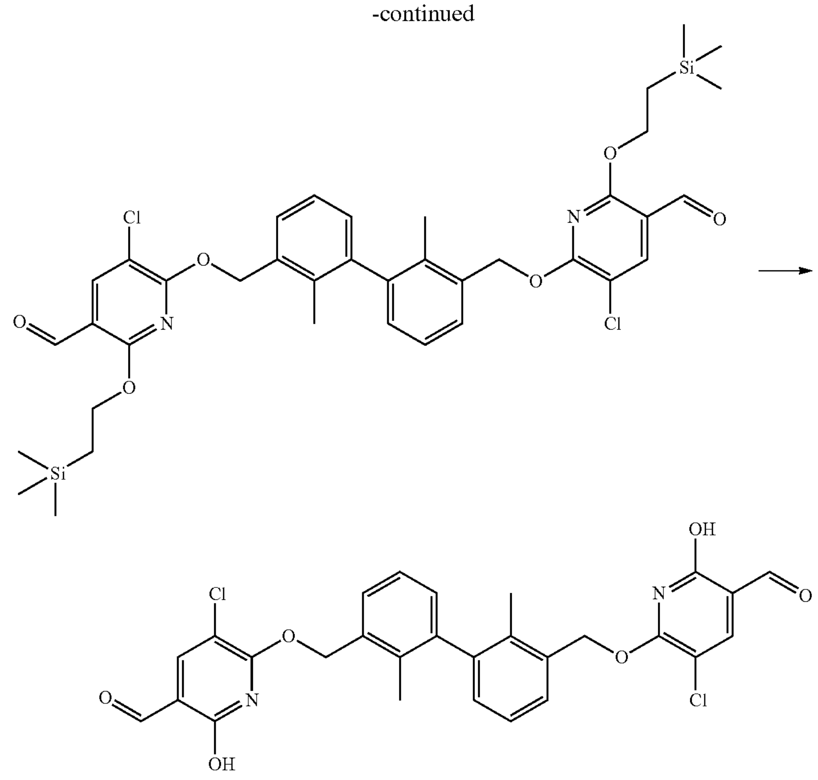

6,6'-(((2,2'-Dimethyl-[1,1'-biphenyl]-3,3'-diyl)bis(methylene))bis(oxy))bis(2-(2-(trimethylsilyl)ethoxy)nicotinaldehyde) (1.8 g, 2.65 mmol), and 2-chloro-1,3-bis(methoxycarbonyl)guanidine (0.19 g, 5.7 mmol) were dissolved in a 1:1 mixture of chloroform and N,N-dimethylformamide (80 mL). 4M HCl in dioxane (1.46 mL, 5.8 mmol) was added dropwise to the stirring solution. After 30 min, the reaction was diluted with methylene chloride (100 mL), and washed with sat. aqueous sodium bicarbonate, and brine. The organic layer was dried over anhydrous sodium sulfate, concentrated, and purified via column chromatography to provide 6,6'-(((2,2'-dimethyl-[1,1'-biphenyl]-3,3'-diyl)bis(methylene))bis(oxy))bis(5-chloro-2-(2-(trimethylsilyl)ethoxy)nicotinaldehyde). $^1$H NMR (400 MHz, Chloroform-d) δ 10.16 (s, 2H), 8.07 (s, 2H), 7.48-7.43 (m, 2H), 7.28-7.21 (m, 2H), 7.13 (dd, J=7.6, 1.4 Hz, 2H), 5.55 (s, 4H), 4.60-4.53 (m, 4H), 2.08 (s, 6H), 1.22-1.16 (m, 4H), 0.07 (s, 18H).

6,6'-(((2,2'-Dimethyl-[1,1'-biphenyl]-3,3'-diyl)bis(methylene))bis(oxy))bis(5-chloro-2-(2-(trimethylsilyl)ethoxy)nicotinaldehyde) (0.90 g, 1.2 mmol) and cesium fluoride (0.73 g, 4.8 mmol) were suspended in N,N-dimethylformamide (8 mL). The suspension was heated to 60° C. for 1.5 h. The reaction was diluted with sat. aqueous ammonium chloride, brine, and extracted with ethyl acetate (2×). The combined organics were dried over anhydrous sodium sulfate, and concentrated to provide 6,6'-(((2,2'-dimethyl-[1,1'-biphenyl]-3,3'-diyl)bis(methylene))bis(oxy))bis(5-chloro-2-hydroxynicotinaldehyde). $^1$H NMR (400 MHz, DMSO-$d_6$) δ 12.48 (s, 2H), 10.00 (s, 2H), 8.01 (s, 2H), 7.52 (dd, J=7.8, 1.4 Hz, 2H), 7.29 (t, J=7.6 Hz, 2H), 7.10 (dd, J=7.6, 1.4 Hz, 2H), 5.55 (s, 4H), 2.01 (s, 6H).

Intermediate 33: (S)-4-amino-3-hydroxybutanamide

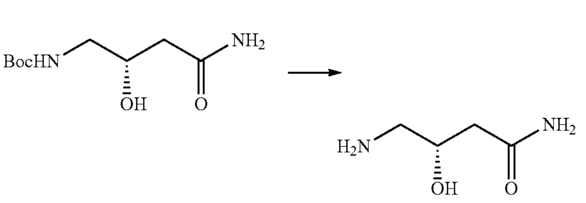

4N hydrogen chloride in 1,4-dioxane (7.4 mL, 7.34 mmol) was added to a solution of the tert-butyl (S)-(4-amino-2-hydroxy-4-oxobutyl)carbamate (811 mg, 3.72 mmol) in methanol-gas evolution. After 1h the solvent was removed under reduced pressure. The residue was co-evaporated with dichloromethane and the residue was subjected to high vacuum, providing (S)-4-amino-3-hydroxybutanamide (402 mg, 91%).

tert-butyl (S)-(4-amino-2-hydroxy-4-oxobutyl)carbamate was prepared following the procedure given in *J. Med. Chem.* 1985,28, 1612-1617.

Intermediate 34: Ethyl (R)-3-amino-2-fluoropropanoate Hydrochloride

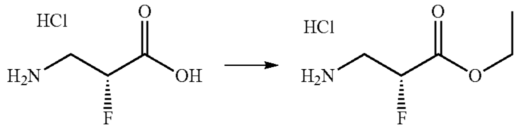

A solution of hydrogen chloride in 1,4-dioxane (4N, 8.8 mL, 35.3 mmol) was added to a solution of (R)-3-amino-2-fluoropropanoic acid hydrochloride (253 mg, 1.76 mmol) in ethanol (8 mL). After 2 hours the solvent was removed under reduced pressure. The residue was co-evaporated with dichloromethane (10 mL). The residue was subjected to high vacuum, providing ethyl (R)-3-amino-2-fluoropropanoate hydrochloride (311 mg, 103%).

Intermediate 35: 4,4'-([4,4'-biindoline]-1,1'-dicarbonyl)bis(2-methoxybenzaldehyde)

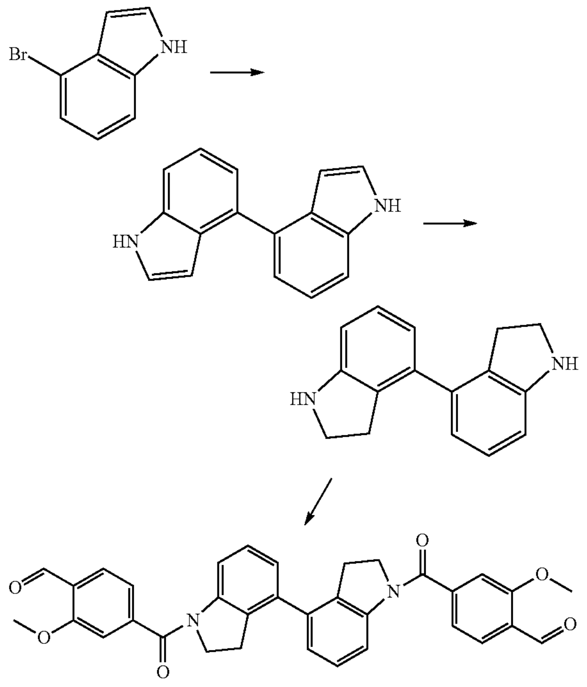

Step 1: In a microwave vial, 4-bromoindole (1.0 g, 5.1 mmol), Xphos (97.0 mg, 0.20 mmol) and $Pd_2(dba)_3$ (52.0 mg, 0.057 mmol) were dissolved in 80.00 mL of dioxane at room temperature. Vial was capped and purged with argon. To this vial, 4,4,5,5-tetramethyl-1,3,2-dioxoborolate (2.2 mL, 15.30 mmol) and trimethylamine (2.1 mL, 15.30 mmol) were added at room temperature. Mixture was stirred at 95° C. for 3 hours under argon. Vial was taken out of the heat and allowed to cold down to room temperature. To this microwave vial, were added 4-bromoindole (1.0 g, 5.1 mmol), $Pd_2(dba)_3$ (52.0 mg, 0.057 mmol), potassium phosphate hydrate (3.5 g, 15.20 mmol) and 8.00 mL of water at room temperature. Vial was capped and purged with argon. Mixture was stirred at 95° C. overnight. Vial was removed from heat and crude was diluted with ethyl acetate and filtered through celite. Then, organic layer was washed with brine and dried over magnesium sulfate. Volatiles were removed under reduced pressure and crude was dry-loaded to a silica column and eluted with 20%-60% ethyl acetate/hexanes to afford 4,4'-biindole.

Step 2: In a round bottom flask, 4,4'-biindole (1.0 g, 4.31 mmol) was dissolved in 30.00 mL of acetic acid at room temperature. To this solution 811.00 mg of sodium cyanoborohydride was added in portions over 20 minutes at room temperature. The mixture was stirred at room temperature for four hours. Crude was quenched with 2.OM NaOH and organic layer was extracted with ethyl acetate. Organic layer was dried over sodium sulfate. Volatiles were removed under reduced pressure and crude was dry-loaded to a silica gel column and eluted with 80-100% ethyl acetate/hexanes to afford 4,4'-biindoline.

Step 3: In a round bottom flask, 4-formyl-3-methoxybenzoic acid (97.00 mg, 0.54 mmol) was dissolved in 3.00 of THF at room temperature. Solution was cooled down to 0° C. and oxalyl chloride (0.10 mL, 1.08 mmol) was added dropwise followed by one drop of DMF. Gas evolution was observed. The mixture was warmed up to room temperature and stirred for 45 minutes. Volatiles were removed under reduced pressure and crude material was redissolved in 3.00 of THF. On a separate vial, 4,4'-biindoline (51.00 mg, 0.22 mmol) was dissolved in 2.00 mL of THF at room temperature. The 4,4'-biindoline solution was added to the crude material at room temperature followed by trimethylamine (0.15 mmol, 1.08 mmol). The mixture was stirred at room temperature for 90 minutes. Solution was quenched with saturated sodium bicarbonate and the organic layer was extracted with ethyl acetate. Organic layer was dried over sodium sulfate and volatiles were removed under reduced pressure. Crude was dry-loaded to a silica gel column and eluted with 20-100% ethyl acetate/hexanes to afford 4,4'-([4,4'-biindoline]-1,1'-dicarbonyl)bis(2-methoxybenzaldehyde).

Intermediate 36: 4,4'-([4,4'-biindoline]-1,1'-dicarbonyl)dibenzaldehyde

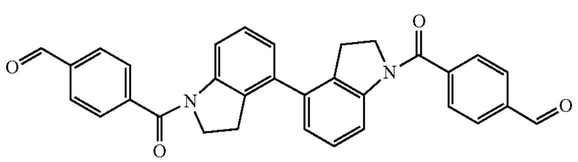 [SMILES: O=Cc1ccc(C(=O)N2CCc3c(-c4cccc5c4CCN5C(=O)c4ccc(C=O)cc4)cccc32)cc1]

4,4'-([4,4'-biindoline]-1,1'-dicarbonyl)dibenzaldehyde was obtained in similar fashion as shown for Intermediate 35, using 4-formylbenzoic acid instead of 4-formyl-3-methoxybenzoic acid.

Intermediate 37: 4,4'-(((2,2'-dimethyl-[1,1'-biphenyl]-3,3'-diyl)bis(methylene))bis(oxy))bis(3-(trifluoromethyl)benzaldehyde)

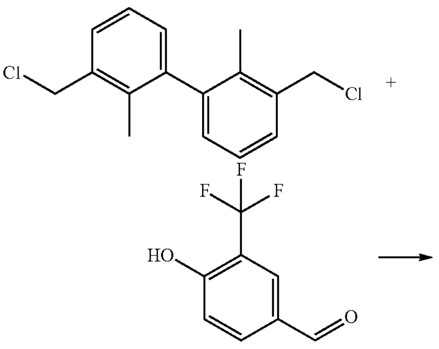

-continued

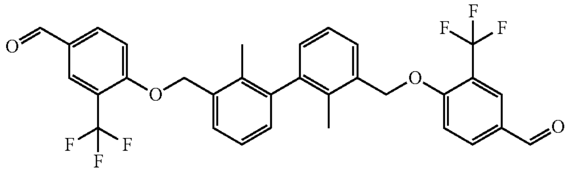

4,4'-(((2,2'-dimethyl-[1,1'-biphenyl]-3,3'-diyl)bis(methylene))bis(oxy))bis(3-(trifluoromethyl)benzaldehyde) was prepared analogous to Intermediate 11 starting from 4-hydroxy-3-(trifluoromethyl)benzaldehyde.

Intermediate 38: 5,5'-((((2,2'-dimethyl-[1,1'-biphenyl]-3,3'-diyl)bis(methylene))bis(oxy))bis(6-formyl-3,1-phenylene))dinicotinonitrile To a 20 mL vial was added 4-((3-bromo-2-methylbenzyl)oxy)-2-hydroxybenzaldehyde (300 mg, 0.94 mmol), 4,4,4',4',5,5,5',5'-octamethyl-2,2'-bi(1,3,2-dioxaborolane) (322 mg, 1.27 mmol, 1.35 equiv), [1,1'-Bis(diphenylphosphino)ferrocene]dichloropalladium(I) (69 mg, 0.09 mmol, 10 mol %), potassium acetate (184 mg, 1.88 mmol, 2.0 equiv), and 1,4-dioxane (9.4 mL, 0.1M) at room temperature. The vessel was sealed, and the mixture was sparged with nitrogen for 5 minutes before being heated to 90° C. for 3 hours. The reaction mixture was then cooled to room temperature, ethyl acetate (10 mL) was added, and the contents of the vial were filtered through celite. The filtrate was concentrated under vacuum, and the crude 2-hydroxy-4-((2-methyl-3-(4,4,5,5-tetramethyl-1,3,2-dioxaborolan-2-yl)benzyl)oxy)benzaldehyde was used without further purification.

To a 20 mL vial was added the crude 2-hydroxy-4-((2-methyl-3-(4,4,5,5-tetramethyl-1,3,2-dioxaborolan-2-yl)ben

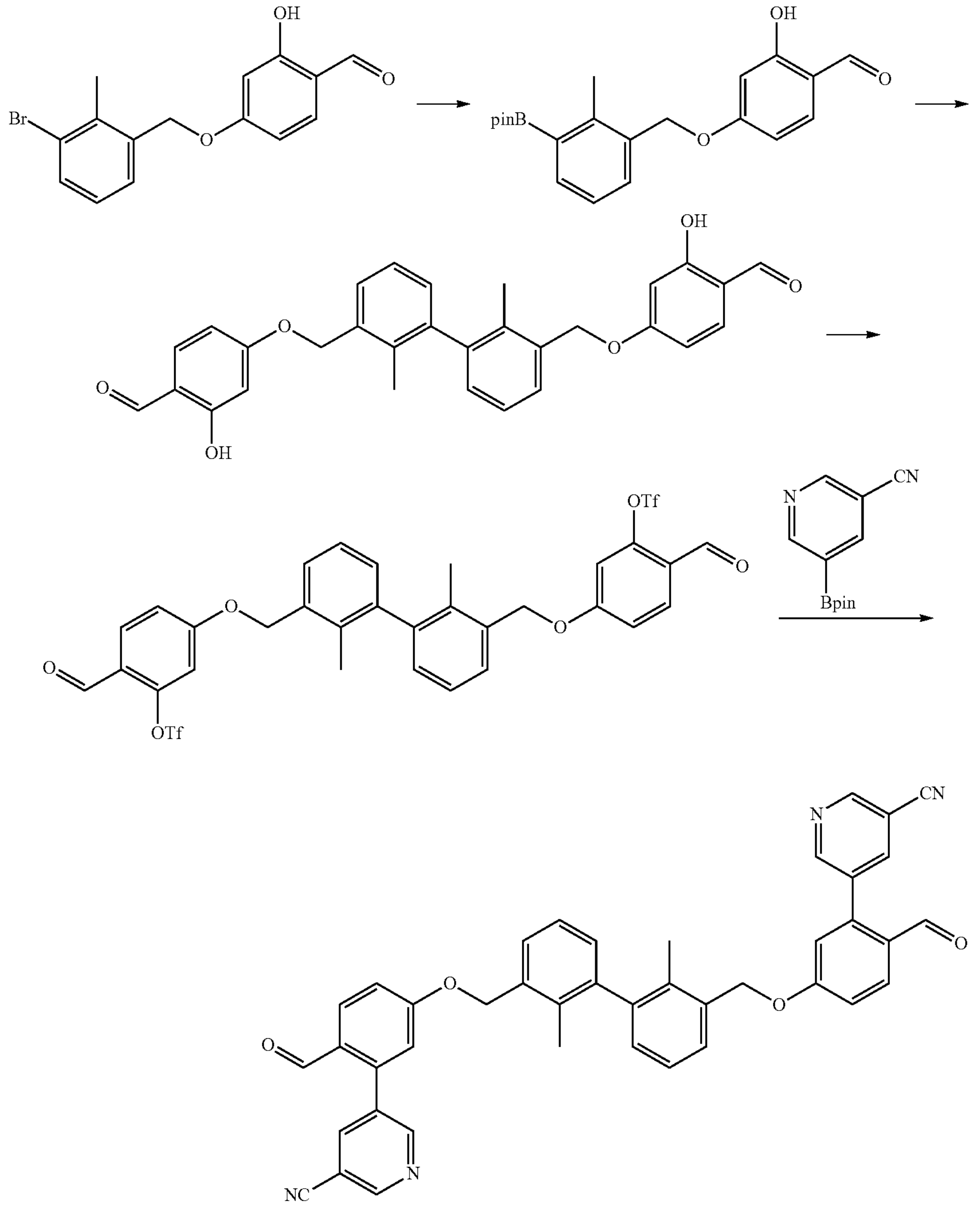

zyl)oxy)benzaldehyde, 4-((3-bromo-2-methylbenzyl)oxy)-2-hydroxybenzaldehyde (300 mg, 0.94 mmol, 1.0 equiv), [1,1'-Bis(diphenylphosphino)ferrocene]dichloropalladium (II) (69 mg, 0.09 mmol, 10 mol %), potassium carbonate (260 mg, 1.88 mmol, 2.0 equiv), N,N-dimethylformamide (9.4 mL, 0.1M), and water (0.9 mL) at room temperature. The vessel was sealed, and the mixture was sparged with nitrogen for 5 minutes before being heated to 90° C. for 1 hours. The reaction mixture was then cooled to room temperature, ethyl acetate (10 mL) was added, and the contents of the vial were filtered through celite. The filtrate was diluted with ethyl acetate (50 mL) and washed once with water and once with brine. The organic layer was then dried over magnesium sulfate, filtered, and concentrated under vacuum. The crude material was purified by silica gel column chromatography using a 0-10% methanol in methylene chloride eluent gradient to provide 4,4'-(((2,2'-dimethyl-[1,1'-biphenyl]-3,3'-diyl)bis(methylene))bis(oxy))bis(2-hydroxybenzaldehyde).

To a 20 mL vial was added 4,4'-(((2,2'-dimethyl-[1,1'-biphenyl]-3,3'-diyl)bis(methylene))bis(oxy))bis(2-hydroxybenzaldehyde) (250 mg, 0.52 mmol) and methylene chloride (5.2 mL, 0.1M) at room temperature under a nitrogen atmosphere. The vessel was cooled to 0° C., and triflic anhydride (0.19 mL, 1.14 mmol, 2.2 equiv) was added dropwise. The reaction mixture was stirred at 0° C. for 1 hour before slowly being warmed to room temperature. After 2 hours, the reaction mixture was diluted with methylene chloride (10 mL), and the contents of the vial were washed ×1 with saturated aqueous sodium bicarbonate, once with water, and once with brine. The organic layer was then dried over magnesium sulfate, filtered, and concentrated under vacuum. The crude material was purified by silica gel column chromatography using a 0-10% methanol in methylene chloride eluent gradient to provide (((2,2'-dimethyl-[1,1'-biphenyl]-3,3'-diyl)bis(methylene))bis(oxy))bis(6-formyl-3,1-phenylene) bis(trifluoromethanesulfonate).

To a 20 mL vial was added (((2,2'-dimethyl-[1,1'-biphenyl]-3,3'-diyl)bis(methylene))bis(oxy))bis(6-formyl-3,1-phenylene) bis(trifluoromethanesulfonate) (279 mg, 0.34 mmol), 5-(4,4,5,5-tetramethyl-1,3,2-dioxaborolan-2-yl)nicotinonitrile (188 mg, 0.82 mmol, 2.4 equiv), [1,1'-Bis(diphenylphosphino)ferrocene]dichloropalladium(II) (26 mg, 0.03 mmol, 10 mol %), potassium carbonate (113 mg, 0.82 mmol, 2.0 equiv), N,N-dimethylformamide (3.4 mL, 0.1M), and water (0.4 mL) at room temperature. The vessel was sealed, and the mixture was sparged with nitrogen for 5 minutes before being heated to 90° C. for 1 hour. The reaction mixture was then cooled to room temperature, ethyl acetate (10 mL) was added, and the contents of the vial were filtered through celite. The filtrate was diluted with ethyl acetate (50 mL) and washed once with water and once with brine. The organic layer was then dried over magnesium sulfate, filtered, and concentrated under vacuum. The crude material was purified by silica gel column chromatography using a 0-10% methanol in methylene chloride eluent gradient to provide 5,5'-((((2,2'-dimethyl-[1,1'-biphenyl]-3,3'-diyl)bis(methylene))bis(oxy))bis(6-formyl-3,1-phenylene))dinicotinonitrile.

Intermediate 39: 5,5'-(((([4,4'-biindoline]-1,1'-dicarbonyl)bis(6-formyl-3,1-phenylene))bis(oxy))bis(methylene))dinicotinonitrile

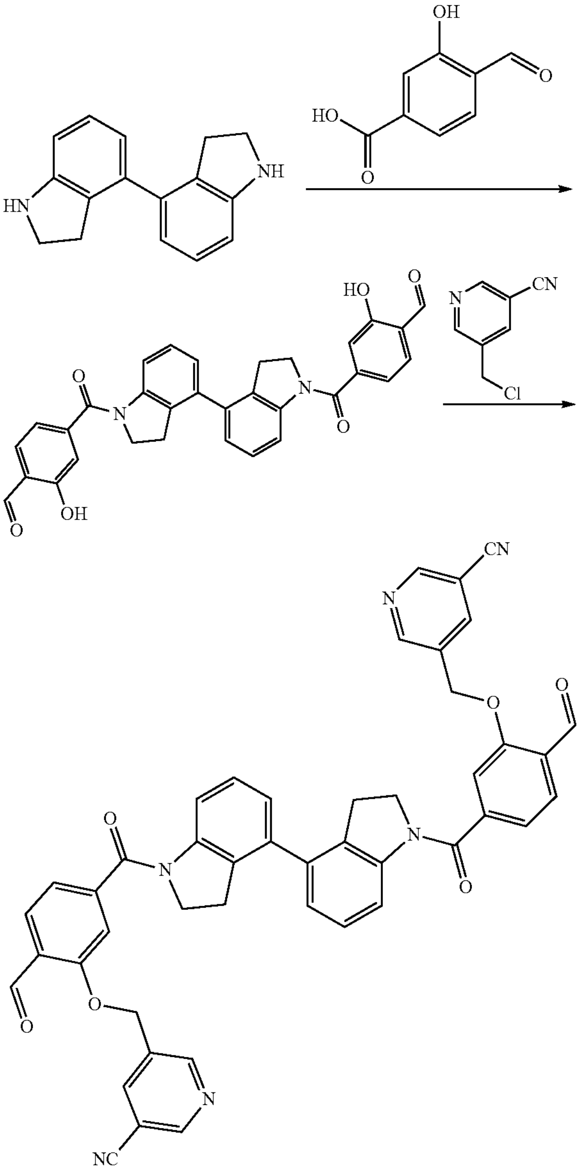

To a 20 mL vial was added 4,4'-biindoline (500 mg, 2.1 mmol), 4-formyl-3-hydroxybenzoic acid (872 mg, 5.25 mmol, 2.5 equiv), N,N-diisopropylethylamine (1.83 mL, 10.5 mmol, 5.0 equiv) and N,N-dimethylformamide (21.0 mL, 0.1M) at room temperature. To the vessel was added 1-[Bis(dimethylamino)methylene]-1H-1,2,3-triazolo[4,5-b]pyridinium 3-oxide hexafluorophosphate (1.76 g, 4.6 mmol, 2.2 equiv), and the reaction mixture was stirred at room temperature for 1 hour before being diluted with ethyl acetate (10 mL). The mixture was acidified to pH=2 with N aqueous hydrochloric acid then washed ×1 with water and ×1 with brine. The organic layer was then dried over magnesium sulfate, filtered, and concentrated under vacuum. The crude material was purified by silica gel column chromatography using a 0-10% methanol in methylene chloride eluent gradient to provide 4,4'-([4,4'-biindoline]-1,1'-dicarbonyl)bis(2-hydroxybenzaldehyde).

To a 20 mL vial was added 4,4'-([4,4'-biindoline]-1,1'-dicarbonyl)bis(2-hydroxybenzaldehyde) (492 mg, 0.92 mmol), 5-(chloromethyl)nicotinonitrile (309 mg, 2.0 mmol, 2.2 equiv), potassium carbonate (381 mg, 2.8 mmol, 3.0 equiv), sodium iodide (35 mg, 0.23 mmol, 25 mol %) and N,N-dimethylformamide (9.2 mL, 0.1M) at room temperature. The reaction mixture was stirred at 60° C. for 1 hour before being cooled to room temperature and diluted with ethyl acetate (30 mL). The mixture was then washed ×1 with water and ×1 with brine. The organic layer was then dried over magnesium sulfate, filtered, and concentrated under vacuum. The crude material was purified by silica gel column chromatography using a 0-10% methanol in methylene chloride eluent gradient to provide 5,5'-((((([4,4'-biindoline]-1,1'-dicarbonyl)bis(6-formyl-3,1-phenylene))bis(oxy))bis(methylene))dinicotinonitrile.

Intermediate 40: 4,4'-(((2,2'-dimethyl-[1,1'-biphenyl]-3,3'-diyl)bis(methylene))bis(oxy))bis(5-chloro-2-(thiazol-2-ylmethoxy)benzaldehyde)

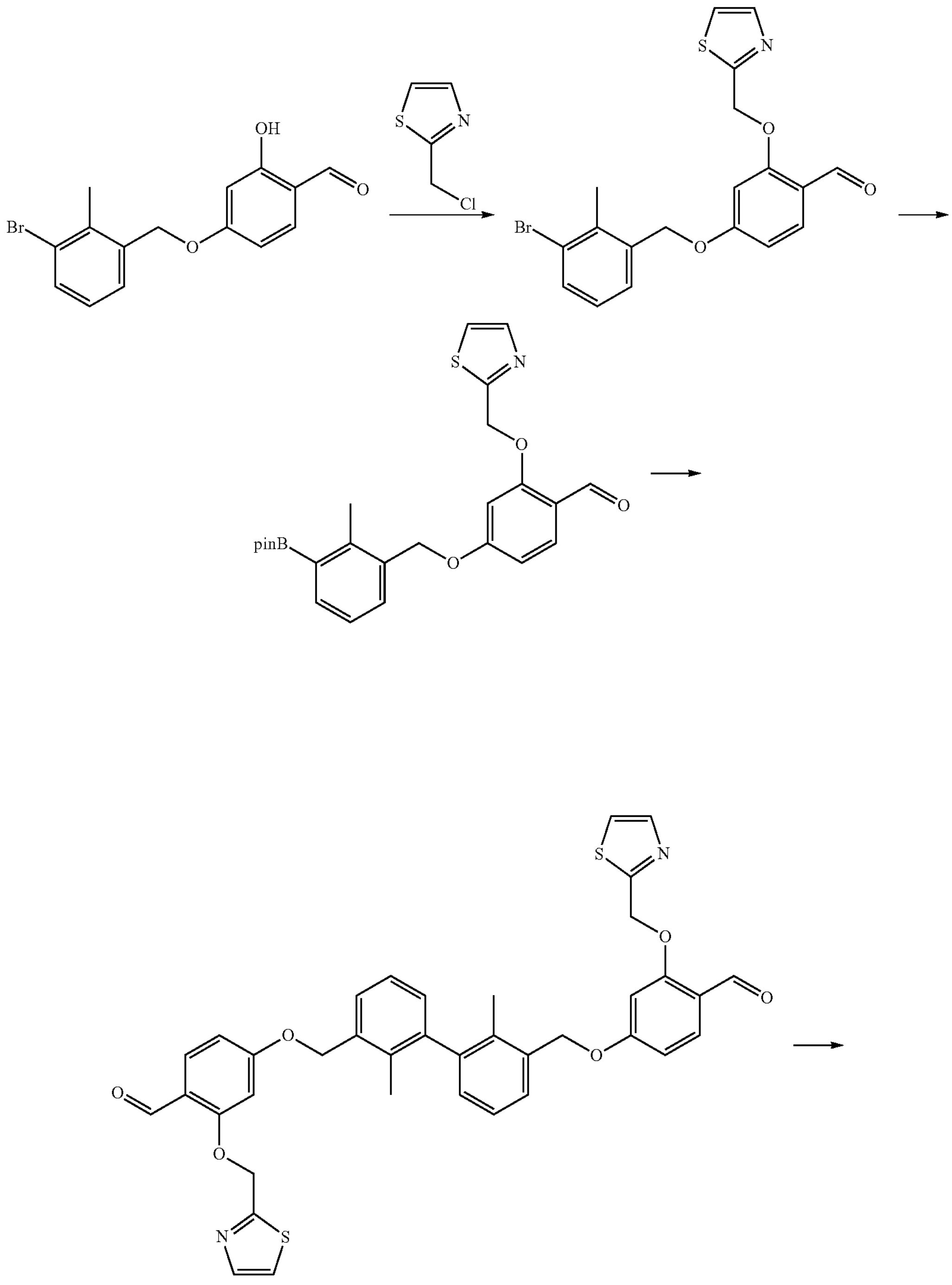

-continued

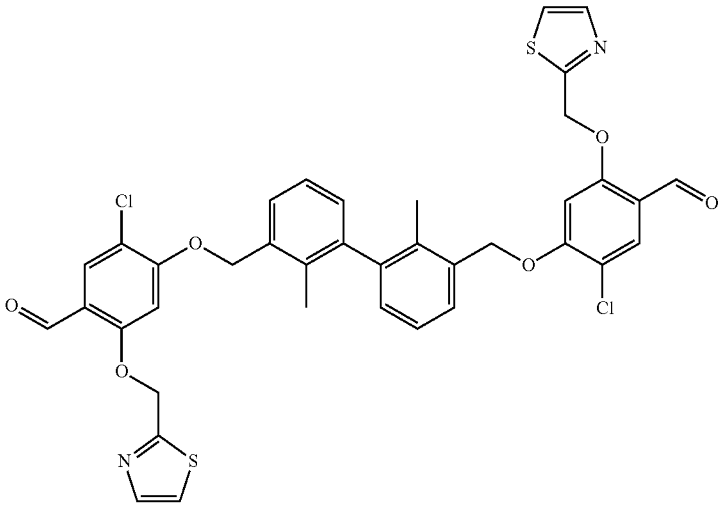

To a 100 mL round bottom flask was added 4-((3-bromo-2-methylbenzyl)oxy)-2-hydroxybenzaldehyde (750 mg, 2.3 mmol), 2-(chloromethyl)thiazole (374 mg, 3.5 mmol, 1.2 equiv), potassium carbonate (336 mg, 2.0 mmol, 1.5 equiv), sodium iodide (62 mg, 0.41 mmol, 25 mol %) and N,N-dimethylformamide (23.0 mL, 1M) at room temperature. The reaction mixture was stirred at 60° C. for 1 hour before being cooled to room temperature and diluted with ethyl acetate (40 mL). The mixture was washed once with water and once with brine. The organic layer was then dried over magnesium sulfate, filtered, and concentrated under vacuum. The crude material was purified by silica gel column chromatography using a 0-10% methanol in methylene chloride eluent gradient to provide 4-((3-bromo-2-methylbenzyl)oxy)-2-(thiazol-2-ylmethoxy)benzaldehyde.

To a 20 mL vial was added 4-((3-bromo-2-methylbenzyl)oxy)-2-(thiazol-2-ylmethoxy)benzaldehyde (460 mg, 1.1 mmol), 4,4,4',4',5,5,5',5'-octamethyl-2,2'-bi(1,3,2-dioxaborolane) (377 mg, 1.49 mmol, 1.35 equiv), [1,1'-Bis(diphenylphosphino)ferrocene]dichloropalladium(II)(81 mg, 0.11 mmol, 10 mol %), potassium acetate (215 mg, 2.20 mmol, 2.0 equiv), and 1,4-dioxane (11.0 mL, 0.1 M) at room temperature. The vessel was sealed, and the mixture was sparged with nitrogen for 5 minutes before being heated to 90° C. for 3 hours. The reaction mixture was then cooled to room temperature, ethyl acetate (10 mL) was added, and the contents of the vial were filtered through celite. The filtrate was concentrated under vacuum, and the crude 4-((2-methyl-3-(4,4,5,5-tetramethyl-1,3,2-dioxaborolan-2-yl)benzyl)oxy)-2-(thiazol-2-ylmethoxy)benzaldehyde was used without further purification.

To a 20 mL vial was added the crude 4-((2-methyl-3-(4,4,5,5-tetramethyl-1,3,2-dioxaborolan-2-yl)benzyl)oxy)-2-(thiazol-2-ylmethoxy)benzaldehyde, 4-((3-bromo-2-methylbenzyl)oxy)-2-(thiazol-2-ylmethoxy)benzaldehyde (460 mg, 1.1 mmol), [1,1'-Bis(diphenylphosphino)ferrocene]dichloropalladium(I) (81 mg, 0.11 mmol, 10 mol %), potassium carbonate (304 mg, 2.2 mmol, 2.0 equiv), N,N-dimethylformamide (11.0 mL, 0.1 M), and water (1.1 mL) at room temperature. The vessel was sealed, and the mixture was sparged with nitrogen for 5 minutes before being heated to 90° C. for 1 hours. The reaction mixture was then cooled to room temperature, ethyl acetate (10 mL) was added, and the contents of the vial were filtered through celite. The filtrate was diluted with ethyl acetate (50 mL) and washed once with water then brine. The organic layer was then dried over magnesium sulfate, filtered, and concentrated under vacuum. The crude material was purified by silica gel column chromatography using a 0-10% methanol in methylene chloride eluent gradient to provide 5,5'-((((((2,2'-dimethyl-[1,1'-biphenyl]-3,3'-diyl)bis(methylene))bis(oxy))bis(6-formyl-3,1-phenylene))bis(oxy))bis(methylene))dinicotinonitrile.

To a 20 mL vial was added 4,4'-(((2,2'-dimethyl-[1,1'-biphenyl]-3,3'-diyl)bis(methylene))bis(oxy))bis(2-(thiazol-2-ylmethoxy)benzaldehyde) (413 mg, 0.61 mmol), N-chlorosuccinimide (204 mg, 1.5 mmol, 2.5 equiv), and chloroform (6.1 mL, 0.1M) at rt. To the mixture was added a drop of 4M hydrochloric acid in dioxane. After 2 hours, 1M aqueous sodium sulfite was added until the color disappeared. To this mixture was added 1N aqueous sodium hydroxide until pH=7. Finally, ethyl acetate (10 mL) and water (10 mL) were added, and the organic layer was washed once with brine, dried over magnesium sulfate, filtered, and concentrated under vacuum. The crude residue of 4,4'-(((2,2'-dimethyl-[1,1'-biphenyl]-3,3'-diyl)bis(methylene))bis(oxy))bis(5-chloro-2-(thiazol-2-ylmethoxy)benzaldehyde) was used without further purification.

Intermediate 41: 2,2'-(((2,2'-dimethyl-[1,1'-biphenyl]-3,3'-diyl)bis(methylene))bis(oxy))bis(5-formyl-6-methoxynicotinonitrile)

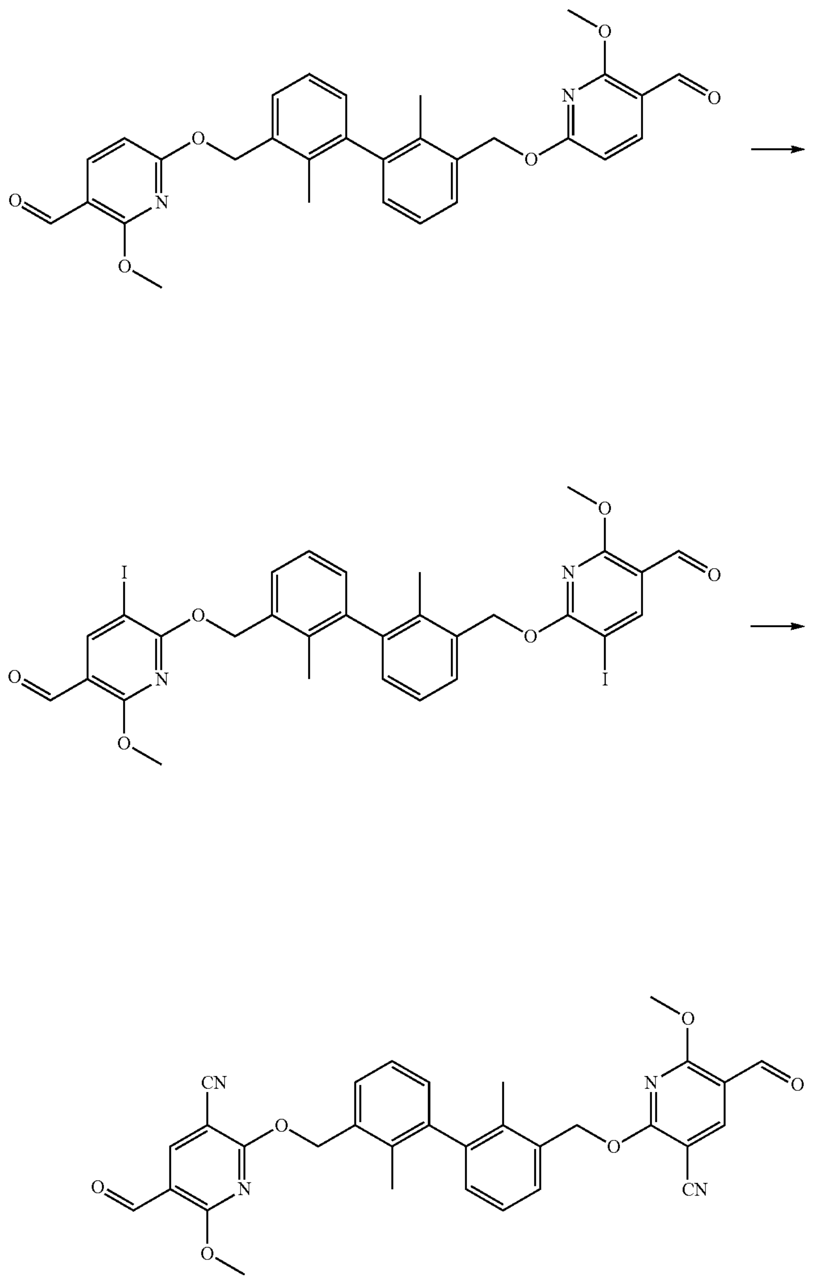

To a 20 mL vial was added 6,6'-(((2,2'-dimethyl-[1,1'-biphenyl]-3,3'-diyl)bis(methylene))bis(oxy))bis(2-methoxynicotinaldehyde) (150 mg, 0.29 mmol), N-iodosuccinimide (144 mg, 0.64 mmol, 2.2 equiv), and methylene chloride (2.9 mL, 0.1M) at rt. To the vessel was added 1 drop of trifluoroacetic acid. After 2 hours, the mixture was diluted with methylene chloride 10 mL) and water (10 mL). The organic layer was washed once with brine, dried over magnesium sulfate, filtered, and concentrated under vacuum. The crude material was purified by silica gel column chromatography using a 0-10% methanol in methylene chloride eluent gradient to provide 6,6'-(((2,2'-dimethyl-[1,1'-biphenyl]-3,3'-diyl)bis(methylene))bis(oxy))bis(5-iodo-2-methoxynicotinaldehyde).

To a 2 dram vial was added 6,6'-(((2,2'-dimethyl-[1,1'-biphenyl]-3,3'-diyl)bis(methylene))bis(oxy))bis(5-iodo-2-methoxynicotinaldehyde) (166 mg, 0.22 mmol), copper(I) cyanide (59 mg, 0.66 mmol, 3.0 equiv), and acetonitrile (0.9 mL, 0.25M). The mixture was heated to reflux for 2 hours then cooled to room temperature. The mixture was diluted with ethyl acetate (5 mL) and filtered through celite. The filtrate of 2,2'-(((2,2'-dimethyl-[1,1'-biphenyl]-3,3'-diyl)bis(methylene))bis(oxy))bis(5-formyl-6-methoxynicotinonitrile) was concentrated under vacuum and used without further purification.

Intermediate 42: 6,6'-(((2,2'-dimethyl-[1,1'-biphenyl]-3,3'-diyl)bis(methylene))bis(oxy))bis(2-methoxy-5-(methylsulfonyl)nicotinaldehyde)

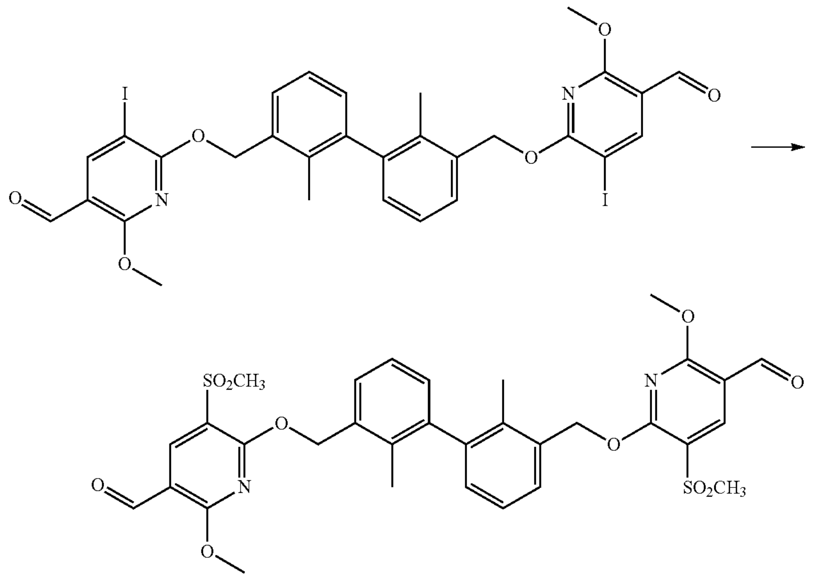 [SMILES: COc1nc(OCc2cccc(-c3cccc(COc4nc(OC)c(C=O)cc4I)c3C)c2C)c(I)cc1C=O ; COc1nc(OCc2cccc(-c3cccc(COc4nc(OC)c(C=O)cc4S(C)(=O)=O)c3C)c2C)c(S(C)(=O)=O)cc1C=O]

To a 2-dram vial was added 6,6'-(((2,2'-dimethyl-[1,1'-biphenyl]-3,3'-diyl)bis(methylene))bis(oxy))bis(5-iodo-2-methoxynicotinaldehyde) (166 mg, 0.22 mmol), potassium metabisulfite (196 mg, 0.88 mmol, 4.0 equiv), sodium formate (66 mg, 0.97 mmol, 4.4 equiv), tetrabutylammonium bromide (156 mg, 0.48 mmol, 2.2 equiv), palladium (II) acetate (5.0 mg, 0.02 mmol, 10 mol %), triphenylphosphine (17 mg, 0.07 mmol, 30 mol %), 1,10-phenanthroline (12 mg, 0.07 mmol, 30 mol %), and DMSO (1.1 mL, 0.2M) at room temperature. The mixture was sparged for 5 minutes with nitrogen and stirred overnight. Then, methyl iodide (0.041 mL, 0.66 mmol, 3.0 equiv) was added, and the mixture was stirred overnight. The mixture was diluted with ethyl acetate (5 mL) and washed once with water then brine. The organic layer was then dried over magnesium sulfate, filtered, and concentrated under vacuum. The crude material was purified by silica gel column chromatography using a 0-10% methanol in methylene chloride eluent gradient to provide 6,6'-(((2,2'-dimethyl-[1,1'-biphenyl]-3,3'-diyl)bis(methylene))bis(oxy))bis(2-methoxy-5-(methylsulfonyl)nicotinaldehyde).

Intermediate 43: (S)-5-(((6-((4-(3-bromo-2-chlorophenyl)-2,3-dihydro-1H-inden-1-yl)oxy)-5-chloro-3-formylpyridin-2-yl)oxy)methyl)nicotinonitrile

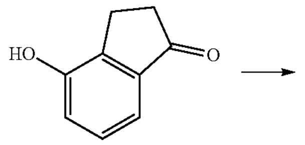

-continued

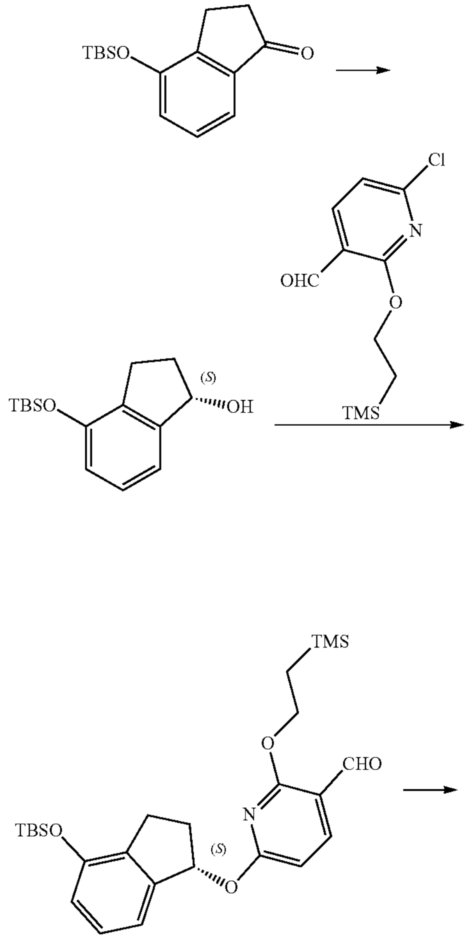

-continued

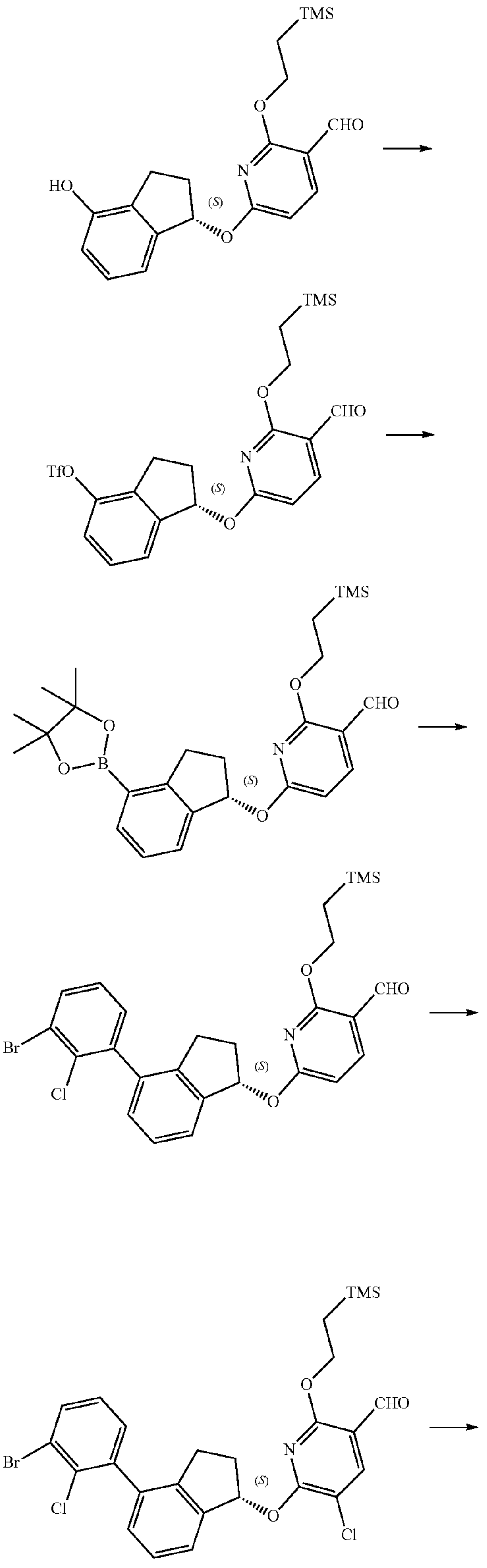

-continued

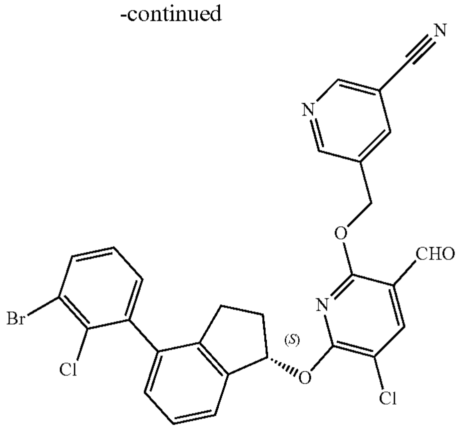

Step 1: To a solution of 4-hydroxy-indan-1-one in CH2Cl2 (500 mL) was added imidazole. The mixture was stirred for 5 minutes, to which was added portion wise tert-butyldimethylsilyl chloride while cooling in an ice bath. The mixture was stirred for 16 hours at room temperature and was diluted with EtOAc. The organic layer was washed with citric acid, water and brine, dried over anhydrous magnesium sulfate, filtered, and concentrated under reduced pressure. The crude residue was purified by column chromatography (Hex-EA) to give 4-(tert-butyl-dimethyl-silanyloxy)-indan-1-one (54 g, 101% yield). $^1$H NMR (400 MHz, $CDCl_3$): δ 7.27 (d, 1H, J=7.5 Hz), 7.15 (t, 1H, J=7.5 Hz), 6.89 (d, 1H, J=7.5 Hz), 2.93 (t, 2H, J=5.7 Hz), 2.57 (t, 2H, J=5.7 Hz), 0.81 (s, 9H), 0.15 (s, 6H).

Step 2: To a 3000 mL rbf was added (R)-(+)-2-methyl-CBS-oxazaborolidine (8.397 g, 30.29 mmol), toluene (30 mL) and borane-dimethylsulfide (105.35 mL, 1111 mmol) under N2. The reaction was stirred at room temperature for 10 min then diluted with DCM (240 mL) and cooled to −20° C. A solution of 4-bromo-2,3-dihydro-1H-inden-1-one (53.0 g, 202 mmol) in DCM (240 mL) was added dropwise over 30 min while maintaining the reaction temperature at −10±5° C. The reaction was stirred for 2 h. Rxn quenched by the dropwise addition of MeOH (500 mL). Cooling bath was removed and reaction warmed to rt, then about half the rxn volume was distilled off using a short-path distillation apparatus. All remaining solvent was then evaporated under reduced pressure to give a solid which was purified by silica gel column chromatography eluting with EA-Hex to provide the desired product (58 g, 109% yield) as an oil that crystallized on standing. ES/MS m/z: [M−OH]+=247. $^1$H NMR (400 MHz, Chloroform-d) δ 7.13 (dt, J=15.3, 0.8 Hz, 1H), 7.02 (d, J=7.4 Hz, 1H), 6.70 (d, J=8.0 Hz, 1H), 5.23 (t, J=6.0 Hz, 1H), 3.00 (ddd, J=16.2, 8.6, 4.7 Hz, 1H), 2.79-2.66 (m, 1H), 2.46 (dddd, J=13.1, 8.3, 6.9, 4.7 Hz, 1H), 1.92 (dddd, J=13.6, 8.6, 6.3, 5.2 Hz, 1H), 1.00 (s, 9H), 0.20 (d, J=1.8 Hz, 6H).

Step 3: A solution of (S)-4-((tert-butyldimethylsilyl)oxy)-2,3-dihydro-1H-inden-1-ol (6.0 g, 22.7 mmol) and 6-chloro-2-(2-(trimethylsilyl)ethoxy)nicotinaldehyde (11.7 g, 45.4 mmol), in toluene (40 mL) was degassed by vigorously bubbling $N_2$ thru solution for 10 min. Then $Pd(OAc)_2$ (1.02 g, 4.54 mmol), t-BuXPhos (3.85 g, 9.07 mmol) and cesium carbonate (29.5 g, 90.8 mmol) were added and the bubbling continued for 5 min more. The reaction was then stirred at 35 C for 48 h under $N_2$. Rxn was cooled to rt and diluted with DCM. Filtered thru celite and loaded directly on silica gel column, eluting with Hex-DCM to provide (S)-6-((4-((tert-butyldimethylsilyl)oxy)-2,3-dihydro-1H-inden-1-yl)

oxy)-2-(2-(trimethylsilyl)ethoxy)nicotinaldehyde (9.51 g, 86% yield) as a light oil that crystallized on standing. $^1$H NMR (400 MHz, Chloroform-d) δ 10.29 (d, J=0.8 Hz, 1H), 8.92 (d, J=2.1 Hz, 1H), 8.86 (d, J=2.0 Hz, 1H), 8.16-8.04 (m, 2H), 7.10 (s, 1H), 7.10 (dt, J=15.5, 0.8 Hz, 1H), 6.93 (d, J=7.5 Hz, 1H), 6.79-6.72 (m, 1H), 6.50-6.41 (m, 2H), 5.68-5.53 (m, 2H), 4.12 (q, J=7.1 Hz, 1H), 3.07 (ddd, J=16.3, 8.8, 5.2 Hz, 1H), 2.86 (ddd, J=16.3, 8.6, 5.5 Hz, 1H), 2.51 (dddd, J=13.9, 8.6, 7.1, 5.3 Hz, 1H), 2.14 (dddd, J=13.9, 8.7, 5.5, 4.4 Hz, 1H), 2.04 (s, 1H), 1.32-1.19 (m, 2H), 1.01 (s, 9H), 0.23 (s, 6H).

Step 4: (S)-6-((4-((tert-butyldimethylsilyl)oxy)-2,3-dihydro-1H-inden-1-yl)oxy)-2-(2-(trimethylsilyl)ethoxy) nicotinaldehyde (4.69 g, 9.66 mmol) was taken up in 50 mL THF and cooled to -78 C. TBAF (9.66 mL, 9.66 mmol) was added dropwise and the reaction allowed to warm up to 0 C over 30 min, providing a dark orange solution. AcOH (0.552 mL, 9,655 mmol) was added dropwise, removing most of the color. Rxn was then diluted with EtOAc and pH 5 citrate buffer. Organic layer was dried (Na2SO4) and the reaction conc. Purification by silica gel chromatography provided (S)-6-((4-hydroxy-2,3-dihydro-1H-inden-1-yl)oxy)-2-(2-(trimethylsilyl)ethoxy)nicotinaldehyde (2.75 g, 77% yield) and an off-white solid. $^1$H NMR (400 MHz, Chloroform-d) δ 10.23 (d, J=0.8 Hz, 1H), 8.04 (d, J=8.4 Hz, 1H), 7.14 (t, J=7.7 Hz, 1H), 7.07-6.96 (m, 1H), 6.78 (dd, J=7.9, 1.0 Hz, 1H), 6.53 (dd, J=7.1, 4.2 Hz, 1H), 6.34 (dd, J=8.4, 0.9 Hz, 1H), 5.20 (s, 1H), 4.66-4.57 (m, 2H), 3.10 (ddd, J=14.5, 8.7, 5.4 Hz, 1H), 2.89 (ddd, J=15.8, 8.7, 5.2 Hz, 1H), 2.66 (dddd, J=14.0, 8.6, 7.0, 5.4 Hz, 1H), 2.26 (dddd, J=13.9, 8.7, 5.2, 4.2 Hz, 1H), 0.91 (s, 2H), 0.08 (s, 9H).

Step 5: A solution of (S)-6-((4-hydroxy-2,3-dihydro-1H-inden-1-yl)oxy)-2-(2-(trimethylsilyl)ethoxy)nicotinaldehyde (5.00 g, 13 mmol) in 55 mL DCM was treated with pyridine (2.76 mL, 34 mmol), DMAP (164 mg, 1.3 mmol) and TEA (3.75 mL, 27 mmol) was cooled to −78 C and treated dropwise with Tf2O (2.50 mL, 15 mmol). Stirred for 15 min, then allowed to warm to rt. After 1 h the reaction was diluted with EtOAc, washed with citric acid soln, dried with Na2SO4 and concentrated. Purification by silica chromatography (hex-DCM) provided (S)-1-((5-formyl-6-(2-(trimethylsilyl)ethoxy)pyridin-2-yl)oxy)-2,3-dihydro-1H-inden-4-yl trifluoromethanesulfonate (6.42 g, 94% yield). [M+H]=503.7. $^1$H NMR (400 MHz, Chloroform-d) δ 10.25 (d, J=0.8 Hz, 1H), 8.07 (d, J=8.3 Hz, 1H), 7.46 (d, J=7.5 Hz, 1H), 7.33 (t, J=7.8 Hz, 1H), 7.23 (d, J=8.1 Hz, 1H), 6.56 (dd, J=7.1, 5.0 Hz, 1H), 6.37 (dd, J=8.4, 0.8 Hz, 1H), 4.60 (td, J=8.2, 1.2 Hz, 2H), 3.27 (ddd, J=16.6, 8.9, 5.1 Hz, 1H), 3.12-2.99 (m, 1H), 2.72 (dddd, J=13.7, 8.5, 7.1, 5.1 Hz, 1H), 2.29 (dddd, J=13.8, 8.8, 6.1, 4.9 Hz, 1H), 1.55 (s, 1H), 1.24-1.18 (m, 2H), 0.07 (s, 9H). 19F NMR δ −74.10.

Step 6: A solution of (S)-6-((4-hydroxy-2,3-dihydro-1H-inden-1-yl)oxy)-2-(2-(trimethylsilyl)ethoxy)nicotinaldehyde (6.42 g, 0.13 mmol), 4,4,4',4',5,5,5',5'-octamethyl-2,2'-bi(1,3,2-dioxaborolane) (3.89 g, 15 mmol), Pd-dppf (0.932 g, 1.27 mmol) and KOAc (3.75 g, 38 mmol) in 55 mL dioxane was stirred at 90 C overnight. Reaction was diluted with EtOAc, filtered thru celite and conc. Purification of the filtrate derived material by ISCO (DCM-hexanes) provided (S)-6-((4-(4,4,5,5-tetramethyl-1,3,2-dioxaborolan-2-yl)-2,3-dihydro-1H-inden-1-yl)oxy)-2-(2-(trimethylsilyl)ethoxy) nicotinaldehyde (4.89 g, 79% yield) as a yellow oil. $^1$H NMR (400 MHz, Chloroform-d) δ 10.24 (d, J=0.9 Hz, 1H), 8.03 (d, J=8.3 Hz, 1H), 7.78 (dd, J=7.3, 1.3 Hz, 1H), 7.53 (d, J=7.6 Hz, 1H), 7.23 (d, J=7.4 Hz, 1H), 6.51 (dd, J=7.1, 4.3 Hz, 1H), 6.33 (dd, J=8.3, 0.9 Hz, 1H), 4.66-4.57 (m, 2H), 3.36 (ddd, J=17.2, 8.7, 5.7 Hz, 1H), 3.15 (ddd, J=17.2, 8.7, 5.6 Hz, 1H), 2.60 (dddd, J=14.1, 8.6, 7.1, 5.6 Hz, 1H), 2.26-2.13 (m, 1H), 1.34 (s, 12H), 1.31-1.18 (m, 2H), 0.07 (s, 9H).

Step 7: A solution of (S)-6-((4-(4,4,5,5-tetramethyl-1,3,2-dioxaborolan-2-yl)-2,3-dihydro-1H-inden-1-yl)oxy)-2-(2-(trimethylsilyl)ethoxy)nicotinaldehyde (3.60 g, 7.5 mmol), 2,6-dibromo-1-chlorobenzene (6.06 g, 22.4 mmol), Pd-dppf (471 mg, 0.748 mmol) and $K_2CO_3$ (2.58 mg, 19 mmol) in 60 mL dioxane was treated with 10 mL water and heated to 90° C. for 2 h. The reaction was then cooled to rt, diluted with EtOAc and dried with $MgSO_4$. The mixture was filtered thru celite and concentrated to provide a crude oil. Purification by column chromatography (ISCO, elution with DCM-hexanes) provided (S)-6-((4-(3-bromo-2-chlorophenyl)-2,3-dihydro-1H-inden-1-yl)oxy)-2-(2-(trimethylsilyl)ethoxy) nicotinaldehyde (3.05 g, 75% Yield). $^1$H NMR (400 MHz, Chloroform-d) δ 10.25 (d, J=0.9 Hz, 1H), 8.06 (d, J=8.3 Hz, 1H), 7.66 (dd, J=7.7, 1.9 Hz, 1H), 7.50 (d, J=7.5 Hz, 1H), 7.39-7.28 (m, 2H), 7.31-7.13 (m, 2H), 6.61 (s, 1H), 6.47-6.31 (m, 1H), 4.67-4.57 (m, 2H), 2.99 (dd, J=15.6, 9.6 Hz, 1H), 2.90-2.74 (m, 1H), 2.65 (m, 1H), 2.21 (m, J=8.5 Hz, 1H), 1.34-1.18 (m, 2H), 0.07 (s, 9H).

Step 8: A solution of (S)-6-((4-(3-bromo-2-chlorophenyl)-2,3-dihydro-1H-inden-1-yl)oxy)-2-(2-(trimethylsilyl) ethoxy)nicotinaldehyde (1.20 g, 2.20 mmol) in 6 mL DCM and 3 mL DMF was treated with Palau-Cl (557 mg, 2.75 mmol) and TFA (33.7 μL, 0.44 mmol). The reaction was stirred for 16h at rt, then diluted with DCM and treated with 10 mL sat thiosulfate and 20 mL $NaHCO_3$. After stirring vigorously for 10 min, the organic layer was separated, dried with $MgSO_4$, filtered and concentrated. Purification by column chromatography (ISCO, elution with DCM-hexanes) provided (S)-6-((4-(3-bromo-2-chlorophenyl)-2,3-dihydro-1H-inden-1-yl)oxy)-5-chloro-2-(2-(trimethylsilyl)ethoxy) nicotinaldehyde (726 mg, 56% Yield). $^1$H NMR (400 MHz, Chloroform-d) δ 10.20 (s, 1H), 8.09 (s, 1H), 7.66 (dd, J=7.7, 1.9 Hz, 1H), 7.51 (d, J=7.5 Hz, 1H), 7.34 (t, J=7.6 Hz, 1H), 7.29-7.14 (m, 1H), 7.20 (s, 2H), 6.58 (d, J=22.9 Hz, 1H), 4.61 (t, J=8.3 Hz, 2H), 2.94-2.77 (m, 2H), 2.69 (m, 2H), 2.28-2.20 (m, 1H), 1.27-1.17 (m, 2H), 0.07 (s, 9H).

Step 9: A solution of (S)-6-((4-(3-bromo-2-chlorophenyl)-2,3-dihydro-1H-inden-1-yl)oxy)-5-chloro-2-(2-(trimethylsilyl)ethoxy)nicotinaldehyde (303 mg, 0.523 mmol) in 5 mL DMF was treated with CsF (318 mg, 2.1 mmol) and stirred for 1 h at 60° C. $K_2CO_3$ (217 mg, 0.569 mmol) and 5-(chloromethyl)nicotinonitrile hydrochloride (148 mg, 0.784 mmol). After 30 min the reaction was partitioned between EtOAc and 2.5% LiCl. Organic layer was washed with 2% LiCl, dried with sodium sulfate, filtered and conc. Purification by column chromatography (ISCO, elution with EtOAc-hexanes) provided (S)-5-(((6-((4-(3-bromo-2-chlorophenyl)-2,3-dihydro-1H-inden-1-yl)oxy)-5-chloro-3-formylpyridin-2-yl)oxy)methyl)nicotinonitrile (Intermediate 43). LCMS-ESI+ (m/z): [M+H]+ calcd for $C_{28}H_{18}BrCl_2N_3O_3$: 593.99; found: 593.79.

Intermediate 44: 6-bromo-1-naphthaldehyde

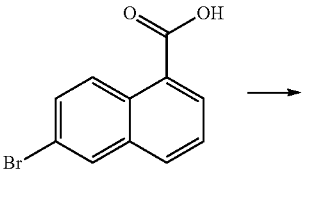

-continued

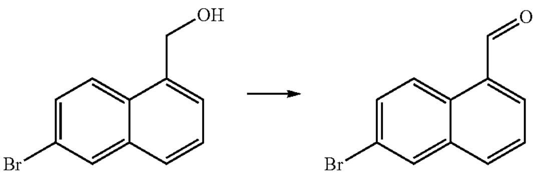

Step 1: A 2 M solution of Borane dimethyl sulfide (4 equiv.) was added dropwise to a slurry of 6-bromo-1-naphthoic acid (250 mg, 0.996 mmol) in THF (2.5 mL) at 0° C. The reaction vessel was then warmed to 35° C. for 1 hour. LC/MS indicated full consumption of starting material. The reaction vessel then cooled to 0° C. and methanol was added dropwise until gas evolution was no longer observed. The reaction was then warmed to room temperature, diluted with water (5 mL), and extracted 3×5 mL) with ethyl acetate. The combined organic layers were dried over sodium sulfate, concentrated in vacuo, and used without further purification.

Step 2: (6-bromonaphthalen-1-yl)methanol from the previous step was taken up in methylene chloride. At room temperature Dess-Martin periodinane (1.2 equiv.) was added in a single portion. The reaction was stirred at room temperature for 1 hour. LC/MS indicated full consumption of starting material. The reaction was concentrated in vacuo. The crude material was purified by column chromatography (EtOAc/Hexanes) to afford 6-bromo-1-naphthaldehyde.

Intermediate 45: 5-((4-chloro-5-((2'-chloro-4"-((dimethylamino)methyl)-6'-fluoro-2-methyl-[1,1':3',1"-terphenyl]-3-yl)methoxy)-2-formylphenoxy)methyl) nicotinonitrile

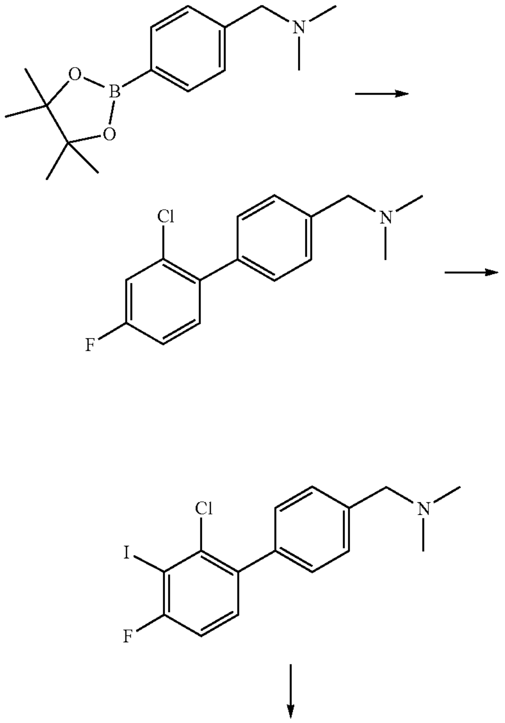

-continued

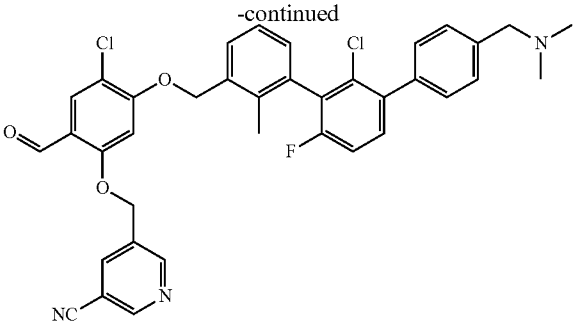

Step 1. A stirred mixture of N,N-dimethyl-1-(4-(4,4,5,5-tetramethyl-1,3,2-dioxaborolan-2-yl)phenyl)methanamine hydrochloride (1.00 g, 3.36 mmol), 1-bromo-2-chloro-4-fluorobenzene (1.06 g, 5.04 mmol), aqueous sodium carbonate solution (2.0 M, 8.4 mL, 16.8 mmol), and chloro(2-dicyclohexylphosphino-2',4',6'-triisopropyl-1,1'-biphenyl)[2-(2'-amino-1,1'-biphenyl)]palladium(II) (79 mg, 0.10 mmol) in 1,4-dioxane was heated to 100° C. After 50 min, the resulting mixture was allowed to cool to room temperature, was filtered through celite, and was concentrated under reduced pressure. The residue was purified by flash column chromatography on silica gel (0 to 20% methanol in dichloromethane) to give 1-(2'-chloro-4'-fluoro-[1,1'-biphenyl]-4-yl)-N,N-dimethylmethanamine.

Step 2. 2,2,6,6-Tetramethylpiperidinylmagnesium chloride lithium chloride complex solution (1.0 M in tetrahydrofuran and toluene, 6.46 mL, 6.5 mmol) was added via syringe to a stirred solution of 1-(2'-chloro-4'-fluoro-[1,1'-biphenyl]-4-yl)-N,N-dimethylmethanamine (775 mg, 2.94 mmol) in tetrahydrofuran (7.0 mL) at room temperature. After 2 h, the resulting mixture was cooled to 0° C., and iodine (1.12 g, 4.41 mmol) was added as a solid under a nitrogen atmosphere. After 20 min, aqueous sodium thiosulfate solution (1.0 M, 5 mL) was added, and the resulting biphasic mixture was allowed to warm to room temperature with vigorous stirring. Diethyl ether (200 mL) was added, and the organic layer was washed sequentially with a mixture of water and saturated aqueous sodium carbonate solution (10:1 v:v, 100 mL) and water (100 mL), was dried over anhydrous magnesium sulfate, was filtered, and was concentrated under reduced pressure. The residue was purified by flash column chromatography on silica gel (0 to 15% methanol in dichloromethane) to give 1-(2'-chloro-4'-fluoro-3'-iodo-[1,1'-biphenyl]-4-yl)-N,N-dimethylmethanamine.

Step 3. A stirred mixture of 5-((4-chloro-2-formyl-5-((2-methyl-3-(4,4,5,5-tetramethyl-1,3,2-dioxaborolan-2-yl)benzyl)oxy)phenoxy)methyl)nicotinonitrile (292 mg, 0.565 mmol), 1-(2'-chloro-4'-fluoro-3'-iodo-[1,1'-biphenyl]-4-yl)-N,N-dimethylmethanamine (200 mg, 0.513 mmol), aqueous sodium carbonate solution (2.0 M, 1.0 mL, 2.0 mmol), and chloro(2-dicyclohexylphosphino-2',4',6'-triisopropyl-1,1'-biphenyl)[2-(2'-amino-1,1'-biphenyl)]palladium(II) (10 mg, 0.013 mmol) in 1,4-dioxane (5.0 mL) was heated to 105° C. in a heating block. After 60 min, the resulting mixture was allowed to cool to room temperature, was filtered through celite, and was concentrated under reduced pressure. The residue was purified by flash column chromatography on silica gel (0 to 20% methanol in dichloromethane) to give 5-((4-chloro-5-((2'-chloro-4"-((dimethylamino)methyl)-6'-fluoro-2-methyl-[1,1':3',1"-terphenyl]-3-yl)methoxy)-2-formylphenoxy)methyl)nicotinonitrile.

Intermediate 46: 5-((4-chloro-5-((2,2'-dimethyl-4"-(quinuclidin-3-yloxy)-[1,1':3',1"-terphenyl]-3-yl)methoxy)-2-formylphenoxy)methyl)nicotinonitrile

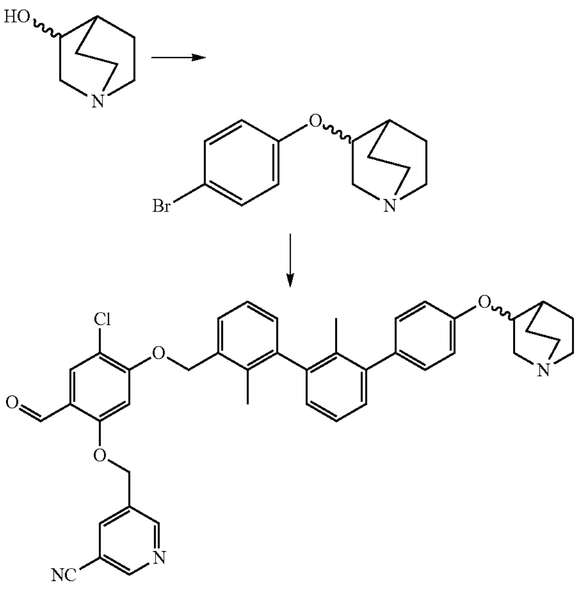

Step 1. Diisopropyl azodicarboxylate (464 mg, 2.29 mmol) was added via syringe to a stirred mixture of quinuclidin-3-ol (117 mg, 0.918 mmol), 4-bromophenol (476 mg, 2.75 mmol), and triphenylphosphine (650 mg, 2.48 mmol) in tetrahydrofuran (5.0 mL) at room temperature. After 5 min, the resulting mixture was heated to 50 C in a heating block. After 2 h, the resulting mixture was allowed to cool to room temperature and was purified by flash column chromatography on silica gel (0 to 100% ethyl acetate in hexanes to 0 to 20% methanol in dichloromethane to 3% triethylamine and 20% methanol in dichloromethane) to give 3-(4-bromophenoxy)quinuclidine.

Step 2. A stirred mixture of 5-((4-chloro-5-((2,2'-dimethyl-3'-(4,4,5,5-tetramethyl-1,3,2-dioxaborolan-2-yl)-[1,1'-biphenyl]-3-yl)methoxy)-2-formylphenoxy)methyl)nicotinonitrile (30 mg, 0.049 mmol), 3-(4-bromophenoxy)quinuclidine (28 mg, 0.099 mmol), aqueous sodium carbonate solution (2.0 M, 200 μL, 0.40 mmol), and chloro(2-dicyclohexylphosphino-2',4',6'-triisopropyl-1,1'-biphenyl)[2-(2'-amino-1,1'-biphenyl)]palladium(II) (2 mg, 0.002 mmol) in 1,4-dioxane (1.5 mL) was heated to 105° C. in a heating block. After 60 min, the resulting mixture was allowed to cool to room temperature. Diethyl ether (20 mL) and ethyl acetate (10 mL) were added, and the organic layer was washed with a mixture of water and saturated aqueous sodium carbonate solution (10:1 v:v, 2×30 mL), was dried over magnesium sulfate, was filtered, and was concentrated under reduced pressure to give 5-((4-chloro-5-((2,2'-dimethyl-4"-(quinuclidin-3-yloxy)-[1,1':3',1"-terphenyl]-3-yl)methoxy)-2-formylphenoxy)methyl)nicotinonitrile.

Intermediate 47: 5-chloro-6-((2,2'-dichloro-4"-(2-((2-hydroxyethyl)amino)ethoxy)-[1,1':3',1"-terphenyl]-3-yl)methoxy)-2-((5-(methylsulfonyl)pyridin-3-yl)methoxy)nicotinaldehyde 2,2,2-trifluoroacetate

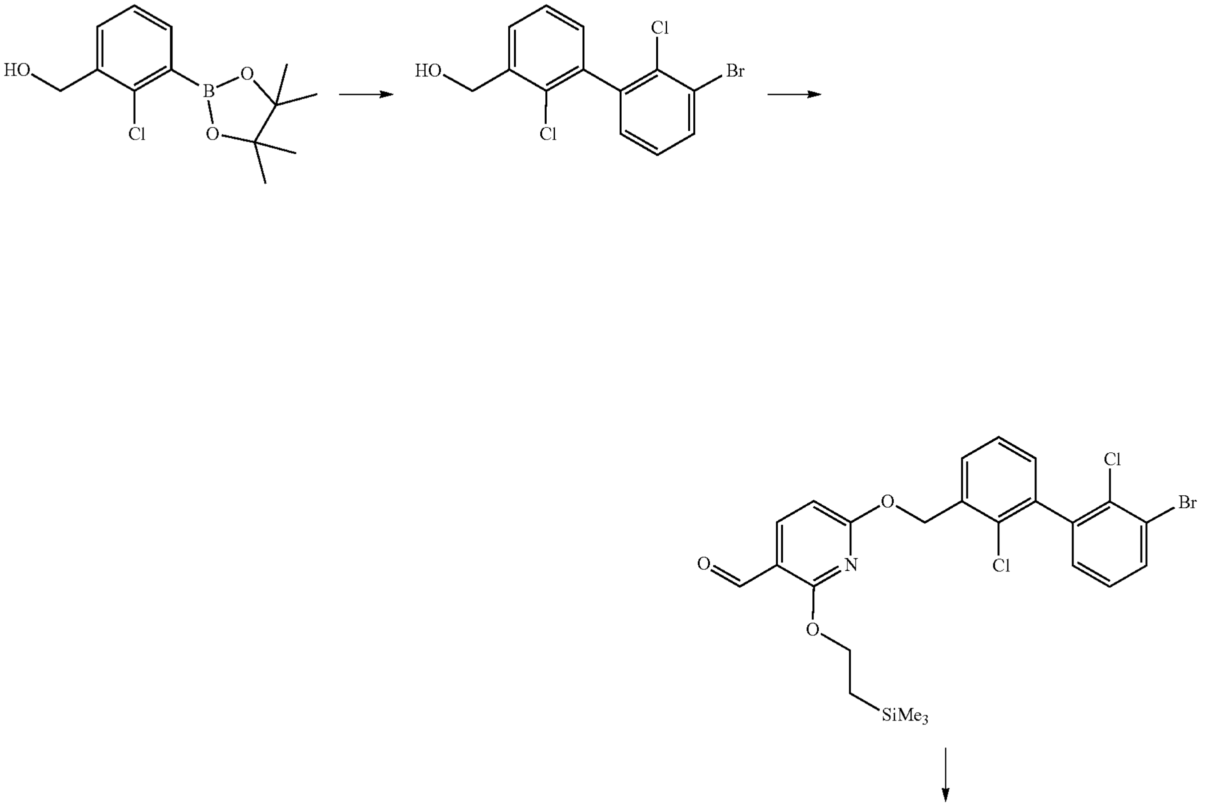

-continued

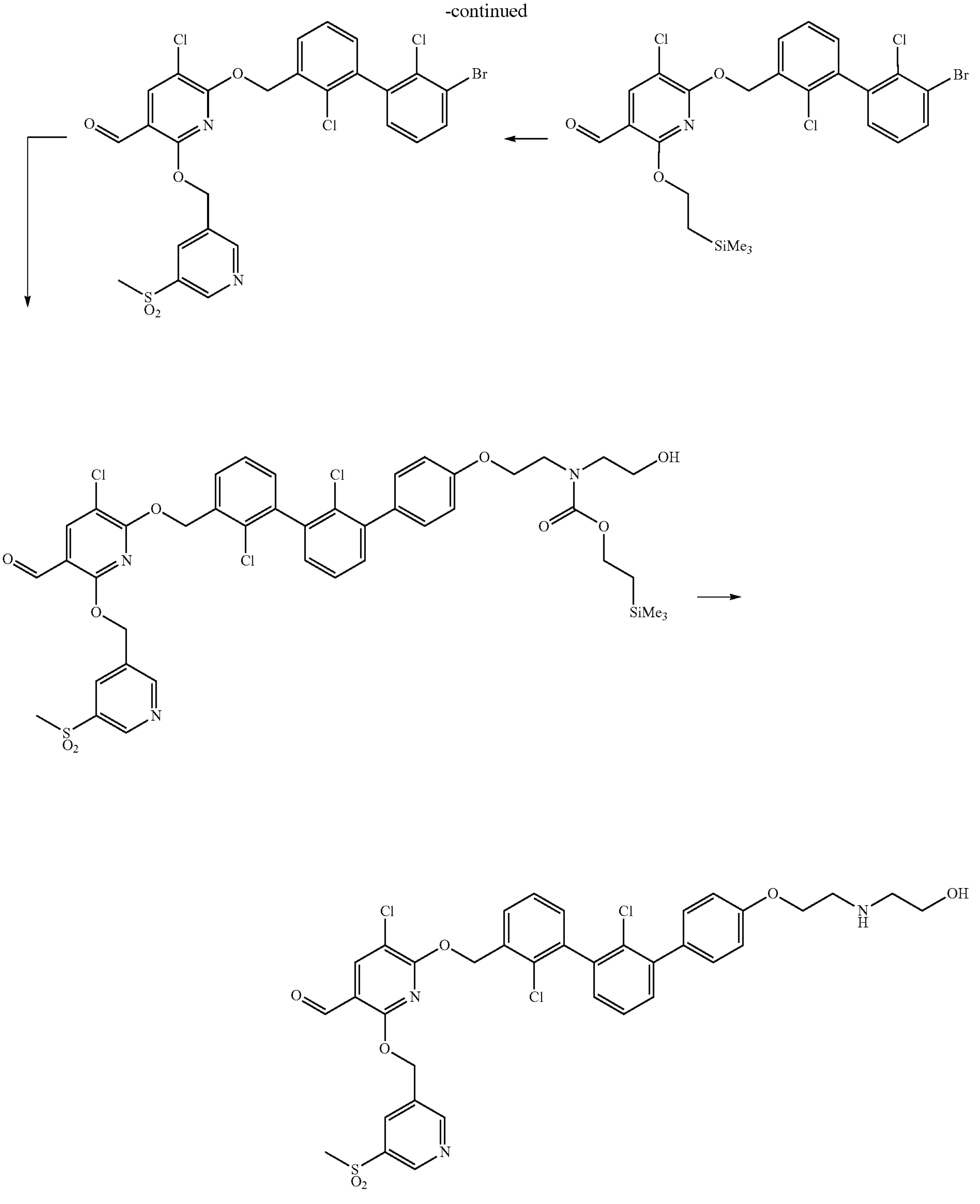

Step 1. A stirred mixture of (2-chloro-3-(4,4,5,5-tetramethyl-1,3,2-dioxaborolan-2-yl)phenyl)methanol (22.4 g, 83.3 mmol), 1,3-dibromo-2-chlorobenzene (33.8 g, 125 mmol), potassium carbonate (27.6 g, 200 mmol), and [1,1'-bis(diphenylphosphino)ferrocene]dichloropalladium(II) (1.83 g, 2.50 mmol) in 1,4-dioxane (150 mL) and water (40 mL) was heated to 115° C. in a heating block. After 90 min, the resulting mixture was allowed to cool to room temperature and was filtered through celite. Ethyl acetate (500 mL) was added, and the organic layer was washed with a mixture of water and brine (1:1 v:v, 300 mL), was dried over anhydrous sodium sulfate, was filtered, and was concentrated under reduced pressure. The residue was purified by flash column chromatography on silica gel (0 to 30% ethyl acetate in hexanes) to give (3'-bromo-2,2'-dichloro-[1,1'-biphenyl]-3-yl)methanol.

Step 2. Sodium hydride (60% w/w dispersion in mineral oil, 1.70 g, 42.4 mmol) was added as a solid under a nitrogen atmosphere to a stirred solution of (3'-bromo-2,2'-dichloro-[1,1'-biphenyl]-3-yl)methanol (11.7 g, 35.3 mmol) in N,N-dimethylformamide (200 mL) at 0° C. After 45 min, 6-chloro-2-(2-(trimethylsilyl)ethoxy)nicotinaldehyde (9.11 g, 35.3 mmol) was added as a solid under a nitrogen atmosphere. After 13.5 h, saturated aqueous ammonium chloride solution (20 mL) was added, and the resulting mixture was concentrated under reduced pressure. Ethyl acetate (267 mL), diethyl ether (400 mL), and tetrahydrofuran (133 mL) were added, and the organic layer was washed with water (800 mL), was dried over anhydrous magnesium sulfate, was filtered, and was concentrated under reduced pressure. The residue was purified by flash column chromatography on silica gel (0 to 20% ethyl acetate in hexanes) to give 6-((3'-bromo-2,2'-dichloro-[1,1'-biphenyl]-3-yl)methoxy)-2-(2-(trimethylsilyl)ethoxy)nicotinaldehyde.

Step 3. Hydrogen chloride solution (4.0 M in 1,4-dioxane, 5.46 mL, 22 mmol) was added via syringe over 5 min to a stirred mixture of 6-((3'-bromo-2,2'-dichloro-[1,1'-biphenyl]-3-yl)methoxy)-2-(2-(trimethylsilyl)ethoxy)nicotinaldehyde (11.0 g, 19.8 mmol) and 2-chloro-1,3-bis(methoxycarbonyl)guanidine (4.58 g, 21.8 mmol) in acetonitrile (100 mL) and chloroform (50 mL) at room temperature. After 30 min, saturated aqueous sodium bicarbonate solution (300 mL) and water (200 mL) were added, and the aqueous layer was extracted with dichloromethane (2×250 mL). The combined organic layers were dried over anhydrous sodium sulfate, were filtered, and were concentrated under reduced pressure. The residue was purified by flash column chromatography on silica gel (0 to 20% ethyl acetate in hexanes) to give 6-((3'-bromo-2,2'-dichloro-[1,1'-biphenyl]-3-yl)methoxy)-5-chloro-2-(2-(trimethylsilyl)ethoxy)nicotinaldehyde.

Step 4. Cesium fluoride (1.55 g, 10.2 mmol) was added as a solid under a nitrogen atmosphere to a stirred solution of 6-((3'-bromo-2,2'-dichloro-[1,1'-biphenyl]-3-yl)methoxy)-5-chloro-2-(2-(trimethylsilyl)ethoxy)nicotinaldehyde (1.50 g, 2.55 mmol) in N,N-dimethylformamide (10 mL) at room temperature, and the resulting mixture was heated to 70° C. in a heating block. After 45 min, 3-(chloromethyl)-5-(methylsulfonyl)pyridine (577 mg, 2.81 mmol) was added as a solid under a nitrogen atmosphere. After 75 min, the resulting mixture was allowed to cool to room temperature. Ethyl acetate (83 mL) and diethyl ether (167 mL) were added, and the organic layer was washed with water (2×250 mL), was dried over anhydrous magnesium sulfate, was filtered, and was concentrated under reduced pressure. The residue was purified by flash column chromatography on silica gel (0 to 100% ethyl acetate in hexanes) to give 6-((3'-bromo-2,2'-dichloro-[1,1'-biphenyl]-3-yl)methoxy)-5-chloro-2-((5-(methylsulfonyl)pyridin-3-yl)methoxy)nicotinaldehyde.

Step 5. A stirred mixture of 6-((3'-bromo-2,2'-dichloro-[1,1'-biphenyl]-3-yl)methoxy)-5-chloro-2-((5-(methylsulfonyl)pyridin-3-yl)methoxy)nicotinaldehyde (500 mg, 0.761 mmol), 2-(trimethylsilyl)ethyl (2-hydroxyethyl)(2-(4-(4,4,5,5-tetramethyl-1,3,2-dioxaborolan-2-yl)phenoxy)ethyl)carbamate (412 mg, 0.914 mmol), saturated aqueous sodium carbonate solution (2.0 M, 1.5 mL, 3.0 mmol), and [1,1'-bis(diphenylphosphino)ferrocene]dichloropalladium(II) (28 mg, 0.076 mmol) in 1,4-dioxane (8 mL) was heated to 105° C. in a heating block. After 5 h, the resulting mixture was purified by flash column chromatography on silica gel (0 to 30% ethyl acetate in hexanes) to give 2-(trimethylsilyl)ethyl (2-((2',2"-dichloro-3"-(((3-chloro-5-formyl-6-((5-(methylsulfonyl)pyridin-3-yl)methoxy)pyridin-2-yl)oxy)methyl)-[1,1':3',1"-terphenyl]-4-yl)oxy)ethyl)(2-hydroxyethyl)carbamate.

Step 6. Trifluoroacetic acid (2.0 mL) was added via syringe to a stirred solution of 2-(trimethylsilyl)ethyl (2-((2',2"-dichloro-3"-(((3-chloro-5-formyl-6-((5-(methylsulfonyl)pyridin-3-yl)methoxy)pyridin-2-yl)oxy)methyl)-[1,1':3',1"-terphenyl]-4-yl)oxy)ethyl)(2-hydroxyethyl)carbamate (100 mg, 0.111 mmol) in dichloromethane (5.0 mL) at room temperature. After 80 min, the resulting mixture was concentrated under reduced pressured. The residue was dried azeotropically by concentration of a toluene solution under reduced pressure (2×3 mL) to give 5-chloro-6-((2,2'-dichloro-4"-(2-((2-hydroxyethyl)amino)ethoxy)-[1,1':3',1"-terphenyl]-3-yl)methoxy)-2-((5-(methylsulfonyl)pyridin-3-yl)methoxy)nicotinaldehyde2,2,2-trifluoroacetate.

Intermediate 48: 5-chloro-6-((2,2'-dichloro-4"-(2-((2-hydroxyethyl)amino)ethoxy)-[1,1':3',1"-terphenyl]-3-yl)methoxy)-2-((5-(methylsulfonyl)pyridin-3-yl)methoxy)nicotinaldehyde2,2,2-trifluoroacetate

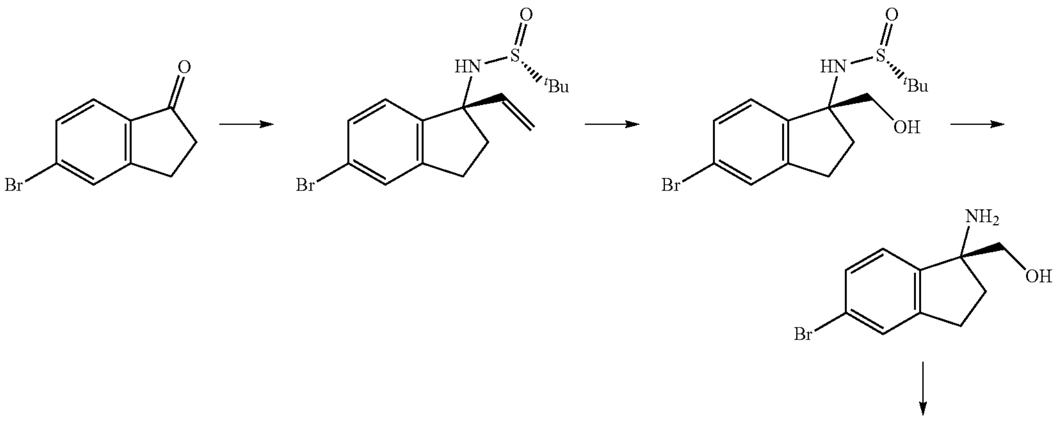

-continued

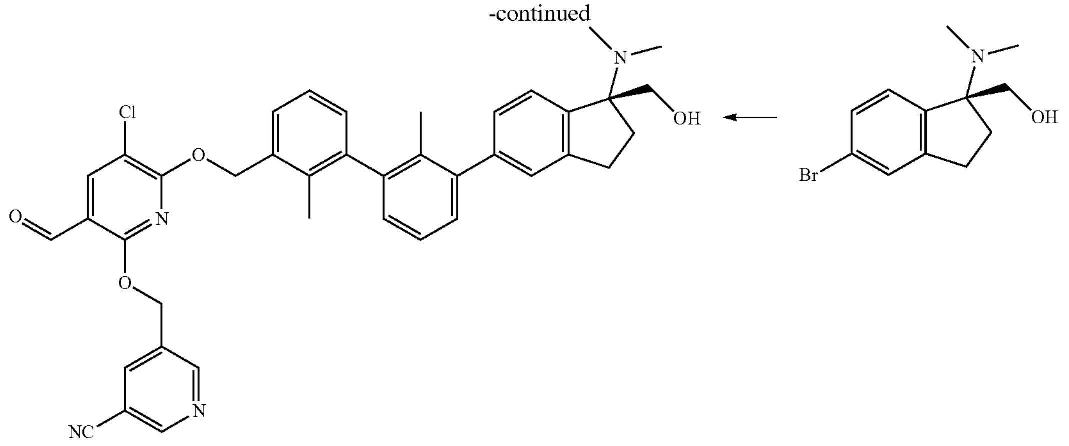

Step 1. A stirred mixture of 5-bromo-2,3-dihydro-1H-inden-1-one (10.0 g, 47.4 mmol), (R)-2-methylpropane-2-sulfinamide (6.32 g, 52.2 mmol), and tetraethoxytitanium (14.9 mL, 71.1 mmol) in toluene (50 mL) was heated to 95° C. in a heating block. After 15 h, the resulting mixture was allowed to cool to room temperature and was poured into vigorously stirred brine (50 mL). The resulting mixture was filtered through celite, and the filter cake was extracted with a mixture of diethyl ether and ethyl acetate (1:1 v:v, 100 mL). The organic layer was washed with brine (50 mL), was dried over anhydrous sodium sulfate, and was filtered through a short plug of silica. The filter cake was extracted with a mixture of diethyl ether and ethyl acetate (1:1 v:v, 100 mL), and the combined organic layers were concentrated under reduced pressure, and the residue was dried azeotropically by concentration of a toluene solution under reduced pressure (2×50 mL). The residue was dissolved in toluene (50 mL) and was stirred at room temperature. After 5 min, the resulting mixture was cooled to −78° C. After 10 min, trimethylaluminum solution (2.0 M in toluene, 13.4 mL, 27 mmol) was added via syringe. In a separate reaction vessel, tetravinylstannane (2.67 mL, 14.6 mmol) was added via syringe to a stirred mixture of of methyllithium solution (1.6 M in diethyl ether, 33.6 mL, 54 mmol) in toluene (100 mL) at 0° C. After 15 min, the resulting mixture was cooled to −78° C. After 15 min, the mixture of the dried residue from the first reaction and trimethylaluminum in toluene was added via cannula over 10 min. After 78 min, the resulting mixture was warmed to 0° C. After 100 min, vinylmagnesium bromide solution (1.0 M in tetrahydrofuran, 48.8 mL, 49 mmol) was added via syringe. After 2 h, saturated aqueous sodium sulfate solution was added over 5 min, and the resulting mixture was allowed to warm to room temperature with vigorous stirring and was filtered through celite. The filter cake was extracted with ethyl acetate (200 mL), and the combined organic layers were washed with brine (100 mL), were dried over anhydrous sodium sulfate, were filtered, and were concentrated under reduced pressure. The residue was purified by flash column chromatography on silica gel (0 to 100% ethyl acetate in hexanes) to give (R)—N—((S)-5-bromo-1-vinyl-2,3-dihydro-1H-inden-1-yl)-2-methylpropane-2-sulfinamide.

Step 2. Ozone was bubbled through a stirred solution of (R)—N—((S)-5-bromo-1-vinyl-2,3-dihydro-1H-inden-1-yl)-2-methylpropane-2-sulfinamide (667 mg, 1.95 mmol) in dichloromethane (20 mL) and methanol (20 mL) at −78° C. for 9 min, at which time a persistently blue colored mixture was obtained. Nitrogen gas was bubbled through the resulting mixture for 11 min, by which time the blue color had dissipated. Sodium borohydride (442 mg, 11.7 mmol) was added as a solid under a nitrogen atmosphere. After 15 min, the resulting mixture was allowed to warm to room temperature over 15 min. After 30 min, aqueous sodium thiosulfate solution (1.0 M, 5 mL) was added, and the resulting mixture was concentrated under reduced pressure. Ethyl acetate (100 mL) and saturated aqueous ammonium chloride solution (20 mL) were added, and the organic layer was washed with brine (50 mL), was dried over anhydrous sodium sulfate, was filtered, and was concentrated under reduced pressure. The residue was purified by flash column chromatography on silica gel (0 to 10% methanol in dichloromethane) to give (R)—N—((R)-5-bromo-1-(hydroxymethyl)-2,3-dihydro-1H-inden-1-yl)-2-methylpropane-2-sulfinamide.

Step 3. Hydrogen chloride solution (5.0 M in 2-propanol, 2.96 mL, 15 mmol) was added via syringe to a stirred solution of (R)—N—((R)-5-bromo-1-(hydroxymethyl)-2,3-dihydro-1H-inden-1-yl)-2-methylpropane-2-sulfinamide (512 mg, 1.48 mmol) in 1,4-dioxane (5.3 mL) at 0° C., and the resulting mixture was allowed to warm to room temperature. After 30 min, the resulting mixture was concentrated under reduced pressure. The residue was dried azeotropically by concentration of a toluene solution under reduced pressure (2×7 mL) to give (R)-(1-amino-5-bromo-2,3-dihydro-1H-inden-1-yl)methanol hydrochloride.

Step 4. Sodium triacetoxyborohydride (761 mg, 3.59 mmol) was added as a solid to a vigorously stirred mixture of (R)-(1-amino-5-bromo-2,3-dihydro-1H-inden-1-yl)methanol hydrochloride (200 mg, 0.718 mmol), aqueous formaldehyde solution (37% w/w, 267 μL, 3.59 mmol) and potassium acetate (141 mg, 1.44 mmol) in dichloromethane (3.6 mL) and tetrahydrofuran (3.6 mL) at room temperature. After 30 min, the resulting mixture was filtered and was concentrated under reduced pressure. The residue was purified by reverse phase preparative hplc (0.1% trifluoroacetic acid in acetonitrile/water) to give (R)-(5-bromo-1-(dimethylamino)-2,3-dihydro-1H-inden-1-yl)methanol 2,2,2-trifluoroacetate.

Step 5. A stirred mixture of 5-((4-chloro-5-((2,2'-dimethyl-3'-(4,4,5,5-tetramethyl-1,3,2-dioxaborolan-2-yl)-[1,1'-biphenyl]-3-yl)methoxy)-2-formylphenoxy)methyl)nicotinonitrile (25 mg, 0.041 mmol), (R)-(5-bromo-1-(dimethylamino)-2,3-dihydro-1H-inden-1-yl)methanol 2,2,2-trifluoroacetate (32 mg, 0.082 mmol), saturated aqueous sodium carbonate solution (2.0 M, 164 μL, 0.33 mmol), and chloro(2-dicyclohexylphosphino-2',4',6'-triisopropyl-1,1'-biphenyl)[2-(2'-amino-1,1'-biphenyl)]palladium(II) (2 mg, 0.002 mmol) in 1,4-dioxane (1.5 mL) was heated to 105° C. in a heating block. After 60 min, the resulting mixture was purified by flash column chromatography on silica gel (0 to 20% methanol in dichloromethane) to give (R)-5-(((5-chloro-6-((3'-(1-(dimethylamino)-1-(hydroxymethyl)-2,3-dihydro-1H-inden-5-yl)-2,2'-dimethyl-[1,1'-biphenyl]-3-yl)methoxy)-3-formylpyridin-2-yl)oxy)methyl)nicotinonitrile.

Intermediate 49: 2,2'-(2,2'-dimethyl-[1,1'-biphenyl]-3,3'-diyl)bis(4,4,5,5-tetramethyl-1,3,2-dioxaborolane)

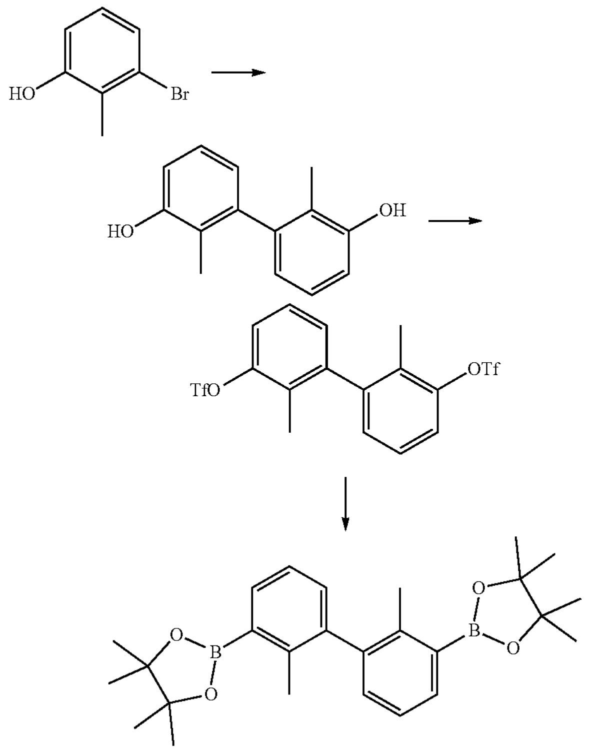

A solution of 3-bromo-2-methylphenol (5 g, 26.7 mmol), $B_2Pin_2$(8.1 g 32.1 mmol), $Pd(dppf)Cl_2$ (3.3 g, 4 mmol) and KOAc (6.9 g, 70 mmol) in dioxane (100 mL) was sparged with argon for 15 min. The reaction mixture was heated at 90° C. for 5 h under argon atmosphere. The reaction was cooled to ambient temperatures followed by addition of a solution of 3-bromo-2-methylphenol (5 g, 26.7 mmol) in 20 mL of dioxane and $K_2CO_3$ (7.4 g, 53 mmol) in 25 mL $H_2O$. The reaction was heated at 90° C. for an additional 16 h. The reaction was cooled to ambient temperatures, and poured into a mixture of sat. aq. $NH_4Cl$ and EtOAc. The layers were separated and the aqueous layer was further extracted with EtOAc. The combined organic layers were washed with brine, dried (over $Na_2SO_4$), filtered and concentrated in vacuo. The crude mixture was purified by $SiO_2$ column chromatography (ISCO gold, 120 g column; 0-60% EtOAc/Hex) to afford 4.4 g (77%) of 2,2'-dimethyl-[1,1'-biphenyl]-3,3'-diol as a white solid. $^1H$ NMR (400 MHz, DMSO-d6) δ 9.28 (s, 1H), 6.97 (t, J=7.8 Hz, 1H), 6.75 (dd, J=8.0, 1.2 Hz, 1H), 6.46 (dd, J=7.5, 1.2 Hz, 1H), 3.30 (s, 1H), 1.76 (s, 3H).

To a solution of 2,2'-dimethyl-[1,1'-biphenyl]-3,3'-diol (824 mg, 3.85 mmol) in $CH_2Cl_2$ (20.0 mL) cooled in an ice-water bath was added N,N-Diisopropylethylamine (2.68 mL, 15.4 mmol) followed by dropwise addition of Trifluoromethanesulfonic Anhydride (1.58 mL, 9.61 mmol). The reaction mixture was maintained in the bath allowing it warm to room temperature over 2 h. The reaction mixture was quenched by the addition of sat $NH_4Cl$ and EtOAc. The layers were separated and the aqueous layer was further extracted with EtOAc. The combined organic layers were washed with brine, dried (over $Na_2SO_4$), filtered and concentrated in vacuo. The crude mixture was purified by SiO2 column chromatography (ISCO gold, 40 g column; 0-100% EtOAc/Hex) to afford 1.6 g (87%) 2,2'-dimethyl-[1,1'-biphenyl]-3,3'-diyl bis(trifluoromethanesulfonate). $^1H$ NMR (400 MHz, Chloroform-d) δ 7.40-7.28 (m, 2H), 7.16 (dd, J=6.6, 2.2 Hz, 1H), 2.05 (s, 3H).

2,2'-dimethyl-[1,1'-biphenyl]-3,3'-diyl bis(trifluoromethanesulfonate) (1.6 g, 3.34 mmol), $B_2Pin_2$ (2.12 g, 8.36 mmol), KOAc (984 mg, 10.0 mmol) and $Pd(dppf)Cl_2$ (553 mg, 0.67 mmol) were suspended in dioxane (32.0 mL) and sparged with argon for 10 min. The reaction mixture was stirred at 90° C. for 16 h. The mixture was cooled to ambient temperatures and quenched by the addition of sat NH4Cl and EtOAc. The layers were separated and the aqueous layer was further extracted with EtOAc. The combined organic layers were washed with brine, dried (over Na2SO4), filtered and concentrated in vacuo. The crude mixture was purified by $SiO_2$ column chromatography (ISCO gold, 40 g column; 0-100% EtOAc/Hex) to afford 2,2'-(2,2'-dimethyl-[1,1'-biphenyl]-3,3'-diyl)bis(4,4,5,5-tetramethyl-1,3,2-dioxaborolane). $^1H$ NMR (400 MHz, Chloroform-d) δ 7.74 (dd, J=7.3, 1.6 Hz, 1H), 7.19 (t, J=7.4 Hz, 1H), 7.12 (dd, J=7.6, 1.6 Hz, 1H), 2.20 (s, 3H), 1.35 (s, 12H).

Intermediate 50: 6,6'-(2,2'-dimethyl-[1,1'-biphenyl]-3,3'-diyl)bis(2-methoxynicotinaldehyde)

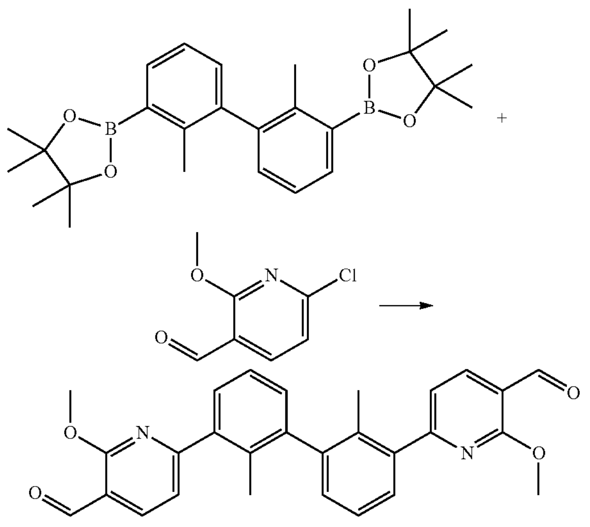

2,2'-(2,2'-dimethyl-[1,1'-biphenyl]-3,3'-diyl)bis(4,4,5,5-tetramethyl-1,3,2-dioxaborolane) (200 mg, 0.46 mmol), 6-chloro-2-methoxynicotinaldehyde (205 mg, 1.2 mmol), Pd(PPh3)4 (80 mg, 0.07 mmol), and K2CO3 (254 mg, 1.84 mmol) were charged in a vial and suspended in Dioxane (10 mL) and water (1 mL). The mixture was sparged with argon for 5 min, and sealed with a teflon coated cap. The mixture was stirred at 90° C. for 8 h. After cooling to room temperature, the reaction was diluted with ethyl acetate and brine. The organic layer was separated, dried with anhydrous sodium sulfate, concentrated, and purified by silica gel chromatography to provide 6,6'-(2,2'-dimethyl-[1,1'-biphenyl]-3,3'-diyl)bis(2-methoxynicotinaldehyde).

Intermediate 51: (R)-1-((2',2"-dimethyl-3"-(4,4,5,5-tetramethyl-1,3,2-dioxaborolan-2-yl)-[1,1':3',1"-terphenyl]-4-yl)methyl)pyrrolidin-3-ol

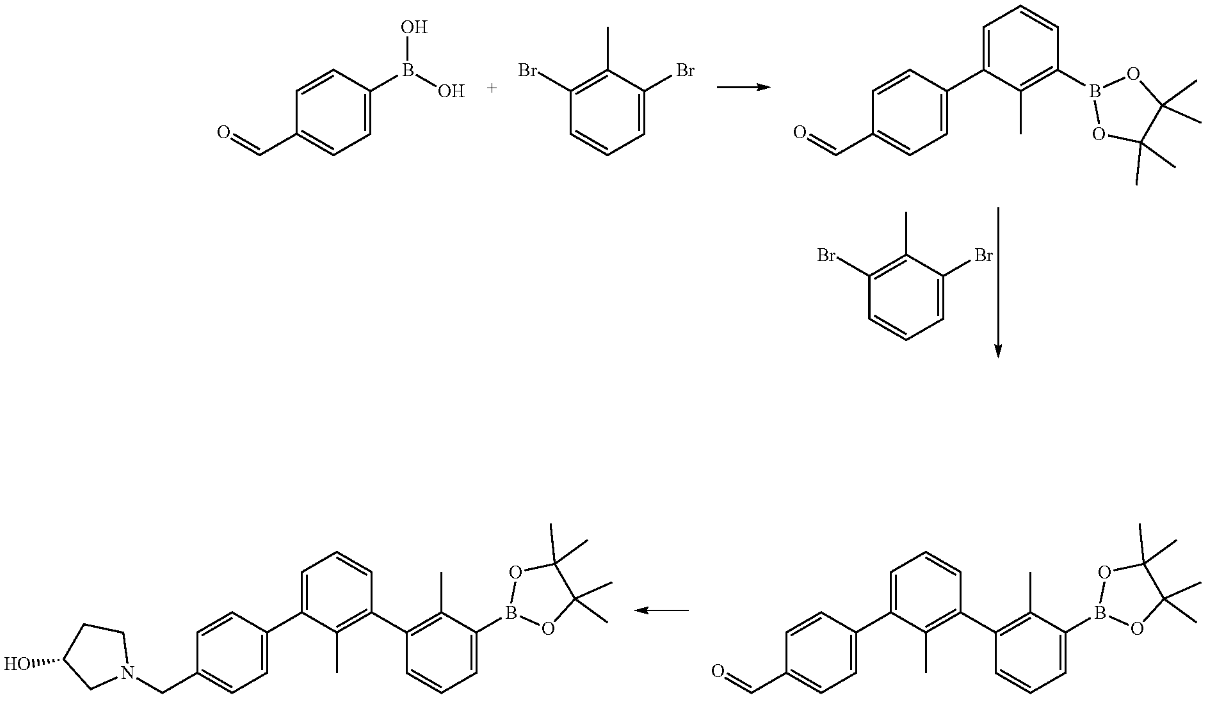

(4-Formylphenyl)boronic acid (2 g, 13.34 mmol), 1,3-dibromo-2-methylbenzene (6.67 g, 26.68 mmol), Pd(dppf) $Cl_2CH_2Cl_2$ (0.55 g, 0.67 mmol) and potassium carbonate (3.7 g, 26.7 mmol) were suspended in 20 mL dioxane and 2 mL water. The mixture was sparged for 10 min with argon and heated to 90° C. in a heating block for 4 h. After cooling to room temperature, the reaction was diluted with EtOAc and brine. The organic layer was separated, dried with $Na_2SO_4$ and concentrated. Purified by silica gel chromatography (eluting with EtOAc-Hex) to provide 2.46 g (67%) of 3'-bromo-2'-methyl-[1,1'-biphenyl]-4-carbaldehyde.

3'-bromo-2'-methyl-[1,1'-biphenyl]-4-carbaldehyde (1.4 g, 5.09 mmol), bis(pinacolato)diboron (1.42 g, 5.6 mmol), KOAc (1.5 g, 15.2 mmol) and [1,1'-bis(diphenylphosphino)ferrocene]palladium(II) dichloride (0.42 g, 0.51 mmol) were suspended in 10 mL dioxane and argon was bubbled through the mixture for 5 min. The reaction was heated to 90° C. for 3 h, after which the reaction was cooled to room temperature and diluted with 100 mL EtOAc. The reaction mixture was filtered through a celite pad, concentrated under reduced pressure, and purified by silica gel chromatography to provide 1.32 g (80.5%) of 2'-methyl-3'-(4,4,5,5-tetramethyl-1,3,2-dioxaborolan-2-yl)-[1,1'-biphenyl]-4-carbaldehyde.

2'-methyl-3'-(4,4,5,5-tetramethyl-1,3,2-dioxaborolan-2-yl)-[1,1'-biphenyl]-4-carbaldehyde (1 g, 3.1 mmol), 1,3-dibromo-2-methylbenzene (1.57 g, 6.2 mmol), Pd(dppf) $Cl_2CH_2Cl_2$ (0.178 g, 0.22 mmol) and potassium carbonate (1.3 g, 9.3 mmol) were suspended in 10 mL dioxane and 1 mL water. The mixture was sparged for 10 min with argon and heated to 90° C. in a heating block for 4 h. After cooling to room temperature, the reaction was diluted with EtOAc and brine. The organic layer was separated, dried with $Na_2SO_4$ and concentrated. Purified by silica gel chromatography (eluting with EtOAc-Hex) to provide 0.72 g (63%) of 3"-bromo-2',2"-dimethyl-[1,1':3',1"-terphenyl]-4-carbaldehyde.

3"-bromo-2',2"-dimethyl-[1,1':3',1"-terphenyl]-4-carbaldehyde (0.720 g, 2.0 mmol), bis(pinacolato)diboron (0.55 g, 2.2 mmol), KOAc (0.58 g, 5.9 mmol) and [1,1'-bis(diphenylphosphino)ferrocene]palladium(II) dichloride (0.16 g, 0.2 mmol) were suspended in 8 mL dioxane and argon was bubbled through the mixture for 5 min. The reaction was heated to 90° C. for 3 h, after which the reaction was cooled to room temperature and diluted with 100 mL EtOAc. The reaction mixture was filtered through a celite pad, concentrated under reduced pressure, and purified by silica gel chromatography to provide 600 mg (74%) of 2',2"-dimethyl-3"-(4,4,5,5-tetramethyl-1,3,2-dioxaborolan-2-yl)-[1,1':3',1"-terphenyl]-4-carbaldehyde.

2',2"-dimethyl-3"-(4,4,5,5-tetramethyl-1,3,2-dioxaborolan-2-yl)-[1,1':3',1"-terphenyl]-4-carbaldehyde (250 mg, 0.61 mmol), in DCM (15 mL) was added a solution of (R)-pyrrolidin-3-ol (80 mg, 1.5 eq) in DCM (10 mL). The resulting solution was allowed to stir for 1 h at room temperature. $Na(OAc)_3BH$ (192.75 mg, 0.91 mmol) was added in one portion, and stirred for an additional 3 h. The reaction was diluted with DCM, and washed with $NaHCO_3$, and Brine. The organic layer was dried over Na2SO4, and concentrated and purified silica gel chromatography (20% MeOH in DCM) to provide (R)-1-((2',2"-dimethyl-3"-(4,4,5,5-tetramethyl-1,3,2-dioxaborolan-2-yl)-[1,1':3',1"-terphenyl]-4-yl)methyl)pyrrolidin-3-ol.

Intermediate 52: Tert-butyl (S)-2-(5-bromo-1H-benzo[d]imidazol-2-yl)pyrrolidine-1-carboxylate

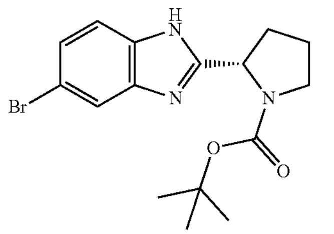 [SMILES: CC(C)(C)OC(=O)N1CCC[C@H]1c1nc2cc(Br)ccc2[nH]1]

Tert-butyl (S)-2-(5-bromo-1H-benzo[d]imidazol-2-yl) pyrrolidine-1-carboxylate was synthesized following procedures in PCT Int. Appl. (2010), WO 2010/132601.

Intermediate 53: 4-((3-bromo-2-methylphenoxy) methyl)-5-chloro-2-hydroxybenzaldehyde

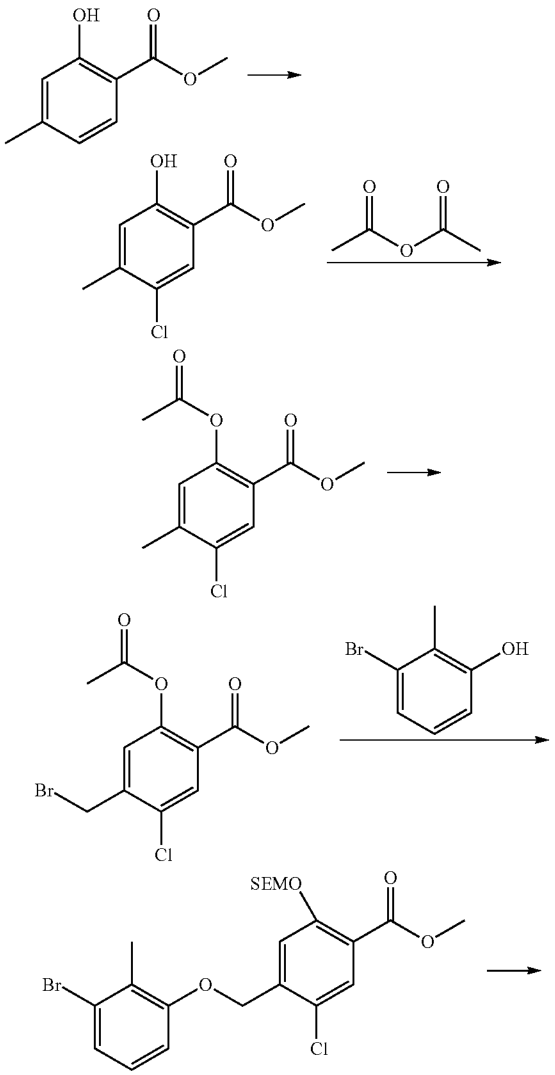

-continued

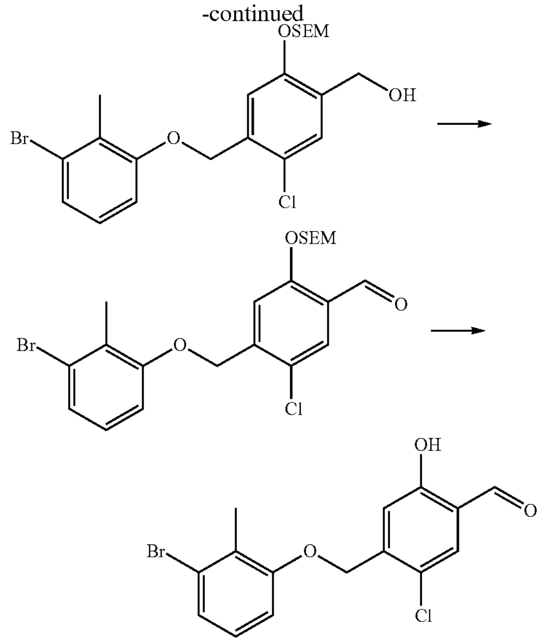

Methyl-4-methylsalicylate (6300 mg, 37.91 mmol) and n-chlorosuccinimide (5568.61 mg, 41.7 mmol) were stirred and heated to 42° C. overnight in acetonitrile (200 mL). Reaction was diluted with EtAc and quenched with aqueous sodium thiosulfate. Reaction was extracted with EtAc (3×) washed with thiosulfate, water then brine, dried over sodium sulfate, filtered and evaporated to dryness. Crude material was purified by silica gel chromatography using Hex/DCM as the eluent to afford 6300 mg (66.3%) of methyl 5-chloro-2-hydroxy-4-methylbenzoate.

Methyl 5-chloro-2-hydroxy-4-methylbenzoate (6300 mg, 31.4 mmol) was taken up in Pyridine (250 mL) and to this was added Acetic Anhydride (5.94 mL, 62.81 mmol) and reaction allowed to stir at room temperature overnight.

Next day solvents were removed under reduced pressure and coevapped with DCM (2×) then placed under high vacuum. Crude material was purified by silica gel chromatography using Hexanes/EtAc as the eluent to provide 7.4 g (97%) of methyl 2-acetoxy-5-chloro-4-methylbenzoate.

To methyl 2-acetoxy-5-chloro-4-methylbenzoate (8300 mg, 34.2 mmol) and N-bromosuccinimide (5783.57 mg, 32.49 mmol) was added CCl4 (400 mL) and reaction stirred at room temperature for 10 minutes then benzoyl peroxide (134.76 mg, 0.56 mmol) was added and reaction was heated to 82° C. overnight. Next day reaction solvents were removed under reduced pressure and crude material was purified by flash chromatography using Hex/DCM as the eluent to obtain 8 g (58.2%) of methyl 2-acetoxy-4-(bromomethyl)-5-chlorobenzoate.

methyl 2-acetoxy-4-(bromomethyl)-5-chlorobenzoate (6500 mg, 20.21 mmol), 3-Bromo-2-methylphenol (7561.69 mg, 40.43 mmol), sodium iodide (6060.08 mg, 40.43 mmol) and cesium carbonate (19758.82 mg, 60.64 mmol) were stirred in DMF (400 mL) and heated to 50° C. under an argon atmosphere. After 60 minutes starting material was consumed. Reaction was cooled on ice water and to this was added 2-(trimethylsilyl)ethoxymethyl chloride (8.94 mL, 50.54 mmol) and reaction allowed to warm for 1 hour or until intermediate is consumed Reaction was diluted with EtAc, and LiCl (aq) extracted with EtAc 3×, washed with LiCl, water, brine, dried over sodium sulfate, filtered and solvents removed under reduced pressure. Crude material was purified by silica gel chromatography using Hexanes/EtAc to afford 12.7 g (85.2%) of methyl 4-((3-bromo-2-methylphenoxy)methyl)-5-chloro-2-((2-(trimethylsilyl)ethoxy)methoxy)benzoate.

Methyl 4-((3-bromo-2-methylphenoxy)methyl)-5-chloro-2-((2-(trimethylsilyl)ethoxy)methoxy)benzoate (12.5 g, 16.96 mmol) was taken up in 300 mL THF at room temperature and purged with argon. To this was added lithium aluminum hydride (95%) (1.09 g, 27.29 mmol). Upon consumption of starting materials sodium sulfate decahydrate (10 g) was slowly added to the reaction and stirred overnight. The following day solids were filtered off and mother liquor was evaporated to dryness under reduced pressure. Crude material was purified by silica gel chromatography using Hexanes/EtAc to afford 6.2 g (74.9%) of (4-((3-bromo-2-methylphenoxy)methyl)-5-chloro-2-((2-(trimethylsilyl)ethoxy)methoxy)phenyl)methanol.

(4-((3-bromo-2-methylphenoxy)methyl)-5-chloro-2-((2-(trimethylsilyl)ethoxy)methoxy)phenyl)methanol (6.2 g, 12.71 mmol) was taken up in DCM (250 mL) at room temperature under argon. To this was added Dess-martin periodinane (6.47 g, 15.25 mmol) and the reaction was stirred overnight. Upon completion reaction was stirred with sodium thiosulfate (aq) for 30 minutes then extracted with DCM (3×), dried over sodium sulfate, filtered and evaporated to dryness. Crude material was purified by silica gel chromatography using Hex/DCM as eluent to afford 4-((3-bromo-2-methylphenoxy)methyl)-5-chloro-2-((2-(trimethylsilyl)ethoxy)methoxy)benzaldehyde.

4-((3-bromo-2-methylphenoxy)methyl)-5-chloro-2-((2-(trimethylsilyl)ethoxy)methoxy)benzaldehyde (5500 mg, 11.32 mmol) and magnesium bromide etherate (5846.36 mg, 22.64 mmol) were stirred in DCM (250 mL) for 1 hour at room temperature or until starting materials were consumed. To the reaction was ammonium chloride (aq.) and extracted with DCM (3×)), dried over sodium sulfate, filtered and evaporated to dryness. Crude material was taken up in DCM and solids were sonicated and filtered off to provide product. Mother liquor was purified by silica gel chromatography using Hex/DCM as eluent to afford 4-((3-bromo-2-methylphenoxy)methyl)-5-chloro-2-hydroxybenzaldehyde.

Intermediate 54: 5-((4-chloro-5-(((3'-((2-chloro-5-((5-cyanopyridin-3-yl)methoxy)-4-formylphenoxy)methyl)-2,2'-dimethyl-[1,1'-biphenyl]-3-yl)oxy)methyl)-2-formylphenoxy)methyl)nicotinonitrile

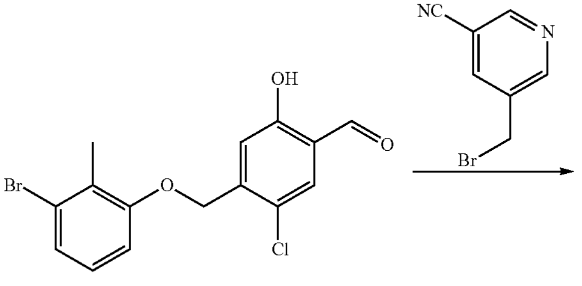

-continued

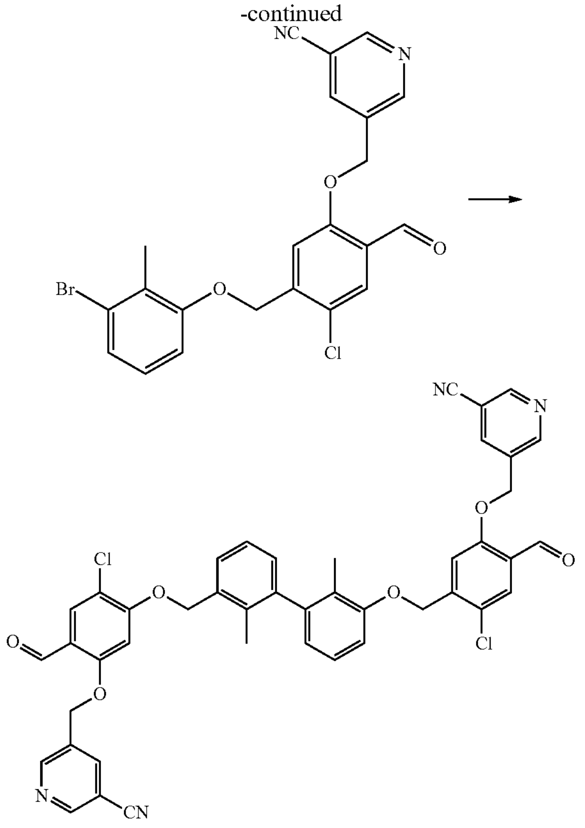

4-((3-bromo-2-methylphenoxy)methyl)-5-chloro-2-hydroxybenzaldehyde (520 mg, 1.46 mmol), 5-(chloromethyl)nicotinonitrile hydrochloride (414.64 mg, 2.19 mmol), Sodium Iodide (657.56 mg, 4.39 mmol), Potassium carbonate (1212.55 mg, 8.77 mmol) and N,N-Dimethylformamide (50 mL) were placed in a round-bottomed flask equipped with stir bar and heated to 65° C. for 12 hours. A t this point reaction was cooled to room temperature and diluted with EtAc/aq. LiCl. Organics were extracted 3× with EtAc, washed with aq. LiCl 3×, water 1×, brine, then dried over sodium sulfate before filtering and evaporating organics under reduced pressure to afford crude residue. Crude material was purified by silica gel chromatography using Hexanes/EtAc as the eluent 260 mg (37.7%) of 5-((5-((3-bromo-2-methylphenoxy)methyl)-4-chloro-2-formylphenoxy)methyl)nicotinonitrile.

5-((5-((3-bromo-2-methylphenoxy)methyl)-4-chloro-2-formylphenoxy)methyl)nicotinonitrile (50 mg, 0.11 mmol), 5-((4-chloro-2-formyl-5-((2-methyl-3-(4,4,5,5-tetramethyl-1,3,2-dioxaborolan-2-yl)benzyl)oxy)phenoxy)methyl)nicotinonitrile, Pd(dppf)$Cl_2$ (10.85 mg, 0.01 mmol) and potassium carbonate (43.95 mg, 0.32 mmol) were placed in a microwave vial equipped with a stir bar and to this was added DMF (5 mL), water (1 mL) then the reaction vessel was sealed and microwaved at 90° C. for 45 minutes.

Reaction was diluted in EtAc/$H_2O$ and extracted with EtAc (3×). Organics were then washed with lithium chloride, water, brine, then dried over sodium sulfate before filtering and evaporating organics under reduced pressure to afford crude residue.

Crude material was purified by silica gel chromatography using DCM/EtAc as the eluent to provide 5-((4-chloro-5-(((3'-((2-chloro-5-((5-cyanopyridin-3-yl)methoxy)-4-formylphenoxy)methyl)-2,2'-dimethyl-[1,1'-biphenyl]-3-yl)oxy)methyl)-2-formylphenoxy)methyl)nicotinonitrile.

Intermediate 55: 5-((4-chloro-5-((3'-((2-chloro-4-formyl-5-methoxybenzyl)oxy)-2,2'-dimethyl-[1,1'-biphenyl]-3-yl)methoxy)-2-formylphenoxy)methyl)nicotinonitrile

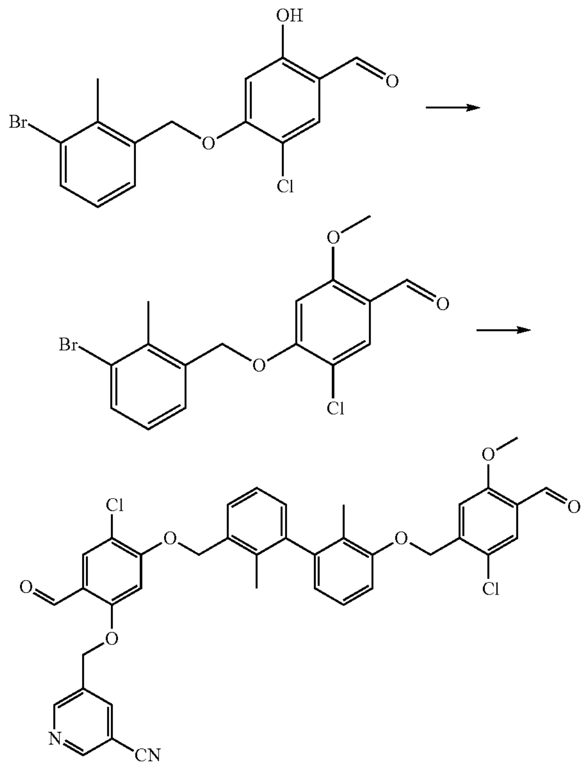

4-((3-bromo-2-methylphenoxy)methyl)-5-chloro-2-hydroxybenzaldehyde (250 mg, 0.7 mmol) was taken up in DMF (25 mL) and to this was added potassium carbonate (388.64 mg, 2.81 mmol) followed by iodomethane (0.22 mL, 2.81 mmol) and the reaction was heated to 45° C. for 3 hours with stirring. Reaction was cooled then diluted in EtAc/aq. LiCl and extracted with EtAc (3×). Organics were then washed with lithium chloride, water, brine, then dried over sodium sulfate before filtering and evaporating organics under reduced pressure to afford crude residue.

Crude material was purified by silica gel chromatography using Hex/EtAc as the eluent to afford 210 mg (80.8%) of 4-((3-bromo-2-methylphenoxy)methyl)-5-chloro-2-methoxybenzaldehyde. [M+1]=370.8

4-((3-bromo-2-methylphenoxy)methyl)-5-chloro-2-methoxybenzaldehyde (80 mg, 0.22 mmol), 5-((4-chloro-2-formyl-5-((2-methyl-3-(4,4,5,5-tetramethyl-1,3,2-dioxaborolan-2-yl)benzyl)oxy)phenoxy)methyl)nicotinonitrile (134.74 mg, 0.26 mmol), Pd(dppf)$Cl_2$ (22.16 mg, 0.03 mmol) and potassium carbonate (89.73 mg, 0.65 mmol) were placed in a microwave vial equipped with a stir bar and to this was added DMF (6 mL), water (2 mL) then the reaction vessel was sealed and microwaved at 95° C. for 45 minutes.

Reaction was diluted in EtAc/H2O and extracted 3× with EtAc. Organics were then washed with ammonium chloride 1×, water 1×, brine, then dried over sodium sulfate before filtering and evaporating organics under reduced pressure to afford crude residue.

Crude material was purified by silica gel chromatography using DCM/EtAc as the eluent to provide 5-((4-chloro-5-((3'-((2-chloro-4-formyl-5-methoxybenzyl)oxy)-2,2'-dimethyl-[1,1'-biphenyl]-3-yl)methoxy)-2-formylphenoxy)methyl)nicotinonitrile.

Intermediate 56: 5-((4-chloro-2-formyl-5-((3'-((5-formylpyridin-2-yl)methoxy)-2,2'-dimethyl-[1,1'-biphenyl]-3-yl)methoxy)phenoxy)methyl)nicotinonitrile

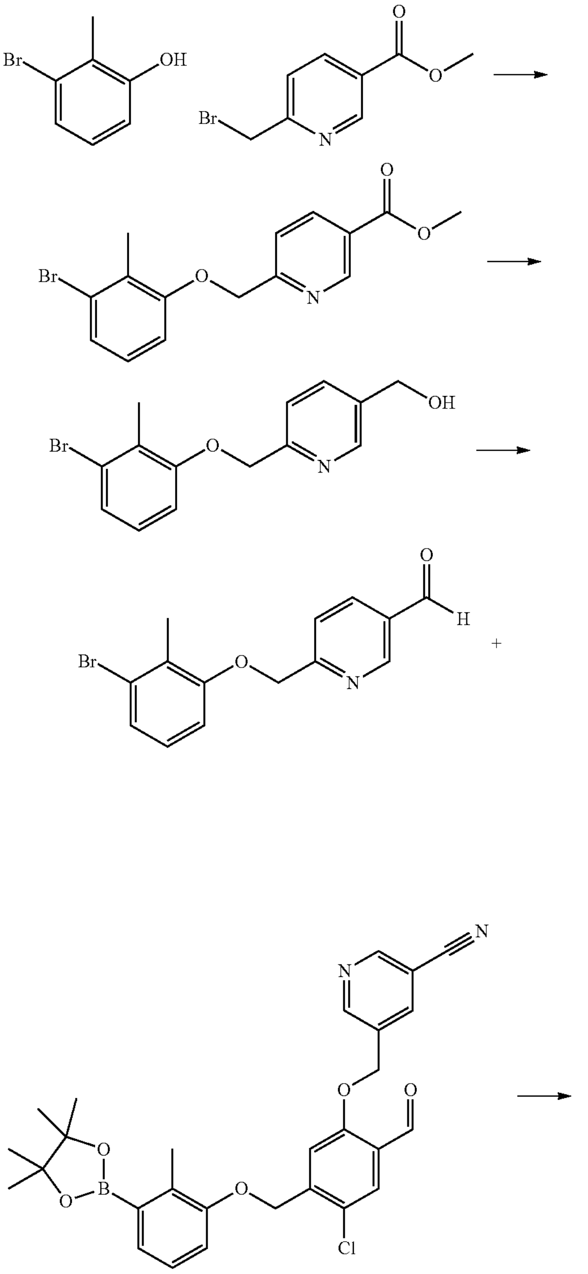

-continued

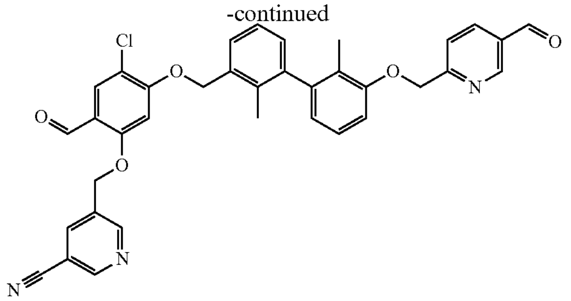

3-bromo-2-methylphenol (0.36 mL, 2.86 mmol) was stirred in DMF (15 mL) at room temperature under argon and to this was added NaH (55%, 149.78 mg, 3.43 mmol) and suspension was stirred for 10 minutes. At this point methyl 6-(bromomethyl)nicotinate (723.88 mg, 3.15 mmol) was added and reaction was stirred until reaction was complete. Reaction was diluted in EtAc and LiCl (aq) and extracted with EtAc (3×). Organics were washed with LiCl (aq), water, brine, dried over sodium sulfate, filtered and evaporated to dryness to afford 990 mg of methyl 6-((3-bromo-2-methylphenoxy)methyl)nicotinate as crude.

methyl 6-((3-bromo-2-methylphenoxy)methyl)nicotinate (990 mg, 2.94 mmol) was dissolved in ether (100 mL) and to this was added lithium aluminum hydride (134.12 mg, 3.53 mmol) and stirred overnight. The next day LCMS shows complete consumption of starting material. Reaction was poured into stirring solution of EtAc and aqueous solution of Rochelle's salt and stirred for 3 hours. Reaction was extracted 3× with EtAc, washed with water and brine, dried over sodium sulfate, filtered and evaporated to dryness to afford 850 mg (93.7%) of (6-((3-bromo-2-methylphenoxy)methyl)pyridin-3-yl)methanol. [M+1]=310.1.

(6-((3-bromo-2-methylphenoxy)methyl)pyridin-3-yl) methanol (850 mg, 2.76 mmol)) was dissolved 100 mL DCM and to this was added Dess-martin periodinane (1286.85 mg, 3.03 mmol) and stirred overnight at room temperature. Reaction was quenched with stirring sodium thiosulfate for 15 minutes the diluted with DCM. Organics were extracted with DCM (3×) washed with water, dried over sodium sulfate, filtered and evaporated to dryness.

Crude material was purified by silica gel chromatography using Hexanes/EtAc as the eluent (to afford 830 mg (98.3%) of 6-((3-bromo-2-methylphenoxy)methyl)nicotinaldehyde. [M+1]=308.0.

5-((4-chloro-2-formyl-5-((2-methyl-3-(4,4,5,5-tetramethyl-1,3,2-dioxaborolan-2-yl)benzyl)oxy)phenoxy)methyl) nicotinonitrile (200 mg, 0.39 mmol), 6-((3-bromo-2-methylphenoxy)methyl)nicotinaldehyde (129.83 mg, 0.42 mmol), Pd(dppf)$Cl_2$ (39.47 mg, 0.0482 mmol), $K_2CO_3$ (79.45 mg, 0.82 mmol), 1,4-Dioxane (8 mL) and water (4 mL) were placed in a microwave vial equipped with stir bar and heated in a microwave at 95° C. for 30 minutes.

Reaction was diluted in EtAc/$H_2O$ and extracted with EtAc (3×). Organics were then washed with ammonium chloride, water, brine, then dried over sodium sulfate before filtering and evaporating organics under reduced pressure to afford crude residue.

Crude material was purified by silica gel chromatography using Hex/EtAc as the eluent to afford 5-((4-chloro-2-formyl-5-((3'-((5-formylpyridin-2-yl)methoxy)-2,2'-dimethyl-[1,1'-biphenyl]-3-yl)methoxy)phenoxy)methyl)nicotinonitrile. [M+1]=618.0.

Intermediate 57: 5-((4-chloro-5-(((2,2'-dimethyl-4"-(2-oxoethoxy)-[1,1':3',1"-terphenyl]-3-yl)oxy)methyl)-2-formylphenoxy)methyl)nicotinonitrile

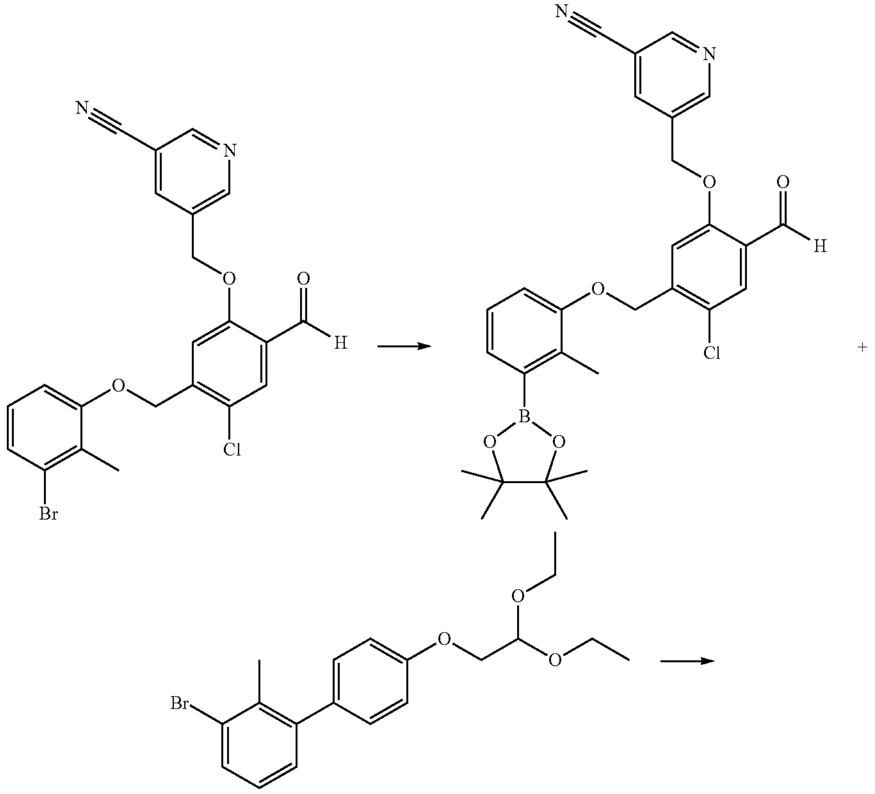

-continued

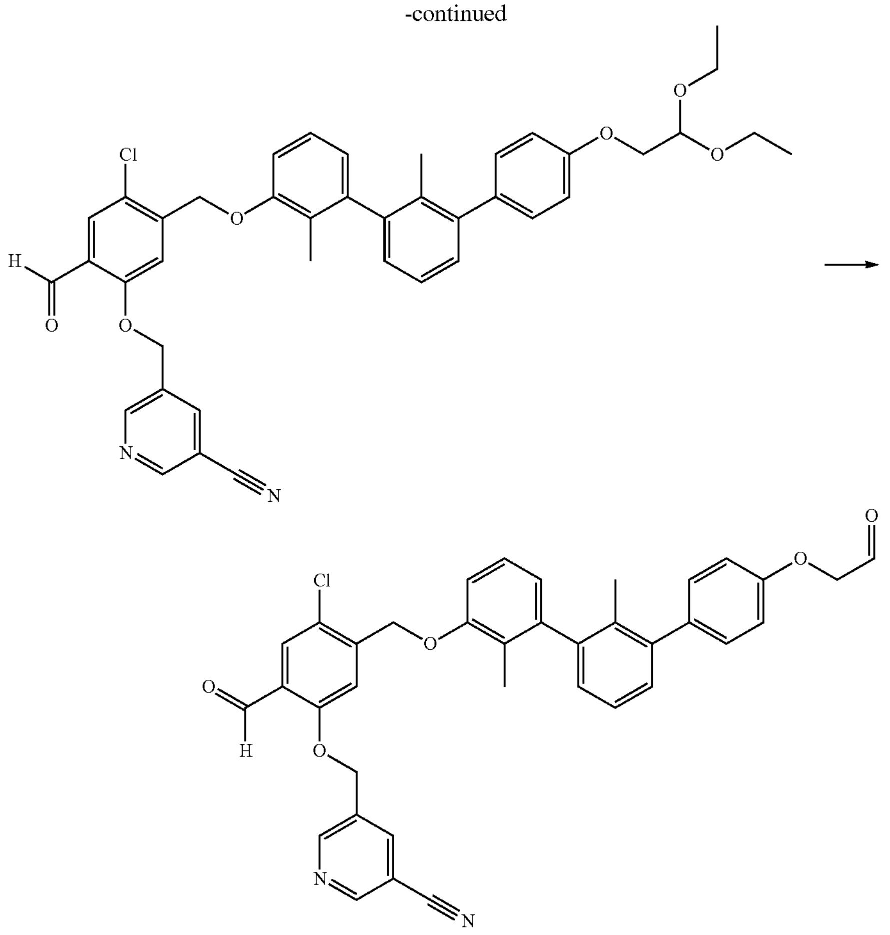

5-((5-((3-bromo-2-methylphenoxy)methyl)-4-chloro-2-formylphenoxy)methyl)nicotinonitrile (410 mg, 0.87 mmol), bis (pinacolato) diboron (331.06 mg, 1.3 mmol), (1,1'-Bis(diphenylphosphino)ferrocene)dichloropalladium (II), complex with dichloromethane (60.84 mg, 0.09 mmol), potassium acetate (156.58 mg, 2.61 mmol) and Dioxane (5 mL) were placed in a sealed vial equipped with stir bar and stirred for 24 hours at 95° C. Reaction was cooled, filtered and solvents removed under reduced pressure. Crude material was purified by silica gel chromatography using Hexanes/EtAc as the eluent to afford 210 mg (46.6%) of 5-((4-chloro-2-formyl-5-((2-methyl-3-(4,4,5,5-tetramethyl-1,3,2-dioxaborolan-2-yl)phenoxy)methyl)phenoxy)methyl) nicotinonitrile.

5-((4-chloro-2-formyl-5-((2-methyl-3-(4,4,5,5-tetramethyl-1,3,2-dioxaborolan-2-yl)phenoxy)methyl)phenoxy) methyl)nicotinonitrile (120 mg, 0.23 mmol), 3-bromo-4'-(2,2-diethoxyethoxy)-2-methyl-1,1'-biphenyl (105.28 mg, 0.28 mmol), Pd(dppf)$Cl_2$ (23.68 mg, 0.03 mmol) and cesium carbonate (158.26 mg, 0.49 mmol) were placed in a microwave vial equipped with a stir bar and to this was added 1,4-Dioxane (8 mL), water (4 mL) then the reaction vessel was sealed and microwaved at 95° C. for 45 minutes. Reaction was diluted in EtAc/$H_2O$ and extracted 3× with EtAc. Organics were then washed with ammonium chloride, water, brine, then dried over sodium sulfate before filtering and evaporating organics under reduced pressure to afford crude residue. Crude material was purified by silica gel chromatography using DCM/EtAc as the eluent to afford 100 mg (62.5%) of 5-((4-chloro-5-(((4"-(2,2-diethoxyethoxy)-2,2'-dimethyl-[1,1':3',1"-terphenyl]-3-yl)oxy) methyl)-2-formylphenoxy)methyl)nicotinonitrile.

5-((4-chloro-5-(((4"-(2,2-diethoxyethoxy)-2,2'-dimethyl-[1,1':3',1"-terphenyl]-3-yl)oxy)methyl)-2-formylphenoxy) methyl)nicotinonitrile (100 mg, 0.14 mmol) was dissolved in 1,4-dioxane (8 mL), 0.2 mL (conc, aq) HCl and stirred for 1 hour at room temperature. Reaction was quenched with saturated ammonium bicarbonate and extracted with EtAc (3×), dried over sodium sulfate and evaporated to dryness to afford 5-((4-chloro-5-(((2,2'-dimethyl-4"-(2-oxoethoxy)-[1,1':3',1"-terphenyl]-3-yl)oxy)methyl)-2-formylphenoxy) methyl)nicotinonitrile.

General Reductive Amination Procedures:

Procedure A—Reductive Amination with DMF/TEA; NaBH$(OAc)_3$

Aldehyde (1 equiv) was suspended in DMF (0.025 M) and to this was added (3S)-4-Amino-3-hydroxybutanoic acid (6 equiv) followed by triethylamine (6 equiv) and the reaction stirred at room temperature for 90 minutes. To this was added sodium triacetoxyborohydride (6 equiv) and the reaction stirred an additional 4 hours. At this point TFA was added slowly dropwise to the reaction until the solution went clear. Reaction was diluted with 2 mL of water, filtered and purified by reverse phase HPLC (0.1% trifluoroacetic acid in acetonitrile/water) providing the final compound upon lyophilization as the bis-TFA salt.

Procedure B—Reductive Amination with DMF/aq NaOH; NaBH$(OAc)_3$

A solution of aldehyde (1 equiv) in DMF (0.014 M) was added to a solution of the (S)-4-amino-3-hydroxybutanoic acid in 1N NaOH (10 equiv). After 2 h sodium triacetoxyborohydride (10 equiv) was added. After 30 min the reaction was complete and TFA was added. Solids were removed by filtration and rinsed with MeOH. Organic phase was removed under reduced pressure, and the crude subjected to purification by reverse phase HPLC (0.1% trifluoroacetic acid in acetonitrile/water) providing the final compound upon lyophilization as the bis-TFA salt.

Procedure C—Reductive Amination with DMF/AcOH; $NaCNBH_3$+$NaBH(OAc)_3$

To a stirred mixture of aldehyde (1 equiv) and (S)-3-aminobutanoic acid (15 equiv) in a 6:1 mixture of DMF/AcOH (0.02 M) at room temperature was added sequentially sodium cyanoborohydride (9 equiv) and sodium triacetoxyborohydride (9 equiv). After 15 min, trifluoroacetic acid was added until the solution went clear. The resulting mixture was purified by reverse phase HPLC (0.1% trifluoroacetic acid in acetonitrile/water) providing the final compound upon lyophilization as the bis-TFA salt.

Procedure D—Reductive Amination with DMSO/AcOH; $NaBH(OAc)_3$

To a stirred mixture of aldehyde (1 equiv) and (1R,2R)-2-aminocyclopentane-1-carboxylic acid (15 equiv) in 5:1 mixture of DMSO/AcOH (0.008 M) at room temperature was added sodium triacetoxyborohydride (9 equiv). After 1 h, TFA was added until the solution went clear. The resulting homogeneous mixture was purified by reverse phase HPLC (0.1% trifluoroacetic acid in acetonitrile/water) providing the final compound upon lyophilization as the bis-TFA salt.

Procedure E—Reductive Amination with MeOH/AcOH; 2-methylpyridine borane

Aldehyde A (1 equiv) was suspended in a 10:1 mixture of MeOH/AcOH (0.01M) and to this was added (3S)-4-amino-3-hydroxybutyric acid (3 equiv) at room temperature. Mixture was stirred at room temperature under argon for 1 hour. To this solution was added 2-methylpyridine borane (3 equiv) at room temperature and the reaction was stirred for an additional 2 hours. At this point, TFA was added dropwise to the reaction mixture until the solution went clear. Reaction was filtered and purified by reverse phase HPLC (0.1% trifluoroacetic acid in acetonitrile/water) providing the final compound upon lyophilization as the bis-TFA salt.

Procedure F—Reductive Amination with DMF/MeOH/AcOH; 2-methylpyridine borane

Aldehyde (1 equiv) was suspended in a 6:3:1 mixture of DMF/MeOH/AcOH (0.01 M) and to this was added (3S)-4-amino-3-hydroxybutyric acid (10 equiv) at room temperature. Mixture was stirred at room temperature under argon for 1 hour. To this solution was added 2-methylpyridine borane (10 equiv) at room temperature and the reaction was stirred for an additional 2 hours. At this point, TFA was added dropwise to the reaction mixture until the solution goes clear. Reaction was filtered and purified by reverse phase HPLC (0.1% trifluoroacetic acid in acetonitrile/water) providing the final compound upon lyophilization as the bis-TFA salt.

Procedure G—Reductive Amination with DCM/EtOH/KOH; $Na(OAc)_3BH$

To aldehyde in DCM (0.05M) was added a pre-sonicated 0.1M solution of KOH (10 equiv) and (3S)-4-amino-3-hydroxybutanoic acid (10 equiv) in EtOH. The reaction was stirred for 1 hour at rt before $Na(OAc)_3BH$ (10 equiv) and AcOH (10 equiv) were added. The cloudy reaction was sonicated for 1 min, and stirred at rt for 2 h. The reaction was quenched with the addition of 1M HCl until the solution clears. The solution was concentrated in-vacuo, diluted with a mixture of MeCN/$H_2O$/DMF (1:1:1), and purified by purified by reverse phase HPLC (0.1% trifluoroacetic acid in acetonitrile/water) providing the final compound upon lyophilization as the bis-TFA salt.

Procedure H—Reductive Amination with DCM/DMF/DIPEA; $Na(OAc)_3BH$

The di aldehyde 6,6'-(((2,2'-dimethyl-[1,1'-biphenyl]-3,3'-diyl)bis(methylene))bis(oxy))bis(5-chloro-2-methoxynicotinaldehyde) (50 mg, 1 equiv) was taken in a vial and dissolved in DCM (1.5 mL). The (2S,4R)-4-hydroxypiperidine-2-carboxylic acid (125 mg, 10 equiv) was dissolved in mixture of DMF (3 mL), and DIPEA (0.15 mL, 10equiv) in a another vial. These two solutions were mixed together and sonicated for 5 min, and allowed to stir for 1 h at room temperature. To well stirred mixture was added Na(OAc) $_3$BH at once and sonicated for 5 min to bring everything in to solution and allowed to stirred for overnight. The solution was concentrated under reduced pressure. The crude product was diluted with a mixture of MeCN/$H_2O$/(2:1, with 0.1% TFA), solids were removed by filtration and purified by reverse phase HPLC (0.1% trifluoroacetic acid in acetonitrile/water) providing the final compound as the bis-TFA salt.

Example 1: ((6-(((1S,1'S)-1'-((5-(((carboxymethyl)amino)methyl)-3-chloro-6-methoxypyridin-2-yl)oxy)-2,2',3,3'-tetrahydro-1H,1'H-[4,4'-biinden]-1-yl)oxy)-2-methoxypyridin-3-yl)methyl)glycine

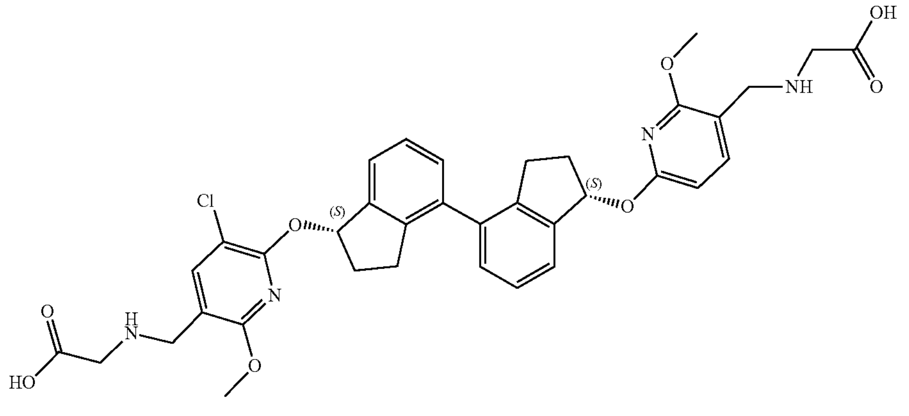

A solution of Intermediate 6 (65 mg, 0.11 mmol) was treated using Method E, substituting glycine for (S)-4-amino-3-hydroxybutanoic acid. Purification by prep RP-HPLC (10-75% acetonitrile in water, 0.1% trifluoroacetic acid) furnished 5-(2-(4-morpholinophenyl)-1-(phenylsulfonyl)-1H-pyrrolo[2,3-b]pyridin-4-yl)-2-((tetrahydro-2H-pyran-3-yl)oxy)benzonitrile. $^1H$ NMR (400 MHz, DMSO-$d_6$) δ 9.09 (s, 4H), 7.92 (s, 1H), 7.72 (d, J=8.1 Hz, 1H), 7.42 (d, J=6.8 Hz, 2H), 7.36-7.27 (m, 4H), 6.59 (dd, J=6.8, 5.3 Hz, 1H), 6.53 (dd, J=6.9, 4.7 Hz, 1H), 6.45 (d, J=8.1 Hz, 1H), 4.09 (s, 4H), 3.97 (d, J=6.2 Hz, 6H), 3.84 (d, J=9.3 Hz, 4H), 2.95-2.85 (m, 2H), 2.81-2.54 (m, 4H), 2.15-2.00 (m, 2H). LCMS-ESI$^+$ (m/z): [M+H]$^+$ calculated for $C_{36}H_{37}ClN_4O_8$: 688.2; found: 688.0.

Example 2: 2,2'-((((((1S,1'S)-2,2',3,3'-tetrahydro-1H,1'H-[4,4'-biindene]-1,1'-diyl)bis(oxy))bis(5-chloro-2-methoxypyridine-6,3-diyl))bis(methylene))bis(azanediyl))diacetic acid (or 2,2'-(((6,6'-(((1S,1'S)-2,2',3,3'-tetrahydro-1H,1'H-[4,4'-biindene]-1,1'-diyl)bis(oxy))bis(5-chloro-2-methoxypyridine-6,3-diyl))bis(methylene))bis(azanediyl))diacetic acid)

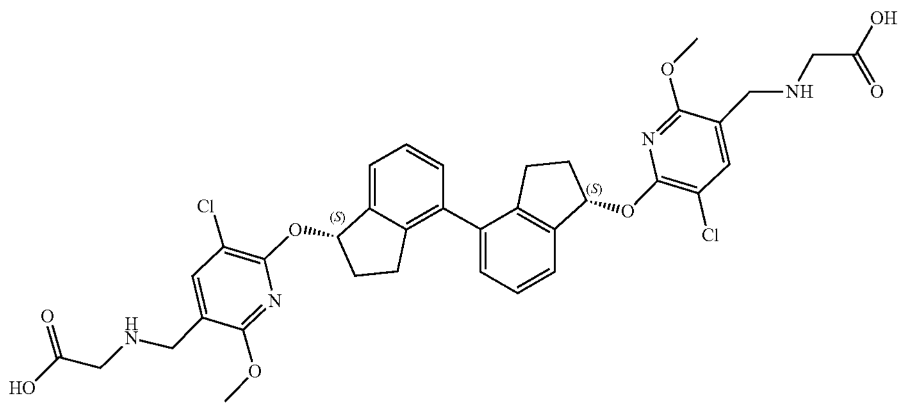

A solution of Intermediate 5 (65 mg, 0.11 mmol) was treated using general reductive amination procedure E, substituting glycine for (S)-4-amino-3-hydroxybutanoic acid. Purification by prep RP-HPLC (10-75% acetonitrile in water, 0.1% trifluoroacetic acid) furnished 2,2'-((((((1S,1'S)-2,2',3,3'-tetrahydro-1H,1'H-[4,4'-biindene]-1,1'-diyl)bis(oxy))bis(5-chloro-2-methoxypyridine-6,3-diyl))bis(methylene))bis(azanediyl))diacetic acid. $^1H$ NMR (400 MHz, DMSO-$d_6$) δ 9.16 (s, 4H), 7.92 (s, 2H), 7.43 (dd, J=6.8, 1.9 Hz, 2H), 7.38-7.29 (m, 4H), 6.60 (dd, J=6.9, 5.0 Hz, 2H), 4.09 (s, 4H), 3.98 (s, 6H), 3.84 (s, 4H), 2.91 (ddd, J=15.6, 8.4, 4.8 Hz, 2H), 2.78 (dt, J=15.7, 7.1 Hz, 2H), 2.71-2.63 (m, 2H), 2.10 (dt, J=10.9, 5.6 Hz, 2H). LCMS-ESI$^+$ (m/z): [M+H]$^+$ calculated for $C_{36}H_{36}Cl_2N_4O_8$: 722.12; found: 721.99.

Example 3: (3R,3'R)-4,4'-((((((1S,1'S)-2,2',3,3'-tetrahydro-1H,1'H-[4,4'-biindene]-1,1'-diyl)bis(oxy))bis(5-bromo-2-methoxypyridine-6,3-diyl))bis(methylene))bis(azanediyl))bis(3-hydroxybutanoic acid) (or(3R,3'R)-4,4'-(((6,6'-(((1S,1'S)-2,2',3,3'-tetrahydro-1H,1'H-[4,4'-biindene]-1,1'-diyl)bis(oxy))bis(5-bromo-2-methoxypyridine-6,3-diyl))bis(methylene))bis(azanediyl))bis(3-hydroxybutanoic acid))

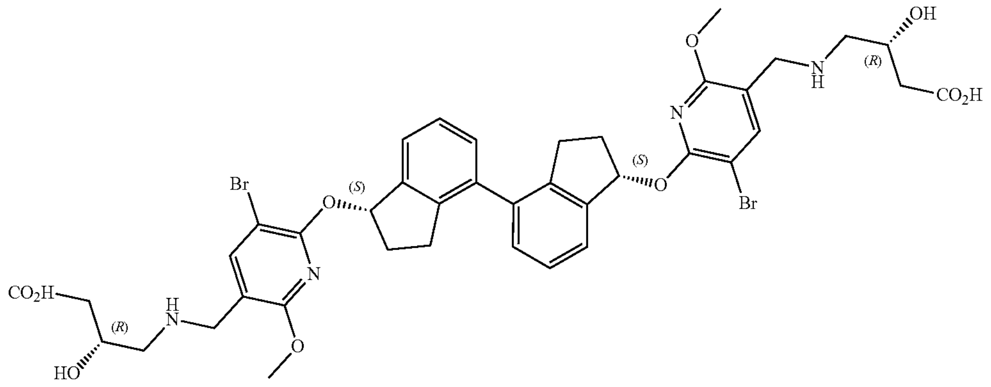

A solution of Intermediate 4 (17 mg, 0.025 mmol) was treated using general reductive amination procedure B, substituting (R)-4-amino-3-hydroxybutanoic acid for (S)-4-amino-3-hydroxybutanoic acid. Purification by prep RP-HPLC (10-75% acetonitrile in water, 0.1% trifluoroacetic acid) furnished (3R,3'R)-4,4'-((((((1S,1'S)-2,2',3,3'-tetrahydro-1H,1'H-[4,4'-biindene]-1,1'-diyl)bis(oxy))bis(5-bromo-2-methoxypyridine-6,3-diyl))bis(methylene))bis(azanediyl))bis(3-hydroxybutanoic acid). $^1$H NMR (400 MHz, DMSO-$d_6$) δ 9.09 (s, 4H), 7.92 (s, 1H), 7.72 (d, J=8.1 Hz, 1H), 7.42 (d, J=6.8 Hz, 2H), 7.36-7.27 (m, 4H), 6.59 (dd, J=6.8, 5.3 Hz, 1H), 6.53 (dd, J=6.9, 4.7 Hz, 1H), 6.45 (d, J=8.1 Hz, 1H), 4.09 (s, 4H), 3.97 (d, J=6.2 Hz, 6H), 3.84 (d, J=9.3 Hz, 4H), 2.95-2.85 (m, 2H), 2.81-2.54 (m, 4H), 2.15-2.00 (m, 2H). LCMS-ESI$^+$ (m/z): $[M+H]^+$ calculated for $C_4H_{44}Br_2N_4O_{10}$: 900.14; found: 900.975.

Example 4: (3S,3'S)-4,4'-((((((1S,1'S)-2,2',3,3'-tetrahydro-1H,1'H-[4,4'-biindene]-1,1'-diyl)bis(oxy))bis(5-bromo-2-((5-cyanopyridin-3-yl)methoxy)pyridine-6,3-diyl))bis(methylene))bis(azanediyl))bis(3-hydroxybutanoic acid)

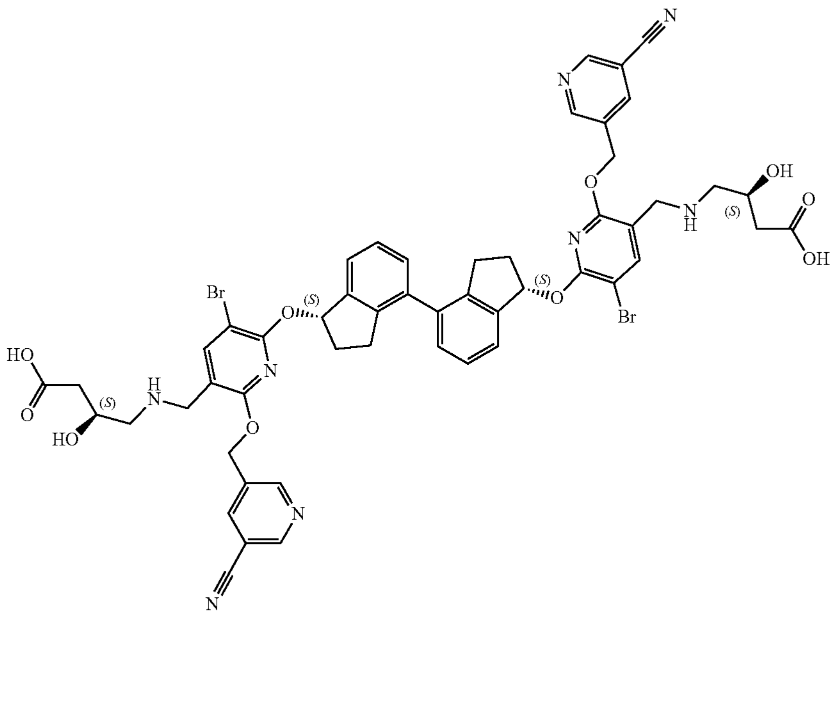

A solution of Intermediate 2 (100 mg, 0.11 mmol) was treated using general reductive amination procedure B. Purification by prep RP-HPLC (10-75% acetonitrile in water, 0.1% trifluoroacetic acid) furnished (3S,3'S)-4,4'-((((((1S,1'S)-2,2',3,3'-tetrahydro-1H,1'H-[4,4'-biindene]-1,1'-diyl)bis(oxy))bis(5-bromo-2-((5-cyanopyridin-3-yl)methoxy)pyridine-6,3-diyl))bis(methylene))bis(azanediyl))bis(3-hydroxybutanoic acid). $^1$H NMR (400 MHz, Acetonitrile-$d_3$/$D_2O$-$d_2$) δ 8.88 (d, J=2.1 Hz, 2H), 8.78 (d, J=1.9 Hz, 2H), 8.24 (s, 2H), 7.95 (s, 2H), 7.26-7.24 (m, 4H), 6.42 (t, J=6.0 Hz, 2H), 5.57 (s, 4H), 4.26-4.23 (m, 4H), 4.21 (s, 4H), 3.16 (dd, J=12.8, 3.1 Hz, 4H), 3.02-2.95 m, 2H), 2.76-2.69 (m, 2H), 2.67-2.58 (m, 5H), 2.56-2.41 (m, 4H). LCMS-ESI$^+$ (m/z): [M+H]$^+$ calculated for $C_{52}H_{48}Br_2N_8O_{10}$: 1104.18; found: 1105.1.

Example 5: ((2S,2'S)-2,2'-((((((1S,1'S)-2,2',3,3'-tetrahydro-1H,1'H-[4,4'-biindene]-1,1'-diyl)bis(oxy))bis(5-bromo-2-methoxypyridine-6,3-diyl))bis(methylene))bis(azanediyl))bis(3-hydroxy-2-methylpropanoic acid)

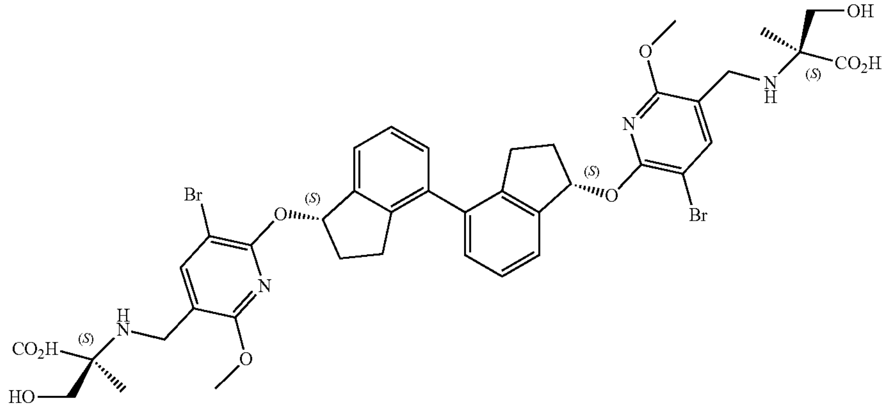

A solution of Intermediate 4 (30 mg, 0.043 mmol) was treated using general reductive amination procedure B, substituting (S)-2-amino-3-hydroxy-2-methylpropanoic acid for (S)-4-amino-3-hydroxybutanoic acid. Purification by prep RP-HPLC (10-75% acetonitrile in water, 0.1% trifluoroacetic acid) furnished (2S,2'S)-2,2'-((((((1S,1'S)-2,2',3,3'-tetrahydro-1H,1'H-[4,4'-biindene]-1,1'-diyl)bis(oxy))bis(5-bromo-2-methoxypyridine-6,3-diyl))bis(methylene))bis(azanediyl))bis(3-hydroxy-2-methylpropanoic acid). $^1$H NMR (400 MHz, Acetonitrile-$d_3$/$D_2O$-$d_2$) δ 7.86 (d, J=4.5 Hz, 2H), 7.46 (d, J=7.7 Hz, 2H), 7.35-7.22 (m, 4H), 6.63-6.55 (m, 2H), 4.09 (d, J=4.2 Hz, 4H), 3.99 (d, J=4.1 Hz, 6H), 3.80-3.72 (m, 2H), 2.88 (d, J=6.7 Hz, 2H), 2.80-2.59 (m, 2H), 2.10 (s, 2H), 1.48 (d, J=4.1 Hz, 6H). LCMS-ESI$^+$ (m/z): [M+H]$^+$ calculated for $C_{40}H_{44}Br_2N_4O_{10}$:900.1; found: 900.2.

Example 6: (3S,3'S)-4,4'-((((((1S,1'S)-2,2',3,3'-tetrahydro-1H,1'H-[4,4'-biindene]-1,1'-diyl)bis(oxy))bis(5-chloro-2-methoxypyridine-6,3-diyl))bis(methylene))bis(azanediyl))bis(3-hydroxybutanoic acid)

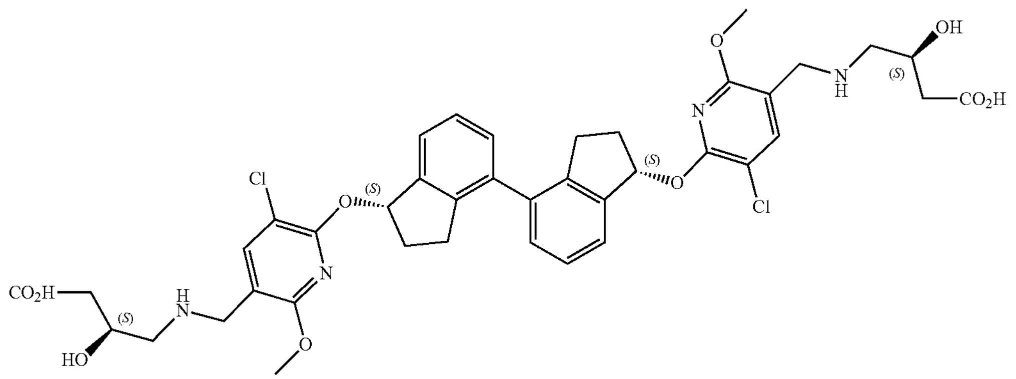

A solution of Intermediate 5 (75 mg, 0.124 mmol) was treated using general reductive amination procedure B. Purification by prep RP-HPLC (10-75% acetonitrile in water, 0.1% trifluoroacetic acid) furnished (3S,3'S)-4,4'-((((((1S,1'S)-2,2',3,3'-tetrahydro-1H,1'H-[4,4'-biindene]-1,1'-diyl)bis(oxy))bis(5-chloro-2-methoxypyridine-6,3-diyl))bis(methylene))bis(azanediyl))bis(3-hydroxybutanoic acid). $^1$H NMR (400 MHz, DMSO-$d_6$) δ 12.35 (s, 2H), 8.70 (s, 4H), 7.96 (s, 2H), 7.42 (dd, J=6.7, 1.9 Hz, 2H), 7.39-7.28 (m, 4H), 6.59 (t, J=6.0 Hz, 2H), 5.59 (s, 2H), 4.16 (s, 2H), 4.07 (s, 4H), 3.98 (s, 6H), 3.03 (s, 2H), 2.93-2.84 (m, 4H), 2.85-2.64 (m, 2H), 2.48-2.32 (m, 2H), 2.07 (dd, J=16.8, 5.6 Hz, 2H). LCMS-ESI$^+$ (m/z): [M+H]$^+$ calculated for $C_{40}H_{44}Cl_2N_4O_{10}$: 810.2; found: 810.2.

Example 7: (3S,3'S)-4,4'-((((((1S,1'S)-2,2',3,3'-tetrahydro-1H,1'H-[4,4'-biindene]-1,1'-diyl)bis(oxy))bis(5-bromo-2-methoxypyridine-6,3-diyl))bis(methylene))bis(azanediyl))bis(3-hydroxybutanoic acid)

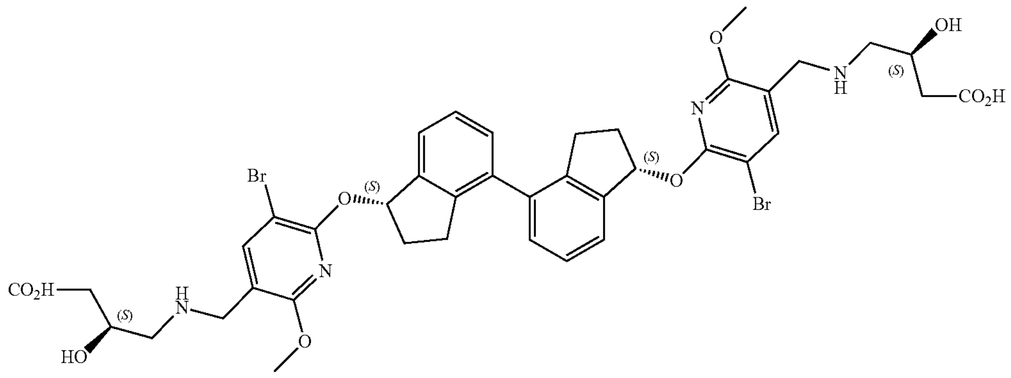

A solution of Intermediate 4 (40 mg, 0.043 mmol) was treated using general reductive amination procedure B. Purification by prep RP-HPLC (10-75% acetonitrile in water, 0.1% trifluoroacetic acid) furnished (3S,3'S)-4,4'-((((((1S,1'S)-2,2',3,3'-tetrahydro-1H,1'H-[4,4'-biindene]-1,1'-diyl)bis(oxy))bis(5-bromo-2-methoxypyridine-6,3-diyl))bis(methylene))bis(azanediyl))bis(3-hydroxybutanoic acid). $^1$H NMR (400 MHz, DMSO-$d_6$) δ 12.35 (s, 2H), 8.64 (s, 4H), 8.08 (s, 2H), 7.46-7.39 (m, 2H), 7.39-7.27 (m, 4H), 6.57 (t, J=6.1 Hz, 2H), 5.57 (s, 2H), 4.16 (s, 2H), 4.07 (s, 4H), 3.98 (s, 6H), 3.03 (m, 2H), 2.89 (m, 2H), 2.78 (m, 2H), 2.68 (m, 2H), 2.48-2.32 (m, 2H), 2.13-2.00 (m, 2H). LCMS-ESI$^+$ (m/z): [M+H]$^+$ calculated for $C_{40}H_{44}Br_2N_4O_{10}$: 900.14; found: 900.0.

Example 8: (S)-4-(((5-bromo-6-(((1S,1'S)-1'-((3-bromo-5-(((2-hydroxyethyl)amino)methyl)-6-methoxypyridin-2-yl)oxy)-2,2',3,3'-tetrahydro-1H,1'H-[4,4'-biinden]-1-yl)oxy)-2-methoxypyridin-3-yl)methyl)amino)-3-hydroxybutanoic acid

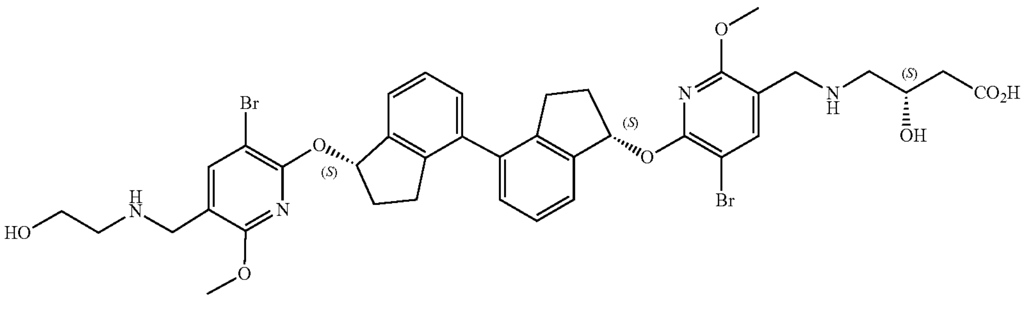

A solution of Intermediate 4 (126 mg, 0.181 mmol) in 2 mL DCM and 5 mL DMSO was treated with ethanolamine (111 mg, 1.81 mmol) and stirred for 2 h. Sodium triacetoxyborohydride (385 mg, 1.81 mmol) was added and the reaction stirred an additional hour. Purification by prep RP-HPLC (10-75% acetonitrile in water, 0.1% trifluoroacetic acid buffer) furnished the intermediate 5-bromo-6-(((1S,1'S)-1'-((3-bromo-5-(((2-hydroxyethyl)amino)methyl)-6-methoxypyridin-2-yl)oxy)-2,2',3,3'-tetrahydro-1H,1'H-[4,4'-biinden]-1-yl)oxy)-2-methoxynicotinaldehyde as a solid. This intermediate was treated using general reductive amination procedure D and purified by RP-HPLC (10-75% acetonitrile in water, 0.1% trifluoroacetic acid) furnished (S)-4-(((5-bromo-6-(((1S,1'S)-1'-((3-bromo-5-(((2-hydroxyethyl)amino)methyl)-6-methoxypyridin-2-yl)oxy)-2,2',3,3'-tetrahydro-1H,1'H-[4,4'-biinden]-1-yl)oxy)-2-methoxypyridin-3-yl)methyl)amino)-3-hydroxybutanoic acid. $^1$H NMR (400 MHz, DMSO-$d_6$) δ 8.66 (s, 4H), 8.07 (d, J=1.0 Hz, 2H), 7.42 (dd, J=7.1, 1.7 Hz, 2H), 7.39-7.28 (m, 4H), 6.57 (t, J=6.1 Hz, 2H), 4.16 (s, 1H), 4.07 (s, 4H), 3.65 (t, J=5.3 Hz, 2H), 3.06-2.95 (m, 2H), 2.95-2.84 (m, 2H), 2.84-2.74 (m, 2H), 2.74-2.64 (m, 2H), 2.42-2.29 (m, 2H), 2.11-2.00 (m, 2H). LCMS-ESI$^+$ (m/z): $[M+H]^+$ calculated for $C_{38}H_{42}Br_2N_4O_8$: 842.13; found: 842.01.

Example 9: (3S,3'S)-4,4'-(((((2,2',3,3'-tetrahydro-1H,1'H-[4,4'-biindene]-1,1'-diyl)bis(oxy))bis(5-chloro-2-methoxypyridine-6,3-diyl))bis(methylene))bis(azanediyl))bis(3-hydroxybutanoic acid)

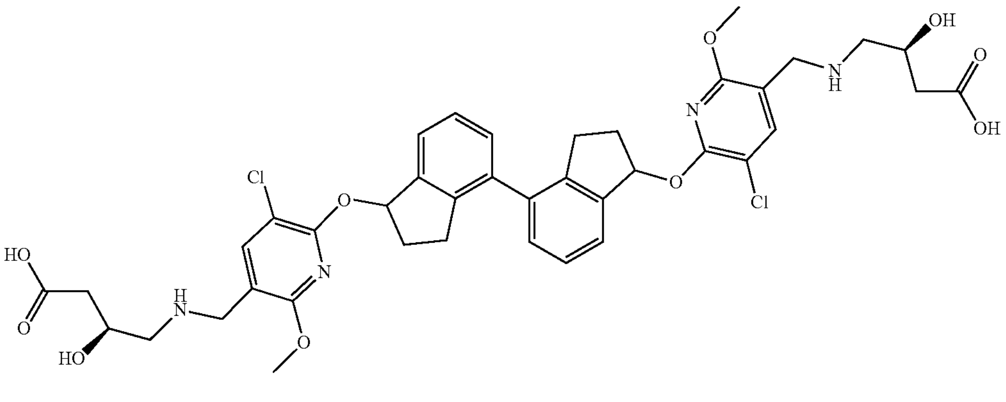 [SMILES: COc1nc(OC2CCc3c(-c4cccc5c4CCC5Oc4nc(OC)c(CNC[C@@H](O)CC(=O)O)cc4Cl)cccc32)c(Cl)cc1CNC[C@@H](O)CC(=O)O]

A solution of Intermediate 6 (17 mg, 0.28 mmol) was treated using general reductive amination procedure B. Purification by prep RP-HPLC (10-75% acetonitrile in water, 0.1% trifluoroacetic acid) furnished (3S,3'S)-4,4'-(((((2,2',3,3'-tetrahydro-1H,1'H-[4,4'-biindene]-1,1'-diyl)bis(oxy))bis(5-chloro-2-methoxypyridine-6,3-diyl))bis(methylene))bis(azanediyl))bis(3-hydroxybutanoic acid). $^1$H NMR (400 MHz, Acetonitrile-$d_3$/$D_2O$) δ 7.75 (s, 2H), 7.48 (d, J=7.5 Hz, 2H), 7.38-7.24 (m, 4H), 6.63 (dd, J=6.8, 4.4 Hz, 2H), 4.24 (t, J=8.5 Hz, 3H), 4.13 (s, 4H), 4.09-3.91 (m, 9H), 3.96 (s, 23H), 3.12 (dd, J=13.0, 3.1 Hz, 2H), 3.01-2.92 (m, 2H), 2.92 (s, 2H), 2.71 (ddt, J=36.6, 13.4, 7.0 Hz, 4H), 2.50 (t, J=6.2 Hz, 4H), 2.16 (ddd, J=13.4, 8.8, 4.4 Hz, 2H), 1.96 (t, J=2.5 Hz, 5H). LCMS-ESI$^+$ (m/z): $[M+H]^+$ calculated for $C_{40}H_{44}Cl_2N_4O_{10}$: 810.2; found: 810.1.

Example 10: 2,2'-((((((1S,1'S)-2,2',3,3'-tetrahydro-1H,1'H-[4,4'-biindene]-1,1'-diyl)bis(oxy))bis(5-bromo-2-methoxypyridine-6,3-diyl))bis(methylene))bis(azanediyl))bis(ethan-1-ol) (or 2,2'-(((6,6'-(((1S,1'S)-2,2',3,3'-tetrahydro-1H,1'H-[4,4'-biindene]-1,1'-diyl)bis(oxy))bis(5-bromo-2-methoxypyridine-6,3-diyl))bis(methylene))bis(azanediyl))bis(ethan-1-ol))

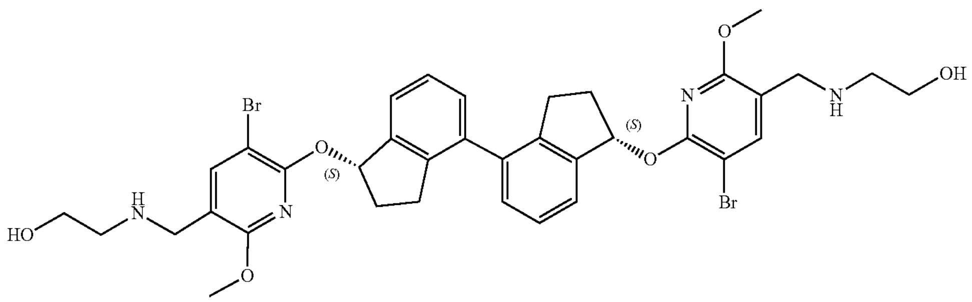

A solution of Intermediate 4 (33 mg, 0.045 mmol) was treated using general reductive amination procedure B, substituting ethanolamine for (S)-4-amino-3-hydroxybutanoic acid. Purification by prep RP-HPLC (10-75% acetonitrile in water, 0.1% trifluoroacetic acid) furnished 2,2'-((((((1S,1'S)-2,2',3,3'-tetrahydro-1H,1'H-[4,4'-biindene]-1,1'-diyl)bis(oxy))bis(5-bromo-2-methoxypyridine-6,3-diyl))bis(methylene))bis(azanediyl))bis(ethan-1-ol). $^1$H NMR (400 MHz, DMSO-$d_6$) δ 8.65 (s, 4H), 8.07 (s, 2H), 7.42 (dd, J=6.8, 1.7 Hz, 2H), 7.37-7.29 (m, 4H), 6.57 (dd, J=6.9, 5.3 Hz, 2H), 5.23 (s, 2H), 4.06 (d, J=5.1 Hz, 4H), 3.98 (s, 6H), 3.65 (s, 4H), 2.99 (s, 4H), 2.94-2.63 (m, 6H), 2.07 (dq, J=13.8, 7.6, 7.1 Hz, 2H). LCMS-ESI$^+$ (m/z): [M+H]$^+$ calculated for $C_{36}H4Br_2N_4O_6$: 784.1; found: 783.0.

Example 11: (3S,3'S)-4,4'-((((((1S,1'S)-2,2',3,3'-tetrahydro-1H,1'H-[4,4'-biindene]-1,1'-diyl)bis(oxy))bis(2-methoxypyridine-6,3-diyl))bis(methylene))bis(azanediyl))bis(3-hydroxybutanoic acid)

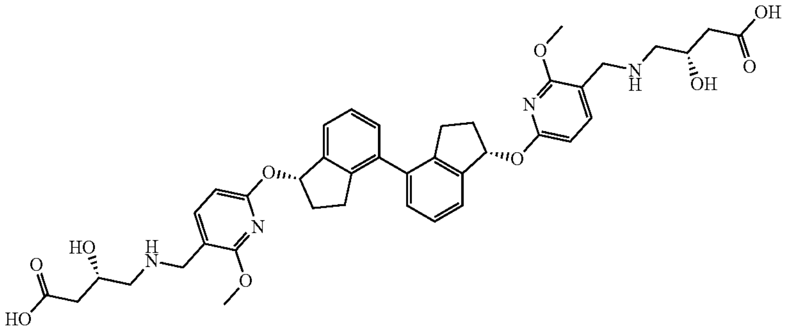 [SMILES: COc1nc(O[C@H]2CCc3c(-c4cccc5c4CC[C@@H]5Oc4ccc(CNC[C@@H](O)CC(=O)O)c(OC)n4)cccc32)ccc1CNC[C@@H](O)CC(=O)O]

A solution of Intermediate 3 (15 mg, 0.028 mmol) was treated using general reductive amination procedure B. Purification by prep RP-HPLC (10-75% acetonitrile in water, 0.1% trifluoroacetic acid) furnished the titled product. $^1$H NMR (400 MHz, DMSO-$d_6$) δ 12.35 (s, 2H), 8.61 (s, 4H), 7.75 (d, J=8.1 Hz, 2H), 7.41 (dd, J=7.0, 1.6 Hz, 2H), 7.36-7.24 (m, 4H), 6.52 (dd, J=6.7, 4.9 Hz, 2H), 6.46 (d, J=8.0 Hz, 2H), 5.58 (s, 2H), 4.17 (s, 2H), 4.10-4.04 (m, 4H), 3.97 (s, 6H), 3.01 (m, 2H), 2.88 (m, 4H), 2.78-2.67 (m, 2H), 2.61 (dt, J=13.7, 7.1 Hz, 2H), 2.53-2.33 (m, 4H) 2.06 (m, 2H). LCMS-ESI$^+$ (m/z): [M+H]$^+$ calculated for $C_4H_{46}N_4O_{10}$: 742.3; found: 742.2.

Example 12: 5,5'-((((((2,2'-dimethyl-[1,1'-biphenyl]-3,3'-diyl)bis(methylene))bis(oxy))bis(4-chloro-6-((ethylamino)methyl)-3,1-phenylene))bis(oxy))bis(methylene))dinicotinonitrile (or 5,5'-((((((2,2'-dimethyl-[1,1'-biphenyl]-3,3'-diyl)bis(methylene))bis(oxy))bis(4-chloro-2-((ethylamino)methyl)-5,1-phenylene))bis(oxy))bis(methylene))dinicotinonitrile)

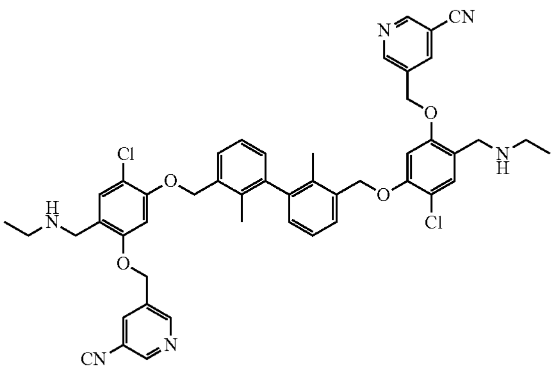

A solution of Intermediate 12 (55 mg, 0.075 mmol) was treated using general reductive amination procedure E substituting ethylamine for (S)-4-amino-3-hydroxybutanoic acid. Purification by prep RP-HPLC (10-75% acetonitrile in water, 0.1% trifluoroacetic acid) furnished 5,5'-((((((2,2'-dimethyl-[1,1'-biphenyl]-3,3'-diyl)bis(methylene))bis(oxy))bis(4-chloro-6-((ethylamino)methyl)-3,1-phenylene))bis(oxy))bis(methylene))dinicotinonitrile. $^{1}H$ NMR (400 MHz, DMSO-$d_6$) δ 9.04 (d, J=2.0 Hz, 2H), 9.03 (d, J=2.1 Hz, 2H), 8.49 (t, J=2.1 Hz, 2H), 7.55 (s, 2H), 7.49 (dd, J=7.6, 1.4 Hz, 2H), 7.29 (t, J=7.6 Hz, 2H), 7.20 (s, 2H), 7.11 (dd, J=7.7, 1.3 Hz, 2H), 5.37 (s, 4H), 5.32 (d, J=2.9 Hz, 4H), 4.09 (t, J=5.8 Hz, 4H), 2.93 (h, J=7.0 Hz, 5H), 2.02 (s, 6H), 1.15 (t, J=7.2 Hz, 6H). LCMS-ESI$^{+}$ (m/z): $[M+H]^{+}$ calculated for $C_{48}H_{46}Cl_2N_6O_4$: 840.3; found: 840.1.

Example 13: (3S,3'S)-4,4'-(((((2,2',3,3'-tetrahydro-1H,1'H-[4,4'-biindene]-1,1'-diyl)bis(oxy))bis(2-methoxypyridine-6,3-diyl))bis(methylene))bis(azanediyl))bis(3-hydroxybutanoic acid) (or (3S,3'S)-4,4'-(((6,6'-((2,2',3,3'-tetrahydro-1H,1'H-[4,4'-biindene]-1,1'-diyl)bis(oxy))bis(2-methoxypyridine-6,3-diyl))bis(methylene))bis(azanediyl))bis(3-hydroxybutanoic acid))

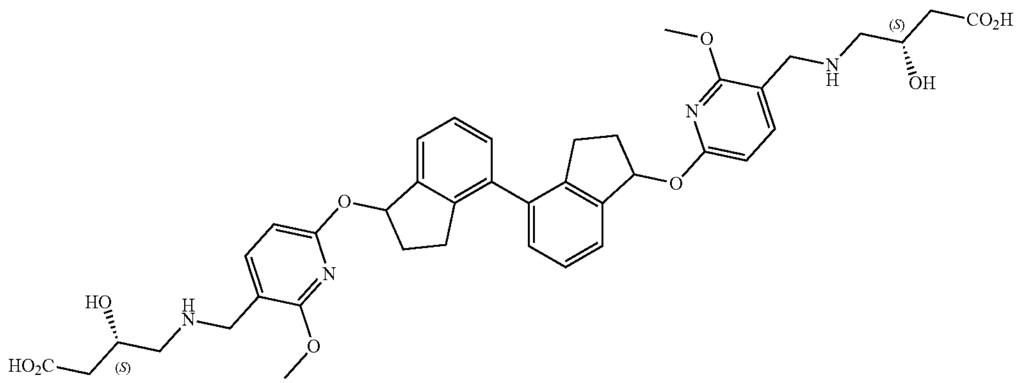

A solution of 6,6'-((2,2',3,3'-tetrahydro-1H,1'H-[4,4'-biindene]-1,1'-diyl)bis(oxy))bis(2-methoxynicotinaldehyde) (35 mg, 0.065 mmol) was treated using general reductive amination procedure E. Purification by prep RP-HPLC (10-75% acetonitrile in water, 0.1% trifluoroacetic acid) furnished (3S,3'S)-4,4'-(((((2,2',3,3'-tetrahydro-1H,1'H-[4,4'-biindene]-1,1'-diyl)bis(oxy))bis(2-methoxypyridine-6,3-diyl))bis(methylene))bis(azanediyl))bis(3-hydroxybutanoic acid). $^{1}H$ NMR (400 MHz, DMSO-$d_6$) δ 8.56 (s, 4H), 7.70 (d, J=8.1 Hz, 2H), 7.42-7.32 (m, 2H), 7.30-7.19 (m, 4H), 6.47 (dd, J=6.8, 4.7 Hz, 2H), 6.41 (d, J=8.1 Hz, 2H), 5.54 (d, J=5.6 Hz, 2H), 4.12 (s, 2H), 4.02 (s, 4H), 3.92 (s, 6H), 2.95 (s, 2H), 2.91-2.75 (m, 4H), 2.69 (dd, J=16.1, 5.1 Hz, 2H), 2.62-2.47 (m, 2H), 2.38-2.23 (m, 2H), 2.10-1.92 (m, 2H). LCMS-ESI$^{+}$ (m/z): $[M+H]^{+}$ calculated for $C_4H_{46}N_4O_{10}$: 742.3; found: 742.2.

Example 14: (2R,2'R)-2,2'-((((((2,2'-dimethyl-[1,1'-biphenyl]-3,3'-diyl)bis(methylene))bis(oxy))bis(2-methoxypyridine-6,3-diyl))bis(methylene))bis(azanediyl))bis(3-hydroxypropanoic acid (or (2R,2'R)-2,2'-(((6,6'-(((2,2'-dimethyl-[1,1'-biphenyl]-3,3'-diyl)bis(methylene))bis(oxy))bis(2-methoxypyridine-6,3-diyl))bis(methylene))bis(azanediyl))bis(3-hydroxypropanoic acid))

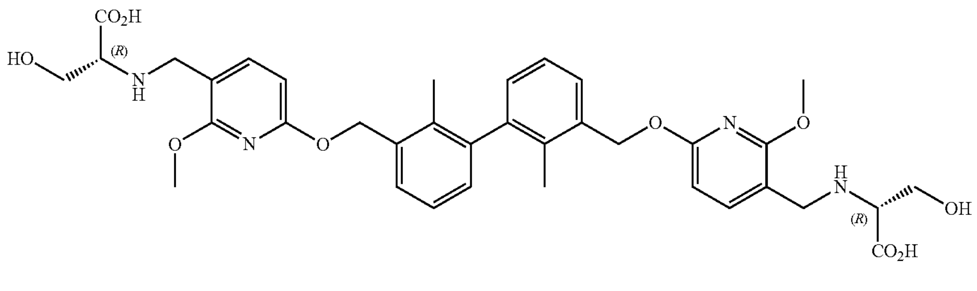

A solution of Intermediate 10 (50 mg, 0.0975 mmol) was treated using general reductive amination procedure E. Purification by prep RP-HPLC (10-75% acetonitrile in water, 0.1% trifluoroacetic acid) furnished (2R,2'R)-2,2'-((((((2,2'-dimethyl-[1,1'-biphenyl]-3,3'-diyl)bis(methylene))bis(oxy))bis(2-methoxypyridine-6,3-diyl))bis(methylene))bis(azanediyl))bis(3-hydroxypropanoic acid. $^1$H NMR (400 MHz, DMSO-$d_6$) δ 7.69 (d, J=8.1 Hz, 2H), 7.39 (d, J=7.4 Hz, 2H), 7.20 (t, J=7.6 Hz, 2H), 7.00 (dd, J=7.6, 1.4 Hz, 2H), 6.46 (d, J=8.1 Hz, 2H), 5.38 (s, 4H), 4.12-3.98 (m, 4H), 3.87-3.71 (m, 6H), 3.83 (s, 6H), 1.95 (s, 6H). LCMS-ESI$^+$ (m/z): [M+H]$^+$ calculated for $C_{36}H_{42}N_4O_{10}$: 690.3; found: 690.1.

Example 15: 5,5'-((((((2,2'-dimethyl-[1,1'-biphenyl]-3,3'-diyl)bis(methylene))bis(oxy))bis(4-chloro-6-(piperidin-1-ylmethyl)-3,1-phenylene))bis(oxy))bis(methylene))dinicotinonitrile (or 5,5'-((((((2,2'-dimethyl-[1,1'-biphenyl]-3,3'-diyl)bis(methylene))bis(oxy))bis(4-chloro-2-(piperidin-1-ylmethyl)-5,1-phenylene))bis(oxy))bis(methylene))dinicotinonitrile)

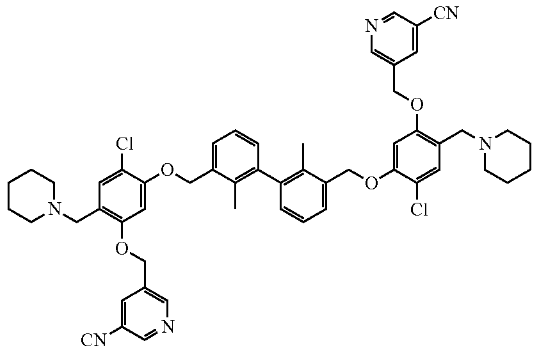

A solution of Intermediate 12 (100 mg, 0.128 mmol) was treated using general reductive amination procedure E, substituting piperidine for (S)-4-amino-3-hydroxybutanoic acid and THF for DMF. Purification by prep RP-HPLC (10-75% acetonitrile in water, 0.1% trifluoroacetic acid) furnished 5,5'-((((((2,2'-dimethyl-[1,1'-biphenyl]-3,3'-diyl)bis(methylene))bis(oxy))bis(4-chloro-6-(piperidin-1-ylmethyl)-3,1-phenylene))bis(oxy))bis(methylene))dinicotinonitrile. $^1$H NMR (400 MHz, DMSO-$d_6$) δ 9.04 (dd, J=6.6, 2.1 Hz, 4H), 8.50 (t, J=2.1 Hz, 2H), 7.61 (s, 2H), 7.52 (dd, J=7.7, 1.4 Hz, 2H), 7.31 (t, J=7.6 Hz, 2H), 7.24 (s, 2H), 7.12 (dd, J=7.6, 1.3 Hz, 2H), 5.40-5.27 (m, 8H), 4.19 (d, J=4.7 Hz, 4H), 3.29 (d, J=11.9 Hz, 4H), 2.87 (q, J=10.7 Hz, 4H), 2.03 (s, 6H), 1.76 (d, J=14.1 Hz, 4H), 1.59 (d, J=15.5 Hz, 6H), 1.33 (d, J=12.4 Hz, 2H). LCMS-ESI$^+$ (m/z): [M+H]$^+$ calculated for $C_{54}H_{54}Cl_2N_6O_4$: 920.4; found: 920.3.

Example 16: (S)-4-((4-((4''-(2-(((S)-3-carboxy-2-hydroxypropyl)amino)ethoxy)-2,2'-dimethyl-[1,1':3',1''-terphenyl]-3-yl)methoxy)-5-chloro-2-((5-cyano-pyridin-3-yl)methoxy)benzyl)amino)-3-hydroxybutanoic acid

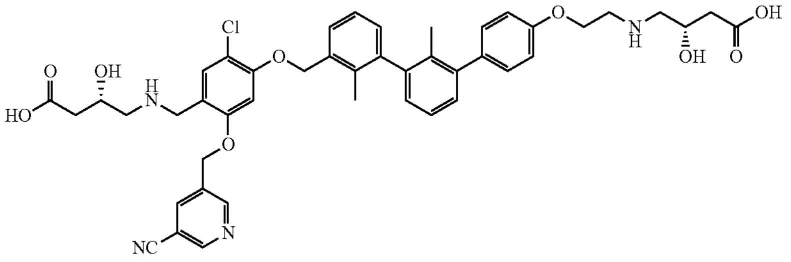 [SMILES: Cc1c(COc2cc(OCc3cncc(C#N)c3)c(CNC[C@@H](O)CC(=O)O)cc2Cl)cccc1-c1cccc(-c2ccc(OCCNC[C@@H](O)CC(=O)O)cc2)c1C]

To a clear solution of (S)-4-amino-3-hydroxybutanoic acid (120 mg, 1 mmol) in 1N NaOH (1 mL) and EtOH (3 mL) was added a solution of 5-((4-chloro-5-((2,2'-dimethyl-4''-(2-oxoethoxy)-[1,1':3',1''-terphenyl]-3-yl)methoxy)-2-formylphenoxy)methyl)nicotinonitrile (62 mg, 0.1 mmol, intermediate 16) in EtOH (1 mL) and dioxane (1 mL). The resulting mixture was stirred at room temperature for 1 h, which became cloudy. The mixture was then heated up to make a clear solution. After cooling, sodium triacetoxyborohydride (280 mg, 1.3 mmol) was added. The mixture was stirred at room temperature for 16 h. A diluted HCl (1N, 1 mL) was added and concentrated. Acetonitrile and methanol were added and concentrated again. DMSO (~3 mL) was then added followed by a few drops of water, which was filtered. The filtrate was loaded onto reverse-phase HPLC and purified, affording (S)-4-((4-((4''-(2-(((S)-3-carboxy-2-hydroxypropyl)amino)ethoxy)-2,2'-dimethyl-[1,1':3',1''-terphenyl]-3-yl)methoxy)-5-chloro-2-((5-cyanopyridin-3-yl)methoxy)benzyl)amino)-3-hydroxybutanoic acid as the bis-TFA salt. [M+H] 823.1, $^1$H NMR (400 MHz, Methanol-$d_4$) δ 8.95 (d, J=2.1 Hz, 1H), 8.92 (d, J=2.0 Hz, 1H), 8.37 (t, J=2.1 Hz, 1H), 7.51 (s, 1H), 7.45 (dd, J=7.7, 1.4 Hz, 1H), 7.34-7.22 (m, 4H), 7.16 (ddd, J=17.3, 7.6, 1.5 Hz, 2H), 7.07 (td, J=7.9, 7.5, 1.8 Hz, 4H), 5.37 (s, 2H), 5.31 (s, 2H), 4.35 (dd, J=5.8, 4.3 Hz, 3H), 4.23 (s, 3H), 3.54 (dd, J=6.0, 4.1 Hz, 2H), 3.36 (dd, J=12.7, 3.0 Hz, 1H), 3.25-3.08 (m, 2H), 3.05-2.93 (m, 1H), 2.58 (d, J=6.3 Hz, 2H), 2.51 (dd, J=6.3, 1.0 Hz, 2H), 2.14 (s, 3H), 1.87 (s, 3H).

Example 17: (S)-4-((4-((3'-((4-((((S)-3-carboxy-2-hydroxypropyl)amino)methyl)-2-chloro-5-((5-cyano-pyridin-3-yl)methoxy)phenoxy)methyl)-2,2'-dimethyl-[1,1'-biphenyl]-3-yl)methoxy)benzyl)amino)-3-hydroxybutanoic acid

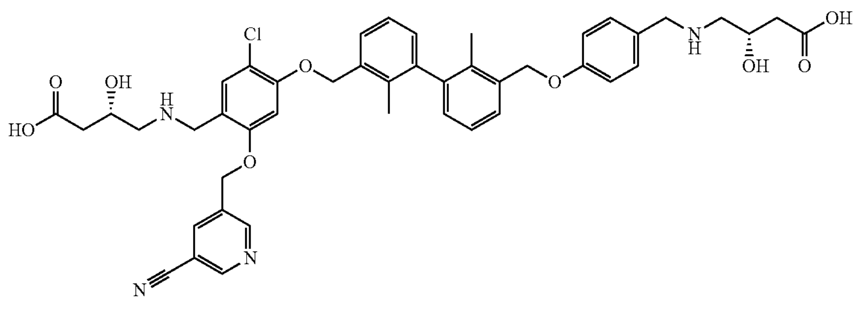 [SMILES: Cc1c(COc2ccc(CNC[C@@H](O)CC(=O)O)cc2)cccc1-c1cccc(COc2cc(OCc3cncc(C#N)c3)c(CNC[C@@H](O)CC(=O)O)cc2Cl)c1C]

To a solution of (3-bromo-2-methylphenyl)methanol (2.0 g, 10 mmol) and triethylamine (2.0 g, 20 mmol) in THF (80 mL) was dropwise added methanesulfonyl chloride (1.38 g, 12 mmol). The resulting mixture was stirred at room temperature for 16 h. The mixture was then partitioned between ethyl acetate and water. The ethyl acetate layer was washed with water, 5% sodium bicarbonate, and then brine. After drying over sodium sulfate, the solution was concentrated to dryness affording 3-bromo-2-methylbenzyl methanesulfonate, which was used for the next reaction without further purification.

To a solution of 4-hydroxybenzaldehyde (400 mg, 3.3 mmol) and 3-bromo-2-methylbenzyl methanesulfonate (920 mg, 3.3 mmol) in DMF (5 mL) was added cesium carbonate (1.4 g, 4.3 mmol) and stirred at room temperature for 16 h. The mixture was then partitioned between ethyl acetate and 3% LiCl in water. The ethyl acetate layer was taken and concentrated. The residue was purified by Combiflash, affording 4-((3-bromo-2-methylbenzyl)oxy)benzaldehyde. $[M+H]^+$ 305.1.

A mixture of 4-((3-bromo-2-methylbenzyl)oxy)benzaldehyde (31 mg, 0.1 mmol), 5-((4-chloro-2-formyl-5-((2-methyl-3-(4,4,5,5-tetramethyl-1,3,2-dioxaborolan-2-yl)benzyl)oxy)phenoxy)methyl)nicotinonitrile (52 mg, 0.1 mmol), DMF (1.5 mL) and 2N potassium carbonate (0.2 mL) was purged with argon for 10 min. [1,1'-Bis(diphenylphosphino) ferrocene]dichloropalladium(II) complex with dichloromethane (8 mg, 0.01 mmol) was then added. The resulting mixture was stirred at 80° C. for 20 min. After cooling, the mixture was partitioned between ethyl acetate and 3% LiCl in water. The ethyl acetate layer was taken and concentrated. The residue was purified by Combiflash, affording 5-((4-chloro-2-formyl-5-((3'-((4-formylphenoxy)methyl)-2,2'-dimethyl-[1,1'-biphenyl]-3-yl)methoxy)phenoxy)methyl) nicotinonitrile. $[M+H]^+$ 617.0.

Following general reductive amination procedure A, 5-((4-chloro-5-((2,2'-dimethyl-4''-(2-oxoethoxy)-[1,1':3',1''-terphenyl]-3-yl)methoxy)-2-formylphenoxy)methyl)nicotinonitrile (44 mg, 0.071 mmol) was converted to (S)-4-((4-((3'-((4-((((S)-3-carboxy-2-hydroxypropyl)amino)methyl)-2-chloro-5-((5-cyanopyridin-3-yl)methoxy)phenoxy)methyl)-2,2'-dimethyl-[1,1'-biphenyl]-3-yl)methoxy) benzyl)amino)-3-hydroxybutanoic acid as the bis-TFA salt. [M+H] 823.1, $^1$H NMR (400 MHz, Methanol-$d_4$) δ 8.96 (d, J=2.1 Hz, 1H), 8.92 (d, J=2.0 Hz, 1H), 8.38 (t, J=2.1 Hz, 1H), 7.51 (s, 1H), 7.50-7.37 (m, 4H), 7.26 (t, J=7.6 Hz, 2H), 7.16-7.04 (m, 5H), 5.38 (s, 2H), 5.31 (s, 2H), 5.17 (s, 2H), 4.36-4.18 (m, 2H), 4.24 (s, 2H), 4.18 (s, 2H), 3.18 (ddd, J=12.6, 11.3, 3.1 Hz, 2H), 3.04-2.92 (m, 2H), 2.52 (dd, J=6.3, 4.2 Hz, 4H), 2.09 (s, 3H), 2.03 (d, J=5.7 Hz, 4H).

Example 18: N,N'-((((((((2,2'-dimethyl-[1,1'-biphenyl]-3,3'-diyl)bis(methylene))bis(oxy))bis(2-methoxypyridine-6,3-diyl))bis(methylene))bis(azanediyl))bis(ethane-2,1-diyl))diacetamide (or N,N'-(((((6,6'-(((2,2'-dimethyl-[1,1'-biphenyl]-3,3'-diyl)bis(methylene))bis(oxy))bis(2-methoxypyridine-6,3-diyl))bis(methylene))bis(azanediyl))bis(ethane-2,1-diyl))diacetamide)

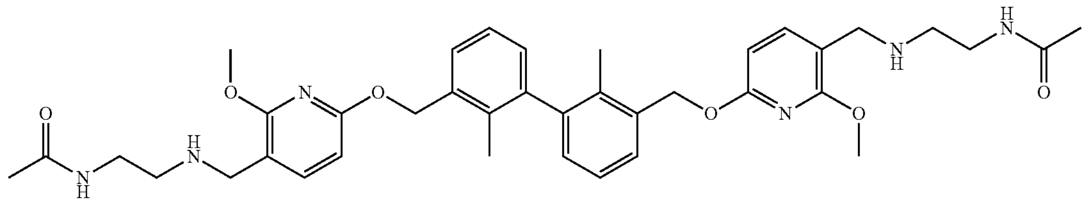 [SMILES: COc1nc(OCc2cccc(-c3cccc(COc4ccc(CNCCNC(C)=O)c(OC)n4)c3C)c2C)ccc1CNCCNC(C)=O]

To a solution of 6,6'-(((2,2'-dimethyl-[1,1'-biphenyl]-3,3'-diyl)bis(methylene))bis(oxy))bis(2-methoxynicotinaldehyde) (80 mg, 0.16 mmol) in DMF (3.0 mL) was added the N-(2-aminoethyl)acetamide (128 mg, 1.25 mmol), sodium cyanoborohydride (78 mg, 1.25 mmol) and acetic acid (0.30 mL) and the mixture was stirred at rt. After 18 h, the reaction mixture was concentrated and purified by reverse phase chromatography to give the title compound as TFA salt. LCMS-ESI$^+$ (m/z): $[M+H]^+$ calculated for $C_{38}H_{48}N_6O_6$: 685.3; found: 685.2. $^1$H NMR (400 MHz, DMSO-$d_6$) δ 8.61 (brs), 8.08 (t, J=5.8 Hz, 2H), 7.74 (d, J=8.1 Hz, 2H), 7.44 (dd, J=7.7, 1.3 Hz, 2H), 7.25 (t, J=7.6 Hz, 2H), 7.05 (dd, J=7.6, 1.3 Hz, 2H), 6.53 (d, J=8.1 Hz, 2H), 5.44 (s, 4H), 4.04-4.02 (m, 4H), 3.92 (s, 6H), 3.41-3.33 (m, 4H), 3.34-3.25 (m, 4H), 2.96-2.92 (m, 4H), 2.00 (s, 6H), 1.82 (s, 6H).

Example 19: (3S,3'S)-4,4'-((((((2,2'-dimethyl-[1,1'-biphenyl]-3,3'-diyl)bis(methylene))bis(oxy))bis(2-methoxypyridine-6,3-diyl))bis(methylene))bis(azanediyl))bis(3-hydroxybutanoic acid) (or (3S,3'S)-4,4'-(((6,6'-(((2,2'-dimethyl-[1,1'-biphenyl]-3,3'-diyl)bis(methylene))bis(oxy))bis(2-methoxypyridine-6,3-diyl))bis(methylene))bis(azanediyl))bis(3-hydroxybutanoic acid))

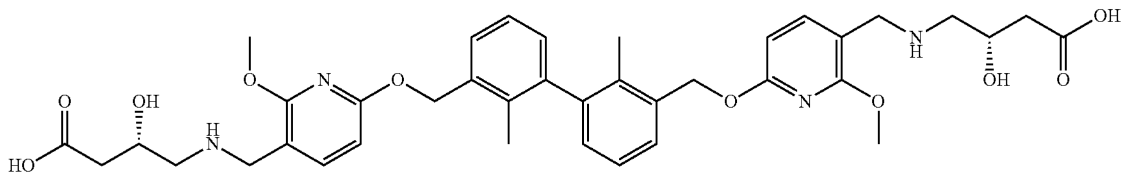 [SMILES: COc1nc(OCc2cccc(-c3cccc(COc4ccc(CNC[C@@H](O)CC(=O)O)c(OC)n4)c3C)c2C)ccc1CNC[C@@H](O)CC(=O)O]

To a solution of 6,6'-(((2,2'-dimethyl-[1,1'-biphenyl]-3,3'-diyl)bis(methylene))bis(oxy))bis(2-methoxynicotinaldehyde) (36 mg, 0.07 mmol) in DMF (2.0 mL) was added the (S)-4-amino-3-hydroxybutanoic acid (67 mg, 0.56 mmol), sodium cyanoborohydride (35 mg, 0.56 mmol) and acetic acid (0.20 mL) and the mixture was stirred at rt. After 18 h, the reaction mixture was concentrated and purified by reverse phase chromatography to give the title compound as TFA salt. LCMS-ESI$^+$ (m/z): $[M+H]^+$ calculated for $C_{38}H_{46}N_4O_{10}$: 719.3; found: 719.2. $^1$H NMR (400 MHz, DMSO-$d_6$) δ 8.65-8.52 (m, 4H), 7.75 (d, J=8.1 Hz, 2H), 7.44 (dd, J=7.5, 1.3 Hz, 2H), 7.25 (t, J=7.6 Hz, 2H), 7.05 (dd, J=7.4, 1.3 Hz, 2H), 6.52 (d, J=8.1 Hz, 2H), 5.57 (brs, 2H), 5.43 (s, 4H), 4.20-3.97 (m, 6H), 3.91 (s, 6H), 2.98-2.86 (m, 4H), 2.39-2.26 (m, 4H), 2.00 (s, 6H).

Example 20: 5,5'-(((((((2-methyl-[1,1'-biphenyl]-3,3'-diyl)bis(methylene))bis(oxy))bis(4-chloro-6-(((2-hydroxyethyl)amino)methyl)-3,1-phenylene))bis(oxy))bis(methylene))dinicotinonitrile (or 5,5'-(((((((2-methyl-[1,1'-biphenyl]-3,3'-diyl)bis(methylene))bis(oxy))bis(4-chloro-2-(((2-hydroxyethyl)amino)methyl)-5,1-phenylene))bis(oxy))bis(methylene))dinicotinonitrile)

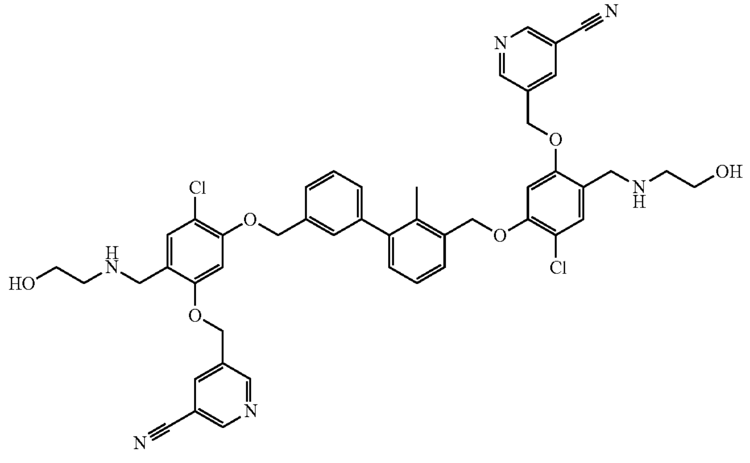 [SMILES: Cc1c(COc2cc(OCc3cncc(C#N)c3)c(CNCCO)cc2Cl)cccc1-c1cccc(COc2cc(OCc3cncc(C#N)c3)c(CNCCO)cc2Cl)c1]

Step 1: To a solution of 5-chloro-2,4-dihydroxybenzaldehyde (227 mg, 1.32 mmol) in DMF (6 mL) and $NaHCO_3$ (109 mg, 1.76 mmol), a separate solution of 1-bromo-3-(chloromethyl)benzene (180 mg, 0.87 mmol) in THF (6 mL) was added after is 5 min at rt, followed by the addition of NaI (131 mg, 0.87 mmol) at once. After 16 h, the reaction mixture was diluted with EtOAc and brine solution. The organic layer was then separated and the aqueous layer was back extracted with EtOAc and the combined organic layers were dried ($MgSO_4$). Filtration, concentration and followed by purification by column chromatography ($SiO_2$, 0% EtOAc/hexanes to 50% EtOAc/hexanes) gave 4-((3-bromobenzyl)oxy)-5-chloro-2-hydroxybenzaldehyde.

Step 2: To a solution of 4-((3-bromobenzyl)oxy)-5-chloro-2-hydroxybenzaldehyde (800 mg, 2.34 mmol) in DMF (3 mL) and $Cs_2CO_3$ (2.3 g, 7.02 mmol), a separate solution of 3-(chloromethyl)pyridine hydrogen chloride (885 mg, 4.68 mmol) in DMF (7 mL) was added followed by the addition of NaI (351 mg, 2.34 mmol) at once. The reaction mixture was heated at 75° C. After 16 h, the reaction mixture was diluted with $CH_2Cl_2$ and brine solution. The organic layer was then separated and the aqueous layer was back extracted with $CH_2Cl_2$ and the combined organic layers were dried ($MgSO_4$). Filtration, concentration and followed by purification by column chromatography ($SiO_2$, 0% EtOAc/hexanes to 100% EtOAc/hexanes) gave 5-((5-((3-bromobenzyl)oxy)-4-chloro-2-formylphenoxy)methyl)nicotinonitrile.

Step 3: To a mixture 5-((5-((3-bromobenzyl)oxy)-4-chloro-2-formylphenoxy)methyl)nicotinonitrile (53 mg, 0.12 mmol) and 5-((4-chloro-2-formyl-5-((2-methyl-3-(4,4,5,5-tetramethyl-1,3,2-dioxaborolan-2-yl)benzyl)oxy)phenoxy)methyl)nicotinonitrile (50 mg, 0.10 mmol) in 1,4-Dioxane/water (3 mL, 2:1) was added $K_2C_3$(20 mg, 0.20 mmol) and Pd(dppf)$Cl_2$ (8 mg, 0.01 mmol) and the reaction mixture was heated at 85° C. for 16h. After cooling to room temperature, the reaction mixture was diluted with EtOAc and water. The organic layer was then separated and the aqueous layer was back extracted with EtOAc and the combined organic layers were dried ($MgSO_4$). Filtration, concentration and followed by purification by column chromatography ($SiO_2$, 0% MeOH/EtOAc to 5% MeOH/EtOAc) gave 5,5'-((((((2-methyl-[1,1'-biphenyl]-3,3'-diyl)bis(methylene))bis(oxy))bis(4-chloro-6-formyl-3,1-phenylene))bis(oxy))bis(methylene))dinicotinonitrile.

Step 4: To a solution of 5,5'-((((((2-methyl-[1,1'-biphenyl]-3,3'-diyl)bis(methylene))bis(oxy))bis(4-chloro-6-formyl-3,1-phenylene))bis(oxy))bis(methylene))dinicotinonitrile (36 mg, 0.05 mmol) in DMF (2.0 mL) was added ethanolamine (17 mg, 0.28 mmol), sodium cyanoborohydride (35 mg, 0.56 mmol) and acetic acid (0.20 mL) and the mixture was stirred at 45° C. After 18 h, the reaction mixture was concentrated and purified by reverse phase chromatography to give the title compound as TFA salt. LCMS-ESI$^+$ (m/z): $[M+H]^+$ calculated for $C_{47}H_{44}Cl_2N_6O_6$: 859.2; found: 859.2. $^1$H NMR (400 MHz, DMSO-$d_6$) δ 9.05 (dd, J=5.1, 2.1 Hz, 1H), 9.00 (d, J=2.0 Hz, 1H), 8.56 (s, 2H), 8.48 (d, J=13.7 Hz, 1H), 7.58 (s, 1H), 7.51 (d, J=6.8 Hz, 1H), 7.46 (d, J=9.7 Hz, 1H), 7.31 (d, J=7.5 Hz, 1H), 7.22 (d, J=14.9 Hz, 1H), 7.15 (s, 1H), 5.38 (d, J=7.4 Hz, 2H), 5.33 (s, 2H), 5.22 (s, 1H), 4.14 (s, 2H), 3.63 (s, 2H), 2.95 (s, 2H), 2.69-2.65 (m, 1H), 2.35-2.31 (m, 1H), 2.25 (s, 1H).

Example 21: 2,2'-((((((2,2'-dimethyl-[1,1'-biphenyl]-3,3'-diyl)bis(methylene))bis(oxy))bis(2-methoxypyridine-6,3-diyl))bis(methylene))bis(azanediyl))bis(ethan-1-ol) (or 2,2'-(((6,6'-(((2,2'-dimethyl-[1,1'-biphenyl]-3,3'-diyl)bis(methylene))bis(oxy))bis(2-methoxypyridine-6,3-diyl))bis(methylene))bis(azanediyl))bis(ethan-1-ol))

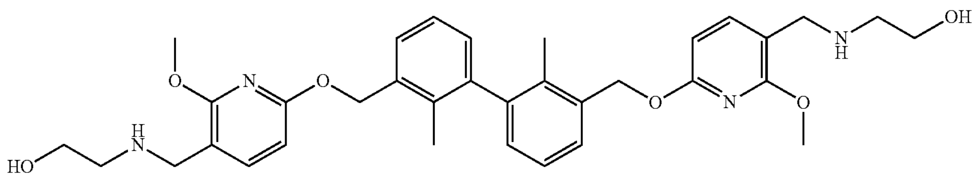 [SMILES: COc1nc(OCc2cccc(-c3cccc(COc4ccc(CNCCO)c(OC)n4)c3C)c2C)ccc1CNCCO]

To a solution of 6,6'-(((2,2'-dimethyl-[1,1'-biphenyl]-3,3'-diyl)bis(methylene))bis(oxy))bis(2-methoxynicotinaldehyde) (39 mg, 0.08 mmol) in DMF (2.0 mL) was added ethanolamine (0.04 mL, 0.61 mmol), sodium cyanoborohydride (38 mg, 0.61 mmol) and acetic acid (0.20 mL) and the mixture was stirred at rt. After 45 min, the reaction mixture was concentrated and purified by reverse phase chromatography to give the title compound as TFA salt. LCMS-ESI$^+$ (m/z): $[M+H]^+$ calculated for $C_{34}H_{42}N_4O_6$: 603.3; found: 603.1. $^1$H NMR (400 MHz, DMSO-d6) δ 8.68-8.62 (s, 4H), 7.75 (d, J=8.1 Hz, 2H), 7.44 (dd, J=7.6, 1.4 Hz, 2H), 7.25 (t, J=7.6 Hz, 2H), 7.05 (dd, J=7.7, 1.3 Hz, 2H), 6.53 (d, J=8.1 Hz, 2H), 5.44 (s, 4H), 4.12-4.05 (m, 4H), 3.92 (s, 6H), 3.68-3.60 (m, 4H), 2.99-2.92 (m, 4H), 2.00 (s, 6H).

Example 22: 2,2'-((((((2,2'-dimethyl-[1,1'-biphenyl]-3,3'-diyl)bis(methylene))bis(oxy))bis(5-chloro-2-(pyridin-3-ylmethoxy)-4,1-phenylene))bis(methylene))bis(azanediyl))bis(ethan-1-ol)

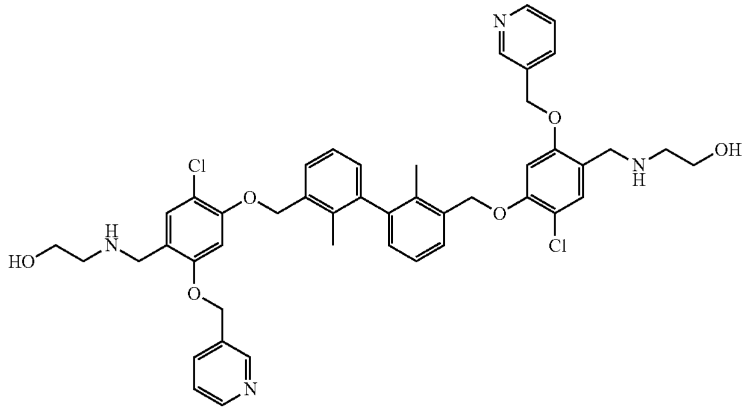 [SMILES: Cc1c(COc2cc(OCc3cccnc3)c(CNCCO)cc2Cl)cccc1-c1cccc(COc2cc(OCc3cccnc3)c(CNCCO)cc2Cl)c1C]

Step 1: To a solution of 4,4'-(((2,2'-dimethyl-[1,1'-biphenyl]-3,3'-diyl)bis(methylene))bis(oxy))bis(5-chloro-2-hydroxybenzaldehyde) (85 mg, 0.15 mmol) in DMF (5 mL) and $Cs_2CO_3$ (121 mg, 0.37 mmol), a separate solution of 3-(chloromethyl)pyridine (47 mg, 0.15 mmol) in DMF (2 mL) was added followed by the addition of NaI (277 mg, 1.85 mmol) at once. The reaction mixture was heated at 75° C. After 16 h, the reaction mixture was diluted with $CH_2Cl_2$ and brine solution. The organic layer was then separated and the aqueous layer was back extracted with $CH_2Cl_2$ and the combined organic layers were dried ($MgSO_4$). Filtration, concentration and followed by purification by column chromatography ($SiO_2$, 1% EtOAc/hexanes to 100% EtOAc/hexanes) gave 4,4'-(((2,2'-dimethyl-[1,1'-biphenyl]-3,3'-diyl)bis(methylene))bis(oxy))bis(5-chloro-2-(pyridin-3-ylmethoxy)benzaldehyde).

Step 2: To a solution of 4,4'-(((2,2'-dimethyl-[1,1'-biphenyl]-3,3'-diyl)bis(methylene))bis(oxy))bis(5-chloro-2-(pyridin-3-ylmethoxy)benzaldehyde) (42 mg, 0.05 mmol) in DMF (2.0 mL) was added ethanolamine (21 mg, 0.34 mmol), sodium cyanoborohydride (43 mg, 0.6 mmol) and acetic acid (0.20 mL) and the mixture was stirred at 45° C. After 18 h, the reaction mixture was concentrated and purified by reverse phase chromatography to give the title compound as TFA salt. LCMS-ESI$^+$ (m/z): $[M+H]^+$ calculated for $C_{46}H_{48}Cl_2N_4O_6$: 823.2; found: 823.2. $^1H$ NMR (400 MHz, DMSO-d6) δ 8.78 (s, 1H), 8.60 (d, J=4.9 Hz, 1H), 7.57 (s, 1H), 7.50 (d, J=10.9 Hz, 2H), 7.32 (t, J=7.6 Hz, 1H), 7.25 (s, 1H), 7.13 (d, J=7.0 Hz, 1H), 5.33 (d, J=7.6 Hz, 4H), 3.62 (s, 1H), 2.93 (s, 2H), 2.67 (t, J=1.8 Hz, 2H), 2.35-2.29 (m, 2H), 2.05 (s, 3H).

Example 23: (2S,2'S)-1,1'-((((((2,2'-dimethyl-[1,1'-biphenyl]-3,3'-diyl)bis(methylene))bis(oxy))bis(2-methoxypyridine-6,3-diyl))bis(methylene))bis(azanediyl))bis(propan-2-ol) (or (2S,2'S)-1,1'-(((6,6'-(((2,2'-dimethyl-[1,1'-biphenyl]-3,3'-diyl)bis(methylene))bis(oxy))bis(2-methoxypyridine-6,3-diyl))bis(methylene))bis(azanediyl))bis(propan-2-ol))

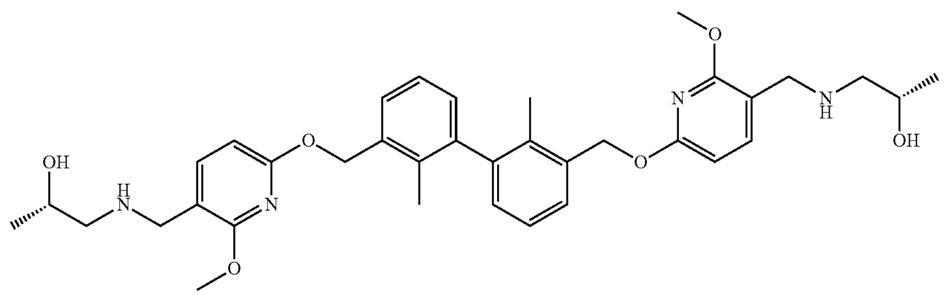 [SMILES: COc1nc(OCc2cccc(-c3cccc(COc4ccc(CNC[C@H](C)O)c(OC)n4)c3C)c2C)ccc1CNC[C@H](C)O]

To a solution of 6,6'-(((2,2'-dimethyl-[1,1'-biphenyl]-3,3'-diyl)bis(methylene))bis(oxy))bis(2-methoxynicotinaldehyde) (39 mg, 0.08 mmol) in DMF (2.0 mL) was added (S)-1-aminopropan-2-ol (46 mg, 0.61 mmol), sodium cyanoborohydride (38 mg, 0.61 mmol) and acetic acid (0.20 mL) and the mixture was stirred at 45° C. After 4h, the reaction mixture was concentrated and purified by reverse phase chromatography to give the title compound as TFA salt. LCMS-ESI$^+$ (m/z): $[M+H]^+$ calculated for $C_{34}H_{46}N_4O_6$: 631.3; found: 631.1. $^1H$ NMR (400 MHz, DMSO-d6) δ 8.53 (brs, 4H), 7.75 (d, J=8.1 Hz, 2H), 7.47-7.39 (m, 2H), 7.25 (t, J=7.6 Hz, 2H), 7.05 (dd, J=7.6, 1.4 Hz, 2H), 6.52 (d, J=8.1 Hz, 2H), 5.43 (s, 4H), 5.32 (brs), 4.10-3.98 (m, 4H), 3.93 (s, 6H), 2.90-2.80 (m, 2H), 2.75-2.62 (m, 4H), 2.88 (d, J=4.9 Hz, 2H), 2.75-2.61 (m, 4H), 2.00 (s, 6H), 1.09 (d, J=6.3 Hz, 6H).

Example 24: (2R,2'R)-1,1'-((((((2,2'-dimethyl-[1,1'-biphenyl]-3,3'-diyl)bis(methylene))bis(oxy))bis(2-methoxypyridine-6,3-diyl))bis(methylene))bis(azanediyl))bis(propan-2-ol) (or (2R,2'R)-1,1'-(((6,6'-(((2,2'-dimethyl-[1,1'-biphenyl]-3,3'-diyl)bis(methylene))bis(oxy))bis(2-methoxypyridine-6,3-diyl))bis(methylene))bis(azanediyl))bis(propan-2-ol))

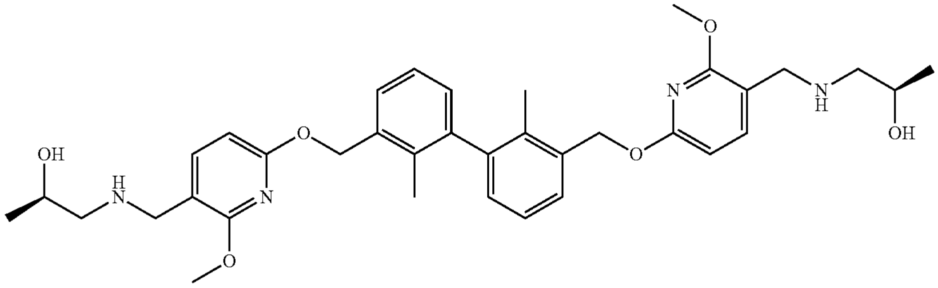 [SMILES: COc1nc(OCc2cccc(-c3cccc(COc4ccc(CNC[C@@H](C)O)c(OC)n4)c3C)c2C)ccc1CNC[C@@H](C)O]

To a solution of 6,6'-(((2,2'-dimethyl-[1,1'-biphenyl]-3,3'-diyl)bis(methylene))bis(oxy))bis(2-methoxynicotinaldehyde) (39 mg, 0.08 mmol) in DMF (2.0 mL) was added (R)-1-aminopropan-2-ol (46 mg, 0.61 mmol), sodium cyanoborohydride (38 mg, 0.61 mmol) and acetic acid (0.20 mL) and the mixture was stirred at 45° C. After 4h, the reaction mixture was concentrated and purified by reverse phase chromatography to give the title compound as TFA salt. LCMS-ESI$^+$ (m/z): $[M+H]^+$ calculated for $C_{34}H_{46}N_4O_6$: 631.3; found: 631.2. $^1H$ NMR (400 MHz, DMSO-d6) δ 8.53 (brs, 4H), 7.75 (d, J=8.1 Hz, 2H), 7.44 (dd, J=7.6, 1.4 Hz, 2H), 7.25 (t, J=7.6 Hz, 2H), 7.05 (dd, J=7.7, 1.4 Hz, 2H), 6.52 (d, J=8.1 Hz, 2H), 5.43 (s, 4H), 5.31 (brs), 4.08-3.99 (m, 4H), 3.91 (s, 6H), 2.90-2.80 (m, 2H), 2.75-2.62 (m, 4H), 2.00 (s, 6H), 1.09 (d, J=6.3 Hz, 6H).

Example 25: 5,5'-((((([1,1'-biphenyl]-3,3'-diylbis(methylene))bis(oxy))bis(4-chloro-6-(((2-hydroxyethyl)amino)methyl)-3,1-phenylene))bis(oxy))bis(methylene))dinicotinonitrile (or 5,5'-((((([1,1'-biphenyl]-3,3'-diylbis(methylene))bis(oxy))bis(4-chloro-2-(((2-hydroxyethyl)amino)methyl)-5,1-phenylene))bis(oxy))bis(methylene))dinicotinonitrile)

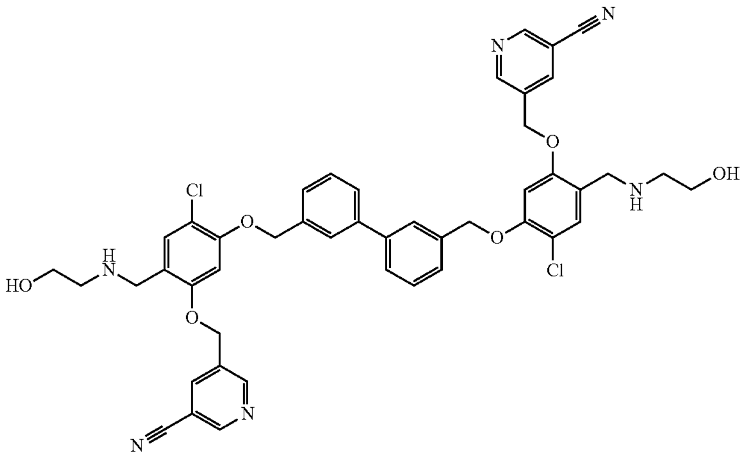 [SMILES: N#Cc1cncc(COc2cc(OCc3cccc(-c4cccc(COc5cc(OCc6cncc(C#N)c6)c(CNCCO)cc5Cl)c4)c3)c(Cl)cc2CNCCO)c1]

Step 1: To a mixture of 5-((5-((3-bromobenzyl)oxy)-4-chloro-2-formylphenoxy)methyl)nicotinonitrile (100 mg, 0.22 mmol), potassium acetate (32 mg, 0.33 mmol), 4,4,5,5,-tetramethyl-2-(4,4,5,5,-tetramethyl-1,3,2-dioxaborolan-2-yl)-1,3,2-dioxaborolane (72 mg, 0.28 mmol) and 1,1'-bis(diphenylphosphino)ferrocene palladium(II) chloride dichloromethane adduct (20 mg, 0.03 mmol) was added 1,4-dioxane (2 mL). The mixture was heated in a heating block in microwave vial at 95° C. for 1h. After cooling to room temperature, the reaction mixture was diluted with EtOAc and water. The organic layer was then separated and the aqueous layer was back extracted with EtOAc and the combined organic layers were dried ($MgSO_4$). Filtration, concentration gave 5-((4-chloro-2-formyl-5-((3-(4,4,5,5-tetramethyl-1,3,2-dioxaborolan-2-yl)benzyl)oxy)phenoxy)methyl)nicotinonitrile which was used further without purification.

Step 2: To a mixture 5,5'-(((((([1,1'-biphenyl]-3,3'-diylbis(methylene))bis(oxy))bis(4-chloro-6-formyl-3,1-phenylene))bis(oxy))bis(methylene))dinicotinonitrile (75 mg, 0.15 mmol) and 5-((5-((3-bromobenzyl)oxy)-4-chloro-2-formylphenoxy)methyl)nicotinonitrile (113 mg, 0.25 mmol) in 1,4-Dioxane/water (6 mL, 2:1) was added $Cs_2CO_3$(96 mg, 0.30 mmol) and PEPSI-iPr (5 mg, 0.007 mmol) and the reaction mixture was heated at 95° C. for 30 min. After cooling to room temperature, the reaction mixture was diluted with EtOAc and water. The organic layer was then separated and the aqueous layer was back extracted with EtOAc and the combined organic layers were dried ($MgSO_4$). Filtration, concentration and followed by purification by column chromatography ($SiO_2$, 0% MeOH/EtOAc to 5% MeOH/EtOAc) gave 5,5'-(((((([1,1'-biphenyl]-3,3'-diylbis(methylene))bis(oxy))bis(4-chloro-6-formyl-3,1-phenylene))bis(oxy))bis(methylene)) dinicotinonitrile.

Step 3: To a solution of 5,5'-(((((([1,1'-biphenyl]-3,3'-diylbis(methylene))bis(oxy))bis(4-chloro-6-formyl-3,1-phenylene))bis(oxy))bis(methylene)) dinicotinonitrile (29 mg, 0.04 mmol) in DMF (2.0 mL) was added ethanolamine (14 mg, 0.23 mmol), sodium cyanoborohydride (30 mg, 0.46 mmol) and acetic acid (0.20 mL) and the mixture was stirred at 45° C. After 18 h, the reaction mixture was concentrated and purified by reverse phase chromatography to give the title compound as TFA salt. LCMS-ESI$^+$ (m/z): $[M+H]^+$ calculated for $C_{46}H_{42}Cl_2N_6O_6$: 845.2; found: 845.2. $^1H$ NMR (400 MHz, DMSO-d6) δ 9.02 (d, J=2.1 Hz, 1H), 8.99 (d, J=2.1 Hz, 1H), 8.44 (s, 1H), 7.79 (s, 1H), 7.65 (d, J=8.0 Hz, 1H), 7.58 (s, 1H), 7.52 (s, 1H), 7.47 (d, J=7.9 Hz, 2H), 7.15 (s, 1H), 5.37 (s, 2H), 5.34 (s, 2H), 4.13 (s, 2H), 2.68-2.65 (m, 3H), 2.35-2.29 (m, 3H), 2.08 (s, 1H).

Example 26: (S)-3-hydroxy-4-(((6-((3'-(((5-(((S)-4-hydroxy-2-oxopyrrolidin-1-yl)methyl)-6-methoxypyridin-2-yl)oxy)methyl)-2,2'-dimethyl-[1,1'-biphenyl]-3-y)methoxy)-2-methoxypyridin-3-yl)methyl)amino)butanoic acid

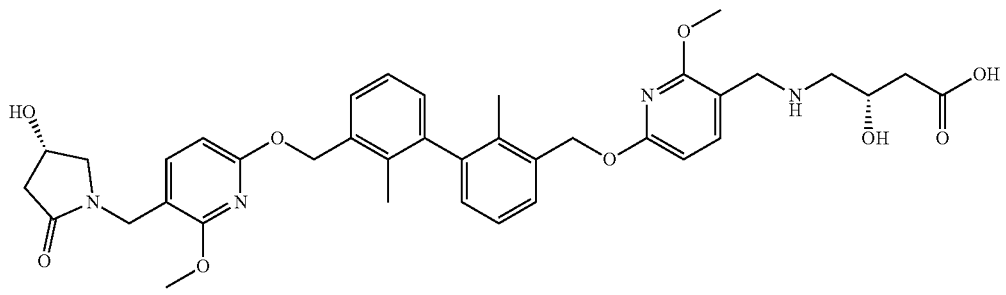 [SMILES: COc1nc(OCc2cccc(-c3cccc(COc4ccc(CN5C[C@@H](O)CC5=O)c(OC)n4)c3C)c2C)ccc1CNC[C@@H](O)CC(=O)O]

To a solution of 6,6'-(((2,2'-dimethyl-[1,1'-biphenyl]-3,3'-diyl)bis(methylene))bis(oxy))bis(2-methoxynicotinaldehyde) (28 mg, 0.06 mmol) in DMF (2.0 mL) was added (S)-4-amino-3-hydroxybutanoic acid (52 mg, 0.43 mmol), sodium cyanoborohydride (27 mg, 0.44 mmol) and acetic acid (0.20 mL) and the mixture was stirred at rt. After 36 h, the reaction mixture was concentrated and purified by reverse phase chromatography to give the title compound as TFA salt. LCMS-ESI$^+$ (m/z): $[M+H]^+$ calculated for $C_{38}H_{44}N_4O_9$: 701.3; found: 701.3. $^1H$ NMR (400 MHz, DMSO-d6) δ 8.19 (d, J=8.1 Hz, 1H), 8.07-7.96 (m, 3H), 7.81 (td, J=7.6, 3.9 Hz, 2H), 7.63 (td, J=7.5, 1.4 Hz, 2H), 6.99 (d, J=8.0 Hz, 1H), 6.92 (d, J=7.9 Hz, 1H), 6.08-5.98 (m, 4H), 4.94-4.75 (m, 4H), 4.68 (s, 2H), 4.54 (s, 3H), 4.48 (s, 3H), 4.09-4.04 (m, 1H), 3.72-3.67 (m, 3H), 3.55-3.49 (m, 2H), 3.17-2.90 (m, 4H), 2.59 (s, 6H).

Example 27: (S)-4-(((6-((3'-((4-((((S)-3-carboxy-2-hydroxypropyl)amino)methyl)-3-methoxyphenoxy)methyl)-2,2'-dimethyl-[1,1'-biphenyl]-3-yl)methoxy)-2-methoxypyridin-3-yl)methyl)amino)-3-hydroxybutanoic acid

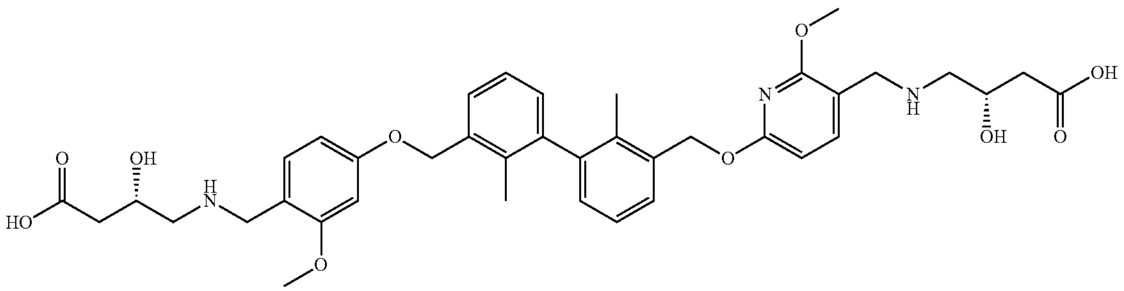 [SMILES: COc1cc(OCc2cccc(-c3cccc(COc4ccc(CNC[C@@H](O)CC(=O)O)c(OC)n4)c3C)c2C)ccc1CNC[C@@H](O)CC(=O)O]

Step 1: To a solution of 4-hydroxy-2-methoxybenzaldehyde (341 mg, 2.24 mmol), (3-bromo-2-methylphenyl)methanol (410 mg, 2.04 mmol), $PPh_3$ (801 mg, 3.06 mmol) in 2-MeTHF (7.0 mL) at 0° C. was added Diisopropyl azodicarboxylate (0.6 mL, 3.06 mmol). The ice bath was removed and the reaction mixture was then stirred at rt. After 4h, the reaction mixture was directly purified by column chromatography ($SiO_2$, 1% EtOAc/hexanes to 50% EtOAc/hexanes) to give 4-((3-bromo-2-methylbenzyl)oxy)-2-methoxybenzaldehyde Step 2: To a mixture 2-methoxy-6-((2-methyl-3-(4,4,5,5-tetramethyl-1,3,2-dioxaborolan-2-yl)benzyl)oxy)nicotinaldehyde (70 mg, 0.18 mmol) and 4-((3-bromo-2-methylbenzyl)oxy)-2-methoxybenzaldehyde (70 mg, 0.21 mmol) in DME/water (3 mL, 2:1) was added $Cs_2CO_3$ (94 mg, 0.29 mmol), KOAc (11 mg, 0.19 mmol) and PEPSI-iPr (7 mg, 0.01 mmol) and the reaction mixture was heated in microwave at 110° C. for 20 min. After cooling to room temperature, the reaction mixture was directly purified by column chromatography ($SiO_2$, 1% EtOAc/hexanes to 50% EtOAc/hexanes) to give 6-((3'-((4-formyl-3-methoxyphenoxy)methyl)-2,2'-dimethyl-[1,1'-biphenyl]-3-yl)methoxy)-2-methoxynicotinaldehyde Step 3: To a solution of 6-((3'-((4-formyl-3-methoxyphenoxy)methyl)-2,2'-dimethyl-[1,1'-biphenyl]-3-y)methoxy)-2-methoxynicotinaldehyde (15 mg, 0.03 mmol) in DMF (2.0 mL) was added (S)-4-amino-3-hydroxybutanoic acid (40 mg, 0.34 mmol), sodium cyanoborohydride (30 mg, 0.48 mmol) and acetic acid (0.20 mL) and the mixture was stirred at rt. After 18 h, the reaction mixture was concentrated and purified by reverse phase chromatography to give the title compound as TFA salt. LCMS-ESI (m/z): $[M+H]^+$ calculated for $C_{39}H_{47}N_3O_{10}$: 718.3; found: 718.2. $^1H$ NMR (400 MHz, Methanol-d4) δ 7.68 (d, J=8.1 Hz, 1H), 7.44 (dt, J=7.7, 1.4 Hz, 2H), 7.35-7.19 (m, 3H), 7.07 (ddd, J=7.7, 5.1, 1.4 Hz, 2H), 6.75 (d, J=2.3 Hz, 1H), 6.70 (dd, J=8.4, 2.3 Hz, 1H), 6.48 (d, J=8.1 Hz, 1H), 5.49 (s, 2H), 5.18 (s, 2H), 4.32-4.28 (m, 2H), 4.19-4.17 (m, 5H), 4.03 (s, 3H), 3.91 (s, 3H), 3.22-3.08 (m, 3H), 3.02-2.83 (m, 3H), 2.57-2.50 (m, 6H), 2.07 (s, 3H), 2.05 (s, 3H).

Example 28: 2,2'-((((((2,2'-dimethyl-[1,1'-biphenyl]-3,3'-diyl)bis(methylene))bis(oxy))bis(5-chloro-2-(2-morpholinoethoxy)-4,1-phenylene))bis(methylene))bis(azanediyl))bis(ethan-1-ol)

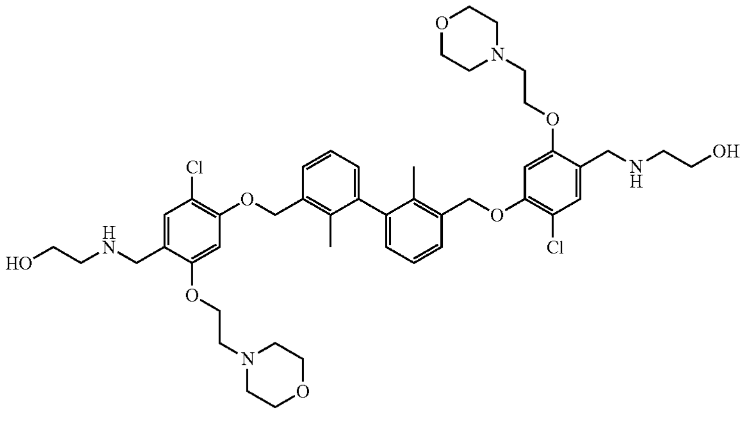 [SMILES: Cc1c(COc2cc(OCCN3CCOCC3)c(CNCCO)cc2Cl)cccc1-c1cccc(COc2cc(OCCN3CCOCC3)c(CNCCO)cc2Cl)c1C]

Step 1: To a solution of 4,4'-(((2,2'-dimethyl-[1,1'-biphenyl]-3,3'-diyl)bis(methylene))bis(oxy))bis(5-chloro-2-hydroxybenzaldehyde) (86 mg, 0.16 mmol) in DMF (3 mL) was added $Cs_2CO_3$ (254 mg, 0.78 mmol), 4-(2-chloroethyl) morpholine (93 mg, 0.62 mmol) and NaI (47 mg, 0.31 mmol). The reaction mixture was heated at 75° C. After 16 h, the reaction mixture was diluted with EtOAc and brine solution. The organic layer was then separated and the aqueous layer was back extracted with EtOAc and the combined organic layers were dried ($MgSO_4$). Filtration, concentration gave 4,4'-(((2,2'-dimethyl-[1,1'-biphenyl]-3,3'-diyl)bis(methylene))bis(oxy))bis(5-chloro-2-(2-morpholinoethoxy)benzaldehyde) which was used further without purification.

Step 2: To a solution of 4,4'-(((2,2'-dimethyl-[1,1'-biphenyl]-3,3'-diyl)bis(methylene))bis(oxy))bis(5-chloro-2-(pyridin-3-ylmethoxy)benzaldehyde) in DMF (2.0 mL) was added ethanolamine (21 mg, 0.34 mmol), sodium cyanoborohydride (43 mg, 0.6 mmol) and acetic acid (0.20 mL) and the mixture was stirred at 45° C. After 1 h, 2 more equiv. of ethanolamine and sodium cyanoborohydride was added and heated at 45° C. After 16 h, Sodium triacetoxyborohydride was added and heated at 45° C. for 3 h. The reaction mixture was concentrated and purified by reverse phase chromatography to give the title compound as TFA salt. LCMS-ESI+ (m/z): $[M+H]^+$ calculated for $C_{46}H_{60}Cl_2N_4O_8$: 868.2; found: 868.3.

Example 29: (3S,3'S)-4,4'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(3-hydroxybutanoic acid) (or (3S,3'S)-4,4'-(((6,6'-(((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(3-hydroxybutanoic acid))

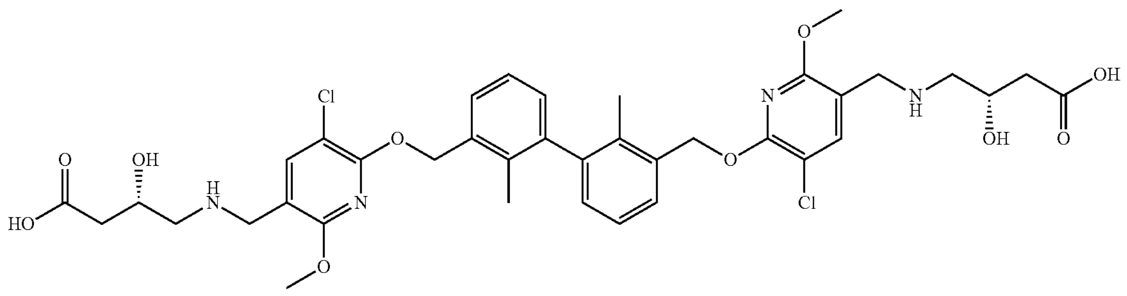 [SMILES: COc1nc(OCc2cccc(-c3cccc(COc4nc(OC)c(CNC[C@@H](O)CC(=O)O)cc4Cl)c3C)c2C)c(Cl)cc1CNC[C@@H](O)CC(=O)O]

-

6,6'-(((2,2'-dimethyl-[1,1'-biphenyl]-3,3'-diyl)bis(methylene))bis(oxy))bis(5-chloro-2-methoxynicotinaldehyde) (6 mg, 0.01 mmol) was converted to the title compound using general reductive amination procedure F. LCMS-ESI+ (m/z): $[M+H]^+$ calculated for $C_{38}H_{44}Cl_2N_4O_{10}$: 787.3; found: 787.2. $^1H$ NMR (400 MHz, Methanol-d4) δ 7.81 (s, 2H), 7.47 (dd, J=7.7, 1.4 Hz, 2H), 7.24 (t, J=7.6 Hz, 2H), 7.07 (dd, J=7.7, 1.3 Hz, 2H), 5.59 (s, 4H), 4.29 (dtd, J=9.4, 6.2, 3.0 Hz, 2H), 4.16 (s, 4H), 4.05 (s, 6H), 3.21 (dd, J=12.8, 3.0 Hz, 2H), 3.00 (dd, J=12.7, 9.8 Hz, 2H), 2.54 (d, J=6.3 Hz, 4H), 2.09 (s, 6H).

Example 30: 6,6'-(((2,2'-dimethyl-[1,1'-biphenyl]-3,3'-diyl)bis(methylene))bis(oxy))bis(5-chloro-3-(4,5-dihydro-1H-imidazol-2-yl)-2-methoxypyridine)

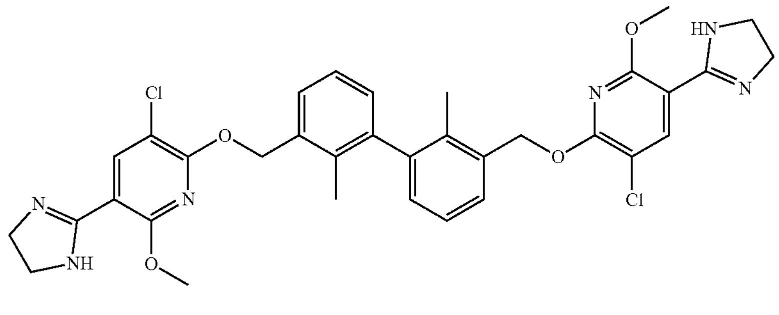 [SMILES: COc1nc(OCc2cccc(-c3cccc(COc4nc(OC)c(C5=NCCN5)cc4Cl)c3C)c2C)c(Cl)cc1C1=NCCN1]

To a stirred solution of Intermediate 18 (1 equiv) and ethylenediamine (2.5 equiv) at 0° C., was added NBS (2.5 equiv) in a single portion. The reaction was allowed to slowly warm to room temperature. After 18 hours at room temperature full conversion was observed by LCMS. The reaction mixture was then diluted with 5:1 DMF/$H_2O$ to a total volume of 4.5 mL and purified by reverse phase HPLC to afford after lyophilization 6,6'-(((2,2'-dimethyl-[1,1'-biphenyl]-3,3'-diyl)bis(methylene))bis(oxy))bis(5-chloro-3-(4,5-dihydro-1H-imidazol-2-yl)-2-methoxypyridine) as the bis TFA salt. $^1$H NMR (400 MHz, Methanol-$d_4$) δ 8.25 (s, 1H), 7.51 (dd, J=7.6, 1.3 Hz, 1H), 7.29 (t, J=7.6 Hz, 1H), 7.13 (dd, J=7.6, 1.4 Hz, 1H), 5.70 (s, 2H), 4.19 (s, 3H), 4.03 (s, 4H), 2.11 (s, 3H). LCMS found 661.276.

Example 31: (S)-4-(((6-(3'-((4-((((S)-3-carboxy-2-hydroxypropyl)amino)methyl)-2-chloro-5-((5-cyanopyridin-3-yl)methoxy)phenoxy)methyl)-2,2'-dimethyl-[1,1'-biphenyl]-3-yl)naphthalen-2-yl)methyl)amino)-3-hydroxybutanoic acid

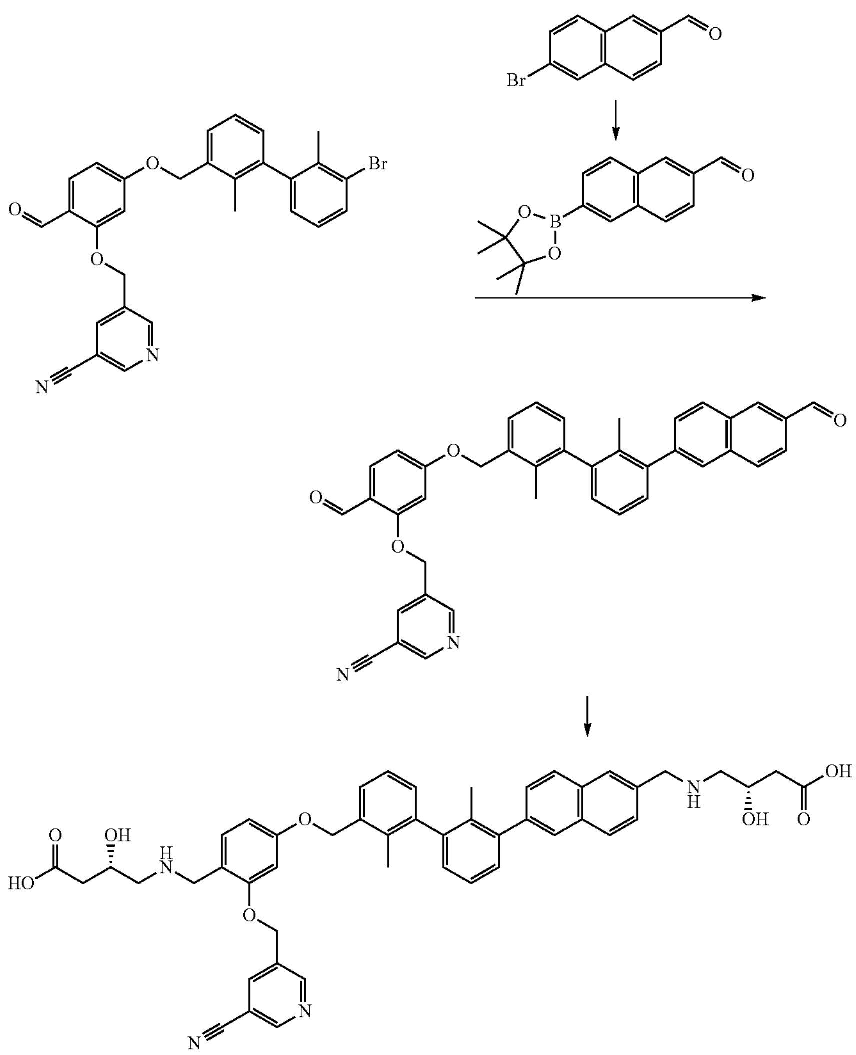

A vial was charged with 6-bromo-2-naphthaldehyde (500 mg, 2.12 mmol, 1 equiv), bis(pinacolato)diboron (648 mg, 2.55 mmol, 1.2 equiv), [1,1'-Bis(diphenylphosphino)ferrocene]dichloropalladium(II) (87 mg, 0.1 mmol) 5 mol %), and KOAc (420 mg, 4.24 mmol, 2 equiv). The vial was sealed and dry dioxane was added via syringe. The mixture was then degassed by sparging with argon for 10 minutes. The vessel was then heated to 100 C for 2 hours. The reaction was diluted with ethyl acetate and filtered through celites. The filter cake was extracted with ethyl acetate (3×3 mL). The filtrate was concentrate in vacuo. The crude material was purified by silica gel chromatography (Hex/EtOAc, 100:0 to 0:100) to afford 6-(4,4,5,5-tetramethyl-1,3,2-dioxaborolan-2-yl)-2-naphthaldehyde.

A vial was charged with Intermediate 19 (1 equiv), 6-(4,4,5,5-tetramethyl-1,3,2-dioxaborolan-2-yl)-2-naphthaldehyde (1.5 equiv), [1,1'-Bis(diphenylphosphino)ferrocene]dichloropalladium(II) (5 mol %), and $K_2CO_3$ (2 equiv). After the vial was sealed dry dioxane (2 mL) and water (0.4 mL) were added via syringe. The mixture was then degassed by sparging with argon for 10 minutes. The vessel was then heated to 100 C for 2 hours. The reaction was diluted with ethyl acetate and filtered through celites. The filter cake was extracted with ethyl acetate (3×3 mL). The filtrate was concentrate in vacuo. The crude material was purified by silica gel chromatography (Hex/EtOAc, 100:0 to 0:100) to afford 5-((4-chloro-2-formyl-5-((3'-(6-formylnaphthalen-2-yl)-2,2'-dimethyl-[1,1'-biphenyl]-3-yl)methoxy)phenoxy) methyl)nicotinonitrile.

5-((4-chloro-2-formyl-5-((3'-(6-formylnaphthalen-2-yl)-2,2'-dimethyl-[1,1'-biphenyl]-3-yl)methoxy)phenoxy) methyl)nicotinonitrile (1 equiv) was suspended in DMF (0.025 M) and to this was added (3S)-4-Amino-3-hydroxybutanoic acid (6 equiv) followed by triethylamine (6 equiv) and the reaction stirred at room temperature for 90 minutes. To this was added sodium triacetoxyborohydride (6 equiv) and the reaction stirred an additional 4 hours. At this point TFA was added slowly dropwise to the reaction until the solution went clear. The reaction mixture was then diluted with DMF to a total volume of 4.5 mL and purified by reverse phase HPLC to afford after lyophilization (S)-4-(((6-(3'-((4-((((S)-3-carboxy-2-hydroxypropyl)amino) methyl)-2-chloro-5-((5-cyanopyridin-3-yl)methoxy)phenoxy)methyl)-2,2'-dimethyl-[1,1'-biphenyl]-3-yl) naphthalen-2-yl)methyl)amino)-3-hydroxybutanoic acid as the bis TFA salt. $^1$H NMR (400 MHz, Methanol-$d_4$) δ 8.96 (d, J=2.1 Hz, 1H), 8.93 (d, J=1.9 Hz, 1H), 8.38 (s, 1H), 8.07 (s, 1H), 8.03 (d, J=8.6 Hz, 1H), 8.00 (d, J=8.6 Hz, 1H), 7.89 (s, 1H), 7.62 (dd, J=8.5, 1.7 Hz, 1H), 7.60-7.56 (m, 1H), 7.52 (s, 1H), 7.48 (d, J=7.6 Hz, 1H), 7.40-7.25 (m, 4H), 7.19 (d, J=7.5 Hz, 1H), 7.17-7.14 (m, 1H), 7.09 (s, 1H), 5.39 (s, 2H), 5.33 (s, 2H), 4.45 (s, 2H), 4.34 (dt, J=6.8, 3.3 Hz, 0H), 4.24 (s, 3H), 3.27-3.16 (m, 2H), 3.07 (dd, J=12.7, 9.8 Hz, 1H), 3.02-2.94 (m, 1H), 2.56 (d, J=6.3 Hz, 2H), 2.54-2.51 (m, 2H), 2.19 (s, 3H), 1.94 (d, J=0.9 Hz, 4H). LCMS found 843.231.

Example 32: (3R,3'R)-4,4'-((((((2,2'-dimethyl-[1,1'-biphenyl]-3,3'-diyl)bis(methylene))bis(oxy))bis(5-chloro-2-((5-cyanopyridin-3-yl)methoxy)pyridine-6,3-diyl))bis(methylene))bis(azanediyl))bis(3-hydroxybutanoic acid) (or (3R,3'R)-4,4'-(((6,6'-(((2,2'-dimethyl-[1,1'-biphenyl]-3,3'-diyl)bis(methylene)) bis(oxy))bis(5-chloro-2-((5-cyanopyridin-3-yl) methoxy)pyridine-6,3-diyl))bis(methylene))bis (azanediyl))bis(3-hydroxybutanoic acid))

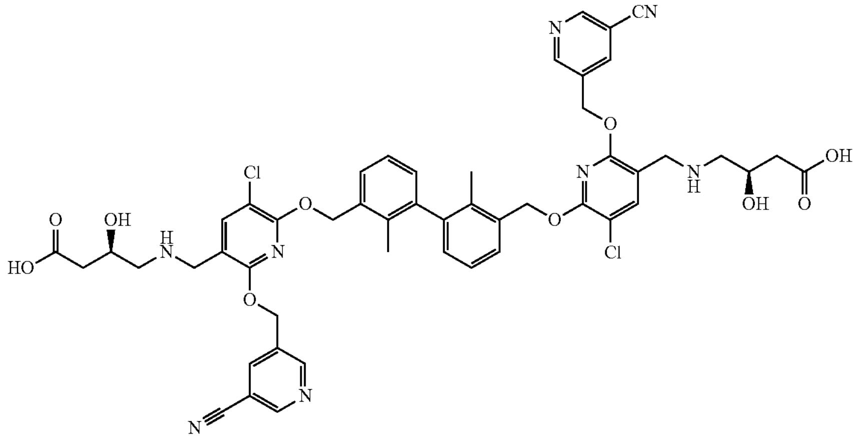 [SMILES: Cc1c(COc2nc(OCc3cncc(C#N)c3)c(CNC[C@H](O)CC(=O)O)cc2Cl)cccc1-c1cccc(COc2nc(OCc3cncc(C#N)c3)c(CNC[C@H](O)CC(=O)O)cc2Cl)c1C]

To a stirred mixture of Intermediate 20 (1 equiv) and (S)-3-aminobutanoic acid (5 equiv) in a 6:1 mixture of DMF/AcOH (0.02 M) at room temperature was added sequentially sodium cyanoborohydride (9 equiv) and sodium triacetoxyborohydride (9 equiv). After 4 hours at room temperature the reaction mixture was diluted with DMF/$H_2O$ (5:1) to a total volume of 4.5 mL. The resulting mixture was purified by reverse phase HPLC (0.1% trifluoroacetic acid in acetonitrile/water) providing the title compound upon lyophilization as the bis-TFA salt. $^1$H NMR (400 MHz, Methanol-$d_4$) δ 8.94 (d, J=2.1 Hz, 1H), 8.87 (d, J=2.0 Hz, 1H), 8.32 (s, 1H), 7.90 (s, 1H), 7.39 (d, J=7.6 Hz, 1H), 7.23 (t, J=7.6 Hz, 1H), 7.11-7.06 (m, 1H), 5.60 (s, 2H), 5.49 (d, J=4.1 Hz, 2H), 4.31-4.21 (m, 3H), 3.24 (dd, J=12.7, 3.1 Hz, 1H), 3.03 (dd, J=12.7, 9.8 Hz, 1H), 2.54 (d, J=6.3 Hz, 2H), 2.03 (s, 3H). LCMS found 991.141 (M+1).

Example 33: (3S,3'S)-4,4'-((((((2,2'-dimethyl-[1,1'-biphenyl]-3,3'-diyl)bis(methylene))bis(oxy))bis(5-bromo-2-((5-cyanopyridin-3-yl)methoxy)-4,1-phenylene))bis(methylene))bis(azanediyl))bis(3-hydroxybutanoic acid)

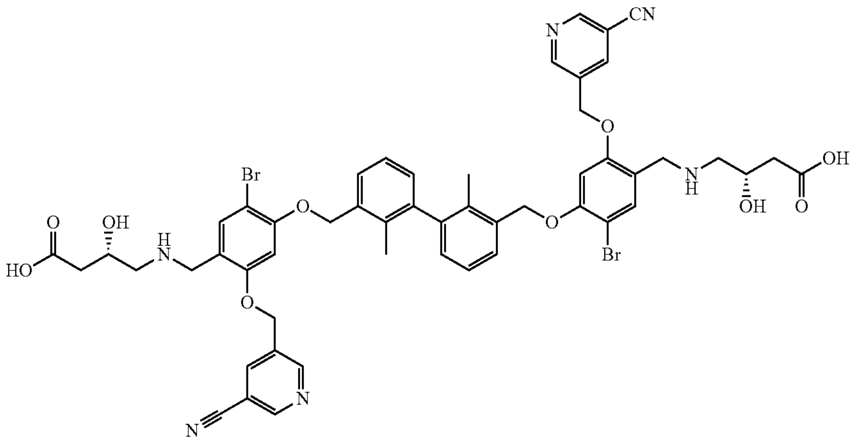 [SMILES: Cc1c(COc2cc(OCc3cncc(C#N)c3)c(CNC[C@@H](O)CC(=O)O)cc2Br)cccc1-c1cccc(COc2cc(OCc3cncc(C#N)c3)c(CNC[C@@H](O)CC(=O)O)cc2Br)c1C]

To a stirred mixture of Intermediate 21 (1 equiv) and (S)-3-aminobutanoic acid (5 equiv) in a 6:1 mixture of DMF/AcOH (0.02 M) at room temperature was added sequentially sodium cyanoborohydride (9 equiv) and sodium triacetoxyborohydride (9 equiv). After 4 hours at room temperature the reaction mixture was diluted with DMF/$H_2O$ (5:1) to a total volume of 4.5 mL. The resulting mixture was purified by reverse phase HPLC (0.1% trifluoroacetic acid in acetonitrile/water) providing the title compound upon lyophilization as the bis-TFA salt. $^1H$ NMR (400 MHz, DMSO-d6) δ 9.04 (dd, J=5.1, 2.0 Hz, 4H), 8.58 (s, 4H), 8.48 (t, J=2.1 Hz, 2H), 7.72 (s, 2H), 7.53 (d, J=7.4 Hz, 2H), 7.31 (t, J=7.6 Hz, 2H), 7.17 (s, 2H), 7.12 (d, J=7.3 Hz, 2H), 5.39 (s, 4H), 5.33 (s, 4H), 4.15 (s, 6H), 2.85 (s, 2H), 2.44 (d, J=5.3 Hz, 2H), 2.37 (dd, J=15.9, 7.2 Hz, 2H), 2.05 (s, 6H). LCMS found 1077.1 (M+1).

Example 34: (3S,3'S)-4,4'-((((((2,2'-dimethyl-[1,1'-biphenyl]-3,3'-diyl)bis(methylene))bis(oxy))bis(5-chloro-2-((5-cyanopyridin-3-yl)methoxy)pyridine-6,3-diyl))bis(methylene))bis(azanediyl))bis(3-hydroxybutanoic acid) (or (3S,3'S)-4,4'-(((6,6'-(((2,2'-dimethyl-[1,1'-biphenyl]-3,3'-diyl)bis(methylene))bis(oxy))bis(5-chloro-2-((5-cyanopyridin-3-yl)methoxy)pyridine-6,3-diyl))bis(methylene))bis(azanediyl))bis(3-hydroxybutanoic acid))

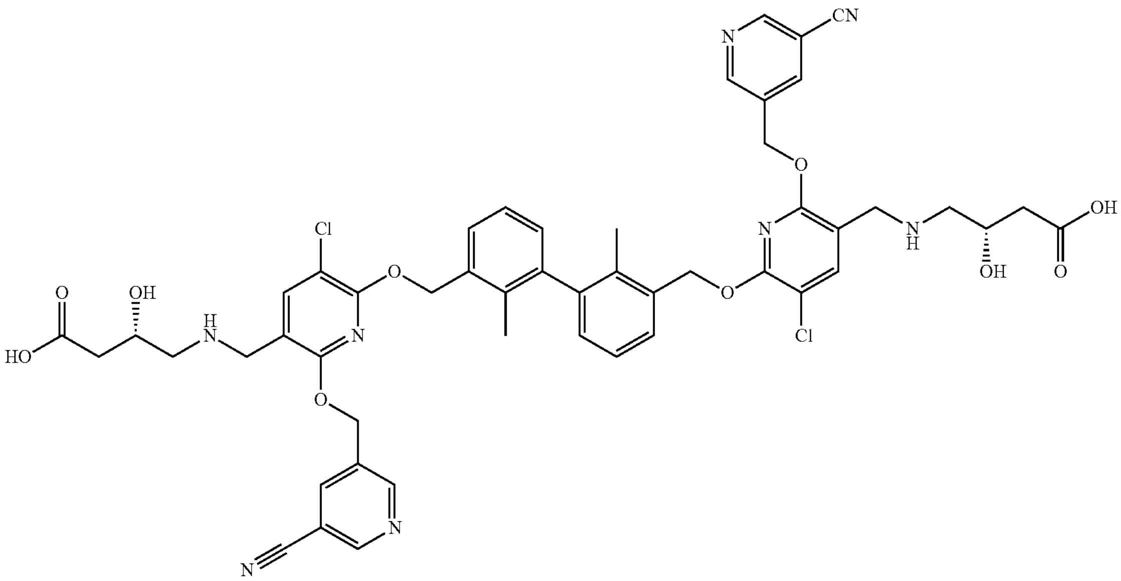 [SMILES: Cc1c(COc2nc(OCc3cncc(C#N)c3)c(CNC[C@@H](O)CC(=O)O)cc2Cl)cccc1-c1cccc(COc2nc(OCc3cncc(C#N)c3)c(CNC[C@@H](O)CC(=O)O)cc2Cl)c1C]

To a stirred mixture of Intermediate 20 (1 equiv) and (S)-3-aminobutanoic acid (5 equiv) in a 6:1 mixture of DMF/AcOH (0.02 M) at room temperature was added sequentially sodium cyanoborohydride (9 equiv) and sodium triacetoxyborohydride (9 equiv). After 4 hours at room temperature the reaction mixture was diluted with DMF/$H_2O$ (5:1) to a total volume of 4.5 mL. The resulting mixture was purified by reverse phase HPLC (0.1% trifluoroacetic acid in acetonitrile/water) providing the title compound upon lyophilization as the bis-TFA salt. $^1H$ NMR (400 MHz, Methanol-d4) δ 8.95 (d, J=2.1 Hz, 1H), 8.88 (d, J=2.0 Hz, 1H), 8.34 (t, J=2.1 Hz, 1H), 7.91 (s, 1H), 7.42-7.38 (m, 1H), 7.24 (t, J=7.6 Hz, 1H), 7.11-7.06 (m, 1H), 5.61 (t, J=2.3 Hz, 1H), 5.52-5.48 (m, 1H), 4.25 (s, 3H), 3.25 (dd, J=12.7, 3.1 Hz, 1H), 3.04 (dd, J=12.7, 9.8 Hz, 1H), 2.55 (d, J=6.3 Hz, 2H), 2.04 (s, 3H). LCMS found 991.178 (M+1).

Example 35: 5,5'-((((((2,2'-dimethyl-[1,1'-biphenyl]-3,3'-diyl)bis(methylene))bis(oxy))bis(5-chloro-3-(((2-hydroxyethyl)amino)methyl)pyridine-6,2-diyl))bis(oxy))bis(methylene))dinicotinonitrile (or 5,5'-(((6,6'-(((2,2'-dimethyl-[1,1'-biphenyl]-3,3'-diyl)bis(methylene))bis(oxy))bis(5-chloro-3-(((2-hydroxyethyl)amino)methyl)pyridine-6,2 diyl))bis(oxy))bis(methylene))dinicotinonitrile)

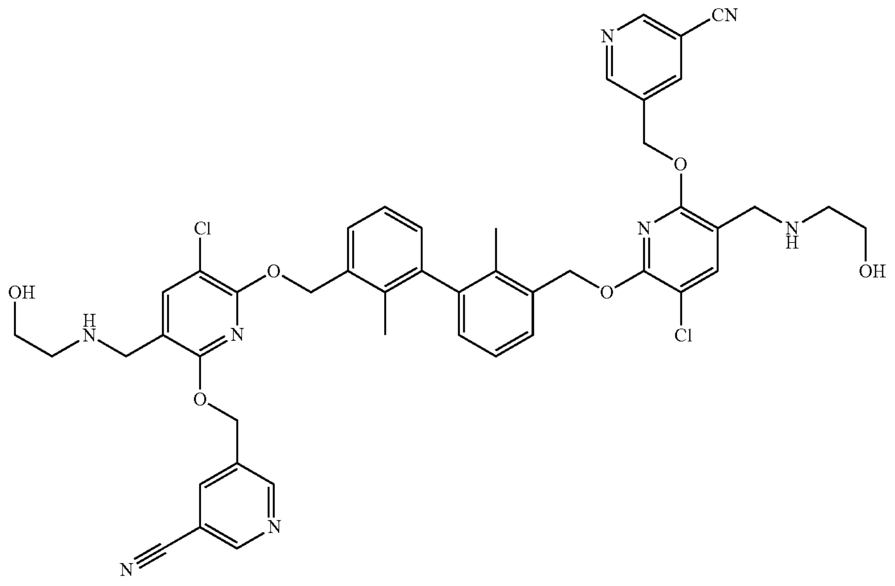 [SMILES: Cc1c(COc2nc(OCc3cncc(C#N)c3)c(CNCCO)cc2Cl)cccc1-c1cccc(COc2nc(OCc3cncc(C#N)c3)c(CNCCO)cc2Cl)c1C]

To a stirred mixture of Intermediate 20 (1 equiv) and ethanolamine (5 equiv) in a 6:1 mixture of DMF/AcOH (0.02 M) at room temperature was added sequentially sodium cyanoborohydride (9 equiv) and sodium triacetoxyborohydride (9 equiv). After 4 hours at room temperature the reaction mixture was diluted with DMF/$H_2O$ (5:1) to a total volume of 4.5 mL. The resulting mixture was purified by reverse phase HPLC (0.1% trifluoroacetic acid in acetonitrile/water) providing the title compound upon lyophilization as the bis-TFA salt. $^1H$ NMR (400 MHz, Methanol-$d_4$) δ 8.95 (d, J=2.1 Hz, 1H), 8.88 (d, J=1.9 Hz, 1H), 8.34 (t, J=2.1 Hz, 1H), 7.91 (s, 1H), 7.40 (dd, J=7.3, 1.3 Hz, 1H), 7.24 (t, J=7.6 Hz, 1H), 7.13-7.05 (m, 1H), 5.50 (d, J=3.8 Hz, 2H), 4.25 (s, 2H), 3.85-3.77 (m, 2H), 3.20-3.13 (m, 2H), 2.04 (s, 3H). LCMS found 875.120 (M+1).

Example 36: 5,5'-((((((2,2'-dimethyl-[1,1'-biphenyl]-3,3'-diyl)bis(methylene))bis(oxy))bis(6-(((2-hydroxyethyl)amino)methyl)-4-vinyl-3,1-phenylene))bis(oxy))bis(methylene))dinicotinonitrile (or 5,5'-((((((2,2'-dimethyl-[1,1'-biphenyl]-3,3'-diyl)bis(methylene))bis(oxy))bis(2-(((2-hydroxyethyl)amino)methyl)-4-vinyl-5,1-phenylene))bis(oxy))bis(methylene))dinicotinonitrile)

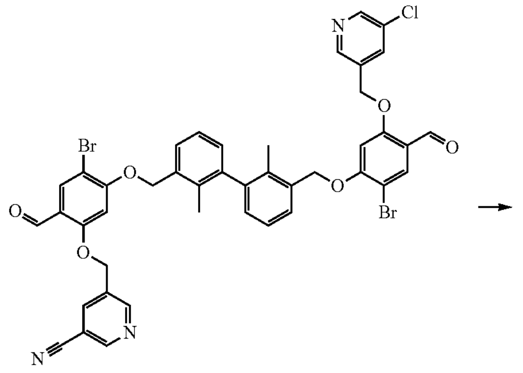

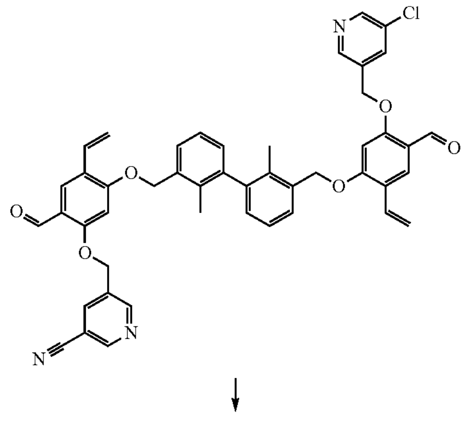

-continued

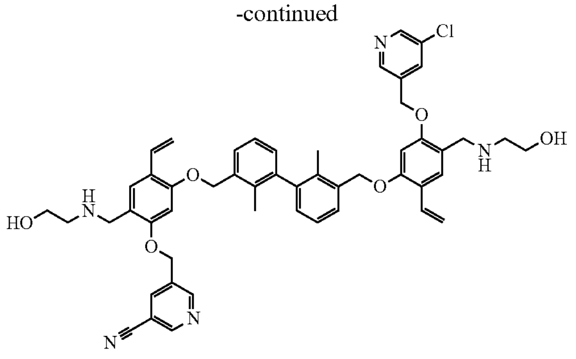

A vial was charged with Intermediate 23 (1 equiv), vinyl potassium trifluoroborate (4.0 equiv), Tetrakis(triphenylphosphine)palladium(0) (10 mol %), and $K_2CO_3$ (3 equiv). After the vial was sealed dry DMF (2 mL) and water (0.2 mL) were added via syringe. The mixture was then degassed by sparging with argon for 10 minutes. The vessel was then heated to 100 C for 2 hours. The reaction was diluted with ethyl acetate and filtered through celites. The filter cake was extracted with ethyl acetate (3x3 mL). The filtrate was concentrate in vacuo. The crude material was used without further purification. LCMS found 767.076 (M+1).

To a stirred mixture of bis-aldehyde (1 equiv) and ethanolamine (5 equiv) in a 6:1 mixture of DMF/AcOH (0.02 M) at room temperature was added sequentially sodium cyanoborohydride (9 equiv) and sodium triacetoxyborohydride (9 equiv). After 4 hours at room temperature the reaction mixture was diluted with DMF/$H_2O$ (5:1) to a total volume of 4.5 mL. The resulting mixture was purified by reverse phase HPLC (0.1% trifluoroacetic acid in acetonitrile/water) providing the title compound upon lyophilization as the bis-TFA salt. $^1$H NMR (400 MHz, DMSO-$d_6$) δ 9.04 (t, J=1.9 Hz, 2H), 8.56 (s, 2H), 8.50 (t, J=2.1 Hz, 1H), 7.66 (s, 1H), 7.31 (t, J=7.5 Hz, 1H), 7.13 (d, J=7.7 Hz, 1H), 7.05 (s, 1H), 6.89 (dd, J=17.7, 11.2 Hz, 1H), 5.69 (dd, J=17.7, 1.6 Hz, 1H), 5.38 (s, 2H), 5.27 (s, 2H), 5.24-5.14 (m, 2H), 4.16 (s, 2H), 3.65 (d, J=5.2 Hz, 2H), 2.97 (s, 2H), 2.55 (t, J=5.5 Hz, 5H), 2.02 (s, 3H). LCMS found 857.083 (M+1).

Example 37: N,N'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azetidine-1,3-diyl))diacetamide (or N,N'-(1,1'-((6,6'-(((2,2'-dimethyl-[1,1'-biphenyl]-3,3'-diyl)bis(methylene))bis(oxy))bis(5-chloro-2-methoxypyridine-6,3-diyl))bis(methylene))bis(azetidine-3,1-diyl))diacetamide)

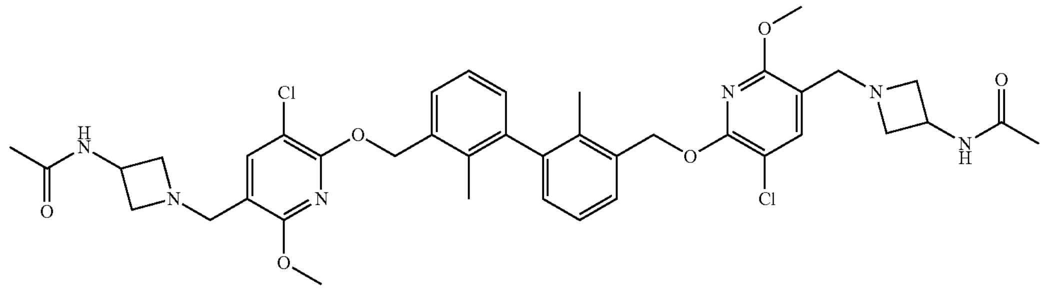 [SMILES: COc1nc(OCc2cccc(-c3cccc(COc4nc(OC)c(CN5CC(NC(C)=O)C5)cc4Cl)c3C)c2C)c(Cl)cc1CN1CC(NC(C)=O)C1]

Intermediate 18 (1 equiv) was suspended in DMF (0.025 M) and to this was added (3S)-4-Amino-3-hydroxybutanoic acid (6 equiv) followed by triethylamine (6 equiv) and the reaction stirred at room temperature for 90 minutes. To this was added sodium triacetoxyborohydride (6 equiv) and the reaction stirred an additional 4 hours. At this point TFA was added slowly dropwise to the reaction until the solution went clear. The reaction mixture was then diluted with DMF to a total volume of 4.5 mL and purified by reverse phase HPLC to afford, after lyophilization, N,N'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azetidine-1,3-diyl))diacetamide as the bis TFA salt. $^1$H NMR (400 MHz, Methanol-d4) δ 7.83 (s, 1H), 7.48 (dd, J=7.6, 1.4 Hz, 1H), 7.25 (t, J=7.6 Hz, 1H), 7.09 (dd, J=7.7, 1.4 Hz, 1H), 5.60 (s, 2H), 4.53 (d, J=9.8 Hz, 1H), 4.41-4.33 (m, 4H), 4.28-4.20 (m, 2H), 4.06 (s, 3H), 2.09 (s, 3H), 1.99 (s, 3H). LCMS found 777.178 (M+1).

Example 38: (S)-4-((5-bromo-4-((3'-((2-bromo-5-((5-cyanopyridin-3-yl)methoxy)-4-(((S)-4-hydroxy-2-oxopyrrolidin-1-yl)methyl)phenoxy)methyl)-2,2'-dimethyl-[1,1'-biphenyl]-3-yl)methoxy)-2-((5-cyanopyridin-3-yl)methoxy)benzyl)amino)-3-hydroxybutanoic acid

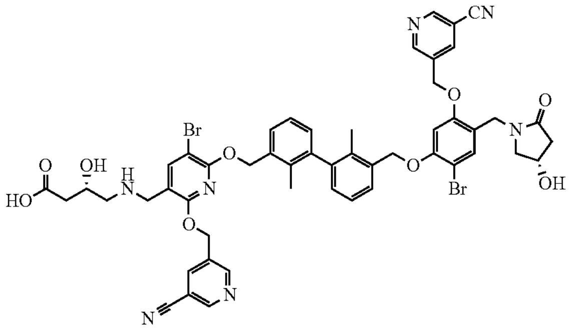 [SMILES: Cc1c(COc2cc(OCc3cncc(C#N)c3)c(CN3C[C@@H](O)CC3=O)cc2Br)cccc1-c1cccc(COc2nc(OCc3cncc(C#N)c3)c(CNC[C@@H](O)CC(=O)O)cc2Br)c1C]

To a stirred mixture of Intermediate 23 (1 equiv) and ethanolamine (5 equiv) in a 6:1 mixture of DMF/AcOH (0.02 M) at room temperature was added sequentially sodium cyanoborohydride (9 equiv) and sodium triacetoxyborohydride (9 equiv). After 4 hours at room temperature the reaction mixture was diluted with DMF/$H_2O$ (5:1) to a total volume of 4.5 mL. The resulting mixture was purified by reverse phase HPLC (0.1% trifluoroacetic acid in acetonitrile/water) providing the title compound upon lyophilization as the bis-TFA salt. $^1$H NMR (400 MHz, DMSO-$d_6$) δ 9.05-8.94 (m, 3H), 8.55 (s, 1H), 8.51-8.39 (m, 2H), 7.70 (s, 1H), 7.64-7.47 (m, 2H), 7.39-7.24 (m, 2H), 7.18-7.06 (m, 3H), 5.31 (t, J=19.1 Hz, 6H), 4.39 (d, J=15.0 Hz, 1H), 4.25 (d, J=15.4 Hz, 1H), 4.13 (dq, J=10.7, 6.5 Hz, 2H), 4.03 (s, 1H), 3.01 (d, J=1.8 Hz, 1H), 2.98 (s, 1H), 2.83 (s, 1H), 2.48-2.30 (m, 2H), 2.02 (d, J=11.1 Hz, 7H). LCMS found 1059.0 (M+1).

Example 39: 5,5'-((((((2,2'-dimethyl-[1,1'-biphenyl]-3,3'-diyl)bis(methylene))bis(oxy))bis(6-(((2-hydroxyethyl)amino)methyl)-4-propyl-3,1-phenylene))bis(oxy))bis(methylene))dinicotinonitrile (or 5,5'-((((((2,2'-dimethyl-[1,1'-biphenyl]-3,3'-diyl)bis(methylene))bis(oxy))bis(2-(((2-hydroxyethyl)amino)methyl)-4-propyl-5,1-phenylene))bis(oxy))bis(methylene))dinicotinonitrile)

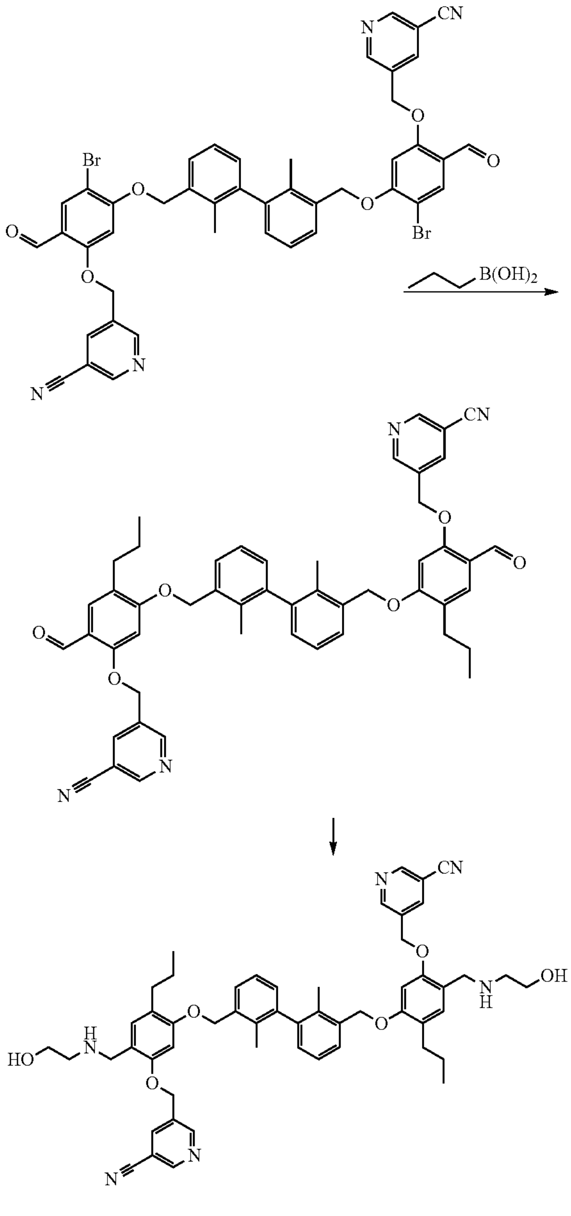

A vial was charged with Intermediate 23 (1 equiv), n-propylboronic acid (10.0 equiv), SPhos Pd G3 (10 mol %), and $K_3PO_4$ (6 equiv). After the vial was sealed dry toluene (2 mL) and water (0.2 mL) were added via syringe. The mixture was then degassed by sparging with argon for 10 minutes. The vessel was then heated to 100° C. for 1 hour. The reaction was diluted with ethyl acetate and filtered through celites. The filter cake was extracted with ethyl acetate (3×3 mL). The filtrate was concentrate in vacuo. The crude material was used without further purification.

To a stirred mixture of bis-aldehyde (1 equiv) and ethanolamine (5 equiv) in a 6:1 mixture of DMF/AcOH (0.02 M) at room temperature was added sequentially sodium cyanoborohydride (9 equiv) and sodium triacetoxyborohydride (9 equiv). After 4 hours at room temperature the reaction mixture was diluted with DMF/$H_2O$ (5:1) to a total volume of 4.5 mL. The resulting mixture was purified by reverse phase HPLC (0.1% trifluoroacetic acid in acetonitrile/water) providing the title compound upon lyophilization as the bis-TFA salt. $^1$H NMR (400 MHz, DMSO-$d_6$) δ 9.04 (t, J=1.6 Hz, 2H), 8.49 (t, J=2.1 Hz, 3H), 7.50-7.45 (m, 1H), 7.31 (t, J=7.6 Hz, 1H), 7.23 (s, 1H), 7.13-7.09 (m, 1H), 7.02 (d, J=2.8 Hz, 1H), 5.34 (d, J=3.0 Hz, 2H), 5.22 (d, J=4.1 Hz, 2H), 4.12 (s, 2H), 3.64 (t, J=5.4 Hz, 3H), 3.00-2.89 (m, 2H), 2.03 (s, 3H), 1.51 (q, J=7.5 Hz, 2H), 0.90-0.81 (m, 4H). LCMS found 889.059 (M+1).

Example 40(2R,2'R)-2,2'-((((((2,2'-dimethyl-[1,1'-biphenyl]-3,3'-diyl)bis(methylene))bis(oxy))bis(5-bromo-2-((5-(methylsulfonyl)pyridin-3-yl)methoxy)pyridine-6,3-diyl))bis(methylene))bis(azanediyl))bis(3-hydroxy-2-methylpropanoic acid) (or (2R,2'R)-2,2'-(((6,6'-(((2,2'-dimethyl-[1,1'-biphenyl]-3,3'-diyl)bis(methylene))bis(oxy))bis(5-bromo-2-((5-(methylsulfonyl)pyridin-3-yl)methoxy)pyridine-6,3-diyl))bis(methylene))bis(azanediyl))bis(3-hydroxy-2-methylpropanoic acid))

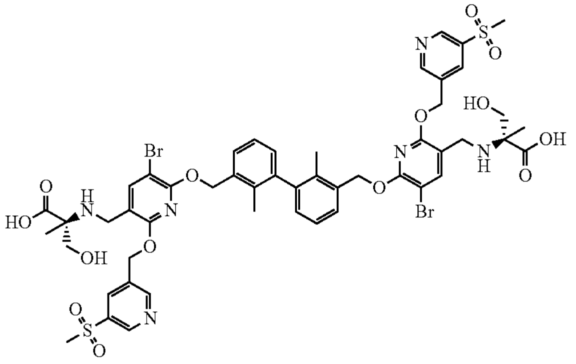 [SMILES: Cc1c(COc2nc(OCc3cncc(S(C)(=O)=O)c3)c(CN[C@](C)(CO)C(=O)O)cc2Br)cccc1-c1cccc(COc2nc(OCc3cncc(S(C)(=O)=O)c3)c(CN[C@](C)(CO)C(=O)O)cc2Br)c1C]

Step-1: To a mix of 6,6'-(((2,2'-dimethyl-[1,1'-biphenyl]-3,3'-diyl)bis(methylene))bis(oxy))bis(5-bromo-2-hydroxynicotinaldehyde) (20 mg, 0.031 mmol), (5-(methylsulfonyl)pyridin-3-yl)methanol (14.6 mg, 0.078 mmol), PPh3 (20.4 mg, 0.078 mmol), in THF (2 mL)under argon was added DIAD (15.8 mg, 0.078 mmol) at once and stirred at RT for 3 h. The solvent was concentrated and purified by column chromatography to afford product 6,6'-(((2,2'-dimethyl-[1,1'-biphenyl]-3,3'-diyl)bis(methylene))bis(oxy))bis(5-bromo-2-((5-(methylsulfonyl)pyridin-3-yl)methoxy)nicotinaldehyde). LC/MS calculated for (M+H)+: 980.8, found: 980.7.

Step-2: Fine powder of NaOH (4.08 mg, 0.1 mmol), (R)-2-amino-3-hydroxy-2-methylpropanoic acid (12.1 mg, 0.102 mmol) were taken in a 8 mL Vial, added Ethanol (1 mL), flushed with argon and sonicated for 10 min. To well stirred mix was added solution of 6,6'-(((2,2'-dimethyl-[1,1'-biphenyl]-3,3'-diyl)bis(methylene))bis(oxy))bis(5-bromo-2-((5-(methylsulfonyl)pyridin-3-yl)methoxy)nicotinaldehyde) (10 mg, 0.01 mmol) in DCM (0.25 mL) at once and stirred at RT for 1h. The reaction mixture was added $NaBH(OAc)_3$ (21.6 mg, 0.102 mmol) at once followed by AcOH (20 uL), sonicated to mix well and stirred at room temperature overnight. The solvent was concentrated and purified by reverse phase HPLC to afford (2R,2'R)-2,2'-((((((2,2'-dimethyl-[1,1'-biphenyl]-3,3'-diyl)bis(methylene))bis(oxy))bis(5-bromo-2-((5-(methylsulfonyl)pyridin-3-yl)methoxy)pyridine-6,3-diyl))bis(methylene))bis(azanediyl))bis(3-hydroxy-2-methylpropanoic acid). $^1$H NMR (400 MHz, Methanol-$d_4$) δ 9.04 (dd, J=4.7, 2.0 Hz, 4H), 8.53 (t, J=2.1 Hz, 2H), 8.06 (s, 2H), 7.42 (d, J=7.8 Hz, 2H), 7.23 (t, J=7.6 Hz, 2H), 7.12-7.04 (m, 2H), 5.64 (t, J=3.1 Hz, 4H), 5.52 (d, J=2.1 Hz, 4H), 4.27 (s, 4H), 4.04 (d, J=12.1 Hz, 2H), 3.83 (d, J=12.1 Hz, 2H), 3.20 (s, 6H), 2.04 (s, 6H), 1.56 (s, 6H). LC/MS calculated for (M+H)+: 1185.1, found: 1187.3.

Example 41: (2S,2'S)-2,2'-((((((2,2'-dimethyl-[1,1'-biphenyl]-3,3'-diyl)bis(methylene))bis(oxy))bis(5-bromo-2-((5-(methylsulfonyl)pyridin-3-yl)methoxy)pyridine-6,3-diyl))bis(methylene))bis(azanediyl))bis(3-hydroxy-2-methylpropanoic acid) (or (2S,2'S)-2,2'-(((6,6'-(((2,2'-dimethyl-[1,1'-biphenyl]-3,3'-diyl)bis(methylene))bis(oxy))bis(5-bromo-2-((5-(methylsulfonyl)pyridin-3-yl)methoxy)pyridine-6,3-diyl))bis(methylene))bis(azanediyl))bis(3-hydroxy-2-methylpropanoic acid))

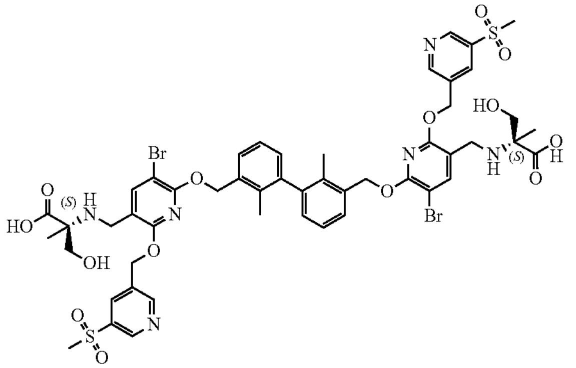

(2S,2'S)-2,2'-((((((2,2'-dimethyl-[1,1'-biphenyl]-3,3'-diyl)bis(methylene))bis(oxy))bis(5-bromo-2-((5-(methylsulfonyl)pyridin-3-yl)methoxy)pyridine-6,3-diyl))bis(methylene))bis(azanediyl))bis(3-hydroxy-2-methylpropanoic acid) was synthesized following the procedure shown in the Example 40. $^1$H NMR (400 MHz, Methanol-$d_4$) δ 9.04 (dd, J=4.7, 2.0 Hz, 4H), 8.53 (t, J=2.1 Hz, 2H), 8.06 (s, 2H), 7.42 (d, J=7.8 Hz, 2H), 7.23 (t, J=7.6 Hz, 2H), 7.12-7.04 (m, 2H), 5.64 (t, J=3.1 Hz, 4H), 5.52 (d, J=2.1 Hz, 4H), 4.27 (s, 4H), 4.04 (d, J=12.1 Hz, 2H), 3.83 (d, J=12.1 Hz, 2H), 3.20 (s, 6H), 2.04 (s, 6H), 1.56 (s, 6H). LC/MS calculated for (M+H)+: 1185.1, found: 1187.3.

Example 42: (3S,3'S)-4,4'-((((((2,2'-dimethyl-[1,1'-biphenyl]-3,3'-diyl)bis(methylene))bis(oxy))bis(5-bromo-2-((5-(methylsulfonyl)pyridin-3-yl)methoxy)pyridine-6,3 diyl))bis(methylene))bis(azanediyl))bis(3-hydroxybutanoic acid) (or (3S,3'S)-4,4'-(((6,6'-(((2,2'-dimethyl-[1,1'-biphenyl]-3,3'-diyl)bis(methylene))bis(oxy))bis(5-bromo-2-((5-(methylsulfonyl)pyridin-3-yl)methoxy)pyridine-6,3-diyl))bis(methylene))bis(azanediyl))bis(3-hydroxybutanoic acid))

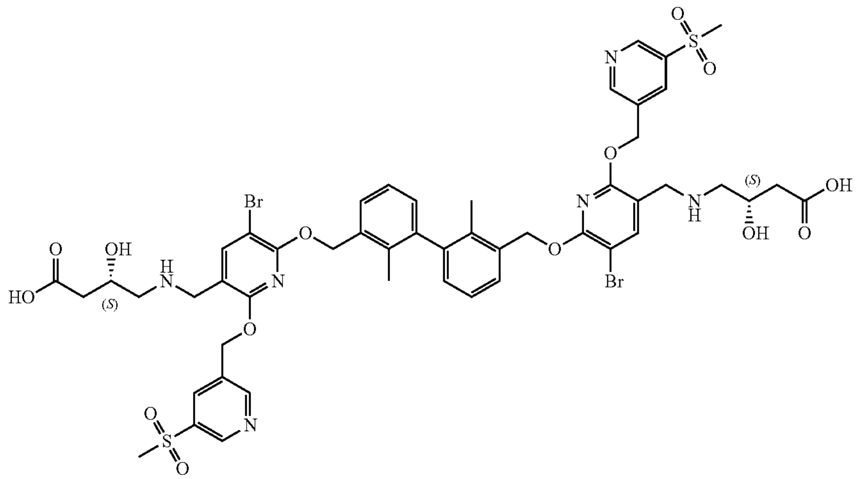

(3S,3'S)-4,4'-((((((2,2'-dimethyl-[1,1'-biphenyl]-3,3'-diyl)bis(methylene))bis(oxy))bis(5-bromo-2-((5-(methylsulfonyl)pyridin-3-yl)methoxy)pyridine-6,3 diyl))bis(methylene))bis(azanediyl))bis(3-hydroxybutanoic acid) was synthesized following procedure shown in Example 40. $^1$H NMR (400 MHz, DMSO-$d_6$) δ 12.33 (s, 2H), 9.05 (dd, J=6.1, 2.0 Hz, 4H), 8.67 (s, 4H), 8.47 (d, J=2.3 Hz, 2H), 8.12 (s, 2H), 7.42 (d, J=7.6 Hz, 2H), 7.25 (t, J=7.6 Hz, 2H), 7.07 (d, J=7.6 Hz, 2H), 5.58 (d, J=22.6 Hz, 6H), 5.47 (d, J=4.2 Hz, 4H), 4.12 (s, 8H), 3.94 (s, 2H), 3.15 (s, 2H), 3.04 (s, 2H), 2.88 (s, 2H), 2.47-2.25 (m, 6H), 1.99 (s, 6H). LC/MS calculated for $(M+H)^+$: 1185.1, found: 1187.3.

Example 43: (2R,2'R)-2,2'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(3-hydroxy-2-methylpropanoic acid) (or (2R,2'R)-2,2'-(((6,6'-(((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(3-hydroxy-2-methylpropanoic acid))

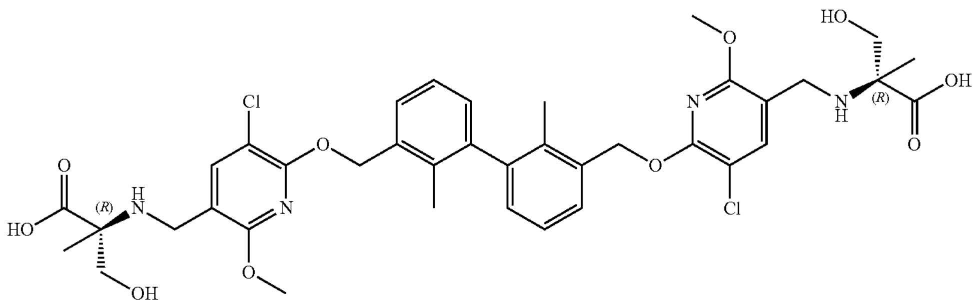

(2R,2'R)-2,2'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(3-hydroxy-2-methylpropanoic acid) was synthesized following the procedure shown in Example 40. $^1$H NMR (400 MHz, Methanol-$d_4$) δ 7.83 (s, 2H), 7.51-7.42 (m, 2H), 7.23 (t, J=7.6 Hz, 2H), 7.06 (dd, J=7.7, 1.4 Hz, 2H), 5.59 (s, 4H), 4.26-4.13 (m, 4H), 4.04 (d, J=2.2 Hz, 7H), 4.03-3.95 (m, 2H), 3.83 (d, J=12.1 Hz, 2H), 2.08 (s, 6H), 1.58 (s, 6H). LC/MS calculated for $(M+H)^+$: 787.2, found: 788.3.

Example 44: (2S,2'S)-2,2'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(3-hydroxy-2-methylpropanoic acid) (or (2S,2'S)-2,2'-(((6,6'-(((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(3-hydroxy-2-methylpropanoic acid))

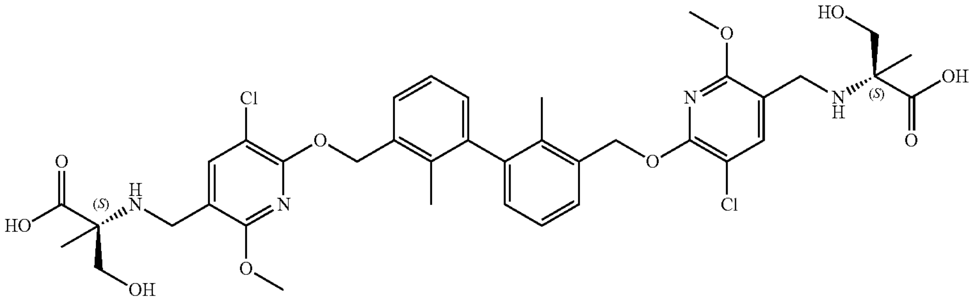

(2S,2'S)-2,2'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(3-hydroxy-2-methylpropanoic acid) was synthesized following the procedure shown in Example 40. $^1$H NMR (400 MHz, Methanol-$d_4$) δ 7.83 (s, 2H), 7.47 (dd, J=7.9, 1.4 Hz, 2H), 7.23 (t, J=7.6 Hz, 2H), 7.06 (dd, J=7.6, 1.4 Hz, 2H), 5.59 (s, 4H), 4.24-4.10 (m, 4H), 4.02 (d, J=14.9 Hz, 8H), 3.81 (d, J=12.1 Hz, 2H), 2.08 (s, 5H), 1.56 (s, 6H). LC/MS calculated for $(M+H)^+$: 787.2, found: 788.0.

Example 45: (2S,2'S)-2,2'-((((((2,2'-dimethyl-[1,1'-biphenyl]-3,3'-diyl)bis(methylene))bis(oxy))bis(5-bromo-2-methoxypyridine-6,3-diyl))bis(methylene))bis(azanediyl))bis(3-hydroxy-2-methylpropanoic acid)

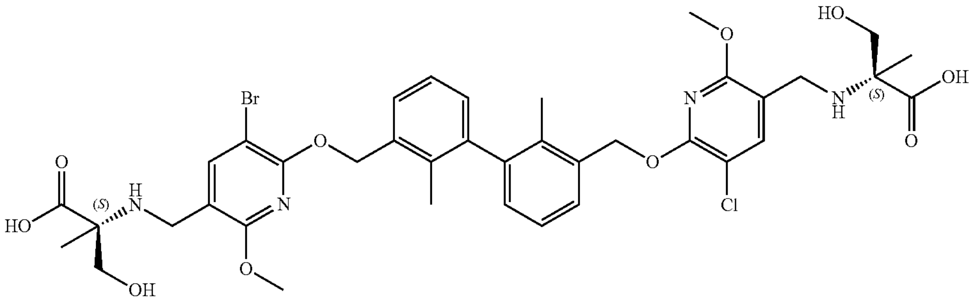

(2S,2'S)-2,2'-((((((2,2'-dimethyl-[1,1'-biphenyl]-3,3'-diyl)bis(methylene))bis(oxy))bis(5-bromo-2-methoxypyridine-6,3-diyl))bis(methylene))bis(azanediyl))bis(3-hydroxy-2-methylpropanoic acid) was synthesized following the procedure shown in Example 40. LC/MS calculated for $(M+H)^+$: 875.1, found: 877.1.

Example 46: (2R,2'R)-2,2'-((((((2,2'-dimethyl-[1,1'-biphenyl]-3,3'-diyl)bis(methylene))bis(oxy))bis(5-bromo-2-methoxypyridine-6,3-diyl))bis(methylene))bis(azanediyl))bis(3-hydroxy-2-methylpropanoic acid)

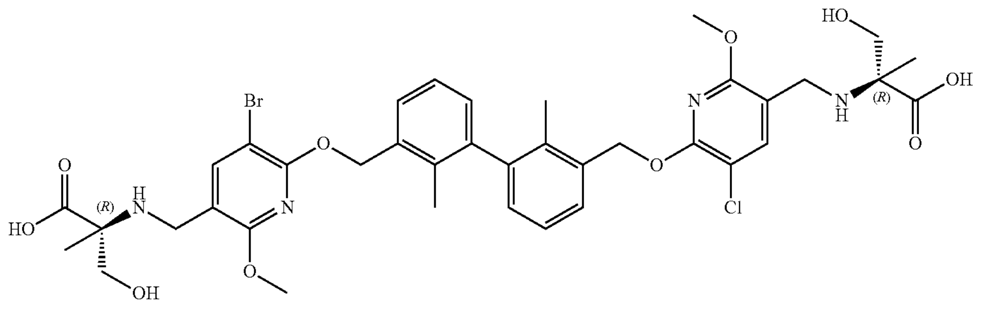

(2R,2'R)-2,2'-((((((2,2'-dimethyl-[1,1'-biphenyl]-3,3'-diyl)bis(methylene))bis(oxy))bis(5-bromo-2-methoxypyridine-6,3-diyl))bis(methylene))bis(azanediyl))bis(3-hydroxy-2-methylpropanoic acid) was synthesized following the procedure shown in Example 40. LC/MS calculated for $(M+H)^+$: 875.1, found: 877.1.

Example 47: (2S,2'S,4R,4'R)-1,1'-(((((2,2'-dimethyl-[1,1'-biphenyl]-3,3'-diyl)bis(methylene))bis(oxy))bis(5-chloro-2-methoxypyridine-6,3-diyl))bis(methylene))bis(4-hydroxypiperidine-2-carboxylic acid) (or (2S,2'S,4R,4'R)-1,1'-((6,6'-(((2,2'-dimethyl-[1,1'-biphenyl]-3,3'-diyl)bis(methylene))bis(oxy))bis(5-chloro-2-methoxypyridine-6,3-diyl))bis(methylene))bis(4-hydroxypiperidine-2-carboxylic acid))

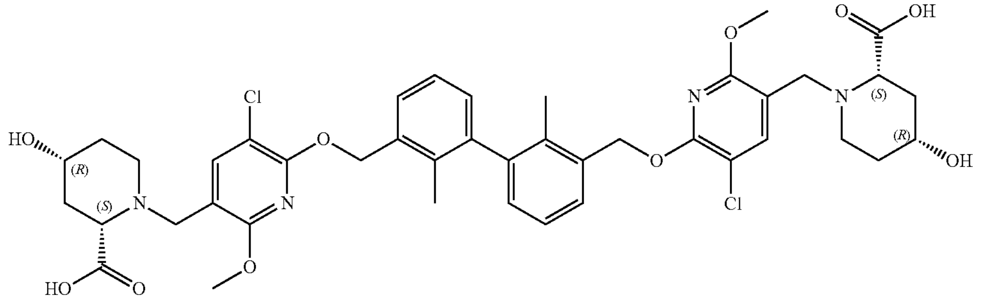

(2S,2'S,4R,4'R)-1,1'-(((((2,2'-dimethyl-[1,1'-biphenyl]-3,3'-diyl)bis(methylene))bis(oxy))bis(5-chloro-2-methoxypyridine-6,3-diyl))bis(methylene))bis(4-hydroxypiperidine-2-carboxylicacid) was synthesized following the general reductive amination procedure H. $^1H$ NMR (400 MHz, Methanol-$d_4$) δ 7.97 (s, 1H), 7.85 (s, 2H), 7.48 (dd, J=7.7, 1.4 Hz, 2H), 7.25 (t, J=7.6 Hz, 2H), 7.09 (dd, J=7.7, 1.3 Hz, 2H), 5.60 (s, 4H), 4.52-4.21 (m, 4H), 4.02 (s, 6H), 3.93-3.39 (m, 4H), 3.22-3.04 (m, 2H), 2.98 (s, 2H), 2.85 (d, J=0.7 Hz, 2H), 2.46 (d, J=13.5 Hz, 2H), 2.09 (s, 8H), 1.88-1.15 (m, 5H). LC/MS calculated for $(M+H)^+$: 839.3, found: 839.5.

Example 48: (2S,2'S,4S,4'S)-1,1'-(((((2,2'-dimethyl-[1,1'-biphenyl]-3,3'-diyl)bis(methylene))bis(oxy))bis(5-chloro-2-methoxypyridine-6,3-diyl))bis(methylene))bis(4-hydroxypyrrolidine-2-carboxylic acid) (or (2S,2'S,4S,4'S)-1,1'-((6,6'-(((2,2'-dimethyl-[1,1'-biphenyl]-3,3'-diyl)bis(methylene))bis(oxy))bis(5-chloro-2-methoxypyridine-6,3-diyl))bis(methylene)) bis(4-hydroxypyrrolidine-2-carboxylic acid))

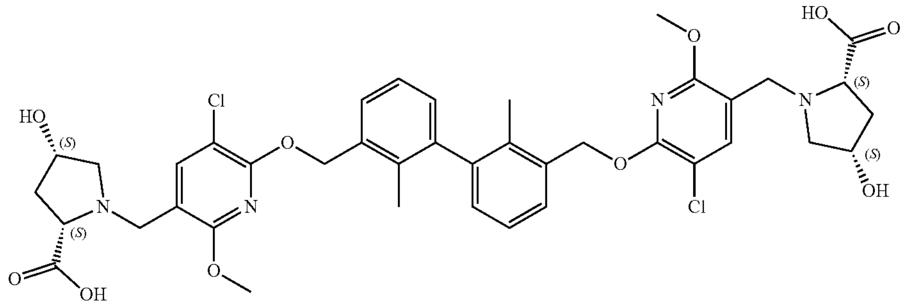

(2S,2'S,4S,4'S)-1,1'-(((((2,2'-dimethyl-[1,1'-biphenyl]-3,3'-diyl)bis(methylene))bis(oxy))bis(5-chloro-2-methoxypyridine-6,3-diyl))bis(methylene))bis(4-hydroxypyrrolidine-2-carboxylic acid) was synthesized following the procedure shown in Example 40. $^{1}$H NMR (400 MHz, Methanol-$d_4$) δ 7.87 (s, 2H), 7.52-7.43 (m, 2H), 7.25 (t, J=7.6 Hz, 2H), 7.09 (dd, J=7.6, 1.4 Hz, 2H), 5.59 (s, 4H), 4.56-4.25 (m, 8H), 4.06 (s, 6H), 3.56 (d, J=11.7 Hz, 2H), 3.35 (dd, J=11.8, 3.8 Hz, 2H), 2.71 (ddd, J=13.9, 10.9, 4.7 Hz, 2H), 2.28-2.18 (m, 2H), 2.09 (s, 6H). LC/MS calculated for $(M+H)^+$: 811.2, found: 812.2.

Example 49: (3R,3'R)-4,4'-((((((2,2'-dimethyl-[1,1'-biphenyl]-3,3'-diyl)bis(methylene))bis(oxy))bis(5-chloro-2-methoxypyridine-6,3-diyl))bis(methylene)) bis(azanediyl))bis(3-hydroxybutanoic acid) (or (3R,3'R)-4,4'-(((6,6'-(((2,2'-dimethyl-[1,1'-biphenyl]-3,3'-diyl)bis(methylene))bis(oxy))bis(5-chloro-2-methoxypyridine-6,3-diyl))bis(methylene))bis (azanediyl))bis(3-hydroxybutanoic acid))

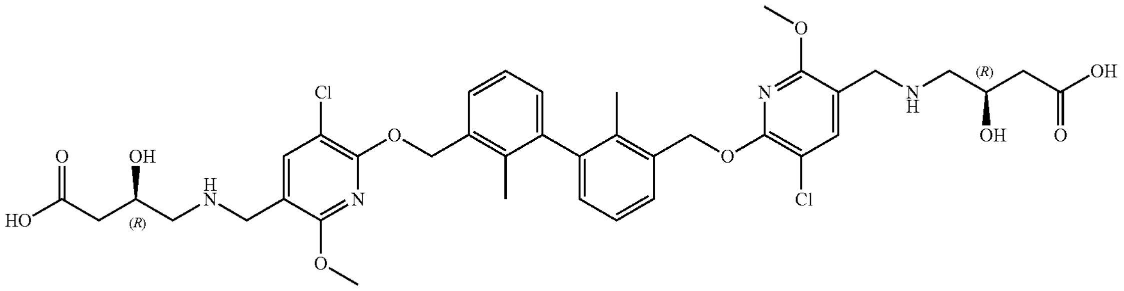

(3R,3'R)-4,4'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(3-hydroxybutanoic acid) was synthesized following the procedure shown in Example 40. $^{1}$H NMR (400 MHz, DMSO-$d_6$) δ 12.34 (s, 2H), 8.62 (s, 4H), 7.95 (s, 2H), 7.46 (d, J=7.6 Hz, 2H), 7.27 (t, J=7.6 Hz, 2H), 7.07 (d, J=7.2 Hz, 2H), 5.56 (s, 4H), 4.14 (s, 2H), 4.03 (s, 4H), 3.94 (s, 6H), 3.01 (s, 2H), 2.86 (s, 2H), 2.47-2.28 (m, 4H), 2.02 (s, 6H). LC/MS calculated for $(M+H)^+$: 787.3, found: 787.2.

Example 50: (2S,2'S)-2,2'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(3-hydroxypropanoic acid) (or (2S,2'S)-2,2'-(((6,6'-(((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(3-hydroxypropanoic acid))

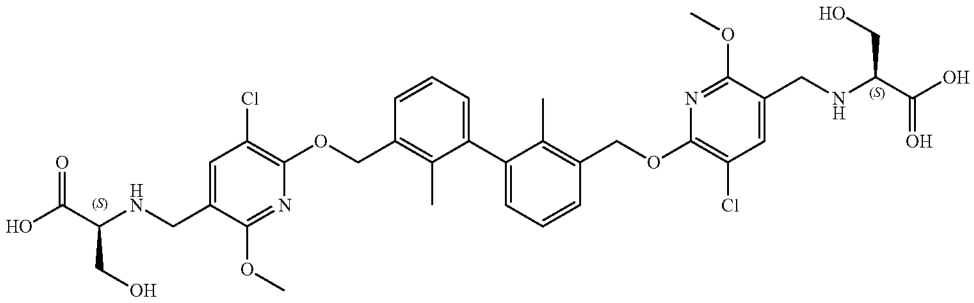

(2S,2'S)-2,2'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(3-hydroxypropanoic acid) was synthesized following the procedure shown in Example 40. $^1$H NMR (400 MHz, DMSO-$d_6$) δ 7.90 (s, 2H), 7.46 (d, J=7.6 Hz, 2H), 7.26 (t, J=7.6 Hz, 2H), 7.07 (d, J=7.5 Hz, 2H), 5.55 (s, 4H), 4.00 (s, 4H), 3.90 (s, 6H), 3.79 (s, 4H), 3.72 (d, J=19.1 Hz, 2H), 2.01 (s, 6H). LC/MS calculated for $(M+H)^+$: 759.3, found: 759.2.

Example 51: (2S,2'S,3R,3'R)-2,2'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(3-hydroxybutanoic acid) (or (2S,2'S,3R,3'R)-2,2'-(((6,6'-(((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(3-hydroxybutanoic acid))

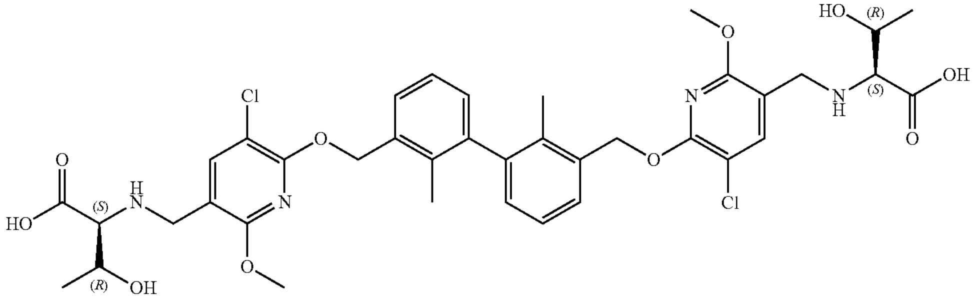

(2S,2'S,3R,3'R)-2,2'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(3-hydroxybutanoic acid) was synthesized following the procedure shown in Example 40. $^1$H NMR (400 MHz, DMSO-$d_6$) δ 7.92 (s, 2H), 7.46 (d, J=7.6 Hz, 2H), 7.27 (t, J=7.6 Hz, 2H), 7.07 (d, J=7.5 Hz, 2H), 5.55 (d, J=2.2 Hz, 4H), 3.98 (d, J=14.1 Hz, 6H), 3.90 (s, 6H), 3.42 (s, 2H), 2.01 (s, 6H), 1.17 (d, J=6.3 Hz, 6H). LC/MS calculated for $(M+H)^+$: 787.2, found: 787.2.

Example 52: 2,2'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(2-(2H-tetrazol-5-yl)ethan-1-ol) (or 2,2'-(((6,6'-(((2,2'-dimethyl-[1,1'-biphenyl]-3,3'-diyl)bis(methylene))bis(oxy))bis(5-chloro-2-methoxy-pyridine-6,3-diyl))bis(methylene))bis(azanediyl))bis(2-(2H-tetrazol-5-yl)ethan-1-ol))

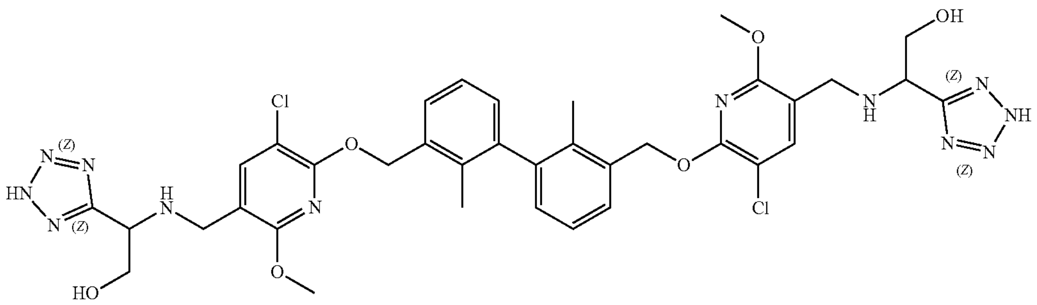

2,2'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(2-(2H-tetrazol-5-yl)ethan-1-ol) was synthesized following the procedure shown in Example 40. $^1$H NMR (400 MHz, Methanol-$d_4$) δ 7.74 (s, 2H), 7.45 (dd, J=7.7, 1.4 Hz, 2H), 7.23 (t, J=7.6 Hz, 2H), 7.06 (dd, J=7.7, 1.4 Hz, 2H), 5.57 (s, 4H), 4.85 (s, 2H), 4.24 (d, J=4.0 Hz, 4H), 4.10 (d, J=5.8 Hz, 4H), 3.96 (s, 6H), 2.07 (s, 6H). LC/MS calculated for $(M+H)^+$: 807.3, found: 807.2.

Example 53: (2S,2'S)-1,1'-(((((2,2'-dimethyl-[1,1'-biphenyl]-3,3'-diyl)bis(methylene))bis(oxy))bis(5-chloro-2-((5-cyanopyridin-3-yl)methoxy)-4,1-phenylene))bis(methylene))bis(piperidine-2-carboxylic acid)

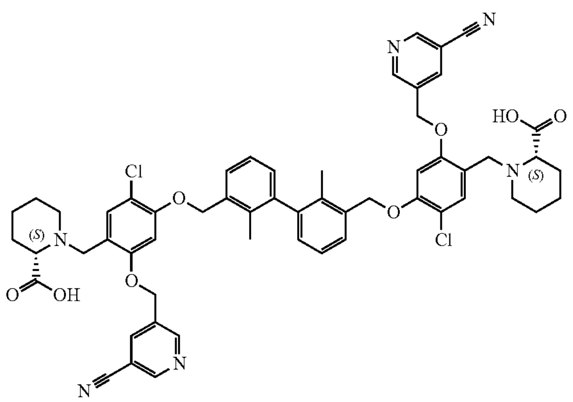

(2S,2'S)-1,1'-(((((2,2'-dimethyl-[1,1'-biphenyl]-3,3'-diyl) bis(methylene))bis(oxy))bis(5-chloro-2-((5-cyanopyridin-3-yl)methoxy)-4,1-phenylene))bis(methylene))bis(piperidine-2-carboxylic acid) was synthesized following the procedure shown in Example 40. LC/MS calculated for $(M+H)^+$: 1009.3, found: 1009.6.

Example 54: (3R,3'R)-4,4'-((((((2,2'-dimethyl-[1,1'-biphenyl]-3,3'-diyl)bis(methylene))bis(oxy))bis(5-cyclopropyl-2-methoxypyridine-6,3-diyl))bis(methylene))bis(azanediyl))bis(3-hydroxybutanoic acid) (or (3R,3'R)-4,4'-(((6,6'-(((2,2'-dimethyl-[1,1'-biphenyl]-3,3'-diyl)bis(methylene))bis(oxy))bis(5-cyclopropyl-2-methoxypyridine-6,3-diyl))bis(methylene)) bis(azanediyl))bis(3-hydroxybutanoic acid))

and the mixture extracted with EtOAc (2×15 mL), the combined organics were washed with brine (10 mL), dried over $MgSO_4$ and concentrated in vacuo. Purification by column chromatography (10% EtOAc in hexanes) afforded the desired compound 6,6'-(((2,2'-dimethyl-[1,1'-biphenyl]-3,3'-diyl)bis(methylene))bis(oxy))bis(5-cyclopropyl-2-methoxynicotinaldehyde). $^1H$ NMR (400 MHz, Chloroform-d) δ 10.18 (s, 2H), 7.65 (d, J=0.7 Hz, 2H), 7.49 (dd, J=7.6, 1.4 Hz, 2H), 7.32-7.21 (m, 2H), 7.14 (dd, J=7.7, 1.4 Hz, 2H), 5.57 (s, 4H), 4.04 (s, 6H), 2.11 (s, 6H), 1.95 (ttd, J=8.4, 5.3, 0.7 Hz, 2H), 0.92-0.80 (m, 4H), 0.67-0.53 (m, 4H).

Step-2: (3R,3'R)-4,4'-((((((2,2'-dimethyl-[1,1'-biphenyl]-3,3'-diyl)bis(methylene))bis(oxy))bis(5-cyclopropyl-2-methoxypyridine-6,3-diyl))bis(methylene))bis(azanediyl)) bis(3-hydroxybutanoic acid) was synthesized following the

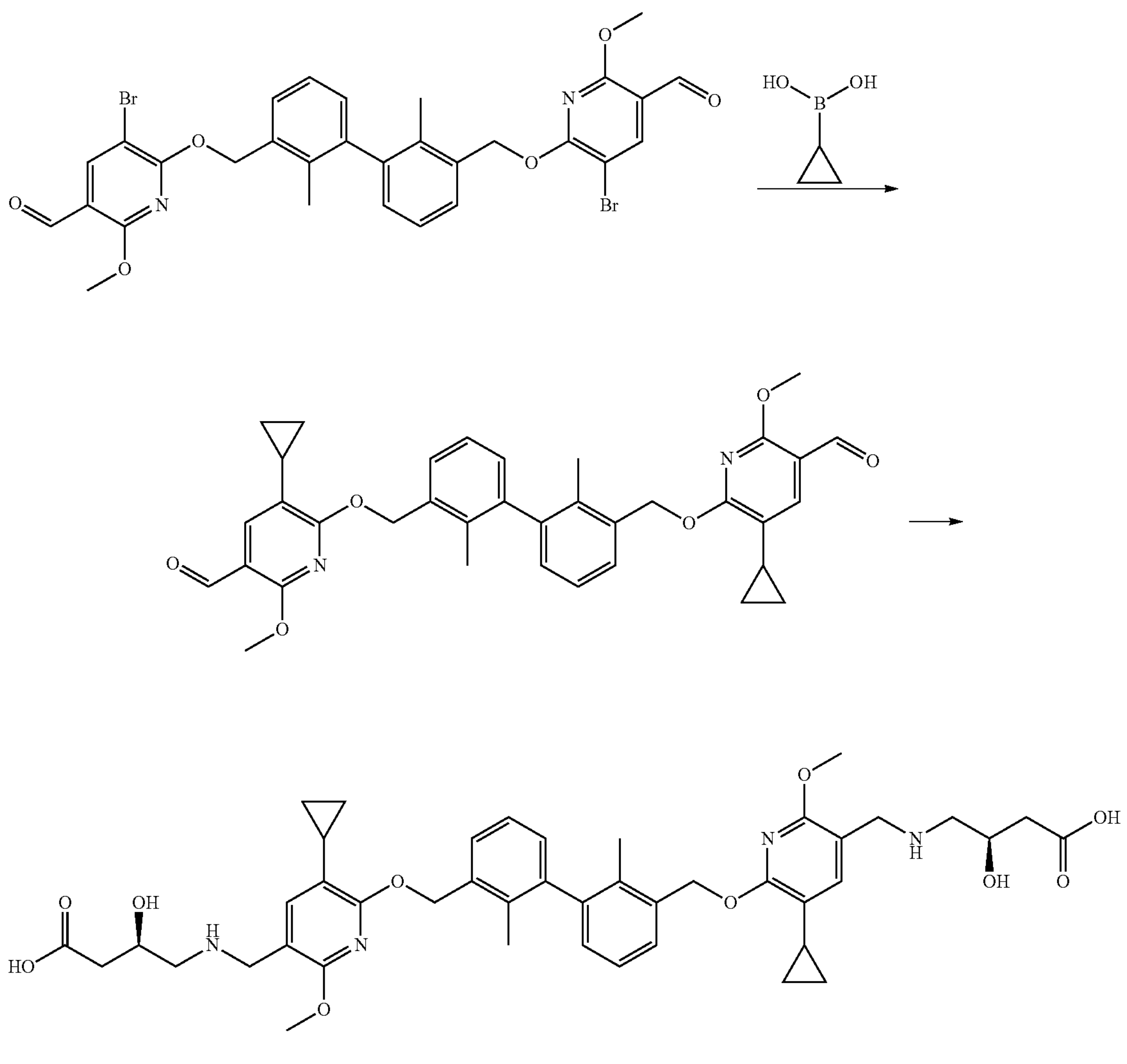

Step-1: To a mixture of 6,6'-(((2,2'-dimethyl-[1,1'-biphenyl]-3,3'-diyl)bis(methylene))bis(oxy))bis(5-bromo-2-methoxynicotinaldehyde) (100 mg, 0.15 mmol) cyclopropylboronic acid (51.4 mg, 0.59 mmol), potassium phosphate (140.4 mg, 1.04 mmol), and tricyclohexylphosphine (33.5 mg, 0.12 mmol) in toluene (5 mL) and water (0.25 mL)under a nitrogen atmosphere was added palladium acetate (6.4 mg, 0.06 mmol). The mixture was heated to 100° C. for 3 h and then cooled to room temperature. Water (10 mL) was added procedure shown in Example 40. $^1H$ NMR (400 MHz, Methanol-d4) δ 7.47 (dd, J=7.7, 1.3 Hz, 2H), 7.32 (s, 2H), 7.23 (t, J=7.6 Hz, 2H), 7.06 (dd, J=7.7, 1.4 Hz, 2H), 5.55 (s, 4H), 4.27 (dq, J=9.7, 3.3 Hz, 2H), 4.12 (s, 4H), 4.01 (s, 7H), 3.16 (dd, J=12.8, 3.0 Hz, 2H), 2.95 (dd, J=12.8, 9.8 Hz, 2H), 2.53 (d, J=6.3 Hz, 4H), 2.10 (s, 6H), 1.97 (td, J=8.5, 4.3 Hz, 2H), 0.95-0.79 (m, 4H), 0.69-0.51 (m, 4H). LC/MS calculated for $(M+H)^+$: 799.4, found: 799.2.

Example 55: (3S,3'S)-4,4'-((((((2,2'-dimethyl-[1,1'-biphenyl]-3,3'-diyl)bis(methylene))bis(oxy))bis(5-cyclopropyl-2-methoxypyridine-6,3-diyl))bis(methylene))bis(azanediyl))bis(3-hydroxybutanoic acid) (or (3S,3'S)-4,4'-(((6,6'-(((2,2'-dimethyl-[1,1'-biphenyl]-3,3'-diyl)bis(methylene))bis(oxy))bis(5-cyclopropyl-2-methoxypyridine-6,3-diyl))bis(methylene))bis(azanediyl))bis(3-hydroxybutanoic acid))

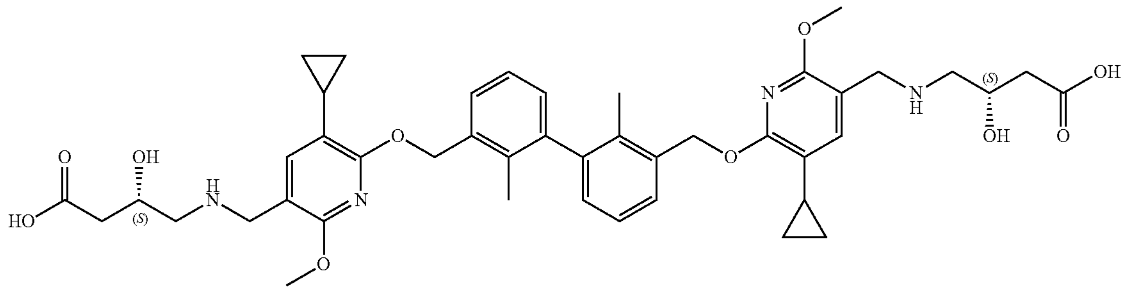

(3S,3'S)-4,4'-((((((2,2'-dimethyl-[1,1'-biphenyl]-3,3'-diyl)bis(methylene))bis(oxy))bis(5-cyclopropyl-2-methoxypyridine-6,3-diyl))bis(methylene))bis(azanediyl))bis(3-hydroxybutanoic acid) was synthesized following the procedure shown in Example 40. $^1$H NMR (400 MHz, Methanol-$d_4$) δ 7.47 (d, J=7.6 Hz, 2H), 7.32 (s, 2H), 7.23 (t, J=7.6 Hz, 2H), 7.06 (d, J=7.5 Hz, 2H), 5.55 (s, 4H), 4.27 (dq, J=9.7, 3.3 Hz, 2H), 4.12 (s, 4H), 4.01 (s, 6H), 3.33 (d, J=9.6 Hz, 2H), 3.16 (dd, J=12.7, 3.0 Hz, 2H), 2.95 (dd, J=12.7, 9.8 Hz, 2H), 2.53 (d, J=6.4 Hz, 4H), 2.10 (s, 6H), 1.97 (tq, J=10.4, 5.1 Hz, 2H), 0.87 (dt, J=8.6, 3.1 Hz, 4H), 0.75-0.45 (m, 4H). LC/MS calculated for $(M+H)^+$: 799.4, found: 799.2.

Example 56: (S)-4-(((5-cyclopropyl-6-((3'-(((3-cyclopropyl-5-((((S)-4-ethoxy-2-hydroxy-4-oxobutyl)amino)methyl)-6-methoxypyridin-2-yl)oxy)methyl)-2,2'-dimethyl-[1,1'-biphenyl]-3-yl)methoxy)-2-methoxypyridin-3-yl)methyl)amino)-3-hydroxybutanoic acid

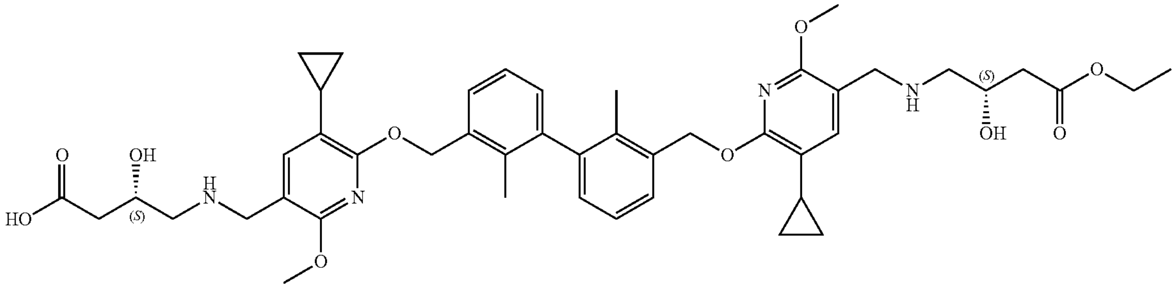

(S)-4-(((5-cyclopropyl-6-((3'-(((3-cyclopropyl-5-((((S)-4-ethoxy-2-hydroxy-4-oxobutyl)amino)methyl)-6-methoxypyridin-2-yl)oxy)methyl)-2,2'-dimethyl-[1,1'-biphenyl]-3-yl)methoxy)-2-methoxypyridin-3-yl)methyl)amino)-3-hydroxybutanoic acid was isolated as byproduct from Example 55. $^1$H NMR (400 MHz, Methanol-$d_4$) δ 7.47 (dd, J=7.6, 1.4 Hz, 2H), 7.32 (s, 2H), 7.23 (t, J=7.6 Hz, 2H), 7.06 (dd, J=7.6, 1.4 Hz, 2H), 5.55 (s, 4H), 4.28 (dp, J=9.6, 2.8 Hz, 2H), 4.14 (d, J=9.7 Hz, 6H), 4.01 (s, 6H), 3.15 (ddd, J=12.9, 10.0, 3.0 Hz, 2H), 2.96 (dd, J=12.8, 9.8 Hz, 2H), 2.54 (t, J=6.2 Hz, 4H), 2.10 (s, 6H), 1.97 (ddt, J=12.6, 9.5, 4.7 Hz, 2H), 1.24 (t, J=7.1 Hz, 3H), 0.95-0.76 (m, 4H), 0.67-0.53 (m, 4H). LC/MS calculated for $(M+H)^+$: 827.4, found: 827.2.

Example-57: (2S,2'S)-2,2'-((((((2,2'-dimethyl-[1,1'-biphenyl]-3,3'-diyl)bis(methylene))bis(oxy))bis(5-chloro-2-((3-(methylsulfonyl)benzyl)oxy)-4,1-phenylene))bis(methylene))bis(azanediyl))bis(3-hydroxy-2-methylpropanoic acid)

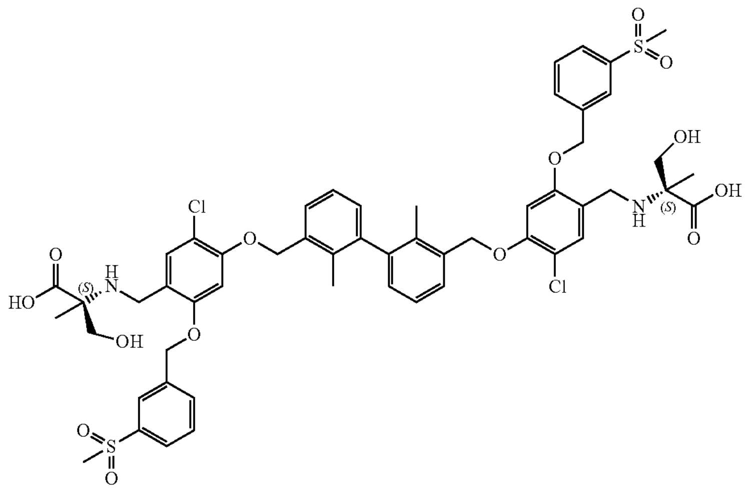

(2S,2'S)-2,2'-((((((2,2'-dimethyl-[1,1'-biphenyl]-3,3'-diyl)bis(methylene))bis(oxy))bis(5-chloro-2-((3-(methylsulfonyl)benzyl)oxy)-4,1-phenylene))bis(methylene))bis(azanediyl))bis(3-hydroxy-2-methylpropanoic acid) was synthesized following the procedure shown in Example 40. $^1$H NMR (400 MHz, Methanol-$d_4$) δ 8.14 (s, 2H), 7.93 (dd, J=18.1, 7.8 Hz, 4H), 7.67 (t, J=7.7 Hz, 2H), 7.52 (s, 2H), 7.44 (d, J=7.6 Hz, 2H), 7.25 (t, J=7.7 Hz, 2H), 7.10 (d, J=7.5 Hz, 2H), 7.03 (s, 2H), 5.33 (d, J=27.2 Hz, 8H), 4.34-4.17 (m, 4H), 3.98 (d, J=12.0 Hz, 2H), 3.79 (d, J=12.1 Hz, 2H), 3.14 (s, 6H), 3.02 (s, 2H), 2.06 (s, 6H), 1.48 (s, 6H). LC/MS calculated for $(M+H)^+$: 1093.3, found: 1093.2.

Example 58: (2S,2'S,4S,4'S)-1,1'-(((((2,2'-dimethyl-[1,1'-biphenyl]-3,3'-diyl)bis(methylene))bis(oxy))bis(5-chloro-2-((5-cyanopyridin-3-yl)methoxy)-4,1-phenylene))bis(methylene))bis(4-hydroxypyrrolidine-2-carboxylic acid)

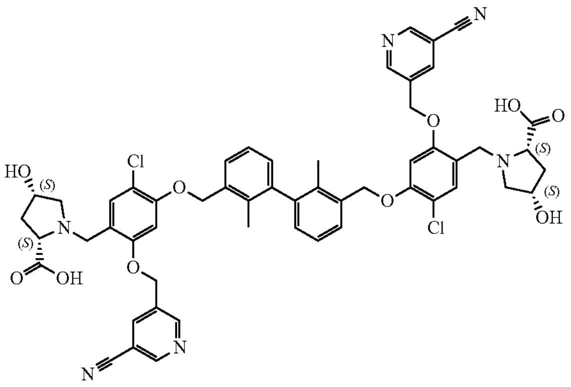

(2S,2'S,4S,4'S)-1,1'-(((((2,2'-dimethyl-[1,1'-biphenyl]-3,3'-diyl)bis(methylene))bis(oxy))bis(5-chloro-2-((5-cyanopyridin-3-yl)methoxy)-4,1-phenylene))bis(methylene))bis(4-hydroxypyrrolidine-2-carboxylic acid) was synthesized following the procedure shown in Example 40. $^1H$ NMR (400 MHz, Acetonitrile-$d_3$) δ 8.98-8.85 (m, 4H), 8.31 (s, 2H), 7.53 (d, J=7.6 Hz, 2H), 7.47 (s, 2H), 7.33 (t, J=7.6 Hz, 3H), 7.18 (d, J=7.5 Hz, 3H), 6.97 (d, J=6.2 Hz, 2H), 5.45-5.12 (m, 10H), 4.44 (d, J=12.3 Hz, 4H), 4.32 (td, J=8.6, 7.4, 4.3 Hz, 4H), 3.57-3.14 (m, 4H), 2.57 (d, J=10.7 Hz, 0H), 2.25 (d, J=14.2 Hz, 2H), 2.05 (d, J=7.8 Hz, 6H). LC/MS calculated for $(M+H)^+$: 1013.3, found: 1013.4.

Example 59: (2S,2'S)-1,1'-(((((2,2'-dimethyl-[1,1'-biphenyl]-3,3'-diyl)bis(methylene))bis(oxy))bis(5-bromo-2-methoxypyridine-6,3-diyl))bis(methylene))bis(azetidine-2-carboxylic acid) (or (2S,2'S)-1,1'-((6,6'-(((2,2'-dimethyl-[1,1'-biphenyl]-3,3'-diyl)bis(methylene))bis(oxy))bis(5-bromo-2-methoxypyridine-6,3-diyl))bis(methylene))bis(azetidine-2-carboxylic acid))

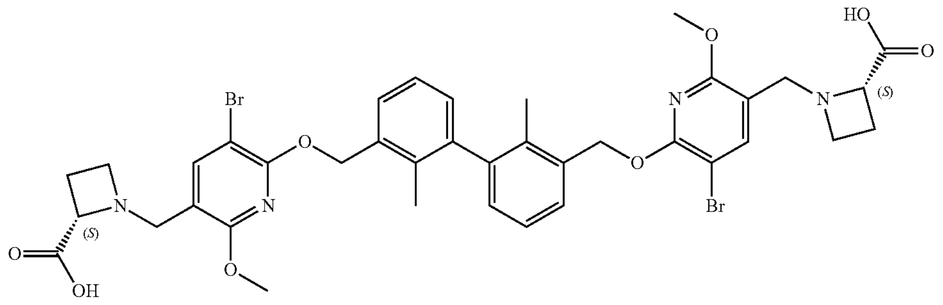

(2S,2'S)-1,1'-(((((2,2'-dimethyl-[1,1'-biphenyl]-3,3'-diyl)bis(methylene))bis(oxy))bis(5-bromo-2-methoxypyridine-6,3-diyl))bis(methylene))bis(azetidine-2-carboxylic acid) was synthesized following the procedure shown in Example 40. LC/MS calculated for $(M+H)^+$: 841.6, found: 841.2.

Example 60: (S)-1-((6-((3'-(((3-bromo-5-(((S)-2-carboxyazetidin-1-yl)methyl)-6-methoxypyridin-2-yl)oxy)methyl)-2,2'-dimethyl-[1,1'-biphenyl]-3-yl)methoxy)-2-methoxypyridin-3-yl)methyl)azetidine-2-carboxylic acid

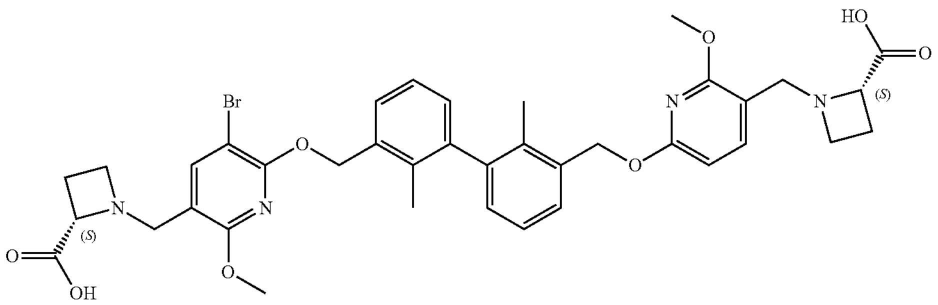

(S)-1-((6-((3'-(((3-bromo-5-(((S)-2-carboxyazetidin-1-yl)methyl)-6-methoxypyridin-2-yl)oxy)methyl)-2,2'-dimethyl-[1,1'-biphenyl]-3-yl)methoxy)-2-methoxypyridin-3-yl)methyl)azetidine-2-carboxylic acid was isolated as side product of Example 59. LC/MS calculated for $(M+H)^+$: 761.2, found: 760.1.

Example 61: (2S,2'S)-2,2'-((((((2,2'-dimethyl-[1,1'-biphenyl]-3,3'-diyl)bis(methylene))bis(oxy))bis(2-methoxypyridine-6,3-diyl))bis(methylene))bis(azanediyl))bis(3-hydroxy-2-methylpropanoic acid) (or (2S,2'S)-2,2'-(((6,6'-(((2,2'-dimethyl-[1,1'-biphenyl]-3,3'-diyl)bis(methylene))bis(oxy))bis(2-methoxypyridine-6,3-diyl))bis(methylene))bis(azanediyl))bis(3-hydroxy-2-methylpropanoic acid)

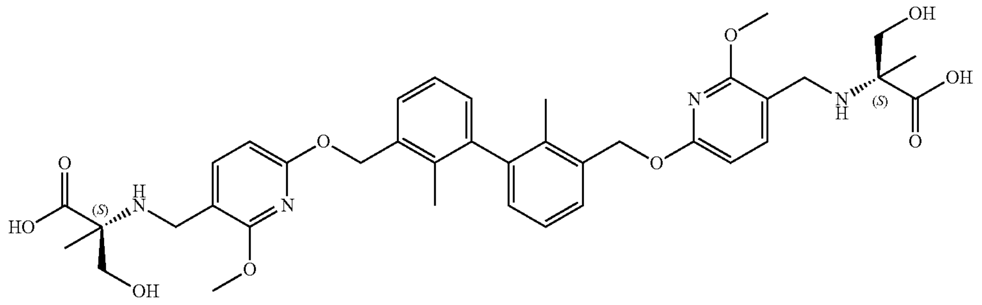

(2S,2'S)-2,2'-((((((2,2'-dimethyl-[1,1'-biphenyl]-3,3'-diyl)bis(methylene))bis(oxy))bis(2-methoxypyridine-6,3-diyl))bis(methylene))bis(azanediyl))bis(3-hydroxy-2-methylpropanoic acid) was synthesized following the procedure shown in Example 40. $^1$H NMR (400 MHz, Methanol-$d_4$) δ 7.72 (d, J=8.1 Hz, 2H), 7.43 (dd, J=7.8, 1.4 Hz, 2H), 7.22 (t, J=7.6 Hz, 2H), 7.04 (dd, J=7.6, 1.4 Hz, 2H), 6.47 (d, J=8.1 Hz, 2H), 5.49 (s, 4H), 4.31-4.09 (m, 4H), 4.02 (s, 8H), 3.91-3.70 (m, 2H), 2.84 (s, 1H), 2.06 (d, J=1.7 Hz, 6H), 1.59 (s, 6H). LC/MS calculated for $(M+H)^+$: 719.3, found: 719.0.

Example 62: 5,5'-(((((2,2'-dimethyl-[1,1'-biphenyl]-3,3'-diyl)bis(methylene))bis(oxy))bis(5-chloro-2-methoxypyridine-6,3-diyl))bis(methylene))bis(4,5,6,7-tetrahydro-1H-imidazo[4,5-c]pyridine-4-carboxylic acid) (or 5,5'-((6,6'-(((2,2'-dimethyl-[1,1'-biphenyl]-3,3'-diyl)bis(methylene))bis(oxy))bis(5-chloro-2-methoxypyridine-6,3-diyl))bis(methylene))bis(4,5,6,7-tetrahydro-1H-imidazo[4,5-c]pyridine-4-carboxylic acid))

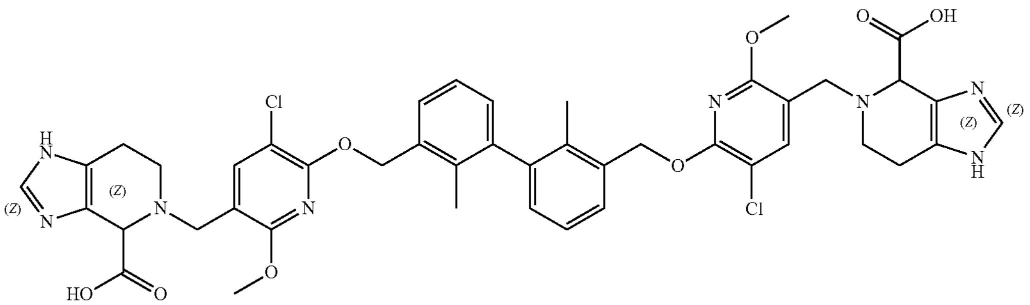 [SMILES: COc1nc(OCc2cccc(-c3cccc(COc4nc(OC)c(CN5CCc6[nH]cnc6C5C(=O)O)cc4Cl)c3C)c2C)c(Cl)cc1CN1CCc2[nH]cnc2C1C(=O)O]

5,5'-(((((2,2'-dimethyl-[1,1'-biphenyl]-3,3'-diyl)bis(methylene))bis(oxy))bis(5-chloro-2-methoxypyridine-6,3-diyl))bis(methylene))bis(4,5,6,7-tetrahydro-1H-imidazo[4,5-c]pyridine-4-carboxylic acid) was synthesized following the procedure shown in Example 40. $^1$H NMR (400 MHz, Methanol-d4) δ 8.78 (s, 2H), 7.86 (s, 2H), 7.54-7.38 (m, 2H), 7.24 (t, J=7.6 Hz, 2H), 7.08 (dd, J=7.6, 1.4 Hz, 2H), 5.56 (s, 4H), 4.68 (s, 2H), 4.03 (d, J=2.3 Hz, 4H), 3.96 (s, 6H), 3.46 (ddd, J=13.7, 9.1, 5.3 Hz, 2H), 3.29 (s, 10H), 2.96 (dt, J=15.6, 6.8 Hz, 2H), 2.87-2.70 (m, 2H), 2.09 (s, 6H). LC/MS calculated for $(M+H)^+$: 883.4, found: 883.3.

Example 63: 5,5'-(((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(methylene))bis(isoxazol-3-ol) (or 5,5'-((((6,6'-(((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(methylene))bis(isoxazol-3-ol))

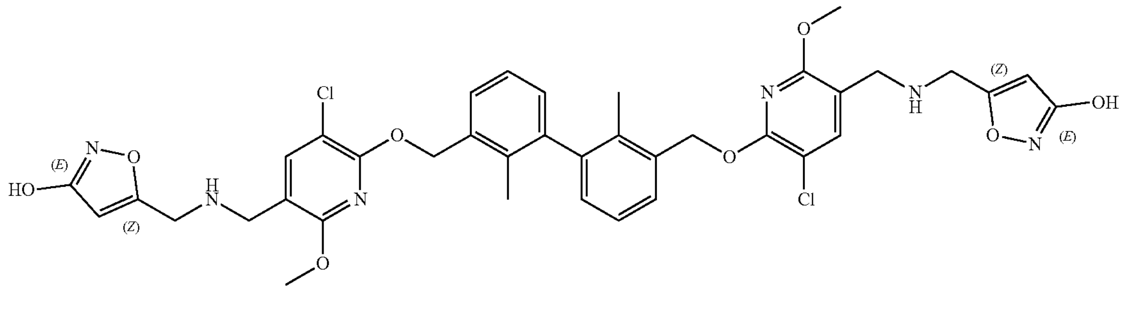

5,5'-(((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(methylene))bis(isoxazol-3-ol) was synthesized following the procedure shown in Example 40. $^1H$ NMR (400 MHz, Methanol-$d_4$) δ 7.78 (s, 2H), 7.47 (dd, J=7.7, 1.4 Hz, 2H), 7.24 (t, J=7.6 Hz, 2H), 7.07 (dd, J=7.7, 1.4 Hz, 2H), 6.18 (s, 2H), 5.59 (s, 4H), 4.35 (s, 4H), 4.17 (s, 4H), 4.04 (s, 6H), 2.08 (s, 6H). LC/MS calculated for $(M+H)^+$: 777.2, found: 779.9.

Example 64: (2R,2'R)-2,2'-((((((2,2'-dimethyl-[1,1'-biphenyl]-3,3'-diyl)bis(methylene))bis(oxy))bis(5-cyclopropyl-2-methoxypyridine-6,3-diyl))bis(methylene))bis(azanediyl))bis(3-hydroxy-2-methylpropanoic acid) (or (2R,2'R)-2,2'-(((6,6'-(((2,2'-dimethyl-[1,1'-biphenyl]-3,3'-diyl)bis(methylene))bis(oxy))bis(5-cyclopropyl-2-methoxypyridine-6,3-diyl))bis(methylene))bis(azanediyl))bis(3-hydroxy-2-methylpropanoic acid))

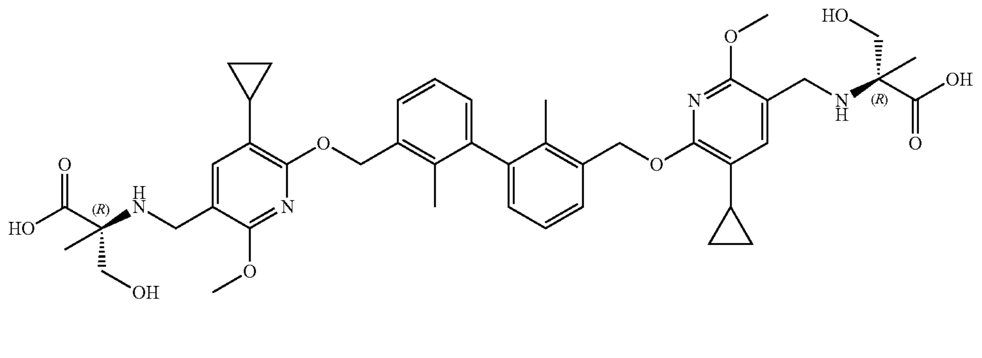

(2R,2'R)-2,2'-((((((2,2'-dimethyl-[1,1'-biphenyl]-3,3'-diyl)bis(methylene))bis(oxy))bis(5-cyclopropyl-2-methoxypyridine-6,3-diyl))bis(methylene))bis(azanediyl))bis(3-hydroxy-2-methylpropanoic acid) was synthesized following the procedure shown in Example 40. LC/MS calculated for $(M+H)^+$: 799.4, found: 799.2.

Example 65:1,1'-(((((2,2'-dimethyl-[1,1'-biphenyl]-3,3'-diyl)bis(methylene))bis(oxy))bis(5-chloro-2-methoxypyridine-6,3-diyl))bis(methylene))bis(azetidine-2-carboxamide) (or 1,1'-((6,6'-(((2,2'-dimethyl-[1,1'-biphenyl]-3,3'-diyl)bis(methylene))bis(oxy))bis(5-chloro-2-methoxypyridine-6,3-diyl))bis(methylene))bis(azetidine-2-carboxamide))

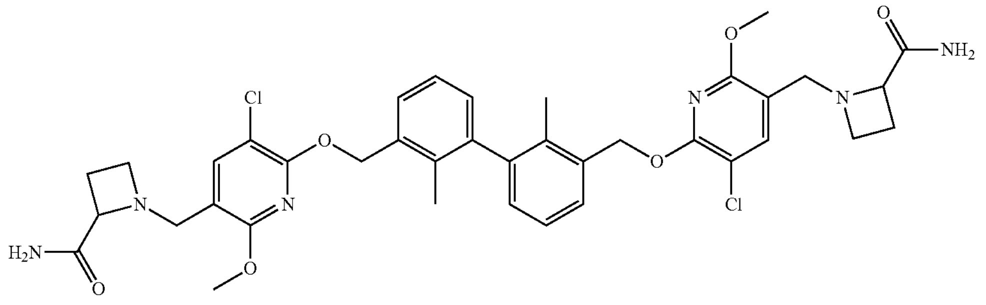 [SMILES: COc1nc(OCc2cccc(-c3cccc(COc4nc(OC)c(CN5CCC5C(N)=O)cc4Cl)c3C)c2C)c(Cl)cc1CN1CCC1C(N)=O]

1,1'-(((((2,2'-dimethyl-[1,1'-biphenyl]-3,3'-diyl)bis(methylene))bis(oxy))bis(5-chloro-2-methoxypyridine-6,3-diyl))bis(methylene))bis(azetidine-2-carboxamide) was synthesized following the reductive amination procedure H. $^1H$ NMR (400 MHz, Methanol-$d_4$) δ 7.78 (s, 2H), 7.46 (dd, J=7.4, 1.1 Hz, 2H), 7.25 (t, J=7.6 Hz, 2H), 7.08 (dd, J=7.6, 1.4 Hz, 2H), 5.57 (s, 4H), 5.07 (t, J=9.4 Hz, 2H), 4.39-4.20 (m, 4H), 4.15 (q, J=9.6 Hz, 2H), 4.04 (s, 6H), 3.97 (td, J=9.6, 3.8 Hz, 2H), 2.80-2.63 (m, 2H), 2.50 (dq, J=11.5, 9.5 Hz, 2H), 2.08 (s, 6H). LC/MS calculated for $(M+H)^+$: 749.3, found: 749.2.

Example 66: (3S,3'S)-4,4'-((((((2,2'-dimethyl-[1,1'-biphenyl]-3,3'-diyl)bis(methylene))bis(oxy))bis(5-chloro-2-((5-cyanopyridin-3-yl)methoxy)-4,1-phenylene))bis(methylene))bis(azanediyl))bis(3-hydroxybutanoic acid)

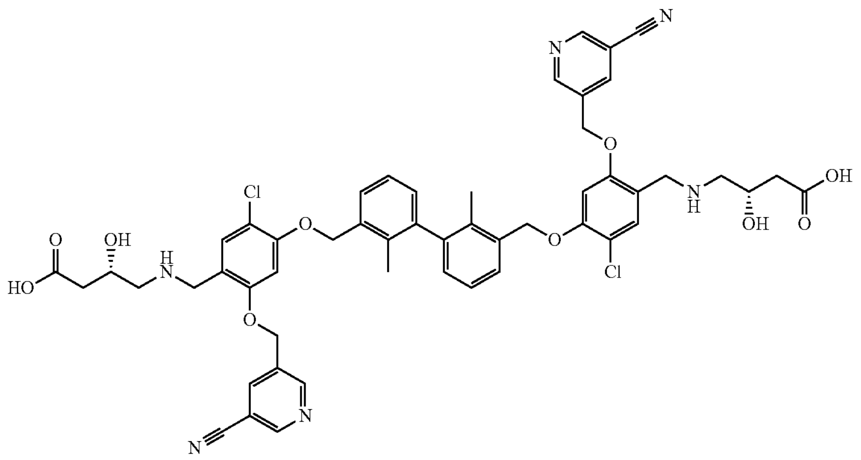 [SMILES: Cc1c(COc2cc(OCc3cncc(C#N)c3)c(CNC[C@@H](O)CC(=O)O)cc2Cl)cccc1-c1cccc(COc2cc(OCc3cncc(C#N)c3)c(CNC[C@@H](O)CC(=O)O)cc2Cl)c1C]

The title compound was prepared from Intermediate 12 following reductive amination procedure C using sodium cyanoborohydride as the reducing agent. purified via prep HPLC (5-95% acetonitrile in water, 0.1% trifluoroacetic acid buffer) $^1H$ NMR (400 MHz, DMSO-$d_6$) $^1H$ NMR (400 MHz, Methanol-d4) δ 8.94 (dd, J=16.2, 2.0 Hz, 4H), 8.39 (t, J=2.0 Hz, 2H), 7.56-7.42 (m, 4H), 7.27 (t, J=7.6 Hz, 2H), 7.16-7.05 (m, 4H), 5.38 (s, 4H), 5.31 (s, 4H), 4.30-4.15 (m, 6H), 3.20 (dd, J=12.8, 3.1 Hz, 2H), 3.03-2.92 (m, 2H), 2.52 (d, J=6.3 Hz, 4H), 2.08 (s, 6H). LCMS-ESI$^+$ (m/z): $[M+H]^+$ calculated for $C_{52}HC_{50}O_2N_6O_{10}$: 989.3; found: 989.3.

Example 67: (S)-4-((4-((3'-((4-((((S)-3-carboxy-2-hydroxypropyl)amino)methyl)-2-chloro-5-((5-cyano-pyridin-3-yl)methoxy)phenoxy)methyl)-2,2'-dimethyl-[1,1'-biphenyl]-3-yl)methoxy)-5-chloro-2-hydroxybenzyl)amino)-3-hydroxybutanoic acid

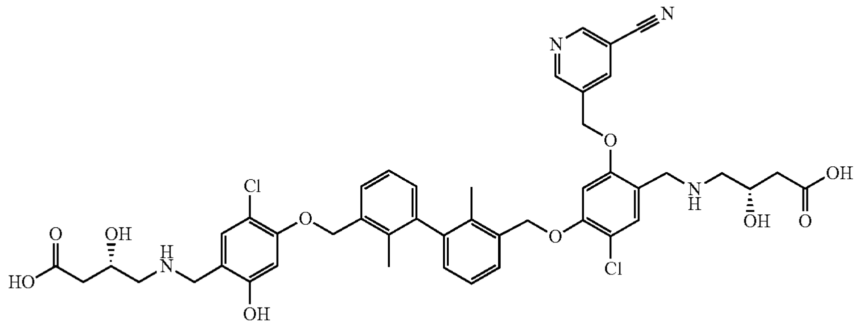 [SMILES: Cc1c(COc2cc(O)c(CNC[C@@H](O)CC(=O)O)cc2Cl)cccc1-c1cccc(COc2cc(OCc3cncc(C#N)c3)c(CNC[C@@H](O)CC(=O)O)cc2Cl)c1C]

The title compound was isolated as a by-product of the synthesis of Example 66. $^{1}$H NMR (400 MHz, Methanol-$d_4$) δ 8.95 (dd, J=12.8, 2.0 Hz, 2H), 8.4 (s, 1H), 7.51 (s, 1H), 7.47 (dt, J=7.7, 1.7 Hz, 2H), 7.37 (s, 1H), 7.27 (td, J=7.6, 3.2 Hz, 2H), 7.16-7.05 (m, 3H), 6.76 (s, 1H), 5.38 (s, 2H), 5.31 (s, 2H), 5.20 (s, 2H), 4.34-4.06 (m, 6H), 3.19 (ddd, J=12.7, 4.7, 3.0 Hz, 2H), 2.97 (dd, J=12.7, 9.9 Hz, 2H), 2.52 (dd, J=6.4, 4.1 Hz, 4H), 2.08 (d, J=8.8 Hz, 6H). LCMS-ESI$^{+}$ (m/z): $[M+H]^{+}$ calculated for $C_{45}H_{46}Cl_2N_4O_{10}$: 873.3; found: 873.4.

Example 68: 5,5'-((((((2,2'-dimethyl-[1,1'-biphenyl]-3,3'-diyl)bis(methylene))bis(oxy))bis(4-chloro-6-(((2-hydroxyethyl)amino)methyl)-3,1-phenylene))bis(oxy))bis(methylene))dinicotinonitrile (or 5,5'-((((((2,2'-dimethyl-[1,1'-biphenyl]-3,3'-diyl)bis(methylene))bis(oxy))bis(4-chloro-2-(((2-hydroxyethyl)amino)methyl)-5,1-phenylene))bis(oxy))bis(methylene))dinicotinonitrile)

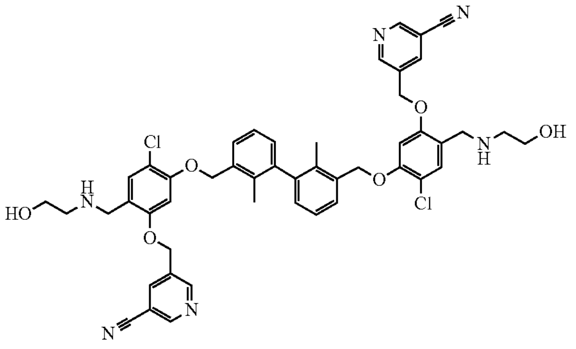 [SMILES: Cc1c(COc2cc(OCc3cncc(C#N)c3)c(CNCCO)cc2Cl)cccc1-c1cccc(COc2cc(OCc3cncc(C#N)c3)c(CNCCO)cc2Cl)c1C]

The title compound was prepared from Intermediate 12 following reductive amination procedure C using sodium cyanoborohydride as the reducing agent. $^{1}$H NMR (400 MHz, Acetonitrile-$d_3$) δ 8.93 (dd, J=8.3, 2.0 Hz, 4H), 8.30 (s, 2H), 8.17 (s, 4H), 7.52 (dd, J=7.6, 1.4 Hz, 2H), 7.47 (s, 2H), 7.33 (t, J=7.6 Hz, 2H), 7.18 (dd, J=7.7, 1.4 Hz, 2H), 6.95 (s, 2H), 5.29 (s, 8H), 4.19 (s, 4H), 3.76-3.65 (m, 4H), 3.08 (s, 4H), 2.06 (s, 6H). LCMS-ESI$^{+}$ (m/z): $[M+H]^{+}$ calculated for $C_{48}H_{46}Cl_2N_6O_6$: 873.3; found: 873.4.

Example 69: 5-((4-chloro-2-(((2-hydroxyethyl)amino)methyl)-5-((3'-((4-(((2-hydroxyethyl)amino)methyl)phenoxy)methyl)-2,2'-dimethyl-[1,1'-biphenyl]-3-yl)methoxy)phenoxy)methyl)nicotinonitrile

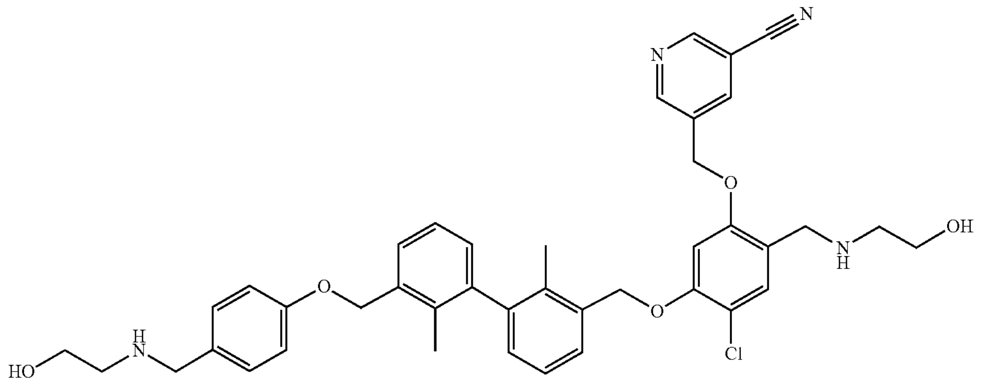 [SMILES: Cc1c(COc2ccc(CNCCO)cc2)cccc1-c1cccc(COc2cc(OCc3cncc(C#N)c3)c(CNCCO)cc2Cl)c1C]

The title compound was prepared from Intermediate 26 using reductive amination procedure C. $^1$H NMR (400 MHz, Acetonitrile-$d_3$) δ 9.00 (d, J=7.7 Hz, 2H), 8.31 (s, 1H), 7.57-7.39 (m, 5H), 7.31 (td, J=7.6, 5.0 Hz, 2H), 7.15 (ddd, J=7.7, 6.3, 1.4 Hz, 2H), 7.12-7.05 (m, 2H), 6.96 (s, 1H), 5.30 (d, J=4.6 Hz, 4H), 5.18 (s, 2H), 4.28-4.10 (m, 4H), 3.82-3.67 (m, 4H), 3.09 (d, J=6.7 Hz, 2H), 2.64 (t, J=5.6 Hz, 2H), 2.06 (s, 3H), 2.03 (s, 3H). LCMS-ESI$^+$ (m/z): [M+H]$^+$ calculated for $C_{41}H_{43}ClN_4O_5$: 707.3; found: 707.2.

Example 70: N,N'-((((((((2,2'-dimethyl-[1,1'-biphenyl]-3,3'-diyl)bis(methylene))bis(oxy))bis(5-chloro-2-((5-cyanopyridin-3-yl)methoxy)-4,1-phenylene))bis(methylene))bis(azanediyl))bis(ethane-2,1-diyl))diacetamide

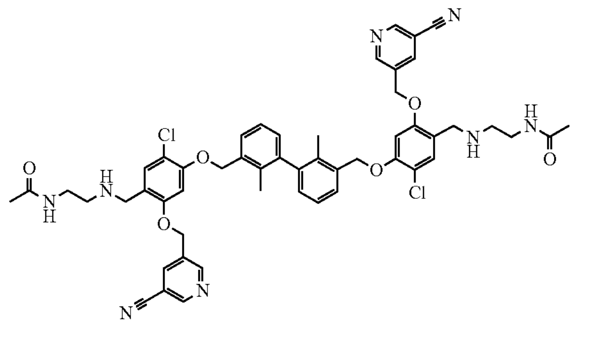 [SMILES: CC(=O)NCCNCc1cc(Cl)c(OCc2cccc(-c3cccc(COc4cc(OCc5cncc(C#N)c5)c(CNCCNC(C)=O)cc4Cl)c3C)c2C)cc1OCc1cncc(C#N)c1]

The title compound was prepared from Intermediate 12 following reductive amination procedure C using sodium cyanoborohydride as the only reducing agent. $^1$H NMR 1H NMR (400 MHz, Acetonitrile-d3) δ 8.94 (dd, J=15.8, 2.0 Hz, 4H), 8.59 (s, 2H), 8.33 (t, J=2.1 Hz, 2H), 7.51 (dd, J=7.7, 1.4 Hz, 2H), 7.45 (s, 2H), 7.32 (t, J=7.6 Hz, 4H), 7.17 (dd, J=7.6, 1.4 Hz, 2H), 6.94 (s, 2H), 5.30 (d, J=7.5 Hz, 8H), 4.15 (s, 4H), 3.34 (d, J=5.4 Hz, 4H), 3.10 (s, 4H), 2.06 (s, 6H), 1.85 (s, 6H). LCMS-ESI$^+$ (m/z): [M+H]$^+$ calculated for $C_{52}H_{52}C_2NO_6$: 955.3; found: 955.4.

Example 71: 5-((4-chloro-5-((3'-((2-chloro-4-(((2-hydroxyethyl)amino)methyl)phenoxy)methyl)-2,2'-dimethyl-[1,1'-biphenyl]-3-yl)methoxy)-2-(((2-hydroxyethyl)amino)methyl)phenoxy)methyl) nicotinonitrile

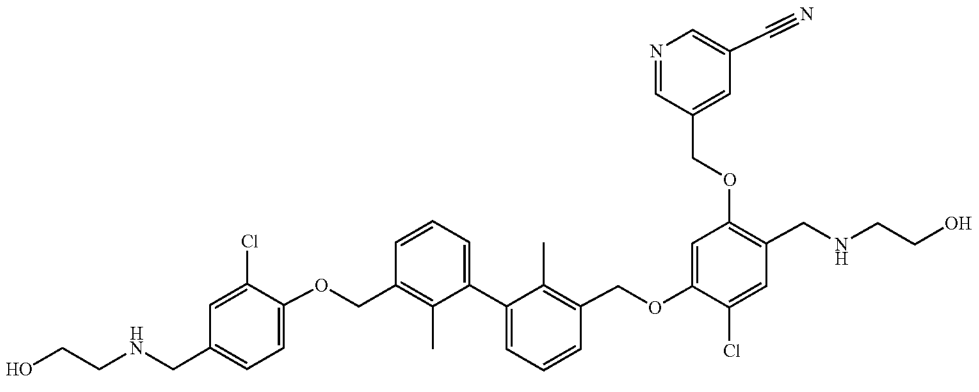 [SMILES: Cc1c(COc2ccc(CNCCO)cc2Cl)cccc1-c1cccc(COc2cc(OCc3cncc(C#N)c3)c(CNCCO)cc2Cl)c1C]

The title compound was prepared following the procedure described in Example 69 using 3-chloro-4-hydroxybenzaldehyde. $^1H$ NMR (400 MHz, Acetonitrile-$d_3$) δ 8.95 (s, 1H), 8.3 (s, 1H), 8.03 (s, 1H), 7.59 (d, J=2.2 Hz, 1H), 7.53 (dt, J=7.6, 1.8 Hz, 2H), 7.48-7.41 (m, 2H), 7.33 (t, J=7.6 Hz, 2H), 7.27 (d, J=8.5 Hz, 1H), 7.17 (d, J=7.6 Hz, 2H), 6.95 (s, 1H), 5.29 (d, J=11.4 Hz, 6H), 4.18 (d, J=14.1 Hz, 4H), 3.75 (dt, J=22.9, 5.1 Hz, 4H), 3.10 (d, J=12.9 Hz, 4H), 2.07 (d, J=7.7 Hz, 6H). LCMS-ESI$^+$ (m/z): $[M+H]^+$ calculated for $C_{41}H_{42}Cl_2N_4O_5$: 741.3; found: 741.2.

Example 72: 3,3'-bis(((5-(((2-hydroxyethyl)amino) methyl)-6-methoxypyridin-2-yl)oxy)methyl)-2'-methyl-[1,1'-biphenyl]-2-carbonitrile

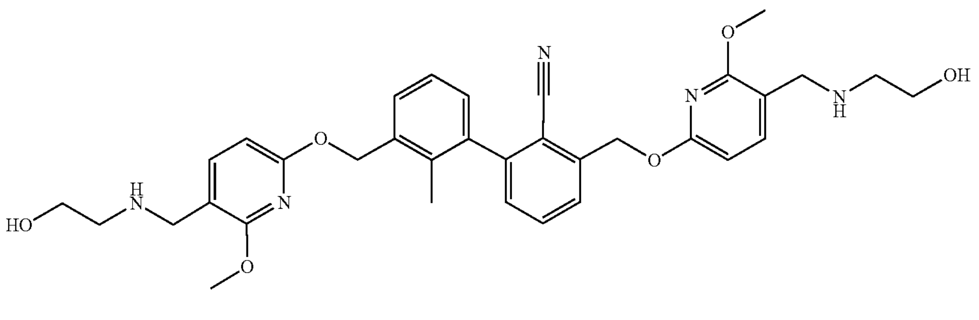 [SMILES: COc1nc(OCc2cccc(-c3cccc(COc4ccc(CNCCO)c(OC)n4)c3C#N)c2C)ccc1CNCCO]

The title compound was prepared from Intermediate 27 following general reductive amination procedure E. $^1H$ NMR (400 MHz, Methanol-$d_4$) δ 7.77-7.65 (m, 4H), 7.57-7.50 (m, 1H), 7.38 (dd, J=6.8, 2.0 Hz, 1H), 7.29 (t, J=7.6 Hz, 1H), 7.17 (dd, J=7.7, 1.4 Hz, 1H), 6.52 (dd, J=21.1, 8.0 Hz, 2H), 5.66 (d, J=3.6 Hz, 2H), 5.60-5.46 (m, 2H), 4.16 (d, J=1.9 Hz, 4H), 4.01 (d, J=5.6 Hz, 6H), 3.83-3.70 (m, 6H), 3.15-3.07 (m, 5H), 3.02 (t, J=5.3 Hz, 2H), 2.19 (s, 3H). LCMS-ESI$^+$ (m/z): $[M+H]^+$ calculated for $C_{34}H_{39}N_5O_6$: 614.3; found: 614.3.

Example 73: 5,5'-((((((2,2'-dimethyl-[1,1'-biphenyl]-3,3'-diyl)bis(methylene))bis(oxy))bis(4-chloro-6-(((3-hydroxypropyl)amino)methyl)-3,1-phenylene))bis(oxy))bis(methylene))dinicotinonitrile (or 5,5'-((((((2,2'-dimethyl-[1,1'-biphenyl]-3,3'-diyl)bis(methylene))bis(oxy))bis(4-chloro-2-(((3-hydroxypropyl)amino)methyl)-5,1-phenylene))bis(oxy))bis(methylene))dinicotinonitrile)

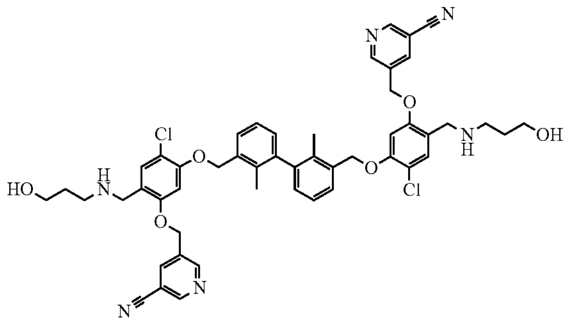 [SMILES: Cc1c(COc2cc(OCc3cncc(C#N)c3)c(CNCCCO)cc2Cl)cccc1-c1cccc(COc2cc(OCc3cncc(C#N)c3)c(CNCCCO)cc2Cl)c1C]

5,5'-((((((2,2'-dimethyl-[1,1'-biphenyl]-3,3'-diyl)bis(methylene))bis(oxy))bis(4-chloro-6-formyl-3,1-phenylene))bis(oxy))bis(methylene))dinicotinonitrile (Intermediate 12, 500 mg, 0.64 mmol) was dissolved in a mixture of THF and methanol (2:1) 12 mL and then sodium borohydride (48 mg, 0.001 mol) was slowly added. Reaction mixture was stirred at room temperature for 10 min, quenched by the addition of water and then extracted with EtOAc. Organic layers were dried over $Mg_2SO_4$ and evaporated under reduced pressure to yield 5,5'-((((((2,2'-dimethyl-[1,1'-biphenyl]-3,3'-diyl)bis(methylene))bis(oxy))bis(4-chloro-6-(hydroxymethyl)-3,1-phenylene))bis(oxy))bis(methylene))dinicotinonitrile.

To a solution of 5,5'-((((((2,2'-dimethyl-[1,1'-biphenyl]-3,3'-diyl)bis(methylene))bis(oxy))bis(4-chloro-6-(hydroxymethyl)-3,1-phenylene))bis(oxy))bis(methylene))dinicotinonitrile (2.4 mmol) in dichloromethane (5 mL), kept at 0° C., was added methanesulfonyl chloride (4.8 mmol) over a period of 10 min. Mixture warmed up to room temperature and stirred for 4 hrs. Reaction mixture was transferred to a separatory funnel and was successively washed with water and dichloromethane. The organic phase was dried with sodium sulfate and evaporated to obtain ((((2,2'-dimethyl-[1,1'-biphenyl]-3,3'-diyl)bis(methylene))bis(oxy))bis(5-chloro-2-((5-cyanopyridin-3-yl)methoxy)-4,1-phenylene))bis(methylene) dimethanesulfonate.

To a solution of ((((2,2'-dimethyl-[1,1'-biphenyl]-3,3'-diyl)bis(methylene))bis(oxy))bis(5-chloro-2-((5-cyanopyridin-3-yl)methoxy)-4,1-phenylene))bis(methylene) dimethanesulfonate (752 mg, 1.36 mmol) in DMF was added 3-aminopropan-1-ol (1.6 gr, 5.4 mmol)under argon atmosphere and stirred at room temperature for 1 hr. and purified via prep HPLC (5-95% acetonitrile in water, 0.1% trifluoroacetic acid). $^1H$ NMR (400 MHz, Methanol-$d_4$) δ 8.94 (dd, J=10.8, 2.1 Hz, 4H), 8.42-8.30 (m, 2H), 7.58-7.42 (m, 4H), 7.26 (t, J=7.6 Hz, 2H), 7.12 (d, J=7.8 Hz, 2H), 7.06 (d, J=6.6 Hz, 2H), 5.34 (dd, J=31.2, 3.2 Hz, 8H), 4.20 (s, 2H), 3.52-3.48 (m, 4H), 3.15 (t, J=7.0 Hz, 2H), 3.05 (t, J=7.2 Hz, 6H), 2.86 (d, J=0.7 Hz, 2H), 2.07 (s, 6H). LCMS-ESI (m/z): $[M+H]^+$ calculated for $C_{50}H_{50}Cl_2N_6O_6$: 901.3; found: 901.4.

Example 74: (3S,3'S)-3,3'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))dibutyric acid ((3S,3'S)-3,3'-(((6,6'-(((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))dibutyric acid)

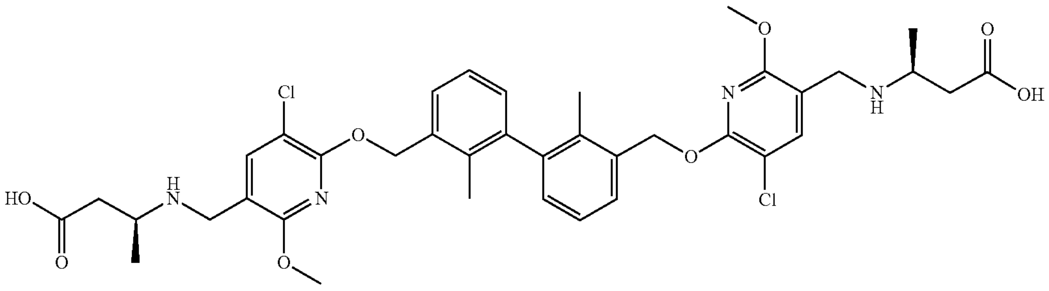 [SMILES: COc1nc(OCc2cccc(-c3cccc(COc4nc(OC)c(CN[C@@H](C)CC(=O)O)cc4Cl)c3C)c2C)c(Cl)cc1CN[C@@H](C)CC(=O)O]

Sodium triacetoxyborohydride (9 equiv) and sodium cyanoborohydride (9 equiv) were added sequentially to a stirred mixture of 6,6'-(((2,2'-dimethyl-[1,1'-biphenyl]-3,3'-diyl)bis(methylene))bis(oxy))bis(5-chloro-2-methoxynicotinaldehyde) and (S)-3-aminobutanoic acid (15 equiv) in N,N-dimethylformamide (40 mL per mmol substrate) and acetic acid (7 mL per mmol substrate) at room temperature. After 15 min, trifluoroacetic acid (0.2 mL) was added. The resulting mixture was purified by reverse phase preparative HPLC (0.1% trifluoroacetic acid in acetonitrile/water) to give (3S,3'S)-3,3'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))dibutyric acid. $^1H$ NMR (400 MHz, Methanol-$d_4$) δ 7.82 (s, 2H), 7.47 (dd, J=7.7, 1.4 Hz, 2H), 7.24 (t, J=7.6 Hz, 2H), 7.07 (dd, J=7.6, 1.4 Hz, 2H), 5.59 (s, 4H), 4.20 (d, J=13.4 Hz, 2H), 4.14 (d, J=13.3 Hz, 2H), 4.06 (s, 6H), 3.64 (h, J=6.6 Hz, 2H), 2.75 (d, J=6.3, 4H), 2.08 (s, 6H), 1.42 (d, J=6.7 Hz, 6H); LRMS: 755.2.

Example 75: (1R,1'R,2R,2'R)-2,2'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(cyclopentane-1-carboxylic acid) (or (1R,1'R,2R,2'R)-2,2'-(((6,6'-(((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(cyclopentane-1-carboxylic acid)

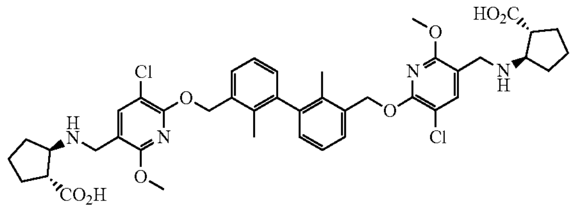 [SMILES: COc1nc(OCc2cccc(-c3cccc(COc4nc(OC)c(CN[C@@H]5CCC[C@H]5C(=O)O)cc4Cl)c3C)c2C)c(Cl)cc1CN[C@@H]1CCC[C@H]1C(=O)O]

Sodium triacetoxyborohydride (9 equiv) was added to a stirred mixture of 6,6'-(((2,2'-dimethyl-[1,1'-biphenyl]-3,3'-diyl)bis(methylene))bis(oxy))bis(5-chloro-2-methoxynicotinaldehyde) and (1R,2R)-2-aminocyclopentane-1-carboxylic acid (15 equiv) in dimethylsulfoxide (100 mL per mmol substrate) and acetic acid (20 mL per mmol substrate) at room temperature. After 60 min, trifluoroacetic acid (0.2 mL) was added. The resulting mixture was purified by reverse phase preparative HPLC (0.1% trifluoroacetic acid in acetonitrile/water) to give (1R,1'R,2R,2'R)-2,2'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(cyclopentane-1-carboxylic acid). $^{1}$H NMR (400 MHz, Methanol-$d_4$) δ 7.82 (s, 2H), 7.47 (dd, J=7.5, 1.4 Hz, 2H), 7.24 (t, J=7.6 Hz, 2H), 7.07 (dd, J=7.6, 1.4 Hz, 2H), 5.59 (s, 4H), 4.15 (d, J=1.9 Hz, 4H), 4.06 (s, 6H), 3.91 (q, J=7.2 Hz, 2H), 2.94 (dt, J=9.4, 7.0 Hz, 2H), 2.32-2.13 (m, 4H), 2.08 (s, 6H), 2.02-1.67 (m, 8H); LRMS: 807.2.

Example 76: 2,2'-((((((2,2'-dimethyl-[1,1'-biphenyl]-3,3'-diyl)bis(methylene))bis(oxy))bis(5-chloro-2-methoxypyridine-6,3-diyl))bis(methylene))bis(methylazanediyl))diacetic acid (or 2,2'-(((6,6'-(((2,2'-dimethyl-[1,1'-biphenyl]-3,3'-diyl)bis(methylene))bis(oxy))bis(5-chloro-2-methoxypyridine-6,3-diyl))bis(methylene))bis(methylazanediyl))diacetic acid)

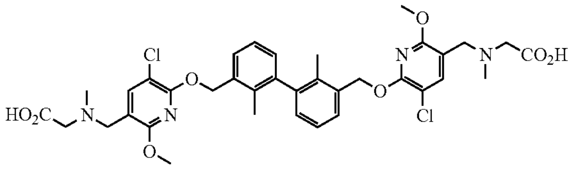 [SMILES: COc1nc(OCc2cccc(-c3cccc(COc4nc(OC)c(CN(C)CC(=O)O)cc4Cl)c3C)c2C)c(Cl)cc1CN(C)CC(=O)O]

2,2'-((((((2,2'-Dimethyl-[1,1'-biphenyl]-3,3'-diyl)bis(methylene))bis(oxy))bis(5-chloro-2-methoxypyridine-6,3-diyl))bis(methylene))bis(methylazanediyl))diacetic acid was synthesized in a manner similar to Procedure D using sarcosine in place of (1R,2R)-2-aminocyclopentane-1-carboxylic acid and with a reaction temperature of 60° C. $^{1}$H NMR (400 MHz, Methanol-$d_4$) δ 7.86 (s, 2H), 7.49 (d, J=7.7 Hz, 2H), 7.26 (t, J=7.6 Hz, 2H), 7.09 (dd, J=7.7, 1.4 Hz, 2H), 5.60 (s, 4H), 4.35 (s, 4H), 4.05 (s, 6H), 4.04 (s, 4H), 2.89 (s, 6H), 2.10 (s, 6H); LRMS: 727.3.

Example 77: 3,3'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(2,2-dimethylpropanoic acid) (or 3,3'-(((6,6'-(((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(2,2-dimethylpropanoic acid))

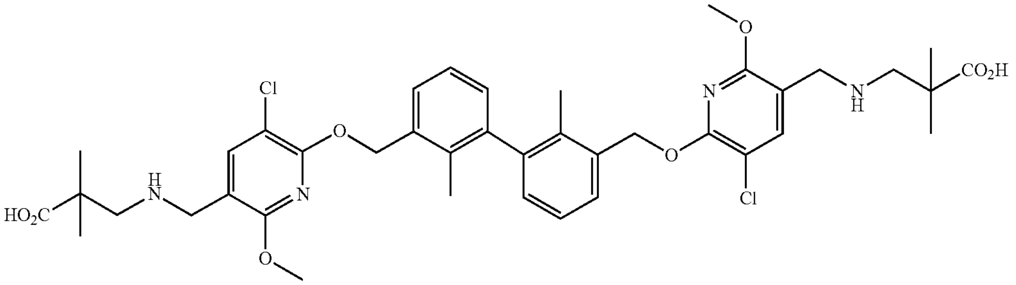 [SMILES: COc1nc(OCc2cccc(-c3cccc(COc4nc(OC)c(CNCC(C)(C)C(=O)O)cc4Cl)c3C)c2C)c(Cl)cc1CNCC(C)(C)C(=O)O]

3,3'-((((((2,2'-Dimethyl-[1,1'-biphenyl]-3,3'-diyl)bis(methylene))bis(oxy))bis(5-chloro-2-methoxypyridine-6,3-diyl))bis(methylene))bis(azanediyl))bis(2,2-dimethylpropanoic acid) was synthesized in a manner similar to Procedure D using 3-amino-2,2-dimethylpropanoic acid in place of (1R,2R)-2-aminocyclopentane-1-carboxylic acid. $^{1}$H NMR (400 MHz, Methanol-d4) δ 7.80 (s, 2H), 7.48 (d, J=7.6 Hz, 2H), 7.24 (t, J=7.6 Hz, 2H), 7.08 (d, J=7.5 Hz, 2H), 5.59 (s, 4H), 4.16 (s, 4H), 4.07 (s, 6H), 3.09 (s, 4H), 2.09 (s, 6H), 1.29 (s, 12H); LRMS: 783.3.

Example 78: 1,1'-((((2,2'-dimethyl-[1,1'-biphenyl]-3,3'-diyl)bis(methylene))bis(oxy))bis(5-chloro-2-methoxypyridine-6,3-diyl))bis(N-(carboxymethyl)-N,N-dimethylmethanaminium) (or 1,1'-(6,6'-(((2,2'-dimethyl-[1,1'-biphenyl]-3,3'-diyl)bis(methylene))bis(oxy))bis(5-chloro-2-methoxypyridine-6,3-diyl))bis(N-(carboxymethyl)-N,N-dimethylmethanaminium))

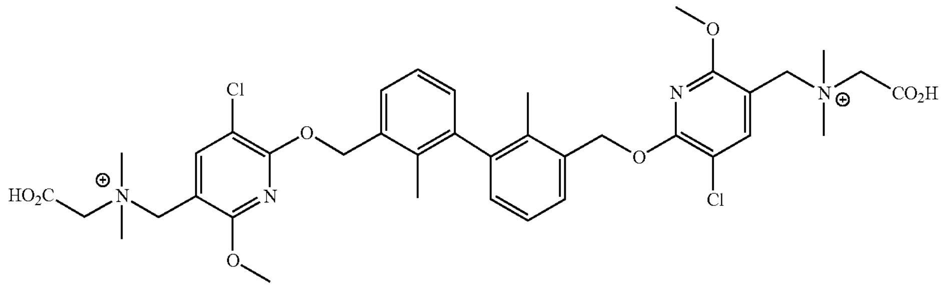 [SMILES: COc1nc(OCc2cccc(-c3cccc(COc4nc(OC)c(C[N+](C)(C)CC(=O)O)cc4Cl)c3C)c2C)c(Cl)cc1C[N+](C)(C)CC(=O)O]

Iodomethane (0.029 mL, 0.47 mmol) was added via syringe to a stirred solution of 2,2'-((((((2,2'-dimethyl-[1,1'-biphenyl]-3,3'-diyl)bis(methylene))bis(oxy))bis(5-chloro-2-methoxypyridine-6,3-diyl))bis(methylene))bis(methyl-azanediyl))diacetic acid (17 mg, 0.023 mmol) in dimethylsulfoxide and aqueous sodium hydroxide solution (2.0 M, 0.47 mL) at room temperature. After 30 min, trifluoroacetic acid (0.1 mL) was added. The resulting mixture was purified by reverse phase preparative HPLC (0.1% trifluoroacetic acid in acetonitrile/water) to give 1,1'-((((2,2'-dimethyl-[1,1'-biphenyl]-3,3'-diyl)bis(methylene))bis(oxy))bis(5-chloro-2-methoxypyridine-6,3-diyl))bis(N-(carboxymethyl)-N,N-dimethylmethanaminium). $^1$H NMR (400 MHz, Methanol-d4) δ 7.87 (s, 2H), 7.49 (d, J=7.6 Hz, 2H), 7.26 (t, J=7.6 Hz, 2H), 7.10 (d, J=7.8 Hz, 2H), 5.62 (s, 4H), 4.67 (s, 4H), 4.11 (s, 4H), 4.04 (s, 6H), 3.24 (s, 12H), 2.10 (s, 6H). LRMS: 378.1 ($[M]^{2+}$).

Example 79: (1S,1'S,2R,2'R)-2,2'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(cyclopentane-1-carboxylicacid) (or (1S,1'S,2R,2'R)-2,2'-(((6,6'-(((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(cyclopentane-1-carboxylic acid))

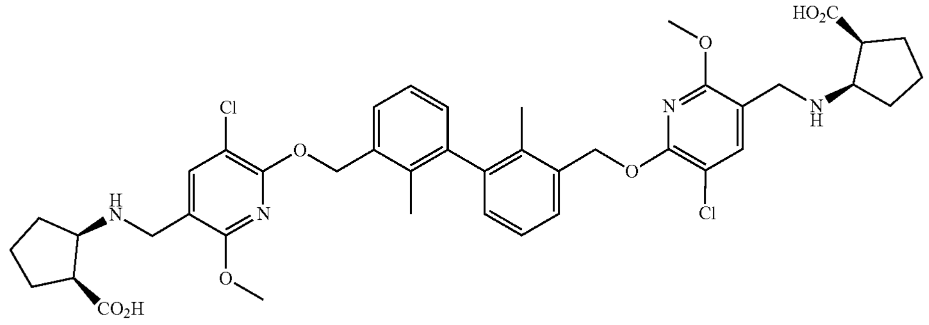 [SMILES: COc1nc(OCc2cccc(-c3cccc(COc4nc(OC)c(CN[C@@H]5CCC[C@@H]5C(=O)O)cc4Cl)c3C)c2C)c(Cl)cc1CN[C@@H]1CCC[C@@H]1C(=O)O]

(1S,1'S,2R,2'R)-2,2'-((((((2,2'-Dimethyl-[1,1'-biphenyl]-3,3'-diyl)bis(methylene))bis(oxy))bis(5-chloro-2-methoxy-pyridine-6,3-diyl))bis(methylene))bis(azanediyl))bis(cyclo-pentane-1-carboxylic acid) was synthesized using general reductive amination procedure D using (1S,2R)-2-aminocyclopentane-1-carboxylic acid in place of (1R,2R)-2-amino-cyclopentane-1-carboxylic acid. $^1$H NMR (400 MHz, Methanol-d4) δ 7.81 (s, 2H), 7.52-7.43 (m, 2H), 7.24 (t, J=7.6 Hz, 2H), 7.11-7.03 (m, 2H), 5.59 (s, 4H), 4.23-4.19 (m, 4H), 4.06 (s, 6H), 3.66 (q, J=7.0 Hz, 2H), 3.17 (q, J=6.7 Hz, 2H), 2.26-1.64 (m, 12H), 2.09 (s, 6H); LRMS: 807.2.

Example 80: (1S,1'S,2S,2'S)-2,2'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(cyclohexane-1-carboxylic acid) (or (1S,1'S,2S,2'S)-2,2'-(((6,6'-(((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(cyclohexane-1-carboxylic acid))

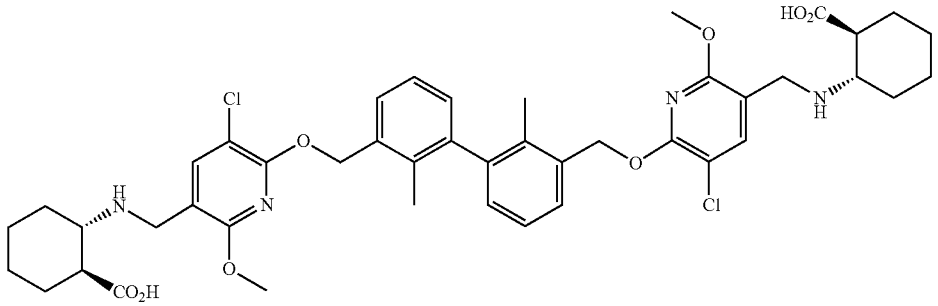 [SMILES: COc1nc(OCc2cccc(-c3cccc(COc4nc(OC)c(CN[C@H]5CCCC[C@@H]5C(=O)O)cc4Cl)c3C)c2C)c(Cl)cc1CN[C@H]1CCCC[C@@H]1C(=O)O]

(1S,1'S,2S,2'S)-2,2'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(cyclohexane-1-carboxylic acid) was synthesized using general reductive amination procedure D using (1S,2S)-2-aminocyclohexane-1-carboxylic acid in place of (1R,2R)-2-aminocyclopentane-1-carboxylic acid. $^{1}$H NMR (400 MHz, Methanol-d4) δ 7.81 (s, 2H), 7.47 (dd, J=7.3, 1.3 Hz, 2H), 7.24 (t, J=7.6 Hz, 2H), 7.12-7.01 (m, 2H), 5.59 (s, 4H), 4.24 (d, J=13.3 Hz, 2H), 4.15 (d, J=13.3 Hz, 2H), 4.07 (s, 6H), 3.38-3.28 (m, 2H), 2.54 (td, J=11.3, 4.0 Hz, 2H), 2.35-2.25 (m, 4H), 2.09 (s, 6H), 1.95-1.87 (m, 2H), 1.85-1.77 (m, 2H), 1.58-1.30 (m, 8H); LRMS: 835.3.

Example 81: (±)-(1R,1'R,2S,2'S)-2,2'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(cyclohexane-1-carboxylic acid) (or (1R,1'R,2S,2'S)-2,2'-(((6,6'-(((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(cyclohexane-1-carboxylic acid)) and (1S,1'R,2R,2'S)-2,2'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(cyclohexane-1-carboxylic acid)

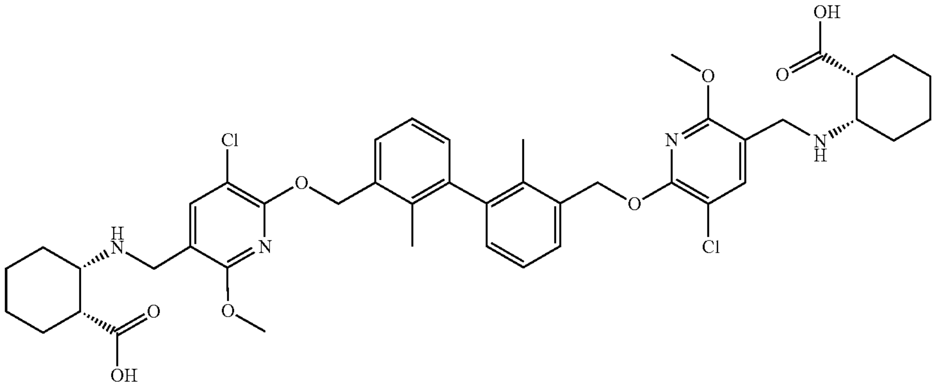

+

-continued

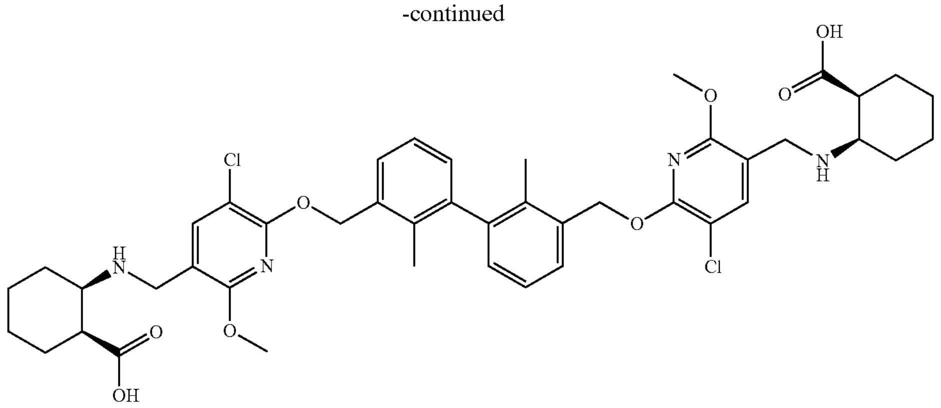

and

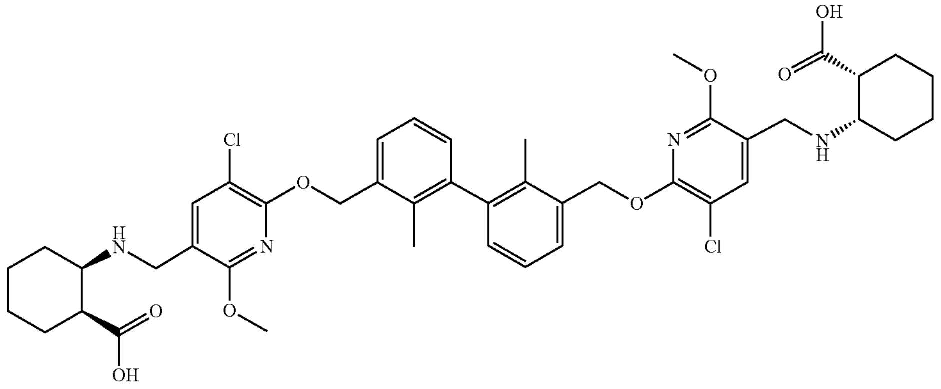

A stereoisomeric mixture of (±)-(1R,1'R,2S,2'S)-2,2'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(cyclohexane-1-carboxylic acid) and (S,1'R,2R,2'S)-2,2'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(cyclohexane-1-carboxylic acid) was synthesized using general reductive amination procedure D using (±)-(1R,2S)-2-aminocyclohexane-1-carboxylic acid in place of (1R,2R)-2-aminocyclopentane-1-carboxylic acid. $^1$H NMR (400 MHz, Methanol-d4) δ 7.79 (s, 2H), 7.47 (d, J=7.6 Hz, 2H), 7.24 (t, J=7.6 Hz, 2H), 7.14-7.00 (m, 2H), 5.59 (s, 4H), 4.21 (d, J=13.4 Hz, 2H), 4.13 (d, J=13.3 Hz, 2H), 4.05 (s, 6H), 3.38-3.28 (m, 2H), 3.18 (q, J=4.4 Hz, 2H), 2.35-2.25 (m, 2H), 2.09 (s, 6H), 2.04-1.94 (m, 2H), 1.93-1.80 (m, 4H), 1.70-1.57 (m, 4H), 1.55-1.20 (m, 4H); LRMS: 835.3.

Example 82: 3,3'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(3-methylbutanoic acid) (or 3,3'-(((6,6'-(((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(3-methylbutanoic acid))

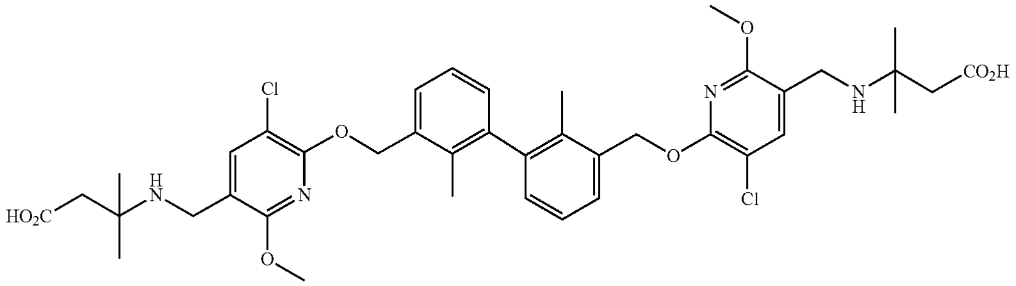 [SMILES: COc1nc(OCc2cccc(-c3cccc(COc4nc(OC)c(CNC(C)(C)CC(=O)O)cc4Cl)c3C)c2C)c(Cl)cc1CNC(C)(C)CC(=O)O]

3,3'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(3-methylbutanoic acid) was synthesized using general reductive amination procedure D using 3-amino-3-methylbutanoic acid in place of (1R,2R)-2-aminocyclopentane-1-carboxylic acid. $^1$H NMR (400 MHz, Methanol-d4) δ 7.81 (s, 2H), 7.46 (d, J=7.5 Hz, 2H), 7.23 (t, J=7.5 Hz, 2H), 7.06 (dd, J=7.5, 1.2 Hz, 2H), 5.59 (s, 4H), 4.14 (s, 4H), 4.06 (s, 6H), 2.82 (s, 4H), 2.09 (s, 6H), 1.50 (s, 12H); LRMS: 783.3.

Example 83: 2,2'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(N,N-dimethylpropanamide) (or 2,2'-(((6,6'-(((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(N,N-dimethylpropanamide))

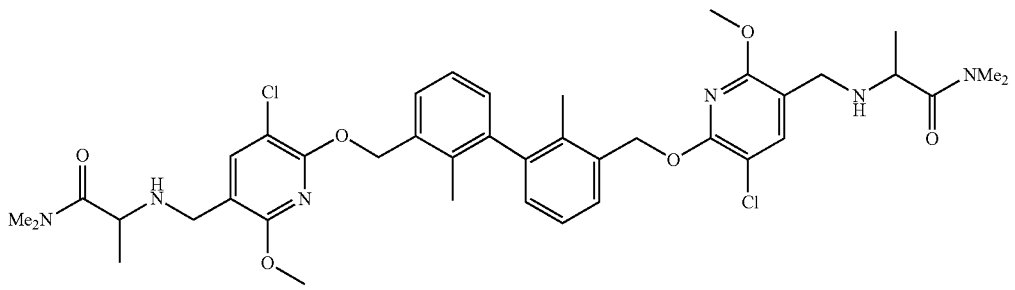 [SMILES: COc1nc(OCc2cccc(-c3cccc(COc4nc(OC)c(CNC(C)C(=O)N(C)C)cc4Cl)c3C)c2C)c(Cl)cc1CNC(C)C(=O)N(C)C]

2,2'-((((((2,2'-Dimethyl-[1,1'-biphenyl]-3,3'-diyl)bis(methylene))bis(oxy))bis(5-chloro-2-methoxypyridine-6,3-diyl))bis(methylene))bis(azanediyl))bis(N,N-dimethylpropanamide) was synthesized using general reductive amination procedure D using (±)-2-amino-N,N-dimethylpropanamide hydrochloride (15 equiv) and N,N-diisopropylethylamine (17 equiv) in place of (1R,2R)-2-aminocyclopentane-1-carboxylic acid. $^1$H NMR (400 MHz, Methanol-d4) δ 7.77 (s, 2H), 7.48 (d, J=7.4 Hz, 2H), 7.24 (t, J=7.6 Hz, 2H), 7.07 (d, J=7.6 Hz, 2H), 5.60 (s, 4H), 4.38 (q, J=6.9 Hz, 2H), 4.11 (d, J=13.3 Hz, 2H), 4.05 (s, 6H), 4.03 (d, J=14.0 Hz, 2H), 3.02 (d, J=0.7 Hz, 6H), 2.92 (d, J=1.7 Hz, 6H), 2.09 (s, 6H), 1.46 (d, J=6.9 Hz, 6H); LRMS: 781.3.

Example 84: 4,4'-((((((2,2'-dimethyl-[1,1'-biphenyl]-3,3'-diyl)bis(methylene))bis(oxy))bis(2-methoxypyridine-6,3-diyl))bis(methylene))bis(azanediyl))bis(2,2-difluoro-3-hydroxybutanoic acid) (or 4,4'-(((6,6'-(((2,2'-dimethyl-[1,1'-biphenyl]-3,3'-diyl)bis(methylene))bis(oxy))bis(2-methoxypyridine-6,3-diyl))bis(methylene))bis(azanediyl))bis(2,2-difluoro-3-hydroxybutanoic acid))

4,4'-((((((2,2'-dimethyl-[1,1'-biphenyl]-3,3'-diyl)bis(methylene))bis(oxy))bis(2-methoxypyridine-6,3-diyl))bis(methylene))bis(azanediyl))bis(2,2-difluoro-3-hydroxybutanoic acid) was synthesized using general reductive amination procedure C using 3-carboxy-3,3-difluoro-2-hydroxypropan-1-aminium 2,2,2-trifluoroacetate (5 equiv) and triethylamine (10 equiv) in place of (S)-3-aminobutanoic acid and using 6,6'-(((2,2'-dimethyl-[1,1'-biphenyl]-3,3'-diyl)bis(methylene))bis(oxy))bis(2-methoxynicotinaldehyde) in place of 6,6'-(((2,2'-dimethyl-[1,1'-biphenyl]-3,3'-diyl)bis(methylene))bis(oxy))bis(5-chloro-2-methoxynicotinaldehyde). $^1$H NMR (400 MHz, Methanol-d4) δ 7.68 (d, J=8.1 Hz, 2H), 7.43 (d, J=7.6 Hz, 2H), 7.22 (t, J=7.6 Hz, 2H), 7.05 (dd, J=7.7, 1.4 Hz, 2H), 6.47 (d, J=8.1 Hz, 2H), 5.49 (s, 4H), 4.42-4.28 (m, 2H), 4.18 (s, 4H), 4.03 (s, 6H), 3.33-3.19 (m, 4H), 2.05 (S, 6H); LRMS: 791.1.

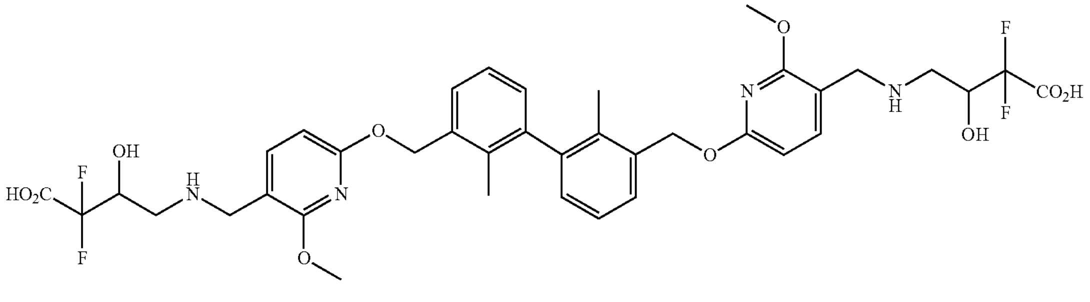 [SMILES: COc1nc(OCc2cccc(-c3cccc(COc4ccc(CNCC(O)C(F)(F)C(=O)O)c(OC)n4)c3C)c2C)ccc1CNCC(O)C(F)(F)C(=O)O]

Example 85: 3,3'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(bicyclo[1.1.1]pentane-1-carboxylic acid) (or 3,3'-(((6,6'-(((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(bicyclo[1.1.1]pentane-1-carboxylic acid))

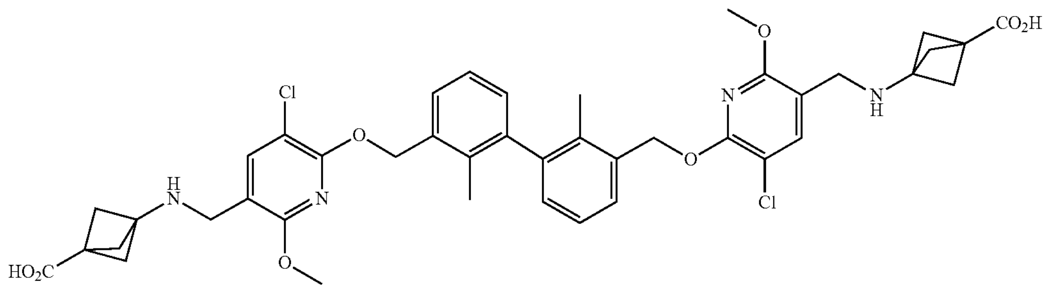 [SMILES: COc1nc(OCc2cccc(-c3cccc(COc4nc(OC)c(CNC56CC(C(=O)O)(C5)C6)cc4Cl)c3C)c2C)c(Cl)cc1CNC12CC(C(=O)O)(C1)C2]

Trifluoroacetic acid (0.8 mL) was added to a stirred solution of 3-((tert-butoxycarbonyl)amino)bicyclo[1.1.1]pentane-1-carboxylic acid (87.9 mg, 0.387 mmol) in dichloromethane (2.0 mL) at room temperature. After 25 min, the resulting mixture was concentrated under reduced pressure. 6,6'-(((2,2'-Dimethyl-[1,1'-biphenyl]-3,3'-diyl)bis(methylene))bis(oxy))bis(5-chloro-2-methoxynicotinaldehyde) (15 mg, 0.026 mmol), N,N-diisopropylethylamine (0.135 mL, 0.774 mmol), N,N-dimethylformamide (1.5 mL), and acetic acid (0.2 mL) were added sequentially, and the resulting mixture was stirred at room temperature. After 5 min, sodium triacetoxyborohydride (54.7, 0.258 mmol) was added. After 7 min, trifluoroacetic acid (0.2 mL) was added. The resulting mixture was purified by reverse phase preparative HPLC (0.1% trifluoroacetic acid in acetonitrile/water) to give 3,3'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(bicyclo[1.1.1]pentane-1-carboxylic acid). $^1$H NMR (400 MHz, Methanol-d4) δ 7.82 (s, 2H), 7.53-7.39 (m, 2H), 7.23 (t, J=7.6 Hz, 2H), 7.07 (d, J=7.5 Hz, 2H), 5.59 (s, 4H), 4.09 (s, 4H), 4.05 (s, 6H), 2.37 (s, 12H), 2.08 (s, 6H); LRMS: 803.1.

Example 86: (2S,2'S)-2,2'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(2-phenylacetic acid) (or (2S,2'S)-2,2'-(((6,6'-(((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(2-phenylacetic acid))

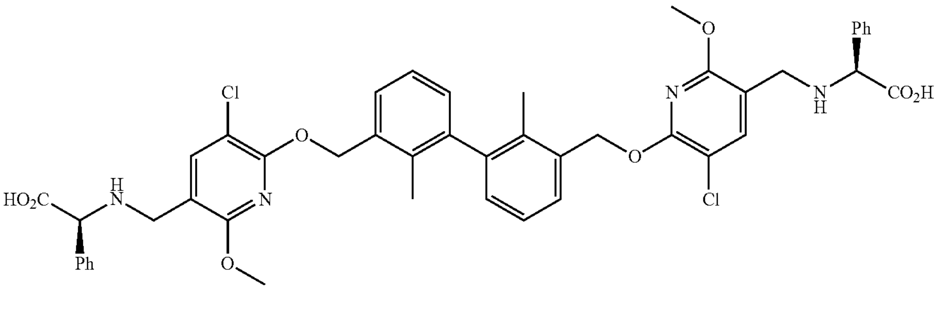 [SMILES: COc1nc(OCc2cccc(-c3cccc(COc4nc(OC)c(CN[C@H](C(=O)O)c5ccccc5)cc4Cl)c3C)c2C)c(Cl)cc1CN[C@H](C(=O)O)c1ccccc1]

A solution of 6,6'-(((2,2'-dimethyl-[1,1'-biphenyl]-3,3'-diyl)bis(methylene))bis(oxy))bis(5-chloro-2-methoxynicotinaldehyde) (7.0 mg, 0.012 mmol) in N,N-dimethylformamide (1.0 mL) was added via syringe to a stirred mixture of (S)-2-amino-2-phenylacetic acid (18.2 mg, 0.120 mmol) and aqueous sodium hydroxide solution (0.120 mL, 0.120 mmol) at room temperature. After 30 min, sodium triacetoxyborohydride (25.5 mg, 0.120 mmol) was added. After 40 min, the resulting mixture was heated to 85° C. After 180 min, the reaction mixture was cooled to room temperature and trifluoroacetic acid (0.2 mL) was added. The resulting mixture was purified by reverse phase preparative HPLC (0.1% trifluoroacetic acid in acetonitrile/water) to give (2S,2'S)-2,2'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(2-phenylacetic acid). $^1$H NMR (400 MHz, Methanol-d4) δ 7.70 (s, 2H), 7.47 (s, 14H), 7.23 (d, J=7.6 Hz, 2H), 7.07 (d, J=7.6 Hz, 2H), 5.57 (s, 4H), 4.87 (s, 2H), 4.12 (d, J=15.6 Hz, 2H), 4.09 (d, J=15.6 Hz, 2H), 3.98 (s, 6H), 2.08 (s, 6H); LRMS: 851.0.

Example 87: 3,3'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(oxetane-3-carboxylic acid) (or 3,3'-(((6,6'-(((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(oxetane-3-carboxylic acid))

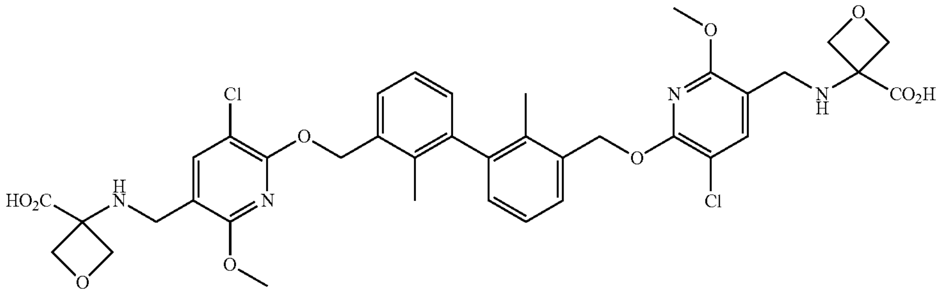 [SMILES: COc1nc(OCc2cccc(-c3cccc(COc4nc(OC)c(CNC5(C(=O)O)COC5)cc4Cl)c3C)c2C)c(Cl)cc1CNC1(C(=O)O)COC1]

3,3'-((((((2,2'-Dimethyl-[1,1'-biphenyl]-3,3'-diyl)bis(methylene))bis(oxy))bis(5-chloro-2-methoxypyridine-6,3-diyl))bis(methylene))bis(azanediyl))bis(oxetane-3-carboxylic acid) was synthesized using general reductive amination procedure C using 3-aminooxetane-3-carboxylic acid (6 equiv) and triethylamine (10 equiv) in place of (S)-3-aminobutanoic acid. $^1$H NMR (400 MHz, Methanol-d4) δ 7.83 (s, 2H), 7.47 (d, J=7.3 Hz, 2H), 7.24 (t, J=7.6 Hz, 2H), 7.07 (dd, J=7.7, 1.4 Hz, 2H), 5.60 (s, 4H), 5.03 (d, J=7.9 Hz, 4H), 4.78 (d, J=7.9 Hz, 4H), 4.21 (s, 4H), 4.06 (s, 6H), 2.08 (s, 6H); LRMS: 805.2 ($[M+Na]^+$).

Example 88: (2S,2'S)-2,2'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(N-methylpropanamide) (or (2R,2'R)-2,2'-(((6,6'-(((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(N-methylpropanamide))

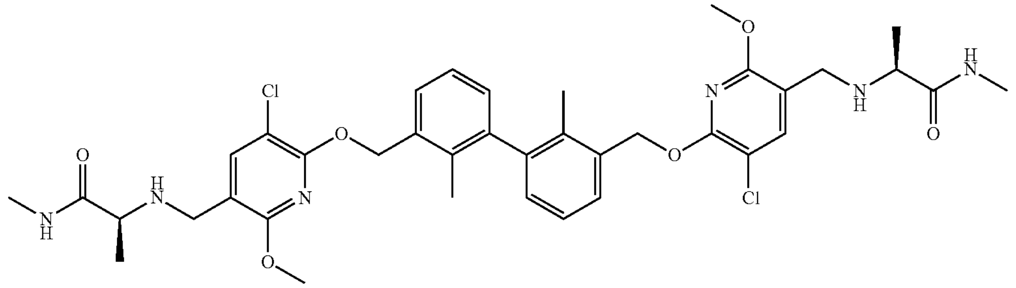

(2S,2'S)-2,2'-((((((2,2'-Dimethyl-[1,1'-biphenyl]-3,3'-diyl)bis(methylene))bis(oxy))bis(5-chloro-2-methoxypyridine-6,3-diyl))bis(methylene))bis(azanediyl))bis(N-methylpropanamide) was synthesized using general reductive amination procedure D using (S)-2-amino-N-methylpropanamide hydrochloride (15 equiv) and N,N-diisopropylethylamine (17 equiv) in place of (1R,2R)-2-aminocyclopentane-1-carboxylic acid. $^1$H NMR (400 MHz, Methanol-d4) δ 7.77 (s, 2H), 7.47 (d, J=7.6 Hz, 2H), 7.24 (t, J=7.6 Hz, 2H), 7.07 (d, J=7.6 Hz, 2H), 5.59 (s, 4H), 4.08 (d, J=3.4 Hz, 4H), 4.05 (s, 6H), 3.82 (q, J=7.0 Hz, 2H), 2.76 (s, 6H), 2.09 (s, 6H), 1.50 (d, J=7.0 Hz, 6H); LRMS: 753.3.

Example 89: Dimethyl 2,2'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))(2R,2'R)-dipropionate (or (2R,2'R)-dimethyl 2,2'-(((6,6'-(((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))dipropionate)

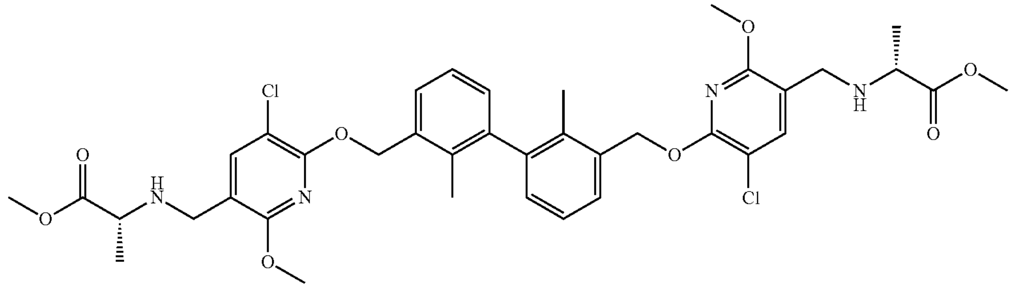

Dimethyl 2,2'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))(2R,2'R)-dipropionate was synthesized using general reductive amination procedure C using methyl D-alaninate hydrochloride (12.5 equiv) and N,N-diisopropylethylamine (20 equiv) in place of (S)-3-aminobutanoic acid. $^1$H NMR (400 MHz, Methanol-d4) δ 7.80 (s, 2H), 7.47 (dd, J=7.5, 1.3 Hz, 2H), 7.24 (t, J=7.6 Hz, 2H), 7.10-7.04 (m, 2H), 5.60 (s, 4H), 4.18 (s, 4H), 4.14 (q, J=7.2 Hz, 2H), 4.05 (s, 6H), 3.84 (s, 6H), 2.09 (s, 6H), 1.58 (d, J=7.2 Hz, 6H); LRMS: 755.3.

Example 90: (2R,2'R)-2,2'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))dipropionic acid (or (2R,2'R)-2,2'-(((6,6'-(((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))dipropionic acid)

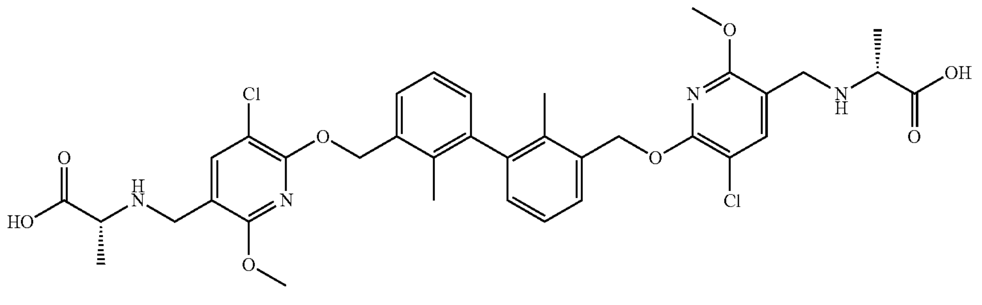 [SMILES: COc1nc(OCc2cccc(-c3cccc(COc4nc(OC)c(CN[C@H](C)C(=O)O)cc4Cl)c3C)c2C)c(Cl)cc1CN[C@H](C)C(=O)O]

Aqueous sodium hydroxide solution (1 M, 0.55 mL) was added via syringe to a stirred solution of dimethyl 2,2'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))(2R,2'R)-dipropionate (17 mg, 0.023 mmol) in dimethylsulfoxide at room temperature. After 120 min, trifluoroacetic acid (0.2 mL) was added. The resulting mixture was purified by reverse phase preparative HPLC (0.1% trifluoroacetic acid in acetonitrile/water) to give (2R,2'R)-2,2'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))dipropionic acid. $^1$H NMR (400 MHz, Methanol-$d_4$) δ 7.80 (s, 2H), 7.47 (d, J=7.6 Hz, 2H), 7.24 (t, J=7.6 Hz, 2H), 7.07 (d, J=7.5 Hz, 2H), 5.59 (s, 4H), 4.15 (s, 4H), 4.04 (s, 6H), 3.88 (q, J=7.2 Hz, 2H), 2.08 (s, 6H), 1.56 (d, J=7.2 Hz, 6H); LRMS: 727.1.

Example 91: 1,1'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(cyclopropane-1-carboxylicacid)(or 1,1'-(((6,6'-(((2,2'-dimethyl-[1,1'-biphenyl]-3,3'-diyl)bis(methylene))bis(oxy))bis(5-chloro-2-methoxy-pyridine-6,3-diyl))bis(methylene))bis(azanediyl))bis(cyclopropane-1-carboxylic acid))

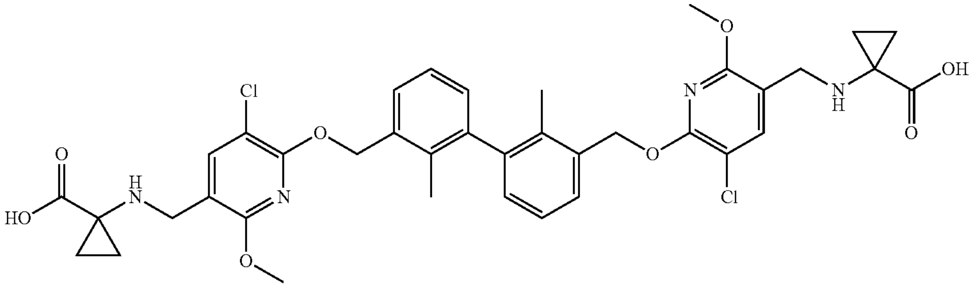 [SMILES: COc1nc(OCc2cccc(-c3cccc(COc4nc(OC)c(CNC5(C(=O)O)CC5)cc4Cl)c3C)c2C)c(Cl)cc1CNC1(C(=O)O)CC1]

1,1'-((((((2,2'-Dimethyl-[1,1'-biphenyl]-3,3'-diyl)bis(methylene))bis(oxy))bis(5-chloro-2-methoxypyridine-6,3-diyl))bis(methylene))bis(azanediyl))bis(cyclopropane-1-carboxylicacid) was synthesized as in Example 89 using methyl 1-aminocyclopropane-1-carboxylate (12.5 equiv) in place of methyl D-alaninate hydrochloride (12.5 equiv) and N,N-diisopropylethylamine (20 equiv). $^1$H NMR (400 MHz, Methanol-$d_4$) δ 7.80 (s, 2H), 7.46 (d, J=7.6 Hz, 2H), 7.23 (t, J=7.6 Hz, 2H), 7.06 (d, J=7.3 Hz, 2H), 5.59 (s, 4H), 4.32 (s, 4H), 4.04 (s, 6H), 2.07 (s, 6H), 1.62-1.45 (m, 4H), 1.38-1.27 (m, 4H); LRMS: 749.3 ([M−H]$^-$).

Example 92: (S)-4-((4-((4"-(2-(((S)-3-carboxy-2-hydroxypropyl)amino)ethoxy)-2,2'-dimethyl-3"-nitro-[1,1':3',1"-terphenyl]-3-yl)methoxy)-5-chloro-2-((5-cyanopyridin-3-yl)methoxy)benzyl)amino)-3-hydroxybutanoic acid

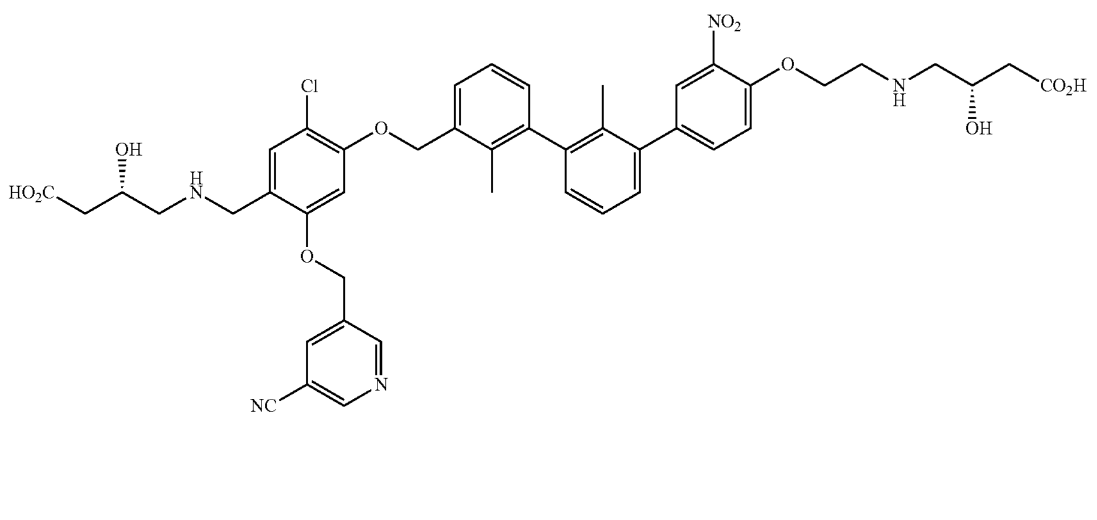 [SMILES: Cc1c(COc2cc(OCc3cncc(C#N)c3)c(CNC[C@@H](O)CC(=O)O)cc2Cl)cccc1-c1cccc(-c2ccc(OCCNC[C@@H](O)CC(=O)O)c([N+](=O)[O-])c2)c1C]

(S)-4-((4-((4"-(2-(((S)-3-carboxy-2-hydroxypropyl)amino)ethoxy)-2,2'-dimethyl-3"-nitro-[1,1':3',1"-terphenyl]-3-yl)methoxy)-5-chloro-2-((5-cyanopyridin-3-yl)methoxy)benzyl)amino)-3-hydroxybutanoic acid was synthesized using general reductive amination procedure D using 5-((4-chloro-5-((2,2'-dimethyl-3"-nitro-4"-(2-oxoethoxy)-[1,1':3',1"-terphenyl]-3-yl)methoxy)-2-formylphenoxy)methyl)nicotinonitrile in place of 6,6'-(((2,2'-dimethyl-[1,1'-biphenyl]-3,3'-diyl)bis(methylene))bis(oxy))bis(5-chloro-2-methoxynicotinaldehyde) and using (S)-4-amino-3-hydroxybutanoic acid in place (1R,2R)-2-aminocyclopentane-1-carboxylic acid. $^1$H NMR (400 MHz, Methanol-$d_4$) δ 8.95 (d, J=2.1 Hz, 1H), 8.93 (d, J=1.9 Hz, 1H), 8.37 (s, 1H), 7.88 (d, J=2.2 Hz, 1H), 7.66 (dd, J=8.6, 2.2 Hz, 1H), 7.51 (s, 1H), 7.47 (d, J=7.5 Hz, 1H), 7.42 (d, J=8.7 Hz, 1H), 7.34 (t, J=7.6 Hz, 1H), 7.26 (q, J=7.3 Hz, 2H), 7.19-7.12 (m, 2H), 7.08 (s, 1H), 5.37 (s, 2H), 5.31 (s, 2H), 4.55 (t, J=5.0 Hz, 2H), 4.38-4.30 (m, 1H), 4.26-4.18 (m, 3H), 3.60 (t, J=5.0 Hz, 2H), 3.53-3.36 (m, 1H), 3.20 (ddd, J=12.6, 6.5, 3.4 Hz, 2H), 3.06-2.92 (m, 1H), 2.59 (dd, J=6.2, 2.4 Hz, 2H), 2.55-2.49 (m, 2H), 2.14 (s, 3H), 1.91 (s, 3H); LRMS: 868.3.

Example 93: (4-((4"-(2-(((S)-1-carboxyethyl)amino)ethoxy)-2,2'-dimethyl-3"-nitro-[1,1':3',1"-terphenyl]-3-yl)methoxy)-5-chloro-2-((5-cyanopyridin-3-yl)methoxy)benzyl)-L-alanine

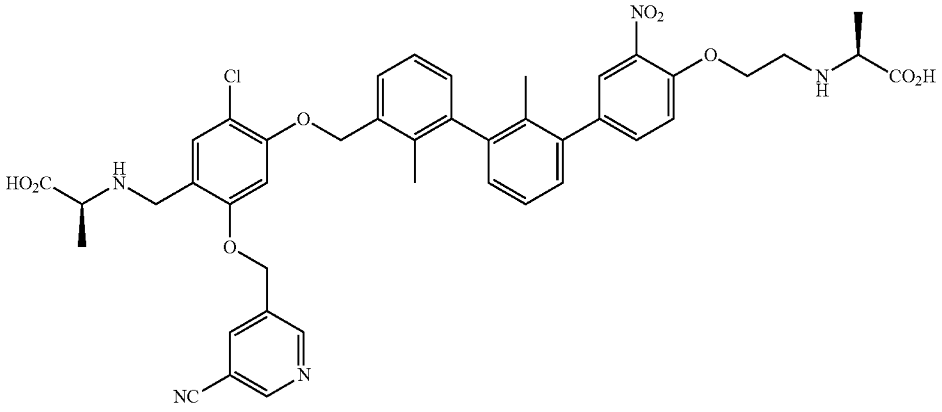

(4-((4"-(2-(((S)-1-carboxyethyl)amino)ethoxy)-2,2'-dimethyl-3"-nitro-[1,1':3',1"-terphenyl]-3-yl)methoxy)-5-chloro-2-((5-cyanopyridin-3-yl)methoxy)benzyl)-L-alanine was synthesized using general reductive amination procedure D using 5-((4-chloro-5-((2,2'-dimethyl-3"-nitro-4"-(2-oxoethoxy)-[1,1':3',1"-terphenyl]-3-yl)methoxy)-2-formylphenoxy)methyl)nicotinonitrile in place of 6,6'-(((2,2'-dimethyl-[1,1'-biphenyl]-3,3'-diyl)bis(methylene))bis(oxy))bis(5-chloro-2-methoxynicotinaldehyde) and using L-alanine in place (1R,2R)-2-aminocyclopentane-1-carboxylic acid. $^1$H NMR (400 MHz, Methanol-$d_4$) δ 8.97 (s, 1H), 8.92 (d, J=1.9 Hz, 1H), 8.40 (s, 1H), 7.89 (d, J=2.2 Hz, 1H), 7.70-7.63 (m, 1H), 7.51 (d, J=4.4 Hz, 1H), 7.47 (d, J=7.7 Hz, 1H), 7.42 (d, J=8.7 Hz, 1H), 7.34 (t, J=7.6 Hz, 1H), 7.31-7.21 (m, 2H), 7.16 (s, 1H), 7.14 (s, 1H), 7.08 (s, 1H), 5.37 (s, 2H), 5.32 (s, 2H), 4.54 (t, J=4.9 Hz, 2H), 4.36-4.15 (m, 3H), 4.01 (d, J=7.3 Hz, 1H), 3.62 (d, J=5.1 Hz, 2H), 2.14 (s, 3H), 1.92 (d, J=5.9 Hz, 3H), 1.65 (d, J=7.2 Hz, 3H), 1.54 (d, J=7.2 Hz, 3H); LRMS: 808.3.

Example 94: (S)-4-((4-((4''-(2-(((S)-3-carboxy-2-hydroxypropyl)amino)ethoxy)-2,2'-dimethyl-3''-(trifluoromethyl)-[1,1':3',1''-terphenyl]-3-yl)methoxy)-5-chloro-2-((5-cyanopyridin-3-yl)methoxy)benzyl)amino)-3-hydroxybutanoic acid

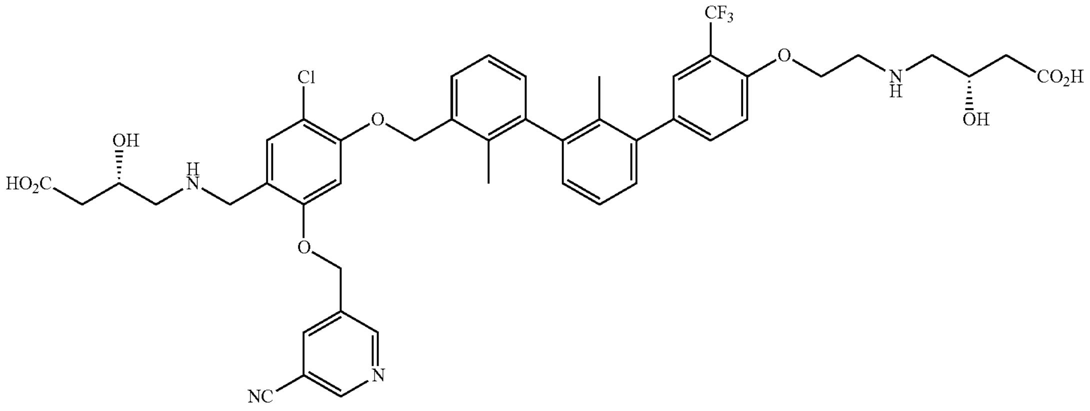

(S)-4-((4-((4''-(2-(((S)-3-Carboxy-2-hydroxypropyl)amino)ethoxy)-2,2'-dimethyl-3''-(trifluoromethyl)-[1,1':3',1''-terphenyl]-3-yl)methoxy)-5-chloro-2-((5-cyanopyridin-3-yl)methoxy)benzyl)amino)-3-hydroxybutanoic acid was synthesized using general reductive amination procedure D using 5-((4-chloro-5-((2,2'-dimethyl-3''-(trifluoromethyl)-4''-(2-oxoethoxy)-[1,1':3',1''-terphenyl]-3-yl)methoxy)-2-formylphenoxy)methyl)nicotinonitrile in place of 6,6'-(((2,2'-dimethyl-[1,1'-biphenyl]-3,3'-diyl)bis(methylene))bis(oxy))bis(5-chloro-2-methoxynicotinaldehyde) and using (S)-4-amino-3-hydroxybutanoic acid in place (1R,2R)-2-aminocyclopentane-1-carboxylic acid. $^1$H NMR (400 MHz, Methanol-$d_4$) δ 8.95 (s, 1H), 8.93 (s, 1H), 8.37 (s, 1H), 7.61 (d, J=9.3 Hz, 1H), 7.58 (s, 1H), 7.53-7.44 (m, 3H), 7.41-7.06 (m, 6H), 5.37 (s, 2H), 5.33 (d, J=14.4 Hz, 2H), 4.49 (t, J=5.1 Hz, 2H), 4.37-4.27 (m, 1H), 4.26-4.17 (m, 3H), 3.60 (t, J=5.0 Hz, 2H), 3.44-3.37 (m, 1H), 3.29-3.14 (m, 2H), 3.05-2.89 (m, 1H), 2.56 (d, J=6.3 Hz, 2H), 2.51 (d, J=6.2 Hz, 2H), 2.14 (s, 3H), 1.88 (s, 3H); LRMS: 891.2.

Example 95: (4-((4''-(2-(((S)-1-carboxyethyl)amino)ethoxy)-2,2'-dimethyl-3''-(trifluoromethyl)-[1,1':3',1''-terphenyl]-3-yl)methoxy)-5-chloro-2-((5-cyanopyridin-3-yl)methoxy)benzyl)-L-alanine

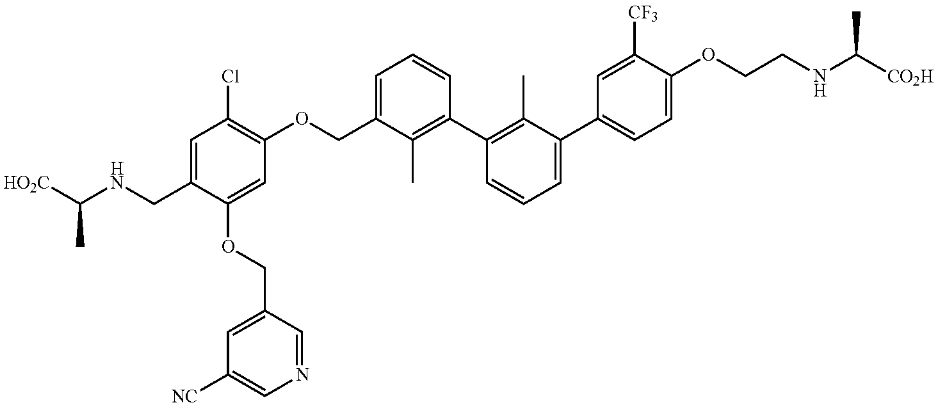 [SMILES: Cc1c(COc2cc(OCc3cncc(C#N)c3)c(CN[C@@H](C)C(=O)O)cc2Cl)cccc1-c1cccc(-c2ccc(OCCN[C@@H](C)C(=O)O)c([N+](=O)[O-])c2)c1C]

(4-((4''-(2-(((S)-1-Carboxyethyl)amino)ethoxy)-2,2'-dimethyl-3''-(trifluoromethyl)-[1,1':3',1''-terphenyl]-3-yl)methoxy)-5-chloro-2-((5-cyanopyridin-3-yl)methoxy)benzyl)-L-alanine was synthesized using general reductive amination procedure D using 5-((4-chloro-5-((2,2'-dimethyl-3''-(trifluoromethyl)-4''-(2-oxoethoxy)-[1,1':3',1''-terphenyl]-3-yl)methoxy)-2-formylphenoxy)methyl)nicotinonitrile in place of 6,6'-(((2,2'-dimethyl-[1,1'-biphenyl]-3,3'-diyl)bis(methylene))bis(oxy))bis(5-chloro-2-methoxynicotinaldehyde) and using L-alanine in place (1R, 2R)-2-aminocyclopentane-1-carboxylic acid. $^1$H NMR (400 MHz, Methanol-$d_4$) δ 8.97 (s, 1H), 8.92 (s, 1H), 8.40 (s, 1H), 7.97 (s, 1H), 7.61 (d, J=8.5 Hz, 1H), 7.58 (s, 1H), 7.51 (d, J=4.5 Hz, 1H), 7.47 (d, J=7.8 Hz, 1H), 7.42-7.06 (m, 6H), 5.37 (s, 2H), 5.33 (d, J=10.9 Hz, 2H), 4.49 (t, J=5.1 Hz, 2H), 4.38-4.16 (m, 3H), 4.01 (q, J=7.4 Hz, 1H), 3.62 (d, J=5.5 Hz, 2H), 2.14 (s, 3H), 1.88 (s, 3H), 1.65 (d, J=7.2 Hz, 3H), 1.55 (d, J=6.2 Hz, 3H); LRMS: 831.3.

Example 96: 2-(((6-((3'-(((5-(aminomethyl)-3-chloro-6-methoxypyridin-2-yl)oxy)methyl)-2,2'-dimethyl-[1,1'-biphenyl]-3-yl)methoxy)-5-chloro-2-methoxypyridin-3-yl)methyl)amino)-2-methylpropanoic acid

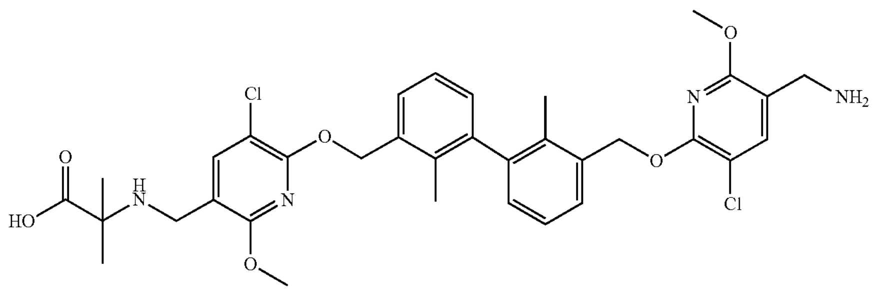 [SMILES: COc1nc(OCc2cccc(-c3cccc(COc4nc(OC)c(CNC(C)(C)C(=O)O)cc4Cl)c3C)c2C)c(Cl)cc1CN]

Trimethylsilyl trifluoromethanesulfonate (0.037 mL, 0.21 mmol) was added via syringe to a stirred mixture of 2-amino-2-methylpropanoic acid (18.6 mg, 0.181 mmol) and N,N-diisopropylethylamine (0.052 mL, 0.30 mmol) in N,N-dimethylformamide (1.0 mL) at room temperature. After 50 min, 6,6'-(((2,2'-dimethyl-[1,1'-biphenyl]-3,3'-diyl)bis(methylene))bis(oxy))bis(5-chloro-2-methoxynicotinaldehyde) (7.0 mg, 0.012 mmol) was added, and the resulting mixture was heated to reflux over 30 seconds and allowed to cool to room temperature. After 10 min, acetic acid (0.15 mL), sodium cyanoborohydride (6.81 mg, 0.108 mmol), and sodium triacetoxyborohydride (23.0 mg, 0.108 mmol) were added sequentially. After 90 min, trifluoroacetic acid (0.2 mL) was added. The resulting mixture was purified by reverse phase preparative HPLC (0.1% trifluoroacetic acid in acetonitrile/water) to give 2-(((6-((3'-(((5-(aminomethyl)-3-chloro-6-methoxypyridin-2-yl)oxy)methyl)-2,2'-dimethyl-[1,1'-biphenyl]-3-yl)methoxy)-5-chloro-2-methoxypyridin-3-yl)methyl)amino)-2-methylpropanoic acid. $^1$H NMR (400 MHz, Methanol-$d_4$) δ 7.84 (s, 1H), 7.81 (s, 1H), 7.53-7.43 (m, 2H), 7.28-7.22 (m, 2H), 7.11-7.04 (m, 2H), 5.60 (s, 4H), 4.21 (s, 2H), 4.13 (s, 2H), 4.06 (s, 3H), 4.05 (s, 3H), 2.09 (s, 3H), 2.09 (s, 3H), 1.65 (s, 6H); LRMS: 755.3.

Example 97: 2,2'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(2-methylpropanoic acid) (or 2,2'-(((6,6'-(((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(2-methylpropanoic acid))

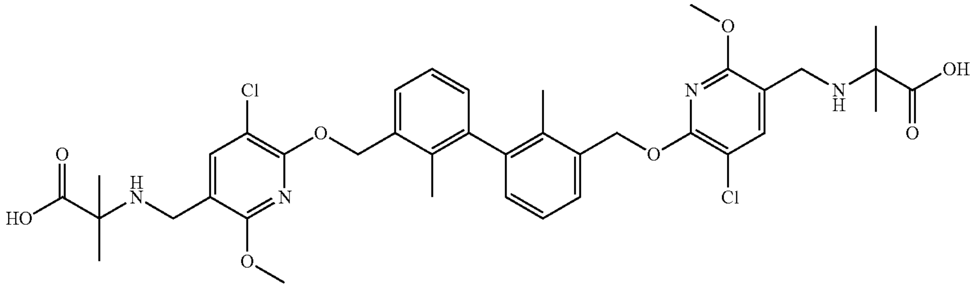 [SMILES: COc1nc(OCc2cccc(-c3cccc(COc4nc(OC)c(CNC(C)(C)C(=O)O)cc4Cl)c3C)c2C)c(Cl)cc1CNC(C)(C)C(=O)O]

2,2'-((((((2,2'-Dimethyl-[1,1'-biphenyl]-3,3'-diyl)bis(methylene))bis(oxy))bis(5-chloro-2-methoxypyridine-6,3-diyl))bis(methylene))bis(azanediyl))bis(2-methylpropanoic acid) was synthesized as described in Example 89 using methyl 2-amino-2-methylpropanoate hydrochloride in place of methyl D-alaninate hydrochloride. $^1$H NMR (400 MHz, Methanol-$d_4$) δ 7.82 (s, 2H), 7.46 (d, J=7.6 Hz, 2H), 7.23 (t, J=7.6 Hz, 2H), 7.06 (d, J=7.3 Hz, 2H), 5.60 (s, 4H), 4.10 (s, 4H), 4.04 (s, 6H), 2.08 (s, 6H), 1.60 (s, 12H); LRMS: 755.2.

Example 98: (2S,2'S)-2,2'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))dipropionic acid (or (2S,2'S)-2,2'-(((6,6'-(((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))dipropionic acid)

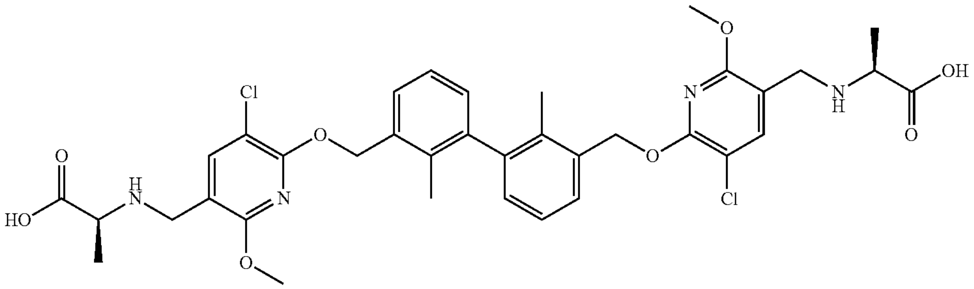 [SMILES: COc1nc(OCc2cccc(-c3cccc(COc4nc(OC)c(CN[C@@H](C)C(=O)O)cc4Cl)c3C)c2C)c(Cl)cc1CN[C@@H](C)C(=O)O]

(2S,2'S)-2,2'-((((((2,2'-Dimethyl-[1,1'-biphenyl]-3,3'-diyl)bis(methylene))bis(oxy))bis(5-chloro-2-methoxypyridine-6,3-diyl))bis(methylene))bis(azanediyl))dipropionic acid was synthesized as shown in Example 89 using methyl L-alaninate hydrochloride in place of methyl D-alaninate hydrochloride. $^1$H NMR (400 MHz, Methanol-$d_4$) δ 7.80 (s, 2H), 7.47 (d, J=7.6 Hz, 2H), 7.24 (t, J=7.6 Hz, 2H), 7.07 (d, J=7.5 Hz, 2H), 5.59 (s, 4H), 4.15 (s, 4H), 4.04 (s, 6H), 3.86 (d, J=7.2 Hz, 2H), 2.08 (s, 6H), 1.55 (d, J=7.2 Hz, 6H); LRMS: 727.0.

Example 99: (2R,2'R)-2,2'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))dibutyric acid (or (2R,2'R)-2,2'-(((6,6'-(((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))dibutyric acid)

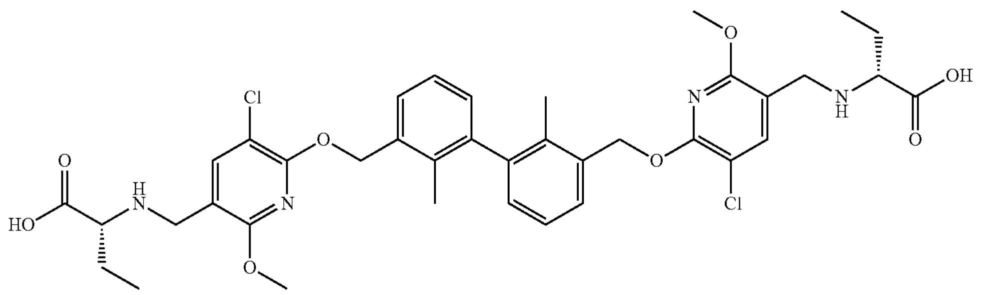 [SMILES: CC[C@@H](NCc1cc(Cl)c(OCc2cccc(-c3cccc(COc4nc(OC)c(CN[C@H](CC)C(=O)O)cc4Cl)c3C)c2C)nc1OC)C(=O)O]

(2R,2'R)-2,2'-((((((2,2'-Dimethyl-[1,1'-biphenyl]-3,3'-diyl)bis(methylene))bis(oxy))bis(5-chloro-2-methoxypyridine-6,3-diyl))bis(methylene))bis(azanediyl))dibutyricacidwassynthesizedusinggeneral reductive amination procedure D using (R)-2-aminobutanoic acid in place of (1R,2R)-2-aminocyclopentane-1-carboxylic acid. $^1$H NMR (400 MHz, Methanol-$d_4$) δ 7.79 (s, 2H), 7.47 (d, J=7.6 Hz, 2H), 7.24 (t, J=7.6 Hz, 2H), 7.07 (d, J=7.6 Hz, 2H), 5.59 (s, 4H), 4.14 (d, J=1.5 Hz, 4H), 4.04 (s, 6H), 3.72 (t, J=5.8 Hz, 2H), 2.08 (s, 6H), 2.06-1.83 (m, 4H), 1.03 (t, J=7.5 Hz, 6H); LRMS: 755.2.

Example 100: Dimethyl 2,2'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))(2S,2'S)-dipropionate (or (2S,2'S)-dimethyl 2,2'-(((6,6'-(((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))dipropionate)

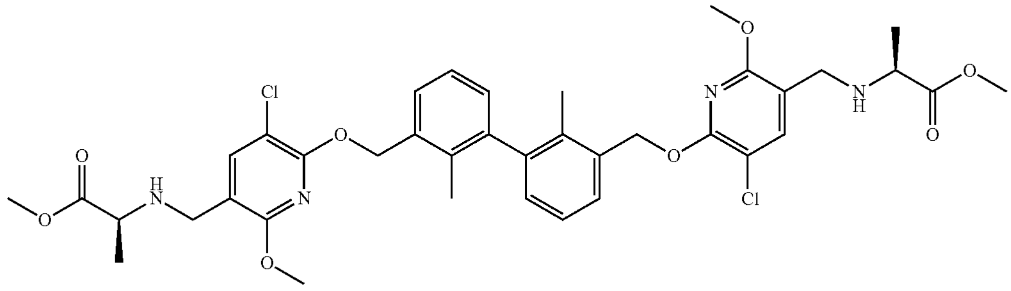

Dimethyl 2,2'-((((((2,2'-Dimethyl-[1,1'-biphenyl]-3,3'-diyl)bis(methylene))bis(oxy))bis(5-chloro-2-methoxypyridine-6,3-diyl))bis(methylene))bis(azanediyl))(2S,2'S)-dipropionate was synthesized using general reductive amination procedure C using methyl L-alaninate hydrochloride in place of methyl D-alaninate hydrochloride. $^1$H NMR (400 MHz, Methanol-$d_4$) δ 7.77 (s, 2H), 7.47 (d, J=7.7 Hz, 2H), 7.24 (t, J=7.7 Hz, 2H), 7.07 (d, J=7.6 Hz, 2H), 5.59 (s, 4H), 4.12-3.97 (m, 6H), 4.08 (s, 4H), 4.04 (s, 6H), 3.80 (s, 6H), 2.09 (s, 6H), 1.53 (d, J=7.1 Hz, 6H); LRMS: 755.2.

Example 101: (2S,2'S)-2,2'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))dipropanamide

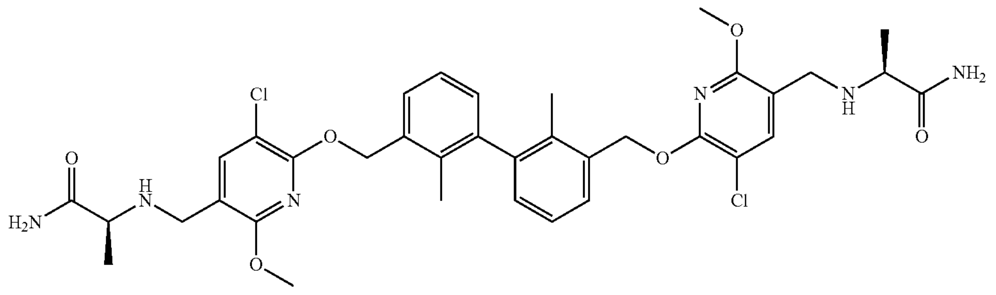 [SMILES: COc1nc(OCc2cccc(-c3cccc(COc4nc(OC)c(CN[C@@H](C)C(N)=O)cc4Cl)c3C)c2C)c(Cl)cc1CN[C@@H](C)C(N)=O]

(2S,2'S)-2,2'-((((((2,2'-Dimethyl-[1,1'-biphenyl]-3,3'-diyl)bis(methylene))bis(oxy))bis(5-chloro-2-methoxypyridine-6,3-diyl))bis(methylene))bis(azanediyl))dipropanamide was synthesized using general reductive amination procedure D using (S)-2-amino-propanamide hydrochloride (15 equiv) and N,N-diisopropylethylamine (17 equiv) in place of (1R,2R)-2-aminocyclopentane-1-carboxylic acid. $^1$H NMR (400 MHz, Methanol-$d_4$) δ 7.76 (s, 2H), 7.47 (d, J=7.6 Hz, 2H), 7.24 (t, J=7.6 Hz, 2H), 7.07 (d, J=7.6 Hz, 2H), 5.58 (s, 4H), 4.04 (s, 10H), 3.83-3.73 (m, 2H), 2.08 (s, 6H), 1.50 (d, J=7.0 Hz, 6H); LRMS: 725.3.

Example 102: (S)-((6-((4-(4'-(2-((2-hydroxyethyl)amino)ethoxy)-2-methyl-[1,1'-biphenyl]-3-yl)-2,3-dihydro-1H-inden-1-yl)oxy)-2-methoxypyridin-3-yl)methyl)glycine

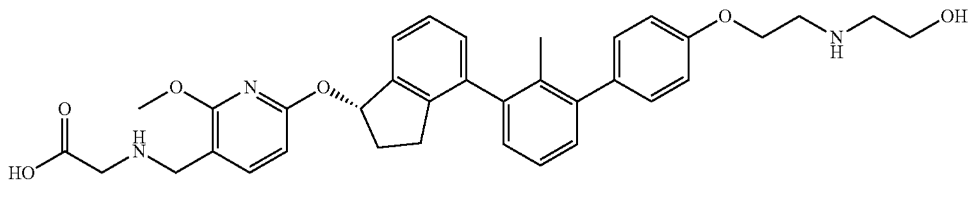 [SMILES: COc1nc(O[C@H]2CCc3c(-c4cccc(-c5ccc(OCCNCCO)cc5)c4C)cccc32)ccc1CNCC(=O)O]

Lithium tetrafluoroborate (38.4 mg, 0.410 mmol) was added to a stirred solution of tert-butyl (S)-((6-((4-(4'-(2,2-diethoxyethoxy)-2-methyl-[1,1'-biphenyl]-3-yl)-2,3-dihydro-1H-inden-1-yl)oxy)-2-methoxypyridin-3-yl)methyl) glycinate (28 mg, 0.041 mmol) in acetonitrile (1.5 mL) and water (0.1 mL) at room temperature, and the resulting mixture was heated to 60° C. After 65 min, the reaction mixture was heated to 79° C. After 75 min, the reaction mixture was allowed to cool to room temperature. Dimethylsulfoxide (0.5 mL), ethanolamine (0.025 mL, 0.41 mmol), N,N-diisopropylethylamine (0.071 mL, 0.41 mmol), and acetic acid (0.15 mL) were added sequentially. After 15 min, sodium triacetoxyborohydride (212 mg, 0.41 mmol) was added. After 30 min, trifluoroacetic acid (0.1 mL) was added. The resulting mixture was purified by reverse phase preparative HPLC (0.1% trifluoroacetic acid in acetonitrile/water) to give tert-butyl (S)-((6-((4-(4'-(2-((2-hydroxyethyl)amino)ethoxy)-2-methyl-[1,1'-biphenyl]-3-yl)-2,3-dihydro-1H-inden-1-yl)oxy)-2-methoxypyridin-3-yl)methyl) glycinate, which was immediately dissolved in dimethylsulfoxide (1.5 mL). The resulting mixture was stirred at room temperature, and aqueous sodium hydroxide solution (1 M, 0.5 mL) was added. After 30 min, trifluoroacetic acid (0.1 mL) was added. The resulting mixture was purified by reverse phase preparative HPLC (0.1% trifluoroacetic acid in acetonitrile/water) to give (S)-((6-((4-(4'-(2-((2-hydroxyethyl)amino)ethoxy)-2-methyl-[1,1'-biphenyl]-3-yl)-2,3-dihydro-1H-inden-1-yl)oxy)-2-methoxypyridin-3-yl)methyl)glycine. $^1$H NMR (400 MHz, Methanol-$d_4$) δ 7.67 (d, J=8.2 Hz, 1H), 7.49-7.21 (m, 5H), 7.21-7.01 (m, 5H), 6.59 (t, J=5.6 Hz, 1H), 6.42 (d, J=8.0 Hz, 1H), 4.35 (t, J=5.0 Hz, 2H), 4.22 (s, 2H), 4.08 (s, 3H), 3.91-3.79 (m, 2H), 3.87 (s, 2H), 3.53 (t, J=5.0 Hz, 2H), 3.26 (t, J=5.3 Hz, 2H), 3.00-2.53 (m, 3H), 2.65 (s, 3H), 2.21-2.07 (m, 1H); LRMS: 620.2 ([M+Na]$^+$).

Example 103: (S)-4-((2-((3'-((S)-1-((5-(((carboxymethyl)amino)methyl)-6-methoxypyridin-2-yl)oxy)-2,3-dihydro-1H-inden-4-yl)-2'-methyl-[1,1'-biphenyl]-4-yl)oxy)ethyl)amino)-3-hydroxybutanoic acid

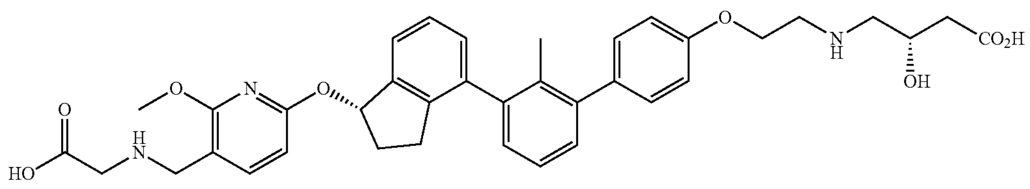 [SMILES: COc1nc(O[C@H]2CCc3c(-c4cccc(-c5ccc(OCCNC[C@@H](O)CC(=O)O)cc5)c4C)cccc32)ccc1CNCC(=O)O]

(S)-4-((2-((3'-((S)-1-((5-(((Carboxymethyl)amino)methyl)-6-methoxypyridin-2-yl)oxy)-2,3-dihydro-1H-inden-4-yl)-2'-methyl-[1,1'-biphenyl]-4-yl)oxy)ethyl)amino)-3-hydroxybutanoic acid was synthesized in a manner similar to Example 102 using (S)-4-amino-3-hydroxybutanoic acid in place of ethanolamine. $^1$H NMR (400 MHz, Methanol-$d_4$) δ 7.68 (d, J=8.1 Hz, 1H), 7.41 (t, J=9.7 Hz, 1H), 7.36-6.96 (m, 9H), 6.59 (d, J=6.0 Hz, 1H), 6.42 (d, J=8.0 Hz, 1H), 4.39-4.31 (m, 3H), 4.22 (s, 2H), 4.08 (s, 3H), 3.89 (s, 2H), 3.57-3.51 (m, 2H), 3.39-3.29 (m, 1H), 3.20-3.02 (m, 1H), 3.02-2.42 (m, 8H), 2.25-2.06 (m, 1H); LRMS: 656.2.

Example 104: (2R,2'R,3S,3'S)-2,2'-((((2,2'-dimethyl-[1,1'-biphenyl]-3,3'-diyl)bis(methylene))bis(oxy))bis(5-chloro-2-methoxypyridine-6,3-diyl))bis(pyrrolidine-3-carboxylic acid) (or (2R,2'R,3S,3'S)-2,2'-(6,6'-(((2,2'-dimethyl-[1,1'-biphenyl]-3,3'-diyl)bis(methylene))bis(oxy))bis(5-chloro-2-methoxypyridine-6,3-diyl))bis(pyrrolidine-3-carboxylic acid))

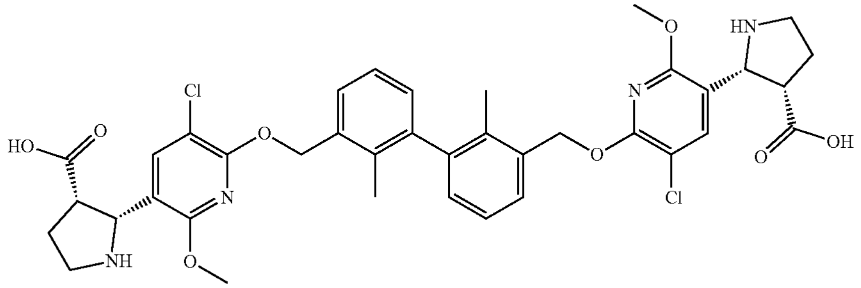 [SMILES: COc1nc(OCc2cccc(-c3cccc(COc4nc(OC)c([C@@H]5NCC[C@@H]5C(=O)O)cc4Cl)c3C)c2C)c(Cl)cc1[C@@H]1NCC[C@@H]1C(=O)O]

Example 105: (2R,3S)-2-(6-((3'-(((5-((2R,3S)-3-((allyloxy)carbonyl)pyrrolidin-2-yl)-3-chloro-6-methoxypyridin-2-yl)oxy)methyl)-2,2'-dimethyl-[1,1'-biphenyl]-3-yl)methoxy)-5-chloro-2-methoxypyridin-3-yl)pyrrolidine-3-carboxylic acid

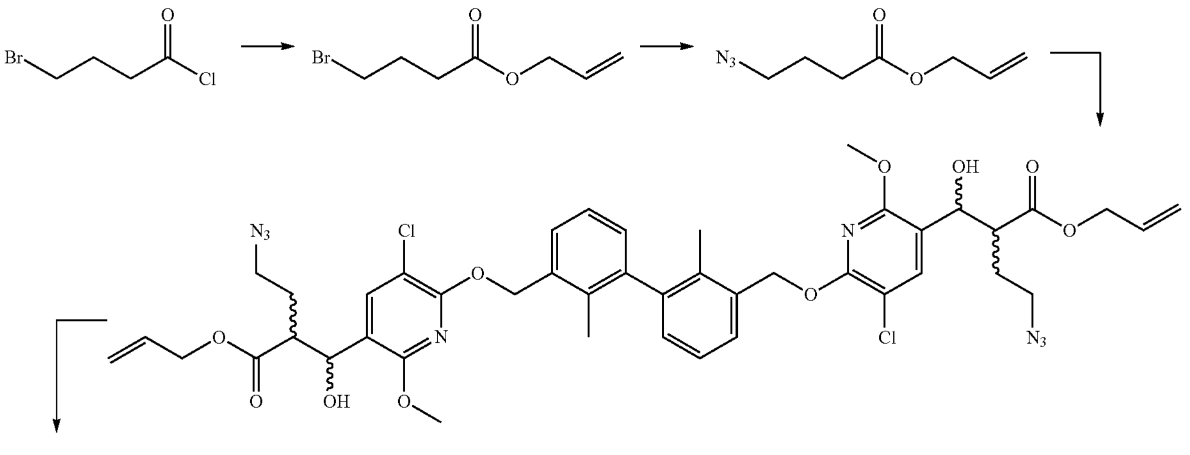

-continued

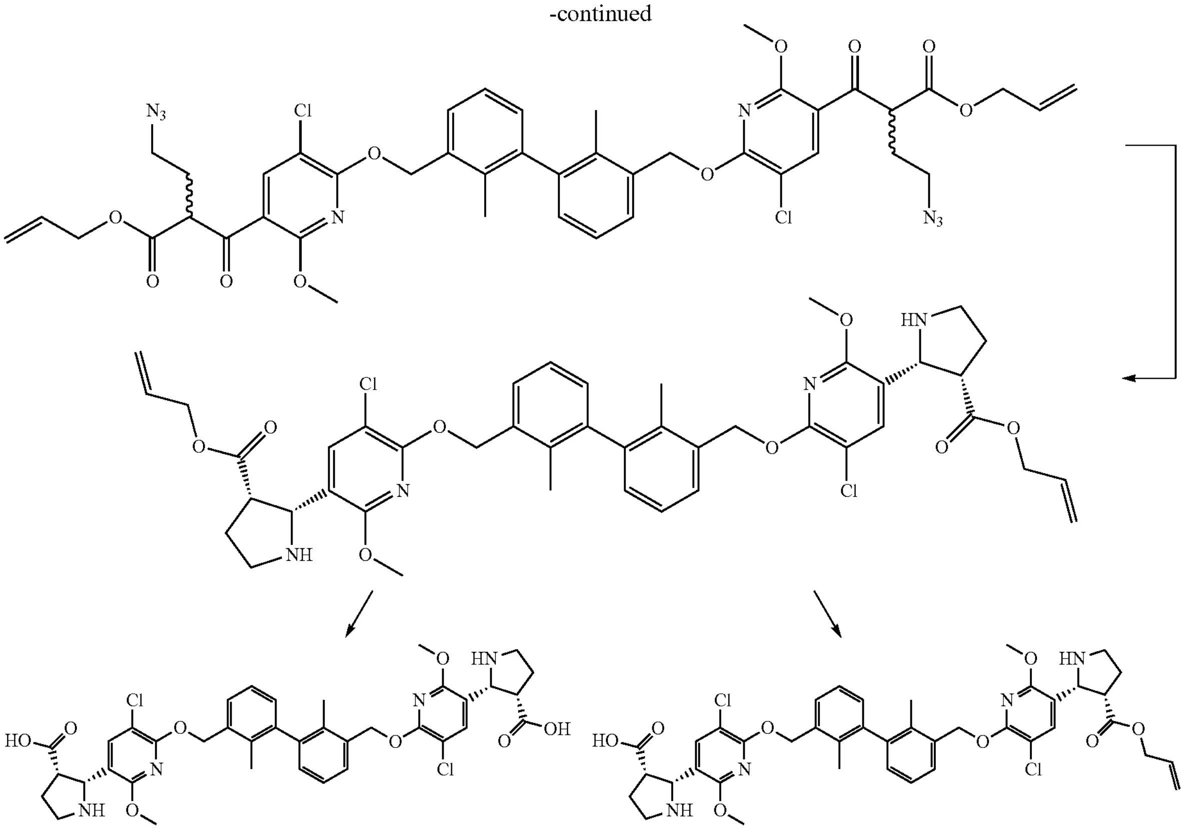

Step 1: 4-Bromobutanoyl chloride (2.00 mL, 17.3 mmol) was added via syringe to a stirred mixture of allyl alcohol (2.94 mL, 43.2 mmol) and 2,6-lutidine (3.02 mL, 25.9 mmol) in tetrahydrofuran (35 mL) at 0° C., and the resulting mixture was allowed to warm to room temperature. After 90 min, diethyl ether (250 mL) was added, and the organic layer was washed sequentially with aqueous hydrogen chloride solution (2×150 mL), saturated aqueous sodium bicarbonate solution (100 mL), and water (100 mL), was dried over anhydrous magnesium sulfate, was filtered, and was concentrated under reduced pressure to give allyl 4-bromobutanoate, which was used in the next step without further purification.

Step 2: A stirred mixture of allyl 4-bromobutanoate (3.58 g, 17.3 mmol) and sodium azide (1.69 g, 25.9 mmol) in dimethylsulfoxide (30 mL) was heated to 65° C. After 20 h, the reaction mixture was allowed to cool to room temperature, and diethyl ether (600 mL) was added. The organic layer was washed with water (2×500 mL), was dried over anhydrous magnesium sulfate, was filtered, and was concentrated under reduced pressure. The residue was purified by flash column chromatography (0 to 5% ethyl acetate in hexanes) to give allyl 4-azidobutanoate.

Step 3: Allyl 4-azidobutanoate (0.086 mL, 0.516 mmol) was added dropwise via syringe over 2 min to a solution of lithium diisopropyl amide (2.0 M in tetrahydrofuran/heptane/ethylbenzene, 0.318 mL, 0.64 mmol) in tetrahydrofuran (3.0 mL) at −78° C. After 40 min, a solution of 6,6'-(((2,2'-dimethyl-[1,1'-biphenyl]-3,3'-diyl)bis(methylene))bis(oxy))bis(5-chloro-2-methoxynicotinaldehyde) (100 mg, 0.172 mmol) in tetrahydrofuran (3.0 mL). After 40 min, a mixture of acetic acid (0.5 mL) and tetrahydrofuran (1.0) mL was added, and the resulting mixture was allowed to warm to room temperature. Ethyl acetate (60 mL) was added, and the organic layer was washed sequentially with saturated aqueous ammonium chloride solution (40 mL) and a 1:1 mixture of saturated aqueous sodium bicarbonate solution and brine (1:1 v:v, 30 mL), was dried over sodium sulfate, was filtered, and was concentrated under reduced pressure. The residue was purified by flash column chromatography (0 to 50% ethyl acetate in hexanes) to give diallyl 2,2'-(((((2,2'-dimethyl-[1,1'-biphenyl]-3,3'-diyl)bis(methylene))bis(oxy))bis(5-chloro-2-methoxypyridine-6,3-diyl))bis(hydroxymethylene))bis(4-azidobutanoate).

Step 4: Dess-Martin periodinane (219 mg, 0.516 mmol) was added to a stirred solution of diallyl 2,2'-(((((2,2'-dimethyl-[1,1'-biphenyl]-3,3'-diyl)bis(methylene))bis(oxy))bis(5-chloro-2-methoxypyridine-6,3-diyl))bis(hydroxymethylene))bis(4-azidobutanoate) (158 mg, 0.172 mmol) in dichloromethane (2.0 mL) at room temperature. After 150 min, aqueous sodium thiosulfate solution (1 M, 1 mL), saturated aqueous sodium bicarbonate solution (10 mL), and ethyl acetate (60 mL) were added sequentially. The organic layer was washed with saturated aqueous sodium bicarbonate solution (2×30 mL), was dried over sodium sulfate, was filtered, and was concentrated under reduced pressure. The residue was purified by flash column chromatography (0 to 50% ethyl acetate in hexanes) to give diallyl 2,2'-(6,6'-(((2,2'-dimethyl-[1,1'-biphenyl]-3,3'-diyl)bis(methylene))bis(oxy))bis(5-chloro-2-methoxynicotinoyl))bis(4-azidobutanoate).

Step 5: Triphenylphosphine (99.2 mg, 0.378 mmol) was added to a stirred solution of diallyl 2,2'-(6,6'-(((2,2'-dimethyl-[1,1'-biphenyl]-3,3'-diyl)bis(methylene))bis(oxy))bis(5-chloro-2-methoxynicotinoyl))bis(4-azidobutanoate) (158 mg, 0.172 mmol) in tetrahydrofuran (2.0 mL) and water (0.015 mL) at room temperature, and the resulting mixture was heated to 65° C. After 50 min, the reaction mixture was cooled to 0° C. over 5 min. Acetonitrile (6.0 mL) and acetic acid (0.4 mL) were added sequentially. After 5 min, sodium triacetoxyborohydride (365 mg, 1.72 mmol) was added, and the resulting mixture was allowed to warm slowly to room temperature over 14 h. Ethyl acetate (80 mL) was added, and the organic layer was washed sequentially with a mixture of water and saturated aqueous sodium carbonate solution (5:1 v:v, 60 mL), saturated aqueous sodium bicarbonate solution (50 mL), and brine (50 mL), was dried over anhydrous sodium sulfate, was filtered, and was concentrated under reduced pressure. The residue was purified by flash column chromatography (0 to 100% ethyl acetate in hexanes, then 0 to 10% methanol in dichloromethane) to give di-allyl 2,2'-((((2,2'-dimethyl-[1,1'-biphenyl]-3,3'-diyl)bis(methylene)) bis(oxy))bis(5-chloro-2-methoxypyridine-6,3-diyl))(2R, 2'R,3S,3'S)-bis(pyrrolidine-3-carboxylate) as a mixture of stereoisomers in which the relative stereochemistry of vicinal substituents on all pyrrolidine rings were cis.

Step 6: Tetrakis(triphenylphosphine)palladium(0) (20 mg, 0.017 mmol) was added to a stirred mixture of di-allyl 2,2'-((((2,2'-dimethyl-[1,1'-biphenyl]-3,3'-diyl)bis(methylene))bis(oxy))bis(5-chloro-2-methoxypyridine-6,3-diyl)) (2R,2'R,3S,3'S)-bis(pyrrolidine-3-carboxylate) (mixture of stereoisomers in which the relative stereochemistry of vicinal substituents on all pyrrolidine rings were cis, 143 mg, 0.172 mmol), triphenylphosphine (9.0 mg, 0.034 mmol), and pyrrolidine (0.287 mL, 3.44 mmol) in acetonitrile (5.0 mL) at 0 C. After 24 min, the reaction mixture was allowed to warm to room temperature. After 136 min, tetrakis (triphenylphosphine)palladium(0) (60 mg, 0.051 mmol) was added. After 45 min, tetrakis(triphenylphosphine)palladium (0) (60 mg, 0.051 mmol) was added. After 12 h, the reaction mixture was concentrated under reduced pressure. N,N-dimethylformamide (1.0 mL), water (0.2 mL), and trifluoroacetic acid (0.2 mL) were added sequentially, and the resulting mixture was purified by reverse phase preparative HPLC (0.1% trifluoroacetic acid in acetonitrile/water) to give (2R,2'R,3S,3'S)-2,2'-((((2,2'-dimethyl-[1,1'-biphenyl]-3,3'-diyl)bis(methylene))bis(oxy))bis(5-chloro-2-methoxypyridine-6,3-diyl))bis(pyrrolidine-3-carboxylic acid) as a mixture of stereoisomers in which the relative stereochemistry of vicinal substituents on all pyrrolidine rings were cis ($^1$H NMR (400 MHz, Methanol-$d_4$) δ 7.77 (s, H), 7.46 (d, J=7.7 Hz, 2H), 7.24 (t, J=7.6 Hz, 2H), 7.08 (d, J=7.6 Hz, 2H), 5.57 (s, 4H), 4.93 (d, J=7.1 Hz, 2H), 4.03 (s, 6H), 3.68 (dt, J=11.6, 7.8 Hz, 2H), 3.63-3.55 (m, 2H), 3.55-3.43 (m, 2H), 2.46 (q, J=7.8 Hz, 4H), 2.08 (s, 6H); LRMS: 751.2) and (2R,3S)-2-(6-((3'-(((5-((2R,3S)-3-((allyloxy)carbonyl)pyrrolidin-2-yl)-3-chloro-6-methoxypyridin-2-yl)oxy)methyl)-2,2'-dimethyl-[1,1'-biphenyl]-3-yl)methoxy)-5-chloro-2-methoxypyridin-3-yl)pyrrolidine-3-carboxylic acid as a mixture of stereoisomers in which the relative stereochemistry of vicinal substituents on all pyrrolidine rings were cis. ($^1$H NMR (400 MHz, Methanol-$d_4$) δ 7.76 (d, J=1.1 Hz, 2H), 7.72-6.89 (m, 6H), 6.26-6.15 (m, 1H), 5.68-5.53 (m, 6H), 4.93 (d, J=7.0 Hz, 2H), 4.05-3.97 (m, 7H), 3.80-3.38 (m, 6H), 2.54-2.40 (m, 2H), 2.09 (s, 6H); LRMS: 791.2).

Example 106: (3S,3'S)-4,4'-((((2',2''-dimethyl-[1,1':3',1'':3'',1'''-quaterphenyl]-4,4'''-diyl)bis(oxy))bis(ethane-2,1-diyl))bis(azanediyl))bis(3-hydroxybutanoic acid)

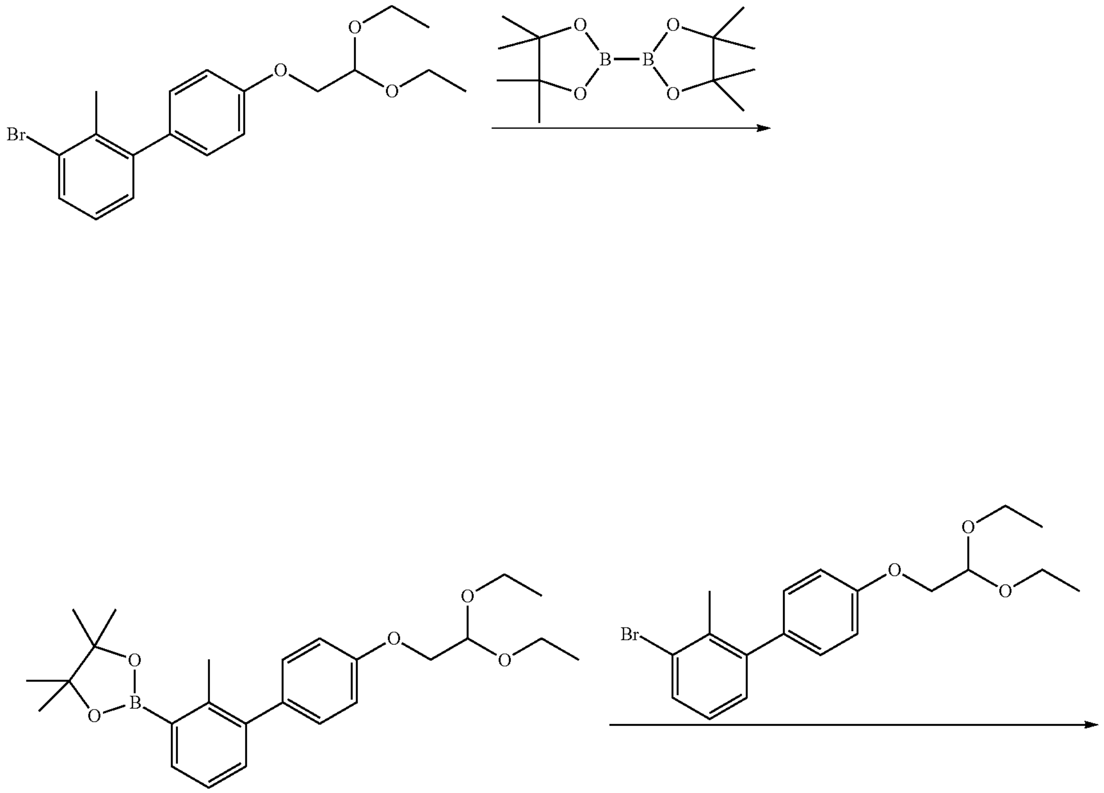

-continued

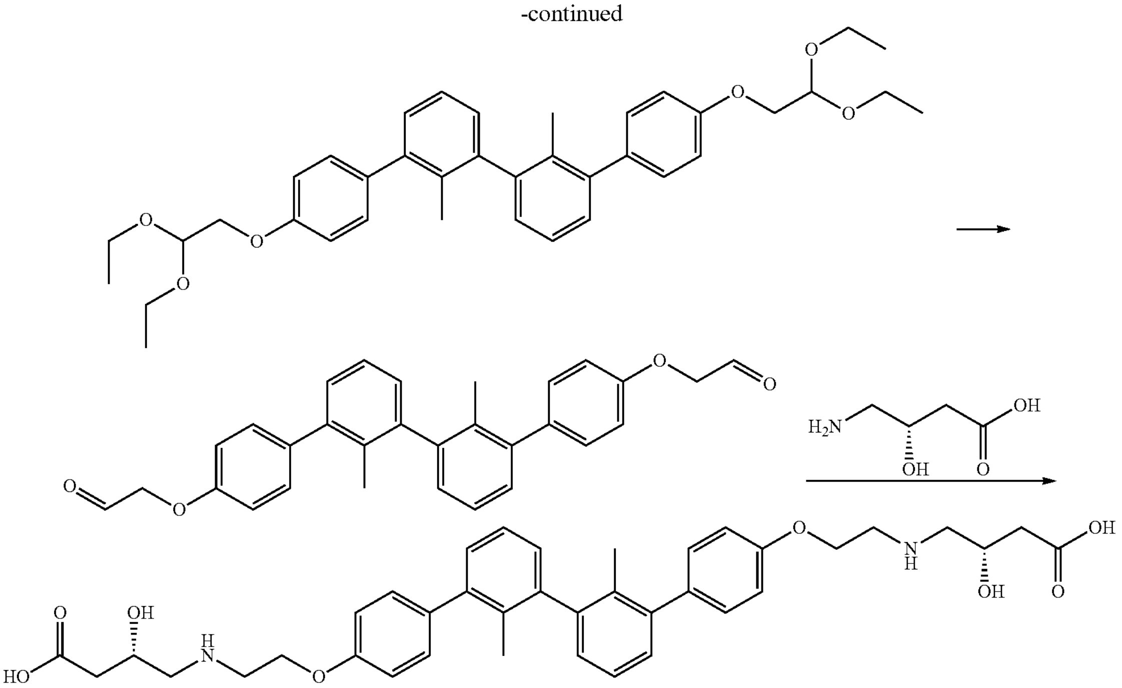

3-Bromo-4'-(2,2-diethoxyethoxy)-2-methyl-1,1'-biphenyl (50 mg, 0.132 mmol) was dissolved in DMF (1 mL), treated with bis(pinacolato)diboron (54 mg, 0.211 mmol), Pd(dppf) $Cl_2$-DCM (9.6 mg, 0.013 mmol) and potassium acetate (38.8 mg, 0.395 mmol). The mixture was purged with argon and then heated at 85° C. for 1.5 h. After cooling to room temperature, the mixture was diluted with EtOAc and water. The organic layer was concentrated and the residue was purified by silica gel chromatography using Hexanes/EtOAc as the eluent to afford 2-(4'-(2,2-diethoxyethoxy)-2-methyl-[1,1'-biphenyl]-3-yl)-4,4,5,5-tetramethyl-1,3,2-dioxaborolane.

3-Bromo-4'-(2,2-diethoxyethoxy)-2-methyl-1,1'-biphenyl (30 mg, 0.079 mmol) and 2-(4'-(2,2-diethoxyethoxy)-2-methyl-[1,1'-biphenyl]-3-yl)-4,4,5,5-tetramethyl-1,3,2-dioxaborolane (33 mg, 0.079 mmol) were suspended in 1,4-dioxane and $H_2O$ (1.8 mL, 5:1), added potassium carbonate (55 mg, 0.395 mmol) and tetrakis(triphenylphosphine)palladium (18 mg, 0.015 mmol). The mixture was purged with argon and then heated at 85° C. After 1h, the mixture was allowed to cool to room temperature. EtOAc and water were added to the mixture. The organic layer was concentrated under reduced pressure and the residue was purified by silica gel chromatography using Hexanes/EtOAc as the eluent to afford 4, 4'''-bis (2, 2-diethoxyethoxy)-2', 2''-dimethyl-1, 1':3', 1'':3'', 1'''-quaterphenyl. 4, 4'''-bis (2, 2-diethoxyethoxy)-2', 2''-dimethyl-1, 1':3', 1'':3'', 1'''-quaterphenyl (21 mg, 0.035 mmol) was dissolved in 1, 4-dioxane (1.8 mL). 37% hydrochloric acid (0.2 mL) was added dropwise to the mixture. After stirring at room temperature for 1h, the reaction was quenched by adding saturated aqueous $NaHCO_3$. The mixture was extracted with EtOAc. The organic layer was dried over sodium sulfate and evaporated under reduced pressure to afford 2,2'-((2',2''-dimethyl-[1,1':3',1'':3'',1'''-quaterphenyl]-4,4'''-diyl)bis(oxy))diacetaldehyde as the crude.

(3S,3'S)-4,4'-((((2',2''-dimethyl-[1,1':3',1'':3'',1'''-quaterphenyl]-4,4'''-diyl)bis(oxy))bis(ethane-2,1-diyl))bis(azanediyl))bis(3-hydroxybutanoic acid) was synthesized from 2,2'-((2',2''-dimethyl-[1,1':3',1'':3'',1'''-quaterphenyl]-4,4'''-diyl)bis(oxy))diacetaldehyde and (S)-4-amino-3-hydroxybutanoic acid using reductive amination procedure G as the bis-TFA salt. MS (m/z) 657.402 $[M+H]^+$. $^1H$ NMR (400 MHz, DMSO-$d_6$) δ 7.39-7.22 (m, 6H), 7.17 (dd, J=7.3, 1.4 Hz, 2H), 7.10 (d, J=7.8 Hz, 2H), 7.04 (d, J=8.6 Hz, 4H), 5.60 (d, J=5.6 Hz, 2H), 4.29 (t, J=5.2 Hz, 4H), 4.20 (s, 2H), 3.39 (s, 2H), 3.21 (s, 2H), 2.99 (s, 2H), 2.45-2.23 (m, 4H), 1.90 (s, 6H).

Example 107: (3R,3'R)-4,4'-((((2',2''-dimethyl-[1,1':3',1'':3'',1'''-quaterphenyl]-4,4'''-diyl)bis(oxy))bis(ethane-2,1-diyl))bis(azanediyl))bis(3-hydroxybutanoic acid)

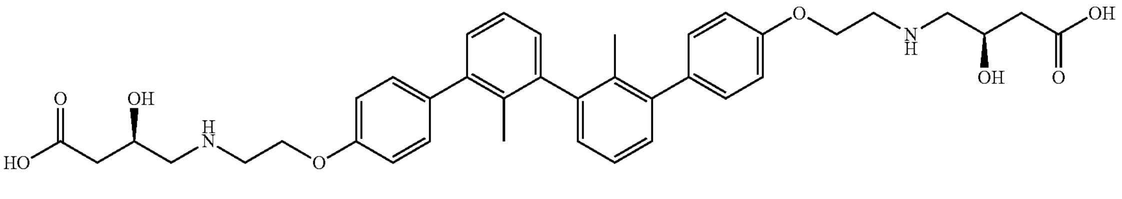 [SMILES: Cc1c(-c2ccc(OCCNC[C@H](O)CC(=O)O)cc2)cccc1-c1cccc(-c2ccc(OCCNC[C@H](O)CC(=O)O)cc2)c1C]

(3R,3'R)-4,4'-((((2',2''-dimethyl-[1,1':3',1'':3'',1'''-quaterphenyl]-4,4'''-diyl)bis(oxy))bis(ethane-2,1-diyl))bis(azanediyl))bis(3-hydroxybutanoic acid) was synthesized from 2,2'-((2',2''-dimethyl-[1,1':3',1'':3'',1'''-quaterphenyl]-4,4'''-diyl)bis(oxy))diacetaldehyde and (R)-4-amino-3-hydroxybutanoic acid using reductive amination procedure G as the bis-TFA salt. MS (m/z) 657.329 $[M+H]^+$. $^1H$ NMR (400 MHz, DMSO-$d_6$) δ 7.38-7.23 (m, 6H), 7.17 (d, J=7.1 Hz, 2H), 7.10 (d, J=7.4 Hz, 2H), 7.04 (d, J=8.6 Hz, 4H), 5.60 (s, 2H), 4.29 (s, 4H), 4.19 (s, 2H), 3.38 (s, 2H), 3.16 (s, 2H), 2.99 (s, 2H), 2.45-2.24 (m, 4H), 1.90 (s, 6H).

Example 108: (3S)-4-((4-((3-(3-((((S)-3-carboxy-2-hydroxypropyl)amino)methyl)-2,3-dihydrobenzo[b][1,4]dioxin-6-yl)-2-methylbenzyl)oxy)-5-chloro-2-((5-cyanopyridin-3-yl)methoxy)benzyl)amino)-3-hydroxybutanoic acid

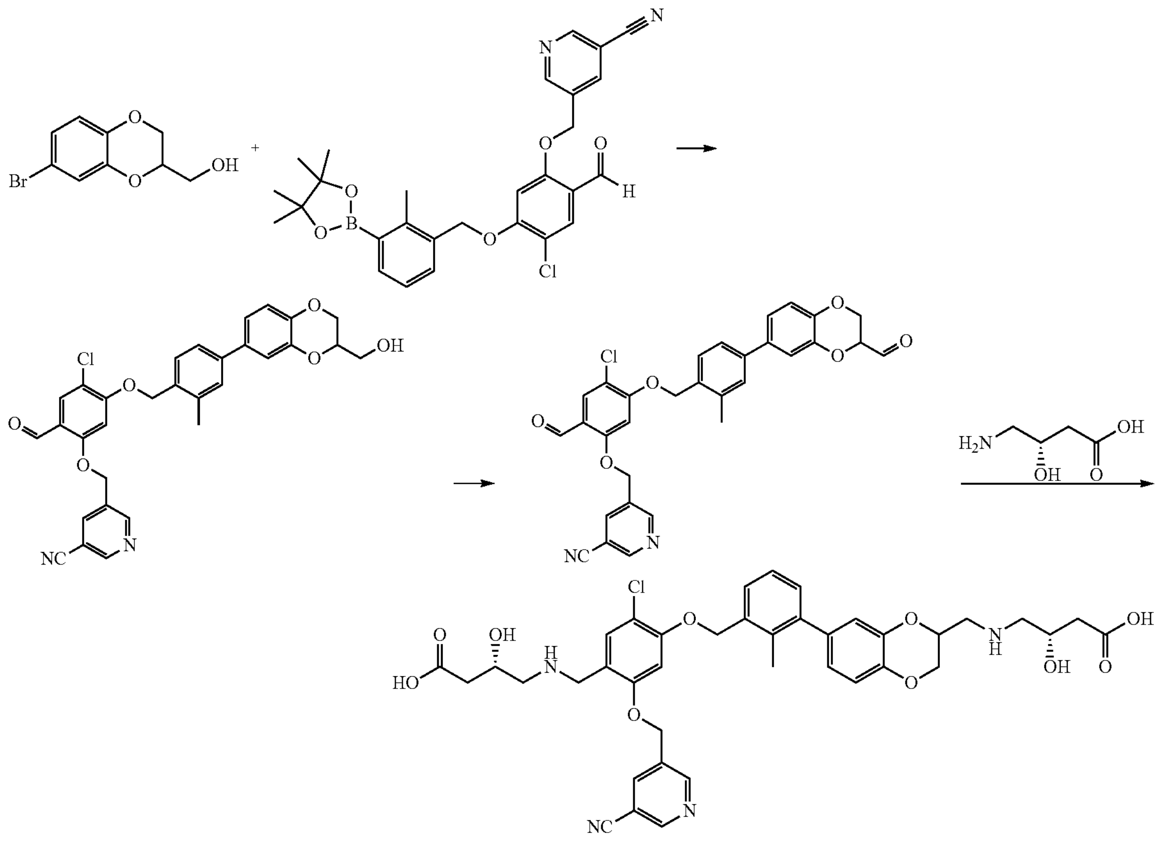

(7-bromo-2, 3-dihydrobenzo[b][1,4]dioxin-2-yl)methanol (synthesized using Ref. *European Journal of Medicinal Chemistry* 120 (2016) 227e243) (100 mg, 0.408 mmol) and 2-(4'-(2,2-diethoxyethoxy)-2-methyl-[1,1'-biphenyl]-3-yl)-4,4,5,5-tetramethyl-1,3,2-dioxaborolane (275 mg, 0.53 mmol) were suspended in 1,4-dioxane and $H_2O$ (4.8 mL, 5:1), added potassium carbonate (282 mg, 2.04 mmol) and tetrakis(triphenylphosphine)palladium (94 mg, 0.082 mmol). The mixture was purged with argon and then heated at 85° C. After 1.5h, the mixture was allowed to cool to room temperature. EtOAc and water were added to the mixture. The organic layer was concentrated and the residue was purified by silica gel chromatography using Hexanes/EtOAc as the eluent to afford 5-((4-chloro-2-formyl-5-((4-(3-(hydroxymethyl)-2,3-dihydrobenzo[b][1,4]dioxin-6-yl)-2-methylbenzyl)oxy)phenoxy)methyl)nicotinonitrile.

5-((4-chloro-2-formyl-5-((4-(3-(hydroxymethyl)-2, 3-dihydrobenzo[b][1,4]dioxin-6-yl)-2-methylbenzyl)oxy)phenoxy)methyl)nicotinonitrile (140 mg, 251 mmol) was dissolved in dichloromethane (5 mL), added Dess-Martin periodinane (213 mg, 503 mmol). The mixture was left stirring at room temperature for 40 min and then filtered through a short bed of Celite. The filtrated was diluted with EtOAc, washed with saturated aqueous $NaHCO_3$, followed by aqueous sodium thiosulfate. The organic layer was evaporated under reduced pressure to give 5-((4-chloro-2-formyl-5-((4-(3-formyl-2, 3-dihydrobenzo[b][1,4]dioxin-6-yl)-2-methylbenzyl)oxy)phenoxy)methyl)nicotinonitrile as the crude.

(3S)-4-((4-((3-(3-((((S)-3-carboxy-2-hydroxypropyl)amino)methyl)-2,3-dihydrobenzo[b][1,4]dioxin-6-yl)-2-methylbenzyl)oxy)-5-chloro-2-((5-cyanopyridin-3-yl)methoxy)benzyl)amino)-3-hydroxybutanoic acid was synthesized from 5-((4-chloro-2-formyl-5-((4-(3-formyl-2,3-dihydrobenzo[b][1,4]dioxin-6-yl)-2-methylbenzyl)oxy)phenoxy)methyl)nicotinonitrile (used crude) and (S)-4-amino-3-hydroxybutanoic acid using reductive amination procedure G as the bis-TFA salt. MS (m/z) 761.068 $[M+H]^+$. $^1H$ NMR (400 MHz, DMSO-$d_6$) δ 9.02 (dd, J=6.0, 2.1 Hz, 2H), 8.81 (s, 2H), 8.56 (s, 2H), 8.45 (t, J=2.1 Hz, 1H), 7.57 (s, 1H), 7.44 (d, J=7.6 Hz, 1H), 7.25 (t, J=7.5 Hz, 1H), 7.17 (d, J=6.5 Hz, 2H), 6.98 (d, J=8.3 Hz, 1H), 6.90-6.69 (m, 2H), 5.36 (s, 2H), 5.28 (s, 2H), 4.68-4.38 (d, J=11.4 Hz, 1H), 4.13-4.02 (m, 6H), 3.12-2.72 (m, 6H), 2.45-2.31 (m, 4H), 2.23 (s, 3H).

Example 109: (S)-4-(((6-((4"-(2-(((S)-3-carboxy-2-hydroxypropyl)amino)ethoxy)-2,2'-dimethyl-[1,1':3',1"-terphenyl]-3-yl)methoxy)-5-chloro-2-methoxy-pyridin-3-yl)methyl)amino)-3-hydroxybutanoic acid
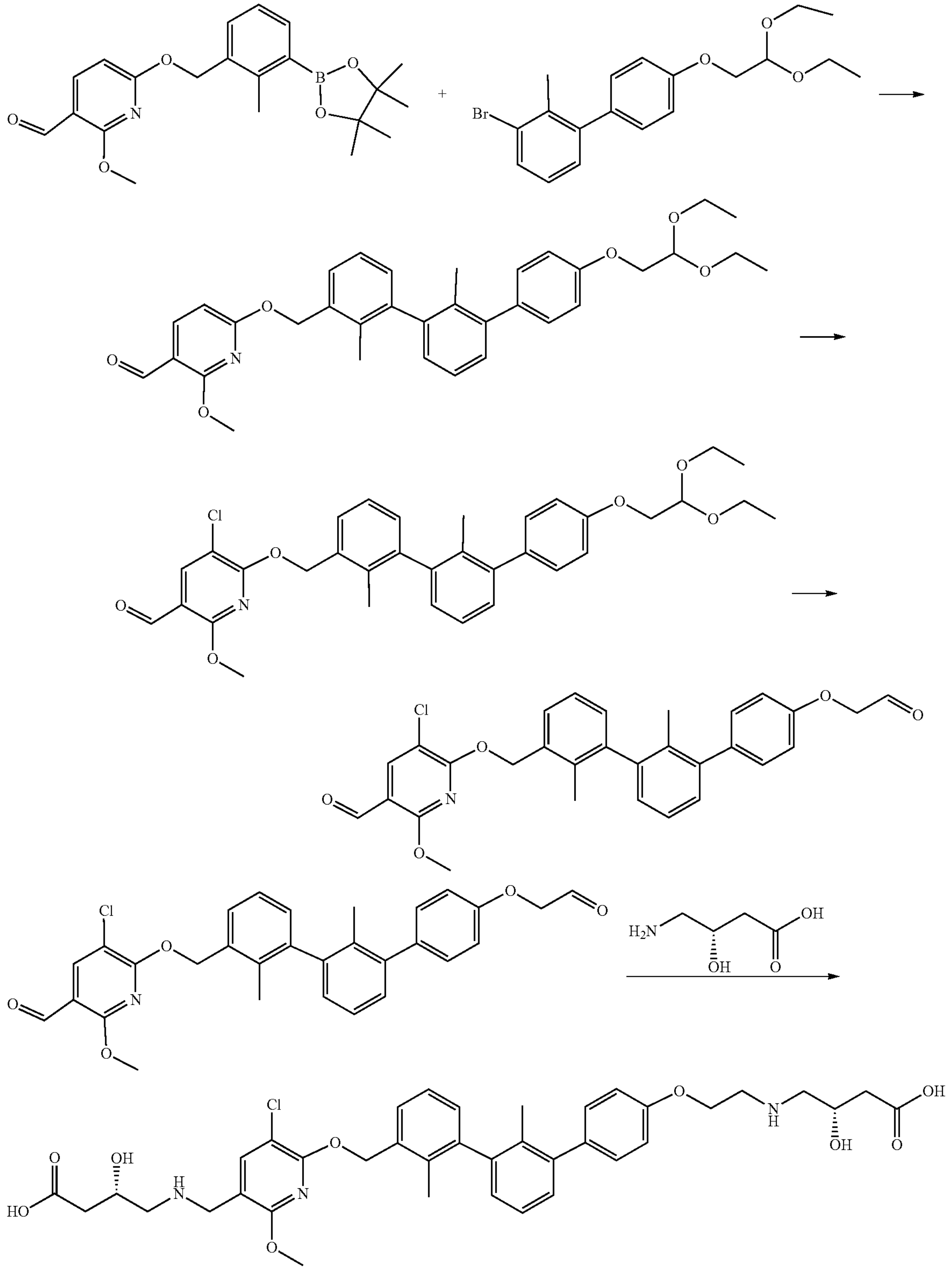

3-Bromo-4'-(2,2-diethoxyethoxy)-2-methyl-1,1'-biphenyl (70 mg, 0.185 mmol) and 2-methoxy-6-((2-methyl-3-(4,4,5,5-tetramethyl-1,3,2-dioxaborolan-2-yl)benzyl)oxy)nicotinaldehyde (99 mg, 0.258 mmol) were suspended in 1,4-dioxane and $H_2O$ (2.4 mL, 5:1), added potassium carbonate (138 mg, 0.923 mmol) and tetrakis(triphenylphosphine) palladium (43 mg, 0.037 mmol). The mixture was purged with argon and then heated at 85° C. After 1h, the mixture was allowed to cool to room temperature. EtOAc and water were added to the mixture. The organic layer was concentrated and the residue was purified by silica gel chromatography using Hexanes/EtOAc as the eluent to afford 6-((4"-(2,2-diethoxyethoxy)-2,2'-dimethyl-[1,1':3',1"-terphenyl]-3-yl)methoxy)-2-methoxynicotinaldehyde.

6-((4"-(2, 2-diethoxyethoxy)-2, 2'-dimethyl-[1, 1':3', 1"-terphenyl]-3-yl)methoxy)-2-methoxynicotinaldehyde (41 mg, 0.074 mmol) was dissolved in DMF/chloroform (2 mL, 1:1), added palau'chlor (29 mg, 0.139 mmol) in one portion. 4 N HCl in 1, 4-dioxane (0.031 mL, 0.124 mmol) was added dropwise. Complete conversion was observed after 30 min stirring at room temperature. The mixture was then diluted with EtOAc, washed with saturated aqueous $NaHCO_3$. The organic layer was evaporated under reduced pressure. The residue was purified by silica gel chromatography using Hexanes/EtOAc as the eluent to afford 5-chloro-6-((4"-(2, 2-diethoxyethoxy)-2, 2'-dimethyl-[1, 1':3', 1"-terphenyl]-3-yl)methoxy)-2-methoxynicotinaldehyde.

5-chloro-6-((4"-(2,2-diethoxyethoxy)-2,2'-dimethyl-[1,1':3',1"-terphenyl]-3-yl)methoxy)-2-methoxynicotinaldehyde (35 mg, 0.059 mmol) was dissolved in 1, 4-dioxane (2 mL). 37% hydrochloric acid (0.2 mL) was added dropwise to the mixture. After stirring at room temperature for 2 h, the reaction was quenched by adding saturated aqueous $NaHCO_3$. The mixture was extracted with EtOAc. The organic layer was dried over sodium sulfate and evaporated under reduced pressure to afford 5-chloro-6-((2,2'-dimethyl-4"-(2-oxoethoxy)-[1,1':3',1"-terphenyl]-3-yl)methoxy)-2-methoxynicotinaldehyde as the crude.

(S)-4-(((6-((4"-(2-(((S)-3-carboxy-2-hydroxypropyl)amino)ethoxy)-2,2'-dimethyl-[1,1':3',1"-terphenyl]-3-yl)methoxy)-5-chloro-2-methoxypyridin-3-yl)methyl)amino)-3-hydroxybutanoic acid was synthesized from 5-chloro-6-((2,2'-dimethyl-4"-(2-oxoethoxy)-[1,1':3',1"-terphenyl]-3-yl)methoxy)-2-methoxynicotinaldehyde (crude) and (S)-4-amino-3-hydroxybutanoic acid using reductive amination procedure G as the bis-TFA salt. MS (m/z) 722.115 $[M+H]^+$. $^1H$ NMR (400 MHz, Methanol-$d_4$) ≢ 7.81 (s, 1H), 7.46 (dd, J=7.7, 1.4 Hz, 1H), 7.38-6.97 (m, 9H), 5.59 (s, 2H), 4.43-4.21 (m, 4H), 4.16 (s, 2H), 4.05 (s, 3H), 3.58-3.47 (m, 2H), 3.35 (dd, J=12.7, 3.1 Hz, 1H), 3.24-3.09 (m, 2H), 3.00 (dd, J=12.8, 9.8 Hz, 1H), 2.56 (dd, J=16.1, 6.3 Hz, 4H), 2.15 (s, 3H), 1.87 (s, 3H).

Example 110: (R)-4-(((6-((4"-(2-(((R)-3-carboxy-2-hydroxypropyl)amino)ethoxy)-2,2'-dimethyl-[1,1':3',1"-terphenyl]-3-yl)methoxy)-5-chloro-2-methoxypyridin-3-yl)methyl)amino)-3-hydroxybutanoic acid

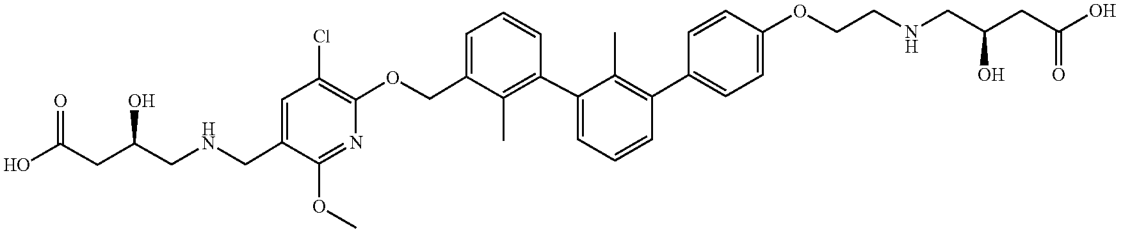 [SMILES: COc1nc(OCc2cccc(-c3cccc(-c4ccc(OCCNC[C@H](O)CC(=O)O)cc4)c3C)c2C)c(Cl)cc1CNC[C@H](O)CC(=O)O]

(R)-4-(((6-((4"-(2-(((R)-3-carboxy-2-hydroxypropyl)amino)ethoxy)-2,2'-dimethyl-[1,1':3',1"-terphenyl]-3-yl)methoxy)-5-chloro-2-methoxypyridin-3-yl)methyl)amino)-3-hydroxybutanoic acid was synthesized from 5-chloro-6-((2,2'-dimethyl-4"-(2-oxoethoxy)-[1,1':3',1"-terphenyl]-3-yl)methoxy)-2-methoxynicotinaldehyde (crude) and (R)-4-amino-3-hydroxybutanoic acid using reductive amination procedure G as the bis-TFA salt. MS (m/z) 722.066 $[M+H]^+$. $^1H$ NMR (400 MHz, Methanol-$d_4$) δ 7.81 (s, 1H), 7.46 (dd, J=7.7, 1.4 Hz, 1H), 7.36-6.96 (m, 9H), 5.59 (s, 2H), 4.44-4.22 (m, 4H), 4.16 (s, 2H), 4.05 (s, 3H), 3.54 (t, J=5.1 Hz, 2H), 3.35 (dd, J=12.7, 3.0 Hz, 1H), 3.26-3.05 (m, 2H), 3.00 (dd, J=12.8, 9.8 Hz, 1H), 2.56 (dd, J=16.2, 6.3 Hz, 4H), 2.15 (s, 3H), 1.87 (s, 3H).

Example 111: (S)-4-((4-((4"-(2-(((S)-3-carboxy-2-hydroxypropyl)amino)ethoxy)-2"-fluoro-2,2'-dimethyl-[1,1':3',1"-terphenyl]-3-yl)methoxy)-5-chloro-2-((5-cyanopyridin-3-yl)methoxy)benzyl)amino)-3-hydroxybutanoic acid (or (S)-4-((4-((4"-(2-(((S)-3-carboxy-2-hydroxypropyl)amino)ethoxy)-2"-fluoro-2,2'-dimethyl-[1,1':3',1"-terphenyl]-3-yl)methoxy)-5-chloro-2-((5-cyanopyridin-3-yl)methoxy)benzyl)amino)-3-hydroxybutanoic acid)

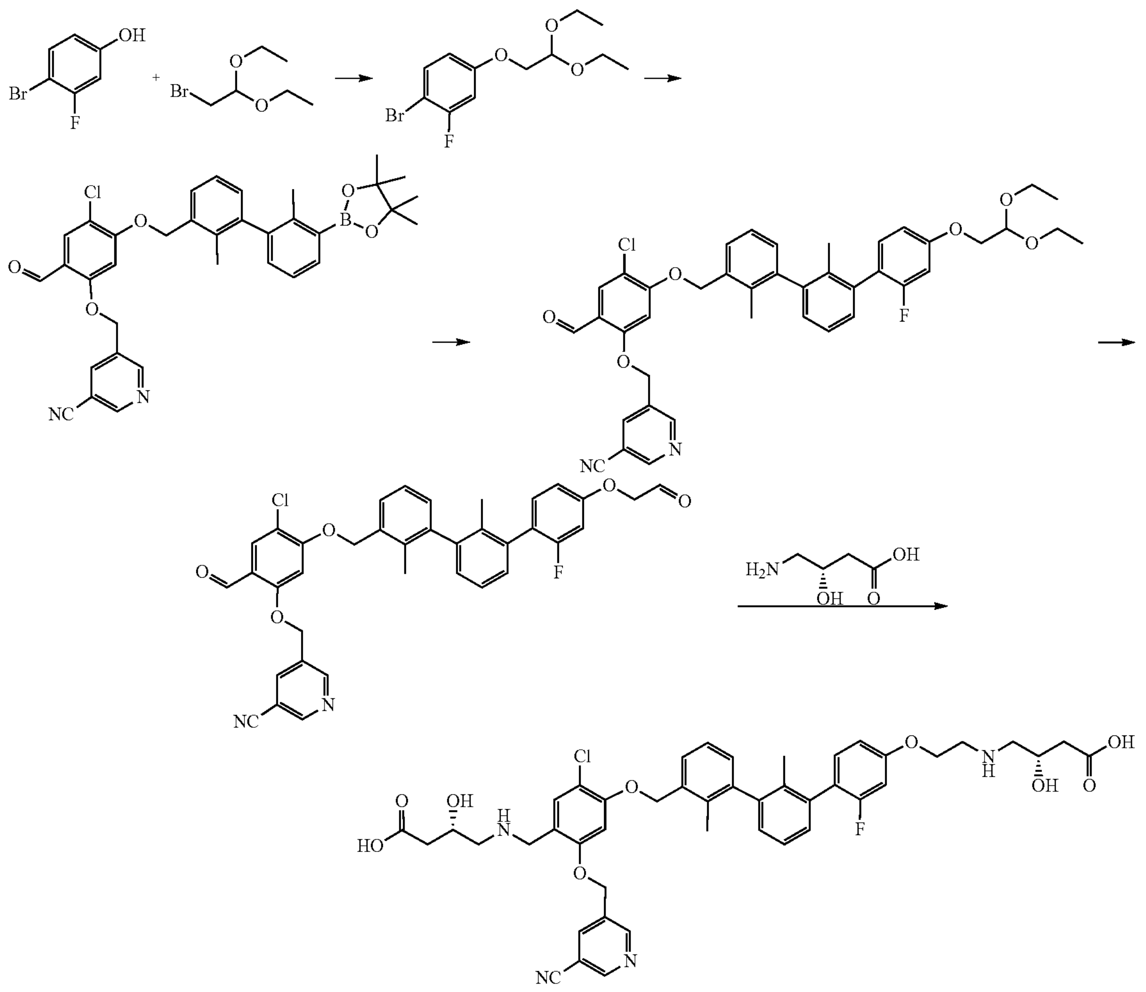

4-bromo-3-fluorophenol (200 mg, 1.05 mmol) was dissolved in DMF (2 mL), added 2-bromo-1, 1-diethoxyethane (495 mg, 2.5 mmol), followed by addition of cesium carbonate (1.70 g, 5.25 mmol). The mixture was heated to 85° C. Clean complete conversion was observed after 3 h, EtOAc and water were added to the mixture, and the organic layer was evaporated under reduced pressure. The residue was purified by silica gel chromatography using Hexanes/EtOAc as the eluent to afford 1-bromo-4-(2, 2-diethoxyethoxy)-2-fluorobenzene.

1-bromo-4-(2,2-diethoxyethoxy)-2-fluorobenzene (38 mg, 0.128 mmol) and 5-((4-chloro-5-((2,2'-dimethyl-3'-(4,4,5,5-tetramethyl-1,3,2-dioxaborolan-2-yl)-[1,1'-biphenyl]-3-yl)methoxy)-2-formylphenoxy)methyl)nicotinonitrile (25 mg, 0.041 mmol) were suspended in 1,4-dioxane and $H_2O$ (1.44 mL, 5:1), added potassium carbonate (22.7 mg, 0.164 mmol) and tetrakis(triphenylphosphine)palladium (9 mg, 0.008 mmol). The mixture was purged with argon and then heated at 85° C. After 1 h, the mixture was allowed to cool to room temperature. EtOAc and water were added to the mixture. The organic layer was concentrated and the residue was purified by silica gel chromatography using Hexanes/EtOAc as the eluent to afford 5-((4-chloro-5-((4"-(2,2-diethoxyethoxy)-2"-fluoro-2,2'-dimethyl-[1,1':3',1"-terphenyl]-3-yl)methoxy)-2-formylphenoxy)methyl) nicotinonitrile.

5-((4-chloro-5-((4"-(2,2-diethoxyethoxy)-2"-fluoro-2,2'-dimethyl-[1,1':3',1"-terphenyl]-3-yl)methoxy)-2-formylphenoxy)methyl)nicotinonitrile (18 mg, 0.025 mmol) was dissolved in 1, 4-dioxane (1 mL). 37% hydrochloric acid (0.1 mL) was added dropwise to the mixture. After stirring at room temperature for 18 h, the reaction was quenched by adding saturated aqueous $NaHCO_3$. The mixture was extracted with EtOAc. The organic layer was dried over sodium sulfate and evaporated under reduced pressure to afford 5-((4-chloro-5-((2"-fluoro-2,2'-dimethyl-4"-(2-oxoethoxy)-[1,1':3',1"-terphenyl]-3-yl)methoxy)-2-formylphenoxy)methyl)nicotinonitrile as the crude.

(S)-4-((4-((4"-(2-(((S)-3-carboxy-2-hydroxypropyl)amino)ethoxy)-2"-fluoro-2,2'-dimethyl-[1,1':3',1"-terphenyl]-3-yl)methoxy)-5-chloro-2-((5-cyanopyridin-3-yl)methoxy)benzyl)amino)-3-hydroxybutanoic acid was synthesized from 5-((4-chloro-5-((2''-fluoro-2,2'-dimethyl-4''-(2-oxoethoxy)-[1,1':3',1''-terphenyl]-3-yl)methoxy)-2-formylphenoxy)methyl)nicotinonitrile (crude) and (S)-4-amino-3-hydroxybutanoic acid using reductive amination procedure G as the bis-TFA salt. MS (m/z) 841.044 $[M+H]^+$. $^1$H NMR (400 MHz, Methanol-$d_4$) δ 8.94 (dd, J=12.0, 2.1 Hz, 2H), 8.37 (d, J=2.2 Hz, 1H), 7.51 (s, 1H), 7.46 (d, J=7.4 Hz, 1H), 7.37-7.02 (m, 7H), 6.99-6.80 (m, 2H), 5.37 (s, 2H), 5.31 (s, 2H), 4.36 (t, J=5.0 Hz, 3H), 4.23 (s, 3H), 3.54 (t, J=5.1 Hz, 2H), 3.41-3.32 (m, 1H), 3.26-3.07 (m, 2H), 2.97 (dd, J=12.7, 9.8 Hz, 1H), 2.58 (d, J=6.3 Hz, 2H), 2.56-2.46 (m, 2H), 2.13 (s, 3H), 1.81 (d, J=1.2 Hz, 3H).

Example 112: (S)-4-((4-((3'-(5-(2-(((S)-3-carboxy-2-hydroxypropyl)amino)ethoxy)pyridin-2-yl)-2,2'-dimethyl-[1,1'-biphenyl]-3-yl)methoxy)-5-chloro-2-((5-cyanopyridin-3-yl)methoxy)benzyl)amino)-3-hydroxybutanoic acid

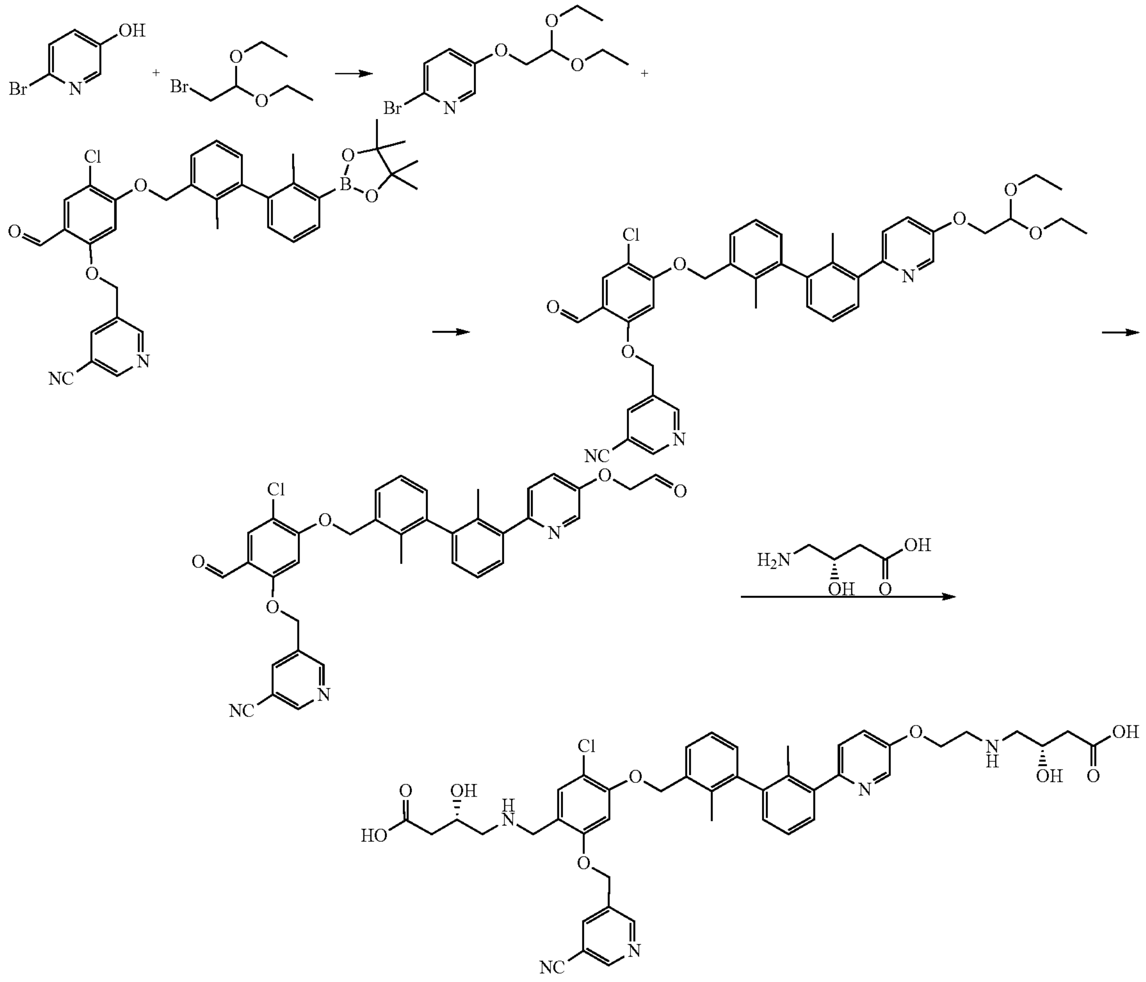

6-Bromopyridin-3-ol (200 mg, 1.15 mmol) was dissolved in DMF (2 mL), added 2-bromo-1, 1-diethoxyethane (566 mg, 2.87 mmol), and followed by addition of cesium carbonate (1.87 g, 5.75 mmol). The mixture was heated to 85° C. Clean complete conversion was observed after 1 h. EtOAc and water were added to the mixture, and the organic layer was evaporated under reduced pressure. The residue was purified by silica gel chromatography using Hexanes/EtOAc as the eluent to afford 2-bromo-5-(2,2-diethoxyethoxy)pyridine.

2-bromo-5-(2,2-diethoxyethoxy)pyridine (43 mg, 0.148 mmol) and 5-((4-chloro-5-((2,2'-dimethyl-3'-(4,4,5,5-tetramethyl-1,3,2-dioxaborolan-2-yl)-[1,1'-biphenyl]-3-yl)methoxy)-2-formylphenoxy)methyl)nicotinonitrile (30 mg, 0.049 mmol) were suspended in 1,4-dioxane and $H_2O$ (1.44 mL, 5:1), added potassium carbonate (27 mg, 0.197 mmol) and tetrakis(triphenylphosphine)palladium (11 mg, 0.01 mmol). The mixture was purged with argon and then heated at 85° C. After 1 h, the mixture was allowed to cool to room temperature. EtOAc and water were added to the mixture. The organic layer was concentrated and the residue was purified by silica gel chromatography using Hexanes/EtOAc as the eluent to afford 5-((4-chloro-5-((3'-(5-(2,2-diethoxyethoxy)pyridin-2-yl)-2,2'-dimethyl-[1,1'-biphenyl]-3-yl)methoxy)-2-formylphenoxy)methyl)nicotinonitrile.

5-((4-chloro-5-((3'-(5-(2,2-diethoxyethoxy)pyridin-2-yl)-2,2'-dimethyl-[1,1'-biphenyl]-3-yl)methoxy)-2-formylphenoxy)methyl)nicotinonitrile (15.9 mg, 0.023 mmol) was dissolved in 1, 4-dioxane (1 mL). 37% hydrochloric acid (0.1 mL) was added dropwise to the mixture. After stirring at room temperature for 18 h, the reaction was quenched by adding saturated aqueous $NaHCO_3$. The mixture was extracted with EtOAc. The organic layer was dried over sodium sulfate and evaporated under reduced pressure to afford 5-((4-chloro-5-((2,2'-dimethyl-3'-(5-(2-oxoethoxy) pyridin-2-yl)-[1,1'-biphenyl]-3-yl)methoxy)-2-formylphenoxy)methyl)nicotinonitrile as the crude.

(S)-4-((4-((3'-(5-(2-(((S)-3-carboxy-2-hydroxypropyl) amino)ethoxy)pyridin-2-yl)-2,2'-dimethyl-[1,1'-biphenyl]-3-yl)methoxy)-5-chloro-2-((5-cyanopyridin-3-yl)methoxy) benzyl)amino)-3-hydroxybutanoic acid was synthesized from 5-((4-chloro-5-((2,2'-dimethyl-3'-(5-(2-oxoethoxy) pyridin-2-yl)-[1,1'-biphenyl]-3-yl)methoxy)-2-formylphenoxy)methyl)nicotinonitrile (crude) and (S)-4-amino-3-hydroxybutanoic acid using reductive amination procedure G as the bis-TFA salt. MS (m/z) 824.129 $[M+H]^+$. $^1H$ NMR (400 MHz, Methanol-$d_4$) δ 8.94 (dd, J=13.2, 2.0 Hz, 2H), 8.48-8.26 (m, 2H), 7.72 (dd, J=8.7, 2.9 Hz, 1H), 7.60 (d, J=8.7 Hz, 1H), 7.52-7.42 (m, 2H), 7.42-7.31 (m, 2H), 7.27 (t, J=7.6 Hz, 1H), 7.20 (dd, J=7.0, 2.0 Hz, 1H), 7.14 (dd, J=7.7, 1.4 Hz, 1H), 7.08 (s, 1H), 5.37 (s, 2H), 5.31 (s, 2H), 4.48 (t, J=5.0 Hz, 2H), 4.35 (dp, J=9.4, 3.2 Hz, 1H), 4.27-4.12 (m, 3H), 3.59 (t, J=5.0 Hz, 2H), 3.37 (dd, J=12.7, 3.0 Hz, 1H), 3.25-3.08 (m, 2H), 2.97 (dd, J=12.7, 9.8 Hz, 1H), 2.59 (d, J=6.3 Hz, 2H), 2.51 (dd, J=6.3, 1.1 Hz, 2H), 2.15 (s, 3H), 1.91 (s, 3H).

Example 113: (3S,3'S)-4,4'-((((((2,2'-dimethyl-[1,1'-biphenyl]-3,3'-diyl)bis(methylene))bis(oxy))bis(5-bromo-2-methoxypyridine-6,3-diyl))bis(methylene)) bis(azanediyl))bis(3-hydroxybutanoic acid) (or (3S, 3'S)-4,4'-(((6,6'-(((2,2'-dimethyl-[1,1'-biphenyl]-3,3'-diyl)bis(methylene))bis(oxy))bis(5-bromo-2-methoxypyridine-6,3-diyl))bis(methylene))bis (azanediyl))bis(3-hydroxybutanoic acid))

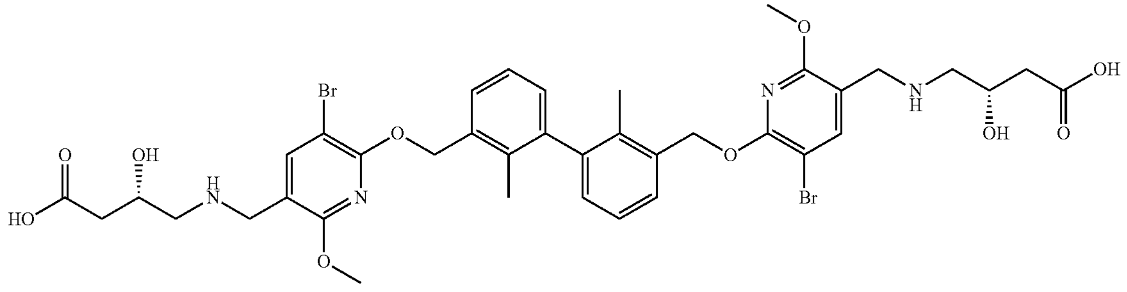 [SMILES: COc1nc(OCc2cccc(-c3cccc(COc4nc(OC)c(CNC[C@@H](O)CC(=O)O)cc4Br)c3C)c2C)c(Br)cc1CNC[C@@H](O)CC(=O)O]

The title compound was prepared from Intermediate 25 following reductive amination procedure G. $^1H$ NMR (400 MHz, Methanol-d) δ 7.95 (s, 2H), 7.49 (d, J=7.3 Hz, 2H), 7.25 (t, J=7.6 Hz, 2H), 7.09 (d, J=7.6 Hz, 2H), 5.59 (s, 4H), 4.38-4.23 (m, 2H), 4.16 (s, 4H), 4.07 (s, 6H), 3.21 (dd, J=12.8, 3.1 Hz, 2H), 3.01 (dd, J=12.8, 9.8 Hz, 2H), 2.55 (d, J=6.3 Hz, 4H), 2.11 (s, 6H). MS (m/z) 876.890 (M+H)+.

Example 114: (3R,3'R)-4,4'-((((((2,2'-dimethyl-[1,1'-biphenyl]-3,3'-diyl)bis(methylene))bis(oxy))bis(5-bromo-2-methoxypyridine-6,3-diyl))bis(methylene)) bis(azanediyl))bis(3-hydroxybutanoic acid) (or (3R, 3'R)-4,4'-(((6,6'-(((2,2'-dimethyl-[1,1'-biphenyl]-3,3'-diyl)bis(methylene))bis(oxy))bis(5-bromo-2-methoxypyridine-6,3-diyl))bis(methylene))bis (azanediyl))bis(3-hydroxybutanoic acid))

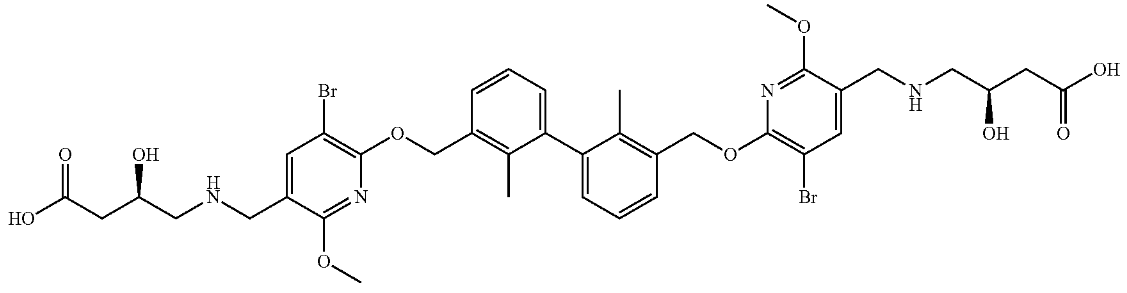 [SMILES: COc1nc(OCc2cccc(-c3cccc(COc4nc(OC)c(CNC[C@H](O)CC(=O)O)cc4Br)c3C)c2C)c(Br)cc1CNC[C@H](O)CC(=O)O]

The title compound was prepared from Intermediate 25 following reductive amination procedure G using (3R)-4-amino-3-hydroxybutanoic acid in place of (3S)-4-amino-3-hydroxybutanoic acid. $^1$H NMR (400 MHz, Methanol-$d_4$) δ 7.94 (s, 2H), 7.48 (dd, J=7.5, 1.3 Hz, 2H), 7.24 (t, J=7.6 Hz, 2H), 7.07 (dd, J=7.8, 1.4 Hz, 2H), 5.58 (s, 4H), 4.28 (dtd, J=9.4, 6.3, 3.0 Hz, 2H), 4.15 (s, 4H), 4.05 (s, 6H), 3.20 (dd, J=12.8, 3.1 Hz, 2H), 3.00 (dd, J=12.8, 9.8 Hz, 2H), 2.54 (d J=6.3 Hz, 4H), 2.09 (s, 6H). MS (m/z) 876.849 (M+H)+.

Example 115: (2S,2'S)-2,2'-((((((2,2'-dimethyl-[1,1'-biphenyl]-3,3'-diyl)bis(methylene))bis(oxy))bis(5-bromo-2-methoxypyridine-6,3-diyl))bis(methylene))bis(azanediyl))bis(5-amino-5-oxopentanoic acid) (or (2S,2'S)-2,2'-(((6,6'-(((2,2'-dimethyl-[1,1'-biphenyl]-3,3'-diyl)bis(methylene))bis(oxy))bis(5-bromo-2-methoxypyridine-6,3-diyl))bis(methylene))bis(azanediyl))bis(5-amino-5-oxopentanoic acid))

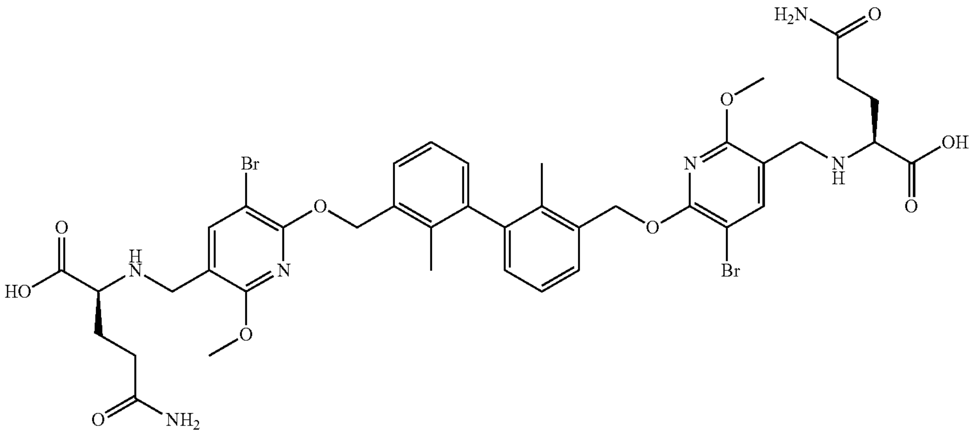 [SMILES: COc1nc(OCc2cccc(-c3cccc(COc4nc(OC)c(CN[C@@H](CCC(N)=O)C(=O)O)cc4Br)c3C)c2C)c(Br)cc1CN[C@@H](CCC(N)=O)C(=O)O]

The title compound was prepared from Intermediate 25 following reductive amination procedure G using L-glutamine in place of (3S)-4-amino-3-hydroxybutanoic acid. $^1$H NMR (400 MHz, Methanol-$d_4$) δ 7.92 (s, 2H), 7.52-7.42 (m, 2H), 7.23 (q, J=7.8 Hz, 2H), 7.08 (d, J=7.2 Hz, 2H), 5.58 (s, 4H), 4.16 (d, J=1.5 Hz, 4H), 4.05 (s, 6H), 3.93-3.87 (m, 2H), 2.63-2.50 (m, 4H), 2.31-2.04 (m, 10H). MS (m/z) 930.8887 (M+H)+.

Example 116: 4,4'-((((((2,2'-dimethyl-[1,1'-biphenyl]-3,3'-diyl)bis(methylene))bis(oxy))bis(5-bromo-2-methoxypyridine-6,3-diyl))bis(methylene))bis(azanediyl))dibutanamide (or 4,4'-(((6,6'-(((2,2'-dimethyl-[1,1'-biphenyl]-3,3'-diyl)bis(methylene))bis(oxy))bis(5-bromo-2-methoxypyridine-6,3-diyl))bis(methylene))bis(azanediyl))dibutanamide)

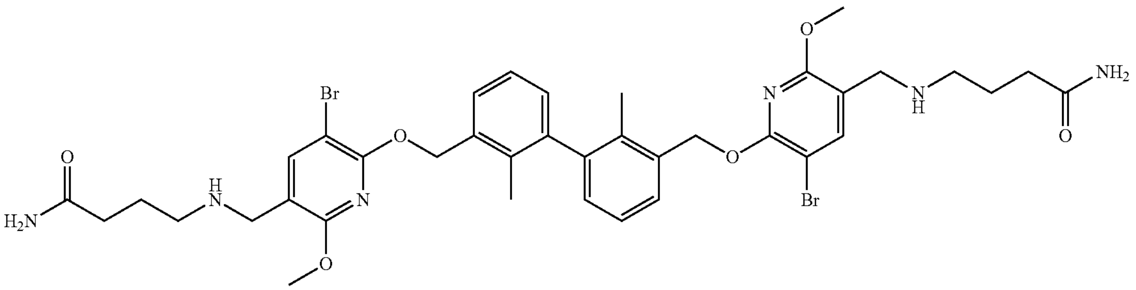 [SMILES: COc1nc(OCc2cccc(-c3cccc(COc4nc(OC)c(CNCCCC(N)=O)cc4Br)c3C)c2C)c(Br)cc1CNCCCC(N)=O]

The title compound was prepared from Intermediate 25 following reductive amination procedure G using 4-aminobutanoic acid hydrochloride in place of (3S)-4-amino-3-hydroxybutanoic acid. $^1$H NMR (400 MHz, Methanol-$d_4$) δ 7.93 (s, 2H), 7.47 (d, J=7.4 Hz, 2H), 7.24 (t, J=7.6 Hz, 2H), 7.11-7.04 (m, 2H), 5.58 (s, 4H), 4.10 (s, 4H), 4.05 (s, 6H), 3.08 (t, J=7.1 Hz, 4H), 2.41 (t, J=6.7 Hz, 4H), 2.09 (s, 6H), 2.00-1.88 (m, 4H). MS (m/z) 842.933 (M+H)+.

Example 117: 2,2'-((((((2,2'-dimethyl-[1,1'-biphenyl]-3,3'-diyl)bis(methylene))bis(oxy))bis(5-bromo-2-methoxypyridine-6,3-diyl))bis(methylene))bis((4-amino-4-oxobutyl)azanediyl))diacetic acid (or 2,2'-(((6,6'-(((2,2'-dimethyl-[1,1'-biphenyl]-3,3'-diyl)bis(methylene))bis(oxy))bis(5-bromo-2-methoxypyridine-6,3-diyl))bis(methylene))bis((4-amino-4-oxobutyl)azanediyl))diacetic acid)

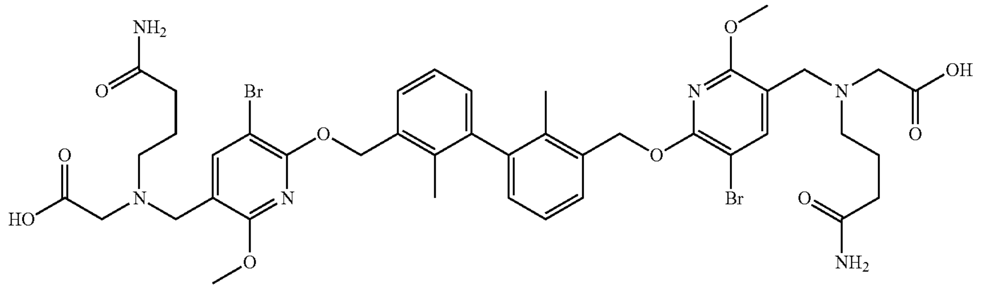 [SMILES: COc1nc(OCc2cccc(-c3cccc(COc4nc(OC)c(CN(CCCC(N)=O)CC(=O)O)cc4Br)c3C)c2C)c(Br)cc1CN(CCCC(N)=O)CC(=O)O]

To Intermediate 25 (50 mg, 0.075 mmol) in methylene chloride (1.5 mL) was added a 3 mL solution of ethanol containing 4-aminobutanoic acid hydrochloride (62 mg, 0.45 mmol) and potassium hydroxide (25 mg, 0.45 mmol). The reaction was stirred for 1 hour at room temperature before $Na(OAc)_3BH$ (156 mg, 0.75 mmol) and AcOH (45 mg, 0.75 mmol) were added. The cloudy reaction was sonicated for 1 min and stirred at room temperature for 2 h. Glyoxalic acid monohydrate (137 mg, 1.5 mmol) was added, and the reaction was stirred for an additional 0.5 h before additional $Na(OAc)_3BH$ (156 mg, 0.75 mmol) was added. After 1 h, the reaction was quenched with the addition of 1M HCl until the solution clears. The solution was concentrated in vacuo, diluted with a mixture of $MeCN/H_2O/DMF$ (1:1:1), and purified by purified by reverse phase HPLC (0.1% trifluoroacetic acid in acetonitrile/water) providing 9 mg of the title compound upon lyophilization as the bis-TFA salt. $^1$H NMR (400 MHz, Methanol-$d_4$) δ 8.03 (s, 2H), 7.55-7.33 (m, 2H), 7.25 (t, J=7.6 Hz, 2H), 7.16-7.00 (m, 2H), 5.58 (s, 4H), 4.39 (s, 4H), 4.05 (s, 6H), 3.98 (s, 4H), 2.46 (t, J=6.4 Hz, 4H), 2.10 (s, 6H), 2.05 (q, J=6.6 Hz, 4H). MS (m/z) 958.931 (M+H)+.

Example 118: N-(4-amino-4-oxobutyl)-N-((6-((3'-(((5-(((4-amino-4-oxobutyl)amino)methyl)-3-bromo-6-methoxypyridin-2-yl)oxy)methyl)-2,2'-dimethyl-[1,1'-biphenyl]-3-yl)methoxy)-5-bromo-2-methoxypyridin-3-yl)methyl)glycine

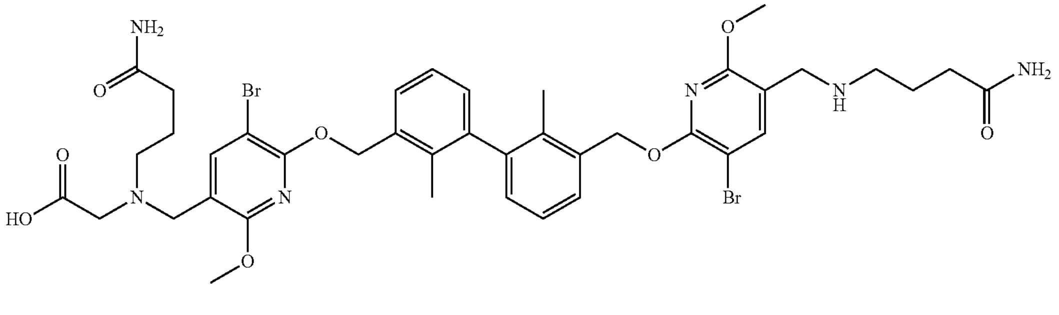 [SMILES: COc1nc(OCc2cccc(-c3cccc(COc4nc(OC)c(CN(CCCC(N)=O)CC(=O)O)cc4Br)c3C)c2C)c(Br)cc1CNCCCC(N)=O]

6 mg of the title compound was isolated as a byproduct from Example 117. $^1$H NMR (400 MHz, Methanol-$d_4$) δ 8.03 (s, 1H), 7.93 (s, 1H), 7.55-7.40 (m, 2H), 7.32-7.15 (m, 2H), 7.15-7.00 (m, 2H), 5.58 (s, 4H), 4.38 (s, 2H), 4.10 (s, 2H), 4.05 (d, J=2.4 Hz, 6H), 3.95 (d, J=3.8 Hz, 2H), 3.08 (t, J=7.2 Hz, 2H), 2.50-2.34 (m, 4H), 2.16-2.06 (m, 6H), 2.08-1.98 (m, 2H), 2.01-1.86 (m, 2H). MS (m/z) 900.996 (M+H)+.

Example 119: (3S,3'S)-4,4'-((((((2,2'-dimethyl-[1,1'-biphenyl]-3,3'-diyl)bis(methylene))bis(oxy))bis(2-methoxy-5-methylpyridine-6,3-diyl))bis(methylene))bis(azanediyl))bis(3-hydroxybutanoic acid)

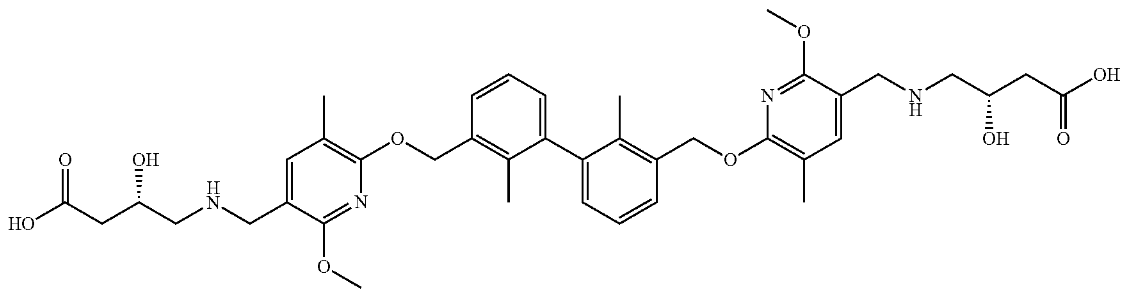 [SMILES: COc1nc(OCc2cccc(-c3cccc(COc4nc(OC)c(CNC[C@@H](O)CC(=O)O)cc4C)c3C)c2C)c(C)cc1CNC[C@@H](O)CC(=O)O]

-

Intermediate 25 (25 mg, 0.037 mmol), potassium carbonate (20.6 mg, 0.15 mmol), trimethylboroxine (18.7 mg, 0.15 mmol), and [1,1'-Bis(diphenylphosphino)ferrocene]dichloropalladium(II) (6 mg, 0.007 mmol) were suspended in dioxane (1 mL) and water (0.1 mL) in a 2 dram vial. The suspension was sparged with nitrogen gas for 5 minutes, sealed, and heated to 90° C. for 1 h. The reaction was diluted with ethyl acetate and washed with brine. The organic phase was dried over anhydrous sodium sulfate, and concentrated to provide the crude product which was used directly in the next step following reductive amination procedure G to provide 6 mg of the title compound as the bis-TFA salt. $^1$H NMR (400 MHz, Methanol-$d_4$) δ 7.51 (s, 2H), 7.44 (d, J=7.4 Hz, 2H), 7.23 (t, J=7.6 Hz, 2H), 7.06 (d, J=7.6 Hz, 2H), 5.53 (s, 4H), 4.28 (d, J=6.3 Hz, 2H), 4.14 (s, 4H), 4.01 (s, 6H), 3.18 (dd, J=12.8, 3.1 Hz, 2H), 2.97 (dd, J=12.7, 9.8 Hz, 2H), 2.53 (d, J=6.3 Hz, 4H), 2.16 (s, 6H), 2.08 (s, 6H). MS (m/z) 747.073 (M+H)+.

Example 120: (3S,3'S)-4,4'-((((((2,2'-dimethyl-[1,1'-biphenyl]-3,3'-diyl)bis(methylene))bis(oxy))bis(2-methoxy-5-vinylpyridine-6,3-diyl))bis(methylene))bis(azanediyl))bis(3-hydroxybutanoic acid) (or (3S,3'S)-4,4'-(((6,6'-(((2,2'-dimethyl-[1,1'-biphenyl]-3,3'-diyl)bis(methylene))bis(oxy))bis(2-methoxy-5-vinylpyridine-6,3-diyl))bis(methylene))bis(azanediyl))bis(3-hydroxybutanoic acid))

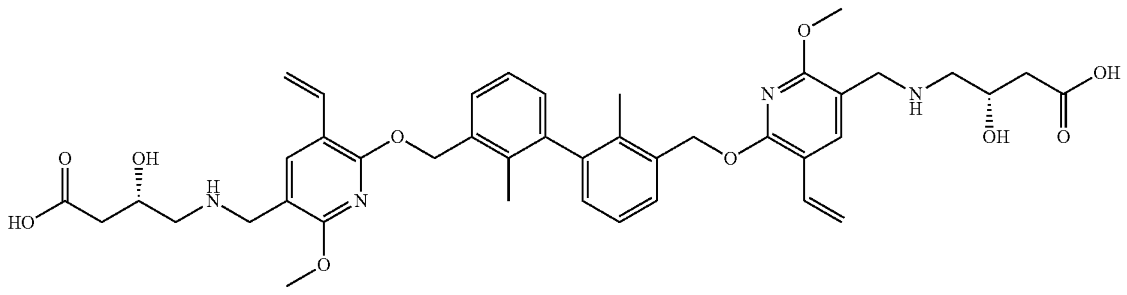 [SMILES: C=Cc1cc(CNC[C@@H](O)CC(=O)O)c(OC)nc1OCc1cccc(-c2cccc(COc3nc(OC)c(CNC[C@@H](O)CC(=O)O)cc3C=C)c2C)c1C]

The title compound was synthesized analogously to Example 119 using potassium vinyltrifluoroborate in place of trimethylboroxine, and following reductive amination procedure G. $^1$H NMR (400 MHz, Methanol-$d_4$) δ 7.89 (s, 2H), 7.44 (d, J=7.7 Hz, 2H), 7.24 (t, J=7.6 Hz, 2H), 7.07 (d, J=7.7 Hz, 2H), 6.83 (dd, J=17.8, 11.3 Hz, 2H), 5.76 (dd, J=17.8, 1.3 Hz, 2H), 5.57 (s, 4H), 5.31-5.14 (m, 2H), 4.35-4.23 (m, 2H), 4.18 (s, 4H), 4.05 (s, 4H), 3.20 (dd, J=12.8, 3.1 Hz, 2H), 2.99 (dd, J=12.7, 9.8 Hz, 2H), 2.54 (d, J=6.3 Hz, 4H), 2.07 (s, 6H). MS (m/z) 771.103 (M+H)+.

Example 121: (3S,3'S)-4,4'-((((((2,2'-dimethyl-[1,1'-biphenyl]-3,3'-diyl)bis(methylene))bis(oxy))bis(5-bromo-2-((3,5-dicyanobenzyl)oxy)pyridine-6,3-diyl))bis(methylene))bis(azanediyl))bis(3-hydroxybutanoic acid) (or (3S,3'S)-4,4'-(((6,6'-(((2,2'-dimethyl-[1,1'-biphenyl]-3,3'-diyl)bis(methylene))bis(oxy))bis(5-bromo-2-((3,5-dicyanobenzyl)oxy)pyridine-6,3-diyl))bis(methylene))bis(azanediyl))bis(3-hydroxybutanoic acid))

Intermediate 24 (24 mg, 0.037 mmol), 5-(hydroxymethyl)isophthalonitrile (17.7 mg, 0.11 mmol), and triphenylphosphine (29.4 mg, 0.11 mmol) were charged into a 2dram vial. The contents was dissolved in tetrahydrofuran (1 mL) and stirred, while diisopropyl azodicarboxylate (22.7 mg, 0.11 mmol) in THF (0.3 mL) was added dropwise. After stirring for 2 h at room temperature, the reaction was concentrated in vacuo, and the crude product was used directly in the next step following reductive amination procedure G to provide 11 mg of the title compound as the bis-TFA salt. $^1$H NMR (400 MHz, Methanol-$d_4$) δ 8.19-8.15 (m, 4H), 8.16-8.12 (m, 2H), 8.04 (s, 2H), 7.38 (d, J=7.0 Hz, 2H), 7.23 (t, J=7.6 Hz, 2H), 7.07 (dd, J=7.5, 1.3 Hz, 2H), 5.58 (t, J=2.7 Hz, 4H), 5.51-5.37 (m, 4H), 4.36-4.21 (m, 6H), 3.26 (dd, J=12.7, 3.1 Hz, 2H), 3.04 (dd, J=12.7, 9.8 Hz, 2H), 2.55 (dd, J=6.2, 0.8 Hz, 4H), 2.02 (s, 6H). MS (m/z) 1128.910 (M+H)+.

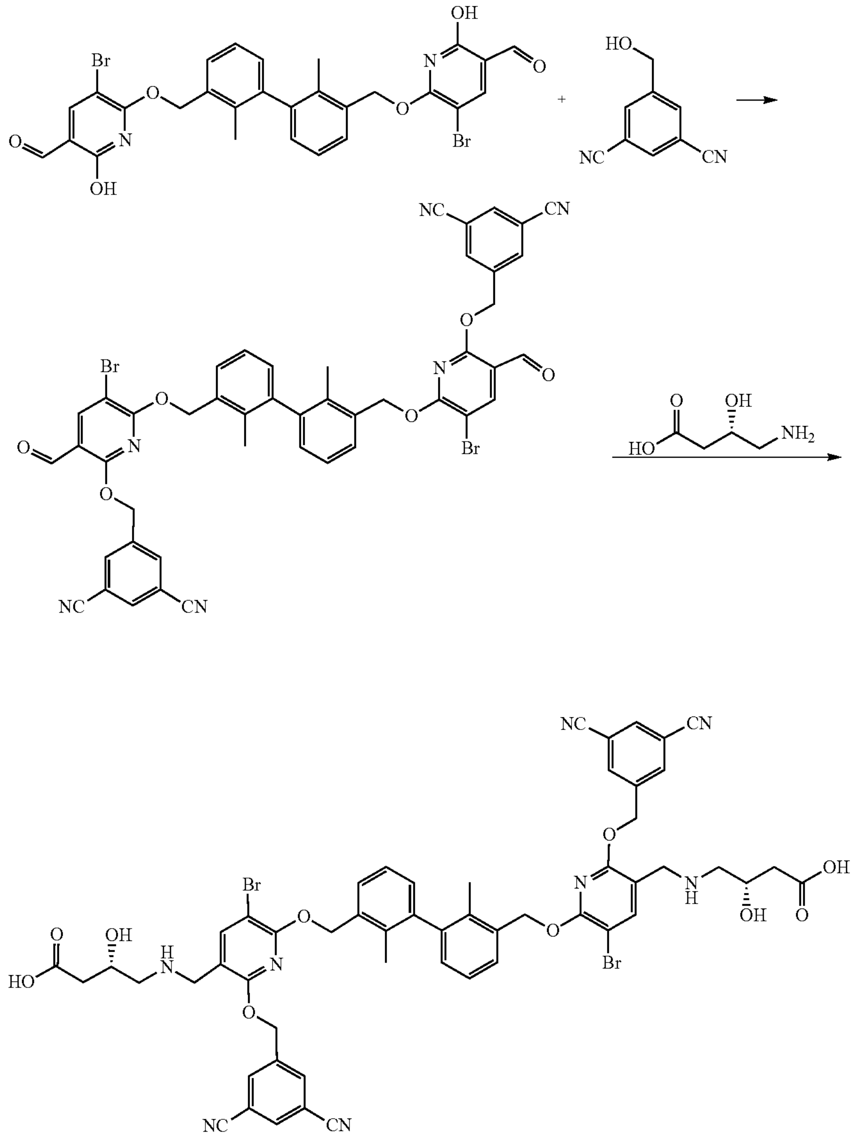

Example 122: (3S,3'S)-4,4'-((((((2,2'-dimethyl-[1,1'-biphenyl]-3,3'-diyl)bis(methylene))bis(oxy))bis(5-chloro-2-((3,5-dicyanobenzyl)oxy)pyridine-6,3-diyl))bis(methylene))bis(azanediyl))bis(3-hydroxybutanoic acid) (or (3S,3'S)-4,4'-(((6,6'-(((2,2'-dimethyl-[1,1'-biphenyl]-3,3'-diyl)bis(methylene))bis(oxy))bis(5-chloro-2-((3,5-dicyanobenzyl)oxy)pyridine-6,3-diyl))bis(methylene))bis(azanediyl))bis(3-hydroxybutanoic acid))

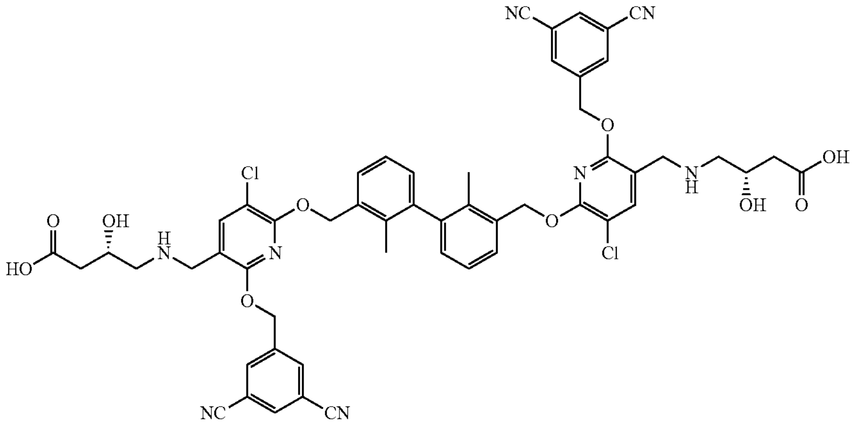 [SMILES: Cc1c(COc2nc(OCc3cc(C#N)cc(C#N)c3)c(CNC[C@@H](O)CC(=O)O)cc2Cl)cccc1-c1cccc(COc2nc(OCc3cc(C#N)cc(C#N)c3)c(CNC[C@@H](O)CC(=O)O)cc2Cl)c1C]

The title compound was synthesized analogously to Example 121 using intermediate 32 in place of intermediate 24. $^1$H NMR (400 MHz, Methanol-$d_4$) δ 8.17 (d, J=1.5 Hz, 4H), 8.15 (d, J=1.5 Hz, 2H), 7.90 (s, 2H), 7.45-7.32 (m, 2H), 7.23 (t, J=7.6 Hz, 2H), 7.16-7.02 (m, 2H), 5.58 (s, 4H), 5.51-5.41 (m, 4H), 4.33-4.19 (m, 6H), 3.26 (dd, J=12.7, 3.1 Hz, 2H), 3.04 (dd, J=12.7, 9.8 Hz, 2H), 2.55 (dd, J=6.3, 1.0 Hz, 4H), 2.02 (s, 6H). MS (m/z) 1038.8985 (M+H)+.

Example 123: (2S,2'S)-2,2'-((((((2,2'-dimethyl-[1,1'-biphenyl]-3,3'-diyl)bis(methylene))bis(oxy))bis(5-chloro-2-((3,5-dicyanobenzyl)oxy)pyridine-6,3-diyl))bis(methylene))bis(azanediyl))bis(3-hydroxy-2-methylpropanoic acid) (or (2S,2'S)-2,2'-(((6,6'-(((2,2'-dimethyl-[1,1'-biphenyl]-3,3'-diyl)bis(methylene))bis(oxy))bis(5-chloro-2-((3,5-dicyanobenzyl)oxy)pyridine-6,3-diyl))bis(methylene))bis(azanediyl))bis(3-hydroxy-2-methylpropanoic acid))

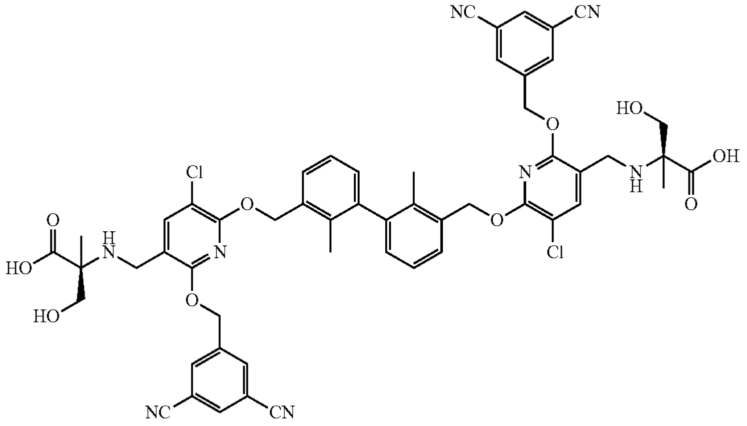 [SMILES: Cc1c(COc2nc(OCc3cc(C#N)cc(C#N)c3)c(CN[C@](C)(CO)C(=O)O)cc2Cl)cccc1-c1cccc(COc2nc(OCc3cc(C#N)cc(C#N)c3)c(CN[C@](C)(CO)C(=O)O)cc2Cl)c1C]

The title compound was synthesized analogously to Example 121 using intermediate 32 in place of intermediate 24 and following reductive amination procedure G using (S)-2-methylserine in place of (3S)-4-amino-3-hydroxybutanoic acid. $^1$H NMR (400 MHz, Methanol-$d_4$) δ 8.20 (d, J=1.5 Hz, 4H), 8.14 (d, J=1.5 Hz, 2H), 7.93 (s, 2H), 7.38 (d, J=7.6 Hz, 2H), 7.22 (t, J=7.6 Hz, 2H), 7.07 (d, J=7.3 Hz, 2H), 5.62-5.53 (m, 4H), 5.53-5.43 (m, 4H), 4.29 (s, 4H), 4.06 (d, J=12.1 Hz, 2H), 3.84 (d, J=12.2 Hz, 2H), 2.02 (s, 6H), 1.58 (s, 6H). MS (m/z) 1039.058 (M+H)+.

Example 124: (2S,2'S)-2,2'-((((((2,2'-dimethyl-[1,1'-biphenyl]-3,3'-diyl)bis(methylene))bis(oxy))bis(5-chloro-2-((3,5-dicyanobenzyl)oxy)pyridine-6,3-diyl))bis(methylene))bis(azanediyl))bis(3-hydroxypropanoic acid)

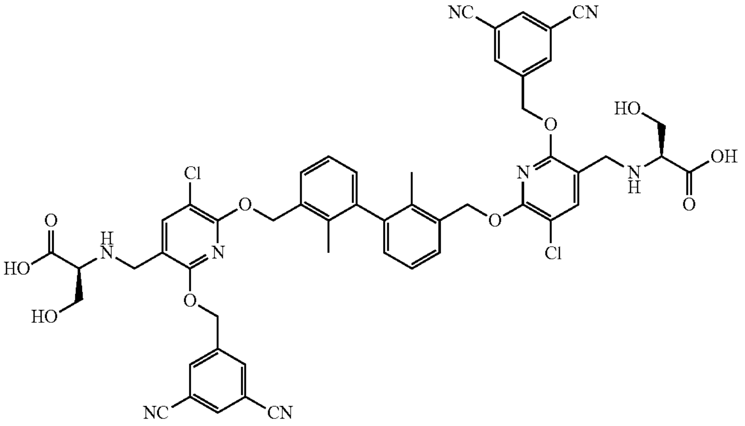 [SMILES: Cc1c(COc2nc(OCc3cc(C#N)cc(C#N)c3)c(CN[C@@H](CO)C(=O)O)cc2Cl)cccc1-c1cccc(COc2nc(OCc3cc(C#N)cc(C#N)c3)c(CN[C@@H](CO)C(=O)O)cc2Cl)c1C]

The title compound was synthesized analogously to Example 121 using intermediate 32 in place of intermediate 24 and following reductive amination procedure G using (L)-serine in place of (3S)-4-amino-3-hydroxybutanoic acid. $^1$H NMR (400 MHz, Methanol-$d_4$) δ 8.18 (s, 4H), 8.14 (d, J=1.6 Hz, 2H), 7.91 (s, 2H), 7.38 (d, J=7.5 Hz, 2H), 7.23 (t, J=7.7 Hz, 2H), 7.07 (d, J=7.5 Hz, 2H), 5.65-5.51 (m, 4H), 5.47 (d, J=3.1 Hz, 4H), 4.33 (q, J=13.5 Hz, 4H), 4.09-3.93 (m, 6H), 2.02 (s, 6H). MS (m/z) 1010.992 (M+H)+.

Example 125: 2,2'-((((((2,2'-dimethyl-[1,1'-biphenyl]-3,3'-diyl)bis(methylene))bis(oxy))bis(5-chloro-2-((3,5-dicyanobenzyl)oxy)pyridine-6,3-diyl))bis(methylene))bis(azanediyl))diacetic acid (or 2,2'-(((6,6'-(((2,2'-dimethyl-[1,1'-biphenyl]-3,3'-diyl)bis(methylene))bis(oxy))bis(5-chloro-2-((3,5-dicyanobenzyl)oxy)pyridine-6,3-diyl))bis(methylene))bis(azanediyl))diacetic acid)

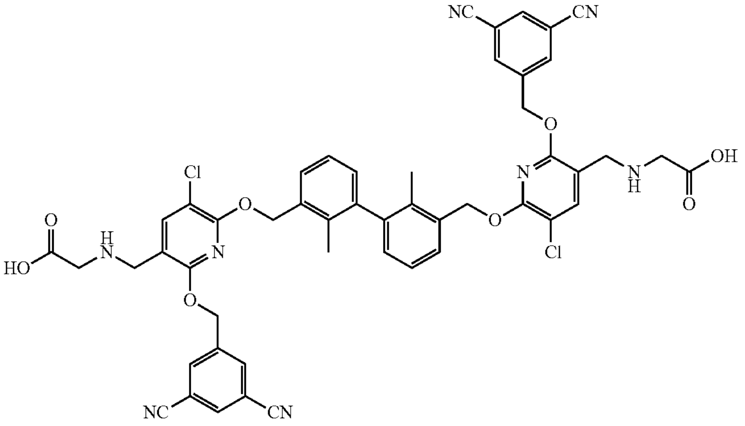 [SMILES: Cc1c(COc2nc(OCc3cc(C#N)cc(C#N)c3)c(CNCC(=O)O)cc2Cl)cccc1-c1cccc(COc2nc(OCc3cc(C#N)cc(C#N)c3)c(CNCC(=O)O)cc2Cl)c1C]

The title compound was synthesized analogously to Example 121 using intermediate 32 in place of intermediate 24 and following reductive amination procedure G using glycine in place of (3S)-4-amino-3-hydroxybutanoic acid. $^1$H NMR (400 MHz, Methanol-$d_4$) δ 8.18 (d, J=1.5 Hz, 4H), 8.14 (t, J=1.6 Hz, 2H), 7.89 (s, 2H), 7.45-7.29 (m, 2H), 7.23 (t, J=7.6 Hz, 2H), 7.14-7.03 (m, 2H), 5.65-5.53 (m, 4H), 5.53-5.42 (m, 4H), 4.28 (s, 4H), 3.92 (s, 4H), 2.02 (s, 6H). MS (m/z) 950.991 (M+H)+.

Example 126: (3S,3'S)-4,4'-((((((2,2'-dimethyl-[1,1'-biphenyl]-3,3'-diyl)bis(methylene))bis(oxy))bis(5-bromo-2-(pyrimidin-5-ylmethoxy)pyridine-6,3-diyl))bis(methylene))bis(azanediyl))bis(3-hydroxybutanoic acid) (or (3S,3'S)-4,4'-(((6,6'-(((2,2'-dimethyl-[1,1'-biphenyl]-3,3'-diyl)bis(methylene))bis(oxy))bis(5-bromo-2-(pyrimidin-5-ylmethoxy)pyridine-6,3-diyl))bis(methylene))bis(azanediyl))bis(3-hydroxybutanoic acid))

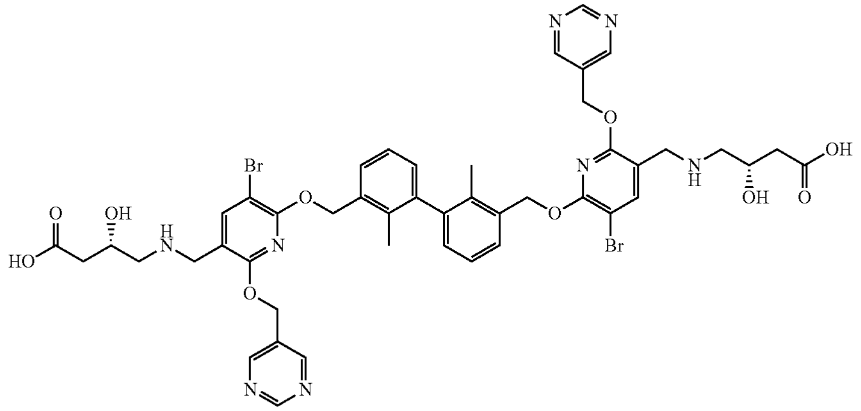 [SMILES: Cc1c(COc2nc(OCc3cncnc3)c(CNC[C@@H](O)CC(=O)O)cc2Br)cccc1-c1cccc(COc2nc(OCc3cncnc3)c(CNC[C@@H](O)CC(=O)O)cc2Br)c1C]

The title compound was synthesized analogously to Example 121 using pyrimidin-5-ylmethanol in place of 5-(hydroxymethyl)isophthalonitrile, and following reductive amination procedure G. $^1$H NMR (400 MHz, Methanol-$d_4$) δ 9.13 (s, 2H), 8.94 (s, 4H), 8.03 (s, 2H), 7.43 (d, J=7.8 Hz, 2H), 7.24 (t, J=7.6 Hz, 2H), 7.09 (d, J=7.3 Hz, 2H), 5.55 (m, 8H), 4.36-4.18 (m, 6H), 3.23 (dd, J=12.7, 3.1 Hz, 2H), 3.01 (dd, J=12.7, 9.8 Hz, 2H), 2.53 (d, J=6.3 Hz, 4H), 2.06 (s, 6H). MS (m/z) 517.059 (M+2H) 2+.

Example 127: (3S,3'S)-4,4'-((((((2,2'-dimethyl-[1,1'-biphenyl]-3,3'-diyl)bis(methylene))bis(oxy))bis(5-bromo-2-(2-(pyrimidin-5-yl)ethoxy)pyridine-6,3-diyl))bis(methylene))bis(azanediyl))bis(3-hydroxybutanoic acid) (or (3S,3'S)-4,4'-(((6,6'-(((2,2'-dimethyl-[1,1'-biphenyl]-3,3'-diyl)bis(methylene))bis(oxy))bis(5-bromo-2-(2-(pyrimidin-5-yl)ethoxy)pyridine-6,3-diyl))bis(methylene))bis(azanediyl))bis(3-hydroxybutanoic acid))

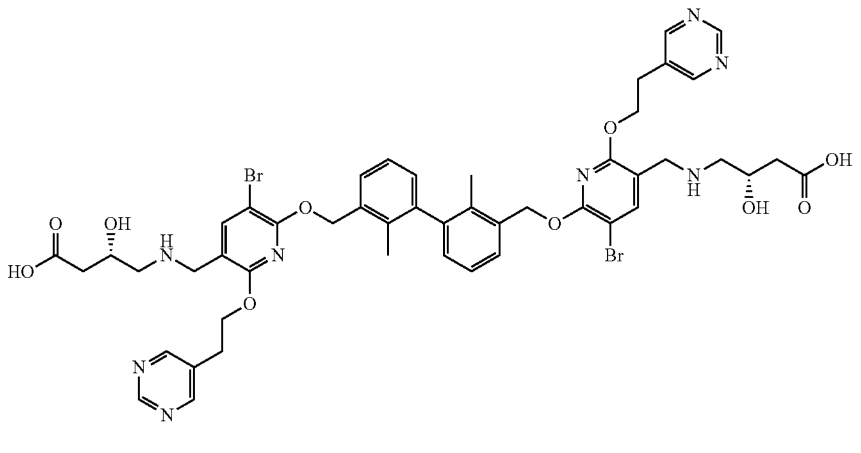 [SMILES: Cc1c(COc2nc(OCCc3cncnc3)c(CNC[C@@H](O)CC(=O)O)cc2Br)cccc1-c1cccc(COc2nc(OCCc3cncnc3)c(CNC[C@@H](O)CC(=O)O)cc2Br)c1C]

The title compound was synthesized analogously to Example 121 using 2-(pyrimidin-5-yl)ethan-1-ol in place of 5-(hydroxymethyl)isophthalonitrile, and following reductive amination procedure G. $^1$H NMR (400 MHz, Methanol-d4) δ 9.03 (s, 2H), 8.77 (s, 4H), 7.96 (s, 2H), 7.44 (d, J=7.2 Hz, 2H), 7.23 (t, J=7.6 Hz, 2H), 7.05 (dd, J=7.7, 1.4 Hz, 2H), 5.54 (s, 4H), 4.71 (t, J=6.4 Hz, 4H), 4.24 (dtd, J=9.4, 6.3, 3.0 Hz, 2H), 4.18-4.04 (m, 6H), 3.25-3.13 (m, 6H), 2.97 (dd, J=12.7, 9.8 Hz, 2H), 2.55 (d, J=6.3 Hz, 4H), 2.06 (s, 6H). MS (m/z) 1060.991 (M+H)+.

Example 128: (3S,3'S)-4,4'-((((((2,2'-dimethyl-[1,1'-biphenyl]-3,3'-diyl)bis(methylene))bis(oxy))bis(5-bromo-2-(2-(4-cyanopyridin-2-yl)ethoxy)pyridine-6,3-diyl))bis(methylene))bis(azanediyl))bis(3-hydroxybutanoic acid) (or (3S,3'S)-4,4'-(((6,6'-(((2,2'-dimethyl-[1,1'-biphenyl]-3,3'-diyl)bis(methylene))bis(oxy))bis(5-bromo-2-(2-(4-cyanopyridin-2-yl)ethoxy)pyridine-6,3-diyl))bis(methylene))bis(azanediyl))bis(3-hydroxybutanoic acid))

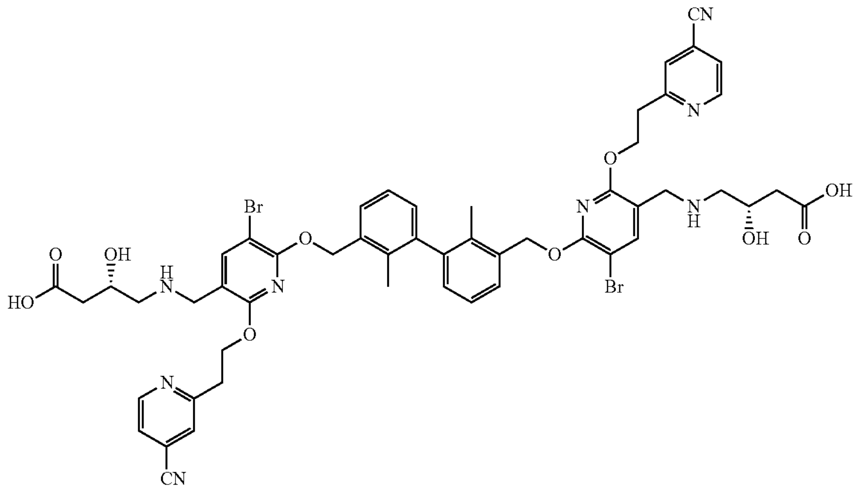 [SMILES: Cc1c(COc2nc(OCCc3cc(C#N)ccn3)c(CNC[C@@H](O)CC(=O)O)cc2Br)cccc1-c1cccc(COc2nc(OCCc3cc(C#N)ccn3)c(CNC[C@@H](O)CC(=O)O)cc2Br)c1C]

The title compound was synthesized analogously to Example 121 using 2-(2-hydroxyethyl)isonicotinonitrile in place of 5-(hydroxymethyl)isophthalonitrile, and following reductive amination procedure G. $^1$H NMR (400 MHz, Methanol-$d_4$) δ 8.76-8.68 (m, 2H), 7.94 (s, 2H), 7.76 (s, 2H), 7.59 (dd, J=5.1, 1.5 Hz, 2H), 7.45 (d, J=7.4 Hz, 2H), 7.22 (t, J=7.6 Hz, 2H), 7.04 (d, J=7.5 Hz, 2H), 5.57-5.50 (m, 4H), 4.26 (dd, J=9.3, 6.6 Hz, 2H), 4.09 (d, J=2.6 Hz, 4H), 3.38 (t, J=6.3 Hz, 5H), 3.20 (dd, J=12.7, 3.1 Hz, 2H), 2.99 (dd, J=12.7, 9.9 Hz, 2H), 2.54 (d, J=6.3 Hz, 4H), 2.06 (s, 6H). MS (m/z) 1108.987 (M+H)+.

Example 129:2,2'-((((((2,2'-dimethyl-[1,1'-biphenyl]-3,3'-diyl)bis(methylene))bis(oxy))bis(5-bromo-2-(((R)-5-oxopyrrolidin-2-yl)methoxy)pyridine-6,3-diyl))bis(methylene))bis(azanediyl))diacetic acid

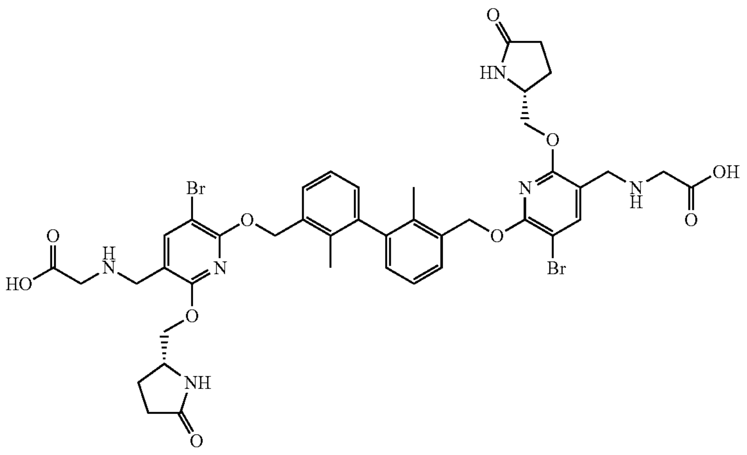 [SMILES: Cc1c(COc2nc(OC[C@H]3CCC(=O)N3)c(CNCC(=O)O)cc2Br)cccc1-c1cccc(COc2nc(OC[C@H]3CCC(=O)N3)c(CNCC(=O)O)cc2Br)c1C]

The title compound was synthesized analogously to Example 121 using (S)-5-(hydroxymethyl)pyrrolidin-2-one in place of 5-(hydroxymethyl)isophthalonitrile, and following reductive amination procedure G using glycine in place of (3S)-4-amino-3-hydroxybutanoic acid. $^1$H NMR (400 MHz, Methanol-$d_4$) δ 7.98 (d, J=0.7 Hz, 2H), 7.45 (d, J=7.6 Hz, 2H), 7.25 (t, J=7.6 Hz, 2H), 7.07 (d, J=7.5 Hz, 2H), 5.57 (m, 4H), 4.60-4.43 (m, 2H), 4.35-4.26 (m, 2H), 4.26-4.10 (m, 6H), 3.93 (s, 4H), 2.55-2.29 (m, 6H), 2.09 (s, 6H), 2.00-1.89 (m, 2H). MS (m/z) 954.980 (M+H)+.

Example 130: 2,2'-((((((2,2'-dimethyl-[1,1'-biphenyl]-3,3'-diyl)bis(methylene))bis(oxy))bis(5-bromo-2-(((S)-5-oxopyrrolidin-2-yl)methoxy)pyridine-6,3-diyl))bis(methylene))bis(azanediyl))diacetic acid

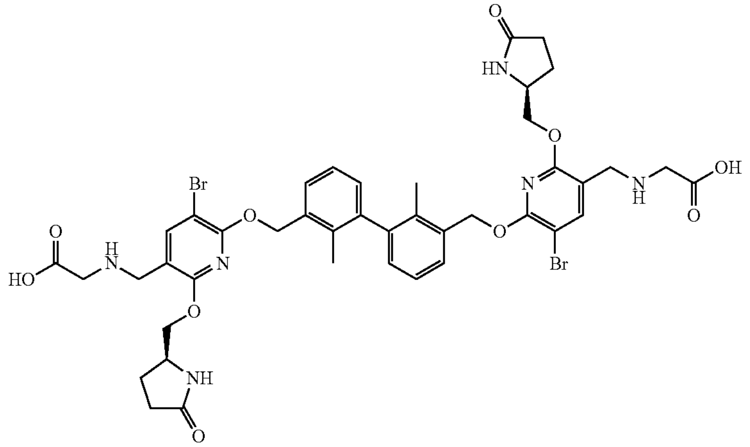 [SMILES: Cc1c(COc2nc(OC[C@@H]3CCC(=O)N3)c(CNCC(=O)O)cc2Br)cccc1-c1cccc(COc2nc(OC[C@@H]3CCC(=O)N3)c(CNCC(=O)O)cc2Br)c1C]

The title compound was synthesized analogously to Example 121 using (R)-5-(hydroxymethyl)pyrrolidin-2-one in place of 5-(hydroxymethyl)isophthalonitrile, and following reductive amination procedure G using glycine in place of (3S)-4-amino-3-hydroxybutanoic acid. $^1$H NMR (400 MHz, Methanol-$d_4$) δ 7.98 (d, J=0.7 Hz, 2H), 7.45 (d, J=7.7 Hz, 2H), 7.25 (t, J=7.6 Hz, 2H), 7.07 (d, J=7.6 Hz, 2H), 5.61-5.51 (m, 4H), 4.55-4.46 (m, 2H), 4.39-4.26 (m, 2H), 4.26-4.09 (m, 6H), 3.91 (s, 4H), 2.50-2.26 (m, 6H), 2.09 (s, 6H), 1.95 (m, 2H). MS (m/z) 955.025 (M+H)+.

Example 131: (3S,3'S)-4,4'-((((((2,2'-dimethyl-[1,1'-biphenyl]-3,3'-diyl)bis(methylene))bis(oxy))bis(5-bromo-2-(oxetan-2-ylmethoxy)pyridine-6,3-diyl))bis(methylene))bis(azanediyl))bis(3-hydroxybutanoic acid) (or (3S,3'S)-4,4'-(((6,6'-(((2,2'-dimethyl-[1,1'-biphenyl]-3,3'-diyl)bis(methylene))bis(oxy))bis(5-bromo-2-(oxetan-2-ylmethoxy)pyridine-6,3-diyl))bis(methylene))bis(azanediyl))bis(3-hydroxybutanoic acid))

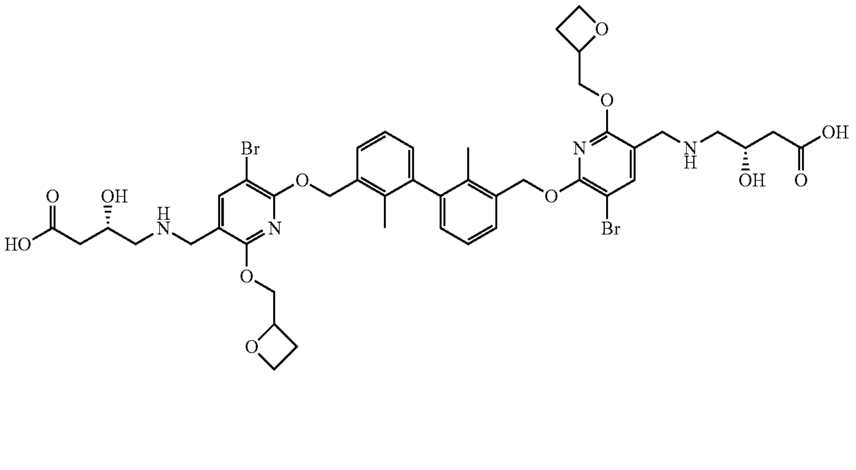 [SMILES: Cc1c(COc2nc(OCC3CCO3)c(CNC[C@@H](O)CC(=O)O)cc2Br)cccc1-c1cccc(COc2nc(OCC3CCO3)c(CNC[C@@H](O)CC(=O)O)cc2Br)c1C]

The title compound was synthesized analogously to Example 121 using oxetan-2-ylmethanol in place of 5-(hydroxymethyl)isophthalonitrile, and following reductive amination procedure G. $^1$H NMR (400 MHz, Methanol-$d_4$) δ 7.99 (s, 2H), 7.46 (d, J=7.5 Hz, 2H), 7.25 (t, J=7.6 Hz, 2H), 7.08 (d, J=7.5 Hz, 2H), 5.68-5.49 (m, 4H), 5.33-5.14 (m, 2H), 4.80-4.72 (m, 2H), 4.69-4.60 (m, 4H), 4.56 (dt, J=11.9, 3.0 Hz, 2H), 4.33-4.23 (m, 2H), 4.23-4.12 (m, 4H), 3.23 (dd, J=12.7, 3.0 Hz, 2H), 3.02 (dd, J=12.7, 10.0 Hz, 2H), 2.78 (q, J=8.5, 6.6 Hz, 2H), 2.65 (p, J=8.3 Hz, 2H), 2.54 (d, J=6.2 Hz, 4H), 2.10 (s, 6H). MS (m/z) 988.919 (M+H)+.

Example 132: (3S,3'S)-4,4'-((((((2,2'-dimethyl-[1,1'-biphenyl]-3,3'-diyl)bis(methylene))bis(oxy))bis(5-bromo-2-(oxetan-3-ylmethoxy)pyridine-6,3-diyl))bis(methylene))bis(azanediyl))bis(3-hydroxybutanoic acid) (or (3S,3'S)-4,4'-(((6,6'-(((2,2'-dimethyl-[1,1'-biphenyl]-3,3'-diyl)bis(methylene))bis(oxy))bis(5-bromo-2-(oxetan-3-ylmethoxy)pyridine-6,3-diyl))bis(methylene))bis(azanediyl))bis(3-hydroxybutanoic acid))

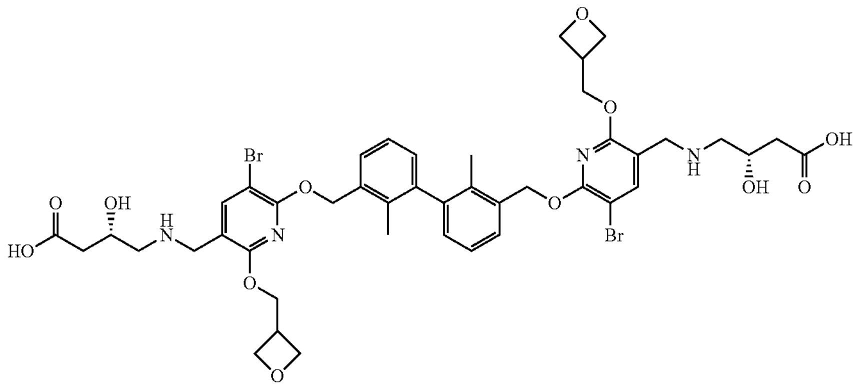 [SMILES: Cc1c(COc2nc(OCC3COC3)c(CNC[C@@H](O)CC(=O)O)cc2Br)cccc1-c1cccc(COc2nc(OCC3COC3)c(CNC[C@@H](O)CC(=O)O)cc2Br)c1C]

The title compound was synthesized analogously to Example 121 using oxetan-3-ylmethanolin place of 5-(hydroxymethyl)isophthalonitrile, and following reductive amination procedure G. $^1$H NMR (400 MHz, Methanol-$d_4$) δ 7.98 (s, 2H), 7.45 (d, J=7.4 Hz, 2H), 7.24 (t, J=7.6 Hz, 2H), 7.08 (d, J=7.6 Hz, 2H), 5.57 (s, 4H), 4.94-4.87 (m, 4H), 4.72-4.63 (m, 4H), 4.58 (q, J=6.4 Hz, 4H), 4.35-4.21 (m, 2H), 4.19 (s, 4H), 3.54-3.40 (m, 2H), 3.24 (dd, J=12.6, 3.0 Hz, 2H), 3.02 (dd, J=12.7, 9.8 Hz, 2H), 2.54 (d, J=6.3 Hz, 4H), 2.09 (s, 6H). MS (m/z) 988.93 (M+H)+.

Example 133: 2,2'-((((((2,2'-dimethyl-[1,1'-biphenyl]-3,3'-diyl)bis(methylene))bis(oxy))bis(5-chloro-2-(2-(pyrimidin-5-yl)ethoxy)pyridine-6,3-diyl))bis(methylene))bis(azanediyl))diacetic acid (or 2,2'-(((6,6'-(((2,2'-dimethyl-[1,1'-biphenyl]-3,3'-diyl)bis(methylene))bis(oxy))bis(5-chloro-2-(2-(pyrimidin-5-yl)ethoxy)pyridine-6,3-diyl))bis(methylene))bis(azanediyl))diacetic acid)

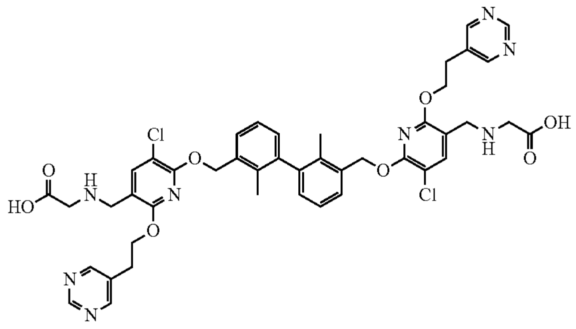 [SMILES: Cc1c(COc2nc(OCCc3cncnc3)c(CNCC(=O)O)cc2Cl)cccc1-c1cccc(COc2nc(OCCc3cncnc3)c(CNCC(=O)O)cc2Cl)c1C]

The title compound was synthesized analogously to Example 121 using intermediate 32 in place of intermediate 24, using 2-(pyrimidin-5-yl)ethan-1-ol in place of 5-(hydroxymethyl)isophthalonitrile, and following reductive amination procedure G using glycine in place of (3S)-4-amino-3-hydroxybutanoic acid. $^1$H NMR (400 MHz, Methanol-$d_4$) δ 9.02 (s, 2H), 8.77 (s, 4H), 7.82 (s, 2H), 7.44 (d, J=7.4 Hz, 2H), 7.23 (t, J=7.6 Hz, 2H), 7.05 (d, J=7.1 Hz, 2H), 5.55 (s, 4H), 4.70 (t, J=6.0 Hz, 4H), 4.14 (s, 4H), 3.84 (s, 4H), 3.20 (t, J=6.3 Hz, 4H), 2.05 (s, 6H). MS (m/z) 883.010 (M+H)+.

Example 134: (3S,3'S)-4,4'-((((((2,2'-dimethyl-[1,1'-biphenyl]-3,3'-diyl)bis(methylene))bis(oxy))bis(5-chloro-2-(3-(methylamino)-3-oxopropoxy)pyridine-6,3-diyl))bis(methylene))bis(azanediyl))bis(3-hydroxybutanoic acid) (or (3S,3'S)-4,4'-(((6,6'-(((2,2'-dimethyl-[1,1'-biphenyl]-3,3'-diyl)bis(methylene))bis(oxy))bis(5-chloro-2-(3-(methylamino)-3-oxopropoxy)pyridine-6,3-diyl))bis(methylene))bis(azanediyl))bis(3-hydroxybutanoic acid))

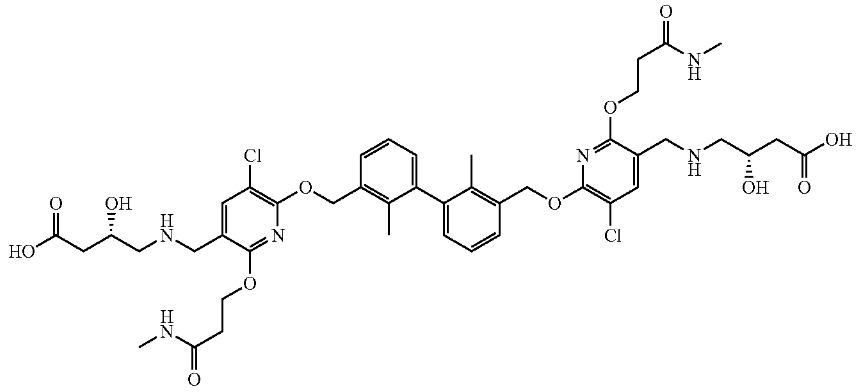 [SMILES: CNC(=O)CCOc1nc(OCc2cccc(-c3cccc(COc4nc(OCCC(=O)NC)c(CNC[C@@H](O)CC(=O)O)cc4Cl)c3C)c2C)c(Cl)cc1CNC[C@@H](O)CC(=O)O]

The title compound was synthesized analogously to Example 121 using intermediate 32 in place of intermediate 24, using 3-hydroxy-N-methylpropanamide in place of 5-(hydroxymethyl)isophthalonitrile, and following reductive amination procedure G. $^1$H NMR (400 MHz, Methanol-$d_4$) δ 7.81 (s, 2H), 7.46 (dd, J=7.7, 1.4 Hz, 2H), 7.25 (t, J=7.6 Hz, 2H), 7.08 (dd, J=7.7, 1.4 Hz, 2H), 5.57 (d, J=1.7 Hz, 4H), 4.67 (t, J=5.8 Hz, 4H), 4.36 (dtd, J=9.4, 6.3, 2.9 Hz, 2H), 4.14 (s, 4H), 3.20 (dd, J=12.8, 3.0 Hz, 2H), 3.00 (dd, J=12.7, 9.9 Hz, 2H), 2.74 (s, 6H), 2.69 (t, J=5.8 Hz, 4H), 2.55 (dd, J=6.3, 2.2 Hz, 4H), 2.08 (s, 6H). MS (m/z) 929.116 (M+H)+.

Example 135: (3S,3'S)-4,4'-((((((2,2'-dimethyl-[1,1'-biphenyl]-3,3'-diyl)bis(methylene))bis(oxy))bis(5-bromo-2-(3-(dimethylamino)-3-oxopropoxy)pyridine-6,3-diyl))bis(methylene))bis(azanediyl))bis(3-hydroxybutanoic acid) (or (3S,3'S)-4,4'-(((6,6'-(((2,2'-dimethyl-[1,1'-biphenyl]-3,3'-diyl)bis(methylene))bis(oxy))bis(5-bromo-2-(3-(dimethylamino)-3-oxopropoxy)pyridine-6,3-diyl))bis(methylene))bis(azanediyl))bis(3-hydroxybutanoic acid))

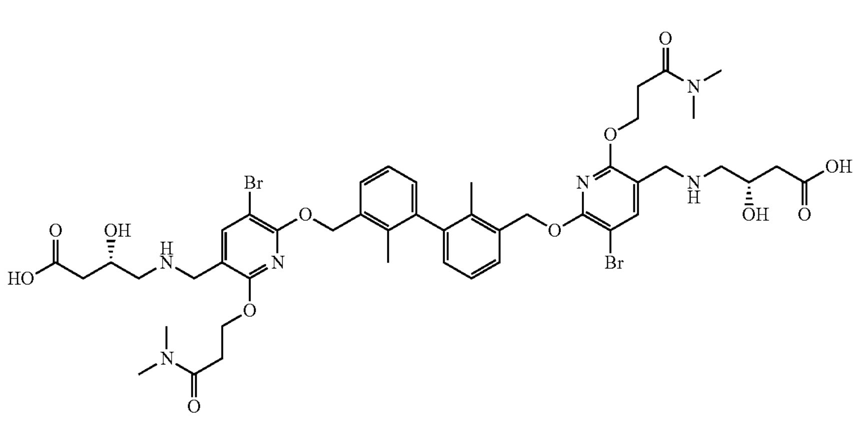 [SMILES: Cc1c(COc2nc(OCCC(=O)N(C)C)c(CNC[C@@H](O)CC(=O)O)cc2Br)cccc1-c1cccc(COc2nc(OCCC(=O)N(C)C)c(CNC[C@@H](O)CC(=O)O)cc2Br)c1C]

The title compound was synthesized analogously to Example 121 using 3-hydroxy-N,N-dimethylpropanamide in place of 5-(hydroxymethyl)isophthalonitrile, and following reductive amination procedure G. $^1$H NMR (400 MHz, Methanol-$d_4$) δ 7.94 (s, 2H), 7.52-7.43 (m, 2H), 7.24 (t, J=7.6 Hz, 2H), 7.08 (d, J=7.2 Hz, 2H), 5.62-5.50 (m, 4H), 4.72-4.62 (m, 4H), 4.40-4.26 (m, 2H), 4.13 (s, 4H), 3.19 (dd, J=12.7, 3.0 Hz, 2H), 3.08 (s, 6H), 3.03-2.98 (m, 2H), 2.96 (s, 6H), 2.92 (t, J=5.8 Hz, 4H), 2.54 (dd, J=6.3, 1.8 Hz, 4H), 2.09 (s, 6H). MS (m/z) 524.252 (M+2H) 2+.

Example 136: (3S,3'S)-4,4'-((((((2,2'-dimethyl-[1,1'-biphenyl]-3,3'-diyl)bis(methylene))bis(oxy))bis(5-chloro-2-((1-methyl-1H-pyrazol-4-yl)methoxy)pyridine-6,3-diyl))bis(methylene))bis(azanediyl))bis(3-hydroxybutanoic acid) (or (3S,3'S)-4,4'-(((6,6'-(((2,2'-dimethyl-[1,1'-biphenyl]-3,3'-diyl)bis(methylene))bis(oxy))bis(5-chloro-2-((1-methyl-1H-pyrazol-4-yl)methoxy)pyridine-6,3-diyl))bis(methylene))bis(azanediyl))bis(3-hydroxybutanoic acid))

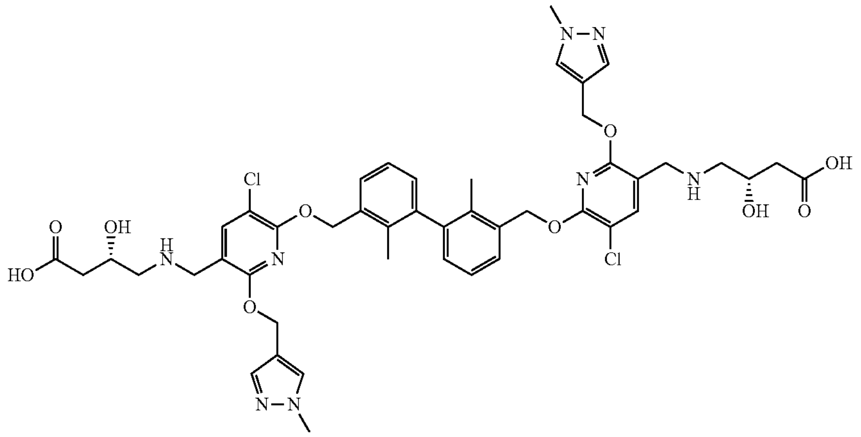 [SMILES: Cc1c(COc2nc(OCc3cnn(C)c3)c(CNC[C@@H](O)CC(=O)O)cc2Cl)cccc1-c1cccc(COc2nc(OCc3cnn(C)c3)c(CNC[C@@H](O)CC(=O)O)cc2Cl)c1C]

The title compound was synthesized analogously to Example 121 using intermediate 32 in place of intermediate 24, using (1-methyl-1H-pyrazol-4-yl)methanolin place of 5-(hydroxymethyl)isophthalonitrile, and following reductive amination procedure G. $^1$H NMR (400 MHz, Methanol-$d_4$) δ 7.83 (s, 2H), 7.59 (s, 2H), 7.51 (s, 2H), 7.45 (d, J=7.4 Hz, 2H), 7.25 (t, J=7.6 Hz, 2H), 7.05 (d, J=7.6 Hz, 2H), 5.72-5.53 (m, 4H), 5.50-5.31 (m, 4H), 4.20 (dp, J=9.6, 3.2 Hz, 2H), 4.12 (s, 4H), 3.83 (s, 6H), 3.13 (dd, J=12.7, 3.1 Hz, 2H), 2.92 (dd, J=12.7, 9.8 Hz, 2H), 2.47 (dd, J=6.3, 2.6 Hz, 4H), 2.07 (s, 6H). MS (m/z) 947.046 (M+H)+.

Example 137: (3S,3'S)-4,4'-((((((2,2'-dimethyl-[1,1'-biphenyl]-3,3'-diyl)bis(methylene))bis(oxy))bis(5-bromo-2-(pyridin-3-ylmethoxy)pyridine-6,3-diyl))bis(methylene))bis(azanediyl))bis(3-hydroxybutanoic acid) (or (3S,3'S)-4,4'-(((6,6'-(((2,2'-dimethyl-[1,1'-biphenyl]-3,3'-diyl)bis(methylene))bis(oxy))bis(5-bromo-2-(pyridin-3-ylmethoxy)pyridine-6,3-diyl))bis(methylene))bis(azanediyl))bis(3-hydroxybutanoic acid))

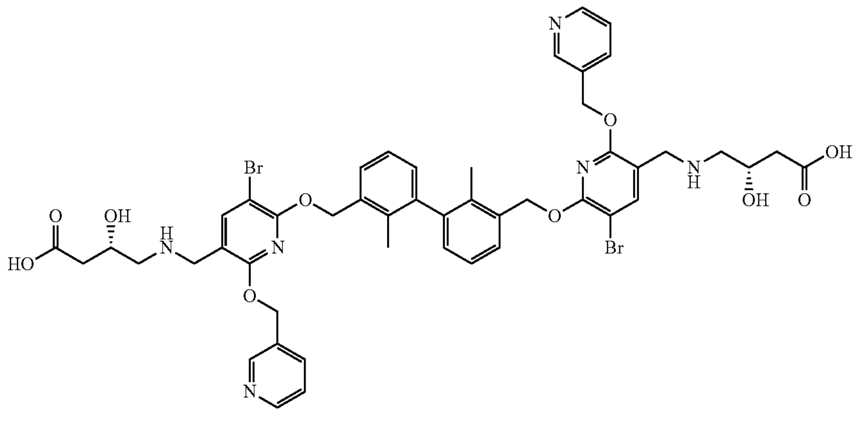 [SMILES: Cc1c(COc2nc(OCc3cccnc3)c(CNC[C@@H](O)CC(=O)O)cc2Br)cccc1-c1cccc(COc2nc(OCc3cccnc3)c(CNC[C@@H](O)CC(=O)O)cc2Br)c1C]

The title compound was synthesized analogously to Example 121 using pyridin-3-ylmethanol in place of 5-(hydroxymethyl)isophthalonitrile, and following reductive amination procedure G. $^1$H NMR (400 MHz, Methanol-$d_4$) δ 8.74 (s, 2H), 8.60-8.50 (m, 2H), 8.07 (d, J=7.8 Hz, 2H), 8.02 (s, 2H), 7.54 (dd, J=8.0, 5.0 Hz, 2H), 7.41 (d, J=8.0 Hz, 2H), 7.23 (t, J=7.6 Hz, 2H), 7.07 (d, J=7.7 Hz, 2H), 5.60 (s, 4H), 5.50 (s, 4H), 4.33-4.13 (m, 6H), 3.22 (dd, J=12.7, 3.0 Hz, 2H), 3.01 (dd, J=12.7, 9.8 Hz, 2H), 2.52 (d, J=6.3 Hz, 4H), 2.05 (s, 6H). MS (m/z) 1030.966 (M+H)+.

Example 138: (3S,3'S)-4,4'-((((((2,2'-dimethyl-[1,1'-biphenyl]-3,3'-diyl)bis(methylene))bis(oxy))bis(5-bromo-2-(thiazol-5-ylmethoxy)pyridine-6,3-diyl))bis(methylene))bis(azanediyl))bis(3-hydroxybutanoic acid) (or (3S,3'S)-4,4'-(((6,6'-(((2,2'-dimethyl-[1,1'-biphenyl]-3,3'-diyl)bis(methylene))bis(oxy))bis(5-bromo-2-(thiazol-5-ylmethoxy)pyridine-6,3-diyl))bis(methylene))bis(azanediyl))bis(3-hydroxybutanoic acid))

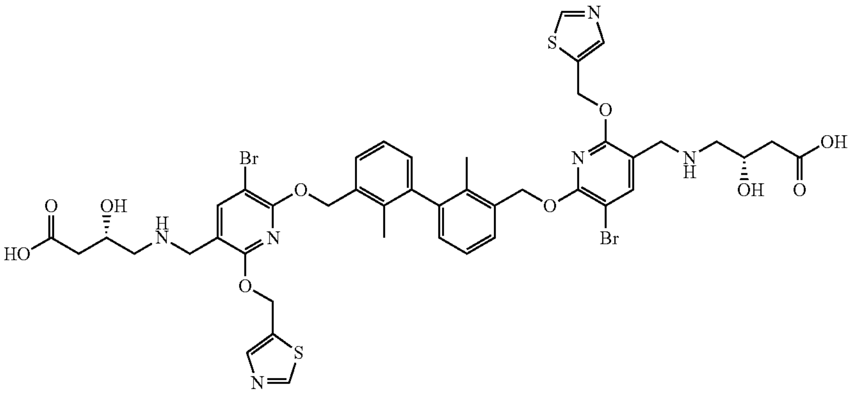 [SMILES: Cc1c(COc2nc(OCc3cncs3)c(CNC[C@@H](O)CC(=O)O)cc2Br)cccc1-c1cccc(COc2nc(OCc3cncs3)c(CNC[C@@H](O)CC(=O)O)cc2Br)c1C]

The title compound was synthesized analogously to Example 121 using thiazol-5-ylmethanol in place of 5-(hydroxymethyl)isophthalonitrile, and following reductive amination procedure G. $^1$H NMR (400 MHz, Methanol-$d_4$) δ 9.00 (d, J=0.8 Hz, 2H), 8.07-7.91 (m, 4H), 7.49-7.40 (m, 2H), 7.26 (t, J=7.6 Hz, 2H), 7.09 (dd, J=7.8, 1.4 Hz, 2H), 5.96-5.72 (m, 4H), 5.62 (s, 4H), 4.35-3.88 (m, 6H), 3.17 (dd, J=12.7, 3.1 Hz, 2H), 2.96 (dd, J=12.7, 9.8 Hz, 2H), 2.49 (dd, J=6.3, 1.7 Hz, 4H), 2.08 (s, 6H). MS (m/z) 1042.936 (M+H)+.

Example 139: (3S,3'S)-4,4'-((((((2,2'-dimethyl-[1,1'-biphenyl]-3,3'-diyl)bis(methylene))bis(oxy))bis(2-((1-benzyl-1H-1,2,3-triazol-5-yl)methoxy)-5-bromopyridine-6,3-diyl))bis(methylene))bis(azanediyl))bis(3-hydroxybutanoic acid) (or (3S,3'S)-4,4'-(((6,6'-(((2,2'-dimethyl-[1,1'-biphenyl]-3,3'-diyl)bis(methylene))bis(oxy))bis(2-((1-benzyl-1H-1,2,3-triazol-5-yl)methoxy)-5-bromopyridine-6,3-diyl))bis(methylene))bis(azanediyl))bis(3-hydroxybutanoic acid))

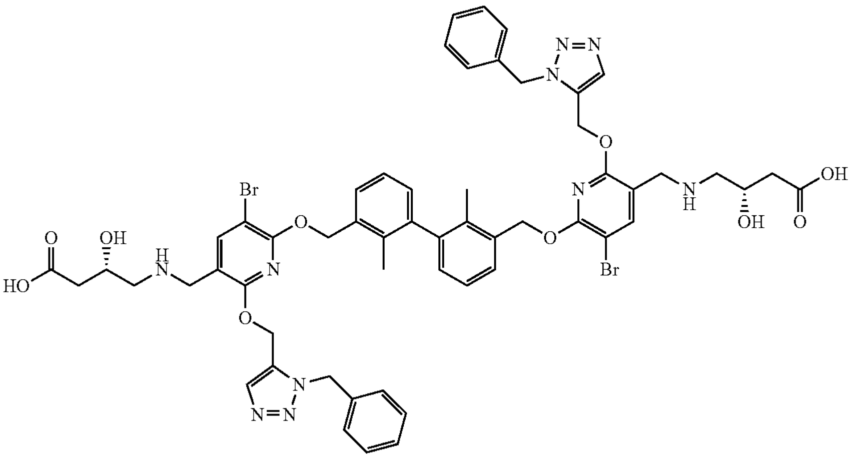 [SMILES: Cc1c(COc2nc(OCc3cnnn3Cc3ccccc3)c(CNC[C@@H](O)CC(=O)O)cc2Br)cccc1-c1cccc(COc2nc(OCc3cnnn3Cc3ccccc3)c(CNC[C@@H](O)CC(=O)O)cc2Br)c1C]

The title compound was synthesized analogously to Example 121 using (1-benzyl-1H-1,2,3-triazol-5-yl)methanol in place of 5-(hydroxymethyl)isophthalonitrile, and following reductive amination procedure G. $^1$H NMR (400 MHz, Methanol-$d_4$) δ 7.98 (d, J=0.9 Hz, 4H), 7.40 (d, J=7.3 Hz, 2H), 7.35-7.25 (m, 10H), 7.20 (t, J=7.6 Hz, 2H), 7.08-6.98 (m, 2H), 5.57 (d, J=2.7 Hz, 8H), 5.47 (s, 4H), 4.27 (dtd, J=9.5, 6.3, 3.0 Hz, 2H), 4.16 (s, 4H), 3.17 (dd, J=12.8, 3.0 Hz, 2H), 2.97 (dd, J=12.7, 9.9 Hz, 2H), 2.50 (d, J=6.2 Hz, 4H), 2.00 (s, 6H). MS (m/z) 1191.132 (M+H)+.

Example 140: (3S,3'S)-4,4'-((((((2,2'-dimethyl-[1,1'-biphenyl]-3,3'-diyl)bis(methylene))bis(oxy))bis(5-bromo-2-((3-cyano-4-fluorobenzyl)oxy)pyridine-6,3-diyl))bis(methylene))bis(azanediyl))bis(3-hydroxybutanoic acid) (or (3S,3'S)-4,4'-(((6,6'-(((2,2'-dimethyl-[1,1'-biphenyl]-3,3'-diyl)bis(methylene))bis(oxy))bis(5-bromo-2-((3-cyano-4-fluorobenzyl)oxy)pyridine-6,3-diyl))bis(methylene))bis(azanediyl))bis(3-hydroxybutanoic acid))

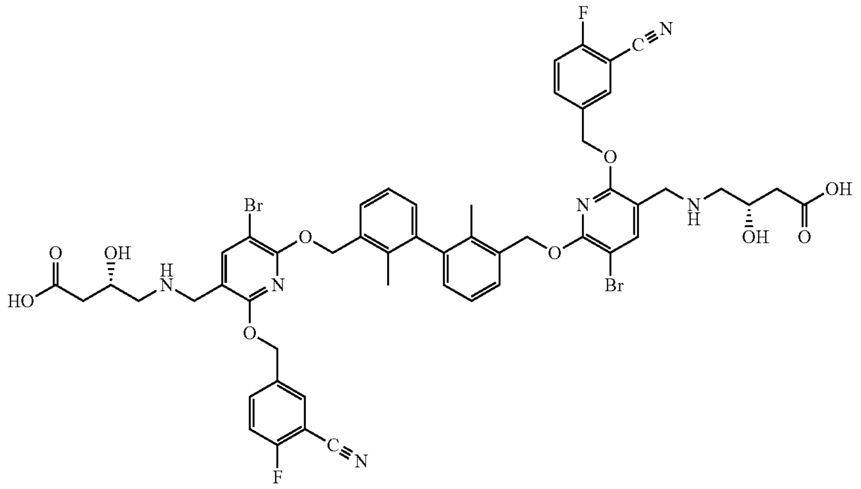 [SMILES: Cc1c(COc2nc(OCc3ccc(F)c(C#N)c3)c(CNC[C@@H](O)CC(=O)O)cc2Br)cccc1-c1cccc(COc2nc(OCc3ccc(F)c(C#N)c3)c(CNC[C@@H](O)CC(=O)O)cc2Br)c1C]

The title compound was synthesized analogously to Example 121 using 2-fluoro-5-(hydroxymethyl)benzonitrile in place of 5-(hydroxymethyl)isophthalonitrile, and following reductive amination procedure G. $^1$H NMR (400 MHz, Methanol-$d_4$) δ 8.01 (s, 2H), 7.89 (dd, J=6.0, 2.2 Hz, 2H), 7.83 (ddd, J=7.9, 5.1, 2.3 Hz, 2H), 7.44-7.29 (m, 4H), 7.23 (t, J=7.6 Hz, 2H), 7.13-7.01 (m, 2H), 5.62-5.37 (m, 8H), 4.34-4.11 (m, 6H), 3.22 (dd, J=12.7, 3.1 Hz, 2H), 3.01 (dd, J=12.7, 9.8 Hz, 2H), 2.53 (dd, J=6.3, 1.4 Hz, 4H), 2.04 (s, 6H). MS (m/z) 1114.939 (M+H)+.

Example 141: (3S,3'S)-4,4'-((((((2,2'-dimethyl-[1,1'-biphenyl]-3,3'-diyl)bis(methylene))bis(oxy))bis(5-bromo-2-(cyclopropylmethoxy)pyridine-6,3-diyl))bis(methylene))bis(azanediyl))bis(3-hydroxybutanoic acid) (or (3S,3'S)-4,4'-(((6,6'-(((2,2'-dimethyl-[1,1'-biphenyl]-3,3'-diyl)bis(methylene))bis(oxy))bis(5-bromo-2-(cyclopropylmethoxy)pyridine-6,3-diyl))bis(methylene))bis(azanediyl))bis(3-hydroxybutanoic acid))

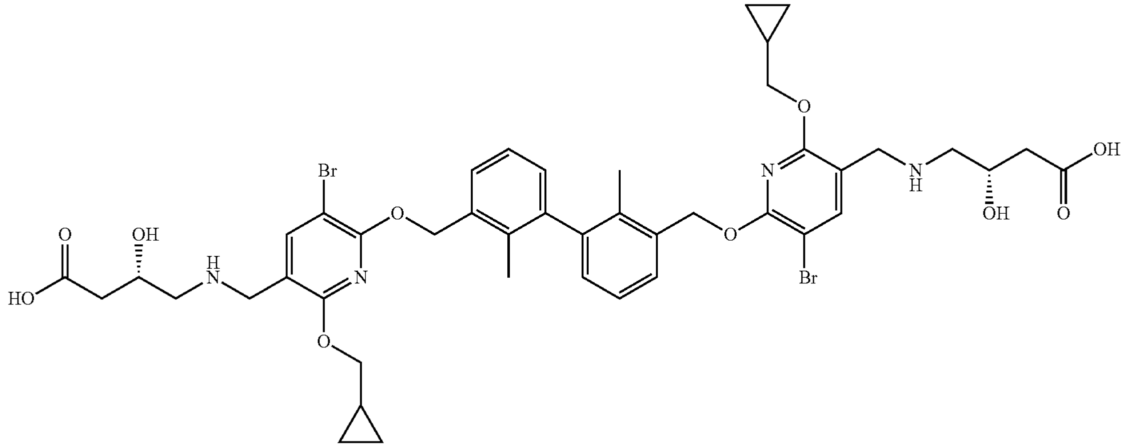 [SMILES: Cc1c(COc2nc(OCC3CC3)c(CNC[C@@H](O)CC(=O)O)cc2Br)cccc1-c1cccc(COc2nc(OCC3CC3)c(CNC[C@@H](O)CC(=O)O)cc2Br)c1C]

The title compound was synthesized analogously to Example 121 using cyclopropylmethanol in place of 5-(hydroxymethyl)isophthalonitrile, and following reductive amination procedure G. $^1$H NMR (400 MHz, Methanol-$d_4$) δ 7.95 (s, 2H), 7.42 (d, J=7.5 Hz, 2H), 7.23 (t, J=7.6 Hz, 2H), 7.06 (d, J=7.3 Hz, 2H), 5.54 (s, 4H), 4.34-4.21 (m, 6H), 4.18 (s, 4H), 3.24 (dd, J=12.7, 3.1 Hz, 2H), 3.02 (dd, J=12.7, 9.8 Hz, 2H), 2.55 (d, J=6.3 Hz, 4H), 2.08 (s, 6H), 1.32 (td, J=7.8, 4.3 Hz, 2H), 0.67-0.49 (m, 4H), 0.45-0.30 (m, 4H). MS (m/z) 956.889 (M+H)+.

Example 142: (3S,3'S)-4,4'-((((((2,2'-dimethyl-[1,1'-biphenyl]-3,3'-diyl)bis(methylene))bis(oxy))bis(2-(2-(1H-pyrazol-3-yl)ethoxy)-5-bromopyridine-6,3-diyl))bis(methylene))bis(azanediyl))bis(3-hydroxybutanoic acid) (or (3S,3'S)-4,4'-(((6,6'-(((2,2'-dimethyl-[1,1'-biphenyl]-3,3'-diyl)bis(methylene))bis(oxy))bis(2-(2-(1H-pyrazol-3-yl)ethoxy)-5-bromopyridine-6,3-diyl))bis(methylene))bis(azanediyl))bis(3-hydroxybutanoic acid))

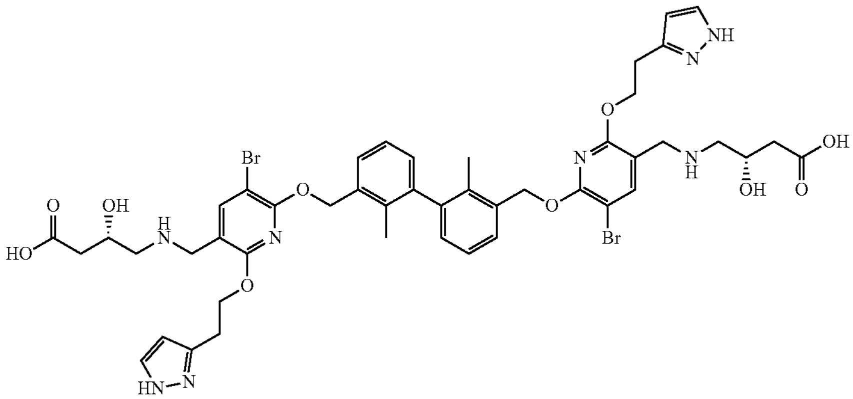 [SMILES: Cc1c(COc2nc(OCCc3cc[nH]n3)c(CNC[C@@H](O)CC(=O)O)cc2Br)cccc1-c1cccc(COc2nc(OCCc3cc[nH]n3)c(CNC[C@@H](O)CC(=O)O)cc2Br)c1C]

The title compound was synthesized analogously to Example 121 using 2-(1H-pyrazol-3-yl)ethan-1-ol in place of 5-(hydroxymethyl)isophthalonitrile, and following reductive amination procedure G. $^1$H NMR (400 MHz, Methanol-$d_4$) δ 7.94 (s, 2H), 7.57 (d, J=2.2 Hz, 2H), 7.44 (d, J=7.6 Hz, 2H), 7.22 (t, J=7.5 Hz, 2H), 7.09-6.97 (m, 2H), 6.23 (d, J=2.2 Hz, 2H), 5.54 (s, 4H), 4.74-4.59 (m, 4H), 4.41-4.20 (m, 2H), 4.12 (s, 4H), 3.20-3.12 (m, 6H), 2.99 (dd, J=12.8, 9.9 Hz, 2H), 2.54 (d, J=6.3 Hz, 4H), 2.07 (s, 6H). MS (m/z) 1037.019 (M+H)+.

Example 143: (3S,3'S)-4,4'-((((((2,2'-dimethyl-[1,1'-biphenyl]-3,3'-diyl)bis(methylene))bis(oxy))bis(5-bromo-2-(4-cyanobutoxy)pyridine-6,3-diyl))bis(methylene))bis(azanediyl))bis(3-hydroxybutanoic acid) (or (3S,3'S)-4,4'-(((6,6'-(((2,2'-dimethyl-[1,1'-biphenyl]-3,3'-diyl)bis(methylene))bis(oxy))bis(5-bromo-2-(4-cyanobutoxy)pyridine-6,3-diyl))bis(methylene))bis(azanediyl))bis(3-hydroxybutanoic acid))

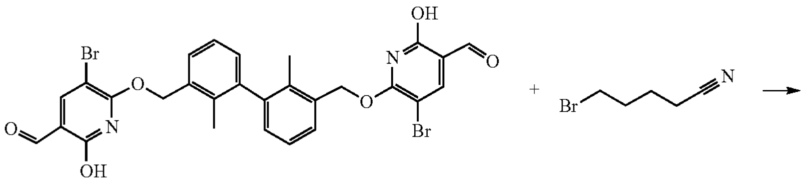

-continued

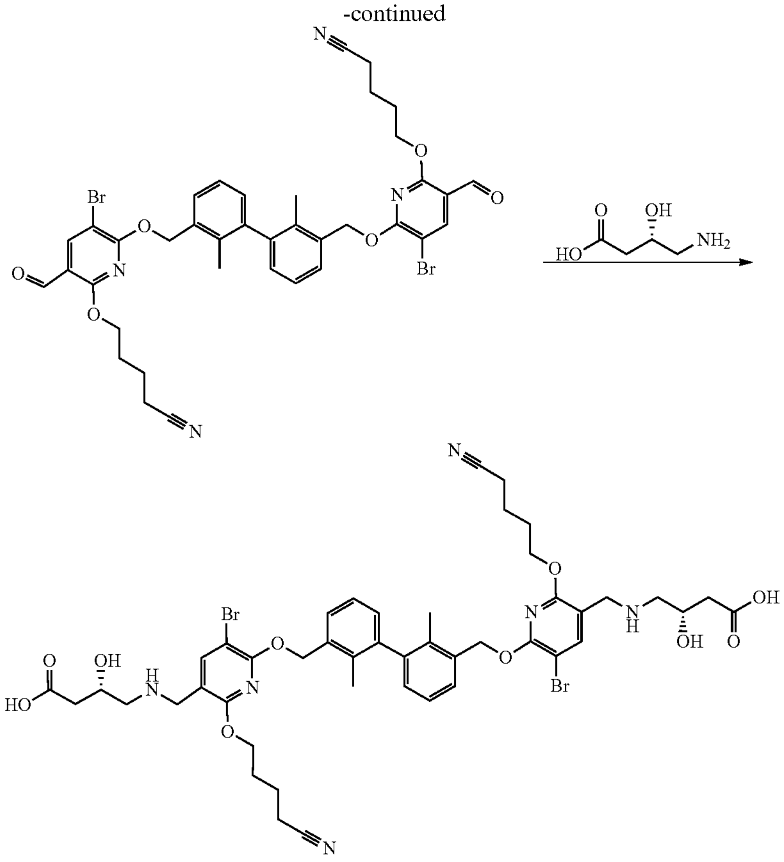

Intermediate 24 (24 mg, 0.037 mmol), 5-bromopentanenitrile (24.2 mg, 0.15 mmol), and potassium carbonate (20.7 mg, 0.15 mmol) were charged into a 2 dram vial. The contents were suspended in N,N-dimethylformamide (0.5 mL) and stirred at 70° C. After 4 h, the reaction was concentrated in vacuo, diluted with methylene chloride, filtered to remove insoluble salts, and concentrated to provide the crude product which was used directly in the next step following reductive amination procedure G to provide 15 mg of the title compound as the bis-TFA salt. $^1H$ NMR (400 MHz, Methanol-$d_4$) δ 7.96 (s, 2H), 7.45 (d, J=7.2 Hz, 2H), 7.25 (t, J=7.6 Hz, 2H), 7.08 (dd, J=7.6, 1.4 Hz, 2H), 5.56 (s, 4H), 4.60-4.38 (m, 4H), 4.27 (dtd, J=9.4, 6.3, 3.0 Hz, 2H), 4.17 (s, 4H), 3.24 (dd, J=12.7, 3.1 Hz, 2H), 3.03 (dd, J=12.7, 9.8 Hz, 2H), 2.59-2.50 (m, 8H), 2.09 (s, 6H), 2.06-1.91 (m, 4H), 1.91-1.71 (m, 4H). MS (m/z) 1011.002 (M+H)+.

Example 144: (3S,3'S)-4,4'-((((((2,2'-dimethyl-[1,1'-biphenyl]-3,3'-diyl)bis(methylene))bis(oxy))bis(5-bromo-2-(3-cyanopropoxy)pyridine-6,3-diyl))bis(methylene))bis(azanediyl))bis(3-hydroxybutanoic acid) (or (3S,3'S)-4,4'-(((6,6'-(((2,2'-dimethyl-[1,1'-biphenyl]-3,3'-diyl)bis(methylene))bis(oxy))bis(5-bromo-2-(3-cyanopropoxy)pyridine-6,3-diyl))bis(methylene))bis(azanediyl))bis(3-hydroxybutanoic acid))

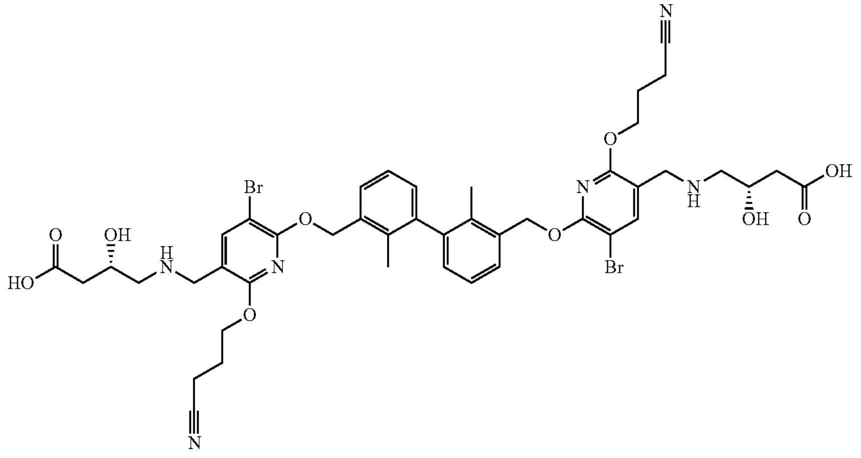 [SMILES: Cc1c(COc2nc(OCCCC#N)c(CNC[C@@H](O)CC(=O)O)cc2Br)cccc1-c1cccc(COc2nc(OCCCC#N)c(CNC[C@@H](O)CC(=O)O)cc2Br)c1C]

The title compound was synthesized analogously to Example 143 using 4-bromobutanenitrile in place of 5-bromopentanenitrile, and following reductive amination procedure G. $^1$H NMR (400 MHz, Methanol-d4) δ 7.98 (s, 2H), 7.46 (dd, J=7.6, 1.4 Hz, 2H), 7.25 (t, J=7.6 Hz, 2H), 7.08 (dd, J=7.7, 1.4 Hz, 2H), 5.57 (s, 4H), 4.56 (td, J=5.6, 5.0, 2.8 Hz, 4H), 4.28 (dtd, J=9.5, 6.3, 3.1 Hz, 2H), 4.21 (s, 4H), 3.25 (dd, J=12.7, 3.1 Hz, 2H), 3.04 (dd, J=12.7, 9.7 Hz, 2H), 2.66 (t, J=6.8 Hz, 4H), 2.17 (p, J=6.4 Hz, 4H), 2.09 (s, 6H). MS (m/z) 982.991 (M+H)+.

Example 145: (3S,3'S)-4,4'-((((((2,2'-dimethyl-[1,1'-biphenyl]-3,3'-diyl)bis(methylene))bis(oxy))bis(2-(3-amino-3-oxopropoxy)-5-bromopyridine-6,3-diyl))bis(methylene))bis(azanediyl))bis(3-hydroxybutanoic acid) (or (3S,3'S)-4,4'-(((6,6'-(((2,2'-dimethyl-[1,1'-biphenyl]-3,3'-diyl)bis(methylene))bis(oxy))bis(2-(3-amino-3-oxopropoxy)-5-bromopyridine-6,3-diyl))bis(methylene))bis(azanediyl))bis(3-hydroxybutanoic acid))

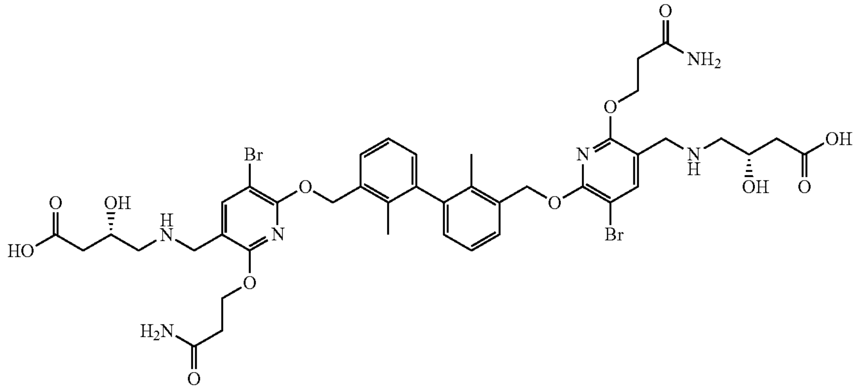 [SMILES: Cc1c(COc2nc(OCCC(N)=O)c(CNC[C@@H](O)CC(=O)O)cc2Br)cccc1-c1cccc(COc2nc(OCCC(N)=O)c(CNC[C@@H](O)CC(=O)O)cc2Br)c1C]

The title compound was synthesized analogously to Example 143 using 3-bromopropanamide in place of 5-bromopentanenitrile, and following reductive amination procedure G. $^1$H NMR (400 MHz, Methanol-$d_4$) δ 7.95 (s, 2H), 7.47 (d, J=7.5 Hz, 2H), 7.25 (t, J=7.6 Hz, 2H), 7.08 (d, J=7.5 Hz, 2H), 5.56 (s, 4H), 4.68 (t, J=5.7 Hz, 4H), 4.32 (d, J=5.4 Hz, 2H), 4.14 (s, 4H), 3.19 (dd, J=12.8, 2.9 Hz, 2H), 3.00 (dd, J=12.8, 9.9 Hz, 2H), 2.74 (t, J=5.8 Hz, 4H), 2.55 (dd, J=6.4, 2.5 Hz, 4H), 2.10 (s, 6H). MS (m/z) 990.943 (M+H)+.

Example 146:2,2'-((((((2,2'-dimethyl-[1,1'-biphenyl]-3,3'-diyl)bis(methylene))bis(oxy))bis(2-(3-amino-3-oxopropoxy)-5-chloropyridine-6,3-diyl))bis(methylene))bis(azanediyl))diacetic acid (or 2,2'-(((6,6'-(((2,2'-dimethyl-[1,1'-biphenyl]-3,3'-diyl)bis(methylene))bis(oxy))bis(2-(3-amino-3-oxopropoxy)-5-chloropyridine-6,3-diyl))bis(methylene))bis(azanediyl))diacetic acid)

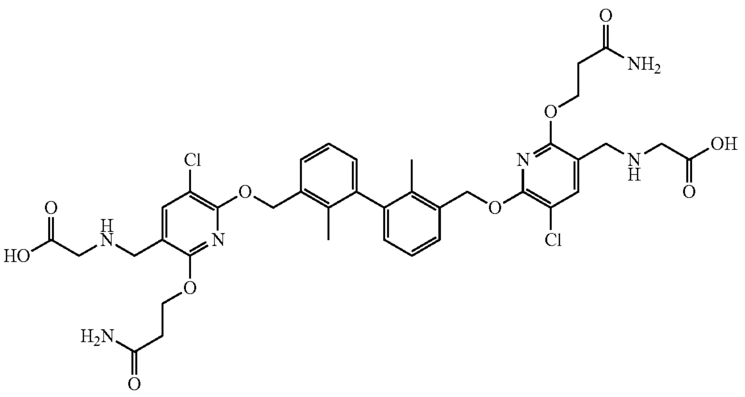 [SMILES: Cc1c(COc2nc(OCCC(N)=O)c(CNCC(=O)O)cc2Cl)cccc1-c1cccc(COc2nc(OCCC(N)=O)c(CNCC(=O)O)cc2Cl)c1C]

The title compound was synthesized analogously to Example 143 using intermediate 32 in place of intermediate 24, using 3-bromopropanamide in place of 5-bromopentanenitrile, and following reductive amination procedure G using glycine in place of (3S)-4-amino-3-hydroxybutanoic acid. $^1$H NMR (400 MHz, Methanol-$d_4$) δ 7.80 (s, 2H), 7.54-7.37 (m, 2H), 7.25 (t, J=7.6 Hz, 2H), 7.11-7.03 (m, 2H), 5.58 (m, 4H), 4.68 (t, J=5.9 Hz, 4H), 4.17 (s, 4H), 3.87 (s, 4H), 2.74 (t, J=5.8 Hz, 4H), 2.09 (s, 6H). MS (m/z) 813.011 (M+H)+.

Example 147: (3S,3'S)-4,4'-((((((2,2'-dimethyl-[1,1'-biphenyl]-3,3'-diyl)bis(methylene))bis(oxy))bis(5-bromo-2-(2-(methylamino)-2-oxoethoxy)pyridine-6,3-diyl))bis(methylene))bis(azanediyl))bis(3-hydroxybutanoic acid) (or (3S,3'S)-4,4'-(((6,6'-(((2,2'-dimethyl-[1,1'-biphenyl]-3,3'-diyl)bis(methylene))bis(oxy))bis(5-bromo-2-(2-(methylamino)-2-oxoethoxy)pyridine-6,3-diyl))bis(methylene))bis(azanediyl))bis(3-hydroxybutanoic acid))

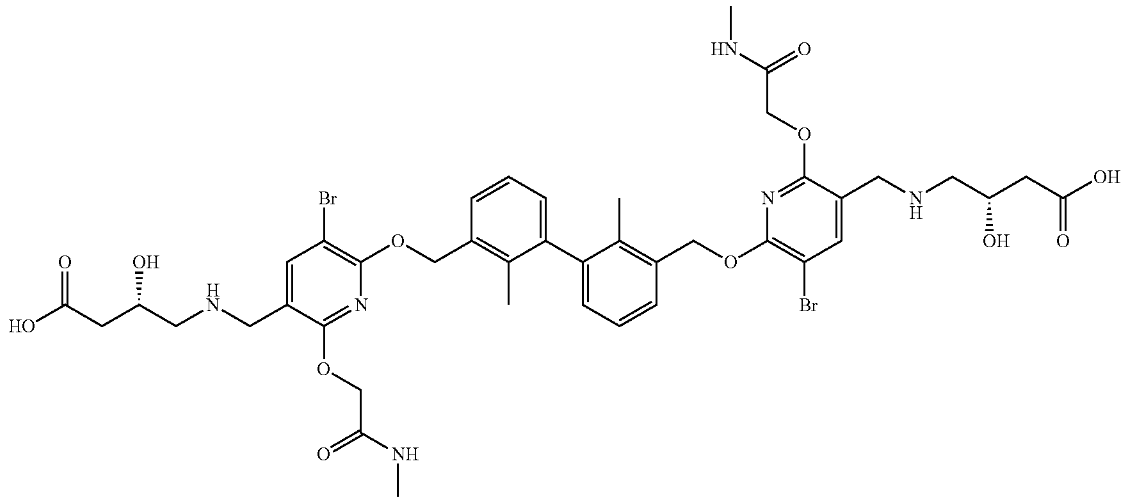 [SMILES: CNC(=O)COc1nc(OCc2cccc(-c3cccc(COc4nc(OCC(=O)NC)c(CNC[C@@H](O)CC(=O)O)cc4Br)c3C)c2C)c(Br)cc1CNC[C@@H](O)CC(=O)O]

The title compound was synthesized analogously to Example 143 using 2-bromo-N-methylacetamide in place of 5-bromopentanenitrile, and following reductive amination procedure G. $^1$H NMR (400 MHz, Methanol-$d_4$) δ 8.02 (s, 2H), 7.45 (d, J=7.3 Hz, 2H), 7.25 (t, J=7.6 Hz, 2H), 7.10 (d, J=7.4 Hz, 2H), 5.55-5.40 (m, 4H), 4.96 (s, 4H), 4.40-4.29 (m, 2H), 4.23 (d, J=1.7 Hz, 4H), 3.28-3.23 (m, 2H), 3.07 (dd, J=12.7, 9.9 Hz, 2H), 2.77 (s, 6H), 2.56 (dd, J=6.3, 2.3 Hz, 4H), 2.07 (s, 6H). MS (m/z) 510.251 (M+2H)2+

Example 148: (3S,3'S)-4,4'-((((((2,2'-dimethyl-[1,1'-biphenyl]-3,3'-diyl)bis(methylene))bis(oxy))bis(5-bromo-2-((4-cyanopyridin-2-yl)methoxy)pyridine-6,3-diyl))bis(methylene))bis(azanediyl))bis(3-hydroxybutanoic acid) (or (3S,3'S)-4,4'-(((6,6'-(((2,2'-dimethyl-[1,1'-biphenyl]-3,3'-diyl)bis(methylene))bis(oxy))bis(5-bromo-2-((4-cyanopyridin-2-yl)methoxy)pyridine-6,3-diyl))bis(methylene))bis(azanediyl))bis(3-hydroxybutanoic acid))

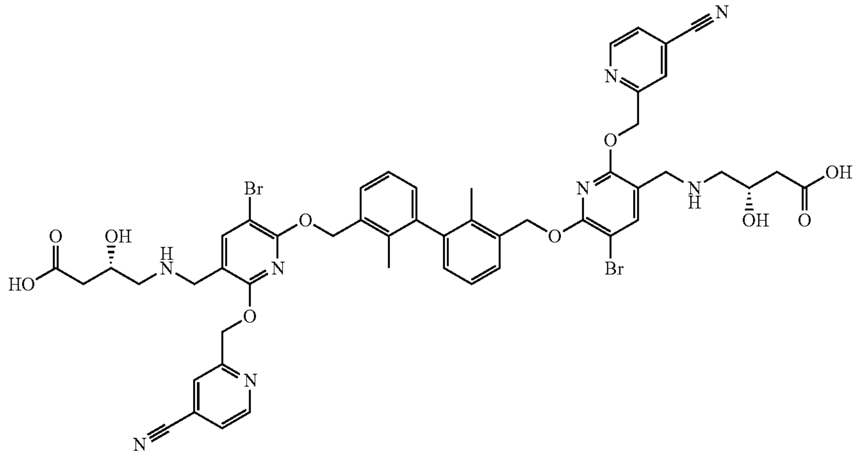 [SMILES: Cc1c(COc2nc(OCc3cc(C#N)ccn3)c(CNC[C@@H](O)CC(=O)O)cc2Br)cccc1-c1cccc(COc2nc(OCc3cc(C#N)ccn3)c(CNC[C@@H](O)CC(=O)O)cc2Br)c1C]

The title compound was synthesized analogously to Example 143 using 2-(bromomethyl)isonicotinonitrile in place of 5-bromopentanenitrile, and following reductive amination procedure G. $^1$H NMR (400 MHz, Methanol-$d_4$) δ 8.76 (dd, J=5.1, 0.9 Hz, 2H), 7.97 (s, 2H), 7.93-7.89 (m, 2H), 7.67 (dd, J=5.2, 1.5 Hz, 2H), 7.39-7.28 (m, 2H), 7.19 (t, J=7.6 Hz, 2H), 7.05 (dd, J=7.7, 1.4 Hz, 2H), 5.78-5.57 (m, 4H), 5.44-5.23 (m, 4H), 4.40-4.19 (m, 6H), 3.32-3.28 (m, 2H), 3.10 (dd, J=12.7, 9.9 Hz, 2H), 2.56 (d, J=6.3 Hz, 4H), 1.99 (s, 6H). MS (m/z) 541.107 (M+2H)2+.

Example 149: (3S,3'S)-4,4'-((((((2,2'-dimethyl-[1,1'-biphenyl]-3,3'-diyl)bis(methylene))bis(oxy))bis(5-bromo-2-(3-methoxypropoxy)pyridine-6,3-diyl))bis(methylene))bis(azanediyl))bis(3-hydroxybutanoic acid) (or (3S,3'S)-4,4'-(((6,6'-(((2,2'-dimethyl-[1,1'-biphenyl]-3,3'-diyl)bis(methylene))bis(oxy))bis(5-bromo-2-(3-methoxypropoxy)pyridine-6,3-diyl))bis(methylene))bis(azanediyl))bis(3-hydroxybutanoic acid))

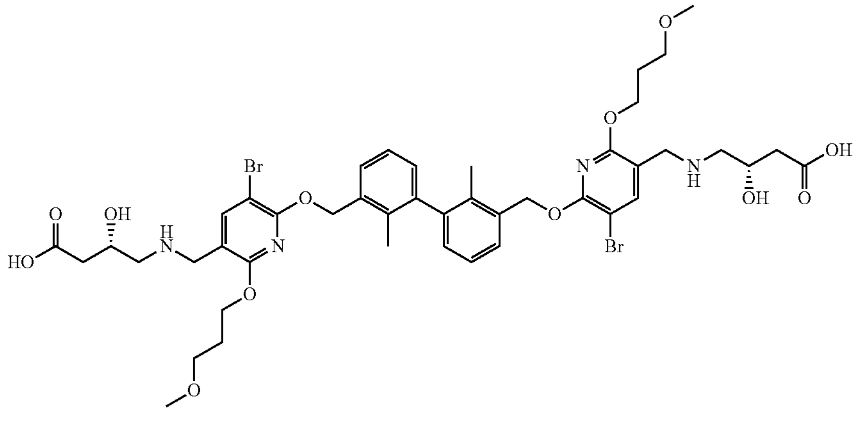 [SMILES: COCCCOc1nc(OCc2cccc(-c3cccc(COc4nc(OCCCOC)c(CNC[C@@H](O)CC(=O)O)cc4Br)c3C)c2C)c(Br)cc1CNC[C@@H](O)CC(=O)O]

The title compound was synthesized analogously to Example 143 using 1-bromo-3-methoxypropane in place of 5-bromopentanenitrile, and following reductive amination procedure G. $^1$H NMR (400 MHz, Methanol-$d_4$) δ 7.94 (s, 2H), 7.56-7.34 (m, 2H), 7.24 (t, J=7.6 Hz, 2H), 7.07 (dd, J=7.7, 1.4 Hz, 2H), 5.56 (d, J=1.8 Hz, 4H), 4.57-4.44 (m, 4H), 4.27 (dtd, J=9.4, 6.3, 2.9 Hz, 2H), 4.16 (s, 4H), 3.57 (t, J=5.9 Hz, 4H), 3.33 (s, 6H), 3.23 (dd, J=12.7, 3.0 Hz, 2H), 3.01 (dd, J=12.7, 9.8 Hz, 2H), 2.55 (d, J=6.3 Hz, 4H), 2.09 (m, 10H). MS (m/z) 993.001 (M+H)+.

Example 150: (3S,3'S)-4,4'-((((((2,2'-dimethyl-[1,1'-biphenyl]-3,3'-diyl)bis(methylene))bis(oxy))bis(5-bromo-2-(2-methoxy-2-oxoethoxy)pyridine-6,3-diyl))bis(methylene))bis(azanediyl))bis(3-hydroxybutanoic acid) (or (3S,3'S)-4,4'-(((6,6'-(((2,2'-dimethyl-[1,1'-biphenyl]-3,3'-diyl)bis(methylene))bis(oxy))bis(5-bromo-2-(2-methoxy-2-oxoethoxy)pyridine-6,3-diyl))bis(methylene))bis(azanediyl))bis(3-hydroxybutanoic acid))

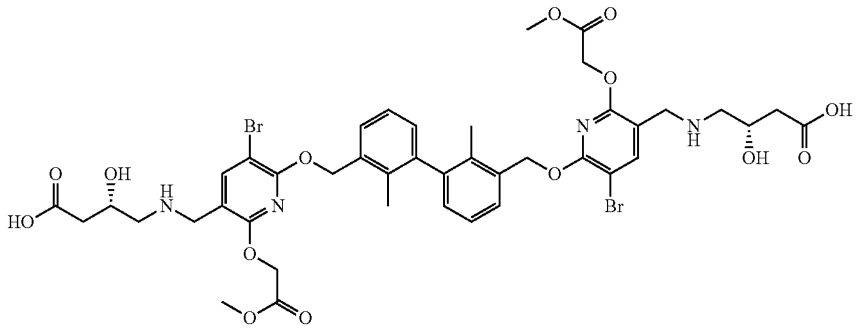 [SMILES: COC(=O)COc1nc(OCc2cccc(-c3cccc(COc4nc(OCC(=O)OC)c(CNC[C@@H](O)CC(=O)O)cc4Br)c3C)c2C)c(Br)cc1CNC[C@@H](O)CC(=O)O]

The title compound was synthesized analogously to Example 143 using methyl 2-bromoacetate in place of 5-bromopentanenitrile, and following reductive amination procedure G. $^1$H NMR (400 MHz, Methanol-$d_4$) δ 8.04 (s, 2H), 7.41 (d, J=7.2 Hz, 2H), 7.25 (t, J=7.6 Hz, 2H), 7.09 (dd, J=7.6, 1.3 Hz, 2H), 5.67-5.34 (m, 4H), 5.19-4.97 (m, 4H), 4.42-4.16 (m, 6H), 3.75 (s, 6H), 3.26 (dd, J=12.7, 3.1 Hz, 2H), 3.05 (dd, J=12.7, 9.9 Hz, 2H), 2.68-2.46 (m, 4H), 2.07 (s, 6H). MS (m/z) 992.861 (M+H)+.

Example 151: (3S,3'S)-4,4'-((((((2,2'-dimethyl-[1,1'-biphenyl]-3,3'-diyl)bis(methylene))bis(oxy))bis(2-(allyloxy)-5-bromopyridine-6,3-diyl))bis(methylene))bis(azanediyl))bis(3-hydroxybutanoic acid) (or (3S,3'S)-4,4'-(((6,6'-(((2,2'-dimethyl-[1,1'-biphenyl]-3,3'-diyl)bis(methylene))bis(oxy))bis(2-(allyloxy)-5-bromopyridine-6,3-diyl))bis(methylene))bis(azanediyl))bis(3-hydroxybutanoic acid))

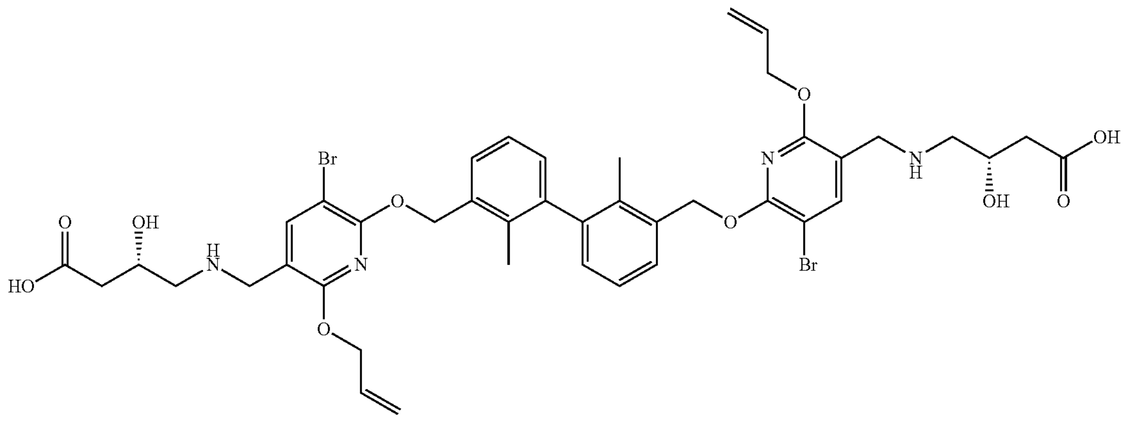 [SMILES: C=CCOc1nc(OCc2cccc(-c3cccc(COc4nc(OCC=C)c(CNC[C@@H](O)CC(=O)O)cc4Br)c3C)c2C)c(Br)cc1CNC[C@@H](O)CC(=O)O]

The title compound was synthesized analogously to Example 143 using 3-bromoprop-1-ene in place of 5-bromopentanenitrile, and following reductive amination procedure G. $^1H$ NMR (400 MHz, Methanol-$d_4$) δ 7.97 (s, 2H), 7.51-7.38 (m, 2H), 7.24 (t, J=7.6 Hz, 2H), 7.16-6.99 (m, 2H), 6.22-5.96 (m, 2H), 5.55 (s, 4H), 5.50-5.34 (m, 2H), 5.28 (dd, J=10.6, 1.4 Hz, 2H), 4.95 (dd, J=5.9, 1.5 Hz, 4H), 4.33-4.21 (m, 2H), 4.18 (s, 4H), 3.22 (dd, J=12.7, 3.1 Hz, 2H), 3.01 (dd, J=12.8, 9.8 Hz, 2H), 2.54 (d, J=6.3 Hz, 4H), 2.09 (s, 6H). MS (m/z) 928.882 (M+H)+.

Example 152: (3S,3'S)-4,4'-((((((2,2'-dimethyl-[1,1'-biphenyl]-3,3'-diyl)bis(methylene))bis(oxy))bis(5-bromo-2-((6-cyanopyridin-2-yl)methoxy)pyridine-6,3-diyl))bis(methylene))bis(azanediyl))bis(3-hydroxybutanoic acid) (or (3S,3'S)-4,4'-(((6,6'-(((2,2'-dimethyl-[1,1'-biphenyl]-3,3'-diyl)bis(methylene))bis(oxy))bis(5-bromo-2-((6-cyanopyridin-2-yl)methoxy)pyridine-6,3-diyl))bis(methylene))bis(azanediyl))bis(3-hydroxybutanoic acid))

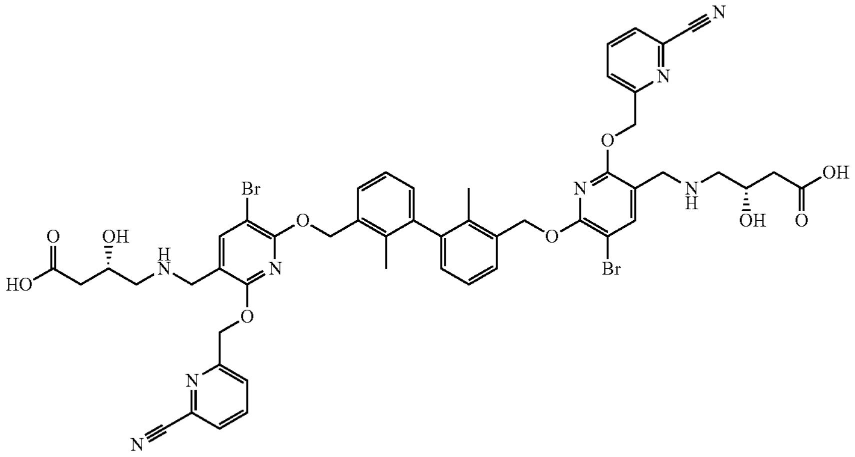 [SMILES: Cc1c(COc2nc(OCc3cccc(C#N)n3)c(CNC[C@@H](O)CC(=O)O)cc2Br)cccc1-c1cccc(COc2nc(OCc3cccc(C#N)n3)c(CNC[C@@H](O)CC(=O)O)cc2Br)c1C]

The title compound was synthesized analogously to Example 143 using 6-(bromomethyl)picolinonitrile in place of 5-bromopentanenitrile, and following reductive amination procedure G. $^1H$ NMR (400 MHz, Methanol-$d_4$) δ 8.07-7.93 (m, 6H), 7.81 (d, J=7.8 Hz, 4H), 7.31 (dd, J=7.7, 1.3 Hz, 2H), 7.19 (t, J=7.6 Hz, 2H), 7.10-6.95 (m, 2H), 5.63 (d, J=2.6 Hz, 4H), 5.35 (d, J=1.7 Hz, 4H), 4.47-4.18 (m, 6H), 3.09 (dd, J=12.8, 9.9 Hz, 2H), 2.56 (d, J=6.3 Hz, 4H), 1.99 (s, 6H). MS (m/z) 541.155 $(M+2H)_2$+

Example 153: (3S,3'S)-4,4'-((((((2,2'-dimethyl-[1,1'-biphenyl]-3,3'-diyl)bis(methylene))bis(oxy))bis(5-chloro-2-((3-cyanobenzyl)oxy)pyridine-6,3-diyl))bis(methylene))bis(azanediyl))bis(3-hydroxybutanoic acid) (or (3S,3'S)-4,4'-(((6,6'-(((2,2'-dimethyl-[1,1'-biphenyl]-3,3'-diyl)bis(methylene))bis(oxy))bis(5-chloro-2-((3-cyanobenzyl)oxy)pyridine-6,3-diyl))bis(methylene))bis(azanediyl))bis(3-hydroxybutanoic acid))

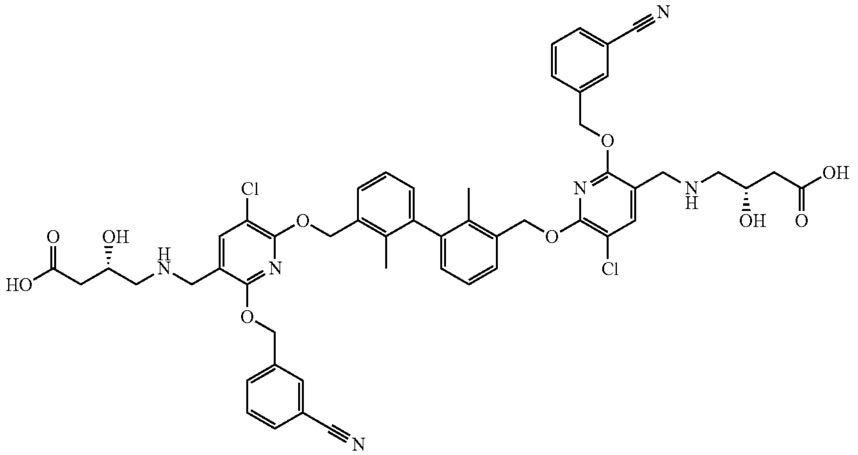 [SMILES: Cc1c(COc2nc(OCc3cccc(C#N)c3)c(CNC[C@@H](O)CC(=O)O)cc2Cl)cccc1-c1cccc(COc2nc(OCc3cccc(C#N)c3)c(CNC[C@@H](O)CC(=O)O)cc2Cl)c1C]

The title compound was synthesized analogously to Example 143 using intermediate 32 in place of intermediate 24, using 3-(bromomethyl)benzonitrile in place of 5-bromopentanenitrile, and following reductive amination procedure G. $^1$H NMR (400 MHz, Methanol-$d_4$) δ 7.87 (d, J=9.3 Hz, 4H), 7.78 (d, J=7.9 Hz, 2H), 7.68 (d, J=7.9 Hz, 2H), 7.55 (t, J=7.7 Hz, 2H), 7.40-7.30 (m, 2H), 7.22 (t, J=7.6 Hz, 2H), 7.05 (d, J=7.4 Hz, 2H), 5.63-5.41 (m, 8H), 4.34-4.19 (m, 6H), 3.23 (dd, J=12.7, 3.1 Hz, 2H), 3.01 (dd, J=12.7, 9.8 Hz, 2H), 2.53 (dd, J=6.3, 1.2 Hz, 4H), 2.01 (s, 6H). MS (m/z) 989.001 (M+H)+.

Example 154: (3S,3'S)-4,4'-((((((2,2'-dimethyl-[1,1'-biphenyl]-3,3'-diyl)bis(methylene))bis(oxy))bis(5-bromo-2-(2,2,2-trifluoroethoxy)pyridine-6,3-diyl))bis(methylene))bis(azanediyl))bis(3-hydroxybutanoic acid) (or (3S,3'S)-4,4'-(((6,6'-(((2,2'-dimethyl-[1,1'-biphenyl]-3,3'-diyl)bis(methylene))bis(oxy))bis(5-bromo-2-(2,2,2-trifluoroethoxy)pyridine-6,3-diyl))bis(methylene))bis(azanediyl))bis(3-hydroxybutanoic acid))

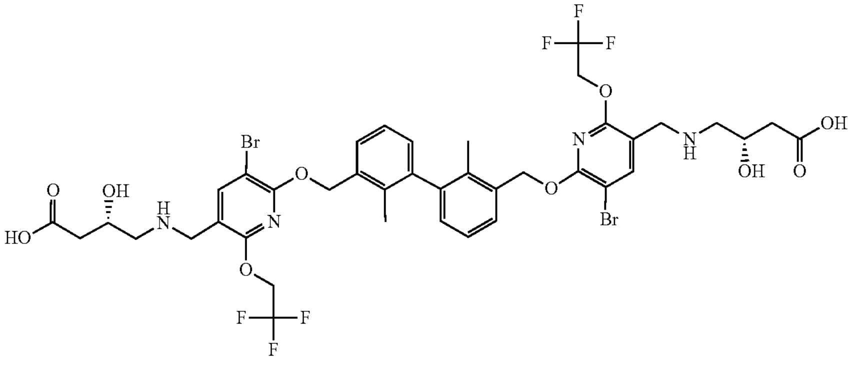 [SMILES: Cc1c(COc2nc(OCC(F)(F)F)c(CNC[C@@H](O)CC(=O)O)cc2Br)cccc1-c1cccc(COc2nc(OCC(F)(F)F)c(CNC[C@@H](O)CC(=O)O)cc2Br)c1C]

The title compound was synthesized analogously to Example 143 using 2,2,2-trifluoroethyl trifluoromethanesulfonate in place of 5-bromopentanenitrile, and following reductive amination procedure G. $^1$H NMR (400 MHz, Methanol-$d_4$) δ 8.08 (s, 2H), 7.45 (dd, J=7.7, 1.4 Hz, 2H), 7.25 (t, J=7.6 Hz, 2H), 7.09 (dd, J=7.7, 1.4 Hz, 2H), 5.57 (s, 4H), 5.02-4.94 (m, 4H), 4.41-4.08 (m, 6H), 3.23 (dd, J=12.7, 3.0 Hz, 2H), 3.02 (dd, J=12.7, 9.9 Hz, 2H), 2.53 (d, J=6.3 Hz, 4H), 2.09 (s, 6H). MS (m/z) 507.070 (M+2H)2+.

Example 155: (3S,3'S)-4,4'-((((((2,2'-dimethyl-[1,1'-biphenyl]-3,3'-diyl)bis(methylene))bis(oxy))bis(2-(2-amino-2-oxoethoxy)-5-bromopyridine-6,3-diyl))bis(methylene))bis(azanediyl))bis(3-hydroxybutanoic acid) (or (3S,3'S)-4,4'-(((6,6'-(((2,2'-dimethyl-[1,1'-biphenyl]-3,3'-diyl)bis(methylene))bis(oxy))bis(2-(2-amino-2-oxoethoxy)-5-bromopyridine-6,3-diyl))bis(methylene))bis(azanediyl))bis(3-hydroxybutanoic acid))

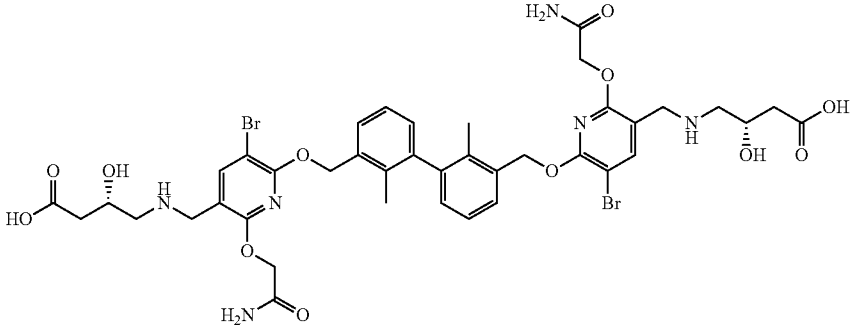 [SMILES: Cc1c(COc2nc(OCC(N)=O)c(CNC[C@@H](O)CC(=O)O)cc2Br)cccc1-c1cccc(COc2nc(OCC(N)=O)c(CNC[C@@H](O)CC(=O)O)cc2Br)c1C]

The title compound was synthesized analogously to Example 143 using 2-bromoacetamide in place of 5-bromopentanenitrile, and following reductive amination procedure G. $^1$H NMR (400 MHz, Methanol-$d_4$) δ 8.01 (s, 2H), 7.48 (d, J=7.5 Hz, 2H), 7.26 (t, J=7.6 Hz, 2H), 7.09 (d, J=7.3 Hz, 2H), 5.51 (s, 4H), 5.00 (d, J=3.5 Hz, 4H), 4.32 (s, 2H), 4.28-4.17 (m, 4H), 3.27-3.22 (m, 2H), 3.06 (dd, J=12.7, 9.9 Hz, 2H), 2.55 (dd, J=6.3, 3.0 Hz, 4H), 2.08 (s, 6H). MS (m/z) 962.931 (M+H)+.

Example 156: (3S,3'S)-4,4'-((((((2,2'-dimethyl-[1,1'-biphenyl]-3,3'-diyl)bis(methylene))bis(oxy))bis(2-methylpyridine-6,3-diyl))bis(methylene))bis(azanediyl))bis(3-hydroxybutanoic acid) (or (3S,3'S)-4,4'-(((6,6'-(((2,2'-dimethyl-[1,1'-biphenyl]-3,3'-diyl)bis(methylene))bis(oxy))bis(2-methylpyridine-6,3-diyl))bis(methylene))bis(azanediyl))bis(3-hydroxybutanoic acid))

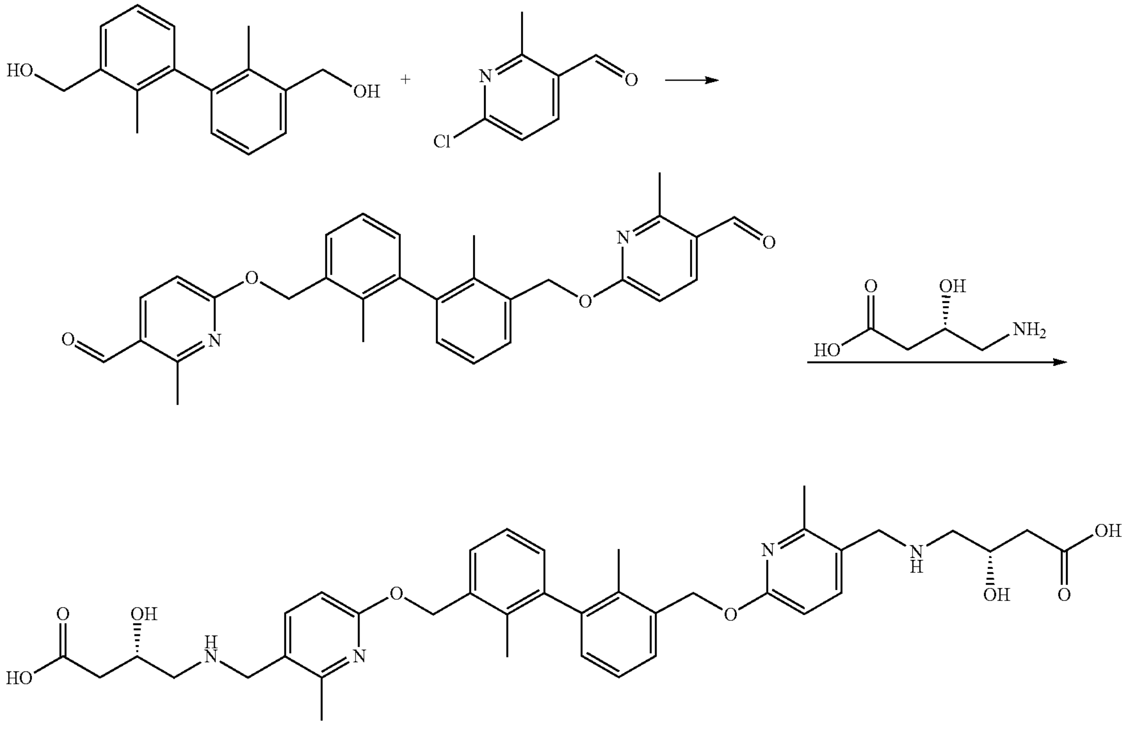

(2,2'-Dimethyl-[1,1'-biphenyl]-3,3'-diyl)dimethanol (60.6 mg, 0.25 mmol) and 6-chloro-2-methylnicotinaldehyde (86 mg, 0.55 mmol) were reacted according to the general palladium arylation reaction using t-ButylXantphos in place of t-ButylXPhos to provide 6,6'-(((2,2'-dimethyl-[1,1'-biphenyl]-3,3'-diyl)bis(methylene))bis(oxy))bis(2-methylnicotinaldehyde). $^{1}$H NMR (400 MHz, Methanol-$d_4$) δ 10.24-10.01 (m, 2H), 8.14-7.99 (m, 2H), 7.52-7.34 (m, 2H), 7.34-7.19 (m, 2H), 7.14-7.00 (m, 2H), 6.90-6.71 (m, 2H), 5.64-5.43 (m, 4H), 2.85-2.69 (m, 6H), 2.15-1.94 (m, 6H).

6,6'-(((2,2'-dimethyl-[1,1'-biphenyl]-3,3'-diyl)bis(methylene))bis(oxy))bis(2-methylnicotinaldehyde) (12 mg, 0.025 mmol) was reacted according to reductive amination procedure E to provide the title compound as the bis-TFA salt. $^{1}$H NMR (400 MHz, Methanol-$d_4$) δ 7.72 (d, J=8.5 Hz, 2H), 7.47-7.39 (m, 2H), 7.22 (t, J=7.6 Hz, 2H), 7.05 (dd, J=7.8, 1.4 Hz, 2H), 6.77 (d, J=8.4 Hz, 2H), 5.45 (d, J=1.3 Hz, 4H), 4.33 (dtd, J=9.3, 6.3, 3.1 Hz, 2H), 4.27 (s, 4H), 3.28-3.24 (m, 2H), 3.08 (dd, J=12.8, 10.0 Hz, 2H), 2.60-2.52 (m, 10H), 2.06 (s, 6H). MS (m/z) 687.157 (M+H)+

Example 157: (3S,3'S)-4,4'-((((((2,2'-dimethyl-[1,1'-biphenyl]-3,3'-diyl)bis(methylene))bis(oxy))bis(2-(pyrimidin-5-ylmethoxy)pyridine-6,3-diyl))bis(methylene))bis(azanediyl))bis(3-hydroxybutanoic acid) (or (3S,3'S)-4,4'-(((6,6'-(((2,2'-dimethyl-[1,1'-biphenyl]-3,3'-diyl)bis(methylene))bis(oxy))bis(2-(pyrimidin-5-ylmethoxy)pyridine-6,3-diyl))bis(methylene))bis(azanediyl))bis(3-hydroxybutanoic acid))

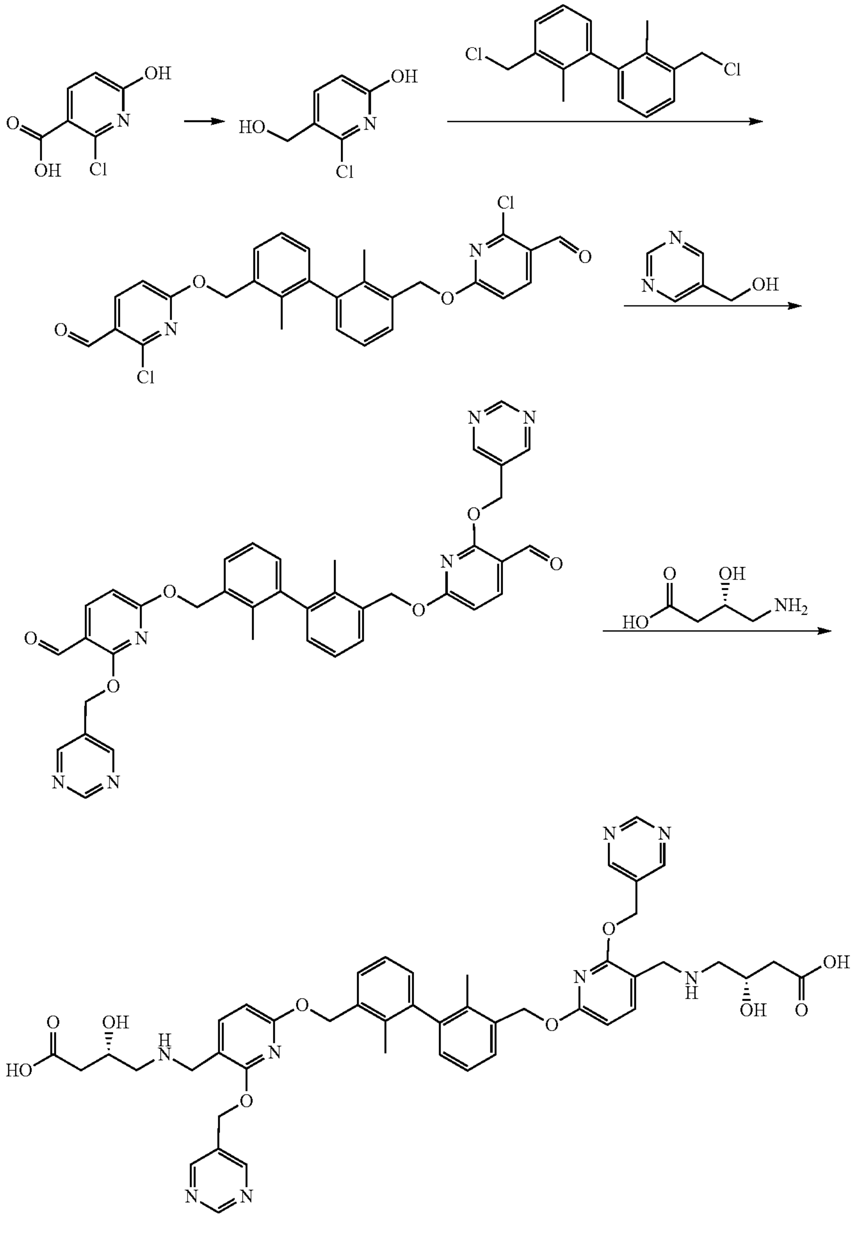

2-Chloro-6-hydroxynicotinic acid (2.3 g, 12 mmol) was pulverized into a fine powder and charged into 200 mL flask. Borane-dimethyl sulfide in THF (2M, 50 mL) was added dropwise and the resulting suspension was stirred for 16 h. The reaction was quenched by slow addition of methanol (50 mL) and refluxed for 1 h. The solution was cooled to room temperature, concentrated, and triturated with diethyl ether. The solids were filtered to provide 6-chloro-5-(hydroxymethyl)pyridin-2-ol. A second batch was obtained from the mother liquor. $^1$H NMR (400 MHz, DMSO-$d_6$) δ 11.23 (s, 1H), 7.72 (d, J=8.2 Hz, 1H), 6.62 (d, J=8.2 Hz, 1H), 5.27 (t, J=5.6 Hz, 1H), 4.41 (d, J=5.5 Hz, 2H).

6-Chloro-5-(hydroxymethyl)pyridin-2-ol (1.22 g, 7.63 mmol), 3,3'-bis(chloromethyl)-2,2'-dimethyl-1,1'-biphenyl (888 mg, 3.18 mmol), potassium carbonate (879 mg, 6.36 mmol), and sodium iodide (45 mg, 0.3 mmol) were suspended in acetone (20 mL). The suspension was heated to 65° C. for 4 h. The resulting purple suspension was diluted with saturated aqueous sodium bicarbonate and extracted with methylene chloride (3×). The organic layer was separated, dried with anhydrous sodium sulfate, concentrated, and to provide ((((2,2'-dimethyl-[1,1'-biphenyl]-3,3'-diyl)bis(methylene))bis(oxy))bis(2-chloropyridine-6,3-diyl))dimethanol. The crude material was suspended in methylene chloride (25 mL) and stirred vigorously at room temperature. Dess-Martin periodinane (2.7 g, 6.36 mmol) was added in one portion and allowed to stir for 10 minutes before water (114 mg, 6.36 mmol) was added dropwise. After 14 h, 1M aqueous sodium hydroxide (30 mL) was added and the reaction was stirred vigorously for 30 min. The organic layer was separated, dried over anhydrous sodium sulfate, concentrated, and purified by column chromatography to provide 6,6'-(((2,2'-dimethyl-[1,1'-biphenyl]-3,3'-diyl)bis(methylene))bis(oxy))bis(2-chloronicotinaldehyde). $^1$H NMR (400 MHz, DMSO-$d_6$) δ 10.16 (d, J=0.8 Hz, 2H), 8.15 (d, J=8.4 Hz, 2H), 7.47 (dd, J=7.5, 1.3 Hz, 2H), 7.27 (t, J=7.6 Hz, 2H), 7.08 (ddd, J=8.5, 7.1, 1.1 Hz, 4H), 5.50 (s, 4H), 2.02 (s, 6H).

Pyrimidin-5-ylmethanol (19.4 mg, 0.176 mmol) in N,N-dimethylformamide (0.5 mL) was treated with sodium hydride (7 mg, 0.176 mmol) at room temperature. After stirring for 15 min, the cloudy alkoxide solution was added dropwise to a suspension of (6,6'-(((2,2'-dimethyl-[1,1'-biphenyl]-3,3'-diyl)bis(methylene))bis(oxy))bis(2-chloronicotinaldehyde) (40 mg, 0.077 mmol) in N,N-dimethylformamide (0.5 mL). After stirring for 15 min at room temperature, the reaction with diluted with saturated aqueous ammonium chloride and ethyl acetate. The organic layer was washed with brine, dried over anhydrous sodium sulfate, and concentrated to provide the crude product which as used directly in the next step following reductive amination procedure A to provide the title compound as the bis-TFA salt. $^1$H NMR (400 MHz, Methanol-$d_4$) δ 9.11 (s, 2H), 8.93 (s, 4H), 7.76 (d, J=8.2 Hz, 2H), 7.38 (d, J=7.8 Hz, 2H), 7.22 (t, J=7.6 Hz, 2H), 7.06 (d, J=7.7 Hz, 2H), 6.56 (d, J=8.1 Hz, 2H), 5.58 (d, J=2.5 Hz, 4H), 5.50-5.36 (m, 4H), 4.23 (s, 6H), 3.22 (dd, J=12.7, 3.1 Hz, 2H), 3.00 (dd, J=12.7, 9.8 Hz, 2H), 2.53 (d, J=6.3 Hz, 4H), 2.01 (s, 6H). MS (m/z) 875.153 (M+H)+.

Example 158: (3S,3'S)-4,4'-((((((2,2'-dimethyl-[1,1'-biphenyl]-3,3'-diyl)bis(methylene))bis(oxy))bis(2-(2-morpholinoethoxy)pyridine-6,3-diyl))bis(methylene))bis(azanediyl))bis(3-hydroxybutanoic acid) (or (3S,3'S)-4,4'-(((6,6'-(((2,2'-dimethyl-[1,1'-biphenyl]-3,3'-diyl)bis(methylene))bis(oxy))bis(2-(2-morpholinoethoxy)pyridine-6,3-diyl))bis(methylene))bis(azanediyl))bis(3-hydroxybutanoic acid))

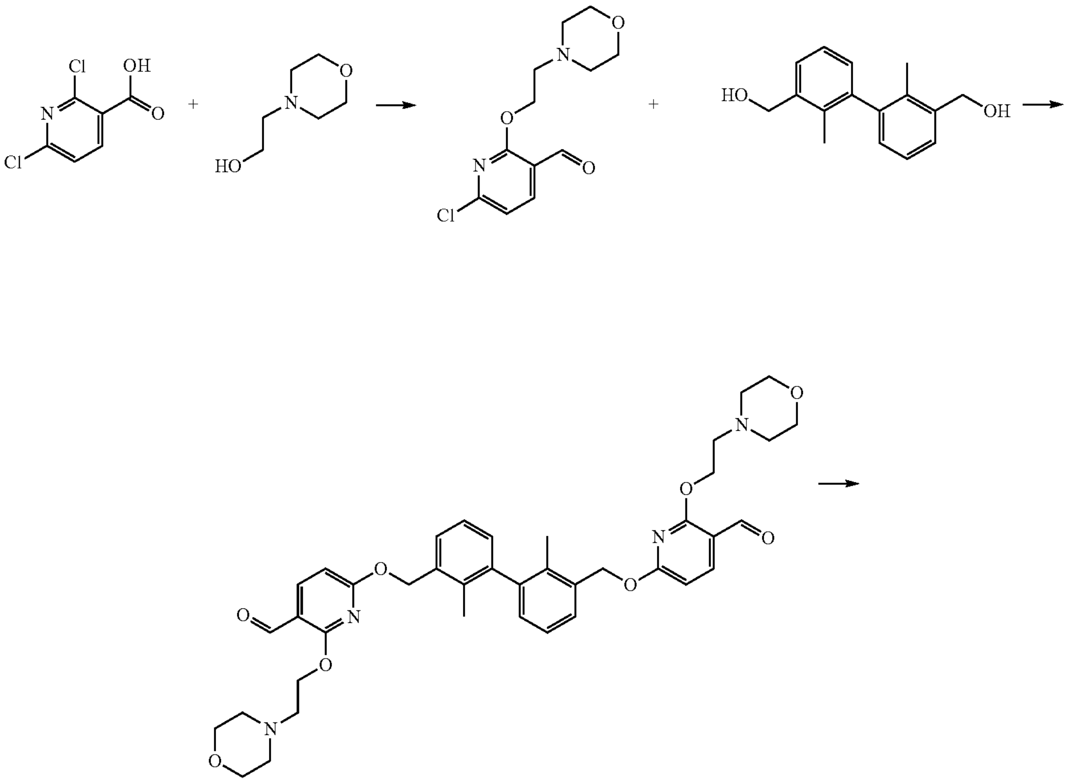

-continued

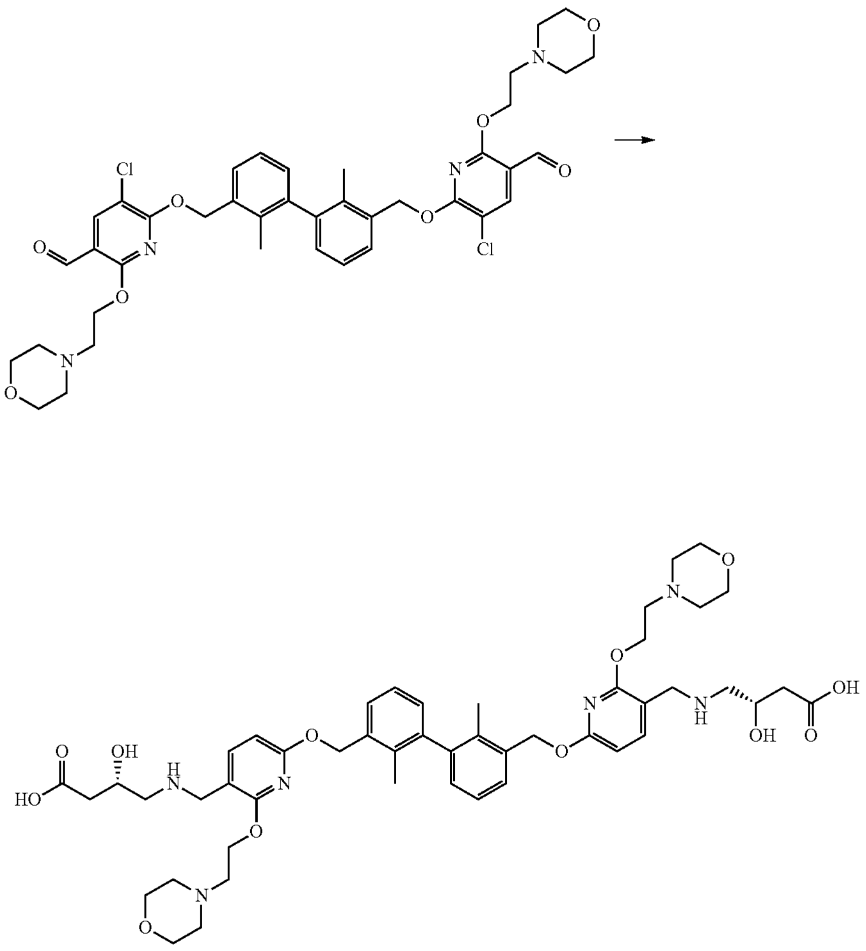

Sodium hydride (300 mg, 7.5 mmol) was charged in a 200 mL RB and THF was added (40 mL). 2-morpholinoethan-1-ol (0.911 mL, 7.5 mmol) was added dropwise, and allowed to stir for 15 min. 2,6-dichloronicotinic acid (576 mg, 3 mmol) was added dropwise as a solution in THF (10 mL) and stirred for 2 h. Borane dimethyl sulfide complex in THF (10.5 mL, 21 mmol, 2M) added dropwise at room temperature. After stirring for 16 h, the reaction was quenched by slow addition of methanol (20 mL) and refluxed for 1 h. The solution was cooled to room temperature, concentrated, and purified by column chromatography to provide (6-chloro-2-(2-morpholinoethoxy)pyridin-3-yl)methanol. $^1$H NMR (400 MHz, Methanol-$d_4$) δ 7.70 (dt, J=7.7, 0.9 Hz, 1H), 6.97 (d, J=7.6 Hz, 1H), 4.55 (d, J=0.9 Hz, 2H), 4.50 (t, J=5.6 Hz, 2H), 3.75-3.64 (m, 4H), 2.79 (t, J=5.6 Hz, 2H), 2.65-2.49 (m, 4H).

(6-Chloro-2-(2-morpholinoethoxy)pyridin-3-yl)methanol (200 mg, 0.73 mmol) was dissolved in methylene chloride and Dess-Martin periodinane (373 mg, 0.88 mmol) was added in one portion. After stirring for 5 minutes, water (12 mg, 0.88 mmol.) was added. After 1.5 h, the reaction was poured into 15 mL of 1N aqueous sodium hydroxide, and extracted with methylene chloride (3×). The combined organics were dried over anhydrous sodium sulfate, concentrated, and purified by column chromatography to provide 6-chloro-2-(2-morpholinoethoxy)nicotinaldehyde (184 mg, 93%) as an orange oil. $^1$H NMR displayed as a mixture of aldehyde to acetal in methanol-$d_4$ $^1$H NMR for aldehyde: (400 MHz, Methanol-$d_4$) δ 10.27 (d, J=0.8 Hz, 1H), 8.11 (d, J=7.9 Hz, 1H), 7.14 (dd, J=7.9, 0.8 Hz, 1H), 4.70-4.55 (m, 2H), 3.69 (m, 4H), 2.86 (t, J=5.6 Hz, 2H), 2.61 (m, 4H).

(2,2'-dimethyl-[1,1'-biphenyl]-3,3'-diyl)dimethanol (72.5 mg, 0.30 mmol) and 6-chloro-2-(2-morpholinoethoxy)nicotinaldehyde (180 mg, 0.66 mmol) were reacted according to the general palladium arylation reaction to provide 6,6'-(((2,2'-dimethyl-[1,1'-biphenyl]-3,3'-diyl)bis(methylene))bis(oxy))bis(2-(2-morpholinoethoxy)nicotinaldehyde) (120 mg, 25%) as an oil. $^1$H NMR (400 MHz, Methanol-$d_4$) δ 10.16 (d, J=0.8 Hz, 2H), 8.07 (d, J=8.4 Hz, 2H), 7.49-7.32 (m, 2H), 7.25 (t, J=7.6 Hz, 2H), 7.09 (dd, J=7.6, 1.4 Hz, 2H), 6.53 (dd, J=8.4, 0.9 Hz, 2H), 5.56 (s, 4H), 4.71-4.55 (m, 4H), 3.73-3.62 (m, 8H), 2.84 (t, J=5.6 Hz, 4H), 2.57 (t, J=4.8 Hz, 8H).

6,6'-(((2,2'-dimethyl-[1,1'-biphenyl]-3,3'-diyl)bis(methylene))bis(oxy))bis(2-(2-morpholinoethoxy)nicotinaldehyde) (30 mg, 0.042 mmol) was reacted according to reductive amination procedure G to provide 17 mg of the title compound as the bis-TFA salt. $^1$H NMR (400 MHz, Methanol-$d_4$) δ 7.76 (d, J=8.2 Hz, 2H), 7.42 (dd, J=7.7, 1.4 Hz, 2H), 7.25 (t, J=7.6 Hz, 2H), 7.08 (dd, J=7.6, 1.4 Hz, 2H), 6.57 (d, J=8.1 Hz, 2H), 5.55-5.31 (m, 4H), 4.33 (dtd, J=9.3, 6.2, 3.1 Hz, 2H), 4.23 (q, J=13.3 Hz, 4H), 3.94 (s, 8H), 3.69 (t, J=4.8 Hz, 4H), 3.45 (s, 8H), 3.26 (d, J=3.1 Hz, 2H), 3.08 (dd, J=12.8, 9.7 Hz, 2H), 2.58 (d, J=6.2 Hz, 4H), 2.05 (s, 6H). MS (m/z) 917.263 (M+H)+.

Example 159: (3S,3'S)-4,4'-((((((2,2'-dimethyl-[1,1'-biphenyl]-3,3'-diyl)bis(methylene))bis(oxy))bis(5-chloro-2-(2-morpholinoethoxy)pyridine-6,3-diyl))bis(methylene))bis(azanediyl))bis(3-hydroxybutanoic acid) (or (3S,3'S)-4,4'-(((6,6'-(((2,2'-dimethyl-[1,1'-biphenyl]-3,3'-diyl)bis(methylene))bis(oxy))bis(5-chloro-2-(2-morpholinoethoxy)pyridine-6,3-diyl))bis(methylene))bis(azanediyl))bis(3-hydroxybutanoic acid))

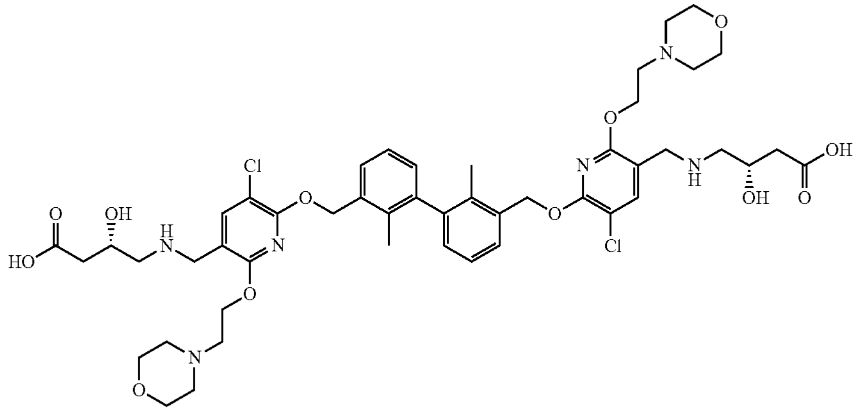 [SMILES: Cc1c(COc2nc(OCCN3CCOCC3)c(CNC[C@@H](O)CC(=O)O)cc2Cl)cccc1-c1cccc(COc2nc(OCCN3CCOCC3)c(CNC[C@@H](O)CC(=O)O)cc2Cl)c1C]

6,6'-(((2,2'-dimethyl-[1,1'-biphenyl]-3,3'-diyl)bis(methylene))bis(oxy))bis(2-(2-morpholinoethoxy)nicotinaldehyde) (46 mg, 0.065 mmol) and N-chlorosuccinimide (60 mg, 0.45 mmol) was dissolved in 1 mL of $CDCl_3$. The resulting clear solution was heated at 50° C. for 1.5 h. The reaction was cooled to room temperature, and concentrated in vacuo to provide the crude product which was used directly in the next step following reductive amination procedure G to provide the title compound. $^1H$ NMR (400 MHz, Methanol-$d_4$) δ 7.88 (s, 2H), 7.47 (dd, J=7.0, 1.4 Hz, 2H), 7.27 (t, J=7.6 Hz, 2H), 7.10 (dd, J=7.6, 1.4 Hz, 2H), 5.67-5.42 (m, 4H), 4.43-4.31 (m, 2H), 4.31-4.18 (m, 4H), 4.09-3.82 (m, 8H), 3.80-3.63 (m, 6H), 3.43 (s, 8H), 3.29-3.26 (m, 2H), 3.22 (q, J=7.4 Hz, 2H), 3.09 (dd, J=12.8, 9.5 Hz, 2H), 2.61-2.56 (m, 4H), 2.08 (s, 6H). MS (m/z) 985.234 (M+H)+.

Example 160: (3S,3'S)-4,4'-((((((2,2'-dimethyl-[1,1'-biphenyl]-3,3'-diyl)bis(methylene))bis(oxy))bis(2-methoxy-5-(trifluoromethyl)pyridine-6,3-diyl))bis(methylene))bis(azanediyl))bis(3-hydroxybutanoic acid) (or (3S,3'S)-4,4'-(((6,6'-(((2,2'-dimethyl-[1,1'-biphenyl]-3,3'-diyl)bis(methylene))bis(oxy))bis(2-methoxy-5-(trifluoromethyl)pyridine-6,3-diyl))bis(methylene))bis(azanediyl))bis(3-hydroxybutanoic acid))

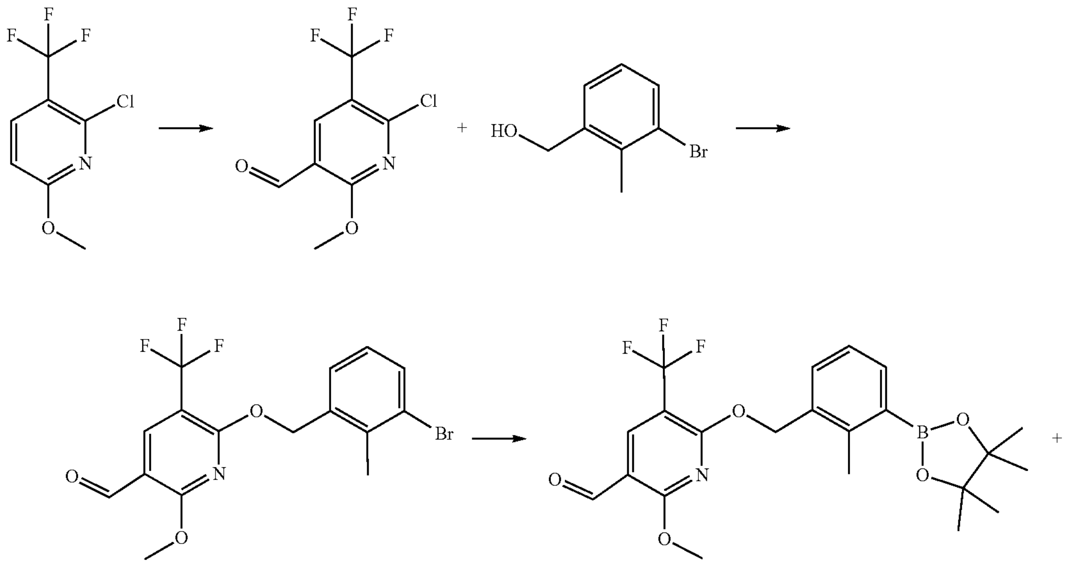

-continued

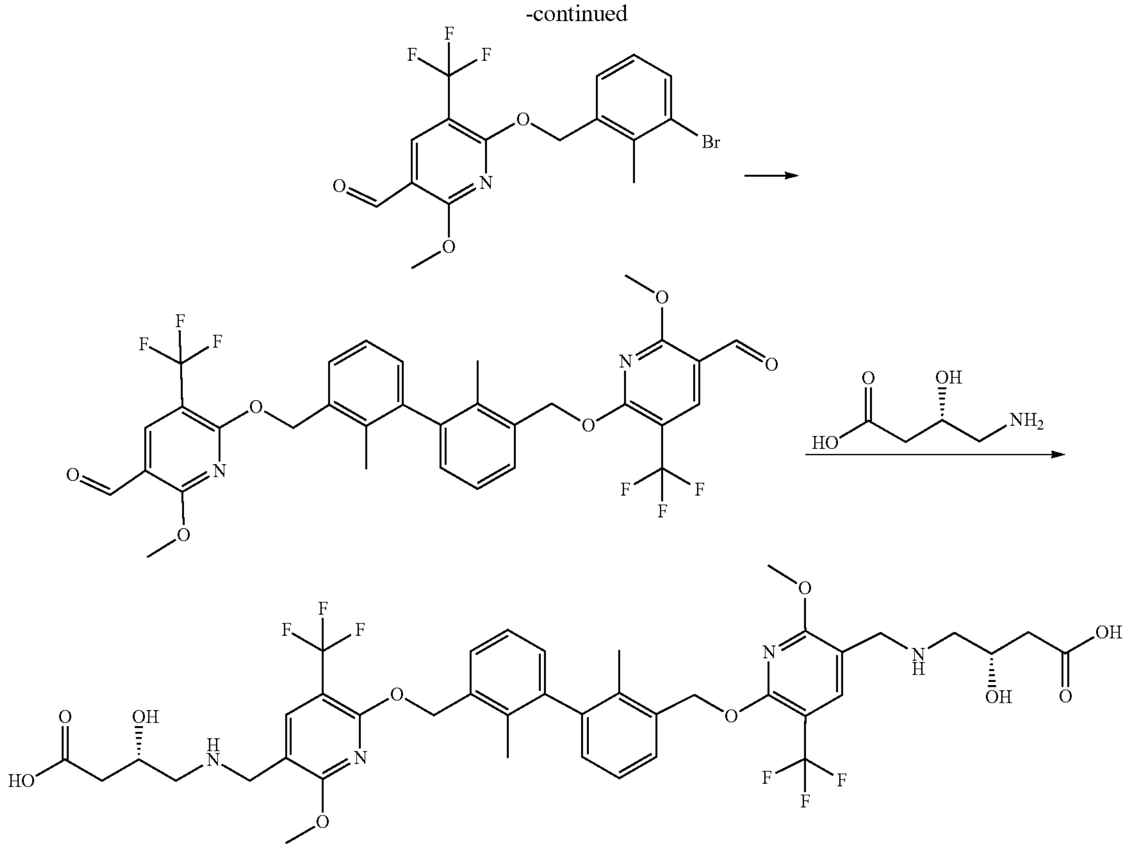

To a stirred solution of 2-chloro-6-methoxy-3-(trifluoromethyl)pyridine (255 mg, 1.2 mmol) in tetrahydrofuran (3 mL) was added t-BuLi (1.7 M solution in n-heptane, 0.9 mL, 1.57 mmol) at −78° C. After 1 h at this temperature, N,N-dimethylformamide (264 mg, 3.6 mmol) was added dropwise. After stirring for 15 min, the reaction was allowed to warm slowly to room temperature. The resulting mixture was quenched with aqueous 1M HCl, brine, and extracted with diethyl ether (3×). The combined organic layer was dried over anhydrous magnesium sulfate, concentrated and purified by column chromatography to provide 6-chloro-2-methoxy-5-(trifluoromethyl)nicotinaldehyde as a clear oil (183 mg, 63%). $^1$H NMR (400 MHz, Chloroform-d) δ 10.30 (s, 1H), 8.39 (s, 1H), 4.16 (s, 3H).

(3-bromo-2-methylphenyl)methanol (184 mg, 0.92 mmol) in N,N-dimethylformamide (0.5 mL) was treated with sodium hydride (37 mg, 0.92 mmol) at room temperature. After stirring for 15 min, the cloudy alkoxide solution was added dropwise to a solution of 6-chloro-2-methoxy-5-(trifluoromethyl)nicotinaldehyde (183 mg, 0.764 mmol) in N,N-dimethylformamide (0.5 mL). After stirring at room temperature for 30 min, the reaction with diluted with saturated aqueous ammonium chloride and ethyl acetate. The organic layer was washed with brine, dried over anhydrous sodium sulfate, concentrated, and purified by column chromatography to provide 6-((3-bromo-2-methylbenzyl)oxy)-2-methoxy-5-(trifluoromethyl)nicotinaldehyde (43 mg, 14%) as a solid. $^1$H NMR (400 MHz, Chloroform-d) δ 10.20 (s, 1H), 8.40-8.24 (m, 1H), 7.56 (d, J=8.0 Hz, 1H), 7.38 (d, J=7.6 Hz, 1H), 7.06 (t, J=7.9 Hz, 1H), 5.58 (s, 2H), 4.11 (s, 3H), 2.47 (s, 3H).

6-((3-bromo-2-methylbenzyl)oxy)-2-methoxy-5-(trifluoromethyl)nicotinaldehyde (15 mg, 0.037 mmol) [1,1'-Bis(diphenylphosphino)ferrocene]dichloropalladium(II) (3 mg, 0.004 mmol), potassium acetate (11 mg, 0.11 mmol), and bis(pinacolato)diboron (9.5 mg, 0.037 mmol) were suspended in dioxane (0.3 mL). The suspension was sparged with nitrogen gas for 1 minute and then heated at 90° C. for 2 h. After cooling to room temperature, the reaction was diluted with ethyl acetate and water. The organic layer was separated, dried with anhydrous sodium sulfate, concentrated and used directly in the next step. Crude 2-methoxy-6-((2-methyl-3-(4,4,5,5-tetramethyl-1,3,2-dioxaborolan-2-yl)benzyl)oxy)-5-(trifluoromethyl)nicotinaldehyde (16 mg, 0.36 mmol), 6-((3-bromo-2-methylbenzyl)oxy)-2-methoxy-5-(trifluoromethyl)nicotinaldehyde (15 mg, 0.38 mmol), [1,1'-Bis(diphenylphosphino)ferrocene]dichloropalladium (II) (3 mg, 0.004 mmol), and potassium carbonate (15.6 mg, 0.11 mmol) were suspended in dioxane (0.7 mL) and water (0.07 mL). The suspension was sparged with nitrogen gas for 5 minutes and then heated at 95° C. for 3 h. After cooling to room temperature, the reaction was diluted with ethyl acetate and water. The organic layer was separated, dried with anhydrous sodium sulfate, concentrated, and purified by silica gel chromatography to provide 6,6'-(((2,2'-dimethyl-[1,1'-biphenyl]-3,3'-diyl)bis(methylene))bis(oxy))bis(2-methoxy-5-(trifluoromethyl)nicotinaldehyde) (20 mg, 82%).

6,6'-(((2,2'-Dimethyl-[1,1'-biphenyl]-3,3'-diyl)bis(methylene))bis(oxy))bis(2-methoxy-5-(trifluoromethyl)nicotinaldehyde) (20 mg, 0.031 mmol) was reacted according to reductive amination procedure G to provide 9 mg of the title compound as the bis-TFA salt. $^1$H NMR (400 MHz, Methanol-d$_4$) δ 8.04 (s, 2H), 7.47 (dd, J=7.8, 1.3 Hz, 2H), 7.24 (t, J=7.6 Hz, 2H), 7.07 (dd, J=7.7, 1.4 Hz, 2H), 5.65 (s, 4H), 4.29 (dtd, J=9.4, 6.3, 3.0 Hz, 2H), 4.21 (s, 4H), 4.13 (s, 6H), 3.23 (dd, J=12.7, 3.1 Hz, 2H), 3.02 (dd, J=12.7, 9.8 Hz, 2H), 2.55 (d, J=6.3 Hz, 4H), 2.06 (s, 6H). MS (m/z) 854.996 (M+H)+.

Example 161: (2R,2'R)-3,3'-((((((2,2'-dimethyl-[1,1'-biphenyl]-3,3'-diyl)bis(methylene))bis(oxy))bis(5-chloro-2-((5-cyanopyridin-3-yl)methoxy)-4,1-phenylene))bis(methylene))bis(azanediyl))bis(2-hydroxypropanoic acid)

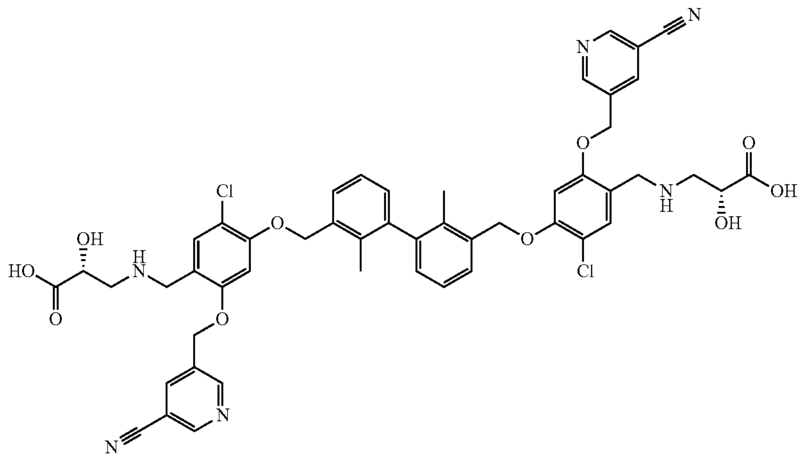 [SMILES: Cc1c(COc2cc(OCc3cncc(C#N)c3)c(CNC[C@@H](O)C(=O)O)cc2Cl)cccc1-c1cccc(COc2cc(OCc3cncc(C#N)c3)c(CNC[C@@H](O)C(=O)O)cc2Cl)c1C]

(2R,2'R)-3,3'-((((((2,2'-Dimethyl-[1,1'-biphenyl]-3,3'-diyl)bis(methylene))bis(oxy))bis(5-chloro-2-((5-cyanopyridin-3-yl)methoxy)-4,1-phenylene))bis(methylene))bis(azanediyl))bis(2-hydroxypropanoic acid) was prepared using general reductive amination procedure B substituting (R)-3-amino-2-hydroxypropanoic acid for (S)-4-amino-3-hydroxybutanoic acid. $^1$H NMR (400 MHz, Methanol-$d_4$) δ 8.96 (d, J=2.0 Hz, 2H), 8.92 (d, J=2.0 Hz, 2H), 8.37 (t, J=2.0 Hz, 2H), 7.51 (s, 2H), 7.47 (d, J=7.5 Hz, 2H), 7.26 (t, J=7.5 Hz, 2H), 7.12 (d, J=7.5 Hz, 2H), 7.08 (s, 2H), 5.38 (s, 4H), 5.31 (s, 4H), 4.40 (dd, J=8.7, 4.0 Hz, 2H), 4.26 (d, J=1.7 Hz, 4H), 3.36 (dd, J=12.9, 4.0 Hz, 2H), 3.17 (dd, J=12.9, 8.7 Hz, 2H), 2.08 (s, 6H). ES/MS (M+1): 961.4

Example 162: (3R,3'R)-4,4'-((((((2,2'-dimethyl-[1,1'-biphenyl]-3,3'-diyl)bis(methylene))bis(oxy))bis(5-chloro-2-((5-cyanopyridin-3-yl)methoxy)-4,1-phenylene))bis(methylene))bis(azanediyl))bis(3-hydroxybutanoic acid)

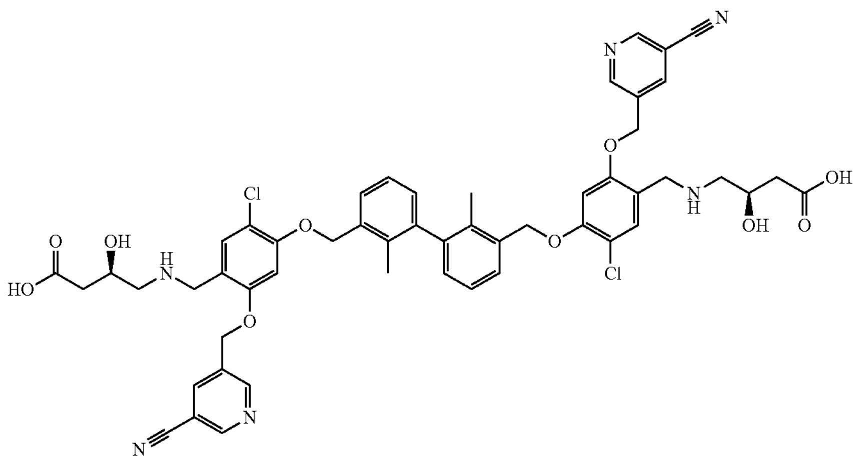 [SMILES: Cc1c(COc2cc(OCc3cncc(C#N)c3)c(CNC[C@H](O)CC(=O)O)cc2Cl)cccc1-c1cccc(COc2cc(OCc3cncc(C#N)c3)c(CNC[C@H](O)CC(=O)O)cc2Cl)c1C]

(3R,3'R)-4,4'-((((((2,2'-dimethyl-[1,1'-biphenyl]-3,3'-diyl)bis(methylene))bis(oxy))bis(5-chloro-2-((5-cyanopyridin-3-yl)methoxy)-4,1-phenylene))bis(methylene))bis(azanediyl))bis(3-hydroxybutanoic acid) was prepared using general reductive amination procedure A substituting (R)-4-amino-3-hydroxybutanoic acid for (S)-4-amino-3-hydroxybutanoic acid. $^1$H NMR (400 MHz, Methanol-$d_4$) δ 8.95 (d, J=2.1 Hz, 2H), 8.92 (d, J=2.0 Hz, 2H), 8.37 (t, J=2.0 Hz, 2H), 7.51 (s, 2H), 7.47 (d, J=7.6 Hz, 2H), 7.27 (t, J=7.6 Hz, 2H), 7.15-7.09 (m, 2H), 7.07 (s, 2H), 5.37 (s, 4H), 5.31 (s, 4H), 4.23 (m, 5H), 3.20 (dd, J=12.7, 3.1 Hz, 2H), 2.97 (dd, J=12.7, 9.8 Hz, 2H), 2.52 (dd, J=6.3, 1.2 Hz, 4H), 2.08 (s, 6H). ES/MS (M+1): 989.1.

Example 163: 5,5'-((((((2,2'-dimethyl-[1,1'-biphenyl]-3,3'-diyl)bis(methylene))bis(oxy))bis(6-((((1H-tetrazol-5-yl)methyl)amino)methyl)-4-chloro-3,1-phenylene))bis(oxy))bis(methylene))dinicotinonitrile (or 5,5'-((((((2,2'-dimethyl-[1,1'-biphenyl]-3,3'-diyl)bis(methylene))bis(oxy))bis(2-((((1H-tetrazol-5-yl)methyl)amino)methyl)-4-chloro-5,1-phenylene))bis(oxy))bis(methylene))dinicotinonitrile)

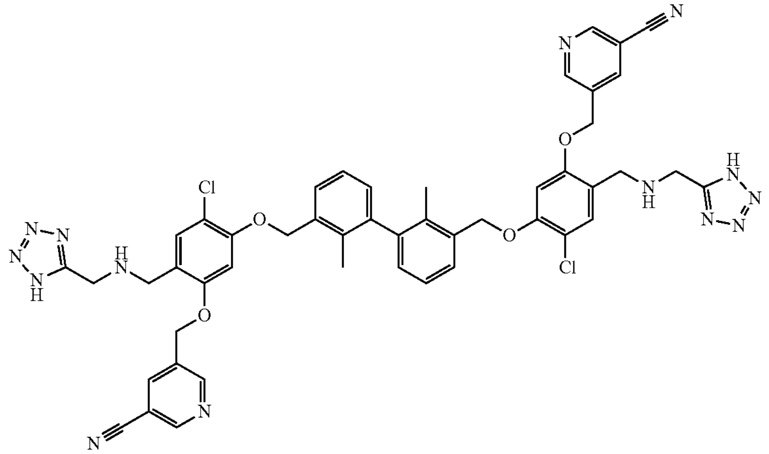 [SMILES: Cc1c(COc2cc(OCc3cncc(C#N)c3)c(CNCc3nnn[nH]3)cc2Cl)cccc1-c1cccc(COc2cc(OCc3cncc(C#N)c3)c(CNCc3nnn[nH]3)cc2Cl)c1C]

5,5'-((((((2,2'-dimethyl-[1,1'-biphenyl]-3,3'-diyl)bis(methylene))bis(oxy))bis(6-((((1H-tetrazol-5-yl)methyl)amino)methyl)-4-chloro-3,1-phenylene))bis(oxy))bis(methylene))dinicotinonitrile was prepared using general reductive amination procedure A substituting (1H-tetrazol-5-yl)methanamine for (3S)-4-amino-3-hydroxybutanoic acid and omitting triethylamine. $^1$H NMR (400 MHz, Methanol-$d_4$) δ 8.92 (dd, J=5.8, 2.0 Hz, 4H), 8.34 (d, J=2.0 Hz, 2H), 7.52 (s, 2H), 7.46 (dd, J=7.6, 1.4 Hz, 2H), 7.26 (t, J=7.6 Hz, 2H), 7.12 (dd, J=7.7, 1.4 Hz, 2H), 7.06 (s, 2H), 5.34 (s, 4H), 5.31 (s, 4H), 4.58 (s, 4H), 4.37 (s, 4H), 2.07 (s, 6H). ES/MS (M+1): 948.9.

Example 164: 4,4'-((((((2,2'-dimethyl-[1,1'-biphenyl]-3,3'-diyl)bis(methylene))bis(oxy))bis(5-chloro-2-((5-cyanopyridin-3-yl)methoxy)-4,1-phenylene))bis(methylene))bis(azanediyl))dibutyric acid

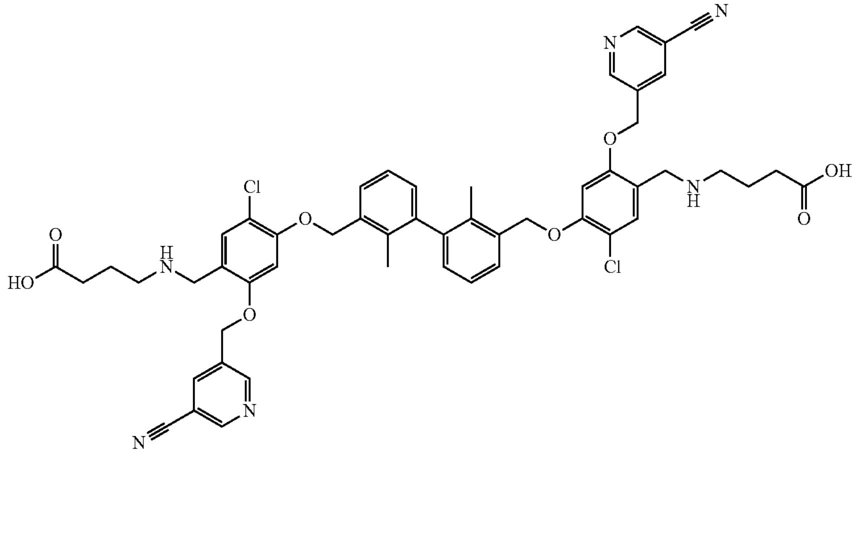 [SMILES: Cc1c(COc2cc(OCc3cncc(C#N)c3)c(CNCCCC(=O)O)cc2Cl)cccc1-c1cccc(COc2cc(OCc3cncc(C#N)c3)c(CNCCCC(=O)O)cc2Cl)c1C]

4,4'-((((((2,2'-dimethyl-[1,1'-biphenyl]-3,3'-diyl)bis(methylene))bis(oxy))bis(5-chloro-2-((5-cyanopyridin-3-yl)methoxy)-4,1-phenylene))bis(methylene))bis(azanediyl))dibutyric acid was prepared using general reductive amination procedure G substituting 4-aminobutanoic acid for (3S)-4-amino-3-hydroxybutanoic acid. $^1$H NMR (400 MHz, Methanol-$d_4$) δ 8.96 (d, J=2.1 Hz, 2H), 8.92 (d, J=2.0 Hz, 2H), 8.36 (t, J=2.1 Hz, 2H), 7.50 (s, 2H), 7.46 (dd, J=7.6, 1.3 Hz, 2H), 7.26 (t, J=7.6 Hz, 2H), 7.12 (dd, J=7.6, 1.3 Hz, 2H), 7.06 (s, 2H), 5.38 (s, 4H), 5.31 (s, 4H), 4.20 (s, 4H), 3.12-3.03 (m, 4H), 2.41 (t, J=6.9 Hz, 4H), 2.07 (s, 6H), 1.97-1.86 (m, 4H). ES/MS (M+1): 957.2.

Example 165: (3S,3'S)-4,4'-((((((2,2'-dimethyl-[1,1'-biphenyl]-3,3'-diyl)bis(methylene))bis(oxy))bis(5-chloro-2-((5-cyanopyridin-3-yl)methoxy)-4,1-phenylene))bis(methylene))bis(azanediyl))bis(3-hydroxybutanamide)

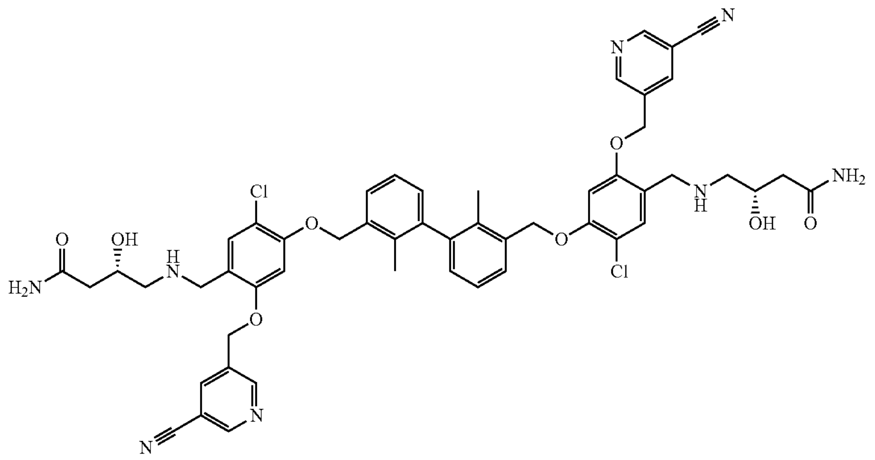 [SMILES: Cc1c(COc2cc(OCc3cncc(C#N)c3)c(CNC[C@@H](O)CC(N)=O)cc2Cl)cccc1-c1cccc(COc2cc(OCc3cncc(C#N)c3)c(CNC[C@@H](O)CC(N)=O)cc2Cl)c1C]

(3S,3'S)-4,4'-((((((2,2'-dimethyl-[1,1'-biphenyl]-3,3'-diyl)bis(methylene))bis(oxy))bis(5-chloro-2-((5-cyanopyridin-3-yl)methoxy)-4,1-phenylene))bis(methylene))bis(azanediyl))bis(3-hydroxybutanamide) was prepared using general reductive amination procedure G substituting (S)-4-amino-3-hydroxybutanamide for (3S)-4-amino-3-hydroxybutanoic acid. $^1$H NMR (400 MHz, Methanol-$d_4$) δ 8.96 (d, J=2.1 Hz, 2H), 8.92 (d, J=2.0 Hz, 2H), 8.39 (t, J=2.1 Hz, 2H), 7.50 (s, 2H), 7.47 (d, J=7.6 Hz, 2H), 7.30-7.23 (m, 2H), 7.12 (d, J=7.3 Hz, 2H), 7.07 (s, 2H), 5.37 (s, 43H), 5.31 (s, 4H), 4.28-4.14 (m, 6H), 3.22-3.17 (m, 1H), 3.04-2.93 (m, 2H), 2.45 (dd, J=6.0, 2.2 Hz, 4H), 2.08 (s, 6H). ES/MS (M+1): 987.1.

Example 166: (2S,2'S)-3,3'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(2-hydroxypropanoic acid) (or (2S,2'S)-3,3'-(((6,6'-(((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(2-hydroxypropanoic acid))

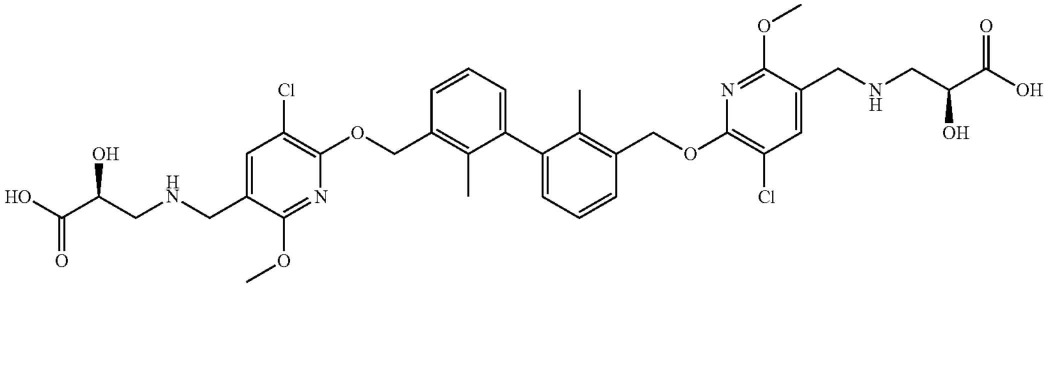 [SMILES: COc1nc(OCc2cccc(-c3cccc(COc4nc(OC)c(CNC[C@H](O)C(=O)O)cc4Cl)c3C)c2C)c(Cl)cc1CNC[C@H](O)C(=O)O]

(2S,2'S)-3,3'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(2-hydroxypropanoic acid) was prepared using general reductive amination procedure G substituting l-isoserine for (3S)-4-amino-3-hydroxybutanoic acid. $^1$H NMR (400 MHz, Methanol-$d_4$) δ 7.81 (s, 2H), 7.51-7.44 (m, 2H), 7.24 (t, J=7.6 Hz, 2H), 7.12-7.04 (m, 2H), 5.59 (s, 4H), 4.42 (dd, J=8.7, 4.0 Hz, 2H), 4.18 (s, 4H), 4.05 (s, 6H), 3.38 (dd, J=12.9, 4.0 Hz, 2H), 3.19 (dd, J=12.9, 8.7 Hz, 2H), 2.09 (s, 6H). ES/MS (M+1): 759.0.

Example 167: (2R,2'R)-3,3'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(2-hydroxypropanoic acid) (or (2R,2'R)-3,3'-(((6,6'-(((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(2-hydroxypropanoic acid))

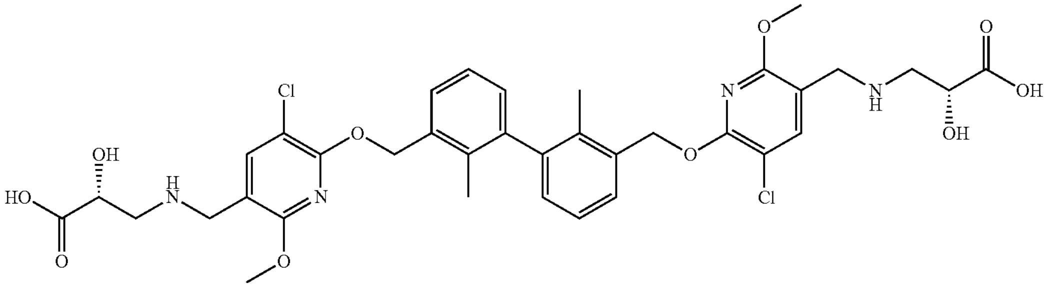 [SMILES: COc1nc(OCc2cccc(-c3cccc(COc4nc(OC)c(CNC[C@@H](O)C(=O)O)cc4Cl)c3C)c2C)c(Cl)cc1CNC[C@@H](O)C(=O)O]

(2R,2'R)-3,3'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(2-hydroxypropanoic acid) was prepared using general reductive amination procedure G substituting d-isoserine for (3S)-4-amino-3-hydroxybutanoic acid. $^1$H NMR (400 MHz, Methanol-$d_4$) δ 7.81 (s, 2H), 7.51-7.44 (m, 2H), 7.24 (t, J=7.6 Hz, 2H), 7.07 (dd, J=7.7, 1.3 Hz, 2H), 5.59 (s, 4H), 4.44 (dd, J=8.8, 3.9 Hz, 2H), 4.18 (s, 4H), 4.05 (s, 6H), 3.39 (dd, J=12.9, 3.9 Hz, 2H), 3.19 (dd, J=12.9, 8.8 Hz, 2H), 2.09 (s, 6H). ES/MS (M+1): 758.9.

Example 168: 2,2'-((((((2,2'-Dimethyl-[1,1'-biphenyl]-3,3'-diyl)bis(methylene))bis(oxy))bis(5-chloro-2-methoxypyridine-6,3-diyl))bis(methylene))bis(azanediyl))bis(N-(methylsulfonyl)acetamide) (or 2,2'-(((6,6'-(((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(N-(methylsulfonyl)acetamide))

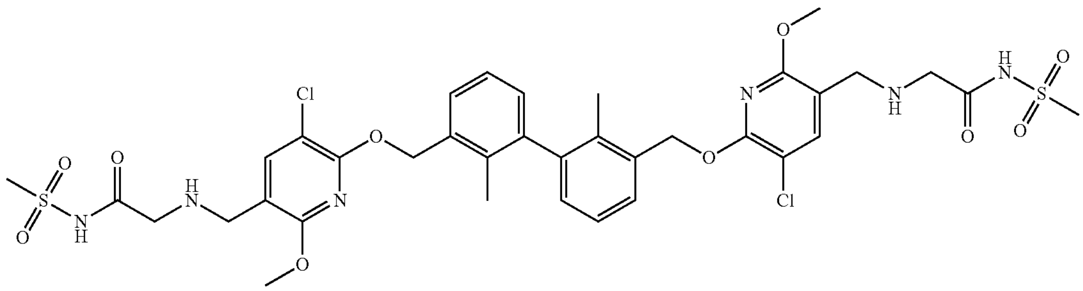

Benzyl (2-(methylsulfonamido)-2-oxoethyl)carbamate: Carbonyldiimidazole (1.55 g, 956 mmol) was added to a solution of ((benzyloxy)carbonyl)glycine (2.00 g, 9.56 mmol) in tetrahydrofuran (40 mL). Mild gas evolution was observed. After 30 min the solution was heated at reflux for 1.5 h. The solution was cooled to RT and methylsulfonamide (0.909 g, 9.56 mmol) was added. The solution was stirred at room temperature for 15 min. A solution of 1,8-Diazabicyclo [5.4.0]undec-7-ene in tetrahydrofuran (5 mL) was added. After 22h the reaction was poured into ice cold 0.75 N hydrochloric acid (100 mL). A solid gradually formed. The solid was isolated by filtration with water washing. The solid was dried under vacuum, providing benzyl (2-(methylsulfonamido)-2-oxoethyl)carbamate.

2-Amino-N-(methylsulfonyl)acetamide: 10% Palladium on carbon (746 mg, 0.701 mmol) was added to a solution of benzyl (2-(methylsulfonamido)-2-oxoethyl)carbamate (2.008 g, 7.01 mmol) in ethanol (30 mL). The atmosphere was exchanged with hydrogen (balloon). After stirring for 1 h a solid had precipitated. The hydrogen was removed. The solid was removed by filtration through celite (along with the catalyst). The solid was washed with water (30 mL). The aqueous phase was filtered through a syringe filter and subjected to lyophilization providing 2-amino-N-(methylsulfonyl)acetamide.

2,2'-((((((2,2'-Dimethyl-[1,1'-biphenyl]-3,3'-diyl)bis(methylene))bis(oxy))bis(5-chloro-2-methoxypyridine-6,3-diyl))bis(methylene))bis(azanediyl))bis(N-(methylsulfonyl)acetamide) was prepared using general reductive amination procedure G substituting 2-amino-N-(methylsulfonyl)acetamide for (3S)-4-amino-3-hydroxybutanoic acid. $^1$H NMR (400 MHz, Methanol-$d_4$) δ 7.80 (s, 2H), 7.47 (dd, J=7.6, 1.4 Hz, 2H), 7.24 (t, J=7.6 Hz, 2H), 7.08 (dd, J=7.6, 1.4 Hz, 2H), 5.60 (s, 4H), 4.19 (s, 4H), 4.06 (s, 6H), 3.90 (s, 4H), 3.24 (s, 6H), 2.09 (s, 6H). ES/MS (M+1): 853.1.

Example 169: 1,1'-((((2,2'-dimethyl-[1,1'-biphenyl]-3,3'-diyl)bis(methylene))bis(oxy))bis(5-chloro-2-methoxypyridine-6,3-diyl))bis(N-((1H-tetrazol-5-yl)methyl)methanamine) (or 1,1'-(6,6'-(((2,2'-dimethyl-[1,1'-biphenyl]-3,3'-diyl)bis(methylene))bis(oxy))bis(5-chloro-2-methoxypyridine-6,3-diyl))bis(N-((1H-tetrazol-5-yl)methyl)methanamine))

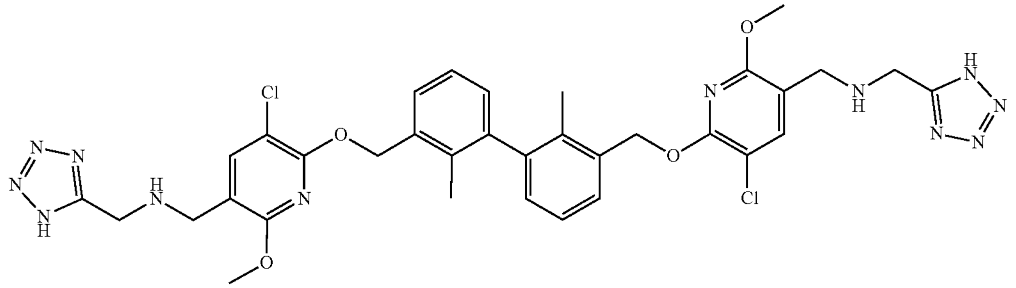 [SMILES: COc1nc(OCc2cccc(-c3cccc(COc4nc(OC)c(CNCc5nnn[nH]5)cc4Cl)c3C)c2C)c(Cl)cc1CNCc1nnn[nH]1]

1,1'-((((2,2'-dimethyl-[1,1'-biphenyl]-3,3'-diyl)bis(methylene))bis(oxy))bis(5-chloro-2-methoxypyridine-6,3-diyl))bis(N-((1H-tetrazol-5-yl)methyl)methanamine) was prepared using general reductive amination procedure A substituting (1H-tetrazol-5-yl)methanamine for (3S)-4-amino-3-hydroxybutanoic acid, omitting triethylamine and adding dichloromethane in equal proportion to dimethylformamide (0.0125 M). $^1$H NMR (400 MHz, Methanol-$d_4$) δ 7.81 (s, 2H), 7.50-7.44 (m, 2H), 7.24 (td, J=7.6, 0.7 Hz, 2H), 7.07 (dd, J=7.7, 1.4 Hz, 2H), 5.59 (s, 4H), 4.57 (s, 4H), 4.27 (s, 4H), 4.03 (s, 6H), 2.08 (s, 6H). ES/MS (M+1): 747.3.

Example 170: 1,1'-((((2,2'-dimethyl-[1,1'-biphenyl]-3,3'-diyl)bis(methylene))bis(oxy))bis(5-chloro-2-methoxypyridine-6,3-diyl))bis(N-((5-methyl-1,3,4-oxadiazol-2-yl)methyl)methanamine) (or 1,1'-(6,6'-(((2,2'-dimethyl-[1,1'-biphenyl]-3,3'-diyl)bis(methylene))bis(oxy))bis(5-chloro-2-methoxypyridine-6,3-diyl))bis(N-((5-methyl-1,3,4-oxadiazol-2-yl)methyl)methanamine))

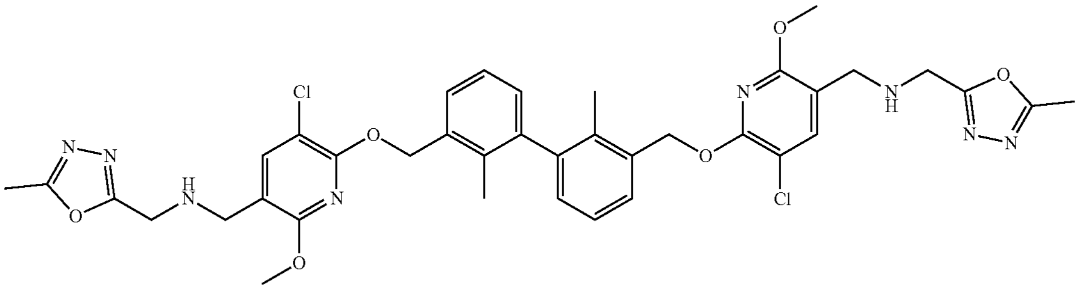

1,1'-((((2,2'-dimethyl-[1,1'-biphenyl]-3,3'-diyl)bis(methylene))bis(oxy))bis(5-chloro-2-methoxypyridine-6,3-diyl))bis(N-((5-methyl-1,3,4-oxadiazol-2-yl)methyl)methanamine) was prepared using general reductive amination procedure A substituting (5-methyl-1,3,4-oxadiazol-2-yl)methanamine for (3S)-4-amino-3-hydroxybutanoic acid. $^1$H NMR (400 MHz, Methanol-$d_4$) δ 7.81 (s, 2H), 7.47 (dd, J=7.5, 1.3 Hz, 2H), 7.24 (t, J=7.6 Hz, 2H), 7.08 (dd, J=7.7, 1.4 Hz, 2H), 5.60 (s, 4H), 4.56 (s, 4H), 4.30 (s, 4H), 4.05 (s, 6H), 2.56 (s, 6H), 2.09 (s, 6H). ES/MS (M+1): 775.2.

Example 171: 1,1'-((((2,2'-dimethyl-[1,1'-biphenyl]-3,3'-diyl)bis(methylene))bis(oxy))bis(5-chloro-2-methoxypyridine-6,3-diyl))bis(N-((1H-1,2,3-triazol-4-yl)methyl)methanamine) (or 1,1'-(6,6'-(((2,2'-dimethyl-[1,1'-biphenyl]-3,3'-diyl)bis(methylene))bis(oxy))bis(5-chloro-2-methoxypyridine-6,3-diyl))bis(N-((1H-1,2,3-triazol-4-yl)methyl)methanamine))

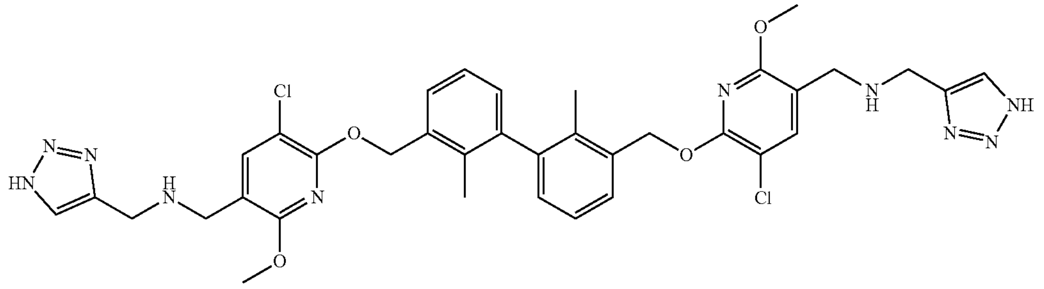 [SMILES: COc1nc(OCc2cccc(-c3cccc(COc4nc(OC)c(CNCc5c[nH]nn5)cc4Cl)c3C)c2C)c(Cl)cc1CNCc1c[nH]nn1]

1,1'-((((2,2'-dimethyl-[1,1'-biphenyl]-3,3'-diyl)bis(methylene))bis(oxy))bis(5-chloro-2-methoxypyridine-6,3-diyl))bis(N-((1H-1,2,3-triazol-4-yl)methyl)methanamine) was prepared using general reductive amination procedure A substituting (1H-1,2,3-triazol-4-yl)methanamine hydrochloride for (3S)-4-amino-3-hydroxybutanoic acid, and adding dichloromethane in equal proportion to dimethylformamide (0.0125 M). $^1$H NMR (400 MHz, Methanol-$d_4$) δ 7.79 (s, 2H), 7.47 (d, J=7.7 Hz, 2H), 7.24 (t, J=7.6 Hz, 2H), 7.07 (dd, J=7.6, 1.4 Hz, 2H), 5.59 (s, 4H), 4.39 (s, 4H), 4.18 (s, 4H), 4.03 (s, 6H), 2.08 (s, 6H). ES/MS (M+1): 745.0.

Example 172: 3,3'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))dipropionic acid

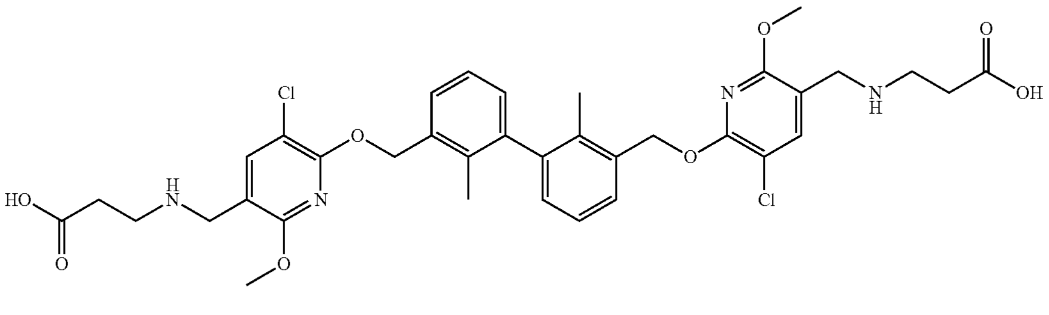 [SMILES: COc1nc(OCc2cccc(-c3cccc(COc4nc(OC)c(CNCCC(=O)O)cc4Cl)c3C)c2C)c(Cl)cc1CNCCC(=O)O]

3,3'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))dipropionic acid was prepared using general reductive amination procedure G substituting 3-aminopropanoic acid for (3S)-4-amino-3-hydroxybutanoic acid. $^1$H NMR (400 MHz, Methanol-$d_4$) δ 7.81 (s, 2H), 7.47 (dd, J=7.7, 1.4 Hz, 2H), 7.24 (t, J=7.6 Hz, 2H), 7.07 (dd, J=7.7, 1.4 Hz, 2H), 5.59 (s, 4H), 4.15 (s, 4H), 4.06 (s, 6H), 3.27 (t, J=6.5 Hz, 4H), 2.75 (t, J=6.5 Hz, 4H), 2.09 (s, 6H). ES/MS (M+1): 726.9.

Example 173: (4R,4'R)-4,4'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(isoxazolidin-3-one) (or (4R,4'R)-4,4'-(((6,6'-(((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(isoxazolidin-3-one))

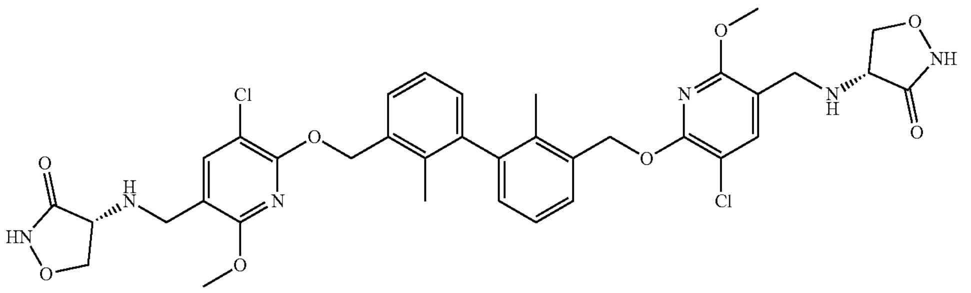 [SMILES: COc1nc(OCc2cccc(-c3cccc(COc4nc(OC)c(CN[C@@H]5CONC5=O)cc4Cl)c3C)c2C)c(Cl)cc1CN[C@@H]1CONC1=O]

(4R,4'R)-4,4'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(isoxazolidin-3-one) was prepared using general reductive amination procedure A substituting (R)-4-aminoisoxazolidin-3-one for (3S)-4-amino-3-hydroxybutanoic acid, and adding dichloromethane in equal proportion to dimethylformamide (0.0125 M). $^1$H NMR (400 MHz, Methanol-$d_4$) δ 7.82 (s, 2H), 7.47 (dd, J=7.7, 1.4 Hz, 2H), 7.24 (t, J=7.6 Hz, 2H), 7.07 (dd, J=7.6, 1.4 Hz, 2H), 5.60 (s, 4H), 4.70 (dd, J=9.7, 8.0 Hz, 2H), 4.51 (t, J=8.1 Hz, 2H), 4.45-4.32 (m, 4H), 4.21 (d, J=13.3 Hz, 2H), 4.05 (s, 6H), 2.08 (s, 6H). ES/MS (M+1): 752.8.

Example 174: 2,2'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(N-(N,N-dimethylsulfamoyl)acetamide)-2-amino-N-(N,N-dimethylsulfamoyl)acetamide (or 2,2'-(((6,6'-(((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(N-(N,N-dimethylsulfamoyl)acetamide))

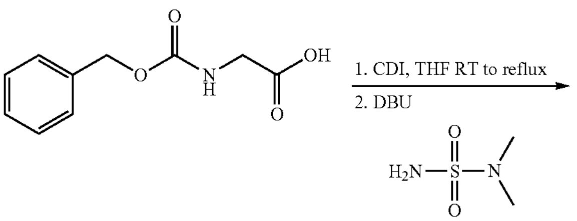

-continued

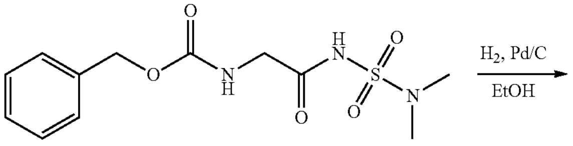

-continued

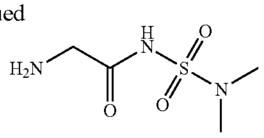

Benzyl(2-((N,N-dimethylsulfamoyl)amino)-2-oxoethyl)carbamate: Carbonyldiimidazole (1.55 g, 956 mmol) was added to a solution of ((benzyloxy)carbonyl)glycine (2.00 g, 9.56 mmol) in tetrahydrofuran (40 mL). Mild gas evolution was observed. After 30 min the solution was heated at reflux for 1.5 h. The solution was cooled to RT and N,N-dimethylsulfamide (1.18 g, 9.56 mmol) was added. The solution was stirred at room temperature for 15 min. A solution of 1,8-Diazabicyclo[5.4.0]undec-7-ene in tetrahydrofuran (5 mL) was added. After 22h the reaction was poured into ice-cold 0.75 N hydrochloric acid (100 mL). The aqueous phase was extracted with ethyl acetate (3×50 mL). The combined organic phases were washed with brine (50 mL) and dried over sodium sulfate. The solvent was removed under reduced pressure. The residue was subjected to flash chromatography (0-100% ethyl acetate/hexanes). The fractions containing product were combined and the solvent was removed under reduced pressure, providing benzyl (2-((N,N-dimethylsulfamoyl)amino)-2-oxoethyl)carbamate.

2-amino-N-(N,N-dimethylsulfamoyl)acetamide: 10% Palladium on carbon (628 mg, 0.590 mmol) was added to a solution of benzyl (2-(methylsulfonamido)-2-oxoethyl)carbamate (1.86 g, 5.90 mmol) in ethanol (30 mL). The atmosphere was exchanged with hydrogen (balloon). After stirring for 1h a solid had precipitated. The hydrogen was removed. The solid was removed by filtration through celite (along with the catalyst). The solid was washed with water (30 mL). The aqueous phase was filtered through a syringe filter and subjected to lyophilization providing 2-amino-N-(N,N-dimethylsulfamoyl)acetamide.

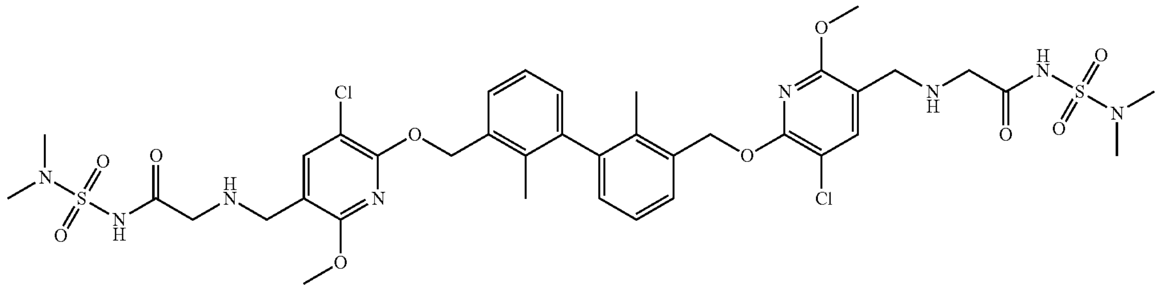

2,2'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(N-(N,N-dimethylsulfamoyl)acetamide) was prepared using general reductive amination procedure G substituting 2-amino-N-(N,N-dimethylsulfamoyl)acetamide for (3S)-4-amino-3-hydroxybutanoic acid. $^1$H NMR (400 MHz, Methanol-$d_4$) δ 7.80 (s, 2H), 7.51-7.44 (m, 2H), 7.25 (t, J=7.6 Hz, 2H), 7.08 (dd, J=7.6, 1.4 Hz, 2H), 5.60 (s, 4H), 4.19 (s, 4H), 4.06 (s, 6H), 3.90 (s, 4H), 2.90 (s, 12H), 2.09 (s, 6H). ES/MS (M+1): 910.9.

Example 175: 1,1'-((((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(methylene))bis(cyclopropan-1-ol) (or 1,1'-((((6,6'-(((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(methylene))bis(cyclopropan-1-ol))

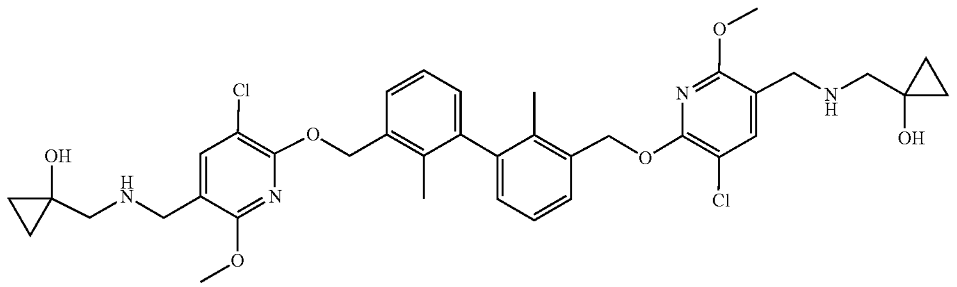 [SMILES: COc1nc(OCc2cccc(-c3cccc(COc4nc(OC)c(CNCC5(O)CC5)cc4Cl)c3C)c2C)c(Cl)cc1CNCC1(O)CC1]

1,1'-((((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(methylene))bis(cyclopropan-1-ol) was prepared using general reductive amination procedure G substituting 1-(aminomethyl)cyclopropan-1-ol for (3S)-4-amino-3-hydroxybutanoic acid, methanol for ethanol and omitting potassium hydroxide. $^1$H NMR (400 MHz, Methanol-$d_4$) δ 7.81 (s, 2H), 7.51-7.44 (m, 2H), 7.24 (t, J=7.6 Hz, 2H), 7.11-7.04 (m, 2H), 5.59 (s, 4H), 4.21 (s, 4H), 4.05 (s, 6H), 3.12 (s, 5H), 2.09 (s, 6H), 0.93-0.85 (m, 4H), 0.74-0.66 (m, 4H). ES/MS (M+1): 722.9.

Example 176: 3,3'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(1,1-difluoropropan-2-ol) (or 3,3'-(((6,6'-(((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(1,1-difluoropropan-2-ol))

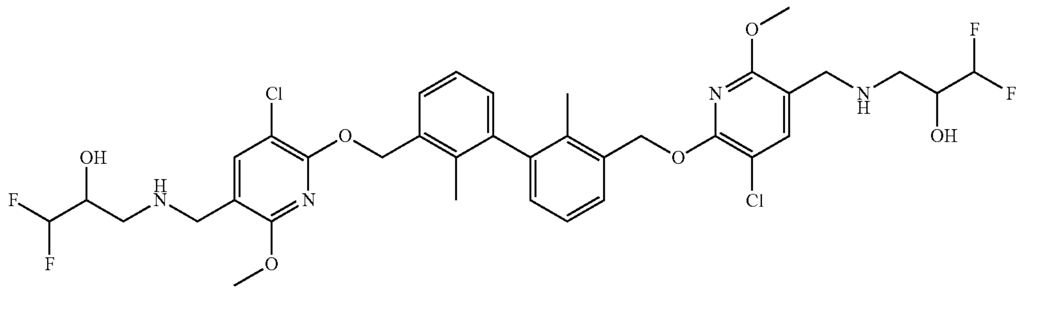 [SMILES: COc1nc(OCc2cccc(-c3cccc(COc4nc(OC)c(CNCC(O)C(F)F)cc4Cl)c3C)c2C)c(Cl)cc1CNCC(O)C(F)F]

3,3'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(1,1-difluoropropan-2-ol) was prepared using general reductive amination procedure A substituting 3-amino-1,1-difluoropropan-2-ol hydrochloride for (3S)-4-amino-3-hydroxybutanoic acid, diisopropylethylamine for triethylamine and adding ethanol in equal proportion to dimethylformamide (0.0125 M). $^1H$ NMR (400 MHz, Methanol-$d_4$) δ 7.81 (s, 2H), 7.51-7.44 (m, 2H), 7.24 (t, J=7.6 Hz, 2H), 7.07 (dd, J=7.6, 1.4 Hz, 2H), 5.98-5.66 (m, 2H), 5.59 (s, 4H), 4.18 (d, J=1.3 Hz, 4H), 4.17-4.05 (m, 2H), 4.05 (s, 6H), 3.24 (dd, J=12.8, 3.3 Hz, 2H), 3.12 (dd, J=13.0, 9.9 Hz, 2H), 2.09 (s, 6H). ES/MS (M+1): 770.8.

Example 177: (3S,3'S)-4,4'-((((((2,2'-dimethyl-[1,1'-biphenyl]-3,3'-diyl)bis(methylene))bis(oxy))bis(3-cyano-4,1-phenylene))bis(methylene))bis(azanediyl))bis(3-hydroxybutanoic acid)

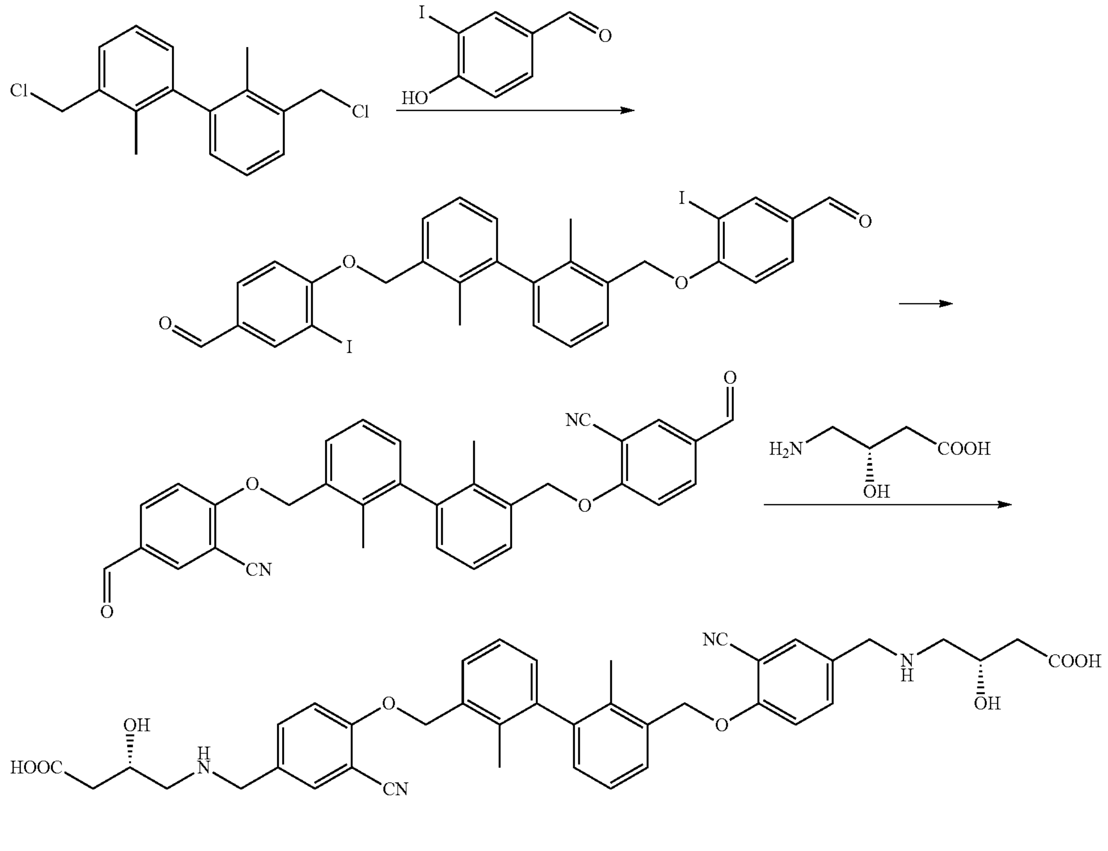

A suspension of 3,3'-bis(chloromethyl)-2,2'-dimethyl-1,1'-biphenyl (100 mg, 0.358 mmol), 4-hydroxy-3-iodobenzaldehyde (266 mg, 1.07 mmol), cesium carbonate (350 mg, 1.07 mmol), and sodium iodide (161 mg, 1.07 mmol) in dimethylformamide (3 mL) was stirred at 20° C. for 20 h. The mixture was diluted with ethyl acetate (30 mL) and washed with water (2×10 mL) and brine (10 mL). The organic phase was dried over sodium sulfate and the solvent was removed under reduced pressure. The residue was subjected to flash chromatography (0-50% ethyl acetate/hexanes). The fractions containing product were combined and the solvent was removed under reduced pressure, providing 4,4'-(((2,2'-dimethyl-[1,1'-biphenyl]-3,3'-diyl)bis(methylene))bis(oxy))bis(3-iodobenzaldehyde).

4,4'-(((2,2'-dimethyl-[1,1'-biphenyl]-3,3'-diyl)bis(methylene))bis(oxy))bis(3-iodobenzaldehyde) (75 mg, 0.107 mmol), and copper (I) cyanide (24 mg, 0.267 mmol) were combined with dimethylformamide (2 mL) and heated at 140° C. for 20 min in a microwave reactor. The reaction had mono CN and desired material. The reaction was diluted with ethyl acetate (10 mL) and water (10 mL). A solid formed which was removed by filtration. The organic phase was washed with water (2×10 mL) and brine (10 mL). The organic phase was dried over sodium sulfate and the solvent was removed under reduced pressure. The residue was subjected to flash chromatography (0-100% ethyl acetate/hexanes). The fractions containing product were combined and the solvent was removed under reduced pressure, providing 6,6'-(((2,2'-dimethyl-[1,1'-biphenyl]-3,3'-diyl)bis(methylene))bis(oxy))bis(3-formylbenzonitrile).

(3S,3'S)-4,4'-((((((2,2'-dimethyl-[1,1'-biphenyl]-3,3'-diyl)bis(methylene))bis(oxy))bis(3-cyano-4,1-phenylene))bis(methylene))bis(azanediyl))bis(3-hydroxybutanoic acid) was prepared following reductive amination procedure A substituting glycine (10 equiv) for (3S)-4-Amino-3-hydroxybutanoic acid (6 equiv) and using 10 eq trimethylamine rather than 6 eq. for a reaction time of 16h. $^1$H NMR (400 MHz, Methanol-$d_4$) δ 7.80 (d, J=2.3 Hz, 2H), 7.77 (dd, J=8.8, 2.3 Hz, 2H), 7.52-7.47 (m, 2H), 7.44 (d, J=8.8 Hz, 2H), 7.28 (t, J=7.6 Hz, 2H), 7.16-7.09 (m, 2H), 5.36 (s, 4H), 4.33-4.24 (m, 1H), 4.23 (s, 4H), 3.20 (dd, J=12.6, 3.1 Hz, 2H), 3.01 (dd, J=12.4, 9.5 Hz, 2H), 2.54 (d, J=6.3 Hz, 4H), 2.09 (s, 6H). ES/MS (M+1): 707.1.

Example 178: 2,2'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))diacetic acid (or 2,2'-(((6,6'-(((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))diacetic acid)

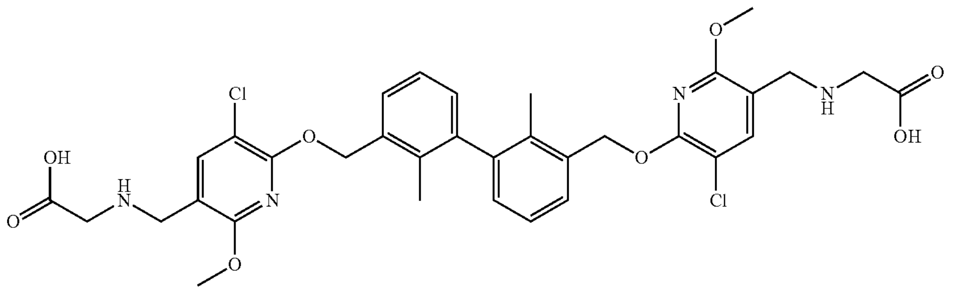 [SMILES: COc1nc(OCc2cccc(-c3cccc(COc4nc(OC)c(CNCC(=O)O)cc4Cl)c3C)c2C)c(Cl)cc1CNCC(=O)O]

2,2'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))diacetic acid was prepared following reductive amination procedure G, substituting glycine for (3S)-4-amino-3-hydroxybutanoic acid. $^1$H NMR (400 MHz, Methanol-$d_4$) δ 7.80 (s, 2H), 7.51-7.44 (m, 2H), 7.24 (t, J=7.6 Hz, 2H), 7.08 (dd, J=7.8, 1.4 Hz, 2H), 5.59 (s, 4H), 4.18 (s, 4H), 4.05 (s, 6H), 3.87 (s, 4H), 2.09 (s, 6H). ES/MS (M+1): 698.8.

Example 179: (2R,2'R)-3,3'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(2-fluoropropanoic acid) (or (2R,2'R)-3,3'-(((6,6'-(((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(2-fluoropropanoic acid))

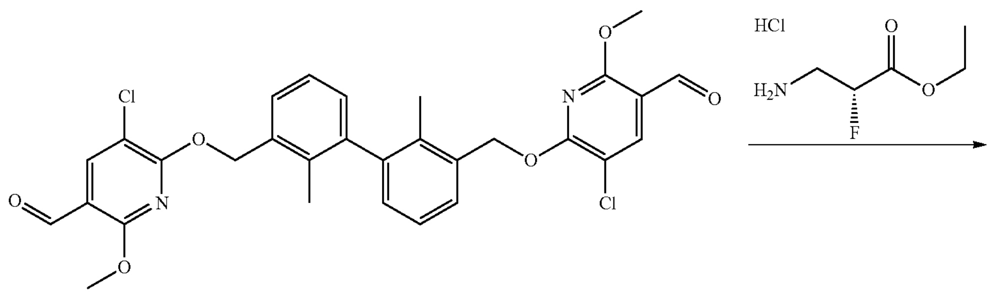

-continued

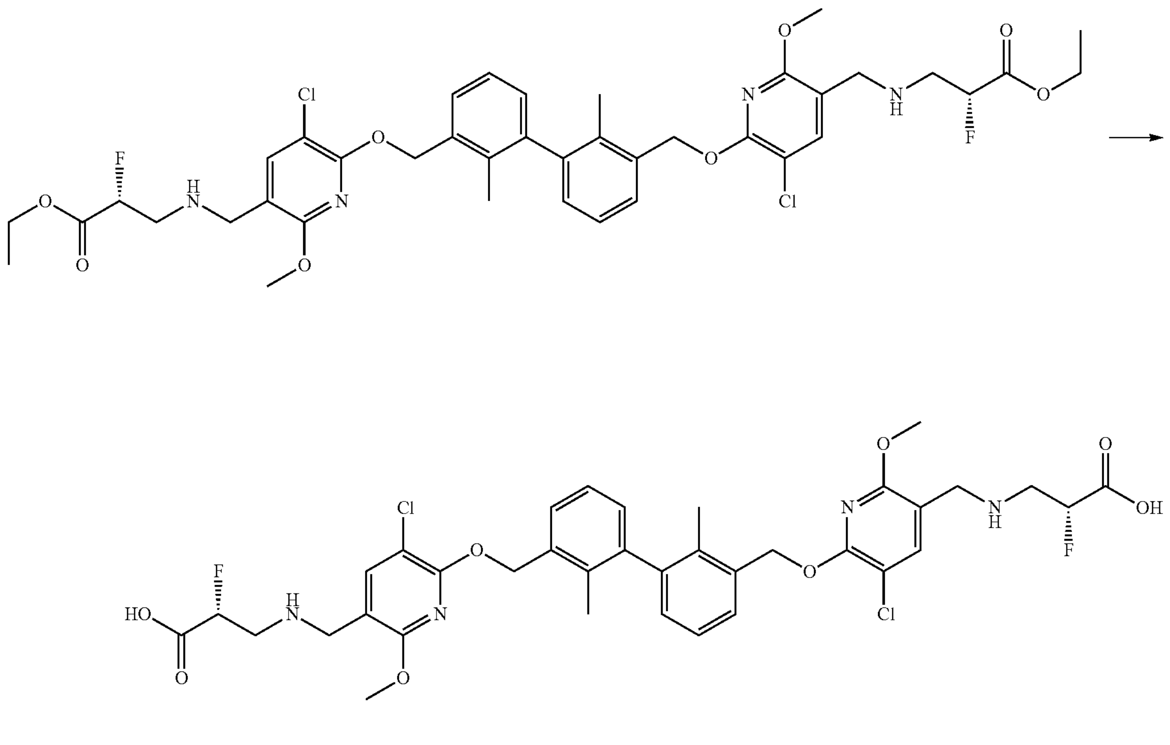

Diethyl 3,3'-((((((2,2'-dimethyl-[1,1'-biphenyl]-3,3'-diyl) bis(methylene))bis(oxy))bis(5-chloro -2-methoxypyridine-6,3-diyl))bis(methylene))bis(azanediyl))(2R,2'R)-bis(2-fluoropropanoate) bis trifluoroacetic acid salt was prepared following reductive amination procedure G, substituting ethyl (R)-3-amino-2-fluoropropanoate hydrochloride for (3S)-4-amino-3-hydroxybutanoic acid.

A solution of lithium hydroxide (4.57 mg, 0.191 mmol) in water (0.5 mL) was added to a solution of diethyl 3,3'-((((((2,2'-dimethyl-[1,1'-biphenyl]-3,3'-diyl)bis(methylene)) bis(oxy))bis(5-chloro-2-methoxypyridine-6,3-diyl))bis (methylene))bis(azanediyl))(2R,2'R)-bis(2-fluoropropanoate) bis trifluoroacetic acid salt (20 mg, 0.0191 mmol) in methanol. After 1 h trifluoroacetic acid (0.2 mL) was added and ~half the solvent was removed under reduced pressure. The solution was subjected to preparative HPLC (eluent: 0.1% trifluoroacetic acid/0.1 acetonitrile). The clean fractions containing product were combined and subjected to lyophilization, providing (2R,2'R)-3,3'-((((((2,2'-dimethyl-[1,1'-biphenyl]-3,3'-diyl)bis(methylene))bis(oxy))bis (5-chloro-2-methoxypyridine-6,3-diyl))bis(methylene))bis (azanediyl))bis(2-fluoropropanoic acid). $^1$H NMR (400 MHz, Methanol-$d_4$) δ 7.82 (s, 2H), 7.50-7.43 (m, 2H), 7.24 (t, J=7.6 Hz, 2H), 7.07 (dd, J=7.7, 1.4 Hz, 2H), 5.60 (s, 4H), 5.36 (dd, J=8.4, 3.2 Hz, 1H), 5.24 (dd, J=8.3, 3.4 Hz, 1H), 4.21 (s, 4H), 4.06 (s, 6H), 3.69-3.45 (m, 4H), 2.08 (s, 6H). $^{19}$F NMR (400 MHz, Methanol-d4) δ −195.66. ES/MS (M+1): 762.9.

Example 180: (3S,3'S)-4,4'-(((([4,4'-biindoline]-1,1'-dicarbonyl)bis(2-methoxy-4,1-phenylene))bis(methylene))bis(azanediyl))bis(3-hydroxybutanoic acid)

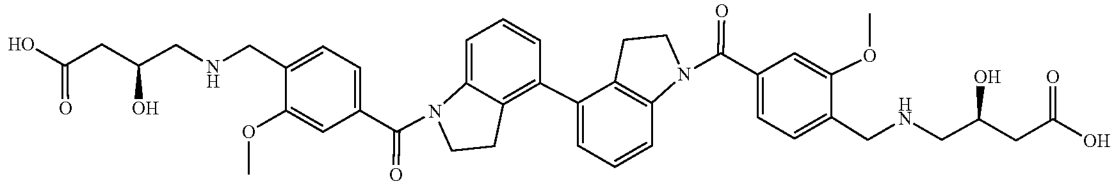 [SMILES: COc1cc(C(=O)N2CCc3c(-c4cccc5c4CCN5C(=O)c4ccc(CNC[C@@H](O)CC(=O)O)c(OC)c4)cccc32)ccc1CNC[C@@H](O)CC(=O)O]

In a round bottom flask, 4,4'-([4,4'-biindoline]-1,1'-dicarbonyl)bis(2-methoxybenzaldehyde) (27.00 mg, 0.048 mmol) was dissolved in a mixture of 12.00 mL of methanol and 1.20 mL of acetic acid. To this solution was added (3S)-4-amino-3-hydroxybutyric acid (18.00 mg, 0.151 mmol) at room temperature. The flask was capped and the solution was stirred at room temperature for 30 min. To this solution, 2-methylpyridine borane (16.00 mg, 0.150 mmol) was added at room temperature. The flask was capped and the mixture was stirred at room temperature for an additional 2 hours. Reaction was filtered and purified by reverse phase HPLC (0.1% trifluoroacetic acid in acetonitrile/water) to afford (3S,3'S)-4,4'-(((([4,4'-biindoline]-1,1'-dicarbonyl)bis (2-methoxy-4,1-phenylene))bis(azanediyl))bis-(3-hydroxybutanoic acid)upon lyophilization as the bis-TFA salt.

$^1$H NMR (400 MHz, Methanol-$d_4$) δ 8.16 (s, 1H), 7.60-7.46 (m, 1H), 7.36-7.18 (m, 3H), 7.02 (s, 1H), 4.41-4.23 (m, 3H), 4.07 (s, 2H), 4.03-3.87 (m, 3H), 3.26-3.16 (m, 1H), 3.01 (dq, J=22.1, 9.0, 7.1 Hz, 3H), 2.55 (q, J=5.4 Hz, 2H). ES/MS $M^{+1}$: 767.33.

Example 181: (3S,3'S)-4,4'-(((([4,4'-biindoline]-1,1'-dicarbonyl)bis(4,1-phenylene))bis(methylene))bis(azanediyl))bis(3-hydroxybutanoic acid)

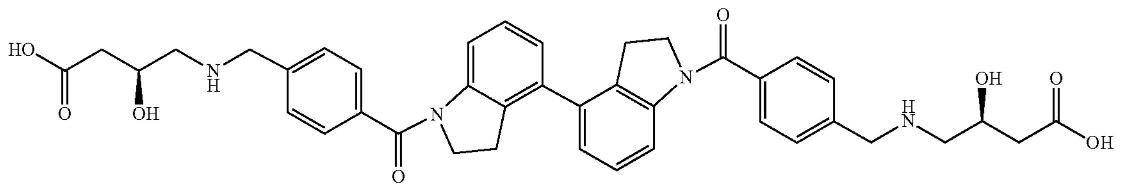 [SMILES: O=C(O)C[C@H](O)CNCc1ccc(C(=O)N2CCc3c(-c4cccc5c4CCN5C(=O)c4ccc(CNC[C@@H](O)CC(=O)O)cc4)cccc32)cc1]

In a round bottom flask, 4,4'-([4,4'-biindoline]-1,1'-dicarbonyl)bis(2-methoxybenzaldehyde) (22.00 mg, 0.044 mmol) was dissolved in a mixture of 5.00 mL of methanol and 5.50 mL of acetic acid. To this solution was added (3S)-4-amino-3-hydroxybutyric acid (16.00 mg, 0.13 mmol) at room temperature. The flask was capped and the solution was stirred at room temperature for 30 min. To this solution, 2-methylpyridine borane (14.00 mg, 0.013 mmol) was added at room temperature. The flask was capped and the mixture was stirred at room temperature for an additional 2 hours. Reaction was filtered and purified by reverse phase HPLC (0.1% trifluoroacetic acid in acetonitrile/water) to afford (3S,3'S)-4,4'-(((([4,4'-biindoline]-1,1'-dicarbonyl)bis(4,1-phenylene))bis(methylene))bis(azanediyl))bis(3-hydroxybutanoic acid)upon lyophilization as the bis-TFA salt.

$^1$H NMR (400 MHz, Methanol-$d_4$) δ 8.65-8.51 (m, 1H), 8.27 (td, J=7.9, 1.7 Hz, 1H), 7.77-7.57 (m, 5H), 4.25 (s, 3H), 4.03 (s, 2H), 3.17 (dd, J=12.6, 3.0 Hz, 1H), 3.03-2.90 (m, 3H), 2.52 (t, J=6.2 Hz, 2H). ES/MS $M^{+1}$: 707.31.

Example 182: (3S,3'S,4R,4'R)-4,4'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(3-hydroxypentanoic acid) (or (3S,3'S,4R,4'R)-4,4'-(((6,6'-(((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(3-hydroxypentanoic acid))

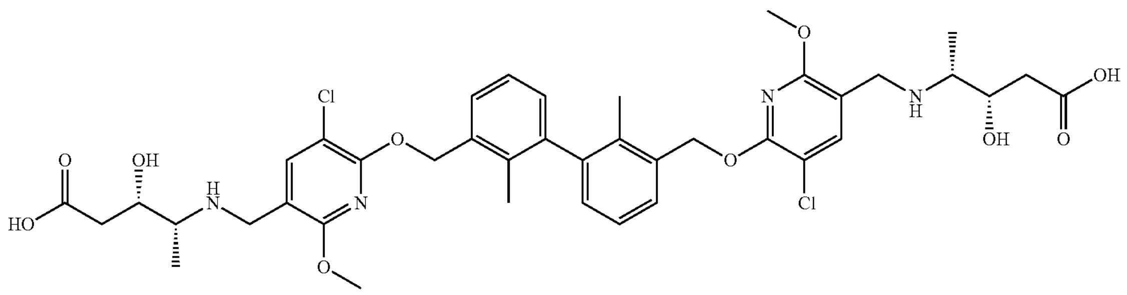 [SMILES: COc1nc(OCc2cccc(-c3cccc(COc4nc(OC)c(CN[C@H](C)[C@@H](O)CC(=O)O)cc4Cl)c3C)c2C)c(Cl)cc1CN[C@H](C)[C@@H](O)CC(=O)O]

In a round bottom flask, (3S)-4-amino-3-hydroxy-4-methylbutyric acid HCl salt (183.77 mg, 1.08 mmol) was dissolved in 6.0 mL of DMF at room temperature and the solution was stirred for 5 min at room temperature. To this solution, 6,6'-(((2,2'-dimethyl-[1,1'-biphenyl]-3,3'-diyl)bis(methylene))bis(oxy))bis(5-chloro-2-methoxynicotinaldehyde) (63.00 mg, 0.108 mmol) was added at room temperature followed by triethylamine (0.100 mL). Flask was capped and solution was stirred at room temperature. After 30 min, sodium cyanoborohydride (68.00 mg, 1.08 mmol) and sodium triacetoxyborohydride (230.00 mg, 1.08 mmol) were added to the mixture at room temperature and the solution was stirred for an additional 4 hours. Reaction was filtered and purified by reverse phase HPLC (0.1% trifluoroacetic acid in acetonitrile/water) to afford (3S,3'S,4R,4'R)-4,4'-((((((2,2'-dimethyl-[1,1'-biphenyl]-3,3'-diyl)bis(methylene))bis(oxy))bis(oxy))bis(5-chloro-2-methoxypyridine-6, 3-diyl))bis(methylene))bis(azanediyl))bis(3-hydroxypentanoic acid)upon lyophilization as the bis-TFA salt. $^1$H NMR (400 MHz, Methanol-$d_4$) δ 7.82 (s, 1H), 7.47 (dd, J=7.7, 1.4 Hz, 1H), 7.24 (t, J=7.6 Hz, 1H), 7.07 (dd, J=7.6, 1.4 Hz, 1H), 5.58 (s, 2H), 4.43 (td, J=6.6, 2.8 Hz, 1H), 4.17 (d, J=2.6 Hz, 2H), 4.04 (s, 3H), 3.39 (qd, J=6.7, 2.7 Hz, 1H), 2.53 (d, J=6.6 Hz, 2H), 2.08 (s, 3H), 1.31 (d, J=6.8 Hz, 3H). ES/MS $M^{+1}$: 815.28.

Example 183: 4,4'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))dibutyric acid (or 4,4'-(((6,6'-(((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))dibutyric acid)

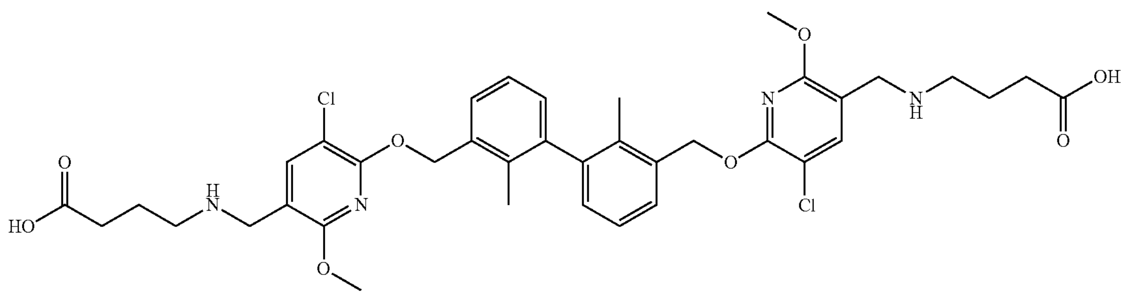 [SMILES: COc1nc(OCc2cccc(-c3cccc(COc4nc(OC)c(CNCCCC(=O)O)cc4Cl)c3C)c2C)c(Cl)cc1CNCCCC(=O)O]

In a round bottom flask, (3S)-4-amino-3-hydroxy-4-methylbutyric acid (124.15 mg, 1.20 mmol) was dissolved in 6.0 mL of DMF at room temperature and the solution was stirred for 5 min at room temperature. To this solution, 6,6'-(((2,2'-dimethyl-[1,1'-biphenyl]-3,3'-diyl)bis(methylene))bis(oxy))bis(5-chloro-2-methoxynicotinaldehyde) (70.00 mg, 0.120 mmol) was added at room temperature. Following general reductive amination procedure C, 4,4'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))dibutyric acid (8.00, 0.01 mmol) was obtained upon lyophilization as the bis-TFA salt. $^1$H NMR (400 MHz, Methanol-$d_4$) δ 7.80 (s, 1H), 7.47 (dd, J=7.7, 1.3 Hz, 1H), 7.24 (t, J=7.6 Hz, 1H), 7.07 (dd, J=7.6, 1.4 Hz, 1H), 5.59 (s, 2H), 4.12 (s, 2H), 4.05 (s, 3H), 3.19-3.03 (m, 2H), 2.98 (s, 1H), 2.85 (t, J=1.1 Hz, 1H), 2.46 (t, J=6.9 Hz, 2H), 2.08 (s, 3H), 1.96 (dt, J=14.8, 7.2 Hz, 2H).). ES/MS $M^{+1}$: 755.26.

Example 184: (1R,1'R,3S,3'S)-3,3'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(cyclohexane-1-carboxylic acid) (or (1R,1'R,3S,3'S)-3,3'-(((6,6'-(((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(cyclohexane-1-carboxylic acid))

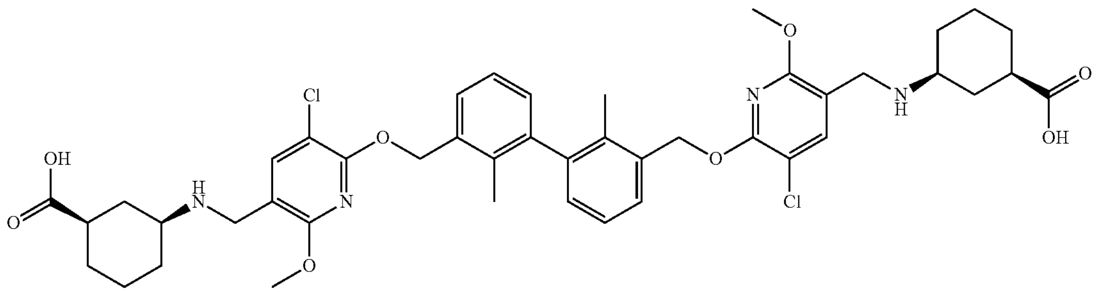 [SMILES: COc1nc(OCc2cccc(-c3cccc(COc4nc(OC)c(CN[C@H]5CCC[C@@H](C(=O)O)C5)cc4Cl)c3C)c2C)c(Cl)cc1CN[C@H]1CCC[C@@H](C(=O)O)C1]

In a round bottom flask, (3S)-4-amino-3-hydroxy-4-methylbutyric acid (123.15 mg, 0.86 mmol) was dissolved in 3.0 mL of DMF at room temperature and the solution was stirred for 5 min at room temperature. To this solution, 6,6'-(((2,2'-dimethyl-[1,1'-biphenyl]-3,3'-diyl)bis(methylene))bis(oxy))bis(5-chloro-2-methoxynicotinaldehyde) (50.00 mg, 0.086 mmol) was added at room temperature. Following general reductive amination procedure C, (1R,1'R,3S,3'S)-3,3'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(cyclohexane-1-carboxylic acid) (20.00 mg, 0.02 mmol) was obtained upon lyophilization as the bis-TFA salt. $^1H$ NMR (400 MHz, Methanol-$d_4$) δ 7.81 (s, 1H), 7.47 (dd, J=7.7, 1.4 Hz, 1H), 7.23 (t, J=7.6 Hz, 1H), 7.06 (dd, J=7.5, 1.4 Hz, 1H), 5.60 (s, 2H), 4.15 (s, 2H), 4.05 (s, 3H), 3.30-3.11 (m, 1H), 2.53-2.35 (m, 2H), 2.18 (d, J=11.9 Hz, 1H), 2.11-1.87 (m, 5H), 1.67-1.16 (m, 4H).). ES/MS $M^{+1}$: 835.32.

Example 185: (1S,1'S,3R,3'R)-3,3'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(cyclopentane-1-carboxylic acid) (or (1S,1'S,3R,3'R)-3,3'-(((6,6'-(((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(cyclopentane-1-carboxylic acid))

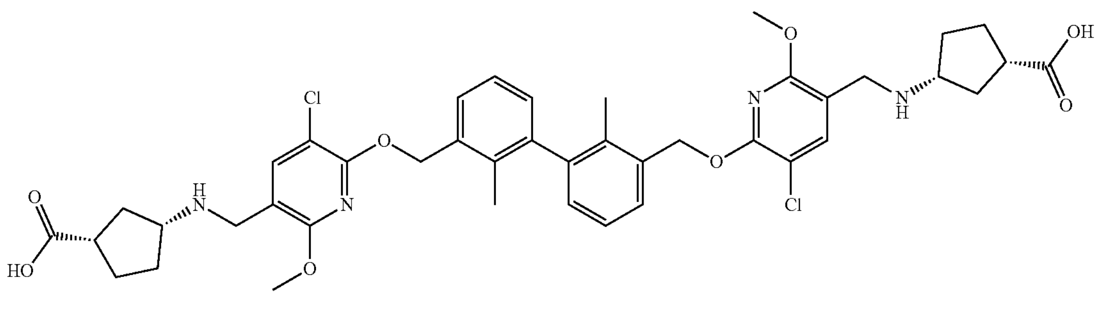 [SMILES: COc1nc(OCc2cccc(-c3cccc(COc4nc(OC)c(CN[C@@H]5CC[C@H](C(=O)O)C5)cc4Cl)c3C)c2C)c(Cl)cc1CN[C@@H]1CC[C@H](C(=O)O)C1]

In a round bottom flask, (3S)-4-amino-3-hydroxy-4-methylbutyric acid (37.00 mg, 0.28 mmol) was dissolved in 3.0 mL of DMF at room temperature and the solution was stirred for 5 min at room temperature. To this solution, 6,6'-(((2,2'-dimethyl-[1,1'-biphenyl]-3,3'-diyl)bis(methylene))bis(oxy))bis(5-chloro-2-methoxynicotinaldehyde) (50.00 mg, 0.086 mmol) was added at room temperature. Following general reductive amination procedure C, (1S,1'S,3R,3'R)-3,3'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(cyclopentane-1-carboxylic acid) (35.00 mg, 0.04 mmol) was obtained upon lyophilization as the bis-TFA salt. $^1H$ NMR (400 MHz, Methanol-$d_4$) δ 7.81 (s, 1H), 7.47 (dd, J=7.7, 1.4 Hz, 1H), 7.23 (t, J=7.6 Hz, 1H), 7.07 (dd, J=7.6, 1.4 Hz, 1H), 5.59 (s, 2H), 4.12 (s, 2H), 4.05 (s, 3H), 3.74-3.60 (m, 1H), 2.98 (s, 3H), 2.85 (d, J=0.7 Hz, 2H), 2.38 (dt, J=13.6, 7.7 Hz, 1H), 2.22 (dd, J=13.6, 6.9 Hz, 1H), 2.12-1.95 (m, 7H), 1.83 (dd, J=13.8, 7.0 Hz, 1H). ES/MS $M^{+1}$: 807.29.

Example 186: 2,2'-((((((2,2'-Dichloro-[1,1'-biphenyl]-3,3'-diyl)bis(methylene))bis(oxy))bis(2-methoxypyridine-6,3-diyl))bis(methylene))bis(azanediyl))bis(ethan-1-ol) (or 2,2'-(((6,6'-(((2,2'-dichloro-[1,1'-biphenyl]-3,3'-diyl)bis(methylene))bis(oxy))bis(2-methoxypyridine-6,3-diyl))bis(methylene))bis(azanediyl))bis(ethan-1-ol))

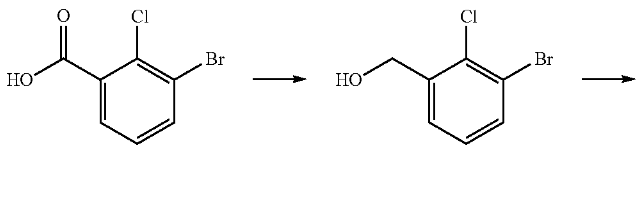

-continued

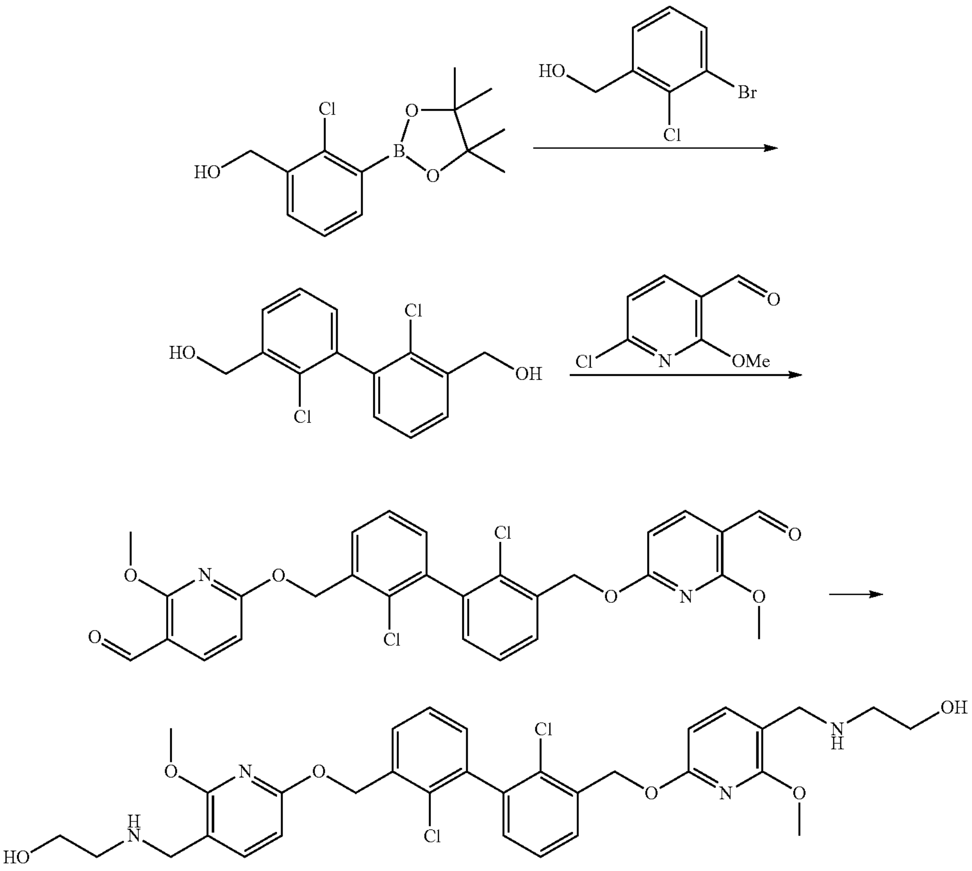

Step 1: (3-Bromo-2-chlorophenyl)methanol: To a solution of 3-bromo-2-chlorobenzoic acid (4.128 g, 17.5 mmol) in anhydrous THF (30 mL)under nitrogen was added dropwise a borane-dimethyl sulphide complex (1.6 mL) at 0° C. After the addition was complete the mixture was heated to reflux for 3 h. The mixture was cooled to room temperature and poured slowly into water. The aqueous layer was extracted with DCM and the combined organic layers were dried ($Na_2SO_4$) and the solvent was removed in vacuum to give the product.

Step 2: (2-Chloro-3-(4,4,5,5-tetramethyl-1,3,2-dioxaborolan-2-yl)phenyl)methanol: Dioxane (30 mL) was charged to a round-bottom flask and nitrogen was bubbled through for 10 minutes. (3-bromo-2-chlorophenyl)methanol (2 g, 9.03 mmol) was added and nitrogen was bubbled through for a while. Potassium acetate (2.66 g, 27.1 mmol) was added. Bis(pinacolato)diboron (3.67 g, 23.87 mmol) was added and then $PdCl_2$(dppf)-$CH_2Cl_2$ (0.66 g, 1.94 mmol) was added. The reaction was heated at 80° C. overnight. The reaction was diluted with ethyl acetate, filtered through a celite bed and the bed washed with ethyl acetate. The combined organic portions were concentrated under vacuum to provide a black pasty residue. This crude residue was purified by silica gel column with 5-30% EtOAc in hexanes to give the product as a solid.

Step 3: (2,2'-Dichloro-[1,1'-biphenyl]-3,3'-diyl)dimethanol: A solution of (3-bromo-2-chlorophenyl)methanol (600 mg, 2.71 mmol), (2-chloro-3-(4,4,5,5-tetramethyl-1,3,2-dioxaborolan-2-yl)phenyl)methanol (728 mg, 2.71 mmol), $K_2CO_3$ (936 mg, 6.77 mmol) in 1,4-dioxane (9 mL) and water (2.3 mL) was purged with nitrogen for 5 min. Pd(dppf) $Cl_2$.DCM (198 mg, 0.27 mmol) was added and the reaction mixture was heated at 100° C. for 12 h. The reaction mixture was filtered through a pad of celite and the pad was washed with MeOH. The filtrate was concentrated to dryness and the residue was purified by silica gel column with 0-30% EtOAc in hexanes to give a product.

Step 4: 6,6'-(((2,2'-Dichloro-[1,1'-biphenyl]-3,3'-diyl)bis(methylene))bis(oxy))bis(2-methoxynicotinaldehyde): A mixture of cesium carbonate (1.3 g, 4.04 mmol), palladium (II) acetate (46 mg, 0.20 mmol), 2-di-tert-butylphosphino-2',4',6'-triisopropylbiphenyl(t-butyl Xphos)(171 mg, 0.40 mmol), 6-chloro-2-methoxynicotinaldehyde (434 mg, 2.53 mmol) and (2,2'-dichloro-[1,1'-biphenyl]-3,3'-diyl)dimethanol (286 mg, 1.01 mmol) in Toluene (6 mL) was heated at 85° C. for 4 h. The reaction mixture was cooled down and purified by column chromatography (1% ethyl acetate/hexanes-50% ethyl acetate/hexanes) to give the product as a solid.

Step 5: 2,2'-((((((2,2'-Dichloro-[1,1'-biphenyl]-3,3'-diyl)bis(methylene))bis(oxy))bis(2-methoxypyridine-6,3-diyl))bis(methylene))bis(azanediyl))bis(ethan-1-ol): The compound was prepared using reductive amination procedure E. $^1$H NMR (400 MHz, DMSO-$d_6$) δ 8.83-8.59 (m, 4H), 7.77 (d, 2H), 7.61 (dd, 2H), 7.44 (t, 2H), 7.30 (dd, 2H), 6.56 (d, 2H), 5.58-5.44 (m, 4H), 4.04 (d, 4H), 3.87 (s, 6H), 3.64 (t, 4H), 2.95 (t, 4H). LCMS-ESI$^+$ (m/z): $[M+H]^+$ calculated for $C_{32}H_{36}Cl_2N_4O_6$: 643.2; found: 643.1.

Example 187: (3S,3'S)-4,4'-((((((2,2'-Dichloro-[1,1'-biphenyl]-3,3'-diyl)bis(methylene))bis(oxy))bis(2-methoxypyridine-6,3-diyl))bis(methylene))bis(azanediyl))bis(3-hydroxybutanoic acid) (or (3S,3'S)-4,4'-(((6,6'-(((2,2'-dichloro-[1,1'-biphenyl]-3,3'-diyl)bis(methylene))bis(oxy))bis(2-methoxypyridine-6,3-diyl))bis(methylene))bis(azanediyl))bis(3-hydroxybutanoic acid))

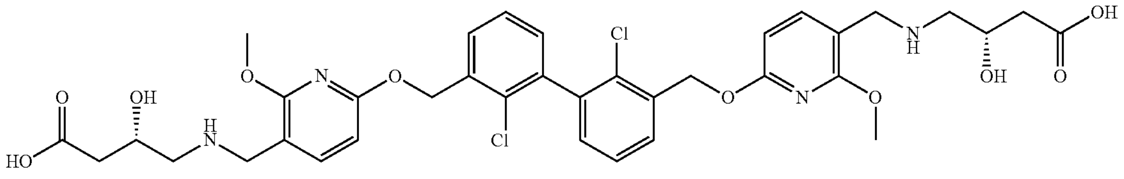 [SMILES: COc1nc(OCc2cccc(-c3cccc(COc4ccc(CNC[C@@H](O)CC(=O)O)c(OC)n4)c3Cl)c2Cl)ccc1CNC[C@@H](O)CC(=O)O]

Reductive amination of 6,6'-(((2,2'-dichloro-[1,1'-biphenyl]-3,3'-diyl)bis(methylene))bis(oxy))bis(2-methoxynicotinaldehyde with (S)-4-amino-3-hydroxybutanoic acid using reductive amination procedure E gave the title compound. $^1$H NMR (400 MHz, DMSO-$d_6$) δ 8.77-8.49 (m, 4H), 7.77 (d, 2H), 7.71-7.53 (m, 4H), 7.45 (t, 2H), 7.30 (dd, 2H), 6.56 (d, 2H), 5.65-5.40 (m, 4H), 4.15 (d, 2H), 4.04 (d, 4H), 3.87 (s, 6H), 2.98 (s, 2H), 2.86 (d, 2H), 2.60 (s, 2H), 2.46-2.27 (m, 4H). LCMS-ESI$^+$ (m/z): $[M+H]^+$ calculated for $C_{36}H_{40}Cl_2N_4O_{10}$: 759.2.2; found: 759.1.

Example 188: (3R,3'R)-4,4'-((((((2,2'-Dichloro-[1,1'-biphenyl]-3,3'-diyl)bis(methylene))bis(oxy))bis(2-methoxypyridine-6,3-diyl))bis(methylene))bis(azanediyl))bis(3-hydroxybutanoic acid) (or (3R,3'R)-4,4'-(((6,6'-(((2,2'-dichloro-[1,1'-biphenyl]-3,3'-diyl)bis(methylene))bis(oxy))bis(2-methoxypyridine-6,3-diyl))bis(methylene))bis(azanediyl))bis(3-hydroxybutanoic acid))

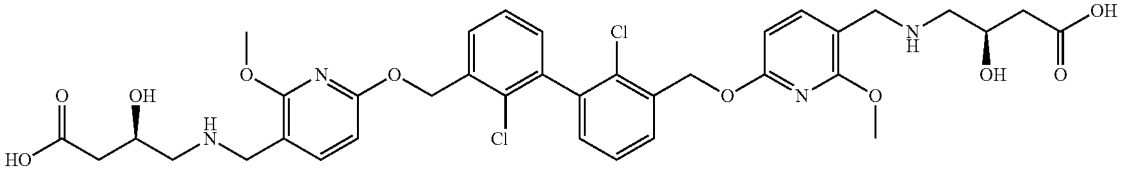 [SMILES: COc1nc(OCc2cccc(-c3cccc(COc4ccc(CNC[C@H](O)CC(=O)O)c(OC)n4)c3Cl)c2Cl)ccc1CNC[C@H](O)CC(=O)O]

Reductive amination of 6,6'-(((2,2'-dichloro-[1,1'-biphenyl]-3,3'-diyl)bis(methylene))bis(oxy))bis(2-methoxynicotinaldehyde with (R)-4-amino-3-hydroxybutanoic acid using reductive amination procedure E gave the title compound. $^1$H NMR (400 MHz, Methanol-$d_4$) δ 7.71 (d, 2H), 7.58 (dd, 2H), 7.38 (t, 2H), 7.23 (dd, 2H), 6.55 (d, 2H), 5.59 (d, 4H), 4.28 (m, 2H), 4.17 (s, 4H), 3.97 (d, 6H), 3.19 (dd, 2H), 2.98 (dd, 2H), 2.54 (d, 4H). LCMS-ESI$^+$ (m/z): $[M+H]^+$ calculated for $C_{36}H_{40}Cl_2N_4O_{10}$: 759.2; found: 759.0.

Example 189: (3S,3'S)-4,4'-((((((2,2'-Dichloro-[1,1'-biphenyl]-3,3'-diyl)bis(methylene))bis(oxy))bis(5-bromo-2-methoxypyridine-6,3-diyl))bis(methylene))bis(azanediyl))bis(3-hydroxybutanoic acid) (or (3S,3'S)-4,4'-(((6,6'-(((2,2'-dichloro-[1,1'-biphenyl]-3,3'-diyl)bis(methylene))bis(oxy))bis(5-bromo-2-methoxypyridine-6,3-diyl))bis(methylene))bis(azanediyl))bis(3-hydroxybutanoic acid))

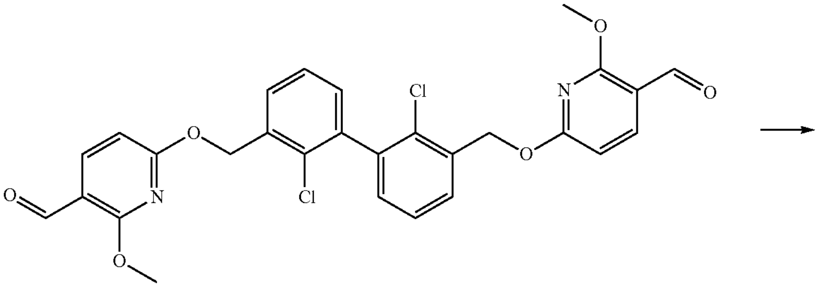

-continued

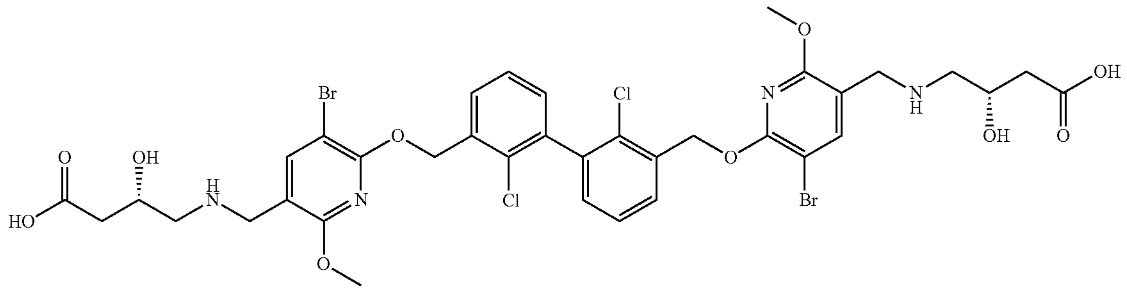

Step 1. 6,6'-(((2,2'-Dichloro-[1,1'-biphenyl]-3,3'-diyl)bis(methylene))bis(oxy))bis(2-methoxynicotinaldehyde) (60 mg, 0.11 mmol), was weighted into a small flask and DCM (1.5 mL) added until all solid dissolved. The reaction mixture was diluted with 1.5 mL DMF and treated with NBS (43 mg, 0.24 mmol) and 10 mol % TFA (0.085 mL, 1% solution in DMF). After 5 h, the reaction mixture was diluted with DCM and washed with 5% sodium thiosulfate. The organic layer was dried with $Na_2SO_4$, filtered and concentrated. The residue was used as crude in next step without further purification.

Step 2: Reductive amination of 6,6'-(((2,2'-dichloro-[1,1'-biphenyl]-3,3'-diyl)bis(methylene))bis(oxy))bis(2-methoxynicotinaldehyde with (S)-4-amino-3-hydroxybutanoic acid using reductive amination procedure G gave the title compound. $^1H$ NMR (400 MHz, Methanol-$d_4$) δ 7.99 (s, 2H), 7.63 (dd, 2H), 7.41 (t, 2H), 7.26 (dd, 2H), 5.67 (d, 4H), 4.28 (m, 2H), 4.16 (s, 4H), 3.99 (s, 6H), 3.21 (dd, 2H), 3.00 (dd, 2H), 2.54 (d, 4H). LCMS-ESI$^+$ (m/z): $[M+H]^+$ calculated for $C_{36}H_{38}Br_2Cl_2N_4O_{10}$: 915.0; found: 916.7.

Example 190: (S)-4-(((6-((3'-(((3-Bromo-5-((((S)-3-carboxy-2-hydroxypropyl)amino)methyl)-6-methoxypyridin-2-yl)oxy)methyl)-2,2'-dichloro-[1,1'-biphenyl]-3-yl)methoxy)-2-methoxypyridin-3-yl)methyl)amino)-3-hydroxybutanoic acid

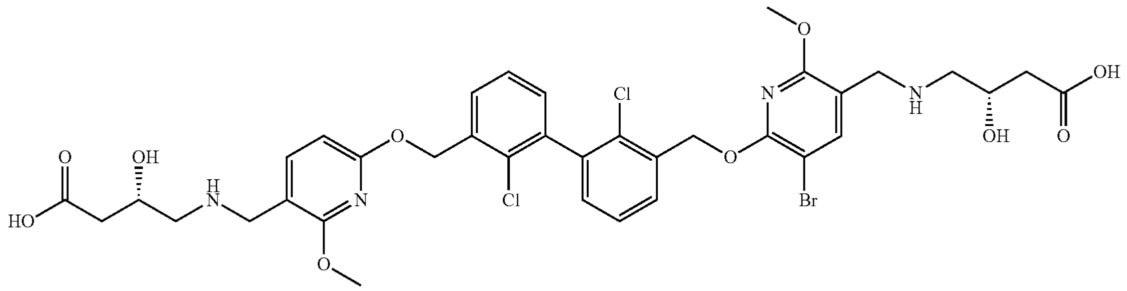 [SMILES: COc1nc(OCc2cccc(-c3cccc(COc4nc(OC)c(CNC[C@@H](O)CC(=O)O)cc4Br)c3Cl)c2Cl)ccc1CNC[C@@H](O)CC(=O)O]

The title compound was isolated as a by-product from Example 189. $^1H$ NMR (400 MHz, Methanol-$d_4$) δ 7.98 (s, 1H), 7.71 (d, 1H), 7.66-7.55 (m, 2H), 7.40 (m, 2H), 7.30-7.20 (m, 2H), 6.55 (d, 1H), 5.67 (d, 2H), 5.63-5.54 (m, 2H), 4.37-4.22 (m, 2H), 4.16 (d, 4H), 3.98 (d, 6H), 3.20 (m, 2H), 2.99 (m, 2H), 2.54 (m, 4H). LCMS-ESI$^+$ (m/z): $[M+H]^+$ calculated for $C_{36}H_{39}BrCl_2N_4O_{10}$: 837.1; found: 838.8.

Example 191: (3R,3'R)-4,4'-((((((2,2'-Dichloro-[1,1'-biphenyl]-3,3'-diyl)bis(methylene))bis(oxy))bis(5-bromo-2-methoxypyridine-6,3-diyl))bis(methylene))bis(azanediyl))bis(3-hydroxybutanoic acid) (or (3R,3'R)-4,4'-(((6,6'-(((2,2'-dichloro-[1,1'-biphenyl]-3,3'-diyl)bis(methylene))bis(oxy))bis(5-bromo-2-methoxypyridine-6,3-diyl))bis(methylene))bis(azanediyl))bis(3-hydroxybutanoic acid))

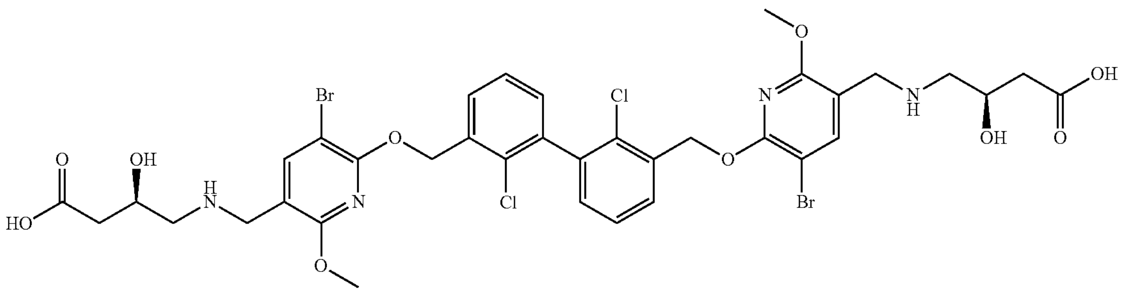 [SMILES: COc1nc(OCc2cccc(-c3cccc(COc4nc(OC)c(CNC[C@H](O)CC(=O)O)cc4Br)c3Cl)c2Cl)c(Br)cc1CNC[C@H](O)CC(=O)O]

Reductive amination of 6,6'-(((2,2'-dichloro-[1,1'-biphenyl]-3,3'-diyl)bis(methylene))bis(oxy))bis(2-methoxynicotinaldehyde with (R)-4-amino-3-hydroxybutanoic acid using reductive amination procedure G gave the title compound. $^1$H NMR (400 MHz, Methanol-$d_4$) δ 7.98 (s, 2H), 7.63 (dd, 2H), 7.41 (t, 2H), 7.26 (dd, 2H), 5.77-5.53 (m, 4H), 4.40-4.23 (m, 2H), 4.16 (s, 4H), 3.21 (dd, 2H), 3.00 (dd, 2H), 2.54 (d, 4H). LCMS-ESI$^+$ (m/z): $[M+H]^+$ calculated for $C_{36}H_{38}Br_2Cl_2N_4O_{10}$: 915.0; found: 917.0.

Example 192: (R)-4-(((6-((3'-(((3-Bromo-5-((((R)-3-carboxy-2-hydroxypropyl)amino)methyl)-6-methoxypyridin-2-yl)oxy)methyl)-2,2'-dichloro-[1,1'-biphenyl]-3-yl)methoxy)-2-methoxypyridin-3-yl)methyl)amino)-3-hydroxybutanoic acid

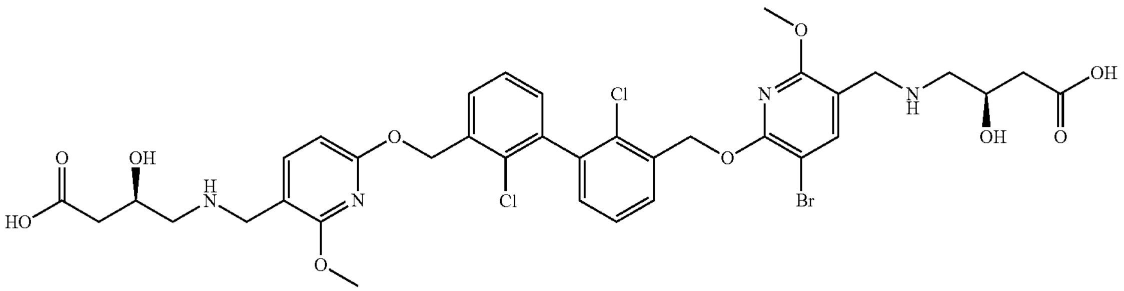 [SMILES: COc1nc(OCc2cccc(-c3cccc(COc4nc(OC)c(CNC[C@H](O)CC(=O)O)cc4Br)c3Cl)c2Cl)ccc1CNC[C@H](O)CC(=O)O]

The title compound was isolated as a byproduct from Example 191. $^1$H NMR (400 MHz, Methanol-$d_4$) δ 7.98 (s, 1H), 7.71 (d, J=8.1 Hz, 1H), 7.60 (m, 2H), 7.40 (dt, 2H), 7.24 (dt, 2H), 6.55 (d, 1H), 5.67 (d, 2H), 5.63-5.53 (m, 2H), 4.28 (m, 2H), 4.16 (d, 4H), 3.98 (d, 6H), 3.20 (m, 2H), 2.99 (m, 2H), 2.54 (dd, 4H). LCMS-ESI$^+$ (m/z): $[M+H]^+$ calculated for $C_{36}H_{39}BrCl_2N_4O_{10}$: 837.1; found: 839.0.

Example 193: (3S,3'S)-4,4'-((((((2,2'-Dichloro-[1,1'-biphenyl]-3,3'-diyl)bis(methylene))bis(oxy))bis(5-bromo-2-((5-cyanopyridin-3-yl)methoxy)pyridine-6,3-diyl))bis(methylene))bis(azanediyl))bis(3-hydroxybutanoic acid) (or (3S,3'S)-4,4'-(((6,6'-(((2,2'-dichloro-[1,1'-biphenyl]-3,3'-diyl)bis(methylene))bis(oxy))bis(5-bromo-2-((5-cyanopyridin-3-yl)methoxy)pyridine-6,3-diyl))bis(methylene))bis(azanediyl))bis(3-hydroxybutanoic acid))
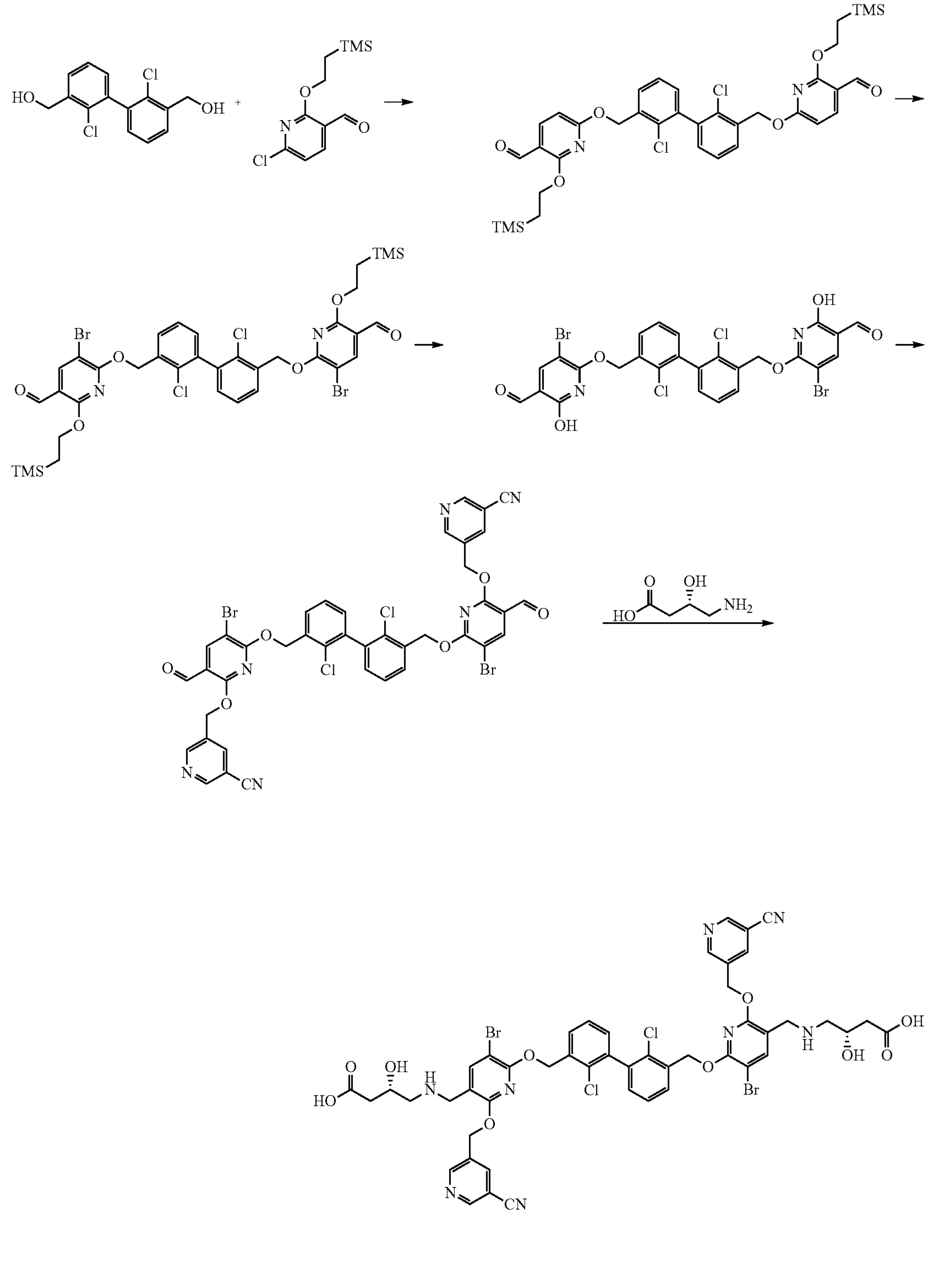

Step 1: 6,6'-(((2,2'-Dichloro-[1,1'-biphenyl]-3,3'-diyl)bis(methylene))bis(oxy))bis(2-(2-(trimethylsilyl)ethoxy)nicotinaldehyde): A mixture of cesium carbonate (2.75 g, 8.47 mmol), palladium (II) acetate (95 mg, 0.42 mmol), 2-di-tert-butylphosphino-2',4',6'-triisopropylbiphenyl(t-butyl Xphos) (225 mg, 0.53 mmol), 6-chloro-2-(2-(trimethylsilyl)ethoxy) nicotinaldehyde (1.256 g, 4.87 mmol) and (2,2'-dichloro-[1,1'-biphenyl]-3,3'-diyl)dimethanol (600 mg, 2.12 mmol) in toluene (6 mL) was heated at 95° C. in a sealed tube. After 3 h, reaction mixture was cooled down and filtered through a pad a celite and rinsed with DCM. The filtrate is concentrated and the residue was purified by column chromatography with 10% to 20% ethyl acetate in hexanes to give the product.

Step 2: 6,6'-(((2,2'-Dichloro-[1,1'-biphenyl]-3,3'-diyl)bis(methylene))bis(oxy))bis(5-bromo-2-(2-(trimethylsilyl)ethoxy)nicotinaldehyde): 6,6'-(((2,2'-Dichloro-[1,1'-biphenyl]-3,3'-diyl)bis(methylene))bis(oxy))bis(2-(2-(trimethylsilyl)ethoxy)nicotinaldehyde) (726 mg) was suspended in 4.5 mL AcOH, and sonicated for 10 min. Sodium acetate (205 mg) and bromine (400 mg, 0.13 mL) in 0.6 mL of AcOH were added. After 40 min, the reaction was diluted with 30 mL DCM and 45 mL of 2M NaOH. After stirring for 10 min, the organic layer was separated, and the aqueous layer extracted with DCM (20 mL). The organic layer was dried, and concentrated to afford a crude product.

Step 3: 6,6'-(((2,2'-Dichloro-[1,1'-biphenyl]-3,3'-diyl)bis(methylene))bis(oxy))bis(5-bromo-2-hydroxynicotinaldehyde): A mixture of 6,6'-(((2,2'-dichloro-[1,1'-biphenyl]-3,3'-diyl)bis(methylene))bis(oxy))bis(5-bromo-2-(2-(trimethylsilyl)ethoxy)nicotinaldehyde) (550 mg) and CsF (390 mg) in DMF (4 mL) was stirred at 60° C. for 90 minutes. The reaction mixture was then quenched with aq. $NH_4Cl$, and extracted with $CH_2Cl_2$. The organic layer was dried over $Na_2SO_4$, filtered, and concentrated. The residue was used for next step.

Step 4: 5,5'-((((((2,2'-Dichloro-[1,1'-biphenyl]-3,3'-diyl)bis(methylene))bis(oxy))bis(5-bromo-3-formylpyridine-6,2-diyl))bis(oxy))bis(methylene))dinicotinonitrile:6,6'-(((2,2'-Dichloro-[1,1'-biphenyl]-3,3'-diyl)bis(methylene))bis(oxy))bis(5-bromo-2-hydroxynicotinaldehyde) (385 mg), 5-(chloromethyl)nicotinonitrile (258 mg) and $K_2CO_3$ (390 mg) is dissolved in 5 mL DMF. NaI (190 mg) was added. The solution is then heated to 60° C. The reaction mixture was diluted with DCM and water. The organic layer was dried over $Na_2SO_4$, filtered, and concentrated. The residue was used for next step.

Step 5: Reductive amination of 5,5'-((((((2,2'-dichloro-[1,1'-biphenyl]-3,3'-diyl)bis(methylene))bis(oxy))bis(5-bromo-3-formylpyridine-6,2-diyl))bis(oxy))bis(methylene))dinicotinonitrile with (S)-4-amino-3-hydroxybutanoic acid using reductive amination procedure G gave the title compound. $^1H$ NMR (400 MHz, Methanol-$d_4$) δ 8.86 (dd, 4H), 8.27 (t, 2H), 8.07 (s, 2H), 7.57 (dd, 2H), 7.41 (t, 2H), 7.32-7.24 (m, 2H), 5.71-5.41 (m, 8H), 4.34-4.20 (m, 6H), 3.25 (dd, 2H), 3.03 (dd, 2H), 2.54 (dd, 4H). LCMS-$ESI^+$ (m/z): $[M+H]^+$ calculated for $C_{48}H_{42}Br_2Cl_2N_8O_{10}$: 1119.1; found: 1121.1.

Example 194: (S)-4-(((6-((3'-(((3-Bromo-5-((((S)-3-carboxy-2-hydroxypropyl)amino)methyl)-6-((5-cyanopyridin-3-yl)methoxy)pyridin-2-yl)oxy)methyl)-2,2'-dichloro-[1,1'-biphenyl]-3-yl)methoxy)-2-((5-cyanopyridin-3-yl)methoxy)pyridin-3-yl)methyl)amino)-3-hydroxybutanoic acid

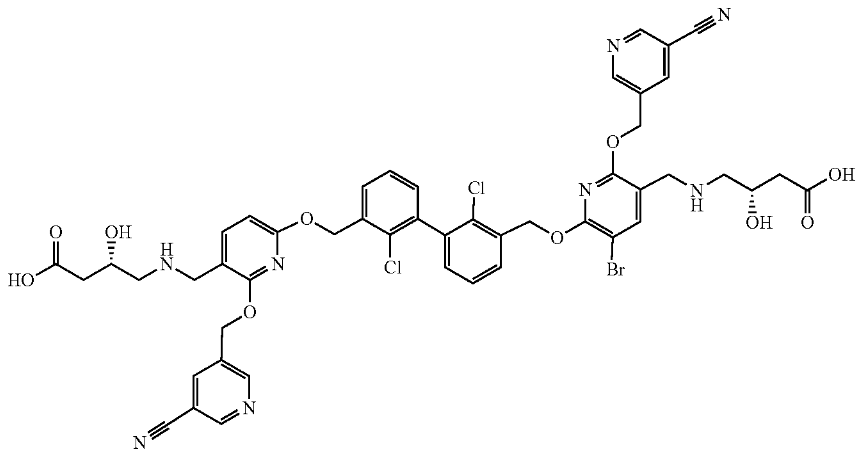 [SMILES: N#Cc1cncc(COc2nc(OCc3cccc(-c4cccc(COc5nc(OCc6cncc(C#N)c6)c(CNC[C@@H](O)CC(=O)O)cc5Br)c4Cl)c3Cl)ccc2CNC[C@@H](O)CC(=O)O)c1]

The title compound was isolated as a by-product from Example 193. $^1H$ NMR (400 MHz, Methanol-$d_4$) δ 8.93-8.72 (m, 4H), 8.32-8.18 (m, 2H), 7.84-7.70 (m, 2H), 7.66-7.43 (m, 2H), 7.36 (m, 2H), 7.30-7.13 (m, 2H), 6.68-6.53 (m, 1H), 5.73-5.36 (m, 8H), 4.37-4.09 (m, 6H), 3.27-2.93 (m, 4H), 2.53 (m, 4H). LCMS-$ESI^+$ (m/z): $[M+H]^+$ calculated for $C_{48}H_{43}BrCl_2N_8O_{10}$: 1041.2; found: 1042.9.

Example 195: (3S,3'S)-4,4'-((((((2,2'-Dichloro-[1,1'-biphenyl]-3,3'-diyl)bis(methylene))bis(oxy))bis(2-((5-cyanopyridin-3-yl)methoxy)pyridine-6,3-diyl))bis(methylene))bis(azanediyl))bis(3-hydroxybutanoic acid) (or (3S,3'S)-4,4'-(((6,6'-(((2,2'-dichloro-[1,1'-biphenyl]-3,3'-diyl)bis(methylene))bis(oxy))bis(2-((5-cyanopyridin-3-yl)methoxy)pyridine-6,3-diyl))bis(methylene))bis(azanediyl))bis(3-hydroxybutanoic acid))

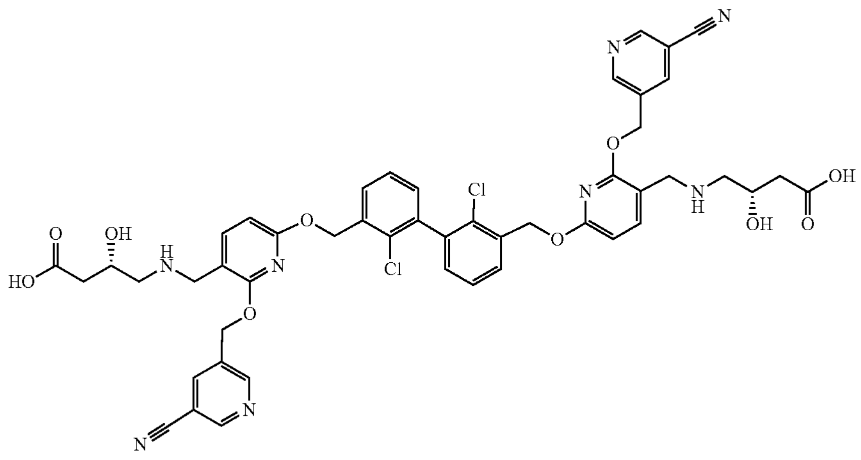 [SMILES: N#Cc1cncc(COc2nc(OCc3cccc(-c4cccc(COc5ccc(CNC[C@@H](O)CC(=O)O)c(OCc6cncc(C#N)c6)n5)c4Cl)c3Cl)ccc2CNC[C@@H](O)CC(=O)O)c1]

Reductive amination of 5,5'-((((((2,2'-dichloro-[1,1'-biphenyl]-3,3'-diyl)bis(methylene))bis(oxy))bis(3-formylpyridine-6,2-diyl))bis(oxy))bis(methylene))dinicotinonitrile with (S)-4-amino-3-hydroxybutanoic acid using reductive amination procedure G gave the title compound. $^1$H NMR (400 MHz, Methanol-$d_4$) δ 8.88 (d, 2H), 8.86-8.75 (m, 2H), 8.25 (t, 2H), 7.80 (d, 2H), 7.60-7.45 (m, 2H), 7.43-7.32 (m, 2H), 7.25 (m, 2H), 6.63 (dd, 2H), 5.53 (m, 8H), 4.26 (d, 6H), 3.23 (dd, 2H), 3.13-2.95 (m, 2H), 2.54 (dd, 4H). LCMS-ESI$^+$ (m/z): $[M+H]^+$ calculated for $C_{48}H_{44}Cl_2N_8O_{10}$: 963.3; found: 963.2.

Example 196: (3R,3'R)-4,4'-((((((2,2'-Dichloro-[1,1'-biphenyl]-3,3'-diyl)bis(methylene))bis(oxy))bis(5-bromo-2-((5-cyanopyridin-3-yl)methoxy)pyridine-6,3-diyl))bis(methylene))bis(azanediyl))bis(3-hydroxybutanoic acid) (or (3R,3'R)-4,4'-(((6,6'-(((2,2'-dichloro-[1,1'-biphenyl]-3,3'-diyl)bis(methylene))bis(oxy))bis(5-bromo-2-((5-cyanopyridin-3-yl)methoxy)pyridine-6,3-diyl))bis(methylene))bis(azanediyl))bis(3-hydroxybutanoic acid))

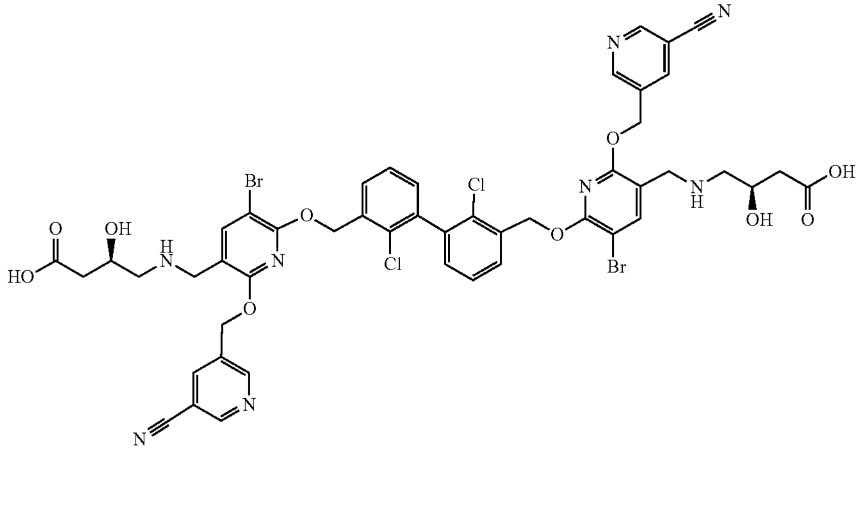 [SMILES: N#Cc1cncc(COc2nc(OCc3cccc(-c4cccc(COc5nc(OCc6cncc(C#N)c6)c(CNC[C@H](O)CC(=O)O)cc5Br)c4Cl)c3Cl)c(Br)cc2CNC[C@H](O)CC(=O)O)c1]

Reductive amination of 5,5'-((((((2,2'-dichloro-[1,1'-biphenyl]-3,3'-diyl)bis(methylene))bis(oxy))bis(5-bromo-3-formylpyridine-6,2-diyl))bis(oxy))bis(methylene))dinicotinonitrile with (R)-4-amino-3-hydroxybutanoic acid using reductive amination procedure G gave the title compound. $^1$H NMR (400 MHz, Methanol-$d_4$) δ 8.89 (d, 2H), 8.84 (dd, 2H), 8.26 (t, 2H), 8.07 (s, 2H), 7.57 (d, 2H), 7.41 (t, 2H), 7.27 (dd, 2H), 5.71-5.30 (m, 8H), 4.26 (m, 6H), 3.25 (dd, 1H), 3.13-2.93 (m, 2H), 2.54 (dd, 4H). LCMS-ESI$^+$ (m/z): $[M+H]^+$ calculated for $C_{48}H_{42}Br_2Cl_2N_8O_{10}$: 1119.1; found: 1120.9.

Example 197: (2S,2'S)-2,2'-((((((2,2'-Dichloro-[1,1'-biphenyl]-3,3'-diyl)bis(methylene))bis(oxy))bis(5-bromo-2-((5-cyanopyridin-3-yl)methoxy)pyridine-6,3-diyl))bis(methylene))bis(azanediyl))bis(3-hydroxy-2-methylpropanoic acid) (or (2S,2'S)-2,2'-(((6,6'-(((2,2'-dichloro-[1,1'-biphenyl]-3,3'-diyl)bis(methylene))bis(oxy))bis(5-bromo-2-((5-cyanopyridin-3-yl)methoxy)pyridine-6,3-diyl))bis(methylene))bis(azanediyl))bis(3-hydroxy-2-methylpropanoic acid))

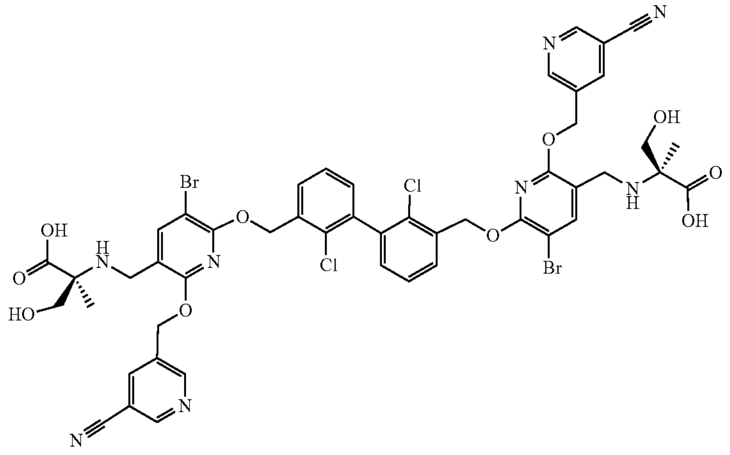 [SMILES: C[C@@](CO)(NCc1cc(Br)c(OCc2cccc(-c3cccc(COc4nc(OCc5cncc(C#N)c5)c(CN[C@@](C)(CO)C(=O)O)cc4Br)c3Cl)c2Cl)nc1OCc1cncc(C#N)c1)C(=O)O]

Reductive amination of 5,5'-((((((2,2'-dichloro-[1,1'-biphenyl]-3,3'-diyl)bis(methylene))bis(oxy))bis(5-bromo-3-formylpyridine-6,2-diyl))bis(oxy))bis(methylene))dinicotinonitrile with (S)-2-amino-3-hydroxy-2-methylpropanoic acid using reductive amination procedure G gave the title compound. $^1$H NMR (400 MHz, Methanol-$d_4$) δ 8.90 (d, 2H), 8.87-8.76 (m, 2H), 8.29 (t, 2H), 8.15-8.07 (m, 2H), 7.63-7.50 (m, 2H), 7.40 (t, 2H), 7.27 (dd, 2H), 5.66-5.43 (m, 8H), 4.25 (s, 4H), 4.00 (d, 2H), 3.80 (d, 2H), 1.54 (d, J=9.9 Hz, 6H). LCMS-ESI$^+$ (m/z): $[M+H]^+$ calculated for $C_{48}H_{42}Br_2Cl_2N_8O_{10}$: 1119.1; found: 1120.8.

Example 198: (2R,2'R)-2,2'-((((((2,2'-Dichloro-[1,1'-biphenyl]-3,3'-diyl)bis(methylene))bis(oxy))bis(5-bromo-2-((5-cyanopyridin-3-yl)methoxy)pyridine-6,3-diyl))bis(methylene))bis(azanediyl))bis(3-hydroxy-2-methylpropanoic acid)

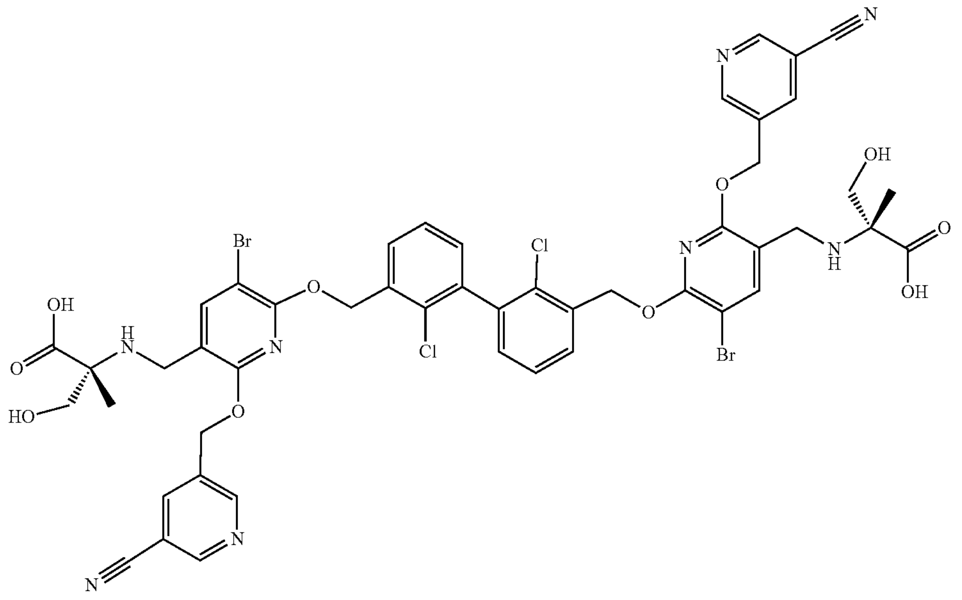 [SMILES: C[C@](CO)(NCc1cc(Br)c(OCc2cccc(-c3cccc(COc4nc(OCc5cncc(C#N)c5)c(CN[C@](C)(CO)C(=O)O)cc4Br)c3Cl)c2Cl)nc1OCc1cncc(C#N)c1)C(=O)O]

Reductive amination of 5,5'-((((((2,2'-dichloro-[1,1'-biphenyl]-3,3'-diyl)bis(methylene))bis(oxy))bis(5-bromo-3-formylpyridine-6,2-diyl))bis(oxy))bis(methylene))dinicotinonitrile with (R)-2-amino-3-hydroxy-2-methylpropanoic acid using reductive amination procedure G gave the title compound. $^1$H NMR (400 MHz, Methanol-$d_4$) δ 8.90 (s, 2H), 8.81 (d, 2H), 8.29 (t, 2H), 8.10 (s, 2H), 7.62-7.51 (m, 2H), 7.40 (t, 2H), 7.27 (dd, 2H), 5.69-5.41 (m, 8H), 4.25 (s, 4H), 4.01 (d, 2H), 3.80 (d, 2H), 1.54 (d, 6H). LCMS-ESI$^+$ (m/z): $[M+H]^+$ calculated for $C_{48}H_{42}Br_2Cl_2N_8O_{10}$: 1119.1; found: 1120.9.

Example 199: 5-((4-Chloro-5-((3'-((2-chloro-5-(cyclopropylmethoxy)-4-(((2-hydroxyethyl)amino)methyl)phenoxy)methyl)-2,2'-dimethyl-[1,1'-biphenyl]-3-yl)methoxy)-2-(((2-hydroxyethyl)amino)methyl)phenoxy)methyl)nicotinonitrile

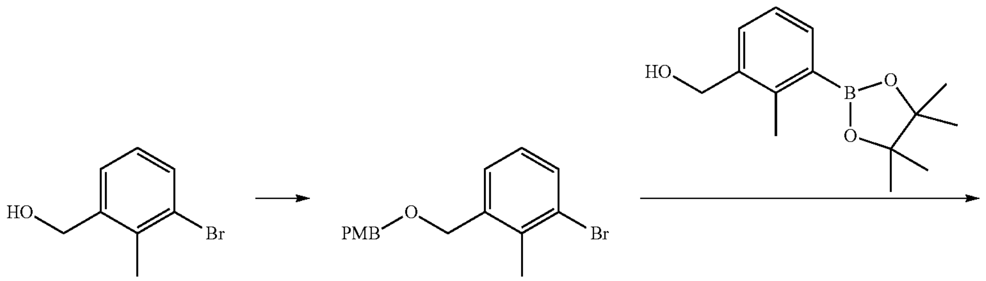

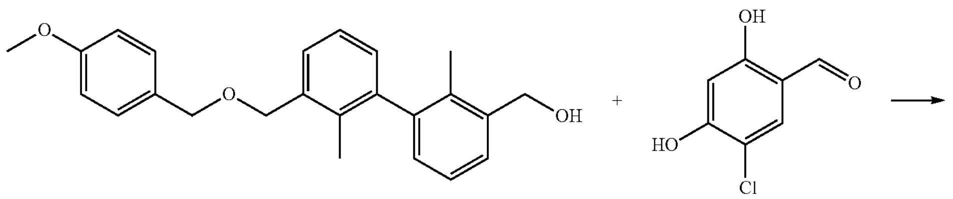

-continued
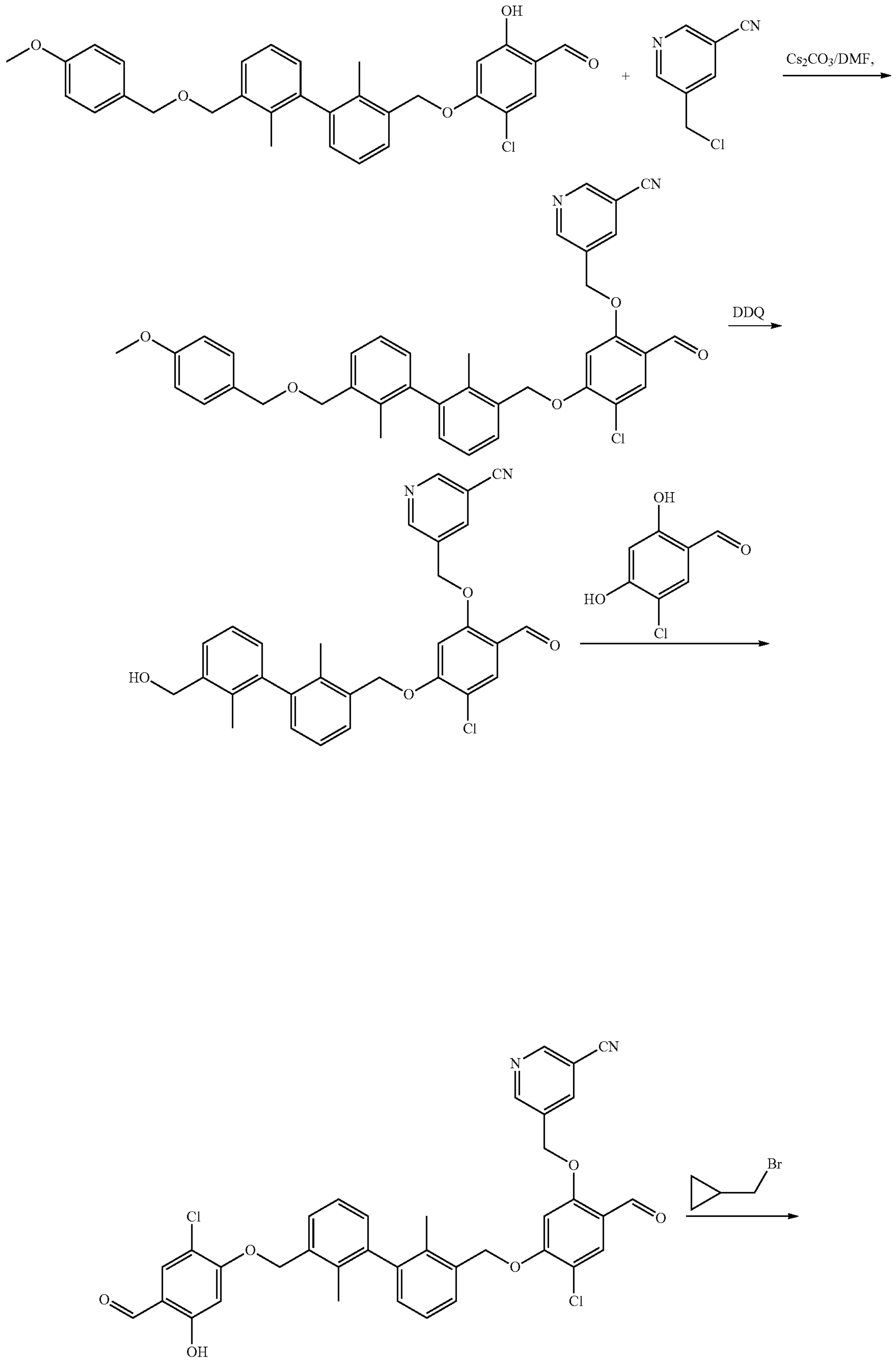

-continued

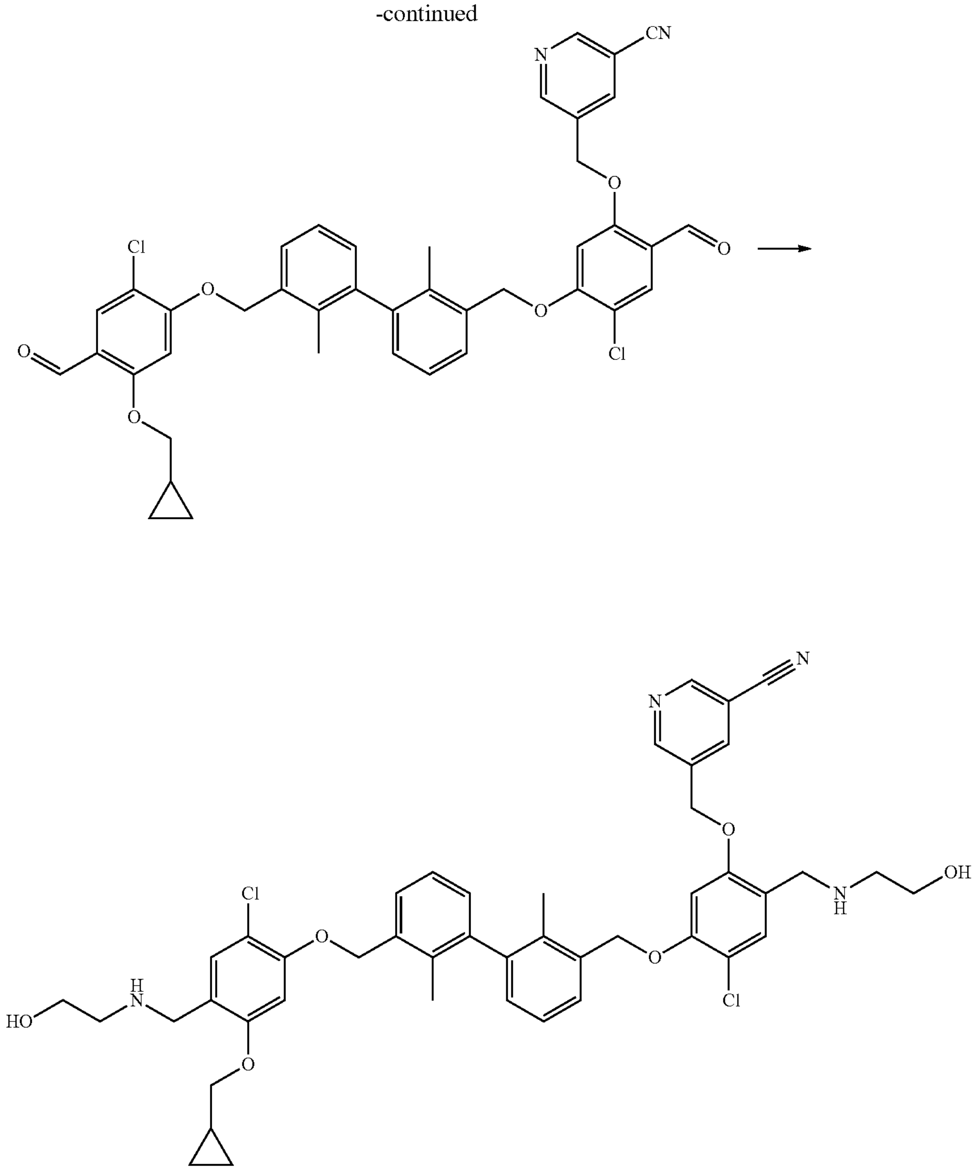

Step 1: 1-Bromo-3-(((4-methoxybenzyl)oxy)methyl)-2-methylbenzene: To a stirred solution of (3-bromo-2-methylphenyl)methanol (2 g, 9.95 mmol) in dry DMF (16 mL) was added 60% NaH (418 mg, 10.44 mmol). After the reaction mixture was stirred for 30 minutes, 1-(chloromethyl)-4-methoxybenzene (1.636 g, 10.44 mmol) was added at 0° C. and the reaction mixture was stirred for another 2 h at room temperature. The reaction was then diluted with $Et_2O$ and water. The organic phase was washed with brine and dried with $Na_2SO_4$ and concentrated under reduced pressure. The residue was purified via silica gel column chromatography with 0-15% EtOAc in hexanes to give the product.

Step 2: (3'-(((4-Methoxybenzyl)oxy)methyl)-2,2'-dimethyl-[1,1'-biphenyl]-3-yl)methanol: A solution of 1-bromo-3-(((4-methoxybenzyl)oxy)methyl)-2-methylbenzene (400 mg, 1.245 mmol), (2-methyl-3-(4,4,5,5-tetramethyl-1,3,2-dioxaborolan-2-yl)phenyl)methanol (340 mg, 1.37 mmol), $K_2CO_3$ (516 mg, 3.74 mmol) in 1,4-dioxane (6 mL) and water (1.5 mL) was purged with nitrogen for 30 min. Pd(dppf)$Cl_2$·DCM (102 mg, 0.125 mmol) was added and the reaction mixture was heated at 100° C. for 12 h. The reaction mixture was filtered through a pad of Celite and the pad was washed with MeOH. The filtrate was concentrated to dryness and the residue was purified by silica gel column chromatography with 0-30% EtOAc in hexanes to give a product.

Step 3: 5-Chloro-2-hydroxy-4-((3'-(((4-methoxybenzyl)oxy)methyl)-2,2'-dimethyl-[1,1'-biphenyl]-3-yl)methoxy)benzaldehyde: Diisopropyl azodicarboxylate (176 mg, 0.87 mmol) in tetrahydrofuran (1.4 mL) was added dropwise to a cooled (0 C) solution of 5-chloro-2,4-dihydroxybenzaldehyde (136 mg, 0.79 mmol), triphenylphosphine (217 mg, 0.88 mmol) and (3'-(((4-methoxybenzyl)oxy)methyl)-2,2'-dimethyl-[1,1'-biphenyl]-3-yl)methanol (315 mg, 0.87 mmol) in dry tetrahydrofuran (2.6 mL). The resulting reaction mixture was allowed to slowly warm to room temperature with stirring overnight. The reaction mixture was concentrated and the residue was purified by silica gel column chromatography with 0-20% EtOAc in hexanes to give the product.

Step 4: 5-((4-Chloro-2-formyl-5-((3'-(((4-methoxybenzyl)oxy)methyl)-2,2'-dimethyl-[1,1'-biphenyl]-3-yl)methoxy)phenoxy)methyl)nicotinonitrile: Cesium carbonate (291 mg, 0.89 mmol), 5-chloro-2-hydroxy-4-((3'-(((4-methoxybenzyl)oxy)methyl)-2,2'-dimethyl-[1,1'-biphenyl]-3-yl)methoxy)benzaldehyde (234 mg, 0.45 mmol) were combined in dimethylformamide (2.2 mL). Added 5-(chloromethyl)nicotinonitrile (138 mg, 0.91 mmol) and stirred at 75 C overnight. The mixture was treated with $CH_2Cl_2$ and water. The organic phase was separated, dried over $Na_2SO_4$, and concentrated. The residue was purified by silica gel column chromatography with 0-20% EtOAc in hexanes to give the product as a solid.

Step 5: 5-((4-Chloro-2-formyl-5-((3'-(hydroxymethyl)-2,2'-dimethyl-[1,1'-biphenyl]-3-yl)methoxy)phenoxy)methyl)nicotinonitrile: 2,3-Dichloro-5,6-dicyanobenzoquinone (263 mg, 1.16 mM) was added to a vigorously stirring, biphasic solution of 5-((4-chloro-2-formyl-5-((3'-(((4-methoxybenzyl)oxy)methyl)-2,2'-dimethyl-[1,1'-biphenyl]-3-yl)methoxy)phenoxy)methyl)nicotinonitrile (612 mg, 0.967 mM) in $CH_2Cl_2$ (20 mL) and water (4 mL) at room temperature. The reaction flask was covered with aluminum foil to exclude light. The reaction mixture was stirred at room temperature for 3 h. The crude material was diluted with $CH_2Cl_2$ and water. The organic layer was separated, dried with $Na_2SO_4$, concentrated. The residue was purified via silica gel column chromatography with 0-5% MeOH in $CH_2Cl_2$ to give the product as a solid.

Step 6: 5-((4-Chloro-5-((3'-((2-chloro-4-formyl-5-hydroxyphenoxy)methyl)-2,2'-dimethyl-[1,1'-biphenyl]-3-yl)methoxy)-2-formylphenoxy)methyl)nicotinonitrile: Diisopropyl azodicarboxylate (116 mg, 0.57 mmol) in tetrahydrofuran (1.1 mL) was added dropwise to a cooled (0° C.) solution of 5-chloro-2,4-dihydroxybenzaldehyde (90 mg, 0.522 mmol), triphenylphosphine (143 mg, 0.58 mmol) and 5-((4-chloro-2-formyl-5-((3'-(hydroxymethyl)-2,2'-dimethyl-[1,1'-biphenyl]-3-yl)methoxy)phenoxy)methyl)nicotinonitrile (200 mg, 0.39 mmol) in dry tetrahydrofuran (14 mL). The resulting reaction mixture was allowed to slowly warm to room temperature with stirring overnight.

The reaction mixture was concentrated and the residue was purified by silica gel column with 0-20% EtOAc in hexanes to give the product.

Step 7: 5-((4-Chloro-5-((3'-((2-chloro-5-(cyclopropylmethoxy)-4-formylphenoxy)methyl)-2,2'-dimethyl-[1,1'-biphenyl]-3-yl)methoxy)-2-formylphenoxy)methyl)nicotinonitrile: 5-((4-chloro-5-((3'-((2-chloro-4-formyl-5-hydroxyphenoxy)methyl)-2,2'-dimethyl-[1,1'-biphenyl]-3-y)methoxy)-2-formylphenoxy)methyl)nicotinonitrile (22 mg, 0.033 mmol) was suspended in dimethylformamide (0.3 mL), cesium carbonate (16 mg, 0.042 mmol) was added and the reaction stirred for approximately 5 minutes in which it appeared to exhibit improved solubility. (Bromomethyl)cyclopropane (9 mg, 0.066 mmol) was added to the reaction. The reaction was capped and stirred at 65° C. for 1.5 h. The mixture was treated with $CH_2Cl_2$ and water. The organic phase was separated, dried over $Na_2SO_4$, and concentrated. The residue was purified by silica gel column with 0-20% EtOAc in hexanes to give the product.

Step 8: 5-((4-Chloro-5-((3'-((2-chloro-5-(cyclopropylmethoxy)-4-(((2-hydroxyethyl)amino)methyl)phenoxy)methyl)-2,2'-dimethyl-[1,1'-biphenyl]-3-yl)methoxy)-2-(((2-hydroxyethyl)amino)methyl)phenoxy)methyl)nicotinonitrile: Reductive amination of 5-((4-chloro-5-((3'-((2-chloro-5-(cyclopropylmethoxy)-4-formylphenoxy)methyl)-2,2'-dimethyl-[1,1'-biphenyl]-3-yl)methoxy)-2-formylphenoxy)methyl)nicotinonitrile with 2-aminoethan-1-ol using reductive amination procedure C gave the title compound. $^1$H NMR (400 MHz, DMSO-$d_6$) δ 9.03 (m, 2H), 8.57 (s, 3H), 8.51-8.43 (m, 1H), 7.61-7.53 (m, 1H), 7.49 (m, 3H), 7.35-7.25 (m, 2H), 7.21 (d, 1H), 7.10 (d, J=7.4 Hz, 2H), 7.01 (s, 1H), 5.36 (d, 2H), 5.35-5.22 (m, 4H), 4.10 (d, 4H), 3.96 (d, 2H), 3.62 (m, 4H), 2.94 (d, 4H), 2.01 (d, 6H), 1.24 (m, 1H), 0.66-0.50 (m, 2H), 0.42-0.27 (m, 2H). LCMS-ESI$^+$ (m/z): $[M+H]^+$ calculated for $C_{45}H_{48}Cl_2N_4O_6$: 811.3; found: 811.2.

Example 200: 5-((4-Chloro-5-((3'-((2-chloro-5-((3-cyano-4-fluorobenzyl)oxy)-4-(((2-hydroxyethyl)amino)methyl)phenoxy)methyl)-2,2'-dimethyl-[1,1'-biphenyl]-3-yl)methoxy)-2-(((2-hydroxyethyl)amino)methyl)phenoxy)methyl)nicotinonitrile

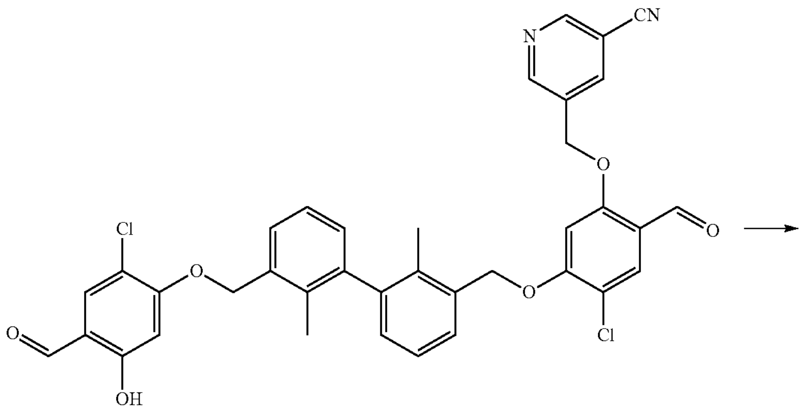

-continued

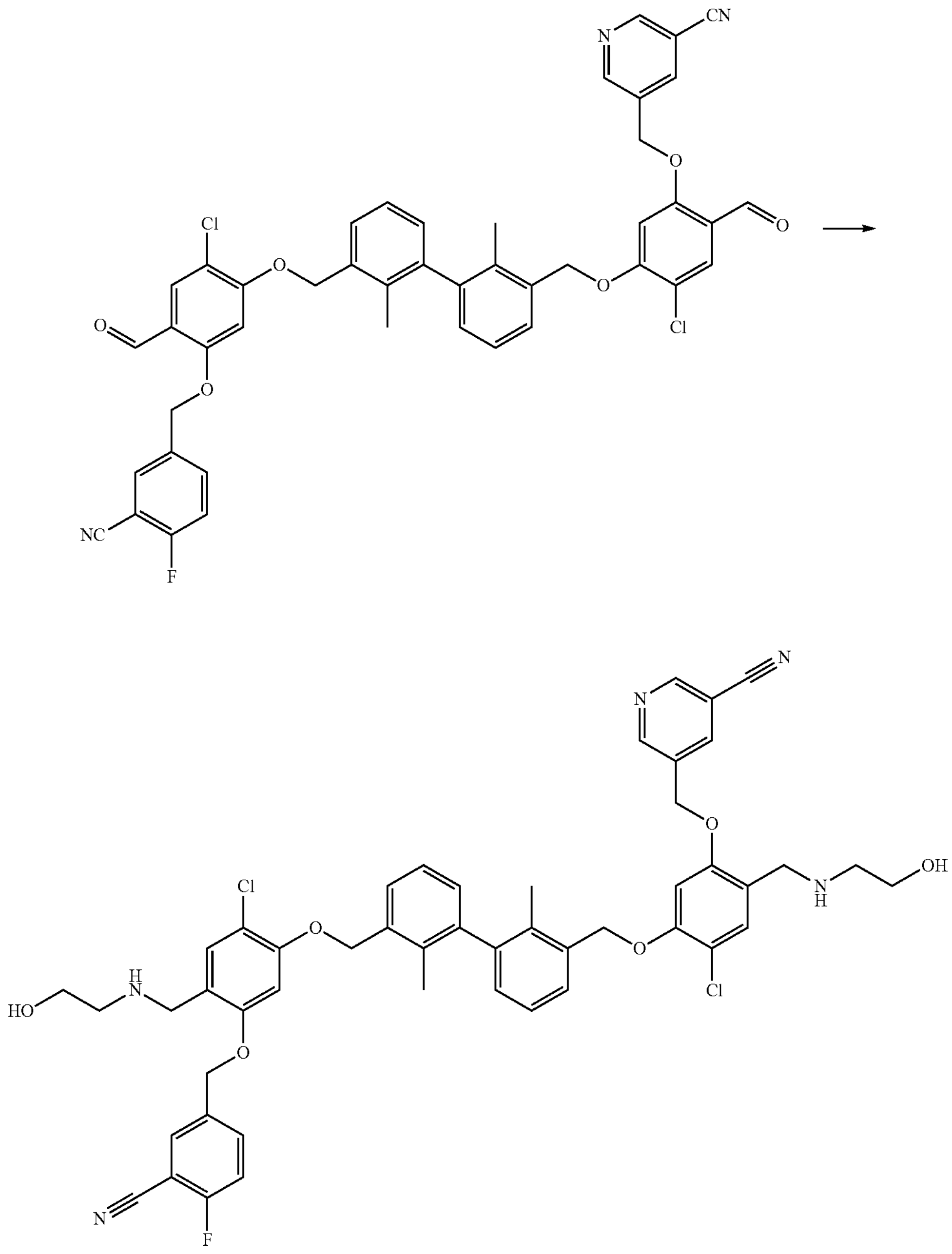

Step 1: 5-((4-Chloro-5-((3'-((2-chloro-5-((3-cyano-4-fluorobenzyl)oxy)-4-formylphenoxy)methyl)-2,2'-dimethyl-[1,1'-biphenyl]-3-yl)methoxy)-2-formylphenoxy)methyl)nicotinonitrile: 5-((4-Chloro-5-((3'-((2-chloro-4-formyl-5-hydroxyphenoxy)methyl)-2,2'-dimethyl-[1,1'-biphenyl]-3-yl)methoxy)-2-formylphenoxy)methyl)nicotinonitrile (22 mg, 0.033 mmol) was suspended in dimethylformamide (0.4 mL), cesium carbonate (13.5 mg, 0.042 mmol) was added and the reaction stirred for approximately 5 minutes in which it appeared to exhibit improved solubility. 5-(Bromomethyl)-2-fluorobenzonitrile (8 mg, 0.036 mmol) was added to the reaction. The reaction was capped and stirred at room temperature overnight. The mixture was treated with $CH_2Cl_2$ and water. The organic phase was separated, dried over $Na_2SO_4$, and concentrated. The residue was purified by silica gel column chromatography with 0-5% MeOH in $CH_2Cl_2$ to give the product.

Step 2: Reductive amination of 5-((4-chloro-5-((3'-((2-chloro-5-((3-cyano-4-fluorobenzyl)oxy)-4-formylphenoxy)methyl)-2,2'-dimethyl-[1,1'-biphenyl]-3-yl)methoxy)-2-formylphenoxy)methyl)nicotinonitrile with 2-aminoethan-1-ol using reductive amination procedure C gave the title compound. $^1$H NMR (400 MHz, DMSO-$d_6$) δ 9.02 (dd, 2H), 8.57 (d, 4H), 8.48 (t, 1H), 8.10 (dd, 1H), 7.93 (m, 1H), 7.62-7.52 (m, 3H), 7.49 (m, 2H), 7.29 (t, m 2H), 7.19 (s, 1H), 7.15 (s, 1H), 7.10 (m, 2H), 5.42-5.22 (m, 8H), 4.12 (m, 4H), 3.62 (m, 4H), 2.94 (s, 4H), 2.02 (s, 6H). LCMS-ESI$^+$ (m/z): $[M+H]^+$ calculated for $C_{49}H_{46}Cl_2FN_5O_6$: 890.3; found: 890.1.

Example 201: 5-((4-Chloro-2-(((2-hydroxyethyl)amino)methyl)-5-((3'-(((5-(((2-hydroxyethyl)amino)methyl)-6-methoxypyridin-2-yl)oxy)methyl)-2,2'-dimethyl-[1,1'-biphenyl]-3-yl)methoxy)phenoxy)methyl)nicotinonitrile

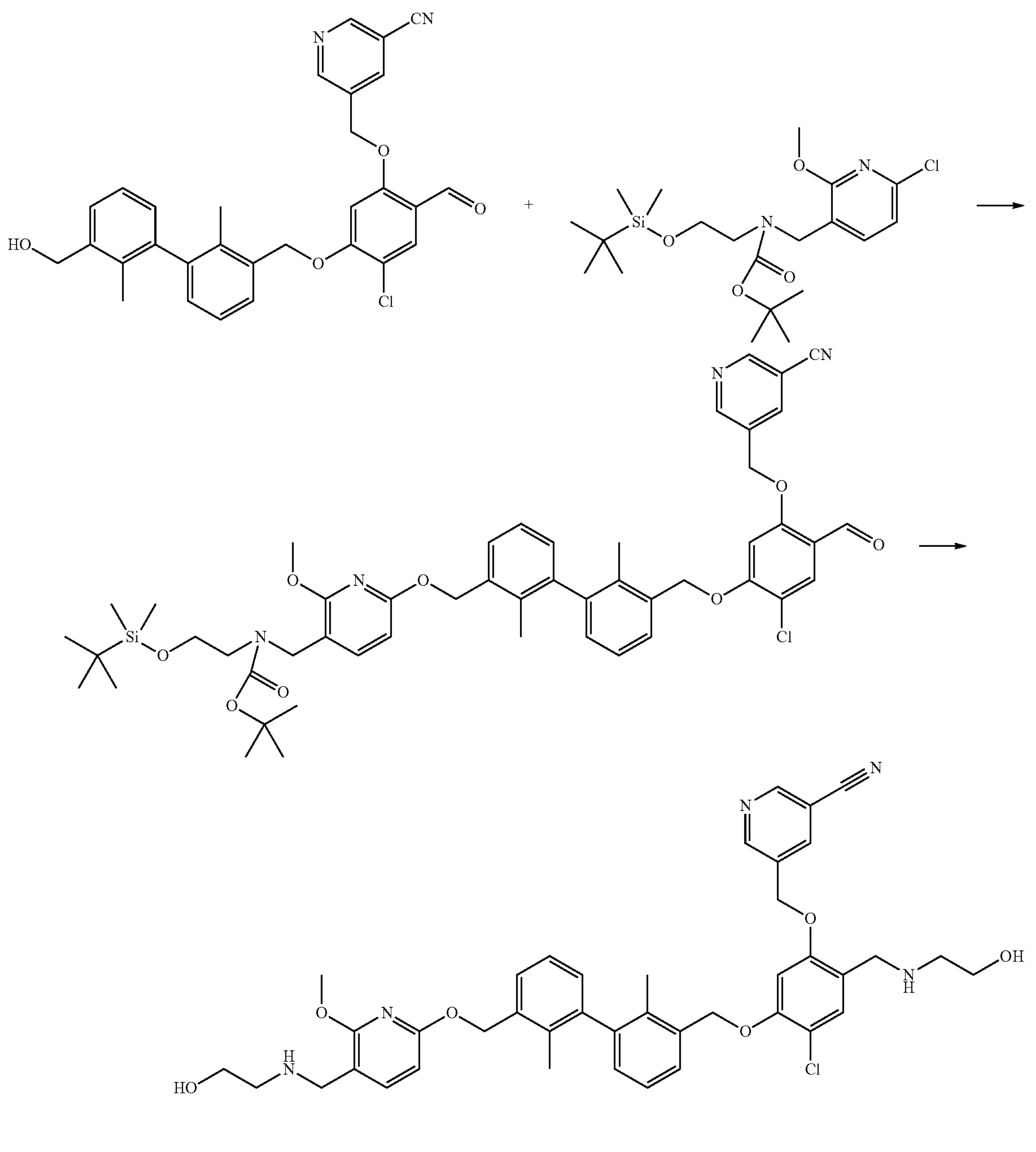

Step 1: tert-Butyl(2-((tert-butyldimethylsilyl)oxy)ethyl)((6-((3'-((2-chloro-5-((5-cyanopyridin-3-yl)methoxy)-4-formylphenoxy)methyl)-2,2'-dimethyl-[1,1'-biphenyl]-3-yl)methoxy)-2-methoxypyridin-3-yl)methyl)carbamate: Cesium carbonate (121 mg, 0.37 mmol), palladium (II) acetate (8.4 mg, 0.037 mmol), 2-di-tert-butylphosphino-2',4',6'-triisopropylbiphenyl(t-butyl Xphos) (16 mg, 0.037 mmol), tert-butyl (2-((tert-butyldimethylsilyl)oxy)ethyl)((6-chloro-2-methoxypyridin-3-yl)methyl)carbamate (80 mg, 0.186 mmol), and 5-((4-chloro-2-formyl-5-((3'-(hydroxymethyl)-2,2'-dimethyl-[1,1'-biphenyl]-3-yl)methoxy)phenoxy)methyl)nicotinonitrile (95 mg, 185.6 μmol) were combined. Toluene (1.2 mL) was added. Toluene (2 mL) was added and the mixture purged with a stream of argon for 5 minutes. The reaction was sealed and heated at 80° C. overnight. The reaction mixture was filtered and the filtrate was concentrated to dryness. The residue was purified chromatography with 0-60% ethyl acetate in hexanes to give a product.

Step 2: 5-((4-Chloro-2-(((2-hydroxyethyl)amino)methyl)-5-((3'-(((5-(((2-hydroxyethyl)amino)methyl)-6-methoxypyridin-2-yl)oxy)methyl)-2,2'-dimethyl-[1,1'-biphenyl]-3-yl)methoxy)phenoxy)methyl)nicotinonitrile: Reductive amination of with 2-aminoethan-1-ol using reductive amination procedure C, followed by deprotection with trifluoroacetic acid gave the title compound. $^1$H NMR (400 MHz, DMSO-$d_6$) δ 9.01 (m, 2H), 8.57 (s, 4H), 8.51-8.43 (m, 1H), 7.74 (d, 1H), 7.56 (s, 1H), 7.46 (dd, 2H), 7.27 (m, 2H), 7.18 (s, 1H), 7.07 (t, 2H), 6.52 (d, 1H), 5.44 (s, 2H), 5.40-5.12 (m, 6H), 4.12 (t, 2H), 4.03 (t, 2H), 3.91 (s, 3H), 3.62 (q, 4H), 2.94 (s, 4H), 2.11-1.90 (m, 6H). LCMS-ESI$^+$ (m/z): $[M+H]^+$ calculated for $C_{41}H_{44}ClN_5O_6$: 738.3; found: 738.1.
Example 202: (S)-4-((5-Chloro-2-((5-cyanopyridin-3-yl)methoxy)-4-((3'-(((5-(((2-hydroxyethyl)amino)methyl)-6-methoxypyridin-2-yl)oxy)methyl)-2,2'-dimethyl-[1,1'-biphenyl]-3-yl)methoxy)benzyl)amino)-3-hydroxybutanoic acid
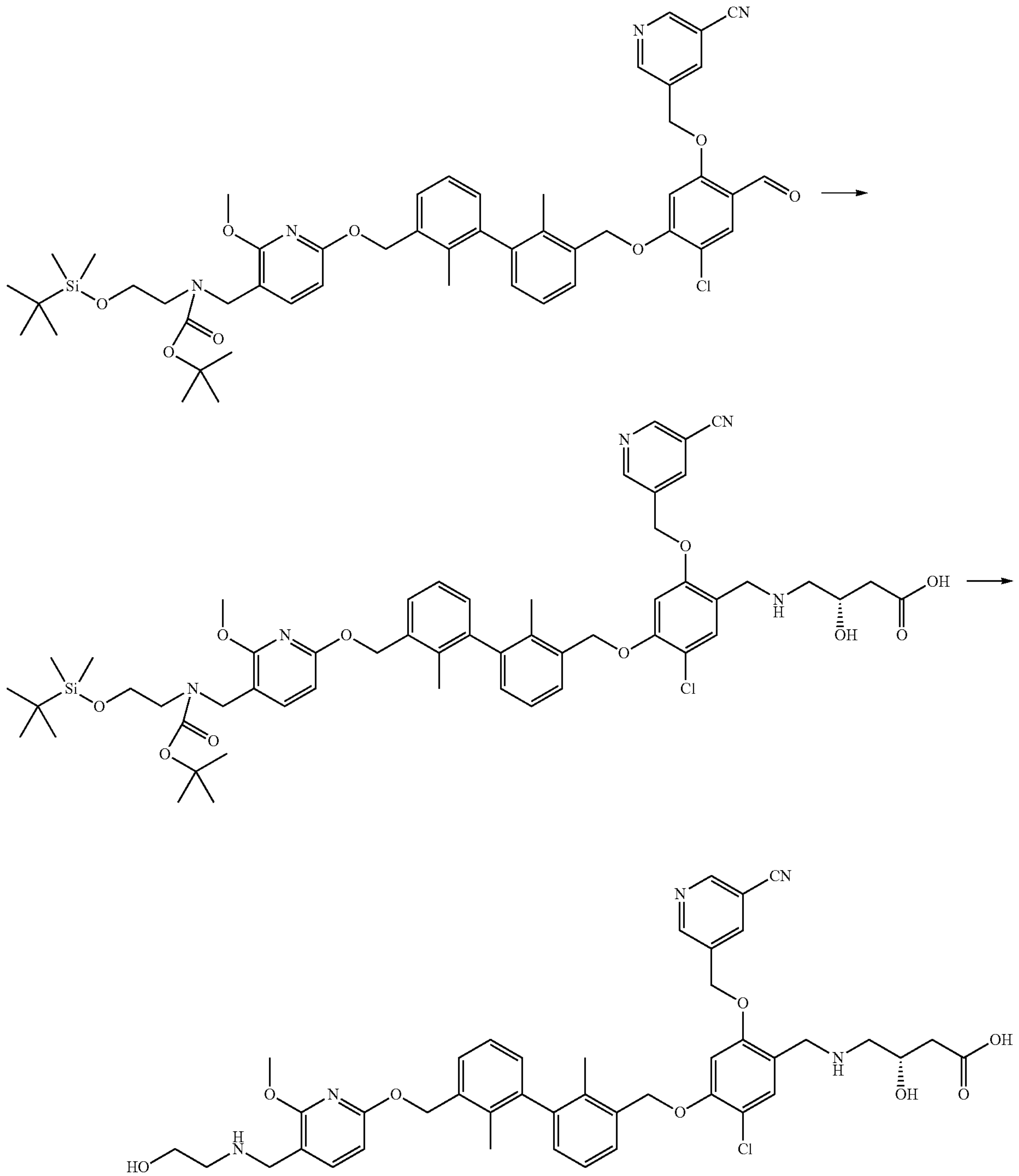

Step 1: (S)-4-((4-((3'-(((5-(((tert-Butoxycarbonyl)(2-((tert-butyldimethylsilyl)oxy)ethyl)amino)methyl)-6-methoxypyridin-2-yl)oxy)methyl)-2,2'-dimethyl-[1,1'-biphenyl]-3-yl)methoxy)-5-chloro-2-((5-cyanopyridin-3-yl)methoxy)benzyl)amino)-3-hydroxybutanoic acid: Reductive amination of tert-butyl (2-((tert-butyldimethylsilyl)oxy)ethyl)((6-((3'-((2-chloro-5-((5-cyanopyridin-3-yl)methoxy)-4-formylphenoxy)methyl)-2,2'-dimethyl-[1,1'-biphenyl]-3-yl)methoxy)-2-methoxypyridin-3-yl)methyl)carbamate with (S)-4-amino-3-hydroxybutanoic acid using reductive amination procedure C gave the intermediate.

Step 2: (S)-4-((5-Chloro-2-((5-cyanopyridin-3-yl)methoxy)-4-((3'-(((5-(((2-hydroxyethyl)amino)methyl)-6-methoxypyridin-2-yl)oxy)methyl)-2,2'-dimethyl-[1,1'-biphenyl]-3-yl)methoxy)benzyl)amino)-3-hydroxybutanoic acid: A solution of tetrabutylammonium fluoride in tetrahydrofuran (1 M, 0.03 mL, 0.03 mmol) was added to the above intermediate in tetrahydrofuran (1.5 mL) at 0° C. The solution was allowed to warm to room temperature and stirred for one hour. The mixture was then cooled to 0° C.

and quenched with water. The mixture was extracted with $CH_2Cl_2$ and washed with brine. The organic phase was dried over sodium sulfate and concentrated under reduced pressure to give a residue. The above residue was stirred in a mixture of $CH_2Cl_2$/TFA (1.25 mL, 4:1) for 2 hrs. Prep-HPLC separation gave the title compound. $^1H$ NMR (400 MHz, Acetonitrile-$d_3$) 6 8.93 (s, 2H), 8.28 (s, 1H), 8.08 (m, 1H), 7.66 (d, 1H), 7.49 (d, 3H), 7.30 (d, 3H), 7.14 (d, 2H), 6.93 (d, 1H), 6.57-6.28 (m, 1H), 5.50 (s, 2H), 5.28 (d, 4H), 4.17 (m, 4H), 3.99 (m, 3H), 3.77 (s, 2H), 3.08 (d, 4H), 2.50 (m, 2H), 2.05 (d, 6H). LCMS-ESI$^+$ (m/z): $[M+H]^+$ calculated for $C_{43}H_{46}ClN_5O_8$: 796.3; found: 796.2.

Example 203: (S)-4-(((6-((3'-((4-((((S)-3-Carboxy-2-hydroxypropyl)amino)methyl)-2-chloro-5-((5-cyanopyridin-3-yl)methoxy)phenoxy)methyl)-2,2'-dimethyl-[1,1'-biphenyl]-3-yl)methoxy)-2-methoxypyridin-3-yl)methyl)amino)-3-hydroxybutanoic acid

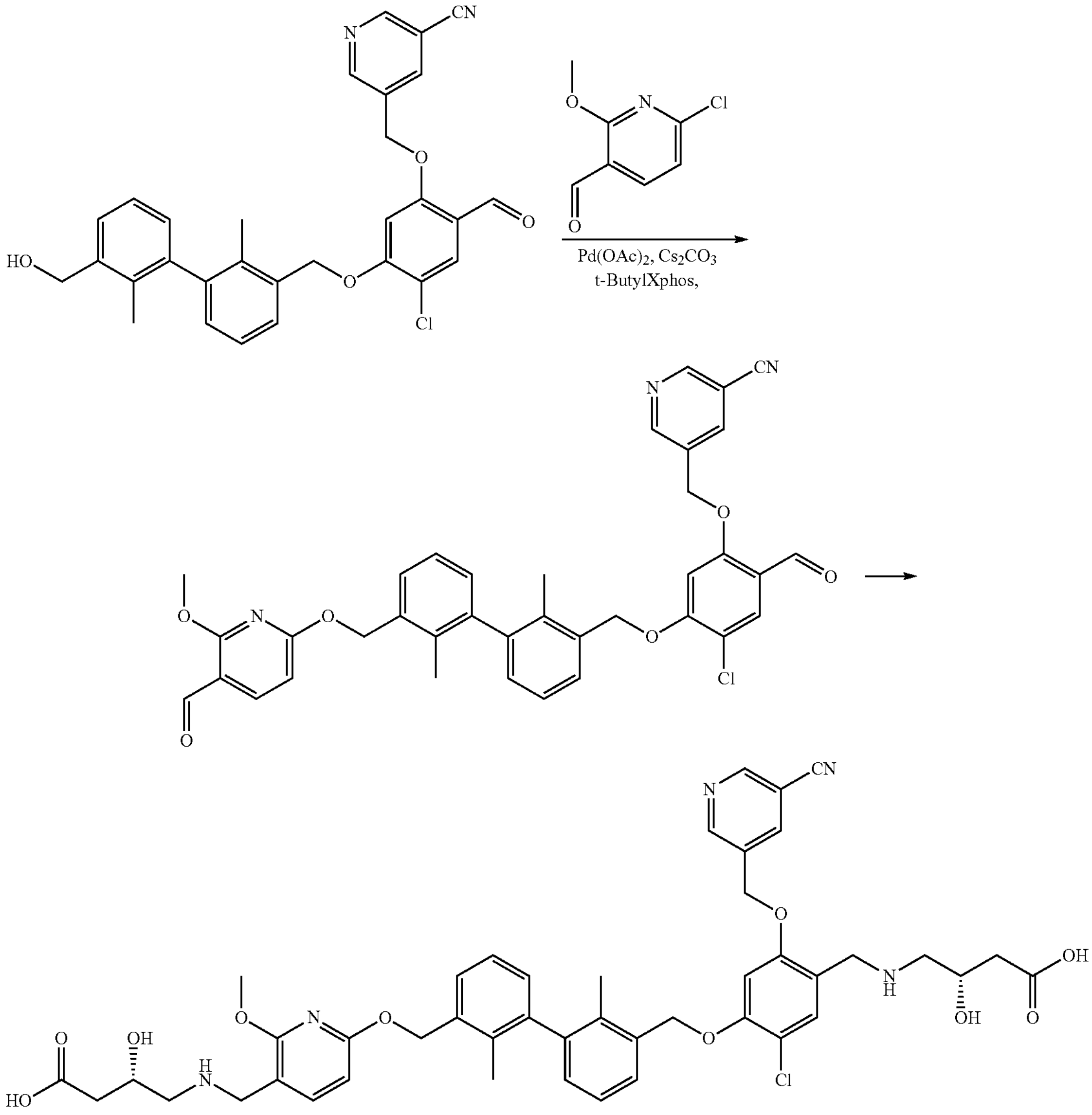

Step 1: 5-((4-Chloro-2-formyl-5-((3'-(((5-formyl-6-methoxypyridin-2-yl)oxy)methyl)-2,2'-dimethyl-[1,1'-biphenyl]-3-yl)methoxy)phenoxy)methyl)nicotinonitrile: Cesium carbonate(46 mg, 0.14 mmol), palladium (II) acetate (2 mg, 0.007 mmol), 2-di-tert-butylphosphino-2',4',6'-triisopropylbiphenyl(t-butyl Xphos) (6 mg, 0.014 mmol), 6-chloro-2-methoxynicotinaldehyde (12 mg, 0.07 mmol), and 5-((4-chloro-2-formyl-5-((3'-(hydroxymethyl)-2,2'-dimethyl-[1,1'-biphenyl]-3-yl)methoxy)phenoxy)methyl) nicotinonitrile (34 mg, 66 □mol) were combined. Toluene (0.4 mL) was added. The reaction was sealed and heated at 80° C. overnight. The reaction mixture was filtered and the filtrate was concentrated to dryness. The residue was purified by silica gel column with 0-50 percent ethyl acetate in hexanes to give the product.

Step 2: (S)-4-(((6-((3'-((4-((((S)-3-Carboxy-2-hydroxypropyl)amino)methyl)-2-chloro-5-((5-cyanopyridin-3-yl) methoxy)phenoxy)methyl)-2,2'-dimethyl-[1,1'-biphenyl]-3-yl)methoxy)-2-methoxypyridin-3-yl)methyl)amino)-3-hydroxybutanoic acid: Reductive amination of 5-((4-chloro-2-formyl-5-((3'-(((5-formyl-6-methoxypyridin-2-yl)oxy) methyl)-2,2'-dimethyl-[1,1'-biphenyl]-3-yl)methoxy) phenoxy)methyl)nicotinonitrile with (S)-4-amino-3-hydroxybutanoic acid using reductive amination procedure C gave the title compound. $^1H$ NMR (400 MHz, Methanol-$d_4$) δ 8.94 (d, 2H), 8.37 (s, 1H), 7.97 (s, 2H), 7.68 (d, 1H), 7.51 (s, 1H), 7.45 (t, 2H), 7.24 (m, 2H), 7.14-7.01 (m, 3H), 6.48 (d, 1H), 5.49 (s, 2H), 5.38 (s, 2H), 5.30 (s, 2H), 4.36-4.19 (m, 2H), 4.17 (s, 2H), 4.03 (s, 3H), 3.25-2.98 (m, 4H), 2.85 (m, 4H), 2.63-2.41 (m, 4H), 2.07 (d, 6H). LCMS-ESI$^+$ (m/z): $[M+H]^+$ calculated for $C_{45}H_{48}ClN_5O_{10}$: 854.3; found: 854.2.

Example 204: 5-((4-Chloro-2-(((2-hydroxyethyl) amino)methyl)-5-((3'-((4-(((2-hydroxyethyl)amino) methyl)-2-(trifluoromethyl)phenoxy)methyl)-2,2'-dimethyl-[1,1'-biphenyl]-3-yl)methoxy)phenoxy) methyl)nicotinonitrile

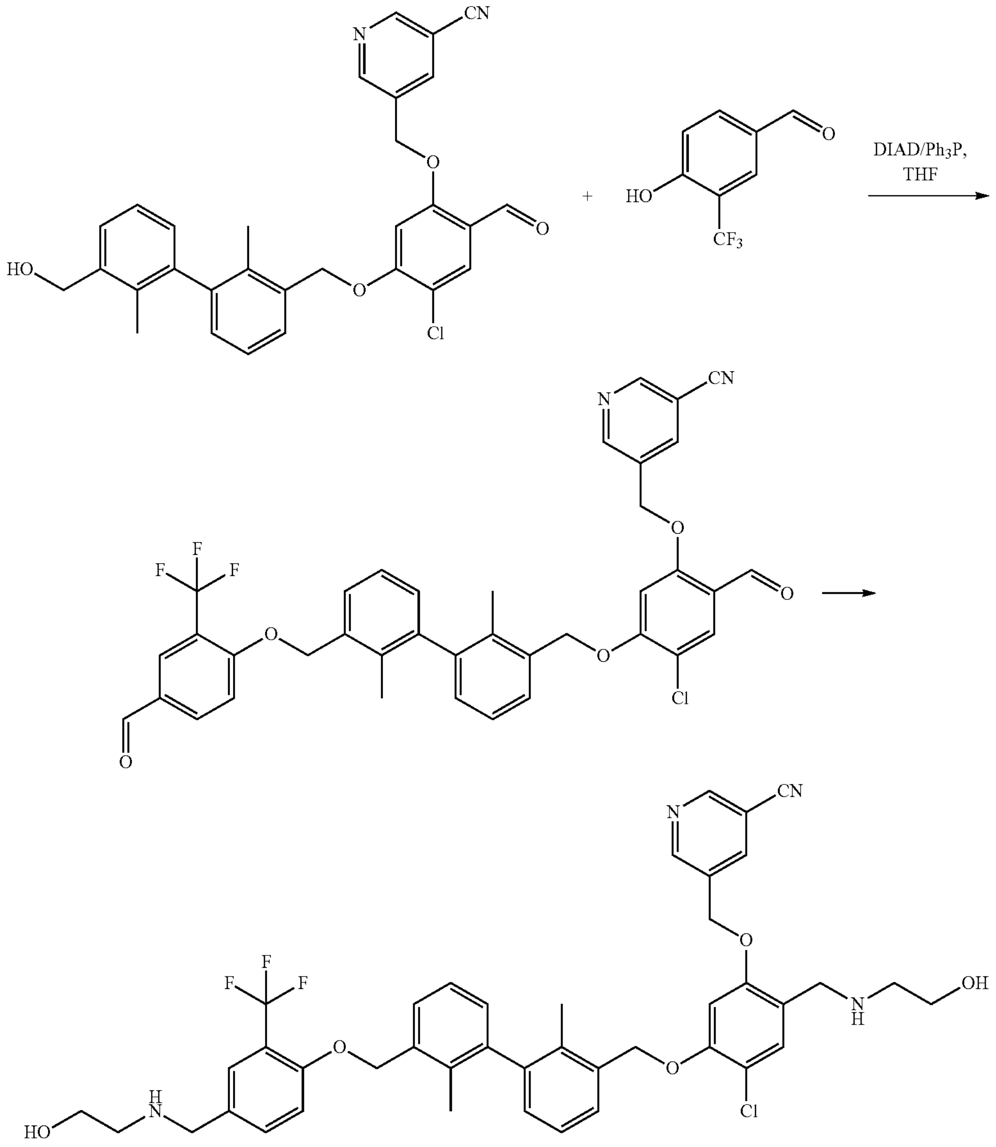

Step 1: 5-((4-Chloro-2-formyl-5-((3'-((4-formyl-2-(trifluoromethyl)phenoxy)methyl)-2,2'-dimethyl-[1,1'-biphenyl]-3-yl)methoxy)phenoxy)methyl)nicotinonitrile: Diisopropylazodicarboxylate (50 mg) in tetrahydrofuran (0.4 mL) was added dropwise to a cooled (0° C.) solution of 4-hydroxy-3-(trifluoromethyl)benzaldehyde (43 mg), triphenylphosphine (61.5 mg) and (5-((4-chloro-2-formyl-5-((3'-(hydroxymethyl)-2,2'-dimethyl-[1,1'-biphenyl]-3-yl)methoxy)phenoxy)methyl)nicotinonitrile (115 mg) in dry tetrahydrofuran (0.75 mL). The resulting reaction mixture was allowed to slowly warm to room temperature with stirring overnight. The reaction mixture was concentrated and the residue was purified by silica gel column chromatography with 20-90% EtOAc in hexanes to give the product.

Step 2: 5-((4-Chloro-2-(((2-hydroxyethyl)amino)methyl)-5-((3'-((4-(((2-hydroxyethyl)amino)methyl)-2-(trifluoromethyl)phenoxy)methyl)-2,2'-dimethyl-[1,1'-biphenyl]-3-yl)methoxy)phenoxy)methyl)nicotinonitrile: Reductive amination of 5-((4-chloro-2-formyl-5-((3'-((4-formyl-2-(trifluoromethyl)phenoxy)methyl)-2,2'-dimethyl-[1,1'-biphenyl]-3-yl)methoxy)phenoxy)methyl)nicotinonitrile with 2-aminoethan-1-ol using reductive amination procedure C gave the title compound. $^1$H NMR (400 MHz, Acetonitrile-$d_3$) δ 8.95 (s, 2H), 8.45 (s, 2H), 8.29 (s, 1H), 7.93 (s, 2H), 7.83 (s, 1H), 7.75 (d, 1H), 7.57-7.49 (m, 2H), 7.47 (s, 1H), 7.41-7.28 (m, 3H), 7.17 (d, 2H), 6.96 (s, 1H), 5.30 (d, 6H), 4.21 (d, 4H), 3.75 (m, 4H), 3.10 (m, 4H), 2.07 (s, 3H), 2.03 (s, 3H). LCMS-ESI$^+$ (m/z): [M+H]$^+$ calculated for $C_{42}H_{42}C_1F_3N_4O_5$: 775.3; found: 775.2.

Example 205: 5-((4-Chloro-5-((3-(1-(3-((5-cyanopyridin-3-yl)methoxy)-4-(((2-hydroxyethyl)amino)methyl)benzoyl)indolin-4-yl)-2-methylbenzyl)oxy)-2-(((2-hydroxyethyl)amino)methyl)phenoxy)methyl)nicotinonitrile

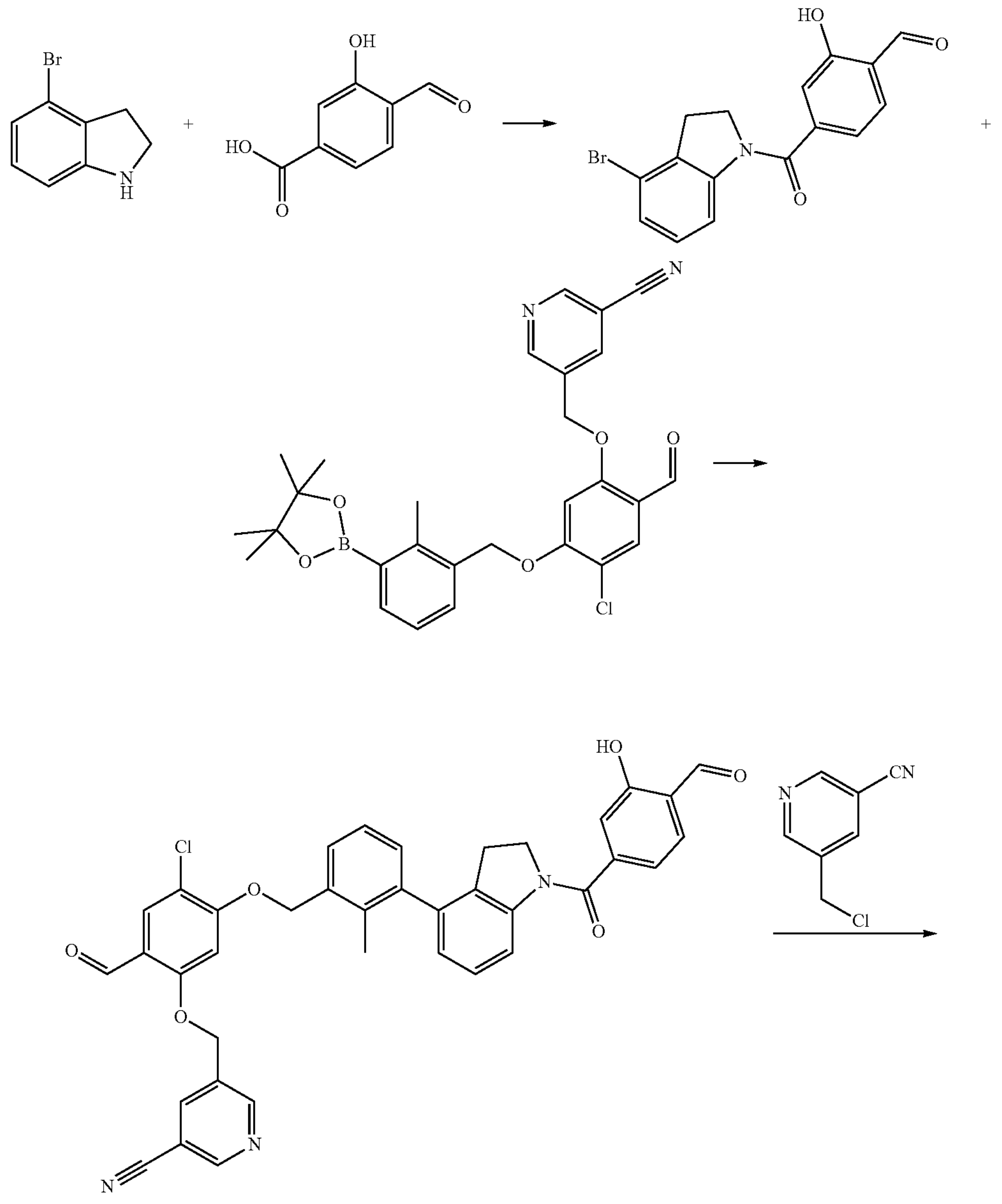

-continued

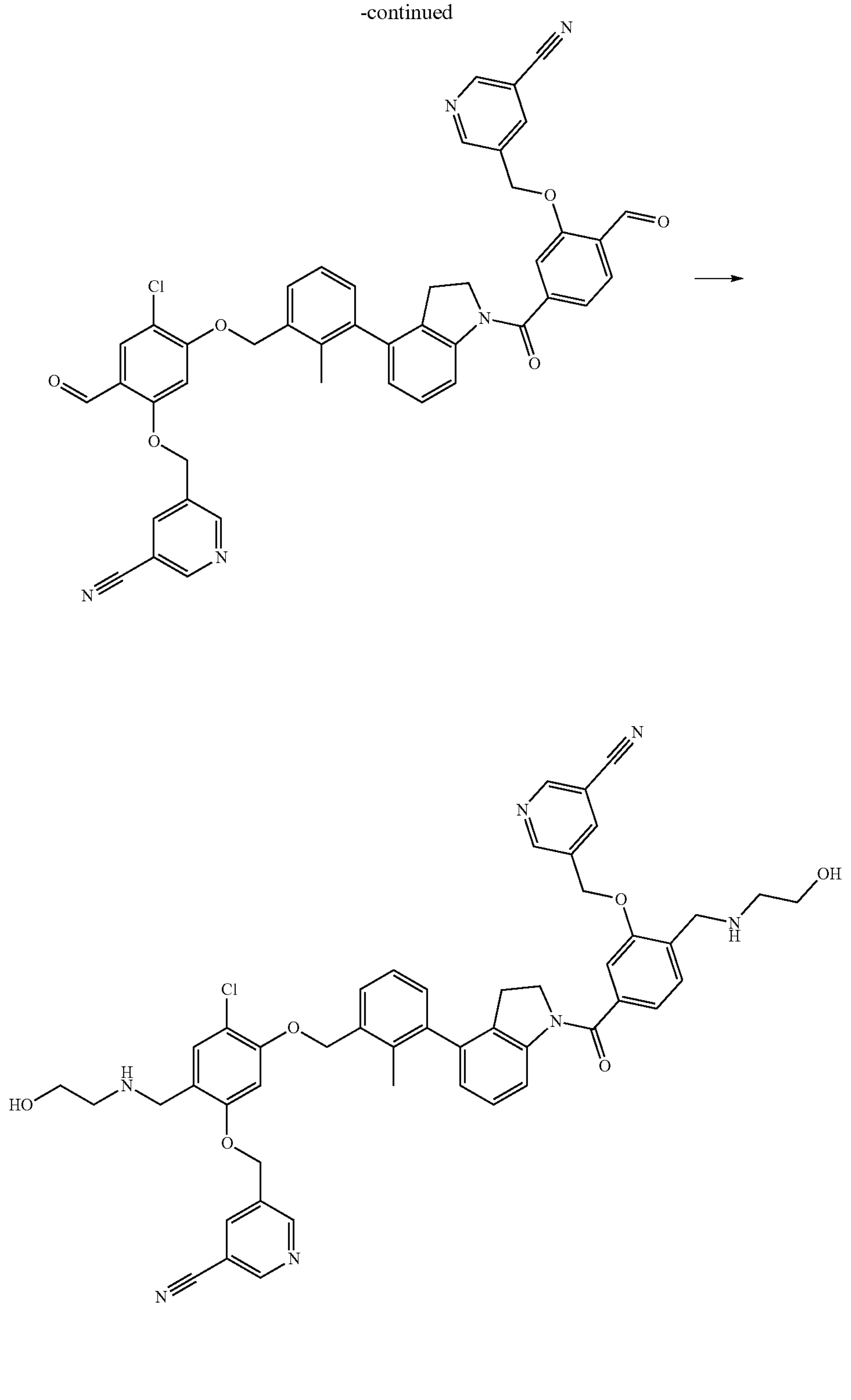

Step 1: 4-(4-Bromoindoline-1-carbonyl)-2-hydroxybenzaldehyde: 4-Formyl-3-hydroxybenzoic acid (830 mg, 5 mmol) was combined with 4-bromoindoline (1089 mg, 5.5 mmol), triethylamine (0.77 mL, 5.5 mmol) and (benzotriazol-1- yloxy)tripyrrolidinophosphonium hexafluorophosphate (PyBOP, 2.86 g, 5.5 mmol) in $CH_2Cl_2$ (10 mL). The mixture was stirred at room temperature overnight, then concentrated and purified by silica gel column chromatography (0-5% MeOH in $CH_2Cl_2$) to afford the product.

Step 2: 5-((4-Chloro-2-formyl-5-((3-(1-(4-formyl-3-hydroxybenzoyl)indolin-4-yl)-2-methylbenzyl)oxy)phenoxy)methyl)nicotinonitrile: To a solution of 4-(4-bromoindoline-1-carbonyl)-2-hydroxybenzaldehyde (150 mg, 0.433 mmol), 5-((4-chloro-2-formyl-5-((2-methyl-3-(4,4,5,5-tetramethyl- 1,3,2-dioxaborolan-2-yl)benzyl)oxy)phenoxy)methyl)nicotinonitrile (220 mg, 0.424 mmol), $NaHCO_3$ (117 mg, 0.85 mmol) in DMF (12 mL) and water (3 mL) was added $Pd(PPh_3)_4$ (61 mg, 0.12 equiv). The reaction mixture was heated at 80° C. for 1 h. Water and EtOAc were added to the reaction mixture. The organic layer was dried, and concentrated. The residue was purified by silica gel column chromatography with 0-10% MeOH in $CH_2Cl_2$ to give the product.

Step 3: 5-((4-Chloro-5-((3-(1-(3-((5-cyanopyridin-3-yl)methoxy)-4-formylbenzoyl)indolin-4-yl)-2-methylbenzyl)oxy)-2-formylphenoxy)methyl)nicotinonitrile: Cesium carbonate (248 mg, 0.76 mmol), 5-((4-chloro-2-formyl-5-((3-(1-(4-formyl-3-hydroxybenzoyl)indolin-4-yl)-2-methylbenzyl)oxy)phenoxy)methyl)nicotinonitrile (250 mg, 0.38 mmol) and 5-(chloromethyl)nicotinonitrile (116 mg, 0.76 mmol) and NaI (12 mg) were stirred at 75 C for 45 minutes in dimethyl formamide (2.5 mL). The reaction was extracted with $CH_2Cl_2$ and water. The organic phase was dried, filtered and concentrated. The residue was purified silica gel column chromatography with 0-10% MeOH in $CH_2Cl_2$ to give the product.

Step 4: 5-((4-Chloro-5-((3-(1-(3-((5-cyanopyridin-3-yl)methoxy)-4-(((2-hydroxyethyl)amino)methyl)benzoyl)indolin-4-yl)-2-methylbenzyl)oxy)-2-(((2-hydroxyethyl)amino)methyl)phenoxy)methyl)nicotinonitrile: Reductive amination of 5-((4-chloro-5-((3-(1-(3-((5-cyanopyridin-3-yl)methoxy)-4-formylbenzoyl)indolin-4-yl)-2-methylbenzyl)oxy)-2-formylphenoxy)methyl)nicotinonitrile with 2-aminoethan-1-ol using reductive amination procedure E gave the title compound. $^1H$ NMR (400 MHz, DMSO-$d_6$) δ 9.06-8.96 (m, 4H), 8.78 (s, 2H), 8.74-8.58 (m, 4H), 8.47 (m, 2H), 8.27 (m, 2H), 7.75 (d, 2H), 7.70 (m, 2H), 7.60-7.53 (m, 2H), 7.49 (d, 2H), 7.27 (m, 2H), 7.21-7.10 (m, 2H), 6.96-6.81 (m, 1H), 5.42-5.24 (m, 6H), 4.27 (s, 2H), 4.13 (s, 2H), 3.89 (s, 2H), 3.63 (m, 4H), 2.97 (d, 4H), 2.64 (s, 4H), 2.12 (s, 3H). LCMS-ESI$^+$ (m/z): $[M+H]^+$ calculated for $C_{49}H_{46}ClN_7O_6$: 864.3; found: 864.2.

Example 206: (S)-4-((4-(4-(3-((4-((((S)-3-Carboxy-2-hydroxypropyl)amino)methyl)-2-chloro-5-((5-cyanopyridin-3-yl)methoxy)phenoxy)methyl)-2-methylphenyl)indoline-1-carbonyl)-2-((5-cyanopyridin-3-yl)methoxy)benzyl)amino)-3-hydroxybutanoic acid

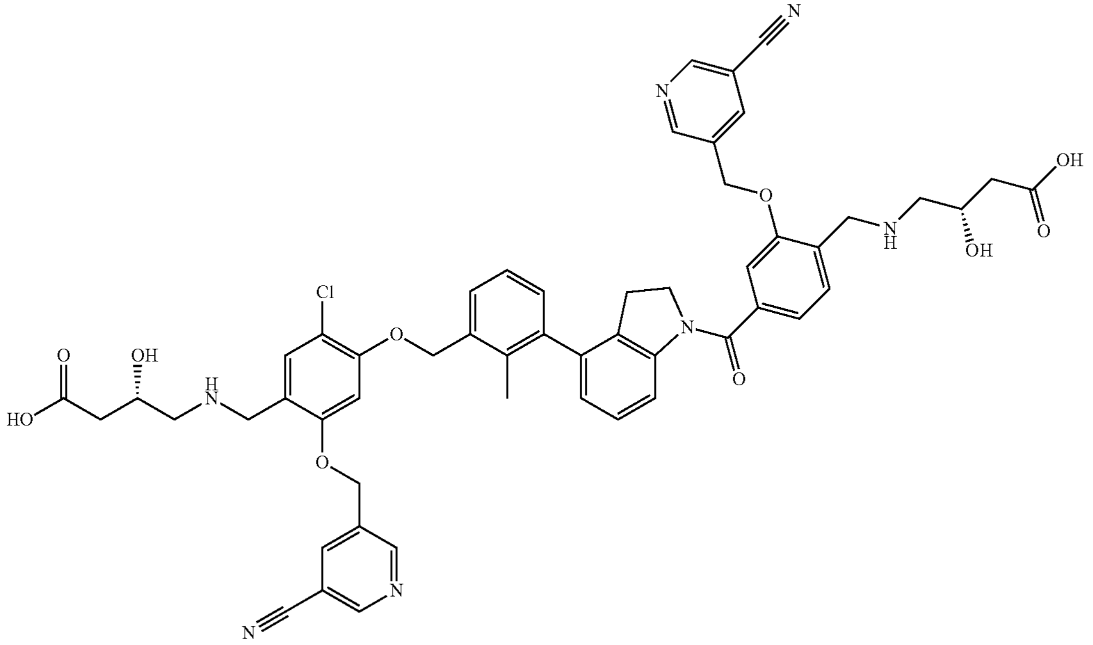 [SMILES: Cc1c(COc2cc(OCc3cncc(C#N)c3)c(CNC[C@@H](O)CC(=O)O)cc2Cl)cccc1-c1cccc2c1CCN2C(=O)c1ccc(CNC[C@@H](O)CC(=O)O)c(OCc2cncc(C#N)c2)c1]

Reductive amination of 5-((4-chloro-5-((3-(1-(3-((5-cyanopyridin-3-yl)methoxy)-4-formylbenzoyl)indolin-4-yl)-2-methylbenzyl)oxy)-2-formylphenoxy)methyl)nicotinonitrile with (S)-4-amino-3-hydroxybutanoic acid using reductive amination procedure E gave the title compound. $^1H$ NMR (400 MHz, Methanol-$d_4$) δ 9.00-8.85 (m, 4H), 8.44-8.34 (m, 2H), 7.60 (d, 1H), 7.51 (s, 1H), 7.50-7.44 (m, 1H), 7.40 (s, 1H), 7.35-7.23 (m, 2H), 7.18 (dd, 1H), 7.08 (s, 1H), 6.94 (s, 1H), 5.45-5.37 (m, 4H), 5.30 (s, 2H), 4.39 (s, 2H), 4.32-4.12 (m, 4H), 3.99 (s, 2H), 3.26-2.70 (m, 6H), 2.61-2.44 (m, 4H), 2.18 (s, 3H). LCMS-ESI$^+$ (m/z): $[M+H]^+$ calculated for $C_{53}H_{50}ClN_7O_{10}$: 980.3; found: 980.3.

Example 207: (S)-4-((5-Chloro-4-((3'-((2-chloro-5-((5-cyanopyridin-3-yl)methoxy)-4-(((2-hydroxyethyl)amino)methyl)phenoxy)methyl)-2,2'-dimethyl-[1,1'-biphenyl]-3-yl)methoxy)-2-((5-cyanopyridin-3-yl)methoxy)benzyl)amino)-3-hydroxybutanoic acid
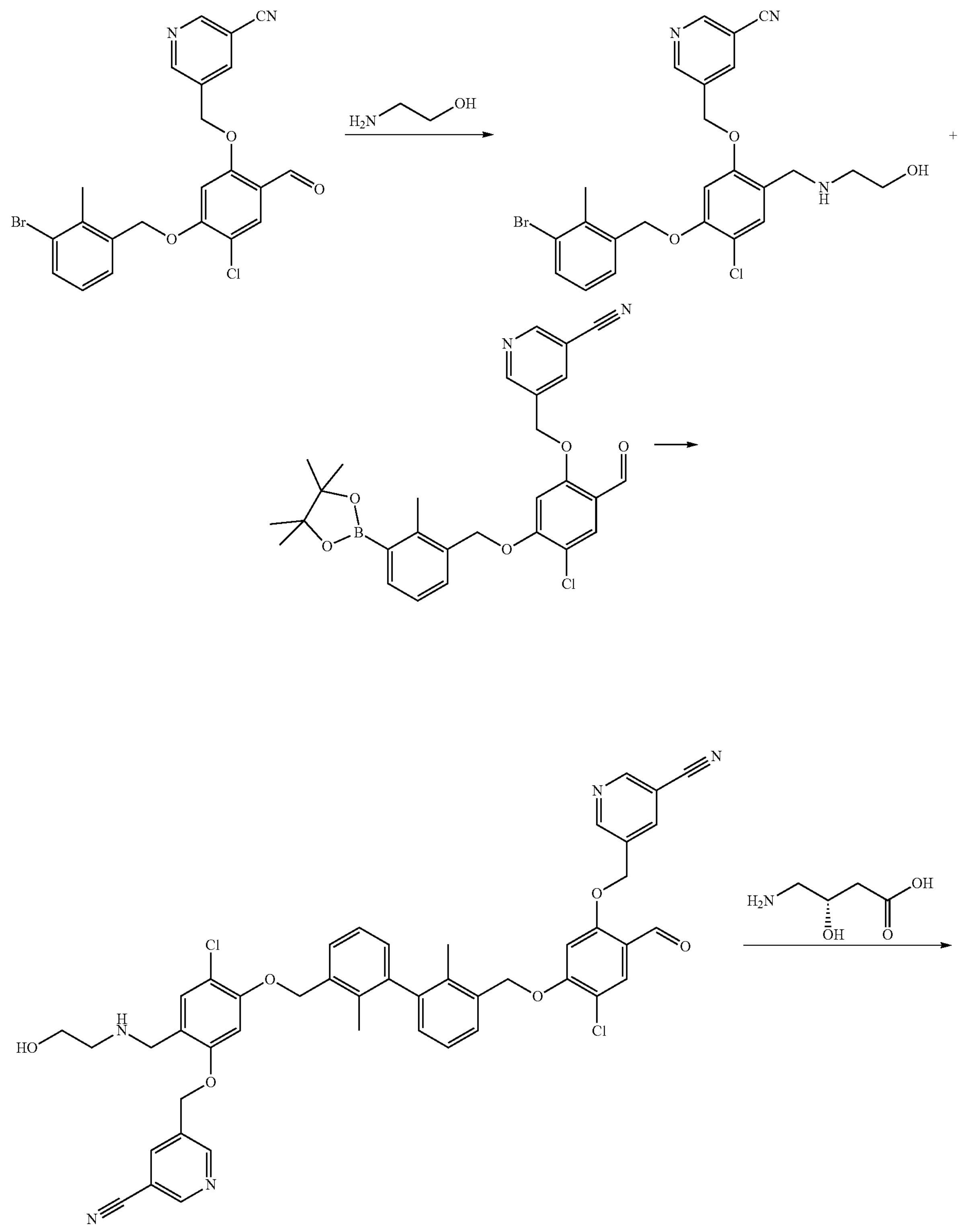

-continued

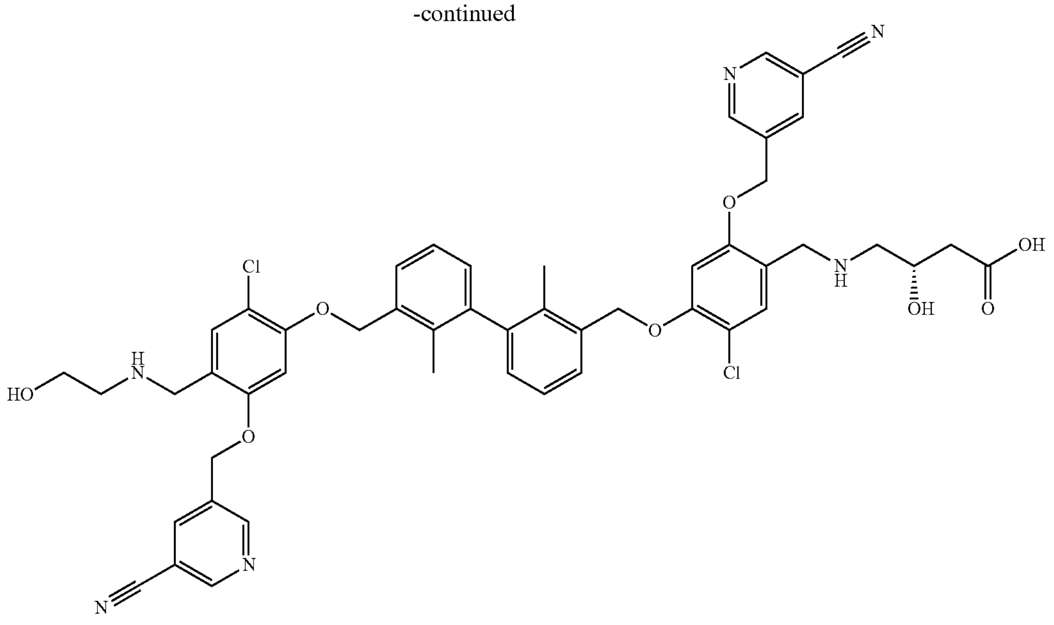

Step 1: 5-((5-((3-Bromo-2-methylbenzyl)oxy)-4-chloro-2-(((2-hydroxyethyl)amino)methyl)phenoxy)methyl)nicotinonitrile: Reductive amination of 5-((5-((3-bromo-2-methylbenzyl)oxy)-4-chloro-2-formylphenoxy)methyl)nicotinonitrile with 2-aminoethan-1-ol using reductive amination procedure E gave the product.

Step 2: 5-((4-Chloro-5-((3'-((2-chloro-5-((5-cyanopyridin-3-yl)methoxy)-4-(((2-hydroxyethyl)amino)methyl)phenoxy)methyl)-2,2'-dimethyl-[1,1'-biphenyl]-3-yl)methoxy)-2-formylphenoxy)methyl)nicotinonitrile: To a solution of 5-((5-((3-bromo-2-methylbenzyl)oxy)-4-chloro-2-(((2-hydroxyethyl)amino)methyl)phenoxy)methyl)nicotinonitrile (86 mg, 0.166 mmol), 5-((4-chloro-2-formyl-5-((2-methyl-3-(4,4,5,5-tetramethyl-1,3,2-dioxaborolan-2-yl)benzyl)oxy)phenoxy)methyl)nicotinonitrile (98 mg, 0.189 mmol), $NaHCO_3$ (65 mg, 0.47 mmol) in DMF (4 mL) and water (1 mL) was added $Pd(PPh_3)_4$ (40 mg). The reaction mixture was heated at 80° C. for 1 h. The reaction mixture was filtered and the filtrate purified by prep-HPLC to give the product.

Step 3: (S)-4-((5-Chloro-4-((3'-((2-chloro-5-((5-cyanopyridin-3-yl)methoxy)-4-(((2-hydroxyethyl)amino)methyl)phenoxy)methyl)-2,2'-dimethyl-[1,1'-biphenyl]-3-yl)methoxy)-2-((5-cyanopyridin-3-yl)methoxy)benzyl)amino)-3-hydroxybutanoic acid: Reductive amination of 5-((4-chloro-5-((3'-((2-chloro-5-((5-cyanopyridin-3-yl)methoxy)-4-(((2-hydroxyethyl)amino)methyl)phenoxy)methyl)-2,2'-dimethyl-[1,1'-biphenyl]-3-yl)methoxy)-2-formylphenoxy)methyl)nicotinonitrile with (S)-4-amino-3-hydroxybutanoic acid using reductive amination procedure E gave the title compound. $^1H$ NMR (400 MHz, Methanol-$d_4$) δ 9.01-8.87 (m, 4H), 8.38 (q, 2H), 7.51 (s, 2H), 7.50-7.41 (m, 2H), 7.27 (t, 2H), 7.12 (dd, 2H), 7.08 (s, 2H), 5.37 (s, 4H), 5.31 (s, 4H), 4.23 (m, 5H), 3.86-3.68 (m, 2H), 3.25-2.87 (m, 4H), 2.51 (d, 2H), 2.08 (s, 6H). LCMS-$ESI^+$ (m/z): $[M+H]^+$ calculated for $C_{50}H_{48}Cl_2N_6O_8$: 931.3; found: 931.2.

Example 208: (S)-4-((4-((5-(3-((4-((((S)-3-Carboxy-2-hydroxypropyl)amino)methyl)-2-chloro-5-((5-cyanopyridin-3-yl)methoxy)phenoxy)methyl)-2-methylphenyl)pyridin-3-yl)methoxy)-5-chloro-2-((5-cyanopyridin-3-yl)methoxy)benzyl)amino)-3-hydroxybutanoic acid

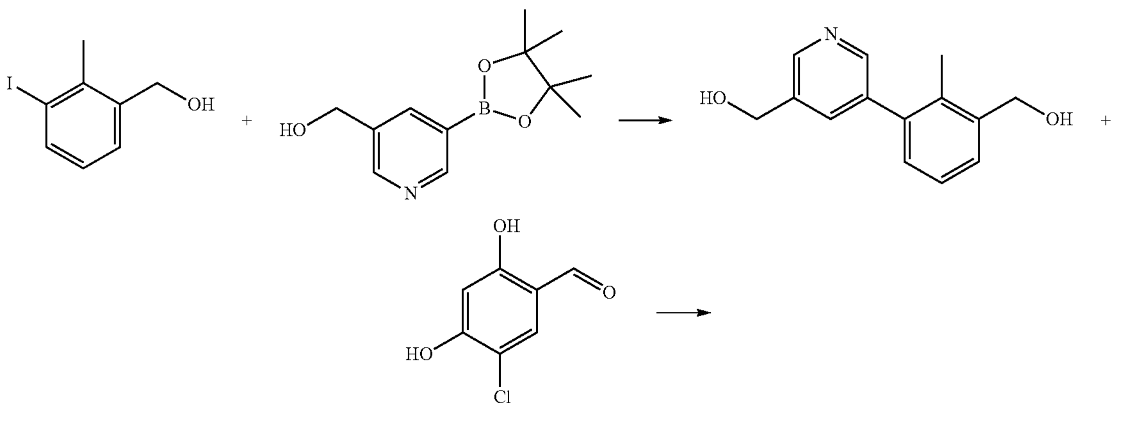

-continued

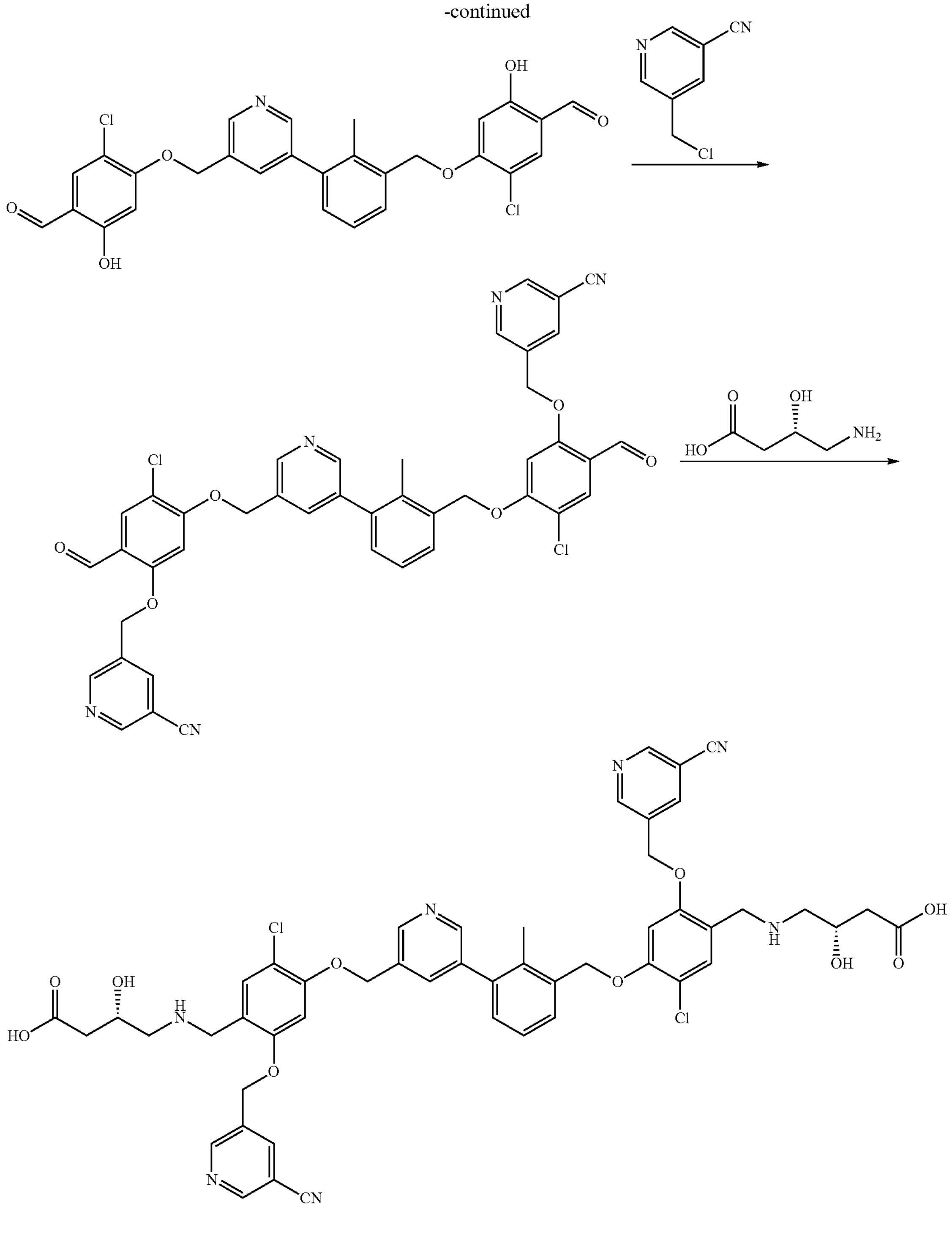

Step 1: (5-(3-(Hydroxymethyl)-2-methylphenyl)pyridin-3-yl)methanol: A solution of (3-iodo-2-methylphenyl) methanol (200 mg, 0.806 mmol)(5-(4,4,5,5-tetramethyl-1,3,2-dioxaborolan-2-yl) pyridin-3-yl)methanol (199 mg, 0.847 mmol), $K_2CO_3$ (334 mg, 2.42 mmol) in 1,4-dioxane (4 mL) and water (1 mL) was purged with nitrogen for 30 min. Pd(dppf)$Cl_2$:DCM (66 mg, 0.081 mmol) was added and the reaction mixture was heated under microwave at 100° C. for 1 h. The reaction mixture was filtered through a pad of celite and the pad was washed with MeOH. The filtrate was concentrated to dryness and the residue was purified by silica gel column with 1-5% MeOH in $CH_2Cl_2$ to give a product.

Step 2: 5-Chloro-4-((5-(3-((2-chloro-4-formyl-5-hydroxyphenoxy)methyl)-2-methylphenyl)pyridin-3-yl) methoxy)-2-hydroxybenzaldehyde: Diisopropyl azodicarboxylate (387 mg, 1.9 mmol) in tetrahydrofuran (3.7 mL) was added dropwise to a cooled (0 C) solution of 5-chloro-2,4-dihydroxybenzaldehyde (300 mg, 1.738 mmol), triphenylphosphine (477 mg, 1.93 mmol) and (5-(3-(hydroxymethyl)-2-methylphenyl)pyridin-3-yl)methanol (200 mg, 0.86 mmol) in dry tetrahydrofuran (7.5 mL). The resulting reaction mixture was allowed to slowly warm to room temperature with stirring overnight. The reaction mixture was concentrated and the residue was purified by silica gel column with 20-60% EtOAc in hexanes to give the product.

Step 3: 5-((4-Chloro-5-((3-(5-((2-chloro-5-((5-cyanopyridin-3-yl)methoxy)-4-formylphenoxy)methyl)pyridin-3-yl)-2-methylbenzyl)oxy)-2-formylphenoxy)methyl)nicotinonitrile: Cesium carbonate (138 mg, 0.42 mmol), 5-chloro-4-((5-(3-((2-chloro-4-formyl-5-hydroxyphenoxy)methyl)-2-methylphenyl)pyridin-3-yl)methoxy)-2-hydroxybenzaldehyde (58 mg, 0.411 mmol) were combined in dimethylformamide (1 mL). 5-(Chloromethyl)nicotinonitrile (138 mg, 0.91 mmol) and NaI (0.1 equiv) were added and the mixture was stirred at 75° C. overnight. The mixture was treated with $CH_2Cl_2$ and water. The organic phase was separated, dried over $Na_2SO_4$, and concentrated. The residue was purified by prep-HPLC to give the product.

Step 4: (S)-4-((4-((5-(3-((4-((((S)-3-Carboxy-2-hydroxypropyl)amino)methyl)-2-chloro-5-((5-cyanopyridin-3-yl)methoxy)phenoxy)methyl)-2-methylphenyl)pyridin-3-yl)methoxy)-5-chloro-2-((5-cyanopyridin-3-yl)methoxy)benzyl)amino)-3-hydroxybutanoic acid: Reductive amination of 5-((4-chloro-5-((3-(5-((2-chloro-5-((5-cyanopyridin-3-yl)methoxy)-4-formylphenoxy)methyl)pyridin-3-yl)-2-methylbenzyl)oxy)-2-formylphenoxy)methyl)nicotinonitrile with (S)-4-amino-3-hydroxybutanoic acid using reductive amination procedure C gave the title compound. $^1H$ NMR (400 MHz, Methanol-$d_4$) δ 8.99-8.86 (m, 4H), 8.70 (s, 1H), 8.54 (s, 1H), 8.36 (d, 2H), 8.01 (s, 1H), 7.53 (dd, 3H), 7.36-7.24 (m, 2H), 7.08 (d, 2H), 5.38 (m, 8H), 4.24 (m, 6H), 3.27-3.09 (m, 2H), 3.06-2.92 (m, 2H), 2.52 (m, 4H), 2.29 (s, 3H). LCMS-ESI$^+$ (m/z): $[M+H]^+$ calculated for $C_{50}H_{47}Cl_2N_7O_{10}$: 976.3; found: 976.2.

Example 209: (S)-4-((4-((3'-(1-(2-(((S)-3-carboxy-2-hydroxypropyl)amino)ethyl)-1H-indazol-5-yl)-2,2'-dimethyl-[1,1'-biphenyl]-3-yl)methoxy)-5-chloro-2-((5-cyanopyridin-3-yl)methoxy)benzyl)amino)-3-hydroxybutanoic acid

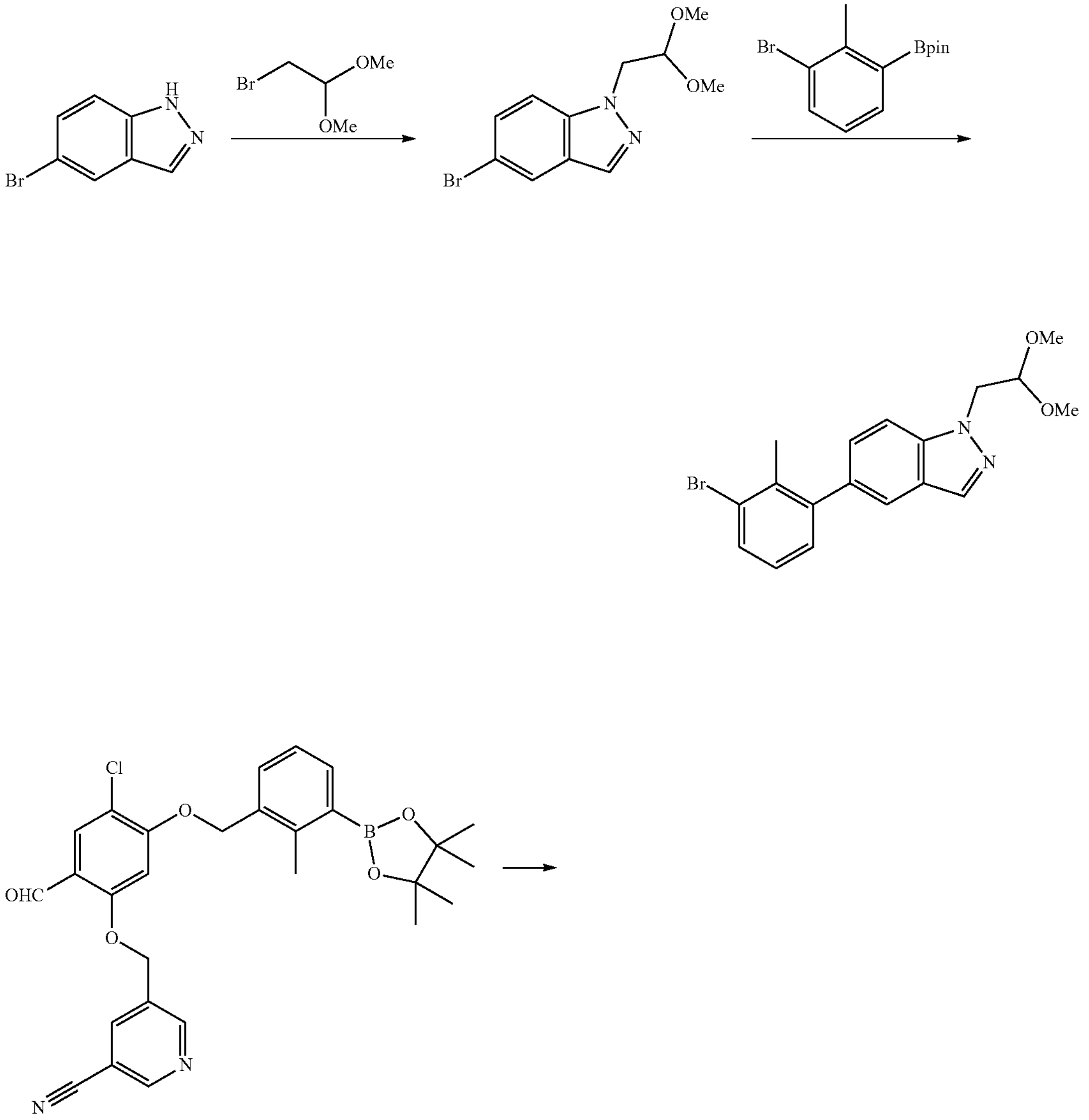

-continued

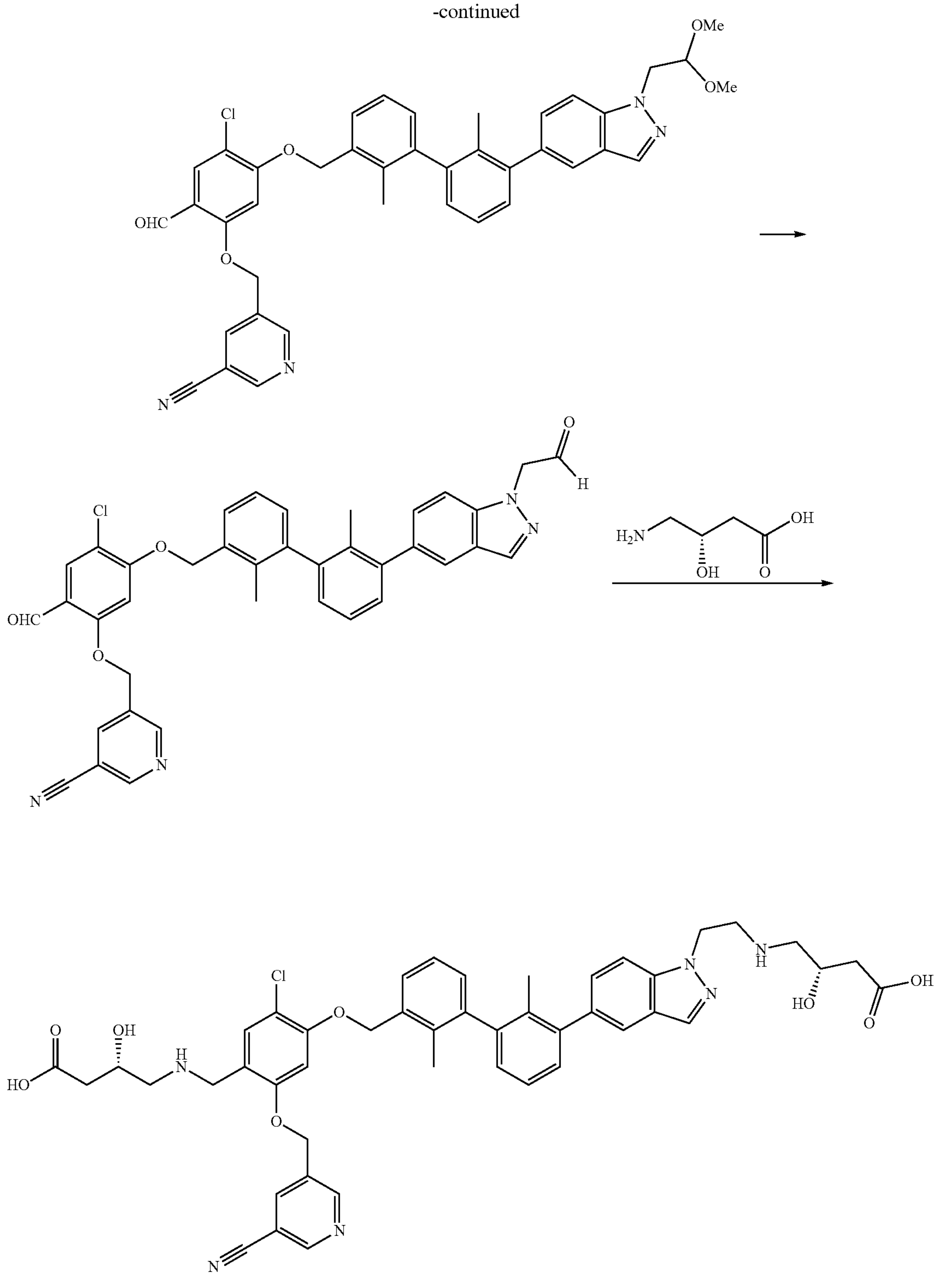

Step 1: To a solution of 5-bromo-1H-indazole (820 mg, 4.16 mmol), bromoacetaldehyde dimethyl acetal (0.980 mL, 8.32 mmol) in DMSO (8.00 mL) was added cesium carbonate (5.42 g, 16.7 mmol). The reaction mixture was stirred at 40° C. for 24h. Analysis by tlc/LCMS indicated formation of the desired product, and a significant amount of the starting material remaining. The reaction mixture was cooled to rt, and quenched by the addition of sat $NH_4Cl$ and EtOAc. The layers were separated and the aqueous layer was further extracted with EtOAc. The organic layers were combined, washed with brine, dried (over $Na_2SO_4$), filtered then concentrated in vacuo. The crude mixture was purified by $SiO_2$ column chromatography (ISCO gold, 40 g column; 0-100% EtOAc/Hex) to afford 5-bromo-1-(2,2-dimethoxyethyl)indazole.

Step 2: 5-bromo-1-(2,2-dimethoxyethyl)indazole (300 mg, 1.05 mmol), (3-Bromo-2-methylphenyl)boronic acid (283 mg, 1.32 mmol), potassium carbonate (436 mg, 3.16 mmol) and tetrakis(triphenylphosphine)palladium (122 mg, 0.105 mmol) were combined in a reaction vessel. Dioxane (10.0 mL) and water (2.0 mL) were injected and the resulting suspension was sparged with argon (via a balloon filled with argon) for 10 minutes. The reaction mixture was stirred at 90° C. for 5 h. Analysis by tlc/LCMS indicated consumption of the bromide starting material and formation of the desired product. The reaction mixture was cooled to rt, and quenched by the addition of sat $NH_4Cl$ and EtOAc. The layers were separated and the aqueous layer was further extracted with EtOAc. The organic layers were combined, washed with brine, dried (over $Na_2SO_4$), filtered then concentrated in vacuo. The crude mixture was purified by $SiO_2$ column chromatography (ISCO gold, 24 g column; 0-50% EtOAc/Hex) to afford 5-(3-bromo-2-methylphenyl)-1-(2,2-dimethoxyethyl)-1H-indazole. (M+1=375.08, 377.05).

Step 3: 5-[[4-chloro-2-formyl-5-[[2-methyl-3-(4,4,5,5-tetramethyl-1,3,2-dioxaborolan-2-yl)phenyl]methoxy]phenoxy]methyl]pyridine-3-carbonitrile (120 mg, 0.23 mmol), 5-(3-bromo-2-methylphenyl)-1-(2,2-dimethoxyethyl)-1H-indazole (80% purity, 160 mg, 0.35 mmol), potassium carbonate (110 mg, 0.81 mmol) and tetrakis(triphenylphosphine)palladium (67 mg, 0.058 mmol) were combined in a sealed vial. Dioxane (3.0 mL) and water (0.75 mL) were injected and the resulting suspension was sparged with argon (via a balloon filled with argon) for 10 minutes. The reaction mixture was stirred at 95° C. for 5 h. Analysis by tlc/LCMS indicated consumption of the boronate starting material and formation of the desired product. The reaction mixture was cooled to rt, and quenched by the addition of sat $NH_4Cl$ and EtOAc. The layers were separated and the aqueous layer was further extracted with EtOAc. The organic layers were combined, washed with brine, dried (over $Na_2SO_4$), filtered then concentrated in vacuo. The crude mixture was purified by SiO2 column chromatography (ISCO gold, 12 g column; 0-50% EtOAc/Hex) to afford 5-((4-chloro-5-((3'-(1-(2,2-dimethoxyethyl)-1H-indazol-5-yl)-2,2'-dimethyl-[1,1'-biphenyl]-3-yl)methoxy)-2-formylphenoxy)methyl)nicotinonitrile. (M+1=688.09).

Step 4: To a solution of 5-((4-chloro-5-((3'-(1-(2,2-dimethoxyethyl)-1H-indazol-5-yl)-2,2'-dimethyl-[1,1'-biphenyl]-3-yl)methoxy)-2-formylphenoxy)methyl)nicotinonitrile in THF (1.0 mL) was added (0.50 mL) of 4N HCl then 10 drops of conc. HCl. The mixture was stirred at rt overnight. Analysis by LCMS indicated formation of the desired product (a mixture of the desired product, and the hydrate and hemiacetal derivatives were observed in the LCMS chromatogram). The reaction mixture was poured into a mixture of brine and EtOAc. The layers were separated and the aqueous layer was further extracted with EtOAc. The organic layers were combined, washed with brine, dried (over $Na_2SO_4$), filtered then concentrated in vacuo. The crude mixture was processed in the next step immediately (M+1=641.35; the 1H NMR of the crude material indicated formation of the desired aldehyde product).

Step 5: 5-((4-chloro-5-((2,2'-dimethyl-3'-(1-(2-oxoethyl)-1H-indazol-5-yl)-[1,1'-biphenyl]-3-yl)methoxy)-2-formylphenoxy)methyl)nicotinonitrile (85 mg, 0.13 mmol) was transformed to the desired product with (3S)-4-amino-3-hydroxy-butanoic acid (160 mg, 1.3 mmol) via reductive amination using a modified version of Procedure G (modification of the work-up as described). The crude mixture was concentrated in vacuo, and then re-dissolved in DMF (3 mL) and TFA (0.1 mL). The resulting solution was purified by reverse-phase HPLC (10-90% MeCN/H2O+0.1% TFA) to afford (S)-4-((4-((3'-(1-(2-(((S)-3-carboxy-2-hydroxypropyl)amino)ethyl)-1H-indazol-5-yl)-2,2'-dimethyl-[1,1'-biphenyl]-3-yl)methoxy)-5-chloro-2-((5-cyanopyridin-3-yl)methoxy)benzyl)amino)-3-hydroxybutanoic acid as the bis-TFA salt: $^1$H NMR (400 MHz, Methanol-$d_4$) δ 8.95 (d, J=2.1 Hz, 1H), 8.92 (d, J=2.0 Hz, 1H), 8.37 (t, J=2.1 Hz, 1H), 8.16 (d, J=0.9 Hz, 1H), 7.74 (t, J=1.1 Hz, 1H), 7.70-7.63 (m, 1H), 7.51 (s, 1H), 7.49-7.43 (m, 2H), 7.34-7.22 (m, 3H), 7.17 (dd, J=7.7, 1.4 Hz, 1H), 7.11 (dd, J=7.4, 1.6 Hz, 1H), 7.07 (s, 1H), 5.37 (s, 2H), 5.32 (s, 2H), 4.83-4.74 (m, 2H), 4.31 (dtd, J=9.5, 6.3, 3.1 Hz, 1H), 4.26-4.15 (m, 3H), 3.82-3.59 (m, 2H), 3.37-3.31 (m, 1H), 3.24-3.07 (m, 2H), 3.06-2.92 (m, 1H), 2.56 (d, J=6.3 Hz, 2H), 2.51 (d, J=6.3 Hz, 2H), 2.16 (s, 3H), 1.88 (s, 3H); 19F NMR (400 MHz, Methanol-d4) δ −77.6; ES/MS: M+1=847.12.

Example 210: (S)-4-(((5-(3'-((4-((((S)-3-carboxy-2-hydroxypropyl)amino)methyl)-2-chloro-5-((5-cyanopyridin-3-yl)methoxy)phenoxy)methyl)-2,2'-dimethyl-[1,1'-biphenyl]-3-yl)benzofuran-2-yl)methyl)amino)-3-hydroxybutanoic acid (or(S)-4-(((5-(3'-((4-((((S)-3-carboxy-2-hydroxypropyl)amino)methyl)-2-chloro-5-((5-cyanopyridin-3-yl)methoxy)phenoxy)methyl)-2,2'-dimethyl-[1,1'-biphenyl]-3-yl)benzofuran-2-yl)methyl)amino)-3-hydroxybutanoic acid)

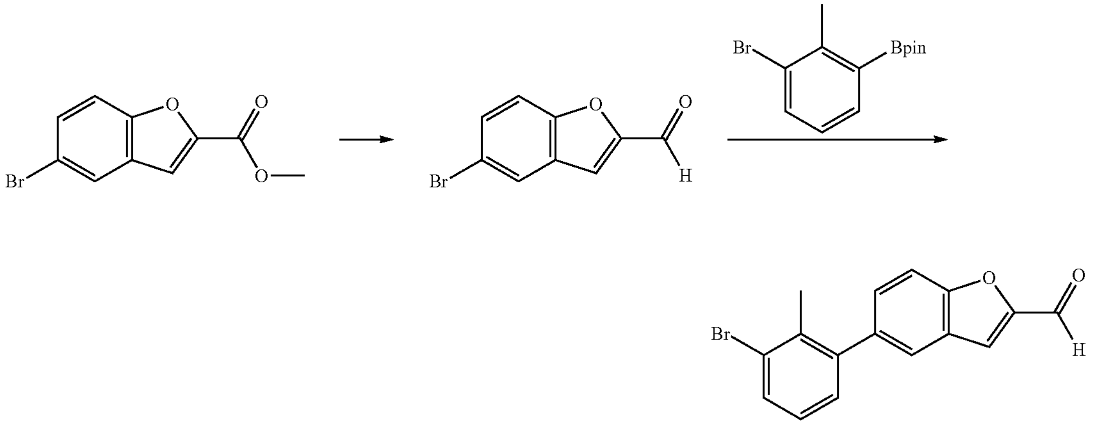

-continued

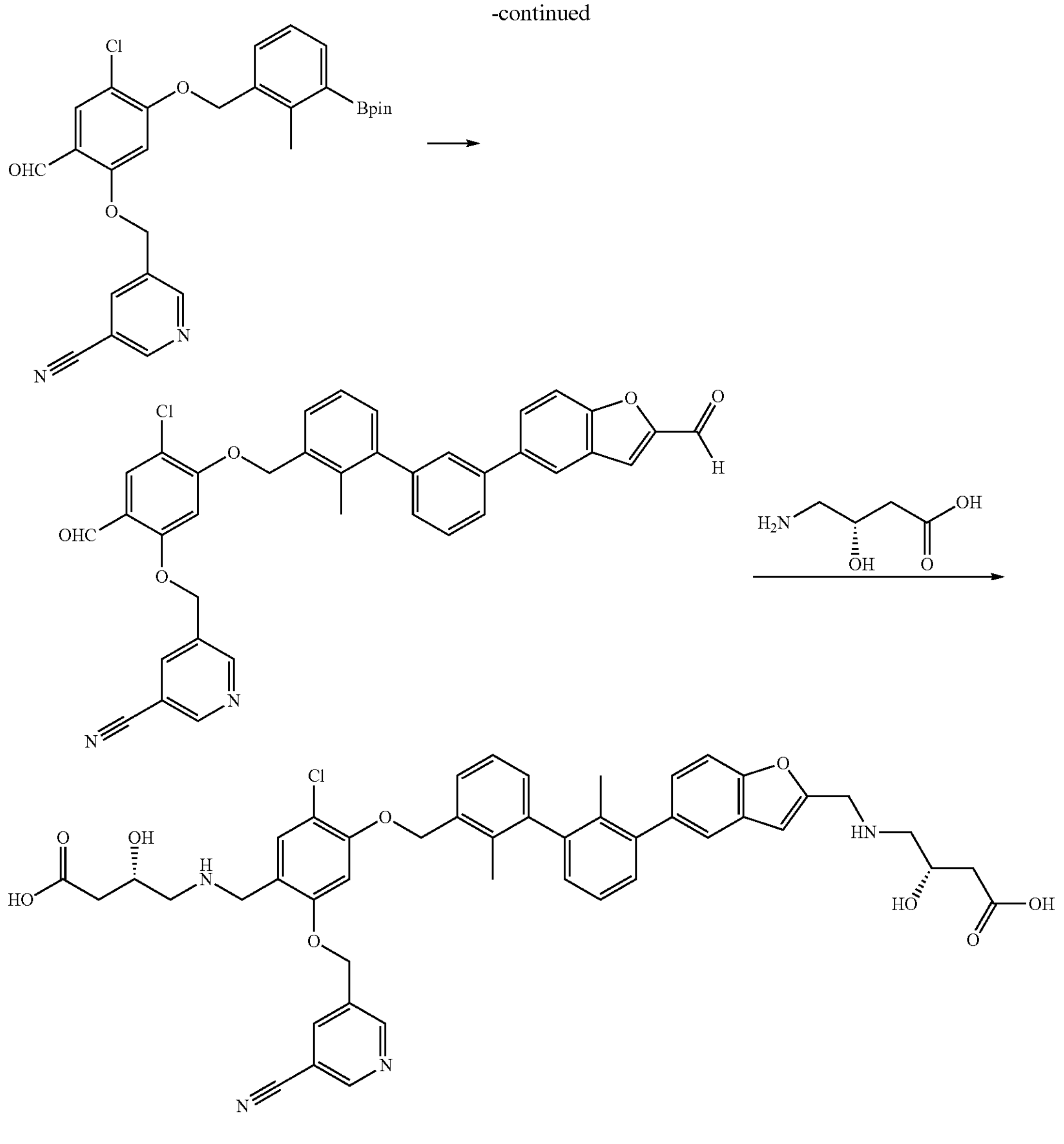

Step 1: To a solution of methyl 5-bromobenzofuran-2-carboxylate (250 mg, 0.98 mmol) in THF (20 mL) cooled in an ice-water bath was added 2M lithium borohydride (0.98 mL) then methanol (79 μL, 2.0 mmol). The reaction mixture was allowed to slowly warm to rt. Analysis by tlc indicated consumption of the starting material. The reaction mixture was quenched by the addition of sat $NaHCO_3$ and EtOAc. After stirring for 5 min (significant evolution of gas was observed), the layers were separated and the aqueous layer was further extracted with EtOAc. The organic layers were combined, washed with brine, dried (over $Na_2SO_4$), filtered then concentrated in vacuo. The crude mixture was processed in the next step immediately.

Step 2: To a solution of intermediate from the preceding step in dichloromethane (20 mL) cooled in an ice-water bath was added Dess-Martin periodinane (620 mg, 1.5 mmol). The reaction mixture was allowed to slowly warm to rt and left overnight. Analysis by TLC indicated consumption of the starting material. The reaction mixture was quenched by the addition of sat $NH_4Cl$ and EtOAc. The layers were separated and the aqueous layer was further extracted with EtOAc. The organic layers were combined, washed with brine, dried (over $Na_2SO_4$), filtered then concentrated in vacuo. The crude mixture was purified by $SiO_2$ column chromatography (ISCO gold, 12 g column; 0-50% EtOAc/Hex) to afford 5-bromobenzofuran-2-carbaldehyde.

Step 3: 5-bromobenzofuran-2-carbaldehyde (180 mg, 0.78 mmol), (3-Bromo-2-methylphenyl)boronic acid (210 mg, 0.97 mmol), potassium carbonate (320 mg, 2.3 mmol) and tetrakis(triphenylphosphine)palladium (90 mg, 0.078 mmol) were combined in a sealed vial. Dioxane (2.0 mL) and water (0.50 mL) were injected and the resulting suspension was sparged with argon (via a balloon filled with argon) for 10 minutes. The reaction mixture was stirred at 90° C. overnight. Analysis by tlc indicated consumption of the bromide starting material. The reaction mixture was cooled to rt, and quenched by the addition of sat $NH_4Cl$ and EtOAc. The layers were separated and the aqueous layer was further extracted with EtOAc. The organic layers were combined, washed with brine, dried (over $Na_2SO_4$), filtered then concentrated in vacuo. The crude mixture was purified by $SiO_2$ column chromatography (ISCO gold, 12 g column;

0-50% EtOAc/Hex) to afford 5-(3-bromo-2-methyl-phenyl) benzofuran-2-carbaldehyde (as a 2:1 mixture with the protodebromination by-product. $^1$H NMR signal of the $CH_3$ group: 2.30 and 2.19 ppm, respectively).

Step 4: 5-(3-bromo-2-methyl-phenyl)benzofuran-2-carbaldehyde (66%, 210 mg, 0.43 mmol), 5-[[4-chloro-2-formyl-5-[[2-methyl-3-(4,4,5,5-tetramethyl-1,3,2-dioxaborolan-2-yl)phenyl]methoxy]phenoxy]methyl]pyridine-3-carbonitrile (150 mg, 0.29 mmol), potassium carbonate (140 mg, 1.0 mmol) and tetrakis(triphenylphosphine)palladium (84 mg, 0.072 mmol) were combined in a sealed vial. Dioxane (2.0 mL) and water (0.50 mL) were injected and the resulting suspension was sparged with argon (via a balloon filled with argon) for 10 minutes. The reaction mixture was stirred at 100° C. for 2 h. Analysis by tlc/LCMS indicated consumption of the boronate starting material and formation of the desired product. The reaction mixture was cooled to rt, and quenched by the addition of sat $NH_4Cl$ and EtOAc. The layers were separated and the aqueous layer was further extracted with EtOAc. The organic layers were combined, washed with brine, dried (over $Na_2SO_4$), filtered then concentrated in vacuo. The crude mixture was purified by $SiO_2$ column chromatography (ISCO gold, 12 g column; 0-50% EtOAc/Hex) to afford 5-((4-chloro-2-formyl-5-((3'-(2-formylbenzofuran-5-yl)-2,2'-dimethyl-[1,1'-biphenyl]-3-yl) methoxy)phenoxy)methyl)nicotinonitrile (M+1=627).

Step 5: 5-((4-chloro-2-formyl-5-((3'-(2-formylbenzofuran-5-yl)-2,2'-dimethyl-[1,1'-biphenyl]-3-yl)methoxy) phenoxy)methyl)nicotinonitrile (35 mg, 0.056 mmol) from the preceding step was transformed to the desired product with (3S)-4-amino-3-hydroxy-butanoic acid (31 mg, 0.56 mmol) via reductive amination using a modified version of Procedure G (modification of the work-up as described). The crude mixture was concentrated in vacuo, then re-dissolved in DMF (2 mL) and TFA (0.1 mL). The resulting solution was purified by reverse-phase HPLC (10-90% MeCN/H2O+0.1% TFA) to afford (S)-4-(((5-(3'-((4-((((S)-3-carboxy-2-hydroxypropyl)amino)methyl)-2-chloro-5-((5-cyanopyridin-3-yl)methoxy)phenoxy)methyl)-2,2'-dimethyl-[1,1'-biphenyl]-3-yl)benzofuran-2-yl)methyl)amino)-3-hydroxybutanoic acid as the bis-TFA salt. $^1$H NMR (400 MHz, Methanol-$d_4$) δ 8.95 (d, J=2.1 Hz, 1H), 8.92 (d, J=2.0 Hz, 1H), 8.37 (t, J=2.1 Hz, 1H), 7.65-7.55 (m, 2H), 7.51 (s, 1H), 7.46 (d, J=7.2 Hz, 1H), 7.35 (dd, J=8.6, 1.7 Hz, 1H), 7.35-7.20 (m, 3H), 7.16 (d, J=7.6 Hz, 1H), 7.14-7.05 (m, 3H), 5.37 (s, 2H), 5.31 (s, 2H), 4.53 (d, J=15.0 Hz, 1H), 4.49 (d, J=14.1 Hz, 1H), 4.32 (ddt, J=12.8, 6.4, 3.0 Hz, 1H), 4.28-4.17 (m, 3H), 3.20 (dd, J=12.8, 3.1 Hz, 1H), 3.10 (dd, J=12.6, 9.9 Hz, 1H), 2.97 (dd, J=12.7, 9.8 Hz, 1H), 2.56 (d, J=6.3 Hz, 2H), 2.51 (dd, J=6.3, 1.2 Hz, 2H), 2.16 (s, 3H), 1.88 (s, 3H) (note: a proton coincided with the methanol (solvent) peak or was not detected and is thus not listed); $^{19}$F NMR (400 MHz, Methanol-d4) δ 77.7; ES/MS: M+1=833.02.

Example 211: (S)-4-(((5-(3'-((4-((((S)-3-carboxy-2-hydroxypropyl)amino)methyl)-3-((5-cyanopyridin-3-yl)methoxy)phenoxy)methyl)-2,2'-dimethyl-[1,1'-biphenyl]-3-yl)benzo[b]thiophen-2-yl)methyl) amino)-3-hydroxybutanoic acid 3.2

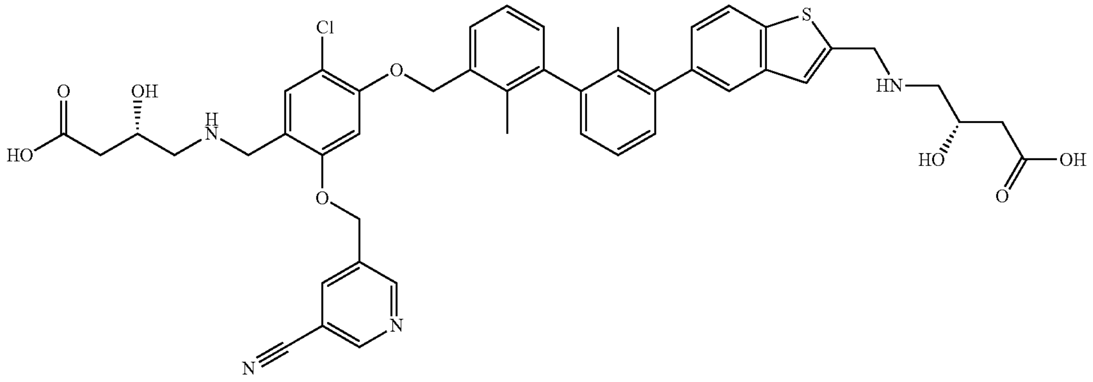 [SMILES: Cc1c(COc2cc(OCc3cncc(C#N)c3)c(CNC[C@@H](O)CC(=O)O)cc2Cl)cccc1-c1cccc(-c2ccc3sc(CNC[C@@H](O)CC(=O)O)cc3c2)c1C]

(S)-4-(((5-(3'-((4-((((S)-3-carboxy-2-hydroxypropyl) amino)methyl)-3-((5-cyanopyridin-3-yl)methoxy)phenoxy) methyl)-2,2'-dimethyl-[1,1'-biphenyl]-3-yl)benzo[b]thiophen-2-yl)methyl)amino)-3-hydroxybutanoic acid was prepared as the bis-TFA salt by a sequence identical to the route used to prepare Example 210 starting with methyl 5-bromobenzo[b]thiophene-2-carboxylate instead of 5-bromobenzofuran-2-carboxylate: $^1$H NMR (400 MHz, Methanol-$d_4$) δ 8.95 (d, J=2.1 Hz, 1H), 8.92 (d, J=2.0 Hz, 1H), 8.37 (t, J=2.1 Hz, 1H), 7.96 (d, J=8.3 Hz, 1H), 7.82 (d, J=1.6 Hz, 1H), 7.61 (s, 1H), 7.51 (s, 1H), 7.46 (d, J=7.5 Hz, 1H), 7.40 (dd, J=8.3, 1.7 Hz, 1H), 7.36-7.24 (m, 3H), 7.17 (dd, J=7.7, 1.4 Hz, 1H), 7.12 (dd, J=7.4, 1.6 Hz, 1H), 7.08 (s, 1H), 5.37 (s, 2H), 5.32 (s, 2H), 4.60 (s, 2H), 4.32 (dtd, J=9.5, 6.3, 3.0 Hz, 1H), 4.28-4.17 (m, 3H), 3.29-3.26 (m, 1H), 3.20 (dd, J=12.7, 3.1 Hz, 1H), 3.08 (dd, J=12.7, 9.9 Hz, 1H), 3.00-2.93 (m, 1H), 2.55 (d, J=6.3 Hz, 2H), 2.51 (dd, J=6.3, 1.1 Hz, 2H), 2.16 (s, 3H), 1.90 (s, 3H); 19F NMR (400 MHz, Methanol-d4) δ −77.7; ES/MS: M+1=849.29.

Example 212: (S)-4-((4-((3'-((4-((((S)-3-carboxy-2-hydroxypropyl)amino)methyl)-2-chloro-5-((6-cyano-pyridin-2-yl)methoxy)phenoxy)methyl)-2,2'-dimethyl-[1,1'-biphenyl]-3-yl)methoxy)-5-chloro-2-methoxybenzyl)amino)-3-hydroxybutanoic acid
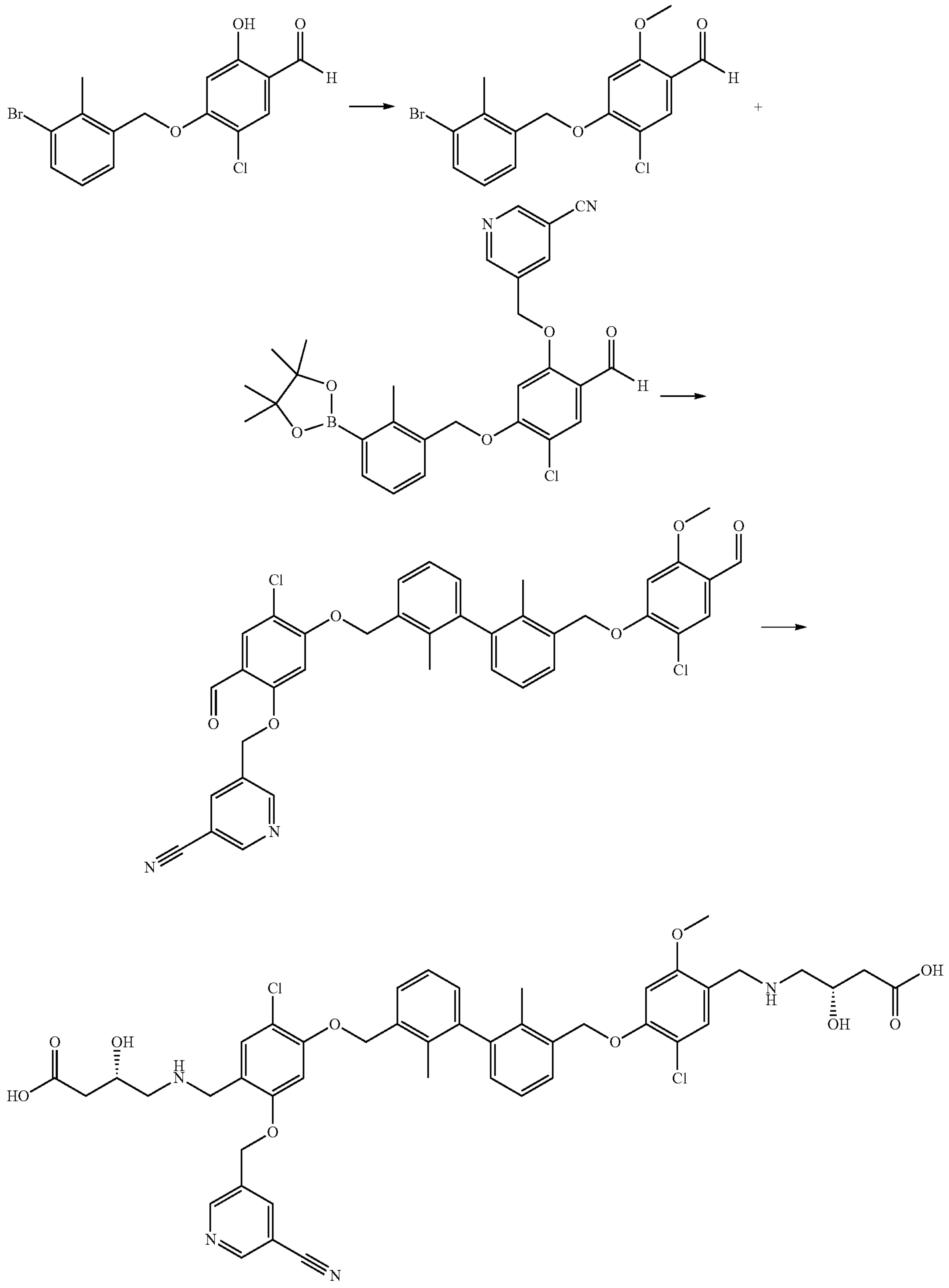

A solution of 4-((3-bromo-2-methylbenzyl)oxy)-5-chloro-2-hydroxybenzaldehyde (750 mg, 2.1 mmol) in 5 mL DMF under $N_2$ was treated with K2CO3 (585 mg, 2.5 mmol, 2 equiv) and the mixture stirred under $N_2$ at rt for 15 min. Iodomethane (0.39 mL, 6.3 mmol, 3 equiv) was added and the reaction stirred under $N_2$ at 40° C. for 4h. The mixture was diluted with water and extracted with EtOAc (2×), then washed with saturated $NH_4Cl$ solution, dried over MgSO4, filtered and concentrated under reduced pressure to yield. 4-((3-bromo-2-methylbenzyl)oxy)-5-chloro-2-methoxybenzaldehyde as a solid. [M+H]=370.88.

A mixture of 3-((4-chloro-2-formyl-5-((2-methyl-3-(4,4,5,5-tetramethyl-1,3,2-dioxaborolan-2-yl)benzyl)oxy)phenoxy)methyl)benzonitrile (280 mg, 0.54 mmol), 4-((3-bromo-2-methylbenzyl)oxy)-5-chloro-2-methoxybenzaldehyde (200 mg, 0.54 mmol), Pd(dppf)$Cl_2CH_2Cl_2$ (55 mg, 0.068 mmol, 0.125 equiv) and potassium carbonate (80 mg, 0.81 mmol, 1.5 equiv) were placed in a microwave vial along with DMF (9 mL) and water (1 mL) and heated to 100° C. in a microwave for 30 min. After cooling to room temperature, the reaction was diluted with EtOAc and water. The organic layer was separated, dried with $Na_2SO_4$ and concentrated. Purified by silica gel chromatography (eluting with DCM-MeOH) to provide 5-((4-chloro-5-((3'-((2-chloro-4-formyl-5-methoxyphenoxy)methyl)-2,2'-dimethyl-[1,1'-biphenyl]-3-yl)methoxy)-2-formylphenoxy)methyl)nicotinonitrile. [M+H]=681.04.

The title compound was synthesized from 5-((4-chloro-5-((3'-((2-chloro-4-formyl-5-methoxyphenoxy)methyl)-2,2'-dimethyl-[1,1'-biphenyl]-3-yl)methoxy)-2-formylphenoxy)methyl)nicotinonitrile in a manner similar to general reductive amination procedure A. $^1$H NMR (400 MHz, Methanol-$d_4$) δ 8.94 (dd, J=14.7, 2.0 Hz, 2H), 8.38 (t, J=2.1 Hz, 1H), 7.56-7.37 (m, 4H), 7.27 (q, J=7.4 Hz, 2H), 7.18-7.02 (m, 3H), 6.95 (s, 1H), 5.37 (s, 2H), 5.31 (s, 3H), 4.39-4.13 (m, 7H), 3.96 (s, 3H), 3.19 (ddd, J=12.2, 8.8, 3.1 Hz, 2H), 2.97 (ddd, J=12.7, 9.8, 2.7 Hz, 2H), 2.52 (dd, J=7.8, 6.2 Hz, 4H), 2.08 (d, J=1.9 Hz, 6H).

Example 213: (2S,2'S)-3,3'-((((((2,2'-dimethyl-[1,1'-biphenyl]-3,3'-diyl)bis(methylene))bis(oxy))bis(5-chloro-2-((5-cyanopyridin-3-yl)methoxy)-4,1-phenylene))bis(methylene))bis(azanediyl))bis(2-hydroxypropanoic acid)

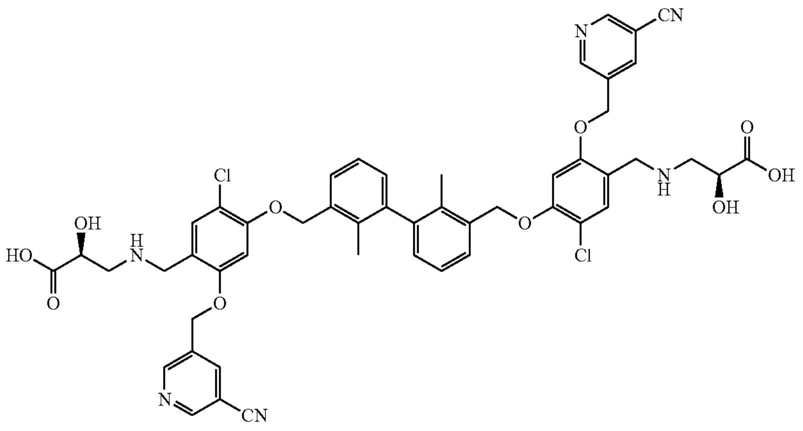 [SMILES: Cc1c(COc2cc(OCc3cncc(C#N)c3)c(CNC[C@H](O)C(=O)O)cc2Cl)cccc1-c1cccc(COc2cc(OCc3cncc(C#N)c3)c(CNC[C@H](O)C(=O)O)cc2Cl)c1C]

The title compound was synthesized from Intermediate 12 in a manner similar to general reductive amination procedure A. $^1$H NMR (400 MHz, Methanol-$d_4$) δ 8.94 (dd, J=15.1, 2.0 Hz, 4H), 8.37 (t, J=2.1 Hz, 2H), 7.48 (d, J=21.4 Hz, 4H), 7.26 (t, J=7.6 Hz, 2H), 7.16-7.05 (m, 4H), 5.38 (s, 4H), 5.31 (s, 4H), 4.40 (dd, J=8.7, 3.9 Hz, 2H), 4.26 (d, J=1.8 Hz, 4H), 3.36 (dd, J=12.9, 4.0 Hz, 4H), 3.17 (dd, J=12.9, 8.8 Hz, 4H), 2.08 (s, 6H). 19F NMR (376 MHz, Methanol-d4) δ −77.68 (d, J=7.6 Hz). [M+H]=961.15.

Example 214: (3S,3'S)-4,4'-((((((2,2'-dimethyl-[1,1'-biphenyl]-3,3'-diyl)bis(methylene))bis(oxy))bis(5-chloro-2-methoxy-4,1-phenylene))bis(methylene))bis(azanediyl))bis(3-hydroxybutanoic acid)

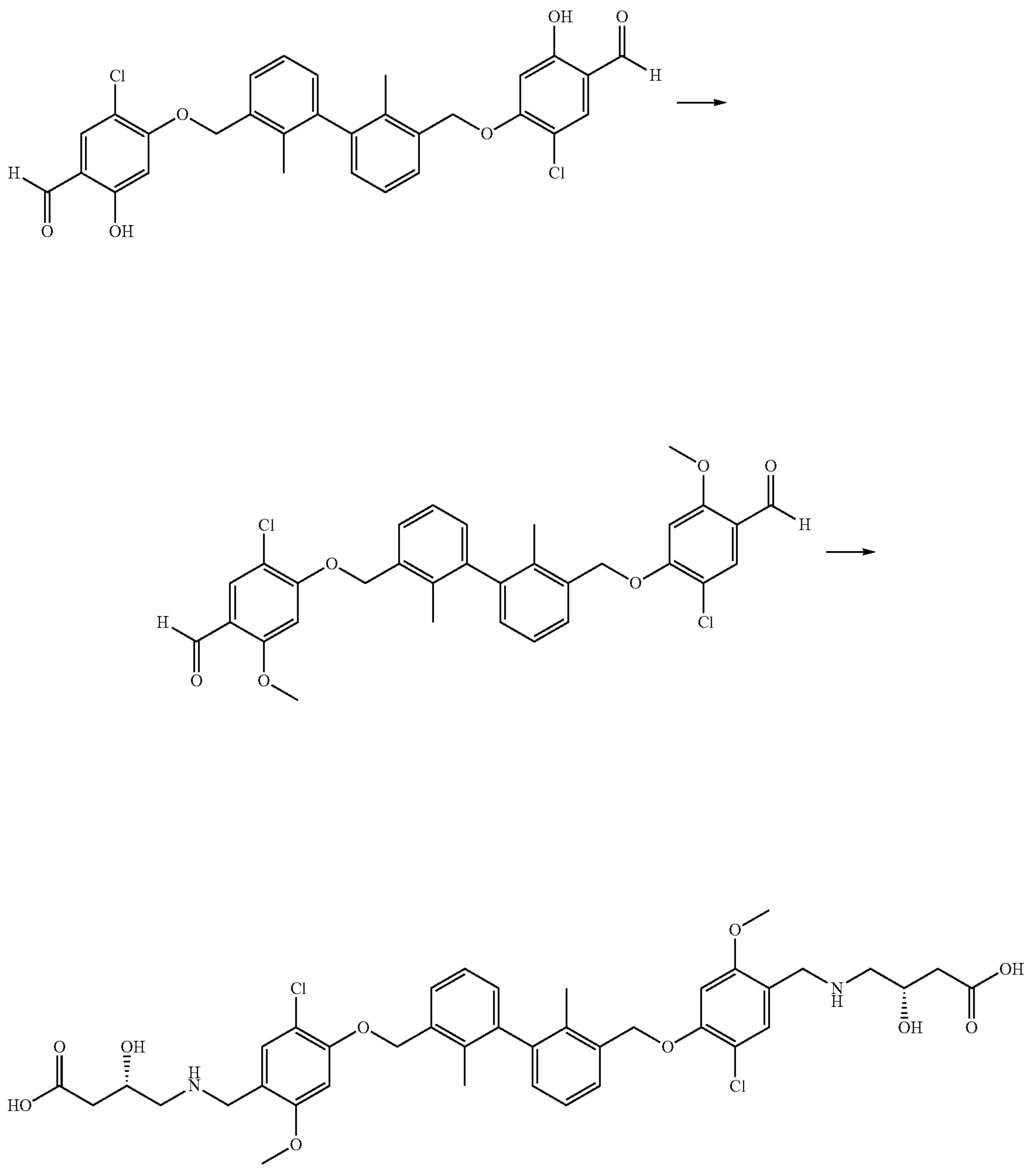

A solution of 4,4'-(((2,2'-dimethyl-[1,1'-biphenyl]-3,3'-diyl)bis(methylene))bis(oxy))bis(5-chloro-2-hydroxybenzaldehyde) (550 mg, 0.99 mmol) in 5 mL DMF under $N_2$ was treated with CS2CO3 (975 mg, 2.99 mmol, 3 equiv) and the mixture stirred under $N_2$ at rt for 15 min. Iodomethane (0.25 mL, 3.99 mmol, 4 equiv) was added and the reaction stirred under $N_2$ at 40° C. for 6 h. The mixture was diluted with water and extracted with EtOAc (2×), then washed with saturated NH4Cl solution, dried over MgSO4, filtered and concentrated under reduced pressure. Purification was carried out with by ISCO (Hex/EtOAc) provided 4,4'-(((2,2'-dimethyl-[1,1'-biphenyl]-3,3'-diyl)bis(methylene))bis(oxy))bis(5-chloro-2-methoxybenzaldehyde) as a solid. [M+H]=580.62.

The title compound was synthesized from 4,4'-(((2,2'-dimethyl-[1,1'-biphenyl]-3,3'-diyl)bis(methylene))bis(oxy))bis(5-chloro-2-methoxybenzaldehyde) in a manner similar to general reductive amination procedure A. $^1$H NMR (400 MHz, DMSO-$d_6$) δ 7.56-7.47 (m, 2H), 7.30 (t, J=7.6 Hz, 1H), 7.14-7.07 (m, 1H), 7.04 (s, 1H), 5.33 (d, J=2.2 Hz, 2H), 4.14 (s, 1H), 4.02 (s, 2H), 3.88 (s, 3H), 3.37 (s, 2H), 2.95 (d, J=12.7 Hz, 1H), 2.85-2.75 (m, 1H), 2.35 (dd, J=15.8, 7.2 Hz, 1H), 2.02 (s, 3H). 19F NMR (376 MHz, DMSO-d6) δ −73.95. [M+H]=785.18

Example 215: (2S,2'S)-4,4'-((((((2,2'-dimethyl-[1,1'-biphenyl]-3,3'-diyl)bis(methylene))bis(oxy))bis(5-chloro-2-((5-cyanopyridin-3-yl)methoxy)-4,1-phenylene))bis(methylene))bis(azanediyl))bis(2-hydroxybutanoic acid)

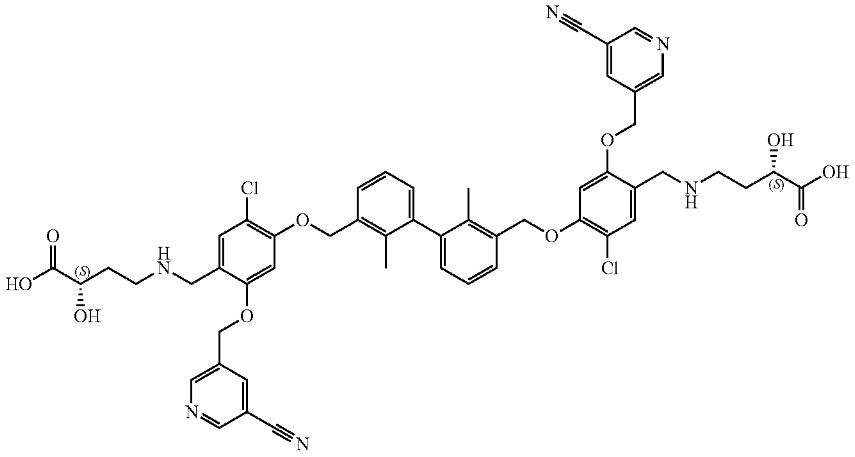

The title compound was synthesized from Intermediate 12 in a manner similar to general reductive amination procedure A. $^{1}H$ NMR (400 MHz, DMSO-$d_6$) δ 9.02 (t, J=2.4 Hz, 2H), 8.63-8.34 (m, 4H), 7.56 (s, 2H), 7.48 (d, J=7.4 Hz, 2H), 7.28 (t, J=7.6 Hz, 2H), 7.19 (s, 2H), 7.10 (d, J=7.2 Hz, 2H), 5.56 (s, 2H), 5.44-5.18 (m, 8H), 4.13 (s, 6H), 4.04 (dd, J=8.5, 4.0 Hz, 4H), 2.99 (s, 6H), 2.02 (s, 8H). $^{19}F$ NMR (376 MHz, DMSO-d6) δ −74.33. [M+H]=989.50.

Example 216: (S)-3-((4-((3'-((4-((((S)-2-carboxy-2-hydroxyethyl)amino)methyl)-2-chloro-5-((5-cyanopyridin-3-yl)methoxy)phenoxy)methyl)-2,2'-dimethyl-[1,1'-biphenyl]-3-yl)methoxy)-5-chloro-2-methoxybenzyl)amino)-2-hydroxypropanoic acid

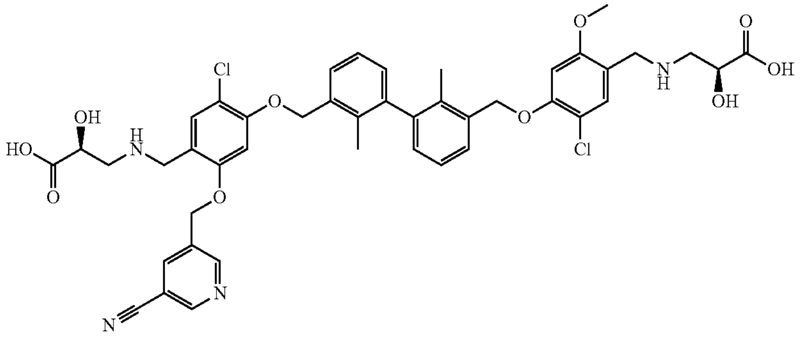 [SMILES: COc1cc(OCc2cccc(-c3cccc(COc4cc(OCc5cncc(C#N)c5)c(CNC[C@H](O)C(=O)O)cc4Cl)c3C)c2C)c(Cl)cc1CNC[C@H](O)C(=O)O]

The title compound was synthesized from 5-((4-chloro-5-((3'-((2-chloro-4-formyl-5-methoxyphenoxy)methyl)-2,2'-dimethyl-[1,1'-biphenyl]-3-yl)methoxy)-2-formylphenoxy)methyl)nicotinonitrile in a manner similar to general reductive amination procedure A. $^{1}H$ NMR (400 MHz, Methanol-$d_4$) δ 8.95 (d, J=15.3 Hz, 4H), 7.56-7.35 (m, 4H), 7.27 (q, J=7.3 Hz, 2H), 7.19-7.05 (m, 2H), 6.96 (s, 2H), 5.38 (s, 2H), 5.32 (s, 3H), 4.43 (ddd, J=19.4, 8.8, 3.9 Hz, 2H), 4.30-4.15 (m, 4H), 3.97 (s, 3H), 3.44-3.35 (m, 3H), 3.17 (ddd, J=12.9, 8.9, 3.9 Hz, 3H), 2.09 (d, J=2.2 Hz, 6H). 19F NMR (376 MHz, Methanol-d4) δ −77.74. [M+H]=859.26.

Example 217: (4-((3'-((4-(((carboxymethyl)amino) methyl)-2-chloro-5-((5-cyanopyridin-3-yl)methoxy) phenoxy)methyl)-2,2'-dimethyl-[1,1'-biphenyl]-3-yl) methoxy)-5-chloro-2-methoxybenzyl)glycine

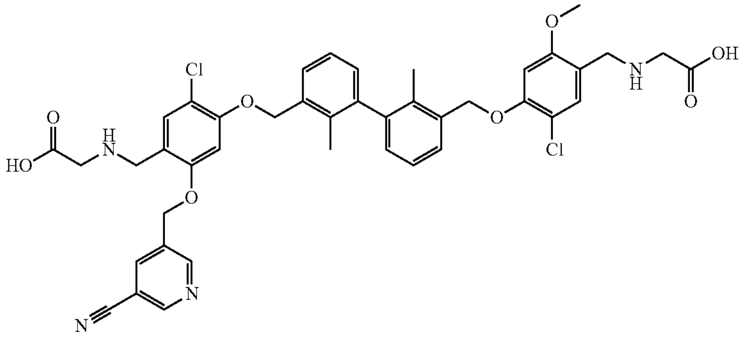 [SMILES: COc1cc(OCc2cccc(-c3cccc(COc4cc(OCc5cncc(C#N)c5)c(CNCC(=O)O)cc4Cl)c3C)c2C)c(Cl)cc1CNCC(=O)O]

The title compound was synthesized from 5-((4-chloro-5-((3'-((2-chloro-4-formyl-5-methoxyphenoxy)methyl)-2,2'-dimethyl-[1,1'-biphenyl]-3-yl)methoxy)-2-formylphenoxy)methyl)nicotinonitrile in a manner similar to general reductive amination procedure A. $^1$H NMR (400 MHz, Methanol-$d_4$) δ 8.94 (d, J=16.3 Hz, 4H), 8.39 (t, J=2.1 Hz, 2H), 7.59-7.45 (m, 2H), 7.42 (s, 2H), 7.27 (q, J=7.3 Hz, 4H), 7.17-7.04 (m, 2H), 5.38 (s, 2H), 5.32 (s, 3H), 4.27 (s, 1H), 4.20 (s, 2H), 3.96 (s, 2H), 3.84 (d, J=8.6 Hz, 3H), 2.09 (d, J=1.6 Hz, 6H). 19F NMR (376 MHz, Methanol-d4) δ −77.71. [M+H]=799.11.

Example 218: 4,4'-((((((2,2'-dimethyl-[1,1'-biphenyl]-3,3'-diyl)bis(methylene))bis(oxy))bis(5-chloro-2-((5-cyanopyridin-3-yl)methoxy)-4,1-phenylene)) bis(methylene))bis(azanediyl))bis(3-hydroxy-3-methylbutanoic acid)

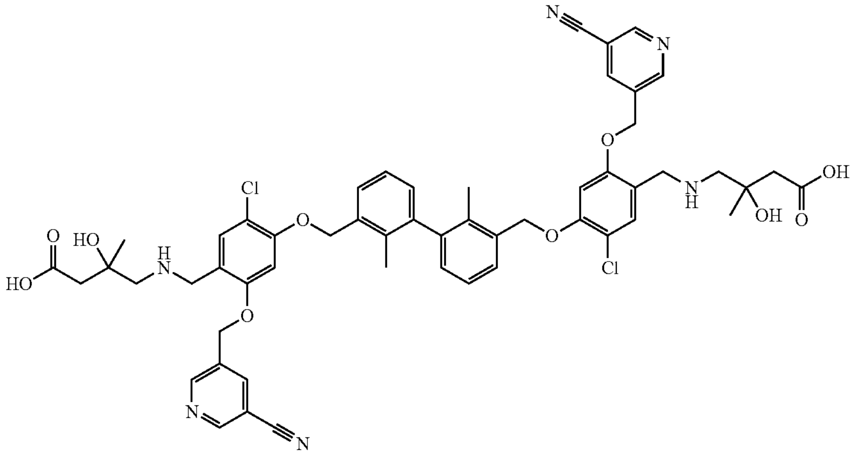 [SMILES: Cc1c(COc2cc(OCc3cncc(C#N)c3)c(CNCC(C)(O)CC(=O)O)cc2Cl)cccc1-c1cccc(COc2cc(OCc3cncc(C#N)c3)c(CNCC(C)(O)CC(=O)O)cc2Cl)c1C]

The title compound was synthesized from Intermediate 12 in a manner similar to general reductive amination procedure A. $^1$H NMR (400 MHz, Methanol-$d_4$) δ 8.95 (dd, J=16.2, 2.0 Hz, 6H), 8.38 (t, J=2.1 Hz, 4H), 7.48 (d, J=15.8 Hz, 4H), 7.27 (t, J=7.6 Hz, 2H), 7.17-6.95 (m, 4H), 5.38 (s, 2H), 5.31 (s, 2H), 4.40-4.05 (m, 4H), 3.25 (d, J=12.7 Hz, 2H), 3.08 (d, J=12.7 Hz, 2H), 2.67-2.49 (m, 4H), 2.09 (s, 6H), 1.31 (s, 6H). 19F NMR (376 MHz, Methanol-d4) δ −77.67. [M+H]=1017.32.

Example 219: (3S,3'S)-4,4'-((((((2,2'-dimethyl-[1,1'-biphenyl]-3,3'-diyl)bis(methylene))bis(oxy))bis(5-chloro-2-((2-cyanopyridin-4-yl)methoxy)-4,1-phenylene))bis(methylene))bis(azanediyl))bis(3-hydroxybutanoic acid)
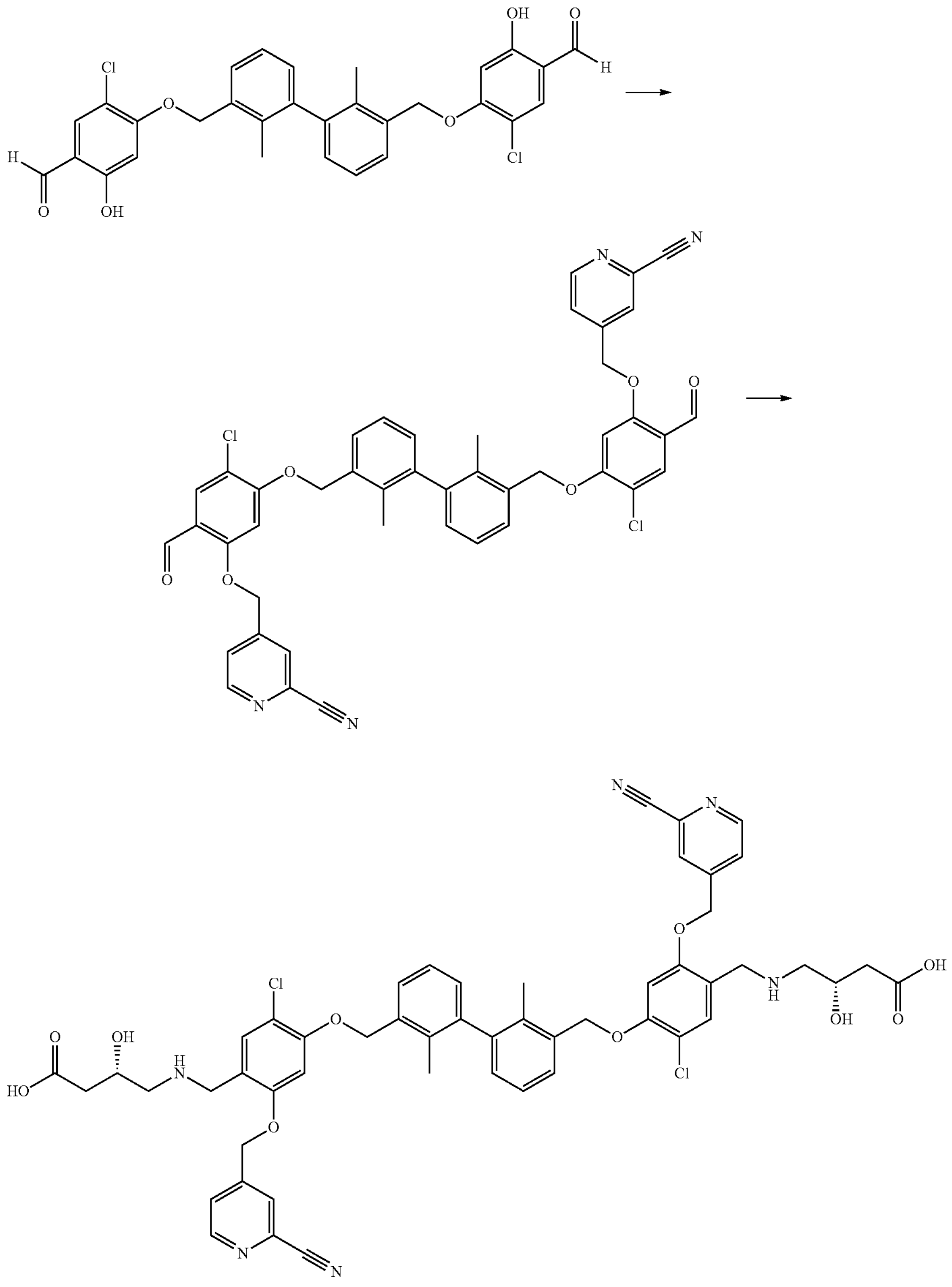

The title compound was synthesized in analogy to Example 214, using 4-(chloromethyl)picolinonitrile instead of methyl iodide. $^1$H NMR (400 MHz, Methanol-d4) δ 8.71 (ddd, J=12.2, 5.1, 0.8 Hz, 2H), 8.01 (dd, J=1.7, 0.8 Hz, 2H), 7.79 (dd, J=5.1, 1.6 Hz, 2H), 7.52 (s, 2H), 7.40 (dd, J=7.7, 1.4 Hz, 2H), 7.23 (t, J=7.6 Hz, 2H), 7.09 (dd, J=7.7, 1.4 Hz, 2H), 6.97 (s, 2H), 5.40 (s, 4H), 5.33 (s, 2H), 5.28 (s, 4H), 4.41-4.24 (m, 6H), 3.25 (dd, J=12.7, 3.0 Hz, 2H), 3.03 (dd, J=12.7, 9.8 Hz, 2H), 2.54 (d, J=6.3 Hz, 4H), 2.09 (s, 6H). 19F NMR (376 MHz, Methanol-d4) δ −77.74. [M+H] =989.35.

Example 220: (3S,3'S)-4,4'-((((((2,2'-dimethyl-[1,1'-biphenyl]-3,3'-diyl)bis(methylene))bis(oxy))bis(5-chloro-2-((3,5-dicyanobenzyl)oxy)-4,1-phenylene))bis(methylene))bis(azanediyl))bis(3-hydroxybutanoic acid)

Into a flask containing 3,5-Dicyanotoluene (0.5 g, 3.52 mmol, obtained from Alfa-Aeser, Ward Hill, Mass., USA) was added NBS (0.75 g, 4.22 mmol, 1.1 equiv), 2,2'-Azobisisobutyronitrile, 98% (0.12 g, 0.7 mmol, 0.2 equiv. and $CCl_4$ (10 mL). The solution was heated to 85 C for 16 hr. After cooling, the mixture was filtered and the filtrate concentrated under reduced pressure. Purification was carried out with by ISCO (Hex/EtOAc) provided of 5-(bromomethyl)isophthalonitrile. $^1$H NMR (400 MHz, CDCl3) δ 7.87 (s, 2H), 7.69 (s, 1H), 4.48 (s, 2H).

The title compound was synthesized in analogy to Example 214. $^1$H NMR (400 MHz, Methanol-$d_4$) δ 8.20 (s, 2H), 7.51 (s, 2H), 7.45 (d, J=7.4 Hz, 2H), 7.26 (t, J=7.6 Hz, 2H), 7.11 (dd, J=7.7, 1.4 Hz, 2H), 7.01 (s, 2H), 5.36 (s, 4H), 5.29 (s, 4H), 4.26 (s, 4H), 3.21 (dd, J=12.8, 3.0 Hz, 4H), 2.99 (dd, J=12.7, 9.8 Hz, 4H), 2.53 (dd, J=6.3, 1.5 Hz, 6H), 2.07 (s, 6H). $^{19}$F NMR (376 MHz, Methanol-$d_4$) δ −77.65. [M+H]=1037.18.

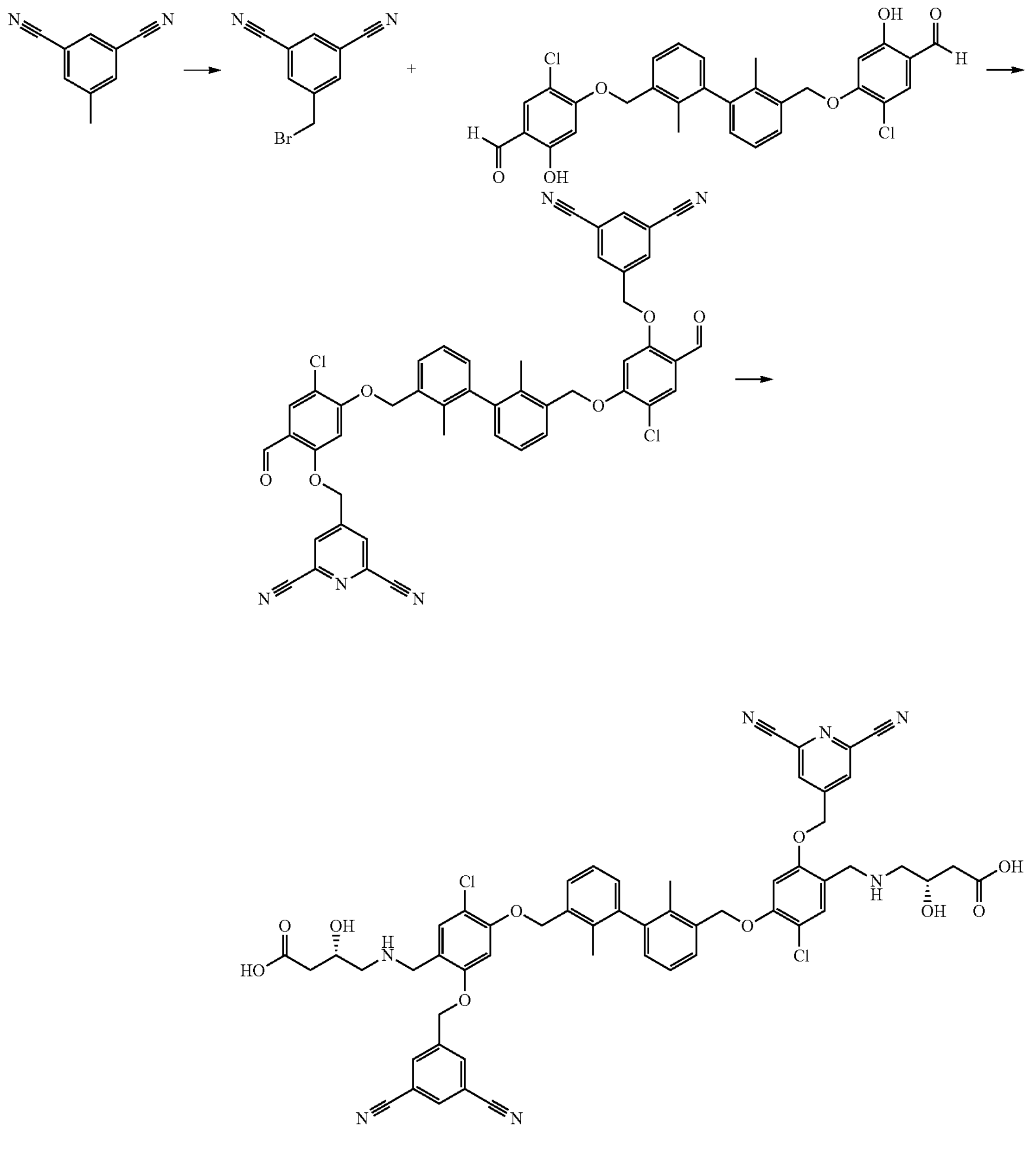

Example 221: (3S,3'S)-4,4'-((((((2,2'-dimethyl-[1,1'-biphenyl]-3,3'-diyl)bis(methylene))bis(oxy))bis(5-chloro-2-((6-cyanopyridin-2-yl)methoxy)-4,1-phenylene))bis(methylene))bis(azanediyl))bis(3-hydroxybutanoic acid)

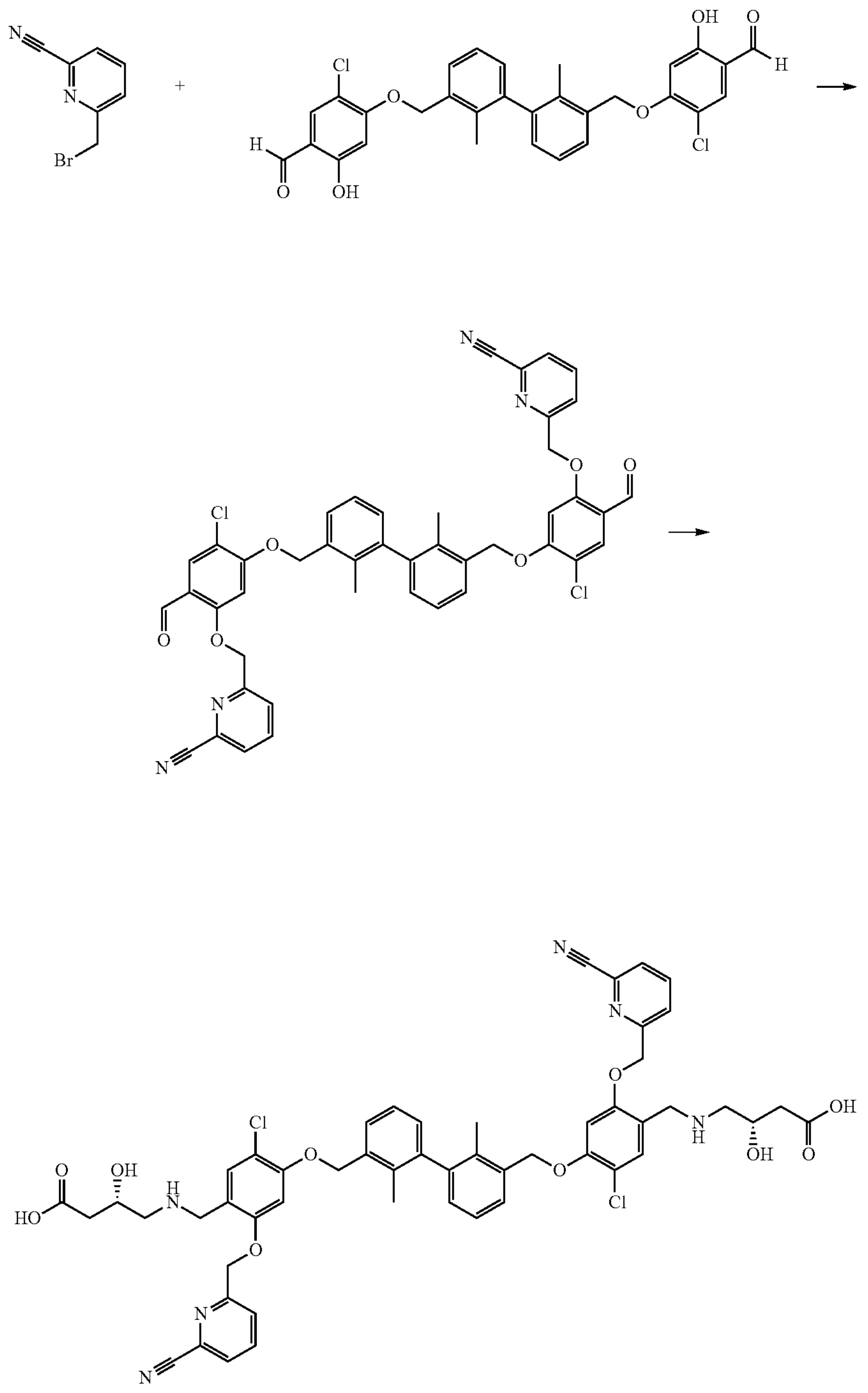

The title compound was synthesized in analogy to Example 214 using 6-(bromomethyl)picolinonitrile instead of methyl iodide. $^{1}$HNMR (400 MHz, Methanol-d4) δ 8.07 (t, J=7.9 Hz, 2H), 7.87 (dd, J=7.9, 3.7 Hz, 4H), 7.51-7.40 (m, 2H), 7.24 (t, J=7.6 Hz, 4H), 7.13-7.02 (m, 4H), 5.44 (s, 4H), 5.27 (s, 4H), 4.30 (dd, J=10.4, 5.0 Hz, 4H), 3.26 (d, J=3.0 Hz, 2H), 3.06 (dd, J=12.8, 9.9 Hz, 2H), 2.54 (d, J=6.3 Hz, 2H), 2.07 (s, 6H). $^{19}$F NMR (376 MHz, Methanol-$d_4$) δ −77.54. [M+H]=989.18.

Example 222: (3S,3'S)-4,4'-((((((2,2'-dimethyl-[1,1'-biphenyl]-3,3'-diyl)bis(methylene))bis(oxy))bis(2-((5-carbamoylpyridin-3-yl)methoxy)-5-chloro-4,1-phenylene))bis(methylene))bis(azanediyl))bis(3-hydroxybutanoic acid)

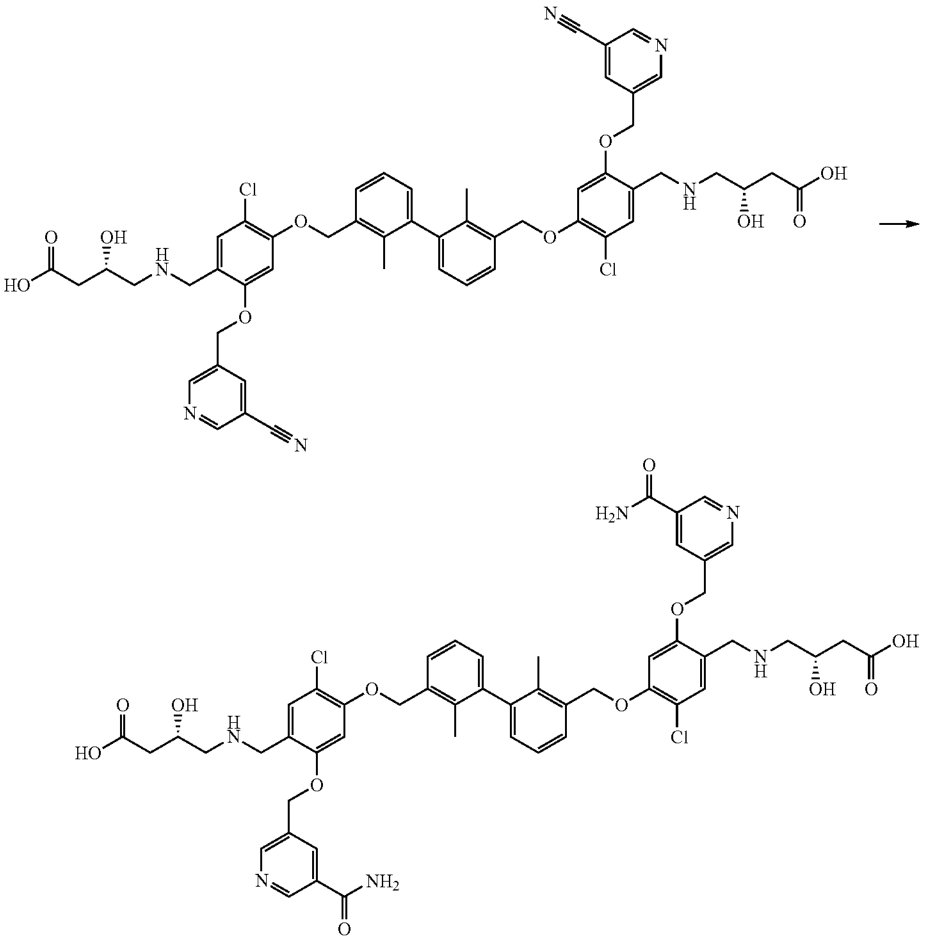

Into a flask containing compound of Example 66 ((S)-4-((4-((3'-((4-((((R)-2-carboxy-2-hydroxyethyl)amino)methyl)-2-chloro-5-((5-cyanopyridin-3-yl)methoxy)phenoxy)methyl)-2,2'-dimethyl-[1,1'-biphenyl]-3-yl)methoxy)-5-chloro-2-((5-cyanopyridin-3-yl)methoxy)benzyl)amino)-3-hydroxybutanoic acid (20 mg, 0.020 mmol) was added DMSO (3 mL), Hydrogen peroxide (0.01 mL, 0.05 mmol) and Potassium carbonate (5.66 mg, 0.04 mmol). The reaction was allowed to stir for several hours after which reaction was complete. It was directly purified by RP-HPLC to furnish the titled compound. $^1$H NMR (400 MHz, Methanol-$d_4$) δ 9.05 (s, 2H), 8.87 (s, 2H), 8.50 (q, J=3.3, 2.1 Hz, 2H), 7.52-7.43 (m, 3H), 7.26 (t, J=7.6 Hz, 2H), 7.12 (d, J=1.3 Hz, 2H), 7.10 (d, J=3.3 Hz, 2H), 5.40 (s, 4H), 5.31 (s, 4H), 4.30-4.18 (m, 6H), 3.21 (dd, J=12.8, 3.1 Hz, 2H), 2.99 (dd, J=12.7, 9.8 Hz, 2H), 2.52 (d, J=6.3 Hz, 4H), 2.08 (s, 6H). $^{19}$F NMR (376 MHz, Methanol-$d_4$) δ −78.03. bis TFA salt. [M+H]=1025.2.

Example 223: 2,2'-((((((2,2'-dimethyl-[1,1'-biphenyl]-3,3'-diyl)bis(methylene))bis(oxy))bis(3-(trifluoromethyl)-4,1-phenylene))bis(methylene))bis(azanediyl))bis(ethan-1-ol)

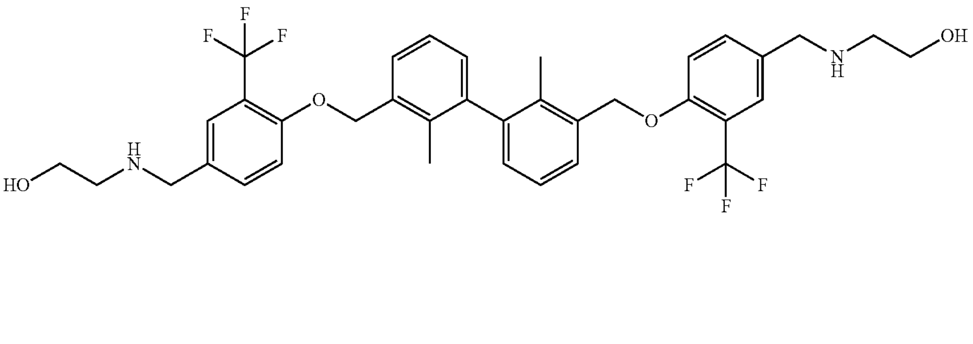 [SMILES: Cc1c(COc2ccc(CNCCO)cc2C(F)(F)F)cccc1-c1cccc(COc2ccc(CNCCO)cc2C(F)(F)F)c1C]

The title compound was synthesized rom Intermediate 37 in a manner similar to genera reductive amination procedure A. $^{1}H$ NMR (400 MHz, DMSO-$d_6$) δ 12.34 (s, 2H), 8.80 (s, 2H), 7.85 (d, J=2.1 Hz, 2H), 7.77 (dd, J=8.4, 2.2 Hz, 2H), 7.61-7.44 (m, 4H), 7.29 (t, J=7.6 Hz, 2H), 7.08 (dd, J=7.8, 1.4 Hz, 2H), 5.58 (s, 2H), 5.32 (d, J=2.4 Hz, 4H), 4.17 (s, 2H), 3.02 (s, 2H), 2.86 (d, J=10.2 Hz, 2H), 2.44-2.27 (m, 2H), 1.97 (s, 6H). $^{19}F$ NMR (376 MHz, DMSO-$d_6$) δ −61.48, −74.03 (d, J=4.2 Hz). [M+H]=677.2.

Example 224: (3S,3'S)-4,4'-((((((2,2'-dimethyl-[1,1'-biphenyl]-3,3'-diyl)bis(methylene))bis(oxy))bis(3-(trifluoromethyl)-4,1-phenylene))bis(methylene))bis(azanediyl))bis(3-hydroxybutanoic acid)

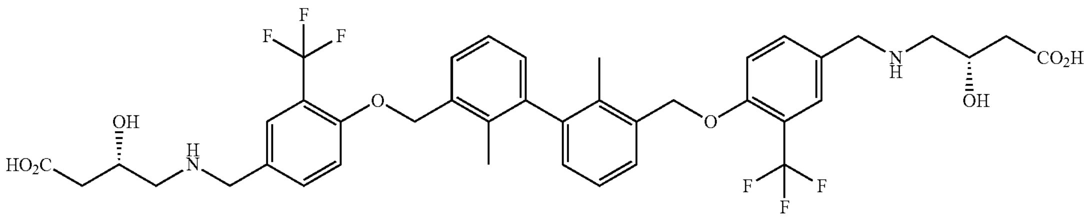 [SMILES: Cc1c(COc2ccc(CNC[C@@H](O)CC(=O)O)cc2C(F)(F)F)cccc1-c1cccc(COc2ccc(CNC[C@@H](O)CC(=O)O)cc2C(F)(F)F)c1C]

The title compound was synthesized from Intermediate 37 in a manner similar to general reductive amination procedure A. $^{1}H$ NMR (400 MHz, DMSO-$d_6$) δ 12.34 (s, 2H), 8.80 (s, 2H), 7.85 (d, J=2.1 Hz, 2H), 7.77 (dd, J=8.4, 2.2 Hz, 2H), 7.61-7.44 (m, 2H), 7.29 (t, J=7.6 Hz, 2H), 7.08 (dd, J=7.8, 1.4 Hz, 2H), 5.58 (s, 4H), 5.32 (d, J=2.4 Hz, 4H), 4.17 (s, 4H), 3.02 (s, 2H), 2.86 (d, J=10.2 Hz, 2H), 2.44-2.27 (m, 4H), 1.97 (s, 6H). $^{19}F$ NMR (376 MHz, DMSO-$d_6$) δ −61.48, −74.03 (d, J=4.2 Hz). [M+H]=793.32.

Example 225: (3S,3'S)-4,4'-((((((2,2'-dimethyl-[1,1'-biphenyl]-3,3'-diyl)bis(methylene))bis(oxy))bis(5-chloro-2-((4-cyanopyridin-2-yl)methoxy)-4,1-phenylene))bis(methylene))bis(azanediyl))bis(3-hydroxybutanoic acid)

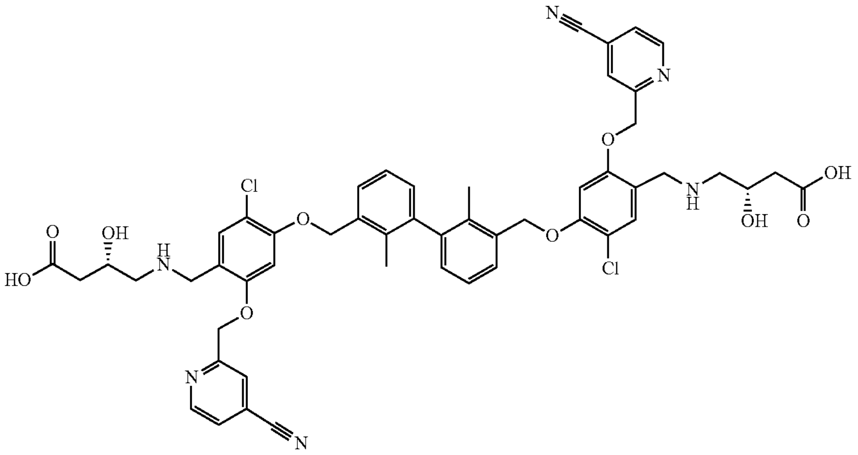 [SMILES: Cc1c(COc2cc(OCc3cc(C#N)ccn3)c(CNC[C@@H](O)CC(=O)O)cc2Cl)cccc1-c1cccc(COc2cc(OCc3cc(C#N)ccn3)c(CNC[C@@H](O)CC(=O)O)cc2Cl)c1C]

The title compound was synthesized in analogy to Example 214 using 2-(chloromethyl)isonicotinonitrile instead of methyl iodide. $^{1}H$ NMR (400 MHz, Methanol-$d_4$) δ 8.82 (dd, J=5.1, 0.9 Hz, 2H), 7.92 (t, J=1.2 Hz, 2H), 7.71 (dd, J=5.1, 1.5 Hz, 2H), 7.48 (s, 2H), 7.42 (dd, J=7.6, 1.4 Hz, 2H), 7.23 (t, J=7.6 Hz, 2H), 7.13-7.04 (m, 3H), 5.49 (s, 4H), 5.26 (s, 4H), 4.33 (td, J=6.5, 3.1 Hz, 2H), 4.28 (s, 4H), 3.34 (s, 3H), 3.26 (dd, J=12.7, 3.0 Hz, 2H), 3.07 (dd, J=12.7, 9.9 Hz, 2H), 2.55 (d, J=6.3 Hz, 4H), 2.05 (s, 6H). [M+H]=989.30.

Example 226: (1R,1'R,2S,2'S)-2,2'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(cyclopentan-1-ol) (or (1R,1'R,2S,2'S)-2,2'-(((6,6'-(((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(cyclopentan-1-ol))

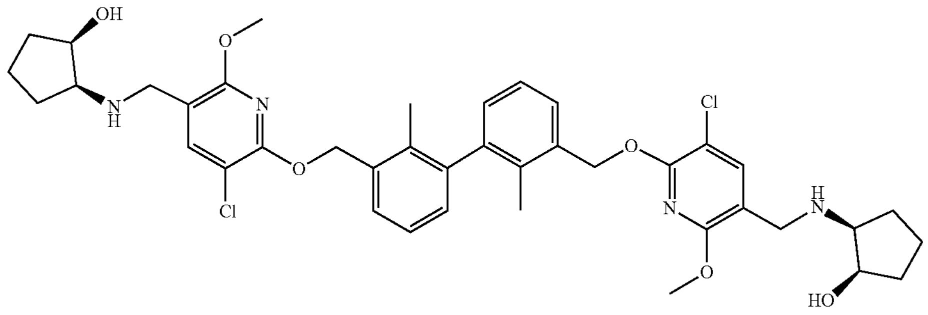 [SMILES: COc1nc(OCc2cccc(-c3cccc(COc4nc(OC)c(CN[C@H]5CCC[C@H]5O)cc4Cl)c3C)c2C)c(Cl)cc1CN[C@H]1CCC[C@H]1O]

To a solution of 6,6'-(((2,2'-dimethyl-[1,1'-biphenyl]-3,3'-diyl)bis(methylene))bis(oxy))bis(5-chloro-2-methoxynicotinaldehyde) (60 mg, 0.10 mmol) in DMF (1 mL) was added (1R,2S)-2-aminocyclopentan-1-ol (142 mg, 1.03 mmol). The mixture was stirred at rt for 1 h, then $NaBH(OAc)_3$ (219 mg, 1.03 mmol) was added. The mixture was stirred for an additional 2 h, then TFA was added until the reaction mixture reached pH 5 (ca. 0.1 mL). The mixture was filtered and purified via preparative reverse-phase HPLC (5-95% MeCN in $H_2O$) to yield the product as a solid. $^1H$ NMR (400 MHz, Methanol-$d_4$) δ 7.81 (s, 2H), 7.46 (d, J=7.5 Hz, 2H), 7.23 (t, J=7.6 Hz, 2H), 7.06 (d, J=7.5 Hz, 2H), 5.58 (s, 4H), 4.40-4.29 (m, 2H), 4.13 (q, J=13.3 Hz, 4H), 4.03 (s, 6H), 3.42 (td, J=8.8, 4.8 Hz, 2H), 3.30 (dt, J=3.3, 1.6 Hz, 2H), 2.08 (s, 6H), 2.00-1.73 (m, 8H), 1.65 (td, J=15.9, 15.4, 6.2 Hz, 2H). LCMS-ESI+ (m/z): $[M+H]^+$ calculated for $C_4H_{49}Cl_2N_4O_6$: 751.30; found: 751.22.

Example 227: (1S,1'S,2R,2'R)-2,2'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(cyclopentan-1-ol) (or (1S,1'S,2R,2'R)-2,2'-(((6,6'-(((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(cyclopentan-1-ol))

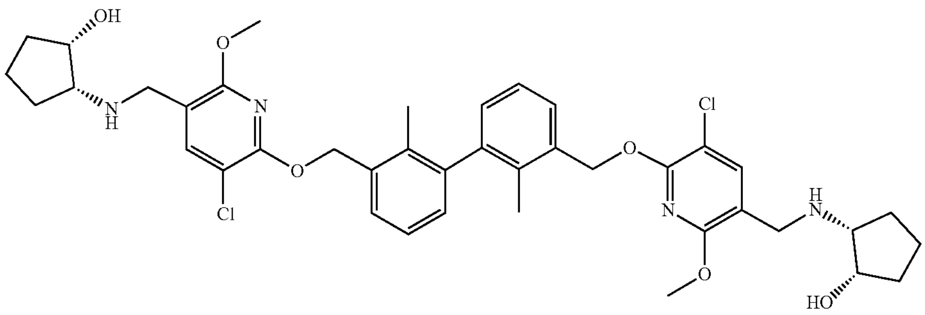 [SMILES: COc1nc(OCc2cccc(-c3cccc(COc4nc(OC)c(CN[C@@H]5CCC[C@@H]5O)cc4Cl)c3C)c2C)c(Cl)cc1CN[C@@H]1CCC[C@@H]1O]

Prepared in a similar manner to Example 226, using (1S,2R)-2-aminocyclopentan-1-ol in place of (1R,2S)-2-aminocyclopentan-1-ol: $^1H$ NMR (400 MHz, Methanol-$d_4$) δ 7.81 (s, 2H), 7.46 (d, J=7.5 Hz, 2H), 7.23 (t, J=7.6 Hz, 2H), 7.06 (d, J=7.5 Hz, 2H), 5.58 (s, 4H), 4.40-4.29 (m, 2H), 4.13 (q, J=13.3 Hz, 4H), 4.03 (s, 6H), 3.42 (td, J=8.8, 4.8 Hz, 2H), 3.30 (dt, J=3.3, 1.6 Hz, 2H), 2.08 (s, 6H), 2.00-1.73 (m, 8H), 1.65 (td, J=15.9, 15.4, 6.2 Hz, 2H). LCMS-ESI+ (m/z): $[M+H]^+$ calculated for $C_{40}H_{49}Cl_2N_4O_6$: 751.30; found: 751.16.

Example 228: (1R,1'R,2S,2'S)-2,2'-((((((2,2'-dimethyl-[1,1'-biphenyl]-3,3'-diyl)bis(methylene))bis(oxy))bis(5-chloro-2-methoxypyridine-6,3-diyl))his(methylene))his(azanediyl))his(cyclohexan-1-ol)

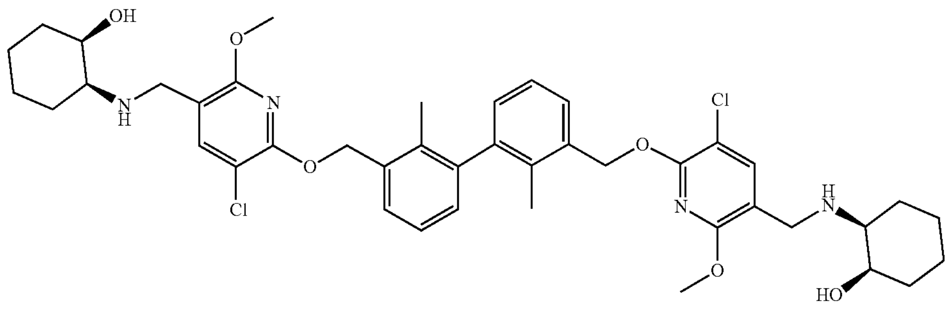 [SMILES: COc1nc(OCc2cccc(-c3cccc(COc4nc(OC)c(CN[C@H]5CCCC[C@H]5O)cc4Cl)c3C)c2C)c(Cl)cc1CN[C@H]1CCCC[C@H]1O]

Prepared in a similar manner to Example 226, using (1R,2S)-2-aminocyclohexan-1-ol in place of (1R,2S)-2-aminocyclopentan-1-ol: $^1H$ NMR (400 MHz, Methanol-$d_4$) δ 7.80 (s, 2H), 7.46 (d, J=7.4 Hz, 2H), 7.23 (t, J=7.6 Hz, 2H), 7.06 (d, J=7.5 Hz, 2H), 5.58 (s, 4H), 4.22-4.04 (m, 6H), 4.03 (s, 6H), 3.15 (dt, J=10.6, 4.1 Hz, 2H), 2.07 (s, 6H), 1.98-1.68 (m, 8H), 1.71-1.18 (m, 8H). LCMS-ESI+ (m/z): $[M+H]^+$ calculated for $C_{42}H_{53}Cl_2N_4O_6$: 779.33; found: 779.22.

Example 229: (1S,1'S,2S,2'S)-2,2'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(cyclohexan-1-ol)

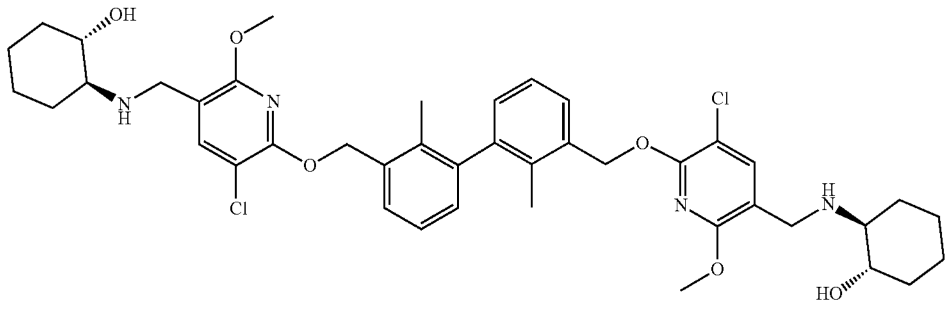 [SMILES: COc1nc(OCc2cccc(-c3cccc(COc4nc(OC)c(CN[C@H]5CCCC[C@@H]5O)cc4Cl)c3C)c2C)c(Cl)cc1CN[C@H]1CCCC[C@@H]1O]

Prepared in a similar manner to Example 226, using (1S,2S)-2-aminocyclohexan-1-ol in place of (1R,2S)-2-aminocyclopentan-1-ol: $^1H$ NMR (400 MHz, Methanol-$d_4$) δ 7.82 (s, 2H), 7.47 (d, J=7.6 Hz, 2H), 7.23 (t, J=7.6 Hz, 2H), 7.06 (d, J=7.5 Hz, 2H), 5.58 (s, 4H), 4.18 (d, J=1.8 Hz, 4H), 4.04 (s, 6H), 3.54 (td, J=9.8, 4.9 Hz, 2H), 2.91-2.80 (m, 2H), 2.22 (d, J=13.1 Hz, 2H), 2.14-2.02 (m, 8H), 1.90-1.72 (m, 4H), 1.54-1.22 (m, 8H). LCMS-ESI+ (m/z): $[M+H]^+$ calculated for $C_{42}H_{53}Cl_2N_4O_6$: 779.33; found: 779.24.

Example 230: (1S,1'S,2S,2'S)-2,2'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(cyclopentan-1-ol) (or (1S,1'S,2S,2'S)-2,2'-(((6,6'-(((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(cyclopentan-1-ol))

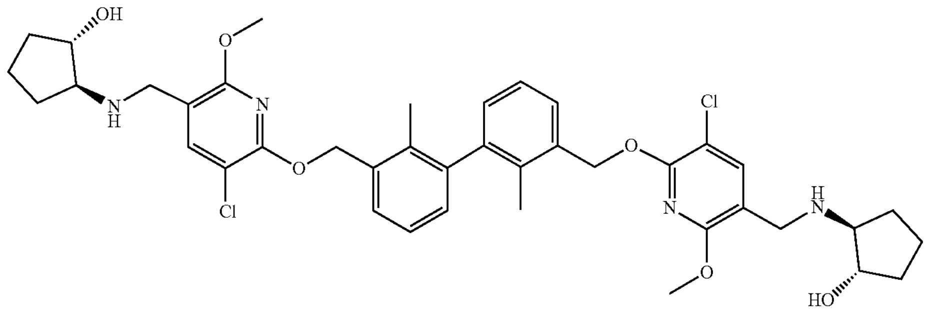 [SMILES: COc1nc(OCc2cccc(-c3cccc(COc4nc(OC)c(CN[C@H]5CCC[C@@H]5O)cc4Cl)c3C)c2C)c(Cl)cc1CN[C@H]1CCC[C@@H]1O]

Prepared in a similar manner to Example 226, using (1S,2S)-2-aminocyclopentan-1-ol in place of (1R,2S)-2-aminocyclopentan-1-ol: $^1$H NMR (400 MHz, Methanol-$d_4$) δ 7.82 (s, 2H), 7.47 (d, J=7.3 Hz, 2H), 7.23 (t, J=7.6 Hz, 2H), 7.07 (d, J=7.6 Hz, 2H), 5.59 (s, 4H), 4.27 (d, J=13.4 Hz, 2H), 4.20 (q, J=6.7 Hz, 2H), 4.14 (d, J=13.4 Hz, 2H), 4.05 (s, 6H), 3.38-3.31 (m, 2H), 2.23 (dt, J=13.5, 6.7 Hz, 2H), 2.08 (s, 6H), 2.04-1.99 (m, 2H), 1.79 (dq, J=15.2, 7.5 Hz, 4H), 1.65 (ddd, J=13.1, 9.8, 5.9 Hz, 4H). LCMS-ESI+ (m/z): $[M+H]^+$ calculated for $C_4H_{49}Cl_2N_4O_6$: 751.30; found: 751.10.

Example 231: 1,1'-((((((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(cyclobutane-1-carbonitrile) (or 1,1'-(((6,6'-(((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(cyclobutane-1-carbonitrile))

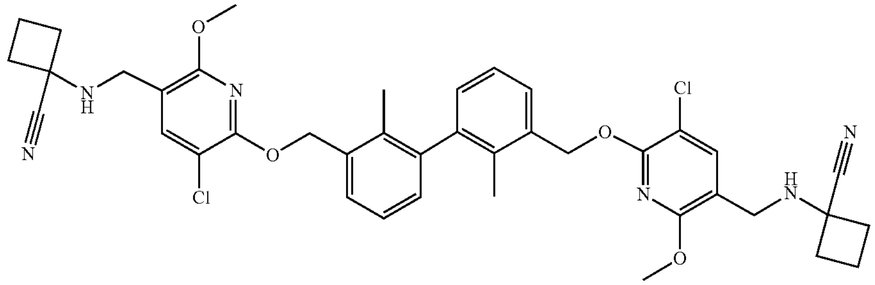 [SMILES: COc1nc(OCc2cccc(-c3cccc(COc4nc(OC)c(CNC5(C#N)CCC5)cc4Cl)c3C)c2C)c(Cl)cc1CNC1(C#N)CCC1]

Prepared in a similar manner to Example 226, using 1-aminocyclobutane-1-carbonitrile in place of (1R,2S)-2-aminocyclopentan-1-ol: $^1$H NMR (400 MHz, Methanol-$d_4$) δ 7.81 (s, 2H), 7.46 (d, J=7.5 Hz, 2H), 7.22 (t, J=7.6 Hz, 2H), 7.06 (d, J=7.5 Hz, 2H), 5.58 (s, 4H), 4.11 (s, 3H), 4.04 (s, 6H), 2.96-2.43 (m, 8H), 2.33-2.20 (m, 2H), 2.20-2.10 (m, 2H), 2.07 (s, 6H). LCMS-ESI+ (m/z): $[M+Na]^+$ calculated for $C_{40}H_{42}Cl_2N_6NaO_4$: 763.2; found: 762.9.

Example 232: (2'S)-(((((2,2'-dimethyl-[1,1'-biphenyl]-3,3'-diyl)bis(methylene))bis(oxy))bis(5-chloro-2-methoxypyridine-6,3-diyl))bis(methylene))di-L-proline (or (2'S)-((6,6'-(((2,2'-dimethyl-[1,1'-biphenyl]-3,3'-diyl)bis(methylene))bis(oxy))bis(5-chloro-2-methoxypyridine-6,3-diyl))bis(methylene)) di-L-proline)

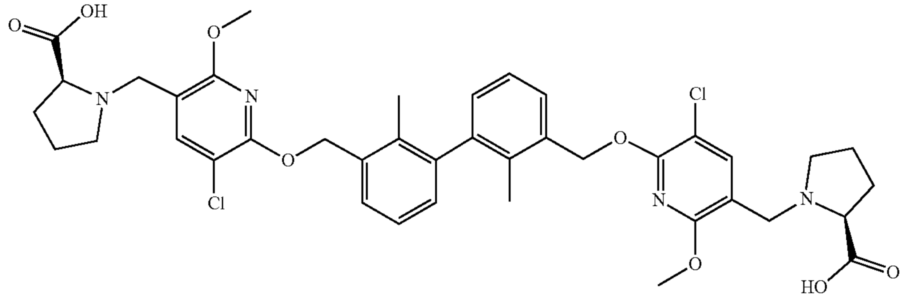 [SMILES: COc1nc(OCc2cccc(-c3cccc(COc4nc(OC)c(CN5CCC[C@H]5C(=O)O)cc4Cl)c3C)c2C)c(Cl)cc1CN1CCC[C@H]1C(=O)O]

Prepared in a similar manner to Example 226, using L-proline in place of (1R,2S)-2-aminocyclopentan-1-ol: $^1H$ NMR (400 MHz, Methanol-$d_4$) δ 7.84 (s, 2H), 7.47 (d, J=7.5 Hz, 2H), 7.25 (t, J=7.6 Hz, 2H), 7.09 (d, J=6.7 Hz, 2H), 5.59 (s, 4H), 4.38 (q, J=13.9 Hz, 4H), 4.32-4.26 (m, 2H), 4.05 (s, 6H), 3.61 (ddd, J=11.0, 7.5, 3.9 Hz, 2H), 3.41-3.31 (m, 2H), 2.62-2.51 (m, 2H), 2.25-2.11 (m, 4H), 2.09 (s, 6H), 2.06-1.96 (m, 2H). LCMS-ESI+ (m/z): $[M+H]^+$ calculated for $C_{40}H_{45}Cl_2N_4O_8$: 779.26; found: 779.10.

Example 233: (3S,3'S)-4,4'-(((((2,2'-dimethyl-[1,1'-biphenyl]-3,3'-diyl)bis(methylene))bis(oxy))bis(5-chloro-2-methoxypyridine-6,3-diyl))bis(methylene)) bis(morpholine-3-carboxylicacid) (or (3S,3'S)-4,4'-((6,6'-(((2,2'-dimethyl-[1,1'-biphenyl]-3,3'-diyl)bis (methylene))bis(oxy))bis(5-chloro-2-methoxypyridine-6,3-diyl))bis(methylene))bis (morpholine-3-carboxylic acid))

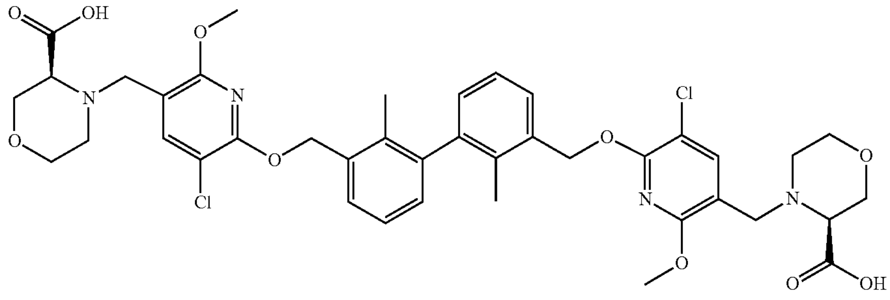 [SMILES: COc1nc(OCc2cccc(-c3cccc(COc4nc(OC)c(CN5CCOC[C@H]5C(=O)O)cc4Cl)c3C)c2C)c(Cl)cc1CN1CCOC[C@H]1C(=O)O]

Prepared in a similar manner to Example 226, using (S)-morpholine-3-carboxylic acid in place of (1R,2S)-2-aminocyclopentan-1-ol: $^1H$ NMR (400 MHz, Methanol-$d_4$) δ 7.86 (s, 2H), 7.48 (d, J=7.1 Hz, 2H), 7.25 (t, J=7.6 Hz, 2H), 7.08 (d, J=7.1 Hz, 2H), 5.60 (s, 4H), 4.52-4.33 (m, 4H), 4.30-4.14 (m, 4H), 4.13-3.90 (m, 8H), 3.87-3.70 (m, 4H), 3.55-3.43 (m, 2H), 3.28-3.18 (m, 2H), 2.09 (s, 6H). LCMS-ESI+ (m/z): $[M+H]^+$ calculated for $C_{40}H_{45}Cl_2N_4O_{10}$: 811.25; found: 810.97.

Example 234: (2'R)-(((((2,2'-dimethyl-[1,1'-biphenyl]-3,3'-diyl)bis(methylene))bis(oxy))bis(5-chloro-2-methoxypyridine-6,3-diyl))bis(methylene))di-D-proline (or (2'R)-((6,6'-(((2,2'-dimethyl-[1,1'-biphenyl]-3,3'-diyl)bis(methylene))bis(oxy))bis(5-chloro-2-methoxypyridine-6,3-diyl))bis(methylene)) di-D-proline)

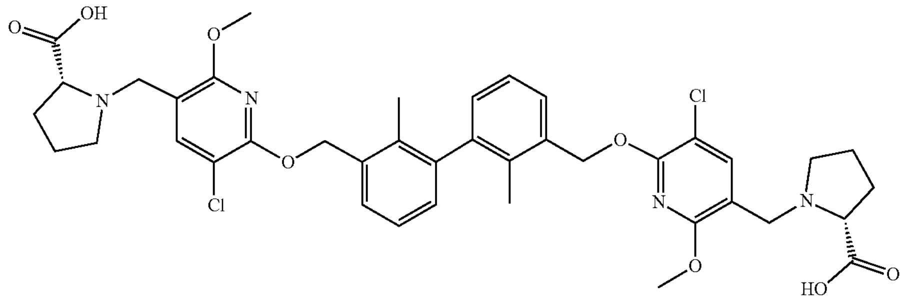 [SMILES: COc1nc(OCc2cccc(-c3cccc(COc4nc(OC)c(CN5CCC[C@@H]5C(=O)O)cc4Cl)c3C)c2C)c(Cl)cc1CN1CCC[C@@H]1C(=O)O]

Prepared in a similar manner to Example 226, using D-proline in place of (1R,2S)-2-aminocyclopentan-1-ol: $^1H$ NMR (400 MHz, Methanol-$d_4$) δ 7.84 (s, 2H), 7.47 (d, J=7.5 Hz, 2H), 7.25 (t, J=7.6 Hz, 2H), 7.09 (d, J=6.7 Hz, 2H), 5.59 (s, 4H), 4.38 (q, J=13.9 Hz, 4H), 4.32-4.26 (m, 2H), 4.05 (s, 6H), 3.61 (ddd, J=11.0, 7.5, 3.9 Hz, 2H), 3.41-3.31 (m, 2H), 2.62-2.51 (m, 2H), 2.25-2.11 (m, 4H), 2.09 (s, 6H), 2.06-1.96 (m, 2H). LCMS-ESI+ (m/z): $[M+H]^+$ calculated for $C_{40}H_{45}Cl_2N_4O_8$: 779.26; found: 779.09.

Example 235: 4,4'-((((2,2'-dimethyl-[1,1'-biphenyl]-3,3'-diyl)bis(methylene))bis(oxy))bis(5-chloro-2-methoxypyridine-6,3-diyl))bis(methylene))bis(morpholine-2-carboxylic acid) (or 4,4'-((6,6'-(((2,2'-dimethyl-[1,1'-biphenyl]-3,3'-diyl)bis(methylene))bis(oxy))bis(5-chloro-2-methoxypyridine-6-diyl))bis(methylene))bis(morpholine-2-carboxylic acid)

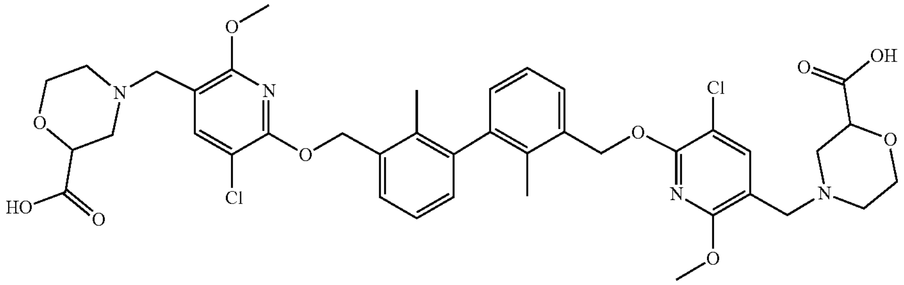 [SMILES: COc1nc(OCc2cccc(-c3cccc(COc4nc(OC)c(CN5CCOC(C(=O)O)C5)cc4Cl)c3C)c2C)c(Cl)cc1CN1CCOC(C(=O)O)C1]

Prepared in a similar manner to Example 226, using morpholine-2-carboxylic acid in place of (1R,2S)-2-aminocyclopentan-1-ol: $^1H$ NMR (400 MHz, Methanol-$d_4$) δ 7.86 (s, 2H), 7.48 (d, J=7.9 Hz, 2H), 7.24 (t, J=7.6 Hz, 2H), 7.08 (d, J=7.4 Hz, 2H), 5.60 (s, 4H), 4.43 (d, J=6.6 Hz, 2H), 4.29 (s, 4H), 4.12 (dt, J=12.4, 2.8 Hz, 2H), 4.05 (s, 6H), 3.90-3.81 (m, 2H), 3.65 (d, J=12.8 Hz, 2H), 3.43-3.31 (m, 4H), 3.23-3.15 (m, 2H), 2.08 (s, 6H). LCMS-ESI+ (m/z): $[M+H]^+$ calculated for $C_{40}H_{45}Cl_2N_4O_{10}$: 811.25; found: 811.00.

Example 236: 3,3'-((((2,2'-dimethyl-[1,1'-biphenyl]-3,3'-diyl)bis(methylene))bis(oxy))bis(5-chloro-2-methoxypyridine-6,3-diyl))bis(3-(dimethylamino) propanoic acid) (or 3,3'-(6,6'-(((2,2'-dimethyl-[1,1'-biphenyl]-3,3'-diyl)bis(methylene))bis(oxy))bis(5-chloro-2-methoxypyridine-6,3-diyl))bis(3-(dimethylamino)propanoic acid))
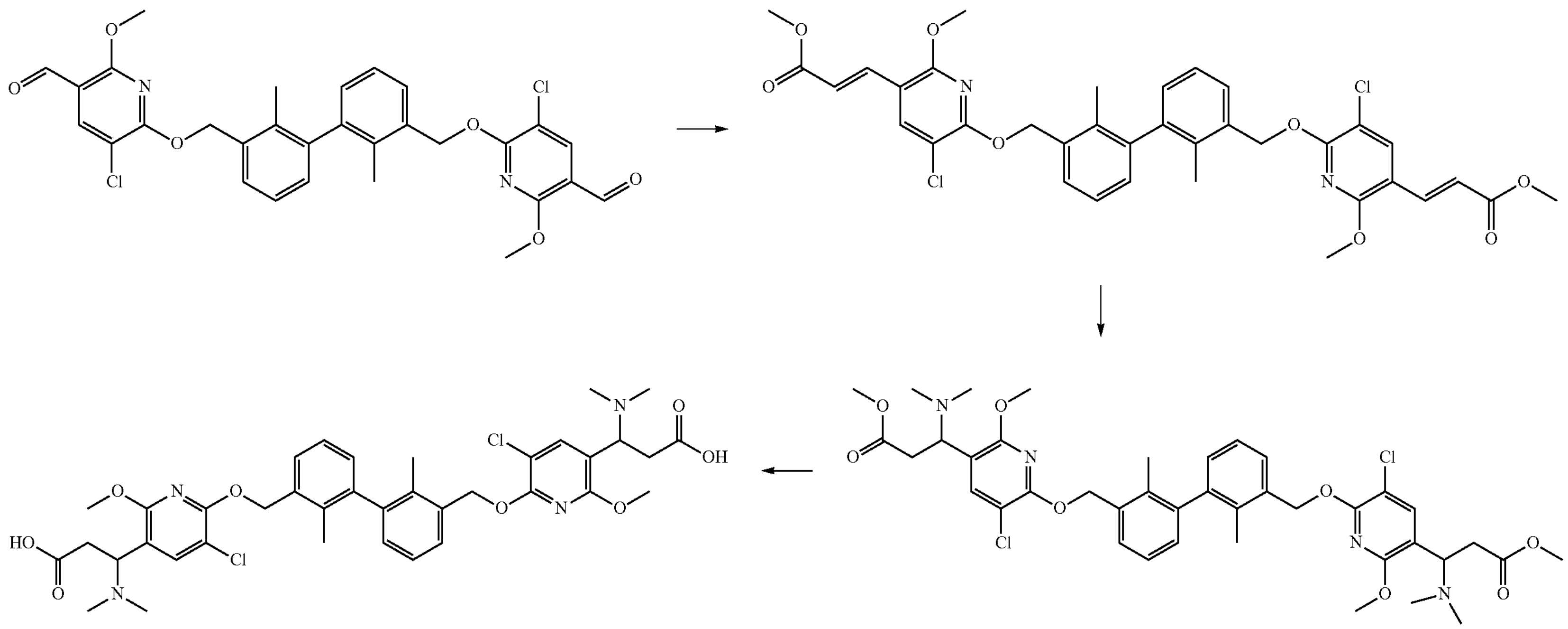

To a solution of methyl 2-(dimethoxyphosphoryl) acetate (0.083 mL, 0.52 mmol) in THF (3 mL) at 0° C. was added n-BuLi (1.94 Min hexane, 0.27 mL, 0.52 mmol) dropwise. The mixture was allowed to warm to rt and stir 20 min 6,6'-(((2,2'-dimethyl-[1,1F-biphenyl]-3,3'-diyl)bis(methylene))bis(oxy))bis(5-chloro-2-methoxynicotinaldehyde) (100 mg, 0.172 mmol) was then added as a solid in one portion, and the mixture was allowed to stir at rt for an additional 30 min. The mixture was poured over $H_2O$, and the aqueous layer was extracted with $CH_2Cl_2$ (3×5 mL). The combined organics were dried ($MgSO_4$) and concentrated, and the residue purified via column chromatography ($SiO_2$, 0-30% EtOAc in hexane) to yield dimethyl 3,3'-((((2,2'-dimethyl-[1,1'-biphenyl]-3,3'-diyl)bis(methylene))bis(oxy))bis(5-chloro-2-methoxypyridine-6,3-diyl))(2E,2'E)-diacrylate as a solid.

To a solution of dimethylamine (2.0 M in THF, 0.43 mL, 0.87 mmol) at −78° C. was added n-BuLi (1.94 M in hexane, 0.45 mL, 0.87 mmol) dropwise. The mixture was stirred at −78° C. for 1 h, then a solution of dimethyl 3,3'-((((2,2'-dimethyl-[1,1'-biphenyl]-3,3'-diyl)bis(methylene))bis(oxy))bis(5-chloro-2-methoxypyridine-6,3-diyl))(2E,2'E)-diacrylate (60 mg, 0.087 mmol) in THF (1 mL) was added dropwise. The mixture was stirred at −78° C. for an additional 1 h, then MeOH (1 mL) was added dropwise. The mixture was warmed to room temperature, concentrated, and purified via preparative reverse-phase HPLC (25-95% MeCN in $H_2O$) to yield dimethyl 3,3'-((((2,2'-dimethyl-[1,1'-biphenyl]-3,3'-diyl)bis(methylene))bis(oxy))bis(5-chloro-2-methoxypyridine-6,3-diyl))bis(3-(dimethylamino)propanoate) as a solid.

To a solution of dimethyl 3,3'-((((2,2'-dimethyl-[1,1'-biphenyl]-3,3'-diyl)bis(methylene))bis(oxy))bis(5-chloro-2-methoxypyridine-6,3-diyl))bis(3-(dimethylamino)propanoate) (65 mg, 0.083 mmol) in THF/$H_2O$/DMSO (1:1:1 by volume, 3 mL) was added LiOH (14 mg, 0.33 mmol). The mixture was stirred vigorously for 30 min, then purified via preparative reverse-phase HPLC (25-98% MeCN in $H_2O$) to yield 3,3'-((((2,2'-dimethyl-[1,1'-biphenyl]-3,3'-diyl)bis(methylene))bis(oxy))bis(5-chloro-2-methoxypyridine-6,3-diyl))bis(3-(dimethylamino)propanoic acid), as an inseparable mixture of diastereomers. $^1H$ NMR (400 MHz, Methanol-$d_4$) δ 7.91 (d, J=1.7 Hz, 2H), 7.47 (t, J=8.5 Hz, 2H), 7.25 (d, J=8.5 Hz, 2H), 7.12-7.06 (m, 2H), 5.60 (s, 4H), 4.95-4.91 (m, 2H), 4.07 (d, J=2.7 Hz, 6H), 3.26-3.10 (m, 4H), 2.82 (s, 12H), 2.09 (d, J=4.0 Hz, 6H). LCMS-ESI+ (m/z): $[M+H]^+$ calculated for $C_{38}H_{45}Cl_2N_4O_8$: 755.26; found: 755.33.

Example 237: (3S,3'S)-4,4'-((6,6'-(((2,2'-dimethyl-[1,1'-biphenyl]-3,3'-diyl)bis(methylene))bis(oxy))bis(5-chloro-2-methoxynicotinoyl))bis(azanediyl))bis(3-hydroxybutanoic acid)

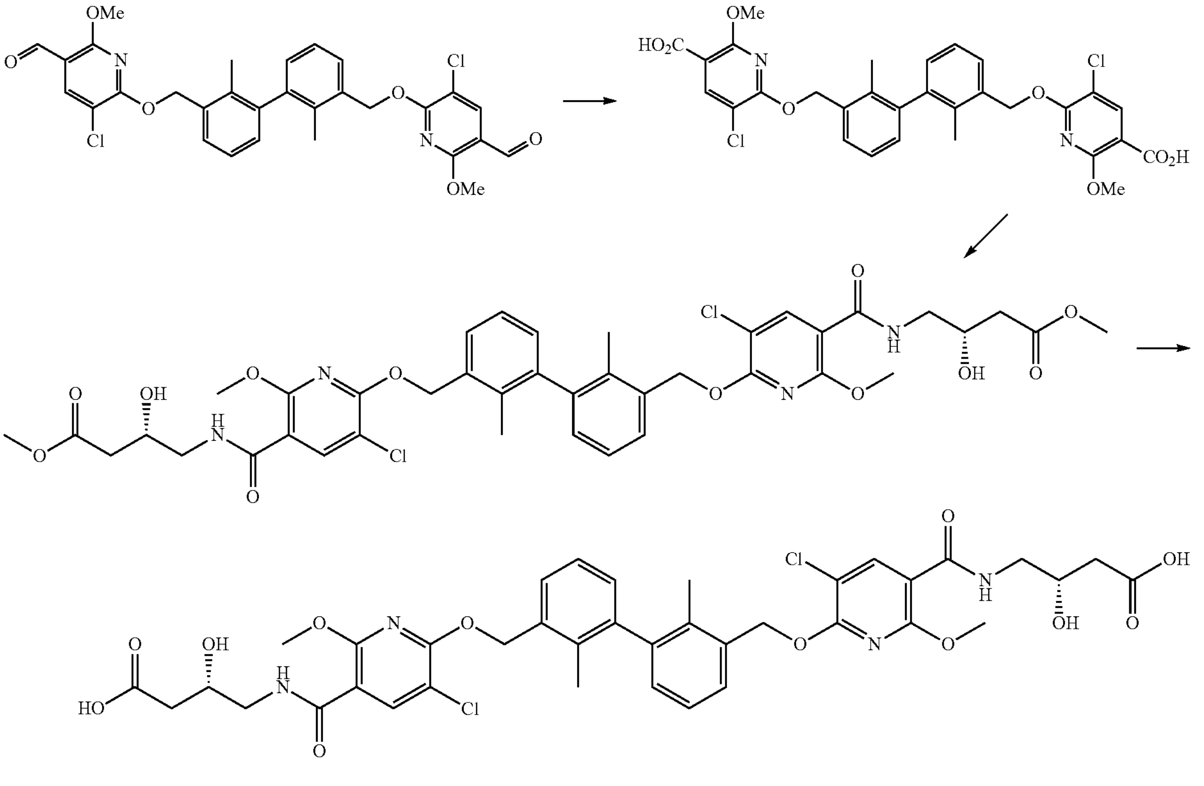

To a slurry of 6,6'-(((2,2'-dimethyl-[1,1'-biphenyl]-3,3'-diyl)bis(methylene))bis(oxy))bis(5-chloro-2-methoxynicotinaldehyde) (390 mg, 0.67 mmol) and 2-methyl-2-butene (1.28 mL, 12.1 mmol) in tBuOH/THF (2:3 v/v, 50 mL) was added a solution of $NaClO_2$ (728 mg, 8.05 mmol) and $NaH_2PO_4$ (1.21 g, 10.1 mmol) in $H_2O$ (20 mL). The mixture was stirred at rt for 16 h, then diluted with EtOAc (50 mL), washed with $NH_4Cl$ (3×50 mL), dried ($Na_2SO_4$), and concentrated. The residue was purified by column chromatography ($SiO_2$, 0-13% MeOH in $CH_2Cl_2$) to yield 6,6'-(((2,2'-dimethyl-[1,1'-biphenyl]-3,3'-diyl)bis(methylene))bis(oxy))bis(5-chloro-2-methoxynicotinic acid) as a solid.

6,6'-(((2,2'-dimethyl-[1,1'-biphenyl]-3,3'-diyl)bis(methylene))bis(oxy))bis(5-chloro-2-methoxynicotinic acid) (389 mg, 0.63 mmol), methyl (S)-4-amino-3-hydroxybutanoate (253 mg, 2 mmol), HATU (579 mg, 2 mmol), and DIPEA (0.74 mL, 3 mmol) were stirred in DMF (20 mL) for 15 min. The mixture was concentrated and the residue purified by preparative reverse-phase HPLC (35-98% MeCN in $H_2O$) to yield dimethyl 4,4'-((6,6'-(((2,2'-dimethyl-[1,1'-biphenyl]-3,3'-diyl)bis(methylene))bis(oxy))bis(5-chloro-2-methoxynicotinoyl))bis(azanediyl))(3S,3'S)-bis(3-hydroxybutanoate) as a solid.

(3S,3'S)-4,4'-((6,6'-(((2,2'-dimethyl-[1,1'-biphenyl]-3,3'-diyl)bis(methylene))bis(oxy))bis(5-chloro-2-methoxynicotinoyl))bis(azanediyl))bis(3-hydroxybutanoic acid) was prepared in a similar manner to Example 36, using dimethyl 4,4'-((6,6'-(((2,2'-dimethyl-[1,1'-biphenyl]-3,3'-diyl)bis(methylene))bis(oxy))bis(5-chloro-2-methoxynicotinoyl))bis(azanediyl))(3S,3'S)-bis(3-hydroxybutanoate) in place of dimethyl 3,3'-((((2,2'-dimethyl-[1,1'-biphenyl]-3,3'-diyl)bis(methylene))bis(oxy))bis(5-chloro-2-methoxypyridine-6,3-diyl))bis(3-(dimethylamino)propanoate). $^1H$ NMR (400 MHz, Acetone-$d_6$) δ 8.35 (s, 2H), 7.54 (d, J=7.6 Hz, 2H), 7.30 (t, J=7.6 Hz, 2H), 7.13 (d, J=7.3 Hz, 2H), 5.68 (s, 4H), 4.21 (s, 2H), 4.14 (s, 6H), 3.66-3.55 (m, 2H), 3.50-3.39 (m, 2H), 2.56 (dd, J=15.6, 4.7 Hz, 2H), 2.46 (dd, J=15.7, 7.9 Hz, 2H), 2.12 (s, 6H). LCMS-ESI+ (m/z): $[M+H]^+$ calculated for $C_{38}H_{41}Cl_2N_4O_{12}$: 815.21; found: 815.31.

Example 238: (3S,3'S)-4,4'-(((((1E,1'E)-(2,2'-dimethyl-[1,1'-biphenyl]-3,3'-diyl)bis(ethene-2,1-diyl))bis(2-methoxypyridine-6,3-diyl))bis(methylene))bis(azanediyl))bis(3-hydroxybutanoic acid) (or(3S,3'S)-4,4'-(((6,6'-((1E,1'E)-(2,2'-dimethyl-[1,1'-biphenyl]-3,3'-diyl)bis(ethene-2,1-diyl))bis(2-methoxypyridine-6,3-diyl))bis(methylene))bis(azanediyl))bis(3-hydroxybutanoic acid))

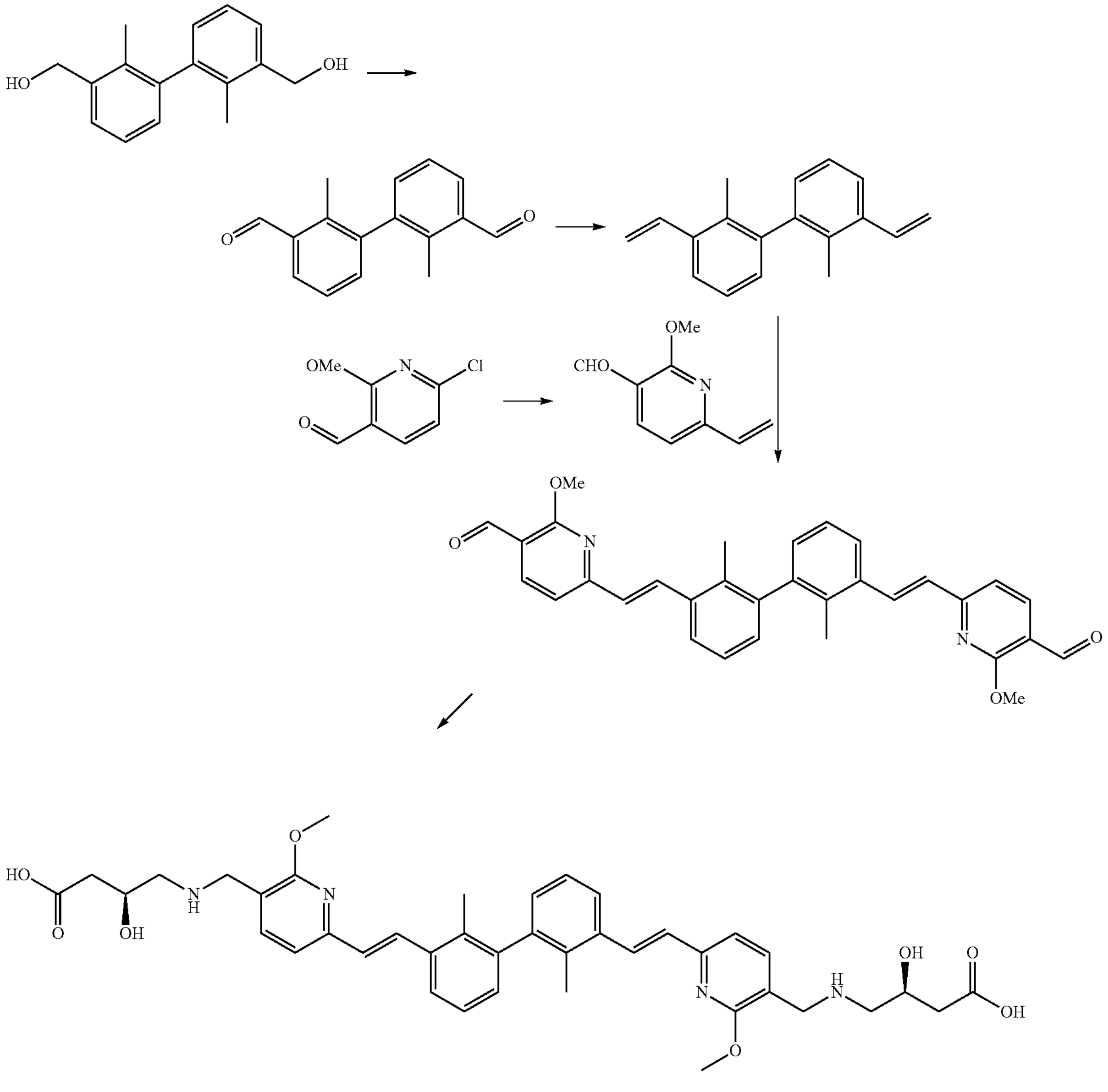

2,2'-dimethyl-[1,1'-biphenyl]-3,3'-dicarbaldehyde: To a solution of (2,2'-dimethyl-[1,1'-biphenyl]-3,3'-diyl)dimethanol (150 mg, 0.62 mmol) in $CH_2Cl_2$(5 mL) was added Dess-Martin periodinane (630 mg, 1.55 mmol). The mixture was stirred at rt for 15 min, then diluted with $CH_2Cl_2$ (10 mL), poured over $Na_2S_2O_3$(1 M aq., 10 mL), and washed with $NaHCO_3$ (saturated aq., 2×10 mL). The organics were dried ($MgSO_4$) and concentrated, and the residue purified via column chromatography ($SiO_2$, 0-25% EtOAc in hexane) to yield the product as a solid.

2,2'-dimethyl-3,3'-divinyl-1,1'-biphenyl: To a slurry of methyl triphenylphosphonium bromide (19.9 g, 53 mmol) in THF (50 mL) at 0° C. was added n-BuLi (1.8 M in hexane, 29 mL, 53 mmol) dropwise. The mixture was stirred for 30 min, then 2,2'-dimethyl-[1,1'-biphenyl]-3,3'-dicarbaldehyde (4.85 g, 20 mmol) in THF (25 mL) was added dropwise. The mixture was allowed to warm to rt and stirred 12 h, then diluted with $Et_2O$ (400 mL), washed with $NH_4C$ (saturated aq., 300 mL). The organics were dried ($MgSO_4$) and concentrated, and the residue purified via column chromatography ($SiO_2$, hexane) to yield the product as a solid.

acid) was prepared in a similar manner to Example 226, using (S)-4-amino-3-hydroxybutanoic acid in place of (1R, 2S)-2-aminocyclopentan-1-ol, and using 6,6'-((1E,1'E)-(2, 2'-dimethyl-[1,1'-biphenyl]-3,3'-diyl)bis(ethene-2,1-diyl)) bis(2-methoxynicotinaldehyde) in place of 6,6'-(((2,2'-dimethyl-[1,1'-biphenyl]-3,3'-diyl)bis(methylene))bis(oxy)) bis(5-chloro-2-methoxynicotinaldehyde): $^1$H NMR (400 MHz, Methanol-$d_4$) δ 8.14 (d, J=15.7 Hz, 1H), 7.75 (d, J=7.5 Hz, 1H), 7.70 (d, J=7.7 Hz, 1H), 7.28 (t, J=7.7 Hz, 1H), 7.12 (d, J=5.1 Hz, 1H), 7.07 (d, J=7.5 Hz, 1H), 4.37-4.29 (m, 1H), 4.25 (s, 2H), 4.10 (s, 3H), 3.24 (dd, J=12.7, 3.0 Hz, 1H), 3.03 (dd, J=12.7, 9.8 Hz, 1H), 2.56 (d, J=6.3 Hz, 2H), 2.15 (s, 3H). LCMS-ESI+ (m/z): $[M+H]^+$ calculated for $C_4H_{47}N_4O_8$: 711.34; found: 711.03.

Example 239: (3S,3'S)-4,4'-(((((1E,1'E)-(2,2'-dimethyl-[1,1'-biphenyl]-3,3'-diyl)bis(ethene-2,1-diyl)) bis(5-chloro-2-methoxypyridine-6,3-diyl))bis(methylene))bis(azanediyl))bis(3-hydroxybutanoic acid) (or (3S,3'S)-4,4'-(((6,6'-((1E,1'E)-(2,2'-dimethyl-[1, 1'-biphenyl]-3,3'-diyl)bis(ethene-2,1-diyl))bis(5-chloro-2-methoxypyridine-6,3-diyl))bis(methylene)) bis(azanediyl))bis(3-hydroxybutanoic acid))

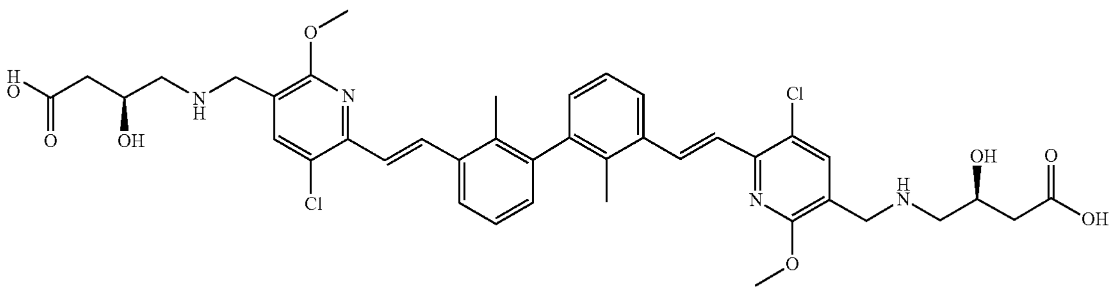 [SMILES: COc1nc(/C=C/c2cccc(-c3cccc(/C=C/c4nc(OC)c(CNC[C@@H](O)CC(=O)O)cc4Cl)c3C)c2C)c(Cl)cc1CNC[C@@H](O)CC(=O)O]

2-methoxy-6-vinylnicotinaldehyde: A mixture of 6-chloro-2-methoxynicotinaldehyde (2.69 g, 16 mmol), 4,4,5,5-tetramethyl-2-vinyl-1,3,2-dioxaborolane (4.22 mL, 39 mmol), palladium tetrakis(triphenylphosphine) (287 mg, 0.78 mmol), and $Na_2CO_3$ (4.99 g, 47 mmol) in dioxane (20 mL) and $H_2O$ (4 mL) were subjected to 3 vacuum/argon cycles, and then heated to 80° C. for 12 h. The mixture was cooled to rt, filtered over Celite, and concentrated. The residue was purified via column chromatography ($Si_2$, 0-15% EtOAc in hexane) to yield the product as an oil.

6,6'-((1E,1'E)-(2,2'-dimethyl-[1,1'-biphenyl]-3,3'-diyl)bis (ethene-2,1-diyl))bis(2-methoxynicotinaldehyde): A mixture of 2,2'-dimethyl-3,3'-divinyl-1,1-biphenyl (500 mg, 2 mmol) and 2-methoxy-6-vinylnicotinaldehyde (870 mg, 5 mmol) in 1,2-dichloroethane (20 mL) was sparged with argon for 15 min. Then, Hoveyda-Grubbs Second Generation Metathesis Catalyst (267 mg, 0.427 mmol) was added, and the mixture was heated to reflux for 20 h. The mixture was concentrated and the residue purified by column chromatography ($SiO_2$, 0-30% EtOAc in hexane) to yield the product as a solid.

(3S,3'S)-4,4'-(((((1E,1'E)-(2,2'-dimethyl-[1,1'-biphenyl]-3,3'-diyl)bis(ethene-2,1-diyl))bis(2-methoxypyridine-6,3-diyl))bis(methylene))bis(azanediyl))bis(3-hydroxybutanoic 5-chloro-2-methoxy-6-vinylnicotinaldehyde: A mixture of 5,6-dichloro-2-methoxynicotinaldehyde (1.4 g, 6.7 mmol), tributyl(vinyl)tin (2.2 mL, 7.4 mmol), LiCl (346 mg, 8.04 mmol), and palladium tetrakis(triphenylphosphine) (550 mg, 0.48 mmol) in dioxane (30 mL) was sparged with argon for 15 min. The mixture was heated to 95° C. for 24 h, then cooled to rt, filtered over celite, and concentrated. The residue was taken up in $CH_2Cl_2$(30 mL) and washed with KF (saturated aq., 3×20 mL). The organics were dried ($MgSO_4$), concentrated, and the residue purified via column chromatography ($SiO_2$, 0-30% EtOAc in hexane) to yield the product as a solid.

(3S,3'S)-4,4'-(((((1E,1'E)-(2,2'-dimethyl-[1,1'-biphenyl]-3,3'-diyl)bis(ethene-2,1-diyl))bis(5-chloro-2-methoxypyridine-6,3-diyl))bis(methylene))bis(azanediyl))bis(3-hydroxybutanoic acid) was prepared in a similar manner to Example 238, using 5-chloro-2-methoxy-6-vinylnicotinaldehyde instead of 2-methoxy-6-vinylnicotinaldehyde. $^1$H NMR (400 MHz, Methanol-$d_4$) δ 8.32 (d, J=15.4 Hz, 2H), 7.86 (s, 2H), 7.73 (d, J=7.9 Hz, 2H), 7.49 (d, J=15.4 Hz, 2H), 7.32 (t, J=7.7 Hz, 2H), 7.12 (d, J=7.2 Hz, 2H), 4.32 (dtd, J=8.0, 5.7, 5.0, 2.4 Hz, 2H), 4.25 (s, 4H), 4.11 (s, 6H), 3.26 (dd, J=12.8, 2.9 Hz, 2H), 3.05 (dd, J=12.7, 9.8 Hz, 2H), 2.56 (d, J=6.3 Hz, 4H), 2.17 (s, 6H). LCMS-ESI+ (m/z): $[M+H]^+$ calculated for $C_{40}H_{45}Cl_2N_4O_8$: 779.26; found: 779.01.

Example 240: (3S,3'S)-4,4'-((((((2,2'-dimethyl-[1,1'-biphenyl]-3,3'-diyl)bis(methylene))bis(oxy))bis(5-bromo-2-((5-cyanopyridin-3-yl)methoxy)pyridine-6,3-diyl))bis(methylene))bis(azanediyl))bis(3-hydroxybutanoic acid) (or (3S,3'S)-4,4'-(((6,6'-(((2,2'-dimethyl-[1,1'-biphenyl]-3,3'-diyl)bis(methylene))bis(oxy))bis(5-bromo-2-((5-cyanopyridin-3-yl)methoxy)pyridine-6,3-diyl))bis(methylene))bis(azanediyl))bis(3-hydroxybutanoic acid))

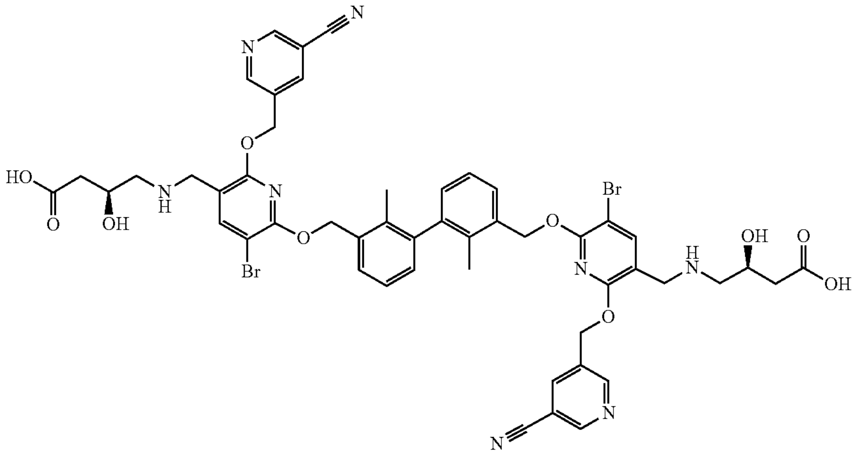 [SMILES: Cc1c(COc2nc(OCc3cncc(C#N)c3)c(CNC[C@@H](O)CC(=O)O)cc2Br)cccc1-c1cccc(COc2nc(OCc3cncc(C#N)c3)c(CNC[C@@H](O)CC(=O)O)cc2Br)c1C]

The title compound was synthesized according to general reductive amination procedure C. [M+1]=1081.8. $^1$H NMR (400 MHz, Methanol-$d_4$) δ 8.91 (dd, J=28.7, 2.1 Hz, 5H), 8.33 (s, 2H), 7.40 (d, J=7.6 Hz, 2H), 7.23 (t, J=7.6 Hz, 2H), 7.08 (d, J=7.5 Hz, 2H), 5.61 (s, 2H), 5.48 (s, 6H), 4.24 (s, 4H), 3.47 (s, 2H), 3.26-3.21 (m, 2H), 3.12 (s, 2H), 3.04 (d, J=10.0 Hz, 2H), 2.54 (d, J=6.3 Hz, 4H), 2.04 (s, 4H).

Example 241: (3S,3'S)-4,4'-((((((2,2'-dimethyl-[1,1'-biphenyl]-3,3'-diyl)bis(methylene))bis(oxy))bis(5-iodo-2-methoxypyridine-6,3-diyl))bis(methylene))bis(azanediyl))bis(3-hydroxybutanoic acid) (or (3S,3'S)-4,4'-(((6,6'-(((2,2'-dimethyl-[1,1'-biphenyl]-3,3'-diyl)bis(methylene))bis(oxy))bis(5-iodo-2-methoxypyridine-6,3-diyl))bis(methylene))bis(azanediyl))bis(3-hydroxybutanoic acid))

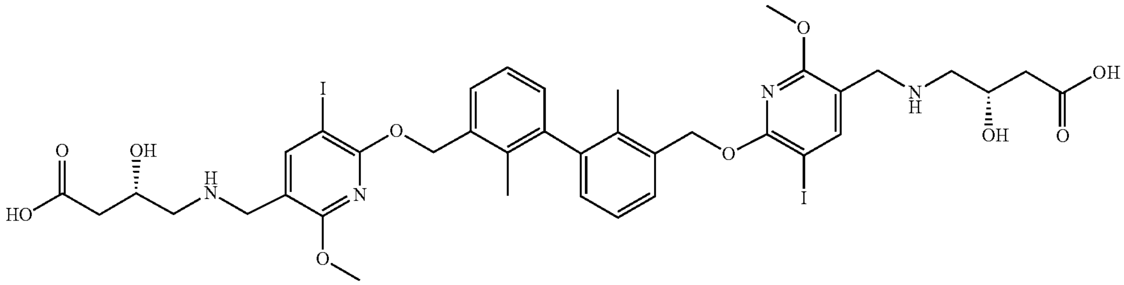 [SMILES: COc1nc(OCc2cccc(-c3cccc(COc4nc(OC)c(CNC[C@@H](O)CC(=O)O)cc4I)c3C)c2C)c(I)cc1CNC[C@@H](O)CC(=O)O]

The title compound was synthesized according to general reductive amination procedure C. [M+1]=971.6. $^1$H NMR (400 MHz, Methanol-$d_4$) δ 8.09 (s, 2H), 7.49 (d, J=7.5 Hz, 2H), 7.24 (t, J=7.6 Hz, 2H), 7.11-7.05 (m, 2H), 5.55 (s, 4H), 4.31-4.22 (m, 2H), 4.14 (s, 4H), 4.05 (s, 6H), 3.20 (dd, J=12.7, 3.1 Hz, 2H), 2.99 (dd, J=12.7, 9.9 Hz, 2H), 2.54 (d, J=6.3 Hz, 4H), 2.12 (s, 6H).

Example 242: (3S,3'S)-4,4'-((((((2,2'-dimethyl-[1,1'-biphenyl]-3,3'-diyl)bis(methylene))bis(oxy))bis(2-((5-cyanopyridin-3-yl)methoxy)pyridine-6,3-diyl))bis(methylene))bis(azanediyl))bis(3-hydroxybutanoic acid) (or (3S,3'S)-4,4'-(((6,6'-(((2,2'-dimethyl-[1,1'-biphenyl]-3,3'-diyl)bis(methylene))bis(oxy))bis(2-((5-cyanopyridin-3-yl)methoxy)pyridine-6,3-diyl))bis(methylene))bis(azanediyl))bis(3-hydroxybutanoic acid))

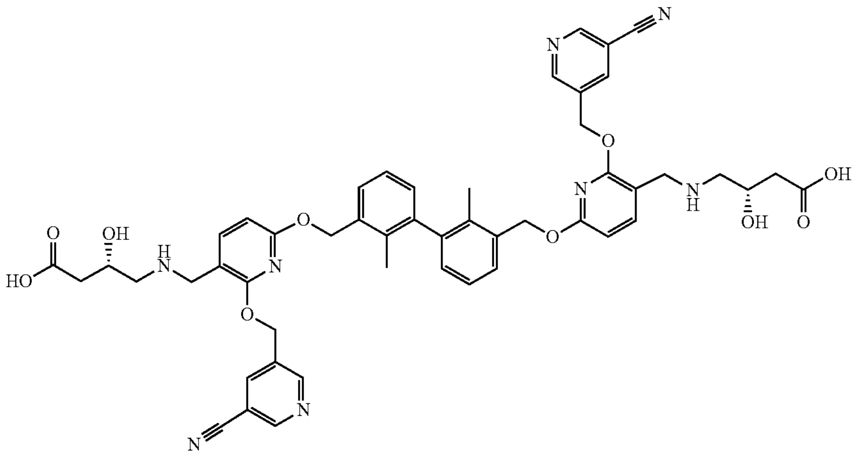 [SMILES: Cc1c(COc2ccc(CNC[C@@H](O)CC(=O)O)c(OCc3cncc(C#N)c3)n2)cccc1-c1cccc(COc2ccc(CNC[C@@H](O)CC(=O)O)c(OCc3cncc(C#N)c3)n2)c1C]

The title compound was synthesized according to general reductive amination procedure C. [M+1]=924.0. $^1$H NMR (400 MHz, Methanol-$d_4$) δ 8.94-8.81 (m, 3H), 8.25 (dd, J=48.8 Hz, 2H), 7.77 (dd, J=8.1, 5.8 Hz, 2H), 7.38 (dd, J=17.4, 7.6 Hz, 2H), 7.28-7.20 (m, 2H), 7.09-7.03 (m, 2H), 6.58 (dd, J=15.5, 8.1 Hz, 2H), 5.63-5.55 (m, 1H), 5.54-5.35 (m, 3H), 4.30-4.20 (m, 4H), 3.49-3.46 (m, 2H), 3.25-2.80 (m, 9H), 2.54 (d, J=6.4 Hz, 2HO, 2.49-2.45 (m, 2H), 2.01 (d, J=16.2 Hz, 6H).

Example 243: (3S,3'S)-4,4'-((((((2,2'-dimethyl-[1,1'-biphenyl]-3,3'-diyl)bis(methylene))bis(oxy))bis(5-cyano-2-methoxypyridine-6,3-diyl))bis(methylene))bis(azanediyl))bis(3-hydroxybutanoic acid) (or (3S,3'S)-4,4'-(((6,6'-(((2,2'-dimethyl-[1,1'-biphenyl]-3,3'-diyl)bis(methylene))bis(oxy))bis(5-cyano-2-methoxypyridine-6,3-diyl))bis(methylene))bis(azanediyl))bis(3-hydroxybutanoic acid))

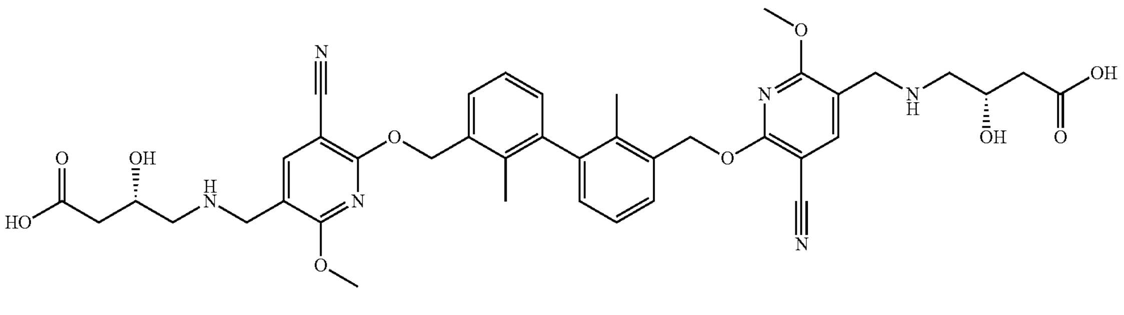 [SMILES: COc1nc(OCc2cccc(-c3cccc(COc4nc(OC)c(CNC[C@@H](O)CC(=O)O)cc4C#N)c3C)c2C)c(C#N)cc1CNC[C@@H](O)CC(=O)O]

The title compound was synthesized according to general reductive amination procedure C. [M+1]=769.8. $^1$H NMR (400 MHz, Methanol-$d_4$) δ 8.06 (s, 2H), 7.50 (d, J=7.8 Hz, 2H), 7.27 (t, J=7.6 Hz, 2H), 7.10 (dd, J=7.5, 1.3 Hz, 2H), 5.67 (s, 4H), 4.33-4.25 (m, 2H), 4.18 (s, 4H), 4.14 (s, 6H), 3.23 (dd, J=12.8, 3.0 Hz, 2H), 3.02 (dd, J=12.8, 9.9 Hz, 2H), 2.55 (d, J=6.3 Hz, 4H), 2.11 (s, 6H).

Example 244: (3S,3'S)-1,1'-(((((2,2'-dimethyl-[1,1'-biphenyl]-3,3'-diyl)bis(methylene))bis(oxy))bis(5-bromo-2-methoxypyridine-6,3-diyl))bis(methylene))bis(pyrrolidin-3-ol) (or (3S,3'S)-1,1'-((6,6'-(((2,2'-dimethyl-[1,1'-biphenyl]-3,3'-diyl)bis(methylene))bis(oxy))bis(5-bromo-2-methoxypyridine-6,3-diyl))bis(methylene))bis(pyrrolidin-3-ol))

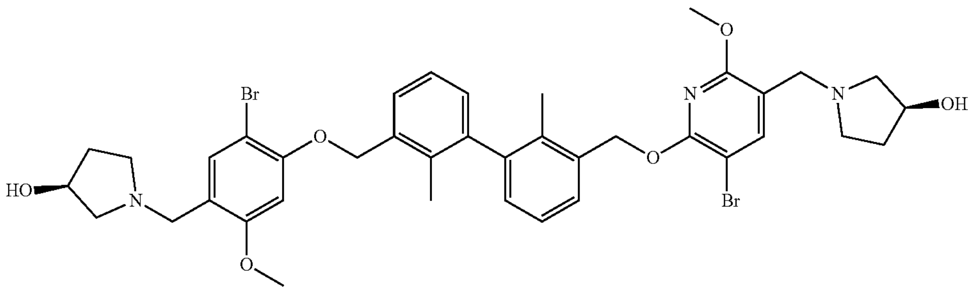 [SMILES: COc1cc(OCc2cccc(-c3cccc(COc4nc(OC)c(CN5CC[C@H](O)C5)cc4Br)c3C)c2C)c(Br)cc1CN1CC[C@H](O)C1]

The title compound was synthesized according to general reductive amination procedure C. [M+1]=813.6. $^1$H NMR (400 MHz, Methanol-$d_4$) δ 8.00 (s, 2H), 7.49 (d, J=7.6 Hz, 2H), 7.25 (t, J=7.6 Hz, 2H), 7.09 (d, J=7.6 Hz, 2H), 5.59 (s, 4H), 4.55-4.50 (m, 2H), 4.33 (d, J=37.0 Hz, 4H), 4.06 (d, J=3.3 Hz, 6H), 3.74-3.40 (m, 7H) 3.25-3.10 (m, 4H), 2.10 (s, 7H).

Example 245: (3S,3'S)-4,4'-((((((2,2'-dimethyl-[1,1'-biphenyl]-3,3'-diyl)bis(methylene))bis(oxy))bis(2-((5-cyanopyridin-3-yl)methoxy)-6-methoxy-4,1-phenylene))bis(methylene))bis(azanediyl))bis(3-hydroxybutanoic acid)

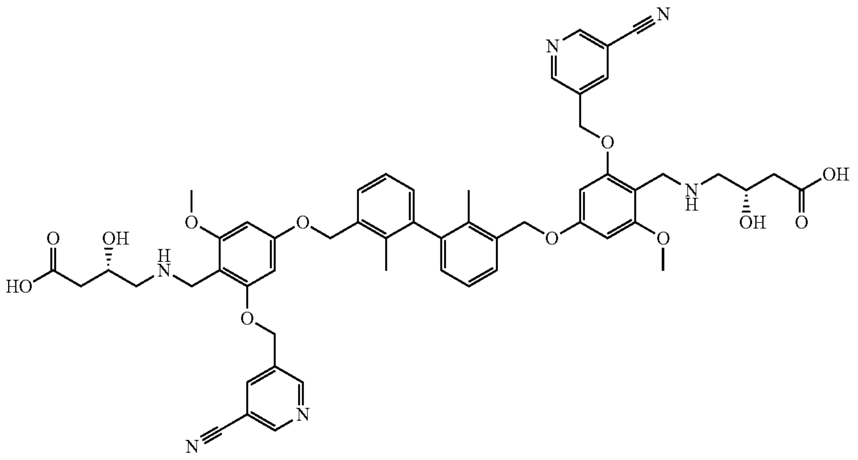 [SMILES: COc1cc(OCc2cccc(-c3cccc(COc4cc(OC)c(CNC[C@@H](O)CC(=O)O)c(OCc5cncc(C#N)c5)c4)c3C)c2C)cc(OCc2cncc(C#N)c2)c1CNC[C@@H](O)CC(=O)O]

The title compound was synthesized according to general reductive amination procedure C. [M+1]=982.1. $^1$H NMR (400 MHz, Methanol-$d_4$) δ 8.91 (dd, J=13.5, 2.0 Hz, 4H), 8.35 (t, J=2.1 Hz, 2H), 7.44 (d, J=7.6 Hz, 2H), 7.26 (t, J=7.6 Hz, 2H), 7.17-7.01 (m, 2H), 6.65-6.34 (m, 4H), 5.25 (d, J=35.1 Hz, 6H), 4.28 (s, 4H), 3.91 (s, 6H), 3.14 (dd, J=12.9, 3.1 Hz, 2H), 2.93 (dd, J=12.8, 10.0 Hz, 2H), 2.50 (dd, J=6.3, 1.7 Hz, 4H), 2.05 (s, 6H).

Example 246: (3S,3'S)-4,4'-((((((2,2'-dimethyl-[1,1'-biphenyl]-3,3'-diyl)bis(methylene))bis(oxy))bis(2-((5-cyanopyridin-3-yl)methoxy)-6-methyl-4,1-phenylene))bis(methylene))bis(azanediyl))bis(3-hydroxybutanoic acid)

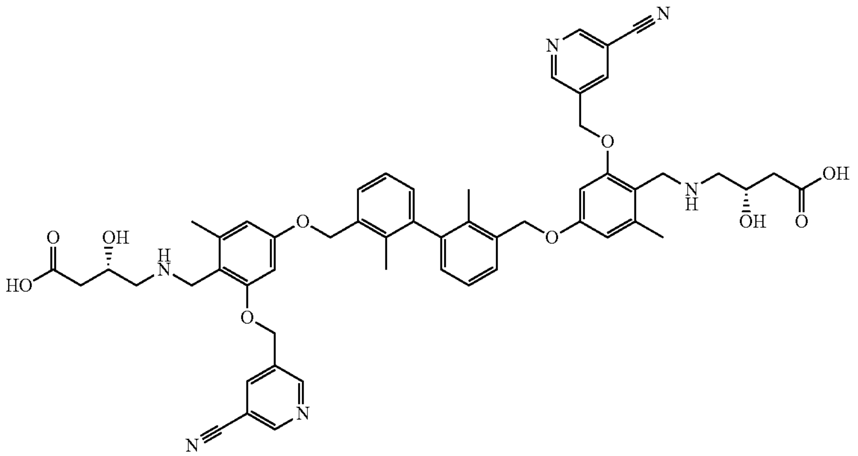 [SMILES: Cc1cc(OCc2cccc(-c3cccc(COc4cc(C)c(CNC[C@@H](O)CC(=O)O)c(OCc5cncc(C#N)c5)c4)c3C)c2C)cc(OCc2cncc(C#N)c2)c1CNC[C@@H](O)CC(=O)O]

The title compound was synthesized according to general reductive amination procedure C. [M+1]=950.1. $^1$H NMR (400 MHz, Methanol-$d_4$) δ 8.91 (dd, J=13.5, 2.0 Hz, 4H), 8.35 (t, J=2.1 Hz, 2H), 7.44 (d, J=7.6 Hz, 2H), 7.26 (t, J=7.6 Hz, 2H), 7.14-7.03 (m, 2H), 6.58-6.40 (m, 4H), 5.24 (d, J=35.1 Hz, 6H), 4.28 (s, 4H), 3.95 (s, 6H), 3.14 (dd, J=12.9, 3.1 Hz, 2H), 2.90 (dd, J=12.8, 10.0 Hz, 2H), 2.50 (dd, J=6.3, 1.7 Hz, 4H), 2.02 (s, 6H).

Example 247: (3R,3'R)-1,1'-(((((2,2'-dimethyl-[1,1'-biphenyl]-3,3'-diyl)bis(methylene))bis(oxy))bis(5-bromo-2-methoxypyridine-6,3-diyl))bis(methylene))bis(pyrrolidin-3-ol) (or (3R,3'R)-1,1'-((6,6'-(((2,2'-dimethyl-[1,1'-biphenyl]-3,3'-diyl)bis(methylene))bis(oxy))bis(5-bromo-2-methoxypyridine-6,3-diyl))bis(methylene))bis(pyrrolidin-3-ol))

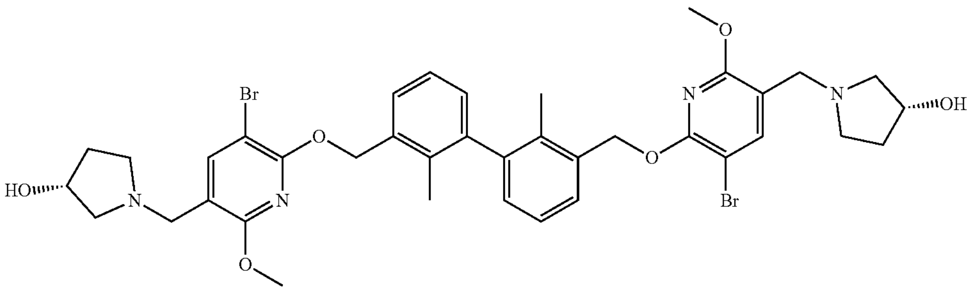 [SMILES: COc1nc(OCc2cccc(-c3cccc(COc4nc(OC)c(CN5CC[C@@H](O)C5)cc4Br)c3C)c2C)c(Br)cc1CN1CC[C@@H](O)C1]

The title compound was synthesized according to general reductive amination procedure C. [M+1]=813.6. $^1$H NMR (400 MHz, Methanol-$d_4$) δ 8.00 (s, 2H), 7.49 (d, J=7.6 Hz, 2H), 7.25 (t, J=7.6 Hz, 2H), 7.09 (d, J=7.6 Hz, 2H), 5.59 (s, 4H), 4.55-4.50 (m, 2H), 4.33 (d, J=37.0 Hz, 4H), 4.06 (d, J=3.3 Hz, 6H), 3.74-3.40 (m, 7H) 3.25-3.10 (m, 4H), 2.10 (s, 7H).

Example 248: (3S,3'S)-4,4'-((((((2,2'-dimethyl-[1,1'-biphenyl]-3,3'-diyl)bis(methylene))bis(oxy))bis(2-((5-cyanopyridin-3-yl)methoxy)-4,1-phenylene))bis(methylene))bis(azanediyl))bis(3-hydroxybutanoic acid)

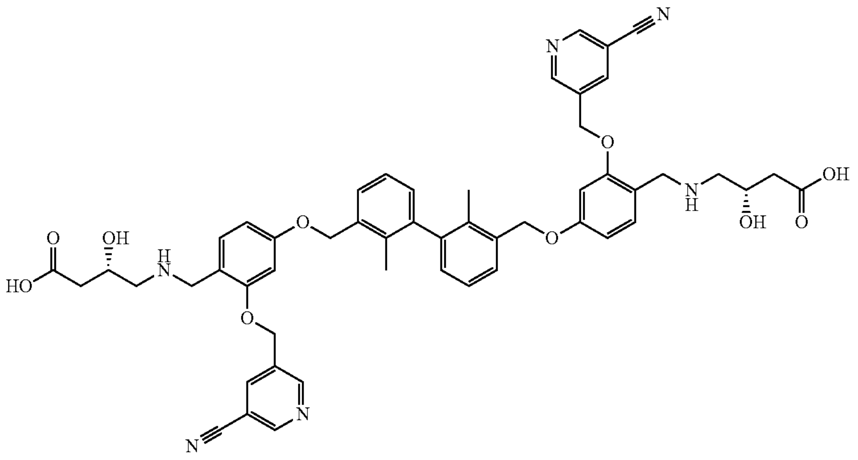 [SMILES: Cc1c(COc2ccc(CNC[C@@H](O)CC(=O)O)c(OCc3cncc(C#N)c3)c2)cccc1-c1cccc(COc2ccc(CNC[C@@H](O)CC(=O)O)c(OCc3cncc(C#N)c3)c2)c1C]

The title compound was synthesized according to general reductive amination procedure C. [M+1]=922.0. $^1$H NMR (400 MHz, Methanol-$d_4$) δ 8.55-8.40 (m, 6H), 7.45 (d, J=7.6 Hz, 2H), 7.38 (d, J=8.4 Hz, 2H), 7.27 (t, J=7.6 Hz, 2H), 7.08 (d, J=7.5 Hz, 2H), 6.88 (d, J=2.3 Hz, 2H), 6.77 (dd, J=8.4, 2.2 Hz, 2H), 5.28 (s, 4H), 5.17 (s, 4H), 4.20-4.05 (m, 6H), 3.05-2.75 (m, 4H), 2.55-2.45 (m, 4H), 1.99 (s, 6H).

Example 249: 3,3'-((((2,2'-dimethyl-[1,1'-biphenyl]-3,3'-diyl)bis(methylene))bis(oxy))bis(5-bromo-2-methoxypyridine-6,3-diyl))dimorpholine (or 3,3'-(6,6'-(((2,2'-dimethyl-[1,1'-biphenyl]-3,3'-diyl)bis(methylene))bis(oxy))bis(5-bromo-2-methoxypyridine-6,3-diyl))dimorpholine)

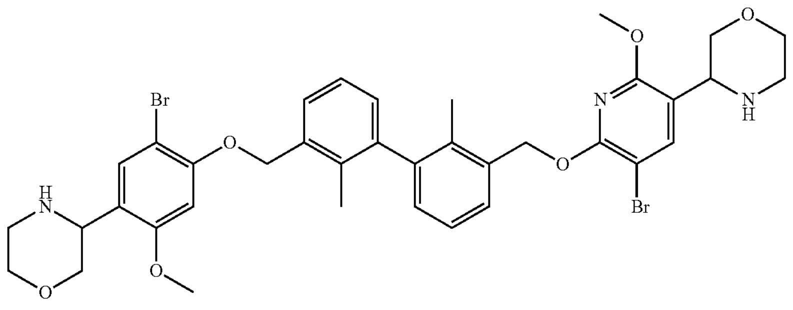 [SMILES: COc1cc(OCc2cccc(-c3cccc(COc4nc(OC)c(C5COCCN5)cc4Br)c3C)c2C)c(Br)cc1C1COCCN1]

To a 2-dram vial was added 6,6'-(((2,2'-dimethyl-[1,1'-biphenyl]-3,3'-diyl)bis(methylene))bis(oxy))bis(5-bromo-2-methoxynicotinaldehyde) (100 mg, 0.15 mmol), 2-((tributylstannyl)methoxy)ethan-1-amine (55 mg, 0.15 mmol, 1.0 equiv), 4 Angstrom molecular sieves (15 mg), and methylene chloride (1.0 mL, 0.15M) at room temperature. The mixture was stirred for 2 hours. In a separate vial was added copper(II) triflate (54 mg, 0.15 mmol, 1.0 equiv), 2,6-lutidine (18 □L, 0.15 mmol, 1.0 equiv), methylene chloride (1.0 mL), and hexafluoro-2-propanol (0.6 mL) at room temperature. The mixture was stirred for 2 hours. To the solution of copper was added the suspension of tin reagent (after filtering off the molecular sieves) dropwise, and the resulting mixture was stirred overnight at room temperature. The suspension was diluted with N,N-dimethylformamide and loaded directly onto a reverse phase preparative HPLC to yield 3,3'-((((2,2'-dimethyl-[1,1'-biphenyl]-3,3'-diyl)bis(methylene))bis(oxy))bis(5-bromo-2-methoxypyridine-6,3-diyl))dimorpholine. [M+1]=785.5. $^1$H NMR (400 MHz, Methanol-$d_4$) δ 7.96 (s, 2H), 7.47 (dd, J=7.4, 1.3 Hz, 2H), 7.24 (t, J=7.6 Hz, 2H), 7.07 (dd, J=7.7, 1.4 Hz, 2H), 5.58 (s, 4H), 4.57 (dd, J=9.7, 3.9 Hz, 2H), 4.18-3.93 (m, 12H), 3.83 (ddd, J=13.3, 9.3, 4.3 Hz, 2H), 3.36 (d, J=3.5 Hz, 4H), 2.09 (s, 6H).

Example 250: N,N'-((((((((2,2'-dimethyl-[1,1'-biphenyl]-3,3'-diyl)bis(methylene))bis(oxy))bis(2-(5-cyanopyridin-3-yl)-4,1-phenylene))bis(methylene))bis(azanediyl))bis(ethane-2,1-diyl))diacetamide

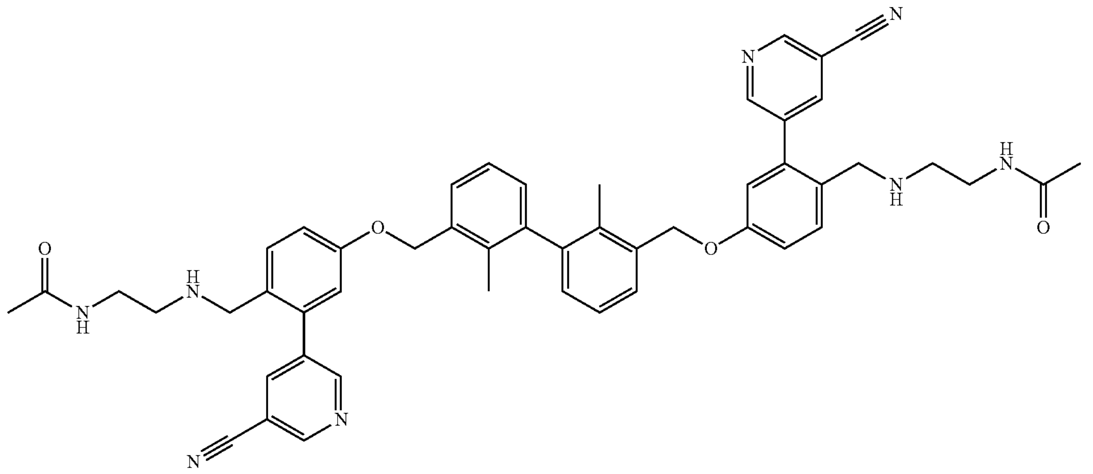 [SMILES: CC(=O)NCCNCc1ccc(OCc2cccc(-c3cccc(COc4ccc(CNCCNC(C)=O)c(-c5cncc(C#N)c5)c4)c3C)c2C)cc1-c1cncc(C#N)c1]

The title compound was synthesized according to general reductive amination procedure C. [M+1]=828.0. $^1$H NMR (400 MHz, Methanol-$d_4$) δ 8.98 (d, J=1.9 Hz, 2H), 8.82 (d, J=2.1 Hz, 2H), 8.25 (t, J=2.1 Hz, 2H), 7.63 (d, J=8.6 Hz, 2H), 7.48-7.36 (m, 2H), 7.34-7.19 (m, 4H), 7.14-6.98 (m, 4H), 5.23 (s, 4H), 4.16 (s, 4H), 3.35 (t, J=5.6 Hz, 4H), 3.04 (t, J=5.6 Hz, 4H), 2.03 (s, 6H), 1.94 (s, 6H).

Example 251: (S)-4-(((6-((3'-(((5-((((S)-3-carboxy-2-hydroxypropyl)amino)methyl)-1-((5-cyanopyridin-3-yl)methyl)-6-oxo-1,6-dihydropyridin-2-yl)oxy)methyl)-2,2'-dimethyl-[1,1'-biphenyl]-3-yl)methoxy)-2-((5-cyanopyridin-3-yl)methoxy)pyridin-3-yl)methyl)amino)-3-hydroxybutanoic acid

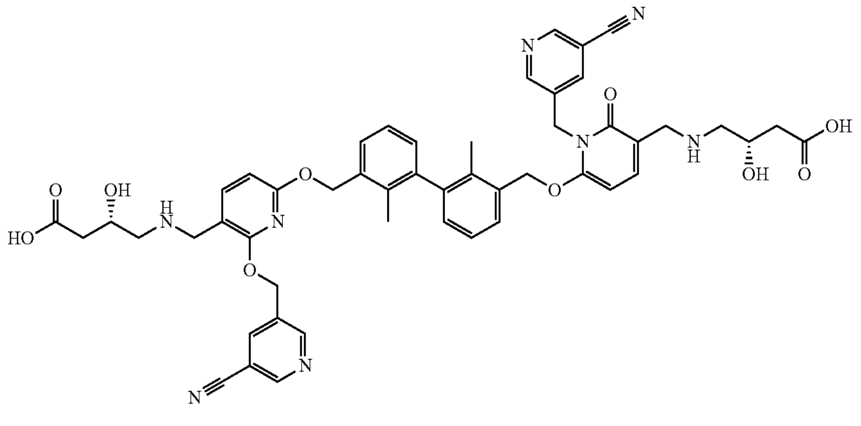 [SMILES: Cc1c(COc2ccc(CNC[C@@H](O)CC(=O)O)c(OCc3cncc(C#N)c3)n2)cccc1-c1cccc(COc2ccc(CNC[C@@H](O)CC(=O)O)c(=O)n2Cc2cncc(C#N)c2)c1C]

The title compound was synthesized according to general reductive amination procedure C. [M+1]=924.0. $^1$H NMR (400 MHz, Methanol-$d_4$) δ 8.92-8.80 (m, 3H), 8.20 (dd, J=48.0 Hz, 2H), 7.75 (dd, J=8.0, 5.8 Hz, 2H), 7.38 (dd, J=17.4, 7.6 Hz, 2H), 7.28-7.20 (m, 2H), 7.09-7.00 (m, 2H), 6.58 (dd, J=15.5, 8.1 Hz, 2H), 5.63-5.55 (m, 1H), 5.54-5.35 (m, 3H), 4.30-4.20 (m, 4H), 3.49-3.46 (m, 2H), 3.25-2.80 (m, 9H), 2.54 (d, J=6.4 Hz, 2HO, 2.49-2.45 (m, 2H), 2.01 (d, J=16.2 Hz, 6H).

Example 252: (3R,3'R)-4,4'-((((((2,2'-dimethyl-[1,1'-biphenyl]-3,3'-diyl)bis(methylene))bis(oxy))bis(5-bromo-2-((5-cyanopyridin-3-yl)methoxy)pyridine-6,3-diyl))bis(methylene))bis(azanediyl))bis(3-hydroxybutanoic acid) (or (3R,3'R)-4,4'-(((6,6'-(((2,2'-dimethyl-[1,1'-biphenyl]-3,3'-diyl)bis(methylene))bis(oxy))bis(5-bromo-2-((5-cyanopyridin-3-yl)methoxy)pyridine-6,3-diyl))bis(methylene))bis(azanediyl))bis(3-hydroxybutanoic acid))

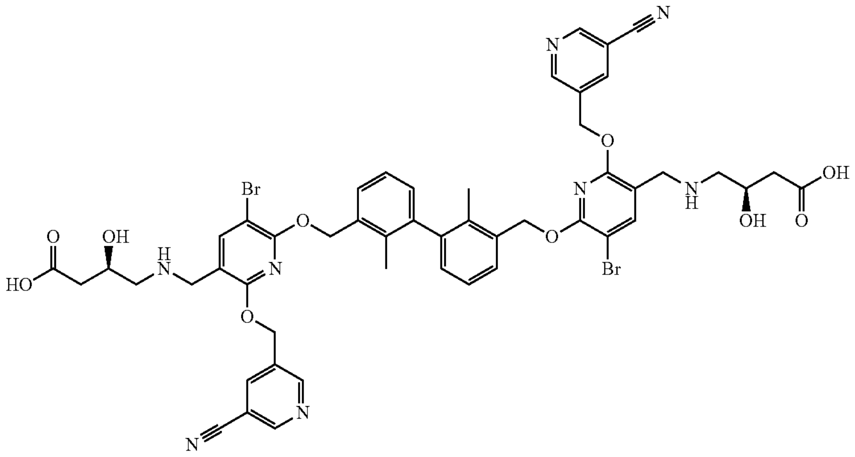 [SMILES: Cc1c(COc2nc(OCc3cncc(C#N)c3)c(CNC[C@H](O)CC(=O)O)cc2Br)cccc1-c1cccc(COc2nc(OCc3cncc(C#N)c3)c(CNC[C@H](O)CC(=O)O)cc2Br)c1C]

The title compound was synthesized according to general reductive amination procedure C. [M+1]=1081.8. $^1$H NMR (400 MHz, Methanol-$d_4$) δ 8.91 (dd, J=28.7, 2.1 Hz, 5H), 8.33 (s, 2H), 7.40 (d, J=7.6 Hz, 2H), 7.23 (t, J=7.6 Hz, 2H), 7.08 (d, J=7.5 Hz, 2H), 5.61 (s, 2H), 5.48 (s, 6H), 4.24 (s, 4H), 3.47 (s, 2H), 3.26-3.21 (m, 2H), 3.12 (s, 2H), 3.04 (d, J=10.0 Hz, 2H), 2.54 (d, J=6.3 Hz, 4H), 2.04 (s, 4H).

Example 253: (3S,3'S)-4,4'-((((((2,2'-dimethyl-[1,1'-biphenyl]-3,3'-diyl)bis(methylene))bis(oxy))bis(5-bromo-2-((6-methoxypyridin-3-yl)methoxy)pyridine-6,3-diyl))bis(methylene))bis(azanediyl))bis(3-hydroxybutanoic acid) (or (3S,3'S)-4,4'-(((6,6'-(((2,2'-dimethyl-[1,1'-biphenyl]-3,3'-diyl)bis(methylene))bis(oxy))bis(5-bromo-2-((6-methoxypyridin-3-yl)methoxy)pyridine-6,3-diyl))bis(methylene))bis(azanediyl))bis(3-hydroxybutanoic acid))

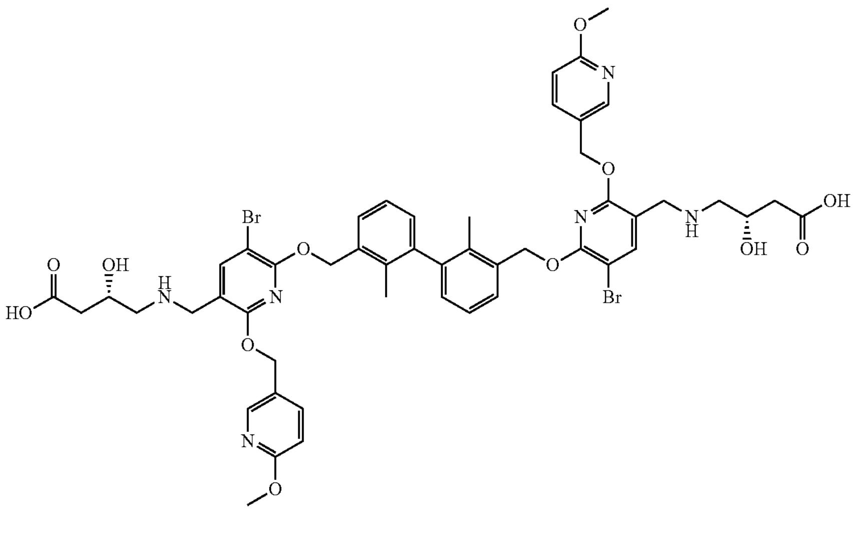 [SMILES: COc1ccc(COc2nc(OCc3cccc(-c4cccc(COc5nc(OCc6ccc(OC)nc6)c(CNC[C@@H](O)CC(=O)O)cc5Br)c4C)c3C)c(Br)cc2CNC[C@@H](O)CC(=O)O)cn1]

The title compound was synthesized according to general reductive amination procedure C. [M+1]=1091.8. $^1$H NMR (400 MHz, Methanol-$d_4$) δ 8.94-8.79 (m, 3H), 8.24 (dd, J=48.8 Hz, 2H), 7.77 (dd, J=8.1, 5.8 Hz, 2H), 7.38 (dd, J=17.0, 7.5 Hz, 2H), 7.28-7.20 (m, 2H), 7.00-7.03 (m, 2H), 6.49 (dd, J=15.4, 8.1 Hz, 2H), 5.63-5.55 (m, 1H), 5.54-5.35 (m, 3H), 4.30-4.19 (m, 4H), 3.49-3.46 (m, 2H), 3.25-2.80 (m, 9H), 2.54 (d, J=6.4 Hz, 2HO, 2.49-2.45 (m, 2H), 1.98 (d, J=16.2 Hz, 6H).

Example 254: 5,5'-((((((2,2'-dimethyl-[1,1'-biphenyl]-3,3'-diyl)bis(methylene))bis(oxy))bis(4-bromo-6-(((2-hydroxyethyl)amino)methyl)-3,1-phenylene)) bis(oxy))bis(methylene))dinicotinonitrile (or 5,5'-((((((2,2'-dimethyl-[1,1'-biphenyl]-3,3'-diyl)bis (methylene))bis(oxy))bis(4-bromo-2-(((2-hydroxyethyl)amino)methyl)-5,1-phenylene))bis (oxy))bis(methylene))dinicotinonitrile)

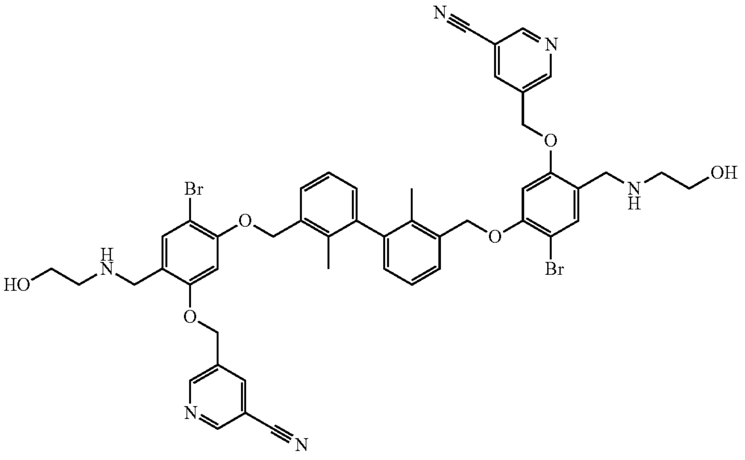 [SMILES: Cc1c(COc2cc(OCc3cncc(C#N)c3)c(CNCCO)cc2Br)cccc1-c1cccc(COc2cc(OCc3cncc(C#N)c3)c(CNCCO)cc2Br)c1C]

The title compound was synthesized according to general reductive amination procedure C. [M+1]=103.3. $^1$H NMR (400 MHz, Acetonitrile-$d_3$) δ 8.94 (dd, J=7.2, 2.0 Hz, 4H), 8.29 (t, J=2.1 Hz, 2H), 7.62 (s, 2H), 7.57-7.48 (m, 2H), 7.33 (t, J=7.6 Hz, 2H), 7.18 (dd, J=7.7, 1.4 Hz, 2H), 6.94 (s, 2H), 5.30 (d, J=7.8 Hz, 8H), 4.21 (s, 4H), 3.75-3.67 (m, 4H), 3.08 (d, J=6.6 Hz, 4H), 2.11 (s, 6H).

Example 255: 1,1'-(((((2,2'-dimethyl-[1,1'-biphenyl]-3,3'-diyl)bis(methylene))bis(oxy))bis(5-bromo-2-methoxypyridine-6,3-diyl))bis(methylene))bis(azetidin-3-ol) (or 1,1'-((6,6'-(((2,2'-dimethyl-[1,1'-biphenyl]-3,3'-diyl)bis(methylene))bis(oxy))bis(5-bromo-2-methoxypyridine-6,3-diyl))bis(methylene)) bis(azetidin-3-ol))

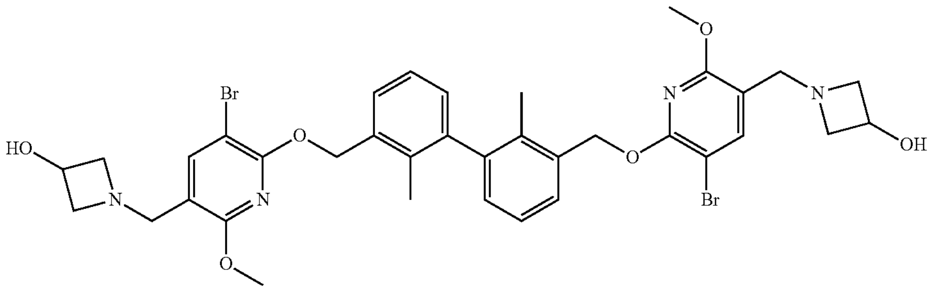 [SMILES: COc1nc(OCc2cccc(-c3cccc(COc4nc(OC)c(CN5CC(O)C5)cc4Br)c3C)c2C)c(Br)cc1CN1CC(O)C1]

The title compound was synthesized according to general reductive amination procedure C. [M+1]=785.5. $^1$H NMR (400 MHz, Methanol-$d_4$) δ 7.96 (s, 2H), 7.48 (d, J=7.3 Hz, 2H), 7.25 (t, J=7.6 Hz, 2H), 7.08 (dd, J=7.7, 1.4 Hz, 2H), 5.58 (s, 4H), 4.63-4.53 (m, 2H), 4.35-4.45 (m, 8H), 4.10-4.00 (m, 10H), 2.09 (s, 6H).

Example 256: 1,1'-(((((2,2'-dimethyl-[1,1'-biphenyl]-3,3'-diyl)bis(methylene))bis(oxy))bis(5-bromo-2-methoxypyridine-6,3-diyl))bis(methylene))bis(N-methylazetidine-3-carboxamide) (or 1,1'-((6,6'-(((2,2'-dimethyl-[1,1'-biphenyl]-3,3'-diyl)bis(methylene))bis(oxy))bis(5-bromo-2-methoxypyridine-6,3-diyl))bis(methylene))bis(N-methylazetidine-3-carboxamide))

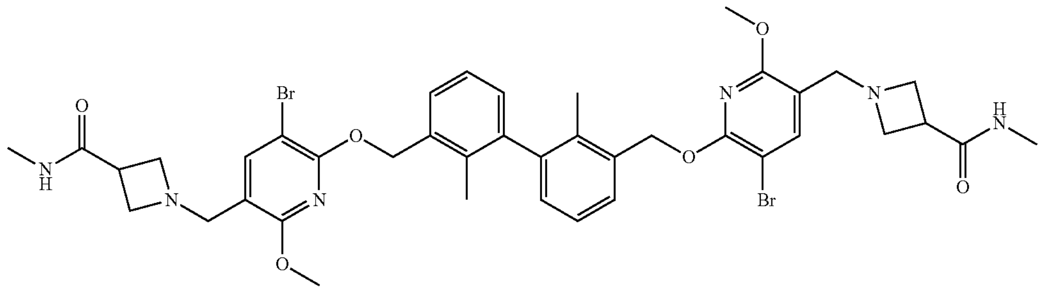

The title compound was synthesized according to general reductive amination procedure C. [M+1]=867.6. $^1$H NMR (400 MHz, Methanol-$d_4$) δ 7.96 (s, 2H), 7.48 (d, J=7.2 Hz, 2H), 7.25 (t, J=7.6 Hz, 2H), 7.08 (dd, J=7.7, 1.4 Hz, 2H), 5.58 (s, 4H), 4.63-4.53 (m, 2H), 4.35-4.45 (m, 8H), 4.15-4.05 (m, 10H), 3.52 (s, 6H), 2.05 (s, 6H).

Example 257: 5,5'-((((((2,2'-dimethyl-[1,1'-biphenyl]-3,3'-diyl)bis(methylene))bis(oxy))bis(4-bromo-6-((((R)-2,3-dihydroxypropyl)amino)methyl)-3,1-phenylene))bis(oxy))bis(methylene))dinicotinonitrile (or 5,5'-((((R)-(((2,2'-dimethyl-[1,1'-biphenyl]-3,3'-diyl)bis(methylene))bis(oxy))bis(4-bromo-2-((((R)-2,3-dihydroxypropyl)amino)methyl)-5,1-phenylene))bis(oxy))bis(methylene))dinicotinonitrile)

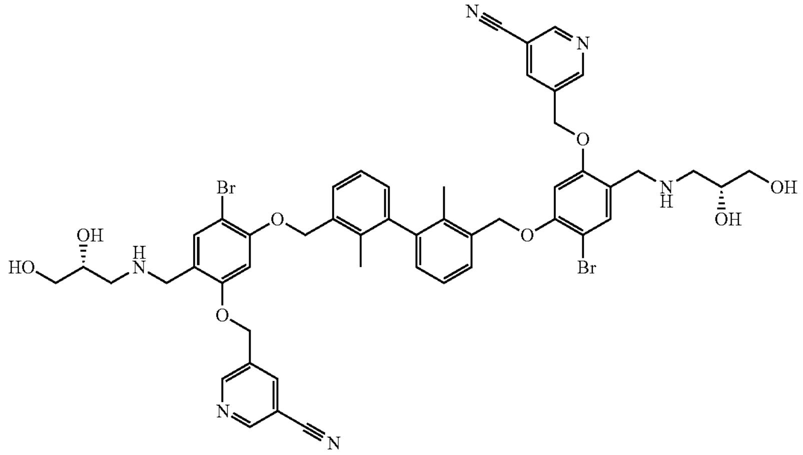 [SMILES: Cc1c(COc2cc(OCc3cncc(C#N)c3)c(CNC[C@@H](O)CO)cc2Br)cccc1-c1cccc(COc2cc(OCc3cncc(C#N)c3)c(CNC[C@@H](O)CO)cc2Br)c1C]

The title compound was synthesized according to general reductive amination procedure C. [M+1]=1023.8. $^1$H NMR (400 MHz, Acetonitrile-$d_3$) 6 8.98-8.84 (m, 4H), 8.28 (s, 2H), 7.62 (d, J=6.0 Hz, 2H), 7.54 (d, J=7.6 Hz, 2H), 7.33 (t, J=7.6 Hz, 2H), 7.18 (d, J=7.5 Hz, 2H), 6.93 (s, 2H), 5.30 (d, J=6.9 Hz, 8H), 4.21 (d, J=10.3 Hz, 4H), 3.53 (s, 4H), 3.09 (d, J=38.5 Hz, 6H), 2.08 (s, 6H).

Example 258: 5,5'-((((((2,2'-dimethyl-[1,1'-biphenyl]-3,3'-diyl)bis(methylene))bis(oxy))bis(4-bromo-6-(((R)-2-(hydroxymethyl)azetidin-1-yl)methyl)-3,1-phenylene))bis(oxy))bis(methylene))dinicotinonitrile (or 5,5'-((((R)-(((2,2'-dimethyl-[1,1'-biphenyl]-3,3'-diyl)bis(methylene))bis(oxy))bis(4-bromo-2-(((R)-2-(hydroxymethyl)azetidin-1-yl)methyl)-5,1-phenylene))bis(oxy))bis(methylene))dinicotinonitrile)

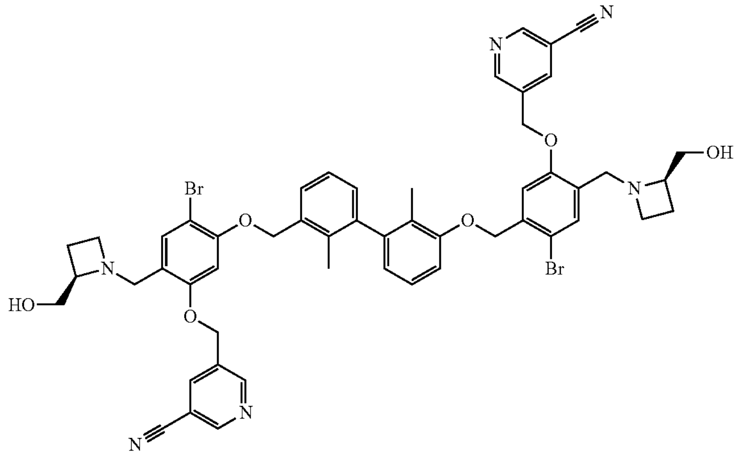 [SMILES: Cc1c(COc2cc(OCc3cncc(C#N)c3)c(CN3CC[C@@H]3CO)cc2Br)cccc1-c1cccc(OCc2cc(OCc3cncc(C#N)c3)c(CN3CC[C@@H]3CO)cc2Br)c1C]

The title compound was synthesized according to general reductive amination procedure C. [M+1]=1015.8. $^1$H NMR (400 MHz, DMSO-$d_6$) δ 9.03 (dd, J=6.5, 2.0 Hz, 4H), 8.50 (s, 2H), 7.69 (s, 2H), 7.52 (d, J=7.6 Hz, 2H), 7.29 (t, J=7.6 Hz, 2H), 7.18 (s, 2H), 7.16-6.99 (m, 2H), 5.37 (s, 4H), 5.31 (s, 4H), 4.53-4.12 (m, 6H), 3.92 (d, J=8.2 Hz, 2H), 3.77 (t, J=6.9 Hz, 2H), 3.55 (d, J=5.6 Hz, 4H), 2.21 (q, J=8.4 Hz, 4H), 2.03 (s, 6H).

Example 259:5,5'-((((((2,2'-dimethyl-[1,1'-biphenyl]-3,3'-diyl)bis(methylene))bis(oxy))bis(4-bromo-6-((((S)-2,3-dihydroxypropyl)amino)methyl)-3,1-phenylene))bis(oxy))bis(methylene))dinicotinonitrile (or 5,5'-((((S)-(((2,2'-dimethyl-[1,1'-biphenyl]-3,3'-diyl)bis(methylene))bis(oxy))bis(4-bromo-2-((((S)-2,3-dihydroxypropyl)amino)methyl)-5,1-phenylene))bis(oxy))bis(methylene))dinicotinonitrile)

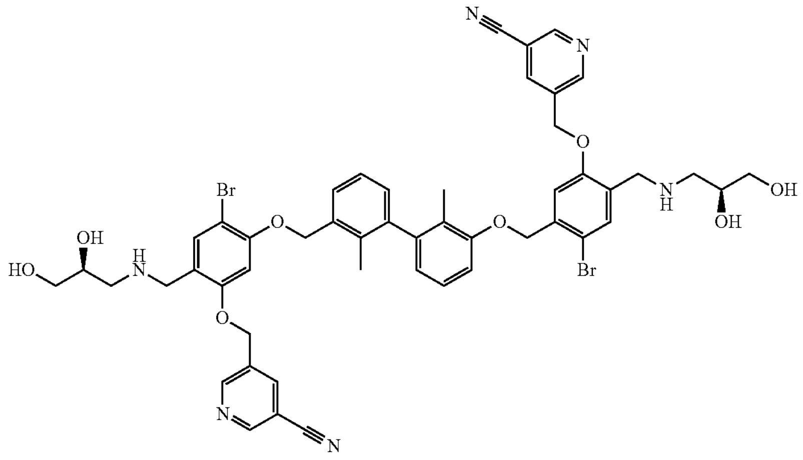 [SMILES: Cc1c(COc2cc(OCc3cncc(C#N)c3)c(CNC[C@H](O)CO)cc2Br)cccc1-c1cccc(OCc2cc(OCc3cncc(C#N)c3)c(CNC[C@H](O)CO)cc2Br)c1C]

The title compound was synthesized according to general reductive amination procedure C. [M+1]=1023.8. $^1$H NMR (400 MHz, Acetonitrile-$d_3$) δ 8.98-8.84 (m, 4H), 8.28 (s, 2H), 7.62 (d, J=6.0 Hz, 2H), 7.54 (d, J=7.6 Hz, 2H), 7.33 (t, J=7.6 Hz, 2H), 7.18 (d, J=7.5 Hz, 2H), 6.93 (s, 2H), 5.30 (d, J=6.9 Hz, 8H), 4.21 (d, J=10.3 Hz, 4H), 3.53 (s, 4H), 3.09 (d, J=38.5 Hz, 6H), 2.08 (s, 6H).

Example 260: 5,5'-((((((2,2'-dimethyl-[1,1'-biphenyl]-3,3'-diyl)bis(methylene))bis(oxy))bis(4-bromo-6-(((S)-2-(hydroxymethyl)azetidin-1-yl)methyl)-3,1-phenylene))bis(oxy))bis(methylene))dinicotinonitrile (or 5,5'-((((S)-(((2,2'-dimethyl-[1,1'-biphenyl]-3,3'-diyl)bis(methylene))bis(oxy))bis(4-bromo-2-(((S)-2-(hydroxymethyl)azetidin-1-yl)methyl)-5,1-phenylene))bis(oxy))bis(methylene))dinicotinonitrile)

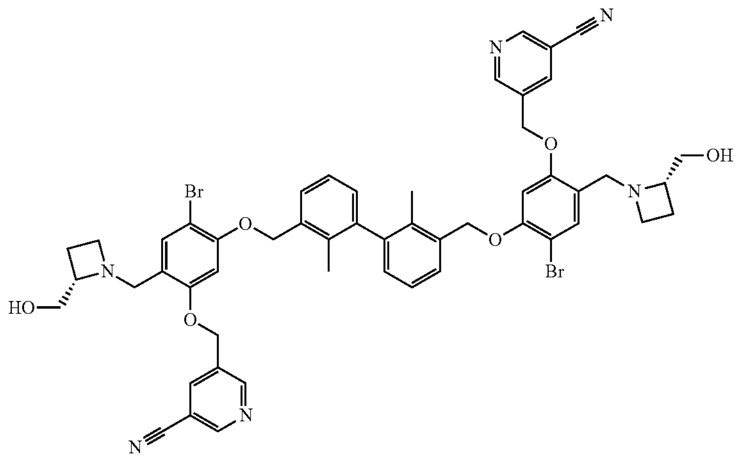 [SMILES: Cc1c(COc2cc(OCc3cncc(C#N)c3)c(CN3CC[C@H]3CO)cc2Br)cccc1-c1cccc(COc2cc(OCc3cncc(C#N)c3)c(CN3CC[C@H]3CO)cc2Br)c1C]

The title compound was synthesized according to genera reductive amination procedure C. [M+1]=1015.8. $^1$H NMR (400 MHz, DMSO-$d_6$) δ 9.03 (dd, J=6.5, 2.0 Hz, 4H), 8.50 (s, 2H), 7.69 (s, 2H), 7.52 (d, J=7.6 Hz, 2H), 7.29 (t, J=7.6 Hz, 2H), 7.18 (s, 2H), 7.16-6.99 (m, 2H), 5.37 (s, 4H), 5.31 (s, 4H), 4.53-4.12 (m, 6H), 3.92 (d, J=8.2 Hz, 2H), 3.77 (t, J=6.9 Hz, 2H), 3.55 (d, J=5.6 Hz, 4H), 2.21 (q, J=8.4 Hz, 4H), 2.03 (s, 6H).

Example 261: 5,5'-((((((2,2'-dimethyl-[1,1'-biphenyl]-3,3'-diyl)bis(methylene))bis(oxy))bis(6-((((1H-imidazol-2-yl)methyl)amino)methyl)-4-bromo-3,1-phenylene))bis(oxy))bis(methylene))dinicotinonitrile (or 5,5'-((((((2,2'-dimethyl-[1,1'-biphenyl]-3,3'-diyl)bis(methylene))bis(oxy))bis(2-((((1H-imidazol-2-yl)methyl)amino)methyl)-4-bromo-5,1-phenylene))bis(oxy))bis(methylene))dinicotinonitrile)

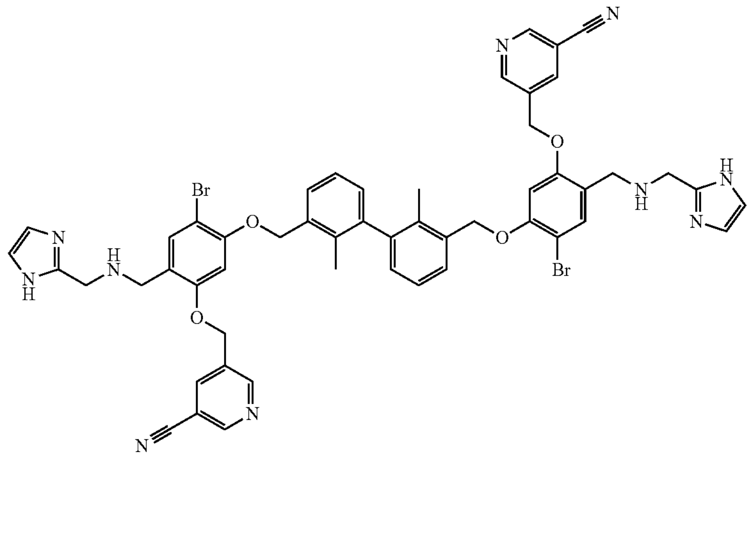 [SMILES: Cc1c(COc2cc(OCc3cncc(C#N)c3)c(CNCc3ncc[nH]3)cc2Br)cccc1-c1cccc(COc2cc(OCc3cncc(C#N)c3)c(CNCc3ncc[nH]3)cc2Br)c1C]

The title compound was synthesized according to general reductive amination procedure C. [M+1]=1035.8. $^1H$ NMR (400 MHz, DMSO-$d_6$) δ 9.09-8.89 (m, 4H), 8.43 (s, 2H), 7.68 (s, 2H), 7.51 (d, J=7.6 Hz, 2H), 7.36-7.19 (m, 6H), 7.15 (s, 2H), 7.10 (d, J=7.6 Hz, 2H), 5.32 (d, J=15.7 Hz, 8H), 4.15 (d, J=11.4 Hz, 8H), 2.03 (s, 6H).

Example 262: (3S,3'S)-4,4'-((((((2,2'-dimethyl-[1,1'-biphenyl]-3,3'-diyl)bis(methylene))bis(oxy))bis(5-chloro-2-(thiazol-2-ylmethoxy)-4,1-phenylene))bis(methylene))bis(azanediyl))bis(3-hydroxybutanoic acid)

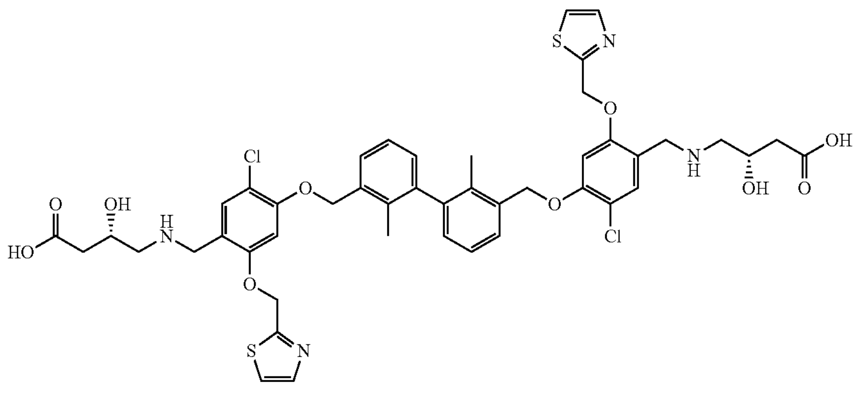 [SMILES: Cc1c(COc2cc(OCc3nccs3)c(CNC[C@@H](O)CC(=O)O)cc2Cl)cccc1-c1cccc(COc2cc(OCc3nccs3)c(CNC[C@@H](O)CC(=O)O)cc2Cl)c1C]

The title compound was synthesized according to general reductive amination procedure C. [M+1]=952.9. $^1H$ NMR (400 MHz, Acetonitrile-$d_3$) δ 7.83 (d, J=3.3 Hz, 2H), 7.59 (d, J=2.8 Hz, 2H), 7.50 (d, J=7.6 Hz, 2H), 7.44 (s, 2H), 7.30 (t, J=7.6 Hz, 2H), 7.15 (d, J=7.6 Hz, 2H), 7.07 (s, 2H), 5.67 (s, 4H), 5.25 (s, 4H), 4.29 (d, J=43.0 Hz, 6H), 3.14 (d, J=52.2 Hz, 4H), 2.53 (t, J=7.8 Hz, 4H), 2.05 (s, 6H).

Example 263: (3S,3'S)-4,4'-((((((2,2'-dimethyl-[1,1'-biphenyl]-3,3'-diyl)bis(methylene))bis(oxy))bis(2-methoxy-5-(methylsulfonyl)pyridine-6,3-diyl))bis(methylene))bis(azanediyl))bis(3-hydroxybutanoic acid) (or (3S,3'S)-4,4'-(((6,6'-(((2,2'-dimethyl-[1,1'-biphenyl]-3,3'-diyl)bis(methylene))bis(oxy))bis(2-methoxy-5-(methylsulfonyl)pyridine-6,3-diyl))bis(methylene))bis(azanediyl))bis(3-hydroxybutanoic acid))

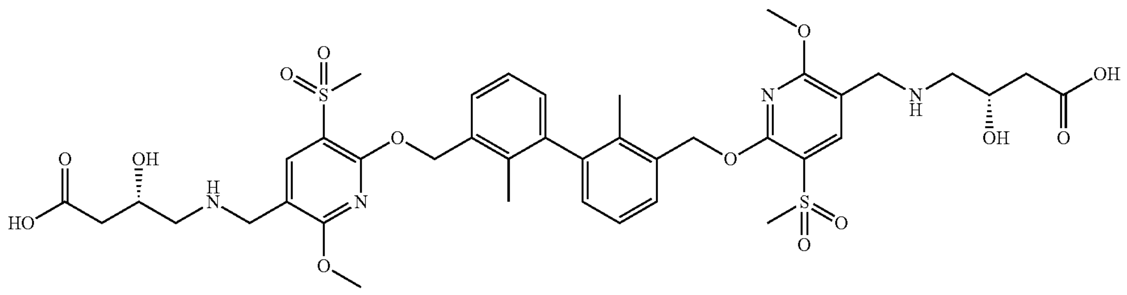 [SMILES: COc1nc(OCc2cccc(-c3cccc(COc4nc(OC)c(CNC[C@@H](O)CC(=O)O)cc4S(C)(=O)=O)c3C)c2C)c(S(C)(=O)=O)cc1CNC[C@@H](O)CC(=O)O]

The title compound was synthesized according to general reductive amination procedure C. [M+1]=875.0. $^1H$ NMR (400 MHz, Methanol-d4) δ 8.21 (s, 2H), 7.50 (d, J=7.5 Hz, 2H), 7.28 (t, J=7.6 Hz, 2H), 7.11-7.00 (m, 2H), 5.55 (s, 4H), 4.31-4.22 (m, 2H), 4.14 (s, 4H), 4.05 (s, 6H), 3.20 (dd, J=12.7, 3.1 Hz, 2H), 3.01 (s, 6H), 2.99 (dd, J=12.7, 9.9 Hz, 2H), 2.54 (d, J=6.3 Hz, 4H), 2.12 (s, 6H).

Example 264: 2,2'-(((((((2,2'-dimethyl-[1,1'-biphenyl]-3,3'-diyl)bis(methylene))bis(oxy))bis(5-bromo-2-methoxypyridine-6,3-diyl))bis(methylene))bis(azanediyl))bis(ethane-2,1-diyl))bis(isothiazolidine 1,1-dioxide) (or 2,2'-((((6,6'-(((2,2'-dimethyl-[1,1'-biphenyl]-3,3'-diyl)bis(methylene))bis(oxy))bis(5-bromo-2-methoxypyridine-6,3-diyl))bis(methylene))bis(azanediyl))bis(ethane-2,1-diyl))bis(isothiazolidine 1,1-dioxide))

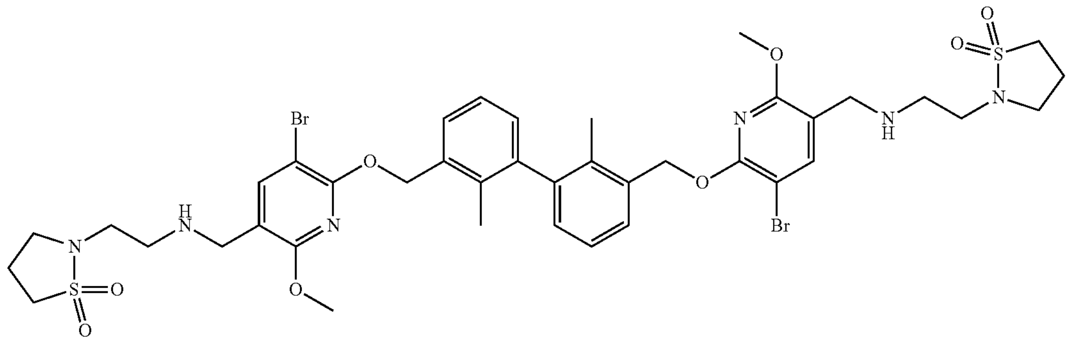 [SMILES: COc1nc(OCc2cccc(-c3cccc(COc4nc(OC)c(CNCCN5CCCS5(=O)=O)cc4Br)c3C)c2C)c(Br)cc1CNCCN1CCCS1(=O)=O]

The title compound was synthesized according to general reductive amination procedure C. [M+1]=967.8. $^1$H NMR (400 MHz, Methanol-$d_4$) δ 7.95 (s, 2H), 7.52-7.42 (m, 2H), 7.24 (t, J=7.6 Hz, 2H), 7.13-7.02 (m, 2H), 5.58 (s, 4H), 4.18 (s, 4H), 4.06 (s, 6H), 3.54-3.03 (m, 8H), 2.37 (p, J=6.9 Hz, 4H), 2.09 (s, 6H).

Example 265: (3S,3'S)-4,4'-((((((2,2'-dimethyl-[1,1'-biphenyl]-3,3'-diyl)bis(methylene))bis(oxy))bis(2-((5-cyano-2-fluorobenzyl)oxy)-4,1-phenylene))bis(methylene))bis(azanediyl))bis(3-hydroxybutanoic acid)

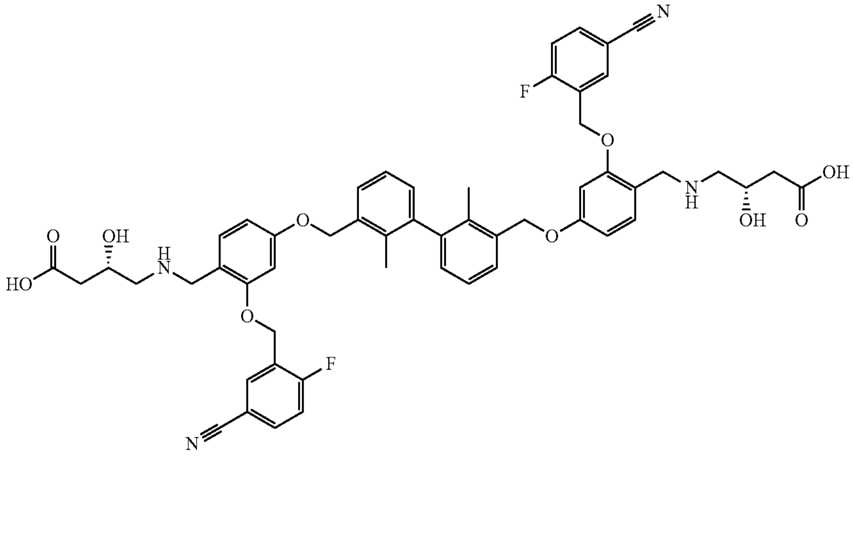 [SMILES: Cc1c(COc2ccc(CNC[C@@H](O)CC(=O)O)c(OCc3cc(C#N)ccc3F)c2)cccc1-c1cccc(COc2ccc(CNC[C@@H](O)CC(=O)O)c(OCc3cc(C#N)ccc3F)c2)c1C]

The title compound was synthesized according to general reductive amination procedure C. [M+1]=956.0. $^1$H NMR (400 MHz, Methanol-$d_4$) δ 7.92 (dd, J=6.1, 2.3 Hz, 2H), 7.89-7.82 (m, 2H), 7.46-7.32 (m, 6H), 7.25 (t, J=7.6 Hz, 2H), 7.11-7.05 (m, 2H), 6.82 (d, J=2.3 Hz, 2H), 6.76 (dd, J=8.4, 2.3 Hz, 2H), 5.22 (s, 4H), 5.17 (s, 4H), 4.23 (s, 6H), 3.18 (dd, J=12.7, 3.0 Hz, 2H), 2.96 (dd, J=12.7, 9.8 Hz, 2H), 2.51 (dd, J=6.4, 2.5 Hz, 4H), 2.03 (s, 6H).

Example 266: N,N'-((((((((2,2'-dimethyl-[1,1'-biphenyl]-3,3'-diyl)bis(methylene))bis(oxy))bis(5-bromo-2-methoxypyridine-6,3-diyl))bis(methylene))bis(azanediyl))bis(ethane-2,1-diyl))dimethanesulfonamide (or N,N'-((((6,6'-(((2,2'-dimethyl-[1,1'-biphenyl]-3,3'-diyl)bis(methylene))bis(oxy))bis(5-bromo-2-methoxypyridine-6,3-diyl))bis(methylene))bis(azanediyl))bis(ethane-2,1-diyl))dimethanesulfonamide)

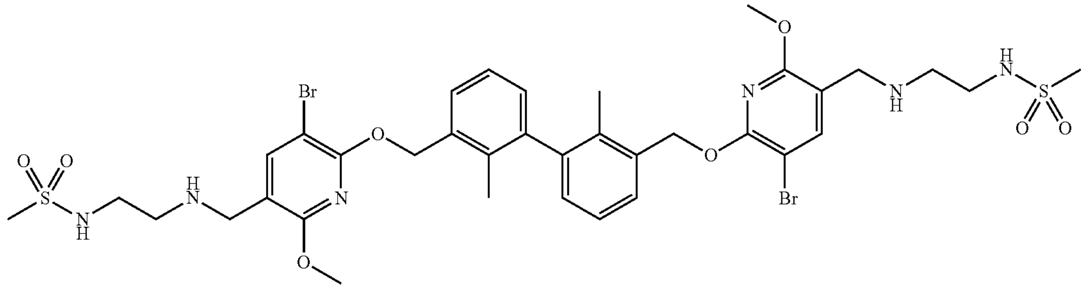

The title compound was synthesized according to general reductive amination procedure C. [M+1]=915.7. $^1$H NMR (400 MHz, Methanol-$d_4$) δ 7.94 (s, 2H), 7.53-7.39 (m, 2H), 7.24 (t, J=7.6 Hz, 2H), 7.07 (dd, J=7.8, 1.4 Hz, 2H), 5.58 (s, 4H), 4.17 (s, 4H), 4.06 (s, 6H), 3.41 (t, J=5.8 Hz, 4H), 3.18 (t, J=5.8 Hz, 4H), 3.00 (s, 6H), 2.09 (s, 6H).

Example 267: (3S,3'S)-4,4'-(((([4,4'-biindoline]-1,1'-dicarbonyl)bis(2-((5-cyanopyridin-3-yl)methoxy)-4,1-phenylene))bis(methylene))bis(azanediyl))bis(3-hydroxybutanoic acid)

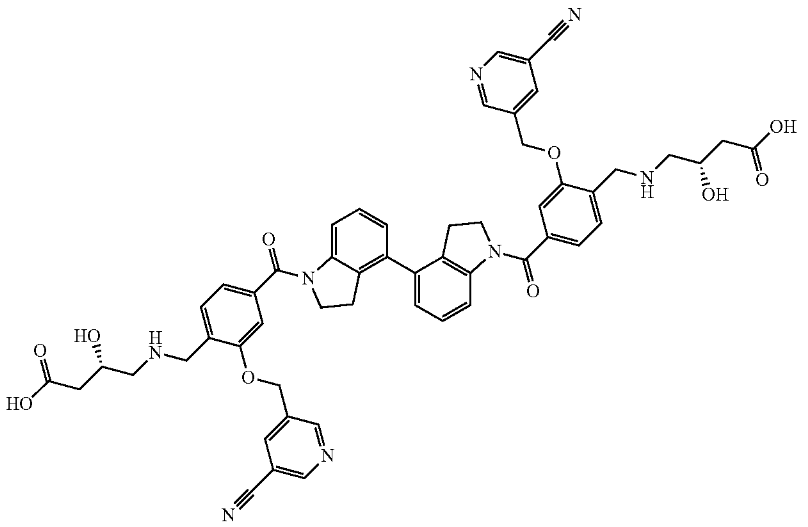 [SMILES: N#Cc1cncc(COc2cc(C(=O)N3CCc4c(-c5cccc6c5CCN6C(=O)c5ccc(CNC[C@@H](O)CC(=O)O)c(OCc6cncc(C#N)c6)c5)cccc43)ccc2CNC[C@@H](O)CC(=O)O)c1]

The title compound was synthesized according to general reductive amination procedure C. [M+1]=972.0. $^1$H NMR (400 MHz, Methanol-$d_4$) δ 8.50-8.39 (m, 6H), 7.44 (d, J=7.6 Hz, 2H), 7.38 (d, J=8.4 Hz, 2H), 7.20 (t, J=7.6 Hz, 2H), 7.08 (d, J=7.5 Hz, 2H), 6.89 (d, J=2.3 Hz, 2H), 6.65 (dd, J=8.4, 2.2 Hz, 2H), 5.26 (s, 4H), 4.25-4.01 (m, 10H), 3.64 (t, J=5.4 Hz, 4H), 3.05-2.75 (m, 4H), 2.55-2.45 (m, 4H).

Example 268: N,N'-(((((2,2'-dimethyl-[1,1'-biphenyl]-3,3'-diyl)bis(methylene))bis(oxy))bis(5-bromo-2-methoxypyridine-6,3-diyl))bis(methylene))bis(N-methyl-2-morpholinoethan-1-amine) (or N,N'-((6,6'-(((2,2'-dimethyl-[1,1'-biphenyl]-3,3'-diyl)bis(methylene))bis(oxy))bis(5-bromo-2-methoxypyridine-6,3-diyl))bis(methylene))bis(N-methyl-2-morpholinoethan-1-amine))

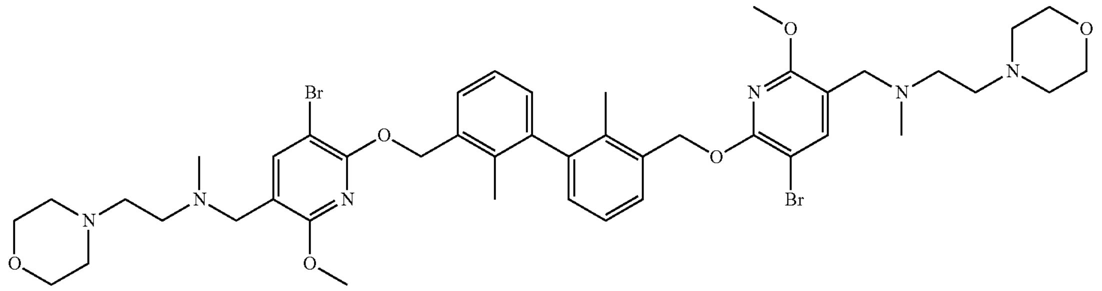 [SMILES: COc1nc(OCc2cccc(-c3cccc(COc4nc(OC)c(CN(C)CCN5CCOCC5)cc4Br)c3C)c2C)c(Br)cc1CN(C)CCN1CCOCC1]

The title compound was synthesized according to general reductive amination procedure C. [M+1]=927.8. $^{1}$H NMR (400 MHz, Methanol-$d_4$) δ 7.98 (s, 2H), 7.48 (d, J=7.6 Hz, 2H), 7.25 (t, J=7.6 Hz, 2H), 7.16-6.99 (m, 2H), 5.60 (s, 4H), 4.23 (s, 4H), 4.06 (s, 6H), 3.70 (t, J=4.8 Hz, 6H), 3.47 (dd, J=3.3, 1.6 Hz, 2H), 3.26 (d, J=6.2 Hz, 4H), 3.12 (t, J=1.6 Hz, 2H), 2.88 (t, J=5.9 Hz, 2H), 2.82 (s, 4H), 2.63 (s, 6H), 2.10 (s, 6H).

Example 269: (3S,3'S)-4,4'-((((((2,2'-dimethyl-[1,1'-biphenyl]-3,3'-diyl)bis(methylene))bis(oxy))bis(5-bromo-2-((6-morpholinopyridin-3-yl)methoxy)pyridine-6,3-diyl))bis(methylene))bis(azanediyl))bis(3-hydroxybutanoic acid) (or (3S,3'S)-4,4'-(((6,6'-(((2,2'-dimethyl-[1,1'-biphenyl]-3,3'-diyl)bis(methylene))bis(oxy))bis(5-bromo-2-((6-morpholinopyridin-3-yl)methoxy)pyridine-6,3-diyl))bis(methylene))bis(azanediyl))bis(3-hydroxybutanoic acid))

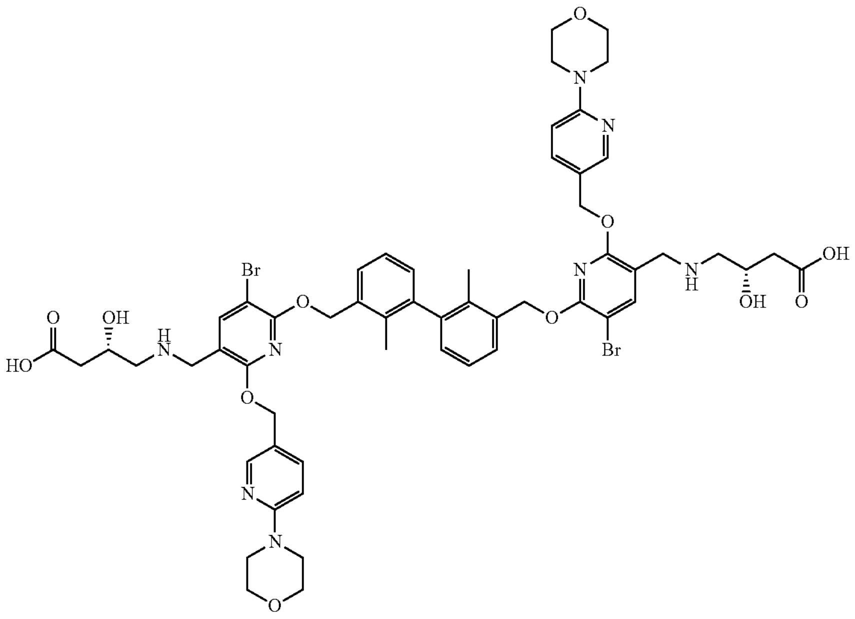 [SMILES: Cc1c(COc2nc(OCc3ccc(N4CCOCC4)nc3)c(CNC[C@@H](O)CC(=O)O)cc2Br)cccc1-c1cccc(COc2nc(OCc3ccc(N4CCOCC4)nc3)c(CNC[C@@H](O)CC(=O)O)cc2Br)c1C]

The title compound was synthesized according to general reductive amination procedure C. [M+1]=1202.0. $^1$H NMR (400 MHz, Methanol-$d_4$) δ 8.19 (d, J=2.1 Hz, 2H), 8.11 (dd, J=9.4, 2.2 Hz, 2H), 8.01 (s, 2H), 7.54-7.43 (m, 2H), 7.35-7.20 (m, 4H), 7.13-7.02 (m, 2H), 5.56 (d, J=2.1 Hz, 2H), 5.48 (s, 4H), 4.19 (s, 2H), 3.92-3.79 (m, 6H), 3.70-3.52 (m, 10H), 3.22-3.10 (m, 4H), 3.03-2.90 (m, 2H), 2.50 (d, J=7.6 Hz, 2H), 2.09 (s, 4H), 1.28 (s, 8H).

Example 270: 4,4'-(((((2,2'-dimethyl-[1,1'-biphenyl]-3,3'-diyl)bis(methylene))bis(oxy))bis(5-bromo-2-methoxypyridine-6,3-diyl))bis(methylene))bis(piperazin-2-one) (or 4,4'-((6,6'-(((2,2'-dimethyl-[1,1'-biphenyl]-3,3'-diyl)bis(methylene))bis(oxy))bis(5-bromo-2-methoxypyridine-6,3-diyl))bis(methylene))bis(piperazin-2-one))

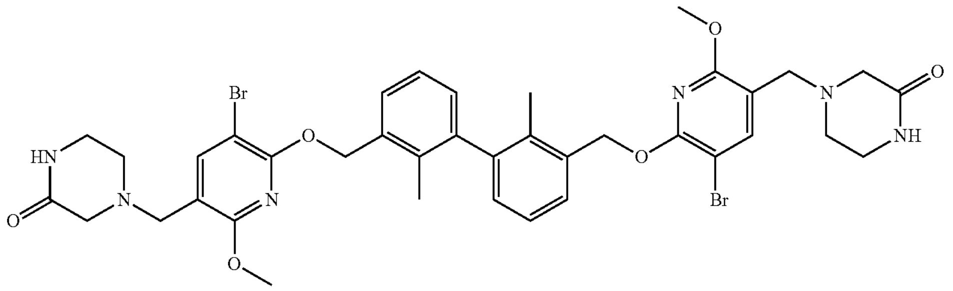 [SMILES: COc1nc(OCc2cccc(-c3cccc(COc4nc(OC)c(CN5CCNC(=O)C5)cc4Br)c3C)c2C)c(Br)cc1CN1CCNC(=O)C1]

The title compound was synthesized according to general reductive amination procedure C. [M+1]=839.6. $^1$H NMR (400 MHz, Methanol-$d_4$) δ 7.95 (s, 2H), 7.48 (d, J=7.6 Hz, 2H), 7.25 (t, J=7.7 Hz, 2H), 7.08 (d, J=7.5 Hz, 2H), 5.58 (s, 4H), 5.48 (s, 2H), 4.11 (s, 4H), 4.04 (s, 4H), 3.63 (s, 4H), 3.57 (s, 2H), 3.47 (t, J=1.6 Hz, 4H), 3.12 (t, J=1.7 Hz, 2H), 2.09 (s, 6H).

Example 271: 2,2'-((((((2,2'-dimethyl-[1,1'-biphenyl]-3,3'-diyl)bis(methylene))bis(oxy))bis(2-ethoxypyridine-6,3-diyl))bis(methylene))bis(azanediyl))bis(ethan-1-ol) (or 2,2'-(((6,6'-(((2,2'-dimethyl-[1,1'-biphenyl]-3,3'-diyl)bis(methylene))bis(oxy))bis(2-ethoxypyridine-6,3-diyl))bis(methylene))bis(azanediyl))bis(ethan-1-ol))

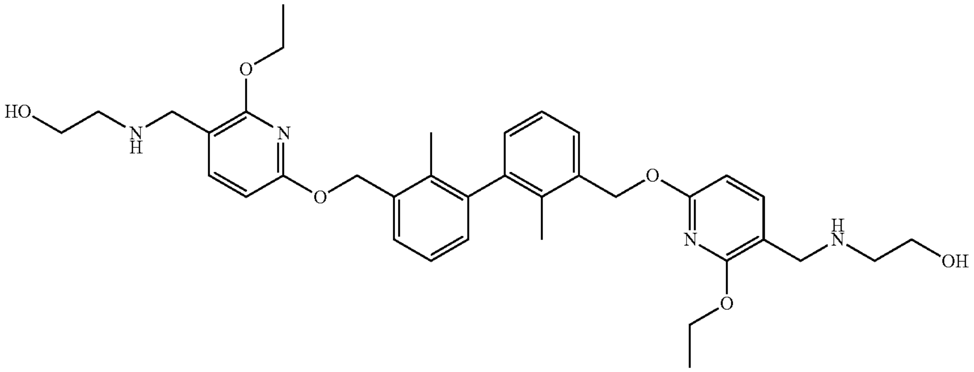 [SMILES: CCOc1nc(OCc2cccc(-c3cccc(COc4ccc(CNCCO)c(OCC)n4)c3C)c2C)ccc1CNCCO]

The title compound was synthesized according to general reductive amination procedure C. [M+1]=631.8. $^1$H NMR (400 MHz, DMSO-$d_6$) δ 7.74 (d, J=8.1 Hz, 2H), 7.40 (dd, J=7.8, 1.4 Hz, 2H), 7.24 (t, J=7.6 Hz, 2H), 7.03 (dd, J=7.7, 1.4 Hz, 2H), 6.51 (d, J=8.1 Hz, 2H), 5.41 (s, 4H), 4.35 (qd, J=7.0, 1.7 Hz, 4H), 4.02 (t, J=5.2 Hz, 4H), 3.63 (t, J=5.3 Hz, 4H), 3.09-2.83 (m, 4H), 1.98 (s, 6H), 1.30 (t, J=7.0 Hz, 6H).

Example 272: (3S,3'S)-4,4'-((((((2,2'-dimethyl-[1,1'-biphenyl]-3,3'-diyl)bis(methylene))bis(oxy))bis(2-(5-cyanopyridin-3-yl)-4,1-phenylene))bis(methylene))bis(azanediyl))bis(3-hydroxybutanoic acid)

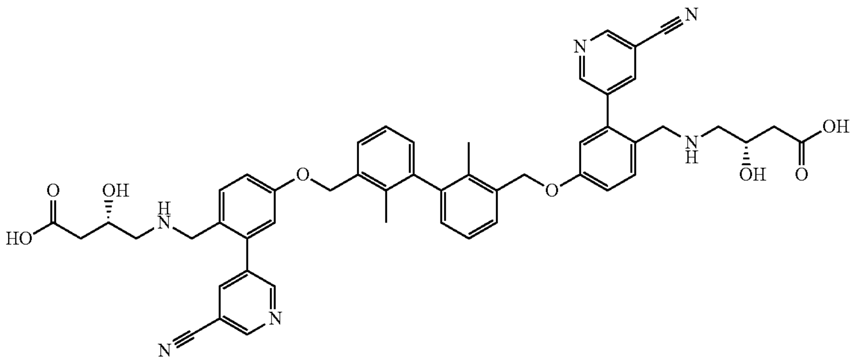 [SMILES: Cc1c(COc2ccc(CNC[C@@H](O)CC(=O)O)c(-c3cncc(C#N)c3)c2)cccc1-c1cccc(COc2ccc(CNC[C@@H](O)CC(=O)O)c(-c3cncc(C#N)c3)c2)c1C]

The title compound was synthesized according to general reductive amination procedure C. [M+1]=862.0. $^1H$ NMR (400 MHz, Methanol-$d_4$) δ 8.98 (d, J=2.0 Hz, 2H), 8.83 (d, J=2.2 Hz, 2H), 8.26 (t, J=2.1 Hz, 2H), 7.65 (d, J=8.7 Hz, 2H), 7.44 (d, J=7.7 Hz, 2H), 7.34-7.19 (m, 4H), 7.15-7.03 (m, 4H), 5.23 (s, 4H), 4.18 (d, J=5.4 Hz, 2H), 4.15-4.02 (m, 2H), 3.61-3.43 (m, 2H), 3.17-3.02 (m, 2H), 2.86 (dd, J=13.0, 9.6 Hz, 2H), 2.46 (d, J=6.3 Hz, 4H), 2.03 (s, 6H).

Example 273: (3S,3'S)-4,4'-((((((2,2'-dimethyl-[1,1'-biphenyl]-3,3'-diyl)bis(methylene))bis(oxy))bis(2-((1H-benzo[d]imidazol-2-yl)methoxy)-5-chloro-4,1-phenylene))bis(methylene))bis(azanediyl))bis(3-hydroxybutanoic acid)

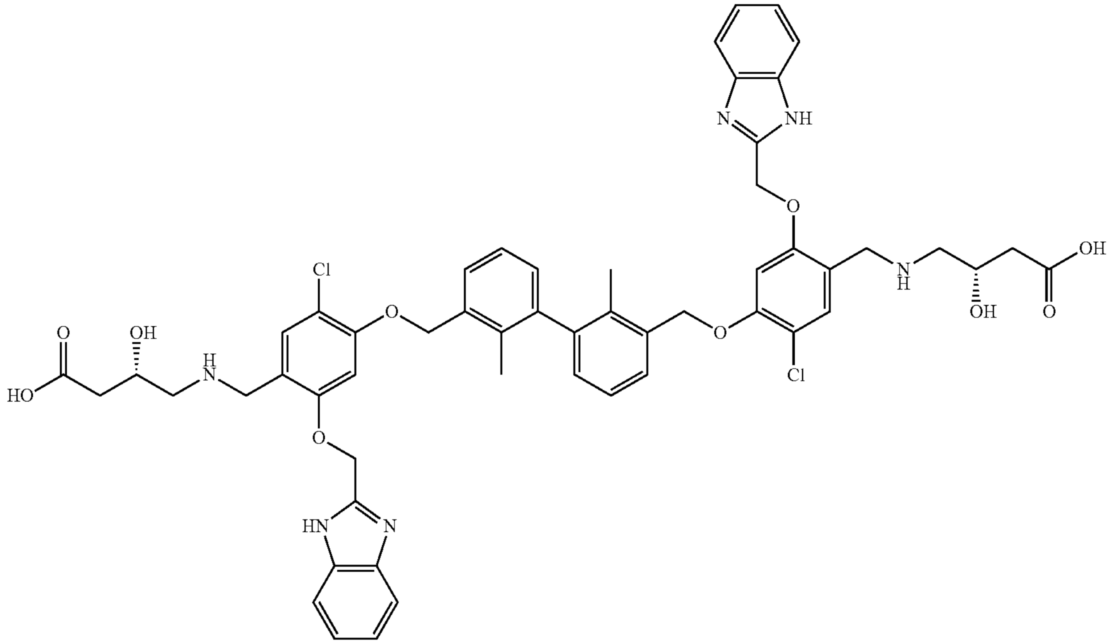 [SMILES: Cc1c(COc2cc(OCc3nc4ccccc4[nH]3)c(CNC[C@@H](O)CC(=O)O)cc2Cl)cccc1-c1cccc(COc2cc(OCc3nc4ccccc4[nH]3)c(CNC[C@@H](O)CC(=O)O)cc2Cl)c1C]

The title compound was synthesized according to general reductive amination procedure C. [M+1]=1018.9. $^1H$ NMR (400 MHz, DMSO-$d_6$) δ 7.56 (dd, J=5.9, 3.3 Hz, 4H), 7.51 (s, 2H), 7.42 (d, J=7.4 Hz, 2H), 7.32 (s, 2H), 7.23-7.10 (m, 6H), 7.01 (d, J=7.6 Hz, 2H), 5.58 (s, 4H), 5.25 (s, 4H), 4.15 (s, 6H), 3.03 (d, J=12.3 Hz, 2H), 2.92-2.76 (m, 2H), 2.33 (dd, J=15.9, 7.4 Hz, 4H), 1.95 (s, 6H).

Example 274: (2S,2'S)-2,2'-((((((2,2'-dimethyl-[1,1'-biphenyl]-3,3'-diyl)bis(methylene))bis(oxy))bis(5-bromo-2-methoxypyridine-6,3-diyl))bis(methylene))bis(azanediyl))bis(3-hydroxy-N,2-dimethylpropanamide) (or (2S,2'S)-2,2'-(((6,6'-(((2,2'-dimethyl-[1,1'-biphenyl]-3,3'-diyl)bis(methylene))bis(oxy))bis(5-bromo-2-methoxypyridine-6,3-diyl))bis(methylene))bis(azanediyl))bis(3-hydroxy-N,2-dimethylpropanamide))

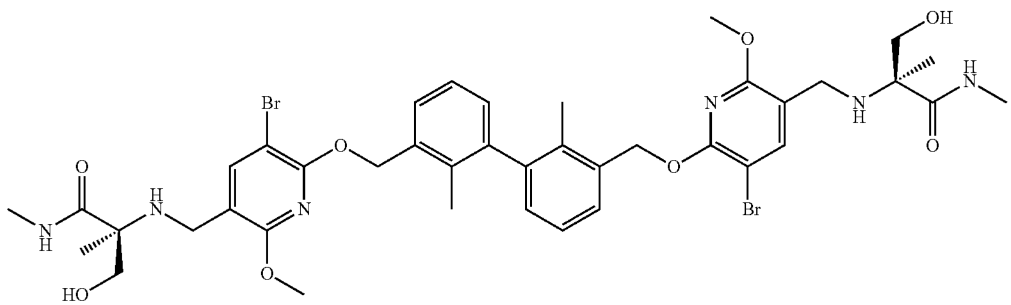

The title compound was synthesized according to general reductive amination procedure C. [M+1]=903.7.

Example 275: 5,5'-((((((2,2'-dimethyl-[1,1'-biphenyl]-3,3'-diyl)bis(methylene))bis(oxy))bis(4-bromo-6-(((pyridin-2-ylmethyl)amino)methyl)-3,1-phenylene))bis(oxy))bis(methylene))dinicotinonitrile

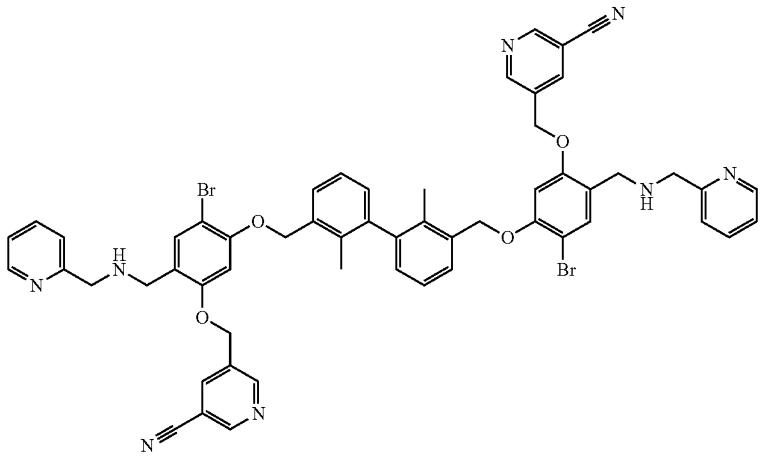 [SMILES: Cc1c(COc2cc(OCc3cncc(C#N)c3)c(CNCc3ccccn3)cc2Br)cccc1-c1cccc(COc2cc(OCc3cncc(C#N)c3)c(CNCc3ccccn3)cc2Br)c1C]

The title compound was synthesized according to general reductive amination procedure C. [M+1]=1057.8. $^{1}$H NMR (400 MHz, DMSO-$d_6$) δ 9.02 (dd, J=12.5, 2.1 Hz, 4H), 8.53 (d, J=5.0 Hz, 2H), 8.43 (t, J=2.0 Hz, 2H), 7.82 (td, J=7.8, 1.8 Hz, 2H), 7.69 (s, 2H), 7.52 (d, J=7.7 Hz, 2H), 7.44 (d, J=7.8 Hz, 2H), 7.37 (dd, J=7.5, 5.0 Hz, 2H), 7.29 (t, J=7.6 Hz, 2H), 7.15 (s, 2H), 7.11 (d, J=7.5 Hz, 2H), 5.33 (d, J=11.6 Hz, 8H), 4.24 (d, J=34.5 Hz, 8H), 2.04 (s, 6H).

Example 276: 5,5'-((((((2,2'-dimethyl-[1,1'-biphenyl]-3,3'-diyl)bis(methylene))bis(oxy))bis(4-chloro-6-((((R)-2-fluoro-3-hydroxy-3-methylbutyl)amino)methyl)-3,1-phenylene))bis(oxy))bis(methylene))dinicotinonitrile (or 5,5'-((((R)-(((2,2'-dimethyl-[1,1'-biphenyl]-3,3'-diyl)bis(methylene))bis(oxy))bis(4-chloro-2-((((R)-2-fluoro-3-hydroxy-3-methylbutyl)amino)methyl)-5,1-phenylene))bis(oxy))bis(methylene))dinicotinonitrile)

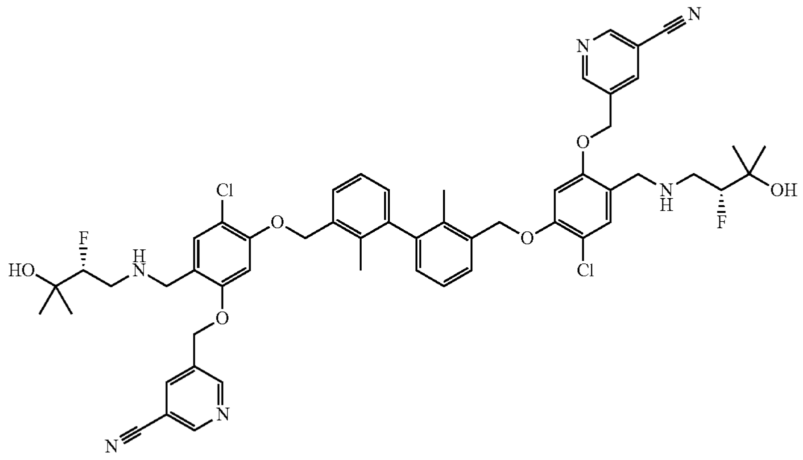 [SMILES: Cc1c(COc2cc(OCc3cncc(C#N)c3)c(CNC[C@@H](F)C(C)(C)O)cc2Cl)cccc1-c1cccc(COc2cc(OCc3cncc(C#N)c3)c(CNC[C@@H](F)C(C)(C)O)cc2Cl)c1C]

The title compound was synthesized according to general reductive amination procedure E. $^1$H NMR (400 MHz, DMSO-$d_6$) δ 9.02 (m, 4H), 8.89 (m, 4H), 8.48 (d, J=2.1 Hz, 2H), 7.56 (s, 2H), 7.50 (d, J=7.6 Hz, 2H), 7.29 (t, J=7.6 Hz, 2H), 7.20 (s, 2H), 7.11 (d, J=7.6 Hz, 2H), 5.35 (m, 8H), 4.62-4.37 (m, 2H), 4.19 (s, 4H), 3.27 (m 4H), 2.02 (s, 6H), 1.09 (s, 12H). ES/MS m/z: 993.5 ($M+H^+$).

Example 277: 5-((4-chloro-5-((3'-((2-chloro-4-((((R)-2-fluoro-3-hydroxy-3-methylbutyl)amino)methyl)-5-hydroxyphenoxy)methyl)-2,2'-dimethyl-[1,1'-biphenyl]-3-yl)methoxy)-2-((((R)-2-fluoro-3-hydroxy-3-methylbutyl)amino)methyl)phenoxy)methyl)nicotinonitrile

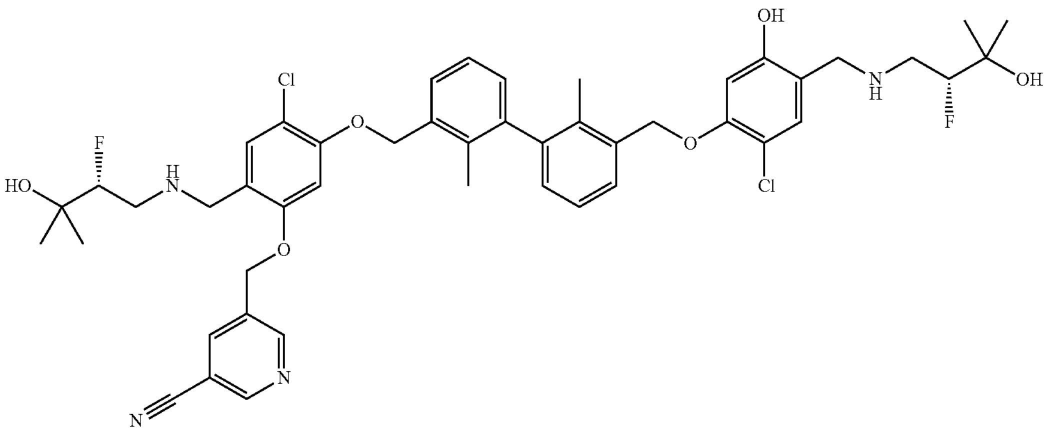 [SMILES: Cc1c(COc2cc(O)c(CNC[C@@H](F)C(C)(C)O)cc2Cl)cccc1-c1cccc(COc2cc(OCc3cncc(C#N)c3)c(CNC[C@@H](F)C(C)(C)O)cc2Cl)c1C]

The title compound was isolated as by-product of Example 276. $^1$H NMR (400 MHz, DMSO-$d_6$) δ 9.02 (dd, J=6.6, 2.0 Hz, 2H), 8.85 (s, 4H), 8.48 (t, J=2.1 Hz, 1H), 7.56 (s, 1H), 7.49 (dd, J=7.6, 2.6 Hz, 2H), 7.44 (s, 1H), 7.29 (td, J=7.5, 4.8 Hz, 2H), 7.21 (s, 1H), 7.10 (d, J=7.5 Hz, 2H), 6.83 (s, 1H), 5.35 (d, J=14.4 Hz, 3H), 5.19 (s, 2H), 4.52 (ddd, J=48.7, 15.4, 8.9 Hz, 2H), 4.19 (s, 2H), 4.08 (s, 2H), 3.27 (d, J=45.4 Hz, 4H), 2.09-1.91 (m, 6H), 1.10 (2×s, 12H). ES/MS m/z: 877.6 ($M+H^+$).

Example 278: 2,2'-((((((2,2'-dimethyl-[1,1'-biphenyl]-3,3'-diyl)bis(oxy))bis(difluoromethylene))bis(4,1-phenylene))bis(methylene))bis(azanediyl))diacetic acid

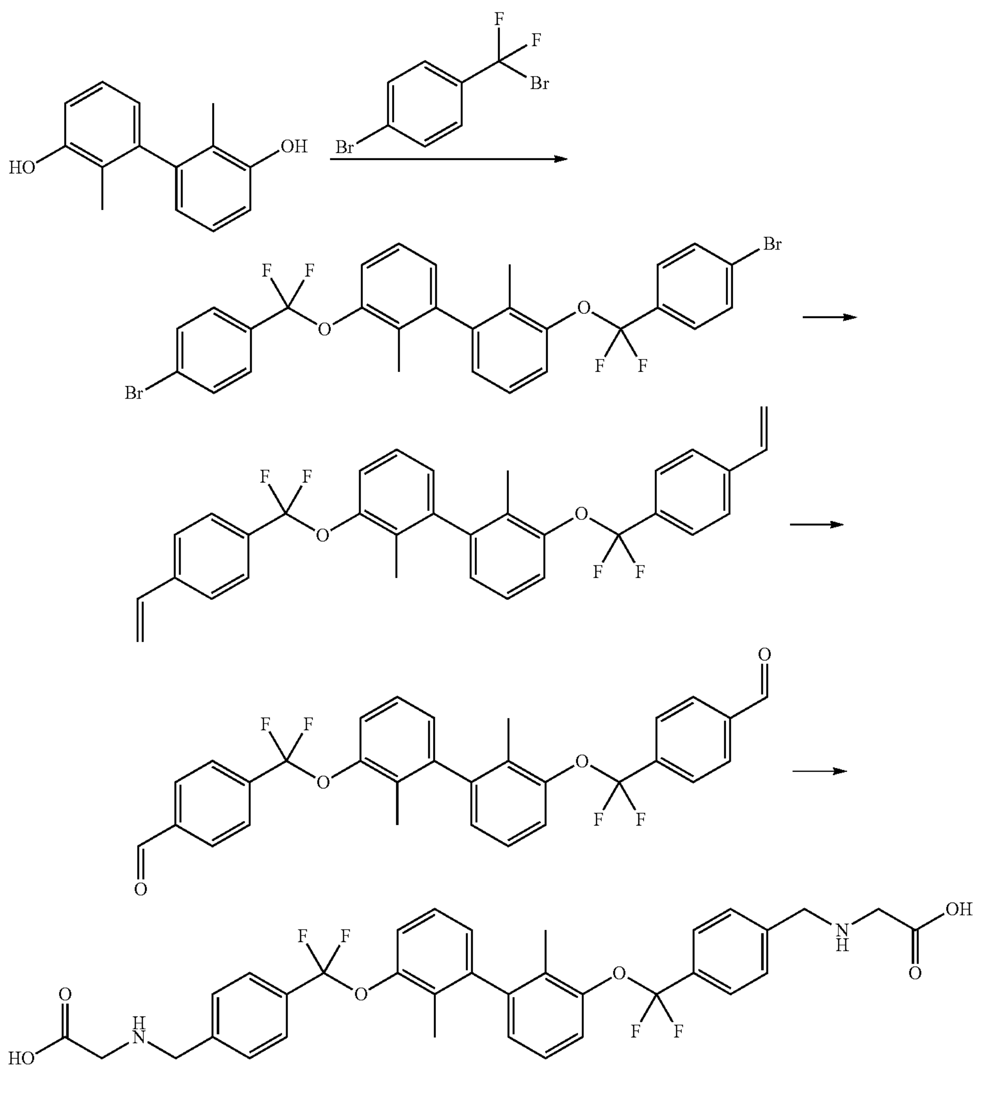

2,2'-dimethyl-[1,1'-biphenyl]-3,3'-diol and sodium hydride (60%) were dissolved in DMF. After 5 minutes added 1-bromo-4-(bromodifluoromethyl)benzene neat. Stirring at room temperature was continued. After 2 hrs, the reaction was heated at 60° C. After 19 hrs, the reaction mixture was cooled to room temperature. EtOAc was added and the reaction was washed with brine and dried over sodium sulfate. Filtration and evaporation o of solvents gave 3,3'-bis((4-bromophenyl)difluoromethoxy)-2,2'-dimethyl-1,1'-biphenyl, which was purified via chromatography on silica gel (el.: EtOAc/hex). $^1$H NMR (400 MHz, DMSO-$d_6$) δ 7.77 (d, J=8.6 Hz, 4H), 7.71 (d, J=8.6 Hz, 4H), 7.48-7.23 (m, 4H), 7.05 (dd, J=6.8, 2.0 Hz, 2H), 1.87 (s, 6H).

A reaction vessel was charged with 3,3'-bis((4-bromophenyl)difluoromethoxy)-2,2'-dimethyl-1,1-biphenyl (500 mg, 0.8 mmol), potassium vinyl trifluoro borate (227 mg, 2.4 mmol), Pd-dppf (140 mg, 0.2 mmol), cesium carbonate (298 mg, 4.8 mmol), DME and water and was heated at 90° C. for 2 hrs. The reaction was cooled to room temperature. The volatiles were removed and the crude was purified via Flash chromatography on silica gel (el EtOAc hex) to yield 3,3'-bis(difluoro(4-vinylphenyl)methoxy)-2,2'-dimethyl-1,1'-biphenyl. $^1$H NMR (400 MHz, Chloroform-d) δ 7.72 (d, J=8.1 Hz, 4H), 7.50 (d, J=8.1 Hz, 4H), 7.37 (dd, J=8.3, 1.6 Hz, 2H), 7.26-7.18 (m, 2H), 7.02 (dd, J=7.7, 1.3 Hz, 2H), 6.76 (dd, J=17.6, 10.9 Hz, 2H), 5.83 (dd, J=17.6, 0.8 Hz, 2H), 5.35 (dd, J=10.9, 0.8 Hz, 2H), 1.98 (s, 6H).

3,3'-bis(difluoro(4-vinylphenyl)methoxy)-2,2'-dimethyl-1,1'-biphenyl (150 mg, 0.29 mmol) was dissolved in THF/water. Osmium tetroxide (50 uL; 2.5% in tert Butanol) was added followed by lutidine (50 uL) and $NaIO_4$ (160 mg, 0.75 mmol). The reaction was stirred at rt for 14 hrs and diluted with EtOAc. The reaction was washed with aq sodium thiosulfate solution and brine, and was dried over sodium sulfate. Filtration and evaporation of solvents gave the crude 4,4'-(((2,2'-dimethyl-[1,1'-biphenyl]-3,3'-diyl)bis(oxy))bis(difluoromethylene))dibenzaldehyde which was used in the next step. H NMR (400 MHz, Chloroform-d) δ 10.11 (s, 2H), 8.08-7.87 (m, 8H), 7.47-7.32 (m, 2H), 7.33-7.24 (m, 6H), 7.05 (dd, J=7.6, 1.3 Hz, 2H), 1.99 (s, 6H).

2,2'-((((((2,2'-dimethyl-[1,1'-biphenyl]-3,3'-diyl)bis(oxy))bis(difluoromethylene))bis(4,1-phenylene))bis(methylene))

bis(azanediyl))diacetic acid was synthesized according to general reductive amination procedure E with the appropriate substitutions. $^{1}H$ NMR (400 MHz, Methanol-$d_4$) δ 7.88 (d, J=8.1 Hz, 4H), 7.67 (d, J=8.1 Hz, 4H), 7.37 (d, J=8.3 Hz, 2H), 7.29 (t, J=7.9 Hz, 2H), 7.03 (dd, J=7.6, 1.3 Hz, 2H), 4.33 (s, 4H), 3.85 (s, 4H), 1.97 (s, 6H). ES/MS m/z: 640.9.

Example 279: (S)-4-((4-(((3'-((4-((((S)-3-carboxy-2-hydroxypropyl)amino)methyl)-2-chloro-5-((5-cyano-pyridin-3-yl)methoxy)phenoxy)methyl)-2,2'-dimethyl-[1,1'-biphenyl]-3-yl)oxy)methyl)benzyl) amino)-3-hydroxybutanoic acid

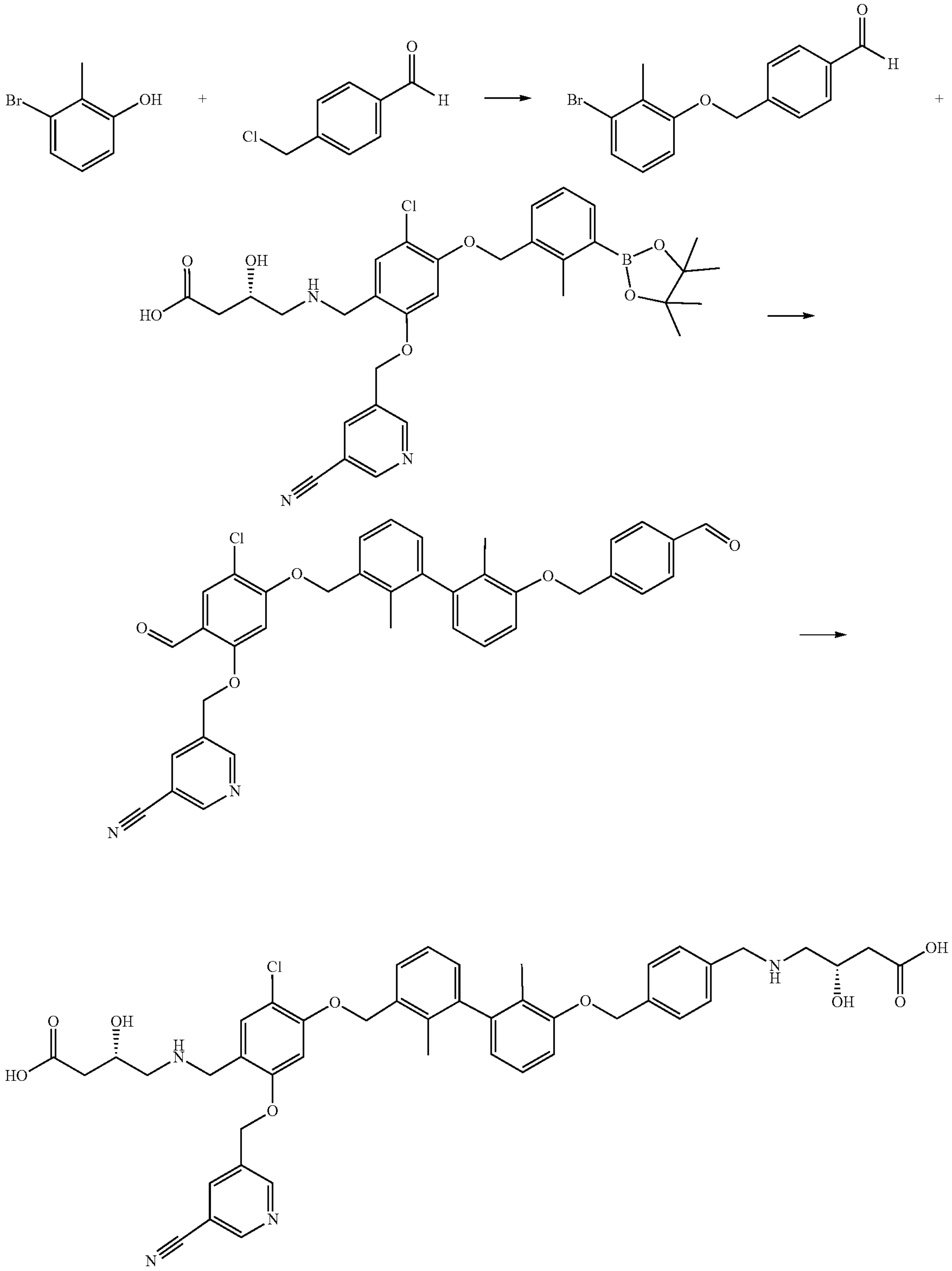

3-Bromo-2-methylphenol (850 mg, 4.54 mmol) was taken up in DMF (15 mL) at room temperature under a nitrogen atmosphere. To this was added sodium hydride 60% dispersion in mineral oil 218.12 mg, 5.45 mmol) and allowed to stir for 15 minutes.

At this point was added 4-(bromomethyl)benzaldehyde (904.58 mg, 4.54 mmol) and reaction allowed to stir for an additional 15 minutes. Reaction was diluted with EtOAc and quenched slowly with dilute aq. ammonium chloride. Reaction was extracted 3× with EtOAc and organics were washed with aq. LiCl (2×), water, brine 1× then dried over sodium sulfate before filtering and removing solvents under reduced pressure to afford crude as a solid.

9.02 (dd, J=5.2, 2.0 Hz, 2H), 8.89 (s, 2H), 8.61 (s, 2H), 8.46 (t, J=2.1 Hz, 1H), 7.56 (d, J=3.6 Hz, 1H), 7.53 (s, 3H), 7.47 (dd, J=7.7, 1.4 Hz, 1H), 7.29-7.15 (m, 3H), 7.10-7.02 (m, 2H), 6.70 (d, J=7.5 Hz, 1H), 5.36 (s, 2H), 5.30 (d, J=2.9 Hz, 2H), 5.17 (d, J=3.1 Hz, 2H), 4.15 (m, 6H), 3.00 (s, 2H), 2.84 (s, 3H), 2.46-2.28 (m, 4H), 2.04 (d, J=9.8 Hz, 3H), 1.86 (s, 3H).

Example 280: (3S,3'S)-4,4'-((((((2,2'-dimethyl-[1,1'-biphenyl]-3,3'-diyl)bis(methylene))bis(oxy))bis(5-chloro-2-((tetrahydrofuran-3-yl)methoxy)-4,1-phenylene))bis(methylene))bis(azanediyl))bis(3-hydroxybutanoic acid)

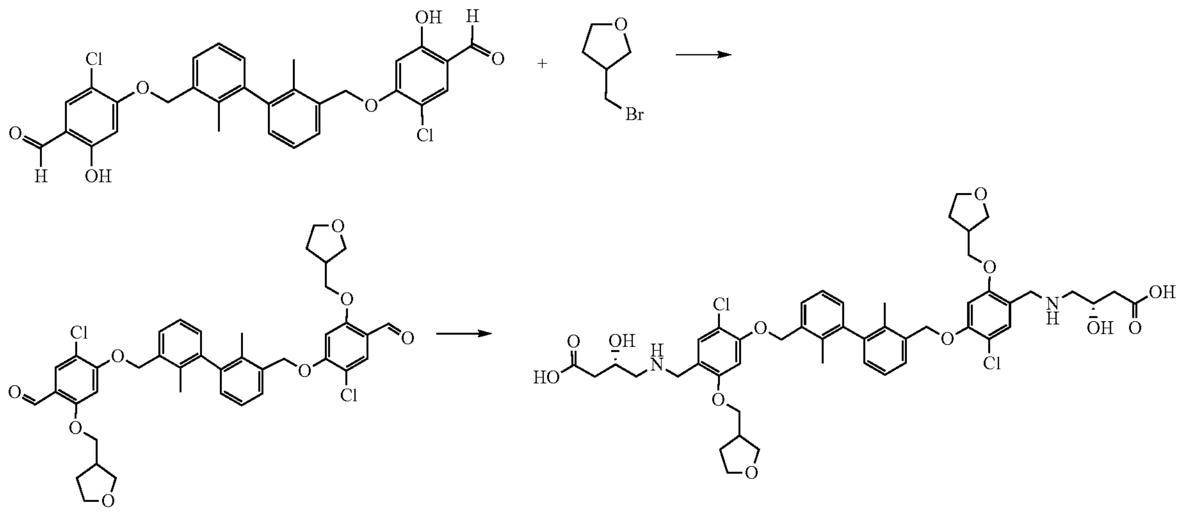

Crude was purified by silica gel chromatography using Hex:EtAc as the eluent to afford 4-((3-bromo-2-methylphenoxy)methyl)benzaldehyde as a solid.

5-((4-chloro-2-formyl-5-((2-methyl-3-(4,4,5,5-tetramethyl-1,3,2-dioxaborolan-2-yl)benzyl)oxy)phenoxy)methyl)nicotinonitrile (250 mg, 0.48 mmol), 4-((3-bromo-2-methylphenoxy)methyl)benzaldehyde (161.76 mg, 0.53 mmol), Pd(dppf)$Cl_2$-DCM (49.33 mg, 0.06 mmol), potassium carbonate (99.31 mg, 1.01 mmol) and 12 mL of 2:1 mixture of dioxane/water were placed in a microwave vial equipped with stir bar, sealed and heated in the microwave at 95° C. for 30 minutes. Reaction was diluted in EtAc/H2O and extracted 3× with EtAc. Organics were then washed with ammonium chloride 1×, water 1×, brine, then dried over sodium sulfate before filtering and evaporating organics under reduced pressure to afford crude residue. Crude material was purified by silica gel chromatography using Hexanes/EtAc as the eluent (0 to 100% EtAc) to afford 5-((4-chloro-2-formyl-5-((3'-((4-formylbenzyl)oxy)-2,2'-dimethyl-[1,1'-biphenyl]-3-yl)methoxy)phenoxy)methyl)nicotinonitrile.

(S)-4-((4-(((3'-((4-((((S)-3-carboxy-2-hydroxypropyl)amino)methyl)-2-chloro-5-((5-cyanopyridin-3-yl)methoxy)phenoxy)methyl)-2,2'-dimethyl-[1,1'-biphenyl]-3-yl)oxy)methyl)benzyl)amino)-3-hydroxybutanoic acid was synthesized from 5-((4-chloro-2-formyl-5-((3'-((4-formylbenzyl)oxy)-2,2'-dimethyl-[1,1'-biphenyl]-3-yl)methoxy)phenoxy)methyl)nicotinonitrile using reductive amination procedure A to afford the desired product as the bis-TFA salt. MS (m/z) 823.3 $[M+H]^+$. $^1H$ NMR (400 MHz, DMSO-$d_6$) δ

4,4'-(((2,2'-dimethyl-[1,1'-biphenyl]-3,3'-diyl)bis(methylene))bis(oxy))bis(2-chloro-5-hydroxybenzaldehyde) (100 mg, 0.18 mmol), sodium Iodide (81.55 mg, 0.54 mmol), potassium carbonate (150.38 mg, 1.09 mmol) and N,N-Dimethylformamide (5 mL) were placed in a sealed vessel, stirred and heated to 70° C. for 12 hours. Reaction was cooled then diluted in EtAc and aqueous lithium chloride and extracted with EtAc (3×). Organics were then washed with lithium chloride (3×), water, brine, then dried over sodium sulfate before filtering and evaporating organics under reduced pressure to afford crude residue. Crude material was purified by silica gel chromatography using Hexanes/EtAc as the eluent (0 to 100% EtAc) to afford 4,4'-(((2,2'-dimethyl-[1,1'-biphenyl]-3,3'-diyl)bis(methylene))bis(oxy))bis(2-chloro-5-((tetrahydrofuran-3-yl)methoxy)benzaldehyde).

(3S,3'S)-4,4'-((((((2,2'-dimethyl-[1,1'-biphenyl]-3,3'-diyl)bis(methylene))bis(oxy))bis(5-chloro-2-((tetrahydrofuran-3-yl)methoxy)-4,1-phenylene))bis(methylene))bis(azanediyl))bis(3-hydroxybutanoic acid) was synthesized from 4,4'-(((2,2'-dimethyl-[1,1'-biphenyl]-3,3'-diyl)bis(methylene))bis(oxy))bis(5-chloro-2-((tetrahydrofuran-3-yl)methoxy)benzaldehyde)following reductive amination procedure A to afford product as the bis-TFA salt. MS (m/z) 925.3 $[M+H]^+$. $^1H$ NMR (400 MHz, Methanol-$d_4$) δ 7.50 (dd, J=7.8, 1.4 Hz, 2H), 7.44 (s, 2H), 7.27 (t, J=7.6 Hz, 2H), 7.11 (dd, J=7.7, 1.4 Hz, 2H), 6.94 (d, J=1.1 Hz, 2H), 5.31 (s, 4H), 4.31-4.05 (m, 10H), 4.01-3.86 (m, 4H), 3.82-3.69 (m, 4H), 3.21 (ddd, J=12.7, 5.2, 3.0 Hz, 2H), 2.99 (ddd, J=12.3, 9.8, 2.0 Hz, 2H), 2.90-2.75 (m, 2H), 2.54 (dd, J=6.4, 1.1 Hz, 4H), 2.20 (tdd, J=13.1, 9.0, 4.9 Hz, 2H), 2.09 (s, 6H), 1.90-1.76 (m, 2H).

Example 281: 5,5'-((((((2,2'-dimethyl-[1,1'-biphenyl]-3,3'-diyl)bis(methylene))bis(oxy))bis(4-chloro-6-(((1,3-dihydroxypropan-2-yl)amino)methyl)-3,1-phenylene))bis(oxy))bis(methylene))dinicotinonitrile (or 5,5'-((((((2,2'-dimethyl-[1,1'-biphenyl]-3,3'-diyl)bis(methylene))bis(oxy))bis(4-chloro-2-(((1,3-dihydroxypropan-2-yl)amino)methyl)-5,1-phenylene))bis(oxy))bis(methylene))dinicotinonitrile)

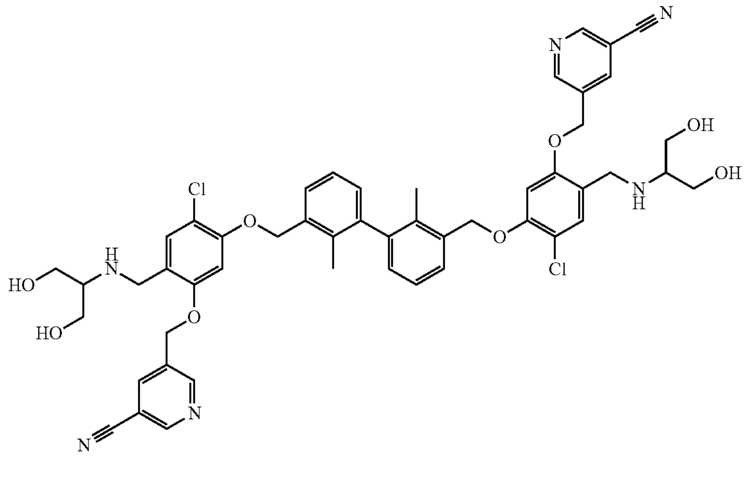 [SMILES: Cc1c(COc2cc(OCc3cncc(C#N)c3)c(CNC(CO)CO)cc2Cl)cccc1-c1cccc(COc2cc(OCc3cncc(C#N)c3)c(CNC(CO)CO)cc2Cl)c1C]

5,5'-((((((2,2'-dimethyl-[1,1'-biphenyl]-3,3'-diyl)bis(methylene))bis(oxy))bis(4-chloro-6-(((1,3-dihydroxypropan-2-yl)amino)methyl)-3,1-phenylene))bis(oxy))bis(methylene))dinicotinonitrile was synthesized from 5,5'-((((((2,2'-dimethyl-[1,1'-biphenyl]-3,3'-diyl)bis(methylene))bis(oxy))bis(4-chloro-6-formyl-3,1-phenylene))bis(oxy))bis(methylene))dinicotinonitrile following reductive amination procedure F using serinol in place of (3S)-4-amino-3-hydroxybutyric acid to afford the product as the bis-TFA salt. MS (m/z) 933.3 [M+H]$^+$. $^1$H NMR (400 MHz, Methanol-$d_4$) δ 8.97 (d, J=2.1 Hz, 2H), 8.92 (d, J=2.0 Hz, 2H), 8.44-8.40 (m, 2H), 7.53 (s, 2H), 7.50-7.45 (m, 2H), 7.31-7.24 (m, 2H), 7.16-7.09 (m, 2H), 7.08 (s, 2H), 5.37 (s, 4H), 5.32 (s, 4H), 4.33 (s, 4H), 3.81 (dd, J=12.0, 4.5 Hz, 4H), 3.71 (dd, J=12.0, 6.4 Hz, 4H), 3.29-3.22 (m, 2H), 2.08 (s, 6H).

Example 282: 5,5'-((((((2,2'-dimethyl-[1,1'-biphenyl]-3,3'-diyl)bis(methylene))bis(oxy))bis(4-chloro-6-(((1,3-dihydroxy-2-(hydroxymethyl)propan-2-yl)amino)methyl)-3,1-phenylene))bis(oxy))bis(methylene))dinicotinonitrile (or 5,5'-((((((2,2'-dimethyl-[1,1'-biphenyl]-3,3'-diyl)bis(methylene))bis(oxy))bis(4-chloro-2-(((1,3-dihydroxy-2-(hydroxymethyl)propan-2-yl)amino)methyl)-5,1-phenylene))bis(oxy))bis(methylene))dinicotinonitrile)

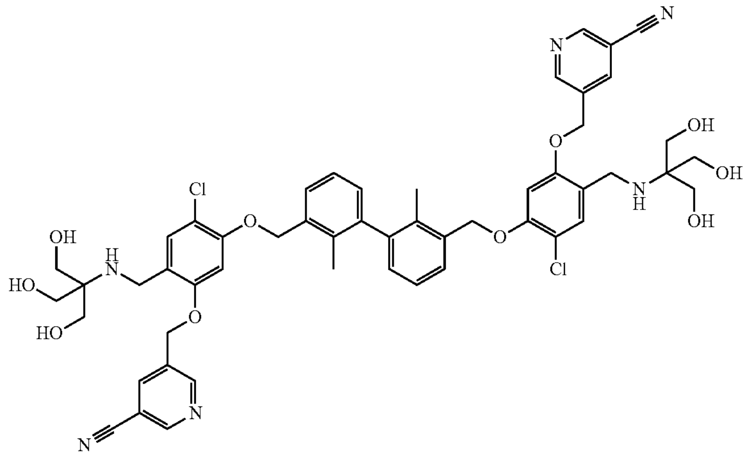 [SMILES: Cc1c(COc2cc(OCc3cncc(C#N)c3)c(CNC(CO)(CO)CO)cc2Cl)cccc1-c1cccc(COc2cc(OCc3cncc(C#N)c3)c(CNC(CO)(CO)CO)cc2Cl)c1C]

5,5'-((((((2,2'-dimethyl-[1,1'-biphenyl]-3,3'-diyl)bis(methylene))bis(oxy))bis(4-chloro-6-(((1,3-dihydroxy-2-(hydroxymethyl)propan-2-yl)amino)methyl)-3,1-phenylene))bis(oxy))bis(methylene))dinicotinonitrile was synthesized from 5,5'-((((((2,2'-dimethyl-[1,1'-biphenyl]-3,3'-diyl)bis(methylene))bis(oxy))bis(4-chloro-6-formyl-3,1-phenylene))bis(oxy))bis(methylene))dinicotinonitrile following reductive amination procedure A using Trizma HCl in place of (3S)-4-amino-3-hydroxybutyric acid and 10 equivalents of TEA to afford product as the bis-TFA salt. MS (m/z) 993.3 $[M+H]^+$. $^1H$ NMR (400 MHz, DMSO-$d_6$) δ 9.01 (t, J=2.1 Hz, 4H), 8.50 (t, J=2.1 Hz, 2H), 8.22 (d, J=8.3 Hz, 4H), 7.53 (s, 2H), 7.51-7.46 (m, 2H), 7.28 (t, J=7.6 Hz, 2H), 7.16 (s, 2H), 7.10 (d, J=7.6 Hz, 2H), 5.33 (d, J=8.0 Hz, 8H), 5.23 (s, 4H), 4.23 (s, 4H), 3.58 (s, 12H), 2.02 (s, 6H).

Example 283: (3S,3'S)-4,4'-((((((2,2'-dimethyl-[1,1'-biphenyl]-3,3'-diyl)bis(methylene))bis(oxy))bis(3-chloro-4,1-phenylene))bis(methylene))bis(azanediyl))bis(3-hydroxybutanoic acid)

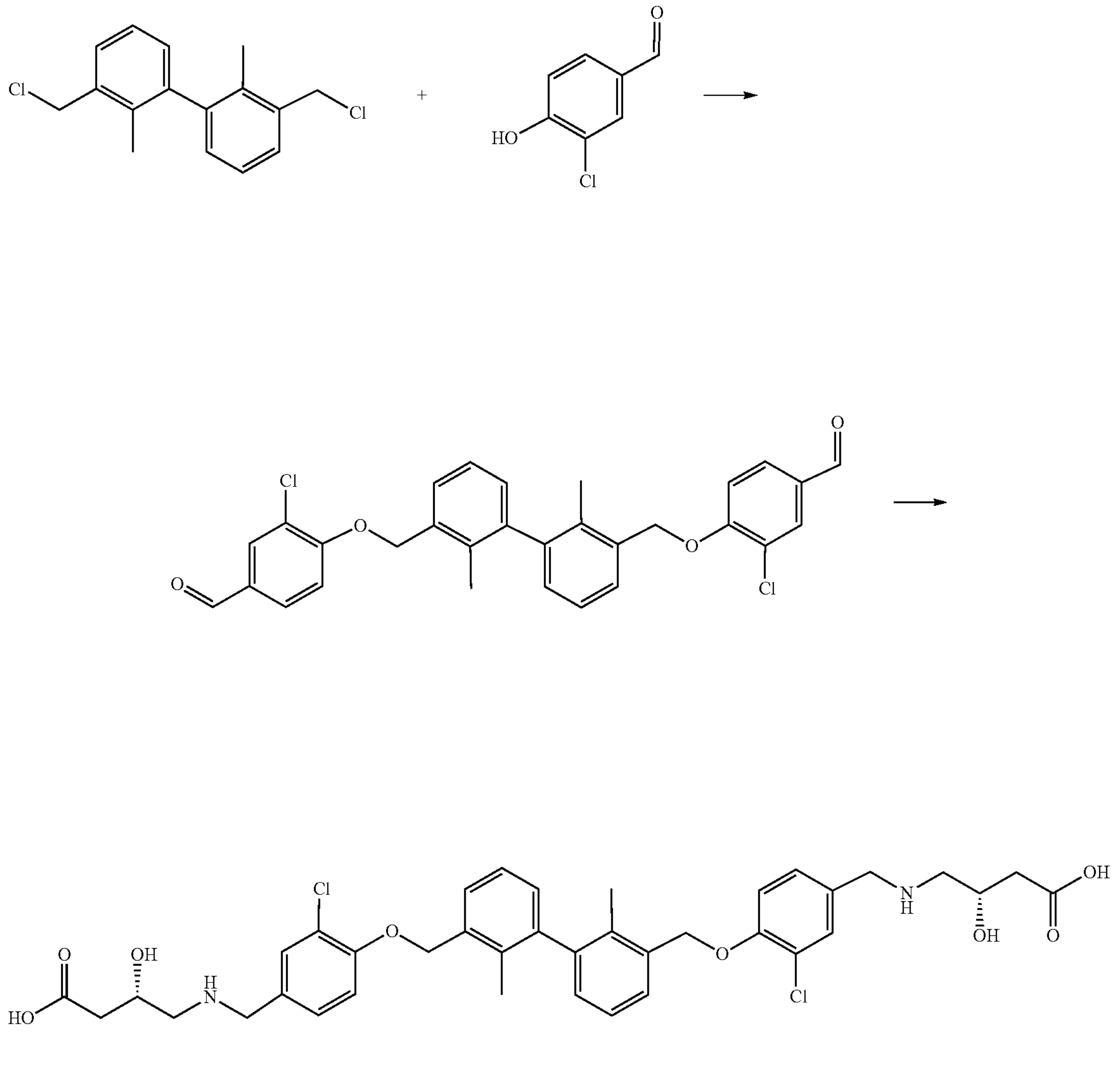

3,3'-bis(chloromethyl)-2,2'-dimethyl-1,1'-biphenyl (150 mg, 0.54 mmol), 3-chloro-4-hydroxybenzaldehyde (176.64 mg, 1.13 mmol), Sodium Iodide (241.59 mg, 1.61 mmol), Sodium carbonate (227.76 mg, 2.15 mmol) and DMF (10 mL) were placed in a round-bottomed flask equipped with stir bar under nitrogen and heated to 45° C. with stirring for 12 hours. Reaction was cooled then diluted in EtAc and aqueous lithium chloride and extracted with EtAc (3×). Organics were then washed with lithium chloride (3×), water, brine, then dried over sodium sulfate before filtering and evaporating organics under reduced pressure to afford 4,4'-(((2,2'-dimethyl-[1,1'-biphenyl]-3,3'-diyl)bis(methylene))bis(oxy))bis(3-chlorobenzaldehyde) as a crude residue.

(3S,3'S)-4,4'-((((((2,2'-dimethyl-[1,1'-biphenyl]-3,3'-diyl)bis(methylene))bis(oxy))bis(3-chloro-4,1-phenylene))bis(methylene))bis(azanediyl))bis(3-hydroxybutanoic acid) was synthesized from 4,4'-(((2,2'-dimethyl-[1,1'-biphenyl]-3,3'-diyl)bis(methylene))bis(oxy))bis(3-chlorobenzaldehyde) using reductive amination procedure A to afford the desired product as the bis-TFA salt. MS (m/z) 725.3 $[M+H]^+$. $^1H$ NMR (400 MHz, Methanol-$d_4$) δ 7.58 (d, J=2.2 Hz, 2H), 7.48 (dd, J=7.7, 1.4 Hz, 2H), 7.42 (dd, J=8.5, 2.2 Hz, 2H), 7.26 (dd, J=16.1, 8.1 Hz, 4H), 7.10 (dd, J=7.7, 1.4 Hz, 2H), 5.25 (s, 4H), 4.29 (m, 2H), 4.18 (s, 4H), 3.19 (dd, J=12.7, 3.1 Hz, 2H), 2.99 (dd, J=12.7, 9.9 Hz, 2H), 2.53 (d, J=6.3 Hz, 4H), 2.06 (s, 6H).

Example 284: 3,3'-((((((2,2'-dimethyl-[1,1'-biphenyl]-3,3'-diyl)bis(methylene))bis(oxy))bis(4-chloro-6-(((2-hydroxyethyl)amino)methyl)-3,1-phenylene))bis(oxy))bis(methylene))dibenzonitrile (or 3,3'-((((((2,2'-dimethyl-[1,1'-biphenyl]-3,3'-diyl)bis(methylene))bis(oxy))bis(4-chloro-2-(((2-hydroxyethyl)amino)methyl)-5,1-phenylene))bis(oxy))bis(methylene))dibenzonitrile)

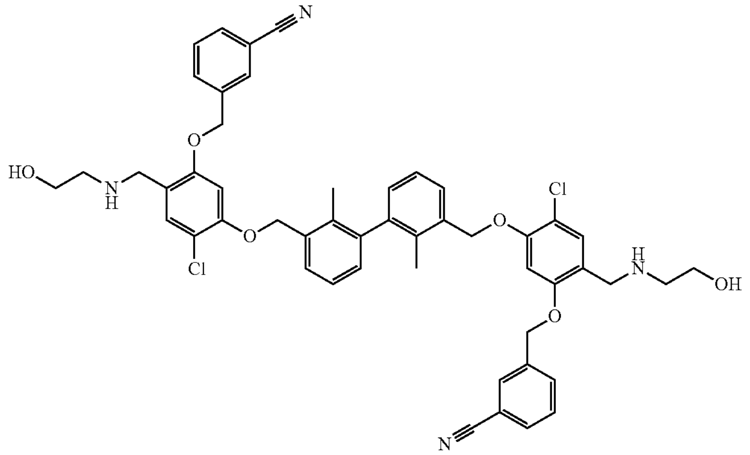 [SMILES: Cc1c(COc2cc(OCc3cccc(C#N)c3)c(CNCCO)cc2Cl)cccc1-c1cccc(COc2cc(OCc3cccc(C#N)c3)c(CNCCO)cc2Cl)c1C]

The title compound was synthesized using reductive amination procedure C, using 2-aminoethan-1-ol and acetic acid. $^1$H NMR (400 MHz, DMSO-$d_6$) δ 8.61 (s, 4H), 8.00 (d, J=1.7 Hz, 2H), 7.88-7.78 (m, 3H), 7.62 (t, J=7.8 Hz, 2H), 7.55 (s, 2H), 7.47 (d, J=7.7 Hz, 2H), 7.28 (dq, J=8.1, 5.3, 4.4 Hz, 2H), 7.17 (s, 2H), 7.12-7.08 (m, 2H), 5.30 (d, J=6.7 Hz, 7H), 4.15-4.05 (m, 4H), 3.62 (t, J=5.4 Hz, 5H), 2.94 (t, J=5.8 Hz, 4H), 2.08-1.98 (m, 6H). LCMS-ESI+ (m/z): $[M+H]^+$ calculated for $C_{49}H_{49}Cl_2N_3O_6$: 871.3; found: 871.2.

Example 285: (3S,3'S)-4,4'-((((((2-fluoro-2'-methyl-[1,1'-biphenyl]-3,3'-diyl)bis(methylene))bis(oxy))bis(2-methoxypyridine-6,3-diyl))bis(methylene))bis(azanediyl))bis(3-hydroxybutanoic acid) (or (3S,3'S)-4,4'-(((6,6'-(((2-fluoro-2'-methyl-[1,1'-biphenyl]-3,3'-diyl)bis(methylene))bis(oxy))bis(2-methoxypyridine-6,3-diyl))bis(methylene))bis(azanediyl))bis(3-hydroxybutanoic acid))

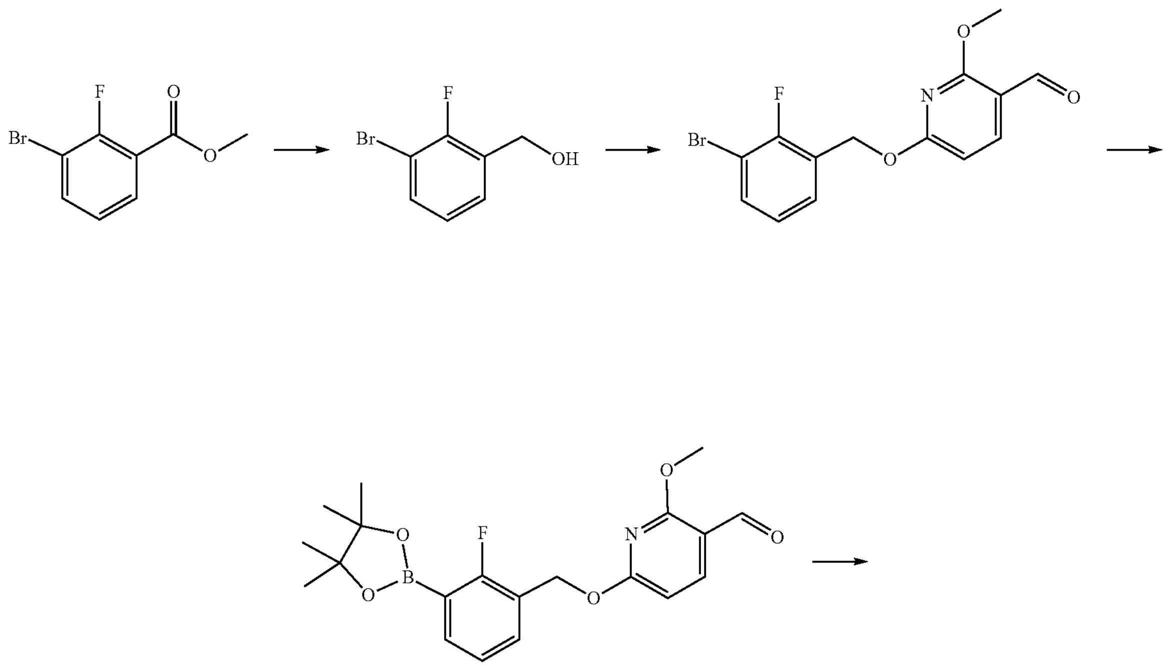

-continued

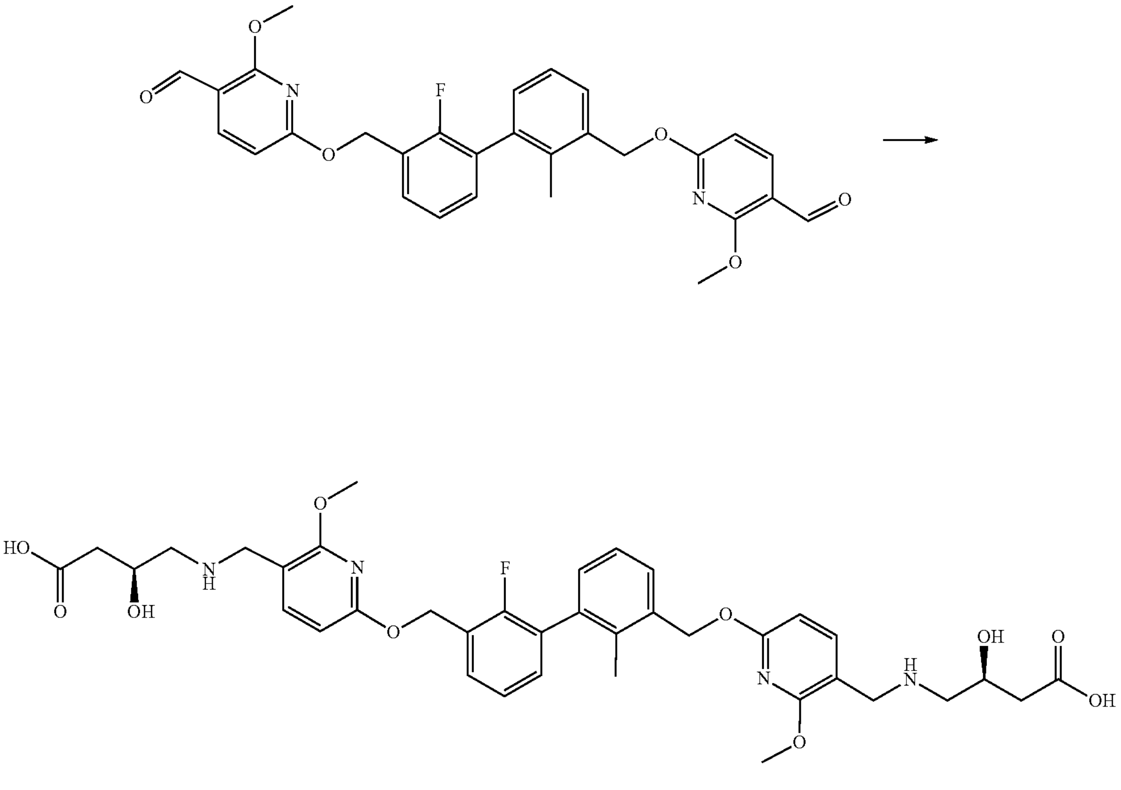

Step 1: Methyl 3-bromo-2-fluorobenzoate (500 mg, 2.15 mmol) dissolved in diethyl ether (15 mL) was cooled to 0° C. and treated with lithium aluminum hydride (81 mg, 2.13 mmol). The reaction mixture was slowly warmed to room temperature and stirred for 6 h. The reaction mixture was again cooled to 0° C. and methanol was added dropwise slowly followed by water. The reaction mixture was diluted with ethyl acetate and washed with water. The organic layer was concentrated to give (3-bromo-2-fluorophenyl)methanol.

Step 2: Preparation of 6-((3-bromo-2-fluorobenzyl)oxy)-2-methoxynicotinaldehyde. (3-bromo-2-fluorophenyl) methanol (342 mg, 1.67 mmol) dissolved in dimethylformamide (10 mL) was treated with sodium hydride (72 mg, 1.80 mmol, 60% dispersion in mineral oil). The suspension was stirred at room temperature for 10 min before 6-chloro-2-methoxynicotinaldehyde (287 mg, 1.67 mmol) was added. The reaction mixture was heated at 90° C. for 2 h. After cooling to room temperature, the reaction mixture was diluted with ethyl acetate and washed with water. The organic layer was concentrated and purified by column chromatography to give 6-((3-bromo-2-fluorobenzyl)oxy)-2-methoxynicotinaldehyde.

Step 3: Preparation of 6-((2-fluoro-3-(4,4,5,5-tetramethyl-1,3,2-dioxaborolan-2-yl)benzyl)oxy)-2-methoxynicotinaldehyde. 6-((3-bromo-2-fluorobenzyl)oxy)-2-methoxynicotinaldehyde (100 mg, 0.29 mmol) dissolved in 1,4-dioxane (3 mL) was treated with bis (pinacolato) diboron (112 mg, 0.44 mmol), [1,1'-Bis(diphenylphosphino) ferrocene]palladium(II) dichloride (25 mg, 0.031 mmol), and potassium acetate (87 mg, 0.89 mmol). The reaction mixture was heated at 85° C. for 4h. After cooling to room temperature, the reaction mixture was diluted with ethyl acetate and washed with water. The organic layer was concentrated and purified by column chromatography to give 6-((2-fluoro-3-(4,4,5,5-tetramethyl-1,3,2-dioxaborolan-2-yl)benzyl)oxy)-2-methoxynicotinaldehyde.

Step 4: Preparation of 6,6'-(((2-fluoro-2'-methyl-[1,1'-biphenyl]-3,3'-diyl)bis(methylene))bis(oxy))bis(2-methoxynicotinaldehyde). 6-((2-fluoro-3-(4,4,5,5-tetramethyl-1,3,2-dioxaborolan-2-yl)benzyl)oxy)-2-methoxynicotinaldehyde (88 mg, 0.23 mmol) and 6-((3-bromo-2-methylbenzyl)oxy)-2-methoxynicotinaldehyde (83 mg, 0.24 mmol) dissolved in 2-methyltetrahydrofuran (2 mL) was treated with tetrakis (triphenylphosphine)palladium(0) (28 mg, 0.02 mmol) and sodium carbonate (190 μl, 0.38 mmol, 2M solution in water). The reaction mixture was heated in the microwave at 105° C. for 90 min. After cooling to room temperature, the reaction mixture was diluted with ethyl acetate and washed with water. The organic layer was concentrated and purified by column chromatography to give 6,6'-(((2-fluoro-2'-methyl-[1,1'-biphenyl]-3,3'-diyl)bis(methylene))bis(oxy)) bis(2-methoxynicotinaldehyde).

Step 5: Preparation of (3S,3'S)-4,4'-((((((2-fluoro-2'-methyl-[1,1'-biphenyl]-3,3'-diyl)bis(methylene))bis(oxy)) bis(2-methoxypyridine-6,3-diyl))bis(methylene))bis (azanediyl))bis(3-hydroxybutanoic acid). The title compound was synthesized using general reductive amination procedure B. $^1$H NMR (400 MHz, DMSO-$d_6$) δ 8.62 (s, 2H), 7.74 (d, J=8.1 Hz, 1H), 7.60-7.48 (m, 1H), 7.28 (qd, J=7.4, 3.1 Hz, 1H), 7.18 (d, J=7.3 Hz, 1H), 6.51 (d, J=8.0 Hz, 1H), 5.45 (t, J=8.4 Hz, 2H), 4.21-4.11 (m, 1H), 4.11-3.98 (m, 2H), 3.90 (d, J=12.8 Hz, 3H), 3.00 (d, J=12.2 Hz, 1H), 2.84 (s, 1H), 2.44-2.35 (m, 1H). LCMS-ESI+ (m/z): $[M+H]^+$ calculated for $C_{37}H_{43}FN_4O_{10}$: 723.3; found: 723.2.

Example 286: (S)-4-(((2-(3'-((4-((((S)-3-carboxy-2-hydroxypropyl)amino)methyl)-2-chloro-5-((5-cyano-pyridin-3-yl)methoxy)phenoxy)methyl)-2,2'-dimethyl-[1,1'-biphenyl]-3-yl)benzo[d]thiazol-6-yl)methyl)amino)-3-hydroxybutanoic acid

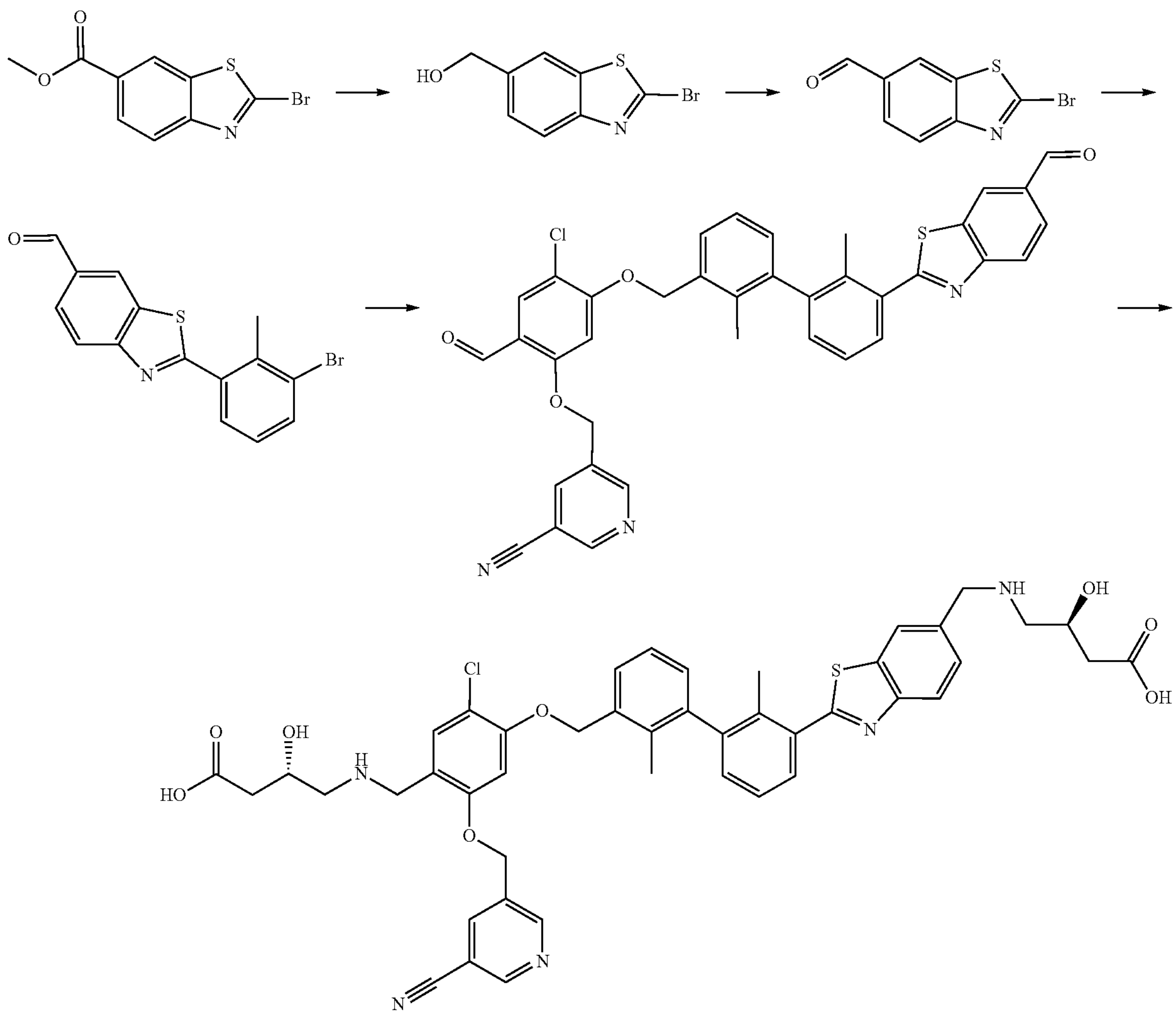

Step 1: Methyl 2-bromobenzo[d]thiazole-6-carboxylate (500 mg, 1.84 mmol) dissolved in diethyl ether (13 mL) was cooled to 0° C. and treated with lithium aluminum hydride (70 mg, 1.84 mmol). The reaction mixture was slowly warmed to room temperature and stirred for 4h. The reaction mixture was again cooled to 0° C. and methanol was added dropwise slowly followed by water. The reaction mixture was diluted with ethyl acetate and washed with water. The organic layer was concentrated to give (2-bromobenzo[d]thiazol-6-yl)methanol.

Step 2: (2-bromobenzo[d]thiazol-6-yl)methanol (374 mg, 1.53 mmol) dissolved in dichloromethane (12 mL) was treated with Dess-Martin periodinane (682 mg, 1.61 mmol). The reaction mixture was stirred at room temperature overnight and quenched by slow dropwise addition of saturated sodium thiosulfate solution. The reaction mixture was diluted with ethyl acetate and washed with water. The organic layer was concentrated to give 2-bromobenzo[d]thiazole-6-carbaldehyde.

Step 3: 2-bromobenzo[d]thiazole-6-carbaldehyde (50 mg, 0.21 mmol) and (3-bromo-2-methylphenyl)boronic acid (25 mg, 0.12 mmol) dissolved in 2-methyltetrahydrofuran (3 mL) was treated with tetrakis(triphenylphosphine)palladium (0) (14 mg, 0.01 mmol) and sodium carbonate (130 μl, 0.26 mmol, 2M solution in water). The reaction mixture was heated in the microwave at 105° C. for 25 min. After cooling to room temperature, the reaction mixture was diluted with ethyl acetate and washed with water. The organic layer was concentrated and purified by column chromatography to give 2-(3-bromo-2-methylphenyl)benzo[d]thiazole-6-carbaldehyde.

Step 4: 2-(3-bromo-2-methylphenyl)benzo[d]thiazole-6-carbaldehyde (28 mg, 0.08 mmol) and 5-((4-chloro-2-formyl-5-((2-methyl-3-(4,4,5,5-tetramethyl-1,3,2-dioxaborolan-2-yl)benzyl)oxy)phenoxy)methyl)nicotinonitrile (28 mg, 0.05 mmol) dissolved in 2-methyltetrahydrofuran (3 mL) was treated with tetrakis(triphenylphosphine)palladium (0) (7 mg, 0.01 mmol) and sodium carbonate (60 μl, 0.12 mmol, 2M solution in water). The reaction mixture was heated in the microwave at 105° C. for 90 min. After cooling to room temperature, the reaction mixture was diluted with ethyl acetate and washed with water. The organic layer was concentrated and purified by column chromatography to give 5-((4-chloro-2-formyl-5-((3'-(6-formylbenzo[d]thiazol-2-yl)-2,2'-dimethyl-[1,1'-biphenyl]-3-yl)methoxy)phenoxy)methyl)nicotinonitrile.

Step 5: (S)-4-(((2-(3'-((4-((((S)-3-carboxy-2-hydroxypropyl)amino)methyl)-2-chloro-5-((5-cyanopyridin-3-yl)methoxy)phenoxy)methyl)-2,2'-dimethyl-[1,1'-biphenyl]-3-yl)benzo[d]thiazol-6-yl)methyl)amino)-3-hydroxybutanoic acid was synthesized using general reductive amination procedure B. $^1$H NMR (400 MHz, DMSO-$d_6$) δ 9.02 (dd, J=5.8, 2.1 Hz, 2H), 8.93 (s, 2H), 8.56 (s, 2H), 8.46 (t, J=2.1 Hz, 1H), 8.28 (d, J=1.6 Hz, 1H), 8.14 (d, J=8.4 Hz, 1H), 7.78 (dd, J=7.9, 1.3 Hz, 1H), 7.69 (dd, J=8.5, 1.7 Hz, 1H), 7.57 (s, 1H), 7.55-7.44 (m, 2H), 7.32 (t, J=7.6 Hz, 2H), 7.21-7.12 (m, 2H), 5.55 (s, 2H), 5.40-5.29 (m, 4H), 4.33 (s, 2H), 4.13 (d, J=11.1 Hz, 4H), 3.02 (s, 3H), 2.86 (d, J=3.9 Hz, 3H), 2.23 (s, 3H), 2.08 (s, 3H). LCMS-ESI+ (m/z): [M+H]+ calculated for $C_{45}H_{44}ClN_5O_8S$: 850.3; found: 850.2.

Example 287: Diethyl 2,2'-((((((1S,1'S)-2,2',3,3'-tetrahydro-1H,1'H-[4,4'-biindene]-1,1'-diyl)bis(oxy))bis(5-chloro-2-methoxypyridine-6,3-diyl))bis(methylene))bis(azanediyl))diacetate (or diethyl 2,2'-(((6,6'-(((1S,1'S)-2,2',3,3'-tetrahydro-1H,1'H-[4,4'-biindene]-1,1'-diyl)bis(oxy))bis(5-chloro-2-methoxypyridine-6,3-diyl))bis methylene))bis(azanediyl)diacetate)

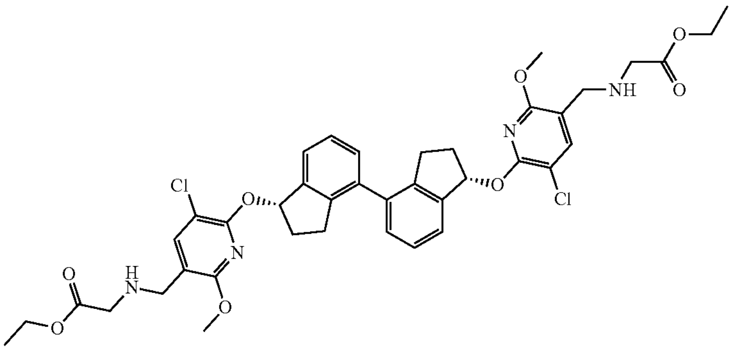 [SMILES: CCOC(=O)CNCc1cc(Cl)c(O[C@H]2CCc3c(-c4cccc5c4CC[C@@H]5Oc4nc(OC)c(CNCC(=O)OCC)cc4Cl)cccc32)nc1OC]

A solution of 6,6'-(((1S,1'S)-2,2',3,3'-tetrahydro-1H,1'H-[4,4'-biindene]-1,1'-diyl)bis(oxy))bis(5-chloro-2-methoxynicotinaldehyde) (130 mg, 0.215 mmol) was treated using general reductive amination procedure E, substituting ethyl glycinate for (S)-4-amino-3-hydroxybutanoic acid. Purification by prep RP-HPLC (10-75% acetonitrile in water, 0.1% trifluoroacetic acid) furnished diethyl 2,2'-((((((1S,1'S)-2,2',3,3'-tetrahydro-1H,1'H-[4,4'-biindene]-1,1'-diyl)bis(oxy))bis(5-chloro-2-methoxypyridine-6,3-diyl))bis(methylene))bis(azanediyl))diacetate as a solid. $^1$H NMR (400 MHz, DMSO-$d_6$) δ 9.26 (s, 4H), 7.93 (s, 2H), 7.43 (dd, J=6.9, 1.9 Hz, 2H), 7.39-7.28 (m, 4H), 6.60 (dd, J=6.9, 5.1 Hz, 2H), 4.20 (q, J=7.1 Hz, 4H), 4.10 (s, 4H), 3.97 (d, J=6.5 Hz, 10H), 2.91 (ddd, J=13.4, 8.4, 4.8 Hz, 2H), 2.85-2.60 (m, 4H), 2.16-2.02 (m, 2H), 1.23 (t, J=7.1 Hz, 6H). LCMS-ESI$^+$ (m/z): [M+H]$^+$ calculated for $C_{40}H_{44}Cl_2N_4O_8$: 778.3; found: 777.8.

Example 288: (S)-4-((4-((4''-(2-(((S)-3-carboxy-2-hydroxypropyl)amino)ethoxy)-3''-chloro-2,2'-dimethyl-[1,1':3',1''-terphenyl]-3-yl)methoxy)-5-chloro-2-((5-cyanopyridin-3-yl)methoxy)benzyl)amino)-3-hydroxybutanoic acid

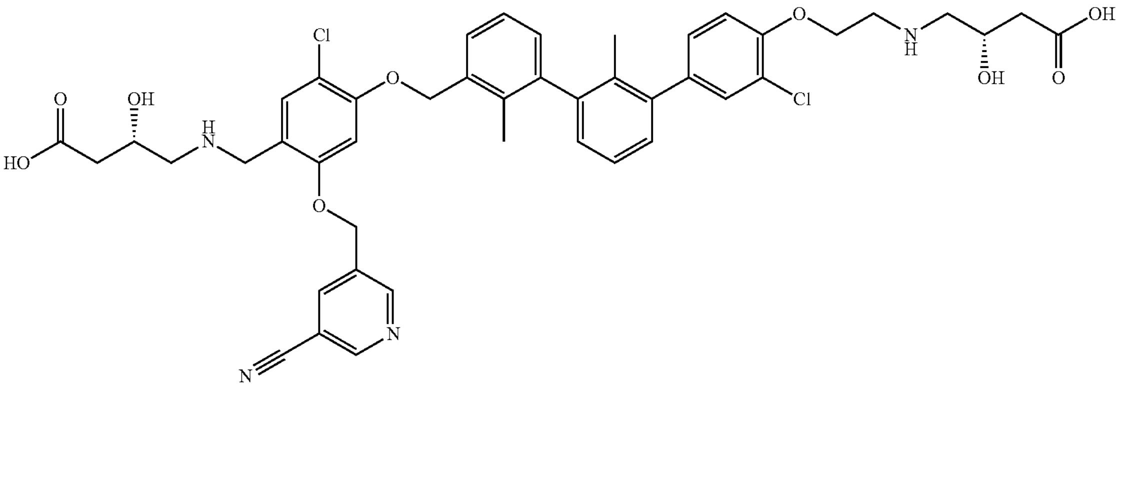

(S)-4-((4-((4''-(2-(((S)-3-carboxy-2-hydroxypropyl) amino)ethoxy)-3''-chloro-2,2'-dimethyl-[1,1':3',1''-terphenyl]-3-yl)methoxy)-5-chloro-2-((5-cyanopyridin-3-yl) methoxy)benzyl)amino)-3-hydroxybutanoic acid was synthesized in analogy to Example 16. $^{1}$H NMR (400 MHz, Methanol-$d_4$) δ 8.94 (dd, J=12.2, 2.1 Hz, 2H), 8.37 (d, J=2.1 Hz, 1H), 7.51 (s, 1H), 7.46 (dd, J=7.7, 1.4 Hz, 1H), 7.39 (d, J=2.1 Hz, 1H), 7.35-6.99 (m, 8H), 5.37 (s, 2H), 5.31 (s, 2H), 4.44 (dd, J=5.6, 4.4 Hz, 2H), 4.35 (dt, J=9.8, 3.2 Hz, 1H), 4.23 (s, 3H), 3.60 (dd, J=5.6, 4.4 Hz, 2H), 3.47 (dd, J=12.7, 3.1 Hz, 1H), 3.26-3.13 (m, 2H), 2.97 (dd, J=12.7, 9.8 Hz, 1H), 2.58 (d, J=6.3 Hz, 2H), 2.51 (dd, J=6.3, 1.2 Hz, 2H), 2.13 (s, 3H), 1.88 (s, 3H). LCMS-ESI$^{+}$ (m/z): $[M+H]^{+}$ calculated for $C_{45}H_{47}Cl_2N_4O_9$: 857.27; found: 857.07.

Example 289: (S)-2-(((5-chloro-6-((4-(2-chloro-4'-sulfamoyl-[1,1'-biphenyl]-3-yl)-2,3-dihydro-1H-inden-1-yl)oxy)-2-((5-cyanopyridin-3-yl)methoxy) pyridin-3-yl)methyl)amino)-2-methylpropanoic acid

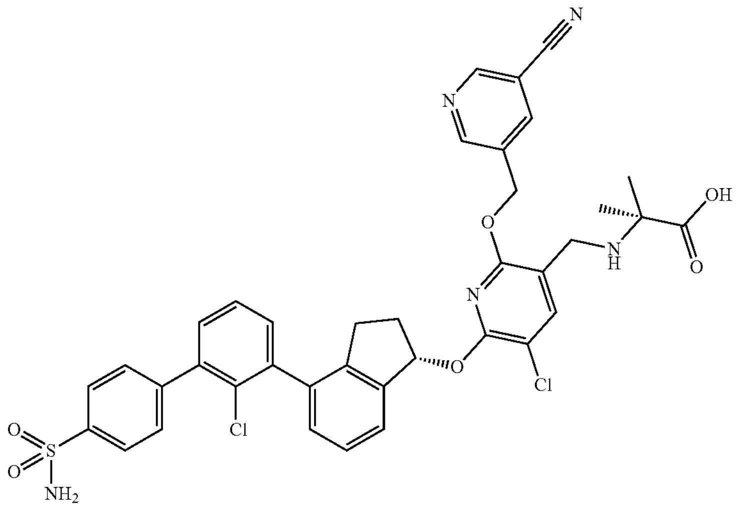

The title compound was synthesized according to general reductive amination procedure D. [M+1]=757.99, 759.82. $^{1}$H NMR (400 MHz, DMSO-$d_6$) δ 9.12-9.02 (m, 3H), 8.97 (d, J=2.0 Hz, 1H), 8.48 (s, 1H), 7.98 (s, 1H), 7.90 (d, J=8.4 Hz, 2H), 7.66 (d, J=8.4 Hz, 2H), 7.57-7.42 (m, 2H), 7.42 (s, 2H), 7.34-7.22 (m, 3H), 6.55 (s, 1H), 5.57 (s, 2H), 4.16 (s, 2H), 2.84 (s, 2H), 2.73 (d, J=12.4 Hz, 1H), 2.52 (s, 1H), 1.95 (dq, J=13.8, 7.3 Hz, 1H), 1.53 (s, 6H).

Example 290: (2S)-2-(((5-chloro-6-(((1S)-4-(2-chloro-4'-(1-methylpyrrolidin-2-yl)-[1,1'-biphenyl]-3-yl)-2,3-dihydro-1H-inden-1-yl)oxy)-2-((5-cyanopyridin-3-yl)methoxy)pyridin-3-yl)methyl)amino)-3-hydroxy-2-methylpropanoic acid

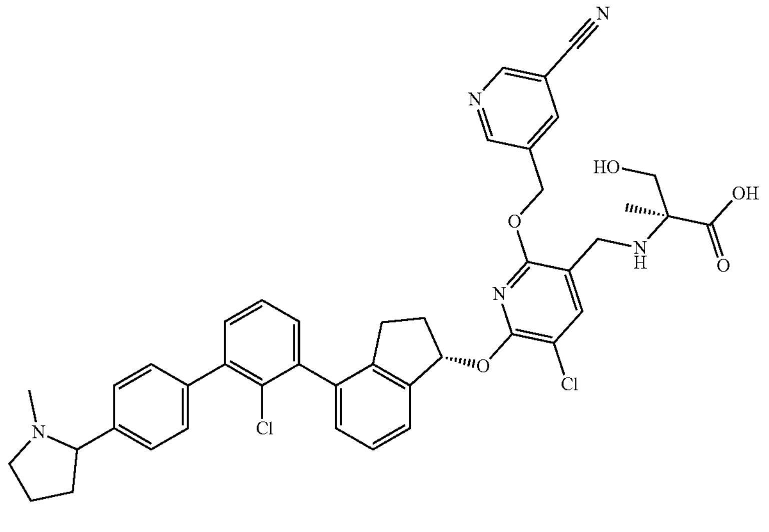 [SMILES: CN1CCCC1c1ccc(-c2cccc(-c3cccc4c3CC[C@@H]4Oc3nc(OCc4cncc(C#N)c4)c(CN[C@@](C)(CO)C(=O)O)cc3Cl)c2Cl)cc1]

The title compound was synthesized according to general reductive amination procedure D. [M+1]=778.05. $^{1}H$ NMR (400 MHz, DMSO-$d_6$) δ 9.84 (s, 1H), 9.06-9.00 (m, 2H), 8.96 (s, 1H), 8.47 (s, 1H), 8.01 (d, J=9.3 Hz, 1H), 7.67-7.56 (m, 4H), 7.51 (t, J=7.6 Hz, 1H), 7.43 (dd, J=7.7, 1.8 Hz, 1H), 7.34-7.24 (m, 2H), 6.53 (s, 1H), 5.56 (s, 2H), 4.46-4.37 (m, 1H), 4.17 (d, J=7.4 Hz, 2H), 3.75 (d, J=11.6 Hz, 2H), 3.28-3.18 (m, 2H), 2.82 (s, 2H), 2.71 (d, J=4.4 Hz, 3H), 2.26-2.09 (m, 1H), 2.15 (s, 2H), 1.94 (s, 2H), 1.43 (s, 3H), 1.20 (d, J=6.7 Hz, 1H).

Example 291: (S)-4-(((5-chloro-6-(((S)-4-(2-chloro-4'-(2-((2-hydroxyethyl)amino)ethoxy)-[1,1'-biphenyl]-3-yl)-2,3-dihydro-1H-inden-1-yl)oxy)-2-((5-cyanopyridin-3-yl)methoxy)pyridin-3-yl)methyl)amino)-3-hydroxybutanoic acid

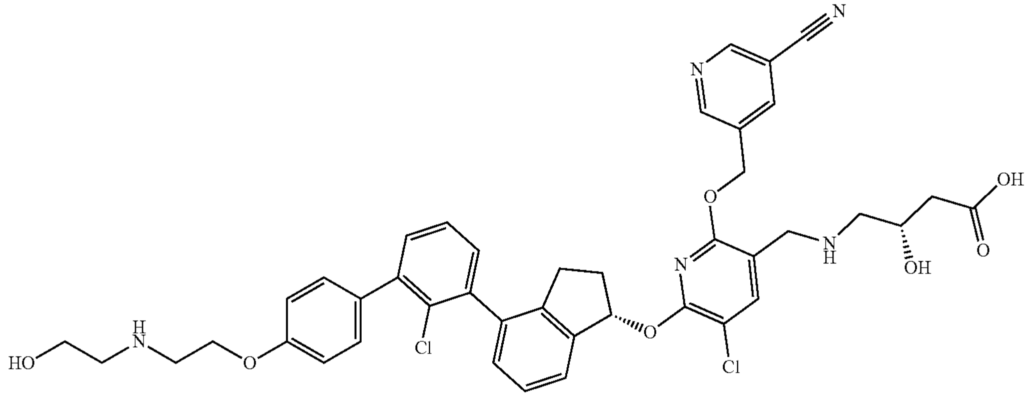 [SMILES: N#Cc1cncc(COc2nc(O[C@H]3CCc4c(-c5cccc(-c6ccc(OCCNCCO)cc6)c5Cl)cccc43)c(Cl)cc2CNC[C@@H](O)CC(=O)O)c1]

The title compound was synthesized according to general reductive amination procedure D. [M+1]=798.03. $^{1}H$ NMR (400 MHz, DMSO-$d_6$) δ 9.02 (d, J=2.0 Hz, 1H), 8.96 (s, 1H), 8.73 (s, 4H), 8.46 (s, 1H), 8.02 (s, 1H), 7.46 (t, J=7.5 Hz, 1H), 7.44-7.37 (m, 3H), 7.37-7.18 (m, 4H), 7.07 (d, J=8.8 Hz, 2H), 6.50 (d, J=5.9 Hz, 1H), 5.63 (s, 1H), 5.57 (s, 2H), 5.27 (s, 1H), 4.30 (t, J=5.1 Hz, 2H), 4.17 (s, 4H), 3.68 (t, J=5.3 Hz, 2H), 3.11 (d, J=7.8 Hz, 3H), 3.00-2.59 (m, 3H), 2.48-2.32 (m, 2H), 1.93 (d, J=6.1 Hz, 1H).

Example 292: (2S)-2-((5-chloro-2-((5-cyanopyridin-3-yl)methoxy)-4-((2,2'-dimethyl-4''-(pyrrolidin-2-ylmethyl)-[1,1':3',1''-terphenyl]-3-yl)methoxy)benzyl)amino)-3-hydroxy-2-methylpropanoic acid

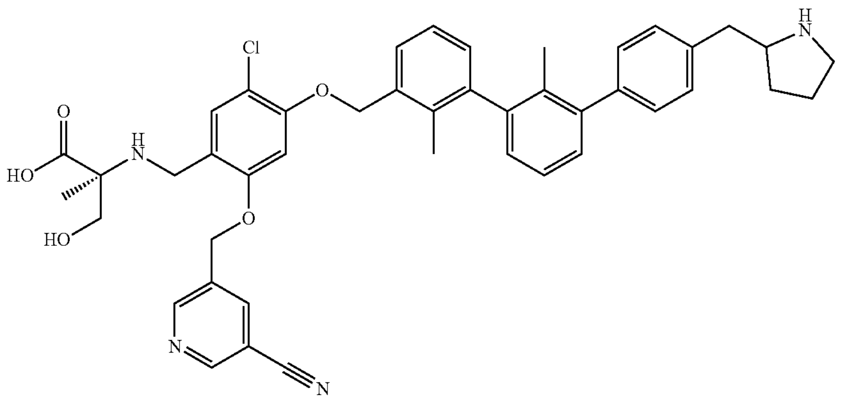 [SMILES: Cc1c(COc2cc(OCc3cncc(C#N)c3)c(CN[C@@](C)(CO)C(=O)O)cc2Cl)cccc1-c1cccc(-c2ccc(CC3CCCN3)cc2)c1C]

The title compound was synthesized according to general reductive amination procedure D. [M+1]=745.07. $^1H$ NMR (400 MHz, DMSO-$d_6$) δ 12.37 (s, 1H), 9.86 (d, J=47.2 Hz, 1H), 9.02 (d, J=2.1 Hz, 1H), 8.96 (s, 1H), 8.67 (s, 3H), 8.46 (s, 1H), 7.80 (d, J=8.2 Hz, 1H), 7.36 (t, J=7.9 Hz, 1H), 7.25 (s, 3H), 7.16 (dd, J=15.4, 3.0 Hz, 1H), 7.16 (s, 1H), 6.92 (d, J=7.4 Hz, 1H), 6.49 (d, J=7.9 Hz, 1H), 6.43 (s, 1H), 5.62 (s, 1H), 5.55 (s, 2H), 5.49 (s, 1H), 4.44 (s, 1H), 4.38 (s, 1H), 4.16 (d, J=5.8 Hz, mH), 3.67 (s, 1H), 3.37 (s, 1H), 3.30 (d, J=6.0 Hz, 1H), 3.17-3.02 (m, 1H), 2.94 (d, J=32.1 Hz, 1H), 2.73 (q, J=7.9, 7.4 Hz, 1H), 2.60 (dt, J=15.8, 7.3 Hz, 1H), 2.52 (s, 2H), 2.48-2.32 (m, 2H), 2.29-2.22 (m, 1H), 2.16 (s, 2H), 1.97-1.78 (m, 2H).

Example 293: (S)-4-(((6-(3'-((4-((((S)-3-carboxy-2-hydroxypropyl)amino)methyl)-2-chloro-5-((5-cyano-pyridin-3-yl)methoxy)phenoxy)methyl)-2,2'-dimethyl-[1,1'-biphenyl]-3-yl)naphthalen-1-yl)methyl) amino)-3-hydroxybutanoic acid

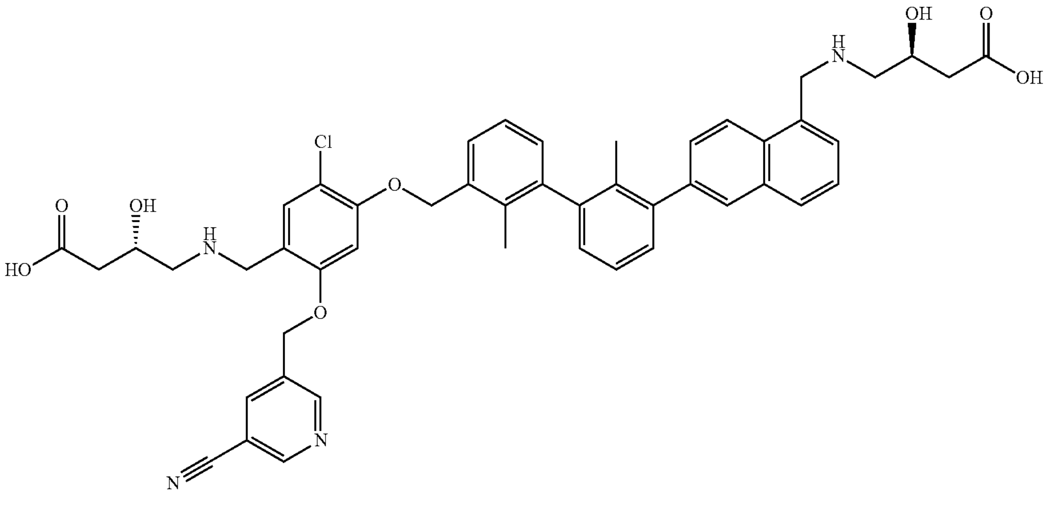 [SMILES: Cc1c(COc2cc(OCc3cncc(C#N)c3)c(CNC[C@@H](O)CC(=O)O)cc2Cl)cccc1-c1cccc(-c2ccc3c(CNC[C@@H](O)CC(=O)O)cccc3c2)c1C]

The title compound was synthesized according to general reductive amination procedure A. 843.427 (M+1). $^1H$ NMR (400 MHz, Methanol-$d_4$) δ 8.96 (d, J=2.1 Hz, 1H), 8.93 (d, J=2.0 Hz, 1H), 8.38 (t, J=2.1 Hz, 1H), 8.25 (d, J=8.7 Hz, 1H), 8.07 (d, J=8.2 Hz, 1H), 7.75-7.71 (m, 1H), 7.69 (dd, J=8.7, 1.8 Hz, 1H), 7.61 (dd, J=8.3, 7.1 Hz, 1H), 7.52 (s, 1H), 7.50-7.46 (m, 1H), 7.40-7.32 (m, 2H), 7.29 (t, J=7.6 Hz, 1H), 7.18 (ddd, J=11.9, 7.4, 1.7 Hz, 2H), 7.09 (s, 1H), 5.39 (s, 2H), 5.33 (s, 2H), 4.82 (s, 2H), 4.42 (dtd, J=9.4, 6.2, 3.0 Hz, 1H), 4.24 (s, 3H), 3.38 (dd, J=12.8, 3.1 Hz, 1H), 3.24-3.14 (m, 2H), 3.02-2.94 (m, 1H), 2.59 (d, J=6.2 Hz, 2H), 2.55-2.50 (m, 2H), 2.19 (s, 3H), 1.95 (s, 3H).

Example 294: (3-((5-chloro-4-((3'-((2-chloro-5-((5-cyanopyridin-3-yl)methoxy)-4-(((3-phosphonopropyl)amino)methyl)phenoxy)methyl)-2,2'-dimethyl-[1,1'-biphenyl]-3-y)methoxy)-2-hydroxybenzyl) amino)propyl)phosphonic acid

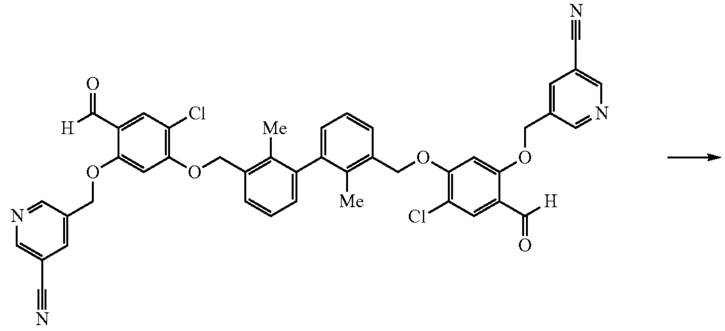

-continued

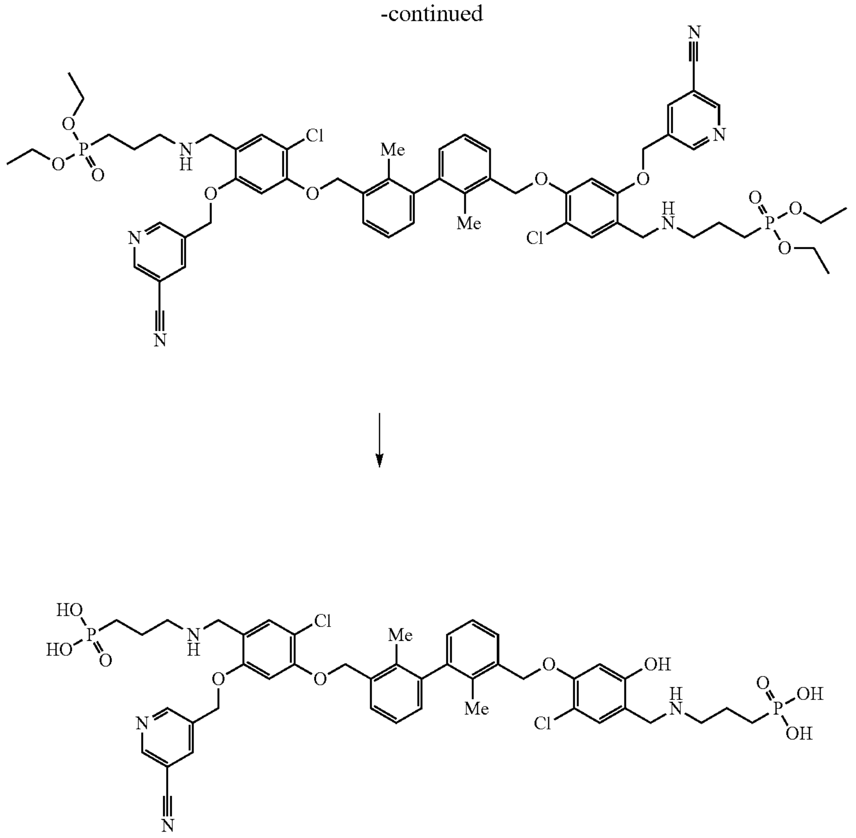

Tetraethyl (((((((2,2'-dimethyl-[1,1'-biphenyl]-3,3'-diyl) bis(methylene))bis(oxy))bis(5-chloro-2-((5-cyanopyridin-3-yl)methoxy)-4,1-phenylene))bis(methylene))bis(azanediyl)) bis(propane-3,1-diyl))bis(phosphonate) was synthesized according to general reductive amination procedure D. MS (Chemical Ionization, TFA): m/z 1041.3 $[M(^{35}Cl)_2+H^+]$, 1043.3 $[M(^{35}Cl)(^{37}C)^+H^+]$, 1045.3 $[M(^{37}C)_2+H^+]$. Phosphodiester (10.2 mg, 0.010 mmol) was dissolved in ACN and 2,6-lutidine (20 μL, 0.17 mmol) added, then TMSBr (63.5 μL, 0.48 mmol) added sequentially in small portions at room temperature. (3-((5-chloro-4-((3'-((2-chloro-5-((5-cyanopyridin-3-yl)methoxy)-4-(((3-phosphonopropyl) amino)methyl)phenoxy)methyl)-2,2'-dimethyl-[1,1'-biphenyl]-3-y)methoxy)-2-hydroxybenzyl)amino)propyl) phosphonic acid isolated by prep. HPLC. MS (Chemical Ionization, TFA): m/z 913.2 $[M(^{35}Cl)_2+H^+]$, 915.2 $[M(^{35}Cl)(^{37}C)^+H^+]$, 917.2 $[M(^{37}C)_2+H^+]$. $^1H$ NMR (400 MHz, DMSO-$d_6$): δ 9.01 (broad s, 2H); 8.48 (broad s, 1H); 7.51 (s, 1H); 7.46 (m, 2H); 7.38 (s, 1H); 7.25 (m, 2H); 7.10 (m, 4H); 6.77 (s, 1H); 5.35 (m, 4H); 5.19 (m, 2H); 4.00 (s, 2H); 3.92 (s, 2H); 2.91 (m, 4H); 1.93 (s, 3H), 1.83 (s, 3H); 1.78 (m, 4H); 1.53 (m, 4H).

Example 295: (S)-2-(((5-chloro-6-(((1S,1'S)-1'-((3-chloro-6-((5-cyanopyridin-3-yl)methoxy)-5-(((2-hydroxyethyl)amino)methyl)pyridin-2-yl)oxy)-2,2',3,3'-tetrahydro-1H,1'H-[4,4'-biinden]-1-yl)oxy)-2-((5-cyanopyridin-3-yl)methoxy)pyridin-3-yl) methylamino)-3-hydroxy-2-methylpropanoic acid

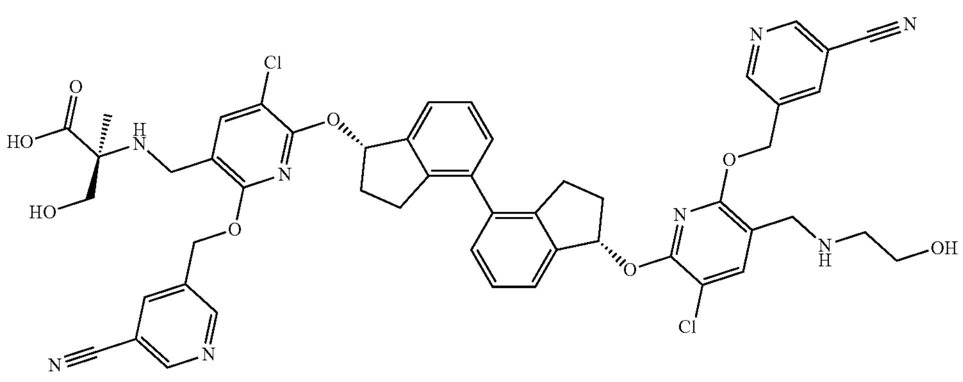

To a mixture of (S)-2-amino-3-hydroxy-2-methylpropanoic acid (88.27 mg, 0.74 mmol), KOH (41.58 mg, 0.74 mmol) in a 40 mL vial was added EtOH (3 mL) and sonicated for 5 min. To this mixture was added solution of 5,5'-((((((1S,1'S)-2,2',3,3'-tetrahydro-1H,1'H-[4,4'-biindene]-1,1'-diyl)bis(oxy))bis(5-chloro-3-formylpyridine-6,2-diyl))bis(oxy))bis(methylene))dinicotinonitrile (60 mg, 0.074 mmol) in $CH_2Cl_2$ (0.5 ml), at once and stirred for 50 min. To this mix was added 2-aminoethan-1-ol (45.27 mg, 0.741 mmol) and allowed to stir for another 50 min. To well stirring mix was added $NaBH(OAc)_3$ (157 mg, 0.741 mmol) followed by AcOH (60 μL). The mixture was left stirring at RT for additional 2 h. At this point the reaction was quenched with 2 N HCl (2 mL, pH ~2) and stirred for 5 min. The solvent was concentrated to dryness under Vacuum. Purification by prep RP-HPLC (10-90% acetonitrile in water, 0.1% trifluoroacetic acid) furnished product (S)-2-(((5-chloro-6-(((S,1'S)-1'-((3-chloro-6-((5-cyanopyridin-3-yl)methoxy)-5-(((2-hydroxyethyl)amino)methyl)pyridin-2-yl)oxy)-2,2',3,3'-tetrahydro-1H,1'H-[4,4'-biinden]-1-yl)oxy)-2-((5-cyanopyridin-3-yl)methoxy)pyridin-3-yl)methyl)amino)-3-hydroxy-2-methylpropanoic acid. [M+1]=958.3. $^1$H NMR (400 MHz, Methanol-$d_4$) δ 8.96 (d, J=2.1 Hz, 2H), 8.84 (d, J=2.0 Hz, 2H), 8.37 (t, J=2.1 Hz, 2H), 7.90 (d, J=3.2 Hz, 2H), 7.33-7.13 (m, 6H), 6.50 (t, J=6.1 Hz, 2H), 5.64 (s, 4H), 4.28 (m, 4H), 3.89-3.78 (m, 4H), 3.20 (t, J=5.2 Hz, 3H), 3.02-2.70 (m, 4H), 2.69-2.45 (m, 4H), 2.20-1.73 (m, 3H).

Example 296: (S)-2-(((3-(3'-((4-((((S)-2-carboxy-1-hydroxypropan-2-yl)amino)methyl)-2-chloro-5-((5-cyanopyridin-3-yl)methoxy)phenoxy)methyl)-2,2'-dimethyl-[1,1'-biphenyl]-3-yl)-8-chloroquinolin-6-yl)methyl)amino)-3-hydroxy-2-methylpropanoic acid

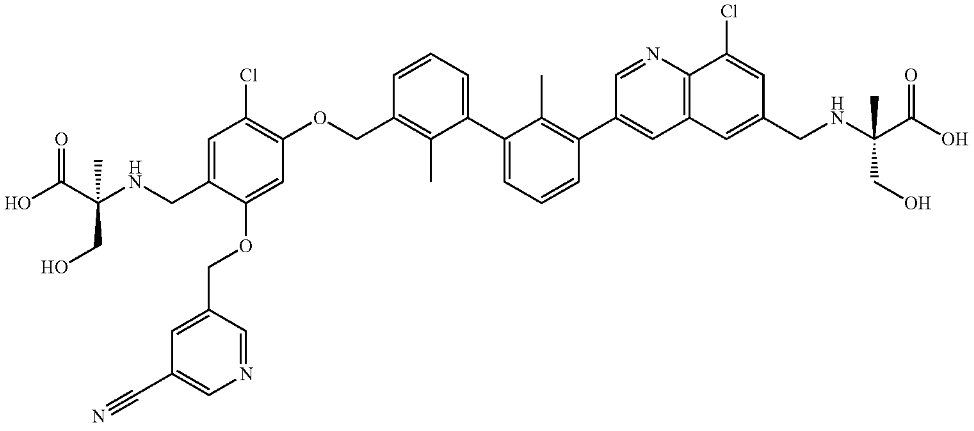

The title compound was synthesized following standard Suzuki coupling procedure described in Example 31 followed by the reductive amination shown in Example 40. [M+1]=879.0. $^1$H NMR (400 MHz, Methanol-$d_4$) δ 9.03 (d, J=2.1 Hz, 1H), 8.98 (d, J=2.1 Hz, 1H), 8.91 (d, J=2.0 Hz, 1H), 8.45 (d, J=2.1 Hz, 1H), 8.42 (t, J=2.0 Hz, 1H), 8.14 (s, 2H), 7.55 (s, 1H), 7.50 (d, J=7.5 Hz, 1H), 7.46-7.36 (m, 2H), 7.30 (t, J=7.6 Hz, 1H), 7.25 (dd, J=7.3, 1.7 Hz, 1H), 7.22-7.16 (m, 1H), 7.10 (s, 1H), 5.36 (d, J=14.5 Hz, 4H), 4.49 (d, J=3.5 Hz, 2H), 4.29 (s, 2H), 4.14 (d, J=12.2 Hz, 1H), 4.01 (d, J=12.1 Hz, 1H), 3.92 (d, J=12.2 Hz, 1H), 3.81 (d, J=12.2 Hz, 1H), 2.19 (s, 3H), 1.97 (s, 3H), 1.67 (s, 4H), 1.53 (s, 3H).

Example 297: (S)-4-(((3-(3'-((4-((((S)-3-carboxy-2-hydroxypropyl)amino)methyl)-2-chloro-5-((5-cyano-pyridin-3-yl)methoxy)phenoxy)methyl)-2,2'-dimethyl-[1,1'-biphenyl]-3-yl)-8-chloroquinolin-6-yl)methyl)amino)-3-hydroxybutanoic acid

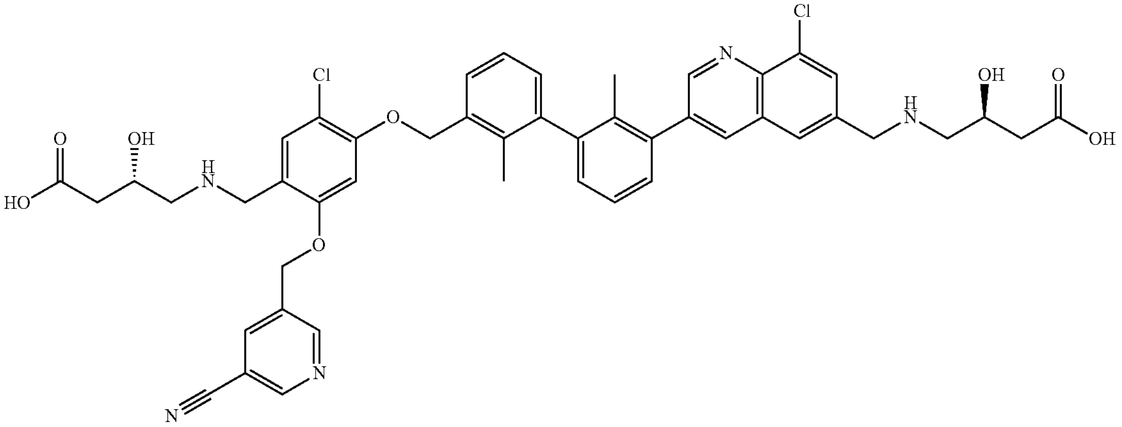 [SMILES: Cc1c(COc2cc(OCc3cncc(C#N)c3)c(CNC[C@@H](O)CC(=O)O)cc2Cl)cccc1-c1cccc(-c2cnc3c(Cl)cc(CNC[C@@H](O)CC(=O)O)cc3c2)c1C]

The title compound was synthesized following standard Suzuki coupling procedure described in Example 31 followed by the reductive amination shown in Example 42. [M+1]=879.0. $^1$H NMR (400 MHz, Methanol-$d_4$) δ 9.03 (d, J=2.1 Hz, 1H), 8.96 (d, J=2.1 Hz, 1H), 8.92 (d, J=2.0 Hz, 1H), 8.44 (d, J=2.1 Hz, 1H), 8.38 (t, J=2.1 Hz, 1H), 8.12 (d, J=1.9 Hz, 1H), 8.10 (d, J=1.8 Hz, 1H), 7.50 (d, J=11.1 Hz, 2H), 7.47-7.37 (m, 2H), 7.30 (t, J=7.6 Hz, 1H), 7.25 (dd, J=7.3, 1.7 Hz, 1H), 7.19 (d, J=7.6 Hz, 1H), 7.09 (s, 1H), 5.38 (s, 2H), 5.33 (s, 2H), 4.47 (s, 2H), 4.33 (ddd, J=9.5, 6.3, 3.0 Hz, 1H), 4.24 (s, 3H), 3.28 (s, 1H), 3.20 (dd, J=12.7, 3.0 Hz, 1H), 3.10 (dd, J=12.6, 9.8 Hz, 1H), 2.97 (dd, J=12.7, 9.8 Hz, 1H), 2.56 (d, J=6.3 Hz, 2H), 2.52 (dd, J=6.3, 1.2 Hz, 2H), 2.18 (s, 3H), 1.97 (s, 3H).

Example 298: (2S,2'S)-2,2'-((((((2,2'-dimethyl-[1,1'-biphenyl]-3,3'-diyl)bis(methylene))bis(oxy))bis(5-chloro-2-((5-(methylsulfonyl)pyridin-3-yl)methoxy)pyridine-6,3-diyl))bis(methylene))bis(azanediyl))bis(3-hydroxy-2-methylpropanoic acid)

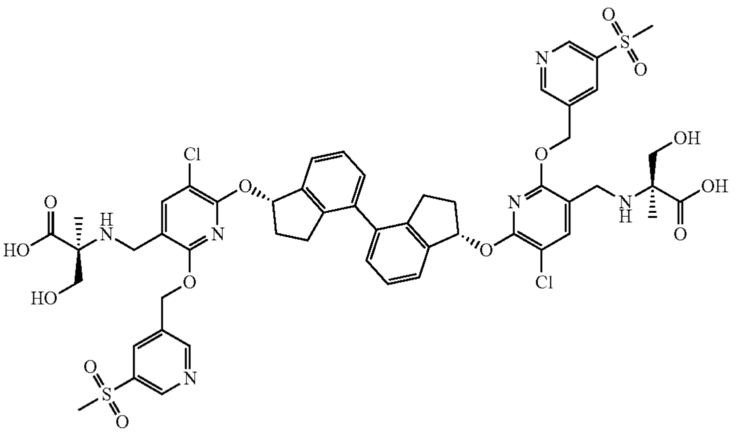

The title compound was synthesized following standard synthesis procedure described in Example 4 using intermediate 6,6'-(((1S,1'S)-2,2',3,3'-tetrahydro-1H,1'H-[4,4'-biindene]-1,1'-diyl)bis(oxy))bis(5-chloro-2-((5-(methylsulfonyl)pyridin-3-yl)methoxy)nicotinaldehyde) and (S)-2-amino-3-hydroxy-2-methylpropanoic acid. [M+1]=1122.0. $^1$H NMR (400 MHz, Methanol-$d_4$) δ 9.05 (dd, J=11.3, 2.1 Hz, 4H), 8.53 (t, J=2.1 Hz, 2H), 7.93 (s, 2H), 7.31-7.14 (m, 6H), 6.53 (dd, J=6.8, 4.9 Hz, 2H), 5.70 (s, 4H), 4.33 (s, 4H), 4.08 (d, J=12.2 Hz, 2H), 3.87 (d, J=12.2 Hz, 2H), 3.31 (s, 4H), 3.17 (s, 6H), 3.02-2.69 (m, 4H), 2.57 (dq, J=13.4, 7.1 Hz, 2H), 2.20-1.99 (m, 2H), 1.61 (s, 6H).

Example 299: (S)-2-((5-chloro-2-((5-cyanopyridin-3-yl)methoxy)-4-((2,2'-dimethyl-3'-(2-((S)-pyrrolidin-2-yl)-1H-benzo[d]imidazol-5-yl)-[1,1'-biphenyl]-3-yl)methoxy)benzyl)amino)-3-hydroxy-2-methylpropanoic acid

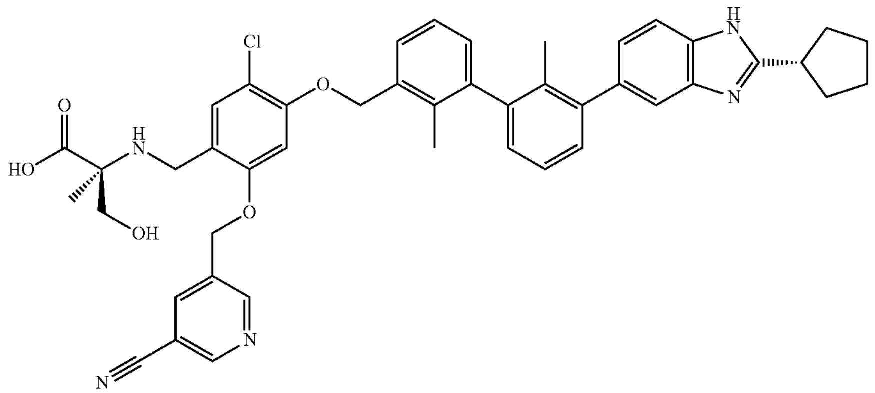

The title compound was synthesized following previously described Suzuki cross coupling, reductive amination, and TFA deprotection procedures. [M+1]=771.3. $^1$H NMR (400 MHz, Methanol-$d_4$) δ 8.98 (d, J=2.1 Hz, 1H), 8.90 (d, J=2.0 Hz, 1H), 8.42 (t, J=2.1 Hz, 1H), 7.70 (d, J=8.3 Hz, 1H), 7.59 (d, J=1.5 Hz, 1H), 7.55 (s, 1H), 7.47 (dd, J=7.7, 1.4 Hz, 1H), 7.37-7.21 (m, 4H), 7.16 (dd, J=7.7, 1.4 Hz, 1H), 7.13-7.04 (m, 2H), 5.36 (s, 2H), 5.33 (s, 2H), 5.11 (t, J=7.8 Hz, 1H), 4.28 (s, 2H), 4.01 (d, J=12.1 Hz, 1H), 3.81 (d, J=12.2 Hz, 1H), 3.70-3.45 (m, 2H), 2.70-2.59 (m, 1H), 2.44 (dd, J=13.2, 7.9 Hz, 1H), 2.40-2.20 (m, 2H), 2.17 (s, 3H), 1.88 (s, 3H), 1.53 (s, 3H).

Example 300: (S)-4-((5-chloro-2-((5-cyanopyridin-3-yl)methoxy)-4-((2,2'-dimethyl-4''-(2-(pyrrolidin-1-yl)ethyl)-[1,1':3',1''-terphenyl]-3-yl)methoxy)benzyl)amino)-3-hydroxybutanoic acid

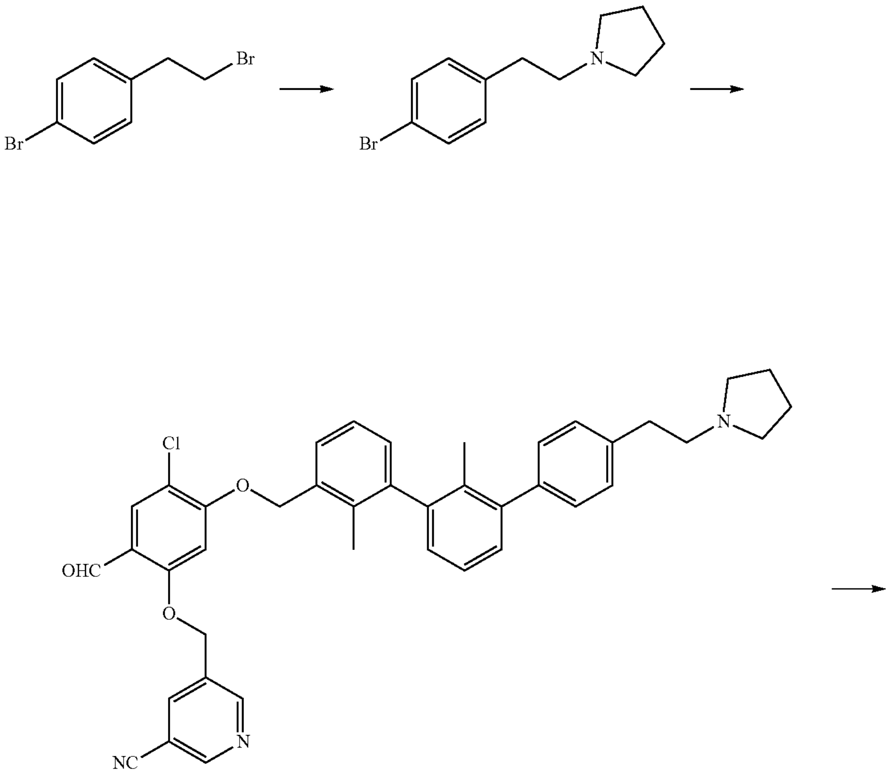

-continued

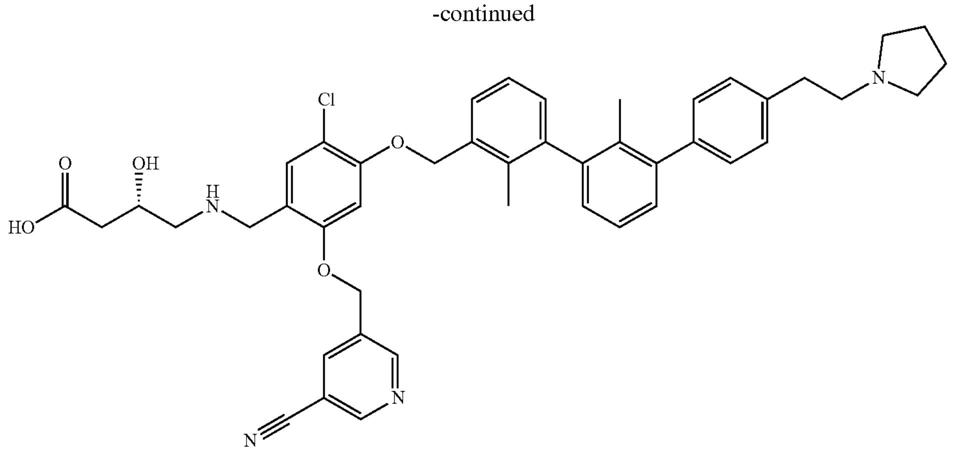

Step 1: The reaction mixture of 1-bromo-4-(2-bromoethyl)benzene (300 mg, 1.13 mmol), potassium carbonate (471.24 mg, 3.41 mmol) and pyrrolidine (0.09 ml, 1.14 mmol) in acetonitrile (6 mL) was stirred at rt overnight. The reaction mixture was then filtered. The filtrate was concentrated down and the residue was purified by silica gel column chromatography to afford 1-(4-bromophenethyl) pyrrolidine.

Step 2: The reaction mixture of 5-((4-chloro-5-((2,2'-dimethyl-3'-(4,4,5,5-tetramethyl-1,3,2-dioxaborolan-2-yl)-[1,1'-biphenyl]-3-yl)methoxy)-2-formylphenoxy)methyl) nicotinonitrile (100 mg, 0.16 mmol), 1-(4-bromophenethyl) pyrrolidine (101.28 mg, 0.4 mmol), Tetrakis (triphenylphosphine)palladium(0) (18.98 mg, 0.02 mmol) and Potassium Carbonate (68.09 mg, 0.49 mmol) in 1,4-dioxane (3 mL) and water (0.4 mL) was stirred at 90° C. for 2 h. After cooling down, the reaction mixture was partitioned between ethyl acetate and water. The ethyl acetate layer was taken and concentrated. The residue was purified by silica gel column, affording 5-((4-chloro-5-((2,2'-dimethyl-4"-(2-(pyrrolidin-1-yl)ethyl)-[1,1':3',1"-terphenyl]-3-yl)methoxy)-2-formylphenoxy)methyl)nicotinonitrile. $[M+H]^+$ 656.9

Step-3: Following general reductive amination procedure G, 5-((4-chloro-5-((2,2'-dimethyl-4"-(2-(pyrrolidin-1-yl) ethyl)-[1,1':3',1"-terphenyl]-3-yl)methoxy)-2-formylphenoxy)methyl)nicotinonitrile was converted to (S)-4-((5-chloro-2-((5-cyanopyridin-3-yl)methoxy)-4-((2,2'-dimethyl-4"-(2-(pyrrolidin-1-yl)ethyl)-[1,1':3',1"-terphenyl]-3-yl)methoxy)benzyl)amino)-3-hydroxybutanoic acid as the bis-TFA salt. [M+1]=759.9. $^1$H NMR (400 MHz, Methanol-$d_4$) δ 8.94 (dd, J=14.7, 2.0 Hz, 2H), 8.37 (t, J=2.1 Hz, 1H), 7.50 (s, 1H), 7.46 (dd, J=7.6, 1.4 Hz, 1H), 7.42-7.23 (m, 6H), 7.16 (ddd, J=16.5, 7.7, 1.5 Hz, 2H), 7.13-7.01 (m, 2H), 5.37 (s, 2H), 5.31 (s, 2H), 4.23 (s, 3H), 3.54-3.45 (m, 2H), 3.24-3.06 (m, 5H), 2.97 (dd, J=12.8, 9.8 Hz, 1H), 2.51 (d, J=6.3 Hz, 2H), 2.18 (s, 2H), 2.14 (s, 3H), 2.04 (s, 2H), 1.87 (s, 3H).

Example 301: (2S)-2-((5-chloro-4-((2'-chloro-4"-((dimethylamino)methyl)-6'-fluoro-2-methyl-[1,1':3',1"-terphenyl]-3-yl)methoxy)-2-((5-cyanopyridin-3-yl)methoxy)benzyl)amino)-3-hydroxy-2-methylpropanoic acid

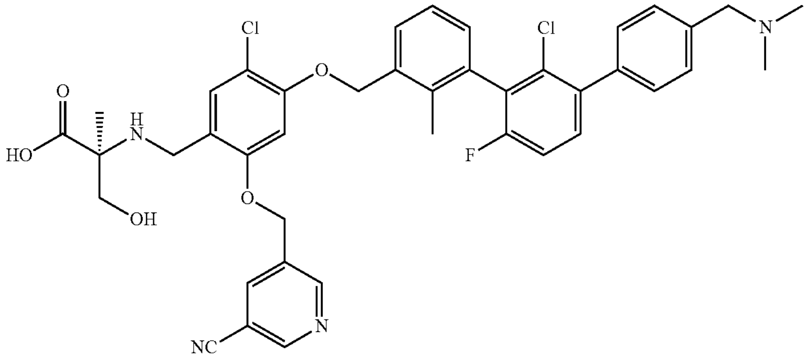 [SMILES: Cc1c(COc2cc(OCc3cncc(C#N)c3)c(CN[C@@](C)(CO)C(=O)O)cc2Cl)cccc1-c1c(F)ccc(-c2ccc(CN(C)C)cc2)c1Cl]

(2S)-2-((5-chloro-4-((2'-chloro-4"-((dimethylamino) methyl)-6'-fluoro-2-methyl-[1,1':3',1"-terphenyl]-3-yl) methoxy)-2-((5-cyanopyridin-3-yl)methoxy)benzyl) amino)-3-hydroxy-2-methylpropanoic acid was synthesized according to general reductive amination procedure D using 5-((4-chloro-5-((2'-chloro-4"-((dimethylamino)methyl)-6'-fluoro-2-methyl-[1,1':3',1"-terphenyl]-3-yl)methoxy)-2-formylphenoxy)methyl)nicotinonitrile in place of 6,6'-(((2,2'-dimethyl-[1,1'-biphenyl]-3,3'-diyl)bis(methylene))bis (oxy))bis(5-chloro-2-methoxynicotinaldehyde) and using (S)-2-amino-3-hydroxy-2-methylpropanoic acid in place (1R,2R)-2-aminocyclopentane-1-carboxylic acid. $^1$H NMR (400 MHz, Methanol-$d_4$) δ 8.97 (d, J=2.1 Hz, 1H), 8.91 (d, J=2.0 Hz, 1H), 8.40 (s, 1H), 7.59 (s, 4H), 7.59-7.48 (m, 2H), 7.46 (dd, J=8.6, 6.0 Hz, 1H), 7.36-7.26 (m, 2H), 7.19 (d, J=7.6 Hz, 1H), 7.04 (s, 1H), 5.35 (s, 2H), 5.33 (s, 2H), 4.37 (s, 2H), 4.27 (s, 2H), 4.00 (d, J=12.1 Hz, 1H), 3.79 (d, J=12.1 Hz, 1H), 2.90 (s, 6H), 2.19 (s, 3H), 1.51 (s, 3H); LRMS: 757.2.

Example 302: (2R)-2-((5-chloro-2-((5-cyanopyridin-3-yl)methoxy)-4-((2,2'-dimethyl-4"-(quinuclidin-3-yloxy)-[1,1':3',1"-terphenyl]-3-yl)methoxy)benzyl) amino)-3-hydroxy-2-methylpropanoic acid

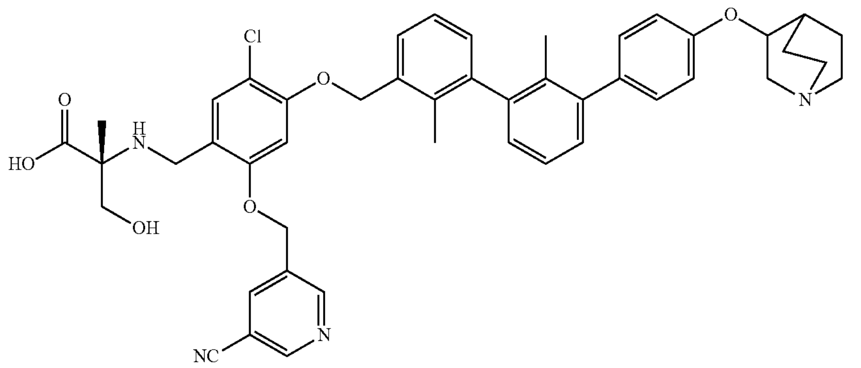 [SMILES: Cc1c(COc2cc(OCc3cncc(C#N)c3)c(CN[C@](C)(CO)C(=O)O)cc2Cl)cccc1-c1cccc(-c2ccc(OC3CN4CCC3CC4)cc2)c1C]

(2R)-2-((5-chloro-2-((5-cyanopyridin-3-yl)methoxy)-4-((2,2'-dimethyl-4"-(quinuclidin-3-yloxy)-[1,1':3',1"-terphenyl]-3-yl)methoxy)benzyl)amino)-3-hydroxy-2-methylpropanoic acid was synthesized according to general reductive amination procedure D using 5-((4-chloro-5-((2,2'-dimethyl-4"-(quinuclidin-3-yloxy)-[1,1':3',1"-terphenyl]-3-yl) methoxy)-2-formylphenoxy)methyl)nicotinonitrile in place of 6,6'-(((2,2'-dimethyl-[1,1'-biphenyl]-3,3'-diyl)bis(methylene))bis(oxy))bis(5-chloro-2-methoxynicotinaldehyde) and using (R)-2-amino-3-hydroxy-2-methylpropanoic acid in place (1R,2R)-2-aminocyclopentane-1-carboxylic acid. $^1$H NMR (400 MHz, Methanol-$d_4$) δ 8.98 (d, J=2.1 Hz, 1H), 8.91 (d, J=1.9 Hz, 1H), 8.42 (s, 1H), 7.64 (dd, J=12.7, 7.5 Hz, 1H), 7.55 (s, 1H), 7.46 (d, J=7.6 Hz, 1H), 7.28 (dd, J=13.2, 7.9 Hz, 4H), 7.18 (d, J=6.8 Hz, 1H), 7.14 (d, J=7.6 Hz, 1H), 7.09-6.98 (m, 3H), 5.36 (s, 2H), 5.32 (s, 2H), 4.93 (s, 1H), 4.28 (s, 2H), 4.01 (d, J=12.1 Hz, 1H), 3.89-3.72 (m, 2H), 3.58-3.30 (m, 5H), 2.55 (s, 1H), 2.43-2.30 (m, 1H), 2.22-2.06 (m, 1H), 2.14 (s, 3H), 2.01 (d, J=8.7 Hz, 1H), 1.96-1.81 (m, 1H), 1.88 (s, 3H), 1.52 (s, 3H); LRMS: 787.3.

Example 303: (2S,4S)-1-((5-chloro-6-((2,2'-dichloro-4"-(2-((2-hydroxyethyl)amino)ethoxy)-[1,1':3',1"-terphenyl]-3-yl)methoxy)-2-((5-(methylsulfonyl)pyridin-3-yl)methoxy)pyridin-3-yl)methyl)-4-hydroxypyrrolidine-2-carboxylic acid

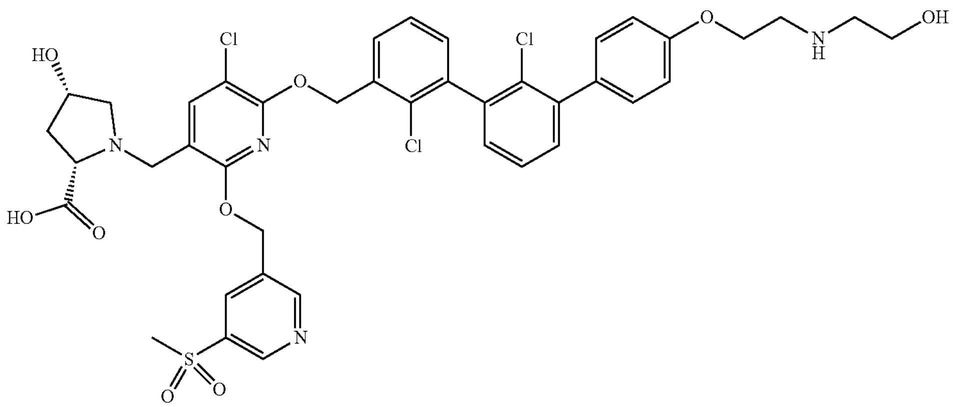 [SMILES: CS(=O)(=O)c1cncc(COc2nc(OCc3cccc(-c4cccc(-c5ccc(OCCNCCO)cc5)c4Cl)c3Cl)c(Cl)cc2CN2C[C@@H](O)C[C@H]2C(=O)O)c1]

(2S,4S)-1-((5-chloro-6-((2,2'-dichloro-4"-(2-((2-hydroxyethyl)amino)ethoxy)-[1,1':3',1"-terphenyl]-3-yl)methoxy)-2-((5-(methylsulfonyl)pyridin-3-yl)methoxy)pyridin-3-yl)methyl)-4-hydroxypyrrolidine-2-carboxylic acid was synthesized according to general reductive amination procedure D using 5-chloro-6-((2,2'-dichloro-4"-(2-((2-hydroxyethyl)amino)ethoxy)-[1,1':3',1"-terphenyl]-3-yl)methoxy)-2-((5-(methylsulfonyl)pyridin-3-yl)methoxy)nicotinaldehyde 2,2,2-trifluoroacetate (1 equiv) and N,N-diisopropylethylamine (3 equiv) in place of 6,6'-(((2,2'-dimethyl-[1,1'-biphenyl]-3,3'-diyl)bis(methylene))bis(oxy))bis(5-chloro-2-methoxynicotinaldehyde) and using (2S,4S)-4-hydroxypyrrolidine-2-carboxylic acid in place (1R,2R)-2-aminocyclopentane-1-carboxylic acid. $^1$H NMR (400 MHz, Methanol-$d_4$) δ 9.04 (d, J=2.3 Hz, 1H), 8.96 (d, J=2.0 Hz, 1H), 8.49 (s, 1H), 7.98 (s, 1H), 7.58 (d, J=7.6 Hz, 1H), 7.46-7.34 (m, 5H), 7.30 (d, J=7.6 Hz, 1H), 7.26 (d, J=7.3 Hz, 1H), 7.09 (d, J=8.3 Hz, 2H), 5.75-5.49 (m, 4H), 4.61-4.26 (m, 6H), 3.90-3.84 (m, 2H), 3.58-3.51 (m, 3H), 3.40-3.27 (m, 1H), 3.29-3.21 (m, 2H), 3.17 (d, J=0.9 Hz, 3H), 2.74-2.67 (m, 1H), 2.23 (d, J=13.9 Hz, 1H); LRMS: 871.2.

Example 304: 2-(((5-chloro-6-((2,2'-dichloro-4"-(2-((2-hydroxyethyl)amino)ethoxy)-[1,1':3',1"-terphenyl]-3-yl)methoxy)-2-((5-(methylsulfonyl)pyridin-3-yl)methoxy)pyridin-3-yl)methyl)amino)-2-methylpropanoic acid

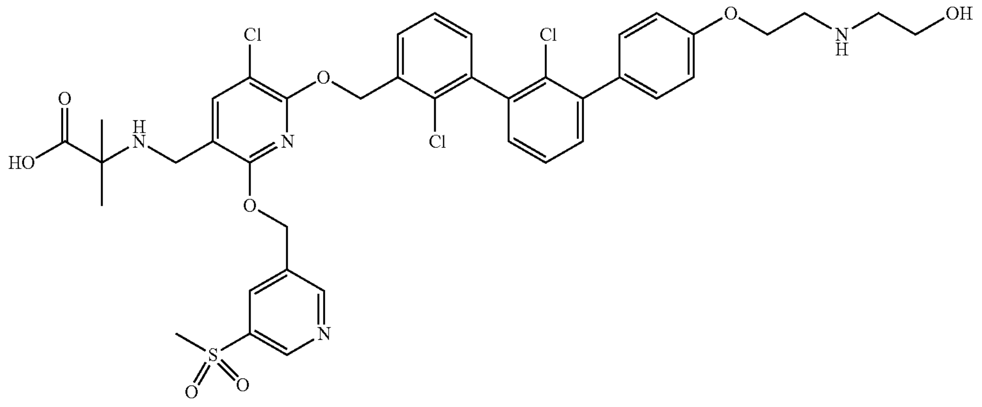 [SMILES: CC(C)(NCc1cc(Cl)c(OCc2cccc(-c3cccc(-c4ccc(OCCNCCO)cc4)c3Cl)c2Cl)nc1OCc1cncc(S(C)(=O)=O)c1)C(=O)O]

N,N-diisopropylethylamine (155 μL, 0.888 mmol) was added via syringe to a stirred mixture of 2-(trimethylsilyl)ethyl (2-((2',2"-dichloro-3"-(((3-chloro-5-formyl-6-((5-(methylsulfonyl)pyridin-3-yl)methoxy)pyridin-2-yl)oxy)methyl)-[1,1':3',1"-terphenyl]-4-yl)oxy)ethyl)(2-hydroxyethyl)carbamate (100 mg, 0.111 mmol) and methyl 2-amino-2-methylpropanoate hydrochloride (102 mg, 0.666 mmol) in dimethylsulfoxide (2.5 mL) at room temperature, and the resulting mixture was heated to 60° C. in a heating block. After 10 min, sodium triacetoxyborohydride (141 mg, 0.666 mmol) was added as a solid. After 1 h, the resulting mixture was allowed to cool to room temperature. Saturated aqueous sodium carbonate solution (10 mL), diethyl ether (40 mL), and ethyl acetate (20 mL) were added sequentially, and the organic layer was washed with water (3×60 mL), was dried over anhydrous magnesium sulfate, was filtered, and was concentrated under reduced pressure. The residue was dissolved with dichloromethane (5.0 mL), and the resulting mixture was stirred at room temperature. Trifluoroacetic acid (2.0 mL) was added via syringe. After 60 min, the resulting mixture was concentrated under reduced pressure, and the residue was dried azeotropically by concentration of a toluene solution under reduced pressure (2×3 mL). The residue was dissolved with dimethylsulfoxide, and the resulting mixture was stirred at room temperature. Aqueous sodium hydroxide solution (2.0 M, 370 μL, 0.64 mmol) was added via syringe. After 15 min, trifluoroacetic acid (200 μL) was added via syringe, and the resulting mixture was filtered and was purified by reverse phase preparative HPLC (0.1% trifluoroacetic acid in acetonitrile/water) to give 2-(((5-chloro-6-((2,2'-dichloro-4"-(2-((2-hydroxyethyl)amino)ethoxy)-[1,1':3',1"-terphenyl]-3-yl)methoxy)-2-((5-(methylsulfonyl)pyridin-3-yl)methoxy)pyridin-3-yl)methyl)amino)-2-methylpropanoic acid. $^1$H NMR (400 MHz, Methanol-$d_4$) δ 9.04 (d, J=2.2 Hz, 1H), 8.96 (d, J=2.0 Hz, 1H), 8.46 (s, 1H), 7.95 (s, 1H), 7.54 (d, J=7.2 Hz, 1H), 7.47-7.35 (m, 5H), 7.28 (d, J=6.8 Hz, 1H), 7.25 (dd, J=7.3, 2.0 Hz, 1H), 7.08 (d, J=8.6 Hz, 2H), 5.71 (d, J=13.6 Hz, 1H), 5.65-5.47 (m, 3H), 4.40-4.31 (m, 2H), 4.21 (s, 2H), 3.90-3.82 (m, 2H), 3.54 (t, J=5.0 Hz, 2H), 3.28-3.23 (m, 2H), 3.16 (s, 3H), 1.61 (s, 6H); LRMS: 843.3.

Example 305: (S)-2-(((5-chloro-2-((5-cyanopyridin-3-yl)methoxy)-6-((3'-((R)-1-(dimethylamino)-1-(hydroxymethyl)-2,3-dihydro-1H-inden-5-yl)-2,2'-dimethyl-[1,1'-biphenyl]-3-yl)methoxy)pyridin-3-yl)methyl)amino)-3-hydroxy-2-methylpropanoic acid

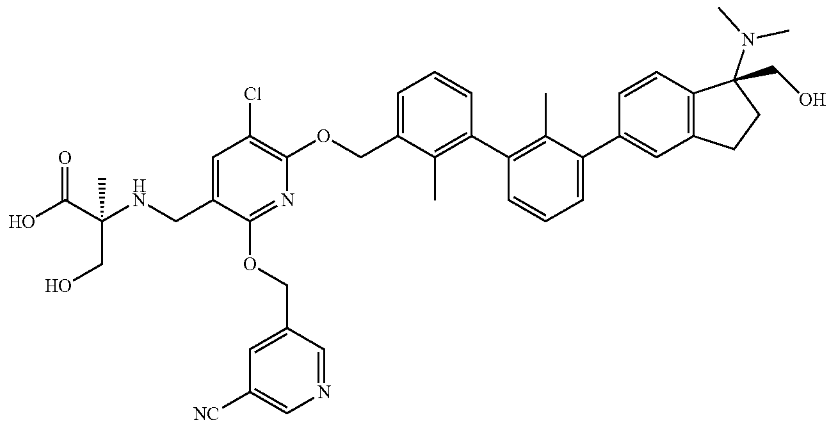 [SMILES: Cc1c(COc2nc(OCc3cncc(C#N)c3)c(CN[C@@](C)(CO)C(=O)O)cc2Cl)cccc1-c1cccc(-c2ccc3c(c2)CC[C@@]3(CO)N(C)C)c1C]

(S)-2-(((5-chloro-2-((5-cyanopyridin-3-yl)methoxy)-6-((3'-((R)-1-(dimethylamino)-1-(hydroxymethyl)-2,3-dihydro-1H-inden-5-yl)-2,2'-dimethyl-[1,1'-biphenyl]-3-yl)methoxy)pyridin-3-yl)methyl)amino)-3-hydroxy-2-methylpropanoic acid was synthesized in a manner similar to Procedure D using 5 (R)-5-(((5-chloro-6-((3'-(1-(dimethylamino)-1-(hydroxymethyl)-2,3-dihydro-1H-inden-5-yl)-2,2'-dimethyl-[1,1'-biphenyl]-3-yl)methoxy)-3-formylpyridin-2-yl)oxy)methyl)nicotinonitrile in place of 6,6'-(((2,2'-dimethyl-[1,1'-biphenyl]-3,3'-diyl)bis(methylene))bis(oxy))bis(5-chloro-2-methoxynicotinaldehyde) and using (S)-2-amino-3-hydroxy-2-methylpropanoic acid in place (1R,2R)-2-aminocyclopentane-1-carboxylic acid. $^1$H NMR (400 MHz, Methanol-$d_4$) δ 8.98 (d, J=2.1 Hz, 1H), 8.91 (d, J=1.9 Hz, 1H), 8.42 (s, 1H), 7.74 (d, J=7.9 Hz, 1H), 7.55 (s, 1H), 7.47 (d, J=7.6 Hz, 1H), 7.40-7.23 (m, 4H), 7.21 (d, J=7.4 Hz, 1H), 7.15 (d, J=7.6 Hz, 1H), 7.11 (d, J=8.2 Hz, 1H), 7.08 (s, 1H), 5.37 (s, 2H), 5.32 (s, 2H), 4.28 (s, 2H), 4.05 (d, J=12.2 Hz, 1H), 4.01 (d, J=12.2 Hz, 1H), 3.93 (d, J=12.1 Hz, 1H), 3.80 (d, J=12.2 Hz, 1H), 3.23-3.13 (m, 2H), 2.92 (s, 3H), 2.70-2.51 (m, 1H), 2.65 (s, 3H), 2.26-2.16 (m, 1H), 2.15 (s, 3H), 1.89 (s, 3H), 1.52 (s, 3H); LRMS: 775.3.

Example 306: 5-(((5-chloro-6-((4''-(2-(dimethylamino)-1-hydroxyethyl)-2,2'-dimethyl-[1,1':3',1''-terphenyl]-3-yl)methoxy)-3-(((2-hydroxyethyl)amino)methyl)pyridin-2-yl)oxy)methyl)nicotinonitrile

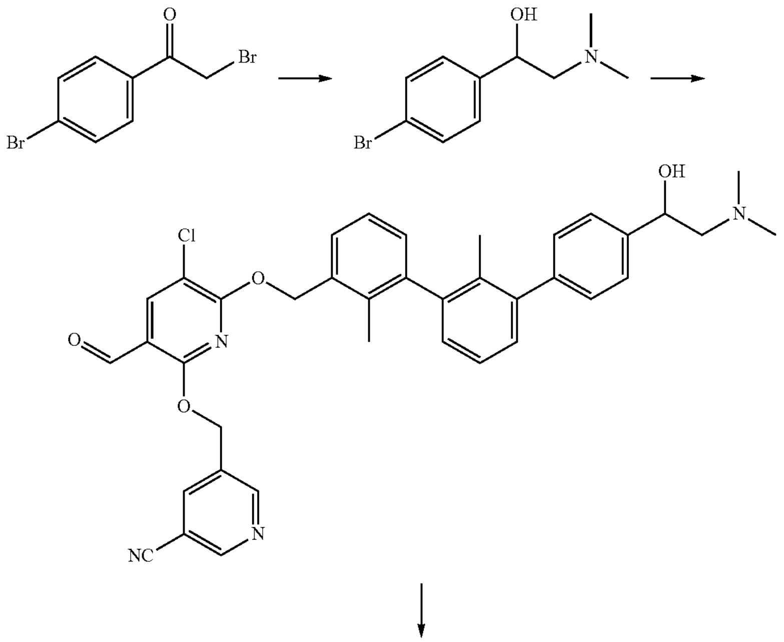

-continued

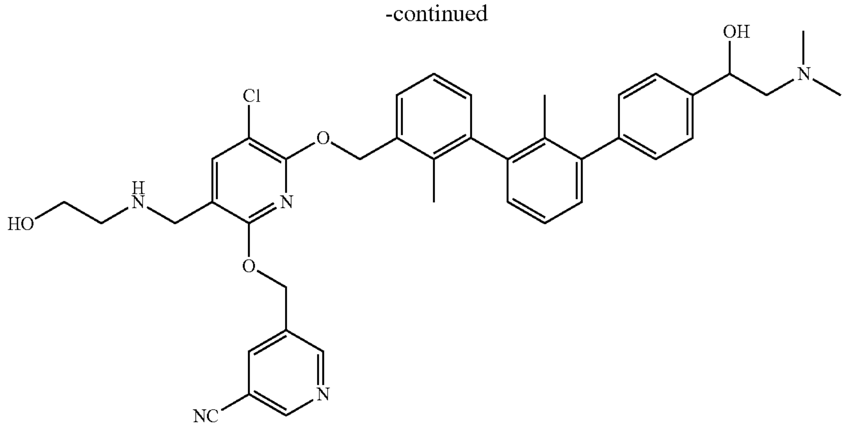

Step 1. 2-Bromo-1-(4-bromophenyl)ethan-1-one (1.50 g, 5.40 mmol) was added as a solid to a stirred mixture of dimethylamine solution (2.0 M in tetrahydrofuran, 8.10 mL, 16 mmol), sodium carbonate (572 mg, 5.40 mmol), and water (2.0 mL) at room temperature, and the resulting mixture was heated to 65° C. in a heating block. After 25 min, methanol (10.0 mL) was added, and the resulting mixture was cooled to 0° C. After 5 min, sodium borohydride (613 mg, 16.2 mmol) was added as a solid under a nitrogen atmosphere, and the resulting mixture was allowed to warm to room temperature. After 15 min, ethyl acetate (70 mL) was added. The organic layer was washed with brine (40 mL), was dried over sodium sulfate, was filtered, and was concentrated under reduced pressure. The residue was purified by flash column chromatography on silica gel (0 to 20% methanol in dichloromethane) to give 1-(4-bromophenyl)-2-(dimethylamino)ethan-1-ol.

Step 2. A stirred mixture of 5-((4-chloro-5-((2,2'-dimethyl-3'-(4,4,5,5-tetramethyl-1,3,2-dioxaborolan-2-yl)-[1,1'-biphenyl]-3-yl)methoxy)-2-formylphenoxy)methyl)nicotinonitrile (25 mg, 0.041 mmol), 1-(4-bromophenyl)-2-(dimethylamino)ethan-1-ol (20 mg, 0.082 mmol), saturated aqueous sodium carbonate solution (2.0 M, 164 μL, 0.33 mmol), and chloro(2-dicyclohexylphosphino-2',4',6'-triisopropyl-1,1'-biphenyl)[2-(2'-amino-1,1'-biphenyl)]palladium (II) (2 mg, 0.002 mmol) in 1,4-dioxane (1.5 mL) was heated to 105° C. in a heating block. After 60 min, the resulting mixture was purified by flash column chromatography on silica gel (0 to 20% methanol in dichloromethane) to give 5-(((5-chloro-6-((4"-(2-(dimethylamino)-1-hydroxyethyl)-2,2'-dimethyl-[1,1':3',1"-terphenyl]-3-yl)methoxy)-3-formylpyridin-2-yl)oxy)methyl)nicotinonitrile.

Step 3. 5-(((5-chloro-6-((4"-(2-(dimethylamino)-1-hydroxyethyl)-2,2'-dimethyl-[1,1':3',1"-terphenyl]-3-yl)methoxy)-3-(((2-hydroxyethyl)amino)methyl)pyridin-2-yl)oxy)methyl)nicotinonitrile was synthesized in a manner similar to Procedure D using 5-(((5-chloro-6-((4"-(2-(dimethylamino)-1-hydroxyethyl)-2,2'-dimethyl-[1,1':3',1"-terphenyl]-3-yl)methoxy)-3-formylpyridin-2-yl)oxy)methyl)nicotinonitrile in place of 6,6'-(((2,2'-dimethyl-[1,1'-biphenyl]-3,3'-diyl)bis(methylene))bis(oxy))bis(5-chloro-2-methoxynicotinaldehyde) and using ethanolamine in place (1R,2R)-2-aminocyclopentane-1-carboxylic acid. $^1$H NMR (400 MHz, Methanol-$d_4$) δ 8.95 (d, J=2.1 Hz, 1H), 8.93 (d, J=2.0 Hz, 1H), 8.38 (s, 1H), 7.53 (d, J=8.1 Hz, 2H), 7.51 (s, 1H), 7.46 (d, J=7.5 Hz, 1H), 7.38 (d, J=8.1 Hz, 2H), 7.33-7.23 (m, 2H), 7.19 (d, J=7.5 Hz, 1H), 7.15 (d, J=7.5 Hz, 1H), 7.13-7.04 (m, 2H), 5.37 (s, 2H), 5.31 (s, 2H), 5.12 (dd, J=10.4, 3.7 Hz, 1H), 4.23 (s, 2H), 3.81-3.75 (m, 2H), 3.17-3.08 (m, 2H), 3.03 (s, 3H), 2.96 (s, 3H), 2.14 (s, 3H), 1.87 (s, 3H); LRMS: 691.3.

Example 307: (S)-4-(((6-(3'-((2-chloro-5-((5-cyanopyridin-3-yl)methoxy)-4-(((R)-3-hydroxypyrrolidin-1-yl)methyl)phenoxy)methyl)-2,2'-dimethyl-[1,1'-biphenyl]-3-yl)-2-methoxypyridin-3-yl)methyl)amino)-3-hydroxybutanoic acid

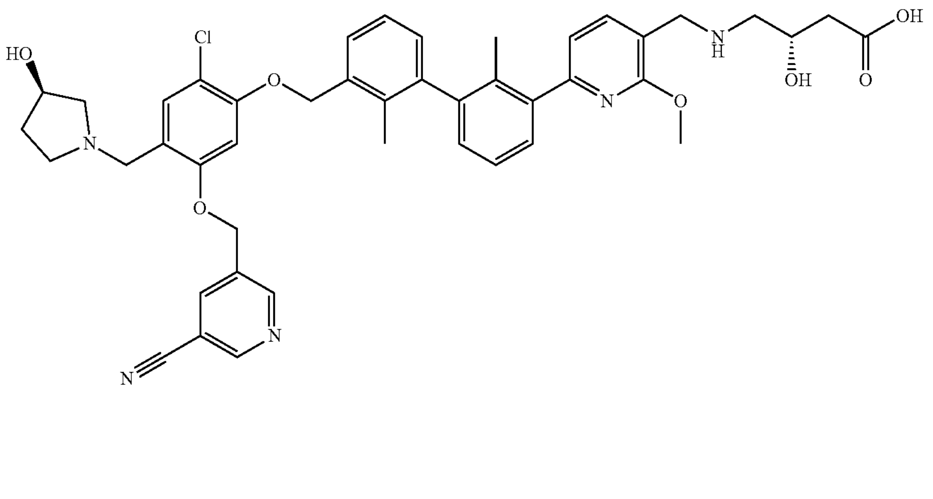 [SMILES: COc1nc(-c2cccc(-c3cccc(COc4cc(OCc5cncc(C#N)c5)c(CN5CC[C@@H](O)C5)cc4Cl)c3C)c2C)ccc1CNC[C@@H](O)CC(=O)O]

The title compound was synthesized according to general reductive amination procedure G. [M+1]=792.084. $^1H$ NMR (400 MHz, Methanol-$d_4$) δ 9.04-8.81 (m, 2H), 8.37 (d, J=8.4 Hz, 1H), 7.86 (d, J=7.5 Hz, 1H), 7.56 (s, 1H), 7.51-7.02 (m, 8H), 5.39 (s, 2H), 5.32 (s, 2H), 4.50 (d, J=21.8 Hz, 2H), 4.33 (d, J=19.1 Hz, 4H), 3.69-3.40 (m, 2H), 3.42-3.15 (m, 3H), 3.15-2.98 (m, 1H), 2.91 (s, 3H), 2.57 (d, J=6.3 Hz, 2H), 2.42-2.00 (m, 2H), 2.14 (s, 3H), 2.04 (s, 3H).
Example 308: (S)-4-(((3"-((2-chloro-5-((5-cyano-pyridin-3-yl)methoxy)-4-(((R)-3-hydroxypyrrolidin-1-yl)methyl)phenoxy)methyl)-2',2"-dimethyl-[1,1':3',1"-terphenyl]-4-yl)methyl)amino)-3-hydroxybutanoic acid
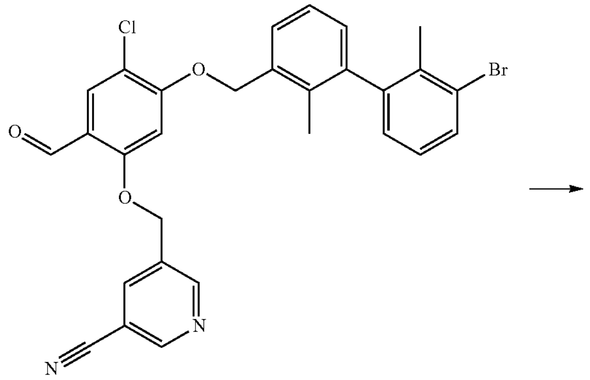
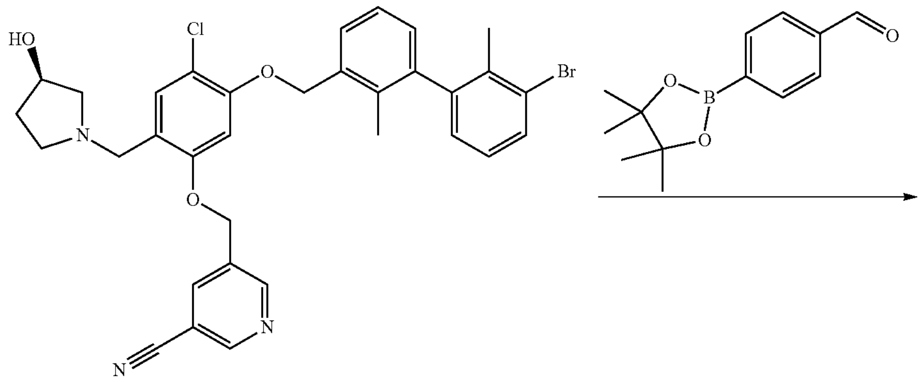
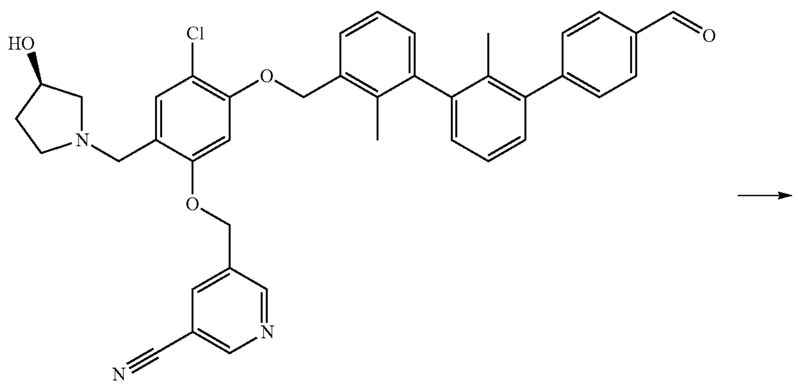

-continued

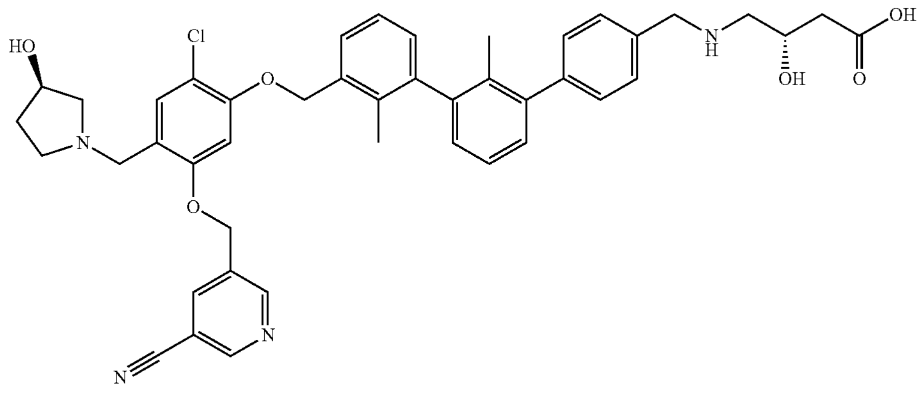

5-((5-((3'-bromo-2, 2'-dimethyl-[1, 1'-biphenyl]-3-yl) methoxy)-4-chloro-2-formylphenoxy) methyl)nicotinonitrile (500 mg, 0.89 mmol) was dissolved in DMF (8 ml) and ethanol (1.6 ml), (R)-pyrrolidin-3-ol (388 mg, 4.45 mmol) was added. The mixture was left stirring at RT for 15 min; sodium triacetoxyborohydride (1.13 g, 5.34 mmol) was added. The mixture was left stirring at RT for 10 min. Complete clean conversion occurred. Ethyl acetate and water were added to quench the reaction. The organic layer was washed with saturated aqueous sodium bicarbonate and then concentrated under vacuum to give (R)-5-((5-((3'-bromo-2, 2'-dimethyl-[1, 1'-biphenyl]-3-yl) methoxy)-4-chloro-2-((3-hydroxypyrrolidin-1-yl) methyl)phenoxy) methyl)nicotinonitrile as the crude. The crude (180 mg, 0.28 mmol) and 4-(4,4,5,5-tetramethyl-1,3,2-dioxaborolan-2-yl) benzaldehyde (106 mg, 0.46 mmol) were dissolved in 1, 4-dioxane (4 ml) and water (0.8 ml), added $K_2CO_3$ (78.6 mg, 0.57 mmol) and tetrakis(triphenylphosphine)palladium(0) (65.7 mg, 0.057 mmol). The mixture was purged with argon and then heated to 82° C. After stirring for 1 h, the mixture was cooled to RT, diluted with ethyl acetate and water. The organic layer was washed with brine, concentrated under vacuum. The residue was purified by silica gel chromatography using EtOAc/MeOH as the eluent to afford (R)-5-((4-chloro-5-((4"-formyl-2,2'-dimethyl-[1,1':3',1"-terphenyl]-3-yl)methoxy)-2-((3-hydroxypyrrolidin-1-yl)methyl) phenoxy)methyl)nicotinonitrile.

(S)-4-(((3"-((2-chloro-5-((5-cyanopyridin-3-yl) methoxy)-4-(((R)-3-hydroxypyrrolidin-1-yl)methyl)phenoxy)methyl)-2',2"-dimethyl-[1,1':3',1"-terphenyl]-4-yl) methyl)amino)-3-hydroxybutanoic acid was synthesized according to general reductive amination procedure G. [M+1]=761.111. $^1$H NMR (400 MHz, Methanol-$d_4$) δ 9.01-8.88 (m, 2H), 8.37 (s, 1H), 7.57 (d, J=8.6 Hz, 3H), 7.53-7.40 (m, 3H), 7.38-7.00 (m, 6H), 5.39 (s, 2H), 5.32 (s, 2H), 4.50 (d, J=21.8 Hz, 2H), 4.42-4.18 (m, 4H), 3.72-3.41 (m, 2H), 3.38-3.22 (m, 2H), 3.25 (dd, J=12.7, 3.1 Hz, 1H), 3.05 (dd, J=12.7, 9.9 Hz, 1H), 2.38-2.05 (m, 2H), 2.55 (d, J=6.3 Hz, 2H), 2.14 (s, 3H), 1.88 (s, 3H).

Example 309: (S)-4-((2-((3"-((2-chloro-5-((5-cyanopyridin-3-yl)methoxy)-4-(((R)-3-hydroxypyrrolidin-1-yl)methyl)phenoxy)methyl)-2',2"-dimethyl-[1,1':3',1"-terphenyl]-4-yl)oxy)ethyl)amino)-3-hydroxybutanoic acid

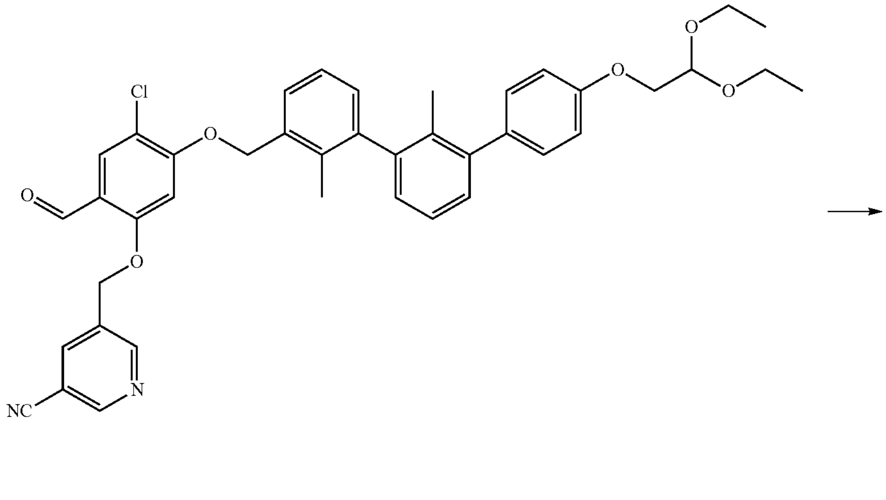

-continued

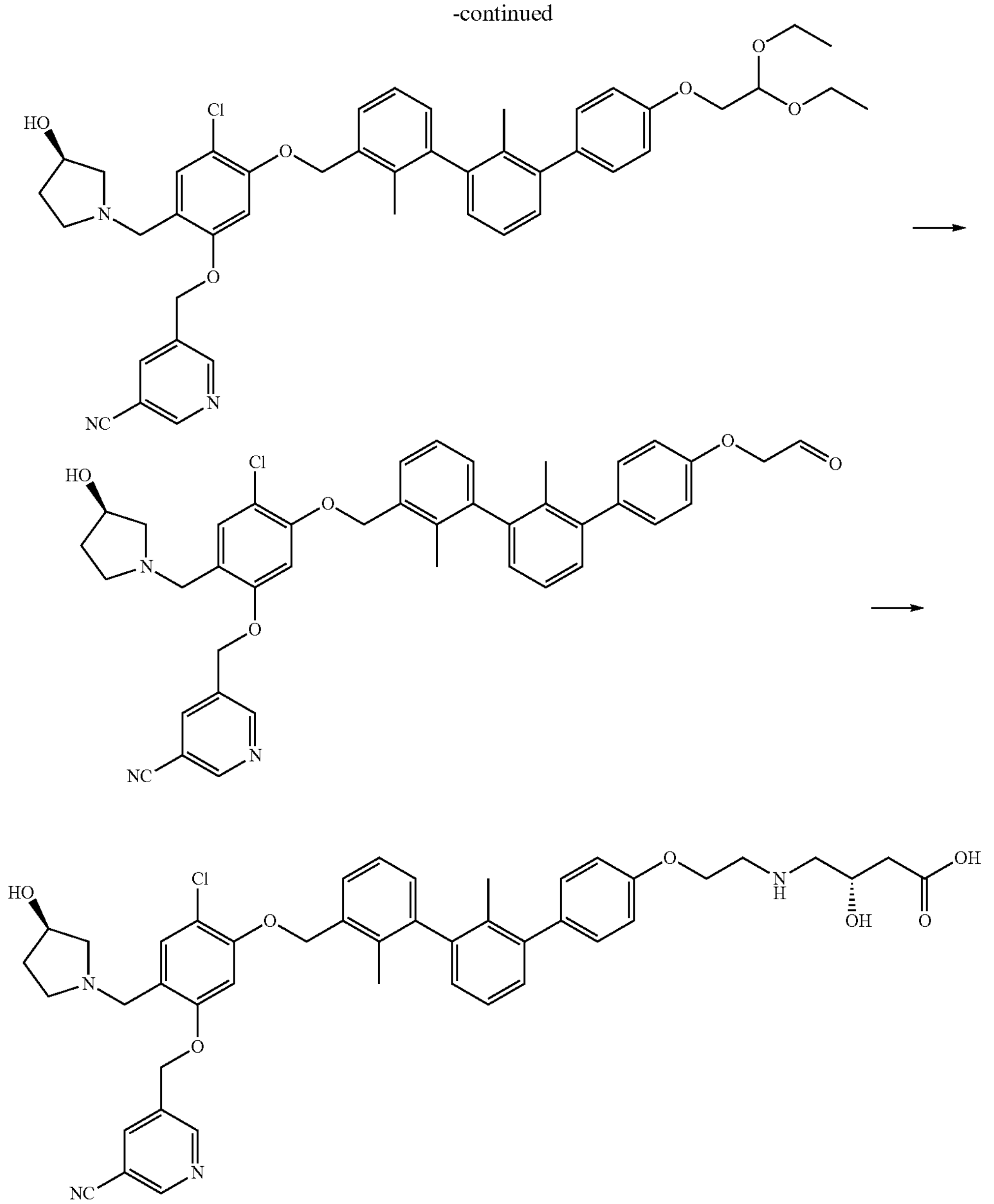

5-((4-chloro-5-((4"-(2,2-diethoxyethoxy)-2,2'-dimethyl-[1,1':3',1"-terphenyl]-3-yl)methoxy)-2-formylphenoxy) methyl)nicotinonitrile (200 mg, 0.29 mmol) was dissolved in DMF (2 ml) and ethanol (0.4 ml), (R)-pyrrolidin-3-ol (126 mg, 1.45 mmol) was added. The mixture was left stirring at RT for 30 min; sodium triacetoxyborohydride (429 mg, 2.03 mmol) was added. The mixture was left stirring at RT for 15 min. Complete clean conversion occurred. Ethyl acetate and water were added to quench the reaction. The organic layer was washed with saturated aqueous sodium bicarbonate and then concentrated under vacuum to give (R)-5-((4-chloro-5-((4"-(2,2-diethoxy-ethoxy)-2,2'-dimethyl-[1,1':3',1"-terphenyl]-3-yl)methoxy)-2-((3-hydroxypyrrolidin-1-yl)methyl)phenoxy)methyl)nicotinonitrile as the crude. The crude was dissolved in 1, 4-dioxane (4 ml), hydrochloric acid (conc., 0.4 ml) was added dropwise, and the mixture was left stirring at RT for 2 h. Ethyl acetate and water were added to the mixture. The organic layer was washed with saturated aqueous sodium bicarbonate and then concentrated under vacuum to give (R)-5-((4-chloro-5-((2,2'-dimethyl-4"-(2-oxoethoxy)-[1,1':3',1"-terphenyl]-3-yl)methoxy)-2-((3-hydroxypyrrolidin-1-yl)methyl)phenoxy)methyl)nicotinonitrile as crude.

(S)-4-((2-((3"-((2-chloro-5-((5-cyanopyridin-3-yl) methoxy)-4-(((R)-3-hydroxypyrrolidin-1-yl)methyl)phenoxy)methyl)-2',2"-dimethyl-[1,1':3',1"-terphenyl]-4-yl) oxy)ethyl)amino)-3-hydroxybutanoic acid was synthesized according to general reductive amination procedure G. [M+1]=791.105. $^1$H NMR (400 MHz, Methanol-$d_4$) δ 9.01-8.89 (m, 2H), 8.37 (s, 1H), 7.56 (s, 1H), 7.46 (d, J=7.6 Hz, 1H), 7.36-7.22 (m, 5H), 7.23-7.00 (m, 5H), 5.39 (s, 2H), 5.32 (s, 2H), 4.50 (d, J=22.2 Hz, 2H), 4.35 (t, J=5.0 Hz, 4H), 3.54 (t, J=5.1 Hz, 3H), 3.35-3.20 (m, 3H), 3.18-3.05 (m, 2H), 2.58 (d, J=6.3 Hz, 2H), 2.35-1.82 (m, 2H), 2.14 (s, 3H), 1.88 (s, 3H).

Example 310: (R)-2-((5-chloro-2-((5-cyanopyridin-3-yl)methoxy)-4-((4"-(2-((2-hydroxyethyl)amino) ethoxy)-2,2'-dimethyl-3"-(methylsulfonyl)-[1,1':3', 1"-terphenyl]-3-yl)methoxy)benzyl)amino)-3-hydroxy-2-methylpropanoic acid

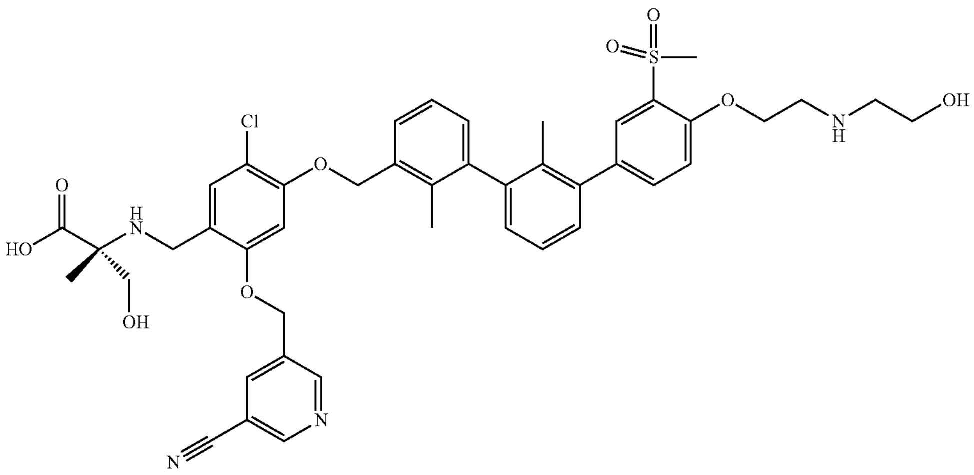 [SMILES: Cc1c(COc2cc(OCc3cncc(C#N)c3)c(CN[C@](C)(CO)C(=O)O)cc2Cl)cccc1-c1cccc(-c2ccc(OCCNCCO)c(S(C)(=O)=O)c2)c1C]

The title compound was synthesized according to general reductive amination procedure G. [M+1]=843.111. $^1$H NMR (400 MHz, Methanol-$d_4$) δ 8.98 (s, 1H), 8.91 (s, 1H), 8.42 (s, 1H), 7.87 (d, J=2.2 Hz, 1H), 7.74 (dd, J=8.5, 2.3 Hz, 1H), 7.55 (s, 1H), 7.53-7.11 (m, 7H), 7.08 (s, 1H), 5.36 (s, 2H), 5.33 (s, 2H), 4.66-4.52 (m, 2H), 4.28 (s, 2H), 4.01 (d, J=12.2 Hz, 1H), 3.93-3.72 (m, 3H), 3.71-3.59 (m, 2H), 3.33 (s, 3H), 3.35-3.30 (m, 2H), 2.15 (s, 3H), 1.90 (s, 3H), 1.52 (s, 3H).

Example 311: (S)-2-((5-chloro-2-((5-cyanopyridin-3-yl) methoxy)-4-((4"-(2-((2-hydroxyethyl) amino) ethoxy)-2, 2'-dimethyl-[1, 1':3',1"-terphenyl]-3-yl) methoxy) benzyl) amino)-3-hydroxy-2-methylpropanoic acid

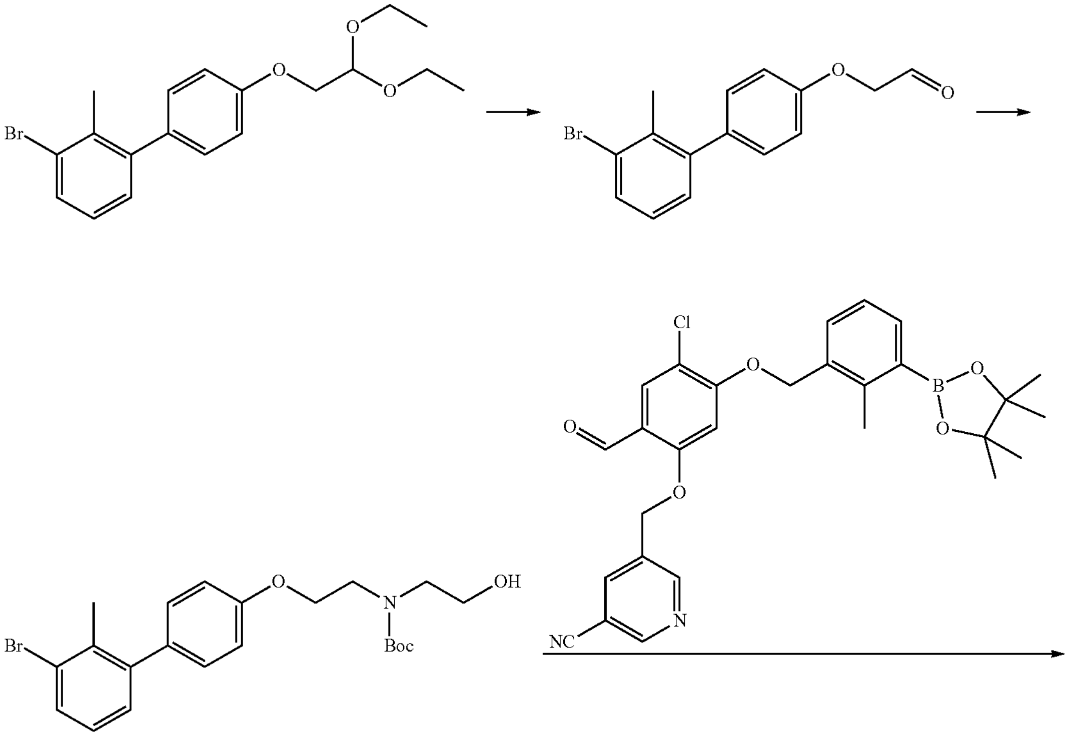

-continued

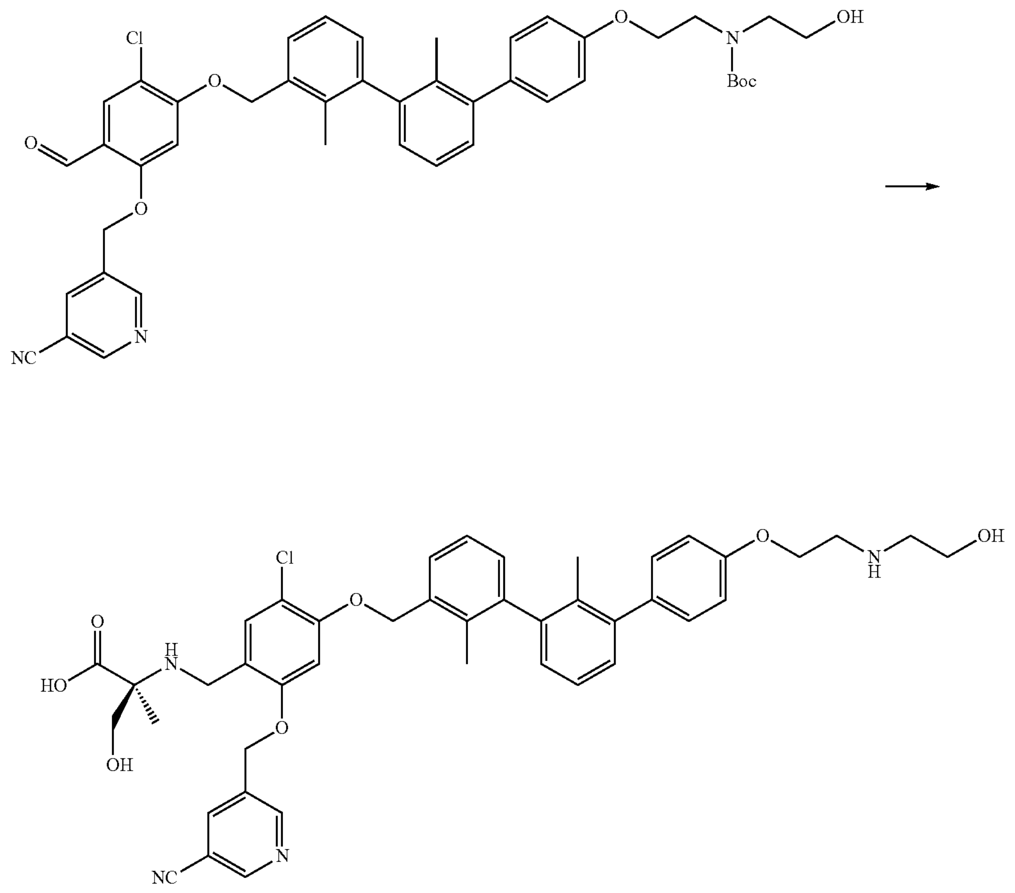

3-bromo-4'-(2, 2-diethoxyethoxy)-2-methyl-1, 1'-biphenyl (1.6 g. 4.22 mmol) was dissolved in 1, 4-dioxane (4 ml). Hydrochloric acid (conc., 0.8 ml) was added dropwise, the mixture was left stirring at RT for 2 h. Ethyl acetate and water were added to the mixture. The organic layer was washed with saturated aqueous sodium bicarbonate and then concentrated under vacuum to give 2-((3'-bromo-2'-methyl-[1, 1'-biphenyl]-4-yl) oxy) acetaldehyde as the crude.

2-aminoethan-1-ol (1.29 g, 21.1.3 mmol) was dissolved in ethanol (20 ml), 2-((3'-bromo-2'-methyl-[1, 1'-biphenyl]-4-yl) oxy) acetaldehyde (the above crude, 4.22 mmol) in $CH_2Cl_2$ (8 ml) was added. The mixture was left stirring at RT for 30 min. Sodium triacetoxyborohydride (5 g, 23.6 mmol) was added. The mixture was left stirring at RT for 30 min, complete conversion occurred. Ethyl acetate and water were added to quench the reaction. The organic layer was washed with saturated aqueous sodium bicarbonate and concentrated under vacuum. The residue crude was then dissolved in THF (15 ml), di-tert-butyl dicarbonate (2 g, 9.19 mmol) was added followed by addition of trimethylamine (1.49 g, 14.7 mmol). The mixture was left stirring at RT. LCMS showed complete conversion after 15 min. Ethyl acetate and water were added to the mixture. The organic layer was concentrated under vacuum. The residue was purified by silica gel chromatography using Hexanes/EtOAc as the eluent to afford tert-butyl (2-((3'-bromo-2'-methyl-[1, 1'-biphenyl]-4-yl) oxy) ethyl) (2-hydroxyethyl) carbamate.

Tert-butyl (2-((3'-bromo-2'-methyl-[1, 1'-biphenyl]-4-yl) oxy) ethyl) (2-hydroxyethyl) carbamate (1.45 g, 3.22 mmol) and 5-((4-chloro-2-formyl-5-((2-methyl-3-(4,4,5,5-tetramethyl-1,3,2-dioxaborolan-2-yl)benzyl)oxy)phenoxy)methyl) nicotinonitrile (2.04 g, 3.93 mmol) were suspended in DMF (25.5 ml) and $H_2O$ (3.7 ml), added $K_2CO_3$ (0.54 g, 3.91 mmol) and [1,1'-bis(diphenylphosphino)ferrocene]dichloropalladium(II), complex with dichloromethane (0.26 g, 0.32 mmol). The mixture was purged with argon and then heated to 83° C. After stirring for 1 h, the mixture was cooled to RT, diluted with ethyl acetate and water. The organic layer was washed with brine, concentrated under vacuum. The residue was purified by silica gel chromatography using Hexanes/EtOAc as the eluent to afford tert-butyl (2-((3"-((2-chloro-5-((5-cyanopyridin-3-yl)methoxy)-4-formylphenoxy)methyl)-2',2"-dimethyl-[1,1':3',1"-terphenyl]-4-yl)oxy)ethyl)(2-hydroxyethyl)carbamate.

The title compound ((S)-2-((5-chloro-2-((5-cyanopyridin-3-yl)methoxy)-4-((4"-(2-((2-hydroxyethyl)amino)ethoxy)-2,2'-dimethyl-[1,1':3',1"-terphenyl]-3-yl)methoxy)benzyl) amino)-3-hydroxy-2-methylpropanoic acid) was synthesized according to general reductive amination procedure G, followed by Boc-deprotection using 20% TFA in $CH_2Cl_2$. [M+1]=765.37. $^1$H NMR (400 MHz, Methanol-$d_4$) δ 8.98 (d, J=2.1 Hz, 1H), 8.91 (d, J=2.0 Hz, 1H), 8.42 (t, J=2.1 Hz, 1H), 7.55 (s, 1H), 7.46 (d, J=7.5 Hz, 1H), 7.39-6.91 (m, 10H), 5.36 (s, 2H), 5.32 (s, 2H), 4.39-4.28 (m, 2H), 4.28 (s, 2H), 4.00 (d, J=12.1 Hz, 1H), 3.92-3.81 (m, 2H), 3.79 (d, J=12.2 Hz, 1H), 3.57-3.48 (m, 2H), 3.29 (s, 2H), 2.14 (s, 3H), 1.87 (s, 3H), 1.52 (s, 3H).

Example 312: (S)-4-((2-((3-carbamoyl-3"-((4-((((S)-3-carboxy-2-hydroxypropyl)amino)methyl)-2-chloro-5-((5-cyanopyridin-3-yl)methoxy)phenoxy)methyl)-2',2"-dimethyl-[1,1':3',1"-terphenyl]-4-yl)oxy)ethyl)amino)-3-hydroxybutanoic acid

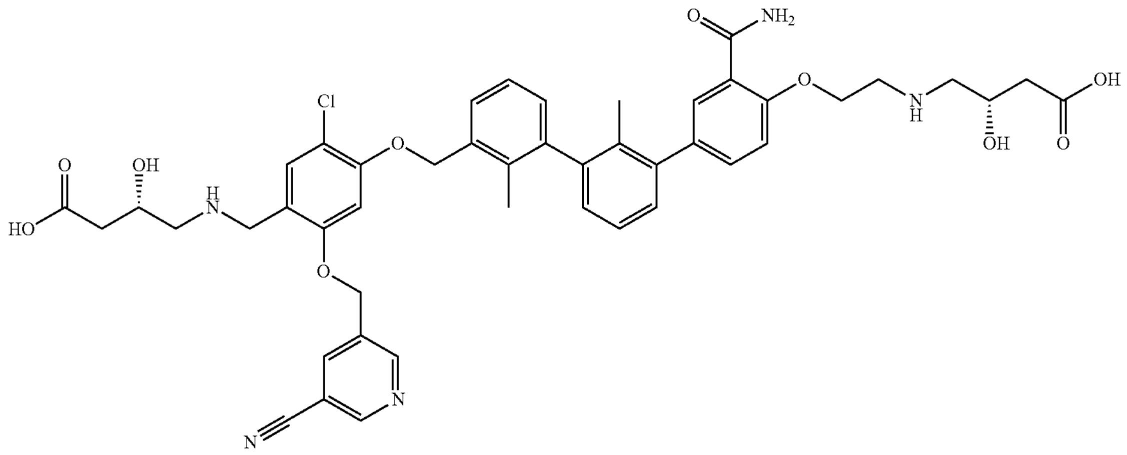 [SMILES: Cc1c(COc2cc(OCc3cncc(C#N)c3)c(CNC[C@@H](O)CC(=O)O)cc2Cl)cccc1-c1cccc(-c2ccc(OCCNC[C@@H](O)CC(=O)O)c(C(N)=O)c2)c1C]

The title compound was synthesized according to general reductive amination procedure G. [M+1]=866.134. $^1$H NMR (400 MHz, Methanol-$d_4$) δ 8.94 (dd, J=10.8, 2.1 Hz, 2H), 8.37 (s, 1H), 7.62 (d, J=2.3 Hz, 1H), 7.55-7.41 (m, 3H), 7.37-6.94 (m, 7H), 5.37 (s, 2H), 5.31 (s, 2H), 4.53-4.44 (m, 2H), 4.23 (s, 3H), 3.54 (d, J=5.0 Hz, 2H), 3.24-3.07 (m, 2H), 2.97 (dd, J=12.8, 9.8 Hz, 1H), 2.65 (s, 2H), 2.58 (dd, J=6.3, 3.7 Hz, 2H), 2.52 (dd, J=6.2, 1.3 Hz, 2H), 2.14 (s, 3H), 1.90 (s, 3H).

Example 313: (S)-2-((4-((4"-(2-(((S)-2-carboxy-1-hydroxypropan-2-yl)amino)ethoxy)-2,2'-dimethyl-[1,1':3',1"-terphenyl]-3-yl)methoxy)-5-chloro-2-((5-cyanopyridin-3-yl)methoxy)benzyl)amino)-3-hydroxy-2-methylpropanoic acid

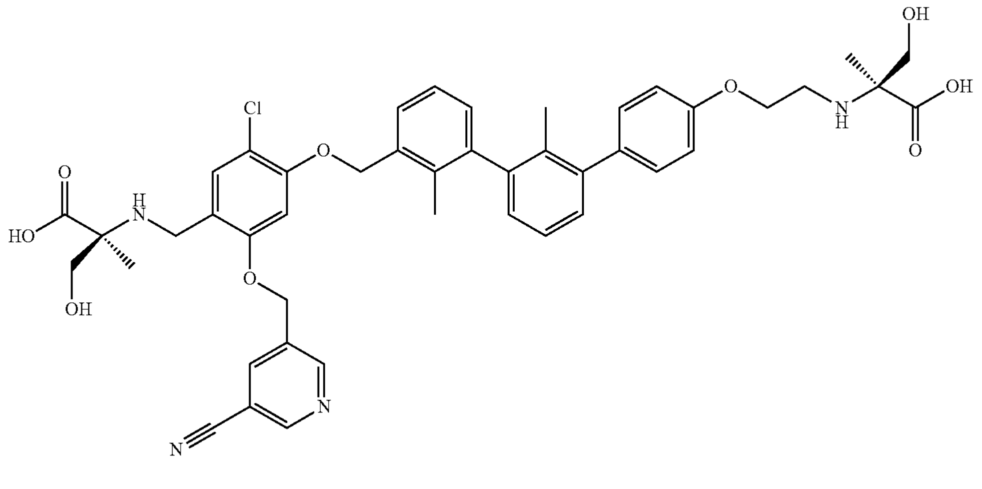 [SMILES: Cc1c(COc2cc(OCc3cncc(C#N)c3)c(CN[C@@](C)(CO)C(=O)O)cc2Cl)cccc1-c1cccc(-c2ccc(OCCN[C@@](C)(CO)C(=O)O)cc2)c1C]

The title compound was synthesized according to general reductive amination procedure G. [M+1]=823.064. $^1$H NMR (400 MHz, Methanol-$d_4$) δ 8.98 (d, J=2.1 Hz, 1H), 8.91 (d, J=2.0 Hz, 1H), 8.42 (s, 1H), 7.55 (s, 1H), 7.46 (d, J=7.6 Hz, 1H), 7.36-6.97 (m, 9H), 5.36 (s, 2H), 5.32 (s, 2H), 4.37 (t, J=5.1 Hz, 2H), 4.28 (s, 2H), 4.03 (dd, J=14.7, 12.1 Hz, 2H), 3.82 (dd, J=16.0, 12.1 Hz, 2H), 3.56 (t, J=5.2 Hz, 2H), 2.15 (s, 3H), 1.88 (s, 3H), 1.60 (s, 3H), 1.52 (s, 3H).

Example 314: (S)-4-((4-((4"-(2-(((S)-3-carboxy-2-hydroxypropyl)amino)ethoxy)-3"-fluoro-2,2'-dimethyl-[1,1':3',1"-terphenyl]-3-yl)methoxy)-5-chloro-2-((5-cyanopyridin-3-yl)methoxy)benzyl)aminol-3-hydroxybutanoic acid

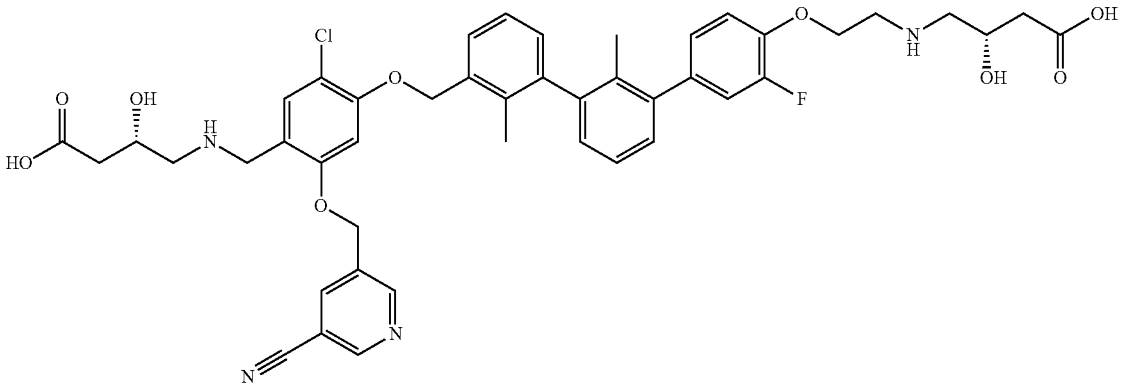 [SMILES: Cc1c(COc2cc(OCc3cncc(C#N)c3)c(CNC[C@@H](O)CC(=O)O)cc2Cl)cccc1-c1cccc(-c2ccc(OCCNC[C@@H](O)CC(=O)O)c(F)c2)c1C]

The title compound was synthesized according to general reductive amination procedure G. [M+1]=841.176. $^{1}$H NMR (400 MHz, Methanol-$d_4$) δ 8.94 (dd, J=11.9, 2.0 Hz, 2H), 8.37 (t, J=2.0 Hz, 1H), 7.51 (s, 1H), 7.50-7.40 (m, 1H), 7.35-7.00 (m, 9H), 5.37 (s, 2H), 5.31 (s, 2H), 4.50-4.36 (m, 2H), 4.35 (dt, J=9.8, 3.3 Hz, 1H), 4.23 (s, 2H), 3.60-3.52 (m, 2H), 3.38 (dd, J=12.7, 3.0 Hz, 1H), 3.24-3.09 (m, 2H), 2.97 (dd, J=12.7, 9.8 Hz, 1H), 2.65 (s, 1H), 2.58 (d, J=6.3 Hz, 2H), 2.51 (dd, J=6.3, 1.0 Hz, 2H), 2.13 (s, 3H), 1.89 (s, 3H).

Example 315: (S)-4-((4-((4"-(2-(((S)-3-carboxy-2-hydroxypropyl)amino)ethoxy)-2"-chloro-2,2'-dimethyl-[1,1':3',1"-terphenyl]-3-yl)methoxy)-5-chloro-2-((5-cyanopyridin-3-yl)methoxy)benzyl)amino)-3-hydroxybutanoic acid

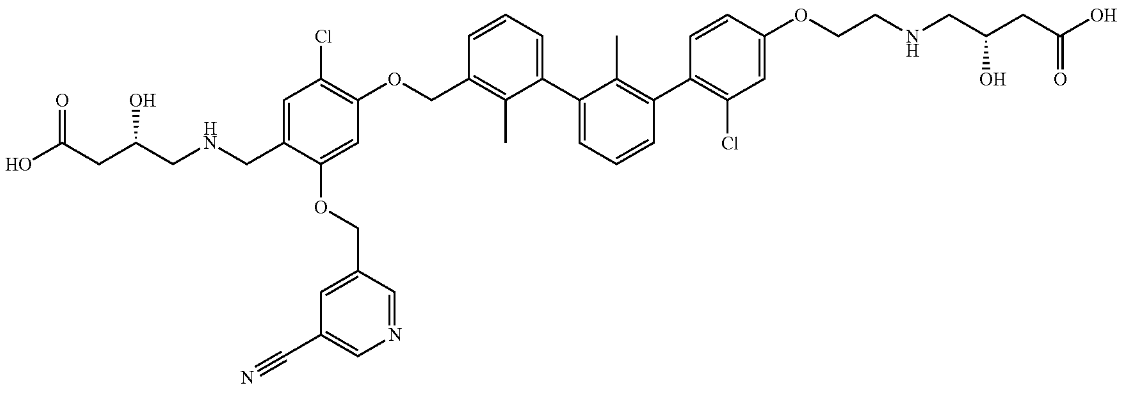 [SMILES: Cc1c(COc2cc(OCc3cncc(C#N)c3)c(CNC[C@@H](O)CC(=O)O)cc2Cl)cccc1-c1cccc(-c2ccc(OCCNC[C@@H](O)CC(=O)O)cc2Cl)c1C]

The title compound was synthesized according to general reductive amination procedure G. [M+1]=857.047. $^{1}$H NMR (400 MHz, Methanol-$d_4$) δ 8.94 (dd, J=11.0, 2.0 Hz, 2H), 8.37 (s, 1H), 7.50 (d, J=1.3 Hz, 1H), 7.46 (d, J=7.5 Hz, 1H), 7.35-6.98 (m, 9H), 5.37 (s, 2H), 5.31 (s, 2H), 4.35 (q, J=6.1, 5.5 Hz, 3H), 4.23 (s, 3H), 3.54 (t, J=5.1 Hz, 2H), 3.41-3.32 (m, 1H), 3.23-3.05 (m, 2H), 2.97 (dd, J=12.7, 9.8 Hz, 1H), 2.58 (d, J=6.3 Hz, 2H), 2.51 (dd, J=6.2, 1.1 Hz, 2H), 2.13 (d, J=4.2 Hz, 3H), 1.74 (d, J=2.5 Hz, 3H).

Example 317: (3S,3'S)-4,4'-(((3,3'''-dimethoxy-2',2''-dimethyl-[1,1':3',1'':3'',1'''-quaterphenyl]-4,4'''-diyl) bis(methylene))bis(azanediyl))bis(3-hydroxybutanoic acid)

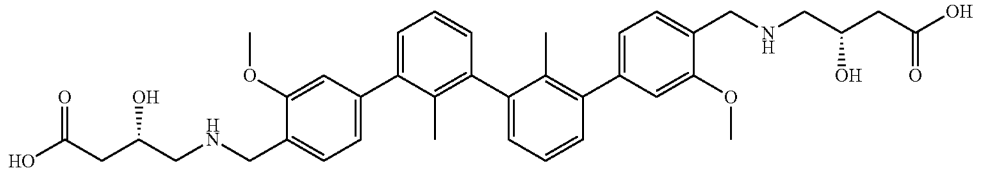 [SMILES: COc1cc(-c2cccc(-c3cccc(-c4ccc(CNC[C@@H](O)CC(=O)O)c(OC)c4)c3C)c2C)ccc1CNC[C@@H](O)CC(=O)O]

The title compound was prepared analogously to Example 322 according to general reductive amination procedure G. [M+1]=657.32. $^{1}H$ NMR (400 MHz, Methanol-$d_4$) δ 7.44 (d, J=7.7 Hz, 2H), 7.32 (t, J=7.6 Hz, 2H), 7.22 (dd, J=7.7, 1.4 Hz, 2H), 7.15 (dd, J=7.5, 1.5 Hz, 2H), 7.06 (d, J=1.4 Hz, 2H), 7.00 (dd, J=7.6, 1.5 Hz, 2H), 4.36-4.24 (m, 6H), 3.95 (s, 6H), 3.24 (dd, J=12.7, 3.1 Hz, 2H), 3.03 (dd, J=12.8, 9.8 Hz, 2H), 2.56 (d, J=6.3 Hz, 4H), 1.96 (s, 6H).

Example 323: (2S)-2-((5-chloro-2-((5-cyanopyridin-3-yl)methoxy)-4-((2,2'-dimethyl-4''-((((5-oxopyrrolidin-2-yl)methyl)amino)methyl)-[1,1':3',1''-terphenyl]-3-yl)methoxy)benzyl)amino)-3-hydroxy-2-methylpropanoic acid

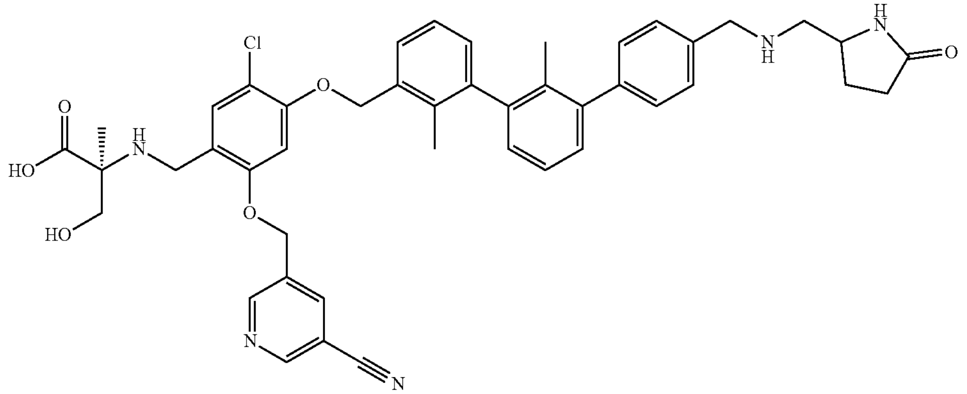 [SMILES: Cc1c(COc2cc(OCc3cncc(C#N)c3)c(CN[C@@](C)(CO)C(=O)O)cc2Cl)cccc1-c1cccc(-c2ccc(CNCC3CCC(=O)N3)cc2)c1C]

The title compound was synthesized according to general reductive amination procedure H with 5-(aminomethyl)pyrrolidin-2-one hydrochloride in place of (2S,4R)-4-hydroxypiperidine-2-carboxylic acid. [M+1]=788.98. $^{1}H$ NMR (400 MHz, Methanol-$d_4$) δ 8.98 (d, J=2.1 Hz, 1H), 8.91 (d, J=1.9 Hz, 1H), 8.45-8.35 (m, 1H), 7.58 (d, J=8.1 Hz, 2H), 7.55 (s, 1H), 7.47 (d, J=8.2 Hz, 3H), 7.32 (t, J=7.6 Hz, 1H), 7.27 (t, J=7.6 Hz, 1H), 7.23-7.17 (m, 1H), 7.17-7.10 (m, 2H), 7.08 (s, 1H), 5.36 (s, 2H), 5.32 (s, 2H), 4.37-4.25 (m, 4H), 4.06-3.97 (m, 2H), 3.80 (d, J=12.1 Hz, 1H), 3.27-3.20 (m, 2H), 2.50-2.30 (m, 3H), 2.14 (s, 3H), 2.00-1.81 (m, 4H), 1.52 (s, 3H).

Example 324: (S)-4-(((3-(3-cyanopropoxy)-4'''-(((R)-3-hydroxypyrrolidin-1-yl)methyl)-2',2''-dimethyl-[1,1':3',1'':3'',1'''-quaterphenyl]-4-yl)methyl) amino)-3-hydroxybutanoic acid

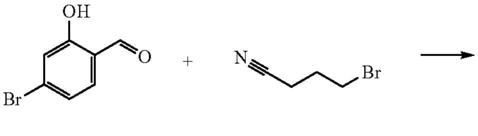

-continued

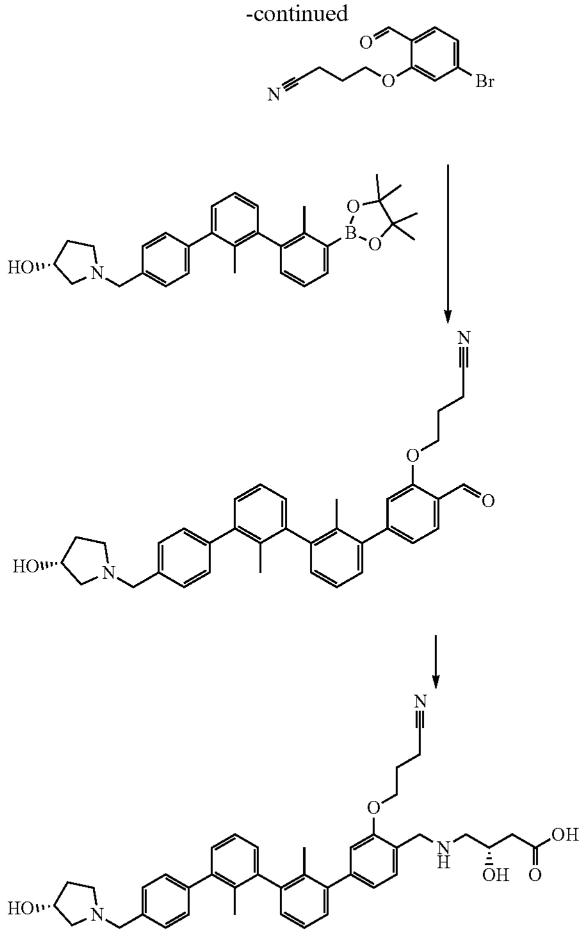

4-bromo-2-hydroxybenzaldehyde (220 mg, 1.1 mmol), 4-bromobutanenitrile (148 mg, 1 mmol) and $K_2CO_3$ (276 mg, 2 mmol) were suspended in DMF (4 mL). The mixture was sealed, and heated at 70° C. for 12 h. The mixture was diluted with ether (50 mL), and washed with aq. 1 M NaOH and brine. The organic layer was dried over $Mg_2SO_4$, and concentrated to provide 260 mg (97%) of 4-(5-bromo-2-formylphenoxy)butanenitrile.

2,2'-(2,2'-dimethyl-[1,1'-biphenyl]-3,3'-diyl)bis(4,4,5,5-tetramethyl-1,3,2-dioxaborolane) (20 mg, 0.04 mmol), 4-(5-bromo-2-formylphenoxy)butanenitrile (14 mg, 0.05 mmol), $Pd(PPh3)_4$ (5 mg, 0.004 mmol), and $K2CO_3$ (20 mg, 0.14 mmol) were charged in a vial and suspended in Dioxane (1 mL) and water (0.1 mL). The mixture was sparged with argon for 2 min, and sealed with a teflon coated cap. The mixture was stirred at 90° C. for 4 h. After cooling to room temperature, the reaction was diluted with ethyl acetate and brine. The organic layer was separated, dried with anhydrous $Na_2SO_4$, filtered, and concentrated to provide (R)-4-((4-formyl-4'''-((3-hydroxypyrrolidin-1-yl)methyl)-2',2''-dimethyl-[1,1':3',1'':3'',1'''-quaterphenyl]-3-yl)oxy)butanenitrile as the crude product.

The title compound was synthesized following general reductive amination procedure G using (R)-4-((4-formyl-4'''-((3-hydroxypyrrolidin-1-yl)methyl)-2',2''-dimethyl-[1,1':3',1'':3'',1'''-quaterphenyl]-3-yl)oxy)butanenitrile as the crude starting material. [M+1]=648.38. $^{1}H$ NMR (400 MHz, Methanol-$d_4$) δ 7.64-7.55 (m, 2H), 7.47 (d, J=7.8 Hz, 3H), 7.32 (t, J=7.9 Hz, 2H), 7.27-7.19 (m, 2H), 7.15 (dt, J=7.5, 1.8 Hz, 2H), 7.08 (d, J=1.5 Hz, 1H), 7.03 (dd, J=7.7, 1.5 Hz, 1H), 4.67-4.28 (m, 6H), 4.25 (t, J=5.7 Hz, 2H), 3.82-3.41 (m, 2H), 3.40-3.21 (m, 3H), 3.08 (dd, J=12.7, 9.8 Hz, 1H), 2.71 (t, J=6.8 Hz, 2H), 2.57 (d, J=6.3 Hz, 2H), 2.50-1.98 (m, 4H), 1.95 (d, J=5.7 Hz, 6H).

Example 325: (S)-3-hydroxy-4-(((4'''-(((R)-3-hydroxypyrrolidin-1-yl)methyl)-2',2''-dimethyl-3-(trifluoromethoxy)-[1,1':3',1'':3'',1'''-quaterphenyl]-4-yl)methyl)amino)butanoic acid

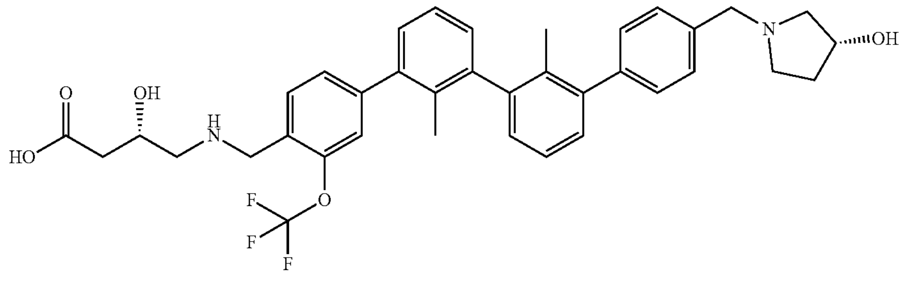 [SMILES: Cc1c(-c2ccc(CN3CC[C@@H](O)C3)cc2)cccc1-c1cccc(-c2ccc(CNC[C@@H](O)CC(=O)O)c(OC(F)(F)F)c2)c1C]

The title compound was prepared analogously to Example 324 according to general reductive amination procedure G using 4-bromo-2-(trifluoromethoxy)benzaldehyde in place of 4-(5-bromo-2-formylphenoxy)butanenitrile in the previous Suzuki cross-coupling step. [M+1]=649.40. $^{1}H$ NMR (400 MHz, Methanol-$d_4$) δ 7.73 (d, J=7.9 Hz, 1H), 7.59 (d, J=8.0 Hz, 2H), 7.53-7.45 (m, 3H), 7.45-7.39 (m, 1H), 7.39-7.29 (m, 2H), 7.29-7.10 (m, 4H), 4.70-4.17 (m, 6H), 3.83-3.42 (m, 2H), 3.33 (m, 3H), 3.11 (dd, J=12.7, 9.9 Hz, 1H), 2.57 (d, J=6.3 Hz, 2H), 2.51-1.99 (m, 2H), 1.99-1.88 (m, 6H).

Example 326: (S)-4-((5-chloro-2-((5-cyanopyridin-3-yl)methoxy)-4-((4"-((((5-cyanopyridin-3-yl)methyl)amino)methyl)-2,2'-dimethyl-[1,1':3',1"-terphenyl]-3-yl)methoxy)benzyl)amino)-3-hydroxybutanoic acid After cooling to room temperature, the reaction was diluted with EtOAc and brine. The organic layer was separated, dried with $Na_2SO_4$ and concentrated. Purified by silica gel chromatography (eluting with EtOAc-Hex) to provide tert-butyl ((3'-bromo-2'-methyl-[1,1'-biphenyl]-4-yl)methyl)carbamate.

Tert-butyl ((3'-bromo-2'-methyl-[1,1'-biphenyl]-4-yl)methyl)carbamate (135 mg, 0.36 mmol) was dissolved in 5 mL DCM. 1 mL of TFA was added dropwise and stirred for 2 h. The reaction was diluted with DCM, and quenched

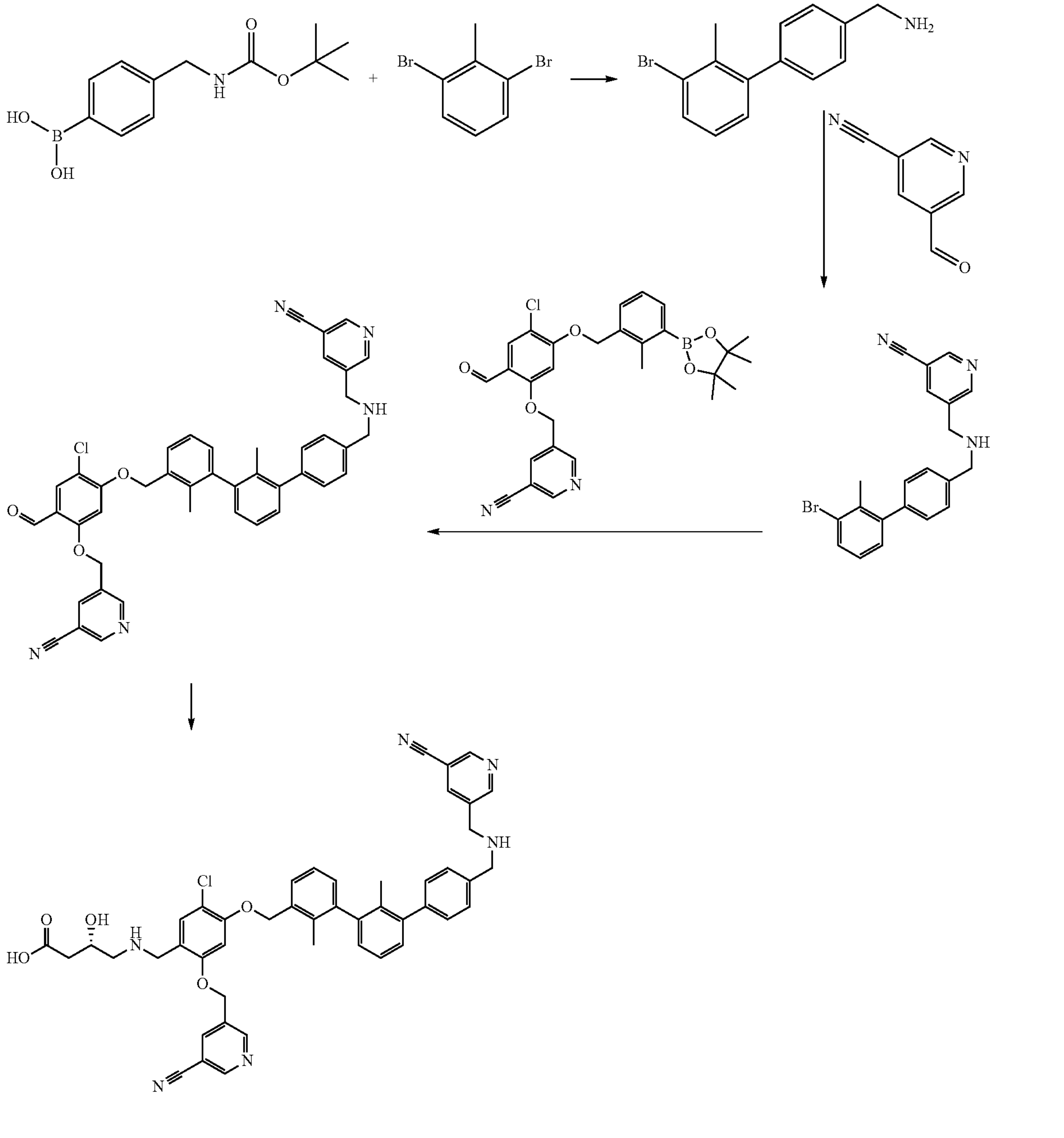

(4-(((tert-butoxycarbonyl)amino)methyl)phenyl)boronic acid (1 g, 4 mmol), 1,3-dibromo-2-methylbenzene (2 g, 8 mmol), $Pd(dppf)Cl_2CH_2Cl_2$ (0.32 g, 0.4 mmol) and potassium carbonate (1.6 g, 12 mmol) were suspended in 10 mL dioxane and 1 mL water. The mixture was sparged for 5 min with argon and heated to 90° C. in a heating block for 4 h.

carefully with sat $NaHCO_3$. The organic layer was separated, and the aqueous layer was extracted with DCM. The combined organics were dried over Na2$SO_4$, filtered, and concentrated to provide the crude amine. To this amine was added 5-formylnicotinonitrile (53 mg, 0.4 mmol), and DCM (5 mL). The resulting solution was allowed to stir for 1 h at room temperature. Sodium triacetoxyborohydride (230.22 mg, 1.09 mmol) was added in one portion, and stirred for an additional 3 h. The reaction was diluted with DCM, and washed with $NaHCO_3$, and Brine. The organic layer was dried over $Na_2SO_4$, and concentrated and purified silica gel chromatography (20% MeOH in DCM) to provide 5-((((3'-bromo-2'-methyl-[1,1'-biphenyl]-4-yl)methyl)amino) methyl)nicotinonitrile.

5-((((3'-bromo-2'-methyl-[1,1'-biphenyl]-4-yl)methyl) amino)methyl)nicotinonitrile (40 mg, 0.1 mmol), Intermediate 13 (40 mg, 0.08 mmol), Pd(PPh3)4 (9 mg, 0.008 mmol), and $K_2CO_3$ (32 mg, 0.23 mmol) were charged in a vial and suspended in Dioxane (2 mL) and water (0.2 mL). The mixture was sparged with argon for 2 min, and sealed with a teflon coated cap. The mixture was stirred at 90° C. for 4 h. After cooling to room temperature, the reaction was diluted with ethyl acetate and brine. The organic layer was separated, dried with anhydrous sodium sulfate, filtered, and concentrated to provide 5-((4-chloro-5-((4"-((((5-cyanopyridin-3-yl)methyl)amino)methyl)-2,2'-dimethyl-[1,1':3',1"-terphenyl]-3-yl)methoxy)-2-formylphenoxy)methyl)nicotinonitrile.

The title compound was synthesized following general reductive amination procedure G using 5-((4-chloro-5-((4"-((((5-cyanopyridin-3-yl)methyl)amino)methyl)-2,2'-dimethyl-[1,1':3',1"-terphenyl]-3-yl)methoxy)-2-formylphenoxy)methyl)nicotinonitrile as the crude starting material. [M+1]=807.73. $^1H$ NMR (400 MHz, Methanol-$d_4$) δ 9.00 (d, J=1.9 Hz, 1H), 8.95 (d, J=2.1 Hz, 1H), 8.93 (t, J=2.4 Hz, 2H), 8.34 (d, J=20.0 Hz, 2H), 7.58 (d, J=8.0 Hz, 2H), 7.52-7.38 (m, 4H), 7.37-7.09 (m, 5H), 7.08 (s, 1H), 5.38 (s, 2H), 5.31 (s, 2H), 4.45 (s, 2H), 4.39 (s, 2H), 4.30-4.17 (m, 3H), 3.20 (dd, J=12.8, 3.0 Hz, 1H), 3.01-2.92 (m, 1H), 2.57-2.46 (m, 2H), 2.14 (s, 3H), 1.88 (s, 3H).

Example 327: (S)-4-((2-((3'-((S)-1-((3-bromo-5-((((S)-3-carboxy-2-hydroxypropyl)amino)methyl)-6-(3-cyanopropoxy)pyridin-2-yl)oxy)-2,3-dihydro-1H-inden-4-yl)-2'-methyl-[1,1'-biphenyl]-4-yl)oxy)ethyl) amino)-3-hydroxybutanoic acid

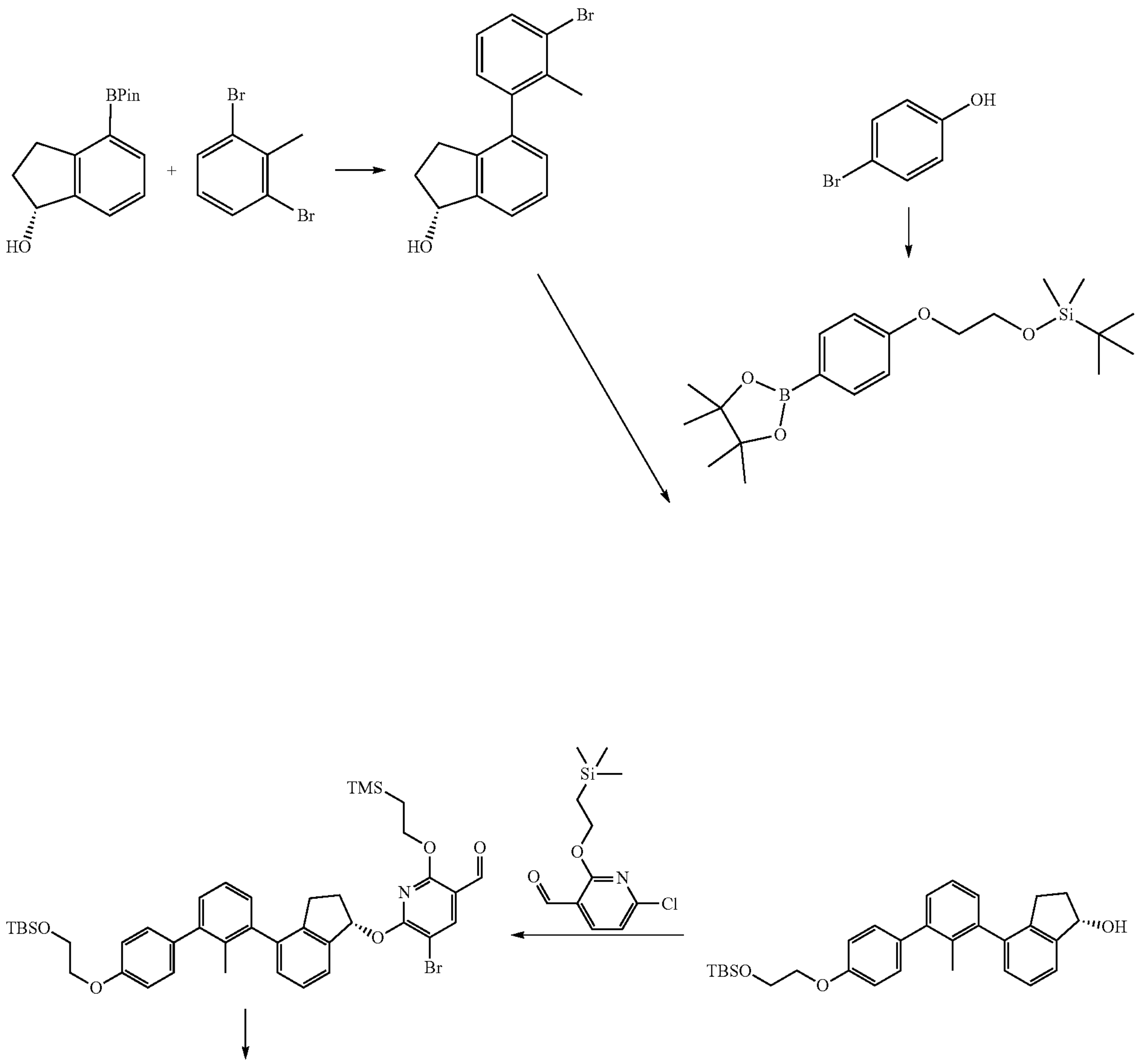

-continued

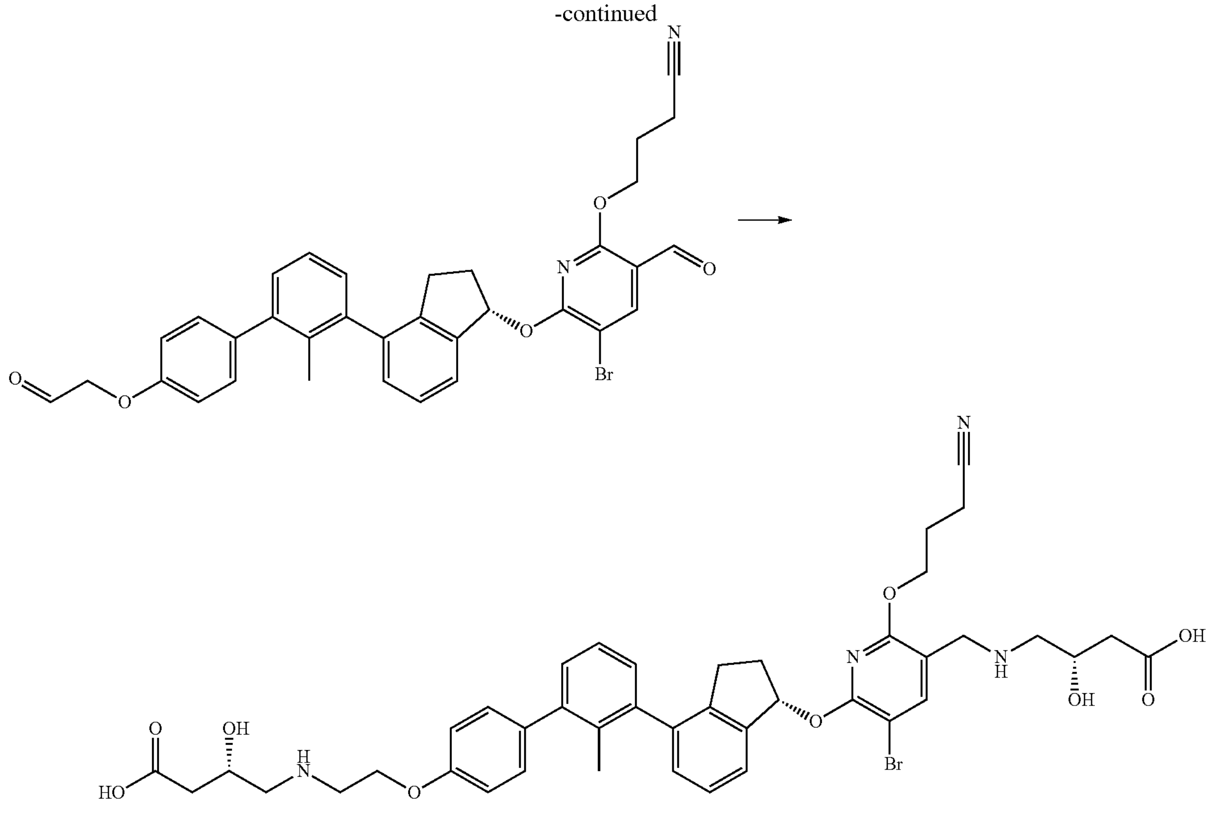

(R)-4-(4,4,5,5-tetramethyl-1,3,2-dioxaborolan-2-yl)-2,3-dihydro-1H-inden-1-ol (2 g, 7.7 mmol), 1,3-dibromo-2-methylbenzene (3.8 g, 15.4 mmol), Pd(dppf)$Cl_2CH_2Cl_2$ (0.44 g, 0.77 mmol) and potassium carbonate (2.1 g, 15.4 mmol) were suspended in 20 mL dioxane and 2 mL water. The mixture was sparged for 10 min with argon and heated to 90° C. in a heating block for 4 h. After cooling to room temperature, the reaction was diluted with EtOAc and brine. The organic layer was separated, dried with $Na_2SO_4$ and concentrated. Purified by silica gel chromatography (eluting with EtOAc-Hex) to provide (R)-4-(3-bromo-2-methylphenyl)-2,3-dihydro-1H-inden-1-ol.

4-bromophenol (2 g, 11.6 mmol), $K_2CO_3$ (3.2 g, 23.12 mmol), and 2-bromoethan-1-ol (4.3 g, 34.7 mmol) were suspended in DMF (15 mL). The reaction was heated at 110° C. for 16 h. The reaction was cooled, and diluted with ether (200 mL). The ether layer was washed with water, aq. 1 M NaOH, brine, dried over anhydrous $MgSO_4$, filtered and concentrated under reduced pressure to provide the crude alcohol. This crude alcohol was added TBSCl (5.2 g, 34 mmol) and suspended in DMF (15 mL). Imidazole (2.4 g, 34.7 mmol) was added in portions, and the mixture was stirred at room temperature for 6 h. The reaction was diluted with ether (200 mL) and was washed with water (2×), brine, dried over anhydrous MgSO4, filtered and concentrated under reduced pressure. Purification by silica gel chromatography (eluting with EtOAc-Hex) provided (2-(4-bromophenoxy)ethoxy)(tert-butyl)dimethylsilane.

(2-(4-bromophenoxy)ethoxy)(tert-butyl)dimethylsilane (2.15 g, 6.5 mmol), bis(pinacolato)diboron (2.0 g, 7.8 mmol), KOAc (1.5 g, 15 mmol) and [1,1'-bis(diphenylphosphino)ferrocene]palladium(II) dichloride (0.41 g, 0.50 mmol) were suspended in 10 mL dioxane and argon was bubbled through the mixture for 5 min. The reaction was heated to 90 C for 3 h, after which the reaction was cooled to room temperature and diluted with 100 mL EtOAc. The reaction mixture was filtered through a celite pad, concentrated under reduced pressure, and purified by silica gel chromatography to provide tert-butyldimethyl(2-(4-(4,4,5,5-tetramethyl-1,3,2-dioxaborolan-2-yl)phenoxy)ethoxy)silane.

(R)-4-(3-bromo-2-methylphenyl)-2,3-dihydro-1H-inden-1-ol (1.5 g, 4.9 mmol), tert-butyldimethyl(2-(4-(4,4,5,5-tetramethyl-1,3,2-dioxaborolan-2-yl)phenoxy)ethoxy)silane. (2.06 g, 5.4 mmol), Pd(dppf)$Cl_2CH_2Cl_2$ (0.20 g, 0.25 mmol) and potassium carbonate (2.1 g, 15 mmol) were suspended in 15 mL dioxane and 1.5 mL water. The mixture was sparged for 10 min with argon and heated to 90° C. in a heating block for 4 h. After cooling to room temperature, the reaction was diluted with EtOAc and brine. The organic layer was separated, dried with $Na_2SO_4$ and concentrated. Purified by silica gel chromatography (eluting with EtOAc-Hex) to provide (S)-4-(4'-(2-((tert-butyldimethylsilyl)oxy)ethoxy)-2-methyl-[1,1'-biphenyl]-3-yl)-2,3-dihydro-1H-inden-1-ol.

(S)-4-(4'-(2-((tert-butyldimethylsilyl)oxy)ethoxy)-2-methyl-[1,1'-biphenyl]-3-yl)-2,3-dihydro-1H-inden-1-ol. (1.75 g, 3.7 mmol), 6-chloro-2-(2-(trimethylsilyl)ethoxy)nicotinaldehyde (1.9 g, 7.37 mmol), cesium carbonate (2.4 g, 7.37 mmol), palladium (II) acetate (83 mg, 0.37 mmol), 2-di-tert-butylphosphino-2',4',6'-triisopropylbiphenyl(t-butyl Xphos) (235 mg, 0.55 mmol) in toluene (20 mL) was heated to 85° C. After 3 h, the resulting mixture was allowed to cool to room temperature, was filtered through celite, and was concentrated under reduced pressure. The residue was purified by flash column chromatography (ethyl acetate in hexanes) to provide (S)-6-((4-(4'-(2-((tert-butyldimethylsilyl)oxy)ethoxy)-2-methyl-[1,1'-biphenyl]-3-yl)-2,3-dihydro-1H-inden-1-yl)oxy)-2-(2-(trimethylsilyl)ethoxy) nicotinaldehyde.

(S)-6-((4-(4'-(2-((tert-butyldimethylsilyl)oxy)ethoxy)-2-methyl-[1,1'-biphenyl]-3-yl)-2,3-dihydro-1H-inden-1-yl) oxy)-2-(2-(trimethylsilyl)ethoxy)nicotinaldehyde 487 mg, 0.7 mmol), and sodium acetate (126 mg, 2.1 mmol) was suspended in 12 mL acetic acid, and the resulting suspension was sonicated for 5 min. Bromine (0.043 ml, 0.84 mmol) was diluted in acetic acid (1 mL) and the resulting solution was added dropwise to the aldehyde. After 40 min, the reaction was diluted with methylene chloride (50 mL) and aqueous 2 M NaOH (100 mL). After stirring for 10 min, the organic layer was separated, and the aqueous extracted with methylene chloride (75 mL). The combined organic layers were dried, concentrated, and purified via column chromatography to provide (S)-5-bromo-6-((4-(4'-(2-((tert-butyldimethylsilyl)oxy)ethoxy)-2-methyl-[1,1'-biphenyl]-3-yl)-2,3-dihydro-1H-inden-1-yl)oxy)-2-(2-(trimethylsilyl)ethoxy) nicotinaldehyde.

(S)-5-bromo-6-((4-(4'-(2-((tert-butyldimethylsilyl)oxy) ethoxy)-2-methyl-[1,1'-biphenyl]-3-yl)-2,3-dihydro-1H-inden-1-yl)oxy)-2-(2-(trimethylsilyl)ethoxy)nicotinaldehyde. (70 mg, 0.09 mmol) and cesium fluoride (109 mg, 0.72 mmol) were suspended in N,N-dimethylformamide (1 mL). The suspension was heated to 60° C. for 1.5 h. After complete desilylation as observed by LCMS, 4-Bromobutyronitrile (80.21 mg, 0.54 mmol) was added and the resulting solution was stirred for an additional 3 h, at 75° C. The reaction was cooled, and diluted with ethyl acetate (25 mL). The organic layer was washed with water, brine, dried over anhydrous MgSO4, filtered and concentrated under reduced pressure to provide the crude alcohol. The crude alcohol was dissolved in DCM (1 mL) and Dess-Martin periodinane (115 mg, 0.27 mmol) was added. After stirring for 12 h at room temperature, the reaction was poured into 15 mL of 1N aqueous sodium hydroxide and extracted with methylene chloride (3×). The combined organics were dried over anhydrous sodium sulfate, filtered, and concentrated to provide (S)-4-((5-bromo-3-formyl-6-((4-(2-methyl-4'-(2-oxoethoxy)-[1,1'-biphenyl]-3-yl)-2,3-dihydro-1H-inden-1-yl)oxy)pyridin-2-yl)oxy)butanenitrile as the crude product.

The title compound was synthesized following general reductive amination procedure G using (S)-4-((5-bromo-3-formyl-6-((4-(2-methyl-4'-(2-oxoethoxy)-[1,1'-biphenyl]-3-yl)-2,3-dihydro-1H-inden-1-yl)oxy)pyridin-2-yl)oxy)butanenitrile as the crude starting material. [M+1]=831.295. $^1$H NMR (400 MHz, Methanol-$d_4$) δ 7.99 (s, 1H), 7.42 (t, J=7.3 Hz, 1H), 7.36-7.23 (m, 4H), 7.21-7.16 (m, 2H), 7.15-7.05 (m, 3H), 6.60 (t, J=5.7 Hz, 1H), 4.61 (t, J=5.9 Hz, 2H), 4.42-4.26 (m, 4H), 4.26-4.21 (m, 2H), 3.54 (t, J=5.2 Hz, 2H), 3.35 (dd, J=12.7, 3.1 Hz, 1H), 3.29-3.25 (m, 1H), 3.18-3.01 (m, 2H), 3.00-2.62 (m, 5H), 2.61-2.48 (m, 4H), 2.33-2.05 (m, 3H), 2.02-1.92 (m, 3H).

Example 328: (3S,3'S)-4,4'-((((((2,2'-dimethyl-[1,1'-biphenyl]-3,3'-diyl)bis(methylene))bis(oxy))bis(5-bromo-2-(((S)-5-oxopyrrolidin-2-yl)methoxy)pyridine-6,3-diyl))bis(methylene))bis(azanediyl))bis(3-hydroxybutanoic acid)

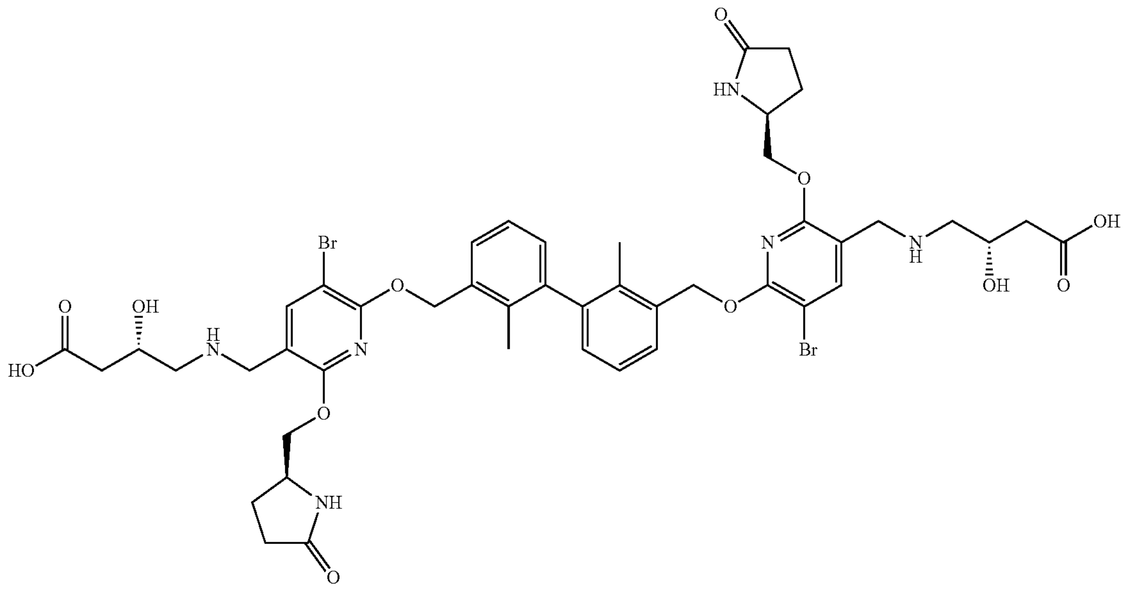 [SMILES: Cc1c(COc2nc(OC[C@@H]3CCC(=O)N3)c(CNC[C@@H](O)CC(=O)O)cc2Br)cccc1-c1cccc(COc2nc(OC[C@@H]3CCC(=O)N3)c(CNC[C@@H](O)CC(=O)O)cc2Br)c1C]

The title compound was synthesized analogously to Example 121 using (S)-5-(hydroxymethyl)pyrrolidin-2-one in place of 5-(hydroxymethyl)isophthalonitrile, and following reductive amination procedure G. MS (m/z) 522.23 $(M+2H)^{2+}$. $^1$H NMR (400 MHz, Methanol-$d_4$) δ 7.96 (s, 2H), 7.50-7.41 (m, 2H), 7.24 (t, J=7.6 Hz, 2H), 7.12-7.02 (m, 2H), 5.66-5.48 (m, 4H), 4.71-4.58 (m, 2H), 4.58-4.44 (m, 2H), 4.38-4.26 (m, 2H), 4.22-4.07 (m, 4H), 3.53-3.34 (m, 4H), 3.26-3.13 (m, 2H), 3.07-2.86 (m, 4H), 2.64-2.46 (m, 4H), 2.45-2.27 (m, 2H), 2.15-1.93 (m, 8H).

Example 329: (S)-2-((4-((3'-(5-(2-aminoethyl)-1,3,4-oxadiazol-2-yl)-2,2'-dimethyl-[1,1'-biphenyl]-3-yl)methoxy)-5-chloro-2-((5-cyanopyridin-3-yl)methoxy)benzyl)amino)-3-hydroxy-2-methylpropanoic acid

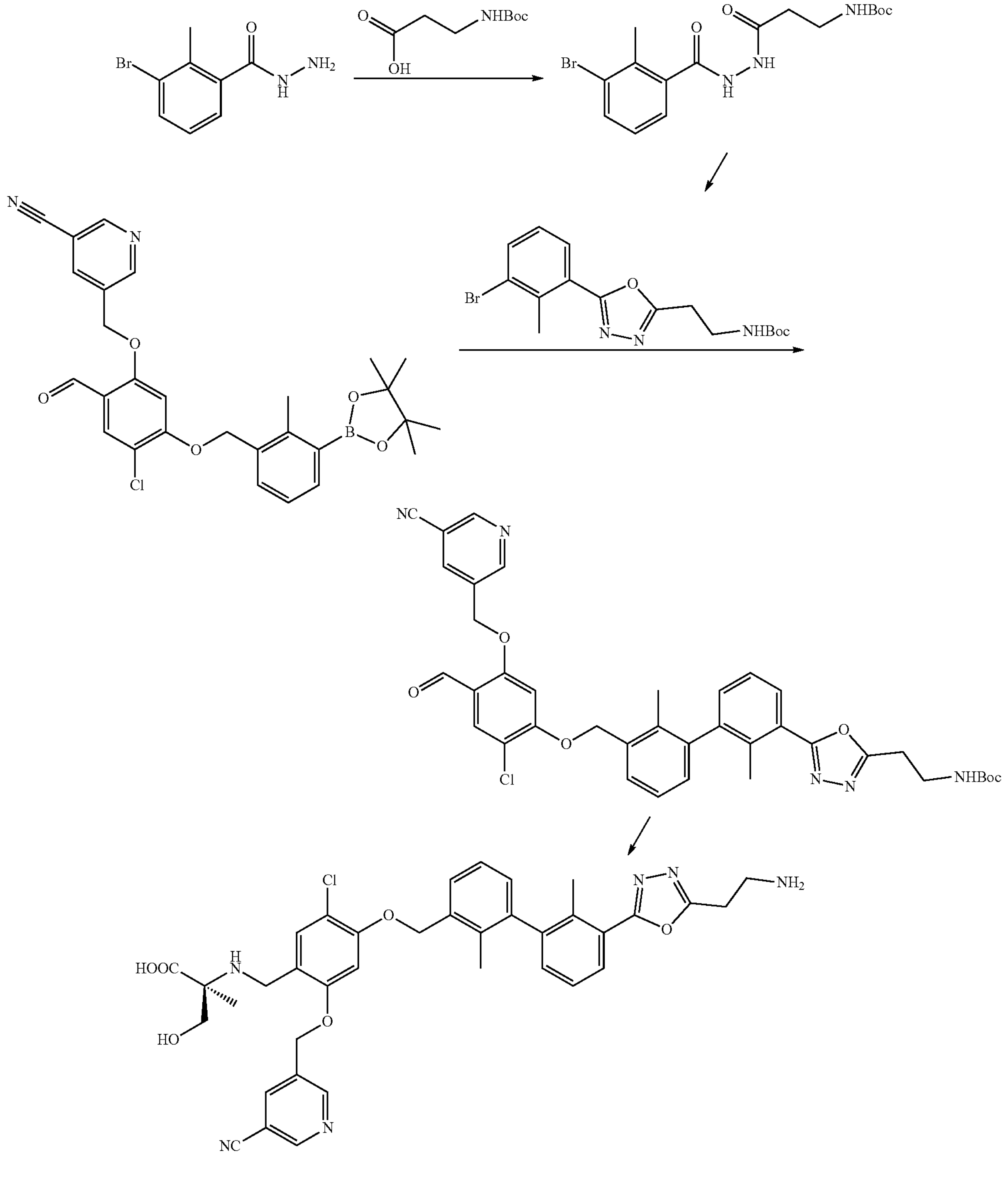

N,N-Diisopropylethylamine (380 μL, 2.18 mmol) was added to a solution of 1-[Bis(dimethylamino)methylene]-1H-1,2,3-triazolo[4,5-b]pyridinium 3-oxide hexafluorophosphate (830 mg, 2.18 mmol), 3-((tert-butoxycarbonyl)amino)propanoic acid (413 mg, 2.18 mmol) and 3-bromo-2-methylbenzohydrazide (500 mg, 2.18 mmol) in dimethylformamide (3 mL). After 18h the reaction was complete. The reaction was diluted with ethyl acetate (20 mL) and washed with water (3×10 mL) and brine (10 mL). The organic phase was dried over sodium sulfate and the solvent was removed under reduced pressure. The residue was subjected to flash chromatography (0-100% ethyl acetate/hexanes). The fractions containing product were combined and the solvent was removed under reduced pressure, providing tert-butyl (3-(2-(3-bromo-2-methylbenzoyl)hydrazinyl)-3-oxopropyl)carbamate.

4-Toluenesulfonyl chloride (539 mg, 2.83 mmol) was added to a mixture of tert-butyl (3-(2-(3-bromo-2-methylbenzoyl)hydrazinyl)-3-oxopropyl)carbamate (755 mg, 1.89 mmol), and triethylamine (789 µL, 5.66 mmol) in dichloromethane (10 mL). After 45 min the solvent was removed under reduced pressure. The residue was taken up in ethyl acetate (70 mL) and washed with saturated ammonium chloride(20 mL), saturated sodium bicarbonate (2×20 mL) and brine (20 mL). The organic phase was dried over sodium sulfate and the solvent was removed under reduced pressure. The residue was subjected to flash chromatography (0-100% ethyl acetate/hexanes). The fractions containing product were combined and the solvent was removed under reduced pressure, providing tert-butyl (2-(5-(3-bromo-2-methylphenyl)-1,3,4-oxadiazol-2-yl)ethyl)carbamate.

5-((4-chloro-2-formyl-5-((2-methyl-3-(4,4,5,5-tetramethyl-1,3,2-dioxaborolan-2-yl)benzyl)oxy)phenoxy)methyl) nicotinonitrile (200 mg, 0.386 mmol), tert-butyl (2-(5-(3-bromo-2-methylphenyl)-1,3,4-oxadiazol-2-yl)ethyl) carbamate (221 mg, 0.578 mmol), tetrakis (triphenylphosphine)palladium (0) (44.5 mg, 0.0386 mmol), potassium carbonate (107 mg, 0.771 mmol) in water (1 mL), and dimethylformamide (10 mL) was degassed with argon for 2 minutes. The above were combined and heated at 90° C. for 1 hour. The reaction was diluted with ethyl acetate (20 mL) and washed with water (3×10 mL) and brine (10 mL). The organic phase was dried over sodium sulfate and the solvent was removed under reduced pressure. The residue was subjected to flash chromatography (0-100% EtOAc/hexanes). The fractions containing product and the solvent was removed under reduced pressure providing tert-butyl (2-(5-(3'-((2-chloro-5-((5-cyanopyridin-3-yl)methoxy)-4-formylphenoxy)methyl)-2,2'-dimethyl-[1,1'-biphenyl]-3-yl)-1,3,4-oxadiazol-2-yl)ethyl)carbamate.

A mixture of (S)-2-amino-3-hydroxy-2-methylpropanoic acid (86 mg, 0.76 mmol), potassium hydroxide (40.4 mg, 0.76 mmol), in ethanol (3 mL) was sonicated until most material dissolved. A solution of tert-butyl (2-(5-(3'-((2-chloro-5-((5-cyanopyridin-3-yl)methoxy)-4-formylphenoxy)methyl)-2,2'-dimethyl-[1,1'-biphenyl]-3-yl)-1,3,4-oxadiazol-2-yl)ethyl)carbamate (100 mg, 0.144 mmol). After 5 minutes acetic acid (1 drop) and sodium triacetoxyborohydride (153 mg, 0.76 mmol). After 45 min the solvent was removed under reduced pressure. The residue was taken up in dimethylformamide (0.7 mL), water (0.5 ml), methanol (0.5 mL) with 0.1 mL of trifluoroacetic acid and filtered. The solution was subjected to preparative HPLC (eluant: 0.1% trifluoroacetic acid in acetonitrile/water). The fractions containing product were combined and subjected to lyophilization. The residue was taken up in dichloromethane (5 mL) and trifluoroacetic acid (0.5 mL). After 40 minutes the reaction was diluted with acetonitrile (5 mL) and co-evaporated until ~1 mL remained. The material was co-evaporated with acetonitrile two more times. The residue was taken up in methanol (0.5 mL) and water (0.5 mL). The solution was subjected to preparative HPLC (eluant: 0.1% trifluoroacetic acid in acetonitrile/water). The fractions containing product were combined and subjected to lyophilization, providing (S)-2-((4-((3'-(5-(2-((tert-butoxycarbonyl)amino)ethyl)-1,3,4-oxadiazol-2-yl)-2,2'-dimethyl-[1,1'-biphenyl]-3-yl)methoxy)-5-chloro-2-((5-cyanopyridin-3-yl)methoxy)benzyl)amino)-3-hydroxy-2-methylpropanoic acid. [M+1]=697.14. $^1$H NMR (400 MHz, Methanol-$d_4$) δ 8.98 (d, J=2.1 Hz, 1H), 8.91 (d, J=2.0 Hz, 1H), 8.43 (d, J=2.1 Hz, 1H), 7.93 (dd, J=7.9, 1.4 Hz, 1H), 7.56 (s, 1H), 7.52 (d, J=7.6 Hz, 1H), 7.47 (t, J=7.7 Hz, 1H), 7.36 (d, J=7.6 Hz, 1H), 7.30 (t, J=7.6 Hz, 1H), 7.14 (d, J=7.6 Hz, 1H), 7.09 (s, 1H), 5.38 (s, 2H), 5.34 (s, 2H), 4.28 (s, 2H), 4.00 (d, J=12.1 Hz, 1H), 3.79 (d, J=12.1 Hz, 1H), 3.52 (t, J=6.8 Hz, 2H), 3.38 (t, J=6.8 Hz, 2H), 2.33 (s, 3H), 2.11 (s, 3H), 1.52 (s, 3H).

Example 330: (S)-4-((5-chloro-2-((5-cyanopyridin-3-yl)methoxy)-4-((2,2'-dimethyl-3'-(1-(piperidin-4-yl)-1H-1,2,3-triazol-4-yl)-[1,1'-biphenyl]-3-yl)methoxy)benzyl)amino)-3-hydroxybutanoic acid

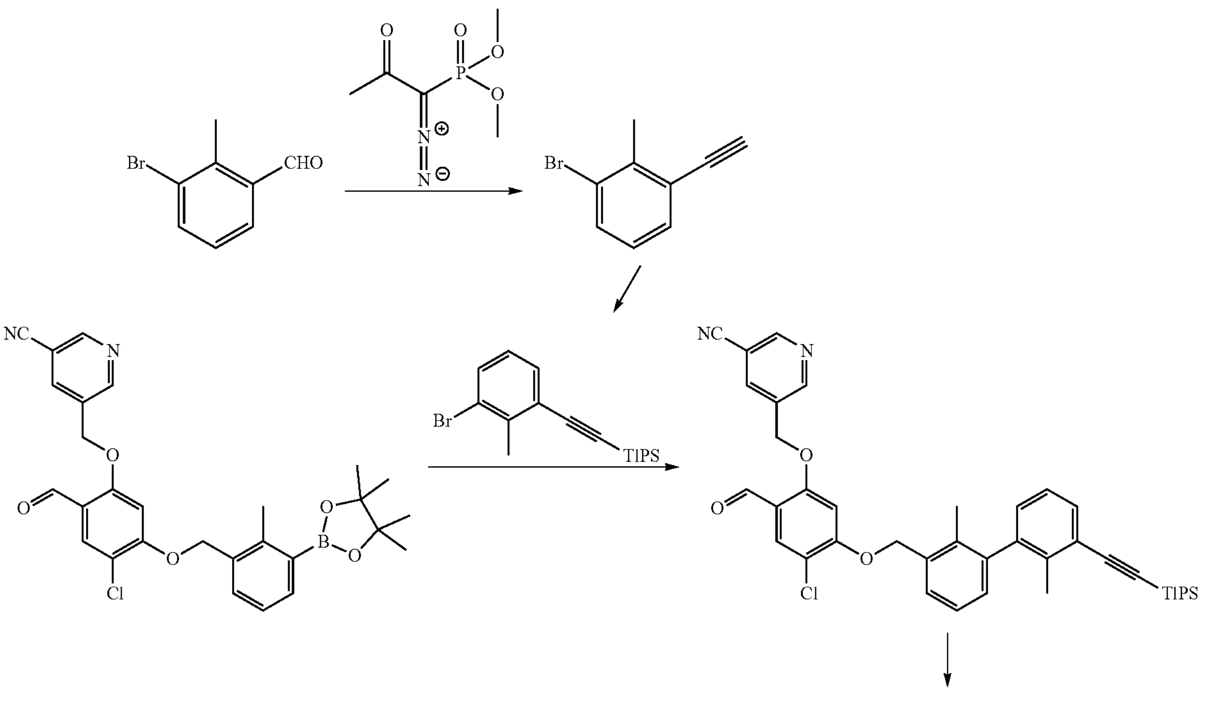

-continued

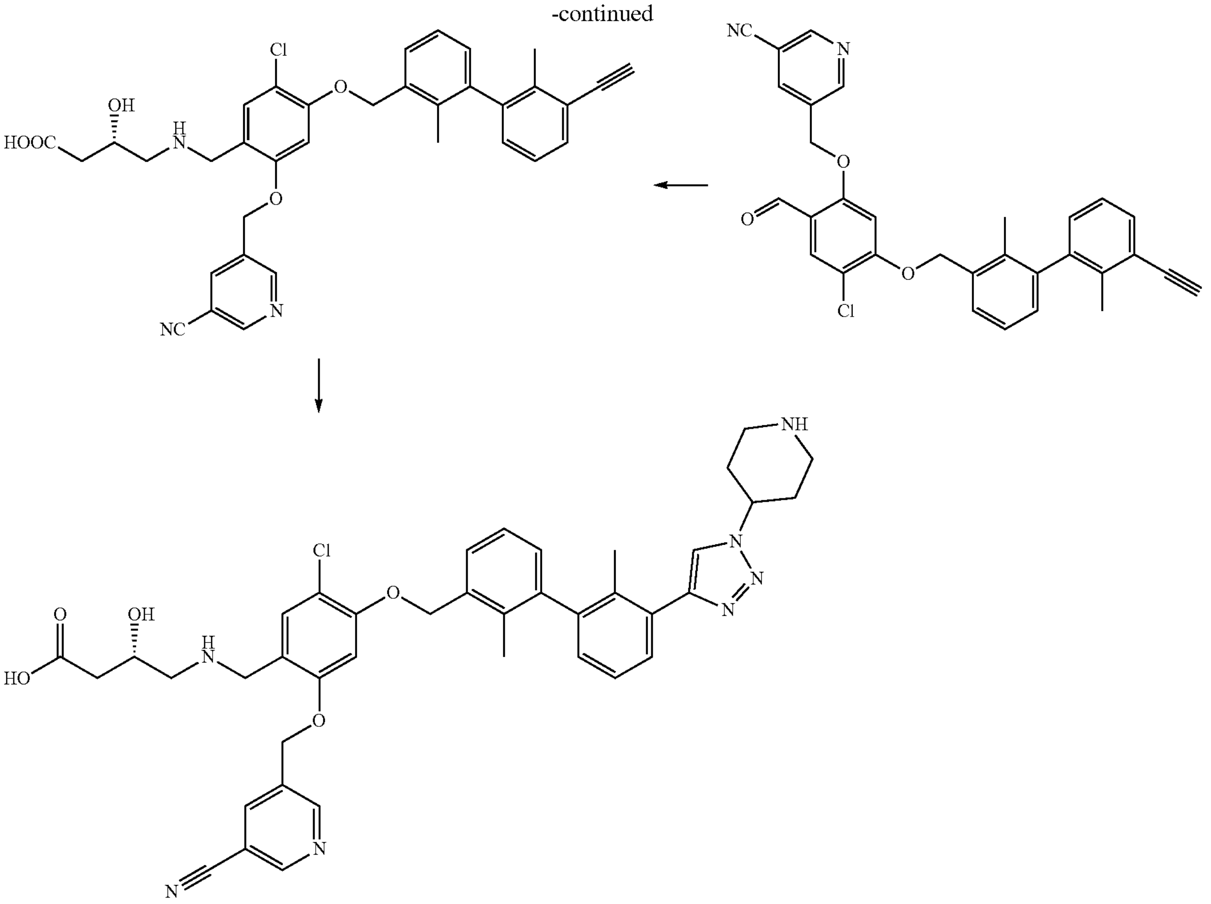

Potassium carbonate (4.44 g, 32.2 mmol) was added to a solution of the 3-bromo-2-methylbenzaldehyde (3.2 g, 16.1 mmol) and dimethyl (1-diazo-2-oxopropyl)phosphonate (3.7 g, 19.3 mol) in methanol (30 mL). After 1h solid was removed by filtration. The solvent was removed under reduced pressure. The residue was subjected to flash chromatography (0-50% ethyl acetate/hexanes). The fractions containing product were combined and the solvent was removed under reduced pressure, providing 1-bromo-3-ethynyl-2-methylbenzene.

A solution of lithium bis(trimethylsilyl)amide in tetrahydrofuran (1 M, 19.9 mL, 19.9 mmol) was added to a solution of 1-bromo-3-ethynyl-2-methylbenzene (2.59 g, 13.3 mmol) in tetrahydrofuran (30 mL) at −78° C. over a period of 2 minutes. After 15 min triisopropylsilyl chloride (3.1 mL, 14.6 mmol) was added dropwise. After 10 min the reaction was warmed to 0° C. After another 20 min the reaction was complete. The reaction was quenched with saturated ammonium chloride (75 mL). The aqueous phase was extracted with DCM (3×50 mL). The combined organic phases were washed with brine (50 mL) and dried over sodium sulfate. The solvent was removed under reduced pressure. The residue was subjected to flash chromatography (0-10% ethyl acetate/hexanes). The fractions containing product were combined and the solvent was removed under reduced pressure, providing ((3-bromo-2-methylphenyl)ethynyl)triisopropylsilane.

5-((4-chloro-2-formyl-5-((2-methyl-3-(4,4,5,5-tetramethyl-1,3,2-dioxaborolan-2-yl)benzyl)oxy)phenoxy)methyl) nicotinonitrile (3.0 g, 5.78 mmol), ((3-bromo-2-methylphenyl)ethynyl)triisopropylsilane (2.64 g, 7.52 mmol), tetrakis (triphenylphosphine)palladium(0) (668 mg, 0.578 mmol), potassium carbonate (1.60 g, 11.6 mmol) in water (5 mL), and dimethylformamide (30 mL) was degassed with argon for 2 minutes. The above were combined and heated at 90° C. for 1 hour. The reaction was diluted with ethyl acetate (100 mL) and washed with water (3×50 mL) and brine (50 mL). The organic phase was dried over sodium sulfate and the solvent was removed under reduced pressure. The residue was subjected to flash chromatography (0-100% EtOAc/hexanes). The fractions containing product and the solvent was removed under reduced pressure providing 5-((4-chloro-5-((2,2'-dimethyl-3'-((triisopropylsilyl)ethynyl)-[1,1'-biphenyl]-3-yl)methoxy)-2-formylphenoxy)methyl)nicotinonitrile.

A solution of tetrabutylammonium fluoride (1 M, 4.7 mL, 4.69 mmol) in tetrahydrofuran was added to a solution of 5-((4-chloro-5-((2,2'-dimethyl-3'-((triisopropylsilyl)ethynyl)-[1,1'-biphenyl]-3-yl)methoxy)-2-formylphenoxy) methyl)nicotinonitrile (2.83 g, 4.27 mmol) in tetrahydrofuran (20 mL) at 0° C. After 10 minutes the reaction was diluted with ethyl acetate (150 ml) and washed with water (2×50 mL) lithium chloride (1 M, 2×50 mL) and brine (50 mL). The organic phase was dried over sodium sulfate and the solvent was removed under reduced pressure. The residue was subjected to flash chromatography (0-100% ethyl acetate/hexanes). The fractions containing product were combined and the solvent was removed under reduced pressure, providing 5-((4-chloro-5-((3'-ethynyl-2,2'-dimethyl-[1,1'-biphenyl]-3-yl)methoxy)-2-formylphenoxy) methyl)nicotinonitrile.

(S)-4-((5-chloro-2-((5-cyanopyridin-3-yl)methoxy)-4-((3'-ethynyl-2,2'-dimethyl-[1,1'-biphenyl]-3-yl)methoxy)benzyl)amino)-3-hydroxybutanoic acid was synthesized according to general reductive amination procedure G.

tert-butyl 4-azidopiperidine-1-carboxylate (14 mg 0.0621 mmol) was added to a mixture of (S)-4-((5-chloro-2-((5-cyanopyridin-3-yl)methoxy)-4-((3'-ethynyl-2,2'-dimethyl-[1,1'-biphenyl]-3-yl)methoxy)benzyl)amino)-3-hydroxybutanoic acid (30 mg, 0.0414 mmol) copper powder (26.3 mg, 0.00415 mmol)saturated copper (II) sulfate (1.26 M, 32 μL, 0.00416 mmol) in tetrahydrofuran (3 mL). After 24 h the solvent was removed under reduced pressure. The residue was taken up in dimethylformamide (0.7 mL), water (0.5 ml), methanol (0.5 mL) with 0.1 mL of trifluoroacetic acid and filtered. The solution was subjected to preparative HPLC (eluant: 0.1% trifluoroacetic acid in acetonitrile/water). The fractions containing product were combined and subjected to lyophilization.

The residue was taken up in dichloromethane (5 mL) and trifluoroacetic acid (0.5 mL). After 40 minutes the reaction was diluted with acetonitrile (5 mL) and co-evaporated until ~1 mL remained. The material was co-evaporated with acetonitrile two more times. The residue was taken up in methanol (0.5 mL) and water (0.5 mL). The solution was subjected to preparative HPLC HPLC (eluant: 0.1% trifluoroacetic acid in acetonitrile/water). The fractions containing product were combined and subjected to lyophilization, providing (S)-4-((5-chloro-2-((5-cyanopyridin-3-yl)methoxy)-4-((2,2'-dimethyl-3'-(1-(piperidin-4-yl)-1H-1,2,3-triazol-4-yl)-[1,1'-biphenyl]-3-yl)methoxy)benzyl)amino)-3-hydroxybutanoic acid bis trifluoroacetate. [M+1]=736.11. $^1$H NMR (400 MHz, Methanol-$d_4$) δ 8.96 (d, J=2.1 Hz, 1H), 8.93 (d, J=2.0 Hz, 1H), 8.38 (t, J=2.1 Hz, 1H), 8.23 (s, 1H), 7.60-7.54 (m, 1H), 7.51 (s, 1H), 7.50-7.46 (m, 1H), 7.39-7.32 (m, 1H), 7.28 (t, J=7.6 Hz, 1H), 7.21-7.11 (m, 2H), 7.09 (s, 1H), 5.38 (s, 2H), 5.32 (s, 2H), 5.00-4.89 (m, 1H), 4.30-4.18 (m, 3H), 3.64 (t, J=4.1 Hz, 1H), 3.60 (t, J=4.1 Hz, 1H), 3.28-3.16 (m, 1H), 2.98 (dd, J=12.8, 9.8 Hz, 1H), 2.57-2.48 (m, 3H), 2.48-2.35 (m, 2H), 2.13 (s, 3H), 2.08 (s, 3H).

Example 331: 5-[[5-[[3-(3-bromo-2-methyl-phenyl)-2-methyl-phenyl]methoxy]-4-chloro-2-formylphenoxy]methyl]pyridine-3-carbonitrile

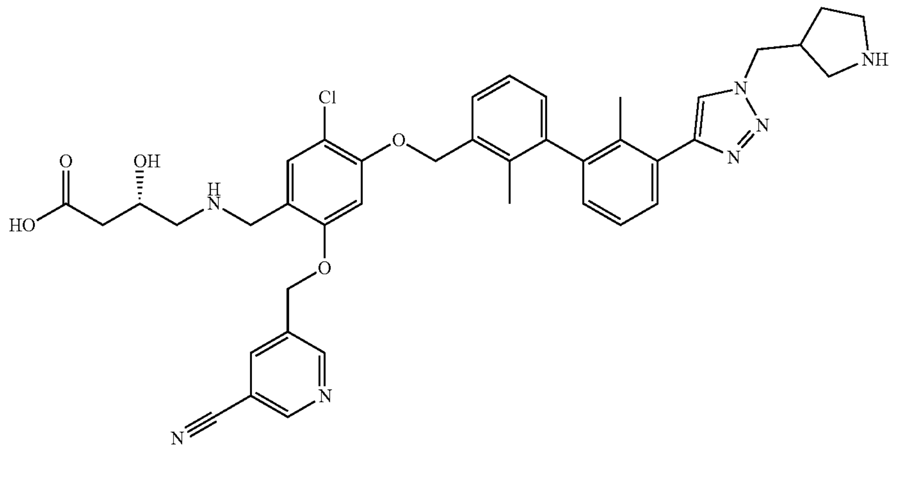 [SMILES: Cc1c(COc2cc(OCc3cncc(C#N)c3)c(CNC[C@@H](O)CC(=O)O)cc2Cl)cccc1-c1cccc(-c2cn(CC3CCNC3)nn2)c1C]

The title compound was synthesized in analogy to Example 330, replacing tert-buty 4-azidopiperidine-1-carboxylate with 3-(azidomethyl)pyrrolidine. [M+1]=736.1. $^1$H NMR (400 MHz, DMSO-$d_6$) δ 9.10 (s, 1H), 9.03 (d, J=2.0 Hz, 1H), 9.02 (d, J=2.2 Hz, 1H), 8.86 (s, 1H), 8.56 (s, 2H), 8.47 (t, J=2.1 Hz, 1H), 8.45 (d, J=0.9 Hz, 1H), 7.74-7.67 (m, 1H), 7.57 (s, 1H), 7.50 (d, J=7.5 Hz, 1H), 7.37 (t, J=7.6 Hz, 1H), 7.30 (t, J=7.6 Hz, 1H), 7.19 (s, 1H), 7.18-7.07 (m, 2H), 5.54 (s, 1H), 5.37 (s, 2H), 5.32 (s, 2H), 4.85-4.66 (m, 2H), 4.21-4.08 (m, 4H), 4.03 (s, 1H), 3.26 (s, 1H), 3.19 (m, 1H), 2.99 (s, 1H), 2.85 (d, J=15.5 Hz, 1H), 2.44-2.36 (m, 1H), 2.14 (m, 1H), 2.08 (s, 3H), 2.06 (s, 3H), 2.02-1.84 (m, 1H), 1.74 (dt, J=12.9, 8.6 Hz, 1H).

Example 332: (S)-2-(((5-chloro-6-(((S)-4-(2-chloro-4'-(2-((2-hydroxyethyl)amino)ethoxy)-[1,1'-biphenyl]-3-yl)-2,3-dihydro-1H-inden-1-yl)oxy)-2-((3,5-dicyanobenzyl)oxy)pyridin-3-yl)methyl)amino)-3-hydroxy-2-methylpropanoic acid

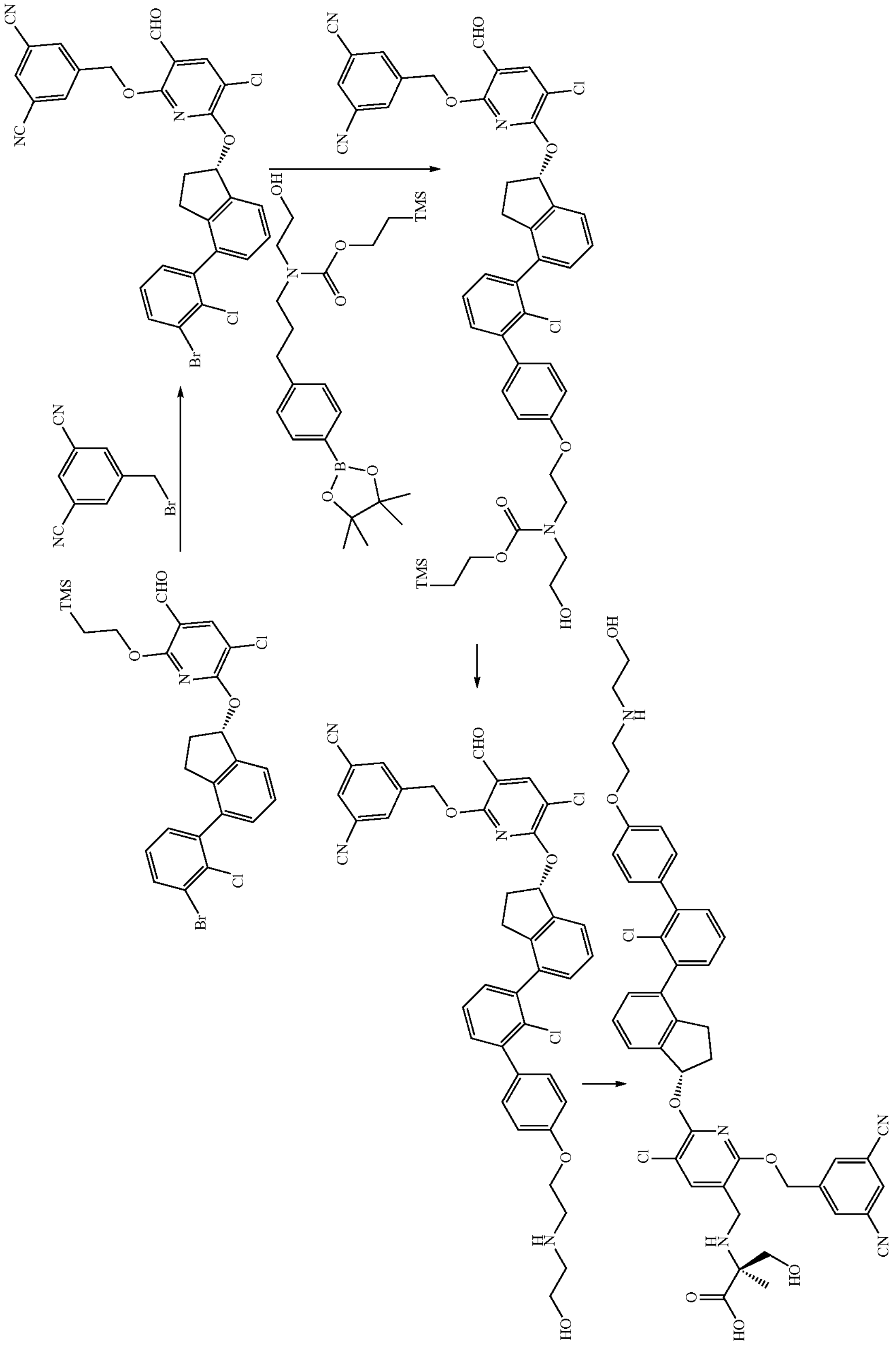

In a glass vial, (S)-6-((4-(3-bromo-2-chlorophenyl)-2,3-dihydro-1H-inden-1-yl)oxy)-5-chloro-2-(2-(trimethylsilyl)ethoxy)nicotinaldehyde (172.00 mg, 0.30 mmol) was dissolved in 5.00 ml of DMF. To this solution, CsF (180.00 mg, 1.0 mmol) was added at room temperature and mixture was stirred at 60° C. LCMS showed formation of desired product after 2 hours. In the same reaction flask, 5-(bromomethyl)isophthalonitrile (140.00 mg, 0.63 mmol) and $K_2CO_3$ (160.00 mg, 1.0 mmol) were added at room temperature. Mixture was then stirred at 60° C. under Argon for 1 hour. Crude was diluted with DCM and washed with water. Organic layer was dried over magnesium sulfate and volatiles were removed under reduced pressure. Crude was dry-loaded to a silica gel column and eluted with 0-20% DCM/EtOAc to afford (S)-5-(((6-((4-(3-bromo-2-chlorophenyl)-2,3-dihydro-1H-inden-1-yl)oxy)-5-chloro-3-formylpyridin-2-yl)oxy)methyl)isophthalonitrile.

In a round flask, 2-(trimethylsilyl)ethyl (2-hydroxyethyl)(2-(4-(4,4,5,5-tetramethyl-1,3,2-dioxaborolan-2-yl)phenoxy)ethyl)carbamate (146.00 mg, 0.32 mmol), (S)-5-(((6-((4-(3-bromo-2-chlorophenyl)-2,3-dihydro-1H-inden-1-yl)oxy)-5-chloro-3-formylpyridin-2-yl)oxy)methyl)isophthalonitrile (200.00 mg, 0.32 mmol), $PdCl_2$(dppf) (24.00 mg, 0.032 mmol), and $K_2CO_3$ (89.00 mg, 0.65 mmol) were dissolved in 10.00 ml of dioxane and 1.00 ml of water. Flask was evacuated and filled with Argon. Mixture was stirred at 85° C. overnight. Crude was diluted with EtOAc and filtrated through celite. Volatiles were removed under reduced pressure and crude was dry-loaded to a silica gel column and eluted with 0-30% EtOAc/Hex to afford 2-(trimethylsilyl)ethyl (S)-(2-((2'-chloro-3'-(1-((3-chloro-6-((3,5-dicyanobenzyl)oxy)-5-formylpyridin-2-yl)oxy)-2,3-dihydro-1H-inden-4-yl)-[1,1'-biphenyl]-4-yl)oxy)ethyl)(2-hydroxyethyl)carbamate.

In a round flask, 2-(trimethylsilyl)ethyl (S)-(2-((2'-chloro-3'-(1-((3-chloro-6-((3,5-dicyanobenzyl)oxy)-5-formylpyridin-2-yl)oxy)-2,3-dihydro-1H-inden-4-yl)-[1,1'-biphenyl]-4-yl)oxy)ethyl)(2-hydroxyethyl)carbamate (268.00 mg, 0.31 mmol) was dissolved in 5.00 ml of DMF and CsF (188.00 mg, 1.0 mmol) was added at room temperature. Mixture was stirred at 60° C. for 3 hours. LCMS showed formation of desired product. Crude was diluted with EtOAc and washed with water. Organic layer was dried over magnesium sulfate and volatiles were removed under reduced pressure. Volatiles were removed under reduced pressure and crude was dry-loaded to a silica gel column and eluted with 30-100% EtOAc/Hex to afford (S)-5-(((5-chloro-6-((4-(2-chloro-4'-(2-((2-hydroxyethyl)amino)ethoxy)-[1,1'-biphenyl]-3-yl)-2,3-dihydro-1H-inden-1-yl)oxy)-3-formylpyridin-2-yl)oxy)methyl)isophthalonitrile.

(S)-2-(((5-chloro-6-(((S)-4-(2-chloro-4'-(2-((2-hydroxyethyl)amino)ethoxy)-[1,1'-biphenyl]-3-yl)-2,3-dihydro-1H-inden-1-yl)oxy)-2-((3,5-dicyanobenzyl)oxy)pyridin-3-yl)methyl)amino)-3-hydroxy-2-methylpropanoic acid was synthesized according to general reductive amination procedure D. [M+1]=822.25. $^1$H NMR (400 MHz, Methanol-d4) δ 8.22 (d, J=8.7 Hz, 2H), 8.05 (d, J=18.6 Hz, 1H), 7.95 (s, 1H), 7.48-7.33 (m, 4H), 7.20 (d, J=6.0 Hz, 2H), 7.10 (d, J=8.5 Hz, 2H), 6.48 (s, 2H), 5.60 (d, J=10.3 Hz, 3H), 4.36 (t, J=5.0 Hz, 2H), 4.29 (s, 2H), 4.02 (d, J=12.1 Hz, 2H), 3.88-3.77 (m, 3H), 3.53 (t, J=4.9 Hz, 2H), 3.47 (s, 1H), 3.28-3.20 (m, 2H), 3.11 (s, 2H), 1.54 (s, 3H).

Example 333: (R)-5-(((3''-((2-chloro-5-((5-cyanopyridin-3-yl)methoxy)-4-((3-hydroxypyrrolidin-1-yl)methyl)phenoxy)methyl)-2',2''-dimethyl-[1,1':3',1''-terphenyl]-4-yl)methyl)amino)pentanoic acid

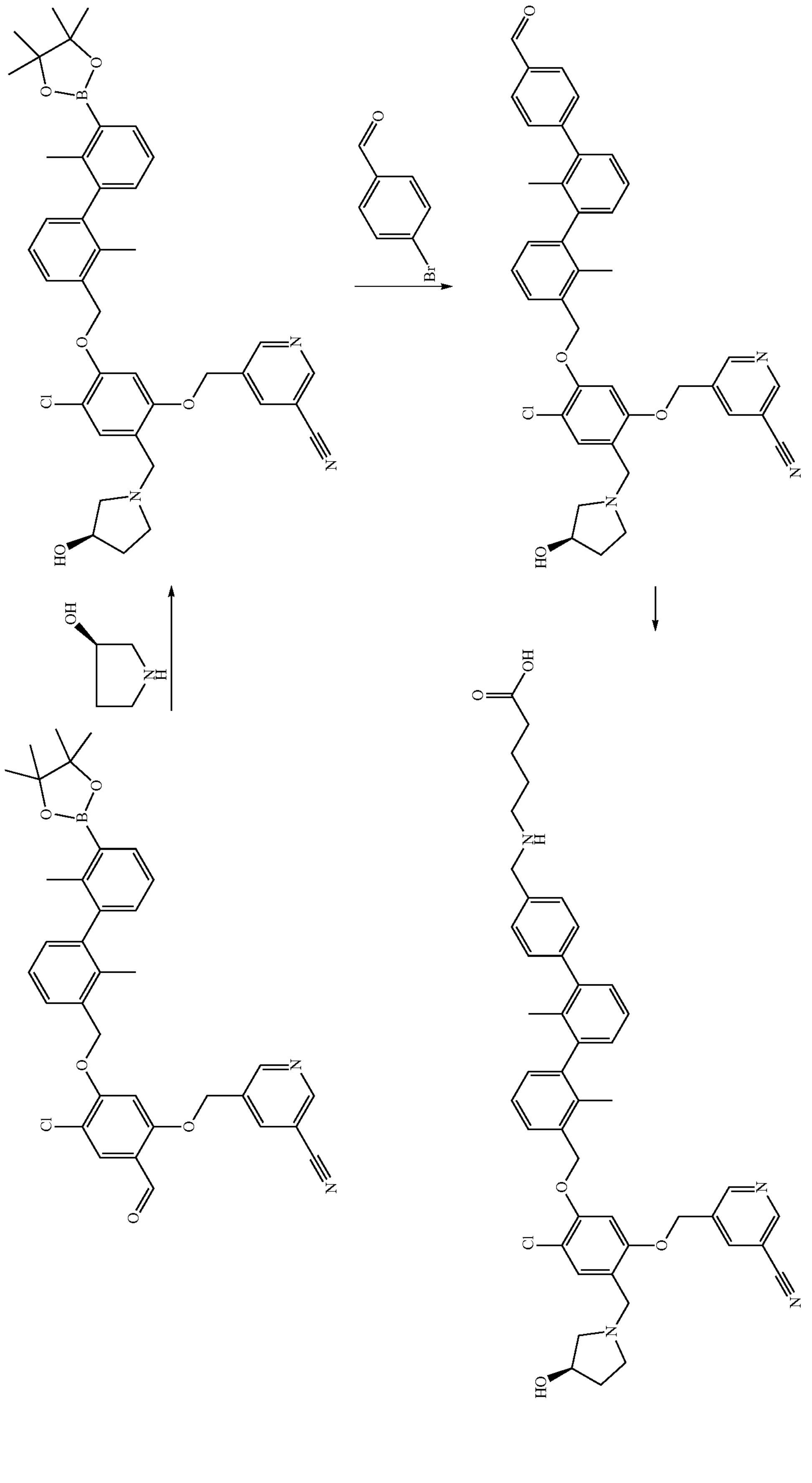

(R)-5-((4-chloro-5-((2,2'-dimethyl-3'-(4,4,5,5-tetramethyl-1,3,2-dioxaborolan-2-yl)-[1,1'-biphenyl]-3-yl)methoxy)-2-((3-hydroxypyrrolidin-1-yl)methyl)phenoxy)methyl)nicotinonitrile was synthesized according to general reductive amination procedure D.

In around flask, (R)-5-((4-chloro-5-((2,2'-dimethyl-3'-(4,4,5,5-tetramethyl-1,3,2-dioxaborolan-2-yl)-[1,1'-biphenyl]-3-yl)methoxy)-2-((3-hydroxypyrrolidin-1-yl)methyl)phenoxy)methyl)nicotinonitrile (560.00 mg, 0.87 mmol), 4-bromobenzaldehyde (166.00 mg, 0.87 mmol), $PdCl_2$dppf (80.00 mg, 0.13 mmol), and $Cs_2CO_3$ (565.00 mg, 2.0 mmol) were dissolved in 15.00 ml of dioxane and 1.50 ml of water. Flask was evacuated and filled with Argon. Mixture was stirred at 85° C. overnight. Crude was diluted with EtOAc and filtrated through celite. Volatiles were removed under reduced pressure and crude was dry-loaded to a silica gel column and eluted with 0-100% EtOAc/Hex to provide (R)-5-((4-chloro-5-((4"-formyl-2,2'-dimethyl-[1,1':3',1"-terphenyl]-3-yl)methoxy)-2-((3-hydroxypyrrolidin-1-yl)methyl)phenoxy)methyl)nicotinonitrile.

(R)-5-(((3"-((2-chloro-5-((5-cyanopyridin-3-yl)methoxy)-4-((3-hydroxypyrrolidin-1-yl)methyl)phenoxy)methyl)-2',2"-dimethyl-[1,1':3',1"-terphenyl]-4-yl)methyl)amino)pentanoic acid was synthesized according to general reductive amination procedure D. [M+1]=759.33. $^1$H NMR (400 MHz, Methanol-d4) δ 9.08-8.79 (m, 2H), 8.37 (d, J=7.6 Hz, 1H), 7.60-7.52 (m, 3H), 7.51-7.42 (m, 3H), 7.29 (dt, J=15.8, 7.6 Hz, 2H), 7.20 (dd, J=7.7, 1.5 Hz, 1H), 7.19-7.07 (m, 4H), 5.39 (s, 2H), 5.32 (s, 2H), 4.50 (d, J=22.4 Hz, 2H), 4.35 (s, 1H), 4.25 (s, 2H), 3.55 (td, J=34.3, 30.5, 9.9 Hz, 2H), 3.29 (s, 2H), 3.15-3.04 (m, 2H), 2.38 (t, J=6.9 Hz, 2H), 2.14 (s, 3H), 2.05 (d, J=35.0 Hz, 2H), 1.88 (s, 3H), 1.83-1.62 (m, 4H).

Example 334:4-(((3"-((2-chloro-5-((5-cyanopyridin-3-yl)methoxy)-4-(((2-hydroxyethyl)amino)methyl)phenoxy)methyl)-2',2"-dimethyl-[1,1':3',1"-terphenyl]-4-yl)methyl)amino)butanoic acid

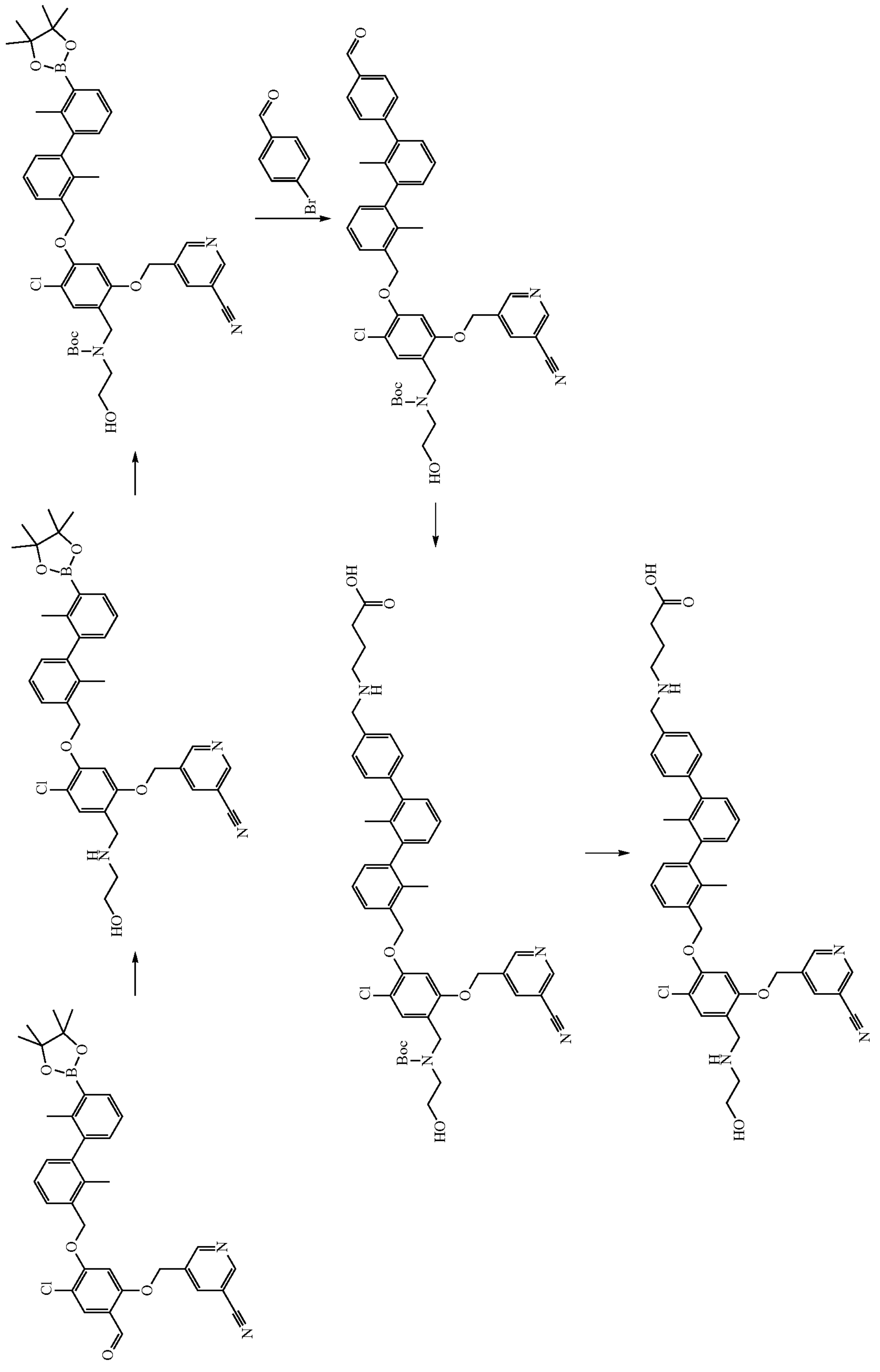

5-((4-chloro-5-((2,2'-dimethyl-3'-(4,4,5,5-tetramethyl-1,3,2-dioxaborolan-2-yl)-[1,1'-biphenyl]-3-yl)methoxy)-2-(((2-hydroxyethyl)amino)methyl)phenoxy)methyl)nicotinonitrilewassynthesized according to general reductive amination procedure E.

In a round bottom flask, Boc anhydride (1.0 g, 2.0 mmol) and 5-((4-chloro-5-((2,2'-dimethyl-3'-(4,4,5,5-tetramethyl-1,3,2-dioxaborolan-2-yl)-[1,1'-biphenyl]-3-yl)methoxy)-2-(((2-hydroxyethyl)amino)methyl)phenoxy)methyl)nicotinonitrile (337.05 mg, 2.0 mmol) were dissolved in 10.00 ml of DCM. To this solution was added one pellet of 4-DMAP at room temperature. Mixture was stirred at room temperature for 30 min. LCMS showed partial conversion to the desired product. An additional 337.00 mg of Boc anhydride were added at room temperature and the mixture was stirred for another 30 min. Methanol was added to the reaction mixture and volatiles were removed under reduced pressure. Crude was dry-loaded to a silica gel column and eluted with 50-100% EtOAc/Hex to afford tert-butyl (5-chloro-2-((5-cyanopyridin-3-yl)methoxy)-4-((2,2'-dimethyl-3'-(4,4,5,5-tetramethyl-1,3,2-dioxaborolan-2-yl)-[1,1'-biphenyl]-3-yl)methoxy)benzyl)(2-hydroxyethyl)carbamate.

In a round bottom flask tert-butyl (5-chloro-2-((5-cyanopyridin-3-yl)methoxy)-4-((2,2'-dimethyl-3'-(4,4,5,5-tetramethyl-1,3,2-dioxaborolan-2-yl)-[1,1'-biphenyl]-3-yl)methoxy)benzyl)(2-hydroxyethyl)carbamate (230.00 mg, 0.31 mmol), 4-bromobenzaldehyde (56.50 mg, 0.31 mmol), $PdCl_2dppf$ (9.00 mg, 0.013 mmol), and $Cs_2CO_3$ (198.00 mg, 0.6 mmol) were dissolved in 10.00 ml of dioxane and 1.00 ml of water. Flask was evacuated and filled with Argon. Mixture was stirred at 100° C. overnight. Crude was diluted with EtOAc and filtrated through celite. Volatiles were removed under reduced pressure and crude was dry-loaded to a silica gel column and eluted with 0-100% EtOAc/Hex to afford tert-butyl (5-chloro-2-((5-cyanopyridin-3-yl)methoxy)-4-((4"-formyl-2,2'-dimethyl-[1,1':3',1"-terphenyl]-3-yl)methoxy)benzyl)(2-hydroxyethyl)carbamate.

4-(((3"-((4-(((tert-butoxycarbonyl)(2-hydroxyethyl)amino)methyl)-2-chloro-5-((5-cyanopyridin-3-yl)methoxy)phenoxy)methyl)-2',2"-dimethyl-[1,1':3',1"-terphenyl]-4-yl)methyl)amino)butanoic acid was synthesized according to general reductive amination procedure D.

In a round bottom flask, 4-(((3"-((4-(((tert-butoxycarbonyl)(2-hydroxyethyl)amino)methyl)-2-chloro-5-((5-cyanopyridin-3-yl)methoxy)phenoxy)methyl)-2',2"-dimethyl-[1,1':3',1"-terphenyl]-4-yl)methyl)amino)butanoic acid was dissolved in 5.00 mL of DCM and 0.8 mL of TFA was added to the solution at room temperature. Mixture was stirred at ambient temperature for 30 min. Volatiles were removed under reduced pressure and crude was dissolved in acetonitrile/water mixture and loaded into Gilson and purified by reverse phase chromatography (0.1% trifluoroacetic acid in acetonitrile/water) providing the final compound upon lyophilization as the bis-TFA salt. [M+1]=719.30. $^1$H NMR (400 MHz, Methanol-d4) δ 8.94 (d, J=13.9 Hz, 2H), 8.38 (d, J=1.7 Hz, 1H), 7.66-7.39 (m, 6H), 7.40-7.10 (m, 5H), 7.08 (s, 1H), 5.37 (s, 2H), 5.31 (s, 2H), 4.25 (d, J=13.0 Hz, 4H), 3.83-3.70 (m, 2H), 3.20-3.07 (m, 4H), 2.48 (t, J=7.0 Hz, 2H), 2.14 (s, 3H), 2.04-1.98 (m, 2H), 1.87 (s, 3H).

Example 335: (S)-4-((5-chloro-2-((5-cyanopyridin-3-yl)methoxy)-4-((4"-(((S)-3-hydroxypyrrolidin-1-yl)methyl)-2,2'-dimethyl-[1,1':3',1"-terphenyl]-3-yl)methoxy)benzyl)amino)-3-hydroxybutanoic acid

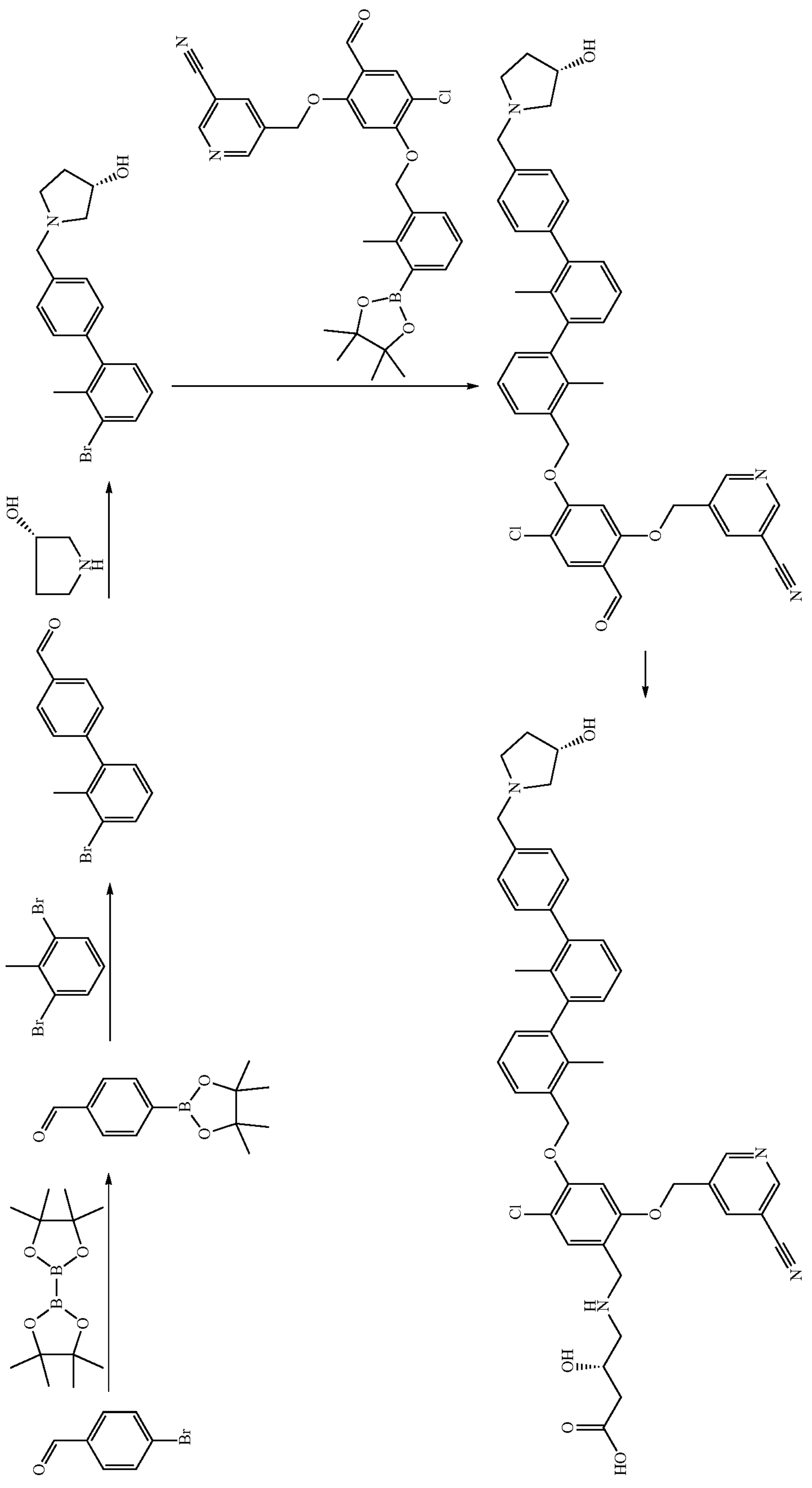

In a round bottom flask, 4-bromobenzaldehyde (2.0 g, 11.00 mmol), $B_2Pin_2$ (3.00 g, 12.00 mmol), $PdCl_2$(dppf) (328.00 mg, 0.5 mmol) and KOAc (3.2 g, 32.00 mmol) were dissolved in 100.00 ml of dioxane. Flask was capped, then evacuated and filled with argon. Mixture was stirred under argon over the weekend at 100° C. Crude was filtered through celite and volatiles were removed under reduced pressure. Crude was dry-loaded to a silica gel column and eluted with 0-30% EtOAc/Hex to afford 4-(4,4,5,5-tetramethyl-1,3,2-dioxaborolan-2-yl)benzaldehyde.

In a round bottom flask, 4-(4,4,5,5-tetramethyl-1,3,2-dioxaborolan-2-yl)benzaldehyde (2.5 g, 11.00 mmol), 2,6-dibromotoluene (2.85 g, 11.00 mmol), $PdCl_2$ (dppf) (457.00 mg, 0.7 mmol) and $Cs_2CO_3$ (8.8 g, 27.00 mmol) were dissolved in 100.00 ml of dioxane and 10.00 ml of water. Flask was capped, then evacuated and filled with argon. Mixture was stirred under argon overnight at 100° C. Crude was filtered through celite and volatiles were removed under reduced pressure. Crude was dry-loaded to a silica gel column and eluted with 0-30% EtOAc/Hex to afford 3'-bromo-2'-methyl-[1,1'-biphenyl]-4-carbaldehyde.

(S)-1-((3'-bromo-2'-methyl-[1,1'-biphenyl]-4-yl)methyl) pyrrolidin-3-ol was synthesized according to general reductive amination procedure E.

under reduced pressure. Crude was dry-loaded to a silica gel column and eluted with 80-100% EtOAc/Hex to afford (S)-5-((4-chloro-2-formyl-5-((4"-((3-hydroxypyrrolidin-1-yl)methyl)-2,2'-dimethyl-[1,1':3',1"-terphenyl]-3-yl) methoxy)phenoxy)methyl)nicotinonitrile.

(S)-4-((5-chloro-2-((5-cyanopyridin-3-yl)methoxy)-4-((4"-(((S)-3-hydroxypyrrolidin-1-yl)methyl)-2,2'-dimethyl-[1,1':3',1"-terphenyl]-3-yl)methoxy)benzyl)amino)-3-hydroxybutanoic acid was synthesized according to general reductive amination procedure D. [M+1]=761.31. $^1$H NMR (400 MHz, Methanol-$d_4$) δ 8.94 (dd, J=11.1, 2.1 Hz, 2H), 8.37 (t, J=2.1 Hz, 1H), 7.59 (d, J=8.1 Hz, 2H), 7.48 (dd, J=14.2, 7.0 Hz, 4H), 7.37-7.09 (m, 5H), 7.08 (s, 1H), 5.38 (s, 2H), 5.31 (s, 2H), 4.76-4.30 (m, 4H), 4.23 (s, 3H), 3.76-3.30 (m, 2H), 3.20 (dd, J=12.7, 3.0 Hz, 1H), 2.97 (dd, J=12.7, 9.8 Hz, 1H), 2.65 (s, 0H), 2.51 (dd, J=6.2, 1.2 Hz, 2H), 2.14 (s, 3H), 1.89 (s, 3H).

Example 336: (S)-2-((5-chloro-2-((5-cyanopyridin-3-yl)methoxy)-4-((4"-(((S)-3-hydroxypyrrolidin-1-yl)methyl)-2,2'-dimethyl-[1,1':3',1"-terphenyl]-3-yl) methoxy)benzyl)amino)-3-hydroxy-2-methylpropanoic acid

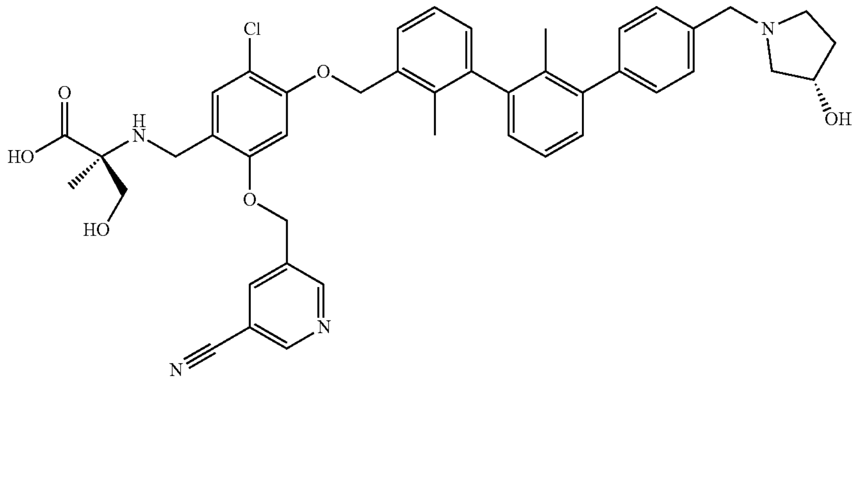 [SMILES: Cc1c(COc2cc(OCc3cncc(C#N)c3)c(CN[C@@](C)(CO)C(=O)O)cc2Cl)cccc1-c1cccc(-c2ccc(CN3CC[C@H](O)C3)cc2)c1C]

In a round bottom flask, (S)-1-((3'-bromo-2'-methyl-[1,1'-biphenyl]-4-yl)methyl)pyrrolidin-3-ol (445.00 mg, 1.10 mmol), 5-((4-chloro-2-formyl-5-((2-methyl-3-(4,4,5,5-tetramethyl-1,3,2-dioxaborolan-2-yl)benzyl)oxy)phenoxy) methyl)nicotinonitrile (600.00 mg, 1.10 mmol), $PdCl_2$(dppf) (24.00 mg, 0.05 mmol) and $Cs_2CO_3$ (942.00 mg, 3.00 mmol) were dissolved in 10.00 ml of dioxane and 1.00 ml of water. Flask was capped, then evacuated and filled with argon. Mixture was stirred under argon for six hours at 100° C. Crude was filtered through celite and volatiles were removed The title compound was synthesized according to Example 335. [M+1]=761.31. $^1$H NMR (400 MHz, Methanol-d4) δ 9.07-8.93 (m, 1H), 8.96-8.85 (m, 1H), 8.42 (t, J=2.0 Hz, 1H), 7.63-7.56 (m, 2H), 7.55 (s, 1H), 7.49-7.45 (m, 3H), 7.35-7.19 (m, 3H), 7.13 (ddd, J=11.3, 7.6, 1.4 Hz, 2H), 7.08 (s, 1H), 5.37 (s, 2H), 5.32 (s, 2H), 4.49 (dd, J=45.7, 26.2 Hz, 3H), 4.28 (s, 2H), 4.01 (d, J=12.1 Hz, 1H), 3.81 (d, J=12.1 Hz, 1H), 3.77-3.42 (m, 2H), 3.40-3.32 (m, 2H), 2.65 (s, 2H), 2.14 (s, 3H), 1.88 (s, 3H), 1.53 (s, 3H).

Example 337: (S)-4-((5-chloro-2-((5-cyanopyridin-3-yl)methoxy)-4-((3'-(4-((2-hydroxyethyl)amino)quinazolin-6-yl)-2,2'-dimethyl-[1,1'-biphenyl]-3-yl)methoxy)benzyl)amino)-3-hydroxybutanoic acid

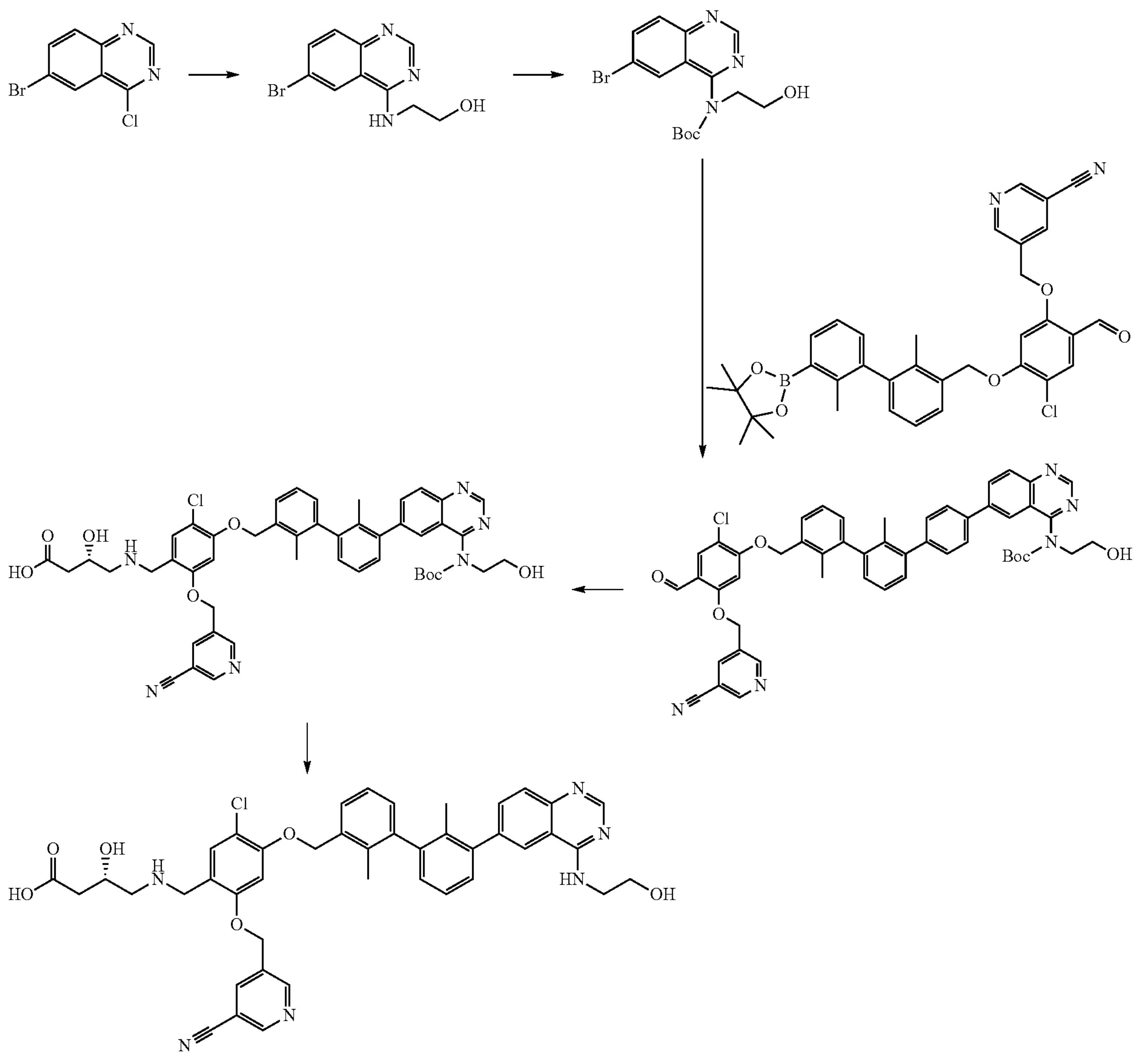

In a glass vial, dissolve 6-bromo-4-chloroquinazoline (100 mg, 0.41 mmol) in 3.00 ml of ethanolamine at room temperature. Vial was capped and solution was stirred at 110° C. overnight. LCMS showed formation of the desired product. Crude was diluted with EtOAc and washed with water. Organic layer was dried over magnesium sulfate and volatiles were removed under reduced pressure to afford 2-((6-bromoquinazolin-4-yl)amino)ethan-1-ol, which was taken to the next step without further purification.

In a round bottom flask, 2-((6-bromoquinazolin-4-yl)amino)ethan-1-ol (110.00 mg, 0.41 mmol) was dissolved in 5.00 ml of DCM. To this solution was added Boc anhydride (223.8 mg, 1.0 mmol) and triethylamine (166.00 mg, 2.0 mmol) at room temperature. Flask was capped and the reaction mixture was stirred at room temperature for 1 hour. LCMS showed conversion of the desired product. Volatiles were removed under reduced pressure to afford tert-butyl (6-bromoquinazolin-4-yl)(2-hydroxyethyl)carbamate.

In a round bottom flask, tert-butyl (6-bromoquinazolin-4-yl)(2-hydroxyethyl)carbamate (80.00 mg, 0.22 mmol), 5-((4-chloro-2-formyl-5-((2-methyl-3-(4,4,5,5-tetramethyl-1,3,2-dioxaborolan-2-yl)benzyl)oxy)phenoxy)methyl)nicotinonitrile (80.00 mg, 0.13 mmol), $PdCl_2(dppf)$ (5.00 mg, 0.008 mmol) and $Cs_2CO_3$ (96.00 mg, 0.29 mmol) were dissolved in 10.00 ml of dioxane and 1.00 ml of water. Flask was capped, then evacuated and filled with argon. Mixture was stirred under argon overnight at 100° C. Crude was filtered through celite and volatiles were removed under reduced pressure. Crude was dry-loaded to a silica gel column and eluted with 80-100% EtOAc/Hex to afford (tert-butyl (6-(3"-((2-chloro-5-((5-cyanopyridin-3-yl)methoxy)-4-formylphenoxy)methyl)-2',2"-dimethyl-[1,1':3',1"-terphenyl]-4-yl)quinazolin-4-yl)(2-hydroxyethyl)carbamate.

(S)-4-((4-((3'-(4-((tert-butoxycarbonyl)(2-hydroxyethyl)amino)quinazolin-6-yl)-2,2'-dimethyl-[1,1'-biphenyl]-3-yl)methoxy)-5-chloro-2-((5-cyanopyridin-3-yl)methoxy)benzyl)amino)-3-hydroxybutanoic acid was synthesized according to general reductive amination procedure D.

In a round bottom flask, (S)-4-((4-((3'-(4-((tert-butoxycarbonyl)(2-hydroxyethyl)amino)quinazolin-6-yl)-2,2'-dimethyl-[1,1'-biphenyl]-3-yl)methoxy)-5-chloro-2-((5-cyanopyridin-3-yl)methoxy)benzyl)amino)-3-hydroxybutanoic acid was dissolved in 5.00 mL of DCM and 0.8 ml of TFA were added to the solution at room temperature. Mixture was stirred at ambient temperature for 30 min. Volatiles were removed under reduced pressure and crude was dissolved in acetonitrile/water mixture and loaded into Gilson and purified by reverse phase chromatography (0.1% trifluoroacetic acid in acetonitrile/water) providing the final compound upon lyophilization as the bis-TFA salt. [M+1]=773.29. $^1$H NMR (400 MHz, Methanol-$d_4$) δ 9.00-8.88 (m, 2H), 8.77 (s, 1H), 8.39 (d, J=14.6 Hz, 2H), 8.07 (d, J=8.6 Hz, 1H), 7.83 (d, J=8.6 Hz, 1H), 7.49 (d, J=14.0 Hz, 2H), 7.41-7.14 (m, 5H), 7.08 (s, 1H), 5.38 (s, 2H), 5.32 (s, 2H), 4.29-4.15 (m, 3H), 3.97 (t, J=5.5 Hz, 2H), 3.86 (t, J=5.4 Hz, 2H), 3.23-3.09 (m, 1H), 3.03-2.91 (m, 1H), 2.56-2.46 (m, 2H), 2.16 (s, 3H), 1.94 (s, 3H).

Example 338: (1R,3S)-3-((5-chloro-2-((5-cyanopyridin-3-yl)methoxy)-4-((4"-(2-((2-hydroxyethyl)amino)ethoxy)-2,2'-dimethyl-[1,1':3',1"-terphenyl]-3-yl)methoxy)benzyl)amino)cyclopentane-1-carboxylic acid

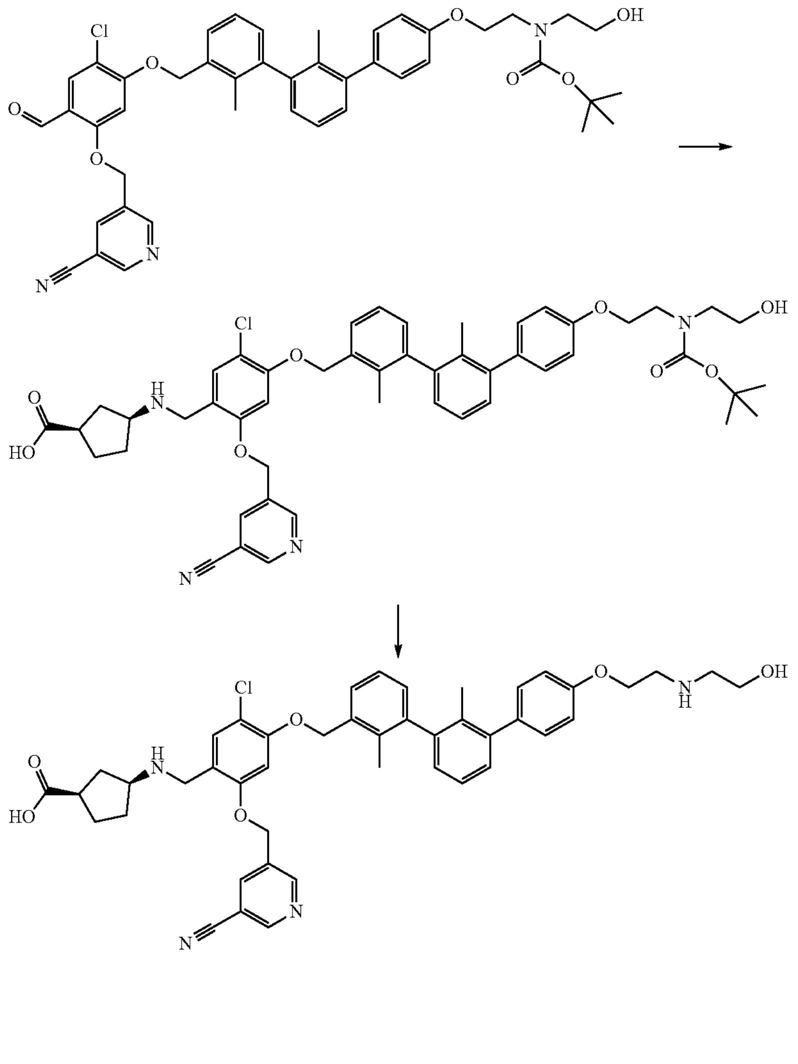

(1R,3S)-3-((4-((4"-(2-((tert-butoxycarbonyl)(2-hydroxyethyl)amino)ethoxy)-2,2'-dimethyl-[1,1':3',1"-terphenyl]-3-yl)methoxy)-5-chloro-2-((5-cyanopyridin-3-yl)methoxy)benzyl)amino)cyclopentane-1-carboxylic acid was synthesized according to general reductive amination procedure E.

In a round bottom flask, (1R,3S)-3-((4-((4"-(2-((tert-butoxycarbonyl)(2-hydroxyethyl)amino)ethoxy)-2,2'-dimethyl-[1,1':3',1"-terphenyl]-3-yl)methoxy)-5-chloro-2-((5-cyanopyridin-3-yl)methoxy)benzyl)amino)cyclopentane-1-carboxylic acid was dissolved in 5.00 mL of DCM and 0.8 ml of TFA were added to the solution at room temperature. Mixture was stirred at ambient temperature for 30 min. Volatiles were removed under reduced pressure and crude was dissolved in acetonitrile/water mixture and loaded into Gilson and purified by reverse phase chromatography (0.1% trifluoroacetic acid in acetonitrile/water) providing the title compound upon lyophilization as the bis-TFA salt. [M+1]=775.33. $^1$H NMR (400 MHz, Methanol-d4) δ 8.95 (dd, J=12.8, 2.0 Hz, 2H), 8.37 (t, J=2.0 Hz, 1H), 7.50 (s, 1H), 7.45 (d, J=7.6 Hz, 1H), 7.33-7.21 (m, 4H), 7.16 (ddd, J=17.9, 7.7, 1.4 Hz, 2H), 7.12-7.03 (m, 4H), 5.37 (s, 2H), 5.31 (s, 2H), 4.40-4.32 (m, 2H), 4.19 (s, 2H), 3.91-3.81 (m, 2H), 3.68 (p, J=7.2 Hz, 1H), 3.53 (t, J=5.0 Hz, 2H), 3.28-3.19 (m, 2H), 2.91 (p, J=7.3 Hz, 1H), 2.29 (dt, J=14.8, 7.7 Hz, 1H), 2.14 (s, 4H), 2.02-1.84 (m, 6H), 1.72 (dq, J=14.6, 7.7 Hz, 1H).

Example 339: (S)-4-((5-chloro-2-((5-cyanopyridin-3-yl)methoxy)-4-((2,2'-dimethyl-4"-(piperazin-1-yl)-[1,1':3',1"-terphenyl]-3-yl)methoxy)benzyl)amino)-3-hydroxybutanoic acid

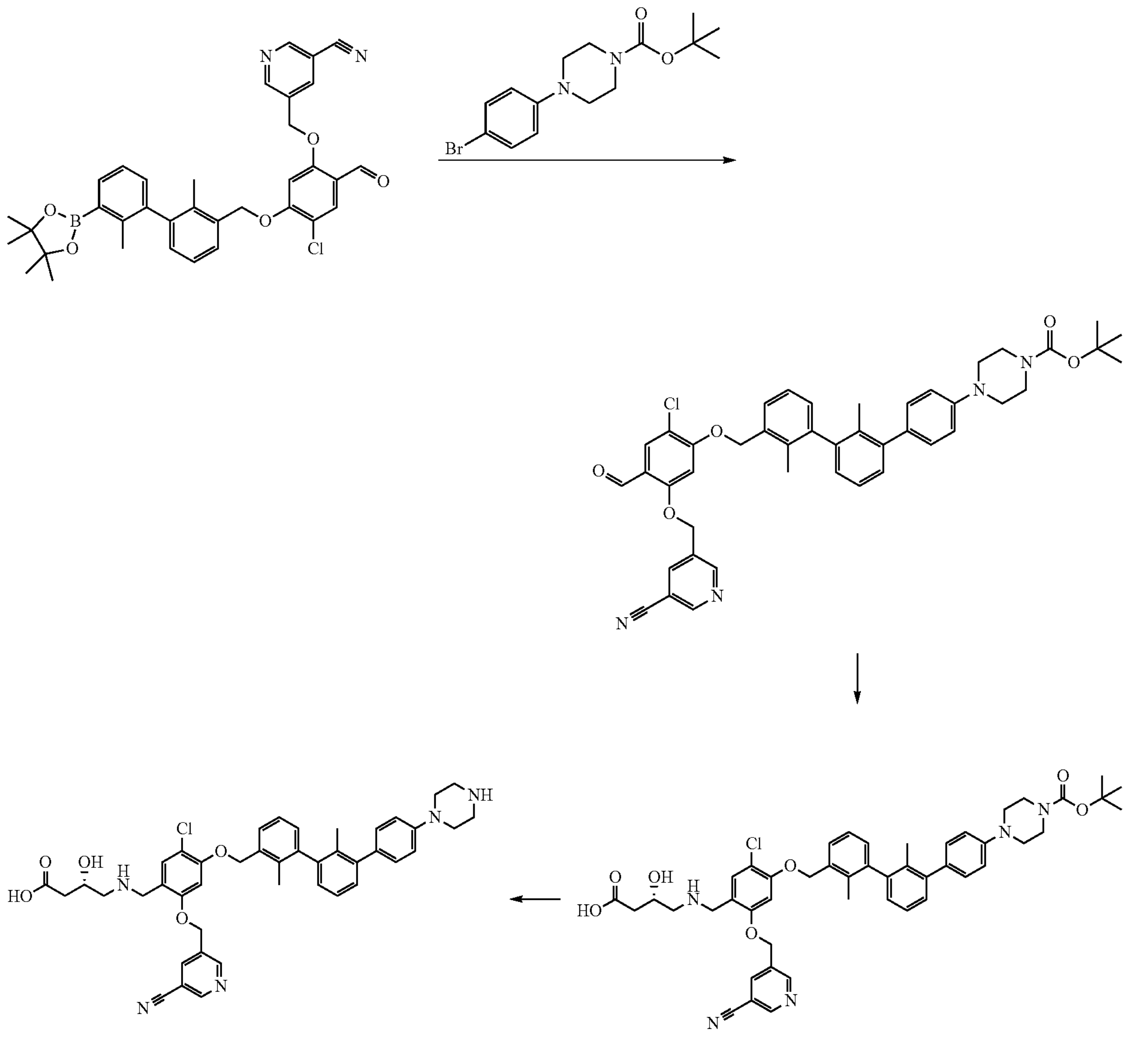

In around bottom flask, tert-butyl 4-(4-bromophenyl)piperazine-1-carboxylate (69.00 mg, 0.20 mmol), 5-((4-chloro-2-formyl-5-((2-methyl-3-(4,4,5,5-tetramethyl-1,3,2-dioxaborolan-2-yl)benzyl)oxy)phenoxy)methyl)nicotinonitrile (117.00 mg, 0.19 mmol), $PdCl_2$(dppf) (5.00 mg, 0.008 mmol) and $Cs_2CO_3$ (125.00 mg, 0.38 mmol) were dissolved in 10.00 ml of dioxane and 1.00 ml of water. Flask was capped, then evacuated and filled with argon. Mixture was stirred under argon overnight at 100° C. Crude was filtered through celite and volatiles were removed under reduced pressure. Crude was dry-loaded to a silica gel column and eluted with 50-100% EtOAc/Hex to tert-butyl 4-(3"-((2-chloro-5-((5-cyanopyridin-3-yl)methoxy)-4-formylphenoxy)methyl)-2',2"-dimethyl-[1,1':3,1"-terphenyl]-4-yl)piperazine-1-carboxylate.

(S)-4-((4-((4"-(4-(tert-butoxycarbonyl)piperazin-1-yl)-2,2'-dimethyl-[1,1':3,1"-terphenyl]-3-yl)methoxy)-5-chloro-2-((5-cyanopyridin-3-yl)methoxy)benzyl)amino)-3-hydroxybutanoic acid was synthesized according to general reductive amination procedure E.

In around bottom flask, (S)-4-((4-((4"-(4-(tert-butoxycarbonyl)piperazin-1-yl)-2,2'-dimethyl-[1,1':3',1"-terphenyl]-3-yl)methoxy)-5-chloro-2-((5-cyanopyridin-3-yl)methoxy)benzyl)amino)-3-hydroxybutanoic acid was dissolved in 5.00 ml of DCM and 0.8 ml of TFA were added to the solution at room temperature. Mixture was stirred at ambient temperature for 30 min Volatiles were removed under reduced pressure and crude was dissolved in acetonitrile/water mixture and loaded into Gilson and purified by reverse phase chromatography (0.1% trifluoroacetic acid in acetonitrile/water) providing the title compound upon lyophilization as the bis-TFA salt. [M+1]=746.31. $^1$H NMR (400 MHz, Methanol-d4) δ 58.94 (dd, J=12.2, 2.0 Hz, 2H), 8.38 (t, J=2.1 Hz, 1H), 7.51 (s, 1H), 7.45 (d, J=7.5 Hz, 1H), 7.36-7.00 (m, 10H), 5.37 (s, 2H), 5.31 (s, 2H), 4.23 (s, 3H), 3.50-3.37 (m, 8H), 3.19 (dd, J=12.7, 3.0 Hz, 1H), 2.97 (dd, J=12.7, 9.8 Hz, 1H), 2.51 (dd, J=6.3, 1.0 Hz, 2H), 2.14 (s, 3H), 1.88 (s, 3H).

Example 340: (S)-2-(((5-chloro-2-((5-cyanopyridin-3-yl)methoxy)-6-((2,2'-dichloro-4"-(2-((2-hydroxy-ethyl)amino)ethoxy)-[1,1':3',1"-terphenyl]-3-yl)methoxy)pyridin-3-yl)methyl)amino)-3-hydroxy-2-methylpropanoic acid
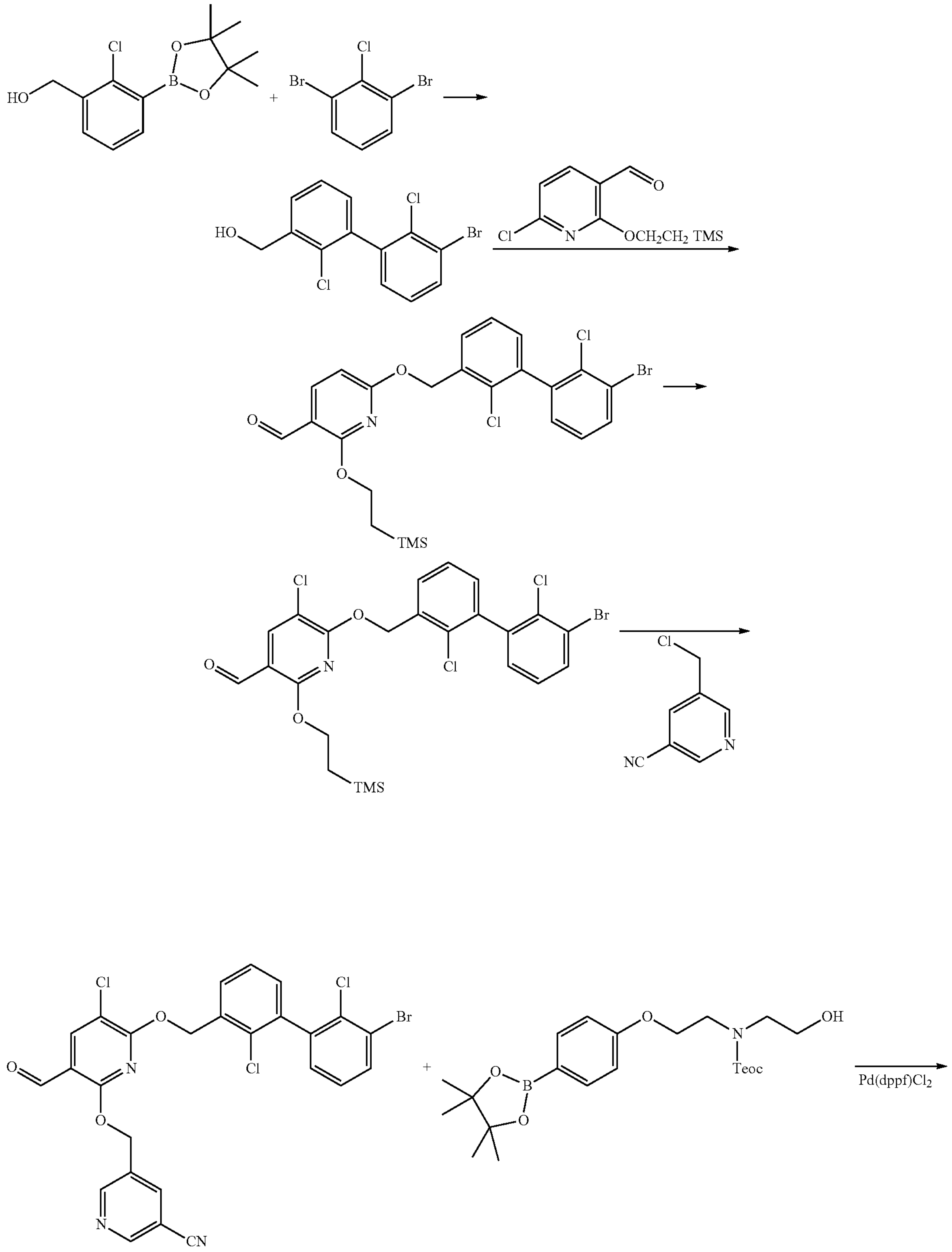

-continued

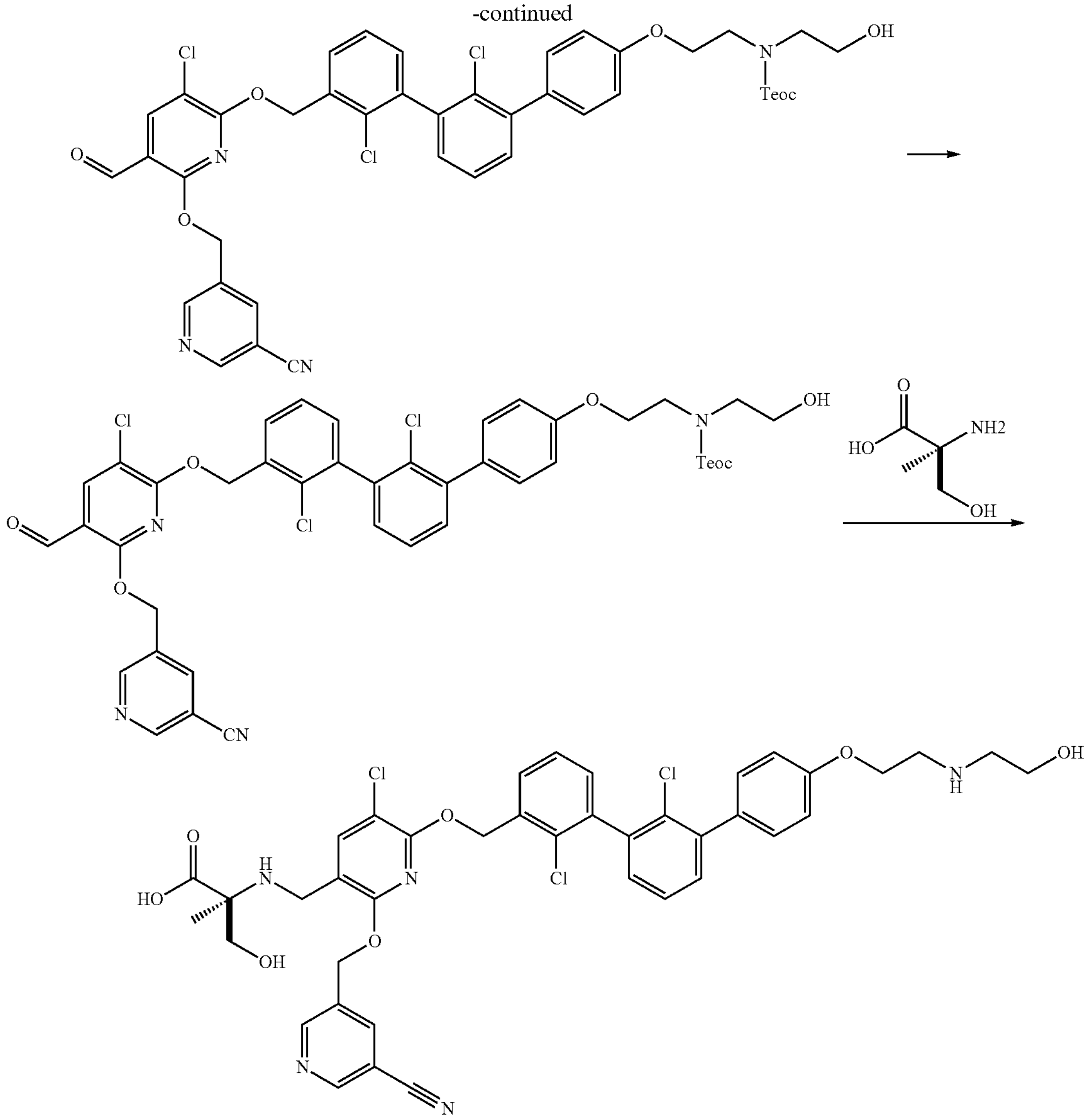

Step 1: To a mixture of (2-chloro-3-(4,4,5,5-tetramethyl-1,3,2-dioxaborolan-2-yl)phenyl)methanol (2.5 g, 9.3 mmol), 1,3-dibromo-2-chlorobenzene (3.775 g, 14.0 mmol), $Pd(dppf)Cl_2CH_2Cl_2$ (760 mg, 0.93 mmol) and potassium carbonate (2.57 g, 18.62 mmol)under $N_2$ was added a mixture of solvents (30 mL dioxane and 7.5 mL water) and heated to 85° C. for 2 h. After cooling to room temperature, the reaction was concentrated and diluted with $CH_2Cl_2$ and water. The organic layer was separated, dried with $Na_2SO_4$ and concentrated. The residue was purified by silica gel chromatography (eluting with 5% to 40% EtOAc-Hex) to give (3'-bromo-2,2'-dichloro-[1,1'-biphenyl]-3-yl)methanol.

Step 2: To (3'-bromo-2,2'-dichloro-[1,1'-biphenyl]-3-yl) methanol (2.90 g, 8.73 mmol) in DMF (25 mL) at 0° C. was added NaH (60%, 420 mg). The reaction mixture was stirred at 0° C. for 1 h. 6-Chloro-2-(2-(trimethylsilyl)ethoxy)nicotinaldehyde (2.25 g, 8.73 mmol) was added into the mixture in one portion, and the mixture was stirred at rt for 12 h. Then the mixture was treated with aq. $NH_4Cl$ (45 mL), extracted with $CH_2Cl_2$ (3×50 mL). The organic phase was washed with water (3×50 mL), dried over $Na_2SO_4$, and concentrated. The residue was purified by silica gel column chromatography (0-30% EtOAc/hex) to yield 6-((3'-bromo-2,2'-dichloro-[1,1'-biphenyl]-3-yl)methoxy)-2-(2-(trimethylsilyl)ethoxy)nicotinaldehyde.

Step 3: To 6-((3'-bromo-2,2'-dichloro-[1,1'-biphenyl]-3-yl)methoxy)-2-(2-(trimethylsilyl)ethoxy)nicotinaldehyde (2.35 g, 4.25 mmol) in a mixture of acetonitrile (10 mL) and chloroform (10 mL) was added CMBG (980 mg, 5 mmol) at 0° C. Then, 4N HCl in dioxane (1.17 mL) was added dropwise in 15 min. The reaction mixture was warmed to rt and stirred for 30 min. Then the mixture was treated with aq. $NaHCO_3$ (30 mL), extracted with DCM (3×30 mL), washed with water (10 mL), dried ($Na_2SO_4$), and concentrated. The residue was purified by silica gel column chromatography (0-15% EtOAc/hex) to yield 6-((3'-bromo-2,2'-dichloro-[1,1'-biphenyl]-3-yl)methoxy)-5-chloro-2-(2-(trimethylsilyl)ethoxy)nicotinaldehyde.

Step 4: To 6-((3'-bromo-2,2'-dichloro-[1,1'-biphenyl]-3-yl)methoxy)-5-chloro-2-(2-(trimethylsilyl)ethoxy)nicotinaldehyde (954 mg, 1.62 mmol) in DMF (8 mL) was added CsF (986 mg, 6 mmol). The mixture was heated to 60° C. for 30 min. 5-(Chloromethyl)nicotinonitrile (371 mg, 2 mmol) was added and the mixture was stirred at 60° C. for additional 90 min. The reaction mixture was cooled to rt, filtered over celite, and concentrated in vacuum, extracted with DCM, washed with water, dried ($Na_2SO_4$), and concentrated. The residue was purified by silica gel column chromatography (0-70% EtOAc/hex) to yield 5-(((6-((3'-bromo-2,2'-dichloro-[1,1'-biphenyl]-3-yl)methoxy)-5-chloro-3-formylpyridin-2-yl)oxy)methyl)nicotinonitrile.

Step 5: To a mixture of 5-(((6-((3'-bromo-2,2'-dichloro-[1,1'-biphenyl]-3-yl)methoxy)-5-chloro-3-formylpyridin-2-yl)oxy)methyl)nicotinonitrile (217 mg, 0.36 mmol), 2-(trimethylsilyl)ethyl (2-hydroxyethyl)(2-(4-(4,4,5,5-tetramethyl-1,3,2-dioxaborolan-2-yl)phenoxy)ethyl)carbamate (243 mg, 0.54 mmol), Pd(dppf)$Cl_2CH_2Cl_2$ (14 mg, 0.018 mmol) and sodium carbonate (152 mg, 1 mmol)under N2 was added a mixture of solvents (2 mL dioxane and 0.2 mL water) and heated to 90° C. for 12 h. The reaction mixture was cooled to rt, filtered over celite, concentrated in vacuum. $CH_2Cl_2$ and water were added. The aqueous layer was extracted with $CH_2Cl_2$. The organic layer was dried and concentrated. The residue was purified by silica gel column chromatography with 0-70% EtOAc in hexanes to give 2-(trimethylsilyl)ethyl (2-((2',2"-dichloro-3"-(((3-chloro-6-((5-cyanopyridin-3-yl)methoxy)-5-formylpyridin-2-yl)oxy)methyl)-[1,1':3',1"-terphenyl]-4-yl)oxy)ethyl)(2-hydroxyethyl)carbamate.

Step 6: To 2-(trimethylsilyl)ethyl (2-((2',2"-dichloro-3"-(((3-chloro-6-((5-cyanopyridin-3-yl)methoxy)-5-formylpyridin-2-yl)oxy)methyl)-[1,1':3',1"-terphenyl]-4-yl)oxy)ethyl)(2-hydroxyethyl)carbamate (300 mg, 0.35 mmol) in DMF (8 mL) was added CsF (215 mg, 1 mmol). The mixture was heated to 60° C. for 90 min. The reaction mixture was cooled to rt, treated with water, extracted with DCM. The organic phase was washed with water, dried ($Na_2SO_4$), and concentrated. The residue was used for next reaction directly.

Step 7: To a mixture of (S)-2-amino-3-hydroxy-2-methylpropanoic acid (115 mg, 0.96 mmol) and 5-(((5-chloro-6-((2,2'-dichloro-4"-(2-((2-hydroxyethyl)amino)ethoxy)-[1,1':3',1"-terphenyl]-3-yl)methoxy)-3-formylpyridin-2-yl)oxy)methyl)nicotinonitrile (85 mg, 0.12 mmol) in DMSO (2.5 mL) was added DIPEA (125 mg, 168 μL, 0.97 mmol). The mixture was heated to 60° C. for 15 min. Then sodium triacetoxyborohydride was added, and the mixture was stirred at 60° C. for 60 min. The mixture was diluted with Acetonitrile and water, filtered and purified by Gilson prepared HPLC (30-85% B in 20 min) to afford (S)-2-(((5-chloro-2-((5-cyanopyridin-3-yl)methoxy)-6-((2,2'-dichloro-4"-(2-((2-hydroxyethyl)amino)ethoxy)-[1,1':3',1"-terphenyl]-3-yl)methoxy)pyridin-3-yl)methyl)amino)-3-hydroxy-2-methylpropanoic acid. $^1H$ NMR (400 MHz, Methanol-$d_4$) δ 8.91 (s, 1H), 8.84 (s, 1H), 8.29 (s, 1H), 7.96 (s, 1H), 7.57 (m, 1H), 7.47-7.33 (m, 5H), 7.32-7.16 (m, 2H), 7.09 (m, 2H), 5.73-5.38 (m, 4H), 4.43 (m, 1H), 4.36 (m, 2H), 4.27 (s, 2H), 4.04 (m, 1H), 3.96-3.79 (m, 5H), 3.61-3.34 (m, 4H), 3.26 (m, 2H), 1.56 (s, 3H). LCMS-ESI$^+$ (m/z): $[M+H]^+$ calcd for $C_4H_{38}C_3N_5O_7$: 806.2; found: 808.0.

Example 341: (S)-4-((4-((4"-(2-(((S)-3-carboxy-2-hydroxypropyl)amino)ethoxy)-2'-chloro-2-methyl-[1,1':3',1"-terphenyl]-3-yl)methoxy)-5-chloro-2-((5-cyanopyridin-3-yl)methoxy)benzyl)amino)-3-hydroxybutanoic acid

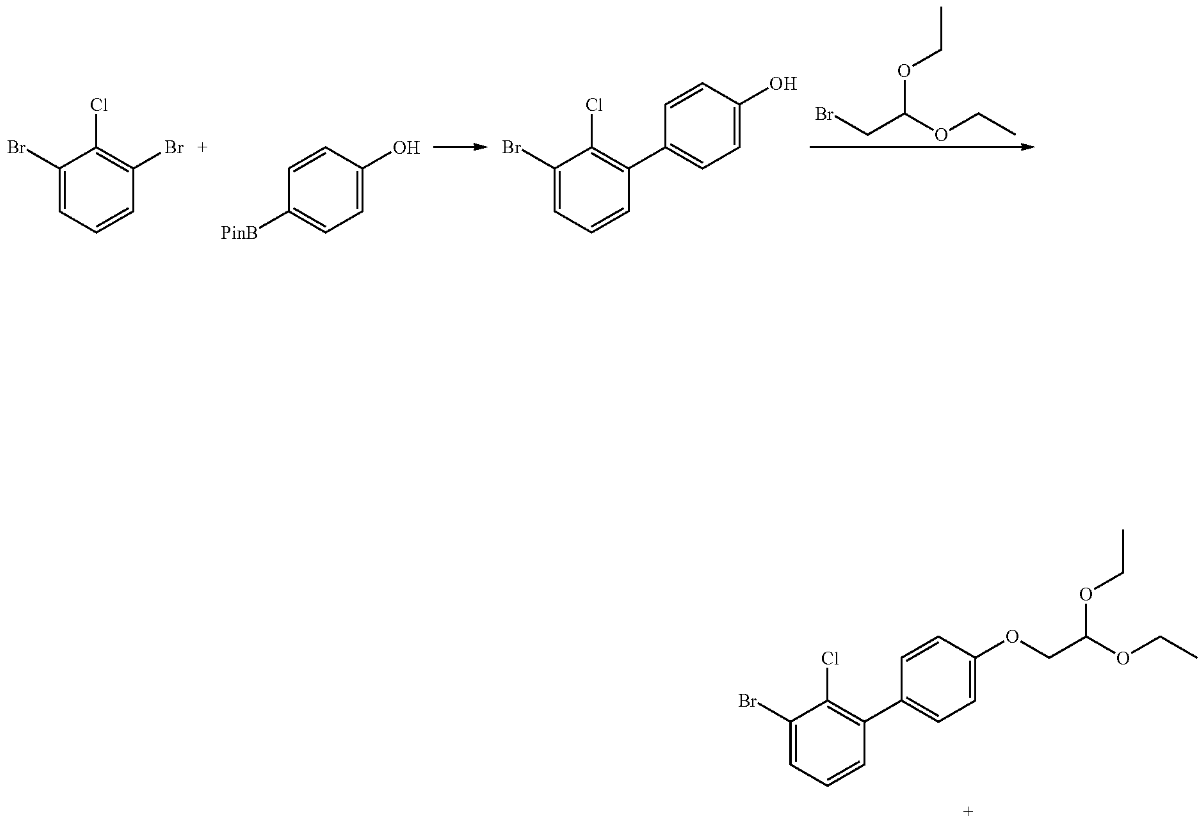

-continued

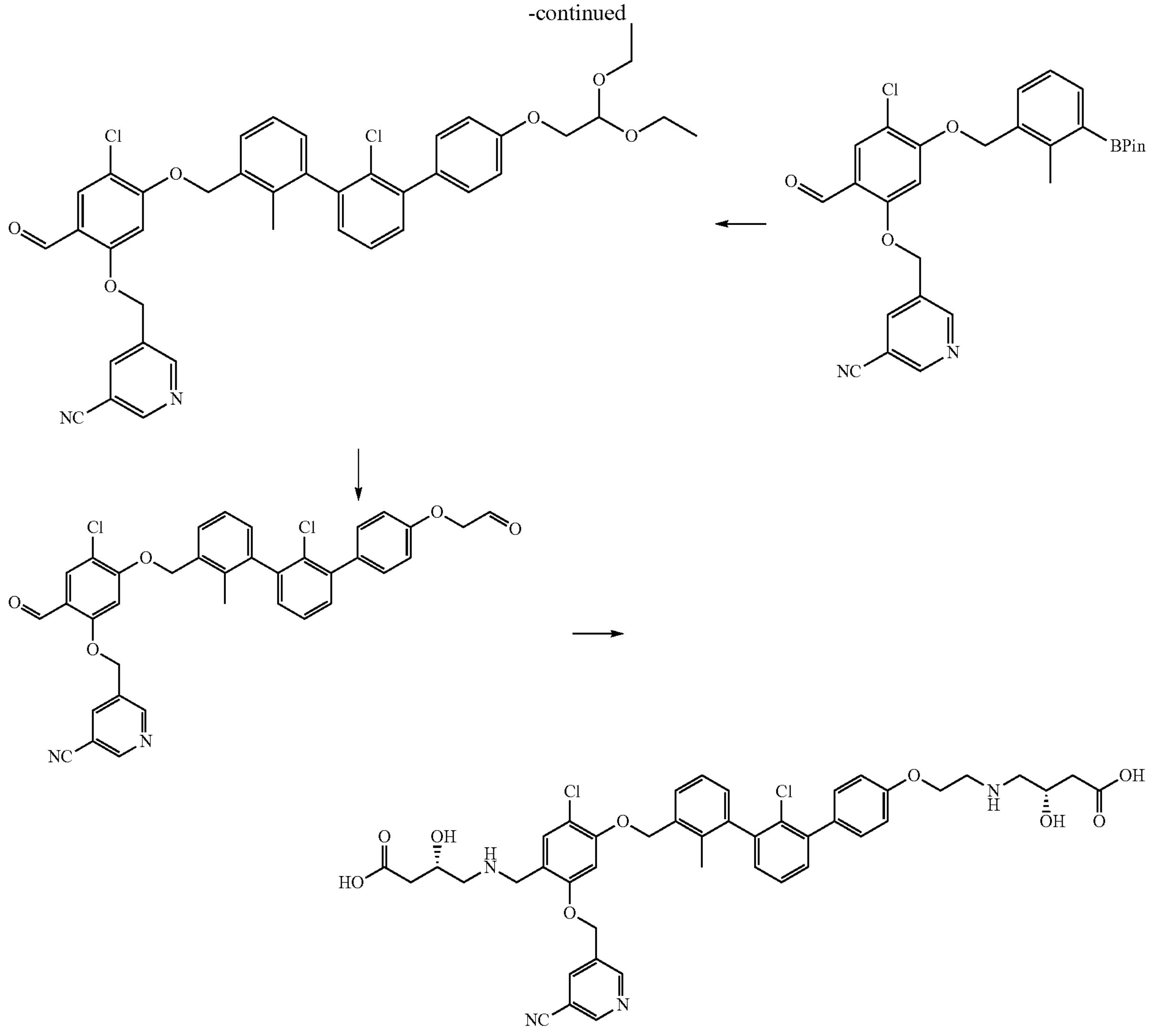

Step 1: To a mixture of 1,3-dibromo-2-chlorobenzene (1.47 g, 5.45 mmol), 4-(4,4,5,5-tetramethyl-1,3,2-dioxaborolan-2-yl)phenol (800 mg, 3.64 mmol), Pd(dppf) $Cl_2CH_2Cl_2$ (297 mg, 0.36 mmol) and potassium carbonate (1.005 g, 7.27 mmol)under N2 was added a mixture of solvents (12 mL and 3 mL water) and heated to 85° C. for 2 h. After cooling to room temperature, the reaction was diluted with $CH_2Cl_2$ and water. The organic layer was separated, dried with $Na_2SO_4$ and concentrated. The residue was purified by silica gel chromatography (eluting with 5% to 40% EtOAc-Hex) to give 3'-bromo-2'-chloro- [1,1'-biphenyl]-4-ol.

Step 2: Powdered potassium carbonate (1250 mg, 9.05 mmol) was added to a stirred solution of 3'-bromo-2'-chloro-[1,1'-biphenyl]-4-ol (1026 mg, 3.6 mmol) and bromoacetaldehyde diethyl acetal (1.13 mL, 7.24 mmol) in anhydrous DMF (10 mL). The resultant mixture is stirred at 95° C. under nitrogen overnight. The mixture was cooled to ambient temperature; then water and $CH_2Cl_2$ are added to the mixture. The organic layer is separated, dried over $Na_2SO_4$, filtered and concentrated. The oil is chromatographed on silica (gradient 5-20 percent EtOAc in hexanes) to give 3-bromo-2-chloro-4'-(2,2-diethoxyethoxy)-1,1'-biphenyl.

Step 3: A mixture of 3-bromo-2-chloro-4'-(2,2-diethoxyethoxy)-1,1'-biphenyl (285 mg, 0.71 mmol), 5-((4-chloro-2-formyl-5-((2-methyl-3-(4,4,5,5-tetramethyl-1,3,2-dioxaborolan-2-yl)benzyl)oxy)phenoxy)methyl)nicotinonitrile (370 mg, 0.71 mmol), tetrakis(triphenylphosphine)palladium(0) (103 mg, 0.089 mmol) and sodium bicarbonate (197 mg, 1.42 mmol)under $N_2$ was added a mixture of solvents (8 mL DMF and 2 mL water) and heated to 85° C. for 1 h. The reaction mixture was concentrated in vacuum, $CH_2Cl_2$ and water were added. The aqueous layer was extracted with $CH_2Cl_2$. The organic layer was dried and concentrated. The residue was purified by silica gel column chromatography with 0-70% EtOAc in hexanes to give 5-((4-chloro-5-((2'-chloro-4''-(2,2-diethoxyethoxy)-2-methyl-[1,1':3',1''-terphenyl]-3-yl)methoxy)-2-formylphenoxy)methyl)nicotinonitrile.

Step 4: 5-((4-chloro-5-((2'-chloro-4''-(2,2-diethoxyethoxy)-2-methyl-[1,1':3',1''-terphenyl]-3-yl)methoxy)-2-formylphenoxy)methyl)nicotinonitrile (55 mg, 0.077 mmol) was dissolved in 1,4-dioxane (2 mL), 0.2 ml (conc, aq) HCl was added to the clear solution. The mixture was left stirring at RT overnight. Sat. $NaHCO_3$ and EtOAc were added to the mixture. The organic layer was concentrated in vacuum. The crude residue was used in the next step.

Step 5: Fine powder of KOH (34 mg, 0.61 mmol), (S)-4-amino-3-hydroxybutanoic acid (73 mg, 0.61 mmol) were taken into a small round bottle flask, added ethanol (3 mL), flushed with $N_2$, sonicated to give a clear solution. To the solution was added solution of 5-((4-chloro-5-((2'-chloro-2-methyl-4"-(2-oxoethoxy)-[1,1':3',1"-terphenyl]-3-yl)methoxy)-2-formylphenoxy)methyl)nicotinonitrile (49 mg, 0.061 mmol) in DCM (3 mL) at once. The mixture is stirred at RT for 30 min. To this was added $NaBH(OAc)_3$ (130 mg, 0.61 mmol) at once followed by 3 drops of AcOH. The reaction mixture was stirred at rt for 3 h. The reaction mixture was diluted with water (2-3 mL), added 2N HCl solution to pH 4, concentrated to small volume, filtered, purified by Gilson prepared HPLC (30-90% B in 20 min) to afford (S)-4-((4-((4"-(2-(((S)-3-carboxy-2-hydroxypropyl)amino)ethoxy)-2'-chloro-2-methyl-[1,1':3',1"-terphenyl]-3-yl)methoxy)-5-chloro-2-((5-cyanopyridin-3-yl)methoxy)benzyl)amino)-3-hydroxybutanoic acid. $^1H$ NMR (400 MHz, Methanol-$d_4$) δ 8.93 (m, 2H), 8.36 (m, 1H), 7.53-7.45 (m, 2H), 7.45-7.38 (m, 3H), 7.36 (m, 1H), 7.31-7.19 (m, 2H), 7.16 (m, 1H), 7.13-7.05 (m, 2H), 7.04 (s, 1H), 5.33 (m, 4H), 4.35 (m, 3H), 4.29-4.15 (m, 3H), 3.61-3.49 (m, 2H), 3.41-3.31 (m, 1H), 3.24-3.07 (m, 2H), 2.97 (m, 1H), 2.58 (d, 2H), 2.51 (m, 2H), 2.18 (s, 3H). LCMS-ESI$^+$ (m/z): $[M+H]^+$ calcd for $C_{44}H_{44}Cl_2N_4O_9$: 843.3; found: 843.2.

Example 342: (S)-2-((5-chloro-2-((5-cyanopyridin-3-yl)methoxy)-4-((2,2'-dimethyl-4"-((R)-pyrrolidin-3-yl)-[1,1':3',1"-terphenyl]-3-yl)methoxy)benzyl)amino)-3-hydroxy-2-methylpropanoic acid and(S)-2-((5-chloro-2-((5-cyanopyridin-3-yl)methoxy)-4-((2,2'-dimethyl-4"-((S)-pyrrolidin-3-yl)-[1,1':3',1"-terphenyl]-3-yl)methoxy)benzyl)amino)-3-hydroxy-2-methylpropanoic

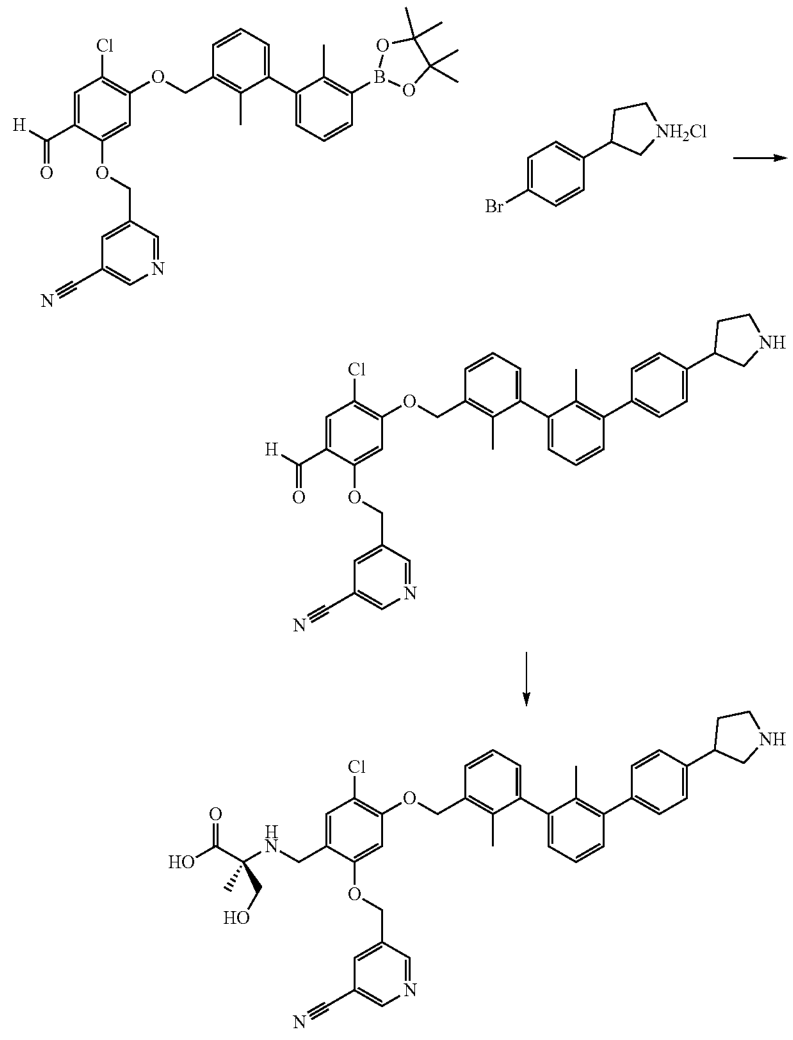

5-((4-chloro-5-((2,2'-dimethyl-3'-(4,4,5,5-tetramethyl-1,3,2-dioxaborolan-2-yl)-[1,1'-biphenyl]-3-yl)methoxy)-2-formylphenoxy)methyl)nicotinonitrile (60 mg, 0.099 mmol), 3-(4-bromophenyl)pyrrolidine hydrochloride (32 mg, 0.12 mmol), potassium carbonate (41 mg, 0.30 mmol) and tetrakis(triphenylphosphine)palladium (11 mg, 0.010 mmol) were combined in a reaction vessel. Dioxane (2.0 mL) and water (0.40 mL) were injected and the resulting suspension was sparged with argon (via a balloon filled with argon) for 10 minutes. The reaction mixture was stirred at 90° C. for 5 h. Analysis by tlc/LCMS indicated consumption of the boronate starting material and formation of the desired product. The reaction mixture was cooled to rt, and quenched by the addition of sat aq $NH_4Cl$ and EtOAc. The layers were separated and the aqueous layer was further extracted with EtOAc. The organic layers were combined, washed with brine, dried (over $Na_2SO_4$), filtered then concentrated in vacuo. The desired product, 5-((4-chloro-5-((2,2'-dimethyl-4"-(pyrrolidin-3-yl)-[1,1':3',1"-terphenyl]-3-yl)methoxy)-2-formylphenoxy)methyl)nicotinonitrile (62 mg, [M+1]=628.97) was carried forward with no further purification.

A solution of 5-((4-chloro-5-((2,2'-dimethyl-4"-(pyrrolidin-3-yl)-[1,1':3',1"-terphenyl]-3-yl)methoxy)-2-formylphenoxy)methyl)nicotinonitrile (25 mg, 0.040 mmol) was treated using general reductive amination procedure G. Purification by prep RP-HPLC (10-90% acetonitrile in water, 0.1% trifluoroacetic acid) furnished (S)-2-((5-chloro-2-((5-cyanopyridin-3-yl)methoxy)-4-((2,2'-dimethyl-4"-((R)-pyrrolidin-3-yl)-[1,1':3',1"-terphenyl]-3-yl)methoxy)benzyl)amino)-3-hydroxy-2-methylpropanoic acid and (S)-2-((5-chloro-2-((5-cyanopyridin-3-yl)methoxy)-4-((2,2'-dimethyl-4"-((S)-pyrrolidin-3-yl)-[1,1':3',1"-terphenyl]-3-yl)methoxy)benzyl)amino)-3-hydroxy-2-methylpropanoic as a mixture of epimers as the bis-TFA salts. LCMS-ESI$^+$ (m/z): $[M+H]^+$ calcd for $C_{43}H_{43}ClN_4O_5$: 731.30; found: 731.71. $^1H$ NMR (400 MHz, Methanol-$d_4$) δ 8.98 (d, J=2.1 Hz, 1H), 8.91 (d, J=2.0 Hz, 1H), 8.45-8.38 (m, 1H), 7.55 (s, 1H), 7.46 (d, J=7.5 Hz, 1H), 7.44-7.38 (m, 2H), 7.38-7.33 (m, 2H), 7.33-7.24 (m, 3H), 7.22-7.18 (m, 1H), 7.14 (d, J=7.6 Hz, 1H), 7.12-7.07 (m, 2H), 5.36 (s, 2H), 5.32 (s, 2H), 4.27 (s, 2H), 3.99 (d, J=12.1 Hz, 1H), 3.82-3.70 (m, 2H), 3.67-3.51 (m, 2H), 3.46-3.33 (m, 1H), 3.25 (t, J=11.0 Hz, 1H), 3.04 (s, 1H), 2.57-2.41 (m, 1H), 2.23-2.15 (m, 1H), 2.14 (s, 3H), 1.87 (s, 3H), 1.51 (s, 3H).

Example 343: (S)-2-((4-((3'-((R)-2-amino-2,3-dihydro-1H-inden-5-yl)-2,2'-dimethyl-[1,1'-biphenyl]-3-yl)methoxy)-5-chloro-2-((5-cyanopyridin-3-yl)methoxy)benzyl)amino)-3-hydroxy-2-methylpropanoic acid and(S)-2-((4-((3'-((S)-2-amino-2,3-dihydro-1H-inden-5-yl)-2,2'-dimethyl-[1,1'-biphenyl]-3-yl)methoxy)-5-chloro-2-((5-cyanopyridin-3-yl)methoxy)benzyl)amino)-3-hydroxy-2-methylpropanoic acid

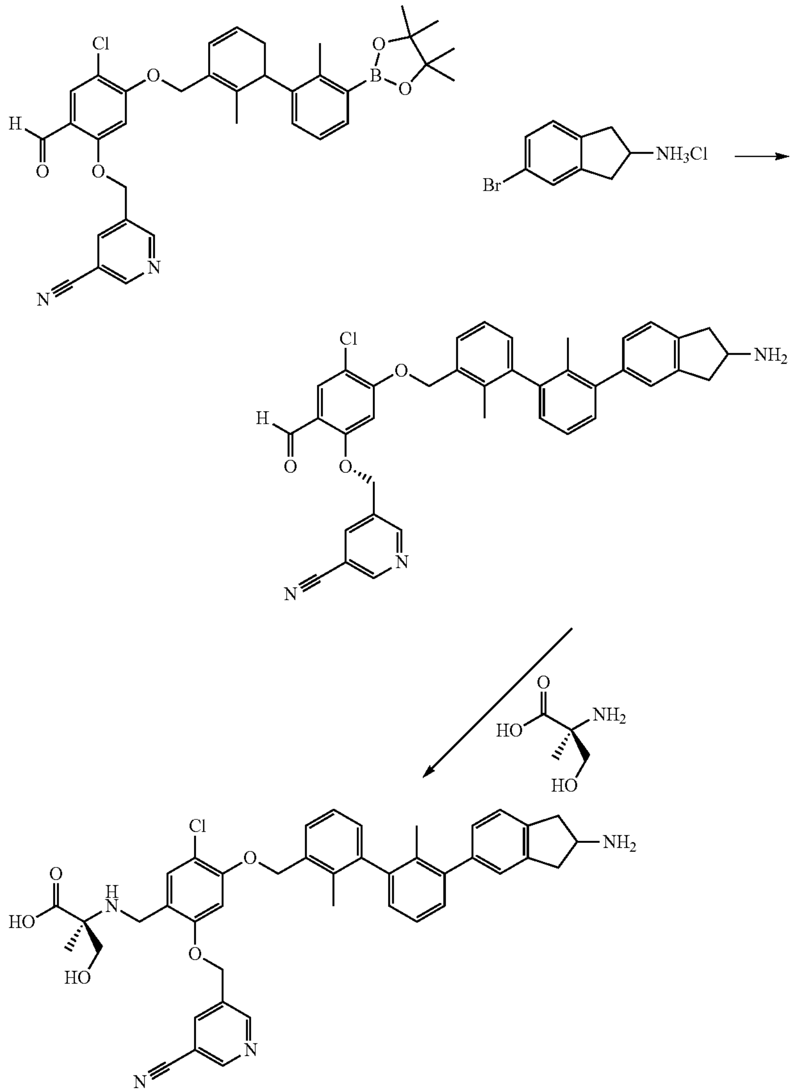

(S)-2-((4-((3'-((R)-2-amino-2,3-dihydro-1H-inden-5-yl)-2,2'-dimethyl-[1,1'-biphenyl]-3-yl)methoxy)-5-chloro-2-((5-cyanopyridin-3-yl)methoxy)benzyl)amino)-3-hydroxy-2-methylpropanoic acid and (S)-2-((4-((3'-((S)-2-amino-2,3-dihydro-1H-inden-5-yl)-2,2'-dimethyl-[1,1'-biphenyl]-3-yl)methoxy)-5-chloro-2-((5-cyanopyridin-3-yl)methoxy)benzyl)amino)-3-hydroxy-2-methylpropanoic acid were prepared as an epmieric mixture of bis-TFA salts by a sequence identical to the route used to prepare Example 342 except 5-bromo-2,3-dihydro-1H-inden-2-amine hydrochloride was used instead of 3-(4-bromophenyl)pyrrolidine hydrochloride, and the intermediate was purified by $SiO_2$ chromatography (0-10% $MeOH/CH_2Cl_2$) prior to reductive amination (via Procedure G). LCMS-ESI$^+$ (m/z): $[M+H]^+$ calcd for $C_{42}H_{41}ClN_4O_5$: 717.28; found: 717.78. $^1$H NMR (400 MHz, DMSO-d6) δ 9.06-8.96 (m, 2H), 8.87 (s, 2H), 8.48 (t, J=2.1 Hz, 1H), 8.03 (m, 2H), 7.57 (s, 1H), 7.50-7.44 (m, 1H), 7.37-7.24 (m, 4H), 7.16 (dt, J=9.9, 7.3 Hz, 4H), 7.07 (dd, J=7.4, 1.4 Hz, 1H), 5.76 (s, 1H), 5.38-5.26 (m, 4H), 4.23-3.98 (m, 3H), 3.79 (d, J=11.8 Hz, 1H), 3.70 (d, J=11.8 Hz, 1H), 2.96 (d, J=16.4 Hz, 2H), 2.08 (s, 3H), 1.84 (s, 3H), 1.33 (s, 3H).

Example 344: (S)-1-(5-chloro-2-((5-cyanopyridin-3-yl)methoxy)-4-((4"-(2-((2-hydroxyethyl)amino)ethoxy)-2,2'-dimethyl-[1,1':3',1"-terphenyl]-3-yl)methoxy)benzyl)piperidine-2-carboxylic acid

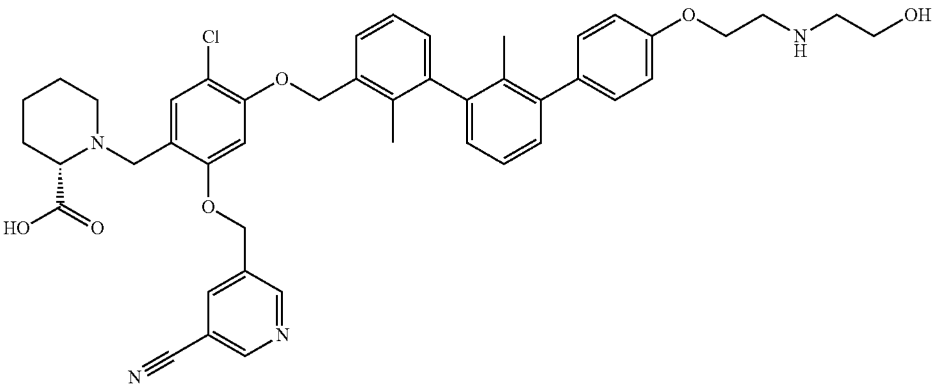 [SMILES: Cc1c(COc2cc(OCc3cncc(C#N)c3)c(CN3CCCC[C@H]3C(=O)O)cc2Cl)cccc1-c1cccc(-c2ccc(OCCNCCO)cc2)c1C]

The title compound was prepared according to general reductive amination procedure H with one modification—DMF was used as the only solvent. LCMS-ESI$^+$ (m/z): $[M+H]^+$ calcd for $C_{45}H_{47}ClN_4O_6$: 775.33; found: 775.90. $^1$H NMR (400 MHz, Methanol-d4) δ 8.94 (d, J=2.1 Hz, 1H), 8.92 (d, J=2.0 Hz, 1H), 8.38 (q, J=1.8 Hz, 1H), 7.57 (s, 1H), 7.46 (dd, J=7.8, 1.9 Hz, 1H), 7.32-7.24 (m, 4H), 7.21-7.12 (m, 2H), 7.11-7.05 (m, 4H), 5.35 (s, 2H), 5.32 (s, 2H), 4.51-4.40 (m, 1H), 4.35 (dd, J=6.8, 3.3 Hz, 3H), 3.98-3.76 (m, 3H), 3.53 (t, J=5.0 Hz, 2H), 3.39 (s, 1H), 3.28-3.21 (m, 2H), 3.08-2.88 (m, 1H), 2.35-2.17 (m, 1H), 2.13 (s, 3H), 1.90-1.49 (m, 9H).

Example 345: (R)-1-(5-chloro-2-((5-cyanopyridin-3-yl)methoxy)-4-((4"-(2-((2-hydroxyethyl)amino)ethoxy)-2,2'-dimethyl-[1,1':3',1"-terphenyl]-3-yl)methoxy)benzyl)pyrrolidine-3-carboxylic acid

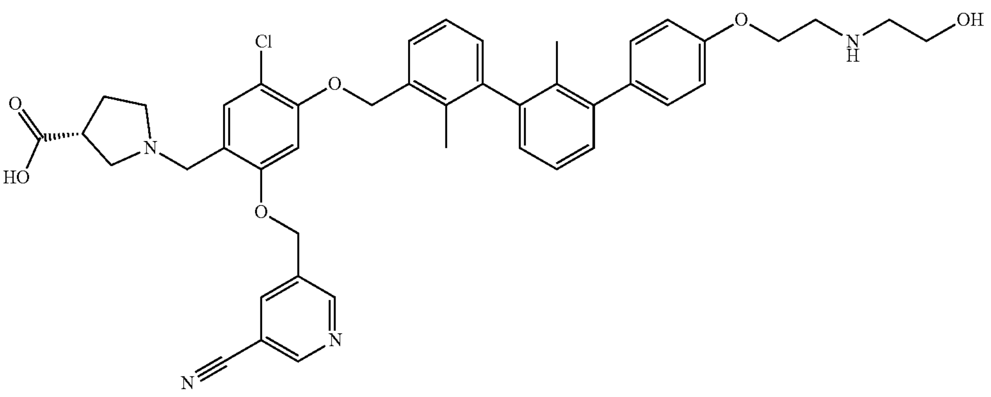 [SMILES: Cc1c(COc2cc(OCc3cncc(C#N)c3)c(CN3CC[C@@H](C(=O)O)C3)cc2Cl)cccc1-c1cccc(-c2ccc(OCCNCCO)cc2)c1C]

The title compound was prepared according to general reductive amination procedure G. LCMS-ESI+ (m/z): $[M+H]^+$ calcd for $C_{40}H_{45}ClN_4O_6$: 761.31; found: 761.68. $^1H$ NMR (400 MHz, Methanol-d4) δ 8.96 (d, J=2.1 Hz, 1H), 8.93 (d, J=2.0 Hz, 1H), 8.37 (t, J=2.1 Hz, 1H), 7.56 (s, 1H), 7.46 (dd, J=7.5, 1.3 Hz, 1H), 7.34-7.23 (m, 4H), 7.17 (ddd, J=15.3, 7.7, 1.4 Hz, 2H), 7.12-7.00 (m, 4H), 5.39 (s, 2H), 5.32 (s, 2H), 4.40 (s, 2H), 4.38-4.30 (m, 2H), 3.94-3.81 (m, 2H), 3.80-3.20 (m, 9H), 2.55-2.25 (m, 2H), 2.14 (s, 3H), 1.87 (s, 3H).

Example 346: (S)-4-(((6-((3'-((4-((((S)-3-carboxy-2-hydroxypropyl)amino)methyl)-2-chloro-5-((5-cyanopyridin-3-yl)methoxy)phenoxy)methyl)-2,2'-dimethyl-[1,1'-biphenyl]-3-yl)carbamoyl)pyridin-3-yl)methyl)amino)-3-hydroxybutanoic acid Step 1: To a solution of 5-(methoxycarbonyl)pyridine-2-carboxylic acid (500 mg, 2.76 mmol), O-(7-azabenzotriazol-1-yl)-N,N,N',N'-tetramethyluronium hexafluorophosphate (HATU reagent, 1.36 g, 3.59 mmol) in DMF (6.0 mL) was added N,N-diisopropyethylamine (1.44 mL, 8.28 mmol). After 10 min, 2-amino-6-bromotoluene (0.410 mL, 3.31 mmol) was added to the reaction mixture. The reaction mixture was maintained at rt overnight, and then quenched by the addition of sat aq $NH_4Cl$ and EtOAc. The layers were separated and the aqueous layer was further extracted with EtOAc. The organic layers were combined, washed with 10% aq LiCl, dried (over $Na_2SO_4$), filtered then concentrated in vacuo. The crude mixture was purified by $SiO_2$ chromatography (eluting with 0-100% EtOAc/hex) to afford methyl 6-((3-bromo-2-methylphenyl)carbamoyl)nicotinate ([M+1]=319.19, 351.20).

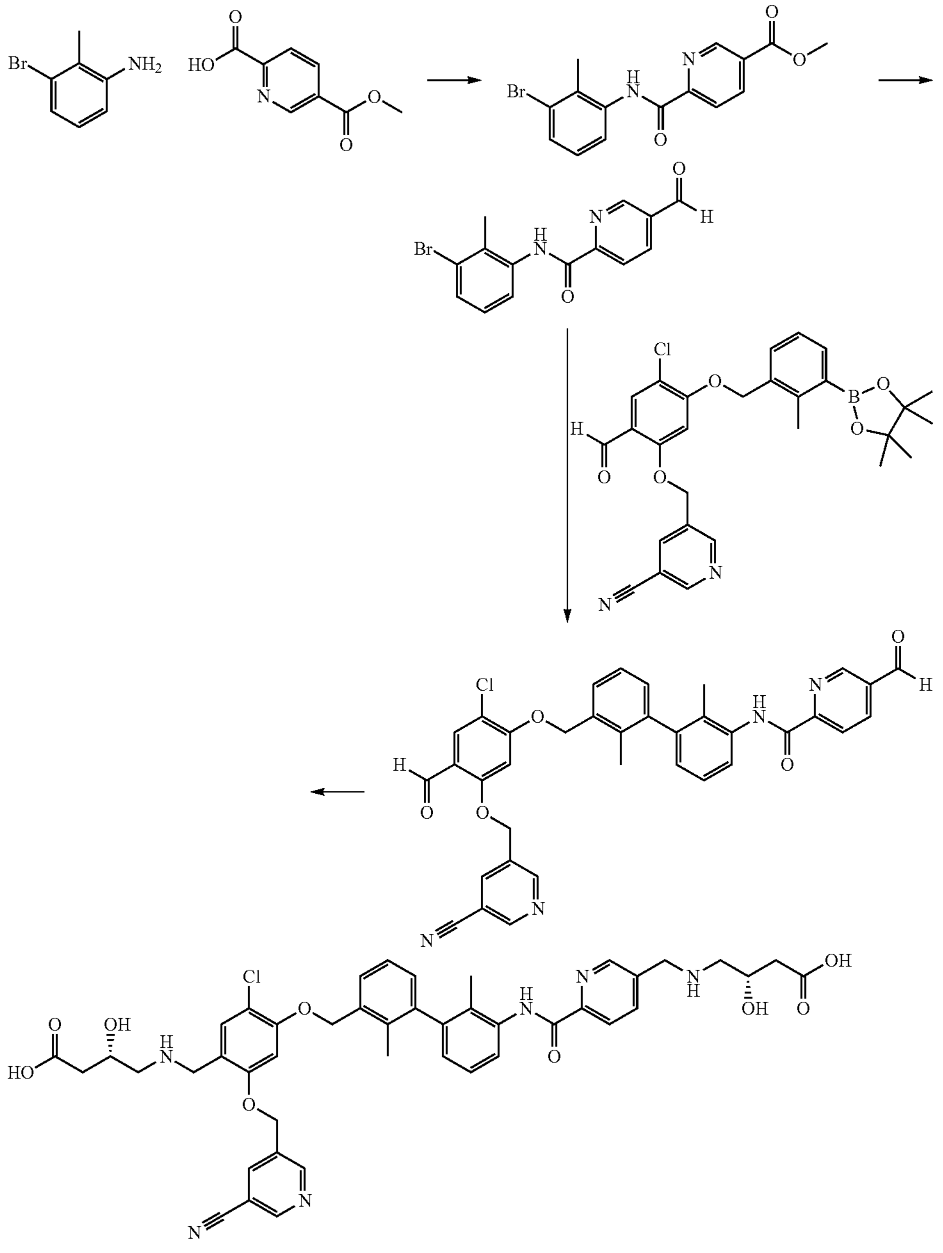

Step 2: To a solution of methyl 6-((3-bromo-2-methylphenyl)carbamoyl)nicotinate (450 mg, 1.29 mmol) in thf (13 mL) was added 2 M Lithium borohydride (1.61 mL) then methanol (0.130 mL, 3.22 mmol, note: evolution of gas during addition, so adequate ventilation of the reaction vessel is required). Analysis by tlc indicated consumption of the starting material. The reaction mixture was quenched by the addition of sat aq $NaHCO_3$ and EtOAc, and the mixture was stirred for 10 min. The layers were separated and the aqueous layer was further extracted with EtOAc. The organic layers were combined, washed with brine, dried (over $Na_2SO_4$), filtered then concentrated in vacuo. The resultant alcohol intermediate was dissolved in dichloromethane (26 mL), cooled in an ice-water bath then Dess-Martin periodinane (820 mg, 1.93 mmol) was added to the reaction mixture. The reaction mixture was stirred in the bath for 3 h (allowing the mixture to slowly to warm to rt). Analysis by tlc/LCMS indicated consumption of the alcohol intermediate and formation of the desired product. The reaction mixture was quenched by the addition of 10% aq sodium thiosulfate and EtOAc and the mixture was stirred for 10 min. The layers were separated and the aqueous layer was further extracted with EtOAc. The organic layers were combined, washed with brine, dried (over $Na_2SO_4$), filtered then concentrated in vacuo. The crude mixture was purified by $SiO_2$ chromatography (0-100% EtOAc/hex) to afford N-(3-bromo-2-methylphenyl)-5-formylpicolinamide ([M+1]=319.28, 321.24).

Step 3: N-(3-Bromo-2-methylphenyl)-5-formylpicolinamide (48 mg, 0.15 mmol), 5-[[4-chloro-2-formyl-5-[[2-methyl-3-(4,4,5,5-tetramethyl-1,3,2-dioxaborolan-2-yl)phenyl]methoxy]phenoxy]methyl]pyridine-3-carbonitrile (60 mg, 0.12 mmol), potassium carbonate (56 mg, 0.41 mmol) and XPhos Palladacycle precatalyst (18 mg, 24 umol) were combined in a reaction vessel. Dioxane (1.0 mL) and water (0.20 mL) were injected and the resulting suspension was sparged with argon (via a balloon filled with argon) for 10 minutes. The reaction mixture was stirred at 95° C. for 10 h. Analysis by tlc/LCMS indicated consumption of the boronate starting material and formation of the desired product. The reaction mixture was cooled to rt, and quenched by the addition of sat aq $NH_4Cl$ and EtOAc. The layers were separated and the aqueous layer was further extracted with EtOAc. The organic layers were combined, washed with brine, dried (over $Na_2SO_4$), filtered then concentrated in vacuo. The crude mixture was purified by $SiO_2$ chromatography (eluting with 0-100% EtOAc/hex) to afford N-(3'-((2-chloro-5-((5-cyanopyridin-3-yl)methoxy)-4-formylphenoxy)methyl)-2,2'-dimethyl-[1,1'-biphenyl]-3-yl)-5-formylpicolinamide ([M+1]=631.41).

Step 4: (S)-4-(((6-((3'-((4-((((S)-3-carboxy-2-hydroxypropyl)amino)methyl)-2-chloro-5-((5-cyanopyridin-3-yl)methoxy)phenoxy)methyl)-2,2'-dimethyl-[1,1'-biphenyl]-3-yl)carbamoyl)pyridin-3-yl)methyl)amino)-3-hydroxybutanoic acid (30 mg, 46%) was prepared as the bis-TFA salt by reductive amination (general procedure G) of N-(3'-((2-chloro-5-((5-cyanopyridin-3-yl)methoxy)-4-formylphenoxy)methyl)-2,2'-dimethyl-[1,1'-biphenyl]-3-yl)-5-formylpicolinamide (39 mg, 0.062 mmol) and (S)-4-amino-3-hydroxybutanoic acid. LCMS-ESI$^+$ (m/z): [M+H]$^+$ calcd for $C_{44}H_{45}ClN_6O_9$: 837.30; found: 837.49. $^1$H NMR (400 MHz, Methanol-d4) δ 1H NMR (400 MHz, Methanol-d4) δ 8.96 (d, J=2.1 Hz, 1H), 8.93 (d, J=2.0 Hz, 1H), 8.82 (dd, J=2.2, 0.9 Hz, 1H), 8.38 (t, J=2.1 Hz, 1H), 8.31 (dd, J=8.1, 0.8 Hz, 1H), 8.18 (dd, J=8.1, 2.2 Hz, 1H), 7.85 (dd, J=8.0, 1.3 Hz, 1H), 7.51 (s, 1H), 7.48 (dd, J=7.7, 1.4 Hz, 1H), 7.33 (t, J=7.8 Hz, 1H), 7.28 (t, J=7.6 Hz, 1H), 7.15 (dd, J=7.6, 1.4 Hz, 1H), 7.09 (s, 1H), 7.04 (dd, J=7.6, 1.3 Hz, 1H), 5.38 (s, 2H), 5.32 (s, 2H), 4.43 (s, 2H), 4.33 (dtd, J=9.4, 6.3, 3.0 Hz, 1H), 4.23 (d, J=6.5 Hz, 3H), 3.20 (dd, J=12.8, 3.1 Hz, 1H), 3.11 (dd, J=12.6, 9.9 Hz, 1H), 3.05-2.92 (m, 1H), 2.57 (d, J=6.3 Hz, 2H), 2.51 (dd, J=6.3, 0.9 Hz, 2H), 2.13 (s, 3H), 2.04 (s, 3H).

Example 347: (S)-4-((4-((3'-(1-(2-(((S)-3-carboxy-2-hydroxypropyl)amino)ethyl)-3-methyl-1H-indazol-5-yl)-2,2'-dimethyl-[1,1'-biphenyl]-3-yl)methoxy)-5-chloro-2-((5-cyanopyridin-3-yl)methoxy)benzyl)amino)-3-hydroxybutanoic acid

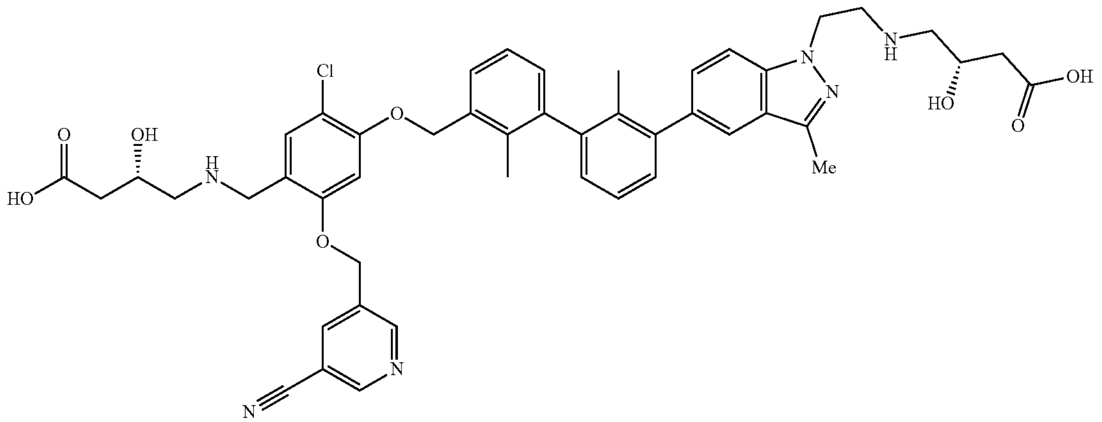 [SMILES: Cc1c(COc2cc(OCc3cncc(C#N)c3)c(CNC[C@@H](O)CC(=O)O)cc2Cl)cccc1-c1cccc(-c2ccc3c(c2)c(C)nn3CCNC[C@@H](O)CC(=O)O)c1C]

(S)-4-((4-((3'-(1-(2-(((S)-3-carboxy-2-hydroxypropyl)amino)ethyl)-3-methyl-1H-indazol-5-yl)-2,2'-dimethyl-[1,1'-biphenyl]-3-yl)methoxy)-5-chloro-2-((5-cyanopyridin-3-yl)methoxy)benzyl)amino)-3-hydroxybutanoic acid was prepared as the bis-TFA salt by a sequence identical to the route used to prepare Example 209 starting with 5-bromo-3-methyl-1H-indazole instead of 5-bromo-1H-indazole. LCMS-ESI$^+$ (m/z): [M+H]$^+$ calcd for $C_{47}H_{50}ClN_6O$: 861.34; found: 861.37. $^1$H NMR (400 MHz, Methanol-d4) δ 8.95 (d, J=2.1 Hz, 1H), 8.92 (d, J=2.0 Hz, 1H), 8.37 (t, J=2.1 Hz, 1H), 7.75-7.63 (m, 1H), 7.64-7.55 (m, 1H), 7.51 (s, 1H), 7.49-7.37 (m, 2H), 7.37-7.21 (m, 3H), 7.21-7.15 (m, 1H), 7.11 (dd, J=7.4, 1.6 Hz, 1H), 7.08 (s, 1H), 5.37 (s, 2H), 5.32 (s, 2H), 4.78-4.59 (m, 2H), 4.31 (dtd, J=9.6, 6.5, 3.2 Hz, 1H), 4.26-4.16 (m, 3H), 3.64 (tq, J=12.9, 6.6, 5.8 Hz, 2H), 3.38-3.31 (m, 1H), 3.25-3.07 (m, 2H), 2.97 (dd, J=12.8, 9.8 Hz, 1H), 2.58 (s, 3H), 2.56 (d, J=6.3 Hz, 2H), 2.51 (dd, J=6.3, 1.1 Hz, 2H), 2.16 (s, 3H), 1.88 (s, 3H).
Example 348: (S)-4-((4-((3'-(3-(2-(((S)-3-carboxy-2-hydroxypropyl)amino)ethyl)benzofuran-6-yl)-2,2'-dimethyl-[1,1'-biphenyl]-3-yl)methoxy)-5-chloro-2-((5-cyanopyridin-3-yl)methoxy)benzyl)amino)-3-hydroxybutanoic acid
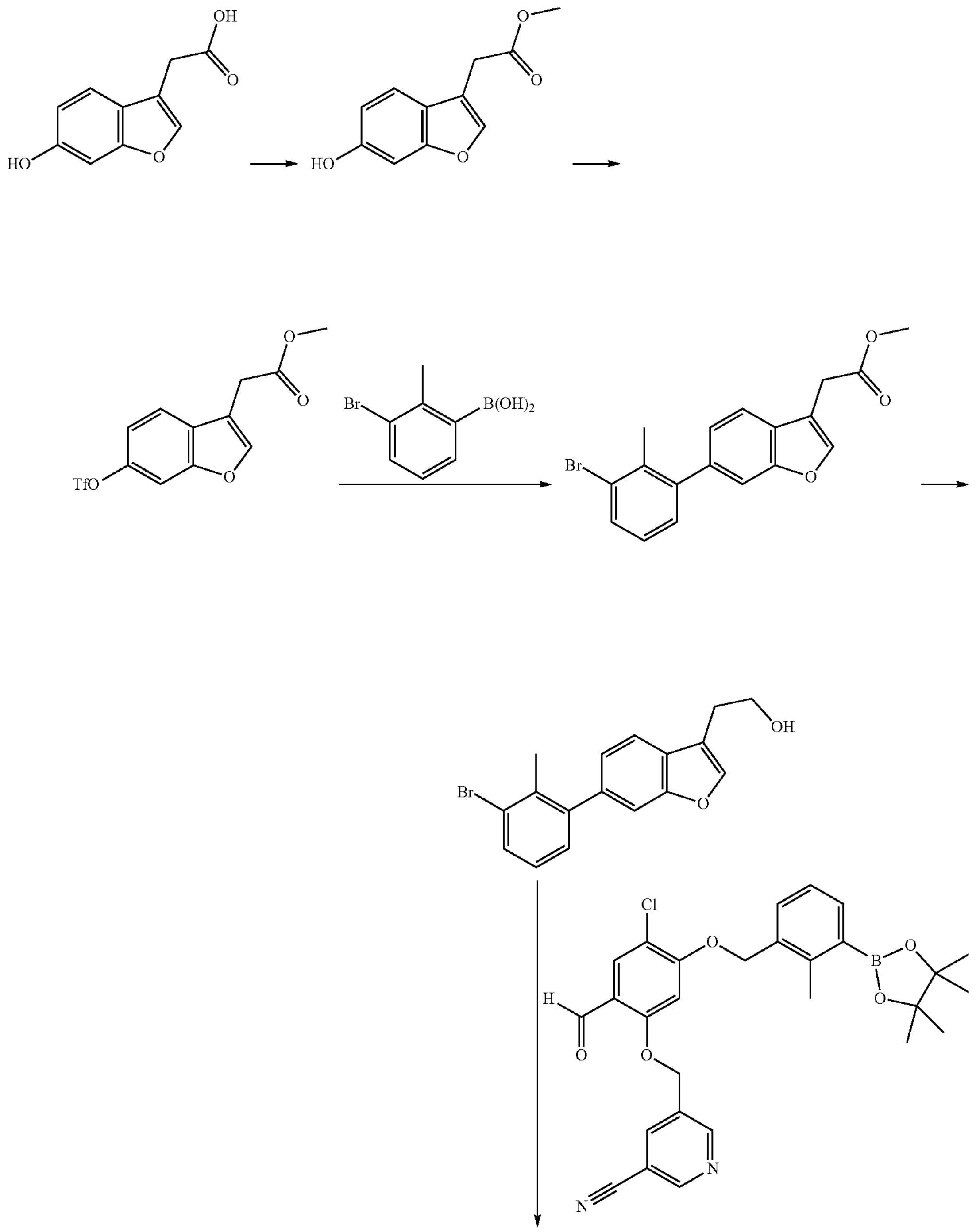

-continued

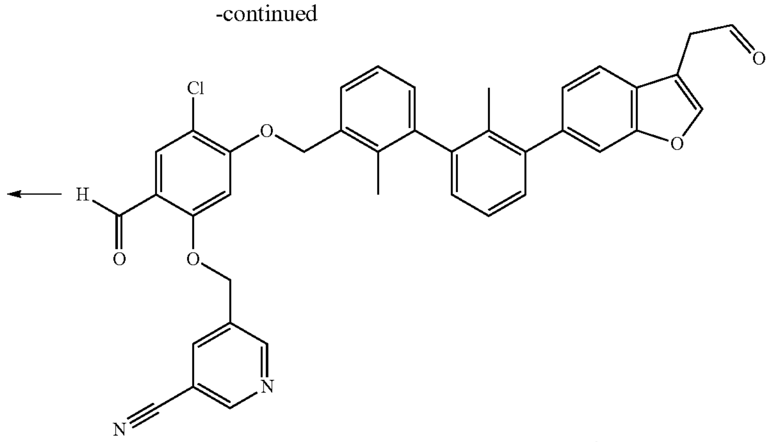

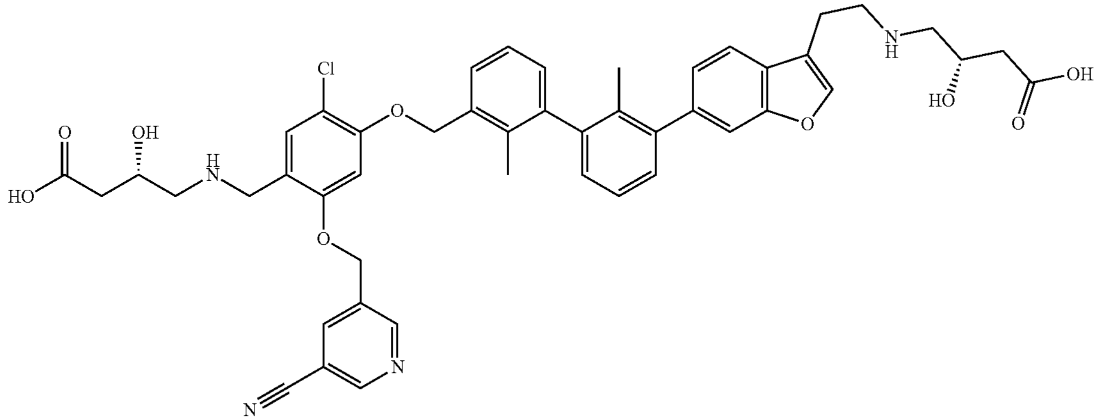

Step 1: To a solution of 2-(6-hydroxy-1-benzofuran-3-yl) acetic acid (2.00 g, 10.4 mmol) in methanol (11.0 mL) was added conc sulfuric acid (1.2 mL). The reaction mixture was stirred at 60° C. overnight. Analysis by tlc/LCMS indicated consumption of the starting material and formation of the amine product ([M+1]=207.09). The reaction mixture was cooled to rt, then carefully quenched by the addition of 1N NaOH (to pH ~6-7) and extracted with EtOAc (3×). The organic layers were combined, washed with brine, dried (over $Na_2SO_4$), filtered then concentrated in vacuo to afford methyl 2-(6-hydroxybenzofuran-3-yl)acetate (2.15 g, quant), which was immediately processed in the subsequent step.

Step 2: To a solution of methyl 2-(6-hydroxybenzofuran-3-yl)acetate (2.15 g, 10.4 mmol) and N,N-diisopropylethylamine (4.53 mL, 26.0 mmol) in dichloromethane (25 mL) cooled in an ice-water bath was slowly added trifluoromethanesulfonic anhydride (2.01 mL, 12.0 mmol) as a steady stream down the side of the reaction vessel. The reaction mixture was maintained in the bath for 1h, and then quenched by the addition of sat aq $NaHCO_3$ and EtOAc. The layers were separated and the aqueous layer was further extracted with EtOAc. The organic layers were combined, washed with brine, dried (over $Na_2SO_4$), filtered then concentrated in vacuo. The crude mixture was purified by $SiO_2$ chromatography (eluting with 0-50% EtOAc/hex) to afford the desired product methyl 2-(6-(((trifluoromethyl)sulfonyl) oxy)benzofuran-3-yl)acetate ([M+1]=339.50).

Step 3: Methyl 2-(6-(((trifluoromethyl)sulfonyl)oxy)benzofuran-3-yl)acetate (500 mg, 1.48 mmol), 2 (3-Bromo-2-methylphenyl)boronic acid (3.18 g, 1.48 mmol), potassium carbonate (613 mg, 4.44 mmol) and tetrakis(triphenylphosphine)palladium (128 mg, 0.111 mmol) were combined in a reaction vessel. Dioxane (10.0 mL) and water (2.00 mL) were added and the resulting suspension was sparged with argon (via a balloon filled with argon) for 10 minutes. The reaction mixture was stirred at 90° C. for 5 h. Analysis by tlc/LCMS indicated consumption of the starting materials. The reaction mixture was cooled to rt, and quenched by the addition of sat aq $NH_4Cl$ and EtOAc. The layers were separated and the aqueous layer was further extracted with EtOAc. The organic layers were combined, washed with brine, dried (over $Na_2SO_4$), filtered then concentrated in vacuo. The crude mixture was purified by $SiO_2$ chromatography (0-100% EtOAc/hex) to afford methyl 2-(6-(3-bromo-2-methylphenyl)benzofuran-3-yl)acetate.

Step 4: To a solution of methyl 2-(6-(3-bromo-2-methylphenyl)benzofuran-3-yl)acetate (350 mg, 0.974 mmol) in thf (10.0 mL) and dichloromethane (10.0 mL) was added 2 M Lithium borohydride (1.46 mL) then methanol (0.118 mL, 2.92 mmol, note: evolution of gas during addition, so adequate ventilation of the reaction vessel is required). Analysis by tlc indicated consumption of the starting material. The reaction mixture was quenched by the addition of sat aq $NaHCO_3$ and EtOAc, and the mixture was stirred for 10 min. The layers were separated and the aqueous layer was further extracted with EtOAc. The organic layers were combined, washed with brine, dried (over $Na_2SO_4$), filtered then concentrated in vacuo to afford the desired product 2-(6-(3-bromo-2-methylphenyl)benzofuran-3-yl)ethanol, which was processed in the subsequent step immediately.

Step 5: 2-(6-(3-bromo-2-methylphenyl)benzofuran-3-yl) ethanol (58 mg, 0.17 mmol), 5-[[4-chloro-2-formyl-5-[[2-methyl-3-(4,4,5,5-tetramethyl-1,3,2-dioxaborolan-2-yl)phenyl]methoxy]phenoxy]methyl]pyridine-3-carbonitrile (60 mg, 0.12 mmol), potassium carbonate (56 mg, 0.41 mmol) and tetrakis(triphenylphosphine)palladium (21 mg, 0.017 mmol) were combined in a reaction vessel. Dioxane (0.80 mL) and water (0.20 mL) were added and the resulting suspension was sparged with argon (via a balloon filled with argon) for 10 minutes. The reaction mixture was stirred at 90° C. for 5 h. Analysis by tlc/LCMS indicated consumption of the starting materials. The reaction mixture was cooled to rt, and quenched by the addition of sat aq $NH_4Cl$ and EtOAc. The layers were separated and the aqueous layer was further extracted with EtOAc. The organic layers were combined, washed with brine, dried (over $Na_2SO_4$), filtered then concentrated in vacuo. The crude mixture (110 mg crude, [M+1]=643.35) was dissolved in dichloromethane (2.0 mL) and cooled in an ice-water bath. Dess-Martin periodinane (59 mg, 0.14 mmol) was added to the reaction mixture, and the mixture was stirred overnight with warming to rt. Analysis by tlc/LCMS indicated consumption of the starting material. The reaction mixture was quenched by the addition of 10% aq sodium thiosulfate and EtOAc and the mixture was stirred for 10 min. The layers were separated and the aqueous layer was further extracted with EtOAc. The organic layers were combined, washed with brine, dried (over $Na_2SO_4$), filtered then concentrated in vacuo. The crude mixture was purified by $SiO_2$ chromatography (0-100% EtOAc/hex) to afford 5-((4-chloro-5-((2,2'-dimethyl-3'-(3-(2-oxoethyl)benzofuran-6-yl)-[1,1'-biphenyl]-3-yl)methoxy)-2-formylphenoxy)methyl)nicotinonitrile ([M+1]=641.39).

Step 6: (S)-4-((4-((3'-(3-(2-(((S)-3-carboxy-2-hydroxypropyl)amino)ethyl)benzofuran-6-yl)-2,2'-dimethyl-[1,1'-biphenyl]-3-yl)methoxy)-5-chloro-2-((5-cyanopyridin-3-yl)methoxy)benzyl)amino)-3-hydroxybutanoic acid was prepared as the bis-TFA salt by reductive amination (general procedure G) of 5-((4-chloro-5-((2,2'-dimethyl-3'-(3-(2-oxoethyl)benzofuran-6-yl)-[1,1'-biphenyl]-3-yl)methoxy)-2-formylphenoxy)methyl)nicotinonitrile and (S)-4-amino-3-hydroxybutanoic acid. LCMS-ESI$^+$ (m/z): $[M+H]^+$ calcd for $C_{47}H_{47}ClN_4O_9$: 847.31; found: 847.37. $^1$H NMR (400 MHz, Methanol-d4) δ 8.95 (d, J=2.1 Hz, 1H), 8.93 (d, J=1.9 Hz, 1H), 8.42-8.31 (m, 1H), 7.76 (s, 1H), 7.71 (d, J=8.0 Hz, 1H), 7.51 (s, 1H), 7.49-7.42 (m, 2H), 7.36-7.23 (m, 4H), 7.21-7.14 (m, 1H), 7.11 (d, J=7.4 Hz, 1H), 7.08 (s, 1H), 5.37 (s, 2H), 5.32 (s, 2H), 4.41-4.22 (m, 1H), 4.22 (d, J=12.9 Hz, 3H), 3.51-3.38 (m, 3H), 3.24-3.05 (m, 6H), 3.03-2.93 (m, 1H), 2.57 (d, J=6.3 Hz, 2H), 2.51 (dd, J=6.3, 1.2 Hz, 2H), 2.16 (s, 3H), 1.90 (s, 3H).

Example 349: (S)-4-((4-((4"-((2-(((S)-3-carboxy-2-hydroxypropyl)amino)ethyl)carbamoyl)-2,2'-dimethyl-[1,1':3',1"-terphenyl]-3-yl)methoxy)-5-chloro-2-((5-cyanopyridin-3-yl)methoxy)benzyl)amino)-3-hydroxybutanoic acid

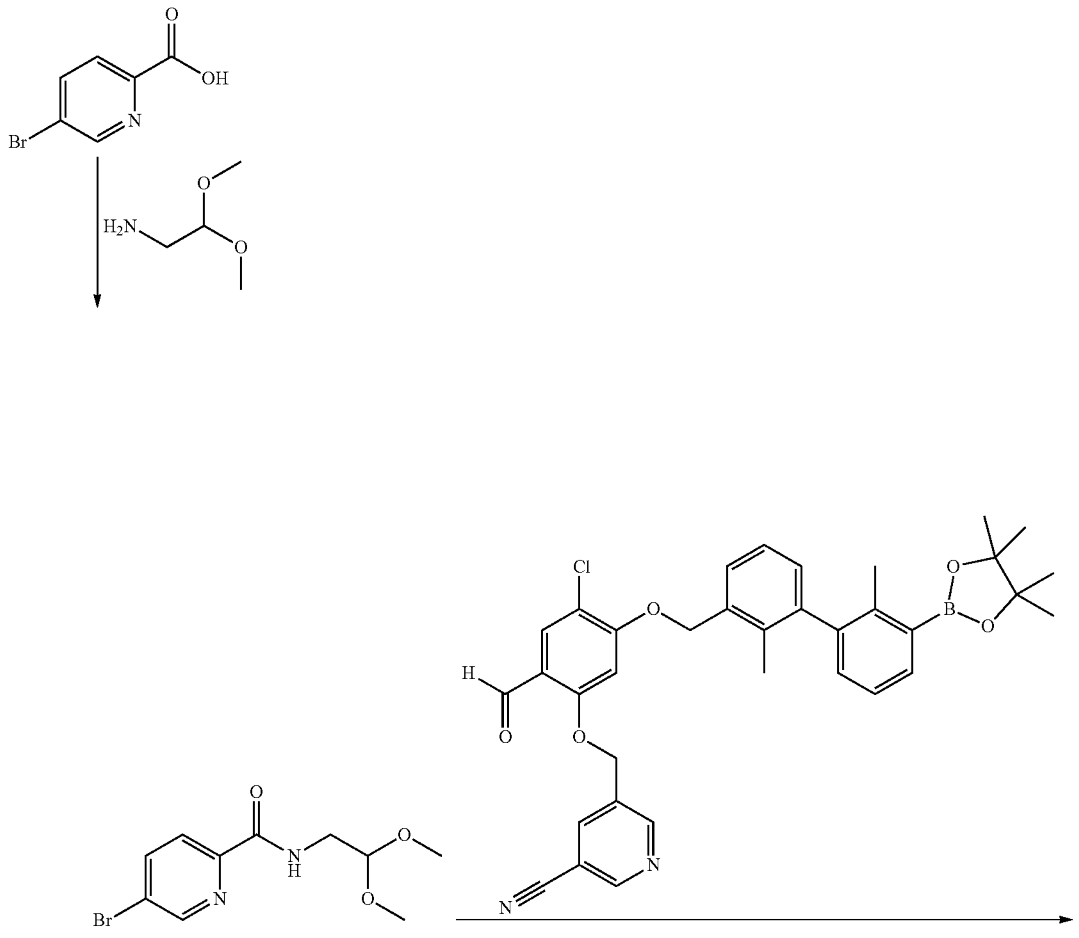

-continued

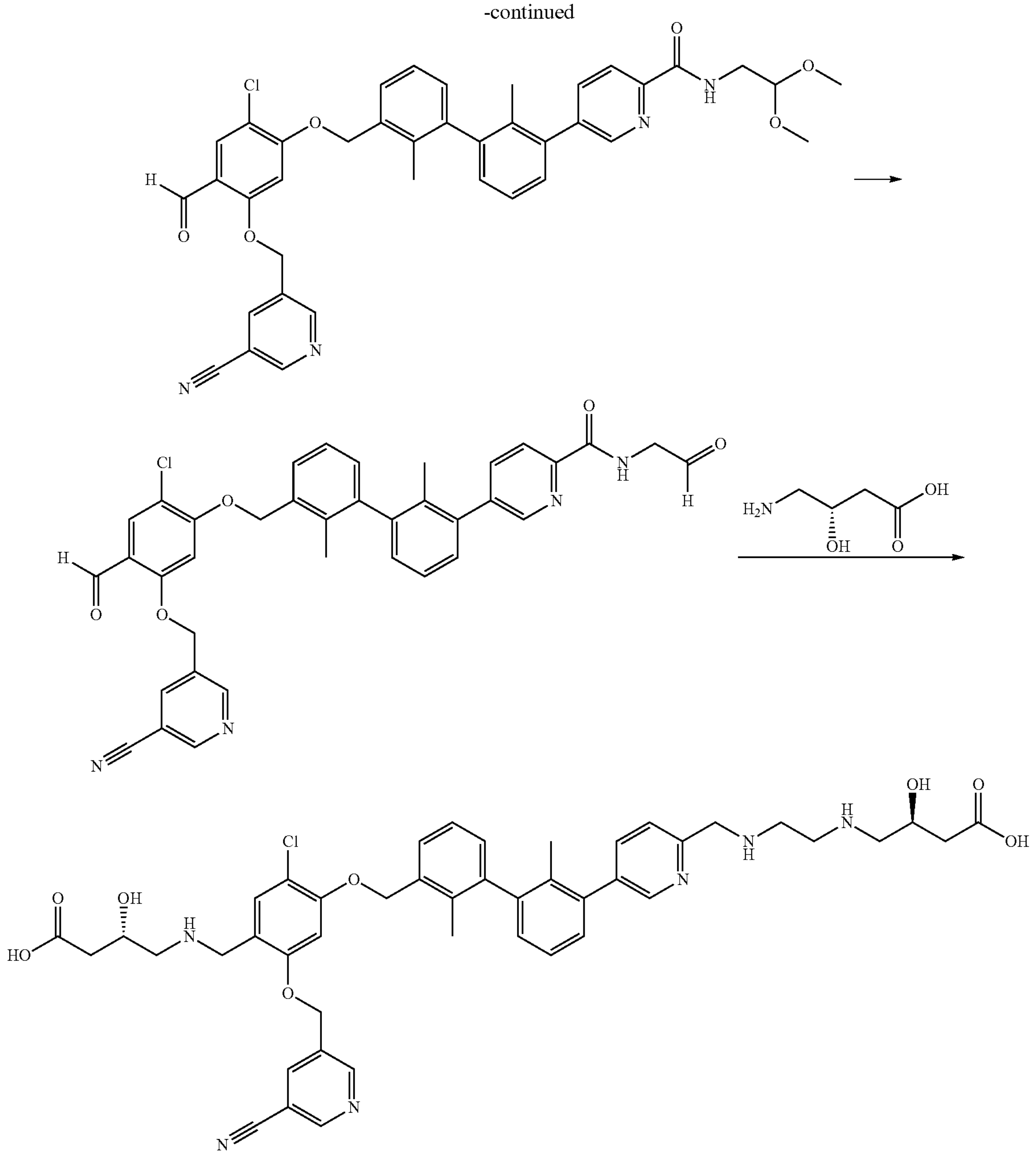

Step 1: To a solution of 5-Bromo-pyridine-2-carboxylic acid (1.00 g, 4.95 mmol), 0-(7-azabenzotriazol-1-yl)-N,N, N',N'-tetramethyluronium hexafluorophosphate (HATU reagent, 2.35 g, 6.19 mmol) and N,N-diisopropyethylamine (1.73 mL, 9.90 mmol) in DMF (10.0 mL) was added 2,2-dimethoxyethylamine (0.810 mL, 7.43 mmol). The reaction mixture was maintained at rt overnight, and then quenched by the addition of sat aq $NH_4Cl$ and EtOAc. The layers were separated and the aqueous layer was further extracted with EtOAc. The organic layers were combined, washed with 10% aq LiCl, dried (over $Na_2SO_4$), filtered then concentrated in vacuo. The crude mixture was purified by $SiO_2$ chromatography (eluting with 0-100% EtOAc/hex) to afford 5-bromo-N-(2,2-dimethoxyethyl)picolinamide.

Step 2: 5-((4-chloro-5-((2,2'-dimethyl-3'-(4,4,5,5-tetramethyl-1,3,2-dioxaborolan-2-yl)-[1,1'-biphenyl]-3-yl)methoxy)-2-formylphenoxy)methyl)nicotinonitrile (100 mg, 0.16 mmol), 4-bromo-N-(2,2-dimethoxyethyl)benzamide (57 mg, 0.20 mmol), potassium carbonate (68 mg, 0.49 mmol) and tetrakis(triphenylphosphine)palladium (9.5 mg, 8.0 umol) were combined in a reaction vessel. Dioxane (2.0 mL) and water (0.40 mL) were injected and the resulting suspension was sparged with argon (via a balloon filled with argon) for 10 minutes. The reaction mixture was stirred at 90° C. for 3 h. Analysis by tlc/LCMS indicated consumption of the boronate starting material and formation of the desired product. The reaction mixture was cooled to rt, and quenched by the addition of sat aq $NH_4Cl$ and EtOAc. The layers were separated and the aqueous layer was further extracted with EtOAc. The organic layers were combined, washed with brine, dried (over $Na_2SO_4$), filtered then concentrated in vacuo. The crude mixture was purified by $SiO_2$ chromatography (eluting with 0-100% EtOAc/hex) to afford, 5-(3'-((2-chloro-5-((5-cyanopyridin-3-yl)methoxy)-4-formylphenoxy)methyl)-2,2'-dimethyl-[1,1'-biphenyl]-3-yl)-N-(2,2-dimethoxyethyl)picolinamide ([M+1]=691.22).

Step 3: To a solution of 5-(3'-((2-chloro-5-((5-cyanopyridin-3-yl)methoxy)-4-formylphenoxy)methyl)-2,2'-dimethyl-[1,1'-biphenyl]-3-yl)-N-(2,2-dimethoxyethyl)picolinamide (60 mg, 0.087 mmol) in THF (1.0 mL) was added (0.50 mL) of 4N HCl then 20 drops of conc. HCl. The mixture was stirred at rt overnight. Analysis by LCMS indicated formation of the desired product. The reaction mixture was poured into a mixture of brine and EtOAc. The layers were separated and the aqueous layer was further extracted with EtOAc. The organic layers were combined, washed with brine, dried (over $Na_2SO_4$), filtered then concentrated in vacuo. 5-(3'-((2-Chloro-5-((5-cyanopyridin-3-yl)methoxy)-4-formylphenoxy)methyl)-2,2'-dimethyl-[1,1'-biphenyl]-3-yl)-N-(2-oxoethyl)picolinamide ([M+1]=645.42) was processed in the next step immediately.

Step 4: ((S)-4-((4-((4''-((2-(((S)-3-carboxy-2-hydroxypropyl)amino)ethyl)carbamoyl)-2,2'-dimethyl-[1,1':3',1''-terphenyl]-3-yl)methoxy)-5-chloro-2-((5-cyanopyridin-3-yl)methoxy)benzyl)amino)-3-hydroxybutanoic acid (13 mg, 16%) was prepared as the bis-TFA salt by reductive amination (general procedure G) of 5-(3'-((2-Chloro-5-((5-cyanopyridin-3-yl)methoxy)-4-formylphenoxy)methyl)-2,2'-dimethyl-[1,1'-biphenyl]-3-yl)-N-(2-oxoethyl)picolinamide and (S)-4-amino-3-hydroxybutanoic acid. LCMS-ESI$^+$ (m/z): $[M+H]^+$ calcd for $C_{45}H_{48}ClN_6O_9$: 851.32; found: 851.41. $^1$H NMR (400 MHz, Methanol-d4) δ 8.96 (d, J=2.1 Hz, 1H), 8.93 (d, J=2.0 Hz, 1H), 8.66 (dd, J=2.3, 0.9 Hz, 1H), 8.38 (d, J=2.2 Hz, 1H), 8.20 (d, J=8.0 Hz, 1H), 7.99 (dd, J=8.0, 2.2 Hz, 1H), 7.51 (s, 1H), 7.48 (d, J=7.6 Hz, 1H), 7.39 (t, J=7.5 Hz, 1H), 7.28 (dd, J=7.6, 4.2 Hz, 2H), 7.24-7.17 (m, 1H), 7.20-7.13 (m, 1H), 7.08 (s, 1H), 5.38 (s, 2H), 5.31 (s, 2H), 4.39-4.13 (m, 4H), 3.79 (t, J=5.9 Hz, 2H), 3.20 (dd, J=12.7, 3.1 Hz, 1H), 3.10 (dd, J=12.5, 9.7 Hz, 1H), 3.03-2.91 (m, 1H), 2.56 (d, J=6.3 Hz, 2H), 2.53-2.48 (m, 2H), 2.15 (s, 3H), 1.91 (s, 3H).

Example 350: (S)-4-((4-((3'-(5-((2-(((S)-3-carboxy-2-hydroxypropyl)amino)ethoxy)methyl)thiazol-2-yl)-2,2'-dimethyl-[1,1'-biphenyl]-3-yl)methoxy)-5-chloro-2-((5-cyanopyridin-3-yl)methoxy)benzyl)amino)-3-hydroxybutanoic acid

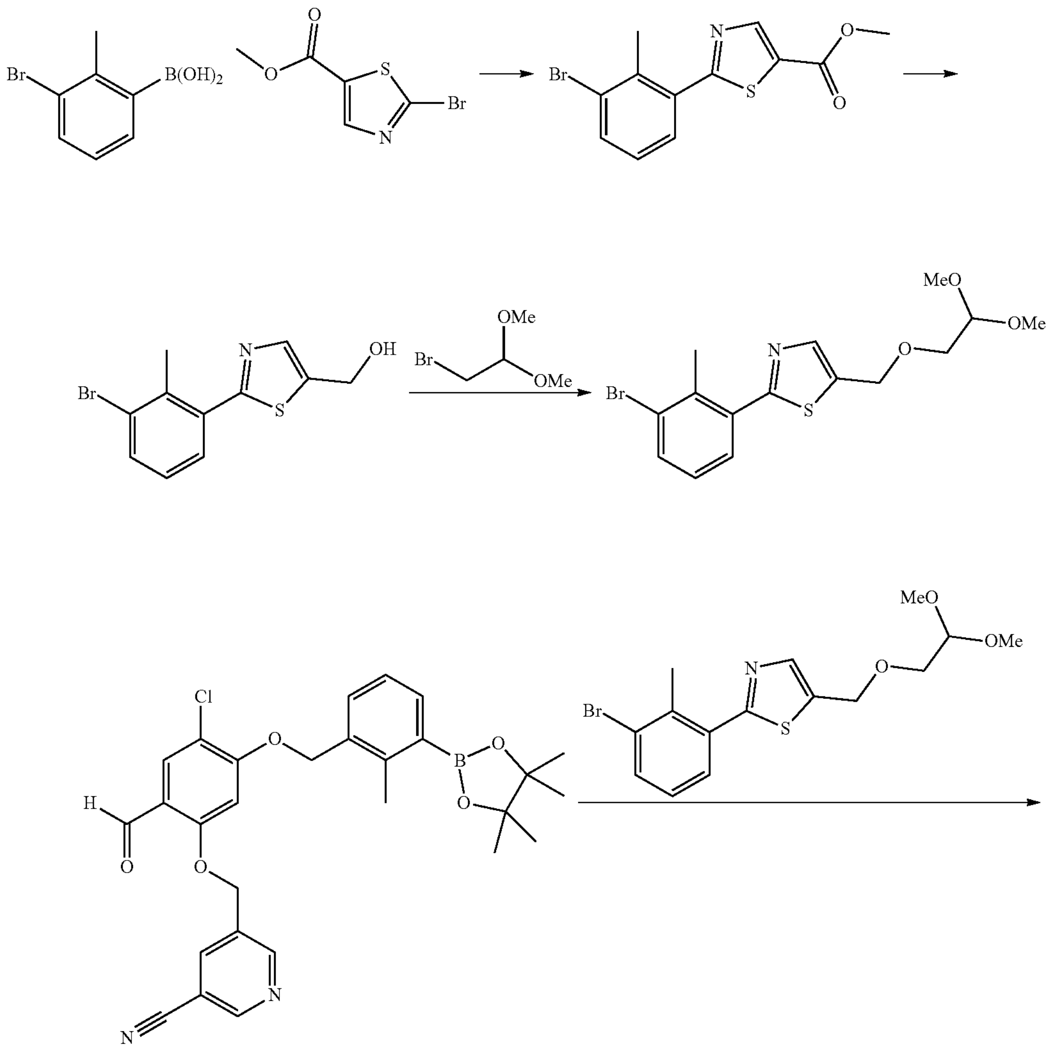

-continued

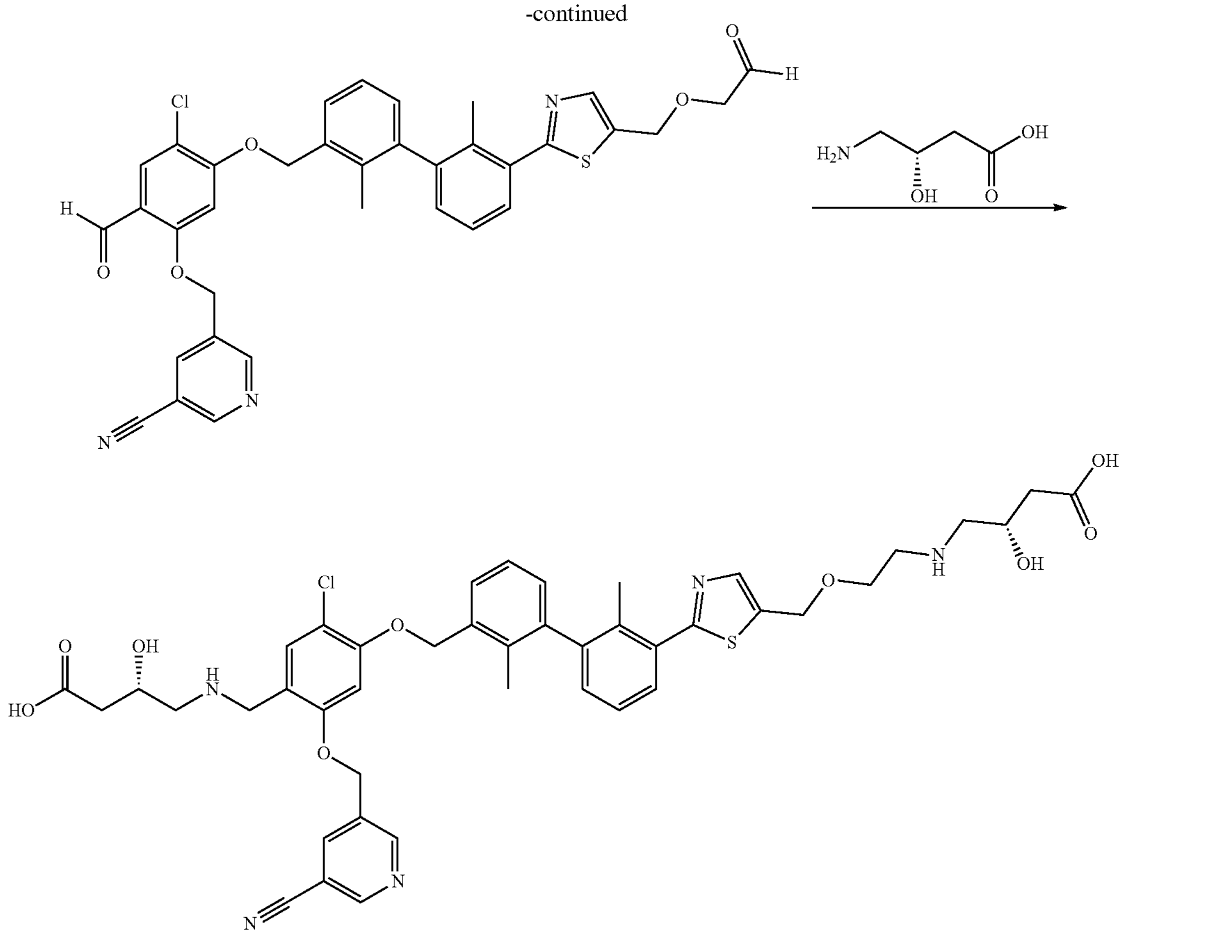

Step 1: (3-bromo-2-methylphenyl)boronic acid (350 mg, 1.63 mmol), methyl 2-bromothiazole-5-carboxylate (470 mg, 2.12 mmol), potassium carbonate (788 mg, 5.70 mmol) and tetrakis(triphenylphosphine)palladium (113 mg, 98.0 umol) were combined in a reaction vessel. Dioxane (12.0 mL) and water (3.00 mL) were added and the resulting suspension was sparged with argon (via a balloon filled with argon) for 10 minutes. The reaction mixture was stirred at 95° C. for 7h. The reaction mixture was cooled to rt, and quenched by the addition of sat aq $NH_4Cl$ and EtOAc. The layers were separated and the aqueous layer was further extracted with EtOAc. The organic layers were combined, washed with brine, dried (over $Na_2SO_4$), filtered then concentrated in vacuo. The crude mixture was purified by $SiO_2$chromatography (eluting with 0-100% EtOAc/hex) to afford methyl 2-(3-bromo-2-methylphenyl)thiazole-5-carboxylate.

Step 2: To a solution of to methyl 2-(3-bromo-2-methylphenyl)thiazole-5-carboxylate (250 mg, 0.801 mmol) in thf (7.00 mL) was added 2 M Lithium borohydride (1.20 mL) then methanol (0.097 mL, 2.40 mmol, note: evolution of gas during addition, so adequate ventilation of the reaction vessel is required). Analysis by tlc indicated consumption of the starting material. The reaction mixture was quenched by the addition of sat aq $NaHCO_3$ and EtOAc, and the mixture was stirred for 10 min. The layers were separated and the aqueous layer was further extracted with EtOAc. The organic layers were combined, washed with brine, dried (over $Na_2SO_4$), filtered then concentrated in vacuo to afford (2-(3-bromo-2-methylphenyl)thiazol-5-yl)methanol ([M+1]=284.35, 286.22).

Step 3: To a solution of (2-(3-bromo-2-methylphenyl)thiazol-5-yl)methanol (100 mg, 0.35 mmol) in DMF (2.0 mL) cooled in an ice-water bath was sodium hydride (60 wt %, 16 mg, 0.42 mmol) then bromoacetaldehyde dimethyl acetal (0.21 mL, 1.8 mmol). The reaction mixture was allowed to stir in the bath overnight (with slow warming to rt). The reaction mixture was quenched by the addition of sat aq $NH_4Cl$ and EtOAc. The layers were separated and the aqueous layer was further extracted with EtOAc. The organic layers were combined, washed with brine, dried (over $Na_2SO_4$), filtered then concentrated in vacuo. The crude mixture was purified by $SiO_2$ chromatography (eluting with 0-100% EtOAc/hex) to afford 2-(3-bromo-2-methylphenyl)-5-((2,2-dimethoxyethoxy)methyl)thiazole ([M+1]=372.48, 374.23).

Step 4: (S)-4-((4-((3'-(5-((2-(((S)-3-carboxy-2-hydroxypropyl)amino)ethoxy)methyl)thiazol-2-yl)-2,2'-dimethyl-[1,1'-biphenyl]-3-yl)methoxy)-5-chloro-2-((5-cyanopyridin-3-yl)methoxy)benzyl)amino)-3-hydroxybutanoic acid was prepared as the bis-TFA salt by a sequence identical to the route used to prepare Example 209 starting with 2-(3-bromo-2-methylphenyl)-5-((2,2-dimethoxyethoxy)methyl)thiazole instead of 5-(3-bromo-2-methylphenyl)-1-(2,2-dimethoxyethyl)-1H-indazole. LCMS-ESI$^+$ (m/z): $[M+H]^+$ calcd for $C_{43}H_{46}ClN_5O_9S$: 844.28; found: 844.14. $^1H$ NMR (400 MHz, Methanol-$d_4$) δ 8.96 (s, 1H), 8.93 (s, 1H), 8.38 (d, J=2.3 Hz, 1H), 7.87 (s, 1H), 7.58 (d, J=7.7 Hz, 1H), 7.56-7.45 (m, 2H), 7.38 (t, J=7.7 Hz, 1H), 7.33-7.22 (m, 2H), 7.14 (d, J=7.6 Hz, 1H), 7.08 (s, 1H), 5.38 (s, 2H), 5.32 (s, 2H), 4.89 (s, 2H), 4.33-4.09 (m, 3H), 3.83 (t, J=5.3 Hz, 2H), 3.28-3.15 (m, 3H), 3.09-2.92 (m, 2H), 2.54 (d, J=6.3 Hz, 2H), 2.52 (d, J=6.4 Hz, 2H), 2.16-2.07 (m, 6H).

Example 351: (S)-4-(((5-chloro-6-((2,2'-dichloro-4"-(2-((2-hydroxyethyl)amino)ethoxy)-[1,1':3',1"-terphenyl]-3-yl)methoxy)-2-((3,5-dicyanobenzyl)oxy)pyridin-3-yl)methyl)amino)-3-hydroxybutanoic acid

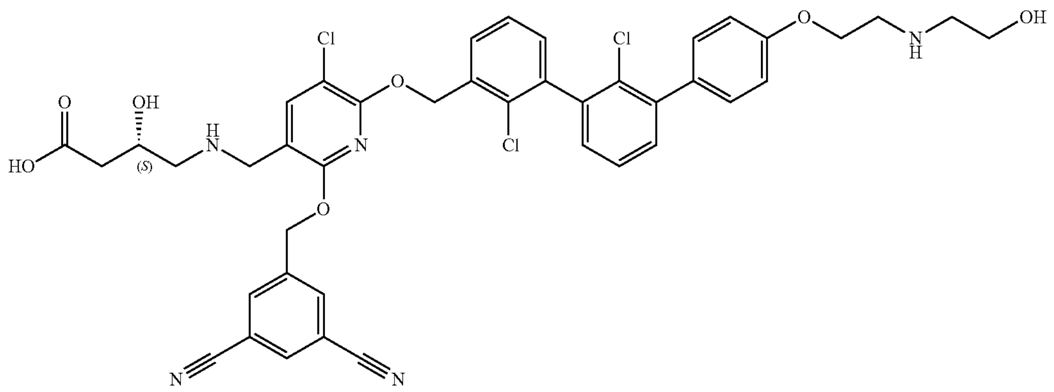

The title compound was synthesized according to general reductive amination procedure D. [M+1]=833.01. $^1$H NMR (400 MHz, Methanol-d4) δ 8.15-8.07 (m, 3H), 7.95 (s, 1H), 7.56-7.49 (m, 1H), 7.48-7.36 (m, 5H), 7.27 (ddd, J=23.0, 7.4, 1.9 Hz, 2H), 7.14-7.06 (m, 2H), 5.63-5.49 (m, 2H), 5.49 (s, 2H), 4.88 (s, 5H), 4.40-4.33 (m, 2H), 4.26 (s, 3H), 3.90-3.82 (m, 2H), 3.58-3.50 (m, 2H), 3.30-3.21 (m, 3H), 3.04 (dd, J=12.8, 9.8 Hz, 1H), 2.55 (d, J=6.4 Hz, 2H).

Example 352: (S)-2-(((5-chloro-6-((2,2'-dichloro-4"-(2-((2-hydroxyethyl)amino)ethoxy)-[1,1':3',1"-terphenyl]-3-yl)methoxy)-2-((3,5-dicyanobenzyl)oxy)pyridin-3-yl)methyl)amino)-3-hydroxy-2-methylpropanoic acid

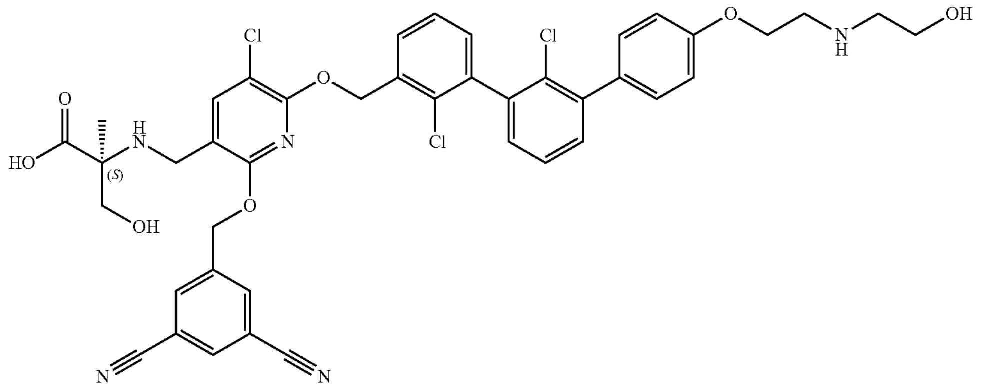

The title compound was synthesized according to general reductive amination procedure D. [M+1]=833.01. $^1$H NMR (400 MHz, Methanol-d4) δ 8.10 (dd, J=7.7, 1.5 Hz, 3H), 7.84 (d, J=8.1 Hz, 1H), 7.51-7.31 (m, 6H), 7.24 (ddd, J=17.7, 7.3, 1.8 Hz, 2H), 7.13-7.06 (m, 2H), 6.64 (d, J=8.1 Hz, 1H), 5.54 (d, J=13.8 Hz, 1H), 5.47 (s, 3H), 4.40-4.32 (m, 2H), 4.29 (s, 2H), 4.05 (d, J=12.1 Hz, 1H), 3.89-3.79 (m, 3H), 3.54 (t, J=5.0 Hz, 2H), 3.30-3.22 (m, 2H), 1.57 (s, 3H), 1.30 (d, J=16.3 Hz, 2H).

Example 353: (S)-4-((4-((4''-((S)-2-amino-3-hydroxypropoxy)-2,2'-dimethyl-[1,1':3',1''-terphenyl]-3-yl)methoxy)-5-chloro-2-((5-cyanopyridin-3-yl)methoxy)benzyl)amino)-3-hydroxybutanoic acid

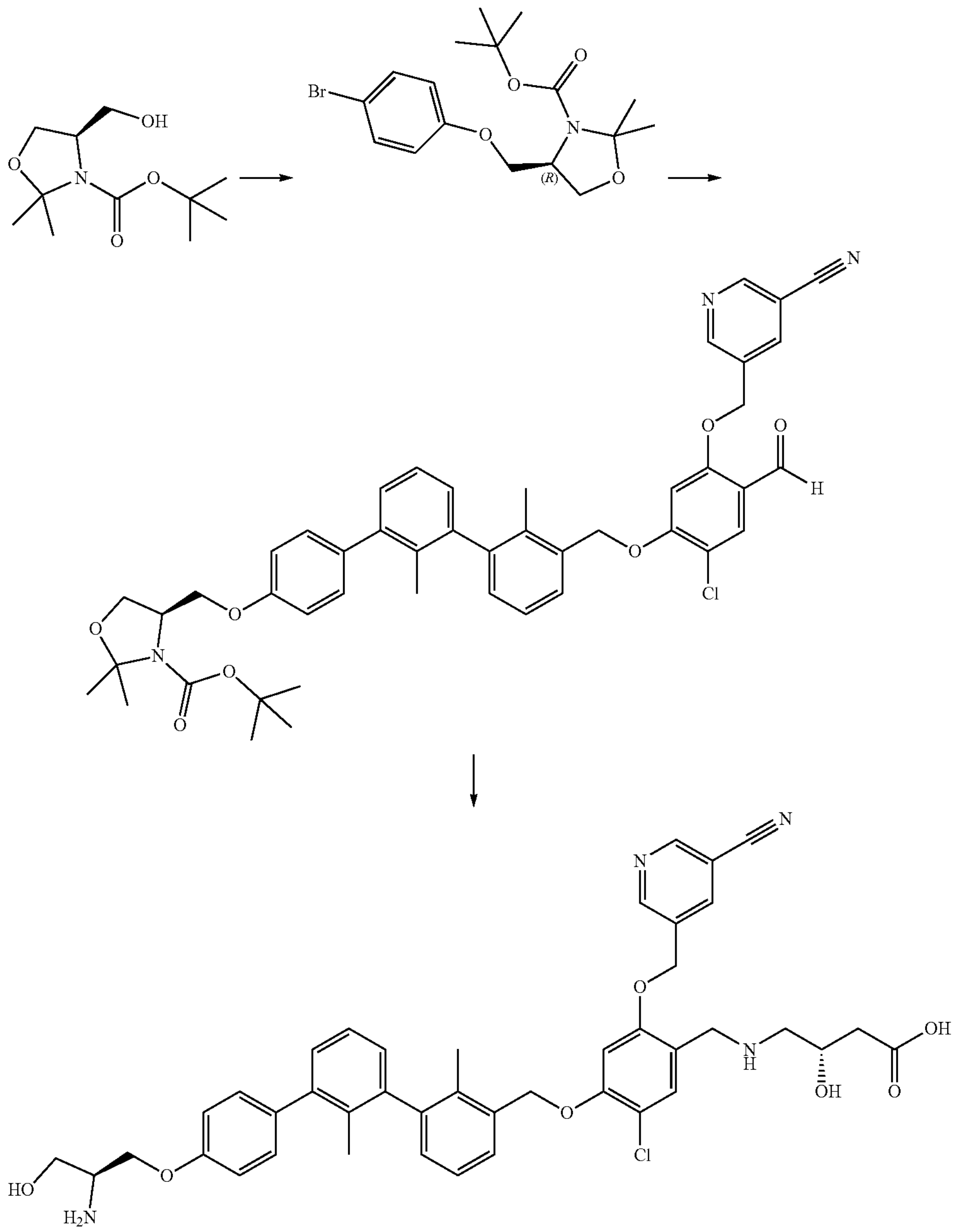

To a solution of (R)-4-Hydroxymethyl-2,2-dimethyl-oxazolidine-3-carboxylic acid tert-butyl ester (0.66 g, 2.86 mmol) and DMF was added NaH (14 mg, 2 equiv.). After 5 min., 1-Bromo-4-fluorobenzene 99% (0.31 ml, 2.86 mmol) was added. The mixture was then warmed to 80 C. After 16 h, the flask was cooled and to it added water and extracted with EtAOc. The organic layers are washed with brine, dried over $MgSO_4$, filtered and concentrated under reduced pressure. Flash column chromatography was carried out using Hexanes-EtOAc to isolate tert-butyl (R)-4-((4-bromophenoxy)methyl)-2,2-dimethyloxazolidine-3-carboxylate. [M+1]=387.3.

Tert-butyl (R)-4-(((3''-((2-chloro-5-((5-cyanopyridin-3-yl)methoxy)-4-formylphenoxy)methyl)-2',2''-dimethyl-[1,1':3',1''-terphenyl]-4-yl)oxy)methyl)-2,2-dimethyloxazolidine-3-carboxylate was prepared analogous to Intermediate 23. [M+1]=789.40.

(S)-4-((4-((4''-((S)-2-amino-3-hydroxypropoxy)-2,2'-dimethyl-[1,1':3',1''-terphenyl]-3-yl)methoxy)-5-chloro-2-((5-cyanopyridin-3-yl)methoxy)benzyl)amino)-3-hydroxybutanoic acid was synthesized according to general reductive amination procedure D after which the mixture was worked up (EtOAc and water, extracted, dried over MgSO4, filtered and concentrated under reduced pressure) before being treated with TFA and DCM. [M+1]=751.01. $^1$H NMR (400

MHz, Methanol-d4) δ 8.94 (dd, J=11.3, 2.0 Hz, 2H), 8.37 (t, J=2.1 Hz, 1H), 7.48 (d, J=24.9 Hz, 2H), 7.33-7.22 (m, 4H), 7.22-7.11 (m, 2H), 7.12-7.04 (m, 3H), 5.34 (d, J=25.9 Hz, 4H), 4.88-4.79 (m, 1H), 4.30 (dd, J=10.4, 4.0 Hz, 1H), 4.24 (s, 3H), 4.25-4.17 (m, 1H), 3.95-3.78 (m, 2H), 3.67 (s, 1H), 3.20 (dd, J=12.7, 3.0 Hz, 1H), 2.98 (dd, J=12.7, 9.8 Hz, 1H), 2.52 (dd, J=6.2, 1.3 Hz, 2H), 2.14 (s, 3H), 1.88 (s, 3H).

Example 354: (S)-4-((5-chloro-2-((5-cyanopyridin-3-yl)methoxy)-4-((4"-(((S)-1-(2-hydroxyethyl)piperidin-3-yl)oxy)-2,2'-dimethyl-[1,1':3',1"-terphenyl]-3-yl)methoxy)benzyl)amino)-3-hydroxybutanoic acid

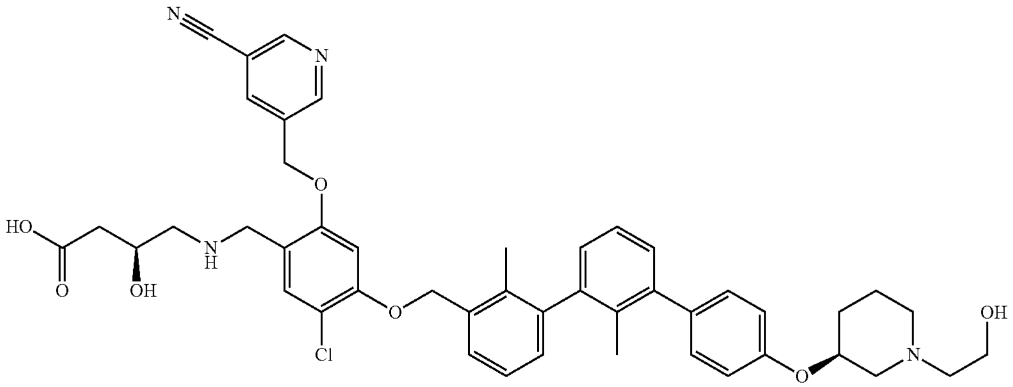 [SMILES: Cc1c(COc2cc(OCc3cncc(C#N)c3)c(CNC[C@@H](O)CC(=O)O)cc2Cl)cccc1-c1cccc(-c2ccc(O[C@H]3CCCN(CCO)C3)cc2)c1C]

(S)-4-((5-chloro-2-((5-cyanopyridin-3-yl)methoxy)-4-((4"-(((S)-1-(2-hydroxyethyl)piperidin-3-yl)oxy)-2,2'-dimethyl-[1,1':3',1"-terphenyl]-3-yl)methoxy)benzyl)amino)-3-hydroxybutanoic acid was prepared in analogy to Example 353. [M+1]=805.37. $^1$H NMR (400 MHz, Methanol-d4) δ 8.94 (dd, J=11.5, 2.1 Hz, 3H), 8.37 (s, 1H), 7.55-7.39 (m, 4H), 7.38-6.91 (m, 17H), 5.34 (d, J=24.9 Hz, 7H), 4.93 (s, 1H), 4.24 (s, 4H), 4.04-3.76 (m, 5H), 3.66-3.34 (m, 1H), 3.20 (dd, J=12.7, 3.0 Hz, 2H), 3.06-2.90 (m, 4H), 2.86 (d, J=0.7 Hz, 2H), 2.52 (dd, J=6.3, 1.2 Hz, 4H), 2.14 (s, 5H), 1.89 (s, 6H).

Example 355: (S)-4-((5-chloro-4-((3'-((2-chloro-5-methoxy-4-(((2-(methylsulfonamido)-2-oxoethyl)amino)methyl)phenoxy)methyl)-2,2'-dimethyl-[1,1'-biphenyl]-3-yl)methoxy)-2-((5-cyanopyridin-3-yl)methoxy)benzyl)amino)-3-hydroxybutanoic acid

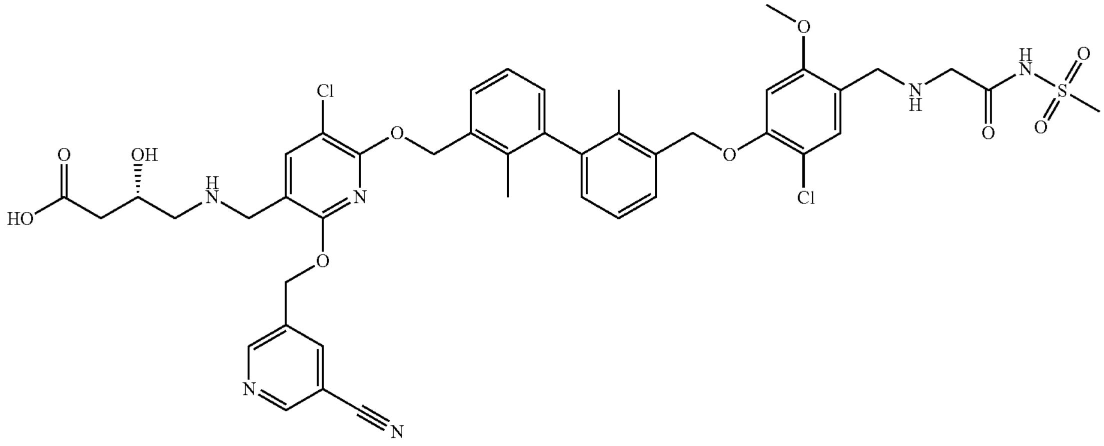 [SMILES: COc1cc(OCc2cccc(-c3cccc(COc4nc(OCc5cncc(C#N)c5)c(CNC[C@@H](O)CC(=O)O)cc4Cl)c3C)c2C)c(Cl)cc1CNCC(=O)NS(C)(=O)=O]

The title compound was prepared according to reductive amination procedure D. [M+1]=920.32. $^1$H NMR (400 MHz, Methanol-$d_4$) δ 8.94 (dd, J=14.9, 2.0 Hz, 2H), 8.38 (t, J=2.1 Hz, 1H), 7.97 (s, 1H), 7.60-7.38 (m, 4H), 7.27 (q, J=7.5 Hz, 1H), 7.12 (ddd, J=7.7, 2.9, 1.4 Hz, 1H), 6.96 (s, 1H), 5.38 (s, 2H), 5.31 (d, J=3.0 Hz, 2H), 4.32-4.15 (m, 2H), 3.97 (s, 3H), 3.87 (s, H), 3.26 (s, 2H), 2.99 (s, 2H), 2.86 (d, J=0.7 Hz, 1H), 2.08 (d, J=1.6 Hz, 6H).

Example 356: (4-((3'-((4-(((carboxymethyl)amino)methyl)-2-chloro-5-((5-cyanopyridin-3-yl)methoxy)phenoxy)methyl)-2,2'-dimethyl-[1,1'-biphenyl]-3-yl)methoxy)-3-methoxy-5-(trifluoromethyl)benzyl)glycine

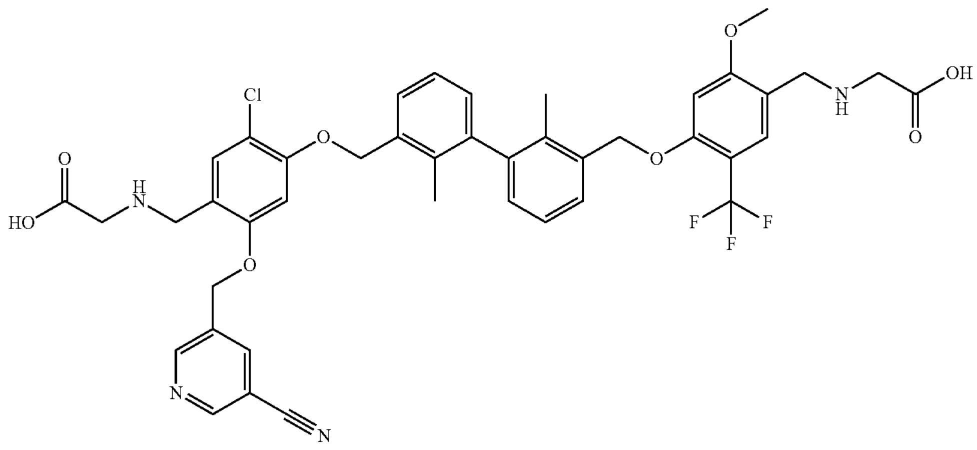 [SMILES: COc1cc(OCc2cccc(-c3cccc(COc4cc(OCc5cncc(C#N)c5)c(CNCC(=O)O)cc4Cl)c3C)c2C)c(C(F)(F)F)cc1CNCC(=O)O]

The title compound was synthesized according to general reductive amination procedure D. [M+1]=833.27. $^1H$ NMR (400 MHz, Methanol-$d_4$) δ 8.95 (dd, J=16.9, 2.0 Hz, 2H), 8.40 (t, J=2.1 Hz, 1H), 7.55-7.44 (m, 3H), 7.28 (q, J=7.7 Hz, 2H), 7.13 (ddd, J=7.7, 4.7, 1.3 Hz, 2H), 7.09 (s, 1H), 7.02 (s, 1H), 5.41-5.30 (m, 5H), 4.27 (d, J=5.7 Hz, 3H), 4.04 (s, 3H), 3.87 (d, J=0.7 Hz, 3H), 2.07 (d, J=9.6 Hz, 5H).

Example 357: (S)-4-((4-((3'-((4-((((S)-3-carboxy-2-hydroxypropyl)amino)methyl)-2-chloro-5-methoxyphenoxy)methyl)-2,2'-dimethyl-[1,1'-biphenyl]-3-yl)methoxy)-2-methoxy-5-(trifluoromethyl)benzyl)amino)-3-hydroxybutanoic acid

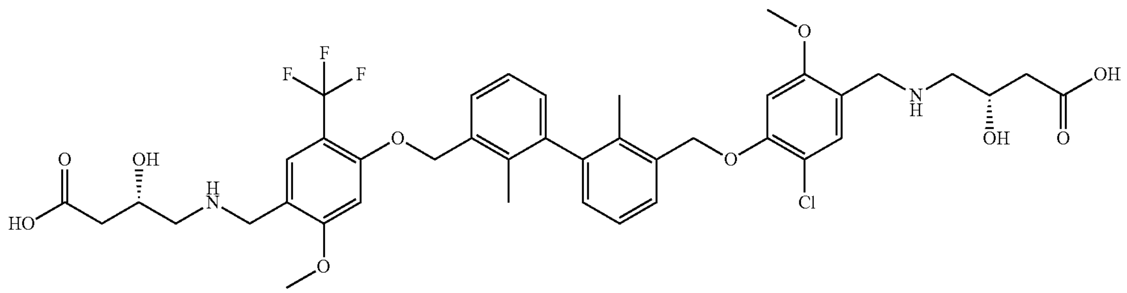 [SMILES: COc1cc(OCc2cccc(-c3cccc(COc4cc(OC)c(CNC[C@@H](O)CC(=O)O)cc4C(F)(F)F)c3C)c2C)c(Cl)cc1CNC[C@@H](O)CC(=O)O]

The title compound was synthesized according to general reductive amination procedure D. [M+1]=819.18. $^1H$ NMR (400 MHz, Methanol-$d_4$) δ 7.51 (dt, J=7.7, 1.7 Hz, 1H), 7.43 (s, 1H), 7.29 (td, J=7.7, 2.2 Hz, 1H), 7.12 (ddd, J=7.7, 2.7, 1.4 Hz, 1H), 7.02 (s, 2H), 5.40-5.27 (m, 3H), 4.29 (tdd, J=9.5, 6.4, 4.2 Hz, 1H), 4.23 (s, 1H), 4.17 (s, 1H), 4.04 (s, 2H), 3.96 (s, 2H), 3.19 (ddd, J=12.7, 8.3, 3.1 Hz, 2H), 2.98 (ddd, J=12.8, 9.8, 8.7 Hz, 2H), 2.54 (dd, J=6.3, 3.3 Hz, 3H), 2.20-2.03 (m, 3H).

Example 358: (S)-2-((5-chloro-2-((5-cyanopyridin-3-yl)methoxy)-4-((2,2'-dimethyl-3"-((methylamino) methyl)-[1,1':3',1"-terphenyl]-3-yl)methoxy)benzyl) amino)-3-hydroxy-2-methylpropanoic acid

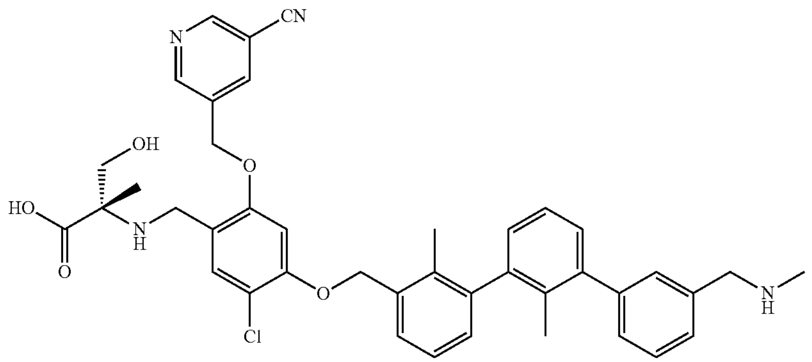 [SMILES: CNCc1cccc(-c2cccc(-c3cccc(COc4cc(OCc5cncc(C#N)c5)c(CN[C@@](C)(CO)C(=O)O)cc4Cl)c3C)c2C)c1]

The title compound was synthesized according to general reductive amination procedure D. [M+1]=705.4. $^1$H NMR (400 MHz, Methanol-$d_4$) δ 8.98 (d, J=2.1 Hz, 1H), 8.91 (d, J=1.9 Hz, 1H), 8.42 (t, J=2.1 Hz, 1H), 7.59-7.51 (m, 2H), 7.51-7.38 (m, 4H), 7.34-7.22 (m, 3H), 7.17-7.06 (m, 3H), 5.37 (s, 2H), 5.32 (s, 2H), 4.29 (s, 2H), 4.25 (s, 2H), 4.01 (d, J=12.1 Hz, 1H), 3.81 (d, J=12.1 Hz, 1H), 2.74 (s, 3H), 2.14 (s, 3H), 1.89 (s, 3H), 1.53 (s, 3H).

Example 359: (S)-4-(((6-(3'-((4-((((S)-3-carboxy-2-hydroxypropyl)amino)methyl)-2-chloro-5-((5-cyano-pyridin-3-yl)methoxy)phenoxy)methyl)-2,2'-dim-ethyl-[1,1'-biphenyl]-3-yl)-4-chloronaphthalen-1-yl) methyl)amino)-3-hydroxybutanoic acid

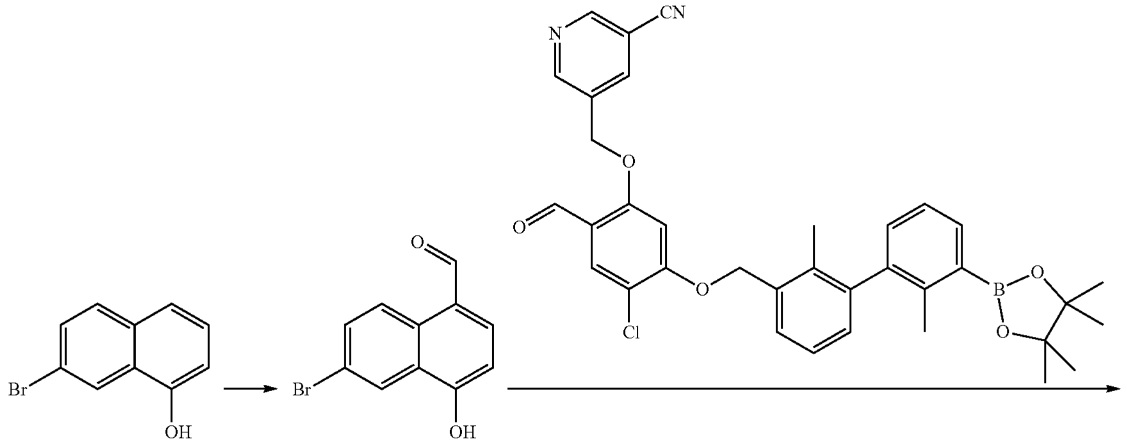

-continued
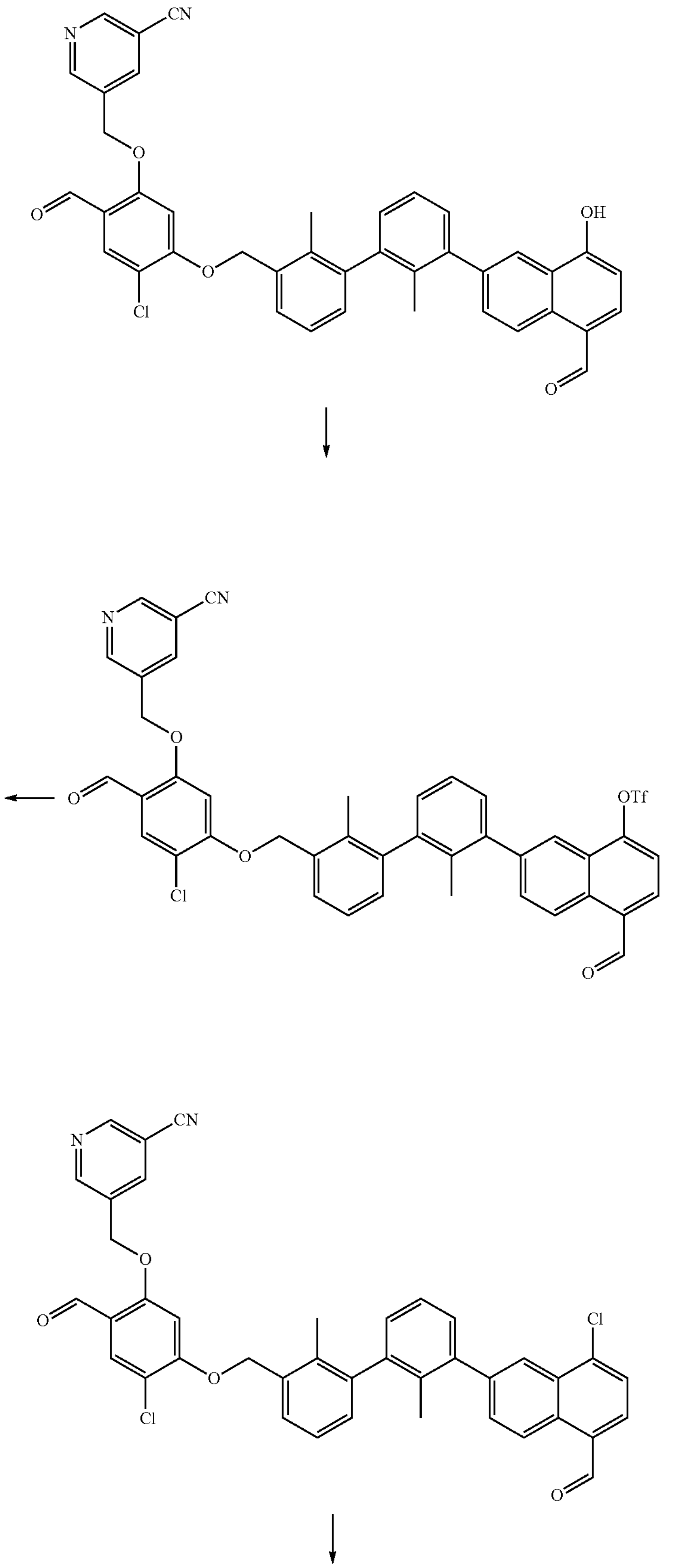

-continued

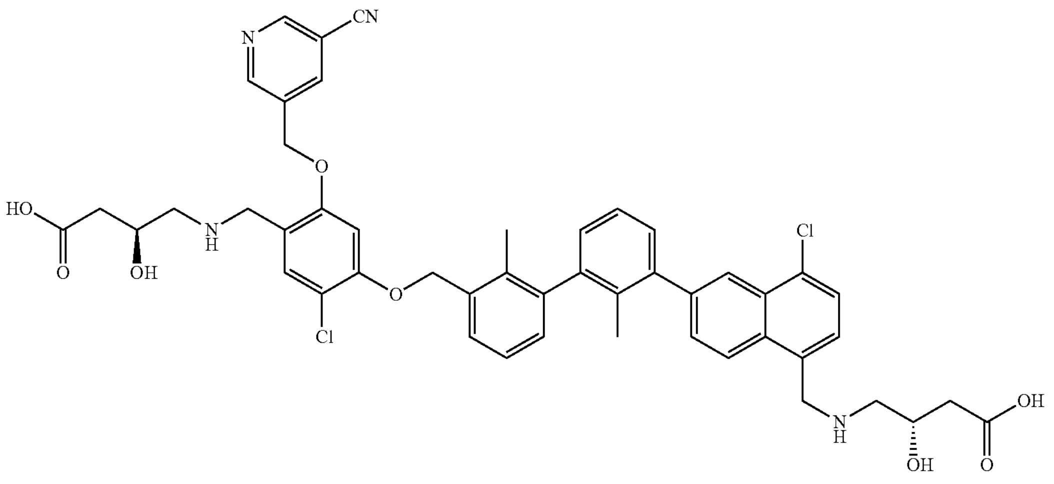

A flask was charged with $TiCl_4$ (1M in DCM, 15.8 mL, 15.8 mmol) and DCM (12 mL). dichloromethyl methyl ether (1.27 mL, 14.4 mmol) was added, and the mixture was cooled to 0° C. A solution of 7-bromonaphthalen-1-ol (1.6 g, 7.2 mmol) in DCM (10 mL) was then added dropwise. The mixture was warmed to rt and stirred 3 h, at which time TLC showed complete consumption of starting material. The mixture was diluted with DCM (100 mL), and 2N HCl (100 mL) was carefully added. The biphasic mixture was filtered to remove titanium salts, and the biphasic mixture separated. The aqueous layer was extracted with DCM (3×100 mL), and the combined organics were dried ($MgSO_4$) and concentrated. The residue was purified by column chromatography ($SiO_2$, 0-100% EtOAc/hex) to yield 6-bromo-4-hydroxy-1-naphthaldehyde.

A flask was charged with 5-((4-chloro-5-((2,2'-dimethyl-3'-(4,4,5,5-tetramethyl-1,3,2-dioxaborolan-2-yl)-[1,1'-biphenyl]-3-yl)methoxy)-2-formylphenoxy)methyl)nicotinonitrile (70 mg, 0.115 mmol), 6-bromo-4-hydroxy-1-naphthaldehyde (35 mg, 0.138 mmol), $Na_2CO_3$ (61 mg, 0.58 mmol), Pd XPhos G2 (4 mg, 0.06 mmol), dioxane (2 mL), and water (0.2 mL). The flask was subjected to 3 vacuum/argon cycles, then heated to 90 C for 2 h. The mixture was cooled to rt, filtered over celite, concentrated, and purified by column chromatography (SiO2, 0-100% EtOAc/hex) to yield 5-((4-chloro-2-formyl-5-((3'-(5-formyl-8-hydroxynaphthalen-2-yl)-2,2'-dimethyl-[1,1'-biphenyl]-3-yl)methoxy)phenoxy)methyl)nicotinonitrile.

To a solution of 5-((4-chloro-2-formyl-5-((3'-(5-formyl-8-hydroxynaphthalen-2-yl)-2,2'-dimethyl-[1,1'-biphenyl]-3-yl)methoxy)phenoxy)methyl)nicotinonitrile (60 mg, 0.092 mmol) and pyridine (0.02 mL, 0.3 mmol) in DCM (5 mL) was added trifluoromethanesulfonic anhydride (0.02 mL, 0.1 mmol). The mixture was stirred for 30 min, then poured over water (10 mL). The aqueous layer was extracted with EtOAc (4×10 mL), and the combined organics dried ($MgSO_4$), concentrated, and purified by column chromatography ($SiO_2$, 0-90% EtOAc/hex) to yield 7-(3'-((2-chloro-5-((5-cyanopyridin-3-yl)methoxy)-4-formylphenoxy)methyl)-2,2'-dimethyl-[1,1'-biphenyl]-3-yl)-4-formylnaphthalen-1-yl trifluoromethanesulfonate.

A vial was charged with $Pd_2(dba)_3$ (1 mg, 0.001 mmol), tBuBrettPhos (2 mg, 0.005 mmol), and dioxane (1 mL). The mixture was subjected to 3 vacuum/argon cycles, then heated to 120° C. for 5 min. The solution was then cooled to rt.

A separate flask was charged with KCl (6 mg, 0.07 mmol), KF (1 mg, 0.02 mmol), 7-(3'-((2-chloro-5-((5-cyanopyridin-3-yl)methoxy)-4-formylphenoxy)methyl)-2,2'-dimethyl-[1,1'-biphenyl]-3-yl)-4-formylnaphthalen-1-yl trifluoromethanesulfonate (30 mg, 0.038 mmol), and dioxane (2 mL). The mixture was subjected to 3 vacuum/argon cycles, and then the catalyst solution was added. The resultant solution was stirred at 100° C. for 16 h, then concentrated and purified by column chromatography ($SiO_2$, 0-75% EtOAc/hex) to yield 5-((4-chloro-5-((3'-(8-chloro-5-formylnaphthalen-2-yl)-2,2'-dimethyl-[1,1'-biphenyl]-3-yl)methoxy)-2-formylphenoxy)methyl)nicotinonitrile.

(S)-4-(((6-(3'-((4-((((S)-3-carboxy-2-hydroxypropyl)amino)methyl)-2-chloro-5-((5-cyanopyridin-3-yl)methoxy)phenoxy)methyl)-2,2'-dimethyl-[1,1'-biphenyl]-3-yl)-4-chloronaphthalen-1-yl)methyl)amino)-3-hydroxybutanoic acid was synthesized according to general reductive amination procedure D. [M+1]=877.3. $^1H$ NMR (400 MHz, Methanol-$d_4$) δ 8.96 (d, J=2.0 Hz, 1H), 8.92 (d, J=2.0 Hz, 1H), 8.38 (t, J=2.0 Hz, 1H), 8.34-8.25 (m, 2H), 7.81-7.73 (m, 2H), 7.68 (d, J=7.8 Hz, 1H), 7.51 (s, 1H), 7.48 (dd, J=7.6, 1.4 Hz, 1H), 7.41-7.33 (m, 2H), 7.29 (t, J=7.6 Hz, 1H), 7.23-7.16 (m, 2H), 7.08 (s, 1H), 5.38 (s, 2H), 5.32 (s, 2H), 4.81 (s, 2H), 4.41 (dtd, J=9.4, 6.2, 3.0 Hz, 1H), 4.28-4.19 (m, 3H), 3.39 (dd, J=12.8, 3.1 Hz, 1H), 3.22-3.15 (m, 2H), 2.97 (dd, J=12.7, 9.8 Hz, 1H), 2.58 (d, J=6.3 Hz, 2H), 2.51 (d, J=6.3 Hz, 2H), 2.19 (s, 3H), 1.93 (s, 3H).

Example 360: (S)-2-((4-((4"-(((2-(1H-imidazol-4-yl) ethyl)amino)methyl)-2,2'-dimethyl-[1,1':3',1"-terphenyl]-3-yl)methoxy)-5-chloro-2-((5-cyanopyridin-3-yl)methoxy)benzyl)amino)-3-hydroxy-2-methylpropanoic acid
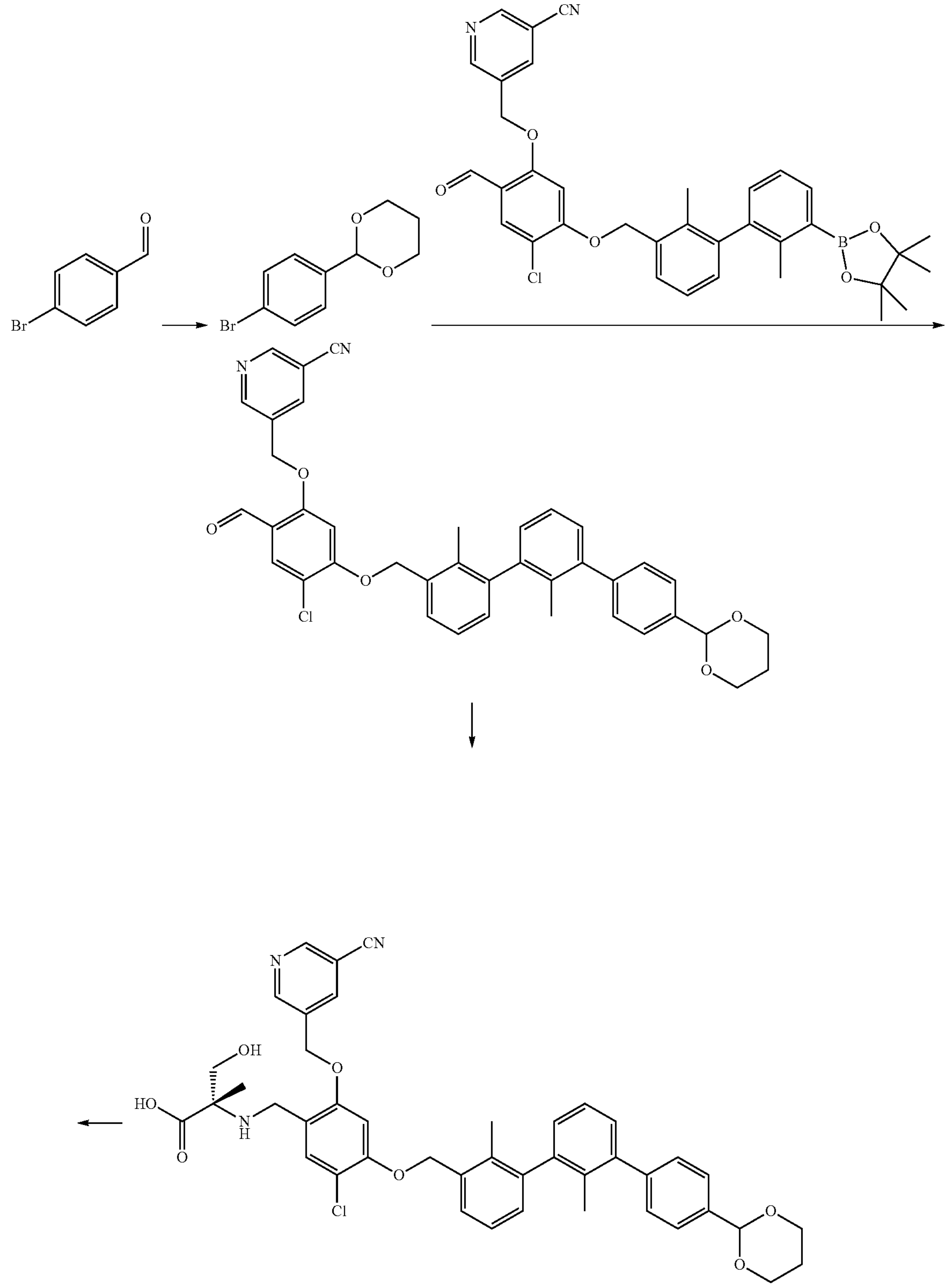

-continued

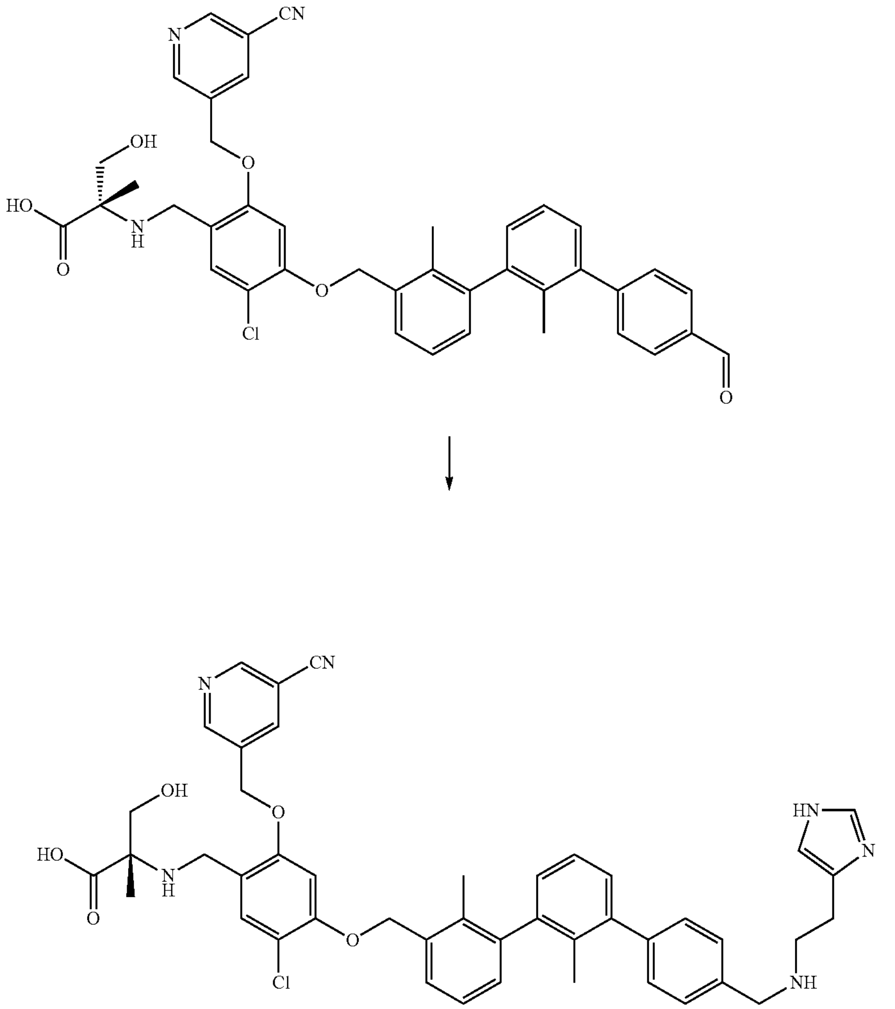

A flask fitted with a Dean-Stark apparatus was charged with 4-bromobenzaldehyde (2.73 g, 14.8 mmol), toluenesulfonic acid (381 mg, 2 mmol), 1,3-propanediol (21.4 mL), and toluene (25 mL). The mixture was heated to reflux for 3 h, then allowed to cool to rt, diluted with EtOAc, and washed with a saturated solution of $NaHCO_3$. The organic layer was dried ($Na_2SO_4$) and concentrated, and the residue purified by column chromatography ($SiO_2$, 0-50% EtOAc/hex) to yield 2-(4-bromophenyl)-1,3-dioxane.

A flask was charged with 5-((4-chloro-5-((2,2'-dimethyl-3'-(4,4,5,5-tetramethyl-1,3,2-dioxaborolan-2-yl)-[1,1'-biphenyl]-3-yl)methoxy)-2-formylphenoxy)methyl)nicotinonitrile (1.00 g, 1.64 mmol), 2-(4-bromophenyl)-1,3-dioxane (1.20 g, 4.93 mmol), $Na_2CO_3$ (696 mg, 7 mmol), Pd XPhos G2 (62 mg, 0.82 mmol), dioxane (10 mL), and water (1 mL). The flask was subjected to 3 vacuum/argon cycles, then heated to 90° C. for 5 h. The mixture was cooled to rt, filtered over celite, concentrated, and purified by column chromatography ($SiO_2$, 0-100% EtOAc/hex) to yield 5-((5-((4"-(1,3-dioxan-2-yl)-2,2'-dimethyl-[1,1':3',1"-terphenyl]-3-yl)methoxy)-4-chloro-2-formylphenoxy)methyl)nicotinonitrile.

(S)-2-((4-((4"-(1,3-dioxan-2-yl)-2,2'-dimethyl-[1,1':3',1"-terphenyl]-3-yl)methoxy)-5-chloro-2-((5-cyanopyridin-3-yl)methoxy)benzyl)amino)-3-hydroxy-2-methylpropanoic acid was synthesized according to general reductive amination procedure D.

To a solution of (S)-2-((4-((4"-(1,3-dioxan-2-yl)-2,2'-dimethyl-[1,1':3',1"-terphenyl]-3-yl)methoxy)-5-chloro-2-((5-cyanopyridin-3-yl)methoxy)benzyl)amino)-3-hydroxy-2-methylpropanoic acid (800 mg, 1.07 mmol) in THF (10 mL) was added 1 N HCl (5 mL, 5 mmol). The biphasic mixture was vigorously stirred for 1 h, then concentrated in vacuo to yield (S)-2-((5-chloro-2-((5-cyanopyridin-3-yl)methoxy)-4-((4"-formyl-2,2'-dimethyl-[1,1':3',1"-terphenyl]-3-yl)methoxy)benzyl)amino)-3-hydroxy-2-methylpropanoic acid, which was carried forward without further purification.

(S)-2-((4-((4"-(((2-(1H-imidazol-4-yl)ethyl)amino)methyl)-2,2'-dimethyl-[1,1':3',1"-terphenyl]-3-yl)methoxy)-5-chloro-2-((5-cyanopyridin-3-yl)methoxy)benzyl)amino)-3-hydroxy-2-methylpropanoic acid was synthesized according to general reductive amination procedure D. [M+1]=785.4. $^1$H NMR (400 MHz, Methanol-$d_4$) δ 8.98 (d, J=2.1 Hz, 1H), 8.91 (d, J=2.0 Hz, 1H), 8.87 (d, J=1.4 Hz, 1H), 8.42 (t, J=2.1 Hz, 1H), 7.61-7.53 (m, 3H), 7.50-7.42 (m, 4H), 7.33-7.24 (m, 2H), 7.20 (dd, J=7.7, 1.4 Hz, 1H), 7.16-7.07 (m, 3H), 5.37 (s, 2H), 5.32 (s, 2H), 4.33 (s, 2H), 4.29 (s, 2H), 4.01 (d, J=12.1 Hz, 1H), 3.81 (d, J=12.2 Hz, 1H), 3.46 (t, J=7.0 Hz, 2H), 3.23 (t, J=7.7 Hz, 2H), 2.14 (s, 3H), 1.87 (s, 3H), 1.53 (s, 3H).

Example 361: (S)-2-((5-chloro-2-((5-cyanopyridin-3-yl)methoxy)-4-((4''-((((1r,4r)-4-hydroxycyclohexyl)amino)methyl)-2,2'-dimethyl-[1,1':3',1''-terphenyl]-3-yl)methoxy)benzyl)amino)-3-hydroxy-2-methylpropanoic acid

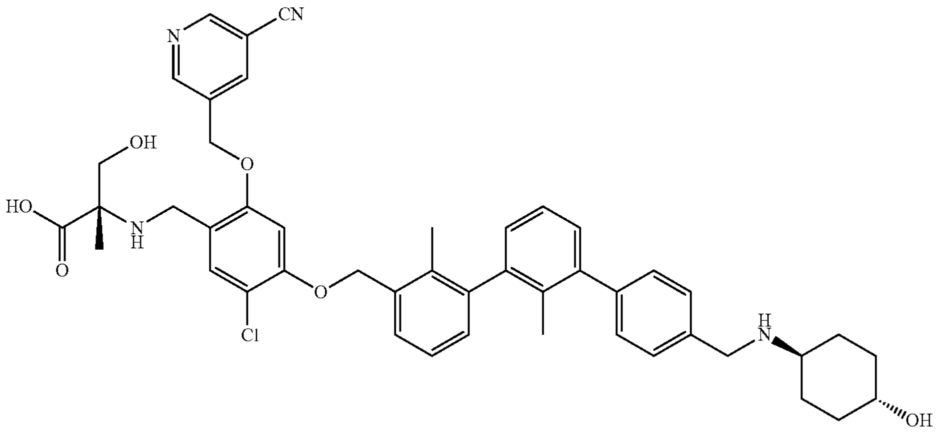 [SMILES: Cc1c(COc2cc(OCc3cncc(C#N)c3)c(CN[C@@](C)(CO)C(=O)O)cc2Cl)cccc1-c1cccc(-c2ccc(CN[C@H]3CC[C@H](O)CC3)cc2)c1C]

The title compound was synthesized according to general reductive amination procedure D. [M+1]=789.5. $^{1}$H NMR (400 MHz, Methanol-$d_4$) δ 8.98 (d, J=2.0 Hz, 1H), 8.91 (d, J=1.9 Hz, 1H), 8.42 (t, J=2.1 Hz, 1H), 7.63-7.52 (m, 3H), 7.52-7.41 (m, 3H), 7.34-7.24 (m, 2H), 7.20 (dd, J=7.7, 1.4 Hz, 1H), 7.17-7.06 (m, 3H), 5.37 (s, 2H), 5.32 (s, 2H), 4.28 (d, J=3.5 Hz, 4H), 4.01 (d, J=12.1 Hz, 1H), 3.81 (d, J=12.2 Hz, 1H), 3.57 (td, J=10.7, 5.4 Hz, 1H), 3.16 (dtd, J=10.2, 7.0, 6.3, 3.0 Hz, 1H), 2.24 (d, J=12.3 Hz, 2H), 2.14 (s, 3H), 2.08 (d, J=12.6 Hz, 2H), 1.87 (s, 3H), 1.59-1.45 (m, 5H), 1.42-1.33 (m, 2H).

Example 362: (S)-2-((4-((4''-(((2-acetamidoethyl)amino)methyl)-2,2'-dimethyl-[1,1':3',1''-terphenyl]-3-yl)methoxy)-5-chloro-2-((5-cyanopyridin-3-yl)methoxy)benzyl)amino)-3-hydroxy-2-methylpropanoic acid

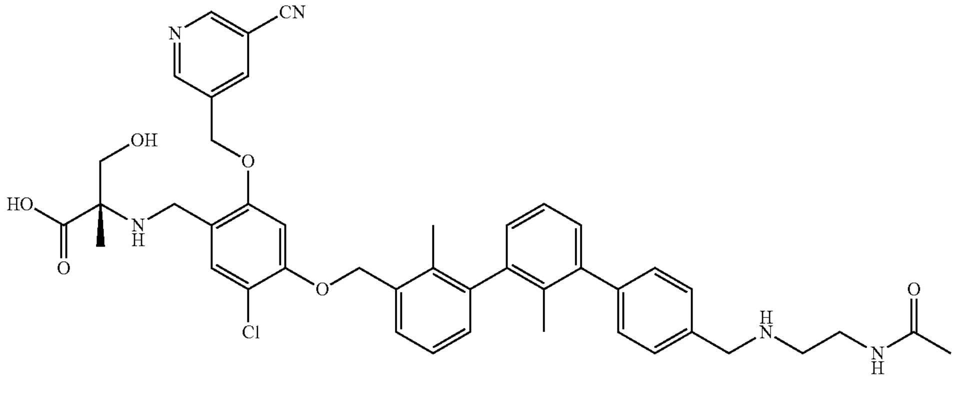 [SMILES: CC(=O)NCCNCc1ccc(-c2cccc(-c3cccc(COc4cc(OCc5cncc(C#N)c5)c(CN[C@@](C)(CO)C(=O)O)cc4Cl)c3C)c2C)cc1]

The title compound was synthesized according to general reductive amination procedure D. [M+1]=776.5. $^{1}$H NMR (400 MHz, Methanol-$d_4$) δ 8.98 (d, J=2.1 Hz, 1H), 8.91 (d, J=1.9 Hz, 1H), 8.42 (t, J=2.1 Hz, 1H), 7.66-7.52 (m, 3H), 7.51-7.37 (m, 3H), 7.35-7.24 (m, 2H), 7.20 (dd, J=7.7, 1.4 Hz, 1H), 7.18-7.04 (m, 3H), 5.37 (s, 2H), 5.32 (s, 2H), 4.39-4.20 (m, 4H), 4.01 (d, J=12.2 Hz, 1H), 3.81 (d, J=12.2 Hz, 1H), 3.53 (t, J=5.8 Hz, 2H), 3.22 (t, J=5.8 Hz, 2H), 2.15 (s, 3H), 1.98 (s, 3H), 1.87 (s, 3H), 1.53 (s, 3H).

Example 363: (2S)-2-((5-chloro-2-((5-cyanopyridin-3-yl)methoxy)-4-((2,2'-dimethyl-4"-(((5-oxopyrrolidin-3-yl)amino)methyl)-[1,1':3',1"-terphenyl]-3-yl)methoxy)benzyl)amino)-3-hydroxy-2-methylpropanoic acid

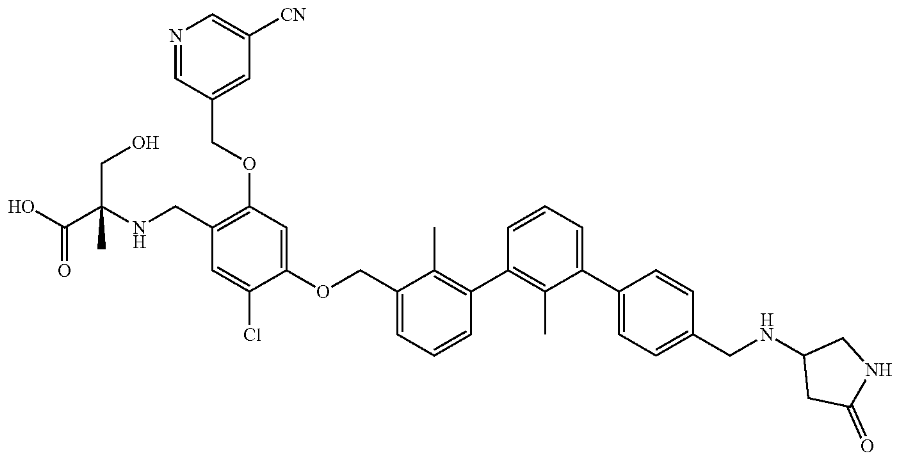 [SMILES: Cc1c(COc2cc(OCc3cncc(C#N)c3)c(CN[C@@](C)(CO)C(=O)O)cc2Cl)cccc1-c1cccc(-c2ccc(CNC3CNC(=O)C3)cc2)c1C]

The title compound was synthesized according to general reductive amination procedure D. [M+1]=774.3. $^1$H NMR (400 MHz, Methanol-$d_4$) δ 8.98 (d, J=2.1 Hz, 1H), 8.91 (d, J=1.9 Hz, 1H), 8.42 (t, J=2.1 Hz, 1H), 7.58 (d, J=8.1 Hz, 2H), 7.55 (s, 1H), 7.51-7.41 (m, 3H), 7.32 (t, J=7.6 Hz, 1H), 7.27 (t, J=7.6 Hz, 1H), 7.23-7.18 (m, 1H), 7.17-7.06 (m, 3H), 5.37 (s, 2H), 5.32 (s, 2H), 4.33 (d, J=2.0 Hz, 2H), 4.28 (s, 2H), 4.22 (tt, J=8.8, 4.5 Hz, 1H), 4.01 (d, J=12.1 Hz, 1H), 3.88-3.79 (m, 2H), 3.57 (dd, J=11.5, 4.2 Hz, 1H), 2.87 (dd, J=17.7, 8.8 Hz, 1H), 2.58 (dd, J=17.7, 5.0 Hz, 1H), 2.14 (s, 3H), 1.87 (s, 3H), 1.53 (s, 3H).

Example 364: (S)-2-((5-chloro-2-((5-cyanopyridin-3-yl)methoxy)-4-((3"-(((2-hydroxyethyl)amino)methyl)-2,2'-dimethyl-4"-(2-(pyridin-3-yl)ethoxy)-[1,1':3',1"-terphenyl]-3-yl)methoxy)benzyl)amino)-3-hydroxy-2-methylpropanoic acid

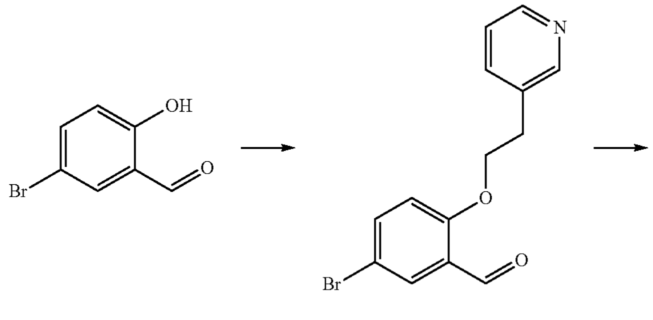

-continued

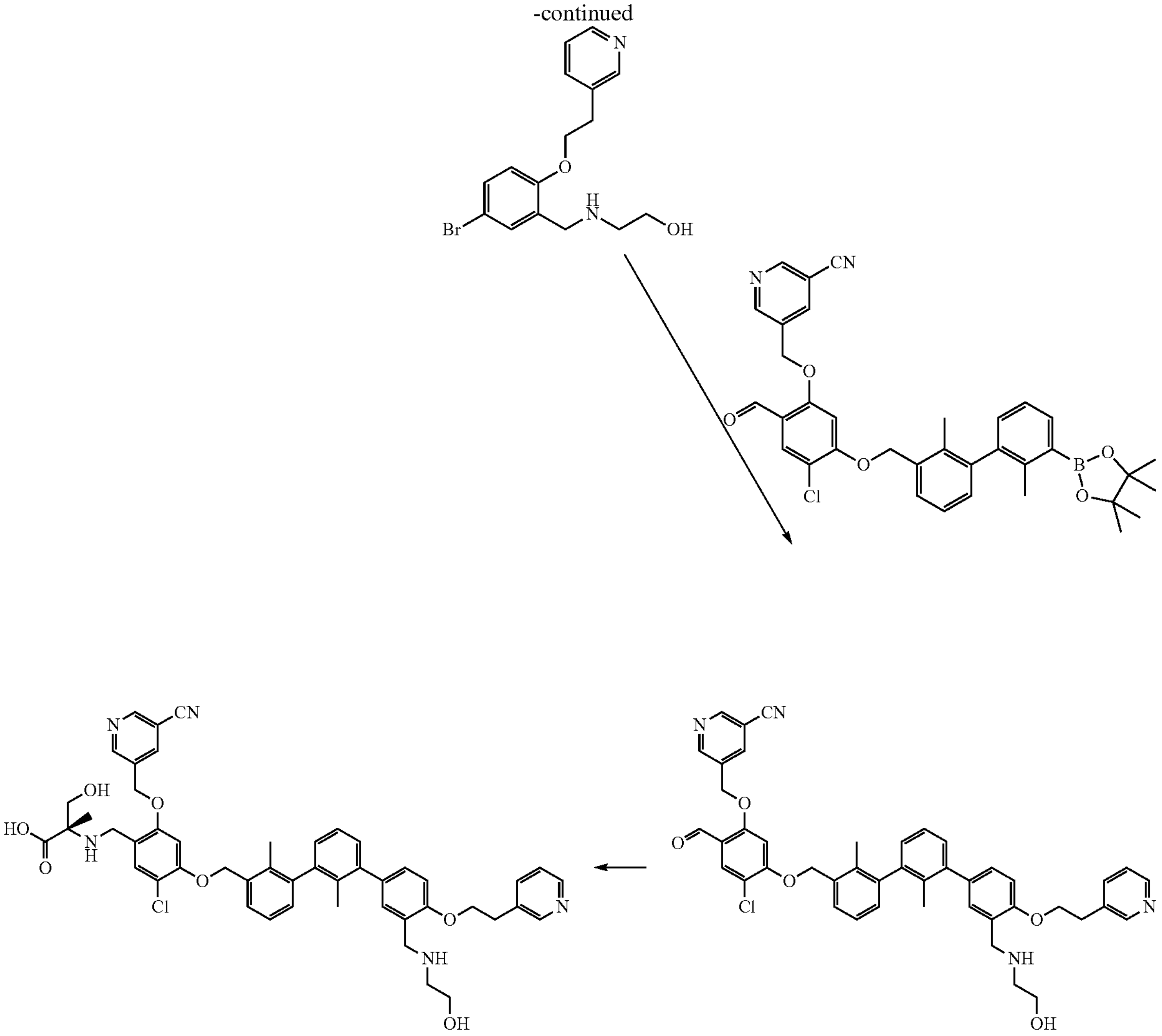

To a solution of 5-bromosalicaldehyde (500 mg, 2.49 mmol) in DMF (8 mL) was added $Cs_2CO_3$ (973 mg, 3.00 mmol) and 4-(2-bromoethyl)pyridine (431 mg, 2.32 mmol). The mixture was heated to 80° C. for 12 h, then cooled to rt, diluted with $Et_2O$ (50 mL), and washed with water (3×10 mL). The organic layer was dried ($MgSO_4$) and concentrated, and the residue purified by column chromatography ($SiO_2$, 0-100% EtOAc/hex) to yield 5-bromo-2-(2-(pyridin-3-yl)ethoxy)benzaldehyde.

2-((5-bromo-2-(2-(pyridin-3-yl)ethoxy)benzyl)amino)ethan-1-ol was synthesized according to general reductive amination procedure D.

A flask was charged with 5-((4-chloro-5-((2,2'-dimethyl-3'-(4,4,5,5-tetramethyl-1,3,2-dioxaborolan-2-yl)-[1,1'-biphenyl]-3-yl)methoxy)-2-formylphenoxy)methyl)nicotinonitrile (100 mg, 0.164 mmol), 2-((5-bromo-2-(2-(pyridin-3-yl)ethoxy)benzyl)amino)ethan-1-ol (231 mg, 0.657 mmol), $Na_2CO_3$ (139 mg, 1.35 mmol), Pd XPhos G2 (6 mg, 0.08 mmol), dioxane (2 mL), and water (0.2 mL). The flask was subjected to 3 vacuum/argon cycles, then heated to 90° C. for 12 h. The mixture was cooled to rt, filtered over celite, concentrated, and purified by preparative HPLC to yield 5-((4-chloro-2-formyl-5-((3"-(((2-hydroxyethyl)amino)methyl)-2,2'-dimethyl-4"-(2-(pyridin-3-yl)ethoxy)-[1,1':3',1"-terphenyl]-3-yl)methoxy)phenoxy)methyl)nicotinonitrile.

(S)-2-((5-chloro-2-((5-cyanopyridin-3-yl)methoxy)-4-((3"-(((2-hydroxyethyl)amino)methyl)-2,2'-dimethyl-4"-(2-(pyridin-3-yl)ethoxy)-[1,1':3',1"-terphenyl]-3-yl)methoxy)benzyl)amino)-3-hydroxy-2-methylpropanoic acid was synthesized according to general reductive amination procedure D. [M+1]=856.4. $^1H$ NMR (400 MHz, Methanol-$d_4$) δ 8.98 (d, J=2.1 Hz, 1H), 8.94 (s, 1H), 8.90 (d, J=2.0 Hz, 1H), 8.76 (d, J=5.6 Hz, 1H), 8.65 (dd, J=8.1, 1.7 Hz, 1H), 8.42 (t, J=2.1 Hz, 1H), 8.04 (dd, J=8.1, 5.7 Hz, 1H), 7.55 (s, 1H), 7.49-7.38 (m, 3H), 7.32-7.18 (m, 4H), 7.15-7.05 (m, 3H), 5.37 (s, 2H), 5.32 (s, 2H), 4.51 (t, J=6.2 Hz, 2H), 4.29 (s, 2H), 4.26 (s, 2H), 4.01 (d, J=12.1 Hz, 1H), 3.87-3.76 (m, 3H), 3.48 (t, J=6.1 Hz, 2H), 3.15 (t, J=5.2 Hz, 2H), 2.13 (s, 3H), 1.88 (s, 3H), 1.53 (s, 3H).

Example 365: 5-((4-chloro-5-((2'-(fluoromethyl)-4"-(((2-hydroxyethyl)amino)methyl)-2-methyl-[1,1':3',1"-terphenyl]-3-yl)methoxy)-2-(((2-hydroxyethyl)amino)methyl)phenoxy)methyl)nicotinonitrile
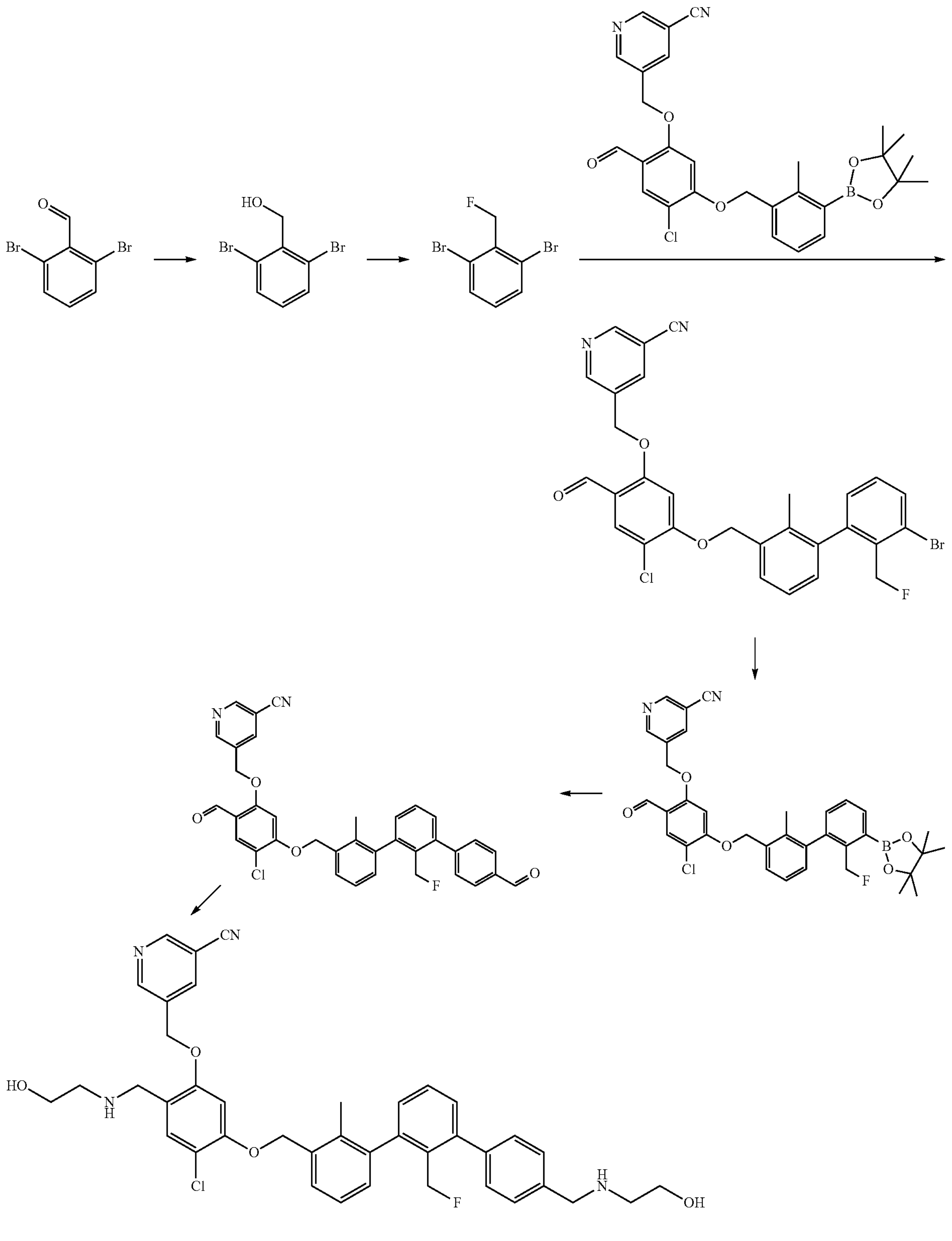

To a solution of 2,6-dibromobenzaldehyde (1.00 g, 3.80 mmol) in THF (10 mL) was added $NaBH_4$ (215 mg, 5.69 mmol). The mixture was stirred for 12 h, then poured over a saturated solution of $NH_4C_1$. The aqueous layer was extracted with EtOAc, and the combined organics dried ($MgSO_4$) and concentrated to yield (2,6-dibromophenyl) methanol as a white solid (1.00 g, 99%) which was carried forward without further purification.

A Teflon reaction tube was charged with (2,6-dibromophenyl)methanol (1.00 g, 3.76 mmol) and DCM (10 mL). The solution was cooled to 0° C. and DAST (0.55 mL, 4.1 mmol) was added. The mixture was stirred for 10 min, then $NaHCO_3$ (saturated solution, 10 mL) was added. The aqueous layer was extracted with DCM and the combined organics dried ($MgSO_4$) and concentrated. The residue was purified by column chromatography ($SiO_2$, 0-30% EtOAc/hex) to yield 1,3-dibromo-2-(fluoromethyl)benzene.

A flask was charged with 55-((4-chloro-2-formyl-5-((2-methyl-3-(4,4,5,5-tetramethyl-1,3,2-dioxaborolan-2-yl)benzyl)oxy)phenoxy)methyl)nicotinonitrile (300 mg, 0.578 mmol), 1,3-dibromo-2-(fluoromethyl)benzene (465 mg, 1.74 mmol), $Na_2CO_3$ (245 mg, 2.89 mmol), Pd(dppf)$Cl_2$ (21 mg, 0.028 mmol), dioxane (4 mL), and water (0.4 mL). The flask was subjected to 3 vacuum/argon cycles, then heated to 90° C. for 12 h. The mixture was cooled to rt, filtered over celite, concentrated, and purified by column chromatography ($SiO_2$, 0-70% EtOAc/hex) to yield 5-((5-((3'-bromo-2'-(fluoromethyl)-2-methyl-[1,1'-biphenyl]-3-yl)methoxy)-4-chloro-2-formylphenoxy)methyl)nicotinonitrile.

A flask was charged with 5-((5-((3'-bromo-2'-(fluoromethyl)-2-methyl-[1,1'-biphenyl]-3-yl)methoxy)-4-chloro-2-formylphenoxy)methyl)nicotinonitrile (270 mg, 0.466 mmol), bis(pinacolato)diboron (142 mg, 0.559 mmol), potassium acetate (123 mg, 1.21 mmol), Pd(dppf)$Cl_2$ (17 mg, 0.023 mmol), and dioxane (2 mL). The mixture was subjected to three vacuum/argon cycles, then stirred at 90° C. for 3 h. The mixture was cooled to rt, filtered over celite, concentrated and purified by column chromatography ($SiO_2$, 0-90% EtOAc/hex) to yield 5-((4-chloro-5-((2'-(fluoromethyl)-2-methyl-3'-(4,4,5,5-tetramethyl-1,3,2-dioxaborolan-2-yl)-[1,1'-biphenyl]-3-yl)methoxy)-2-formylphenoxy) methyl)nicotinonitrile.

A flask was charged with 5-((4-chloro-5-((2'-(fluoromethyl)-2-methyl-3'-(4,4,5,5-tetramethyl-1,3,2-dioxaborolan-2-yl)-[1,1'-biphenyl]-3-yl)methoxy)-2-formylphenoxy) methyl)nicotinonitrile (232 mg, 0.370 mmol), 4-bromobenzaldehyde (205 mg, 1.11 mmol), $Na_2CO_3$ (157 mg, 1.48 mmol), Pd(dppf)$Cl_2$ (14 mg, 0.019 mmol), dioxane (4 mL), and water (0.4 mL). The flask was subjected to 3 vacuum/argon cycles, then heated to 90 C for 12 h. The mixture was cooled to rt, filtered over celite, concentrated, and purified by column chromatography ($SiO_2$, 0-70% EtOAc/hex) to yield 5-((4-chloro-5-((2'-(fluoromethyl)-4"-formyl-2-methyl-[1,1':3',1"-terphenyl]-3-yl)methoxy)-2-formylphenoxy)methyl)nicotinonitrile.

5-((4-chloro-5-((2'-(fluoromethyl)-4"-(((2-hydroxyethyl) amino)methyl)-2-methyl-[1,1':3',1"-terphenyl]-3-yl) methoxy)-2-(((2-hydroxyethyl)amino)methyl)phenoxy) methyl)nicotinonitrile was synthesized according to general reductive amination procedure D. [M+1]=695.2. $^1$H NMR (400 MHz, Methanol-$d_4$) δ 8.95 (d, J=1.9 Hz, 1H), 8.89 (d, J=1.8 Hz, 1H), 8.38 (t, J=2.0 Hz, 1H), 7.61 (d, J=8.3 Hz, 2H), 7.58-7.45 (m, 5H), 7.39 (d, J=7.7 Hz, 1H), 7.25 (t, J=7.7 Hz, 2H), 7.19 (d, J=7.4 Hz, 1H), 7.04 (s, 1H), 5.40-5.27 (m, 4H), 4.90 (td, J=38.7, 38.7, 10.7 Hz, 2H), 4.32 (s, 2H), 4.24 (s, 2H), 3.85 (t, J=5.3 Hz, 2H), 3.78 (t, J=5.8 Hz, 2H), 3.19 (t, J=5.1 Hz, 2H), 3.12 (t, J=5.8, 5.3 Hz, 2H), 2.12 (s, 3H).

Example 366: 5-((4-chloro-2-((dimethylamino) methyl)-5-((3'-(5-((dimethylamino)methyl)thiophen-2-yl)-2,2'-dimethyl-[1,1'-biphenyl]-3-yl)methoxy) phenoxy)methyl)nicotinonitrile

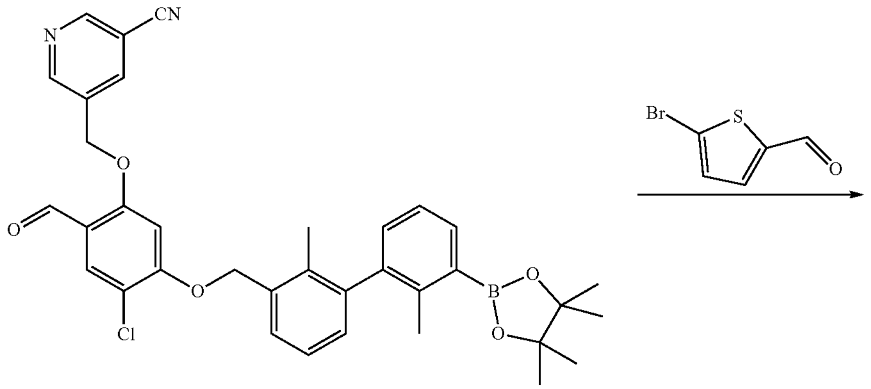

-continued

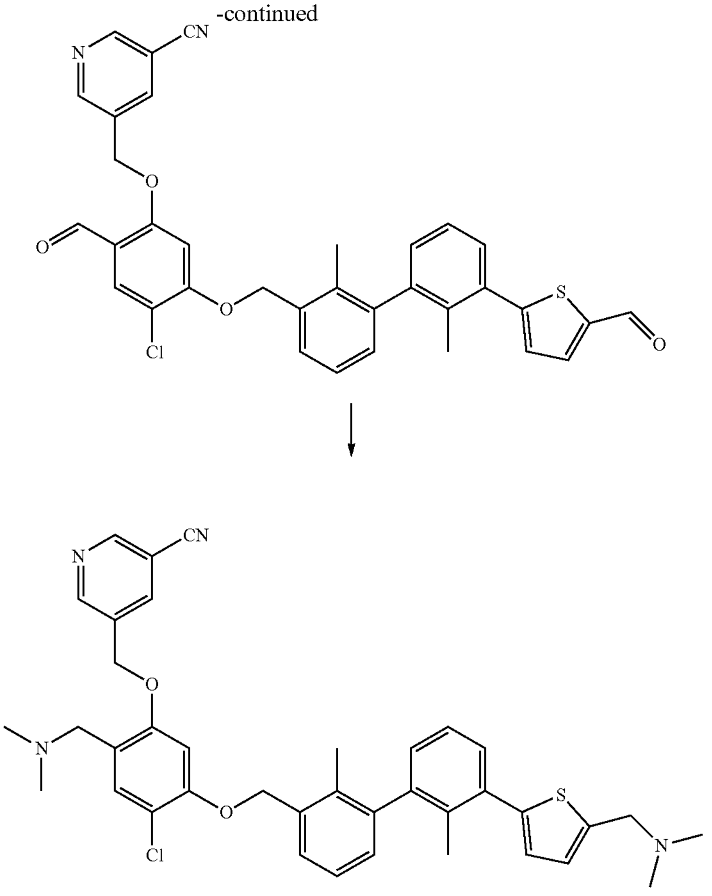

A flask was charged with 5-((4-chloro-5-((2,2'-dimethyl-3'-(4,4,5,5-tetramethyl-1,3,2-dioxaborolan-2-yl)-[1,1'-biphenyl]-3-yl)methoxy)-2-formylphenoxy)methyl)nicotinonitrile (104 mg, 0.171 mmol), 5-bromothiophene-2-carbaldehyde (0.06 mL, 0.5 mmol), $Na_2CO_3$ (72 mg, 0.68 mmol), Pd XPhos G2 (6 mg, 0.08 mmol), dioxane (2 mL), and water (0.2 mL). The flask was subjected to 3 vacuum/argon cycles, then heated to 90 C for 3 h. The mixture was cooled to rt, filtered over celite, concentrated, and purified by column chromatography ($SiO_2$, 0-90% EtOAc/hex) to yield 5-((4-chloro-2-formyl-5-((3'-(5-formylthiophen-2-yl)-2,2'-dimethyl-[1,1'-biphenyl]-3-yl)methoxy)phenoxy)methyl)nicotinonitrile.

5-((4-chloro-2-((dimethylamino)methyl)-5-((3'-(5-((dimethylamino)methyl)thiophen-2-yl)-2,2'-dimethyl-[1,1'-biphenyl]-3-yl)methoxy)phenoxy)methyl)nicotinonitrile was synthesized according to general reductive amination procedure D. [M+1]=651.2. $^1$H NMR (400 MHz, Methanol-$d_4$) δ 8.96 (d, J=2.1 Hz, 1H), 8.92 (d, J=2.0 Hz, 1H), 8.37 (t, J=2.1 Hz, 1H), 7.54 (s, 1H), 7.48 (dd, J=7.7, 1.4 Hz, 1H), 7.40 (dd, J=7.8, 1.4 Hz, 1H), 7.35-7.24 (m, 3H), 7.18-7.05 (m, 4H), 5.39 (s, 2H), 5.32 (s, 2H), 4.58 (s, 2H), 4.30 (s, 2H), 2.92 (s, 6H), 2.83 (s, 6H), 2.12 (s, 3H), 2.05 (s, 3H).

Example 367:5-((4-chloro-2-((((1S,2S)-2-hydroxycyclohexyl)amino)methyl)-5-((3''-(2-((2-hydroxyethyl)amino)ethoxy)-2,2'-dimethyl-[1,1':3',1''-terphenyl]-3-yl)methoxy)phenoxy)methyl)nicotinonitrile

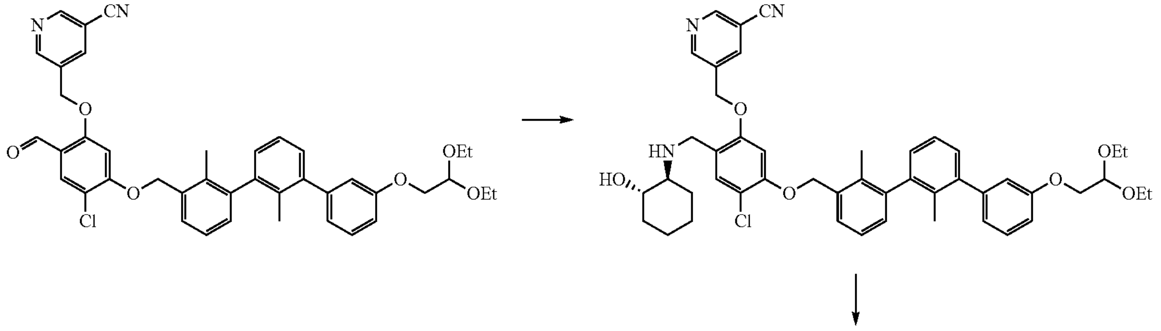

-continued

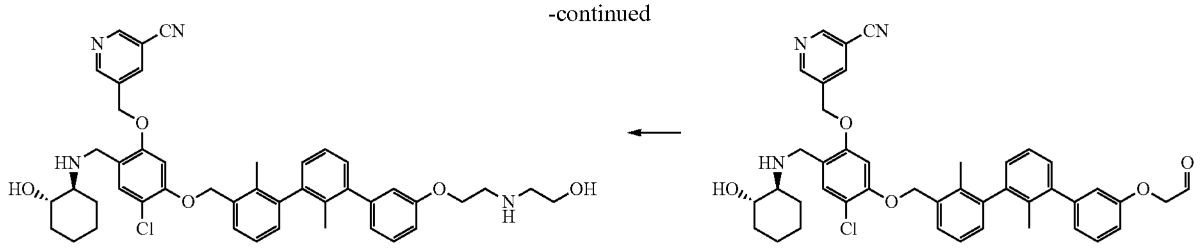

5-((4-chloro-5-((3"-(2,2-diethoxyethoxy)-2,2'-dimethyl-[1,1':3',1"-terphenyl]-3-yl)methoxy)-2-((((1S,2S)-2-hydroxycyclohexyl)amino)methyl)phenoxy)methyl)nicotinonitrilewassynthesized according to general reductive amination procedure D.

To a solution of 5-((4-chloro-5-((3"-(2,2-diethoxyethoxy)-2,2'-dimethyl-[1,1':3',1"-terphenyl]-3-yl)methoxy)-2-((((1S,2S)-2-hydroxycyclohexyl)amino)methyl)phenoxy)methyl)nicotinonitrile (183 mg, 0.16 mmol) in dioxane (3 mL) was added HCl (conc., 0.3 mL). The mixture was stirred for 3 h, then concentrated to yield 5-((4-chloro-5-((2,2'-dimethyl-3"-(2-oxoethoxy)-[1,1':3',1"-terphenyl]-3-yl)methoxy)-2-((((1S,2S)-2-hydroxycyclohexyl)amino)methyl)phenoxy)methyl)nicotinonitrile which was carried forward without further purification.

5-((4-chloro-2-((((1S,2S)-2-hydroxycyclohexyl)amino)methyl)-5-((3"-(2-((2-hydroxyethyl)amino)ethoxy)-2,2'-dimethyl-[1,1':3',1"-terphenyl]-3-yl)methoxy)phenoxy)methyl)nicotinonitrile was synthesized according to general reductive amination procedure D. [M+1]=761.3. $^1$H NMR (400 MHz, Methanol-$d_4$) δ 8.97 (d, J=1.7 Hz, 1H), 8.92 (d, J=1.6 Hz, 1H), 8.40 (s, 1H), 7.50 (s, 1H), 7.46 (d, J=7.4 Hz, 1H), 7.31-7.21 (m, 4H), 7.18 (dd, J=7.6, 1.2 Hz, 1H), 7.13 (d, J=7.6 Hz, 1H), 7.11-7.00 (m, 4H), 5.35 (s, 2H), 5.31 (s, 2H), 4.35 (t, 2H), 4.25 (d, J=13.1 Hz, 1H), 4.18-4.10 (m, 2H), 3.86 (t, 2H), 3.54 (t, 2H), 3.26 (t, 2H), 3.11 (dt, J=11.2, 3.5 Hz, 1H), 2.14 (s, 3H), 1.86 (s, 3H), 1.76-1.57 (m, 4H), 1.52-1.24 (m, 4H).

Example 368: 2-(1-((3"-((2-chloro-5-((5-cyanopyridin-3-yl)methoxy)-4-((((1R,2S)-2-hydroxycyclopentyl)amino)methyl)phenoxy)methyl)-2',2"-dimethyl-[1,1':3',1"-terphenyl]-4-yl)methyl)azetidin-3-yl) acetic acid

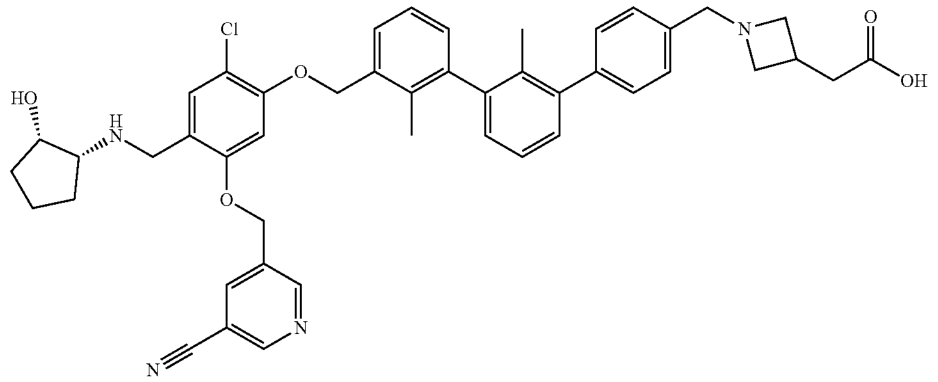 [SMILES: Cc1c(COc2cc(OCc3cncc(C#N)c3)c(CN[C@@H]3CCC[C@@H]3O)cc2Cl)cccc1-c1cccc(-c2ccc(CN3CC(CC(=O)O)C3)cc2)c1C]

The title compound was synthesized according to general reductive amination procedure C. [M+1]=771.3. $^1$H NMR (400 MHz, Methanol-$d_4$) δ 8.95 (dd, J=11.8, 2.0 Hz, 2H), 8.38 (s, 1H), 7.58 (d, J=8.0 Hz, 2H), 7.50-7.44 (m, 3H), 7.34-7.06 (m, 7H), 5.34 (d, J=19.0 Hz, 3H), 4.57-4.47 (m, 2H), 4.29 (s, 3H), 4.18-4.05 (m, 3H), 3.48-3.34 (m, 3H), 3.28-3.21 (m, 2H), 3.12 (s, 1H), 3.05-2.94 (m, 2H), 2.79 (dd, J=17.5, 8.6 Hz, 2H), 2.47 (dd, J=17.5, 7.7 Hz, 2H), 2.14 (s, 3H), 1.87 (s, 3H).

Example 369: (3S)-1-(5-(3'-((2-chloro-5-((5-cyano-pyridin-3-yl)methoxy)-4-((((1R,2S)-2-hydroxycyclo-pentyl)amino)methyl)phenoxy)methyl)-2,2'-dim-ethyl-[1,1'-biphenyl]-3-yl)-2,3-dihydro-1H-inden-1-yl)pyrrolidine-3-carboxylic acid

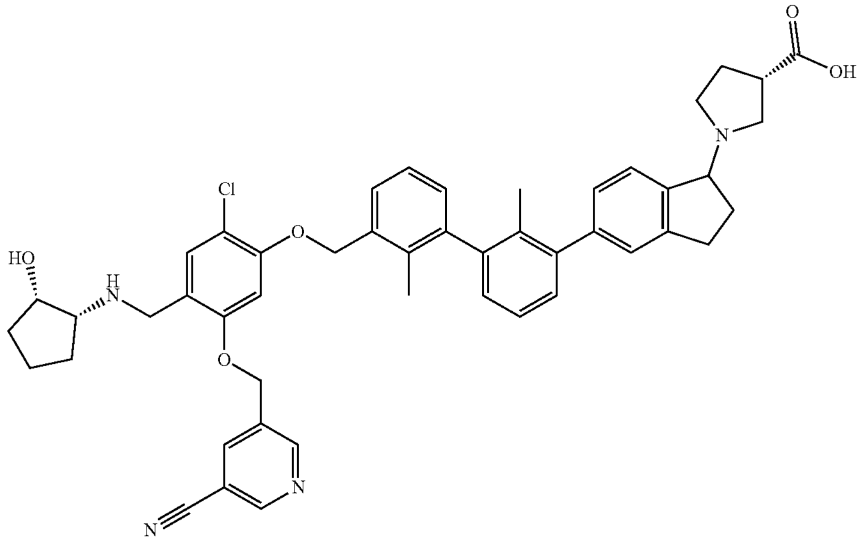 [SMILES: Cc1c(COc2cc(OCc3cncc(C#N)c3)c(CN[C@@H]3CCC[C@@H]3O)cc2Cl)cccc1-c1cccc(-c2ccc3c(c2)CCC3N2CC[C@H](C(=O)O)C2)c1C]

The title compound was synthesized according to general reductive amination procedure C. [M+1]=797.3. $^1$H NMR (400 MHz, Methanol-$d_4$) δ 8.95 (dd, J=10.5, 2.0 Hz, 2H), 8.39 (s, 1H), 7.66 (d, J=8.0 Hz, 1H), 7.51 (s, 1H), 7.46 (d, J=7.6 Hz, 1H), 7.39 (s, 1H), 7.34-7.07 (m, 7H), 5.34 (d, J=16.6 Hz, 4H), 5.00 (d, J=7.6 Hz, 1H), 4.27 (d, J=13.1 Hz, 2H), 4.15 (d, J=13.2 Hz, 1H), 3.49-3.37 (m, 3H), 3.10 (d, J=17.7 Hz, 3H), 2.61 (s, 4H), 2.14 (s, 3H), 2.02 (s, 2H), 1.87 (s, 4H), 1.82-1.56 (m, 5H).

Example 370: (3R)-1-(5-(3'-((2-chloro-5-((5-cyano-pyridin-3-yl)methoxy)-4-(((R)-3-hydroxypyrrolidin-1-yl)methyl)phenoxy)methyl)-2,2'-dimethyl-[1,1'-biphenyl]-3-yl)-2,3-dihydro-1H-inden-1-yl) pyrrolidine-3-carboxylic acid

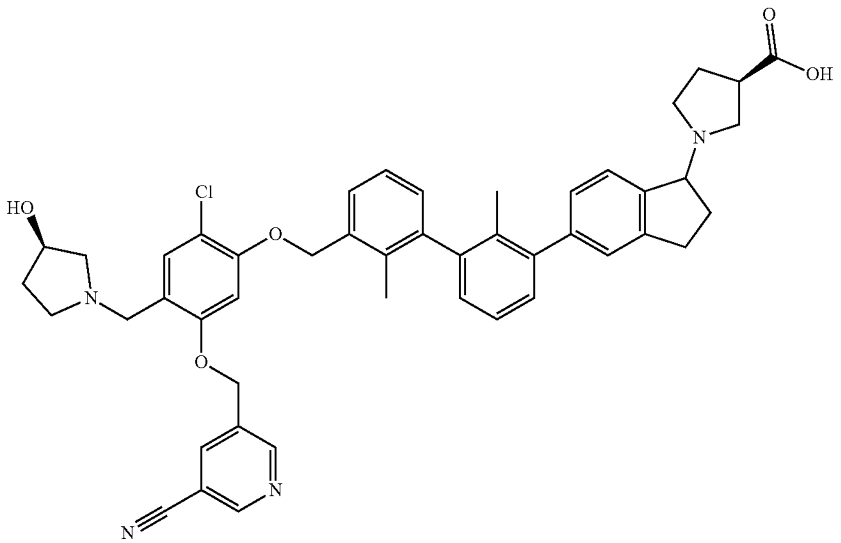 [SMILES: Cc1c(COc2cc(OCc3cncc(C#N)c3)c(CN3CC[C@@H](O)C3)cc2Cl)cccc1-c1cccc(-c2ccc3c(c2)CCC3N2CC[C@@H](C(=O)O)C2)c1C]

The title compound was synthesized according to general reductive amination procedure C. [M+1]=783.3. $^1$H NMR (400 MHz, Methanol-$d_4$) δ 8.94 (dd, J=8.7, 2.0 Hz, 2H), 8.37 (s, 1H), 7.66 (d, J=7.6 Hz, 1H), 7.56 (s, 1H), 7.47 (d, J=7.6 Hz, 1H), 7.40 (s, 1H), 7.37-7.25 (m, 3H), 7.18 (dd, J=20.1, 7.4 Hz, 2H), 7.11 (d, J=4.5 Hz, 2H), 5.39 (s, 2H), 5.32 (s, 2H), 5.00 (d, J=7.7 Hz, 1H), 4.53 (s, 2H), 4.41 (s, 2H), 3.78-3.35 (m, 8H), 3.10 (d, J=17.7 Hz, 2H), 2.63 (dd, J=15.4, 7.7 Hz, 2H), 2.49 (s, 1H), 2.14 (s, 3H), 2.04 (s, 1H), 1.88 (s, 3H).

Example 371: (2S)-2-((5-chloro-2-((5-cyanopyridin-3-yl)methoxy)-4-((2,2'-dimethyl-3'-(1-(3-methylazetidin-1-yl)-2,3-dihydro-1H-inden-5-yl)-[1,1'-biphenyl]-3-yl)methoxy)benzyl)amino)-3-hydroxy-2-methylpropanoic acid

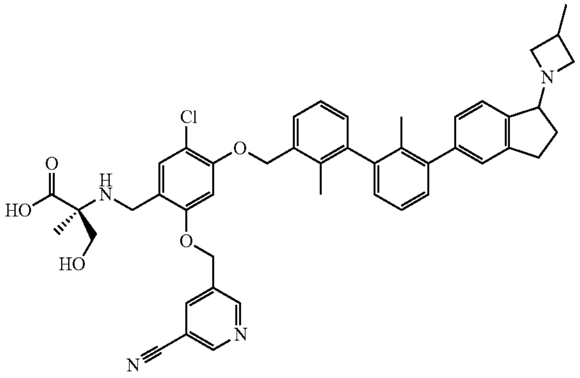 [SMILES: Cc1c(COc2cc(OCc3cncc(C#N)c3)c(CN[C@@](C)(CO)C(=O)O)cc2Cl)cccc1-c1cccc(-c2ccc3c(c2)CCC3N2CC(C)C2)c1C]

The title compound was synthesized according to general reductive amination procedure C. [M+1]=771.3. $^1$H NMR (400 MHz, Methanol-$d_4$) δ 8.97 (s, 2H), 8.41 (s, 1H), 7.60-7.44 (m, 3H), 7.37 (s, 1H), 7.28 (dt, J=15.9, 7.4 Hz, 3H), 7.21-7.05 (m, 4H), 5.34 (d, J=17.9 Hz, 4H), 4.36-4.06 (m, 6H), 4.00 (d, J=12.1 Hz, 2H), 3.79 (d, J=12.2 Hz, 2H), 3.14-2.94 (m, 3H), 2.55 (s, 1H), 2.14 (s, 3H), 1.86 (s, 3H), 1.52 (s, 3H), 1.36 (d, J=7.0 Hz, 1H), 1.28 (d, J=6.6 Hz, 2H).

Example 372: (3S)-4-((5-chloro-2-((5-cyanopyridin-3-yl)methoxy)-4-((3'-(1-(dimethylamino)-6-fluoro-2,3-dihydro-1H-inden-5-yl)-2,2'-dimethyl-[1,1'-biphenyl]-3-yl)methoxy)benzyl)amino)-3-hydroxybutanoic acid

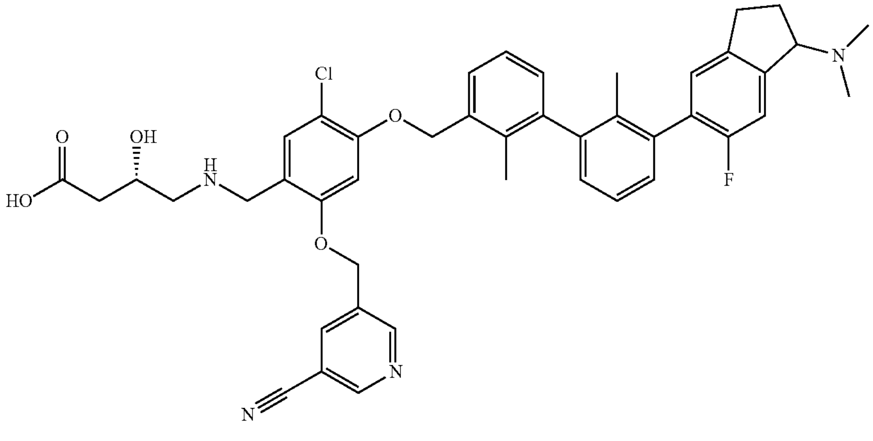 [SMILES: Cc1c(COc2cc(OCc3cncc(C#N)c3)c(CNC[C@@H](O)CC(=O)O)cc2Cl)cccc1-c1cccc(-c2cc3c(cc2F)C(N(C)C)CC3)c1C]

The title compound was synthesized according to general reductive amination procedure C. [M+1]=763.3. $^1$H NMR (400 MHz, Methanol-$d_4$) δ 8.94 (dd, J=11.3, 2.1 Hz, 2H), 8.37 (s, 1H), 7.51 (s, 1H), 7.49-7.33 (m, 4H), 7.33-7.19 (m, 3H), 7.16 (s, 1H), 7.08 (s, 1H), 5.37 (s, 2H), 5.31 (s, 2H), 5.06 (d, J=8.2 Hz, 1H), 4.23 (s, 3H), 3.24-3.15 (m, 2H), 3.09 (d, J=8.4 Hz, 1H), 2.97 (dd, J=12.8, 9.8 Hz, 2H), 2.91 (s, 2H), 2.76 (s, 2H), 2.69-2.56 (m, 2H), 2.51 (d, J=6.3 Hz, 3H), 2.13 (s, 3H), 1.82 (s, 3H).

Example 373: 5-((4-chloro-2-(((2-hydroxyethyl)amino)methyl)-5-((3'-(1-((S)-3-hydroxypyrrolidin-1-yl)-2,3-dihydro-1H-inden-5-yl)-2,2'-dimethyl-[1,1'-biphenyl]-3-yl)methoxy)phenoxy)methyl)nicotinonitrile

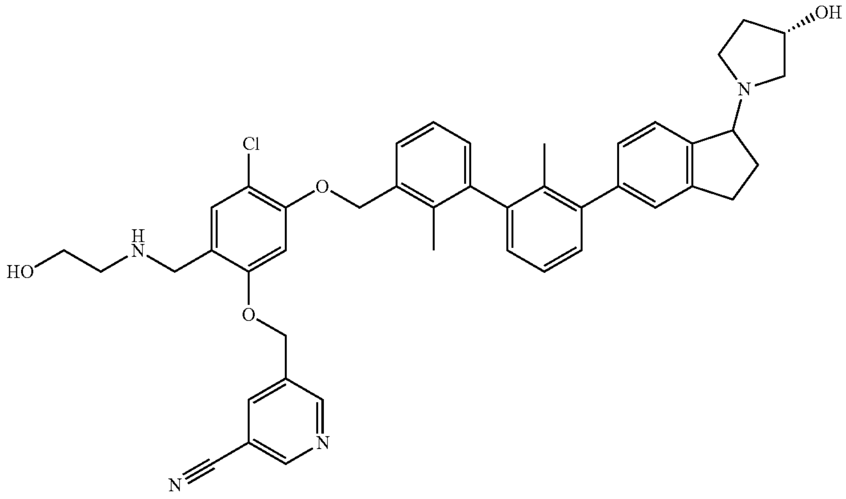 [SMILES: Cc1c(COc2cc(OCc3cncc(C#N)c3)c(CNCCO)cc2Cl)cccc1-c1cccc(-c2ccc3c(c2)CCC3N2CC[C@H](O)C2)c1C]

The title compound was synthesized according to general reductive amination procedure C. [M+1]=729.3. $^1$H NMR (400 MHz, Methanol-$d_4$) δ 8.98-8.88 (m, 2H), 8.38 (s, 1H), 7.66 (d, J=8.2 Hz, 1H), 7.53-7.43 (m, 2H), 7.38 (s, 1H), 7.34-7.07 (m, 7H), 5.48 (s, 4H), 5.37 (s, 2H), 5.31 (s, 2H), 5.08-4.96 (m, 2H), 4.61-4.51 (m, 2H), 4.23 (s, 2H), 3.77 (s, 3H), 3.47 (d, J=1.7 Hz, 2H), 3.10 (d, J=5.2 Hz, 3H), 2.14 (s, 3H), 1.88 (s, 3H).

Example 374: (2S)-2-((5-chloro-2-((5-cyanopyridin-3-yl)methoxy)-4-((4"-(1-(2-hydroxyethyl)pyrrolidin-2-yl)-2,2'-dimethyl-[1,1':3',1"-terphenyl]-3-yl)methoxy)benzyl)amino)-3-hydroxy-2-methylpropanoic acid

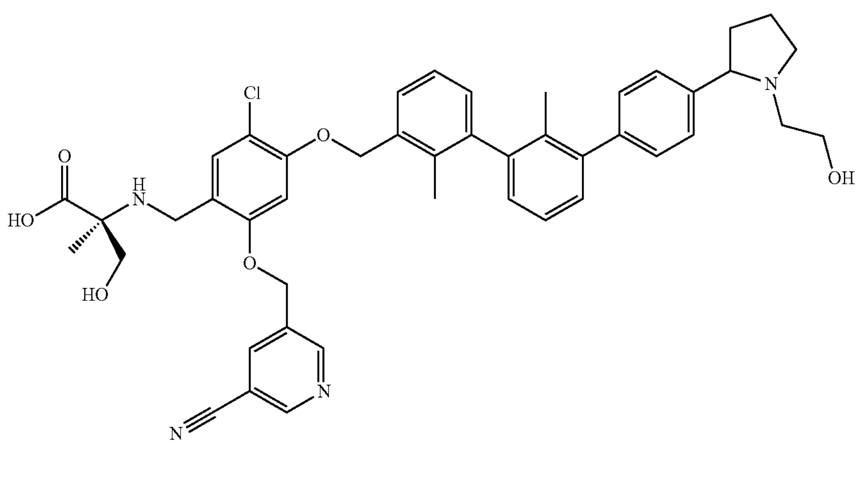 [SMILES: Cc1c(COc2cc(OCc3cncc(C#N)c3)c(CN[C@@](C)(CO)C(=O)O)cc2Cl)cccc1-c1cccc(-c2ccc(C3CCCN3CCO)cc2)c1C]

The title compound was synthesized according to general reductive amination procedure C. [M+1]=775.3. $^1$H NMR (400 MHz, Methanol-$d_4$) δ 8.90 (s, 2H), 7.63 (d, J=8.1 Hz, 2H), 7.57-7.47 (m, 3H), 7.31-7.07 (m, 6H), 5.34 (d, J=18.0 Hz, 4H), 4.26 (s, 2H), 3.98 (d, J=12.2 Hz, 2H), 3.81-3.67 (m, 4H), 3.47 (t, J=1.6 Hz, 2H), 3.12 (s, 2H), 2.37-2.28 (m, 3H), 2.15 (s, 3H), 1.89 (s, 3H), 1.50 (s, 3H).

Example 375: (2S)-2-((5-chloro-2-((5-cyanopyridin-3-yl)methoxy)-4-((3'-(1-((2-hydroxyethyl)(methyl)amino)-2,3-dihydro-1H-inden-5-yl)-2,2'-dimethyl-[1,1'-biphenyl]-3-yl)methoxy)benzyl)amino)-3-hydroxy-2-methylpropanoic acid

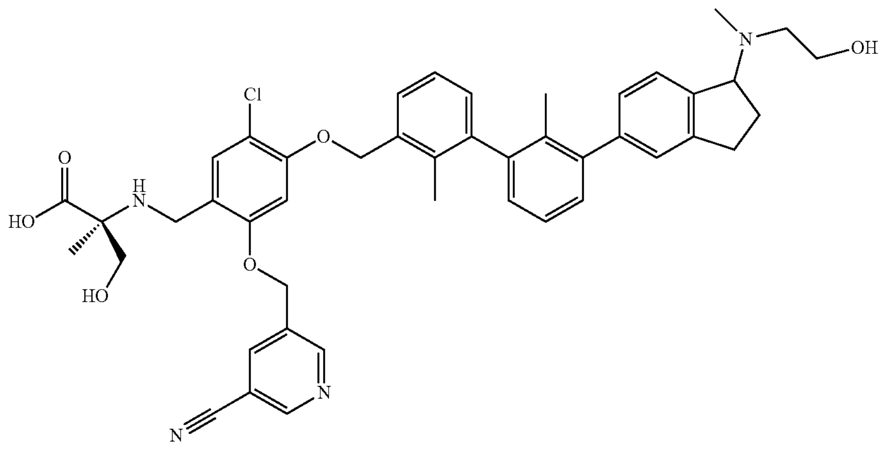 [SMILES: Cc1c(COc2cc(OCc3cncc(C#N)c3)c(CN[C@@](C)(CO)C(=O)O)cc2Cl)cccc1-c1cccc(-c2ccc3c(c2)CCC3N(C)CCO)c1C]

The title compound was synthesized according to general reductive amination procedure C. [M+1]=775.3. $^1$H NMR (400 MHz, Methanol-$d_4$) δ 8.98 (d, J=2.1 Hz, 1H), 8.91 (d, J=2.0 Hz, 1H), 8.42 (s, 1H), 7.64 (d, J=8.2 Hz, 1H), 7.55 (s, 1H), 7.47 (d, J=7.4 Hz, 1H), 7.39-7.07 (m, 8H), 5.34 (d, J=17.0 Hz, 4H), 4.27 (s, 2H), 4.00 (d, J=12.1 Hz, 2H), 3.92 (s, 1H), 3.79 (d, J=12.2 Hz, 2H), 3.12 (t, J=1.7 Hz, 2H), 2.94 (s, 2H), 2.79 (s, 1H), 2.68-2.57 (m, 2H), 2.47 (s, 2H), 2.15 (s, 3H), 1.88 (s, 3H), 1.52 (s, 3H).

Example 376: (2S)-2-((5-chloro-2-((5-cyanopyridin-3-yl)methoxy)-4-((3'-(3-(dimethylamino)-2,3-dihydrobenzofuran-6-yl)-2,2'-dimethyl-[1,1'-biphenyl]-3-yl)methoxy)benzyl)amino)-3-hydroxy-2-methylpropanoic acid

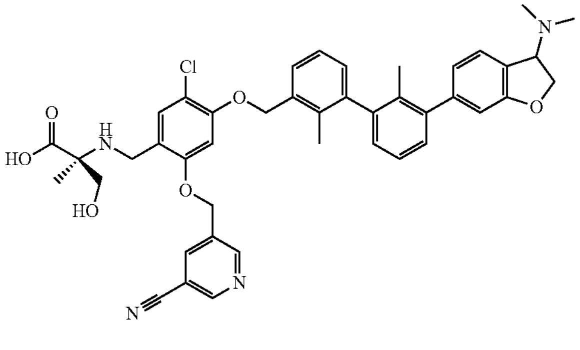 [SMILES: Cc1c(COc2cc(OCc3cncc(C#N)c3)c(CN[C@@](C)(CO)C(=O)O)cc2Cl)cccc1-c1cccc(-c2ccc3c(c2)OCC3N(C)C)c1C]

The title compound was synthesized according to general reductive amination procedure C. [M+1]=747.3. $^1$H NMR (400 MHz, Methanol-$d_4$) δ 8.41 (s, 1H), 7.64 (d, J=7.9 Hz, 1H), 7.55 (s, 1H), 7.47 (d, J=7.7 Hz, 1H), 7.33-7.19 (m, 3H), 7.18-7.03 (m, 4H), 6.99 (s, 1H), 5.34 (d, J=16.8 Hz, 4H), 5.22 (d, J=7.2 Hz, 1H), 5.02 (d, J=12.6 Hz, 1H), 4.71 (d, J=12.1 Hz, 1H), 4.27 (s, 2H), 3.99 (d, J=12.2 Hz, 2H), 3.78 (d, J=12.1 Hz, 2H), 2.83 (s, 4H), 2.14 (s, 3H), 1.89 (s, 3H), 1.51 (s, 3H).

Example 377: (2S,4S)-1-(5-chloro-2-((5-cyanopyridin-3-yl)methoxy)-4-((3'-((R)-1-(dimethylamino)-2,3-dihydro-1H-inden-5-yl)-2,2'-dimethyl-[1,1'-biphenyl]-3-yl)methoxy)benzyl)-4-hydroxypyrrolidine-2-carboxylic acid

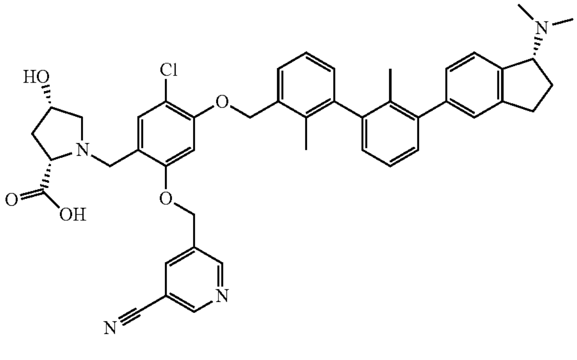 [SMILES: Cc1c(COc2cc(OCc3cncc(C#N)c3)c(CN3C[C@@H](O)C[C@H]3C(=O)O)cc2Cl)cccc1-c1cccc(-c2ccc3c(c2)CC[C@H]3N(C)C)c1C]

The title compound was synthesized according to general reductive amination procedure C. [M+1]=757.3. $^1$H NMR (400 MHz, Methanol-$d_4$) δ 8.97 (s, 1H), 8.92 (d, J=1.8 Hz, 1H), 8.42 (s, 1H), 7.60 (d, J=7.9 Hz, 1H), 7.49 (d, J=13.9 Hz, 2H), 7.41-7.08 (m, 8H), 5.40 (s, 1H), 5.31 (s, 1H), 5.04 (d, J=6.5 Hz, 1H), 4.46 (d, J=13.9 Hz, 2H), 4.37 (d, J=13.9 Hz, 1H), 4.20 (dd, J=10.9, 3.8 Hz, 1H), 3.34 (s, 4H), 3.22 (dd, J=16.8, 8.7 Hz, 2H), 2.90 (s, 2H), 2.75 (s, 2H), 2.67-2.53 (m, 3H), 2.49 (d, J=8.4 Hz, 1H), 2.25 (d, J=12.9 Hz, 2H), 2.14 (s, 3H), 1.88 (s, 3H).

Example 378: (S)-2-((5-chloro-2-((5-cyanopyridin-3-yl)methoxy)-4-((3'-((R)-1-(dimethylamino)-2,3-dihydro-1H-inden-5-yl)-2,2'-dimethyl-[1,1'-biphenyl]-3-yl)methoxy)benzyl)amino)-3-hydroxy-2-methylpropanoic acid

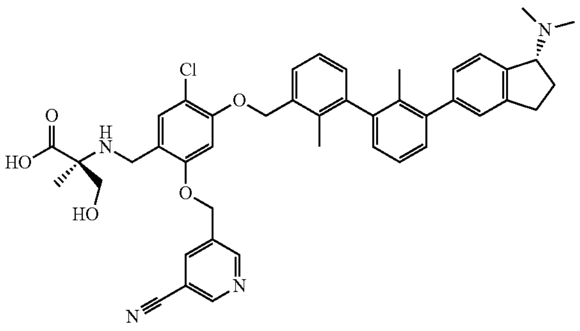 [SMILES: Cc1c(COc2cc(OCc3cncc(C#N)c3)c(CN[C@@](C)(CO)C(=O)O)cc2Cl)cccc1-c1cccc(-c2ccc3c(c2)CC[C@H]3N(C)C)c1C]

The title compound was synthesized according to general reductive amination procedure C. [M+1]=745.3. $^1H$ NMR (400 MHz, Methanol-$d_4$) δ 8.98 (d, J=2.0 Hz, 1H), 8.91 (d, J=1.9 Hz, 1H), 8.41 (s, 1H), 7.62-7.54 (m, 2H), 7.47 (d, J=7.5 Hz, 1H), 7.40 (s, 1H), 7.36-7.05 (m, 7H), 5.34 (d, J=16.8 Hz, 4H), 5.04 (d, J=8.7 Hz, 1H), 4.27 (s, 2H), 4.00 (d, J=12.1 Hz, 1H), 3.79 (d, J=12.2 Hz, 1H), 3.26-3.18 (m, 1H), 2.90 (s, 2H), 2.75 (s, 2H), 2.62-2.43 (m, 3H), 2.15 (s, 3H), 1.88 (s, 3H), 1.52 (s, 3H).

Example 379:5-((4-chloro-5-((2,2'-dimethyl-4''-(pyrrolidin-2-yl)-[1,1':3',1''-terphenyl]-3-yl)methoxy)-2-(((2-hydroxyethyl)amino)methyl)phenoxy)methyl) nicotinonitrile

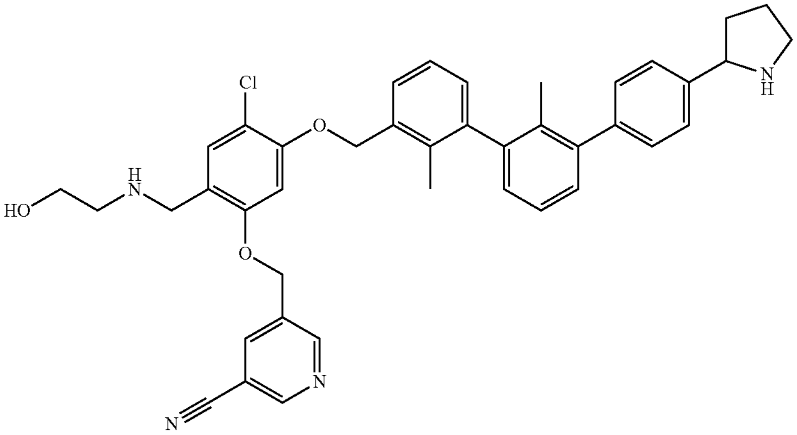 [SMILES: Cc1c(COc2cc(OCc3cncc(C#N)c3)c(CNCCO)cc2Cl)cccc1-c1cccc(-c2ccc(C3CCCN3)cc2)c1C]

The title compound was synthesized according to general reductive amination procedure C. [M+1]=673.3. HPLC $T_R$=4.87 min.

Example 380: (S)-4-((5-chloro-2-((5-cyanopyridin-3-yl)methoxy)-4-((4"-((S)-1-(dimethylamino)ethyl)-2,2'-dimethyl-[1,1':3',1"-terphenyl]-3-yl)methoxy)benzyl)amino)-3-hydroxybutanoic acid

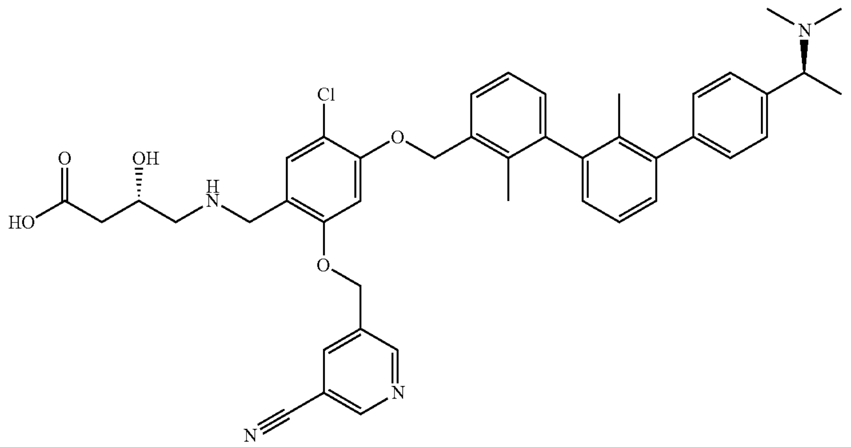 [SMILES: Cc1c(COc2cc(OCc3cncc(C#N)c3)c(CNC[C@@H](O)CC(=O)O)cc2Cl)cccc1-c1cccc(-c2ccc([C@H](C)N(C)C)cc2)c1C]

The title compound was synthesized according to general reductive amination procedure C. [M+1]=733.3. $^1$H NMR (400 MHz, Methanol-$d_4$) δ 8.94 (dd, J=12.0, 2.0 Hz, 2H), 8.37 (s, 1H), 7.57 (d, J=8.0 Hz, 2H), 7.53-7.42 (m, 4H), 7.35-7.19 (m, 3H), 7.17-7.05 (m, 3H), 5.38 (s, 2H), 5.31 (s, 2H), 4.37 (s, 2H), 4.23 (s, 3H), 3.20 (dd, J=12.7, 3.0 Hz, 2H), 3.00-2.94 (m, 1H), 2.90 (s, 6H), 2.51 (dd, J=6.3, 1.1 Hz, 2H), 2.14 (s, 3H), 1.89 (s, 3H).

Example 381: (3S)-4-((5-chloro-2-((5-cyanopyridin-3-yl)methoxy)-4-((3'-(1-(dimethylamino)-2,3-dihydro-1H-inden-5-yl)-2,2'-dimethyl-[1,1'-biphenyl]-3-yl)methoxy)benzyl)amino)-3-hydroxybutanoic acid

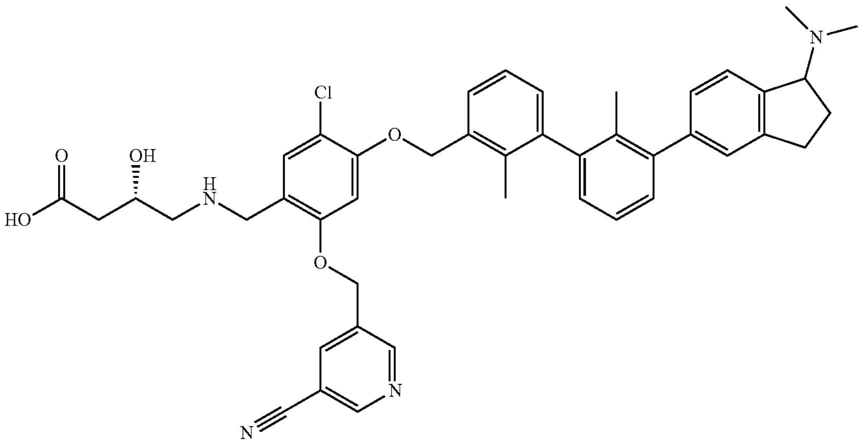 [SMILES: Cc1c(COc2cc(OCc3cncc(C#N)c3)c(CNC[C@@H](O)CC(=O)O)cc2Cl)cccc1-c1cccc(-c2ccc3c(c2)CCC3N(C)C)c1C]

The title compound was synthesized according to general reductive amination procedure C. [M+1]=745.3. $^1$H NMR (400 MHz, Methanol-$d_4$) δ 8.94 (dd, J=12.6, 2.1 Hz, 2H), 8.37 (s, 1H), 7.58-7.42 (m, 3H), 7.29 (td, J=13.6, 7.0 Hz, 4H), 7.22-7.05 (m, 4H), 5.37 (s, 2H), 5.31 (s, 2H), 4.23 (s, 4H), 3.29-3.15 (m, 3H), 3.02 (ddd, J=37.3, 13.9, 8.8 Hz, 3H), 2.90 (s, 6H), 2.74-2.60 (m, 2H), 2.51 (dd, J=6.3, 1.1 Hz, 2H), 2.14 (s, 3H), 2.04-1.91 (m, 1H), 1.86 (s, 3H).

Example 382: 5-((4-chloro-2-((dimethylamino)methyl)-5-((3'-(6-((dimethylamino)methyl)pyridin-3-yl)-2,2'-dimethyl-[1,1'-biphenyl]-3-yl)methoxy)phenoxy)methyl)nicotinonitrile

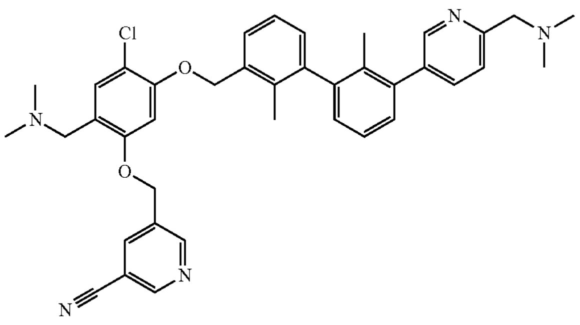

The title compound was synthesized according to general reductive amination procedure C. [M+1]=646.3. $^1$H NMR (400 MHz, Methanol-$d_4$) δ 8.95 (dd, J=6.3, 2.0 Hz, 2H), 8.69 (s, 1H), 8.36 (d, J=2.2 Hz, 1H), 7.92 (dd, J=7.9, 2.2 Hz, 1H), 7.59-7.45 (m, 3H), 7.41-7.34 (m, 1H), 7.29 (t, J=7.9 Hz, 2H), 7.23-7.09 (m, 3H), 5.40 (s, 2H), 5.32 (s, 2H), 4.54 (s, 2H), 4.30 (s, 2H), 2.99 (s, 6H), 2.83 (s, 6H), 2.15 (s, 3H), 1.92 (s, 3H).

Example 383: (S)-4-((5-chloro-2-((5-cyanopyridin-3-yl)methoxy)-4-((4"-((dimethylamino)methyl)-2,2'-dimethyl-[1,1':3',1"-terphenyl]-3-yl)methoxy)benzyl)amino)-3-hydroxybutanoic acid

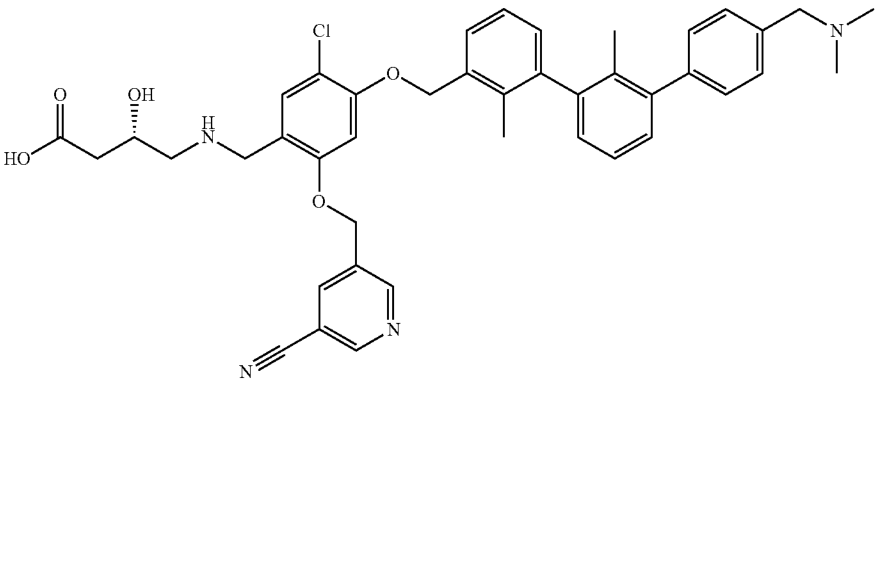 [SMILES: Cc1c(COc2cc(OCc3cncc(C#N)c3)c(CNC[C@@H](O)CC(=O)O)cc2Cl)cccc1-c1cccc(-c2ccc(CN(C)C)cc2)c1C]

The title compound was synthesized according to general reductive amination procedure C. [M+1]=719.3. $^1$H NMR (400 MHz, Methanol-$d_4$) δ 8.95 (dd, J=12.0, 2.0 Hz, 2H), 8.35 (s, 1H), 7.57 (d, J=8.0 Hz, 2H), 7.53-7.43 (m, 4H), 7.37-7.19 (m, 3H), 7.19-7.00 (m, 3H), 5.40 (s, 2H), 5.31 (s, 2H), 4.36 (s, 2H), 4.23 (s, 3H), 3.20 (dd, J=12.7, 3.0 Hz, 1H), 3.01-2.94 (m, 1H), 2.90 (s, 5H), 2.51 (dd, J=6.3, 1.1 Hz, 2H), 2.10 (s, 3H), 1.90 (s, 3H).

Example 384: (S)-4-((4-((4"-((((S)-3-carboxy-2-hydroxypropyl)amino)methyl)-2,2'-dimethyl-[1,1':3',1"-terphenyl]-3-yl)methoxy)-5-chloro-2-((5-cyanopyridin-3-yl)methoxy)benzyl)amino)-3-hydroxybutanoic acid

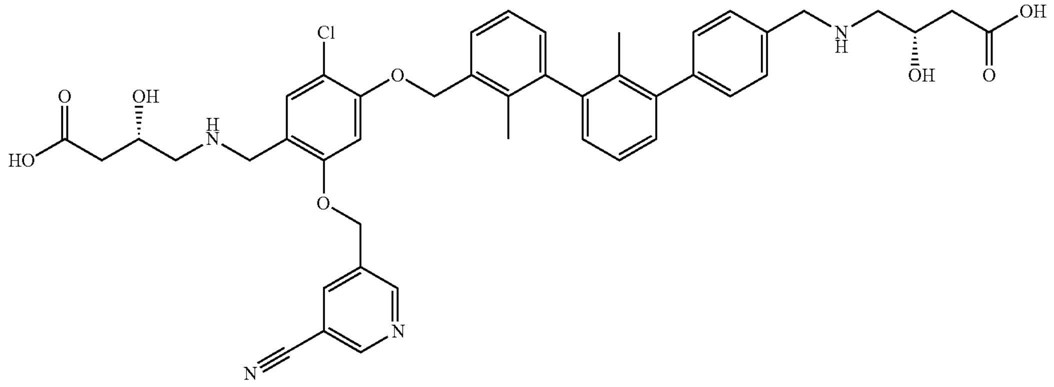 [SMILES: Cc1c(COc2cc(OCc3cncc(C#N)c3)c(CNC[C@@H](O)CC(=O)O)cc2Cl)cccc1-c1cccc(-c2ccc(CNC[C@@H](O)CC(=O)O)cc2)c1C]

The title compound was synthesized according to general reductive amination procedure C. [M+1]=793.3. $^1$H NMR (400 MHz, Methanol-$d_4$) δ 8.94 (dd, J=11.8, 2.0 Hz, 2H), 8.38 (s, 1H), 7.59 (d, J=8.0 Hz, 2H), 7.51-7.45 (m, 3H), 7.35-7.06 (m, 7H), 5.38 (s, 2H), 5.31 (s, 2H), 4.42 (s, 2H), 4.23 (s, 3H), 4.06 (s, 1H), 3.74 (s, 1H), 3.42 (s, 1H), 3.20 (dd, J=12.8, 3.0 Hz, 2H), 3.02-2.92 (m, 2H), 2.51 (d, J=6.3 Hz, 2H), 2.14 (s, 3H), 1.89 (s, 3H).

Example 385: (S)-4-((2-((3"-(((3-bromo-5-((((S)-3-carboxy-2-hydroxypropyl)amino)methyl)-6-((5-cyanopyridin-3-yl)methoxy)pyridin-2-yl)oxy)methyl)-2',2"-dimethyl-[1,1':3',1"-terphenyl]-4-yl)oxy)ethyl)amino)-3-hydroxybutanoic acid

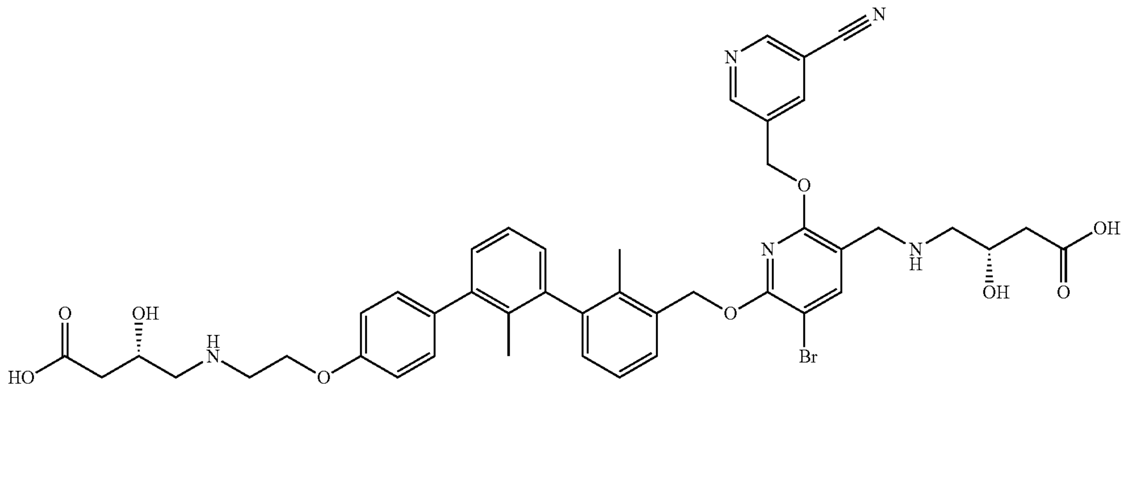 [SMILES: Cc1c(COc2nc(OCc3cncc(C#N)c3)c(CNC[C@@H](O)CC(=O)O)cc2Br)cccc1-c1cccc(-c2ccc(OCCNC[C@@H](O)CC(=O)O)cc2)c1C]

The title compound was synthesized according to general reductive amination procedure C. [M+1]=868.3. HPLC $T_R$=4.98 min.

Example 386: (S)-4-((4-((3'-(4-(aminomethyl)-1H-1,2,3-triazol-1-yl)-2,2'-dimethyl-[1,1'-biphenyl]-3-yl)methoxy)-5-chloro-2-((5-cyanopyridin-3-yl)methoxy)benzyl)amino)-3-hydroxybutanoic acid
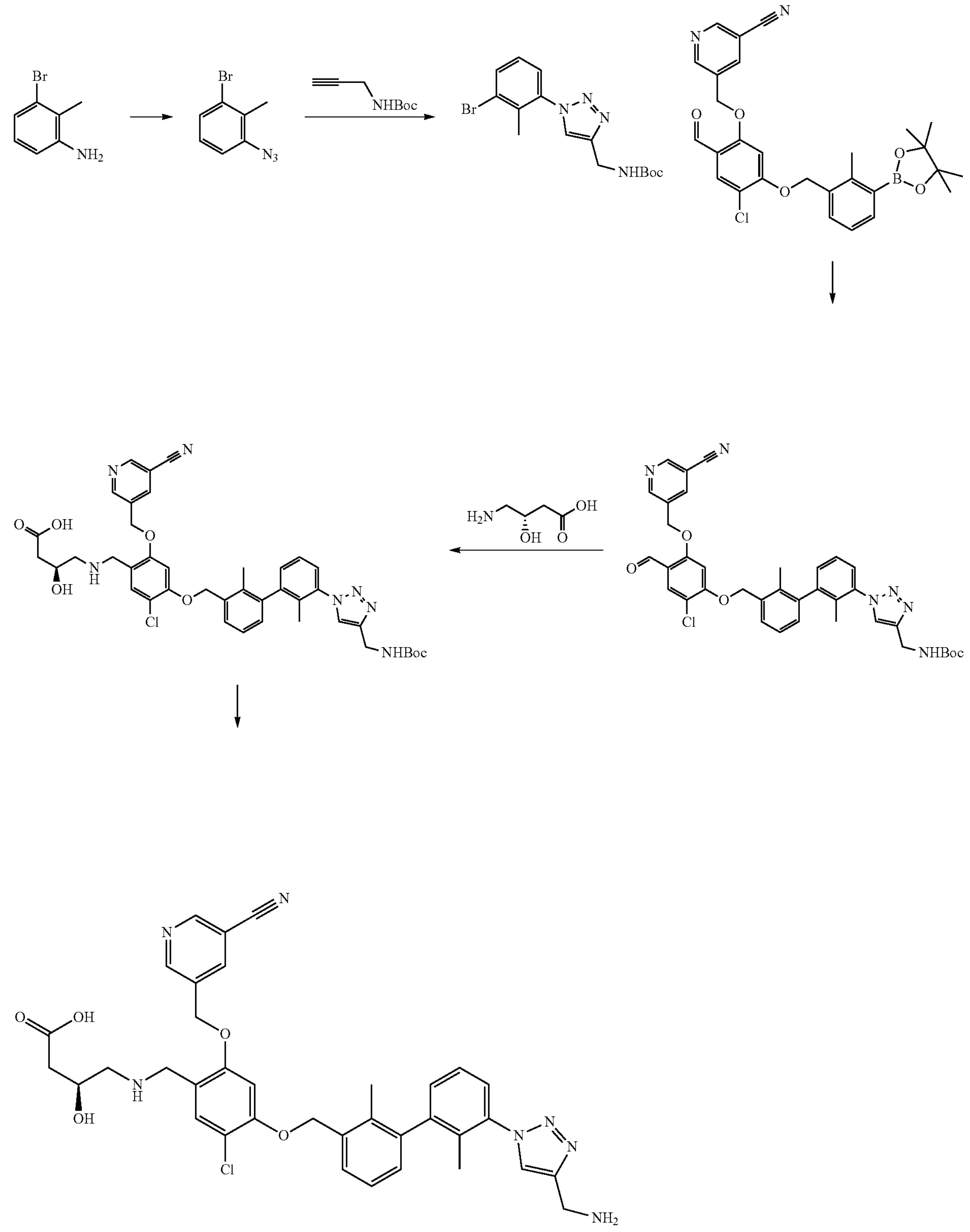

2-Azido-1,3-dimethylimidazolinium hexafluorophosphate (1.149 g, 4.03 mmol) was added to a solution of 3-bromo-2-methylaniline (500 mg, 2.69 mmol) and 4-(dimethylamino)pyridine (657 mg, 5.37 mmol) in dichloromethane (15 mL). After 14 hours saturated sodium bicarbonate (15 mL) was added. The aqueous phase was extracted with ethyl acetate (3×20 mL). The combined organic extracts were washed with saturated sodium bicarbonate (25 mL) and brine (25 mL). The organic phase was dried over sodium sulfate and the solvent was removed under reduced pressure. The residue was subjected to flash chromatography (0-100% ethyl acetate/hexanes). The fractions containing product were combined and the solvent was removed under reduced pressure, providing 1-azido-3-bromo-2-methylbenzene.

1-Azido-3-bromo-2-methylbenzene (50 mg, 0.236 mmol) was added to a mixture of tert-butyl prop-2-yn-1-ylcarbamate (73.2 mg, 0.472 mmol) and copper(I) thiophene-2-carboxylate (3.02 mg, 0.02 mmol) in tetrahydrofuran (1 mL). After 14 hours the solvent was removed under reduced pressure. The residue was subjected to flash chromatography (0-100% ethyl acetate/hexanes). The fractions containing product were combined and the solvent was removed under reduced pressure, tert-butyl ((1-(3-bromo-2-methylphenyl)-1H-1,2,3-triazol-4-yl)methyl)carbamate.

5-((4-chloro-2-formyl-5-((2-methyl-3-(4,4,5,5-tetramethyl-1,3,2-dioxaborolan-2-yl)benzyl)oxy)phenoxy)methyl)nicotinonitrile (80 mg, 0.154 mmol), tert-butyl ((1-(3-bromo-2-methylphenyl)-1H-1,2,3-triazol-4-yl)methyl)carbamate (79.3 mg, 0.216 mmol), Tetrakis (triphenylphosphine)palladium (0) (17.8 mg, 0.015 mmol), potassium carbonate (19 mg, 0.308 mmol) in water (0.4 mL), and dimethoxyethane (4 mL) was degassed with argon for 2 minutes. The above were combined and heated at 85° C. for 3 hours. The reaction was diluted with ethyl acetate (100 mL) and washed with water (3×50 mL) and brine (50 mL). The organic phase was dried over sodium sulfate and the solvent was removed under reduced pressure. The residue was subjected to flash chromatography (0-100% EtOAc/hexanes). The fractions containing product and the solvent was removed under reduced pressure providing tert-butyl ((1-(3'-((2-chloro-5-((5-cyanopyridin-3-yl)methoxy)-4-formylphenoxy)methyl)-2,2'-dimethyl-[1,1'-biphenyl]-3-yl)-1H-1,2,3-triazol-4-yl)methyl)carbamate.

(S)-4-((4-((3'-(4-(((tert-butoxycarbonyl)amino)methyl)-1H-1,2,3-triazol-1-yl)-2,2'-dimethyl-[1,1'-biphenyl]-3-yl)methoxy)-5-chloro-2-((5-cyanopyridin-3-yl)methoxy)benzyl)amino)-3-hydroxybutanoic acid was synthesized according to general reductive amination procedure G.

Trifluoroacetic acid (0.3 mL) was added to a solution (S)-4-((4-((3'-(4-(((tert-butoxycarbonyl)amino)methyl)-1H-1,2,3-triazol-1-yl)-2,2'-dimethyl-[1,1'-biphenyl]-3-yl)methoxy)-5-chloro-2-((5-cyanopyridin-3-yl)methoxy)benzyl)amino)-3-hydroxybutanoic acid (42 mg, 0.0537 mmol) in dichloromethane (0.7 mL) and After 20 minutes the reaction was diluted with acetonitrile (5 mL) and co-evaporated until ~1 mL remained. The material was co-evaporated with acetonitrile two more times. The residue was taken up in methanol (0.5 mL) and water (0.5 mL). The solution was subjected to preparative HPLC (eluant: 0.1% trifluoroacetic acid in acetonitrile/water). The fractions containing product were combined and subjected to lyophilization, providing (S)-4-((4-((3'-(4-(aminomethyl)-1H-1,2,3-triazol-1-yl)-2,2'-dimethyl-[1,1'-biphenyl]-3-yl)methoxy)-5-chloro-2-((5-cyanopyridin-3-yl)methoxy)benzyl)amino)-3-hydroxybutanoic acid. [M+1]=682.0. $^1$H NMR (400 MHz, Methanol-$d_4$) δ 8.94 (m, 2H), 8.38 (s, 1H), 8.32 (s, 1H), 7.58-7.46 (m, 3H), 7.40 (ddd, J=10.5, 7.6, 1.5 Hz, 2H), 7.31 (t, J=7.6 Hz, 1H), 7.22-7.13 (m, 1H), 7.09 (s, 1H), 5.39 (s, 2H), 5.32 (s, 2H), 4.36 (s, 2H), 4.24 (m, 3H), 3.20 (dd, J=12.7, 3.1 Hz, 1H), 3.05-2.91 (m, 1H), 2.52 (dd, J=6.2, 1.1 Hz, 2H), 2.15 (s, 3H), 1.82 (s, 3H).

Example 387: (S)-4-((3-(4-(3'-((4-((((S)-3-carboxy-2-hydroxypropyl)amino)methyl)-2-chloro-5-((5-cyanopyridin-3-yl)methoxy)phenoxy)methyl)-2,2'-dimethyl-[1,1'-biphenyl]-3-yl)-1H-1,2,3-triazol-1-yl)propyl)amino)-3-hydroxybutanoic acid

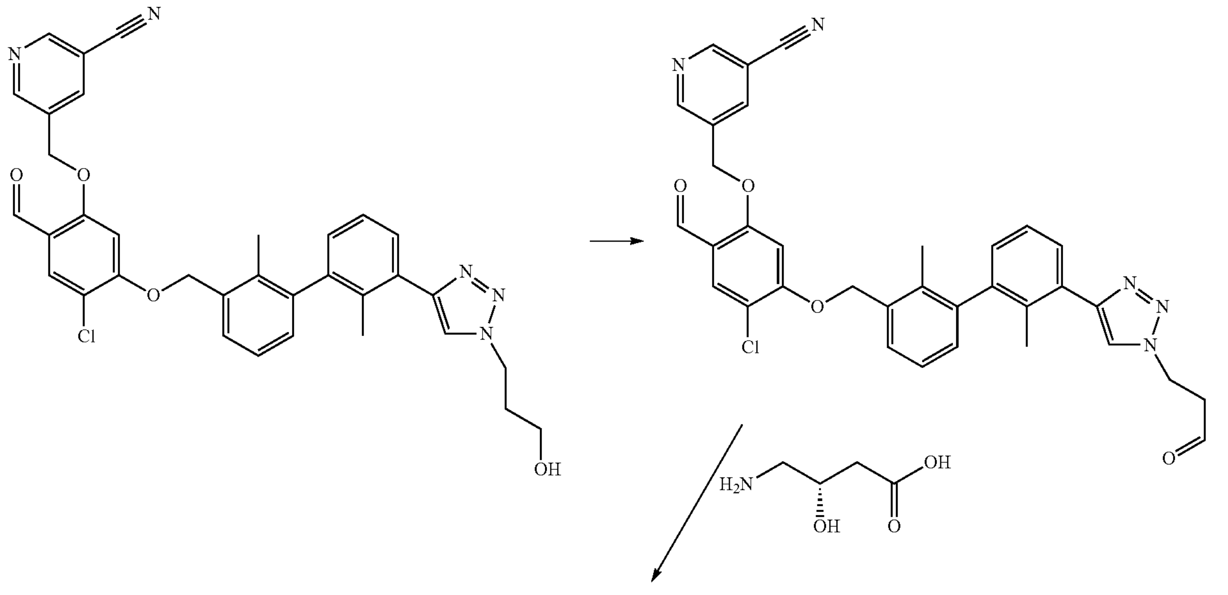

-continued

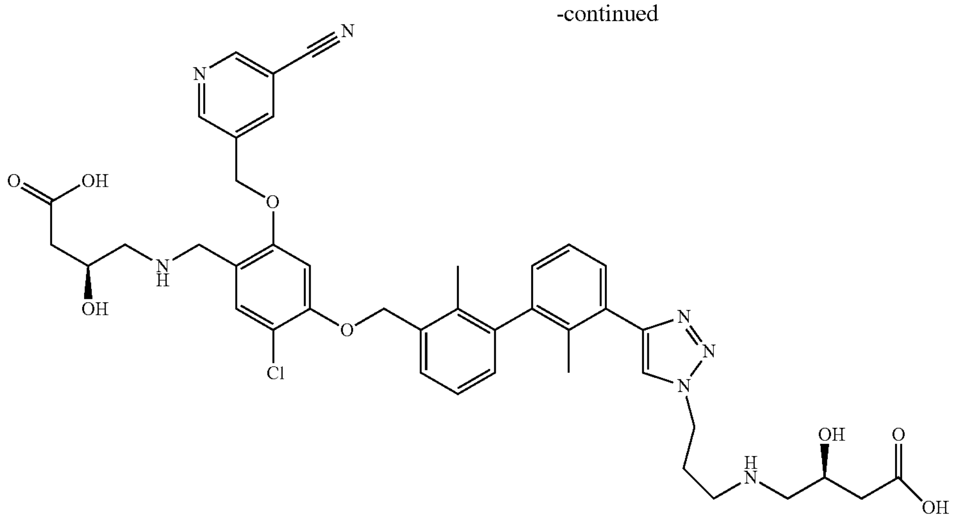

5-((4-chloro-2-formyl-5-((3'-(1-(3-hydroxypropyl)-1H-1,2,3-triazol-4-yl)-2,2'-dimethyl-[1,1'-biphenyl]-3-yl)methoxy)phenoxy)methyl)nicotinonitrile was prepared analogously to Example 330.

Dess-martin periodinane was added to a solution of 5-((4-chloro-2-formyl-5-((3'-(1-(3-hydroxypropyl)-1H-1,2,3-triazol-4-yl)-2,2'-dimethyl-[1,1'-biphenyl]-3-yl)methoxy)phenoxy)methyl)nicotinonitrile (70 mg, 0.115 mmol) in dichloromethane (4 mL). After 30 minutes the reaction was diluted with ethyl acetate (25 mL) and washed with saturated sodium bicarbonate (15 mL) and brine (15 mL). The organic phase was dried over sodium sulfate and the solvent was removed under reduced pressure, providing 5-((4-chloro-5-((2,2'-dimethyl-3'-(1-(3-oxopropyl)-1H-1,2,3-triazol-4-yl)-[1,1'-biphenyl]-3-yl)methoxy)-2-formylphenoxy)methyl)nicotinonitrile.

(S)-4-((3-(4-(3'-((4-((((S)-3-carboxy-2-hydroxypropyl)amino)methyl)-2-chloro-5-((5-cyanopyridin-3-yl)methoxy)phenoxy)methyl)-2,2'-dimethyl-[1,1'-biphenyl]-3-yl)-1H-1,2,3-triazol-1-yl)propyl)amino)-3-hydroxybutanoic acid was synthesized according to general reductive amination procedure G. [M+1]=812.0. $^{1}$H NMR (400 MHz, Methanol-$d_4$) δ 8.94 (m, 2H), 8.38 (s, 1H), 8.20 (s, 1H), 7.63-7.55 (m, 1H), 7.54-7.43 (m, 2H), 7.35 (t, J=7.6 Hz, 1H), 7.28 (t, J=7.6 Hz, 1H), 7.21-7.01 (m, 3H), 5.38 (s, 2H), 5.32 (s, 2H), 4.63 (t, J=6.8 Hz, 2H), 4.35-4.12 (m, 4H), 3.25-3.10 (m, 4H), 3.11-2.89 (m, 4H), 2.62-2.48 (m, 4H), 2.48-2.29 (m, 2H), 2.13 (s, 3H), 2.08 (s, 3H).

Example 388: (S)-2-((4-(((4"-(2-(((S)-2-carboxy-1-hydroxypropan-2-yl)amino)ethoxy)-2,2'-dimethyl-[1,1':3',1"-terphenyl]-3-yl)oxy)methyl)-5-chloro-2-((5-cyanopyridin-3-yl)methoxy)benzyl)amino)-3-hydroxy-2-methylpropanoic acid

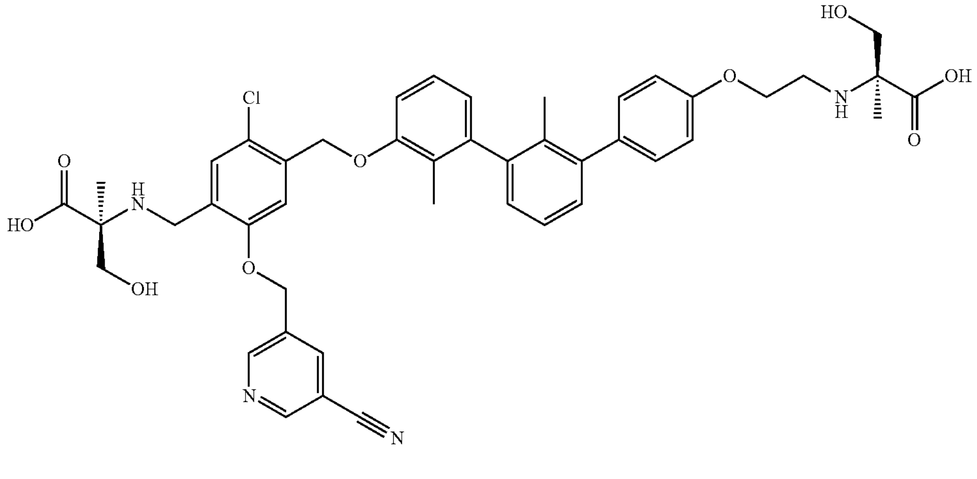

The title compound was synthesized according to general reductive amination procedure D. [M+1]=823.2. $^{1}$H NMR (400 MHz, Acetonitrile-$d_3$) δ 8.88 (s, 1H), 8.84 (s, 1H), 8.24 (s, 1H), 7.55 (s, 1H), 7.36-7.11 (m, 6H), 7.09-7.01 (m, 4H), 6.80 (d, J=7.6 Hz, 1H), 5.28 (s, 2H), 5.21 (s, 2H), 4.33 (t, J=5.0 Hz, 2H), 4.28 (s, 2H), 3.95 (dd, J=18.4, 12.4 Hz, 2H), 3.79 (dd, J=18.9, 12.4 Hz, 2H), 3.50 (t, J=5.0 Hz, 2H), 1.95 (s, 3H), 1.88 (s, 3H), 1.54 (s, 3H), 1.49 (s, 3H).

Example 389: (S)-4-((4-(((3'-((4-((((S)-3-carboxy-2-hydroxypropyl)amino)methyl)-2-chloro-5-((5-cyanopyridin-3-yl)methoxy)phenoxy)methyl)-2,2'-dimethyl-[1,1'-biphenyl]-3-yl)oxy)methyl)-5-chloro-2-methoxybenzyl)amino)-3-hydroxybutanoic acid

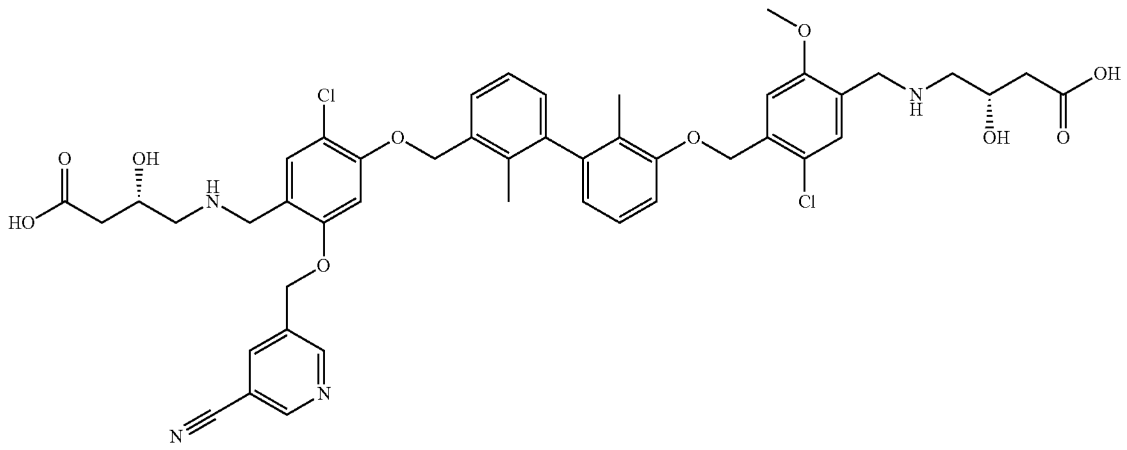 [SMILES: COc1cc(COc2cccc(-c3cccc(COc4cc(OCc5cncc(C#N)c5)c(CNC[C@@H](O)CC(=O)O)cc4Cl)c3C)c2C)c(Cl)cc1CNC[C@@H](O)CC(=O)O]

The title compound was synthesized according to general reductive amination procedure A. [M+1]=887.1. $^1$H (400 MHz, Acetonitrile-$d_3$) δ 8.91 (dd, J=8.3, 2.0 Hz, 2H), 8.27 (t, J=2.1 Hz, 1H), 7.91 (s, 1H), 7.46 (d, J=3.9 Hz, 2H), 7.34 (s, 1H), 7.27 (q, J=8.0 Hz, 2H), 7.13 (dd, J=7.7, 1.4 Hz, 1H), 7.10-7.05 (m, 1H), 6.95 (s, 1H), 6.81-6.74 (m, 1H), 5.32 (s, 2H), 5.25 (s, 2H), 5.23 (s, 2H), 4.36 20-4.09 (m, 6H), 3.87 (s, 3H), 3.17-3.06 (m, 4H), 2.79 (d, J=0.7 Hz, 3H), 2.48 (ddd, J=12.8, 6.3, 3.4 Hz, 4H), 2.07 (s, 3H).

Example 390: (S)-4-((4-((3'-((4-((((S)-3-carboxy-2-hydroxypropyl)amino)methyl)-2-chloro-5-((5-cyanopyridin-3-yl)methoxy)benzyl)oxy)-2,2'-dimethyl-[1,1'-biphenyl]-3-yl)methoxy)-5-chloro-2-((5-cyanopyridin-3-yl)methoxy)benzyl)amino)-3-hydroxybutanoic acid

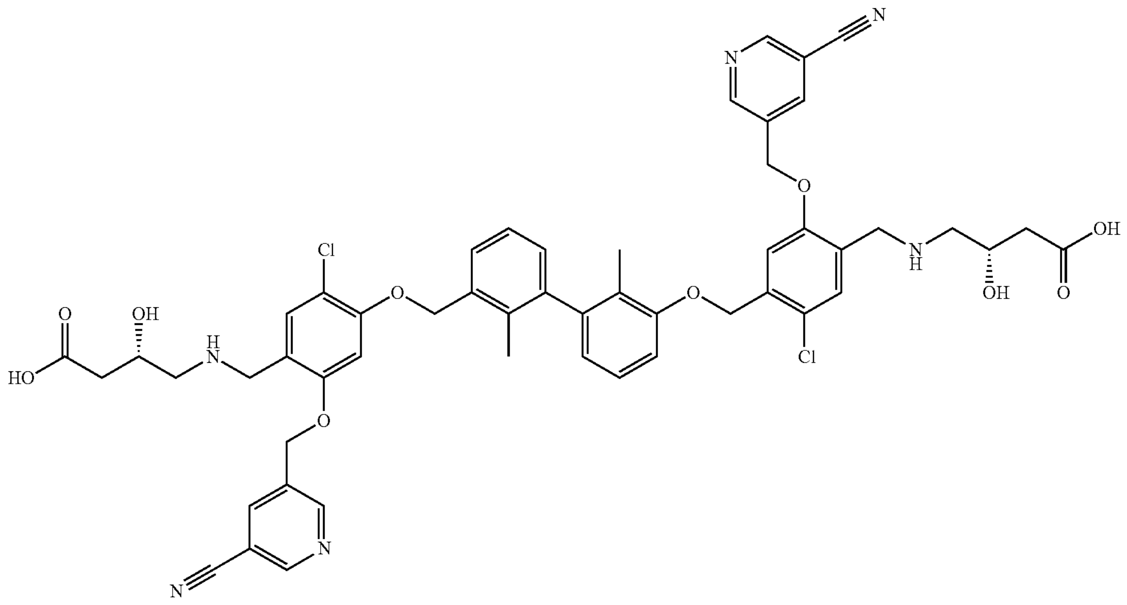 [SMILES: Cc1c(COc2cc(OCc3cncc(C#N)c3)c(CNC[C@@H](O)CC(=O)O)cc2Cl)cccc1-c1cccc(OCc2cc(OCc3cncc(C#N)c3)c(CNC[C@@H](O)CC(=O)O)cc2Cl)c1C]

The title compound was synthesized according to general reductive amination procedure A. [M+1]=989.1. $^1$H (400 MHz, Acetonitrile-$d_3$) δ 8.89 (d, J=21.5 Hz, 4H), 8.28 (s, 1H), 8.22 (s, 1H), 7.54 (s, 1H), 7.49 (d, J=7.5 Hz, 1H), 7.46 (s, 1H), 7.35 (s, 1H), 7.30 (t, J=7.6 Hz, 1H), 7.25 (t, J=7.9

Hz, 1H), 7.15 (d, J=7.5 Hz, 1H), 7.04 (d, J=8.2 Hz, 1H), 6.96 (s, 1H), 6.79 (d, J=7.6 Hz, 1H), 5.32 (s, 2H), 5.29 (s, 2H), 5.27 (s, 2H), 5.22 (s, 2H), 4.40-3.99 (m, 6H), 3.16 (ddd, J=17.9, 12.8, 3.1 Hz, 2H), 2.96 (ddd, J=17.2, 12.8, 9.7 Hz, 2H), 2.48 (td, J=6.7, 6.2, 4.1 Hz, 4H), 2.07 (s, 3H), 1.90 (s, 3H).

Example 391: 5-((4-chloro-2-((((1-hydroxycyclopropyl)methyl)amino)methyl)-5-((4"-(2-((2-hydroxyethyl)amino)ethoxy)-2,2'-dimethyl-[1,1':3',1"-terphenyl]-3-yl)methoxy)phenoxy)methyl) nicotinonitrile

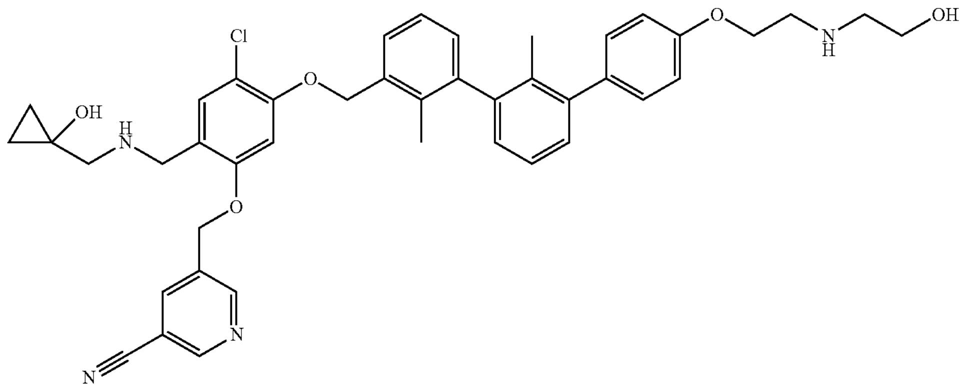 [SMILES: Cc1c(COc2cc(OCc3cncc(C#N)c3)c(CNCC3(O)CC3)cc2Cl)cccc1-c1cccc(-c2ccc(OCCNCCO)cc2)c1C]

The title compound was synthesized according to general reductive amination procedure A, followed by DCM/TFA Boc deprotection. [M+1]=733.1. $^{1}$H NMR (400 MHz, DMSO-$d_6$) δ 9.02 (dd, J=5.4, 2.1 Hz, 2H), 8.72 (s, 4H), 8.48 (t, J=2.1 Hz, 1H), 7.56 (s, 1H), 7.52-7.43 (m, 1H), 7.36-7.24 (m, 4H), 7.22-7.11 (m, 3H), 7.09-7.01 (m, 3H), 5.35 (s, 2H), 5.32 (d, J=2.3 Hz, 2H), 4.29 (t, J=5.1 Hz, 2H), 4.18 (d, J=5.6 Hz, 2H), 3.68 (t, J=5.3 Hz, 2H), 3.40 (t, J=5.5 Hz, 2H), 3.15-3.07 (m, 2H), 2.99 (t, J=5.6 Hz, 2H), 2.08 (s, 3H), 1.85 (s, 3H), 0.72-0.66 (m, 2H), 0.60 (t, J=3.3 Hz, 2H).

Example 392: (S)-4-(((6-(((3'-((4-((((S)-3-carboxy-2-hydroxypropyl)amino)methyl)-2-chloro-5-((5-cyanopyridin-3-yl)methoxy)phenoxy)methyl)-2,2'-dimethyl-[1,1'-biphenyl]-3-yl)oxy)methyl)pyridin-3-yl)methyl)amino)-3-hydroxybutanoic acid

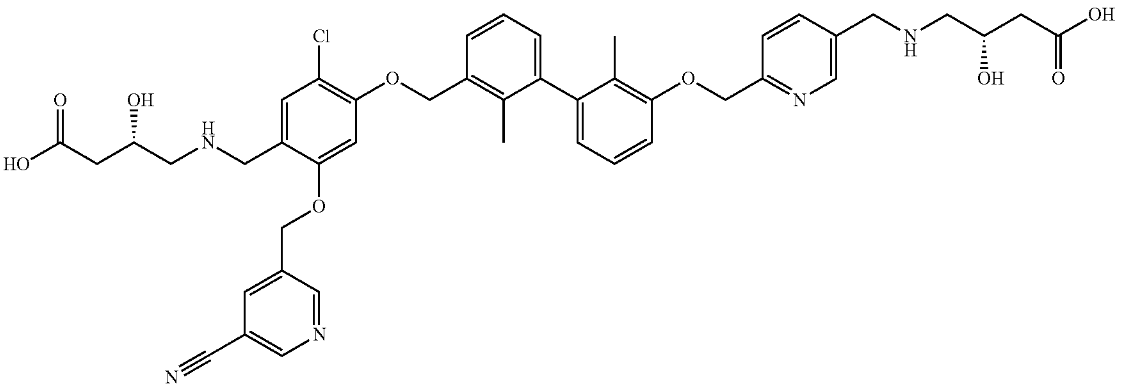 [SMILES: Cc1c(COc2cc(OCc3cncc(C#N)c3)c(CNC[C@@H](O)CC(=O)O)cc2Cl)cccc1-c1cccc(OCc2ccc(CNC[C@@H](O)CC(=O)O)cn2)c1C]

The title compound was synthesized according to general reductive amination procedure [M+1]=824.4. $^{1}$H (400 MHz, DMSO-d6) δ 9.04 (dd, J=5.6, 2.0 Hz, 2H), 8.99 (s, 2H), 8.71 (d, J=2.1 Hz, 1H), 8.62 (s, 2H), 8.49 (t, J=2.1 Hz, 1H), 8.01 (dd, J=8.1, 2.2 Hz, 1H), 7.66 (d, J=8.1 Hz, 1H), 7.59 (s, 1H), 7.50 (d, J=7.6 Hz, 1H), 7.29 (t, J=7.6 Hz, 1H), 7.26-7.16 (m, 2H), 7.13-7.02 (m, 2H), 6.73 (d, J=7.5 Hz, 1H), 5.38 (s, 2H), 5.31 (dd, J=11.8, 3.0 Hz, 2H), 5.26 (d, J=3.1 Hz, 2H), 4.25 (s, 2H), 4.17 (d, J=15.3 Hz, 4H), 3.04 (d, J=27.4 Hz, 2H), 2.86 (s, 2H), 2.48-2.28 (m, 4H), 2.05 (s, 3H), 1.93 (s, 3H).

Example 393: (S)-4-(((2-(3'-((4-((((S)-3-carboxy-2-hydroxypropyl)amino)methyl)-2-chloro-5-((5-cyano-pyridin-3-yl)methoxy)phenoxy)methyl)-2,2'-dimethyl-[1,1'-biphenyl]-3-yl)-8-chloro-[1,2,4]triazolo [1,5-a]pyridin-6-yl)methyl)amino)-3-hydroxybutanoic acid Step 3: (2-bromo-8-chloro[1,2,4]triazolo[1,5-a]pyridine-6-yl)methanol (500 mg, 1.91 mmol) dissolved in dichloromethane (20 mL) was treated with Dess-Martin periodinane (848 mg, 2.00 mmol). The reaction mixture was stirred at room temperature overnight. The reaction mixture was quenched by adding saturated sodium thiosulfate solution and then concentrated. The residue was dissolved in ethyl

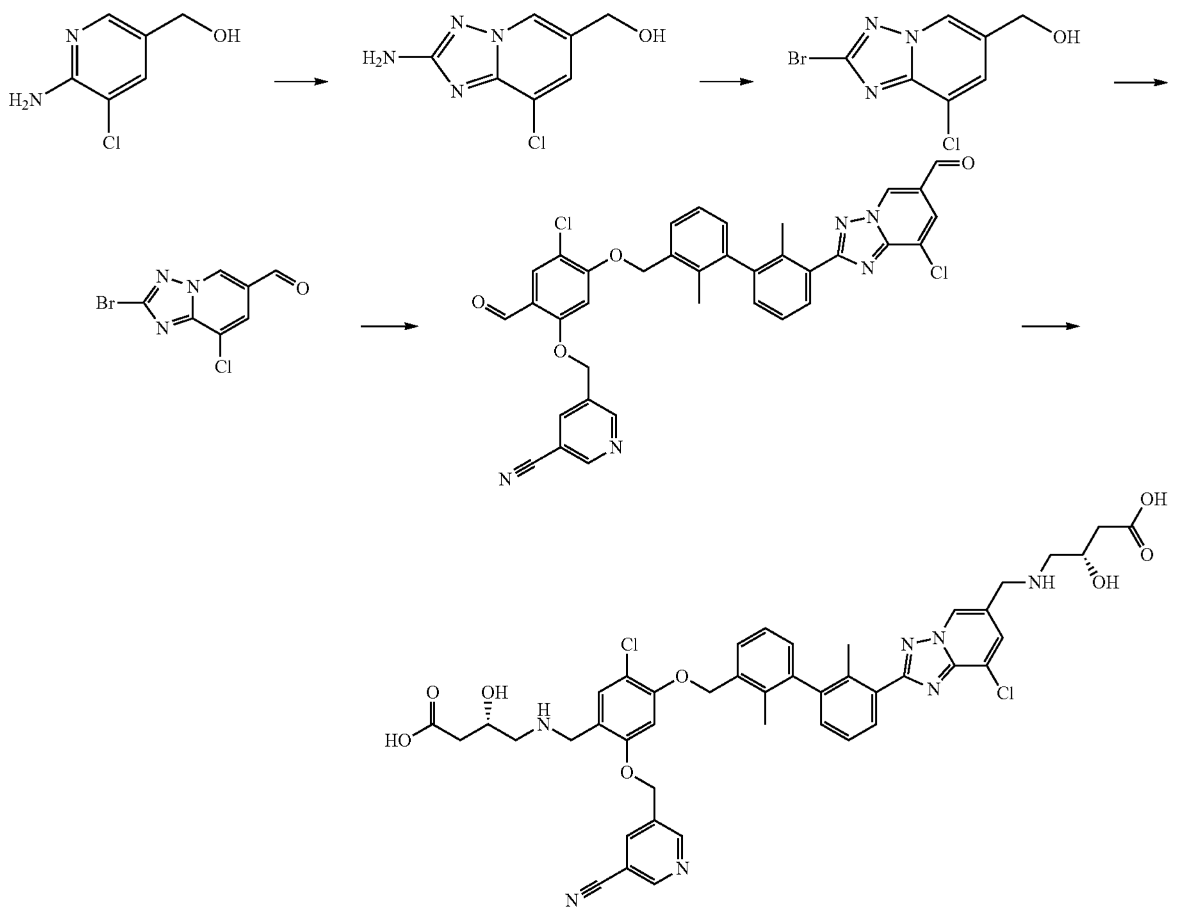

Step 1: Ethoxycarbonyl isothiocyanate (480 μL, 4.07 mmol) was added dropwise to 6-amino-5-chloropyridin-3-yl)methanol (550 mg, 3.47 mmol) dissolved in 1,4-dioxane (9 mL). The reaction mixture was stirred at rt overnight. The precipitate was filtered and washed with dichloromethane. The mother liquor was concentrated and filtered again. The two crops of solids were combined and dried. The product was dissolved in methanol (7 mL) and ethanol (7 mL) and treated with N,N-diisopropylethylamine (900 μL, 5.17 mmol) and hydroxylamine hydrochloride (600 mg, 8.63 mmol). The reaction mixture was heated at 50° C. for 2 h. After cooling to room temperature, the reaction mixture was concentrated and the residue was used in the next step.

Step 2: (2-amino-8-chloro[1,2,4]triazolo[1,5-a]pyridine-6-yl)methanol (690 mg, 3.47 mmol) suspended in acetonitrile (35 mL) was treated with copper (II) bromide (1160 mg, 5.19 mmol) and tert-butyl nitrite (990 μL, 8.29 mmol). The reaction mixture was stirred at room temperature for 3 h. The reaction mixture was concentrated. The residue was suspended in ethyl acetate and washed with water. The organic layer was concentrated and purified by column chromatography to give (2-bromo-8-chloro[1,2,4]triazolo[1,5-a]pyridine-6-yl)methanol.

acetate and washed with water. The organic layer was concentrated and purified by column chromatography to give 2-bromo-8-chloro-[1,2,4]triazolo[1,5-a]pyridine-6-carbaldehyde.

Step 4: 2-bromo-8-chloro-[1,2,4]triazolo[1,5-a]pyridine-6-carbaldehyde (70 mg, 0.27 mmol) and 5-((4-chloro-5-((2,2'-dimethyl-3'-(4,4,5,5-tetramethyl-1,3,2-dioxaborolan-2-yl)-[1,1'-biphenyl]-3-yl)methoxy)-2-formylphenoxy) methyl)nicotinonitrile (96 mg, 0.16 mmol) suspended in 2-methyltetrahydrofuran (3 mL) was treated with [1,1'-Bis (diphenylphosphino)ferrocene]palladium(II) dichloride (14 mg, 0.02 mmol) and 2 M sodium carbonate solution (240 μL, 0.48 mmol). The reaction mixture was heated in the microwave at 110° C. for 3 h. After cooling to room temperature, the reaction mixture was concentrated. The residue was suspended in ethyl acetate and washed with water. The organic layer was concentrated and purified by column chromatography to give 5-((4-chloro-5-((3'-(8-chloro-6-formyl-[1,2,4]triazolo[1,5-a]pyridin-2-yl)-2,2'-dimethyl-[1,1'-biphenyl]-3-yl)methoxy)-2-formylphenoxy) methyl)nicotinonitrile.

Step 5: (S)-4-(((2-(3'-((4-((((S)-3-carboxy-2-hydroxypropyl)amino)methyl)-2-chloro-5-((5-cyanopyridin-3-yl)

methoxy)phenoxy)methyl)-2,2'-dimethyl-[1,1'-biphenyl]-3-yl)-8-chloro-[1,2,4]triazolo[1,5-a]pyridin-6-yl)methyl) amino)-3-hydroxybutanoic acid was synthesized in the same manner as Procedure C using (S)-4-amino-3-hydroxybutanoic acid. $^1$H NMR (400 MHz, DMSO-$d_6$) δ 9.01 (d, J=6.5 Hz, 4H), 8.46 (s, 2H), 7.97 (d, J=8.2 Hz, 2H), 7.56-7.47 (m, 4H), 7.42 (s, 5H), 7.30 (d, J=7.6 Hz, 3H), 7.24 (d, J=7.4 Hz, 3H), 7.16 (d, J=7.4 Hz, 4H), 6.49 (s, 3H), 5.34 (d, J=10.7 Hz, 6H), 2.52 (s, 2H), 2.26 (s, 3H), 2.07 (s, 3H). LCMS-ESI+ (m/z): [M+H]+ calcd for C44H43Cl2N7O8: 868.3; found: 868.1.

Example 394: (S)-4-(((2-(3'-((4-((((S)-3-carboxy-2-hydroxypropyl)amino)methyl)-2-chloro-5-((5-cyano-pyridin-3-yl)methoxy)phenoxy)methyl)-2,2'-dimethyl-[1,1'-biphenyl]-3-yl)imidazo[1,2-a]pyridin-6-yl)methyl)amino)-3-hydroxybutanoic acid Step 1: Methyl 2-bromoimidazo[1,2-a]pyridine-6-carboxylate (300 mg, 1.18 mmol) dissolved in diethyl ether (12 mL) and cooled to 0° C. was treated with lithium aluminum hydride (46 mg, 1.21 mmol). The reaction mixture was allowed to warm to room temperature and stirred overnight. After cooling to 0° C. again, the reaction mixture was quenched by addition of sodium sulfate decahydrate. The mixture was stirred for 20 min and filtered. The filtrate was concentrated to give (2-bromoimidazo[1,2-a]pyridin-6-yl) methanol.

Steps 2-4: Prepared in the same manner as step 3-5 of Example 393. $^1$H NMR (400 MHz, DMSO-$d_6$) δ 9.02 (dd, J=5.6, 2.0 Hz, 2H), 8.94 (s, 2H), 8.72 (s, 1H), 8.58 (s, 2H), 8.47 (t, J=2.1 Hz, 1H), 8.36 (s, 1H), 7.80-7.71 (m, 2H), 7.57 (s, 1H), 7.56-7.48 (m, 2H), 7.38 (t, J=7.7 Hz, 1H), 7.30 (t, J=7.6 Hz, 1H), 7.19 (s, 1H), 7.14 (d, J=7.8 Hz, 2H), 5.59 (d, J=28.8 Hz, 4H), 5.41-5.30 (m, 3H), 4.24 (s, 3H), 4.12 (d, J=9.9 Hz, 4H), 3.06 (s, 4H), 2.85 (s, 3H), 2.15 (s, 3H), 2.08 (s, 3H). LCMS-ESI+ (m/z): [M+H]+ calcd for $C_{45}H_{45}ClN_6O_8$: 833.3; found: 833.3.

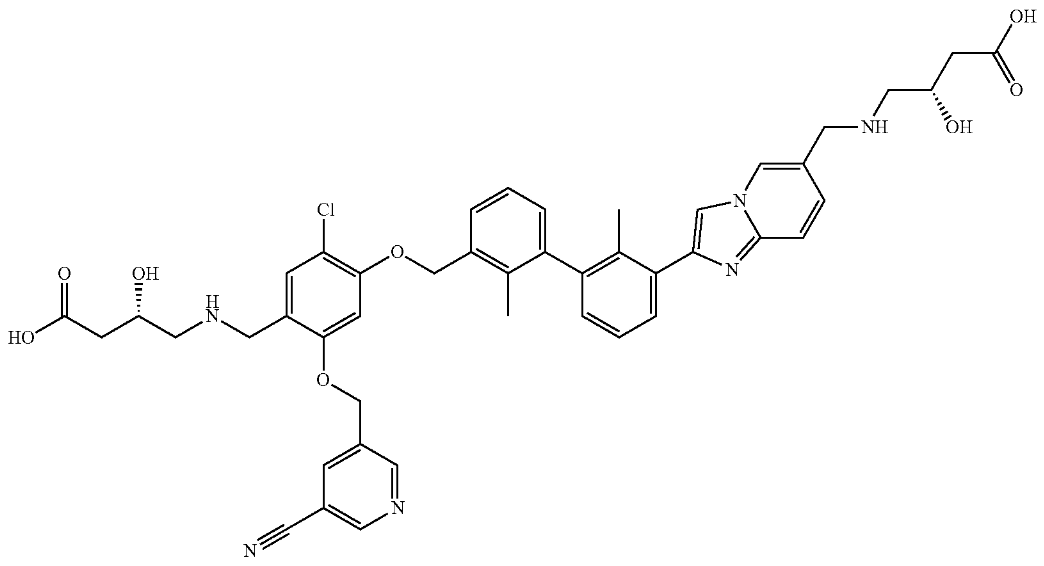 [SMILES: Cc1c(COc2cc(OCc3cncc(C#N)c3)c(CNC[C@@H](O)CC(=O)O)cc2Cl)cccc1-c1cccc(-c2cn3cc(CNC[C@@H](O)CC(=O)O)ccc3n2)c1C]

Example 395: (S)-4-(((2-(3'-((4-((((S)-3-carboxy-2-hydroxypropyl)amino)methyl)-2-chloro-5-((5-cyano-pyridin-3-yl)methoxy)phenoxy)methyl)-2,2'-dimethyl-[1,1'-biphenyl]-3-yl)-4-methylbenzo[d]thiazol-5-yl)methyl)amino)-3-hydroxybutanoic acid

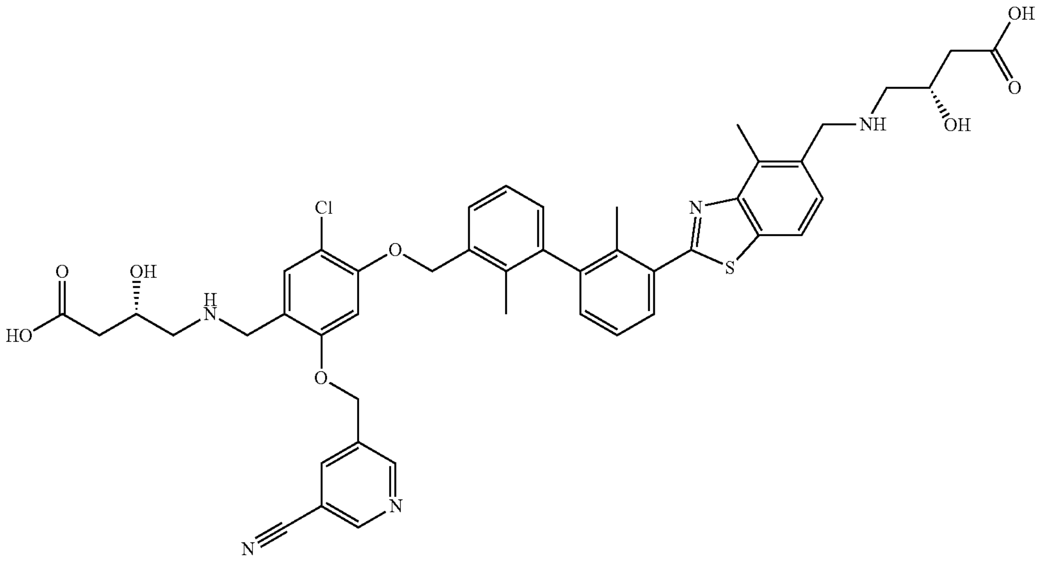 [SMILES: Cc1c(COc2cc(OCc3cncc(C#N)c3)c(CNC[C@@H](O)CC(=O)O)cc2Cl)cccc1-c1cccc(-c2nc3c(C)c(CNC[C@@H](O)CC(=O)O)ccc3s2)c1C]

Synthesized analogous to Example 393 using the appropriate heterocyclic bromoaldehyde. $^1$H NMR (400 MHz, DMSO-$d_6$) δ 9.02 (dd, J=6.0, 2.0 Hz, 2H), 8.90 (s, 2H), 8.57 (s, 2H), 8.46 (t, J=2.0 Hz, 1H), 7.57 (s, 1H), 7.51 (d, J=3.8 Hz, 2H), 7.48 (t, J=7.7 Hz, 1H), 7.31 (t, J=7.7 Hz, 2H), 7.18 (d, J=7.6 Hz, 2H), 5.56 (s, 2H), 5.35 (d, J=10.1 Hz, 4H), 4.27 (s, 2H), 4.14 (d, J=23.4 Hz, 5H), 3.00 (d, J=16.5 Hz, 2H), 2.85 (d, J=11.1 Hz, 3H), 2.69 (s, 3H), 2.40-2.33 (m, 3H), 2.25 (s, 3H), 2.08 (s, 3H). LCMS-ESI+ (m/z): [M+H]+ calcd for $C_{46}H_{46}ClN_5O_8S$: 864.3; found: 864.0.

Example 396: (S)-4-(((2-(3-((S)-1-((5-((((S)-3-carboxy-2-hydroxypropyl)amino)methyl)-3-chloro-6-((5-cyanopyridin-3-yl)methoxy)pyridin-2-yl)oxy)-2,3-dihydro-1H-inden-4-yl)-2-methylphenyl)benzo[d]thiazol-6-yl)methyl)amino)-3-hydroxybutanoic acid

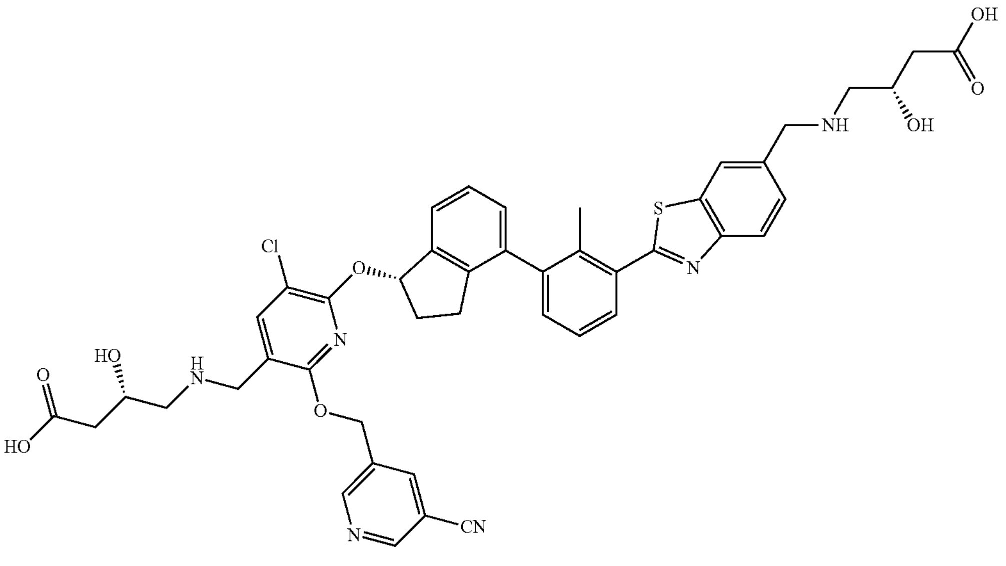 [SMILES: Cc1c(-c2nc3ccc(CNC[C@@H](O)CC(=O)O)cc3s2)cccc1-c1cccc2c1CC[C@@H]2Oc1nc(OCc2cncc(C#N)c2)c(CNC[C@@H](O)CC(=O)O)cc1Cl]

Step 1: (S)-5-(((2-((4-(3-bromo-2-methylphenyl)-2,3-dihydro-1H-inden-1-yl)oxy)-6-chloro-4-formylpyridin-3-yl)oxy)methyl)nicotinonitrile (40 mg, 0.07 mmol) dissolved in 1,4-dioxane (8 mL) was treated with bis (pinacolato) diboron (27 mg, 0.11 mmol), [1,1'-Bis(diphenylphosphino)ferrocene]palladium(II) dichloride (6 mg, 0.007 mmol), and potassium acetate (21 mg, 0.21 mmol). The reaction mixture was heated at 80° C. overnight. After cooling to room temperature, the reaction mixture was diluted with ethyl acetate and washed with water. The organic layer was concentrated and purified by column chromatography to give(S)-5-(((5-chloro-3-formyl-6-((4-(2-methyl-3-(4,4,5,5-tetramethyl-1,3,2-dioxaborolan-2-yl)phenyl)-2,3-dihydro-1H-inden-1-yl)oxy)pyridin-2-yl)oxy)methyl)nicotinonitrile.

Step 2: 2-bromobenzo[d]thiazole-6-carbaldehyde (25 mg, 0.10 mmol) and (S)-5-(((5-chloro-3-formyl-6-((4-(2-methyl-3-(4,4,5,5-tetramethyl-1,3,2-dioxaborolan-2-yl)phenyl)-2,3-dihydro-1H-inden-1-yl)oxy)pyridin-2-yl)oxy)methyl)nicotinonitrile (40 mg, 0.06 mmol) suspended in 2-methyltetrahydrofuran (2 mL) was treated with [1,1'-Bis(diphenylphosphino)ferrocene]palladium(II) dichloride (6 mg, 0.007 mmol) and 2 M sodium carbonate solution (90 μL, 0.18 mmol). The reaction mixture was heated in the microwave at 110° C. for 90 min. After cooling to room temperature, the reaction mixture was concentrated. The residue was suspended in ethyl acetate and washed with water. The organic layer was concentrated and purified by column chromatography to give (S)-5-(((5-chloro-3-formyl-6-((4-(3-(6-formylbenzo[d]thiazol-2-yl)-2-methylphenyl)-2,3-dihydro-1H-inden-1-yl)oxy)pyridin-2-yl)oxy)methyl)nicotinonitrile.

Step 3: (S)-4-(((2-(3-((S)-1-((5-((((S)-3-carboxy-2-hydroxypropyl)amino)methyl)-3-chloro-6-((5-cyanopyridin-3-yl)methoxy)pyridin-2-yl)oxy)-2,3-dihydro-1H-inden-4-yl)-2-methylphenyl)benzo[d]thiazol-6-yl)methyl)amino)-3-hydroxybutanoic acid was prepared according to general reductive amination procedure C using (S)-4-amino-3-hydroxybutanoic acid. $^1$H NMR (400 MHz, DMSO-$d_6$) δ 9.02 (d, J=2.1 Hz, 1H), 8.69 (s, 2H), 8.45 (s, 1H), 8.28 (d, J=1.4 Hz, 1H), 8.14 (d, J=8.4 Hz, 1H), 8.03 (s, 1H), 7.82-7.75 (m, 1H), 7.70 (dd, J=8.3, 1.7 Hz, 1H), 7.47 (t, J=7.6 Hz, 1H), 7.43-7.32 (m, 1H), 7.32-7.25 (m, 1H), 7.23 (d, J=6.7 Hz, 1H), 6.51 (s, 1H), 5.58 (s, 4H), 4.32 (d, J=5.7 Hz, 3H), 4.17 (s, 5H), 3.07 (s, 3H), 2.88 (s, 3H), 2.69 (s, 1H), 2.39-2.34 (m, 2H), 2.31 (d, J=9.9 Hz, 5H), 1.95 (s, 2H). LCMS-ESI+ (m/z): [M+H]+ calcd for $C_{45}H_{43}ClN_6O_8$: 863.3; found: 863.0.

Example 397: (S)-4-(((7-(3'-((4-((((S)-3-carboxy-2-hydroxypropyl)amino)methyl)-2-chloro-5-((5-cyanopyridin-3-yl)methoxy)phenoxy)methyl)-2,2'-dimethyl-[1,1'-biphenyl]-3-yl)imidazo[1,2-a]pyridin-2-yl)methyl)amino)-3-hydroxybutanoic acid

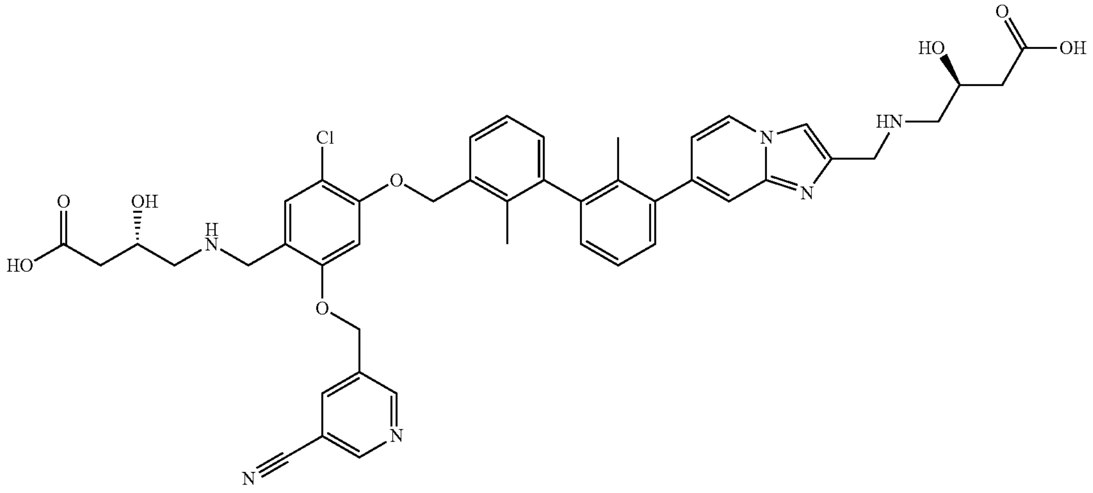 [SMILES: Cc1c(COc2cc(OCc3cncc(C#N)c3)c(CNC[C@@H](O)CC(=O)O)cc2Cl)cccc1-c1cccc(-c2ccn3cc(CNC[C@@H](O)CC(=O)O)nc3c2)c1C]

The title compound was prepared in the same manner as Example 393 using 7-bromoimidazo[1,2-a]pyridine-2-carbaldehyde. $^1$H NMR (400 MHz, DMSO-$d_6$) δ 9.02 (dd, J=6.3, 2.0 Hz, 2H), 8.56 (s, 2H), 8.46 (t, J=2.1 Hz, 1H), 8.07 (s, 1H), 7.55 (d, J=14.3 Hz, 2H), 7.49 (d, J=7.6 Hz, 1H), 7.32 (ddd, J=17.2, 14.8, 7.5 Hz, 4H), 6.49 (s, 3H), 5.54 (s, 3H), 5.34 (d, J=17.4 Hz, 4H), 4.30 (s, 2H), 4.13 (s, 5H), 3.09 (d, J=12.9 Hz, 2H), 2.91 (d, J=60.1 Hz, 5H), 2.36 (dd, J=8.0, 6.1 Hz, 3H), 2.10 (s, 3H), 1.92 (s, 3H). LCMS-ESI+ (m/z): [M+H]+ calcd for $C_{45}H_{45}ClN_6O_8$: 833.3; found: 833.4.

Example 398: (S)-4-(((2-(3'-((4-((((S)-3-carboxy-2-hydroxypropyl)amino)methyl)-2-chloro-5-((5-cyano-pyridin-3-yl)methoxy)phenoxy)methyl)-2,2'-dimethyl-[1,1'-biphenyl]-3-yl)quinolin-6-yl)methyl)amino)-3-hydroxybutanoic acid

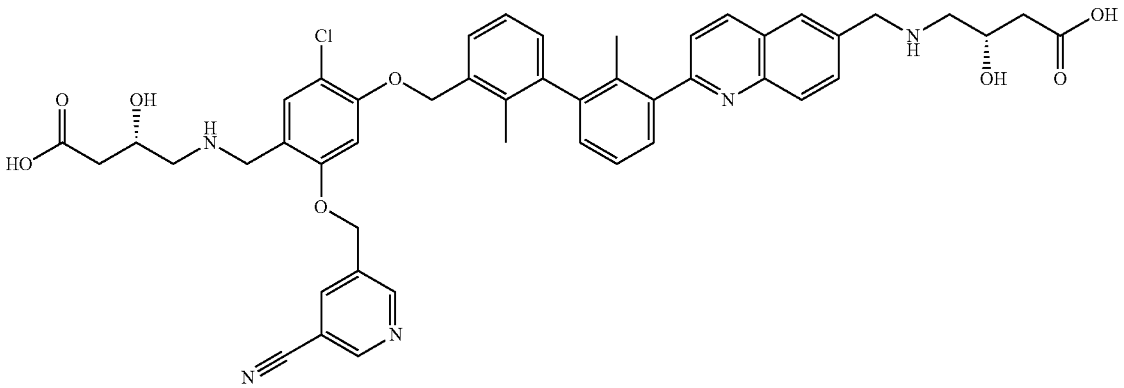 [SMILES: Cc1c(COc2cc(OCc3cncc(C#N)c3)c(CNC[C@@H](O)CC(=O)O)cc2Cl)cccc1-c1cccc(-c2ccc3cc(CNC[C@@H](O)CC(=O)O)ccc3n2)c1C]

The title compound was prepared in the same manner as Example 393 using 2-chloroquinoline-6-carbaldehyde. $^1H$ NMR (400 MHz, DMSO-$d_6$) δ 9.02 (dd, J=5.3, 2.1 Hz, 3H), 8.57 (s, 2H), 8.46 (dd, J=5.4, 3.3 Hz, 2H), 8.14 (d, J=1.9 Hz, 1H), 8.08 (d, J=8.7 Hz, 1H), 7.90 (dd, J=8.7, 1.9 Hz, 1H), 7.76 (d, J=8.5 Hz, 1H), 7.57 (s, 1H), 7.53-7.46 (m, 2H), 7.42 (t, J=7.5 Hz, 1H), 7.31 (t, J=7.6 Hz, 1H), 7.23-7.10 (m, 3H), 5.56 (s, 3H), 5.34 (d, J=13.5 Hz, 4H), 4.38 (s, 2H), 4.23-4.05 (m, 4H), 3.07 (s, 4H), 2.90 (s, 4H), 2.11 (s, 3H), 1.97 (s, 3H), 1.10 (d, J=6.1 Hz, 1H). LCMS-ESI+ (m/z): [M+H]+ calcd for $C_{47}H_{46}ClN_5O$: 844.3; found: 844.3.

Example 399: (S)-4-(((5-(3'-((4-((((S)-3-carboxy-2-hydroxypropyl)amino)methyl)-2-chloro-5-((5-cyano-pyridin-3-yl)methoxy)phenoxy)methyl)-2,2'-dimethyl-[1,1'-biphenyl]-3-yl)benzo[d]thiazol-2-yl)methyl)amino)-3-hydroxybutanoic acid

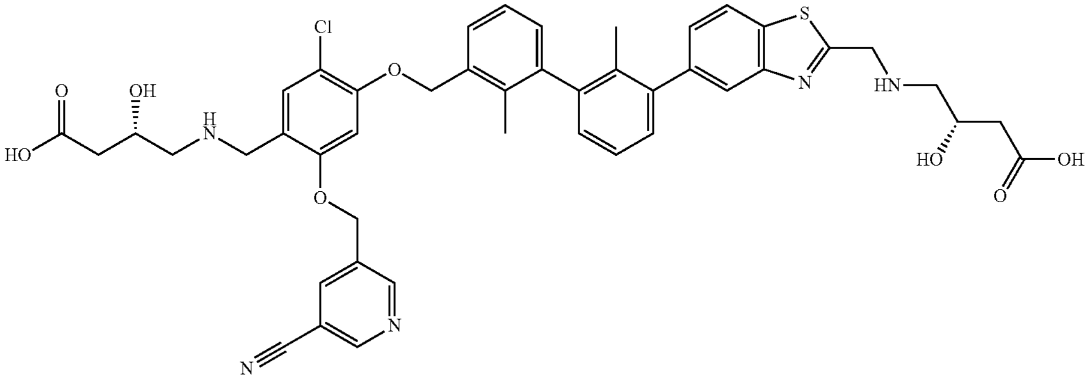 [SMILES: Cc1c(COc2cc(OCc3cncc(C#N)c3)c(CNC[C@@H](O)CC(=O)O)cc2Cl)cccc1-c1cccc(-c2ccc3sc(CNC[C@@H](O)CC(=O)O)nc3c2)c1C]

The title compound was prepared in the same manner as Example 393 using 5-bromobenzo[d]thiazole-2-carbaldehyde. $^1H$ NMR (400 MHz, DMSO-$d_6$) δ 9.44 (d, J=66.6 Hz, 2H), 9.02 (dd, J=6.2, 2.1 Hz, 2H), 8.58 (s, 2H), 8.24 (d, J=8.4 Hz, 1H), 8.01 (d, J=1.6 Hz, 1H), 7.60-7.43 (m, 3H), 7.41-7.23 (m, 3H), 7.22-7.06 (m, 3H), 5.55 (s, 2H), 5.34 (d, J=17.4 Hz, 4H), 4.77 (s, 2H), 4.12 (s, 5H), 3.24 (d, J=12.5 Hz, 2H), 2.98 (s, 3H), 2.83 (s, 2H), 2.36 (ddd, J=18.1, 15.5, 6.9 Hz, 2H), 2.11 (s, 3H), 1.88 (s, 3H). LCMS-ESI+ (m/z): [M+H]+ calcd $C_{45}H_{44}ClN_5O_8S$: 850.3; found: 850.3.

The following compounds were prepared according to the methods provided herein using the appropriate starting material.

| Example No. | Structure |
|---|---|
| 400 | 5-((4-chloro-5-((4''-((dimethylamino)methyl)-3''-(4-hydroxybut-1-yn-1-yl)-2,2'-dimethyl-[1,1':3',1''-terphenyl]-3-yl)methoxy)-2-(((2-hydroxyethyl)amino)methyl)phenoxy)methyl)nicotinonitrile 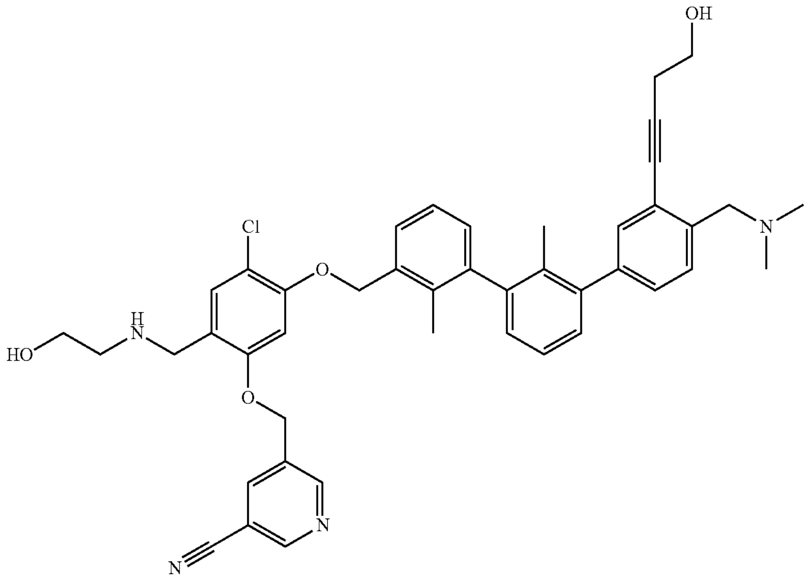 [SMILES: Cc1c(COc2cc(OCc3cncc(C#N)c3)c(CNCCO)cc2Cl)cccc1-c1cccc(-c2ccc(CN(C)C)c(C#CCCO)c2)c1C] |
| 401 | (S)-2-((5-chloro-2-((5-cyanopyridin-3-yl)methoxy)-4-((4''-((dimethylamino)methyl)-3''-(4-hydroxybut-1-yn-1-yl)-2,2'-dimethyl-[1,1':3',1''-terphenyl]-3-yl)methoxy)benzyl)amino)-3-hydroxy-2-methylpropanoic acid 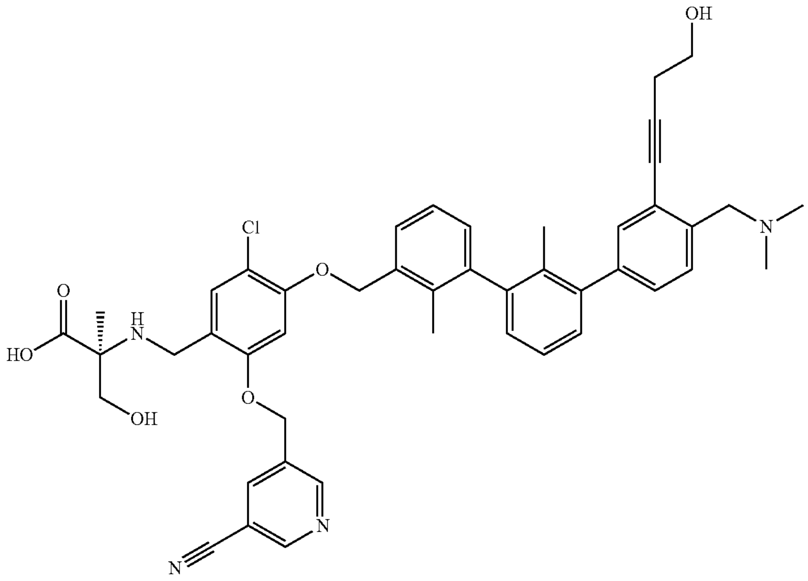 [SMILES: Cc1c(COc2cc(OCc3cncc(C#N)c3)c(CN[C@@](C)(CO)C(=O)O)cc2Cl)cccc1-c1cccc(-c2ccc(CN(C)C)c(C#CCCO)c2)c1C] |

-continued 402 2,2'-(((6,6'-(((2,2'-dimethyl-[1,1'-biphenyl]-3,3'-diyl)bis(methylene))bis(oxy))bis(5-bromo-2-methoxypyridine-6,3-diyl))bis(methylene))bis(azanediyl))bis(3-hydroxy-2-methylpropanoic acid)

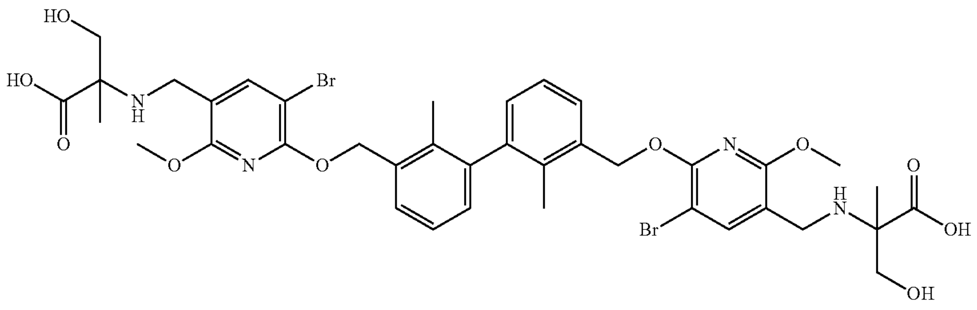 [SMILES: COc1nc(OCc2cccc(-c3cccc(COc4nc(OC)c(CNC(C)(CO)C(=O)O)cc4Br)c3C)c2C)c(Br)cc1CNC(C)(CO)C(=O)O]

404 (1S,1'S,2R,2'R)-2,2'-(((6,6'-(((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(cyclohexan-1-ol)

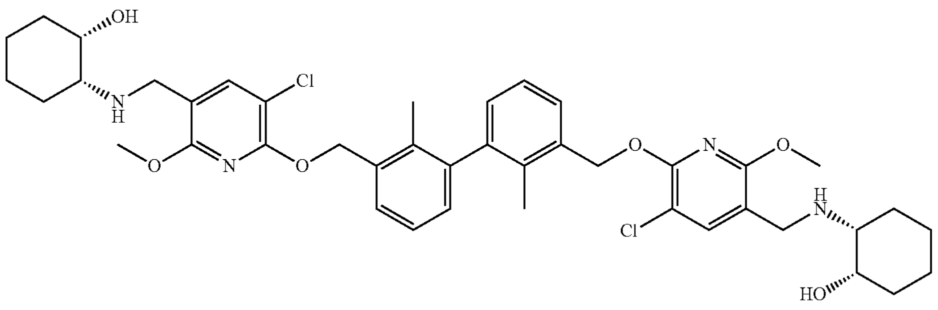 [SMILES: COc1nc(OCc2cccc(-c3cccc(COc4nc(OC)c(CN[C@@H]5CCCC[C@@H]5O)cc4Cl)c3C)c2C)c(Cl)cc1CN[C@@H]1CCCC[C@@H]1O]

405 (1R,1'R,2R,2'R)-2,2'-(((6,6'-(((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))bis(cyclohexan-1-ol)

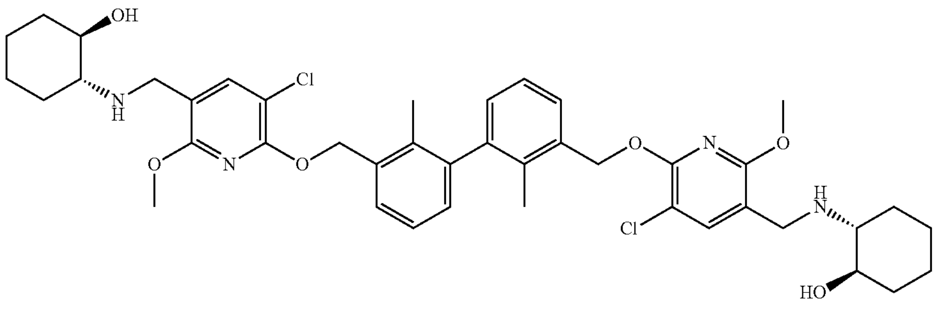 [SMILES: COc1nc(OCc2cccc(-c3cccc(COc4nc(OC)c(CN[C@@H]5CCCC[C@H]5O)cc4Cl)c3C)c2C)c(Cl)cc1CN[C@@H]1CCCC[C@H]1O]

-continued 406 (3S,3'S)-4,4'-(((2,2'-(((2,2'-dimethyl-[1,1'-biphenyl]-3,3'-diyl)bis(methylene))bis(oxy))bis(4-((5-cyanopyridin-3-yl)methoxy)pyrimidine-5,2-diyl))bis(methylene))bis(azanediyl))bis(3-hydroxybutanoic acid)

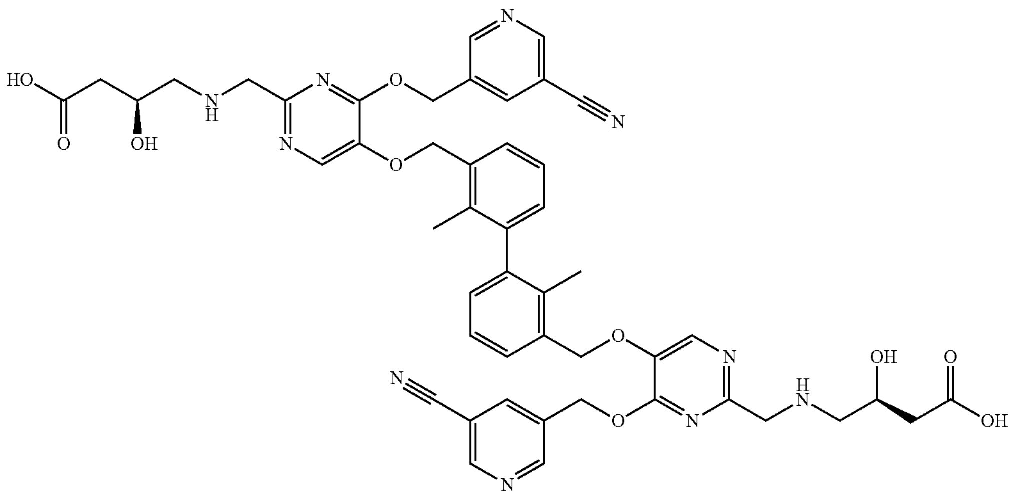 [SMILES: Cc1c(COc2cnc(CNC[C@@H](O)CC(=O)O)nc2OCc2cncc(C#N)c2)cccc1-c1cccc(COc2cnc(CNC[C@@H](O)CC(=O)O)nc2OCc2cncc(C#N)c2)c1C]

407 (3R,3'R)-4,4'-(((6,6'-(((1S,1'S)-2,2',3,3'-tetrahydro-1H,1'H-[4,4'-biindene]-1,1'-diyl)bis(oxy))bis(2-methoxypyridine-6,3-diyl))bis(methylene))bis(azanediyl))bis(3-hydroxybutanoic acid)

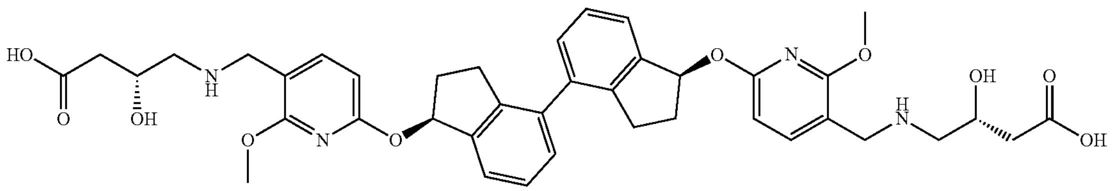 [SMILES: COc1nc(O[C@H]2CCc3c(-c4cccc5c4CC[C@@H]5Oc4ccc(CNC[C@H](O)CC(=O)O)c(OC)n4)cccc32)ccc1CNC[C@H](O)CC(=O)O]

408 N,N'-(((((([4,4'-biindoline]-1,1'-dicarbonyl)bis(2-((5-cyanopyridin-3-yl)methoxy)-4,1-phenylene))bis(methylene))bis(azanediyl))bis(ethane-2,1-diyl))diacetamide

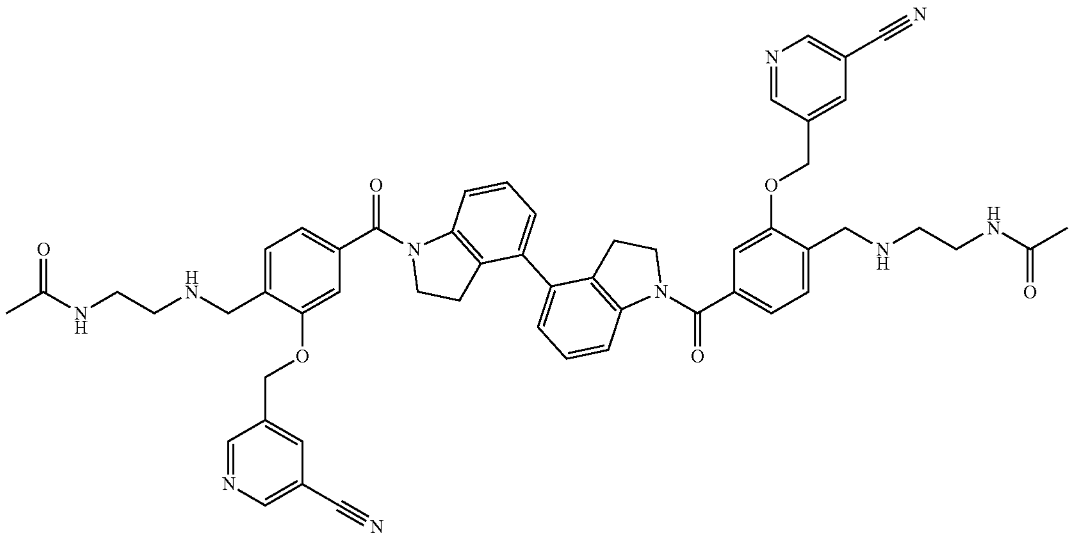 [SMILES: CC(=O)NCCNCc1ccc(C(=O)N2CCc3c(-c4cccc5c4CCN5C(=O)c4ccc(CNCCNC(C)=O)c(OCc5cncc(C#N)c5)c4)cccc32)cc1OCc1cncc(C#N)c1]

-continued 409 (3S,3'S)-4,4'-(((([4,4'-biindoline]-1,1'-dicarbonyl)bis(2-((5-cyanopyridin-3-yl)methoxy)-5,1-phenylene))bis(methylene))bis(azanediyl))bis(3-hydroxybutanoic acid)

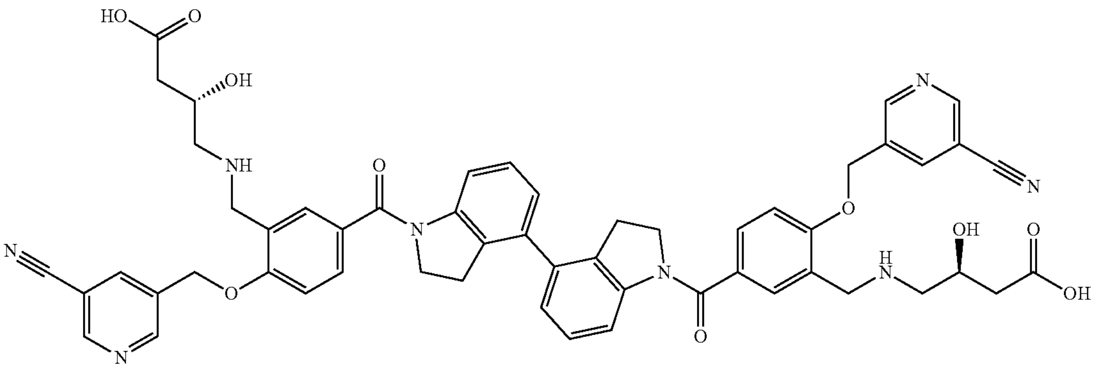 [SMILES: N#Cc1cncc(COc2ccc(C(=O)N3CCc4c(-c5cccc6c5CCN6C(=O)c5ccc(OCc6cncc(C#N)c6)c(CNC[C@@H](O)CC(=O)O)c5)cccc43)cc2CNC[C@@H](O)CC(=O)O)c1]

410 (3S,3'S)-4,4'-(((([4,4'-biindoline]-1,1'-dicarbonyl)bis(2-methoxy-5,1-phenylene))bis(methylene))bis(azanediyl))bis(3-hydroxybutanoic acid)

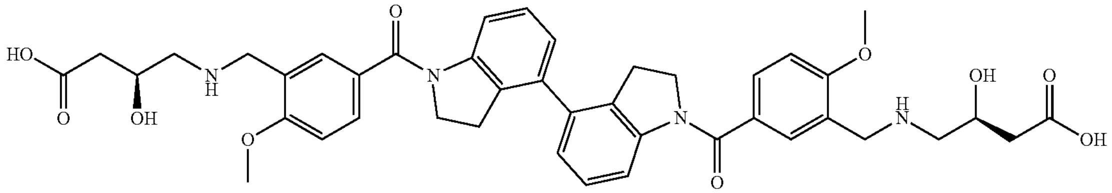 [SMILES: COc1ccc(C(=O)N2CCc3c(-c4cccc5c4CCN5C(=O)c4ccc(OC)c(CNC[C@@H](O)CC(=O)O)c4)cccc32)cc1CNC[C@@H](O)CC(=O)O]

411 [4,4'-biindoline]-1,1'-diylbis((3-(((2-hydroxyethyl)amino)methyl)phenyl)methanone)

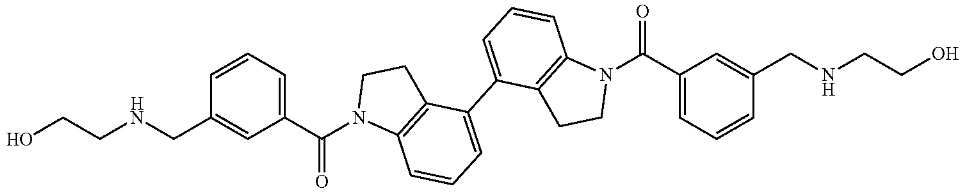 [SMILES: O=C(c1cccc(CNCCO)c1)N1CCc2c(-c3cccc4c3CCN4C(=O)c3cccc(CNCCO)c3)cccc21]

412 (3S,3'S)-4,4'-(((([4,4'-biindoline]-1,1'-dicarbonyl)bis(3,1-phenylene))bis(methylene))bis(azanediyl))bis(3-hydroxybutanoic acid)

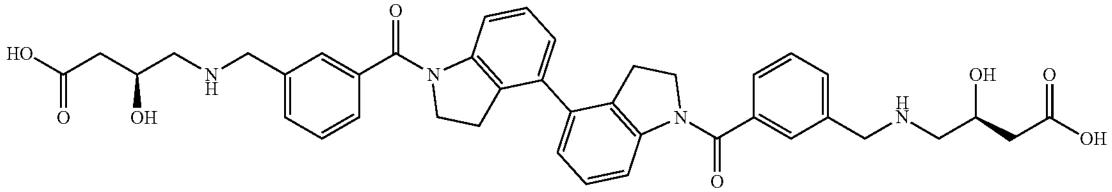 [SMILES: O=C(O)C[C@H](O)CNCc1cccc(C(=O)N2CCc3c(-c4cccc5c4CCN5C(=O)c4cccc(CNC[C@@H](O)CC(=O)O)c4)cccc32)c1]

413 (S)-4-hydroxy-1-(4-(1'-(4-(((R)-4-hydroxy-2-oxopyrrolidin-1-yl)methyl)-2-methylbenzoyl)-[4,4'-biindoline]-1-carbonyl)-3-methylbenzyl)pyrrolidin-2-one[4,4'-biindoline]-1,1'-diylbis(phenylmethanone)

414 [4,4'-biindoline]-1,1'-diylbis((4-(((2-hydroxyethyl)amino)methyl)phenyl)methanone)

415 (3S,3'S)-4,4'-(((([4,4'-biindoline]-1,1'-dicarbonyl)bis(4-methyl-3,1-phenylene))bis(methylene))bis(azanediyl))bis(3-hydroxybutanoic acid)

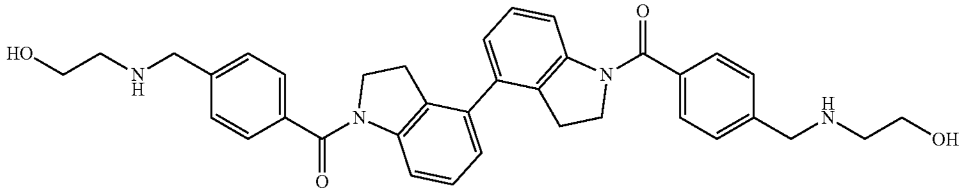 [SMILES: O=C(c1ccc(CNCCO)cc1)N1CCc2c(-c3cccc4c3CCN4C(=O)c3ccc(CNCCO)cc3)cccc21]

-continued 416 (S)-4-hydroxy-1-(3-(1'-(5-(((R)-4-hydroxy-2-oxopyrrolidin-1-yl)methyl)-2-methylbenzoyl)-[4,4'-biindoline]-1-carbonyl)-4-methylbenzyl)pyrrolidin-2-one
417 (S)-3-hydroxy-4-((3-(1'-(5-(((S)-4-hydroxy-2-oxopyrrolidin-1-yl)methyl)-2-methylbenzoyl)-[4,4'-biindoline]-1-carbonyl)-4-methylbenzyl)amino)butanoic acid
418 (3S,3'S)-4,4'-(((([4,4'-biindoline]-1,1'-dicarbonyl)bis(3-methyl-4,1-phenylene))bis(methylene))bis(azanediyl))bis(3-hydroxybutanoic acid)

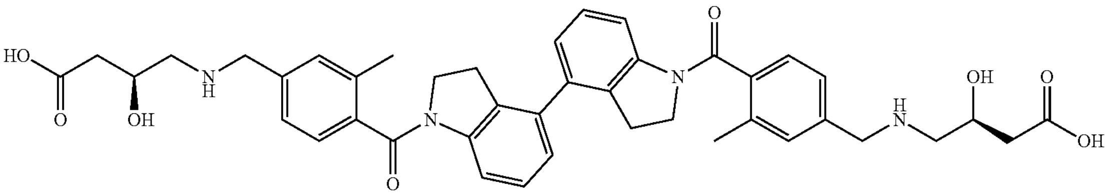 [SMILES: Cc1cc(CNC[C@@H](O)CC(=O)O)ccc1C(=O)N1CCc2c(-c3cccc4c3CCN4C(=O)c3ccc(CNC[C@@H](O)CC(=O)O)cc3C)cccc21]

419 (S)-3-hydroxy-4-((4-(1'-(4-(((S)-4-hydroxy-2-oxopyrrolidin-1-yl)methyl)-2-methylbenzoyl)-[4,4'-biindoline]-1-carbonyl)-3-methylbenzyl)amino)butanoic acid
420 1,1'-((([4,4'-biindoline]-1,1'-dicarbonyl)bis(3-methyl-4,1-phenylene))bis(methylene))bis(pyrrolidin-2-one)

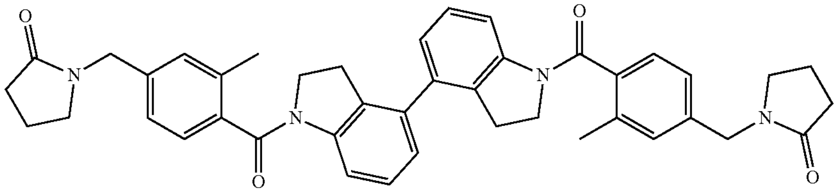 [SMILES: Cc1cc(CN2CCCC2=O)ccc1C(=O)N1CCc2c(-c3cccc4c3CCN4C(=O)c3ccc(CN4CCCC4=O)cc3C)cccc21]

422 (2R,2'R)-2,2'-(((6,6'-(((2,2'-dimethyl-[1,1'-biphenyl]-3,3'-diyl)bis(methylene))bis(oxy))bis(5-chloro-2-methoxypyridine-6,3-diyl))bis(methylene))bis(azanediyl))dipropanamide

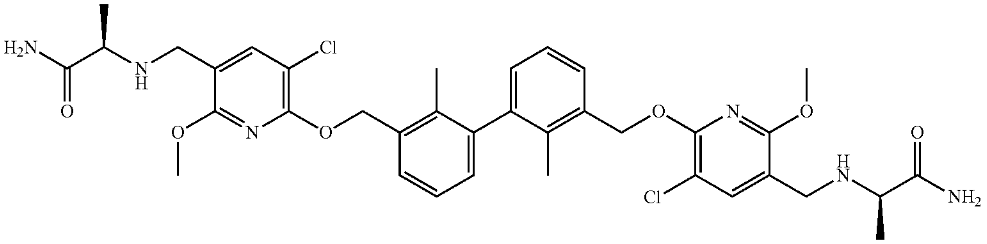 [SMILES: COc1nc(OCc2cccc(-c3cccc(COc4nc(OC)c(CN[C@H](C)C(N)=O)cc4Cl)c3C)c2C)c(Cl)cc1CN[C@H](C)C(N)=O]

423 (3R,3'R)-4,4'-(((2,2'-(2,2'-dimethyl-[1,1'-biphenyl]-3,3'-diyl)bis(benzo[d]thiazole-6,2-diyl))bis(methylene))bis(azanediyl))bis(3-hydroxybutanoic acid)

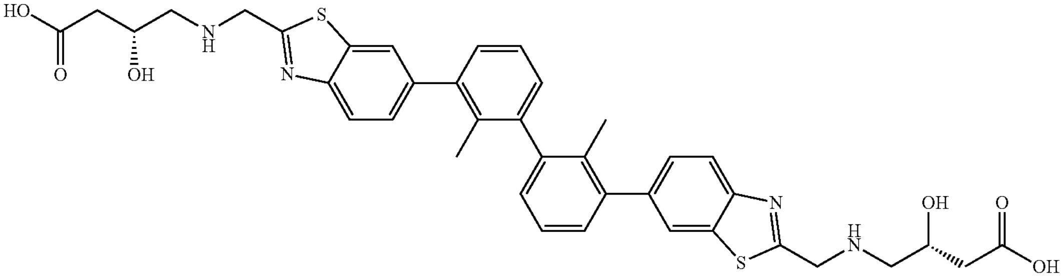 [SMILES: Cc1c(-c2ccc3nc(CNC[C@H](O)CC(=O)O)sc3c2)cccc1-c1cccc(-c2ccc3nc(CNC[C@H](O)CC(=O)O)sc3c2)c1C]

425

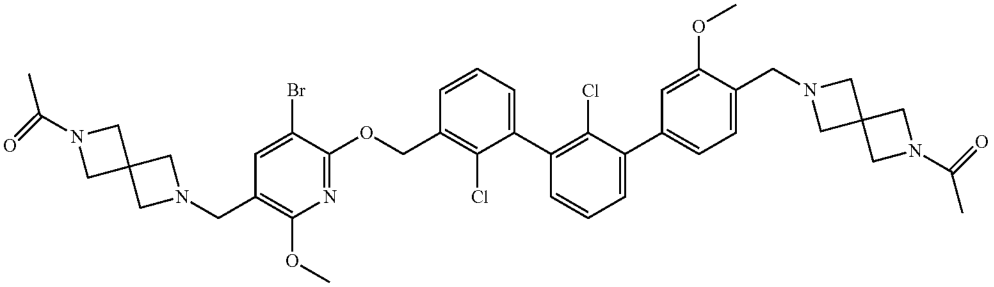 [SMILES: COc1cc(-c2cccc(-c3cccc(COc4nc(OC)c(CN5CC6(C5)CN(C(C)=O)C6)cc4Br)c3Cl)c2Cl)ccc1CN1CC2(C1)CN(C(C)=O)C2]

-continued
426
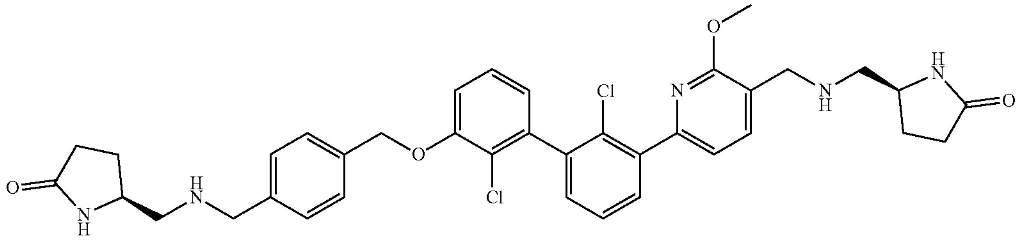 [SMILES: COc1nc(-c2cccc(-c3cccc(OCc4ccc(CNC[C@@H]5CCC(=O)N5)cc4)c3Cl)c2Cl)ccc1CNC[C@@H]1CCC(=O)N1]
428
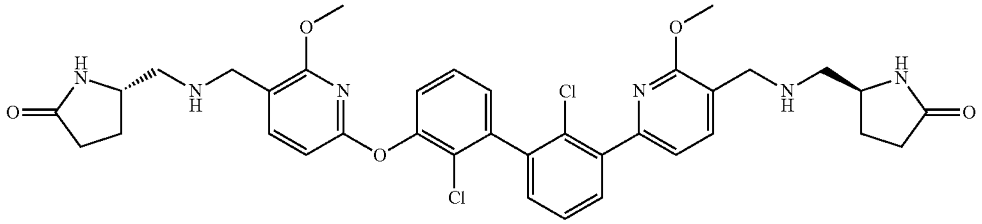 [SMILES: COc1nc(Oc2cccc(-c3cccc(-c4ccc(CNC[C@@H]5CCC(=O)N5)c(OC)n4)c3Cl)c2Cl)ccc1CNC[C@@H]1CCC(=O)N1]
429
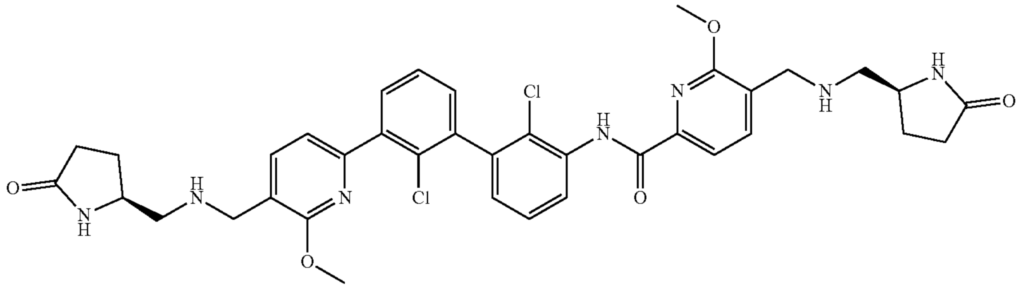 [SMILES: COc1nc(C(=O)Nc2cccc(-c3cccc(-c4ccc(CNC[C@@H]5CCC(=O)N5)c(OC)n4)c3Cl)c2Cl)ccc1CNC[C@@H]1CCC(=O)N1]
430
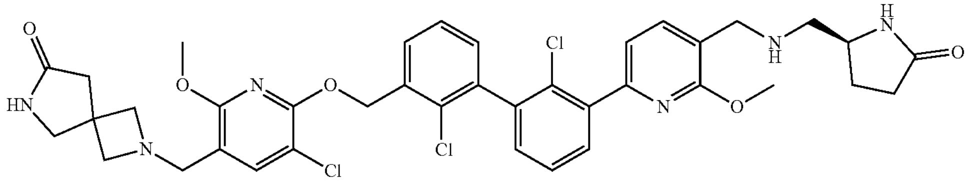 [SMILES: COc1nc(-c2cccc(-c3cccc(COc4nc(OC)c(CN5CC6(CNC(=O)C6)C5)cc4Cl)c3Cl)c2Cl)ccc1CNC[C@@H]1CCC(=O)N1]
431
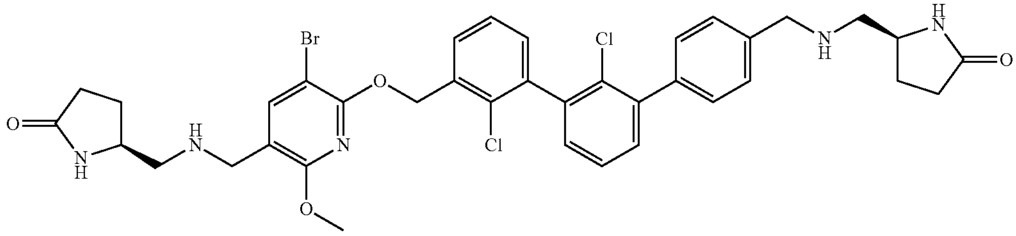 [SMILES: COc1nc(OCc2cccc(-c3cccc(-c4ccc(CNC[C@@H]5CCC(=O)N5)cc4)c3Cl)c2Cl)c(Br)cc1CNC[C@@H]1CCC(=O)N1]
432
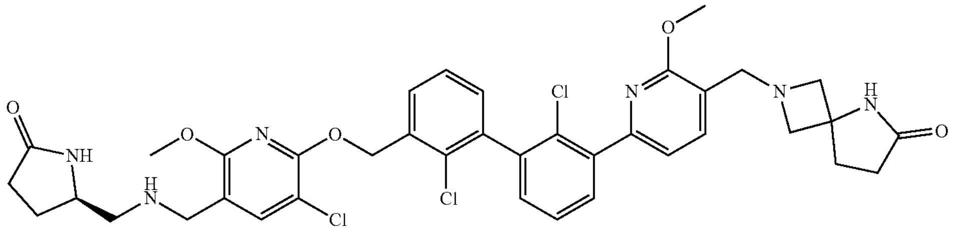 [SMILES: COc1nc(-c2cccc(-c3cccc(COc4nc(OC)c(CNC[C@H]5CCC(=O)N5)cc4Cl)c3Cl)c2Cl)ccc1CN1CC2(CCC(=O)N2)C1]

-continued
433
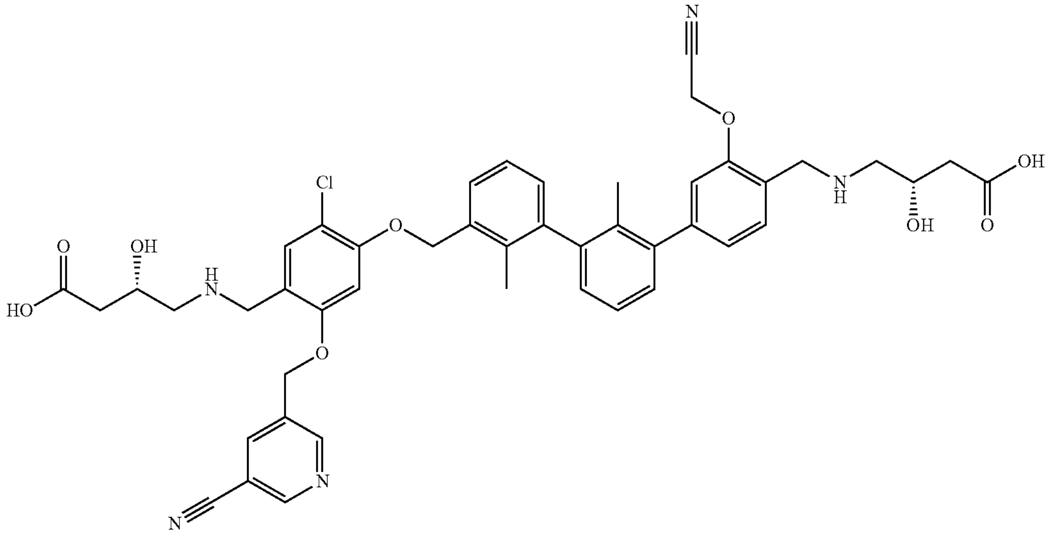 [SMILES: Cc1c(COc2cc(OCc3cncc(C#N)c3)c(CNC[C@@H](O)CC(=O)O)cc2Cl)cccc1-c1cccc(-c2ccc(CNC[C@@H](O)CC(=O)O)c(OCC#N)c2)c1C]
434
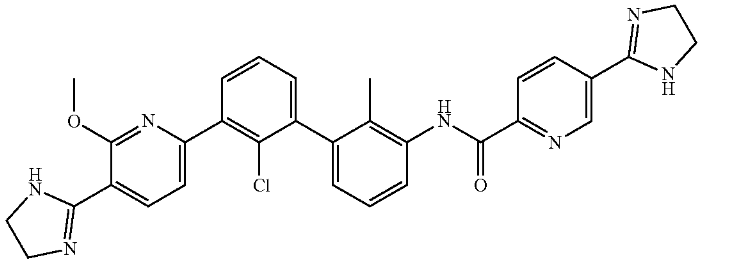 [SMILES: COc1nc(-c2cccc(-c3cccc(NC(=O)c4ccc(C5=NCCN5)cn4)c3C)c2Cl)ccc1C1=NCCN1]
435
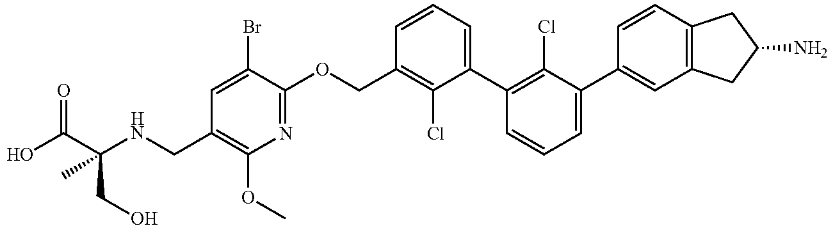 [SMILES: COc1nc(OCc2cccc(-c3cccc(-c4ccc5c(c4)C[C@@H](N)C5)c3Cl)c2Cl)c(Br)cc1CN[C@@](C)(CO)C(=O)O]
436
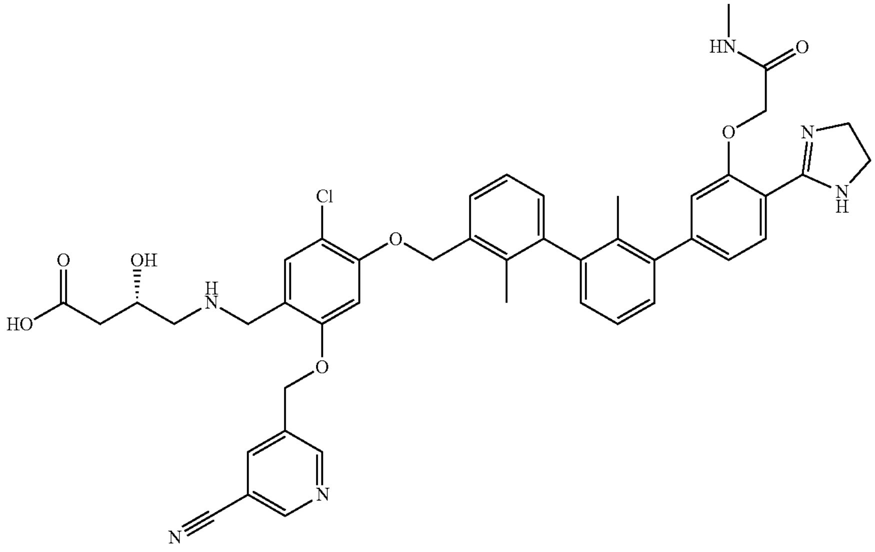 [SMILES: CNC(=O)COc1cc(-c2cccc(-c3cccc(COc4cc(OCc5cncc(C#N)c5)c(CNC[C@@H](O)CC(=O)O)cc4Cl)c3C)c2C)ccc1C1=NCCN1]

-continued
437
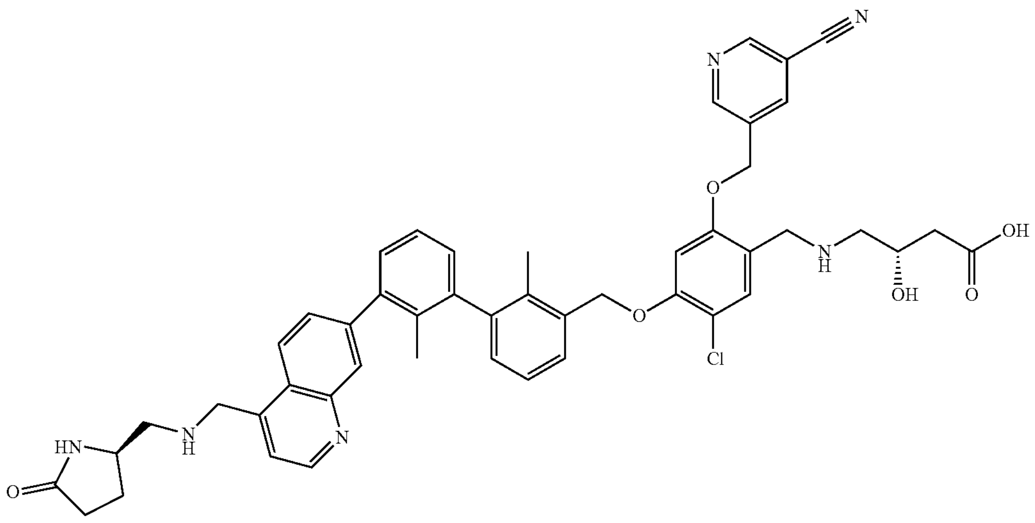 [SMILES: Cc1c(COc2cc(OCc3cncc(C#N)c3)c(CNC[C@@H](O)CC(=O)O)cc2Cl)cccc1-c1cccc(-c2ccc3c(CNC[C@H]4CCC(=O)N4)ccnc3c2)c1C]
438
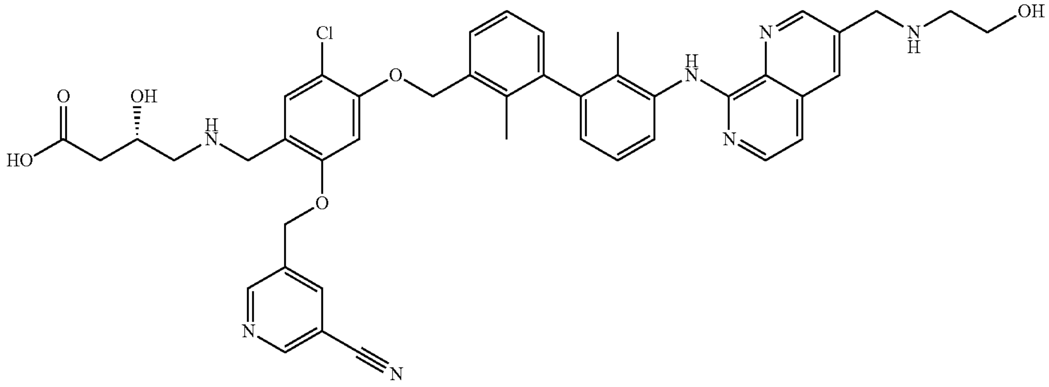 [SMILES: Cc1c(COc2cc(OCc3cncc(C#N)c3)c(CNC[C@@H](O)CC(=O)O)cc2Cl)cccc1-c1cccc(Nc2nccc3cc(CNCCO)cnc23)c1C]
439
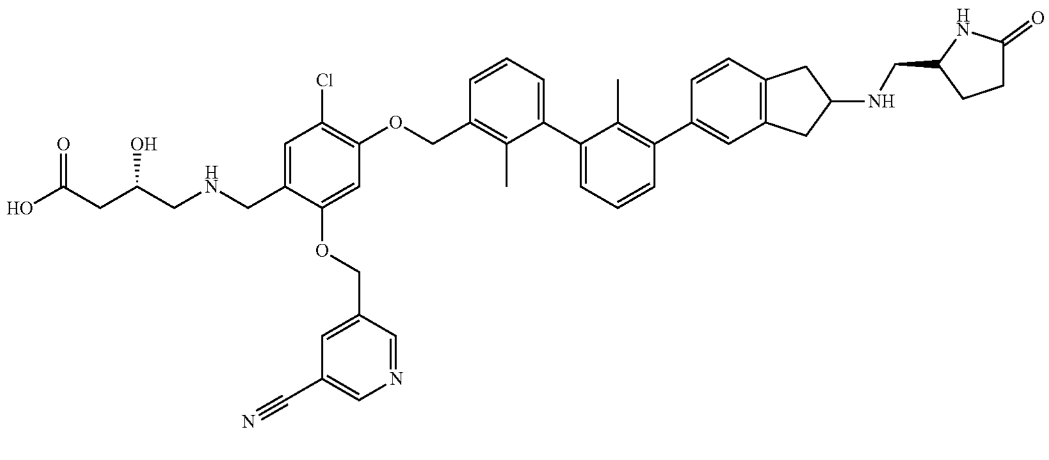

-continued
440
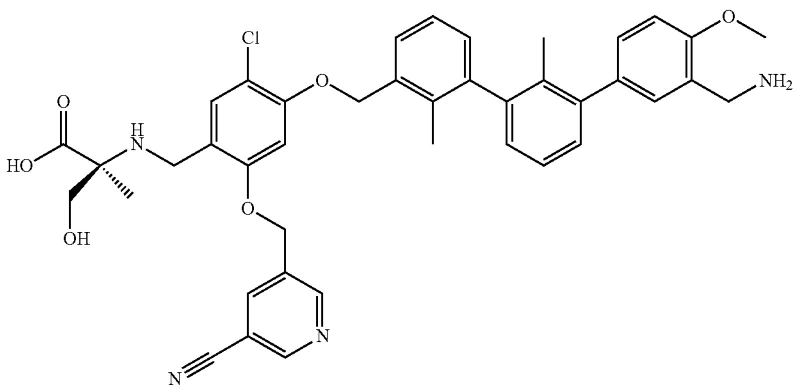 [SMILES: COc1ccc(-c2cccc(-c3cccc(COc4cc(OCc5cncc(C#N)c5)c(CN[C@@](C)(CO)C(=O)O)cc4Cl)c3C)c2C)cc1CN]
441
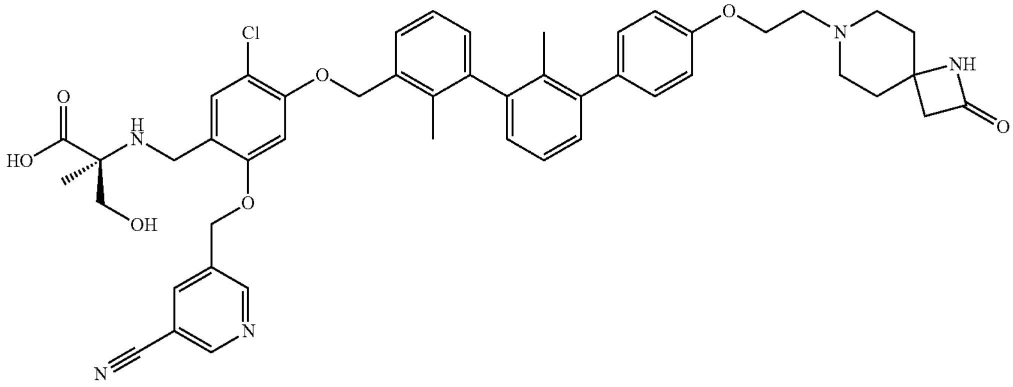 [SMILES: Cc1c(COc2cc(OCc3cncc(C#N)c3)c(CN[C@@](C)(CO)C(=O)O)cc2Cl)cccc1-c1cccc(-c2ccc(OCCN3CCC4(CC3)CC(=O)N4)cc2)c1C]
442
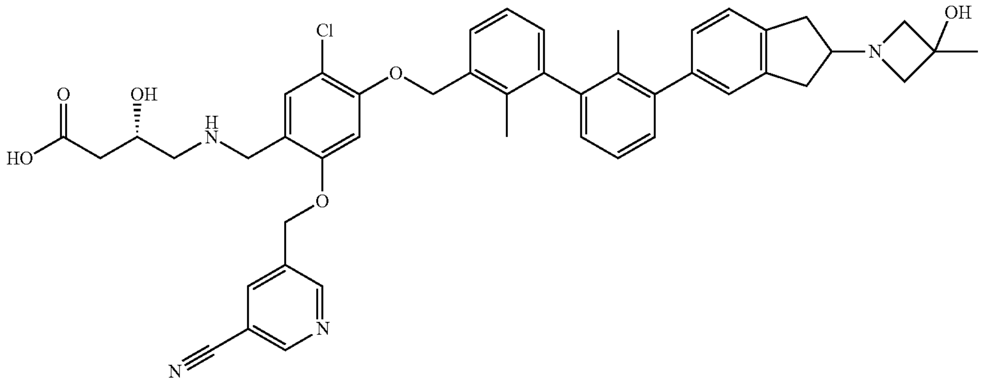 [SMILES: Cc1c(COc2cc(OCc3cncc(C#N)c3)c(CNC[C@@H](O)CC(=O)O)cc2Cl)cccc1-c1cccc(-c2ccc3c(c2)CC(N2CC(C)(O)C2)C3)c1C]
443
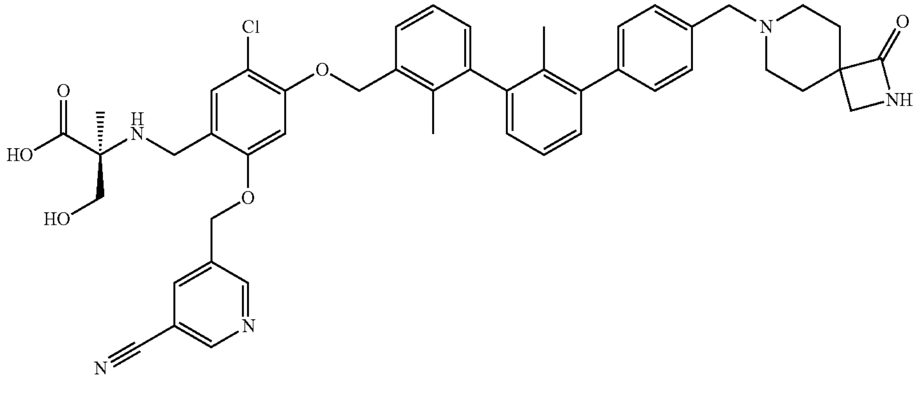

-continued
444
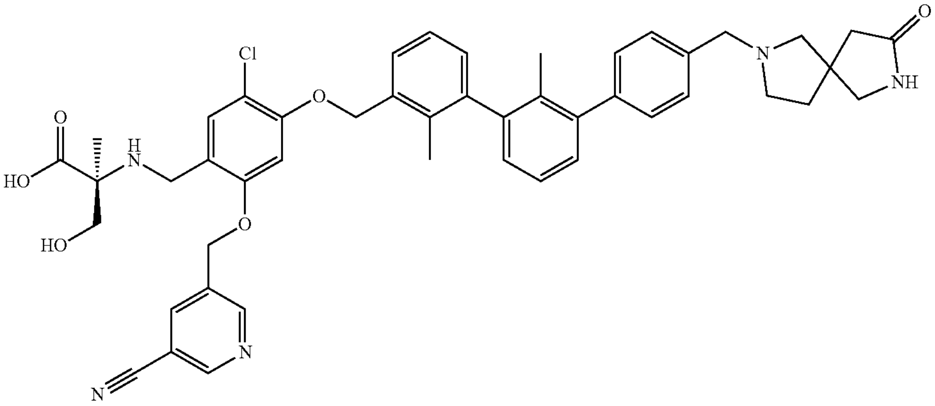
445
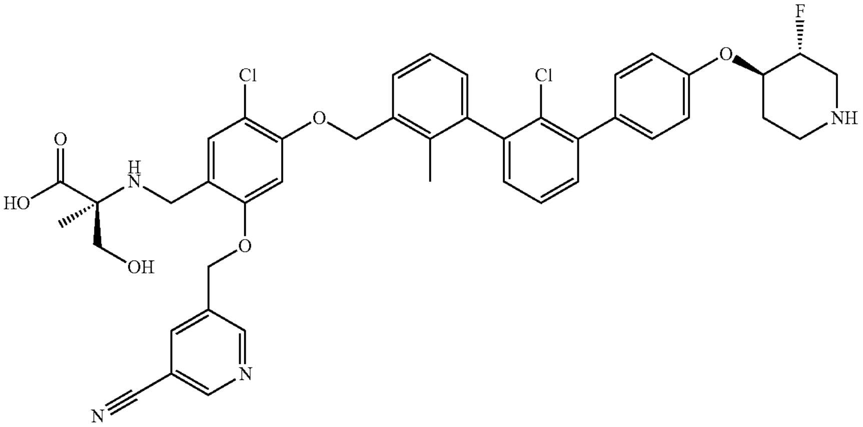 [SMILES: Cc1c(COc2cc(OCc3cncc(C#N)c3)c(CN[C@@](C)(CO)C(=O)O)cc2Cl)cccc1-c1cccc(-c2ccc(O[C@@H]3CCNC[C@H]3F)cc2)c1Cl]
446
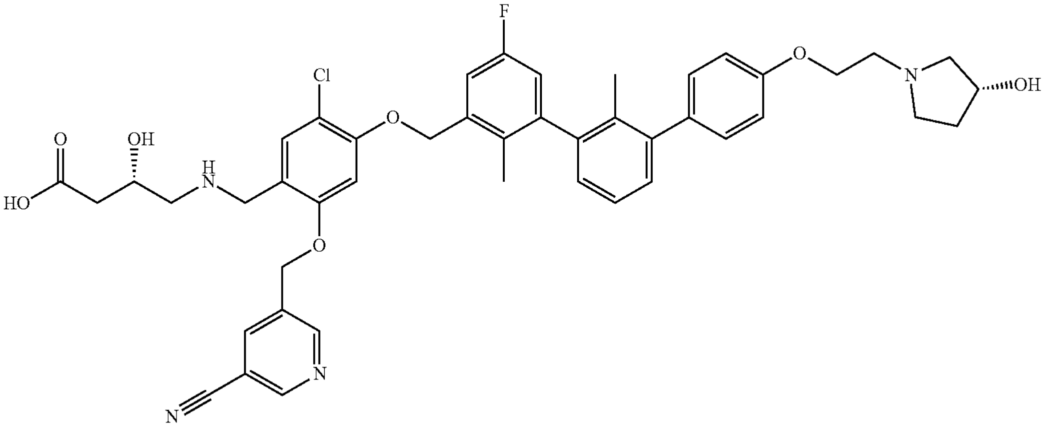 [SMILES: Cc1c(COc2cc(OCc3cncc(C#N)c3)c(CNC[C@@H](O)CC(=O)O)cc2Cl)cc(F)cc1-c1cccc(-c2ccc(OCCN3CC[C@@H](O)C3)cc2)c1C]

-continued
448
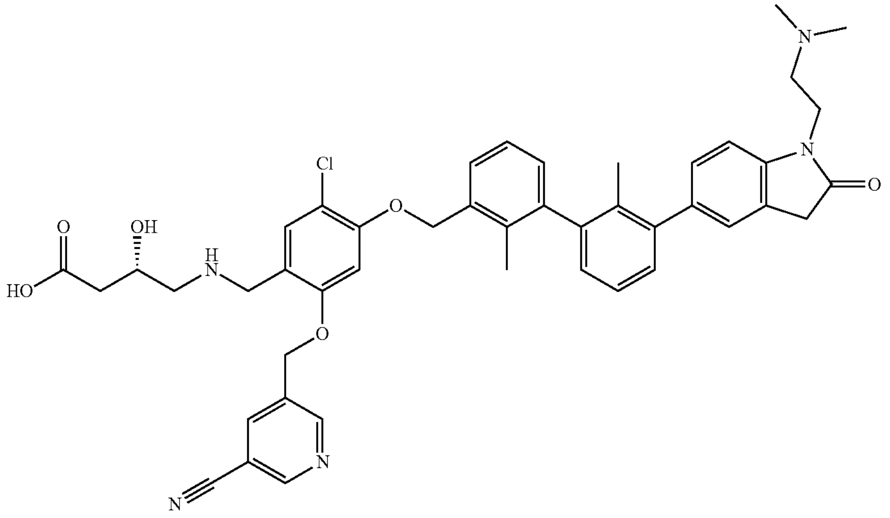 [SMILES: Cc1c(COc2cc(OCc3cncc(C#N)c3)c(CNC[C@@H](O)CC(=O)O)cc2Cl)cccc1-c1cccc(-c2ccc3c(c2)CC(=O)N3CCN(C)C)c1C]
449
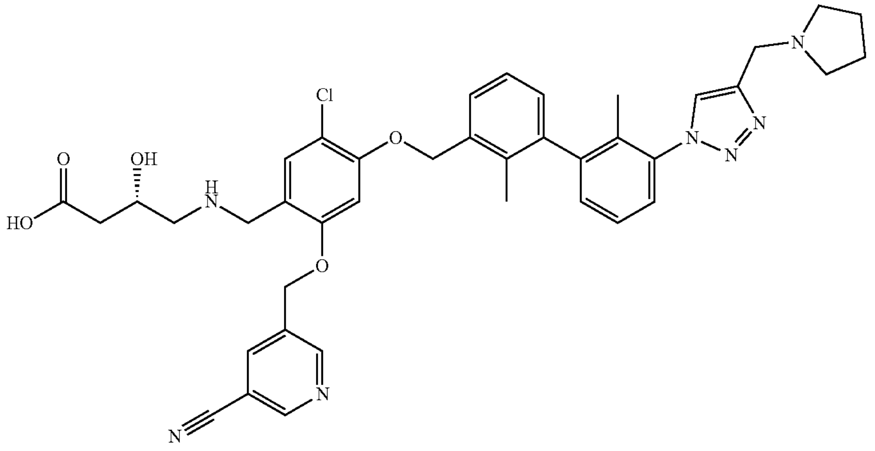 [SMILES: Cc1c(COc2cc(OCc3cncc(C#N)c3)c(CNC[C@@H](O)CC(=O)O)cc2Cl)cccc1-c1cccc(-n2cc(CN3CCCC3)nn2)c1C]
450
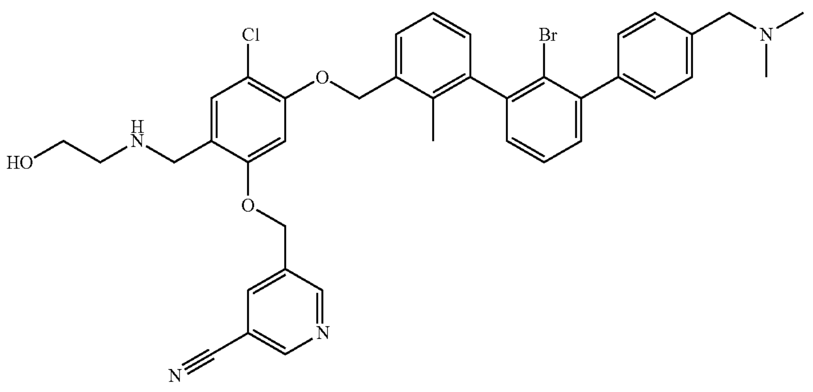 [SMILES: Cc1c(COc2cc(OCc3cncc(C#N)c3)c(CNCCO)cc2Cl)cccc1-c1cccc(-c2ccc(CN(C)C)cc2)c1Br]

-continued
451
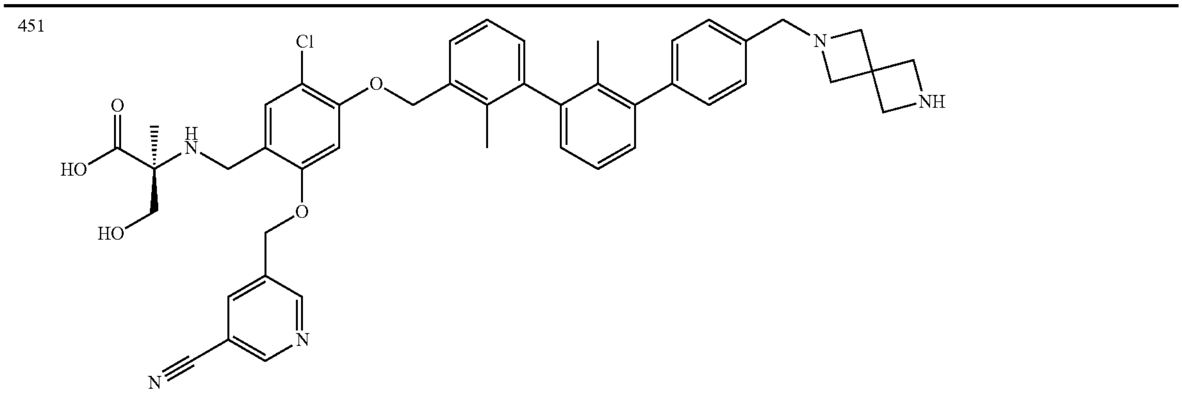
452
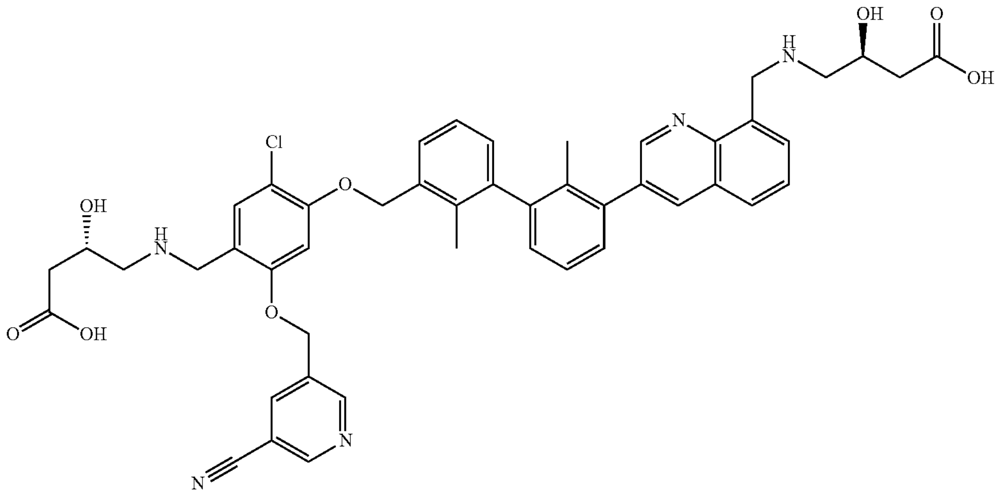 [SMILES: Cc1c(COc2cc(OCc3cncc(C#N)c3)c(CNC[C@@H](O)CC(=O)O)cc2Cl)cccc1-c1cccc(-c2cnc3c(CNC[C@@H](O)CC(=O)O)cccc3c2)c1C]
453
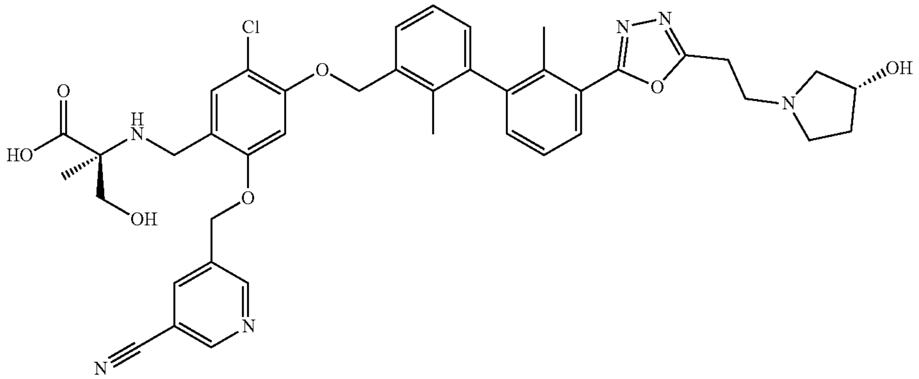 [SMILES: Cc1c(COc2cc(OCc3cncc(C#N)c3)c(CN[C@@](C)(CO)C(=O)O)cc2Cl)cccc1-c1cccc(-c2nnc(CCN3CC[C@@H](O)C3)o2)c1C]
454
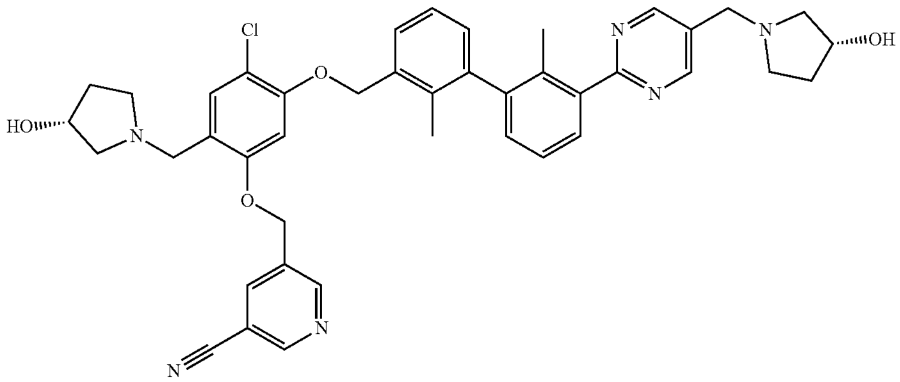 [SMILES: Cc1c(COc2cc(OCc3cncc(C#N)c3)c(CN3CC[C@@H](O)C3)cc2Cl)cccc1-c1cccc(-c2ncc(CN3CC[C@@H](O)C3)cn2)c1C]

-continued
455
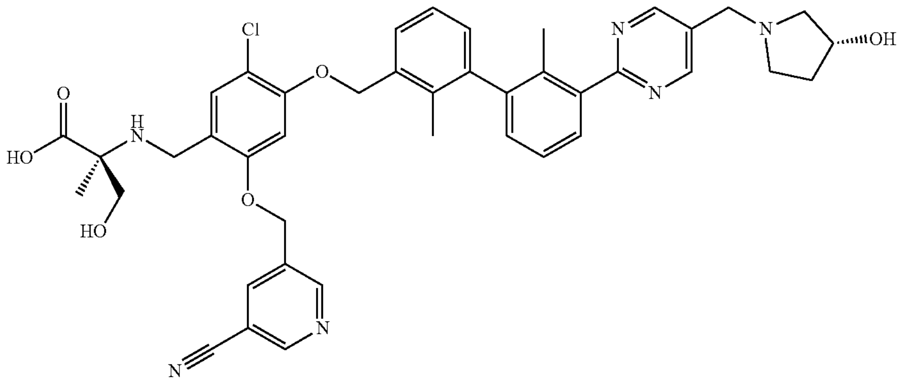 [SMILES: Cc1c(COc2cc(OCc3cncc(C#N)c3)c(CN[C@@](C)(CO)C(=O)O)cc2Cl)cccc1-c1cccc(-c2ncc(CN3CC[C@@H](O)C3)cn2)c1C]
456
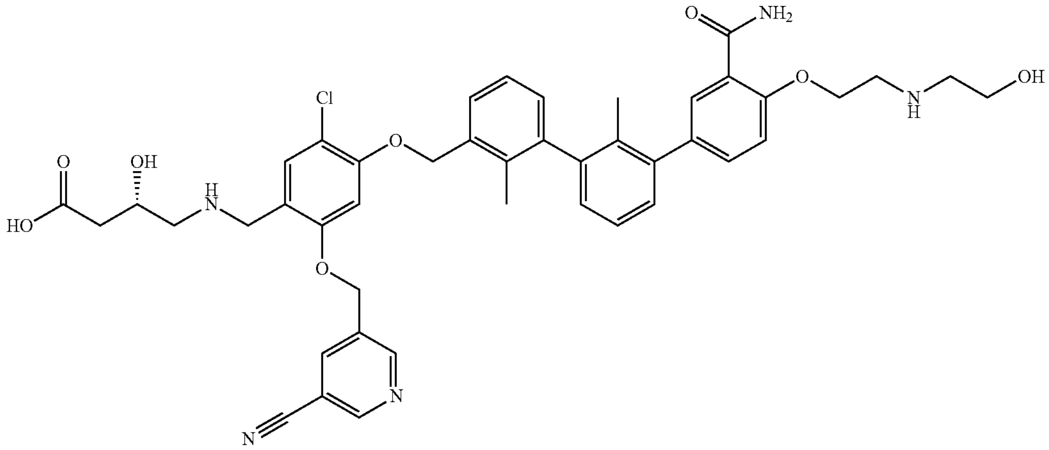 [SMILES: Cc1c(COc2cc(OCc3cncc(C#N)c3)c(CNC[C@@H](O)CC(=O)O)cc2Cl)cccc1-c1cccc(-c2ccc(OCCNCCO)c(C(N)=O)c2)c1C]
457
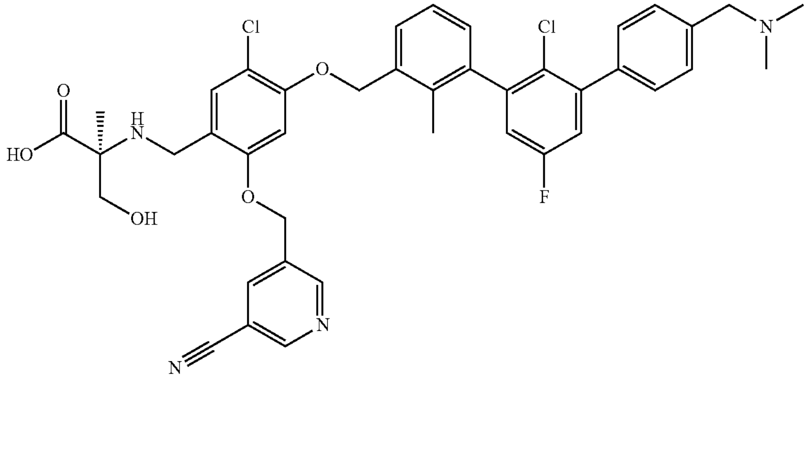 [SMILES: Cc1c(COc2cc(OCc3cncc(C#N)c3)c(CN[C@@](C)(CO)C(=O)O)cc2Cl)cccc1-c1cc(F)cc(-c2ccc(CN(C)C)cc2)c1Cl]

-continued
| | | |
|---|---|---|
| 458 | 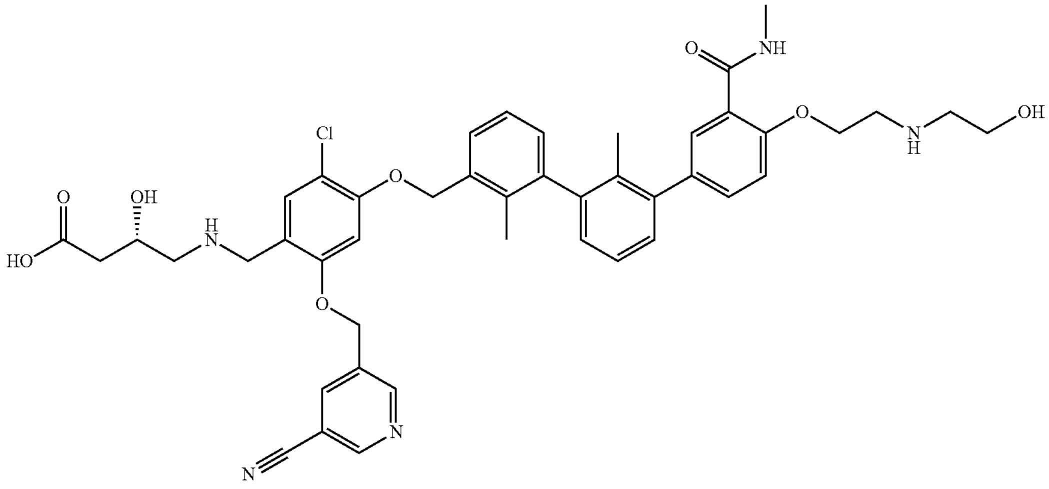 [SMILES: CNC(=O)c1cc(-c2cccc(-c3cccc(COc4cc(OCc5cncc(C#N)c5)c(CNC[C@@H](O)CC(=O)O)cc4Cl)c3C)c2C)ccc1OCCNCCO] | |
| 459 | 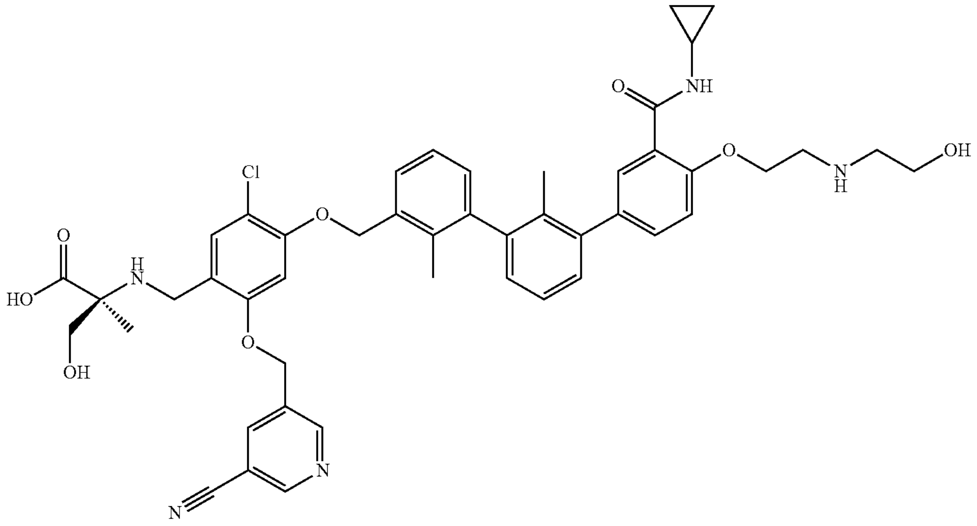 [SMILES: Cc1c(COc2cc(OCc3cncc(C#N)c3)c(CN[C@@](C)(CO)C(=O)O)cc2Cl)cccc1-c1cccc(-c2ccc(OCCNCCO)c(C(=O)NC3CC3)c2)c1C] | |
| Example No. | Structure | ES/MS (m/z, M + H+) |
|---|---|---|
| 460 | 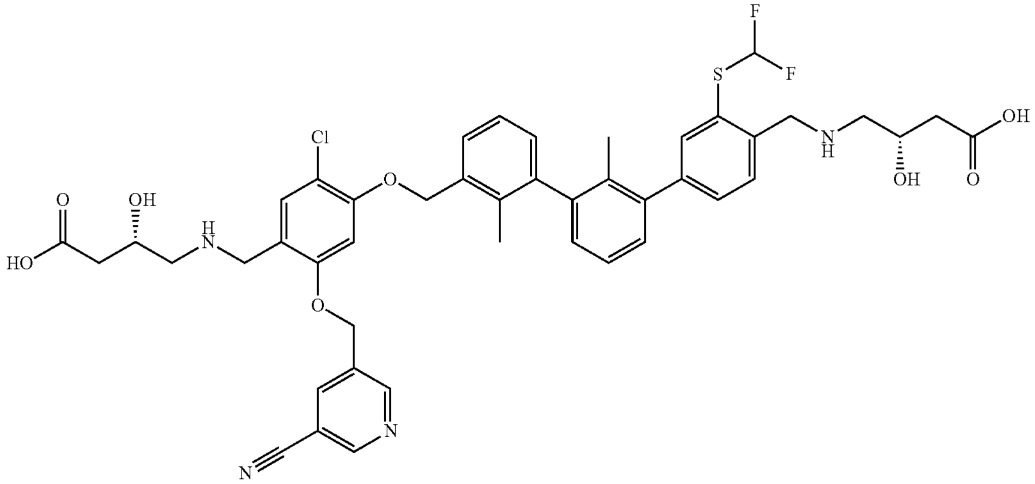 | 875.03 |

-continued
| | | |
|---|---|---|
| 461 | 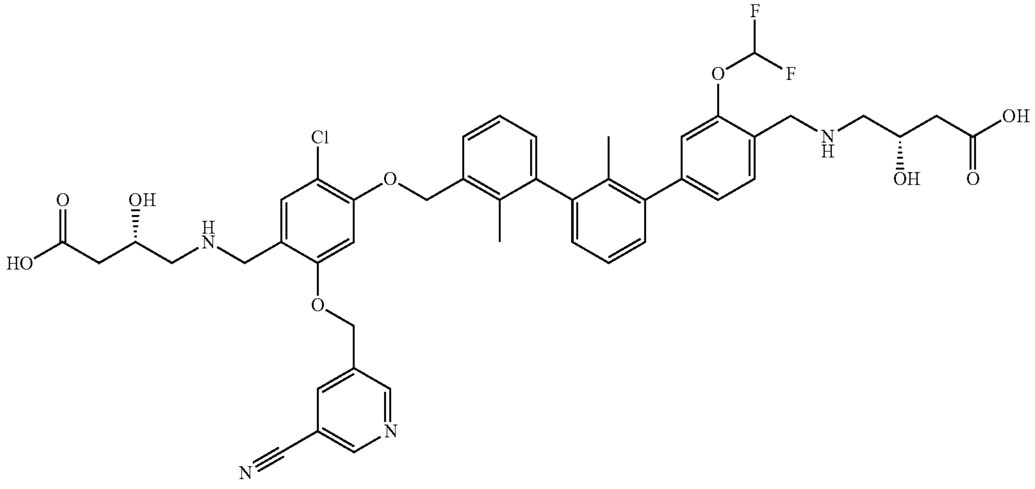 [SMILES: Cc1c(COc2cc(OCc3cncc(C#N)c3)c(CNC[C@@H](O)CC(=O)O)cc2Cl)cccc1-c1cccc(-c2ccc(CNC[C@@H](O)CC(=O)O)c(SC(F)F)c2)c1C] | 859.06 |
| 463 | 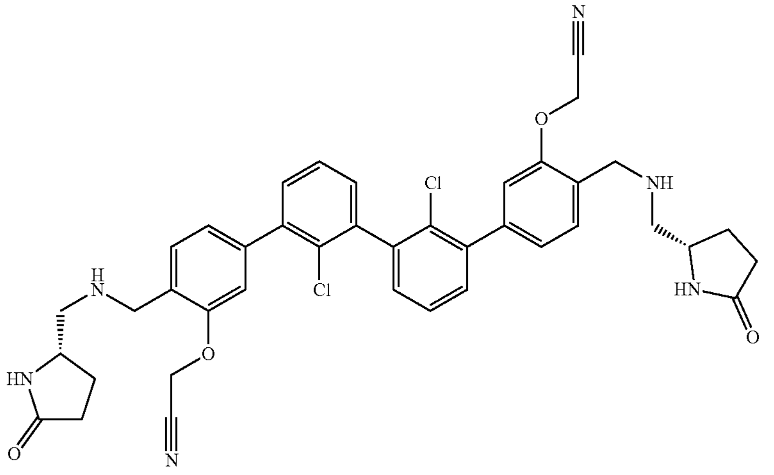 [SMILES: N#CCOc1cc(-c2cccc(-c3cccc(-c4ccc(CNC[C@@H]5CCC(=O)N5)c(OCC#N)c4)c3Cl)c2Cl)ccc1CNC[C@@H]1CCC(=O)N1] | 737.17 |
| 464 | 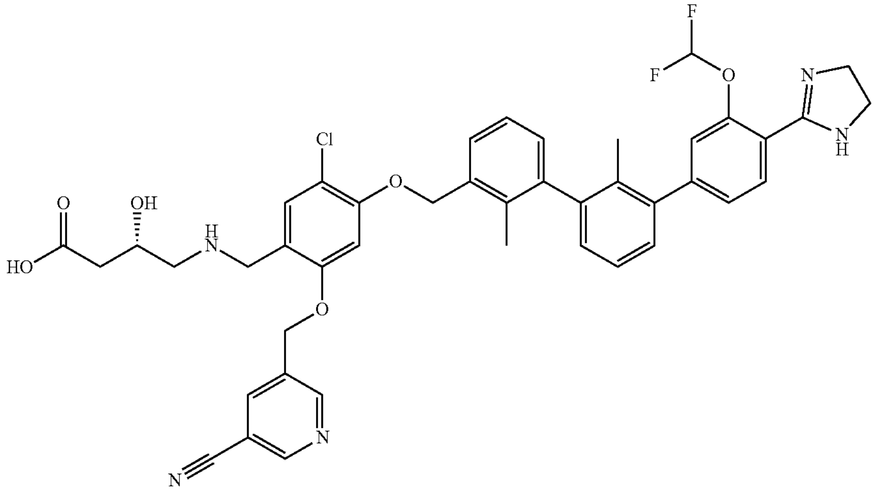 [SMILES: Cc1c(COc2cc(OCc3cncc(C#N)c3)c(CNC[C@@H](O)CC(=O)O)cc2Cl)cccc1-c1cccc(-c2ccc(C3=NCCN3)c(OC(F)F)c2)c1C] | 796.31 |

-continued
| | | |
|---|---|---|
| 465 | 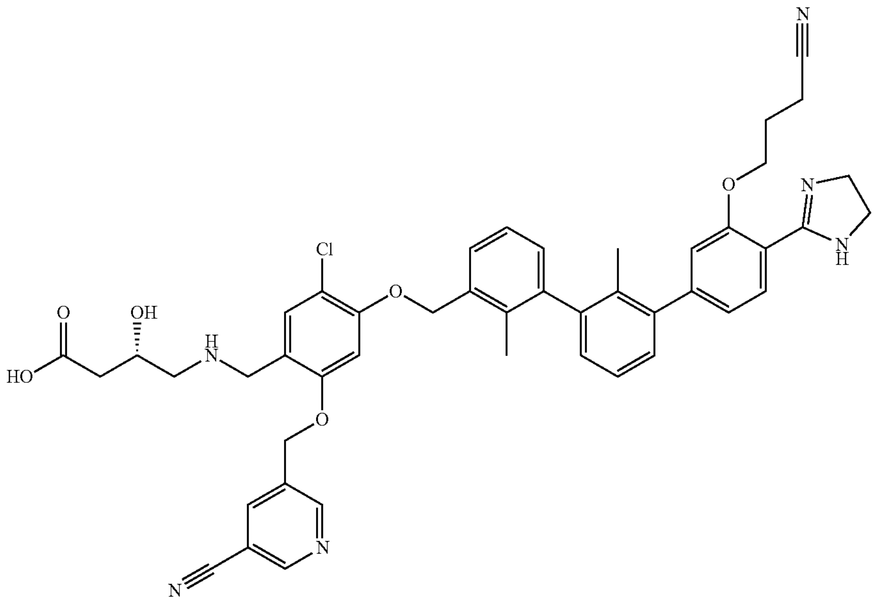 [SMILES: Cc1c(COc2cc(OCc3cncc(C#N)c3)c(CNC[C@@H](O)CC(=O)O)cc2Cl)cccc1-c1cccc(-c2ccc(C3=NCCN3)c(OCCCC#N)c2)c1C] | 813.17 |
| 466 | 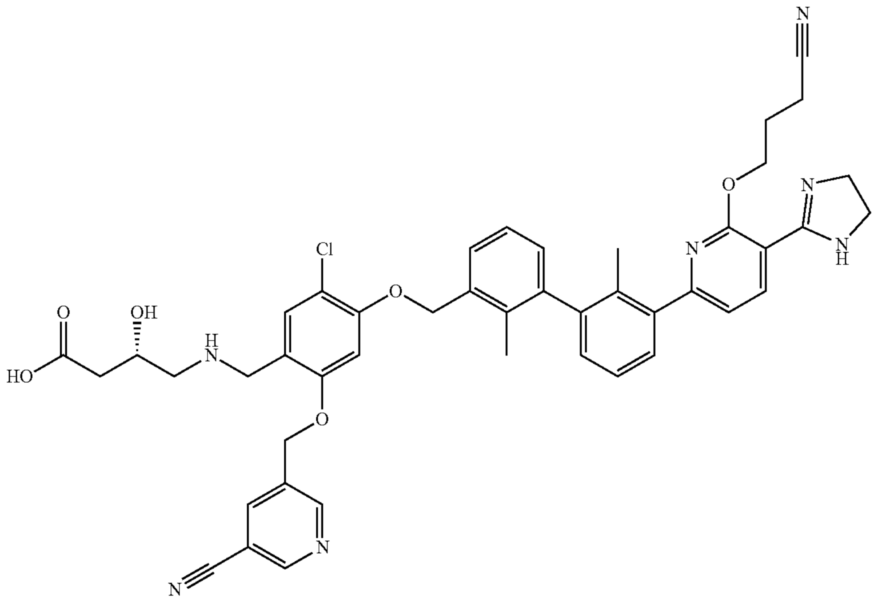 [SMILES: Cc1c(COc2cc(OCc3cncc(C#N)c3)c(CNC[C@@H](O)CC(=O)O)cc2Cl)cccc1-c1cccc(-c2ccc(C3=NCCN3)c(OCCCC#N)n2)c1C] | 814.21 |
| 467 | 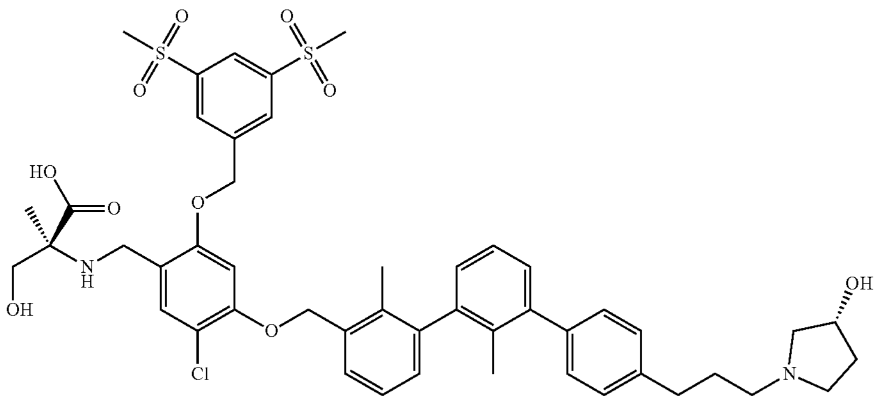 [SMILES: Cc1c(COc2cc(OCc3cc(S(C)(=O)=O)cc(S(C)(=O)=O)c3)c(CN[C@@](C)(CO)C(=O)O)cc2Cl)cccc1-c1cccc(-c2ccc(CCCN3CC[C@@H](O)C3)cc2)c1C] | 921.2 |

-continued
| | | |
|---|---|---|
| 468 | 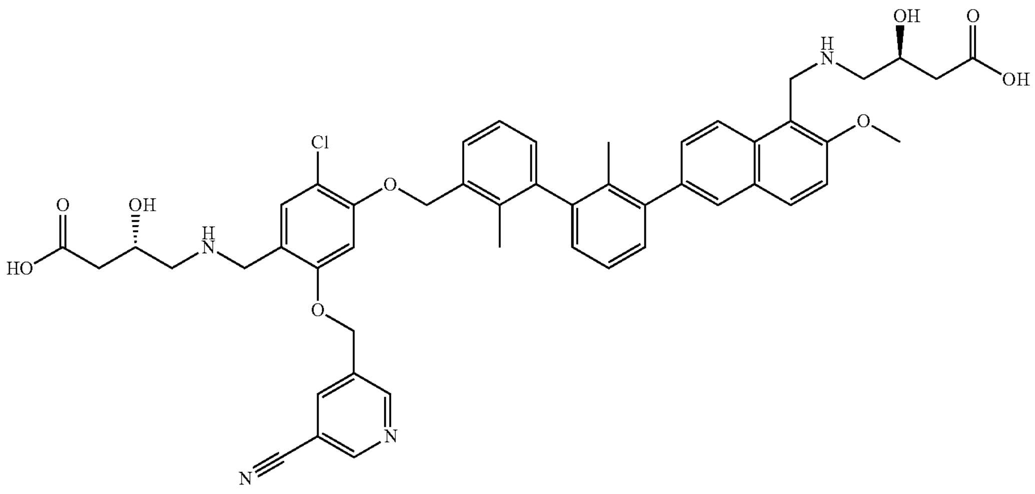 [SMILES: COc1ccc2cc(-c3cccc(-c4cccc(COc5cc(OCc6cncc(C#N)c6)c(CNC[C@@H](O)CC(=O)O)cc5Cl)c4C)c3C)ccc2c1CNC[C@@H](O)CC(=O)O] | 873.9 |
| 469 | 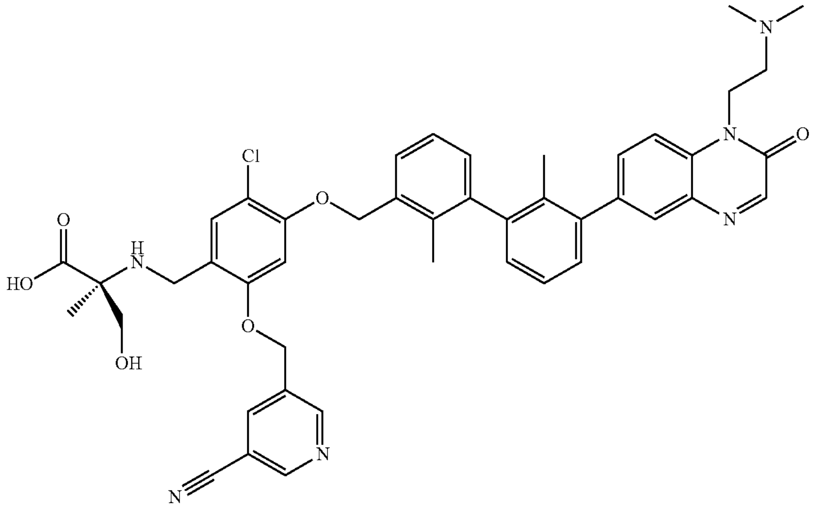 [SMILES: Cc1c(COc2cc(OCc3cncc(C#N)c3)c(CN[C@@](C)(CO)C(=O)O)cc2Cl)cccc1-c1cccc(-c2ccc3c(c2)ncc(=O)n3CCN(C)C)c1C] | 801.12 |
| 470 | 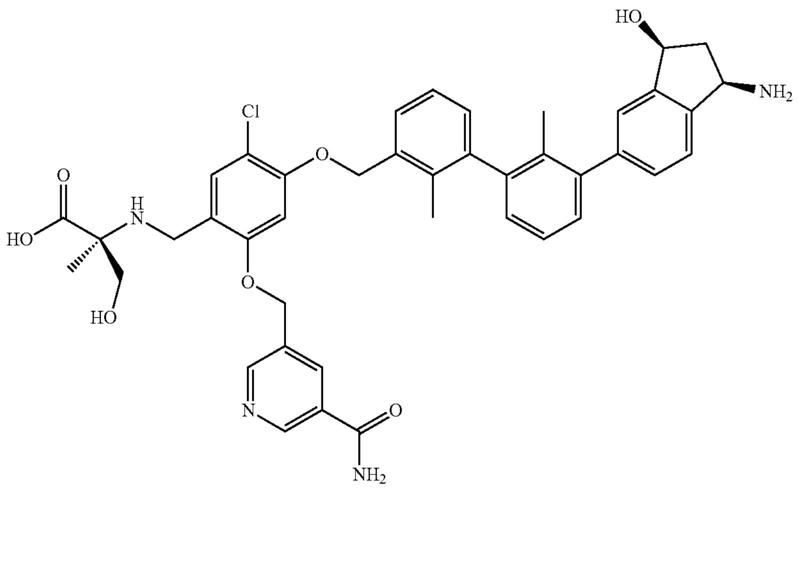 [SMILES: Cc1c(COc2cc(OCc3cncc(C(N)=O)c3)c(CN[C@@](C)(CO)C(=O)O)cc2Cl)cccc1-c1cccc(-c2ccc3c(c2)[C@@H](O)C[C@H]3N)c1C] | 751.3 |

-continued
| | | |
|---|---|---|
| 471 | 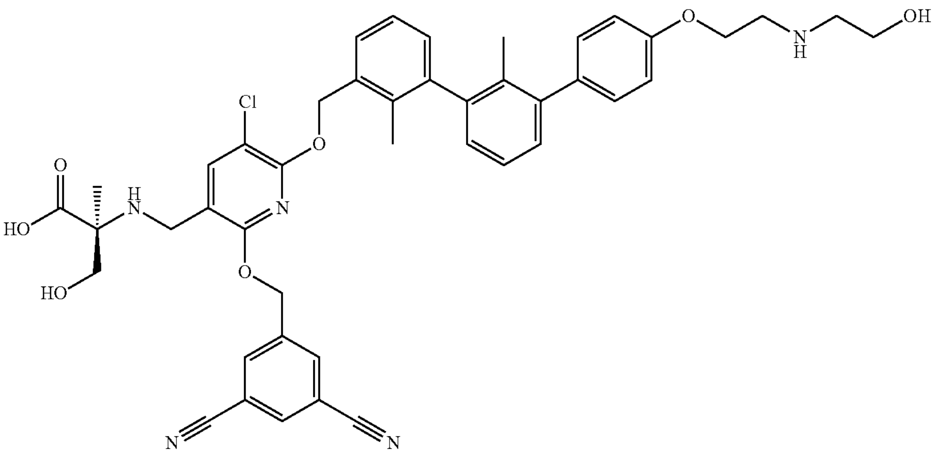 | 790.3 |
| 472 | 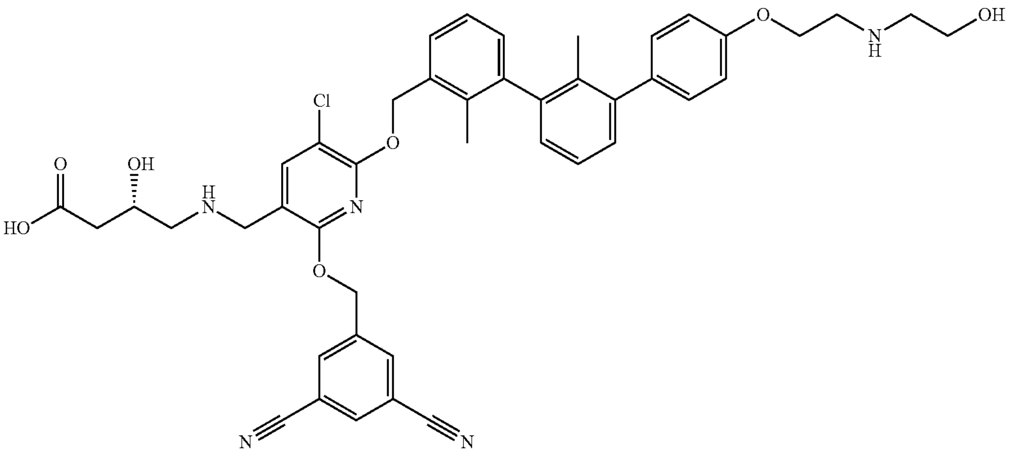 [SMILES: Cc1c(COc2nc(OCc3cc(C#N)cc(C#N)c3)c(CNC[C@@H](O)CC(=O)O)cc2Cl)cccc1-c1cccc(-c2ccc(OCCNCCO)cc2)c1C] | 790.3 |
| 473 | 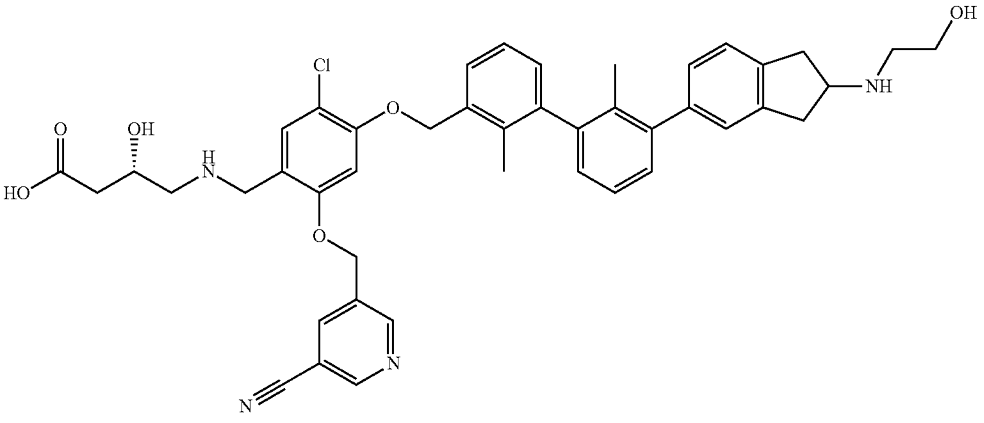 [SMILES: Cc1c(COc2cc(OCc3cncc(C#N)c3)c(CNC[C@@H](O)CC(=O)O)cc2Cl)cccc1-c1cccc(-c2ccc3c(c2)CC(NCCO)C3)c1C] | 761.1 |

-continued
| | | |
|---|---|---|
| 474 | 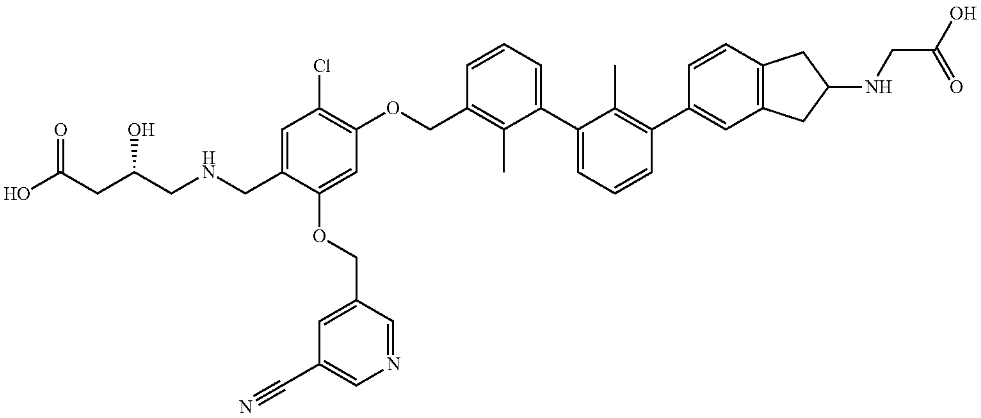 [SMILES: Cc1c(COc2cc(OCc3cncc(C#N)c3)c(CNC[C@@H](O)CC(=O)O)cc2Cl)cccc1-c1cccc(-c2ccc3c(c2)CC(NCC(=O)O)C3)c1C] | 775.2 |
| 475 | 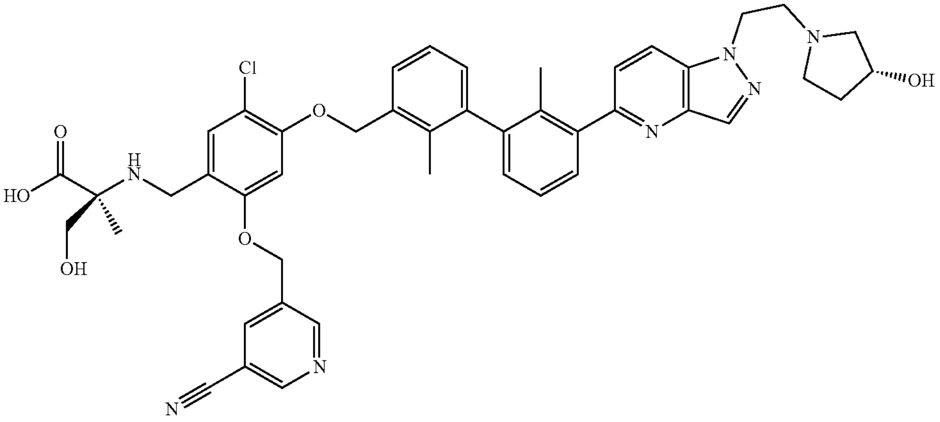 [SMILES: Cc1c(COc2cc(OCc3cncc(C#N)c3)c(CN[C@@](C)(CO)C(=O)O)cc2Cl)cccc1-c1cccc(-c2ccc3c(cnn3CCN3CC[C@@H](O)C3)n2)c1C] | 816.2 |
| 476 | 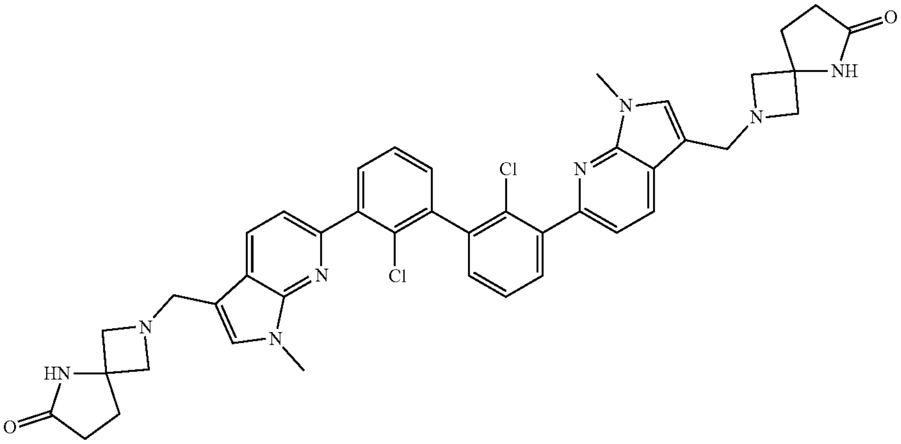 [SMILES: Cn1cc(CN2CC3(CCC(=O)N3)C2)c2ccc(-c3cccc(-c4cccc(-c5ccc6c(CN7CC8(CCC(=O)N8)C7)cn(C)c6n5)c4Cl)c3Cl)nc21] | 759.2 |
| 477 | 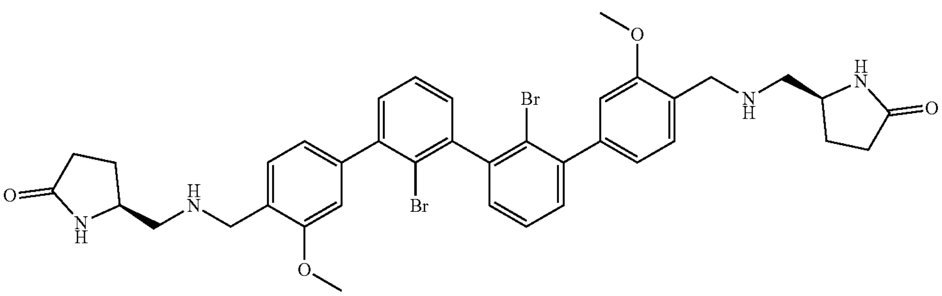 [SMILES: COc1cc(-c2cccc(-c3cccc(-c4ccc(CNC[C@@H]5CCC(=O)N5)c(OC)c4)c3Br)c2Br)ccc1CNC[C@@H]1CCC(=O)N1] | 775 |

-continued
478 1117.1
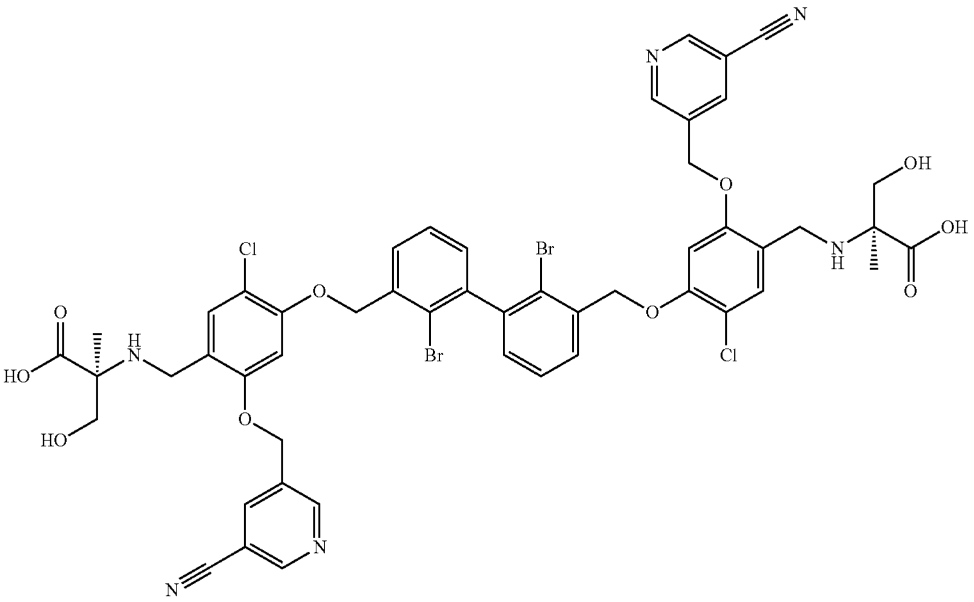 [SMILES: C[C@@](CO)(NCc1cc(Cl)c(OCc2cccc(-c3cccc(COc4cc(OCc5cncc(C#N)c5)c(CN[C@@](C)(CO)C(=O)O)cc4Cl)c3Br)c2Br)cc1OCc1cncc(C#N)c1)C(=O)O]
479 1117.1
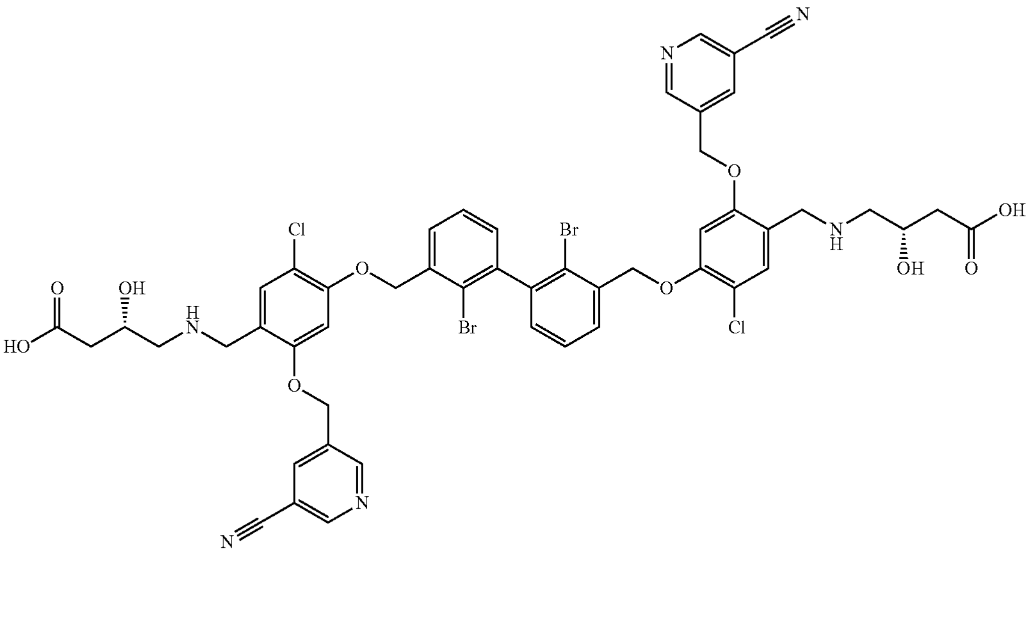 [SMILES: N#Cc1cncc(COc2cc(OCc3cccc(-c4cccc(COc5cc(OCc6cncc(C#N)c6)c(CNC[C@@H](O)CC(=O)O)cc5Cl)c4Br)c3Br)c(Cl)cc2CNC[C@@H](O)CC(=O)O)c1]

-continued
| | | |
|---|---|---|
| 480 | 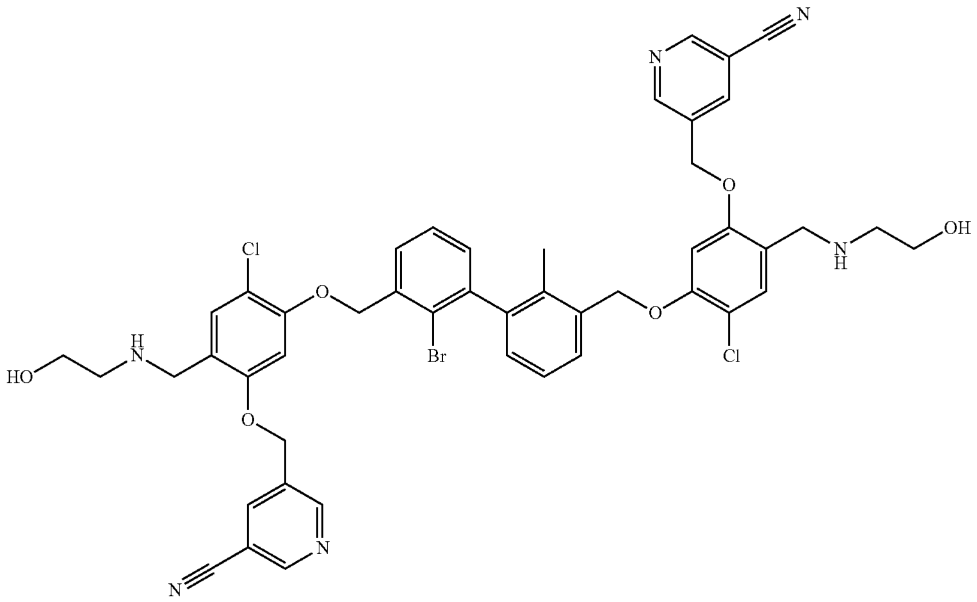 [SMILES: Cc1c(COc2cc(OCc3cncc(C#N)c3)c(CNCCO)cc2Cl)cccc1-c1cccc(COc2cc(OCc3cncc(C#N)c3)c(CNCCO)cc2Cl)c1Br] | 937.2 |
| 481 | 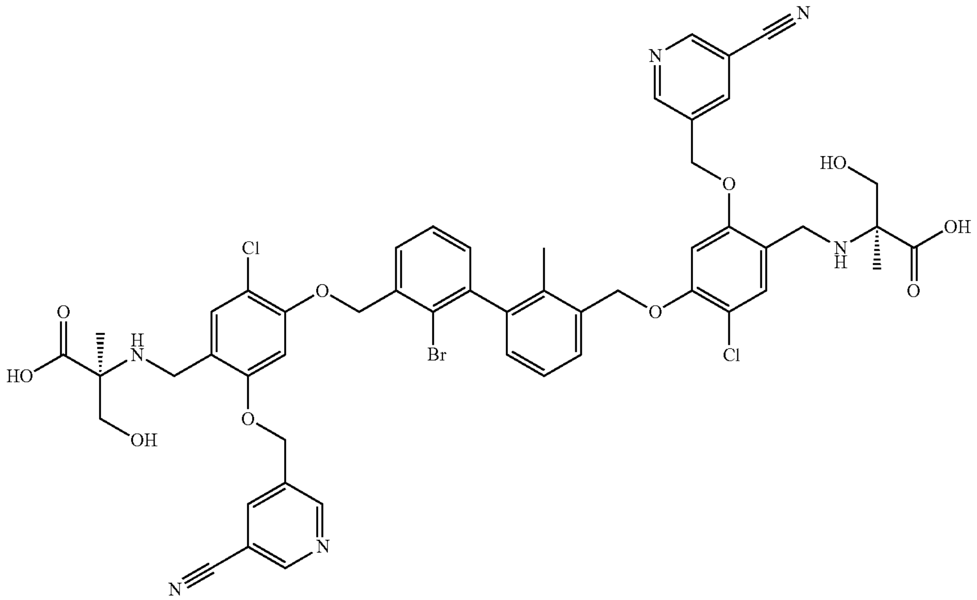 [SMILES: Cc1c(COc2cc(OCc3cncc(C#N)c3)c(CN[C@@](C)(CO)C(=O)O)cc2Cl)cccc1-c1cccc(COc2cc(OCc3cncc(C#N)c3)c(CN[C@@](C)(CO)C(=O)O)cc2Cl)c1Br] | 1053.2 |
| 482 | 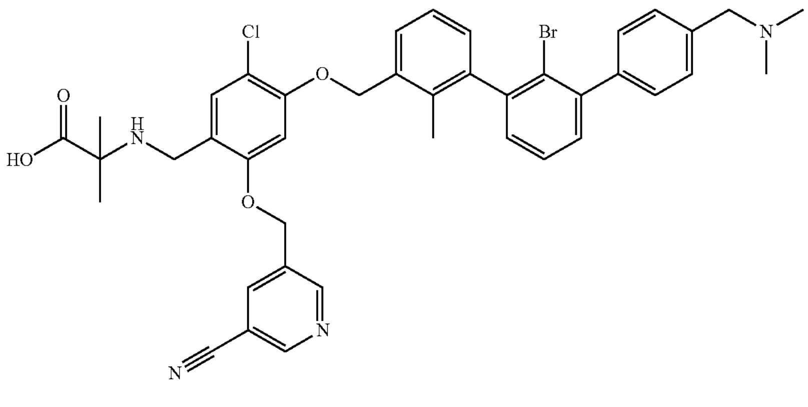 [SMILES: Cc1c(COc2cc(OCc3cncc(C#N)c3)c(CNC(C)(C)C(=O)O)cc2Cl)cccc1-c1cccc(-c2ccc(CN(C)C)cc2)c1Br] | 767.2 |

-continued
| | | |
|---|---|---|
| 483 | 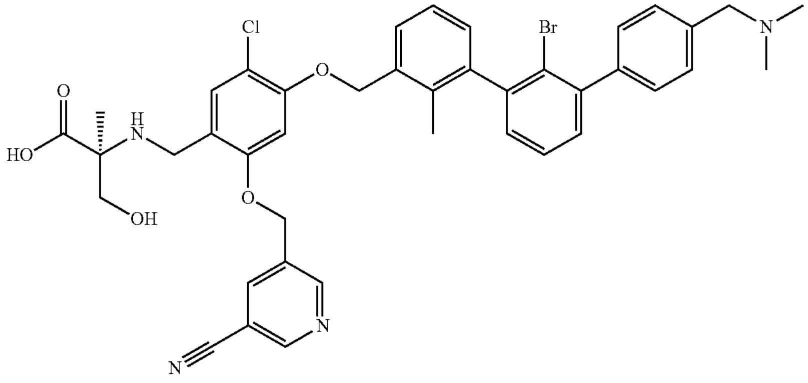 [SMILES: Cc1c(COc2cc(OCc3cncc(C#N)c3)c(CN[C@@](C)(CO)C(=O)O)cc2Cl)cccc1-c1cccc(-c2ccc(CN(C)C)cc2)c1Br] | 783.2 |
| 484 | 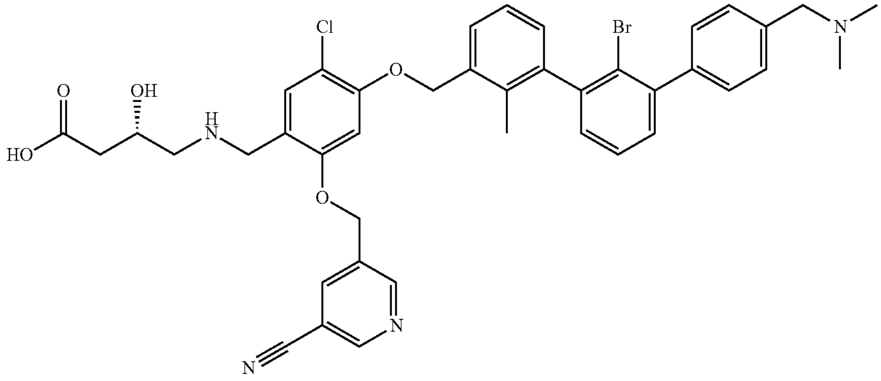 [SMILES: Cc1c(COc2cc(OCc3cncc(C#N)c3)c(CNC[C@@H](O)CC(=O)O)cc2Cl)cccc1-c1cccc(-c2ccc(CN(C)C)cc2)c1Br] | 783.2 |
| 485 | 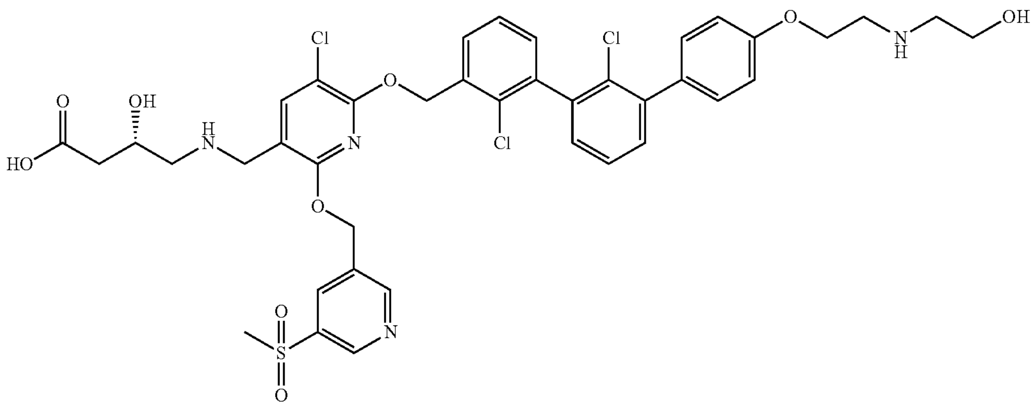 [SMILES: CS(=O)(=O)c1cncc(COc2nc(OCc3cccc(-c4cccc(-c5ccc(OCCNCCO)cc5)c4Cl)c3Cl)c(Cl)cc2CNC[C@@H](O)CC(=O)O)c1] | 859.3 |
| 486 | 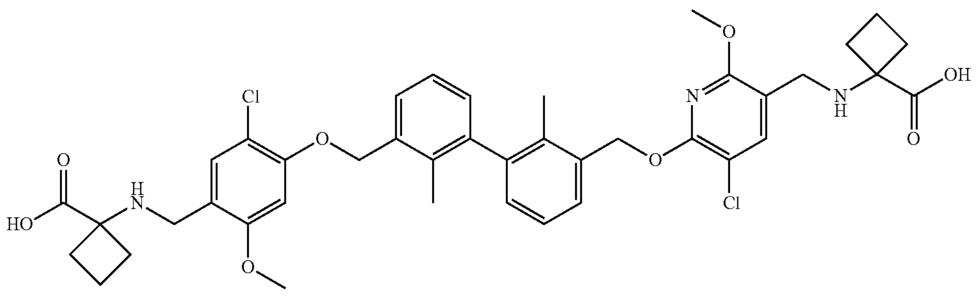 [SMILES: COc1cc(OCc2cccc(-c3cccc(COc4nc(OC)c(CNC5(C(=O)O)CCC5)cc4Cl)c3C)c2C)c(Cl)cc1CNC1(C(=O)O)CCC1] | 779.2 |

-continued
| | | |
|---|---|---|
| 487 | 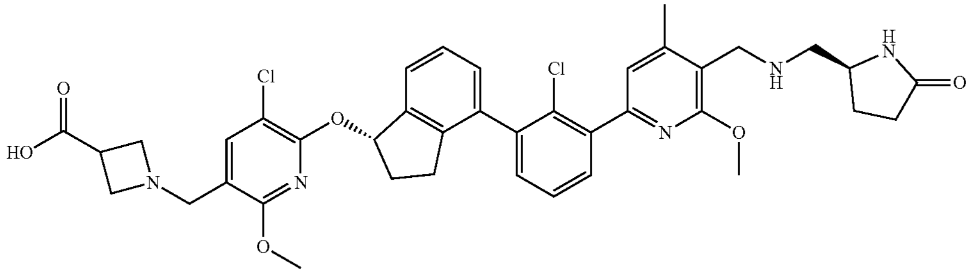 [SMILES: COc1nc(O[C@H]2CCc3c(-c4cccc(-c5cc(C)c(CNC[C@@H]6CCC(=O)N6)c(OC)n5)c4Cl)cccc32)c(Cl)cc1CN1CC(C(=O)O)C1] | 745.98 |
| 488 | 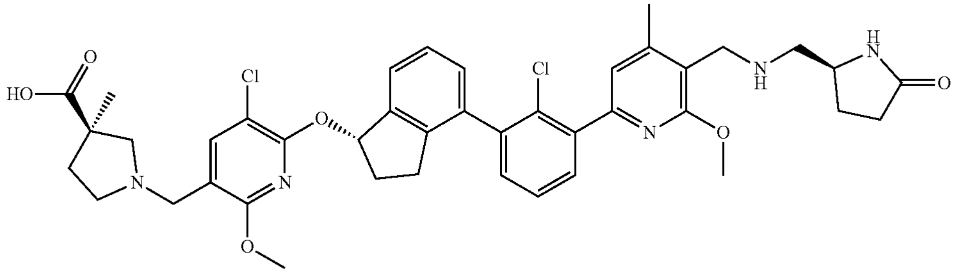 [SMILES: COc1nc(O[C@H]2CCc3c(-c4cccc(-c5cc(C)c(CNC[C@@H]6CCC(=O)N6)c(OC)n5)c4Cl)cccc32)c(Cl)cc1CN1CC[C@@](C)(C(=O)O)C1] | 773.942 |
| 489 | 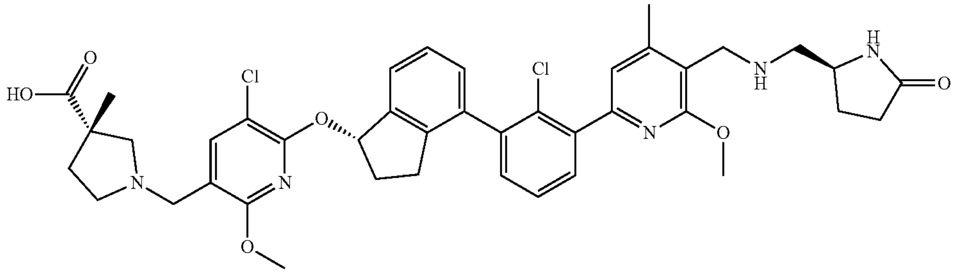 [SMILES: COc1nc(O[C@H]2CCc3c(-c4cccc(-c5cc(C)c(CNC[C@@H]6CCC(=O)N6)c(OC)n5)c4Cl)cccc32)c(Cl)cc1CN1CC[C@](C)(C(=O)O)C1] | 773.946 |
| 490 | 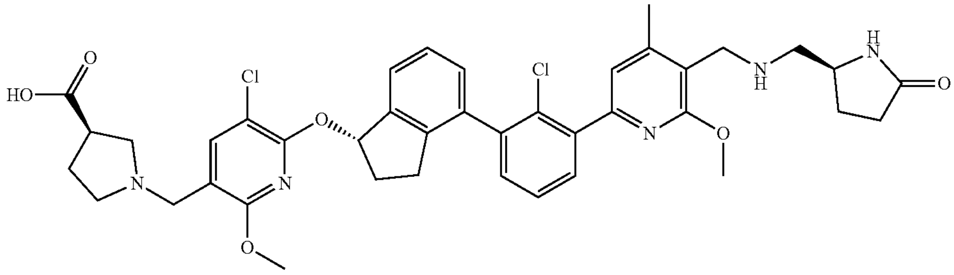 [SMILES: COc1nc(O[C@H]2CCc3c(-c4cccc(-c5cc(C)c(CNC[C@@H]6CCC(=O)N6)c(OC)n5)c4Cl)cccc32)c(Cl)cc1CN1CC[C@@H](C(=O)O)C1] | 759.991 |
| 491 | 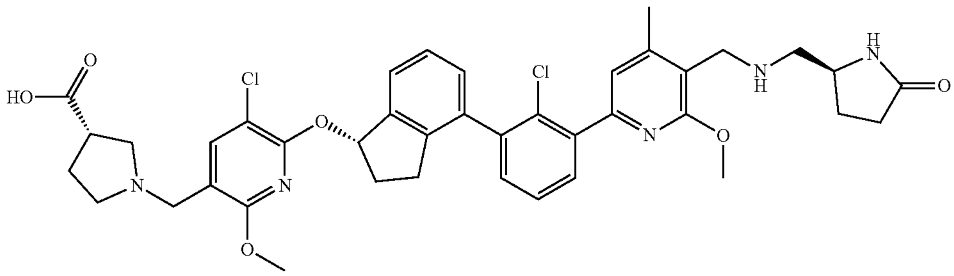 [SMILES: COc1nc(O[C@H]2CCc3c(-c4cccc(-c5cc(C)c(CNC[C@@H]6CCC(=O)N6)c(OC)n5)c4Cl)cccc32)c(Cl)cc1CN1CC[C@H](C(=O)O)C1] | 759.933 |

-continued
497 783.164
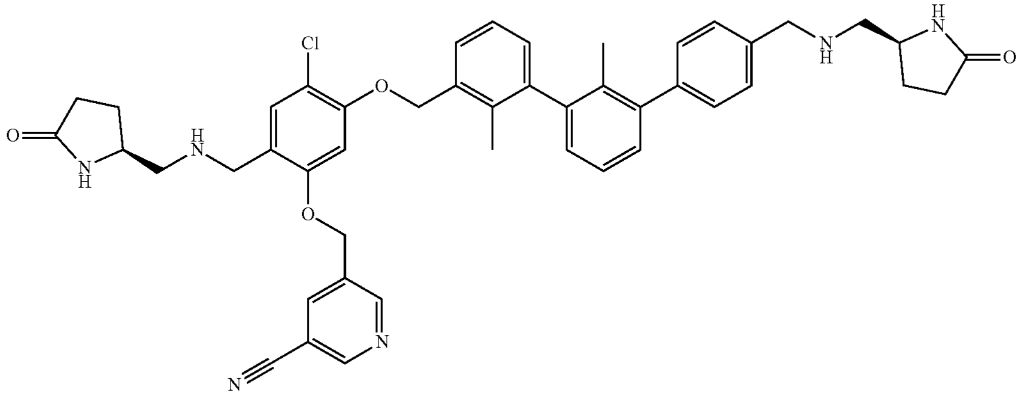 [SMILES: Cc1c(COc2cc(OCc3cncc(C#N)c3)c(CNC[C@@H]3CCC(=O)N3)cc2Cl)cccc1-c1cccc(-c2ccc(CNC[C@@H]3CCC(=O)N3)cc2)c1C]
498 705.004
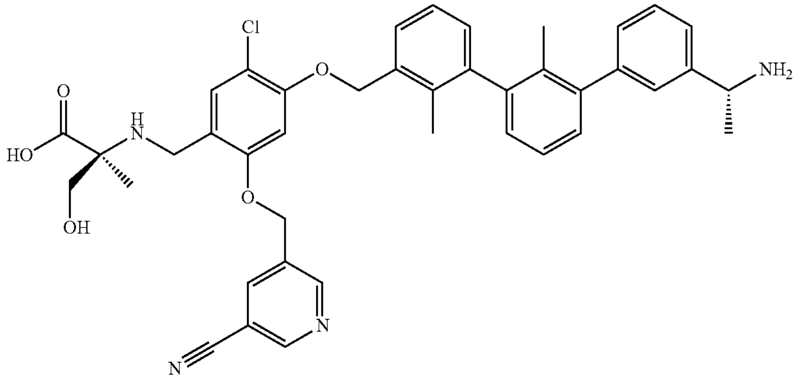 [SMILES: Cc1c(COc2cc(OCc3cncc(C#N)c3)c(CN[C@@](C)(CO)C(=O)O)cc2Cl)cccc1-c1cccc(-c2cccc([C@@H](C)N)c2)c1C]
499 705.008
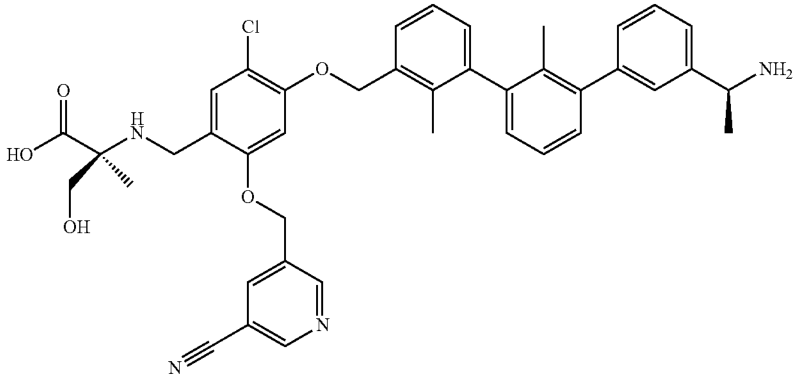 [SMILES: Cc1c(COc2cc(OCc3cncc(C#N)c3)c(CN[C@@](C)(CO)C(=O)O)cc2Cl)cccc1-c1cccc(-c2cccc([C@H](C)N)c2)c1C]
500 731.089
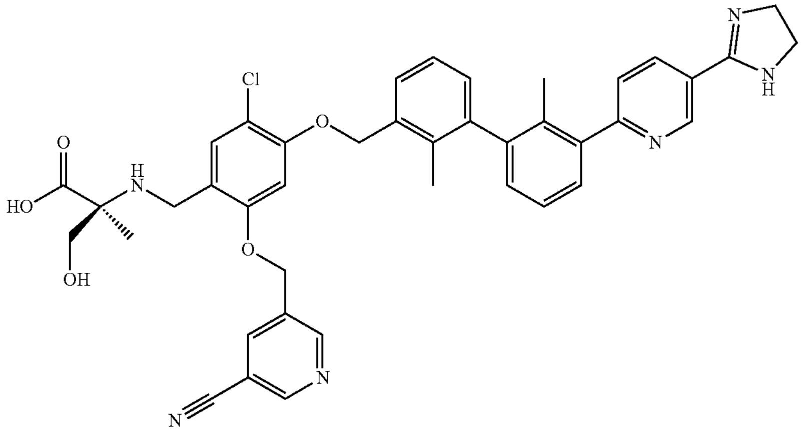 [SMILES: Cc1c(COc2cc(OCc3cncc(C#N)c3)c(CN[C@@](C)(CO)C(=O)O)cc2Cl)cccc1-c1cccc(-c2ccc(C3=NCCN3)cn2)c1C]

-continued
501 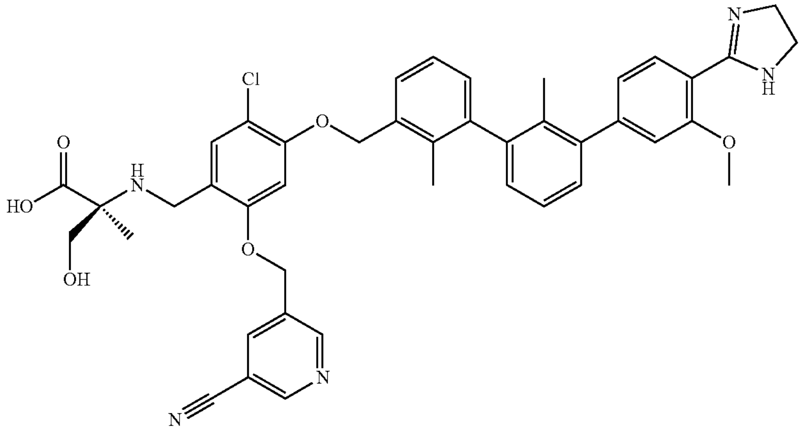 760.244
502 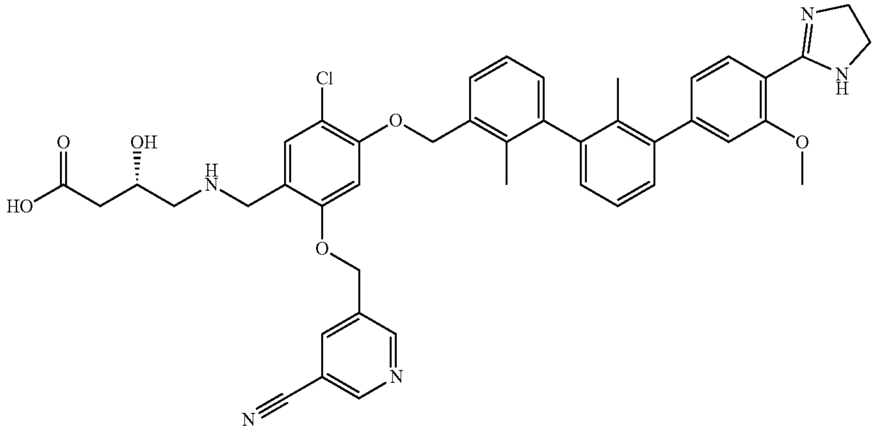 [SMILES: COc1cc(-c2cccc(-c3cccc(COc4cc(OCc5cncc(C#N)c5)c(CNC[C@@H](O)CC(=O)O)cc4Cl)c3C)c2C)ccc1C1=NCCN1] 760.31
503 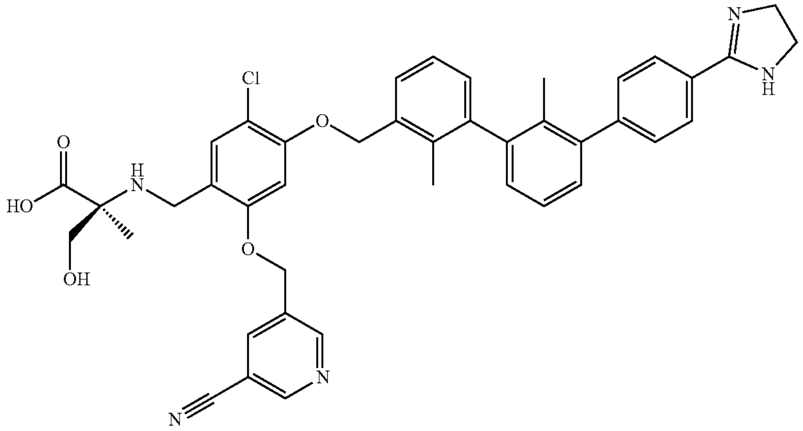 [SMILES: Cc1c(COc2cc(OCc3cncc(C#N)c3)c(CN[C@@](C)(CO)C(=O)O)cc2Cl)cccc1-c1cccc(-c2ccc(C3=NCCN3)cc2)c1C] 730.131

-continued
504 761.175
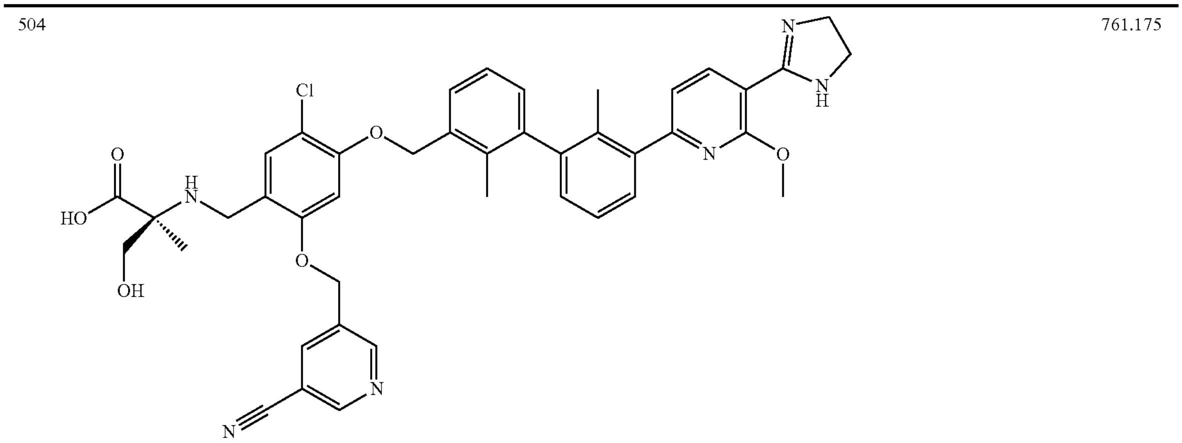
505 761.175
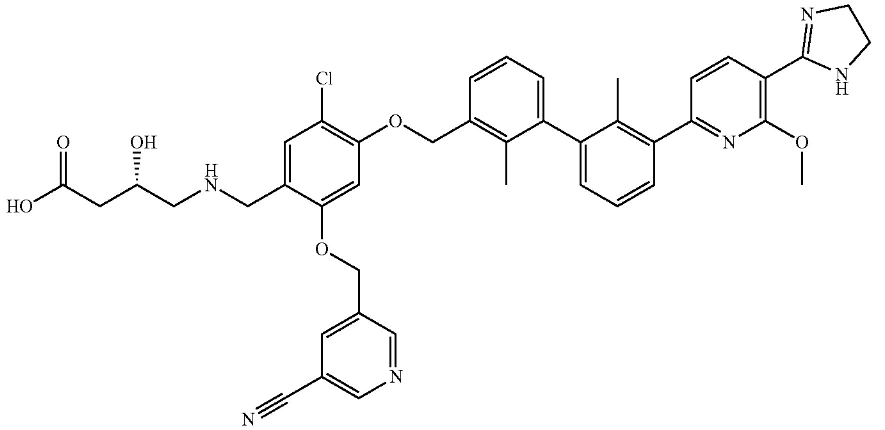 [SMILES: COc1nc(-c2cccc(-c3cccc(COc4cc(OCc5cncc(C#N)c5)c(CNC[C@@H](O)CC(=O)O)cc4Cl)c3C)c2C)ccc1C1=NCCN1]
506 721.033
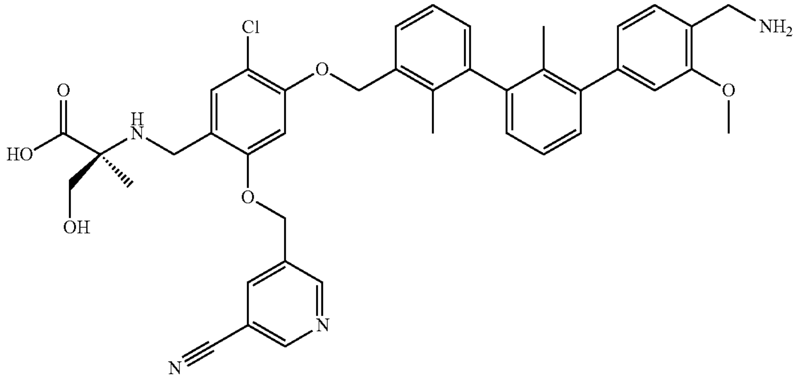 [SMILES: COc1cc(-c2cccc(-c3cccc(COc4cc(OCc5cncc(C#N)c5)c(CN[C@@](C)(CO)C(=O)O)cc4Cl)c3C)c2C)ccc1CN]
507 721.087
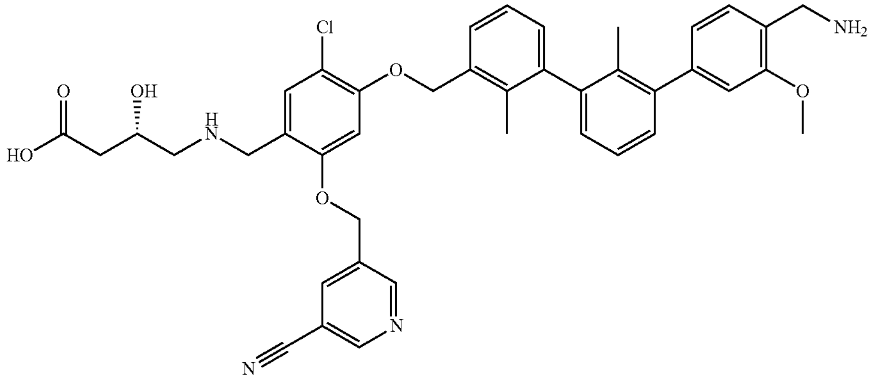 [SMILES: COc1cc(-c2cccc(-c3cccc(COc4cc(OCc5cncc(C#N)c5)c(CNC[C@@H](O)CC(=O)O)cc4Cl)c3C)c2C)ccc1CN]

-continued
| | | |
|---|---|---|
| 508 | 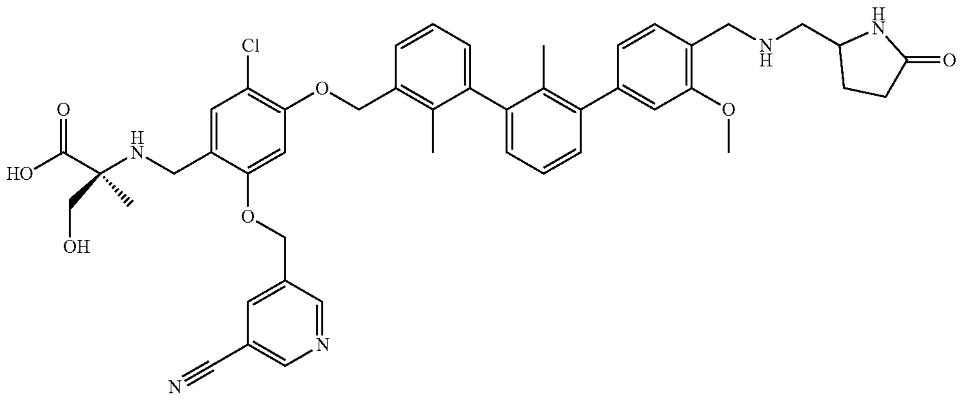 [SMILES: COc1cc(-c2cccc(-c3cccc(COc4cc(OCc5cncc(C#N)c5)c(CN[C@@](C)(CO)C(=O)O)cc4Cl)c3C)c2C)ccc1CNCC1CCC(=O)N1] | 818.131 |
| 509 | 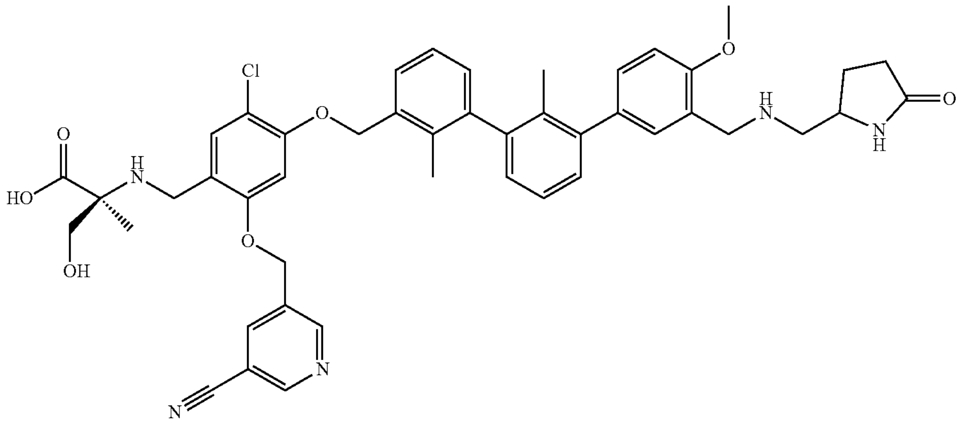 [SMILES: COc1ccc(-c2cccc(-c3cccc(COc4cc(OCc5cncc(C#N)c5)c(CN[C@@](C)(CO)C(=O)O)cc4Cl)c3C)c2C)cc1CNCC1CCC(=O)N1] | 818.128 |
| 510 | 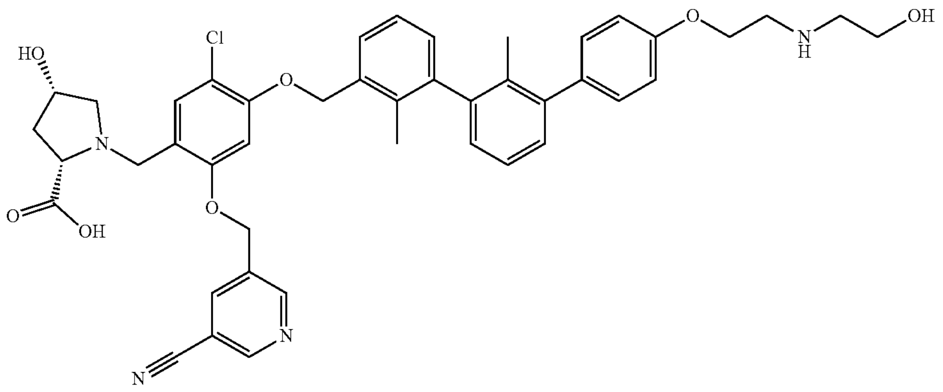 [SMILES: Cc1c(COc2cc(OCc3cncc(C#N)c3)c(CN3C[C@@H](O)C[C@H]3C(=O)O)cc2Cl)cccc1-c1cccc(-c2ccc(OCCNCCO)cc2)c1C] | 777.1 |
| 511 | 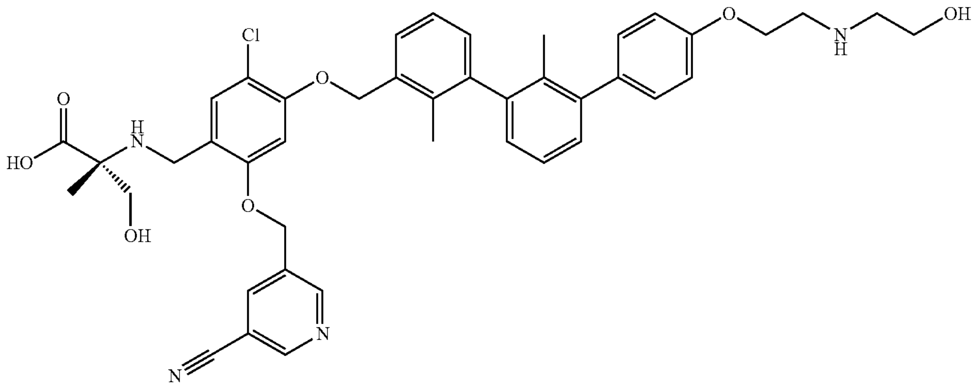 [SMILES: Cc1c(COc2cc(OCc3cncc(C#N)c3)c(CN[C@](C)(CO)C(=O)O)cc2Cl)cccc1-c1cccc(-c2ccc(OCCNCCO)cc2)c1C] | 765.053 |

-continued
512 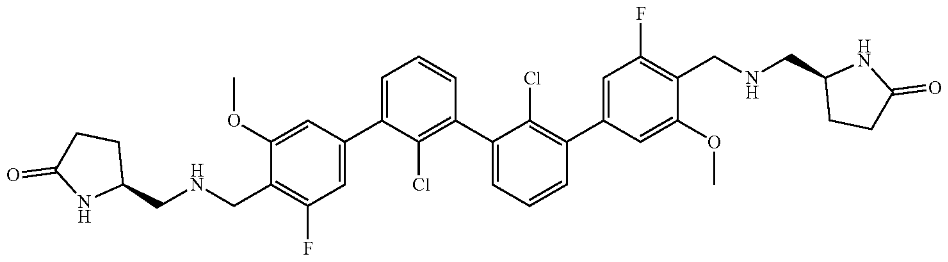 [SMILES: COc1cc(-c2cccc(-c3cccc(-c4cc(F)c(CNC[C@@H]5CCC(=O)N5)c(OC)c4)c3Cl)c2Cl)cc(F)c1CNC[C@@H]1CCC(=O)N1] 723.65
513 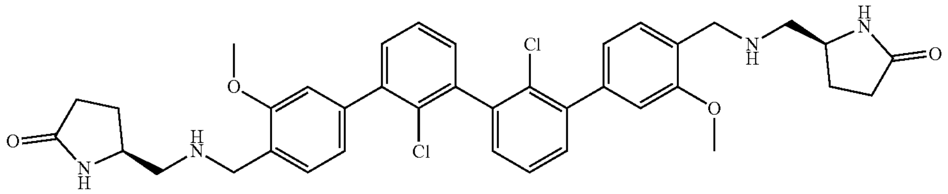 [SMILES: COc1cc(-c2cccc(-c3cccc(-c4ccc(CNC[C@@H]5CCC(=O)N5)c(OC)c4)c3Cl)c2Cl)ccc1CNC[C@@H]1CCC(=O)N1] 687.67
514 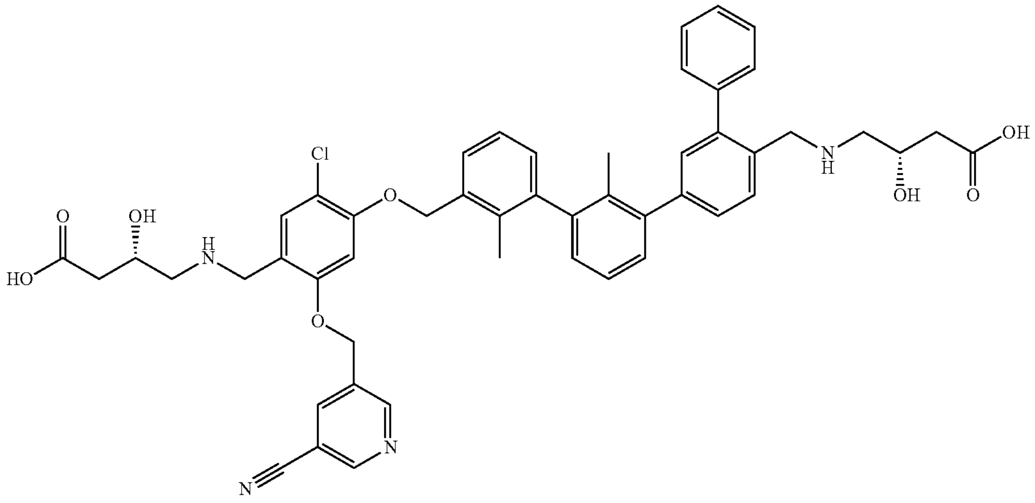 [SMILES: Cc1c(COc2cc(OCc3cncc(C#N)c3)c(CNC[C@@H](O)CC(=O)O)cc2Cl)cccc1-c1cccc(-c2ccc(CNC[C@@H](O)CC(=O)O)c(-c3ccccc3)c2)c1C] 869.62
515 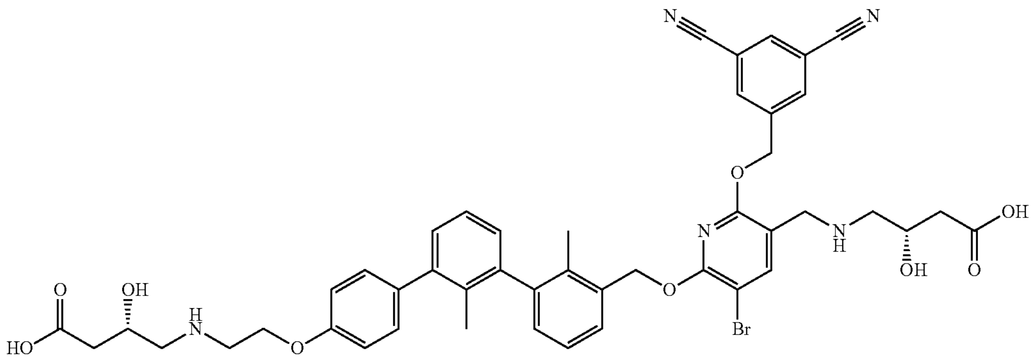 [SMILES: Cc1c(COc2nc(OCc3cc(C#N)cc(C#N)c3)c(CNC[C@@H](O)CC(=O)O)cc2Br)cccc1-c1cccc(-c2ccc(OCCNC[C@@H](O)CC(=O)O)cc2)c1C] 892.19

-continued
516 872.26
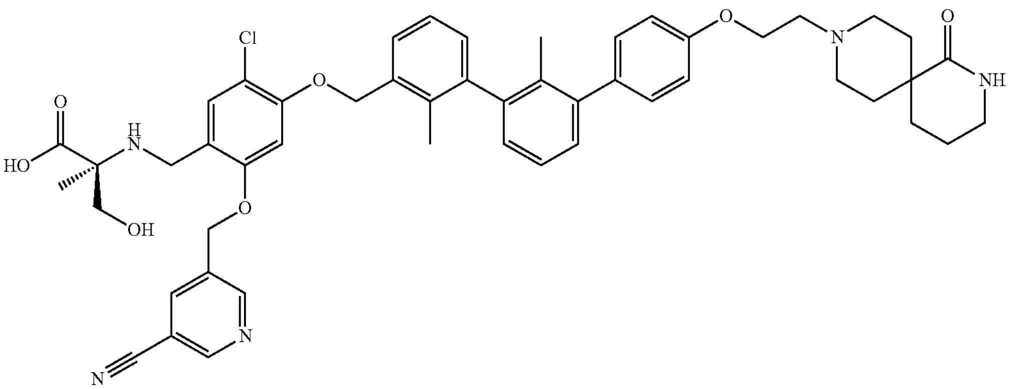 [SMILES: Cc1c(COc2cc(OCc3cncc(C#N)c3)c(CN[C@@](C)(CO)C(=O)O)cc2Cl)cccc1-c1cccc(-c2ccc(OCCN3CCC4(CCCNC4=O)CC3)cc2)c1C]
517 818.12
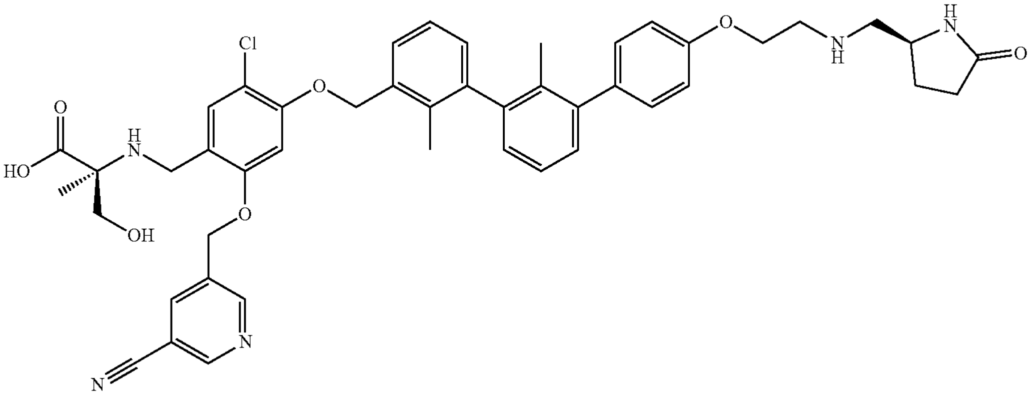 [SMILES: Cc1c(COc2cc(OCc3cncc(C#N)c3)c(CN[C@@](C)(CO)C(=O)O)cc2Cl)cccc1-c1cccc(-c2ccc(OCCNC[C@@H]3CCC(=O)N3)cc2)c1C]
518 818.1
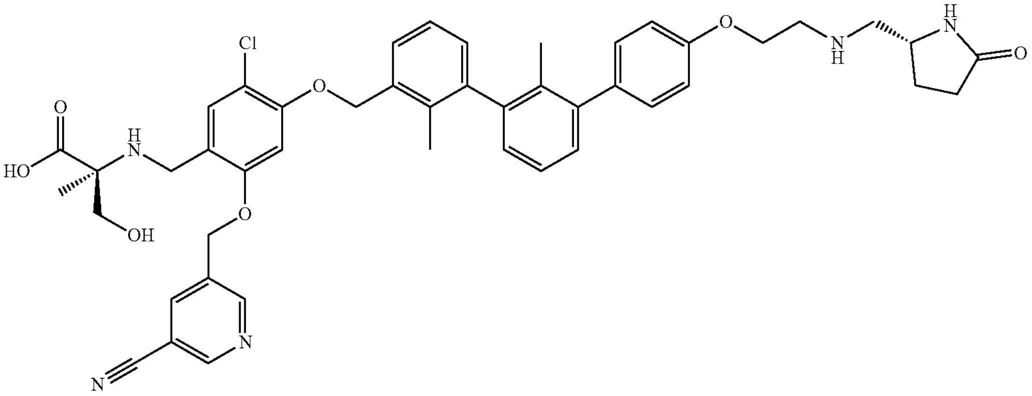 [SMILES: Cc1c(COc2cc(OCc3cncc(C#N)c3)c(CN[C@@](C)(CO)C(=O)O)cc2Cl)cccc1-c1cccc(-c2ccc(OCCNC[C@H]3CCC(=O)N3)cc2)c1C]
519 830.12
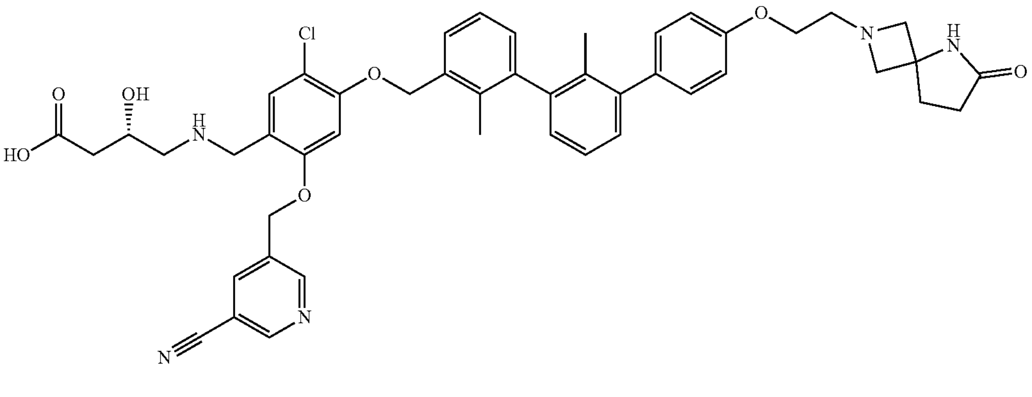 [SMILES: Cc1c(COc2cc(OCc3cncc(C#N)c3)c(CNC[C@@H](O)CC(=O)O)cc2Cl)cccc1-c1cccc(-c2ccc(OCCN3CC4(CCC(=O)N4)C3)cc2)c1C]

-continued
520 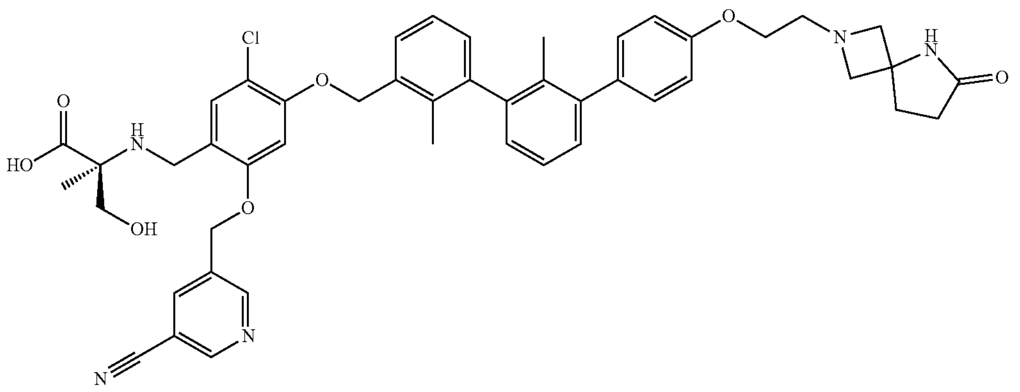 [SMILES: Cc1c(COc2cc(OCc3cncc(C#N)c3)c(CN[C@@](C)(CO)C(=O)O)cc2Cl)cccc1-c1cccc(-c2ccc(OCCN3CC4(CCC(=O)N4)C3)cc2)c1C] 830.07
521 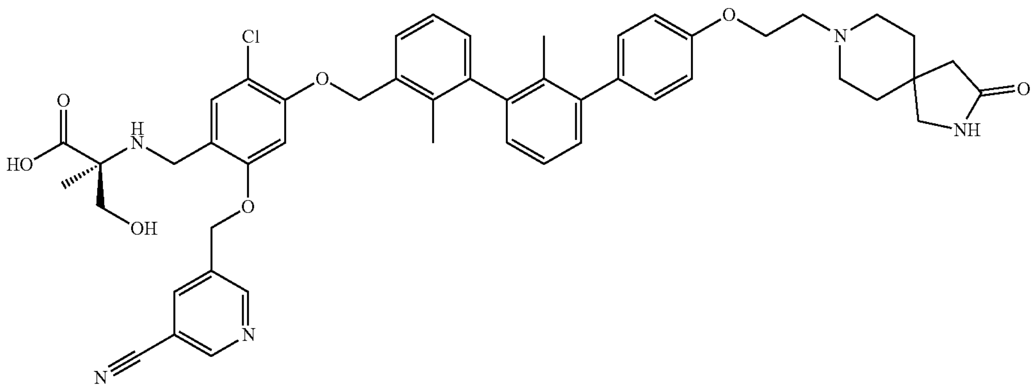 [SMILES: Cc1c(COc2cc(OCc3cncc(C#N)c3)c(CN[C@@](C)(CO)C(=O)O)cc2Cl)cccc1-c1cccc(-c2ccc(OCCN3CCC4(CC3)CNC(=O)C4)cc2)c1C] 858.05
522 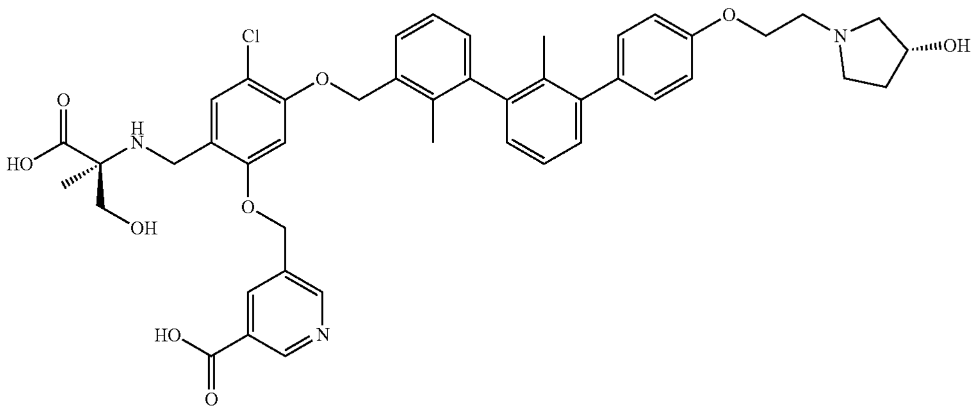 [SMILES: Cc1c(COc2cc(OCc3cncc(C(=O)O)c3)c(CN[C@@](C)(CO)C(=O)O)cc2Cl)cccc1-c1cccc(-c2ccc(OCCN3CC[C@@H](O)C3)cc2)c1C] 810.01
523 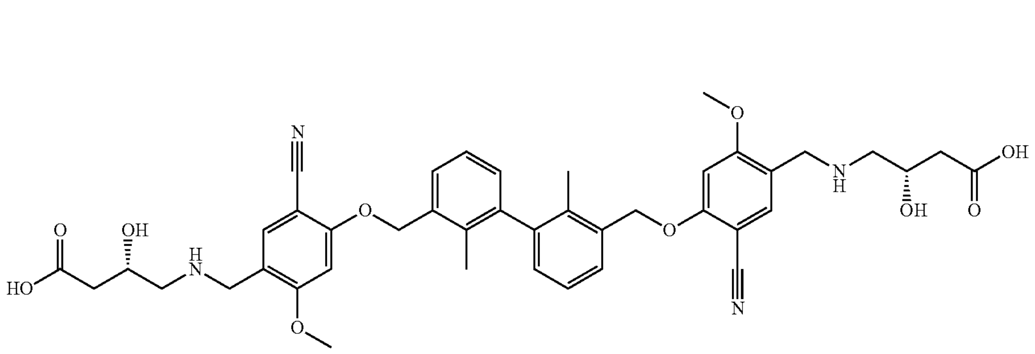 [SMILES: COc1cc(OCc2cccc(-c3cccc(COc4cc(OC)c(CNC[C@@H](O)CC(=O)O)cc4C#N)c3C)c2C)c(C#N)cc1CNC[C@@H](O)CC(=O)O] 767.16

-continued
| | | |
|---|---|---|
| 524 | 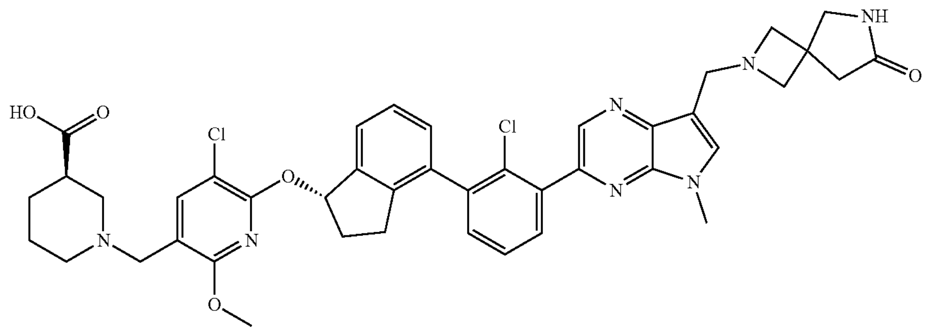 [SMILES: COc1nc(O[C@H]2CCc3c(-c4cccc(-c5cnc6c(CN7CC8(CNC(=O)C8)C7)cn(C)c6n5)c4Cl)cccc32)c(Cl)cc1CN1CCC[C@@H](C(=O)O)C1] | 796.09 |
| 525 | 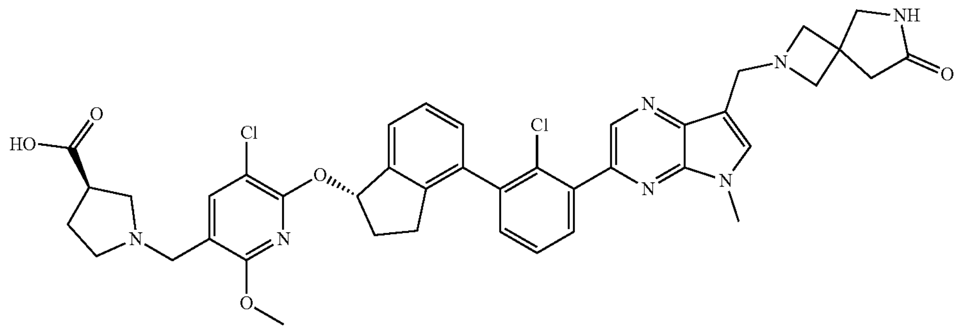 [SMILES: COc1nc(O[C@H]2CCc3c(-c4cccc(-c5cnc6c(CN7CC8(CNC(=O)C8)C7)cn(C)c6n5)c4Cl)cccc32)c(Cl)cc1CN1CC[C@@H](C(=O)O)C1] | 782.06 |
| 526 | 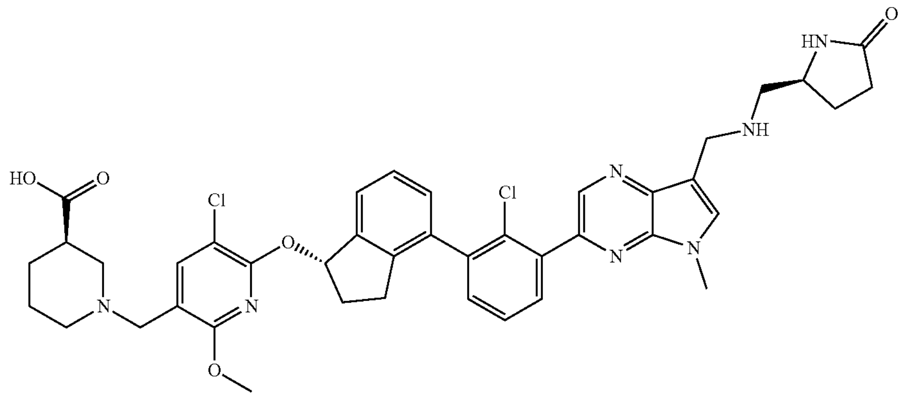 [SMILES: COc1nc(O[C@H]2CCc3c(-c4cccc(-c5cnc6c(CNC[C@@H]7CCC(=O)N7)cn(C)c6n5)c4Cl)cccc32)c(Cl)cc1CN1CCC[C@@H](C(=O)O)C1] | 784.1 |
| 527 | 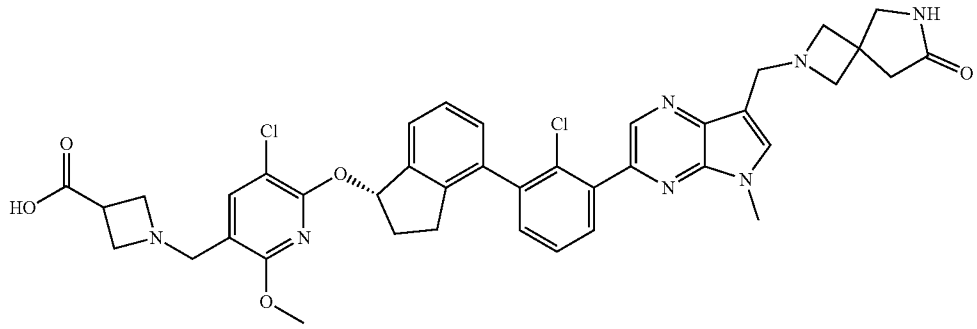 [SMILES: COc1nc(O[C@H]2CCc3c(-c4cccc(-c5cnc6c(CN7CC8(CNC(=O)C8)C7)cn(C)c6n5)c4Cl)cccc32)c(Cl)cc1CN1CC(C(=O)O)C1] | 768.05 |

-continued
| | | |
|---|---|---|
| 528 | 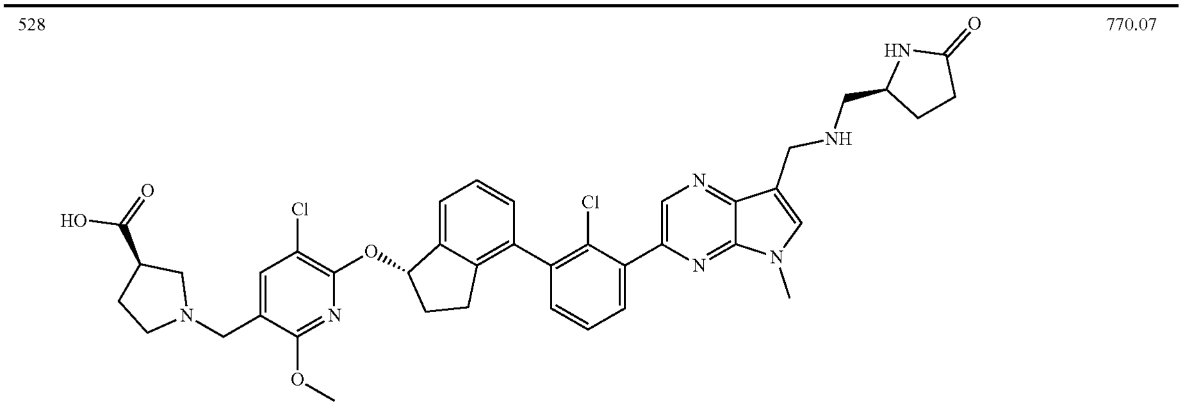 | 770.07 |
| 529 | 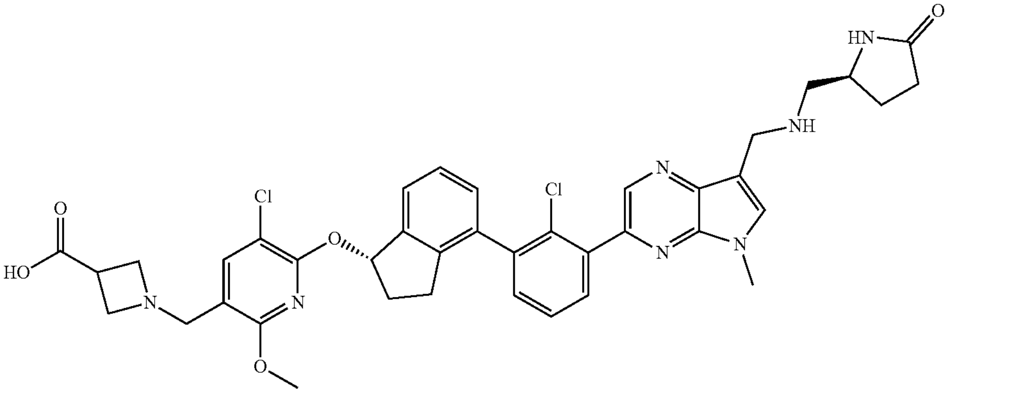 [SMILES: COc1nc(O[C@H]2CCc3c(-c4cccc(-c5cnc6c(CNC[C@@H]7CCC(=O)N7)cn(C)c6n5)c4Cl)cccc32)c(Cl)cc1CN1CC(C(=O)O)C1] | 756.04 |
| 540 | 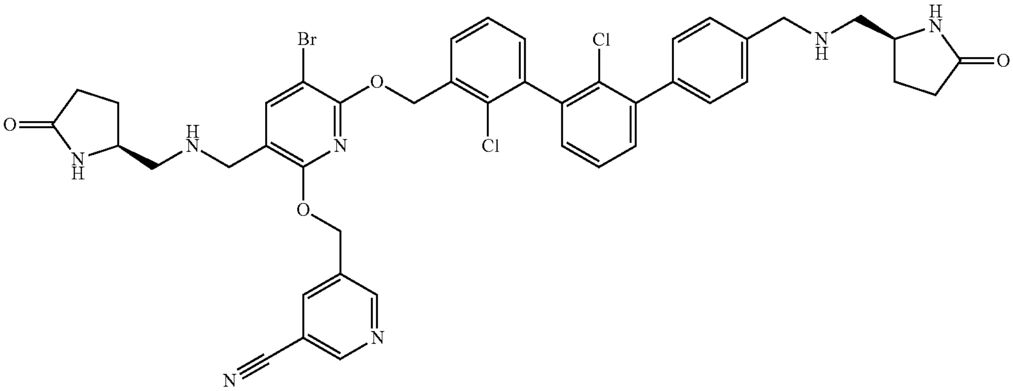 [SMILES: N#Cc1cncc(COc2nc(OCc3cccc(-c4cccc(-c5ccc(CNC[C@@H]6CCC(=O)N6)cc5)c4Cl)c3Cl)c(Br)cc2CNC[C@@H]2CCC(=O)N2)c1] | 869.99 |
| 541 | 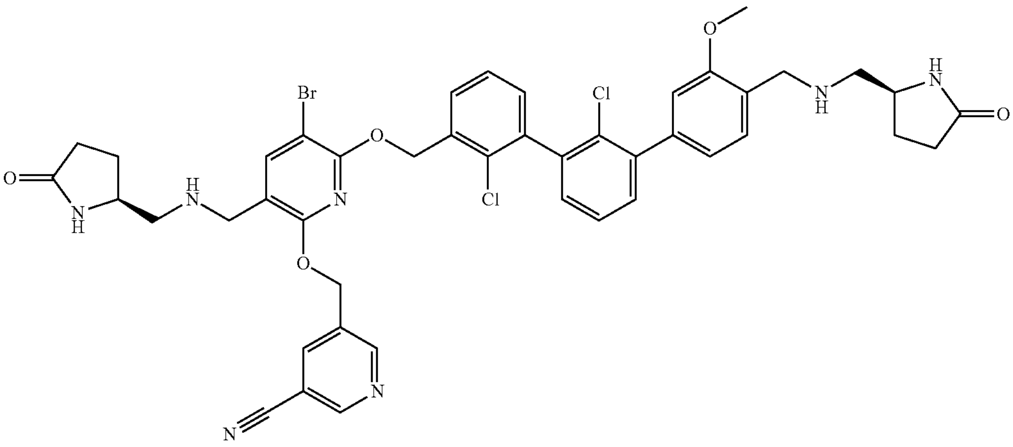 [SMILES: COc1cc(-c2cccc(-c3cccc(COc4nc(OCc5cncc(C#N)c5)c(CNC[C@@H]5CCC(=O)N5)cc4Br)c3Cl)c2Cl)ccc1CNC[C@@H]1CCC(=O)N1] | 900.02 |

-continued
542 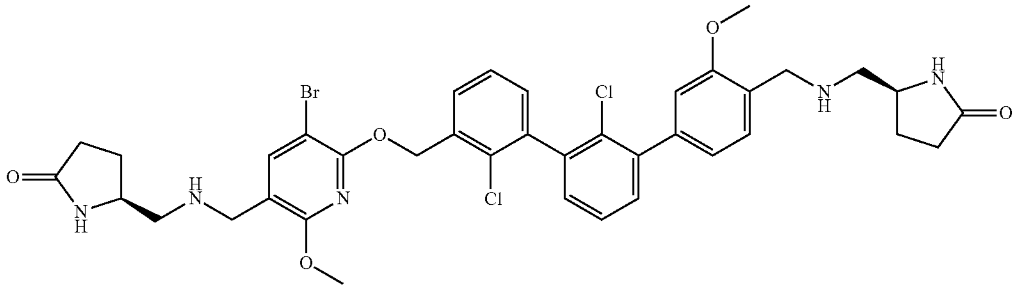 [SMILES: COc1cc(-c2cccc(-c3cccc(COc4nc(OC)c(CNC[C@@H]5CCC(=O)N5)cc4Br)c3Cl)c2Cl)ccc1CNC[C@@H]1CCC(=O)N1] 797.93
543 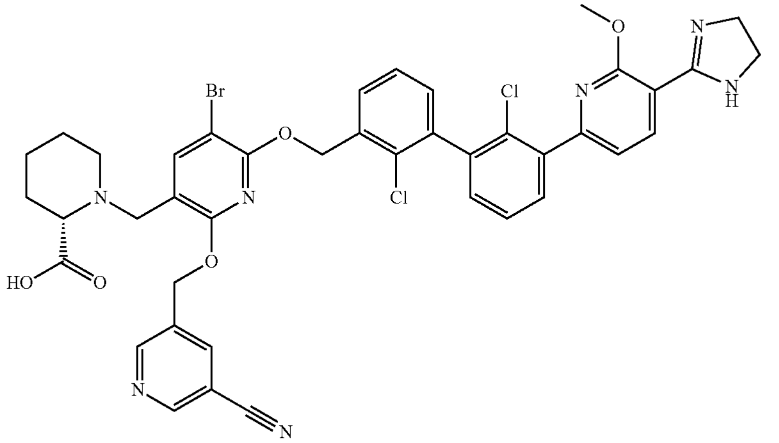 [SMILES: COc1nc(-c2cccc(-c3cccc(COc4nc(OCc5cncc(C#N)c5)c(CN5CCCC[C@H]5C(=O)O)cc4Br)c3Cl)c2Cl)ccc1C1=NCCN1] 858.11
544 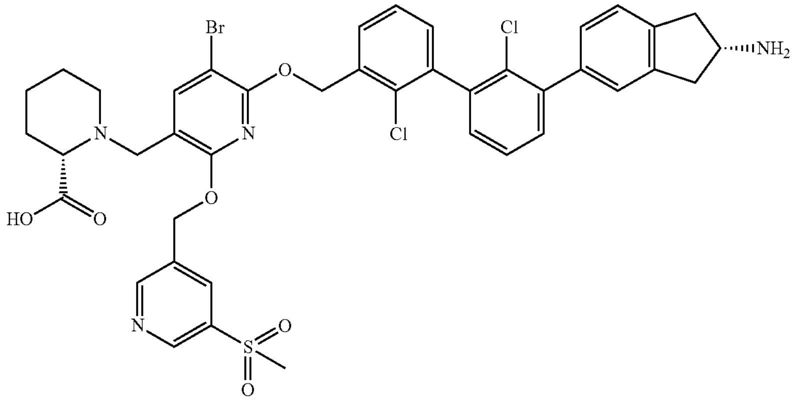 [SMILES: CS(=O)(=O)c1cncc(COc2nc(OCc3cccc(-c4cccc(-c5ccc6c(c5)C[C@@H](N)C6)c4Cl)c3Cl)c(Br)cc2CN2CCCC[C@H]2C(=O)O)c1] 867.01
545 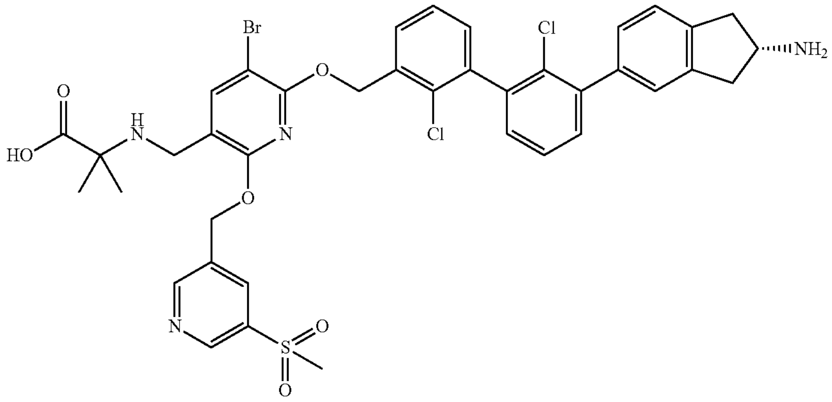 [SMILES: CC(C)(NCc1cc(Br)c(OCc2cccc(-c3cccc(-c4ccc5c(c4)C[C@@H](N)C5)c3Cl)c2Cl)nc1OCc1cncc(S(C)(=O)=O)c1)C(=O)O] 840.91

-continued
546 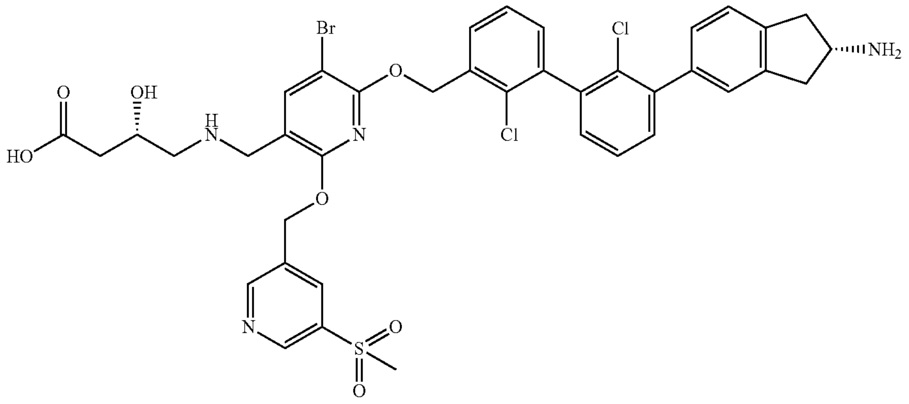 [SMILES: CS(=O)(=O)c1cncc(COc2nc(OCc3cccc(-c4cccc(-c5ccc6c(c5)C[C@@H](N)C6)c4Cl)c3Cl)c(Br)cc2CNC[C@@H](O)CC(=O)O)c1] 857
547 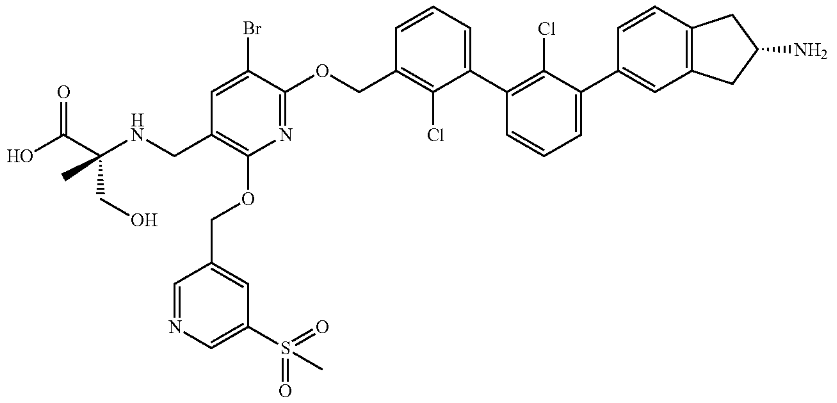 [SMILES: C[C@](CO)(NCc1cc(Br)c(OCc2cccc(-c3cccc(-c4ccc5c(c4)C[C@@H](N)C5)c3Cl)c2Cl)nc1OCc1cncc(S(C)(=O)=O)c1)C(=O)O] 856.96
548 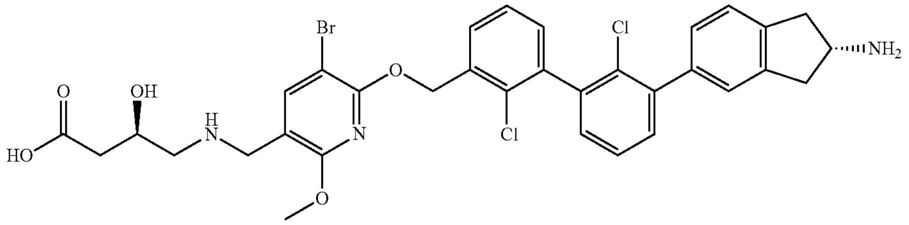 [SMILES: COc1nc(OCc2cccc(-c3cccc(-c4ccc5c(c4)C[C@@H](N)C5)c3Cl)c2Cl)c(Br)cc1CNC[C@H](O)CC(=O)O] 701.85
549 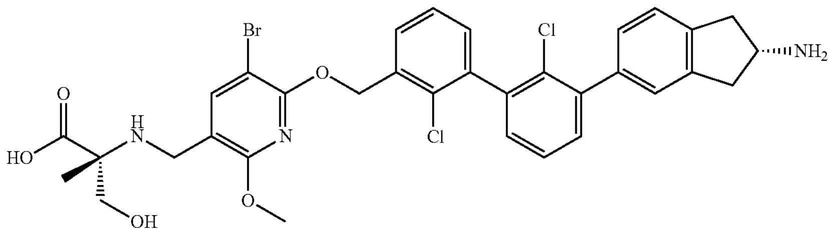 [SMILES: COc1nc(OCc2cccc(-c3cccc(-c4ccc5c(c4)C[C@@H](N)C5)c3Cl)c2Cl)c(Br)cc1CN[C@](C)(CO)C(=O)O] 701.78

-continued
| | | |
|---|---|---|
| 550 | 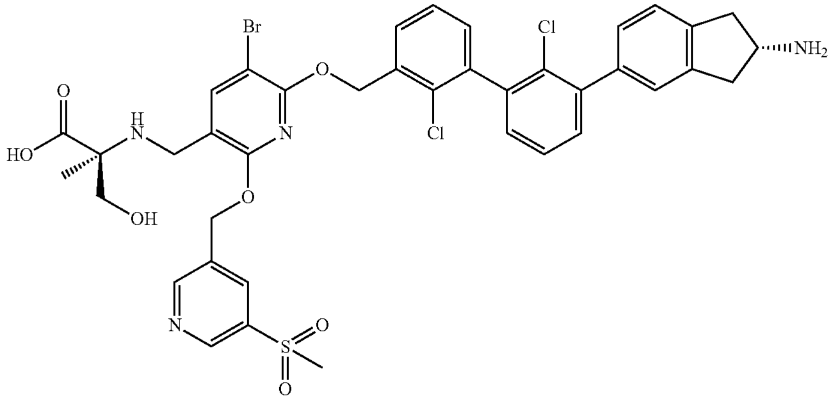 [SMILES: C[C@@](CO)(NCc1cc(Br)c(OCc2cccc(-c3cccc(-c4ccc5c(c4)C[C@@H](N)C5)c3Cl)c2Cl)nc1OCc1cncc(S(C)(=O)=O)c1)C(=O)O] | 856.88 |
| 551 | 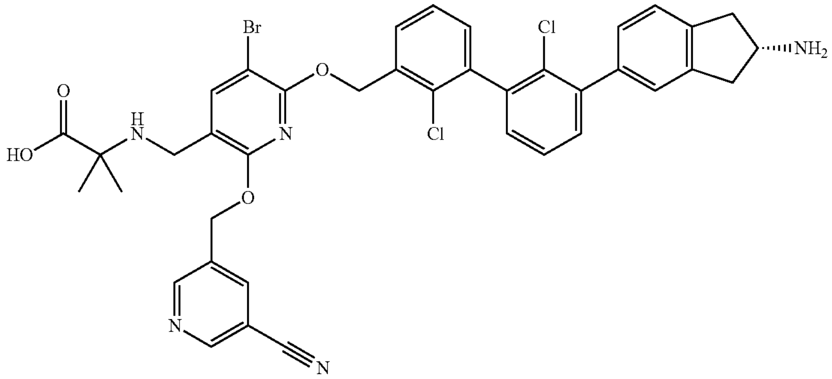 [SMILES: CC(C)(NCc1cc(Br)c(OCc2cccc(-c3cccc(-c4ccc5c(c4)C[C@@H](N)C5)c3Cl)c2Cl)nc1OCc1cncc(C#N)c1)C(=O)O] | 787.9 |
| 552 | 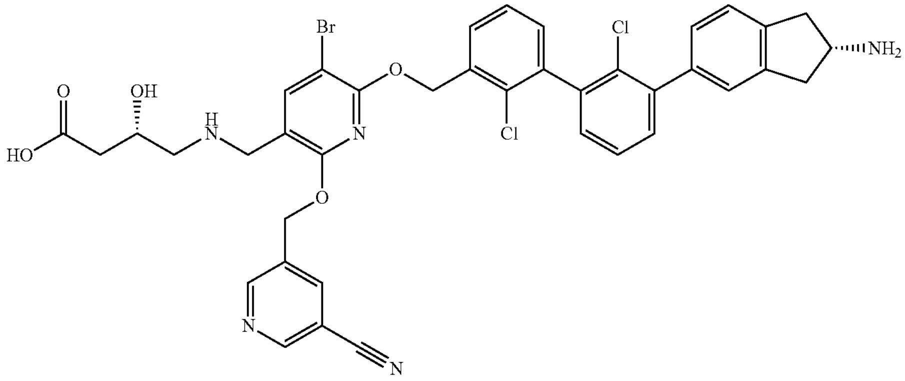 [SMILES: N#Cc1cncc(COc2nc(OCc3cccc(-c4cccc(-c5ccc6c(c5)C[C@@H](N)C6)c4Cl)c3Cl)c(Br)cc2CNC[C@@H](O)CC(=O)O)c1] | 803.99 |
| 553 | 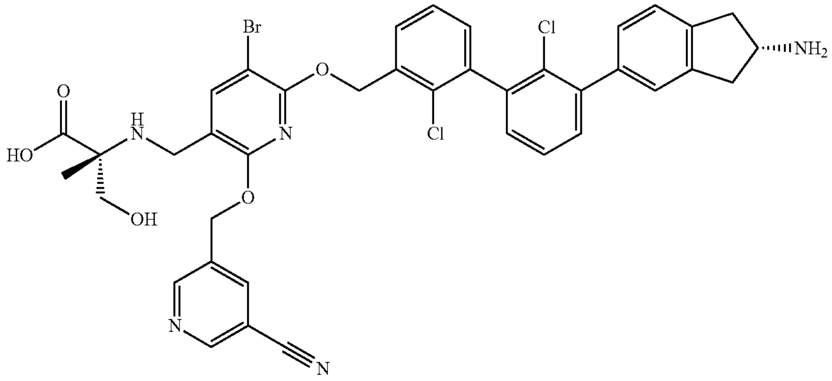 [SMILES: C[C@](CO)(NCc1cc(Br)c(OCc2cccc(-c3cccc(-c4ccc5c(c4)C[C@@H](N)C5)c3Cl)c2Cl)nc1OCc1cncc(C#N)c1)C(=O)O] | 803.91 |

-continued
| | | |
|---|---|---|
| 554 | 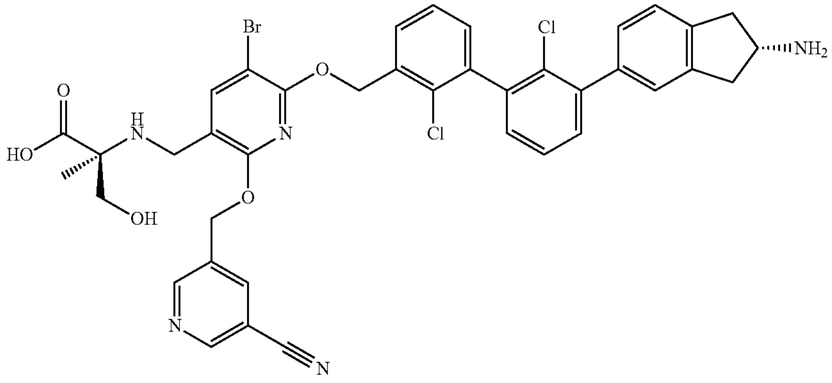 [SMILES: C[C@@](CO)(NCc1cc(Br)c(OCc2cccc(-c3cccc(-c4ccc5c(c4)C[C@@H](N)C5)c3Cl)c2Cl)nc1OCc1cncc(C#N)c1)C(=O)O] | 803.85 |
| 555 | 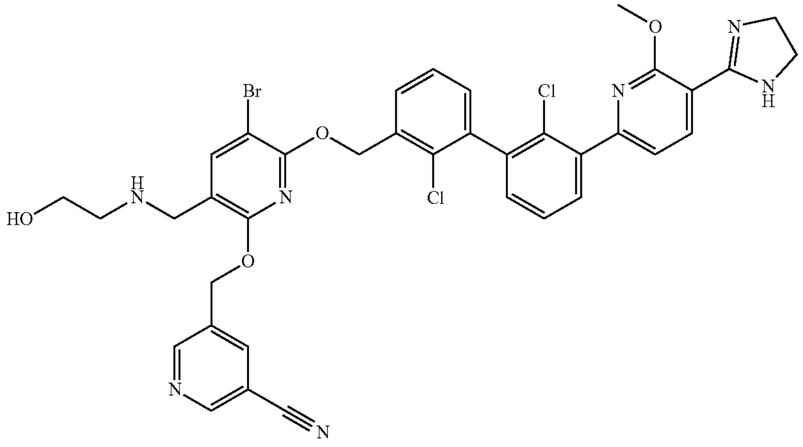 [SMILES: COc1nc(-c2cccc(-c3cccc(COc4nc(OCc5cncc(C#N)c5)c(CNCCO)cc4Br)c3Cl)c2Cl)ccc1C1=NCCN1] | 788.07 |
| 556 | 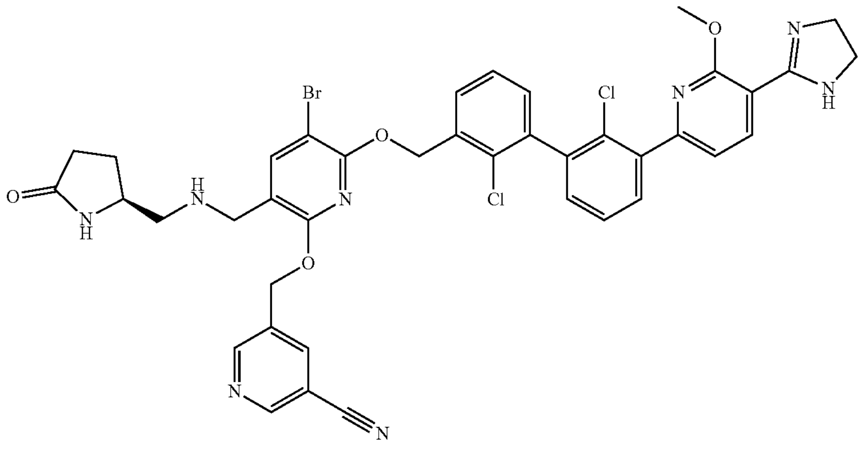 [SMILES: COc1nc(-c2cccc(-c3cccc(COc4nc(OCc5cncc(C#N)c5)c(CNC[C@@H]5CCC(=O)N5)cc4Br)c3Cl)c2Cl)ccc1C1=NCCN1] | 843.19 |

-continued
557 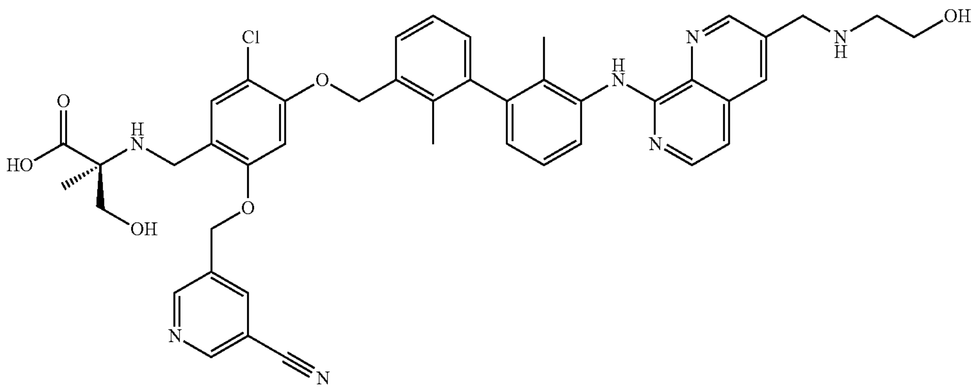 [SMILES: Cc1c(COc2cc(OCc3cncc(C#N)c3)c(CN[C@@](C)(CO)C(=O)O)cc2Cl)cccc1-c1cccc(Nc2nccc3cc(CNCCO)cnc23)c1C] 803.28
558 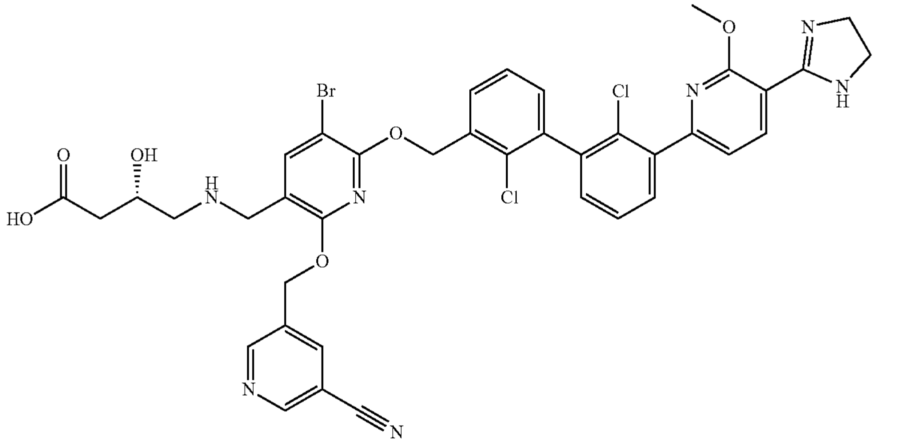 [SMILES: COc1nc(-c2cccc(-c3cccc(COc4nc(OCc5cncc(C#N)c5)c(CNC[C@@H](O)CC(=O)O)cc4Br)c3Cl)c2Cl)ccc1C1=NCCN1] 846.09
559 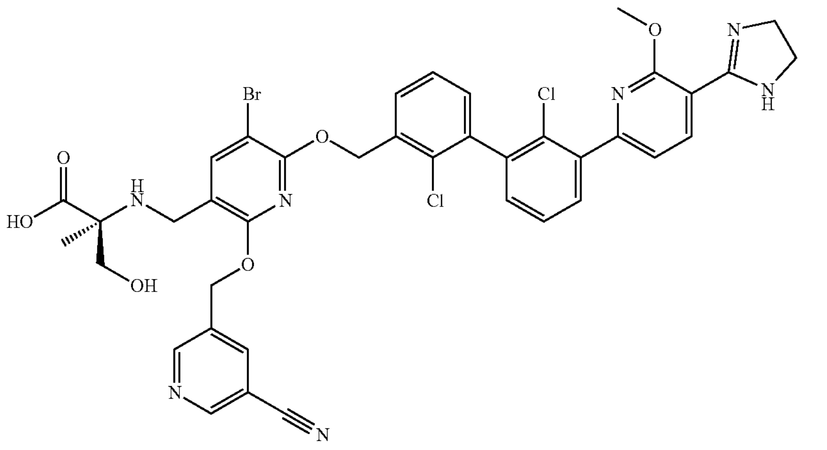 [SMILES: COc1nc(-c2cccc(-c3cccc(COc4nc(OCc5cncc(C#N)c5)c(CN[C@@](C)(CO)C(=O)O)cc4Br)c3Cl)c2Cl)ccc1C1=NCCN1] 848.05

-continued
| | | |
|---|---|---|
| 560 | 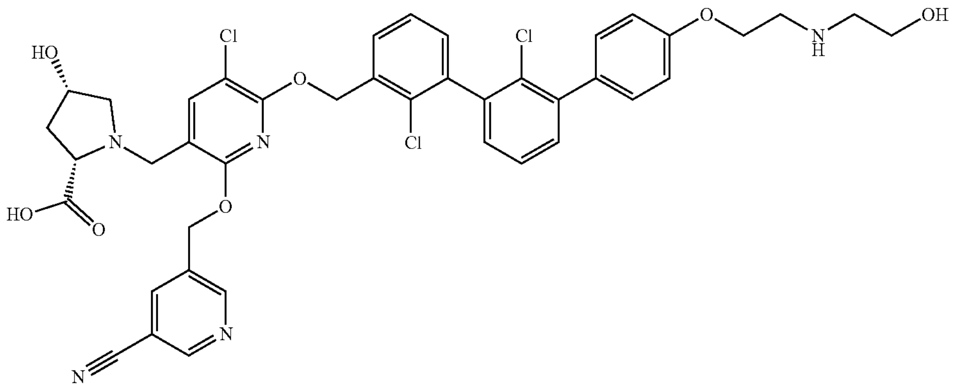 [SMILES: N#Cc1cncc(COc2nc(OCc3cccc(-c4cccc(-c5ccc(OCCNCCO)cc5)c4Cl)c3Cl)c(Cl)cc2CN2C[C@@H](O)C[C@H]2C(=O)O)c1] | 818.05 |
| 561 | 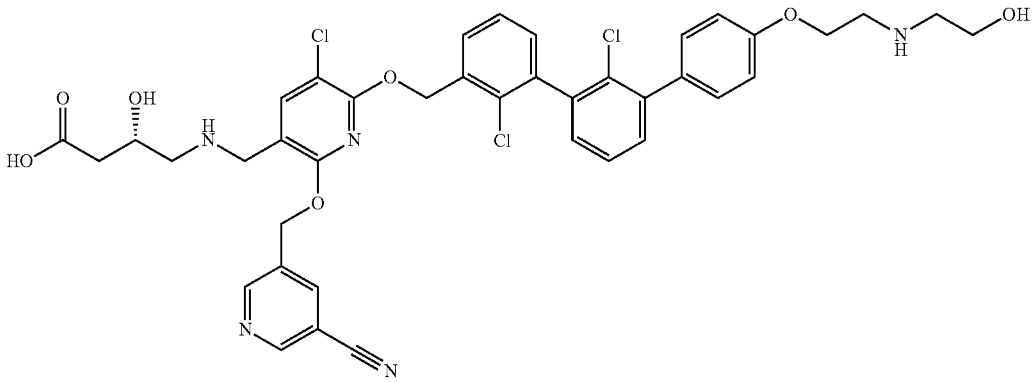 [SMILES: N#Cc1cncc(COc2nc(OCc3cccc(-c4cccc(-c5ccc(OCCNCCO)cc5)c4Cl)c3Cl)c(Cl)cc2CNC[C@@H](O)CC(=O)O)c1] | 808.02 |
| 562 | 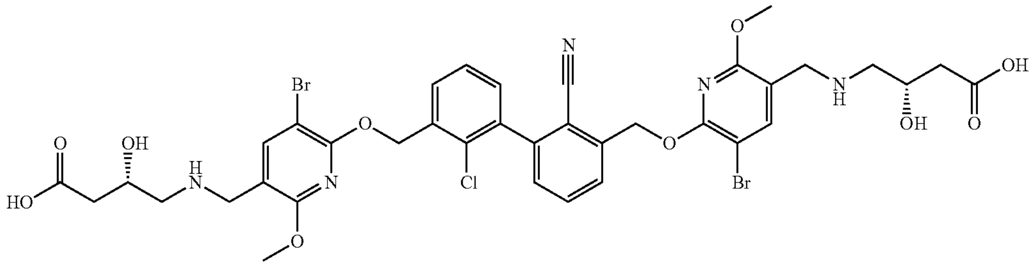 [SMILES: COc1nc(OCc2cccc(-c3cccc(COc4nc(OC)c(CNC[C@@H](O)CC(=O)O)cc4Br)c3C#N)c2Cl)c(Br)cc1CNC[C@@H](O)CC(=O)O] | 907.7 |
| 563 | 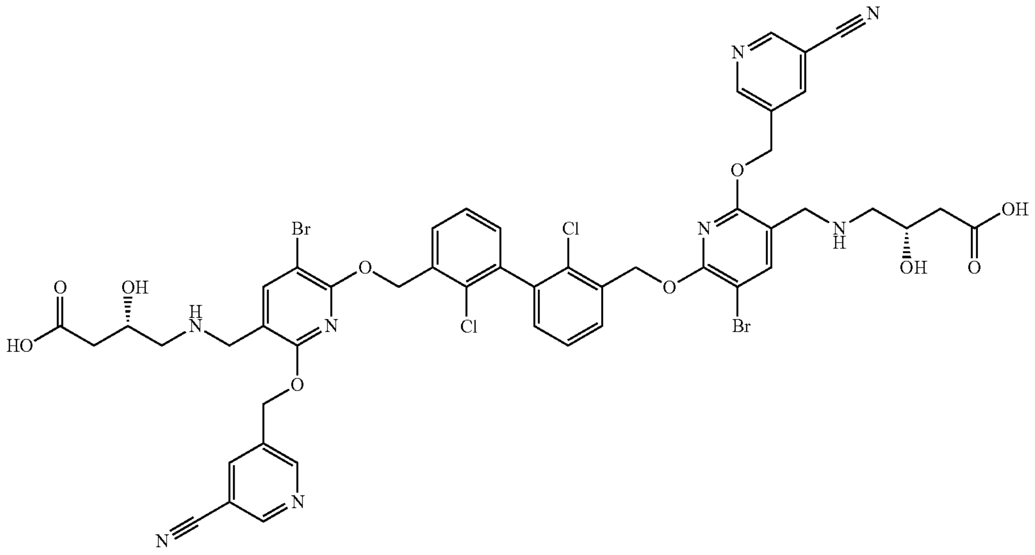 [SMILES: N#Cc1cncc(COc2nc(OCc3cccc(-c4cccc(COc5nc(OCc6cncc(C#N)c6)c(CNC[C@@H](O)CC(=O)O)cc5Br)c4Cl)c3Cl)c(Br)cc2CNC[C@@H](O)CC(=O)O)c1] | 1120.94 |

-continued
564 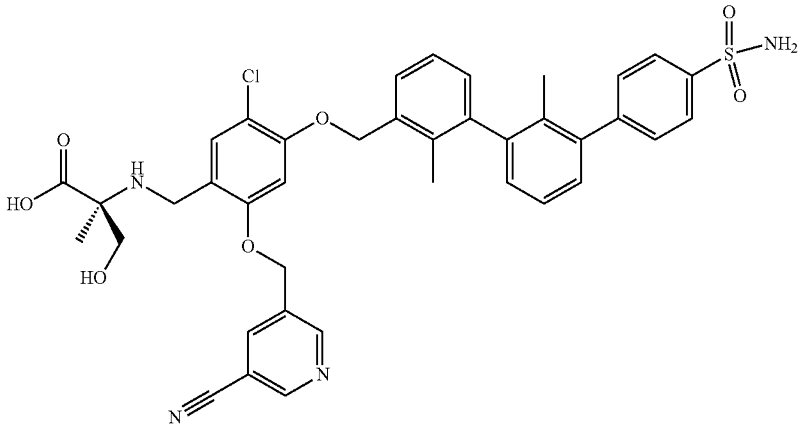 [SMILES: Cc1c(COc2cc(OCc3cncc(C#N)c3)c(CN[C@@](C)(CO)C(=O)O)cc2Cl)cccc1-c1cccc(-c2ccc(S(N)(=O)=O)cc2)c1C] 741.2
565 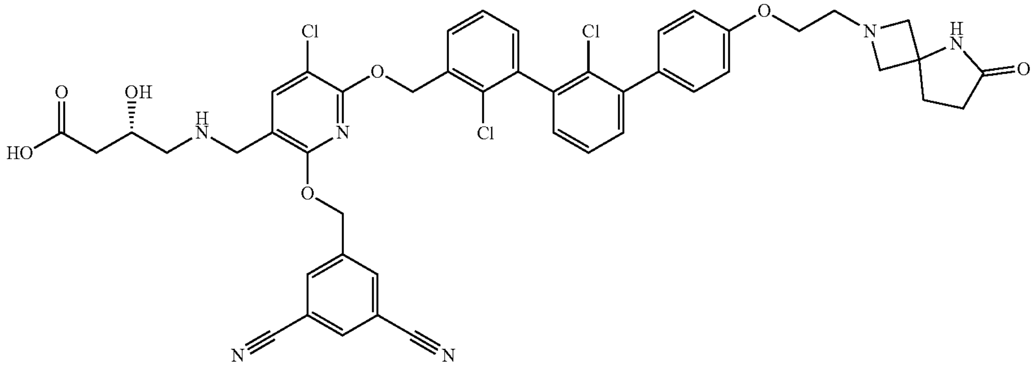 [SMILES: N#Cc1cc(C#N)cc(COc2nc(OCc3cccc(-c4cccc(-c5ccc(OCCN6CC7(CCC(=O)N7)C6)cc5)c4Cl)c3Cl)c(Cl)cc2CNC[C@@H](O)CC(=O)O)c1] 895.02
566 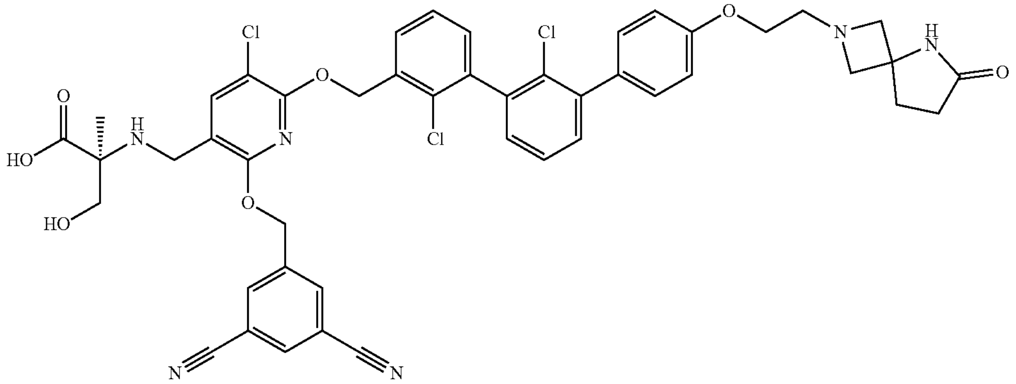 [SMILES: C[C@@](CO)(NCc1cc(Cl)c(OCc2cccc(-c3cccc(-c4ccc(OCCN5CC6(CCC(=O)N6)C5)cc4)c3Cl)c2Cl)nc1OCc1cc(C#N)cc(C#N)c1)C(=O)O] 894.96
567 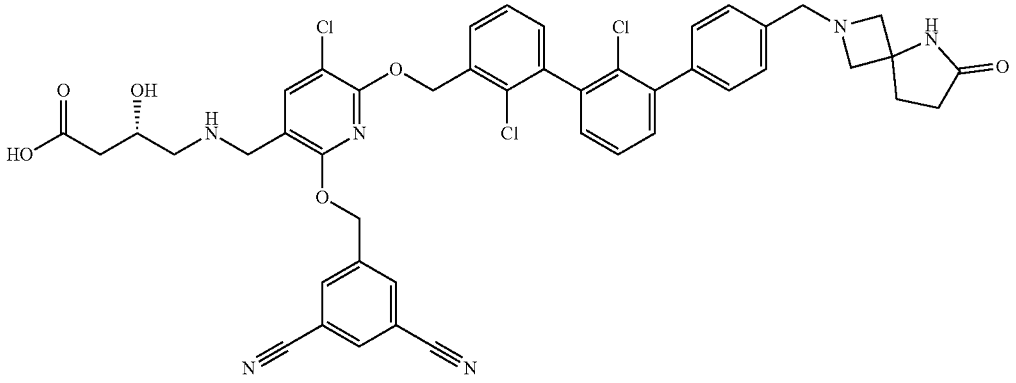 [SMILES: N#Cc1cc(C#N)cc(COc2nc(OCc3cccc(-c4cccc(-c5ccc(CN6CC7(CCC(=O)N7)C6)cc5)c4Cl)c3Cl)c(Cl)cc2CNC[C@@H](O)CC(=O)O)c1] 867.01

-continued
568 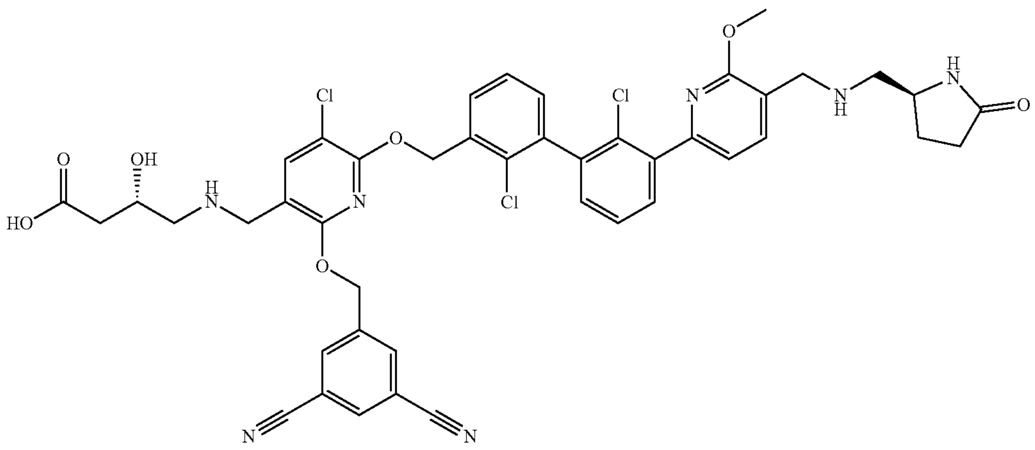 [SMILES: COc1nc(-c2cccc(-c3cccc(COc4nc(OCc5cc(C#N)cc(C#N)c5)c(CNC[C@@H](O)CC(=O)O)cc4Cl)c3Cl)c2Cl)ccc1CNC[C@@H]1CCC(=O)N1] 856.21
569 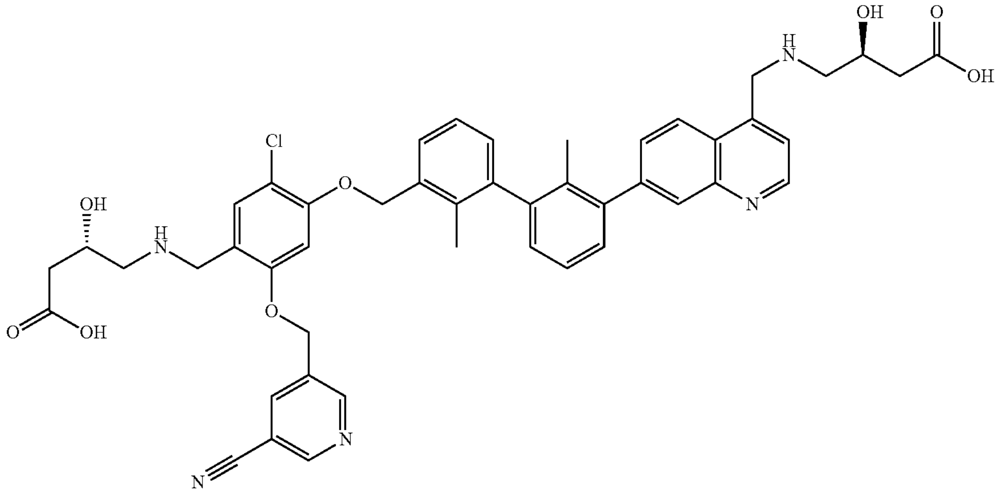 [SMILES: Cc1c(COc2cc(OCc3cncc(C#N)c3)c(CNC[C@@H](O)CC(=O)O)cc2Cl)cccc1-c1cccc(-c2ccc3c(CNC[C@@H](O)CC(=O)O)ccnc3c2)c1C] 844.15
570 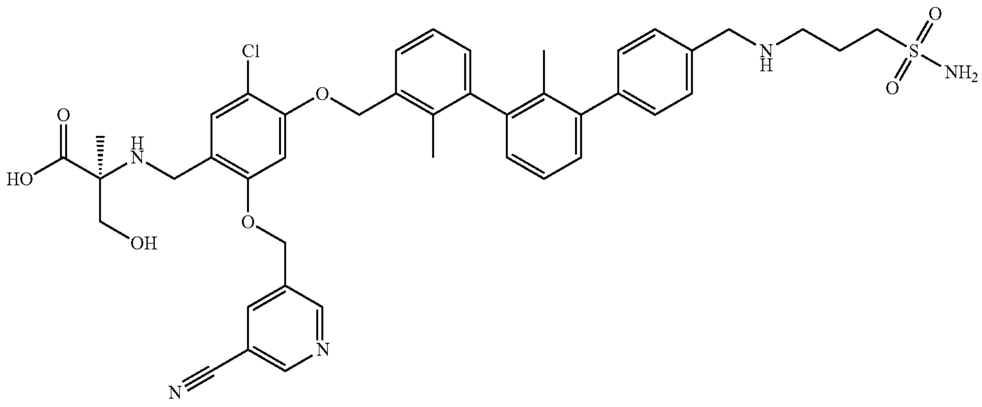 [SMILES: Cc1c(COc2cc(OCc3cncc(C#N)c3)c(CN[C@@](C)(CO)C(=O)O)cc2Cl)cccc1-c1cccc(-c2ccc(CNCCCS(N)(=O)=O)cc2)c1C] 812.06

-continued
| | | |
|---|---|---|
| 571 | 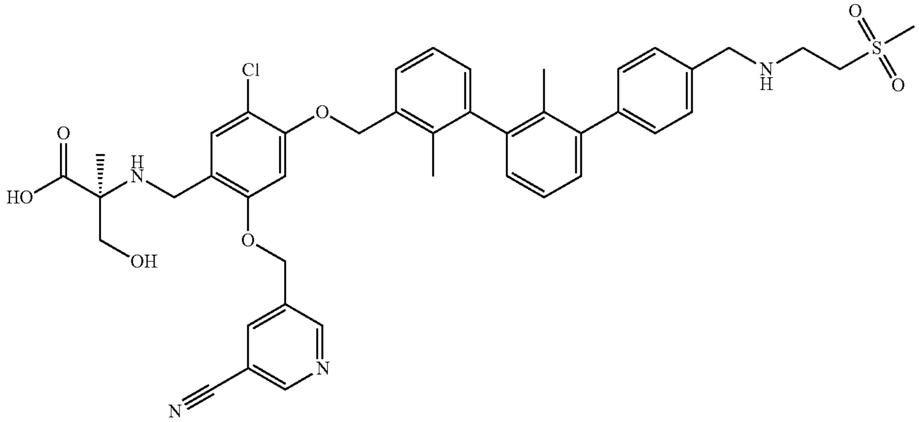 [SMILES: Cc1c(COc2cc(OCc3cncc(C#N)c3)c(CN[C@@](C)(CO)C(=O)O)cc2Cl)cccc1-c1cccc(-c2ccc(CNCCS(C)(=O)=O)cc2)c1C] | 797.05 |
| 572 | 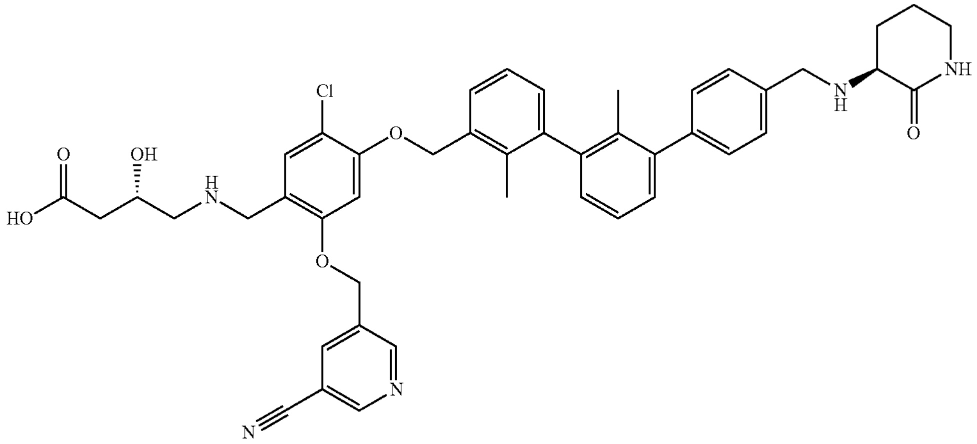 [SMILES: Cc1c(COc2cc(OCc3cncc(C#N)c3)c(CNC[C@@H](O)CC(=O)O)cc2Cl)cccc1-c1cccc(-c2ccc(CN[C@H]3CCCNC3=O)cc2)c1C] | 788.16 |
| 573 | 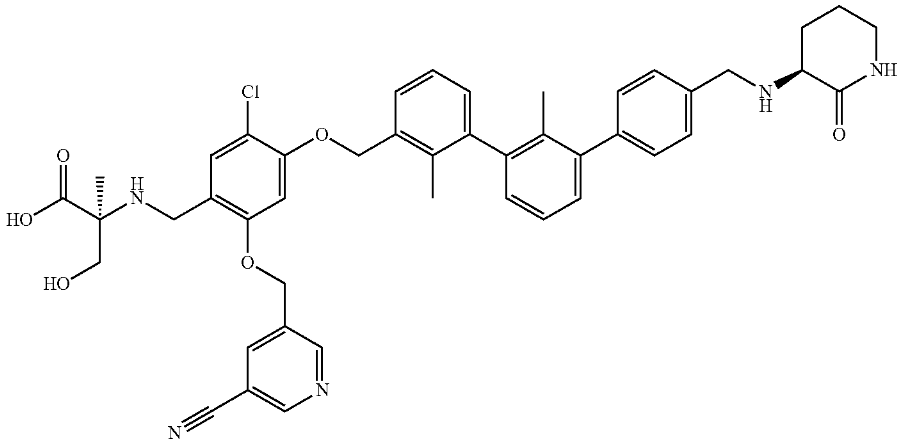 [SMILES: Cc1c(COc2cc(OCc3cncc(C#N)c3)c(CN[C@@](C)(CO)C(=O)O)cc2Cl)cccc1-c1cccc(-c2ccc(CN[C@H]3CCCNC3=O)cc2)c1C] | 788.12 |

-continued
574 788.12
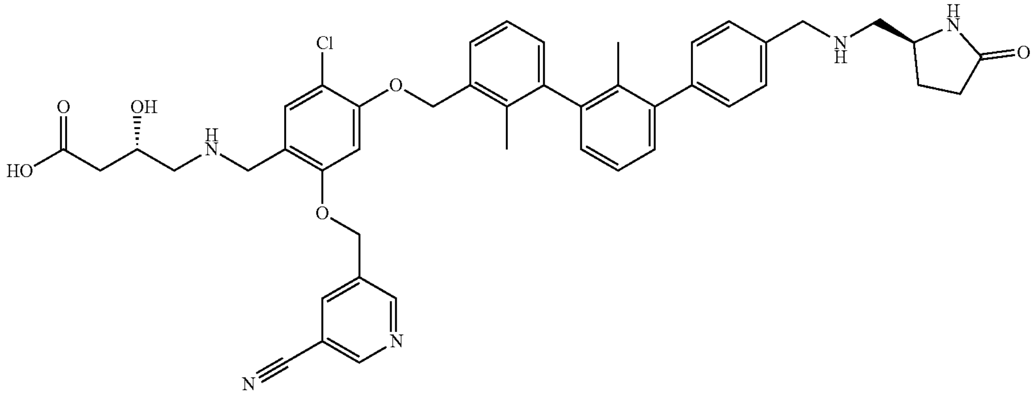 [SMILES: Cc1c(COc2cc(OCc3cncc(C#N)c3)c(CNC[C@@H](O)CC(=O)O)cc2Cl)cccc1-c1cccc(-c2ccc(CNC[C@@H]3CCC(=O)N3)cc2)c1C]
575 788.17
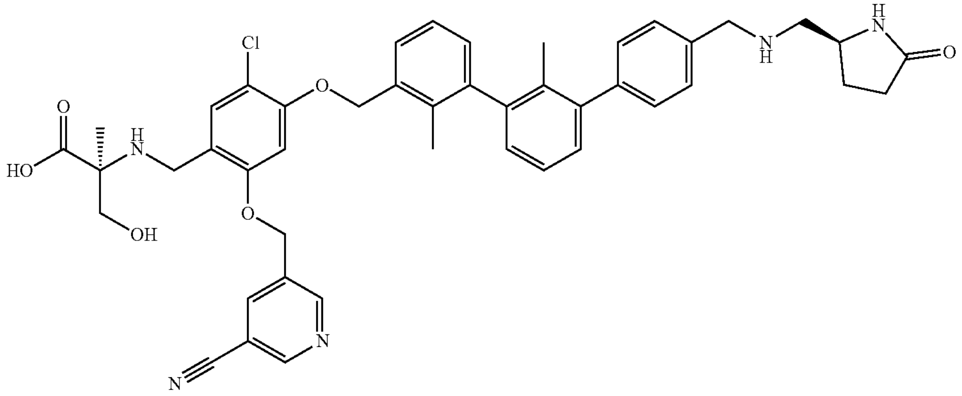 [SMILES: Cc1c(COc2cc(OCc3cncc(C#N)c3)c(CN[C@@](C)(CO)C(=O)O)cc2Cl)cccc1-c1cccc(-c2ccc(CNC[C@@H]3CCC(=O)N3)cc2)c1C]
576 855.06
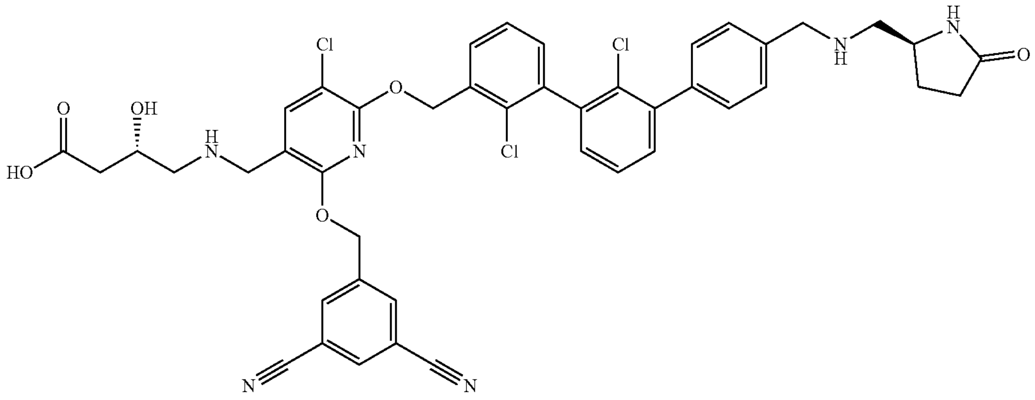 [SMILES: N#Cc1cc(C#N)cc(COc2nc(OCc3cccc(-c4cccc(-c5ccc(CNC[C@@H]6CCC(=O)N6)cc5)c4Cl)c3Cl)c(Cl)cc2CNC[C@@H](O)CC(=O)O)c1]
577 853.03
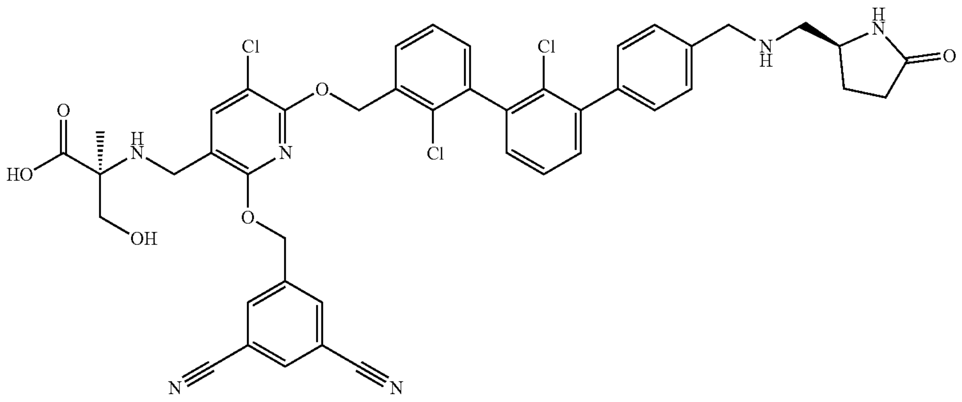 [SMILES: C[C@@](CO)(NCc1cc(Cl)c(OCc2cccc(-c3cccc(-c4ccc(CNC[C@@H]5CCC(=O)N5)cc4)c3Cl)c2Cl)nc1OCc1cc(C#N)cc(C#N)c1)C(=O)O]

-continued
578 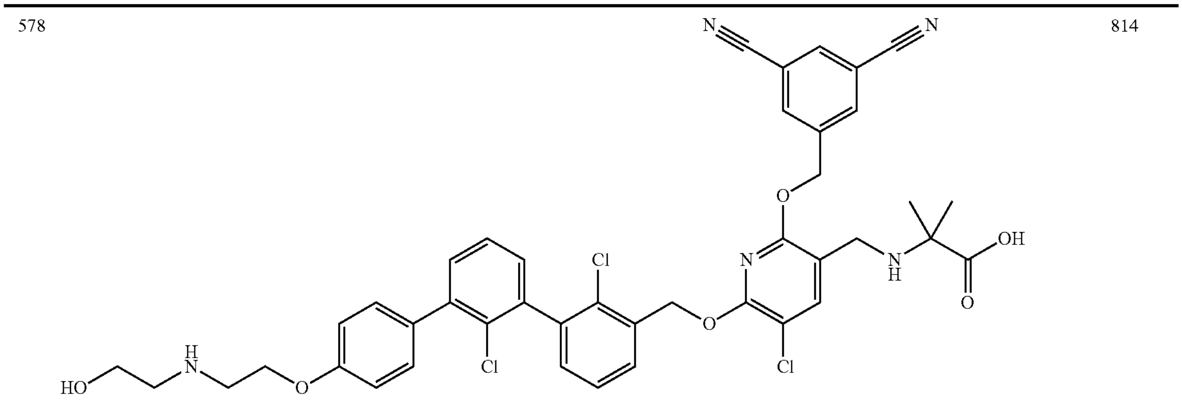 814
579 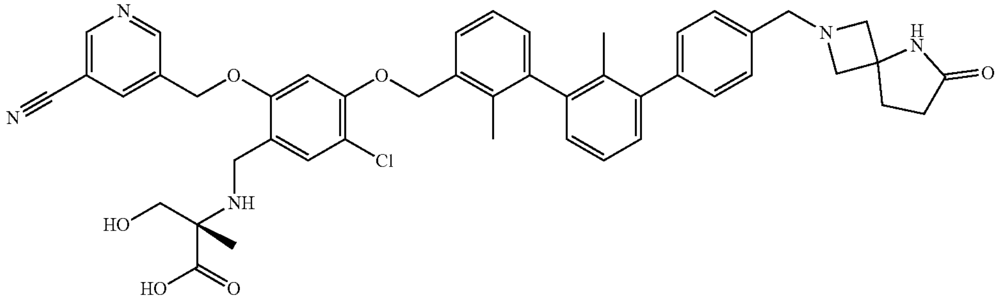 [SMILES: Cc1c(COc2cc(OCc3cncc(C#N)c3)c(CN[C@@](C)(CO)C(=O)O)cc2Cl)cccc1-c1cccc(-c2ccc(CN3CC4(CCC(=O)N4)C3)cc2)c1C] 800.2
580 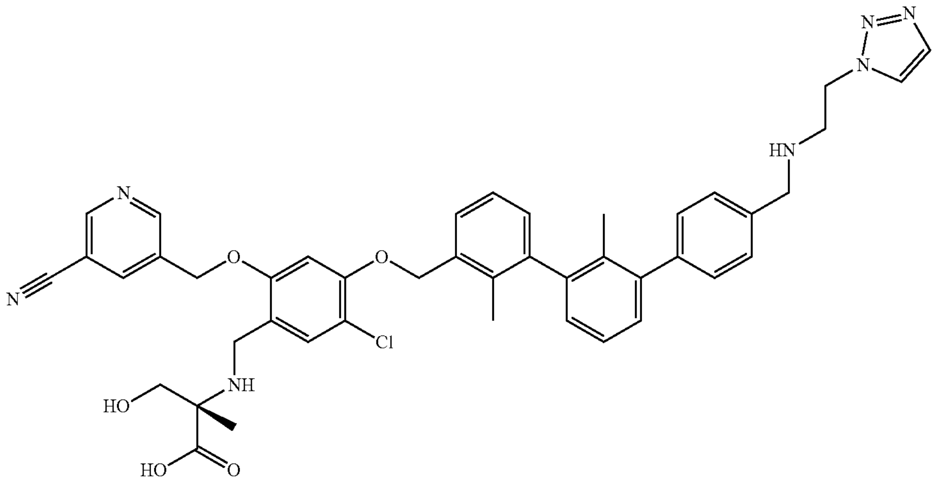 [SMILES: Cc1c(COc2cc(OCc3cncc(C#N)c3)c(CN[C@@](C)(CO)C(=O)O)cc2Cl)cccc1-c1cccc(-c2ccc(CNCCn3ccnn3)cc2)c1C] 786.1
581 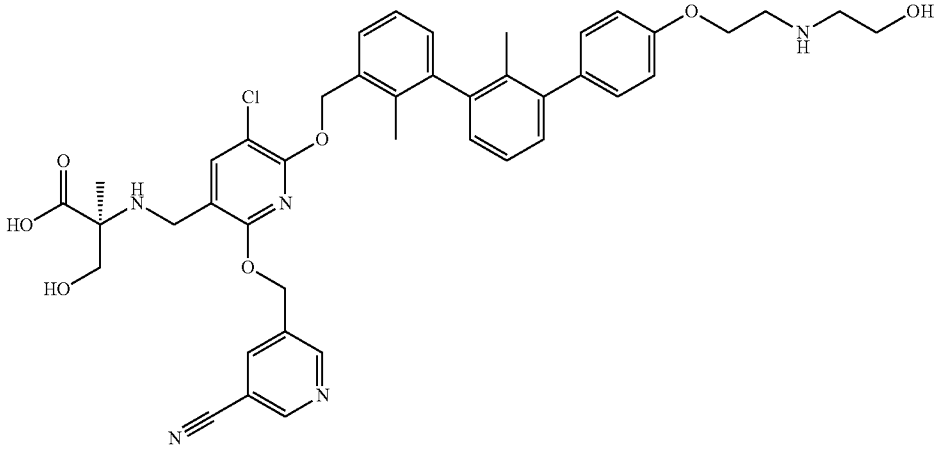 [SMILES: Cc1c(COc2nc(OCc3cncc(C#N)c3)c(CN[C@@](C)(CO)C(=O)O)cc2Cl)cccc1-c1cccc(-c2ccc(OCCNCCO)cc2)c1C] 766.2

-continued
582 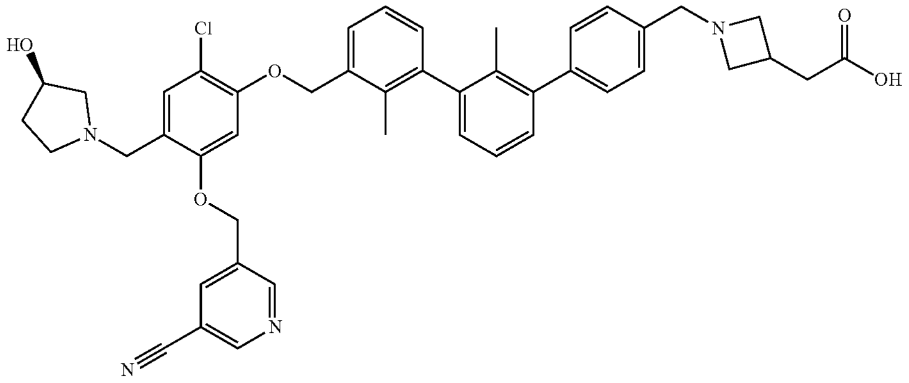 [SMILES: Cc1c(COc2cc(OCc3cncc(C#N)c3)c(CN3CC[C@@H](O)C3)cc2Cl)cccc1-c1cccc(-c2ccc(CN3CC(CC(=O)O)C3)cc2)c1C] 757.3
583 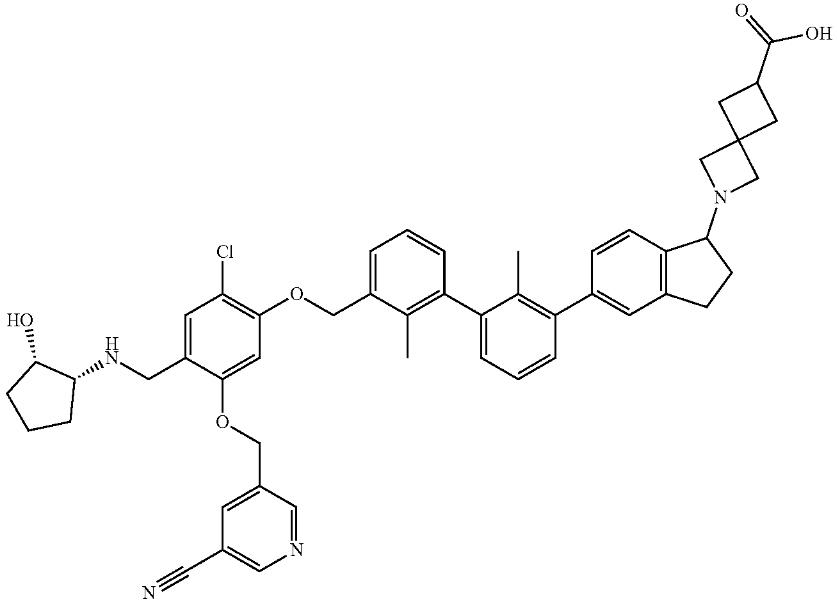 [SMILES: Cc1c(COc2cc(OCc3cncc(C#N)c3)c(CN[C@@H]3CCC[C@@H]3O)cc2Cl)cccc1-c1cccc(-c2ccc3c(c2)CCC3N2CC3(CC(C(=O)O)C3)C2)c1C] 823.2
584 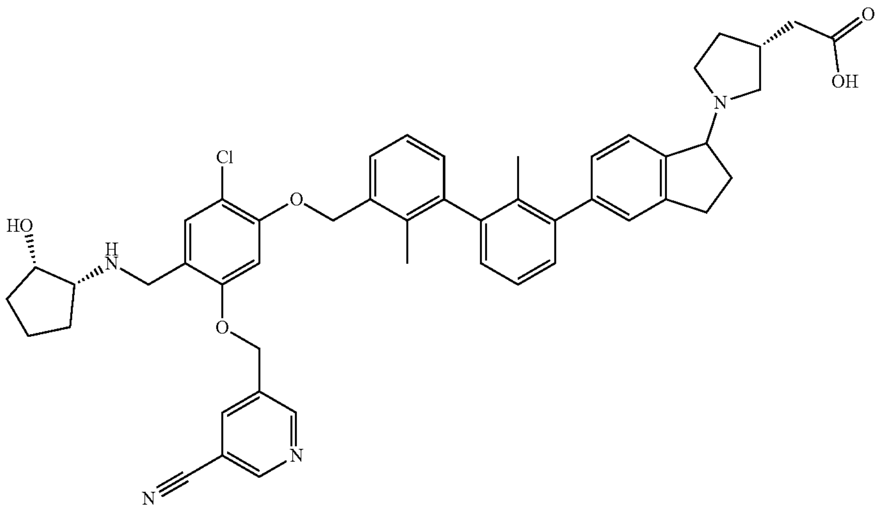 [SMILES: Cc1c(COc2cc(OCc3cncc(C#N)c3)c(CN[C@@H]3CCC[C@@H]3O)cc2Cl)cccc1-c1cccc(-c2ccc3c(c2)CCC3N2CC[C@H](CC(=O)O)C2)c1C] 811

-continued
585 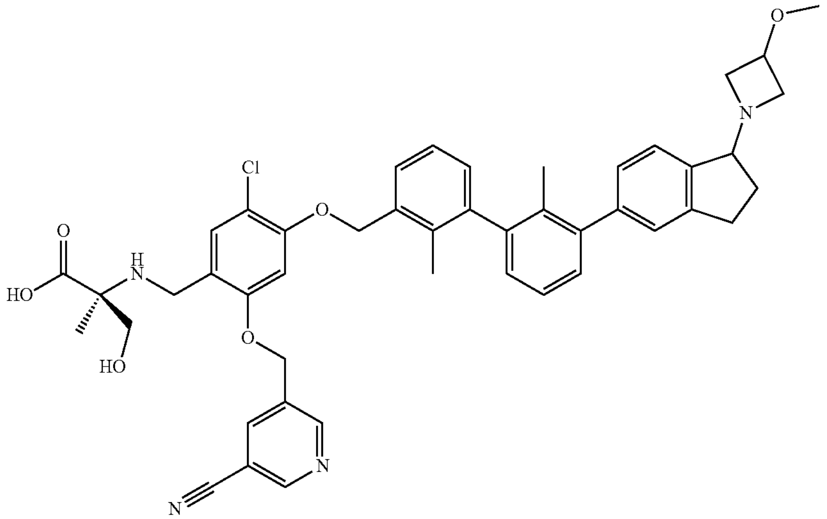 [SMILES: COC1CN(C2CCc3cc(-c4cccc(-c5cccc(COc6cc(OCc7cncc(C#N)c7)c(CN[C@@](C)(CO)C(=O)O)cc6Cl)c5C)c4C)ccc32)C1] 787.1
586 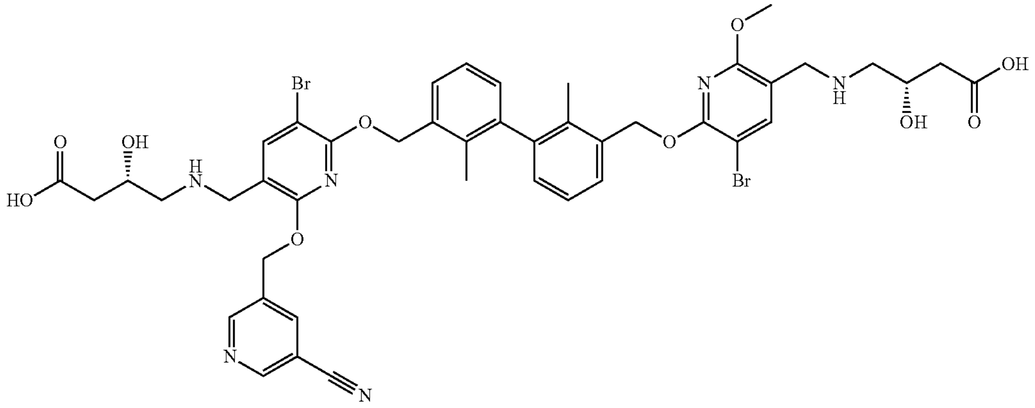 [SMILES: COc1nc(OCc2cccc(-c3cccc(COc4nc(OCc5cncc(C#N)c5)c(CNC[C@@H](O)CC(=O)O)cc4Br)c3C)c2C)c(Br)cc1CNC[C@@H](O)CC(=O)O] 977.2
587 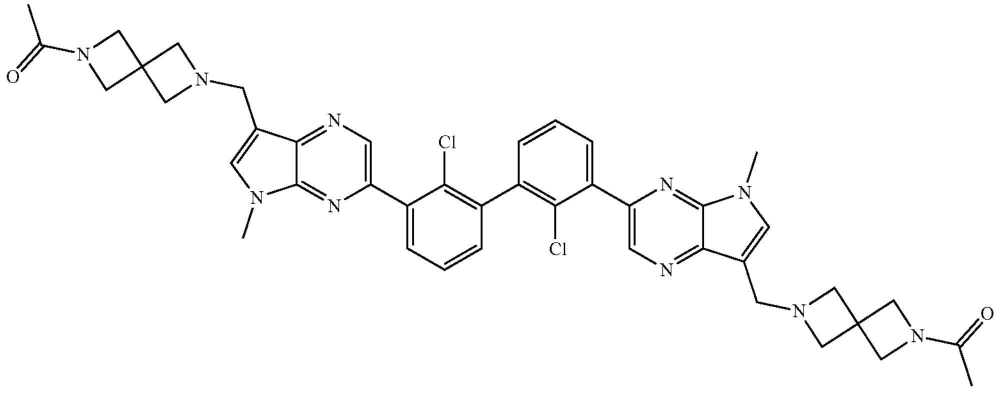 [SMILES: CC(=O)N1CC2(CN(Cc3cn(C)c4nc(-c5cccc(-c6cccc(-c7cnc8c(CN9CC%10(C9)CN(C(C)=O)C%10)cn(C)c8n7)c6Cl)c5Cl)cnc34)C2)C1] 789.2

-continued
588 761.136
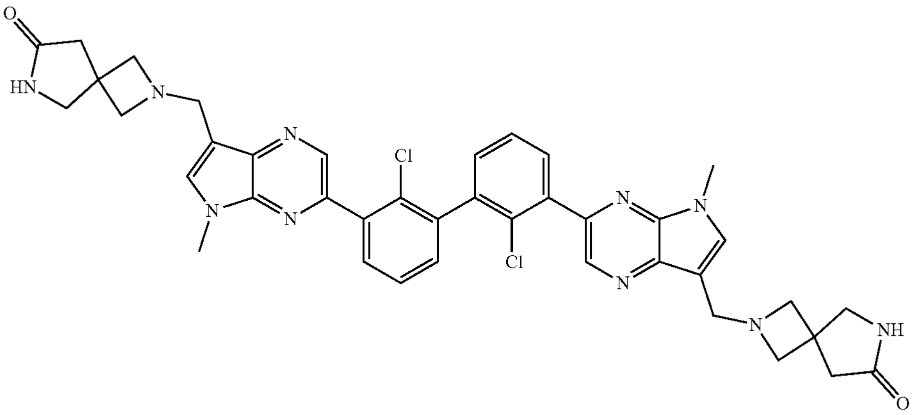 [SMILES: Cn1cc(CN2CC3(CNC(=O)C3)C2)c2ncc(-c3cccc(-c4cccc(-c5cnc6c(CN7CC8(CNC(=O)C8)C7)cn(C)c6n5)c4Cl)c3Cl)nc21]
589 761.195
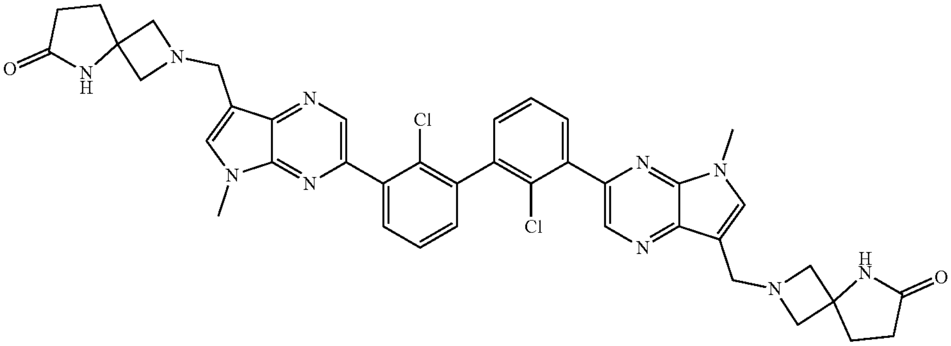 [SMILES: Cn1cc(CN2CC3(CCC(=O)N3)C2)c2ncc(-c3cccc(-c4cccc(-c5cnc6c(CN7CC8(CCC(=O)N8)C7)cn(C)c6n5)c4Cl)c3Cl)nc21]
590 757.9
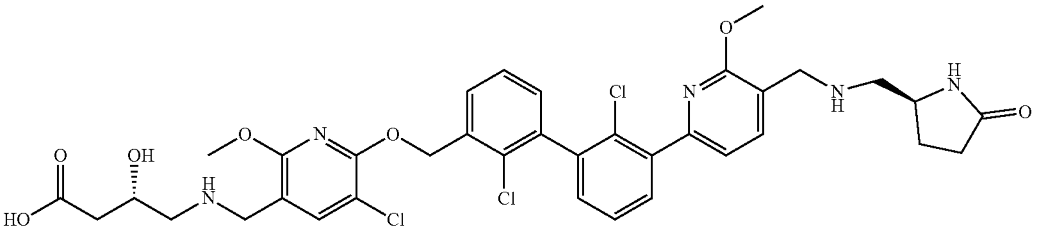 [SMILES: COc1nc(-c2cccc(-c3cccc(COc4nc(OC)c(CNC[C@@H](O)CC(=O)O)cc4Cl)c3Cl)c2Cl)ccc1CNC[C@@H]1CCC(=O)N1]
591 758.9
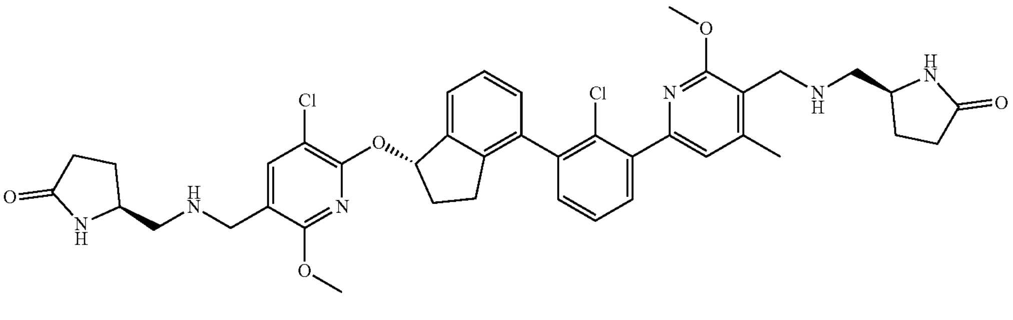 [SMILES: COc1nc(O[C@H]2CCc3c(-c4cccc(-c5cc(C)c(CNC[C@@H]6CCC(=O)N6)c(OC)n5)c4Cl)cccc32)c(Cl)cc1CNC[C@@H]1CCC(=O)N1]

-continued
592 834.1
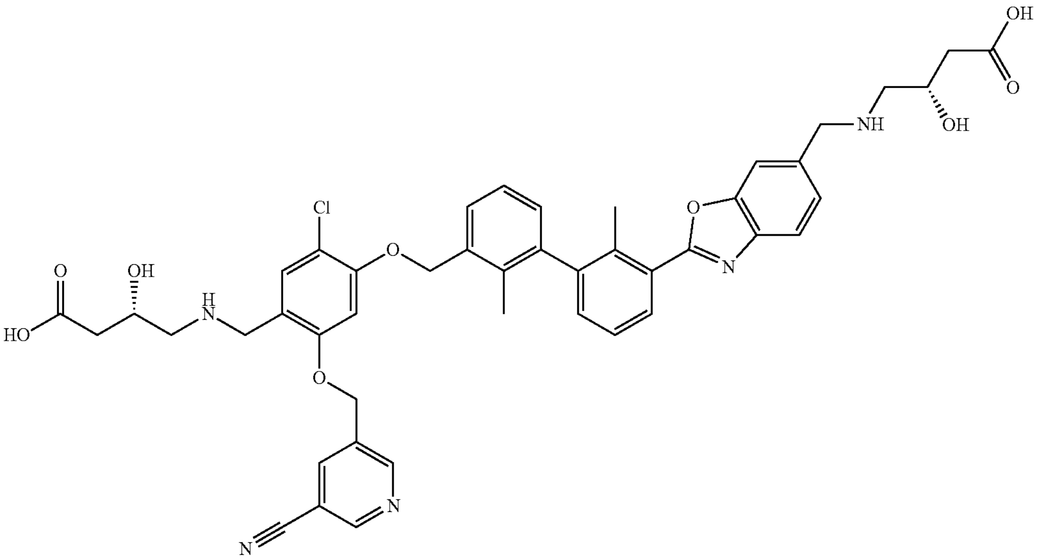 [SMILES: Cc1c(COc2cc(OCc3cncc(C#N)c3)c(CNC[C@@H](O)CC(=O)O)cc2Cl)cccc1-c1cccc(-c2nc3ccc(CNC[C@@H](O)CC(=O)O)cc3o2)c1C]
593 834.2
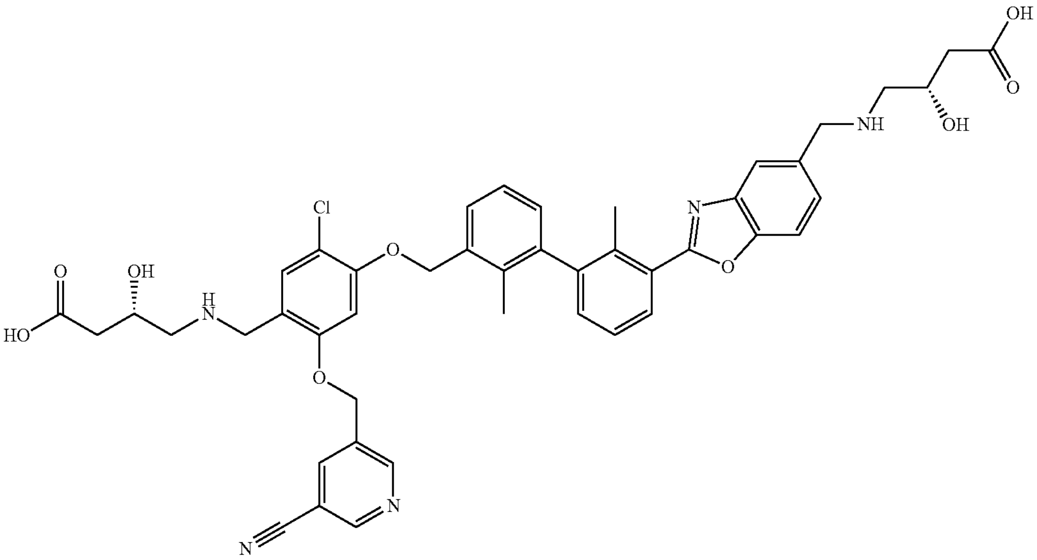 [SMILES: Cc1c(COc2cc(OCc3cncc(C#N)c3)c(CNC[C@@H](O)CC(=O)O)cc2Cl)cccc1-c1cccc(-c2nc3cc(CNC[C@@H](O)CC(=O)O)ccc3o2)c1C]

-continued

595

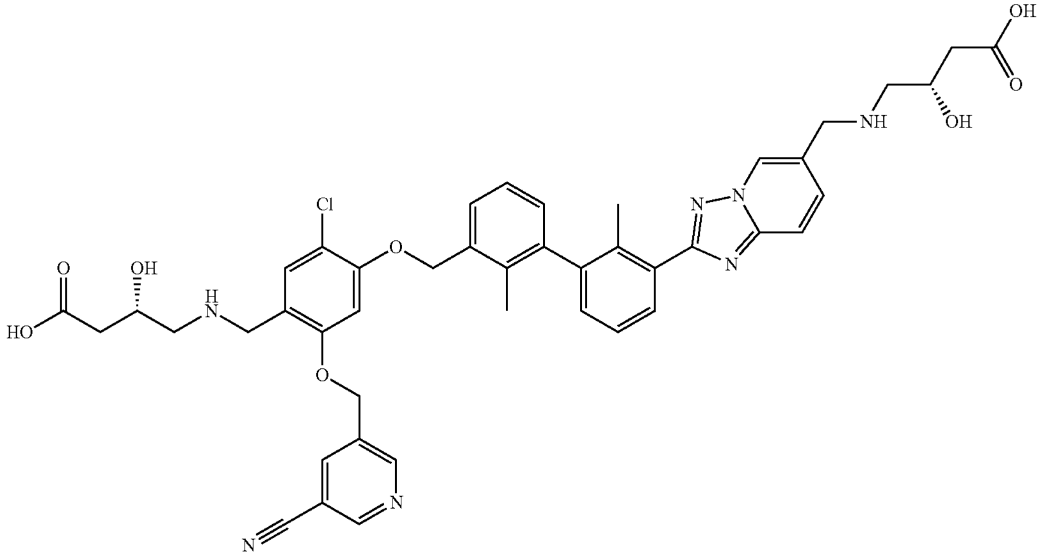 [SMILES: Cc1c(COc2cc(OCc3cncc(C#N)c3)c(CNC[C@@H](O)CC(=O)O)cc2Cl)cccc1-c1cccc(-c2nc3ccc(CNC[C@@H](O)CC(=O)O)cn3n2)c1C]

835.1

Intermediate 58: 2,2'-(2,2'-dichloro-[1,1'-biphenyl]-3,3'-diyl)bis(4,4,5,5-tetramethyl-1,3,2-dioxaborolane

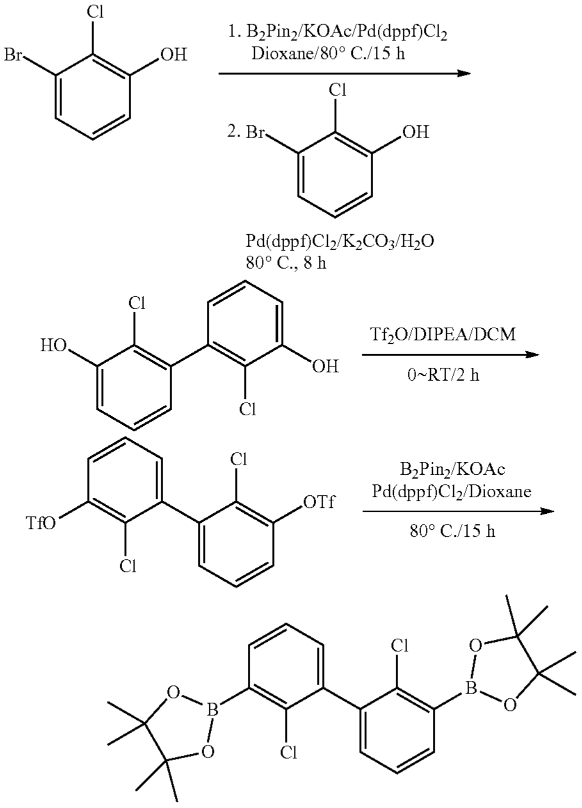

A mixture of 3-bromo-2-chlorophenol (73.5 g, 0.355 mol, 1.0 eq), $B_2Pin_2$ (98 g, 0.391 mol, 1.1 eq), KOAc (96.7 g, 0.987 mol, 2.78 eq) and Pd(dppf)$Cl_2$-DCM (25.97 g, 35.5 mmol, 0.1 eq) were suspended in dioxane (1.2 L) was stirred at 80° C. for 15 h under positive pressure of nitrogen. The resulting mixture was cooled to ambient temperature and filtered. The filter cake was washed with dioxane (500 mL). The filtrates were combined.

3-bromo-2-chlorophenol (73.5 g, 0.355 mol, 1.0 eq), $K_2CO_3$ (122 g, 0.888 mol, 2.5 eq) and Pd(dppf)$Cl_2$-DCM (8.8 g, 10.65 mmol, 0.03 eq) were added to the filtrate prepared above. The reaction was stirred at 80° C. for 8 h under positive pressure of nitrogen. The resulting mixture was cooled to ambient temperature and filtered. The filter cake was washed with dioxane (500 mL). The filtrate were combined and concentrated. The residue was dissolved with ethyl acetate (2 L). The solution was washed with water, brine, dried over sodium sulfate and concentrated. The crude was purified by silica gel chromatography (PE:EA=5:1) to give 2,2'-dichloro-[1,1'-biphenyl]-3,3'-diol.

To a solution of compound 2 (63.8 g, 0.251 mol, 1.0 eq) and DIPEA (121.5 g, 0.944 mol, 3.76 eq) in DCM (2 L) at 0° C. was added $Tf_2O$ (166 g, 0.590 mol, 2.35 eq) dropwise slowly. Then the reaction was warmed to rt and stirred for 2 h. The pH of the reaction solution was greater than 7. Water (2 L) was added. The layers were separated, and the organic phase was washed with aqueous solution $NaHCO_3$, and brine, and dried over anhydrous sodium sulfate and concentrated. The crude was purified by silica gel chromatography, eluting with PE/DCM/EtOAc (1:1:0-1:1:0.2) to give 2,2'-dichloro-[1,1'-biphenyl]-3,3'-diyl bis(trifluoromethanesulfonate).

A mixture of 2,2'-dichloro-[1,1'-biphenyl]-3,3'-diyl bis (trifluoromethanesulfonate) (150 g, 0.289 mol, 1.0 eq), $Bin_2Pin_2$ (180 g, 0.722 mol, 2.5 eq) KOAc (113 g, 1.156 mol, 4.0 eq) and Pd(dppf)$Cl_2$-DCM (31.72 g, 0.0434 mol, 0.15 eq) in dioxane (1.5 L) was stirred at 80° C. for 15 h under positive pressure of nitrogen. The resulting mixture was cooled to ambient temperature. DCM (1.5 L) was added, and the mixture was stirred for 15 min at rt. The mixture was filtered and the filter cake was washed with DCM (500 mL). The filtrates were combined and concentrated. The crude was purified by silica gel chromatography (PE:EA, 10:1-5:1) to give the title compound. $^1$H NMR (400 MHz, DMSO-d6) δ 7.63 (d, J=6.7 Hz, 2H), 7.46-7.30 (m, 4H), 1.34 (s, 24H).

Intermediate 59: 6-(3-bromo-2-chlorophenyl)-2-methoxynicotinaldehyde

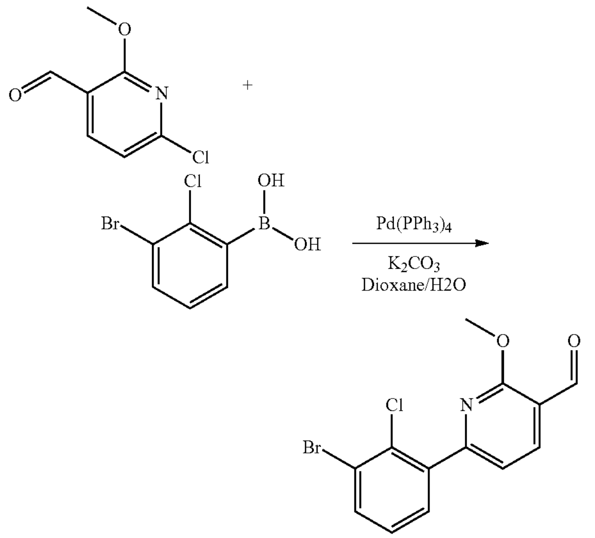

6-chloro-2-methoxynicotinaldehyde (1.2 g, 7.01 mmol), (3-bromo-2-chlorophenyl)boronic acid (1.5 g, 6.38 mmol), Potassium Carbonate (1.76 g, 12.75 mmol), and Tetrakis (triphenylphosphine)palladium(0) (0.37 g, 0.32 mmol), are suspended in 30 mL of a 10:1 mixture of dioxane and water. The mixture is sparged with argon gas for 10 minutes, and heated in a 95 C hot plate for 3 h. The solution is cooled to rt, and diluted with dichloromethane (100 mL), water (50 mL), and brine (50 mL). The organic layer was separated, and aqueous layer extracted 1× with dichloromethane (50 mL). The combined organics were dried over $Na2SO_4$, filtered, concentrated, and purified via column chromatography with dichloromethane eluent (dry loaded, solubility issues if DCM is not used). The fractions containing the product are concentrated to yield the crude yellow solid that is contaminated with unreacted 6-chloro-2-methoxynicotinaldehyde. The yellow solid is crushed, and diluted with Et2O, sonicated, and filtered. The filtrate is washed 2× with Et2O to give 6-(3-bromo-2-chlorophenyl)-2-methoxynicotinaldehyde. $^1$H NMR (400 MHz, DMSO-$d_6$) δ 10.30 (s, 1H), 8.22 (d, J=7.7 Hz, 1H), 7.93 (dd, J=8.1, 1.5 Hz, 1H), 7.65 (dd, J=7.7, 1.5 Hz, 1H), 7.53-7.31 (m, 2H), 4.04 (s, 3H).

Intermediate 60: 6-(2-chloro-3-(4,4,5,5-tetramethyl-1,3,2-dioxaborolan-2-yl)phenyl)-2-methoxynicotinaldehyde

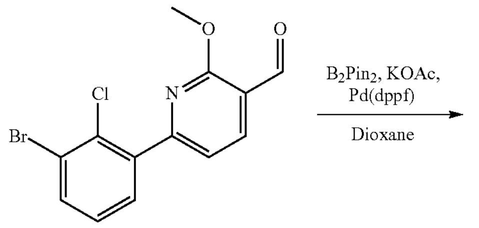

-continued

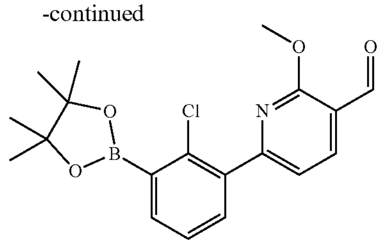

6-(3-bromo-2-chlorophenyl)-2-methoxynicotinaldehyde (720 mg, 2.2 mmol), Bis(pinacolato)diborane (615.85 mg, 2.43 mmol), potassium acetate (605.85 mg, 6.17 mmol), and 1,1'-Bis(diphenylphosphino)ferrocene-palladium(II)dichloride dichloromethane complex (182.27 mg, 0.22 mmol) was suspended in 20 mL of Dioxane. The resulting suspension was sparged with argon for 5 min. The reaction was sealed and stirred at 95 C for 6 h. The reaction was diluted with EtOAc, and filtered through a plug of celite. The filtrate was concentrated and purified by silica gel chromatography, eluting with EtOAc (0-10%) in Hexanes to provide 6-(2-chloro-3-(4,4,5,5-tetramethyl-1,3,2-dioxaborolan-2-yl)phenyl)-2-methoxynicotinaldehyde. $^1$H NMR (400 MHz, DMSO-$d_6$) δ 10.30 (s, 1H), 8.20 (d, J=7.7 Hz, 1H), 7.88-7.61 (m, 2H), 7.49 (t, J=7.5 Hz, 1H), 7.42 (d, J=7.7 Hz, 1H), 4.04 (s, 3H), 1.34 (s, 12H).

Intermediate 61: 6-(3'-bromo-2,2'-dichloro-[1,1'-biphenyl]-3-yl)-2-methoxynicotinaldehyde

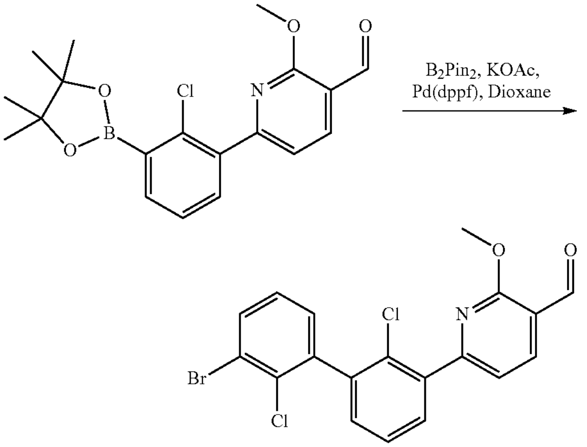

6-(2-chloro-3-(4,4,5,5-tetramethyl-1,3,2-dioxaborolan-2-yl)phenyl)-2-methoxynicotinaldehyde (400 mg, 1.07 mmol), Potassium Carbonate (354.57 mg, 2.57 mmol), 1,1'-Bis(diphenylphosphino)ferrocene-palladium(II)dichloride dichloromethane complex (88.5 mg, 0.11 mmol), and 1,3-dibromo-2-chlorobenzene (578.84 mg, 2.14 mmol) was suspended in 10 mL of a 9:1 mixture of Dioxane:water. The resulting suspension was sparged with argon for 10 minutes, sealed, and stirred at 95 C for 4 h. The suspension was cooled and diluted with EtOAc. The organic layer was washed with water and brine. The combined organics were dried over $Na2SO_4$, concentrated, and purified by silica gel chromatography, eluting with Hexane/EtOAc (0-10%). The fractions were collected to afford 6-(3'-bromo-2,2'-dichloro-[1,1'-biphenyl]-3-yl)-2-methoxynicotinaldehyde. $^1$H NMR (400 MHz, DMSO-$d_6$) δ 10.31 (s, 1H), 8.22 (d, J=7.7, Hz1H), 7.88 (dd, J=7.8, 1.8 Hz, 1H), 7.76 (dd, J=7.8, 1.7 Hz, 1H), 7.61 (t, J=7.6 Hz, 1H), 7.54-7.29 (m, 4H), 4.07 (s, 3H).

Intermediate 62: 6-(2,2'-dichloro-3'-(4,4,5,5-tetramethyl-1,3,2-dioxaborolan-2-yl)-[1,1'-biphenyl]-3-yl)-2-methoxynicotinaldehyde

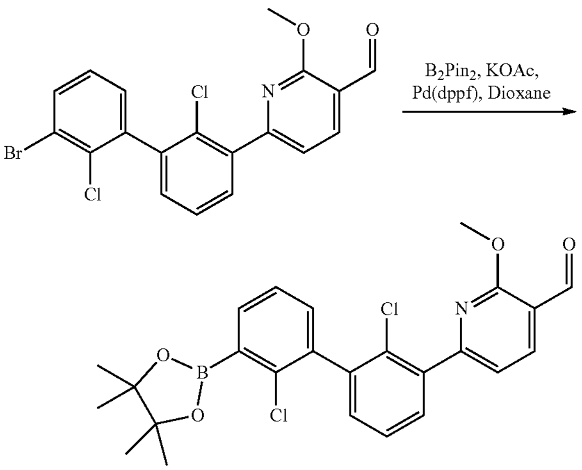

6-(3'-bromo-2,2'-dichloro-[1,1'-biphenyl]-3-yl)-2-methoxynicotinaldehyde (200 mg, 0.46 mmol), Bis(pinacolato)diborane (127.81 mg, 0.5 mmol), potassium acetate (125.73 mg, 1.28 mmol), and 1,1'-Bis(diphenylphosphino)ferrocene-palladium(II)dichloride dichloromethane complex (37.83 mg, 0.05 mmol) was suspended in 5 mL of Dioxane. The resulting suspension was sparged with argon for 5 min. The reaction was sealed and stirred at 95 C for 4 h. The reaction was diluted with EtOAc, and filtered through a plug of celite. The filtrate was concentrated and purified by silica gel chromatography, eluting with EtOAc (0-10%) in Hexanes to provide 6-(2,2'-dichloro-3'-(4,4,5,5-tetramethyl-1,3,2-dioxaborolan-2-yl)-[1,1'-biphenyl]-3-yl)-2-methoxynicotinaldehyde. $^1$H NMR (400 MHz, DMSO-$d_6$) δ 10.31 (s, 1H), 8.22 (d, J=7.8 Hz, 1H), 7.71 (ddd, J=15.5, 7.2, 1.9 Hz, 2H), 7.58 (t, J=7.6 Hz, 1H), 7.54-7.41 (m, 4H), 4.07 (s, 3H), 1.33 (s, 12H).

Example 596: (S)-5-((((6-(3'-(1-(2-aminoethyl)-1H-pyrazol-4-yl)-2,2'-dichloro-[1,1'-biphenyl]-3-yl)-2-methoxypyridin-3-yl)methyl)amino)methyl)pyrrolidin-2-one

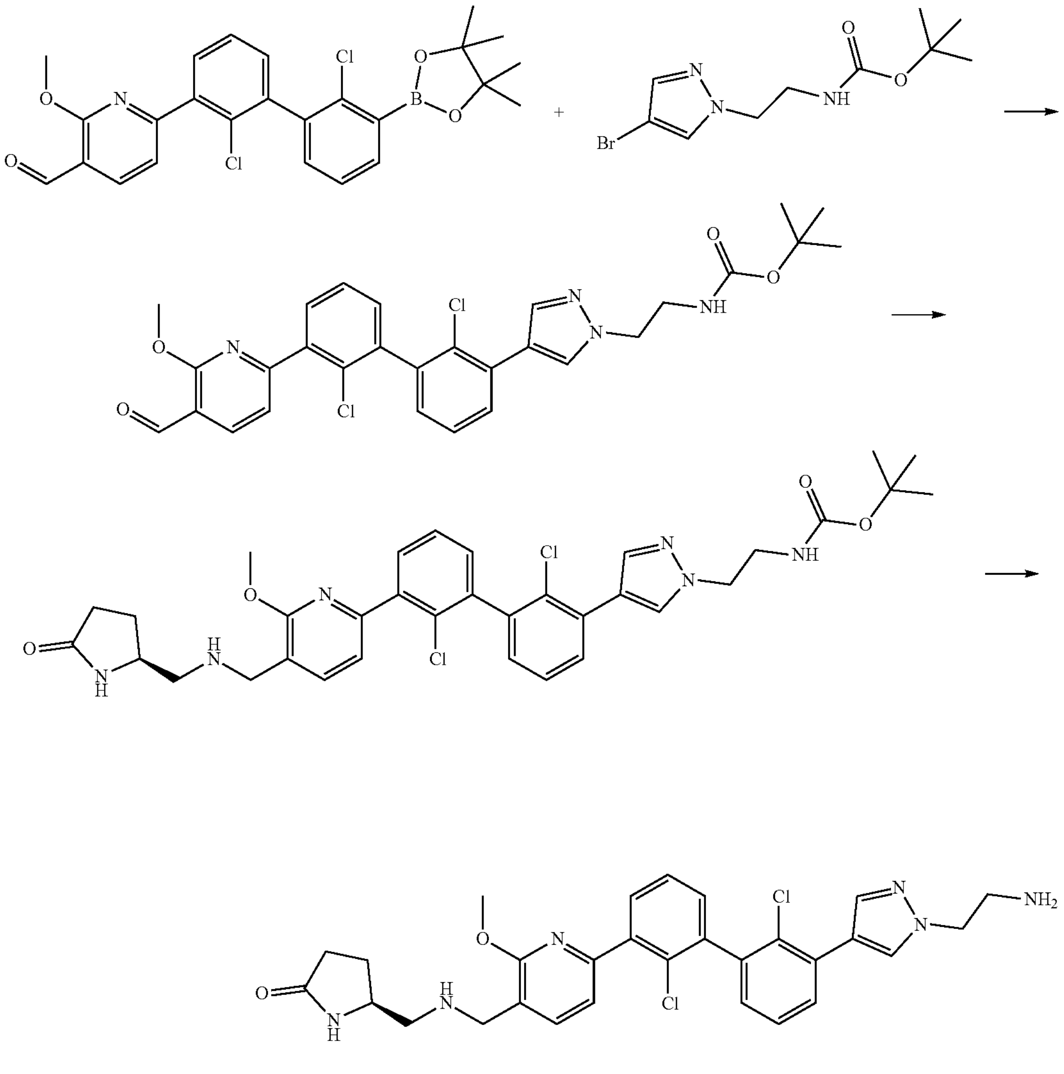

A mixture of tert-butyl (2-(4-bromo-1H-pyrazol-1-yl) ethyl)carbamate (290 mg, 1 mmol), 6-(2,2'-dichloro-3'-(4,4,5,5-tetramethyl-1,3,2-dioxaborolan-2-yl)-[1,1'-biphenyl]-3-yl)-2-methoxynicotinaldehyde (484 mg, 1 mmol), DMF (3 mL) and 2N potassium carbonate (0.5 mL) was purged with argon for 10 min. [1,1'-Bis(diphenylphosphino)ferrocene] dichloropalladium(II) complex with dichloromethane (41 mg, 0.05 mmol) was then added. The resulting mixture was stirred at 90° C. for 1 h. After cooling, the mixture was partitioned between ethyl acetate and 3% LiCl in water. The ethyl acetate layer was taken and concentrated. The residue was purified by Combiflash (70% EtOAc in hexanes), affording tert-butyl (2-(4-(2,2'-dichloro-3'-(5-formyl-6-methoxypyridin-2-yl)-[1,1'-biphenyl]-3-yl)-1H-pyrazol-1-yl)ethyl)carbamate. $[M+H]^+$ 566.9.

tert-Butyl (2-(4-(2,2'-dichloro-3'-(5-formyl-6-methoxy-pyridin-2-yl)-[1,1'-biphenyl]-3-yl)-1H-pyrazol-1-yl)ethyl) carbamate was then subjected to the reductive amination using (S)-5-(aminomethyl)pyrrolidin-2-one and sodium tri-acetoxyborohydride, affording tert-butyl (S)-(2-(4-(2,2'-di-chloro-3'-(6-methoxy-5-((((5-oxopyrrolidin-2-yl)methyl) amino)methyl)pyridin-2-yl)-[1,1'-biphenyl]-3-yl)-1H-pyrazol-1-yl)ethyl)carbamate. $[M+H]^+$ 664.8.

To a solution of tert-butyl (S)-(2-(4-(2,2'-dichloro-3'-(6-methoxy-5-((((5-oxopyrrolidin-2-yl)methyl)amino)methyl) pyridin-2-yl)-[1,1'-biphenyl]-3-yl)-1H-pyrazol-1-yl)ethyl) carbamate (100 mg, 0.15 mmol) in dichloromethane (2 mL) was added trifluoroacetic acid (1 mL). After stirring for 30 min. at room temperature, the mixture was concentrated and the residue was purified by reverse-phase HPLC, affording (S)-5-((((6-(3'-(1-(2-aminoethyl)-1H-pyrazol-4-yl)-2,2'-di-chloro-[1,1'-biphenyl]-3-yl)-2-methoxypyridin-3-yl) methyl)amino)methyl)pyrrolidin-2-one as the bisTFA salt. $^1H$ NMR (400 MHz, Methanol-$d_4$) δ 8.14 (d, J=0.8 Hz, 1H), 7.96 (d, J=0.8 Hz, 1H), 7.88 (d, J=7.6 Hz, 1H), 7.69-7.59 (m, 2H), 7.50 (t, J=7.6 Hz, 1H), 7.42 (t, J=7.7 Hz, 1H), 7.38-7.32 (m, 2H), 7.24 (dd, J=7.5, 1.7 Hz, 1H), 4.55-4.45 (m, 2H), 4.34 (dd, J=2.6 Hz, 2H), 4.09 (s, 3H), 4.06 (t, J=6.5 Hz, 1H), 3.48 (t, J=5.7 Hz, 2H), 3.25 (dd, J=6.2, 4.2 Hz, 2H), 2.52-2.30 (m, 3H), 1.99-1.84 (m, 1H). $[M+H]^+$ 565.1.

Example 597: (S)-5-((((6-(2-chloro-3-(4-(6-methoxy-5-(((((S)-5-oxopyrrolidin-2-yl)methyl) amino)methyl)pyridin-2-yl)thiophen-2-yl)phenyl)-2-methoxypyridin-3-yl)methyl)amino)methyl) pyrrolidin-2-one

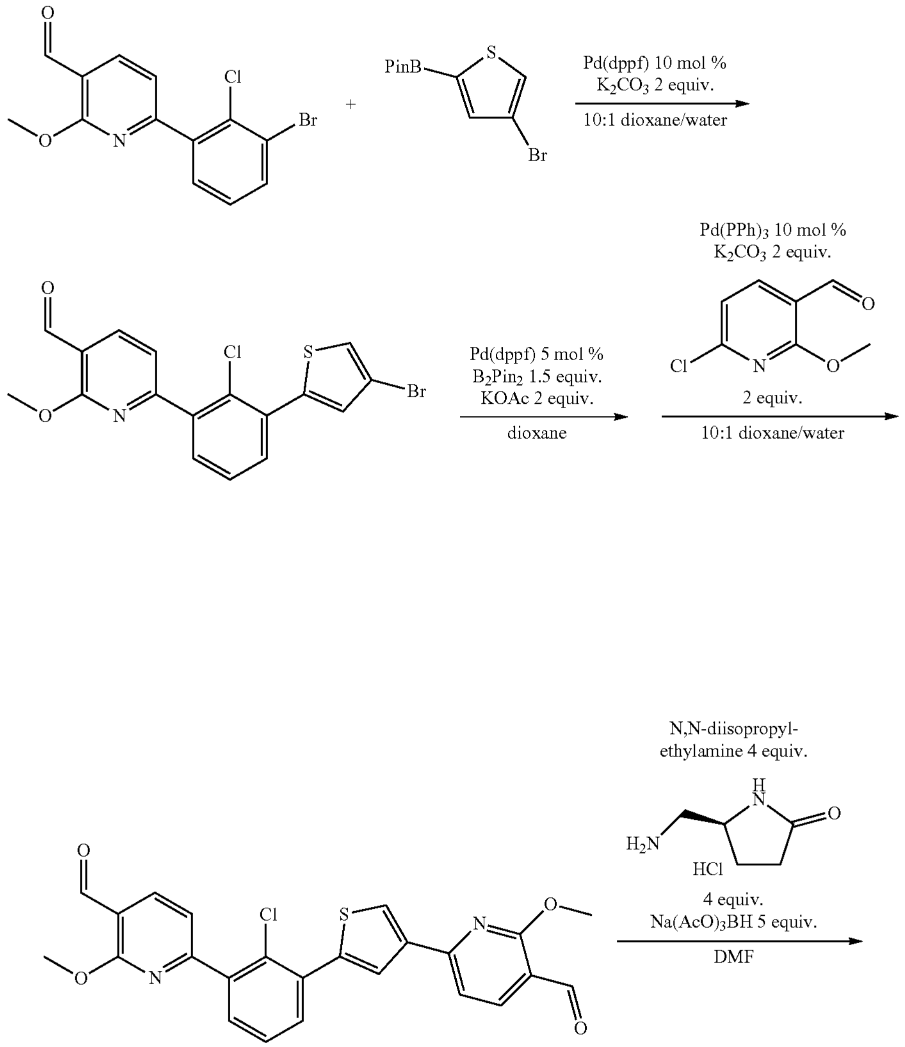

-continued

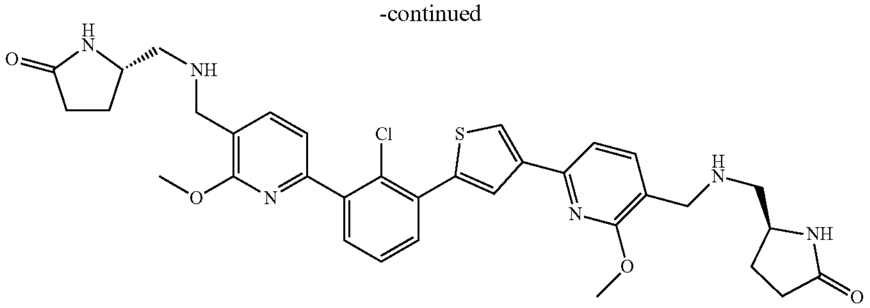

A 40 mL reaction vial, fitted with a stir bar, was charged with 2-(4-bromothiophen-2-yl)-4,4,5,5-tetramethyl-1,3,2-dioxaborolane (0.150 g), 6-(3-bromo-2-chlorophenyl)-2-methoxynicotinaldehyde (0.203 g), Pd(dppf) (0.018 g) and potassium carbonate (0.143 g). DriSolv 1,4-Dioxane (5 mL) and distilled water (0.5 mL) were then added by syringe, and the mixture de-gassed by bubbling argon for 5 min while mixing. The reaction vial was then sealed with a septum cap and the reaction heated to 85° C. using a heating block, the reaction was monitored by LC/MS. Upon complete consumption of starting material, saturated NaCl in water was added and the reaction mixture was extracted three times with ethyl acetate. The organic layers were collected, volatiles removed and crude mixture purified by silica gel column chromatography. LCMS m/z 410.00 M+1.

A 40 mL screw cap vial, fitted with a stir bar, was charged with 6-(3-(4-bromothiophen-2-yl)-2-chlorophenyl)-2-methoxynicotinaldehyde (0.070 g), bis(pinacolato)diboron (0.065 g), potassium acetate (0.034 g) and Pd(dppf) (0.007 g). DriSolv 1,4-Dioxane (2 mL) was then added by syringe, and the mixture was de-gassed by bubbling argon through for 5 min while mixing. The vial was then sealed and the mixture heated to 85° C., the reaction was monitored by LC/MS and upon complete consumption of the starting material the crude mixture was carried through to the next reaction without any purification (boronic ester intermediate LCMS m/z 456.128 M+1). To the previous reaction was added 6-chloro-2-methoxynicotinaldehyde (0.059 g), Pd(PPh3)4 (0.020 g), potassium carbonate (0.047 g) and distilled water (0.2 mL), the mixture was de-gassed by bubbling argon through for 5 min while mixing. The vial was sealed with a septum cap and the mixture heated to 85° C. using a heating block, the reaction was monitored by LC/MS. Upon complete consumption of arylboronic ester a saturated solution of NaCl in water was added to the reaction mixture in equal-volume to the initial reaction volume. The resulting mixture was extracted three times with ethyl acetate, the organic layers collected, volatiles removed in vacuo and purified by silica gel column chromatography. LCMS m/z 465.100 M+1.

A 20 mL reaction vial, fitted with a stir bar, was charged with 6-(2-chloro-3-(4-(5-formyl-6-methoxypyridin-2-yl)thiophen-2-yl)phenyl)-2-methoxynicotinaldehyde (0.028 g), (S)-5-(aminomethyl)pyrrolidin-2-one hydrochloride (0.036 g) N,N-diisopropyl-ethylamine (0.042 mL) and dimethylformamide (1 mL) and allowed to mix for 0.5 h. Sodium triacetoxy-borohydride (0.064 g) was then added and the reaction allowed to mix overnight. The next day the reaction was quenched with trifluoroacetic acid (1.205 mmol), filtered, diluted with a 1:4 solution DMF/water and purified by HPLC to give (S)-5-((((6-(2-chloro-3-(4-(6-methoxy-5-(((((S)-5-oxopyrrolidin-2-yl)methyl)amino)methyl)pyridin-2-yl)thiophen-2-yl)phenyl)-2-methoxypyridin-3-yl)methyl)amino)methyl)pyrrolidin-2-one. $^1$H NMR (400 MHz, Methanol-$d_4$) δ 8.23 (d, J=1.4 Hz, 1H), 7.93 (d, J=1.4 Hz, 1H), 7.89 (d, J=7.5 Hz, 1H), 7.81 (d, J=7.7 Hz, 1H), 7.68 (dd, J=7.6, 1.9 Hz, 1H), 7.55 (dd, J=7.7, 1.8 Hz, 1H), 7.52-7.46 (m, 2H), 7.33 (d, J=7.5 Hz, 1H), 4.40-4.23 (m, 4H), 4.18-3.99 (m, 8H), 3.28-3.14 (m, 3H), 2.49-2.31 (m, 6H), 1.99-1.82 (m, 2H). ES/MS m/z: 661.281 M+1.

Example 598: (S)-5-((((6-(2,2'-dichloro-3'-(1-(2-(dimethylamino)ethyl)-1H-indol-5-yl)-[1,1'-biphenyl]-3-yl)-2-methoxypyridin-3-yl)methyl)amino)methyl)pyrrolidin-2-one

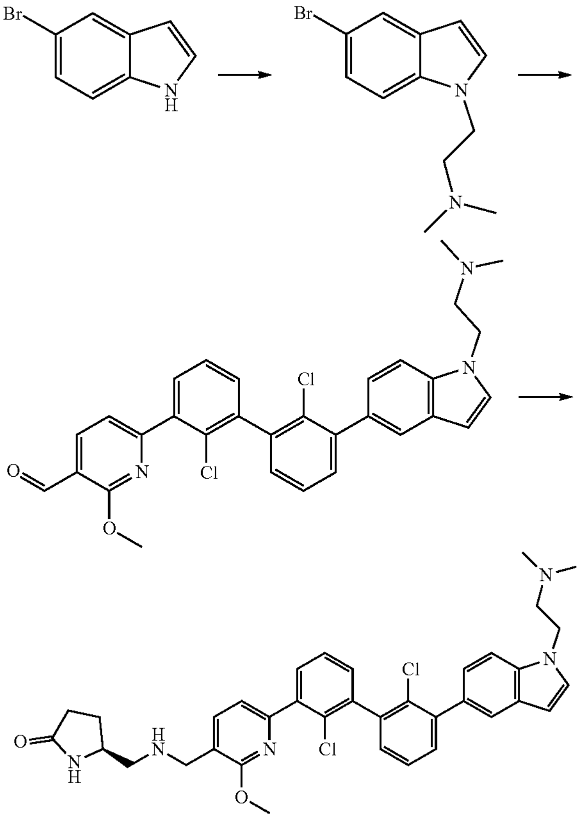

To a stirred solution of 5-Bromoindole (200 mg) in DMF at room temperature was added NaH (2.2 equiv.). After gas evolution ceased (2-chloroethyl)dimethylamine hydrochloride (1.2 equiv.) was added. The reaction was stirred until complete consumption was observed by LC/MS. The reaction was then diluted with water and extracted 3×5 mL with EtOAc. The combined organic layers were dried over sodium sulfate and concentrated in vacuo. The crude material was subjected to column chromatography (0%-10% MeOH/DCM+0.1% $NEt_3$) to afford 2-(5-bromo-1H-indol-1-yl)-N,N-dimethylethan-1-amine.

2-(5-bromo-1H-indol-1-yl)-N,N-dimethylethan-1-amine (1.2 equiv.), $Pd(PPh_3)_4$ (0.1 equiv.), $K_2CO_3$ (2.0 equiv.), and 6-(2,2'-dichloro-3'-(4,4,5,5-tetramethyl-1,3,2-dioxaborolan-2-yl)-[1,1'-biphenyl]-3-yl)-2-methoxynicotinaldehyde (40 mg, 1.0 equiv.) were place in a vial. The vial was charged with a stir bar and sealed. Dioxane (1 mL) and water (0.25 mL) were added via syringe. The vial was then subjected to 4 cycles of evacuation followed by back-filling with argon. The reaction vessel was then heated to 90° C. for 2 hours. LC/MS indicated full consumption of pinacol boronate. The reaction mixture was then diluted with water (3 mL) and extracted 3×5 mL EtOAc. The combined organic layers were dried over sodium sulfate and concentrated in vacuo. The crude material was subjected to column chromatography (0%-10% MeOH/DCM+0.1% $NEt_3$) to afford 6-(2,2'-dichloro-3'-(1-(2-(dimethylamino)ethyl)-1H-indol-5-yl)-[1,1'-biphenyl]-3-yl)-2-methoxynicotinaldehyde.

To a vial charged with 6-(2,2'-dichloro-3'-(1-(2-(dimethylamino)ethyl)-1H-indol-5-yl)-[1,1'-biphenyl]-3-yl)-2-methoxynicotinaldehyde (20 mg, 1.0 equiv.), (S)-5-(aminomethyl)pyrrolidin-2-one hydrochloride (3.0 equiv.), and triethylamine (3.0 equiv.) was added 0.75 mL of DMF. To this slurry was added sodium cyanoborohydride (5.0 equiv.). Upon complete consumption of starting material according to LC/MS the reaction mixture was diluted with a 5:1 DMF/water solution to a total volume of 4 mL. Purification by reverse phase HPLC afforded (S)-5-((((6-(2,2'-dichloro-3'-(1-(2-(dimethylamino)ethyl)-1H-indol-5-yl)-[1,1'-biphenyl]-3-yl)-2-methoxypyridin-3-yl)methyl)amino)methyl) pyrrolidin-2-one as a bis-TFA salt. ES/MS (m/z, $M+H^+$): 642.2.

Example 599: 5-((6-acetyl-2,6-diazaspiro[3.3]heptan-2-yl)methyl)-2-(3'-(5-((6-acetyl-2,6-diazaspiro[3.3]heptan-2-yl)methyl)-6-methoxypyridin-2-yl)-2,2'-dichloro-[1,1'-biphenyl]-3-yl)isoindolin-1-one

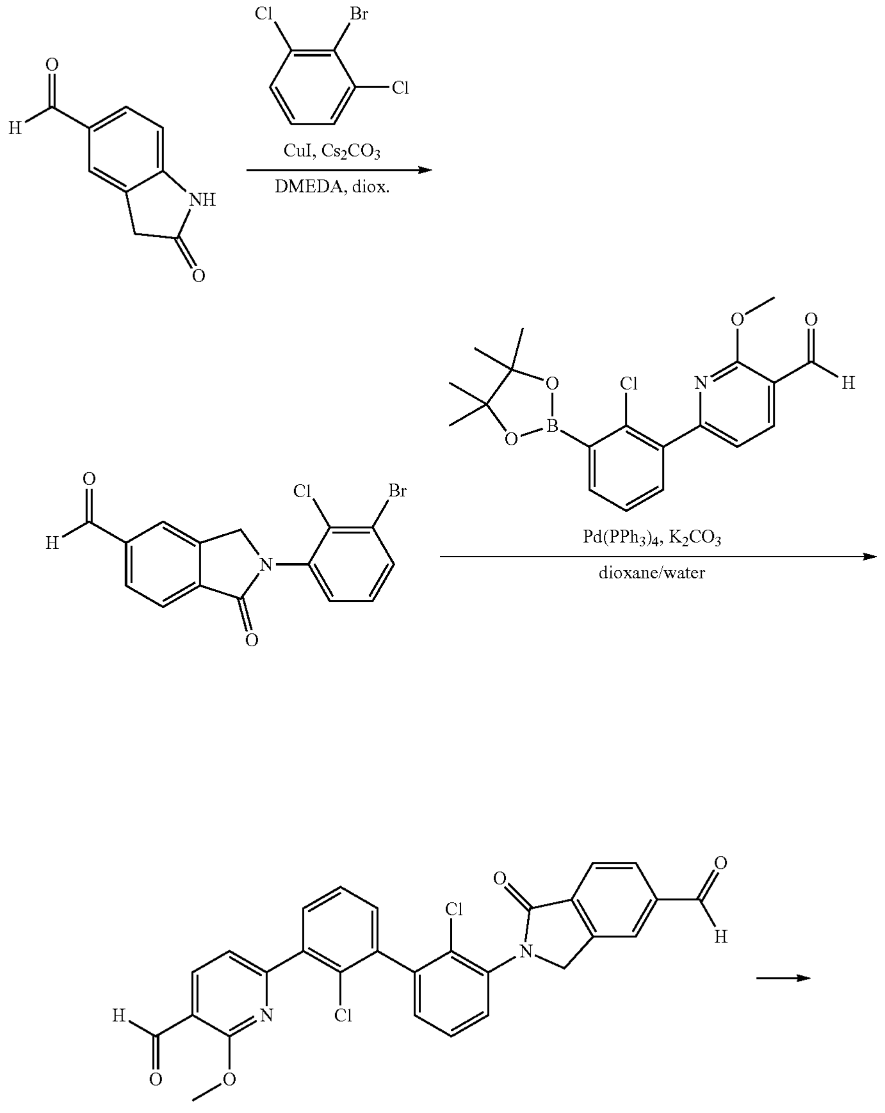

-continued

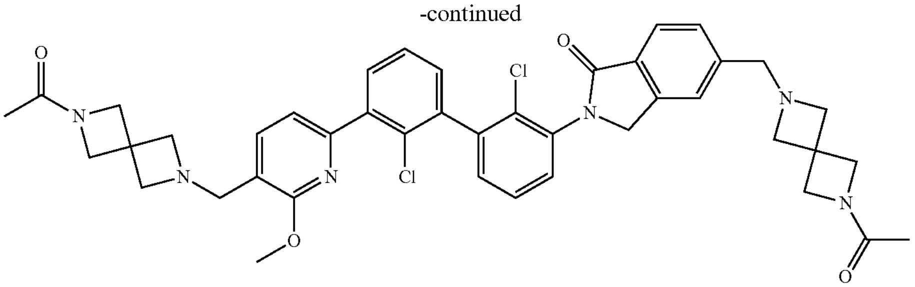

Into a flask containing 2-oxoindoline-5-carbaldehyde 1 (500 mg, 3.1 mmol) is added 1,3-dibromo-2-chlorobenzene (1677.51 mg, 6.21 mmol), along with cesium carbonate (2022 mg, 6.21 mmol), N,N'-dimethylethylenediamine 99% (0.34 mL) 3.1 mmol) and dioxane (15 mL). After flushing the reaction with nitrogen several times, the reaction was bubbled with $N_2$through the resulting suspension for 30 min before Copper(i) iodide (295 mg, 1.55 mmol) was added. A reflux condenser was attached to the flask, and the reaction mixture was heated at 105° C. overnight. The mixture was cooled to room temperature and filtered. The filtrate was diluted with ethyl acetate (40 mL) and water (20 mL), and the layers were separated. The aqueous layer was extracted with ethyl acetate (50 mL), and the combined organic layers were washed with brine (20 mL) and dried over sodium sulfate. The drying agent was removed by filtration. The filtrate was concentrated under reduced pressure, and the resulting residue was purified by flash column chromatography (silica, 80:20 Hex/EtOAc) to provide 2-(3-bromo-2-chlorophenyl)-1-oxoisoindoline-5-carbaldehyde. MS (ESI+) m/z 352.1 (M+H).

Into a microwave vial is placed 2-(3-bromo-2-chlorophenyl)-1-oxoisoindoline-5-carbaldehyde (250 mg, 0.71 mmol), 6-(2-chloro-3-(4,4,5,5-tetramethyl-1,3,2-dioxaborolan-2-yl)phenyl)-2-methoxynicotinaldehyde (293 mg, 0.78 mmol), Potassium Carbonate (197 mg, 1.43 mmol), Tetrakis (triphenylphosphine)palladium(0) (82 mg, 0.07 mmol and dioxane/water (4:1, 10 mL). The mixture was flushed with $N_2$ and heated at 110° C. for 1 hr. The mixture was diluted with EtOAc and water. The organic layer was separated, washed with brine and dried over $MgSO_4$, filtered and concentrated under reduced pressure before and the resulting residue was purified by flash column chromatography (silica, 80:20 Hex/EtOAc) to provide 2-(2,2'-dichloro-3'-(5-formyl-6-methoxypyridin-2-yl)-[1,1'-biphenyl]-3-yl)-1-oxoisoindoline-5-carbaldehyde. MS ($ESI^+$) m/z 517.31 (M+H).

The title compound was obtained using reductive amination condition A(DCM/MeOH then $Na(OAc)_3BH$ and AcOH) followed by HPLC purification. $^1H$ NMR (400 MHz, Methanol-$d_4$) δ7.97 (d, J=7.9 Hz, 1H), 7.87 (d, J=7.6 Hz, 1H), 7.75 (s, 1H), 7.66 (ddd, J=6.0, 2.9, 1.7 Hz, 2H), 7.67-7.39 (n, 6H), 7.36 (d, J=7.5 Hz, 1H), 4.97 (s, 2H), 4.53 (s, 2H), 4.47-4.36 (n, 18H), 4.16 (s, 5H), 4.08 (s, 3H), 1.84 (s, 6H). $^{19}F$ NMR (376 MHz, Methanol-$d_4$) δ −77.63. MS ($ESI^+$) m/z 765.15 (M+H).

The following compounds were prepared according to the procedures described herein using the appropriate starting material(s) and appropriate protecting group chemistry as needed.

| Example No. | Structure | ES/MS (m/z, M + H$^+$) |
| --- | --- | --- |
| 600 | 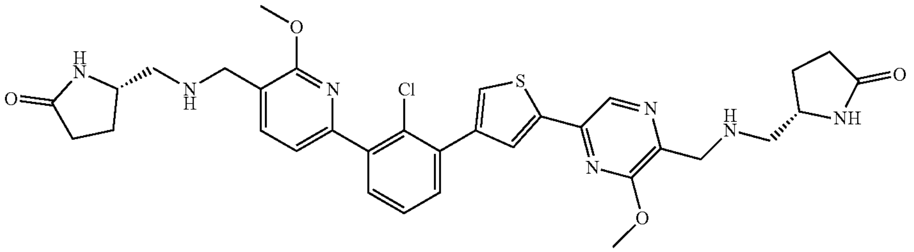 [SMILES: COc1nc(-c2cccc(-c3csc(-c4cnc(CNC[C@@H]5CCC(=O)N5)c(OC)n4)c3)c2Cl)ccc1CNC[C@@H]1CCC(=O)N1] | 662.264 |
| 601 | 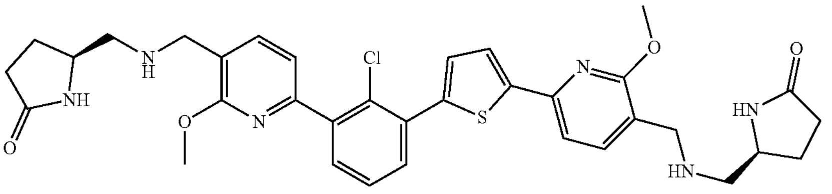 [SMILES: COc1nc(-c2ccc(-c3cccc(-c4ccc(CNC[C@@H]5CCC(=O)N5)c(OC)n4)c3Cl)s2)ccc1CNC[C@@H]1CCC(=O)N1] | 660.809 |

-continued
| Example No. | Structure | ES/MS (m/z, M + H⁺) |
|---|---|---|
| 602 | 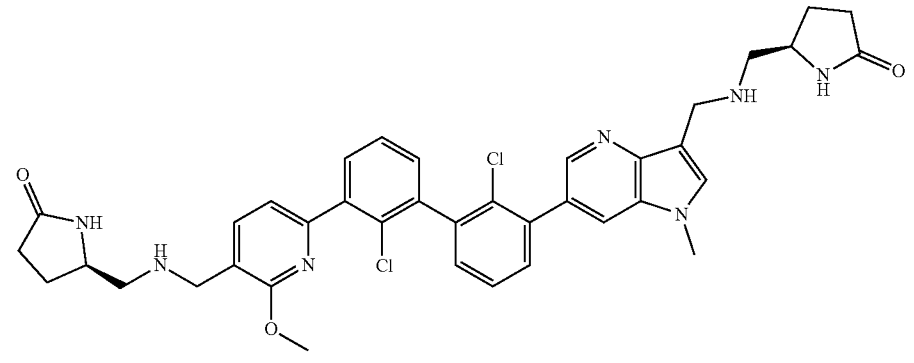 [SMILES: COc1nc(-c2cccc(-c3cccc(-c4cnc5c(CNC[C@H]6CCC(=O)N6)cn(C)c5c4)c3Cl)c2Cl)ccc1CNC[C@H]1CCC(=O)N1] | 712.3 |
| 603 | 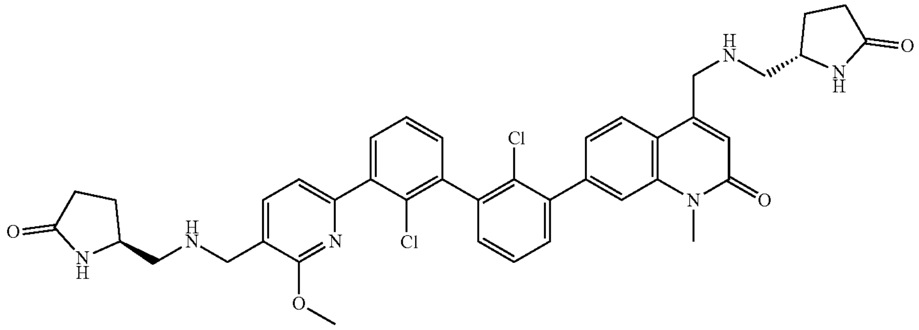 [SMILES: COc1nc(-c2cccc(-c3cccc(-c4ccc5c(CNC[C@@H]6CCC(=O)N6)cc(=O)n(C)c5c4)c3Cl)c2Cl)ccc1CNC[C@@H]1CCC(=O)N1] | 739.3 |
| 604 | 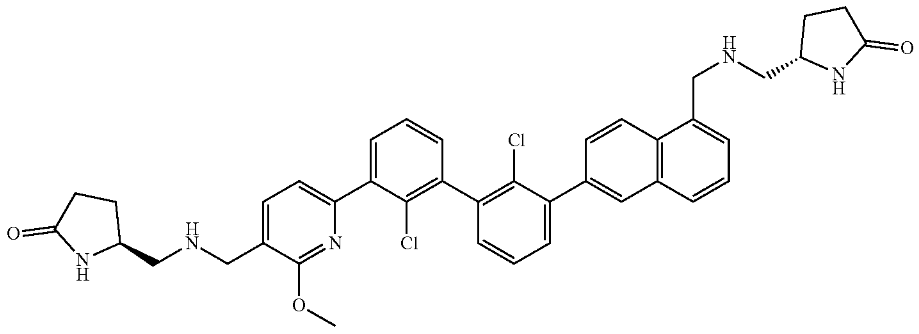 [SMILES: COc1nc(-c2cccc(-c3cccc(-c4ccc5c(CNC[C@@H]6CCC(=O)N6)cccc5c4)c3Cl)c2Cl)ccc1CNC[C@@H]1CCC(=O)N1] | 708.2 |
| 605 | 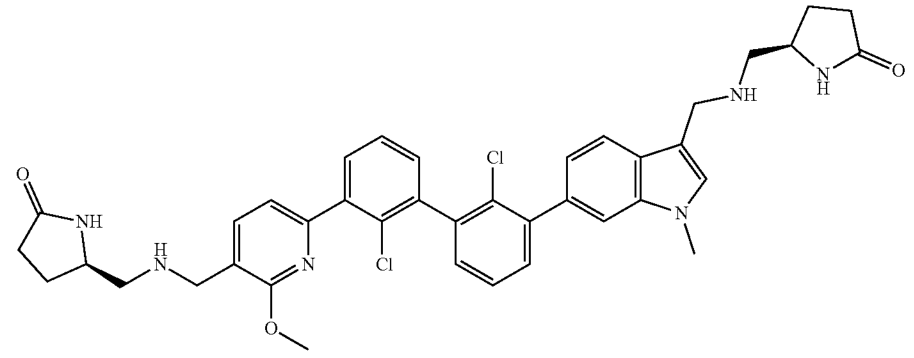 [SMILES: COc1nc(-c2cccc(-c3cccc(-c4ccc5c(CNC[C@H]6CCC(=O)N6)cn(C)c5c4)c3Cl)c2Cl)ccc1CNC[C@H]1CCC(=O)N1] | 711.4 |

-continued
| Example No. | Structure | ES/MS (m/z, M + H+) |
|---|---|---|
| 606 | 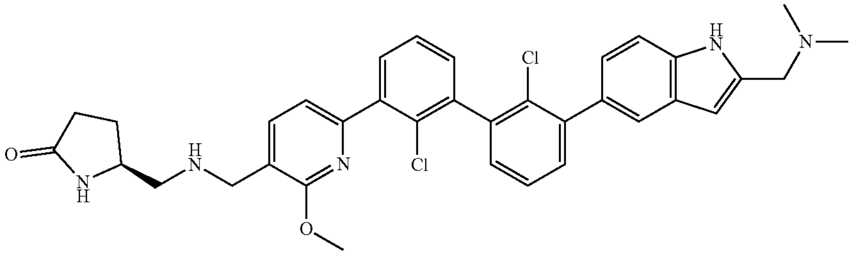 [SMILES: COc1nc(-c2cccc(-c3cccc(-c4ccc5[nH]c(CN(C)C)cc5c4)c3Cl)c2Cl)ccc1CNC[C@@H]1CCC(=O)N1] | 628.2 |
| 607 | 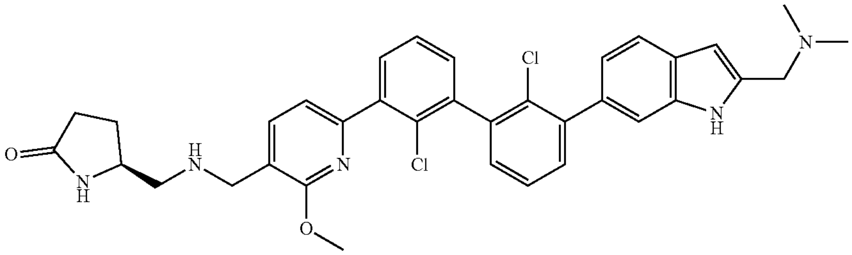 [SMILES: COc1nc(-c2cccc(-c3cccc(-c4ccc5cc(CN(C)C)[nH]c5c4)c3Cl)c2Cl)ccc1CNC[C@@H]1CCC(=O)N1] | 628.2 |
| 608 | 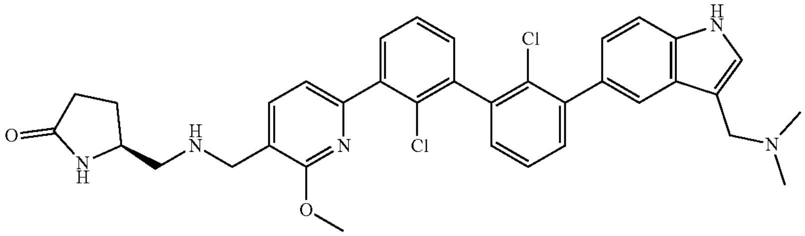 [SMILES: COc1nc(-c2cccc(-c3cccc(-c4ccc5[nH]cc(CN(C)C)c5c4)c3Cl)c2Cl)ccc1CNC[C@@H]1CCC(=O)N1] | 628.2 |
| 609 | 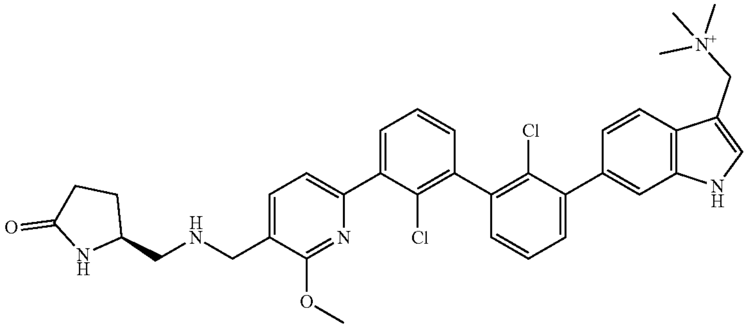 [SMILES: COc1nc(-c2cccc(-c3cccc(-c4ccc5c(C[N+](C)(C)C)c[nH]c5c4)c3Cl)c2Cl)ccc1CNC[C@@H]1CCC(=O)N1] | 642.2 ($M^+$) |
| 610 | 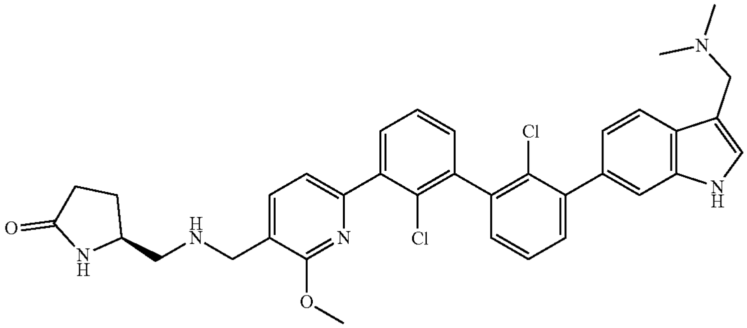 [SMILES: COc1nc(-c2cccc(-c3cccc(-c4ccc5c(CN(C)C)c[nH]c5c4)c3Cl)c2Cl)ccc1CNC[C@@H]1CCC(=O)N1] | 628.9 |

-continued
| Example No. | Structure | ES/MS (m/z, M + H⁺) |
|---|---|---|
| 611 | 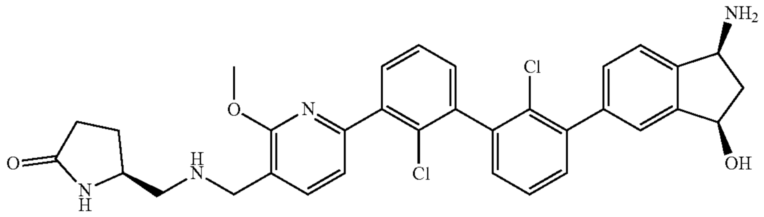 [SMILES: COc1nc(-c2cccc(-c3cccc(-c4ccc5c(c4)[C@H](O)C[C@@H]5N)c3Cl)c2Cl)ccc1CNC[C@@H]1CCC(=O)N1] | 603.2 |
| 612 | 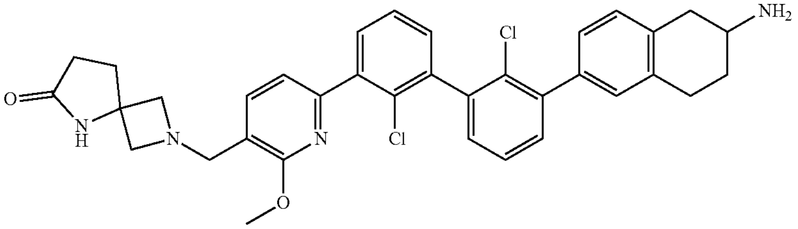 [SMILES: COc1nc(-c2cccc(-c3cccc(-c4ccc5c(c4)CCC(N)C5)c3Cl)c2Cl)ccc1CN1CC2(CCC(=O)N2)C1] | 613.1 |
| 613 | 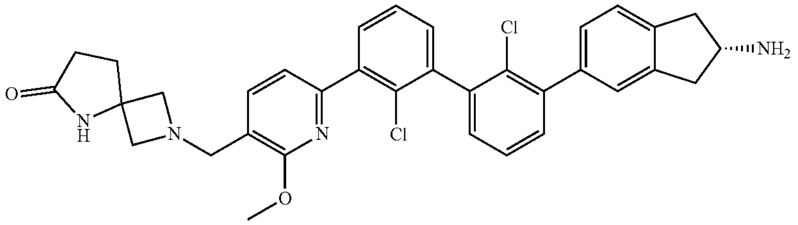 [SMILES: COc1nc(-c2cccc(-c3cccc(-c4ccc5c(c4)C[C@@H](N)C5)c3Cl)c2Cl)ccc1CN1CC2(CCC(=O)N2)C1] | 599 |
| 614 | 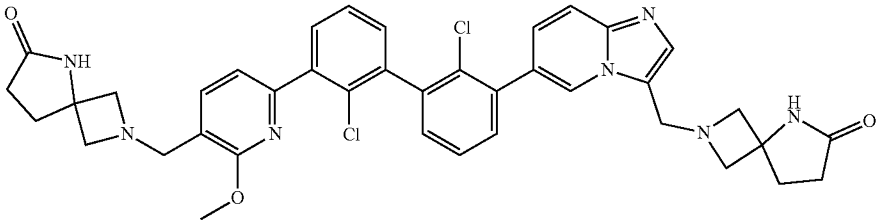 [SMILES: COc1nc(-c2cccc(-c3cccc(-c4ccc5ncc(CN6CC7(CCC(=O)N7)C6)n5c4)c3Cl)c2Cl)ccc1CN1CC2(CCC(=O)N2)C1] | 722.2 |
| 615 | 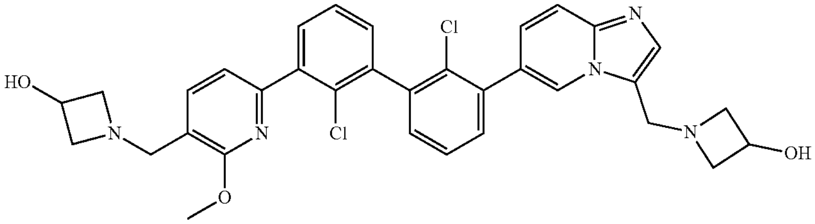 [SMILES: COc1nc(-c2cccc(-c3cccc(-c4ccc5ncc(CN6CC(O)C6)n5c4)c3Cl)c2Cl)ccc1CN1CC(O)C1] | 616.1 |
| 616 | 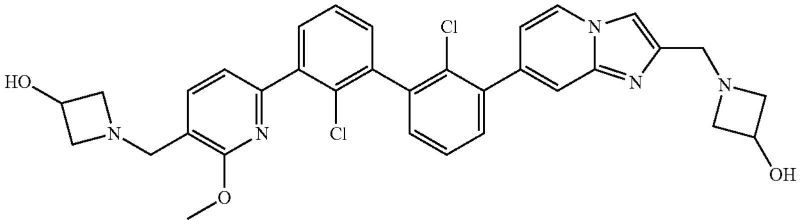 [SMILES: COc1nc(-c2cccc(-c3cccc(-c4ccn5cc(CN6CC(O)C6)nc5c4)c3Cl)c2Cl)ccc1CN1CC(O)C1] | 616.1 |

-continued
| Example No. | Structure | ES/MS (m/z, M + H+) |
|---|---|---|
| 617 | 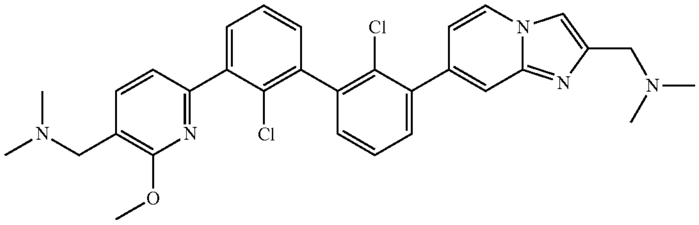 | 560.2 |
| 618 | 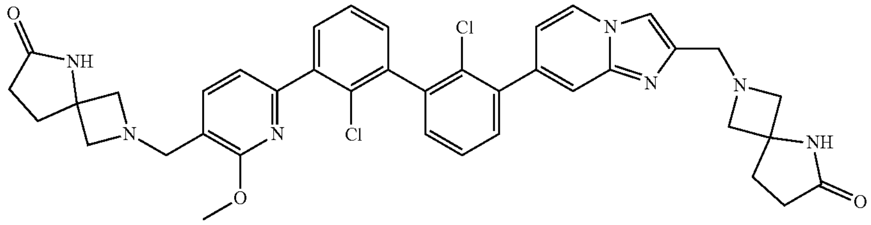 [SMILES: COc1nc(-c2cccc(-c3cccc(-c4ccn5cc(CN6CC7(CCC(=O)N7)C6)nc5c4)c3Cl)c2Cl)ccc1CN1CC2(CCC(=O)N2)C1] | 722.2 |
| 619 | 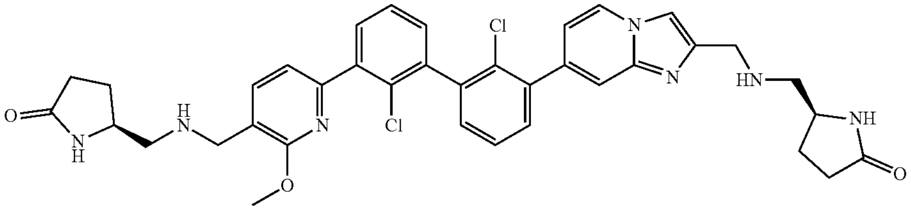 [SMILES: COc1nc(-c2cccc(-c3cccc(-c4ccn5cc(CNC[C@@H]6CCC(=O)N6)nc5c4)c3Cl)c2Cl)ccc1CNC[C@@H]1CCC(=O)N1] | 698.2 |
| 620 | 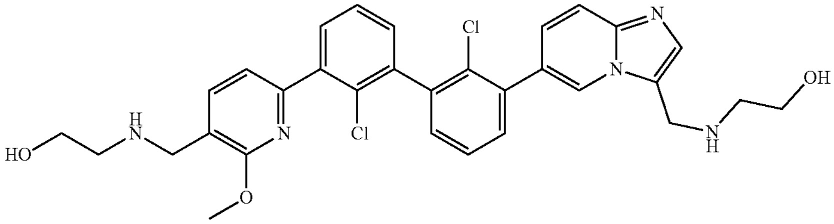 [SMILES: COc1nc(-c2cccc(-c3cccc(-c4ccc5ncc(CNCCO)n5c4)c3Cl)c2Cl)ccc1CNCCO] | 592.1 |
| 621 | 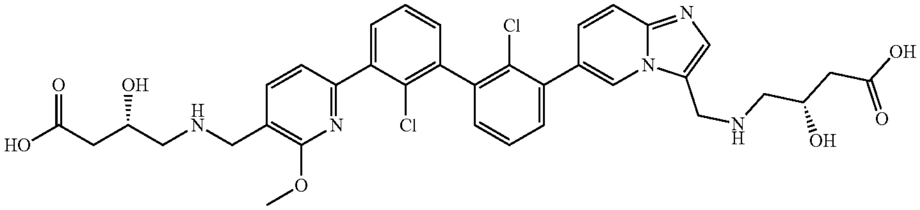 [SMILES: COc1nc(-c2cccc(-c3cccc(-c4ccc5ncc(CNC[C@@H](O)CC(=O)O)n5c4)c3Cl)c2Cl)ccc1CNC[C@@H](O)CC(=O)O] | 708.1 |
| 622 | 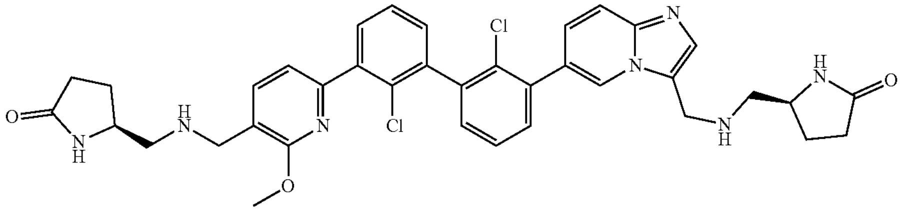 [SMILES: COc1nc(-c2cccc(-c3cccc(-c4ccc5ncc(CNC[C@@H]6CCC(=O)N6)n5c4)c3Cl)c2Cl)ccc1CNC[C@@H]1CCC(=O)N1] | 698.1 |

-continued
| Example No. | Structure | ES/MS (m/z, M + H+) |
|---|---|---|
| 623 | 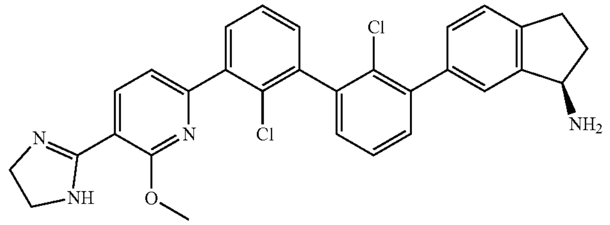 [SMILES: COc1nc(-c2cccc(-c3cccc(-c4ccc5c(c4)[C@H](N)CC5)c3Cl)c2Cl)ccc1C1=NCCN1] | 530 |
| 624 | 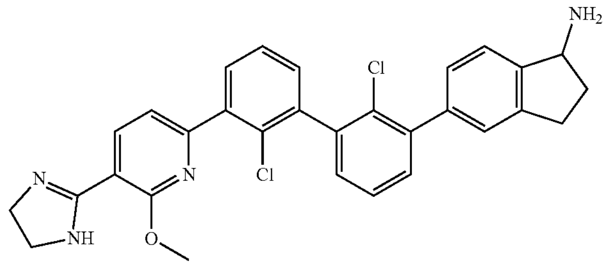 [SMILES: COc1nc(-c2cccc(-c3cccc(-c4ccc5c(c4)CCC5N)c3Cl)c2Cl)ccc1C1=NCCN1] | 529.9 |
| 625 | 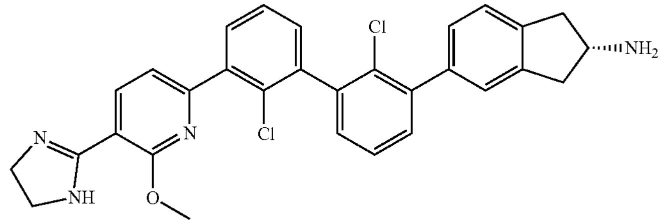 [SMILES: COc1nc(-c2cccc(-c3cccc(-c4ccc5c(c4)C[C@@H](N)C5)c3Cl)c2Cl)ccc1C1=NCCN1] | 529.6 |
| 626 | 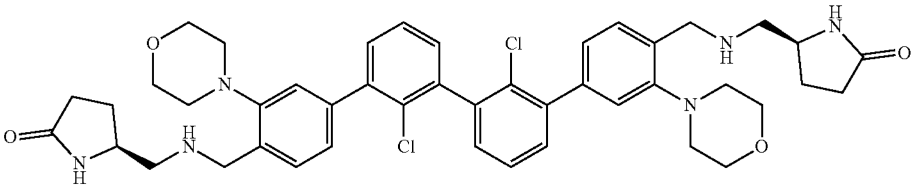 [SMILES: O=C1CC[C@@H](CNCc2ccc(-c3cccc(-c4cccc(-c5ccc(CNC[C@@H]6CCC(=O)N6)c(N6CCOCC6)c5)c4Cl)c3Cl)cc2N2CCOCC2)N1] | 797.65 |
| 627 | 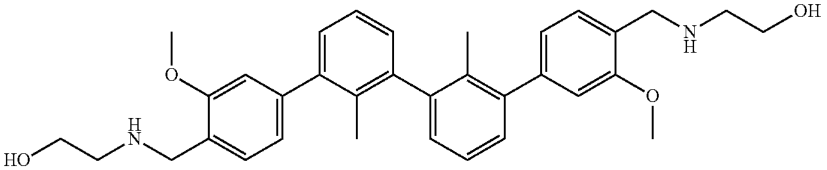 [SMILES: COc1cc(-c2cccc(-c3cccc(-c4ccc(CNCCO)c(OC)c4)c3C)c2C)ccc1CNCCO] | 541.2 |
| 629 | 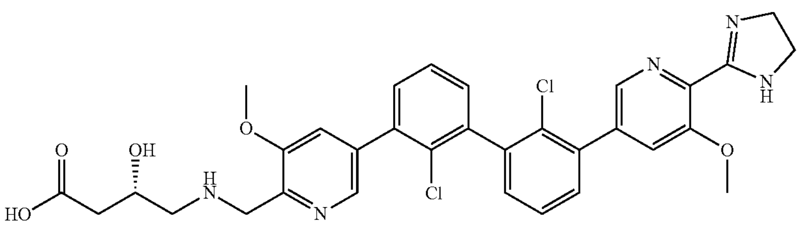 [SMILES: COc1cc(-c2cccc(-c3cccc(-c4cnc(C5=NCCN5)c(OC)c4)c3Cl)c2Cl)cnc1CNC[C@@H](O)CC(=O)O] | 636.33 |

-continued
| Example No. | Structure | ES/MS (m/z, M + H⁺) |
|---|---|---|
| 630 | 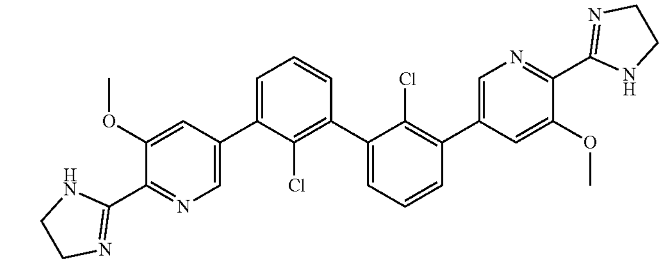 [SMILES: COc1cc(-c2cccc(-c3cccc(-c4cnc(C5=NCCN5)c(OC)c4)c3Cl)c2Cl)cnc1C1=NCCN1] | 573.27 |
| 631 | 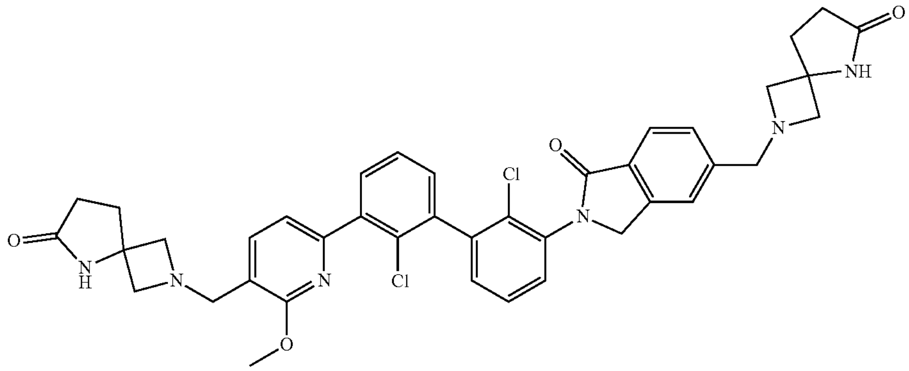 [SMILES: COc1nc(-c2cccc(-c3cccc(N4Cc5cc(CN6CC7(CCC(=O)N7)C6)ccc5C4=O)c3Cl)c2Cl)ccc1CN1CC2(CCC(=O)N2)C1] | 737.16 |
| 632 | 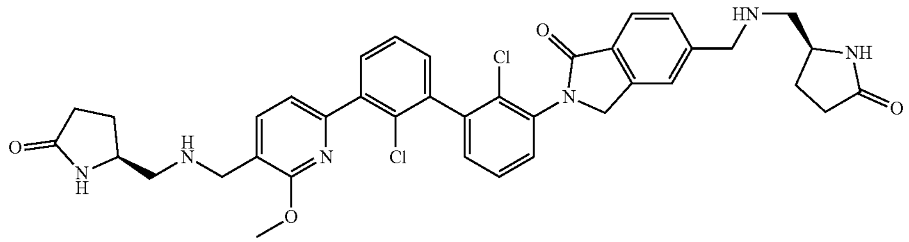 [SMILES: COc1nc(-c2cccc(-c3cccc(N4Cc5cc(CNC[C@@H]6CCC(=O)N6)ccc5C4=O)c3Cl)c2Cl)ccc1CNC[C@@H]1CCC(=O)N1] | 713.12 |
| 633 | 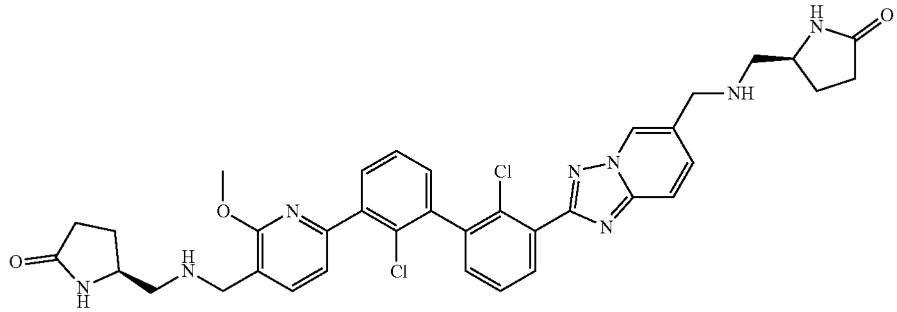 [SMILES: COc1nc(-c2cccc(-c3cccc(-c4nc5ccc(CNC[C@@H]6CCC(=O)N6)cn5n4)c3Cl)c2Cl)ccc1CNC[C@@H]1CCC(=O)N1] | 699.1 |
| 634 | 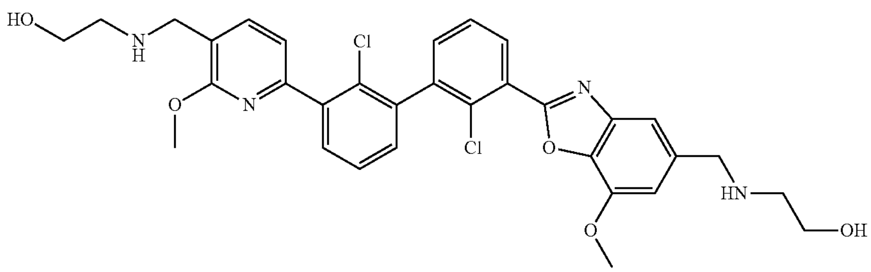 [SMILES: COc1nc(-c2cccc(-c3cccc(-c4nc5cc(CNCCO)cc(OC)c5o4)c3Cl)c2Cl)ccc1CNCCO] | 623.0 |

-continued

| Example No. | Structure | ES/MS (m/z, M + H+) |
|---|---|---|
| 635 | 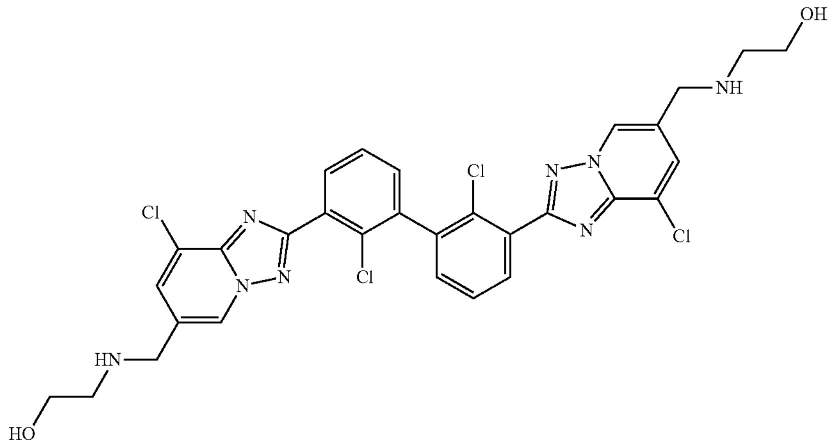 [SMILES: OCCNCc1cc(Cl)c2nc(-c3cccc(-c4cccc(-c5nc6c(Cl)cc(CNCCO)cn6n5)c4Cl)c3Cl)nn2c1] | 673.2 |
| 636 | 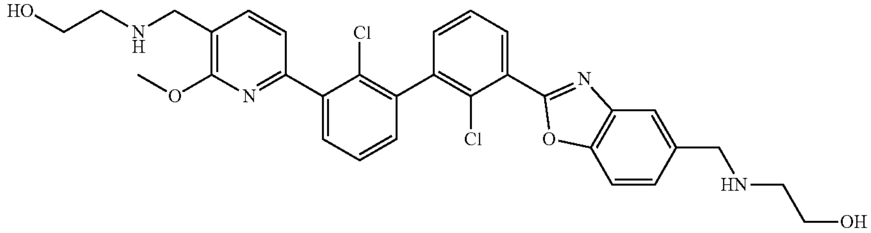 [SMILES: COc1nc(-c2cccc(-c3cccc(-c4nc5cc(CNCCO)ccc5o4)c3Cl)c2Cl)ccc1CNCCO] | 593.0 |

NMR data for select compounds is shown below.

| Example No. | NMR |
|---|---|
| 600 | 1H NMR (400 MHz, Methanol-d4) δ 8.70 (s, 1H), 8.04 (d, J = 1.4 Hz, 1H), 7.89 (d, J = 7.6 Hz, 1H), 7.74 (d, J = 1.3 Hz, 1H), 7.56 (ddd, J = 13.5, 7.5, 1.9 Hz, 2H), 7.47 (t, J = 7.6 Hz, 1H), 7.32 (d, J = 7.5 Hz, 1H), 4.51-4.28 (m, 4H), 4.10 (d, J = 18.6 Hz, 7H), 2.51-2.28 (m, 6H), 2.04-1.83 (m, 2H). |
| 601 | 1H NMR (400 MHz, Methanol-d4) δ 7.93 (d, J = 7.6 Hz, 1H), 7.84 (d, J = 7.7 Hz, 1H), 7.79 (d, J = 3.9 Hz, 1H), 7.71 (dd, J = 7.6, 1.9 Hz, 1H), 7.63-7.46 (m, 3H), 7.41 (d, J = 3.9 Hz, 1H), 7.36 (d, J = 7.6 Hz, 1H), 4.35 (dd, J = 24.8, 2.6 Hz, 4H), 4.20-4.01 (m, 7H), 3.01 (s, 1H), 2.88 (d, J = 0.8 Hz, 1H), 2.55-2.32 (m, 5H), 2.03-1.84 (m, 2H). |
| 602 | 1H NMR (400 MHz, Methanol-d4) δ 8.63 (s, 1H), 8.24 (d, J = 1.6 Hz, 1H), 7.90 (d, J = 7.7 Hz, 2H), 7.66 (dd, J = 7.7, 1.7 Hz, 1H), 7.58 (q, J = 3.8, 3.0 Hz, 2H), 7.53 (t, J = 7.7 Hz, 1H), 7.44 (ddd, J = 7.7, 4.7, 2.4 Hz, 2H), 7.38 (d, J = 7.5 Hz, 1H), 4.64-4.53 (m, 2H), 4.40-4.29 (m, 2H), 4.11 (s, 3H), 4.06 (s, 2H), 3.98 (s, 3H), 3.29-3.21 (m, 3H), 2.49-2.30 (m, 6H), 1.92 (ddd, J = 10.5, 6.5, 2.8 Hz, 2H). |
| 603 | 1H NMR (400 MHz, Methanol-d4) δ 7.98 (d, J = 8.4 Hz, 1H), 7.90 (d, J = 7.6 Hz, 1H), 7.75 (d, J = 1.5 Hz, 1H), 7.66 (dd, J = 7.7, 1.7 Hz, 1H), 7.58-7.50 (m, 4H), 7.46-7.41 (m, 2H), 7.37 (d, J = 7.5 Hz, 1H), 6.89 (d, J = 1.1 Hz, 1H), 4.74-4.66 (m, 2H), 4.35 (d, J = 2.5 Hz, 2H), 4.10 (s, 5H), 3.80 (s, 3H), 3.49-3.34 (m, 2H), 3.27 (dd, J = 6.2, 4.2 Hz, 2H), 2.52-2.31 (m, 6H), 2.02-1.86 (m, 2H). |
| 605 | 1H NMR (400 MHz, Methanol-$d_4$) δ 7.89 (d, J = 7.6 Hz, 1H), 7.80 (d, J = 8.4 Hz, 1H), 7.64 (dd, J = 7.7, 1.7 Hz, 1H), 7.53 (d, J = 8.5 Hz, 3H), 7.51-7.47 (m, 2H), 7.42 (dd, J = 7.6, 1.8 Hz, 1H), 7.38 (d, J = 7.5 Hz, 1H), 7.34 (dd, J = 6.4, 3.0 Hz, 1H), 7.31 (dd, J = 8.2, 1.5 Hz, 1H), 4.56-4.45 (m, 2H), 4.35 (d, J = 2.7 Hz, 2H), 4.11 (s, 3H), 4.09-3.97 (m, 3H), 3.89 (s, 3H), 3.25 (ddd, J = 13.4, 6.0, 3.4 Hz, 4H), 2.38 (dtd, J = 16.9, 10.8, 9.9, 6.6 Hz, 7H), 1.99-1.84 (m, 2H). |
| 611 | $^1$H (MeOH-$d_4$, 400 MHz, d): 7.87 (d, 1H); 7.63 (dd, 1H); 7.62-7.57 (m, 3H); 7.54-7.45 (m, 3H); 7.42-7.33 (m, 4H); 5.25 (t, 1H); 4.70 (t, 1H); 4.35 (m, 2H); 4.09 (s, 3H); 4.05 (m, 2H); 3.25 (m, 2H); 3.04 (dt, 1H); 2.50-2.30 (m, 2H); 2.02-1.85 (m, 2H). |
| 619 | 1H NMR (400 MHz, Methanol-d4) δ 8.61 (dd, J = 7.1, 1.0 Hz, 1H), 8.15 (s, 1H), 7.92 (d, J = 7.6 Hz, 1H), 7.76 (s, 1H), 7.69 (dd, J = 7.7, 1.7 Hz, 1H), 7.62-7.53 (m, 3H), 7.49-7.43 (m, 2H), 7.39 (d, J = 7.5 Hz, 1H), 7.25 (dd, J = 7.1, 1.7 Hz, 1H), 4.51 (d, J = 2.8 Hz, 2H), 4.37 (d, J = 2.6 Hz, 2H), 4.12 (s, 3H), 4.07 (dt, J = 13.3, 7.1 Hz, 2H), 3.32-3.21 (m, 4H), 2.52-2.28 (m, 6H), 2.05-1.84 (m, 2H). |
| 631 | 1H NMR (400 MHz, Methanol-d4) δ 7.98 (d, J = 7.9 Hz, 1H), 7.87 (d, J = 7.6 Hz, 1H), 7.77 (s, 1H), 7.72-7.40 (m, 8H), 7.37 (d, J = 7.5 Hz, 1H), 4.97 (s, 2H), 4.53 (d, J = 31.4 Hz, |

-continued

| Example No. | NMR |
|---|---|
| | 4H), 4.37 (d, J = 19.8 Hz, 8H), 4.08 (s, 3H), 3.37-3.28 (m, 2H), 2.50 (q, J = 6.4, 4.8 Hz, 4H), 2.44-2.35 (m, 4H). |
| 633 | 1H NMR (400 MHz, DMSO-d6) δ 8.15 (s, 1H), 7.91-7.80 (m, 4H), 7.61 (s, 2H), 6.55 (s, 2H), 3.75 (p, J = 6.3 Hz, 2H), 3.58 (s, 3H), 3.30 (d, J = 7.1 Hz, 4H), 2.87 (qd, J = 12.9, 5.9 Hz, 4H), 2.55 (s, 3H), 2.27-2.08 (m, 7H), 1.77 (h, J = 8.8, 7.8 Hz, 3H), 1.17 (s, 2H). |
| 634 | 1H NMR (400 MHz, DMSO-d6) δ 8.21-8.15 (m, 1H), 7.96 (d, J = 7.6 Hz, 1H), 7.72 (t, J = 5.6 Hz, 2H), 7.65-7.60 (m, 2H), 7.53 (d, J = 7.4 Hz, 1H), 7.40 (d, J = 7.5 Hz, 1H), 7.34 (s, 1H), 6.55 (s, 1H), 5.27 (s, 2H), 4.31 (s, 2H), 4.21 (s, 2H), 4.05 (s, 2H), 3.99 (s, 3H), 3.69 (dd, J = 10.7, 5.4 Hz, 3H), 3.58 (s, 2H), 3.07 (s, 2H), 2.99 (s, 2H). |
| 635 | 1H NMR (400 MHz, DMSO-d6) δ 9.21 (s, 1H), 8.98 (s, 2H), 8.11 (s, 1H), 8.03 (d, J = 7.3 Hz, 1H), 7.65 (dd, J = 14.8, 7.5 Hz, 3H), 6.55 (s, 1H), 5.15 (s, 1H), 4.33 (s, 2H), 3.67 (s, 2H), 3.57 (d, J = 2.0 Hz, 3H), 3.05 (s, 2H), 2.87 (s, 2H). |
| 636 | 1H NMR (400 MHz, DMSO-d6) δ 8.96 (s, 2H), 8.83 (s, 2H), 8.19 (dd, J = 6.1, 3.4 Hz, 1H), 8.07 (s, 1H), 7.95 (dd, J = 10.3, 8.1 Hz, 2H), 7.72 (dd, J = 6.7, 3.7 Hz, 3H), 7.68-7.59 (m, 2H), 7.53 (dd, J = 7.5, 1.7 Hz, 1H), 7.40 (d, J = 7.5 Hz, 1H), 6.55 (s, 1H), 5.29 (s, 2H), 4.36 (s, 2H), 4.22 (s, 2H), 3.99 (s, 3H), 3.70 (dt, J = 12.1, 5.1 Hz, 4H), 3.05 (d, J = 33.0 Hz, 4H). |

Intermediate 63: 6-chloro-3-(4,5-dihydro-1H-imidazol-2-yl)-2-methoxypyridine

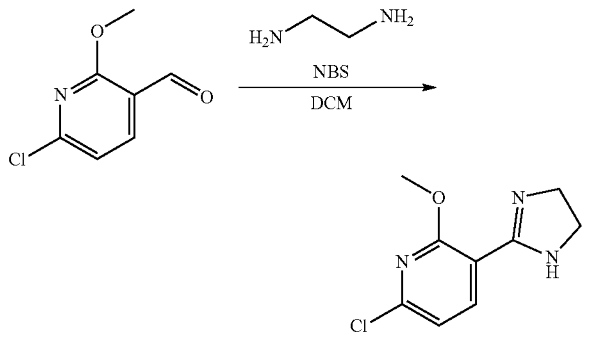

To a solution of aldehyde (3.5 g, 20.4 mmol) in 60 mL DCM at 0° C. was added ethylenediamine (1.50 mL, 22.44 mmol) dropwise. The solution was stirred at 0° C. for 30 minutes, then N-bromosuccinimide (3.99 g, 22.44 mmol) was added in one portion, and the reaction mixture was stirred for 16 hours with gradual warming to ambient temperature. Reaction was taken up in DCM and stirred vigorously with 1:1 sat. sodium thiosulfate and sat. sodium carbonate for 15 min. The organic later was dried with $MgSO_4$, filtered and concentrated to provide 6-chloro-3-(4,5-dihydro-1H-imidazol-2-yl)-2-methoxypyridine.

Example 637: (S)-4-(((5-chloro-6-(((S)-4-(2-chloro-4'-(2-((2-hydroxyethyl)amino)ethoxy)-[1,1'-biphenyl]-3-yl)-2,3-dihydro-1H-inden-1-yl)oxy)-2-((5-(methylsulfonyl)pyridin-3-yl)methoxy)pyridin-3-yl)methyl)amino)-3-hydroxybutanoic acid

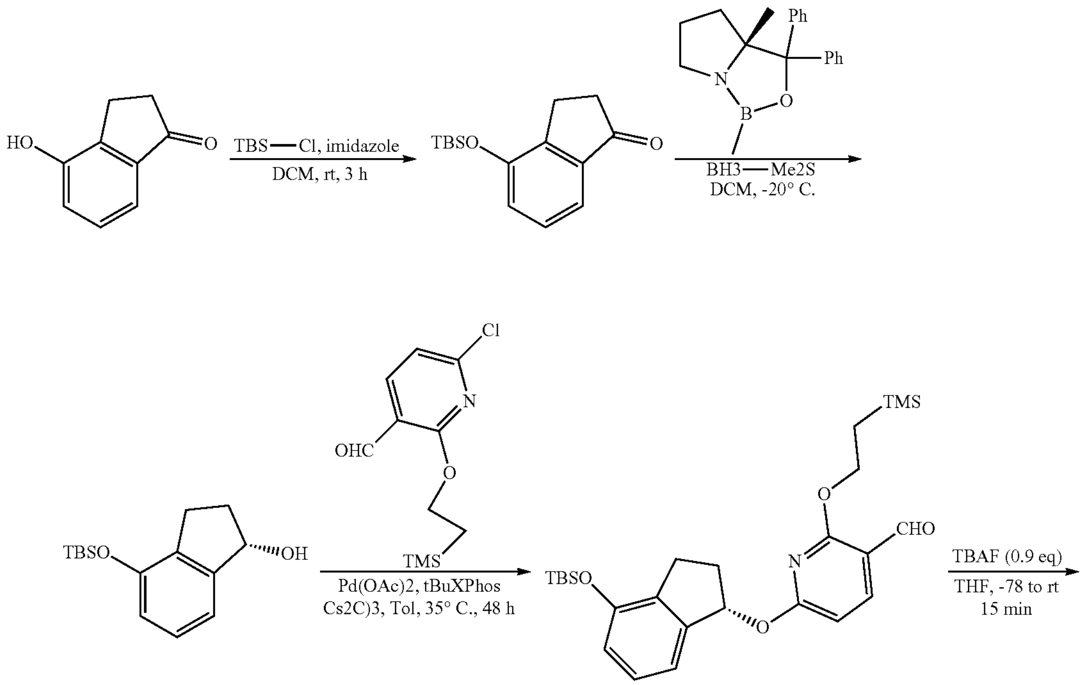

-continued
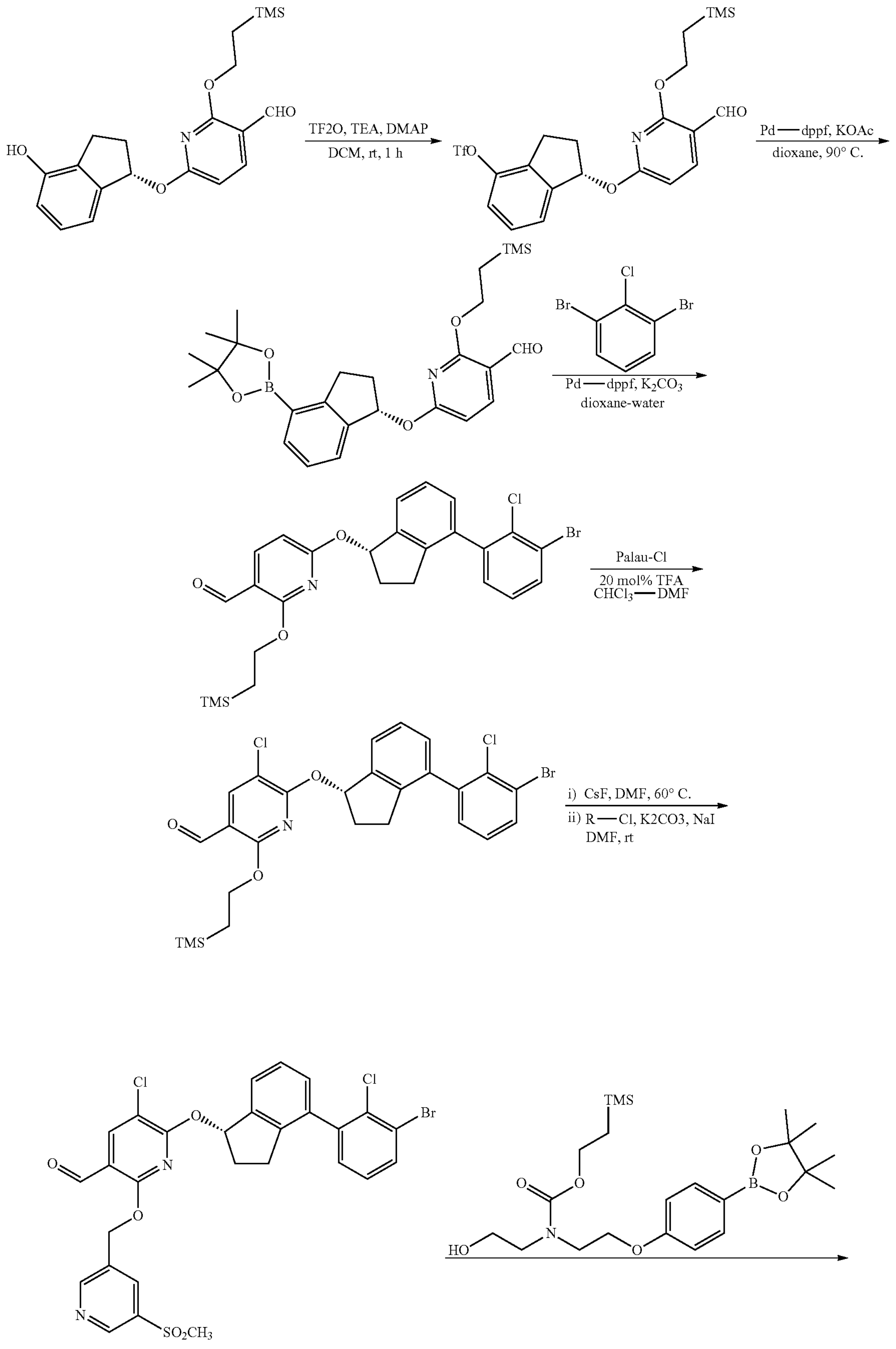

-continued

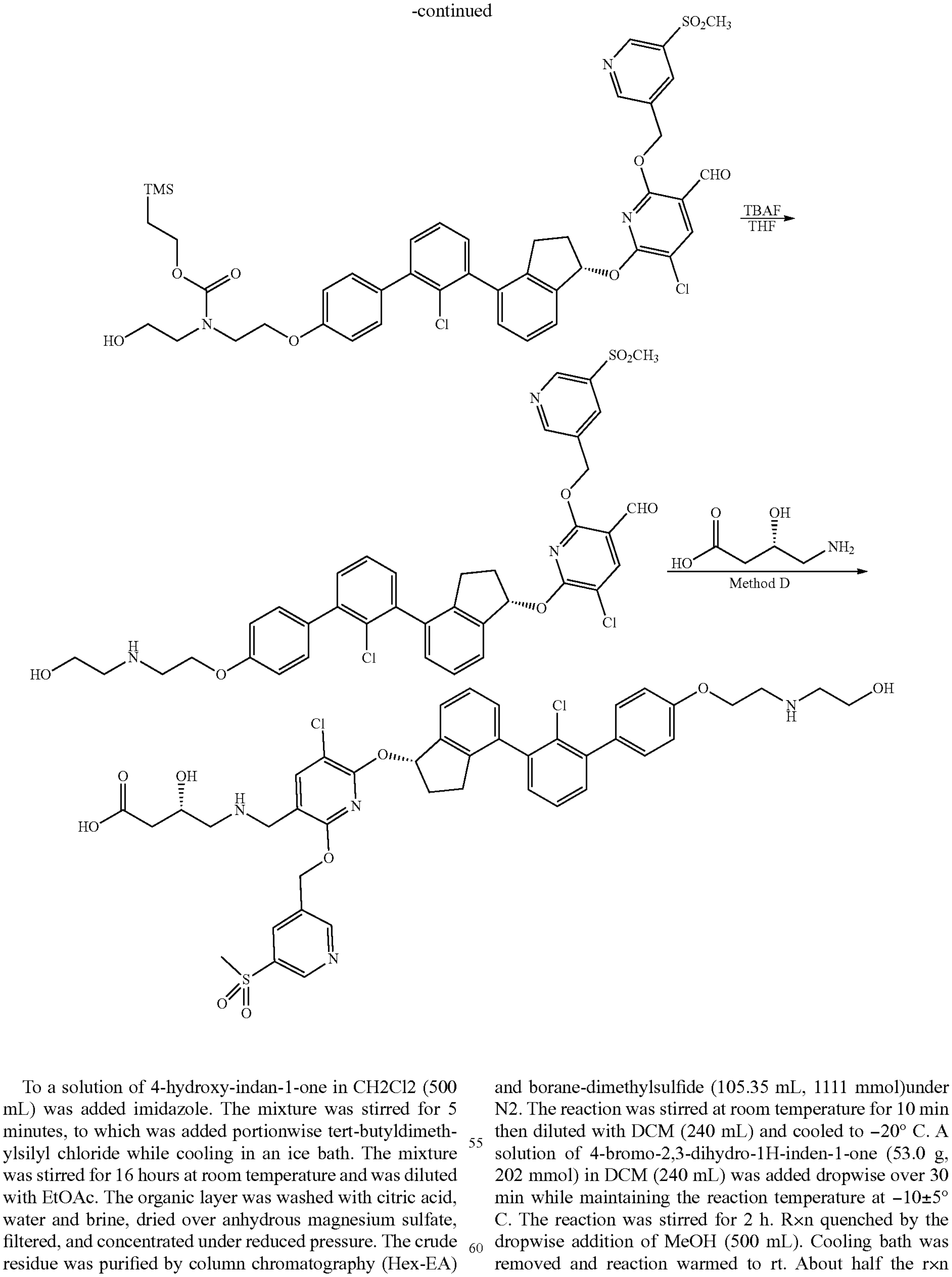

To a solution of 4-hydroxy-indan-1-one in CH2Cl2 (500 mL) was added imidazole. The mixture was stirred for 5 minutes, to which was added portionwise tert-butyldimethylsilyl chloride while cooling in an ice bath. The mixture was stirred for 16 hours at room temperature and was diluted with EtOAc. The organic layer was washed with citric acid, water and brine, dried over anhydrous magnesium sulfate, filtered, and concentrated under reduced pressure. The crude residue was purified by column chromatography (Hex-EA) to give 4-(tert-butyl-dimethyl-silanyloxy)-indan-1-one. 1H NMR (400 MHz, CDCl3): δ 7.27 (d, 1H, J=7.5 Hz), 7.15 (t, 1H, J=7.5 Hz), 6.89 (d, 1H, J=7.5 Hz), 2.93 (t, 2H, J=5.7 Hz), 2.57 (t, 2H, J=5.7 Hz), 0.81 (s, 9H), 0.15 (s, 6H).

To a 3000 mL rbf was added (R)-(+)-2-methyl-CBS-oxazaborolidine (8.397 g, 30.29 mmol), Toluene (30 mL) and borane-dimethylsulfide (105.35 mL, 1111 mmol)under N2. The reaction was stirred at room temperature for 10 min then diluted with DCM (240 mL) and cooled to −20° C. A solution of 4-bromo-2,3-dihydro-1H-inden-1-one (53.0 g, 202 mmol) in DCM (240 mL) was added dropwise over 30 min while maintaining the reaction temperature at −10±5° C. The reaction was stirred for 2 h. Rxn quenched by the dropwise addition of MeOH (500 mL). Cooling bath was removed and reaction warmed to rt. About half the rxn volume was distilled off using a short-path distillation apparatus. All remaining solvent was then evaporated under reduced pressure to give a solid which was purified by silica gel column chromatography eluting with EA-Hex to provide (S)-4-((tert-butyldimethylsilyl)oxy)-2,3-dihydro-1H-inden-1-ol. ES/MS m/z: [M−OH]+=247. 1H NMR (400 MHz, Chloroform-d) δ 7.13 (dt, J=15.3, 0.8 Hz, 1H), 7.02 (d, J=7.4 Hz, 1H), 6.70 (d, J=8.0 Hz, 1H), 5.23 (t, J=6.0 Hz, 1H), 3.00 (ddd, J=16.2, 8.6, 4.7 Hz, 1H), 2.79-2.66 (m, 1H), 2.46 (dddd, J=13.1, 8.3, 6.9, 4.7 Hz, 1H), 1.92 (dddd, J=13.6, 8.6, 6.3, 5.2 Hz, 1H), 1.00 (s, 9H), 0.20 (d, J=1.8 Hz, 6H).

A solution of (S)-4-((tert-butyldimethylsilyl)oxy)-2,3-dihydro-1H-inden-1-ol (6.0 g, 22.7 mmol) and 6-chloro-2-(2-(trimethylsilyl)ethoxy)nicotinaldehyde (11.7 g, 45.4 mmol), in toluene (40 mL) was degassed by vigorously bubbling N2 thru solution for 10 min. Then $Pd(OAc)_2$ (1.02 g, 4.54 mmol), t-BuXPhos (3.85 g, 9.07 mmol) and cesium carbonate (29.5 g, 90.8 mmol) were added and the bubbling continued for 5 min more. The reaction was then stirred at 35 C for 48 h under N2. R×n was cooled to rt and diluted with DCM. Filtered thru celite and loaded directly on silica gel column, eluting with Hex-DCM to provide (S)-6-((4-((tert-butyldimethylsilyl)oxy)-2,3-dihydro-1H-inden-1-yl)oxy)-2-(2-(trimethylsilyl)ethoxy)nicotinaldehyde. 1H NMR (400 MHz, Chloroform-d) δ 10.29 (d, J=0.8 Hz, 1H), 8.92 (d, J=2.1 Hz, 1H), 8.86 (d, J=2.0 Hz, 1H), 8.16-8.04 (m, 2H), 7.10 (s, 1H), 7.10 (dt, J=15.5, 0.8 Hz, 1H), 6.93 (d, J=7.5 Hz, 1H), 6.79-6.72 (m, 1H), 6.50-6.41 (m, 2H), 5.68-5.53 (m, 2H), 4.12 (q, J=7.1 Hz, 1H), 3.07 (ddd, J=16.3, 8.8, 5.2 Hz, 1H), 2.86 (ddd, J=16.3, 8.6, 5.5 Hz, 1H), 2.51 (dddd, J=13.9, 8.6, 7.1, 5.3 Hz, 1H), 2.14 (dddd, J=13.9, 8.7, 5.5, 4.4 Hz, 1H), 2.04 (s, 1H), 1.32-1.19 (m, 2H), 1.01 (s, 9H), 0.23 (s, 6H).

(S)-6-((4-((tert-butyldimethylsilyl)oxy)-2,3-dihydro-1H-inden-1-yl)oxy)-2-(2-(trimethylsilyl)ethoxy)nicotinaldehyde (4.69 g, 9.66 mmol) was taken up in 50 mL THF and cooled to -78 C. TBAF (9.66 mL, 9.66 mmol) was added dropwise and the reaction allowed to warm up to 0 C over 30 min, providing a dark orange solution. AcOH (0.552 mL, 9,655 mmol) was added dropwise, removing most of the color. Diluted with EtOAc and pH 5 citrate buffer. Organic layer was dried ($Na2SO_4$) and conc. Purification by silica gel chromatography provided (S)-6-((4-hydroxy-2,3-dihydro-1H-inden-1-yl)oxy)-2-(2-(trimethylsilyl)ethoxy)nicotinaldehyde. 1H NMR (400 MHz, Chloroform-d) δ 10.23 (d, J=0.8 Hz, 1H), 8.04 (d, J=8.4 Hz, 1H), 7.14 (t, J=7.7 Hz, 1H), 7.07-6.96 (m, 1H), 6.78 (dd, J=7.9, 1.0 Hz, 1H), 6.53 (dd, J=7.1, 4.2 Hz, 1H), 6.34 (dd, J=8.4, 0.9 Hz, 1H), 5.20 (s, 1H), 4.66-4.57 (m, 2H), 3.10 (ddd, J=14.5, 8.7, 5.4 Hz, 1H), 2.89 (ddd, J=15.8, 8.7, 5.2 Hz, 1H), 2.66 (dddd, J=14.0, 8.6, 7.0, 5.4 Hz, 1H), 2.26 (dddd, J=13.9, 8.7, 5.2, 4.2 Hz, 1H), 0.91 (s, 2H), 0.08 (s, 9H).

A solution of (S)-6-((4-hydroxy-2,3-dihydro-1H-inden-1-yl)oxy)-2-(2-(trimethylsilyl)ethoxy)nicotinaldehyde (5.00 g, 13 mmol) in 55 mL DCM was treated with pyridine (2.76 mL, 34 mmol), DMAP (164 mg, 1.3 mmol) and TEA (3.75 mL, 27 mmol) was cooled to −78 C and treated dropwise with Tf2O (2.50 mL, 15 mmol). Stirred for 15 min, then allowed to warm to rt. After 1 h the reaction was diluted with EtOAc, washed with citric acid soln, dried with $Na2SO_4$ and concentrated. Purification by silica chromatography (hex-DCM) provided (S)-1-((5-formyl-6-(2-(trimethylsilyl)ethoxy)pyridin-2-yl)oxy)-2,3-dihydro-1H-inden-4-yl trifluoromethanesulfonate (6.42 g, 94% yield). [M+H]=503.7. 1H NMR (400 MHz, Chloroform-d) δ 10.25 (d, J=0.8 Hz, 1H), 8.07 (d, J=8.3 Hz, 1H), 7.46 (d, J=7.5 Hz, 1H), 7.33 (t, J=7.8 Hz, 1H), 7.23 (d, J=8.1 Hz, 1H), 6.56 (dd, J=7.1, 5.0 Hz, 1H), 6.37 (dd, J=8.4, 0.8 Hz, 1H), 4.60 (td, J=8.2, 1.2 Hz, 2H), 3.27 (ddd, J=16.6, 8.9, 5.1 Hz, 1H), 3.12-2.99 (m, 1H), 2.72 (dddd, J=13.7, 8.5, 7.1, 5.1 Hz, 1H), 2.29 (dddd, J=13.8, 8.8, 6.1, 4.9 Hz, 1H), 1.55 (s, 1H), 1.24-1.18 (m, 2H), 0.07 (s, 9H). $^{19}F$ NMR δ −74.10.

A solution of (S)-6-((4-hydroxy-2,3-dihydro-1H-inden-1-yl)oxy)-2-(2-(trimethylsilyl)ethoxy)nicotinaldehyde (6.42 g, 0.13 mmol), 4,4,4',4',5,5,5',5'-octamethyl-2,2'-bi(1,3,2-dioxaborolane) (3.89 g, 15 mmol), Pd-dppf (0.932 g, 1.27 mmol) and KOAc (3.75 g, 38 mmol) in 55 mL dioxane was stirred at 90 C overnight. Reaction was diluted with EtOAc, filtered thru celite and concentrated. Purification of the filtrate derived material by silica chromatography (DCM-hexanes) provided (S)-6-((4-(4,4,5,5-tetramethyl-1,3,2-dioxaborolan-2-yl)-2,3-dihydro-1H-inden-1-yl)oxy)-2-(2-(trimethylsilyl)ethoxy)nicotinaldehyde. 1H NMR (400 MHz, Chloroform-d) δ 10.24 (d, J=0.9 Hz, 1H), 8.03 (d, J=8.3 Hz, 1H), 7.78 (dd, J=7.3, 1.3 Hz, 1H), 7.53 (d, J=7.6 Hz, 1H), 7.23 (d, J=7.4 Hz, 1H), 6.51 (dd, J=7.1, 4.3 Hz, 1H), 6.33 (dd, J=8.3, 0.9 Hz, 1H), 4.66-4.57 (m, 2H), 3.36 (ddd, J=17.2, 8.7, 5.7 Hz, 1H), 3.15 (ddd, J=17.2, 8.7, 5.6 Hz, 1H), 2.60 (dddd, J=14.1, 8.6, 7.1, 5.6 Hz, 1H), 2.26-2.13 (m, 1H), 1.34 (s, 12H), 1.31-1.18 (m, 2H), 0.07 (s, 9H).

A solution of (S)-6-((4-(4,4,5,5-tetramethyl-1,3,2-dioxaborolan-2-yl)-2,3-dihydro-1H-inden-1-yl)oxy)-2-(2-(trimethylsilyl)ethoxy)nicotinaldehyde (3.20 g, 6.71 mmol), 1,3-dibromo-2-chlorobenzene (5,44 g, 20.1 mmol), Pd-dppf (0.490 g, 0.67 mmol) and $K_2CO_3$ (2.34 g, 17 mmol) in 60 mL dioxane and 6 mL water was stirred at 90 C for 5 h. Reaction was diluted with EtOAc, dried with $MgSO_4$ and filtered thru celite and conc. Purification of the filtrate derived material by silica chromatography (DCM-hexanes) provided (S)-6-((4-(3-bromo-2-chlorophenyl)-2,3-dihydro-1H-inden-1-yl)oxy)-2-(2-(trimethylsilyl)ethoxy)nicotinaldehyde. 1H NMR (400 MHz, Chloroform-d) δ 10.24 (d, J=0.8 Hz, 1H), 8.06 (d, J=8.4 Hz, 1H), 7.66 (dd, J=7.7, 1.9 Hz, 1H), 7.50 (d, J=7.6 Hz, 1H), 7.33 (t, J=7.6 Hz, 1H), 7.26-7.13 (m, 3H), 6.59 (d, J=16.5 Hz, 1H), 6.38 (s, 1H), 4.62 (t, J=8.3 Hz, 2H), 2.82 (tq, J=16.5, 8.5, 6.8 Hz, 1H), 2.68-2.59 (m, 2H), 2.24-2.15 (m, 1H), 1.30-1.18 (m, 3H), 0.07 (s, 9H).

A solution of (S)-6-((4-(3-bromo-2-chlorophenyl)-2,3-dihydro-1H-inden-1-yl)oxy)-2-(2-(trimethylsilyl)ethoxy)nicotinaldehyde (1.31 g, 2.41 mmol) in 6 mL Chloroform and 3 mL DMF was treated with Palau-Cl (2-chloro-1,3-bis(methoxycarbonyl)guanidine (Baran CBMG Reagent) 631 mg, 3.01 mmol) and TFA (37 uL, 0.48 mmol) as a 10% soln in DMF. The reaction was stirred for 16h at rt, then diluted with DCM and treated with 10 mL sat thiosulfate and 20 mL $NaHCO_3$. After stirring vigorously for 10 min, the organic layer was separated, dried with MgSO4, filtered and concentrated. Purification by column chromatography (ISCO, elution with DCM-hexanes) provided (S)-6-((4-(3-bromo-2-chlorophenyl)-2,3-dihydro-1H-inden-1-yl)oxy)-5-chloro-2-(2-(trimethylsilyl)ethoxy)nicotinaldehyde. 120 mg of starting material was also obtained. 1H NMR (400 MHz, Chloroform-d) δ 10.20 (s, 1H), 8.09 (s, 1H), 7.66 (dd, J=7.7, 1.9 Hz, 1H), 7.51 (d, J=7.5 Hz, 1H), 7.34 (t, J=7.6 Hz, 1H), 7.29-7.14 (m, 1H), 7.20 (s, 2H), 6.58 (d, J=22.9 Hz, 1H), 4.61 (t, J=8.3 Hz, 2H), 2.94-2.77 (m, 2H), 2.69 (m, 2H), 2.28-2.20 (m, 1H), 1.27-1.17 (m, 2H), 0.07 (s, 9H).

A solution of (S)-6-((4-(3-bromo-2-chlorophenyl)-2,3-dihydro-1H-inden-1-yl)oxy)-5-chloro-2-(2-(trimethylsilyl)ethoxy)nicotinaldehyde (500 mg, 0.86 mmol) in 6 mL DMF was treated with CsF (524 mg, 3.45 mmol) and stirred for 1 h at 60° C. Cooled to 0 C and treated with $K_2CO_3$ (357 mg, 2.6 mmol), 3-(chloromethyl)-5-(methylsulfonyl)pyridine hydrochloride (251 mg, 1.04 mmol) and NaI (130 mg, 0.86 mmol). Allowed to warm to rt and stir overnight. The reaction was partitioned between EtOAc and water. Organic layer was washed with 2% LiCl, dried with sodium sulfate, filtered and conc. Purification by column chromatography (ISCO, elution with EtOAc-hexanes) provided (S)-6-((4-(3-bromo-2-chlorophenyl)-2,3-dihydro-1H-inden-1-yl)oxy)-5-chloro-2-((5-(methylsulfonyl)pyridin-3-yl)methoxy)nicotinaldehyde. LCMS-ESI+ (m/z): [M+H]+ calcd for C28H22BrCl2N2O5S: 648.97; found: 648.94.

A solution of (S)-6-((4-(3-bromo-2-chlorophenyl)-2,3-dihydro-1H-inden-1-yl)oxy)-5-chloro-2-((5-(methylsulfonyl)pyridin-3-yl)methoxy)nicotinaldehyde (291 mg, 0.45 mmol) in 5 mL DMF and 0.5 mL H2O was treated with 2-(trimethylsilyl)ethyl (2-hydroxyethyl)(2-(4-(4,4,5,5-tetramethyl-1,3,2-dioxaborolan-2-yl)phenoxy)ethyl)carbamate (233 mg, 0.52 mmol), K2CO3 (186 mg, 1.4 mmol) and Pd-dppf (33 mg, 0.045 mmol) and stirred for 16 h at 80° C. Cooled to rt and diluted with EtOAc, dried with sodium sulfate, filtered and conc. Purification by column chromatography (ISCO, elution with EtOAc-hexanes) provided 2-(trimethylsilyl)ethyl (S)-(2-((2'-chloro-3'-(1-((3-chloro-5-formyl-6-((5-(methylsulfonyl)pyridin-3-yl)methoxy)pyridin-2-yl)oxy)-2,3-dihydro-1H-inden-4-yl)-[1,1'-biphenyl]-4-yl)oxy)ethyl)(2-hydroxyethyl)carbamate. LCMS-ESI+ (m/z): [M+H]+ calcd for C44H48Cl2N3O9SSi: 892.22; found: 891.83.

A solution of 2-(trimethylsilyl)ethyl (S)-(2-((2'-chloro-3'-(1-((3-chloro-5-formyl-6-((5-(methylsulfonyl)pyridin-3-yl)methoxy)pyridin-2-yl)oxy)-2,3-dihydro-1H-inden-4-yl)-[1,1'-biphenyl]-4-yl)oxy)ethyl)(2-hydroxyethyl)carbamate (290 mg, 0.32 mmol) in 2 mL THF was treated with 1.0 M TBAF in THF (0.487 mL, 0.487 mmol) and stirred for 18 h at 20° C. The reaction was partitioned between EtOAc and water. Organic layer was washed with water, dried with sodium sulfate, filtered and concentrated to provide (S)-5-chloro-6-((4-(2-chloro-4'-(2-((2-hydroxyethyl)amino)ethoxy)-[1,1'-biphenyl]-3-yl)-2,3-dihydro-1H-inden-1-yl)oxy)-2-((5-(methylsulfonyl)pyridin-3-yl)methoxy)nicotinaldehyde. LCMS-ESI+ (m/z): $[M+H]^+$ calcd for C38H36Cl2N3O7S: 748.12; found: 748.03.

(S)-4-(((5-chloro-6-(((S)-4-(2-chloro-4'-(2-((2-hydroxyethyl)amino)ethoxy)-[1,1'-biphenyl]-3-yl)-2,3-dihydro-1H-inden-1-yl)oxy)-2-((5-(methylsulfonyl)pyridin-3-yl)methoxy)pyridin-3-yl)methyl)amino)-3-hydroxybutanoic acid was prepared from (S)-5-chloro-6-((4-(2-chloro-4'-(2-((2-hydroxyethyl)amino)ethoxy)-[1,1'-biphenyl]-3-yl)-2,3-dihydro-1H-inden-1-yl)oxy)-2-((5-(methylsulfonyl)pyridin-3-yl)methoxy)nicotinaldehyde using general reductive amination procedure D. 1H NMR (400 MHz, Methanol-d4) δ 9.03 (s, 2H), 8.50 (s, 1H), 7.90 (s, 1H), 7.54 (s, 4H), 7.45 (t, J=7.5 Hz, 1H), 7.41-7.32 (m, 2H), 7.29-7.18 (m, 3H), 6.52 (s, 1H), 5.70 (s, 2H), 4.29 (s, 2H), 4.18 (s, 2H), 3.27 (d, J=3.1 Hz, 1H), 3.17 (d, J=5.5 Hz, 3H), 3.07 (dd, J=12.7, 9.8 Hz, 1H), 2.95-2.87 (m, 2H), 2.76 (s, 1H), 2.57 (d, J=6.3 Hz, 3H), 2.10 (s, 1H). LCMS-ESI+ (m/z): [M+H]+ calcd for $C_{42}H_{45}Cl_2N_4O_9S$: 851.22; found: 851.00.

Example 638: (S)-2-(((2-(2-chloro-3-(1-((3-chloro-5-(((2-hydroxyethyl)amino)methyl)-6-methoxypyridin-2-yl)oxy)-2,3-dihydro-1H-inden-4-yl)phenyl)-[1,2,4]triazolo[1,5-a]pyridin-7-yl)methyl)amino)ethan-1-ol

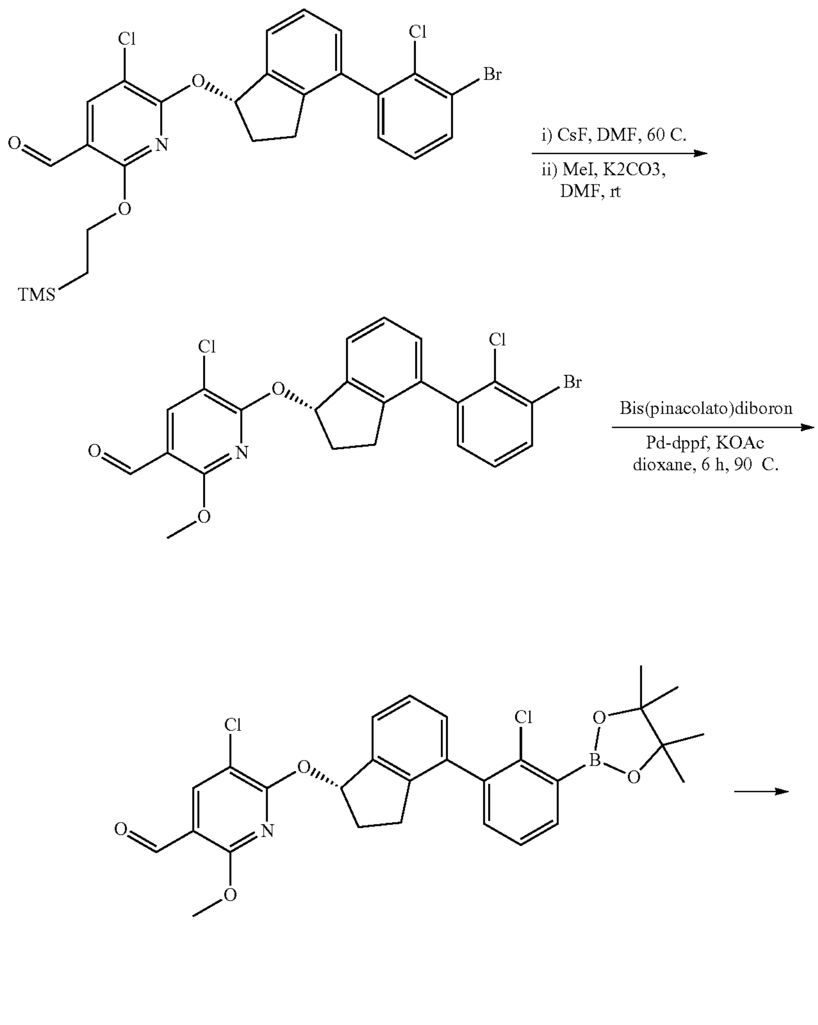

-continued

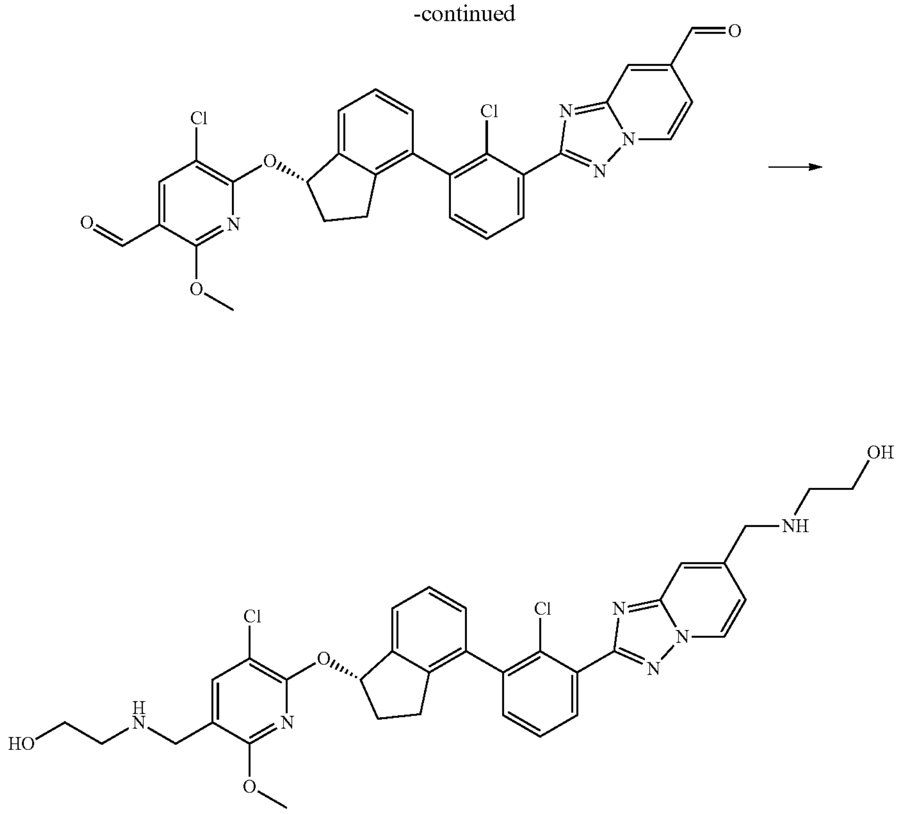

A solution of (S)-6-((4-(3-bromo-2-chlorophenyl)-2,3-dihydro-1H-inden-1-yl)oxy)-5-chloro-2-(2-(trimethylsilyl)ethoxy)nicotinaldehyde (400 mg, 0.69 mmol) in 3 mL DMF was treated with CsF (419 mg, 2.76 mmol) and stirred for 1 h at 60° C. Cooled to 0 C and treated with K2CO3 (286 mg, 2.07 mmol) and methyl iodide (64 μL, 1.04 mmol). Allowed to warm to rt and stir for 2 h. The reaction was partitioned between EtOAc and water. Organic layer was washed with 2% LiCl, dried with sodium sulfate, filtered and conc. Purification by column chromatography (ISCO, elution with EtOAc-hexanes) (S)-6-((4-(3-bromo-2-chlorophenyl)-2,3-dihydro-1H-inden-1-yl)oxy)-5-chloro-2-methoxynicotinaldehyde. LCMS-ESI+ (m/z): [M+H]+ calcd for $C_{22}H_{17}BrCl_2NO_3$: 491.97; found: 491.83.

A solution of (S)-6-((4-(3-bromo-2-chlorophenyl)-2,3-dihydro-1H-inden-1-yl)oxy)-5-chloro-2-methoxynicotinaldehyde (357 mg, 0.72 mmol) in 5 mL dioxane was treated with inacoldiboron (221 mg, 0.87 mmol), Pd-dppf (53 mg, 0.073 mmol) and KOAc (213 mg, 2.2 mmol) and heated at 90 C for 1h. The reaction was diluted with EtOAc and filtered. Purification by column chromatography (ISCO, elution with EtOAc-hexanes) (S)-5-chloro-6-((4-(2-chloro-3-(4,4,5,5-tetramethyl-1,3,2-dioxaborolan-2-yl)phenyl)-2,3-dihydro-1H-inden-1-yl)oxy)-2-methoxynicotinaldehyde. LCMS-ESI+ (m/z): [M+H]+ calcd for C28H28BCl2NO5: 540.14; found: 540.32.

A solution of (S)-5-chloro-6-((4-(2-chloro-3-(4,4,5,5-tetramethyl-1,3,2-dioxaborolan-2-yl)phenyl)-2,3-dihydro-1H-inden-1-yl)oxy)-2-methoxynicotinaldehyde (45 mg, 0.083 mmol), 2-bromo-[1,2,4]triazolo[1,5-a]pyridine-7-carbaldehyde (26 mg, 0.115 mmol), [1,1'-Bis(diphenylphosphino)ferrocene]palladium(II) dichloride (7 mg, 0.009 mmol) and sodium carbonate (120 μL, 0.24 mmol, 2M solution in water). The reaction mixture was heated in the microwave at 110° C. for 45 min. After cooling to room temperature, the reaction mixture was diluted with ethyl acetate and washed with water and brine. The organic layer was dried over sodium sulfate and filtered. The filtrate was concentrated and purified by ISCO silica gel chromatography to give (S)-2-(2-chloro-3-(1-((3-chloro-5-formyl-6-methoxypyridin-2-yl)oxy)-2,3-dihydro-1H-inden-4-yl)phenyl)-[1,2,4]triazolo[1,5-a]pyridine-7-carbaldehyde.

Ethanolamine (15 μL, 0.25 mmol) was first dissolved in dimethyl sulfoxide (3 mL) and acetic acid (0.6 mL). After stirring for 10 min, (S)-2-(2-chloro-3-(1-((3-chloro-5-formyl-6-methoxypyridin-2-yl)oxy)-2,3-dihydro-1H-inden-4-yl)phenyl)-[1,2,4]triazolo[1,5-a]pyridine-7-carbaldehyde (17 mg, 0.03 mmol) dissolved in dimethyl sulfoxide (1 mL) was then added slowly dropwise. The reaction mixture was stirred at rt for 4h before sodium triacetoxyborohydride (57 mg, 0.27 mmol) was added. After 1 h, the reaction was quenched by adding 400 μL of trifluoroacetic acid. Purification on reversed-phase HPLC provided(S)-2-(((2-(2-chloro-3-(1-((3-chloro-5-(((2-hydroxyethyl)amino)methyl)-6-methoxypyridin-2-yl)oxy)-2,3-dihydro-1H-inden-4-yl)phenyl)-[1,2,4]triazolo[1,5-a]pyridin-7-yl)methyl)amino)ethan-1-ol. $^1H$ NMR (400 MHz, DMSO-$d_6$) δ 9.15 (d, J=7.1 Hz, 2H), 8.70 (s, 2H), 8.07 (d, J=1.5 Hz, 1H), 7.99 (s, 1H), 7.94 (dd, J=7.3, 2.2 Hz, 1H), 7.60 (d, J=7.2 Hz, 1H), 7.50 (s, 1H), 7.44-7.37 (m, 2H), 7.31 (dd, J=7.6, 1.2 Hz, 1H), 6.64 (s, 1H), 5.30 (d, J=21.2 Hz, 2H), 4.39 (s, 2H), 4.09 (s, 2H), 4.02 (s, 3H), 3.68 (dt, J=9.3, 4.6 Hz, 3H), 3.04 (d, J=19.4 Hz, 4H), 2.93-2.83 (m, 1H), 2.79-2.66 (m, 2H), 2.11 (d, J=19.3 Hz, 1H). ES/MS (m/z, M+$H^+$): 648.9.

Example 639: (3S,3'S)-4,4'-((((((1R,1'R,2R,2'R)-2,2'-difluoro-2,2',3,3'-tetrahydro-1H,1'H-[4,4'-biindene]-1,1'-diyl)bis(oxy))bis(5-chloro-2-methoxy-pyridine-6,3-diyl))bis(methylene))bis(azanediyl))bis(3-hydroxybutanoic acid)
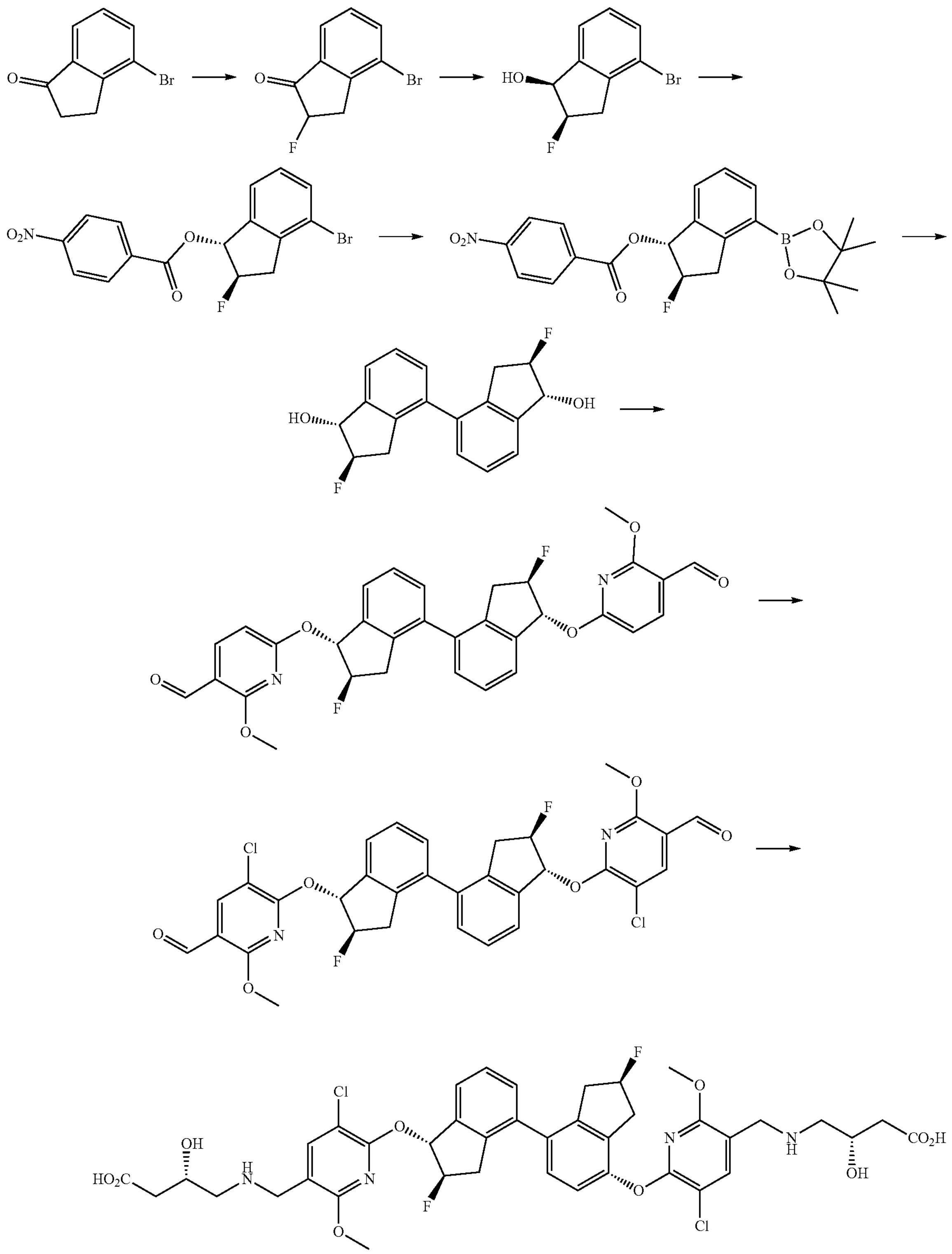

A stirred mixture of 4-bromo-2,3-dihydro-1H-inden-1-one (3.00 g, 14.2 mmol), 1-(chloromethyl)-4-fluoro-1,4-diazabicyclo[2.2.2]octane-1,4-diium tetrafluoroborate (6.04 g, 17.1 mmol), and sulfuric acid (75.8 μL, 1.42 mmol) in methanol (30 mL) was heated to 62° C. After 22 h, the resulting mixture was cooled to room temperature. Ethyl acetate (50 mL) and diethyl ether (200 mL) were added. The organic layer was washed with water (200 mL), was dried over anhydrous magnesium sulfate, was filtered, and was concentrated under reduced pressure. The residue was purified by flash column chromatography on silica gel (0 to 10% ethyl acetate in hexanes) to give 4-bromo-2-fluoro-2,3-dihydro-1H-inden-1-one.

[N-[(1R,2R)-2-(Amino-κN)-1,2-diphenylethyl]-4-methylbenzenesulfonamidato-κN]chloro[(1,2,3,4,5,6-η)-1-methyl-4-(1-methylethyl)benzene]-ruthenium (21 mg, 0.033 mmol) was added to a stirred mixture of 4-bromo-2-fluoro-2,3-dihydro-1H-inden-1-one (750 mg, 3.27 mmol), formic acid (890 μL, 24 mmol), triethylamine (2.7 mL, 20 mmol), and dichloromethane (400 μL) at room temperature. After 24 h, diethyl ether (50 mL) was added. The organic layer was washed with saturated aqueous sodium bicarbonate solution (2×30 mL), was dried over anhydrous magnesium sulfate, was filtered, and was concentrated under reduced pressure. The residue was purified by flash column chromatography on silica gel (0 to 30% ethyl acetate in hexanes) to give (1S,2R)-4-bromo-2-fluoro-2,3-dihydro-1H-inden-1-ol.

Diisopropyl azodicarboxylate (572 μL, 2.95 mmol) was added over 2 min via syringe to a stirred mixture of (1S,2R)-4-bromo-2-fluoro-2,3-dihydro-1H-inden-1-ol (455 mg, 1.97 mmol), 4-nitrobenzoic acid (494 mg, 2.95 mmol), and triphenylphosphine (826 mg, 3.15 mmol) in tetrahydrofuran (10 mL) at 0° C. After 5 min, the resulting mixture was warmed to room temperature. After 13 h, the resulting mixture was concentrated under reduced pressure. The residue was purified by flash column chromatography on silica gel (0 to 20% ethyl acetate in hexanes) to give (1R,2R)-4-bromo-2-fluoro-2,3-dihydro-1H-inden-1-yl 4-nitrobenzoate.

A vigorously stirred mixture of (1R,2R)-4-bromo-2-fluoro-2,3-dihydro-1H-inden-1-yl 4-nitrobenzoate (287 mg, 0.754 mmol), 4,4,4',4',5,5,5',5'-octamethyl-2,2'-bi(1,3,2-dioxaborolane) (230 mg, 0.905 mmol), potassium acetate (197 mg, 2.01 mmol), and bis(diphenylphosphino)ferrocene]dichloropalladium(II) (28 mg, 0.038 mmol) in 1,4-dioxane (7.0 mL) was heated to 95° C. After 13 h, the resulting mixture was cooled to room temperature, was filtered through celite, and was concentrated under reduced pressure. The residue was purified by flash column chromatography on silica gel (0 to 12% ethyl acetate in hexanes) to give (1R,2R)-2-fluoro-4-(4,4,5,5-tetramethyl-1,3,2-dioxaborolan-2-yl)-2,3-dihydro-1H-inden-1-yl 4-nitrobenzoate.

A vigorously stirred mixture of (1R,2R)-4-bromo-2-fluoro-2,3-dihydro-1H-inden-1-yl 4-nitrobenzoate (287 mg, 0.754 mmol), (1R,2R)-2-fluoro-4-(4,4,5,5-tetramethyl-1,3,2-dioxaborolan-2-yl)-2,3-dihydro-1H-inden-1-yl 4-nitrobenzoate (322 mg, 0.754 mmol), saturated aqueous sodium carbonate solution (943 μL), and chloro(2-dicyclohexylphosphino-2',4',6'-triisopropyl-1,1'-biphenyl)[2-(2'-amino-1,1'-biphenyl)]palladium(II) (59 mg, 0.075 mmol) in 1,4-dioxane (3.0 mL) was heated to 90° C. After 5 h, the resulting mixture was cooled to room temperature, and ethyl acetate (60 mL) was added. The organic layer was washed with a mixture of brine and water (2:1 v:v, 30 mL), was dried over anhydrous sodium sulfate, was filtered, and was concentrated under reduced pressure. The residue was purified by flash column chromatography on silica gel (0 to 50% ethyl acetate in hexanes) to give a mixture of (1R,1'R,2R,2'R)-2,2'-difluoro-2,2',3,3'-tetrahydro-1H,1'H-[4,4'-biindene]-1,1'-diylbis(4-nitrobenzoate), (1R,1'R,2R,2'R)-2,2'-difluoro-1'-hydroxy-2,2',3,3'-tetrahydro-1H,1'H-[4,4'-biinden]-1-yl 4-nitrobenzoate, and (1R,1'R,2R,2'R)-2,2'-difluoro-2,2',3,3'-tetrahydro-1H,1'H-[4,4'-biindene]-1,1'-diol. The mixture was dissolved in tetrahydrofuran (15 mL) and methanol (15 mL) and was stirred at room temperature. Aqueous sodium hydroxide solution (1.0 M, 6.0 mL, 6.0 mmol) was added. After 20 min, ethyl acetate (63 mL) and diethyl ether (63 mL) were added. The organic layer was washed sequentially with water (100 mL), a mixture of saturated aqueous sodium bicarbonate solution and water (1:1 v:v, 100 mL), and water (100 mL), was dried over anhydrous magnesium sulfate, was filtered, and was concentrated under reduced pressure to give (1R,1'R,2R,2'R)-2,2'-difluoro-2,2',3,3'-tetrahydro-1H,1'H-[4,4'-biindene]-1,1'-diol.

A vigorously stirred mixture of (1R,1'R,2R,2'R)-2,2'-difluoro-2,2',3,3'-tetrahydro-1H,1'H-[4,4'-biindene]-1,1'-diol (185 mg, 0.612 mmol), 6-chloro-2-methoxynicotinaldehyde (420 mg, 2.45 mmol), cesium carbonate (917 mg, 2.82 mmol), and [(2-di-tert-butylphosphino-2',4',6'-triisopropyl-1,1'-biphenyl)-2-(2'-amino-1,1'-biphenyl)] palladium(II) methanesulfonate (97 mg, 0.12 mmol) in toluene (7.0 mL) was heated to 100° C. After 14.5 h, the resulting mixture was cooled to room temperature, was filtered through celite, and was concentrated under reduced pressure. The residue was purified by flash column chromatography on silica gel (0 to 30% ethyl acetate in hexanes) to give 6,6'-(((1R,1'R,2R,2'R)-2,2'-difluoro-2,2',3,3'-tetrahydro-1H,1'H-[4,4'-biindene]-1,1'-diyl)bis(oxy))bis(2-methoxynicotinaldehyde).

Hydrogen chloride solution (4.0 M in 1,4-dioxane, 96.3 μL, 0.385 mmol) was added via syringe to a stirred mixture of 6,6'-(((1R,1'R,2R,2'R)-2,2'-difluoro-2,2',3,3'-tetrahydro-1H,1'H-[4,4'-biindene]-1,1'-diyl)bis(oxy))bis(2-methoxynicotinaldehyde) (103 mg, 0.179 mmol) and 2-chloro-1,3-bis(methoxycarbonyl)guanidine (82.7 mg, 0.394 mmol) in acetonitrile (8.0 mL) and chloroform (8.0 mL) at room temperature. After 40 min, 2-chloro-1,3-bis(methoxycarbonyl)guanidine (37.6 mg, 0.179 mmol) was added. After 1 min, hydrogen chloride solution (4.0 M in 1,4-dioxane, 44.8 μL, 0.179 mmol) was added via syringe. After 30 min, ethyl acetate (60 mL) was added. The organic layer was washed sequentially with water (30 mL) and brine (30 mL), was dried over anhydrous sodium sulfate, was filtered, and was concentrated under reduced pressure. The residue was purified by flash column chromatography on silica gel (0 to 30% ethyl acetate in hexanes) to give 6,6'-(((1R,1'R,2R,2'R)-2,2'-difluoro-2,2',3,3'-tetrahydro-1H,1'H-[4,4'-biindene]-1,1'-diyl)bis(oxy))bis(5-chloro-2-methoxynicotinaldehyde).

Sodium triacetoxyborohydride (126 mg, 0.596 mmol) was added to a stirred mixture of 6,6'-(((1R,1'R,2R,2'R)-2,2'-difluoro-2,2',3,3'-tetrahydro-1H,1'H-[4,4'-biindene]-1,1'-diyl)bis(oxy))bis(5-chloro-2-methoxynicotinaldehyde) (38 mg, 0.060 mmol), (S)-4-amino-3-hydroxybutanoic acid (85.1 mg, 0.715 mmol), and acetic acid (0.20 mL) in dimethylsulfoxide (1.5 mL) at room temperature. After 45 min, trifluoroacetic acid (60 μL) was added, and the resulting mixture was purified by reverse phase preparative HPLC (0.1% trifluoroacetic acid in acetonitrile/water) to give (3S,3'S)-4,4'-((((((1R,1'R,2R,2'R)-2,2'-difluoro-2,2',3,3'-tetrahydro-1H,1'H-[4,4'-biindene]-1,1'-diyl)bis(oxy))bis(5-chloro-2-methoxypyridine-6,3-diyl))bis(methylene))bis(azanediyl))bis(3-hydroxybutanoic acid). ES/MS (m/z, $M+H^+$): 847.2.

Example 640: (3S,3'S)-4,4'-((((((1R,1'R,2S,2'S)-2,2'-difluoro-2,2',3,3'-tetrahydro-1H,1'H-[4,4'-biindene]-1,1'-diyl)bis(oxy))bis(5-chloro-2-methoxypyridine-6,3-diyl))bis(methylene))bis(azanediyl))bis(3-hydroxybutanoic acid)

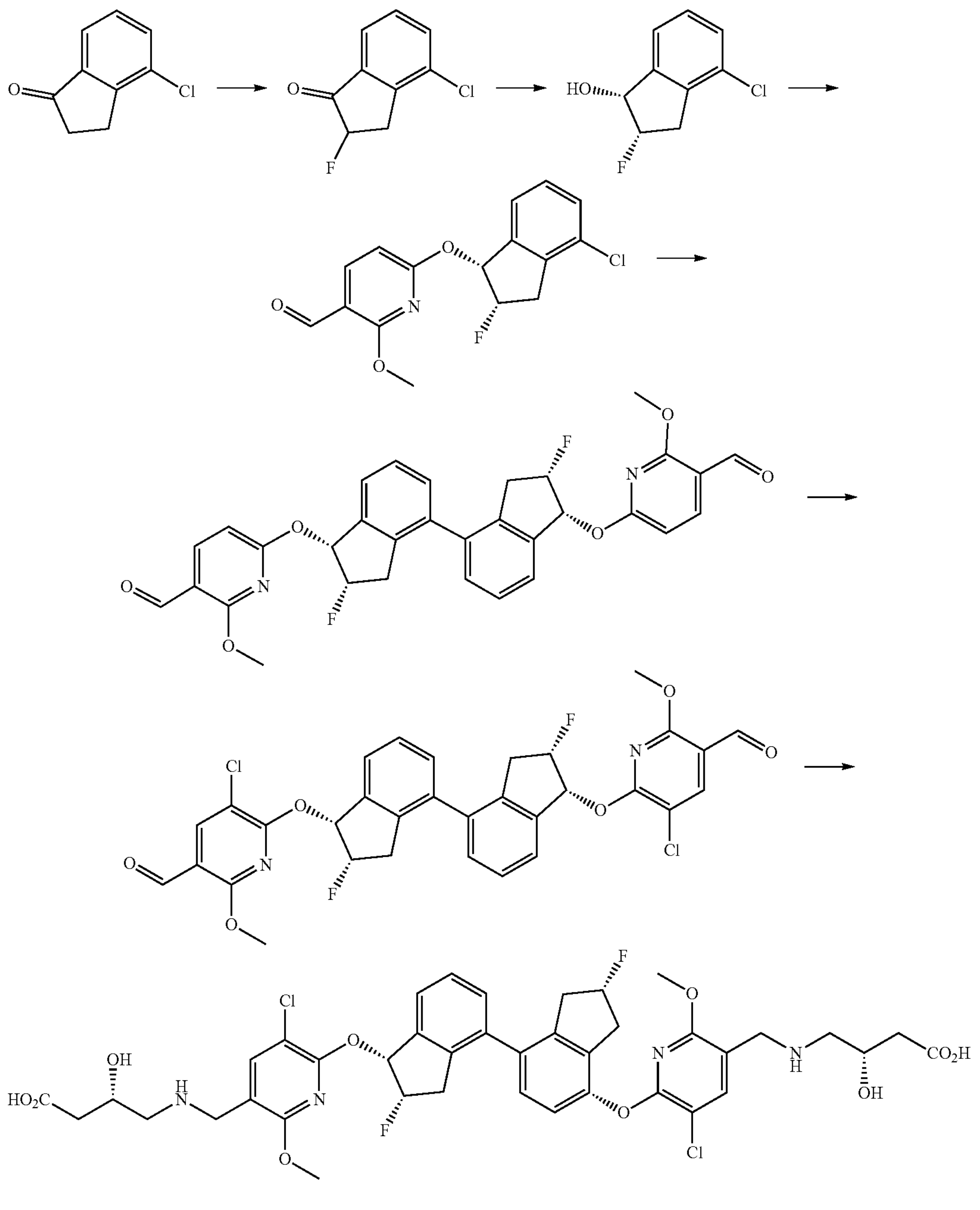

A stirred mixture of 4-chloro-2,3-dihydro-1H-inden-1-one (3.00 g, 18.0 mmol), 1-(chloromethyl)-4-fluoro-1,4-diazabicyclo[2.2.2]octane-1,4-diium tetrafluoroborate (7.66 g, 21.6 mmol), and sulfuric acid (96.0 μL, 1.80 mmol) in methanol (40 mL) was heated to 65° C. After 18 h, the resulting mixture was cooled to room temperature. Ethyl acetate (50 mL) and diethyl ether (200 mL) were added. The organic layer was washed with water (200 mL), was dried over anhydrous magnesium sulfate, was filtered, and was concentrated under reduced pressure. The residue was purified by flash column chromatography on silica gel (0 to 10% ethyl acetate in hexanes) to give 4-chloro-2-fluoro-2,3-dihydro-1H-inden-1-one.

[N-[(1S,2S)-2-(Amino-κN)-1,2-diphenylethyl]-4-methylbenzenesulfonamidato-κN]chloro[(1,2,3,4,5,6-η)-1-methyl-4-(1-methylethyl)benzene]-ruthenium (90.9 mg, 0.143 mmol) was added to a stirred mixture of 4-chloro-2-fluoro-2,3-dihydro-1H-inden-1-one (2.64 g, 14.3 mmol), formic acid (3.88 mL, 103 mmol), triethylamine (12 mL, 86 mmol), and dichloromethane (1.5 mL) at room temperature. After 18 h, diethyl ether (150 mL) was added. The organic layer was washed with saturated aqueous sodium bicarbonate solution (2×90 mL), was dried over anhydrous magnesium sulfate, was filtered, and was concentrated under reduced pressure.

The residue was purified by flash column chromatography on silica gel (0 to 20% ethyl acetate in hexanes) to give (1R,2S)-4-chloro-2-fluoro-2,3-dihydro-1H-inden-1-ol.

A vigorously stirred mixture of (1R,2S)-4-chloro-2-fluoro-2,3-dihydro-1H-inden-1-ol (1.00 g, 5.36 mmol), 6-chloro-2-methoxynicotinaldehyde (1.10 g, 6.43 mmol), cesium carbonate (2.27 g, 6.97 mmol), and [(2-di-tert-butylphosphino-2',4',6'-triisopropyl-1,1'-biphenyl)-2-(2'-amino-1,1'-biphenyl)]palladium(II) methanesulfonate (128 mg, 0.161 mmol) in toluene (8.0 mL) was heated to 105° C. After 3.5 h, the resulting mixture was cooled to room temperature, was filtered through celite, and was concentrated under reduced pressure. The residue was purified by flash column chromatography on silica gel (0 to 20% ethyl acetate in hexanes) to give 6-(((1R,2S)-4-chloro-2-fluoro-2,3-dihydro-1H-inden-1-yl)oxy)-2-methoxynicotinaldehyde.

A vigorously stirred mixture of 6-(((1R,2S)-4-chloro-2-fluoro-2,3-dihydro-1H-inden-1-yl)oxy)-2-methoxynicotinaldehyde (312 mg, 0.970 mmol), 4,4,4',4',5,5,5',5'-octamethyl-2,2'-bi(1,3,2-dioxaborolane) (123 mg, 0.485 mmol), saturated aqueous sodium carbonate solution (1.94 mL), and chloro(2-dicyclohexylphosphino-2',4',6'-triisopropyl-1,1'-biphenyl)[2-(2'-amino-1,1'-biphenyl)]palladium(II) (76 mg, 0.097 mmol) in 1,4-dioxane (9.0 mL) was heated to 100° C. After 15 h, the resulting mixture was cooled to room temperature, and ethyl acetate (50 mL) was added. The organic layer was washed with a mixture of brine and water (2:1 v:v, 30 mL), was filtered, and was concentrated under reduced pressure. The residue was purified by flash column chromatography on silica gel (0 to 30% ethyl acetate in hexanes) to give 6,6'-(((1R,1'R,2S,2'S)-2,2'-difluoro-2,2',3,3'-tetrahydro-1H,1'H-[4,4'-biindene]-1,1'-diyl)bis(oxy))bis(2-methoxynicotinaldehyde).

Hydrogen chloride solution (4.0 M in 1,4-dioxane, 136 μL, 0.542 mmol) was added via syringe to a stirred mixture of 6,6'-(((1R,1'R,2S,2'S)-2,2'-difluoro-2,2',3,3'-tetrahydro-1H,1'H-[4,4'-biindene]-1,1'-diyl)bis(oxy))bis(2-methoxynicotinaldehyde) (144 mg, 0.252 mmol) and 2-chloro-1,3-bis(methoxycarbonyl)guanidine (116 mg, 0.555 mmol) in acetonitrile (8.0 mL) and chloroform (8.0 mL) at room temperature. After 65 min, 2-chloro-1,3-bis(methoxycarbonyl)guanidine (29.1 mg, 0.139 mmol) was added. After 1 min, hydrogen chloride solution (4.0 M in 1,4-dioxane, 31.5 μL, 0.126 mmol) was added via syringe. After 15 min, ethyl acetate (60 mL) was added. The organic layer was washed sequentially with water (30 mL) and brine (30 mL), was dried over anhydrous sodium sulfate, was filtered, and was concentrated under reduced pressure. The residue was purified by flash column chromatography on silica gel (0 to 30% ethyl acetate in hexanes) to give 6,6'-(((1R,1'R,2S,2'S)-2,2'-difluoro-2,2',3,3'-tetrahydro-1H,1'H-[4,4'-biindene]-1,1'-diyl)bis(oxy))bis(5-chloro-2-methoxynicotinaldehyde).

Sodium triacetoxyborohydride (463 mg, 2.18 mmol) was added to a stirred mixture of 6,6'-(((1R,1'R,2S,2'S)-2,2'-difluoro-2,2',3,3'-tetrahydro-1H,1'H-[4,4'-biindene]-1,1'-diyl)bis(oxy))bis(5-chloro-2-methoxynicotinaldehyde) (140 mg, 0.218 mmol), (S)-4-amino-3-hydroxybutanoic acid (156 mg, 1.31 mmol), and acetic acid (0.20 mL) in dimethylsulfoxide (1.5 mL) at room temperature. After 60 min, trifluoroacetic acid (150 μL) was added, and the resulting mixture was purified by reverse phase preparative HPLC (0.1% trifluoroacetic acid in acetonitrile/water) to give (3S,3'S)-4,4'-((((((1R,1'R,2S,2'S)-2,2'-difluoro-2,2',3,3'-tetrahydro-1H,1'H-[4,4'-biindene]-1,1'-diyl)bis(oxy))bis(5-chloro-2-methoxypyridine-6,3-diyl))bis(methylene))bis(azanediyl))bis(3-hydroxybutanoic acid). ES/MS (m/z, M+H+): 847.2.

The following compounds were prepared according to the procedures described herein (e.g., according to Example 637 or 638) using the appropriate starting material(s) and appropriate protecting group chemistry as needed.

| Example No. | Structure | ES/MS (m/z, M + H+) |
|---|---|---|
| 641 | 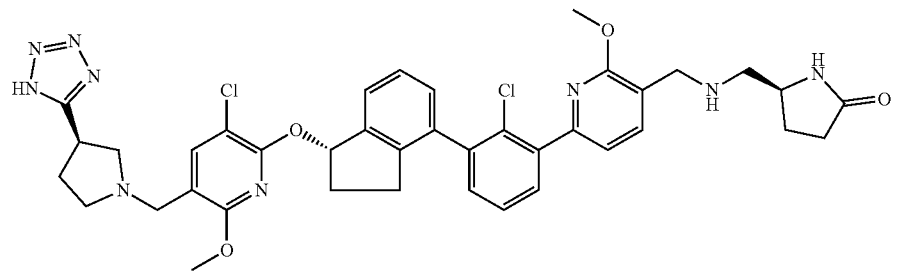 [SMILES: COc1nc(-c2cccc(-c3cccc4c3CC[C@@H]4Oc3nc(OC)c(CN4CC[C@@H](c5nnn[nH]5)C4)cc3Cl)c2Cl)ccc1CNC[C@@H]1CCC(=O)N1] | 769.92 |
| 642 | 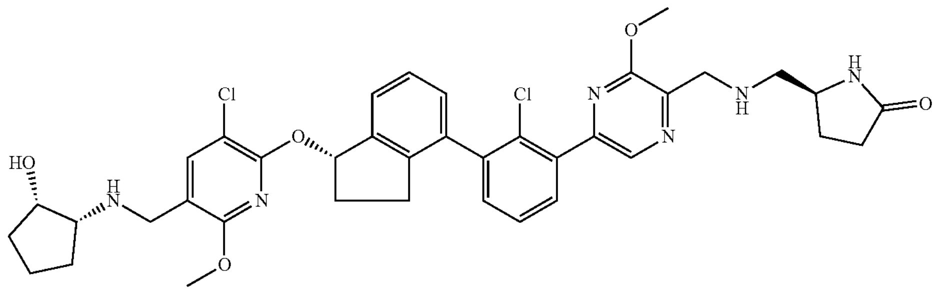 [SMILES: COc1nc(O[C@H]2CCc3c(-c4cccc(-c5cnc(CNC[C@@H]6CCC(=O)N6)c(OC)n5)c4Cl)cccc32)c(Cl)cc1CN[C@@H]1CCC[C@@H]1O] | 733.03 |

-continued
| Example No. | Structure | ES/MS (m/z, M + H+) |
|---|---|---|
| 643 | 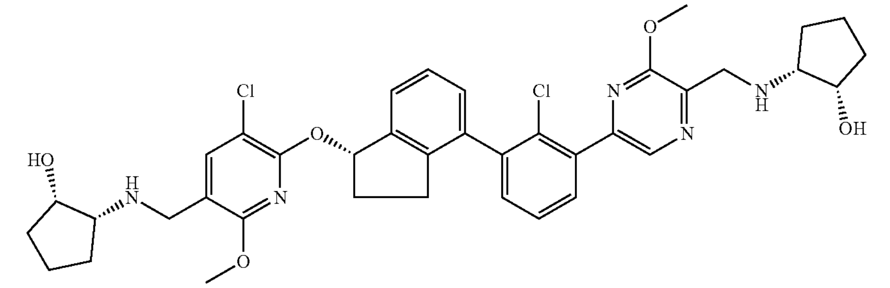 [SMILES: COc1nc(O[C@H]2CCc3c(-c4cccc(-c5cnc(CN[C@@H]6CCC[C@@H]6O)c(OC)n5)c4Cl)cccc32)c(Cl)cc1CN[C@@H]1CCC[C@@H]1O] | 720.07 |
| 644 | 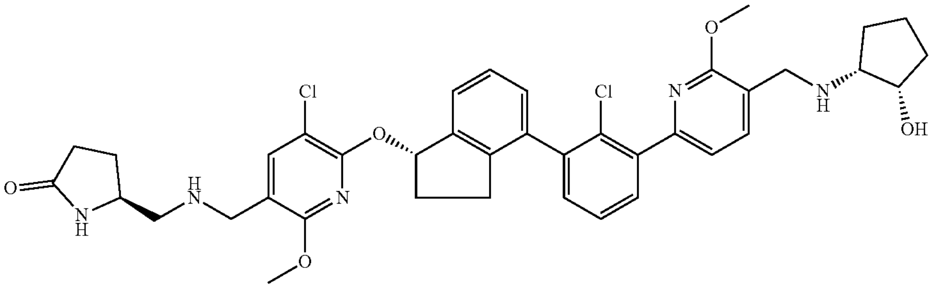 [SMILES: COc1nc(-c2cccc(-c3cccc4c3CC[C@@H]4Oc3nc(OC)c(CNC[C@@H]4CCC(=O)N4)cc3Cl)c2Cl)ccc1CN[C@@H]1CCC[C@@H]1O] | 732.06 |
| 645 | 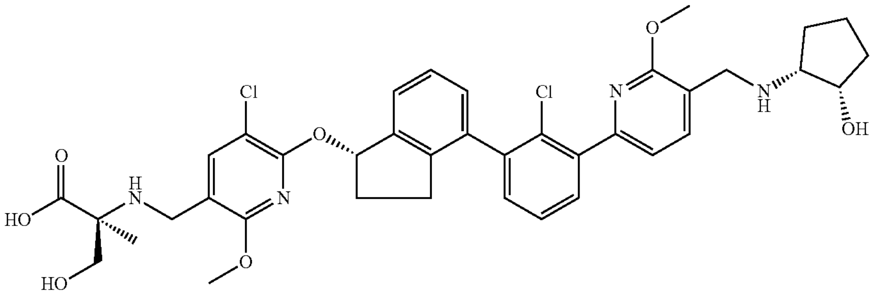 [SMILES: COc1nc(-c2cccc(-c3cccc4c3CC[C@@H]4Oc3nc(OC)c(CN[C@@](C)(CO)C(=O)O)cc3Cl)c2Cl)ccc1CN[C@@H]1CCC[C@@H]1O] | 736.98 |
| 646 | 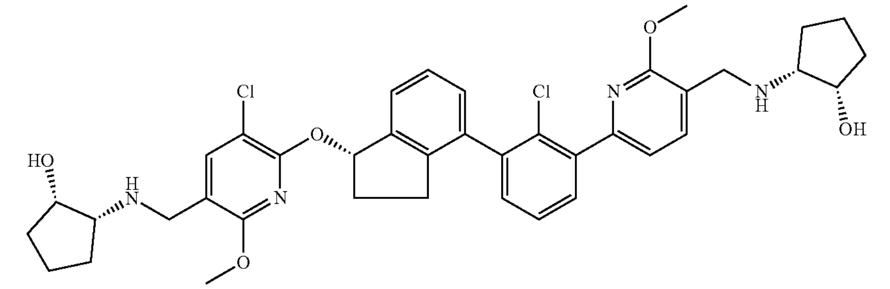 [SMILES: COc1nc(-c2cccc(-c3cccc4c3CC[C@@H]4Oc3nc(OC)c(CN[C@@H]4CCC[C@@H]4O)cc3Cl)c2Cl)ccc1CN[C@@H]1CCC[C@@H]1O] | 718.97 |
| 647 | 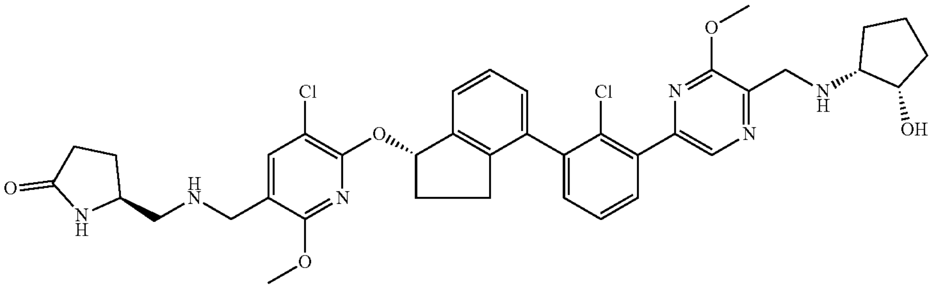 [SMILES: COc1nc(O[C@H]2CCc3c(-c4cccc(-c5cnc(CN[C@@H]6CCC[C@@H]6O)c(OC)n5)c4Cl)cccc32)c(Cl)cc1CNC[C@@H]1CCC(=O)N1] | 733.08 |

-continued
| Example No. | Structure | ES/MS (m/z, M + H+) |
|---|---|---|
| 648 | 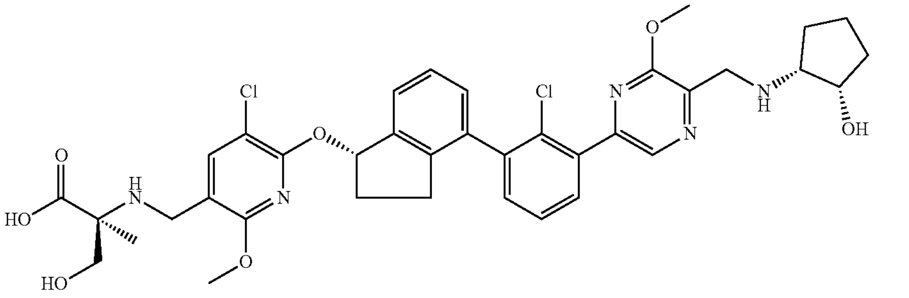 [SMILES: COc1nc(O[C@H]2CCc3c(-c4cccc(-c5cnc(CN[C@@H]6CCC[C@@H]6O)c(OC)n5)c4Cl)cccc32)c(Cl)cc1CN[C@@](C)(CO)C(=O)O] | 737.98 |
| 649 | 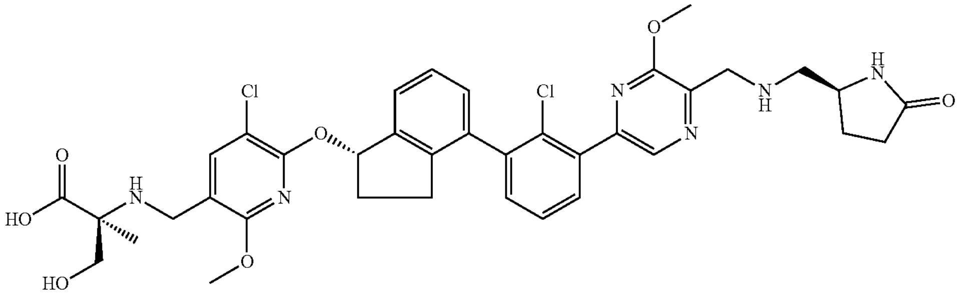 [SMILES: COc1nc(O[C@H]2CCc3c(-c4cccc(-c5cnc(CNC[C@@H]6CCC(=O)N6)c(OC)n5)c4Cl)cccc32)c(Cl)cc1CN[C@@](C)(CO)C(=O)O] | 750.9 |
| 650 | 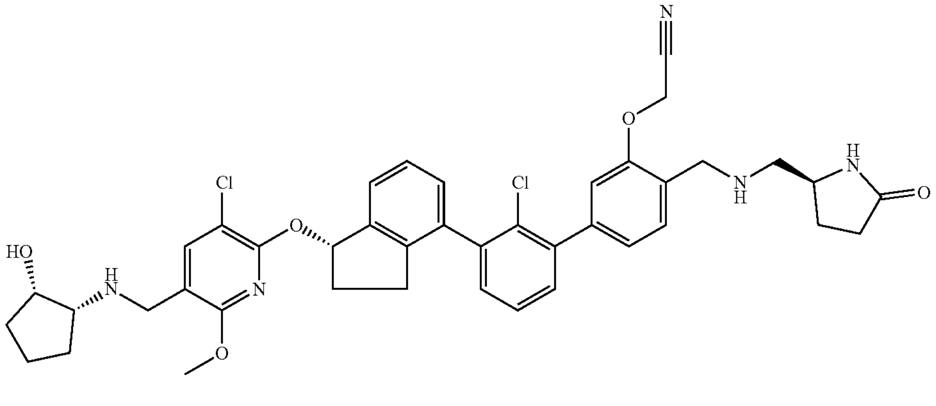 [SMILES: COc1nc(O[C@H]2CCc3c(-c4cccc(-c5ccc(CNC[C@@H]6CCC(=O)N6)c(OCC#N)c5)c4Cl)cccc32)c(Cl)cc1CN[C@@H]1CCC[C@@H]1O] | 756.03 |
| 651 | 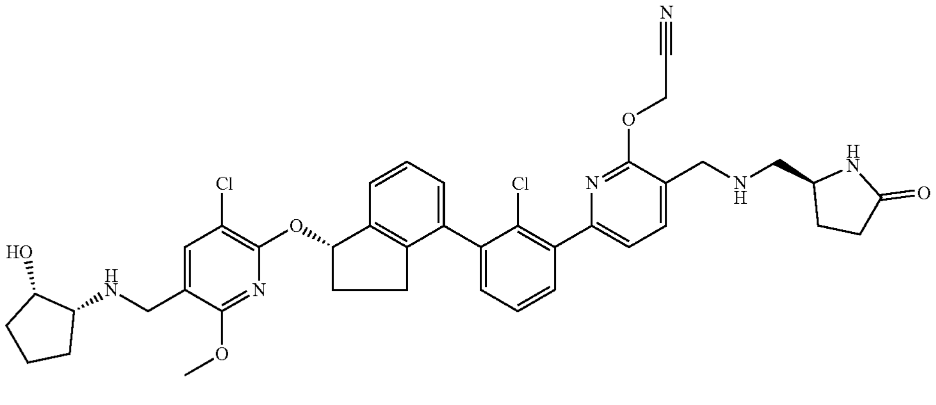 [SMILES: COc1nc(O[C@H]2CCc3c(-c4cccc(-c5ccc(CNC[C@@H]6CCC(=O)N6)c(OCC#N)n5)c4Cl)cccc32)c(Cl)cc1CN[C@@H]1CCC[C@@H]1O] | 757 |

-continued
| Example No. | Structure | ES/MS (m/z, M + H+) |
|---|---|---|
| 652 | 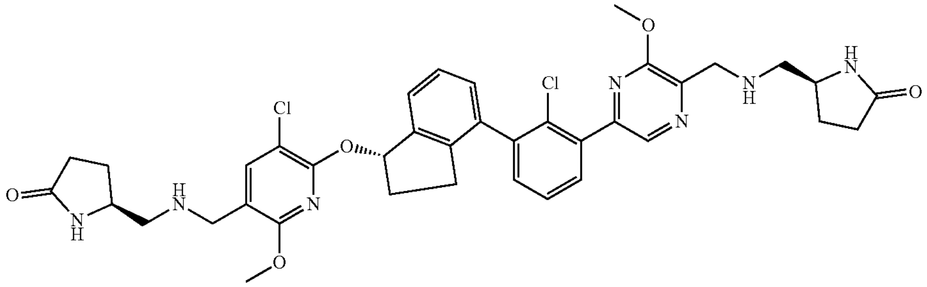 [SMILES: COc1nc(O[C@H]2CCc3c(-c4cccc(-c5cnc(CNC[C@@H]6CCC(=O)N6)c(OC)n5)c4Cl)cccc32)c(Cl)cc1CNC[C@@H]1CCC(=O)N1] | 745.93 |
| 653 | 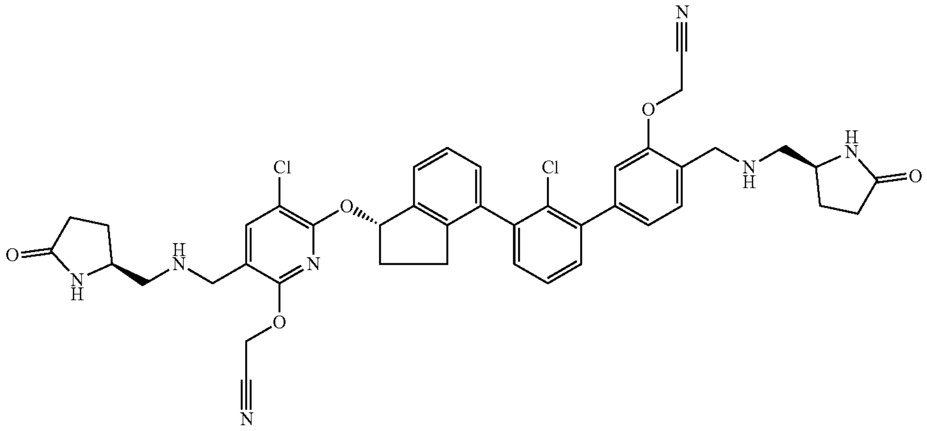 [SMILES: N#CCOc1cc(-c2cccc(-c3cccc4c3CC[C@@H]4Oc3nc(OCC#N)c(CNC[C@@H]4CCC(=O)N4)cc3Cl)c2Cl)ccc1CNC[C@@H]1CCC(=O)N1] | 794.02 |
| 654 | 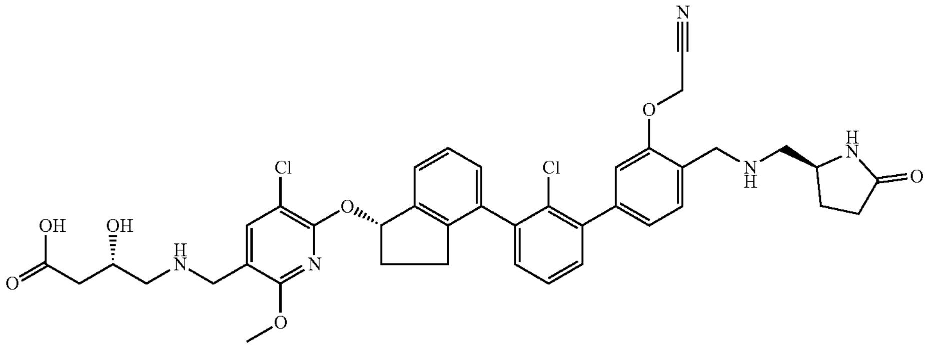 [SMILES: COc1nc(O[C@H]2CCc3c(-c4cccc(-c5ccc(CNC[C@@H]6CCC(=O)N6)c(OCC#N)c5)c4Cl)cccc32)c(Cl)cc1CNC[C@@H](O)CC(=O)O] | 774 |
| 655 | 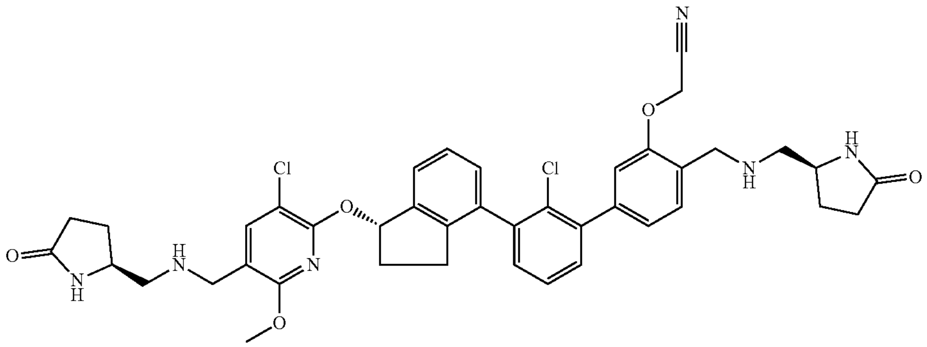 [SMILES: COc1nc(O[C@H]2CCc3c(-c4cccc(-c5ccc(CNC[C@@H]6CCC(=O)N6)c(OCC#N)c5)c4Cl)cccc32)c(Cl)cc1CNC[C@@H]1CCC(=O)N1] | 769.01 |

-continued
| Example No. | Structure | ES/MS (m/z, M + H+) |
|---|---|---|
| 656 | 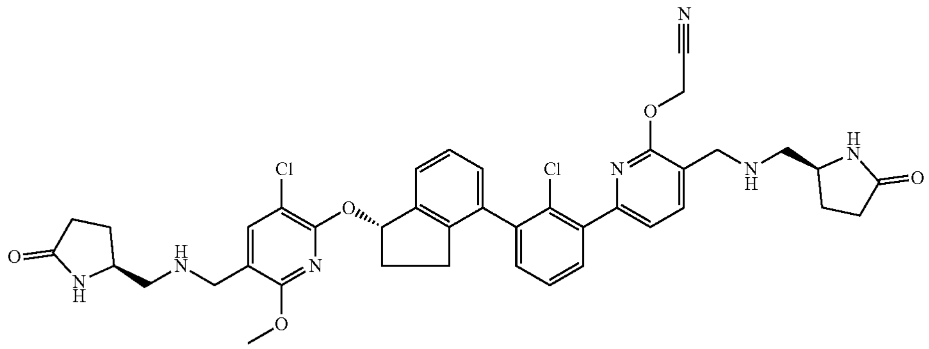 [SMILES: COc1nc(O[C@H]2CCc3c(-c4cccc(-c5ccc(CNC[C@@H]6CCC(=O)N6)c(OCC#N)n5)c4Cl)cccc32)c(Cl)cc1CNC[C@@H]1CCC(=O)N1] | 769.9 |
| 657 | 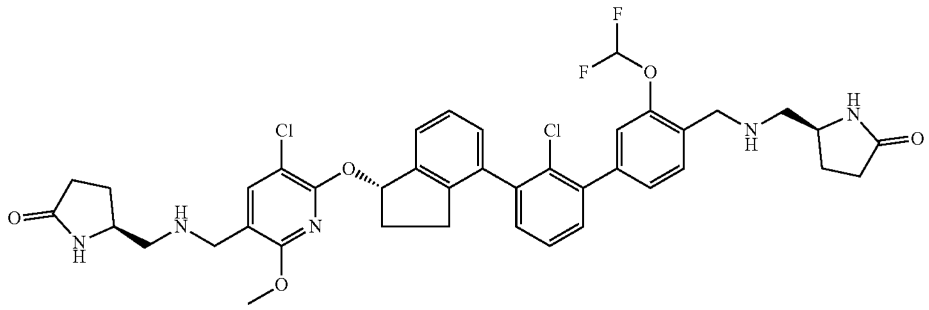 [SMILES: COc1nc(O[C@H]2CCc3c(-c4cccc(-c5ccc(CNC[C@@H]6CCC(=O)N6)c(OC(F)F)c5)c4Cl)cccc32)c(Cl)cc1CNC[C@@H]1CCC(=O)N1] | 779.91 |
| 658 | 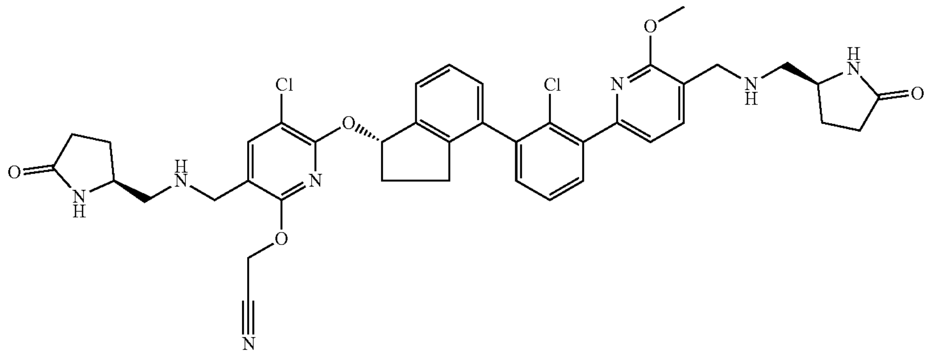 [SMILES: COc1nc(-c2cccc(-c3cccc4c3CC[C@@H]4Oc3nc(OCC#N)c(CNC[C@@H]4CCC(=O)N4)cc3Cl)c2Cl)ccc1CNC[C@@H]1CCC(=O)N1] | 769.97 |
| 659 | 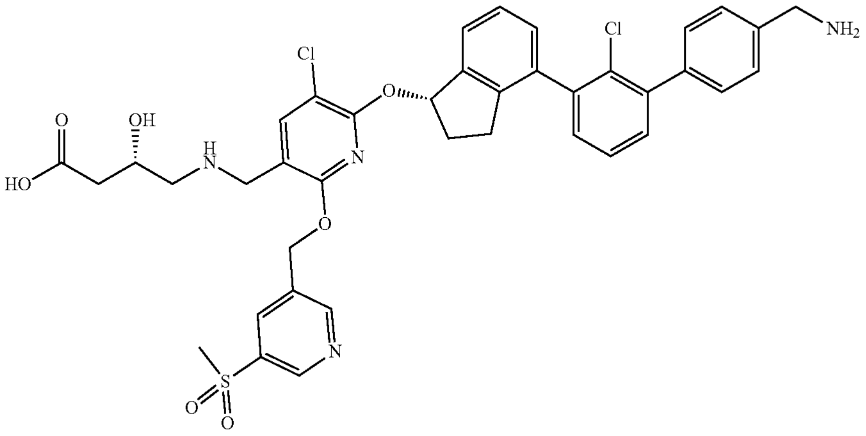 [SMILES: CS(=O)(=O)c1cncc(COc2nc(O[C@H]3CCc4c(-c5cccc(-c6ccc(CN)cc6)c5Cl)cccc43)c(Cl)cc2CNC[C@@H](O)CC(=O)O)c1] | 776.97 |

-continued
| Example No. | Structure | ES/MS (m/z, M + H+) |
|---|---|---|
| 660 | 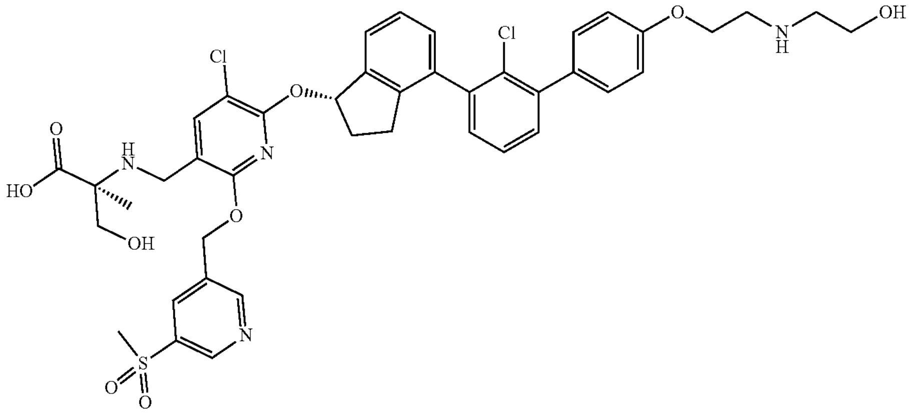 [SMILES: C[C@@](CO)(NCc1cc(Cl)c(O[C@H]2CCc3c(-c4cccc(-c5ccc(OCCNCCO)cc5)c4Cl)cccc32)nc1OCc1cncc(S(C)(=O)=O)c1)C(=O)O] | 851.05 |
| 661 | 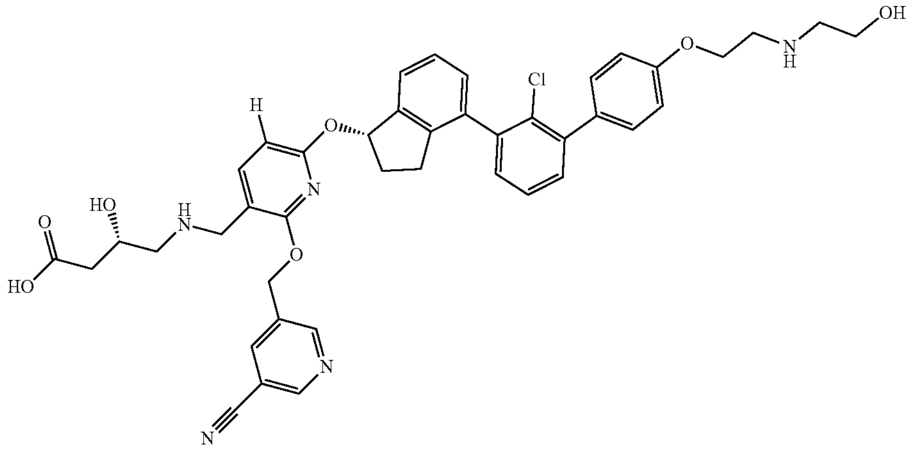 [SMILES: N#Cc1cncc(COc2nc(O[C@H]3CCc4c(-c5cccc(-c6ccc(OCCNCCO)cc6)c5Cl)cccc43)ccc2CNC[C@@H](O)CC(=O)O)c1] | 763.96 |
| 662 | 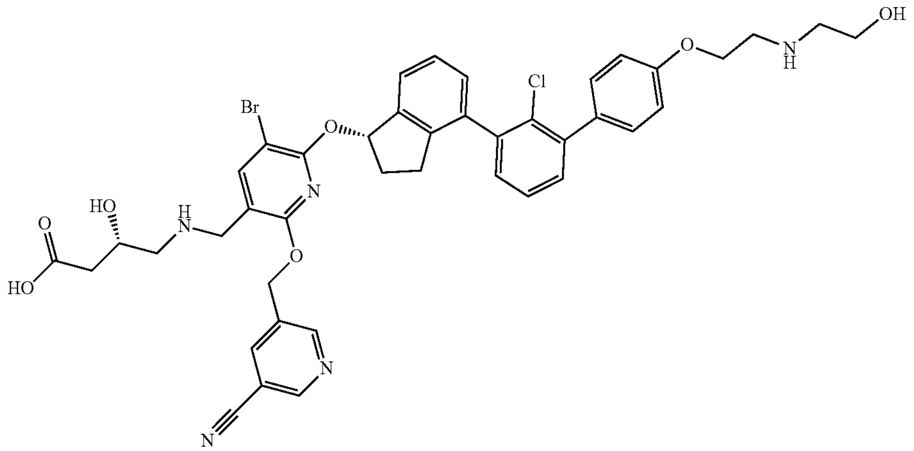 [SMILES: N#Cc1cncc(COc2nc(O[C@H]3CCc4c(-c5cccc(-c6ccc(OCCNCCO)cc6)c5Cl)cccc43)c(Br)cc2CNC[C@@H](O)CC(=O)O)c1] | 841.93 |

-continued
| Example No. | Structure | ES/MS (m/z, M + H+) |
|---|---|---|
| 663 | 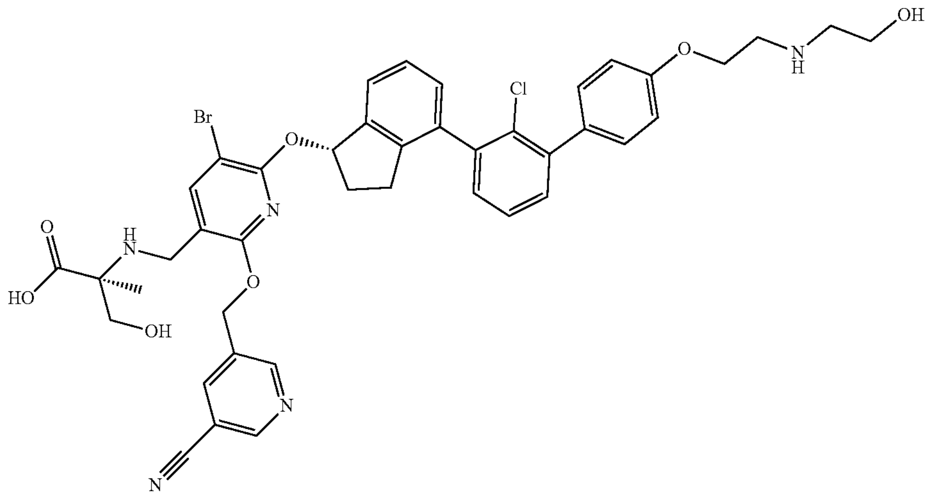 [SMILES: C[C@@](CO)(NCc1cc(Br)c(O[C@H]2CCc3c(-c4cccc(-c5ccc(OCCNCCO)cc5)c4Cl)cccc32)nc1OCc1cncc(C#N)c1)C(=O)O] | 841.88 |
| 664 | 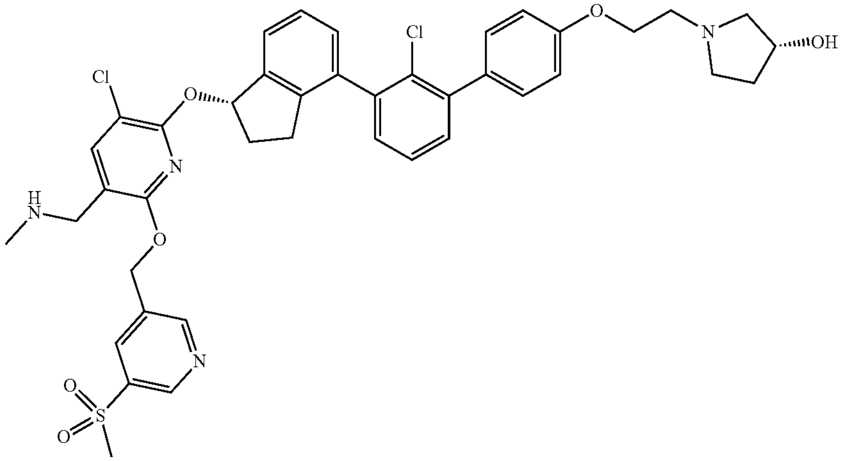 [SMILES: CNCc1cc(Cl)c(O[C@H]2CCc3c(-c4cccc(-c5ccc(OCCN6CC[C@@H](O)C6)cc5)c4Cl)cccc32)nc1OCc1cncc(S(C)(=O)=O)c1] | 789.23 |
| 665 | 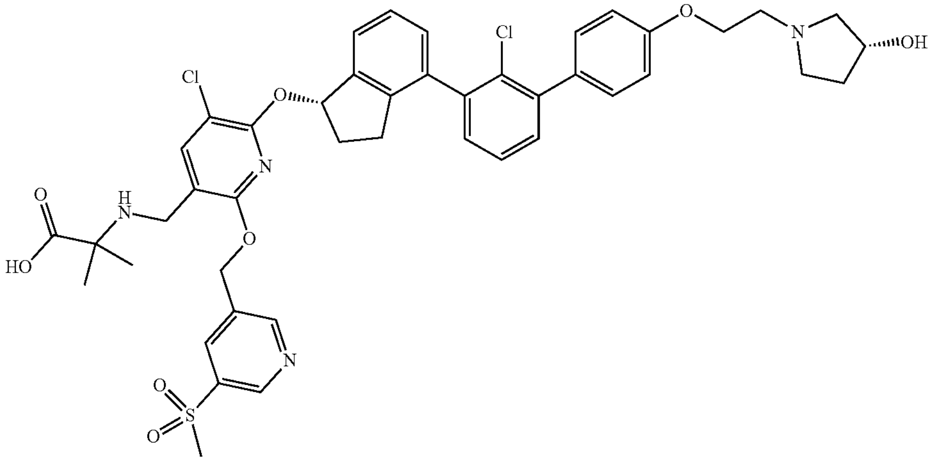 [SMILES: CC(C)(NCc1cc(Cl)c(O[C@H]2CCc3c(-c4cccc(-c5ccc(OCCN6CC[C@@H](O)C6)cc5)c4Cl)cccc32)nc1OCc1cncc(S(C)(=O)=O)c1)C(=O)O] | 860.97 |

-continued
| Example No. | Structure | ES/MS (m/z, M + H+) |
|---|---|---|
| 666 | 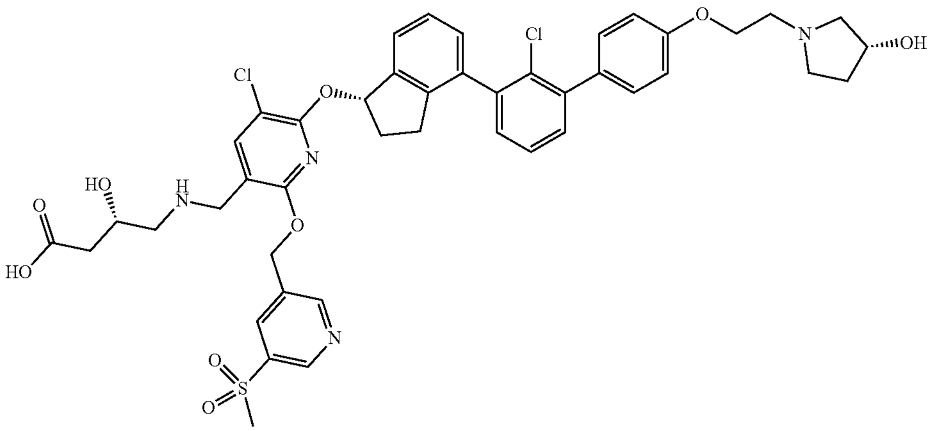 [SMILES: CS(=O)(=O)c1cncc(COc2nc(O[C@H]3CCc4c(-c5cccc(-c6ccc(OCCN7CC[C@@H](O)C7)cc6)c5Cl)cccc43)c(Cl)cc2CNC[C@@H](O)CC(=O)O)c1] | 877.03 |
| 667 | 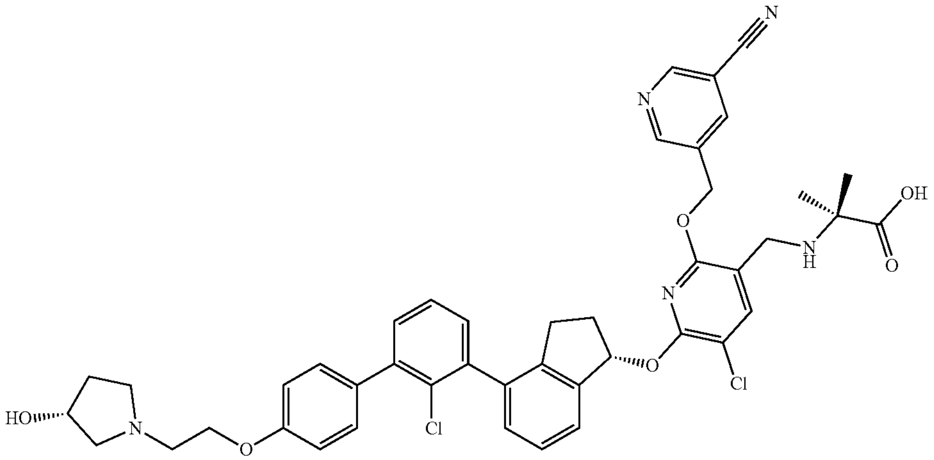 | 808.07 |
| 668 | 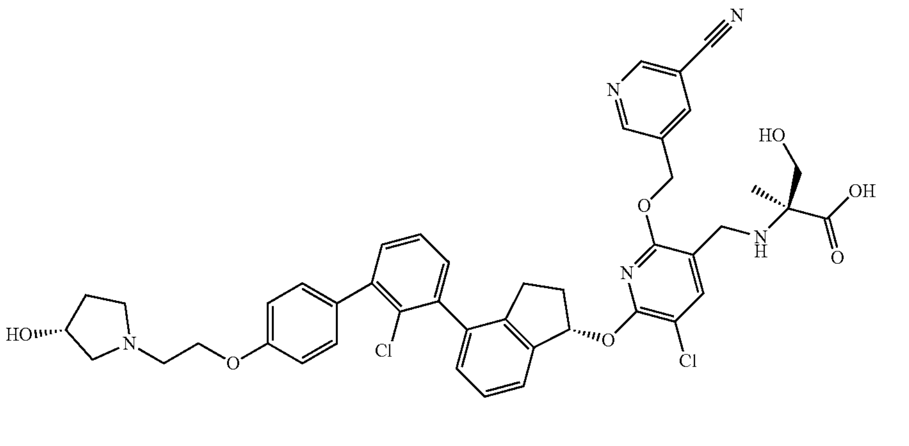 [SMILES: C[C@@](CO)(NCc1cc(Cl)c(O[C@H]2CCc3c(-c4cccc(-c5ccc(OCCN6CC[C@@H](O)C6)cc5)c4Cl)cccc32)nc1OCc1cncc(C#N)c1)C(=O)O] | 824.09 |

-continued
| Example No. | Structure | ES/MS (m/z, M + H+) |
|---|---|---|
| 669 | 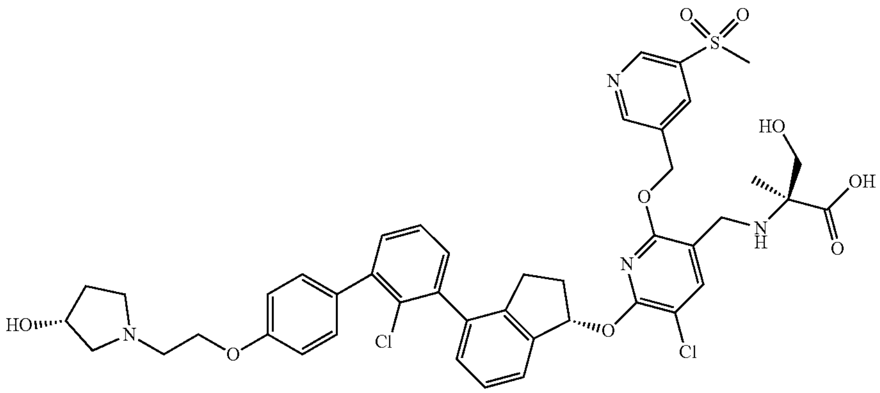 [SMILES: C[C@@](CO)(NCc1cc(Cl)c(O[C@H]2CCc3c(-c4cccc(-c5ccc(OCCN6CC[C@@H](O)C6)cc5)c4Cl)cccc32)nc1OCc1cncc(S(C)(=O)=O)c1)C(=O)O] | 876.99 |
| 670 | 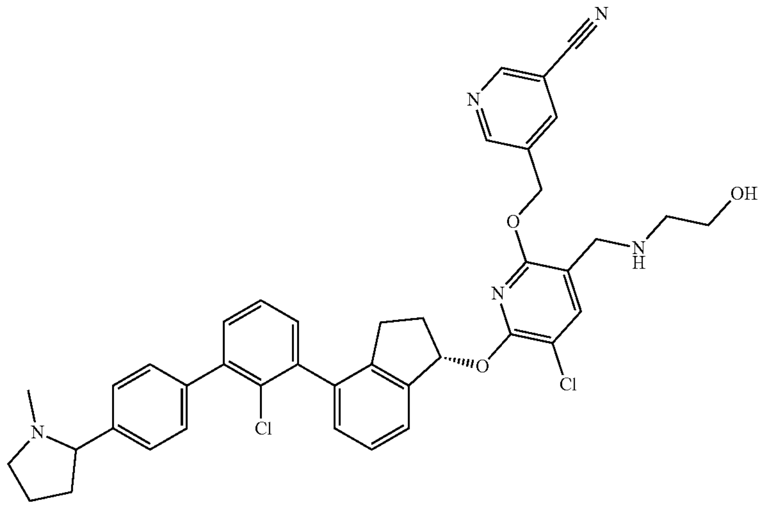 [SMILES: CN1CCCC1c1ccc(-c2cccc(-c3cccc4c3CC[C@@H]4Oc3nc(OCc4cncc(C#N)c4)c(CNCCO)cc3Cl)c2Cl)cc1] | 720.02 |
| 671 | 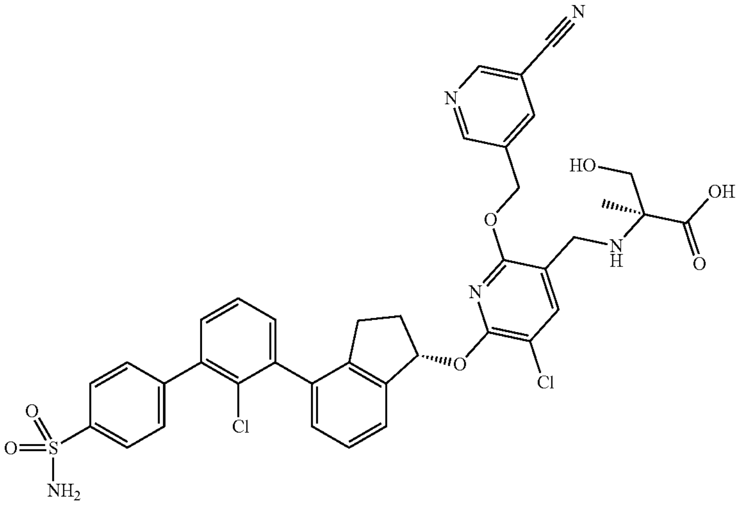 [SMILES: C[C@@](CO)(NCc1cc(Cl)c(O[C@H]2CCc3c(-c4cccc(-c5ccc(S(N)(=O)=O)cc5)c4Cl)cccc32)nc1OCc1cncc(C#N)c1)C(=O)O] | 773.88 |

-continued
| Example No. | Structure | ES/MS (m/z, M + H+) |
|---|---|---|
| 672 | 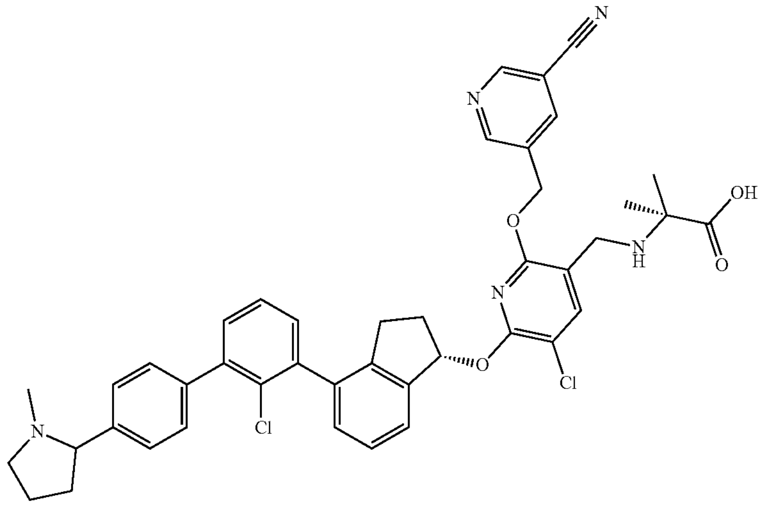 | 762.04 |
| 673 | 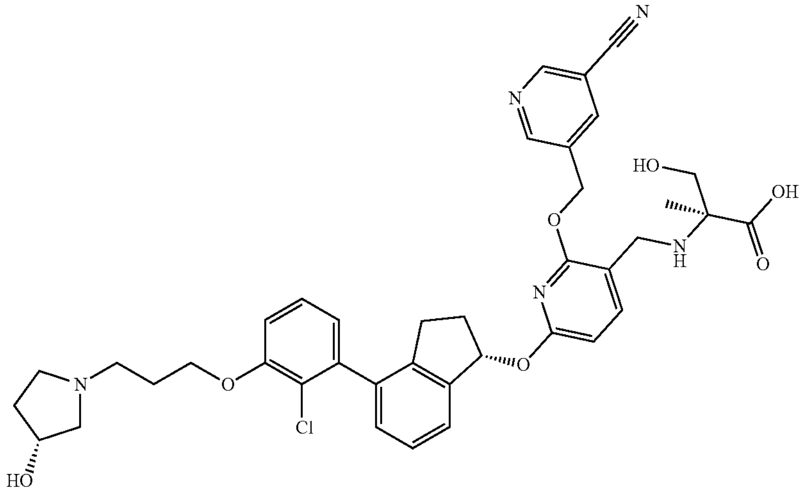 [SMILES: C[C@@](CO)(NCc1ccc(O[C@H]2CCc3c(-c4cccc(OCCCN5CC[C@@H](O)C5)c4Cl)cccc32)nc1OCc1cncc(C#N)c1)C(=O)O] | 728.08 |
| 674 | 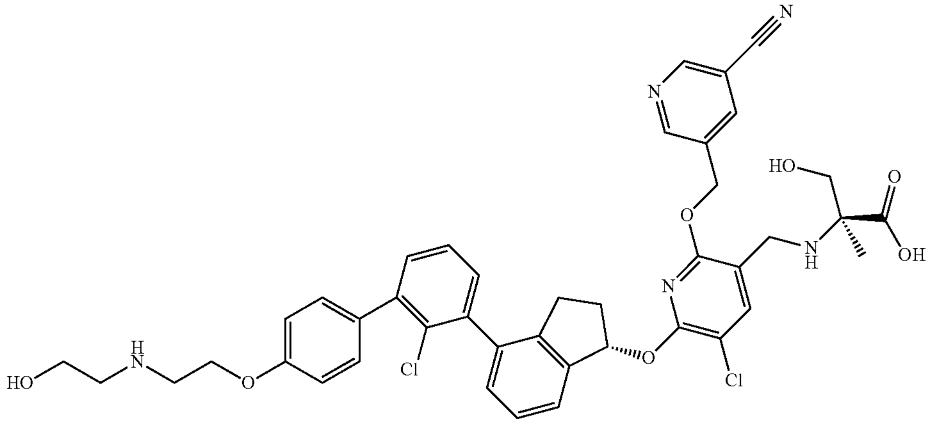 [SMILES: C[C@@](CO)(NCc1cc(Cl)c(O[C@H]2CCc3c(-c4cccc(-c5ccc(OCCNCCO)cc5)c4Cl)cccc32)nc1OCc1cncc(C#N)c1)C(=O)O] | 797.96 |

-continued
| Example No. | Structure | ES/MS (m/z, M + H+) |
|---|---|---|
| 675 | 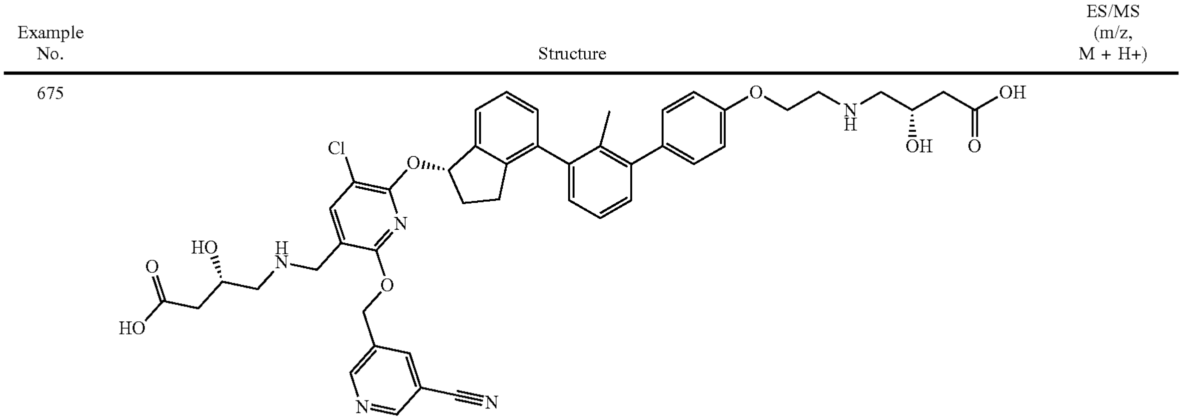 | |
| 676 | 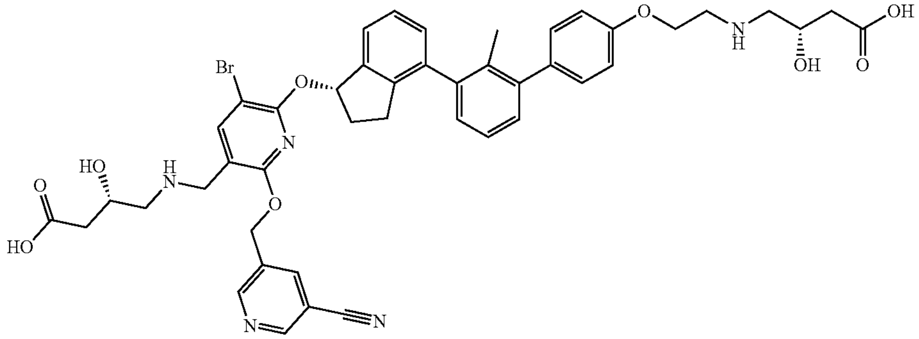 [SMILES: Cc1c(-c2ccc(OCCNC[C@@H](O)CC(=O)O)cc2)cccc1-c1cccc2c1CC[C@@H]2Oc1nc(OCc2cncc(C#N)c2)c(CNC[C@@H](O)CC(=O)O)cc1Br] | 882.12 |
| 677 | 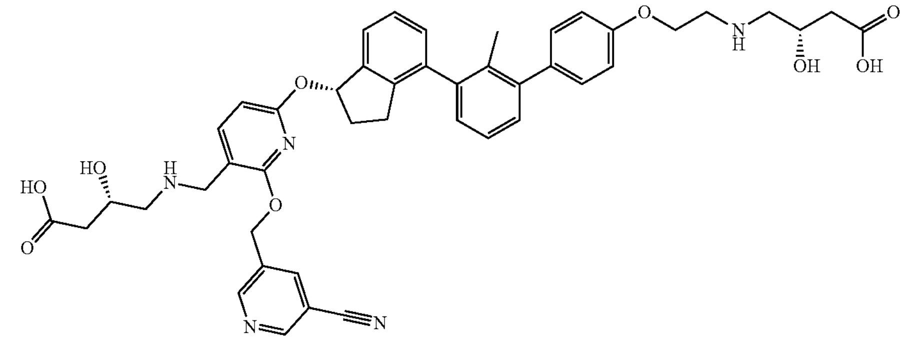 [SMILES: Cc1c(-c2ccc(OCCNC[C@@H](O)CC(=O)O)cc2)cccc1-c1cccc2c1CC[C@@H]2Oc1ccc(CNC[C@@H](O)CC(=O)O)c(OCc2cncc(C#N)c2)n1] | 802.22 |
| 678 | 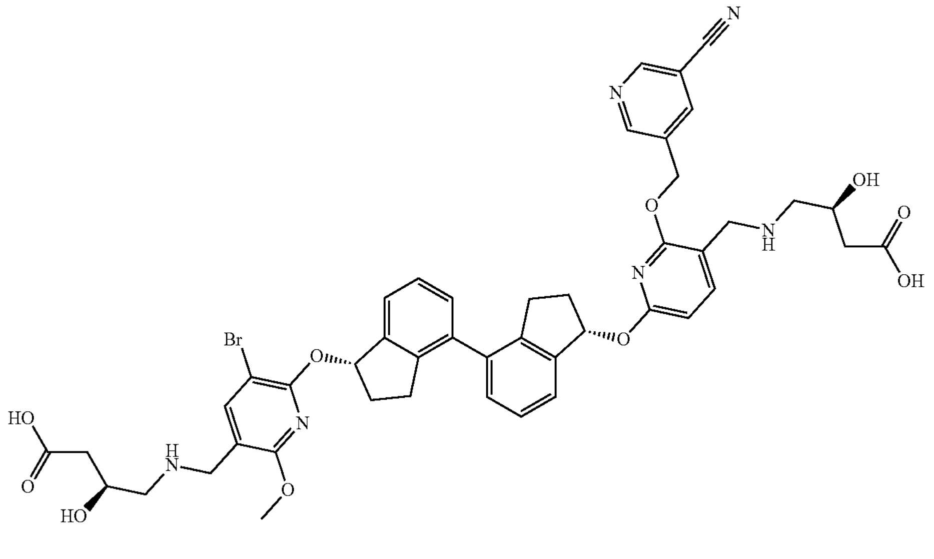 [SMILES: COc1nc(O[C@H]2CCc3c(-c4cccc5c4CC[C@@H]5Oc4ccc(CNC[C@@H](O)CC(=O)O)c(OCc5cncc(C#N)c5)n4)cccc32)c(Br)cc1CNC[C@@H](O)CC(=O)O] | 923.25 |

-continued
| Example No. | Structure | ES/MS (m/z, M + H+) |
|---|---|---|
| 679 | 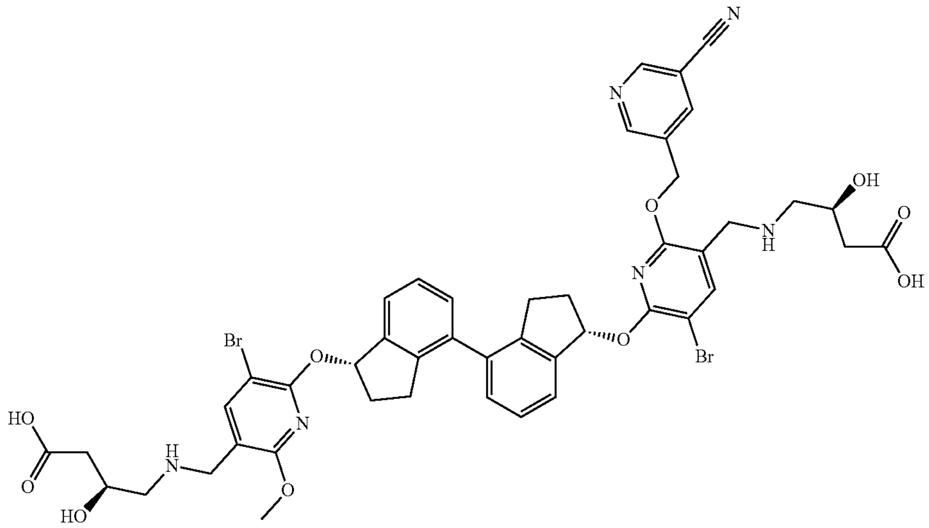 [SMILES: COc1nc(O[C@H]2CCc3c(-c4cccc5c4CC[C@@H]5Oc4nc(OCc5cncc(C#N)c5)c(CNC[C@@H](O)CC(=O)O)cc4Br)cccc32)c(Br)cc1CNC[C@@H](O)CC(=O)O] | 1003.13 |
| 681 | 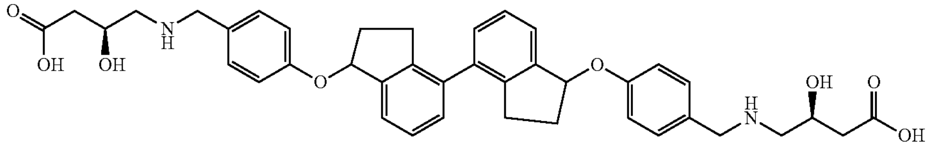 [SMILES: O=C(O)C[C@H](O)CNCc1ccc(OC2CCc3c(-c4cccc5c4CCC5Oc4ccc(CNC[C@@H](O)CC(=O)O)cc4)cccc32)cc1] | 679.93 |
| 682 | 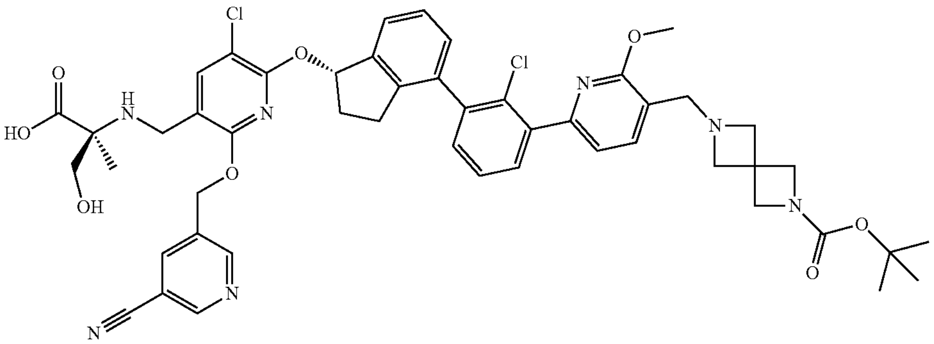 [SMILES: COc1nc(-c2cccc(-c3cccc4c3CC[C@@H]4Oc3nc(OCc4cncc(C#N)c4)c(CN[C@@](C)(CO)C(=O)O)cc3Cl)c2Cl)ccc1CN1CC2(C1)CN(C(=O)OC(C)(C)C)C2] | 936 |
| 683 | 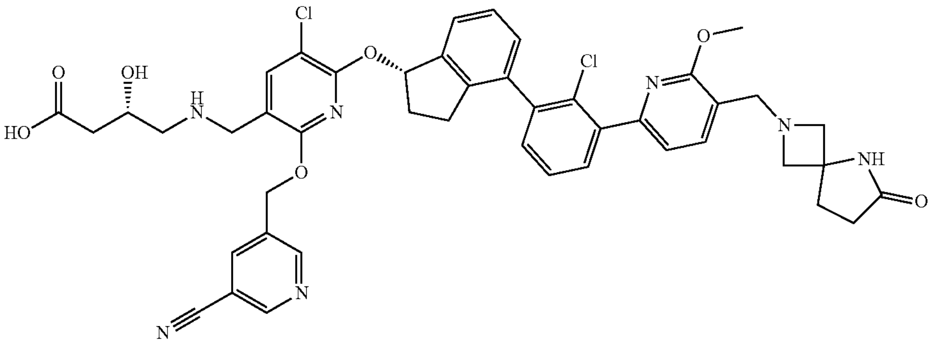 [SMILES: COc1nc(-c2cccc(-c3cccc4c3CC[C@@H]4Oc3nc(OCc4cncc(C#N)c4)c(CNC[C@@H](O)CC(=O)O)cc3Cl)c2Cl)ccc1CN1CC2(CCC(=O)N2)C1] | 863.9 |

-continued
| Example No. | Structure | ES/MS (m/z, M + H+) |
|---|---|---|
| 684 | 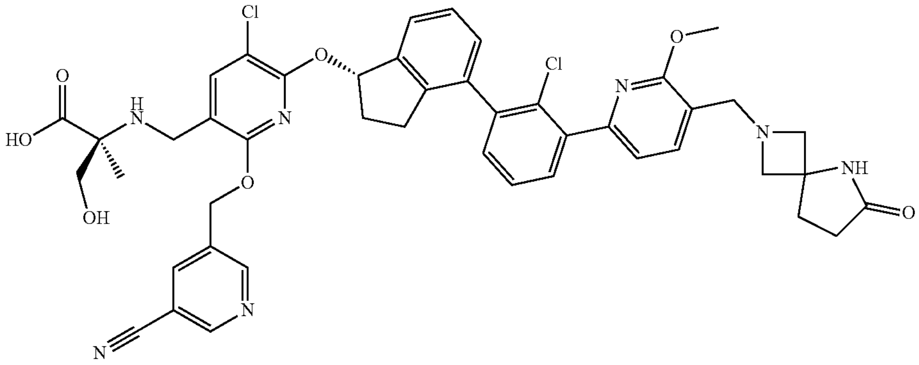 [SMILES: COc1nc(-c2cccc(-c3cccc4c3CC[C@@H]4Oc3nc(OCc4cncc(C#N)c4)c(CN[C@@](C)(CO)C(=O)O)cc3Cl)c2Cl)ccc1CN1CC2(CCC(=O)N2)C1] | 863.9 |
| 685 | 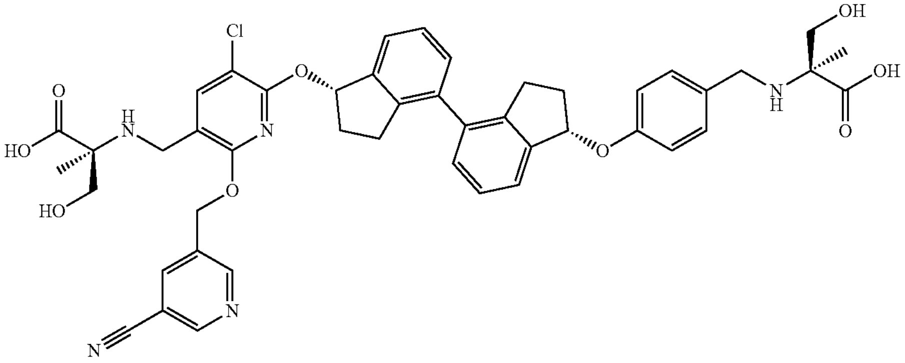 [SMILES: C[C@@](CO)(NCc1ccc(O[C@H]2CCc3c(-c4cccc5c4CC[C@@H]5Oc4nc(OCc5cncc(C#N)c5)c(CN[C@@](C)(CO)C(=O)O)cc4Cl)cccc32)cc1)C(=O)O] | 848 |
| 686 | 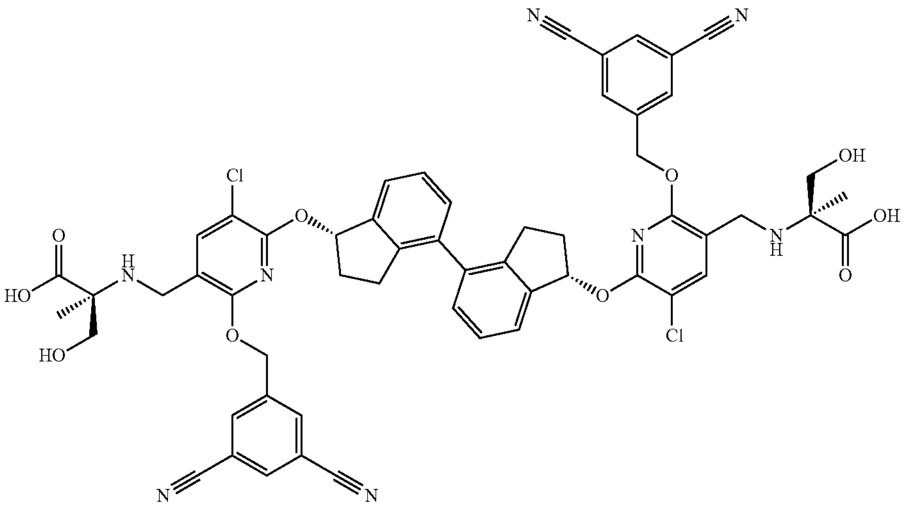 [SMILES: C[C@@](CO)(NCc1cc(Cl)c(O[C@H]2CCc3c(-c4cccc5c4CC[C@@H]5Oc4nc(OCc5cc(C#N)cc(C#N)c5)c(CN[C@@](C)(CO)C(=O)O)cc4Cl)cccc32)nc1OCc1cc(C#N)cc(C#N)c1)C(=O)O] | 1063 |

-continued
| Example No. | Structure | ES/MS (m/z, M + H+) |
|---|---|---|
| 687 | 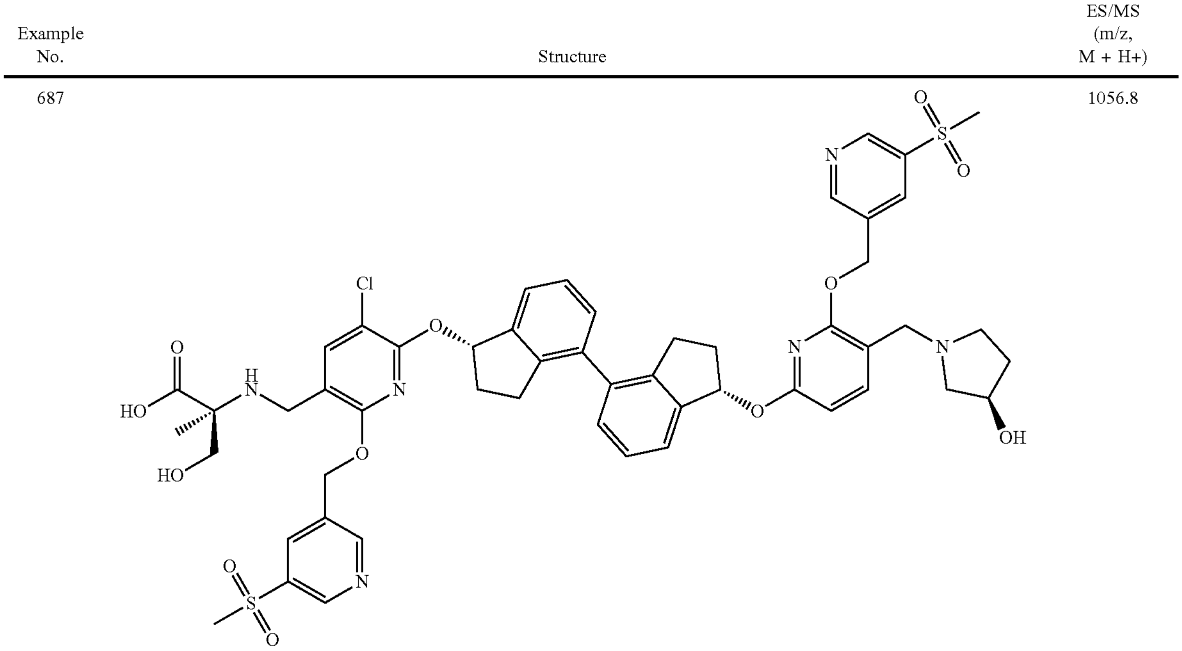 | 1056.8 |
| 688 | 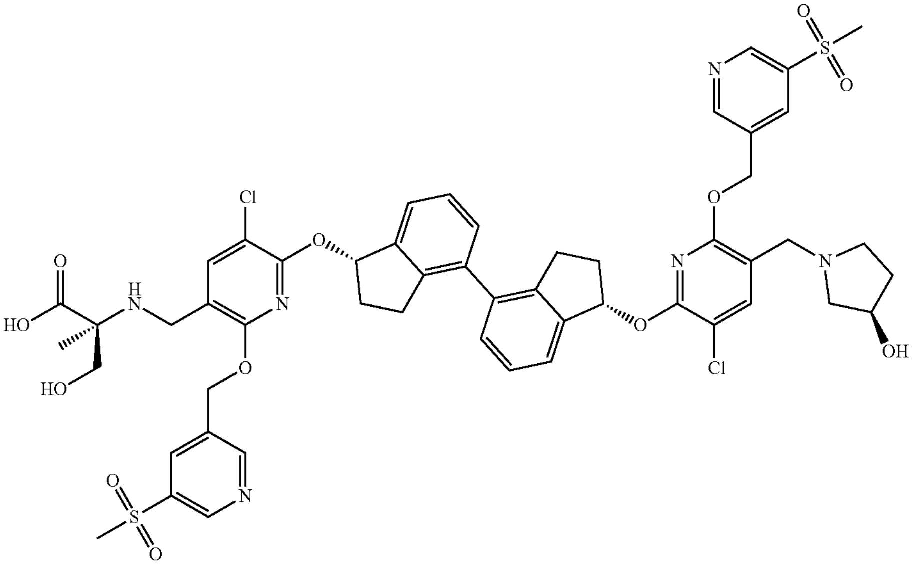 [SMILES: C[C@@](CO)(NCc1cc(Cl)c(O[C@H]2CCc3c(-c4cccc5c4CC[C@@H]5Oc4nc(OCc5cncc(S(C)(=O)=O)c5)c(CN5CC[C@@H](O)C5)cc4Cl)cccc32)nc1OCc1cncc(S(C)(=O)=O)c1)C(=O)O] | 1088.9 |
| 689 | 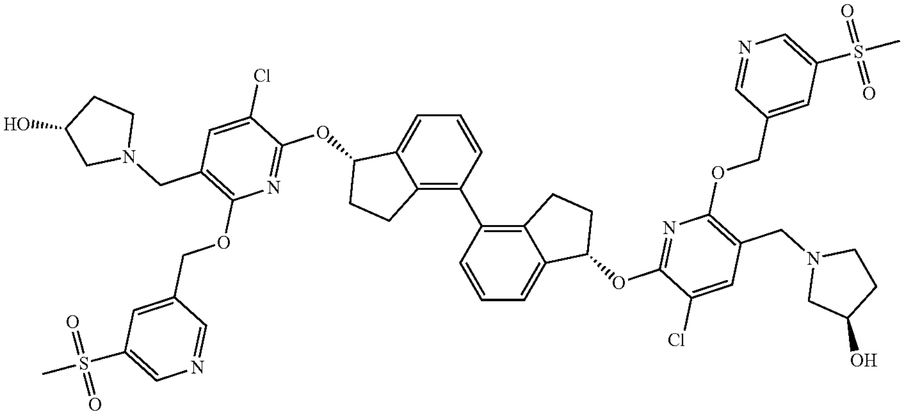 [SMILES: CS(=O)(=O)c1cncc(COc2nc(O[C@H]3CCc4c(-c5cccc6c5CC[C@@H]6Oc5nc(OCc6cncc(S(C)(=O)=O)c6)c(CN6CC[C@@H](O)C6)cc5Cl)cccc43)c(Cl)cc2CN2CC[C@@H](O)C2)c1] | 1056.8 |

-continued
| Example No. | Structure | ES/MS (m/z, M + H+) |
|---|---|---|
| 690 | 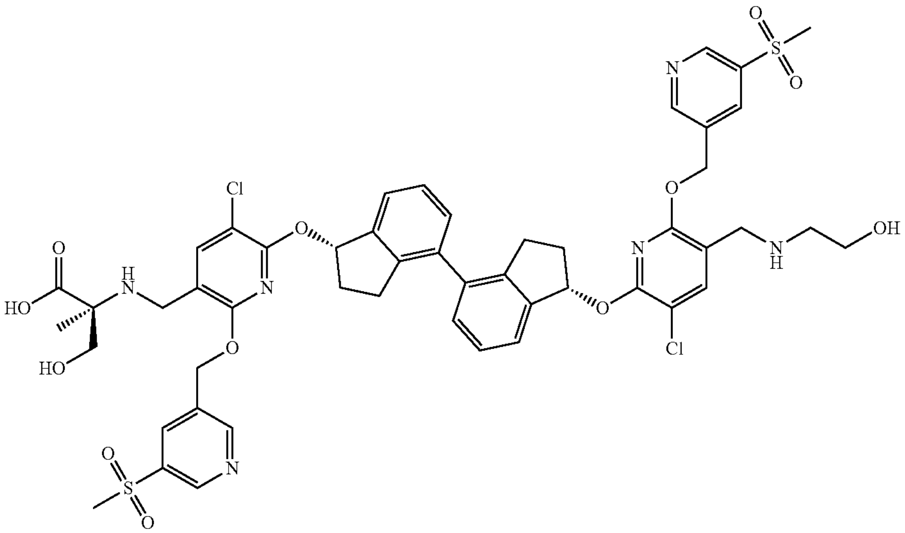 [SMILES: C[C@@](CO)(NCc1cc(Cl)c(O[C@H]2CCc3c(-c4cccc5c4CC[C@@H]5Oc4nc(OCc5cncc(S(C)(=O)=O)c5)c(CNCCO)cc4Cl)cccc32)nc1OCc1cncc(S(C)(=O)=O)c1)C(=O)O] | 1063.5 |
| 691 | 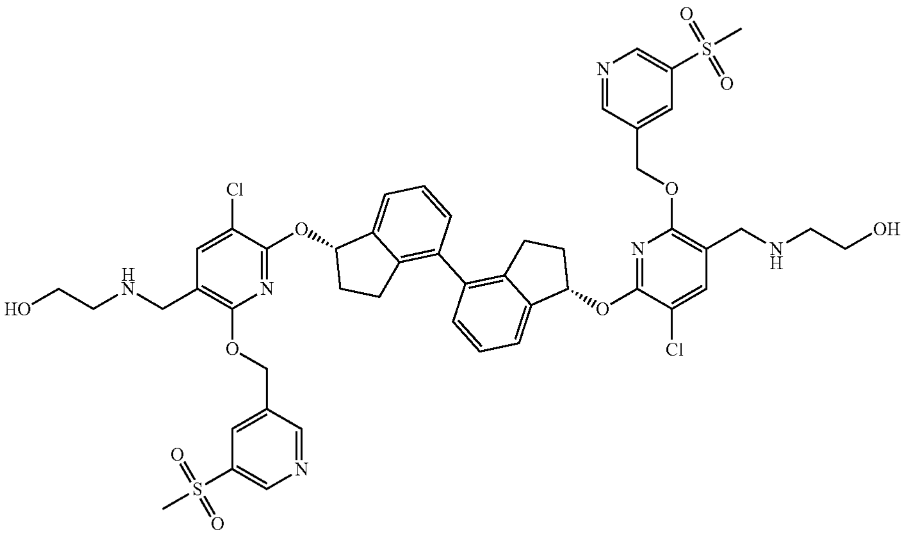 [SMILES: CS(=O)(=O)c1cncc(COc2nc(O[C@H]3CCc4c(-c5cccc6c5CC[C@@H]6Oc5nc(OCc6cncc(S(C)(=O)=O)c6)c(CNCCO)cc5Cl)cccc43)c(Cl)cc2CNCCO)c1] | 899.1 |

-continued
| Example No. | Structure | ES/MS (m/z, M + H+) |
|---|---|---|
| 692 | 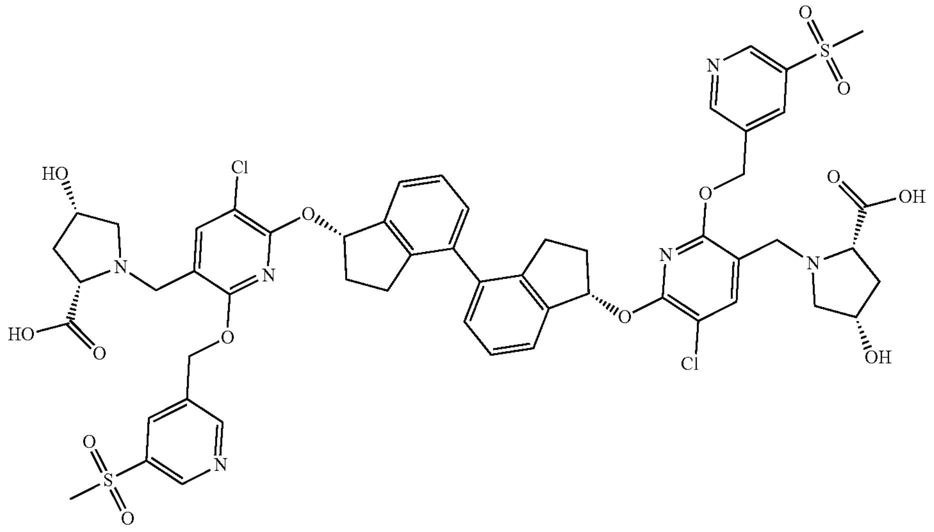 [SMILES: CS(=O)(=O)c1cncc(COc2nc(O[C@H]3CCc4c(-c5cccc6c5CC[C@@H]6Oc5nc(OCc6cncc(S(C)(=O)=O)c6)c(CN6C[C@@H](O)C[C@H]6C(=O)O)cc5Cl)cccc43)c(Cl)cc2CN2C[C@@H](O)C[C@H]2C(=O)O)c1] | 1121.7 |
| 693 | 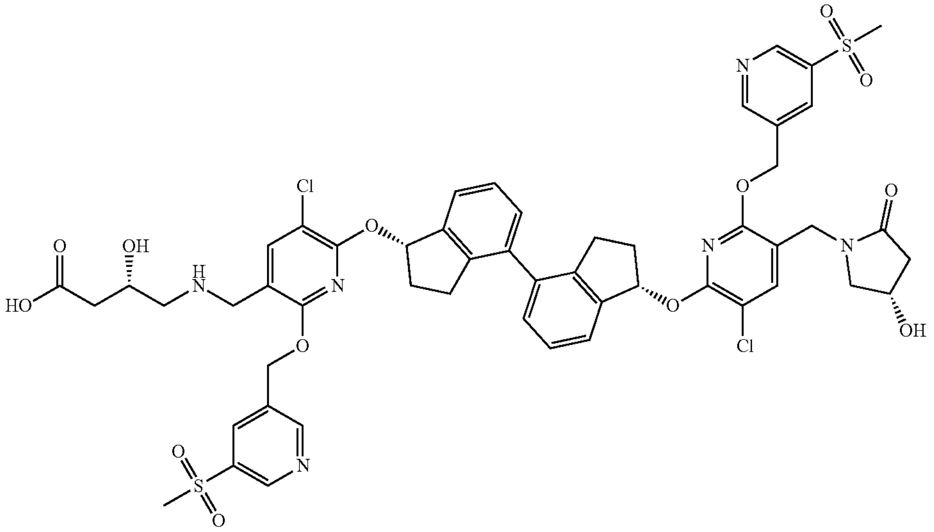 [SMILES: CS(=O)(=O)c1cncc(COc2nc(O[C@H]3CCc4c(-c5cccc6c5CC[C@@H]6Oc5nc(OCc6cncc(S(C)(=O)=O)c6)c(CN6C[C@@H](O)CC6=O)cc5Cl)cccc43)c(Cl)cc2CNC[C@@H](O)CC(=O)O)c1] | 1103.5 |
| 694 | 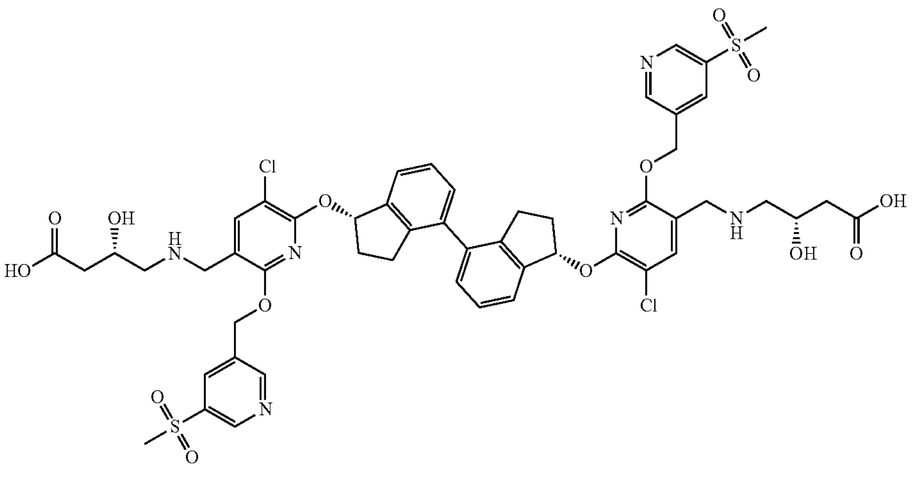 [SMILES: CS(=O)(=O)c1cncc(COc2nc(O[C@H]3CCc4c(-c5cccc6c5CC[C@@H]6Oc5nc(OCc6cncc(S(C)(=O)=O)c6)c(CNC[C@@H](O)CC(=O)O)cc5Cl)cccc43)c(Cl)cc2CNC[C@@H](O)CC(=O)O)c1] | 1121.3 |

-continued
| Example No. | Structure | ES/MS (m/z, M + H+) |
| --- | --- | --- |
| 695 | 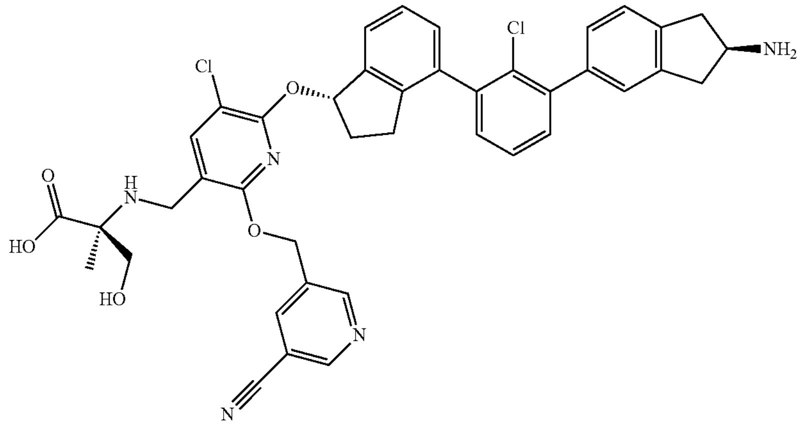 [SMILES: C[C@@](CO)(NCc1cc(Cl)c(O[C@H]2CCc3c(-c4cccc(-c5ccc6c(c5)C[C@H](N)C6)c4Cl)cccc32)nc1OCc1cncc(C#N)c1)C(=O)O] | 751.1 |
| 696 | 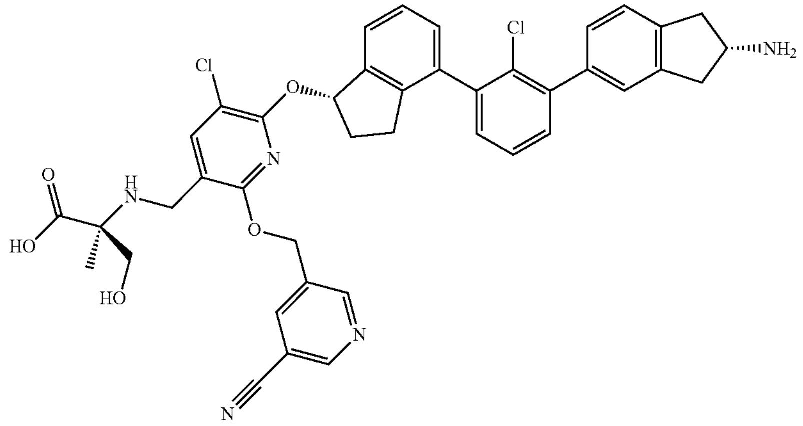 [SMILES: C[C@@](CO)(NCc1cc(Cl)c(O[C@H]2CCc3c(-c4cccc(-c5ccc6c(c5)C[C@@H](N)C6)c4Cl)cccc32)nc1OCc1cncc(C#N)c1)C(=O)O] | 750.8 |
| 697 | 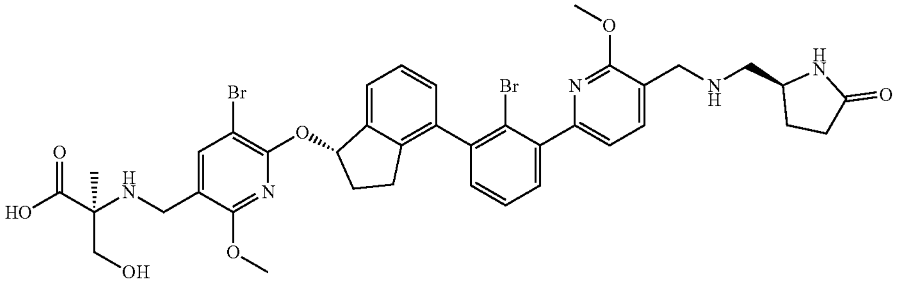 [SMILES: COc1nc(-c2cccc(-c3cccc4c3CC[C@@H]4Oc3nc(OC)c(CN[C@@](C)(CO)C(=O)O)cc3Br)c2Br)ccc1CNC[C@@H]1CCC(=O)N1] | 860.0 (M + Na)+ |
| 698 | 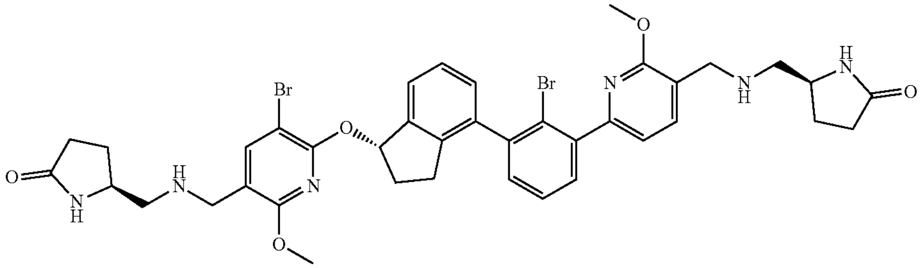 [SMILES: COc1nc(-c2cccc(-c3cccc4c3CC[C@@H]4Oc3nc(OC)c(CNC[C@@H]4CCC(=O)N4)cc3Br)c2Br)ccc1CNC[C@@H]1CCC(=O)N1] | 855.2 (M + Na)+ |

-continued
| Example No. | Structure | ES/MS (m/z, M + H+) |
|---|---|---|
| 699 | 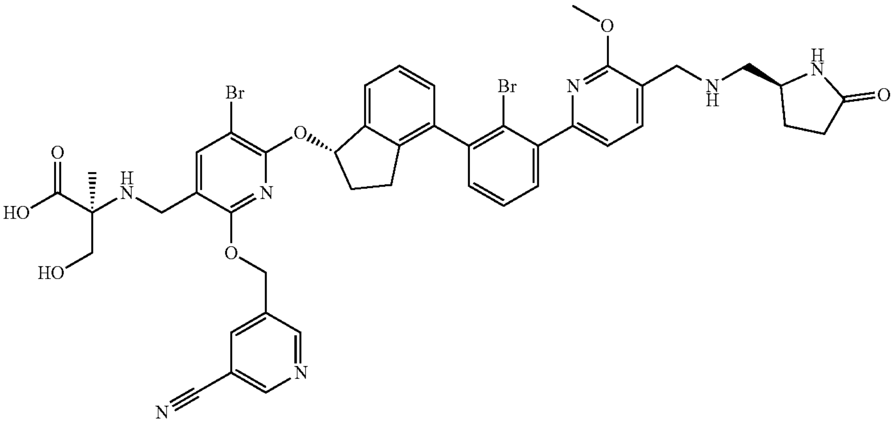 [SMILES: COc1nc(-c2cccc(-c3cccc4c3CC[C@@H]4Oc3nc(OCc4cncc(C#N)c4)c(CN[C@@](C)(CO)C(=O)O)cc3Cl)c2Br)ccc1CNC[C@@H]1CCC(=O)N1] | 940 |
| 700 | 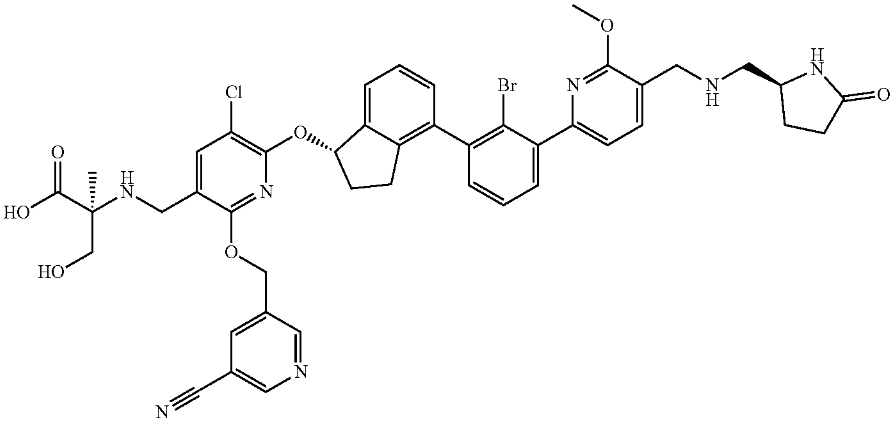 | 896.3 |
| 701 | 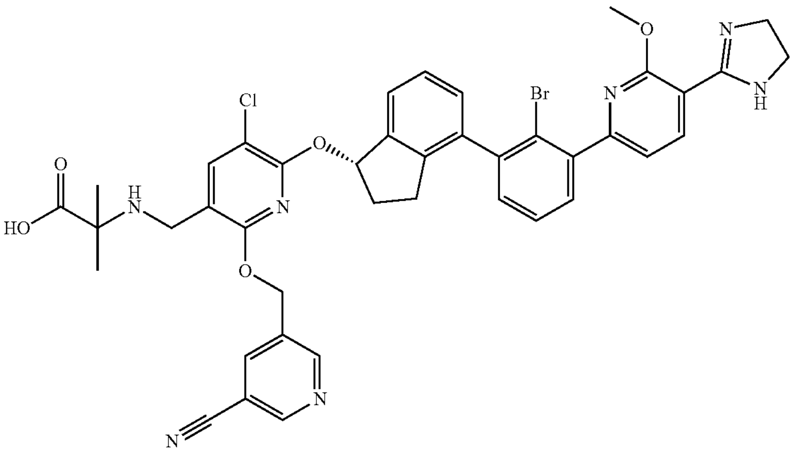 [SMILES: COc1nc(-c2cccc(-c3cccc4c3CC[C@@H]4Oc3nc(OCc4cncc(C#N)c4)c(CNC(C)(C)C(=O)O)cc3Cl)c2Br)ccc1C1=NCCN1] | 822.3 |

-continued
| Example No. | Structure | ES/MS (m/z, M + H+) |
|---|---|---|
| 702 | 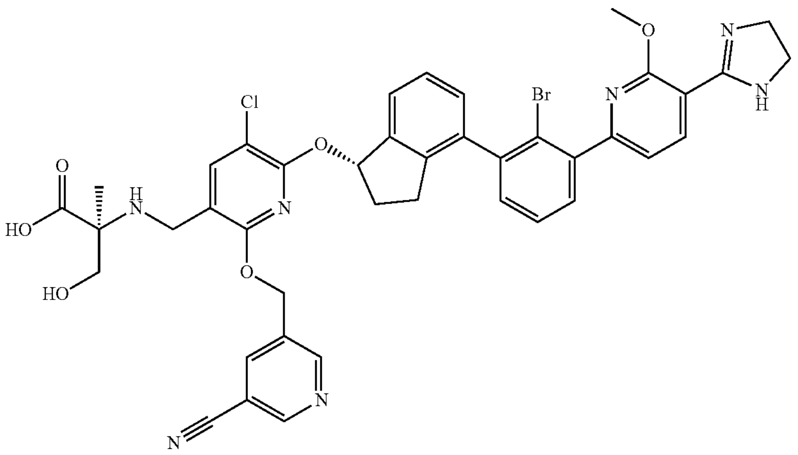 [SMILES: COc1nc(-c2cccc(-c3cccc4c3CC[C@@H]4Oc3nc(OCc4cncc(C#N)c4)c(CN[C@@](C)(CO)C(=O)O)cc3Cl)c2Br)ccc1C1=NCCN1] | 838.3 |
| 703 | 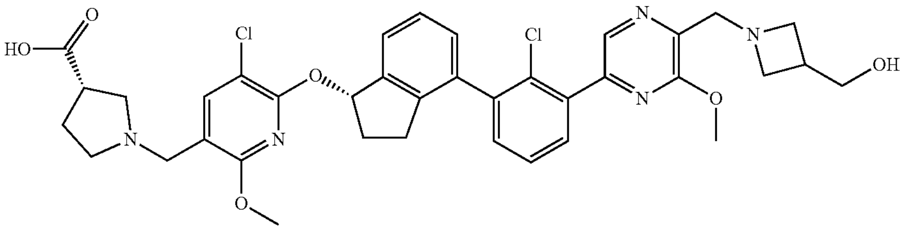 [SMILES: COc1nc(O[C@H]2CCc3c(-c4cccc(-c5cnc(CN6CC(CO)C6)c(OC)n5)c4Cl)cccc32)c(Cl)cc1CN1CC[C@H](C(=O)O)C1] | 719.992 |
| 704 | 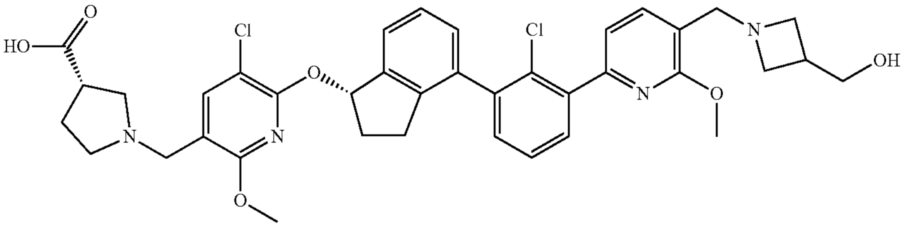 [SMILES: COc1nc(-c2cccc(-c3cccc4c3CC[C@@H]4Oc3nc(OC)c(CN4CC[C@H](C(=O)O)C4)cc3Cl)c2Cl)ccc1CN1CC(CO)C1] | 718.945 |
| 705 | 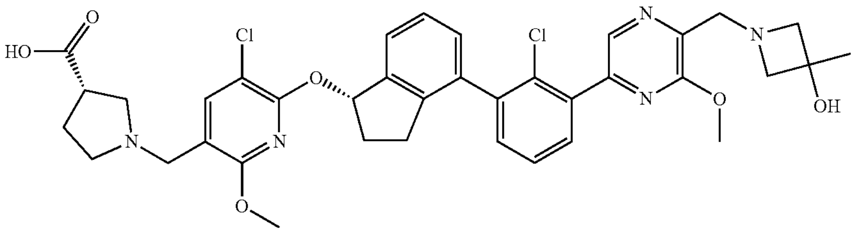 [SMILES: COc1nc(O[C@H]2CCc3c(-c4cccc(-c5cnc(CN6CC(C)(O)C6)c(OC)n5)c4Cl)cccc32)c(Cl)cc1CN1CC[C@H](C(=O)O)C1] | 719.956 |
| 706 | 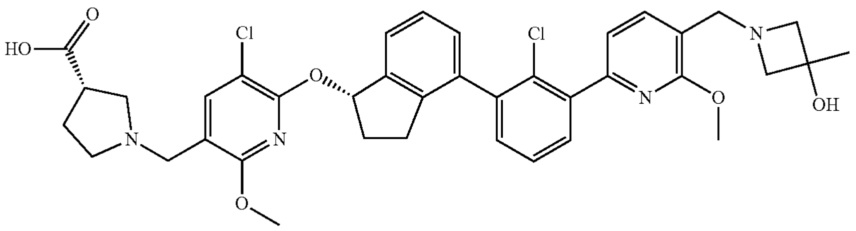 [SMILES: COc1nc(-c2cccc(-c3cccc4c3CC[C@@H]4Oc3nc(OC)c(CN4CC[C@H](C(=O)O)C4)cc3Cl)c2Cl)ccc1CN1CC(C)(O)C1] | 718.918 |

-continued
| Example No. | Structure | ES/MS (m/z, M + H+) |
|---|---|---|
| 707 | 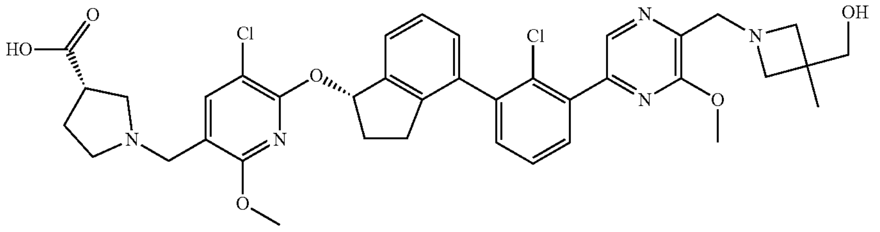 [SMILES: COc1nc(O[C@H]2CCc3c(-c4cccc(-c5cnc(CN6CC(C)(CO)C6)c(OC)n5)c4Cl)cccc32)c(Cl)cc1CN1CC[C@H](C(=O)O)C1] | 733.933 |
| 708 | 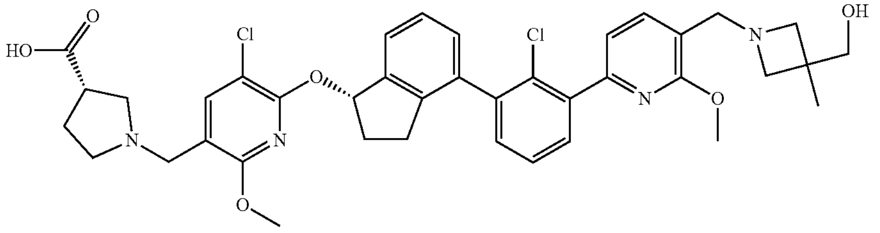 [SMILES: COc1nc(-c2cccc(-c3cccc4c3CC[C@@H]4Oc3nc(OC)c(CN4CC[C@H](C(=O)O)C4)cc3Cl)c2Cl)ccc1CN1CC(C)(CO)C1] | 732.974 |
| 709 | 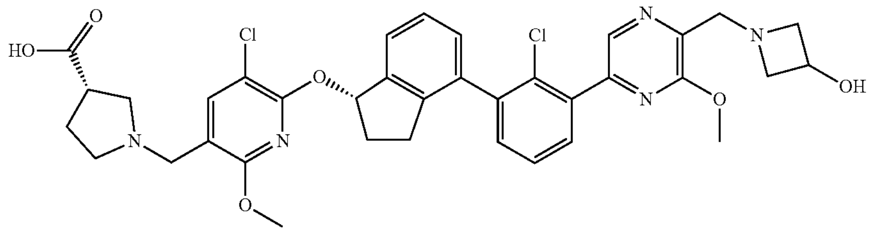 [SMILES: COc1nc(O[C@H]2CCc3c(-c4cccc(-c5cnc(CN6CC(O)C6)c(OC)n5)c4Cl)cccc32)c(Cl)cc1CN1CC[C@H](C(=O)O)C1] | 705.9 |
| 710 | 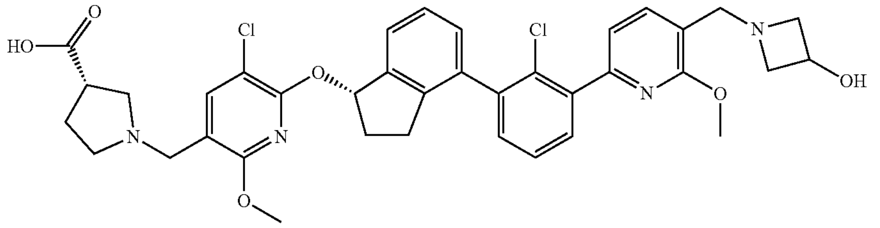 [SMILES: COc1nc(-c2cccc(-c3cccc4c3CC[C@@H]4Oc3nc(OC)c(CN4CC[C@H](C(=O)O)C4)cc3Cl)c2Cl)ccc1CN1CC(O)C1] | 704.884 |
| 711 | 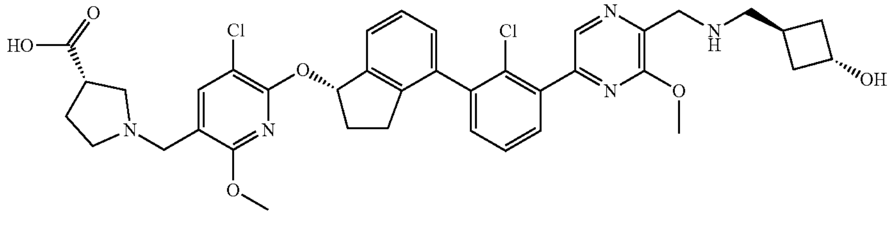 [SMILES: COc1nc(O[C@H]2CCc3c(-c4cccc(-c5cnc(CNC[C@H]6C[C@H](O)C6)c(OC)n5)c4Cl)cccc32)c(Cl)cc1CN1CC[C@H](C(=O)O)C1] | 733.881 |
| 712 | 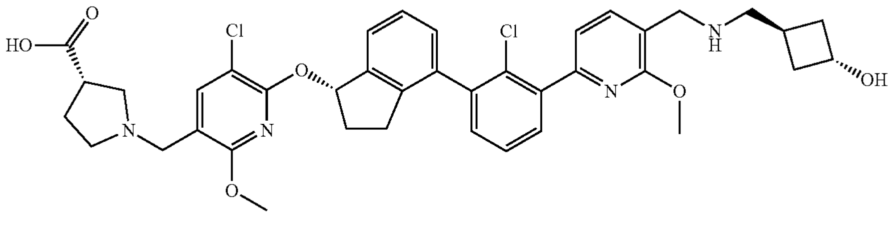 [SMILES: COc1nc(-c2cccc(-c3cccc4c3CC[C@@H]4Oc3nc(OC)c(CN4CC[C@H](C(=O)O)C4)cc3Cl)c2Cl)ccc1CNC[C@H]1C[C@H](O)C1] | 732.962 |

-continued
| Example No. | Structure | ES/MS (m/z, M + H+) |
|---|---|---|
| 713 | 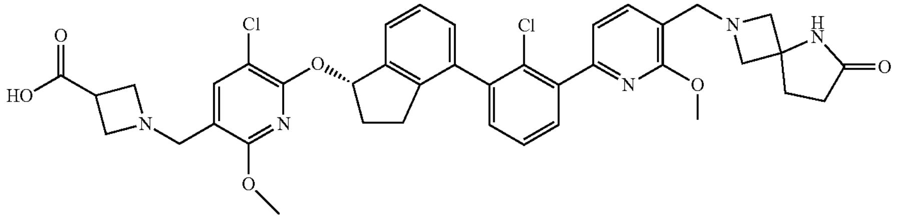 [SMILES: COc1nc(-c2cccc(-c3cccc4c3CC[C@@H]4Oc3nc(OC)c(CN4CC(C(=O)O)C4)cc3Cl)c2Cl)ccc1CN1CC2(CCC(=O)N2)C1] | 743.963 |
| 714 | 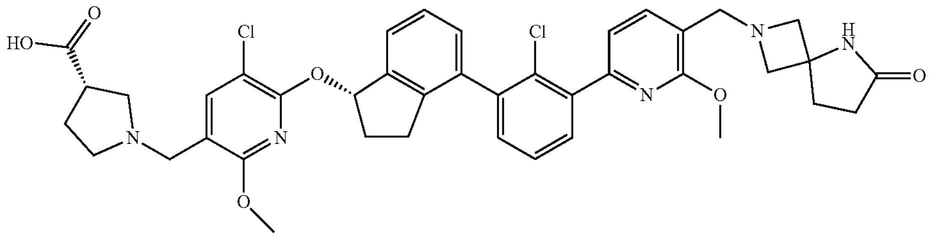 [SMILES: COc1nc(-c2cccc(-c3cccc4c3CC[C@@H]4Oc3nc(OC)c(CN4CC[C@H](C(=O)O)C4)cc3Cl)c2Cl)ccc1CN1CC2(CCC(=O)N2)C1] | 757.982 |
| 715 | 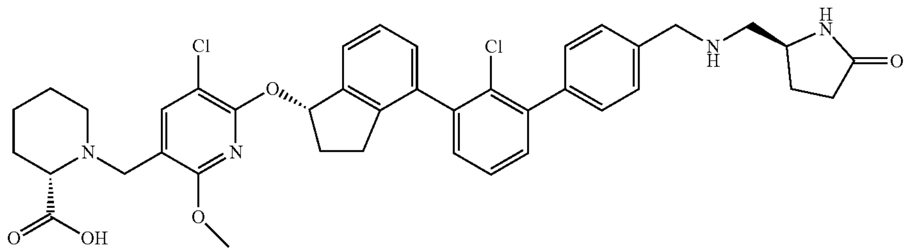 [SMILES: COc1nc(O[C@H]2CCc3c(-c4cccc(-c5ccc(CNC[C@@H]6CCC(=O)N6)cc5)c4Cl)cccc32)c(Cl)cc1CN1CCCC[C@H]1C(=O)O] | 729.004 |
| 716 | 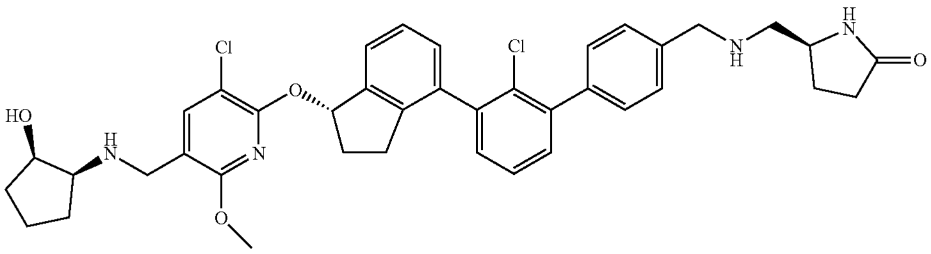 [SMILES: COc1nc(O[C@H]2CCc3c(-c4cccc(-c5ccc(CNC[C@@H]6CCC(=O)N6)cc5)c4Cl)cccc32)c(Cl)cc1CN[C@H]1CCC[C@H]1O] | 700.996 |
| 717 | 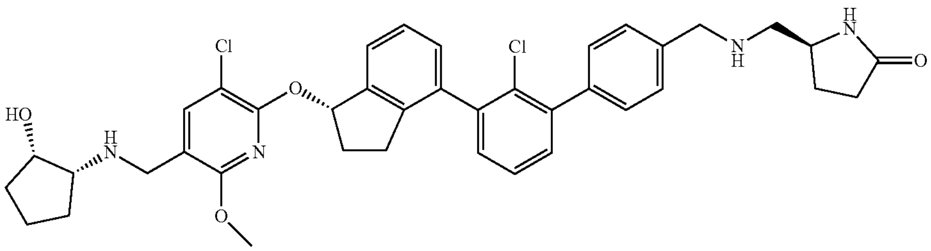 [SMILES: COc1nc(O[C@H]2CCc3c(-c4cccc(-c5ccc(CNC[C@@H]6CCC(=O)N6)cc5)c4Cl)cccc32)c(Cl)cc1CN[C@@H]1CCC[C@@H]1O] | 700.961 |
| 718 | 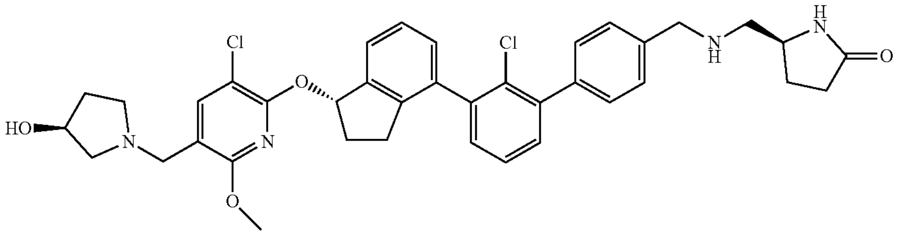 [SMILES: COc1nc(O[C@H]2CCc3c(-c4cccc(-c5ccc(CNC[C@@H]6CCC(=O)N6)cc5)c4Cl)cccc32)c(Cl)cc1CN1CC[C@H](O)C1] | 686.973 |

-continued
| Example No. | Structure | ES/MS (m/z, M + H+) |
|---|---|---|
| 719 | 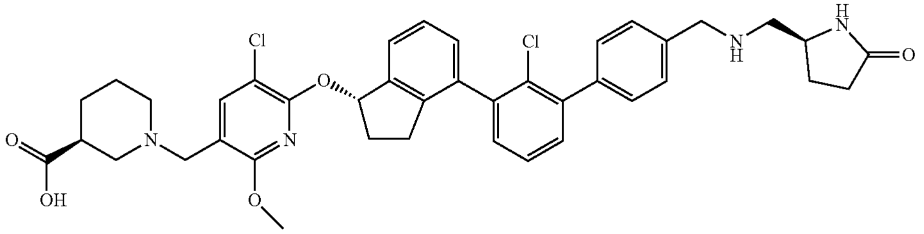 [SMILES: COc1nc(O[C@H]2CCc3c(-c4cccc(-c5ccc(CNC[C@@H]6CCC(=O)N6)cc5)c4Cl)cccc32)c(Cl)cc1CN1CCC[C@H](C(=O)O)C1] | 728.979 |
| 720 | 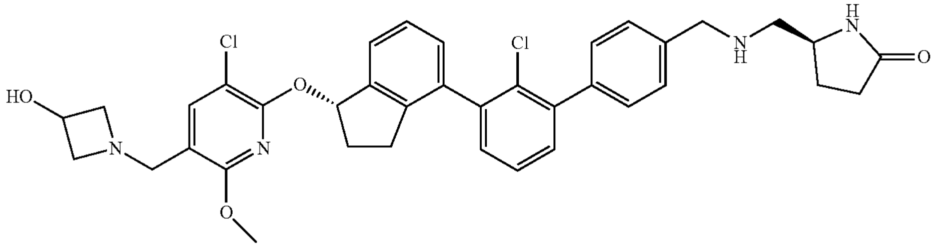 [SMILES: COc1nc(O[C@H]2CCc3c(-c4cccc(-c5ccc(CNC[C@@H]6CCC(=O)N6)cc5)c4Cl)cccc32)c(Cl)cc1CN1CC(O)C1] | 672.956 |
| 721 | 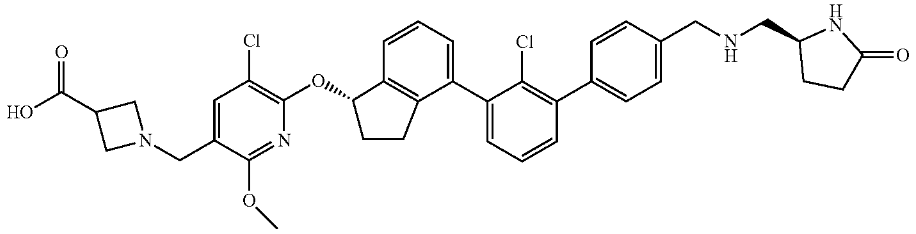 [SMILES: COc1nc(O[C@H]2CCc3c(-c4cccc(-c5ccc(CNC[C@@H]6CCC(=O)N6)cc5)c4Cl)cccc32)c(Cl)cc1CN1CC(C(=O)O)C1] | 700.951 |
| 722 | 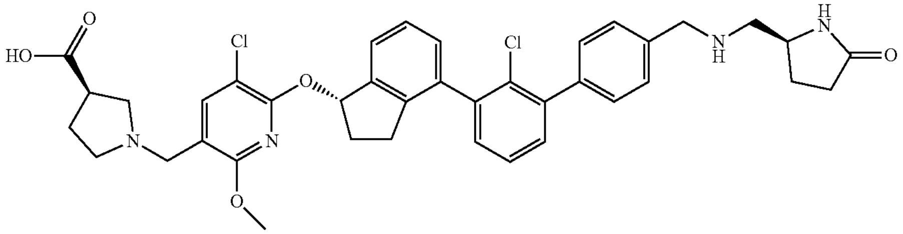 [SMILES: COc1nc(O[C@H]2CCc3c(-c4cccc(-c5ccc(CNC[C@@H]6CCC(=O)N6)cc5)c4Cl)cccc32)c(Cl)cc1CN1CC[C@@H](C(=O)O)C1] | 715.035 |
| 723 | 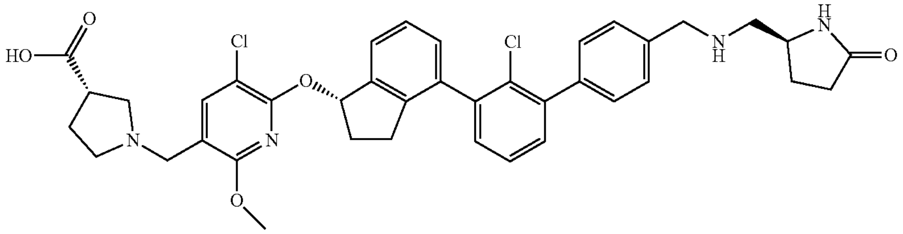 [SMILES: COc1nc(O[C@H]2CCc3c(-c4cccc(-c5ccc(CNC[C@@H]6CCC(=O)N6)cc5)c4Cl)cccc32)c(Cl)cc1CN1CC[C@H](C(=O)O)C1] | 714.998 |
| 724 | 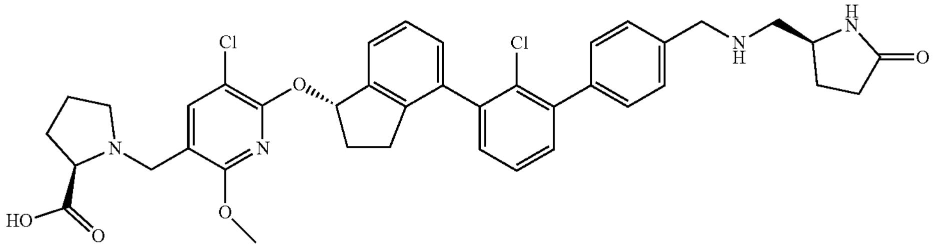 [SMILES: COc1nc(O[C@H]2CCc3c(-c4cccc(-c5ccc(CNC[C@@H]6CCC(=O)N6)cc5)c4Cl)cccc32)c(Cl)cc1CN1CCC[C@@H]1C(=O)O] | 715.028 |

-continued
| Example No. | Structure | ES/MS (m/z, M + H+) |
|---|---|---|
| 725 | 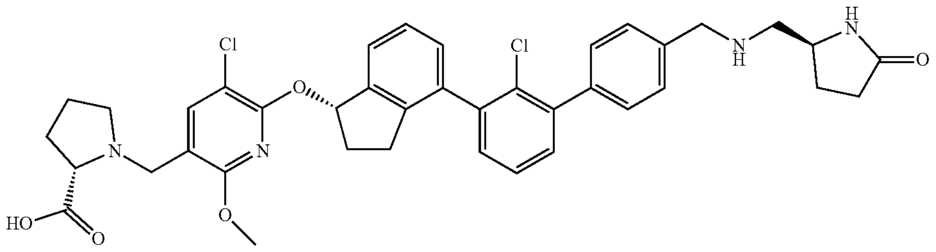 [SMILES: COc1nc(O[C@H]2CCc3c(-c4cccc(-c5ccc(CNC[C@@H]6CCC(=O)N6)cc5)c4Cl)cccc32)c(Cl)cc1CN1CCC[C@H]1C(=O)O] | 714.965 |
| 726 | 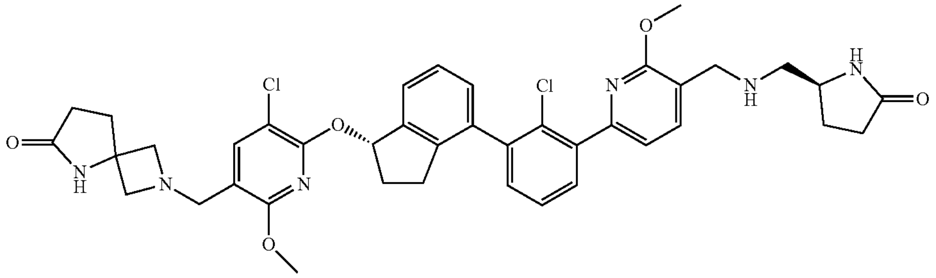 [SMILES: COc1nc(-c2cccc(-c3cccc4c3CC[C@@H]4Oc3nc(OC)c(CN4CC5(CCC(=O)N5)C4)cc3Cl)c2Cl)ccc1CNC[C@@H]1CCC(=O)N1] | 756.972 |
| 727 | 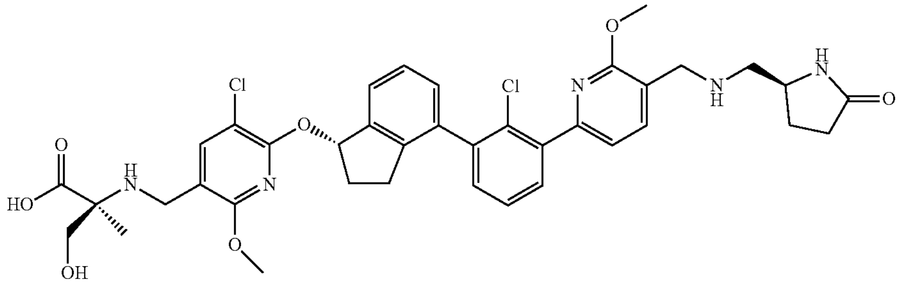 [SMILES: COc1nc(-c2cccc(-c3cccc4c3CC[C@@H]4Oc3nc(OC)c(CN[C@@](C)(CO)C(=O)O)cc3Cl)c2Cl)ccc1CNC[C@@H]1CCC(=O)N1] | 749.9 |
| 728 | 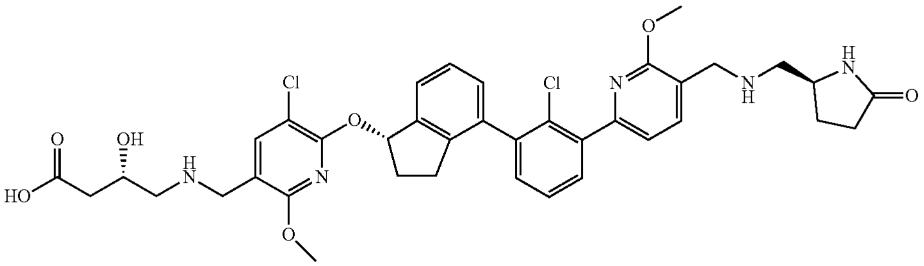 [SMILES: COc1nc(-c2cccc(-c3cccc4c3CC[C@@H]4Oc3nc(OC)c(CNC[C@@H](O)CC(=O)O)cc3Cl)c2Cl)ccc1CNC[C@@H]1CCC(=O)N1] | 750.001 |
| 729 | 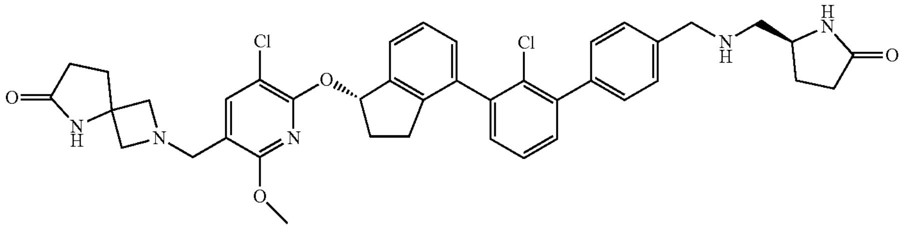 [SMILES: COc1nc(O[C@H]2CCc3c(-c4cccc(-c5ccc(CNC[C@@H]6CCC(=O)N6)cc5)c4Cl)cccc32)c(Cl)cc1CN1CC2(CCC(=O)N2)C1] | 726.012 |

-continued
| Example No. | Structure | ES/MS (m/z, M + H+) |
|---|---|---|
| 730 | 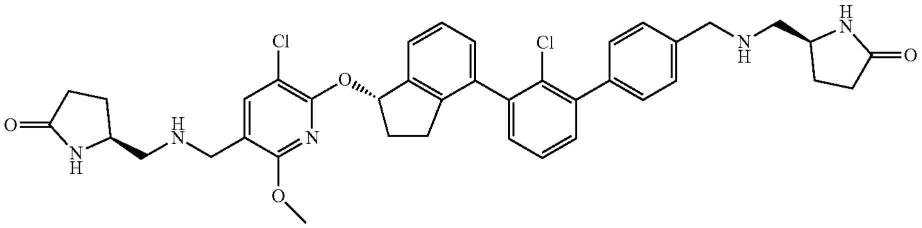 [SMILES: COc1nc(O[C@H]2CCc3c(-c4cccc(-c5ccc(CNC[C@@H]6CCC(=O)N6)cc5)c4Cl)cccc32)c(Cl)cc1CNC[C@@H]1CCC(=O)N1] | 713.977 |
| 731 | 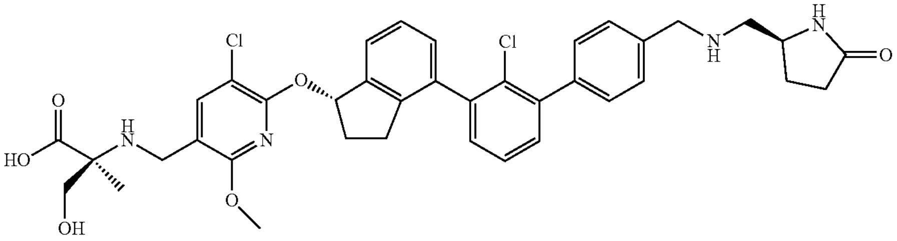 [SMILES: COc1nc(O[C@H]2CCc3c(-c4cccc(-c5ccc(CNC[C@@H]6CCC(=O)N6)cc5)c4Cl)cccc32)c(Cl)cc1CN[C@@](C)(CO)C(=O)O] | 718.946 |
| 732 | 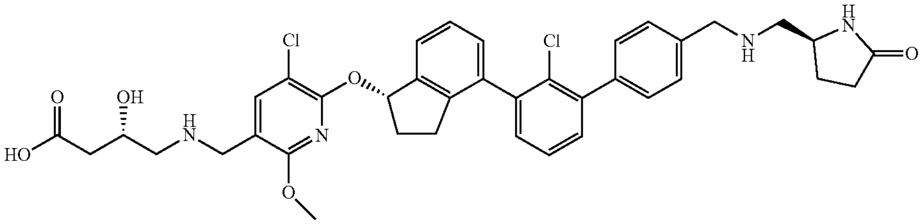 [SMILES: COc1nc(O[C@H]2CCc3c(-c4cccc(-c5ccc(CNC[C@@H]6CCC(=O)N6)cc5)c4Cl)cccc32)c(Cl)cc1CNC[C@@H](O)CC(=O)O] | 718.958 |
| 733 | 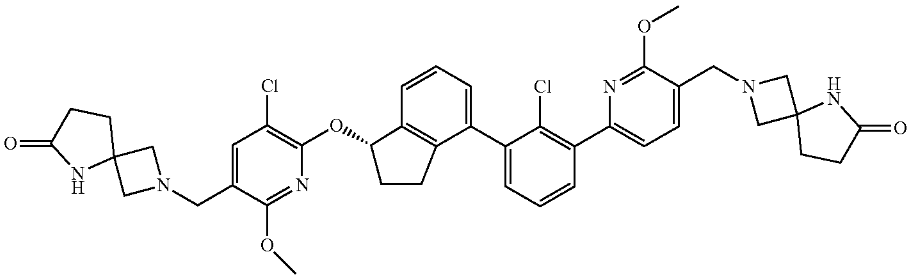 [SMILES: COc1nc(-c2cccc(-c3cccc4c3CC[C@@H]4Oc3nc(OC)c(CN4CC5(CCC(=O)N5)C4)cc3Cl)c2Cl)ccc1CN1CC2(CCC(=O)N2)C1] | 769.015 |
| 734 | 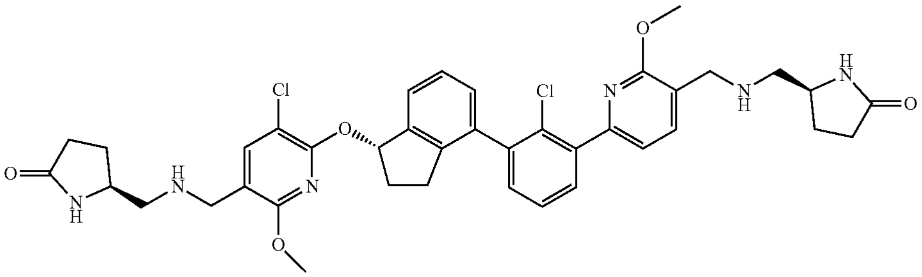 [SMILES: COc1nc(-c2cccc(-c3cccc4c3CC[C@@H]4Oc3nc(OC)c(CNC[C@@H]4CCC(=O)N4)cc3Cl)c2Cl)ccc1CNC[C@@H]1CCC(=O)N1] | 744.933 |

-continued
| Example No. | Structure | ES/MS (m/z, M + H+) |
|---|---|---|
| 735 | 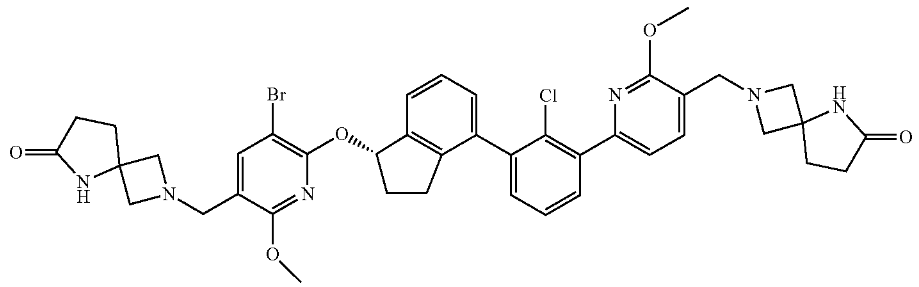 [SMILES: COc1nc(-c2cccc(-c3cccc4c3CC[C@@H]4Oc3nc(OC)c(CN4CC5(CCC(=O)N5)C4)cc3Br)c2Cl)ccc1CN1CC2(CCC(=O)N2)C1] | 812.906 |
| 736 | 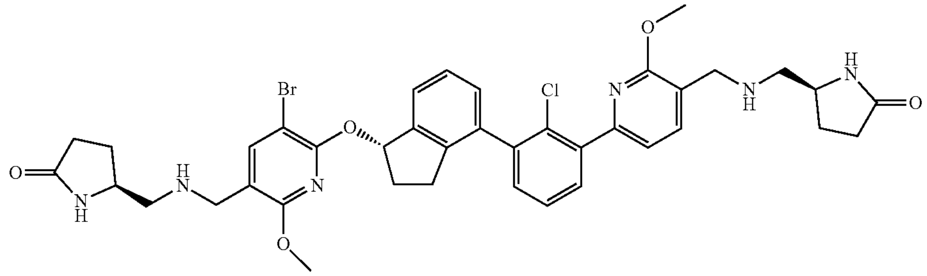 | 788.853 |
| 737 | 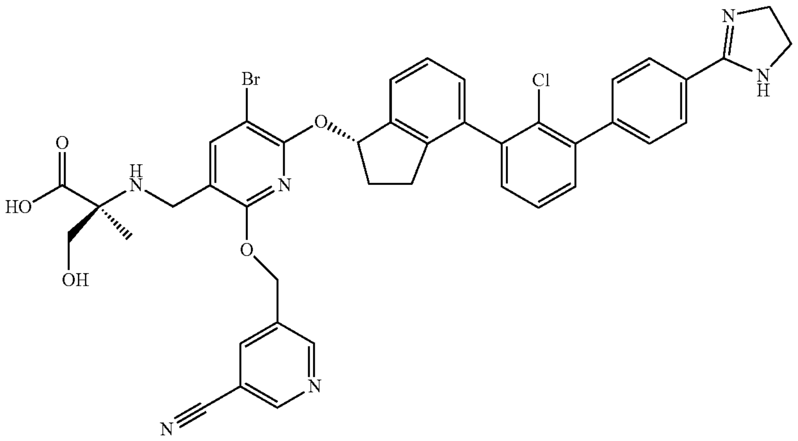 [SMILES: C[C@@](CO)(NCc1cc(Br)c(O[C@H]2CCc3c(-c4cccc(-c5ccc(C6=NCCN6)cc5)c4Cl)cccc32)nc1OCc1cncc(C#N)c1)C(=O)O] | 807.022 |
| 738 | 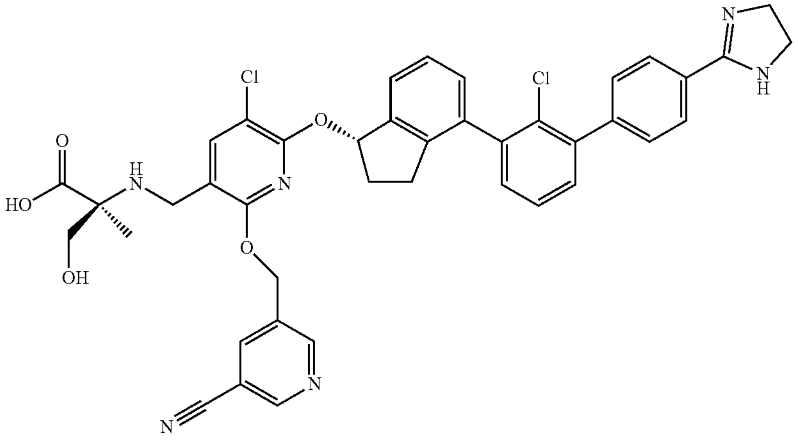 [SMILES: C[C@@](CO)(NCc1cc(Cl)c(O[C@H]2CCc3c(-c4cccc(-c5ccc(C6=NCCN6)cc5)c4Cl)cccc32)nc1OCc1cncc(C#N)c1)C(=O)O] | 763.09 |

-continued
| Example No. | Structure | ES/MS (m/z, M + H+) |
|---|---|---|
| 739 | 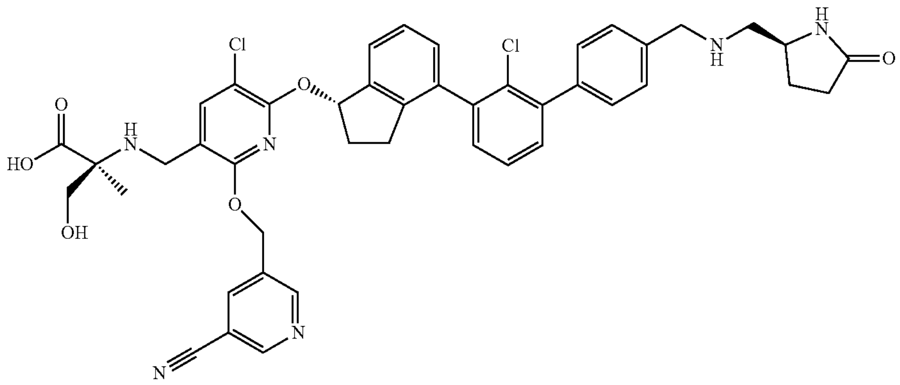 [SMILES: C[C@@](CO)(NCc1cc(Cl)c(O[C@H]2CCc3c(-c4cccc(-c5ccc(CNC[C@@H]6CCC(=O)N6)cc5)c4Cl)cccc32)nc1OCc1cncc(C#N)c1)C(=O)O] | 788.853 |
| 740 | 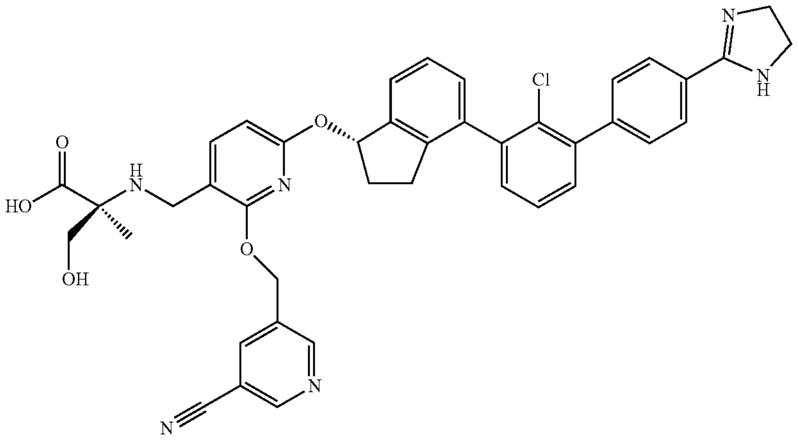 [SMILES: C[C@@](CO)(NCc1ccc(O[C@H]2CCc3c(-c4cccc(-c5ccc(C6=NCCN6)cc5)c4Cl)cccc32)nc1OCc1cncc(C#N)c1)C(=O)O] | 729.093 |
| 741 | 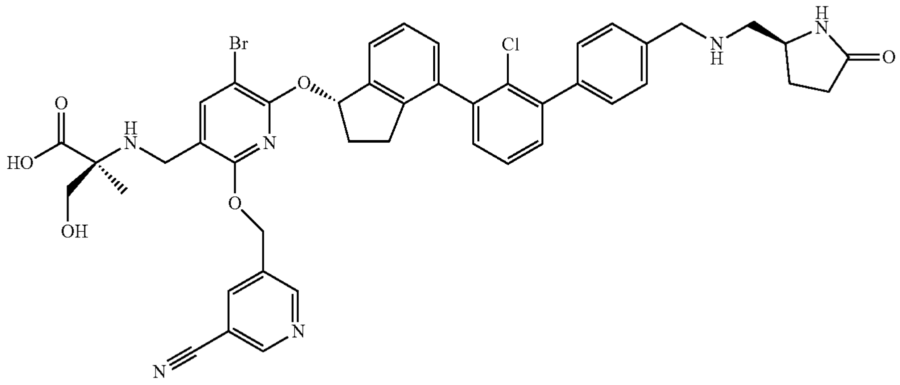 [SMILES: C[C@@](CO)(NCc1cc(Br)c(O[C@H]2CCc3c(-c4cccc(-c5ccc(CNC[C@@H]6CCC(=O)N6)cc5)c4Cl)cccc32)nc1OCc1cncc(C#N)c1)C(=O)O] | 864.968 |

-continued
| Example No. | Structure | ES/MS (m/z, M + H+) |
|---|---|---|
| 742 | 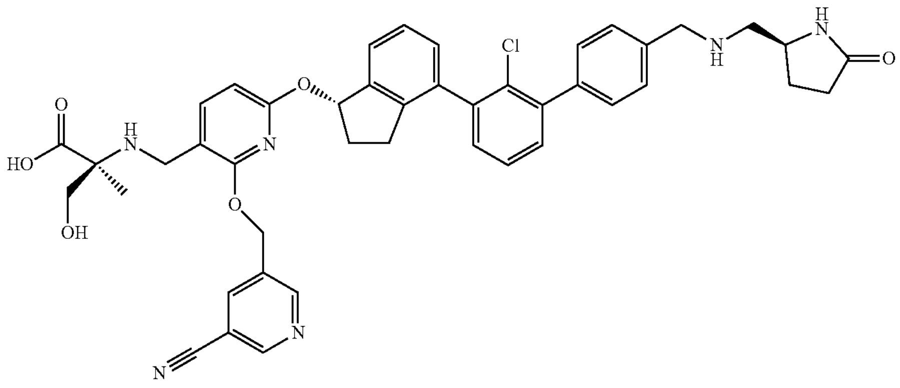 [SMILES: C[C@@](CO)(NCc1ccc(O[C@H]2CCc3c(-c4cccc(-c5ccc(CNC[C@@H]6CCC(=O)N6)cc5)c4Cl)cccc32)nc1OCc1cncc(C#N)c1)C(=O)O] | 787.071 |
| 743 | 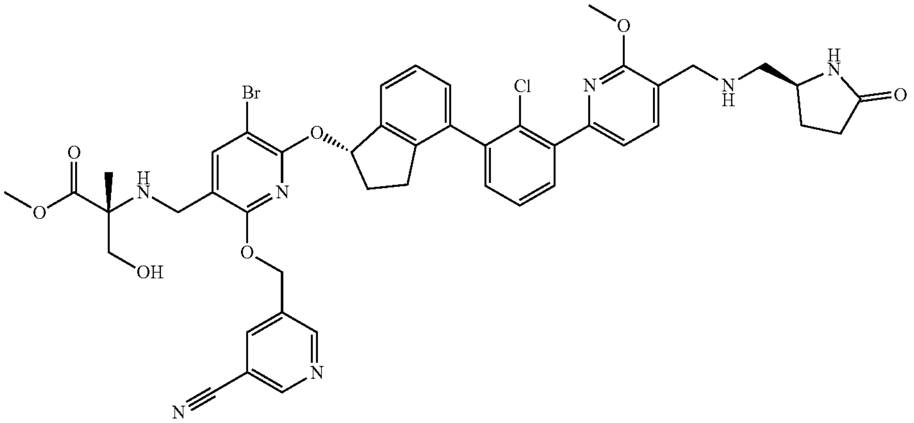 [SMILES: COC(=O)[C@@](C)(CO)NCc1cc(Br)c(O[C@H]2CCc3c(-c4cccc(-c5ccc(CNC[C@@H]6CCC(=O)N6)c(OC)n5)c4Cl)cccc32)nc1OCc1cncc(C#N)c1] | 910.49 |
| 744 | 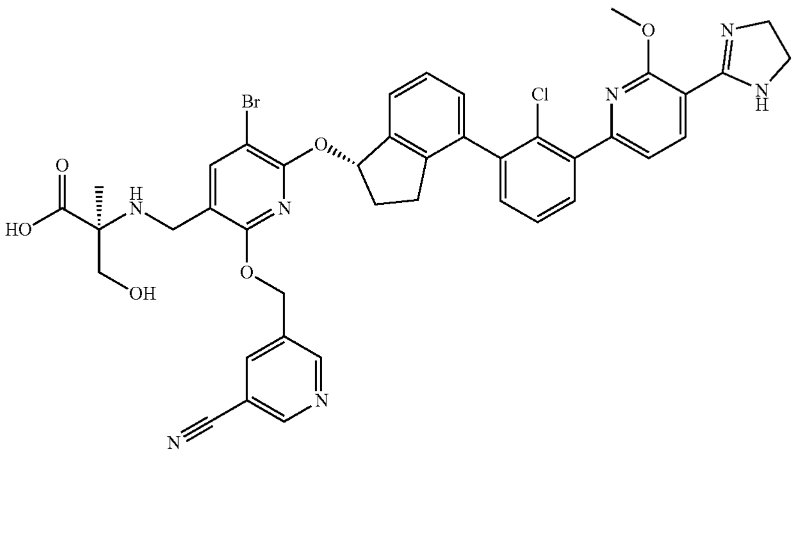 | 838.88 |

-continued
| Example No. | Structure | ES/MS (m/z, M + H+) |
|---|---|---|
| 745 | 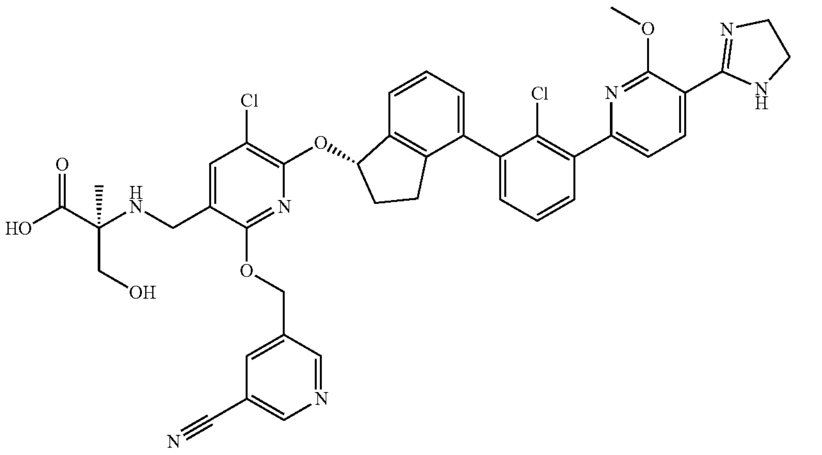 [SMILES: COc1nc(-c2cccc(-c3cccc4c3CC[C@@H]4Oc3nc(OCc4cncc(C#N)c4)c(CN[C@@](C)(CO)C(=O)O)cc3Cl)c2Cl)ccc1C1=NCCN1] | 794.76 |
| 746 | 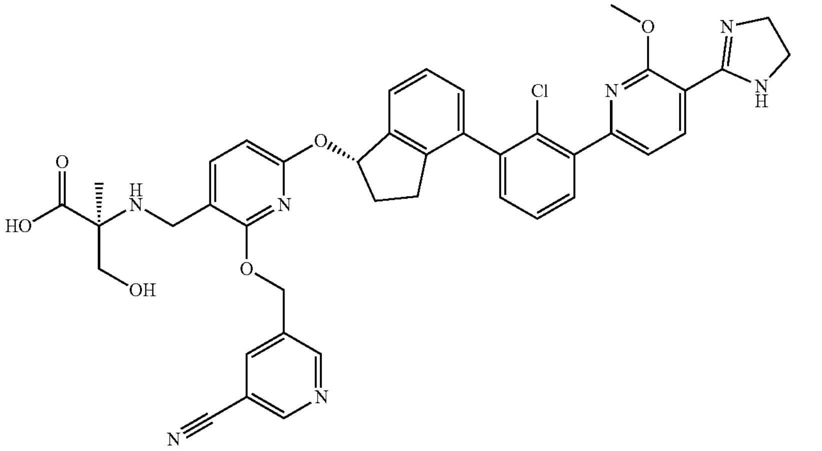 [SMILES: COc1nc(-c2cccc(-c3cccc4c3CC[C@@H]4Oc3ccc(CN[C@@](C)(CO)C(=O)O)c(OCc4cncc(C#N)c4)n3)c2Cl)ccc1C1=NCCN1] | 760.86 |
| 747 | 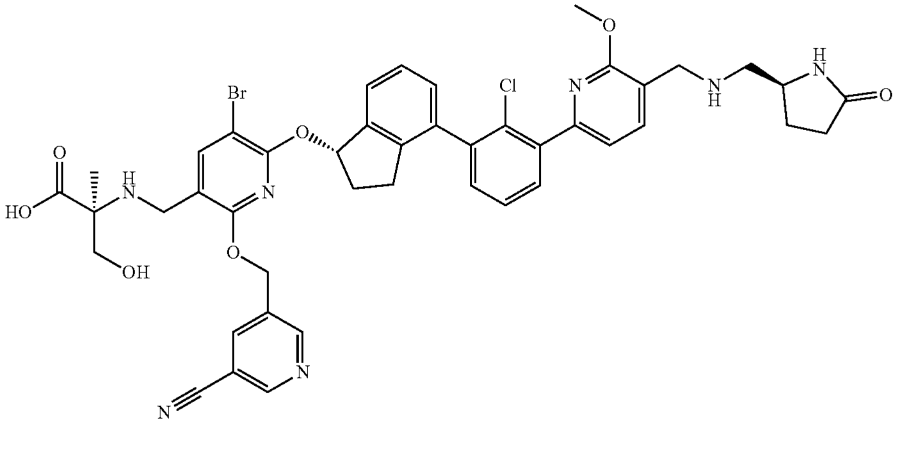 [SMILES: COc1nc(-c2cccc(-c3cccc4c3CC[C@@H]4Oc3nc(OCc4cncc(C#N)c4)c(CN[C@@](C)(CO)C(=O)O)cc3Br)c2Cl)ccc1CNC[C@@H]1CCC(=O)N1] | 896.48 |

-continued
| Example No. | Structure | ES/MS (m/z, M + H+) |
|---|---|---|
| 748 | 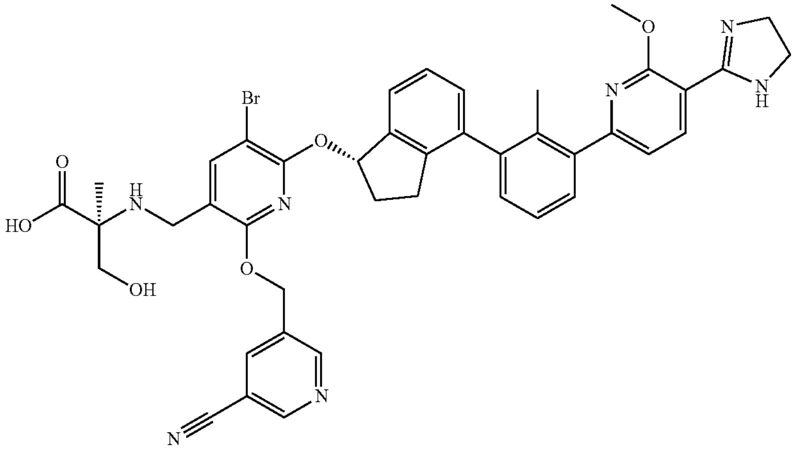 [SMILES: COc1nc(-c2cccc(-c3cccc4c3CC[C@@H]4Oc3nc(OCc4cncc(C#N)c4)c(CN[C@@](C)(CO)C(=O)O)cc3Cl)c2C)ccc1C1=NCCN1] | 818.59 |
| 749 | 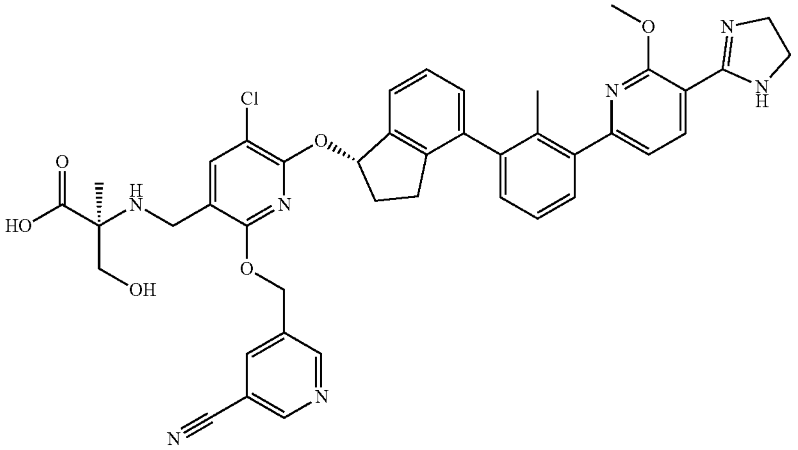 | 774.74 |
| 750 | 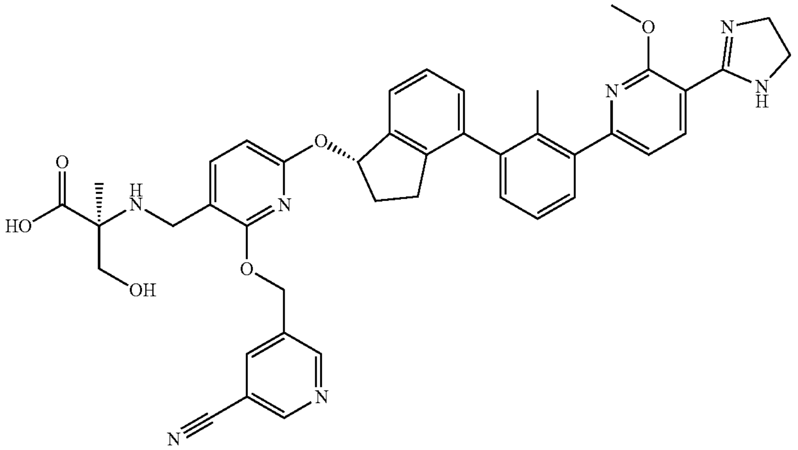 | 740.48 |

-continued
| Example No. | Structure | ES/MS (m/z, M + H+) |
|---|---|---|
| 751 | 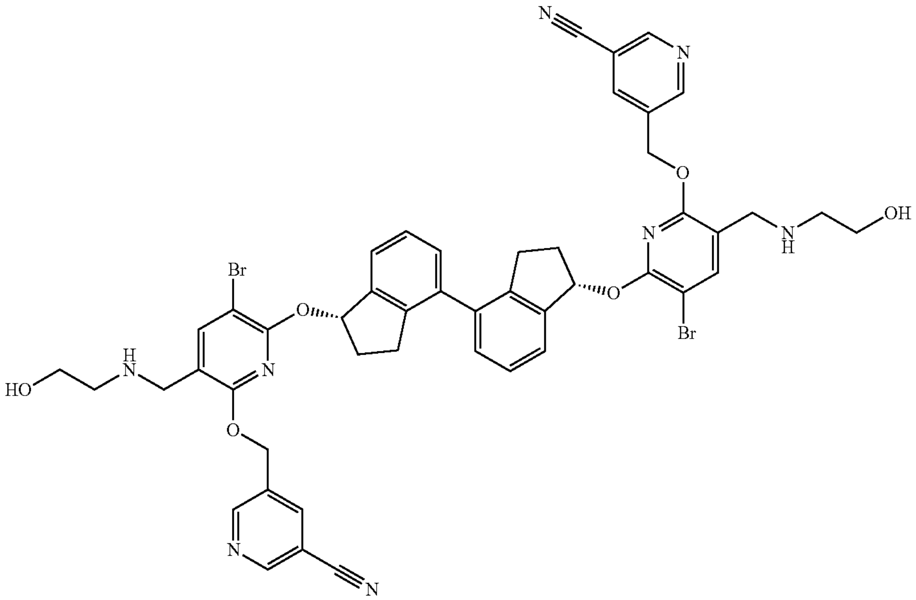 [SMILES: N#Cc1cncc(COc2nc(O[C@H]3CCc4c(-c5cccc6c5CC[C@@H]6Oc5nc(OCc6cncc(C#N)c6)c(CNCCO)cc5Br)cccc43)c(Br)cc2CNCCO)c1] | 987.2 |
| 752 | 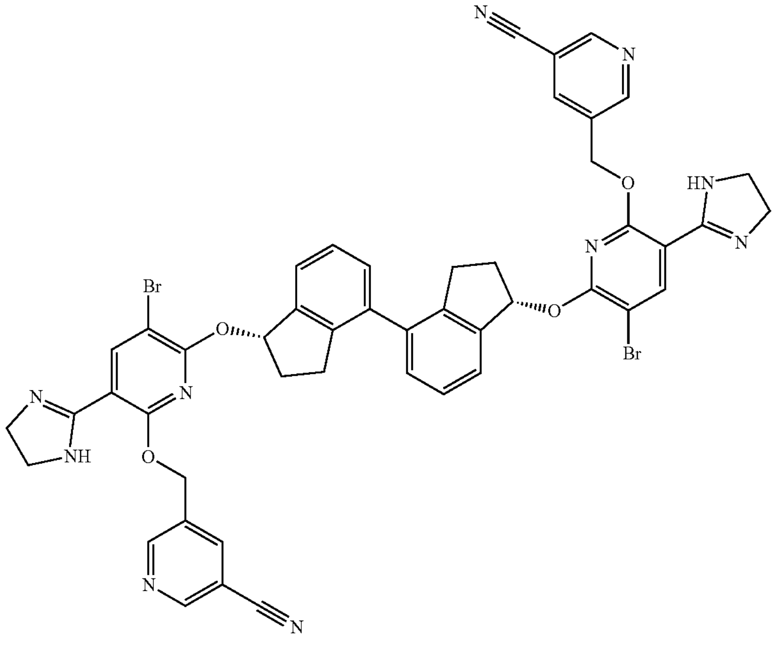 [SMILES: N#Cc1cncc(COc2nc(O[C@H]3CCc4c(-c5cccc6c5CC[C@@H]6Oc5nc(OCc6cncc(C#N)c6)c(C6=NCCN6)cc5Br)cccc43)c(Br)cc2C2=NCCN2)c1] | 977.78 |
| 753 | 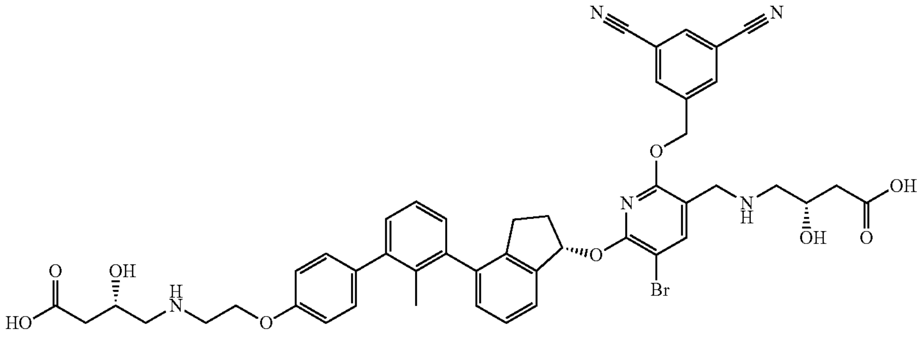 [SMILES: Cc1c(-c2ccc(OCCNC[C@@H](O)CC(=O)O)cc2)cccc1-c1cccc2c1CC[C@@H]2Oc1nc(OCc2cc(C#N)cc(C#N)c2)c(CNC[C@@H](O)CC(=O)O)cc1Br] | 903.94 |

-continued
| Example No. | Structure | ES/MS (m/z, M + H+) |
|---|---|---|
| 754 | 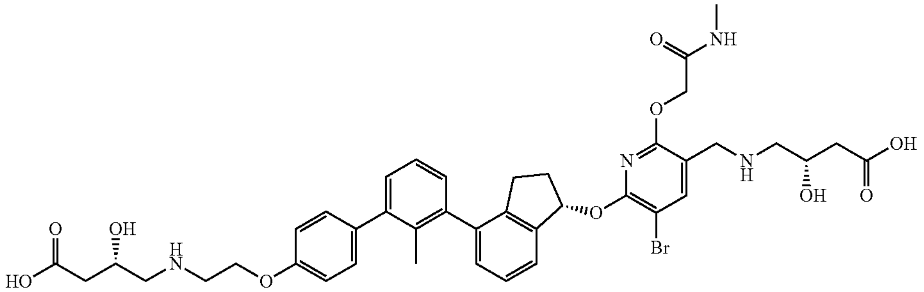 [SMILES: CNC(=O)COc1nc(O[C@H]2CCc3c(-c4cccc(-c5ccc(OCCNC[C@@H](O)CC(=O)O)cc5)c4C)cccc32)c(Br)cc1CNC[C@@H](O)CC(=O)O] | 835.11 |
| 755 | 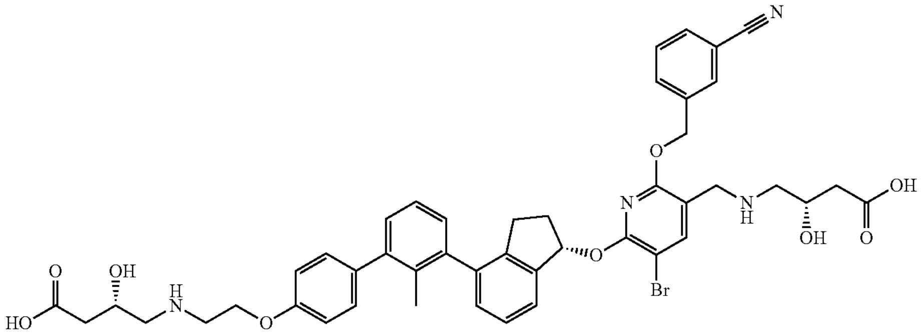 [SMILES: Cc1c(-c2ccc(OCCNC[C@@H](O)CC(=O)O)cc2)cccc1-c1cccc2c1CC[C@@H]2Oc1nc(OCc2cccc(C#N)c2)c(CNC[C@@H](O)CC(=O)O)cc1Br] | 879.99 |
| 756 | 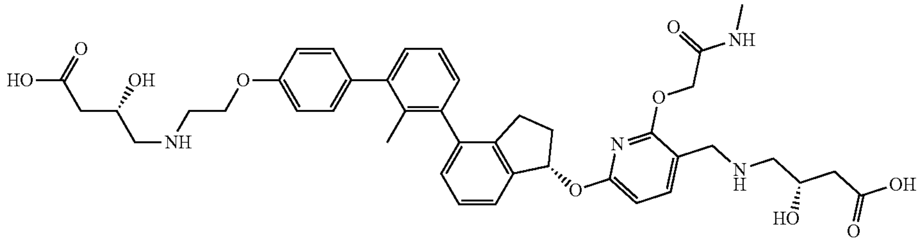 [SMILES: CNC(=O)COc1nc(O[C@H]2CCc3c(-c4cccc(-c5ccc(OCCNC[C@@H](O)CC(=O)O)cc5)c4C)cccc32)ccc1CNC[C@@H](O)CC(=O)O] | 757.06 |
| 757 | 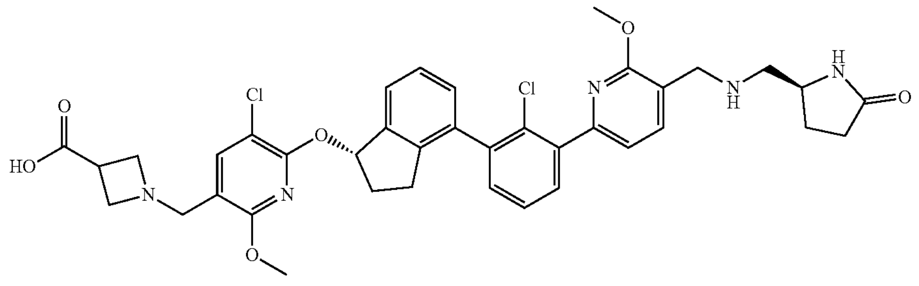 [SMILES: COc1nc(-c2cccc(-c3cccc4c3CC[C@@H]4Oc3nc(OC)c(CN4CC(C(=O)O)C4)cc3Cl)c2Cl)ccc1CNC[C@@H]1CCC(=O)N1] | 731.99 |
| 758 | 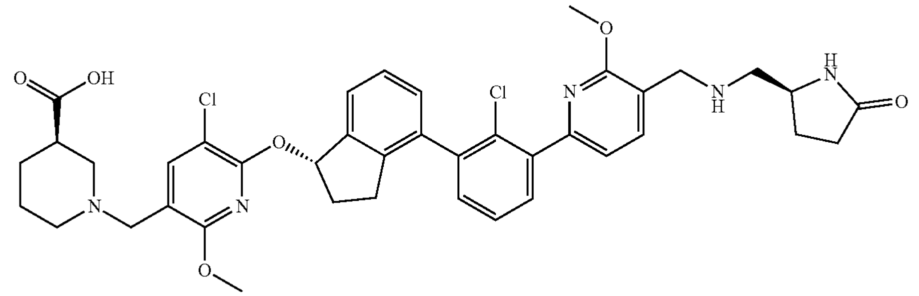 [SMILES: COc1nc(-c2cccc(-c3cccc4c3CC[C@@H]4Oc3nc(OC)c(CN4CCC[C@@H](C(=O)O)C4)cc3Cl)c2Cl)ccc1CNC[C@@H]1CCC(=O)N1] | 761.23 |

-continued
| Example No. | Structure | ES/MS (m/z, M + H+) |
|---|---|---|
| 759 | 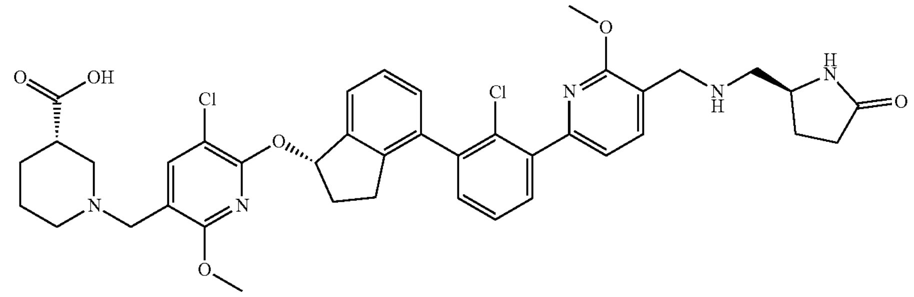 [SMILES: COc1nc(-c2cccc(-c3cccc4c3CC[C@@H]4Oc3nc(OC)c(CN4CCC[C@H](C(=O)O)C4)cc3Cl)c2Cl)ccc1CNC[C@@H]1CCC(=O)N1] | 760.12 |
| 760 | 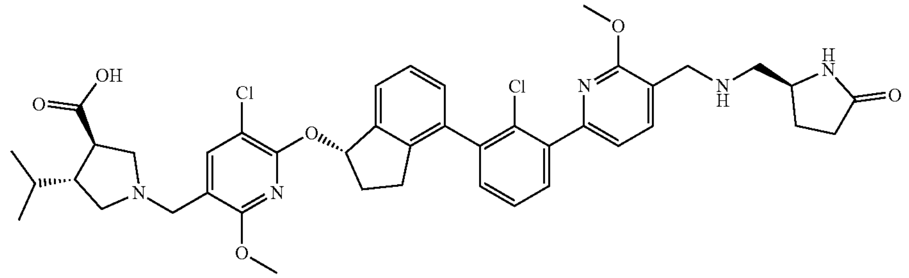 [SMILES: COc1nc(-c2cccc(-c3cccc4c3CC[C@@H]4Oc3nc(OC)c(CN4C[C@H](C(=O)O)[C@@H](C(C)C)C4)cc3Cl)c2Cl)ccc1CNC[C@@H]1CCC(=O)N1] | 789.08 |
| 761 | 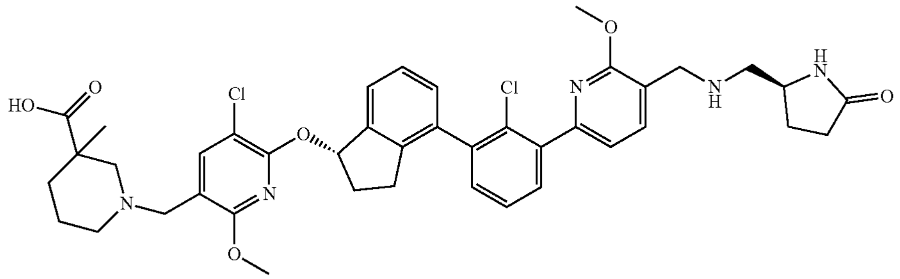 [SMILES: COc1nc(-c2cccc(-c3cccc4c3CC[C@@H]4Oc3nc(OC)c(CN4CCCC(C)(C(=O)O)C4)cc3Cl)c2Cl)ccc1CNC[C@@H]1CCC(=O)N1] | 774.14 |
| 762 | 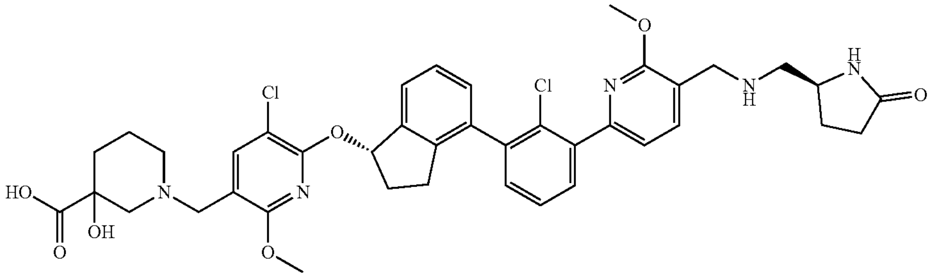 [SMILES: COc1nc(-c2cccc(-c3cccc4c3CC[C@@H]4Oc3nc(OC)c(CN4CCCC(O)(C(=O)O)C4)cc3Cl)c2Cl)ccc1CNC[C@@H]1CCC(=O)N1] | 776 |
| 763 | 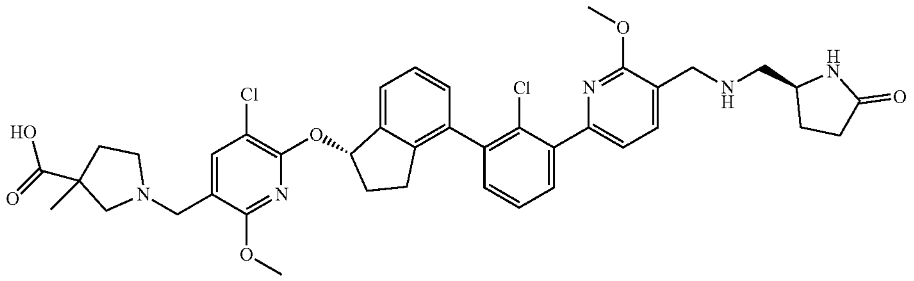 [SMILES: COc1nc(-c2cccc(-c3cccc4c3CC[C@@H]4Oc3nc(OC)c(CN4CCC(C)(C(=O)O)C4)cc3Cl)c2Cl)ccc1CNC[C@@H]1CCC(=O)N1] | 760.14 |

-continued
| Example No. | Structure | ES/MS (m/z, M + H+) |
|---|---|---|
| 764 | 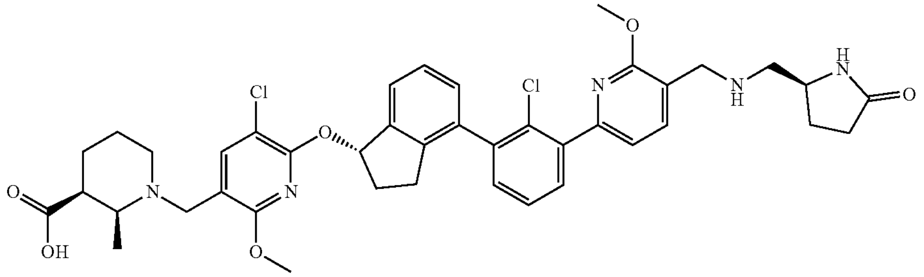 [SMILES: COc1nc(-c2cccc(-c3cccc4c3CC[C@@H]4Oc3nc(OC)c(CN4CCC[C@H](C(=O)O)[C@@H]4C)cc3Cl)c2Cl)ccc1CNC[C@@H]1CCC(=O)N1] | 774.13 |
| 765 | 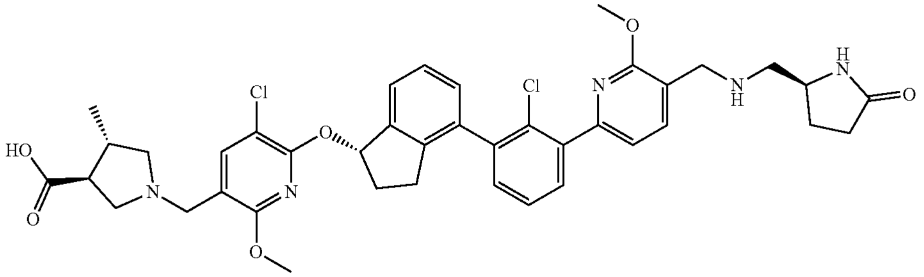 [SMILES: COc1nc(-c2cccc(-c3cccc4c3CC[C@@H]4Oc3nc(OC)c(CN4C[C@@H](C)[C@H](C(=O)O)C4)cc3Cl)c2Cl)ccc1CNC[C@@H]1CCC(=O)N1] | 760.09 |
| 766 | 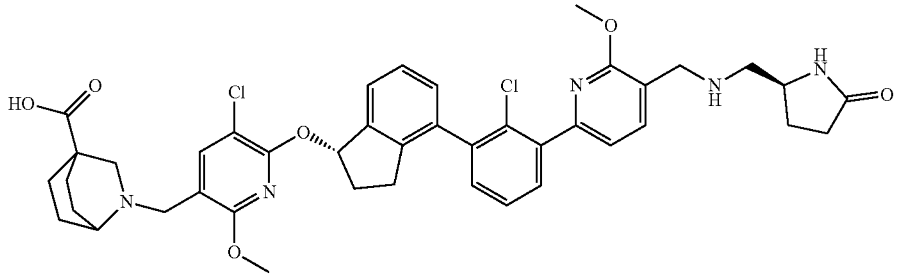 [SMILES: COc1nc(-c2cccc(-c3cccc4c3CC[C@@H]4Oc3nc(OC)c(CN4CC5(C(=O)O)CCC4CC5)cc3Cl)c2Cl)ccc1CNC[C@@H]1CCC(=O)N1] | 786.09 |
| 767 | 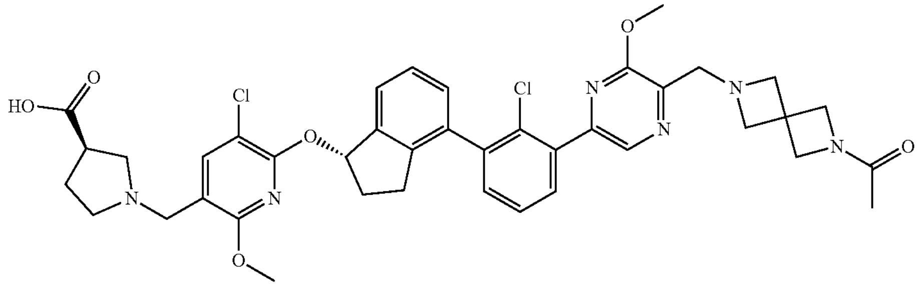 [SMILES: COc1nc(O[C@H]2CCc3c(-c4cccc(-c5cnc(CN6CC7(C6)CN(C(C)=O)C7)c(OC)n5)c4Cl)cccc32)c(Cl)cc1CN1CC[C@@H](C(=O)O)C1] | 773.02 |
| 768 | 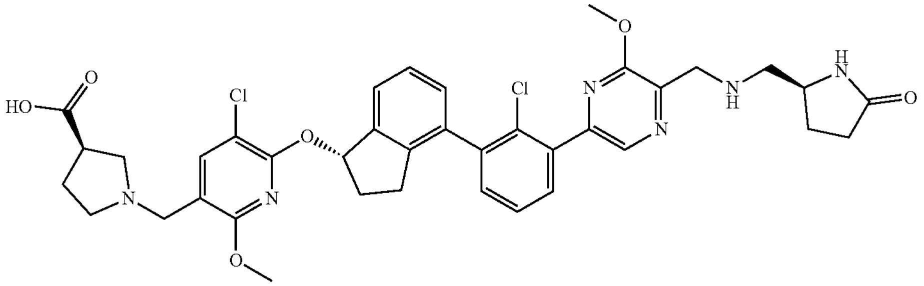 [SMILES: COc1nc(O[C@H]2CCc3c(-c4cccc(-c5cnc(CNC[C@@H]6CCC(=O)N6)c(OC)n5)c4Cl)cccc32)c(Cl)cc1CN1CC[C@@H](C(=O)O)C1] | 746.98 |

-continued
| Example No. | Structure | ES/MS (m/z, M + H+) |
|---|---|---|
| 769 | 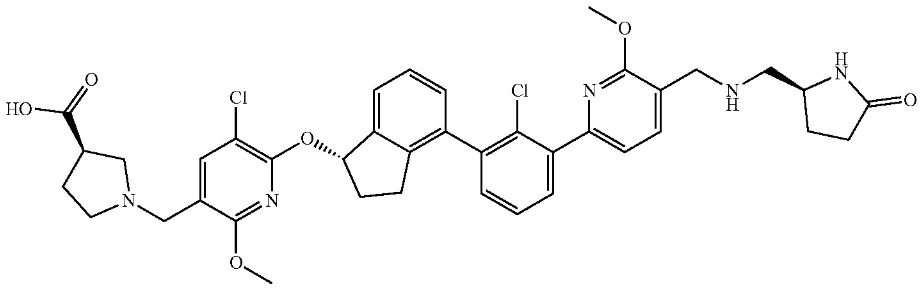 [SMILES: COc1nc(-c2cccc(-c3cccc4c3CC[C@@H]4Oc3nc(OC)c(CN4CC[C@@H](C(=O)O)C4)cc3Cl)c2Cl)ccc1CNC[C@@H]1CCC(=O)N1] | 745.93 |
| 770 | 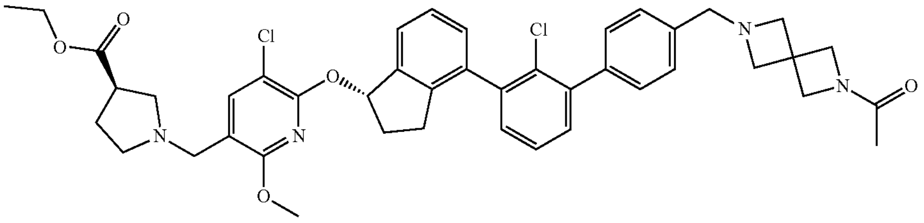 [SMILES: CCOC(=O)[C@@H]1CCN(Cc2cc(Cl)c(O[C@H]3CCc4c(-c5cccc(-c6ccc(CN7CC8(C7)CN(C(C)=O)C8)cc6)c5Cl)cccc43)nc2OC)C1] | 769.18 |
| 771 | 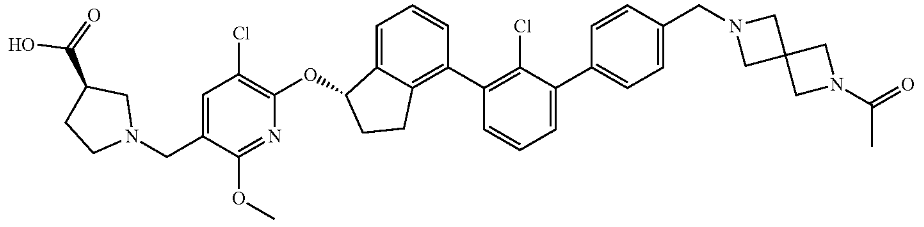 [SMILES: COc1nc(O[C@H]2CCc3c(-c4cccc(-c5ccc(CN6CC7(C6)CN(C(C)=O)C7)cc5)c4Cl)cccc32)c(Cl)cc1CN1CC[C@@H](C(=O)O)C1] | 740.95 |
| 772 | 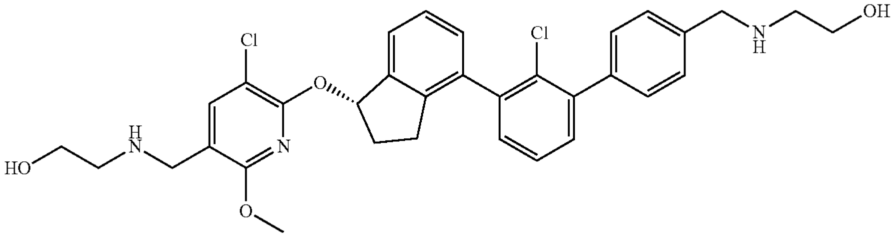 [SMILES: COc1nc(O[C@H]2CCc3c(-c4cccc(-c5ccc(CNCCO)cc5)c4Cl)cccc32)c(Cl)cc1CNCCO] | 608.11 |
| 773 | 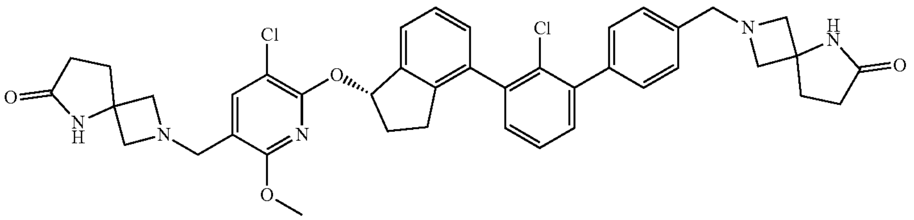 [SMILES: COc1nc(O[C@H]2CCc3c(-c4cccc(-c5ccc(CN6CC7(CCC(=O)N7)C6)cc5)c4Cl)cccc32)c(Cl)cc1CN1CC2(CCC(=O)N2)C1] | 737.25 |

-continued
| Example No. | Structure | ES/MS (m/z, M + H+) |
|---|---|---|
| 774 | 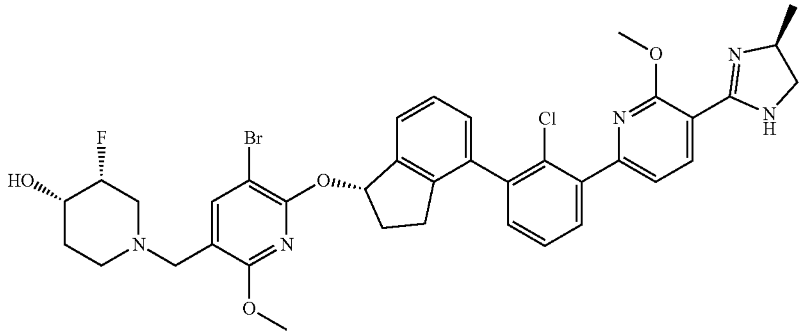 [SMILES: COc1nc(O[C@H]2CCc3c(-c4cccc(-c5ccc(C6=N[C@@H](C)CN6)c(OC)n5)c4Cl)cccc32)c(Br)cc1CN1CC[C@H](O)[C@H](F)C1] | 752.06 |
| 775 | 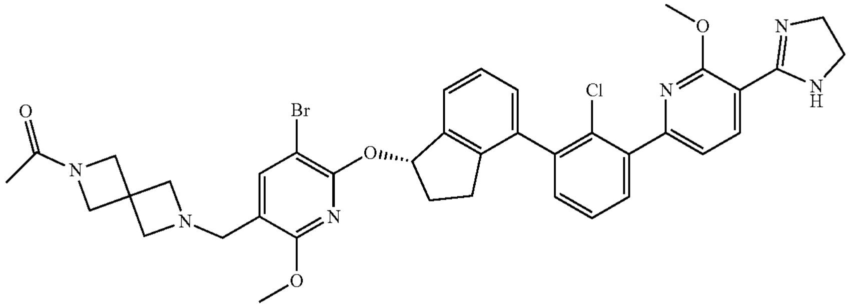 [SMILES: COc1nc(O[C@H]2CCc3c(-c4cccc(-c5ccc(C6=NCCN6)c(OC)n5)c4Cl)cccc32)c(Br)cc1CN1CC2(C1)CN(C(C)=O)C2] | 759.19 |
| 776 | 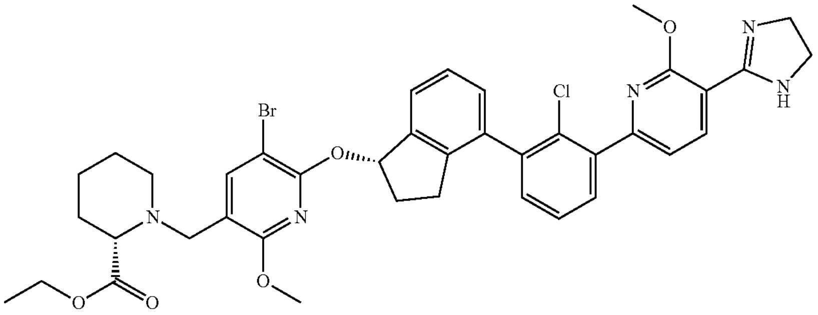 [SMILES: CCOC(=O)[C@@H]1CCCCN1Cc1cc(Br)c(O[C@H]2CCc3c(-c4cccc(-c5ccc(C6=NCCN6)c(OC)n5)c4Cl)cccc32)nc1OC] | 775.96 |
| 777 | 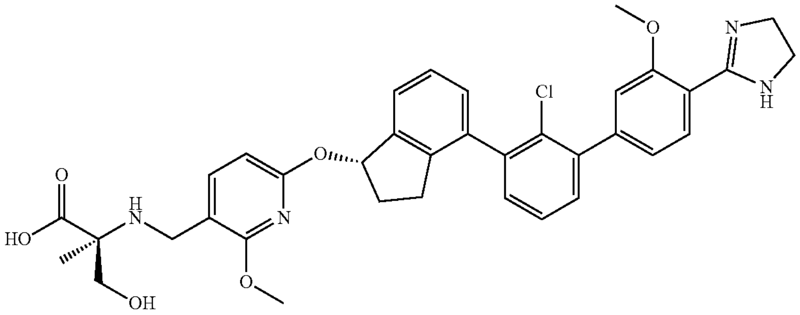 [SMILES: COc1cc(-c2cccc(-c3cccc4c3CC[C@@H]4Oc3ccc(CN[C@@](C)(CO)C(=O)O)c(OC)n3)c2Cl)ccc1C1=NCCN1] | 657.16 |

-continued
| Example No. | Structure | ES/MS (m/z, M + H+) |
|---|---|---|
| 778 | 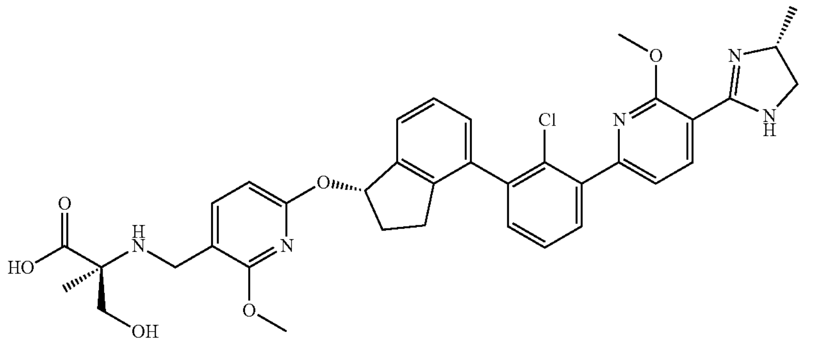 [SMILES: COc1nc(O[C@H]2CCc3c(-c4cccc(-c5ccc(C6=N[C@H](C)CN6)c(OC)n5)c4Cl)cccc32)ccc1CN[C@@](C)(CO)C(=O)O] | 672.11. |
| 779 | 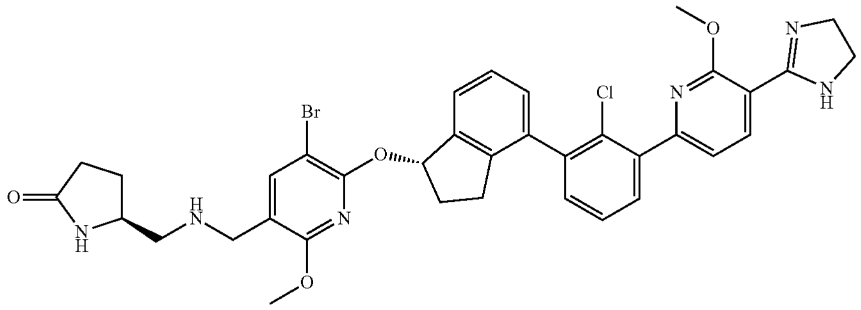 [SMILES: COc1nc(O[C@H]2CCc3c(-c4cccc(-c5ccc(C6=NCCN6)c(OC)n5)c4Cl)cccc32)c(Br)cc1CNC[C@@H]1CCC(=O)N1] | 733.15 |
| 780 | 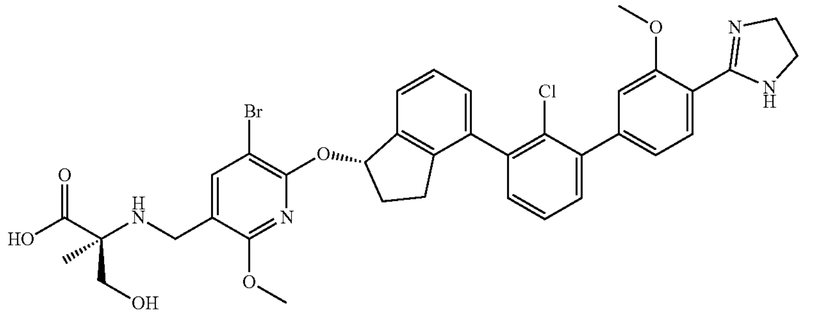 [SMILES: COc1cc(-c2cccc(-c3cccc4c3CC[C@@H]4Oc3nc(OC)c(CN[C@@](C)(CO)C(=O)O)cc3Br)c2Cl)ccc1C1=NCCN1] | 737.03 |
| 781 | 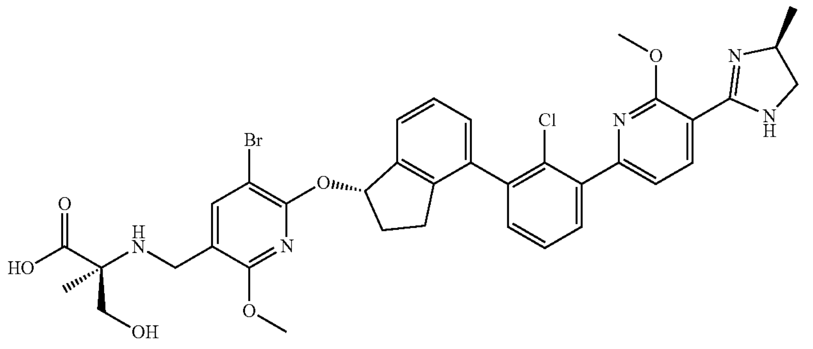 [SMILES: COc1nc(O[C@H]2CCc3c(-c4cccc(-c5ccc(C6=N[C@@H](C)CN6)c(OC)n5)c4Cl)cccc32)c(Br)cc1CN[C@@](C)(CO)C(=O)O] | 752.06 |

-continued
| Example No. | Structure | ES/MS (m/z, M + H+) |
|---|---|---|
| 782 | 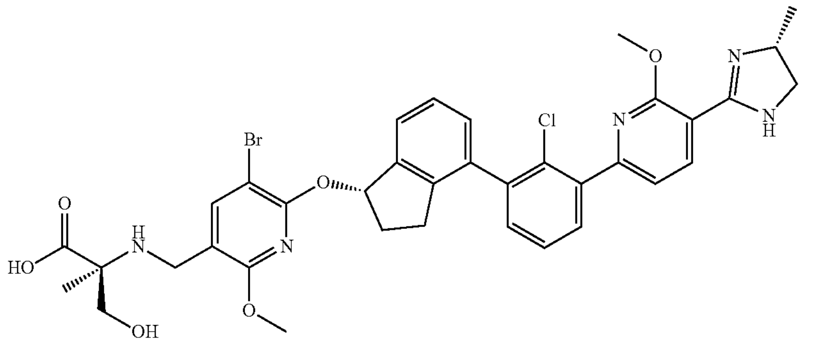 [SMILES: COc1nc(O[C@H]2CCc3c(-c4cccc(-c5ccc(C6=N[C@H](C)CN6)c(OC)n5)c4Cl)cccc32)c(Br)cc1CN[C@@](C)(CO)C(=O)O] | 751.94 |
| 783 | 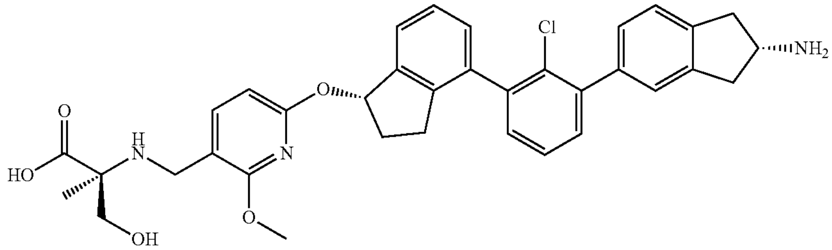 [SMILES: COc1nc(O[C@H]2CCc3c(-c4cccc(-c5ccc6c(c5)C[C@@H](N)C6)c4Cl)cccc32)ccc1CN[C@@](C)(CO)C(=O)O] | 613.89 |
| 784 | 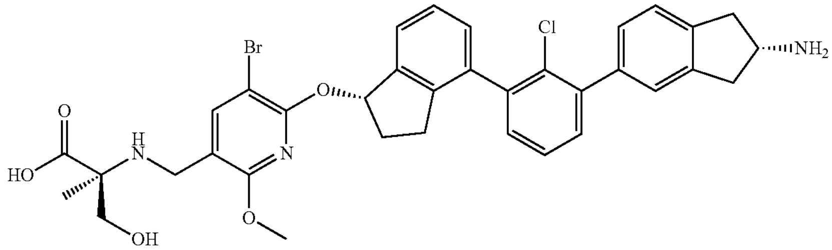 [SMILES: COc1nc(O[C@H]2CCc3c(-c4cccc(-c5ccc6c(c5)C[C@@H](N)C6)c4Cl)cccc32)c(Br)cc1CN[C@@](C)(CO)C(=O)O] | 693.84 |
| 785 | 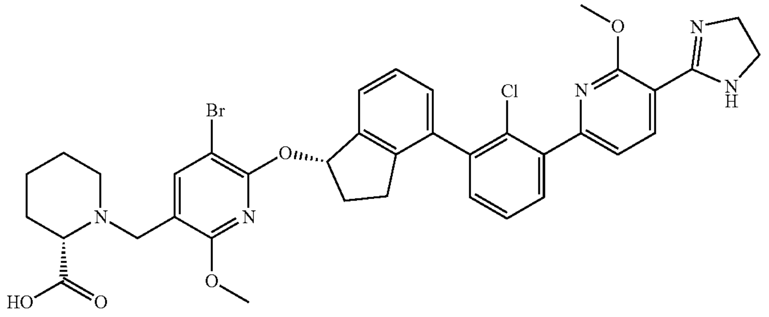 [SMILES: COc1nc(O[C@H]2CCc3c(-c4cccc(-c5ccc(C6=NCCN6)c(OC)n5)c4Cl)cccc32)c(Br)cc1CN1CCCC[C@H]1C(=O)O] | 748.08 |
| 786 | 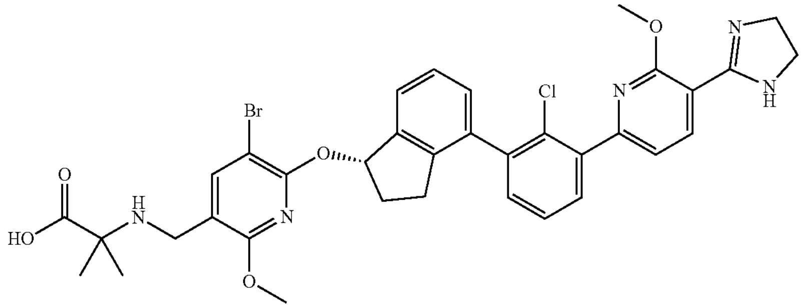 [SMILES: COc1nc(O[C@H]2CCc3c(-c4cccc(-c5ccc(C6=NCCN6)c(OC)n5)c4Cl)cccc32)c(Br)cc1CNC(C)(C)C(=O)O] | 720.2 |

-continued
| Example No. | Structure | ES/MS (m/z, M + H+) |
|---|---|---|
| 787 | 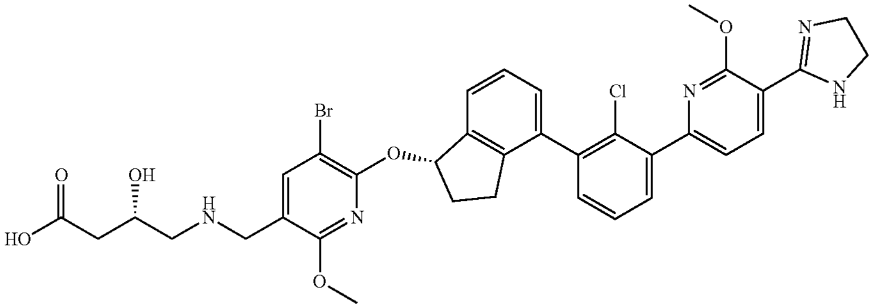 [SMILES: COc1nc(O[C@H]2CCc3c(-c4cccc(-c5ccc(C6=NCCN6)c(OC)n5)c4Cl)cccc32)c(Br)cc1CNC[C@@H](O)CC(=O)O] | 738.04 |
| 788 | 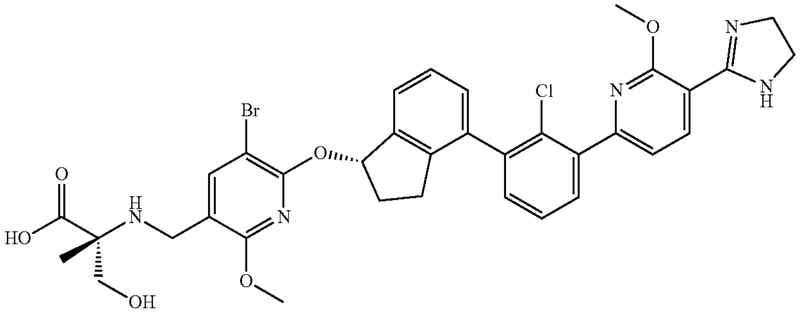 [SMILES: COc1nc(O[C@H]2CCc3c(-c4cccc(-c5ccc(C6=NCCN6)c(OC)n5)c4Cl)cccc32)c(Br)cc1CN[C@](C)(CO)C(=O)O] | 738.01 |
| 789 | 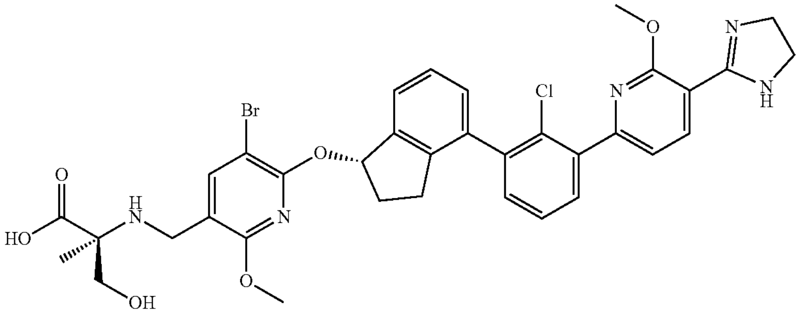 [SMILES: COc1nc(O[C@H]2CCc3c(-c4cccc(-c5ccc(C6=NCCN6)c(OC)n5)c4Cl)cccc32)c(Br)cc1CN[C@@](C)(CO)C(=O)O] | 738.01 |
| 790 | 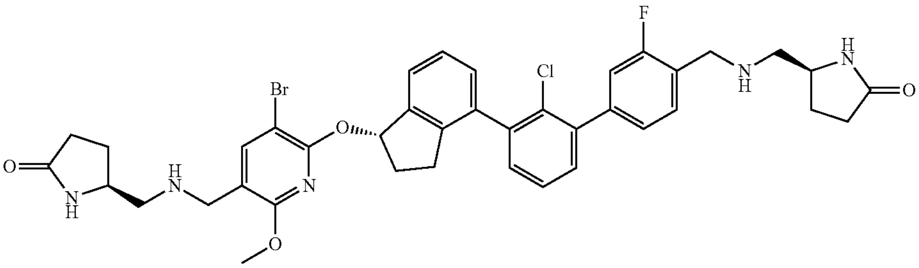 | 777.86 |
| 791 | 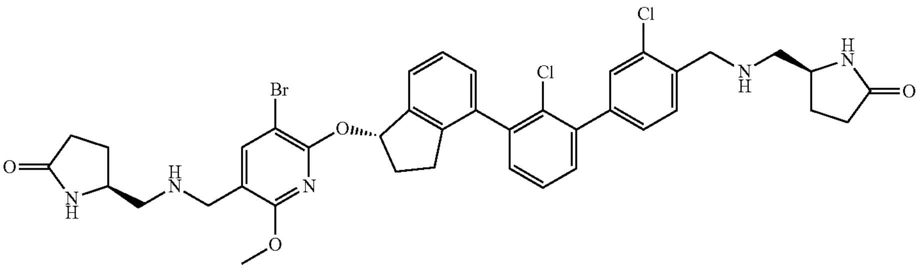 [SMILES: COc1nc(O[C@H]2CCc3c(-c4cccc(-c5ccc(CNC[C@@H]6CCC(=O)N6)c(F)c5)c4Cl)cccc32)c(Br)cc1CNC[C@@H]1CCC(=O)N1] | 793.16 |

-continued
| Example No. | Structure | ES/MS (m/z, M + H+) |
|---|---|---|
| 792 | 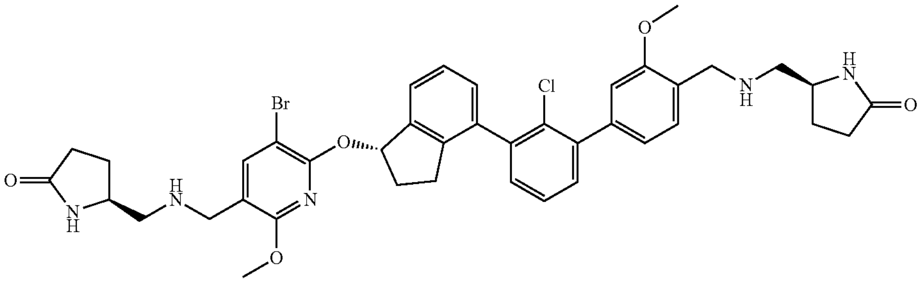 [SMILES: COc1cc(-c2cccc(-c3cccc4c3CC[C@@H]4Oc3nc(OC)c(CNC[C@@H]4CCC(=O)N4)cc3Br)c2Cl)ccc1CNC[C@@H]1CCC(=O)N1] | 789.92 |
| 793 | 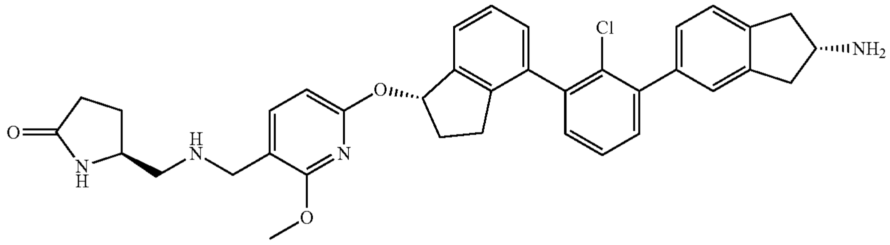 [SMILES: COc1nc(O[C@H]2CCc3c(-c4cccc(-c5ccc6c(c5)C[C@@H](N)C6)c4Cl)cccc32)ccc1CNC[C@@H]1CCC(=O)N1] | 608.78 |
| 794 | 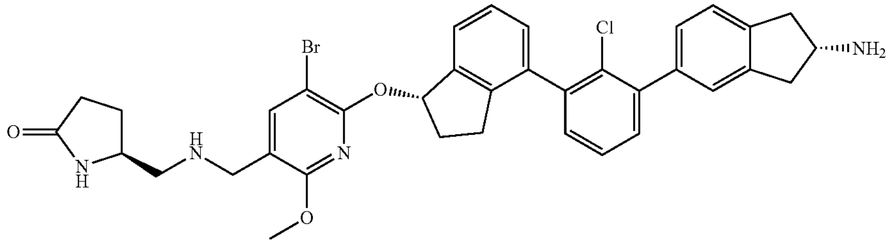 [SMILES: COc1nc(O[C@H]2CCc3c(-c4cccc(-c5ccc6c(c5)C[C@@H](N)C6)c4Cl)cccc32)c(Br)cc1CNC[C@@H]1CCC(=O)N1] | 688.75 |
| 795 | 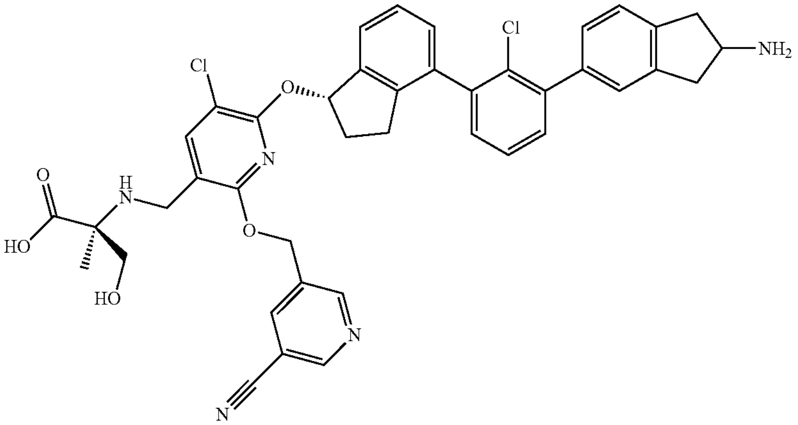 [SMILES: C[C@@](CO)(NCc1cc(Cl)c(O[C@H]2CCc3c(-c4cccc(-c5ccc6c(c5)CC(N)C6)c4Cl)cccc32)nc1OCc1cncc(C#N)c1)C(=O)O] | 750.2 |
| 796 | 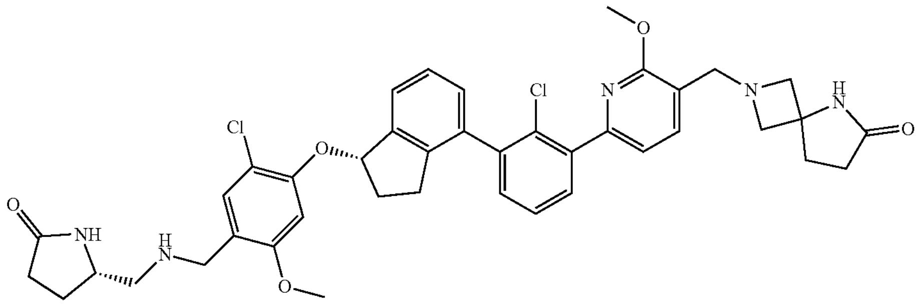 [SMILES: COc1cc(O[C@H]2CCc3c(-c4cccc(-c5ccc(CN6CC7(CCC(=O)N7)C6)c(OC)n5)c4Cl)cccc32)c(Cl)cc1CNC[C@@H]1CCC(=O)N1] | 756 |

-continued
| Example No. | Structure | ES/MS (m/z, M + H+) |
|---|---|---|
| 797 | 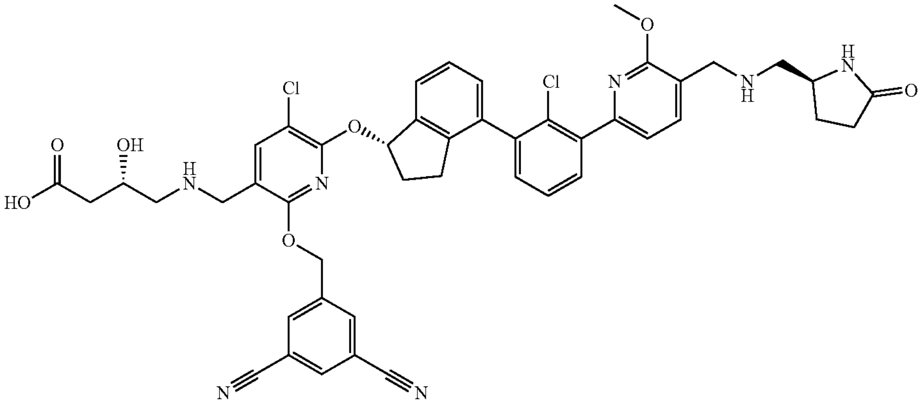 [SMILES: COc1nc(-c2cccc(-c3cccc4c3CC[C@@H]4Oc3nc(OCc4cc(C#N)cc(C#N)c4)c(CNC[C@@H](O)CC(=O)O)cc3Cl)c2Cl)ccc1CNC[C@@H]1CCC(=O)N1] | 876.2 |
| 798 | 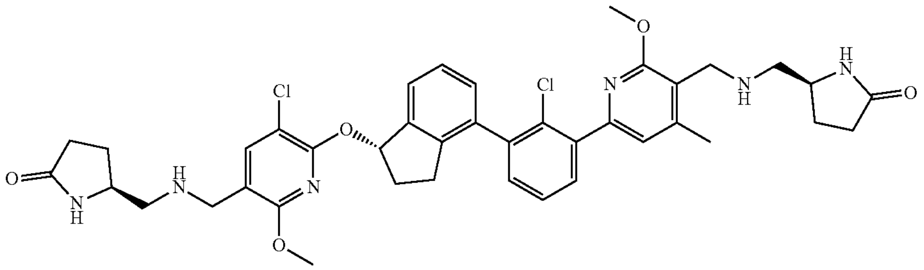 [SMILES: COc1nc(O[C@H]2CCc3c(-c4cccc(-c5cc(C)c(CNC[C@@H]6CCC(=O)N6)c(OC)n5)c4Cl)cccc32)c(Cl)cc1CNC[C@@H]1CCC(=O)N1] | 758.9 |
| 799 | 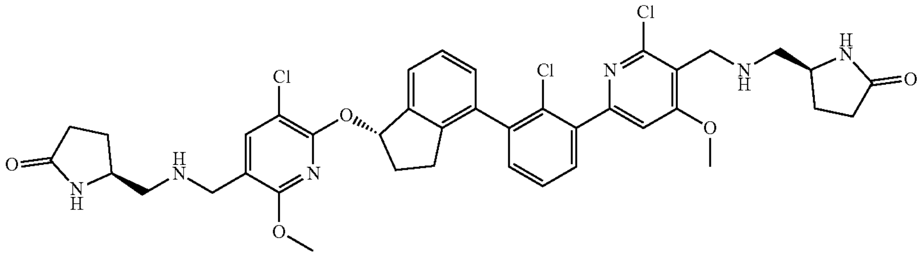 [SMILES: COc1cc(-c2cccc(-c3cccc4c3CC[C@@H]4Oc3nc(OC)c(CNC[C@@H]4CCC(=O)N4)cc3Cl)c2Cl)nc(Cl)c1CNC[C@@H]1CCC(=O)N1] | 780.1 |
| 800 | 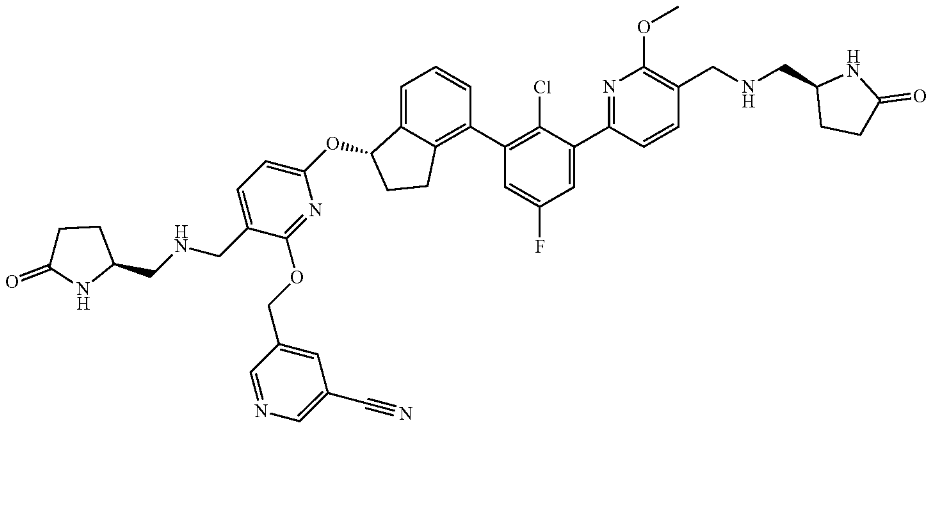 [SMILES: COc1nc(-c2cc(F)cc(-c3cccc4c3CC[C@@H]4Oc3ccc(CNC[C@@H]4CCC(=O)N4)c(OCc4cncc(C#N)c4)n3)c2Cl)ccc1CNC[C@@H]1CCC(=O)N1] | 831.1 |

-continued
| Example No. | Structure | ES/MS (m/z, M + H+) |
|---|---|---|
| 801 | 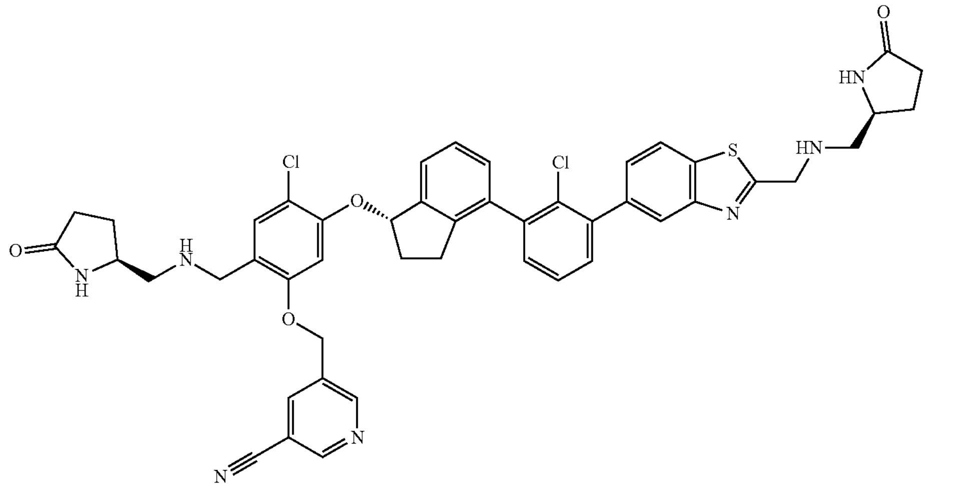 [SMILES: N#Cc1cncc(COc2cc(O[C@H]3CCc4c(-c5cccc(-c6ccc7sc(CNC[C@@H]8CCC(=O)N8)nc7c6)c5Cl)cccc43)c(Cl)cc2CNC[C@@H]2CCC(=O)N2)c1] | 873.0 |
| 802 | 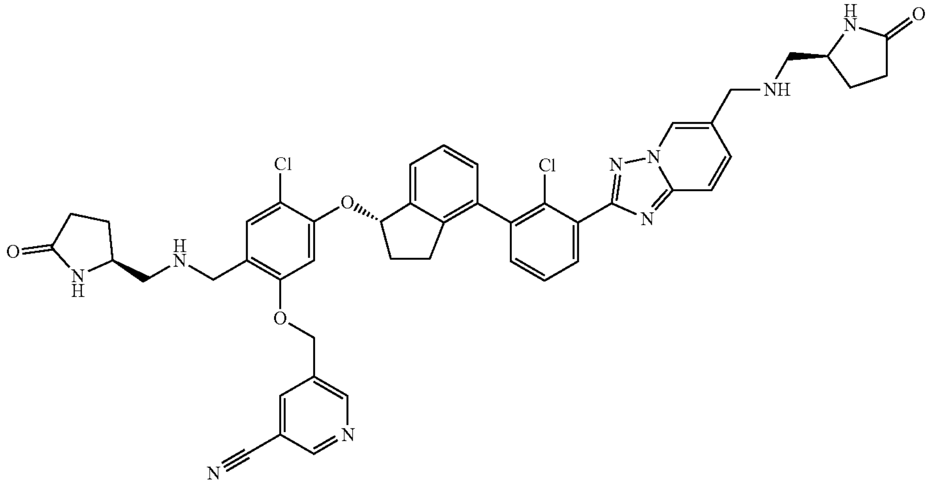 [SMILES: N#Cc1cncc(COc2cc(O[C@H]3CCc4c(-c5cccc(-c6nc7ccc(CNC[C@@H]8CCC(=O)N8)cn7n6)c5Cl)cccc43)c(Cl)cc2CNC[C@@H]2CCC(=O)N2)c1] | 857.0 |
| 803 | 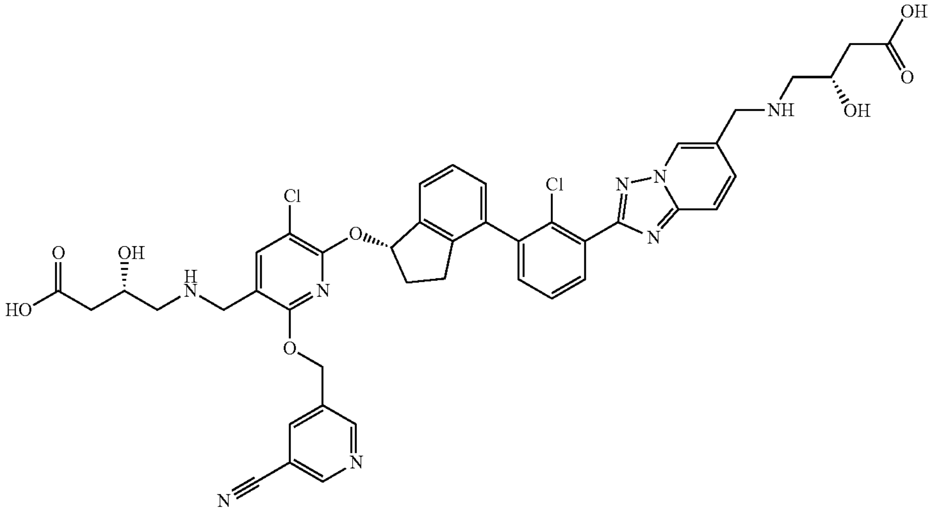 [SMILES: N#Cc1cncc(COc2nc(O[C@H]3CCc4c(-c5cccc(-c6nc7ccc(CNC[C@@H](O)CC(=O)O)cn7n6)c5Cl)cccc43)c(Cl)cc2CNC[C@@H](O)CC(=O)O)c1] | 867.0 |

NMR data for select compounds is shown below.

| Example No. | NMR |
|---|---|
| 637 | 1H NMR (400 MHz, Methanol-d4) d 9.03 (s, 2H), 8.50 (s, 1H), 7.90 (s, 1H), 7.54 (s, 4H), 7.45 (t, J = 7.5 Hz, 1H), 7.41-7.32 (m, 2H), 7.29-7.18 (m, 3H), 6.52 (s, 1H), 5.70 (s, 2H), 4.29 (s, 2H), 4.18 (s, 2H), , 3.27 (d, J = 3.1 Hz, 1H), 3.17 (d, J = 5.5 Hz, 3H), 3.07 (dd, J = 12.7, 9.8 Hz, 1H), 2.95-2.87 (m, 2H), 2.76 (s, 1H), 2.57 (d, J = 6.3 Hz, 3H), 2.10 (s, 1H). |
| 638 | 1H NMR (400 MHz, DMSO-d6) δ 9.15 (d, J = 7.1 Hz, 2H), 8.70 (s, 2H), 8.07 (d, J = 1.5 Hz, 1H), 7.99 (s, 1H), 7.94 (dd, J = 7.3, 2.2 Hz, 1H), 7.60 (d, J = 7.2 Hz, 1H), 7.50 (s, 1H), 7.44-7.37 (m, 2H), 7.31 (dd, J = 7.6, 1.2 Hz, 1H), 6.64 (s, 1H), 5.30 (d, J = 21.2 Hz, 2H), 4.39 (s, 2H), 4.09 (s, 2H), 4.02 (s, 3H), 3.68 (dt, J = 9.3, 4.6 Hz, 3H), 3.04 (d, J = 19.4 Hz, 4H), 2.93-2.83 (m, 1H), 2.79-2.66 (m, 2H), 2.11 (d, J = 19.3 Hz, 1H). |
| 641 | 1H NMR (400 MHz, DMSO-d6) d 8.84 (s, 1H), 8.63 (s, 1H), 8.01 (s, 1H), 7.94 (d, J = 7.6 Hz, 1H), 7.62 (dd, J = 7.6, 1.8 Hz, 1H), 7.56 (d, J = 2.5 Hz, 1H), 7.55-7.45 (m, 2H), 7.38 (dd, J = 13.8, 7.3 Hz, 2H), 7.28 (d, J = 7.5 Hz, 1H), 6.61 (s, 1H),, 4.33 (s, 2H), 4.21 (s, 2H), 4.00 (s, 3H), 3.97 (s, 3H), 3.88 (d, J = 6.3 Hz, 1H), 3.42 (m, 6H), 3.10 (d, J = 26.0 Hz, 2H), 2.93-2.82 (m, 1H), 2.81-2.61 (m, 2H), 2.34-2.03 (m, 5H), 1.85-1.71 (m, 1H). |
| 642 | 1H NMR (400 MHz, Acetonitrile-d3) d 8.52 (d, J = 1.1 Hz, 1H), 7.84 (s, 1H), 7.73 (dd, J = 7.6, 1.6 Hz, 1H), 7.63 (t, J = 7.1 Hz, 2H), 7.53 (s, 2H), 7.49-7.40 (m, 1H), 7.36 (d, J = 7.5 Hz, 1H), 6.72 (s, 1H), 4.47 (s, 2H), 4.41 (d, J = 2.9 Hz, 1H), 4.19 (s, 2H), 4.11 (s, 6H), 3.84 (d, J = 12.4 Hz, 1H), 3.68-3.53 (m, 1H), 3.11-2.62 (m, 5H), 2.40-2.00 (m, 2H), 2.00-1.62 (m, 3H), 1.57 (d, J = 1.2 Hz, 3H). |
| 643 | 1H NMR (400 MHz, DMSO-d6) d 9.04 (s, 1H), 8.89 (s, 1H), 8.77-8.70 (m, 1H), 8.58 (s, 1H), 8.45 (s, 1H), 7.95 (s, 1H), 7.69 (dd, J = 7.6, 1.9 Hz, 1H), 7.59 (t, J = 7.5 Hz, 1H), 7.47 (s, 2H), 7.37 (t, J = 7.5 Hz, 1H), 7.29 (dd, J = 7.6, 1.2 Hz, 1H), 6.61 (d, J = 6.6 Hz, 1H), 5.54 (s, 2H), 4.36 (d, J = 6.4 Hz, 2H), 4.26 (d, J = 18.3 Hz, 2H), 4.04 (s, 2H), 4.02 (s, 3H), 3.98 (s, 3H), 2.95-2.63 (m, 4H), 2.10 (s, 1H), 2.06-1.89 (m, 2H), 1.79 (td, J = 8.8, 8.1, 5.2 Hz, 4H), 1.78-1.61 (m, 3H), 1.60-1.47 (m, 2H). |
| 644 | 1H NMR (400 MHz, Acetonitrile-d3) ? 7.83 (d, J = 7.6 Hz, 1H), 7.75 (d, J = 1.3 Hz, 1H), 7.62 (dd, J = 7.7, 1.8 Hz, 1H), 7.51 (td, J = 7.7, 4.5 Hz, 2H), 7.38 (q, J = 10.1, 7.7 Hz, 2H), 7.34-7.19 (m, 2H), 6.65 (s, 1H), 4.30 (t, J = 3.5 Hz, 1H), 4.29-4.16 (m, 2H), 4.11 (s, 2H), 4.01 (d, J = 12.6 Hz, 7H), 3.39 (td, J = 8.6, 4.8 Hz, 1H), 3.15-3.01 (m, 2H), 2.93 (s, 1H), 2.76 (m, 1H), 2.68 (dd, J = 14.5, 7.6 Hz, 1H), 2.41-2.25 (m, 4H), 2.17 (s, 2H), 2.05 (ddt, J = 12.2, 8.4, 4.5 Hz, 1H), 1.91-1.52 (m, 4H). |
| 645 | 1H NMR (400 MHz, Acetonitrile-d3) d 7.82 (d, J = 7.6 Hz, 1H), 7.76 (s, 1H), 7.61 (dd, J = 7.6, 1.8 Hz, 1H), 7.51 (q, J = 7.8 Hz, 2H), 7.36 (t, J = 7.6 Hz, 1H), 7.32-7.24 (m, 3H), 6.65 (d, J = 6.8 Hz, 1H), 4.32-4.25 (m, 1H), 4.22 (d, J = 3.7 Hz, 2H), 4.11 (s, 2H), 4.01 (d, J = 14.6 Hz, 6H), 3.75 (d, J = 12.4 Hz, 1H), 3.39 (td, J = 8.7, 4.6 Hz, 1H), 2.92 (s, 1H), 2.83-2.55 (m, 4H), 2.23-2.10 (m, 1H), 2.10-2.00 (m, 1H), 1.90-1.66 (m, 2H), 1.66-1.52 (m, 1H), 1.48 (s, 3H). |
| 650 | 1H NMR (400 MHz, DMSO-d6) d 8.84 (s, 1H), 8.73 (s, 1H), 8.62 (s, 1H), 8.44 (s, 1H), 7.95 (s, 1H), 7.63-7.50 (m, 3H), 7.45 (dd, J = 7.5, 1.7 Hz, 1H), 7.44-7.32 (m, 2H), 7.31-7.24 (m, 2H), 6.61 (s, 1H), 5.55 (s, 1H), 5.30 (s, 2H), 4.23 (s, 3H), 4.04 (d, J = 5.4 Hz, 2H), 3.98 (s, 3H), 3.88 (d, J = 7.6 Hz, 1H), 3.31 (s, 1H), 3.13 (s, 1H), 3.06 (s, 1H), 2.91-2.84 (m, 1H), 2.82-2.61 (m, 2H), 2.26-2.07 (m, 4H), 1.99-1.89 (m, 1H), 1.84-1.60 (m, 5H), 1.53 (m, 1H). |
| 651 | 1H NMR (400 MHz, DMSO-d6) d 8.93 (s, 1H), 8.74 (s, 2H), 8.45 (s, 1H), 8.06 (d, J = 7.7 Hz, 1H), 7.95 (s, 1H), 7.70 (dd, J = 7.6, 1.8 Hz, 1H), 7.63-7.53 (m, 3H), 7.46 (s, 2H), 7.37 (t, J = 7.5 Hz, 1H), 7.29 (dd, J = 7.5, 1.2 Hz, 1H), 6.60 (d, J = 5.5 Hz, 1H), 5.55 (s, 1H), 5.29 (s, 2H), 4.25 (s, 3H), 4.04 (s, 2H), 3.98 (s, 3H), 3.89 (s, 1H), 3.32 (s, 1H), 3.16 (s, 1H), 3.09 (s, 1H), 2.88 (s, 1H), 2.80-2.67 (m, 3H), 2.26-2.07 (m, 2H), 2.01-1.89 (m, 1H), 1.78 (s, 4H), 1.83-1.63 (m, 2H) , 1.53 (m, 1H). |
| 652 | 1H NMR (400 MHz, Chloroform-d) d 9.27 (s, 1H), 9.17 (s, 1H), 8.84 (s, 1H), 8.63 (s, 1H), 8.02 (s, 1H), 7.74 (dd, J = 7.6, 1.8 Hz, 1H), 7.71-7.56 (m, 3H), 7.52 (d, J = 9.8 Hz, 2H), 7.42 (t, J = 7.5 Hz, 1H), 7.36-7.31 (m, 1H), 6.66 (d, J = 6.8 Hz, 1H), 4.50 (s, 2H), 4.14 (s, 2H), 4.07 (s, 3H), 4.04 (s, 3H), 3.98 (d, J = 6.5 Hz, 1H), 3.88 (m, 2H), 3.24 (s, 2H), 3.10 (s, 1H), 3.04 (s, 1H), 2.92 (s, 1H), 2.79 (d, J = 17.8 Hz, 1H), 2.71 (d, J = 19.0 Hz, 1H), 2.29-2.13 (m, 6H), 1.88-1.76 (m, 2H). |
| 653 | 1H NMR (400 MHz, Chloroform-d) d 8.86 (d, J = 22.3 Hz, 2H), 8.65 (s, 2H), 8.04 (s, 1H), 7.68-7.56 (m, 4H), 7.56-7.46 (m, 3H), 7.46-7.38 (m, 2H), 7.33 (d, J = 7.5 Hz, 2H), 6.78-6.58 (m, 1H), 5.36 (s, 2H), 4.45 (s, 2H), 4.29 (s, 2H), 4.15 (d, J = 5.0 Hz, 2H), 3.98-3.86 (m, 2H), 3.27-3.00 (m, 8H), 3.01-2.63 (m, 3H), 2.32-2.15 (m, 5H), 1.84 (td, J = 10.2, 5.2 Hz, 2H). |
| 654 | 1H NMR (400 MHz, DMSO-d6) d 8.85 (s, 1H), 8.67 (s, 3H), 7.96 (s, 1H), 7.63-7.50 (m, 3H), 7.50-7.41 (m, 3H), 7.44-7.32 (m, 2H), 7.27 (d, J = 7.6 Hz, 2H), 6.60 (s, 1H), 5.59 (s, 1H), 5.30 (s, 2H), 4.23 (s, 2H), 4.16 (s, 1H), 4.09-4.03 (m, 2H), 3.98 (s, 3H), 3.89 (s, 1H), 3.13 (s, 1H), 3.05 (s, 2H), 2.88 (s, 2H), 2.87 (d, J = 4.4 Hz, 1H), 2.80-2.70 (m, 1H), 2.69 (s, 1H), 2.51 (d, J = 4.9 Hz, 0H), 2.45 (s, 0H), 2.37 (dd, J = 15.9, 7.3 Hz, 1H), 2.26-2.07 (m, 4H), 1.78 (q, J = 9.8 Hz, 1H). |
| 655 | 1H NMR (400 MHz, Chloroform-d) d 8.86 (d, J = 22.3 Hz, 2H), 8.65 (s, 2H), 8.04 (s, 1H), 7.68-7.56 (m, 4H), 7.56-7.46 (m, 3H), 7.46-7.38 (m, 2H), 7.33 (d, J = 7.5 Hz, 2H), 6.78-6.58 (m, 1H), 5.36 (s, 2H), 4.29 (s, 2H), 4.15 (d, J = 5.0 Hz, 2H), 4.06 (s, 3H), 3.98-3.86 (m, 2H), 3.27-3.00 (m, 8H), 3.01-2.63 (m, 3H), 2.32-2.15 (m, 5H), 1.84 (td, J = 10.2, 5.2 Hz, 2H). |
| 658 | 1H NMR (400 MHz, DMSO-d6) d 8.83 (s, 2H), 8.64 (s, 2H), 8.10 (s, 1H), 7.94 (d, J = 7.6 Hz, 1H), 7.62 (dd, J = 7.6, 1.8 Hz, 1H), 7.55 (dd, J = 10.0, 5.9 Hz, 3H), 7.47 (s, 2H), 7.38 (dd, J = 10.8, 7.1 Hz, 2H), 7.30 (d, J = 7.5 Hz, 1H), 6.68 (s, 1H), 5.40-5.26 (m, 2H), |

-continued

| Example No. | NMR |
|---|---|
| | 4.21 (s, 2H), 4.12 (s, 2H), 3.97 (s, 3H), 3.89-3.81 (m, 2H), 3.14 (s, 1H), 3.07 (s, 2H), 3.01 (s, 1H), 2.97-2.71 (m, 3H), 2.27-2.03 (m, 5H), 1.77 (s, 2H). |
| 659 | 1H NMR (400 MHz, Methanol-d4) d 9.03 (s, 2H), 8.50 (s, 1H), 7.90 (s, 1H), 7.54 (s, 4H), 7.45 (t, J = 7.5 Hz, 1H), 7.41-7.32 (m, 2H), 7.29-7.18 (m, 3H), 6.52 (s, 1H), 5.70 (s, 2H), 4.29 (s, 2H), 4.18 (s, 2H), , 3.27 (d, J = 3.1 Hz, 1H), 3.17 (d, J = 5.5 Hz, 3H), 3.07 (dd, J = 12.7, 9.8 Hz, 1H), 2.95-2.87 (m, 2H), 2.76 (s, 1H), 2.57 (d, J = 6.3 Hz, 3H), 2.10 (s, 1H). |
| 675 | 1H NMR (400 MHz, Acetonitrile-d3) d 8.89 (d, J = 2.1 Hz, 1H), 8.79 (d, J = 1.9 Hz, 1H), 8.24 (s, 1H), 7.82 (s, 1H), 7.36-7.15 (m, 8H), 7.05 (d, J = 8.4 Hz, 2H), 6.53-6.39 (m, 1H), 5.58 (s, 2H), 4.39 (m, 1H), 4.29 (q, J = 6.6, 5.8 Hz, 3H), 4.23 (dd, J = 15.5, 1.7 Hz, 2H), 3.54 (s, 1H), 3.52-3.44 (m, 2H), 3.27 (dd, J = 12.9, 3.1 Hz, 1H), 3.21-3.05 (m, 3H), 3.00 (dd, J = 12.8, 9.8 Hz, 2H), 2.87 (d, J = 14.8 Hz, 1H), 2.72 (m, 2H), 2.63-2.44 (m, 6H), 2.02 (d, J = 8.1 Hz, 1H). |
| 676 | 1H NMR (400 MHz, Acetonitrile-d3) d 8.90 (s, 1H), 8.80 (d, J = 2.0 Hz, 1H), 8.25 (d, J = 2.1 Hz, 1H), 8.01 (dd, J = 8.0, 1.2 Hz, 1H), 7.95 (s, 1H), 7.79 (dd, J = 7.8, 1.7 Hz, 1H), 7.47 (td, J = 7.6, 1.2 Hz, 1H), 7.37-7.12 (m, 9H), 7.09-7.02 (m, 2H), 6.46 (t, J = 5.9 Hz, 1H), 5.58 (s, 2H), 4.35-4.24 (m, 4H), 4.21 (d, J = 2.2 Hz, 2H), 3.28 (dd, J = 12.8, 3.0 Hz, 2H), 3.22-3.04 (m, 3H), 3.00 (dd, J = 12.8, 9.8 Hz, 2H), 2.94-2.81 (m, 1H), 2.72 (d, J = 7.7 Hz, 2H), 2.65-2.37 (m, 6H). |
| 679 | 1H NMR (400 MHz, Acetonitrile-d3) d 8.85 (d, J = 2.1 Hz, 1H), 8.75 (d, J = 1.9 Hz, 1H), 8.21 (t, J = 2.1 Hz, 1H), 7.93 (s, 1H), 7.86 (s, 1H), 7.45 (d, J = 7.4 Hz, 1H), 7.31 (t, J = 7.5 Hz, 1H), 7.27-7.20 (m, 2H), 7.15 (dd, J = 5.4, 3.6 Hz, 1H), 6.62-6.54 (m, 1H), 6.39 (t, J = 5.9 Hz, 1H), 5.55 (s, 2H), 4.30-4.20 (m, 3H), 4.19 (s, 2H), 4.10 (s, 2H), 3.99 (s, 3H), 3.11 (ddd, J = 16.3, 12.9, 3.0 Hz, 2H), 3.02-2.76 (m, 4H), 2.69 (ddt, J = 26.4, 13.1, 7.0 Hz, 3H), 2.57-2.42 (m, 4H), 2.41 (dt, J = 13.6, 6.0 Hz, 1H), 2.11 (ddt, J = 13.8, 9.1, 5.0 Hz, 1H). |
| 683 | 1H NMR (400 MHz, Methanol-d4) d 8.96 (d, J = 2.1 Hz, 1H), 8.90-8.79 (m, 1H), 8.37 (d, J = 8.0 Hz, 1H), 7.88 (d, J = 15.1 Hz, 2H), 7.60 (dd, J = 7.7, 1.8 Hz, 1H), 7.49 (t, J = 7.6 Hz, 1H), 7.45-7.39 (m, 1H), 7.36 (d, J = 7.6 Hz, 1H), 7.29 (s, 1H), 7.24 (s, 2H), 6.54 (d, J = 23.0 Hz, 1H), 5.64 (s, 2H), 4.59-4.25 (m, 8H), 4.08 (s, 3H), 3.27-2.78 (m,3H), 2.69-2.46 (m, 6H), 2.40 (dd, J = 8.2, 6.4 Hz, 2H), 2.20-2.01 (m, 2H). |
| 684 | 1H NMR (400 MHz, Methanol-d4) d 8.99 (s, 1H), 8.84 (s, 1H), 8.40 (s, 1H), 7.95-7.84 (m, 2H), 7.60 (dd, J = 7.7, 1.8 Hz, 1H), 7.49 (t, J = 7.6 Hz, 1H), 7.44-7.33 (m, 2H), 7.28 (d, J = 19.1 Hz, 2H), 6.96 (d, J = 7.6 Hz, 1H), 6.55 (s, 1H), 5.63 (s, 2H), 4.65-4.26 (m, 8H), 4.15-4.04 (m, 4H), 4.00-3.80 (m, 2H), 3.03-2.67 (m, 1H), 2.54 (dt, J = 31.0, 7.2 Hz, 3H), 2.40 (dd, J = 8.1, 6.4 Hz, 2H), 2.10 (dq, J = 13.8, 6.9 Hz, 1H), 1.60 (s, 3H). |
| 694 | 1H NMR (400 MHz, Methanol-d4) d 9.03 (dd, J = 5.5, 2.1 Hz, 4H), 8.50 (t, J = 2.1 Hz, 2H), 7.90 (s, 2H), 7.31-7.21 (m, 4H), 7.19 (dd, J = 5.8, 3.0 Hz, 2H), 6.50 (dd, J = 6.9, 5.0 Hz, 2H), 5.70 (s, 4H), 4.41-4.19 (m, 6H), 3.27 (d, J = 3.0 Hz, 2H), 3.18 (s, 6H), 3.08 (dd, J = 12.7, 9.8 Hz, 2H), 2.99-2.69 (m, 4H), 2.68-2.41 (m, 6H), 2.16-1.98 (m, 2H). |
| 697 | 1H NMR (400 MHz, Methanol-d4) δ 7.98 (s, 1H), 7.88 (d, J = 7.6 Hz, 1H), 7.60-7.25 (m, 6H), 7.24-7.16 (m, 1H), 6.67-6.57 (m, 1H), 4.42-4.30 (m, 2H), 4.30-4.15 (m, 2H), 4.10 (s, 3H), 4.09 (s, 3H), 4.09-3.76 (m, 3H), 3.30-3.20 (m, 2H), 3.08-2.52 (m, 2H), 2.52-2.31 (m, 4H), 2.27-2.08 (m, 1H), 1.99-1.84 (m, 1H).1.59 (s, 3H). |
| 700 | 1H NMR (400 MHz, Methanol-d4) δ 8.99 (s, 1H), 8.83 (d, J = 7.3 Hz, 1H), 8.39 (d, J = 8.5 Hz, 1H), 7.94 (s, 1H), 7.89 (d, J = 7.5 Hz, 1H), 7.55-7.49 (m, 2H), 7.38 (td, J = 6.7, 2.5 Hz, 1H), 7.34-7.10 (m, 4H), 6.53 (q, J = 5.4 Hz, 1H), 5.65-5.57 (m, 2H), 4.34 (s, 2H), 4.31 (s, 2H), 4.10 (s, 3H), 4.09-4.00 (m, 2H), 3.85 (d, J = 12.2 Hz, 1H), 3.29-3.21 (m, 2H), 2.99-2.62 (m, 2H), 2.62-2.49 (m, 1H), 2.49-2.30 (m, 3H), 2.17-2.03 (m, 1H), 1.97-1.85 (m, 1H), 1.58 (s, 3H). |
| 703 | 1H NMR (400 MHz, Methanol-d4) δ 8.50 (s, 1H), 7.90 (s, 1H), 7.67 (dd, J = 7.6, 1.8 Hz, 1H), 7.63-7.31 (m, 4H), 7.28 (d, J = 7.4 Hz, 1H), 6.68 (d, J = 6.0 Hz, 1H), 4.83-4.06 (m, 14H), 4.00-2.10 (m, 14H). |
| 704 | 1H NMR (400 MHz, Methanol-d4) δ 7.90 (d, J = 7.1 Hz, 2H), 7.63 (dd, J = 7.7, 1.7 Hz, 1H), 7.57-7.31 (m, 5H), 7.27 (d, J = 7.4 Hz, 1H), 6.68 (d, J = 6.2 Hz, 1H), 4.59-4.01 (m, 14H), 4.00-2.11(m, 14H). |
| 705 | 1H NMR (400 MHz, Methanol-d4) δ 8.51 (s, 1H), 7.90 (s, 1H), 7.67 (dd, J = 7.7, 1.8 Hz, 1H), 7.62-7.32 (m, 4H), 7.28 (d, J = 7.4 Hz, 1H), 6.68 (d, J = 6.4 Hz, 1H), 4.75 (d, J = 28.8 Hz, 2H), 4.55-4.17 (m, 5H), 4.13 (s, 7H), 4.03-2.12 (m, 11H), 1.59 (d, J = 22.4 Hz, 3H). |
| 706 | 1H NMR (400 MHz, Methanol-d4) δ 7.91 (d, J = 6.0 Hz, 2H), 7.63 (dd, J = 7.6, 1.8 Hz, 1H), 7.60-7.31 (m, 5H), 7.27 (d, J = 7.5 Hz, 1H), 6.68 (s, 1H), 4.60-4.32 (m, 4H), 4.23 (t, J = 10.4 Hz, 2H), 4.19-4.03 (m, 8H), 4.01-2.10 (m, 11H), 1.56 (s, 3H). |
| 707 | 1H NMR (400 MHz, Methanol-d4) δ 8.50 (s, 1H), 7.90 (s, 1H), 7.67 (d, J = 7.7 Hz, 1H), 7.55 (dd, J = 15.8, 7.8 Hz, 3H), 7.38 (t, J = 7.6 Hz, 1H), 7.28 (dd, J = 7.6, 1.2 Hz, 1H), 6.68 (s, 1H), 4.70 (d, J = 19.3 Hz, 2H), 4.49 (d, J = 10.5 Hz, 1H), 4.38 (s, 2H), 4.24-4.06 (m, 8H), 4.02 (d, J = 10.7 Hz, 1H), 3.97-2.15 (m, 13H), 1.36 (d, J = 32.1 Hz, 3H). |
| 708 | 1H NMR (400 MHz, Methanol-d4) δ 7.89 (d, J = 8.9 Hz, 2H), 7.62 (dd, J = 6.0, 3.7 Hz, 1H), 7.58-7.31 (m, 5H), 7.27 (dd, J = 7.5, 1.2 Hz, 1H), 6.67 (s, 1H), 4.48 (d, J = 8.1 Hz, 2H), 4.38 (s, 2H), 4.23 (dd, J = 10.9, 4.6 Hz, 2H), 4.16-4.05 (m, 6H), 4.07-2.11 (m, 15H), 1.32 (d, J = 11.0 Hz, 3H). |
| 709 | 1H NMR (400 MHz, Methanol-d4) δ 8.51 (s, 1H), 7.90 (s, 1H), 7.67 (dd, J = 7.6, 1.8 Hz, 1H), 7.60-7.41 (m, 3H), 7.38 (t, J = 7.6 Hz, 1H), 7.28 (d, J = 7.4 Hz, 1H), 6.68 (s, 1H), 4.74 (d, J = 10.5 Hz, 4H), 4.36 (d, J = 25.7 Hz, 4H), 4.13 (d, J = 1.1 Hz, 8H), 3.99-2.13 (m, 10H). |

-continued

| Example No. | NMR |
|---|---|
| 710 | 1H NMR (400 MHz, Methanol-d4) δ 7.91 (d, J = 7.0 Hz, 2H), 7.63 (dd, J = 7.7, 1.8 Hz, 1H), 7.58-7.30 (m, 5H), 7.27 (d, J = 7.4 Hz, 1H), 6.67 (s, 1H), 4.81-4.57 (m, 1H), 4.56-4.26 (m, 7H), 4.12 (d, J = 11.3 Hz, 8H), 4.01-2.14 (m, 10H). |
| 711 | 1H NMR (400 MHz, Methanol-d4) δ 8.55 (s, 1H), 7.90 (s, 1H), 7.68 (dd, J = 7.7, 1.8 Hz, 1H), 7.64-7.41 (m, 3H), 7.38 (t, J = 7.6 Hz, 1H), 7.28 (d, J = 7.5 Hz, 1H), 6.68 (s, 1H), 4.47 (s, 2H), 4.46-4.28 (m, 3H), 4.14 (d, J = 1.1 Hz, 6H), 4.04-2.12 (m, 18H). |
| 712 | 1H NMR (400 MHz, Methanol-d4) δ 7.89 (d, J = 8.1 Hz, 2H), 7.62 (dd, J = 7.7, 1.8 Hz, 1H), 7.59-7.19 (m, 6H), 6.68 (s, 1H), 4.47-4.30 (m, 3H), 4.28 (s, 2H), 4.12 (d, J = 9.6 Hz, 6H), 3.95-2.21 (m, 18H). |
| 713 | 1H NMR (400 MHz, Methanol-d4) δ 7.99-7.83 (m, 2H), 7.72-7.21 (m, 7H), 6.67 (s, 1H), 4.56-4.27 (m, 11H), 4.13 (d, J = 2.9 Hz, 6H), 3.77-3.62 (m, 1H), 3.13-2.15 (m, 9H). |
| 714 | 1H NMR (400 MHz, Methanol-d4) δ 7.90 (s, 2H), 7.68-7.21 (m, 7H), 6.68 (s, 1H), 4.58-4.25 (m, 8H), 4.13 (d, J = 7.3 Hz, 6H), 3.56 (d, J = 46.3 Hz, 4H), 3.14-2.15 (m, 11H). |
| 715 | 1H NMR (400 MHz, Methanol-d4) δ 7.90 (s, 1H), 7.63 (d, J = 2.1 Hz, 4H), 7.59-7.17 (m, 6H), 6.68 (s, 1H), 4.55-4.25 (m, 4H), 4.13-3.99 (m, 4H), 3.94-3.82 (m, 1H), 3.31-3.20 (m, 2H), 3.22-1.52 (m, 16H). |
| 721 | 1H NMR (400 MHz, Methanol-d4) δ 7.86 (s, 1H), 7.63 (d, J = 2.5 Hz, 4H), 7.57-7.31 (m, 5H), 7.26 (d, J = 7.6 Hz, 1H), 6.67 (s, 1H), 4.48-4.27 (m, 7H), 4.13 (s, 3H), 4.05 (d, J = 6.3 Hz, 1H), 3.72 (p, J = 8.5 Hz, 1H), 3.31-3.20 (m, 2H), 3.16-1.84 (m, 9H). |
| 722 | 1H NMR (400 MHz, Methanol-d4) δ 7.90 (s, 1H), 7.63 (d, J = 2.1 Hz, 4H), 7.50 (t, J = 9.4 Hz, 2H), 7.38 (dd, J = 23.8, 7.6 Hz, 3H), 7.27 (d, J = 7.5 Hz, 1H), 6.68 (s, 1H), 4.52-4.29 (m, 4H), 4.14 (s, 3H), 4.05 (d, J = 7.4 Hz, 1H), 3.95-3.45 (m, 4H), 3.31-3.20 (m, 2H), 3.17-2.62 (m, 4H), 2.55-2.34 (m, 4H), 2.24 (s, 2H), 2.02-1.85 (m, 1H). |
| 723 | 1H NMR (400 MHz, Methanol-d4) δ 7.90 (s, 1H), 7.63 (d, J = 2.4 Hz, 4H), 7.51 (t, J = 9.4 Hz, 2H), 7.39 (dd, J = 23.7, 7.6 Hz, 3H), 7.27 (d, J = 7.6 Hz, 1H), 6.68 (s, 1H), 4.49-4.27 (m, 4H), 4.14 (s, 3H), 4.05 (d, J = 6.8 Hz, 1H), 4.00-3.41 (m, 4H), 3.31-3.20 (m, 2H), 3.12-2.53 (m, 4H), 2.53-2.32 (m, 4H), 2.24 (s, 2H), 2.05-1.82 (m, 1H). |
| 725 | 1H NMR (400 MHz, Methanol-d4) δ 7.88 (s, 1H), 7.63 (s, 4H), 7.50 (t, J = 8.5 Hz, 2H), 7.46-7.32 (m, 3H), 7.26 (d, J = 7.5 Hz, 1H), 6.66 (s, 1H), 4.49-4.30 (m, 4H), 4.18 (t, J = 8.1 Hz, 1H), 4.13 (s, 3H), 4.04 (d, J = 6.8 Hz, 1H), 3.73-3.64 (m, 1H), 3.31-3.20 (m, 2H), 3.14-1.83(m, 13H). |
| 726 | 1H NMR (400 MHz, Methanol-d4) δ 7.98-7.79 (m, 2H), 7.71-7.19 (m, 7H), 6.68 (s, 1H), 4.54-4.23 (m, 8H), 4.14 (d, J = 2.6 Hz, 7H), 3.33-3.21 (m, 2H), 3.14-2.63 (m, 3H), 2.45 (tt, J = 17.1, 9.7 Hz, 7H), 2.23 (s, 1H), 2.04-1.80 (m, 1H). |
| 727 | 1H NMR (400 MHz, Methanol-d4) δ 8.00-7.83 (m, 2H), 7.71-7.58 (m, 1H), 7.60-7.19 (m, 6H), 6.68 (s, 1H), 4.37 (d, J = 2.6 Hz, 2H), 4.24 (s, 2H), 4.20-4.02 (m, 8H), 3.86 (d, J = 12.1 Hz, 1H), 3.33-3.20 (m, 2H), 3.15-2.66(m, 3H), 2.58-2.34 (m, 3H), 2.23 (s, 1H), 2.13-1.90 (m, 1H), 1.61 (s, 3H). |
| 728 | 1H NMR (400 MHz, Methanol-d4) δ 7.91 (d, J = 7.6 Hz, 1H), 7.85 (s, 1H), 7.69-7.59 (m, 1H), 7.60-7.19 (m, 6H), 6.68 (s, 1H), 4.43-4.27 (m, 3H), 4.22 (s, 2H), 4.13 (s, 7H), 3.53-3.49 (m, 1H), 3.33-3.19 (m, 2H), 3.16 (s, 1H), 3.14-2.67 (m, 3H), 2.58 (d, J = 6.3 Hz, 2H), 2.55-2.34 (m, 3H), 2.23 (s, 1H), 2.04-1.84 (m, 1H). |
| 730 | 1H NMR (400 MHz, Methanol-d4) δ 7.87 (s, 1H), 7.63 (d, J = 2.2 Hz, 4H), 7.57-7.21 (m, 6H), 6.68 (s, 1H), 4.45-4.31 (m, 2H), 4.25 (d, J = 2.7 Hz, 2H), 4.15 (s, 3H), 4.05 (t, J = 6.4 Hz, 2H), 3.30-3.20 (m, 4H), 3.11-2.64 (m, 3H), 2.55-2.34 (m, 6H), 2.23 (s, 1H), 1.95 (d, J = 13.0 Hz, 2H). |
| 731 | 1H NMR (400 MHz, Methanol-d4) δ 7.88 (s, 1H), 7.70-7.16 (m, 10H), 6.68 (s, 1H), 4.36 (d, J = 2.2 Hz, 2H), 4.25 (s, 2H), 4.10 (d, J = 22.7 Hz, 5H), 3.88 (d, J = 12.1 Hz, 1H), 3.28 (d, J = 4.9 Hz, 1H), 3.14-2.62 (m, 3H), 2.56-2.32 (m, 3H), 2.23 (s, 1H), 2.03-1.88 (m, 1H), 1.63 (s, 3H). |
| 732 | 1H NMR (400 MHz, Methanol-d4) δ 7.85 (s, 1H), 7.63 (d, J = 2.0 Hz, 4H), 7.57-7.17 (m, 6H), 6.67 (s, 1H), 4.48-4.27 (m, 3H), 4.22 (s, 2H), 4.13 (s, 3H), 4.04 (d, J = 6.7 Hz, 1H), 3.33-3.22 (m, 4H), 3.11-2.64 (m, 3H), 2.59 (d, J = 6.3 Hz, 2H), 2.56-2.30 (m, 3H), 2.23 (s, 1H), 2.02-1.81 (m, 1H). |
| 734 | 1H NMR (400 MHz, Methanol-d4) δ 7.92 (d, J = 7.6 Hz, 1H), 7.87 (s, 1H), 7.63 (dd, J = 7.5, 1.7 Hz, 1H), 7.57-7.31 (m, 5H), 7.28 (d, J = 7.5 Hz, 1H), 6.68 (s, 1H), 4.37 (d, J = 2.6 Hz, 2H), 4.25 (d, J = 2.5 Hz, 2H), 4.20-3.98 (m, 8H), 3.33-3.21 (m, 4H), 3.13-2.63 (m, 3H), 2.58-2.33 (m, 6H), 2.24 (s, 1H), 2.07-1.77 (m, 2H). |
| 735 | 1H NMR (400 MHz, Methanol-d4) δ 7.98 (s, 1H), 7.90 (d, J = 7.4 Hz, 1H), 7.63 (dd, J = 7.7, 1.8 Hz, 1H), 7.59-7.17 (m, 6H), 6.65 (s, 1H), 4.62-4.23 (m, 12H), 4.13 (d, J = 5.5 Hz, 6H), 3.10-2.65 (m, 3H), 2.68-2.32 (m, 8H), 2.22 (s, 1H). |
| 736 | 1H NMR (400 MHz, Methanol-d4) δ 8.01 (s, 1H), 7.92 (d, J = 7.6 Hz, 1H), 7.63 (dd, J = 7.7, 1.8 Hz, 1H), 7.58-7.30 (m, 5H), 7.27 (d, J = 7.5 Hz, 1H), 6.65 (s, 1H), 4.37 (d, J = 2.6 Hz, 2H), 4.25 (d, J = 2.4 Hz, 2H), 4.20-3.97 (m, 8H), 3.33-3.20 (m, 4H), 3.15-2.61 (m, 3H), 2.59-2.30 (m, 6H), 2.22 (s, 1H), 2.07-1.83 (m, 2H). |
| 737 | 1H NMR (400 MHz, Methanol-d4) δ 9.02 (d, J = 2.0 Hz, 1H), 8.87 (s, 1H), 8.44 (s, 1H), 8.11 (s, 1H), 7.98 (d, J = 8.1 Hz, 2H), 7.79 (d, J = 8.2 Hz, 2H), 7.60-7.39 (m, 3H), 7.30 (d, J = 26.0 Hz, 3H), 6.57 (s, 1H), 5.66 (s, 2H), 4.35 (s, 2H), 4.17 (s, 4H), 4.11 (d, J = 12.2 Hz, 1H), 3.90 (d, J = 12.2 Hz, 1H), 2.85 (dd, J = 47.3, 25.8 Hz, 2H), 2.60 (d, J = 10.9 Hz, 1H), 2.13 (dq, J = 13.6, 6.7 Hz, 1H), 1.63 (s, 3H). |
| 738 | 1H NMR (400 MHz, Methanol-d4) δ 9.02 (s, 1H), 8.87 (s, 1H), 8.43 (s, 1H), 8.11-7.91 (m, 3H), 7.88-7.67 (m, 3H), 7.65-7.12 (m, 5H), 6.58 (s, 1H), 5.67 (s, 2H), 4.35 (s, 2H), 4.17 (s, 4H), 4.11 (d, J = 11.9 Hz, 1H), 3.89 (d, J = 12.2 Hz, 1H), 3.05-2.71 (m, 2H), 2.60 (s, 1H), 2.13 (d, J = 10.8 Hz, 1H), 1.63 (s, 3H). |

-continued

| Example No. | NMR |
|---|---|
| 739 | 1H NMR (400 MHz, Methanol-d4) δ 8.01 (s, 1H), 7.92 (d, J = 7.6 Hz, 1H), 7.63 (dd, J = 7.7, 1.8 Hz, 1H), 7.58-7.30 (m, 5H), 7.27 (d, J = 7.5 Hz, 1H), 6.65 (s, 1H), 4.37 (d, J = 2.6 Hz, 2H), 4.25 (d, J = 2.4 Hz, 2H), 4.20-3.97 (m, 8H), 3.33-3.20 (m, 4H), 3.15-2.61 (m, 3H), 2.59-2.30 (m, 6H), 2.22 (s, 1H), 2.07-1.83 (m, 2H). |
| 741 | 1H NMR (400 MHz, Methanol-d4) δ 9.02 (d, J = 2.0 Hz, 1H), 8.89 (d, J = 12.1 Hz, 1H), 8.43 (s, 1H), 8.10 (s, 1H), 7.74-7.14 (m, 10H), 6.56 (s, 1H), 5.66 (s, 2H), 4.44-4.28 (m, 4H), 4.20-4.00 (m, 2H), 3.90 (d, J = 12.2 Hz, 1H), 3.27 (t, J = 5.8 Hz, 2H), 3.11-2.52 (m, 3H), 2.53-2.32 (m, 3H), 2.13 (dt, J = 13.1, 6.7 Hz, 1H), 1.94 (q, J = 6.9, 6.5 Hz, 1H), 1.63 (s, 3H). |
| 743 | 1H NMR (400 MHz, Methanol-d4) δ 9.01 (s, 1H), 8.89 (s, 1H), 8.51 (s, 1H), 8.11 (s, 1H), 7.92 (d, J = 7.5 Hz, 1H), 7.64 (d, J = 7.2 Hz, 1H), 7.53 (t, J = 7.6 Hz, 1H), 7.49-7.21 (m, 5H), 6.67-6.49 (m, 1H), 5.67 (s, 2H), 4.45-4.24 (m, 4H), 4.20-3.99 (m, 5H), 3.96-3.84 (m, 4H), 3.31-3.26 (m, 2H), 3.10-2.70 (m, 2H), 2.70-2.53 (m, 1H), 2.53-2.27 (m, 3H), 2.22-2.05 (m, 1H), 2.05-1.79 (m, 1H), 1.64 (s, 3H). |
| 744 | 1H NMR (400 MHz, Methanol-d4) δ 9.02 (s, 1H), 8.87 (s, 1H), 8.43 (s, 1H), 8.30 (d, J = 8.0 Hz, 1H), 8.10 (s, 1H), 7.75-7.69 (m, 1H), 7.65-7.52 (m, 2H), 7.52-7.45 (m, 1H), 7.39-7.19 (m, 3H), 6.60-6.48 (m, 1H), 5.66 (s, 2H), 4.34 (s, 2H), 4.21 (s, 3H), 4.18-4.04 (m, 5H), 3.99-3.84 (m, 1H), 3.07-2.68 (m, 2H), 2.68-2.50 (m, 1H), 2.25-2.04 (m, 1H), 1.63 (s, 3H). |
| 747 | 1H NMR (400 MHz, Methanol-d4) δ 9.02 (s, 1H), 8.87 (s, 1H), 8.44 (s, 1H), 8.10 (s, 1H), 7.92 (d, J = 7.7 Hz, 1H), 7.63 (dd, J = 7.8, 1.9 Hz, 1H), 7.52 (t, J = 7.6 Hz, 1H), 7.48-7.17 (m, 5H), 6.56 (s, 1H), 5.66 (s, 2H), 4.45-4.29 (m, 4H), 4.18-4.01 (m, 5H), 3.95-3.84 (m, 1H), 3.30-3.25 (m, 2H), 3.06-2.67 (m, 2H), 2.67-2.53 (m, 1H), 2.53-2.33 (m, 3H), 2.20-2.07 (m, 1H), 2.01-1.84 (m, 1H), 1.64 (s, 3H). |
| 748 | 1H NMR (400 MHz, Methanol-d4) δ 8.99 (d, J = 2.1 Hz, 1H), 8.84 (d, J = 2.0 Hz, 1H), 8.40 (s, 1H), 8.27 (d, J = 8.0 Hz, 1H), 8.08 (s, 1H), 7.50 (dd, J = 7.6, 1.5 Hz, 1H), 7.46-7.35 (m, 2H), 7.34-7.13 (m, 4H), 6.59-6.48 (m, 1H), 5.69-5.57 (m, 2H), 4.32 (s, 2H), 4.16 (s, 3H), 4.12-4.04 (m, 5H), 3.87 (d, J = 12.2 Hz, 1H), 3.01-2.41 (m, 3H), 2.17 (d, J = 9.3 Hz, 3H), 2.14-2.01 (m, 1H), 1.60 (s, 3H). |
| 749 | 1H NMR (400 MHz, Methanol-d4) δ 8.99 (d, J = 2.2 Hz, 1H), 8.84 (d, J = 2.0 Hz, 1H), 8.39 (s, 1H), 8.27 (d, J = 8.0 Hz, 1H), 7.93 (s, 1H), 7.50 (dd, J = 7.7, 1.5 Hz, 1H), 7.45-7.35 (m, 2H), 7.33-7.12 (m, 4H), 6.62-6.50 (m, 1H), 5.64 (s, 2H), 4.32 (s, 2H), 4.16 (s, 3H), 4.12-4.03 (m, 5H), 3.87 (d, J = 12.2 Hz, 1H), 2.98-2.44 (m, 3H), 2.27-2.03 (m, 4H), 1.61 (s, 3H). |
| 753 | 1H NMR (400 MHz, Methanol-d4) δ 8.21-8.18 (m, 2H), 8.12-8.05 (m, 2H), 7.37-7.03 (m, 10H), 6.46 (t, J = 6.4 Hz, 1H), 5.67-5.57 (m, 2H), 4.47-4.14 (m, 6H), 3.54 (t, J = 5.1 Hz, 2H), 3.40-3.32 (m, 2H), 3.19-3.03 (m, 2H), 2.97-2.60 (m, 2H), 2.60-2.41 (m, 5H), 2.10-1.99 (m, 1H), 1.96 (d, J = 4.4 Hz, 3H). |
| 757 | 1H NMR (400 MHz, Methanol-d4) δ 7.95-7.84 (m, 2H), 7.63 (dd, J = 7.7, 1.8 Hz, 1H), 7.51 (d, J = 7.8 Hz, 2H), 7.44-7.31 (m, 3H), 7.27 (d, J = 7.3 Hz, 1H), 6.66 (s, 1H), 4.41-4.29 (m, 7H), 4.13 (d, J = 0.9 Hz, 7H), 3.72 (q, J = 8.6 Hz, 1H), 3.37 (s, 1H), 3.28 (dd, J = 6.2, 3.7 Hz, 2H), 3.01 (s, 1H), 2.71 (d, J = 26.4 Hz, 2H), 2.51-2.35 (m, 3H), 2.22 (s, 1H), 2.00-1.89 (m, 1H). |
| 758 | 1H NMR (400 MHz, Methanol-d4) δ 7.95-7.87 (m, 2H), 7.63 (dd, J = 7.7, 1.8 Hz, 1H), 7.52 (s, 2H), 7.48-7.33 (m, 3H), 7.27 (d, J = 7.6 Hz, 1H), 6.69 (s, 1H), 4.43-4.32 (m, 2H), 4.31 (ddd, J = 9.0, 7.3, 2.0 Hz, 5H), 4.13 (s, 4H), 4.07 (q, J = 6.6 Hz, 1H), 3.71 (dd, J = 8.6, 2.6 Hz, 1H), 3.37 (s, 1H), 3.31-3.25 (m, 1H), 3.12 (s, 3H), 3.04-2.96 (m, 2H), 2.72 (d, J = 32.0 Hz, 3H), 2.51-2.35 (m, 2H), 2.27-2.17 (m, 3H), 2.00-1.88 (m, 2H). |
| 759 | 1H NMR (400 MHz, Methanol-d4) δ 7.95-7.87 (m, 2H), 7.63 (dd, J = 7.7, 1.8 Hz, 1H), 7.53 (d, J = 7.7 Hz, 2H), 7.48-7.35 (m, 3H), 7.27 (d, J = 7.4 Hz, 1H), 6.69 (s, 1H), 4.43-4.29 (m, 3H), 4.17-3.96 (m, 7H), 3.77-3.69 (m, 1H), 3.69-3.61 (m, 1H), 3.53 (d, J = 15.2 Hz, 1H), 3.28 (dd, J = 6.2, 3.8 Hz, 2H), 3.12 (s, 2H), 2.99 (d, J = 13.8 Hz, 1H), 2.87-2.70 (m, 2H), 2.51-2.35 (m, 3H), 2.23 (s, 2H), 2.12-2.03 (m, 1H), 1.99-1.86 (m, 2H), 1.85-1.72 (m, 1H), 1.66-1.58 (m, 1H). |
| 761 | 1H NMR (400 MHz, Methanol-d4) δ 7.95-7.82 (m, 2H), 7.63 (dd, J = 7.6, 1.8 Hz, 1H), 7.52 (s, 2H), 7.39 (d, J = 7.5 Hz, 2H), 7.27 (d, J = 7.6 Hz, 1H), 6.68 (s, 1H), 4.37 (d, J = 2.8 Hz, 2H), 4.35-4.22 (m, 2H), 4.18-4.04 (m, 6H), 3.62 (d, J = 12.1 Hz, 1H), 3.52 (d, J = 7.0 Hz, 1H), 3.37 (s, 1H), 3.29 (dd, J = 6.2, 3.7 Hz, 2H), 3.01 (t, J = 12.2 Hz, 2H), 2.84 (d, J = 12.4 Hz, 1H), 2.76 (s, 2H), 2.72-2.63 (m, 1H), 2.51-2.35 (m, 3H), 2.23 (d, J = 13.2 Hz, 2H), 2.03-1.89 (m, 2H), 1.80 (dd, J = 13.2, 2.7 Hz, 1H), 1.64-1.52 (m, 1H), 1.29 (s, 3H). |
| 762 | 1H NMR (400 MHz, Methanol-d4) δ 7.95-7.87 (m, 2H), 7.66-7.59 (m, 1H), 7.53 (d, J = 7.6 Hz, 2H), 7.43-7.32 (m, 3H), 7.27 (d, J = 7.5 Hz, 1H), 6.68 (s, 1H), 4.40-4.26 (m, 4H), 4.16-4.02 (m, 7H), 3.37 (s, 3H), 2.82-2.70 (m, 3H), 2.72-2.63 (m, 1H), 2.49-2.36 (m, 4H), 2.26-2.18 (m, 3H), 1.95 (ddd, J = 19.9, 16.9, 8.4 Hz, 5H). |
| 763 | 1H NMR (400 MHz, Methanol-d4) δ 7.91 (d, J = 7.8 Hz, 2H), 7.63 (dd, J = 7.7, 1.8 Hz, 1H), 7.52 (s, 3H), 7.43-7.33 (m, 2H), 7.27 (d, J = 7.6 Hz, 1H), 6.68 (s, 1H), 4.43-4.34 (m, 4H), 4.14 (d, J = 3.4 Hz, 6H), 4.07 (d, J = 8.5 Hz, 2H), 3.66 (s, 2H), 3.37 (s, 6H), 2.72 (d, J = 32.0 Hz, 1H), 2.49-2.36 (m, 2H), 2.23 (s, 2H), 1.94 (d, J = 7.7 Hz, 1H), 1.49 (d, J = 16.3 Hz, 4H). |
| 764 | 1H NMR (400 MHz, Methanol-d4) δ 7.96-7.85 (m, 2H), 7.63 (dd, J = 7.6, 1.8 Hz, 1H), 7.53 (d, J = 7.1 Hz, 2H), 7.43-7.36 (m, 3H), 7.28 (d, J = 7.3 Hz, 1H), 6.68 (s, 1H), 4.43-4.31 (m, 3H), 4.15 (d, J = 16.4 Hz, 6H), 4.14-4.04 (m, 1H), 3.69 (s, 1H), 3.37 (s, 1H), 3.31-3.23 (m, 4H), 3.02 (d, J = 5.3 Hz, 2H), 2.79-2.65 (m, 3H), 2.51-2.35 (m, 3H), 2.24 (s, 1H), 2.07-1.98 (m, 2H), 1.98-1.89 (m, 1H), 1.64-1.56 (m, 2H), 1.51-1.43 (m, 2H). |

-continued

| Example No. | NMR |
|---|---|
| 765 | 1H NMR (400 MHz, Methanol-d4) δ 7.91 (t, J = 6.9 Hz, 2H), 7.63 (dd, J = 7.7, 1.8 Hz, 1H), 7.52 (s, 2H), 7.38 (dd, J = 13.8, 7.3 Hz, 3H), 7.27 (d, J = 7.4 Hz, 1H), 6.68 (s, 1H), 4.43-4.29 (m, 4H), 4.13 (d, J = 3.0 Hz, 7H), 3.91 (s, 1H), 3.69 (s, 1H), 3.61 (d, J = 11.3 Hz, 1H), 3.29 (dd, J = 6.2, 3.7 Hz, 2H), 3.01 (d, J = 12.5 Hz, 2H), 2.81 (s, 6H), 2.61-2.51 (m, 1H), 2.51-2.35 (m, 3H), 2.23 (s, 1H), 1.32 (d, J = 7.3 Hz, 3H). |
| 766 | 1H NMR (400 MHz, Methanol-d4) δ 7.97-7.88 (m, 2H), 7.63 (dd, J = 7.7, 1.8 Hz, 1H), 7.52 (s, 2H), 7.44-7.33 (m, 3H), 7.27 (d, J = 7.6 Hz, 1H), 6.68 (s, 1H), 4.49-4.31 (m, 4H), 4.13 (s, 6H), 4.08 (t, J = 6.6 Hz, 1H), 3.63 (d, J = 12.4 Hz, 1H), 3.38 (d, J = 7.8 Hz, 2H), 3.31-3.21 (m, 4H), 2.81-2.65 (m, 3H), 2.51-2.33 (m, 3H), 2.29-2.18 (m, 1H), 2.15-1.90 (m, 6H), 1.38-1.27 (m, 1H). |
| 769 | 1H NMR (400 MHz, Methanol-d4) δ 7.92 (d, J = 8.3 Hz, 2H), 7.67-7.60 (m, 1H), 7.52 (s, 2H), 7.49-7.33 (m, 3H), 7.28 (d, J = 7.6 Hz, 1H), 6.69 (s, 1H), 4.37 (d, J = 2.7 Hz, 3H), 4.14 (d, J = 3.4 Hz, 7H), 3.95-3.83 (m, 1H), 3.81-3.74 (m, 1H), 3.63 (d, J = 8.8 Hz, 2H), 3.32-3.25 (m, 1H), 2.99 (dd, J = 13.1, 6.7 Hz, 2H), 2.81 (s, 2H), 2.79-2.65 (m, 2H), 2.61-2.52 (m, 1H), 2.49-2.35 (m, 3H), 2.23 (d, J = 12.3 Hz, 2H), 1.98-1.90 (m, 1H). |
| 775 | 1H NMR (400 MHz, Methanol-d4) δ 8.27 (dd, J = 8.0, 1.5 Hz, 1H), 7.95 (s, 1H), 7.68 (dd, J = 7.6, 1.8 Hz, 1H), 7.60-7.38 (m, 4H), 7.34 (t, J = 7.6 Hz, 1H), 7.29-7.21 (m, 1H), 6.62 (s, 1H), 4.33 (d, J = 18.8 Hz, 7H), 4.18 (s, 3H), 4.15 (s, 3H), 4.10 (d, J = 3.0 Hz, 7H), 3.07-2.61 (m, 3H), 2.20 (d, J = 11.8 Hz, 1H), 1.85 (s, 3H). |
| 779 | 1H NMR (400 MHz, Methanol-d4) δ 8.29 (dd, J = 7.9, 1.3 Hz, 1H), 7.97 (s, 1H), 7.68 (dd, J = 7.6, 1.8 Hz, 1H), 7.63-7.29 (m, 6H), 7.25 (dd, J = 7.6, 1.2 Hz, 1H), 6.62 (s, 1H), 4.21 (d, J = 2.1 Hz, 2H), 4.18 (s, 3H), 4.10 (d, J = 1.9 Hz, 7H), 4.04 (t, J = 6.1 Hz, 1H), 3.27-3.11 (m, 2H), 3.07-2.61 (m, 3H), 2.47-2.29 (m, 2H), 2.25-2.12 (m, 1H), 1.98-1.84 (m, 1H). |
| 780 | 1H NMR (400 MHz, Methanol-d4) δ 7.98 (s, 1H), 7.85 (d, J = 8.2 Hz, 1H), 7.58-7.18 (m, 8H), 6.62 (s, 1H), 4.30-4.17 (m, 2H), 4.14-3.99 (m, 12H), 3.86 (d, J = 12.1 Hz, 1H), 3.10-2.58 (m, 3H), 2.19 (s, 1H), 1.61 (s, 3H). |
| 781 | 1H NMR (400 MHz, Methanol-d4) δ 8.32-8.23 (m, 1H), 7.98 (s, 1H), 7.68 (dd, J = 7.6, 1.8 Hz, 1H), 7.62-7.37 (m, 4H), 7.34 (t, J = 7.5 Hz, 1H), 7.24 (dd, J = 7.6, 1.1 Hz, 1H), 6.70-6.55 (m, 1H), 4.60-4.47 (m, 1H), 4.23 (d, J = 11.6 Hz, 3H), 4.18 (s, 4H), 4.09 (s, 4H), 4.05 (d, J = 12.1 Hz, 1H), 3.85 (dd, J = 12.1, 2.5 Hz, 1H), 3.68 (dd, J = 11.5, 7.9 Hz, 1H), 3.12-2.60 (m, 3H), 2.25-2.11 (m, 1H), 1.60 (d, J = 1.7 Hz, 3H), 1.48 (d, J = 6.4 Hz, 3H). |
| 782 | 1H NMR (400 MHz, Methanol-d4) δ 8.27 (dd, J = 8.0, 1.1 Hz, 1H), 7.98 (s, 1H), 7.68 (dd, J = 7.6, 1.8 Hz, 1H), 7.62-7.38 (m, 4H), 7.34 (t, J = 7.5 Hz, 1H), 7.29-7.16 (m, 1H), 6.63 (s, 1H), 4.54 (ddd, J = 11.3, 7.8, 6.2 Hz, 1H), 4.28-4.21 (m, 3H), 4.18 (s, 3H), 4.06 (d, J = 21.7 Hz, 4H), 3.92-3.80 (m, 1H), 3.68 (dd, J = 11.5, 8.0 Hz, 1H), 3.17-2.60 (m, 3H), 2.19 (s, 1H), 1.60 (d, J = 1.2 Hz, 3H), 1.48 (d, J = 6.4 Hz, 3H). |
| 785 | 1H NMR (400 MHz, Methanol-d4) δ 8.28 (d, J = 8.0 Hz, 1H), 8.00 (s, 1H), 7.68 (dd, J = 7.6, 1.8 Hz, 1H), 7.62-7.22 (m, 5H), 6.63 (s, 1H), 4.48-4.25 (m, 1H), 4.18 (s, 3H), 4.10 (s, 5H), 4.06 (s, 3H), 3.89 (s, 1H), 3.34 (s, 5H), 3.18-2.61 (m, 3H), 2.42-1.54 (m, 6H). |
| 786 | 1H NMR (400 MHz, Methanol-d4) δ 8.28 (d, J = 8.0 Hz, 1H), 7.96 (s, 1H), 7.68 (dd, J = 7.6, 1.8 Hz, 1H), 7.61-7.39 (m, 5H), 7.34 (t, J = 7.6 Hz, 1H), 7.28-7.20 (m, 1H), 6.62 (s, 1H), 4.17 (d, J = 6.5 Hz, 6H), 4.10 (d, J = 3.5 Hz, 8H), 3.16-2.60 (m, 3H), 2.19 (s, 1H), 1.66 (s, 6H). |
| 787 | 1H NMR (400 MHz, Methanol-d4) δ 8.29 (dd, J = 8.0, 1.2 Hz, 1H), 7.96 (s, 1H), 7.68 (dd, J = 7.6, 1.8 Hz, 1H), 7.60-7.39 (m, 4H), 7.34 (t, J = 7.6 Hz, 1H), 7.25 (dd, J = 7.6, 1.1 Hz, 1H), 6.62 (d, J = 6.3 Hz, 1H), 4.31 (dtd, J = 9.6, 6.3, 3.0 Hz, 1H), 4.18 (d, J = 4.7 Hz, 5H), 4.10 (d, J = 3.4 Hz, 7H), 3.23 (dd, J = 12.7, 3.0 Hz, 1H), 3.09-2.64 (m, 3H), 2.56 (d, J = 6.3 Hz, 2H), 2.19 (d, J = 10.0 Hz, 1H). |
| 788 | 1H NMR (400 MHz, Methanol-d4) δ 8.28 (dd, J = 8.0, 1.0 Hz, 1H), 7.98 (s, 1H), 7.68 (dd, J = 7.6, 1.8 Hz, 1H), 7.61-7.38 (m, 4H), 7.34 (t, J = 7.6 Hz, 1H), 7.29-7.20 (m, 1H), 6.62 (s, 1H), 4.22 (d, J = 6.2 Hz, 1H), 4.18 (s, 3H), 4.10 (d, J = 5.6 Hz, 7H), 4.06 (d, J = 12.1 Hz, 1H), 3.85 (d, J = 12.1 Hz, 1H), 3.11-2.60 (m, 3H), 2.19 (s, 1H), 1.60 (s, 3H). |
| 789 | 1H NMR (400 MHz, Methanol-d4) δ 8.28 (dt, J = 7.9, 1.0 Hz, 1H), 7.98 (s, 1H), 7.68 (dd, J = 7.6, 1.8 Hz, 1H), 7.61-7.39 (m, 4H), 7.34 (t, J = 7.6 Hz, 1H), 7.28-7.19 (m, 1H), 6.62 (s, 1H), 4.22 (d, J = 2.3 Hz, 2H), 4.18 (s, 4H), 4.10 (d, J = 5.6 Hz, 9H), 4.04 (s, 1H), 3.86 (d, J = 12.1 Hz, 1H), 3.14-2.62 (m, 1H), 2.19 (s, 1H), 1.60 (s, 3H). |
| 790 | 1H NMR (400 MHz, Methanol-d4) δ 7.97 (s, 1H), 7.66 (t, J = 7.9 Hz, 1H), 7.48 (dd, J = 7.5, 4.2 Hz, 2H), 7.44-7.28 (m, 4H), 7.23 (dd, J = 7.6, 1.1 Hz, 1H), 6.61 (d, J = 7.2 Hz, 1H), 4.42 (d, J = 1.8 Hz, 2H), 4.21 (d, J = 2.1 Hz, 2H), 4.10 (s, 3H), 4.04 (p, J = 5.9, 5.4 Hz, 2H), 3.31-3.25 (m, 5H), 3.07-2.61 (m, 2H), 2.51-2.28 (m, 6H), 2.17-1.82 (m, 4H). |
| 792 | 1H NMR (400 MHz, Methanol-d4) δ 7.97 (s, 1H), 7.56-7.29 (m, 5H), 7.26-7.17 (m, 2H), 7.12 (dd, J = 7.7, 1.4 Hz, 1H), 6.61 (d, J = 7.0 Hz, 1H), 4.41-4.28 (m, 2H), 4.21 (d, J = 2.1 Hz, 2H), 4.10 (s, 3H), 4.04 (dd, J = 7.4, 5.7 Hz, 1H), 3.97 (s, 3H), 3.27-3.12 (m, 4H), 3.07-2.56 (m, 3H), 2.48-2.29 (m, 6H), 2.17-1.90 (m, 5H). |
| 797 | 1H NMR (400 MHz, Methanol-d4) δ 8.18 (s, 2H), 8.07 (d, J = 16.7 Hz, 1H), 7.95-7.83 (m, 2H), 7.63-7.56 (m, 2H), 7.46 (dt, J = 19.9, 9.7 Hz, 2H), 7.35 (t, J = 7.2 Hz, 1H), 7.23 (d, J = 6.7 Hz, 2H), 7.00 (s, 1H), 6.48 (s, 1H), 5.61 (s, 2H), 4.37-4.28 (m, 4H), 4.10 (d, J = 4.7 Hz, 3H), 3.29-3.22 (m, 1H), 3.13-3.02 (m, 1H), 2.88 (s, 1H), 2.79 (s, 1H), 2.58 (dd, J = 6.4, 4.4 Hz, 4H), 2.46-2.33 (m, 2H), 2.05 (d, J = 19.7 Hz, 1H), 1.91 (s, 2H), 1.32-1.26 (m, 1H). |

-continued

| Example No. | NMR |
|---|---|
| 798 | 1H NMR (400 MHz, Methanol-d4) δ 7.87 (s, 1H), 7.60 (dd, J = 7.7, 1.8 Hz, 1H), 7.51 (d, J = 7.5 Hz, 2H), 7.47-7.33 (m, 2H), 7.26 (d, J = 7.8 Hz, 2H), 6.67 (d, J = 6.2 Hz, 1H), 4.42 (s, 2H), 4.24 (d, J = 2.3 Hz, 2H), 4.12 (d, J = 9.0 Hz, 6H), 4.06 (dt, J = 12.8, 6.5 Hz, 2H), 3.29-3.19 (m, 2H), 3.00 (dd, J = 31.1, 13.1 Hz, 1H), 2.92-2.70 (m, 2H), 2.68 (s, 1H), 2.54 (s, 3H), 2.52-2.34 (m, 6H), 2.25 (d, J = 15.3 Hz, 1H), 2.05-1.86 (m, 2H). |
| 799 | 1H NMR (400 MHz, DMSO-d6) δ 8.89 (d, J = 50.9 Hz, 2H), 8.66 (d, J = 29.3 Hz, 2H), 8.00 (s, 1H), 7.58 (d, J = 2.4 Hz, 3H), 7.49 (d, J = 3.7 Hz, 2H), 7.40 (t, J = 7.5 Hz, 1H), 7.30 (d, J = 7.2 Hz, 1H), 6.64 (d, J = 6.8 Hz, 1H), 4.34 (s, 2H), 4.12 (d, J = 5.3 Hz, 2H), 4.03 (d, J = 4.0 Hz, 5H), 3.88 (dt, J = 13.0, 8.1 Hz, 3H), 3.28-2.96 (m, 5H), 2.96-2.65 (m, 4H), 2.25-2.13 (m, 5H), 1.88-1.74 (m, 2H). |
| 800 | 1H NMR (400 MHz, DMSO-d6) δ 9.05 (s, 1H), 8.99 (s, 2H), 8.84 (s, 1H), 8.68 (s, 2H), 8.49 (s, 1H), 7.99 (d, J = 7.6 Hz, 1H), 7.84 (d, J = 8.1 Hz, 1H), 7.63-7.51 (m, 3H), 7.45 (t, J = 9.9 Hz, 2H), 7.38-7.23 (m, 3H), 6.54 (d, J = 8.1 Hz, 1H), 6.48 (s, 1H), 5.60 (s, 2H), 4.24 (s, 4H), 4.01 (s, 3H), 3.90 (t, J = 6.6 Hz, 2H), 3.10 (s, 5H), 2.87 (s, 2H), 2.72 (s, 2H), 2.19 (tq, J = 12.3, 6.5 Hz, 6H). |
| 801 | 1H NMR (400 MHz, DMSO-d6) δ 9.06 (d, J = 2.1 Hz, 1H), 9.00 (d, J = 1.9 Hz, 1H), 8.81 (s, 2H), 8.67 (s, 1H), 8.50 (s, 1H), 8.30 (s, 1H), 8.15 (s, 1H), 8.08 (s, 1H), 7.69-7.53 (m, 4H), 7.45 (d, J = 18.0 Hz, 2H), 7.33 (s, 2H), 7.26 (s, 1H), 6.55 (s, 2H), 5.62 (s, 2H), 4.85 (s, 3H), 4.22 (s, 3H), 3.88 (s, 3H), 2.25-2.10 (m, 5H), 1.98 (s, 2H), 1.79 (d, J = 22.4 Hz, 3H). |
| 802 | 1H NMR (400 MHz, DMSO-d6) δ 9.21 (s, 1H), 9.03 (d, J = 21.4 Hz, 3H), 8.50 (s, 2H), 8.08 (s, 2H), 7.95 (d, J = 7.5 Hz, 2H), 7.88 (s, 2H), 7.60 (d, J = 10.1 Hz, 3H), 7.34 (d, J = 16.5 Hz, 3H), 6.54 (s, 2H), 5.63 (s, 2H), 4.37 (s, 2H), 4.23 (s, 2H), 3.87 (s, 3H), 3.58 (s, 4H), 2.19 (d, J = 7.9 Hz, 4H). |
| 803 | 1H NMR (400 MHz, DMSO-d6) δ 9.16 (s, 1H), 8.99 (d, J = 23.2 Hz, 2H), 7.72 (s, 4H), 7.30 (d, J = 16.6 Hz, 2H), 6.50 (s, 3H), 5.51 (d, J = 52.9 Hz, 3H), 4.30 (s, 1H), 4.09 (d, J = 56.2 Hz, 4H), 2.92 (d, J = 40.3 Hz, 3H), 2.68 (d, J = 6.3 Hz, 3H), 2.24-1.87 (m, 5H). |

Biological Activity

PD-1/PD-L1 & CTLA/CD80 Biochemical Protein-Protein Interaction Assay

Compounds were tested in biochemical protein-protein interaction assays to determine if they can specifically block the interaction between the extracellular domains of PD-1/PD-L1 or CTLA/CD80. Binding of the protein pairs is measured using a bead based Amplified Luminescent Proximity Homogeneous Assay (ALPHA) platform. Binding of each protein pair results in proximity of the donor and acceptor beads which leads to an increase in ALPHA signal. Disruption of the protein-protein interaction with a test compound results in a decrease in ALPHA signal. Assays are performed in 25 mM Hepes (pH 7.4), 150 mM NaCl, 3.4 mM EDTA, 0.005% Tween 20, and 0.01% BSA. Final protein concentration in the assays were 0.3 nM (His tagged PD-L1), 2.5 nM (biotinylated Fc-PD-1), 1 nM (His tagged CTLA4) and 1 nM (biotinylated CD80). After an assay reaction time of 60 minutes at 25° C., binding was measured with addition of 20 μg/mL ALPHA assay acceptor beads (anti-His coated) and 20 pg/mL ALPHA assay donor beads (streptavidin coated). $IC_{50}$ values were calculated from the fit of the dose-response curves to a four-parameter equation. Representative data are shown below in Table 1.

TABLE 1

| Example | $IC_{50}$ PD-L1-PD-1 Alpha $IC_{50}$-mono PD-L1-fcP-D1 (nM) |
|---|---|
| 3 | 0.2 |
| 4 | 0.1 |
| 5 | 0.1 |
| 6 | 0.1 |
| 7 | 0.1 |
| 9 | 0.5 |
| 11 | 0.4 |

TABLE 1-continued

| Example | $IC_{50}$ PD-L1-PD-1 Alpha $IC_{50}$-mono PD-L1-fcP-D1 (nM) |
|---|---|
| 12 | 11.1 |
| 13 | 2.2 |
| 14 | 2.1 |
| 15 | 1250 |
| 16 | 0.1 |
| 17 | 0.3 |
| 18 | 16.2 |
| 19 | 1.1 |
| 20 | 12.6 |
| 21 | 17 |
| 22 | 34.9 |
| 23 | 40.6 |
| 24 | 41.7 |
| 25 | 20.9 |
| 26 | 16.2 |
| 27 | 2.3 |
| 28 | 12.7 |
| 29 | 0.8 |
| 32 | 0.3 |
| 33 | 0.4 |
| 34 | 0.4 |
| 35 | 15.6 |
| 36 | 21.6 |
| 38 | 2.8 |
| 39 | 166.6 |
| 40 | 0.1 |
| 41 | 0.2 |
| 42 | 0.3 |
| 58 | 0.3 |
| 59 | 0.1 |
| 60 | 2.3 |
| 61 | 0.7 |
| 66 | 0.4 |
| 67 | 1 |
| 68 | 10.3 |
| 69 | 14.2 |
| 70 | 10.6 |
| 71 | 26.5 |

TABLE 1-continued

| Example | $IC_{50}$ PD-L1-PD-1 Alpha $IC_{50}$-mono PD-L1-fcP-D1 (nM) |
|---|---|
| 72 | 8 |
| 73 | 56.1 |
| 84 | 0.9 |
| 106 | 0.4 |
| 113 | 0.6 |
| 114 | 0.5 |
| 119 | 0.8 |
| 120 | 2 |
| 121 | 1.4 |
| 126 | 0.1 |
| 127 | 0.2 |
| 132 | 0.3 |
| 137 | 0.6 |
| 138 | 1 |
| 139 | 5.1 |
| 141 | 3.6 |
| 147 | 0.3 |
| 150 | 0.5 |
| 151 | 2.2 |
| 154 | 3.8 |
| 155 | 0.2 |
| 156 | 2.3 |
| 157 | 0.2 |
| 158 | 2 |
| 159 | 0.5 |
| 160 | 0.6 |
| 161 | 2.8 |
| 162 | 0.2 |
| 163 | 0.6 |
| 164 | 0.2 |
| 165 | 5.8 |
| 166 | 2 |
| 167 | 2.2 |
| 177 | 0.1 |
| 178 | 0.2 |
| 180 | 4.6 |
| 181 | 3.3 |
| 186 | 18.8 |
| 187 | 0.6 |
| 188 | 0.3 |
| 199 | 187.8 |
| 200 | 138.3 |
| 201 | 31.2 |
| 202 | 3.2 |
| 203 | 1 |
| 204 | 25.7 |
| 205 | 6.9 |
| 206 | 0.2 |
| 207 | 2 |
| 208 | 1.4 |
| 213 | 1.6 |
| 214 | 0.2 |
| 215 | 1.26 |
| 219 | 0.2 |
| 220 | 2 |
| 221 | 1.5 |
| 222 | 0.3 |
| 223 | 34.6 |
| 224 | 1.8 |
| 238 | 0.9 |
| 239 | 8.1 |
| 240 | 0.4 |
| 241 | 0.6 |
| 242 | 0.2 |
| 243 | 0.2 |
| 245 | 0.6 |
| 246 | 1 |
| 248 | 0.2 |
| 250 | 63.6 |
| 251 | 2 |
| 252 | 0.3 |
| 253 | 4.6 |
| 254 | 20.8 |
| 257 | 24 |

TABLE 1-continued

| Example | $IC_{50}$ PD-L1-PD-1 Alpha $IC_{50}$-mono PD-L1-fcP-D1 (nM) |
|---|---|
| 258 | 6.3 |
| 259 | 22.7 |
| 261 | 120 |
| 262 | 1.5 |
| 263 | 1.8 |
| 265 | 3.2 |
| 267 | 1.1 |
| 269 | 12.3 |
| 271 | 56 |
| 272 | 2.5 |
| 273 | 200.2 |
| 275 | 153.9 |
| 276 | 77.8 |
| 277 | 124.8 |
| 280 | 0.3 |
| 281 | 8.7 |
| 283 | 0.8 |
| 287 | 456.6100 |
| 289 | 0.075 |
| 290 | 0.068 |
| 291 | 0.175 |
| 292 | 0.509 |
| 293 | 0.226 |
| 294 | 9.237 |
| 295 | 0.312 |
| 296 | 0.064 |
| 297 | 0.187 |
| 298 | 0.051 |
| 299 | 0.761 |
| 300 | 0.673 |
| 301 | 0.109 |
| 302 | 0.348 |
| 303 | 0.166 |
| 304 | 0.064 |
| 305 | 0.158 |
| 306 | 1.972 |
| 307 | 0.536 |
| 308 | 0.346 |
| 309 | 0.168 |
| 310 | 0.069 |
| 311 | 0.064 |
| 312 | 0.051 |
| 313 | 0.051 |
| 314 | 0.064 |
| 315 | 0.242 |
| 317 | 0.577 |
| 323 | 0.074 |
| 324 | 0.505 |
| 325 | 1.375 |
| 326 | 1.15 |
| 327 | 0.051 |
| 328 | 0.142 |
| 329 | 0.284 |
| 330 | 0.188 |
| 331 | 0.273 |
| 332 | 0.114 |
| 333 | 0.289 |
| 334 | 0.143 |
| 335 | 0.414 |
| 336 | 0.124 |
| 337 | 0.287 |
| 338 | 0.179 |
| 339 | 1.304 |
| 340 | 0.087 |
| 341 | 0.064 |
| 342 | 0.4 |
| 343 | 0.218 |
| 344 | 0.064 |
| 345 | 0.09 |
| 346 | 0.074 |
| 347 | 0.211 |
| 348 | 0.122 |
| 349 | 0.064 |
| 350 | 0.105 |

TABLE 1-continued

| Example | $IC_{50}$ PD-L1-PD-1 Alpha $IC_{50}$-mono PD-L1-fcP-D1 (nM) |
|---|---|
| 351 | 0.982 |
| 352 | 0.207 |
| 353 | 0.311 |
| 354 | 0.241 |
| 355 | 0.148 |
| 356 | 0.264 |
| 357 | 0.358 |
| 358 | 0.137 |
| 359 | 2.108 |
| 360 | 1.116 |
| 361 | 0.13 |
| 362 | 0.104 |
| 363 | 0.081 |
| 364 | 0.304 |
| 365 | 1.574 |
| 366 | 2.335 |
| 367 | 2.534 |
| 368 | 1.879 |
| 369 | 0.164 |
| 370 | 0.139 |
| 371 | 0.074 |
| 372 | 1.126 |
| 373 | 2.59 |
| 374 | 0.136 |
| 375 | 0.21 |
| 376 | 0.346 |
| 377 | 0.178 |
| 378 | 0.127 |
| 379 | 2.382 |
| 380 | 0.282 |
| 381 | 0.158 |
| 382 | 0.304 |
| 383 | 0.252 |
| 384 | 0.112 |
| 385 | 0.051 |
| 386 | 0.302 |
| 387 | 0.051 |
| 389 | 0.374 |
| 390 | 0.324 |
| 391 | 1.415 |
| 392 | 0.051 |
| 393 | 0.064 |
| 394 | 0.102 |
| 395 | 0.217 |
| 396 | 0.064 |
| 397 | 0.064 |
| 425 | 0.755 |
| 426 | 0.397 |
| 428 | 1.37 |
| 429 | 0.14 |
| 430 | 2.056 |
| 431 | 1.316 |
| 432 | 1.525 |
| 433 | 0.08 |
| 434 | 0.077 |
| 435 | 0.234 |
| 436 | 0.064 |
| 437 | 1.608 |
| 438 | 0.476 |
| 439 | 0.376 |
| 440 | 0.115 |
| 441 | 0.212 |
| 442 | 0.697 |
| 443 | 0.064 |
| 444 | 0.064 |
| 445 | 0.719 |
| 446 | 0.453 |
| 448 | 0.618 |
| 449 | 0.653 |
| 450 | 1.562 |
| 451 | 0.104 |
| 452 | 0.076 |
| 453 | 0.111 |
| 454 | 1.012 |

TABLE 1-continued

| Example | $IC_{50}$ PD-L1-PD-1 Alpha $IC_{50}$-mono PD-L1-fcP-D1 (nM) |
|---|---|
| 455 | 0.172 |
| 456 | 0.269 |
| 457 | 0.064 |
| 458 | 0.325 |
| 459 | 0.064 |
| 460 | 0.147 |
| 461 | 0.064 |
| 463 | 0.159 |
| 464 | 0.099 |
| 465 | 0.116 |
| 466 | 0.064 |
| 467 | 0.161 |
| 468 | 0.558 |
| 469 | 0.064 |
| 470 | 0.096 |
| 471 | 0.205 |
| 473 | 0.159 |
| 474 | 0.064 |
| 475 | 0.088 |
| 476 | 1.109 |
| 477 | 1.038 |
| 478 | 0.064 |
| 479 | 0.098 |
| 480 | 1.125 |
| 481 | 0.064 |
| 482 | 0.064 |
| 483 | 0.064 |
| 484 | 0.205 |
| 485 | 0.321 |
| 486 | 0.146 |
| 487 | 0.064 |
| 488 | 0.064 |
| 489 | 0.064 |
| 490 | 0.064 |
| 491 | 0.064 |
| 497 | 1.433 |
| 498 | 0.115 |
| 499 | 0.093 |
| 500 | 0.064 |
| 501 | 0.064 |
| 502 | 0.081 |
| 503 | 0.064 |
| 504 | 0.064 |
| 505 | 0.064 |
| 506 | 0.239 |
| 507 | 0.693 |
| 508 | 0.084 |
| 509 | 0.097 |
| 510 | 0.064 |
| 511 | 0.082 |
| 512 | 0.526 |
| 513 | 0.301 |
| 514 | 0.735 |
| 515 | 0.203 |
| 516 | 0.065 |
| 517 | 0.064 |
| 518 | 0.064 |
| 519 | 0.064 |
| 520 | 0.064 |
| 521 | 0.064 |
| 522 | 0.064 |
| 523 | 0.295 |
| 524 | 0.064 |
| 525 | 0.064 |
| 526 | 0.064 |
| 527 | 0.064 |
| 528 | 0.068 |
| 529 | 0.064 |
| 540 | 0.593 |
| 541 | 0.641 |
| 542 | 1.243 |
| 543 | 0.07 |
| 544 | 0.09 |
| 545 | 0.089 |

TABLE 1-continued

| Example | $IC_{50}$ PD-L1-PD-1 Alpha $IC_{50}$-mono PD-L1-fcP-D1 (nM) |
|---|---|
| 546 | 0.515 |
| 547 | 0.363 |
| 548 | 0.676 |
| 549 | 0.355 |
| 550 | 0.134 |
| 551 | 0.064 |
| 552 | 0.716 |
| 553 | 0.101 |
| 554 | 0.15 |
| 555 | 0.396 |
| 556 | 0.194 |
| 557 | 0.201 |
| 558 | 0.065 |
| 559 | 0.064 |
| 560 | 0.135 |
| 561 | 0.531 |
| 562 | 0.102 |
| 563 | 0.317 |
| 564 | 0.293 |
| 565 | 0.259 |
| 566 | 0.11 |
| 567 | 0.327 |
| 568 | 0.064 |
| 569 | 0.085 |
| 570 | 0.092 |
| 571 | 0.091 |
| 572 | 0.431 |
| 573 | 0.154 |
| 574 | 0.071 |
| 575 | 0.073 |
| 576 | 0.169 |
| 577 | 0.064 |
| 578 | 0.111 |
| 579 | 0.064 |
| 580 | 0.215 |
| 581 | 0.182 |
| 582 | 1.304 |
| 583 | 0.296 |
| 584 | 0.124 |
| 585 | 0.098 |
| 586 | 0.836 |
| 587 | 0.145 |
| 588 | 0.081 |
| 589 | 0.163 |
| 590 | 0.186 |
| 591 | 0.064 |
| 592 | 0.095 |
| 593 | 0.064 |
| 595 | 0.064 |
| 596 | 0.671 |
| 597 | 1.26 |
| 598 | 3.004 |
| 599 | 0.214 |
| 600 | 0.39 |
| 601 | 5.267 |
| 602 | 0.236 |
| 603 | 0.206 |
| 604 | 4.867 |
| 605 | 1.055 |
| 606 | 6.234 |
| 607 | 1.187 |
| 608 | 1.718 |
| 609 | 0.387 |
| 610 | 0.746 |
| 611 | 0.482 |
| 612 | 2.446 |
| 613 | 1.381 |
| 614 | 11.52 |
| 615 | 7.883 |
| 616 | 0.295 |
| 617 | 0.17 |
| 618 | 0.224 |
| 619 | 0.159 |
| 620 | 2.842 |

TABLE 1-continued

| Example | $IC_{50}$ PD-L1-PD-1 Alpha $IC_{50}$-mono PD-L1-fcP-D1 (nM) |
|---|---|
| 621 | 1.039 |
| 622 | 0.567 |
| 623 | 5.197 |
| 624 | 0.109 |
| 625 | 0.238 |
| 626 | 3.075 |
| 627 | 2.443 |
| 629 | 0.0640 |
| 630 | 0.0640 |
| 631 | 0.13 |
| 632 | 0.147 |
| 633 | 1.261 |
| 634 | 0.208 |
| 635 | 0.1 |
| 636 | 0.188 |
| 637 | 0.0640 |
| 638 | 0.0640 |
| 639 | 1.8540 |
| 640 | 1.0940 |
| 641 | 0.0640 |
| 642 | 2.3580 |
| 643 | 0.7340 |
| 644 | 1.9450 |
| 645 | 0.0640 |
| 646 | 6.2550 |
| 647 | 1.8850 |
| 648 | 0.0640 |
| 649 | 0.0640 |
| 650 | 0.2880 |
| 651 | 0.2970 |
| 652 | 0.1580 |
| 653 | 0.1700 |
| 654 | 0.0900 |
| 655 | 0.4040 |
| 656 | 0.2900 |
| 657 | 0.7950 |
| 658 | 0.2210 |
| 659 | 0.0640 |
| 660 | 0.0640 |
| 661 | 0.2560 |
| 662 | 0.1390 |
| 663 | 0.0640 |
| 664 | 2.6040 |
| 665 | 0.0640 |
| 666 | 0.0760 |
| 667 | 0.0640 |
| 668 | 0.0640 |
| 669 | 0.0640 |
| 670 | 1.7390 |
| 671 | 0.1590 |
| 672 | 0.0640 |
| 673 | 0.1540 |
| 674 | 0.0640 |
| 675 | 0.0640 |
| 676 | 0.0640 |
| 677 | 0.0630 |
| 678 | 0.1050 |
| 679 | 0.0580 |
| 681 | 8.9150 |
| 682 | 0.4210 |
| 683 | 0.1040 |
| 684 | 0.0640 |
| 685 | 0.5520 |
| 686 | 0.2820 |
| 687 | 0.6590 |
| 688 | 0.4120 |
| 689 | 0.0640 |
| 690 | 0.2800 |
| 691 | 2.3500 |
| 692 | 0.0510 |
| 693 | 0.5850 |
| 694 | 0.0510 |
| 695 | 0.0640 |
| 696 | 0.0990 |

TABLE 1-continued

| Example | $IC_{50}$ PD-L1-PD-1 Alpha $IC_{50}$-mono PD-L1-fcP-D1 (nM) |
|---|---|
| 697 | 0.0680 |
| 698 | 0.7040 |
| 699 | 0.1200 |
| 700 | 0.0640 |
| 701 | 0.8180 |
| 702 | 0.3160 |
| 703 | 0.0640 |
| 704 | 0.0640 |
| 705 | 0.0640 |
| 706 | 0.0640 |
| 707 | 0.0640 |
| 708 | 0.0640 |
| 709 | 0.0640 |
| 710 | 0.0640 |
| 711 | 0.0690 |
| 712 | 0.0640 |
| 713 | 0.0640 |
| 714 | 0.0640 |
| 715 | 0.0640 |
| 716 | 0.4030 |
| 717 | 0.5720 |
| 718 | 0.2420 |
| 719 | 0.0640 |
| 720 | 0.2620 |
| 721 | 0.0640 |
| 722 | 0.0640 |
| 723 | 0.0640 |
| 724 | 0.0640 |
| 725 | 0.0640 |
| 726 | 0.1250 |
| 727 | 0.0640 |
| 728 | 0.0640 |
| 729 | 0.9350 |
| 730 | 0.7400 |
| 731 | 0.0640 |
| 732 | 0.0740 |
| 733 | 0.2220 |
| 734 | 0.4630 |
| 735 | 0.3450 |
| 736 | 0.1530 |
| 737 | 0.0640 |
| 738 | 0.0640 |
| 739 | 0.0640 |
| 740 | 0.0640 |
| 741 | 0.0640 |
| 742 | 0.0640 |
| 743 | 0.3120 |
| 744 | 0.0640 |
| 745 | 0.0640 |
| 746 | 0.0640 |
| 747 | 0.0640 |
| 748 | 0.0640 |
| 749 | 0.0640 |
| 750 | 0.0640 |
| 751 | 4.5080 |
| 752 | 0.7790 |
| 753 | 0.0640 |
| 754 | 0.0910 |
| 755 | 0.1550 |
| 756 | 1.1610 |
| 757 | 0.0640 |
| 758 | 0.0640 |
| 759 | 0.0640 |
| 760 | 0.0640 |
| 761 | 0.0640 |
| 762 | 0.0640 |
| 763 | 0.0640 |
| 764 | 0.0640 |
| 765 | 0.0640 |
| 766 | 0.0640 |
| 767 | 0.0640 |

TABLE 1-continued

| Example | $IC_{50}$ PD-L1-PD-1 Alpha $IC_{50}$-mono PD-L1-fcP-D1 (nM) |
|---|---|
| 768 | 0.0640 |
| 769 | 0.0640 |
| 770 | 0.4180 |
| 771 | 0.0640 |
| 772 | 0.5520 |
| 773 | 0.6380 |
| 774 | 1.3120 |
| 775 | 0.2760 |
| 776 | 8.3100 |
| 777 | 0.0640 |
| 778 | 0.1130 |
| 779 | 0.3530 |
| 780 | 0.0640 |
| 781 | 0.0640 |
| 782 | 0.0640 |
| 783 | 0.2590 |
| 784 | 0.0640 |
| 785 | 0.0640 |
| 786 | 0.0640 |
| 787 | 0.0660 |
| 788 | 0.0640 |
| 789 | 0.0640 |
| 790 | 0.8650 |
| 791 | 2.8370 |
| 792 | 0.5340 |
| 793 | 1.7450 |
| 794 | 1.7340 |
| 795 | 0.0640 |
| 796 | 0.7620 |
| 797 | 0.0640 |
| 798 | 0.0640 |
| 799 | 0.3410 |
| 800 | 1.2940 |
| 801 | 9.6910 |
| 802 | 0.0840 |
| 803 | 0.0640 |

The above data shows that compounds of the present disclosure are generally effective at blocking the PD-1/PD-L1 interaction.

$EC_{50}$-CHO/PD-L1-Capture Assay:

Compounds were tested in a cell capture assay to determine if they can specifically block the interaction between the recombinant extracellular domain (ECD) of PD-1 and native cell-bound PD-L1. Binding affinity of stable CHO cells overexpressing PD-L1 with its cognate recombinant ligand coated on plates was measured by counting the number of 'captured' cells. High-capacity streptavidin-coated plates were incubated with biotylated-Fc-PD-1 for 2 hours in PBS. Unbound ligand was washed out. CHO-PD-L1 cells (resuspended in PBS pH 7.4, 0.5 mM EDTA, and 2% bovine serum albumin) were pre-incubated for 1 hr with compound, dispensed into each PD-1 ECD coated well and then incubated for 75 min at room temperature. To stop the capture assay, a fixative/staining solution (final concentrations are 1.3% glutaraldehyde and 1.67 μM Draq5) was gently added to the cells and incubated for 2 hrs at room temperature. Unbound cells were then washed out and 'captured' cells were enumerated using a high-content microscopy system. $EC_{50}$ values were calculated from the fit of the dose-response curves to a four-parameter equation. Representative data are shown below in Table 2.

TABLE 2

| Example No. | $EC_{50}$-CHO/ PD-L1-capture |
|---|---|
| 1 | 381.5 |
| 2 | 1274.4 |
| 4 | 15.6 |
| 5 | 38.1 |
| 6 | 63.8 |
| 7 | 56 |
| 8 | 79.7 |
| 9 | 101.5 |
| 10 | 185 |
| 11 | 169.8 |
| 13 | 456.7 |
| 16 | 6 |
| 29 | 217.5 |
| 30 | 52.1 |
| 31 | 30.1 |
| 32 | 42.1 |
| 34 | 321.2 |
| 35 | 263.6 |
| 39 | 267.2 |
| 41 | 248.4 |
| 42 | 149.2 |
| 43 | 65.2 |
| 45 | 165.6 |
| 47 | 225.8 |
| 48 | 297.5 |
| 49 | 123.5 |
| 54 | 232.8 |
| 55 | 314.6 |
| 61 | 199.9 |
| 68 | 279.2 |
| 74 | 175.7 |
| 76 | 83.2 |
| 78 | 187.4 |
| 90 | 218.6 |
| 91 | 195.8 |
| 92 | 25.9 |
| 93 | 44.4 |
| 94 | 228.2 |
| 106 | 110.2 |
| 109 | 7.5 |
| 110 | 6.5 |
| 111 | 45.7 |
| 112 | 34.4 |
| 113 | 148.5 |
| 114 | 140.3 |
| 116 | 134.2 |
| 117 | 158.2 |
| 118 | 169.4 |
| 121 | 176.2 |
| 122 | 191.6 |
| 123 | 137.3 |
| 124 | 146.8 |
| 126 | 179.6 |
| 127 | 68.6 |
| 129 | 220.7 |
| 130 | 123.4 |
| 131 | 231 |
| 132 | 194.2 |
| 133 | 129.1 |
| 134 | 111.9 |
| 135 | 221.4 |
| 143 | 296.3 |
| 145 | 63.6 |
| 146 | 184.3 |
| 147 | 116.9 |
| 148 | 131.8 |
| 149 | 275.4 |
| 155 | 210.7 |
| 157 | 81.1 |
| 159 | 189.8 |
| 160 | 190.9 |
| 162 | 262.5 |
| 165 | 155.8 |
| 166 | 41.6 |
| 167 | 62.3 |
| 172 | 50.6 |
| 178 | 71.6 |
| 179 | 318.7 |
| 182 | 91.4 |
| 183 | 69.1 |
| 185 | 276.9 |
| 192 | 31.2 |
| 198 | 100.91 |
| 203 | 316.7 |
| 205 | 394 |
| 206 | 160.8 |
| 20 | 752 |
| 209 | 13.1 |
| 211 | 45.6 |
| 212 | 92.2 |
| 213 | 165.3 |
| 214 | 22.3 |
| 216 | 205.6 |
| 217 | 71.6 |
| 231 | 276.6 |
| 232 | 141.8 |
| 234 | 131.8 |
| 240 | 216.7 |
| 241 | 165.6 |
| 242 | 129.4 |
| 243 | 90.6 |
| 245 | 308.5 |
| 248 | 200.3 |
| 279 | 27.7 |
| 280 | 207.9 |
| 282 | 253.7 |
| 288 | 10.3 |

The above data shows that compounds of the present disclosure are generally effective at inhibiting PG or specifically blocking the interaction between the recombinant extracellular domain (ECD) of PD-1 and native cell-bound PD-L1.

PD-1/PD-L1 NEAT Reporter Assay:

Compounds were tested in afunctional co-culture reporter assay in which TCR-mediated NFAT activity is inhibited by the engagement of PD-1 with PD-L1. Blocking the PD-/PD-L interaction impairs PD-1 mediated blunting of TCR signaling and significantly increases NFAT-mediated transcription of luciferase. CHO cells expressing surface-bound anti-CD3 antibodies and PD-L1 (artificial antigen presenting cells, aAPC-PD-L1) were first seeded overnight. Jurkat cells overexpressing PD-1 and expressing a luciferase construct under NFAT control are diluted in RPMI assay medium (RPMI 1640 with 2% FBS), mixed with compounds, and immediately seeded on the monolayer of aAPC-PD-L1. The co-culture is then incubated for 6 hrs at 37° C. Luciferase activity is assessed by adding the ONE-Glo reagent and measuring luminescence with a plate reader. $EC_{50}$ values are calculated from the fit of the dose-response curves to a four-parameter equation (Table 3).

PD-L1/PD-L1 Dimerization Biochemical Protein-Protein Interaction Assay:

Compounds were tested in biochemical protein-protein interaction assays to determine if they can specifically dimerize the extracellular domains of PD-L1. Dimerization of the proteins (His-tagged PD-L1 and FLAG-tagged PD-L1) is measured using a bead based Amplified Luminescent Proximity Homogeneous Assay (ALPHA) platform.

Compound induced dimerization of PD-L1 results in proximity of the donor and acceptor beads which leads to an increase in ALPHA signal. Assays are performed in 25 mM Hepes (pH 7.4), 150 mM NaCl, 3.4 mM EDTA, 0.005% Tween 20, and 0.01% BSA. Final protein concentration in the assays were 0.5 nM (His tagged PD-L) and 0.5 nM (FLAG tagged PD-L1). After an assay reaction time of 2 hours at 25° C., 20 μg/mL (final assay concentration) ALPHA assay acceptor beads (anti-His coated) were added and incubated for 60 minutes at 25° C. Binding was measured following a final 60 minute incubation with 40 μg/mL (final assay concentration) ALPHA assay donor beads (anti-FLAG coated). $AC_{50}$ values were calculated from the fit of the dose-response curves to a four-parameter equation (Table 3).

TABLE 3

| Ex. | $AC_{50}$ PDL1 Dimer Alpha 1 nM | $EC_{50}$ NFAT Luciferase |
|---|---|---|
| 1 | | 516 |
| 2 | | 456 |
| 3 | | 48 |
| 4 | 67.228 | 17 |
| 5 | | 29 |
| 6 | 90.878 | 148 |
| 7 | 140.42 | 89 |
| 8 | | 290 |
| 9 | | 340 |
| 10 | | 502 |
| 11 | | 1100 |
| 12 | | 653 |
| 13 | | 4802 |
| 14 | | 13076 |
| 15 | | 5706 |
| 16 | 100.07 | 88 |
| 17 | | 1607 |
| 18 | | 50000 |
| 19 | | 5136 |
| 20 | | 1198 |
| 21 | | 1372 |
| 22 | | 2073 |
| 23 | | 50000 |
| 24 | | 1887 |
| 25 | | 3763 |
| 26 | | 18881 |
| 27 | | 25293 |
| 28 | | 663 |
| 29 | | 244 |
| 30 | 369.04 | 50000 |
| 31 | | 687 |
| 32 | | 127 |
| 33 | | 322 |
| 34 | | 195 |
| 35 | | 296 |
| 36 | | 1070 |
| 37 | | 894 |
| 38 | | 2667 |
| 39 | | 50000 |
| 40 | | 176 |
| 41 | | 188 |
| 42 | | 123 |
| 43 | 10000 | 79 |
| 44 | | 62 |
| 45 | | 75 |
| 46 | | 87 |
| 47 | | 503 |
| 48 | | 412 |
| 49 | | 274 |
| 50 | | 76 |
| 51 | | 105 |
| 52 | | 19786 |
| 53 | | 722 |
| 54 | | 997 |
| 55 | | 1516 |
| 56 | | 50000 |

TABLE 3-continued

| Ex. | $AC_{50}$ PDL1 Dimer Alpha 1 nM | $EC_{50}$ NFAT Luciferase |
|---|---|---|
| 57 | | 351 |
| 58 | | 822 |
| 59 | | 1247 |
| 60 | | 50000 |
| 61 | | 6780 |
| 62 | | 19476 |
| 63 | | 50000 |
| 64 | | 9781 |
| 65 | | 3348 |
| 66 | 369.76 | 338 |
| 67 | | 1317 |
| 68 | | 553 |
| 69 | | 1744 |
| 70 | | 902 |
| 71 | | 1030 |
| 72 | | 2512 |
| 73 | | 2618 |
| 74 | 10000 | 138 |
| 75 | | 384 |
| 76 | | 1056 |
| 77 | | 50000 |
| 78 | | 395 |
| 79 | | 381 |
| 80 | | 50000 |
| 81 | | 50000 |
| 82 | | 1706 |
| 83 | | 1680 |
| 84 | | 10003 |
| 85 | | 9771 |
| 86 | | 50000 |
| 87 | | 50000 |
| 88 | | 4146 |
| 89 | | 670 |
| 90 | 10000 | 113 |
| 91 | 10000 | 523 |
| 92 | 170.13 | 63 |
| 93 | 145.16 | 127 |
| 94 | | 210 |
| 95 | | 639 |
| 96 | | 912 |
| 97 | | 28 |
| 98 | | 70 |
| 99 | | 157 |
| 100 | | 482 |
| 101 | | 1799 |
| 102 | | 13240 |
| 103 | | 14939 |
| 104 | | 50000 |
| 105 | | 50000 |
| 106 | | 5271 |
| 107 | | 35026 |
| 108 | | 13867 |
| 109 | 112.6 | 662 |
| 110 | 194.34 | 354 |
| 111 | | 129 |
| 112 | 183.78 | 286 |
| 113 | | 193 |
| 114 | | 186 |
| 115 | | 50000 |
| 116 | | 702 |
| 117 | 361.32 | 779 |
| 118 | | 823 |
| 119 | | 863 |
| 120 | | 1302 |
| 121 | | 74 |
| 122 | | 79 |
| 123 | 198.44 | 75 |
| 124 | 10000 | 74 |
| 125 | | 158 |
| 126 | | 327 |
| 127 | 166.03 | 193 |
| 128 | | 234 |
| 129 | 166.51 | 198 |
| 130 | 236.56 | 164 |
| 131 | | 964 |
| 132 | 279.48 | 391 |

TABLE 3-continued

| Ex. | $AC_{50}$ PDL1 Dimer Alpha 1 nM | $EC_{50}$ NFAT Luciferase |
|---|---|---|
| 133 | 281.64 | 288 |
| 134 | | 660 |
| 135 | 249.98 | 812 |
| 136 | | 529 |
| 137 | 195.02 | 1453 |
| 138 | | 392 |
| 139 | | 23869 |
| 140 | | 239 |
| 141 | | 50000 |
| 142 | | 235 |
| 143 | 395.15 | 217 |
| 144 | 205.78 | 201 |
| 145 | | 362 |
| 146 | 334.48 | 2300 |
| 147 | | 1202 |
| 148 | | 124 |
| 149 | | 668 |
| 150 | | 50000 |
| 151 | | 50000 |
| 152 | | 594 |
| 153 | | 329 |
| 154 | | 50000 |
| 155 | | 6487 |
| 156 | | 34156 |
| 157 | | 465 |
| 158 | | 28121 |
| 159 | | 538 |
| 160 | | 139 |
| 161 | | 310 |
| 162 | 236.19 | 160 |
| 163 | | 343 |
| 164 | | 500 |
| 165 | | 352 |
| 166 | | 139 |
| 167 | 10000 | 109 |
| 168 | | 308 |
| 169 | | 225 |
| 170 | | 50000 |
| 171 | | 7716 |
| 172 | 10000 | 139 |
| 173 | | 50000 |
| 174 | | 50000 |
| 175 | | 808 |
| 176 | | 2875 |
| 177 | | 20608 |
| 178 | 10000 | 115 |
| 179 | | 655 |
| 180 | | 24816 |
| 181 | | 30930 |
| 182 | | 439 |
| 183 | 260.25 | 141 |
| 184 | | 1390 |
| 185 | | 195 |
| 186 | | 1512 |
| 187 | | 3201 |
| 188 | | 1550 |
| 189 | | 106 |
| 190 | | 516 |
| 191 | 10000 | 60 |
| 192 | 267.46 | 197 |
| 193 | 132.45 | 99 |
| 194 | | 1261 |
| 195 | | 408 |
| 196 | 222.8 | 151 |
| 197 | | 98 |
| 198 | | 69 |
| 199 | | 2151 |
| 200 | | 893 |
| 201 | | 1115 |
| 202 | | 1919 |
| 203 | | 696 |
| 204 | | 927 |
| 205 | | 1431 |
| 206 | | 672 |
| 207 | | 1547 |
| 208 | | 10575 |

TABLE 3-continued

| Ex. | $AC_{50}$ PDL1 Dimer Alpha 1 nM | $EC_{50}$ NFAT Luciferase |
|---|---|---|
| 209 | 70.478 | 73 |
| 210 | 83.051 | 114 |
| 211 | 81.193 | 304 |
| 212 | 229.64 | 306 |
| 213 | 255.38 | 182 |
| 214 | 187.53 | 172 |
| 215 | | 413 |
| 216 | | 514 |
| 217 | | 589 |
| 218 | | 680 |
| 219 | | 558 |
| 220 | | 177 |
| 221 | | 274 |
| 222 | | 856 |
| 223 | | 50000 |
| 224 | | 24920 |
| 225 | 422.99 | 145 |
| 226 | | 775 |
| 227 | | 615 |
| 228 | | 844 |
| 229 | | 1222 |
| 230 | | 821 |
| 231 | | 962 |
| 232 | 313.88 | 331 |
| 233 | | 11557 |
| 234 | | 444 |
| 235 | | 50000 |
| 236 | | 5030 |
| 237 | | 50000 |
| 238 | | 2124 |
| 239 | | 1118 |
| 240 | 366.95 | 108 |
| 241 | | 275 |
| 242 | | 288 |
| 243 | | 393 |
| 244 | | 390 |
| 245 | | 3436 |
| 246 | | 1200 |
| 247 | | 776 |
| 248 | | 540 |
| 249 | | 50000 |
| 250 | | 7492 |
| 251 | | 25882 |
| 252 | | 333 |
| 253 | | 304 |
| 254 | | 689 |
| 255 | | 50000 |
| 256 | | 758 |
| 257 | | 657 |
| 258 | | 419 |
| 259 | | 511 |
| 260 | | 463 |
| 261 | | 3168 |
| 262 | | 8621 |
| 263 | | 36360 |
| 264 | | 1293 |
| 265 | | 7058 |
| 266 | | 1381 |
| 267 | | 8541 |
| 268 | | 993 |
| 269 | | 50000 |
| 270 | | 50000 |
| 271 | | 50000 |
| 272 | | 37700 |
| 273 | | 50000 |
| 274 | | 1203 |
| 275 | | 10367 |
| 276 | | 2049 |
| 277 | | 50000 |
| 278 | | 50000 |
| 279 | 109.03 | 260 |
| 280 | | 592 |
| 281 | | 488 |
| 282 | 326.84 | 463 |
| 283 | | 20893 |
| 284 | | 1462 |

TABLE 3-continued

| Ex. | $AC_{50}$ PDL1 Dimer Alpha 1 nM | $EC_{50}$ NFAT Luciferase |
|---|---|---|
| 285 | | 9688 |
| 286 | | 232 |
| 287 | | 958 |
| 288 | | 57 |
| 289 | 10000 | 70 |
| 290 | 25.132 | 311 |
| 291 | 27.528 | 46 |
| 292 | 230.22 | 615 |
| 293 | 125.16 | 73 |
| 294 | 547.21 | 714 |
| 295 | 67.628 | 279 |
| 296 | 108.27 | 844 |
| 297 | 187.45 | 266 |
| 298 | | 21 |
| 299 | 161.64 | 326 |
| 300 | 222.67 | 3720 |
| 301 | 95.867 | 1023 |
| 302 | 76.204 | 283 |
| 303 | 101.04 | 289 |
| 304 | 16.481 | 79 |
| 305 | 150.01 | 1765 |
| 306 | 291.81 | 547 |
| 307 | 598.97 | 702 |
| 308 | 203.4 | 373 |
| 309 | 102.96 | 240 |
| 310 | 120.6 | 215 |
| 311 | 75.526 | 104 |
| 312 | 143.95 | 97 |
| 313 | 91.301 | 152 |
| 314 | | 188 |
| 315 | | 1248 |
| 317 | 1179.2 | 1099 |
| 323 | 67.101 | 168 |
| 324 | 1023.6 | 894 |
| 325 | 633.12 | 2575 |
| 326 | 1211.6 | 439 |
| 327 | | 114 |
| 328 | 241 | 146 |
| 329 | 289.72 | 466 |
| 330 | 209.33 | 1638 |
| 331 | 500.24 | 232 |
| 332 | 18.738 | 47 |
| 333 | 202.79 | 481 |
| 335 | 230.8 | 437 |
| 336 | 108.74 | 398 |
| 337 | | 1924 |
| 338 | 140.24 | 1058 |
| 339 | | 2216 |
| 340 | 27.769 | 217 |
| 341 | 38.336 | 284 |
| 342 | 118.42 | 447 |
| 343 | 81.128 | 158 |
| 344 | 55 | 475 |
| 345 | 228.95 | 552 |
| 346 | 181.34 | 214 |
| 347 | 124.8 | 142 |
| 348 | 80.408 | 381 |
| 349 | 62.843 | 320 |
| 350 | 252.44 | 527 |
| 351 | 168.24 | 235 |
| 352 | 56.314 | 105 |
| 353 | 214.6 | 153 |
| 354 | 341.99 | 1882 |
| 355 | | 712 |
| 356 | 237.38 | 733 |
| 357 | 10000 | 202 |
| 358 | 100.37 | 2090 |
| 359 | 540.45 | 216 |
| 360 | 223.56 | 520 |
| 361 | 137.79 | 314 |
| 362 | 108.06 | 221 |
| 363 | 170.84 | 168 |
| 364 | 98.276 | 353 |
| 365 | 174.12 | 408 |
| 366 | | 2842 |
| 367 | 227.46 | 376 |

TABLE 3-continued

| Ex. | $AC_{50}$ PDL1 Dimer Alpha 1 nM | $EC_{50}$ NFAT Luciferase |
|---|---|---|
| 368 | 274.21 | 118 |
| 369 | 57.569 | 107 |
| 370 | 81.369 | 577 |
| 371 | 78.017 | 210 |
| 372 | 425.11 | 860 |
| 373 | 168 | 339 |
| 374 | 164.76 | 788 |
| 375 | 173.05 | 389 |
| 376 | | 770 |
| 377 | 231.43 | 262 |
| 378 | | 191 |
| 379 | 153.36 | 415 |
| 380 | 184.26 | 652 |
| 381 | 143.98 | 219 |
| 382 | 334.26 | 1232 |
| 383 | 157.24 | 467 |
| 384 | 153.77 | 154 |
| 385 | | 84 |
| 386 | | 868 |
| 387 | | 362 |
| 388 | 10000 | 225 |
| 389 | 119.85 | 306 |
| 390 | 97.456 | 120 |
| 391 | 242.51 | 305 |
| 392 | 232.4 | 351 |
| 393 | 84.033 | 118 |
| 394 | 130.25 | 435 |
| 395 | 89.645 | 151 |
| 396 | 37.94 | 105 |
| 397 | | 709 |
| 398 | 728.01 | 1096 |
| 399 | 288.86 | 319 |
| 425 | 225.89 | 544 |
| 426 | 408.29 | 634 |
| 428 | 525.26 | 282 |
| 429 | 240.33 | 680 |
| 430 | 290.48 | 268 |
| 431 | 249.39 | 275 |
| 432 | 538.83 | 289 |
| 433 | 166.99 | 290 |
| 434 | 105.68 | 332 |
| 435 | 86.182 | 316 |
| 436 | 77.818 | 544 |
| 437 | 476.69 | 476 |
| 438 | 168.29 | 222 |
| 439 | 153.58 | 270 |
| 440 | 112.89 | 251 |
| 441 | 301.38 | 260 |
| 442 | 327.98 | 930 |
| 443 | 154.06 | 276 |
| 444 | 133.01 | 296 |
| 445 | 265.84 | 1493 |
| 446 | 457.95 | 315 |
| 448 | 902.63 | 1005 |
| 449 | 1493.4 | 2566 |
| 450 | 110.23 | 277 |
| 451 | 105.3 | 472 |
| 452 | 144.49 | 253 |
| 453 | 325.73 | 895 |
| 454 | 942.69 | 953 |
| 455 | 686.13 | 1544 |
| 456 | 182.03 | 1230 |
| 457 | 49.346 | 1557 |
| 458 | 138.59 | 429 |
| 459 | 89.904 | 1201 |
| 460 | 302.01 | 112 |
| 461 | 127.63 | 47 |
| 463 | 71.305 | 123 |
| 464 | 87.623 | 152 |
| 465 | 84.765 | 193 |
| 466 | 44.128 | 93 |
| 467 | 111.22 | 197 |
| 468 | 131.28 | 183 |
| 469 | 73.532 | 125 |
| 470 | 126.83 | 217 |
| 471 | 79.996 | 144 |

TABLE 3-continued

| Ex. | $AC_{50}$ PDL1 Dimer Alpha 1 nM | $EC_{50}$ NFAT Luciferase |
|---|---|---|
| 472 | | 51 |
| 473 | 76.813 | 86 |
| 474 | 137.4 | 59 |
| 475 | 134.26 | 117 |
| 476 | 149.11 | 196 |
| 477 | 359.77 | 179 |
| 478 | 267.83 | 48 |
| 479 | 347.71 | 45 |
| 480 | 113.77 | 147 |
| 481 | 92.888 | 155 |
| 482 | 25.491 | 47 |
| 483 | 40.947 | 69 |
| 484 | 107.98 | 138 |
| 485 | 61.295 | 200 |
| 486 | | 112 |
| 487 | 25.228 | 16 |
| 488 | 25.557 | 26 |
| 489 | 18.276 | 18 |
| 490 | 14.082 | 19 |
| 491 | 19.794 | 21 |
| 497 | 302.1 | 182 |
| 498 | 84.694 | 111 |
| 499 | 86.519 | 59 |
| 500 | 50.08 | 97 |
| 501 | 35.261 | 60 |
| 502 | 85.226 | 100 |
| 503 | 42.089 | 81 |
| 504 | 47.85 | 68 |
| 505 | 54.984 | 80 |
| 506 | 172.49 | 204 |
| 507 | 262.46 | 210 |
| 508 | 77.969 | 156 |
| 509 | 128.55 | 89 |
| 510 | 232.49 | 147 |
| 511 | 36.86 | 197 |
| 512 | 255.17 | 131 |
| 513 | 89.301 | 47 |
| 514 | 358.78 | 156 |
| 515 | | 95 |
| 516 | 104.22 | 92 |
| 517 | 91.652 | 154 |
| 518 | 96.106 | 159 |
| 519 | 102.68 | 125 |
| 520 | 57.454 | 97 |
| 521 | 124.63 | 106 |
| 522 | 74.343 | 195 |
| 523 | 10000 | 129 |
| 524 | 67.668 | 39 |
| 525 | 34.846 | 27 |
| 526 | 73.609 | 110 |
| 527 | 69.901 | 46 |
| 528 | 63.33 | 89 |
| 529 | 56.181 | 165 |
| 540 | 126.03 | 103 |
| 541 | 70.351 | 93 |
| 542 | 135.98 | 197 |
| 543 | 49.676 | 187 |
| 544 | 17.344 | 109 |
| 545 | 24.445 | 145 |
| 546 | 39.174 | 109 |
| 547 | 20.054 | 51 |
| 548 | 74.563 | 197 |
| 549 | 54.558 | 177 |
| 550 | 47.657 | 163 |
| 551 | 12.434 | 100 |
| 552 | 74.724 | 152 |
| 553 | 17.727 | 70 |
| 554 | 39.501 | 148 |
| 555 | 23.089 | 84 |
| 556 | 37.72 | 86 |
| 557 | 137.33 | 135 |
| 558 | 33.558 | 51 |
| 559 | 18.667 | 53 |
| 560 | 77.784 | 163 |
| 561 | 193.04 | 146 |
| 562 | 126.34 | 162 |

TABLE 3-continued

| Ex. | $AC_{50}$ PDL1 Dimer Alpha 1 nM | $EC_{50}$ NFAT Luciferase |
|---|---|---|
| 563 | | |
| 564 | | 80 |
| 565 | 73.433 | 112 |
| 566 | 39.38 | 86 |
| 567 | 68.718 | 85 |
| 568 | 44.311 | 65 |
| 569 | 128.37 | 74 |
| 570 | 56.457 | 115 |
| 571 | 155.58 | 126 |
| 572 | 452.86 | 129 |
| 573 | 215.25 | 120 |
| 574 | 55.956 | 72 |
| 575 | 40.589 | 34 |
| 576 | 24.313 | 32 |
| 577 | 9.732 | 16 |
| 578 | 37.182 | 135 |
| 579 | 34.754 | 191 |
| 580 | 231.43 | 200 |
| 581 | 60.308 | 158 |
| 582 | 346.58 | 147 |
| 583 | 38.272 | 180 |
| 584 | 38.566 | 149 |
| 585 | | 182 |
| 586 | | 181 |
| 587 | 324.37 | 45 |
| 588 | 206.48 | 50 |
| 589 | 164.01 | 89 |
| 590 | 134.21 | 140 |
| 591 | 22.717 | 20 |
| 592 | 107.3 | 172 |
| 593 | 124.18 | 113 |
| 595 | 77.049 | 65 |
| 596 | 415.02 | 169 |
| 597 | 310.22 | 231 |
| 598 | 480.36 | 1836 |
| 599 | 7925.6 | 50000 |
| 600 | 261.4 | 240 |
| 601 | 1125.1 | 748 |
| 602 | 124.08 | 242 |
| 603 | 235.05 | 158 |
| 604 | 934.65 | 552 |
| 605 | 351.78 | 130 |
| 606 | 557.85 | 50000 |
| 607 | 296.48 | 1732 |
| 608 | 214.46 | 50000 |
| 609 | 143.28 | 541 |
| 610 | 104.78 | 50000 |
| 611 | 408.3 | 223 |
| 612 | 728.92 | 50000 |
| 613 | 157.64 | 484 |
| 614 | 10000 | 50000 |
| 615 | 10000 | 50000 |
| 616 | 155.9 | 50000 |
| 617 | 264.72 | 50000 |
| 618 | 389.37 | 50000 |
| 619 | 118.12 | 187 |
| 620 | 10000 | 50000 |
| 621 | 10000 | 50000 |
| 622 | 10000 | 50000 |
| 623 | 10000 | 50000 |
| 624 | 20.923 | 50000 |
| 625 | 98.154 | 50000 |
| 626 | 10000 | 50000 |
| 627 | 480.39 | 50000 |
| 629 | 10000 | 251 |
| 630 | 10000 | 165 |
| 631 | 440.7 | 50000 |
| 632 | 313.61 | 2985 |
| 633 | 2841.4 | 2275 |
| 634 | 96.94 | 495 |
| 635 | 340.05 | 50000 |
| 636 | 83.554 | 180 |
| 637 | 20.779 | 90 |
| 638 | 23.809 | 429 |
| 639 | | 942 |
| 640 | | 50000 |

TABLE 3-continued

| Ex. | $AC_{50}$ PDL1 Dimer Alpha 1 nM | $EC_{50}$ NFAT Luciferase |
|---|---|---|
| 641 | 34.707 | 60 |
| 642 | 67.167 | 194 |
| 643 | 39.001 | 89 |
| 644 | 135.96 | 82 |
| 645 | 30.693 | 30 |
| 646 | 73.171 | 145 |
| 647 | 211.12 | 234 |
| 648 | 60.881 | 57 |
| 649 | 38.806 | 29 |
| 650 | 8.201 | 39 |
| 651 | 29.501 | 41 |
| 652 | 140.25 | 59 |
| 653 | 105.23 | 93 |
| 654 | 10.897 | 27 |
| 655 | 25.985 | 28 |
| 656 | 37.666 | 24 |
| 657 | 156.4 | 197 |
| 658 | 78.516 | 51 |
| 659 | 22.096 | 51 |
| 660 | 15.245 | 107 |
| 661 | 125.67 | 159 |
| 662 | 14.486 | 83 |
| 663 | 6.56 | 118 |
| 664 | 10000 | 50000 |
| 665 | 16.491 | 150 |
| 666 | 22.851 | 418 |
| 667 | 17.028 | 1893 |
| 668 | 16.485 | 886 |
| 669 | 17.179 | 637 |
| 670 | 74.789 | 50000 |
| 671 | 10000 | 235 |
| 672 | 24.53 | 435 |
| 673 | 398.99 | 583 |
| 674 | 11.32 | 44 |
| 675 | | 95 |
| 676 | | 62 |
| 677 | 180.38 | 145 |
| 678 | 253.53 | 264 |
| 679 | 100.56 | 64 |
| 681 | | 50000 |
| 682 | 193.69 | 243 |
| 683 | 115.93 | 98 |
| 684 | 41.209 | 36 |
| 685 | 1822.3 | 625 |
| 686 | 136.97 | 46 |
| 687 | 3096.1 | 605 |
| 688 | 140.78 | 50000 |
| 689 | 114.12 | 139 |
| 690 | 80.795 | 287 |
| 691 | 193.17 | 443 |
| 692 | | 198 |
| 693 | | 120 |
| 694 | | 96 |
| 695 | 21.64 | 26 |
| 696 | 16.885 | 12 |
| 697 | 51.001 | 50 |
| 698 | 111.18 | 152 |
| 699 | 24.684 | 136 |
| 700 | 22.122 | 43 |
| 701 | 332.27 | 3053 |
| 702 | 332.32 | 1311 |
| 703 | 24.212 | 11 |
| 704 | 66.777 | 11 |
| 705 | 60.582 | 20 |
| 706 | 42.831 | 14 |
| 707 | 39.298 | 31 |
| 708 | 38.593 | 34 |
| 709 | 49.36 | 21 |
| 710 | 54.611 | 22 |
| 711 | 102.77 | 69 |
| 712 | 32.999 | 12 |
| 713 | 69.421 | 25 |
| 714 | 66.315 | 26 |
| 715 | 7.886 | 35 |
| 716 | 15.094 | 343 |
| 717 | 16.161 | 484 |

TABLE 3-continued

| Ex. | $AC_{50}$ PDL1 Dimer Alpha 1 nM | $EC_{50}$ NFAT Luciferase |
|---|---|---|
| 718 | 70.434 | 704 |
| 719 | 32.67 | 110 |
| 720 | 94.892 | 558 |
| 721 | 18.996 | 14 |
| 722 | 16.05 | 47 |
| 723 | 35.134 | 41 |
| 724 | 21.158 | 120 |
| 725 | 14.262 | 88 |
| 726 | 81.94 | 76 |
| 727 | 15.841 | 27 |
| 728 | 14.976 | 25 |
| 729 | 48.994 | 652 |
| 730 | 40.706 | 100 |
| 731 | 15.975 | 26 |
| 732 | 2.694 | 14 |
| 733 | 129.31 | 120 |
| 734 | 45.993 | 36 |
| 735 | 104.09 | 95 |
| 736 | 18.388 | 22 |
| 737 | 8.231 | 80 |
| 738 | 8.059 | 72 |
| 739 | 3.815 | 10 |
| 740 | 53.577 | 288 |
| 741 | 3.104 | 12 |
| 742 | 42.007 | 32 |
| 743 | 82.234 | 50 |
| 744 | 9.532 | 44 |
| 745 | 19.203 | 113 |
| 746 | 103.63 | 143 |
| 747 | 5.356 | 10 |
| 748 | 10.056 | 24 |
| 749 | 16.809 | 77 |
| 750 | 72.114 | 222 |
| 751 | 181.6 | 355 |
| 752 | 82.454 | 471 |
| 753 | | 35 |
| 754 | | 434 |
| 755 | 39.227 | 139 |
| 756 | | 6586 |
| 757 | 17.559 | 15 |
| 758 | 36.654 | 29 |
| 759 | 18.894 | 16 |
| 760 | 44.242 | 63 |
| 761 | 13.202 | 10 |
| 762 | 13.558 | 18 |
| 763 | 11.335 | 10 |
| 764 | 31.93 | 23 |
| 765 | 13.146 | 11 |
| 766 | 19.366 | 21 |
| 767 | 75.724 | 57 |
| 768 | 47.439 | 33 |
| 769 | 28.129 | 25 |
| 770 | 700.16 | 856 |
| 771 | 45.017 | 130 |
| 772 | 19.477 | 50000 |
| 773 | 10000 | 2100 |
| 774 | 2726.7 | 463 |
| 775 | 68.021 | 84 |
| 776 | 10000 | 1443 |
| 777 | 45.788 | 179 |
| 778 | 258.91 | 212 |
| 779 | 112.82 | 68 |
| 780 | 14.393 | 50 |
| 781 | 23.265 | 34 |
| 782 | 23.072 | 38 |
| 783 | 823.38 | 2987 |
| 784 | 28.933 | 182 |
| 785 | 16.139 | 66 |
| 786 | 12.246 | 86 |
| 787 | 35.352 | 58 |
| 788 | 11.785 | 39 |
| 789 | 17.884 | 58 |
| 790 | 75.688 | 84 |
| 791 | 205.9 | 175 |
| 792 | 22.685 | 40 |
| 793 | 186.83 | 1813 |

TABLE 3-continued

| Ex. | $AC_{50}$ PDL1 Dimer Alpha 1 nM | $EC_{50}$ NFAT Luciferase |
|---|---|---|
| 794 | 94.243 | 794 |
| 795 | 9.646 | 41 |
| 796 | 227.82 | 151 |
| 797 | 41.412 | 30 |
| 798 | 22.717 | 20 |
| 799 | 150.12 | 167 |
| 800 | 536.96 | 246 |
| 801 | 10000 | 50000 |
| 802 | 55.521 | 177 |
| 803 | 11.741 | 49 |

The invention claimed is:

1. A compound of formula (VIII):

(VIII)

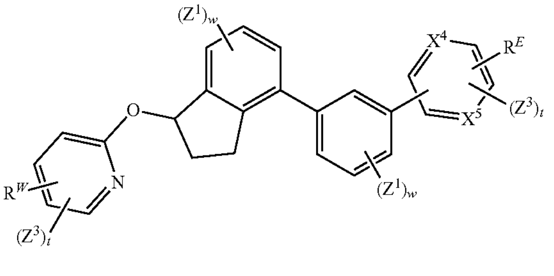

wherein:

each of $X^4$ and $X^5$ are independently N, CH, or $CZ^3$;

each $Z^1$ is independently halo, —$OR^a$, —$NO_2$, —CN, —$NR^aR^b$, —$N_3$, —$SO_2R^a$, —$C_{1-6}$ alkyl, —$C_{1-6}$ haloalkyl, —$C_{2-6}$alkenyl, —$C_{2-6}$ alkynyl, —O—$C_{1-6}$ alkyl, —O—$C_{1-6}$ haloalkyl, —$C_{3-8}$ cycloalkyl, or —$C_{1-6}$ alkyl-$C_{3-8}$ cycloalkyl; and wherein each alkyl, alkenyl, alkynyl, and cycloalkyl is optionally substituted with 1 to 4 groups independently selected from oxo, —$NO_2$, —$N_3$, —$OR^a$, halo, and cyano;

each w is independently 0, 1, or 2;

each $Z^3$ is independently halo, —$OR^a$, —$N_3$, —$NO_2$, —CN, —$NR^1R^2$, —$SO_2R^a$, —$SO_2NR^aR^b$, —$NR^aSO_2R^a$, —$NR^aC(O)R^a$, —$C(O)R^a$, —$C(O)OR^a$, —$C(O)NR^aR^b$, —$NR^aC(O)OR^a$, —$NR^aC(O)NR^1R^2$, —$OC(O)NR^aR^b$, —$NR^aSO_2NR^aR^b$, —C(O)$NR^aSO_2NR^aR^b$, —$C_{1-6}$ alkyl, —$C_{2-6}$ alkenyl, —$C_{2-6}$ alkynyl, —O—$C_{1-6}$ alkyl, —$C_{3-8}$ cycloalkyl, —$C_{1-6}$ alkyl$C_{3-8}$ cycloalkyl, aryl, heteroaryl, heterocyclyl, or RN, and wherein the alkyl, alkenyl, alkynyl, $C_{3-8}$ cycloalkyl, aryl, heteroaryl, or heterocyclyl group is optionally substituted with 1 to 4 groups independently selected from oxo, —$NO_2$, —$N_3$, —$OR^a$, halo, cyano, —$NR^aR^b$, —$C(O)R^a$, —$C(O)OR^a$, —O—$C_{1-6}$cyanoalkyl, —$C(O)NR^aR^b$, $NR^aC(O)R^a$, —$NR^aC(O)OR^a$, —$SO_2R^a$, —$NR^aSO_2R^b$, —$SO_2NR^aR^b$, —$NR^aSO_2NR^aR^b$, —C(O)$NR^aSO_2NR^aR^b$, and —$C_{3-8}$ cycloalkyl;

$R^N$ is independently —$C_{1-6}$ alkyl$NR^1R^2$, —O—$C_{1-6}$ alkyl$NR^1R^2$, —$C_{1-6}$ alkyl$OC_{1-6}$ alkyl$NR^1R^2$, —$NR^aC_{1-6}$ alkyl$NR^1R^2$, —$C_{1-6}$ alkylC(O)$NR^1R^2$, —O—$C_{1-6}$ alkylC(O)$NR^1R^2$, —O—$C_{1-6}$ alkylC(O)$OR^1$, —$SC_{1-6}$ alkyl$NR^1R^2$, —$C_{1-6}$ alkyl$OR^a$, or

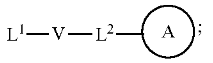

wherein: $L^1$ is independently a bond, O, $NR^a$, S, SO, or $SO_2$;

V is independently selected from a bond, $C_{1-6}$alkyl, $C_{2-6}$alkenyl, and $C_{2-6}$alkynyl;

wherein each alkyl, alkenyl, or alkynyl is optionally independently substituted with $OR^a$, halo, cyano, —$NR^aR^b$, or —$C_{3-8}$ cycloalkyl;

$L^2$ is independently a bond, O, $NR^a$, S, SO, or $SO_2$;

ring A is independently cycloalkyl, aryl, heteroaryl, or heterocyclyl;

wherein each cycloalkyl, aryl, heteroaryl, or heterocyclyl is optionally substituted with 1 to 4 groups independently selected from oxo, —$NO_2$, —$N_3$, —$OR^a$, halo, cyano, —$C_{1-6}$ alkyl, —$C_{1-6}$ haloalkyl, —$C_{2-6}$alkenyl, —$C_{2-6}$ alkynyl, —O—$C_{1-6}$ haloalkyl, $NR^aR^b$, —$C(O)R^a$, —$C(O)OR^a$, —O—$C_{1-6}$ alkylCN, —$C(O)NR^aR^b$, —$NR^aC(O)R^a$, —$NR^aC(O)OR^a$, —$C(O)N(R^a)OR^b$, —$SO_2R^a$, —$SO_2NR^aR^b$, —$NR^aSO_2R^b$, —$NR^aSO_2NR^aR^b$, —C(O)$NR^aSO_2NR^aR^b$, $C_{3-8}$cycloalkyl, and $C_{1-6}$alkyl$C_{3-8}$ cycloalkyl; and wherein the alkyl, alkenyl, or alkynyl group is optionally independently substituted with —$OR^a$, halo, cyano, —$NR^aR^b$, or —$C_{3-8}$ cycloalkyl;

each t is independently 0, 1, or 2;

$R^E$ and $R^W$ are each independently —$NR^1R^2$, —$C_{1-6}$ alkyl$NR^1R^2$, —O—$C_{1-6}$ alkyl$NR^1R^2$, —$C_{1-6}$ alkyl$OC_{1-6}$alkyl$NR^1R^2$, —$NR^a$—$C_{1-6}$ alkyl$NR^1R^2$, —$C_{1-6}$ alkyl$N^+R^1R^2R^3$, —S—$C_{1-6}$ alkyl$NR^1R^2$, —C(O)$NR^1R^2$, —$SO_2R^a$, —$(CH_2)_uSO_2NR^1R^2$, —$(CH_2)_uNR^a$—$SO_2NR^aR^b$, —$SO_2NR^a$—$C_{1-6}$ alkyl$NR^1R^2$, —$NR^aSO_2$—$C_{1-6}$ alkyl$NR^1R^2$, —$(CH_2)_uC(O)NR^aSO_2NR^aR^b$, —$(CH_2)_uN^+R^1R^2O^-$, —$(CH_2)_uP^+R^bR^cR^d$, $(CH_2)_uP^+R^cR^dO^-$, —$(CH_2)_uP^+O[NR^aR^b][NR^cR^d]$, —$(CH_2)_uNR^cP(O)(OR^c)_2$, —$(CH_2)_uCH_2OP(O)(OR^c)(OR^d)$, —$(CH_2)_uOP(O)(OR^c)(OR^d)$, —$(CH_2)_uOP(O)NR^aR^b)(OR^a)$, or

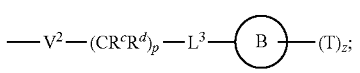

wherein:

$V^2$ is independently a bond, O, $NR^a$, S, SO, $SO_2$, C(O)$NR^a$, $NR^aC(O)$, $SO_2NR^1$, or $NR^aSO_2$;

$L^3$ is independently a bond, O, $NR^a$, S, SO, $SO_2$, C(O)$NR^a$, $NR^aC(O)$, $SO_2NR^1$, or $NR^aSO_2$;

ring B is independently cycloalkyl, aryl, heteroaryl, or heterocyclyl;

T is independently H, $OR^a$, $(CH_2)_qNR^1R^2$, $(CH_2)_qNR^aC(O)R^e$, or $(CH_2)_qC(O)R^e$;

p is independently 0, 1, 2, 3, 4, or 5;

q is independently 0, 1, 2, 3, 4, or 5;

u is 0, 1, 2, 3, or 4;

z is 0, 1, 2, or 3; and wherein the alkyl, cycloalkyl, aryl, heteroaryl, or heterocyclyl of $R^E$ or $R^W$ is optionally substituted with 1 to 3 substituents independently selected from the group consisting of $NR^aR^b$, halo, cyano, oxo, $OR^a$, —$C_{1-6}$ alkyl, —$C_{1-6}$ haloalkyl, —$C_{1-6}$ cyanoalkyl, —$C_{1-6}$ alkylNR$^a$R$^b$, —C$_{1-6}$ alkylOH, —C$_{3-8}$ cycloalkyl, and —C$_{1-3}$ alkylC$_{3-8}$cycloalkyl;

provided that at least one of V$^2$, L$^3$, ring B, and T contains a nitrogen atom;

each R$^1$ is independently selected from H, —C$_{1-8}$ alkyl, —C$_{2-6}$ alkenyl, —C$_{2-6}$ alkynyl, —C$_{3-6}$ cycloalkyl, aryl, heteroaryl, heterocyclyl, —C$_{1-6}$ alkylaryl, —C$_{1-6}$ alkylheteroaryl, —C$_{1-6}$ alkylheterocyclyl, —C$_{1-6}$ alkylC(O)OR$^a$, —C$_{2-6}$ alkenylC(O)OR$^a$, —SO$_2$R$^a$, —SO$_2$NR$^a$R$^b$, —C(O)NR$^a$SO$_2$R$^a$, and C$_{1-6}$ alkylC$_{3-8}$cycloalkyl;

wherein each alkyl, alkenyl, cycloalkyl, aryl, heteroaryl, or heterocyclyl is optionally substituted with 1 to 4 groups independently selected from —OR$^a$, —CN, halo, C$_{1-6}$alkyl, —C$_{1-6}$ alkylOR$^a$, —C$_{1-6}$ cyanoalkyl, —C$_{1-6}$ haloalkyl, C$_{3-8}$ cycloalkyl, —C$_{1-3}$ alkylC$_{3-8}$cycloalkyl, —C(O)R$^a$, —C$_{1-6}$ alkylC(O)R$^a$, —C(O)OR$^a$, —C$_{1-6}$ alkylC(O)OR$^a$, —NR$^a$R$^b$, —OC(O)NR$^a$R$^b$, NR$^a$C(O)OR$^b$, —C$_{1-6}$ alkylNR$^a$R$^b$, —C(O)NR$^a$R$^b$, —C$_{1-6}$ alkylC(O)NR$^a$R$^b$, —SO$_2$R$^a$, —C$_{1-6}$ alkylSO$_2$R$^a$, —SO$_2$NR$^a$R$^b$, —C$_{1-6}$ alkylSO$_2$NR$^a$R$^b$, —C(O)NR$^a$SO$_2$R$^b$, —C$_{1-6}$ alkylC(O)NR$^a$SO$_2$R$^b$, —NR$^a$C(O)R$^b$, and —C$_{1-6}$alkylNR$^a$C(O)R$^b$;

each R$^2$ is independently selected from H, —C$_{1-6}$ alkyl, —C$_{2-6}$ alkenyl, —C$_{2-6}$ alkynyl, —C$_{3-6}$ cycloalkyl, aryl, heteroaryl, heterocyclyl, —C$_{1-6}$ alkylaryl, —C$_{1-6}$ alkylheteroaryl, —C$_{1-6}$ alkylheterocyclyl, —C$_{2-6}$ alkyl-OR$^a$, —C$_{1-6}$ alkylC(O)OR$^a$, and —C$_{2-6}$ alkenylC(O)OR$^a$;

wherein each alkyl, alkenyl, alkynyl, cycloalkyl, aryl, heteroaryl, or heterocyclyl is optionally substituted with 1 to 4 groups independently selected from —OR$^a$, —CN, halo, C$_{1-6}$alkyl, —C$_{1-6}$ alkylOR$^a$, —C$_{1-6}$ cyanoalkyl, —C$_{1-6}$ haloalkyl, —C$_{3-8}$ cycloalkyl, —C$_{1-3}$ alkylC$_{3-8}$cycloalkyl, —C(O)R$^a$, —C$_{1-6}$ alkylC(O)R$^a$, —C(O)OR$^a$, —C$_{1-6}$ alkylC(O)OR$^a$, —NR$^a$R$^b$, —C$_{1-6}$ alkylNR$^a$R$^b$, —C(O)NR$^a$R$^b$, C$_{1-6}$ alkylC(O)NR$^a$R$^b$, —SO$_2$R$^a$, —C$_{1-6}$ alkylSO$_2$R$^a$, —SO$_2$NR$^a$R$^b$, —C$_{1-6}$ alkylSO$_2$NR$^a$R$^b$, —C(O)NR$^a$SO$_2$R$^b$, and —NR$^a$C(O)R$^b$;

or R$^1$ and R$^2$ combine to form a heterocyclyl group optionally containing 1, 2, or 3 additional heteroatoms independently selected from oxygen, sulfur, and nitrogen, and optionally substituted with 1 to 3 groups independently selected from oxo, —C$_{1-6}$ alkyl, —C$_{3-8}$ cycloalkyl, —C$_{2-6}$ alkenyl, —C$_{2-6}$ alkynyl, —OR$^a$, —C(O)OR$^a$, —C$_{1-6}$ cyanoalkyl, —C$_{1-6}$ alkylOR$^a$, —C$_{1-6}$ haloalkyl, —C$_{1-3}$ alkylC$_{3-8}$cycloalkyl, —C(O)R$^a$, C$_{1-6}$ alkylC(O)R$^a$, —C$_{1-6}$ alkylC(O)OR$^a$, —NR$^a$R$^b$, —C$_{1-6}$alkylNR$^a$R$^b$, —C(O)NR$^a$R$^b$, —C$_{1-6}$ alkylC(O)NR$^a$R$^b$, —SO$_2$R$^a$, —C$_{1-6}$ alkylSO$_2$R$^a$, —SO$_2$NR$^a$R$^b$, and C$_{1-6}$ alkylSO$_2$NR$^a$R$^b$;

each R$^3$ is independently H, —C$_{1-6}$ alkyl, —C$_{2-6}$ alkenyl, —C$_{3-6}$ cycloalkyl, aryl, heteroaryl, heterocyclyl, —C$_{1-6}$ alkylaryl, —C$_{1-6}$ alkylheteroaryl, —C$_{1-6}$ alkylheterocyclyl, —C$_{2-6}$ alkyl-OR$^a$, —C$_{1-6}$ alkylC(O)OR$^a$, or —C$_{2-6}$ alkenylC(O)OR$^a$;

each R$^a$ is independently selected from H, —C$_{1-6}$ alkyl, —C$_{3-8}$ cycloalkyl, aryl, heteroaryl, heterocyclyl, —C$_{1-3}$ alkylC$_{3-8}$cycloalkyl, —C$_{1-6}$ alkylaryl, —C$_{1-6}$ alkylheteroaryl, and —C$_{1-6}$alkylheterocyclyl;

each R$^b$ is independently selected from H, —C$_{1-6}$ alkyl, —C$_{3-8}$ cycloalkyl, aryl, heteroaryl, heterocyclyl, —C$_{1-3}$ alkylC$_{3-8}$cycloalkyl, —C$_{1-6}$ alkylaryl, —C$_{1-6}$ alkylheteroaryl, and —C$_{1-6}$ alkylheterocyclyl;

or R$^a$ and R$^b$ may combine together to form a ring consisting of 3-8 ring atoms that are C, N, O, or S; wherein the ring is optionally substituted with 1 to 4 groups independently selected from —OR$^f$, —CN, halo, —C$_{1-6}$ alkylOR$^f$, —C$_{1-6}$ cyanoalkyl, —C$_{1-6}$ haloalkyl, —C$_{3-8}$ cycloalkyl, —C$_{1-3}$ alkylC$_{3-8}$cycloalkyl, —C(O)R$^f$, —C$_{1-6}$ alkylC(O)R$^f$, —C(O)OR$^f$, —C$_{1-6}$ alkylC(O)OR$^f$, —NR$^f$R$^g$, —C$_{1-6}$ alkylNR$^f$R$^g$, —C(O)NR$^f$R$^g$, —C$_{1-6}$ alkylC(O)NR$^f$R$^g$, —SO$_2$R$^f$, —C$_{1-6}$ alkylSO$_2$R$^f$, —SO$_2$NR$^f$R$^g$, —C$_{1-6}$ alkylSO$_2$NR$^f$R$^g$, —C(O)NR$^f$SO$_2$R$^g$, and —NR$^f$C(O)R$^g$;

each R$^c$ is independently selected from H, OH, —C$_{1-6}$ alkyl, —C$_{3-8}$ cycloalkyl, aryl, heteroaryl, heterocyclyl, —C$_{1-3}$ alkylC$_{3-8}$ cycloalkyl, —C$_{1-6}$ alkylaryl, —C$_{1-6}$ alkylheteroaryl, and —C$_{1-6}$ alkylheterocyclyl;

R$^d$ is independently selected from H, —C$_{1-6}$ alkyl, —C$_3$-C$_8$cycloalkyl, aryl, heteroaryl, heterocyclyl, —C$_{1-3}$ alkylC$_{3-8}$cycloalkyl, —C$_{1-6}$ alkylaryl, —C$_{1-6}$ alkylheteroaryl, and —C$_{1-6}$ alkylheterocyclyl;

each R$^e$ is independently selected from H, —C$_{1-6}$ alkyl, —O—C$_{1-6}$alkyl, —C$_{3-8}$ cycloalkyl, aryl, heteroaryl, heterocyclyl, —O—C$_{3-8}$ cycloalkyl, —O-aryl, —O-heteroaryl, —O-heterocyclyl, —C$_{1-3}$ alkylC$_{3-8}$cycloalkyl, —C$_{1-6}$ alkylaryl, —C$_{1-6}$alkylheteroaryl, —NR$^f$R$^g$, —C$_{1-6}$ alkylNR$^f$R$^g$, —C(O)NR$^f$R$^g$, —C$_{1-6}$ alkylC(O)NR$^f$R$^g$, —NHSO$_2$R$^f$, —C$_{1-6}$ alkylSO$_2$R$^f$, and —C$_{1-6}$ alkylSO$_2$NR$^f$R$^g$;

each R$^f$ is independently selected from H, —C$_{1-6}$ alkyl, —C$_{3-8}$ cycloalkyl, aryl, heteroaryl, heterocyclyl, —C$_{1-3}$ alkylC$_{3-8}$ cycloalkyl, —C$_{1-6}$ alkylaryl, —C$_{1-6}$ alkylheteroaryl, and —C$_{1-6}$ alkylheterocyclyl; and each R$^g$ is independently selected from H, —C$_{1-6}$ alkyl, —C$_{3-8}$ cycloalkyl, aryl, heteroaryl, heterocyclyl, —C$_{1-3}$ alkylC$_{3-8}$ cycloalkyl, —C$_{1-6}$ alkylaryl, —C$_{1-6}$ alkylheteroaryl, and —C$_{1-6}$ alkylheterocyclyl;

or a pharmaceutically acceptable salt thereof.

2. The compound of claim 1, wherein the compound is represented by a compound of formula (VIIIa):

(VIIIa)

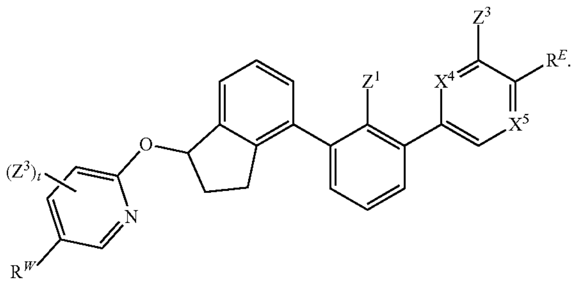

3. The compound of claim 1, wherein the compound is represented by a compound of formula (VIIIe):

(VIIIe)

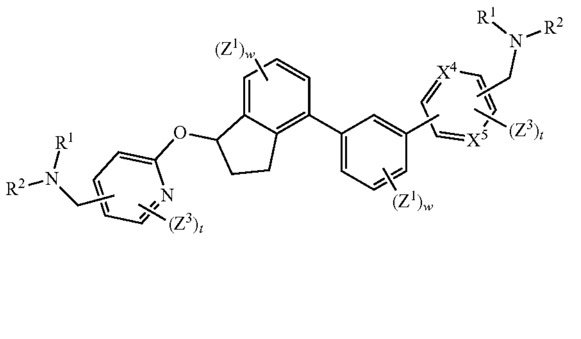

wherein:

each of $X^4$ and $X^5$ are independently N, CH, or $CZ^3$;

each $Z^1$ is independently halo, —$OR^a$, —CN, or —$C_{1-6}$ alkyl;

each w is independently 0, 1, or 2;

each $Z^3$ is independently halo, —$OR^a$, —$N_3$, —$NO_2$, —CN, —$NR^1R^2$, —$SO_2R^a$, —$SO_2NR^aR^b$, —$NR^aSO_2R^a$, —$NR^aC(O)R^a$, —$C(O)R^a$, —$C(O)OR^a$, —$C(O)NR^aR^b$, —$NR^aC(O)OR^a$, —$NR^aC(O)NR^1R^2$, —$OC(O)NR^aR^b$, —$NR^aSO_2NR^aR^b$, —$C(O)NR^aSO_2NR^aR^b$, —$C_{1-6}$ alkyl, —$C_{2-6}$ alkenyl, —$C_{2-6}$ alkynyl, —O—$C_{1-6}$ alkyl, —$C_{3-8}$ cycloalkyl, —$C_{1-6}$ alkyl$C_{3-8}$ cycloalkyl, aryl, heteroaryl, heterocyclyl, or $R^N$, and wherein the alkyl, alkenyl, alkynyl, $C_{3-8}$ cycloalkyl, aryl, heteroaryl, or heterocyclyl group is optionally substituted with 1 to 4 groups independently selected from oxo, —$NO_2$, —$N_3$, —$OR^a$, halo, cyano, —$NR^aR^b$, —$C(O)R^a$, —$C(O)OR^a$, —O—$C_{1-6}$cyanoalkyl, —$C(O)NR^aR^b$, $NR^aC(O)R^a$, —$NR^aC(O)OR^a$, —$SO_2R^a$, —$NR^aSO_2R^b$, —$SO_2NR^aR^b$, —$NR^aSO_2NR^aR^b$, —$C(O)NR^aSO_2NR^aR^b$, and —$C_{3-8}$ cycloalkyl;

$R^N$ is independently —$C_{1-6}$ alkyl$NR^1R^2$, —O—$C_{1-6}$ alkyl$NR^1R^2$, —$C_{1-6}$ alkyl$OC_{1-6}$ alkyl$NR^1R^2$, —$NR^a$—$C_{1-6}$ alkyl$NR^1R^2$, —$C_{1-6}$ alkyl$C(O)NR^1R^2$, —O—$C_{1-6}$ alkyl$C(O)NR^1R^2$, —O—$C_{1-6}$ alkyl$C(O)OR^1$, —S—$C_{1-6}$ alkyl$NR^1R^2$, —$C_{1-6}$ alkyl$OR^a$, or

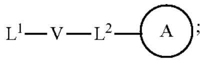;

wherein: $L^1$ is independently a bond, O, $NR^a$, S, SO, or $SO_2$;

V is independently selected from a bond, $C_{1-6}$alkyl, $C_{2-6}$alkenyl, and $C_{2-6}$alkynyl;

wherein each alkyl, alkenyl, or alkynyl is optionally independently substituted with $OR^a$, halo, cyano, —$NR^aR^b$, or —$C_{3-8}$ cycloalkyl;

$L^2$ is independently a bond, O, $NR^a$, S, SO, or $SO_2$;

ring A is independently cycloalkyl, aryl, heteroaryl, or heterocyclyl;

wherein each cycloalkyl, aryl, heteroaryl, or heterocyclyl is optionally substituted with 1 to 4 groups independently selected from oxo, —$NO_2$, —$N_3$, —$OR^a$, halo, cyano, —$C_{1-6}$ alkyl, —$C_{1-6}$ haloalkyl, —$C_{2-6}$alkenyl, —$C_{2-6}$ alkynyl, —O—$C_{1-6}$ haloalkyl, $NR^aR^b$, —$C(O)R^a$, —$C(O)OR^a$, —O—$C_{1-6}$ alkylCN, —$C(O)NR^aR^b$, —$NR^aC(O)R^a$, —$NR^aC(O)OR^a$, —$C(O)N(R^a)OR^b$, —$SO_2R^a$, —$SO_2NR^aR^b$, —$NR^aSO_2R^b$, —$NR^aSO_2NR^aR^b$, —$C(O)NR^aSO_2NR^aR^b$, $C_{3-8}$cycloalkyl, and $C_{1-6}$alkyl$C_{3-8}$ cycloalkyl; and wherein the alkyl, alkenyl, or alkynyl group is optionally independently substituted with —$OR^a$, halo, cyano, —$NR^aR^b$ or —$C_{3-8}$ cycloalkyl;

each t is independently 0, 1, or 2;

each $R^1$ is independently selected from H, —$C_{1-8}$ alkyl, —$C_{2-6}$ alkenyl, —$C_{2-6}$ alkynyl, —$C_{3-6}$ cycloalkyl, aryl, heteroaryl, heterocyclyl, —$C_{1-6}$ alkylaryl, —$C_{1-6}$ alkylheteroaryl, —$C_{1-6}$ alkylheterocyclyl, —$C_{1-6}$ alkyl$C(O)OR^a$, —$C_{2-6}$ alkenyl$C(O)OR^a$, —$SO_2R^a$, —$SO_2NR^aR^b$, —$C(O)NR^aSO_2R^a$, and $C_{1-6}$ alkyl $C_{3-8}$cycloalkyl;

wherein each alkyl, alkenyl, cycloalkyl, aryl, heteroaryl, or heterocyclyl is optionally substituted with 1 to 4 groups independently selected from —$OR^a$, —CN, halo, $C_{1-6}$alkyl, —$C_{1-6}$ alkyl$OR^a$, —$C_{1-6}$ cyanoalkyl, —$C_{1-6}$ haloalkyl, $C_{3-8}$ cycloalkyl, —$C_{1-3}$ alkyl$C_{3-8}$cycloalkyl, —$C(O)R^a$, —$C_{1-6}$ alkyl$C(O)R^a$, —$C(O)OR^a$, —$C_{1-6}$ alkyl$C(O)OR^a$, —$NR^aR^b$, —$OC(O)NR^aR^b$, —$NR^aC(O)OR^b$, —$C_{1-6}$ alkyl$NR^aR^b$, —$C(O)NR^aR^b$, —$C_{1-6}$ alkyl$C(O)NR^aR^b$, —$SO_2R^a$, —$C_{1-6}$ alkyl$SO_2R^a$, —$SO_2NR^aR^b$, —$C_{1-6}$ alkyl$SO_2NR^aR^b$, —$C(O)NR^aSO_2R^b$, —$C_{1-6}$ alkyl$C(O)NR^aSO_2R^b$, —$NR^aC(O)R^b$, and —$C_{1-6}$alkyl$NR^aC(O)R^b$;

each $R^2$ is independently selected from H, —$C_{1-6}$ alkyl, —$C_{2-6}$ alkenyl, —$C_{2-6}$ alkynyl, —$C_{3-6}$ cycloalkyl, aryl, heteroaryl, heterocyclyl, —$C_{1-6}$ alkylaryl, —$C_{1-6}$ alkylheteroaryl, —$C_{1-6}$ alkylheterocyclyl, —$C_{2-6}$ alkyl-$OR^a$, —$C_{1-6}$ alkyl$C(O)OR^a$, and —$C_{2-6}$ alkenyl$C(O)OR^a$;

wherein each alkyl, alkenyl, alkynyl, cycloalkyl, aryl, heteroaryl, or heterocyclyl is optionally substituted with 1 to 4 groups independently selected from —$OR^a$, —CN, halo, $C_{1-6}$alkyl, —$C_{1-6}$ alkyl$OR^a$, —$C_{1-6}$ cyanoalkyl, —$C_{1-6}$ haloalkyl, —$C_{3-8}$ cycloalkyl, —$C_{1-3}$ alkyl$C_{3-8}$cycloalkyl, —$C(O)R^a$, —$C_{1-6}$ alkyl$C(O)R^a$, —$C(O)OR^a$, —$C_{1-6}$ alkyl$C(O)OR^a$, —$NR^aR^b$, —$C_{1-6}$ alkyl$NR^aR^b$, —$C(O)NR^aR^b$, $C_{1-6}$ alkyl$C(O)NR^aR^b$, —$SO_2R^a$, —$C_{1-6}$ alkyl$SO_2R^a$, —$SO_2NR^aR^b$, —$C_{1-6}$ alkyl$SO_2NR^aR^b$, —$C(O)NR^aSO_2R^b$, and —$NR^aC(O)R^b$;

or $R^1$ and $R^2$ combine to form a heterocyclyl group optionally containing 1, 2, or 3 additional heteroatoms independently selected from oxygen, sulfur, and nitrogen, and optionally substituted with 1 to 3 groups independently selected from oxo, —$C_{1-6}$ alkyl, —$C_{3-8}$ cycloalkyl, —$C_{2-6}$ alkenyl, —$C_{2-6}$ alkynyl, —$OR^a$, —$C(O)OR^a$, —$C_{1-6}$ cyanoalkyl, —$C_{1-6}$ alkyl$OR^a$, —$C_{1-6}$ haloalkyl, —$C_{1-3}$ alkyl$C_{3-8}$cycloalkyl, —$C(O)R^a$, $C_{1-6}$ alkyl$C(O)R^a$, —$C_{1-6}$ alkyl$C(O)OR^a$, —$NR^aR^b$, —$C_{1-6}$alkyl$NR^aR^b$, —$C(O)NR^aR^b$, —$C_{1-6}$ alkyl$C(O)NR^aR^b$, —$SO_2R^a$, —$C_{1-6}$ alkyl$SO_2R^a$, —$SO_2NR^aR^b$, and $C_{1-6}$ alkyl$SO_2NR^aR^b$;

each $R^3$ is independently H, —$C_{1-6}$ alkyl, —$C_{2-6}$ alkenyl, —$C_{3-6}$ cycloalkyl, aryl, heteroaryl, heterocyclyl, —$C_{1-6}$ alkylaryl, —$C_{1-6}$ alkylheteroaryl, —$C_{1-6}$ alkylheterocyclyl, —$C_{2-6}$ alkyl-$OR^a$, —$C_{1-6}$ alkyl$C(O)OR^a$, or —$C_{2-6}$ alkenyl$C(O)OR^a$;

each $R^a$ is independently selected from H, —$C_{1-6}$ alkyl, —$C_{3-8}$ cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$alkylheterocyclyl;

each $R^b$ is independently selected from H, —$C_{1-6}$ alkyl, —$C_{3-8}$ cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$ alkylheterocyclyl;

or $R^a$ and $R^b$ may combine together to form a ring consisting of 3-8 ring atoms that are C, N, O, or S; wherein the ring is optionally substituted with 1 to 4 groups independently selected from —$OR^f$, —CN, halo, —$C_{1-6}$ alkyl$OR^f$, —$C_{1-6}$ cyanoalkyl, —$C_{1-6}$ haloalkyl, —$C_{3-8}$ cycloalkyl, —$C_{1-3}$ alkyl$C_{3-8}$cycloalkyl, —$C(O)R^f$, —$C_{1-6}$ alkyl$C(O)R^f$, —$C(O)OR^f$, —$C_{1-6}$ alkyl$C(O)OR^f$, —$NR^fR^g$, —$C_{1-6}$ alkyl$NR^fR^g$, —$C(O)NR^fR^g$, —$C_{1-6}$ alkyl$C(O)NR^fR^g$, —$SO_2R^f$, —$C_{1-6}$ alkyl$SO_2R^f$, —$SO_2NR^fR^g$, —$C_{1-6}$ alkyl$SO_2NR^fR^g$, —$C(O)NR^fSO_2R^g$, and —$NR^fC(O)R^g$;

each $R^c$ is independently selected from H, OH, —$C_{1-6}$ alkyl, —$C_{3-8}$ cycloalkyl, aryl, heteroaryl, heterocyclyl, —$C_{1-3}$ alkyl$C_{3-8}$ cycloalkyl, —$C_{1-6}$ alkylaryl, —$C_{1-6}$ alkylheteroaryl, and —$C_{1-6}$ alkylheterocyclyl;

each $R^d$ is independently selected from H, —$C_{1-6}$ alkyl, —$C_3$-$C_8$cycloalkyl, aryl, heteroaryl, heterocyclyl, —$C_{1-3}$ alkyl$C_{3-8}$cycloalkyl, —$C_{1-6}$ alkylaryl, —$C_{1-6}$ alkylheteroaryl, and —$C_{1-6}$ alkylheterocyclyl;

each $R^f$ is independently selected from H, —$C_{1-6}$ alkyl, —$C_{3-8}$ cycloalkyl, aryl, heteroaryl, heterocyclyl, —$C_{1-3}$ alkyl$C_{3-8}$ cycloalkyl, —$C_{1-6}$ alkylaryl, —$C_{1-6}$ alkylheteroaryl, and —$C_{1-6}$ alkylheterocyclyl; and each $R^g$ is independently selected from H, —$C_{1-6}$ alkyl, —$C_{3-8}$ cycloalkyl, aryl, heteroaryl, heterocyclyl, —$C_{1-3}$ alkyl$C_{3-8}$ cycloalkyl, —$C_{1-6}$ alkylaryl, —$C_{1-6}$ alkylheteroaryl, and —$C_{1-6}$ alkylheterocyclyl;

or a pharmaceutically acceptable salt thereof.

4. The compound of claim 3, wherein the compound is represented by a compound of formula (VIIIf):

(VIIIf)

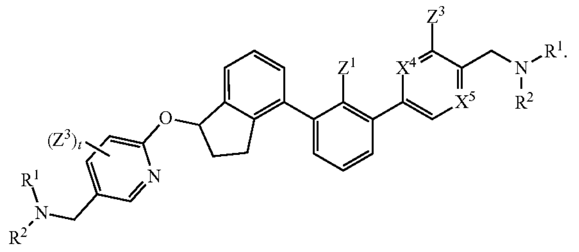

5. The compound of claim 1, wherein the compound is represented by a compound of formula (VIIIg):

(VIIIg)

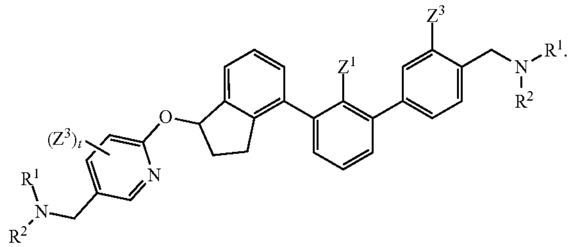

6. The compound of claim 1, wherein the compound is represented by a compound of formula (VIIIh):

(VIIIh)

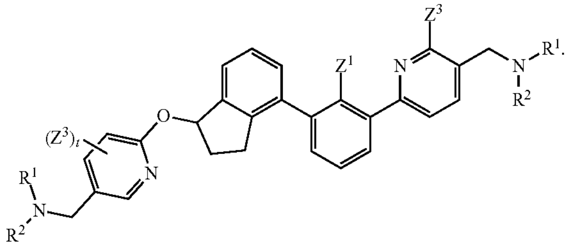

7. The compound of claim 1, wherein the compound is represented by a compound of formula (VIIIi):

(VIIIi)

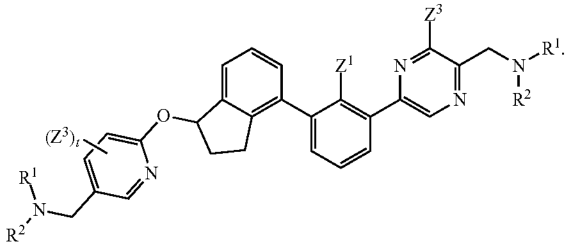

8. The compound of claim 1, wherein each $Z^1$ is independently halo.

9. The compound of claim 1, wherein each $Z^3$ is independently halo or $C_{1-6}$ alkoxy.

10. The compound according to claim 1, wherein $R^E$ and $R^W$ are independently selected from —$NR^1R^2$, —$C_{1-6}$ alkyl$NR^1R^2$, —$OC_{1-6}$ alkyl$NR^1R^2$, —$C_{1-6}$ alkyl $OC_{1-6}$alkyl$NR^1R^2$, —$NR^aC_{1-6}$ alkyl$NR^1R^2$, —$C_{1-6}$ alkyl$N^+R^1R^2R^3$, —$SC_{1-6}$ alkyl$NR^1R^2$, —$C(O)NR^1R^2$, —$SO_2R^a$, —$(CH_2)_uSO_2NR^1R^2$, —$(CH_2)_uNR^aSO_2NR^aR^b$, —$SO_2NR^aC_{1-6}$ alkyl$NR^1R^2$, —$NR^aSO_2C_{1-6}$ alkyl$NR^1R^2$, —$(CH_2)_uC(O)NR^aSO_2NR^aR^b$, —$(CH_2)_uN^+R^1R^2O^-$, —$(CH_2)_uP^+R^bR^cR^d$, $(CH_2)_uP^+R^cR^dO^-$, —$(CH_2)_uP^+O[NR^aR^b][NR^cR^d]$, —$(CH_2)_uNR^cP(O)(OR^c)_2$, —$(CH_2)_uCH_2OP(O)(OR^c)(OR^d)$, —$(CH_2)_uOP(O)(OR^c)(OR^d)$, and —$(CH_2)_uOP(O)NR^aR^b)(OR^a)$;

$R^1$ is H, —$C_{1-6}$alkyl, —$C_{3-6}$cycloalkyl, heterocyclyl, —$C_{2-6}$alkyl-$OR^a$, or —$C_{1-6}$alkylC(O)$OR^a$;

wherein each alkyl, cycloalkyl, or heterocyclyl is optionally substituted with 1 to 2 groups independently selected from —$OR^a$, —CN, halo, —$C_{1-6}$alkyl$OR^a$, —$C_{1-6}$cyanoalkyl, —$C_{1-3}$haloalkyl, —$C(O)R^a$, —$C_{1-6}$alkyl$C(O)R^a$, —$C(O)OR^a$, —$C_{1-6}$ alkyl$C(O)OR^a$, —$C(O)NR^aR^b$, and —$C_{1-6}$ alkyl$C(O)NR^aR^b$;

$R^2$ is selected from —$C_{1-6}$ alkyl, —$C_{3-6}$ cycloalkyl, heterocyclyl, —$C_{2-6}$ alkyl-$OR^a$, and —$C_{1-6}$ alkyl$C(O)OR^a$;

wherein each alkyl, cycloalkyl, or heterocyclyl is optionally substituted with 1 to 2 groups independently selected from —$OR^a$, —CN, —$C_{1-6}$alkyl$OR^a$, —$C_{1-6}$cyanoalkyl, —$C_{1-3}$haloalkyl, —$C_{3-8}$cycloalkyl, —$C_{1-3}$alkyl$C_{3-8}$cycloalkyl, —$C(O)R^a$, —$C_{1-6}$alkylC(O)$R^a$, —C(O)O$R^3$, —$C_{1-6}$ alkylC(O)O$R^a$, —C(O)N$R^aR^b$, and $C_{1-6}$ alkylC(O)N$R^aR^b$, or $R^1$ and $R^2$ combine to form a heterocyclyl optionally containing an additional heteroatom selected from oxygen, sulfur or nitrogen, and optionally substituted with 1 to 3 groups independently selected from oxo, —$C_{1-6}$alkyl, —O$R^a$, —C(O)O$R^a$, —C(O)$R^a$, $C_{1-6}$ alkylC(O)$R^a$, —$C_{1-6}$alkylC(O)O$R^a$, —N$R^aR^b$, —$C_{1-6}$ alkylN$R^aR^b$, and —C(O)N$R^aR^b$;

$R^3$ is independently H, —$C_{1-6}$ alkyl, —$C_{2-6}$ alkenyl, —$C_{3-6}$ cycloalkyl, aryl, heteroaryl, heterocyclyl, or —$C_{1-6}$ alkylaryl;

$R^a$ is independently H or —$C_{1-6}$ alkyl;

$R^b$ is independently H or —$C_{1-6}$ alkyl;

$R^c$ is independently selected from H, —$C_{1-6}$ alkyl, —$C_{3-8}$ cycloalkyl, and —$C_{1-3}$ alkyl$C_{3-8}$ cycloalkyl;

$R^d$ is independently selected from H, —$C_{1-6}$ alkyl, —$C_3$-$C_8$cycloalkyl, and —$C_{1-3}$alkyl$C_{3-8}$cycloalkyl; and u is 0, 1, 2, or 3;

or a pharmaceutically acceptable salt thereof.

11. The compound according to claim 1, wherein the groups $R^E$ and $R^W$ are each independently:

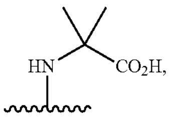 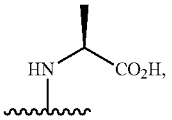 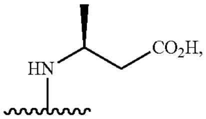

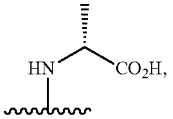 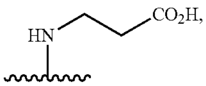 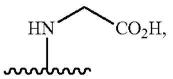

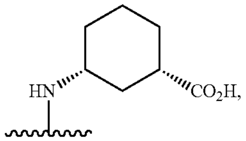 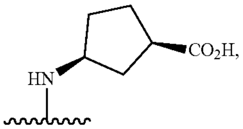

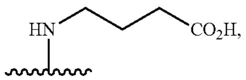 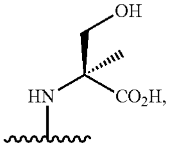

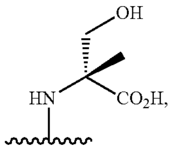 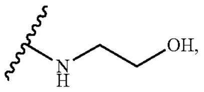

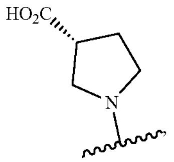 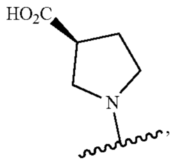

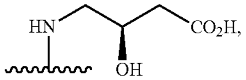 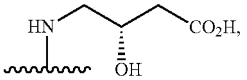

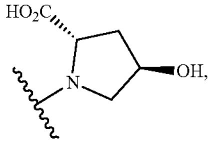 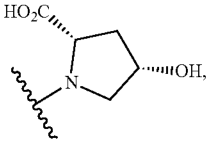

-continued

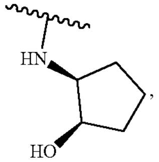 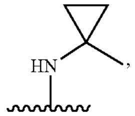 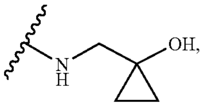

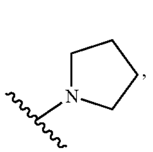 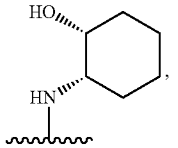 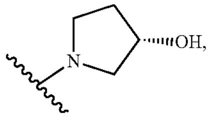

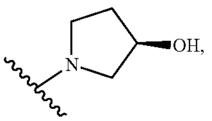 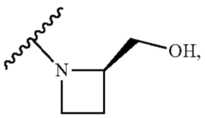

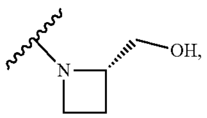 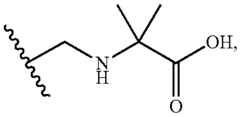

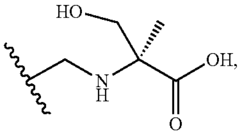 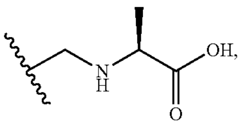

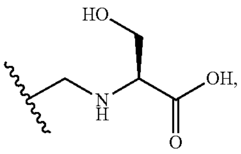 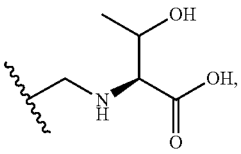

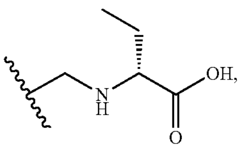 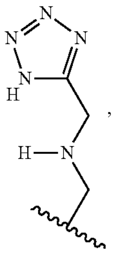 ,

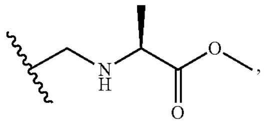 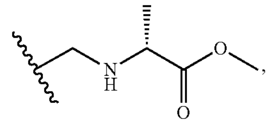

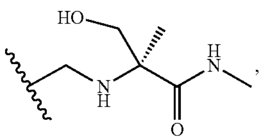 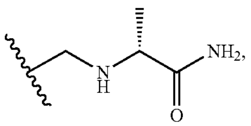 or

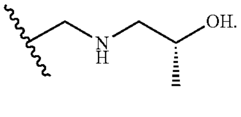

12. The compound of claim 1, having the structure:
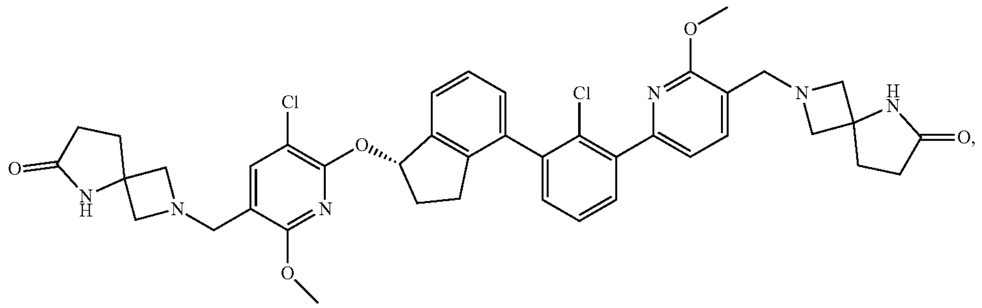 [SMILES: COc1nc(-c2cccc(-c3cccc4c3CC[C@@H]4Oc3nc(OC)c(CN4CC5(CCC(=O)N5)C4)cc3Cl)c2Cl)ccc1CN1CC2(CCC(=O)N2)C1]
or a pharmaceutically acceptable salt thereof.
13. The compound of claim 1, having the structure:
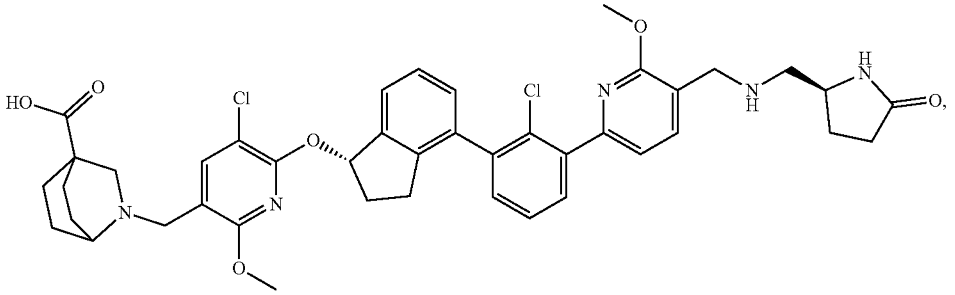 [SMILES: COc1nc(-c2cccc(-c3cccc4c3CC[C@@H]4Oc3nc(OC)c(CN4CC5(C(=O)O)CCC4CC5)cc3Cl)c2Cl)ccc1CNC[C@@H]1CCC(=O)N1]
or a pharmaceutically acceptable salt thereof.
14. A compound selected from:
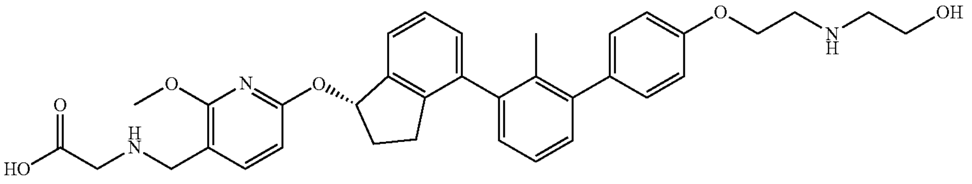
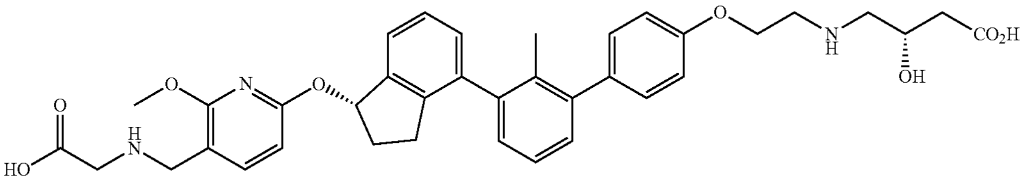

-continued
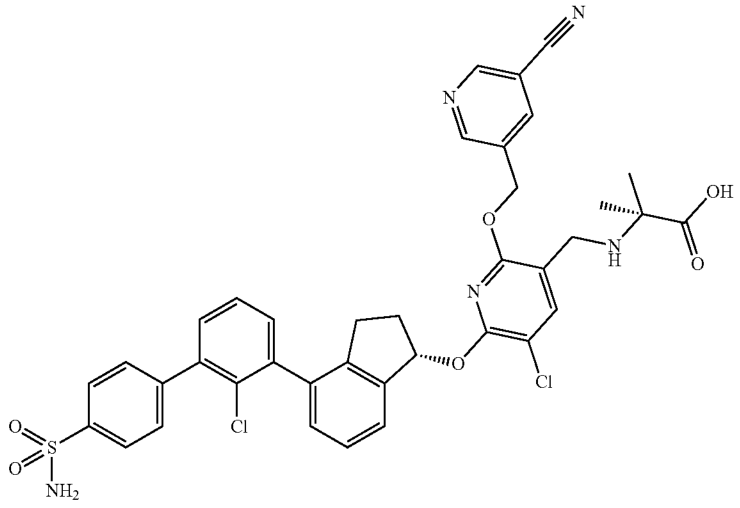
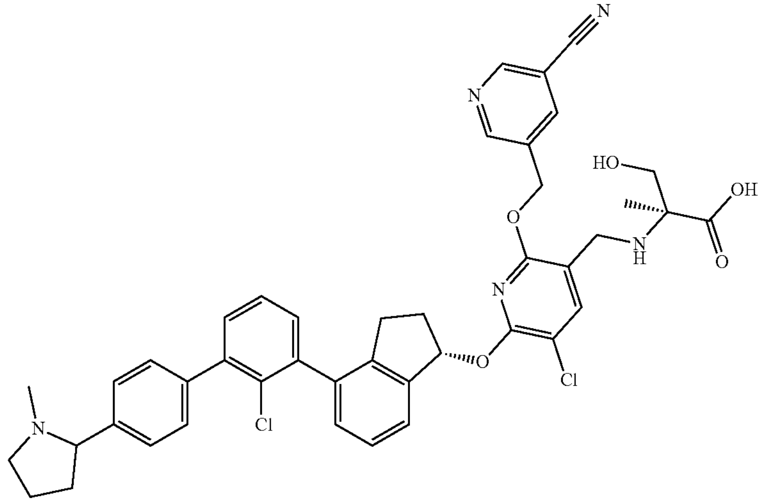
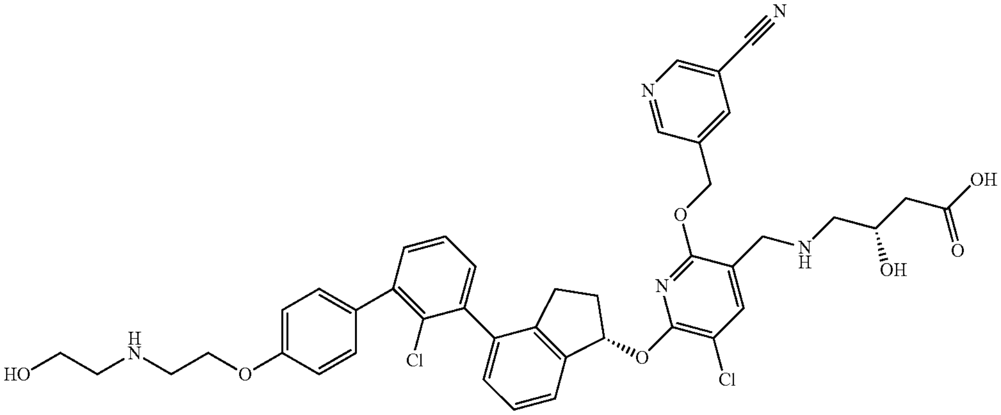

-continued
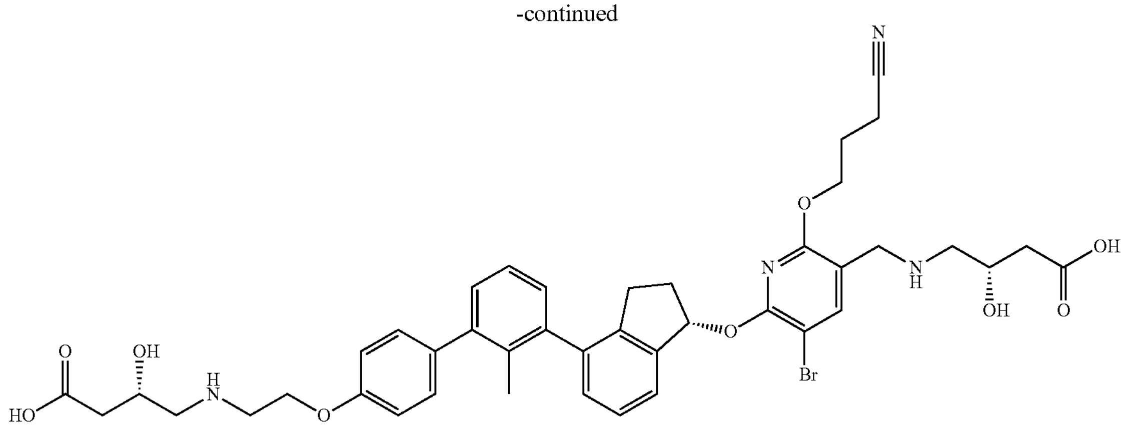
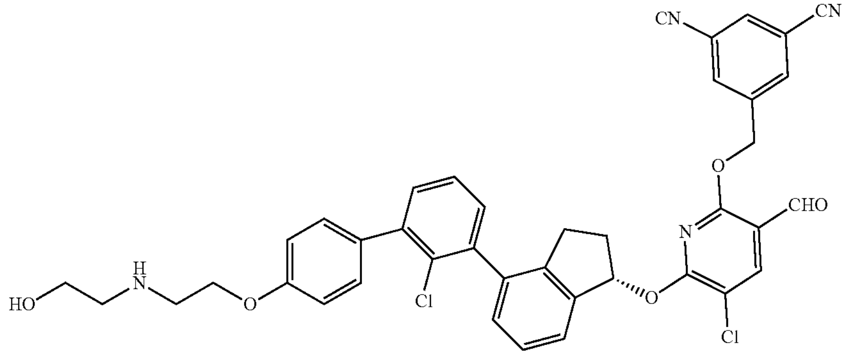
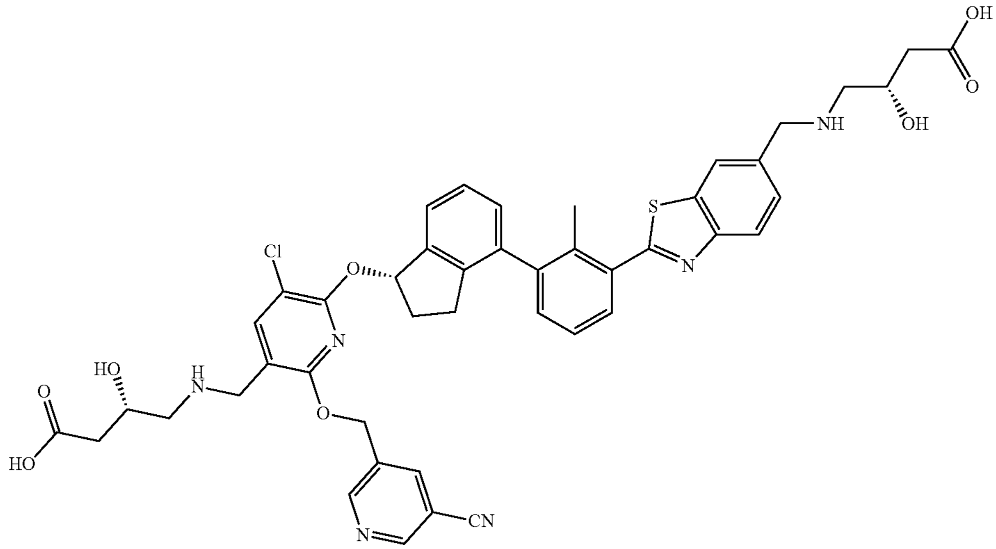
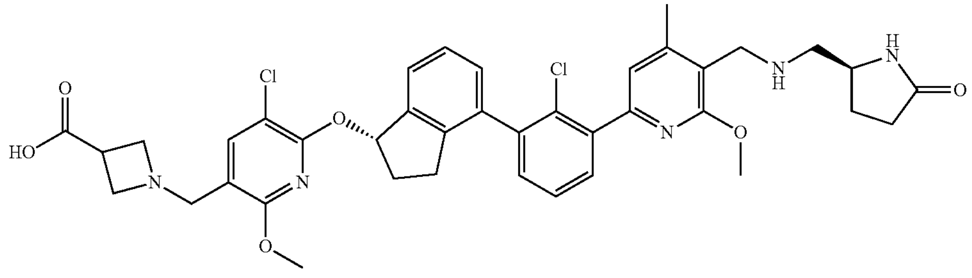

-continued
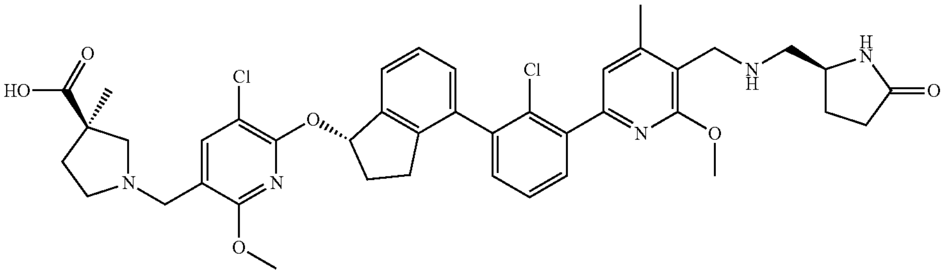
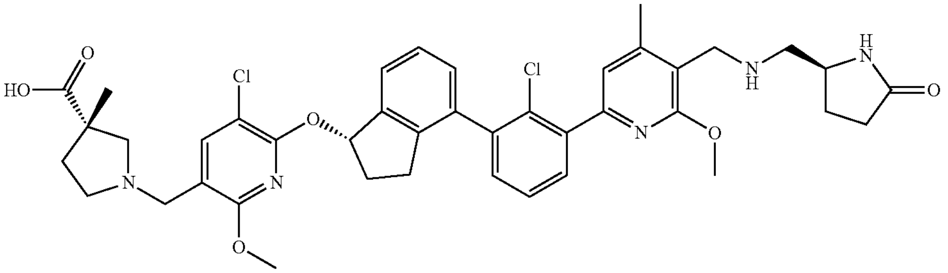
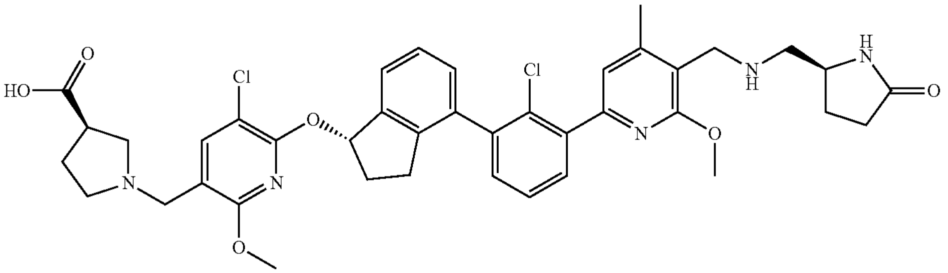
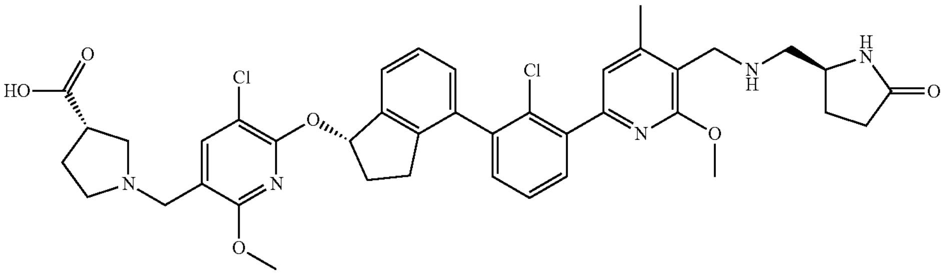
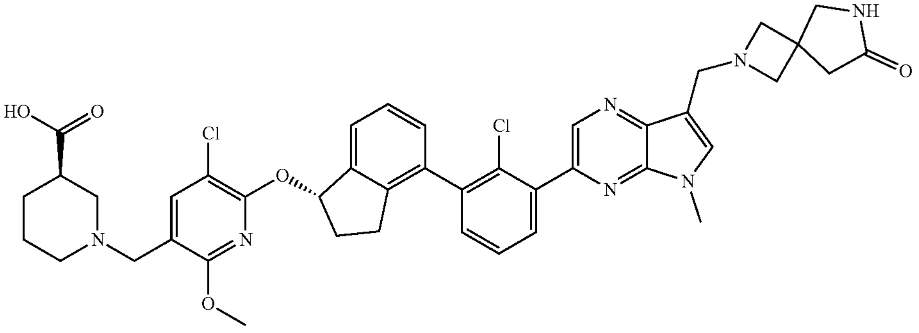

-continued
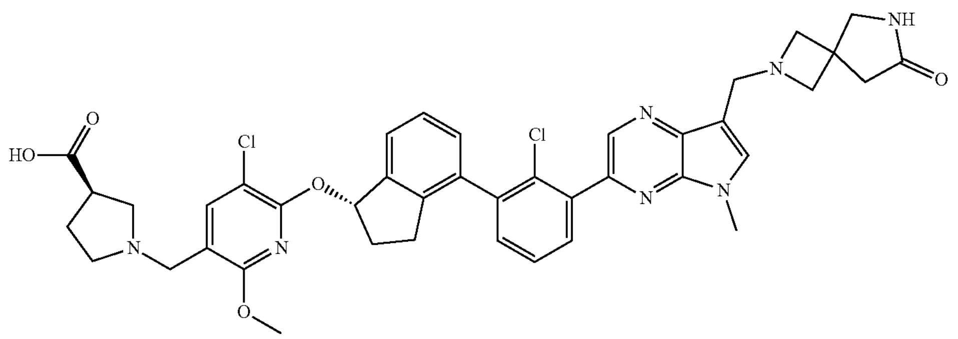
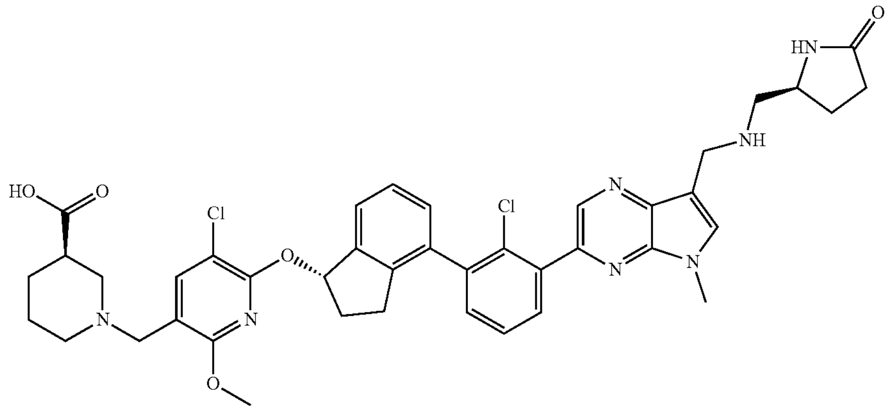
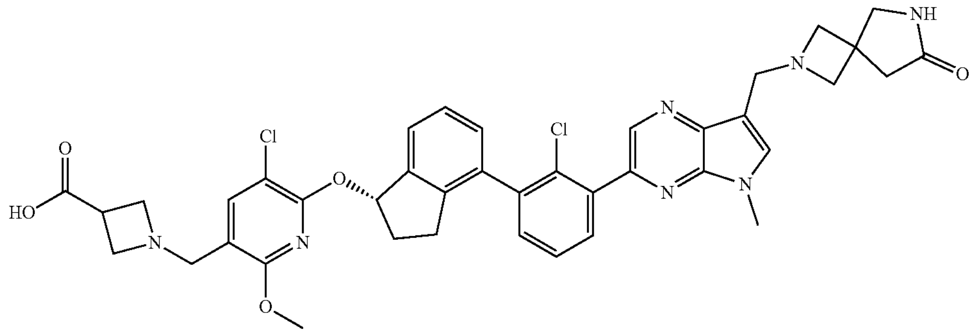
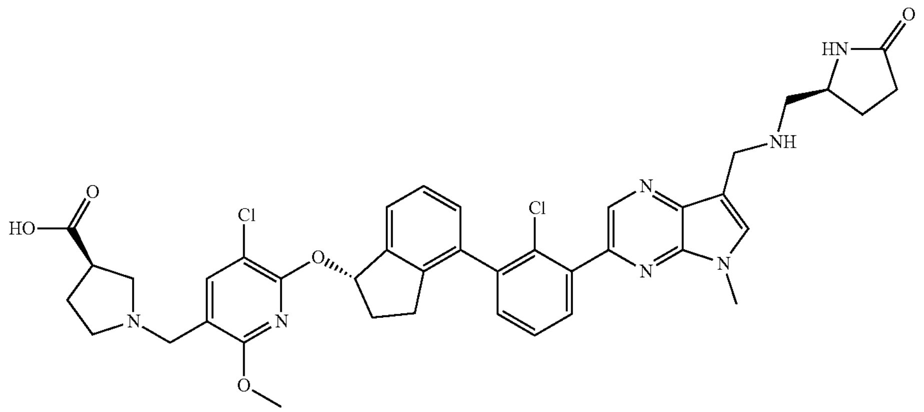

-continued
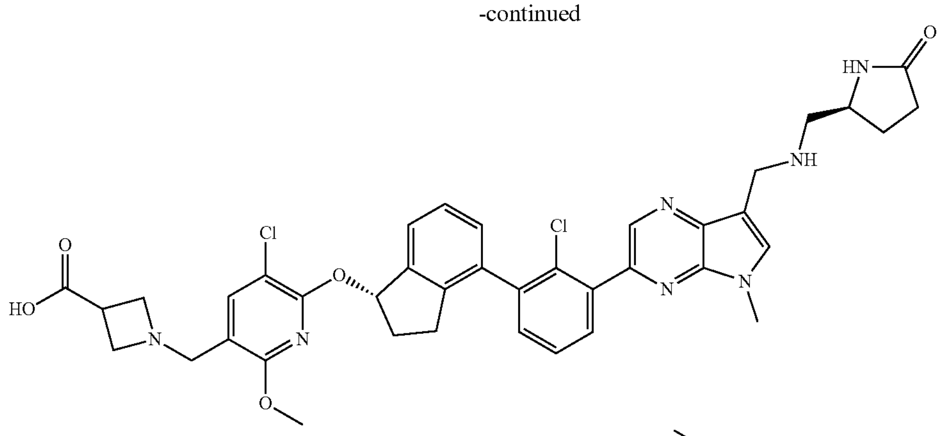
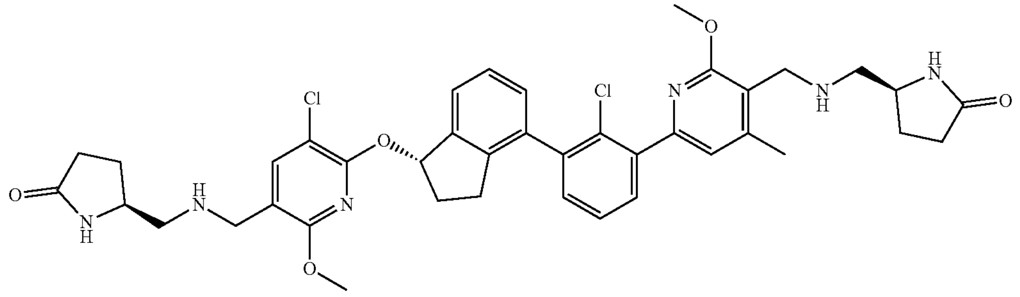
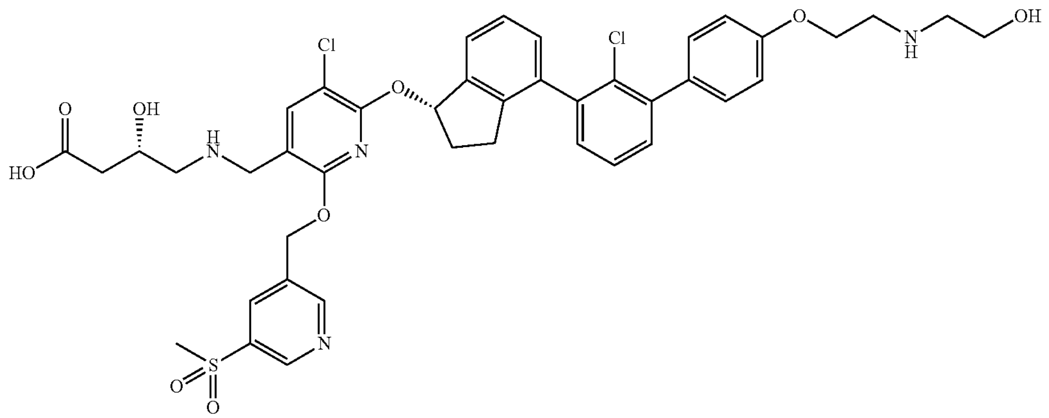
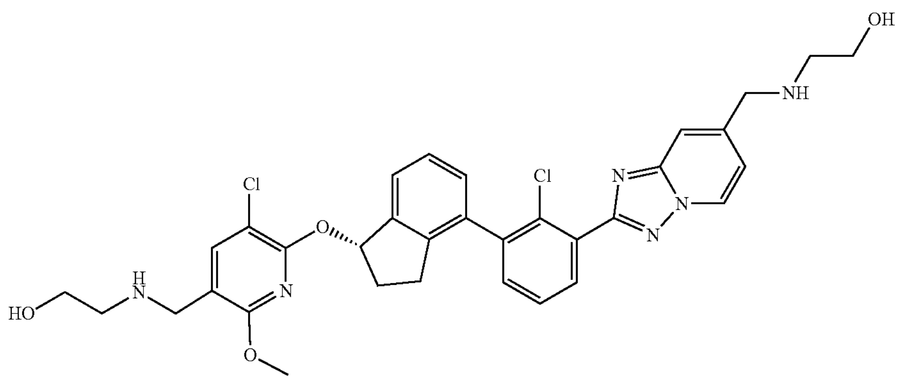

-continued
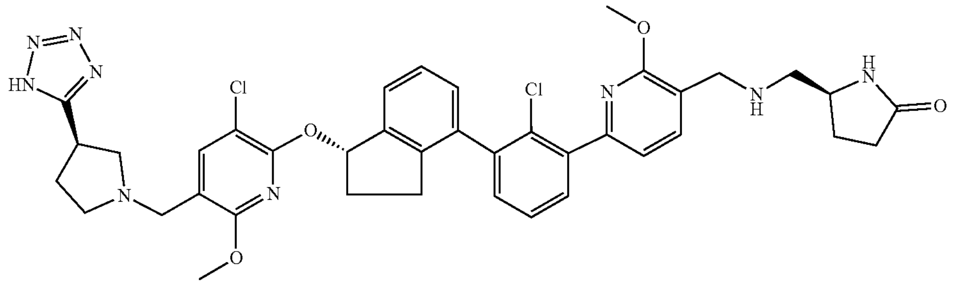
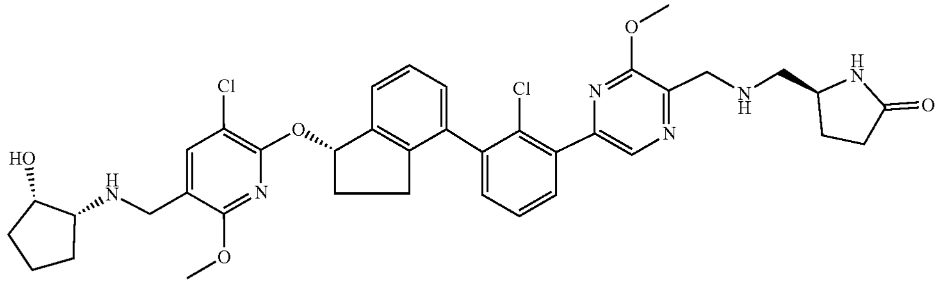
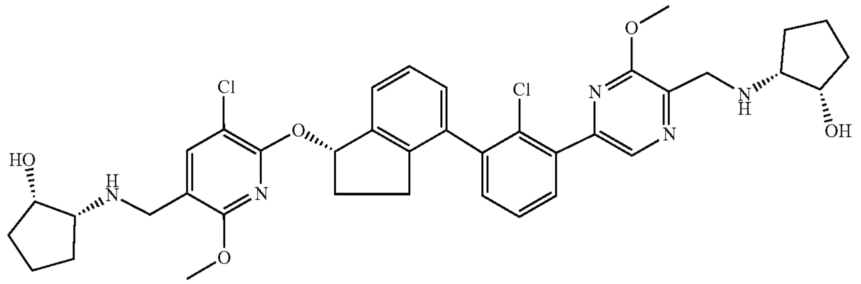
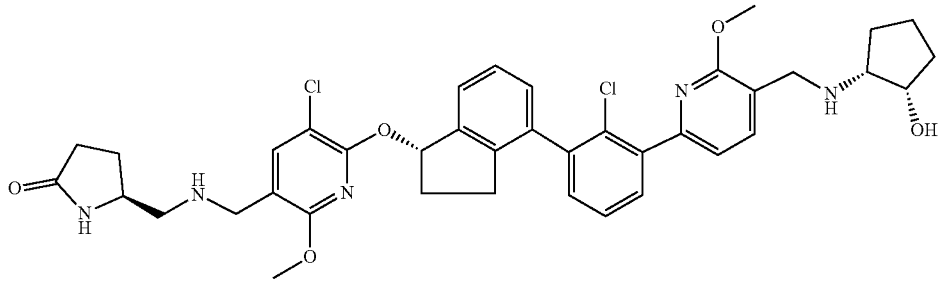
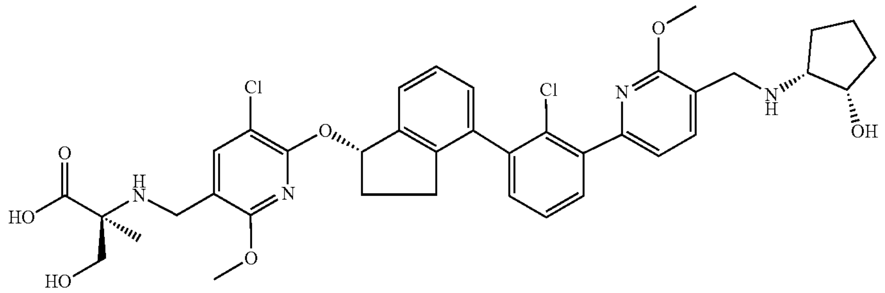
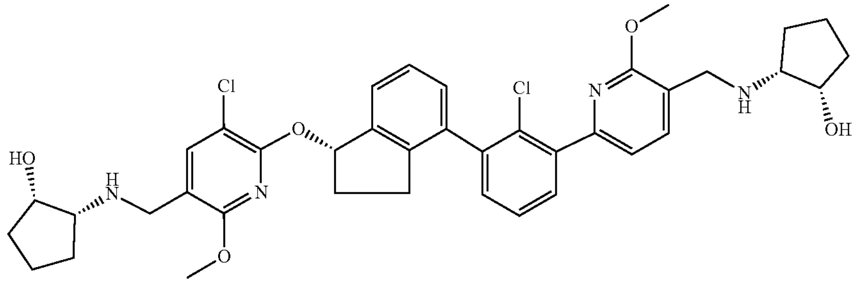

-continued
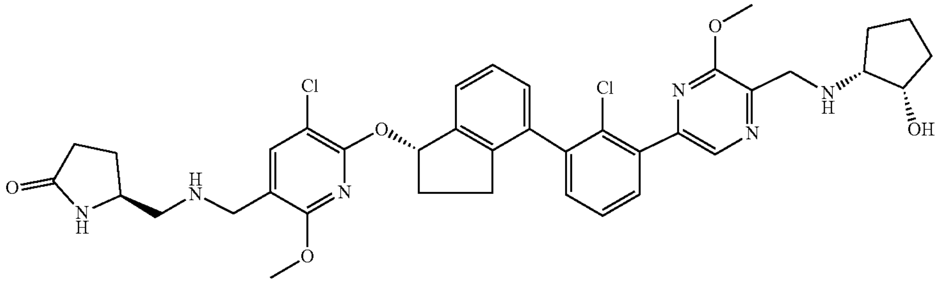
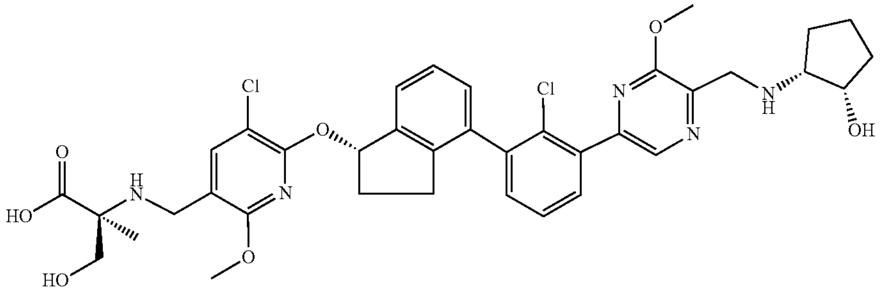
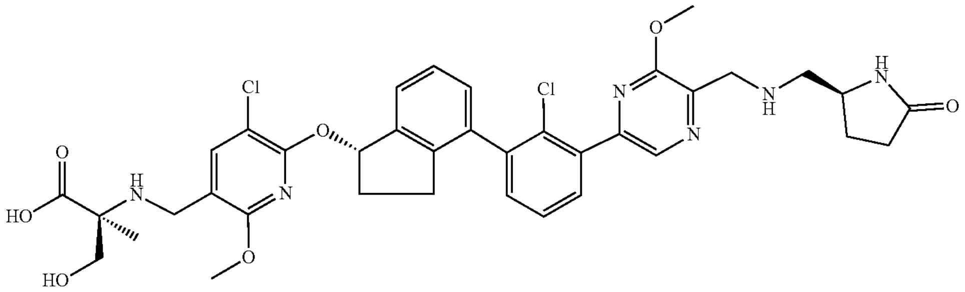
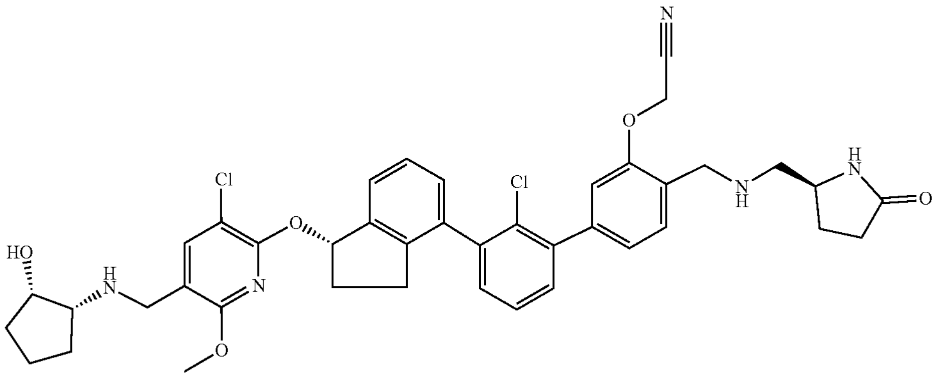
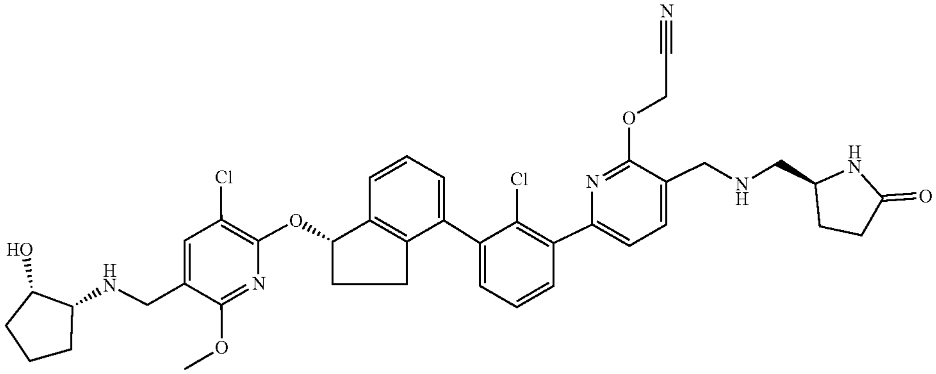

-continued
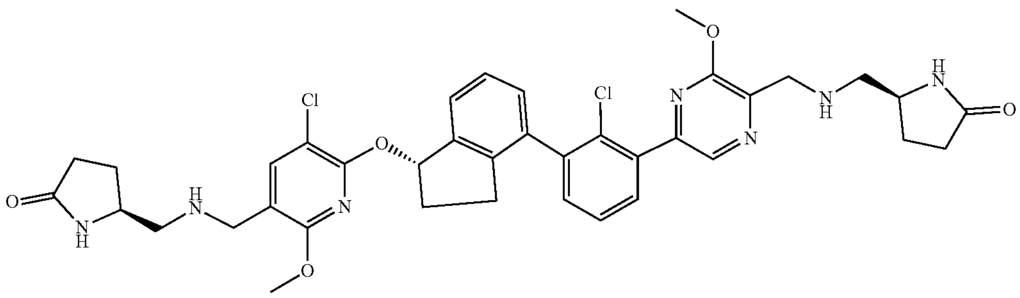
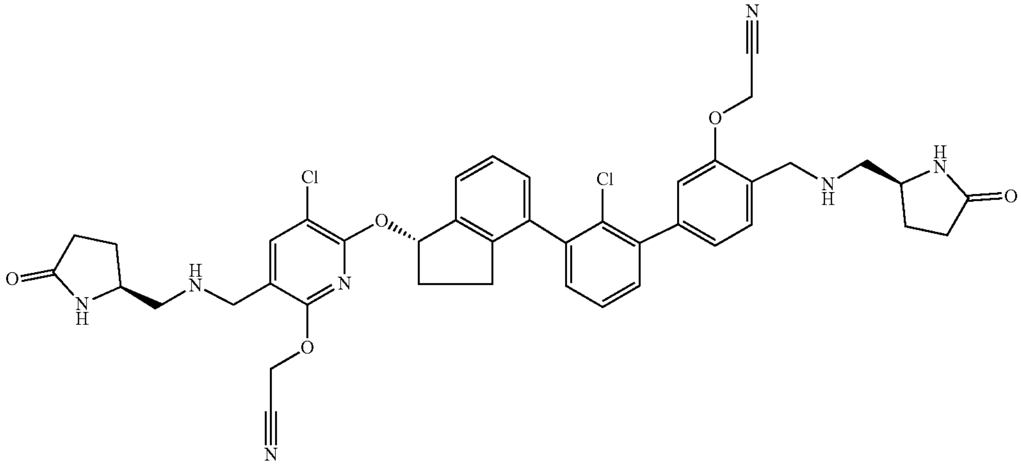
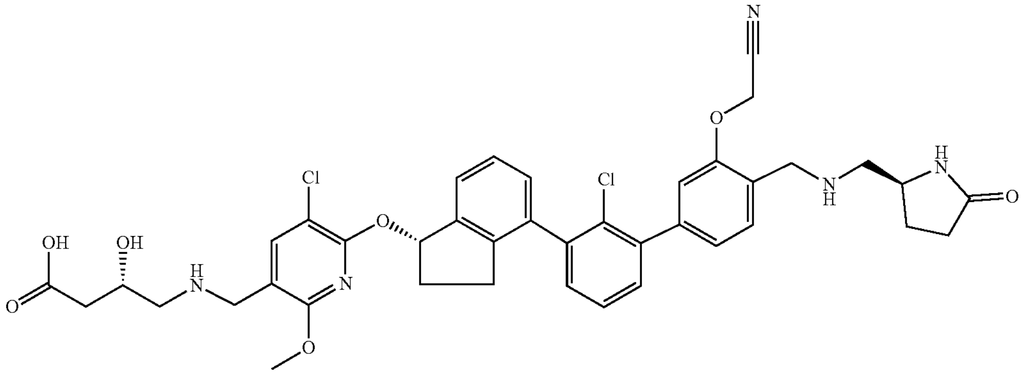
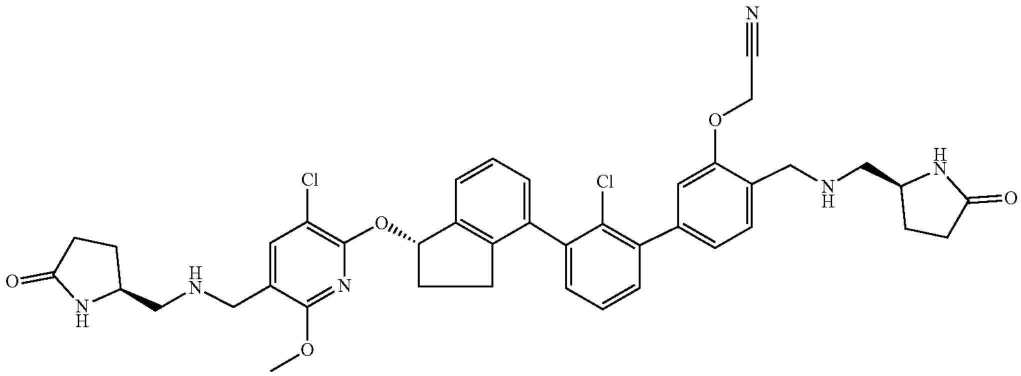

-continued
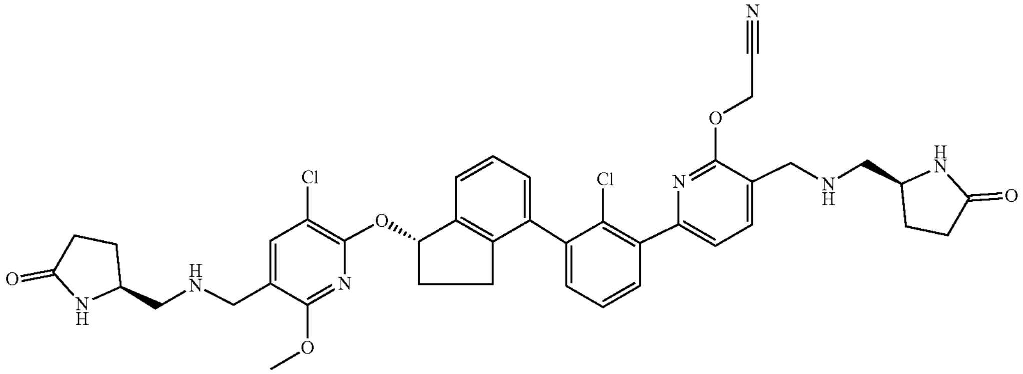
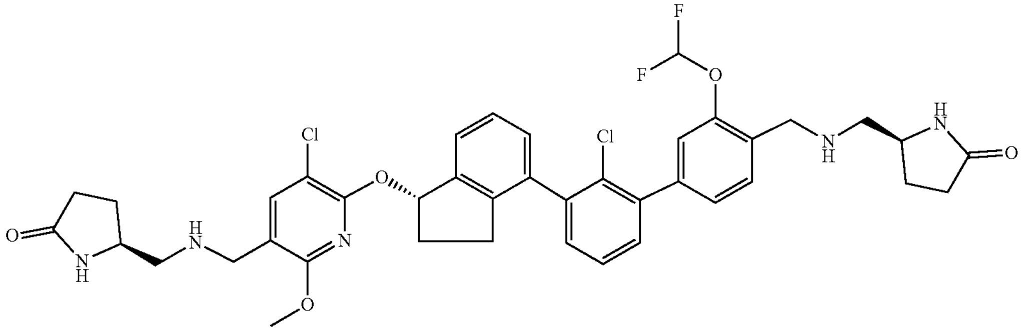
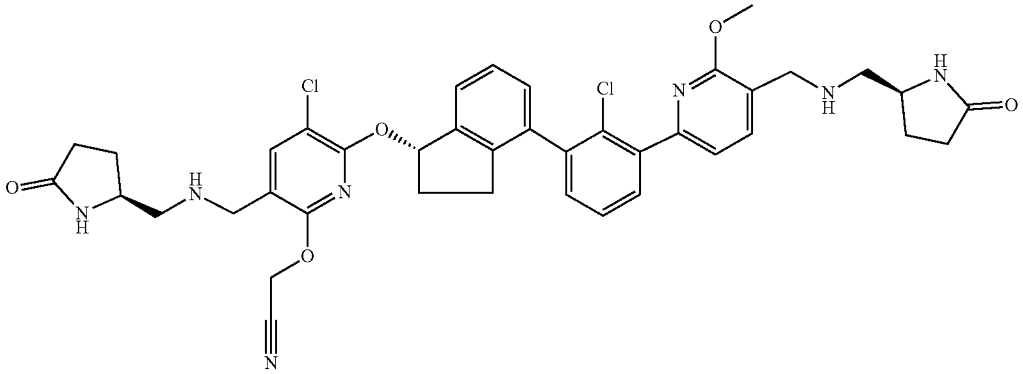
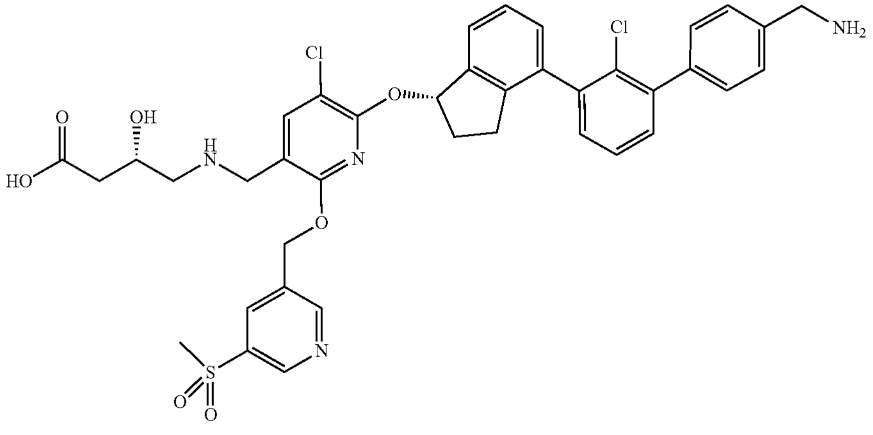

-continued
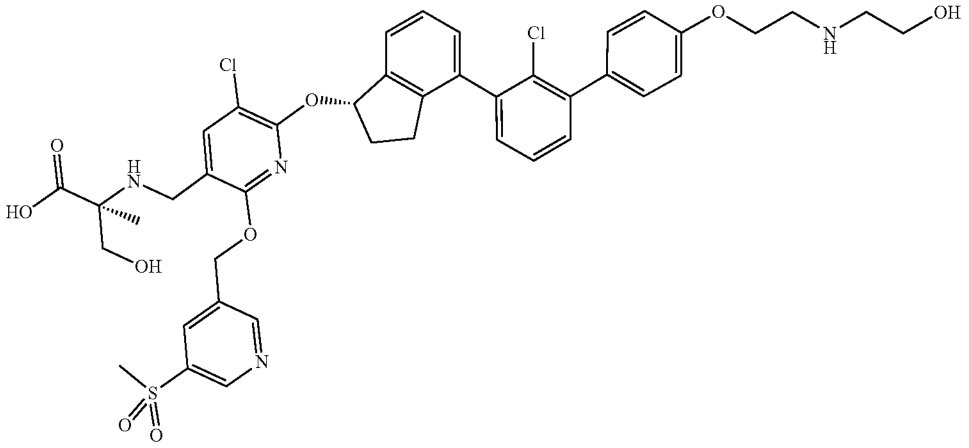
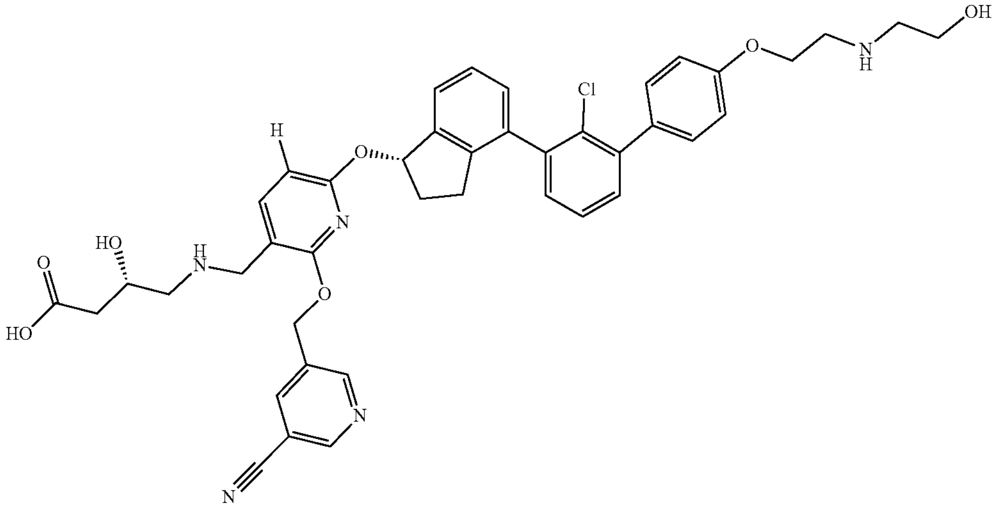
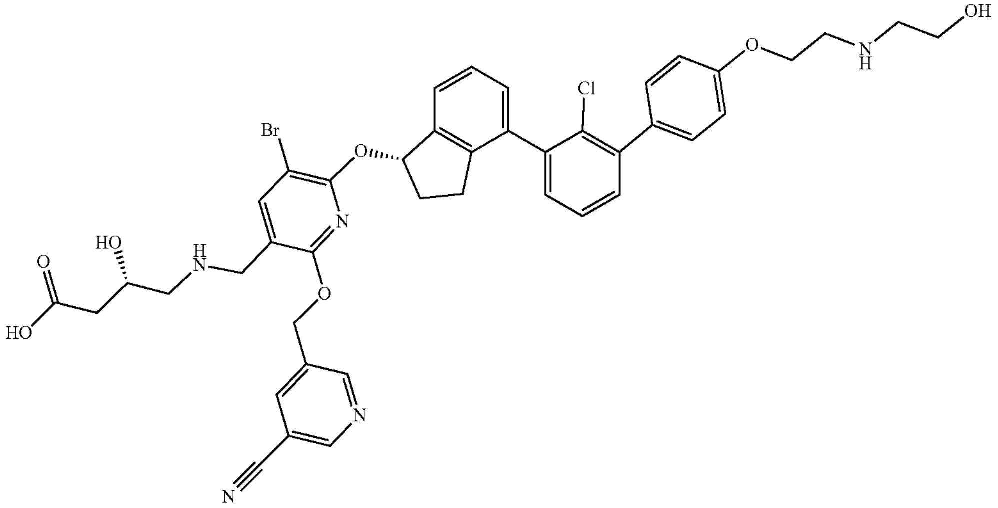

-continued
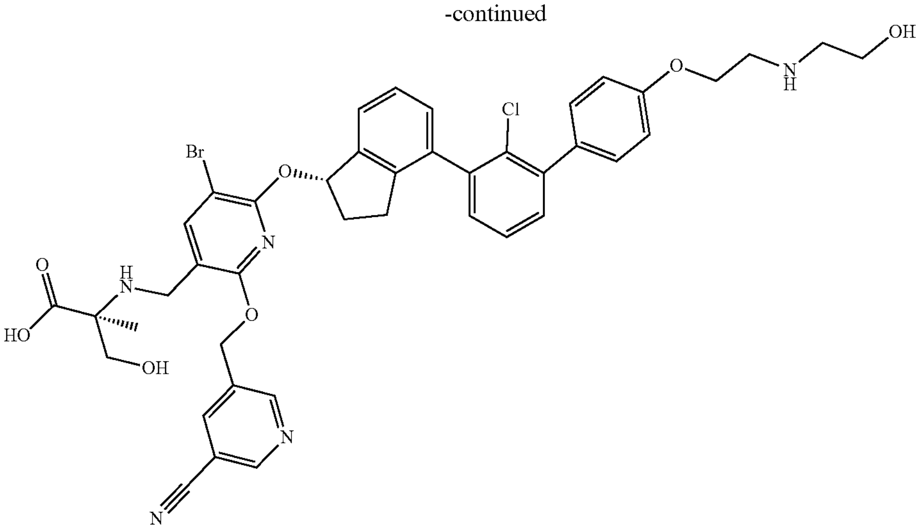
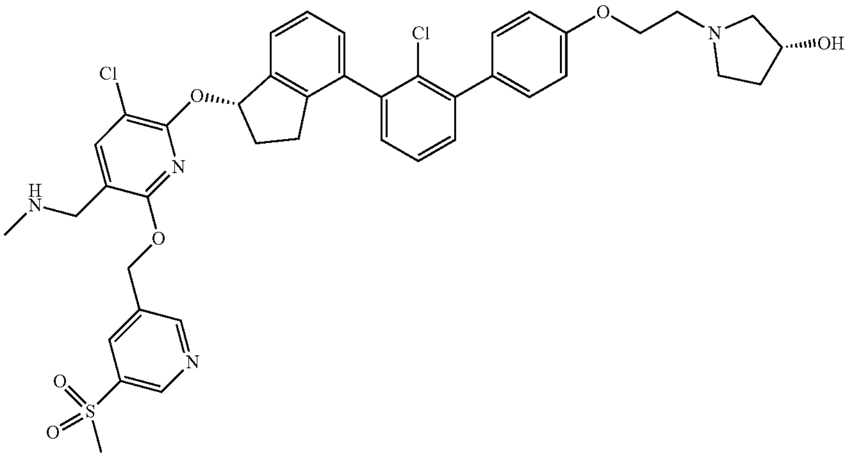
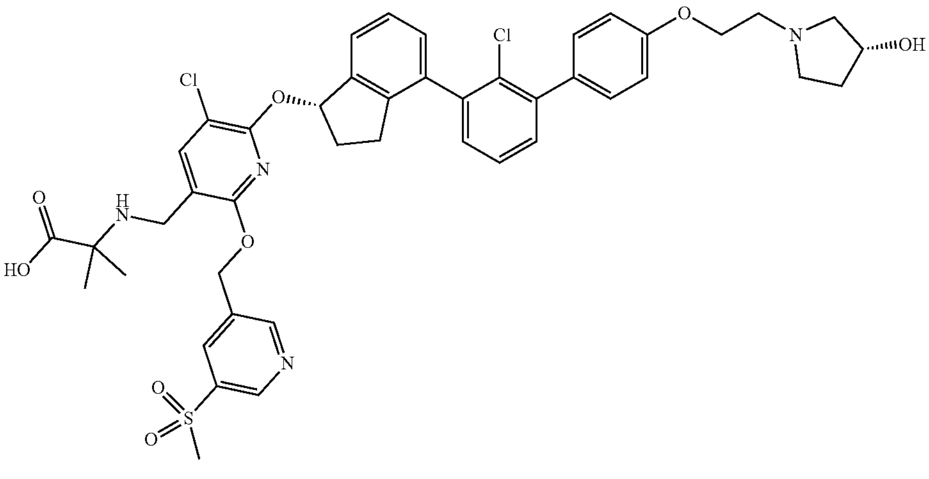

-continued
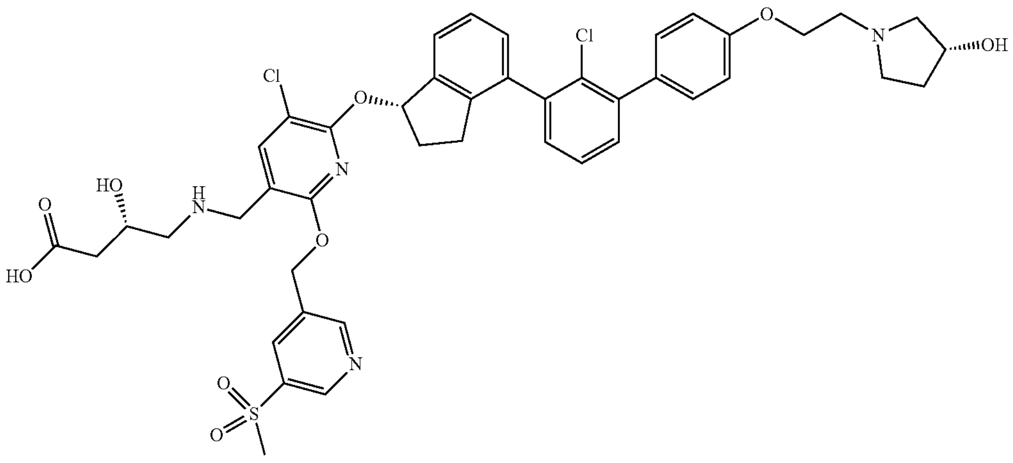
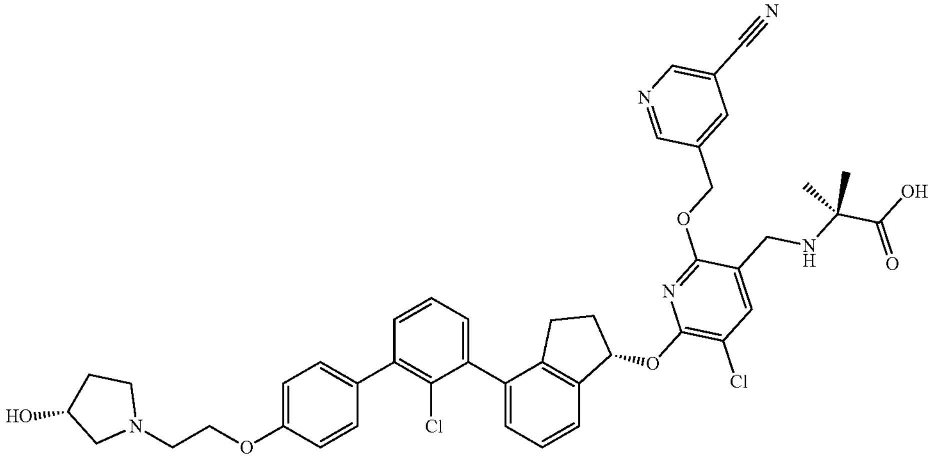
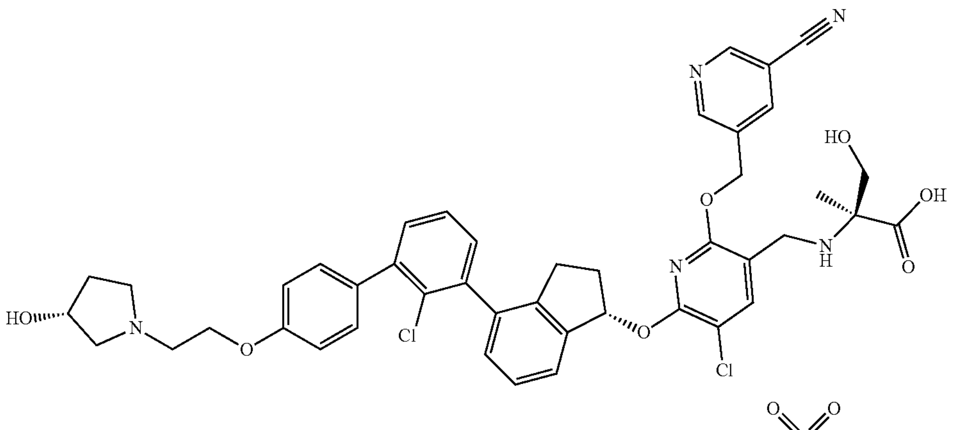
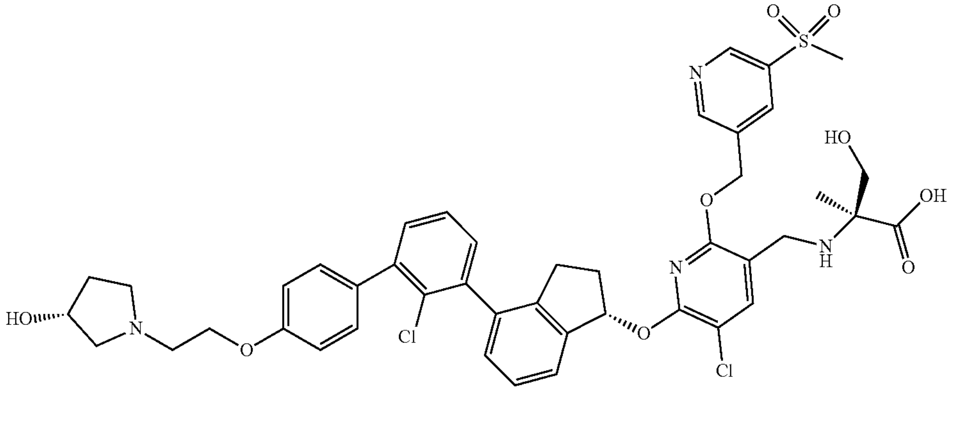

-continued
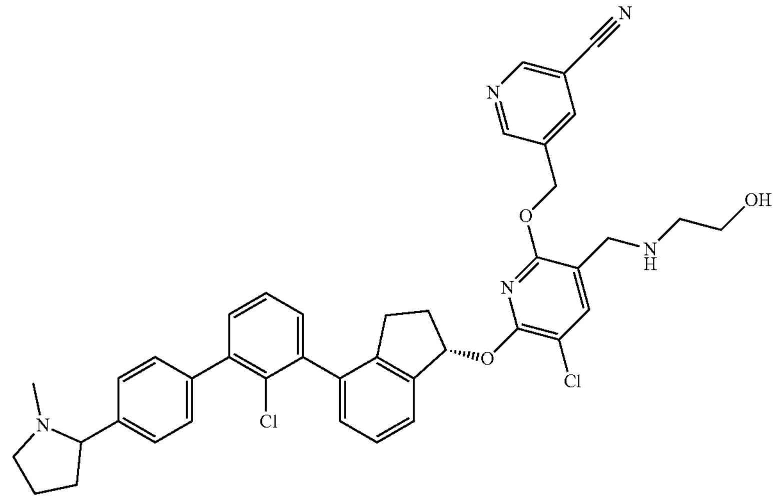
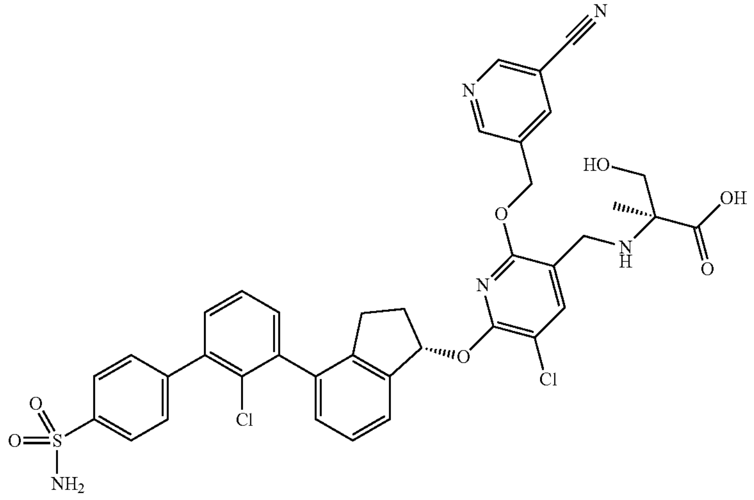
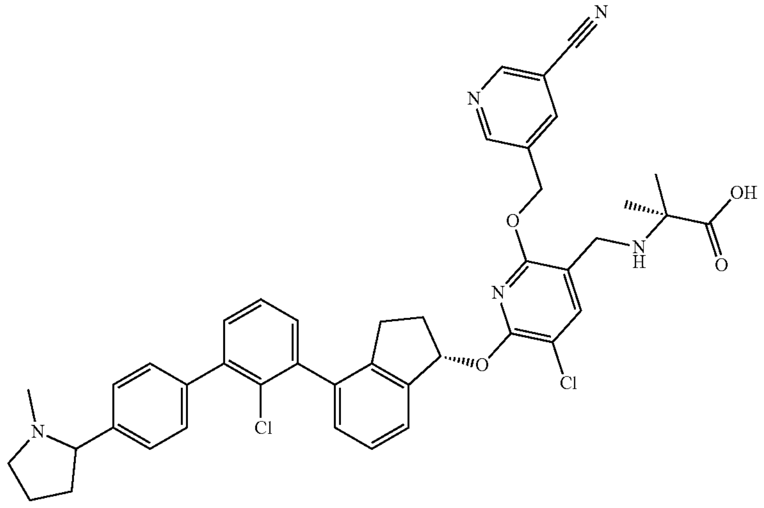

-continued
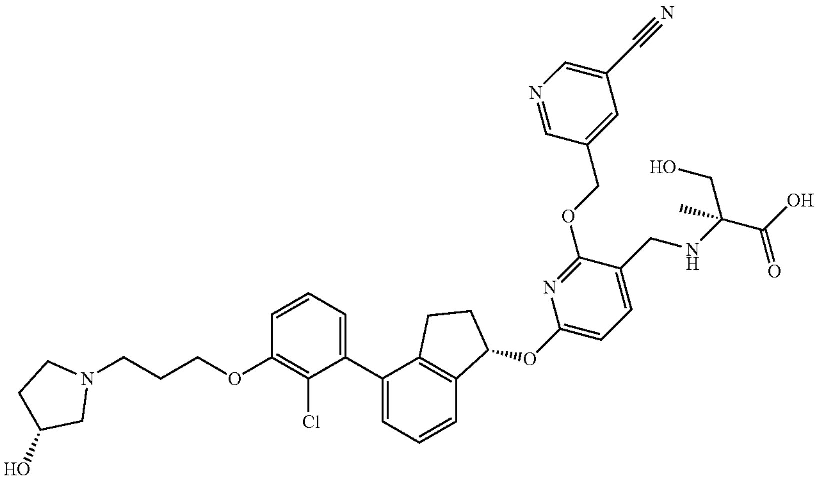
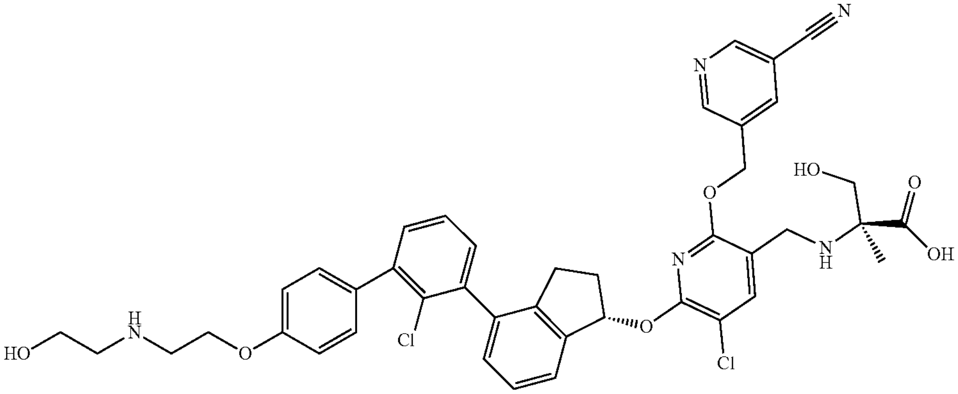
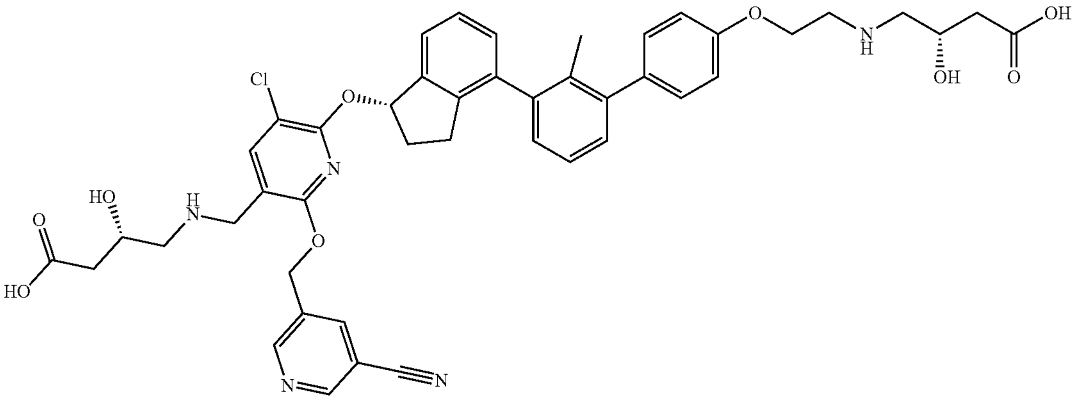
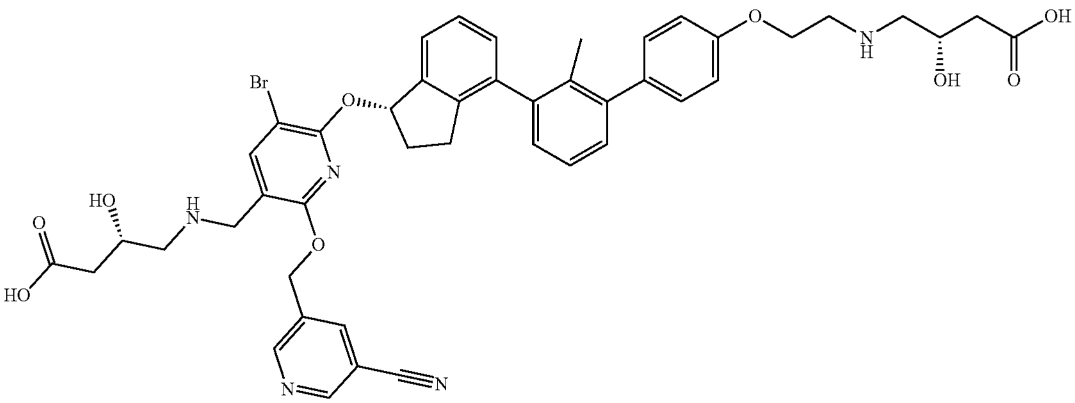

-continued
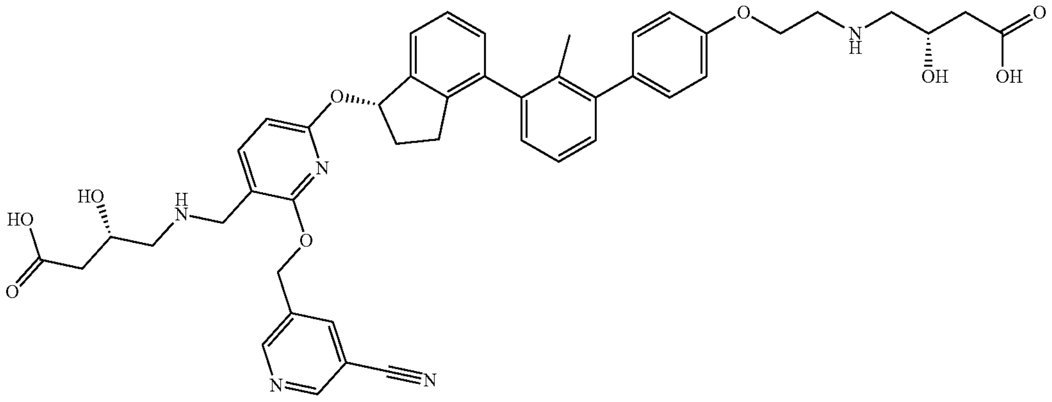 [SMILES: Cc1c(-c2ccc(OCCNC[C@@H](O)CC(=O)O)cc2)cccc1-c1cccc2c1CC[C@@H]2Oc1ccc(CNC[C@@H](O)CC(=O)O)c(OCc2cncc(C#N)c2)n1]
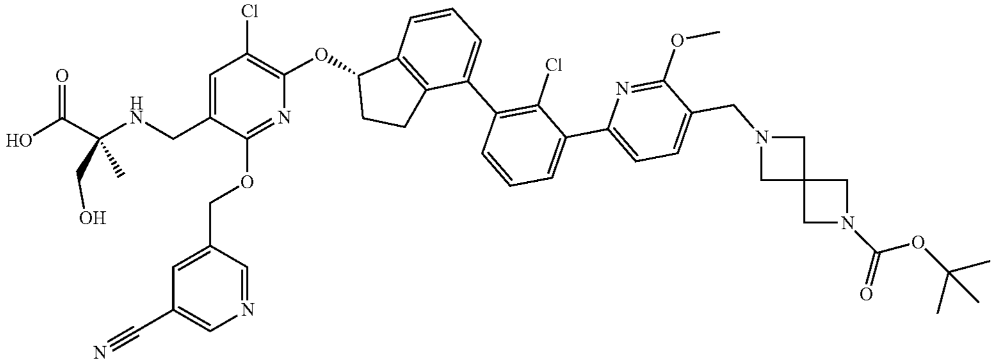
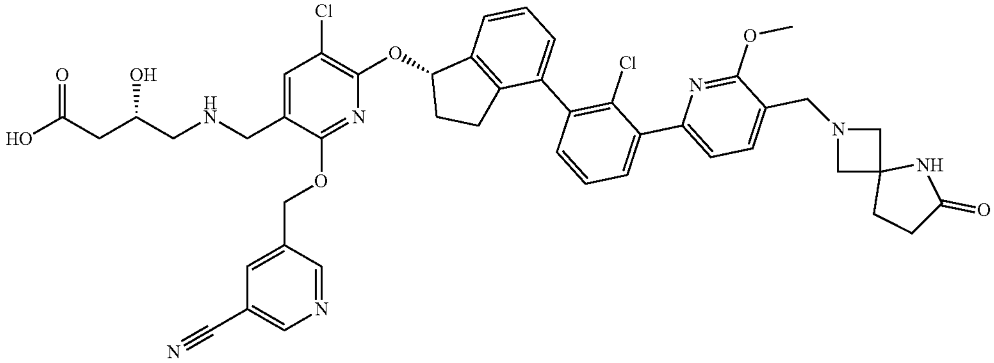
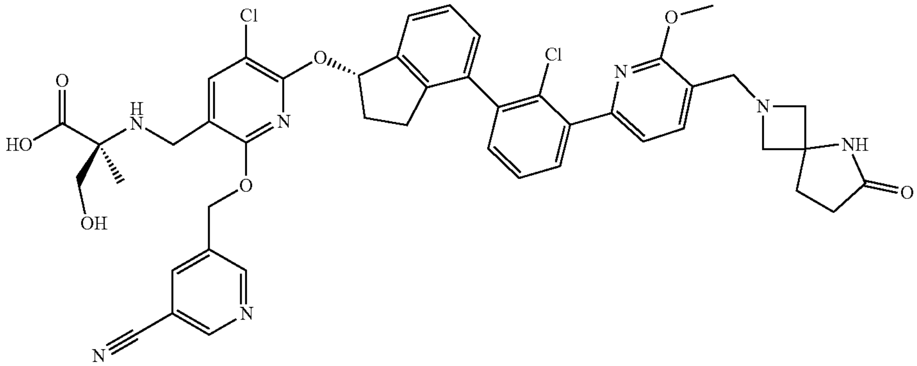

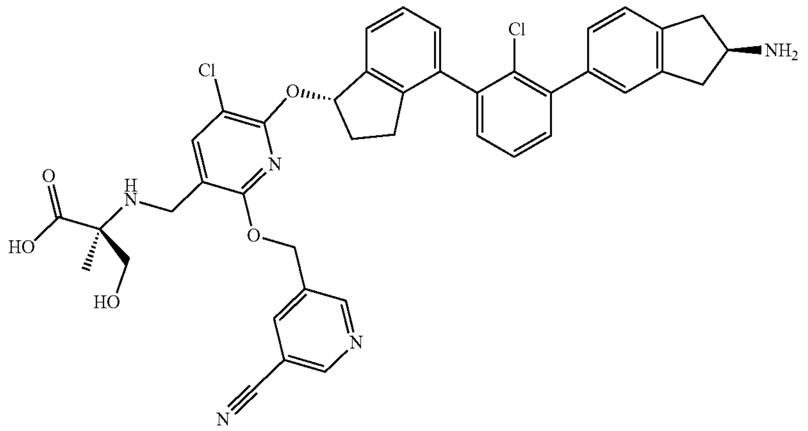
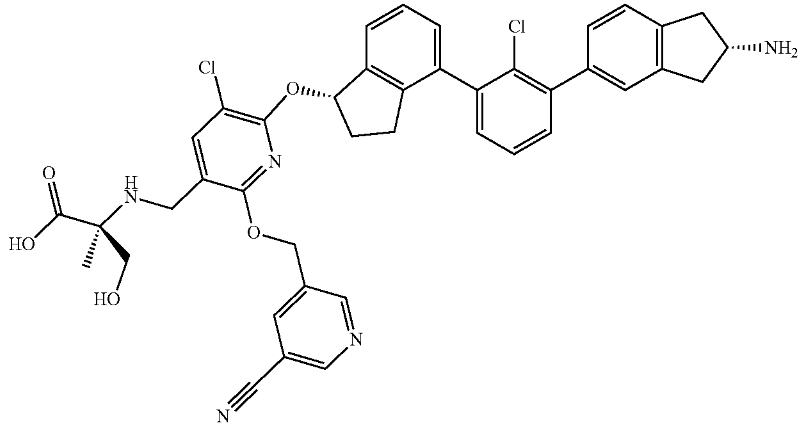
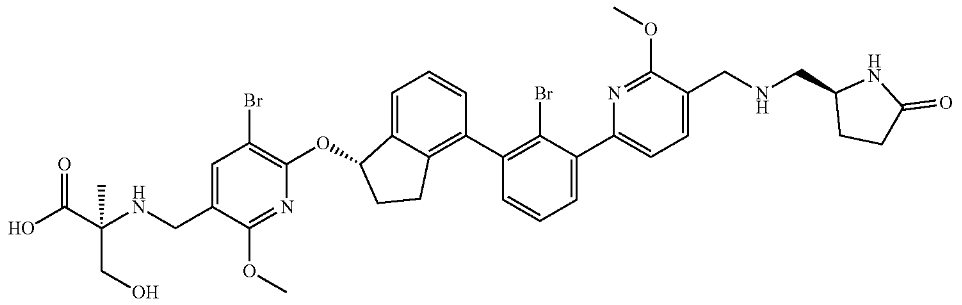
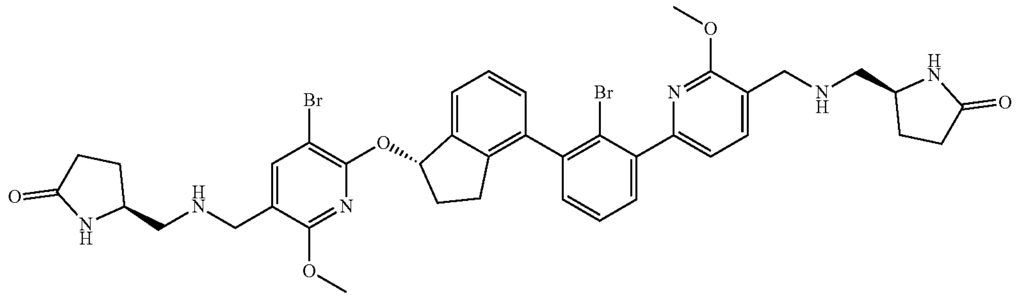

-continued
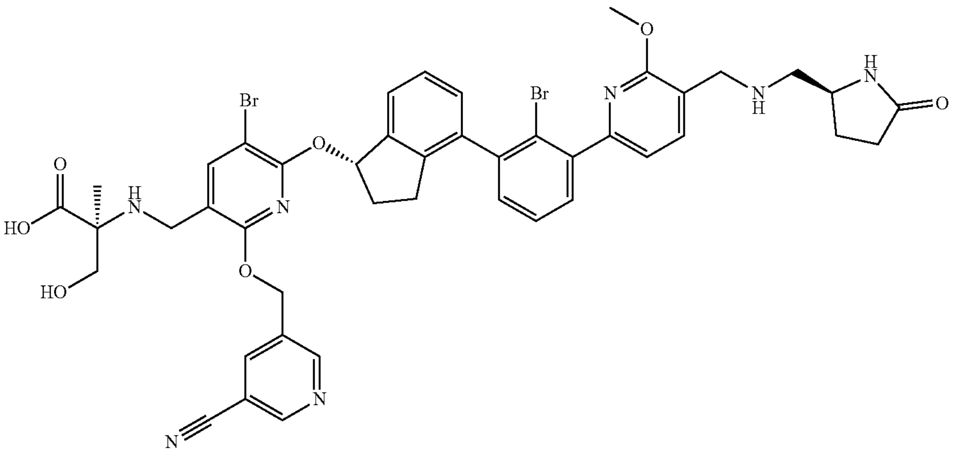
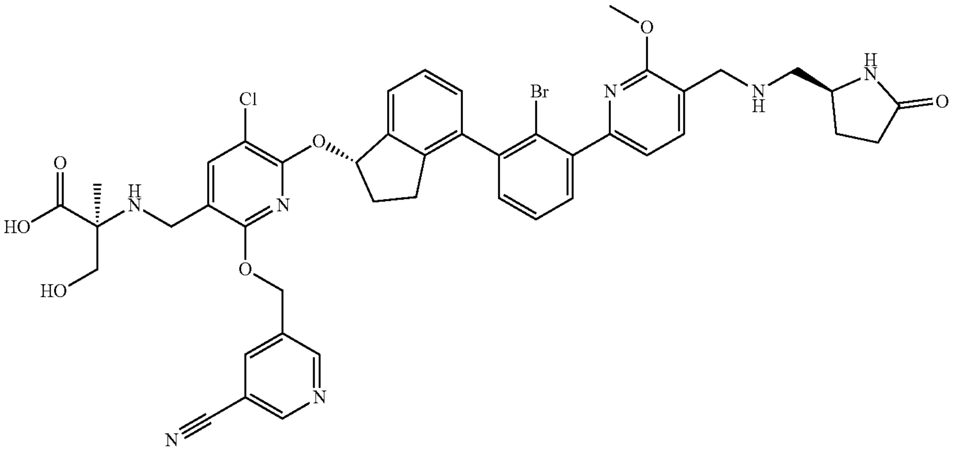
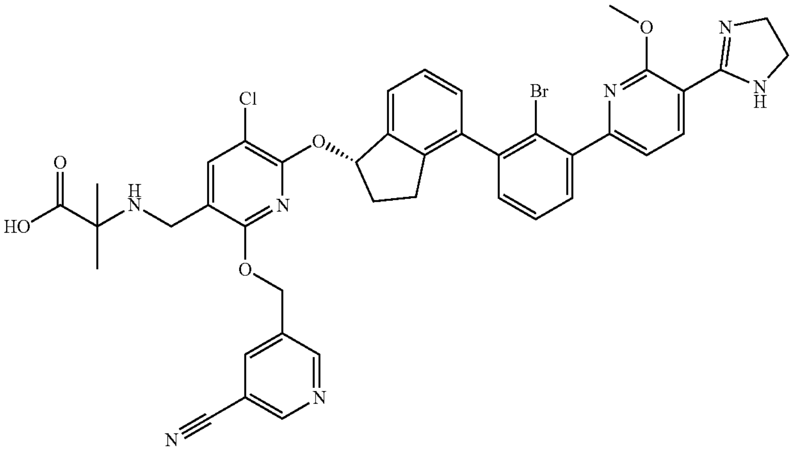

-continued
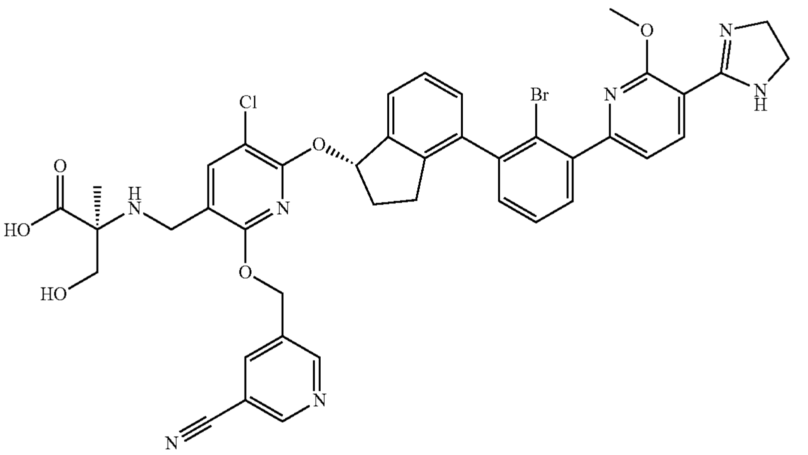
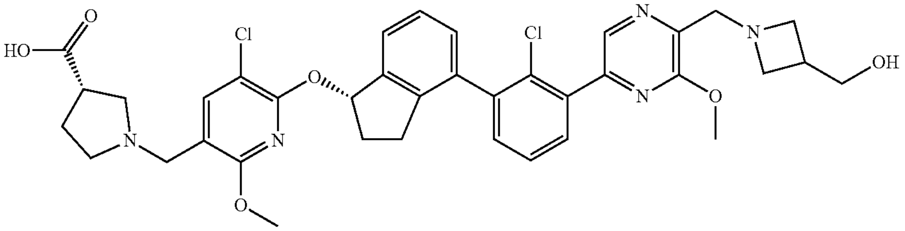
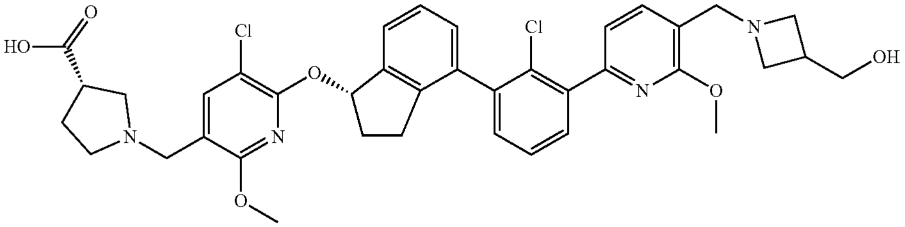
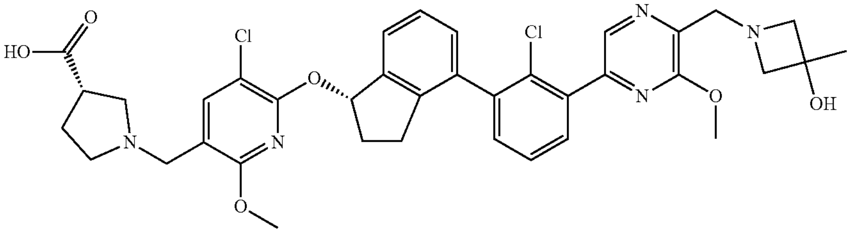
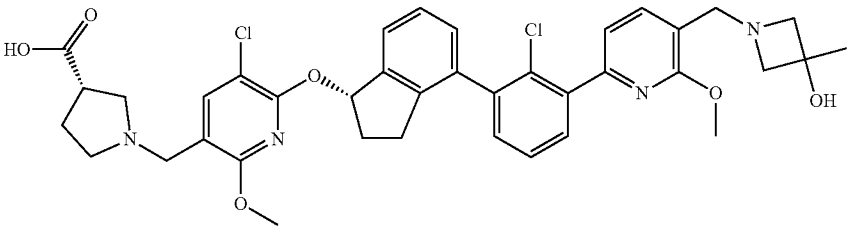
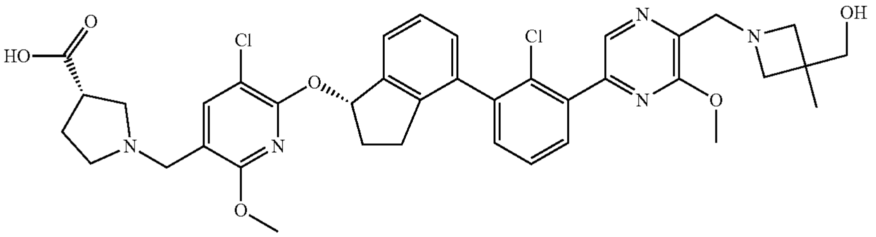

-continued
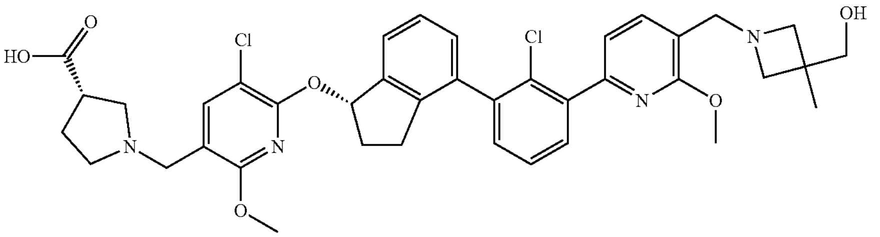
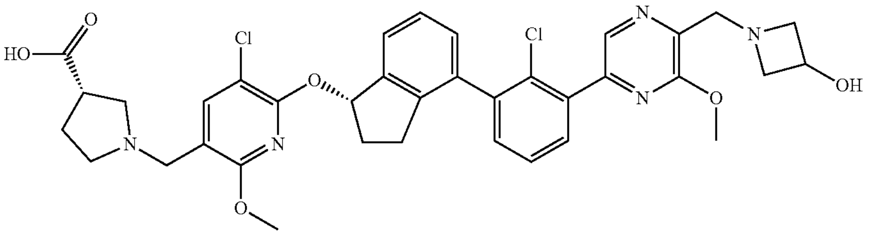
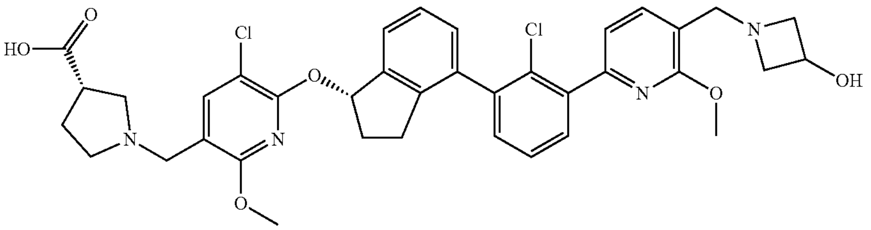
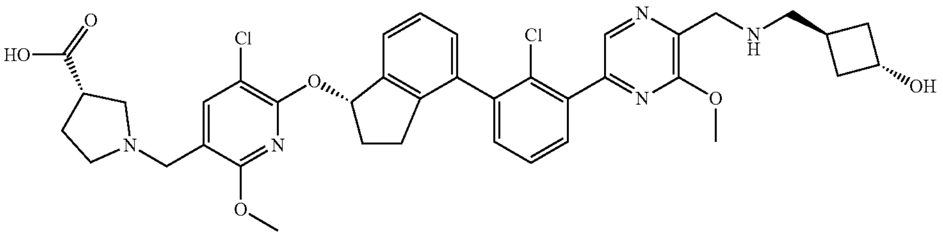
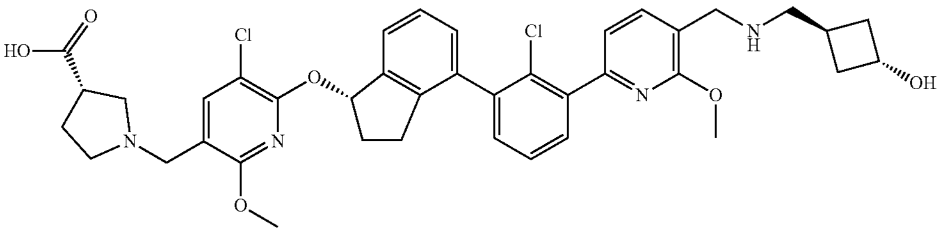
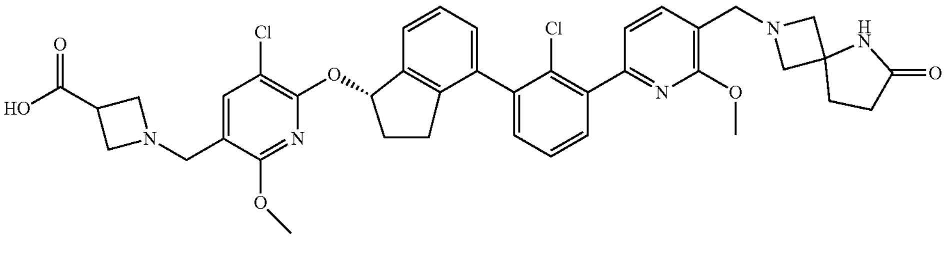
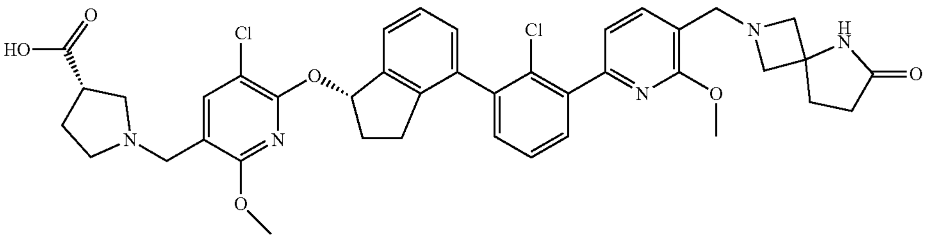

-continued
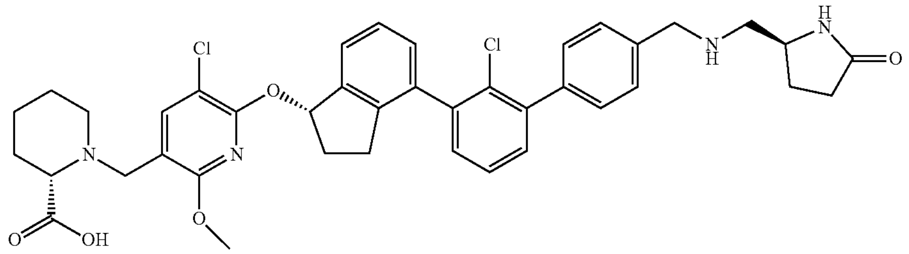
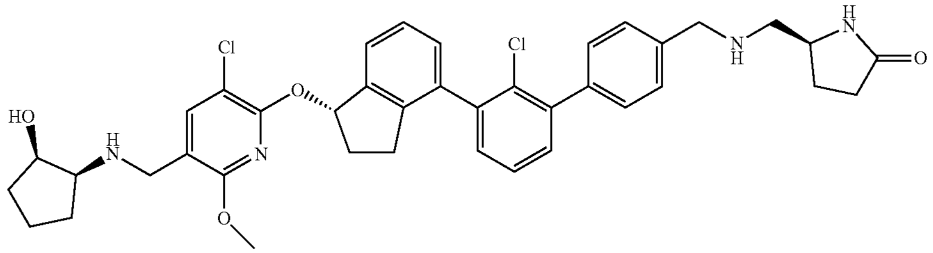
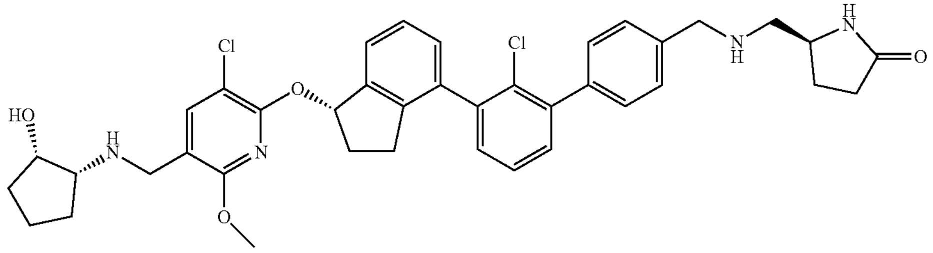
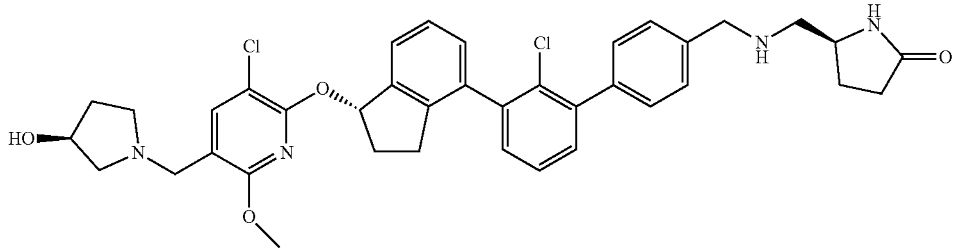
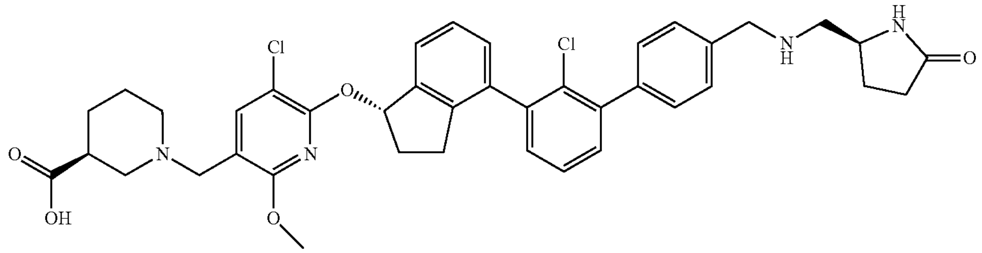
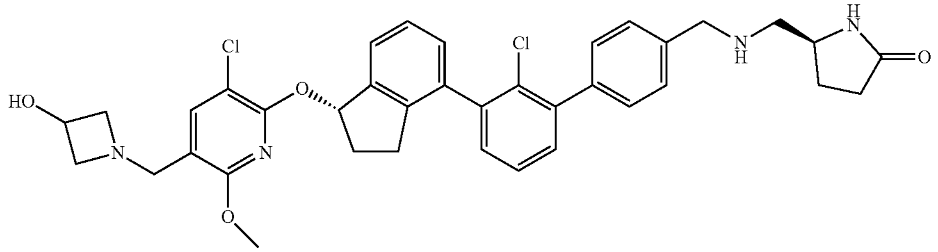

-continued
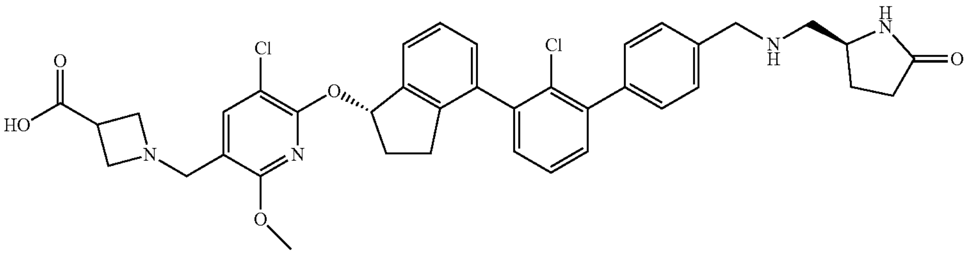
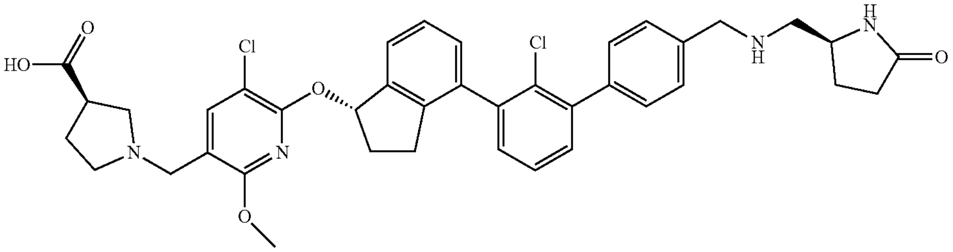
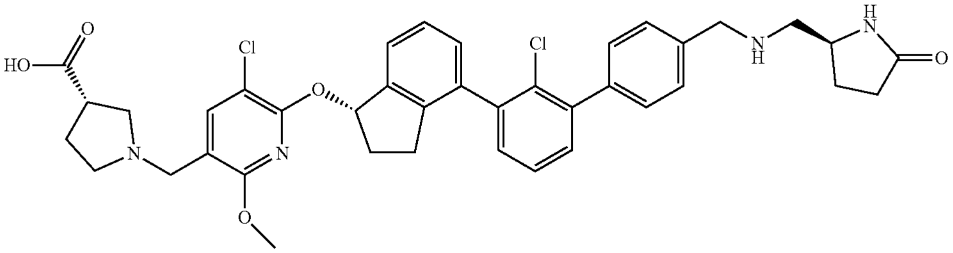
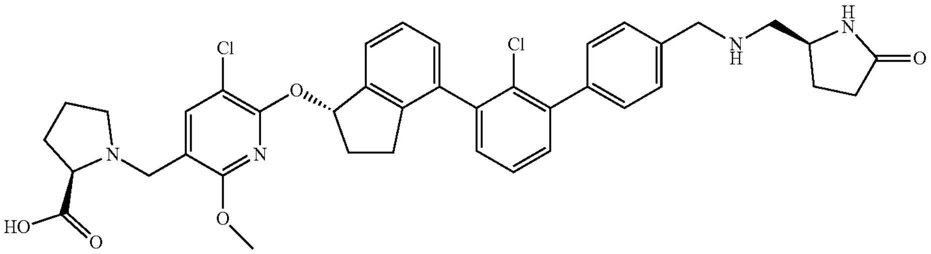
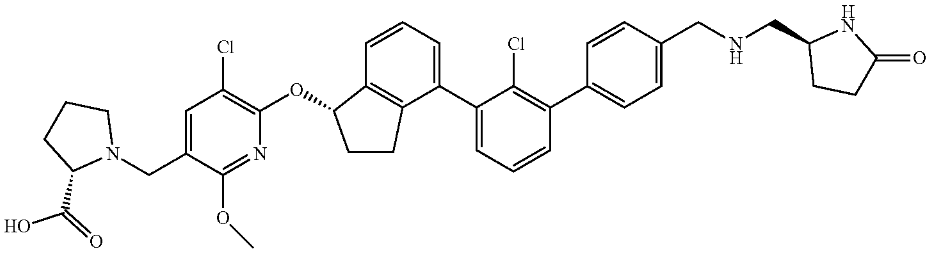
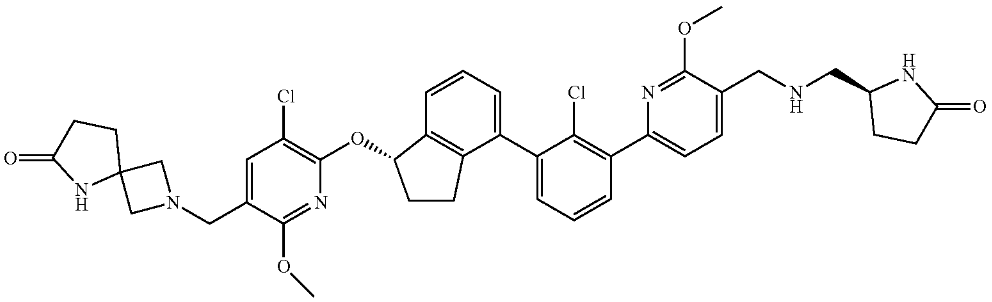

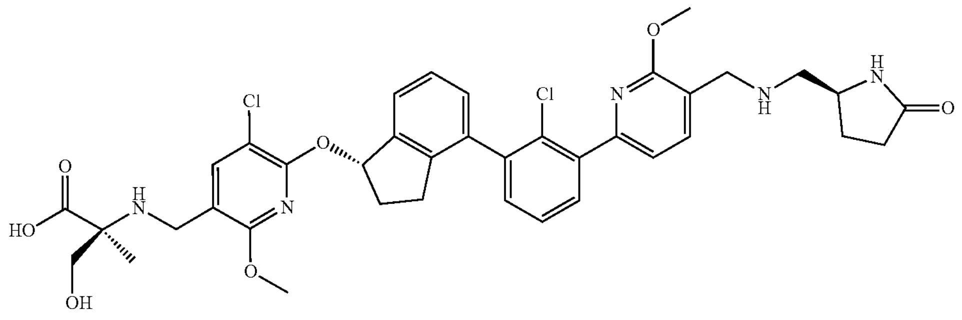
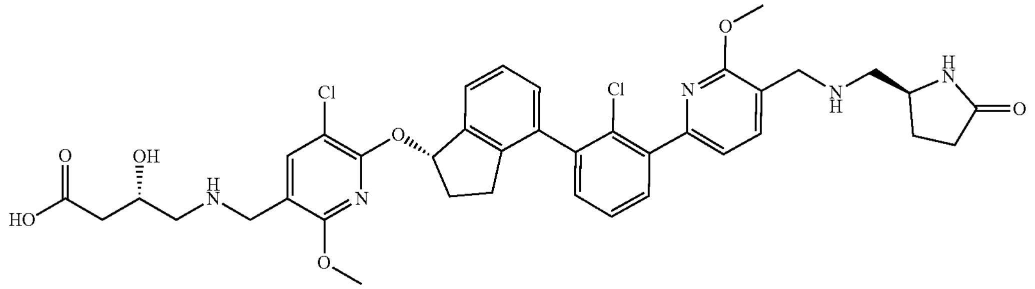
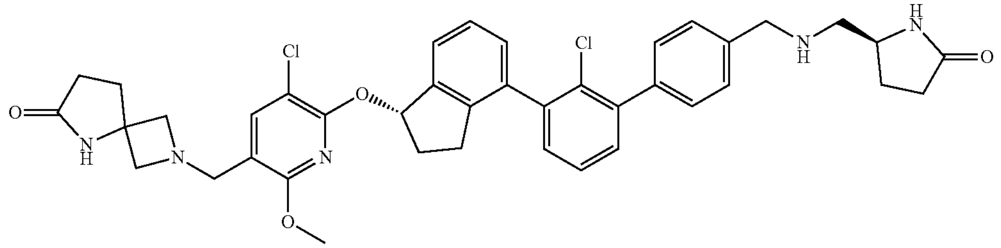
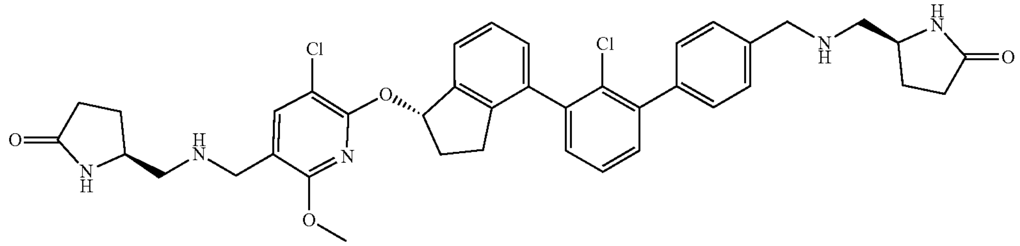
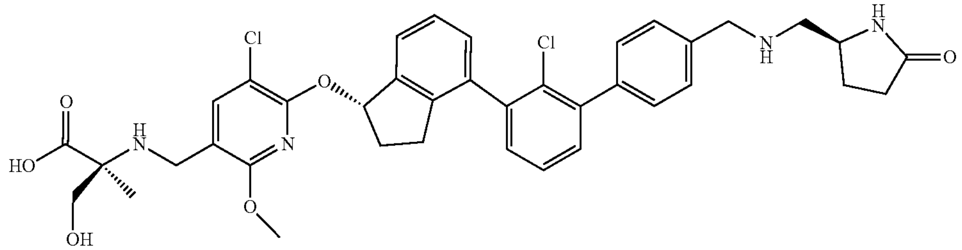
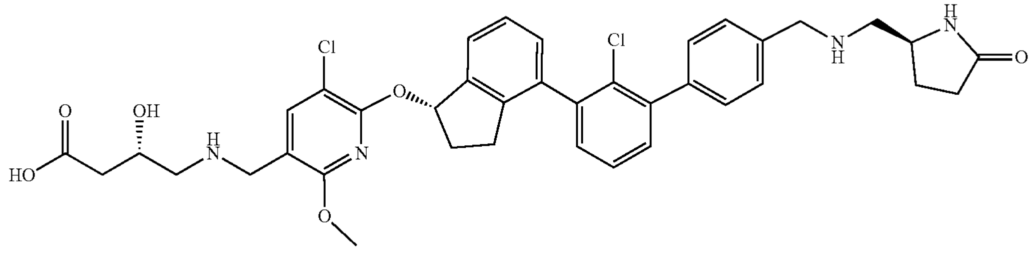

-continued
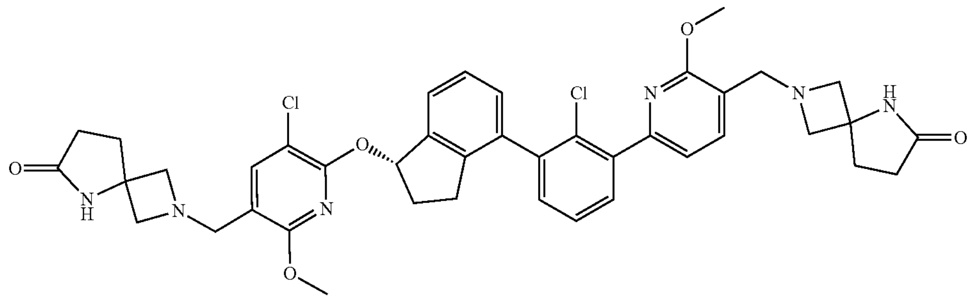
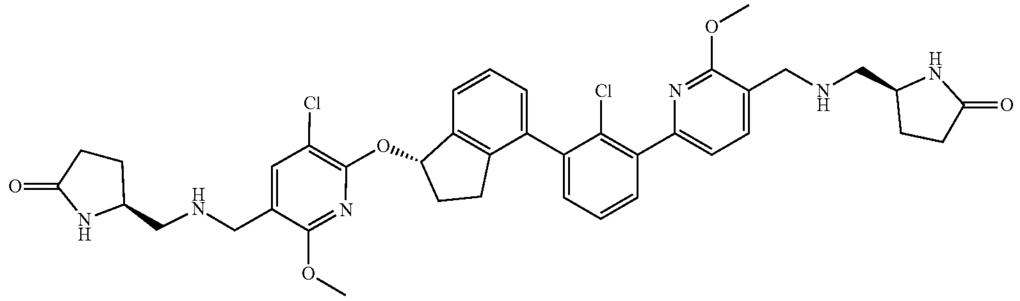
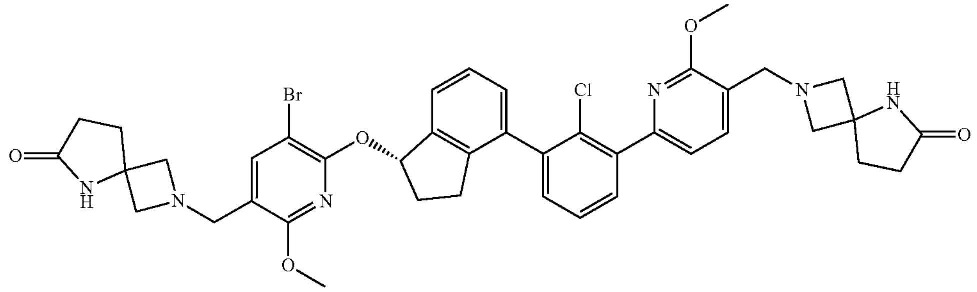
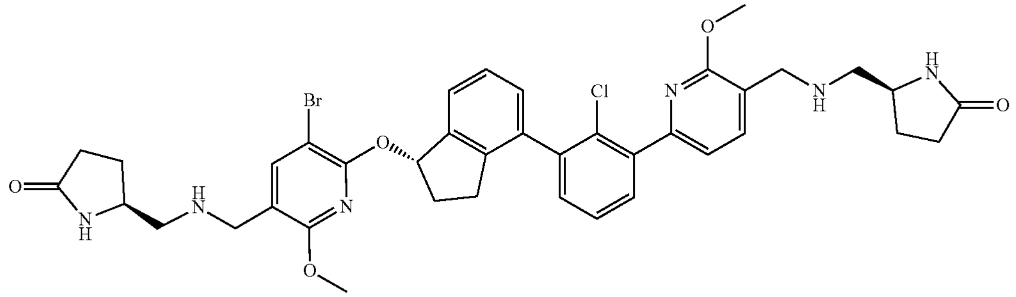
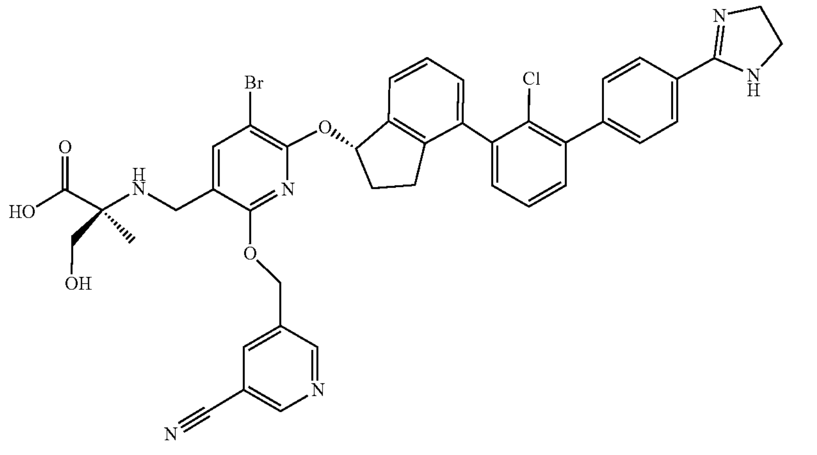

-continued
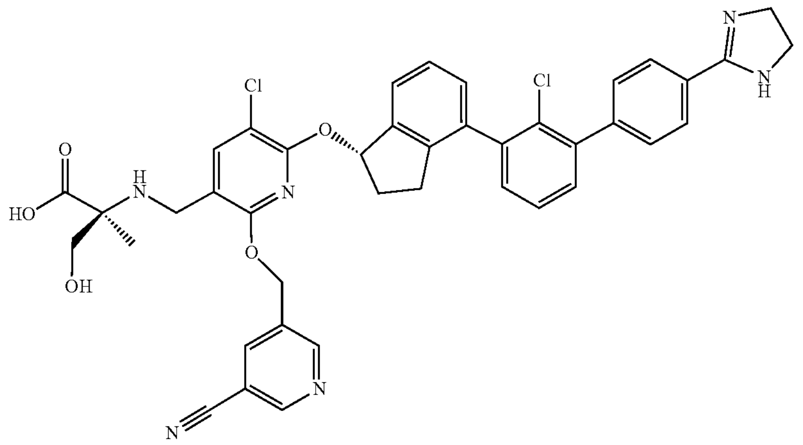
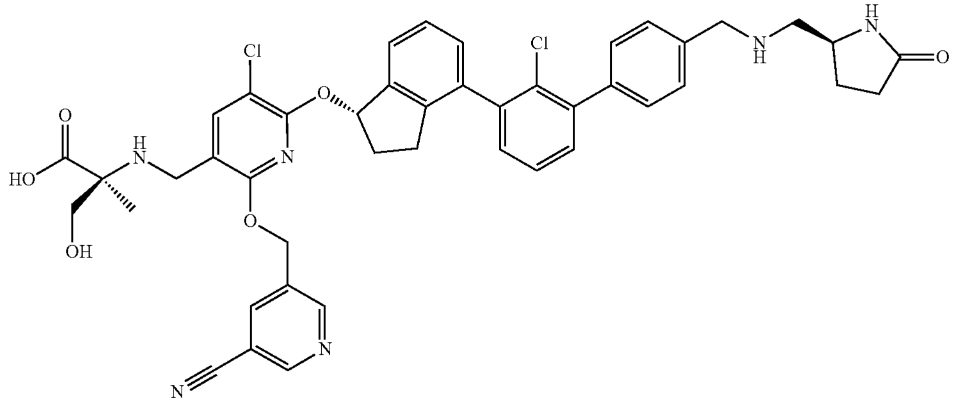
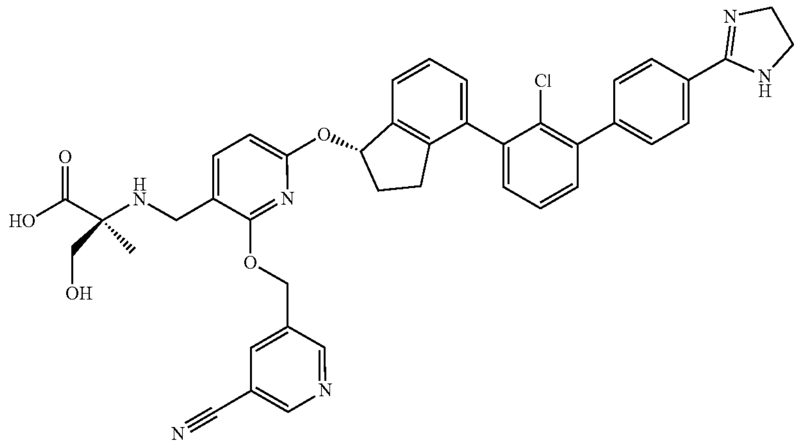
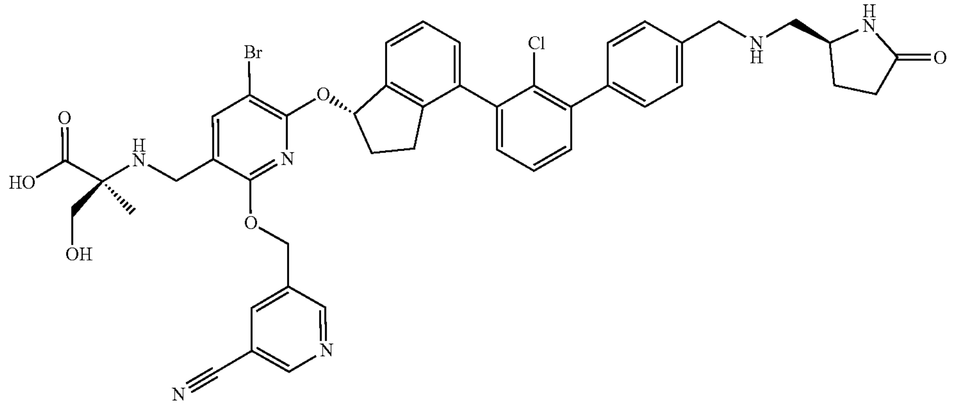

-continued
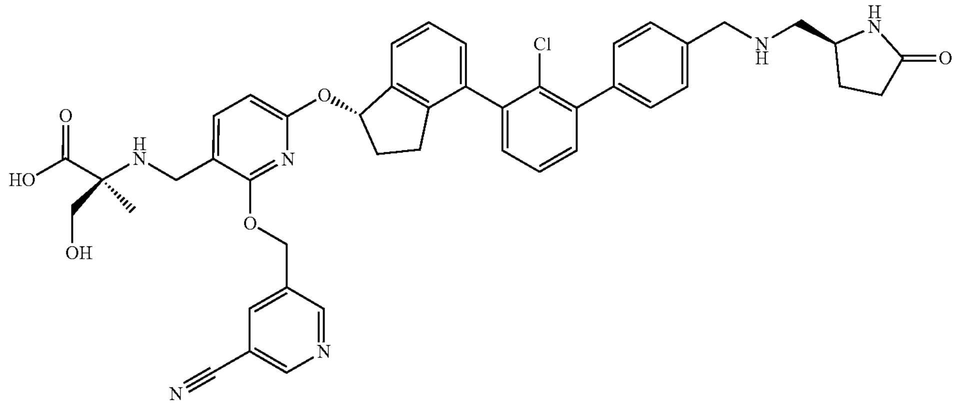
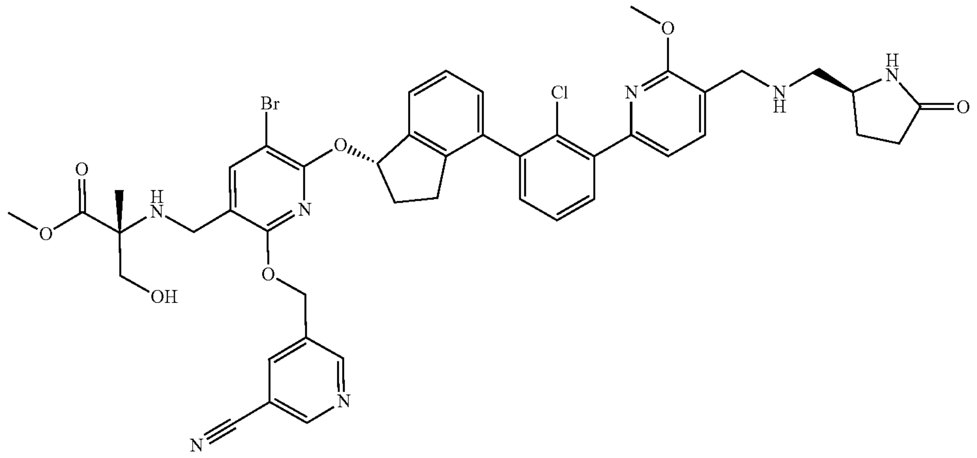
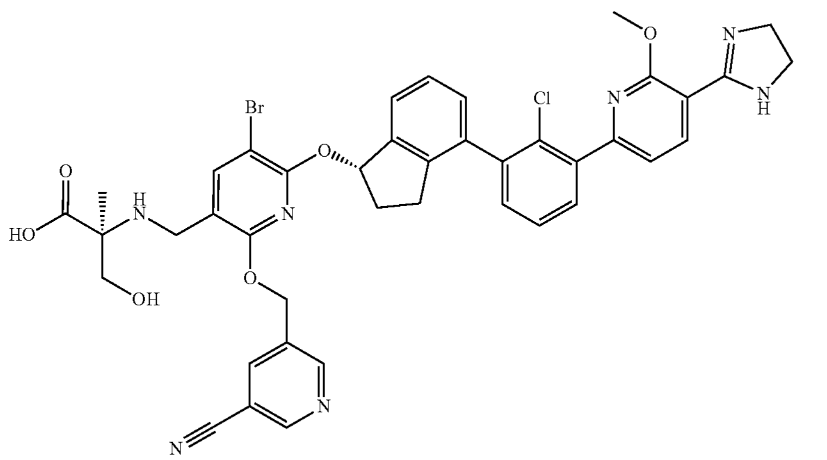

-continued
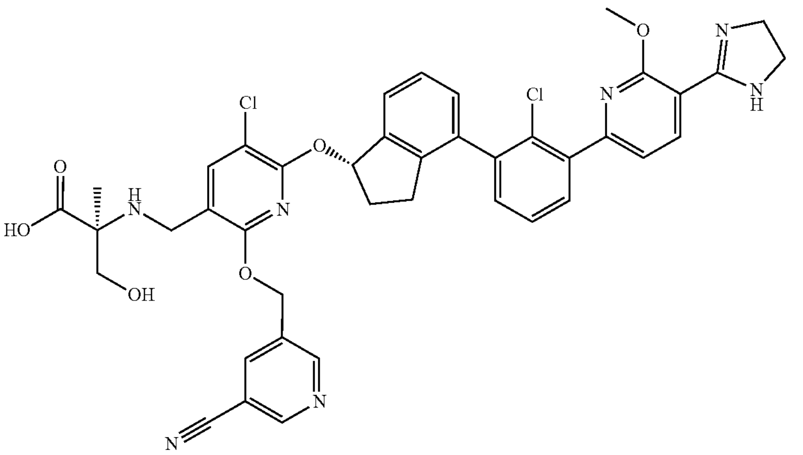
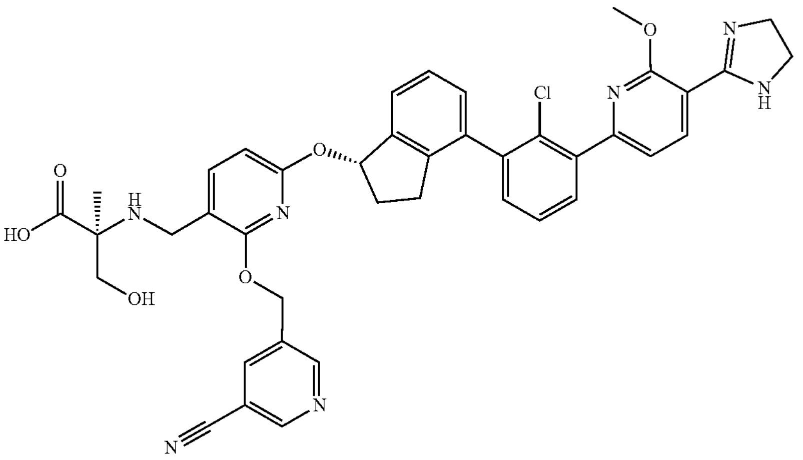
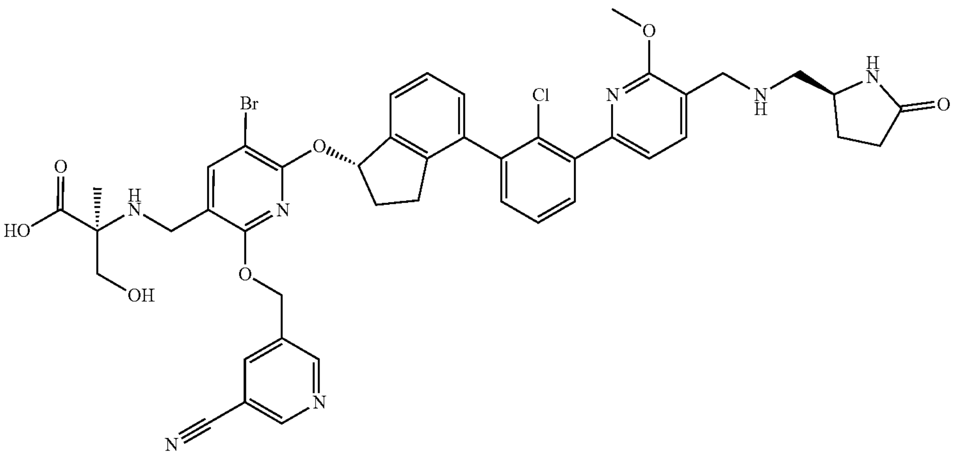

-continued
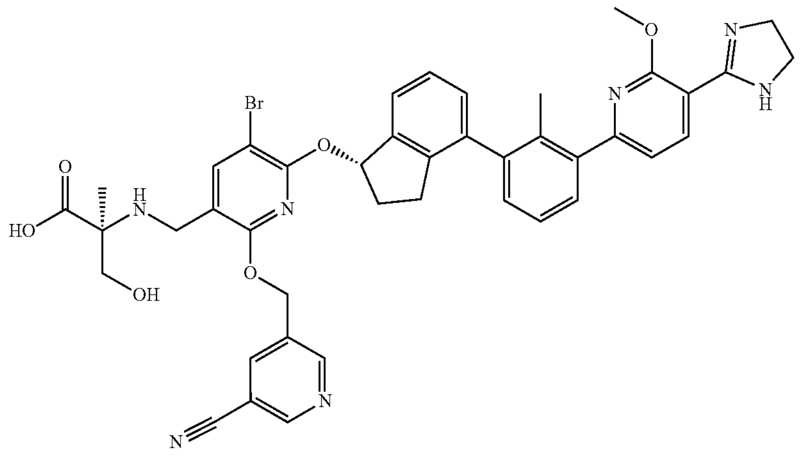
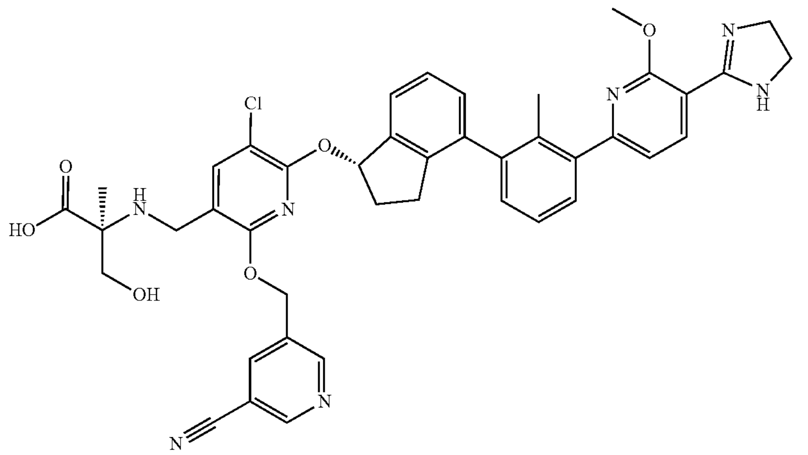
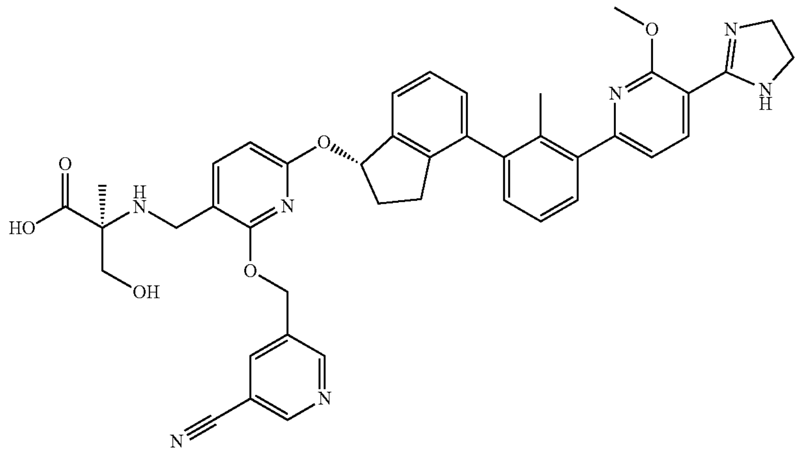

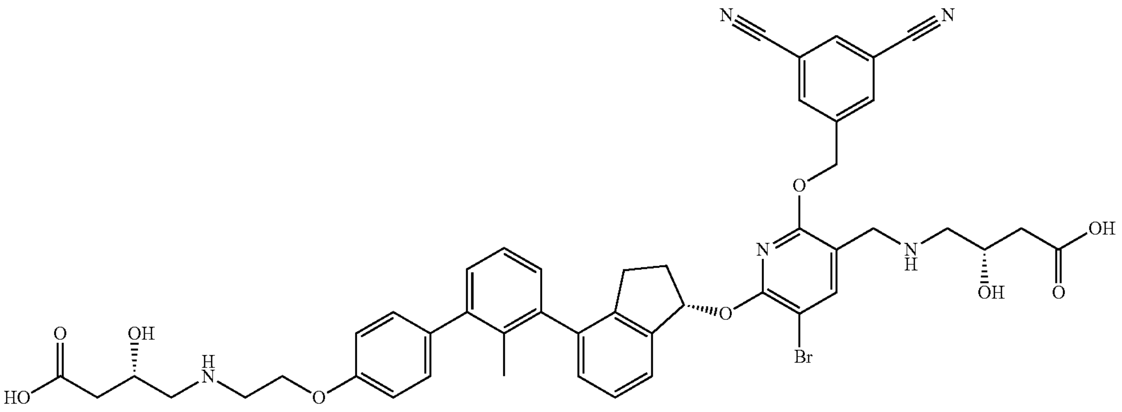
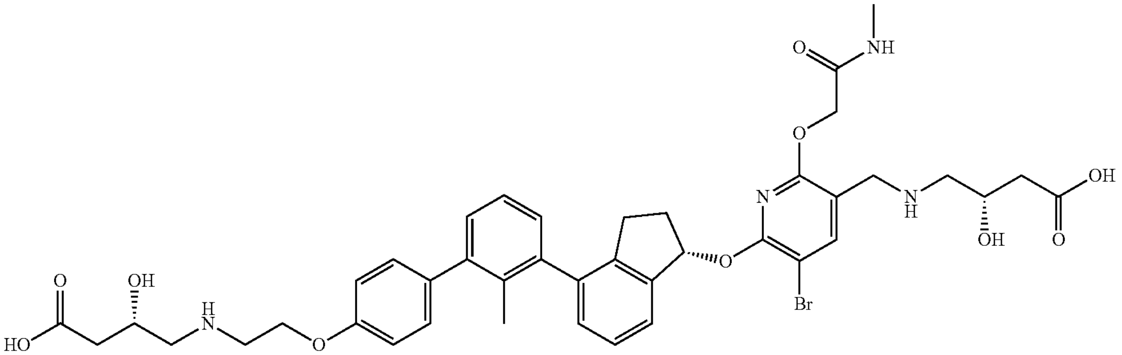
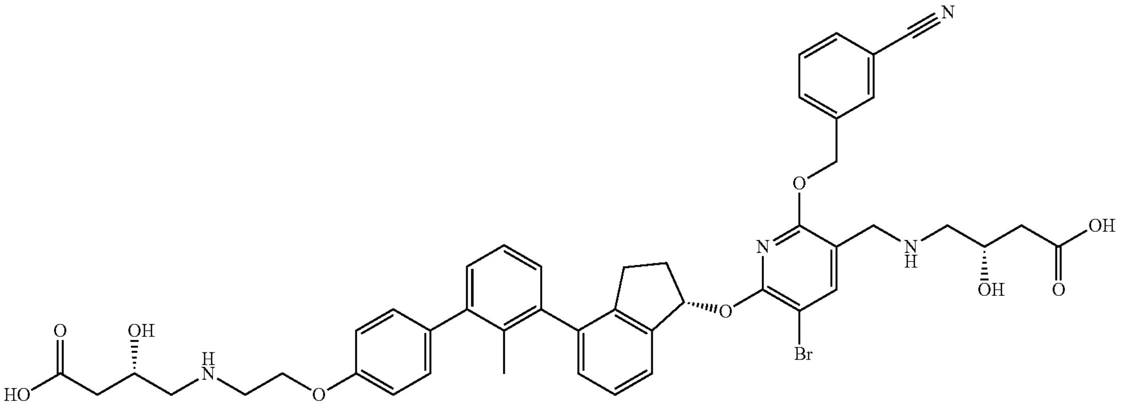
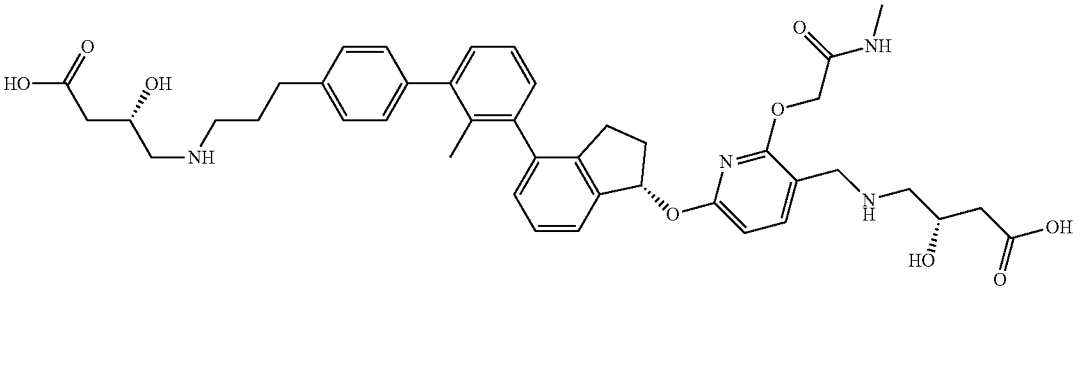

-continued
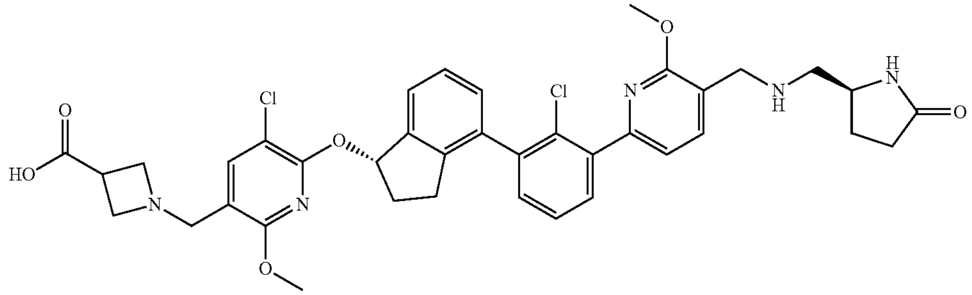
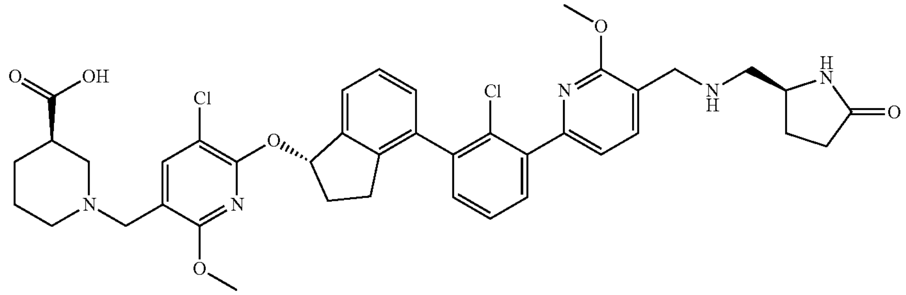
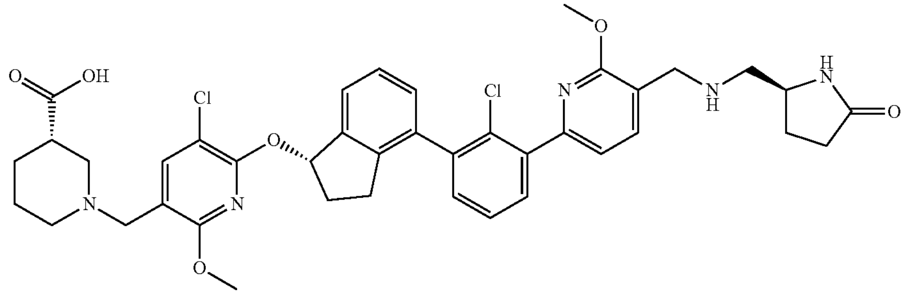
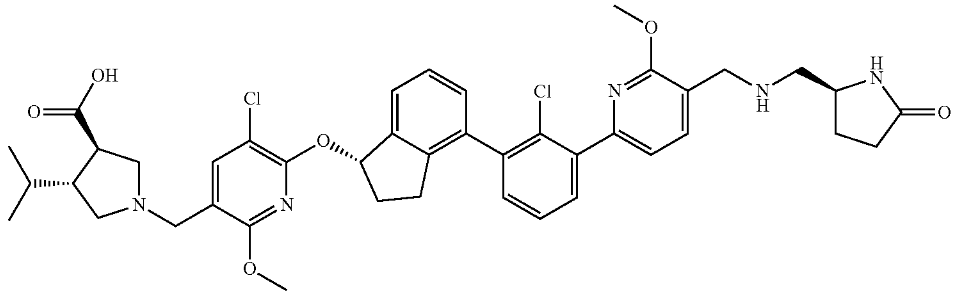
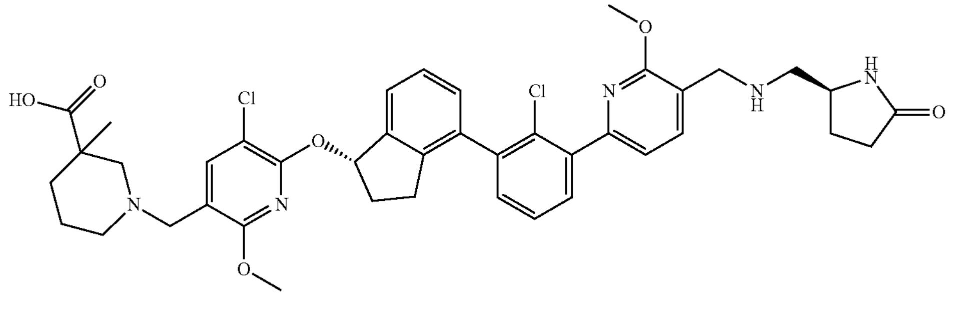

-continued
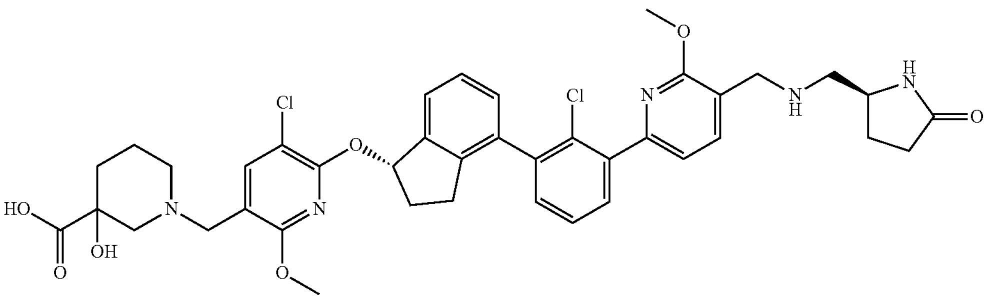
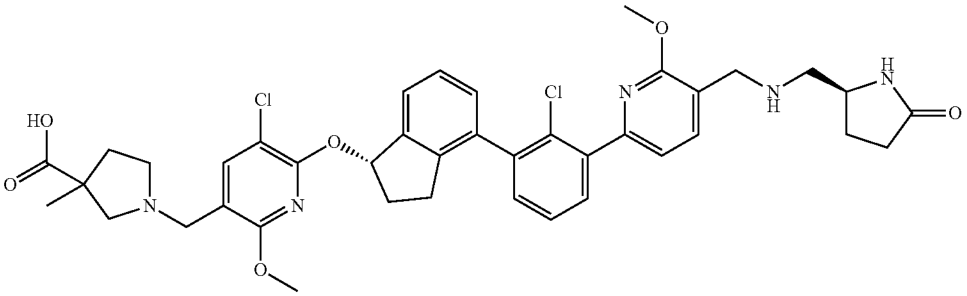
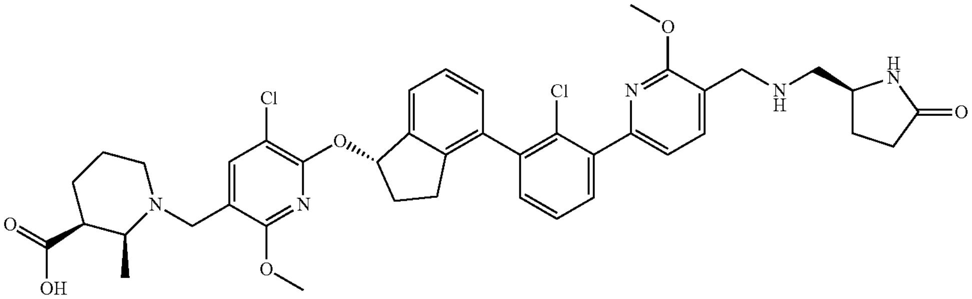
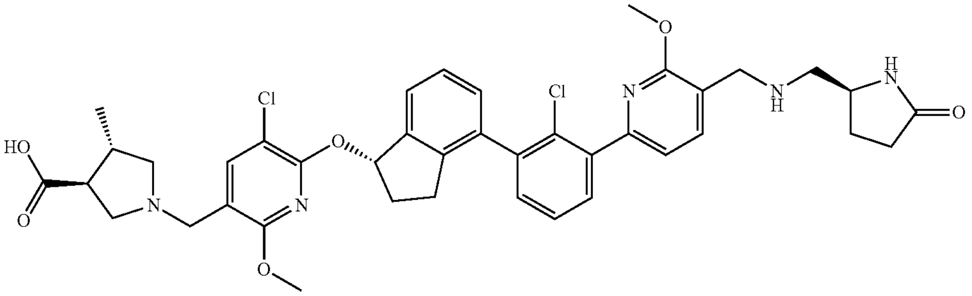
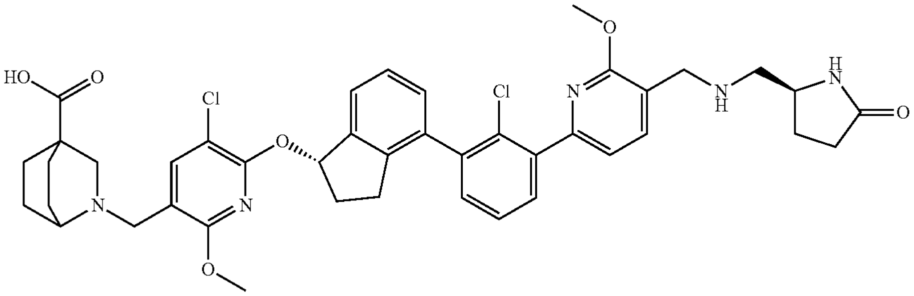

-continued
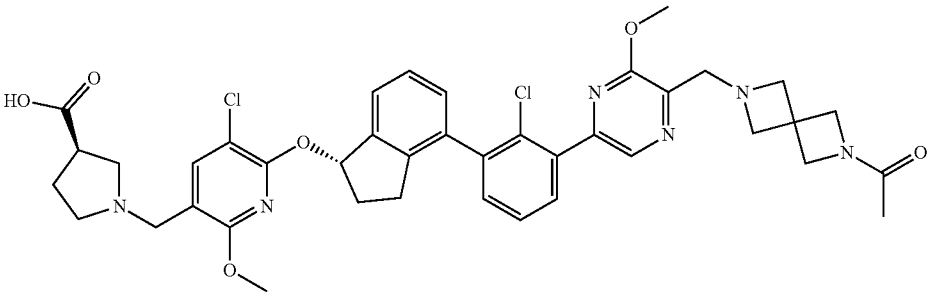
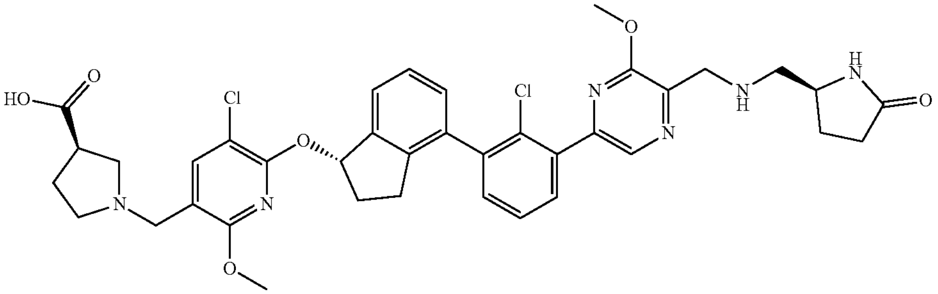
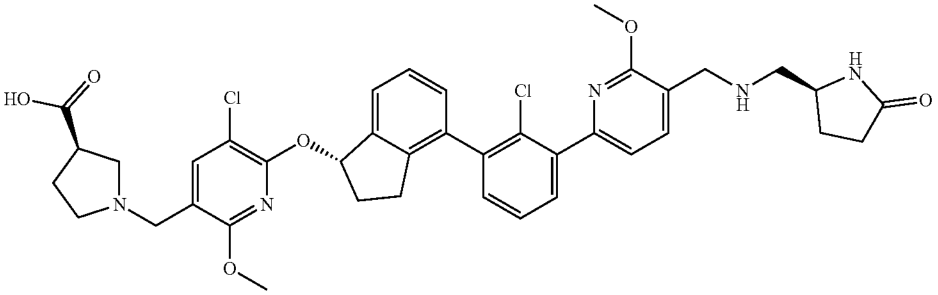
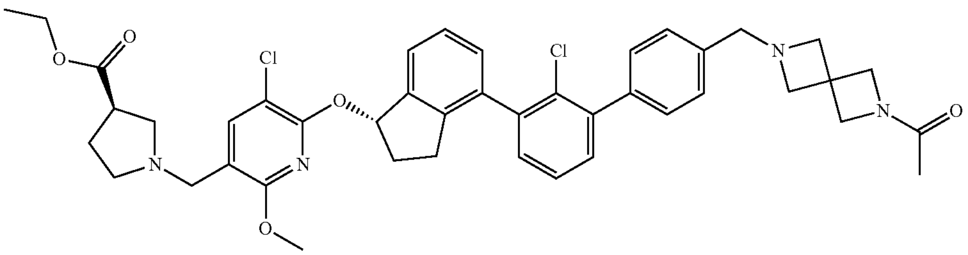
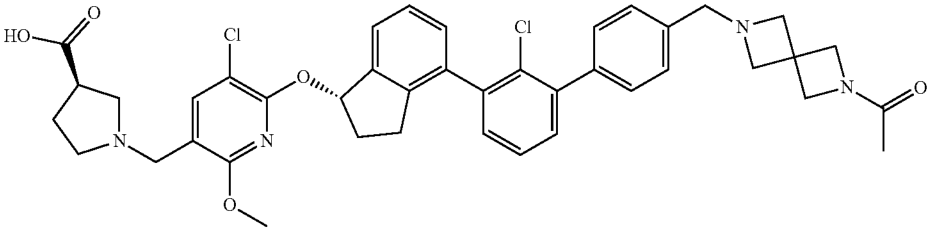
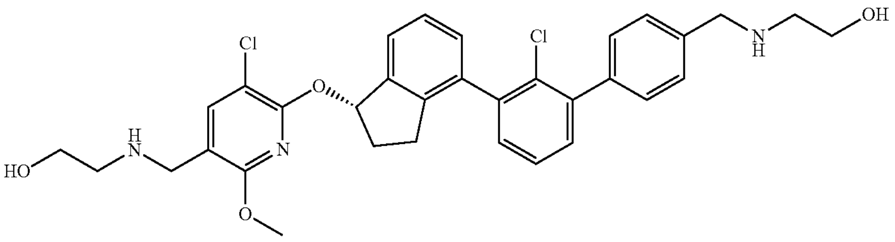

-continued
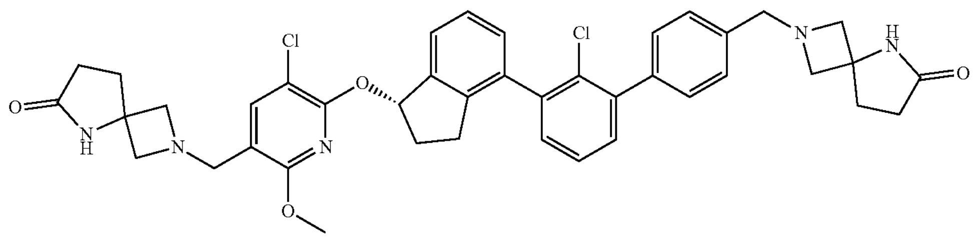
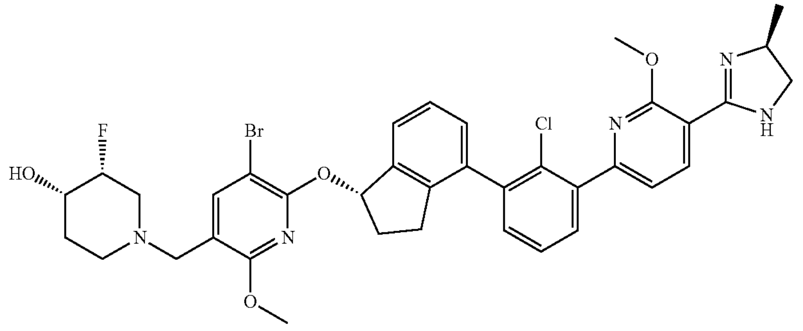
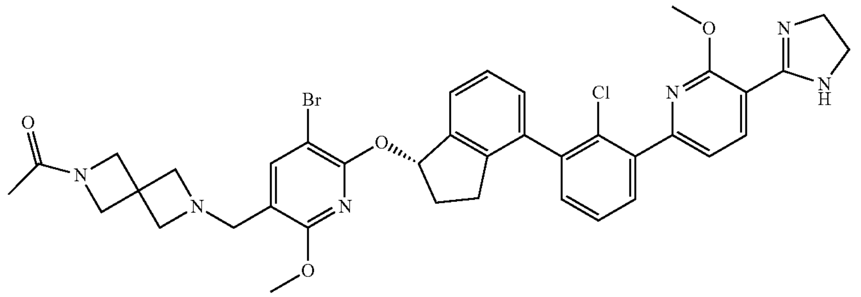
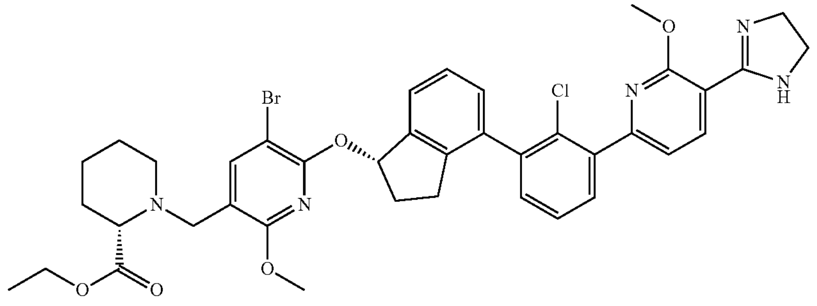
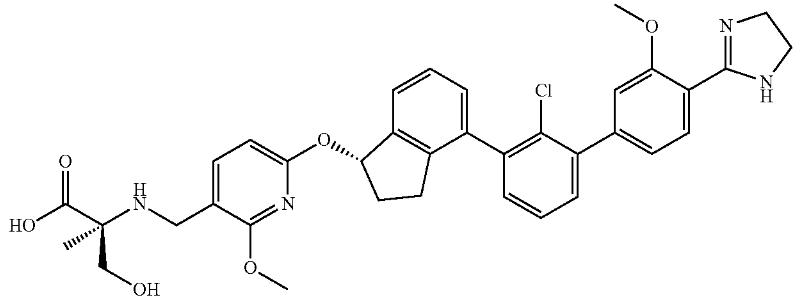

-continued
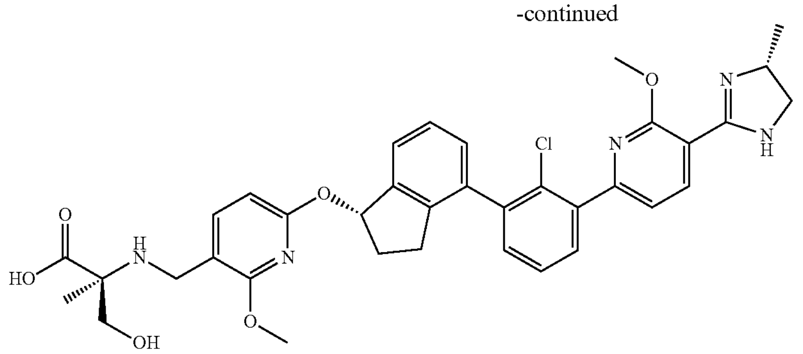
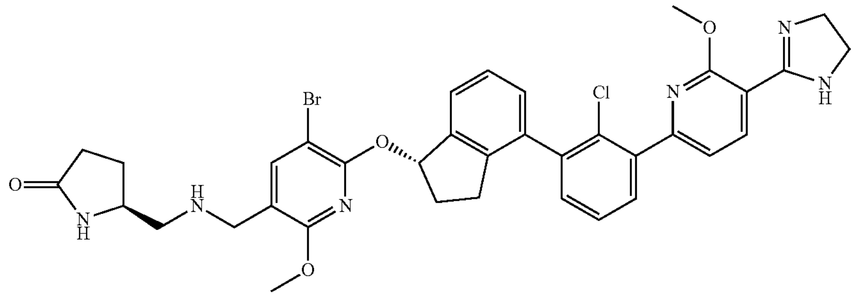
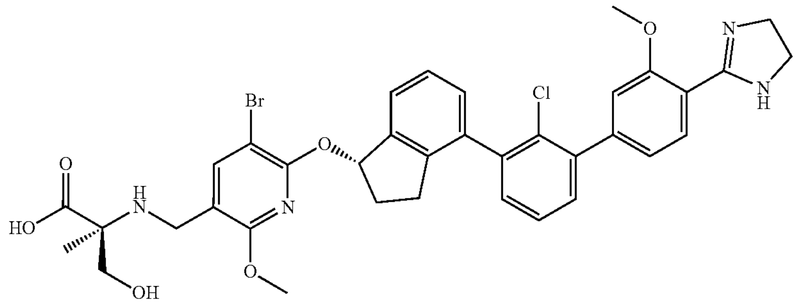
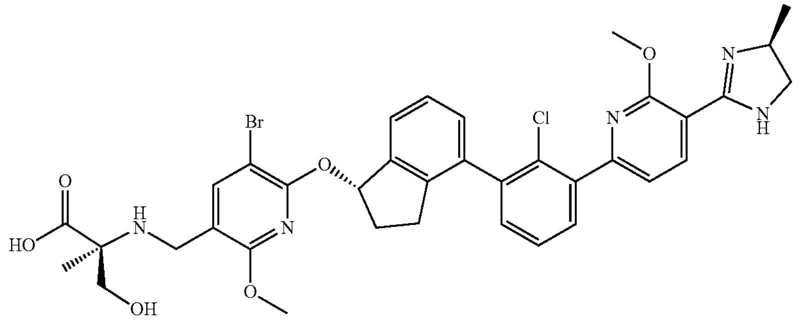
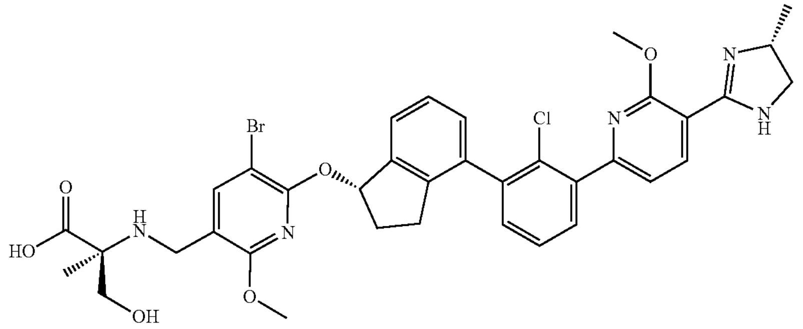

-continued
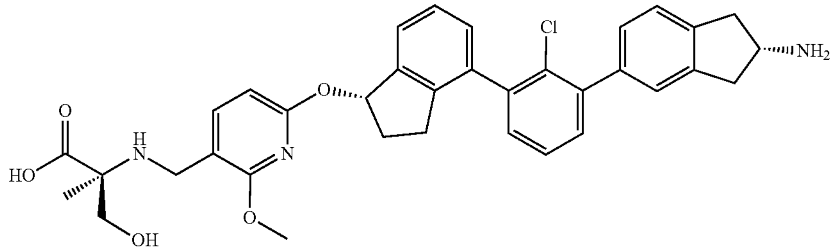
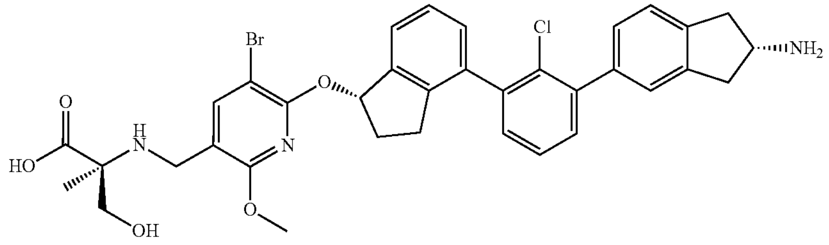
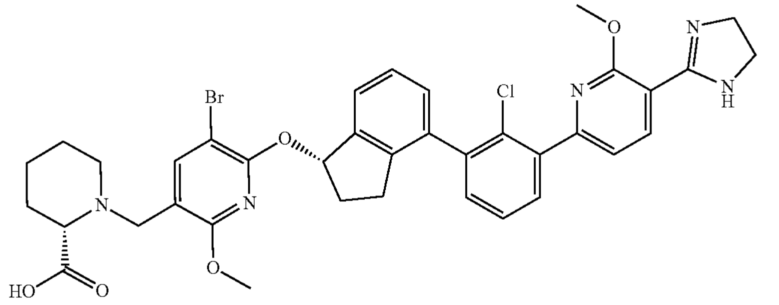
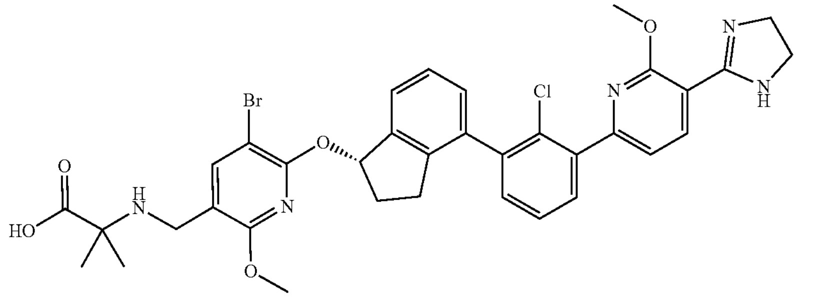
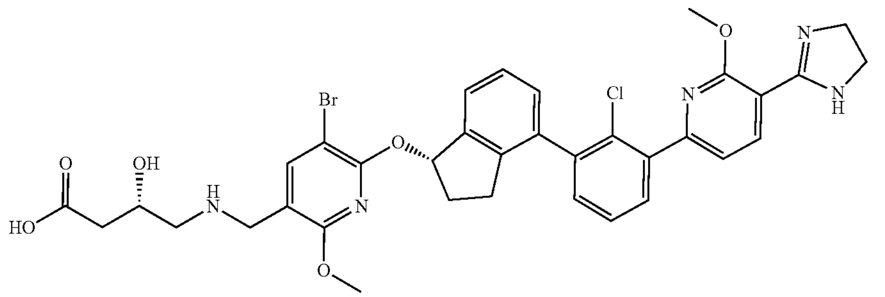
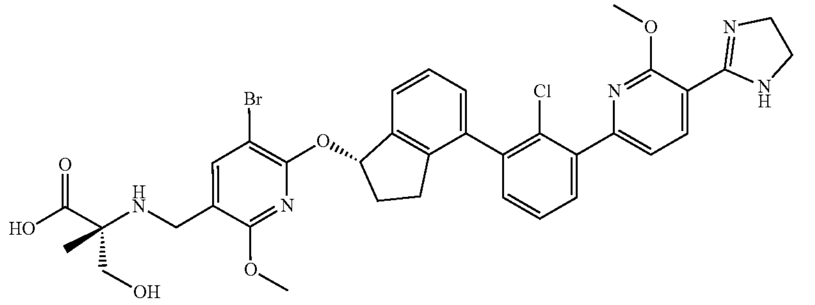

-continued
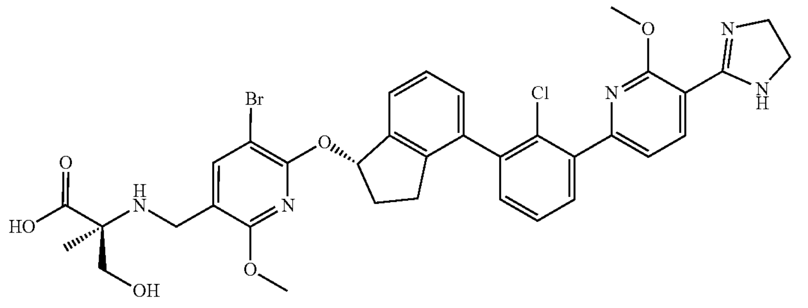
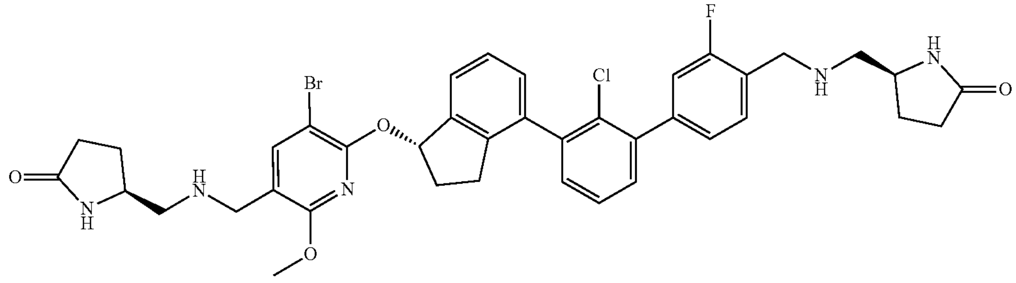
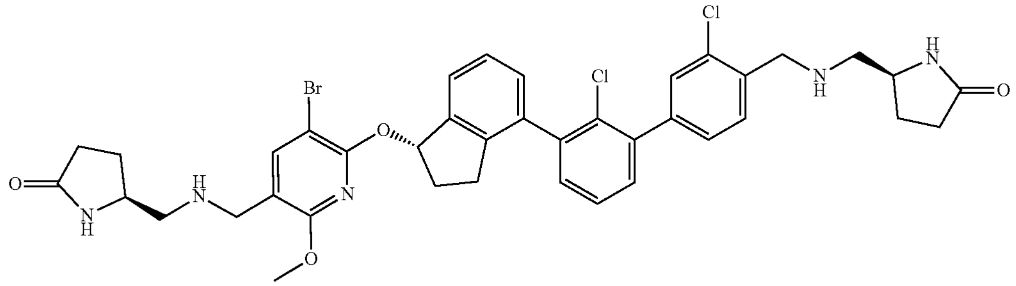
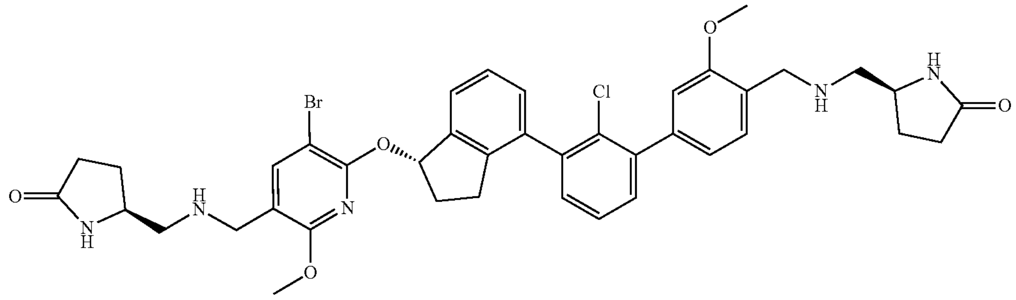
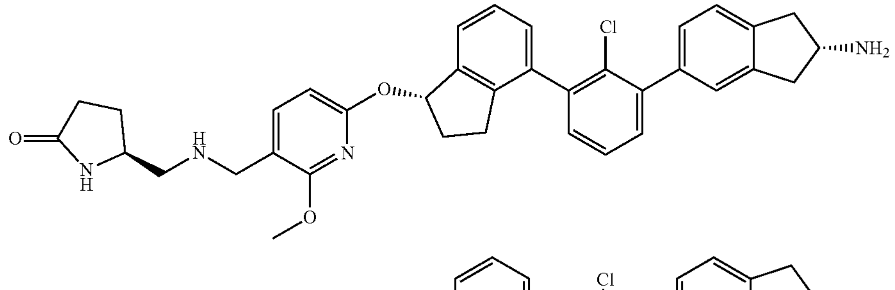
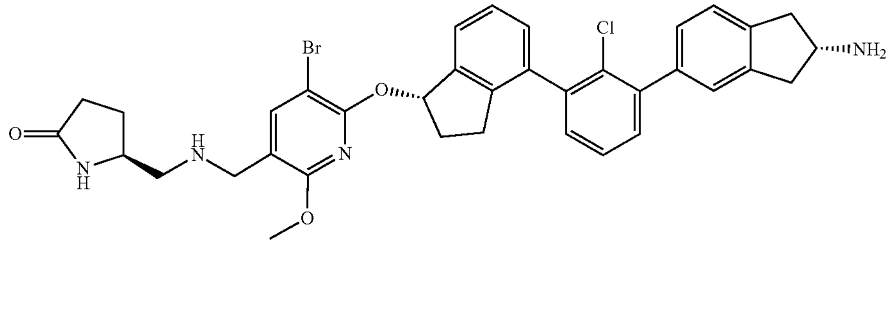

-continued
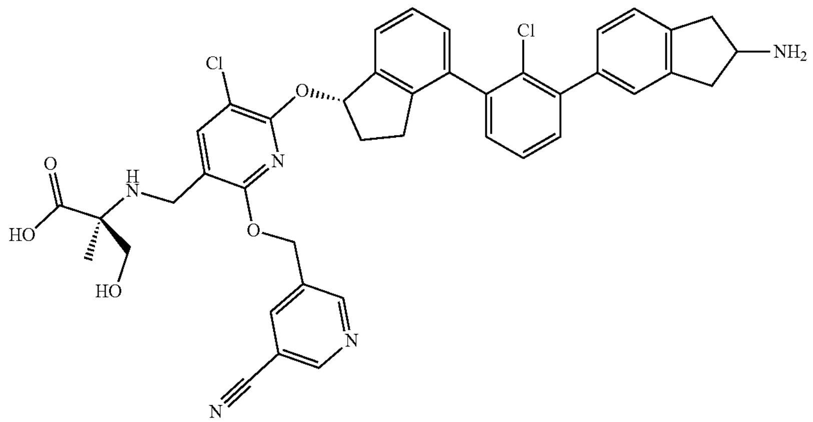
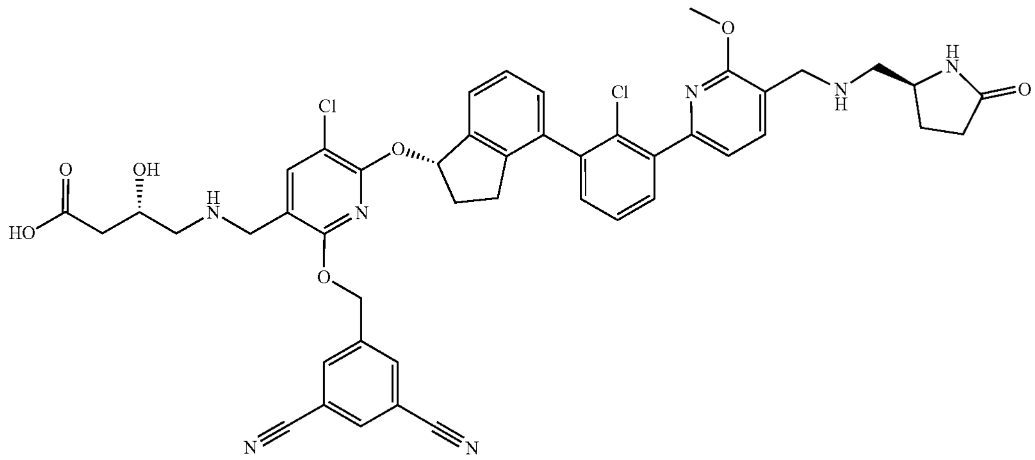
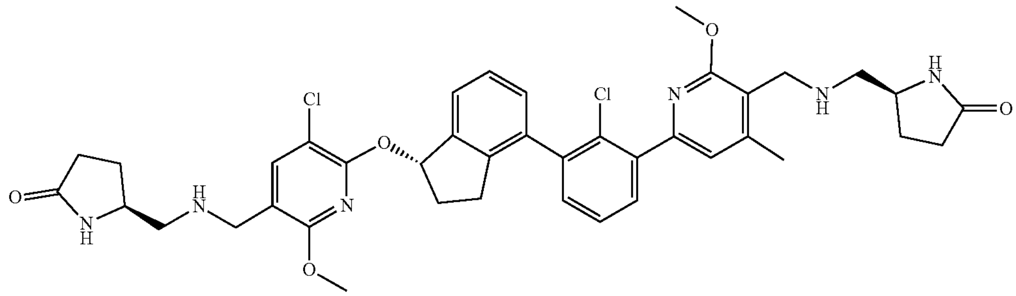
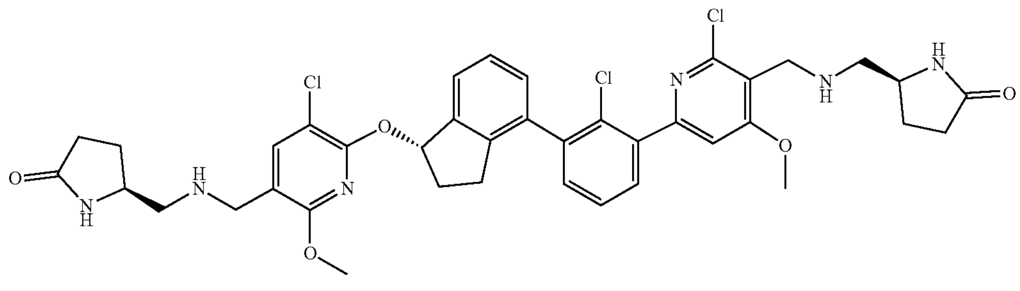

-continued

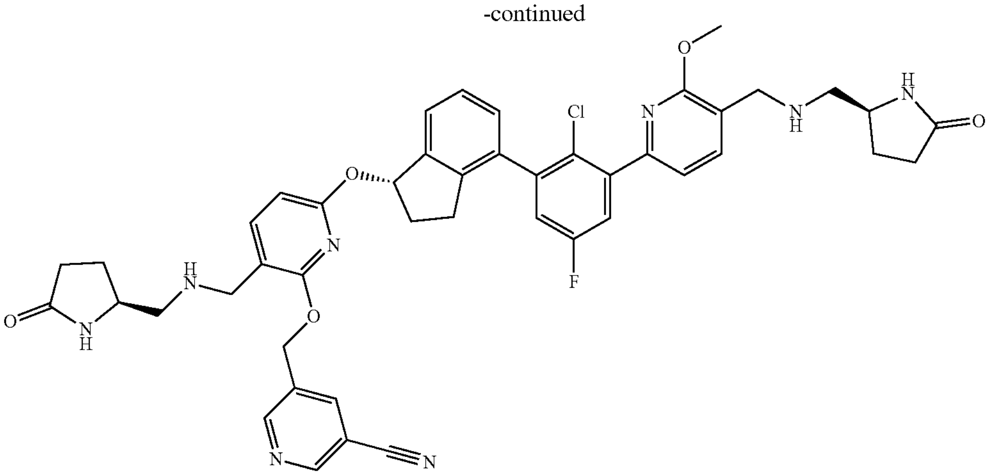

and

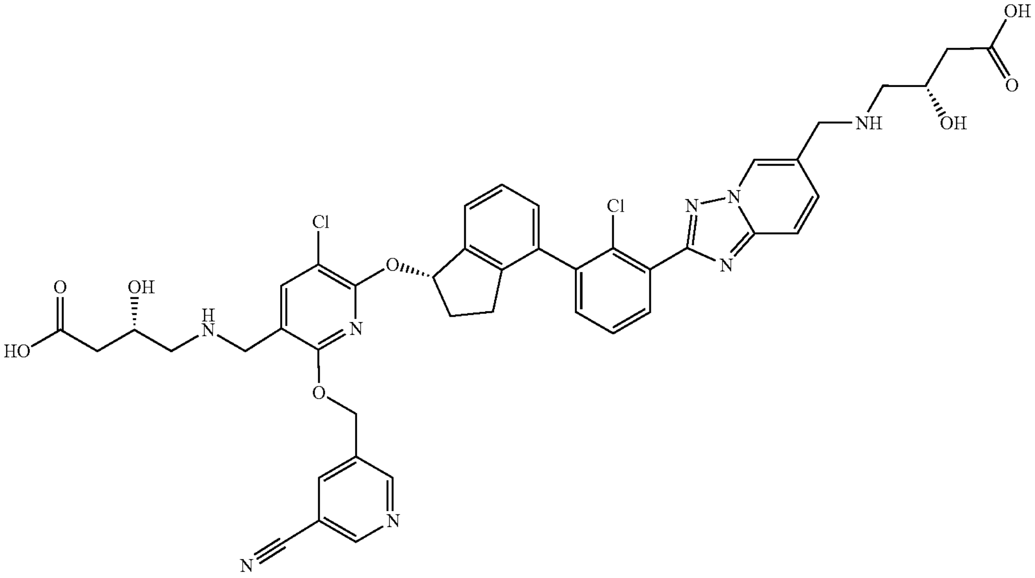

or a pharmaceutically acceptable salt thereof.

15. A pharmaceutical composition comprising a compound according to claim 1 or a pharmaceutically acceptable salt thereof, and at least one pharmaceutically acceptable excipient.

16. The pharmaceutical composition according to claim 15, further comprising at least one additional anticancer agent or therapy.

17. The pharmaceutical composition according to claim 15, further comprising at least one additional anticancer agent or therapy selected from rituxan, doxorubicin, gemcitabine, nivolumab, pembrolizumab, and ipilimumab, and at least one pharmaceutically acceptable excipient.

18. A method for inhibiting PD-1, PD-L1 and/or the PD-1/PD-L1 interaction comprising administering a compound according to claim 1 or a pharmaceutically acceptable salt thereof, to a patient in need thereof.

* * * * *